United States Patent
Bacon et al.

(10) Patent No.: US 10,344,019 B2
(45) Date of Patent: Jul. 9, 2019

(54) ANTIVIRAL COMPOUNDS

(71) Applicant: GILEAD PHARMASSET LLC, Foster City, CA (US)

(72) Inventors: Elizabeth M. Bacon, Burlingame, CA (US); Jeromy J. Cottell, Redwood City, CA (US); Ashley Anne Katana, San Mateo, CA (US); Darryl Kato, San Francisco, CA (US); Evan S. Krygowski, Washington, DC (US); John O. Link, San Francisco, CA (US); James G. Taylor, San Mateo, CA (US); Chinh Tran, Union City, CA (US); Teresa Alejandra Trejo Martin, Union City, CA (US); Zheng-Yu Yang, Palo Alto, CA (US); Sheila M. Zipfel, San Mateo, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 0 days.

(21) Appl. No.: 14/814,392

(22) Filed: Jul. 30, 2015

(65) Prior Publication Data

US 2015/0353529 A1 Dec. 10, 2015

Related U.S. Application Data

(63) Continuation of application No. 13/884,578, filed as application No. PCT/US2011/060966 on Nov. 16, 2011, now Pat. No. 9,156,823.

(60) Provisional application No. 61/504,924, filed on Jul. 6, 2011, provisional application No. 61/414,818, filed on Nov. 17, 2010.

(51) Int. Cl.
| | |
|---|---|
| *C07D 403/14* | (2006.01) |
| *C07D 405/14* | (2006.01) |
| *A61K 31/4178* | (2006.01) |
| *A61K 45/06* | (2006.01) |
| *A61K 31/4184* | (2006.01) |
| *A61K 31/4188* | (2006.01) |
| *C07D 417/14* | (2006.01) |
| *C07D 471/08* | (2006.01) |
| *C07D 491/10* | (2006.01) |
| *C07D 493/04* | (2006.01) |
| *C07D 495/04* | (2006.01) |
| *C07D 513/04* | (2006.01) |
| *A61K 31/5377* | (2006.01) |
| *C07D 491/107* | (2006.01) |
| *C07D 491/113* | (2006.01) |

(52) U.S. Cl.
CPC ........ *C07D 403/14* (2013.01); *A61K 31/4178* (2013.01); *A61K 31/4184* (2013.01); *A61K 31/4188* (2013.01); *A61K 31/5377* (2013.01); *A61K 45/06* (2013.01); *C07D 405/14* (2013.01); *C07D 417/14* (2013.01); *C07D 471/08* (2013.01); *C07D 491/10* (2013.01); *C07D 491/107* (2013.01); *C07D 491/113* (2013.01); *C07D 493/04* (2013.01); *C07D 495/04* (2013.01); *C07D 513/04* (2013.01)

(58) Field of Classification Search
CPC  C07D 403/14; C07D 405/14; A61K 31/4178; A61K 45/06
USPC ............... 514/43, 397; 548/312.1, 313.1
See application file for complete search history.

(56) References Cited

U.S. PATENT DOCUMENTS

| | | | |
|---|---|---|---|
| 5,858,389 | A | 1/1999 | Elsherbini |
| 6,841,566 | B2 | 1/2005 | Beaulieu et al. |
| 7,386,398 | B2 | 6/2008 | Coulombe et al. |
| 7,741,347 | B2 | 6/2010 | Bachand et al. |
| 8,147,818 | B2 | 4/2012 | Bachand et al. |
| 8,575,135 | B2 | 11/2013 | Bacon et al. |
| 8,618,076 | B2 | 12/2013 | Ross et al. |
| 8,891,379 | B2 | 11/2014 | Ninan et al. |
| 8,921,341 | B2 | 12/2014 | Bacon et al. |
| 8,940,718 | B2 | 1/2015 | Bacon et al. |
| 9,051,340 | B2 | 6/2015 | Bacon et al. |
| 9,079,887 | B2 * | 7/2015 | Bacon .................. C07D 401/14 |
| 9,125,904 | B1 * | 9/2015 | Wiles ................. A61K 31/4709 |
| 9,156,818 | B2 | 10/2015 | Or et al. |
| 9,156,823 | B2 | 10/2015 | Bacon et al. |
| 9,221,833 | B2 | 12/2015 | Bacon et al. |
| 9,233,974 | B2 | 1/2016 | Link et al. |
| 2009/0202478 | A1 | 8/2009 | Bachand et al. |
| 2009/0291138 | A1 | 11/2009 | Watanabe et al. |
| 2010/0256184 | A1 | 10/2010 | Rowe et al. |

(Continued)

FOREIGN PATENT DOCUMENTS

| | | |
|---|---|---|
| CA | 2815082 | 5/2013 |
| CN | 100457776 | 2/2009 |

(Continued)

OTHER PUBLICATIONS

Glossary of medical education terms, Institute of International Medical Education. http://www.iime.org/glossary.htm Accessed in Mar. 2013.*

(Continued)

*Primary Examiner* — Yih-Horng Shiao
(74) *Attorney, Agent, or Firm* — Sheppard Mullin Richter & Hampton LLP

(57) ABSTRACT

The invention is related to anti-viral compounds, compositions containing such compounds, and therapeutic methods that include the administration of such compounds, as well as to processes and intermediates useful for preparing such compounds.

7 Claims, No Drawings

(56) References Cited

U.S. PATENT DOCUMENTS

| | | | |
|---|---|---|---|
| 2010/0310512 A1* | 12/2010 | Guo | C07D 403/04 424/85.7 |
| 2011/0064698 A1* | 3/2011 | Or | A61K 38/21 424/85.5 |
| 2011/0251152 A1 | 10/2011 | Ross et al. | |
| 2011/0286961 A1* | 11/2011 | Belema | C07D 403/14 424/85.2 |
| 2013/0156732 A1 | 6/2013 | Bacon et al. | |
| 2013/0164260 A1 | 6/2013 | Bacon et al. | |
| 2013/0177530 A1 | 7/2013 | Bacon et al. | |
| 2013/0309196 A1 | 11/2013 | Link et al. | |
| 2014/0018313 A1 | 1/2014 | Bacon et al. | |
| 2014/0112885 A1 | 4/2014 | Bacon et al. | |
| 2014/0178336 A1 | 6/2014 | Link et al. | |
| 2014/0309432 A1 | 10/2014 | Bacon et al. | |
| 2014/0316144 A1 | 10/2014 | Bacon et al. | |
| 2015/0064252 A1 | 3/2015 | Gorman et al. | |
| 2015/0064253 A1 | 3/2015 | Gorman et al. | |
| 2015/0141326 A1 | 5/2015 | Bacon et al. | |
| 2015/0299213 A1 | 10/2015 | Bacon et al. | |
| 2015/0353529 A1 | 12/2015 | Bacon et al. | |
| 2016/0083394 A1 | 3/2016 | Bacon et al. | |
| 2016/0083395 A1 | 3/2016 | Bacon et al. | |
| 2016/0115175 A1 | 4/2016 | Bacon et al. | |
| 2016/0362416 A1 | 12/2016 | Link et al. | |
| 2017/0145027 A1 | 5/2017 | Bacon et al. | |

FOREIGN PATENT DOCUMENTS

| | | |
|---|---|---|
| CN | 101754966 A | 6/2010 |
| JP | 2011-511837 A | 4/2011 |
| JP | 2011-511840 A | 4/2011 |
| JP | 2016-051146 | 3/2016 |
| WO | WO-2003/007945 A1 | 1/2003 |
| WO | WO-2004/099241 | 11/2004 |
| WO | WO-2005/082880 | 9/2005 |
| WO | WO-2008/021927 | 2/2008 |
| WO | WO-2008/021928 | 2/2008 |
| WO | WO-2008/021936 | 2/2008 |
| WO | WO-2008/144380 | 11/2008 |
| WO | WO-2009/102318 | 8/2009 |
| WO | WO-2009/102325 | 8/2009 |
| WO | WO-2009/102568 | 8/2009 |
| WO | WO-2009/102633 | 8/2009 |
| WO | WO-2010/062821 | 6/2010 |
| WO | WO-2010/065681 | 6/2010 |
| WO | WO-2010/096777 | 8/2010 |
| WO | WO-2010/099527 | 9/2010 |
| WO | WO-2010/111534 | 9/2010 |
| WO | WO-2010/111673 | 9/2010 |
| WO | WO-2010/132538 | 11/2010 |
| WO | WO-2010/132601 | 11/2010 |
| WO | WO-2010/138368 | 12/2010 |
| WO | WO-2011/028596 | 3/2011 |
| WO | WO-2011/031904 | 3/2011 |
| WO | WO-2011/066241 | 6/2011 |
| WO | WO-2011/075439 | 6/2011 |
| WO | WO-2011/075607 A1 | 6/2011 |
| WO | WO-2011/087740 | 7/2011 |
| WO | WO-2011/112429 | 9/2011 |
| WO | WO-2011/146401 | 11/2011 |
| WO | WO-2012/027712 | 3/2012 |
| WO | WO-2012/048421 | 4/2012 |
| WO | WO-2012/068234 | 5/2012 |
| WO | WO-2012/087976 | 6/2012 |
| WO | WO-2013/075029 | 5/2013 |
| WO | WO-2013/173488 A1 | 11/2013 |
| WO | WO-2013/173492 | 11/2013 |
| WO | WO-2014/100500 | 6/2014 |
| WO | WO-2015/030853 A1 | 3/2015 |
| WO | WO-2015/030854 A1 | 3/2015 |
| WO | WO-2015/191431 | 12/2015 |
| WO | WO-2015/191437 | 12/2015 |

OTHER PUBLICATIONS

Curry et al. Sofosbuvir and Ribavirin Prevent Recurrence of HCV Infection After Liver Transplantation: An Open-Label StudyGastroenterology 148:100-107, 2015.*
International Search Report and Written Opinion for PCT/US2012/065681 dated Jan. 25, 2013, 3 pages.
International Search Report and Written Opinion for PCT/US2011/060966 dated Sep. 19, 2012, 42 pages.
Lam et al., "Genotype and Subtype Profiling of PSI-7977 as a Nucleotide Inhibitor of Hepatitis C Virus," Antimicrobial Agents and Chemotherapy, (2012), 56(6):3359-3368.
STN Registry No. 1190307-88-0. "Sofosbuvir," Retrieved from STN Registry File Oct. 25, 2013, 1 page.
U.S. Appl. No. 15/207,415, filed Jul. 11, 2016, Bacon et al.
U.S. Appl. No. 15/282,128, filed Sep. 30, 2016, Gorman et al.
Chiou et al., "Crystallization of Amorphous Components in Spray-Dried Powders", Drying Technology, 25:1427-1435, 2007.
Curry et al., "Sofosbuvir and Ribavirin Prevent Recurrence of HCV Infection After Liver Transplantation: An Open-Label Study", Gastroenterology 2015;148:100-107.
Examination Report for Australia Application No. 2015243078 dated Apr. 14, 2016. (9 pages).
Examination Report for New Zealand Application No. 610531 dated Aug. 20, 2015. (2 pages).
Examination Report for New Zealand Application No. 710567 dated Aug. 20, 2015. (3 pages).
Glossary of Medical Education Terms, Institute for International Medical Education. http://www.iime.org/glossary.htm. Accessed in Mar. 2013.
International Preliminary Report on Patentability for International Application No. PCT/US2011/060966 dated May 21, 2013. (27 pages).
International Preliminary Report on Patentability for International Application No. PCT/US2013/041201 dated Nov. 18, 2014. (6 pages).
International Preliminary Report on Patentability for International Application No. PCT/US2014/013930 dated Mar. 1, 2016. (5 pages).
International Preliminary Report on Patentability for International Application No. PCT/US2014/013933 dated Mar. 1, 2016. (7 pages).
International Preliminary Report on Patentability for International Application No. PCT/US2012/065681 dated May 20, 2014. (5 pages).
International Search Report and Written Opinion for International Application No. PCT/US2013/041201 dated Jul. 5, 2013. (10 pages).
International Search Report and Written Opinion for International Application No. PCT/US2014/013930 dated May 8, 2014. (7 pages).
International Search Report and Written Opinion for International Application No. PCT/US2014/013933 dated Apr. 28, 2014. (10 pages).
Office Action and Search Report for Taiwan Application No. 100141839 dated Oct. 6, 2015. (9 pages).
Office Action for European Application No. 11791700.5 dated Oct. 5, 2015. (3 pages).
Office Action for Israel Application No. 226346 dated Jul. 20, 2015. (4 pages).
Office Action for U.S. Appl. No. 14/814,392 dated Jul. 28, 2016. (21 pages).
Official Action for Japanese Application No. 2013-539970 dated Aug. 24, 2015. (4 pages).
Official Action for Vietnam Application No. 1-2013-01720 dated Nov. 30, 2015. (1 page).
Zheng et al., "Syntheses and initial evaluation of a series of indolo-fused heterocyclic inhibitors of the polymerase enzyme (NSSB) of the hepatitis C virus", Bioorganic & Medicinal Chemistry Letters, 21(2011), pp. 2925-2929.
Brunton, et al., "Goodman and Gilam's the Pharmacological Basis of Therapeutics," 11th Edition, McGraw-Hill, 4103-4105, lines 1-7, (2005).
Caira, M.R., Topics in Current Chemistry 1998. vol. 198, Jan. 1, 1998, pp. 163-208.

(56) References Cited

OTHER PUBLICATIONS

Examination Report for Australian Application No. 2011328980 dated Dec. 18, 2014. (9 pages).
Examination Report for New Zealand Application No. 726475 dated Dec. 12, 2016. (4 pages).
Office Action dated Jan. 5, 2017 for Taiwanese Application No. 105118984. (3 pages).
Office Action dated Mar. 28, 2017 for Israeli Application No. 226346. (4 pages).
Office Action dated Apr. 28, 2017 for New Zealand Application No. 726475. (2 pages).
Office Action dated May 11, 2017 for South Korean Application No. 10-2013-7015201. (6 pages).
Office Action dated Dec. 22, 2014 for U.S. Appl. No. 13/884,578. (9 pages).
Office Action dated Mar. 14, 2014 for European Application No. 11791700.5. (7 pages).
Office Action dated Apr. 7, 2015 for Bolivian Application No. SP-0347-2011. (2 pages).
Office Action dated Sep. 23, 2014 for Bolivian Application No. SP-0347-2011. (14 pages).
Official Action dated Feb. 14, 2017 for Japanese Application No. 2016-051146. (2 pages).
Substantive Examination Report dated Jul. 29, 2016 for Vietnamese Application No. 1-2013-01720. (1 page).
Tripathi, D.D, "Essentials of Medical Pharmacology," 5th Edition, Jaypee Brothers Medical Publishers Lrd, 4106-4017, lines 10-13, (2004).
Examination Report for Australia Application No. 2017202461 dated Mar. 21, 2018. (2 pages).
Extended Search Report for European Application No. 17169675.0 dated Dec. 7, 2017. (15 pages).
Final Office Action for Japanese Application No. 2016-51146 dated Aug. 18, 2017. (1 page).
Office Action for Canadian Application No. 2,817,840 dated Oct. 24, 2017. (5 pages).
Official Action for Bolivian Application No. SP-0347-2011-F1 dated Nov. 16, 2017. (16 pages).
Examination Report for New Zealand Patent Application No. 742894 dated Jul. 5, 2018. (3 pages).
Examiner's Requisition for Canadian Patent Application No. 2,817,840 dated Jul. 6, 2018. (5 pages).
Notice of Preliminary Rejection for Korean Patent Application No. 10-2018-7005807 dated Apr. 25, 2018. (5 pages).

\* cited by examiner

ANTIVIRAL COMPOUNDS

PRIORITY OF INVENTION

This application is a continuation of U.S. patent application Ser. No. 13/884,578, filed Jul. 23, 2013, now U.S. Pat. No. 9,156,823, which is a U.S. National Stage Application under 35 U.S.C. § 371 of International Application No. PCT/US11/60966, filed Nov. 16, 2011, which claims priority to United States Provisional Application Nos. 61/414,818, filed Nov. 17, 2010 and 61/504,924 filed Jul. 6, 2011. The entire content of each of these applications is incorporated herein by reference.

BACKGROUND OF THE INVENTION

Hepatitis C is recognized as a chronic viral disease of the liver which is characterized by liver disease. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

There is a need for new HCV therapeutic agents. In particular, there is a need for HCV therapeutic agents that have broad activity against HCV genotypes (e.g. genotypes 1a, 1b, 2a, 3a, 4a). There is also a particular need for agents that are less susceptible to viral resistance. Resistance mutations to inhibitors have been described for HCV NS5A for genotypes 1a and 1b in Antimicrobial Agents and Chemotherapy, Sep. 2010, Volume 54, p. 3641-3650.

SUMMARY OF THE INVENTION

In one embodiment the invention provides a compound of the invention which is compound of formula (I):

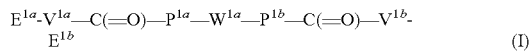

(I)

wherein:

$E^{1a}$ is $E^0$, $E^1$, or $E^2$, or $E^{1a}$-$V^{1a}$ taken together are $R^{9a}$;
$E^{1b}$ is $E^0$, $E^1$, or $E^2$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
$P^{1a}$ is selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;
$P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $E^2$ is independently —$NHR^{Ef}$ wherein $R^{Ef}$ is cycloalkylcarbonyl or cycloalkyloxycarbonyl;

each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, ($NR^XR^Y$)alkyl-, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, ($NR^XR^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $P^0$ is independently:

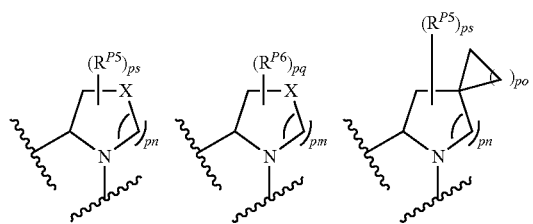

-continued

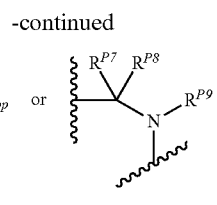

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;
each P$^1$ is independently:

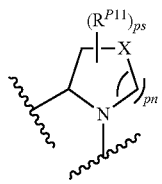

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocycly-loxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclooxyalkyloxy, (NR$^h$R$^h$)alkyloxy, cyanoalkoxy, cyanocycloalkyloxy, cycloalkyloxy, oxo and heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

ps is 1, 2, 3, or 4;
pn is 0, 1, or 2;
each P$^3$ is independently a ring of the formula:

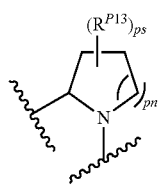

wherein:
the ring is substituted with one or more oxo group;
each R$^{P13}$ is independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

ps is 0, 1, 2, 3, or 4;
pn is 0, 1, or 2;

each $P^5$ is independently a ring of the formula:

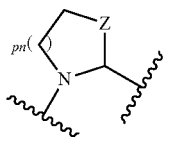

wherein:
the ring is optionally substituted with one or more groups $R^{P15}$ that are independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pn is 0, 1, or 2;
Z is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $-S(=O)_2NR^hR^h$, $-S(=O)_2R^h$, $C(=O)R^h$, $C(=O)OR^h$, $-C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

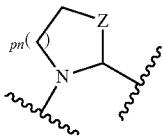

wherein:
the ring is substituted with one or more oxo and is optionally substituted with one or more groups $R^{P16}$ that are independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
Z is O, S, S(=O), S(=O)$_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $-S(=O)_2NR^hR^h$, $-S(=O)_2R^h$, $C(=O)R^h$, $C(=O)OR^h$, $-C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;
each $P^8$ is independently a ring of the formula:

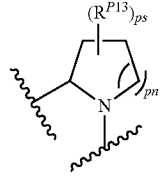

wherein:
ps is 2, 3, 4, 5, or 6;
pn is 0, 1 or 2;
each $R^{P13}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
each $P^{10}$ is independently:

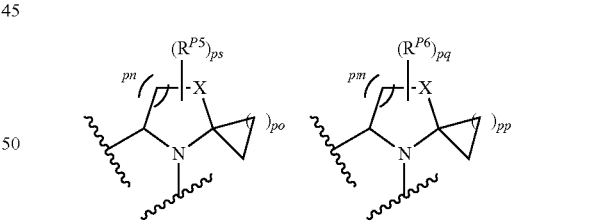

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each $R^{P10}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;
each $P^{12}$ is independently:

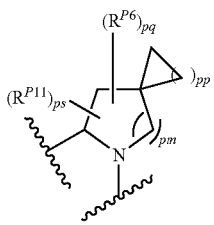

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq is independently 0, 1, 2, 3, or 4;
pm is independently 0, 1, or 2;
pp is independently 1, 2, or 3;
ps is 1, 2, 3, or 4;

$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl. (NR$^h$R$^h$)sulfonyl, heteroarylsulfonyl, —S(=O)$_2$R$^h$, —C(=O)R$^h$, —C(=O)NR$^h$R$^h$; and the remaining $R^{P11}$ are independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each $P^{15}$ is:

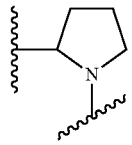

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

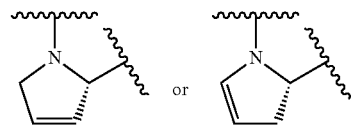 [SMILES: *[C@@H]1C=CCN1* ; *[C@@H]1CC=CN1*]

which is optionally substituted, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl with one or two groups independently selected from halo, alkyl, alkoxyalkyl, haloalkyl, cycloalkyl, and cycloalkylalkyl;

each $P^{19}$ is:

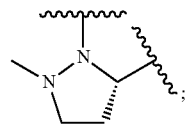

each $P^{30}$ is independently a ring of the formula:

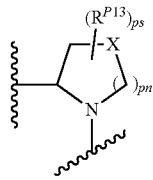

ps is 2
pn is 0, 1 or 2;
X is selected from O, S, S(O), SO$_2$, or CH$_2$; provided that when pn is 0, X is CH$_2$.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each R$^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl; and W$^{1a}$ is selected from:

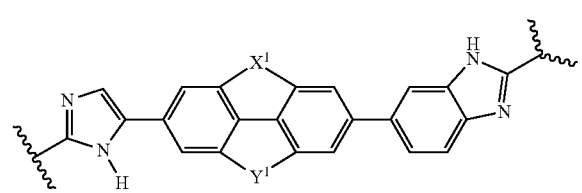

101

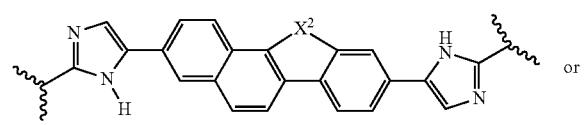

102 or

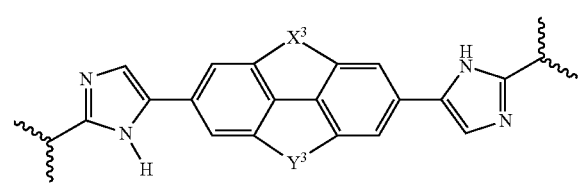

103

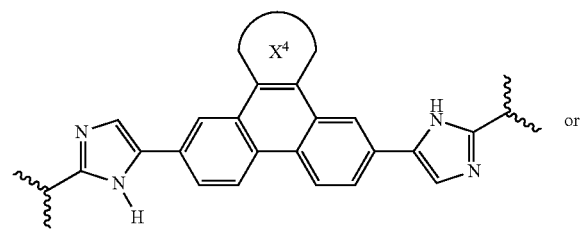

104 or

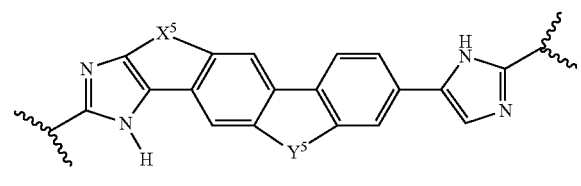

105

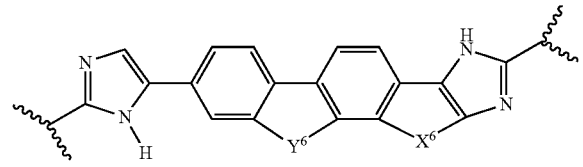

106

-continued

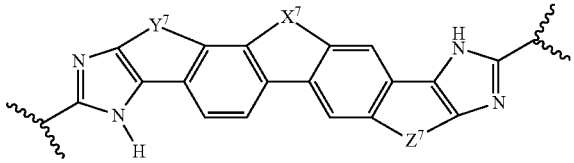
107

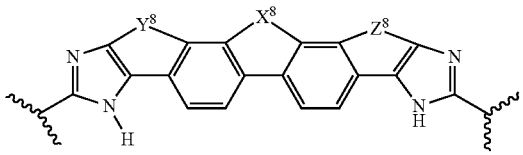
108 and

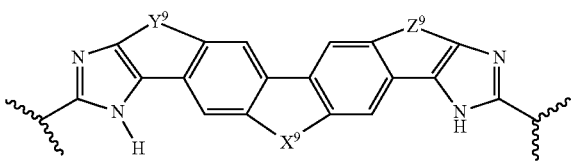
109 wherein each $W^{1a}$ is optionally substituted with one or more (e.g. 1, 2, 3, or 4) groups independently selected from halo, alkyl, haloalkyl, cyano and

;

wherein each R is independently H, alkyl, haloalkyl, cycloalkyl, aryl, or heteroaryl;

$X^1$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$Y^1$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$X^2$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$X^3$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$Y^3$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$X^4$ is a six membered aromatic or heteroaromatic or five membered heteroraromatic ring;

$X^5$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$Y^5$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$X^6$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$Y^6$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$X^7$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$Y^7$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$Z^7$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$X^8$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$Y^8$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$Z^8$ is —$CH_2$—, —$CH_2$—$CH_2$—, —$CH_2$—O—, —$CH_2$—O—$CH_2$—, —S—, —S(O)$_2$—, —C(O)—, —$CF_2$—, —OC(O)—, —(O)CO—, or —CH=CH—;

$X^9$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

$Y^9$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—; and $Z^9$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —$CF_2$—, —O—, —S—$CH_2$—, —$CH_2$—S—, —OC(O)—, —(O)CO—, or —CH=CH—;

or a pharmaceutically acceptable salt or prodrug thereof.

In another embodiment the invention provides a compound of the invention which is compound of formula (I):

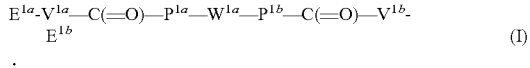
(I)

wherein:
$E^{1a}$ is $E^0$, $E^1$, or $E^2$, or $E^{1a}$-$V^{1a}$ taken together are $R^{9a}$;
$E^{1b}$ is $E^0$, $E^1$, or $E^2$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
one of $P^{1a}$ and $P^{1b}$ is selected from $P^1$, $P^3$, $P^5$, $P^6$, $P^7$, $P^8$, $P^{10}$, $P^{12}$, $P^{15}$, $P^{18}$, $P^{19}$ and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$;

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR^eR^f)alkyl, (NR^eR^f)alkylcarbonyl, (NR^eR^f)carbonyl, (NR^eR^f)sulfonyl, —C(NCN)OR', and —C(NCN)NR^XR^Y, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR^eR^f group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each E¹ is independently selected from hydrogen, hydroxy, alkyl, haloalkyl, —NHhaloalkyl, aryl, and heterocyclyl;

each E² is independently —NHR^Ef wherein R^Ef is cycloalkylcarbonyl or cycloalkyloxycarbonyl;

each V⁰ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR^XR^Y, (NR^XR^Y)alkyl-, oxo, and —P(O)OR₂, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR^XR^Y, (NR^XR^Y)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each P⁰ is independently:

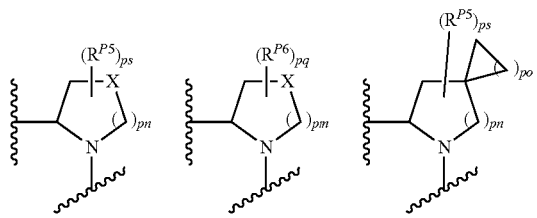

-continued

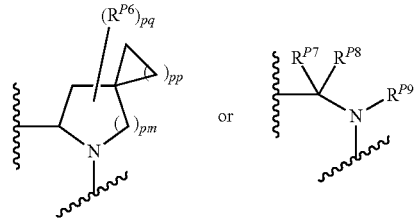

wherein:

X is selected from O, S, S(O), SO₂, CH₂, CHR^P10, and C(R^P10)₂; provided that when pn or pm is 0, X is selected from CH₂, CHR^P10, and C(R^P10)₂;

each R^P10 is independently selected from alkoxy, alkyl, aryl, halo, haloalkyl, hydroxy, and —NR^PaR^Pb, wherein the alkyl can optionally form a fused three- to six-membered ring with an adjacent carbon atom, wherein the three- to six-membered ring is optionally substituted with one or two alkyl groups;

each R^P5 and R^P6 is independently selected from alkoxy, alkyl, aryl, halo, haloalkyl, hydroxy, and —NR^PaR^Pb, wherein the alkyl can optionally form a fused three- to six-membered ring with an adjacent carbon atom, wherein the three- to six-membered ring is optionally substituted with one or two alkyl groups;

R^Pa and R^Pb are each independently H, alkyl, aryl, or arylalkyl; or R^Pa and R^Pb taken together with the atom to which they are attached form a heterocycle;

pq and ps are independently 0, 1, 2, 3, or 4;
pm and pn are independently 0, 1, or 2;
po and pp are independently 1, 2, or 3;
R^P7 and R^P8 are each independently selected from hydrogen, alkenyl, alkoxyalkyl, alkyl, haloalkyl, and (NR^PaR^Pb)alkyl; or R^P7 and R^P8, together with the carbon atom to which they are attached, form a five or six membered saturated ring optionally containing one or two heteroatoms selected from NR^Pz, O, and S; wherein R^Pz is selected from hydrogen and alkyl;

R^P9 is selected from hydrogen and alkyl;

each P¹ is independently:

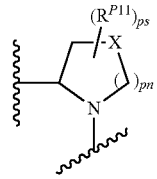

wherein:

X is selected from O, S, S(O), SO₂, CH₂, CHR^P10, and C(R^P10)₂; provided that when pn is 0, X is selected from CH₂, CHR^P10, and C(R^P10)₂;

each R^P10 is independently selected from alkoxy, alkyl, aryl, halo, haloalkyl, hydroxy, and —NR^PaR^Pb, wherein the alkyl can optionally form a fused three- to six-membered ring with an adjacent carbon atom, wherein the three- to six-membered ring is optionally substituted with one or two alkyl groups;

at least one R^P11 is independently selected from cyano, alkylsulfonyl, arylsulfonyl, (NR^hR^h)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo and heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl sulfonylalkyl; and when two R$^h$ groups are present then they may come together with the atoms to which they are bound to form a 4-15 membered heterocyclic ring;

ps is 1, 2, 3, or 4;

pn is 0, 1, or 2;

each P$^3$ is independently a ring of the formula:

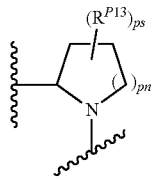

wherein:

the ring is substituted with one or more oxo group;

each R$^{P13}$ is independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

ps is 0, 1, 2, 3, or 4;

pn is 0, 1, or 2;

each P$^5$ is independently a ring of the formula:

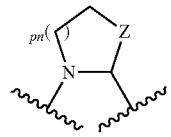

wherein:

the ring is optionally substituted with one or more groups R$^{P15}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups R$^{P15}$ that are attached to the same carbon when taken together with the carbon to which they are attached can form a 3-6 membered carbocyclic or heterocyclic ring;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pn is 0, 1, or 2;

Z is O, S, S(=O), S(=O)$_2$, or NR$^f$;

each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;

each P$^6$ is independently a ring of the formula:

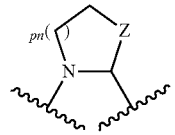

wherein:

the ring is substituted with one or more oxo and is optionally substituted with one or more groups R$^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

Z is O, S, S(=O), S(=O)$_2$, or NR$^f$;

pn is 0, 1, or 2;

each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;

each P$^7$ is a bridged 5-15 membered bicyclic heterocyclic ring that is attached to the remainder of the compound of formula I through one N-link and through one C-link; wherein the ring is optionally substituted with one or more groups independently selected from R$^{P6}$ and R$^{P11}$;

each P$^8$ is independently a ring of the formula:

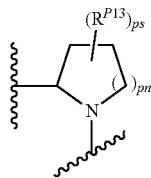

wherein:
ps is 2, 3, 4, 5, or 6;
pn is 0, 1 or 2;
each R$^{P13}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; where in at least one case two groups R$^{P13}$ that are attached to the same carbon are taken together with the carbon to which they are attached and form a 4-6 membered heterocyclic ring;
R$^{Pa}$ and R$^{Pb}$ are each independently H, alkyl, aryl, or arylalkyl; or R$^{Pa}$ and R$^{Pb}$ taken together with the atom to which they are attached form a heterocycle;

each P$^{10}$ is independently:

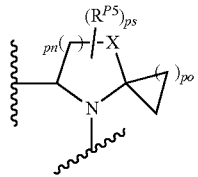 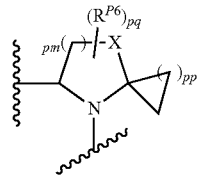

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
pq and ps are independently 0, 1, 2, 3, or 4;
pm and pn are independently 0, 1, or 2;
po and pp are independently 1, 2, or 3;
each P$^{12}$ is independently:

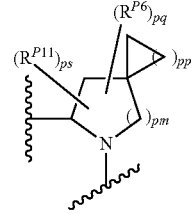

wherein:
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
pq is independently 0, 1, 2, 3, or 4;
pm is independently 0, 1, or 2;
pp is independently 1, 2, or 3;
ps is 1, 2, 3, or 4;
R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each P¹⁵ is:

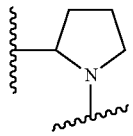

which is substituted with one or two groups independently selected from alkoxyalkyl, haloalkoxyalkyl, alkylsulfanyl, alkylsulfanylalkyl, cyanoalkyl, and cycloalkylalkyl;

each P¹⁸ is:

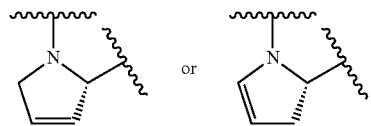

which is optionally substituted with one or two groups independently selected from halo, alkyl, alkoxyalkyl, haloalkyl, cycloalkyl, and cycloalkylalkyl;

each P¹⁹ is:

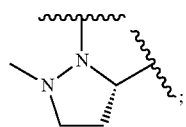

each P³⁰ is independently a ring of the formula:

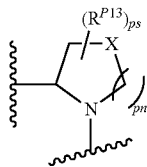

ps is 2
pn is 0, 1 or 2;
X is selected from O, S, S(O), SO₂, or CH₂; provided that when pn is 0, X is CH₂.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

W$^{1a}$ is selected from:

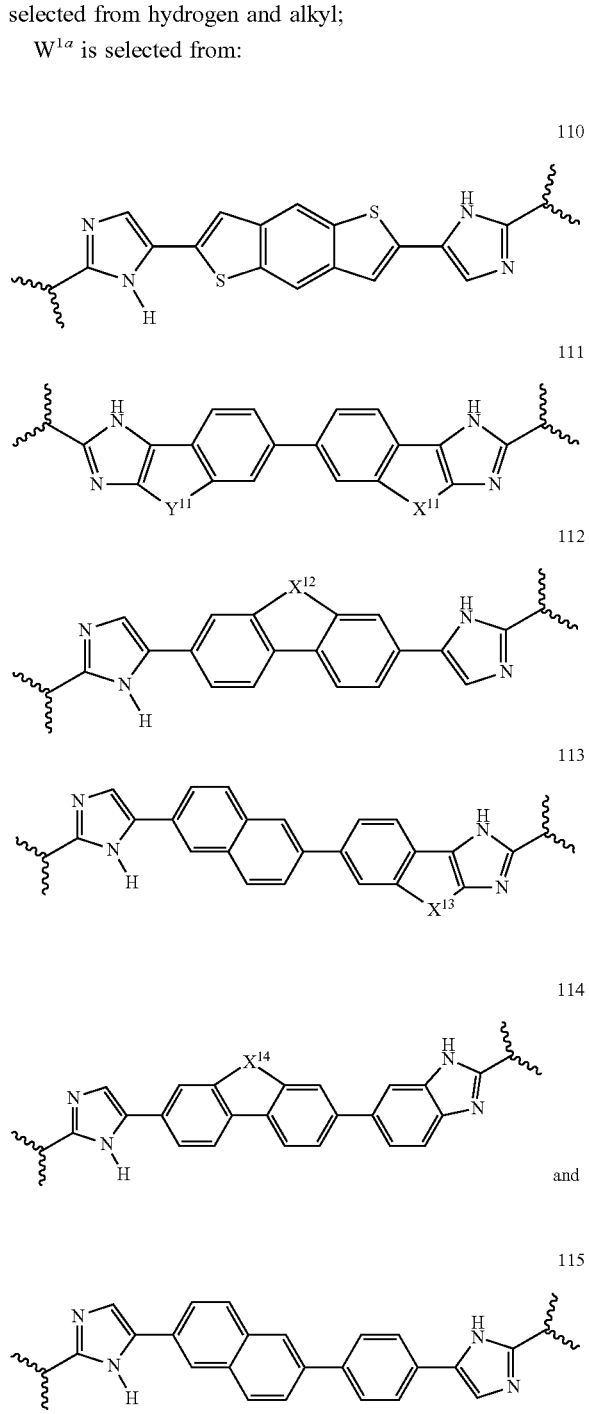

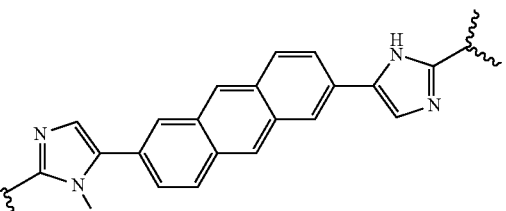

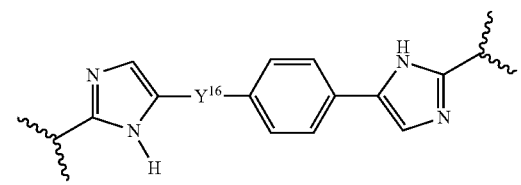

wherein each W$^{1a}$ is optionally substituted with one or more (e.g. 1, 2, 3, or 4) groups independently selected from halo, alkyl, haloalkyl, cyano, and

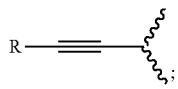

wherein each R is independently H, alkyl, haloalkyl, cycloalkyl, aryl, or heteroaryl;

X$^{11}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

Y$^{11}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

X$^{12}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

X$^{13}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—; and X$^{14}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—; and each Y$^{16}$ is a bicyclic aromatic ring system comprising eight to 12 atoms optionally including one or more heteroatoms selected from O, S, and N, which bicyclic ring system is optionally with one or more groups independently selected from halo, haloalkyl, alkyl and oxo.

or a pharmaceutically acceptable salt or prodrug thereof.

In another embodiment the invention provides a compound of the invention which is compound of formula (I):

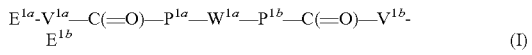

wherein:
$E^{1a}$ is $E^0$, $E^1$, or $E^2$, or $E^{1a}$-$V^{1a}$ taken together are $R^{9a}$;
$E^{1b}$ is $E^0$, $E^1$, or $E^2$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
one of $P^{1a}$ and $P^{1b}$ is selected from $P^1$, $P^3$, $P^5$, $P^6$, $P^7$, $P^8$, $P^{10}$, $P^{12}$, $P^{15}$, $P^{18}$, $P^{19}$ and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$;

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, aryl, and heterocyclyl;
each $E^2$ is independently —$NHR^{Ef}$ wherein $R^{Ef}$ is cycloalkylcarbonyl or cycloalkyloxycarbonyl;
each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, $(NR^XR^Y)$alkyl-, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a heterocyclyl group, heterocyclylalkyl, heterocyclylcarbonyl, hydroxy, hydroxyalkyl, nitro, —$NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$W^{1a}$ is:

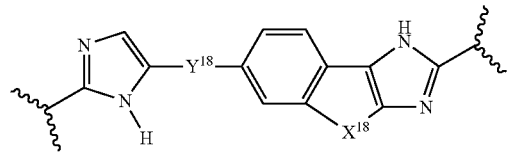

118 wherein $W^{1a}$ is optionally substituted with one or more (e.g. 1, 2, 3, or 4) groups independently selected from halo, alkyl, haloalkyl, cyano, and

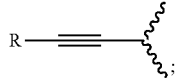

wherein each R is independently H, alkyl, haloalkyl, cycloalkyl, aryl, or heteroaryl;
$Y^{18}$ is selected from $A^0$, $A^1$, $A^2$, $A^3$, $A^7$, $A^{15}$, $A^{16}$, and $A^{20}$;
each $A^0$ is independently:

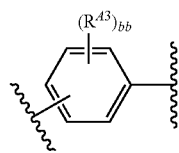

wherein:
each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$ $(NR^aR^b)$alkyl, and $(NR^aR^b)$carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each
bb is independently 0, 1, 2, 3, or 4; or
each $A^0$ is independently a six-membered heteroaromatic ring containing one, two, or three nitrogen atoms, which ring is optionally substituted with 1, 2, 3, or 4 $R^{43}$ groups;
each $A^1$ is independently:

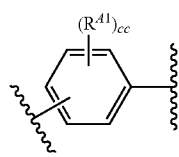

wherein:
each $R^{A1}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and
each $R^4$ is independently selected from H, alkyl, haloalkyl, aryl, and arylalkyl;
each cc is independently 1, 2, 3, or 4;
each $A^2$ is independently:

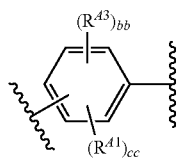

wherein:
each $R^{A1}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^{A3}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, $(NR^aR^b)$alkyl, and $(NR^aR^b)$carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $R^4$ is independently selected from H, alkyl, haloalkyl, aryl, and arylalkyl;
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each bb is 0, 1, 2, 3, or 4; each cc is 1, 2, 3, or 4; and the sum of bb and cc is 1, 2, 3, or 4;
each $A^3$ is independently a six-membered heteroaromatic ring containing one, two, or three nitrogen atoms, which ring is substituted with one or more $R^{A1}$ groups, and which ring is optionally substituted with one or more $R^{A3}$ groups;
each $A^7$ is independently:

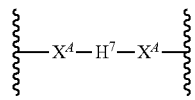

wherein:
each $H^7$ is independently a five-membered heteroaromatic ring, which $H^7$ is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent; and each R is independently selected from H or alkyl;

each $A^{15}$ is independently:

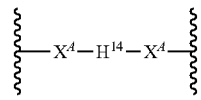

wherein:
each $H^{14}$ is independently a fused unsaturated, partially unsaturated or saturated tricyclic carbocycle which is optionally substituted with one or more groups independently selected from oxo, $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^{16}$ is independently:

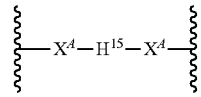

wherein:
each $H^{15}$ is independently a fused unsaturated, partially unsaturated or saturated tricyclic heterocycle that comprises at least one heteroatom in the ring system, which ring system is optionally substituted with one or more groups independently selected from $R^{A1}$ and $R^{A3}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^{20}$ is independently a 5 or 6 membered heteroaryl ring that is optionally substituted with one or more groups independently selected from $R^{A1}$ and $R^{A3}$;
each $P^0$ is independently:

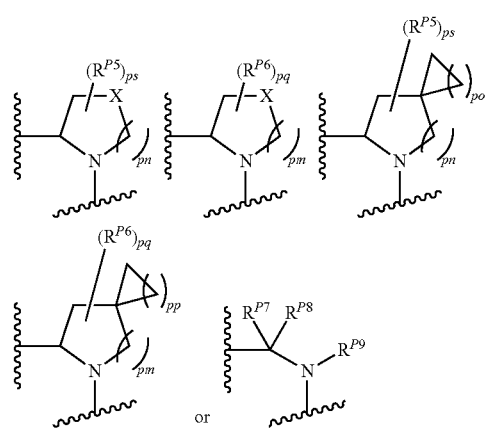

wherein:
X is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

$R^{P7}$ and $R^{P8}$ are each independently selected from hydrogen, alkenyl, alkoxyalkyl, alkyl, haloalkyl, and ($NR^{Pa}R^{Pb}$)alkyl; or $R^{P7}$ and $R^{P8}$, together with the carbon atom to which they are attached, form a five or six membered saturated ring optionally containing one or two heteroatoms selected from $NR^{Pz}$, O, and S; wherein $R^{Pz}$ is selected from hydrogen and alkyl;

$R^{P9}$ is selected from hydrogen and alkyl;
each $P^1$ is independently:

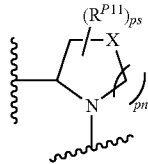

wherein:
X is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

at least one $R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclyloxyalkyloxy, ($NR^hR^h$)alkyloxy, cyanoalkoxy, cyanocycloalkoxy, cycloalkyloxy, oxo, heterocyclyl, —$NR^{hh}R^h$, ($NR^{hh}R^h$)alkyl, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo and heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;
each $P^3$ is independently a ring of the formula:

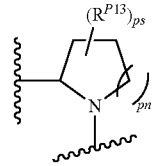

wherein:
the ring is substituted with one or more oxo group;
each $R^{P13}$ is independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 0, 1, 2, 3, or 4;
pn is 0, 1, or 2;
each $P^5$ is independently a ring of the formula:

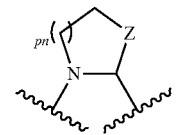

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pn is 0, 1, or 2;

Z is O, S, S(=O), S(=O)$_2$, or $NR^f$;

each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^6$ is independently a ring of the formula:

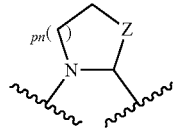

wherein:

the ring is substituted with one or more oxo and is optionally substituted with one or more groups $R^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

Z is O, S, S(=O), S(=O)$_2$, or $NR^f$;

pn is 0, 1, or 2;

each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula I through one N-link and through one C-link;

wherein the ring is optionally substituted with one or more groups independently selected from $R^{P6}$ and $R^{P11}$;

each $P^8$ is independently a ring of the formula:

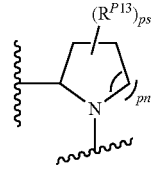

wherein:

ps is 2, 3, 4, 5, or 6;

pn is 0, 1 or 2;

each $R^{P13}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

each $P^{10}$ is independently:

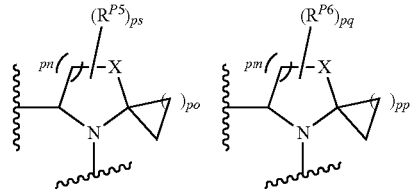

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;

pm and pn are independently 0, 1, or 2;

po and pp are independently 1, 2, or 3;

each $P^{12}$ is independently:

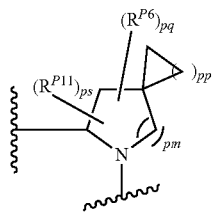

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq is independently 0, 1, 2, 3, or 4;
pm is independently 0, 1, or 2;
pp is independently 1, 2, or 3;
ps is 1, 2, 3, or 4;
$R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$) alkyloxy, cyanoalkoxy, cyanocycloalkyloxy, cycloalkyloxy, oxo, heterocyclyl, —$NR^{hh}R^h$, ($NR^{hh}R^h$)alkyl, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$) sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
each $P^{15}$ is:

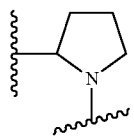 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;
each $P^{18}$ is:

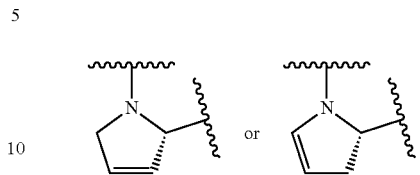

which is optionally substituted with one or two groups independently selected from halo, alkyl, alkoxyalkyl, haloalkyl, cycloalkyl, and cycloalkylalkyl;
each $P^{19}$ is:

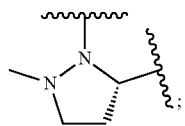 [SMILES: *[C@@H]1CCN(C)N1*]

each $P^{20}$ is:

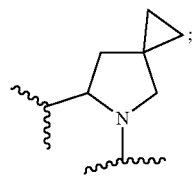 [SMILES: *C1CC2(CC2)CN1*]

each $P^{30}$ is independently a ring of the formula:

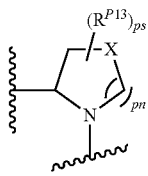

ps is 2
pn is 0, 1 or 2;
X is selected from O, S, S(O), $SO_2$, or $CH_2$; provided that when pn is 0, X is $CH_2$.
each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;
each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —$(NR^XR^Y)$alkyl, and —$(NR^XR^Y)$carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl; and each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —$(NR^XR^Y)$alkyl, and —$(NR^XR^Y)$carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl;

$X^{18}$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —O—C(O)—, —C(O)—O—, —CH=N—; —N=CH—; or —CH=CH—;

or a pharmaceutically acceptable salt or prodrug thereof.

In another embodiment the invention provides a compound of the invention which is compound of formula (I):

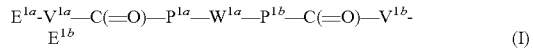

$$E^{1a}\text{-}V^{1a}\text{—}C(=O)\text{—}P^{1a}\text{—}W^{1a}\text{—}P^{1b}\text{—}C(=O)\text{—}V^{1b}\text{-}E^{1b} \quad (I)$$

wherein:

$E^{1a}$ is $E^0$, $E^1$, or $E^2$, Or $E^{1a}\text{-}V^{1a}$ taken together are $R^{9a}$;
$E^{1b}$ is $E^0$, $E^1$, or $E^2$, or $E^{1b}\text{-}V^{1b}$ taken together are $R^{9b}$;
$V^{1a}$ is $V^0$ or $E^{1a}\text{-}V^{1a}$ taken together are $R^{9a}$;
$V^{1b}$ is $V^0$ or $E^{1b}\text{-}V^{1b}$ taken together are $R^{9b}$;

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, aryl, and heterocyclyl;

each $E^2$ is independently —$NHR^{Ef}$ wherein $R^{Ef}$ is cycloalkylcarbonyl or cycloalkyloxycarbonyl;

each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, $(NR^XR^Y)$alkyl-, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$P^{1a}$ and $P^{1b}$ are each independently selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;

each $P^0$ is independently:

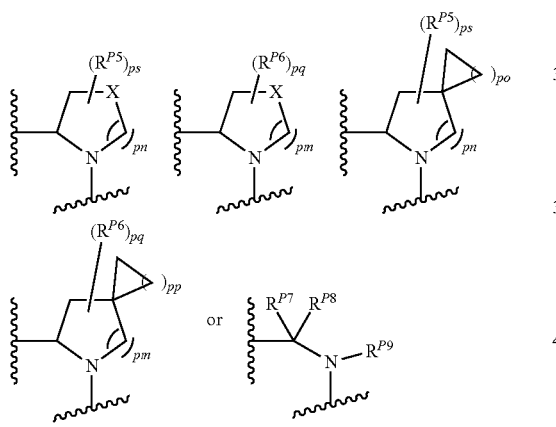

wherein:
X is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

$R^{P7}$ and $R^{P8}$ are each independently selected from hydrogen, alkenyl, alkoxyalkyl, alkyl, haloalkyl, and $(NR^{Pa}R^{Pb})$alkyl; or $R^{P7}$ and $R^{P8}$, together with the carbon atom to which they are attached, form a five or six membered saturated ring optionally containing one or two heteroatoms selected from $NR^{Pz}$, O, and S; wherein $R^{Pz}$ is selected from hydrogen and alkyl;

$R^{P9}$ is selected from hydrogen and alkyl;

each $P^1$ is independently:

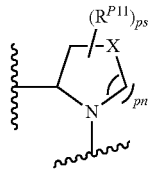

wherein:
X is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

at least one $R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclyloxyalkyloxy, $(NR^hR^h)$alkyloxy, cyanoalkoxy, cyanocycloalkyloxy, cycloalkyloxy, oxo, heterocyclyl, —$NR^{hh}R^h$, $(NR^{hh}R^h)$alkyl, $(NR^{hh}R^h)$carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocloooxyalkyloxy, $(NR^hR^h)$alkyloxy, cyanoalkoxy, cyanocycloalkyloxy, cycloalkyloxy, oxo and heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 1, 2, 3, or 4;
pn is 0, 1, or 2;
each $P^3$ is independently a ring of the formula:

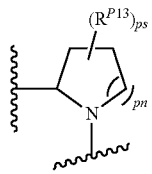

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;
each $P^5$ is independently a ring of the formula:

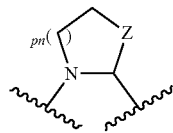

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pn is 0, 1, or 2;
Z is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$$NR^hR^h$, —S(=O)$_2R^h$, C(=O)$R^h$, C(=O)O$R^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

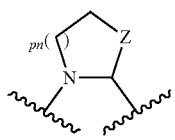

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
Z is O, S, S(=O), S(=O)$_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(—O)$_2NR^hR^h$, —S(=O)$_2R^h$, C(=O)$R^h$, C(=O)O$R^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;
each $P^8$ is independently a ring of the formula:

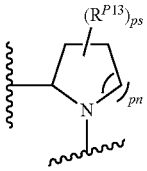

wherein:
ps is 2, 3, 4, 5, or 6;
pn is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

each $P^{10}$ is independently:

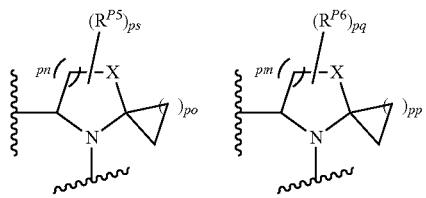

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^b$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;
each $P^{12}$ is independently:

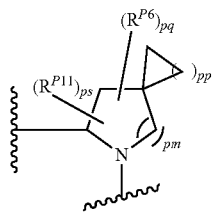

wherein:

each $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq is independently 0, 1, 2, 3, or 4;

pm is independently 0, 1, or 2;
pp is independently 1, 2, or 3;
ps is 1, 2, 3, or 4;

$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each $P^{15}$ is:

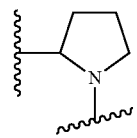

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

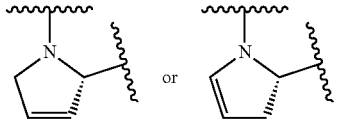 [SMILES: *[C@@H]1C=CCN1* ; *[C@@H]1CC=CN1*]

which is optionally substituted with one or two groups independently selected from halo, alkyl, alkoxyalkyl, haloalkyl, cycloalkyl, and cycloalkylalkyl;

each $P^{19}$ is:

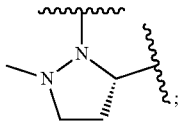 [SMILES: *[C@@H]1CCN(C)N1*]

each P³⁰ is independently a ring of the formula:

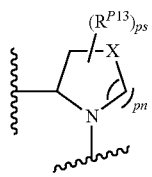

ps is 2
pn is 0, 1 or 2;
X is selected from O, S, S(O), SO₂, or CH₂; provided that when pn is 0, X is CH₂.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

$W^{1a}$ is selected from:

120

121

122 and

123 wherein each $W^{1a}$ is optionally substituted with one or more (e.g. 1, 2, 3, or 4) groups independently selected from halo, alkyl, haloalkyl, cyano, and

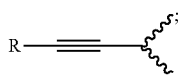

wherein each R is independently H, alkyl, haloalkyl, cycloalkyl, aryl, or heteroaryl;

$X^{20}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

$Y^{21}$ is a bicyclic aromatic ring system comprising eight to 12 atoms optionally including one or more heteroatoms selected from O, S, and N, which bicyclic ring system is optionally with one or more groups independently selected from halo, haloalkyl, alkyl and oxo;

$Y^{22}$ is selected from $A^0$, $A^1$, $A^2$, $A^3$, $A^7$, $A^{15}$, $A^{16}$, and $A^{20}$;

each $A^0$ is independently:

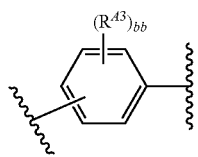

wherein:

each $R^{A3}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or each $A^0$ is independently a six-membered heteroaromatic ring containing one, two, or three nitrogen atoms, which ring is optionally substituted with 1, 2, 3, or 4 $R^{A3}$ groups;

each $A^1$ is independently:

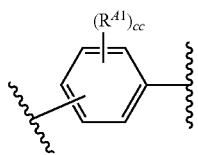

wherein:

each $R^{A1}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and each R$^4$ is independently selected from H, alkyl, haloalkyl, aryl, and arylalkyl;

each cc is independently 1, 2, 3, or 4;

each $A^2$ is independently:

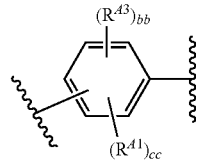

wherein:

each $R^{A1}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^{A3}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each R$^4$ is independently selected from H, alkyl, haloalkyl, aryl, and arylalkyl;

R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each bb is 0, 1, 2, 3, or 4; each cc is 1, 2, 3, or 4; and the sum of bb and cc is 1, 2, 3, or 4;

each $A^3$ is independently a six-membered heteroaromatic ring containing one, two, or three nitrogen atoms, which ring is substituted with one or more $R^{A1}$ groups, and which ring is optionally substituted with one or more $R^{A3}$ groups;

each $A^7$ is independently:

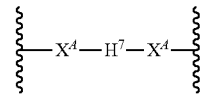

wherein:

each $H^7$ is independently a five-membered heteroaromatic ring, which $H^7$ is optionally substituted with one or more groups independently selected from $R^{A1}$ and $R^{A3}$; and each $X^4$ is independently O, NR, SO, SO$_2$, C(=O), NRC(=O), C(=O)NR, CR=CR, NRC(=O)NR, allenyl, alkynyl, or absent; and each R is independently selected from H or alkyl;

each $A^{15}$ is independently:

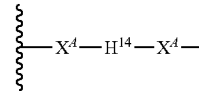

wherein:

each $H^{14}$ is independently a fused unsaturated, partially unsaturated or saturated tricyclic carbocycle which is optionally substituted with one or more groups independently selected from oxo, $R^{A1}$ and $R^{A3}$; and each $X^4$ is independently O, NR, SO, SO$_2$, C(=O), NRC(=O), C(=O)NR, CR=CR, NRC(=O)NR, allenyl, alkynyl, or absent and each R is independently selected from H or alkyl;

each $A^{16}$ is independently:

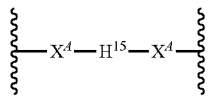

wherein:

each $H^{15}$ is independently a fused unsaturated, partially unsaturated or saturated tricyclic heterocycle that comprises at least one heteroatom in the ring system, which ring system is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^{20}$ is independently a 5 or 6 membered heteroaryl ring that is optionally substituted with one or more groups independently selected from $R^{41}$ and $R^{43}$;

each $L^9$ is independently a fused-tetracyclic saturated, partially unsaturated, or aromatic heterocyclic ring system that is optionally substituted with one or more groups independently selected from oxo, halo, $-R^{L9}$, $-OR^{L9}$, $-SR^{L9}$, $-CF_3$, $-CCl_3$, $-OCF_3$, $-CN$, $-NO_2$, $-N(R^{L9})C(=O)R^{L9}$, $-C(=O)R^{L9}$, $-OC(=O)R^{L9}$, $-C(O)OR^{L9}$, $-C(=O)NR^{L9}$, $-S(=O)R^{L9}$, $-S(=O)_2OR^{L9}$, $-S(=O)_2R^{L9}$, $-OS(=O)_2OR^{L9}$, $-S(=O)_2NR^{L9}$, alkoxyalkyl, arylalkoxycarbonyl, halo, haloalkyl, hydroxyalkyl, $-NR^aR^b$, $(NR^aR^b)$alkyl, and $(NR^aR^b)$carbonyl;

each $R^{L9}$ is independently $-H$, alkyl, aryl, arylalkyl, or heterocycle; and $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

or a pharmaceutically acceptable salt or prodrug thereof.

In another embodiment the invention provides a compound of the invention which is compound of formula (I):

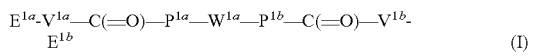

(I)

wherein:

$E^{1a}$ is $E^0$, $E^1$, or $E^2$, or $E^{1a}$-$V^{1a}$ taken together are $R^{9a}$;
$E^{1b}$ is $E^0$, $E^1$, or $E^2$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;

each $E^0$ is independently $-NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, $-C(NCN)OR'$, and $-C(NCN)NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one $-NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkylcarbonyl, the heterocyclylalkyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, $-NH$haloalkyl, aryl, and heterocyclyl;

each $E^2$ is independently $-NHR^{Ef}$ wherein $R^{Ef}$ is cycloalkylcarbonyl or cycloalkyloxycarbonyl;

each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, $-NR^XR^Y$, $(NR^XR^Y)$alkyl-, oxo, and $-P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, $-NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$P^{1a}$ and $P^{1b}$ are each independently selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$;

each $P^0$ is independently:

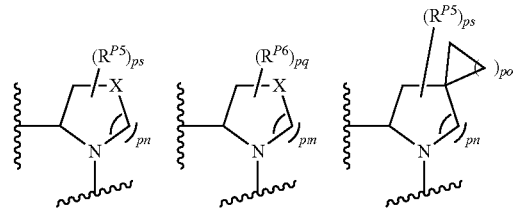

-continued

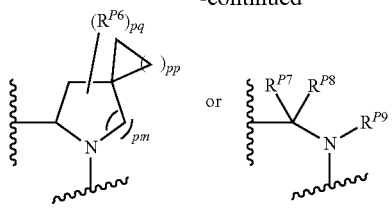

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;
each P$^1$ is independently:

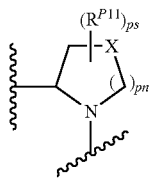

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyloxyalkyloxy, aryloxyalkyloxy, heteroaryloxyakyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo and heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

ps is 1, 2, 3, or 4;
pn is 0, 1, or 2;
each P$^3$ is independently a ring of the formula:

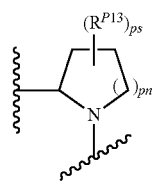

wherein:
the ring is substituted with one or more oxo group;
each R$^{P13}$ is independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

ps is 0, 1, 2, 3, or 4;
pn is 0, 1, or 2;

each $P^5$ is independently a ring of the formula:

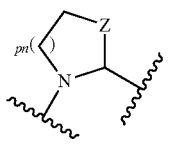

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pn is 0, 1, or 2;
Z is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$$NR^hR^h$, —S(=O)$_2R^h$, C(=O)$R^h$, C(=O)O$R^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

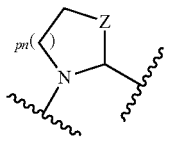

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
Z is O, S, S(=O), S(=O)$_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$$NR^hR^h$, —S(=O)$_2R^h$, C(=O)$R^h$, C(=O)O$R^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;
each $P^8$ is independently a ring of the formula:

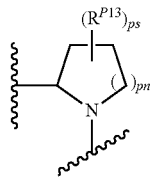

wherein:
ps is 2, 3, 4, 5, or 6;
pn is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle; each $P^{10}$ is independently:

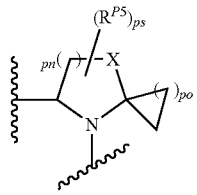 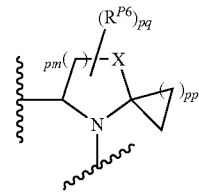

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

pq and ps are independently 0, 1, 2, 3, or 4;
pm and pn are independently 0, 1, or 2;
po and pp are independently 1, 2, or 3;
each P$^{12}$ is independently:

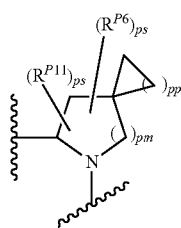

wherein:
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq is independently 0, 1, 2, 3, or 4;
pm is independently 0, 1, or 2;
pp is independently 1, 2, or 3;
ps is 1, 2, 3, or 4;

R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alk-enyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each P$^{15}$ is:

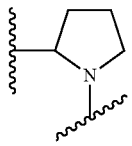 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each P$^{18}$ is:

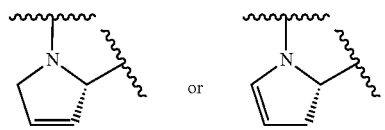 [SMILES: *[C@@H]1C=CCN1* ; *[C@@H]1CC=CN1*]

which is optionally substituted with one or two groups independently selected from halo, alkyl, alkoxyalkyl, haloalkyl, cycloalkyl, and cycloalkylalkyl;

each P$^{19}$ is:

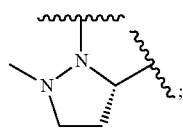

each R$^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

$W^{1a}$ is selected from:

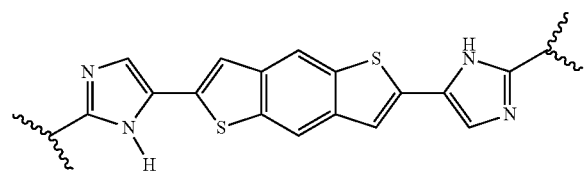
110

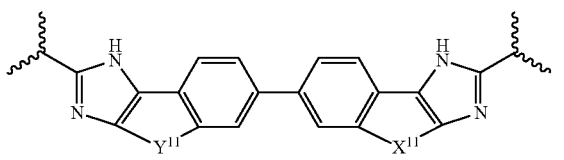
111

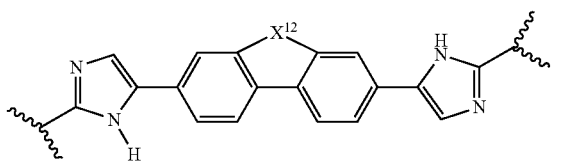
112

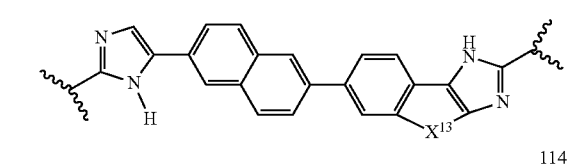
113

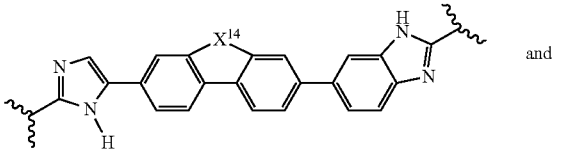
114
and

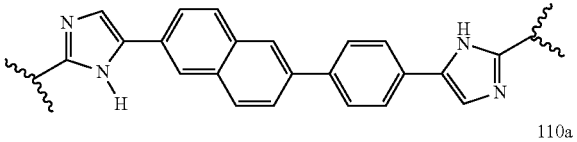
115

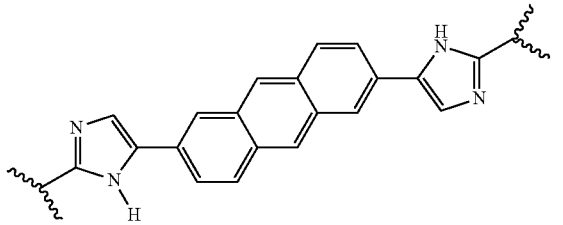
110a wherein each $W^{1a}$ is optionally substituted with one or more (e.g. 1, 2, 3, or 4) groups independently selected from halo, alkyl, haloalkyl, cyano, and wherein each $W^{1a}$ is substituted with one or more (e.g. 1, 2, 3, or 4):

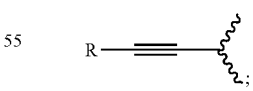

wherein each R is independently H, alkyl, haloalkyl, cycloalkyl, aryl, or heteroaryl;

$X^{11}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

$Y^{11}$ is —CH$_2$—, —CH$_2$—CH$_2$—, —CH$_2$—O—, —O—CH$_2$—, —CH$_2$—O—CH$_2$—, —S—, —S(O)$_2$—,

—C(O)—, —CF$_2$—, —O—, —S—CH$_2$—, —CH$_2$—S—, —O—C(O)—, —C(O)—O—, —CH═N—; —N═CH—; or —CH═CH—

X$^{12}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH═N—; —N═CH—; or —CH═CH—

X$^{13}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH═N—; —N═CH—; or —CH═CH—; and X$^{14}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH═N—; —N═CH—; or —CH═CH—;

or a pharmaceutically acceptable salt or prodrug thereof.

In another embodiment the invention provides a compound of the invention which is compound of formula (I):

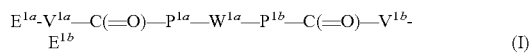

$$E^{1a}\text{-}V^{1a}\text{—}C(═O)\text{—}P^{1a}\text{—}W^{1a}\text{—}P^{1b}\text{—}C(═O)\text{—}V^{1b}\text{-}E^{1b} \quad (I)$$

wherein:
E$^{1a}$ is E$^0$, E$^1$, or E$^2$, or E$^{1a}$-V$^{1a}$ taken together are R$^{9a}$;
E$^{1b}$ is E$^0$, E$^1$, or E$^2$, or E$^{1b}$-V$^{1b}$ taken together are R$^{9b}$;
V$^{1a}$ is V$^0$ or E$^{1a}$-V$^{1a}$ taken together are R$^{9a}$;
V$^{1b}$ is V$^0$ or E$^{1b}$-V$^{1b}$ taken together are R$^{9b}$;
one of P$^{1a}$ and P$^{1b}$ is selected from P$^{0a}$ and the other of P$^{1a}$ and P$^{1b}$ is selected from P$^1$, P$^3$, P$^5$, P$^6$, P$^7$, P$^8$, P$^{10}$, P$^{12}$, P$^{15}$, P$^{18}$, P$^{19}$, and P$^{30}$;

each E$^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each E$^1$ is independently selected from hydrogen, hydroxy, alkyl, aryl, and heterocyclyl;
each E$^2$ is independently —NHR$^{Ef}$ wherein R$^{Ef}$ is cycloalkylcarbonyl or cycloalkyloxycarbonyl;
each V$^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

W$^{1a}$ is:

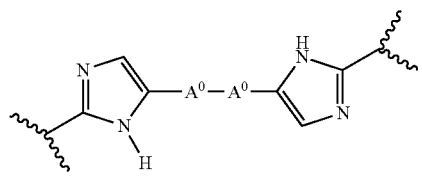

XX1 wherein W$^{1a}$ is optionally substituted with one or more (e.g. 1, 2, 3, or 4) groups independently selected from halo, alkyl, haloalkyl, cyano, and

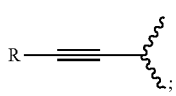

wherein each R is independently H, alkyl, haloalkyl, cycloalkyl, aryl, or heteroaryl;
each P$^{0a}$ is independently:

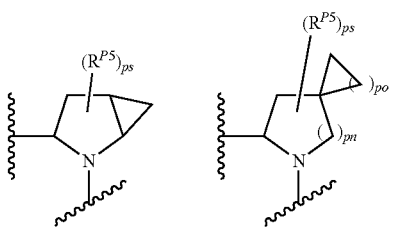

each $R^{P5}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

ps is independently 0, 1, 2, 3, or 4;
pn is independently 0, 1, or 2;
po is independently 1, 2, or 3;
each $P^1$ is independently:

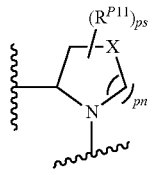

wherein:
X is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
at least one $R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^ha$)lkyloxy, cyanoalkoxy, cyanocycloalkyloxy, cycloalkyloxy, oxo, heterocyclyl, —$NR^{hh}R^h$, ($NR^{hh}R^h$)alkyl, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;
each $P^3$ is independently a ring of the formula:

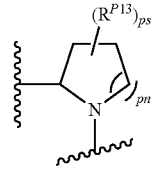

wherein:
the ring is substituted with one or more oxo group;
each $R^{P13}$ is independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;
each $P^5$ is independently a ring of the formula:

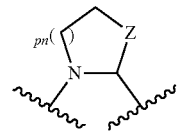

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
pn is 0, 1, or 2;
Z is O, S, S(=O), $S(=O)_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —$S(=O)_2NR^hR^h$, —$S(=O)_2R^h$, $C(=O)R^h$, $C(=O)OR^h$, —$C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each P⁶ is independently a ring of the formula:

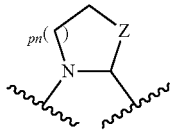

wherein:
the ring is substituted with one or more oxo and is optionally substituted with one or more groups R^{P16} that are independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
Z is O, S, S(=O), S(=O)₂, or NR^f;
pn is 0, 1, or 2;
each R^f is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)₂NR^hR^h, —S(=O)₂R^h, C(=O)R^h, C(=O)OR^h, —C(=O)NR^hR^h; each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R^h groups are present then they may come together with the atoms to which they are bound to form a 4-15 membered heterocyclic ring;
each P⁷ is a bridged 5-15 membered bicyclic heterocyclic ring that is attached to the remainder of the compound of formula I through one N-link and through one C-link; wherein the ring is optionally substituted with one or more groups independently selected from R^{P6} and R^{P11};
each P⁸ is independently a ring of the formula:

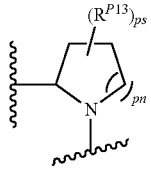

wherein:
ps is 2, 3, 4, 5, or 6;
pn is 0, 1 or 2;
each R^{P13} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups; where in at least one case two groups R^{P13} that are attached to the same carbon are taken together with the carbon to which they are attached and form a 4-6 membered heterocyclic ring;

each P¹⁰ is independently:

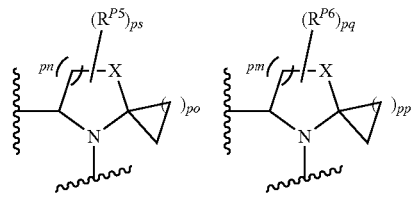

wherein:
X is selected from O, S, S(O), SO₂, CH₂, CHR^{P10}, and C(R^{P10})₂; provided that when pn or pm is 0, X is selected from CH₂, CHR^{P10}, and C(R^{P10})₂;
each R^{P10} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
each R^{P5} and R^{P6} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;
each P¹² is independently:

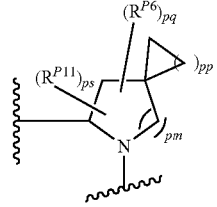

wherein:
each R^{P6} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
pp is independently 1, 2, or 3;
ps is 1, 2, 3, or 4;
R^{P11} is independently selected from cyano, alkylsulfonyl, arylsulfonyl, (NR^hR^h)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR^hR^h)alkyloxy, cyanoalkoxy, cyanocycloalkyloxy, cycloalkyloxy, oxo, heterocyclyl, —NR^{hh}R^h, (NR^{hh}R^h)alkyl, (NR^{hh}R^h)carbonyl, wherein each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R^h groups are present then they may come together with the atoms to which they are bound to form a 4-15 membered heterocyclic ring; wherein each R^{hh} is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(═O)$_2$R$^h$, —C(═O)R$^h$, —C(═O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each P$^{15}$ is:

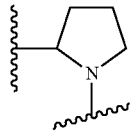

which is substituted with one or two groups independently selected from alkoxyalkyl, haloalkoxyalkyl, alkylsulfanyl, alkylsulfanylalkyl, cyanoalkyl, and cycloalkylalkyl;

each P$^{18}$ is:

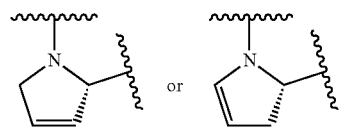

which is optionally substituted with one or two groups independently selected from halo, alkyl, alkoxyalkyl, haloalkyl, cycloalkyl, and cycloalkylalkyl;

each R$^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocycly-loxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each R$^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocycly-loxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

or a pharmaceutically acceptable salt or prodrug thereof.

In another embodiment the invention provides a compound of the invention which is compound of formula (I):

wherein:

E$^{1a}$ is E$^0$, E$^1$, or E$^2$, or E$^{1a}$-V$^{1a}$ taken together are R$^{9a}$;
E$^{1b}$ is E$^0$, E$^1$, or E$^2$, or E$^{1b}$-V$^{1b}$ taken together are R$^{9b}$;

$V^{1a}$ is $V^0$ or $E^{1a}$-$V^{1a}$ taken together are $R^{9a}$;

$V^{1b}$ is $V^0$ or $E^{1b}$-$V^{1b}$ taken together are $R^{9b}$;

one of $P^{1a}$ and $P^{1b}$ is selected from $P^{0b}$ and the other of $P^{1a}$ and $P^{1b}$ is selected from $P^{21}$, $P^3$, $P^6$, $P^7$, $P^{28}$, $P^{12}$, $P^{15}$ and $P^{38}$;

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, aryl, and heterocyclyl;

each $E^2$ is independently —$NHR^{Ef}$ wherein $R^{Ef}$ is cycloalkylcarbonyl or cycloalkyloxycarbonyl;

each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —($NR^XR^Y$)alkyl, oxo, and —P(O)$OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, ($NR^XR^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$W^{1a}$ is:

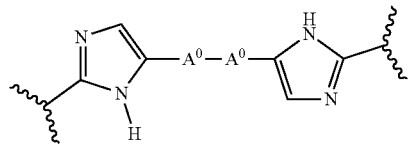

XX1 wherein $W^{1a}$ is optionally substituted with one or more (e.g. 1, 2, 3, or 4) groups independently selected from halo, alkyl, haloalkyl, cyano, and

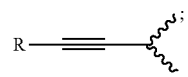

wherein each R is independently H, alkyl, haloalkyl, cycloalkyl, aryl, or heteroaryl;

each $P^{0b}$ is independently:

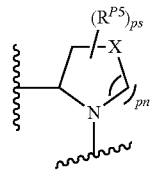

X is selected from O, S, S(O), $SO_2$, $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$ each $R^{P5}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

ps is independently 0, 1, 2, 3, or 4;

pn is independently 0, 1, or 2;

each $P^{21}$ is independently:

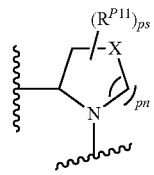

wherein:

X is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

at least one $R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclooxyalkyloxy, ($NR^hR^h$)alkyloxy, cyanoalkoxy, cyanocycloalkyloxy, cycloalkyloxy, oxo, —$NR^{hh}R^h$, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl;

ps is 1, 2, 3, or 4;
pn is 0, 1, or 2;
each $P^3$ is independently a ring of the formula:

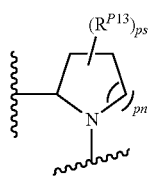

wherein:
the ring is substituted with one or more oxo group;
each $R^{P13}$ is independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;

each $P^6$ is independently a ring of the formula:

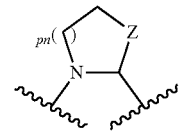

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
Z is O, S, $S(=O)$, $S(=O)_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —$S(=O)_2NR^hR^h$, —$S(=O)_2R^h$, $C(=O)R^h$, $C(=O)OR^h$, —$C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;

each $P^{28}$ is independently a ring of the formula:

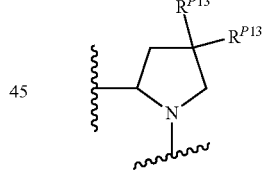

wherein:
each $R^{P13}$ is independently selected from alkoxy, alkyl, aryl, halo, haloalkyl, hydroxy, and —$NR^{Pa}R^{Pb}$, where in two $R^{P13}$ groups are taken together with the carbon to which they are attached and form a 4-6 membered heterocyclic ring;

each $P^{12}$ is independently:

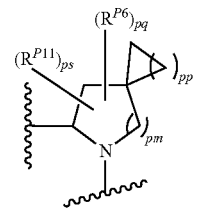

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
pp is independently 1, 2, or 3;
ps is 1, 2, 3, or 4;
$R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl, —$NR^{hh}R^h$, ($NR^{hh}R^h$)alkyl, ($NR^hR^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
each $P^{15}$ is:

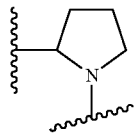 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;
each $P^{38}$ is:

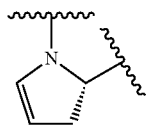

which is optionally substituted with one or two groups independently selected from halo, alkyl, alkoxyalkyl, haloalkyl, cycloalkyl, and cycloalkylalkyl;
each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —$C(NCN)OR'$, and —$C(NCN)NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —($NR^{X'}R^{Y'}$)alkyl, and —($NR^{X'}R^{Y'}$)carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl, wherein $R^{X'}$ and $R^{Y'}$ are independently selected from hydrogen and alkyl;
each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —$C(NCN)OR'$, and —$C(NCN)NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —$(NR^XR^Y)$alkyl, and —$(NR^XR^Y)$carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl;

or a pharmaceutically acceptable salt or prodrug thereof.

In another embodiment the invention provides a compound of the invention which is a compound of any one of formulae 1-25, 25b, 25c, and 25d as shown in Table 1, or a pharmaceutically acceptable salt or prodrug thereof.

In another embodiment the invention provides a compound of the invention which is a compound of any one of formulae 26-102 as shown in Table 2, or a pharmaceutically acceptable salt or prodrug thereof.

In another embodiment the invention provides a compound of the invention which is a compound of any one of formulae 103-289 as shown in Table 3, or a pharmaceutically acceptable salt or prodrug thereof.

The invention also provides isotopically enriched compounds that are compounds of the invention that comprise an enriched isotope at one or more positions in the compound.

The present invention also provides a pharmaceutical composition comprising a compound of the invention and at least one pharmaceutically acceptable carrier.

The present invention also provides a pharmaceutical composition for use in treating disorders associated with HCV.

The present invention also provides a pharmaceutical composition further comprising an interferon or pegylated interferon.

The present invention also provides a pharmaceutical composition further comprising a nucleoside analog.

The present invention also provides for a pharmaceutical composition wherein said nucleoside analogue is selected from ribavirin, viramidine, levovirin, an L-nucleoside, and isatoribine and said interferon is α-interferon or pegylated α-interferon.

The present invention also provides for a method of treating disorders associated with hepatitis C, said method comprising administering to an individual a pharmaceutical composition which comprises a therapeutically effective amount of a compound of the invention.

The present invention also provides a method of inhibiting HCV, comprising administering to a mammal afflicted with a condition associated with HCV activity, an amount of a compound of the invention, effective to inhibit HCV.

The present invention also provides a compound of the invention for use in medical therapy (e.g. for use in inhibiting HCV activity or treating a condition associated with HCV activity), as well as the use of a compound of the invention for the manufacture of a medicament useful for inhibiting HCV or the treatment of a condition associated with HCV activity in a mammal.

The present invention also provides synthetic processes and novel intermediates disclosed herein which are useful for preparing compounds of the invention. Some of the compounds of the invention are useful to prepare other compounds of the invention.

In another aspect the invention provides a compound of the invention, or a pharmaceutically acceptable salt or prodrug thereof, for use in the prophylactic or therapeutic treatment of hepatitis C or a hepatitis C associated disorder.

In another aspect the invention provides a method of inhibiting HCV activity in a sample comprising treating the sample with a compound of the invention.

Compounds of formula (I) have been found to possess useful activity against HCV genotypes 1 and 4. Compounds of formula (I) wherein $W^{1a}$ is selected from structures 103-109 have been found to possess useful activity against HCV genotypes 1-4. Additionally certain compounds of formula (I) wherein $W^{1a}$ is selected from structures 101-109 and at least one of $V^{1a}$ and $V^{1b}$ is selected from:

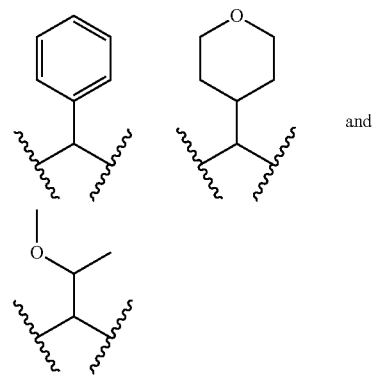

and are improved in potency against resistant variants in GT1 compared to the corresponding compounds wherein $V^{1a}$ and $V^{1b}$ are each selected from:

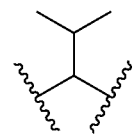

Accordingly, certain compounds of formula (I) wherein $W^{1a}$ is selected from structures 101-102 possess beneficial pharmacokinetic properties that make them well suited to fulfil the current need for HCV agents with such beneficial properties. Additionally compounds of formula (I) wherein $W^{1a}$ is selected from structures 101, 102 and at least one of $V^{1a}$ and $V^{1b}$ is selected from:

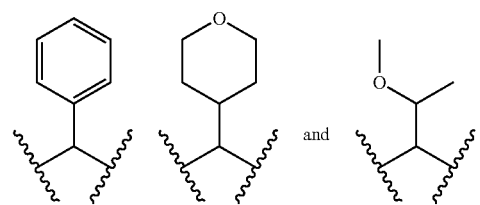

have been found to possess improved activity against HCV genotypes 2 and 3 compared to the corresponding compounds wherein $V^{1a}$ and $V^{1b}$ are each selected from:

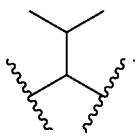

Accordingly, certain compounds of formula (I) wherein $W^{1a}$ is selected from structures 101, 102 possess beneficial pharmacokinetic properties that make them well suited to fulfil the current need for HCV agents with such beneficial properties.

Compounds of formula (I) wherein $W^{1a}$ is selected from structures 110, 111, 112, 118 and 125 have been found to possess useful activity against HCV genotypes 1-4. Additionally certain compounds of formula (I) wherein $W^{1a}$ is selected from structures 110, 111, 112, 118 and 125 and at least one of $V^{1a}$ and $V^{1b}$ is selected from:

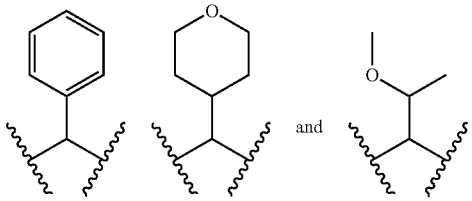

are improved in potency against resistant variants in GT1 compared to the corresponding compounds wherein $V^{1a}$ and $V^{1b}$ are each selected from:

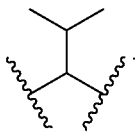

Accordingly, certain compounds of formula (I) wherein $W^{1a}$ is selected from structures 113, 114, 115, 116, 130 possess beneficial pharmacokinetic properties that make them well suited to fulfil the current need for HCV agents with such beneficial properties.

Additionally certain compounds of formula (I) wherein $W^{1a}$ is selected from structures 113, 114, 115, 116, 130 and at least one of $V^{1a}$ and $V^{1b}$ is selected from:

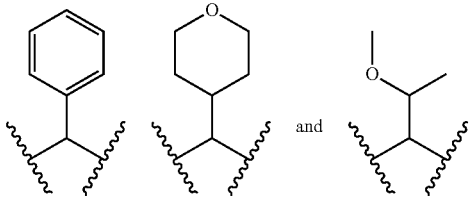

are improved in potency against resistant variants in GT1 compared to the corresponding compounds wherein $V^{1a}$ and $V^{1b}$ are each selected from:

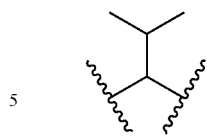

Additionally certain compounds of formula (I) wherein $W^{1a}$ is selected from structures 120-123 and at least one of $V^{1a}$ and $V^{1b}$ is selected from:

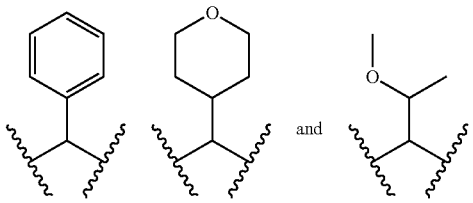

are improved in potency against resistant variants in GT1 compared to the corresponding compounds wherein $V^{1a}$ and $V^{1b}$ are each selected from:

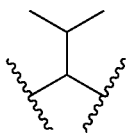

Compounds of formula (I) wherein $W^{1a}$ is selected from structure XX1 been found to possess useful activity against HCV genotypes 1-4. Additionally certain compounds of formula (I) wherein $W^{1a}$ is selected from structures XX1 and at least one of $V^{1a}$ and $V^{1b}$ is selected from:

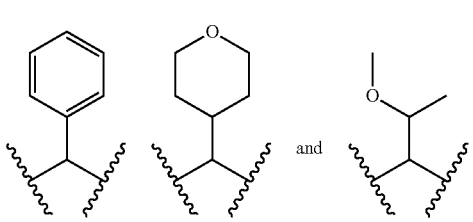

are improved in potency against resistant variants in GT1 compared to the corresponding compounds wherein $V^{1a}$ and $V^{1b}$ are each selected from:

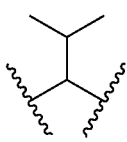

It has been further found that certain compounds of formula (I) with particular $W^{1a}$ groups have improved potency in genotypes 2, 2a and 2b ("GT2", "GT2a", and "GT2b") when a methionine is present at the residue 31 position of NS5A ("with M31 present") (in the data tables herein the GT2a J6 replicon clone and the GT2b replicon have the more resistant M31 residue present and the GT2a JFH replicon clone has the less resistant L31 residue). These certain compounds of formula (I) also can have improved potency against some resistant mutants in genotype 1 and other genotypes. One such example of a resistant mutant in genotype 1a is where residue 30 has been changed from Q to R (Q30R). This mutant is represented in the data tables. Enhanced potencies can be further improved when the particular $W^{1a}$ groups are combined with certain select P groups, or select V groups, and/or select E or $R^9$ groups independently as described below.

Compounds possessing enhanced potency against GT2a, GT2b (both with M31 present) and against some resistant variants in genotype 1 and other genotypes include those where $W^{1a}$ is selected from structures 103, 105, 111, and 118.

Included are particular compounds of formula (I) wherein $W^{1a}$ is selected from structure 103 of the formula:

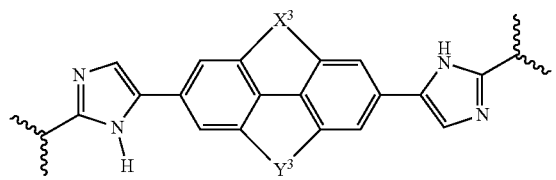

103 wherein $X^3$ is —CH₂—CH₂—, —CH₂—O—, or —O—CH₂—; and $Y^3$ is —CH₂—CH₂—, —CH₂—O—, —O—CH₂—, or —CH=CH—. Further included are compounds where $W^{1a}$ is:

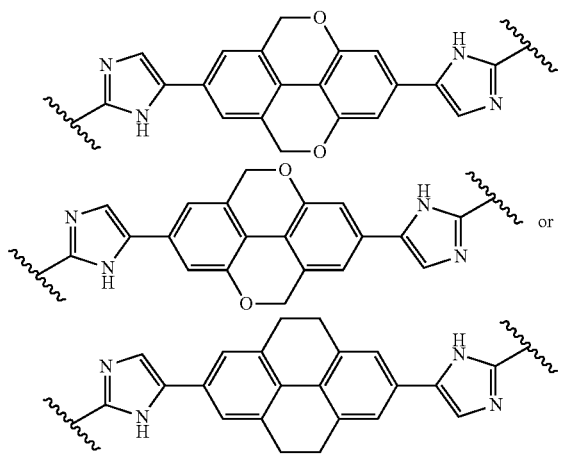

Further included are compounds where $W^{1a}$ is:

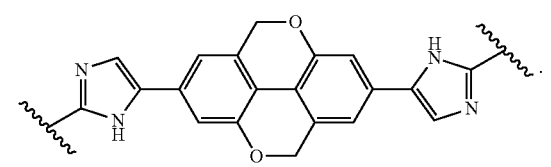 [SMILES: *c1ncc(-c2cc3c4c(c2)OCc2cc(-c5cnc(*)[nH]5)cc(c2-4)OC3)[nH]1]

Also included are particular compounds of formula (I) wherein $W^{1a}$ is selected from structure 118 of the formula:

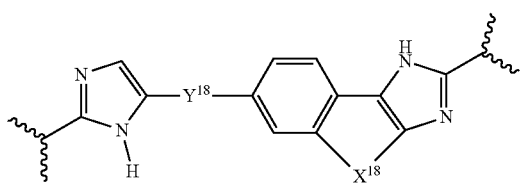

118 wherein $X^{18}$ is —CH=CH—, —CH₂CH₂—, or —OCH₂—; and $Y^{18}$ is phenyl. Further included are compounds where $W^{1a}$ is:

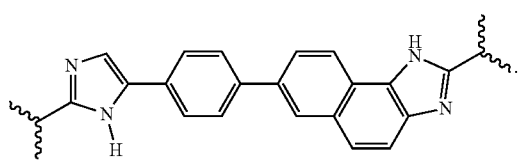 [SMILES: *c1ncc(-c2ccc(-c3ccc4c(ccc5nc(*)[nH]c54)c3)cc2)[nH]1]

Also included are particular compounds of formula (I) wherein $W^{1a}$ is selected from structure 111 of the formula:

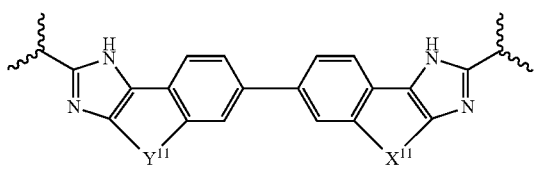

111 wherein $X^{11}$ is —CH₂—CH₂—, —O—CH₂—, or —CH=CH—; and $Y^{11}$ is —CH=CH—, —O—CH₂—. Further included are compounds where $W^{1a}$ is:

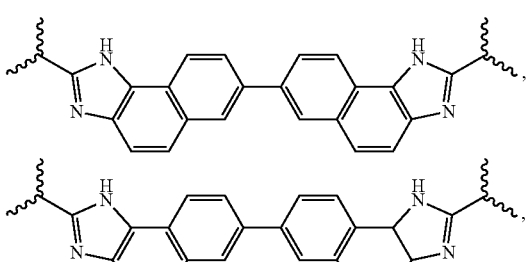

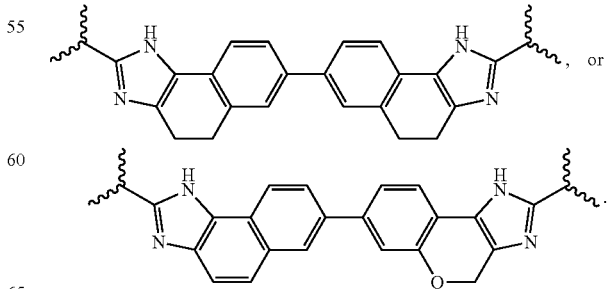

Further included are compounds where $W^{1a}$ is:

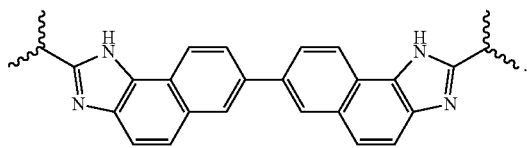 [SMILES: *c1nc2ccc3cc(-c4ccc5c(ccc6nc(*)[nH]c65)c4)ccc3c2[nH]1]

Also included are particular compounds of formula (I) wherein $W^{1a}$ is selected from structure 105 of the formula:

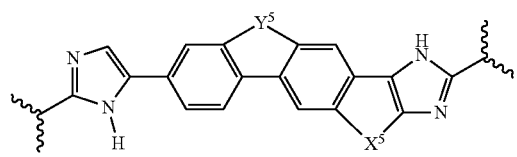

wherein $Y^5$ is —O—CH$_2$—, or —CH$_2$—O—; and $X^5$ is —CH$_2$—CH$_2$— or —CH=CH—.

Further included are compounds where $W^{1a}$ is:

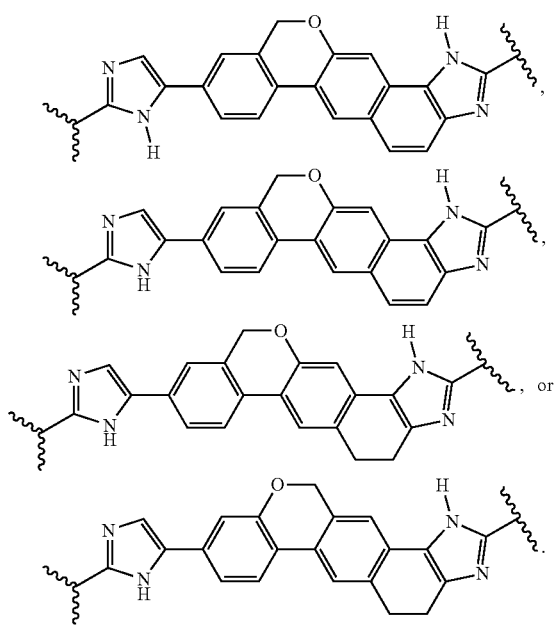

Further included are compounds where $W^{1a}$ is:

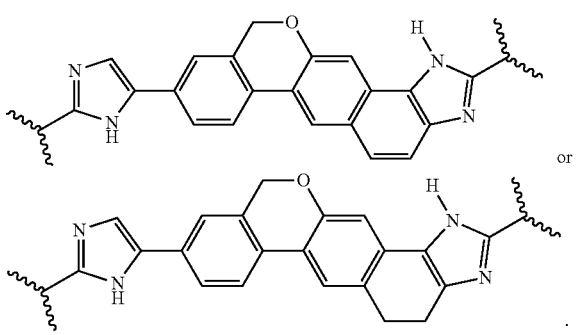

Further included are compounds where $W^{1a}$ is:

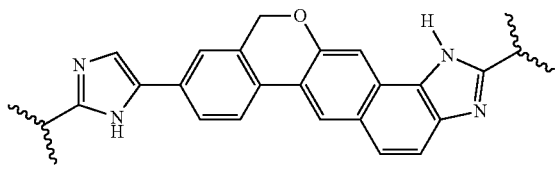

Additionally, when combined with P groups, V groups, and/or E or $R^9$ groups independently selected from groups described below, certain compounds of formula (I) wherein $W^{1a}$ is structure 130 can have improved potency in GT2a and GT2b (both with M31):

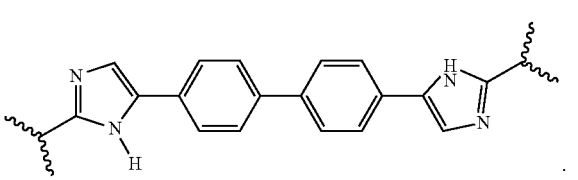

The observed en

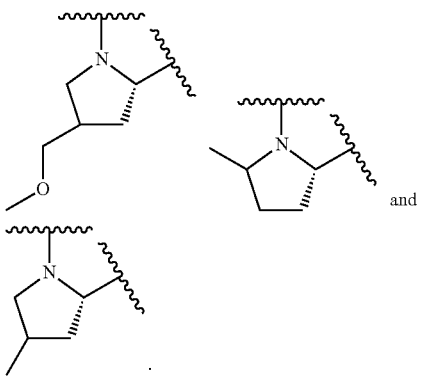

Particularly beneficial in providing enhanced potency against GT2a, GT2b (both with M31 present) and against some resistant variants in genotype 1 and other genotypes are compounds where $P^{1a}$ or $P^{1b}$ is selected from:

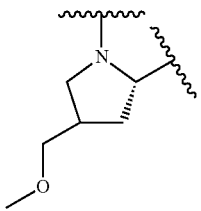

Other select combination groups include those where $P^{1a}$ is:

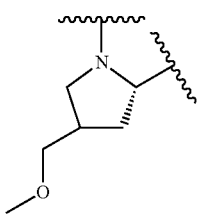

and $V^{1a}$ is selected from:

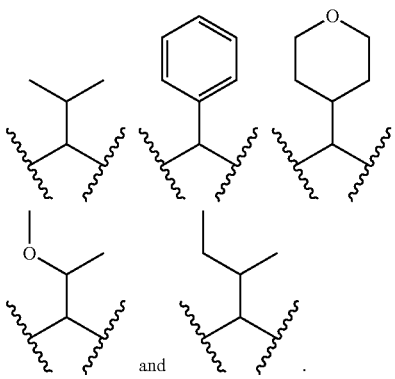

Other select combination groups include those where $P^{1b}$ is:

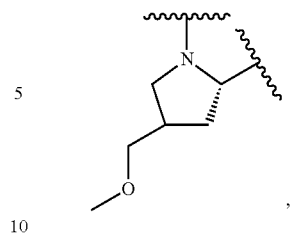

and $V^{1b}$ is selected from:

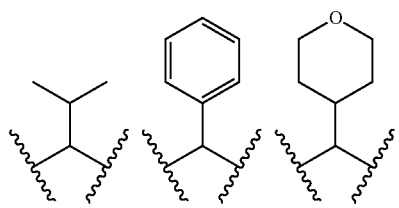

Other select combination groups include those where $P^{1a}$ is:

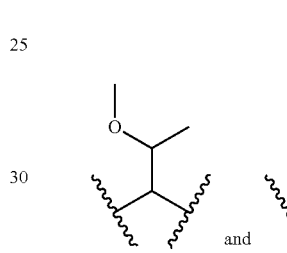

and $V^{1a}$ is selected from:

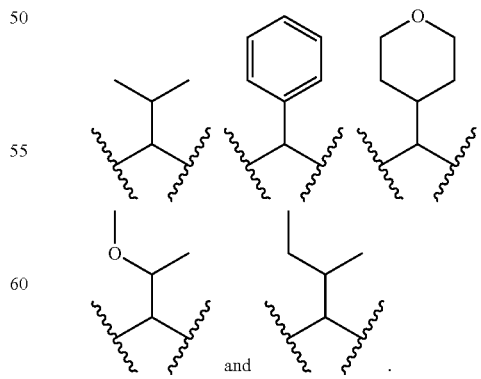

Other select combination groups include those where $P^{1b}$ is:

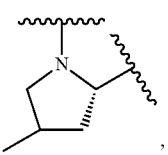

and the $V^{1b}$ is selected from:

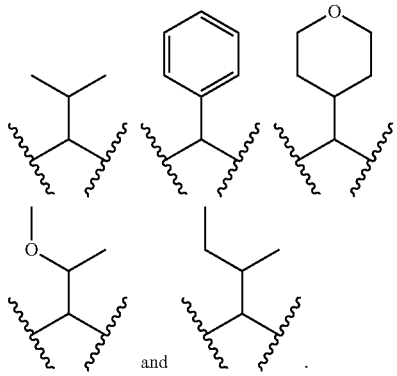

Other select combination groups include those where $P^{1a}$ is:

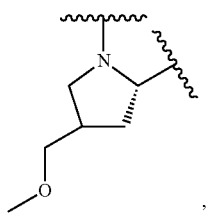

and the $V^{1a}$ is,

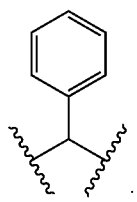 [SMILES: *C(*)c1ccccc1]

Other select combination groups include those where $P^{1b}$ is:

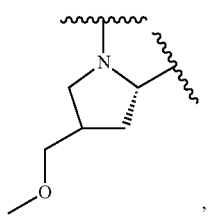

and the $V^{1b}$ is,

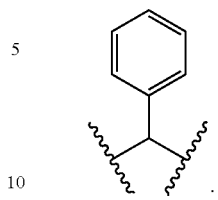

Other select combination groups include those where $P^{1a}$ is:

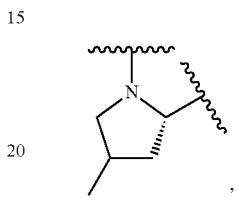

and $V^{1a}$ is,

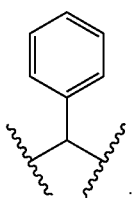

Other select combination groups include those where $P^{1b}$ is:

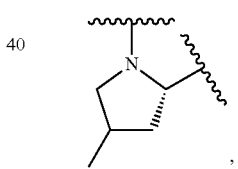

and $V^{1b}$ is,

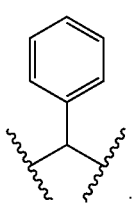

Other select combination groups include those where $P^{1a}$ is:

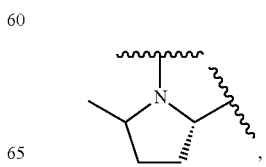

and V$^{1a}$ is selected from:

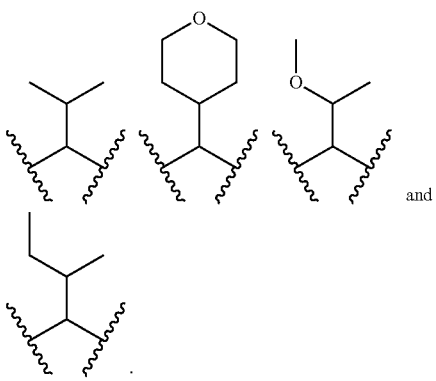

and

Other select combination groups include those where P$^{1b}$ is:

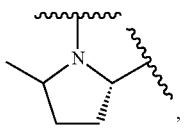

and V$^{1b}$ is selected from:

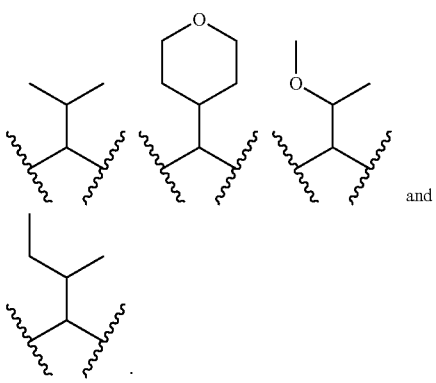

and

Furthermore, additional potency against GT2a, GT2b (both with M31 present) and against some resistant variants in genotype 1 and other genotypes is observed in compounds wherein E$^{1a}$-V$^{1a}$ taken together are R$^{9a}$ or wherein E$^{1b}$-V$^{1b}$ taken together are R$^{9b}$, wherein R$^{9a}$ or R$^{9b}$ is selected from:

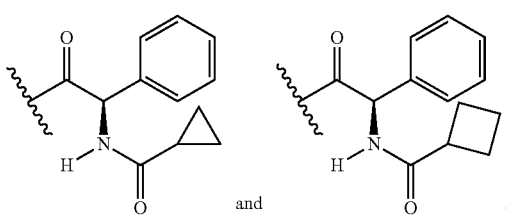

and

Accordingly, certain compounds of formula (I) possess beneficial pharmacological properties that make them well suited to fulfil the current need for HCV agents with such beneficial properties.

In one embodiment the invention provides a compound having improved inhibitory or pharmacokinetic properties, including enhanced activity against development of viral resistance, improved oral bioavailability, greater potency (for example, in inhibiting HCV activity) or extended effective half-life in vivo. Certain compounds of the invention may have fewer side effects, less complicated dosing schedules, or be orally active.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the embodiments.

Compounds of the Invention

The compounds of the invention exclude compounds heretofore known. However, it is within the invention to use compounds that previously were not known to have antiviral properties for antiviral purposes (e.g. to produce an antiviral effect in an animal). With respect to the United States, the compounds or compositions herein exclude compounds that are anticipated under 35 USC § 102 or that are obvious under 35 USC § 103.

Whenever a compound described herein is substituted with more than one of the same designated group, e.g., "R$^1$" or "A$^3$", then it will be understood that the groups may be the same or different, i.e., each group is independently selected.

"Absent"—Some groups are defined such that they can be absent. When a group is absent it becomes a bond connector. The two groups that would otherwise be connected to that absent group are connected to each other through a bond. For example, when W is absent, M is bonded to M.

"Alkyl" is $C_1$-$C_{18}$ hydrocarbon containing normal, secondary, tertiary or cyclic carbon atoms. Examples are methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and cyclopropylmethyl

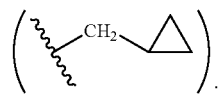

"Alkenyl" is $C_2$-$C_{18}$ hydrocarbon containing normal, secondary, tertiary or cyclic carbon atoms with at least one site of unsaturation, i.e. a carbon-carbon, sp² double bond. Examples include, but are not limited to, ethylene or vinyl (—CH=CH₂), allyl (—CH₂CH=CH₂), cyclopentenyl (—C₅H₇), and 5-hexenyl (—CH₂CH₂CH₂CH₂CH=CH₂).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH₂C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH₂—) 1,2-ethyl (—CH₂CH₂—), 1,3-propyl (—CH₂CH₂CH₂—), 1,4-butyl (—CH₂CH₂CH₂CH₂—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH₂C≡C—), and 4-pentynyl (—CH₂CH₂CH₂C≡CH).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or sp³ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

The term "polycarbocycle" refers to a saturated or unsaturated polycyclic ring system having from about 6 to about 25 carbon atoms and having two or more rings (e.g. 2, 3, 4, or 5 rings). The rings can be fused and/or bridged to form the polycyclic ring system. For example, the term includes bicycle [4,5], [5,5], [5,6] or [6,6] ring systems, as well as the following bridged ring systems:

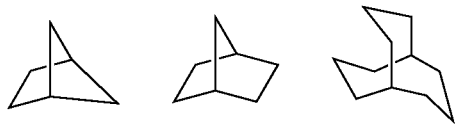

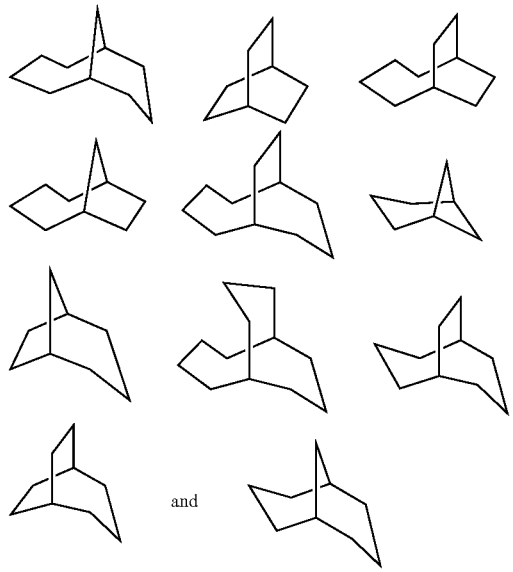

and (i.e., [2.1.1], [2.2.1], [3.3.3], [4.3.1], [2.2.2], [4.2.2], [4.2.1], [4.3.2], [3.1.1], [3.2.1], [4.3.3], [3.3.2], [3.2.2] and [3.3.1] polycyclic rings, respectively) that can be linked to the remainder of the compound of formula (I) through any synthetically feasible position. Like the other polycarbocycles, these representative bicyclo and fused ring systems can optionally comprise one or more double bonds in the ring system.

The term "polyheterocycle" refers to a polycarbocycle as defined herein, wherein one or more carbon atoms is replaced with a heteroatom (e.g., O, S, S(O), S(O)₂, N⁺(O⁻) $R_x$, or $NR_x$); wherein each $R_x$ is independently H, (C1-10) alkyl, (C2-10)alkenyl, (C2-10)alkynyl, (C1-10)alkanoyl, $S(O)_2NR_nR_p$, $S(O)_2R_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo).

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to: halo (e.g. F, Cl, Br, I), —R, —OR, —SR, —NR₂, —CF₃, —CCl₃, —OCF₃, —CN, —NO₂, —N(R)C(=O)R, —C(=O)R, —OC(=O)R, —C(O)OR, —C(=O)NRR, —S(=O)R, —S(=O)₂OR, —S(=O)₂R, —OS(=O)₂OR, —S(=O)₂NRR, and each R is independently —H, alkyl, aryl, arylalkyl, or heterocycle. Alkylene, alkenylene, and alkynylene groups may also be similarly substituted.

The term "optionally substituted" in reference to a particular moiety of the compound of formula I, (e.g., an optionally substituted aryl group) refers to a moiety having 0, 1, 2, or more substituents.

The symbol " " in a ring structure means that a bond is a single or double bond. In a non-limiting example,

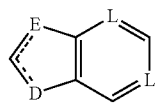

can be

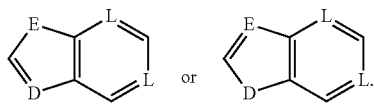

"Haloalkyl" as used herein includes an alkyl group substituted with one or more halogens (e.g. F, Cl, Br, or I). Representative examples of haloalkyl include trifluoromethyl, 2,2,2-trifluoroethyl, and 2,2,2-trifluoro-1-(trifluoromethyl)ethyl.

"Heterocycle" or "heterocyclyl" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The term heterocycle also includes "heteroaryl" which is a heterocycle wherein at least one heterocyclic rings is aromatic.

Examples of heterocycles include by way of example and not limitation pyridyl, dihydropyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

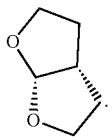

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having up to about 25 carbon atoms. Typically, a carbocycle has about 3 to 7 carbon atoms as a monocycle, about 7 to 12 carbon atoms as a bicycle, and up to about 25 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo[4,5], [5,5], [5,6] or [6,6] system, or 9 or 10 ring atoms arranged as a bicyclo[5,6] or [6,6] system. The term carbocycle includes "cycloalkyl" which is a saturated or unsaturated carbocycle. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The invention includes all stereoisomers of the compounds described herein.

The term "heterocyclylsulfonyl," as used herein, refers to hetercyclyl group attached to the parent molecular moiety through a sulfonyl group.

The term "heteroarylsulfonyl," as used herein, refers to heteroaryl group attached to the parent molecular moiety through a sulfonyl group.

The term "alkyloxy," as used herein, refers to an alkyl group attached to the parent molecular moiety through an oxygen atom.

The term "alkoxyalkyloxy," as used herein, refers to an alkyloxy group substituted with one, two, or three alkoxy groups.

The term "haloalkoxyalkyloxy," as used herein, refers to an alkyloxy group substituted with one, two, or three haloalkoxy groups.

The term "cycloalkyloxyalkyloxy," as used herein, refers to an alkyloxy group substituted with one, two, or three cycloalkyloxy groups.

The term "aryloxyalkyloxy," as used herein, refers to an alkyloxy group substituted with one, two, or three aryloxy groups.

The term "heteroaryloxyalkyloxy," as used herein, refers to an alkyloxy group substituted with one, two, or three heteroaryloxy groups.

The term "heterocyclyloxyalkyloxy," as used herein, refers to an alkyloxy group substituted with one, two, or three heterocyclyloxy groups.

The term "cyanoalkyloxy," as used herein, refers to an alkyloxy group substituted with one, two, or three cyano groups.

The term "cyanocycloalkyloxy," as used herein, refers to a cycloalkyloxy group substituted with one, two, or three cyano groups.

The term "haloalkoxyalkyl," as used herein, refers to an alkyl group substituted with one, two, or three haloalkoxy groups.

The term "amino," as used herein, refers to —NH$_2$.

The term "alkylamino," as used herein, refers to an amino group substituted with one alkyl group (i.e. —NH(alkyl)).

The term "dialkylamino," as used herein, refers to an amino group substituted with two alkyl groups (i.e. —N(alkyl)$_2$).

The term "aminoalkyl," as used herein, refers to an alkyl group substituted with one, two, or three amino groups.

The term "alkylaminoalkyl," as used herein, refers to an alkyl group substituted with one, two, or three alkylamino groups.

The term "dialkylaminoalkyl," as used herein, refers to an alkyl group substituted with one, two, or three dialkylamino groups.

The term "alkoxyamino," as used herein, refers to an amino group substituted with one alkoxy group.

The term "sulfonylalkyl," as used herein, refers to an alkyl group substituted with at least one SO$_3$H group.

Specific Definitions for Groups A$^0$, P$^0$, V$^0$, Z$^0$, and E$^0$

For the groups A$^0$, P$^0$, V$^0$, Z$^0$, and E$^0$ the following definitions apply. These definitions also apply for all other A, P, V, Z, and E groups unless those groups are otherwise defined herein.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term 'aryl'.

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxyalkylcarbonylalkyl," as used herein, refers to an alkyl group substituted with one, two, or three alkoxyalkylcarbonyl groups.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to six carbon atoms.

The term "alkylcarbonyl," as used herein, refers to an alkyl group attached to the parent molecular moiety through a carbonyl group.

The term "alkylcarbonylalkyl," as used herein, refers to an alkyl group substituted with one, two, or three alkylcarbonyl groups.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfanylalkyl," as used herein, refers to an alkyl group substituted with one, two, or three alkylsulfanyl groups.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkenyl," as used herein, refers to an alkenyl group substituted with one, two, or three aryl groups.

The term "arylalkoxy," as used herein, refers to an aryl group attached to the parent molecular moiety through an alkoxy group.

The term "arylalkoxyalkyl," as used herein, refers to an alkyl group substituted with one, two, or three arylalkoxy groups.

The term "arylalkoxyalkylcarbonyl," as used herein, refers to an arylalkoxyalkyl group attached to the parent molecular moiety through a carbonyl group.

The term "arylalkoxyalkylcarbonylalkyl," as used herein, refers to an alkyl group substituted with one, two, or three arylalkoxyalkylcarbonyl groups.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —NR$^c$R$^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^X$R$^Y$;

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with one, two, or three aryloxy groups.

The term "aryloxycarbonyl," as used herein, refers to an aryloxy group attached to the parent molecular moiety through a carbonyl group.

The term "arylsulfanyl," as used herein, refers to an aryl group attached to the parent molecular moiety through a sulfur atom.

The term "arylsulfonyl," as used herein, refers to an aryl group attached to the parent molecular moiety through a sulfonyl group.

The terms "Cap" and "cap" as used herein, refer to the group which is placed on the nitrogen atom of the terminal nitrogen-containing ring. It should be understood that "Cap" or "cap" can refer to the reagent used to append the group to the terminal nitrogen-containing ring or to the fragment in the final product.

The term "carbonyl," as used herein, refers to —C(=O)—.

The term "carboxy," as used herein, refers to —CO$_2$H.

The term "carboxyalkyl," as used herein, refers to an alkyl group substituted with one, two, or three carboxy groups.

The term "cyano," as used herein, refers to —CN.

The term "cyanoalkyl" as used herein, refers to an alkyl group having at least one —CN substituent.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —NR$^x$R$^y$ wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkenyl," as used herein, refers to an alkenyl group substituted with one, two, or three cycloalkyl groups.

The term "(cycloalkyl)alkyl," as used herein, refers to an alkyl group substituted with one, two, or three cycloalkyl groups. The alkyl part of the (cycloalkyl)alkyl is further optionally substituted with one or two groups independently selected from hydroxy and —NR$^c$R$^d$.

The term "cycloalkyloxy," as used herein, refers to a cycloalkyl group attached to the parent molecular moiety through an oxygen atom.

The term "cycloalkyloxyalkyl," as used herein, refers to an alkyl group substituted with one, two, or three cycloalkyloxy groups.

The term "cycloalkylsulfonyl," as used herein, refers to a cycloalkyl group attached to the parent molecular moiety through a sulfonyl group.

The term "formyl," as used herein, refers to —CHO.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted by one, two, three, or four halogen atoms.

The term "haloalkylsulfanyl," as used herein, refers to a haloalkyl group attached to the parent molecular moiety through a sulfur atom.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a fourto six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure are optionally substituted with one, two, three, four, or five substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, —$(NR^XR^Y)$alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkenyl," as used herein, refers to an alkenyl group substituted with one, two, or three heterocyclyl groups.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —$NR^cR^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —$NR^XR^Y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclylcarbonylalkyl," as used herein, refers to an alkyl group substituted with one, two, or three heterocyclylcarbonyl groups.

The term "heterocyclyloxy," as used herein, refers to a heterocyclyl group attached to the parent molecular moiety through an oxygen atom.

The term "heterocyclyloxyalkyl," as used herein, refers to an alkyl group substituted with one, two, or three heterocyclyloxy groups.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —$NO_2$.

The term "—$NR^aR^b$," as used herein, refers to two groups, $R^a$ and $R^b$, which are attached to the parent molecular moiety through a nitrogen atom. $R^a$ and $R^b$ are independently selected from hydrogen, alkenyl, and alkyl.

The term "$(NR^aR^b)$alkyl," as used herein, refers to an alkyl group substituted with one, two, or three —$NR^aR^b$ groups.

The term "$(NR^aR^b)$carbonyl," as used herein, refers to an —$NR^aR^b$ group attached to the parent molecular moiety through a carbonyl group.

The term "—$NR^cR^d$," as used herein, refers to two groups, $R^c$ and $R^d$, which are attached to the parent molecular moiety through a nitrogen atom. $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "$(NR^cR^d)$alkenyl," as used herein, refers to an alkenyl group substituted with one, two, or three —$NR^cR^d$ groups.

The term "$(NR^cR^d)$alkyl," as used herein, refers to an alkyl group substituted with one, two, or three —$NR^cR^d$ groups. The alkyl part of the $(NR^cR^d)$alkyl is further optionally substituted with one or two additional groups selected from alkoxy, alkoxyalkylcarbonyl, alkoxycarbonyl, alkylsulfanyl, arylalkoxyalkylcarbonyl, carboxy, heterocyclyl, heterocyclylcarbonyl, hydroxy, and $(NR^eR^f)$carbonyl; wherein the heterocyclyl is further optionally substituted with one, two, three, four, or five substituents independently selected from alkoxy, alkyl, cyano, halo, haloalkoxy, haloalkyl, and nitro.

The term "$(NR^cR^d)$carbonyl," as used herein, refers to an —$NR^cR^d$ group attached to the parent molecular moiety through a carbonyl group.

The term "—$NR^eR^f$," as used herein, refers to two groups, $R^e$ and $R^f$, which are attached to the parent molecular moiety through a nitrogen atom. $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl.

The term "(NR$^e$R$^f$)alkyl," as used herein, refers to an alkyl group substituted with one, two, or three —NR$^e$R$^f$ groups.

The term "(NR$^e$R$^f$)alkylcarbonyl," as used herein, refers to an (NR$^e$R$^f$)alkyl group attached to the parent molecular moiety through a carbonyl group.

The term "(NR$^e$R$^f$)carbonyl," as used herein, refers to an —NR$^e$R$^f$ group attached to the parent molecular moiety through a carbonyl group.

The term "(NR$^e$R$^f$)sulfonyl," as used herein, refers to an —NR$^e$R$^f$ group attached to the parent molecular moiety through a sulfonyl group.

The term "—NR$^X$R$^Y$," as used herein, refers to two groups, R$^X$ and R$^Y$, which are attached to the parent molecular moiety through a nitrogen atom. R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl.

The term "(NR$^X$R$^Y$)alkyl," as used herein, refers to an alkyl group substituted with one, two, or three —NR$^X$R$^Y$ groups.

The term "oxo," as used herein, refers to =O.

The term "sulfonyl," as used herein, refers to —SO$_2$—.

The term "trialkylsilyl," as used herein, refers to —SiR$_3$, wherein R is alkyl. The R groups may be the same or different The term "trialkylsilylalkyl," as used herein, refers to an alkyl group substituted with one, two, or three trialkylsilyl groups.

The term "trialkylsilylalkoxy," as used herein, refers to a trialkylsilylalkyl group attached to the parent molecular moiety through an oxygen atom.

The term "trialkylsilylalkoxyalkyl," as used herein, refers to an alkyl group substituted with one, two, or three trialkylsilylalkoxy groups.

The "P" groups (eg P$^{1a}$, P$^{1b}$, P$^O$, etc) defined for formula (I) herein have one bond to a —C(=O)— of formula (I) and one bond to a W$^{1a}$ group. It is to be understood that a nitrogen of the P group is connected to the —C(=O)— group of formula (I) and that a carbon of the P group is connected to the W$^{1a}$ group.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The invention includes all stereoisomers of the compounds described herein.

Prodrugs

The term "prodrug" as used herein refers to any compound that when administered to a biological system generates a compound of the invention that inhibits HCV activity ("the active inhibitory compound"). The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —CH$_2$OC(=O)R$^{99}$ and acyloxymethyl carbonates —CH$_2$OC(=O)OR$^{99}$ where R$^{99}$ is C$_1$-C$_6$ alkyl, C$_1$-C$_6$ substituted alkyl, C$_6$-C$_{20}$ aryl or C$_6$-C$_{20}$ substituted aryl. The acyloxyalkyl ester was first used as a prodrug strategy for carboxylic acids and then applied to phosphates and phosphonates by Farquhar et al. (1983) *J Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —CH$_2$OC(=O)C(CH$_3$)$_3$. An exemplary acyloxymethyl carbonate prodrug moiety is pivaloyloxymethylcarbonate (POC) —CH$_2$OC(=O)OC(CH$_3$)$_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) J Med. Chem. 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans*. 112345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

By way of example and not limitation, $R^1$, $R^3$, $R^{41}$, $R^{43}$, and $X^4$ are recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. Whenever a compound described herein is substituted with more than one of the same designated group, e.g., "$R^1$" or "$R^3$", then it will be understood that the groups may be the same or different, i.e., each group is independently selected. Wavy lines indicate the site of covalent bond attachments to the adjoining groups, moieties, or atoms.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of physiologically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Physiologically acceptable salts of a hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Specific Embodiments

In one specific embodiment of the invention the compound of formula (I) is not:

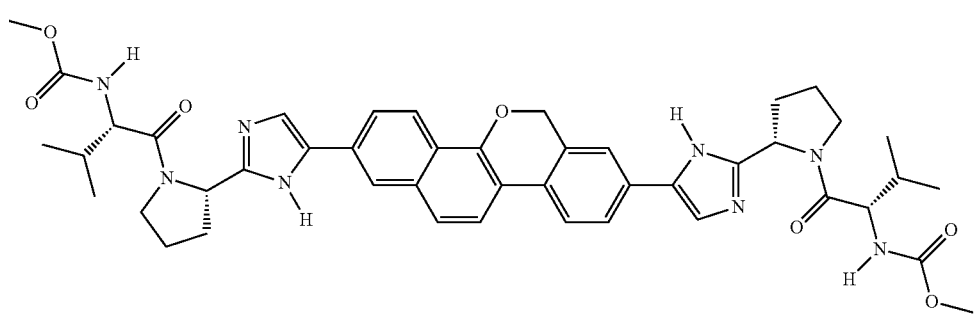

Compound

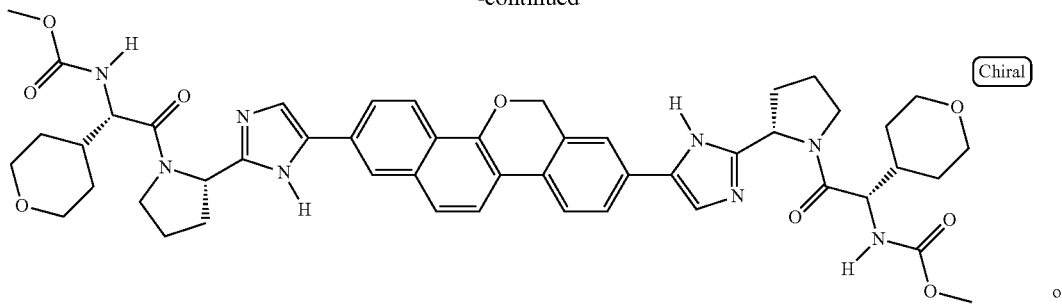
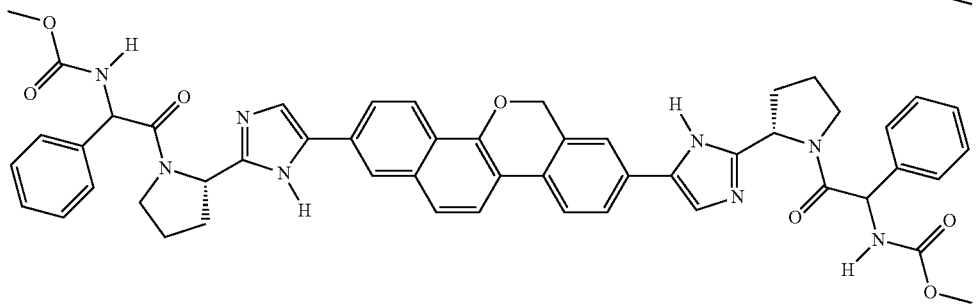
or
In one specific embodiment of the invention the compound of formula (I) is not:
Compound
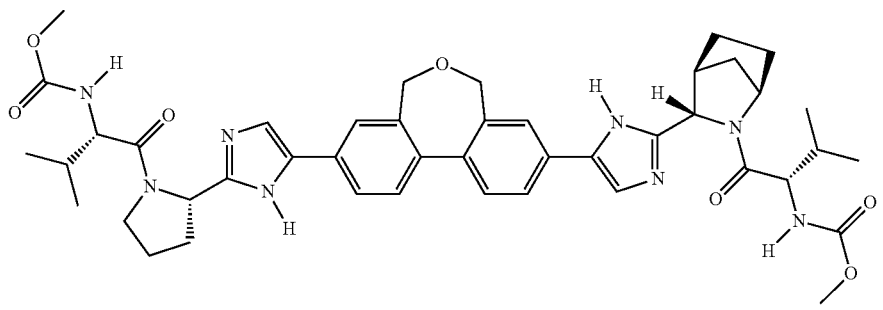
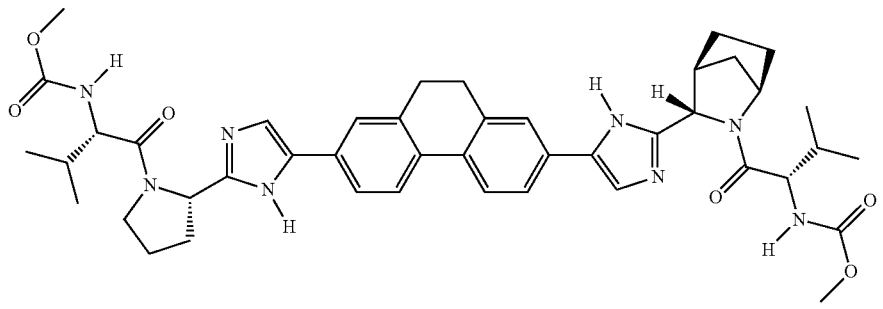
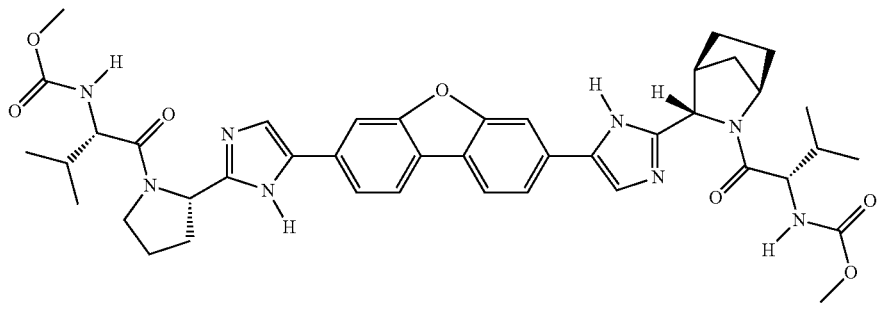

-continued
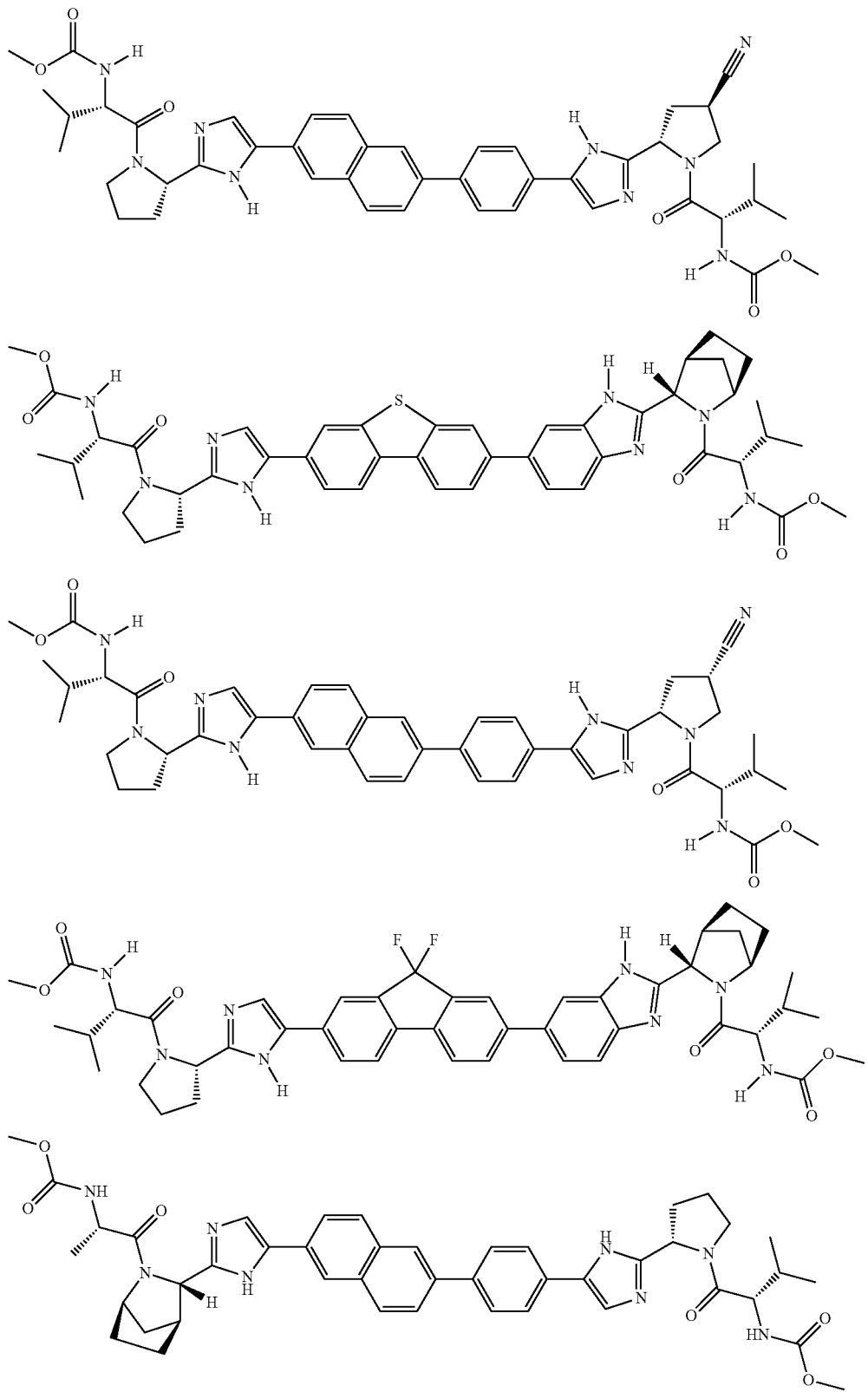

-continued
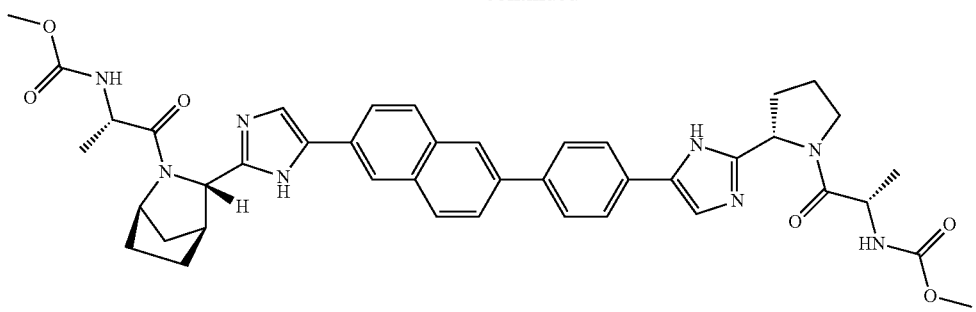
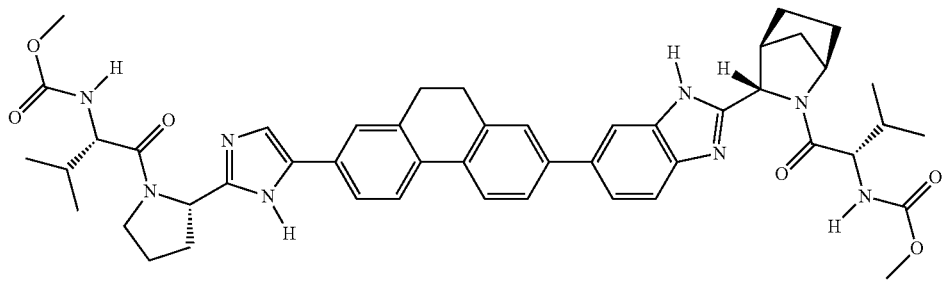
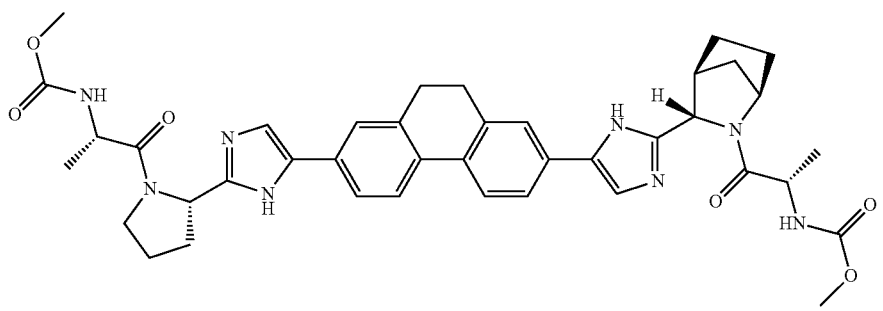
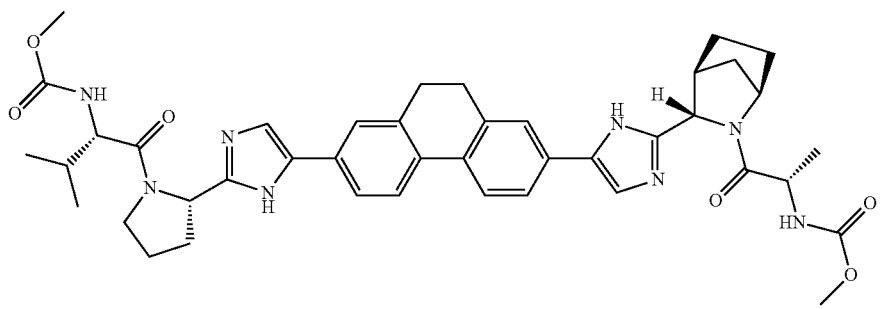
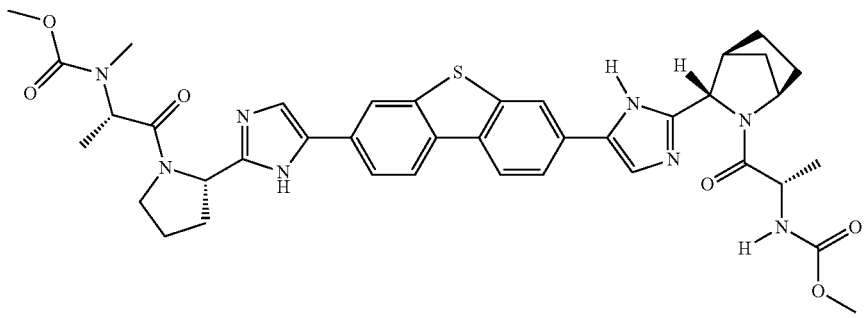

-continued
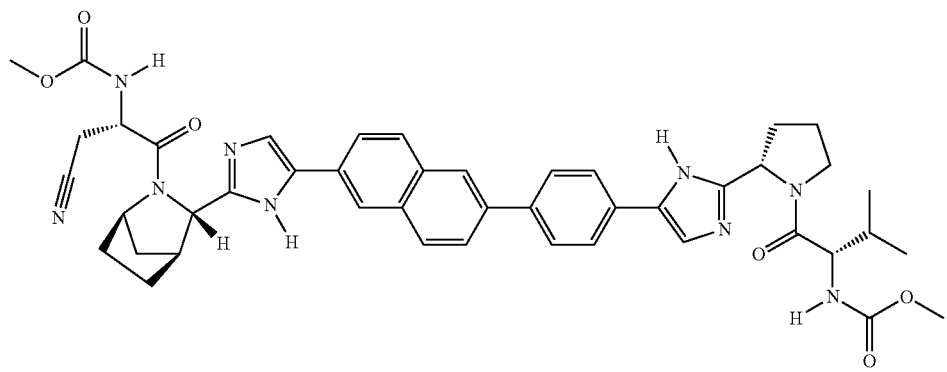
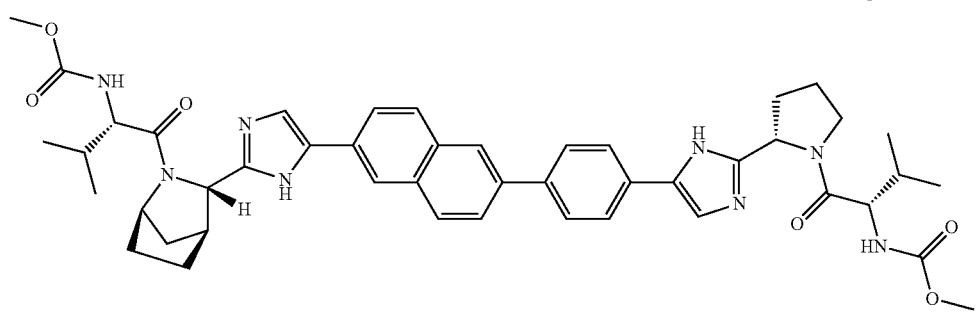
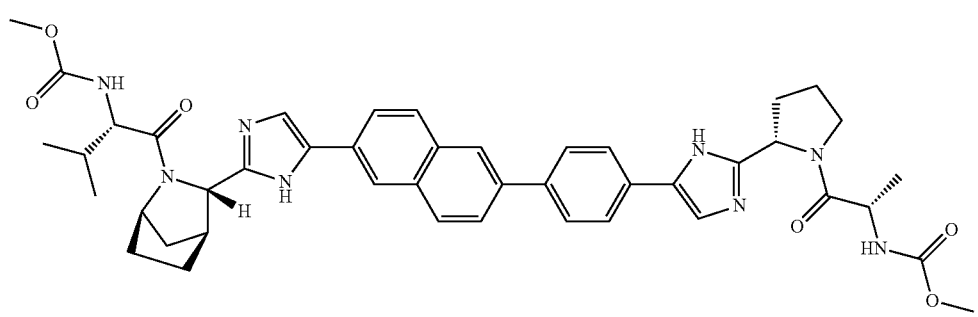
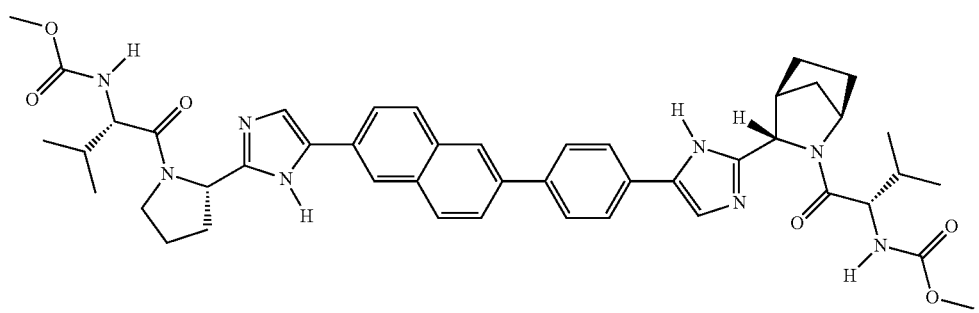
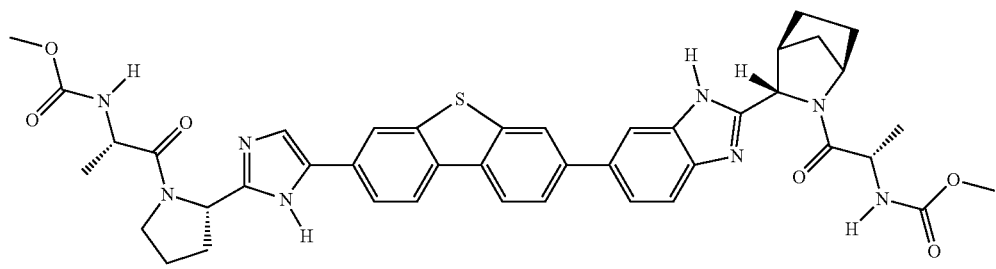

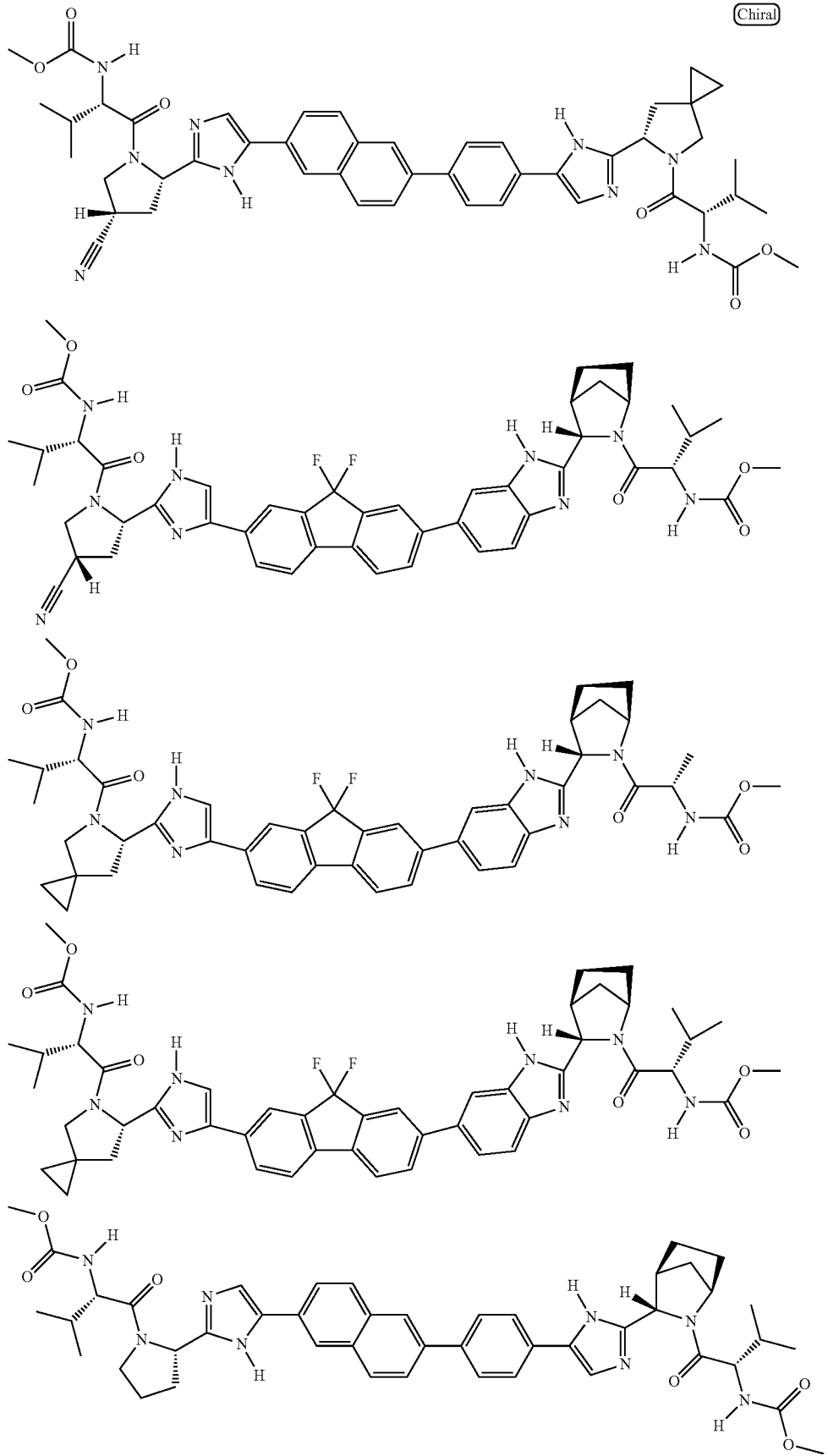

-continued
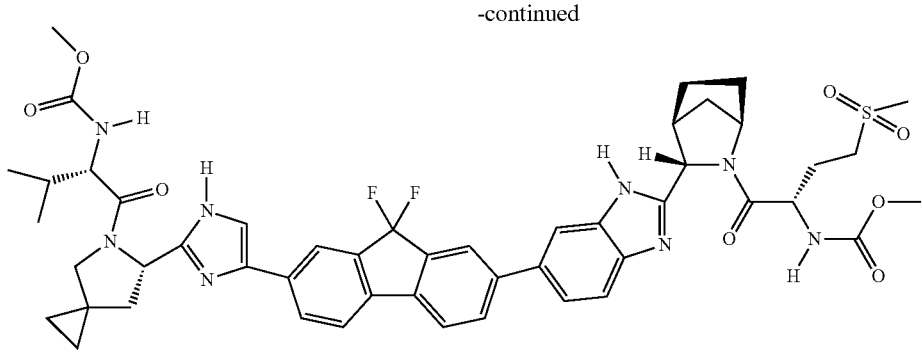
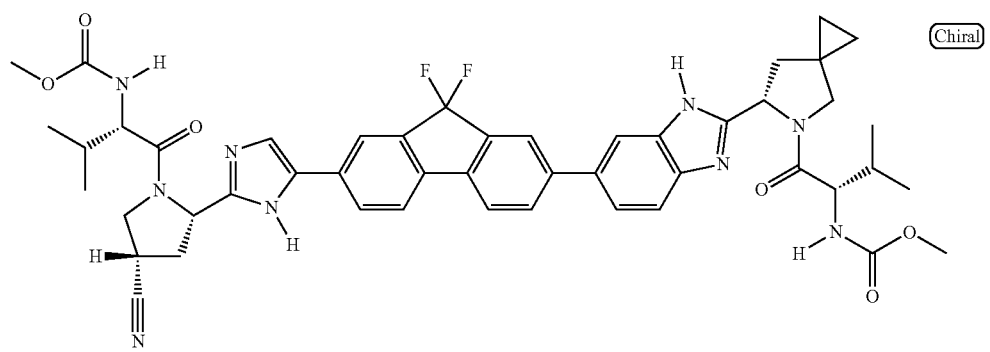
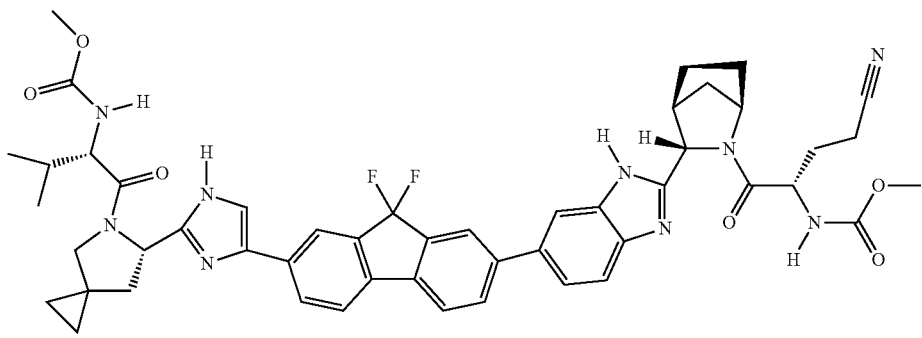
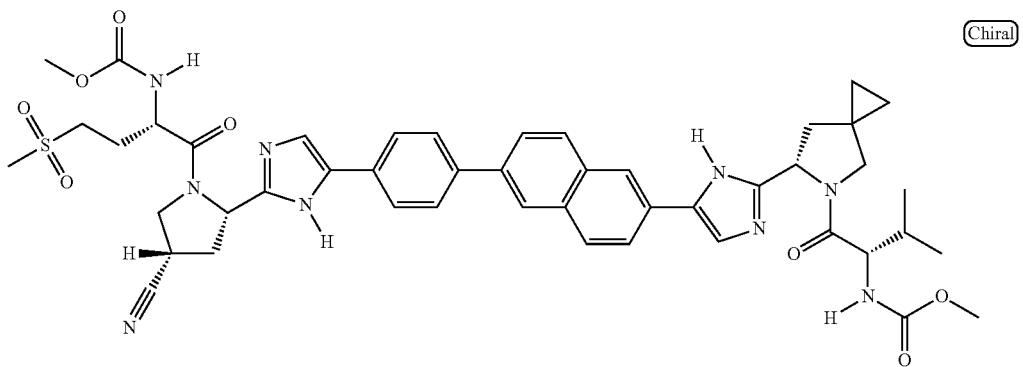

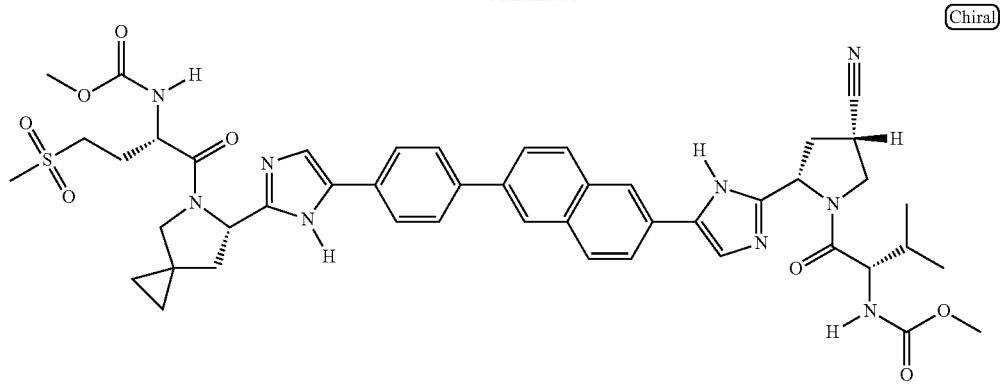
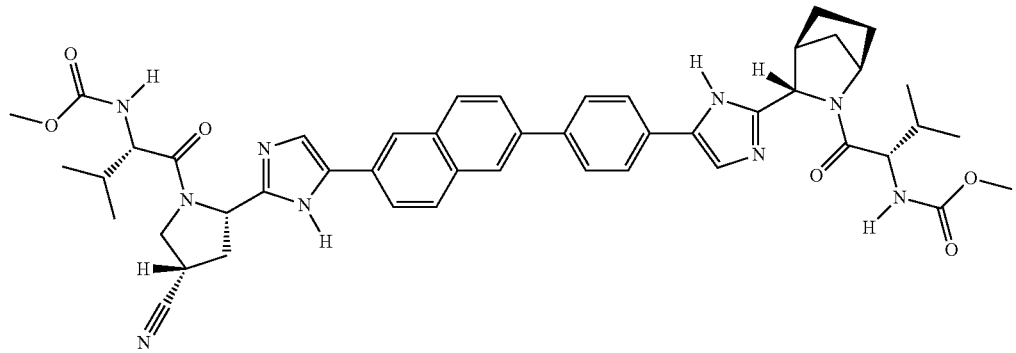
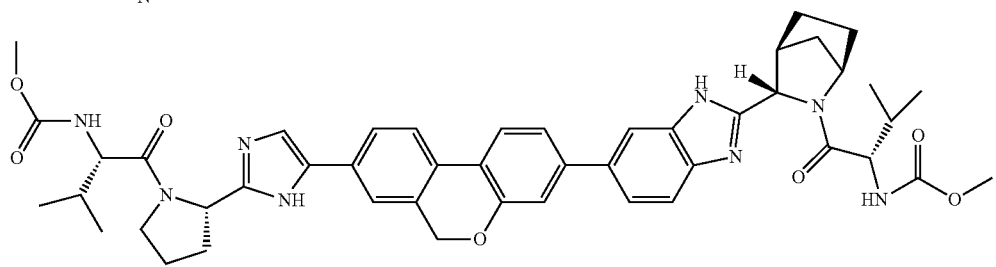
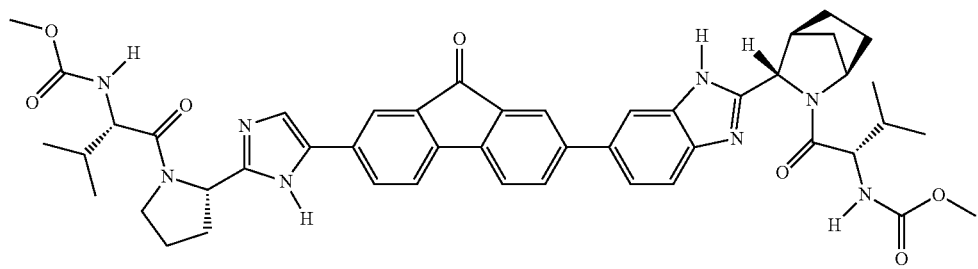
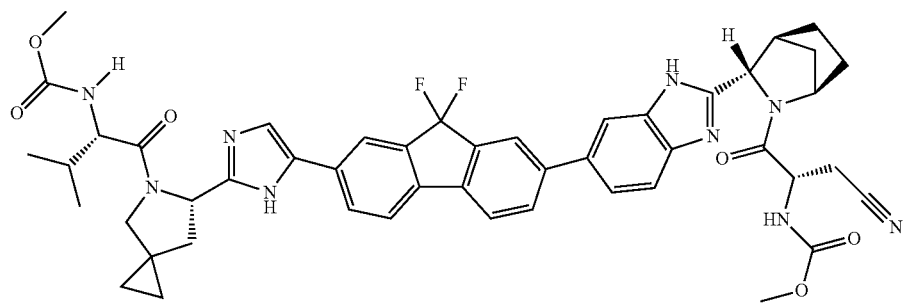

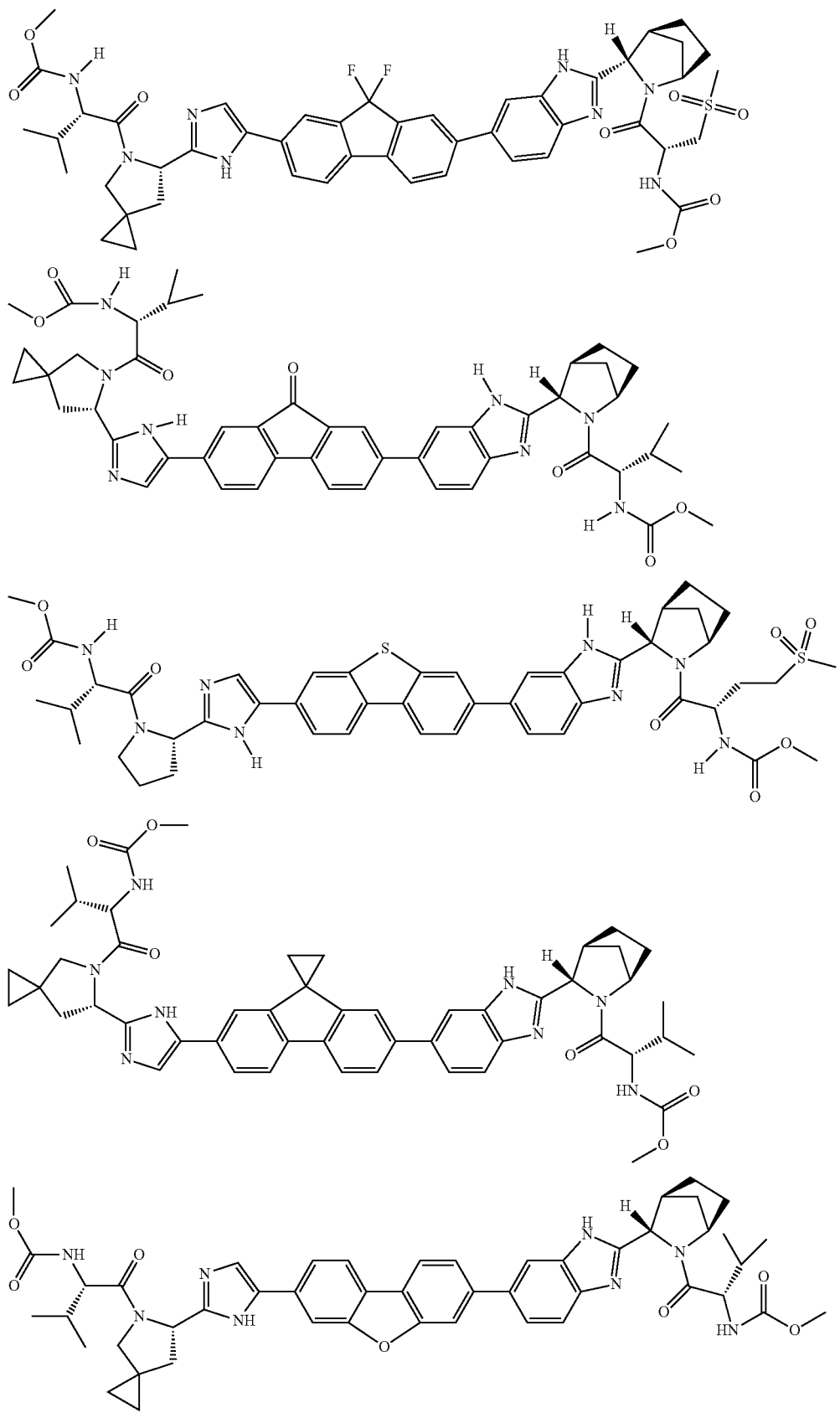

-continued
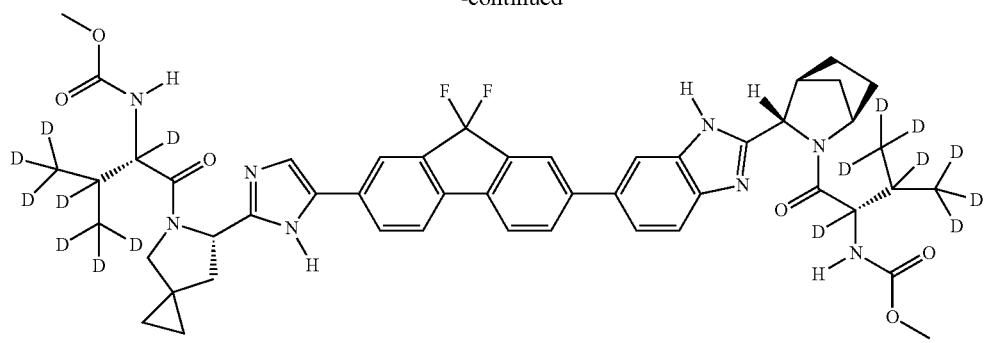
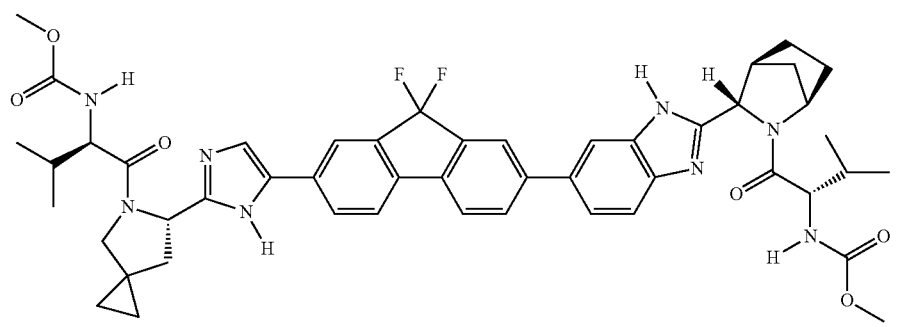
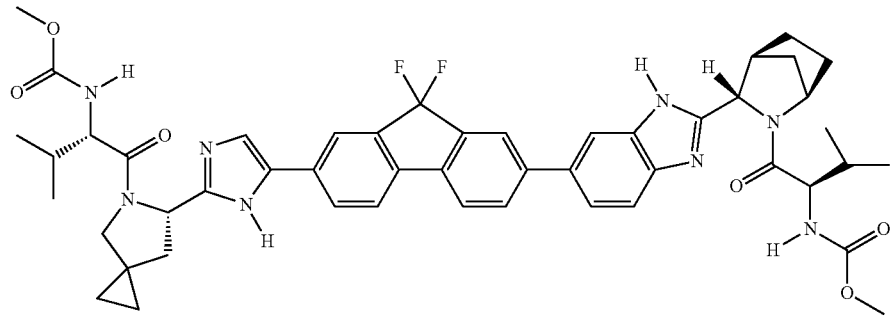
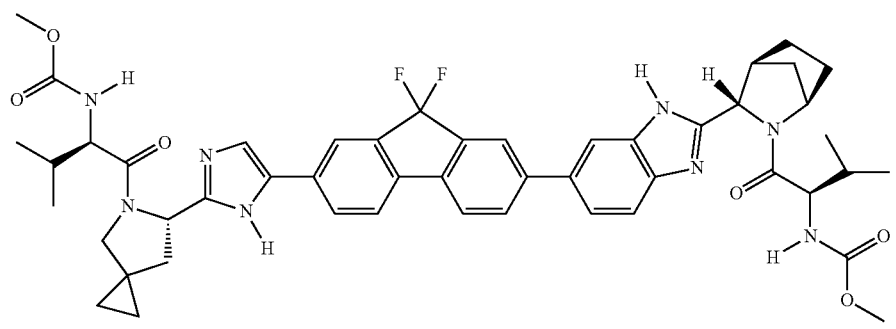
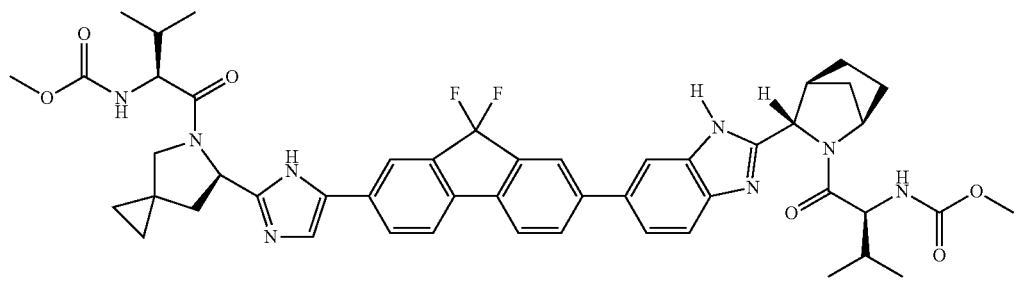

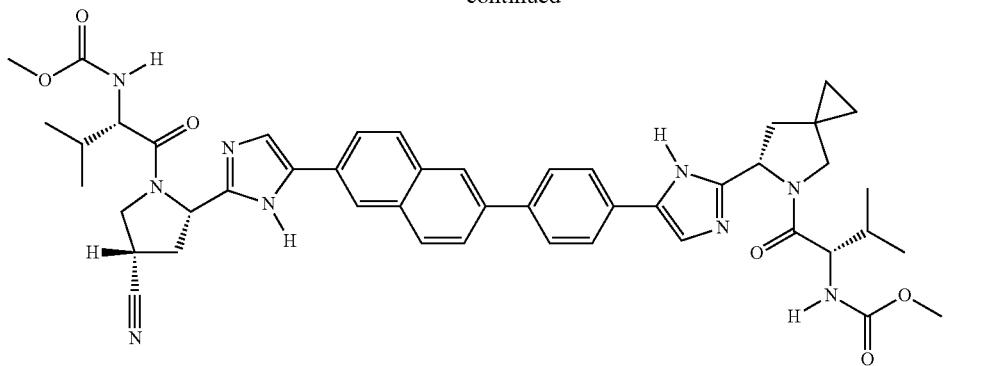
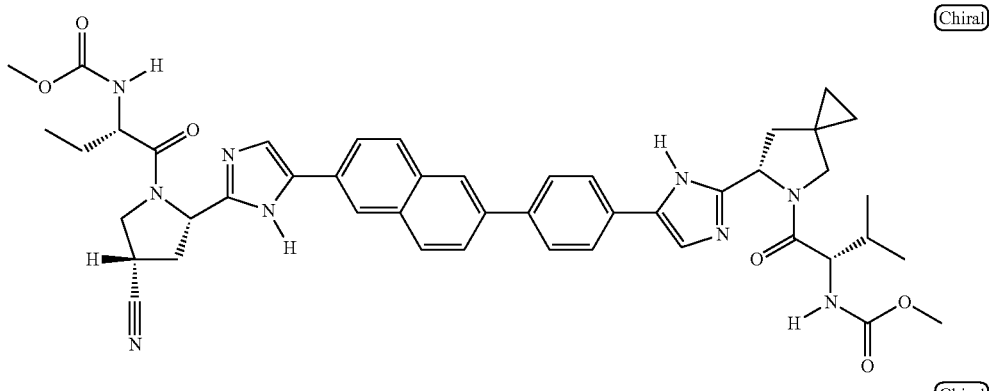
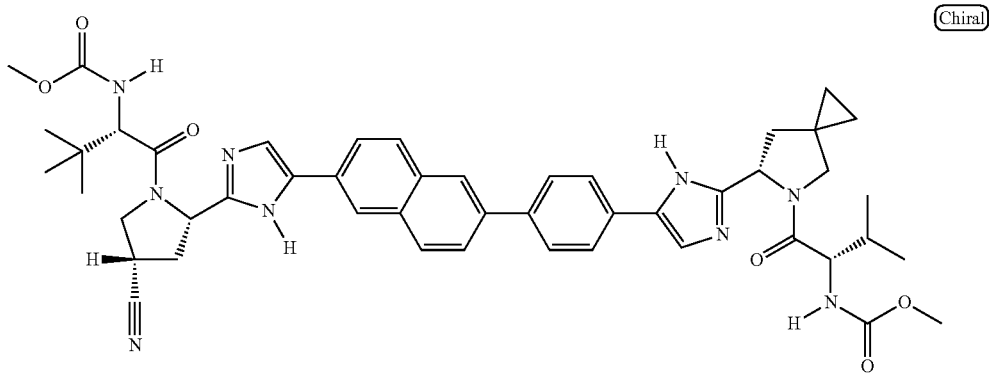
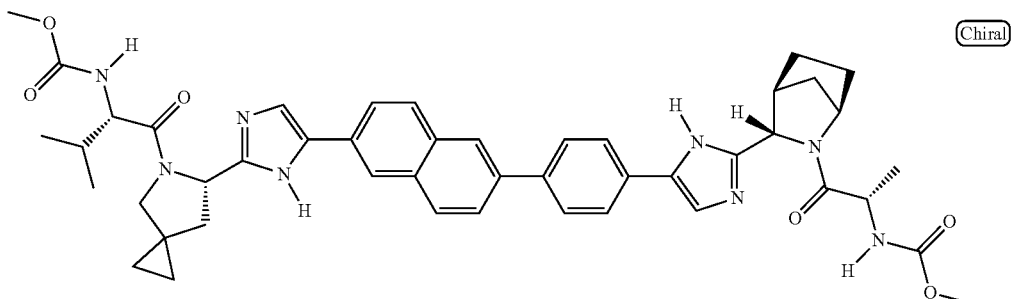
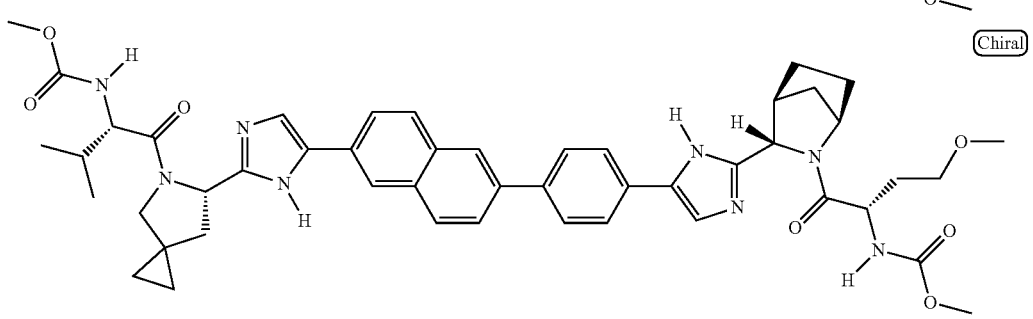

-continued

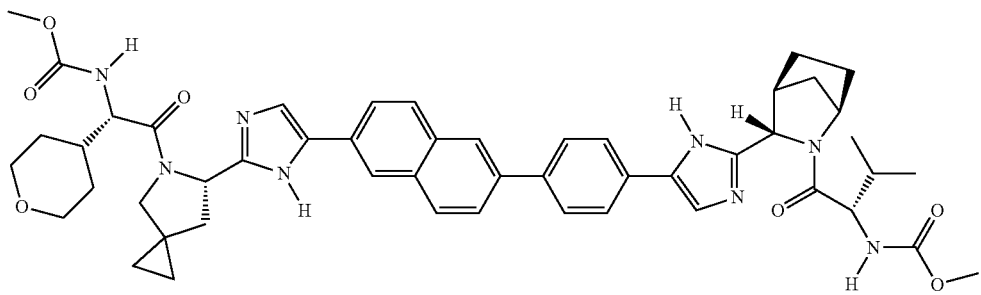
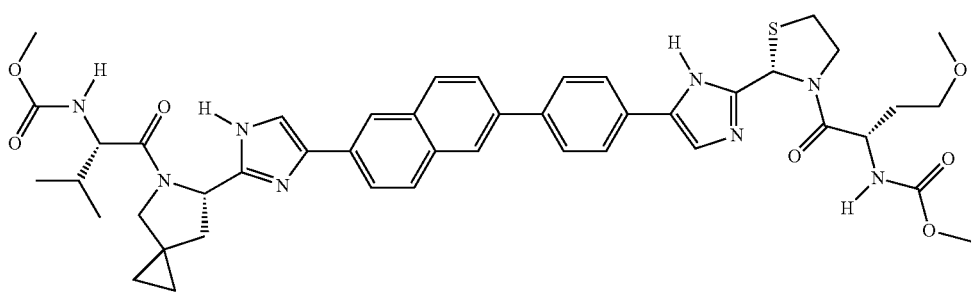
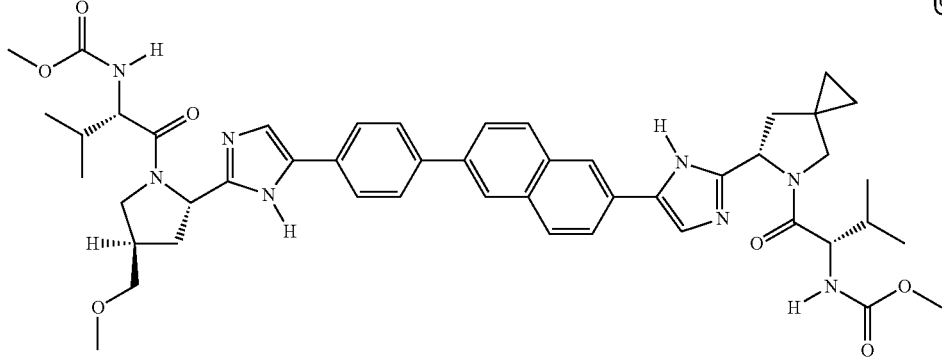

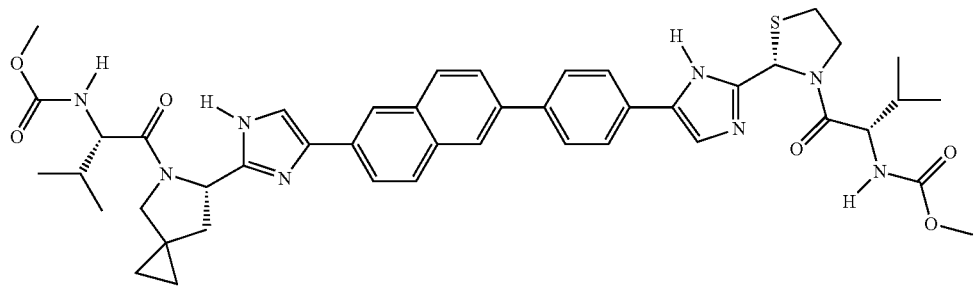
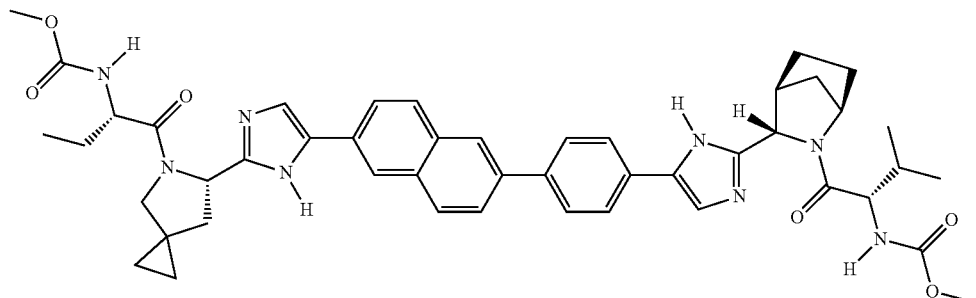
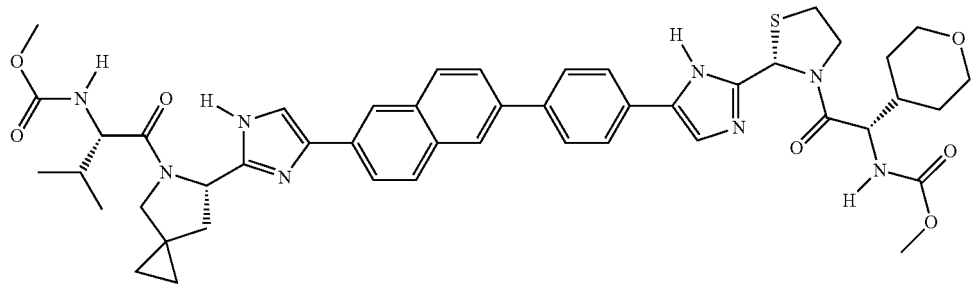
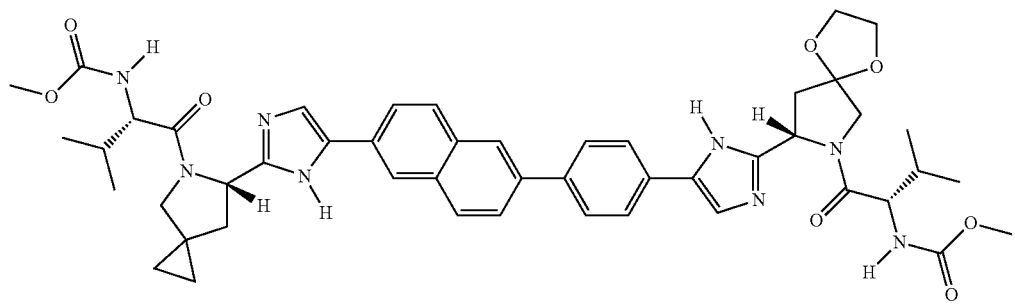
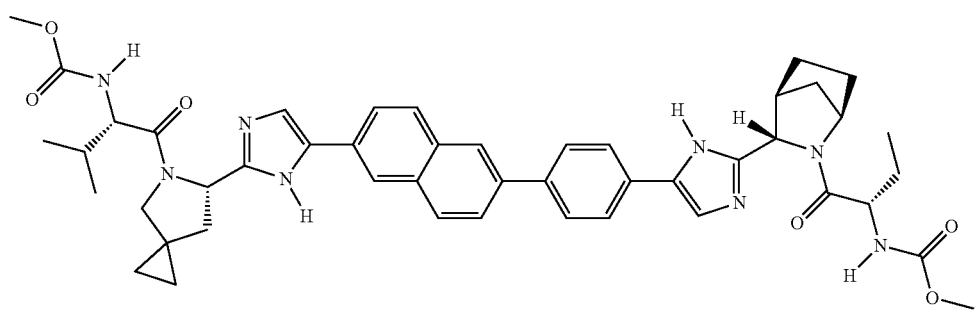

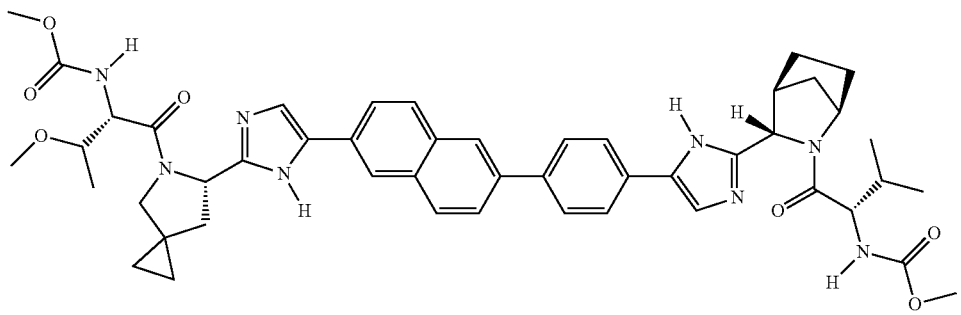
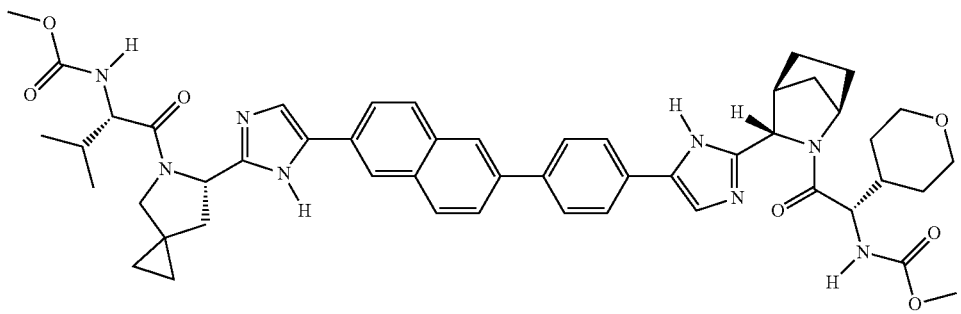
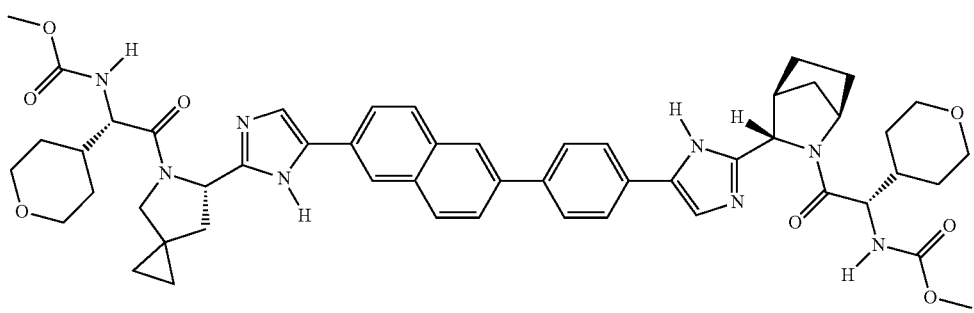
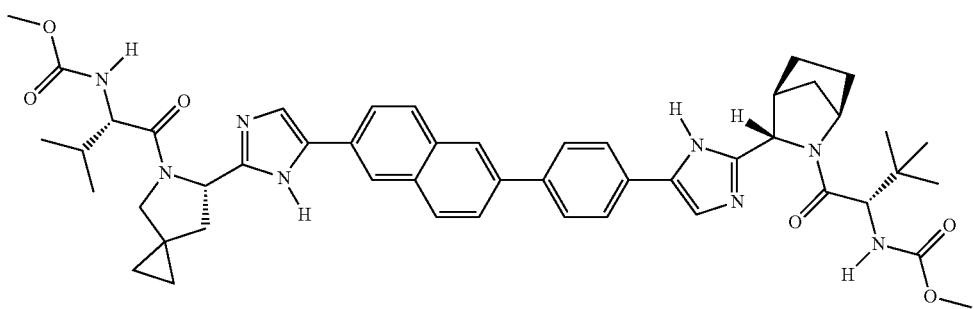
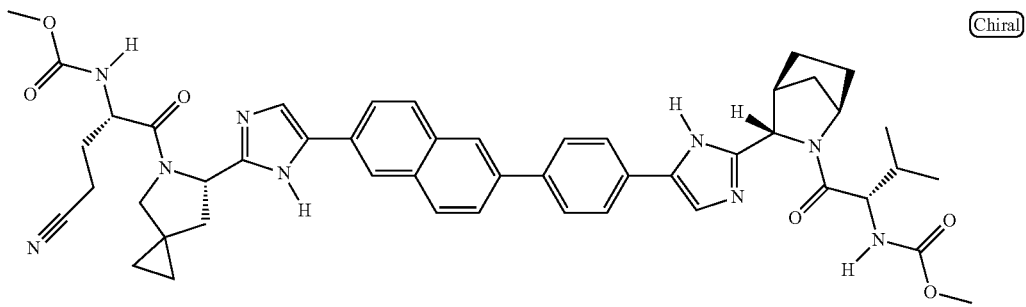

-continued
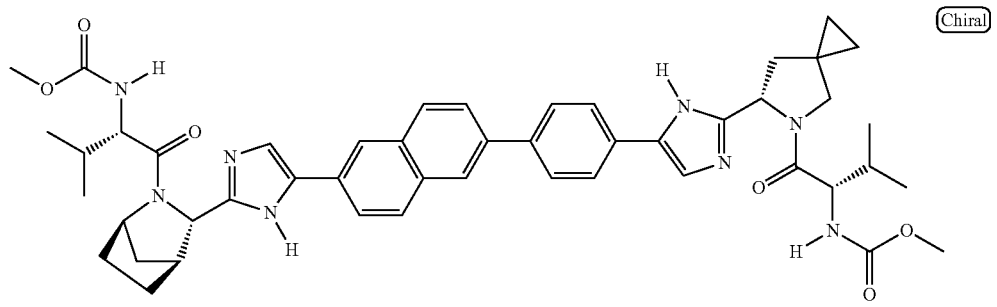
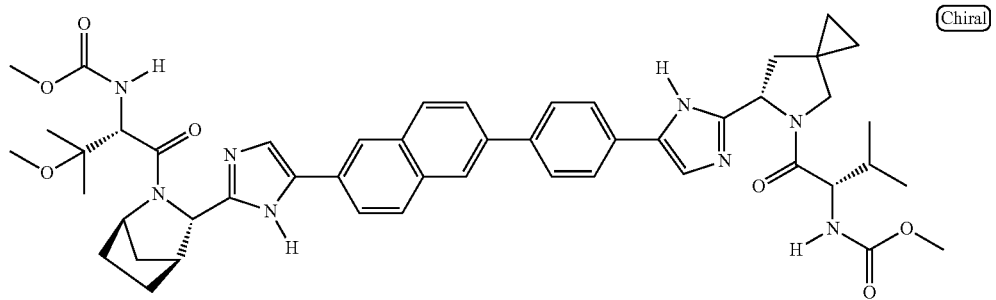
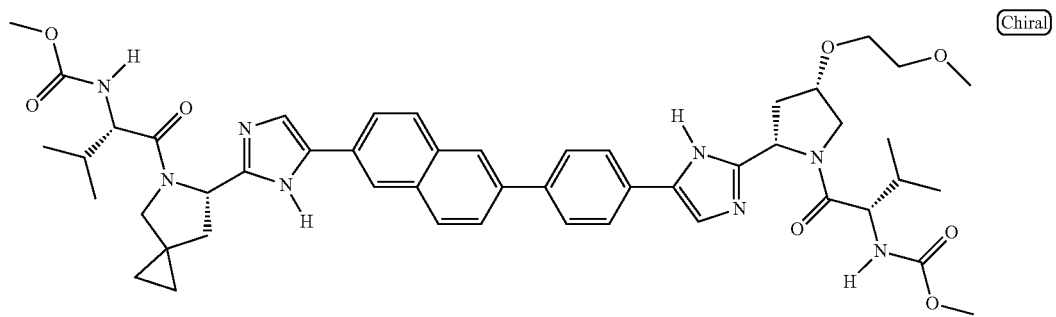
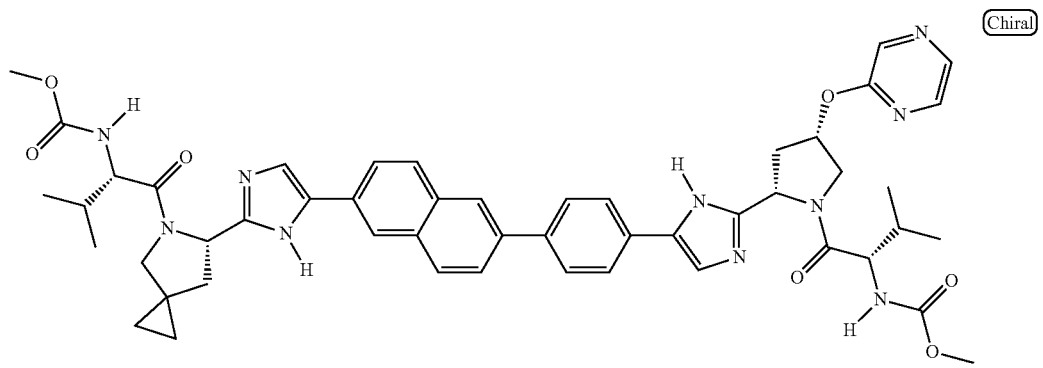
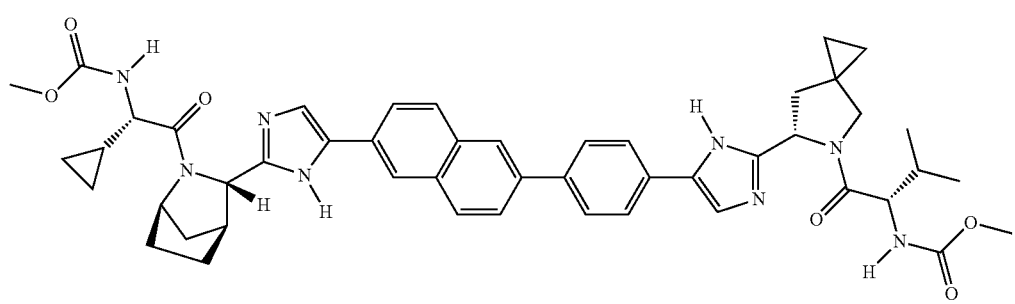

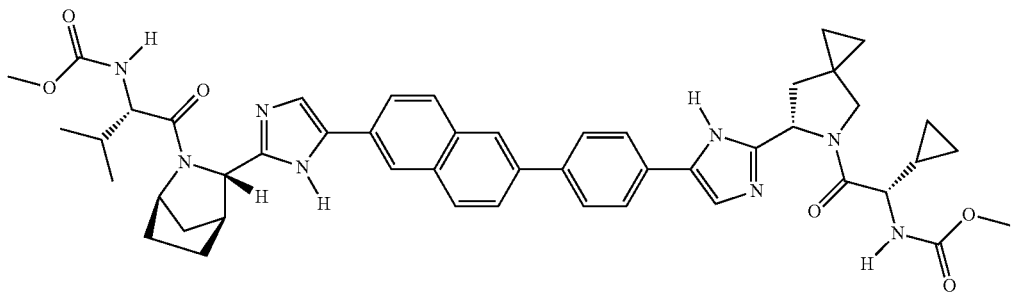
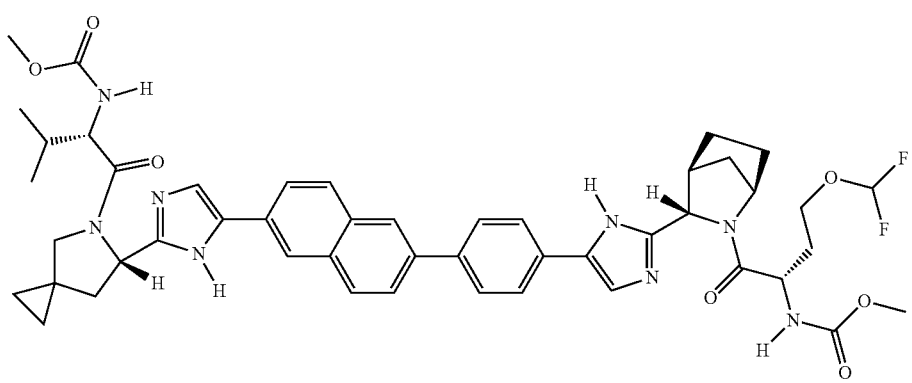
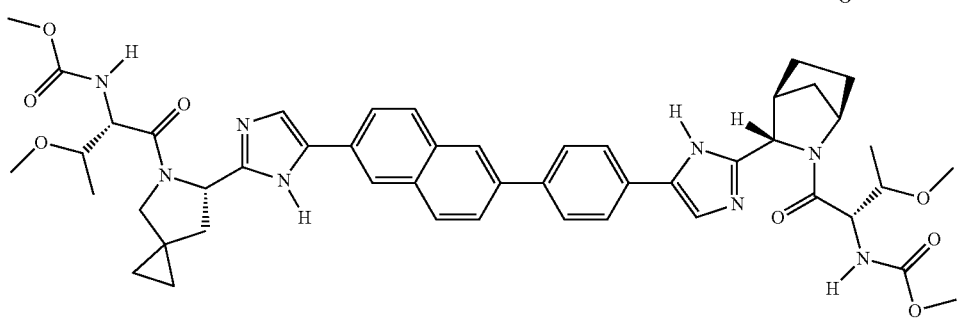
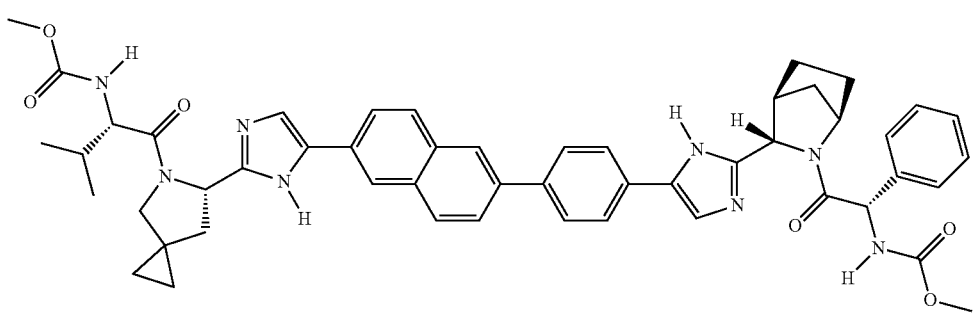
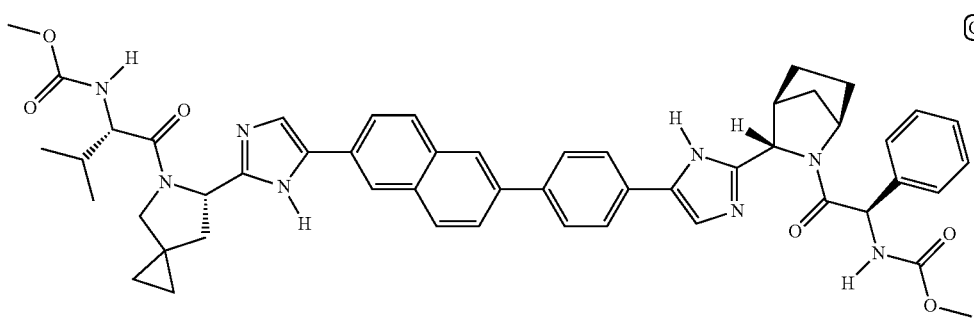

-continued
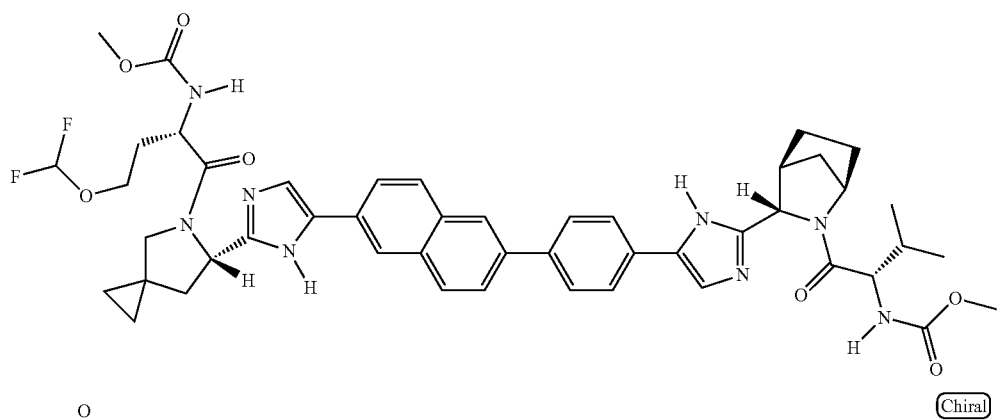
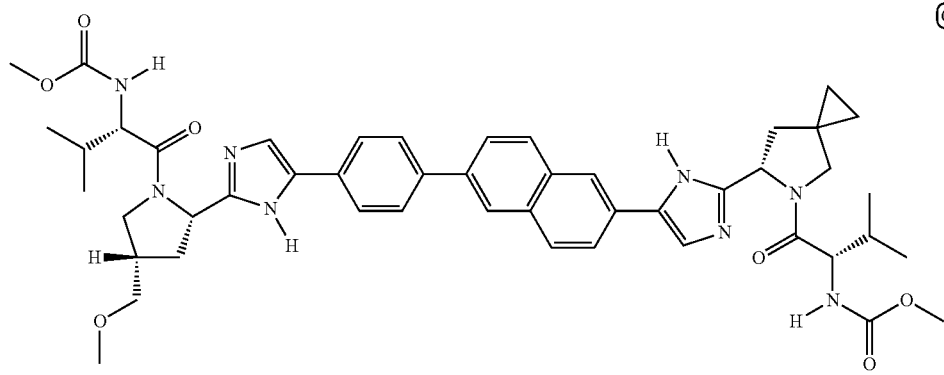
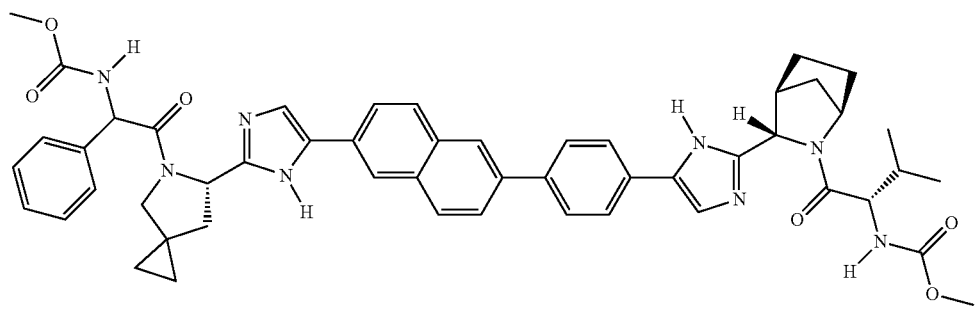
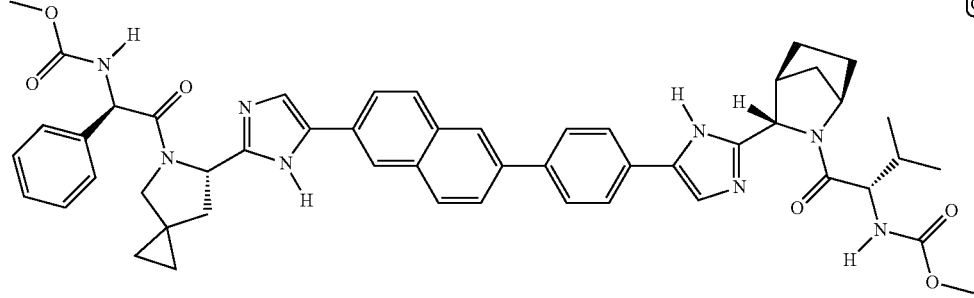
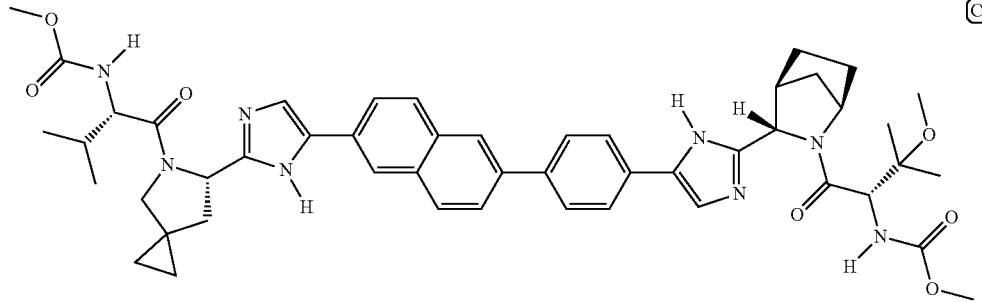

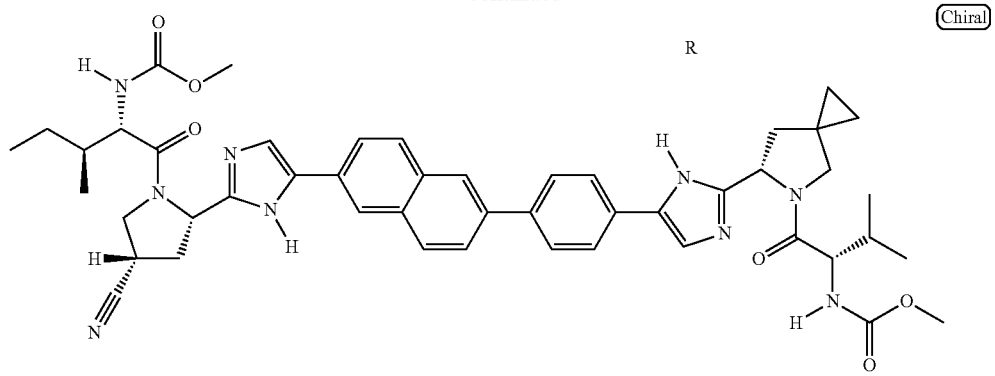
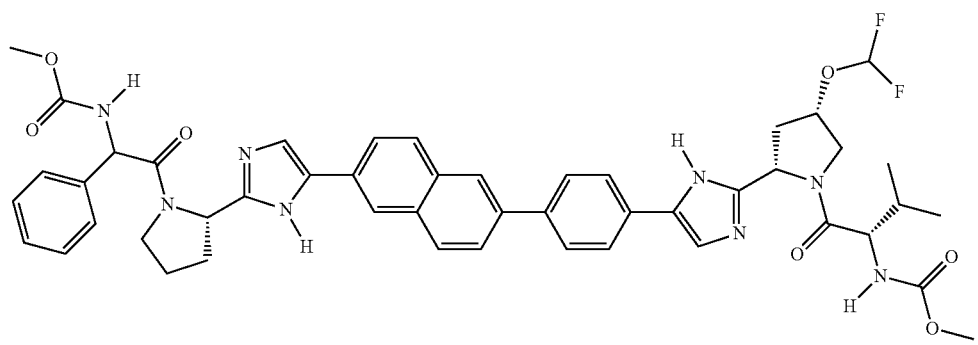
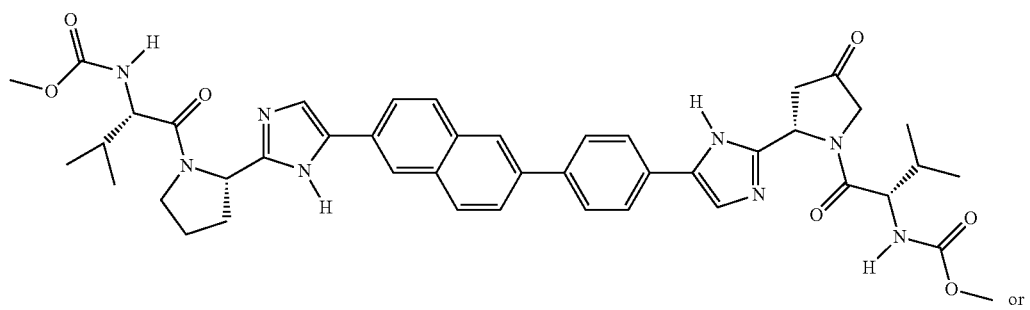
or
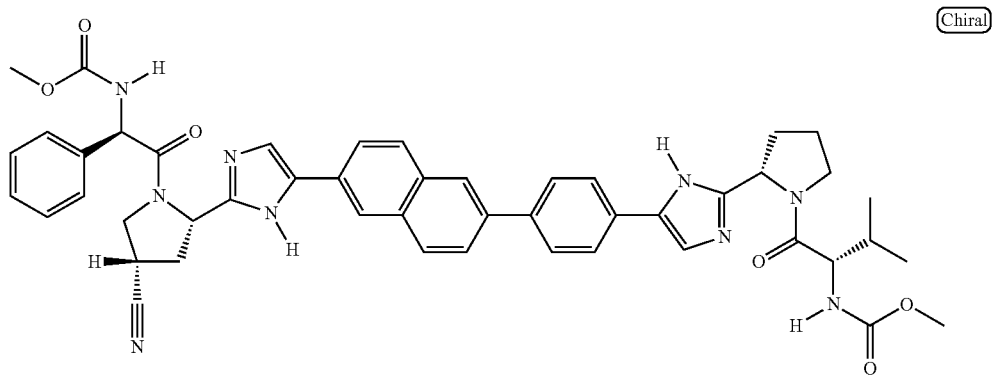
In one specific embodiment of the invention the compound of formula (I) is not:

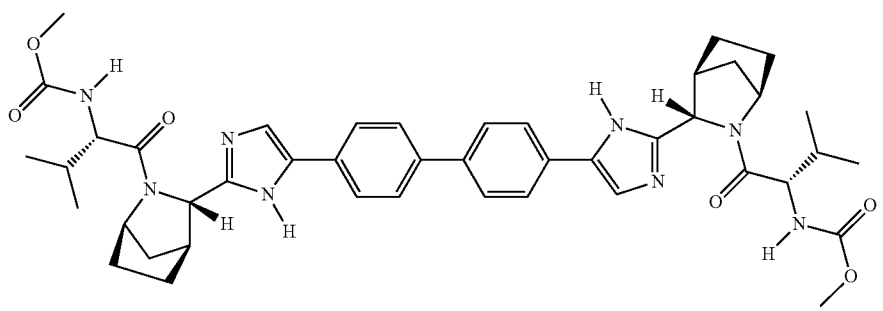
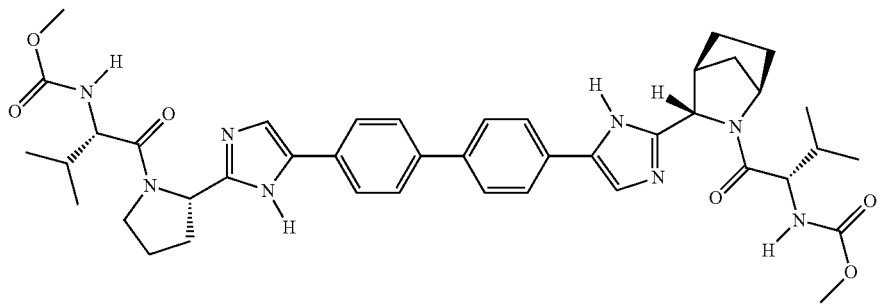
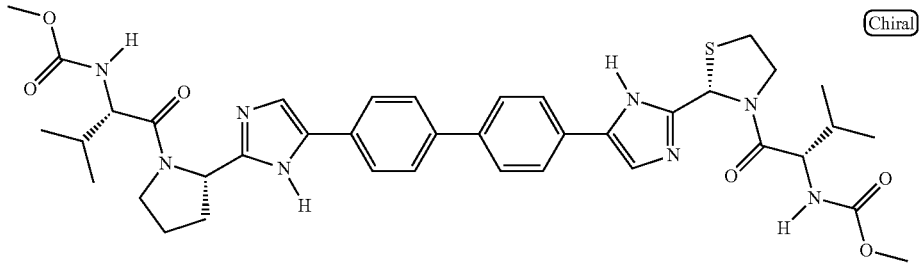
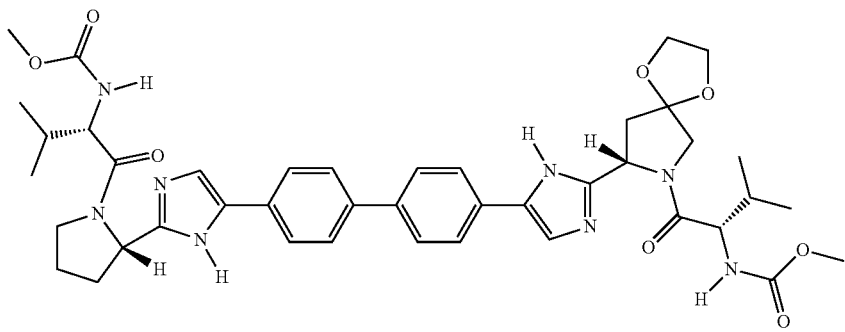
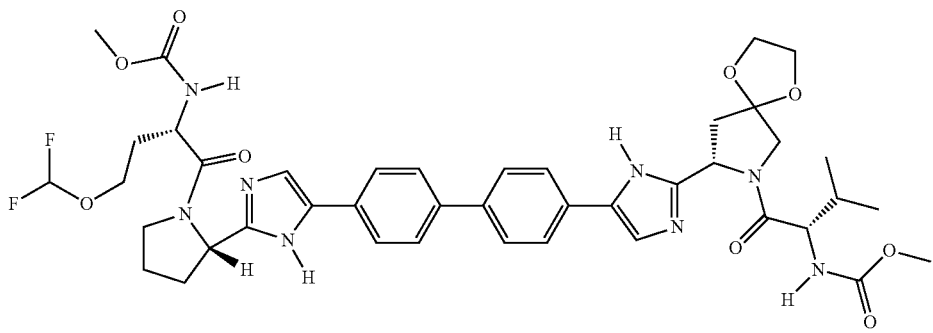

-continued

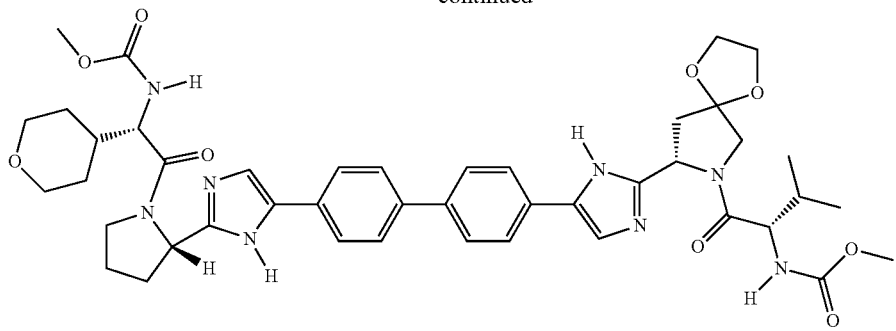

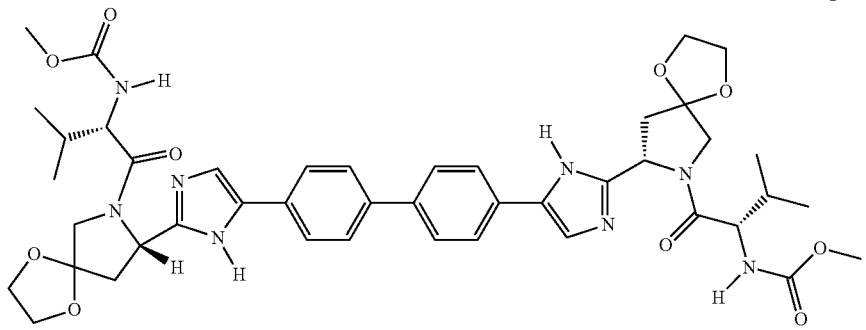

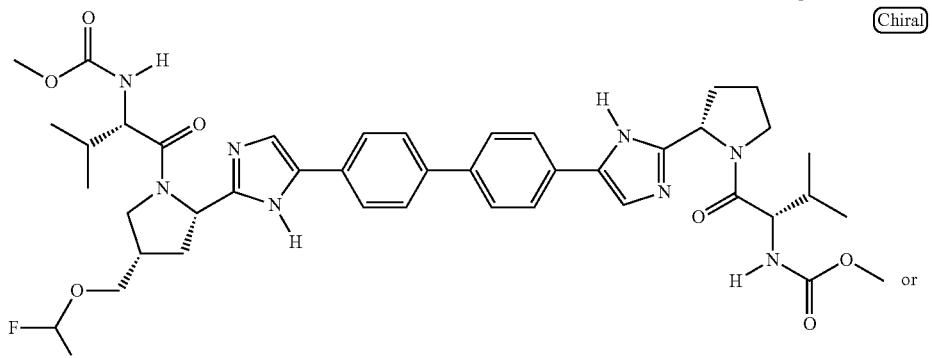

or

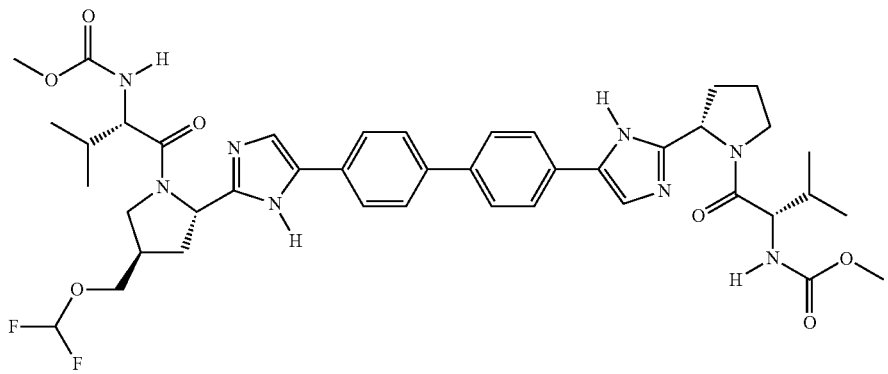

Methods of Inhibition of HCV

Another aspect of the invention relates to methods of inhibiting the activity of HCV comprising the step of treating a sample suspected of containing HCV with a compound or composition of the invention.

Compounds of the invention may act as inhibitors of HCV, as intermediates for such inhibitors or have other utilities as described below. The inhibitors will generally bind to locations on the surface or in a cavity of the liver. Compounds binding in the liver may bind with varying degrees of reversibility. Those compounds binding substantially irreversibly are ideal candidates for use in this method of the invention. Once labeled, the substantially irreversibly binding compounds are useful as probes for the detection of HCV. Accordingly, the invention relates to methods of detecting NS3 in a sample suspected of containing HCV comprising the steps of: treating a sample suspected of containing HCV with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino. In one embodiment the invention provides a compound of any one of formulae (I)-(XIII) that comprises or that is bound or linked to one or more detectable labels. Within the context of the invention samples suspected of containing HCV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HCV. Samples can be contained in any medium including water and organic solvent/water mixtures. Samples include living organisms such as humans, and man made materials such as cell cultures.

The treating step of the invention comprises adding the compound of the invention to the sample or it comprises adding a precursor of the composition to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as observation of the physiological properties of a living organism are also applicable.

Many organisms contain HCV. The compounds of this invention are useful in the treatment or prophylaxis of conditions associated with HCV activation in animals or in man.

However, in screening compounds capable of inhibiting HCV activity it should be kept in mind that the results of enzyme assays may not always correlate with cell culture assays. Thus, a cell based assay should typically be the primary screening tool.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

HCV Combination Therapy

In another embodiment, non-limiting examples of suitable combinations include combinations of one or more compounds of the present invention with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), TMC435350, BI-1335, BI-1230, MK-7009, VBY-376, VX-500, GS-9256, GS-9451, BMS-790052, BMS-605339, PHX-1766, AS-101, YH-5258, YH5530, YH5531, and ITMN-191, 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, BCX-4678, valopicitabine (NM-283), and MK-0608, 7) non-nucleoside inhibitors of HCV NS5B polymerase, e.g., PF-868554, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), BMS-790052, and A-689, 9) TLR-7 agonists, e.g., imiquimod, 852A, GS-9524, ANA-773, ANA-975, AZD-8848 (DSP-3025), and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, and VX-497 (merimepodib).

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound of the present invention can be any agent having a therapeutic effect when used in combination with the compound of the present invention. For example, the therapeutic agent used in combination with the compound of the present invention can be interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, levovirin, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811 and a pharmaceutically acceptable carrier or excipient.

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Combinations of the compounds of formula I and additional active therapeutic agents may be selected to treat patients infected with HCV and other conditions such as HIV infections. Accordingly, the compounds of formula I may be combined with one or more compounds useful in treating HIV, for example HIV protease inhibiting compounds, non-nucleoside inhibitors of HIV reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, R00334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+ emtricitabine, tenofovir disoproxil fumarate+emtricitabine+ efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, levoviron, VX-497, and viramidine (taribavirin) 13) NS5a inhibitors, e.g., A-831, A-689, and BMS-790052, 14) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating Hepatitis C, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 19) pharmacokinetic enhancers, e.g., BAS-100 and SPI452, 20) RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS 119, ALG889, and PA-1050040.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV-inhibitory activity of their own.

Methods for determining stability of compounds in surrogate gastrointestinal secretions are known.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing). Other methods suitable for preparing compounds of the invention are described in International Patent Application Publication Number WO 2006/020276.

A number of exemplary methods for the preparation of the compositions of the invention are provided in the schemes and examples below. These methods are intended to illustrate the nature of such preparations and are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis is used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the Examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113, 3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched substrate. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Schemes and Examples

General aspects of these exemplary methods are described below and in the Examples. Each of the products of the following processes is optionally separated, isolated, and/or purified prior to its use in subsequent processes.

A number of exemplary methods for the preparation of compounds of the invention are provided herein, for example, in the Examples below. These methods are intended to illustrate the nature of such preparations and are not intended to limit the scope of applicable methods. Certain compounds of the invention can be used as intermediates for the preparation of other compounds of the invention. In the exemplary methods described herein, the fragment E-V— can also be written as R9-. PG represents a protecting group common for the given functional group that it is attached. The installation and removal of the protecting group can be accomplished using standard techniques, such as those described in Wuts, P. G. M., Greene, T. *Protective Groups in Organic Synthesis*, 4th ed.; John Wiley & Sons, Inc.: Hoboken, N.J., 2007.

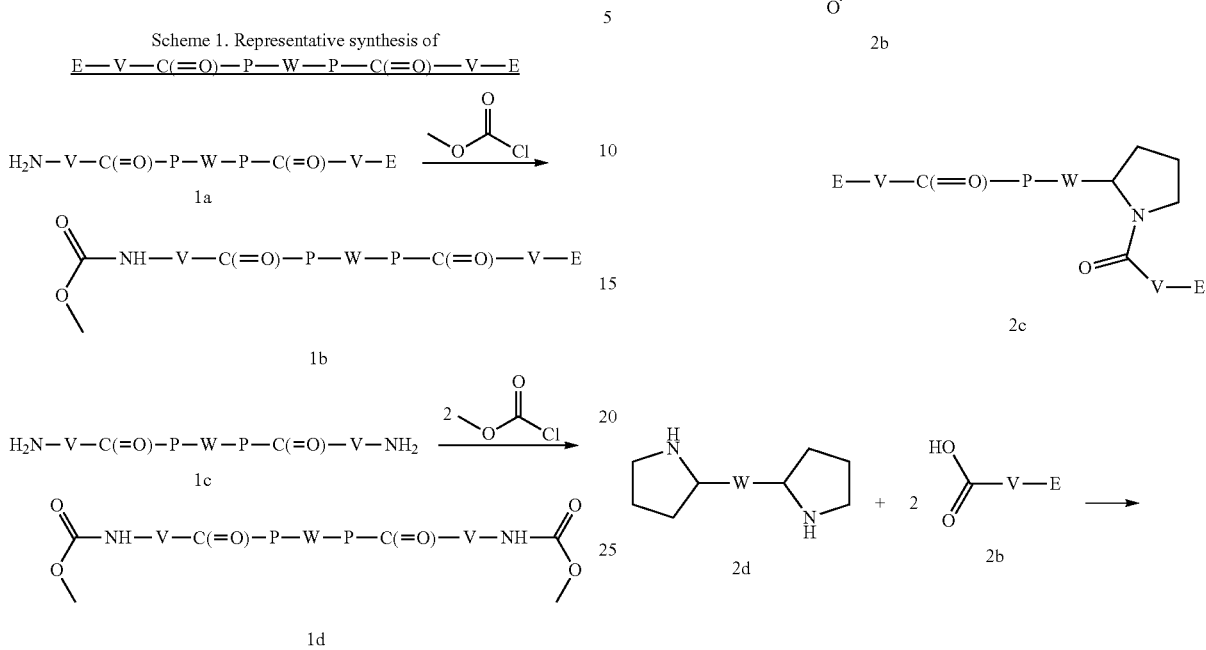

Scheme 1 shows a general synthesis of an E-V—C(=O)—P—W—P—C(=O)—V-E molecule of the invention wherein, for illustrative purposes, E is methoxycarbonylamino. The treatment of either 1a or 1c with one or two equivalents respectively of methyl chloroformate under basic conditions (e.g. sodium hydroxide) provides the molecule 1b or 1d.

Scheme 2 shows a general synthesis of an E-V—C(=O)—P—W—P—C(=O)—V-E molecule of the invention wherein, for illustrative purposes, P is pyrrolidine. Coupling of amine 2a with acid 2b is accomplished using a peptide coupling reagent (e.g. HATU) to afford 2c. Alternatively, amine 2d is coupled with two equivalents of 2b under similar conditions to provide 2e.

Scheme 3 shows a general synthesis of an E-V—C(=O)—P—W—P—C(=O)—V-E molecule of the invention wherein, for illustrative purposes, W is a four aromatic ring unit constructed via a transition metal mediated cross-coupling reaction. For illustrative purposes, the Suzuki reaction is employed to couple a boronic ester to either an aryl- or heteroarylbromide. Boronic ester 3b is coupled with an appropriate coupling partner (e.g. 3a) using a palladium catalyst, such as Pd(PPh3)4, to afford 3c. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings.

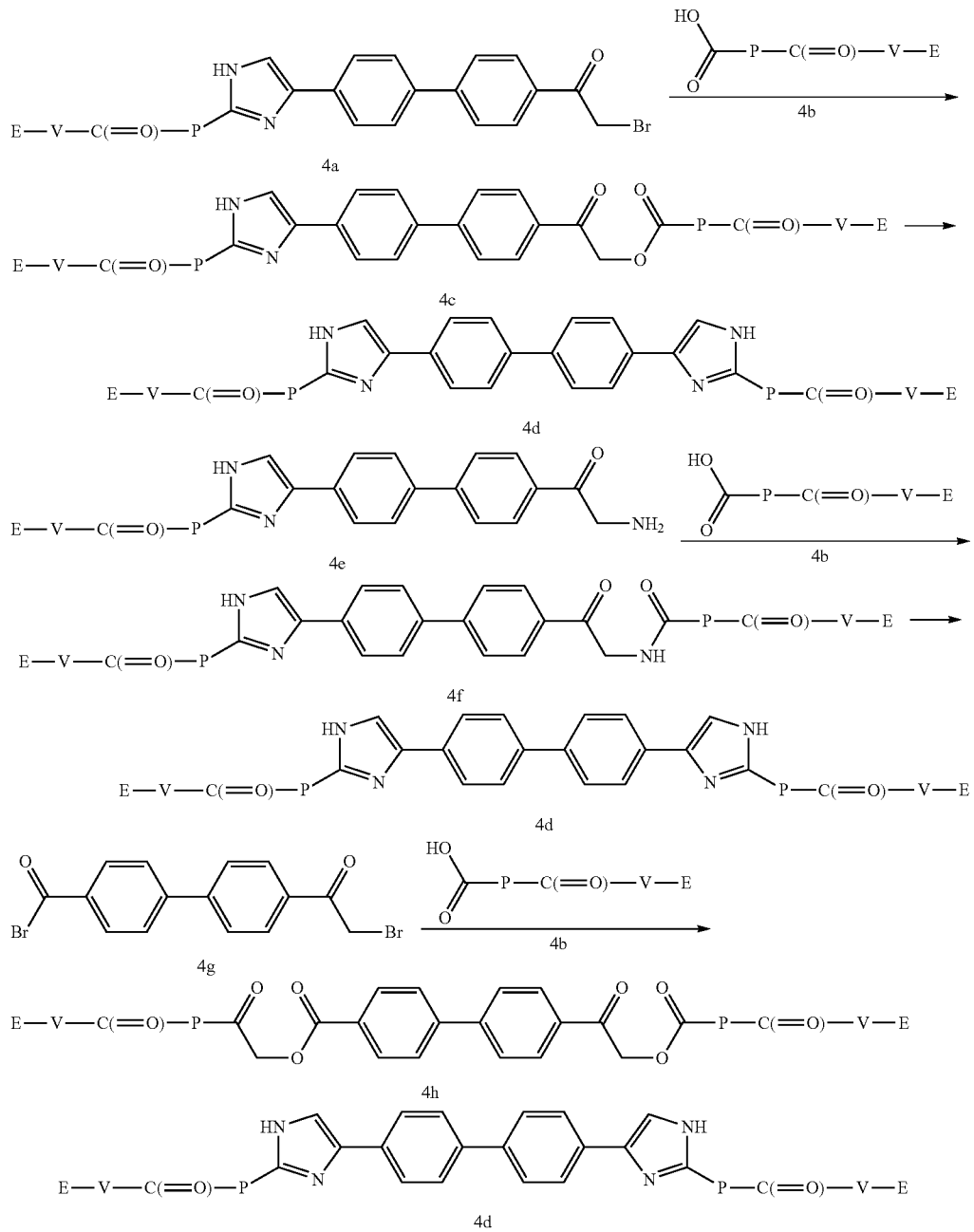

Scheme 4 shows a general synthesis of an E-V—C(=O)—P—W—P—C(=O)—V-E molecule of the invention wherein, for illustrative purposes, W is a four aromatic ring unit constructed by the formation of a substituted imidazole ring. The formation of the imidazole is accomplished by coupling the acid 4b with an α-haloketone, such as α-bromoketone 4a, under basic conditions (e.g. Et₃N) to afford 4c. Alternatively, the acid 4b is coupled with an α-aminoketone 4e, under amide formation conditions (e.g. EDC, Et₃N) to afford 4f. Reaction of 4c or 4f with an amine or amine salt (e.g. ammonium acetate) affords the imidazole containing molecule 4d.

The formation of multiple imidazoles is performed in the same manner, starting with a bis-α-haloketone such as α-bromoketone 4g, to provide molecule 4d.

aromatic ring unit constructed by the formation of a substituted benzimidazole ring. The formation of the benzimidazole is accomplished by coupling the acid 5b with an arylamine 5a, using a peptide coupling reagent such as HATU, to afford 5c. Cyclization of the amide 5c in the presence an acid (such as acetic acid) affords the benzimidazole containing molecule 5d.

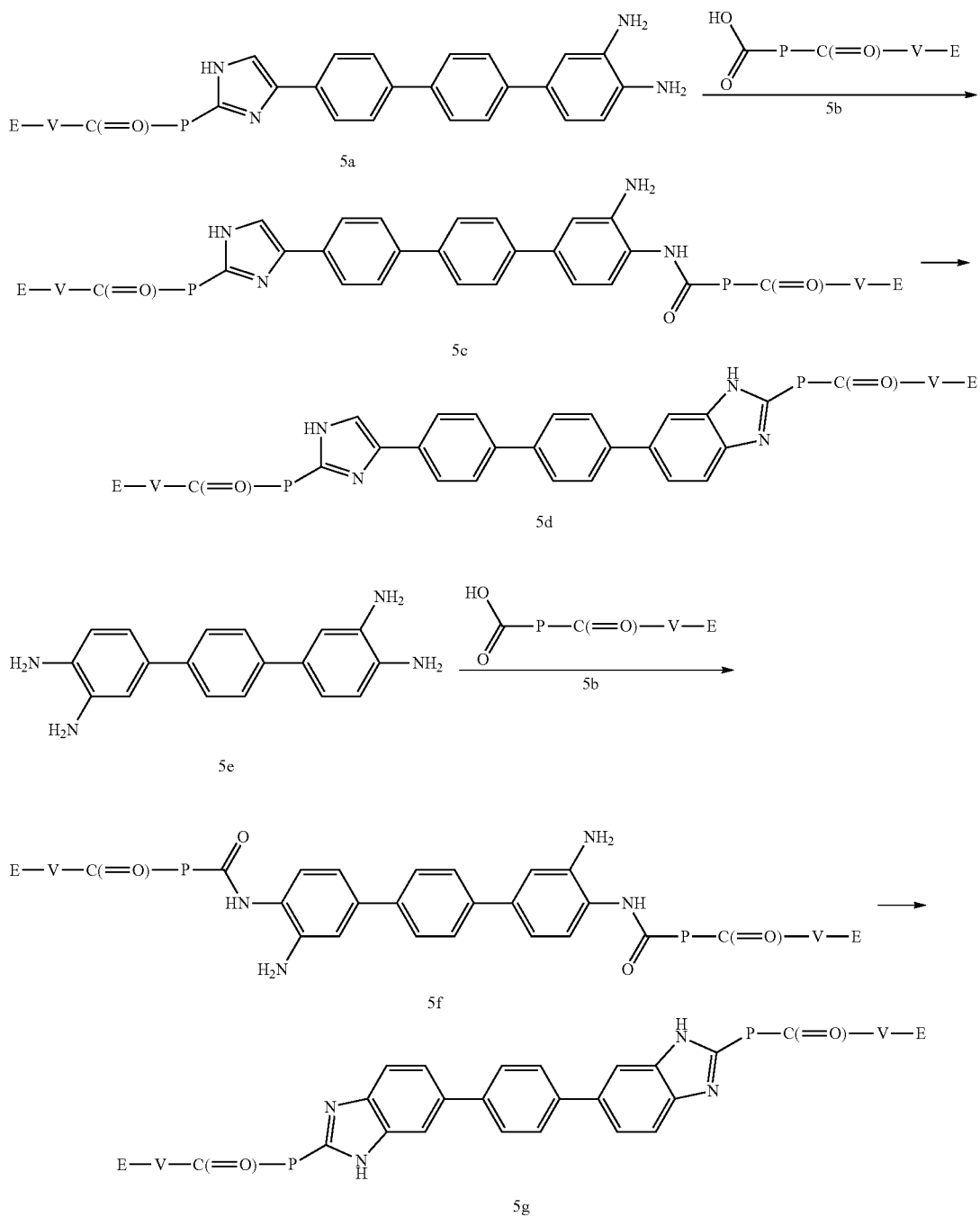

Scheme 5 shows a general synthesis of an E-V—C(=O)—P—W—P—C(=O)—V-E molecule of the invention wherein, for illustrative purposes, W is a three or four The formation of multiple benzimidazoles is performed in the same manner, starting with a bis-diamine such as 5f, to provide molecule 5g.

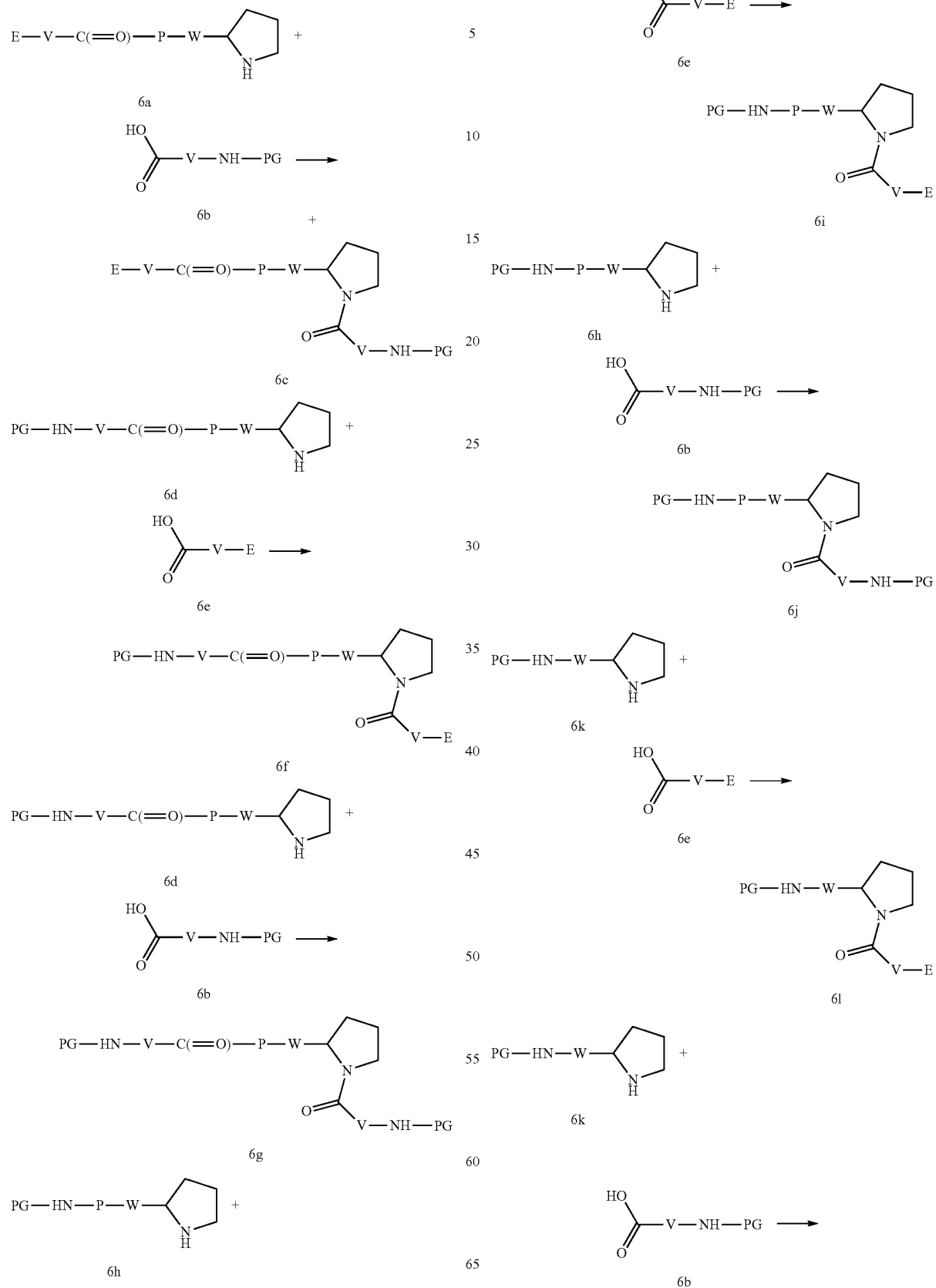

-continued

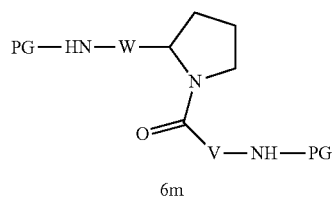

Scheme 6 shows a general synthesis of an R¹—V—C(=O)—P—R² intermediate wherein, for illustrative purposes, P is pyrrolidine, R¹ is a generic group that is depicted as either -E or a amino protecting group, and R² is a generic group that is depicted as —W—P—C(=O)—V-E, —W—P—C(=O)—V-NH-PG, —W—P-NH-PG, or —W—NH-PG. Coupling of amine 6a (or 6d, 6h, 6k) with acid 6b or 6e is accomplished using a peptide coupling reagent (e.g. HATU) to afford 6c (or 6f, 6g, 6i, 6j, 6l, 6m) respectively.

Scheme 7. Representative synthesis of E—V—C(=O)—R¹

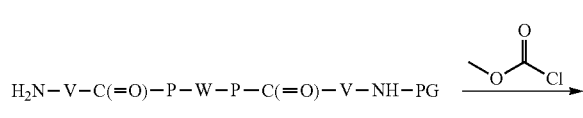

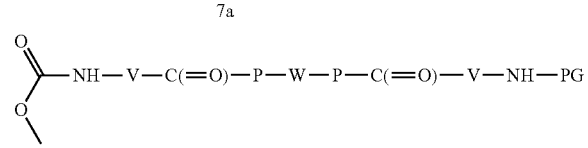

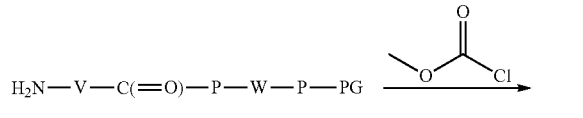

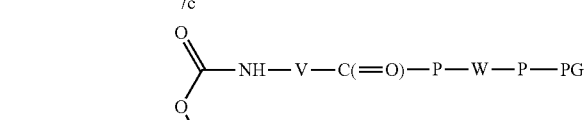

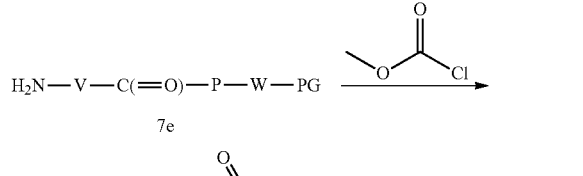

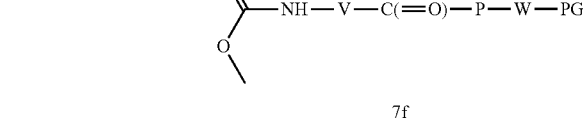

-continued

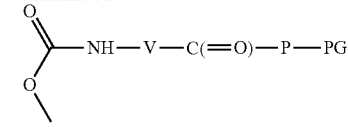

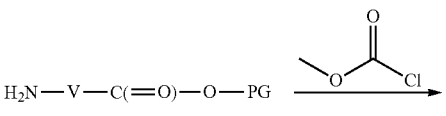

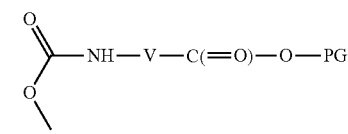

Scheme 7 shows a general synthesis of an E-V—C(=O)—R¹ intermediate wherein, for illustrative purposes, E is methoxycarbonylamino and R¹ is a generic group that is depicted as either —P—W—P—C(=O)—V-NH-PG, —P—W—P-PG, —P—W-PG, —P-PG, or —O-PG. Treatment of 7a (or 7c, 7e, 7g, 7i) with methyl chloroformate under basic conditions (e.g. sodium hydroxide) provides the molecule 7b (or 7d, 7f, 7h, 7j).

Scheme 8. Representative synthesis of R¹—P—R²

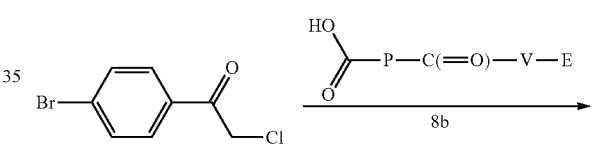

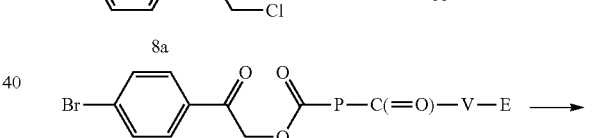

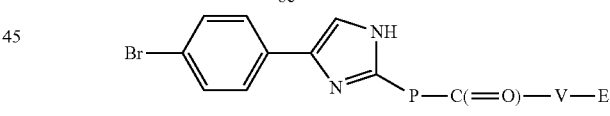

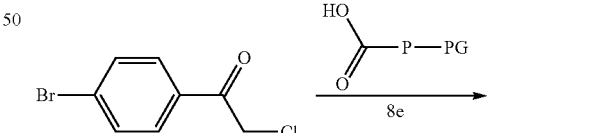

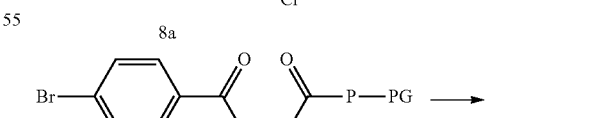

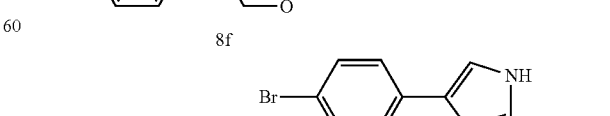

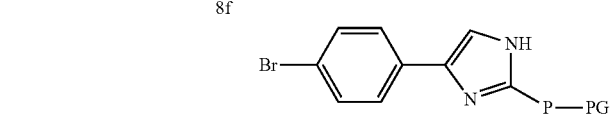

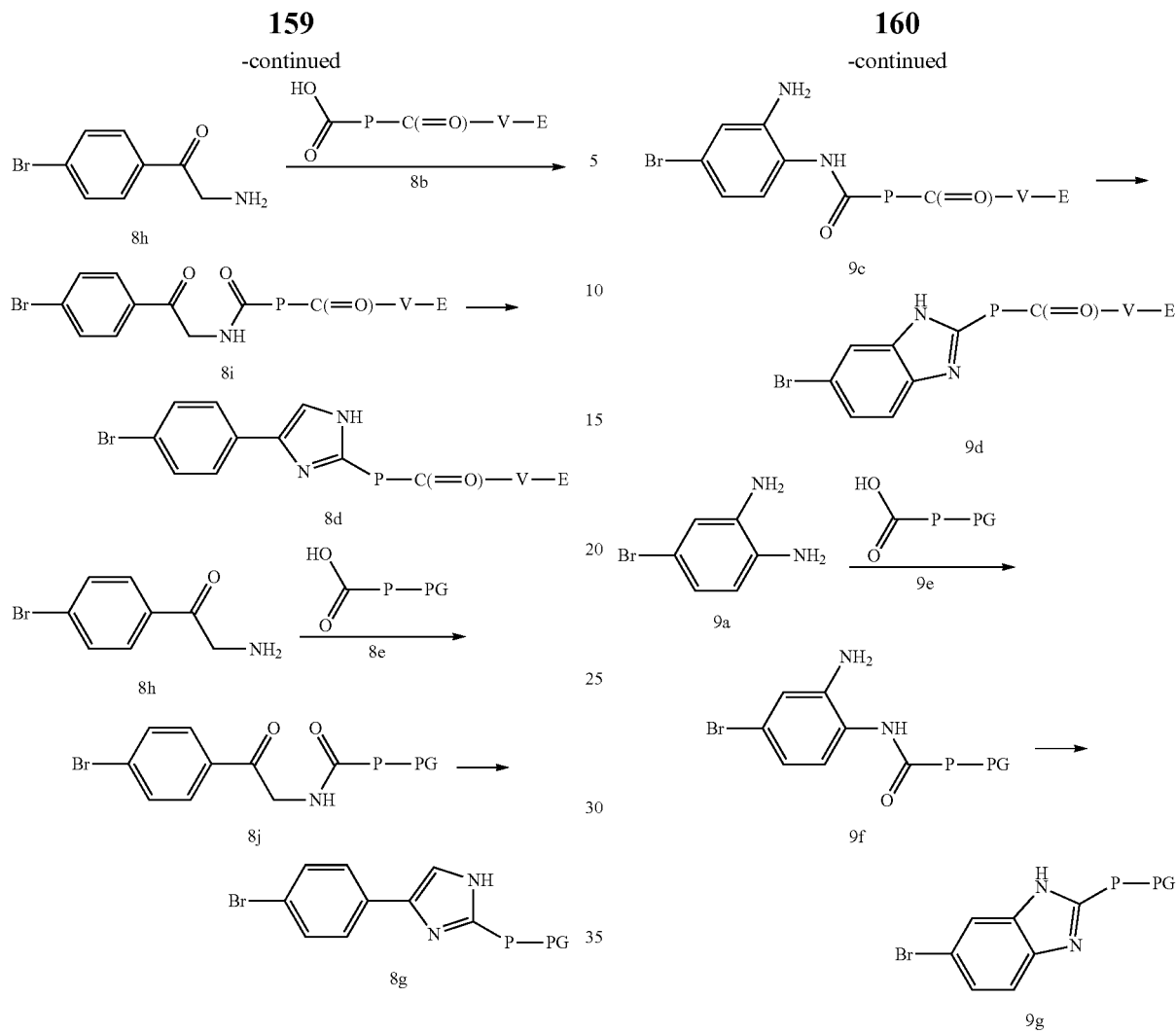

Scheme 8 shows a general synthesis of an $R^1$—P—$R^2$ intermediate wherein, for illustrative purposes, $R^1$ is —C(=O)—V-E or a protecting group and $R^2$ is a substituted imidazole. The formation of the imidazole is accomplished by coupling the acid 8b or 8e with an α-haloketone, such as α-chloroketone 8a, under basic conditions (e.g. $Et_3N$) to afford 8c or 8f. Alternatively, the acid 8b or 8e is coupled with an α-aminoketone 8h, under amide formation conditions (e.g. EDC, $Et_3N$) to afford 8i or 8j. Reaction of 8c (or 8f, 8i, 8j) with an amine or amine salt (e.g. ammonium acetate) affords the imidazole containing molecule 8d or 8g. The formation of multiple imidazoles is performed in the same manner, starting with a bis-α-haloketone to provide the corresponding bis-imidazole.

Scheme 9 shows a general synthesis of an $R^1$—P—$R^2$ intermediate wherein, for illustrative purposes, $R^1$ is —C(=O)—V-E or a protecting group and $R^2$ is a substituted benzamidazole. The formation of the benzimidazole is accomplished by coupling the acid 9b or 9e with an arylamine 9a, using a peptide coupling reagent such as HATU, to afford 9c or 9d. Cyclization of the amide in the presence an acid (such as acetic acid) affords the benzimidazole containing molecule 9d or 9g.

The formation of multiple benzimidazoles is performed in the same manner, starting with a bis-diamine to provide the corresponding bis-benzamidazole.

Scheme 9. Representative synthesis of $R^1$—P—$R^2$

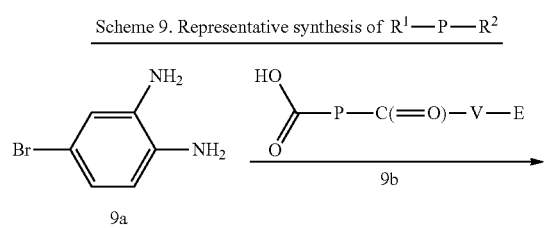

Scheme 10. Representative synthesis of $R^1$—P—$R^2$

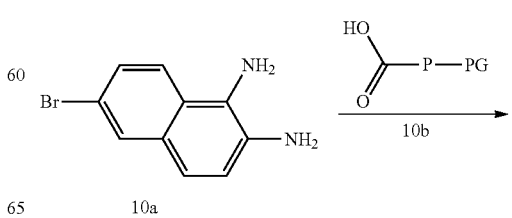

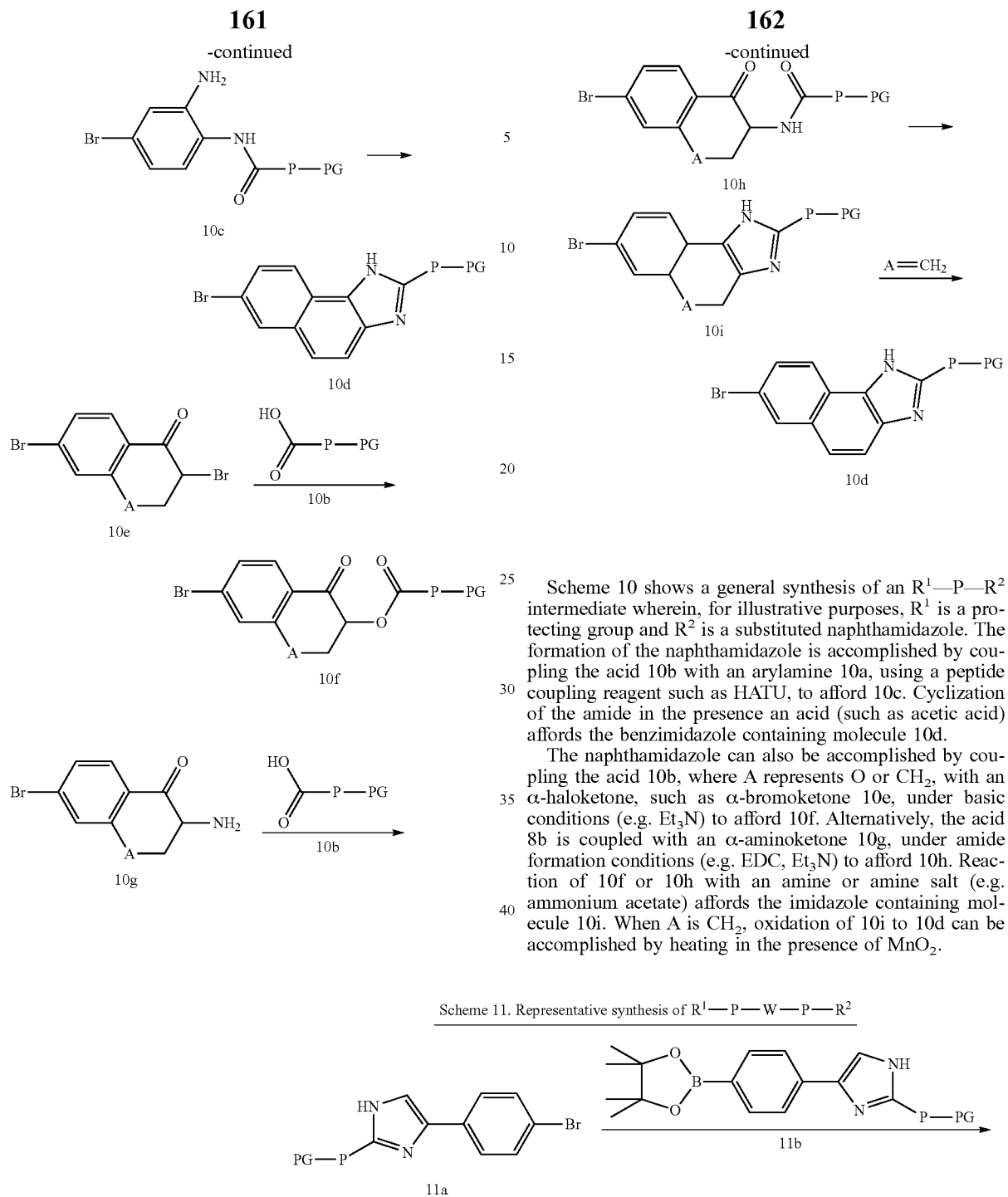

Scheme 10 shows a general synthesis of an $R^1$—P—$R^2$ intermediate wherein, for illustrative purposes, $R^1$ is a protecting group and $R^2$ is a substituted naphthamidazole. The formation of the naphthamidazole is accomplished by coupling the acid 10b with an arylamine 10a, using a peptide coupling reagent such as HATU, to afford 10c. Cyclization of the amide in the presence an acid (such as acetic acid) affords the benzimidazole containing molecule 10d.

The naphthamidazole can also be accomplished by coupling the acid 10b, where A represents O or $CH_2$, with an α-haloketone, such as α-bromoketone 10e, under basic conditions (e.g. $Et_3N$) to afford 10f. Alternatively, the acid 8b is coupled with an α-aminoketone 10g, under amide formation conditions (e.g. EDC, $Et_3N$) to afford 10h. Reaction of 10f or 10h with an amine or amine salt (e.g. ammonium acetate) affords the imidazole containing molecule 10i. When A is $CH_2$, oxidation of 10i to 10d can be accomplished by heating in the presence of $MnO_2$.

Scheme 11. Representative synthesis of $R^1$—P—W—P—$R^2$

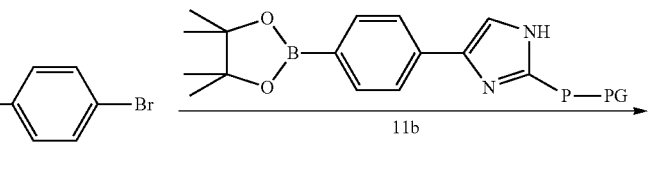

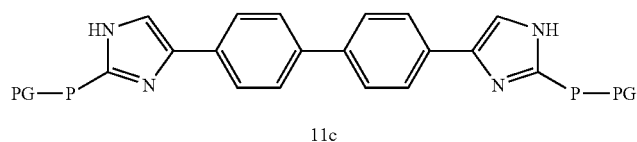

Scheme 11 shows a general synthesis of an $R^1$—P—W—P—$R^2$ intermediate of the invention wherein, for illustrative purposes, $R^1$ and $R^2$ are independent protecting groups and W is a four aromatic ring unit constructed via a transition metal mediated cross-coupling reaction. For illustrative purposes, the Suzuki reaction is employed to couple a boronic ester to either an aryl- or heteroarylbromide. Boronic ester 11b is coupled with an appropriate coupling partner (e.g. 11a) using a palladium catalyst, such as Pd(PPh3)4, to afford 11c. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings.

Scheme 12. Representative synthesis of $R^1$—P—$R^2$

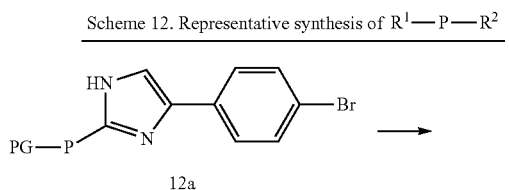

12a

-continued

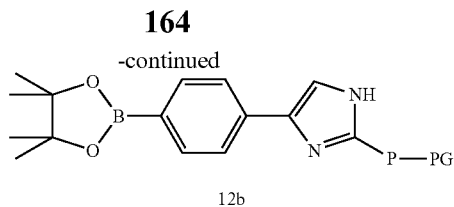

12b

Scheme 12 shows a general synthesis of an $R^1$—P—$R^2$ intermediate of the invention wherein, for illustrative purposes, $R^1$ is a generic group that is depicted as a protecting group and $R^2$ is a generic group that is depicted as an aryl boronic ester. A transition metal-mediated cross-coupling reaction is utilized to install the boronic ester. Treatment of the corresponding aryl bromide with a palladium catalyst, such as $PdCl_2$(dppf), and a boron source such as bis(pinacolato)diboron provides the boronic ester 12b.

Scheme 13. Representative synthesis of $R^{1*}$—P—W—P—$R^2$

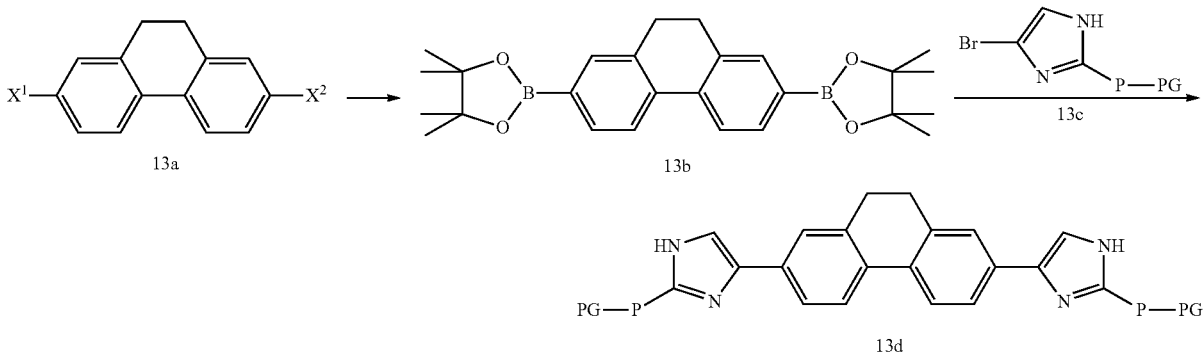

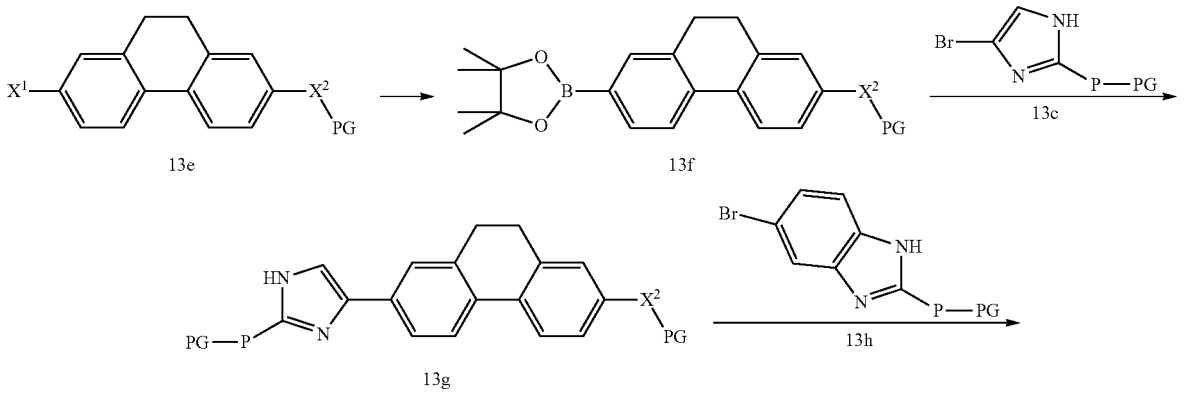

Scheme 13 shows a general synthesis of an R¹—P—W—P—R² intermediate of the invention wherein, for illustrative purposes, R¹ and R² are independent protecting groups and W is a three aromatic ring unit constructed via a transition metal mediated cross-coupling reaction. For illustrative purposes, W is constructed from a tricyclic aromatic ring, wherein X¹ and X² are independent halogens or halogen equivalents that may be suitably protected. For illustrative purposes, a transition metal-mediated cross-coupling reaction is utilized to install the boronic ester and the Suzuki reaction is employed to couple the boronic ester to a heteroarylbromide. Treatment of the 13a or 13e with a palladium catalyst, such as PdCl$_2$(dppf), and a boron source such as bis(pinacolato)diboron provides the boronic ester 13b or 13f. The boronic ester is coupled with an appropriate coupling partner (e.g. 13c or 13h) using a palladium catalyst, such as Pd(PPh3)4, to afford 13d or 13i. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings.

Scheme 14. Representative synthesis of R¹—P—W—P—R²

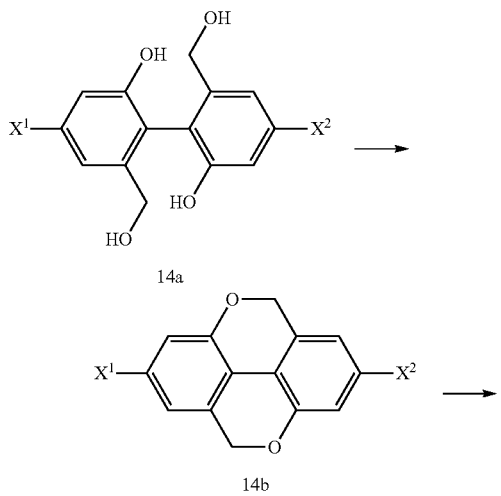

14a

14b

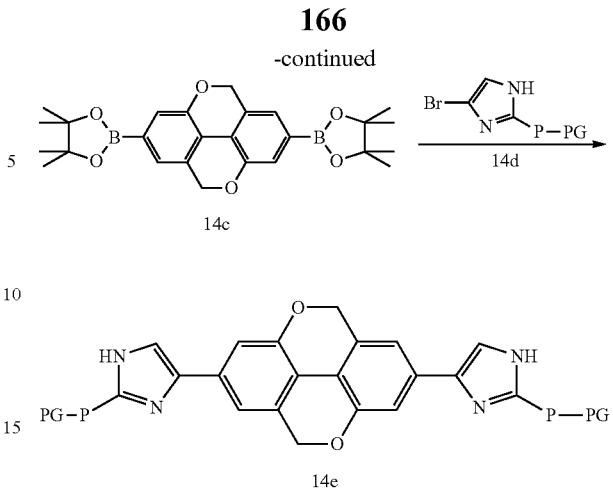

14c

14e

Scheme 14 shows a general synthesis of an R¹—P—W—P—R² intermediate of the invention wherein, for illustrative purposes, R¹ and R² are independent protecting groups and W is a three aromatic ring unit constructed via a transition metal mediated cross-coupling reaction. For illustrative purposes, W is constructed from a tetracyclic aromatic ring, wherein X¹ and X² are independent halogens or halogen equivalents that may be suitably protected. The construction of the tetracyclic compound 14b can be accomplished from a suitably functionalized biphenyl intermediate (e.g. 14a) by activation with PBr$_3$ followed by treatment with a base, such as cesium carbonate. For illustrative purposes, a transition metal-mediated cross-coupling reaction is utilized to install the boronic ester and the Suzuki reaction is employed to couple the boronic ester to a heteroarylbromide. Treatment of the 14b with a palladium catalyst, such as PdCl$_2$(dppf), and a boron source such as bis(pinacolato)diboron provides the boronic ester 14c. The boronic ester is coupled with an appropriate coupling partner (e.g. 14d) using a palladium catalyst, such as Pd(PPh3)4, to afford 14e. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings.

Scheme 15. Representative synthesis of R¹—P—W—P—R²

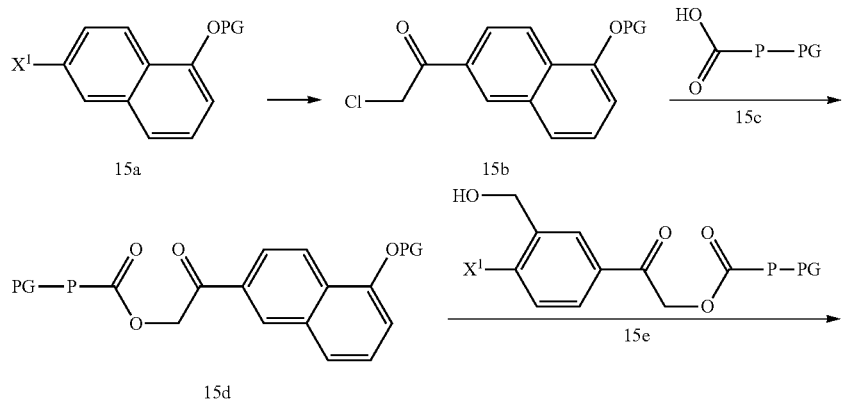

15a      15b      15c 15d      15e

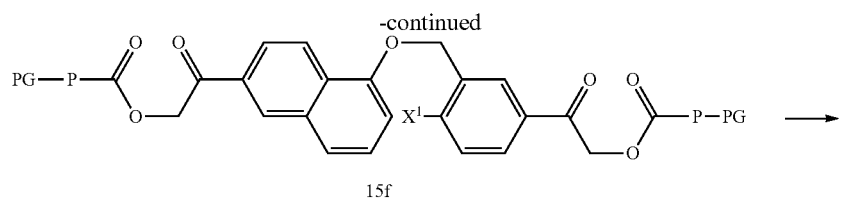

15f

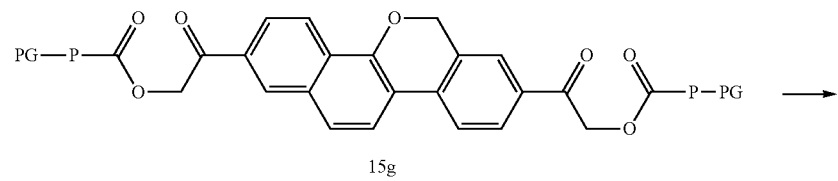

15g

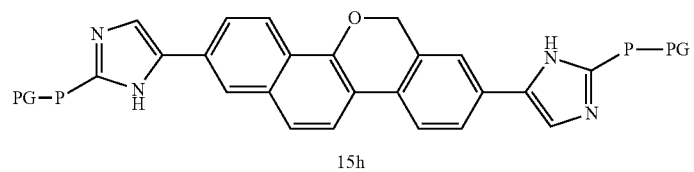

15h

Scheme 15 shows a general synthesis of an $R^1$—P—W—P—$R^2$ intermediate of the invention wherein, for illustrative purposes, $R^1$ and $R^2$ are independent protecting groups and W is a three aromatic ring unit constructed via a transition metal mediated cyclization. For illustrative purposes, W includes a tetracyclic aromatic ring. Metalation of 15a with either n-BuLi or i-PrMgCl, followed by treatment with 2-Chloro-N-methoxy-N-methyl-acetamide provides the α-haloketone 15b. Treatment with an acid, such as 15c, under basic conditions (e.g. $Et_3N$) provides the ester 15d. Activation of 15e, and treatment with 15d, under basic conditions provides the ether 15f. Cyclization in the presence of a transition metal catalyst, such as $Pd(OAc)_2$ provides 15g. Reaction of 15g with an amine or amine salt (e.g. ammonium acetate) affords the imidazole containing molecule 15h.

tion wherein, for illustrative purposes, W is a three aromatic ring unit constructed via a transition metal mediated cross-coupling reaction. For illustrative purposes, the Suzuki reaction is employed to couple a boronic ester to either an aryl- or heteroarylbromide. Boronic ester 16b is coupled with an appropriate coupling partner (e.g. 16a) using a palladium catalyst, such as Pd(PPh3)4, to afford 16c. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings. For the preparation of alternate three aromatic ring containing W groups, this general scheme can

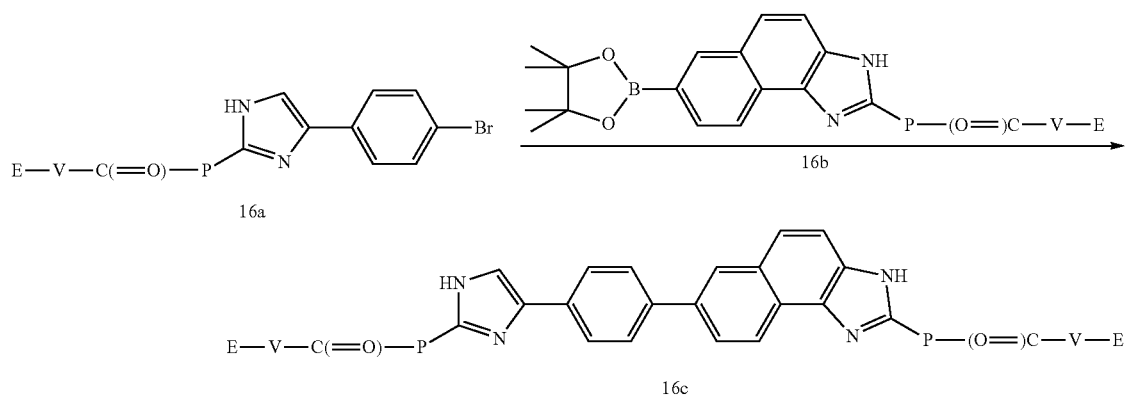

Scheme 16. Representative synthesis of
E—V—C(=O)—P—W—P—C(=O)—V—E

Scheme 16 shows a general synthesis of an E-V—C(=O)—P—W—P—C(=O)—V-E molecule of the invention be applied through the choice of the appropriate cross coupling partners and reagents.

Scheme 17. Representative synthesis of R¹—P—W—P—R²

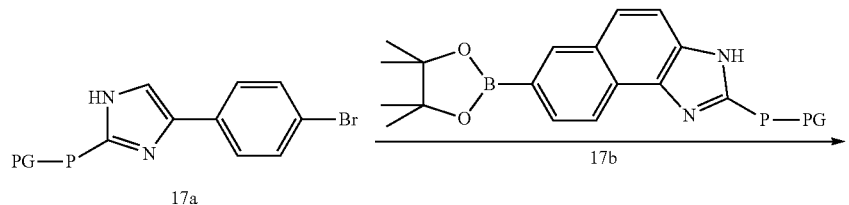

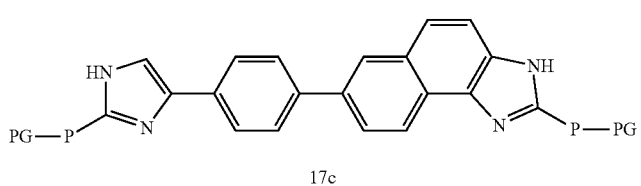

Scheme 17 shows a general synthesis of an R¹—P—W—P—R² intermediate of the invention wherein, for illustrative purposes, R¹ and R² are independent protecting groups and W is a three aromatic ring unit constructed via a transition metal mediated cross-coupling reaction. For illustrative purposes, the Suzuki reaction is employed to couple a boronic ester to either an aryl- or heteroarylbromide. Boronic ester 17b is coupled with an appropriate coupling partner (e.g. 17a) using a palladium catalyst, such as Pd(PPh$_3$)$_4$, to afford 17c. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings. For the preparation of alternate three aromatic ring containing W groups, this general scheme can be applied through the choice of the appropriate cross coupling partners and reagents.

Scheme 18 shows a general synthesis of an E-V—C(=O)—P—W—P—C(=O)—V-E molecule of the invention wherein, for illustrative purposes, W is a two aromatic ring unit constructed via a transition metal mediated cross-coupling reaction. For illustrative purposes, the Suzuki reaction is employed to couple a boronic ester to either an aryl- or heteroarylbromide. Boronic ester 18b is coupled with an appropriate coupling partner (e.g. 18a) using a palladium catalyst, such as Pd(PPh3)4, to afford 18c. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings. For the preparation of alternate two aromatic ring containing W groups, this general scheme can be applied through the choice of the appropriate cross coupling partners and reagents.

Scheme 18. Representative synthesis of
E—V—C(=O)—P—W—P—C(=O)—V—E

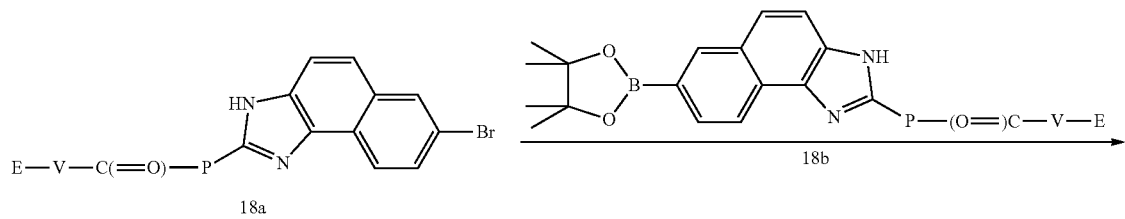

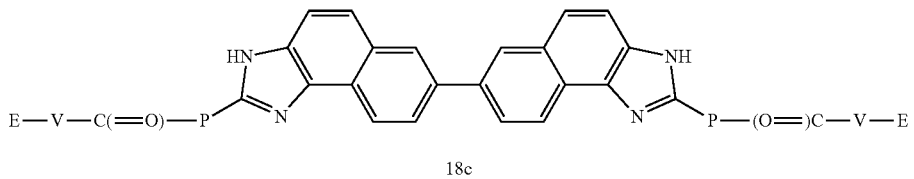

Scheme 19. Representative synthesis of R¹—P—W—P—R²

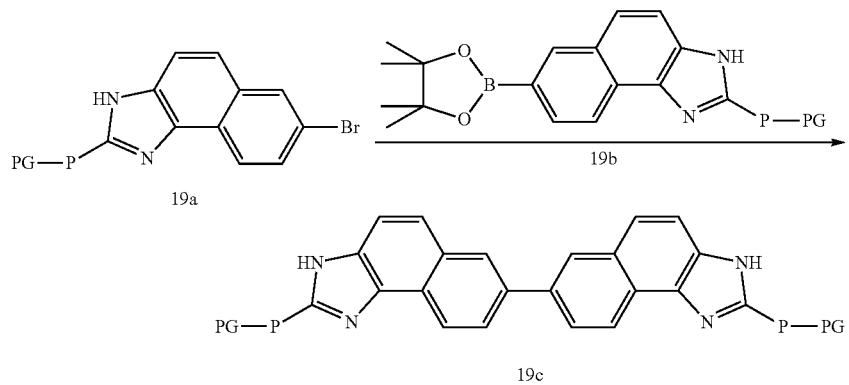

Scheme 19 shows a general synthesis of an R¹—P—W—P—R² intermediate of the invention wherein, for illustrative purposes, R¹ and R² are independent protecting groups and W is a two aromatic ring unit constructed via a transition metal mediated cross-coupling reaction. For illustrative purposes, the Suzuki reaction is employed to couple a boronic ester to either an aryl- or heteroarylbromide. Boronic ester 19b is coupled with an appropriate coupling partner (e.g. 19a) using a palladium catalyst, such as Pd(PPh₃)₄, to afford 19c. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings. For the preparation of alternate two aromatic ring containing W groups, this general scheme can be applied through the choice of the appropriate cross coupling partners and reagents.

Scheme 20. Representative synthesis of R¹—P—W—P—R²

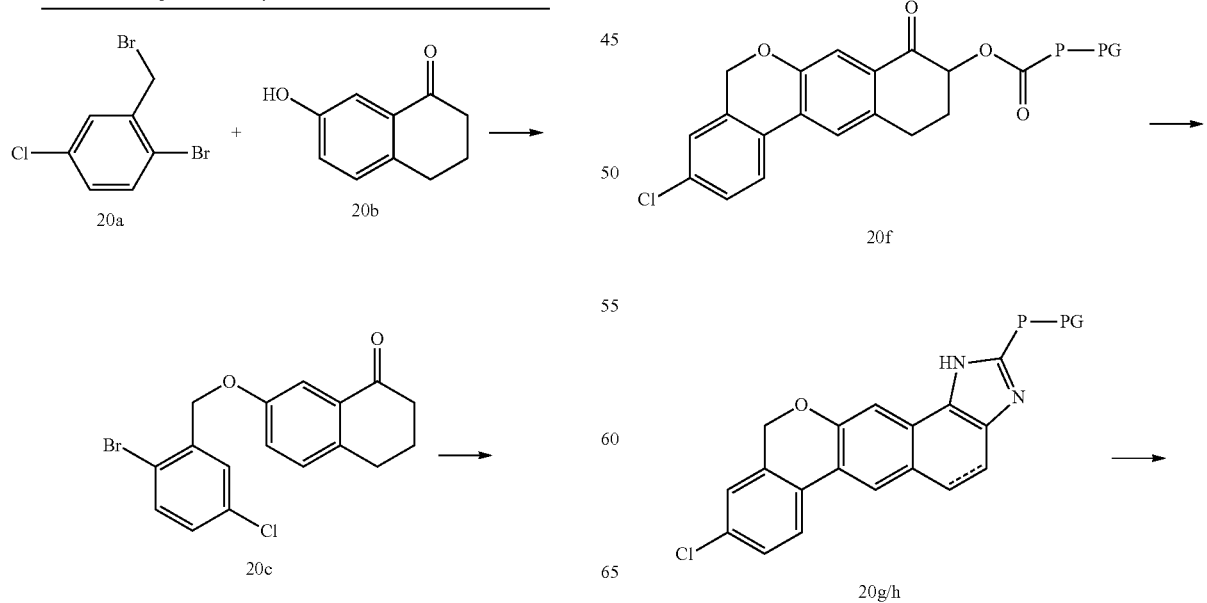

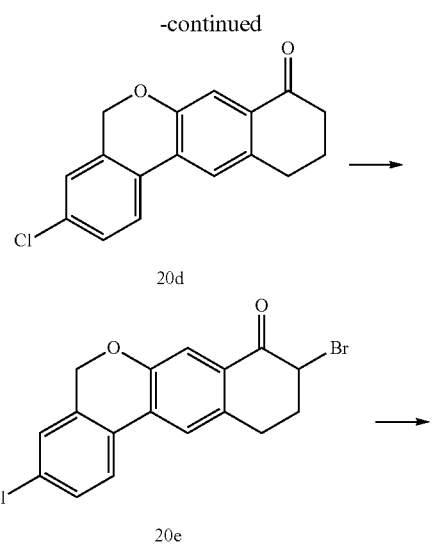

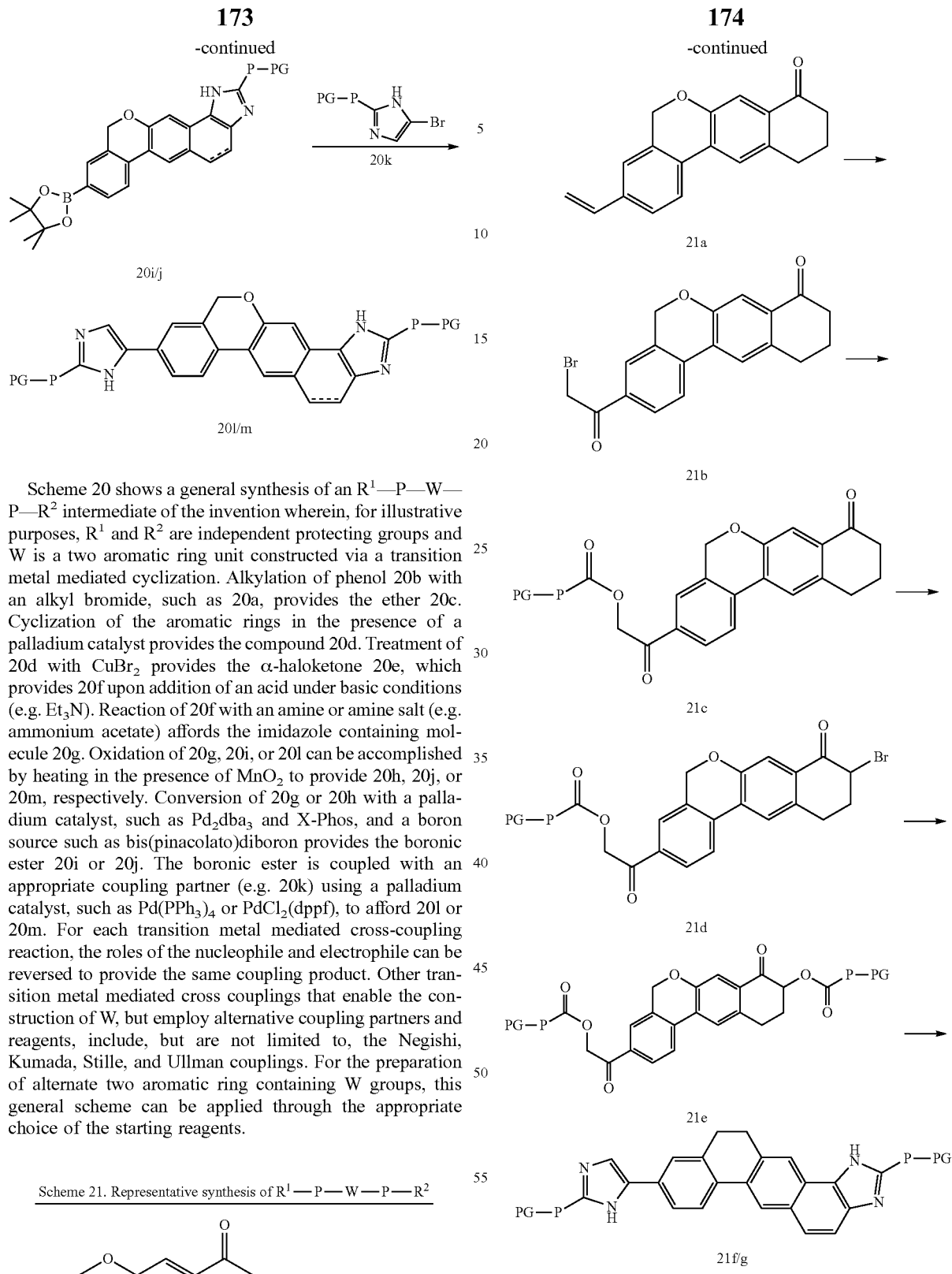

Scheme 20 shows a general synthesis of an R¹—P—W—P—R² intermediate of the invention wherein, for illustrative purposes, $R^1$ and $R^2$ are independent protecting groups and W is a two aromatic ring unit constructed via a transition metal mediated cyclization. Alkylation of phenol 20b with an alkyl bromide, such as 20a, provides the ether 20c. Cyclization of the aromatic rings in the presence of a palladium catalyst provides the compound 20d. Treatment of 20d with $CuBr_2$ provides the α-haloketone 20e, which provides 20f upon addition of an acid under basic conditions (e.g. $Et_3N$). Reaction of 20f with an amine or amine salt (e.g. ammonium acetate) affords the imidazole containing molecule 20g. Oxidation of 20g, 20i, or 20l can be accomplished by heating in the presence of $MnO_2$ to provide 20h, 20j, or 20m, respectively. Conversion of 20g or 20h with a palladium catalyst, such as $Pd_2dba_3$ and X-Phos, and a boron source such as bis(pinacolato)diboron provides the boronic ester 20i or 20j. The boronic ester is coupled with an appropriate coupling partner (e.g. 20k) using a palladium catalyst, such as $Pd(PPh_3)_4$ or $PdCl_2(dppf)$, to afford 20l or 20m. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings. For the preparation of alternate two aromatic ring containing W groups, this general scheme can be applied through the appropriate choice of the starting reagents.

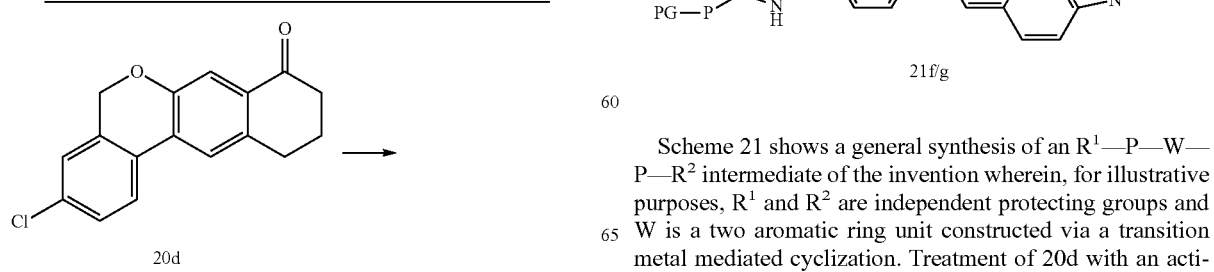

Scheme 21 shows a general synthesis of an R¹—P—W—P—R² intermediate of the invention wherein, for illustrative purposes, $R^1$ and $R^2$ are independent protecting groups and W is a two aromatic ring unit constructed via a transition metal mediated cyclization. Treatment of 20d with an activated vinyl reagent (e.g. potassium vinyltrifluoroborate) in the presence of a palladium catalyst (e.g. palladium acetate and S-Phos) provides the vinyl compound 21a. Conversion to the corresponding α-halo ketone can be accomplished by bromination with N-bromosuccinimide, followed by oxidation with MnO₂. Displacement of the α-halo ketone proceeds by the addition of an acid under basic conditions (e.g. Et₃N). Bromination of 21d proceeds upon treatment with pyridinium tribromide, and is followed by the addition of a second acid under basic conditions to provide the diester 21e. Reaction of 21e with an amine or amine salt (e.g. ammonium acetate) affords the imidazole containing molecule 21f. Oxidation of 21f can be accomplished in the presence of MnO₂ to provide 21g.

Scheme 22 shows a general synthesis of an E-V—C(=O)—P—W—P—R intermediate of the invention wherein, for illustrative purposes, R is a protecting group and W is a two aromatic ring unit. Displacement of the α-halo ketone 21b proceeds by the addition of an acid under basic conditions (e.g. Et₃N). Bromination of 22b proceeds upon treatment with pyridinium tribromide, and is followed by the addition of a second acid under basic conditions to provide the diester 22c. Reaction of 22c with an amine or amine salt (e.g. ammonium acetate) affords the imidazole containing molecule 22d. Oxidation of 22d can be accomplished in the presence of MnO₂ to provide 22e.

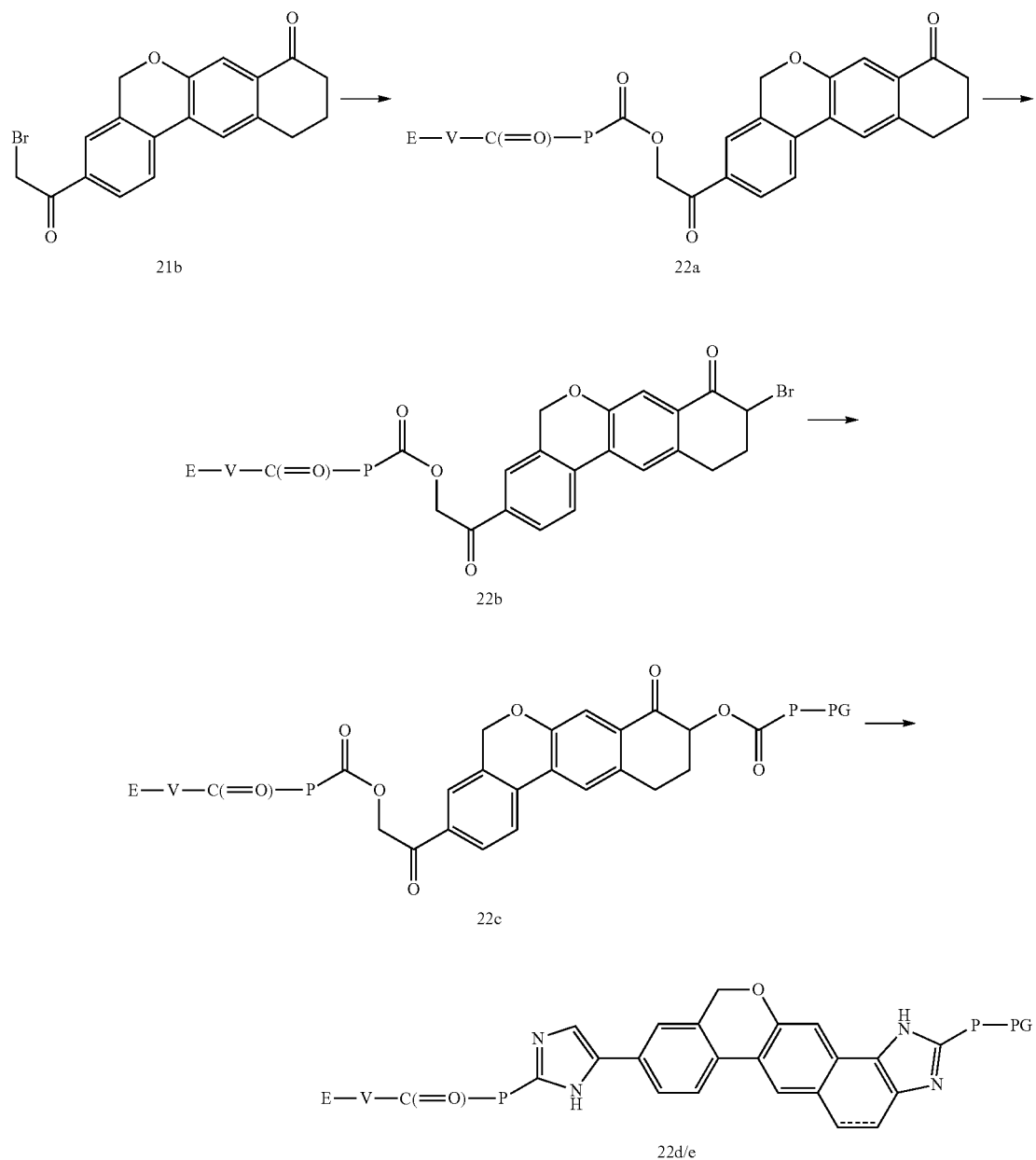

Scheme 23. Representative synthesis of R—P—W—P—C(=O)—V—E

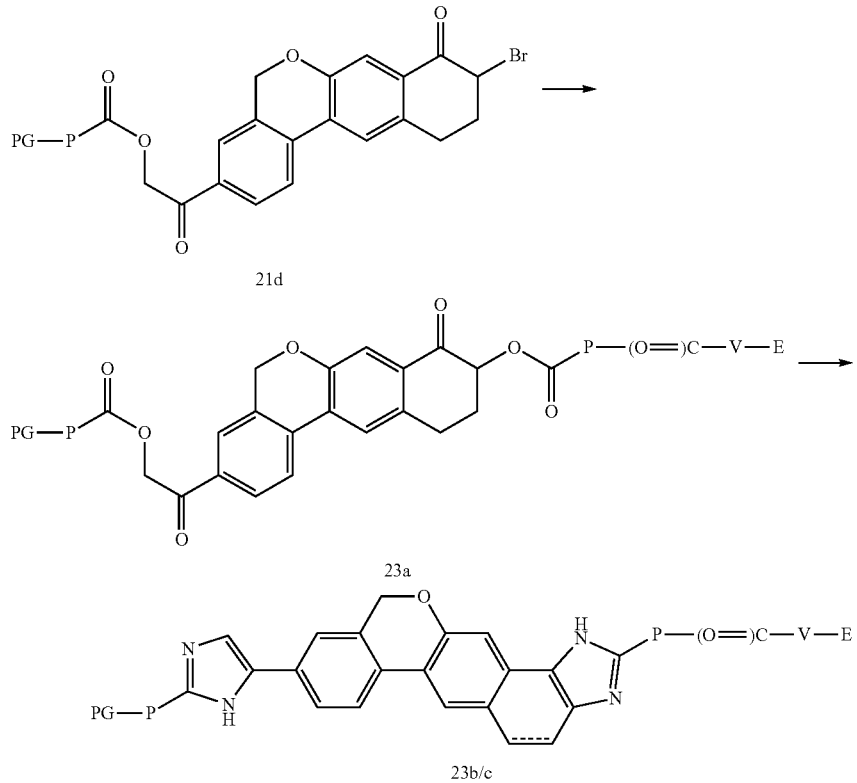

Scheme 23 shows a general synthesis of an E-V—C (=O)—P—W—P—R intermediate of the invention wherein, for illustrative purposes, R is a protecting group and W is a two aromatic ring unit. Displacement of the α-halo ketone 21d proceeds by the addition of an acid under basic conditions (e.g. Et$_3$N). Reaction of 23a with an amine or amine salt (e.g. ammonium acetate) affords the imidazole containing molecule 23b. Oxidation of 23b can be accomplished in the presence of MnO$_2$ to provide 23c.

Scheme 24. Representative synthesis of R$^1$—P—W—P—R$^2$

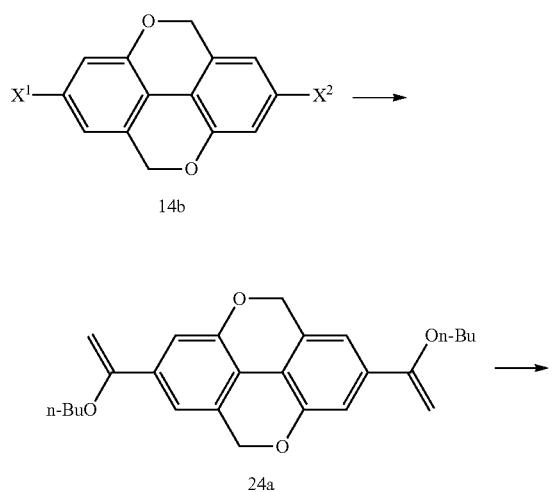

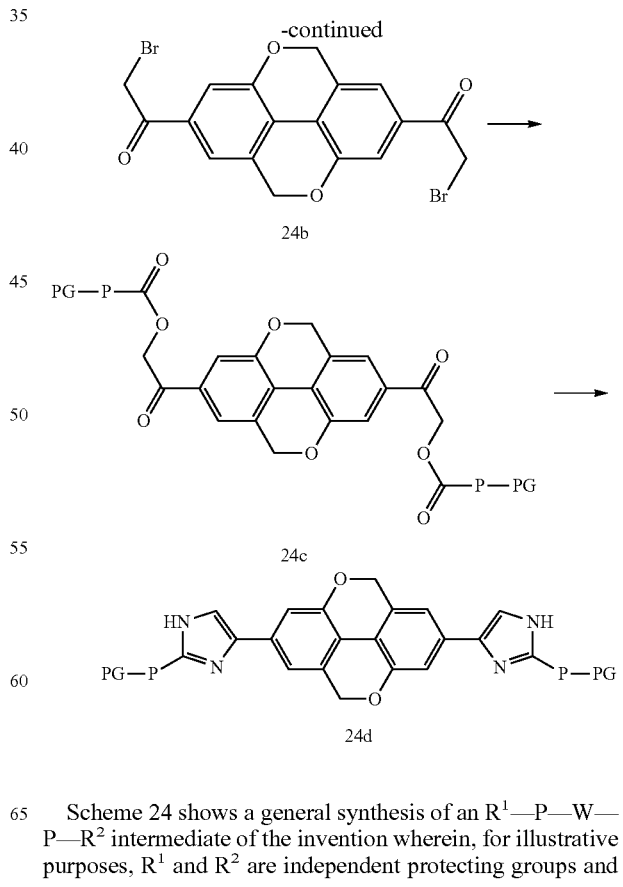

Scheme 24 shows a general synthesis of an R$^1$—P—W—P—R$^2$ intermediate of the invention wherein, for illustrative purposes, R$^1$ and R$^2$ are independent protecting groups and W is a three aromatic ring unit constructed via a transition metal mediated cross-coupling reaction. For illustrative purposes, W is constructed from a tetracyclic aromatic ring, wherein $X^1$ and $X^2$ are independent halogens or halogen equivalents that may be suitably protected. A transition metal-mediated cross-coupling reaction with butylvinylether, in the presence of palladium acetate and dppp, provides the divinyl compound 24a. Treatment of 24a with N-bromosuccinimide installs the corresponding a-halo ketone. Displacement of the α-halo ketone 24b proceeds by the addition of two equivalents of acid under basic conditions (e.g. $Et_3N$). Reaction of 24c with an amine or amine salt (e.g. ammonium acetate) affords the bis-imidazole containing molecule 24d.

arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclyl- Scheme 25. Representative synthesis of E—V—C(=O)—P—W—P—C(=O)—V—E

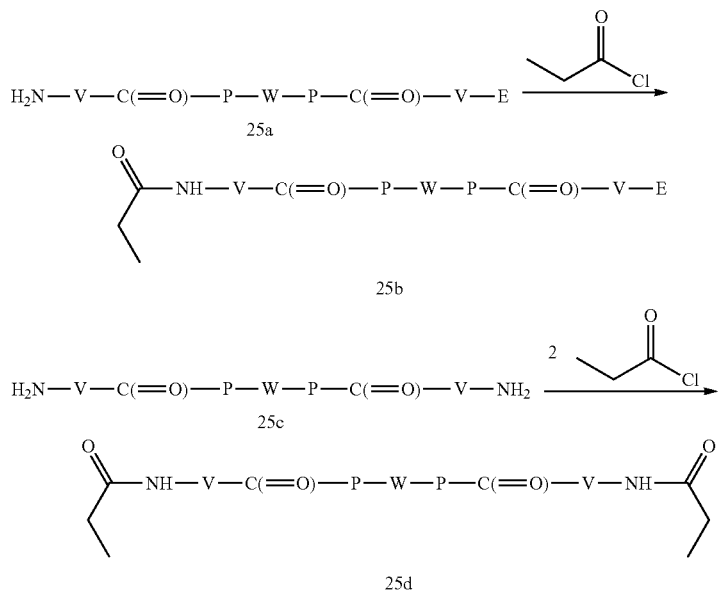

Scheme 25 shows a general synthesis of an E-V—C(=O)—P—W—P—C(=O)—V-E molecule of the invention wherein, for illustrative purposes, E is ethylcarbonylamino. The treatment of either 25a or 25c with one or two equivalents respectively of propionyl chloride under basic conditions (e.g. sodium hydroxide) provides the molecule 25b or 25d.

In one embodiment the invention provides a compound of the invention which is compound of formula (I):

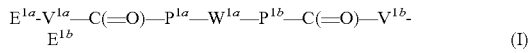

wherein:
$E^{1a}$ is $E^0$ or $E^1$, or $E^{1a}$-$V^{1a}$ taken together are $R^{9a}$;
$E^{1b}$ is $E^0$ or $E^1$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
$P^{1a}$ is selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;
$P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;
each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, alkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, (NR$^X$R$^Y$)alkyl-, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each P$^0$ is independently:

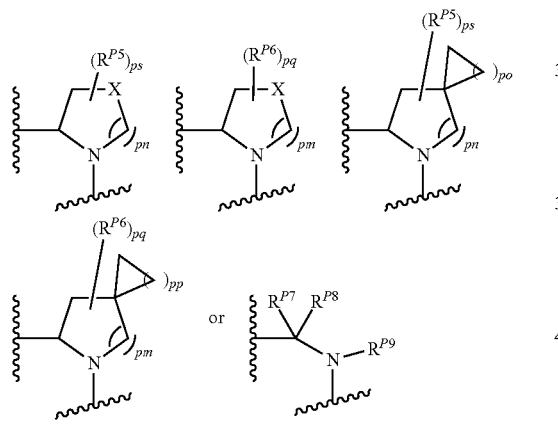

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

R$^{P7}$ and R$^{P8}$ are each independently selected from hydrogen, alkenyl, alkoxyalkyl, alkyl, haloalkyl, and (NR$^{Pa}$R$^{Pb}$) alkyl; or R$^{P7}$ and R$^{P5}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;
each P$^1$ is independently:

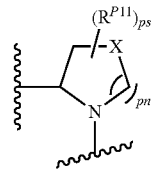

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo and heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
ps is 1, 2, 3, or 4;
pn is 0, 1, or 2;

each P³ is independently a ring of the formula:

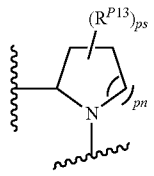

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;
each P⁵ is independently a ring of the formula:

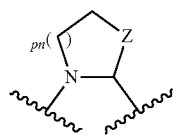

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pn is 0, 1, or 2;
Z is O, S, S(=O), S(=O)₂, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)₂$NR^hR^h$, —S(=O)₂$R^h$, C(=O)R, C(=O)$OR^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each P⁶ is independently a ring of the formula:

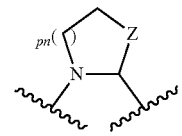

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
Z is O, S, S(=O), S(=O)₂, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)₂$NR^hR^h$, —S(=O)₂$R^h$, C(=O)$R^h$, C(=O)$OR^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each P⁷ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;
each P⁸ is independently a ring of the formula:

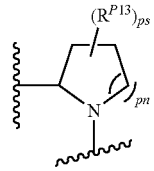

wherein:
ps is 2, 3, 4, 5, or 6;
pn is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

each $P^{10}$ is independently:

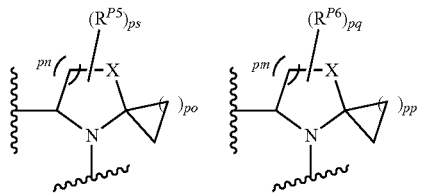

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

each $P^{12}$ is independently:

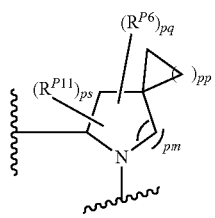

wherein:

each $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq is independently 0, 1, 2, 3, or 4;
pm is independently 0, 1, or 2;
pp is independently 1, 2, or 3;
ps is 1, 2, 3, or 4;

$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$) alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$) sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each $P^{15}$ is:

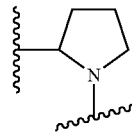 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

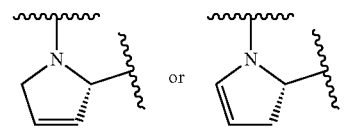 [SMILES: *[C@@H]1C=CCN1* ; *[C@@H]1CC=CN1*]

which is optionally substituted, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl with one or two groups independently selected from halo, alkyl, alkoxyalkyl, haloalkyl, cycloalkyl, and cycloalkylalkyl;

each $P^{19}$ is:

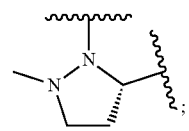

each P³⁰ is independently a ring of the formula:

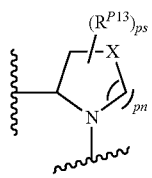

ps is 2
pn is 0, 1 or 2;
X is selected from O, S, S(O), SO₂, or CH₂; provided that when pn is 0, X is CH₂.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl; and $W^{1a}$ is selected from:

101 or

102

103 or

-continued

104 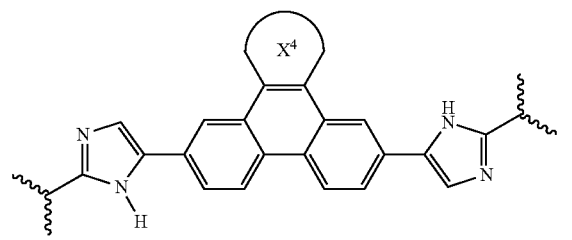

105 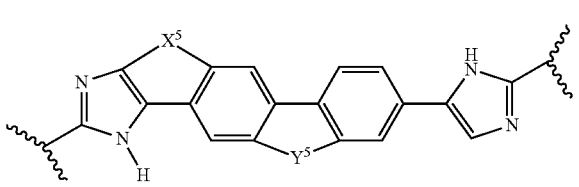

106 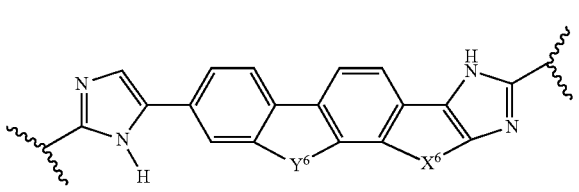

107 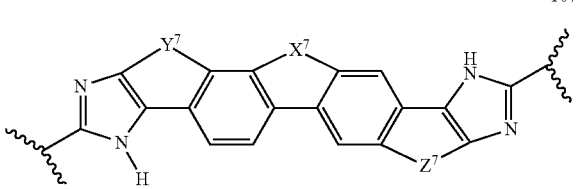

108 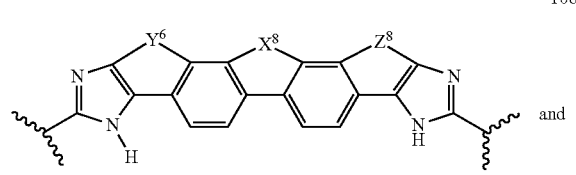 and

109 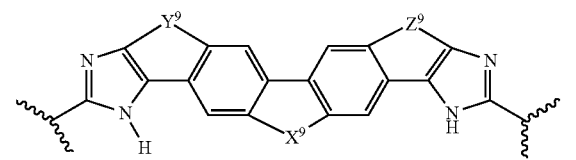

wherein each $W^{1a}$ is optionally substituted with one or more (e.g. 1, 2, 3, or 4) groups independently selected from halo, alkyl, haloalkyl, cyano, and

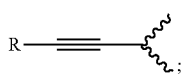;

wherein each R is independently H, alkyl, haloalkyl, cycloalkyl, aryl, or heteroaryl;

$X^1$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$Y^1$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$X^2$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$X^3$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$Y^3$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$X^4$ is a six membered aromatic or heteroaromatic or five membered heteroraromatic ring;

$X^5$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$Y^5$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$X^6$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$Y^6$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$X^7$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$Y^7$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$Z^7$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$X^8$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$Y^8$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$Z^8$ is —$CH_2$—, —$CH_2$—$CH_2$—, —$CH_2$—O—, —$CH_2$—O—$CH_2$—, —S—, —S(O)$_2$—, —C(O)—, —CF$_2$—, —OC(O)—, —(O)CO—, or —CH═CH—;

$X^9$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—;

$Y^9$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—$CH_2$—, —$CH_2$—S—, —OC(O)—, —(O)CO—, or —CH═CH—; and $Z^9$ is —$CH_2$—, —$CH_2$—$CH_2$—, —$CH_2$—O—, —O—$CH_2$—, —$CH_2$—O—$CH_2$—, —S—, —S(O)$_2$—, —C(O)—, —CF$_2$—, —O—, —S—CH$_2$—, —CH$_2$—S—, —OC(O)—, —(O)CO—, or —CH═CH—;

or a pharmaceutically acceptable salt or prodrug thereof.

In another embodiment the invention provides a compound of the invention which is compound of formula (I):

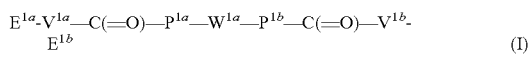

(I)

wherein:

E$^{1a}$ is E$^0$ or E$^1$, or E$^{1a}$-V$^{1a}$ taken together are R$^{9a}$;

E$^{1b}$ is E$^0$ or E$^1$, or E$^{1b}$-V$^{1b}$ taken together are R$^{9b}$;

V$^{1a}$ is V$^0$ or E$^{1a}$-V$^{1a}$ taken together are R$^{9a}$;

V$^{1b}$ is V$^0$ or E$^{1b}$-V$^{1b}$ taken together are R$^{9b}$;

one of P$^{1a}$ and P$^{1b}$ is selected from P$^1$, P$^3$, P$^5$, P$^6$, P$^7$, P$^8$, P$^{10}$, P$^{12}$, P$^{15}$, P$^{18}$, P$^{19}$ and P$^{30}$; and the other of P$^{1a}$ and P$^{1b}$ is selected from P$^0$, P$^1$, P$^3$, P$^5$, P$^6$, P$^7$, P$^8$, P$^{10}$, P$^{12}$, P$^{15}$, P$^{18}$, P$^{19}$ and P$^{30}$;

each E$^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each E$^1$ is independently selected from hydrogen, hydroxy, alkyl, haloalkyl, —NHhaloalkyl, aryl, and heterocyclyl;

each V$^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each P$^0$ is independently:

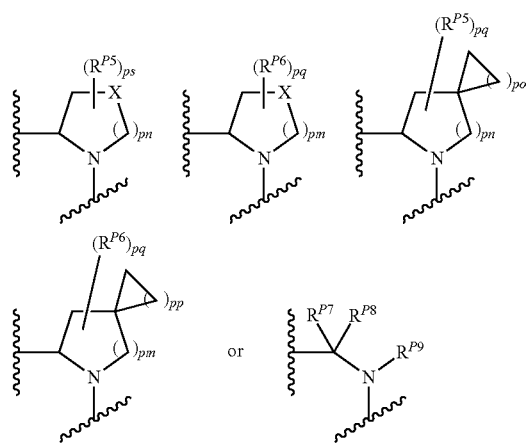

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;

pm and pn are independently 0, 1, or 2;

po and pp are independently 1, 2, or 3;

R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

$R^{P9}$ is selected from hydrogen and alkyl;

each $P^1$ is independently:

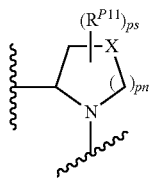

wherein:

X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

at least one $R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, C(=O)R$^h$, —C(=O)NR$^h$R$^h$; and the remaining $R^{P11}$ are independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo and heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl sulfonylalkyl; and when two R$^h$ groups are present then they may come together with the atoms to which they are bound to form a 4-15 membered heterocyclic ring;

ps is 1, 2, 3, or 4;

pn is 0, 1, or 2;

each $P^3$ is independently a ring of the formula:

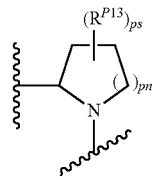

wherein:

the ring is substituted with one or more oxo group;

each $R^{P13}$ is independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

ps is 0, 1, 2, 3, or 4;

pn is 0, 1, or 2;

each $P^5$ is independently a ring of the formula:

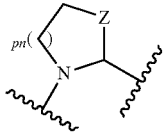

wherein:

the ring is optionally substituted with one or more groups $R^{P15}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pn is 0, 1, or 2;

Z is O, S, S(=O), S(=O)$_2$, or NR$^f$;

each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;
each $P^6$ is independently a ring of the formula:

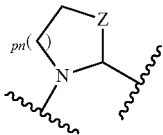

wherein:
the ring is substituted with one or more oxo and is optionally substituted with one or more groups $R^{P16}$ that are independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
Z is O, S, S(=O), S(=O)$_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $-S(=O)_2NR^hR^h$, $-S(=O)_2R^h$, $C(=O)R^h$, $C(=O)OR^h$, $-C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$.
each $P^8$ is independently a ring of the formula:

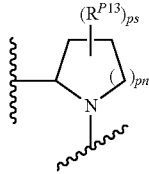

wherein:
ps is 2, 3, 4, 5, or 6;
pn is 0, 1 or 2;
each $R^{P13}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
each $P^{10}$ is independently:

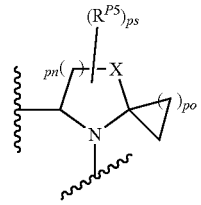 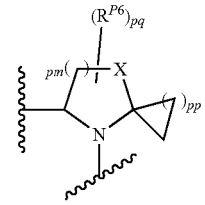

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each $R^{P10}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq and ps are independently 0, 1, 2, 3, or 4;
pm and pn are independently 0, 1, or 2;
po and pp are independently 1, 2, or 3;
each $P^{12}$ is independently:

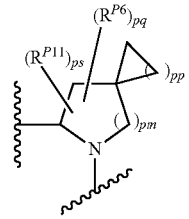

wherein:
each $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq is independently 0, 1, 2, 3, or 4;
pm is independently 0, 1, or 2;
pp is independently 1, 2, or 3;
ps is 1, 2, 3, or 4;

$R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl, —$NR^{hh}R^h$, $(NR^{hh}R^h)$alkyl, $(NR^{hh}R^h)$carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$ sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{15}$ is:

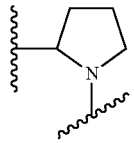

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

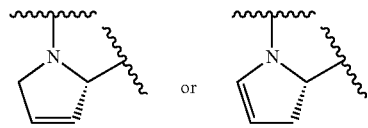 [SMILES: *[C@@H]1C=CCN1* ; *[C@@H]1CC=CN1*]

which is optionally substituted with one or two groups independently selected from halo, alkyl, alkoxyalkyl, haloalkyl, cycloalkyl, and cycloalkylalkyl;

each $P^{19}$ is:

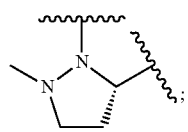 [SMILES: *[C@@H]1CCN(C)N1*]

each $P^{30}$ is independently a ring of the formula:

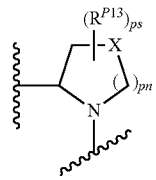

ps is 2 pn is 0, 1 or 2;

X is selected from O, S, S(O), $SO_2$, or $CH_2$; provided that when pn is 0, X is $CH_2$.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —$C(NCN)NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —$(NR^XR^Y)$alkyl, and —$(NR^XR^Y)$carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocycly-loxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

W$^{1a}$ is selected from:

110

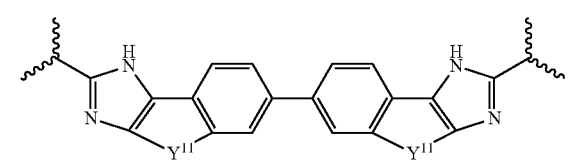

111

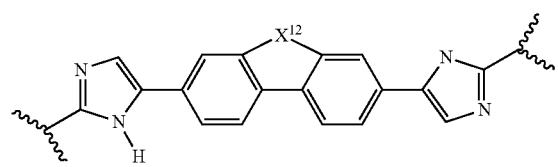

112

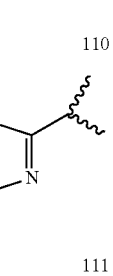

113

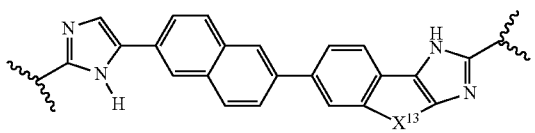

114

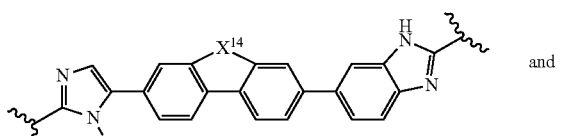

and

115

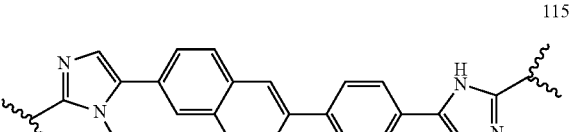

116

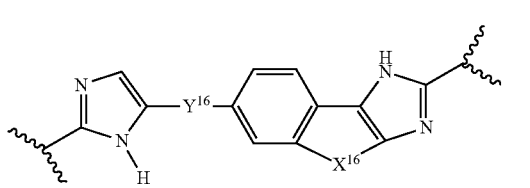

125

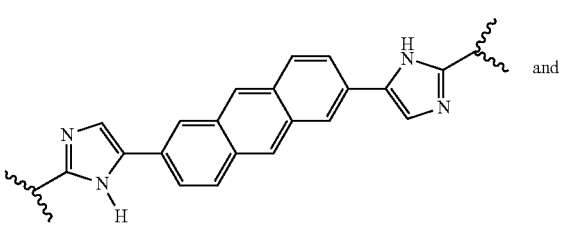

and

130

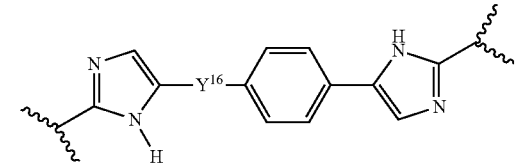

wherein each W$^{1a}$ is optionally substituted with one or more (e.g. 1, 2, 3, or 4) groups independently selected from halo, alkyl, haloalkyl, cyano, and

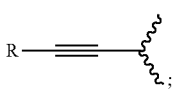

wherein each R is independently H, alkyl, haloalkyl, cycloalkyl, aryl, or heteroaryl;

X$^{11}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

Y$^{11}$ is —CH$_2$—, —CH$_2$—CH$_2$—, —CH$_2$—O—, —O—CH$_2$—, —CH$_2$—O—CH$_2$—, —S—, —S(O)$_2$—,

—C(O)—, —CF₂—, —O—, —S—CH₂—, —CH₂—S—, —O—C(O)—, —C(O)—O—, —CH═N—; —N═CH—; or —CH═CH—

X¹² is —CH₂—, —CH₂—CH₂—, —CH₂—O—, —O—CH₂—, —CH₂—O—CH₂—, —S—, —S(O)₂—, —C(O)—, —CF₂—, —O—, —S—CH₂—, —CH₂—S—, —O—C(O)—, —C(O)—O—, —CH═N—; —N═CH—; or —CH═CH—

X¹³ is —CH₂—, —CH₂—CH₂—, —CH₂—O—, —O—CH₂—, —CH₂—O—CH₂—, —S—, —S(O)₂—, —C(O)—, —CF₂—, —O—, —S—CH₂—, —CH₂—S—, —O—C(O)—, —C(O)—O—, —CH═N—; —N═CH—; or —CH═CH—; and X¹⁴ is —CH₂—, —CH₂—CH₂—, —CH₂—O—, —O—CH₂—, —CH₂—O—CH₂—, —S—, —S(O)₂—, —C(O)—, —CF₂—, —O—, —S—CH₂—, —CH₂—S—, —O—C(O)—, —C(O)—O—, —CH═N—; —N═CH—; or —CH═CH—; and each $Y^{16}$ is a bicyclic aromatic ring system comprising eight to 12 atoms optionally including one or more heteroatoms selected from O, S, and N, which bicyclic ring system is optionally with one or more groups independently selected from halo, haloalkyl, alkyl and oxo.

or a pharmaceutically acceptable salt or prodrug thereof.

In another embodiment the invention provides a compound of the invention which is compound of formula (I):

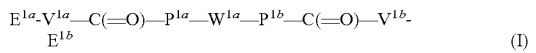

(I)

wherein:

$E^{1a}$ is $E^0$ or $E^1$, or $E^{1a}$-$V^{1a}$ taken together are $R^{9a}$;
$E^{1b}$ is $E^0$ or $E^1$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
one of $P^{1a}$ and $P^{1b}$ is selected from $P^1$, $P^3$, $P^5$, $P^6$, $P^7$, $P^8$, $P^{10}$, $P^{12}$, $P^{15}$, $P^{18}$, $P^{19}$ and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$;

each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, aryl, and heterocyclyl;

each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)OR₂, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$W^{1a}$ is:

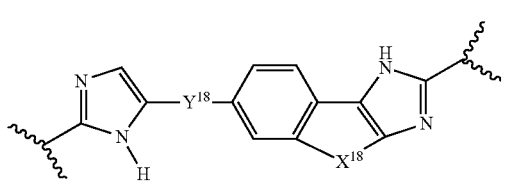

118 wherein $W^{1a}$ is optionally substituted with one or more (e.g. 1, 2, 3, or 4) groups independently selected from halo, alkyl, haloalkyl, cyano, and

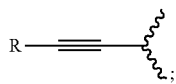

wherein each R is independently H, alkyl, haloalkyl, cycloalkyl, aryl, or heteroaryl;

$Y^{18}$ is selected from $A^0$, $A^1$, $A^2$, $A^3$, $A^7$, $A^{15}$, $A^{16}$, and $A^{20}$;

each $A^0$ is independently:

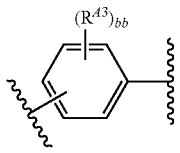

wherein:
each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, $(NR^aR^b)$alkyl, and $(NR^aR^b)$carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each
bb is independently 0, 1, 2, 3, or 4; or
each $A^0$ is independently a six-membered heteroaromatic ring containing one, two, or three nitrogen atoms, which ring is optionally substituted with 1, 2, 3, or 4 $R^{43}$ groups;
each $A^1$ is independently:

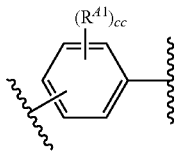

wherein:
each $R^{41}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and
each $R^4$ is independently selected from H, alkyl, haloalkyl, aryl, and arylalkyl;
each cc is independently 1, 2, 3, or 4;
each $A^2$ is independently:

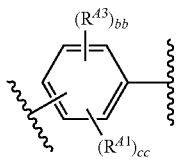

wherein:
each $R^{41}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, $(NR^aR^b)$alkyl, and $(NR^aR^b)$carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $R^4$ is independently selected from H, alkyl, haloalkyl, aryl, and arylalkyl;
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each bb is 0, 1, 2, 3, or 4; each cc is 1, 2, 3, or 4; and the sum of bb and cc is 1, 2, 3, or 4;
each $A^3$ is independently a six-membered heteroaromatic ring containing one, two, or three nitrogen atoms, which ring is substituted with one or more $R^{41}$ groups, and which ring is optionally substituted with one or more $R^{43}$ groups;
each $A^7$ is independently:

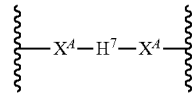

wherein:
each $H^7$ is independently a five-membered heteroaromatic ring, which $H^7$ is optionally substituted with one or more groups independently selected from $R^{41}$ and $R^{43}$; and
each $X^A$ is independently O, NR, SO, $SO_2$, C(=O), NRC(=O), C(=O)NR, CR=CR, NRC(=O)NR, allenyl, alkynyl, or absent; and each R is independently selected from H or alkyl;
each $A^{15}$ is independently:

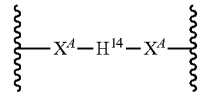

wherein:
each $H^{14}$ is independently a fused unsaturated, partially unsaturated or saturated tricyclic carbocycle which is optionally substituted with one or more groups independently selected from oxo, $R^{41}$ and $R^{43}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^{16}$ is independently:

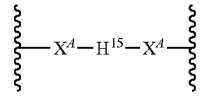

wherein:
each $H^{15}$ is independently a fused unsaturated, partially unsaturated or saturated tricyclic heterocycle that comprises at least one heteroatom in the ring system, which ring system is optionally substituted with one or more groups independently selected from $R^{41}$ and $R^{43}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^{20}$ is independently a 5 or 6 membered heteroaryl ring that is optionally substituted with one or more groups independently selected from $R^{41}$ and $R^{43}$;

each $P^0$ is independently:

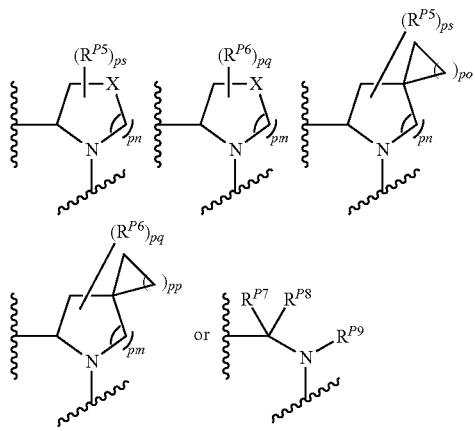

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

$R^{P7}$ and $R^{P8}$ are each independently selected from hydrogen, alkenyl, alkoxyalkyl, alkyl, haloalkyl, and (NR$^{Pa}$R$^{Pb}$)alkyl; or $R^{P7}$ and $R^{P8}$, together with the carbon atom to which they are attached, form a five or six membered saturated ring optionally containing one or two heteroatoms selected from NR$^{Pz}$, O, and S; wherein $R^{Pz}$ is selected from hydrogen and alkyl;

$R^{P9}$ is selected from hydrogen and alkyl;

each $P^1$ is independently:

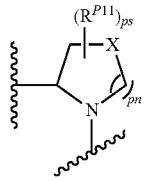

wherein:

X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

at least one $R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining $R^{P11}$ are independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocloooxyalkyloxy, (NR$^h$R$^h$)alkyloxy, cyanoalkoxy, cyanocycloalkyloxy, cycloalkyloxy, oxo and heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;

each $P^3$ is independently a ring of the formula:

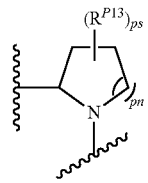

wherein:

the ring is substituted with one or more oxo group;

each $R^{P13}$ is independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

ps is 0, 1, 2, 3, or 4;
pn is 0, 1, or 2;
each P$^5$ is independently a ring of the formula:

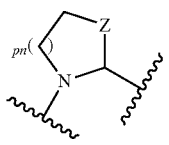

wherein:
the ring is optionally substituted with one or more groups R$^{P15}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups R$^{P15}$ that are attached to the same carbon when taken together with the carbon to which they are attached can form a 3-6 membered carbocyclic or heterocyclic ring;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
pn is 0, 1, or 2;
Z is O, S, S(=O), S(=O)$_2$, or NR$^f$;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;
each P$^6$ is independently a ring of the formula:

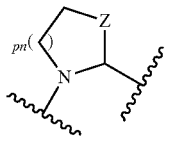

wherein:
the ring is substituted with one or more oxo and is optionally substituted with one or more groups R$^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
Z is O, S, S(=O), S(=O)$_2$, or NR$^f$;
pn is 0, 1, or 2;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;
each P$^7$ is a bridged 5-15 membered bicyclic heterocyclic ring that is attached to the remainder of the compound of formula I through one N-link and through one C-link; wherein the ring is optionally substituted with one or more groups independently selected from R$^{P6}$ and R$^{P11}$;
each P$^8$ is independently a ring of the formula:

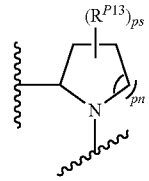

wherein:
ps is 2, 3, 4, 5, or 6;
pn is 0, 1 or 2;
each R$^{P13}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; where in at least one case two groups R$^{P13}$ that are attached to the same carbon are taken together with the carbon to which they are attached and form a 4-6 membered heterocyclic ring;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
each P$^{10}$ is independently:

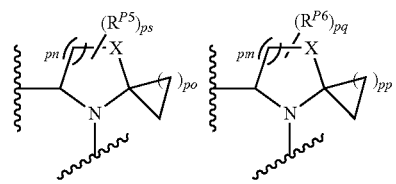

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
pq and ps are independently 0, 1, 2, 3, or 4;
pm and pn are independently 0, 1, or 2;
po and pp are independently 1, 2, or 3;
each P$^{12}$ is independently:

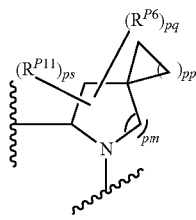

wherein:
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
pq is independently 0, 1, 2, 3, or 4;
pm is independently 0, 1, or 2;
pp is independently 1, 2, or 3;
ps is 1, 2, 3, or 4;
R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(═O)$_2$R$^h$, —C(═O)R$^h$, —C(═O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
each P$^{15}$ is:

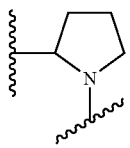

which is substituted with one or two groups independently selected from alkoxyalkyl, haloalkoxyalkyl, alkylsulfanyl, alkylsulfanylalkyl, cyanoalkyl, and cycloalkylalkyl;
each P$^{18}$ is:

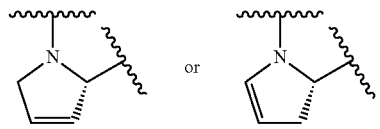 [SMILES: *[C@@H]1C=CCN1* ; *[C@@H]1CC=CN1*]

which is optionally substituted with one or two groups independently selected from halo, alkyl, alkoxyalkyl, haloalkyl, cycloalkyl, and cycloalkylalkyl;
each P$^{19}$ is:

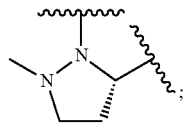 [SMILES: *[C@@H]1CCN(C)N1*]

each P$^{20}$ is:

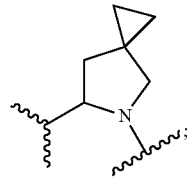 [SMILES: *C1CC2(CC2)CN1*]

each P$^{30}$ is independently a ring of the formula:

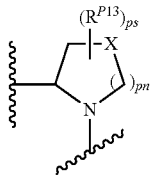

ps is 2
pn is 0, 1 or 2;
X is selected from O, S, S(O), SO₂, or CH₂; provided that when pn is 0, X is CH₂.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl; and each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

$X^{18}$ is —CH₂—, —CH₂—CH₂—, —CH₂—O—, —O—CH₂—, —CH₂—O—CH₂—, —S—, —S(O)₂—, —C(O)—, —CF₂—, —O—, —S—CH₂—, —CH₂—S—, —O—C(O)—, —C(O)—O—, —CH=N—; —N=CH—; or —CH=CH—;

or a pharmaceutically acceptable salt or prodrug thereof.

In another embodiment the invention provides a compound of the invention which is compound of formula (I):

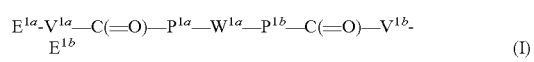

wherein:
$E^{1a}$ is $E^0$ or $E^1$, or $E^{1a}$-$V^{1a}$ taken together are $R^{9a}$;
$E^{1b}$ is $E^0$ or $E^1$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, aryl, and heterocyclyl;

each $V^o$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$P^{1a}$ and $P^{1b}$ are each independently selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;

each $P^0$ is independently:

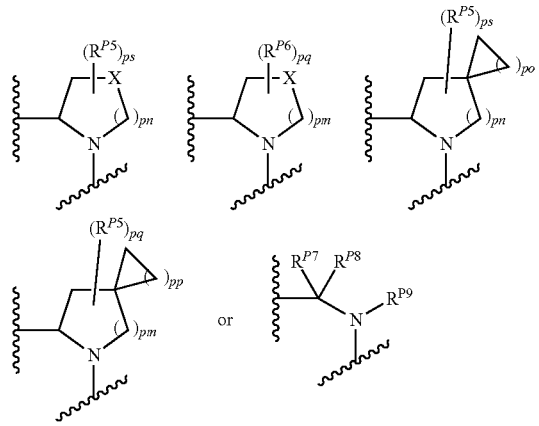

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;
R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;
each P$^1$ is independently:

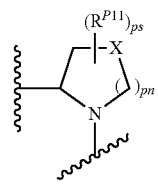

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, $—S(=O)_2R^h$, $—C(=O)R^h$, $—C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo and heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;
each $P^3$ is independently a ring of the formula:

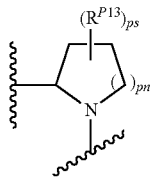

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;
each $P^5$ is independently a ring of the formula:

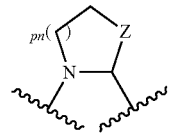

wherein:
the ring is optionally substituted with one or more groups $R^{P15}$ that are independently selected from alkoxy, alkyl, aryl, halo, haloalkyl, hydroxy, and $—NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pn is 0, 1, or 2;
Z is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $—S(=O)_2NR^hR^h$, $—S(=O)_2R^h$, $C(=O)R^h$, $C(=O)OR^h$, $—C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

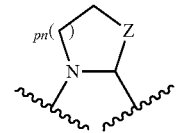

wherein:
the ring is substituted with one or more oxo and is optionally substituted with one or more groups $R^{P16}$ that are independently selected from alkoxy, alkyl, aryl, halo, haloalkyl, hydroxy, and $—NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
Z is O, S, S(=O), S(=O)$_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $—S(=O)_2NR^hR^h$, $—S(=O)_2R^h$, $C(=O)R^h$, $C(=O)OR^h$, $—C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;

each $P^8$ is independently a ring of the formula:

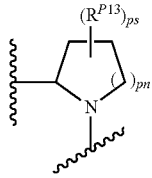

wherein:
ps is 2, 3, 4, 5, or 6;
pn is 0, 1 or 2;
each $R^{P13}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;

each $P^{10}$ is independently:

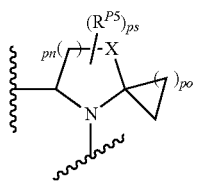 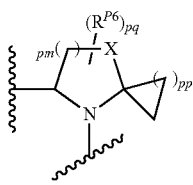

wherein:
X is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;
each $R^{P10}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq and ps are independently 0, 1, 2, 3, or 4;
pm and pn are independently 0, 1, or 2;
po and pp are independently 1, 2, or 3;

each $P^{12}$ is independently:

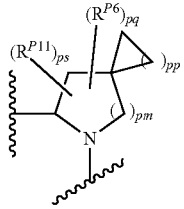

wherein:
each $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq is independently 0, 1, 2, 3, or 4;
pm is independently 0, 1, or 2;
pp is independently 1, 2, or 3;
ps is 1, 2, 3, or 4;
$R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl, $-NR^{hh}R^h$, $(NR^{hh}R^h)$alkyl, $(NR^{hh}R^h)$carbonyl, wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, $-S(=O)_2R^h$, $-C(=O)R^h$, $-C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{15}$ is:

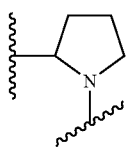

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

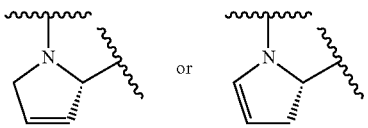 [SMILES: *[C@@H]1C=CCN1* ; *[C@@H]1CC=CN1*]

which is optionally substituted with one or two groups independently selected from halo, alkyl, alkoxyalkyl, haloalkyl, cycloalkyl, and cycloalkylalkyl;

each $P^{19}$ is:

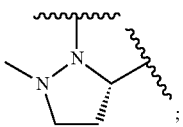

each $P^{30}$ is independently a ring of the formula:

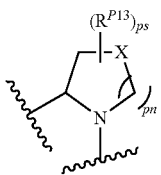

ps is 2 pn is 0, 1 or 2;

X is selected from O, S, S(O), SO$_2$, or CH$_2$; provided that when pn is 0, X is CH$_2$.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

$W^{1a}$ is selected from:

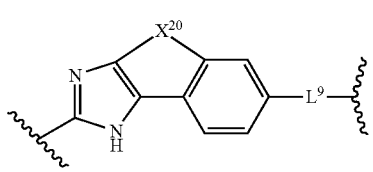

120

-continued

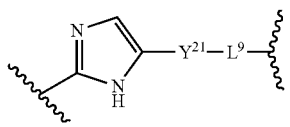
121

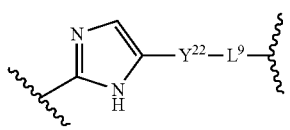
122 and

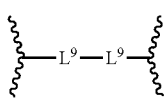
123 wherein each $W^{1a}$ is optionally substituted with one or more (e.g. 1, 2, 3, or 4) groups independently selected from halo, alkyl, haloalkyl, cyano, and

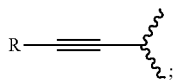

wherein each R is independently H, alkyl, haloalkyl, cycloalkyl, aryl, or heteroaryl;

$X^{20}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

$Y^{21}$ is a bicyclic aromatic ring system comprising eight to 12 atoms optionally including one or more heteroatoms selected from O, S, and N, which bicyclic ring system is optionally with one or more groups independently selected from halo, haloalkyl, alkyl and oxo;

$Y^{22}$ is selected from $A^0$, $A^1$, $A^2$, $A^3$, $A^7$, $A^{15}$, $A^{16}$, and $A^{20}$;

each $A^0$ is independently:

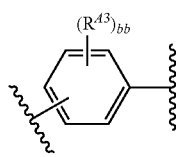

wherein:

each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or each $A^0$ is independently a six-membered heteroaromatic ring containing one, two, or three nitrogen atoms, which ring is optionally substituted with 1, 2, 3, or 4 $R^{43}$ groups;

each $A^1$ is independently:

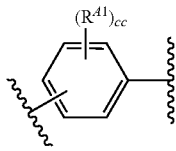

wherein:

each $R^{41}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and each $R^4$ is independently selected from H, alkyl, haloalkyl, aryl, and arylalkyl;

each cc is independently 1, 2, 3, or 4;

each $A^2$ is independently:

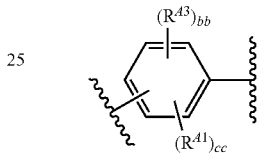

wherein:

each $R^{41}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $R^4$ is independently selected from H, alkyl, haloalkyl, aryl, and arylalkyl;

R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each bb is 0, 1, 2, 3, or 4; each cc is 1, 2, 3, or 4; and the sum of bb and cc is 1, 2, 3, or 4;

each $A^3$ is independently a six-membered heteroaromatic ring containing one, two, or three nitrogen atoms, which ring is substituted with one or more $R^{41}$ groups, and which ring is optionally substituted with one or more $R^{43}$ groups;

each $A^7$ is independently:

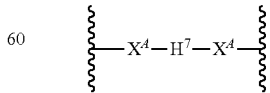

wherein:

each $H^7$ is independently a five-membered heteroaromatic ring, which $H^7$ is optionally substituted with one or more groups independently selected from $R^{41}$ and $R^{43}$; and each $X^A$ is independently O, NR, SO, SO$_2$, C(=O), NRC(=O), C(=O)NR, CR=CR, NRC(=O)NR, allenyl, alkynyl, or absent; and each R is independently selected from H or alkyl;

each $A^{15}$ is independently:

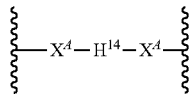

wherein:
each $H^{14}$ is independently a fused unsaturated, partially unsaturated or saturated tricyclic carbocycle which is optionally substituted with one or more groups independently selected from oxo, $R^{41}$ and $R^{43}$; and
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;

each $A^{16}$ is independently:

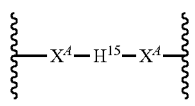

wherein:
each $H^{15}$ is independently a fused unsaturated, partially unsaturated or saturated tricyclic heterocycle that comprises at least one heteroatom in the ring system, which ring system is optionally substituted with one or more groups independently selected from $R^{41}$ and $R^{43}$; and
each $X^A$ is independently O, NR, SO, SO$_2$, C(=O), NRC(=O), C(=O)NR, CR=CR, NRC(=O)NR, allenyl, alkynyl, or absent and each R is independently selected from H or alkyl;
each $A^{20}$ is independently a 5 or 6 membered heteroaryl ring that is optionally substituted with one or more groups independently selected from $R^{41}$ and $R^{43}$;
each $L^9$ is independently a fused-tetracyclic saturated, partially unsaturated, or aromatic heterocyclic ring system that is optionally substituted with one or more groups independently selected from oxo, halo, —$R^{L9}$, —$OR^{L9}$, —$SR^{L9}$, —$CF_3$, —$CCl_3$, —$OCF_3$, —CN, —$NO_2$, —N($R^{L9}$)C(=O)$R^{L9}$, —C(=O)$R^{L9}$, —OC(=O)$R^{L9}$, —C(O)O$R^{L9}$, —C(=O)N$R^{L9}$, —S(=O)$R^{L9}$, —S(=O)$_2$O$R^{L9}$, S(=O)$_2$$R^{L9}$, —OS(=O)$_2$O$R^{L9}$, —S(=O)$_2$N$R^{L9}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;
each $R^{L9}$ is independently —H, alkyl, aryl, arylalkyl, or heterocycle; and
R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
or a pharmaceutically acceptable salt or prodrug thereof.

In another embodiment the invention provides a compound of the invention which is compound of formula (I):

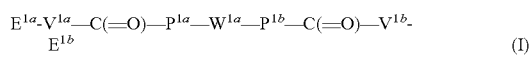 (I)

wherein:
$E^{1a}$ is $E^0$ or $E^1$, or $E^{1a}$-$V^{1a}$ taken together are $R^{9a}$;
$E^{1b}$ is $E^0$ or $E^1$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;
each $E^1$ is independently selected from hydrogen, hydroxy, alkyl, haloalkyl, —NHhaloalkyl, aryl, and heterocyclyl;
each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$P^{1a}$ and $P^{1b}$ are each independently selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;

each $P^0$ is independently:

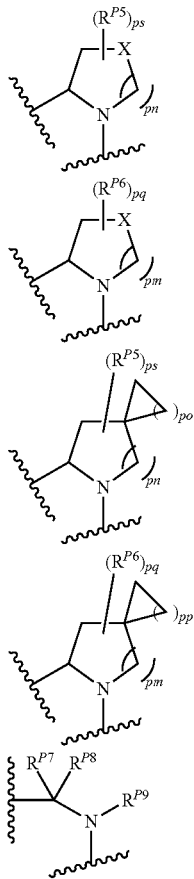

or wherein:

X is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

$R^{P7}$ and $R^{P8}$ are each independently selected from hydrogen, alkenyl, alkoxyalkyl, alkyl, haloalkyl, and $(NR^{Pa}R^{Pb})$alkyl; or $R^{P7}$ and $R^{P8}$, together with the carbon atom to which they are attached, form a five or six membered saturated ring optionally containing one or two heteroatoms selected from $NR^{Pz}$, O, and S; wherein $R^{Pz}$ is selected from hydrogen and alkyl;

$R^{P9}$ is selected from hydrogen and alkyl;

each $P^1$ is independently:

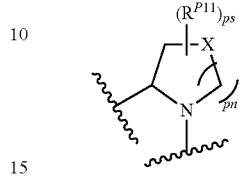

wherein:

X is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

at least one $R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyloxyalkyloxy, aryloxyalkyloxy, heteroaryloxyakyloxy, heterocyclyloxyalkyloxy, $(NR^hR^h)$alkyloxy, cyanoalkoxy, cyanocycloalkyloxy, cycloalkyloxy, oxo, heterocyclyl, $-NR^{hh}R^h$, $(NR^{hh}R^h)$alkyl, $(NR^{hh}R^h)$carbonyl, wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, $-S(=O)_2R^h$, $-C(=O)R^h$, $-C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo and heterocyclyl; wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;

each $P^3$ is independently a ring of the formula:

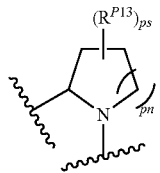

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;
each $P^5$ is independently a ring of the formula:

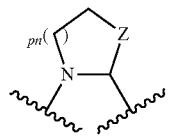

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pn is 0, 1, or 2;
Z is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

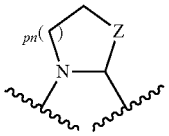

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
Z is O, S, S(=O), S(=O)$_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;
each $P^8$ is independently a ring of the formula:

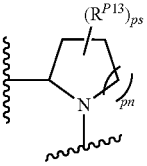

wherein:
ps is 2, 3, 4, 5, or 6;
pn is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

each $P^{10}$ is independently:

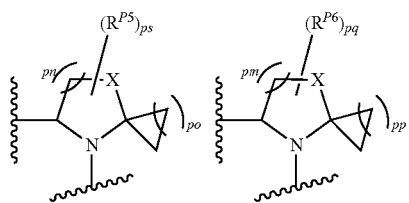

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

each $R^{P5}$ and $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

pq and ps are independently 0, 1, 2, 3, or 4;
pm and pn are independently 0, 1, or 2;
po and pp are independently 1, 2, or 3;
each $P^{12}$ is independently:

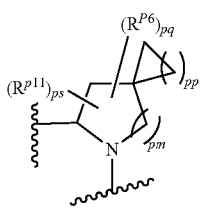

wherein:

each $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq is independently 0, 1, 2, 3, or 4;
pm is independently 0, 1, or 2;
pp is independently 1, 2, or 3;
ps is 1, 2, 3, or 4;

$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each $P^{15}$ is:

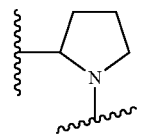 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

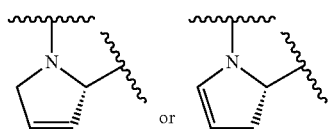 [SMILES: *[C@@H]1C=CCN1* ; *[C@@H]1CC=CN1*]

which is optionally substituted with one or two groups independently selected from halo, alkyl, alkoxyalkyl, haloalkyl, cycloalkyl, and cycloalkylalkyl;

each $P^{19}$ is:

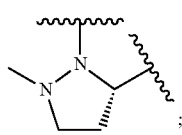 [SMILES: *[C@@H]1CCN(C)N1*];

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —($NR^XR^Y$)alkyl, and —($NR^XR^Y$)carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl, wherein $R^{X'}$ and R' are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —($NR^XR^Y$)alkyl, and —($NR^XR^Y$)carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl, wherein $R^{X'}$ and R' are independently selected from hydrogen and alkyl;

$W^{1a}$ is selected from:

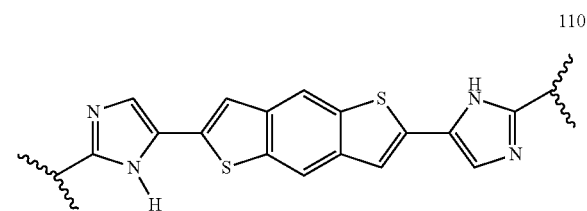

110

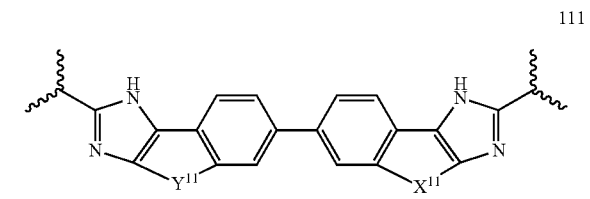

111

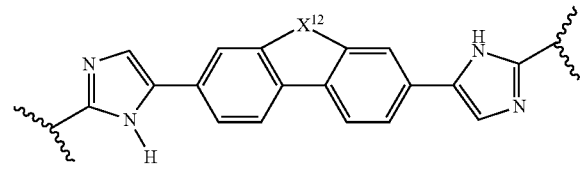

112


113

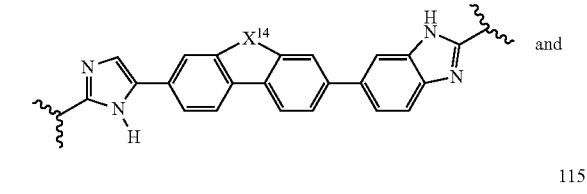

114 and

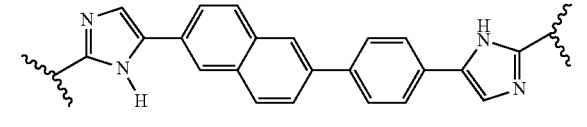

115

-continued

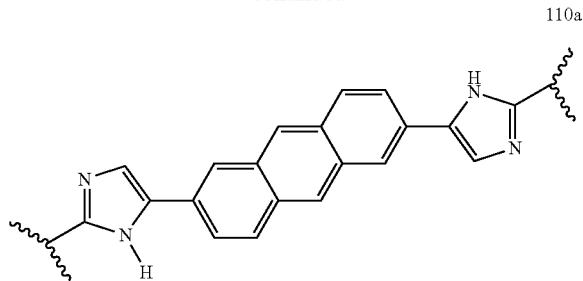
110a wherein each $W^{1a}$ is optionally substituted with one or more (e.g. 1, 2, 3, or 4) groups independently selected from halo, alkyl, haloalkyl, cyano, and wherein each $W^{1a}$ is substituted with one or more (e.g. 1, 2, 3, or 4):

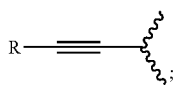

wherein each R is independently H, alkyl, haloalkyl, cycloalkyl, aryl, or heteroaryl;

$X^{11}$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —O—C(O)—, —C(O)—O—, —CH=N—; —N=CH—; or —CH=CH—

$Y^{11}$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —O—C(O)—, —C(O)—O—, —CH=N—; —N=CH—; or —CH=CH—

$X^{12}$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —O—C(O)—, —C(O)—O—, —CH=N—; —N=CH—; or —CH=CH—

$X^{13}$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —O—C(O)—, —C(O)—O—, —CH=N—; —N=CH—; or —CH=CH—; and $X^{14}$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —O—C(O)—, —C(O)—O—, —CH=N—; —N=CH—; or —CH=CH—;

or a pharmaceutically acceptable salt or prodrug thereof.

In another embodiment the invention provides a compound of the invention which is compound of formula (I):

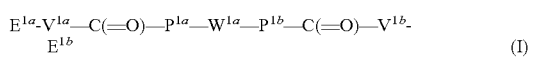
(I)

wherein:
$E^{1a}$ is $E^0$ or $E^1$, or $E^{1a}$-$V^{1a}$ taken together are $R^{9a}$;
$E^{1b}$ is $E^0$ or $E^1$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
one of $P^{1a}$ and $P^{1b}$ is selected from $P^{0a}$ and the other of $P^{1a}$ and $P^{1b}$ is selected from $P^1$, $P^3$, $P^5$, $P^6$, $P^7$, $P^8$, $P^{10}$, $P^{12}$, $P^{15}$, $P^{18}$, $P^{19}$, and $P^{30}$;
each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, aryl, and heterocyclyl;

each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —($NR^XR^Y$)alkyl, oxo, and —P(O)$OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, ($NR^XR^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$W^{1a}$ is:

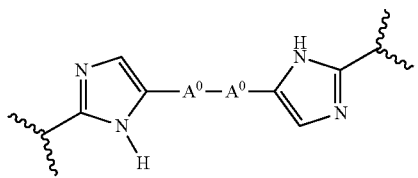

wherein $W^{1a}$ is optionally substituted with one or more (e.g. 1, 2, 3, or 4) groups independently selected from halo, alkyl, haloalkyl, cyano, and

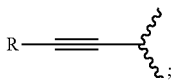

wherein each R is independently H, alkyl, haloalkyl, cycloalkyl, aryl, or heteroaryl;

each $P^{0a}$ is independently:

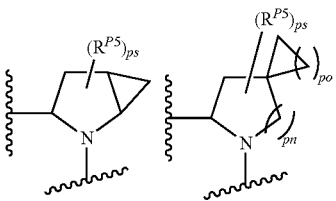

each $R^{P5}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

ps is independently 0, 1, 2, 3, or 4;
pn is independently 0, 1, or 2;
po is independently 1, 2, or 3;
each $P^1$ is independently:

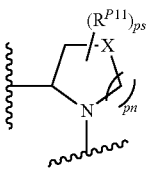

wherein:
X is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
at least one $R^{P11}$ is independently selected from cyano, alkylsulfonyl, arylsulfonyl, ($NR^hR^h$)sulfonyl, hetero-cyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$a)lkyloxy, cyanoalkoxy, cyanocycloalkyloxy, cycloalkyloxy, oxo, heterocyclyl, —$NR^{hh}R^h$, ($NR^{hh}R^h$)alkyl, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;
each $P^3$ is independently a ring of the formula:

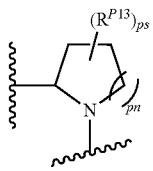

wherein:
the ring is substituted with one or more oxo group;
each $R^{P13}$ is independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;

each P⁵ is independently a ring of the formula:

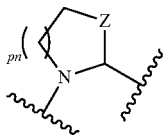

wherein:
the ring is optionally substituted with one or more groups R^{P15} that are independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups; and where two groups R^{P15} that are attached to the same carbon when taken together with the carbon to which they are attached can form a 3-6 membered carbocyclic or heterocyclic ring;
pn is 0, 1, or 2;
Z is O, S, S(=O), S(=O)₂, or NR^f;
each R^f is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)₂NR^hR^h, —S(=O)₂R^h, C(=O)R, C(=O)OR^h, —C(=O)NR^hR^h; each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R^h groups are present then they may come together with the atoms to which they are bound to form a 4-15 membered heterocyclic ring;
each P⁶ is independently a ring of the formula:

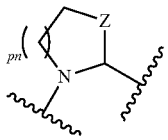

wherein:
the ring is substituted with one or more oxo and is optionally substituted with one or more groups R^{P16} that are independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
Z is O, S, S(=O), S(=O)₂, or NR^f;
pn is 0, 1, or 2;
each R^f is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)₂NR^hR^h, —S(=O)₂R^h, C(=O)R^h, C(=O)OR^h, —C(=O)NR^hR^h; each R^h is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R^h groups are present then they may come together with the atoms to which they are bound to form a 4-15 membered heterocyclic ring;
each P⁷ is a bridged 5-15 membered bicyclic heterocyclic ring that is attached to the remainder of the compound of formula I through one N-link and through one C-link; wherein the ring is optionally substituted with one or more groups independently selected from R^{P6} and R^{P11};
each P⁸ is independently a ring of the formula:

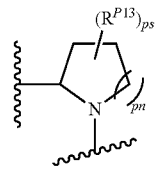

wherein:
ps is 2, 3, 4, 5, or 6;
pn is 0, 1 or 2;
each R^{P13} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups; where in at least one case two groups R^{P13} that are attached to the same carbon are taken together with the carbon to which they are attached and form a 4-6 membered heterocyclic ring;
each P¹⁰ is independently:

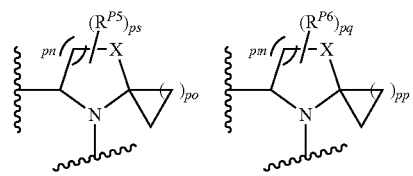

wherein:
X is selected from O, S, S(O), SO₂, CH₂, CHR^{P10}, and C(R^{P10})₂; provided that when pn or pm is 0, X is selected from CH₂, CHR^{P10}, and C(R^{P10})₂;
each R^{P10} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
each R^{P5} and R^{P6} is independently selected from alkoxy, alkyl, aryl, halo, haloalkyl, hydroxy, and —NR^{Pa}R^{Pb}, wherein the alkyl can optionally form a fused three- to six-membered ring with an adjacent carbon atom, wherein the three- to six-membered ring is optionally substituted with one or two alkyl groups;
pq and ps are independently 0, 1, 2, 3, or 4;
pm and pn are independently 0, 1, or 2;
po and pp are independently 1, 2, or 3;

each $P^{12}$ is independently:

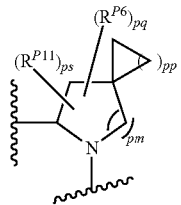

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
pp is independently 1, 2, or 3;
ps is 1, 2, 3, or 4;
$R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl, —$NR^{hh}R^h$, ($NR^{hh}R^h$)alkyl, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
each $P^{15}$ is:

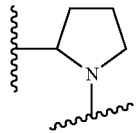

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

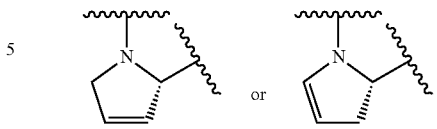

which is optionally substituted with one or two groups independently selected from halo, alkyl, alkoxyalkyl, haloalkyl, cycloalkyl, and cycloalkylalkyl;
each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —$C(NCN)OR'$, and —$C(NCN)NR^XR^Y$, wherein $R'$ is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —($NR^XR^Y$)alkyl, and —($NR^XR^Y$)carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl, wherein $R^{X'}$ and $R^{Y'}$ are independently selected from hydrogen and alkyl;
each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —$(NR^XR^Y)$alkyl, and —$(NR^XR^Y)$carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl;

or a pharmaceutically acceptable salt or prodrug thereof.

In another embodiment the invention provides a compound of the invention which is compound of formula (I):

$$E^{1a}\text{-}V^{1a}\text{—}C(\!=\!O)\text{—}P^{1a}\text{—}W^{1a}\text{—}P^{1b}\text{—}C(\!=\!O)\text{—}V^{1b}\text{-}E^{1b} \quad (I)$$

wherein:

$E^{1a}$ is $E^0$ or $E^1$, or $E^{1a}\text{-}V^{1a}$ taken together are $R^{9a}$;
$E^{1b}$ is $E^0$ or $E^1$, or $E^{1b}\text{-}V^{1b}$ taken together are $R^{9b}$;
$V^{1a}$ is $V^0$ or $E^{1a}\text{-}V^{1a}$ taken together are $R^{9a}$;
$V^{1b}$ is $V^0$ or $E^{1b}\text{-}V^{1b}$ taken together are $R^{9b}$;
one of $P^{1a}$ and $P^{1b}$ is selected from $P^{0b}$ and the other of $P^{1a}$ and $P^{1b}$ is selected from $P^{21}$, $P^3$, $P^6$, $P^7$, $P^{28}$, $P^{12}$, $P^{15}$ and $P^{38}$;
each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, aryl, and heterocyclyl;

each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —$(NR^XR^Y)$alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$W^{1a}$ is:

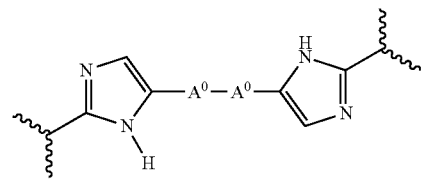

XX1 wherein $W^{1a}$ is optionally substituted with one or more (e.g. 1, 2, 3, or 4) groups independently selected from halo, alkyl, haloalkyl, cyano, and

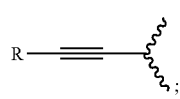

wherein each R is independently H, alkyl, haloalkyl, cycloalkyl, aryl, or heteroaryl;

each P$^{Ob}$ is independently:

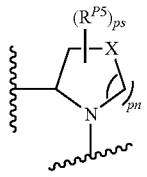

X is selected from O, S, S(O), SO$_2$, CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$;
each R$^{P5}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
ps is independently 0, 1, 2, 3, or 4;
pn is independently 0, 1, or 2;
each P$^{21}$ is independently:

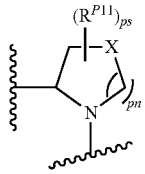

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclooxyalkyloxy, (NR$^h$R$^h$)alkyloxy, cyanoalkoxy, cyanocycloalkyloxy, cycloalkyloxy, oxo, —NR$^{hh}$R$^h$, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl;
ps is 1, 2, 3, or 4;
pn is 0, 1, or 2;
each P$^3$ is independently a ring of the formula:

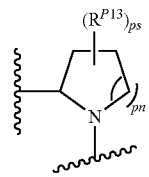

wherein:
the ring is substituted with one or more oxo group;
each R$^{P13}$ is independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
ps is 0, 1, 2, 3, or 4;
pn is 0, 1, or 2;
each P$^6$ is independently a ring of the formula:

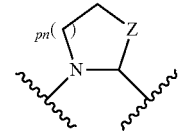

wherein:
the ring is substituted with one or more oxo and is optionally substituted with one or more groups R$^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
Z is O, S, S(=O), S(=O)$_2$, or NR$^f$;
pn is 0, 1, or 2;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)

NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;

each P$^7$ is a bridged 5-15 membered bicyclic heterocyclic ring that is attached to the remainder of the compound of formula I through one N-link and through one C-link; wherein the ring is optionally substituted with one or more groups independently selected from R$^{P6}$ and R$^{P11}$;

each P$^{28}$ is independently a ring of the formula:

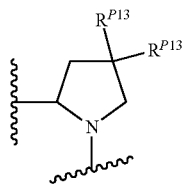

wherein:
each R$^{P13}$ is independently selected from alkoxy, alkyl, aryl, halo, haloalkyl, hydroxy, and —NR$^{Pa}$R$^{Pb}$, where in two R$^{P13}$ groups are taken together with the carbon to which they are attached and form a 4-6 membered heterocyclic ring;

each P$^{12}$ is independently:

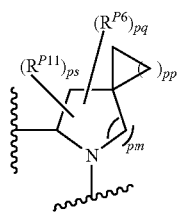

wherein:
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
pp is independently 1, 2, or 3;
ps is 1,2, 3, or 4;
R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^h$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each P$^{15}$ is:

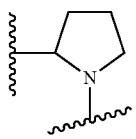 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each P$^{38}$ is:

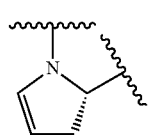 [SMILES: *[C@@H]1CC=CN1*]

which is optionally substituted with one or two groups independently selected from halo, alkyl, alkoxyalkyl, haloalkyl, cycloalkyl, and cycloalkylalkyl;

each R$^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

or a pharmaceutically acceptable salt or prodrug thereof.

In another embodiment the invention provides a compound of the invention which is a compound of any one of formulae 1-25, 25b, 25c, and 25d as shown in Table 1, or a pharmaceutically acceptable salt or prodrug thereof.

In another embodiment the invention provides a compound of the invention which is a compound of any one of formulae 26-102 as shown in Table 2, or a pharmaceutically acceptable salt or prodrug thereof.

In another embodiment the invention provides a compound of the invention which is a compound of any one of formulae 103-289 as shown in Table 3, or a pharmaceutically acceptable salt or prodrug thereof.

In another embodiment the invention provides a compound of the invention which is a compound formula (I):

$$E^{1a}\text{-}V^{1a}\text{—}C(=O)\text{—}P^{1a}\text{—}W^{1a}\text{—}P^{1b}\text{—}C(=O)\text{—}V^{1b}\text{-}E^{1b} \quad (I)$$

wherein:

$E^{1a}$ is $E^0$ or $E^1$, or $E^{1a}\text{-}V^{1a}$ taken together are $R^{9a}$;
$E^{1b}$ is $E^0$ or $E^1$, or $E^{1b}\text{-}V^{1b}$ taken together are $R^{9b}$;
$V^{1a}$ is $V^0$ or $E^{1a}\text{-}V^{1a}$ taken together are $R^{9a}$;
$V^{1b}$ is $V^0$ or $E^{1b}\text{-}V^{1b}$ taken together are $R^{9b}$;
$P^{1a}$ is selected from $P^0, P^1, P^3, P^5, P^6, P^7, P^8, P^{10}, P^{12}, P^{15}, P^{18}, P^{19}$, and $P^{30}$;
$P^{1b}$ is selected from $P^0, P^1, P^3, P^5, P^6, P^7, P^8, P^{10}, P^{12}, P^{15}, P^{18}, P^{19}$, and $P^{30}$;

each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each P$^0$ is independently:

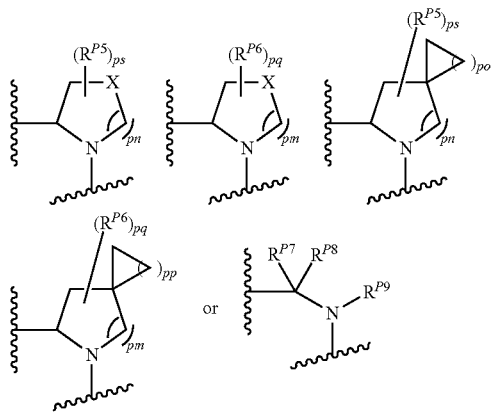

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;
R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;

each P$^1$ is independently:

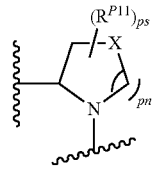

wherein:

X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocloxyalkyloxy, (NR$^h$R$^h$)alkyloxy, cyanoalkoxy, cyanocycloalkyloxy, cycloalkyloxy, oxo and heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

ps is 1, 2, 3, or 4;
pn is 0, 1, or 2;

each P³ is independently a ring of the formula:

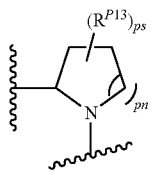

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyoxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;
each P⁵ is independently a ring of the formula:

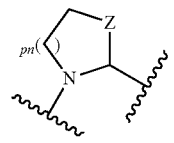

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pn is 0, 1, or 2;
Z is O, S, S(=O), S(=O)₂, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, sulfonylalkyl, —S(=O)₂$NR^hR^h$, —S(=O)₂$R^h$, C(=O)$R^h$, C(=O)O$R^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each P⁶ is independently a ring of the formula:

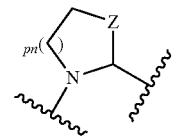

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
Z is O, S, S(=O), S(=O)₂, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)₂$NR^hR^h$, —S(=O)₂$R^h$, C(=O)$R^h$, C(=O)O$R^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each P⁷ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;
each P⁸ is independently a ring of the formula:

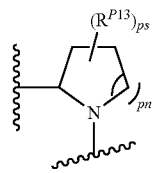

wherein:
ps is 2, 3, 4, 5, or 6;
pn is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

each $P^{10}$ is independently:

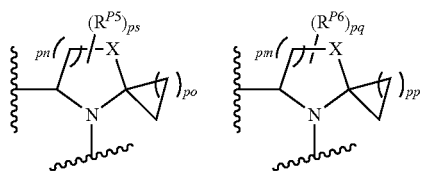

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;
each $P^{12}$ is independently:

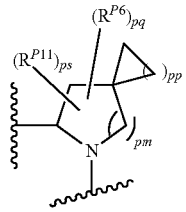

wherein:

each $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq is independently 0, 1, 2, 3, or 4;
pm is independently 0, 1, or 2;
pp is independently 1, 2, or 3;
ps is 1, 2, 3, or 4;

$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining $R^{P11}$ are independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{15}$ is:

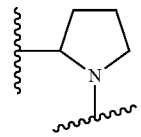

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

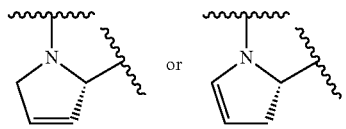 [SMILES: *[C@@H]1C=CCN1* ; *[C@@H]1CC=CN1*]

which is optionally substituted, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl with one or two groups independently selected from halo, alkyl, alkoxyalkyl, haloalkyl, cycloalkyl, and cycloalkylalkyl;

each $P^{19}$ is:

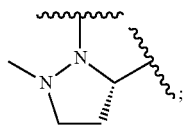

255 each P³⁰ is independently a ring of the formula:

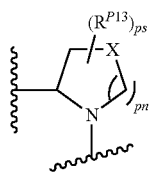

ps is 2
pn is 0, 1 or 2;
X is selected from O, S, S(O), SO₂, or CH₂; provided that when pn is 0, X is CH₂.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl; and $W^{1a}$ is selected from:

101

102 or

103

-continued

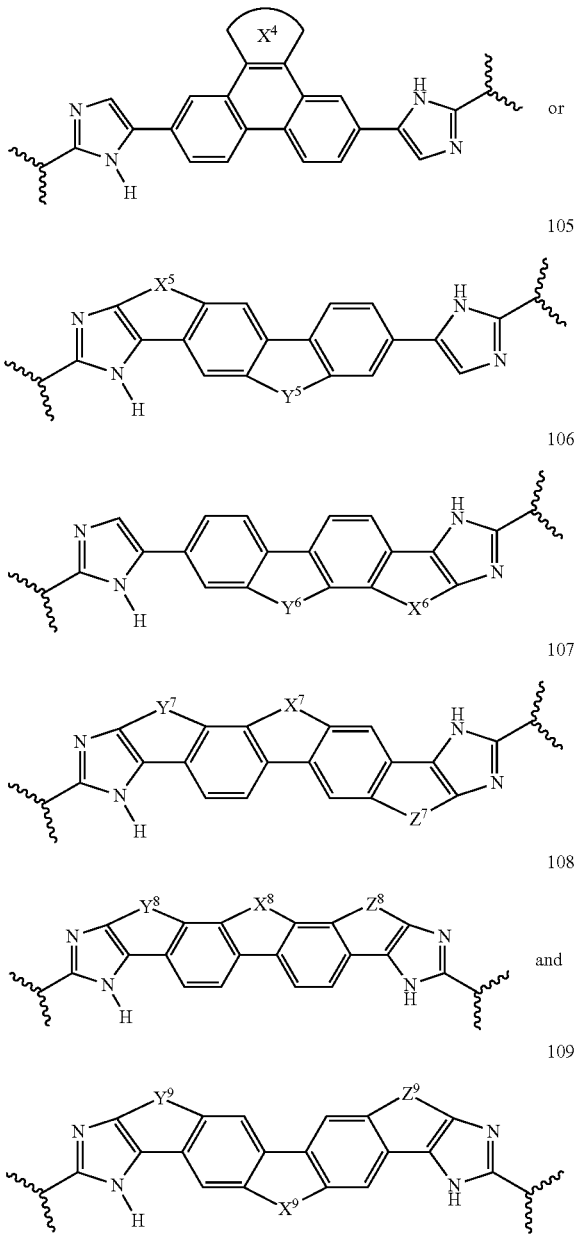

wherein each $W^{1a}$ is optionally substituted with one or more (e.g. 1, 2, 3, or 4) groups independently selected from halo, alkyl, haloalkyl, cyano, and

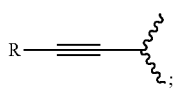

wherein each R is independently H, alkyl, haloalkyl, cycloalkyl, aryl, or heteroaryl;

$X^1$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$Y^1$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$X^2$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$X^3$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$Y^3$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$X^4$ is a six membered aromatic or heteroaromatic or five membered heteroraromatic ring;

$X^5$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$Y^5$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$X^6$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$Y^6$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$X^7$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$Y^7$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$Z^7$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$X^8$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$Y^8$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$Z^8$ is —$CH_2$—, —$CH_2$—$CH_2$—, —$CH_2$—O—, —$CH_2$—O—$CH_2$—, —S—, —$S(O)_2$—, —C(O)—, —$CF_2$—, —OC(O)—, —(O)CO—, or —CH=CH—;

$X^9$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

$Y^9$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—; and $Z^9$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —OC(O)—, —(O)CO—, or —CH=CH—;

or a pharmaceutically acceptable salt or prodrug thereof;

provided the compound of formula (I) is not:
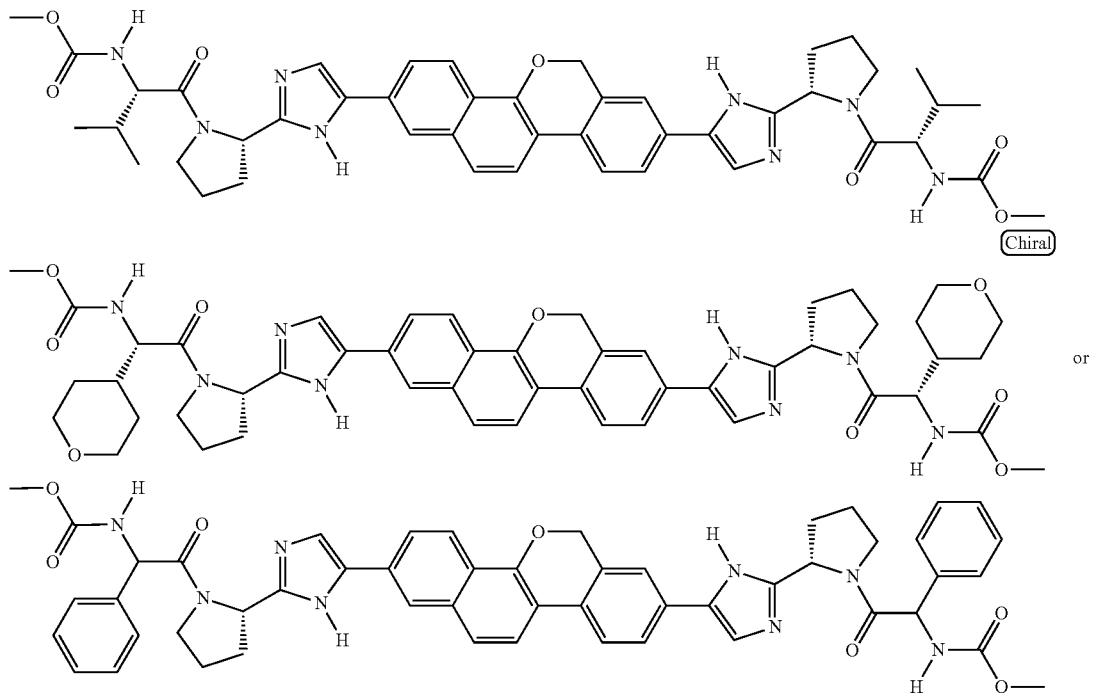
In one specific embodiment $E^{1a}$ is $E^0$.
In one specific embodiment $E^{1a}$ is $E^1$.
In one specific embodiment $E^{1a}$ is selected from:
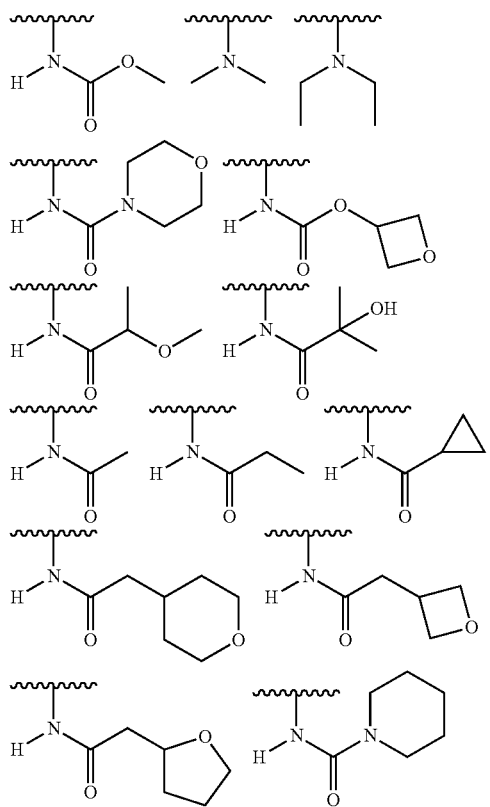
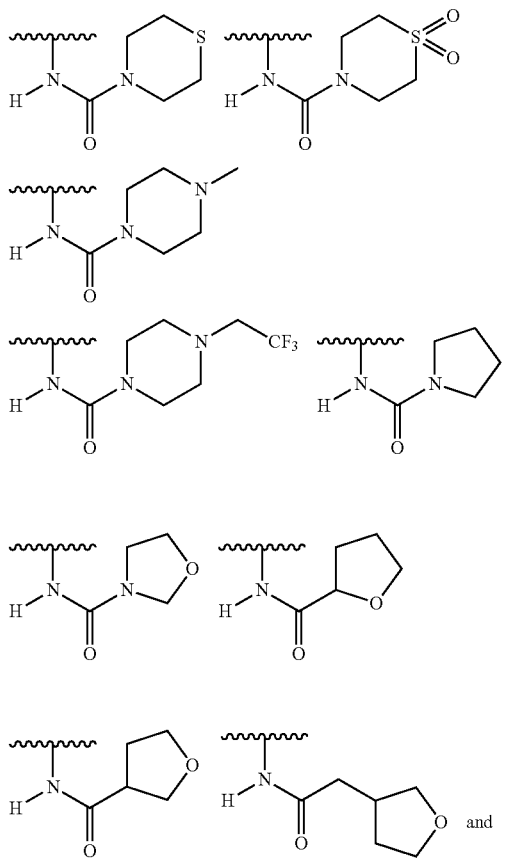
and

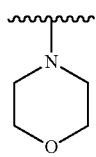

In one specific embodiment $E^{1a}$ is —N(H)alkoxycarbonyl.
In one specific embodiment $E^{1a}$ is —N(H)C(=O)OMe.
In one specific embodiment $E^{1b}$ is $E^0$.
In one specific embodiment
In one specific embodiment $E^{1b}$ is $E^1$.
In one specific embodiment $E^{1b}$ is selected from:

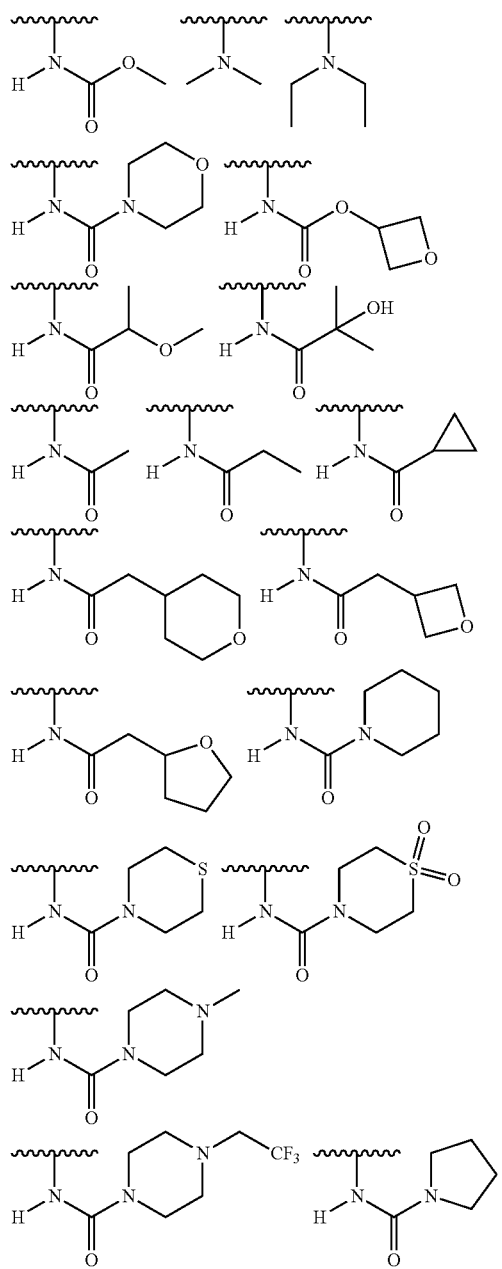

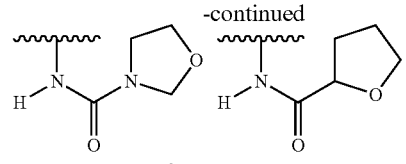

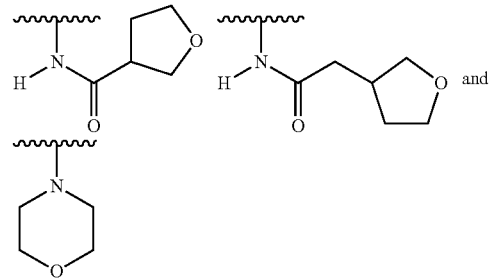

In one specific embodiment $E^{1b}$ is —N(H)alkoxycarbonyl.
In one specific embodiment $E^{1b}$ is —N(H)C(=O)OMe.
In one specific embodiment $V^{1a}$ is $V^0$.
In one specific embodiment $V^{1a}$ is selected from:

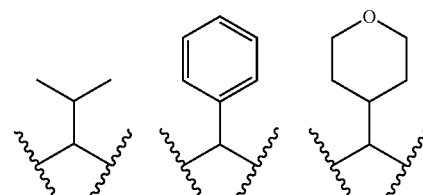
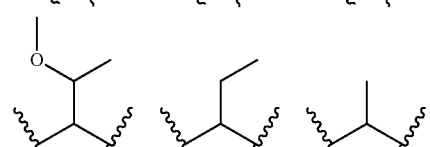
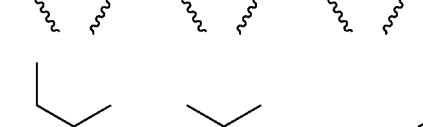
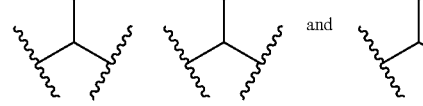

In one specific embodiment $V^{1b}$ is $V^0$.
In one specific embodiment $V^{1b}$ is selected from:

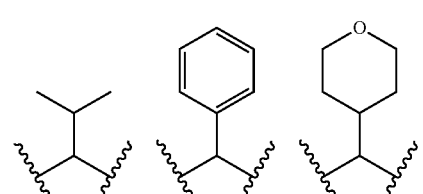
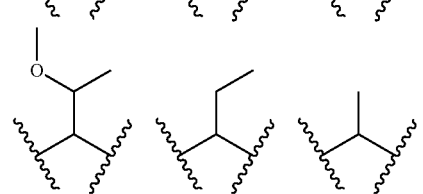

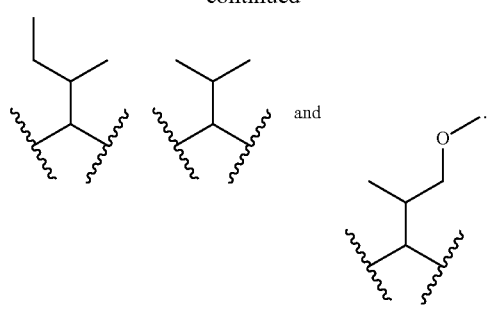
In one specific embodiment $E^{1a}$-$V^{1a}$ taken together are $R^{9a}$.
In one specific embodiment $R^{9a}$ is selected from:
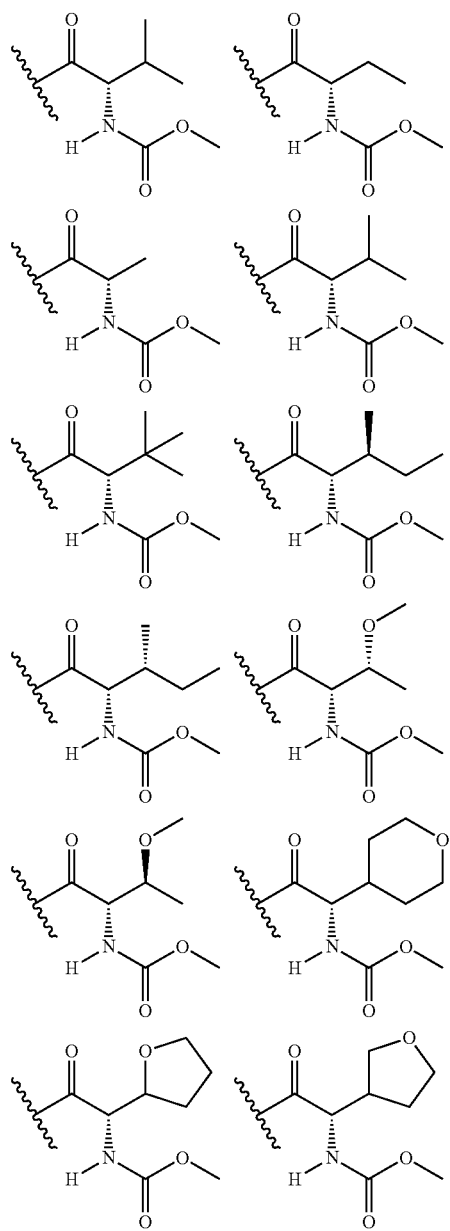
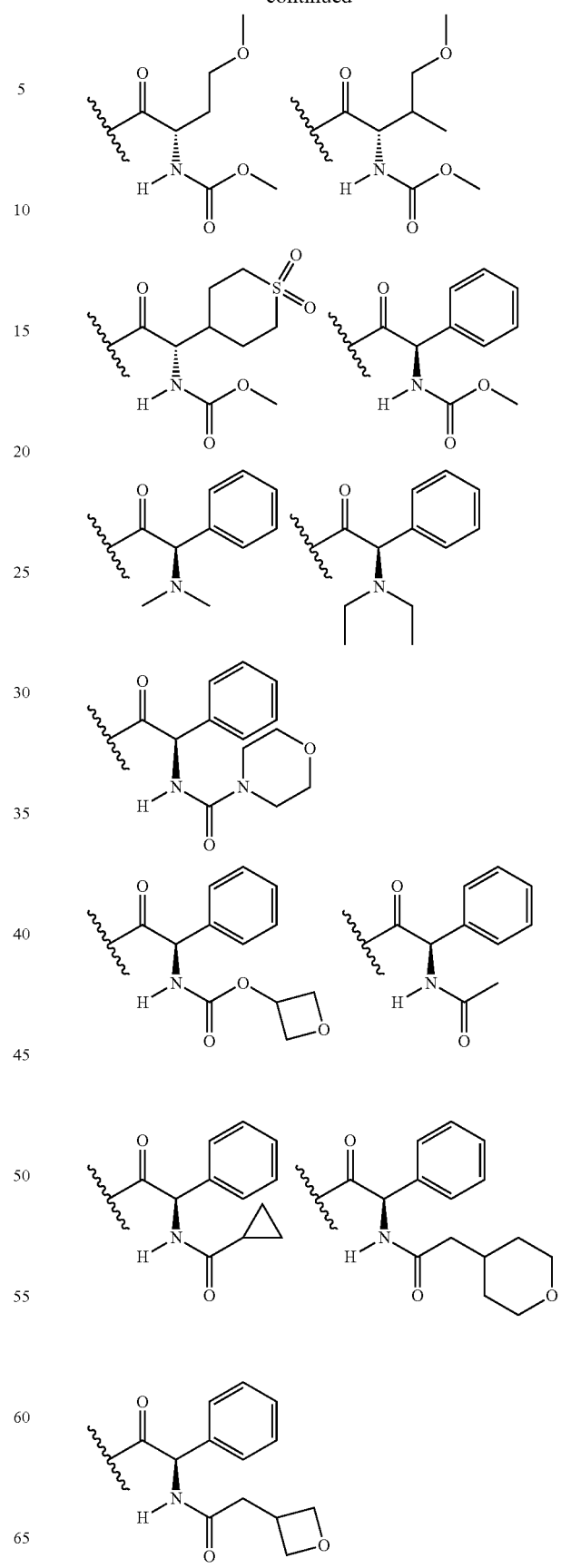

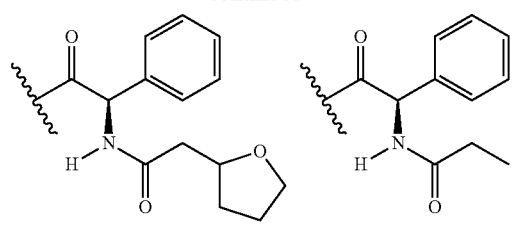
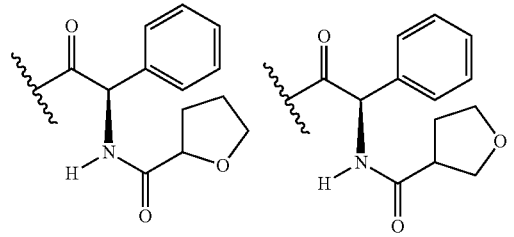
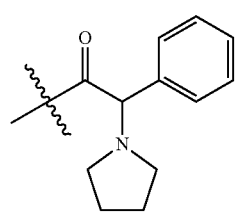
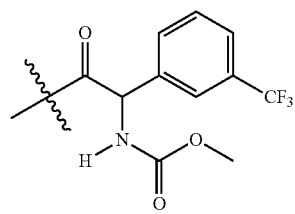
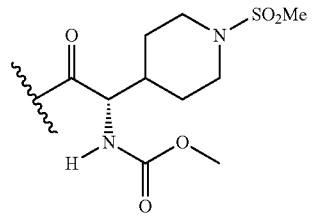
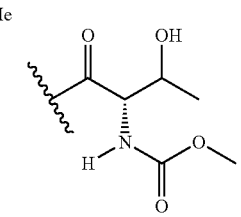
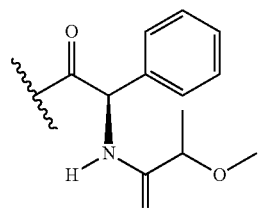
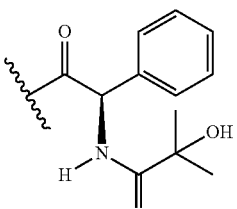
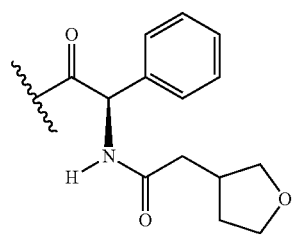
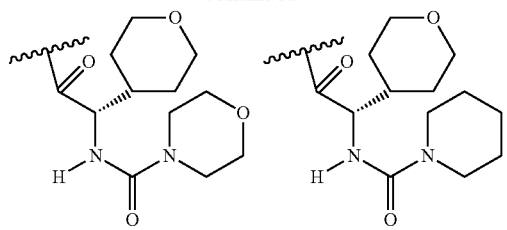
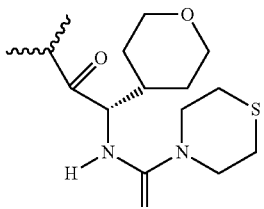
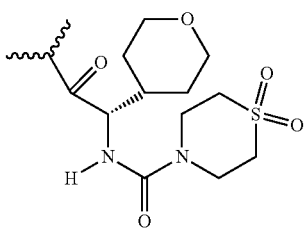
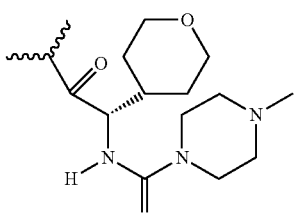
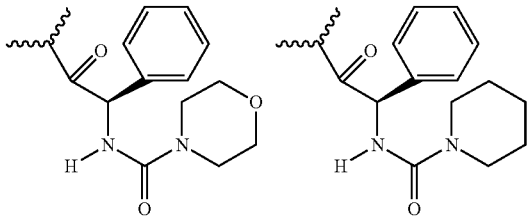
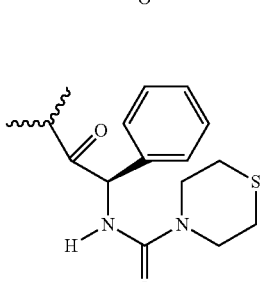
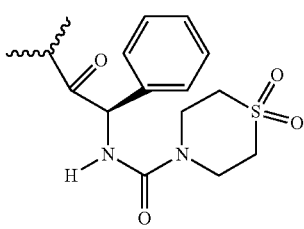

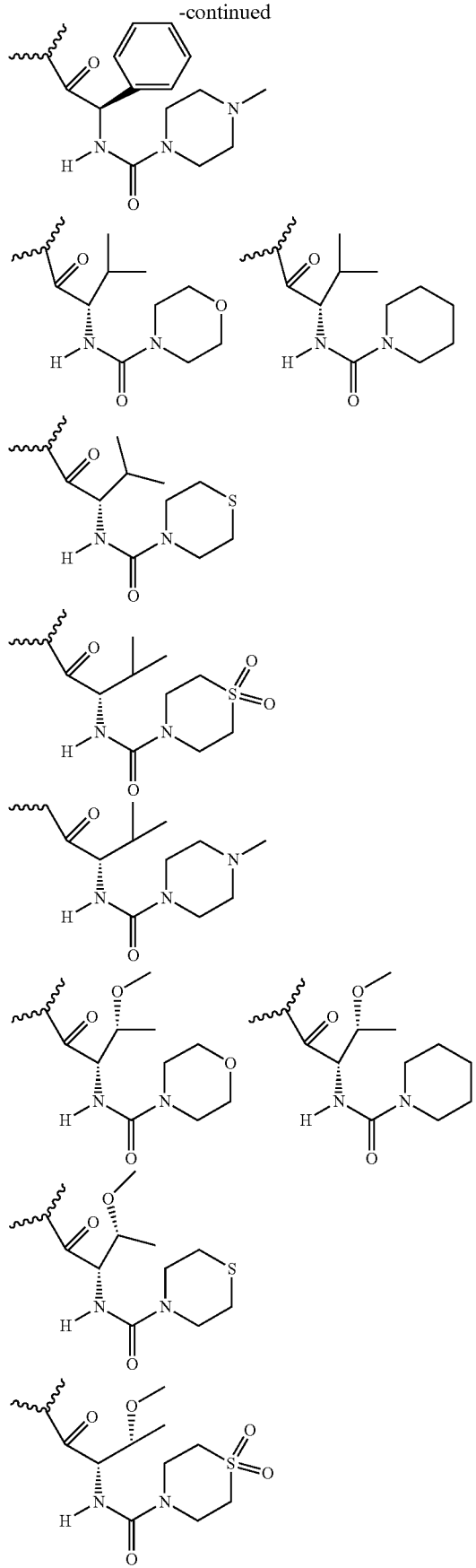
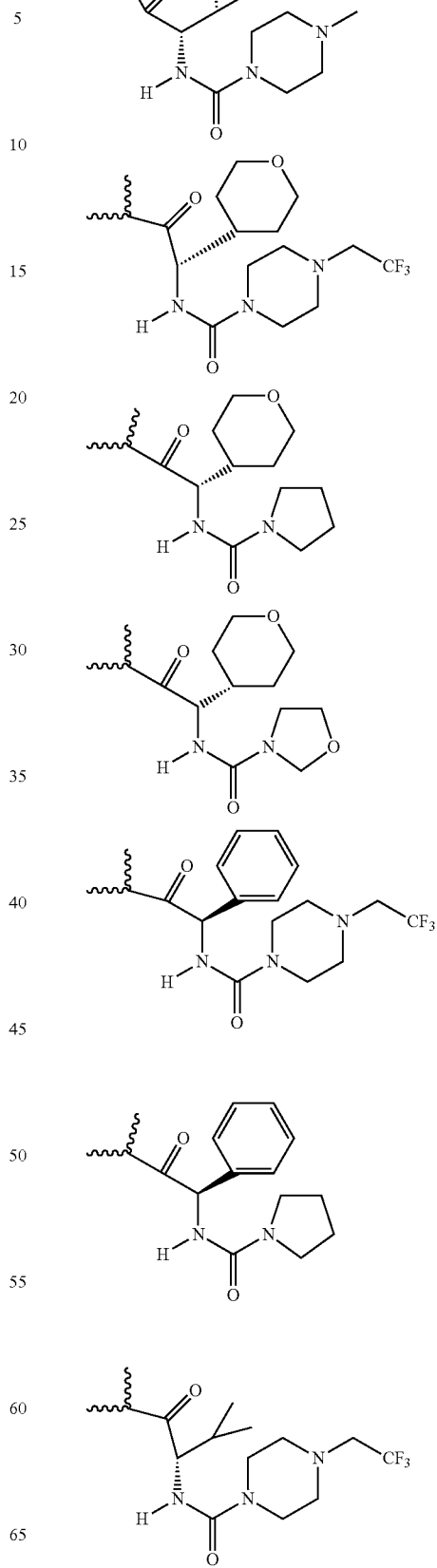

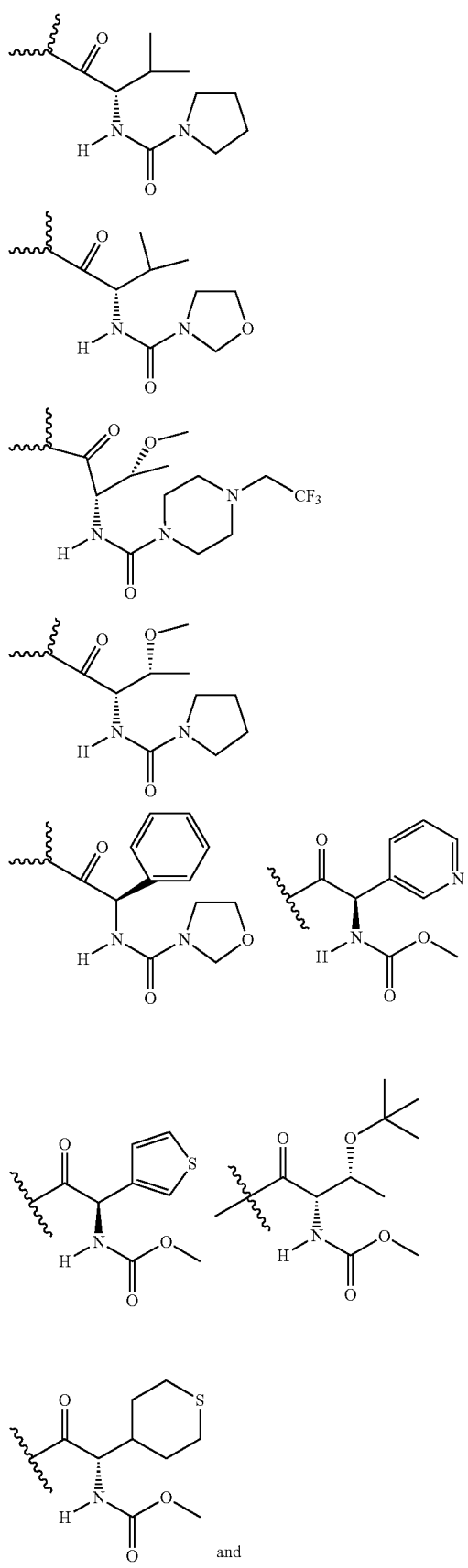
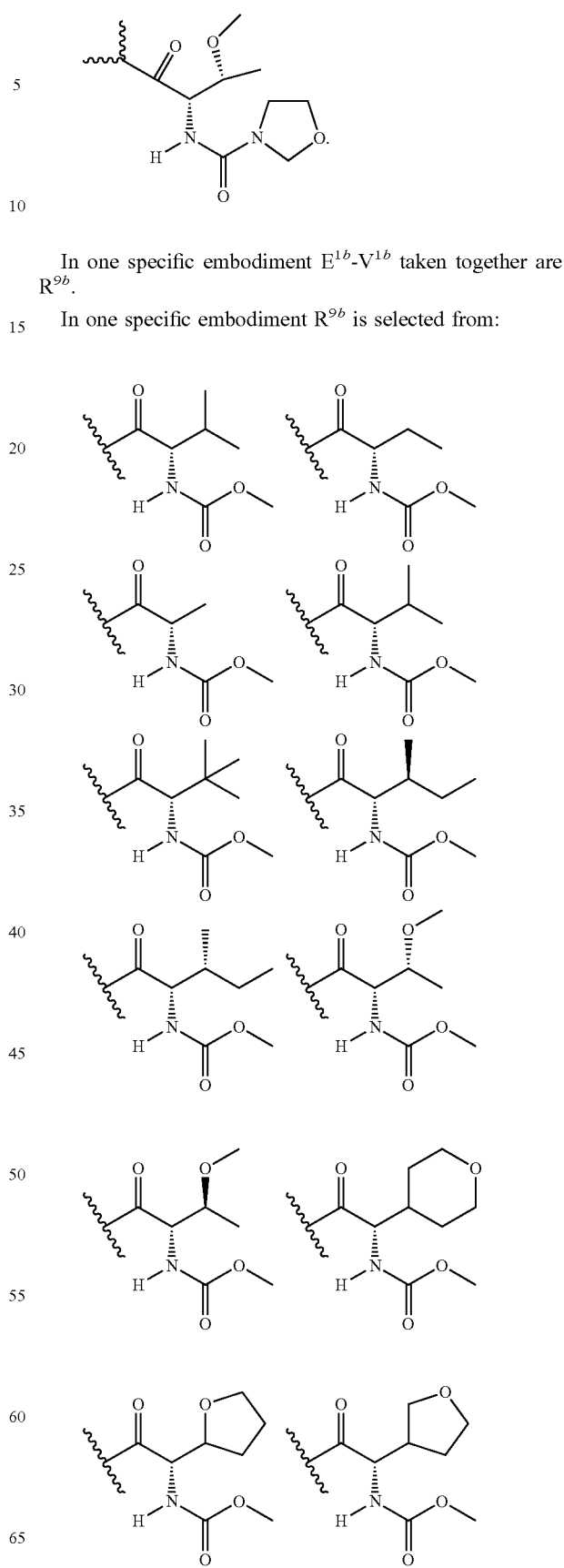
In one specific embodiment $E^{1b}$-$V^{1b}$ taken together are $R^{9b}$.
In one specific embodiment $R^{9b}$ is selected from:

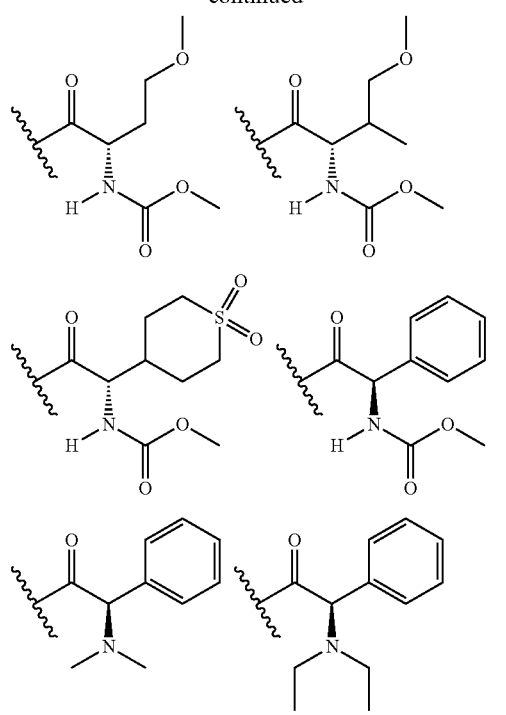
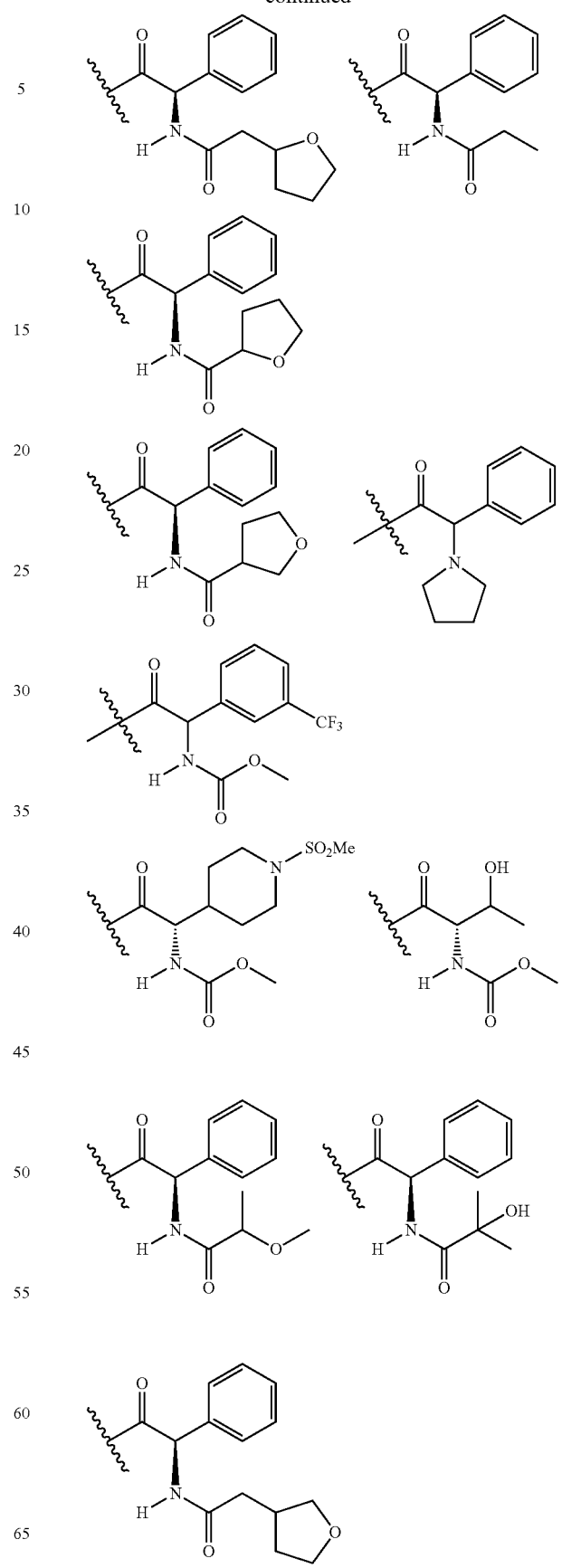

273
-continued
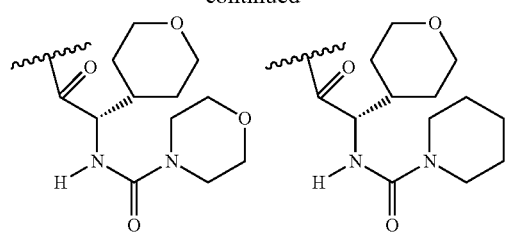
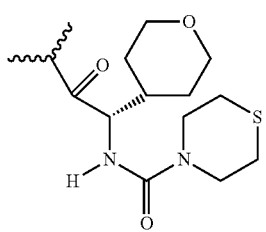
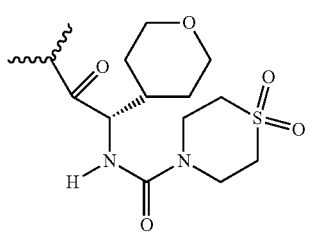
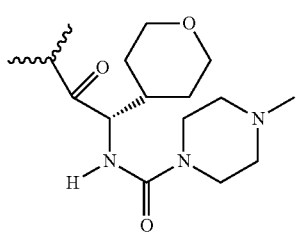
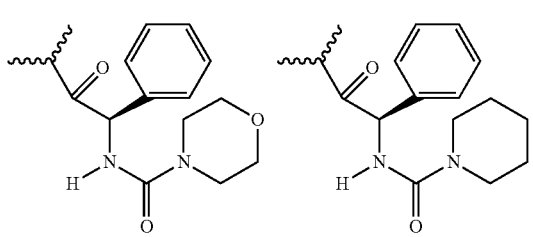
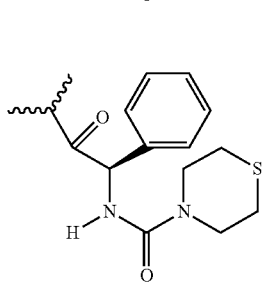
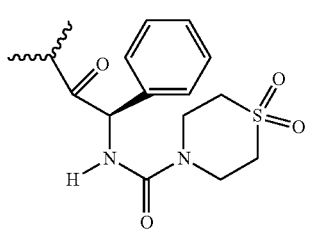
274
-continued
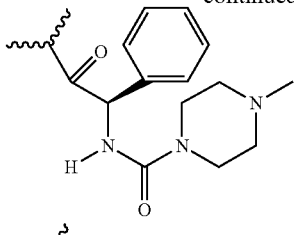
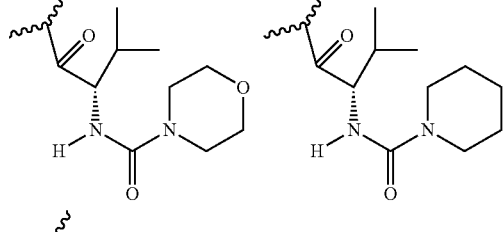
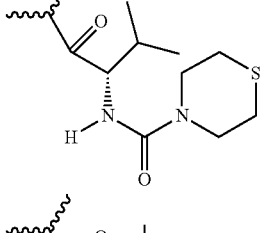
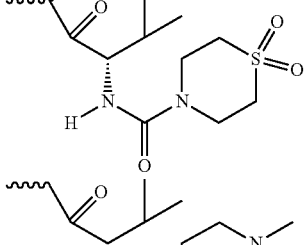
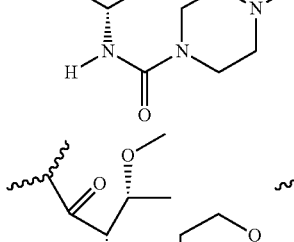
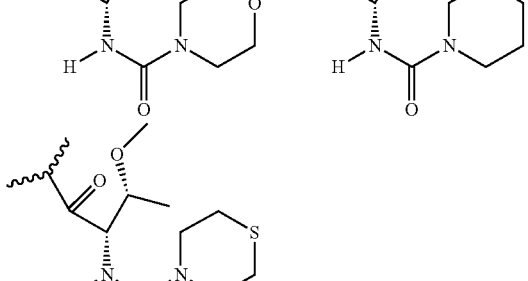
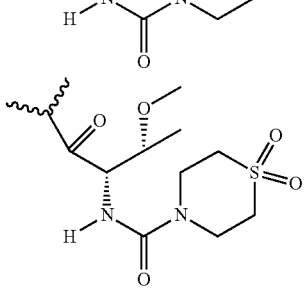

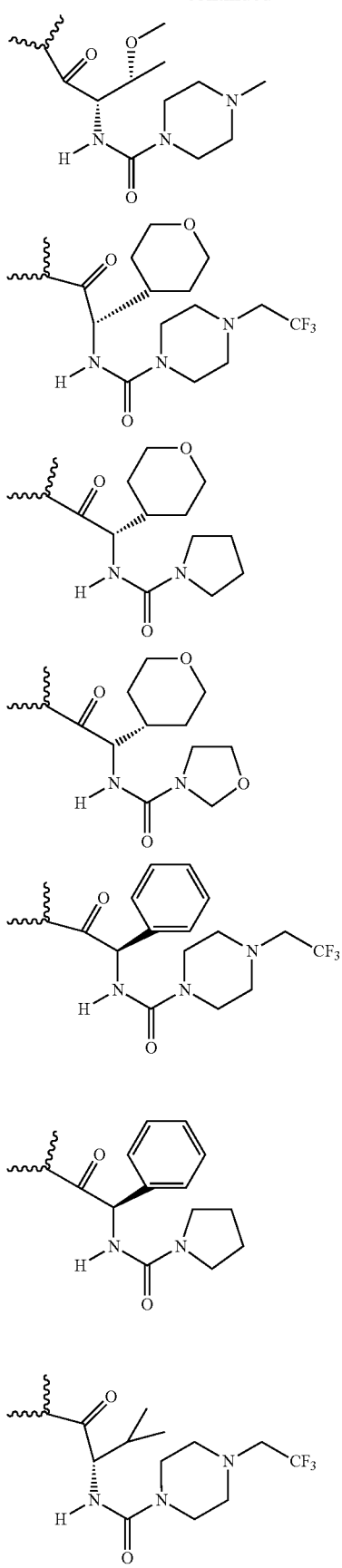
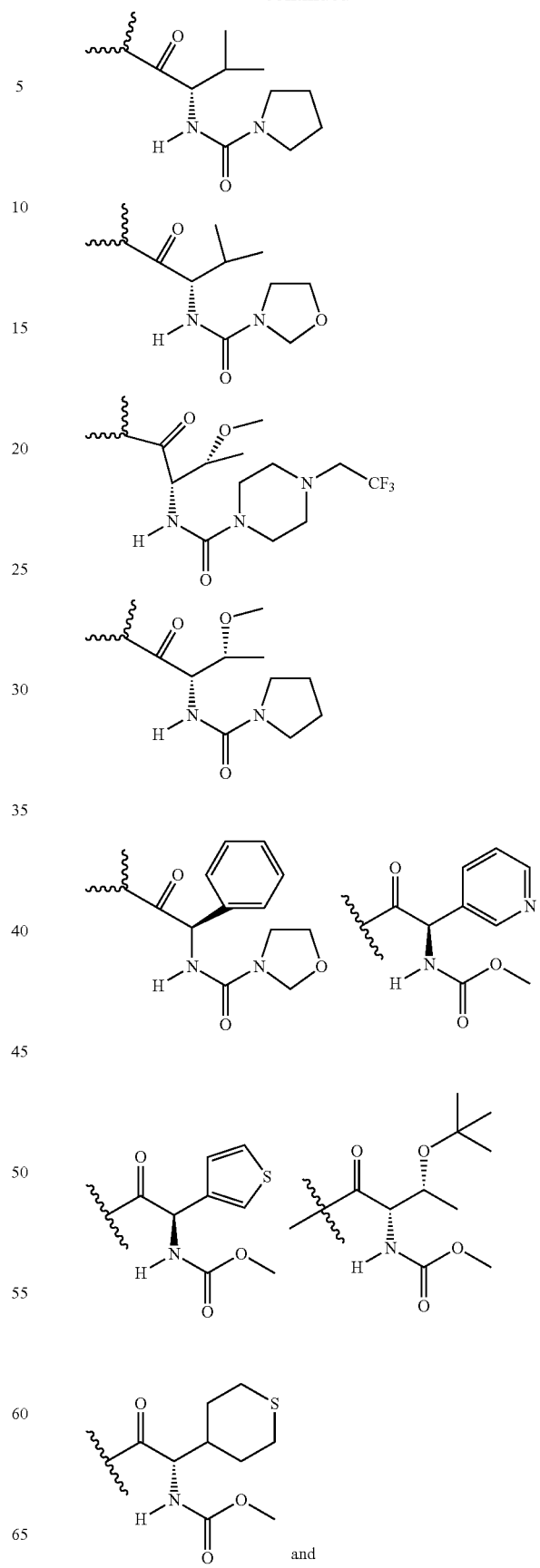
and

-continued

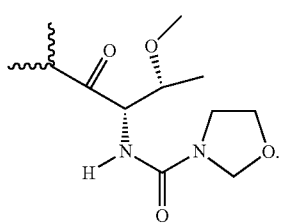

In one specific embodiment $P^{1a}$ is $P^0$.
In one specific embodiment $P^{1a}$ is selected from:

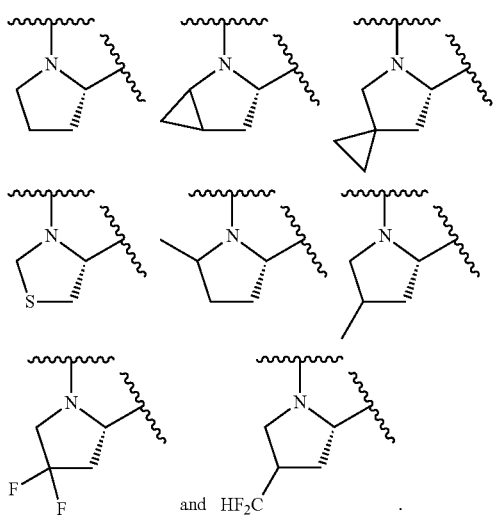

In one specific embodiment $P^{1a}$ is $P^1$.
In one specific embodiment $P^{1a}$ is selected from:

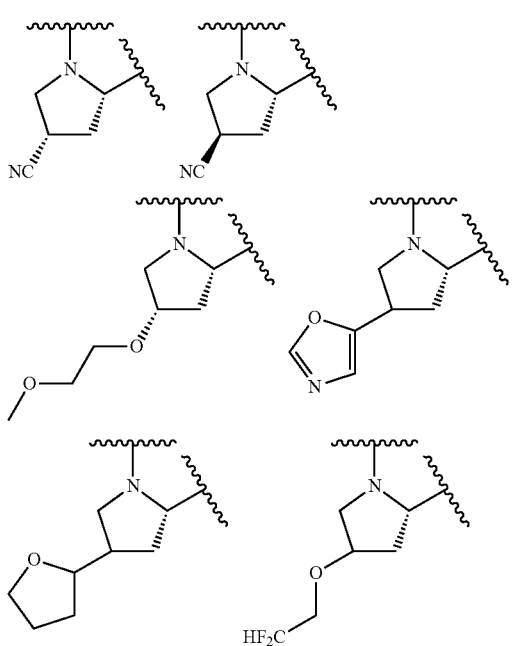

-continued

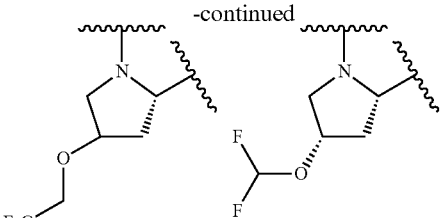

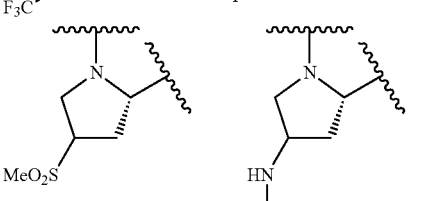

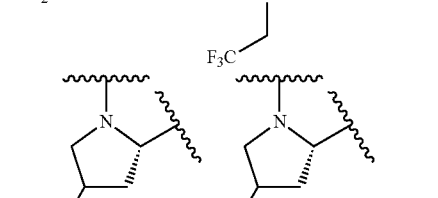

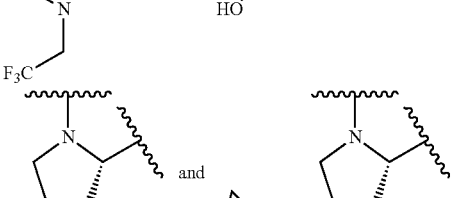

In one specific embodiment $P^{1a}$ is $P^3$.
In one specific embodiment $P^{1a}$ is selected from:


In one specific embodiment $P^{1a}$ is $P^5$.
In one specific embodiment $P^{1a}$ is selected from:

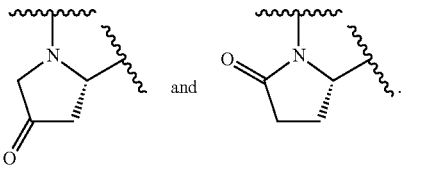 [SMILES: *[C@@H]1CC(=O)CN1* ; *[C@@H]1CCC(=O)N1*]

In one specific embodiment $P^{1a}$ is $P^6$.
In one specific embodiment $P^{1a}$ is:

In one specific embodiment $P^{1a}$ is $P^7$.

In one specific embodiment $P^{1a}$ is:

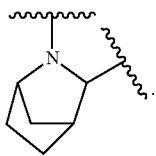 [SMILES: *C1C2CCC(C2)N1*]

In one specific embodiment $P^{1a}$ is $P^8$.
In one specific embodiment $P^{1a}$ is selected from:

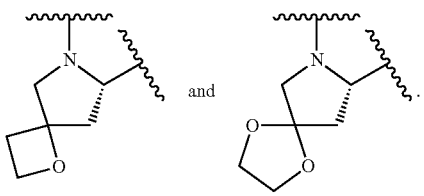

In one specific embodiment $P^{1a}$ is $P^{10}$.
In one specific embodiment $P^{1a}$ is:

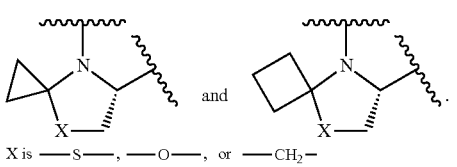

X is —S—, —O—, or —CH$_2$—

In one specific embodiment $P^{1a}$ is $P^{12}$.
In one specific embodiment $P^{1a}$ is $P^{15}$.
In one specific embodiment $P^{1a}$ is selected from:

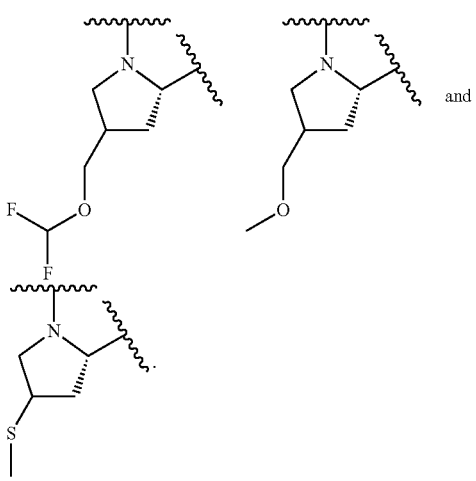

In one specific embodiment $P^{1a}$ is $P^{18}$.
In one specific embodiment $P^{1a}$ is:

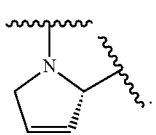 [SMILES: *[C@@H]1C=CCN1*]

In one specific embodiment $P^{1b}$ is $P^0$.

In one specific embodiment $P^{1b}$ is selected from:

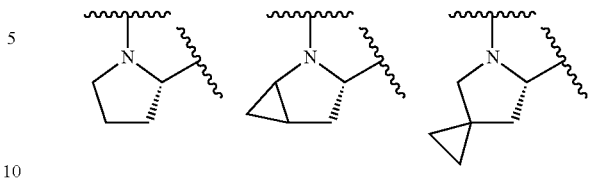

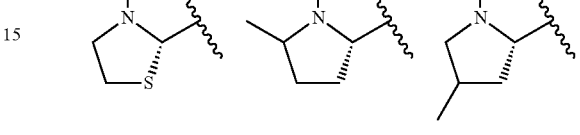

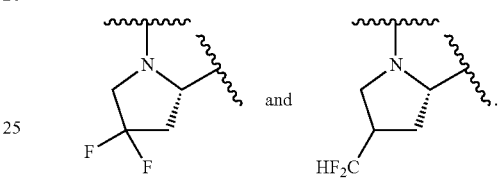

In one specific embodiment $P^{1b}$ is $P^1$.
In one specific embodiment $P^{1b}$ is selected from:

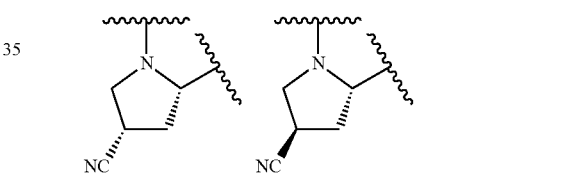

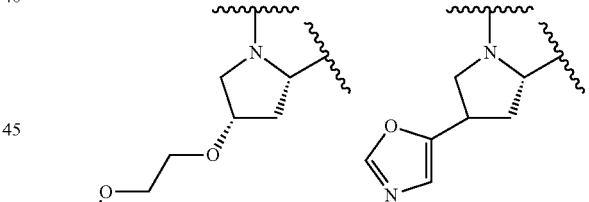

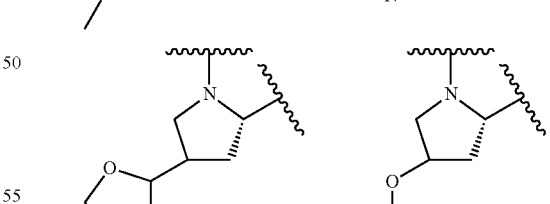

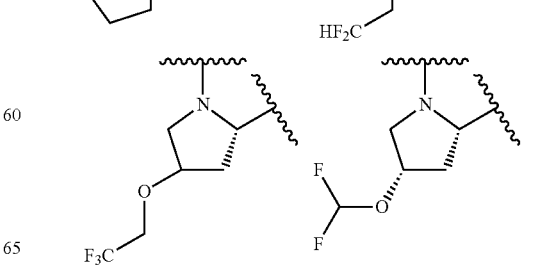

-continued

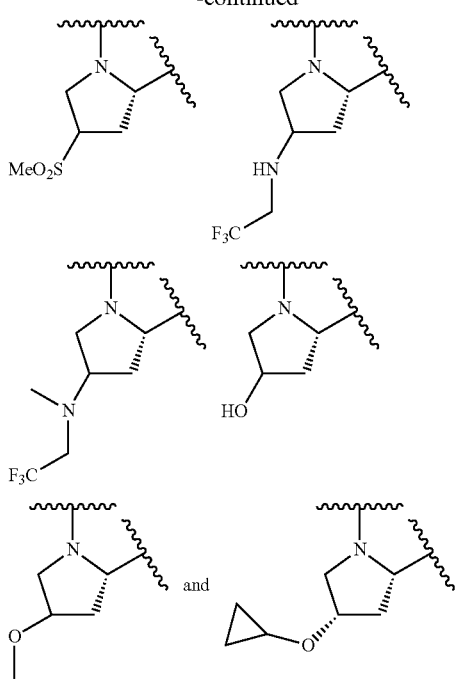

In one specific embodiment $P^{1b}$ is $P^3$.
In one specific embodiment $P^{1b}$ is selected from:

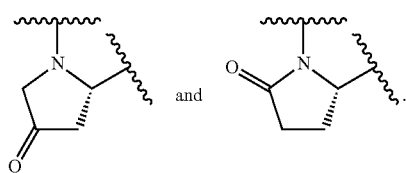 [SMILES: *[C@@H]1CC(=O)CN1* ; *[C@@H]1CCC(=O)N1*]

In one specific embodiment $P^{1b}$ is $P^5$.
In one specific embodiment $P^{1b}$ is selected from:

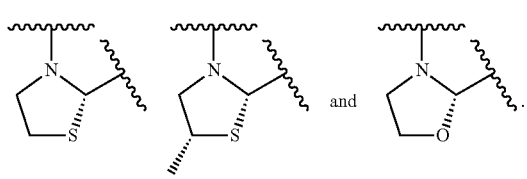

In one specific embodiment $P^{1b}$ is $P^6$.
In one specific embodiment $P^{1b}$ is:

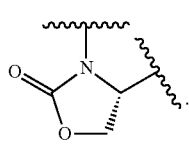

In one specific embodiment $P^{1b}$ is $P^7$.

In one specific embodiment $P^{1b}$ is:

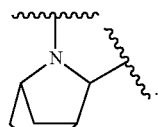

In one specific embodiment $P^{1b}$ is $P^8$.
In one specific embodiment $P^{1b}$ is selected from:

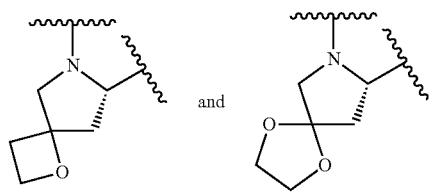

In one specific embodiment $P^{1b}$ is $P^{10}$.
In one specific embodiment $P^{1b}$ is:

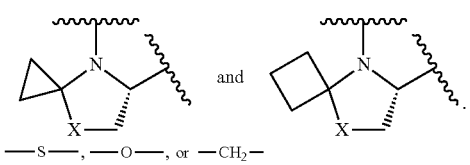

X is —S—, —O—, or —CH$_2$—

In one specific embodiment $P^{1b}$ is $P^{12}$.
In one specific embodiment $P^{1b}$ is $P^{15}$.
In one specific embodiment $P^{1a}$ is selected from:

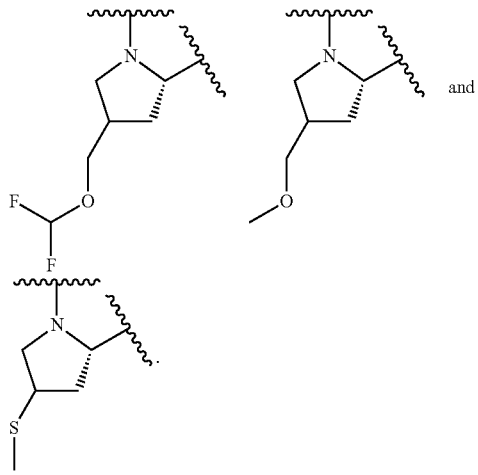

In one specific embodiment $P^{1b}$ is $P^{18}$.
In one specific embodiment $P^{1b}$ is:

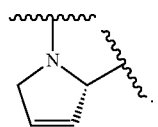

In one specific embodiment at least one of $P^{1a}$ and $P^{1b}$ is:

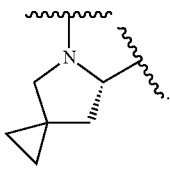 [SMILES: *[C@@H]1CC2(CC2)CN1*]

In one specific embodiment at least one of $P^{1a}$ and $P^{1b}$ is selected from:

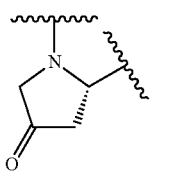 and 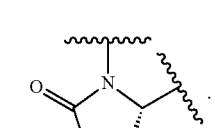

In one specific embodiment at least one of $P^{1a}$ and $P^{1b}$ is selected from:

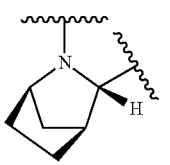 and 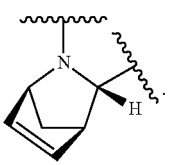

In one specific embodiment at least one of $P^{1a}$ and $P^{1b}$ is selected from:

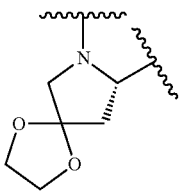 and 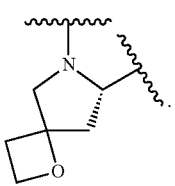

In one specific embodiment at least one of $P^{1a}$ and $P^{1b}$:

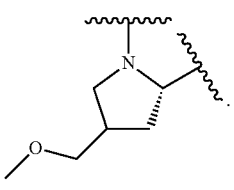

In one specific embodiment at least one of $P^{1a}$ and $P^{1b}$:

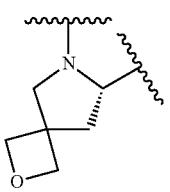 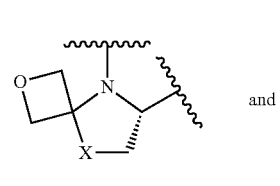 and

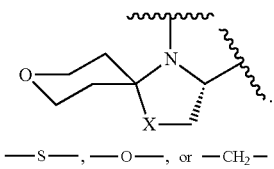

X is —S—, —O—, or —CH$_2$—

In one specific embodiment at least one of $P^{1a}$ and $P^{1b}$:

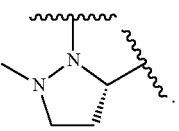

In one specific embodiment $P^{1a}$ is:

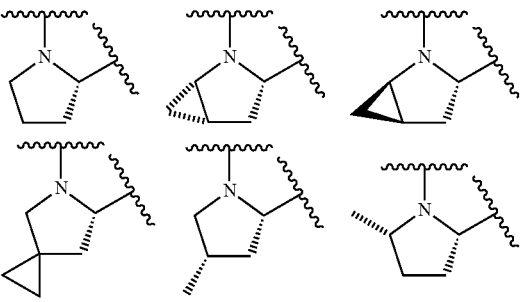

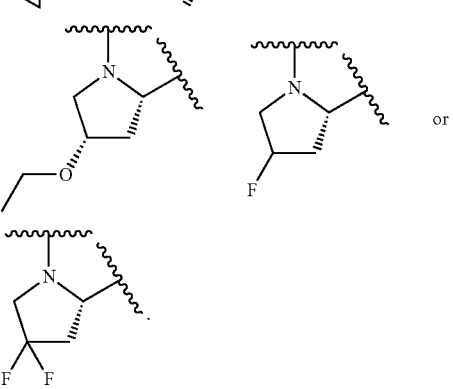

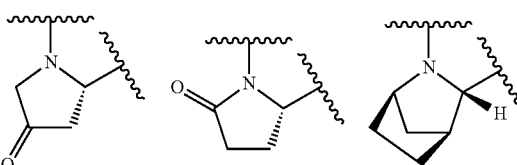

In one specific embodiment $P^{1a}$ is selected from:

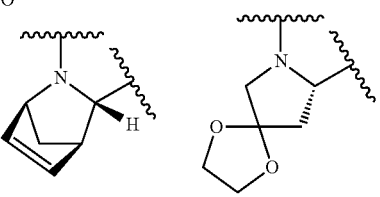

-continued

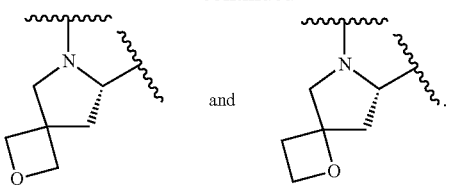

In one specific embodiment P$^{1b}$ is selected from

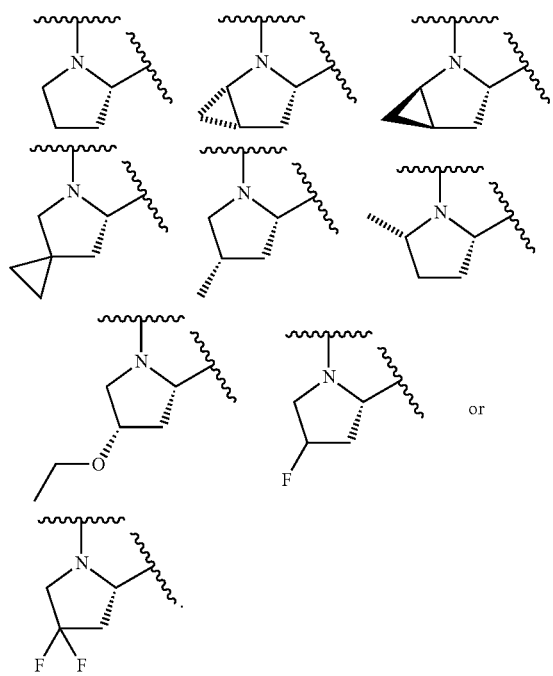

In one specific embodiment P$^{1b}$ is selected from:

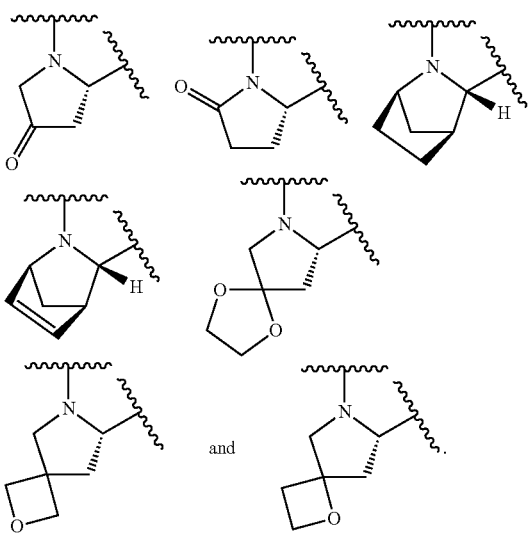

In one specific embodiment W$^{1a}$ is 101, 102, 103, or 104.
In one specific embodiment W$^{1a}$ is 105 or 106.

In one specific embodiment W$^{1a}$ is

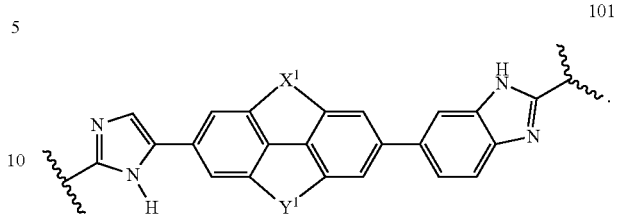

In one specific embodiment X$^1$ is —CH$_2$—, —CH$_2$—CH$_2$—, —CH$_2$—O—, —O—CH$_2$—, —CH$_2$—O—CH$_2$—, or —CH=CH—.

In one specific embodiment Y$^1$ is —CH$_2$—, —CH$_2$—CH$_2$—, —CH$_2$—O—, —O—CH$_2$—, —CH$_2$—O—CH$_2$—, or —CH=CH—.

In one specific embodiment W$^{1a}$ is:

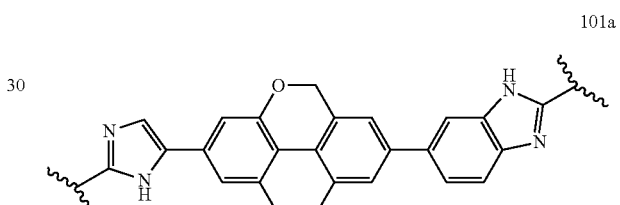

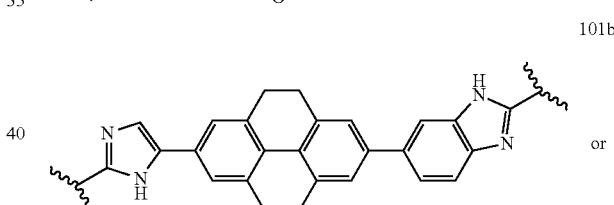

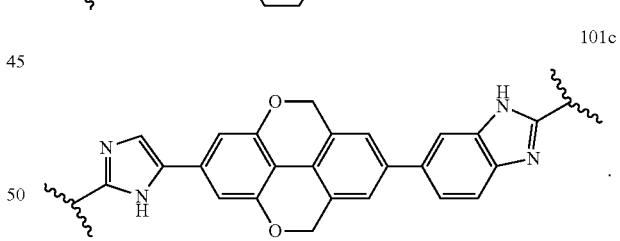

In one specific embodiment W$^{1a}$ is

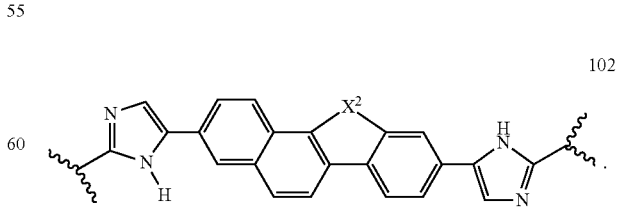

In one specific embodiment X$^2$ is —CH$_2$—, —CH$_2$—CH$_2$—, —CH$_2$—O—, —O—CH$_2$—, —CH$_2$—O—CH$_2$—, or —CH=CH—.

In one specific embodiment $W^{1a}$ is:

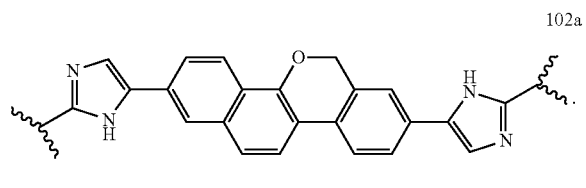 [SMILES: *c1ncc(-c2ccc3c(c2)COc2c-3ccc3cc(-c4cnc(*)[nH]4)ccc23)[nH]1]
102a

In one specific embodiment $W^{1a}$ is:

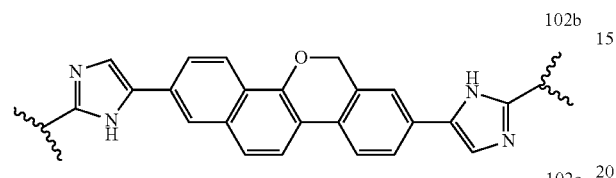
102b

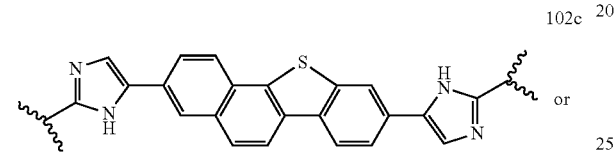
102c or

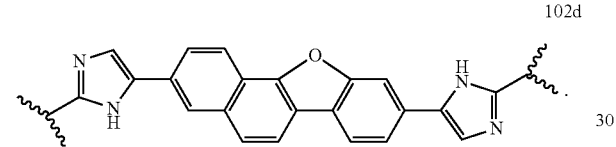
102d

In one specific embodiment $W^{1a}$ is

103

In one specific embodiment $X^3$ is —CH$_2$—, —CH$_2$—CH$_2$—, —CH$_2$—O—, —O—CH$_2$—, —CH$_2$—O—CH$_2$—, or —CH=CH—.

In one specific embodiment $Y^3$ is —CH$_2$—, —CH$_2$—CH$_2$—, —CH$_2$—O—, —O—CH$_2$—, —CH$_2$—O—CH$_2$—, or —CH=CH—.

In one specific embodiment $W^{1a}$ is:

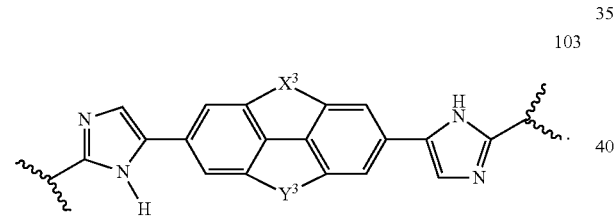
103a

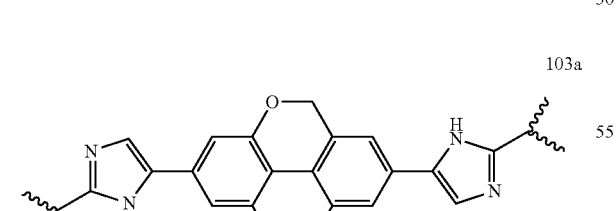
103b or

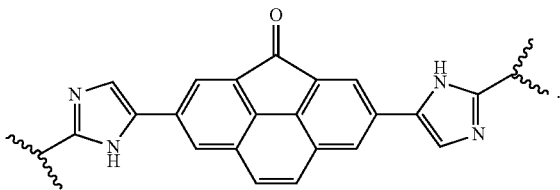
103c

In one specific embodiment $W^{1a}$ is:

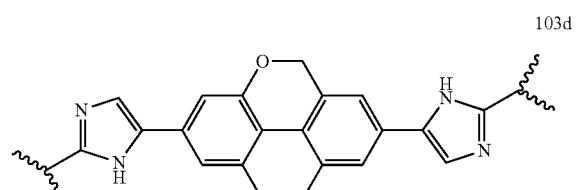
103d

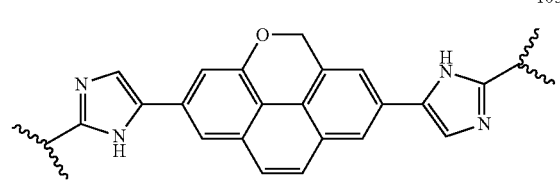
103e

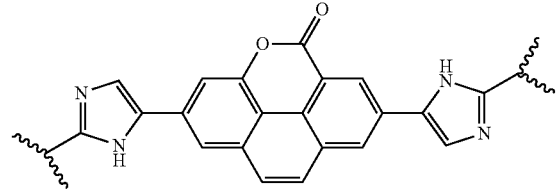
103f

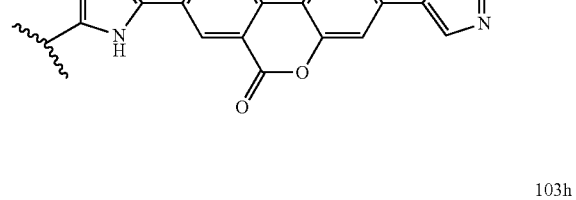
103g

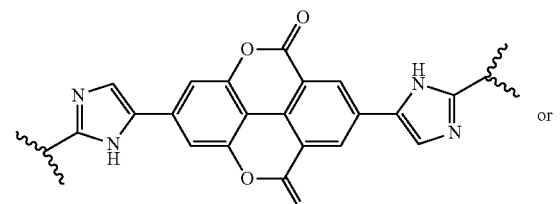
103h or

103i
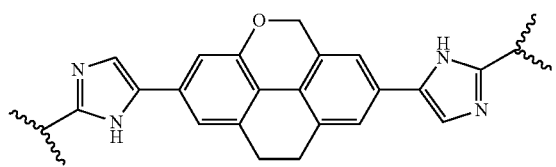
In one specific embodiment $W^{1a}$ is
104a
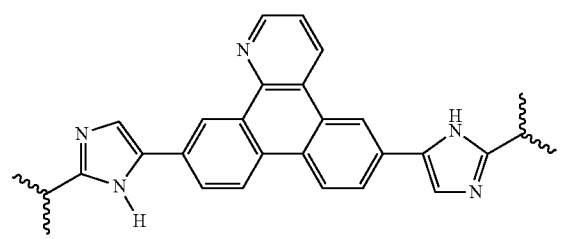
104b
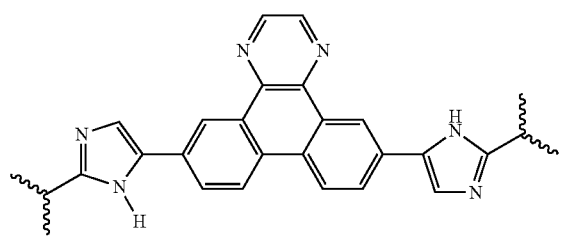
104c
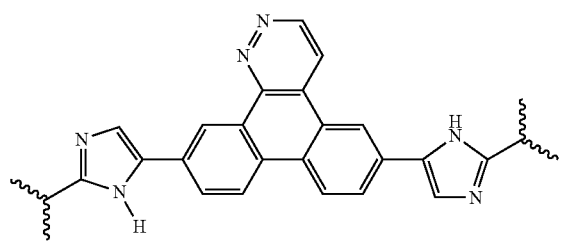
104d
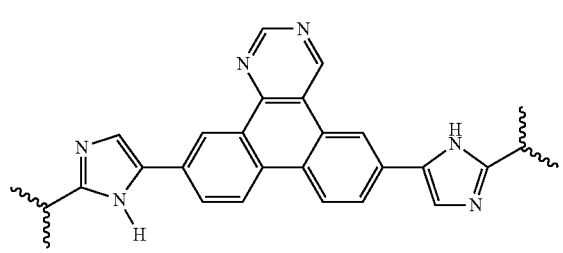
104e
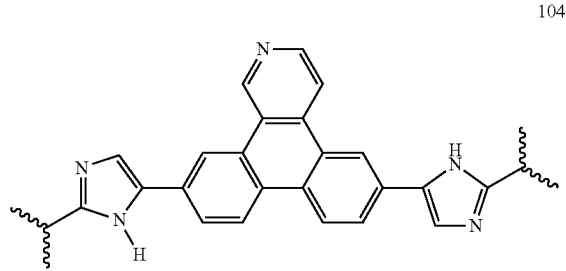
104f
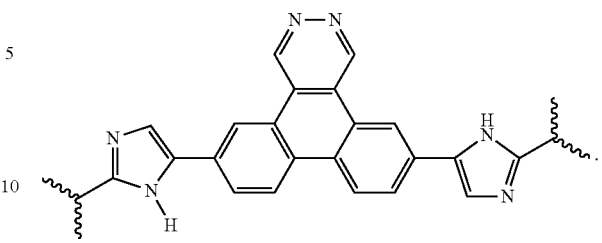
In one specific embodiment $W^{1a}$ is
104g
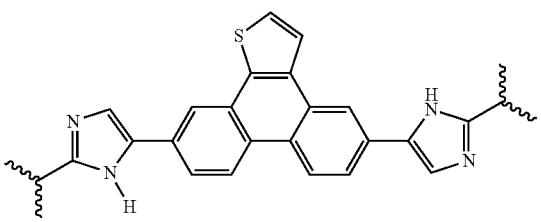
104h
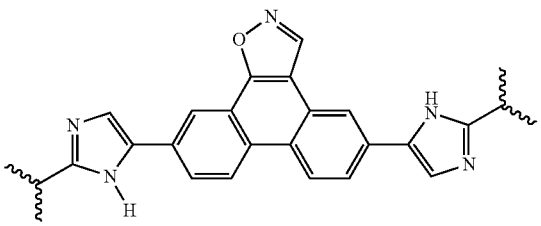
104o
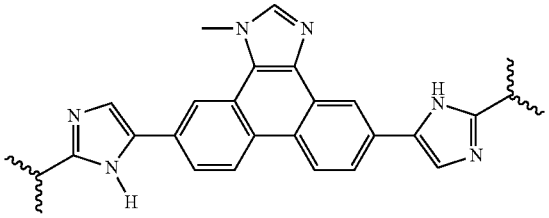
104i
104j
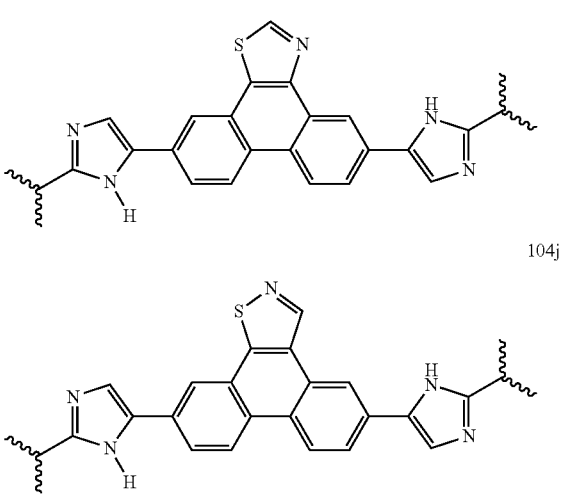

104p
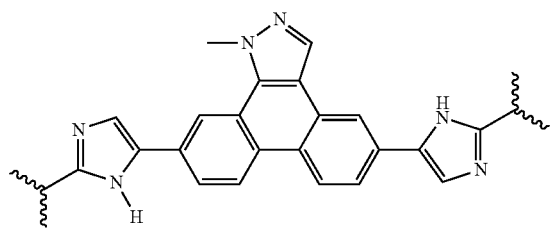

104k
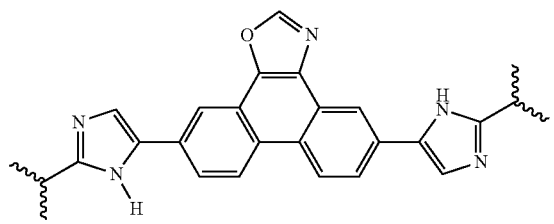

104l
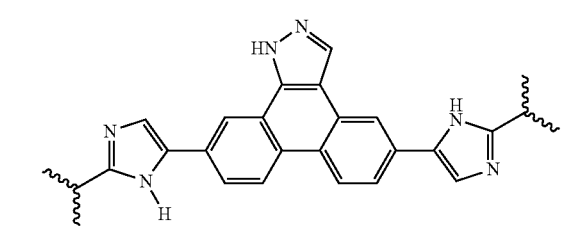

104m
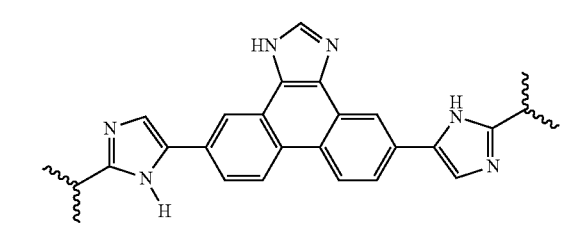

104n
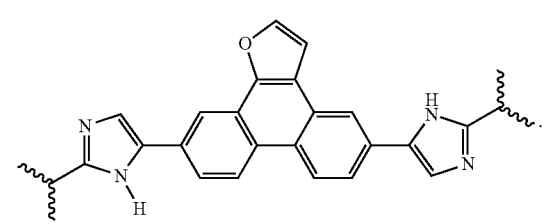

In one specific embodiment $W^{1a}$ is:

101a
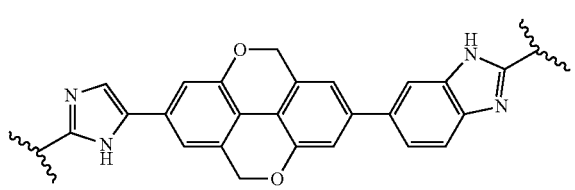

In one specific embodiment $W^{1a}$ is:

101b
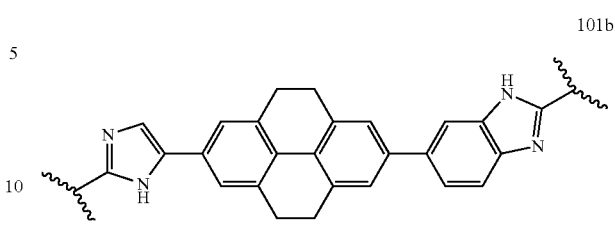

In one specific embodiment $W^{1a}$ is:

104q
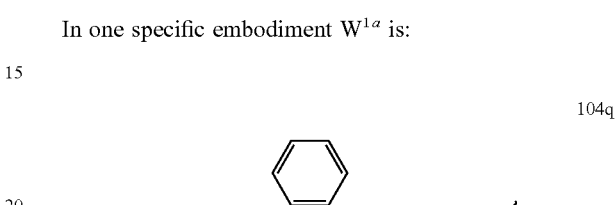

or

104b
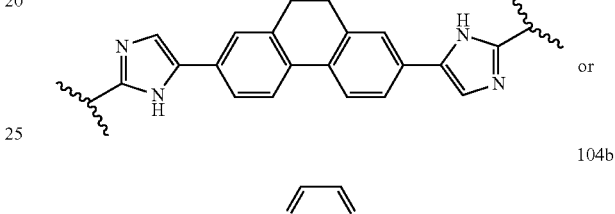

In one specific embodiment $W^{1a}$ is

105
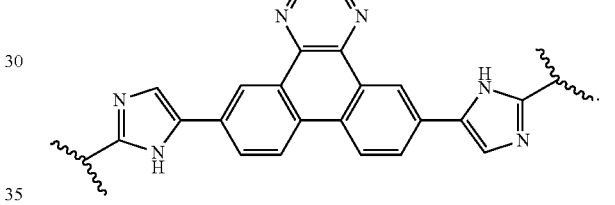

In one specific embodiment $X^5$ is —CH$_2$—, —CH$_2$—CH$_2$—, —CH$_2$—O—, —O—CH$_2$—, —CH$_2$—O—CH$_2$—, or —CH=CH—.

In one specific embodiment $Y^5$ is —CH$_2$—, —CH$_2$—CH$_2$—, —CH$_2$—O—, —O—CH$_2$—, —CH$_2$—O—CH$_2$—, or —CH=CH—.

In one specific embodiment $W^{1a}$ is

106
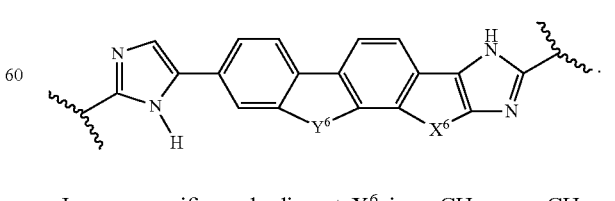

In one specific embodiment $X^6$ is —CH$_2$—, —CH$_2$—CH$_2$—, —CH$_2$—O—, —O—CH$_2$—, —CH$_2$—O—CH$_2$—, or —CH=CH—.

In one specific embodiment $Y^6$ is —$CH_2$—, —$CH_2$—$CH_2$—, —$CH_2$—O—, —O—$CH_2$—, —$CH_2$—O—$CH_2$—, or —CH=CH—.

In one specific embodiment $W^{1a}$ is

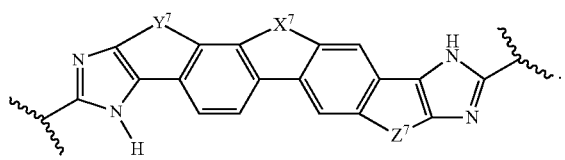

107

In one specific embodiment $X^7$ is —$CH_2$—, —$CH_2$—$CH_2$—, —$CH_2$—O—, —O—$CH_2$—, —$CH_2$—O—$CH_2$—, or —CH=CH—.

In one specific embodiment $Y^7$ is —$CH_2$—, —$CH_2$—$CH_2$—, —$CH_2$—O—, —O—$CH_2$—, —$CH_2$—O—$CH_2$—, or —CH=CH—.

In one specific embodiment $Z^7$ is —$CH_2$—, —$CH_2$—$CH_2$—, —$CH_2$—O—, —O—$CH_2$—, —$CH_2$—O—$CH_2$—, or —CH=CH—.

In one specific embodiment $W^{1a}$ is

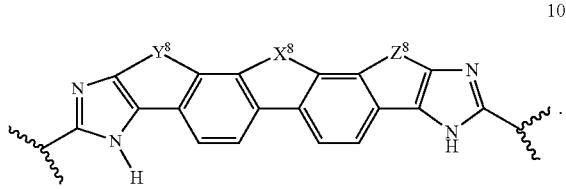

108

In one specific embodiment $X^8$ is —$CH_2$—, —$CH_2$—$CH_2$—, —$CH_2$—O—, —O—$CH_2$—, —$CH_2$—O—$CH_2$—, or —CH=CH—.

In one specific embodiment $Y^8$ is —$CH_2$—, —$CH_2$—$CH_2$—, —$CH_2$—O—, —O—$CH_2$—, —$CH_2$—O—$CH_2$—, or —CH=CH—.

In one specific embodiment $Z^8$ is —$CH_2$—, —$CH_2$—$CH_2$—, —$CH_2$—O—, —O—$CH_2$—, —$CH_2$—O—$CH_2$—, or —CH=CH—.

In one specific embodiment $W^{1a}$ is

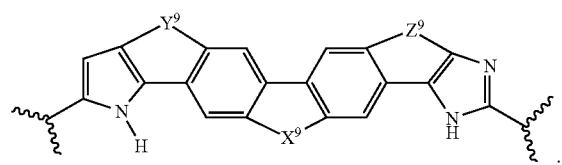

109

In one specific embodiment $X^9$ is —$CH_2$—, —$CH_2$—$CH_2$—, —$CH_2$—O—, —O—$CH_2$—, —$CH_2$—O—$CH_2$—, or —CH=CH—.

In one specific embodiment $Y^9$ is —$CH_2$—, —$CH_2$—$CH_2$—, —$CH_2$—O—, —O—$CH_2$—, —$CH_2$—O—$CH_2$—, or —CH=CH—.

In one specific embodiment $Z^9$ is —$CH_2$—, —$CH_2$—$CH_2$—, —$CH_2$—O—, —O—$CH_2$—, —$CH_2$—O—$CH_2$—, or —CH=CH—.

In one specific embodiment $W^{1a}$ is optionally substituted with one or more (e.g. 1, 2, 3, or 4) groups independently selected from halo, alkyl, haloalkyl, cyano, and

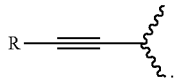

In one specific embodiment $W^{1a}$ is 107, 108, or 109.
In one specific embodiment $W^{1a}$ is 103a.
In one specific embodiment $W^{1a}$ is 103b.
In one specific embodiment $W^{1a}$ is 103d.
In one specific embodiment $W^{1a}$ is 103e.
In one specific embodiment $W^{1a}$ is 103i.
In one specific embodiment $P^{1a}$ is

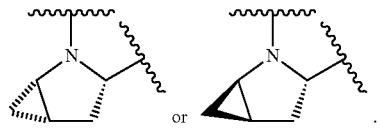

In one specific embodiment $P^{1b}$ is

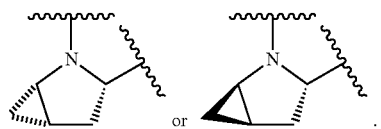

In one specific embodiment $P^{1a}$ is

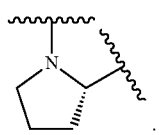

In one specific embodiment $P^{1b}$ is

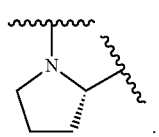

In one specific embodiment $W^{1a}$ is substituted with one or more (e.g. 1, 2, 3, or 4) groups independently selected from

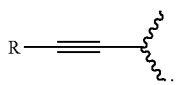

In one specific embodiment $W^{1a}$ is substituted with one or more (e.g. 1, 2, 3, or 4) fluoro.

In one specific embodiment the invention provides a compound which has any one of formulae 1-25, 25b, 25c, and 25d as shown in Table 1 hereinabove, or a pharmaceutically acceptable salt or prodrug thereof.

In one specific embodiment the compound is not a compound of formula:

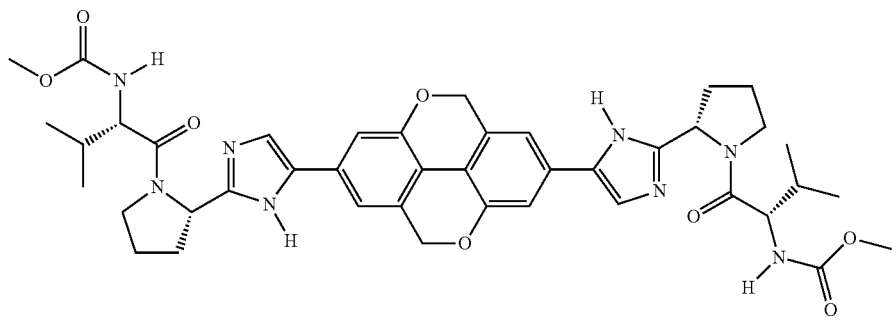

or a pharmaceutically acceptable salt or prodrug thereof.

In one specific embodiment $P^{30}$ is:

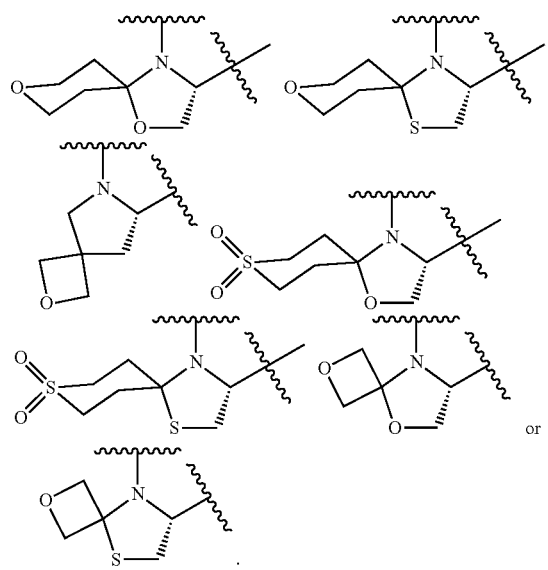

In one specific embodiment the invention provides the compound:

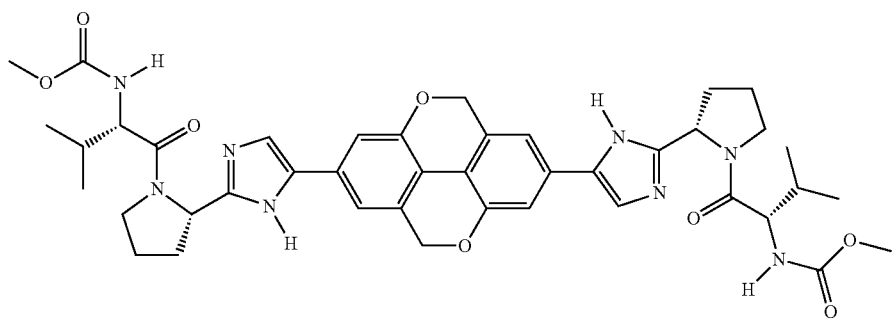

or a pharmaceutically acceptable salt or prodrug thereof.

In one specific embodiment the invention provides a compound of formula (I):

$$E^{1a}\text{-}V^{1a}\text{—}C(\!\!=\!\!O)\text{—}P^{1a}\text{—}W^{1a}\text{—}P^{1b}\text{—}C(\!\!=\!\!O)\text{—}V^{1b}\text{-}E^{1b} \quad (I)$$

wherein:

$E^{1a}$ is $E^0$ or $E^1$, or $E^{1a}\text{-}V^{1a}$ taken together are $R^{9a}$;

$E^{1b}$ is $E^0$ or $E^1$, or $E^{1b}\text{-}V^{1b}$ taken together are $R^{9b}$;

$V^{1a}$ is $V^0$ or $E_a\text{-}V^{1a}$ taken together are $R^{9a}$;

$V^{1b}$ is $V^0$ or $E^{1b}\text{-}V^{1b}$ taken together are $R^{9b}$;

one of $P^{1a}$ and $P^{1b}$ is selected from $P^1$, $P^3$, $P^5$, $P^6$, $P^7$, $P^8$, $P^{10}$, $P^{12}$, $P^{15}$, $P^{18}$, $P^{19}$ and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$;

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $V^o$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, $(NR^XR^Y)$alkyl-, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $P^o$ is independently:

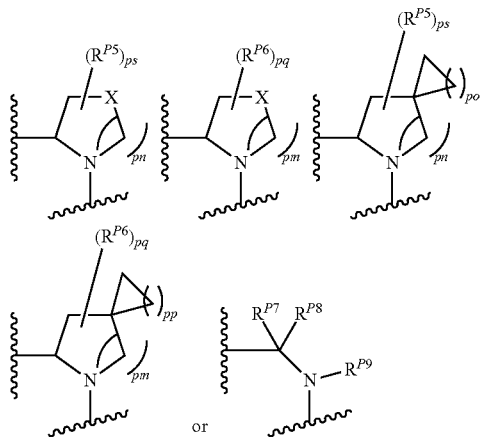

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

R$^{P7}$ and R$^{P8}$ are each independently selected from hydrogen, alkenyl, alkoxyalkyl, alkyl, haloalkyl, and (NR$^{Pa}$R$^{Pb}$) alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;
each P$^1$ is independently:

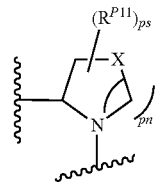

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo and heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl sulfonylalkyl; and when two R$^h$ groups are present then they may come together with the atoms to which they are bound to form a 4-15 membered heterocyclic ring;
ps is 1, 2, 3, or 4;
pn is 0, 1, or 2;
each P$^3$ is independently a ring of the formula:

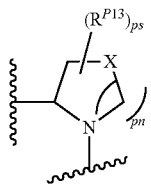

wherein:
the ring is substituted with one or more oxo group;
each R$^{P13}$ is independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
ps is 0, 1, 2, 3, or 4;
pn is 0, 1, or 2;
each P$^5$ is independently a ring of the formula:

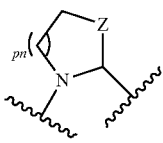

wherein:
the ring is optionally substituted with one or more groups R$^{P15}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups R$^{P15}$ that are attached to the same carbon when taken together with the carbon to which they are attached can form a 3-6 membered carbocyclic or heterocyclic ring;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
pn is 0, 1, or 2;
Z is O, S, S(=O), S(=O)$_2$, or NR$^f$;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;
each P$^6$ is independently a ring of the formula:

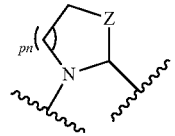

wherein:
the ring is substituted with one or more oxo and is optionally substituted with one or more groups R$^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
Z is O, S, S(=O), S(=O)$_2$, or NR$^f$;
pn is 0, 1, or 2;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;
each P$^7$ is a bridged 5-15 membered bicyclic heterocyclic ring that is attached to the remainder of the compound of formula I through one N-link and through one C-link;

wherein the ring is optionally substituted with one or more groups independently selected from $R^{P6}$ and $R^{P11}$;

each $P^8$ is independently a ring of the formula:

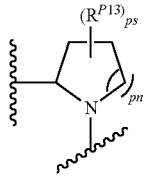

wherein:
ps is 2, 3, 4, 5, or 6;
pn is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
each $P^{10}$ is independently:

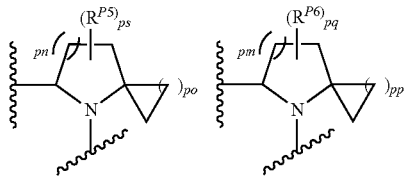

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq and ps are independently 0, 1, 2, 3, or 4;
pm and pn are independently 0, 1, or 2;
po and pp are independently 1, 2, or 3;

each $P^{12}$ is independently:

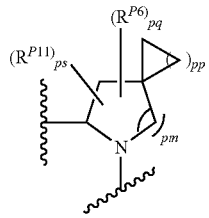

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq is independently 0, 1, 2, 3, or 4;
pm is independently 0, 1, or 2;
pp is independently 1, 2, or 3;
ps is 1, 2, 3, or 4;
$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each $P^{15}$ is:

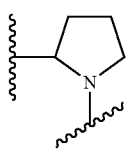

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

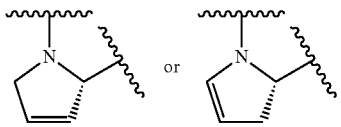

which is optionally substituted with one or two groups independently selected from halo, alkyl, alkoxyalkyl, haloalkyl, cycloalkyl, and cycloalkylalkyl;

each $P^{19}$ is:

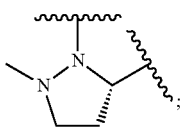 [SMILES: *[C@@H]1CCN(C)N1*]

each $P^{30}$ is independently a ring of the formula:

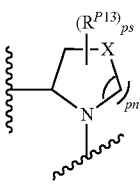

ps is 2
pn is 0, 1 or 2;
X is selected from O, S, S(O), $SO_2$, or $CH_2$; provided that when pn is 0, X is $CH_2$.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —($NR^XR^Y$)alkyl, and —($NR^XR^Y$)carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl, wherein $R^{X'}$ and $R^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —($NR^XR^Y$)alkyl, and —($NR^XR^Y$)carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl, wherein $R^{X'}$ and $R^{Y'}$ are independently selected from hydrogen and alkyl;

$W^{1a}$ is selected from:

110
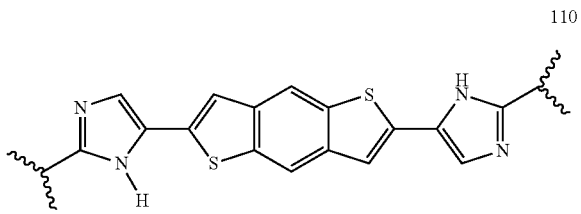

111
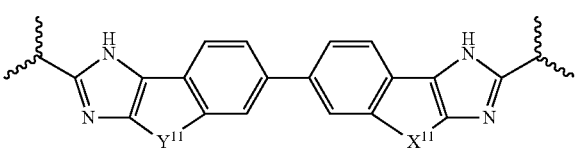

112
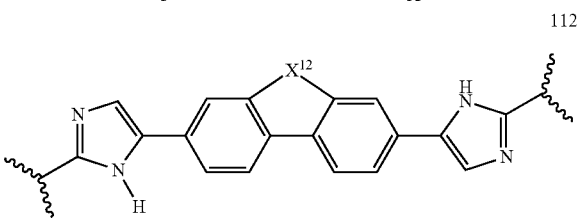

113
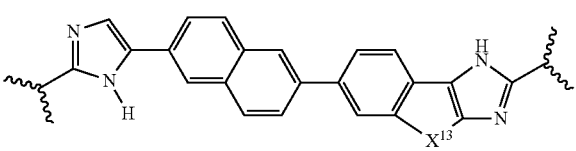

114
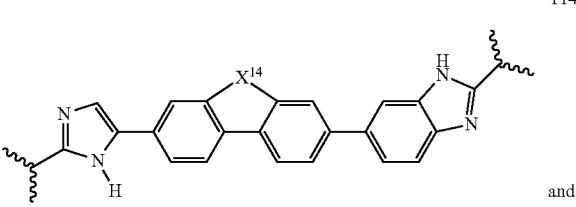

115
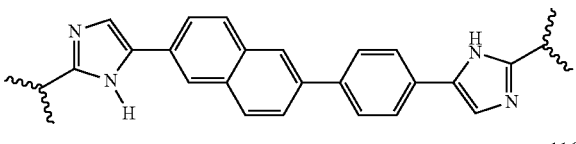

116
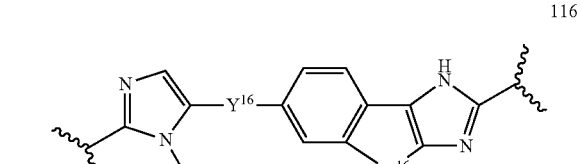

125

and

130
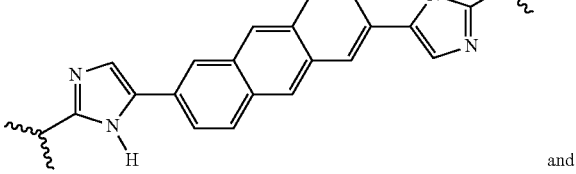

wherein each $W^{1a}$ is optionally substituted with one or more (e.g. 1, 2, 3, or 4) groups independently selected from halo, alkyl, haloalkyl, cyano, and

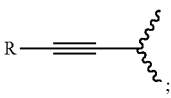;

wherein each R is independently H, alkyl, haloalkyl, cycloalkyl, aryl, or heteroaryl;

$X^{11}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

$Y^{11}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

$X^{12}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

$X^{13}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—; and $X^{14}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—; and each $Y^{16}$ is a bicyclic aromatic ring system comprising eight to 12 atoms optionally including one or more heteroatoms selected from O, S, and N, which bicyclic ring system is optionally with one or more groups independently selected from halo, haloalkyl, alkyl and oxo.

or a pharmaceutically acceptable salt or prodrug thereof;

provided the compound of formula (I) is not:
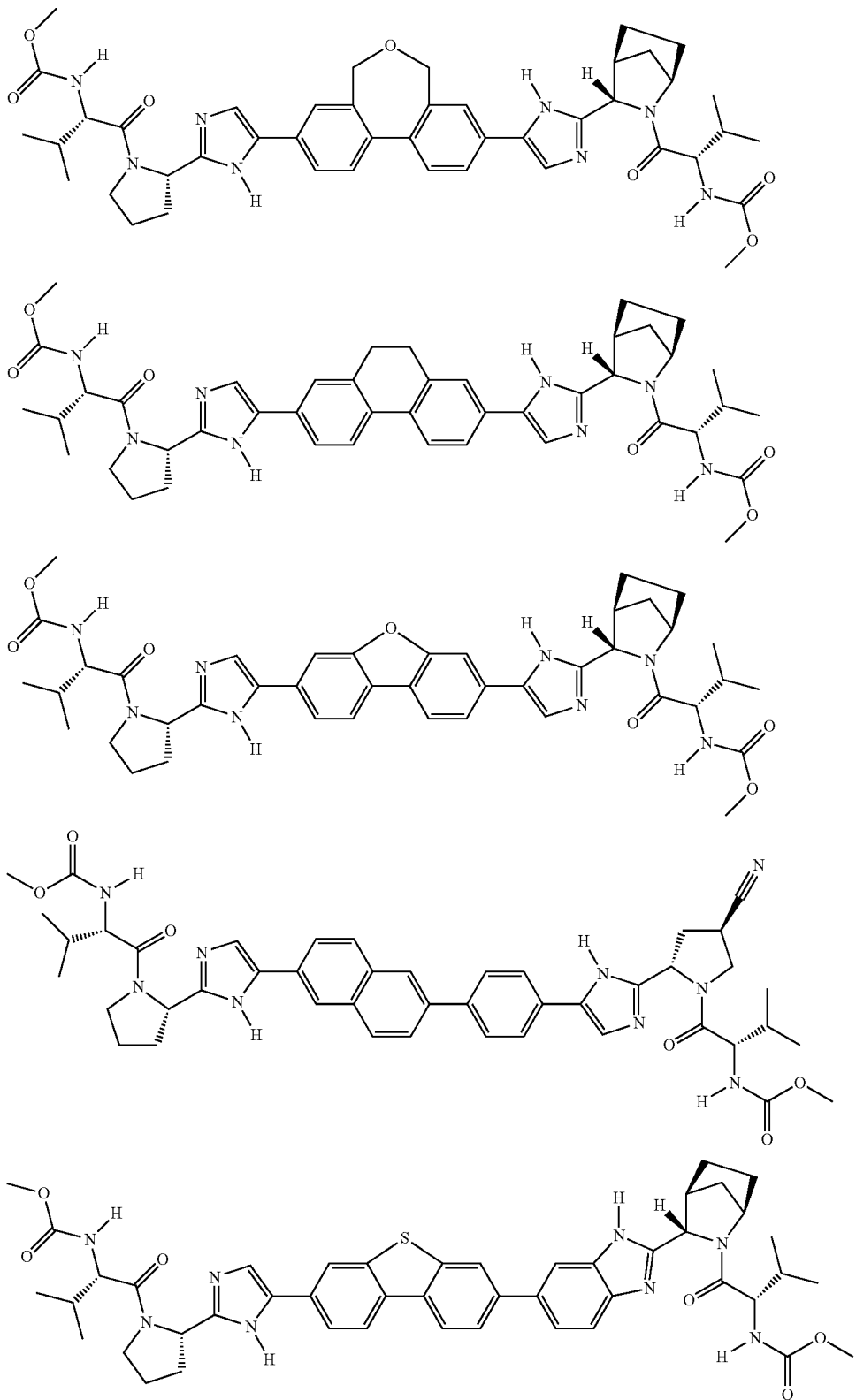

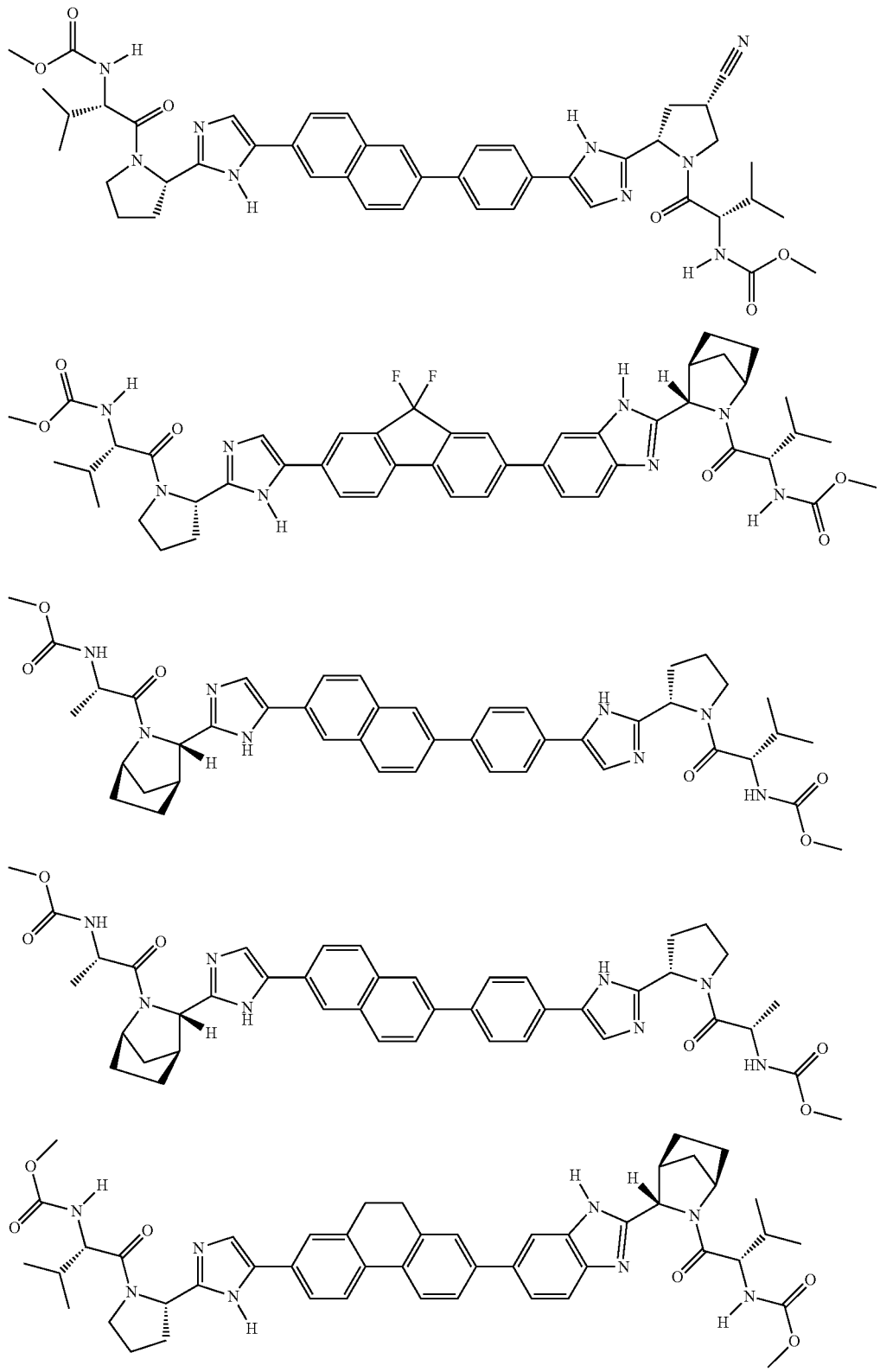

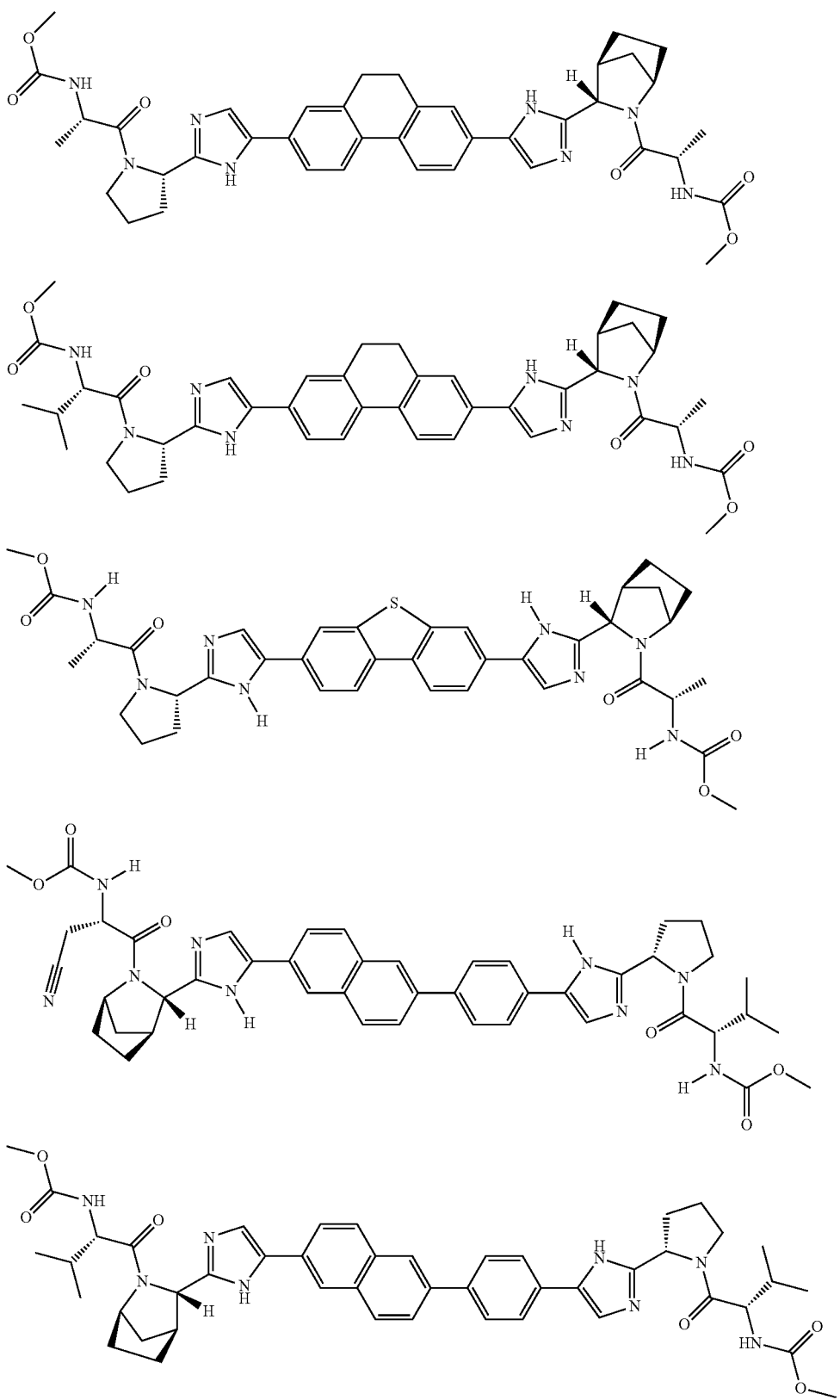

-continued
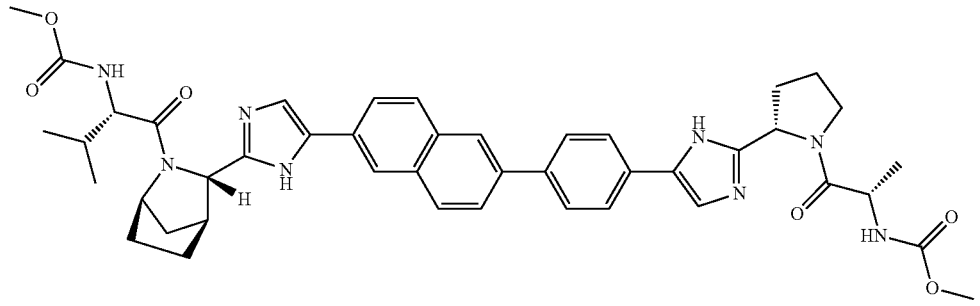
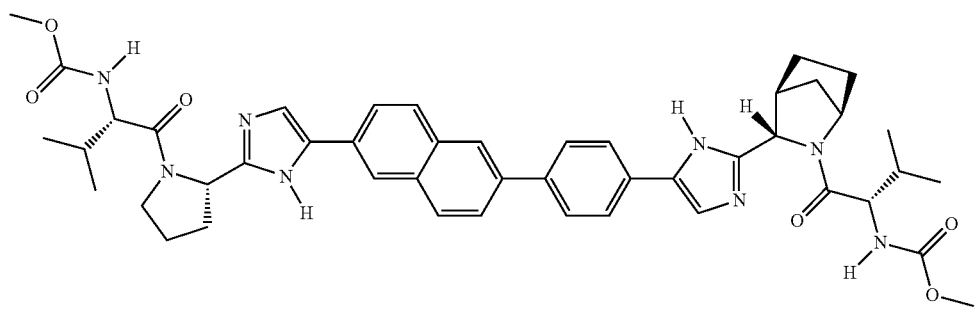
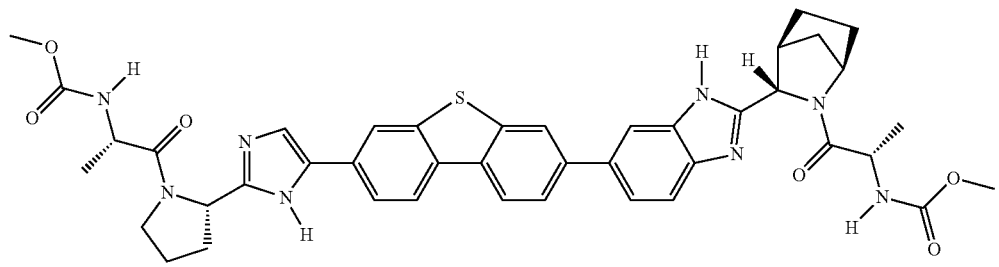
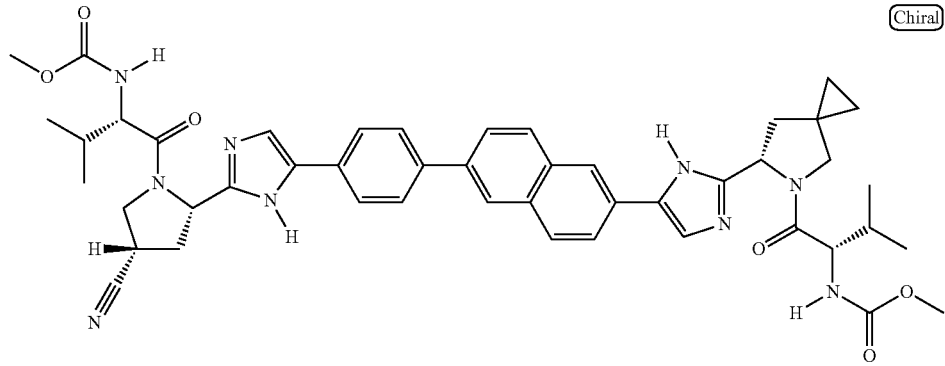
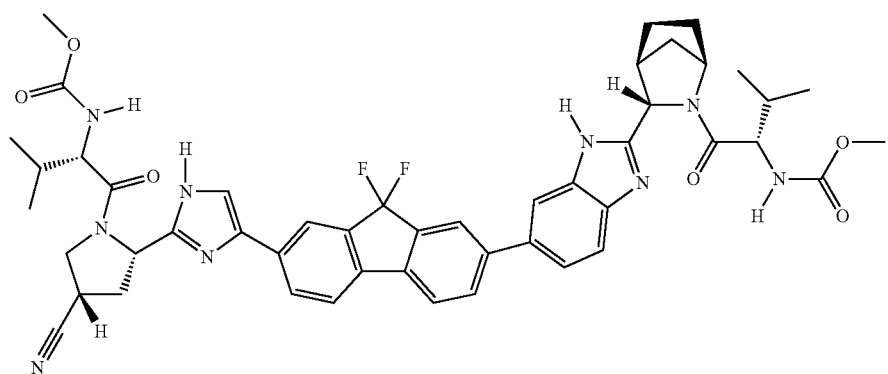

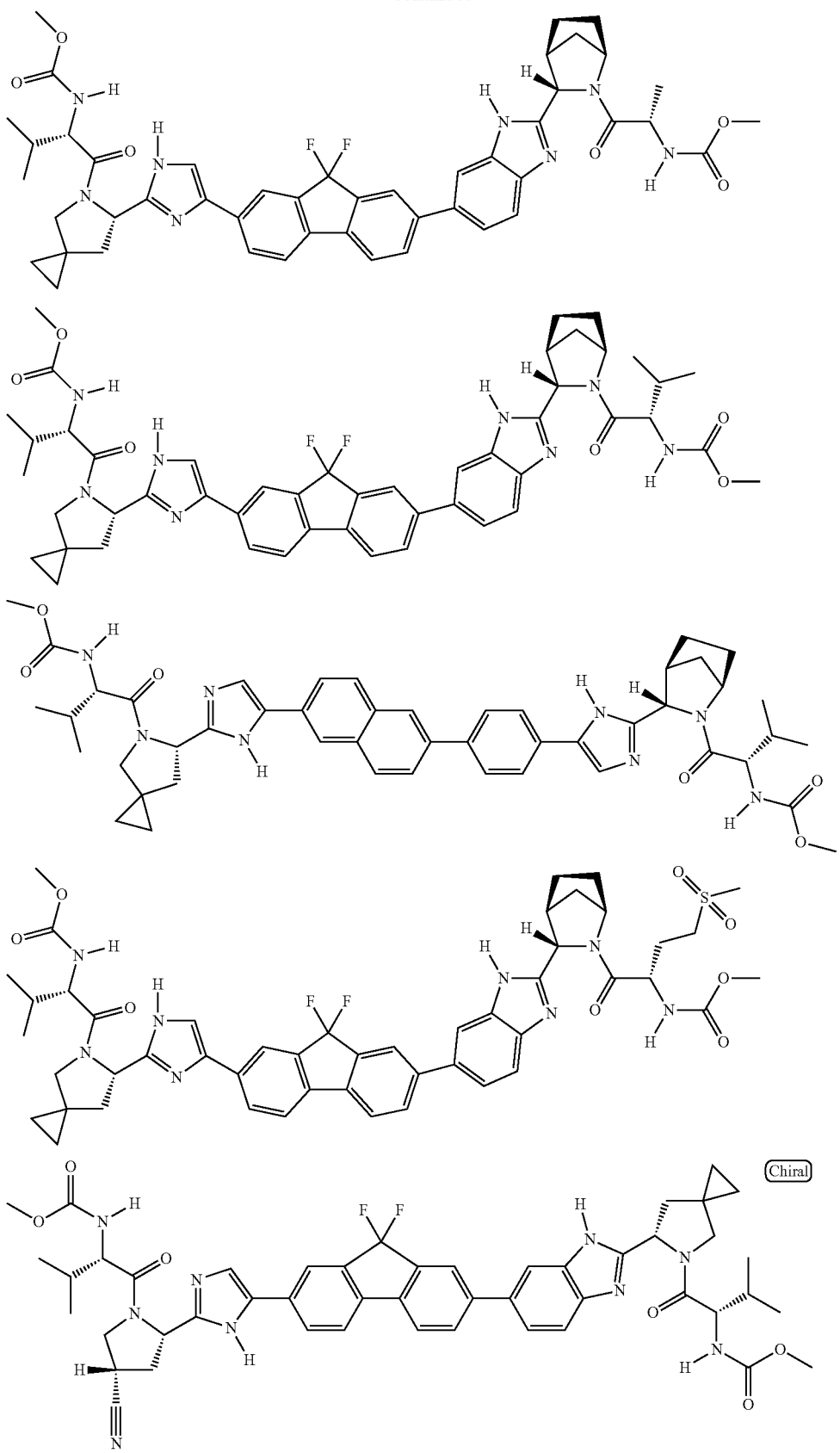

-continued
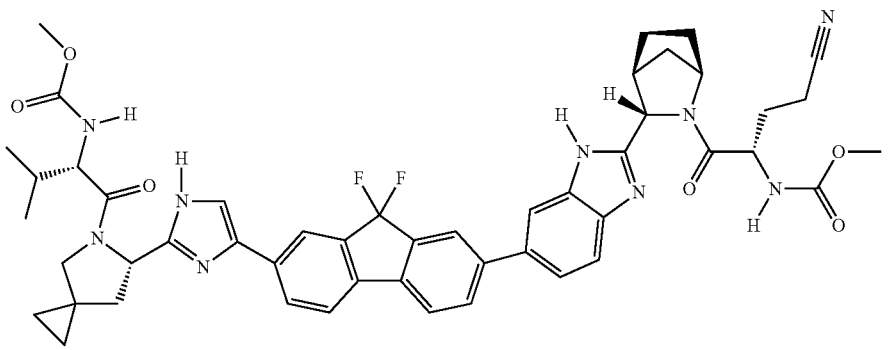
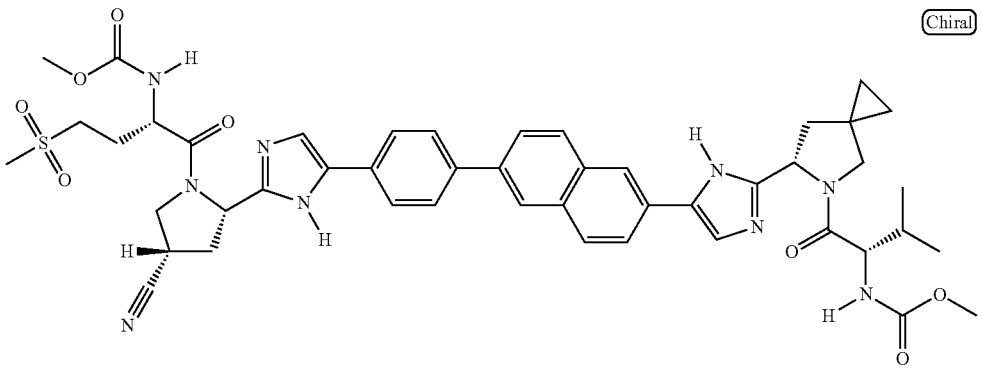
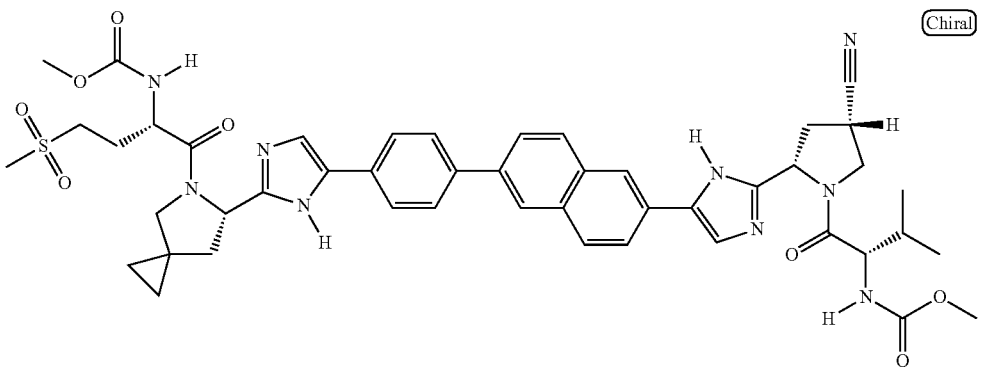
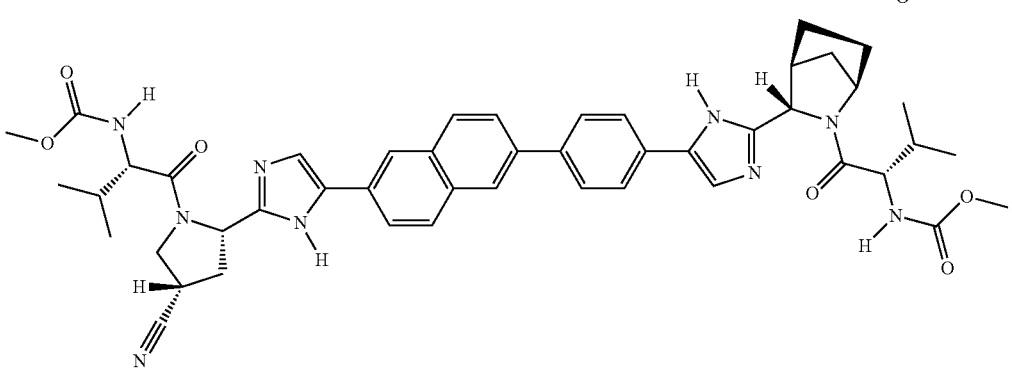
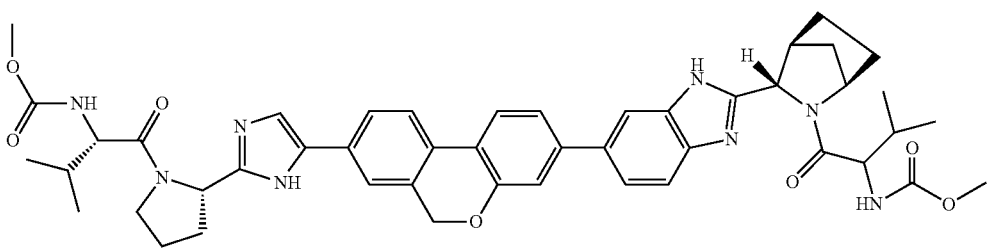

-continued
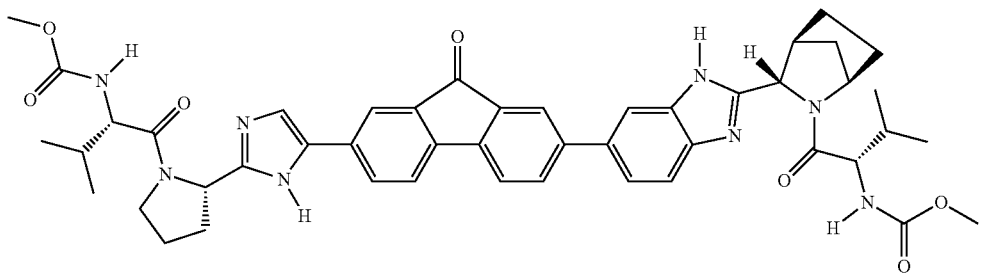
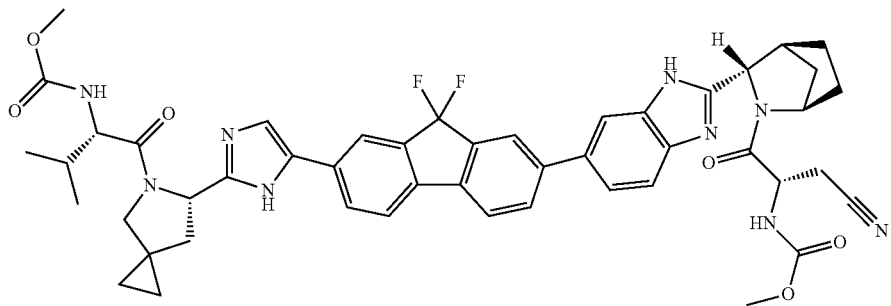
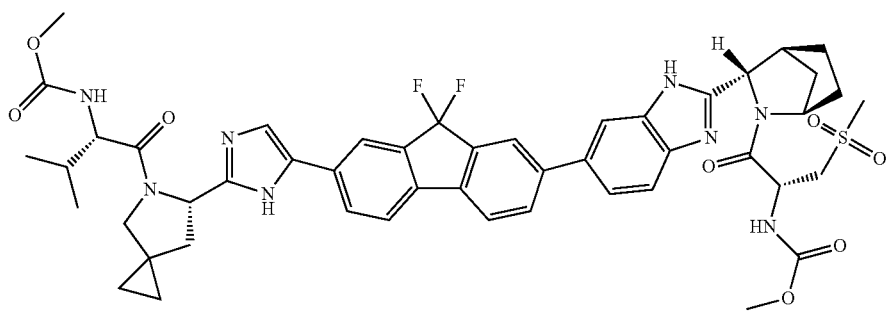
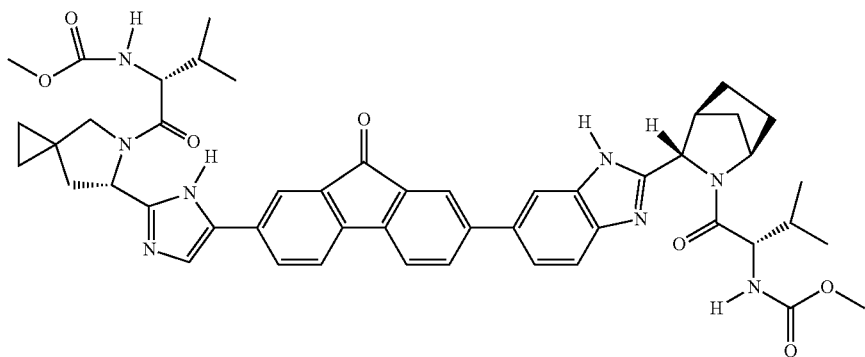
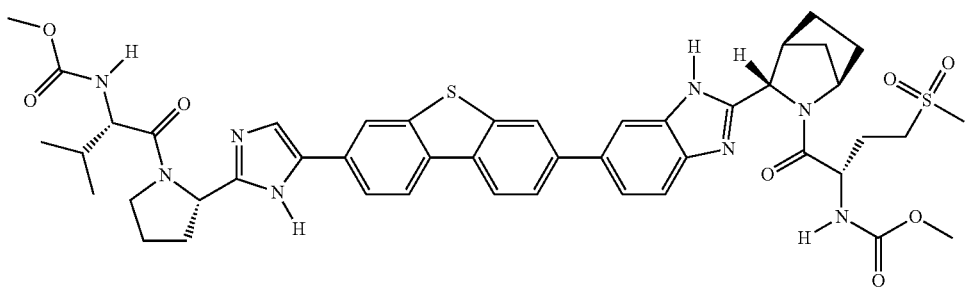

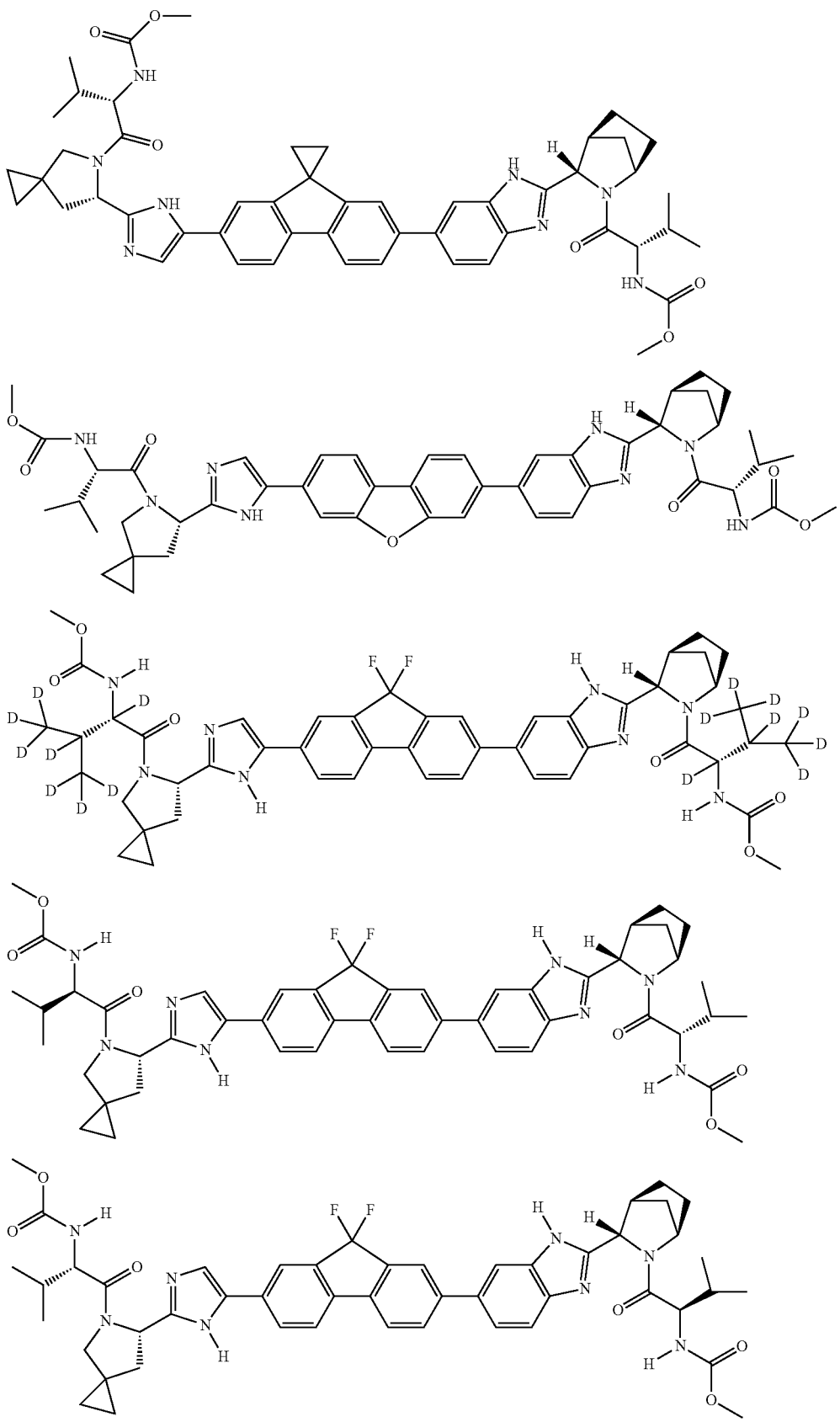

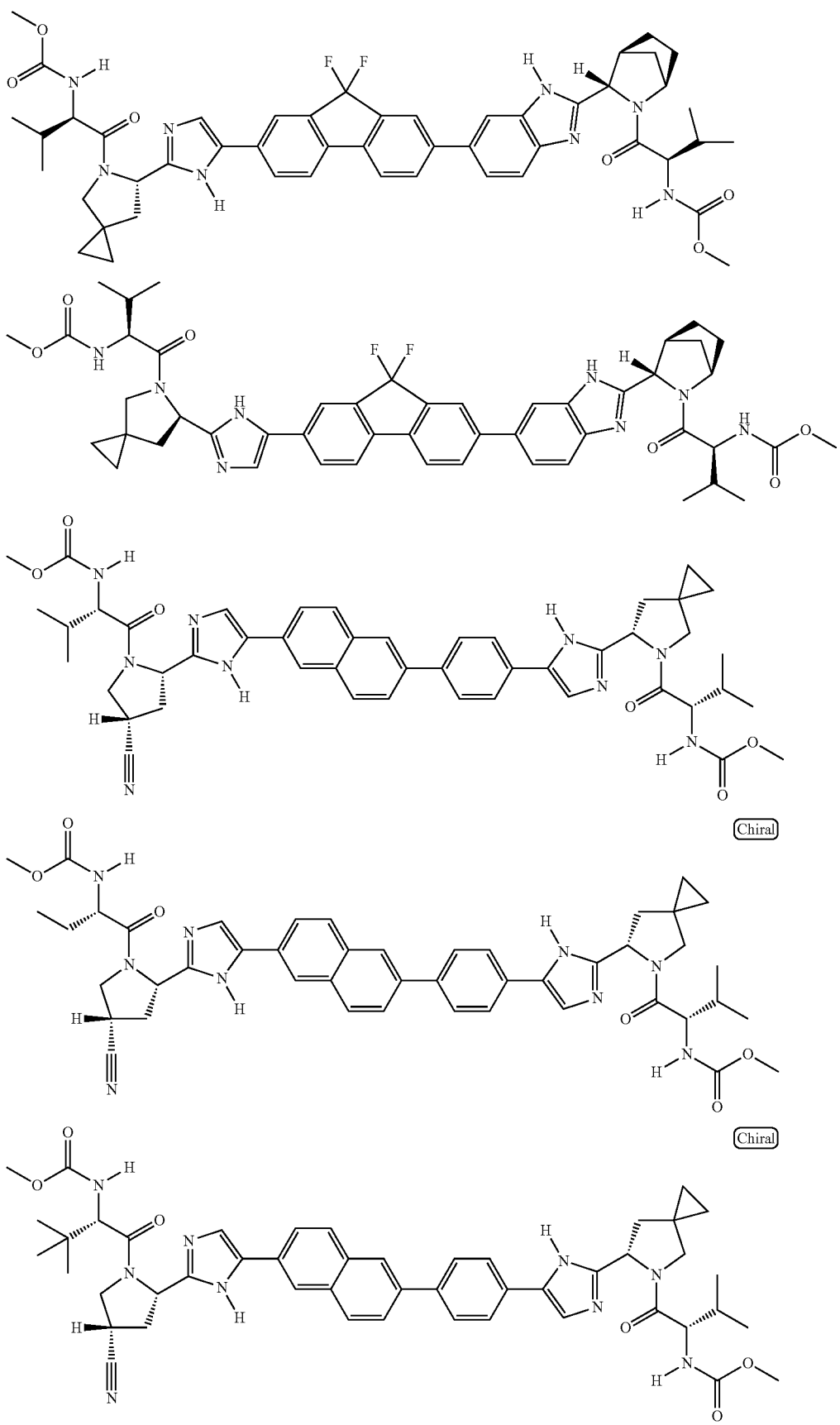

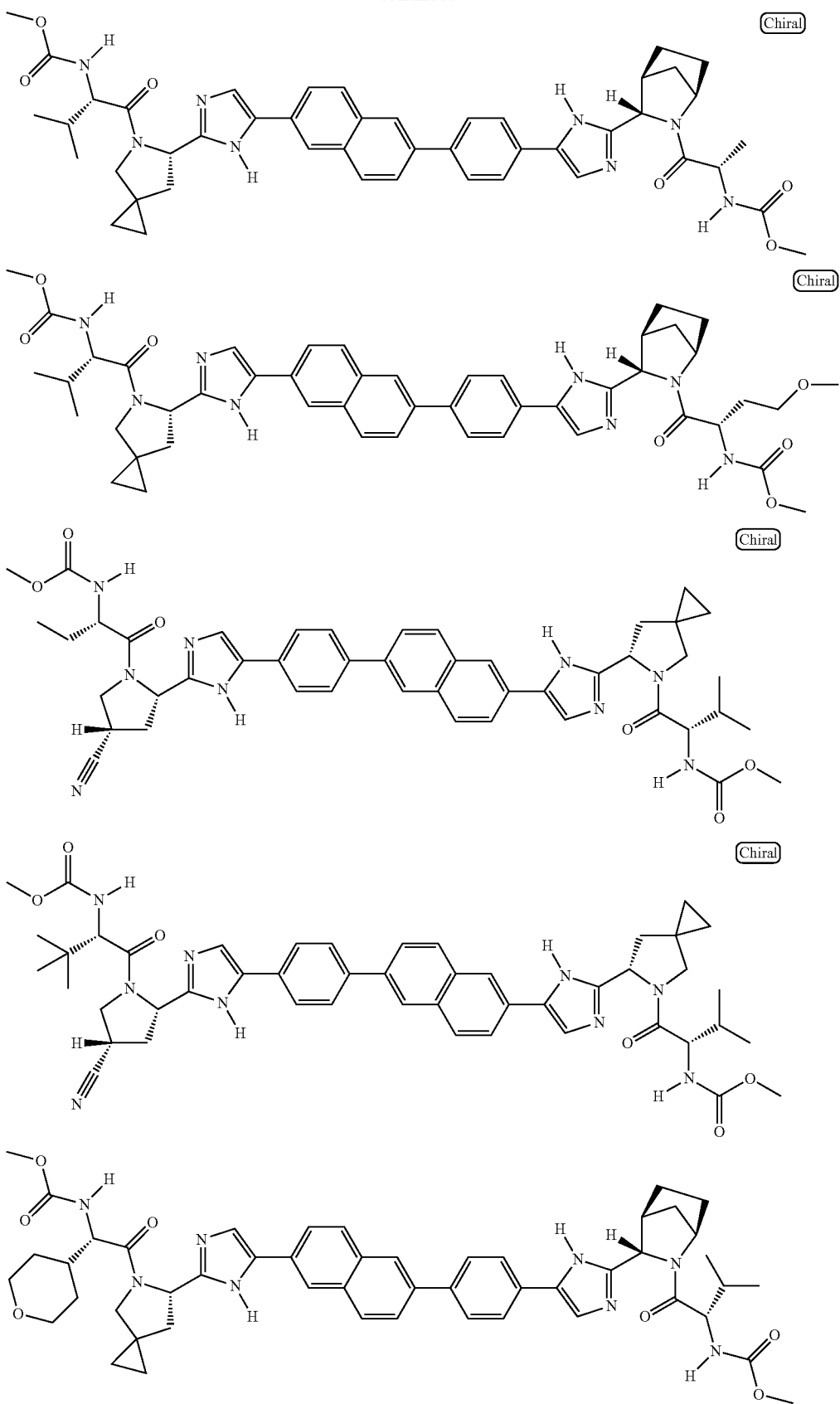

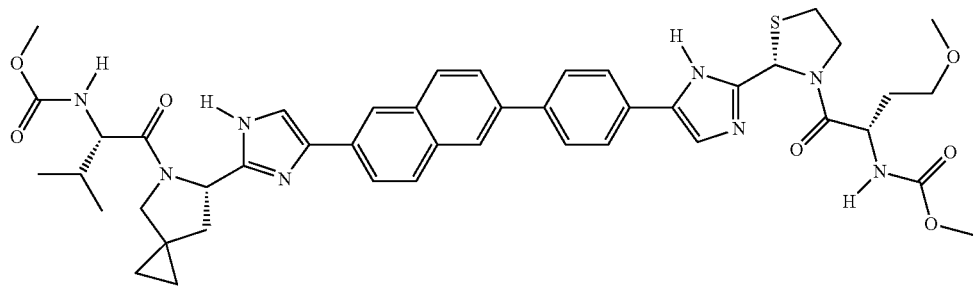
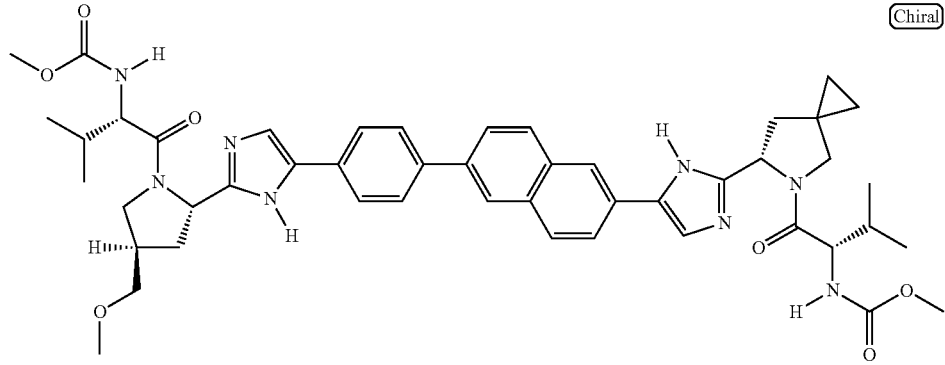
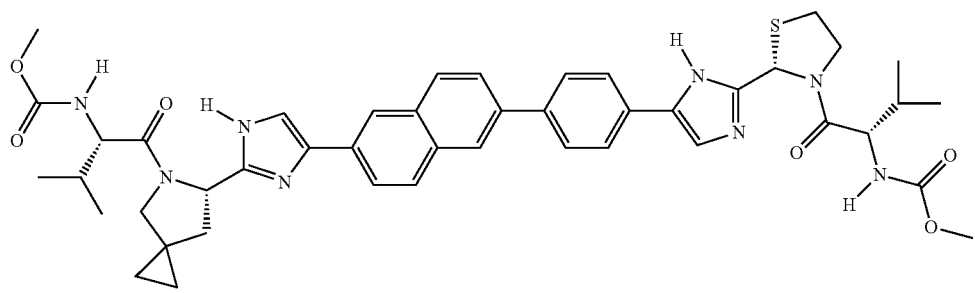
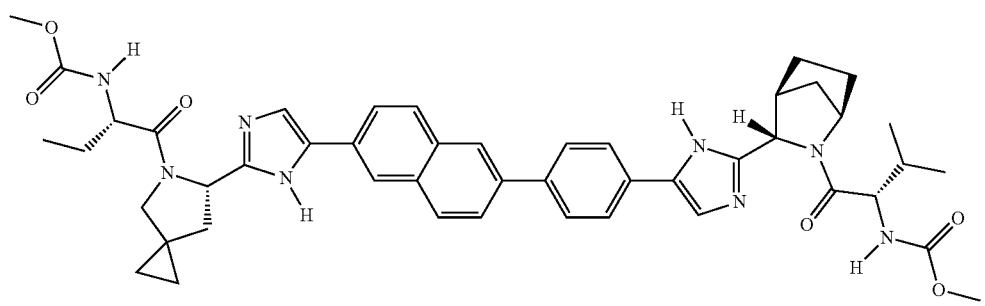
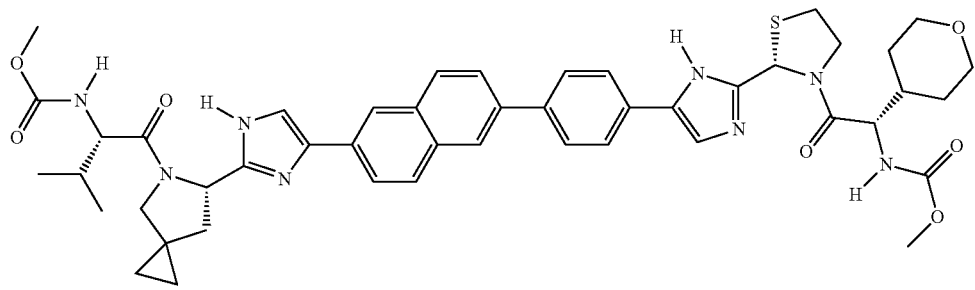

329 330
-continued
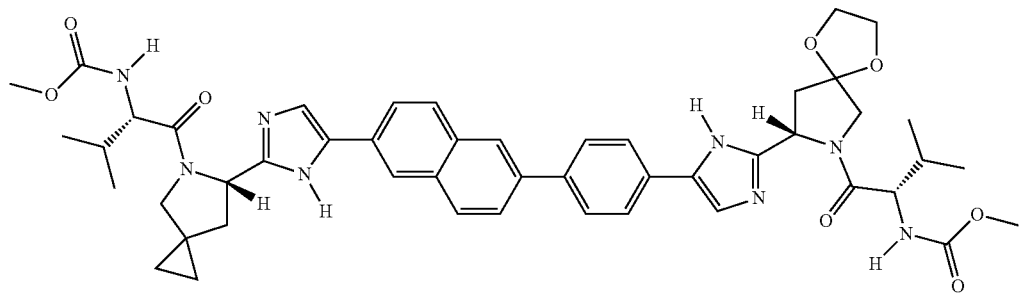
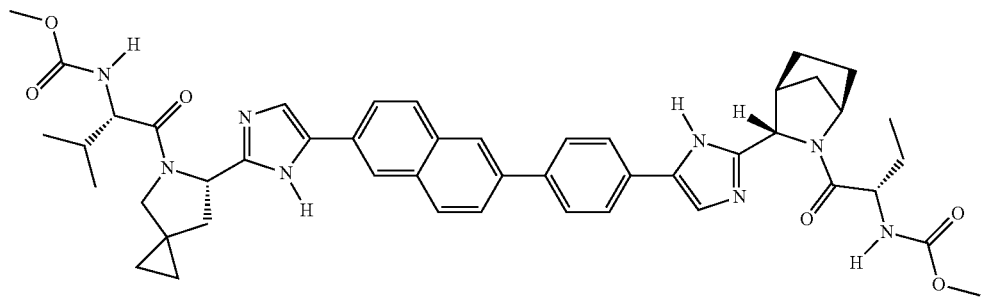
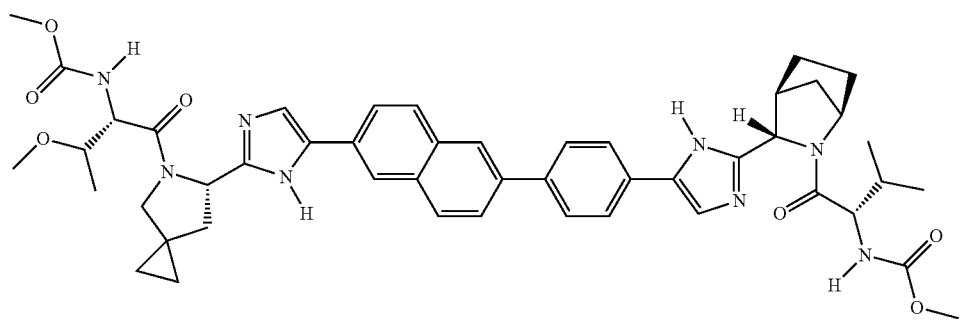
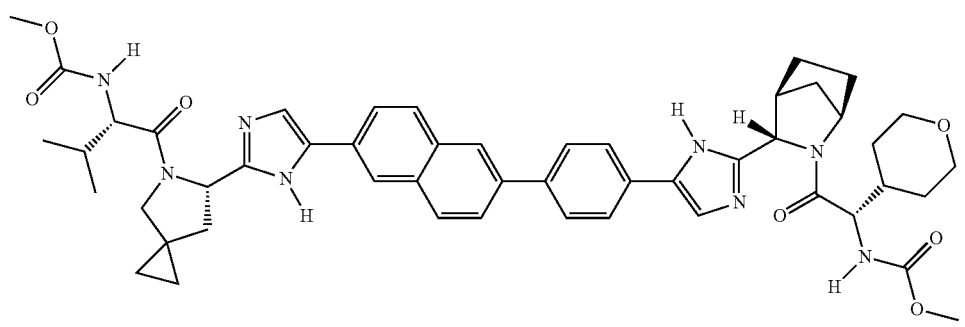
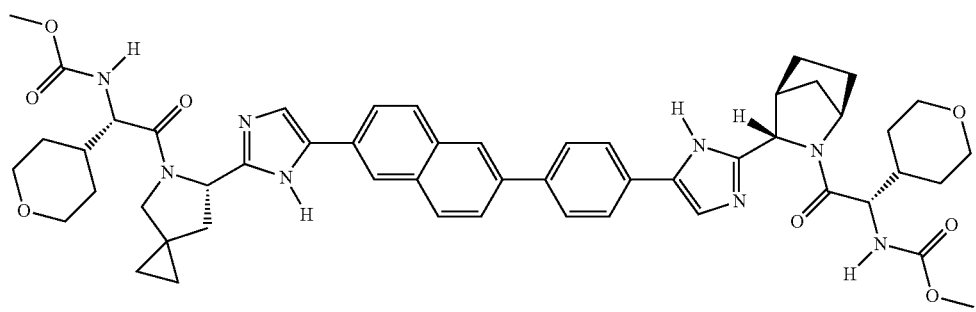

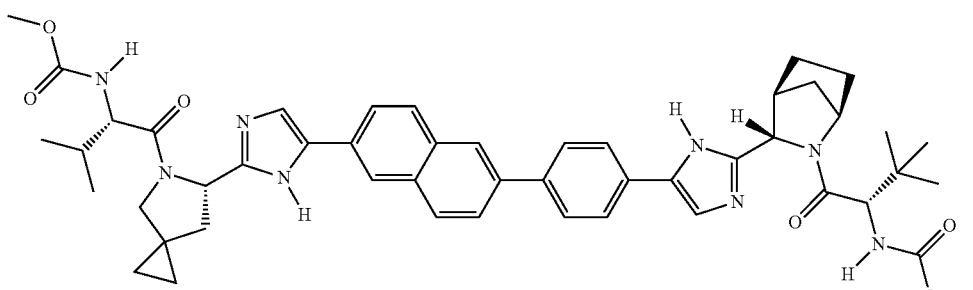
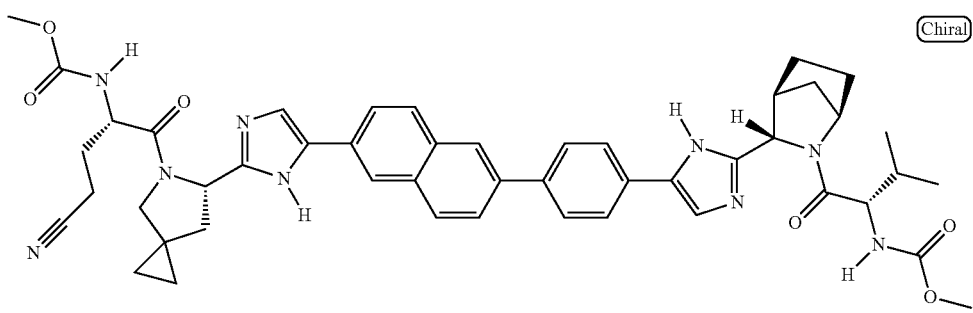
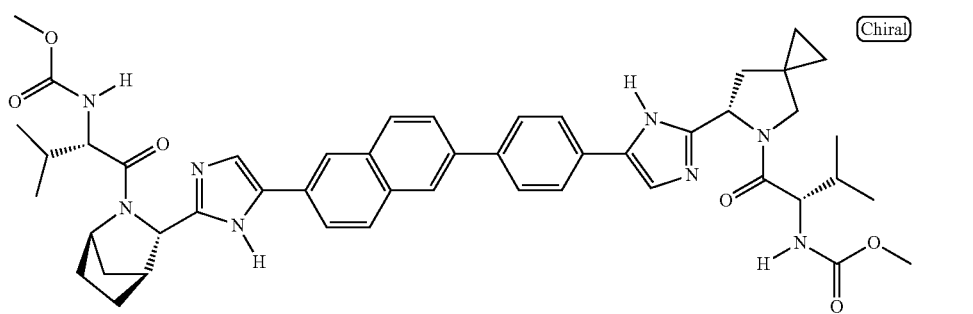
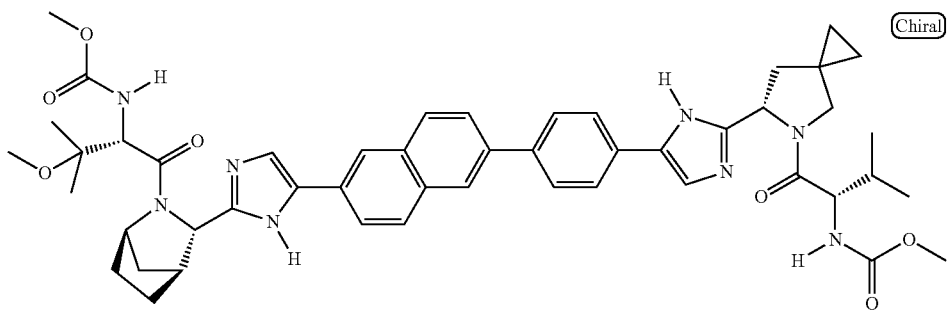
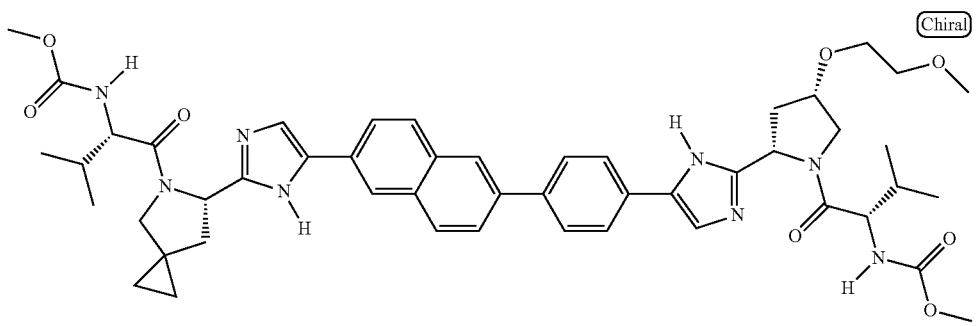

-continued
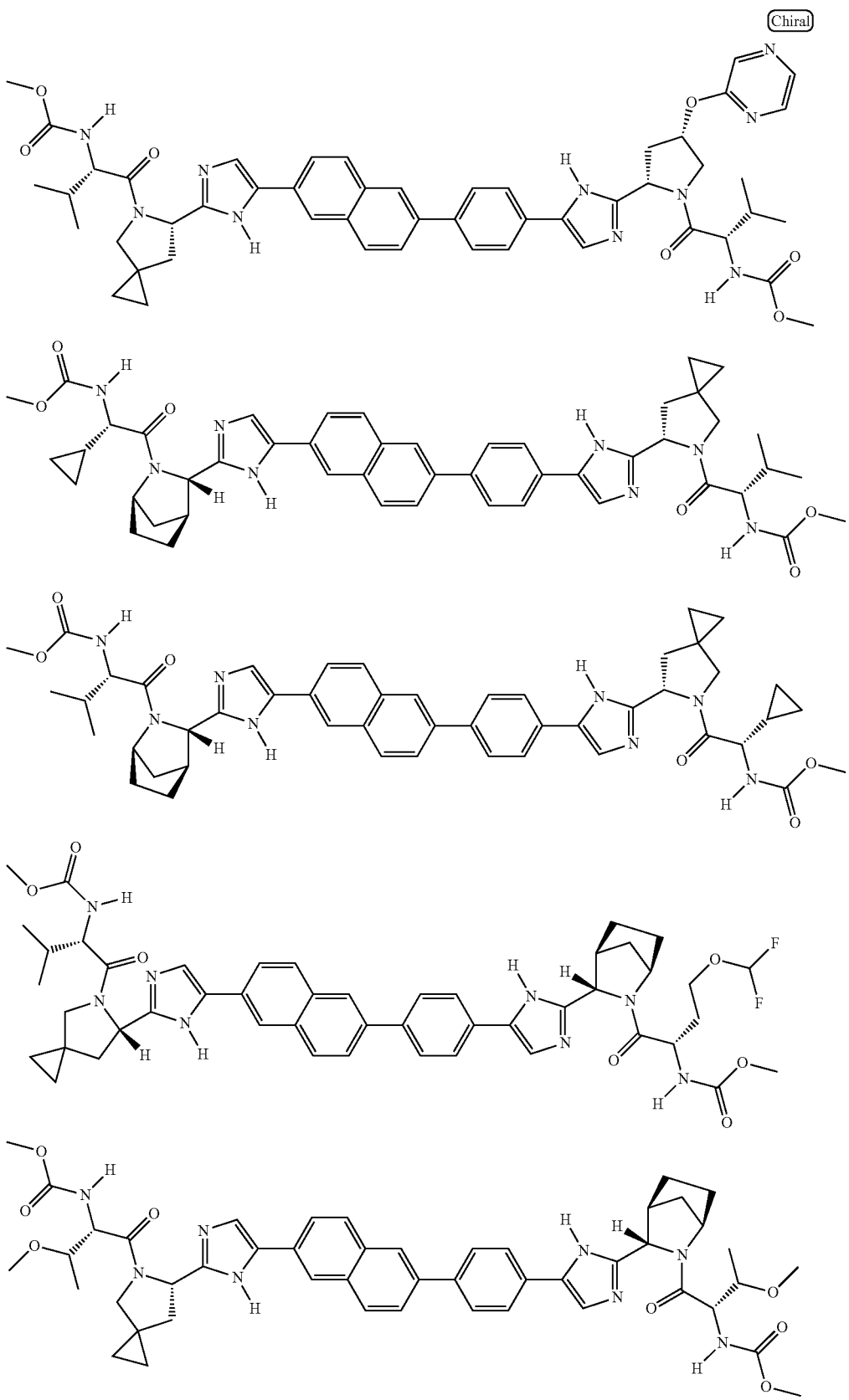

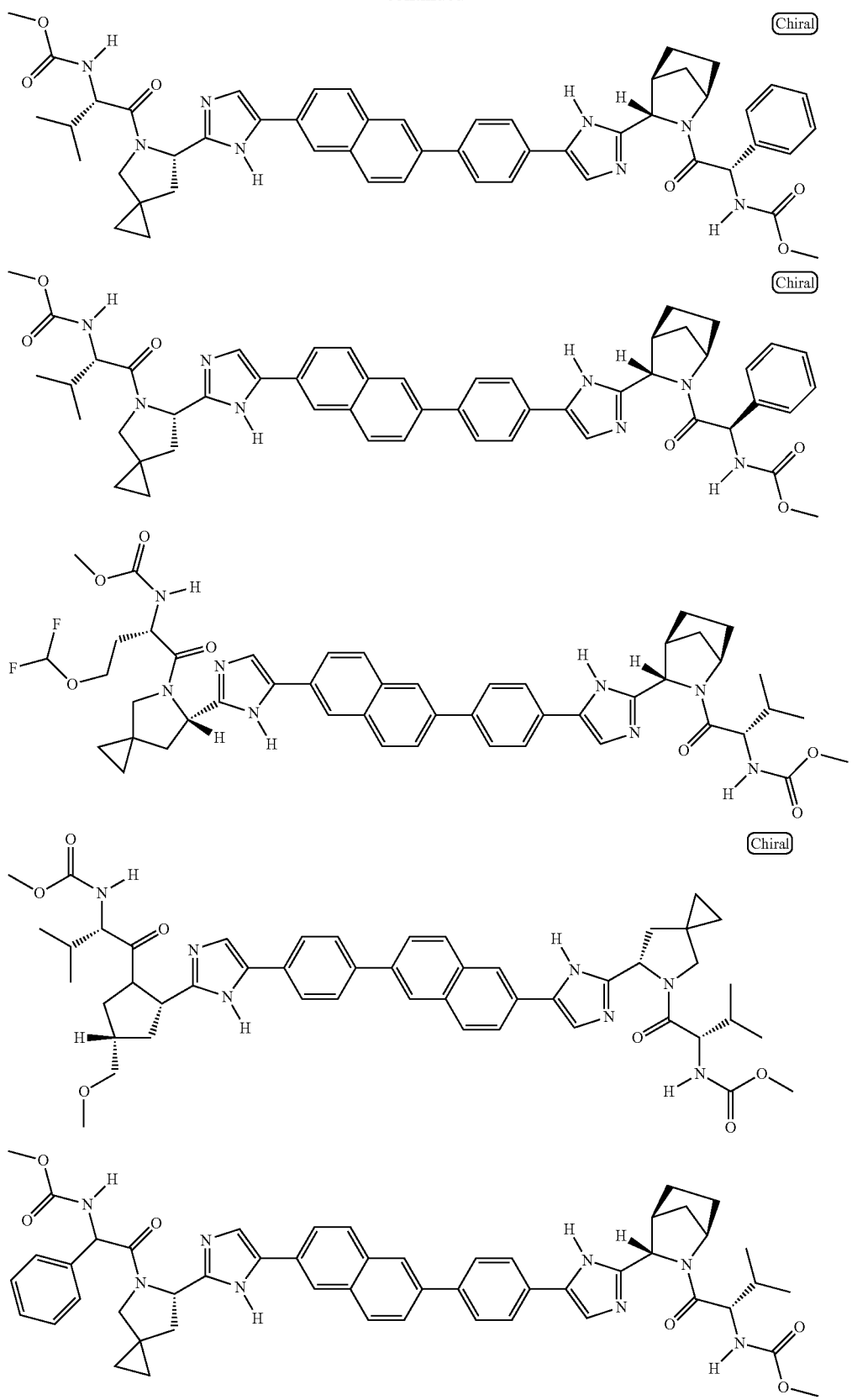

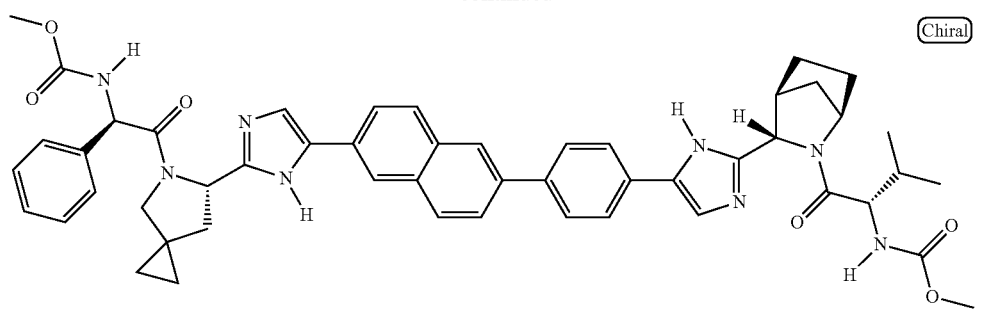
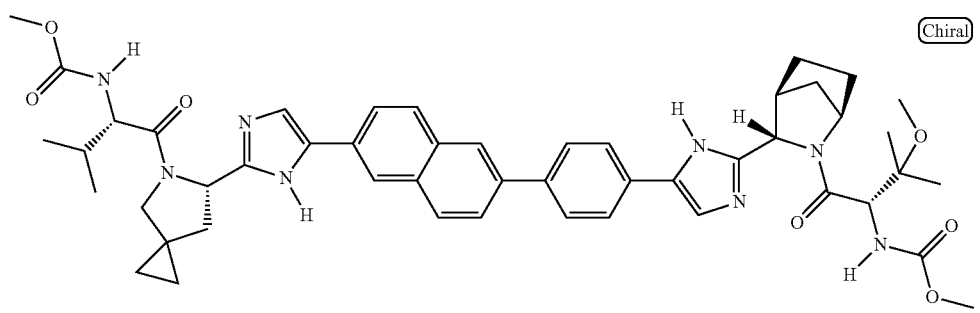
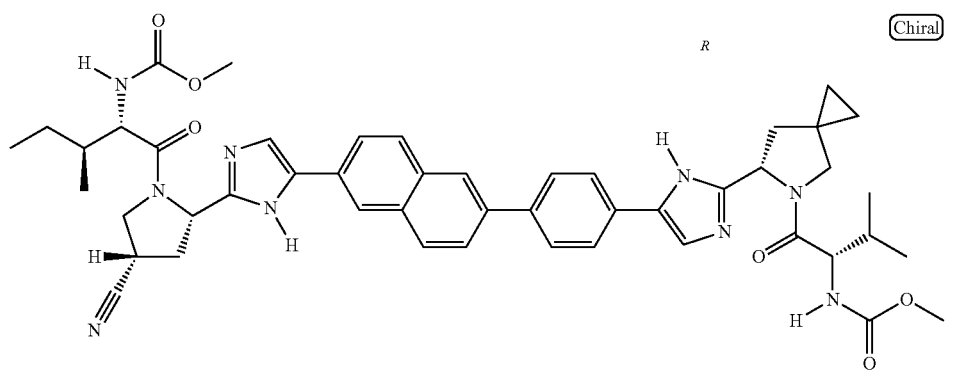
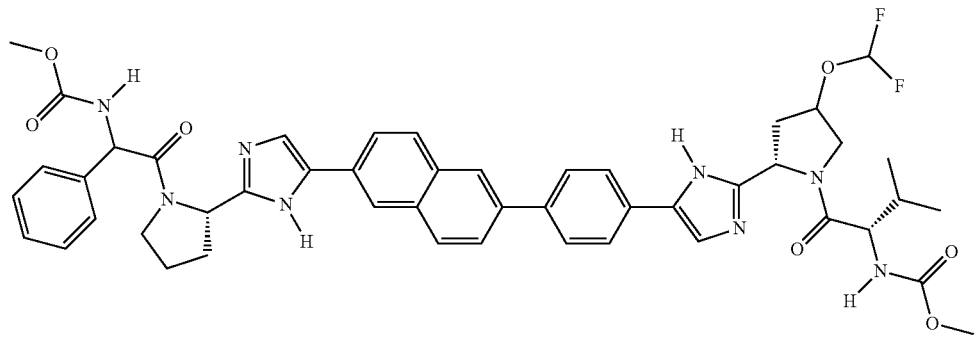
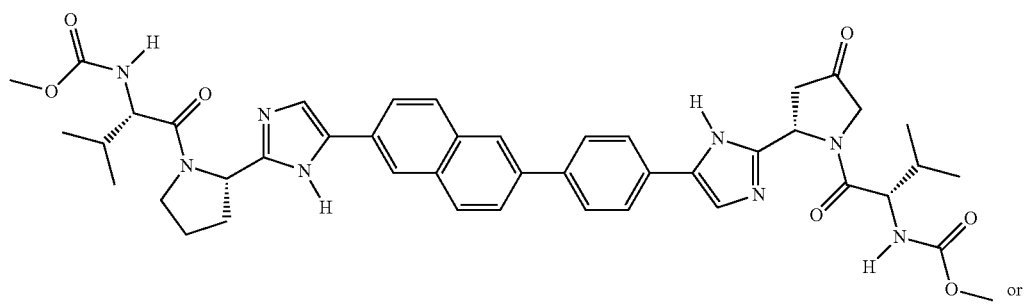

-continued
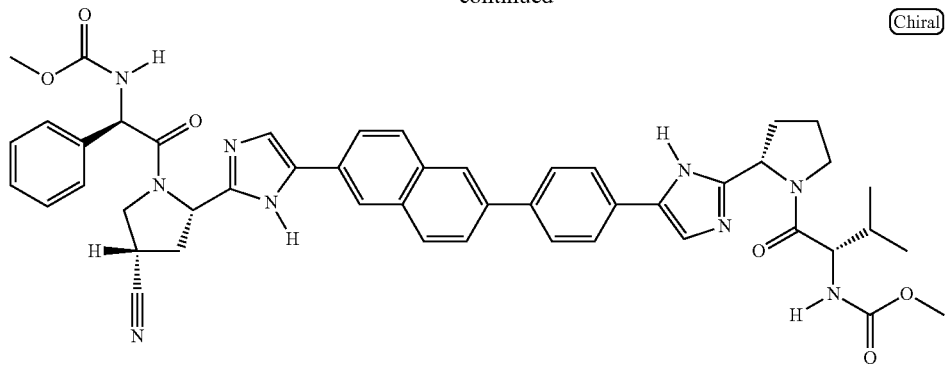
In one specific embodiment $W^{1a}$ is formula 116.
In one specific embodiment $W^{1a}$ is:
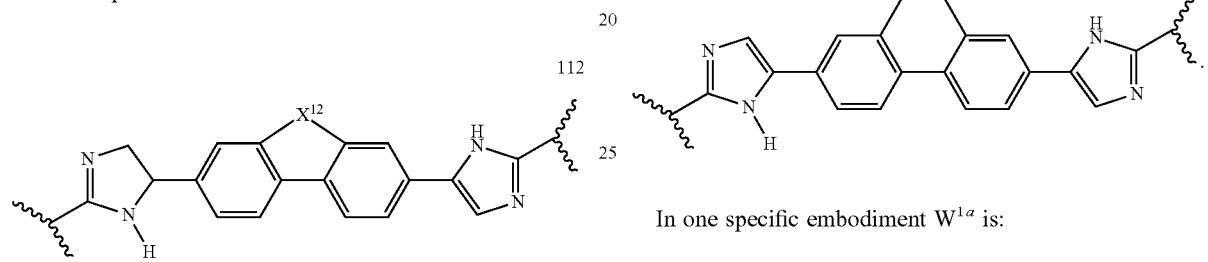
112
In one specific embodiment $X^{12}$ is: $X^{12}$ is —CH$_2$—CH$_2$—, —CH$_2$—O—, —O—CH$_2$—, —S—, —O—, —CO—, —CF$_2$—, or —CH=CH—.
In one specific embodiment $W^{1a}$ is:
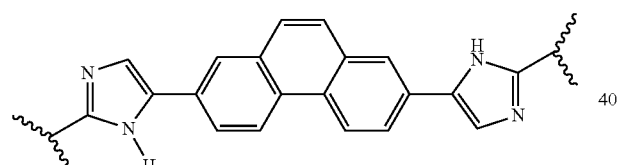
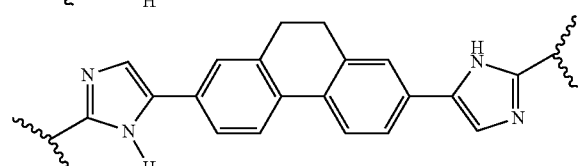
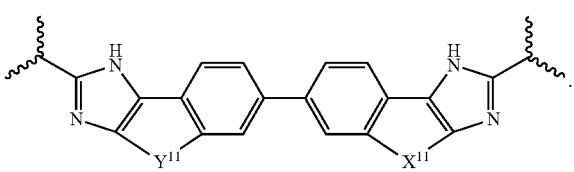
In one specific embodiment $W^{1a}$ is:
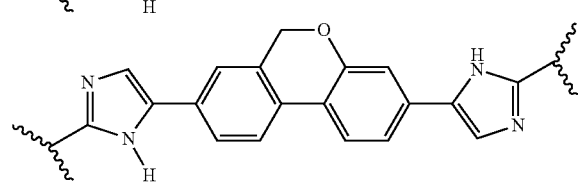
In one specific embodiment $W^{1a}$ is:
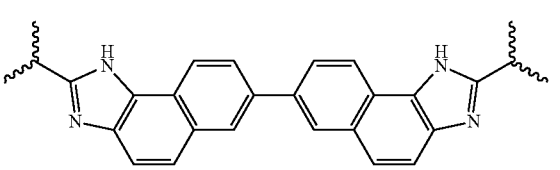
In one specific embodiment $W^{1a}$ is:
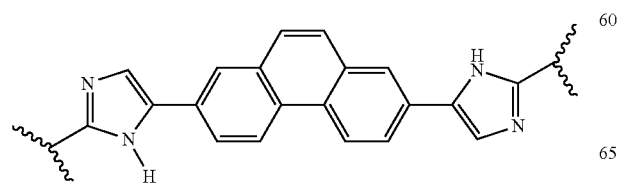
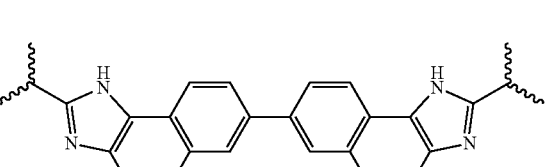

-continued

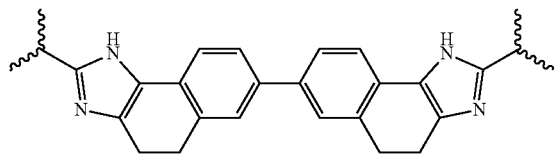
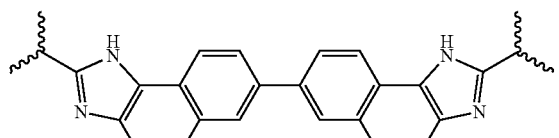
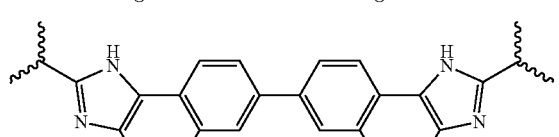
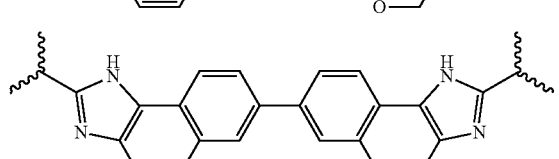
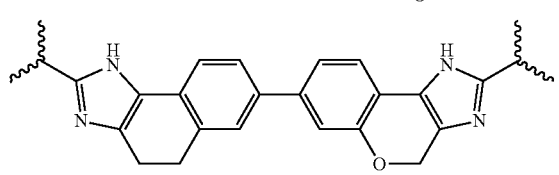
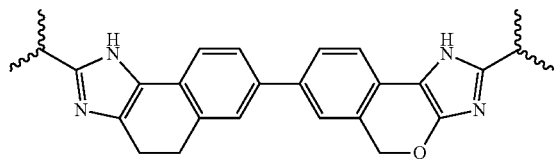
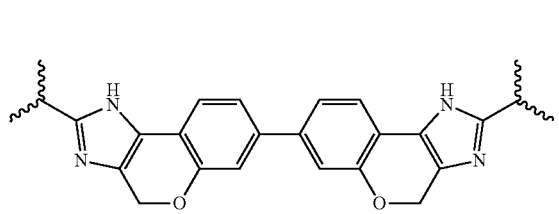
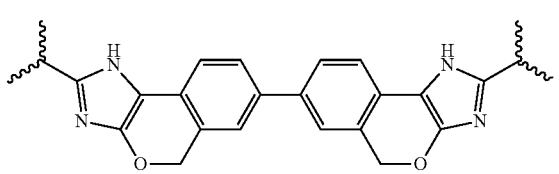

or

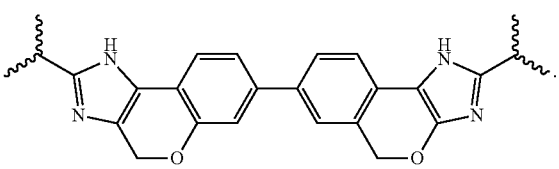

In one specific embodiment $W^{1a}$ is:


In one specific embodiment $X^{14}$ is —CH$_2$—CH$_2$—, —CH$_2$—O—, —O—CH$_2$—, —S—, —O—, —CO—, —CF$_2$—, or —CH=CH—

In one specific embodiment $W^{1a}$ is:

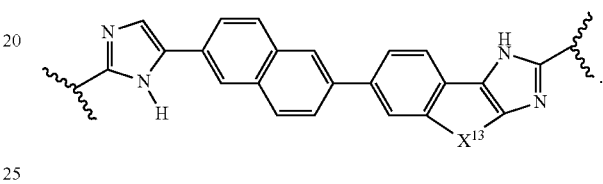

In one specific embodiment $X^{13}$ is:
$X^{13}$ is —CH$_2$—CH$_2$—, —CH$_2$—O—, —O—CH$_2$—, —S—, —O—, —CO—, —CF$_2$—, or —CH=CH—

In one specific embodiment $W^{1a}$ is:

116

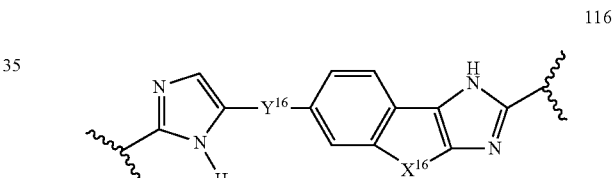

wherein $W^{1a}$ is optionally substituted with one or more (e.g. 1, 2, 3, or 4) groups independently selected from halo, alkyl, haloalkyl, cyano, and

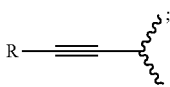

wherein each R is independently H, alkyl, haloalkyl, cycloalkyl, aryl, or heteroaryl;

$X^{16}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—; and $Y^{16}$ is a bicyclic aromatic ring system comprising eight to 12 atoms optionally including one or more heteroatoms selected from O, S, and N, which bicyclic ring system is optionally with one or more groups independently selected from halo, haloalkyl, alkyl and oxo.

In one specific embodiment $Y^{16}$ is benzothiophene, quinoline, isoquinoline, and quinazoline.

In one specific embodiment W$^{1a}$ is:
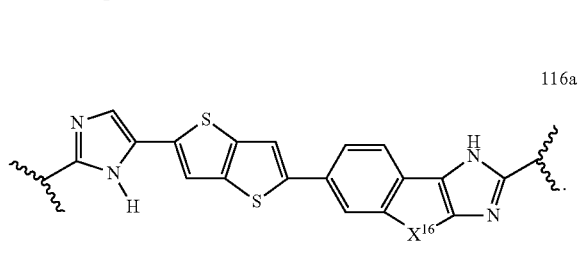
In one specific embodiment W$^{1a}$ is:
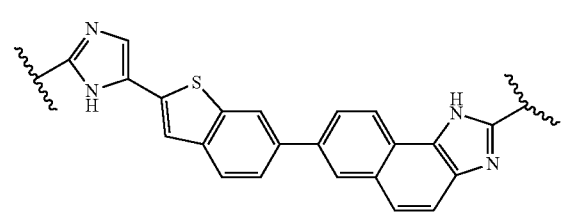
In one specific embodiment X$^{16}$ is: X$^{16}$ is —CH$_2$—CH$_2$—, —CH$_2$—O—, —O—CH$_2$—, —S—, —O—, —CO—, —CF$_2$—, or —CH=CH—.
In one specific embodiment W$^{1a}$ is:
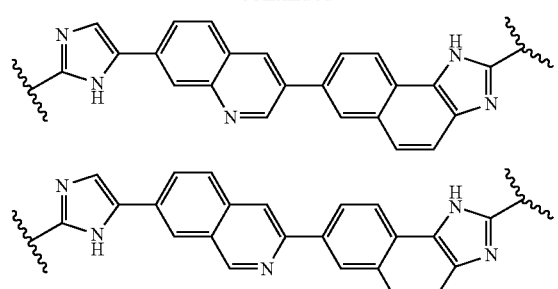
In one specific embodiment W$^{1a}$ is:
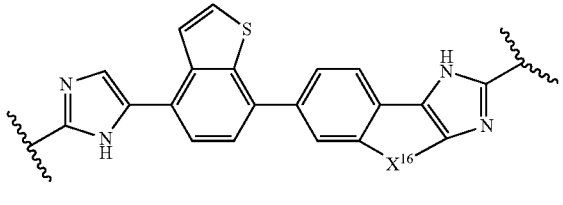

-continued

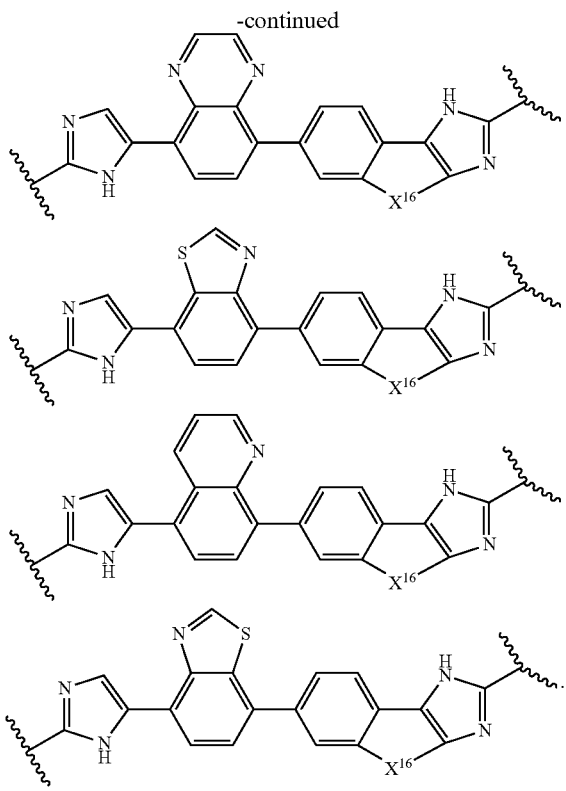

In one specific embodiment $X^{16}$ is CH2-CH2, CH2-O, O—CH2-, —S—, —O—, —CO—, —CF2—, or CH=CH.

In one specific embodiment the invention provides a compound of formula (I):

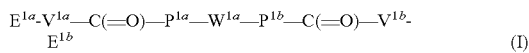

(I)

wherein:
$E^{1a}$ is $E^0$ or $E^1$, or $E^{1a}$-$V^{1a}$ taken together are $R^{9a}$;
$E^{1b}$ is $E^0$ or $E^1$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
one of $P^{1a}$ and $P^{1b}$ is selected from $P^1$, $P^3$, $P^5$, $P^6$, $P^7$, $P^8$, $P^{10}$, $P^{12}$, $P^{15}$, $P^{18}$, $P^{19}$ and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$;

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, aryl, and heterocyclyl;

each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, $(NR^XR^Y)$alkyl-, oxo, and —P(O)OR_2, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$W^{1a}$ is:

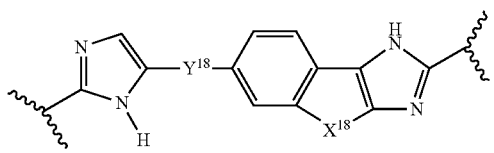

118 wherein $W^{1a}$ is optionally substituted with one or more (e.g. 1, 2, 3, or 4) groups independently selected from halo, alkyl, haloalkyl, cyano, and

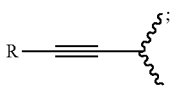

wherein each R is independently H, alkyl, haloalkyl, cycloalkyl, aryl, or heteroaryl;

$Y^{18}$ is selected from $A^0, A^1, A^2, A^3, A^7, A^{15}, A^{16},$ and $A^{20}$;

each $A^0$ is independently:

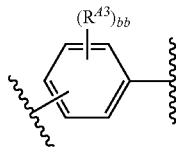

wherein:

each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or each $A^0$ is independently a six-membered heteroaromatic ring containing one, two, or three nitrogen atoms, which ring is optionally substituted with 1, 2, 3, or 4 $R^{43}$ groups;

each $A^1$ is independently:

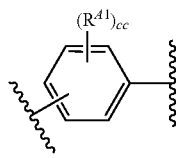

wherein:

each $R^{41}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and each R$^4$ is independently selected from H, alkyl, haloalkyl, aryl, and arylalkyl;

each cc is independently 1, 2, 3, or 4;

each $A^2$ is independently:

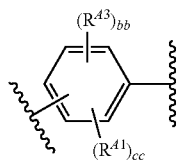

wherein:

each $R^{41}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each R$^4$ is independently selected from H, alkyl, haloalkyl, aryl, and arylalkyl;

R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each bb is 0, 1, 2, 3, or 4; each cc is 1, 2, 3, or 4; and the sum of bb and cc is 1, 2, 3, or 4;

each $A^3$ is independently a six-membered heteroaromatic ring containing one, two, or three nitrogen atoms, which ring is substituted with one or more $R^{41}$ groups, and which ring is optionally substituted with one or more $R^{43}$ groups;

each $A^7$ is independently:

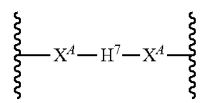

wherein:

each $H^7$ is independently a five-membered heteroaromatic ring, which $H^7$ is optionally substituted with one or more groups independently selected from $R^{41}$ and $R^{43}$; and each $X^4$ is independently O, NR, SO, SO$_2$, C(=O), NRC(=O), C(=O)NR, CR=CR, NRC(=O)NR, allenyl, alkynyl, or absent; and each R is independently selected from H or alkyl;

each $A^{15}$ is independently:

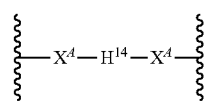

wherein:

each $H^{14}$ is independently a fused unsaturated, partially unsaturated or saturated tricyclic carbocycle which is optionally substituted with one or more groups independently selected from oxo, $R^{41}$ and $R^{43}$; and each $X^4$ is independently O, NR, SO, SO$_2$, C(=O), NRC(=O), C(=O)NR, CR=CR, NRC(=O)NR, allenyl, alkynyl, or absent and each R is independently selected from H or alkyl;

each $A^{16}$ is independently:

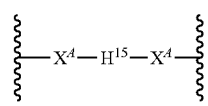

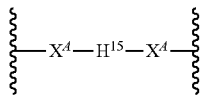

wherein:
each $H^{15}$ is independently a fused unsaturated, partially unsaturated or saturated tricyclic heterocycle that comprises at least one heteroatom in the ring system, which ring system is optionally substituted with one or more groups independently selected from $R^{41}$ and $R^{43}$; and
each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
each $A^{20}$ is independently a 5 or 6 membered heteroaryl ring that is optionally substituted with one or more groups independently selected from $R^{41}$ and $R^{43}$;
each $P^0$ is independently:

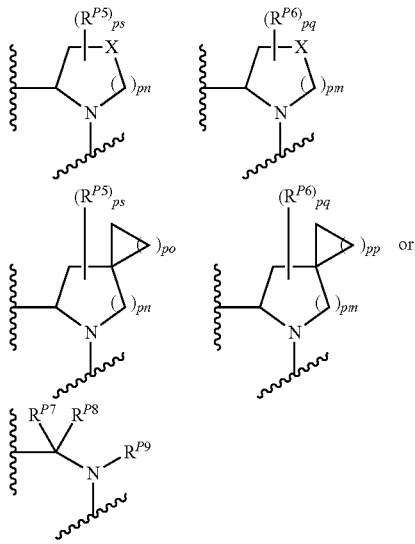

wherein:
X is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq and ps are independently 0, 1, 2, 3, or 4;
pm and pn are independently 0, 1, or 2;
po and pp are independently 1, 2, or 3;

$R^{P7}$ and $R^{P8}$ are each independently selected from hydrogen, alkenyl, alkoxyalkyl, alkyl, haloalkyl, and ($NR^{Pa}R^{Pb}$)alkyl; or $R^{P7}$ and $R^{P8}$, together with the carbon atom to which they are attached, form a five or six membered saturated ring optionally containing one or two heteroatoms selected from $NR^{Pz}$, O, and S; wherein $R^{Pz}$ is selected from hydrogen and alkyl;
$R^{P9}$ is selected from hydrogen and alkyl;
each $P^1$ is independently:

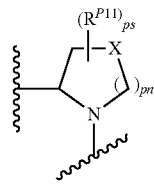

wherein:
X is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
at least one $R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocycyloxyalkyloxy, ($NR^hR^h$)alkyloxy, cyanoalkoxy, cyanocycloalkyloxy, cycloalkyloxy, oxo, heterocyclyl, —$NR^{hh}R^h$, ($NR^{hh}R^h$)alkyl, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —S(=O)$_2R^h$, —C(=O)$R^h$, —C(==)$NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo and heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 1, 2, 3, or 4;
pn is 0, 1, or 2;
each $P^3$ is independently a ring of the formula:

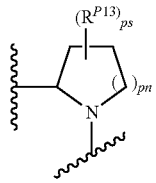

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;
each $P^5$ is independently a ring of the formula:

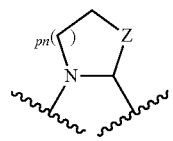

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pn is 0, 1, or 2;
Z is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

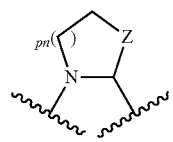

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
Z is O, S, S(=O), S(=O)$_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$.
each $P^8$ is independently a ring of the formula:

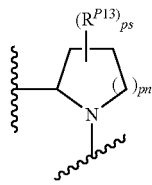

wherein:
ps is 2, 3, 4, 5, or 6;
pn is 0, 1 or 2;

each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

each $P^{10}$ is independently:

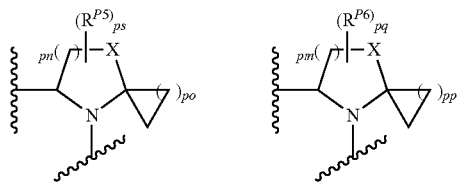

wherein:

X is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;
each $P^{12}$ is independently:

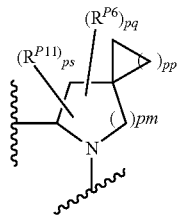

wherein:

each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq is independently 0, 1, 2, 3, or 4;
pm is independently 0, 1, or 2;
pp is independently 1, 2, or 3;
ps is 1, 2, 3, or 4;

$R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl, —$NR^{hh}R^h$, ($NR^{hh}R^h$)alkyl, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{15}$ is:

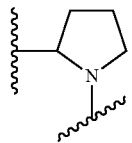

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

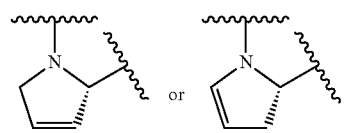 [SMILES: *[C@@H]1C=CCN1* ; *[C@@H]1CC=CN1*]

which is optionally substituted with one or two groups independently selected from halo, alkyl, alkoxyalkyl, haloalkyl, cycloalkyl, and cycloalkylalkyl;

each $P^{19}$ is:

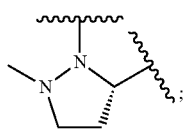 [SMILES: *[C@@H]1CCN(C)N1*]

each $P^{20}$ is:

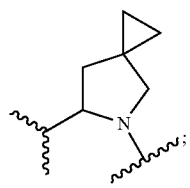 [SMILES: *C1CC2(CC2)CN1*]

each $P^{30}$ is independently a ring of the formula:

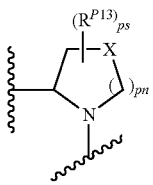

ps is 2
pn is 0, 1 or 2;
X is selected from O, S, S(O), SO$_2$, or CH$_2$; provided that when pn is 0, X is CH$_2$.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl; and each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

$X^{18}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—;

or a pharmaceutically acceptable salt or prodrug thereof.

357

In one specific embodiment $W^{1a}$ is:

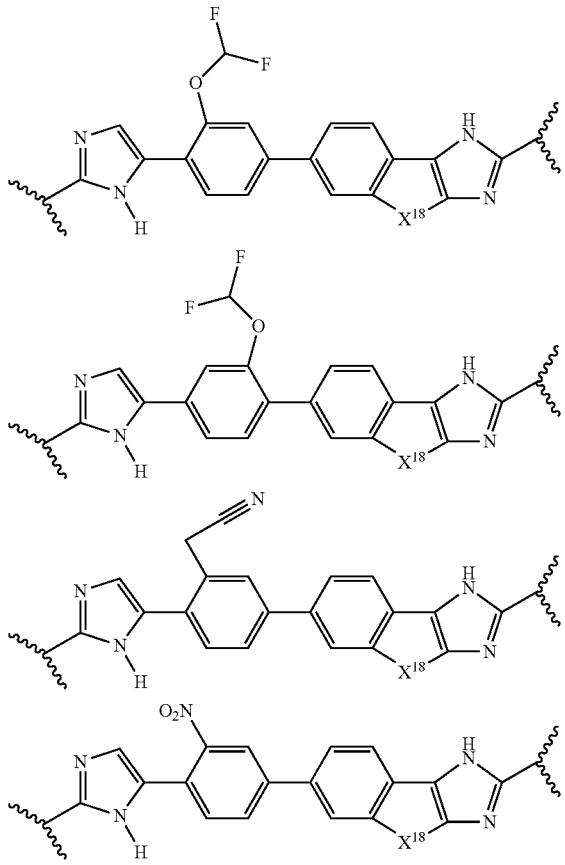

In one specific embodiment $X^{18}$ is: $X^{16}$ is —CH$_2$—CH$_2$—, —CH$_2$—O—, —O—CH$_2$—, —S—, —O—, —CO—, —CF$_2$—, or —CH═CH—.

In one specific embodiment $W^{1a}$ is:

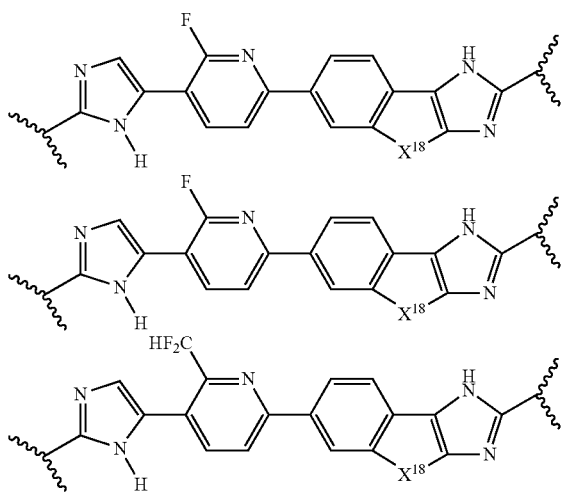

In one specific embodiment $X^{18}$ is $X^{16}$ is —CH$_2$—CH$_2$—, —CH$_2$—O—, —O—CH$_2$—, —S—, —O—, —CO—, —CF$_2$—, or —CH═CH—.

358

In one specific embodiment $W^{1a}$ is:

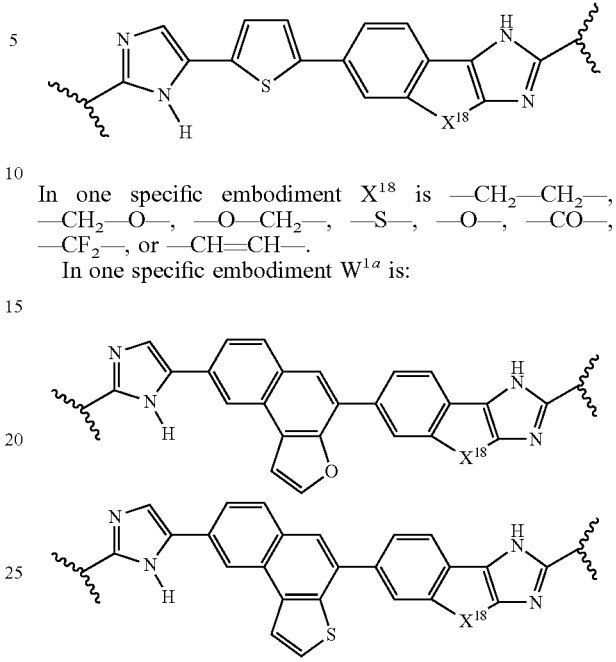

In one specific embodiment $X^{18}$ is —CH$_2$—CH$_2$—, —CH$_2$—O—, —O—CH$_2$—, —S—, —O—, —CO—, —CF$_2$—, or —CH═CH—.

In one specific embodiment $W^{1a}$ is:

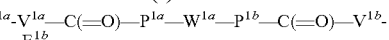

In one specific embodiment $X^{18}$ is —CH$_2$—CH$_2$—, —CH$_2$—O—, —O—CH$_2$—, —S—, —O—, —CO—, —CF$_2$—, or —CH═CH—.

In one specific embodiment the invention provides a compound of formula (I):

$$E^{1a}\text{-}V^{1a}\text{—C}(\text{=O})\text{—}P^{1a}\text{—}W^{1a}\text{—}P^{1b}\text{—C}(\text{=O})\text{—}V^{1b}\text{-}E^{1b} \quad (I)$$

wherein:

$E^{1a}$ is $E^0$ or $E^1$, or $E^{1a}$-$V^{1a}$ taken together are $R^{9a}$;
$E^{1b}$ is $E^0$ or $E^1$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, aryl, and heterocyclyl;

359 each $V^o$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$P^{1a}$ and $P^{1b}$ are each independently selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;

each $P^0$ is independently:

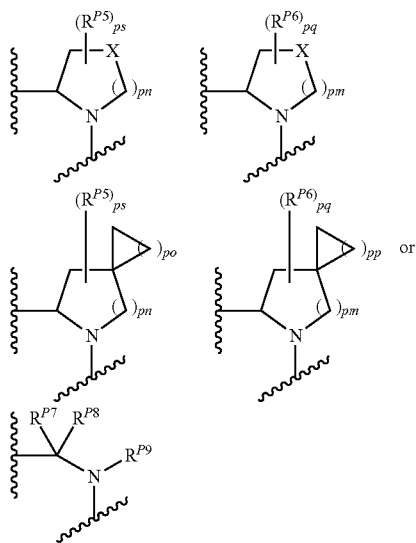

360 wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;
R$^{P7}$ and R$^{P11}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;
each P$^1$ is independently:

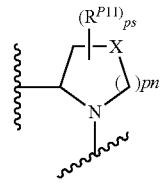

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, —S(=O)$_2R^h$, —C(=O)$R^h$, —C(=O)$NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo and heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;
each $P^3$ is independently a ring of the formula:

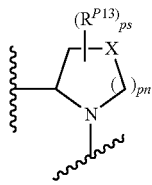

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 0, 1, 2, 3, or 4;
pn is 0, 1, or 2;
each $P^5$ is independently a ring of the formula:

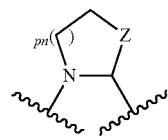

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pn is 0, 1, or 2;
Z is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2NR^hR^h$, —S(=O)$_2R^h$, C(=O)$R^h$, C(=O)O$R^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

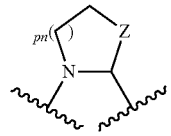

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
Z is O, S, S(=O), S(=O)$_2$, or $NR^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2NR^hR^h$, —S(=O)$_2R^h$, C(=O)$R^h$, C(=O)O$R^h$, —C(=O)$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;

each $P^8$ is independently a ring of the formula:

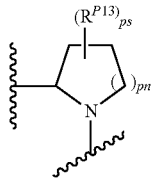

wherein:
ps is 2, 3, 4, 5, or 6;
pn is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
each $P^{10}$ is independently:

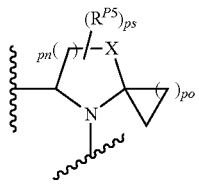 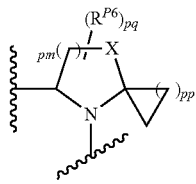

wherein:
X is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq and ps are independently 0, 1, 2, 3, or 4;

pm and pn are independently 0, 1, or 2;
po and pp are independently 1, 2, or 3;
each $P^{12}$ is independently:

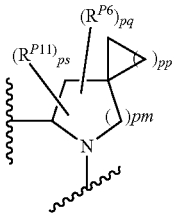

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq is independently 0, 1, 2, 3, or 4;
pm is independently 0, 1, or 2;
pp is independently 1, 2, or 3;
ps is 1, 2, 3, or 4;
$R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl, —$NR^{hh}R^h$, $(NR^{hh}R^h)$alkyl, $(NR^{hh}R^h)$carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each P¹⁵ is:

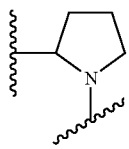 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each P¹⁸ is:

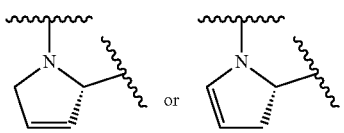 [SMILES: *[C@@H]1C=CCN1* ; *[C@@H]1CC=CN1*]

which is optionally substituted with one or two groups independently selected from halo, alkyl, alkoxyalkyl, haloalkyl, cycloalkyl, and cycloalkylalkyl;

each P¹⁹ is:

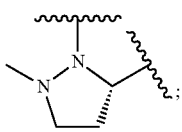

each P³⁰ is independently a ring of the formula:

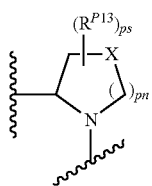

ps is 2
pn is 0, 1 or 2;
X is selected from O, S, S(O), SO₂, or CH₂; provided that when pn is 0, X is CH₂.

each $R^{P13}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P13}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl, wherein $R^{X'}$ and $R^{Y'}$ are independently selected from hydrogen and alkyl;

$W^{1a}$ is selected from:

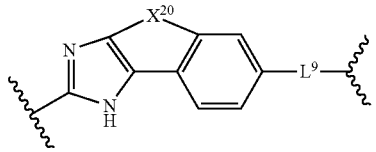
120

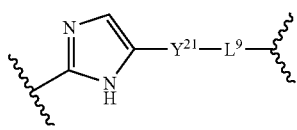
121

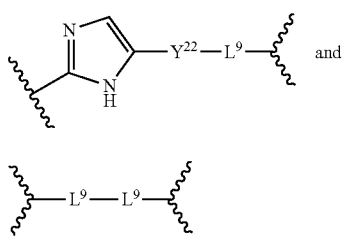
122 and

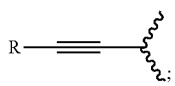
123 wherein each $W^{1a}$ is optionally substituted with one or more (e.g. 1, 2, 3, or 4) groups independently selected from halo, alkyl, haloalkyl, cyano, and

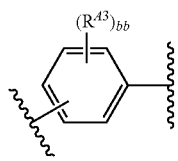

wherein each R is independently H, alkyl, haloalkyl, cycloalkyl, aryl, or heteroaryl;

$X^{20}$ is —$CH_2$—, —$CH_2$—$CH_2$—, —$CH_2$—O—, —O—$CH_2$—, —$CH_2$—O—$CH_2$—, —S—, —$S(O)_2$—, —C(O)—, —$CF_2$—, —O—, —S—$CH_2$—, —$CH_2$—S—, —O—C(O)—, —C(O)—O—, —CH=N—; —N=CH—; or —CH=CH—

$Y^{21}$ is a bicyclic aromatic ring system comprising eight to 12 atoms optionally including one or more heteroatoms selected from O, S, and N, which bicyclic ring system is optionally with one or more groups independently selected from halo, haloalkyl, alkyl and oxo;

$Y^{22}$ is selected from $A^0$, $A^1$, $A^2$, $A^3$, $A^7$, $A^{15}$, $A^{16}$, and $A^{20}$;

each $A^0$ is independently:

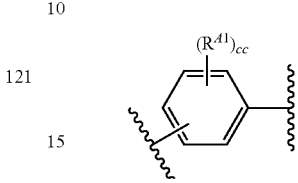

wherein:
each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, and ($NR^aR^b$)carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or each $A^0$ is independently a six-membered heteroaromatic ring containing one, two, or three nitrogen atoms, which ring is optionally substituted with 1, 2, 3, or 4 $R^{43}$ groups;

each $A^1$ is independently:

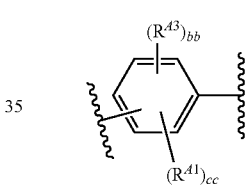

wherein:
each $R^{41}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and
each $R^4$ is independently selected from H, alkyl, haloalkyl, aryl, and arylalkyl;
each cc is independently 1, 2, 3, or 4;
each $A^2$ is independently:

wherein:
each $R^{41}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, and ($NR^aR^b$)carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $R^4$ is independently selected from H, alkyl, haloalkyl, aryl, and arylalkyl;
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each bb is 0, 1, 2, 3, or 4; each cc is 1, 2, 3, or 4; and the sum of bb and cc is 1, 2, 3, or 4;
each $A^3$ is independently a six-membered heteroaromatic ring containing one, two, or three nitrogen atoms, which ring is substituted with one or more $R^{41}$ groups, and which ring is optionally substituted with one or more $R^{43}$ groups;

each A⁷ is independently:

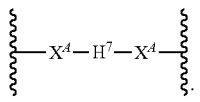

wherein:
each H⁷ is independently a five-membered heteroaromatic ring, which H⁷ is optionally substituted with one or more groups independently selected from R^{A1} and R^{A3}; and
each X⁴ is independently O, NR, SO, SO₂, C(=O), NRC(=O), C(=O)NR, CR=CR, NRC(=O)NR, allenyl, alkynyl, or absent; and each R is independently selected from H or alkyl;
each A¹⁵ is independently:

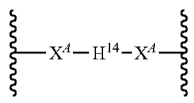

wherein:
each H¹⁴ is independently a fused unsaturated, partially unsaturated or saturated tricyclic carbocycle which is optionally substituted with one or more groups independently selected from oxo, R^{A1} and R^{A3}; and
each X⁴ is independently O, NR, SO, SO₂, C(=O), NRC(=O), C(=O)NR, CR=CR, NRC(=O)NR, allenyl, alkynyl, or absent and each R is independently selected from H or alkyl;
each A¹⁶ is independently:

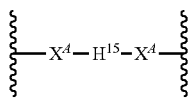

wherein:
each H¹⁵ is independently a fused unsaturated, partially unsaturated or saturated tricyclic heterocycle that comprises at least one heteroatom in the ring system, which ring system is optionally substituted with one or more groups independently selected from R^{A1} and R^{A3}; and
  each X⁴ is independently O, NR, SO, SO₂, C(=O), NRC(=O), C(=O)NR, CR=CR, NRC(=O)NR, allenyl, alkynyl, or absent and each R is independently selected from H or alkyl;
  each A²⁰ is independently a 5 or 6 membered heteroaryl ring that is optionally substituted with one or more groups independently selected from R^{A1} and R^{A3};
  each L⁹ is independently a fused-tetracyclic saturated, partially unsaturated, or aromatic heterocyclic ring system that is optionally substituted with one or more groups independently selected from oxo, halo, —R^{L9}, —OR^{L9}, —SR^{L9}, —CF₃, —CCl₃, —OCF₃, —CN, —NO₂, —N(R^{L9})C(=O)R^{L9}, —C(=O)R^{L9}, —OC(=O)R^{L9}, —C(O)OR^{L9}, —C(=O)NR^{L9}, —S(=O)R^{L9}, —S(=O)₂OR^{L9}, —S(=O)₂R^{L9}, —OS(=O)₂OR^{L9}, —S(O)₂NR^{L9}, alkoxyalkyl, arylalkoxycarbonyl, halo, haloalkyl, hydroxyalkyl, —NR^aR^b, (NR^aR^b)alkyl, and (NR^aR^b)carbonyl;
  each R^{L9} is independently —H, alkyl, aryl, arylalkyl, or heterocycle; and R^a and R^b are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
  or a pharmaceutically acceptable salt or prodrug thereof.
In one specific embodiment W^{1a} is:

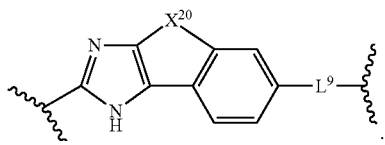

In one specific embodiment W^{1a} is:

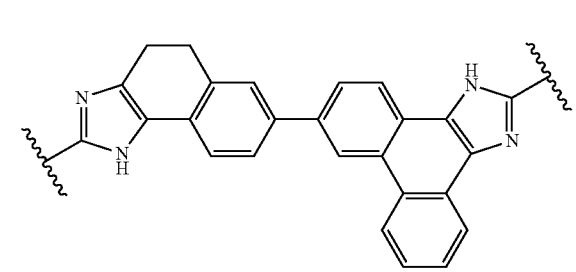

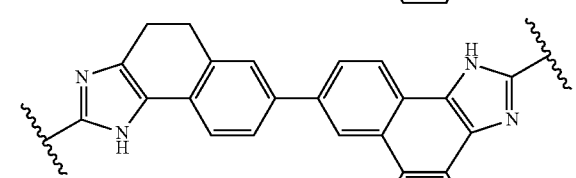

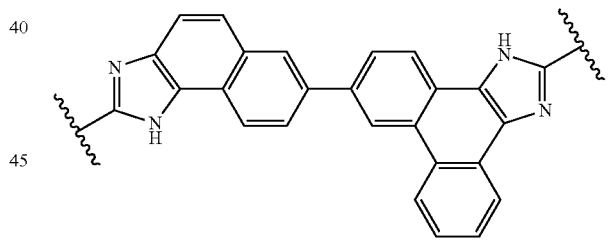

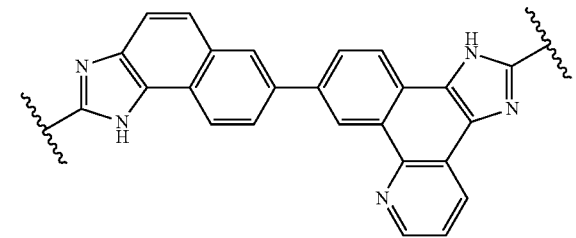

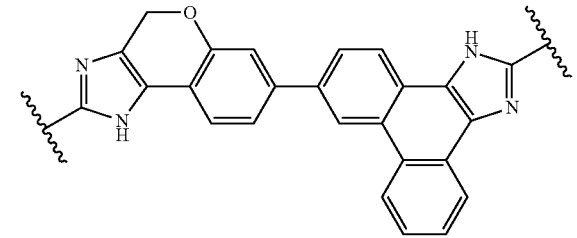

371
-continued
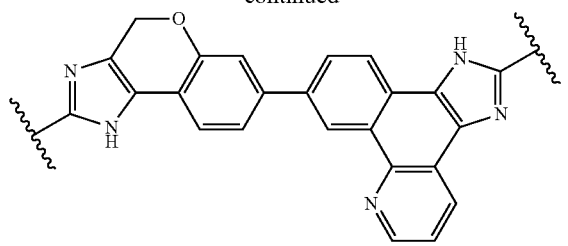
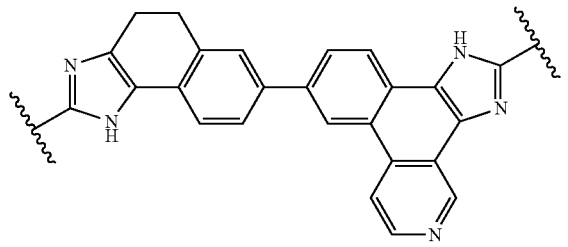
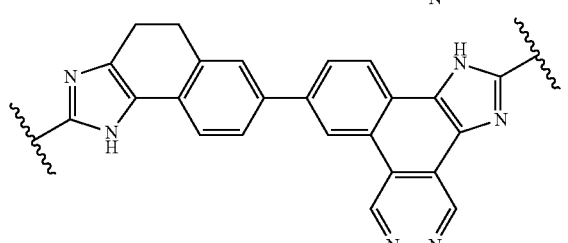
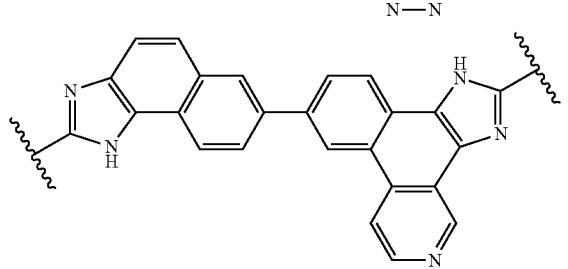
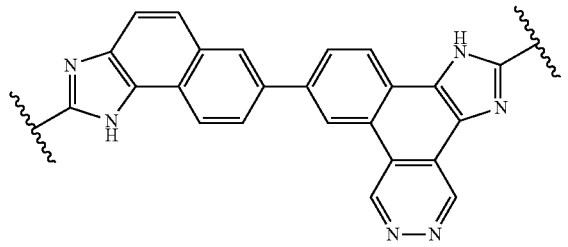
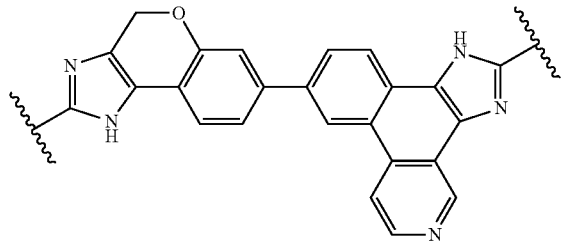
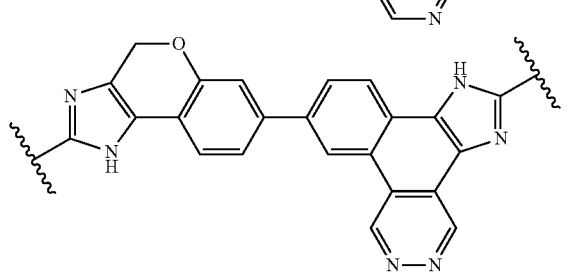
372
-continued
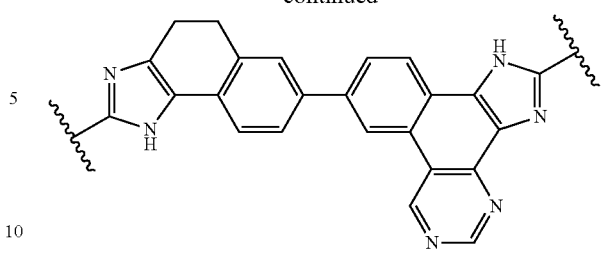

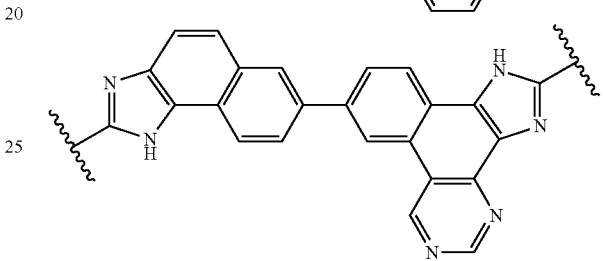

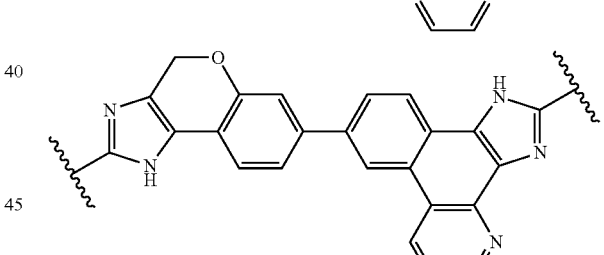
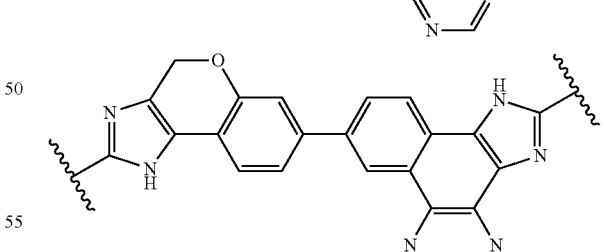
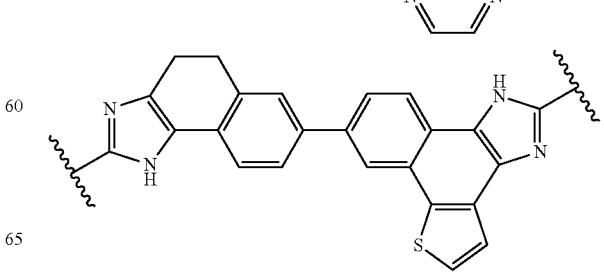

373
-continued
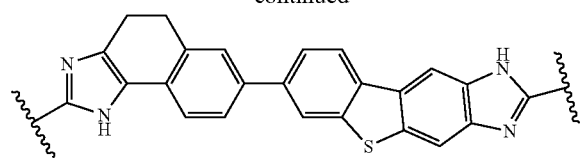
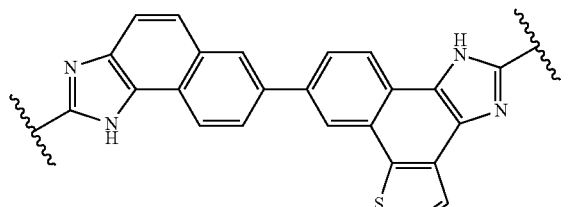
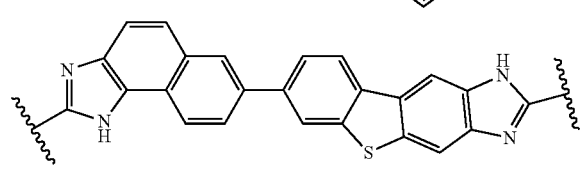
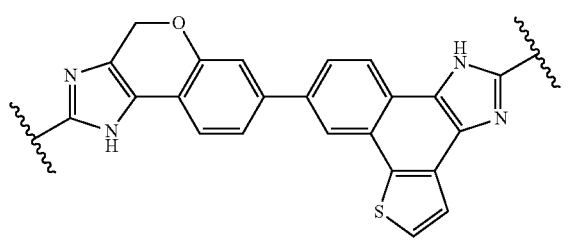
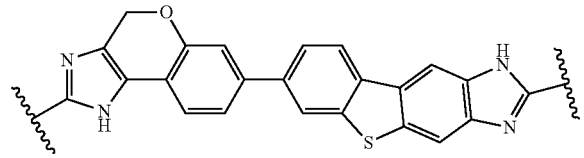
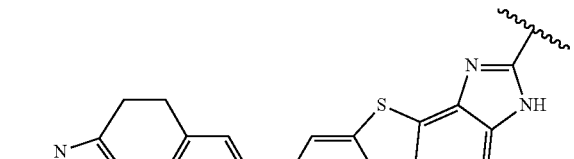
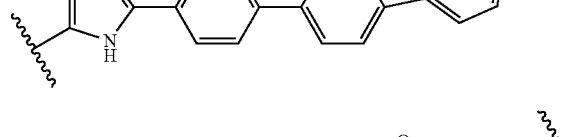
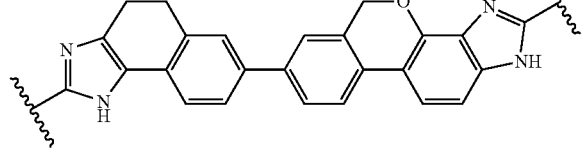
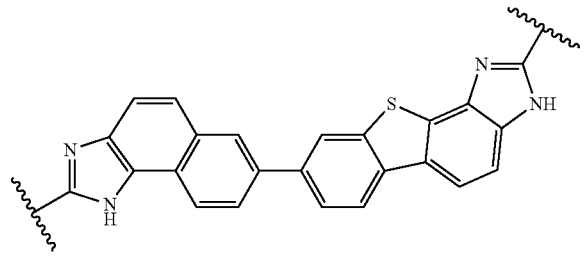
374
-continued
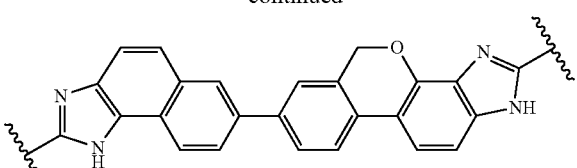
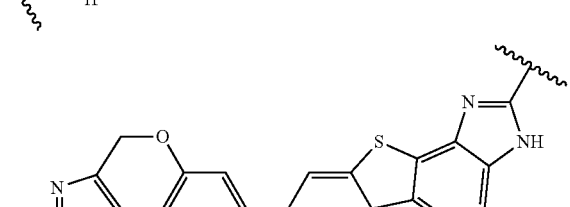
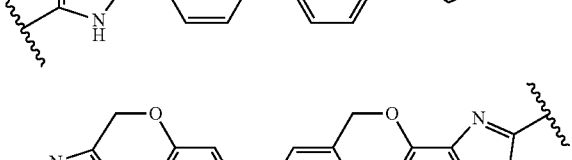
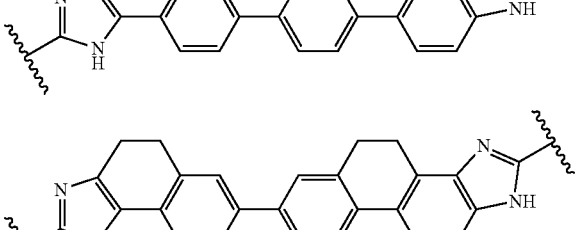
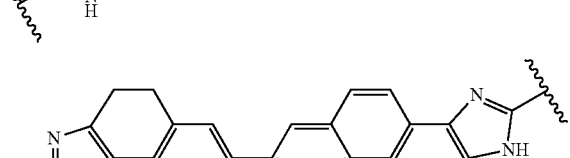
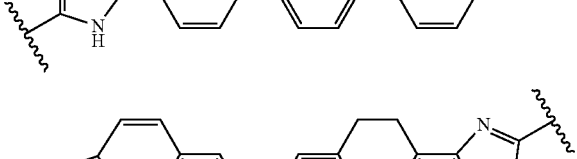
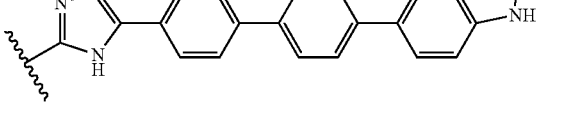
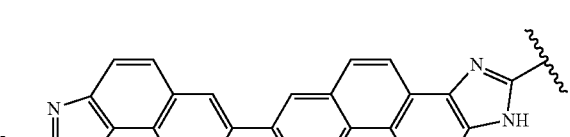
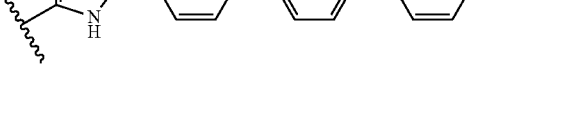
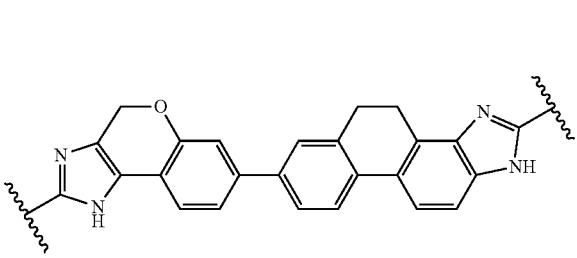

-continued
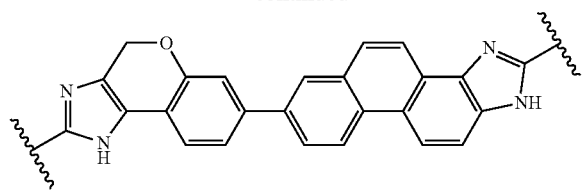
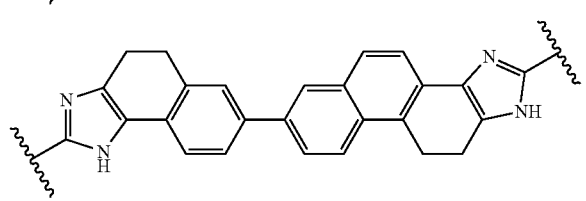
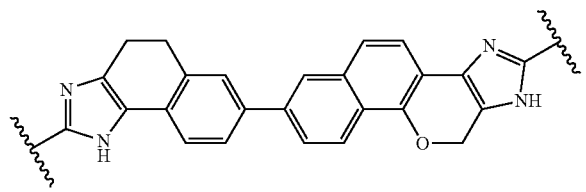
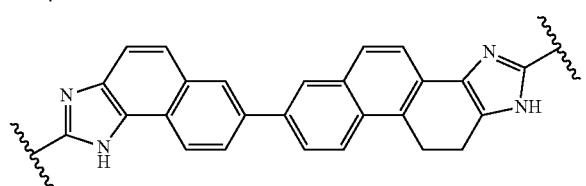
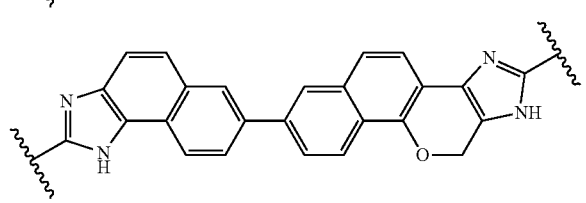
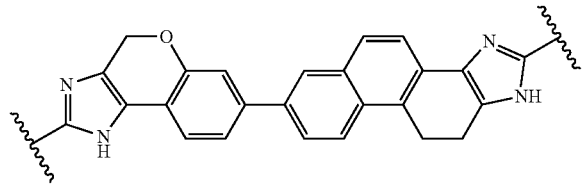
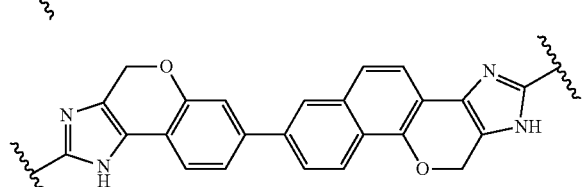
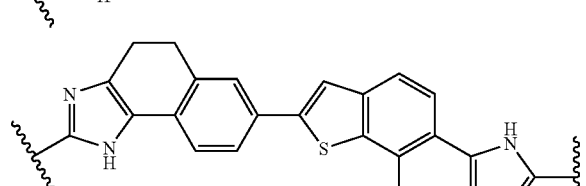
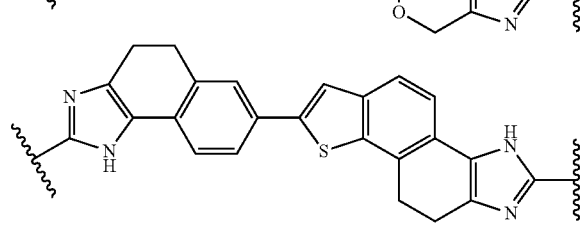
-continued
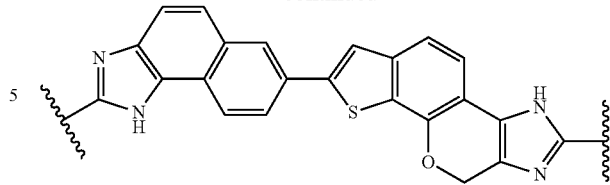
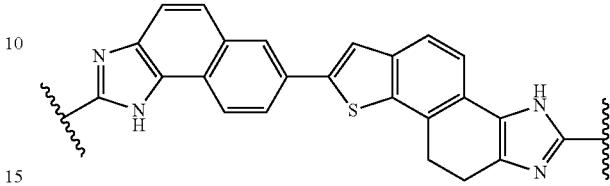
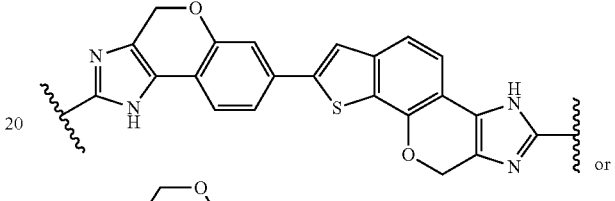

or
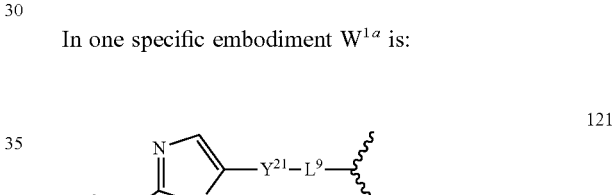.
In one specific embodiment $W^{1a}$ is:
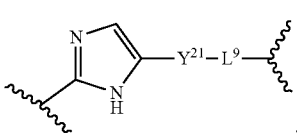
121
In one specific embodiment $W^{1a}$ is:
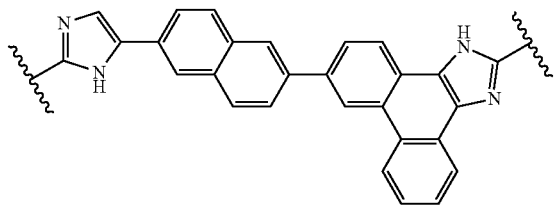
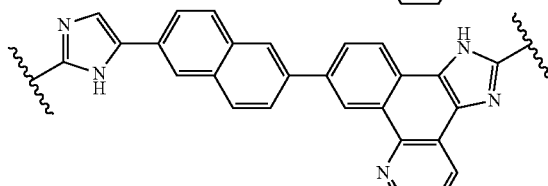
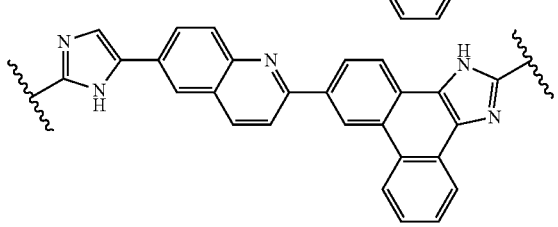

377
-continued
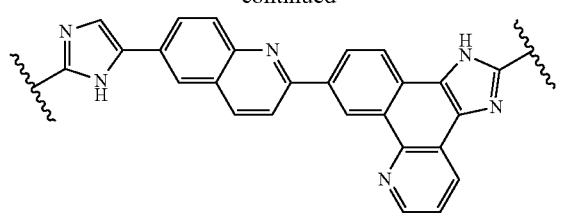
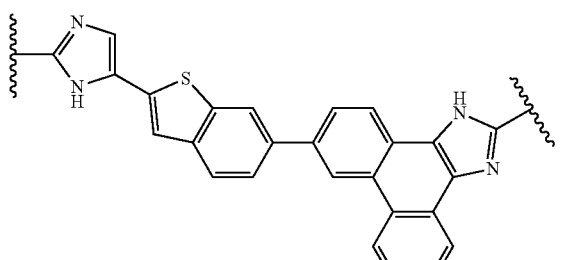
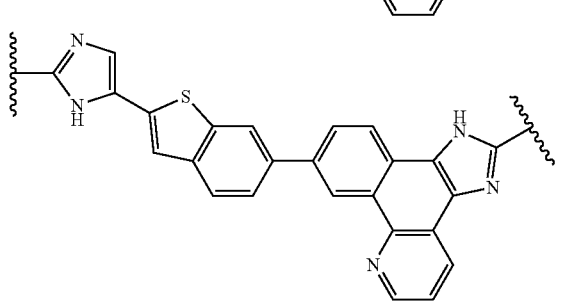
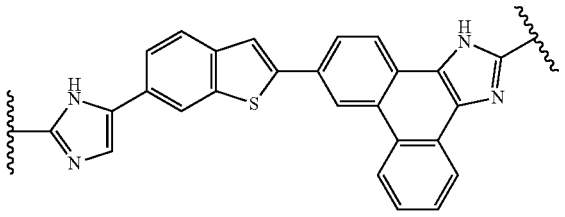
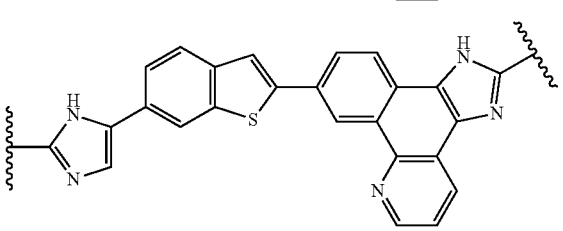
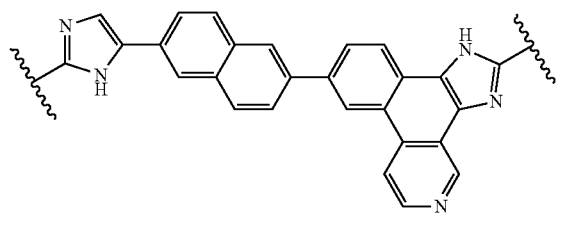
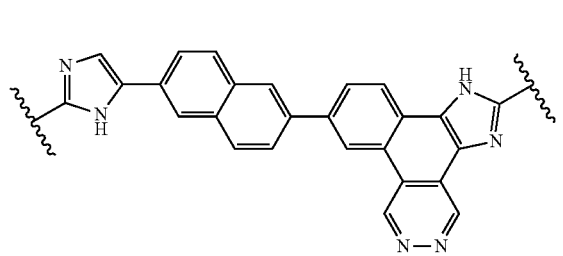
378
-continued
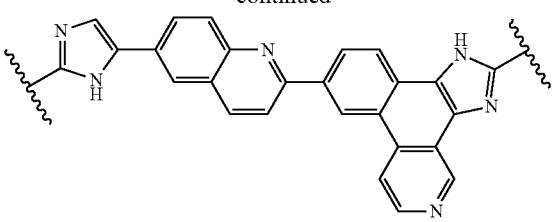
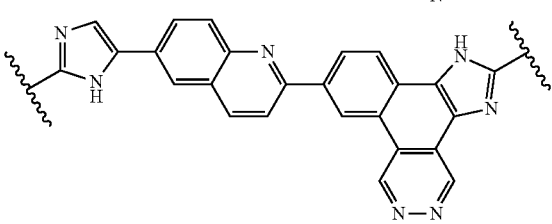
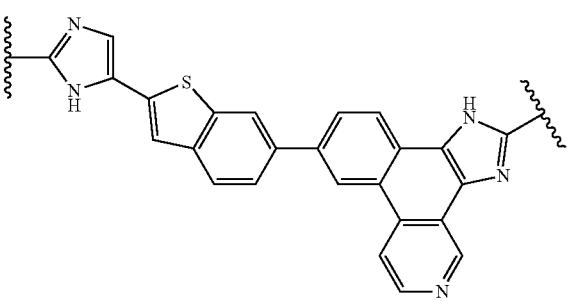
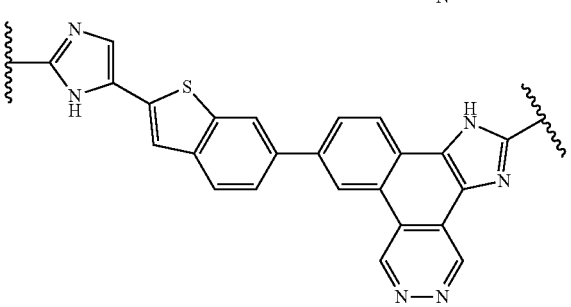
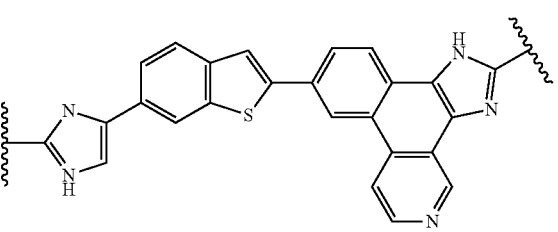
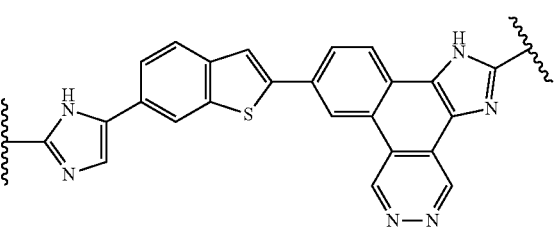
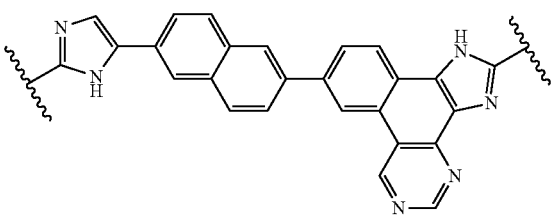

379
-continued
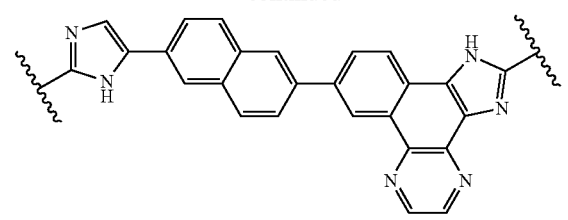
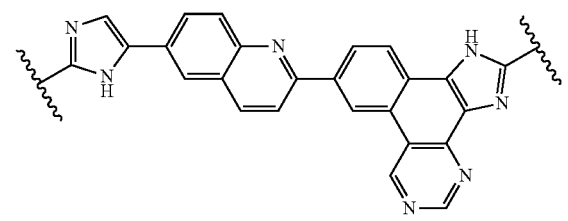
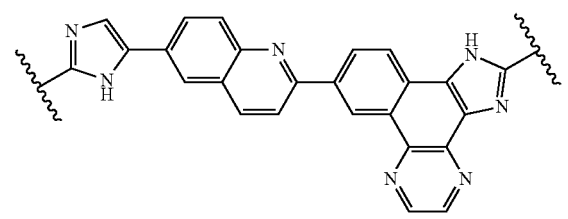
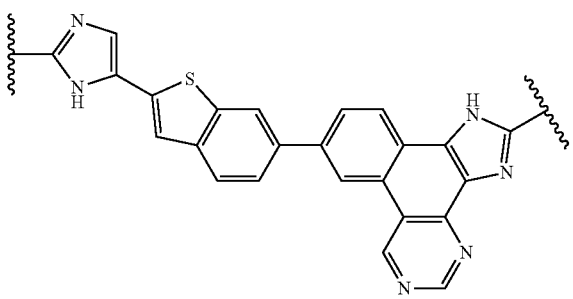
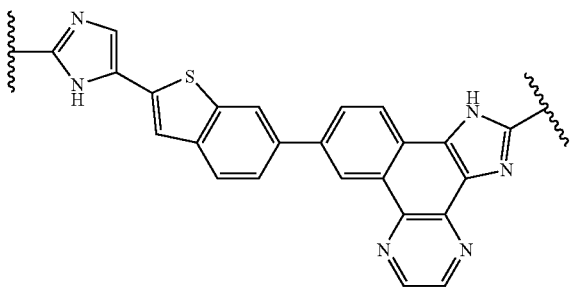
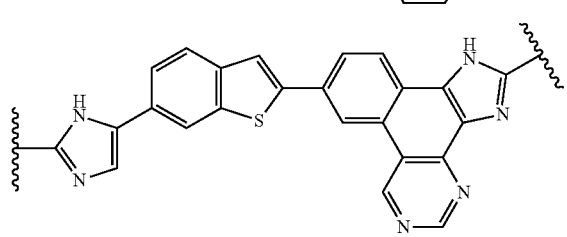
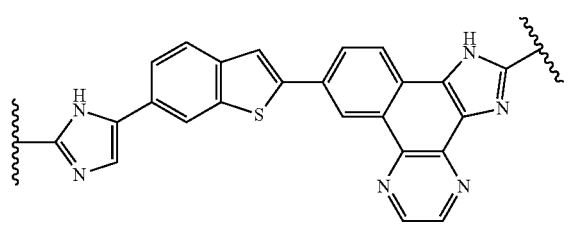
380
-continued
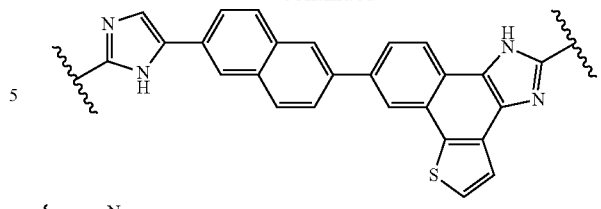
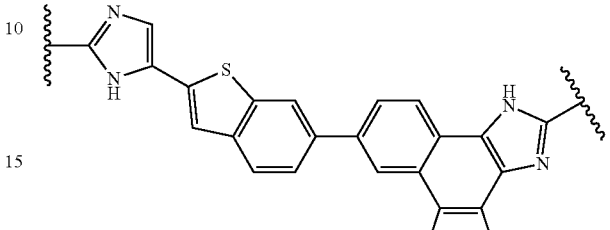
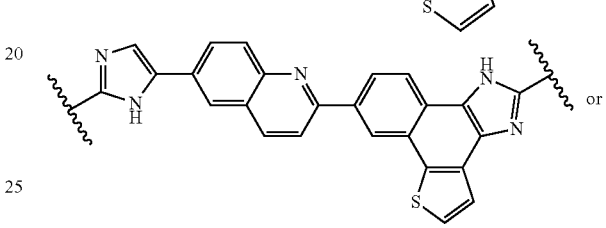
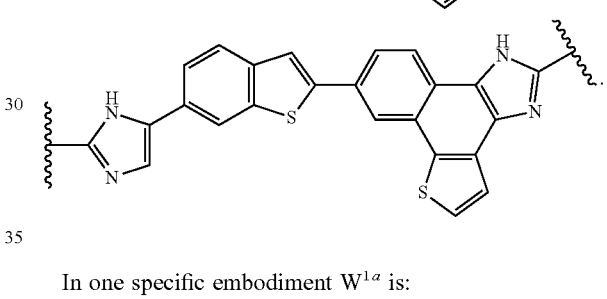
In one specific embodiment $W^{1a}$ is:
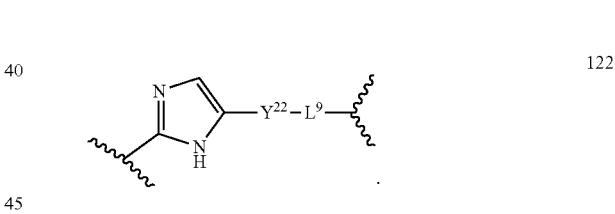
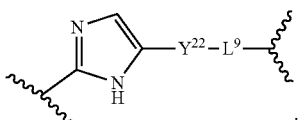
In one specific embodiment $W^{1a}$ is:
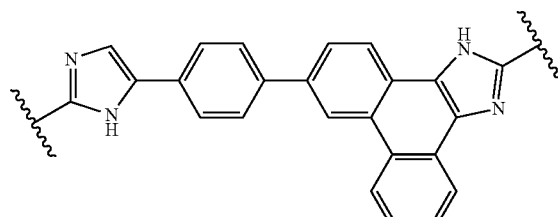
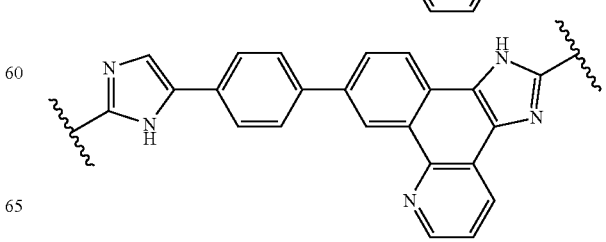

381
-continued
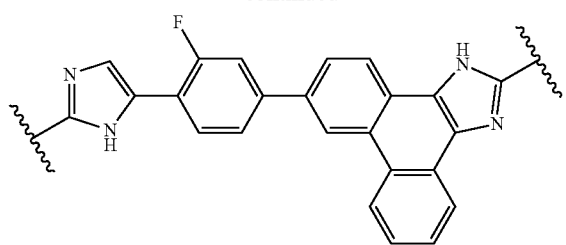
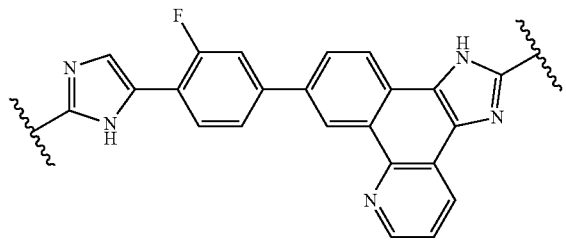
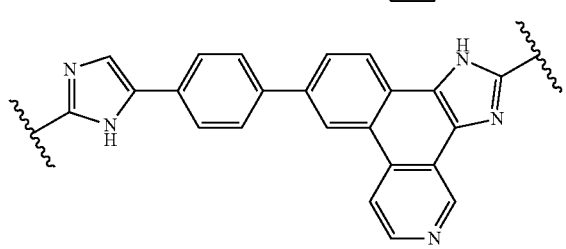
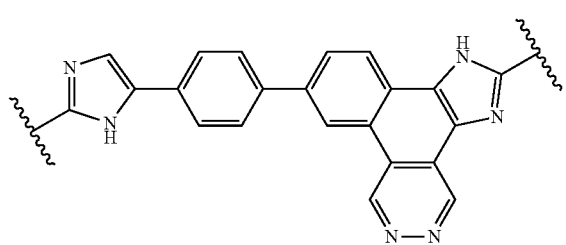
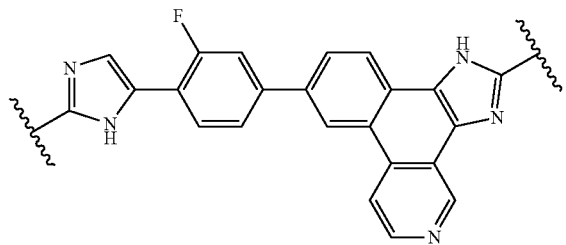
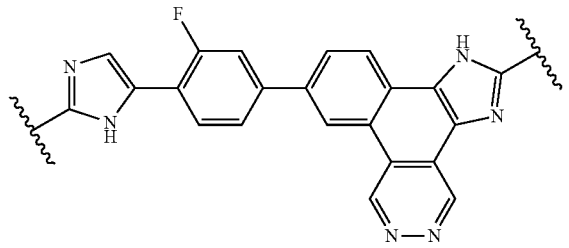
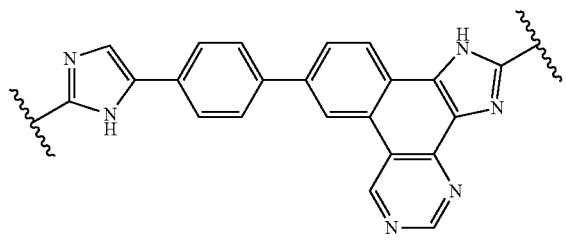
382
-continued
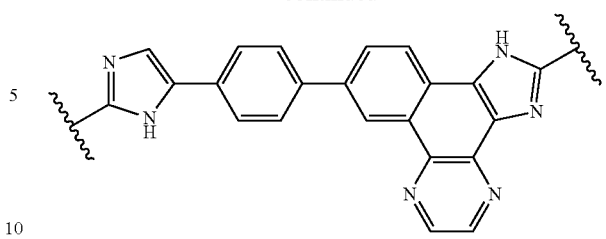
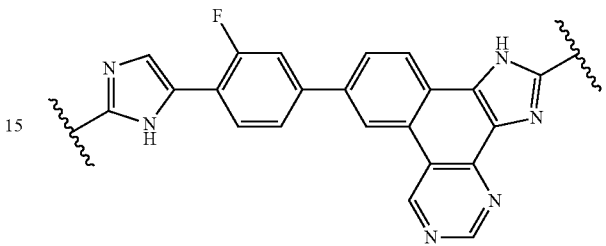
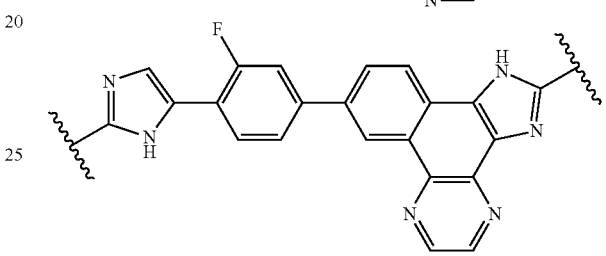
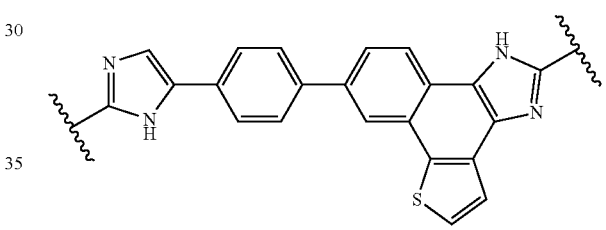
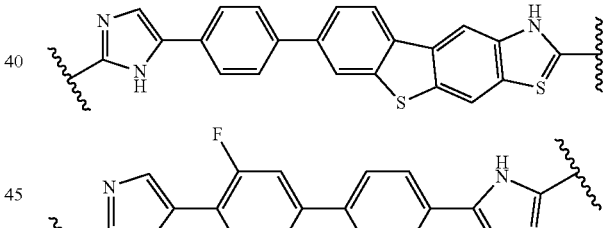
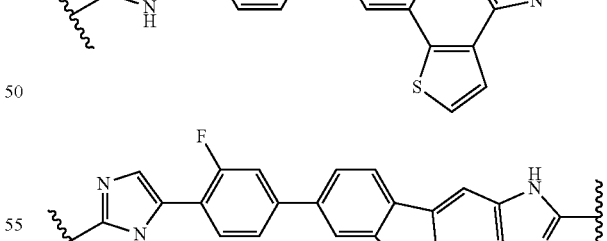
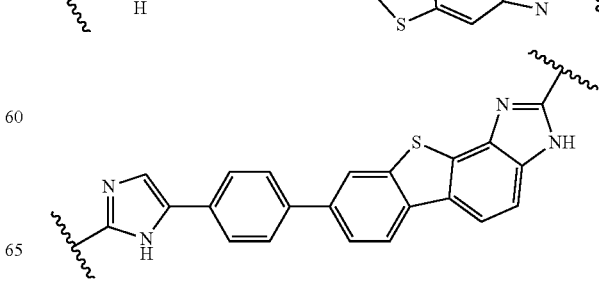

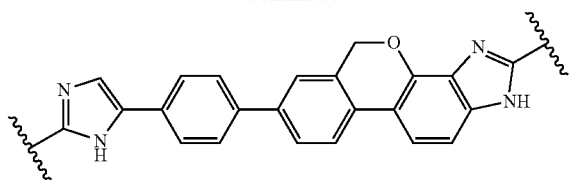
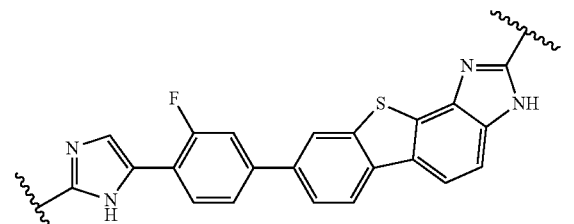
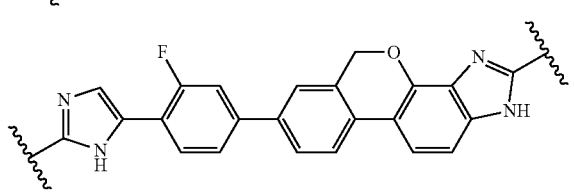
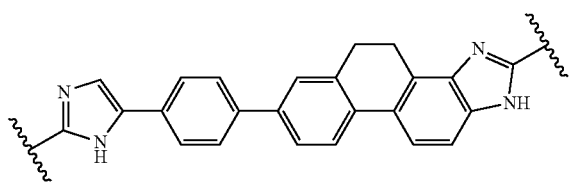
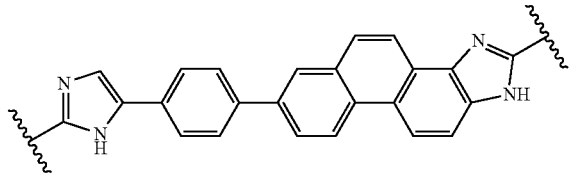
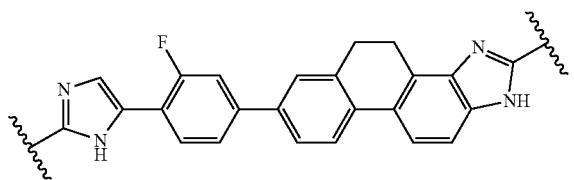
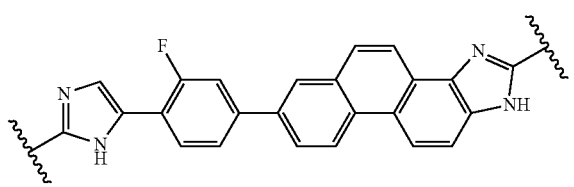
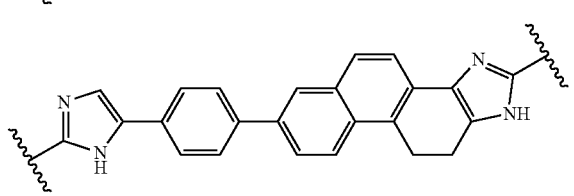
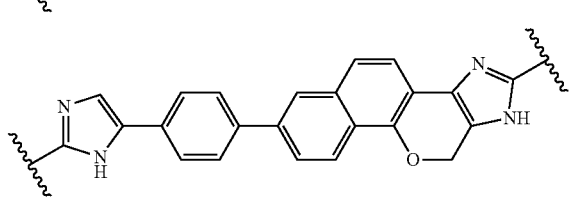
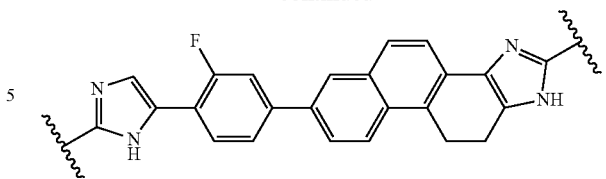

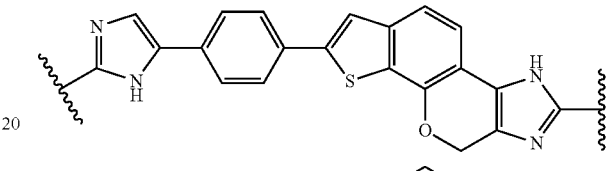
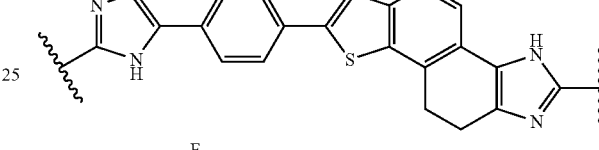
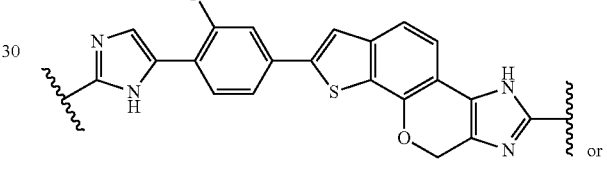
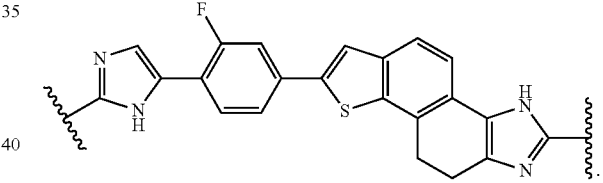
In one specific embodiment $W^{1a}$ is:
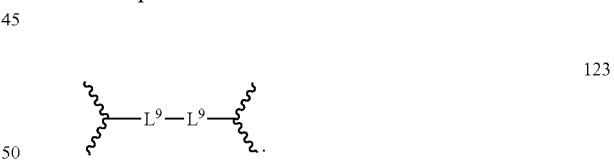
In one specific embodiment $W^{1a}$ is:
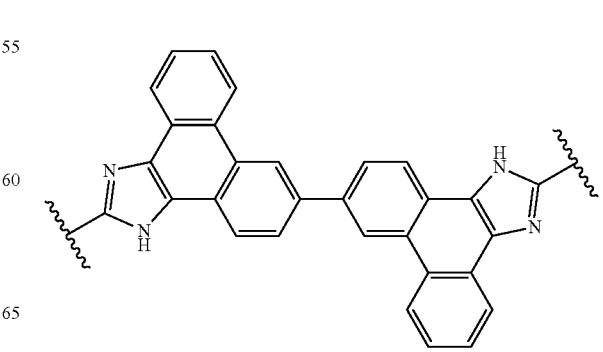

385
-continued
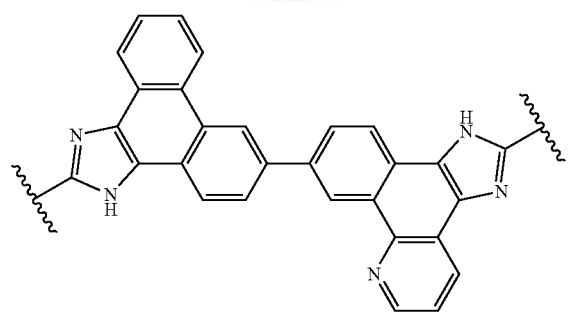
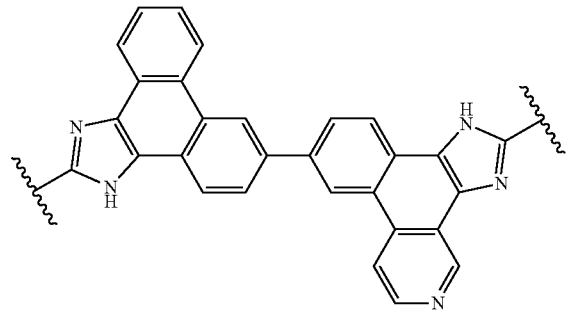
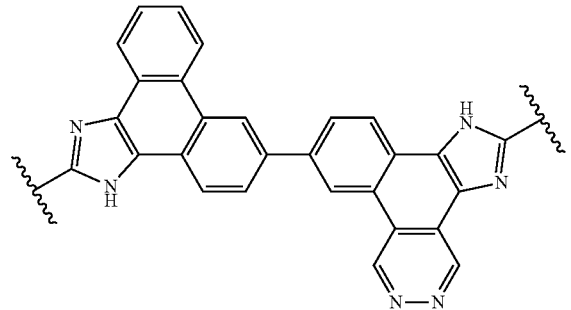
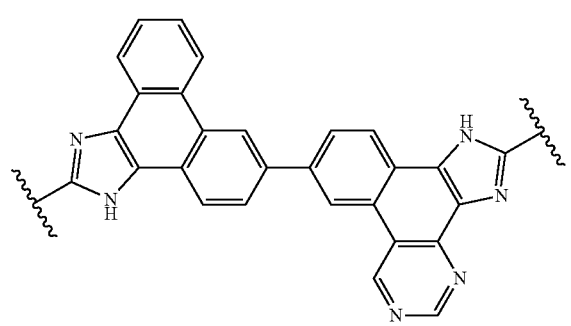
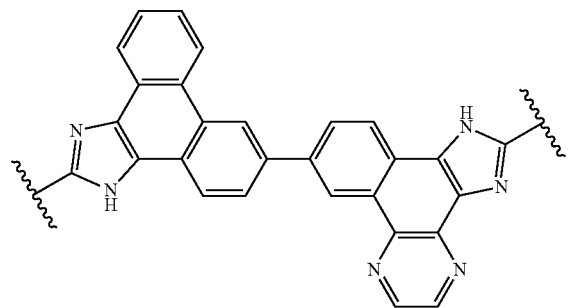
386
-continued
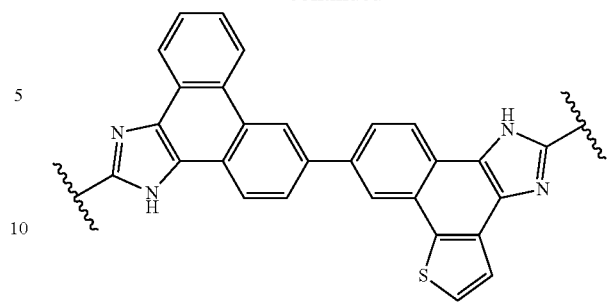
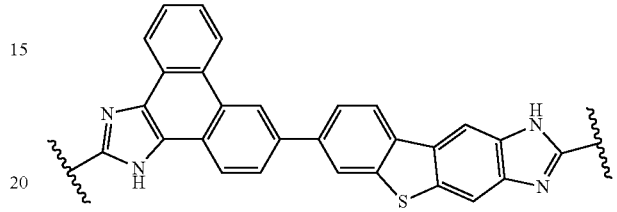
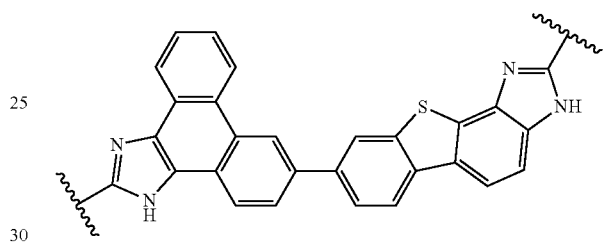
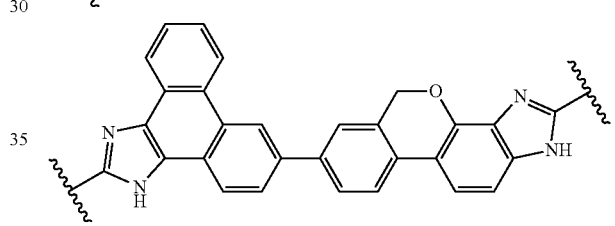
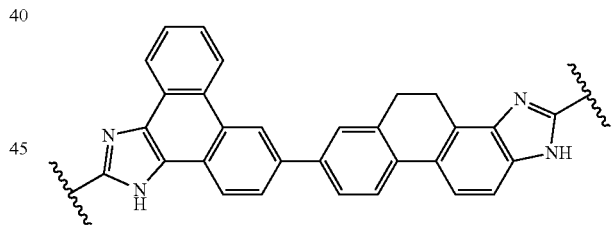
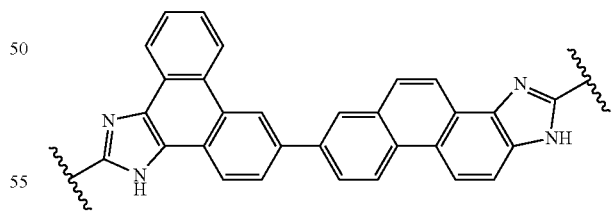
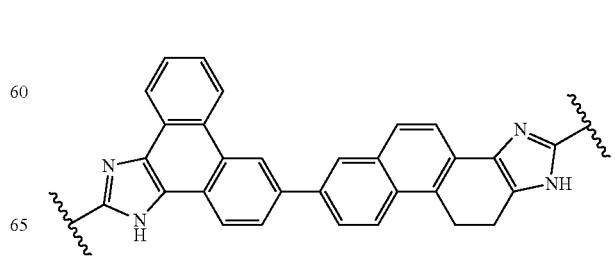

387
-continued
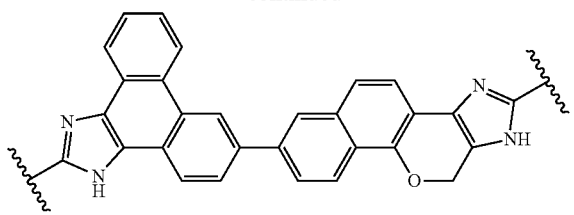
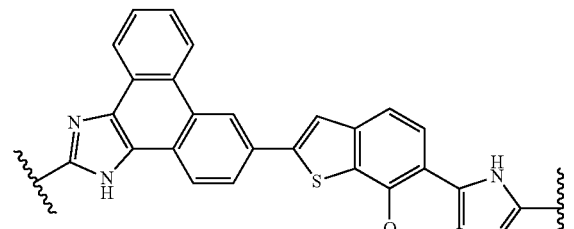
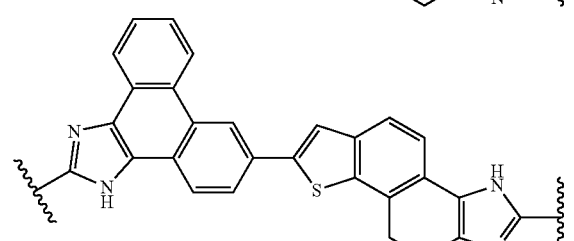
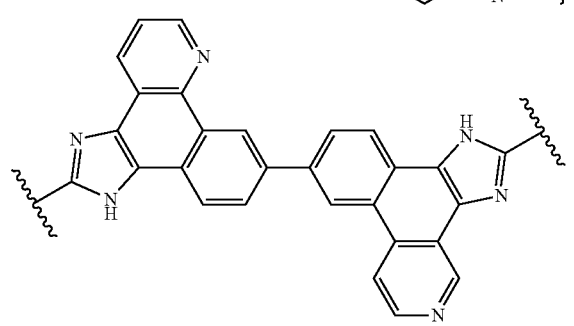
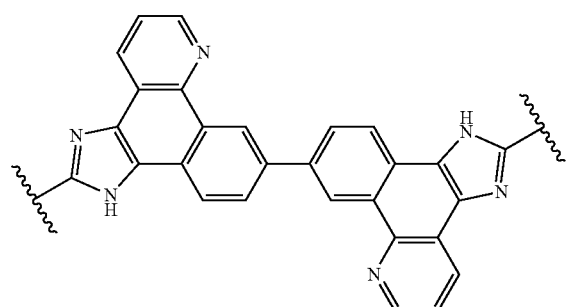
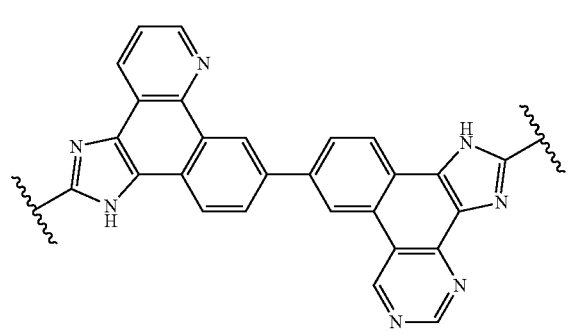
388
-continued
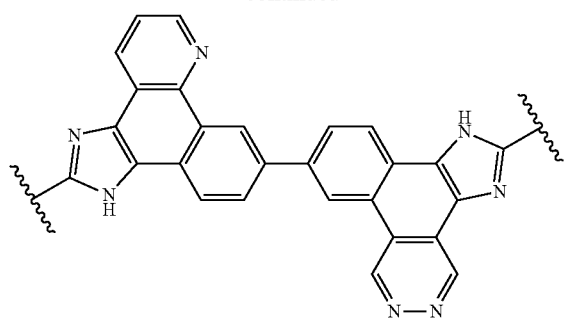
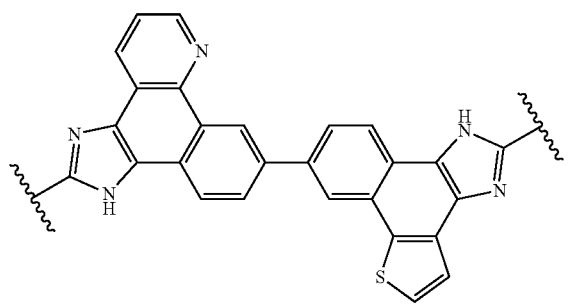
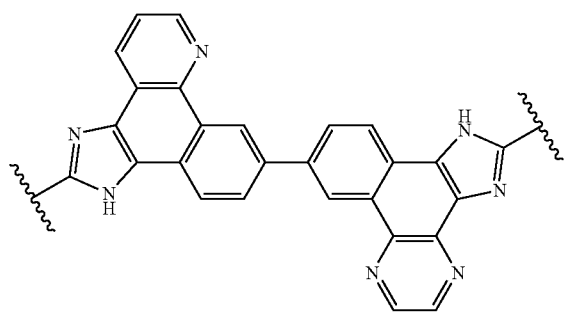
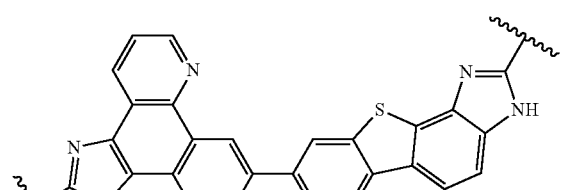
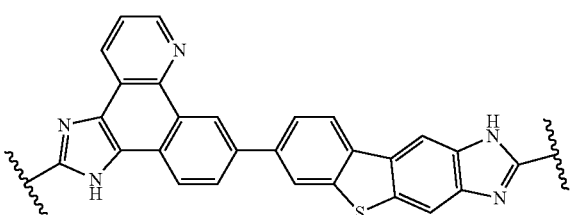
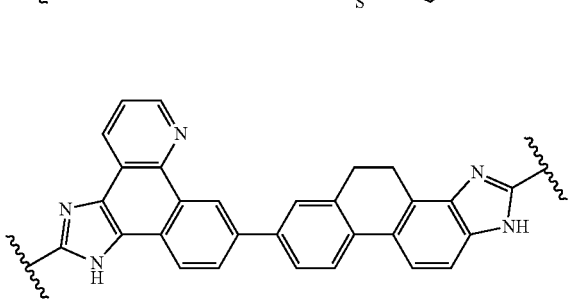

| 389 | 390 |
|---|---|
| -continued | -continued |
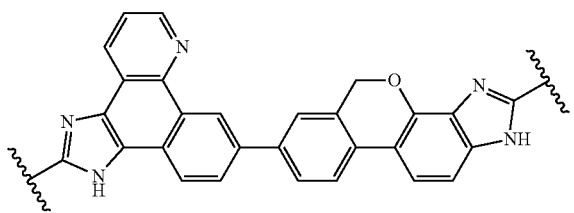
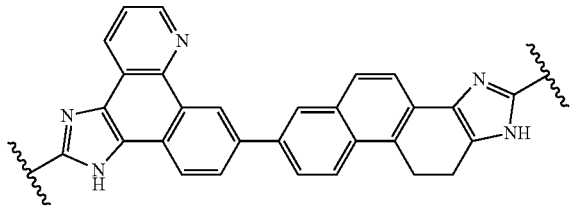
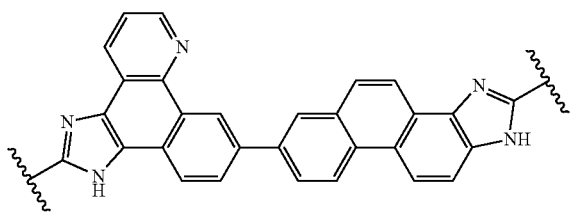
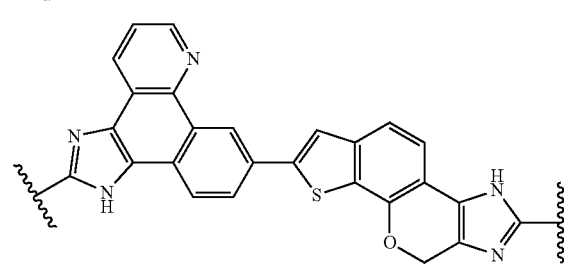
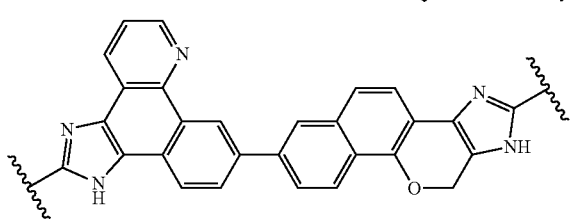
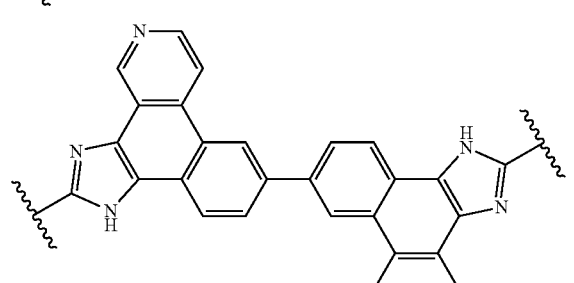
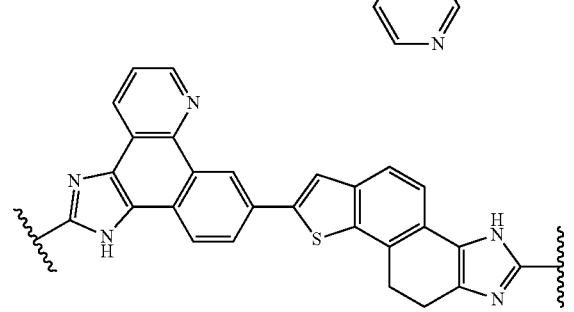
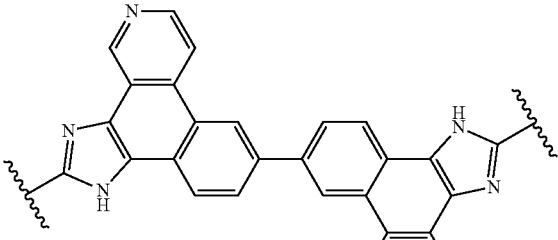
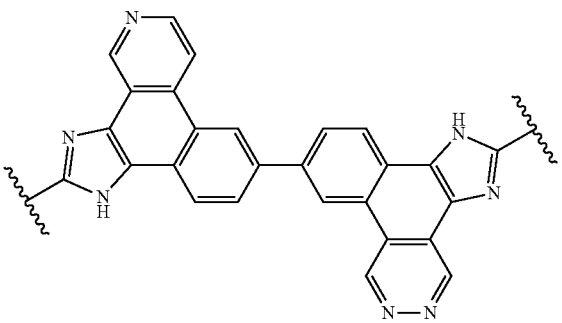
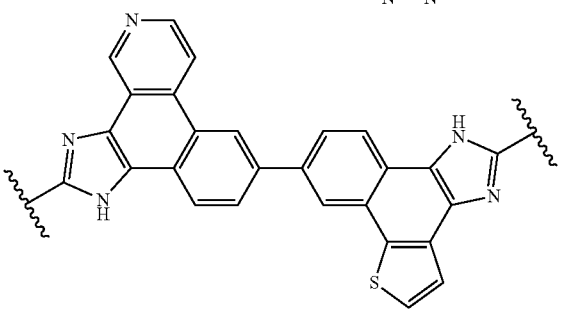
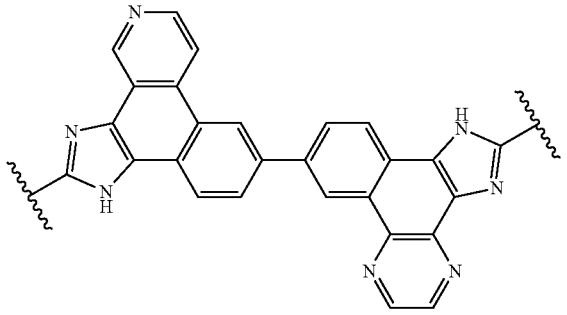
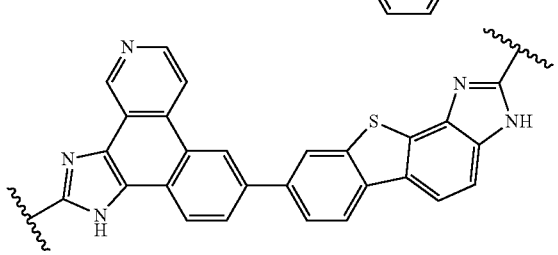
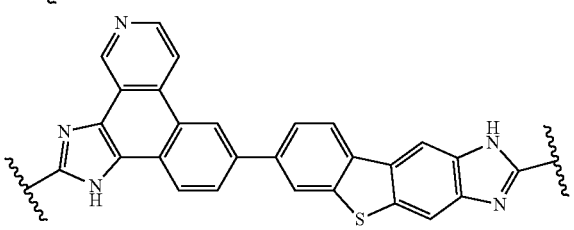

391
-continued
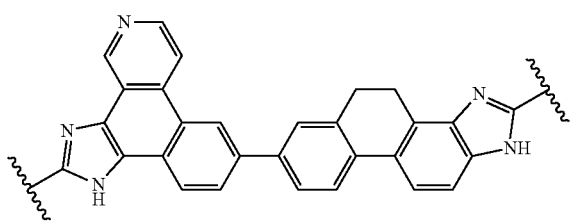
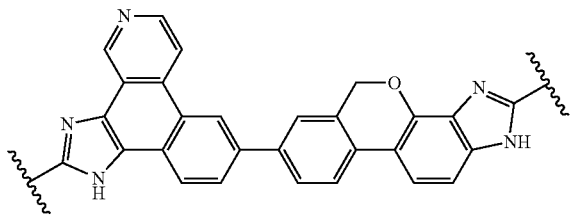
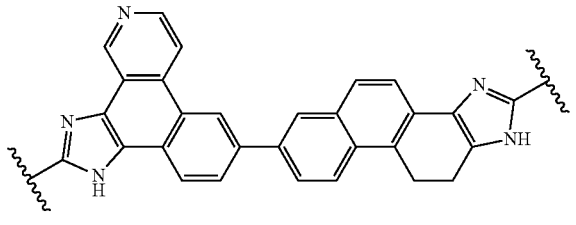
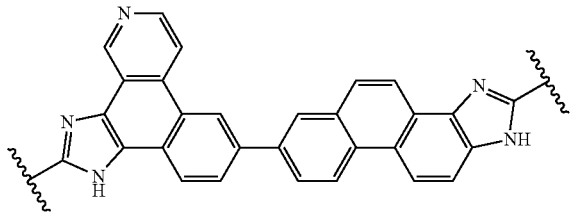
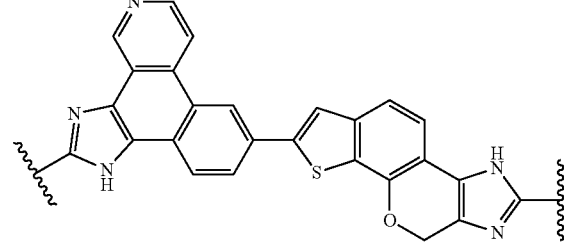
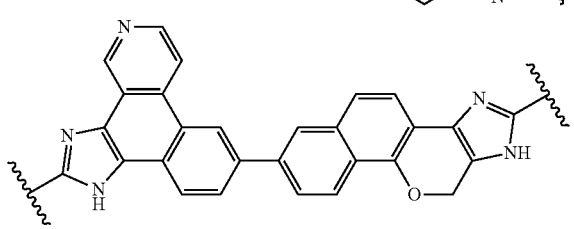

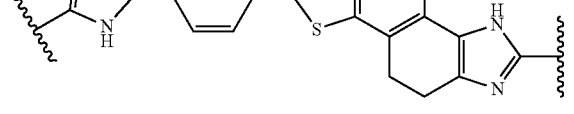
392
-continued
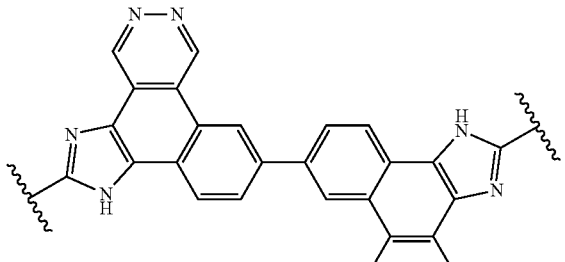
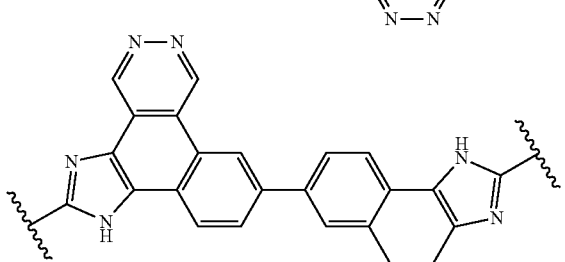
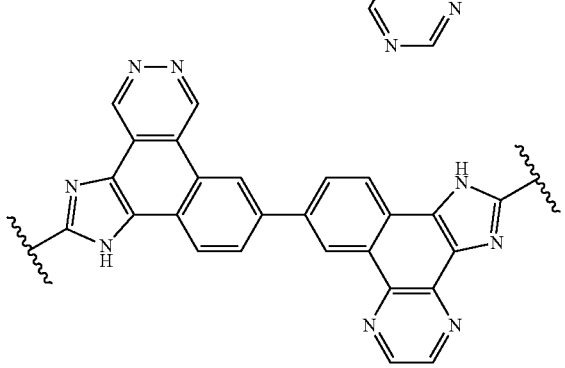
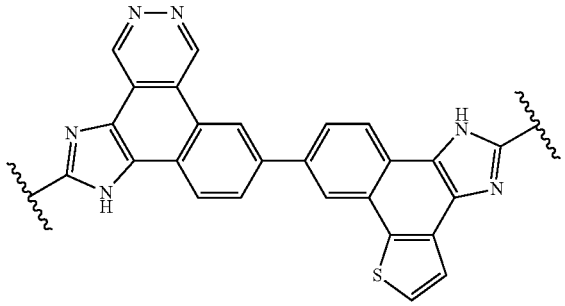
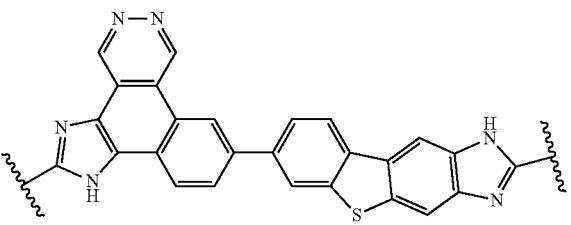
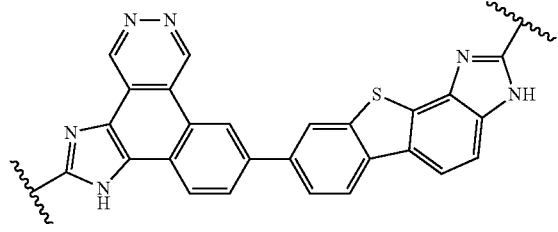

393
-continued
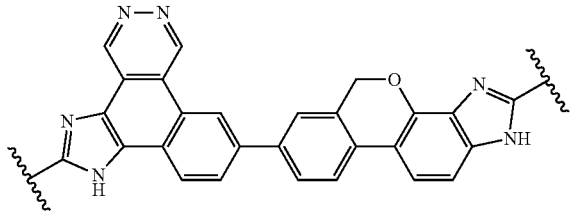
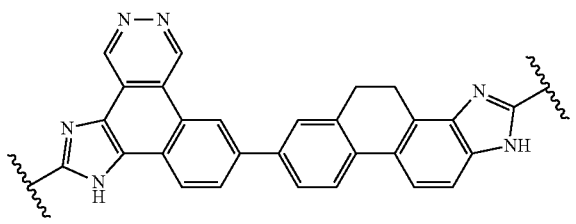
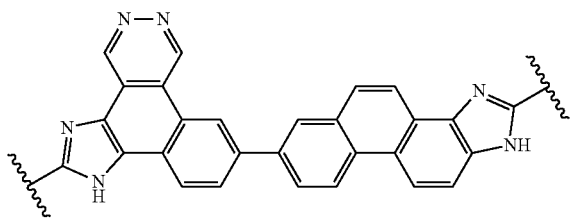
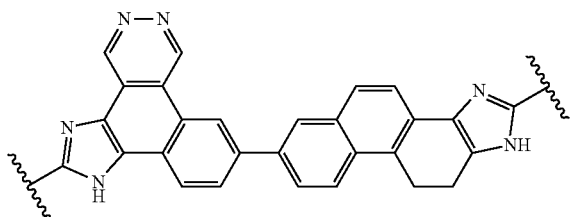
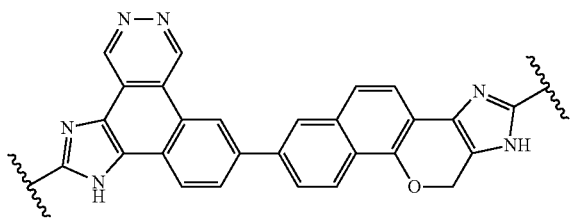
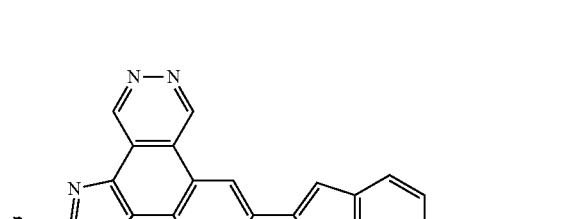
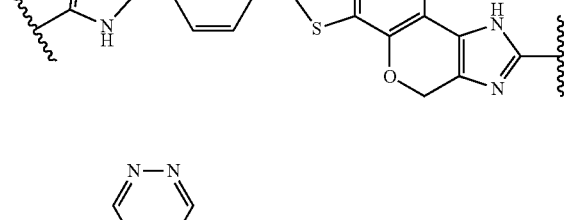
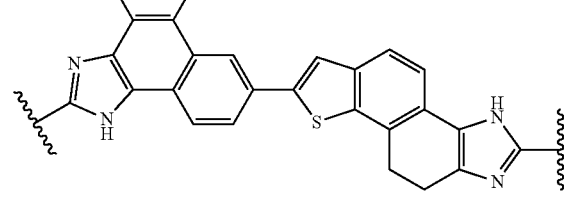
394
-continued
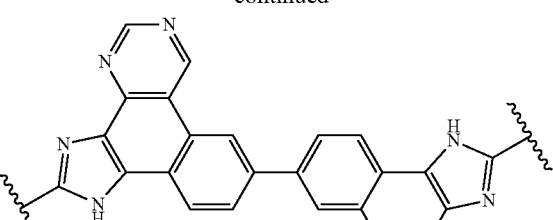
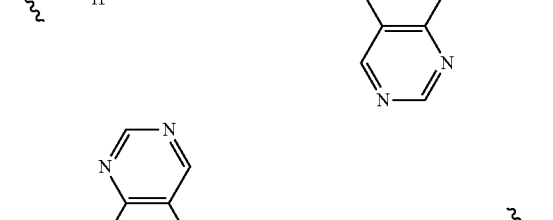
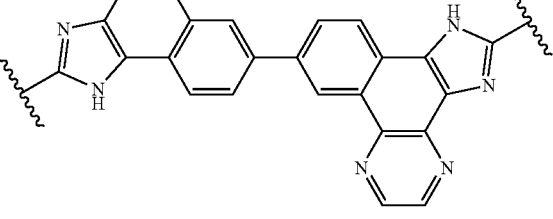
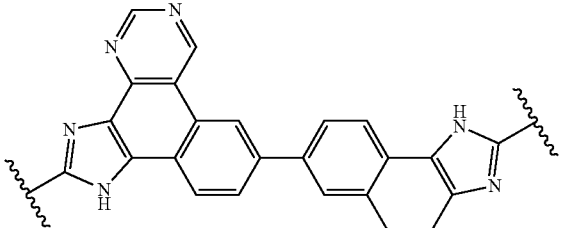
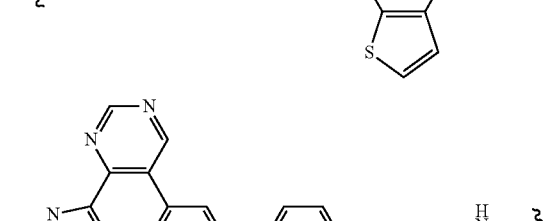
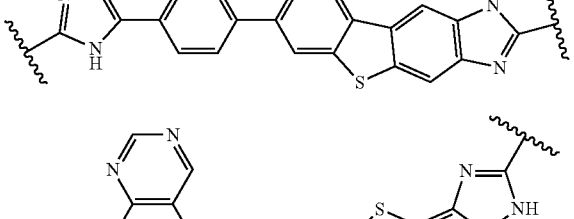
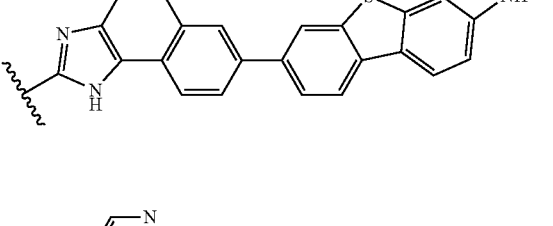
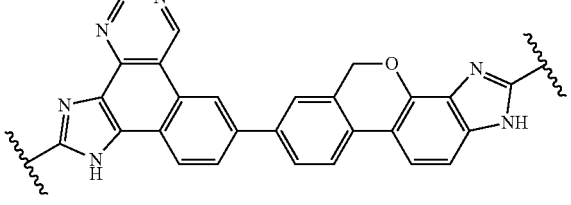

395
-continued
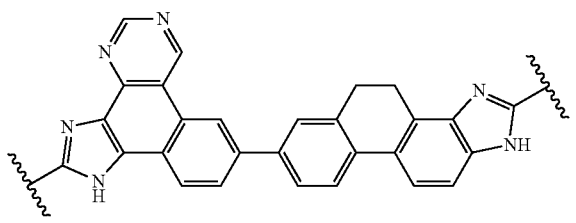
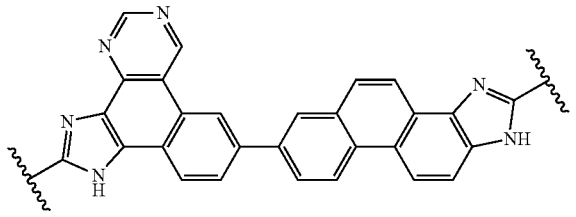
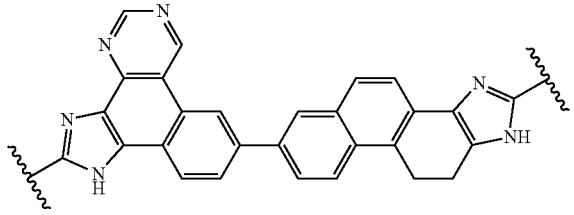
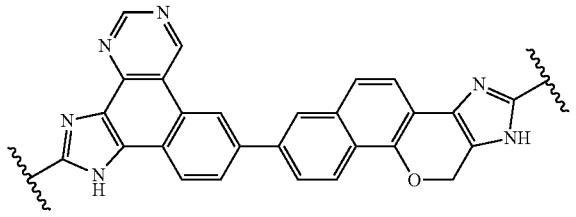
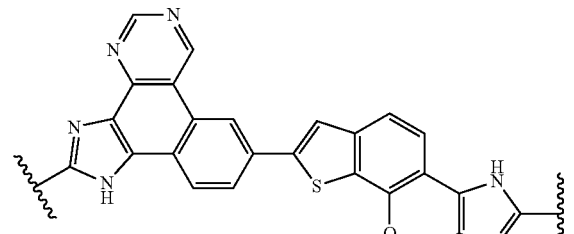
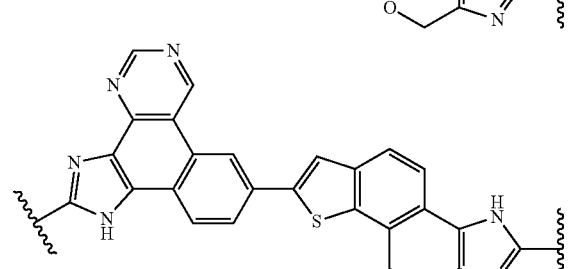
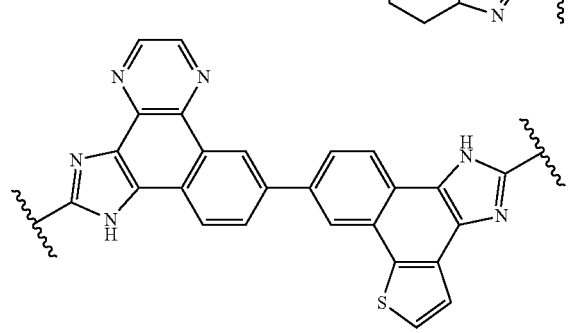
396
-continued
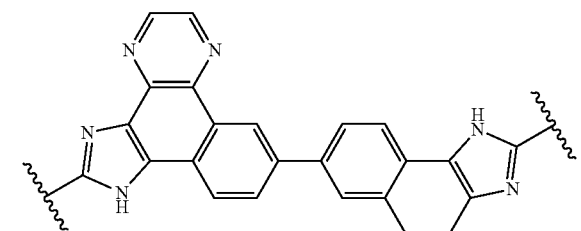

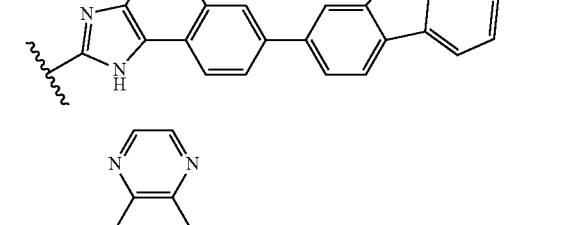
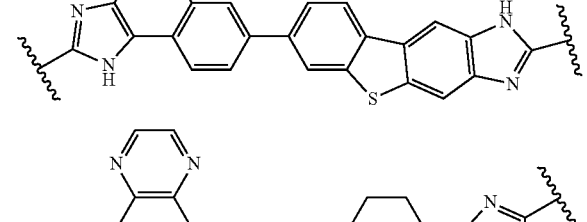
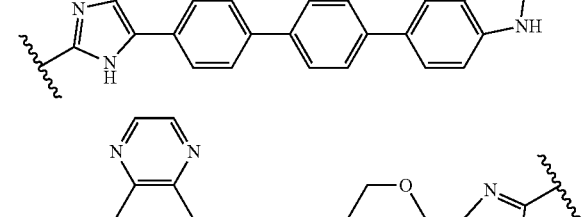
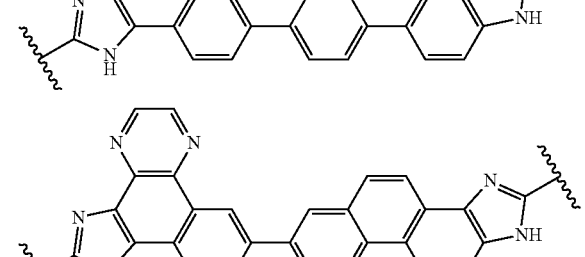
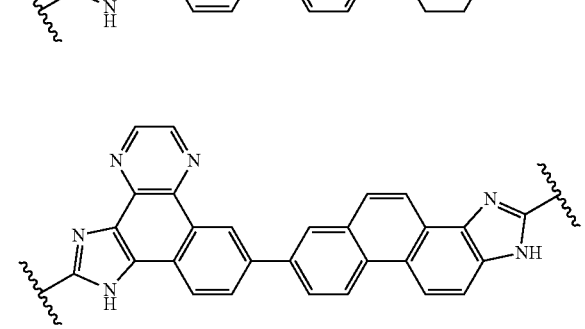

-continued

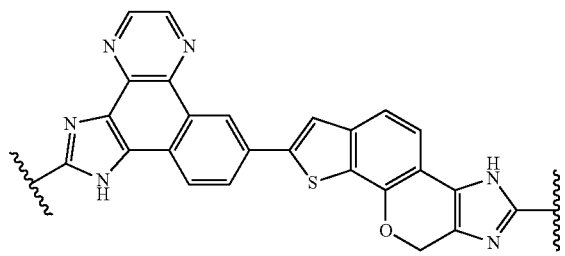

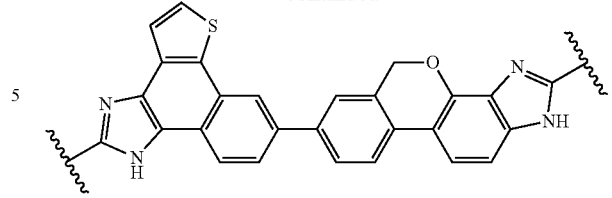
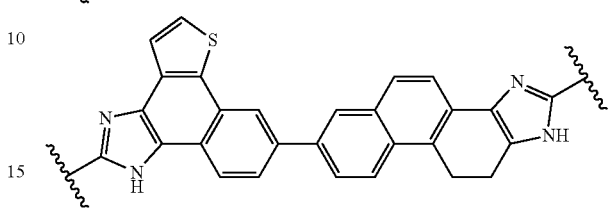
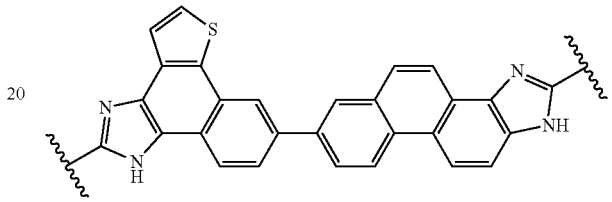
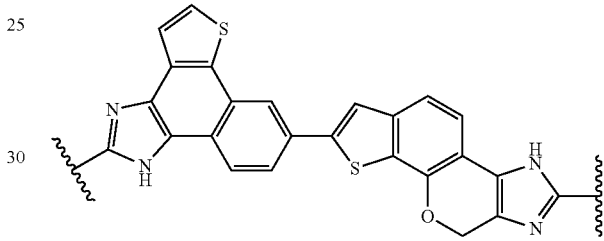
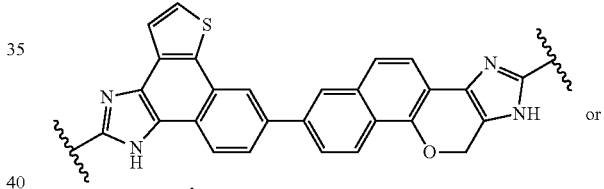
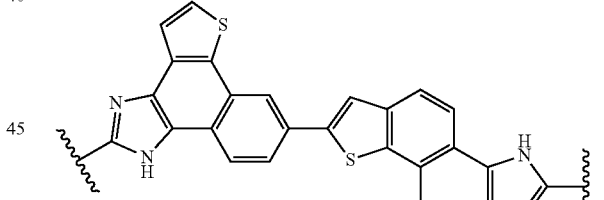

or

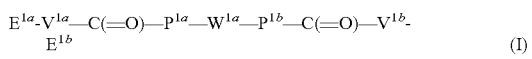

In one specific embodiment the invention provides a compound of formula (I):

$$E^{1a}\text{-}V^{1a}\text{—}C(=O)\text{—}P^{1a}\text{—}W^{1a}\text{—}P^{1b}\text{—}C(=O)\text{—}V^{1b}\text{-}E^{1b} \quad (I)$$

wherein:
$E^{1a}$ is $E^0$ or $E^1$, or $E^{1a}$-$V^{1a}$ taken together are $R^{9a}$;
$E^{1b}$ is $E^0$ or $E^1$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$P^{1a}$ and $P^{1b}$ are each independently selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;

each $P^0$ is independently:

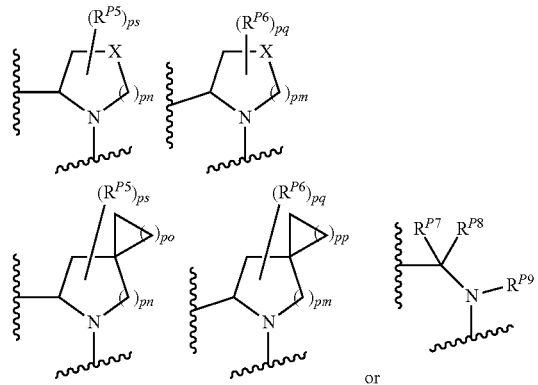

or wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;

each $P^1$ is independently:

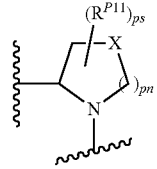

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

at least one $R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyloxyalkyloxy, aryloxyalkyloxy, heteroaryloxyakyloxy, heterocyclyloxyalkyloxy, $(NR^hR^h)$alkyloxy, cyanoalkoxy, cyanocycloalkyloxy, cycloalkyloxy, oxo, heterocyclyl, —$NR^{hh}R^h$, $(NR^{hh}R^h)$alkyl, $(NR^{hh}R^h)$carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo and heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;
each $P^3$ is independently a ring of the formula:

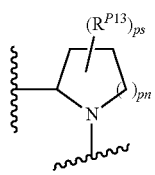

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 0, 1, 2, 3, or 4;
pn is 0, 1, or 2;
each $P^5$ is independently a ring of the formula:

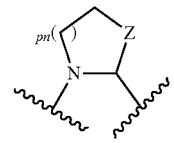

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pn is 0, 1, or 2;
Z is O, S, $S(=O)$, $S(=O)_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —$S(=O)_2NR^hR^h$, —$S(=O)_2R^h$, $C(=O)R^h$, $C(=O)OR^h$, —$C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^6$ is independently a ring of the formula:

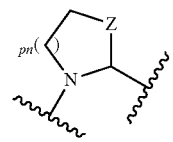

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

Z is O, S, S(=O), S(=O)$_2$, or NR$^f$;

pn is 0, 1, or 2;

each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;

each P$^7$ is a bridged 5-15 membered bicyclic heterocyclic ring that is attached to the remainder of the compound of formula I through one N-link and through one C-link; wherein the ring is optionally substituted with one or more groups independently selected from R$^{P6}$ and R$^{P11}$;

each P$^8$ is independently a ring of the formula:

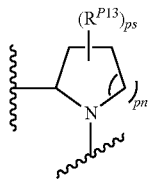

wherein:

ps is 2, 3, 4, 5, or 6;

pn is 0, 1 or 2;

each R$^{P13}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; where in at least one case two groups R$^{P13}$ that are attached to the same carbon are taken together with the carbon to which they are attached and form a 4-6 membered heterocyclic ring;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

each P$^{10}$ is independently:

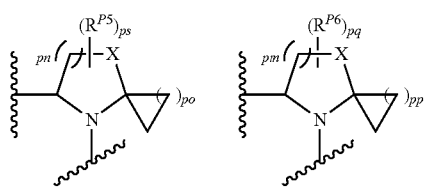

wherein:

X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

pq and ps are independently 0, 1, 2, 3, or 4;

pm and pn are independently 0, 1, or 2;

po and pp are independently 1, 2, or 3;

each P$^{12}$ is independently:

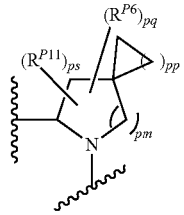

wherein:

each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq is independently 0, 1, 2, 3, or 4;

pm is independently 0, 1, or 2;

pp is independently 1, 2, or 3;

ps is 1, 2, 3, or 4;

R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each P$^{15}$ is:

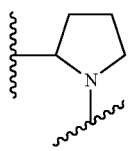 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each P$^{18}$ is:

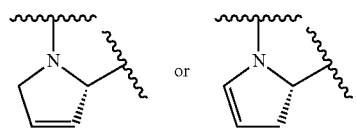 [SMILES: *[C@@H]1C=CCN1* ; *[C@@H]1CC=CN1*]

which is optionally substituted with one or two groups independently selected from halo, alkyl, alkoxyalkyl, haloalkyl, cycloalkyl, and cycloalkylalkyl;

each P$^{19}$ is:

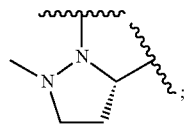

each R$^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each R$^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

W$^{1a}$ is selected from:

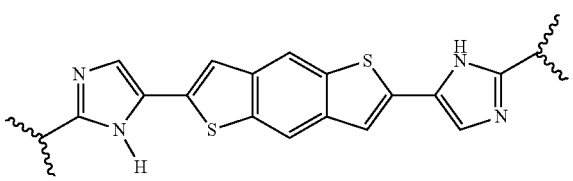

110

-continued

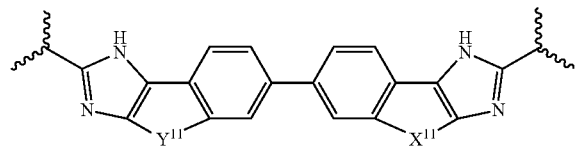
111

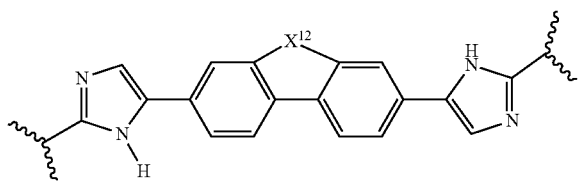
112

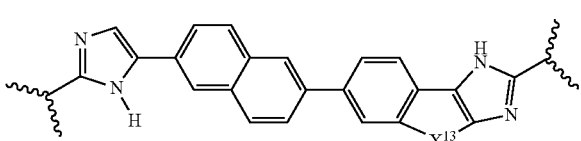
113

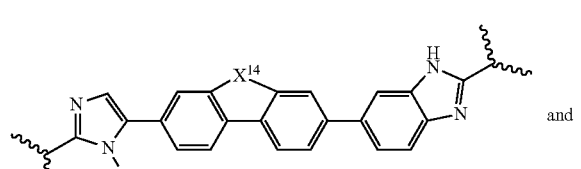
114
and

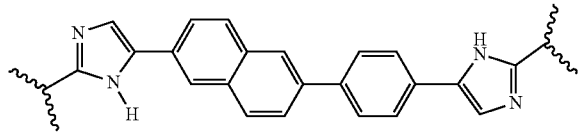
115

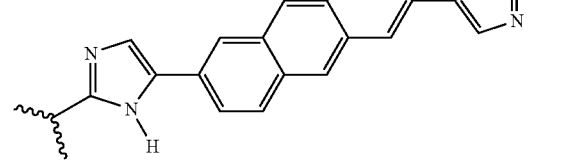
110a wherein each $W^{1a}$ is optionally substituted with one or more (e.g. 1, 2, 3, or 4) groups independently selected from halo, alkyl, haloalkyl, cyano, and wherein each $W^{1a}$ is substituted with one or more (e.g. 1, 2, 3, or 4):

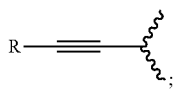

wherein each R is independently H, alkyl, haloalkyl, cycloalkyl, aryl, or heteroaryl;

$X^{11}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

$Y^{11}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

$X^{12}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—

$X^{13}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—; and $X^{14}$ is —CH$_2$—, —CH$_2$—CH$_2$—, —CH$_2$—O—, —O—CH$_2$—, —CH$_2$—O—CH$_2$—, —S—, —S(O)$_2$—, —C(O)—, —CF$_2$—, —O—, —S—CH$_2$—, —CH$_2$—S—, —O—C(O)—, —C(O)—O—, —CH=N—; —N=CH—; or —CH=CH—;

or a pharmaceutically acceptable salt or prodrug thereof.

In one specific embodiment $W^{1a}$ is:

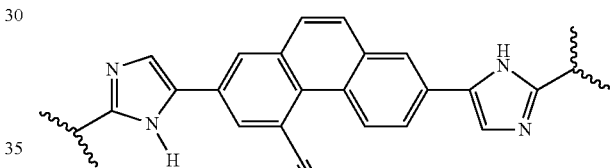

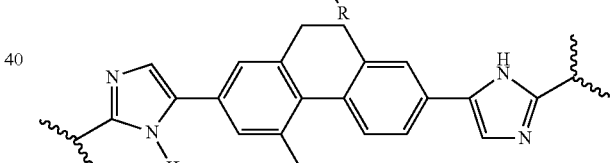

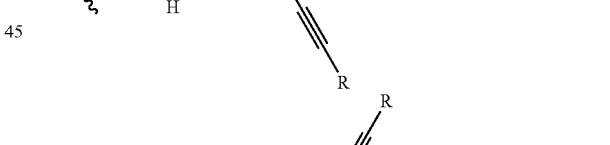

or

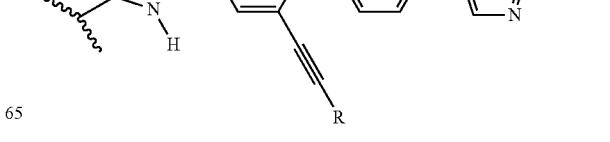

In one specific embodiment $W^{1a}$ is:

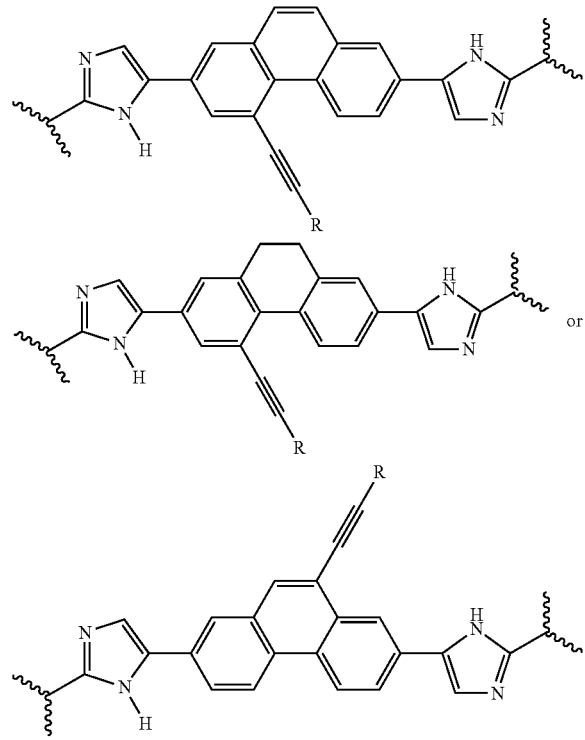

In one specific embodiment $W^{1a}$ is:

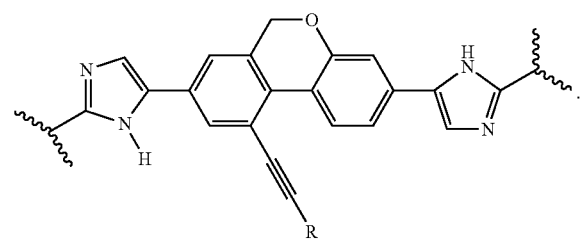

In one specific embodiment $W^{1a}$ is:

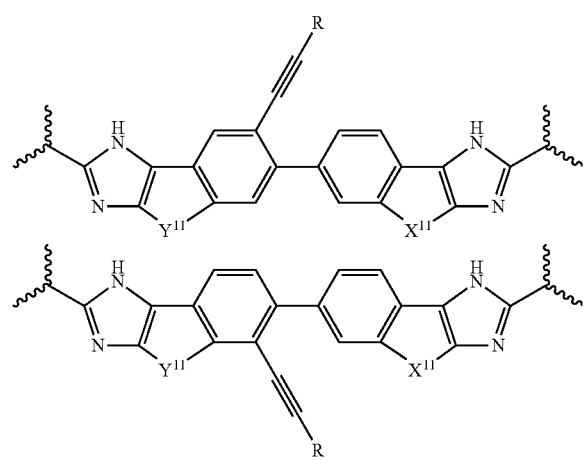

-continued

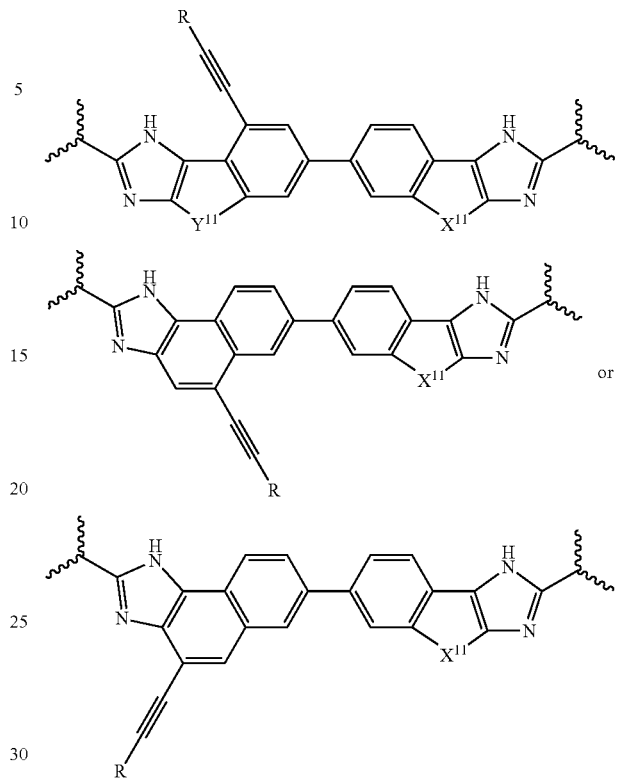

In one specific embodiment $X^{11}$ is —CH$_2$—CH$_2$—, —CH$_2$—O—, —O—CH$_2$—, or —CH=CH—.

In one specific embodiment $Y^{11}$ is —CH$_2$—CH$_2$—, —CH$_2$—O—, —O—CH$_2$—, or —CH=CH—.

In one specific embodiment $W^{1a}$ is:

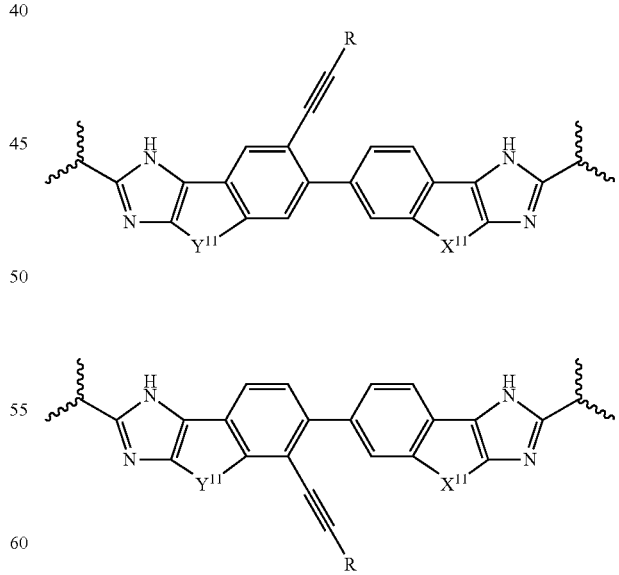

In one specific embodiment $X^{11}$ is —CH$_2$—CH$_2$—, —CH$_2$—O—, —O—CH$_2$—, or —CH=CH—.

In one specific embodiment $Y^{11}$ is —CH$_2$—CH$_2$—, —CH$_2$—O—, —O—CH$_2$—, or —CH=CH—.

In one specific embodiment $W^{1a}$ is:

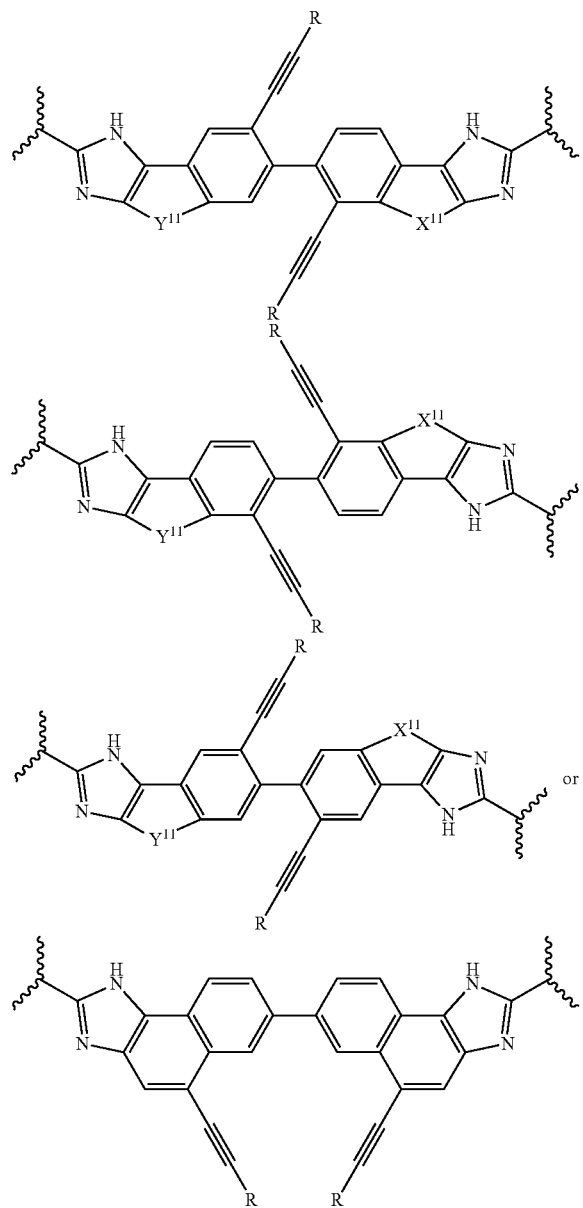

In one specific embodiment $X^{11}$ is —CH$_2$—CH$_2$—, —CH$_2$—O—, —O—CH$_2$—, or —CH=CH—.
In one specific embodiment $Y^{11}$ is —CH$_2$—CH$_2$—, —CH$_2$—O—, —O—CH$_2$—, or —CH=CH—.
In one specific embodiment $W^{1a}$ is:

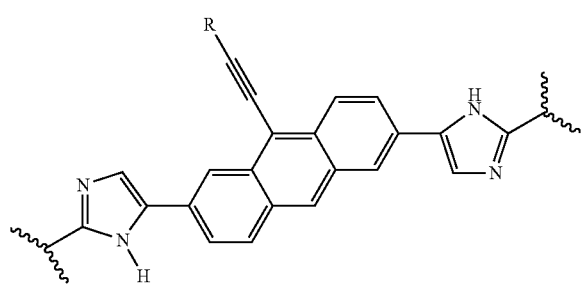

-continued

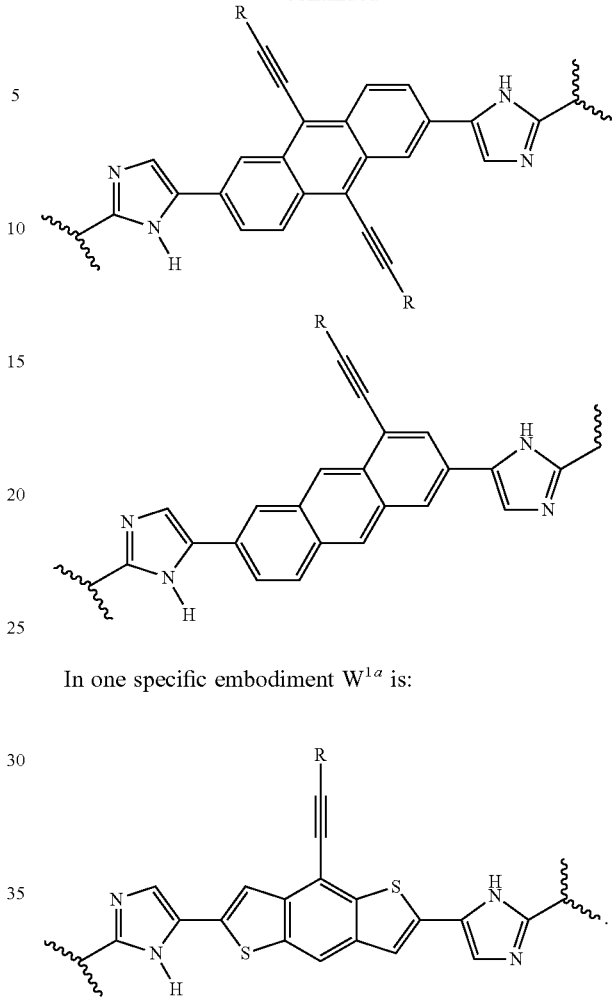

In one specific embodiment R is H, methyl, cyclopropyl, phenyl, or

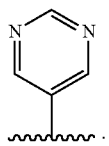

In one specific embodiment the invention provides a compound of formula (I):

$$E^{1a}\text{-}V^{1a}\text{—}C(=O)\text{—}P^{1a}\text{—}W^{1a}\text{—}P^{1b}\text{—}C(=O)\text{—}V^{1b}\text{-}E^{1b} \quad (I)$$

wherein:
$E^{1a}$ is $E^0$ or $E^1$, or $E^{1a}$-$V^{1a}$ taken together are $R^{9a}$;
$E^{1b}$ is $E^0$ or $E^1$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
one of $P^{1a}$ and $P^{1b}$ is selected from $P^{0a}$ and the other of $P^{1a}$ and $P^{1b}$ is selected from $P^1$, $P^3$, $P^5$, $P^6$, $P^7$, $P^8$, $P^{10}$, $P^{12}$, $P^{15}$, $P^{18}$, $P^{19}$, and $P^{30}$;
each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, aryl, and heterocyclyl;

each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$W^{1a}$ is:

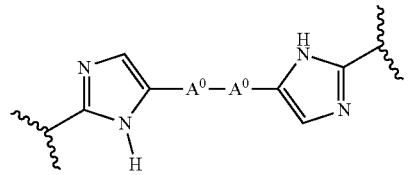

XX1 wherein $W^{1a}$ is optionally substituted with one or more (e.g. 1, 2, 3, or 4) groups independently selected from halo, alkyl, haloalkyl, cyano, and

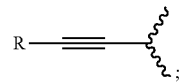

wherein each R is independently H, alkyl, haloalkyl, cycloalkyl, aryl, or heteroaryl;

each $A^0$ is independently:

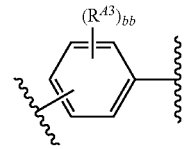

wherein:
each $R^{A3}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each
bb is independently 0, 1, 2, 3, or 4; or
each $A^0$ is independently a six-membered heteroaromatic ring containing one, two, or three nitrogen atoms, which ring is optionally substituted with 1, 2, 3, or 4 $R^3$ groups;
each $P^{0a}$ is independently:

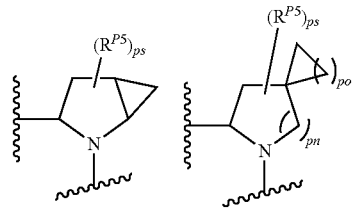

wherein:
each $R^{P5}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

ps is independently 0, 1, 2, 3, or 4;
pn is independently 0, 1, or 2;
po is independently 1, 2, or 3;
each P$^1$ is independently:

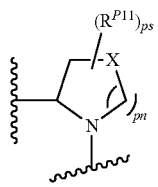

wherein:
X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$a)lkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
ps is 1, 2, 3, or 4;
pn is 0, 1, or 2;
each P$^3$ is independently a ring of the formula:

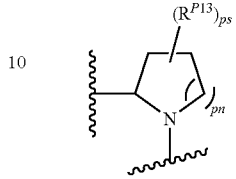

wherein:
the ring is substituted with one or more oxo group;
each R$^{P13}$ is independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
ps is 0, 1, 2, 3, or 4;
pn is 0, 1, or 2;
each P$^5$ is independently a ring of the formula:

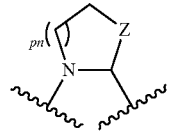

wherein:
the ring is optionally substituted with one or more groups R$^{P15}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups R$^{P15}$ that are attached to the same carbon when taken together with the carbon to which they are attached can form a 3-6 membered carbocyclic or heterocyclic ring;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
pn is 0, 1, or 2;
Z is O, S, S(=O), S(=O)$_2$, or NR$^f$;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)

$NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^6$ is independently a ring of the formula:

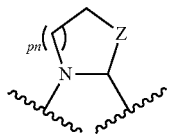

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

Z is O, S, S(=O), S(=O)$_2$, or $NR^f$;

pn is 0, 1, or 2;

each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P6}$ and $R^{P11}$;

each $P^8$ is independently a ring of the formula:

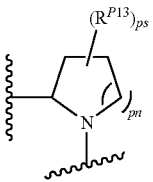

wherein:
ps is 2, 3, 4, 5, or 6;
pn is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

each $P^{10}$ is independently:

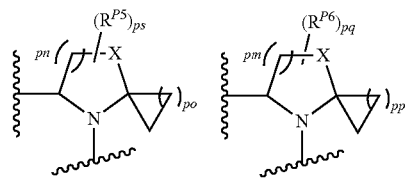

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;
each $P^{12}$ is independently:

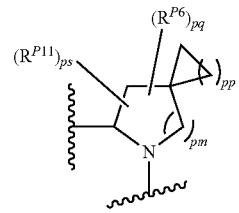

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq is independently 0, 1, 2, 3, or 4;
pm is independently 0, 1, or 2;
pp is independently 1, 2, or 3;
ps is 1, 2, 3, or 4;
$R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl, —$NR^{hh}R^h$, $(NR^{hh}R^hR^h)$alkyl, $(NR^{hh}R^h)$carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{15}$ is:

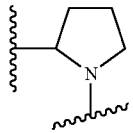 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

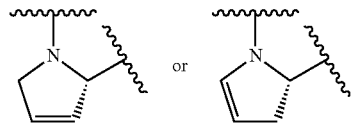

which is optionally substituted with one or two groups independently selected from halo, alkyl, alkoxyalkyl, haloalkyl, cycloalkyl, and cycloalkylalkyl;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —$C(NCN)OR'$, and —$C(NCN)NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —$(NR^XR^Y)$alkyl, and —$(NR^XR^Y)$carbonyl; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl, wherein $R^{X'}$ and $R^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —$C(NCN)OR'$, and —$C(NCN)NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

or a pharmaceutically acceptable salt or prodrug thereof. In one specific embodiment the invention provides a compound of formula (I):

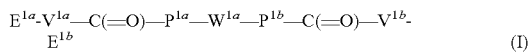

(I)

wherein:

$E^{1a}$ is $E^0$ or $E^1$, or $E^{1a}$-$V^{1a}$ taken together are $R^{9a}$;
$E^{1b}$ is $E^0$ or $E^1$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
one of $P^{1a}$ and $P^{1b}$ is selected from $P^{0b}$ and the other of $P^{1a}$ and $P^{1b}$ is selected from $P^{21}$, $P^3$, $P^6$, $P^7$, $P^{28}$, $P^{12}$, $P^{15}$ and $P^{38}$;
each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;
each $E^1$ is independently selected from hydrogen, hydroxy, alkyl, aryl, and heterocyclyl;
each $V^0$ is independently alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$W^{1a}$ is:

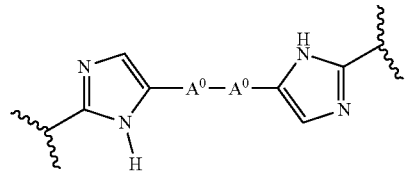

XX1 wherein $W^{1a}$ is optionally substituted with one or more (e.g. 1, 2, 3, or 4) groups independently selected from halo, alkyl, haloalkyl, cyano, and

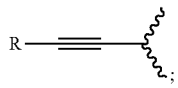

wherein each R is independently H, alkyl, haloalkyl, cycloalkyl, aryl, or heteroaryl;
each $A^0$ is independently:

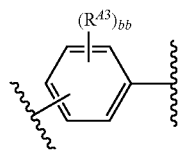

wherein:
each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or each $A^O$ is independently a six-membered heteroaromatic ring containing one, two, or three nitrogen atoms, which ring is optionally substituted with 1, 2, 3, or 4 $R^{A3}$ groups;

each $P^{Ob}$ is independently:

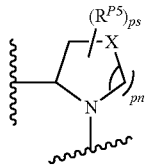

X is selected from O, S, S(O), SO$_2$, CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$ each $R^{P5}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

ps is independently 0, 1, 2, 3, or 4;

pn is independently 0, 1, or 2;

each $P^{21}$ is independently:

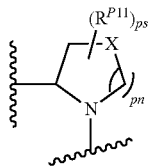

wherein:

X is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

at least one $R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclooxyalkyloxy, (NR$^h$R$^h$)alkyloxy, cyanoalkoxy, cyanocycloalkyloxy, cycloalkyloxy, oxo, —NR$^{hh}$R$^h$, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining $R^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl;

ps is 1, 2, 3, or 4;

pn is 0, 1, or 2;

each $P^3$ is independently a ring of the formula:

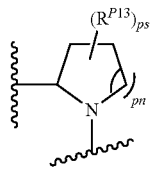

wherein:

the ring is substituted with one or more oxo group;

each $R^{P13}$ is independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

ps is 0, 1, 2, 3, or 4;

pn is 0, 1, or 2;

each $P^6$ is independently a ring of the formula:

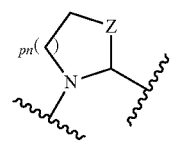

wherein:

the ring is substituted with one or more oxo and is optionally substituted with one or more groups $R^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

Z is O, S, S(=O), S(=O)$_2$, or NR$^f$;

pn is 0, 1, or 2;

each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;

each P$^7$ is a bridged 5-15 membered bicyclic heterocyclic ring that is attached to the remainder of the compound of formula I through one N-link and through one C-link; wherein the ring is optionally substituted with one or more groups independently selected from R$^{P6}$ and R$^{P11}$;

each P$^{28}$ is independently a ring of the formula:

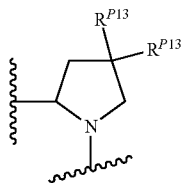

wherein:

each R$^{P13}$ is independently selected from alkoxy, alkyl, aryl, halo, haloalkyl, hydroxy, and —NR$^{Pa}$R$^{Pb}$, where in two R$^{P13}$ groups are taken together with the carbon to which they are attached and form a 4-6 membered heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

each P$^{12}$ is independently:

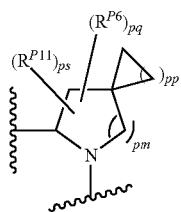

wherein:

each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq is independently 0, 1, 2, 3, or 4;

pm is independently 0, 1, or 2;

pp is independently 1, 2, or 3;

ps is 1, 2, 3, or 4;

R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each P$^{15}$ is:

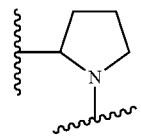 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each P$^{38}$ is:

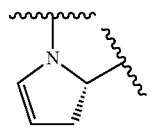 [SMILES: *[C@@H]1CC=CN1*]

which is optionally substituted with one or two groups independently selected from halo, alkyl, alkoxyalkyl, haloalkyl, cycloalkyl, and cycloalkylalkyl;

each R$^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each R$^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —(NR$^X$R$^Y$)alkyl, and —(NR$^X$R$^Y$)carbonyl; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

or a pharmaceutically acceptable salt or prodrug thereof;
provided the compound of formula (I) is not:

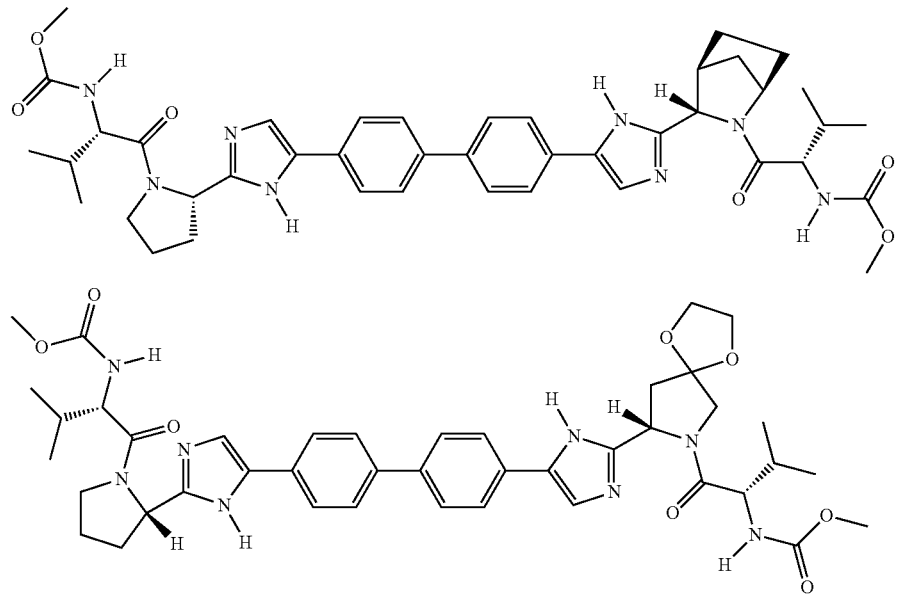

-continued
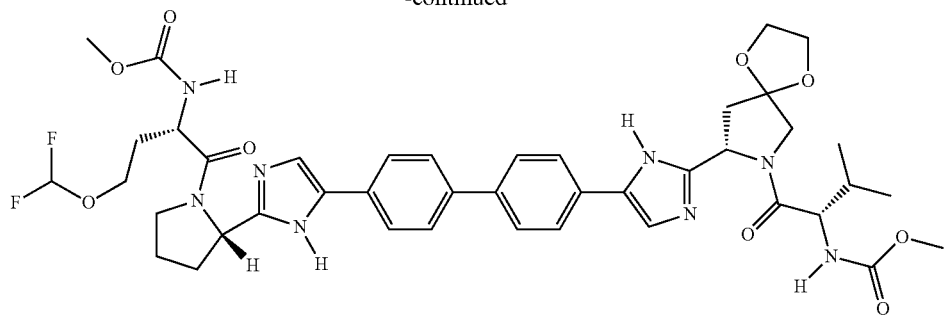
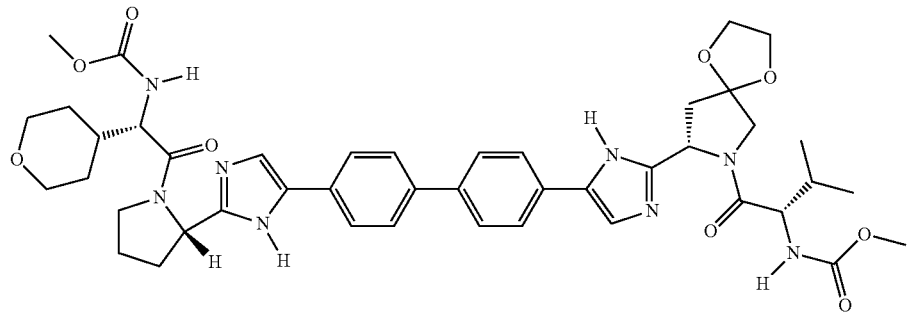
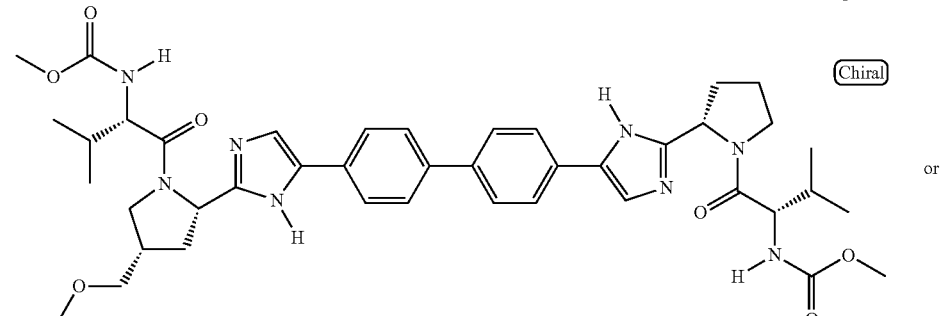
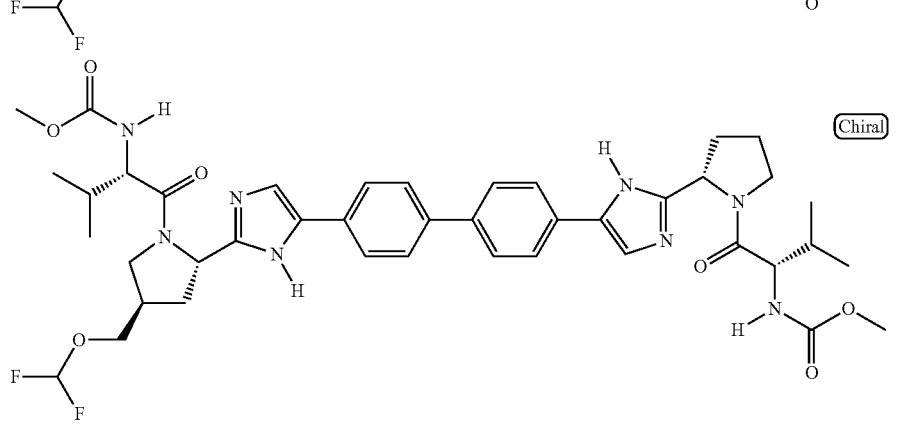
In one specific embodiment E$^{1a}$ is E$^0$.
In one specific embodiment E$^{1a}$ is E$^1$.
In one specific embodiment E$^{1a}$ is selected from:
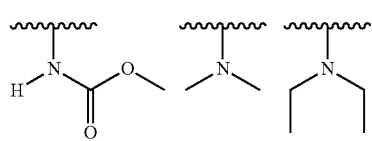
-continued
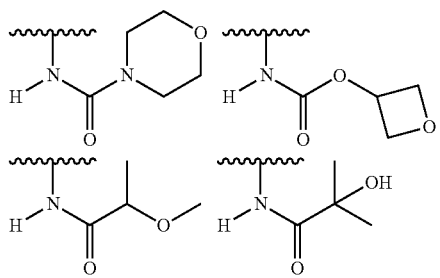

431

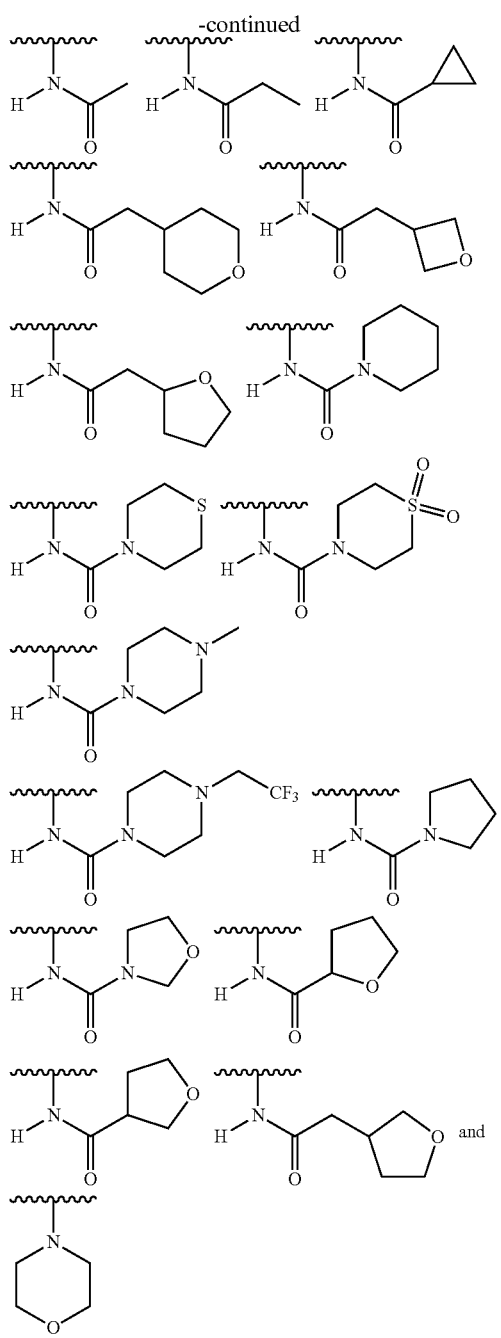

In one specific embodiment $E^{1a}$ is —N(H)alkoxycarbonyl.

In one specific embodiment $E^{1a}$ is —N(H)C(=O)OMe.

In one specific embodiment $E^{1b}$ is $E^0$.

In one specific embodiment $E^{1b}$ is $E^1$.

In one specific embodiment $E^{1b}$ is selected from:

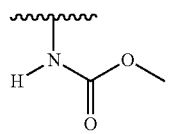 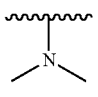 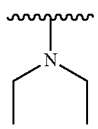

432

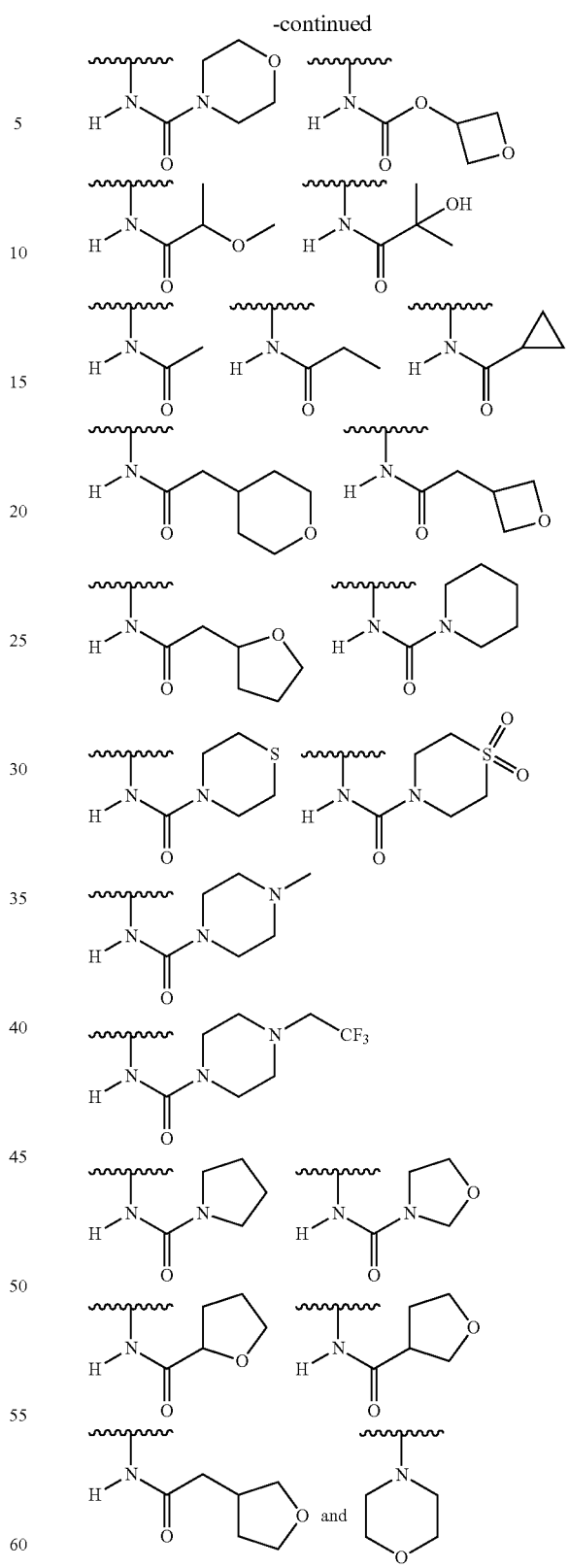

In one specific embodiment $E^{1b}$ is —N(H)alkoxycarbonyl.

In one specific embodiment $E^{1b}$ is —N(H)C(=O)OMe.

In one specific embodiment $V^{1a}$ is $V^0$.

In one specific embodiment $V^{1b}$ is selected from:
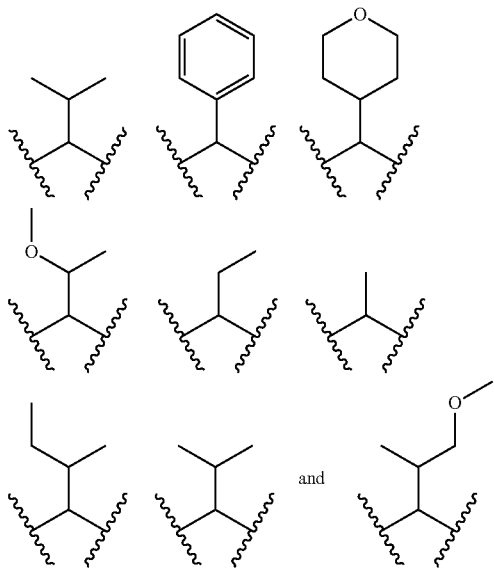
In one specific embodiment $E^{1a}$-$V^{1a}$ taken together are $R^{9a}$.
In one specific embodiment $R^{9a}$ is selected from:
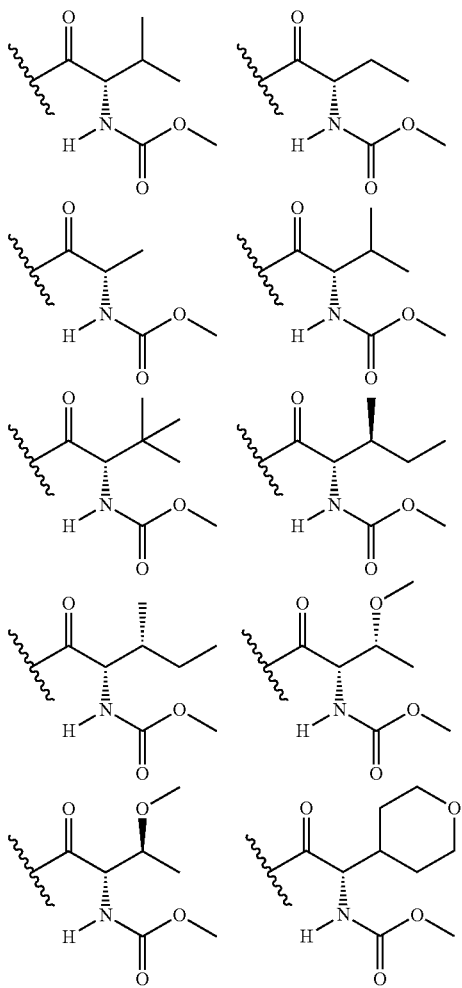
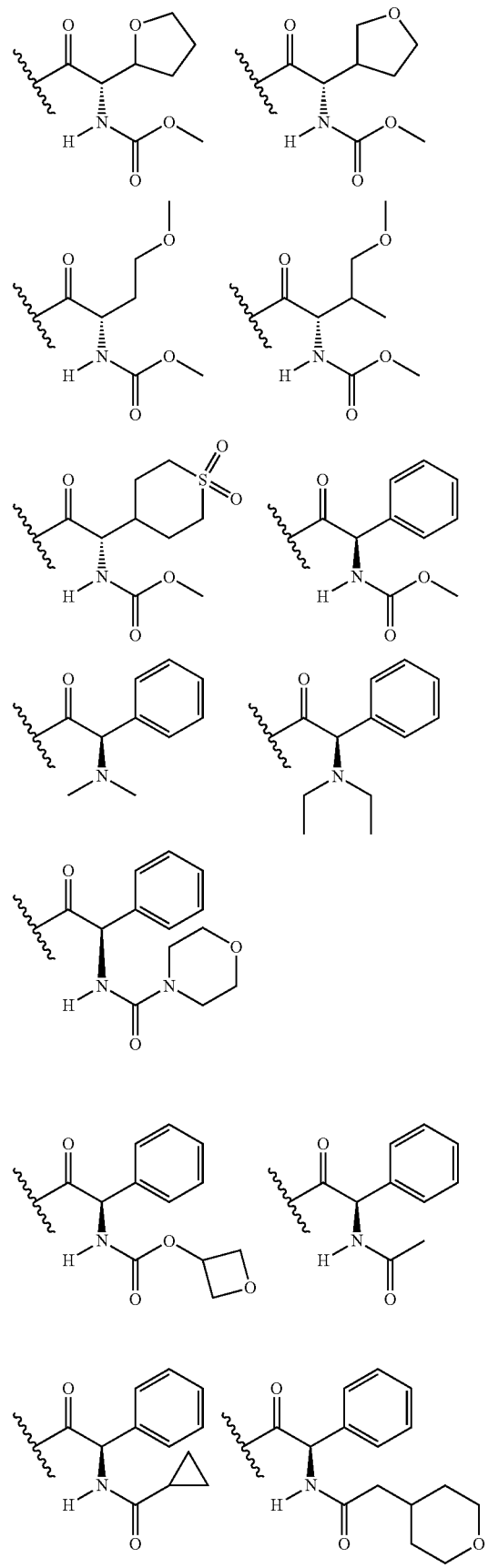

435
-continued
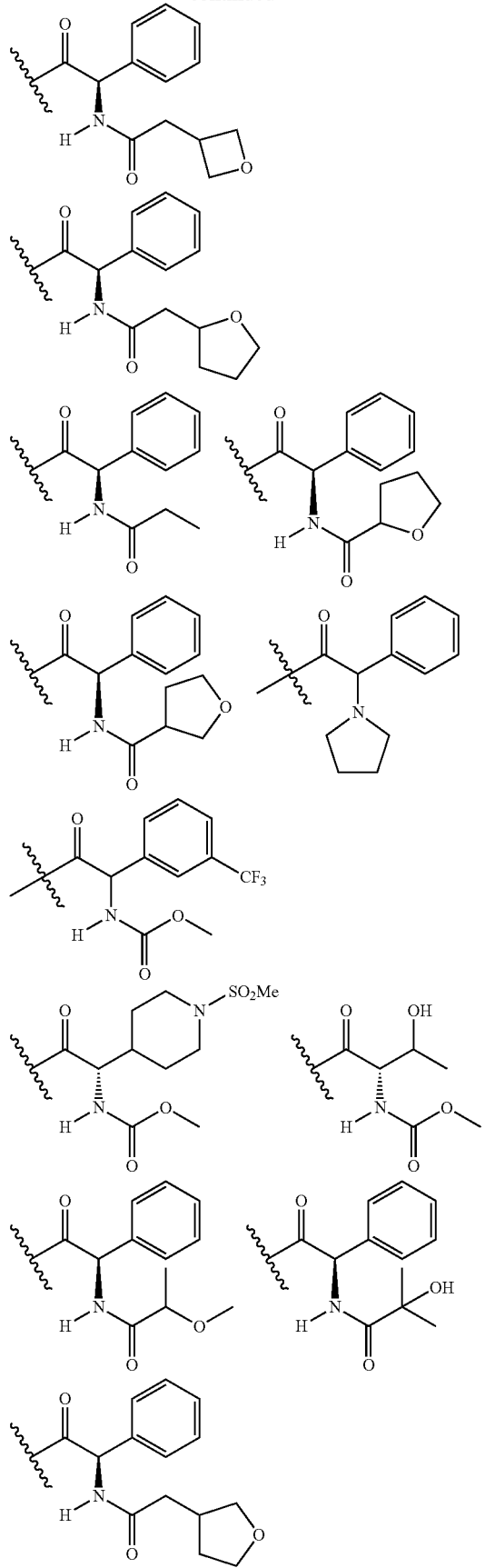
436
-continued
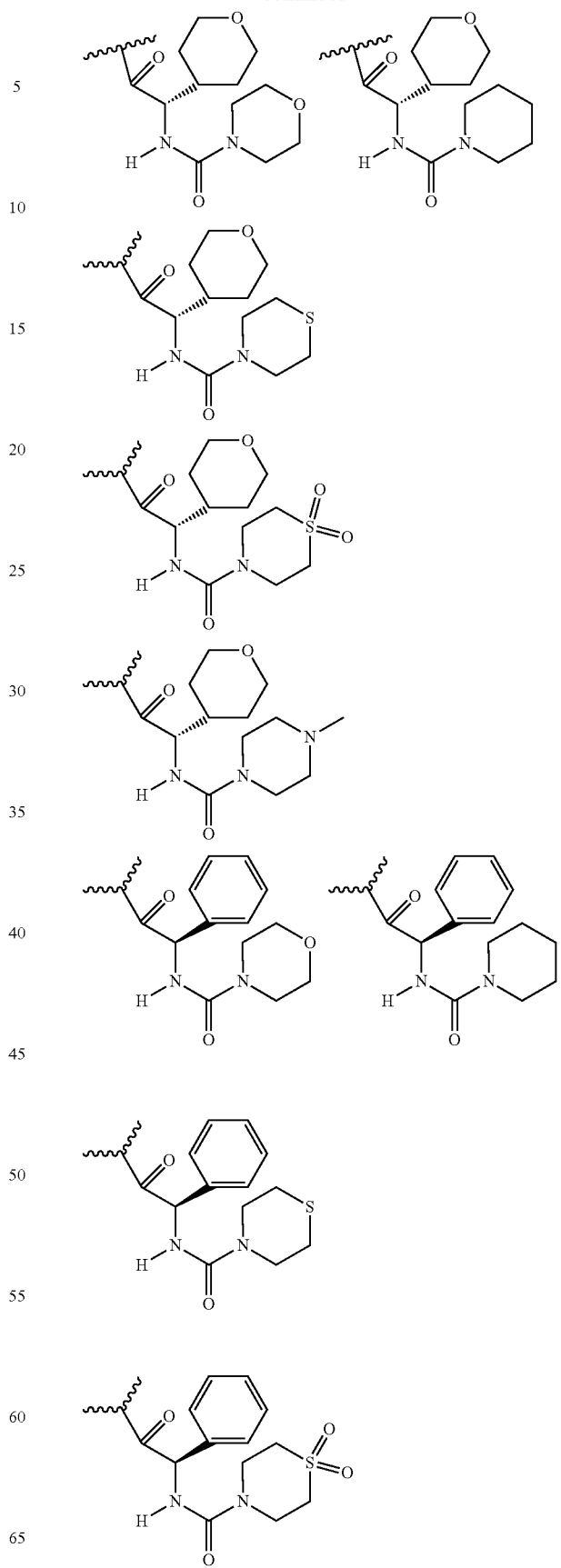

437
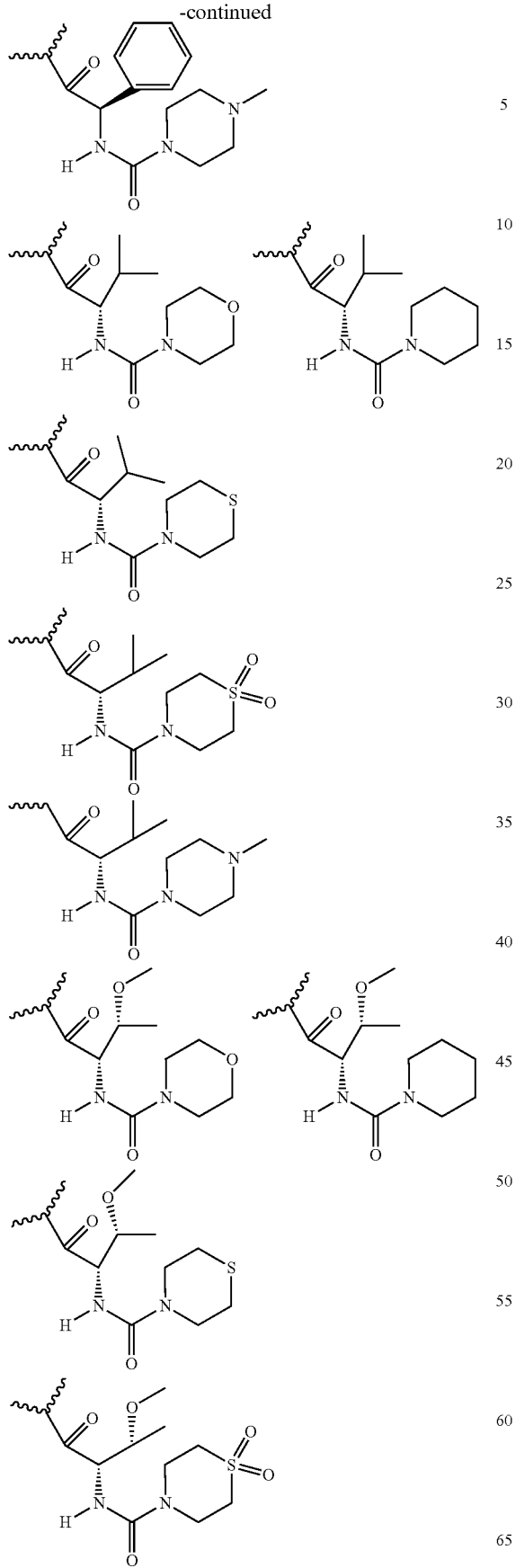
438
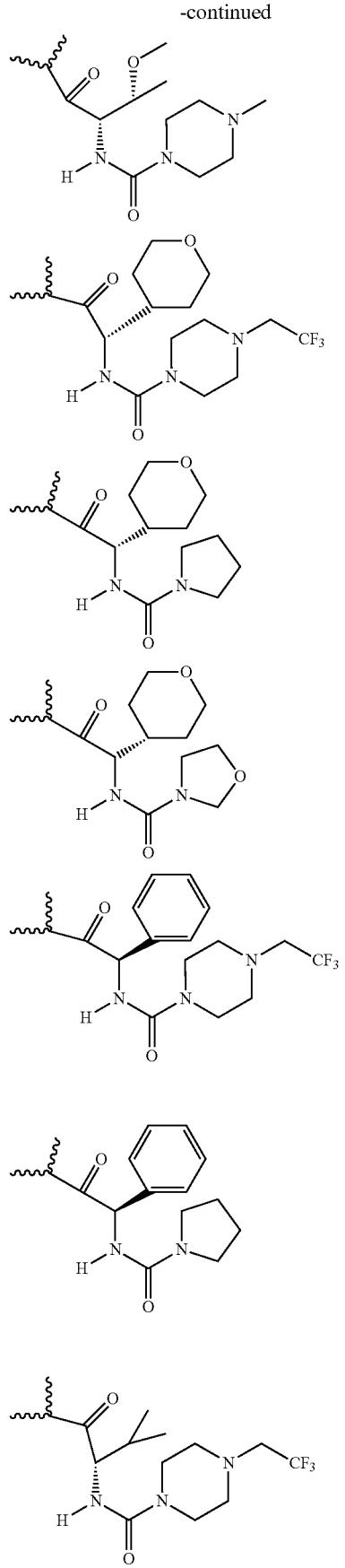

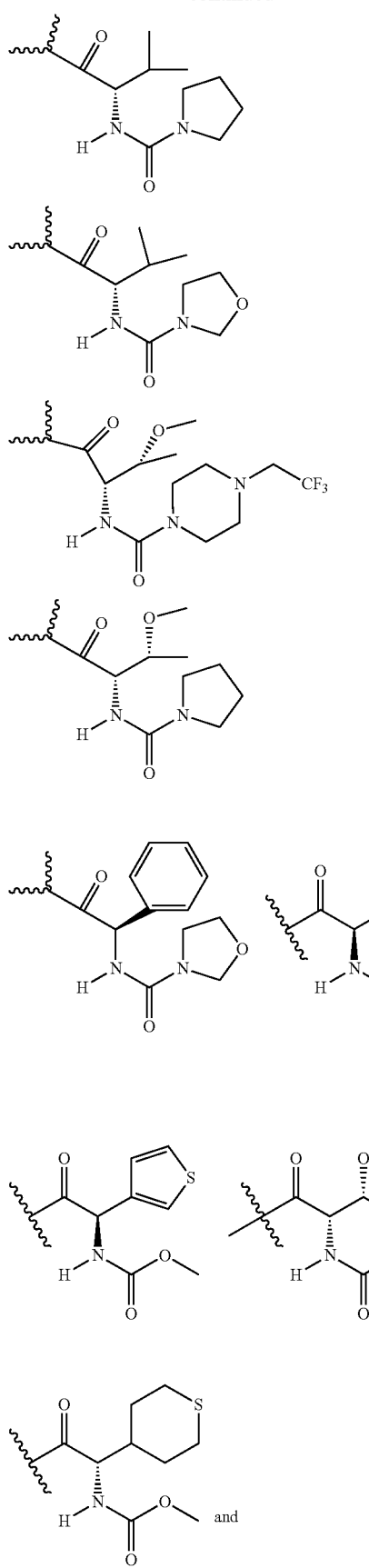
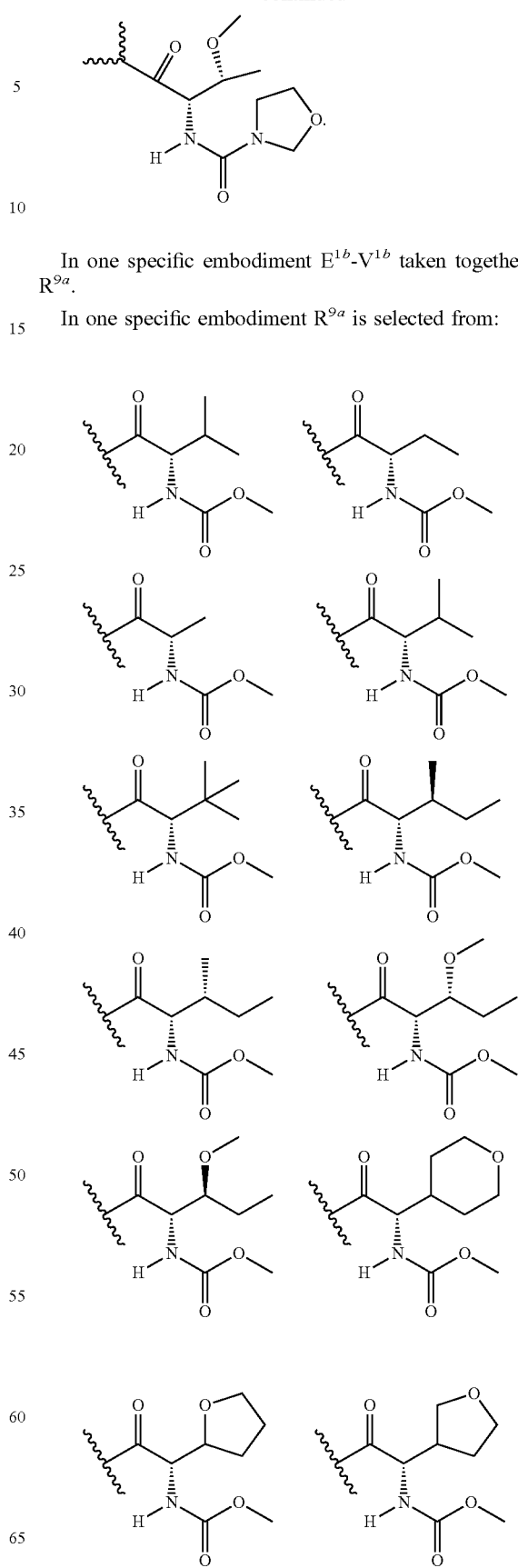
In one specific embodiment $E^{1b}$-$V^{1b}$ taken together are $R^{9a}$.
In one specific embodiment $R^{9a}$ is selected from:

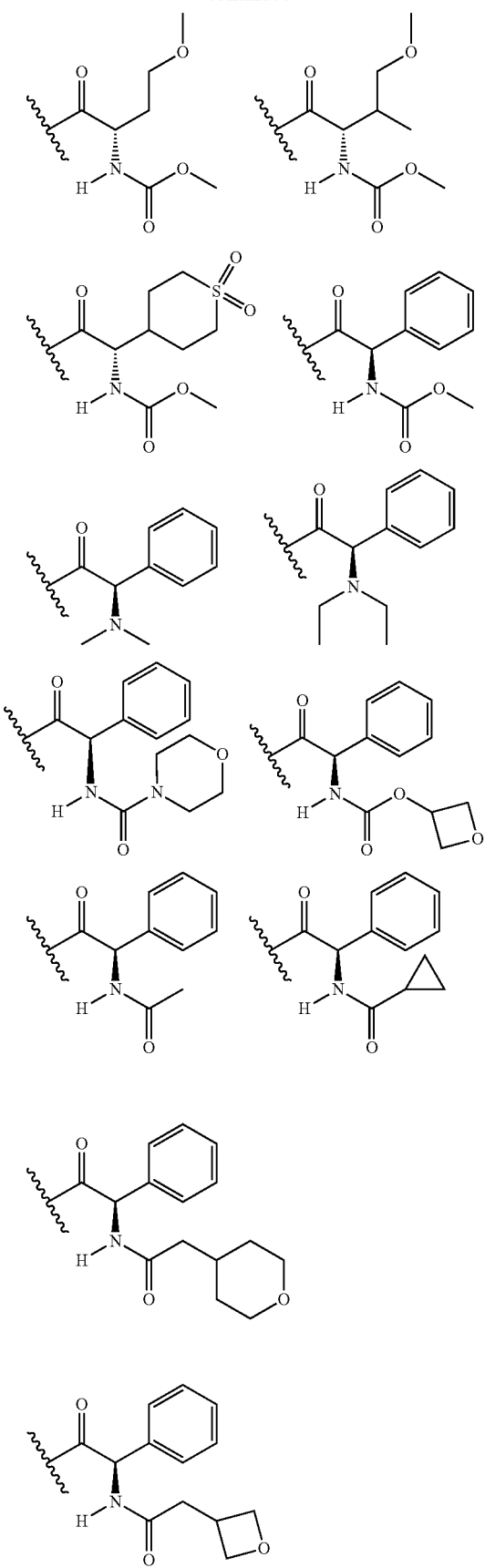
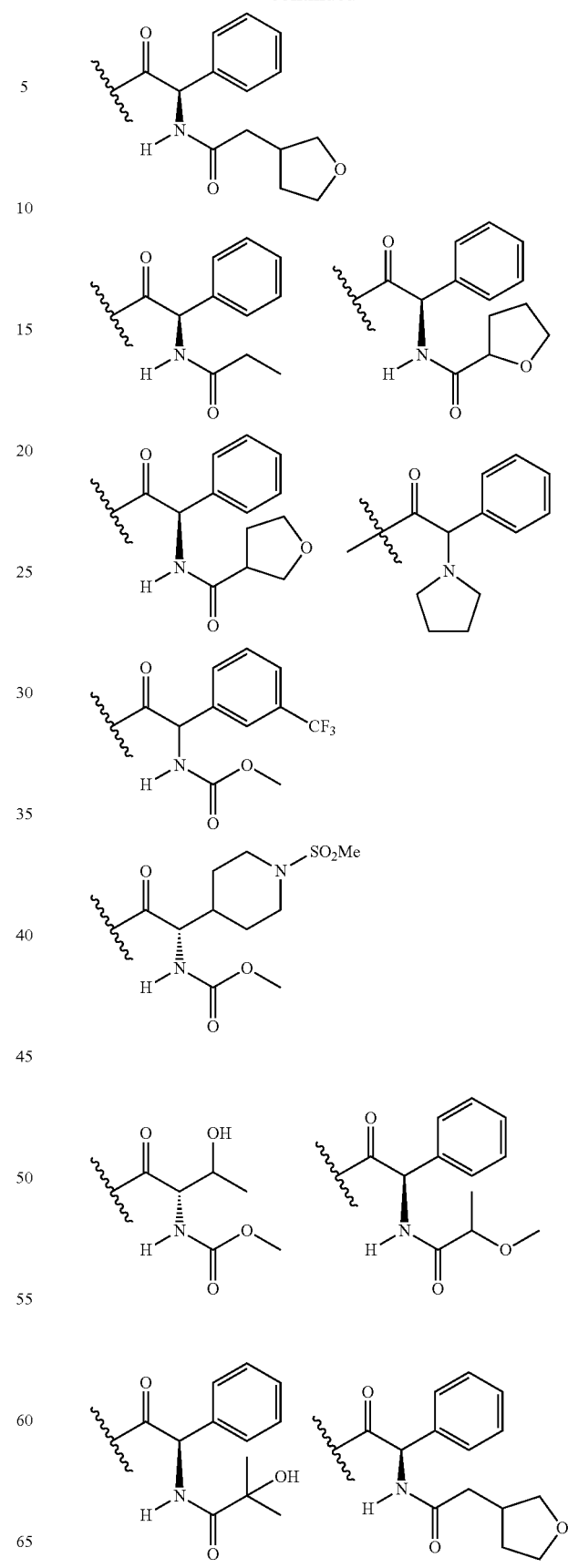

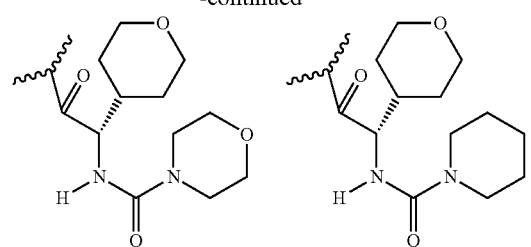
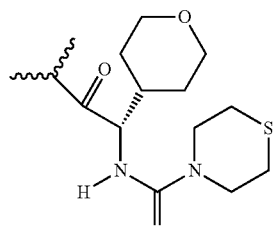
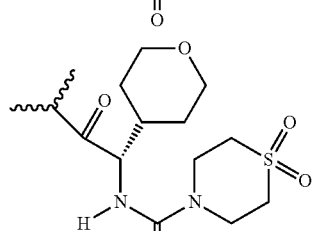
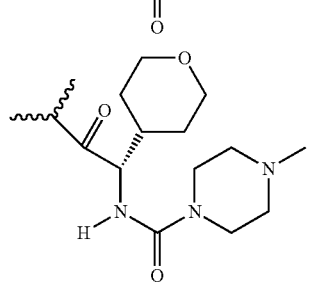
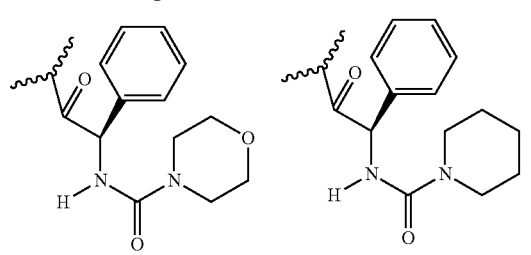
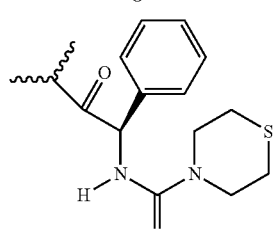
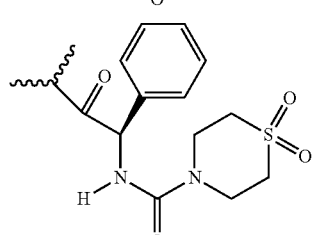
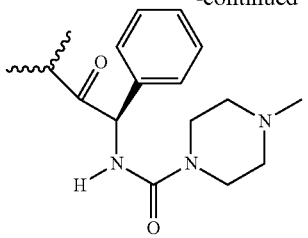
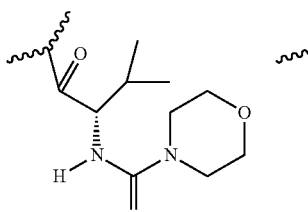
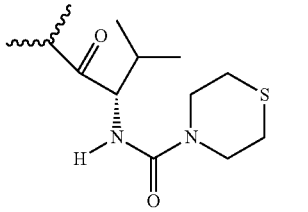
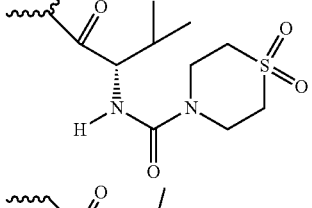
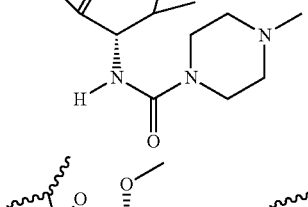
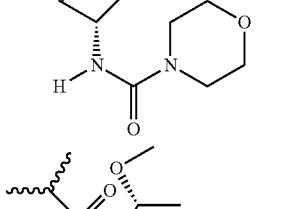
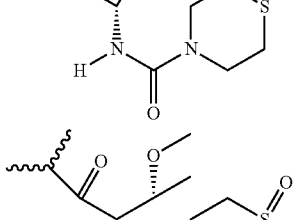
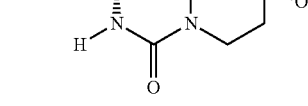

445
-continued
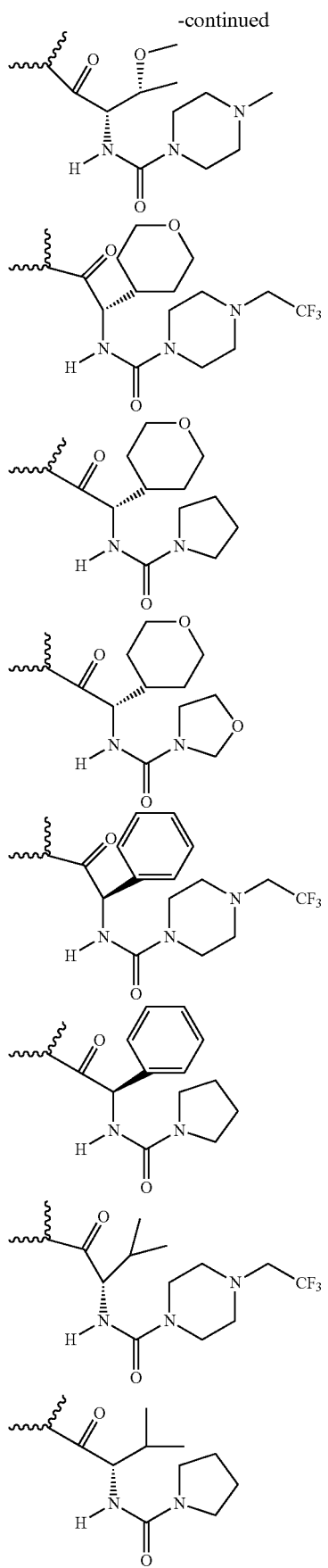
446
-continued
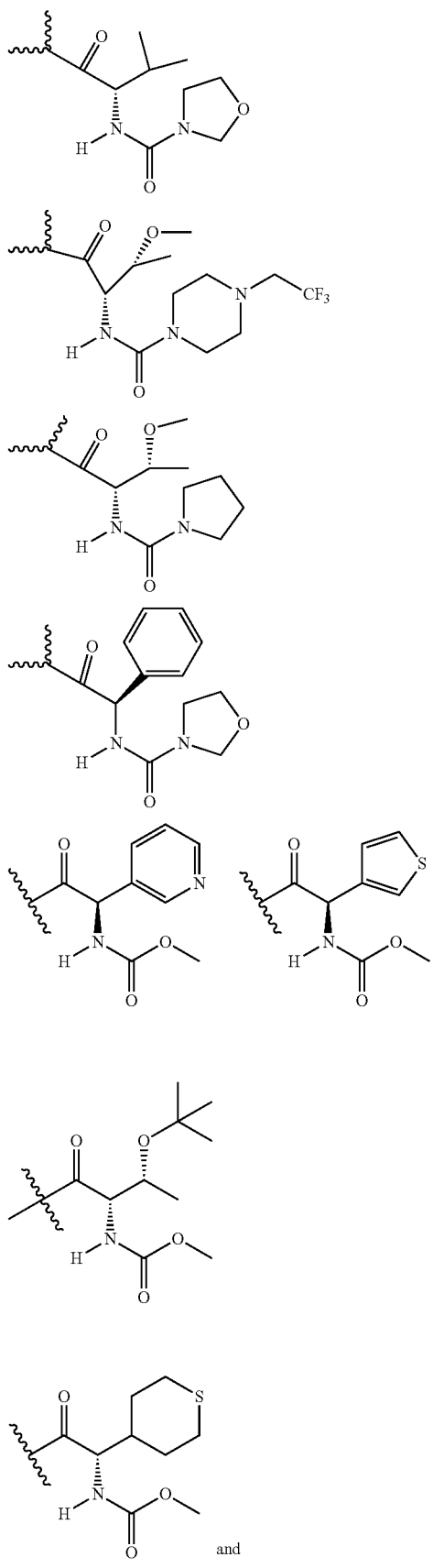
and

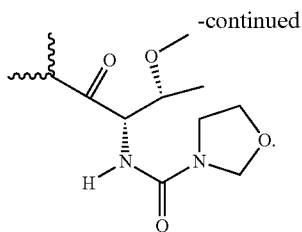

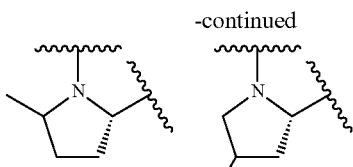

In one specific embodiment one of $P^{1a}$ and $P^{1b}$ is selected from $P^3$, $P^5$, $P^6$, $P^7$, $P^8$, $P^{10}$, $P^{12}$, $P^{15}$, $P^{18}$, $P^{19}$ and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

In one specific embodiment one of $P^{1a}$ and $P^{1b}$ is selected from $P^3$, $P^5$, $P^6$, $P^7$, $P^8$, $P^{10}$, $P^{12}$, $P^{15}$, $P^{18}$, $P^{19}$ and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{18}$, $P^{19}$ and $P^{30}$.

In one specific embodiment one of $P^{1a}$ and $P^{1b}$ is selected from $P^3$, $P^5$, $P^6$, $P^7$, $P^8$, $P^{12}$, $P^{15}$, $P^{18}$, $P^{19}$ and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

In one specific embodiment one of $P^{1a}$ and $P^{1b}$ is selected from $P^3$, $P^5$, $P^6$, $P^7$, $P^8$, $P^{15}$, $P^{18}$, $P^{19}$ and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

In one specific embodiment one of $P^{1a}$ and $P^{1b}$ is selected from $P^3$, $P^5$, $P^6$, $P^7$, $P^8$, $P^{15}$, $P^{18}$, $P^{19}$ and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

In one specific embodiment one of $P^{1a}$ and $P^{1b}$ is selected from $P^3$, $P^5$, $P^6$, $P^7$, $P^8$, $P^{15}$, $P^{18}$, and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

In one specific embodiment one of $P^{1a}$ and $P^{1b}$ is selected from $P^3$, $P^5$, $P^6$, $P^7$, $P^8$, $P^{15}$, and $P^{18}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

In one specific embodiment one of $P^{1a}$ and $P^{1b}$ is selected from $P^7$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

In one specific embodiment one of $P^{1a}$ and $P^{1b}$ is selected from $P^3$, $P^5$, $P^6$, $P^7$, $P^{18}$, and $P^{19}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

In one specific embodiment one of $P^{1a}$ and $P^{1b}$ is selected from $P^3$, $P^5$, $P^6$, $P^7$, $P^8$, $P^{10}$, $P^{12}$, $P^{18}$, and $P^{30}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

In one specific embodiment one of $P^{1a}$ and $P^{1b}$ is selected from $P^3$, $P^6$, $P^7$, $P^{10}$, and $P^{18}$; and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

In one specific embodiment $P^{1a}$ is $P^0$.

In one specific embodiment $P^{1a}$ is selected from:

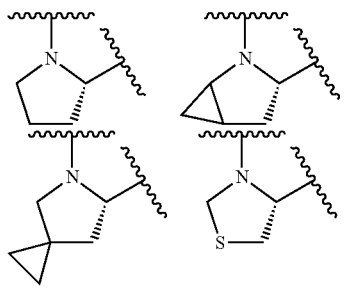

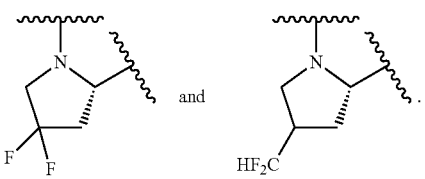

In one specific embodiment $P^{1a}$ is $P^1$.

In one specific embodiment $P^{1a}$ is selected from:

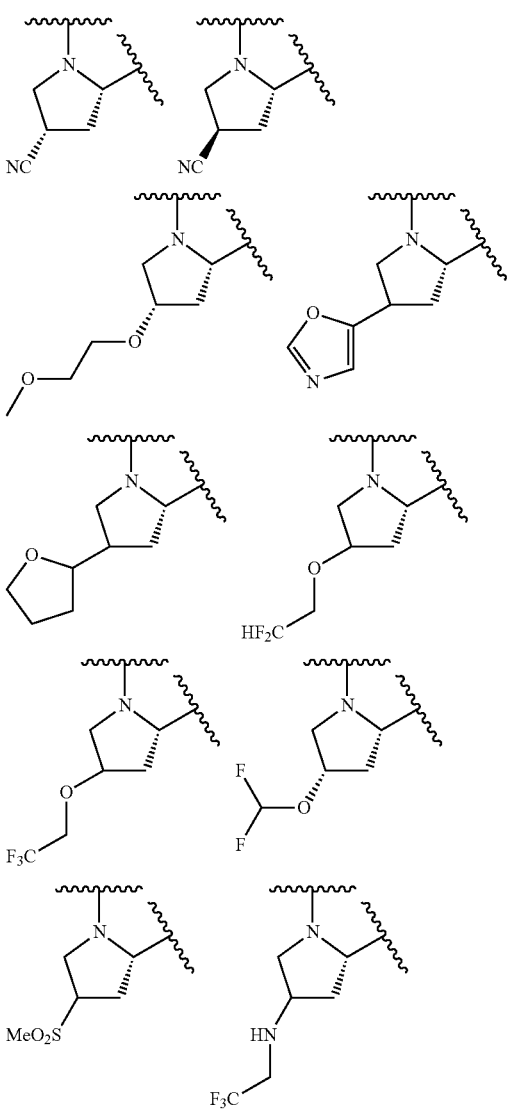

-continued

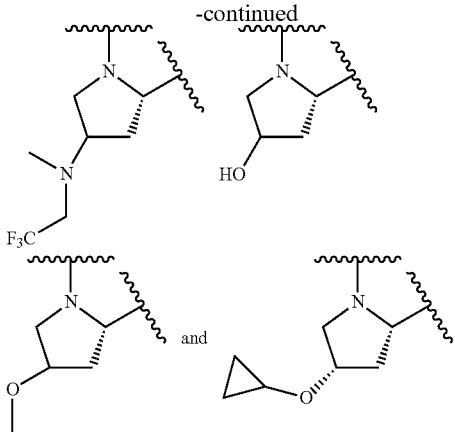

In one specific embodiment P$^{1a}$ is P$^3$.
In one specific embodiment P$^{1a}$ is selected from:

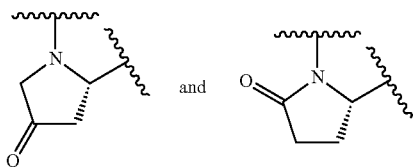

In one specific embodiment P$^{1a}$ is P$^5$.
In one specific embodiment P$^{1a}$ is selected from:

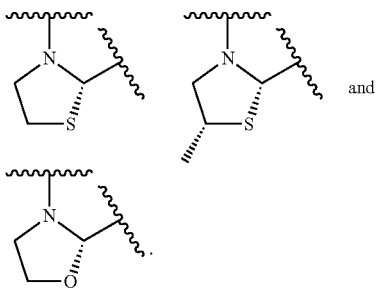

In one specific embodiment P$^{1a}$ is P$^6$.
In one specific embodiment P$^{1a}$ is:

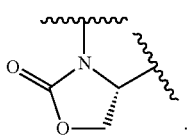

In one specific embodiment P$^{1a}$ is P$^7$.
In one specific embodiment P$^{1a}$ is:

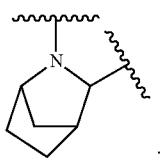 [SMILES: *C1C2CCC(C2)N1*]

In one specific embodiment P$^{1a}$ is P$^8$.

In one specific embodiment P$^{1a}$ is selected from:

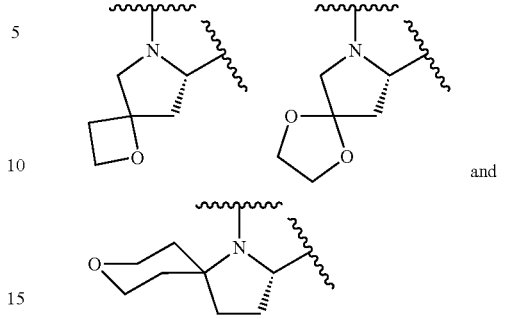

In one specific embodiment P$^{1a}$ is P$^{10}$.
In one specific embodiment P$^{1a}$ is:

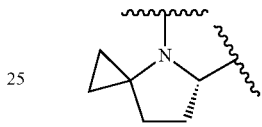

In one specific embodiment P$^{1a}$ is P$^{12}$.
In one specific embodiment P$^{1a}$ is P$^{15}$.
In one specific embodiment P$^{1a}$ is selected from:

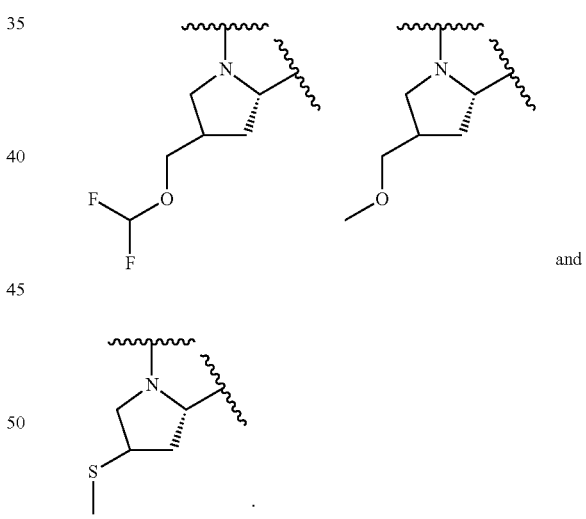

In one specific embodiment P$^{1a}$ is P$^{18}$.
In one specific embodiment P$^{1a}$ is:

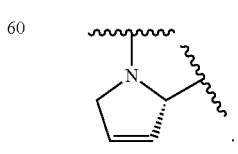

In one specific embodiment P$^{1b}$ is P$^0$.

In one specific embodiment $P^{1b}$ is selected from:

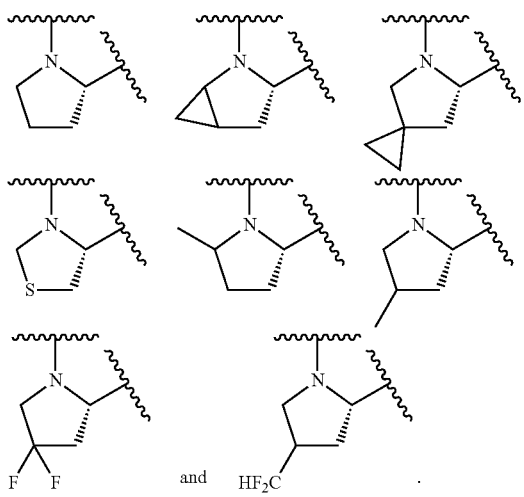

In one specific embodiment $P^{1b}$ is $P^1$.
In one specific embodiment $P^{1b}$ is selected from:

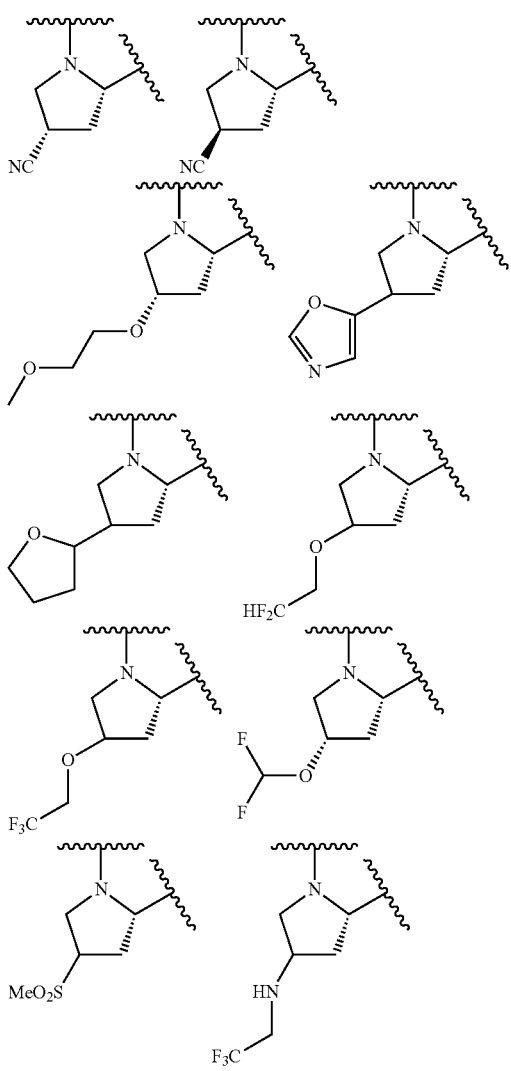

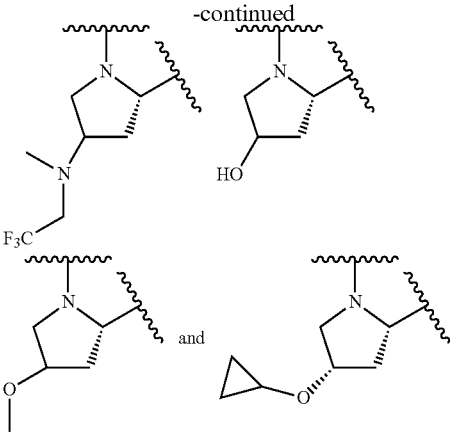

In one specific embodiment $P^{1b}$ is $P^3$.
In one specific embodiment $P^{1b}$ is selected from:

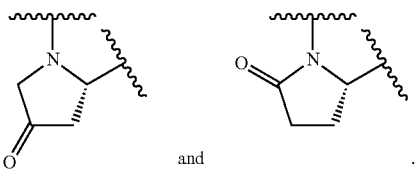 [SMILES: *[C@@H]1CC(=O)CN1* ; *[C@@H]1CCC(=O)N1*]

In one specific embodiment $P^{1b}$ is $P^5$.
In one specific embodiment $P^{1b}$ is selected from:

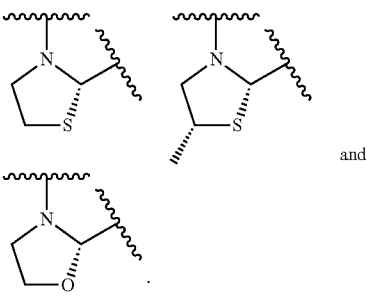

In one specific embodiment $P^{1b}$ is $P^6$.
In one specific embodiment $P^{1b}$ is:

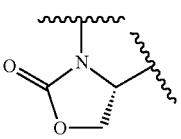

In one specific embodiment $P^{1b}$ is $P^7$.
In one specific embodiment $P^{1b}$ is:

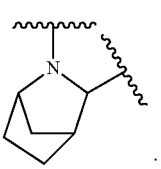 [SMILES: *C1C2CCC(C2)N1*]

In one specific embodiment $P^{1b}$ is $P^8$.

In one specific embodiment $P^{1b}$ is selected from:

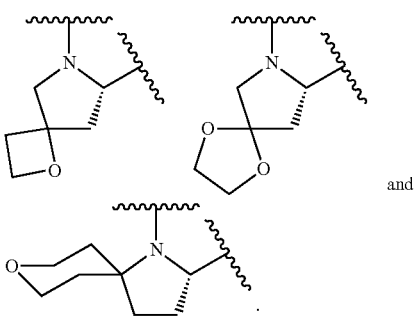

and

In one specific embodiment $P^{1b}$ is $P^{10}$.
In one specific embodiment $P^{1b}$ is:

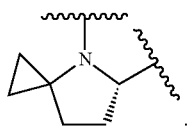 [SMILES: *[C@@H]1CCC2(CC2)N1*]

In one specific embodiment $P^{1b}$ is $P^{12}$.
In one specific embodiment $P^{1b}$ is $P^{15}$.
In one specific embodiment $P^{1b}$ is selected from:

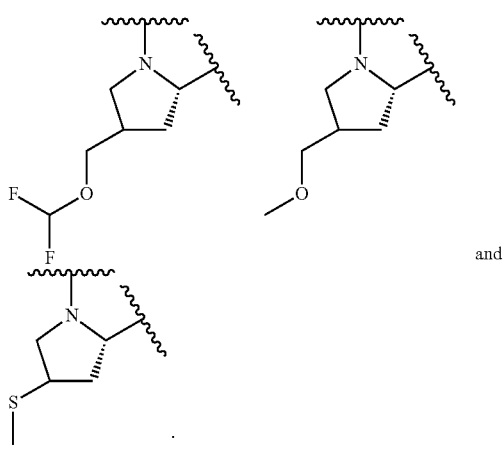

and

In one specific embodiment $P^{1b}$ is $P^{18}$.
In one specific embodiment $P^{1b}$ is:

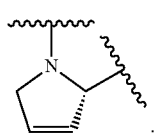

In one specific embodiment at least one of $P^{1a}$ and $P^{1b}$ is:

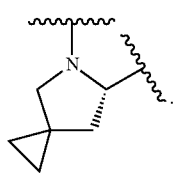 [SMILES: *[C@@H]1CC2(CC2)CN1*]

In one specific embodiment at least one of $P^{1a}$ and $P^{1b}$ is selected from:

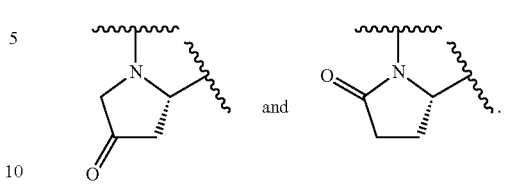

and

In one specific embodiment at least one of $P^{1a}$ and $P^{1b}$ is selected from:

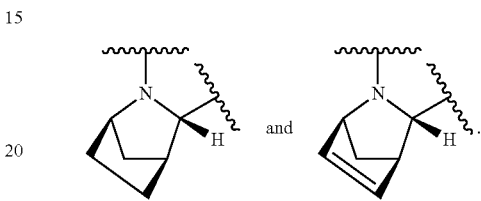

and

In one specific embodiment at least one of $P^{1a}$ and $P^{1b}$ is selected from:

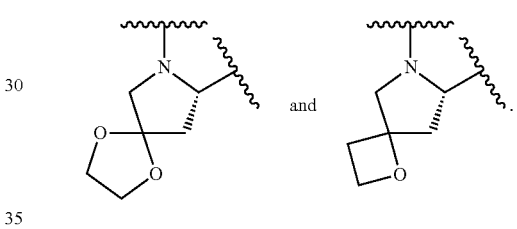

and

In one specific embodiment at least one of $P^{1a}$ and $P^{1b}$:

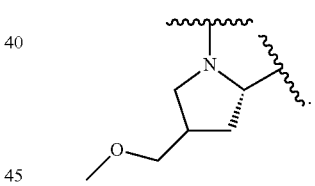

In one specific embodiment at least one of $P^{1a}$ and $P^{1b}$:

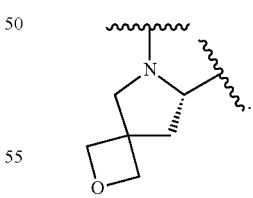

In one specific embodiment at least one of $P^{1a}$ and $P^{1b}$:

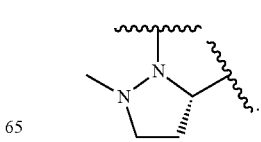

In one specific embodiment P$^{1a}$ is

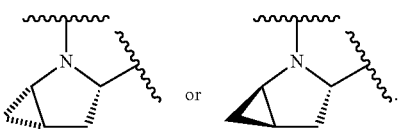

In one specific embodiment P$^{1b}$ is

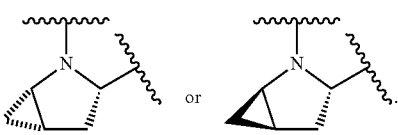

In one specific embodiment P$^{1a}$ is

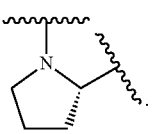

In one specific embodiment P$^{1b}$ is

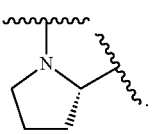 [SMILES: *[C@@H]1CCCN1*]

In one specific embodiment the invention provides compound which is any one of formulae 26-102 as shown in Table 2, or a pharmaceutically acceptable salt or prodrug thereof.

In one specific embodiment the invention provides compound which is any one of formulae 103-289 as shown in Table 3, or a pharmaceutically acceptable salt or prodrug thereof.

In one specific embodiment the invention provides compound which is any one of formulae 290-539, or a pharmaceutically acceptable salt or prodrug thereof.

In one specific embodiment the invention provides compound which is a prodrug or a pharmaceutically acceptable salt thereof.

In one specific embodiment the invention provides a pharmaceutical composition comprising a compound of the invention and at least one pharmaceutically acceptable carrier.

In one specific embodiment the invention provides for the use of a compound of the invention in treating disorders associated with HCV. In one specific embodiment the composition can optionally further comprise at least one additional therapeutic agent. In one specific embodiment the additional therapeutic agent is selected from the group consisting of interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV. In one specific embodiment the composition can optionally further comprise a nucleoside analogue. In one specific embodiment the composition can optionally further comprise an interferon or pegylated interferon. In one specific embodiment the composition the nucleoside analogue is selected from ribavirin, viramidine, levovirin, a L-nucleoside, and isatoribine and said interferon is α-interferon or pegylated interferon.

In one specific embodiment the invention provides a method of treating disorders associated with hepatitis C, said method comprising administering to an individual a pharmaceutical composition which comprises a therapeutically effective amount of the compound as described in any of claims 1-288 or a pharmaceutically acceptable salt, or prodrug thereof.

In one specific embodiment the invention provides a compound of the invention for use in medical therapy.

In one specific embodiment the invention provides the use of a compound of the invention for preparing a medicament for treating hepatitis C or a hepatitis C associated disorder.

In one specific embodiment the invention provides a compound of the invention for use in the prophylactic or therapeutic treatment of hepatitis C or a or a hepatitis C associated disorder.

In one specific embodiment the invention provides a novel compound as described herein.

In one specific embodiment the invention provides a novel synthetic method as described herein.

Specific Embodiment A

In one specific embodiment the invention provides a compound of formula (I) wherein W$^{1a}$ is:

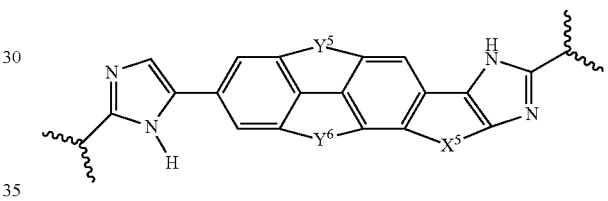

wherein W$^{1a}$ is optionally substituted with one or more (e.g. 1, 2, 3, or 4) groups independently selected from halo, alkyl, haloalkyl, cyano, and

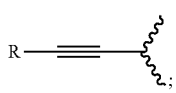

each R is independently H, alkyl, haloalkyl, cycloalkyl, aryl, or heteroaryl;
wherein:
either Y$^5$ is absent and Y$^6$ is —CH$_2$—CH$_2$—, —O—CH$_2$—, —CH$_2$—O—, or —CH═CH—; or Y$^6$ is absent and Y$^5$ is —CH$_2$—CH$_2$—, —O—CH$_2$—, —CH$_2$—O—, or —CH═CH—; and
X$^5$ is —CH$_2$—CH$_2$— or —CH═CH—;
or a pharmaceutically acceptable salt or prodrug thereof.

In one specific embodiment the invention provides a compound of formula I wherein W$^{1a}$ has the formula:

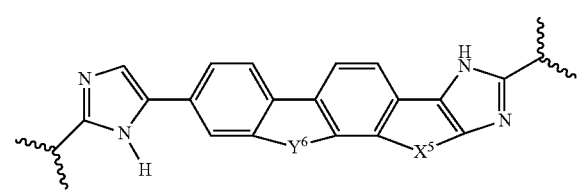

wherein $W^{1a}$ is optionally substituted with one or more (e.g. 1, 2, 3, or 4) groups independently selected from halo, alkyl, haloalkyl, cyano, and

R—≡—⌇ ;

each R is independently H, alkyl, haloalkyl, cycloalkyl, aryl, or heteroaryl;

$Y^6$ is —CH$_2$—CH$_2$—, —O—CH$_2$—, —CH$_2$—O—, or —CH=CH—; and $X^5$ is —CH$_2$—CH$_2$— or —CH=CH—;

or a pharmaceutically acceptable salt or prodrug thereof.

In one specific embodiment the invention provides a compound of formula (I) wherein $W^{1a}$ has the formula

[structure]

wherein $W^{1a}$ is optionally substituted with one or more (e.g. 1, 2, 3, or 4) groups independently selected from halo, alkyl, haloalkyl, cyano, and

R—≡—⌇ ;

each R is independently H, alkyl, haloalkyl, cycloalkyl, aryl, or heteroaryl;

$Y^5$ is —CH$_2$—CH$_2$—, —O—CH$_2$—, —CH$_2$—O—, or —CH=CH—; and $X^5$ is —CH$_2$—CH$_2$— or —CH=CH—;

or a pharmaceutically acceptable salt or prodrug thereof

In one specific embodiment the invention provides a compound of formula (I):

$$E^{1a}\text{-}V^{1a}\text{—C(=O)—}P^{1a}\text{—}W^{1a}\text{—}P^{1b}\text{—C(=O)—}V^{1b}\text{-}E^{1b} \quad (I)$$

wherein:

$W^{1a}$ has the formula:

[structure]

and $W^{1a}$ is optionally substituted with one or more (e.g. 1, 2, 3, or 4) groups independently selected from halo, alkyl, haloalkyl, cyano, and

R—≡—⌇ ;

each R is independently H, alkyl, haloalkyl, cycloalkyl, aryl, or heteroaryl;

$Y^5$ is —O—CH$_2$—, or —CH$_2$—O—;

$X^5$ is —CH$_2$—CH$_2$— or —CH=CH—;

$E^{1a}$ is $E^0$, $E^1$, or $E^2$, or $E^{1a}\text{-}V^{1a}$ taken together are $R^{9a}$;

$E^{1b}$ is $E^0$, $E^1$, or $E^2$, or $E^{1b}\text{-}V^{1b}$ taken together are $R^{9b}$;

$V^{1a}$ is $V^0$ or $E^{1a}\text{-}V^{1a}$ taken together are $R^{9a}$;

$V^{1b}$ is $V^0$ or $E^{1b}\text{-}V^{1b}$ taken together are $R^{9b}$;

$P^{1a}$ is selected from $P^0$, $P^1$, $P^3$, $P^5$, $P^6$, $P^7$, $P^8$, $P^{15}$, $P^{18}$, $P^{19}$, and $P^{30}$;

$P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;

each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $E^2$ is independently —NHR$^{Ef}$ wherein R$^{Ef}$ is cycloalkylcarbonyl or cycloalkyloxycarbonyl;

each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NR$^{VO1}$R$^{VO1}$COalkyl, wherein each R$^{VO1}$ is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)(OR$^{VO2}$)$_2$, wherein each R$^{VO2}$ is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, ($NR^XR^Y$)alkyl-, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $P^0$ is independently:

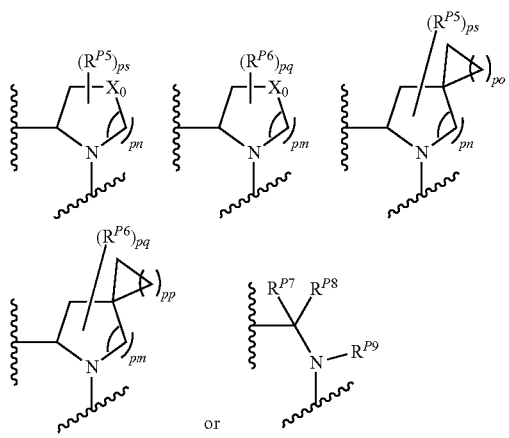

wherein:

$X_0$ is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;

pm and pn are independently 0, 1, or 2;

po and pp are independently 1, 2, or 3;

$R^{P7}$ and $R^{P8}$ are each independently selected from hydrogen, alkenyl, alkoxyalkyl, alkyl, haloalkyl, and ($NR^{Pa}R^{Pb}$)alkyl; or $R^{P7}$ and $R^{P8}$, together with the carbon atom to which they are attached, form a five or six membered saturated ring optionally containing one or two heteroatoms selected from $NR^{Pz}$, O, and S; wherein $R^{Pz}$ is selected from hydrogen and alkyl;

$R^{P9}$ is selected from hydrogen and alkyl;

each $P^1$ is independently:

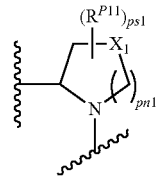

wherein:

$X_1$ is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

at least one $R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclyloxyalkyloxy, ($NR^hR^h$)alkyloxy, cyanoalkoxy, cyanocycloalkyloxy, cycloalkyloxy, oxo, heterocyclyl, —$NR^{hh}R^h$, ($NR^{hh}R^h$)alkyl, ($NR^{hh}R^h$)carbonyl-, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P100}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocloooxyalkyloxy, ($NR^hR^h$)alkyloxy, cyanoalkoxy, cyanocycloalkyloxy, cycloalkyloxy, oxo and heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{P100}$ is independently selected from alkoxy, alkyl, aryl, halo, haloalkyl, hydroxy, and —$NR^{P101}R^{P102}$, wherein the alkyl can optionally form a fused three- to six-membered ring with an adjacent carbon atom, wherein the three- to six-membered ring is optionally substituted with one or two alkyl groups; and $R^{P101}$ and $R^{P102}$ are each independently H, alkyl, aryl, or arylalkyl; or $R^{P101}$ and $R^{P102}$ taken together with the atom to which they are attached form a heterocycle;

ps1 is 1, 2, 3, or 4;
pn1 is 0, 1, or 2;
each $P^3$ is independently a ring of the formula:

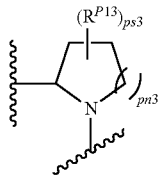

wherein:
the ring is substituted with one or more oxo group;
each $R^{P13}$ is independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps3 is 0, 1, 2, 3, or 4;
pn3 is 0, 1, or 2;
each $P^5$ is independently a ring of the formula:

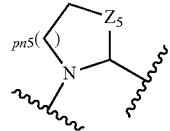

wherein:
the ring is optionally substituted with one or more groups $R^{P15}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;

pn3 is 0, 1, or 2;
$Z_5$ is O, S, S(=O), S(=O)$_2$, or $NR^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

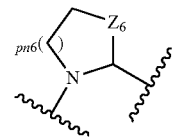

wherein:
the ring is substituted with one or more oxo and is optionally substituted with one or more groups $R^{P16}$ that are independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
$Z_6$ is O, S, S(=O), S(=O)$_2$, or $NR^f$;
pn6 is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P67}$ and $R^{P207}$; wherein $R^{P67}$ is independently selected from alkoxy, alkyl, aryl, halo, haloalkyl, hydroxy, and —$NR^{P205}R^{P206}$, wherein the alkyl can optionally form a fused three- to six-membered ring with an adjacent carbon atom, wherein the three- to six-membered ring is optionally substituted with one or two alkyl groups; $R^{P205}$ and $R^{P206}$ are each independently H, alkyl, aryl, or arylalkyl; or $R^{P205}$ and $R^{P206}$ taken together with the atom to which they are attached form a heterocycle; and $R^{P207}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclyloxyalkyloxy, $(NR^hR^h)$alkyloxy, cyanoalkoxy, cyanocycloalkyloxy, cycloalkyloxy, oxo, heterocyclyl, —$NR^{hh}R^h$, $(NR^{hh}R^h)$alkyl, $(NR^{hh}R^h)$carbonyl-, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, —$S(=O)_2R^h$, —$C(=O)R^h$, —$C(=O)NR^hR^h$;

each $P^8$ is independently a ring of the formula:

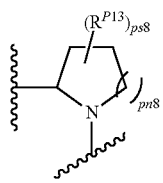

wherein:
ps8 is 2, 3, 4, 5, or 6;
pn8 is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;

each $P^{10}$ is independently:

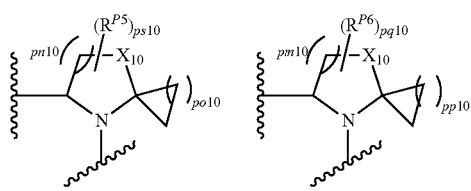

wherein:
$X_{10}$ is selected from O, S, S(O), $SO_2$, $CH_2$, $CHR^{P10}$, and $C(R^{P10})_2$; provided that when pn or pm is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq10 and ps10 are independently 0, 1, 2, 3, or 4;
pm10 and pn10 are independently 0, 1, or 2;
po10 and pp10 are independently 1, 2, or 3;
each $P^{12}$ is independently:

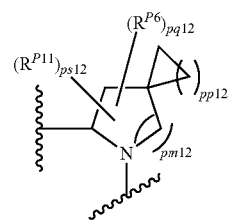

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq12 is independently 0, 1, 2, 3, or 4;
pm12 is independently 0, 1, or 2;
pp12 is independently 1, 2, or 3;
ps12 is 1, 2, 3, or 4;
$R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, $(NR^hR^h)$alkyloxy, cyanoalkoxy, cyanocycloalkyloxy, cycloalkyloxy, oxo, heterocyclyl, —$NR^{hh}R^h$, $(NR^{hh}R^h)$alkyl-, $(NR^{hh}R^h)$carbonyl-, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;

each P$^{15}$ is:

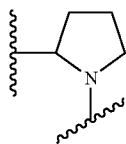 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each P$^{18}$ is:

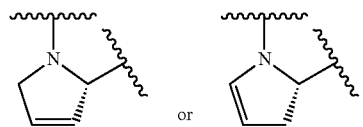 [SMILES: *[C@@H]1C=CCN1* ; *[C@@H]1CC=CN1*]

which is optionally substituted, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl with one or two groups independently selected from halo, alkyl, alkoxyalkyl, haloalkyl, cycloalkyl, and cycloalkylalkyl;

each P$^{19}$ is:

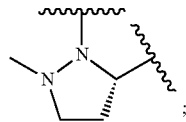 [SMILES: *[C@@H]1CCN(C)N1*]

each P$^{30}$ is independently a ring of the formula:

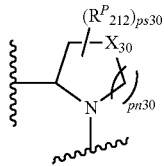

ps30 is 2
pn30 is 0, 1 or 2;
X$_{30}$ is selected from O, S, S(O), SO$_2$, or CH$_2$; provided that when pn is 0, X is CH$_2$.

each R$^{P212}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups R$^{P212}$ that are attached to the same carbon are taken together with the carbon to which they are attached and form a 4-6 membered heterocyclic ring;

each R$^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^X$R$^Y$)alkyl-, and (NR$^X$R$^Y$)carbonyl-; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl-, wherein R$^{X'}$ and R$^{Y'}$ are independently selected from hydrogen and alkyl;

each R$^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, $(NR^XR^Y)$alkyl-, and $(NR^XR^Y)$carbonyl-; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl-, wherein $R^{X'}$ and $R^{Y'}$ are independently selected from hydrogen and alkyl;

or a pharmaceutically acceptable salt or prodrug thereof.

In one specific embodiment the invention provides a compound which has formula:

wherein:

$W^{1a}$ has the formula:

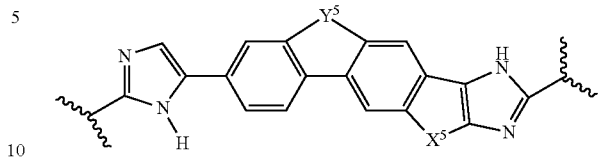

and $W^{1a}$ is optionally substituted with one or more (e.g. 1, 2, 3, or 4) groups independently selected from halo, alkyl, haloalkyl, cyano, and

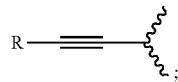

wherein each R is independently H, alkyl, haloalkyl, cycloalkyl, aryl, or heteroaryl;

$Y^5$ is $-O-CH_2-$, or $-CH_2-O-$;
$X^5$ is $-CH_2-CH_2-$ or $-CH=CH-$;

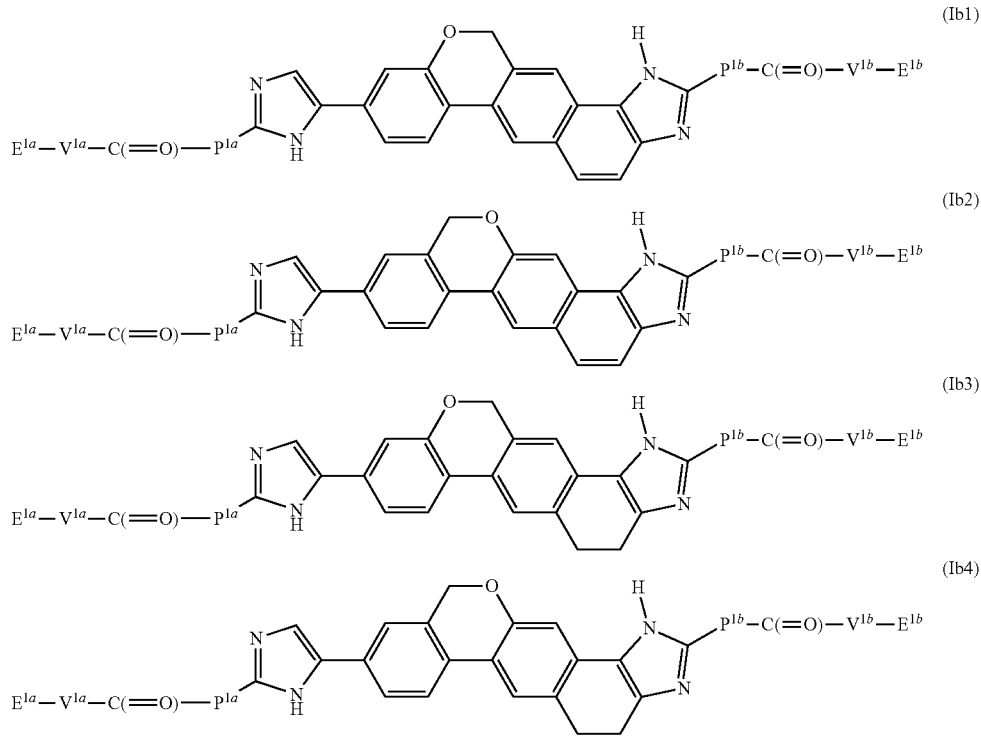

wherein the imidazole ring shown in formula Ib1, Ib2, Ib3, and Ib4 is optionally substituted with one or more (e.g. 1, 2, 3, or 4) groups independently selected from halo, haloalkyl, and alkyl;

or a pharmaceutically acceptable salt or prodrug thereof.

In one specific embodiment the invention provides a compound of formula (I):

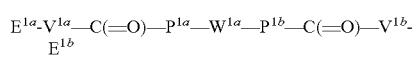

$E^{1a}$ is $E^0$, $E^1$, or $E^2$, or $E^{1a}$-$V^{1a}$ taken together are $R^{9a}$;
$E^{1b}$ is $E^0$, $E^1$, or $E^2$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;

each $E^0$ is independently $-NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each E$^1$ is independently selected from hydrogen, hydroxy, alkyl, haloalkyl, —NHhaloalkyl, aryl, and heterocyclyl;

each E$^2$ is independently —NHR$^{Ef}$ wherein R$^{Ef}$ is cycloalkylcarbonyl or cycloalkyloxycarbonyl;

each V$^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NR$^{VO1}$R$^{VO1}$COalkyl, wherein each R$^{VO1}$ is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)(OR$^{VO2}$)$_2$, wherein each R$^{VO1}$ is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl-, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

P$^{1a}$ and P$^{1b}$ are each independently selected from:

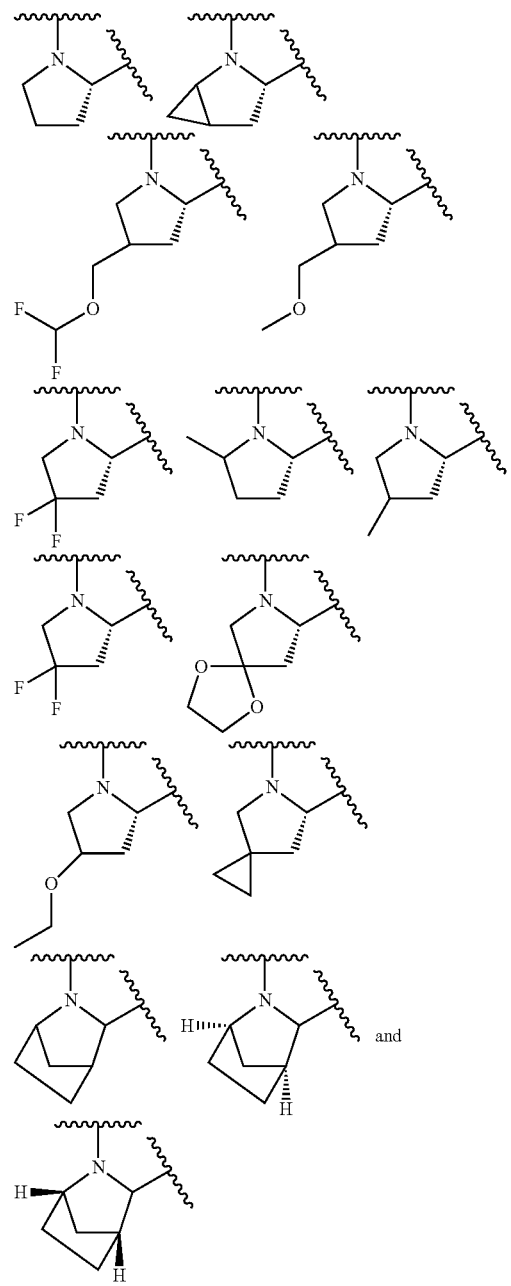

each R$^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)

alkyl-, (NR$^e$R$^f$)alkylcarbonyl-, (NR$^e$R$^f$)carbonyl-, (NR$^e$R$^f$) sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^X$R$^Y$)alkyl-, and (NR$^X$R$^Y$)carbonyl-; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl-, wherein R$^{X'}$ and R$^{Y'}$ are independently selected from hydrogen and alkyl;

each R$^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$) alkyl-, (NR$^e$R$^f$)alkylcarbonyl-, (NR$^e$R$^f$)carbonyl-, (NR$^e$R$^f$) sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^X$R$^Y$)alkyl-, and (NR$^X$R$^Y$)carbonyl-; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl-, wherein R$^{X'}$ and R$^{Y'}$ are independently selected from hydrogen and alkyl; or a pharmaceutically acceptable salt or prodrug thereof.

In one specific embodiment at least one of E$^{1a}$ and E$^{1b}$ is —N(H)(alkoxycarbonyl).

In one specific embodiment at least one of E$^{1a}$ and E$^{1b}$ is —N(H)C(=O)OMe.

In one specific embodiment at least one of E$^{1a}$ and E$^{1b}$ is —N(H)(cycloalkylcarbonyl) or —N(H)(cycloalkyloxycarbonyl).

In one specific embodiment at least one of E$^{1a}$ and E$^{1b}$ is cyclopropylcarbonylamino, cyclobutylcarbonylamino, cyclopropyloxycarbonylamino or cyclobutyloxycarbonylamino.

In one specific embodiment E$^{1a}$ and E$^{1b}$ are each independently selected from cyclopropylcarbonylamino, cyclobutylcarbonylamino, cyclopropyloxycarbonylamino and methoxycarbonylamino.

In one specific embodiment at least one of V$^{1a}$ and V$^{1b}$ is V$^0$.

In one specific embodiment at least one of V$^{1a}$ and V$^{1b}$ is selected from:

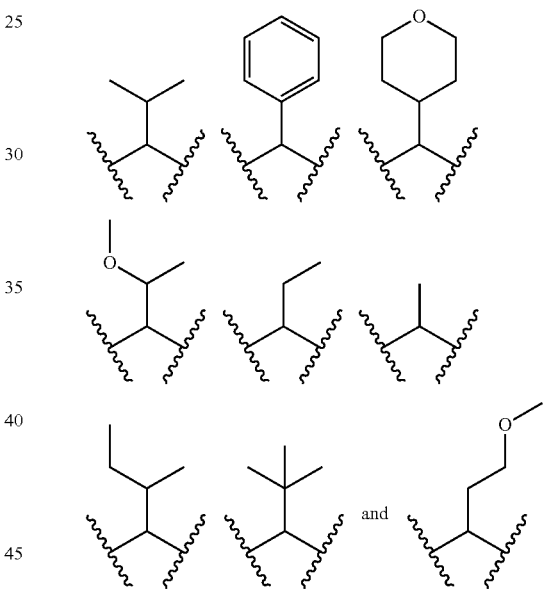

In one specific embodiment at least one of V$^{1a}$ and V$^{1b}$ is selected from:

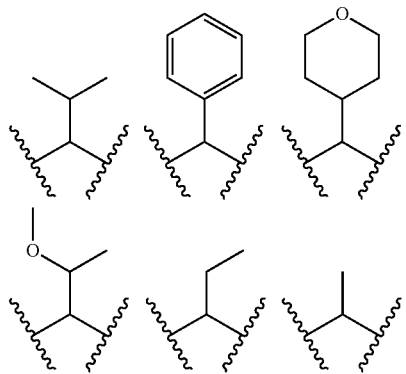

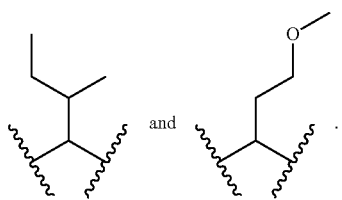

In one specific embodiment at least one of $V^{1a}$ and $V^{1b}$ is:

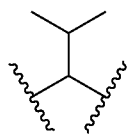 [SMILES: *C(*)C(C)C]

In one specific embodiment at least one of $V^{1a}$ and $V^{1b}$ is selected from:

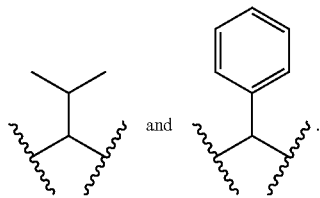

In one specific embodiment at least one of $V^{1a}$ and $V^{1b}$ is selected from:

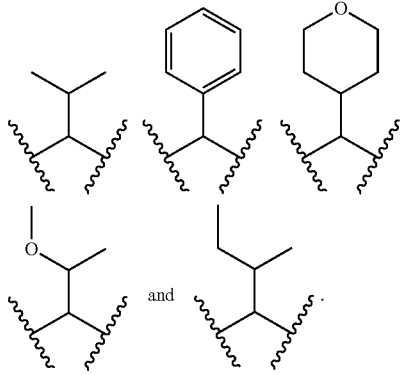

In one specific embodiment $V^{1a}$ and $V^{1b}$ are each independently selected from:

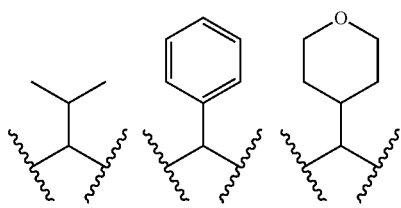

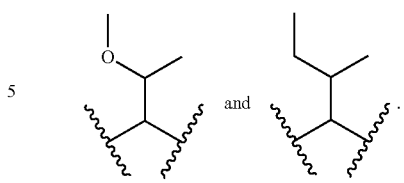

In one specific embodiment at least one of $P^{1a}$ and $P^{1b}$ is selected from $P^0$ and $P^{15}$.

In one specific embodiment $P^{1a}$ and $P^{1b}$ are each independently selected from:

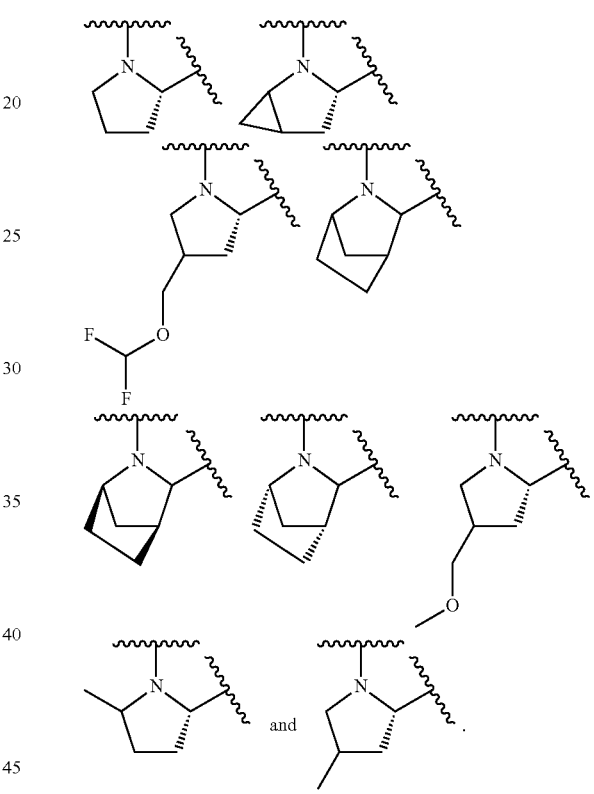

In one specific embodiment at least one of $P^{1a}$ and $P^{1b}$ is selected from:

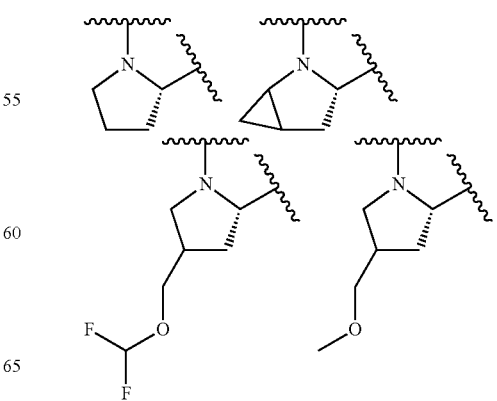

-continued

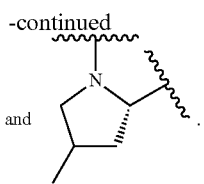

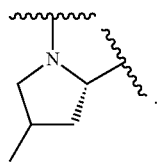

In one specific embodiment $P^{1a}$ and $P^{1b}$ are each independently selected from:

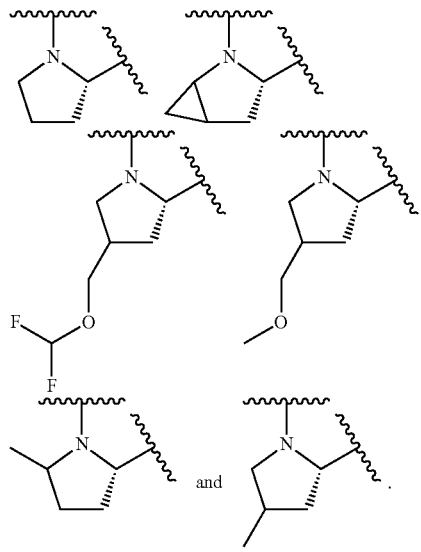

In one specific embodiment at least one of $P^{1a}$ and $P^{1b}$ is selected from:

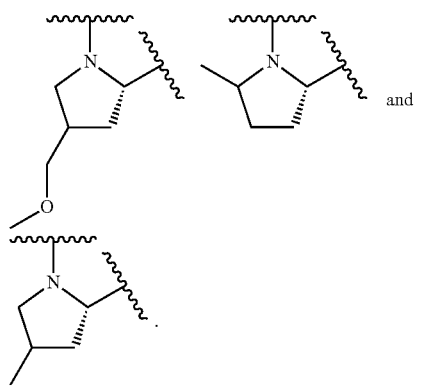

In one specific embodiment $P^{1a}$ and $P^{1b}$ are each independently selected from:

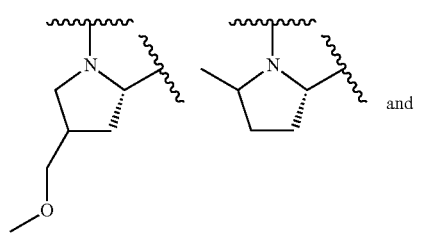

-continued

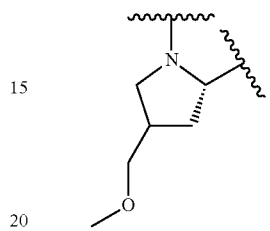

In one specific embodiment one of $P^{1a}$ and $P^{1b}$ is:

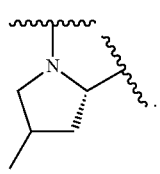

and the other of $P^{1a}$ and $P^{1b}$ is:

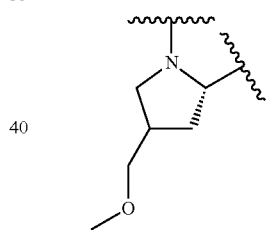

In one specific embodiment one of $P^{1a}$ and $P^{1b}$ is:

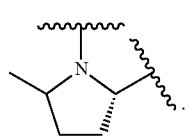

and the other of $P^{1a}$ and $P^{1b}$ is:

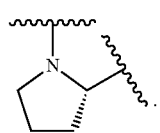 [SMILES: *[C@@H]1CCCN1*]

In one specific embodiment one of $P^{1a}$ and $P^{1b}$ is $P^0$.

In one specific embodiment at least one of $P^{1a}$ and $P^{1b}$ is:

In one specific embodiment at least one of $P^{1a}$ and $P^{1b}$ is $P^7$.

In one specific embodiment at least one of $P^{1a}$ and $P^{1b}$ is:

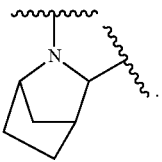 [SMILES: *C1C2CCC(C2)N1*]

In one specific embodiment at least one of $P^{1a}$ and $P^{1b}$ is:

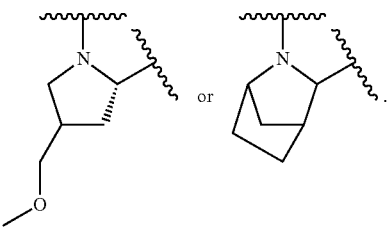 or

In one specific embodiment at least one of $P^{1a}$ and $P^{1b}$ is:

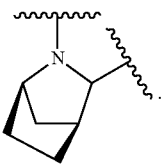 [SMILES: *C1[C@H]2CC[C@H](C2)N1*]

In one specific embodiment at least one of $P^{1a}$ and $P^{1b}$ is:

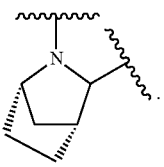 [SMILES: *C1[C@@H]2CC[C@@H](C2)N1*]

In one specific embodiment at least one of $P^{1a}$ and $P^{1b}$ is $P^{15}$.

In one specific embodiment at least one of $P^{1a}$ and $P^{1b}$ is:

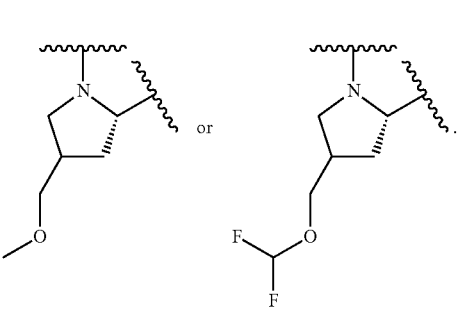

In one specific embodiment at least one of $P^{1a}$ and $P^{1b}$ is:

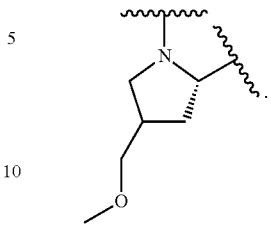

In one specific embodiment at least one of $P^{1a}$ and $P^{1b}$ is selected from $P^7$ and $P^{15}$.

In one specific embodiment at least one of $-V^{1a}-C(=O)-P^{1a}-$ and $-P^{1b}-C(=O)-V^{1b}-$ is:

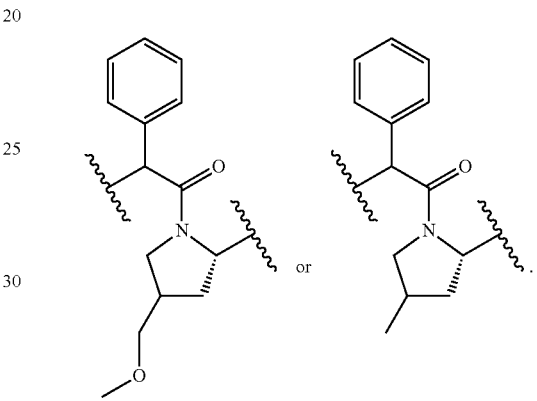

In one specific embodiment at least one of $-V^{1a}-C(=O)-P^{1a}-$ and $-P^{1b}-C(=O)-V^{1b}-$ is:

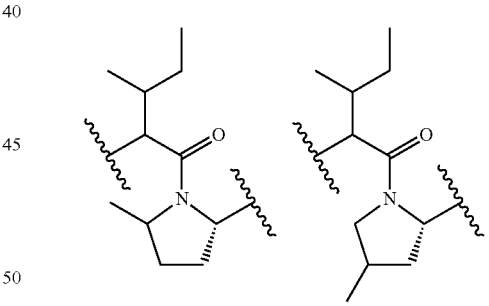

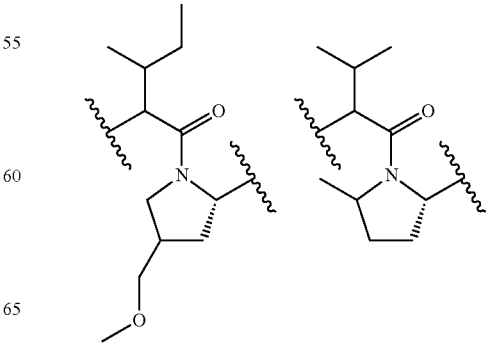

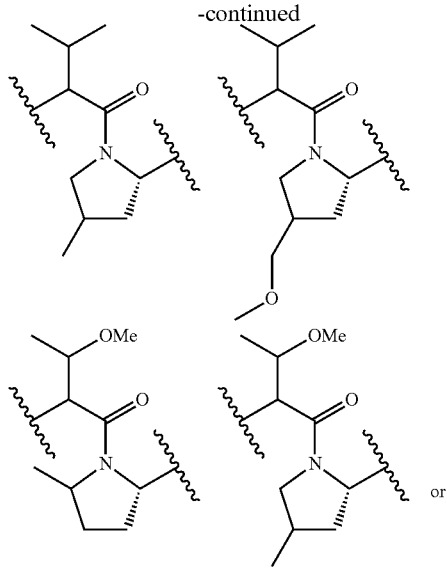 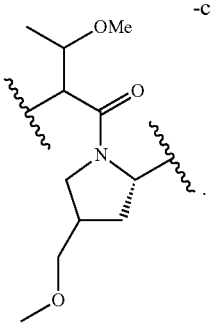
In one specific embodiment the invention provides a compound prepared in the Examples herein that is a compound of specific Embodiment A, or a salt or a prodrug thereof.
In one specific embodiment the invention provides the compound:
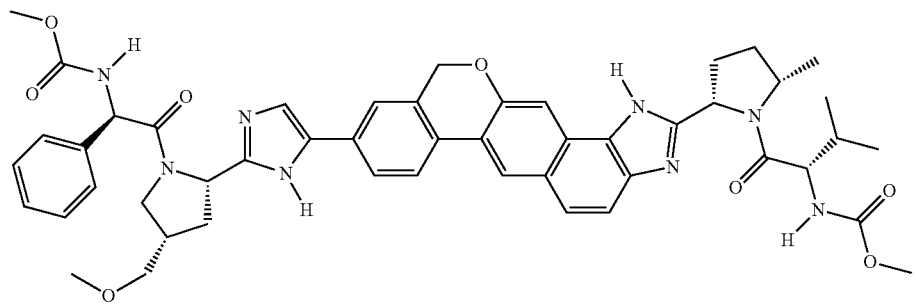
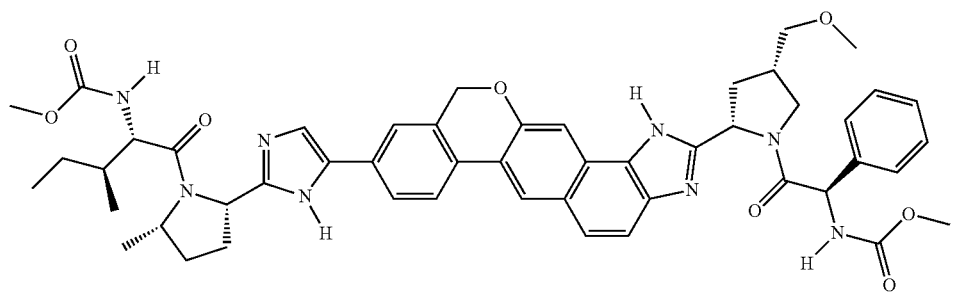
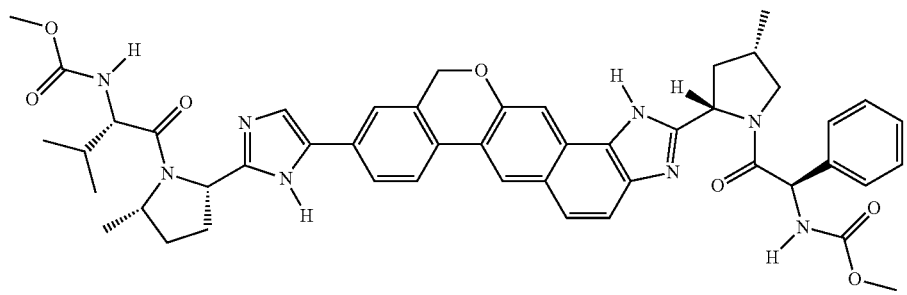

-continued
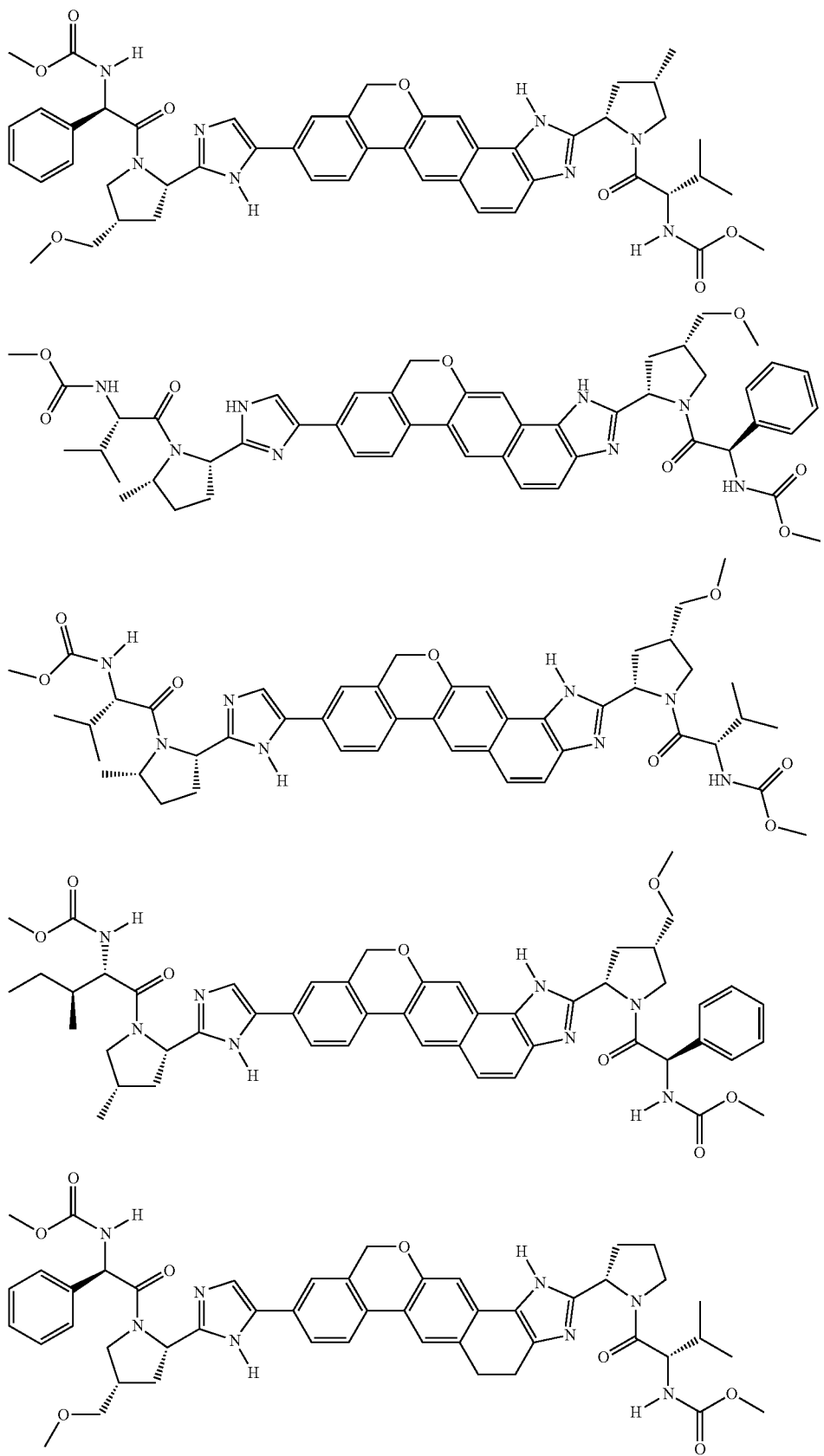

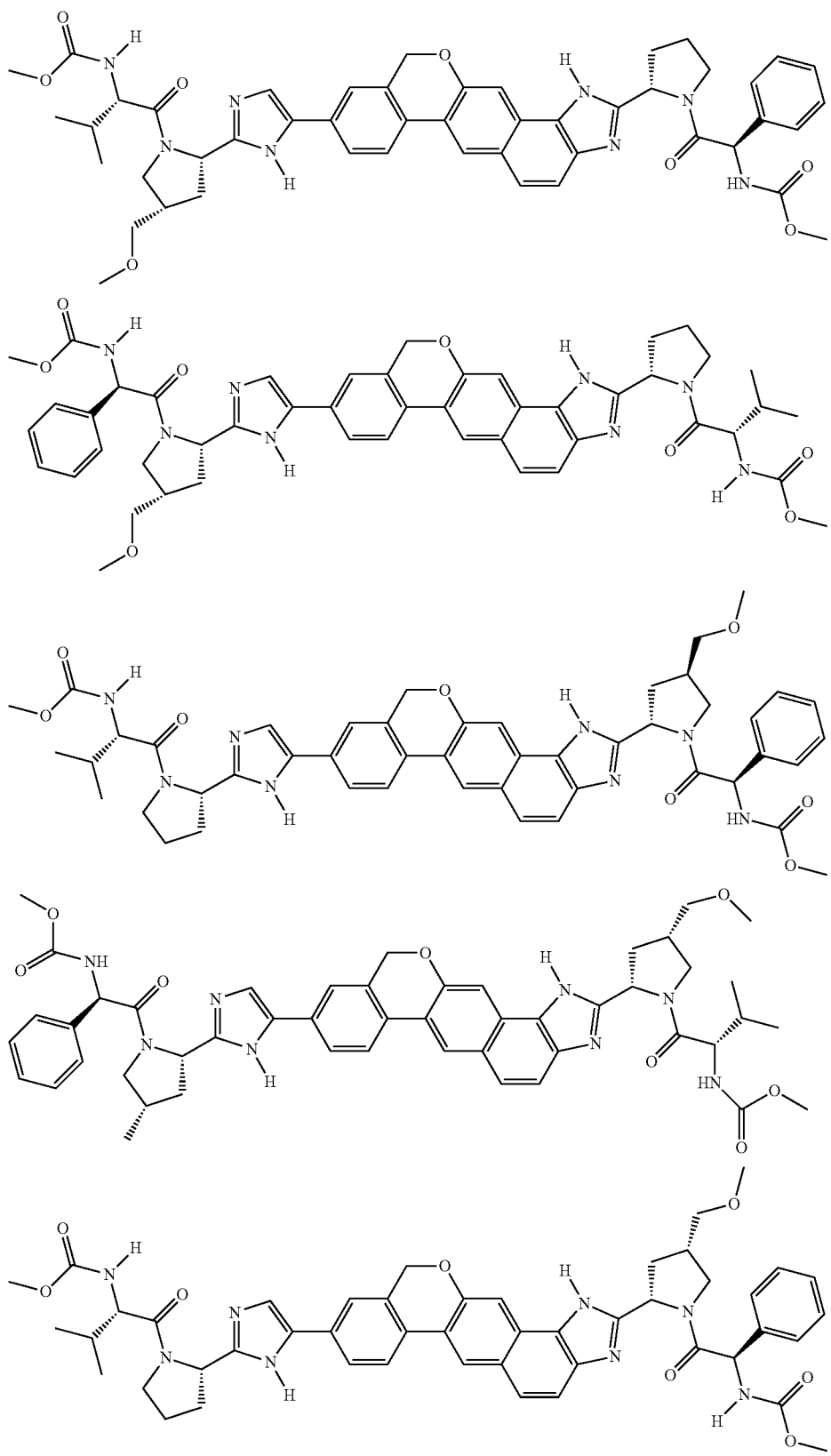

-continued
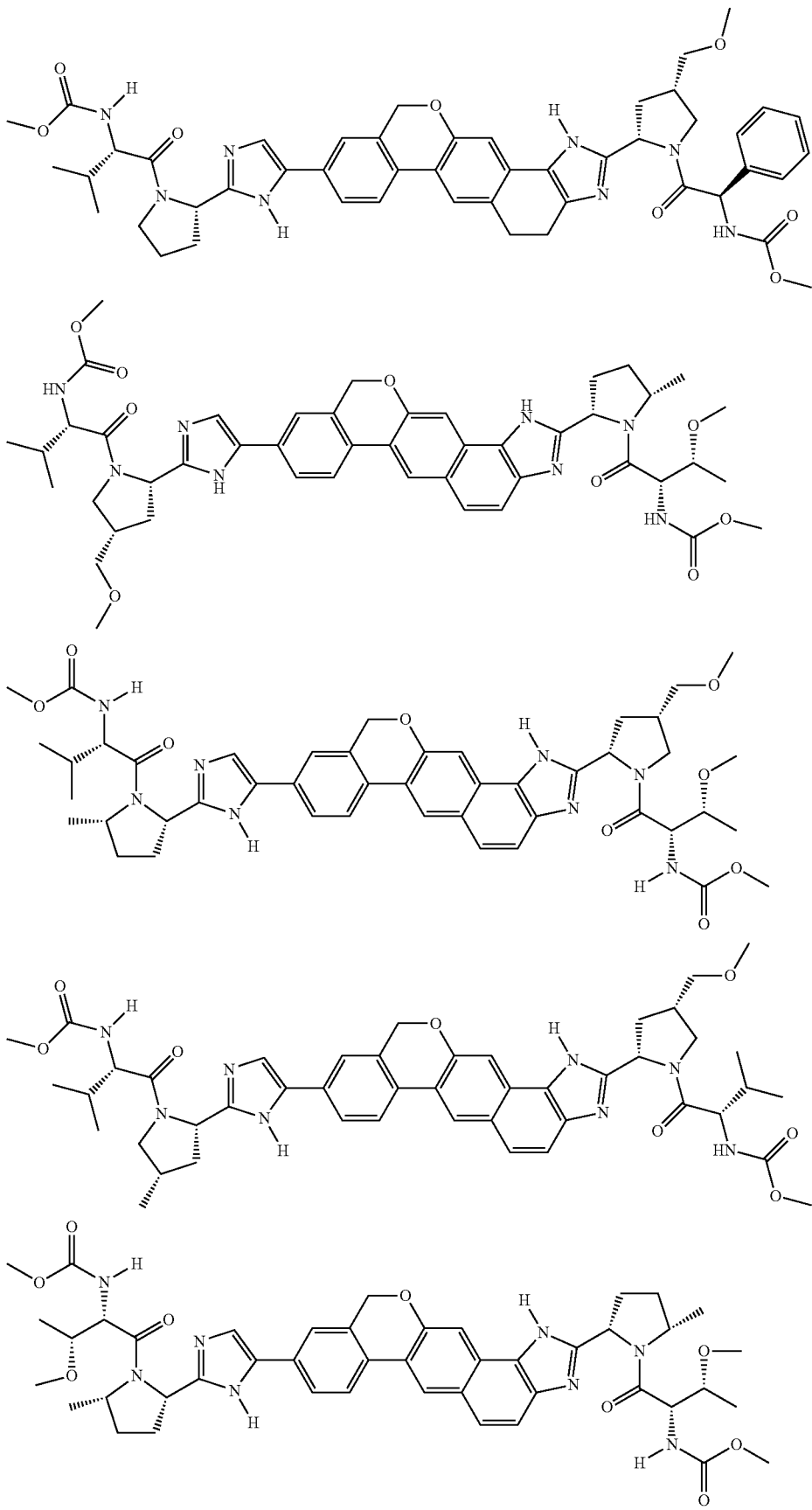

-continued
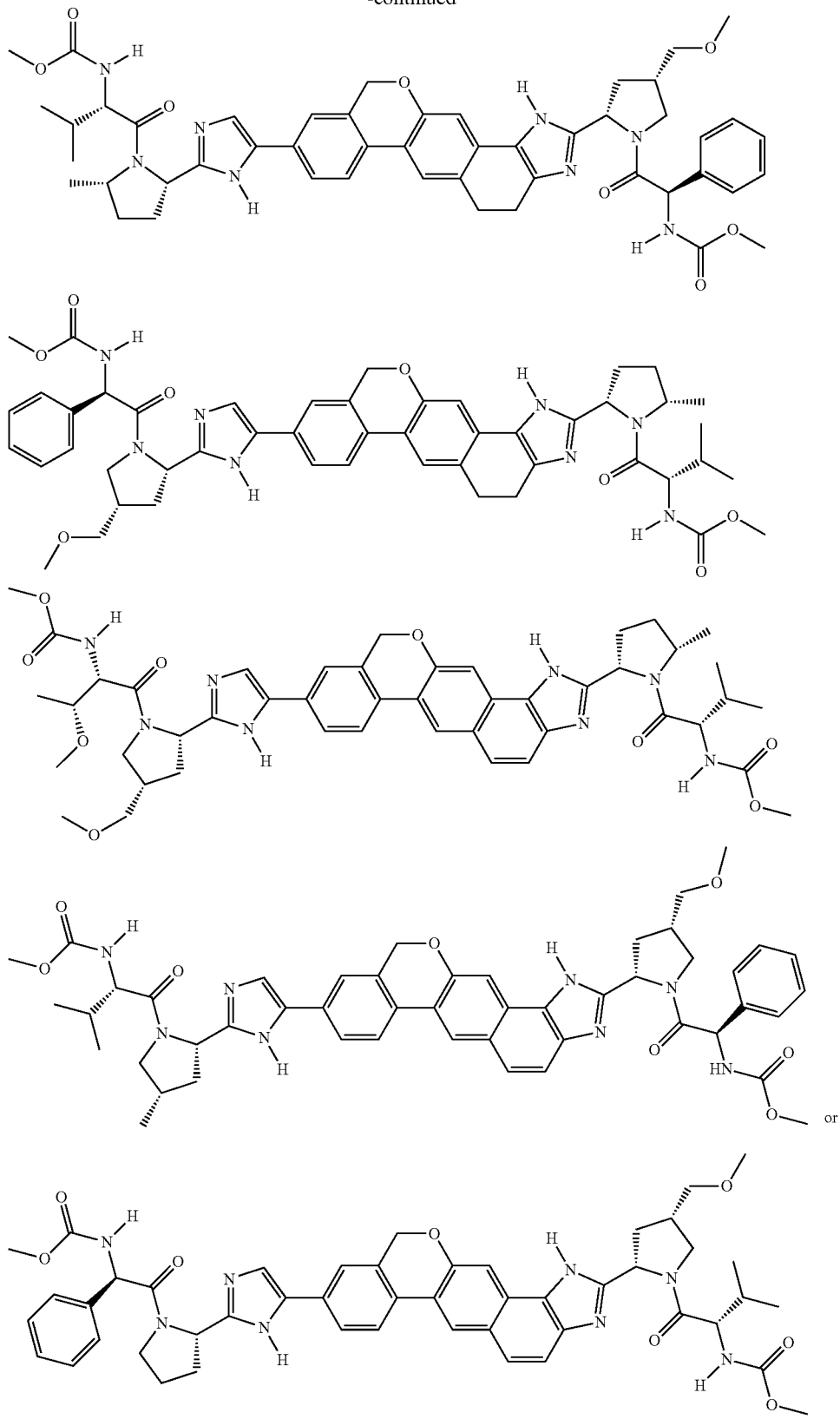
or a pharmaceutically acceptable salt or prodrug thereof.

Specific Embodiment B

In one specific embodiment the invention provides a compound of formula (I):

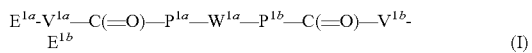

wherein:

$W^{1a}$ has the formula:

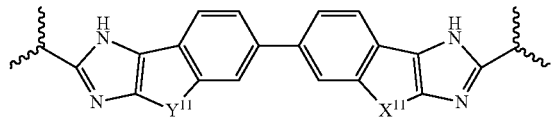

wherein:
$X^{11}$ is —CH$_2$—CH$_2$—, —O—CH$_2$—, or —CH=CH—
$Y^{11}$ is —CH=CH—
and $W^{1a}$ is optionally substituted with one or more (e.g. 1, 2, 3, or 4) groups independently selected from halo, alkyl, haloalkyl, cyano, and

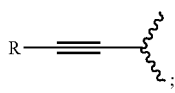

wherein each R is independently H, alkyl, haloalkyl, cycloalkyl, aryl, or heteroaryl;
$E^{1a}$ is $E^0$, $E^1$, or $E^2$, or $E^{1a}$-$V^{1a}$ taken together are $R^{9a}$;
$E^{1b}$ is $E^0$, $E^1$, or $E^2$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
one of $P^{1a}$ and $P^{1b}$ is

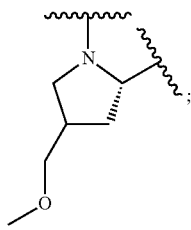

and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$.

each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $E^2$ is independently —NHR$^{Ef}$ wherein R$^{Ef}$ is cycloalkylcarbonyl or cycloalkyloxycarbonyl;

each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NR$^{VO1}$R$^{VO1}$COalkyl, wherein each R$^{VO1}$ is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)(OR$^{VO2}$)$_2$, wherein each R$^{VO1}$ is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl-, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $P^0$ is independently:

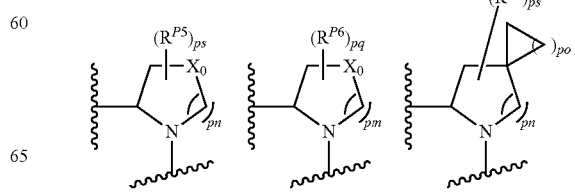

-continued

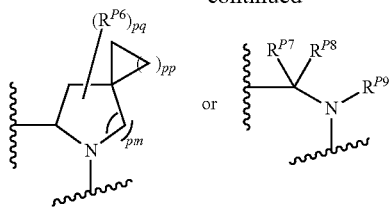

wherein:

$X_0$ is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;

each P$^1$ is independently:

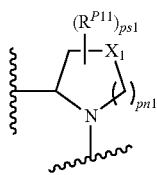

wherein:

$X_1$ is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxy-alkyloxy, haloalkoxyalkyloxy, cycloalkyoxyalkyloxy, aryloxyalkyloxy, heteroaryloxyalkyloxy, heterocylyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl-, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(═O)$_2$R$^h$, —C(═O)R$^h$, —C(═O)NR$^h$R$^h$; and the remaining R$^{P11}$ are independently selected from R$^{P100}$, cyano, alkylsulfonyl, arylsulfonyl, (NR$^h$R$^h$)sulfonyl, heterocyclylsulfonyl, heteroarylsulfonyl, haloalkoxy, alkoxy-alkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo and heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{P100}$ is independently selected from alkoxy, alkyl, aryl, halo, haloalkyl, hydroxy, and —NR$^{P101}$R$^{P102}$, wherein the alkyl can optionally form a fused three- to six-membered ring with an adjacent carbon atom, wherein the three- to six-membered ring is optionally substituted with one or two alkyl groups; and R$^{P101}$ and R$^{P102}$ are each independently H, alkyl, aryl, or arylalkyl; or R$^{P101}$ and R$^{P102}$ taken together with the atom to which they are attached form a heterocycle;

ps1 is 1, 2, 3, or 4;
pn1 is 0, 1, or 2;
each P$^3$ is independently a ring of the formula:

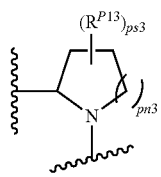

wherein:
the ring is substituted with one or more oxo group;
each R$^{P13}$ is independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxy-alkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps3 is 0, 1, 2, 3, or 4;

pn3 is 0, 1, or 2;

each $P^5$ is independently a ring of the formula:

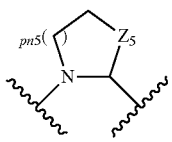

wherein:
the ring is optionally substituted with one or more groups $R^{P15}$ that are independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pn3 is 0, 1, or 2;

$Z_5$ is O, S, S(=O), S(=O)$_2$, or NR$^f$;

each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $-S(=O)_2NR^hR^h$, $-S(=O)_2R^h$, $C(=O)R^h$, $C(=O)OR^h$, $-C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^6$ is independently a ring of the formula:

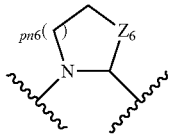

wherein:
the ring is substituted with one or more oxo and is optionally substituted with one or more groups $R^{P16}$ that are independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

$Z_6$ is O, S, S(=O), S(=O)$_2$, or NR$^f$;

pn6 is 0, 1, or 2;

each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $-S(=O)_2NR^hR^h$, $-S(=O)_2R^h$, $C(=O)R^h$, $C(=O)OR^h$, $-C(=O)NR^hR^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P67}$ and $R^{P207}$; wherein $R^{P67}$ is independently selected from alkoxy, alkyl, aryl, halo, haloalkyl, hydroxy, and $-NR^{P205}R^{P206}$, wherein the alkyl can optionally form a fused three- to six-membered ring with an adjacent carbon atom, wherein the three- to six-membered ring is optionally substituted with one or two alkyl groups; $R^{P205}$ and $R^{P206}$ are each independently H, alkyl, aryl, or arylalkyl; or $R^{P205}$ and $R^{P206}$ taken together with the atom to which they are attached form a heterocycle; and $R^{P207}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclyloxyalkyloxy, $(NR^hR^h)$alkyloxy, cyanoalkoxy, cyanocycloalkyloxy, cycloalkyloxy, oxo, heterocyclyl, $-NR^{hh}R^h$, $(NR^{hh}R^h)$alkyl, $(NR^{hh}R^h)$carbonyl-, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, $-S(=O)_2R^h$, $-C(=O)R^h$, $-C(=O)NR^hR^h$;

each $P^8$ is independently a ring of the formula:

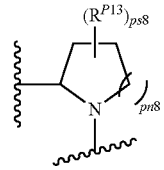

wherein:
ps8 is 2, 3, 4, 5, or 6;
pn8 is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
each $P^{10}$ is independently:

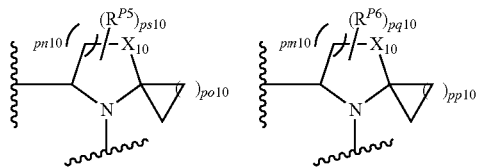

wherein:
$X_{10}$ is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq10 and ps10 are independently 0, 1, 2, 3, or 4;
pm10 and pn10 are independently 0, 1, or 2;
po10 and pp10 are independently 1,2, or 3;
each $P^{12}$ is independently:

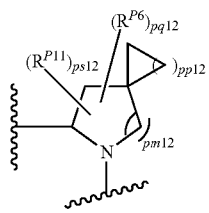

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom,
wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pq12 is independently 0, 1, 2, 3, or 4;
pm12 is independently 0, 1, or 2;
pp12 is independently 1, 2, or 3;
ps12 is 1, 2, 3, or 4;
$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl-, (NR$^{hh}$R$^h$)carbonyl-, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining $R^{P11}$ are independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
each $P^{15}$ is:

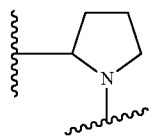 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;
each $P^{18}$ is:

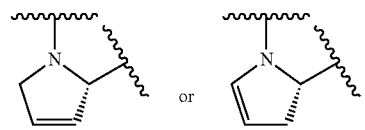 [SMILES: *[C@@H]1C=CCN1* ; *[C@@H]1CC=CN1*]

which is optionally substituted, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl with one or two groups independently selected from halo, alkyl, alkoxyalkyl, haloalkyl, cycloalkyl, and cycloalkylalkyl;

each $P^{19}$ is:

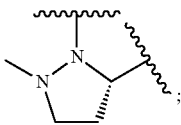

each $P^{30}$ is independently a ring of the formula:

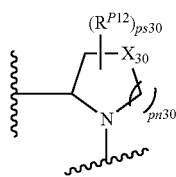

ps30 is 2
pn30 is 0, 1 or 2;
$X_{30}$ is selected from O, S, S(O), $SO_2$, or $CH_2$; provided that when pn is 0, X is $CH_2$.

each $R^{P212}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P212}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl-, ($NR^eR^f$)alkylcarbonyl-, ($NR^eR^f$)carbonyl-, ($NR^eR^f$)sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, ($NR^XR^Y$)alkyl-, and ($NR^XR^Y$)carbonyl-;

$R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl-, wherein $R^{X'}$ and $R^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl-, ($NR^eR^f$)alkylcarbonyl-, ($NR^eR^f$)carbonyl-, ($NR^eR^f$)sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, ($NR^XR^Y$)alkyl-, and ($NR^XR^Y$)carbonyl-; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl-, wherein $R^{X'}$ and $R^{Y'}$ are independently selected from hydrogen and alkyl; or a pharmaceutically acceptable salt or prodrug thereof.

In one specific embodiment the invention provides a compound of formula (I):

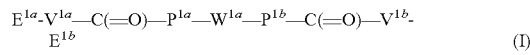
(I)

wherein:
$W^{1a}$ has the formula:

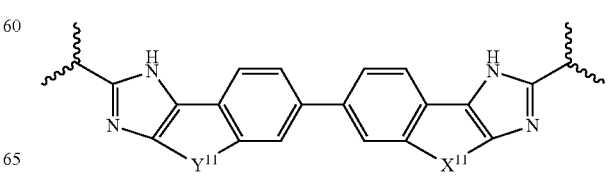

111 wherein:

$X^{11}$ is —CH$_2$—CH$_2$—, —O—CH$_2$—, or —CH=CH—

$Y^{11}$ is —CH=CH— and $W^{1a}$ is optionally substituted with one or more (e.g. 1, 2, 3, or 4) groups independently selected from halo, alkyl, haloalkyl, cyano, and

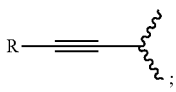

wherein each R is independently H, alkyl, haloalkyl, cycloalkyl, aryl, or heteroaryl;

$E^{1a}$ is $E^0$, $E^1$, or $E^2$, or $E^{1a}$-$V^{1a}$ taken together are $R^{9a}$;

$E^{1b}$ is $E^0$, $E^1$, or $E^2$, or $E^{1b}$-$V^{1b}$ taken together are $R^{9b}$;

$V^{1a}$ is $V^0$ or $E^{1a}$-$V^{1a}$ taken together are $R^{9a}$;

$V^{1b}$ is $V^0$ or $E^{1b}$-$V^{1b}$ taken together are $R^{9b}$;

one of $P^{1a}$ and $P^{1b}$ is

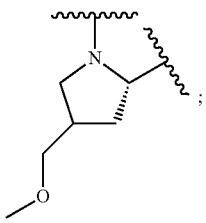

and the other of $P^{1a}$ and $P^{1b}$ is selected:

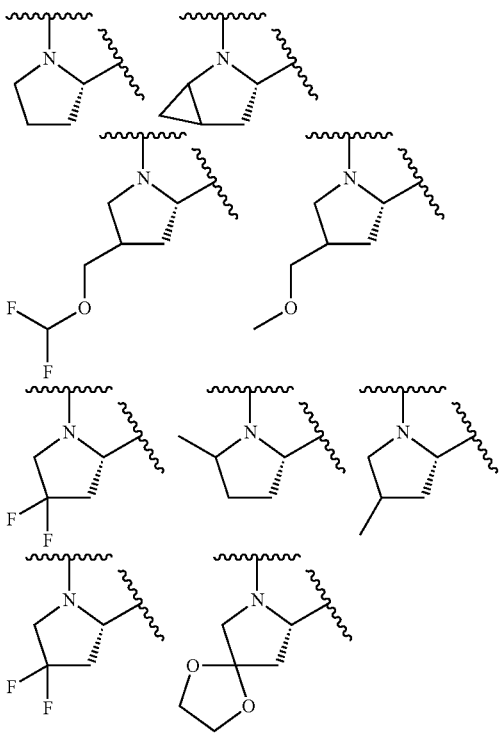

-continued

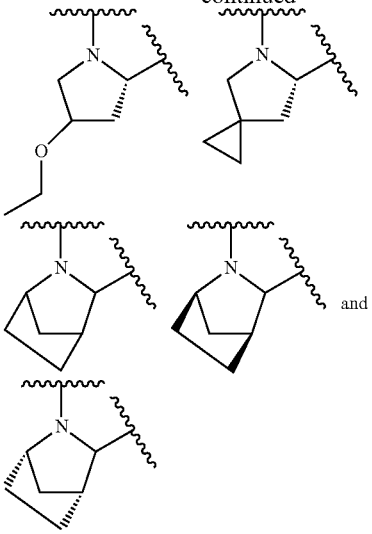

and each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $E^2$ is independently —NHR$^{Ef}$ wherein R$^{Ef}$ is cycloalkylcarbonyl or cycloalkyloxycarbonyl;

each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NR$^{VO1}$R$^{VO1}$COalkyl, wherein each R$^{VO1}$ is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)(OR$^{VO2}$)$_2$, wherein each R$^{VO1}$ is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl-, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each R$^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^X$R$^Y$)alkyl-, and (NR$^X$R$^Y$)carbonyl-; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl-, wherein R$^{X'}$ and R$^{Y'}$ are independently selected from hydrogen and alkyl;

each R$^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^X$R$^Y$)alkyl-, and (NR$^X$R$^Y$)carbonyl-; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl-, wherein R$^{X'}$ and R$^{Y'}$ are independently selected from hydrogen and alkyl; or a pharmaceutically acceptable salt or prodrug thereof.

In one specific embodiment at least one of $E^{1a}$ and $E^{1b}$ is —N(H)(alkoxycarbonyl).

In one specific embodiment at least one of $E^{1a}$ and $E^{1b}$ is —N(H)C(=O)OMe.

In one specific embodiment at least one of $E^{1a}$ and $E^{1b}$ is —N(H)(cycloalkylcarbonyl) or —N(H)(cycloalkyloxycarbonyl).

In one specific embodiment at least one of $E^{1a}$ and $E^{1b}$ is cyclopropylcarbonylamino, cyclobutylcarbonylamino, cyclopropyloxycarbonylamino or cyclobutyloxycarbonylamino.

In one specific embodiment $E^{1a}$ and $E^{1b}$ are each independently selected from cyclopropylcarbonylamino, cyclobutylcarbonylamino, cyclopropyloxycarbonylamino and methoxycarbonylamino.

In one specific embodiment at least one of $V^{1a}$ and $V^{1b}$ is $V^0$.

In one specific embodiment at least one of $V^{1a}$ and $V^{1b}$ is selected from:

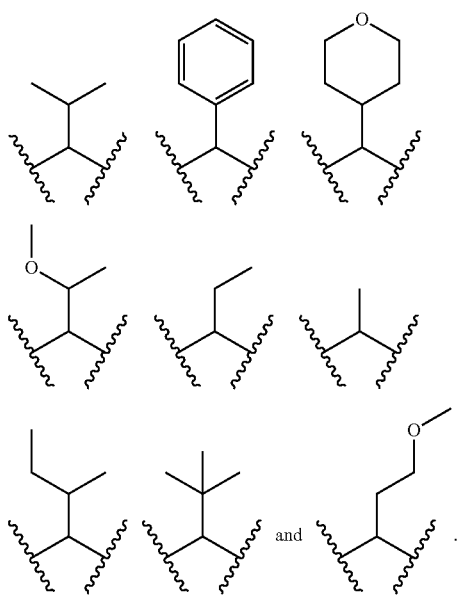

In one specific embodiment at least one of $V^{1a}$ and $V^{1b}$ is selected from:

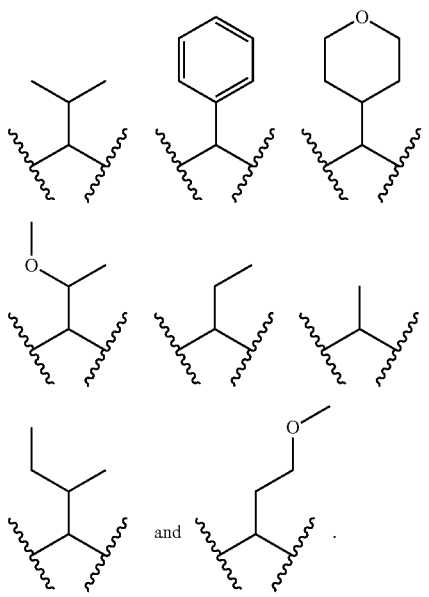

In one specific embodiment at least one of $V^{1a}$ and $V^{1b}$ is:

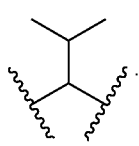

In one specific embodiment at least one of $V^{1a}$ and $V^{1b}$ is selected from:

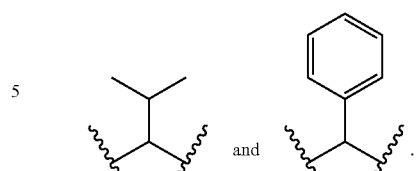

In one specific embodiment at least one of $V^{1a}$ and $V^{1b}$ is selected from:

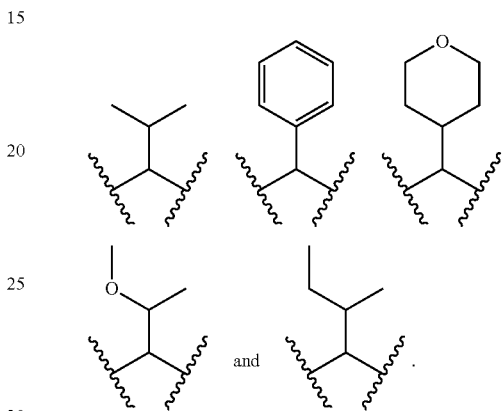

In one specific embodiment $V^{1a}$ and $V^{1b}$ are each independently selected from:

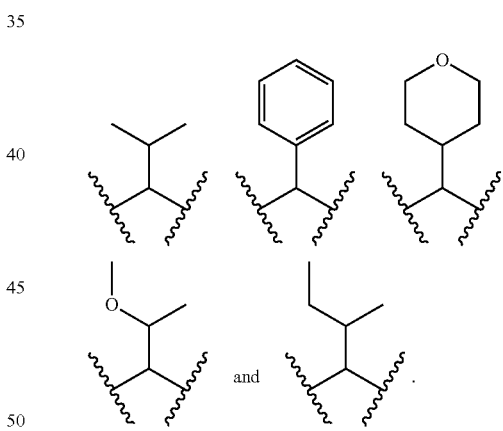

In one specific embodiment at least one of $P^{1a}$ and $P^{1b}$ is $P^0$.

In one specific embodiment one of $P^{1a}$ and $P^{1b}$ is

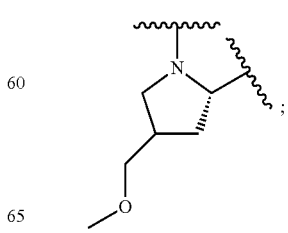

and the other of $P^{1a}$ and $P^{1b}$ is selected from:

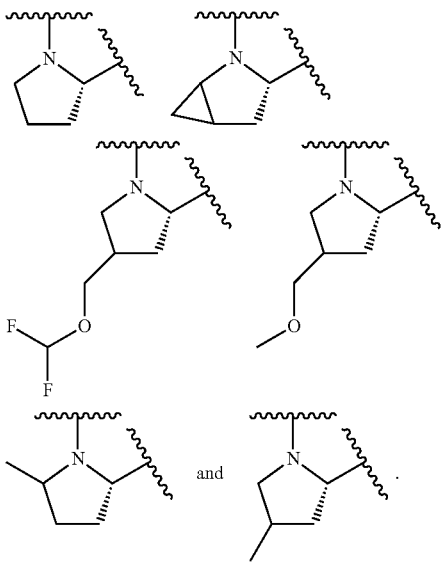

In one specific embodiment at least one of $P^{1a}$ and $P^{1b}$ is selected from:

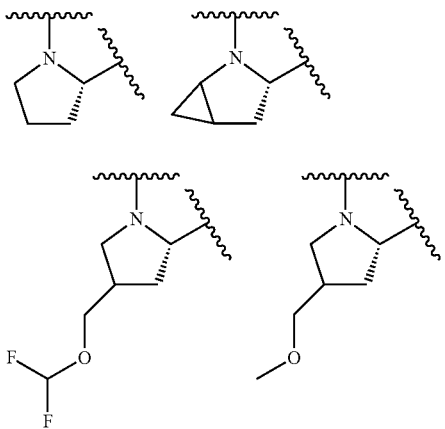

-continued

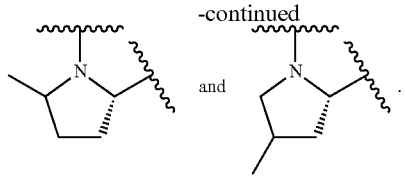

In one specific embodiment at least one of $P^{1a}$ and $P^{1b}$ is:

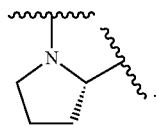

In one specific embodiment $P^{1a}$ and $P^{1b}$ are each independently selected from:

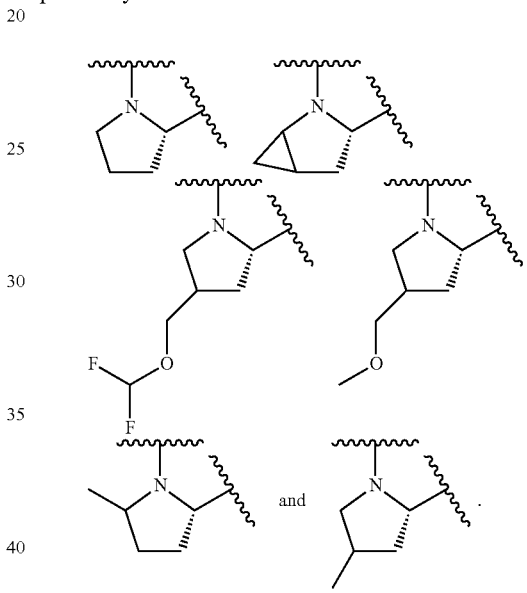

In one specific embodiment the invention provides a compound prepared in the Examples herein that is a compound of specific Embodiment B, or a salt or a prodrug thereof.

In one specific embodiment the invention provides the compound:

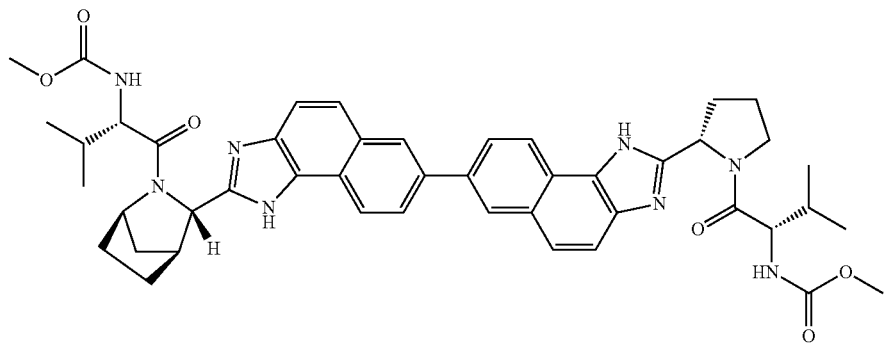

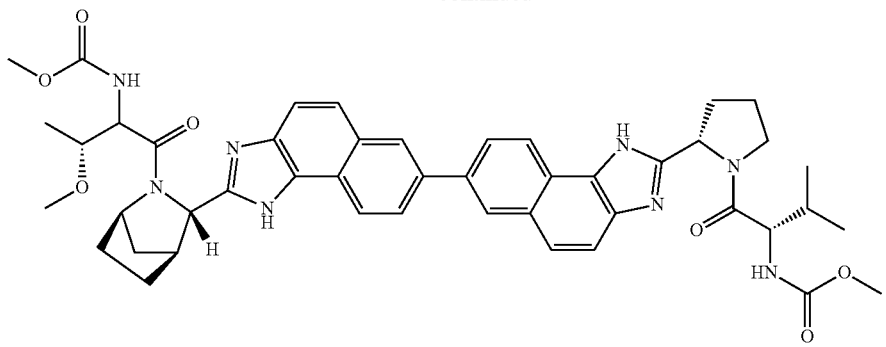
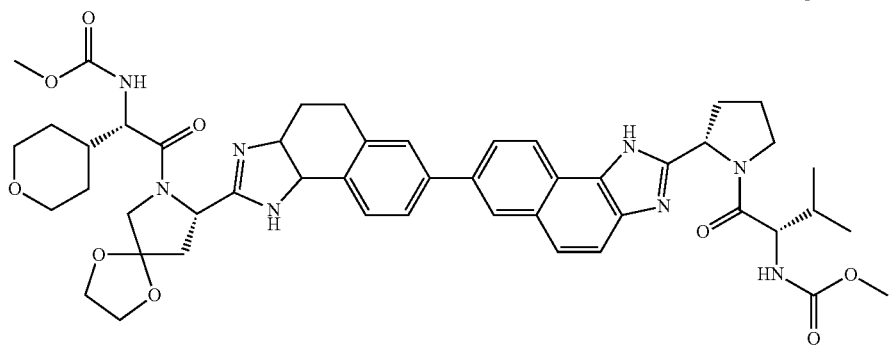
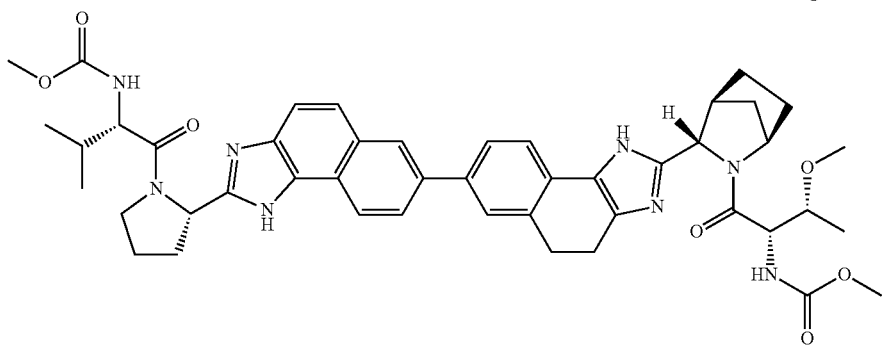
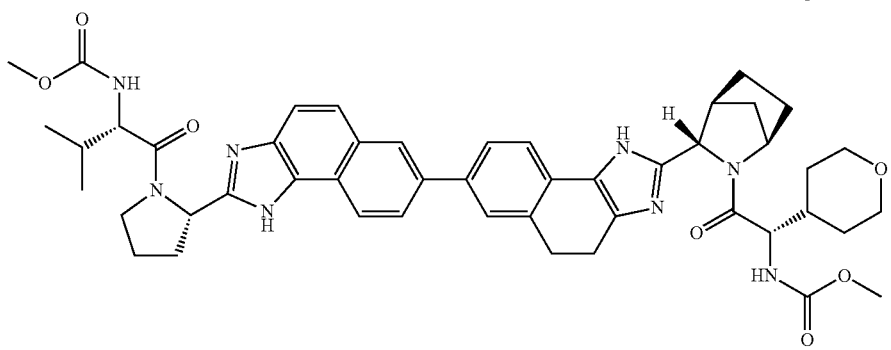
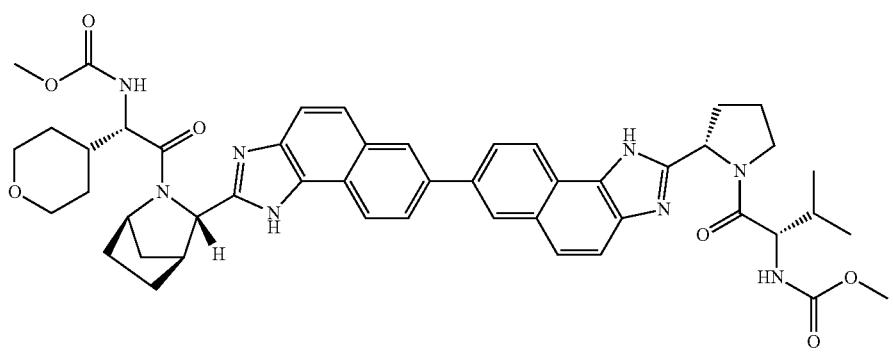

-continued
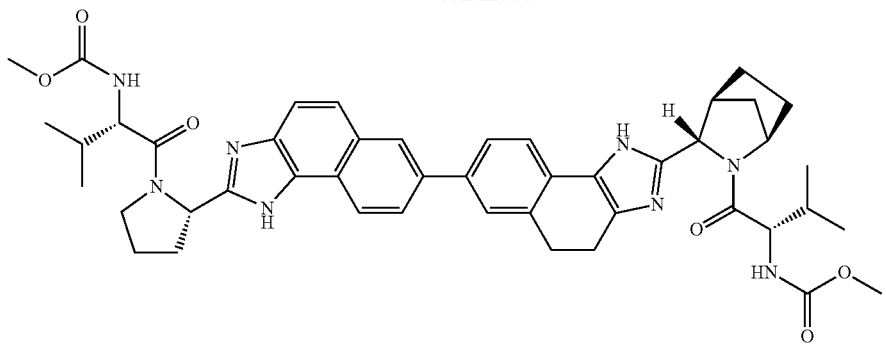
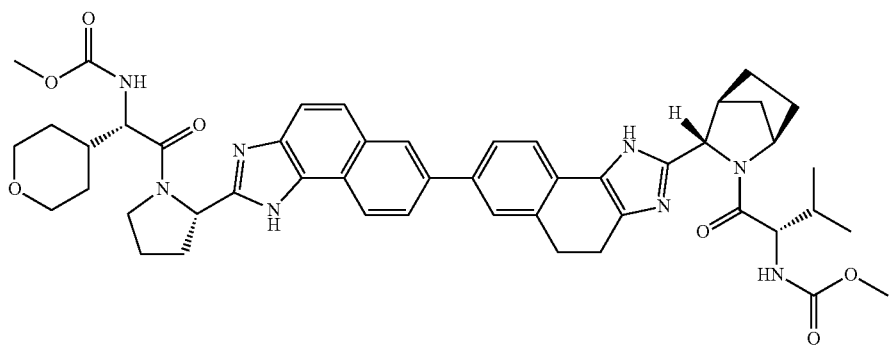
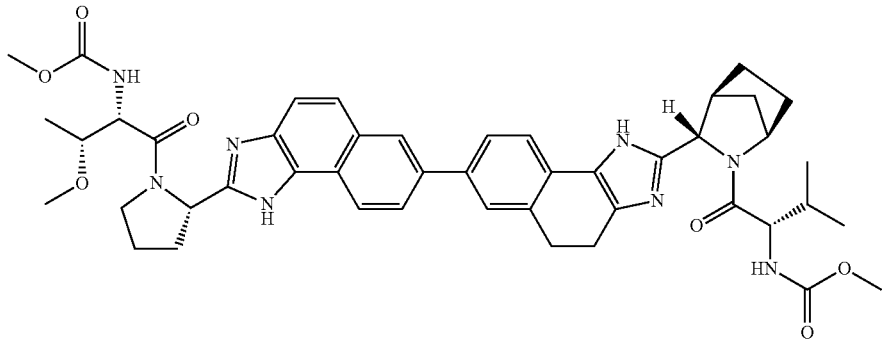
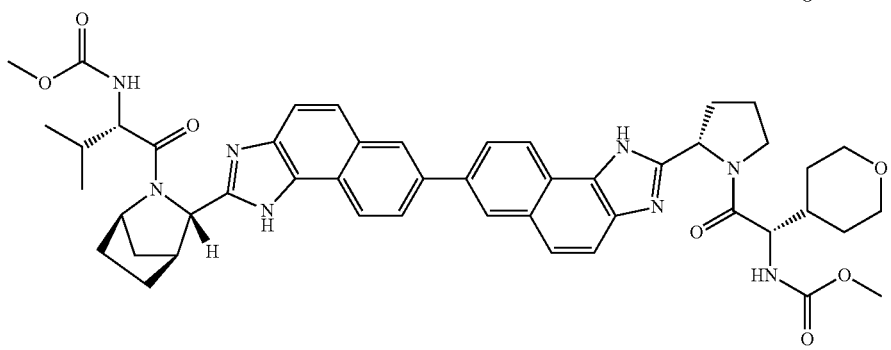
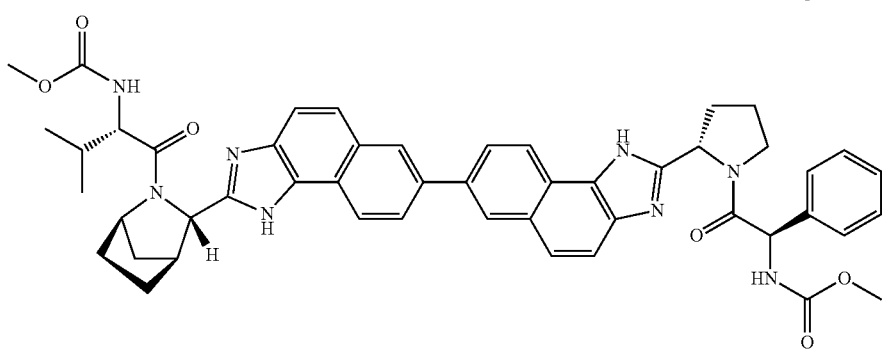

-continued
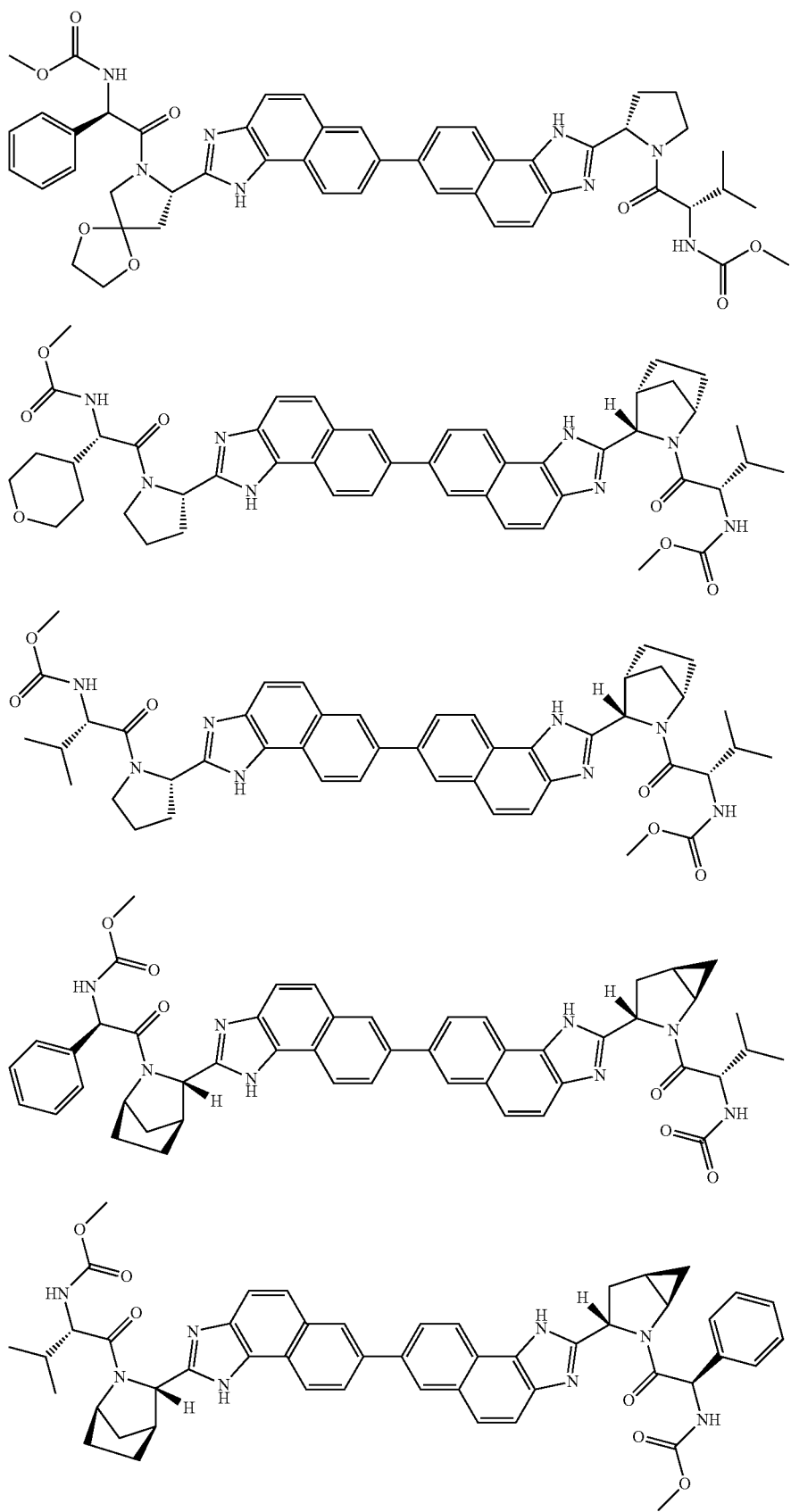

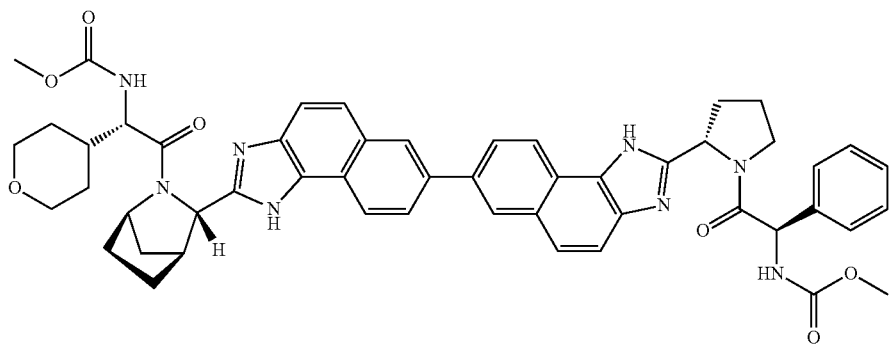
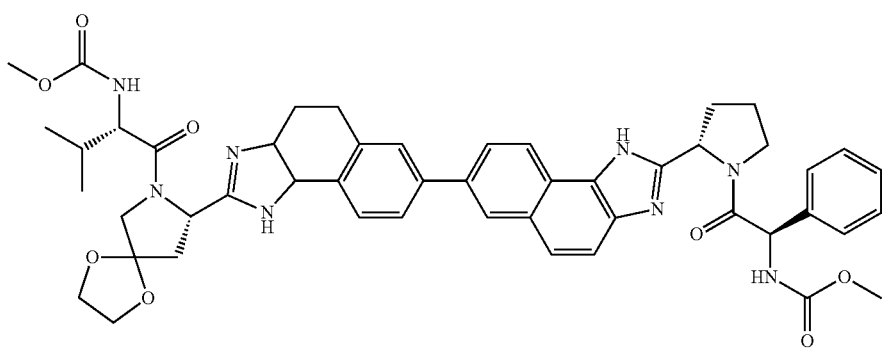
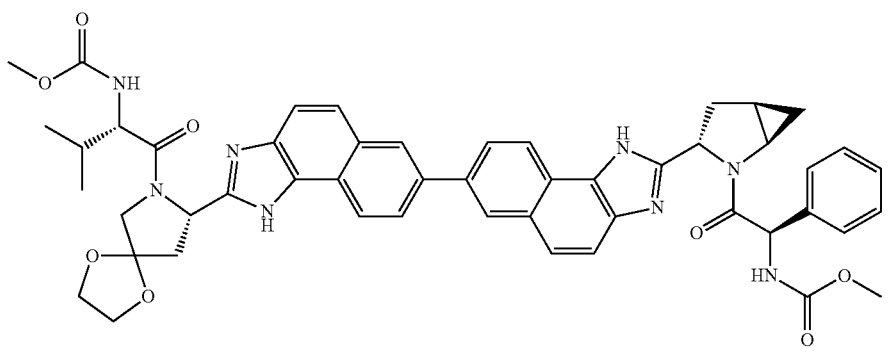
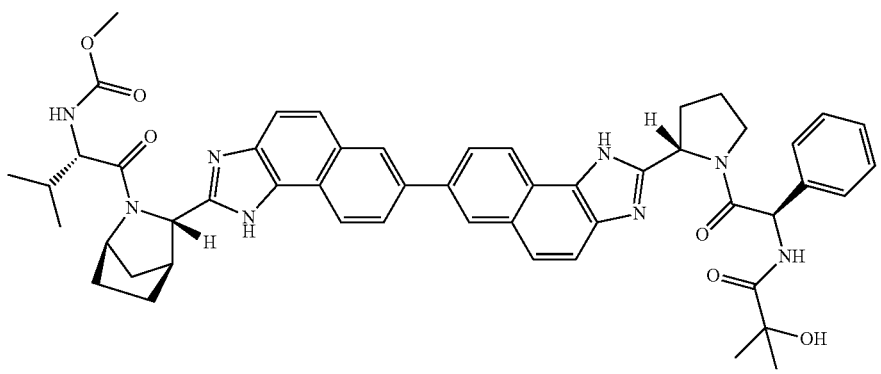

-continued
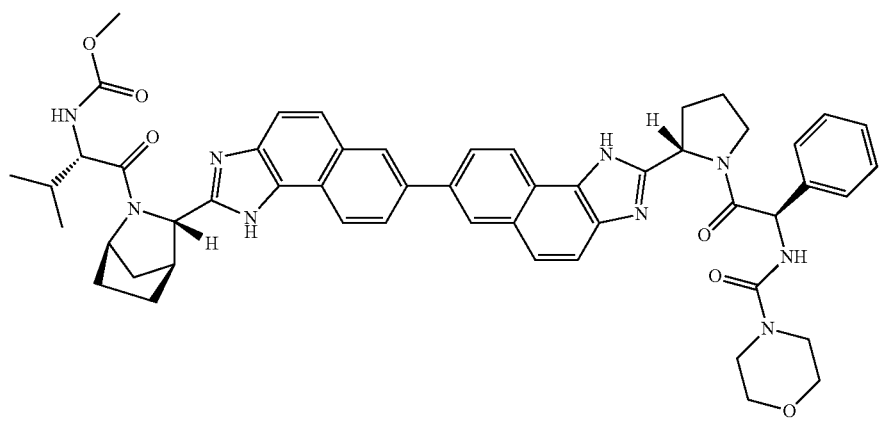
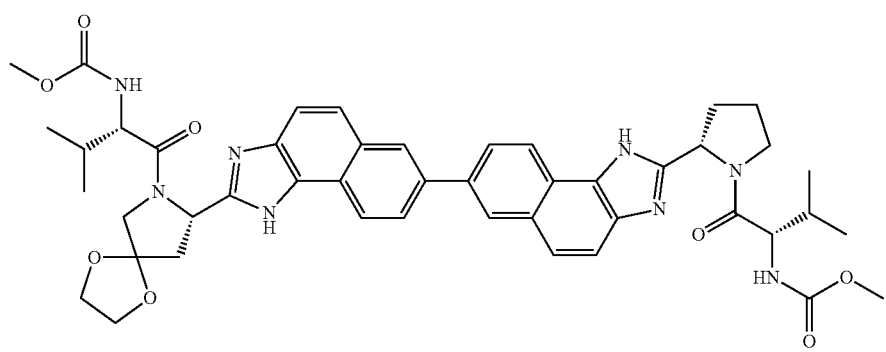
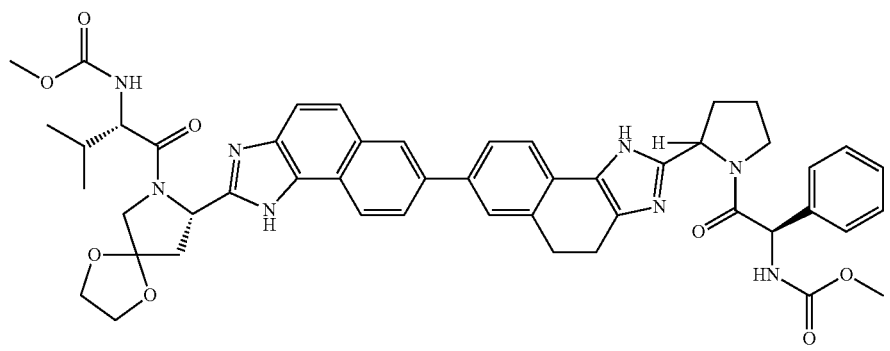
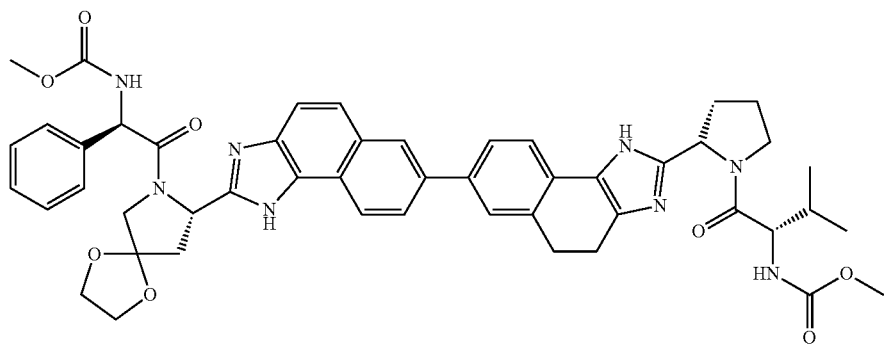

517 518
-continued
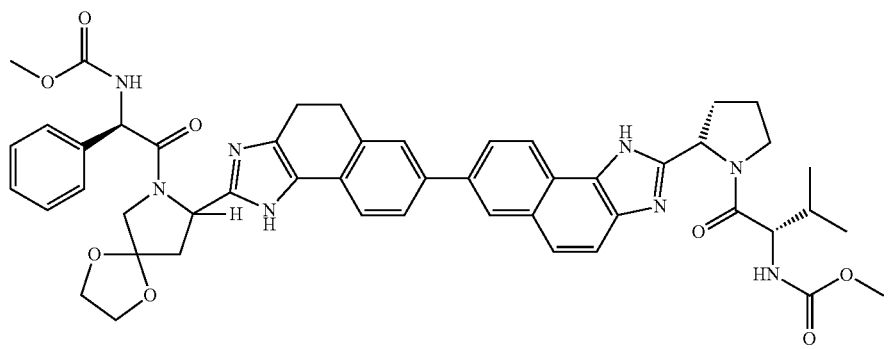
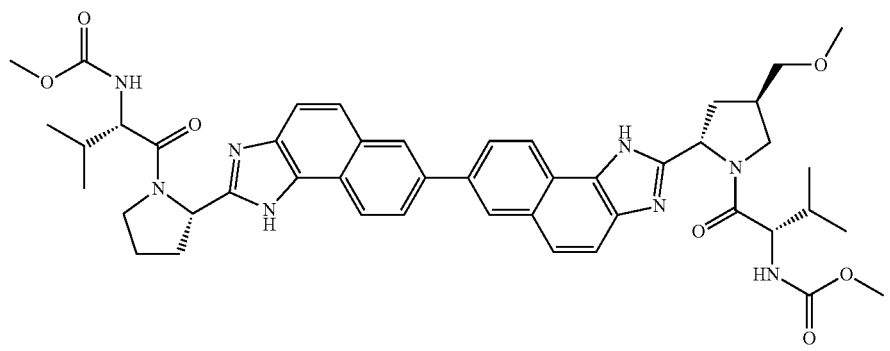
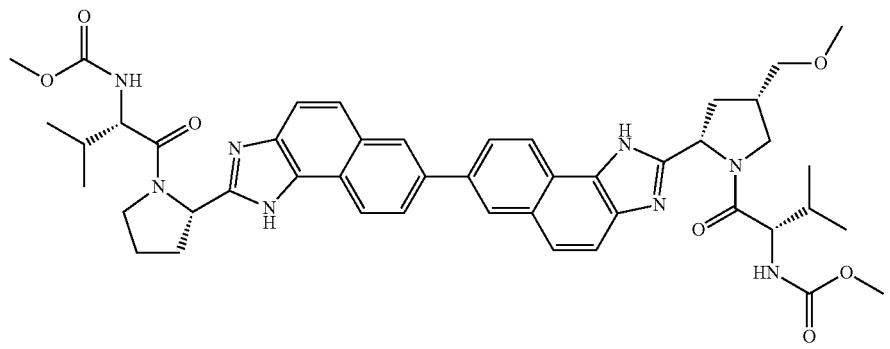
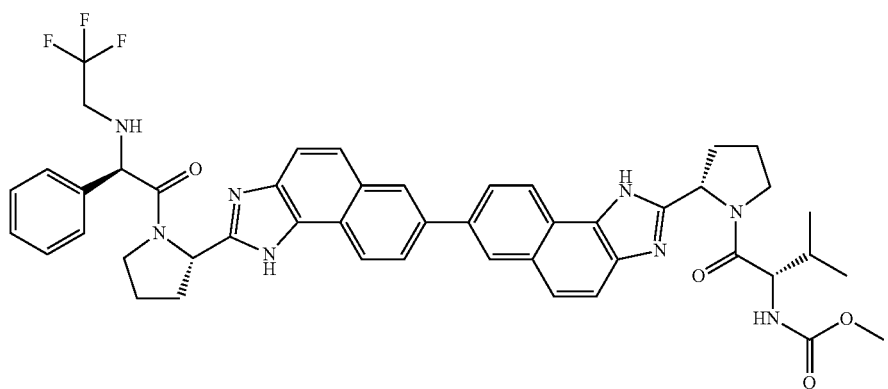
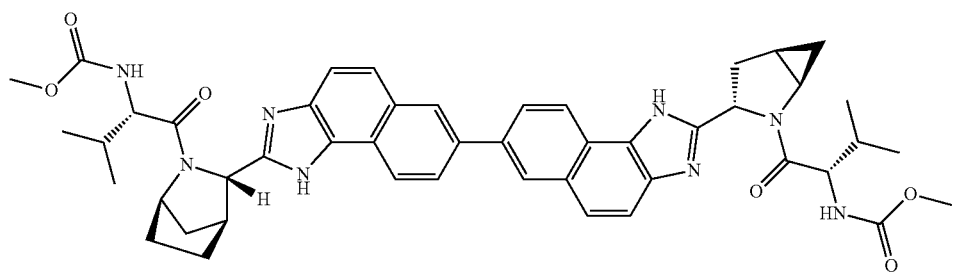

-continued
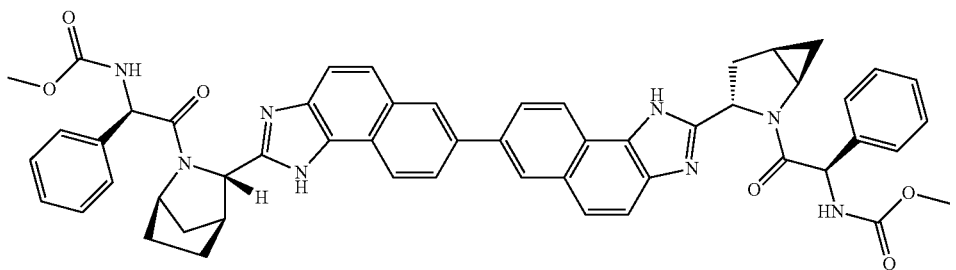
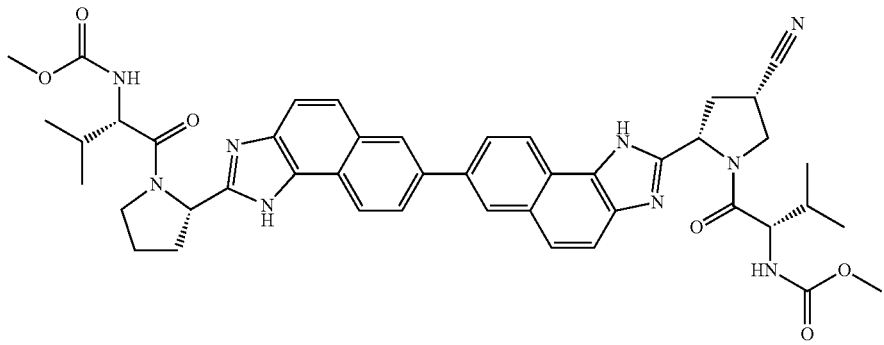
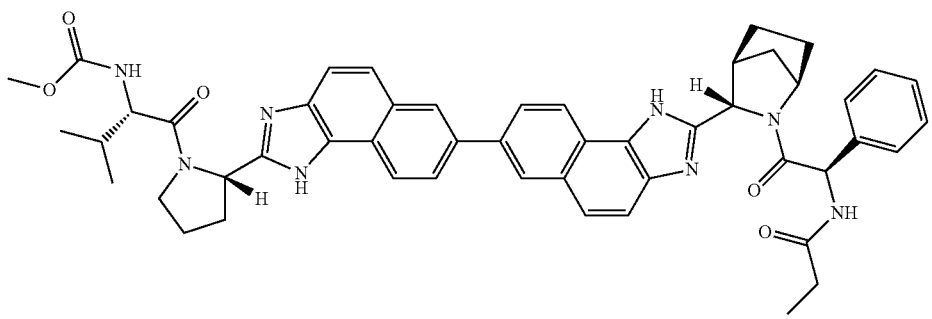
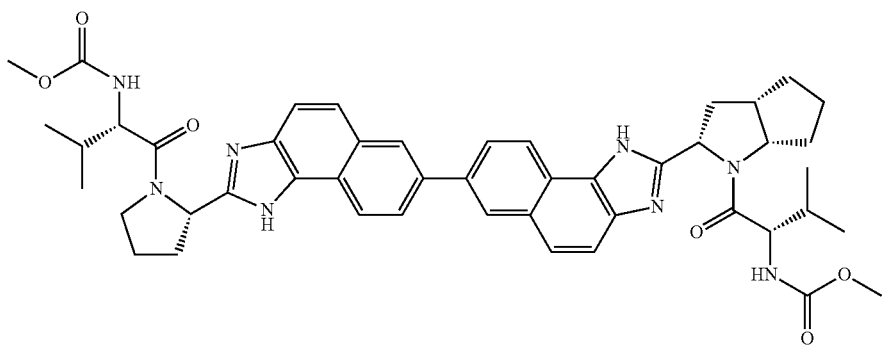
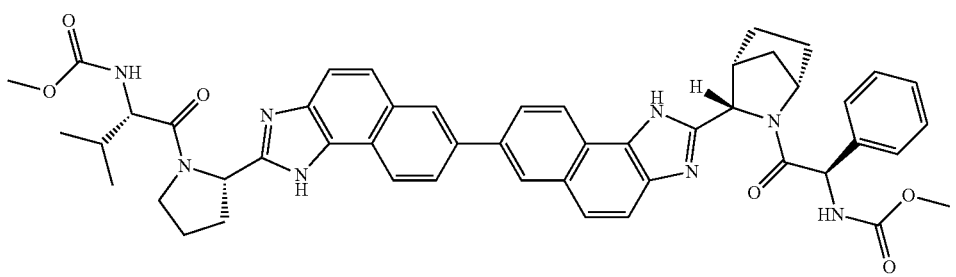

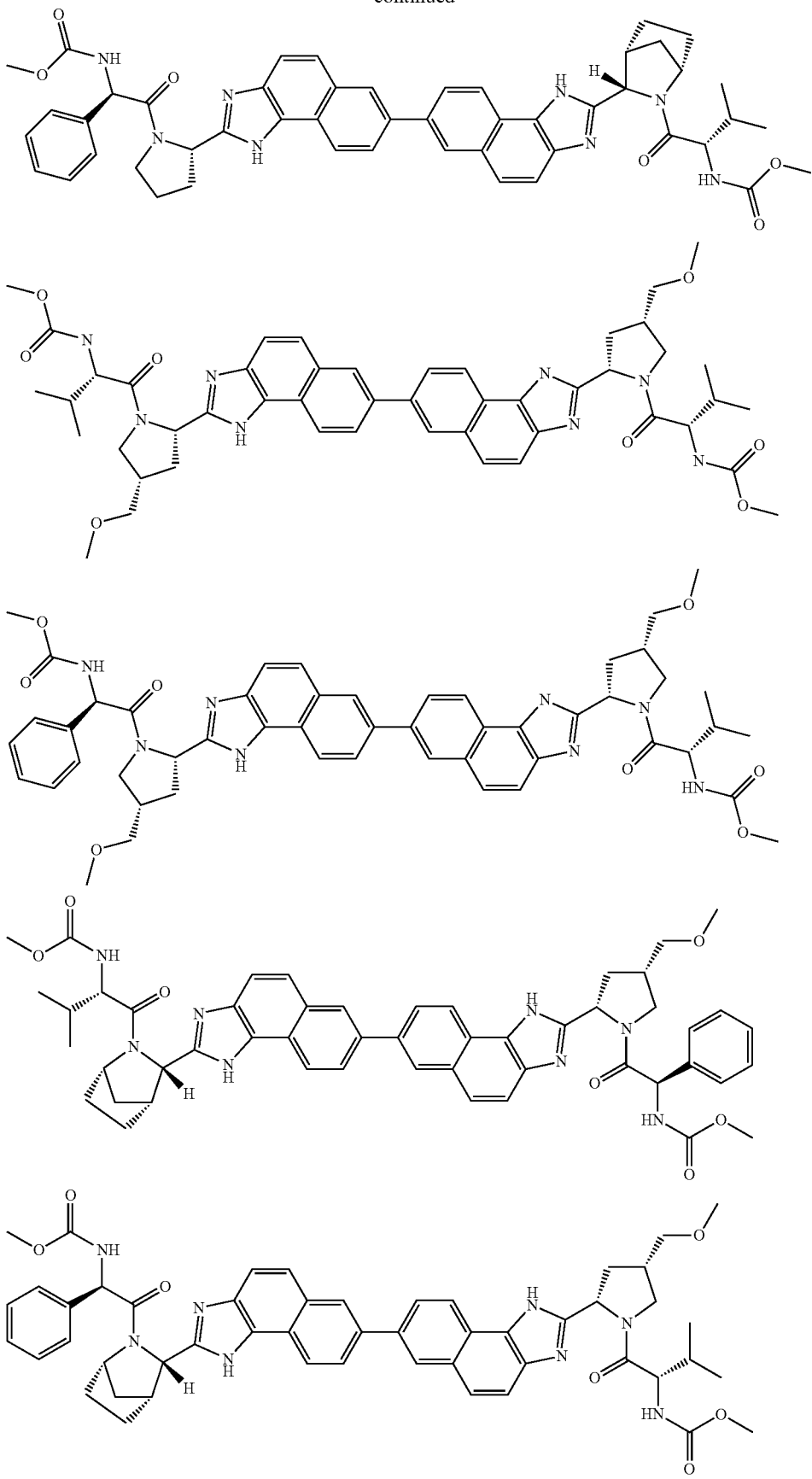

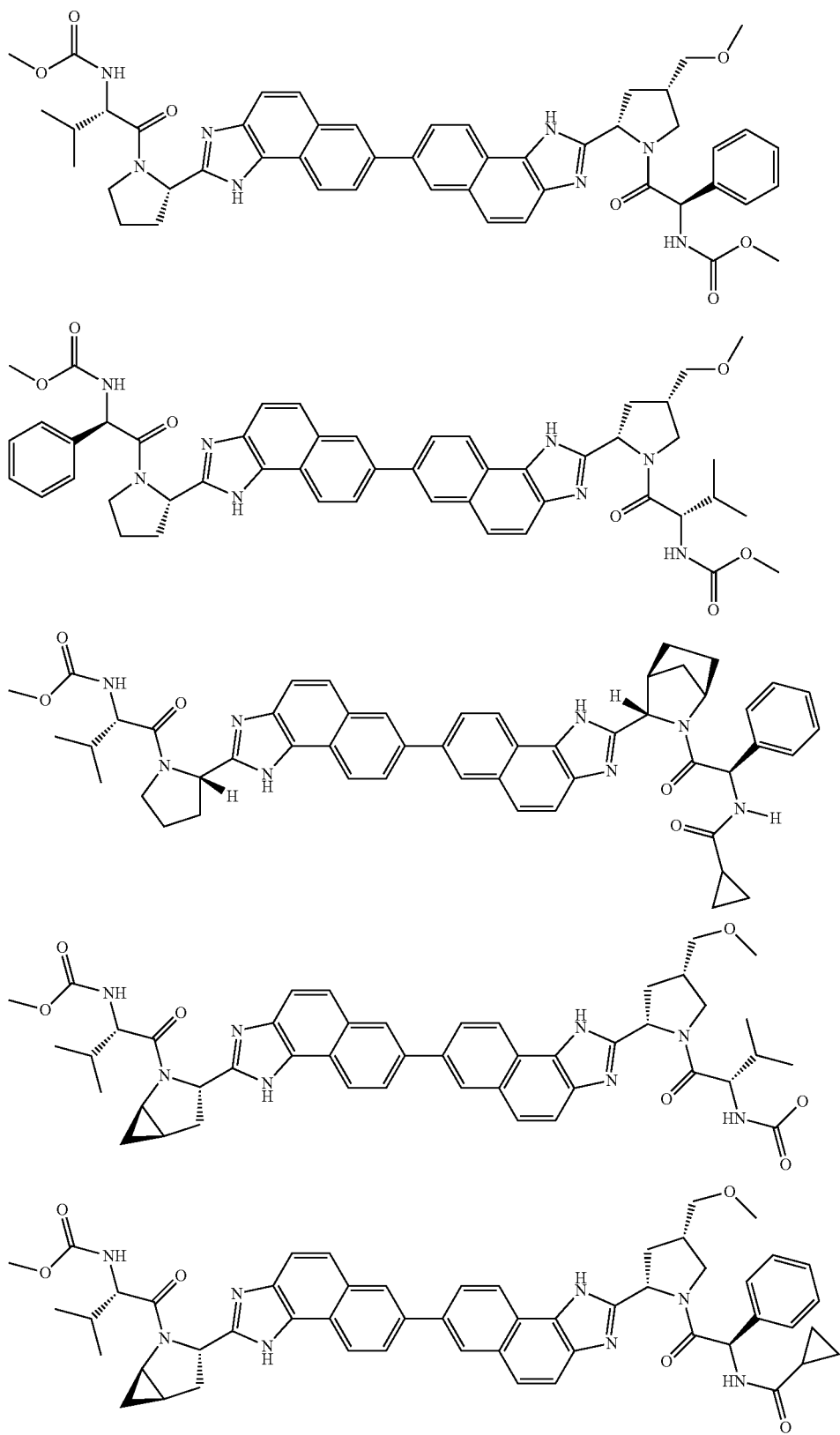

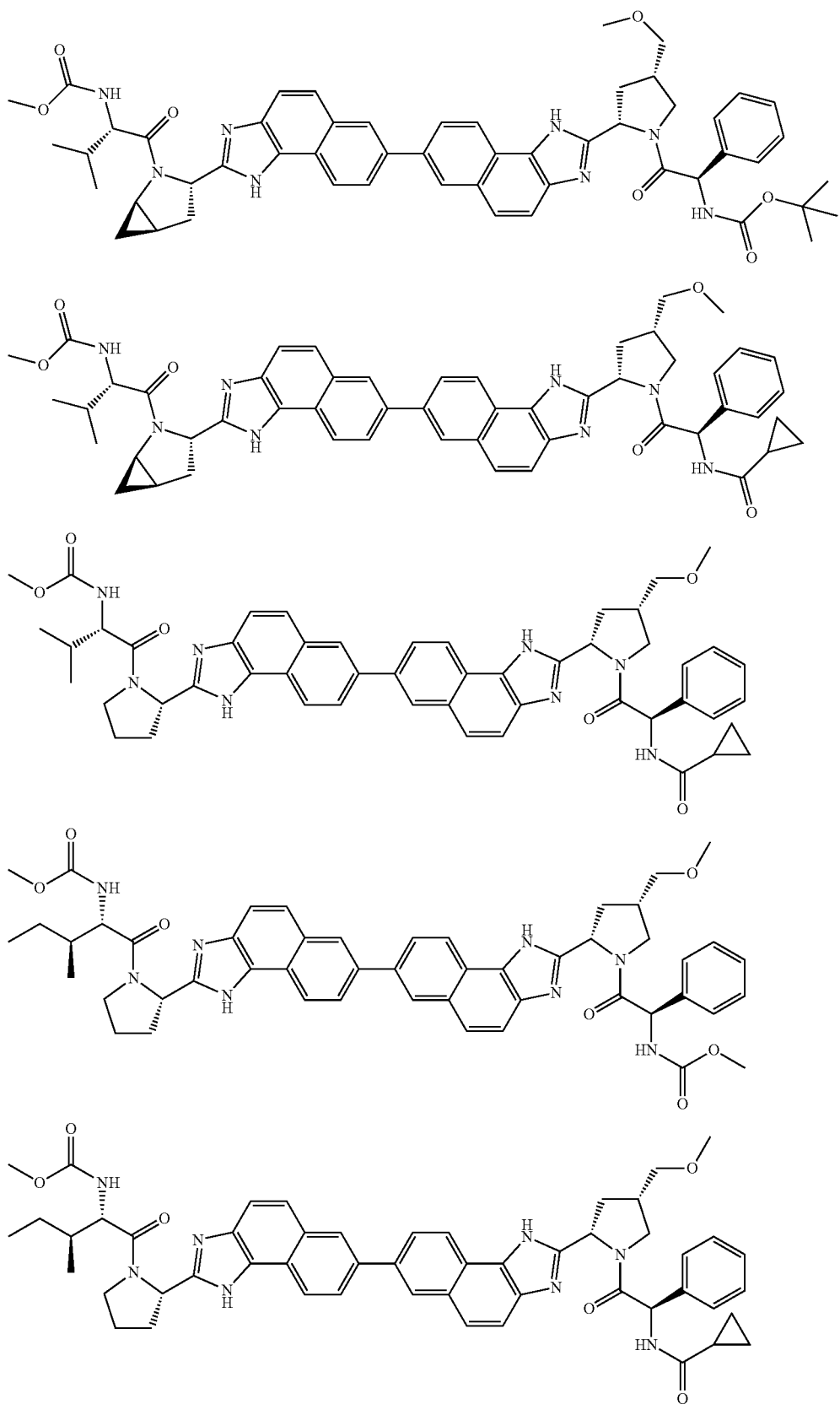

-continued
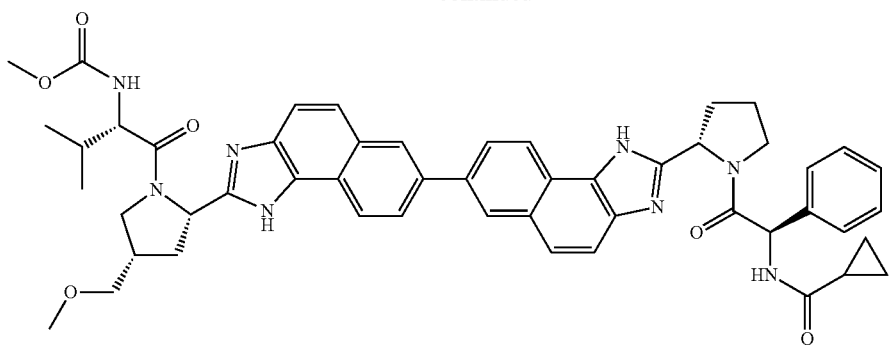
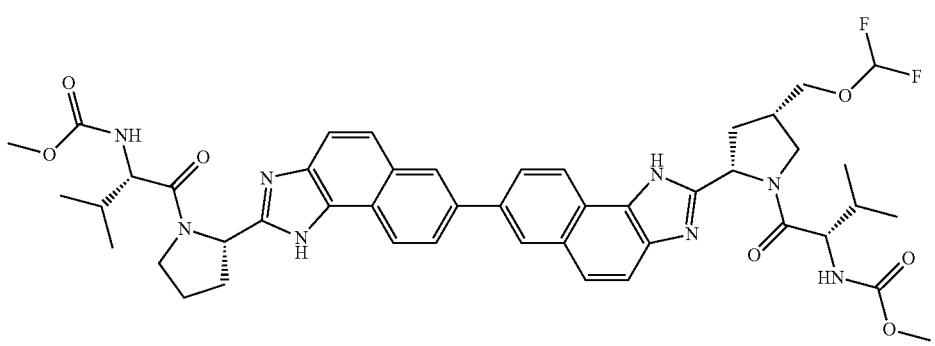
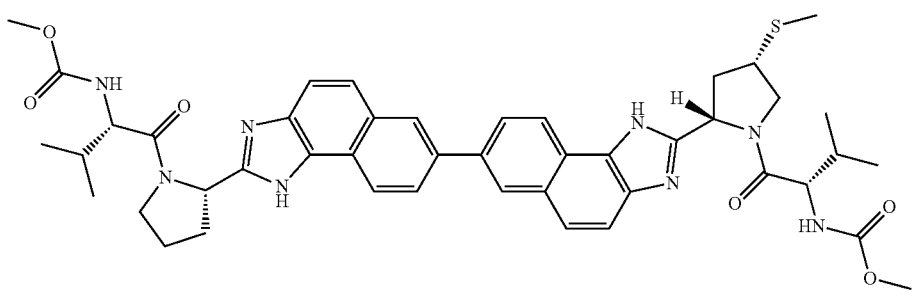
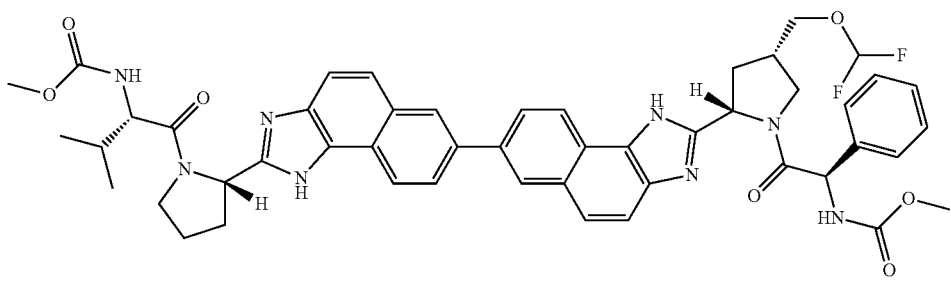
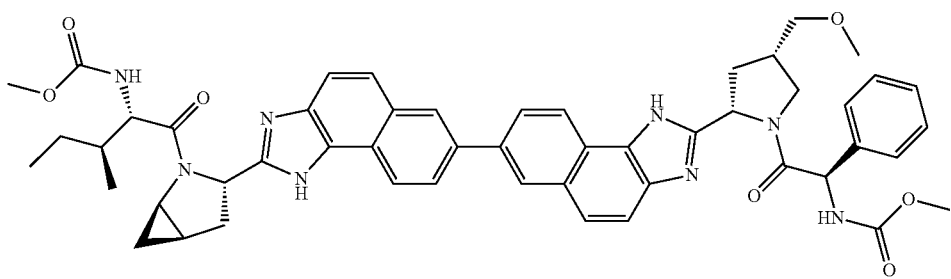

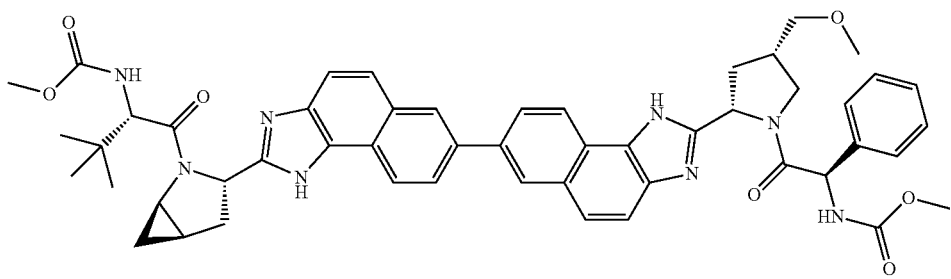
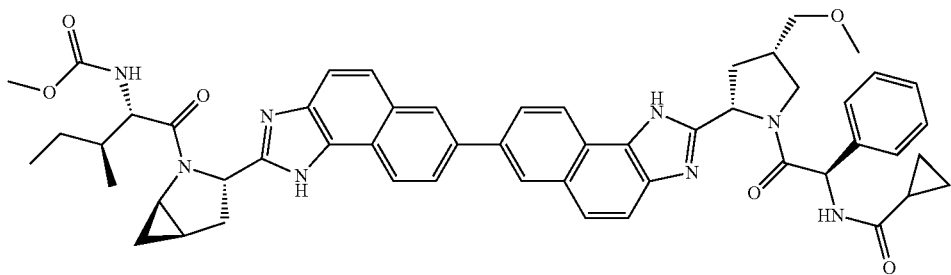
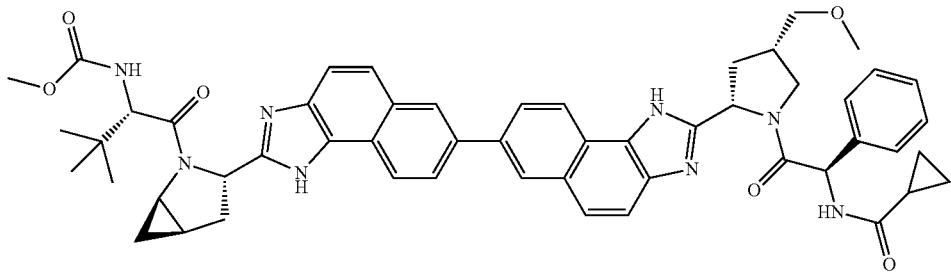
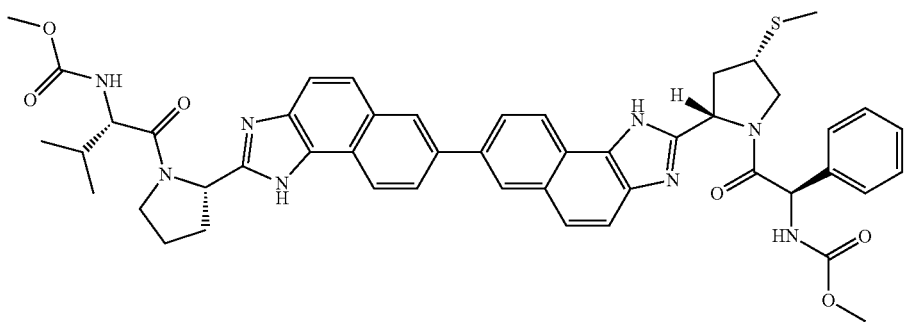
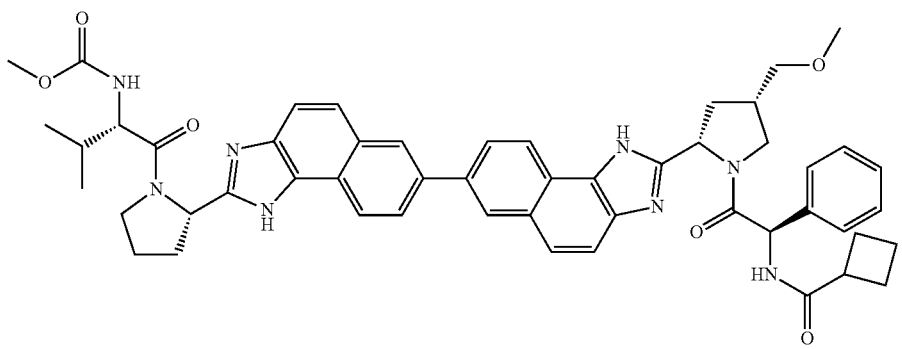

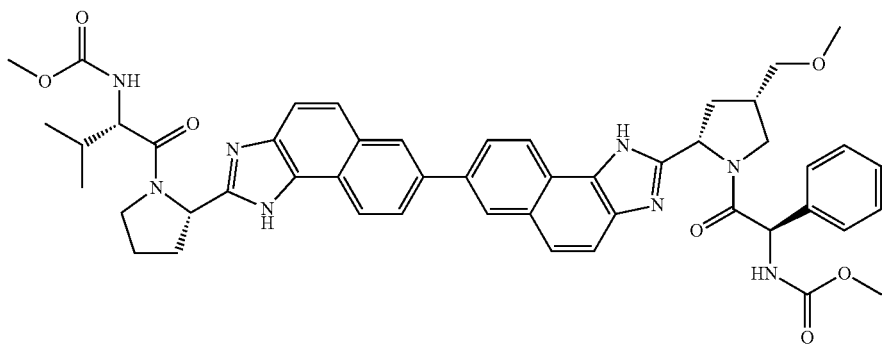
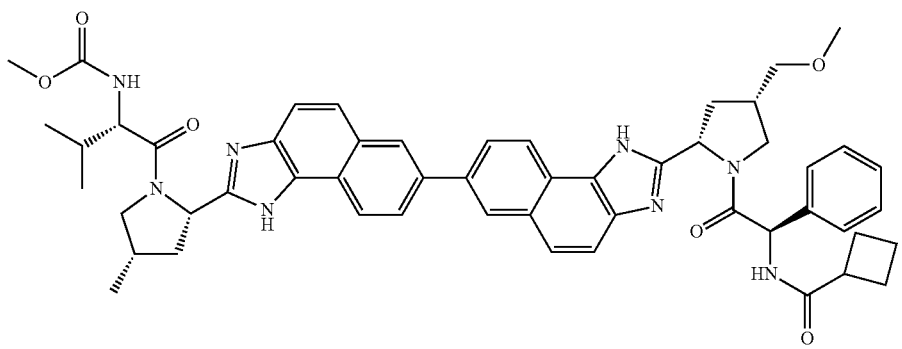
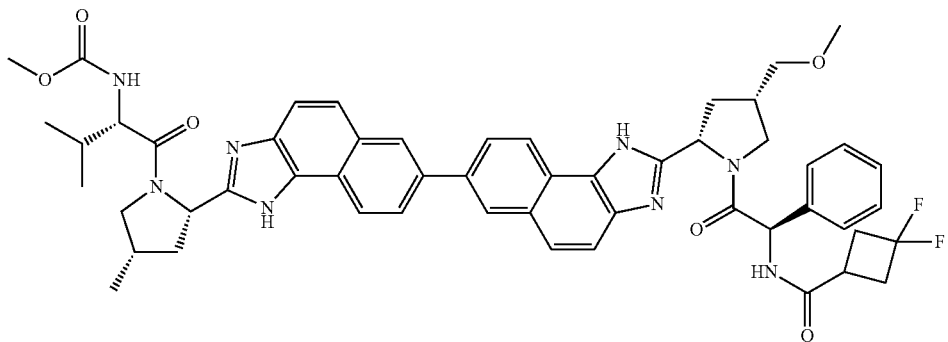
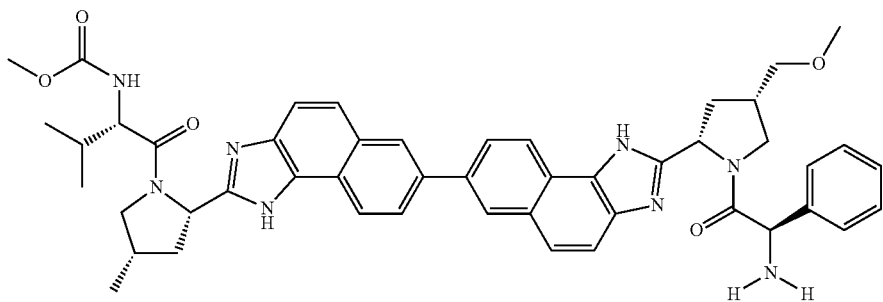
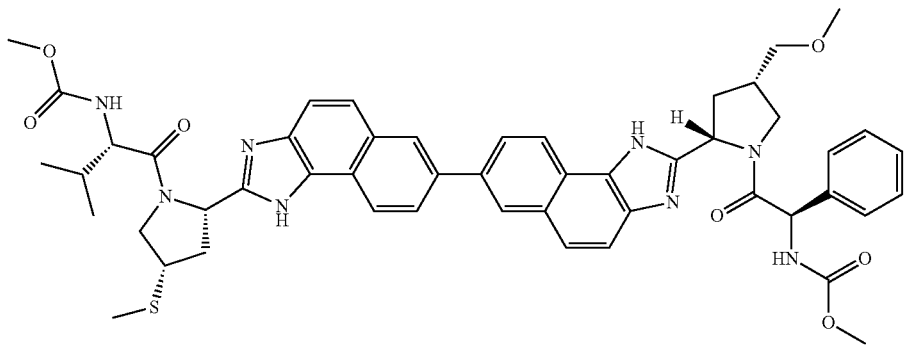

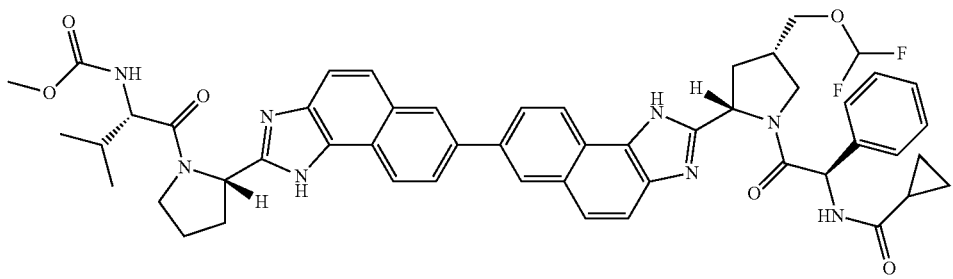
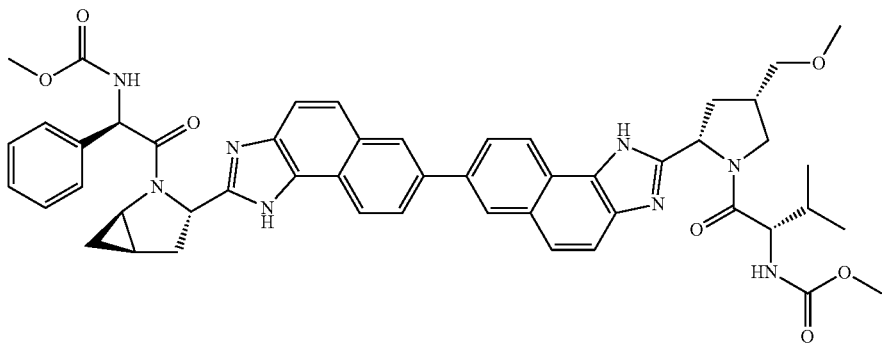
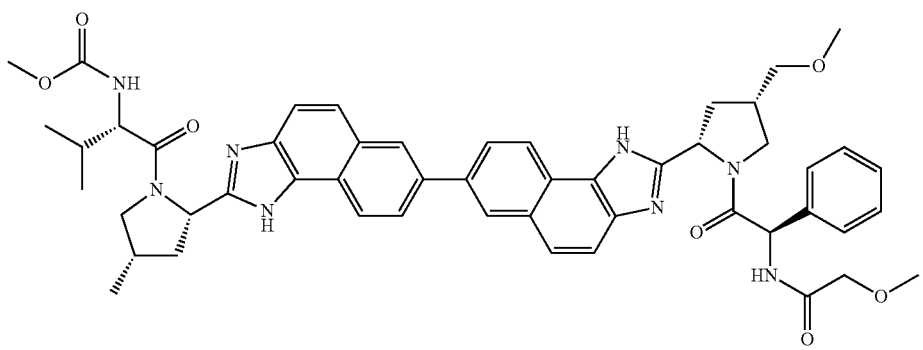
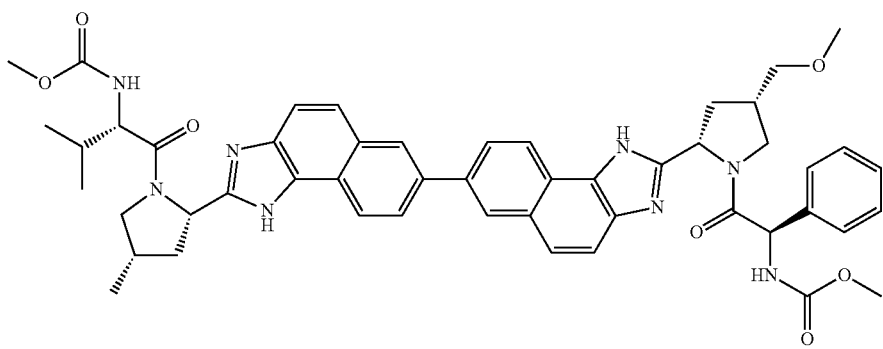
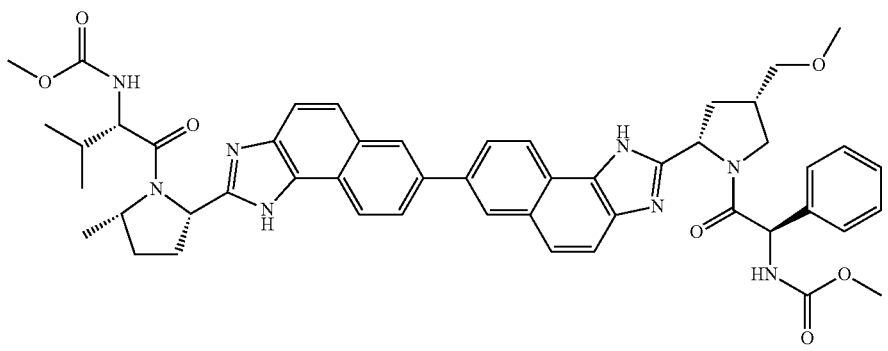

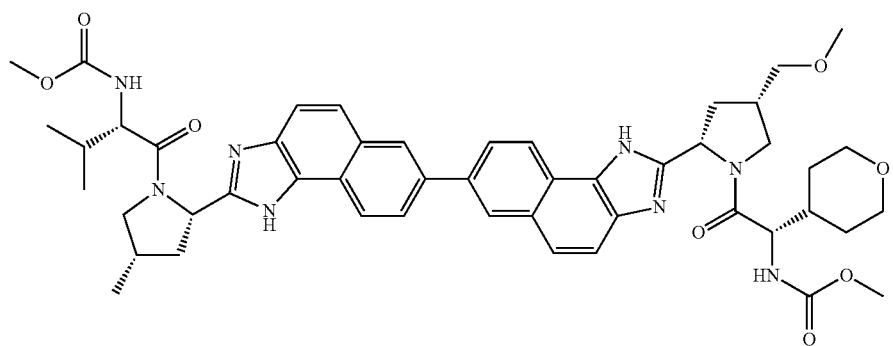
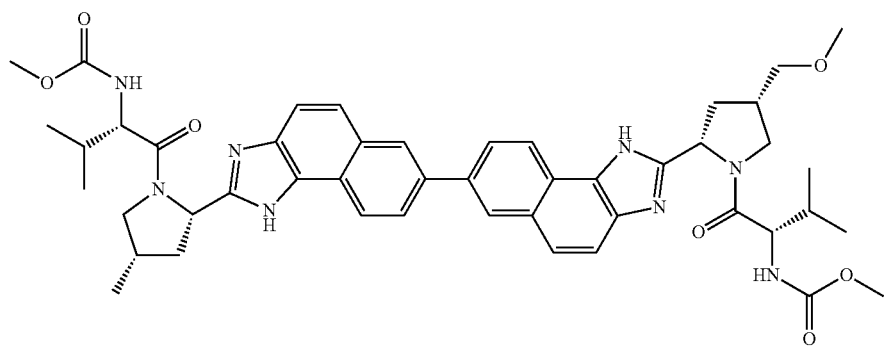
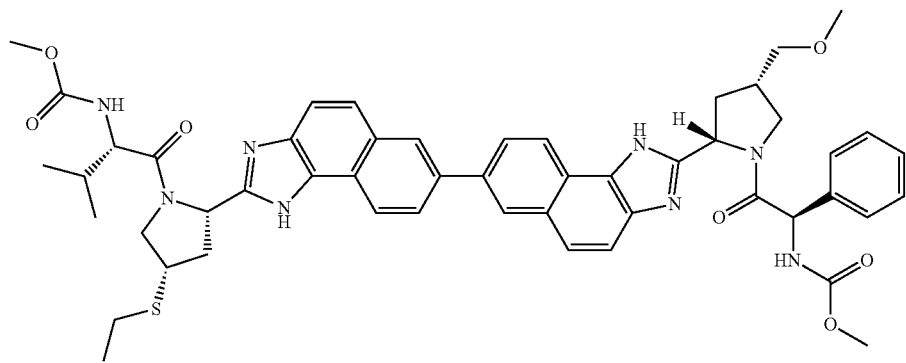
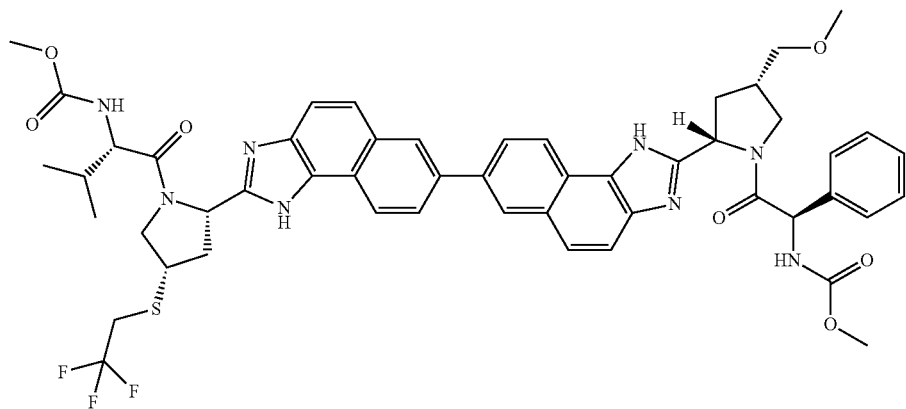

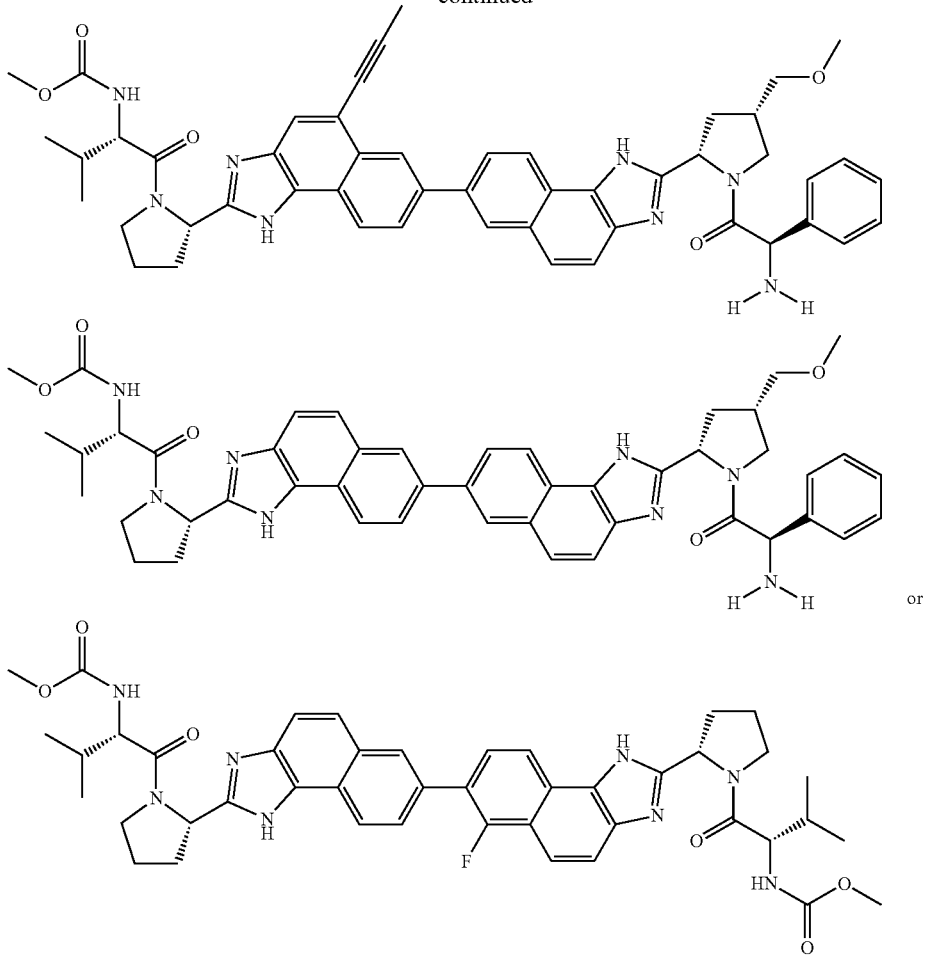

or a pharmaceutically acceptable salt or prodrug thereof.

Specific Embodiment C

In one specific embodiment the invention provides a compound of formula (I):

$$E^{1a}\text{-}V^{1a}\text{—}C(=O)\text{—}P^{1a}\text{—}W^{1a}\text{—}P^{1b}\text{—}C(=O)\text{—}V^{1b}\text{-}E^{1b} \quad (I)$$

wherein:

$W^{1a}$ is:

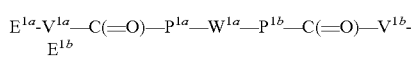

118 wherein $W^{1a}$ is optionally substituted with one or more (e.g. 1, 2, 3, or 4) groups independently selected from halo, alkyl, haloalkyl, cyano, and

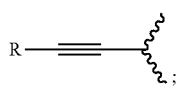

wherein each R is independently H, alkyl, haloalkyl, cycloalkyl, aryl, or heteroaryl;

$X^{18}$ is —CH=CH—, —CH$_2$CH$_2$—, or —OCH$_2$—;

$Y^{18}$ is selected from $A^0, A^1, A^2, A^3, A^7, A^{15}, A^{16}$, and $A^{20}$;

each $A^0$ is independently:

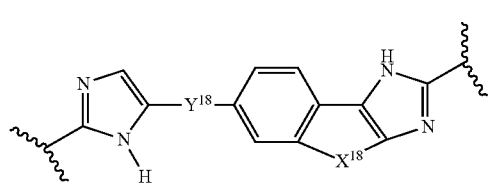

wherein:

each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or each $A^0$ is independently a six-membered heteroaromatic ring containing one, two, or three nitrogen atoms, which ring is optionally substituted with 1, 2, 3, or 4 $R^{43}$ groups;

each $A^1$ is independently:

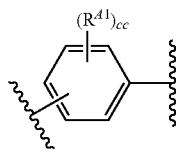

wherein:

each $R^{41}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and each $R^4$ is independently selected from H, alkyl, haloalkyl, aryl, and arylalkyl;

each cc is independently 1, 2, 3, or 4;

each $A^2$ is independently:

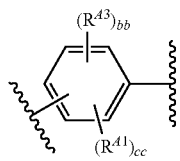

wherein:

each $R^{41}$ is independently selected from cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, ($NR^aR^b$)alkyl, and ($NR^aR^b$)carbonyl; $R^a$ and $R^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each $R^4$ is independently selected from H, alkyl, haloalkyl, aryl, and arylalkyl;

$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each bb is 0, 1, 2, 3, or 4; each cc is 1, 2, 3, or 4; and the sum of bb and cc is 1, 2, 3, or 4;

each $A^3$ is independently a six-membered heteroaromatic ring containing one, two, or three nitrogen atoms, which ring is substituted with one or more $R^{41}$ groups, and which ring is optionally substituted with one or more $R^{43}$ groups;

each $A^7$ is independently:

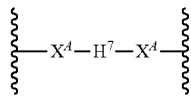

wherein:

each $H^7$ is independently a five-membered heteroaromatic ring, which $H^7$ is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent; and each R is independently selected from H or alkyl;

each $A^{15}$ is independently:

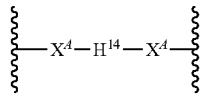

wherein:

each $H^{14}$ is independently a fused unsaturated, partially unsaturated or saturated tricyclic carbocycle which is optionally substituted with one or more groups independently selected from oxo, $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^{16}$ is independently:

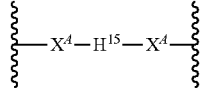

wherein:

each $H^{15}$ is independently a fused unsaturated, partially unsaturated or saturated tricyclic heterocycle that comprises at least one heteroatom in the ring system, which ring system is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^{20}$ is independently a 5 or 6 membered heteroaryl ring that is optionally substituted with one or more groups independently selected from $R^{41}$ and $R^{43}$;

$E^{1a}$ is $E^0$, $E^1$, or $E^2$, or $E^{1a}$-$V^{1a}$ taken together are $R^{9a}$;

$E^{1b}$ is $E^0$, $E^1$, or $E^2$, or $E^{1b}$-$V^{1b}$ taken together are $R^{9b}$;

$V^{1a}$ is $V^0$ or $E^{1a}$-$V^{1a}$ taken together are $R^{9a}$;

$V^{1b}$ is $V^0$ or $E^{1b}$-$V^{1b}$ taken together are $R^{9b}$;

one of $P^{1a}$ and $P^{1b}$ is

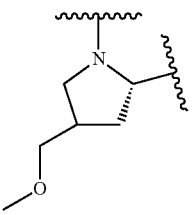

and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$;

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $E^2$ is independently —NHR$^{Ef}$ wherein R$^{Ef}$ is cycloalkylcarbonyl or cycloalkyloxycarbonyl;

each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NR$^{VO1}$R$^{VO1}$COalkyl, wherein each R$^{VO1}$ is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)(OR$^{VO2}$)$_2$, wherein each R$^{VO1}$ is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl-, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $P^0$ is independently:

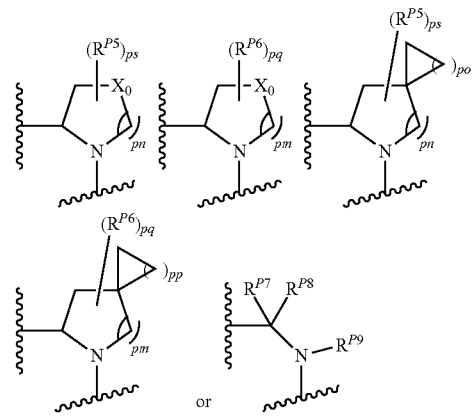

wherein:

$X_0$ is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;

pm and pn are independently 0, 1, or 2;

po and pp are independently 1, 2, or 3;

R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pz}$, O, and S; wherein R$^{Pz}$ is selected from hydrogen and alkyl;

R$^{P9}$ is selected from hydrogen and alkyl;

each P¹ is independently:

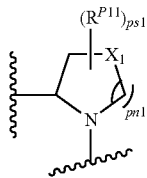

wherein:
$X_1$ is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl-, wherein each R$^h$ is independently —H, alkyl, alkoxyamino, aryl, arylalkyl, heterocycle, heterocyclyloxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P100}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo and heterocyclyl; wherein each R$^h$ is independently —H, alkyl, alkoxyamino, aryl, arylalkyl, heterocycle, heterocyclyloxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{P100}$ is independently selected from alkoxy, alkyl, aryl, halo, haloalkyl, hydroxy, and —NR$^{P101}$R$^{P102}$, wherein the alkyl can optionally form a fused three- to six-membered ring with an adjacent carbon atom, wherein the three- to six-membered ring is optionally substituted with one or two alkyl groups; and R$^{P101}$ and R$^{P102}$ are each independently H, alkyl, aryl, or arylalkyl; or R$^{P101}$ and R$^{P102}$ taken together with the atom to which they are attached form a heterocycle;

ps1 is 1, 2, 3, or 4;
pn1 is 0, 1, or 2;
each P³ is independently a ring of the formula:

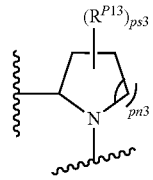

wherein:
the ring is substituted with one or more oxo group;
each R$^{P13}$ is independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring;
ps3 is 0, 1, 2, 3, or 4;
pn3 is 0, 1, or 2;
each P⁵ is independently a ring of the formula:

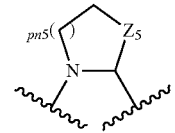

wherein:
the ring is optionally substituted with one or more groups R$^{P15}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups R$^{P15}$ that are attached to the same carbon when taken together with the carbon to which they are attached can form a 3-6 membered carbocyclic or heterocyclic ring;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pn3 is 0, 1, or 2;
$Z_5$ is O, S, S(=O), S(=O)$_2$, or NR$^f$;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;

each P$^6$ is independently a ring of the formula:

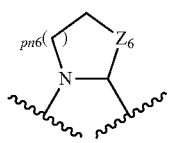

wherein:
the ring is substituted with one or more oxo and is optionally substituted with one or more groups R$^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

Z$_6$ is O, S, S(=O), S(=O)$_2$, or NR$^f$;
pn6 is 0, 1, or 2;

each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;

each P$^7$ is a bridged 5-15 membered bicyclic heterocyclic ring that is attached to the remainder of the compound of formula I through one N-link and through one C-link; wherein the ring is optionally substituted with one or more groups independently selected from R$^{P67}$ and R$^{P207}$; wherein R$^{P67}$ is independently selected from alkoxy, alkyl, aryl, halo, haloalkyl, hydroxy, and —NR$^{P205}$R$^{P206}$, wherein the alkyl can optionally form a fused three- to six-membered ring with an adjacent carbon atom, wherein the three- to six-membered ring is optionally substituted with one or two alkyl groups; R$^{P205}$ and R$^{P206}$ are each independently H, alkyl, aryl, or arylalkyl; or R$^{P205}$ and R$^{P206}$ taken together with the atom to which they are attached form a heterocycle; and R$^{P207}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl-, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$;

each P$^8$ is independently a ring of the formula:

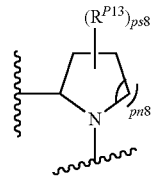

wherein:
ps8 is 2, 3, 4, 5, or 6;
pn8 is 0, 1 or 2;

each R$^{P13}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; where in at least one case two groups R$^{P13}$ that are attached to the same carbon are taken together with the carbon to which they are attached and form a 4-6 membered heterocyclic ring;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

each P$^{10}$ is independently:

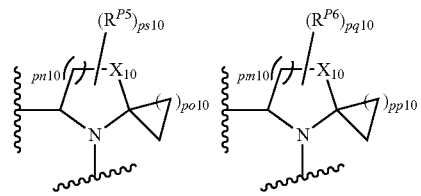

wherein:
X$_{10}$ is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq10 and ps10 are independently 0, 1, 2, 3, or 4;
pm10 and pn10 are independently 0, 1, or 2;
po10 and pp10 are independently 1, 2, or 3;
each $P^{12}$ is independently:

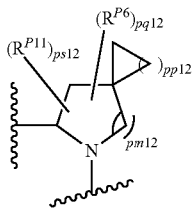

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq12 is independently 0, 1, 2, 3, or 4;
pm12 is independently 0, 1, or 2;
pp12 is independently 1, 2, or 3;
ps12 is 1, 2, 3, or 4;

$R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl, —$NR^{hh}R^h$, ($NR^{hh}R^h$)alkyl-, ($NR^{hh}R^h$)carbonyl-, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{15}$ is:

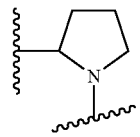 [SMILES: *C1CCCN1*]

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

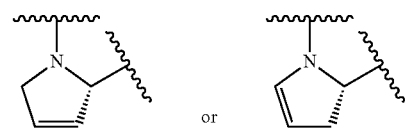 [SMILES: *[C@@H]1C=CCN1* ; *[C@@H]1CC=CN1*]

which is optionally substituted, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl with one or two groups independently selected from halo, alkyl, alkoxyalkyl, haloalkyl, cycloalkyl, and cycloalkylalkyl;

each $P^{19}$ is:

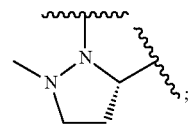 [SMILES: *[C@@H]1CCN(C)N1*]

each $P^{30}$ is independently a ring of the formula:

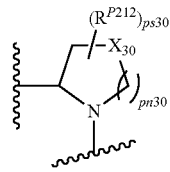

ps30 is 2;
pn30 is 0, 1 or 2;
$X_{30}$ is selected from O, S, S(O), $SO_2$, or $CH_2$; provided that when pn is 0, X is $CH_2$.

each $R^{P212}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P212}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$) alkyl-, (NR$^e$R$^f$)alkylcarbonyl-, (NR$^e$R$^f$)carbonyl-, (NR$^e$R$^f$) sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^X$R$^Y$)alkyl-, and (NR$^X$R$^Y$)carbonyl-; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl-, wherein R$^{X'}$ and R$^{Y'}$ are independently selected from hydrogen and alkyl;

each R$^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl; R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$) alkyl-, (NR$^e$R$^f$)alkylcarbonyl-, (NR$^e$R$^f$)carbonyl-, (NR$^e$R$^f$) sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^X$R$^Y$)alkyl-, and (NR$^X$R$^Y$)carbonyl-; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl-, wherein R$^{X'}$ and R$^{Y'}$ are independently selected from hydrogen and alkyl; or a pharmaceutically acceptable salt or prodrug thereof.

In one specific embodiment X$^{18}$ is —CH=CH—.
In one specific embodiment X$^{18}$ is —CH$_2$CH$_2$—.
In one specific embodiment X$^{18}$ is —OCH$_2$—.
In one specific embodiment Y$^{18}$ is selected from A$^0$ and A$^1$.
In one specific embodiment Y$^{18}$ is selected from A$^0$.
In one specific embodiment Y$^{18}$:

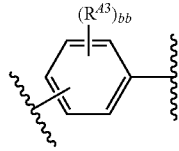

wherein each R$^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and bb is independently 0, 1, 2, 3, or 4.

In one specific embodiment Y$^{18}$:

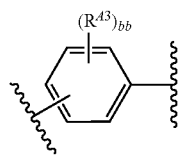

wherein each R$^{43}$ is independently selected from alkoxy, alkoxyalkyl, alkoxycarbonyl, alkyl, arylalkoxycarbonyl, carboxy, formyl, halo, haloalkyl, hydroxy, and hydroxyalkyl; and bb is independently 0, 1, 2, 3, or 4.

In one specific embodiment Y$^{18}$ is phenyl.
In one specific embodiment at least one of E$^{1a}$ and E$^{1b}$ is —N(H)(alkoxycarbonyl).
In one specific embodiment at least one of E$^{1a}$ and E$^{1b}$ is —N(H)C(=O)OMe.
In one specific embodiment at least one of E$^{1a}$ and E$^{1b}$ is —N(H)(cycloalkylcarbonyl) or —N(H)(cycloalkyloxycarbonyl).
In one specific embodiment at least one of E$^{1a}$ and E$^{1b}$ is cyclopropylcarbonylamino, cyclobutylcarbonylamino, cyclopropyloxycarbonylamino or cyclobutyloxycarbonylamino.
In one specific embodiment E$^{1a}$ and E$^{1b}$ are each independently selected from cyclopropylcarbonylamino, cyclobutylcarbonylamino, cyclopropyloxycarbonylamino and methoxycarbonylamino.

In one specific embodiment at least one of $V^{1a}$ and $V^{1b}$ is $V^0$.

In one specific embodiment at least one of $V^{1a}$ and $V^{1b}$ is selected from:

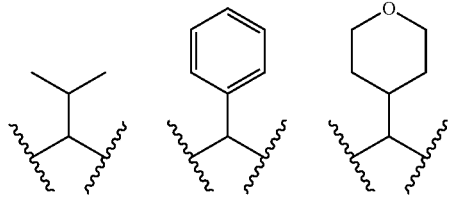

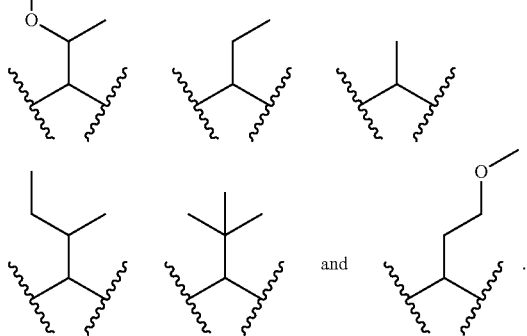

and

In one specific embodiment at least one of $V^{1a}$ and $V^{1b}$ is selected from:

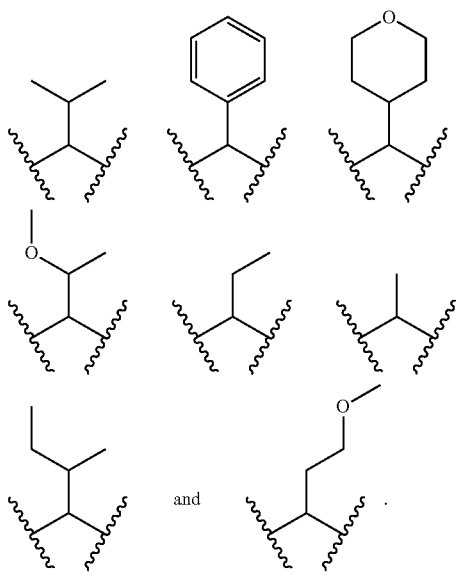

and

In one specific embodiment at least one of $V^{1a}$ and $V^{1b}$ is:

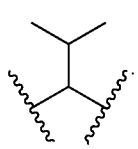 [SMILES: *C(*)C(C)C]

In one specific embodiment at least one of $V^{1a}$ and $V^{1b}$ is selected from:

and

In one specific embodiment at least one of $V^{1a}$ and $V^{1b}$ is selected from:

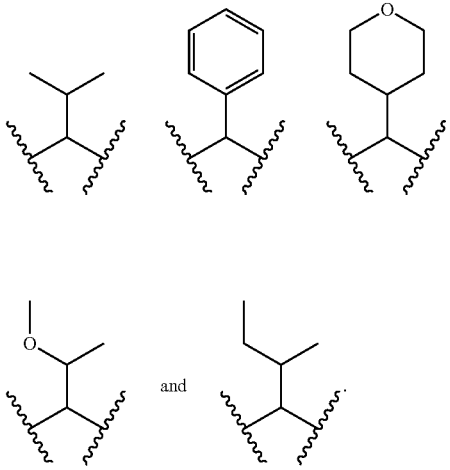

and

In one specific embodiment $V^{1a}$ and $V^{1b}$ are each independently selected from:

and

In one specific embodiment $P^{1a}$ and $P^{1b}$ are each independently selected from:

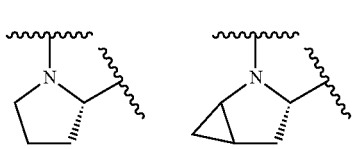

-continued

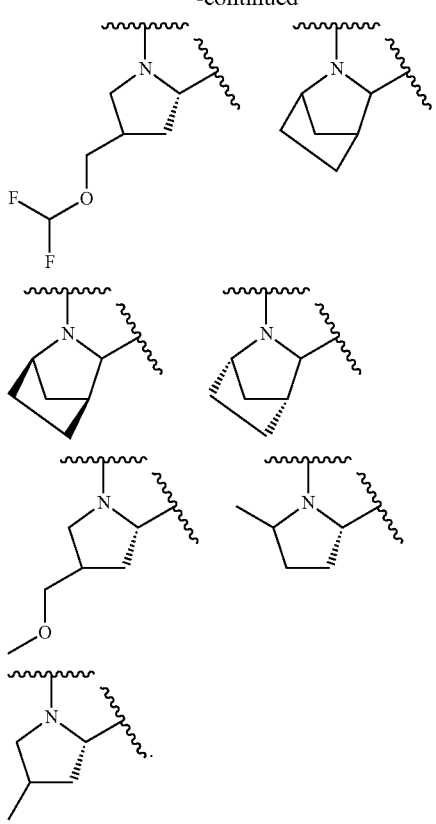

In one specific embodiment at least one of $P^{1a}$ and $P^{1b}$ is $P^0$.

In one specific embodiment at least one of $P^{1a}$ and $P^{1b}$ is selected from:

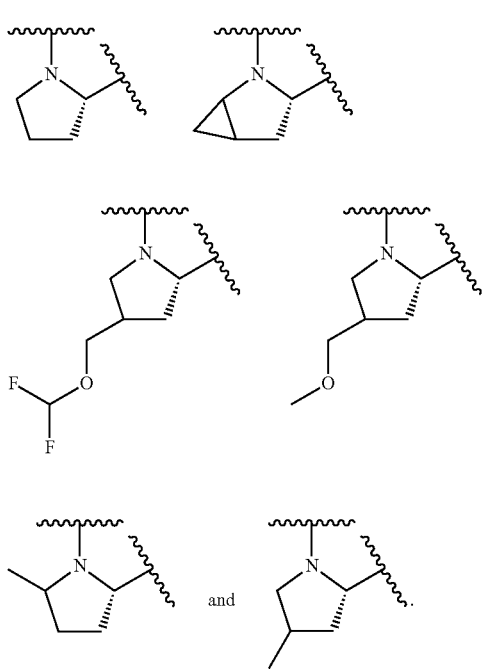

In one specific embodiment at least one of $P^{1a}$ and $P^{1b}$ is:

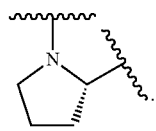 [SMILES: *[C@@H]1CCCN1*]

In one specific embodiment $P^{1a}$ and $P^{1b}$ are each independently selected from:

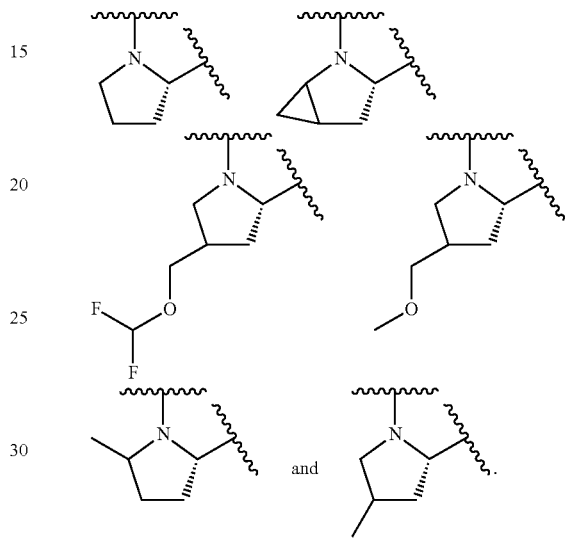

In one specific embodiment the invention provides a compound prepared in the Examples herein that is a compound of specific Embodiment C, or a salt or a prodrug thereof.

Specific Embodiment D

In one specific embodiment the invention provides a compound of formula (I):

$$E^{1a}\text{-}V^{1a}\text{---}C(=O)\text{---}P^{1a}\text{---}W^{1a}\text{---}P^{1b}\text{---}C(=O)\text{---}V^{1b}\text{-}E^{1b} \quad (I)$$

wherein:
$W^{1a}$ has the formula:

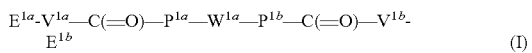

and $W^{1a}$ is optionally substituted with one or more (e.g. 1, 2, 3, or 4) groups independently selected from halo, alkyl, haloalkyl, cyano, and

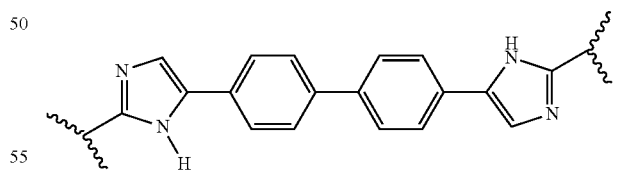

wherein each R is independently H, alkyl, haloalkyl, cycloalkyl, aryl, or heteroaryl;

$E^{1a}$ is $E^0$, $E^1$, or $E^2$, or $E^{1a}$-$V^{1a}$ taken together are $R^{9a}$;
$E^{1b}$ is $E^0$, $E^1$, or $E^2$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
one of $P^{1a}$ and $P^{1b}$ is

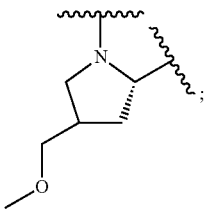

and the other of $P^{1a}$ and $P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$ and $P^{30}$;

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $E^2$ is independently —NHR$^{Ef}$ wherein R$^{Ef}$ is cycloalkylcarbonyl or cycloalkyloxycarbonyl;

each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NR$^{VO1}$R$^{VO1}$COalkyl, wherein each R$^{VO1}$ is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)(OR$^{VO2}$)$_2$, wherein each R$^{VO1}$ is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl-, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $P^0$ is independently:

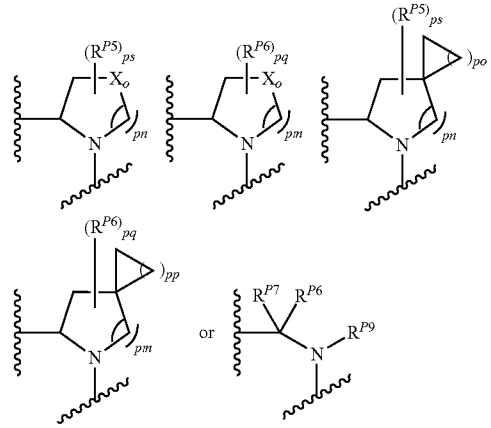

wherein:
$X_0$ is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;
R$^{P7}$ and R$^{P8}$ are each independently selected from hydrogen, alkenyl, alkoxyalkyl, alkyl, haloalkyl, and (NR$^{Pa}$R$^{Pb}$)

alkyl; or $R^{P7}$ and $R^{P8}$, together with the carbon atom to which they are attached, form a five or six membered saturated ring optionally containing one or two heteroatoms selected from $NR^{Pz}$, O, and S; wherein $R^{Pz}$ is selected from hydrogen and alkyl;

$R^{P9}$ is selected from hydrogen and alkyl;

each $P^1$ is independently:

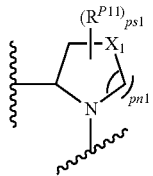

wherein:
$X_1$ is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;
each $R^{P10}$ is independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
at least one $R^{P11}$ is independently selected from cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclyloxyalkyloxy, $(NR^hR^h)$alkyloxy, cyanoalkoxy, cyanocycloalkyloxy, cycloalkyloxy, oxo, heterocyclyl, $-NR^{hh}R^h$, $(NR^{hh}R^h)$alkyl, $(NR^{hh}R^h)$carbonyl-, wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, $(NR^hR^h)$sulfonyl, heteroarylsulfonyl, $-S(=O)_2R^h$, $-C(=O)R^h$, $-C(=O)NR^hR^h$; and the remaining $R^{P11}$ are independently selected from $R^{P100}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocloooxyalkyloxy, $(NR^hR^h)$alkyloxy, cyanoalkoxy, cyanocycloalkyloxy, cycloalkyloxy, oxo and heterocyclyl; wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{P100}$ is independently selected from alkoxy, alkyl, aryl, halo, haloalkyl, hydroxy, and $-NR^{P101}R^{P102}$, wherein the alkyl can optionally form a fused three- to six-membered ring with an adjacent carbon atom, wherein the three- to six-membered ring is optionally substituted with one or two alkyl groups; and $R^{P101}$ and $R^{P102}$ are each independently H, alkyl, aryl, or arylalkyl; or $R^{P101}$ and $R^{P102}$ taken together with the atom to which they are attached form a heterocycle;
ps1 is 1, 2, 3, or 4;
pn1 is 0, 1, or 2;
each $P^3$ is independently a ring of the formula:

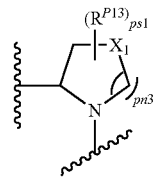

wherein:
the ring is substituted with one or more oxo group;
each $R^{P13}$ is independently selected from $R^{P5}$, cyano, alkylsulfonyl, arylsulfonyl, $(NR^hR^h)$sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocloooxyalkyloxy, $(NR^hR^h)$alkyloxy, cyanoalkoxy, cyanocycloalkyloxy, cycloalkyloxy, oxo, heterocyclyl; wherein each $R^h$ is independently $-H$, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps3 is 0, 1, 2, 3, or 4;
pn3 is 0, 1, or 2;
each $P^5$ is independently a ring of the formula:

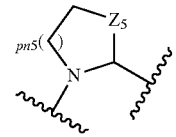

wherein:
the ring is optionally substituted with one or more groups $R^{P15}$ that are independently selected from alkoxy, alkyl, aryl, halo, haloalkyl, hydroxy, and $-NR^{Pa}R^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;

pn3 is 0, 1, or 2;
Z$_5$ is O, S, S(=O), S(=O)$_2$, or NR$^f$;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;
each P$^6$ is independently a ring of the formula:

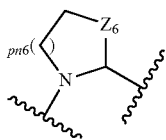

wherein:
the ring is substituted with one or more oxo and is optionally substituted with one or more groups R$^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
Z$_6$ is O, S, S(=O), S(=O)$_2$, or NR$^f$;
pn6 is 0, 1, or 2;
each R$^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two R$^h$ groups are present then they may come together with the atoms to which they are bound to form a 4-15 membered heterocyclic ring;
each P$^7$ is a bridged 5-15 membered bicyclic heterocyclic ring that is attached to the remainder of the compound of formula I through one N-link and through one C-link; wherein the ring is optionally substituted with one or more groups independently selected from R$^{P67}$ and R$^{P207}$; wherein R$^{P67}$ is independently selected from alkoxy, alkyl, aryl, halo, haloalkyl, hydroxy, and —NR$^{P205}$R$^{P206}$, wherein the alkyl can optionally form a fused three- to six-membered ring with an adjacent carbon atom, wherein the three- to six-membered ring is optionally substituted with one or two alkyl groups; R$^{P205}$ and R$^{P206}$ are each independently H, alkyl, aryl, or arylalkyl; or R$^{P205}$ and R$^{P206}$ taken together with the atom to which they are attached form a heterocycle; and R$^{P207}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl-, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$;
each P$^8$ is independently a ring of the formula:

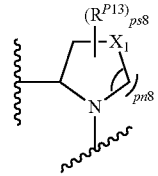

wherein:
ps8 is 2, 3, 4, 5, or 6;
pn8 is 0, 1 or 2;
each R$^{P13}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; where in at least one case two groups R$^{P13}$ that are attached to the same carbon are taken together with the carbon to which they are attached and form a 4-6 membered heterocyclic ring;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
each P$^{10}$ is independently:

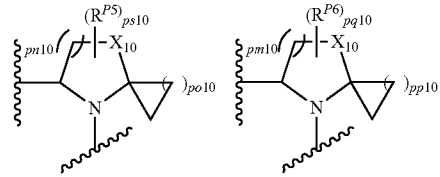

wherein:
X$_{10}$ is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq10 and ps10 are independently 0, 1, 2, 3, or 4;
pm10 and pn10 are independently 0, 1, or 2;
po10 and pp10 are independently 1, 2, or 3;
each $P^{12}$ is independently:

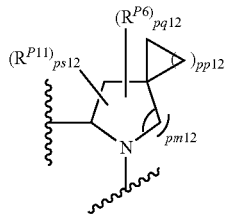

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

$R^{Pa}$ and $R^{Pb}$ are each independently H, alkyl, aryl, or arylalkyl; or $R^{Pa}$ and $R^{Pb}$ taken together with the atom to which they are attached form a heterocycle;

pq12 is independently 0, 1, 2, 3, or 4;
pm12 is independently 0, 1, or 2;
pp12 is independently 1, 2, or 3;
ps12 is 1, 2, 3, or 4;

$R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl, —$NR^{hh}R^h$, ($NR^{hh}R^h$)alkyl-, ($NR^{hh}R^h$)carbonyl-, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —S(=O)$_2R^h$, —C(=O)$R^h$, —C(=O)$NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{15}$ is:

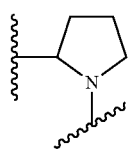

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

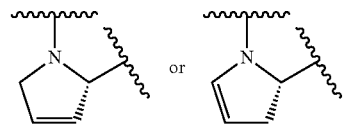 [SMILES: *[C@@H]1C=CCN1* ; *[C@@H]1CC=CN1*]

which is optionally substituted, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl with one or two groups independently selected from halo, alkyl, alkoxyalkyl, haloalkyl, cycloalkyl, and cycloalkylalkyl;

each $P^{19}$ is:

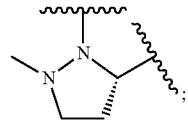

each $P^{30}$ is independently a ring of the formula:

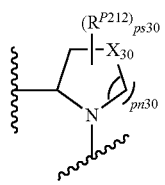

ps30 is 2;
pn30 is 0, 1 or 2;
$X_{30}$ is selected from O, S, S(O), SO$_2$, or CH$_2$; provided that when pn is 0, X is CH$_2$.

each $R^{P212}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P212}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl-, ($NR^eR^f$)alkylcarbonyl-, ($NR^eR^f$)carbonyl-, ($NR^eR^f$)sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, ($NR^XR^Y$)alkyl-, and ($NR^XR^Y$)carbonyl-; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl-, wherein $R^{X'}$ and $R^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl-, ($NR^eR^f$)alkylcarbonyl-, ($NR^eR^f$)carbonyl-, ($NR^eR^f$)sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, ($NR^XR^Y$)alkyl-, and ($NR^XR^Y$)carbonyl-; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl-, wherein $R^{X'}$ and $R^{Y'}$ are independently selected from hydrogen and alkyl;

or a pharmaceutically acceptable salt or prodrug thereof.

In one specific embodiment the invention provides a compound of formula (I):

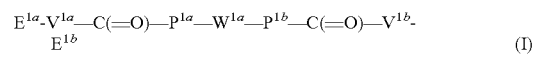

$$E^{1a}\text{-}V^{1a}\text{—}C(=O)\text{—}P^{1a}\text{—}W^{1a}\text{—}P^{1b}\text{—}C(=O)\text{—}V^{1b}\text{-}E^{1b} \qquad (I)$$

wherein:

$W^{1a}$ has the formula:

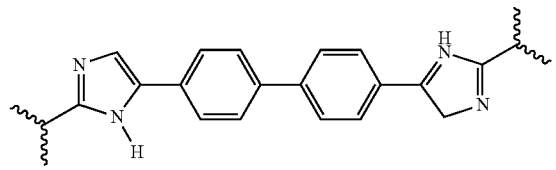

and $W^{1a}$ is optionally substituted with one or more (e.g. 1, 2, 3, or 4) groups independently selected from halo, alkyl, haloalkyl, cyano, and

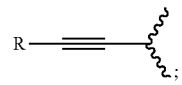

wherein each R is independently H, alkyl, haloalkyl, cycloalkyl, aryl, or heteroaryl;

$E^{1a}$ is $E^0$, $E^1$, or $E^2$, or $E^{1a}\text{-}V^{1a}$ taken together are $R^{9a}$;

$E^{1b}$ is $E^0$, $E^1$, or $E^2$, or $E^{1b}\text{-}V^{1b}$ taken together are $R^{9b}$;

$V^{1a}$ is $V^0$ or $E^{1a}\text{-}V^{1a}$ taken together are $R^{9a}$;

$V^{1b}$ is $V^0$ or $E^{1b}\text{-}V^{1b}$ taken together are $R^{9b}$;

one of $P^{1a}$ and $P^{1b}$ is

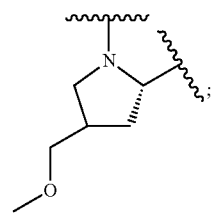

and the other of $P^{1a}$ and $P^{1b}$ $P^{1a}$ is selected from:

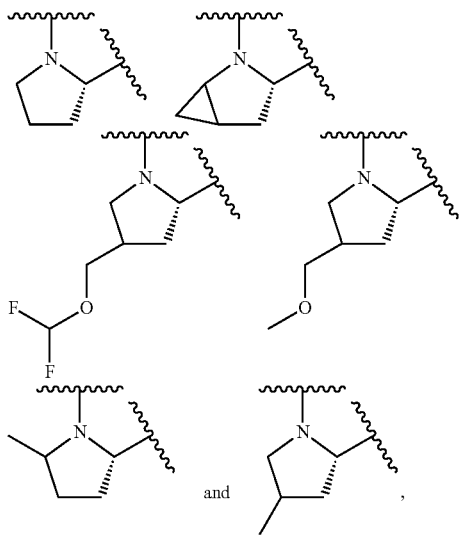

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl-, $(NR^eR^f)$alkylcarbonyl-, $(NR^eR^f)$carbonyl-, $(NR^eR^f)$sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $E^2$ is independently —$NHR^{Ef}$ wherein $R^{Ef}$ is cycloalkylcarbonyl or cycloalkyloxycarbonyl;

each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, $NR^{VO1}R^{VO1}$COalkyl, wherein each $R^{VO1}$ is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, $(NR^XR^Y)$alkyl-, oxo, and —$P(O)(OR^{VO2})_2$, wherein each $R^{VO1}$ is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl-, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl-, $(NR^eR^f)$alkylcarbonyl-, $(NR^eR^f)$carbonyl-, $(NR^eR^f)$sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, $(NR^XR^Y)$alkyl-, and $(NR^XR^Y)$carbonyl-; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl-, wherein $R^{X'}$ and $R^{Y'}$ are independently selected from hydrogen and alkyl; and each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl-, ($NR^eR^f$)alkylcarbonyl-, ($NR^eR^f$)carbonyl-, ($NR^eR^f$)sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, ($NR^XR^Y$)alkyl-, and ($NR^XR^Y$)carbonyl-; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl-, wherein $R^{X'}$ and $R^{Y'}$ are independently selected from hydrogen and alkyl;

or a pharmaceutically acceptable salt or prodrug thereof.

In one specific embodiment at least one of $E^{1a}$ and $E^{1b}$ is —N(H)(alkoxycarbonyl).

In one specific embodiment at least one of $E^{1a}$ and $E^{1b}$ is —N(H)C(=O)OMe.

In one specific embodiment at least one of $E^{1a}$ and $E^{1b}$ is —N(H)(cycloalkylcarbonyl) or —N(H)(cycloalkyloxycarbonyl).

In one specific embodiment at least one of $E^{1a}$ and $E^{1b}$ is cyclopropylcarbonylamino, cyclobutylcarbonylamino, cyclopropyloxycarbonylamino or cyclobutyloxycarbonylamino.

In one specific embodiment $E^{1a}$ and $E^{1b}$ are each independently selected from cyclopropylcarbonylamino, cyclobutylcarbonylamino, cyclopropyloxycarbonylamino and methoxycarbonylamino.

In one specific embodiment at least one of $V^{1a}$ and $V^{1b}$ is $V^0$.

In one specific embodiment at least one of $V^{1a}$ and $V^{1b}$ is selected from:

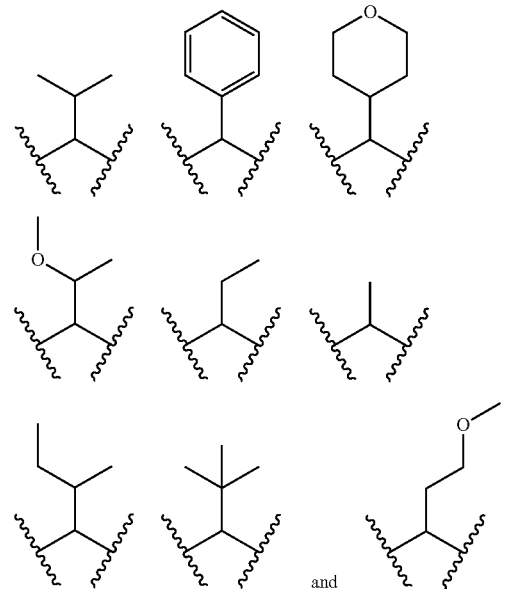

In one specific embodiment at least one of $V^{1a}$ and $V^{1b}$ is selected from:

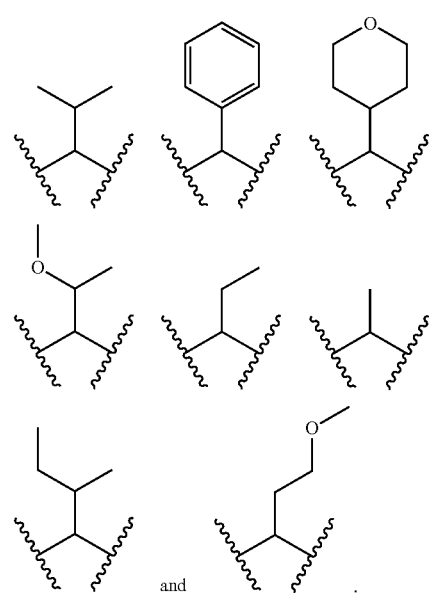

In one specific embodiment at least one of $V^{1a}$ and $V^{1b}$ is:

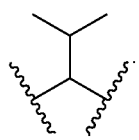 [SMILES: *C(*)C(C)C]

In one specific embodiment at least one of $V^{1a}$ and $V^{1b}$ is selected from:

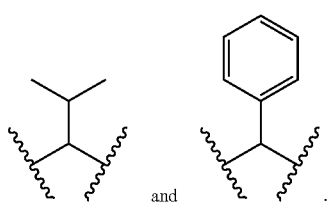

In one specific embodiment at least one of $V^{1a}$ and $V^{1b}$ is selected from:

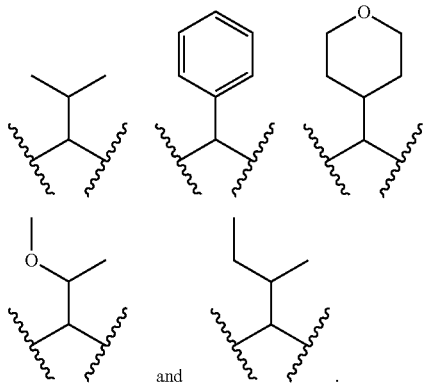

In one specific embodiment $V^{1a}$ and $V^{1b}$ are each independently selected from:

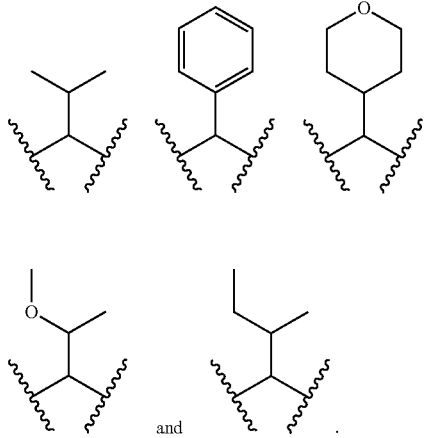

In one specific embodiment one of $P^{1a}$ and $P^{1b}$ is

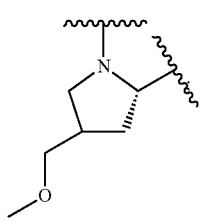

and the other of $P^{1a}$ and $P^{1b}$ $P^{1a}$ is selected from:

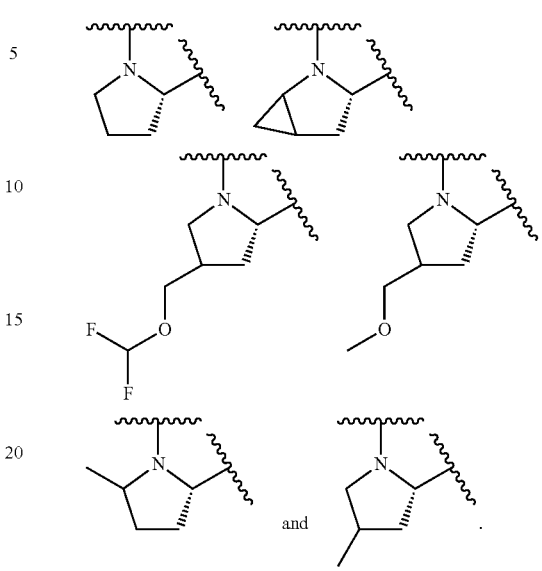

In one specific embodiment at least one of $P^{1a}$ and $P^{1b}$ is $P^0$.

In one specific embodiment at least one of $P^{1a}$ and $P^{1b}$ is selected from:

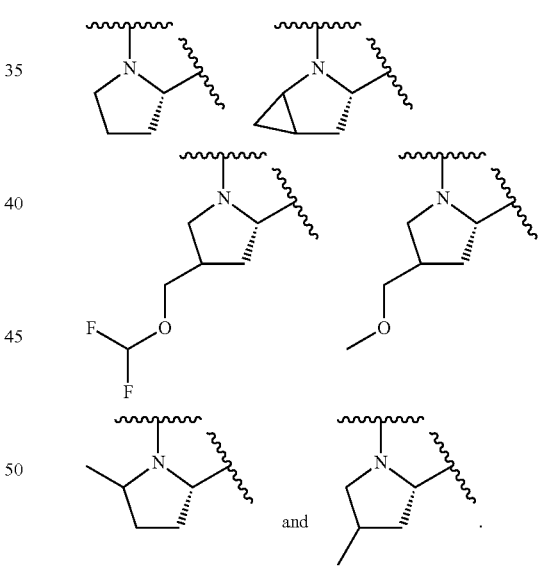

In one specific embodiment at least one of $P^{1a}$ and $P^{1b}$ is:

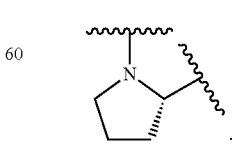

In one specific embodiment $P^{1a}$ and $P^{1b}$ are each independently selected from:

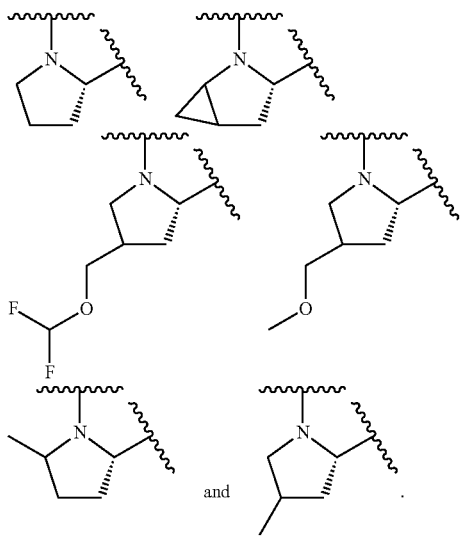

In one specific embodiment $E^{1a}$-$V^{1a}$ taken together are $R^{9a}$ or $E^{1b}$-$V^{1b}$ taken together are $R^{9b}$; wherein $R^{9a}$ or $R^{9b}$ is selected from:

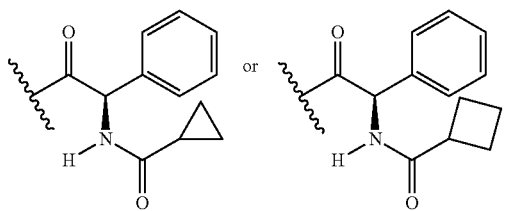

In one specific embodiment the invention provides a compound prepared in the Examples herein that is a compound of specific Embodiment D, or a salt or a prodrug thereof.

Specific Embodiment E

In one specific embodiment the invention provides a compound of formula (I):

$$E^{1a}\text{-}V^{1a}\text{—}C(=O)\text{—}P^{1a}\text{—}W^{1a}\text{—}P^{1b}\text{—}C(=O)\text{—}V^{1b}\text{-}E^{1b} \quad (I)$$

wherein:
$W^{1a}$ has the formula:

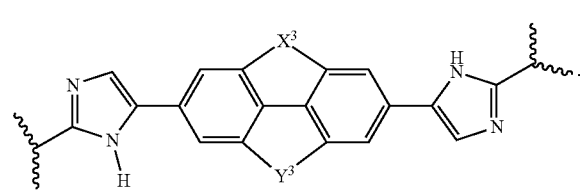

$X^3$ is —CH$_2$—CH$_2$—, —CH$_2$—O—, or —O—CH$_2$—;
$Y^3$ is —CH$_2$—CH$_2$—, —CH$_2$—O—, —O—CH$_2$—, or —CH=CH—.
and $W^{1a}$ is optionally substituted with one or more (e.g. 1, 2, 3, or 4) groups independently selected from halo, alkyl, haloalkyl, cyano, and

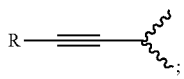

wherein each R is independently H, alkyl, haloalkyl, cycloalkyl, aryl, or heteroaryl;
$Y^5$ is —O—CH$_2$—, or —CH$_2$—O—;
$X^5$ is —CH$_2$—CH$_2$— or —CH=CH—;
$E^{1a}$ is $E^0$, $E^1$, or $E^2$, or $E^{1a}$-$V^{1a}$ taken together are $R^{9a}$;
$E^{1b}$ is $E^0$, $E^1$, or $E^2$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;
$P^{1a}$ is selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;
$P^{1b}$ is selected from $P^0$, $P^1$, $P^3$, $P^5$, $P^6$, $P^7$, $P^8$, $P^{10}$, $P^{12}$, $P^{15}$, $P^{18}$, $P^{19}$, and $P^{30}$;
each $E^0$ is independently —NR$^{Ec}$R$^{Ed}$ wherein R$^{Ec}$ and R$^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl-, (NR$^e$R$^f$)alkylcarbonyl-, (NR$^e$R$^f$)carbonyl-, (NR$^e$R$^f$)sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;
each $E^1$ is independently selected from hydrogen, hydroxy, alkyl, haloalkyl, —NHhaloalkyl, aryl, and heterocyclyl;
each $E^2$ is independently —NHR$^{Ef}$ wherein R$^{Ef}$ is cycloalkylcarbonyl or cycloalkyloxycarbonyl;
each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, NR$^{VO1}$R$^{VO1}$COalkyl, wherein each R$^{VO1}$ is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, (NR$^X$R$^Y$)alkyl-, oxo, and —P(O)(OR$^{VO2}$)$_2$, wherein each R$^{VO1}$ is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, (NR$^X$R$^Y$)alkyl-, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each P$^0$ is independently:

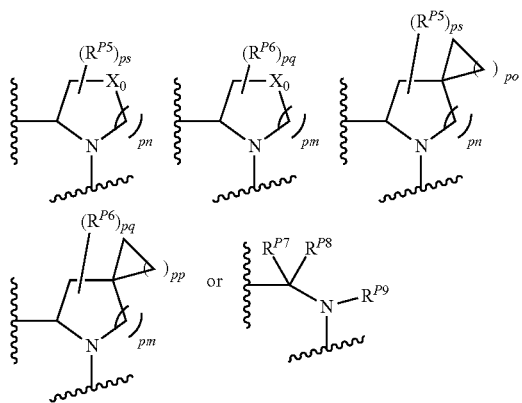

wherein:

X$_0$ is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

pq and ps are independently 0, 1, 2, 3, or 4;

pm and pn are independently 0, 1, or 2;

po and pp are independently 1, 2, or 3;

R$^{P7}$ and R$^{P8}$ are each independently selected from hydrogen, alkenyl, alkoxyalkyl, alkyl, haloalkyl, and (NR$^{Pa}$R$^{Pb}$)alkyl; or R$^{P7}$ and R$^{P8}$, together with the carbon atom to which they are attached, form a five or six membered saturated ring optionally containing one or two heteroatoms selected from NR$^{Pa}$, O, and S; wherein R$^{Pz}$ is selected from hydrogen and alkyl;

R$^{P9}$ is selected from hydrogen and alkyl;

each P$^1$ is independently:

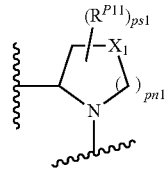

wherein:

X$_1$ is selected from O, S, S(O), SO$_2$, CH$_2$, CHR$^{P10}$, and C(R$^{P10}$)$_2$; provided that when pn is 0, X is selected from CH$_2$, CHR$^{P10}$, and C(R$^{P10}$)$_2$;

each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

R$^{Pa}$ and R$^{Pb}$ are each independently H, alkyl, aryl, or arylalkyl; or R$^{Pa}$ and R$^{Pb}$ taken together with the atom to which they are attached form a heterocycle;

at least one R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocyclyloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl-, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P100}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo and heterocyclyl; wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{P100}$ is independently selected from alkoxy, alkyl, aryl, halo, haloalkyl, hydroxy, and —NR$^{P101}$R$^{P102}$, wherein the alkyl can optionally form a fused three- to six-membered ring with an adjacent carbon atom, wherein the three- to six-membered ring is optionally substituted with one or two alkyl groups; and $R^{P101}$ and $R^{P102}$ are each independently H, alkyl, aryl, or arylalkyl; or $R^{P101}$ and $R^{P102}$ taken together with the atom to which they are attached form a heterocycle;

ps1 is 1, 2, 3, or 4;
pn1 is 0, 1, or 2;
each $P^3$ is independently a ring of the formula:

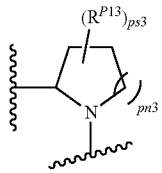

wherein:
the ring is substituted with one or more oxo group;
each $R^{P13}$ is independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps3 is 0, 1, 2, 3, or 4;
pn3 is 0, 1, or 2;
each $P^5$ is independently a ring of the formula:

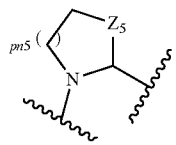

wherein:
the ring is optionally substituted with one or more groups $R^{15}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups $R^{P15}$ that are attached to the same carbon when taken together with the carbon to which they are attached can form a 3-6 membered carbocyclic or heterocyclic ring;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
pn3 is 0, 1, or 2;
$Z_5$ is O, S, S(=O), S(=O)$_2$, or NR$^f$;

each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

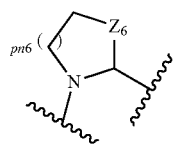

wherein:
the ring is substituted with one or more oxo and is optionally substituted with one or more groups $R^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
$R^{Pa}$ and $R^{Pb}$ are each independently H, alkyl, aryl, or arylalkyl; or $R^{Pa}$ and $R^{Pb}$ taken together with the atom to which they are attached form a heterocycle;
$Z_6$ is O, S, S(=O), S(=O)$_2$, or NR$^f$;
pn6 is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^7$ is a bridged 5-15 membered bicyclic heterocyclic ring that is attached to the remainder of the compound of formula I through one N-link and through one C-link; wherein the ring is optionally substituted with one or more groups independently selected from $R^{P67}$ and $R^{P207}$; wherein $R^{P67}$ is independently selected from alkoxy, alkyl, aryl, halo, haloalkyl, hydroxy, and —NR$^{P205}$R$^{P206}$, wherein the alkyl can optionally form a fused three- to six-membered ring with an adjacent carbon atom, wherein the three- to six-membered ring is optionally substituted with one or two alkyl groups; $R^{P205}$ and $R^{P206}$ are each independently H, alkyl, aryl, or arylalkyl; or $R^{P205}$ and $R^{P206}$ taken together with the atom to which they are attached form a heterocycle; and $R^{P207}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyalkyloxy, heterocycloxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^{hh}$R$^h$)carbonyl-, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$;

each P$^8$ is independently a ring of the formula:

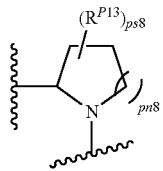

wherein:
ps8 is 2, 3, 4, 5, or 6;
pn8 is 0, 1 or 2;
each R$^{P13}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; where in at least one case two groups R$^{P13}$ that are attached to the same carbon are taken together with the carbon to which they are attached and form a 4-6 membered heterocyclic ring;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
each P$^{10}$ is independently:

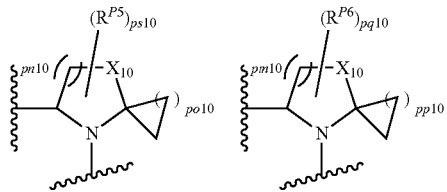

wherein:
X$_{10}$ is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each R$^{P10}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;

each R$^{P5}$ and R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
pq10 and ps10 are independently 0, 1, 2, 3, or 4;
pm10 and pn10 are independently 0, 1, or 2;
po10 and pp10 are independently 1, 2, or 3;
each P$^{12}$ is independently:

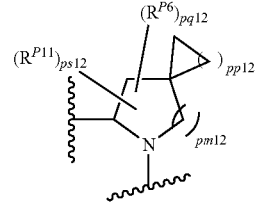

wherein:
each R$^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
R$^{Pa}$ and R$^{Pb}$ are each independently H, alkyl, aryl, or arylalkyl; or R$^{Pa}$ and R$^{Pb}$ taken together with the atom to which they are attached form a heterocycle;
pq12 is independently 0, 1, 2, 3, or 4;
pm12 is independently 0, 1, or 2;
pp12 is independently 1, 2, or 3;
ps12 is 1, 2, 3, or 4;
R$^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl-, (NR$^{hh}$R$^h$)carbonyl-, wherein each R$^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two R$^h$ groups are present then they may come together with the atoms to which they are bound to form a 4-15 membered heterocyclic ring; wherein each R$^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining R$^{P11}$ are independently selected from R$^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{15}$ is:

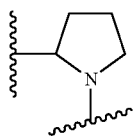

which is substituted with one or two groups independently selected from alkoxyalkyl, haloalkoxyalkyl, alkylsulfanyl, alkylsulfanylalkyl, cyanoalkyl, and cycloalkylalkyl;

each $P^{18}$ is:

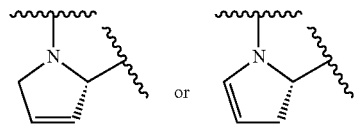

which is optionally substituted, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl; $R^c$ and $R^d$ are independently selected from hydrogen, alkenyloxycarbonyl with one or two groups independently selected from halo, alkyl, alkoxyalkyl, haloalkyl, cycloalkyl, and cycloalkylalkyl;

each $P^{19}$ is:

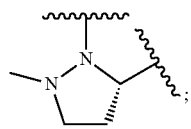 [SMILES: *[C@@H]1CCN(C)N1*]

each $P^{30}$ is independently a ring of the formula:

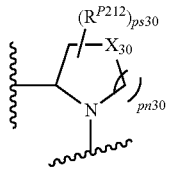

ps30 is 2;
pn30 is 0, 1 or 2;
$X_{30}$ is selected from O, S, S(O), $SO_2$, or $CH_2$; provided that when pn is 0, X is $CH_2$.

each $R^{P212}$ is independently selected from alkyl-, alkoxyalkyl-, hydroxyalkyl-, alkyl-S-alkyl-, sulfanylalkyl-, aminoalkyl-, alkylaminoalkyl-, dialkylaminoalkyl-, alkyl-SO2-alkyl where two groups $R^{P212}$ that are attached to the same carbon are taken together with the carbon to which they are attached and form a 4-6 membered heterocyclic ring;

each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl-, $(NR^eR^f)$alkylcarbonyl-, $(NR^eR^f)$carbonyl-, $(NR^eR^f)$sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, $(NR^XR^Y)$alkyl-, and $(NR^XR^Y)$carbonyl-; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl-, wherein $R^{X'}$ and $R^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl-, $(NR^eR^f)$alkylcarbonyl-, $(NR^eR^f)$carbonyl-, $(NR^eR^f)$sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, $(NR^XR^Y)$alkyl-, and $(NR^XR^Y)$carbonyl-; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl-, wherein $R^{X'}$ and $R^{Y'}$ are independently selected from hydrogen and alkyl;

or a pharmaceutically acceptable salt or prodrug thereof.

In one specific embodiment $W^{1a}$ is:

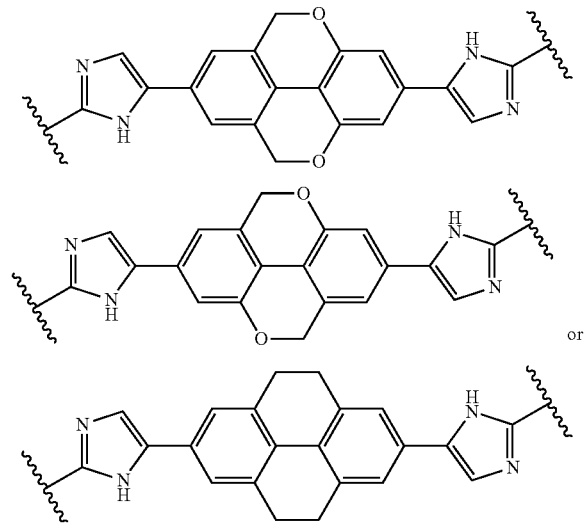

wherein any imidazole ring shown in $W^{1a}$ is optionally substituted with one or more (e.g. 1, 2, 3, or 4) groups independently selected from halo, haloalkyl, and alkyl.

In one specific embodiment the invention provides a compound of formula (I):

$$E^{1a}\text{-}V^{1a}\text{-}C(=O)\text{-}P^{1a}\text{-}W^{1a}\text{-}P^{1b}\text{-}C(=O)\text{-}V^{1b}\text{-}E^{1b} \quad (I)$$

wherein:

$W^{1a}$ has the formula:

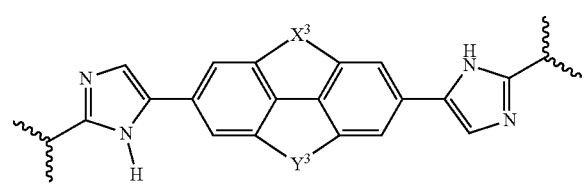

and $W^{1a}$ is optionally substituted with one or more (e.g. 1, 2, 3, or 4) groups independently selected from halo, alkyl, haloalkyl, cyano, and

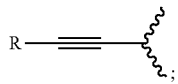

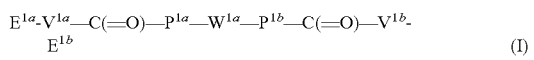

wherein each R is independently H, alkyl, haloalkyl, cycloalkyl, aryl, or heteroaryl;

$X^3$ is —$CH_2$—$CH_2$—, —$CH_2$—O—, or —O—$CH_2$—;

$Y^3$ is —$CH_2$—$CH_2$—, —$CH_2$—O—, —O—$CH_2$—, or —CH=CH—;

$E^{1a}$ is $E^0$, $E^1$, or $E^2$, or $E^{1a}$-$V^{1a}$ taken together are $R^{9a}$;
$E^{1b}$ is $E^0$, $E^1$, or $E^2$, or $E^{1b}$-$V^{1b}$ taken together are $R^{9b}$;
$V^{1a}$ is $V^0$ or $E^{1a}$-$V^{1a}$ taken together are $R^{9a}$;
$V^{1b}$ is $V^0$ or $E^{1b}$-$V^{1b}$ taken together are $R^{9b}$;

each $E^0$ is independently —$NR^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl-, $(NR^eR^f)$alkylcarbonyl-, $(NR^eR^f)$carbonyl-, $(NR^eR^f)$sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each $E^1$ is independently selected from hydrogen, hydroxy, alkyl, haloalkyl, —NHhaloalkyl, aryl, and heterocyclyl;

each $E^2$ is independently —$NHR^{Ef}$ wherein $R^{Ef}$ is cycloalkylcarbonyl or cycloalkyloxycarbonyl;

each $V^0$ is independently alkyl, arylalkyl, alkenyl, CO, (cycloalkyl)alkyl, cycloalkyl, alkoxyalkyl, alkoxyalkylcarbonylalkyl, alkoxycarbonylalkyl, alkylsulfanylalkyl, arylalkoxyalkylcarbonylalkyl, carboxyalkyl, heterocyclylalkyl, heterocyclylcarbonylalkyl, hydroxyalkyl, $NR^{VO1}R^{VO1}$COalkyl, wherein each $R^{VO1}$ is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy; and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, $(NR^XR^Y)$alkyl-, oxo, and —P(O)(OR$^{VO2}$)$_2$, wherein each $R^{VO1}$ is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl-, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

$P^{1a}$ and $P^{1b}$ are each independently selected from:

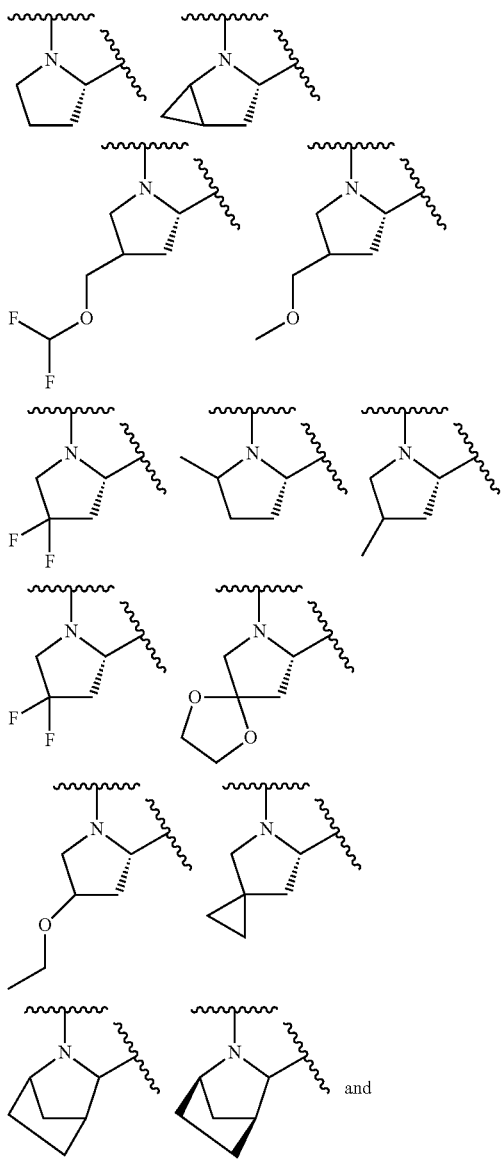

-continued

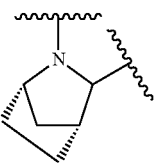

and each $R^{9a}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl-, $(NR^eR^f)$alkylcarbonyl-, $(NR^eR^f)$carbonyl-, $(NR^eR^f)$sulfonyl-, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, $(NR^XR^Y)$alkyl-, and $(NR^XR^Y)$carbonyl-; $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{X'}R^{Y'})$carbonyl-, wherein $R^{X'}$ and $R^{Y'}$ are independently selected from hydrogen and alkyl;

each $R^{9b}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl; $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl-, $(NR^eR^f)$alkylcarbonyl-, $(NR^eR^f)$carbonyl-, $(NR^eR^f)$ sulfonyl-, —C(NCN)OR', and —C(NCN)NR$^X$R$^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^X$R$^Y$)alkyl-, and (NR$^X$R$^Y$)carbonyl-; R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl-, wherein R$^{X'}$ and R$^{Y'}$ are independently selected from hydrogen and alkyl;

or a pharmaceutically acceptable salt or prodrug thereof.

In one specific embodiment at least one of $E^{1a}$ and $E^{1b}$ is —N(H)(alkoxycarbonyl).

In one specific embodiment at least one of $E^{1a}$ and $E^{1b}$ is —N(H)C(=O)OMe.

In one specific embodiment at least one of $E^{1a}$ and $E^{1b}$ is —N(H)(cycloalkylcarbonyl) or —N(H)(cycloalkyloxycarbonyl).

In one specific embodiment at least one of $E^{1a}$ and $E^{1b}$ is cyclopropylcarbonylamino, cyclobutylcarbonylamino, cyclopropyloxycarbonylamino or cyclobutyloxycarbonylamino.

In one specific embodiment $E^{1a}$ and $E^{1b}$ are each independently selected from cyclopropylcarbonylamino, cyclobutylcarbonylamino, cyclopropyloxycarbonylamino and methoxycarbonylamino.

In one specific embodiment at least one of $V^{1a}$ and $V^{1b}$ is $V^0$.

In one specific embodiment at least one of $V^{1a}$ and $V^{1b}$ is selected from:

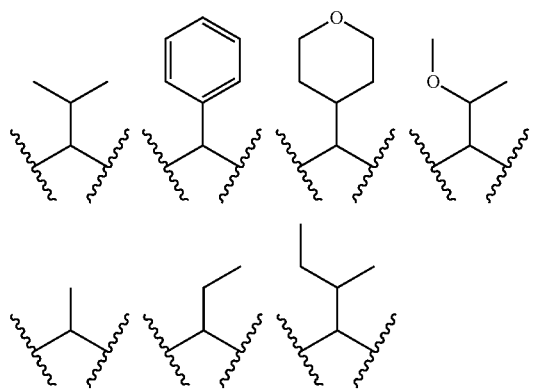

-continued

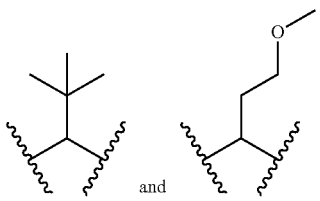

In one specific embodiment at least one of $V^{1a}$ and $V^{1b}$ is selected from:

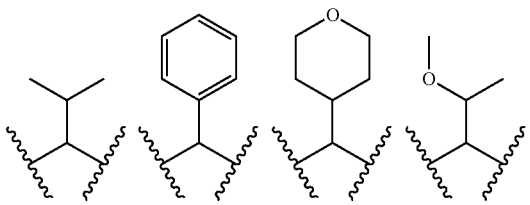

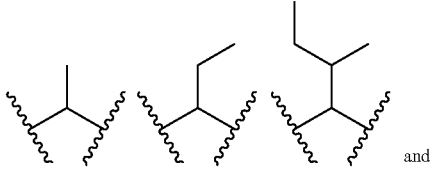

In one specific embodiment at least one of $V^{1a}$ and $V^{1b}$ is:

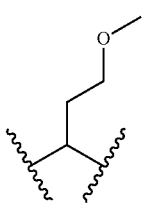

In one specific embodiment at least one of $V^{1a}$ and $V^{1b}$ is selected from:

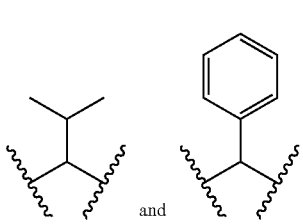

In one specific embodiment at least one of $V^{1a}$ and $V^{1b}$ is selected from:

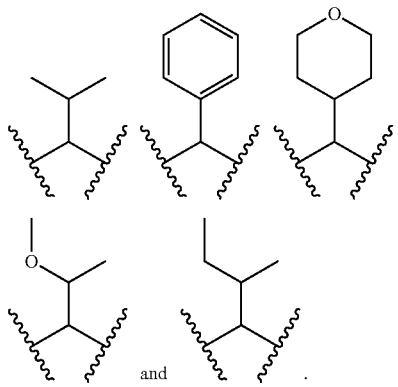

In one specific embodiment $V^{1a}$ and $V^{1b}$ are each independently selected from:

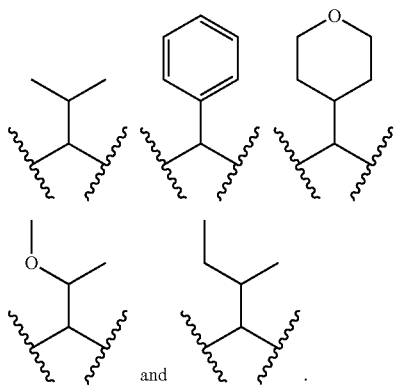

In one specific embodiment $P^{1a}$ and $P^{1b}$ are each independently selected from:

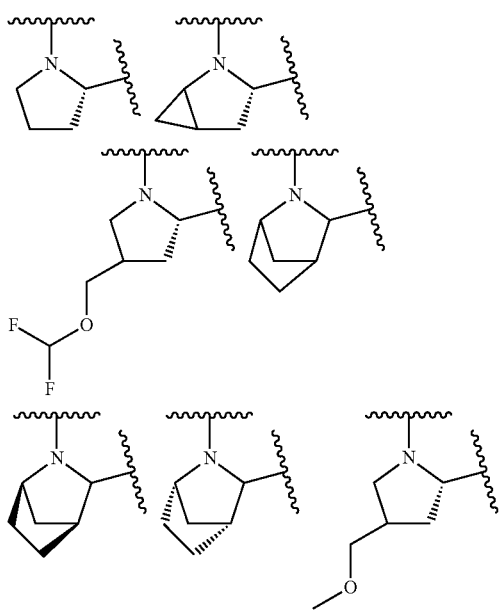

-continued

In one specific embodiment at least one of $P^{1a}$ and $P^{1b}$ is selected from $P^0$ and $P^{15}$.

In one specific embodiment at least one of $P^{1a}$ and $P^{1b}$ is selected from:

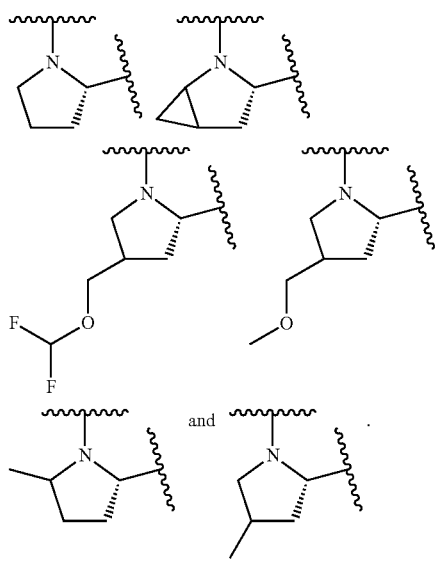

In one specific embodiment $P^{1a}$ and $P^{1b}$ are each independently selected from:

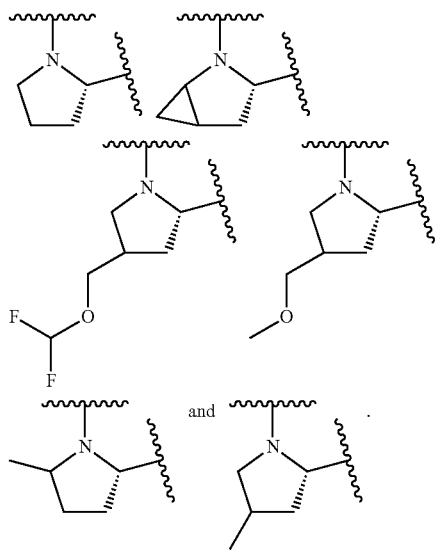

In one specific embodiment at least one of $P^{1a}$ and $P^{1b}$ is selected from:

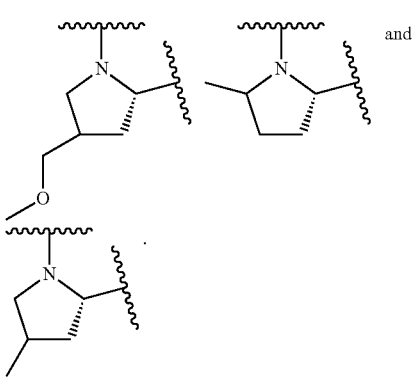

In one specific embodiment $P^{1a}$ and $P^{1b}$ are each independently selected from:

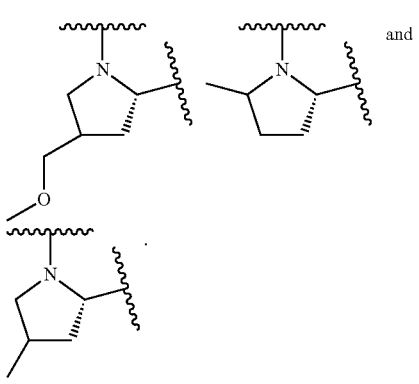

In one specific embodiment one of $P^{1a}$ and $P^{1b}$ is:

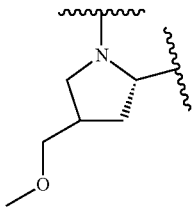

and the other of $P^{1a}$ and $P^{1b}$ is:

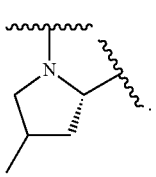

In one specific embodiment one of $P^{1a}$ and $P^{1b}$ is:

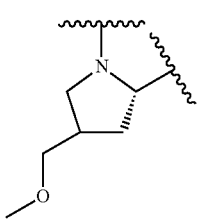

and the other of $P^{1a}$ and $P^{1b}$ is:

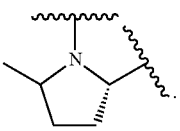

In one specific embodiment one of $P^{1a}$ and $P^{1b}$ is $P^0$.

In one specific embodiment at least one of $P^{1a}$ and $P^{1b}$ is:

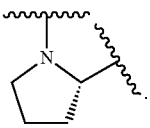 [SMILES: *[C@@H]1CCCN1*]

In one specific embodiment at least one of $P^{1a}$ and $P^{1b}$ is $P^7$.

In one specific embodiment at least one of $P^{1a}$ and $P^{1b}$ is:

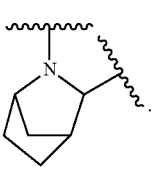 [SMILES: *C1C2CCC(C2)N1*]

In one specific embodiment at least one of $P^{1a}$ and $P^{1b}$ is:

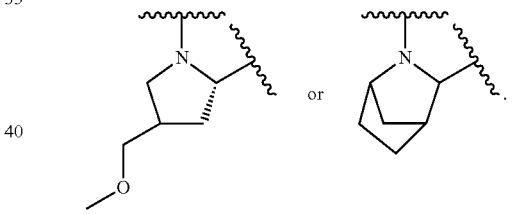

In one specific embodiment at least one of $P^{1a}$ and $P^{1b}$ is:

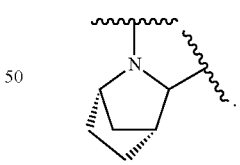

In one specific embodiment at least one of $P^{1a}$ and $P^{1b}$ is:

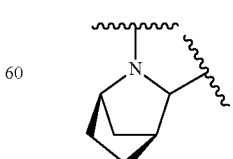

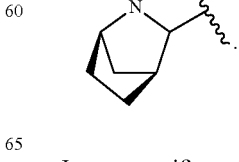

In one specific embodiment at least one of $P^{1a}$ and $P^{1b}$ is $P^{15}$.

In one specific embodiment at least one of $P^{1a}$ and $P^{1b}$ is:

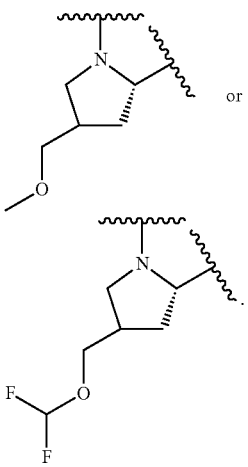

In one specific embodiment at least one of $P^{1a}$ and $P^{1b}$ is:

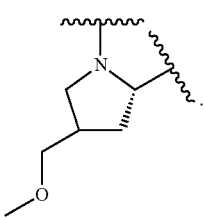

In one specific embodiment at least one of $P^{1a}$ and $P^{1b}$ is selected from $P^7$ and $P^{15}$.

In one specific embodiment at least one of —$V^{1a}$—C(=O)—$P^{1a}$— and —$P^{1b}$—C(=O)—$V^{1b}$— is: at least one of —$V^{1a}$—C(=O)—$P^{1a}$— and —$P^{1b}$—C(=O)—$V^{1b}$— is:

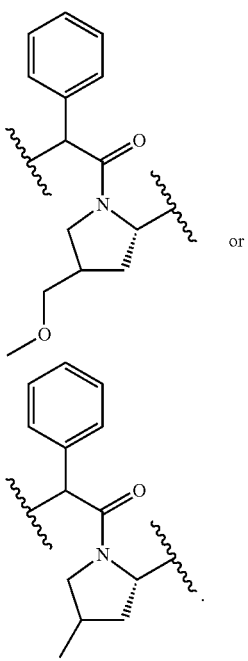

In one specific embodiment at least one of —$V^{1a}$—C(=O)—$P^{1a}$— and —$P^{1b}$—C(=O)—$V^{1b}$— is:

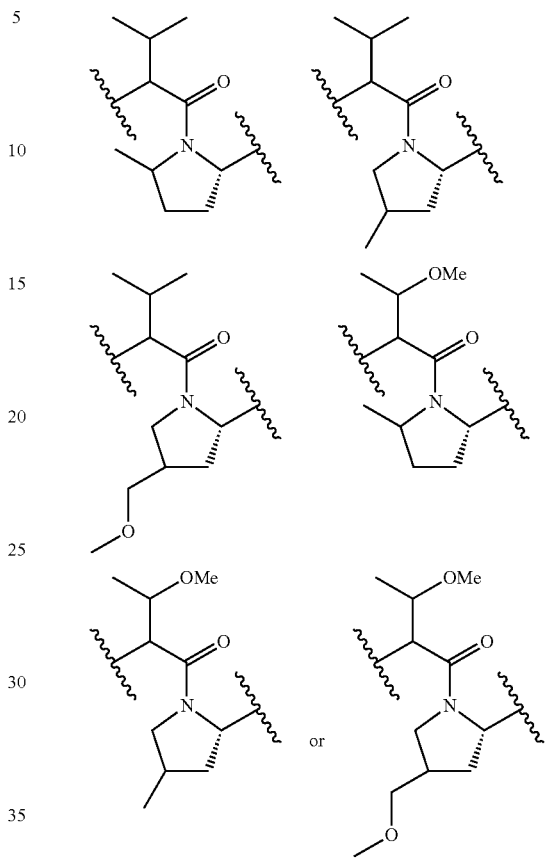

Other Specific Embodiments

In one specific embodiment the invention provides a compound of formula (I):

$$E^{1a}\text{-}V^{1a}\text{—}C(=O)\text{—}P^{1a}\text{—}W^{1a}\text{—}P^{1b}\text{—}C(=O)\text{—}V^{1b}\text{-}E^{1b} \quad (I)$$

wherein:

$W^{1a}$ is selected from A, B, C, D, and E:

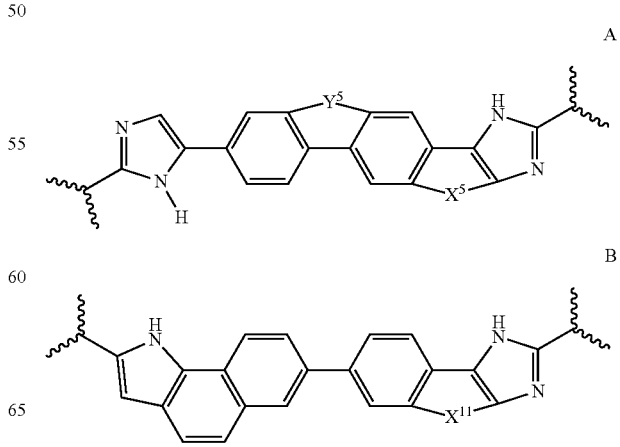

593
-continued

C

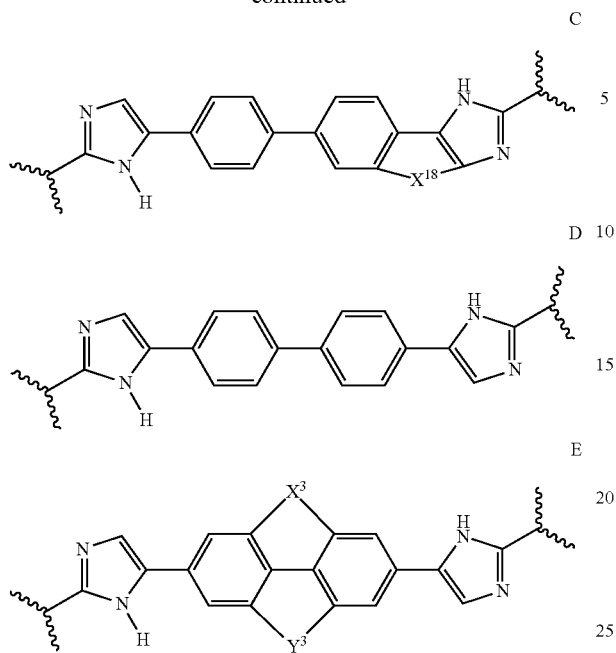

D

E and W$^{1a}$ is optionally substituted with one or more groups independently selected from halo, alkyl, haloalkyl, and cyano;

Y$^5$ is —O—CH$_2$—, or —CH$_2$—O—; X$^5$ is —CH$_2$—CH$_2$— or —CH=CH—;

X$^{11}$ is —CH$_2$—CH$_2$—, —O—CH$_2$—, or —CH=CH—;

X$^{18}$ is —CH=CH—, —CH$_2$CH$_2$—, or —OCH$_2$—;

X$^3$ is —CH$_2$—CH$_2$—, —CH$_2$—O—, or —O—CH$_2$—;

Y$^3$ is —CH$_2$—CH$_2$—, —CH$_2$—O—, or —CH=CH—;

E$^{1a}$ is —N(H)(alkoxycarbonyl), —N(H)(cycloalkylcarbonyl) or —N(H)(cycloalkyloxycarbonyl); or E$^{1a}$-V$^{1a}$ taken together are R$^{9a}$;

E$^{1b}$ is —N(H)(alkoxycarbonyl), —N(H)(cycloalkylcarbonyl) or —N(H)(cycloalkyloxycarbonyl); or E$^{1b}$-V$^{1b}$ taken together are R$^{9b}$;

V$^{1a}$ and V$^{1b}$ are each independently selected from:

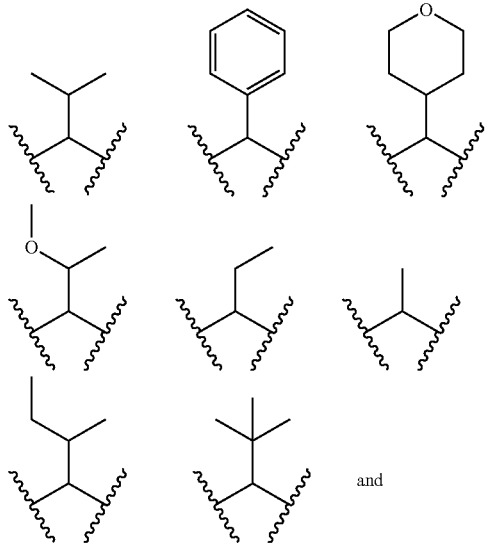

594
-continued

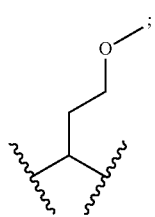

when W$^{1a}$ is selected from A and E, then P$^{1a}$ and P$^{1b}$ are each independently selected from:

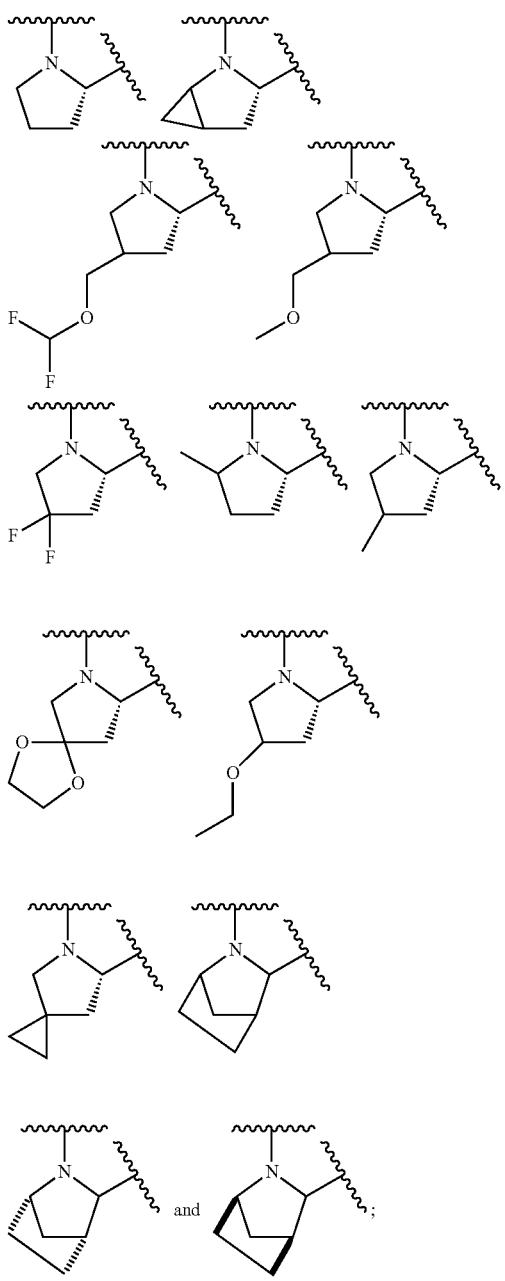

when W$^{1a}$ is selected from B, C, and D then one of P$^{1a}$ and P$^{1b}$ is

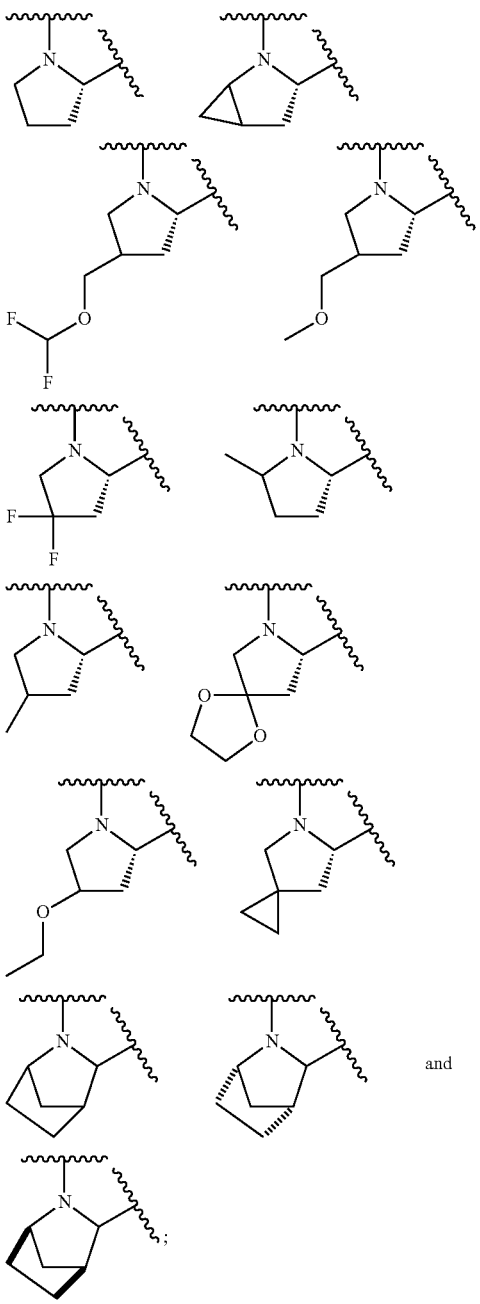

and the other of $P^{1a}$ and $P^{1b}$ $P^{1a}$ is selected from:

and $R^{9a}$ and $R^{9b}$ are each independently:

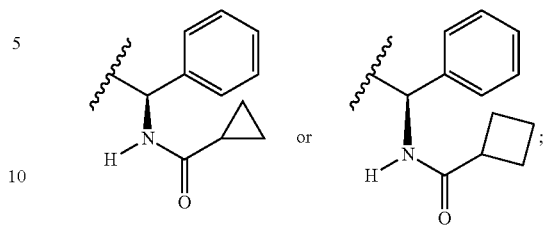

or a pharmaceutically acceptable salt or prodrug thereof.

In one specific embodiment the invention provides a compound wherein $W^{1a}$ has the formula:

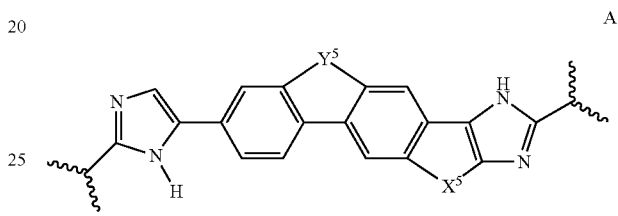

A and $W^{1a}$ is optionally substituted with one or more groups independently selected from halo, alkyl, haloalkyl, and cyano.

In one specific embodiment the invention provides a compound wherein $W^{1a}$ has the formula:

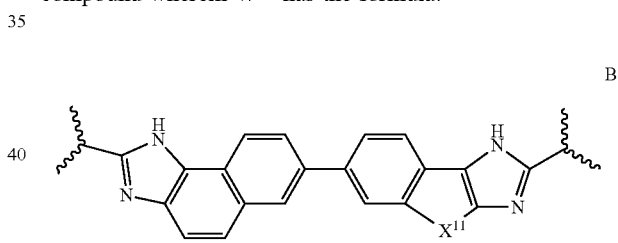

B and $W^{1a}$ is optionally substituted with one or more groups independently selected from halo, alkyl, haloalkyl, and cyano;

In one specific embodiment the invention provides a compound wherein $W^{1a}$ has the formula:

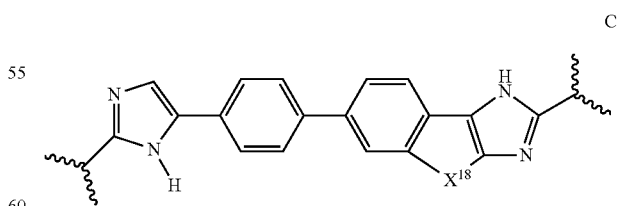

C and $W^{1a}$ is optionally substituted with one or more groups independently selected from halo, alkyl, haloalkyl, and cyano.

In one specific embodiment the invention provides a compound wherein $W^{1a}$ has the formula:

D

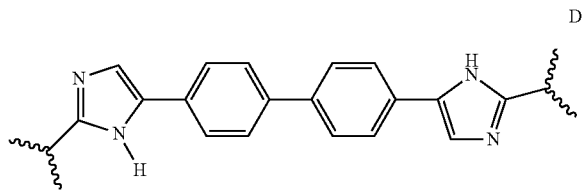 [SMILES: *c1ncc(-c2ccc(-c3ccc(-c4cnc(*)[nH]4)cc3)cc2)[nH]1]

and $W^{1a}$ is optionally substituted with one or more groups independently selected from halo, alkyl, haloalkyl, and cyano.

In one specific embodiment the invention provides a compound wherein $W^{1a}$ has the formula:

E

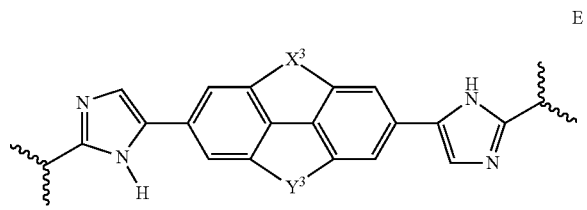

and $W^{1a}$ is optionally substituted with one or more groups independently selected from halo, alkyl, haloalkyl, and cyano.

In one specific embodiment the invention provides a compound which has formula:

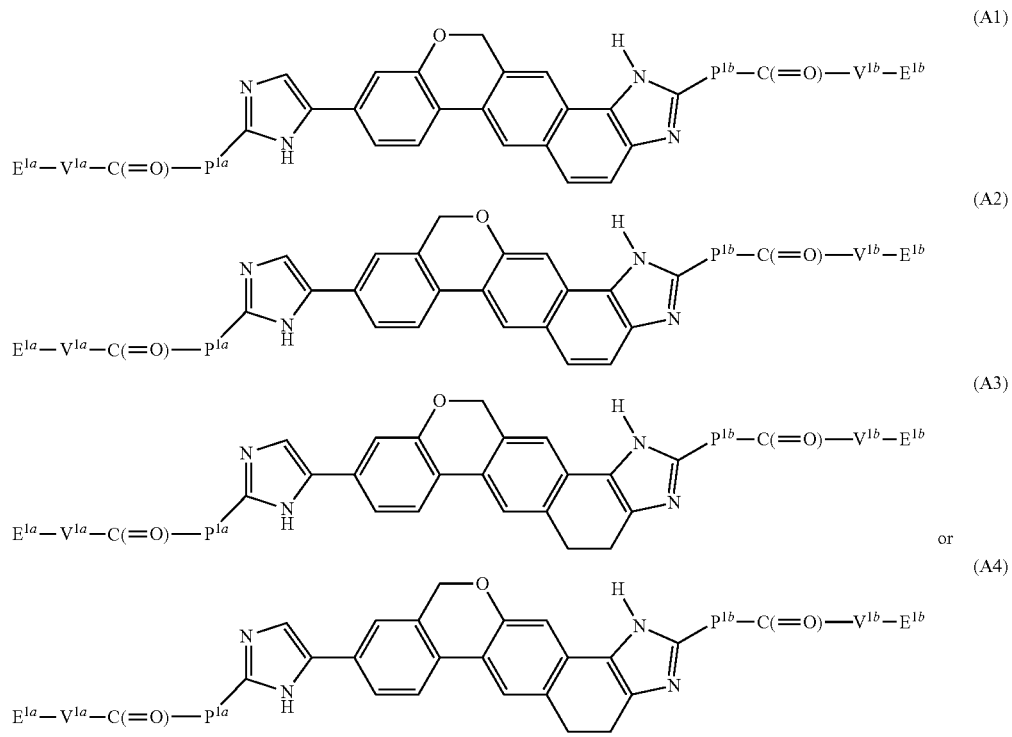

(A1)

(A2)

(A3)

or (A4)

wherein the imidazole ring shown in formula A1, A2, A3, and A4 is optionally substituted with one or more groups independently selected from halo, haloalkyl, cyano, and alkyl;

or a pharmaceutically acceptable salt or prodrug thereof.

In one specific embodiment the invention provides a compound which has formula:

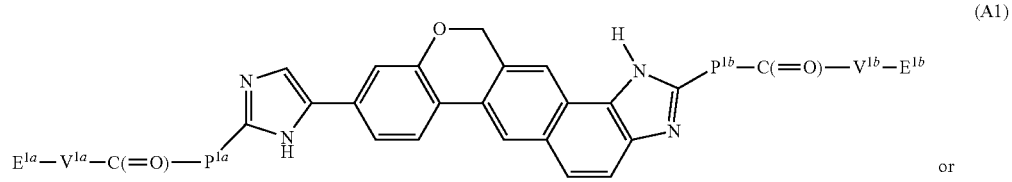

(A1)

or (A3)

[Chemical structure: E^{1a}—V^{1a}—C(=O)—P^{1a}—[imidazole-fused polycyclic system with O bridge]—P^{1b}—C(=O)—V^{1b}—E^{1b}]

wherein the imidazole ring shown in formula Ib1 and Ib3 is optionally substituted with one or more groups independently selected from halo, haloalkyl, cyano, and alkyl;

or a pharmaceutically acceptable salt or prodrug thereof.

In one specific embodiment the invention provides a compound wherein $X^{18}$ is —CH=CH—.

In one specific embodiment the invention provides a compound wherein $X^{18}$ is —CH$_2$CH$_2$—.

In one specific embodiment the invention provides a compound wherein $X^{18}$ is —OCH$_2$—.

In one specific embodiment the invention provides a compound wherein $W^{1a}$ is:

[Three chemical structures of fused polycyclic imidazole systems]

wherein any imidazole ring shown in $W^{1a}$ is optionally substituted with one or more groups independently selected from halo, haloalkyl, cyano, and alkyl.

In one specific embodiment the invention provides a compound wherein at least one of $E^{1a}$ and $E^{1b}$ is —N(H)(alkoxycarbonyl).

In one specific embodiment the invention provides a compound wherein at least one of $E^{1a}$ and $E^{1b}$ is —N(H)C(=O)OMe.

In one specific embodiment the invention provides a compound wherein both of $E^{1a}$ and $E^{1b}$ are —N(H)C(=O)OMe.

In one specific embodiment the invention provides a compound wherein at least one of $E^{1a}$ and $E^{1b}$ is —N(H)(cycloalkylcarbonyl) or —N(H)(cycloalkyloxycarbonyl).

In one specific embodiment the invention provides a compound wherein at least one of $E^{1a}$ and $E^{1b}$ is cyclopropylcarbonylamino, cyclobutylcarbonylamino, cyclopropyloxycarbonylamino or cyclobutyloxycarbonylamino.

In one specific embodiment the invention provides a compound wherein $E^{1a}$ and $E^{1b}$ are each independently selected from cyclopropylcarbonylamino, cyclobutylcarbonylamino, cyclopropyloxycarbonylamino and methoxycarbonylamino.

In one specific embodiment the invention provides a compound wherein at least one of $V^{1a}$ and $V^{1b}$ is selected from:

[Multiple chemical substructure drawings showing isopropyl, phenyl-substituted, tetrahydropyranyl, methoxy-substituted, and related branched groups]

and

[Additional methoxy-containing substructure]

In one specific embodiment the invention provides a compound wherein at least one of $V^{1a}$ and $V^{1b}$ is:

[Chemical substructure drawing]

In one specific embodiment the invention provides a compound wherein at least one of $V^{1a}$ and $V^{1b}$ is selected from:

[Chemical substructure drawings: isopropyl, phenyl, tetrahydropyranyl, methoxymethyl groups]

-continued

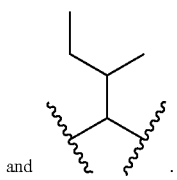

and

In one specific embodiment the invention provides a compound wherein $V^{1a}$ and $V^{1b}$ are each independently selected from:

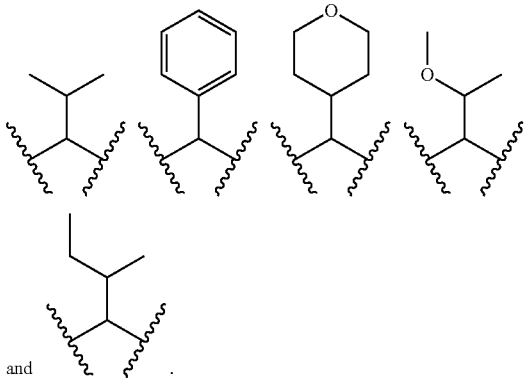

and

In one specific embodiment the invention provides a compound wherein $R^{9a}$ or $R^{9b}$ is selected from:

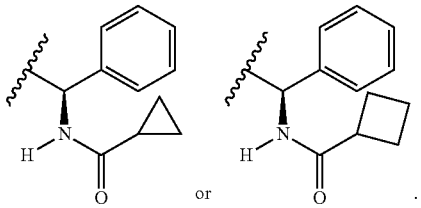 [SMILES: *[C@H](NC(=O)C1CC1)c1ccccc1 ; *[C@H](NC(=O)C1CCC1)c1ccccc1]

or

In one specific embodiment the invention provides a compound wherein at least one of $P^{1a}$ and $P^{1b}$ is selected from:

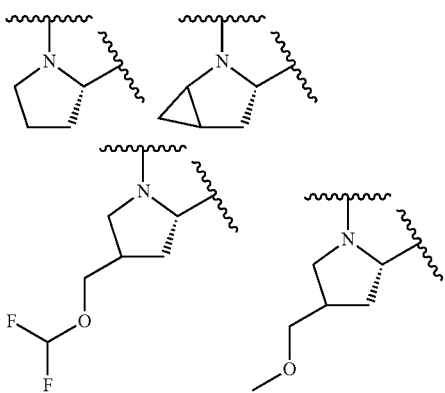

-continued

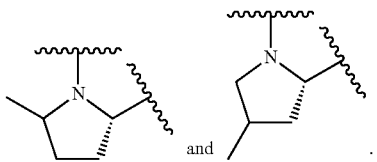

and

In one specific embodiment the invention provides a compound wherein $P^{1a}$ and $P^{1b}$ are each independently selected from:

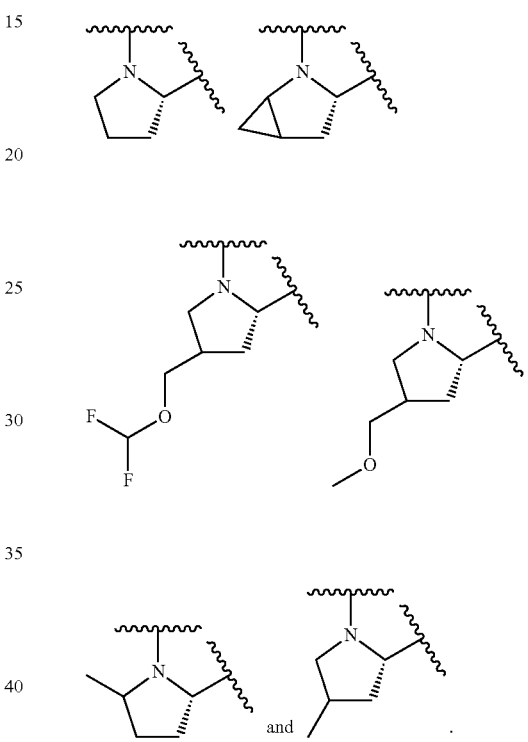

and

In one specific embodiment the invention provides a compound wherein at least one of $P^{1a}$ and $P^{1b}$ is selected from:

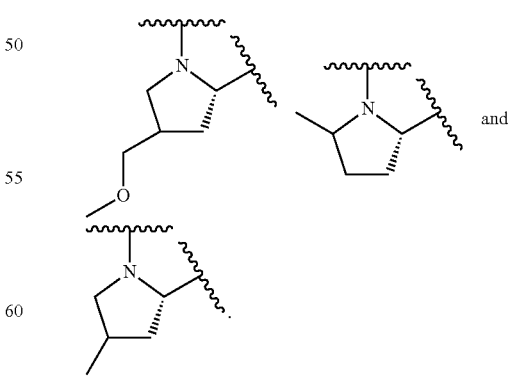

and

In one specific embodiment the invention provides a compound wherein $P^{1a}$ and $P^{1b}$ are each independently selected from:

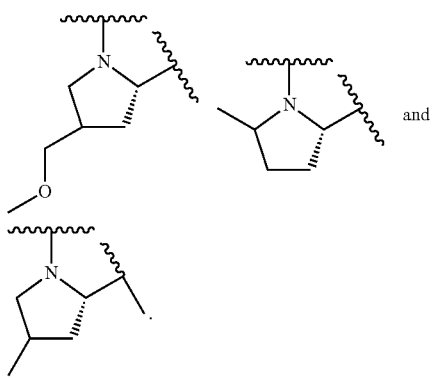

and

In one specific embodiment the invention provides a compound wherein one of $P^{1a}$ and $P^{1b}$ is:

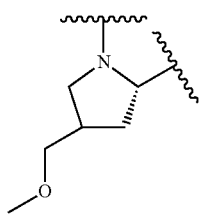

and the other of $P^{1a}$ and $P^{1b}$ is:

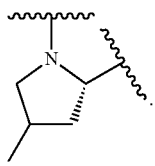

In one specific embodiment the invention provides a compound wherein one of $P^{1a}$ and $P^{1b}$ is:

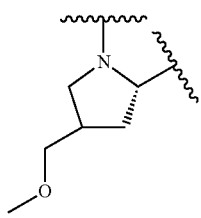

and the other of $P^{1a}$ and $P^{1b}$ is:

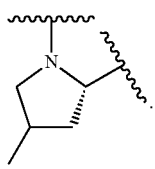

In one specific embodiment the invention provides a compound wherein at least one of $P^{1a}$ and $P^{1b}$ is:

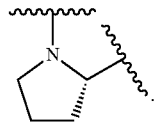

In one specific embodiment the invention provides a compound wherein at least one of $P^{1a}$ and $P^{1b}$ is:

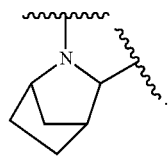 [SMILES: *C1C2CCC(C2)N1*]

In one specific embodiment the invention provides a compound wherein at least one of $P^{1a}$ and $P^{1b}$ is:

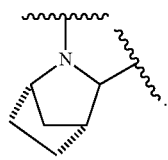 [SMILES: *C1[C@@H]2CC[C@@H](C2)N1*]

In one specific embodiment the invention provides a compound wherein at least one of $P^{1a}$ and $P^{1b}$ is:

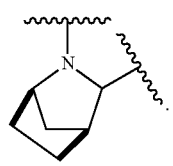 [SMILES: *C1[C@H]2CC[C@H](C2)N1*]

In one specific embodiment the invention provides a compound wherein at least one of $P^{1a}$ and $P^{1b}$ is:

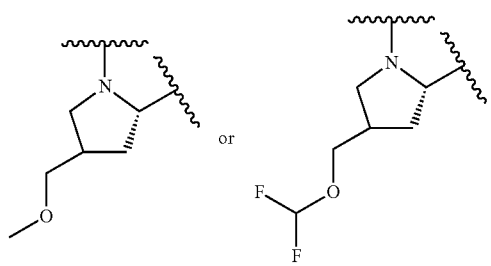

or

In one specific embodiment the invention provides a compound wherein at least one of $P^{1a}$ and $P^{1b}$ is:

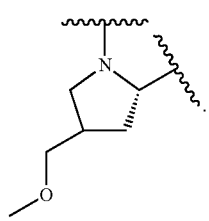

In one specific embodiment the invention provides a compound wherein at least one of —V$^{1a}$—C(=O)—P$^{1a}$— and —P$^{1b}$—C(=O)—V$^{1b}$— is:

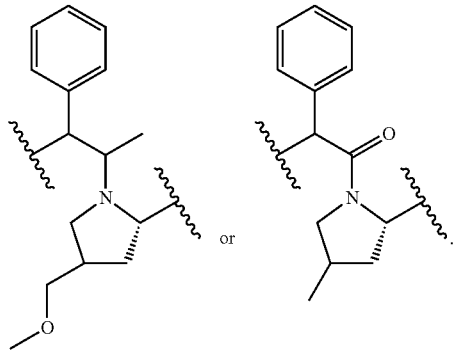

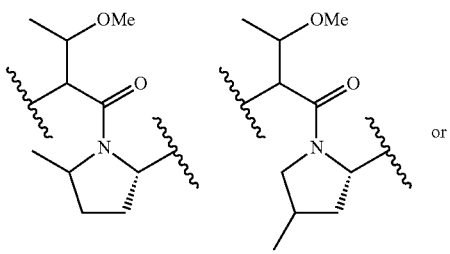

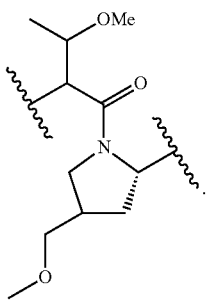

In one specific embodiment the invention provides a compound wherein at least one of —V$^{1a}$—C(=O)—P$^{1a}$— and —P$^{1b}$—C(=O)—V$^{1b}$— is:

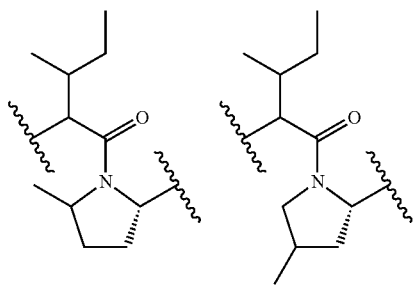

In one specific embodiment the invention provides a compound wherein both of —V$^{1a}$—C(=O)—P$^{1a}$— and —P$^{1b}$—C(=O)—V$^{1b}$— are independently selected from:

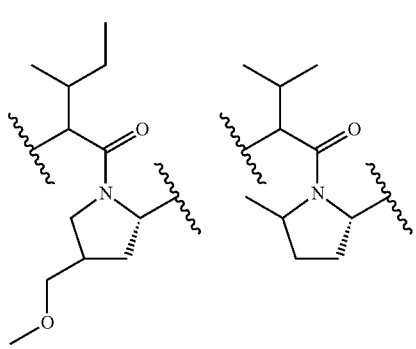

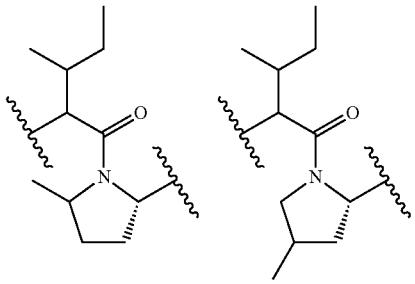

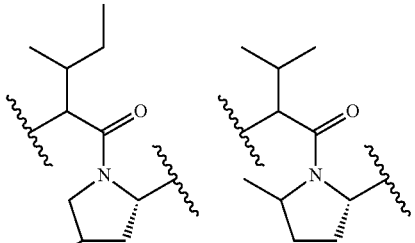

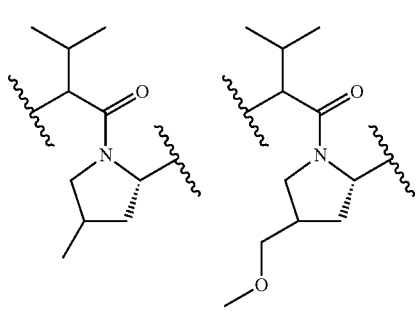

-continued
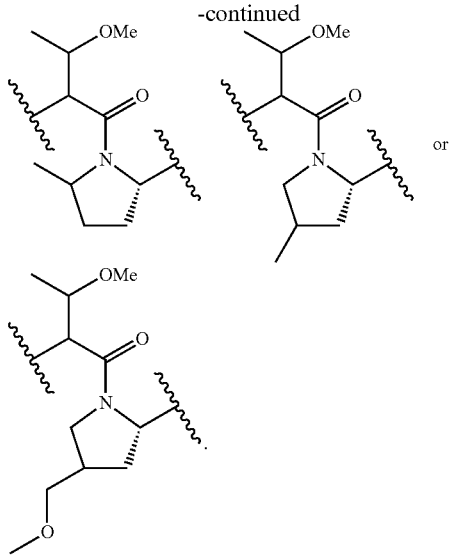
In one specific embodiment the invention provides a compound wherein one of —$V^{1a}$—C(=O)—$P^{1a}$— and —$P^{1b}$—C(=O)—$V^{1b}$— is:
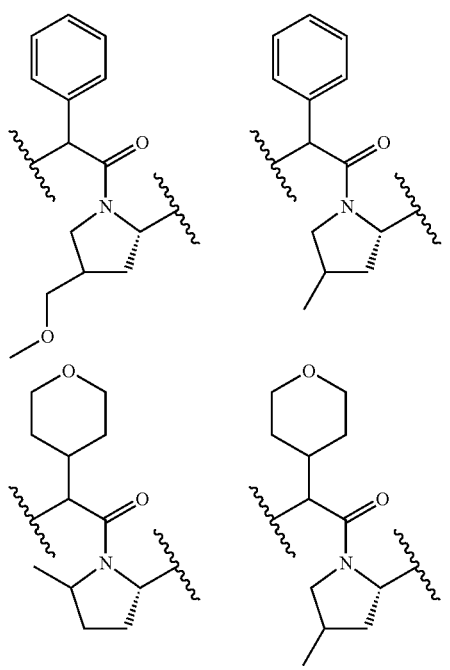
and the other of —$V^{1a}$—C(=O)—$P^{1a}$— and —$P^{1b}$—C(=O)—$V^{1b}$— is:
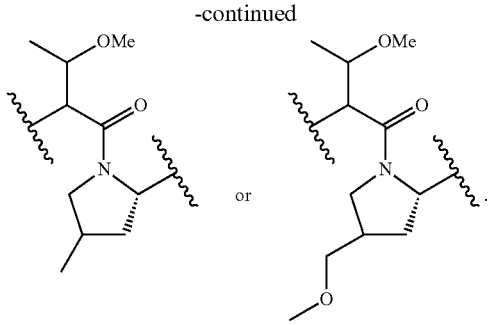
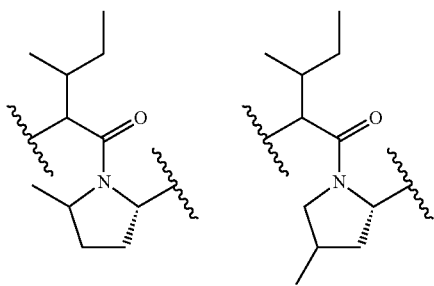
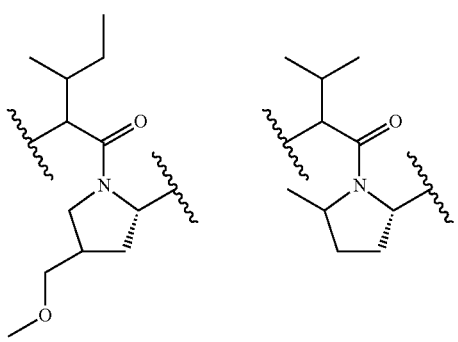
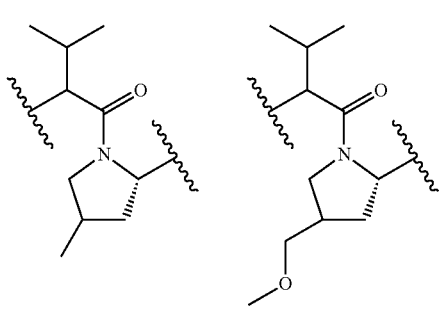

609
-continued
610
-continued
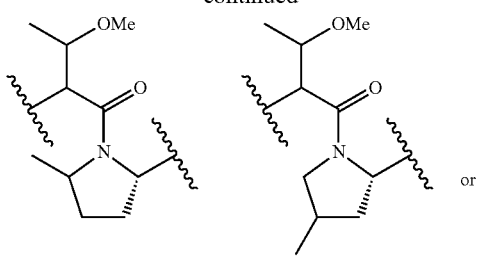
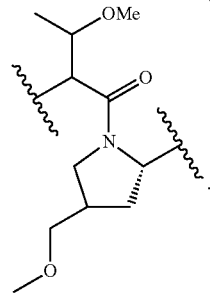
or
In one specific embodiment the invention provides a compound of formula:
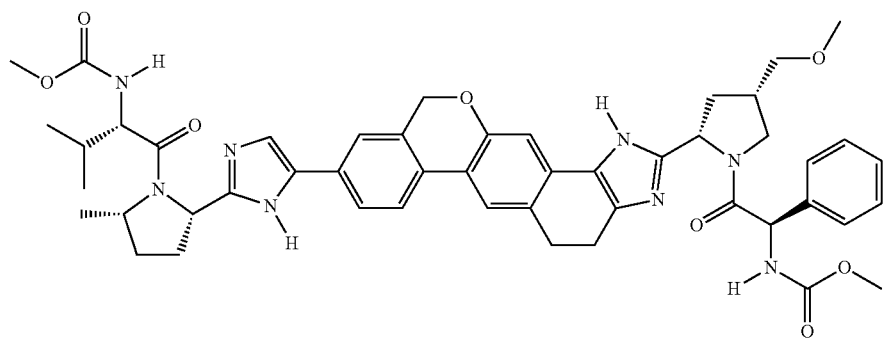
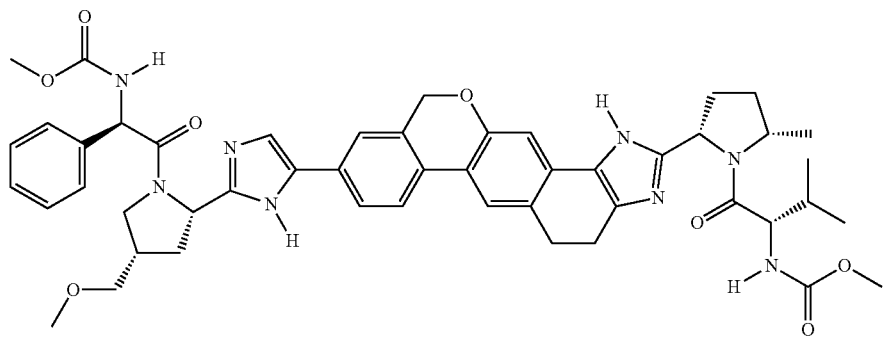
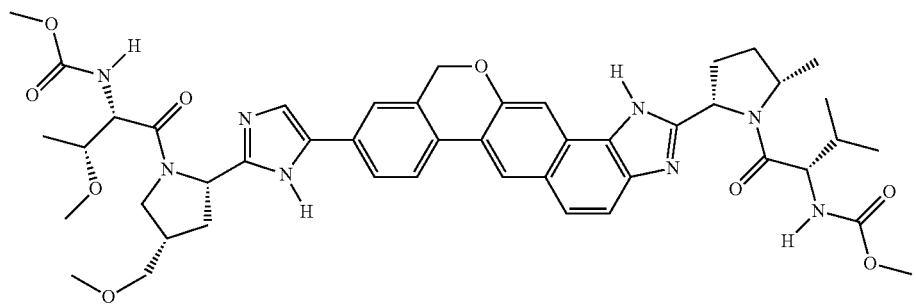

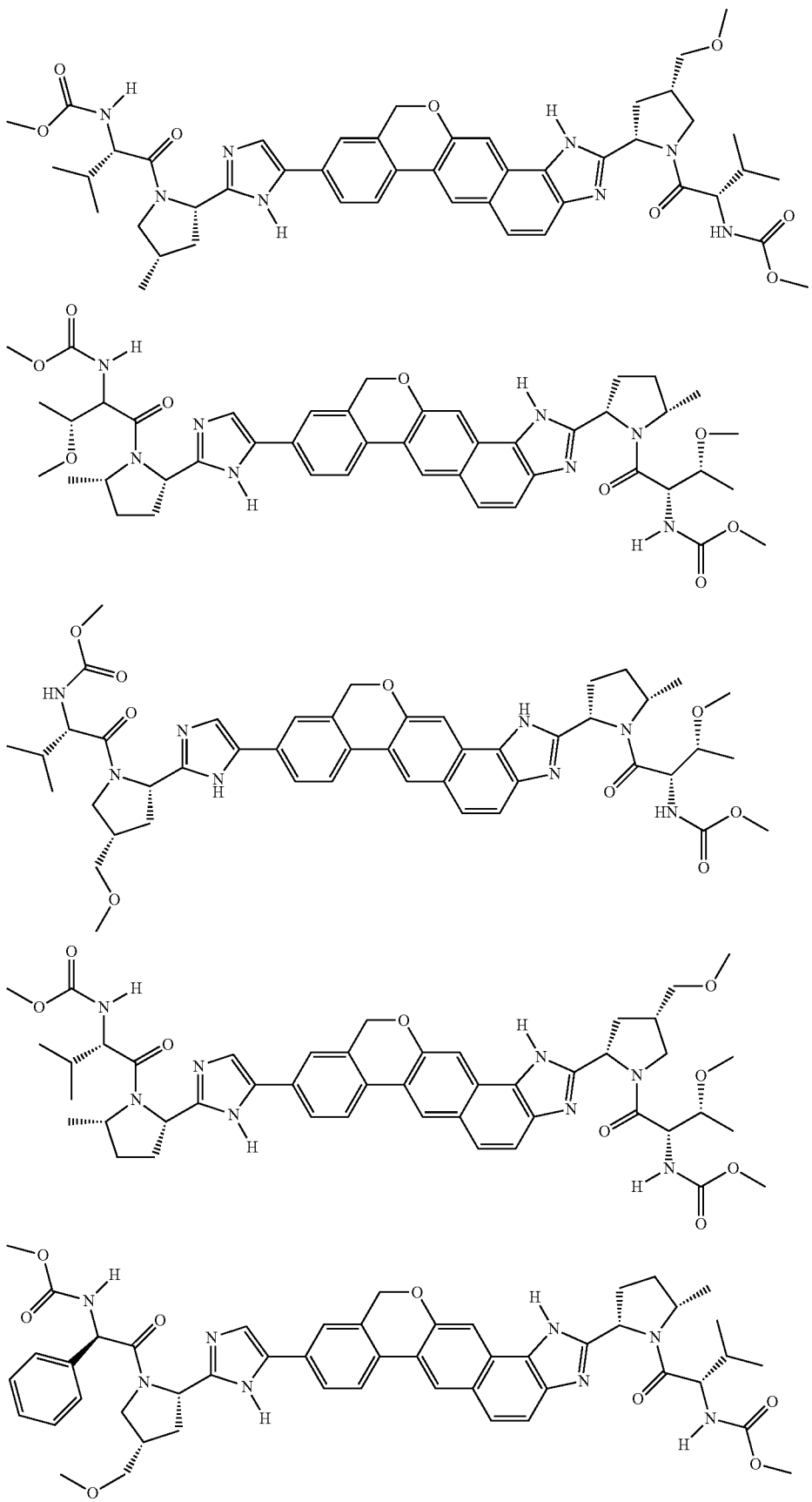

-continued
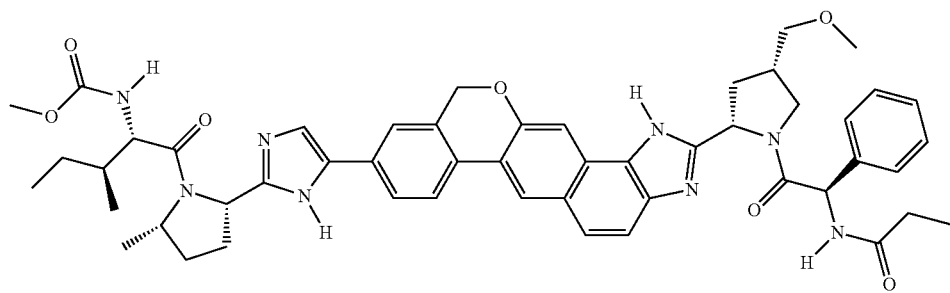
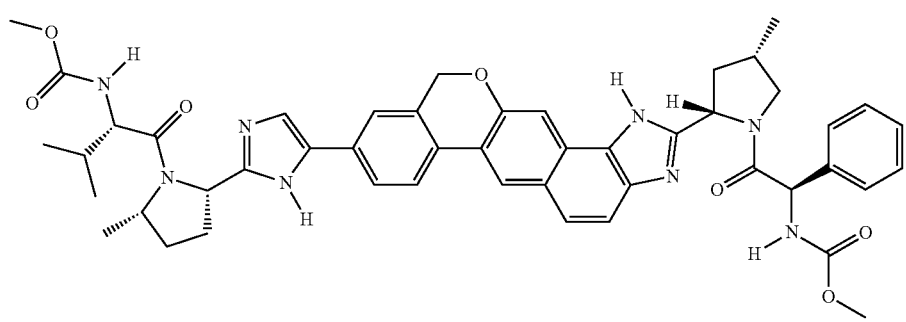
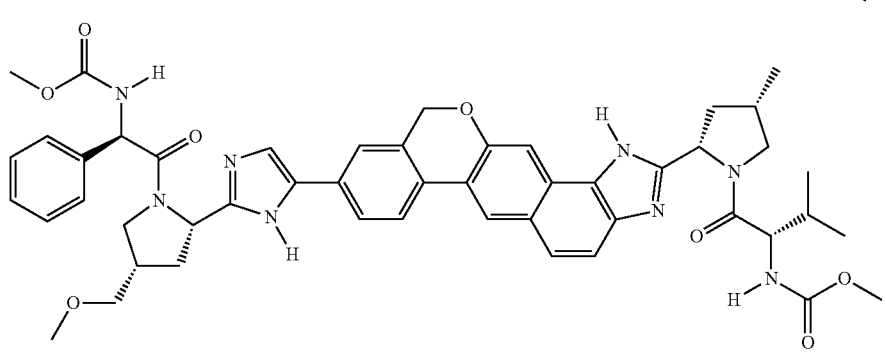
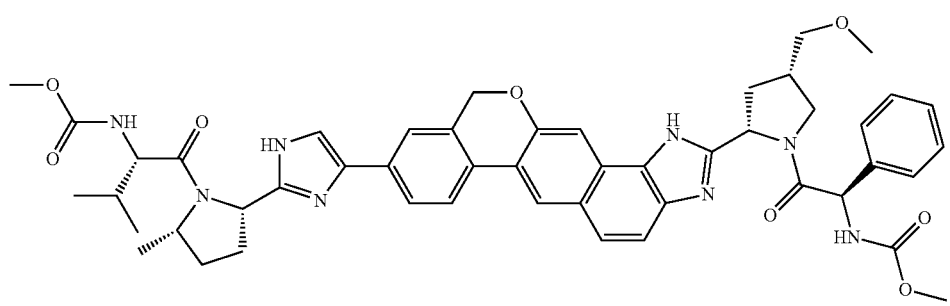
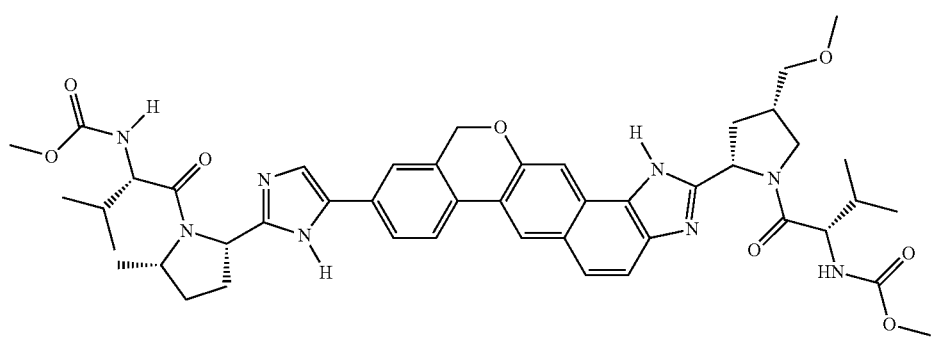

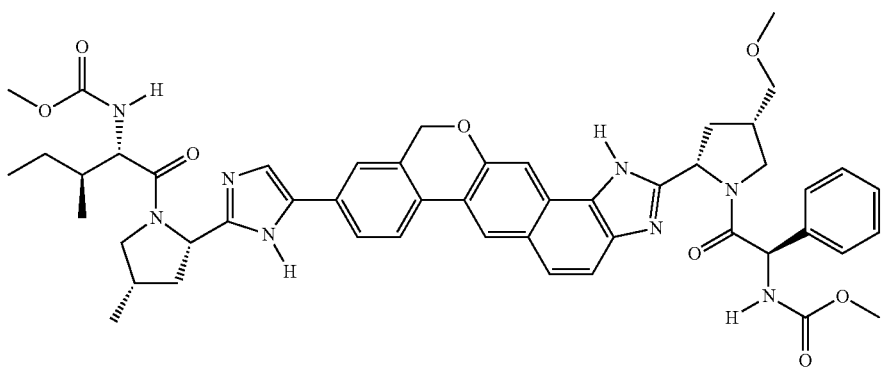
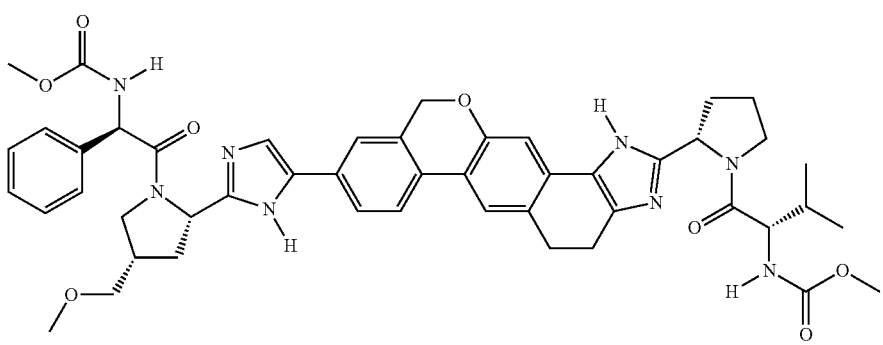
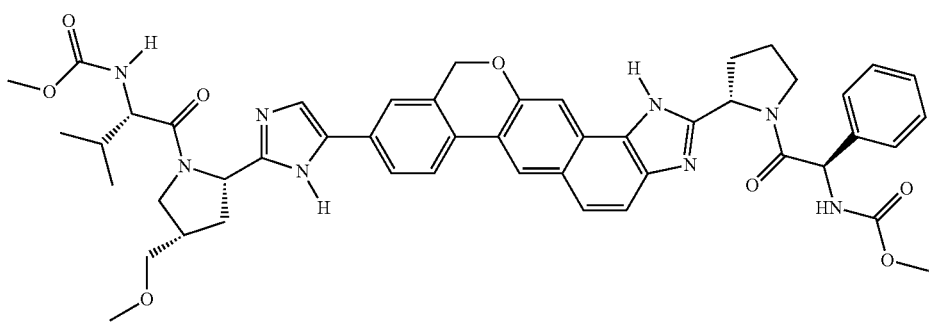
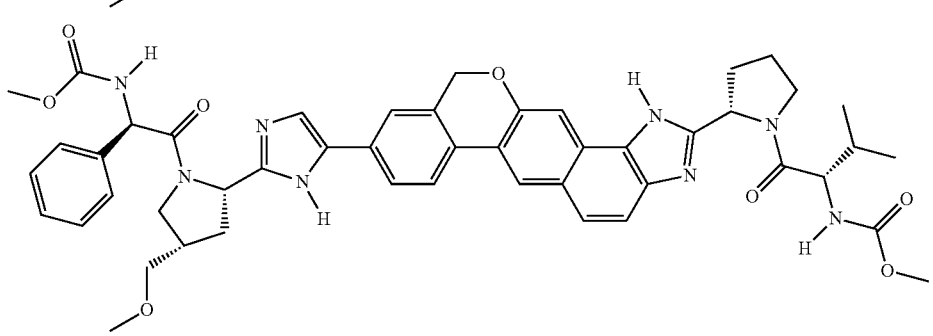
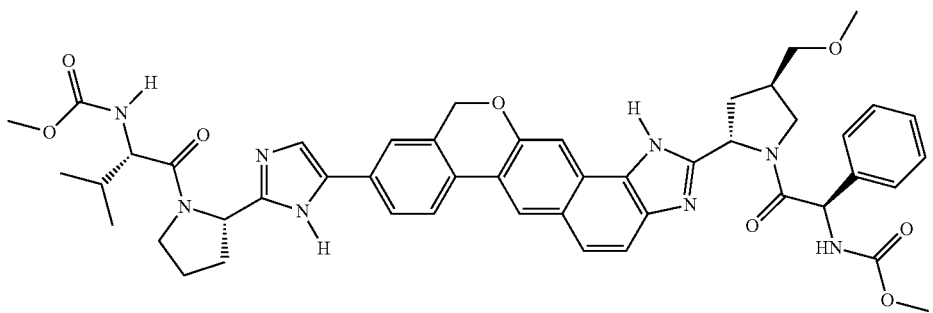

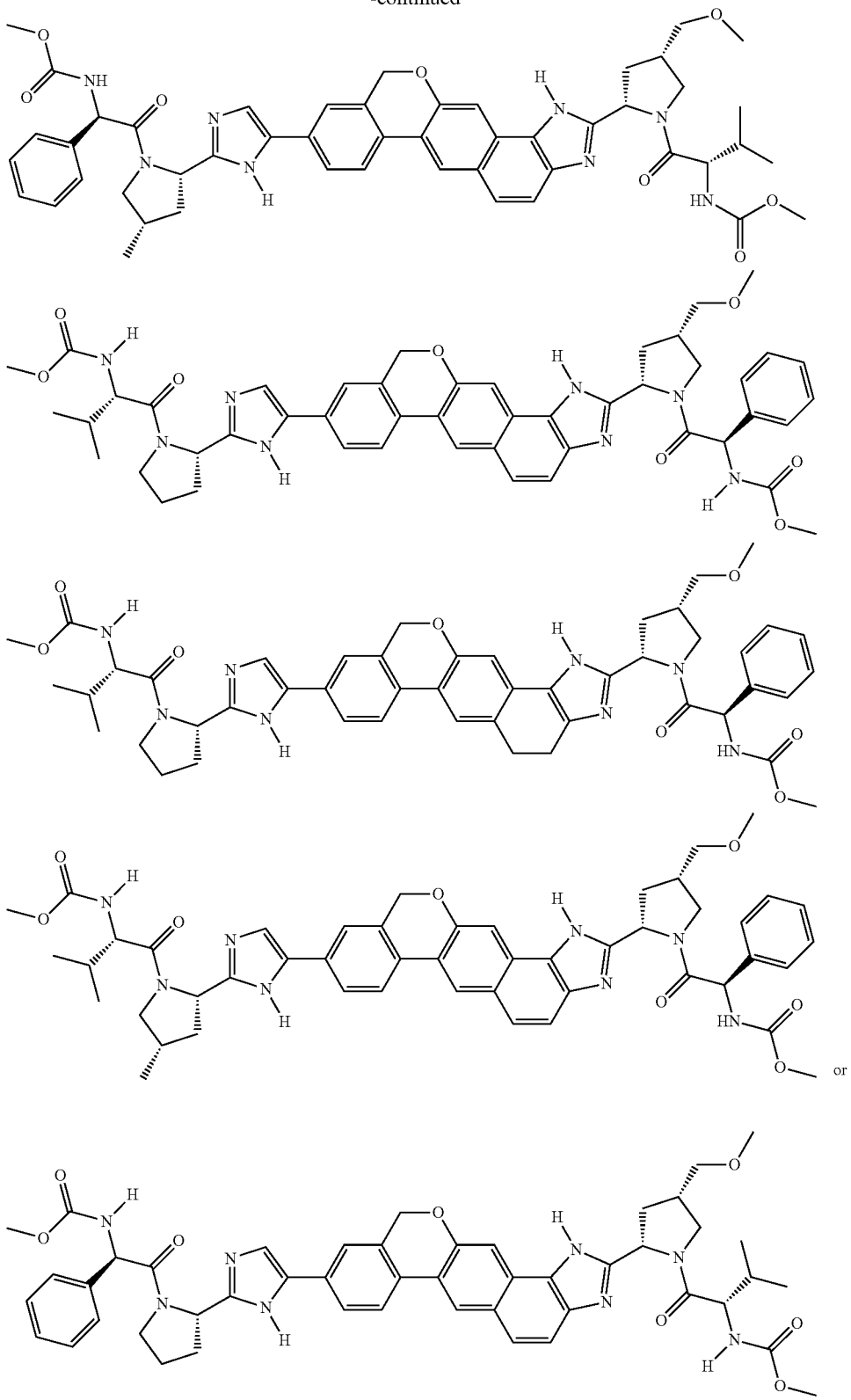
or a pharmaceutically acceptable salt or prodrug thereof.
In one specific embodiment the invention provides a compound of formula:

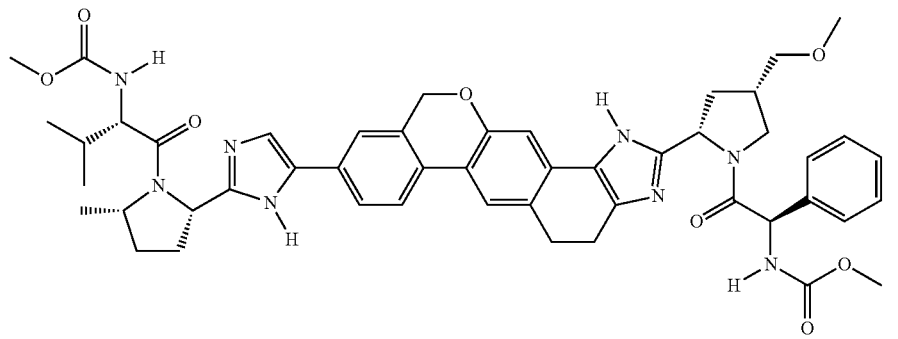
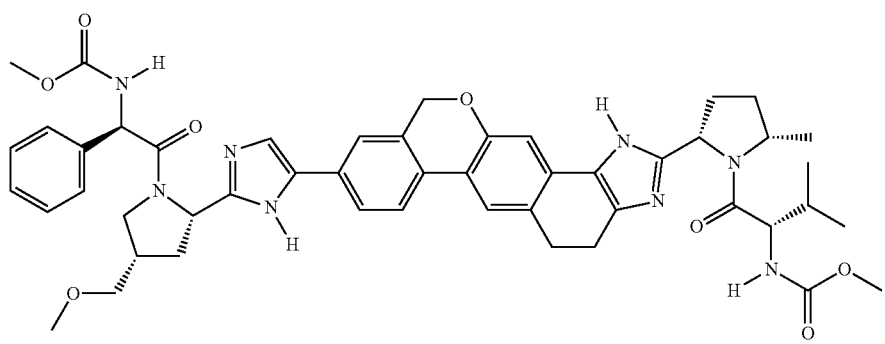
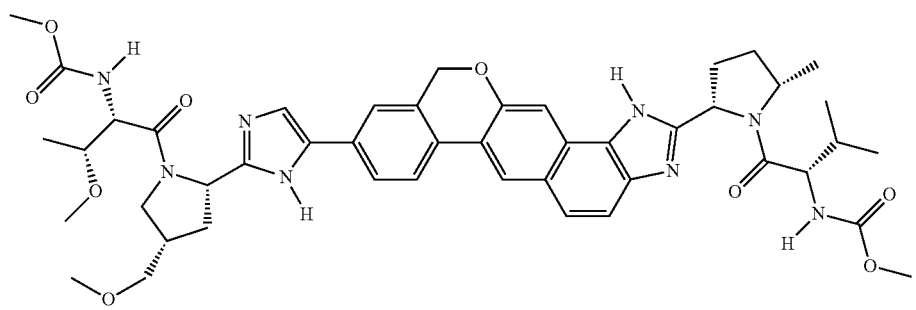
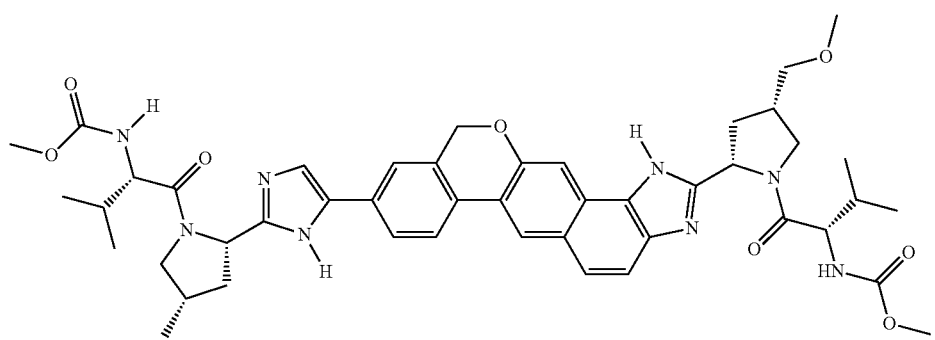
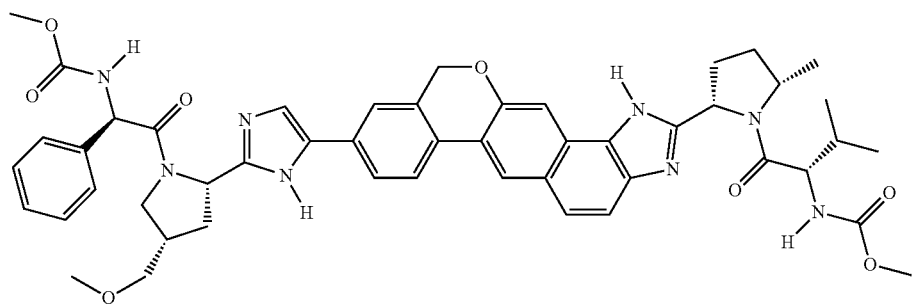

-continued
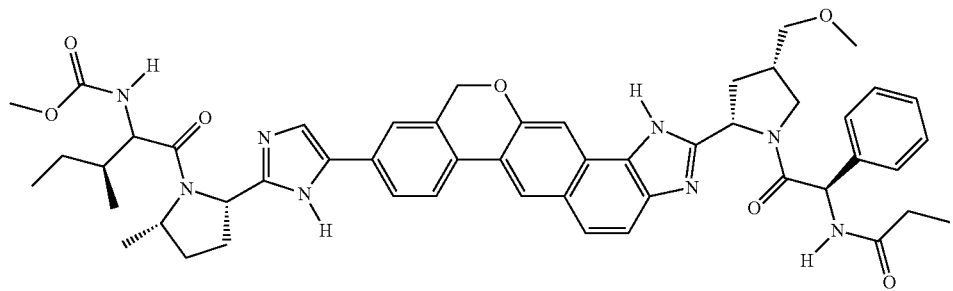
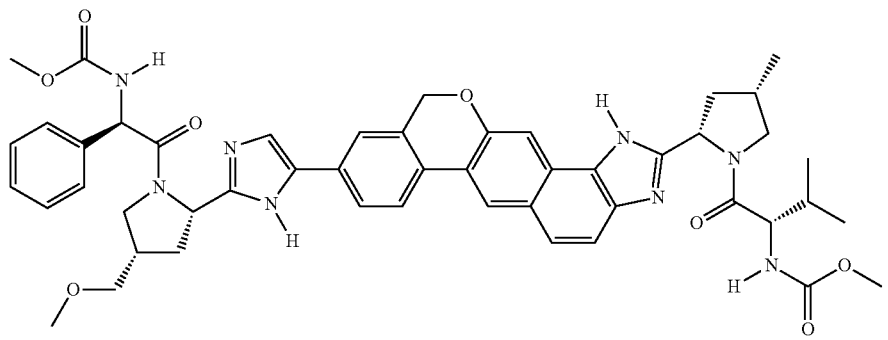
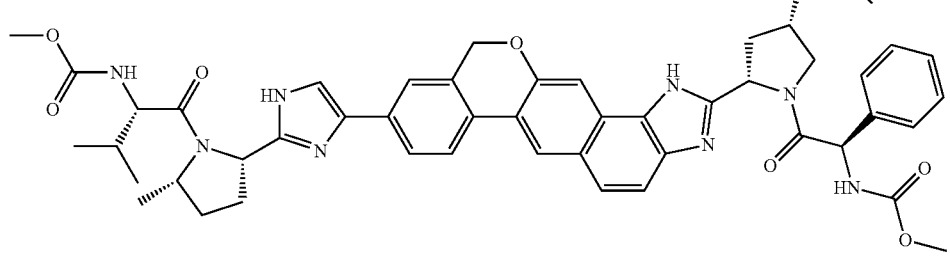
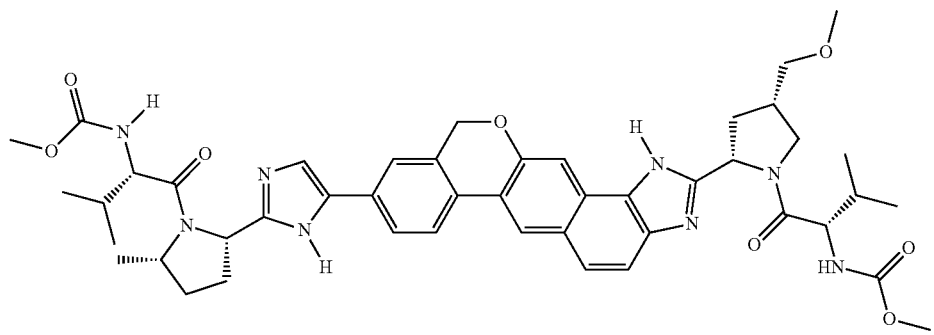
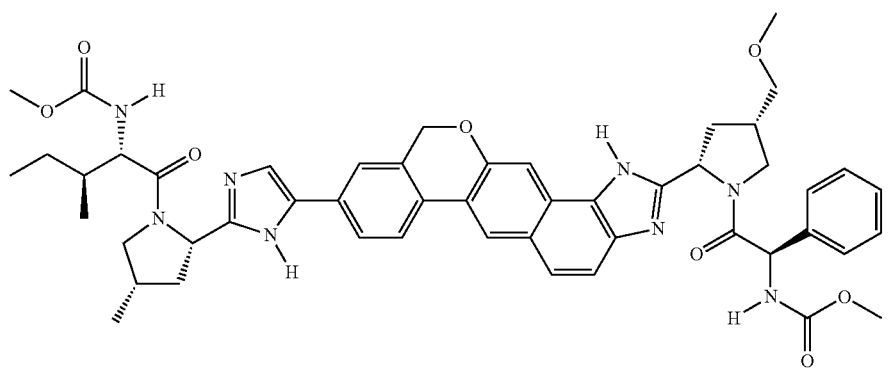

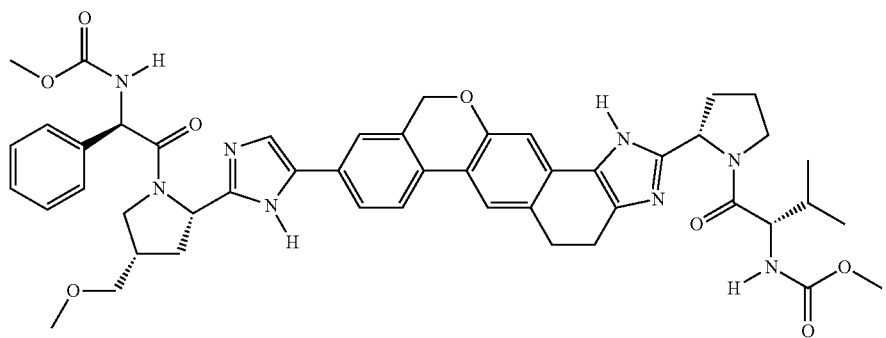
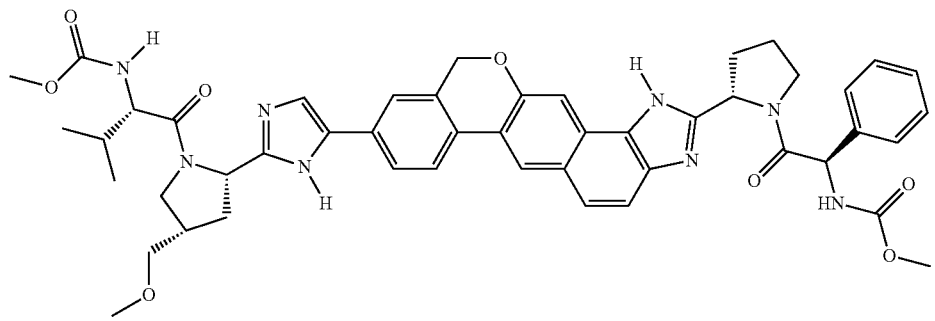
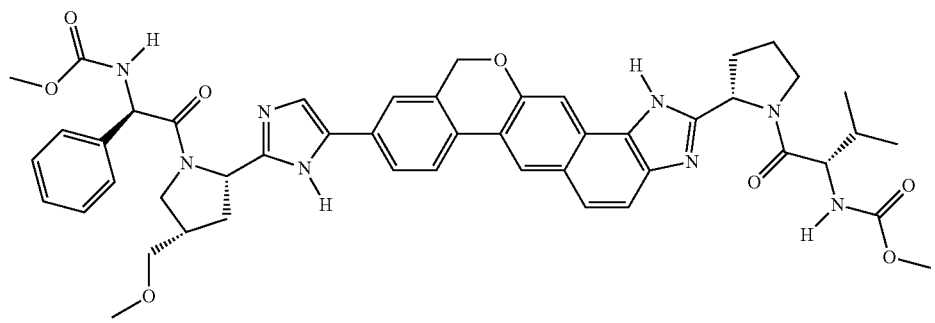
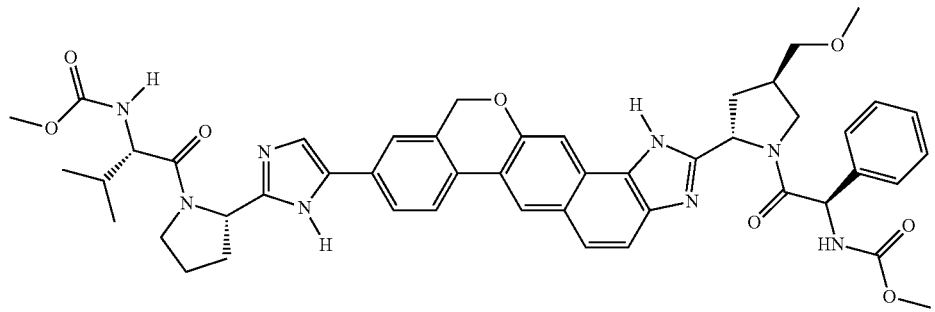
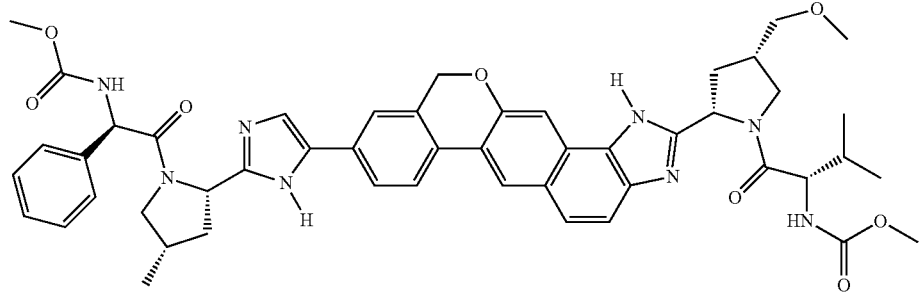

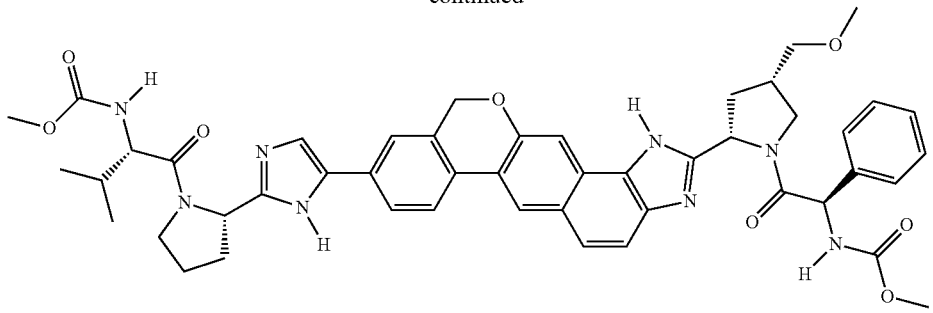

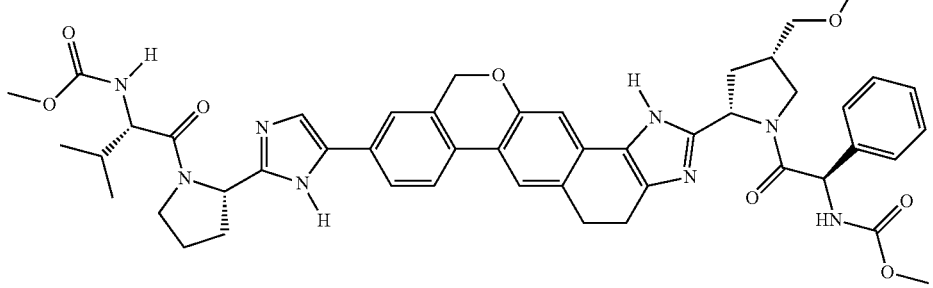

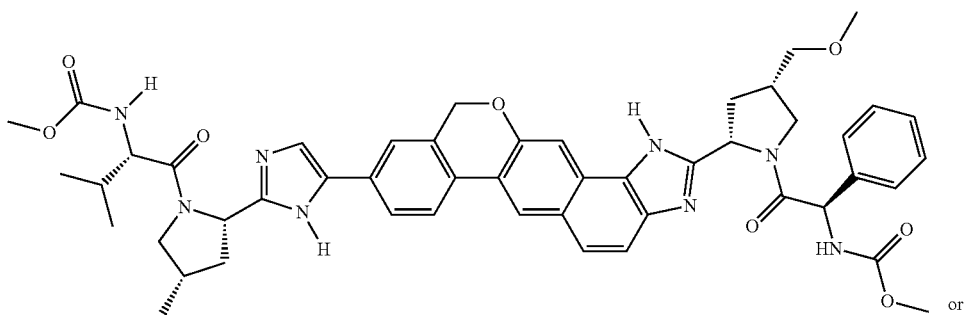

or

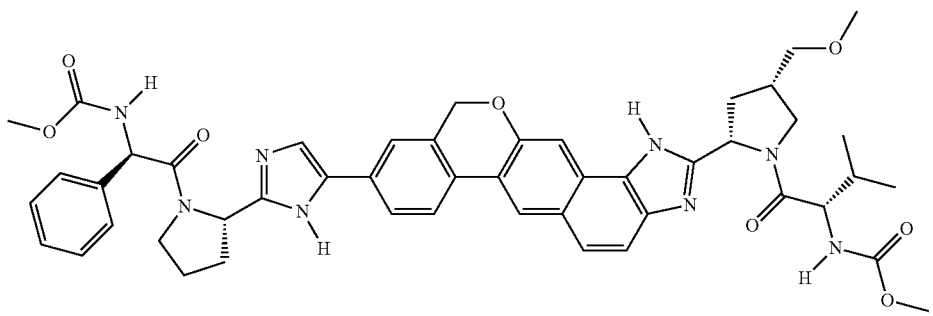

or a pharmaceutically acceptable salt or prodrug thereof.

In one specific embodiment the invention provides a compound prepared in the Examples herein that is a compound of specific Embodiment E, or a salt or a prodrug thereof.

In one specific embodiment the invention provides the compound of Example 538, 544, 555, 561, 562, 572, 587, 589, 590, 592, 594, 599, 606, 608, 610, 614, 615, 617, 622, 625, 627, 637, or 639, or a pharmaceutically acceptable salt or prodrug thereof.

In one specific embodiment the invention provides the compound of Example 506, 519, 527, or 591 or a pharmaceutically acceptable salt or prodrug thereof.

In one specific embodiment the invention provides the compound of Example 451, 453, 472, 509, 528, 529, 554, 559, 560, or 568, or a pharmaceutically acceptable salt or prodrug thereof.

In one specific embodiment the invention provides the compound of Example 460, 520, 564, 586, 596, 611, or 616 or a pharmaceutically acceptable salt or prodrug thereof.

In one specific embodiment the invention provides the compound of Example 433, 442, or 446, or a pharmaceutically acceptable salt or prodrug thereof.

The invention will now be illustrated by the following non-limiting Examples.

EXAMPLES

Example A

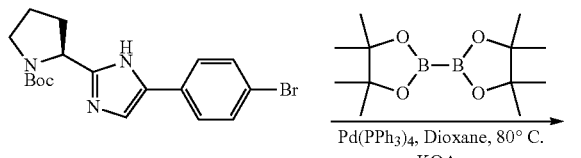

2-[5-(4-Bromo-phenyl)-1H-imidazol-2-yl]-pyrrolidine-1-carboxylic acid tert-butyl ester

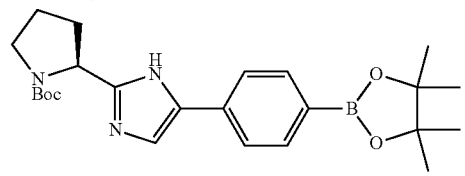

2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester (S)-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester 1,4-Dioxane (300 mL) was added to a mixture of (S)-2-[5-(4-bromo-phenyl)-1H-imidazol-2-yl]-pyrrolidine-1-carboxylic acid tert-butyl ester (21.1 g, 53.7 mmol), bis(pinacolato)diboron (27.3g, 107.5 mmol), tetrakis(triphenylphosphine)palladium (0) (3.10 g, 2.68 mmol), and potassium acetate (15.02 g, 153.0 mmol), and heated at 80° C. for 16 hours. The mixture was cooled and the resulting solid was filtered. The majority of the 1,4-dioxane was removed from the filtrate under reduced pressure and resulting residue was taken up in ethyl acetate (300 mL). The organic phase was washed with saturated sodium bicarbonate (2×150 mL), brine (100 mL) and dried over sodium sulfate. After filtration the solvent was removed from the filtrate under reduced pressure. The resulting oil was subjected to silica gel chromatography using a 330 g Isco column and effluent of 20-100% ethyl acetate and hexanes. The fractions containing product were combined and the solvent was removed under reduced pressure to provide (S)-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester (18 g, 76%) and light yellow solid.

Example AA

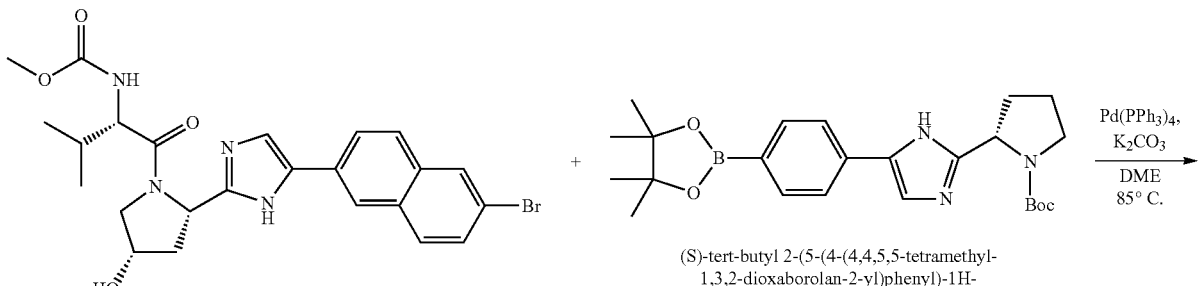

methyl (S)-1-((2S, 4S)-2-(5-(6-bromonaphthalen-2-yl)-1H-imidazol-2-yl)-4-hydroxypyrrolidin-1-yl)-3-methyl-1-oxobutan-2-ylcarbamate (S)-tert-butyl 2-(5-(4-(4,4,5,5-tetramethyl-1,3,2-dioxaborolan-2-yl)phenyl)-1H-imidazol-2-yl)pyrrolidine-1-carboxylate

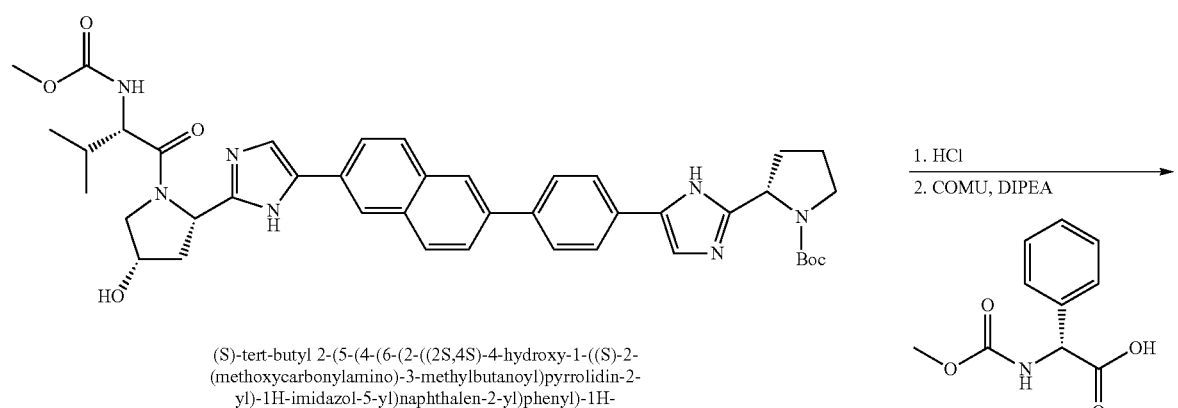

(S)-tert-butyl 2-(5-(4-(6-(2-((2S,4S)-4-hydroxy-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate -continued

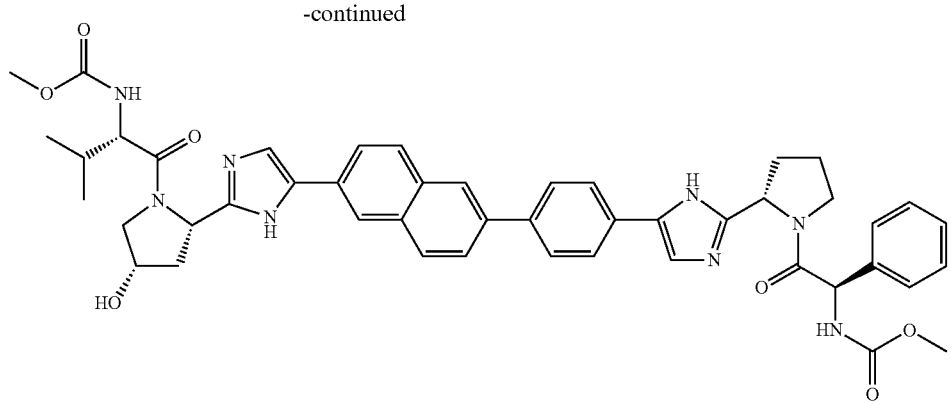

methyl (R)-2-((S)-2-(5-(4-(6-(2-((2S,4S)-4-hydroxy-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxo-1-phenylethylcarbamate (S)-tert-butyl 2-(5-(4-(6-(2-((2S,4S)-4-hydroxy-1-((S)-2-(methoxycarbonylamino)-3-methyl butanoyl)pyrrolidin-2-yl)-1H-imidazol-5-yl)naphthalen-2-yl)phenyl)-1H-imidazol-2-yl)pyrrolidine-1-carboxylate To a solution of methyl (S)-1-((2S,4S)-2-(5-(6-bromonaphthalen-2-yl)-1H-imidazol-2-yl)-4-hydroxypyrrolidin-1-yl)-3-methyl-1-oxobutan-2-ylcarbamate (100 mg, 0.19 mmol) in DME (2 mL) was added (S)-tert-butyl 2-(5-(4-(4,4,5,5-tetramethyl-1,3,2-dioxaborolan-2-yl)phenyl)-1H-imidazol-2-yl)pyrrolidine-1-carboxylate (83 mg, 0.19 mmol), Pd(PPh$_3$)$_4$ (22 mg, 0.019 mmol), and K$_2$CO$_3$ (2M in H$_2$O, 0.32 mL, 0.63 mmol). The solution was degassed with N$_2$ for 10 min, then heated to 85° C. for 18 h. The mixture was cooled to rt, diluted with EtOAc, and washed with sat. NaHCO$_3$, brine, dried over MgSO$_4$, and concentrated. The residue was purified by silica gel chromatography to yield product (61 mg).

Methyl (R)-2-((S)-2-(5-(4-(6-(2-((2S,4S)-4-hydroxy-1-((S)-2-(methoxycarbonylamino)-3-methyl butanoyl)pyrrolidin-2-yl)-1H-imidazol-5-yl)naphthalen-2-yl)phenyl)-1H-imidazol-2-yl)pyrrolidin-1-yl)-2-oxo-1-phenylethylcarbamate To (S)-tert-butyl 2-(5-(4-(6-(2-((2S,4S)-4-hydroxy-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate (61 mg, 0.082 mmol) in MeOH (2.5 mL) was added HCl (4M in dioxane, 0.5 mL). The solution stirred o/n, and the solvent was removed. The intermediate was dissolved in DMF (2 mL). (R)-2-(methoxycarbonylamino)-2-phenylacetic acid (19 mg, 0.09 mmol), COMU (39 mg, 0.082 mmol), and DIPEA (0.07 mL, 0.41 mmol) were added sequentially. The solution was stirred o/n and the mixture was purified by HPLC to yield product (15.5 mg). LCMS-ESI$^+$: calc'd for C$_{47}$H$_{50}$N$_8$O$_7$: 838.95 (M$^+$). Found: 839.29 (M+H$^+$)

Example AB

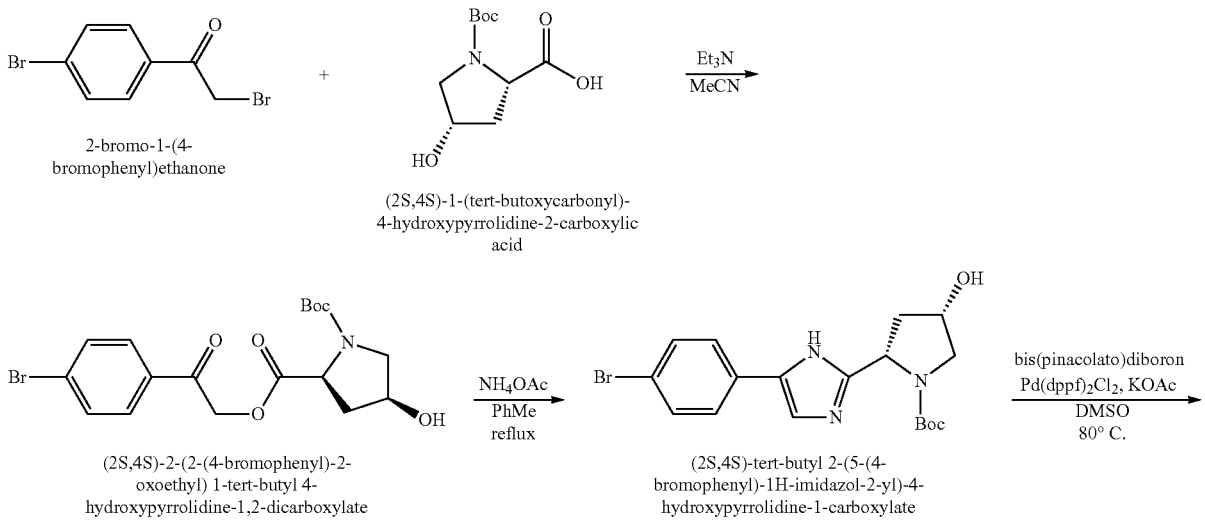

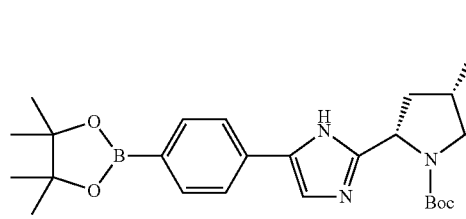

(2S,4S)-tert-butyl 4-hydroxy-2-(5-(4-(4,4,5,5-tetramethyl-1,3,2-dioxaborolan-2-yl)phenyl)-1H-imidazol-2-yl)pyrrolidine-1-carboxylate

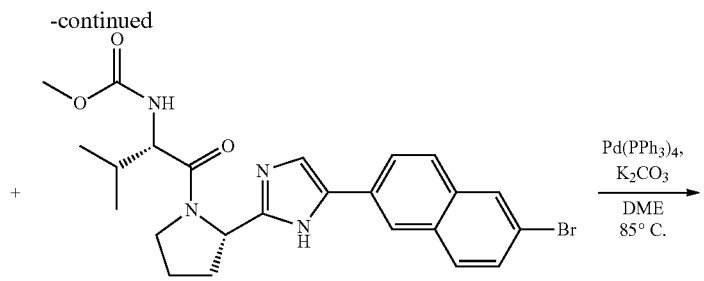

methyl (S)-1-((2S, 4S)-2-(5-(6-bromonaphthalen-2-yl)-1H-imidazol-2-yl)pyrrolidin-1-yl)-3-methyl-1-oxobutan-2-ylcarbamate

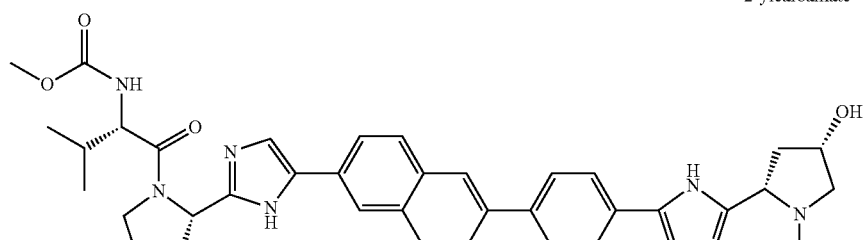

(2S,4S)-tert-butyl 4-hydoxy-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate

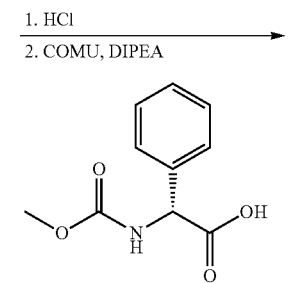

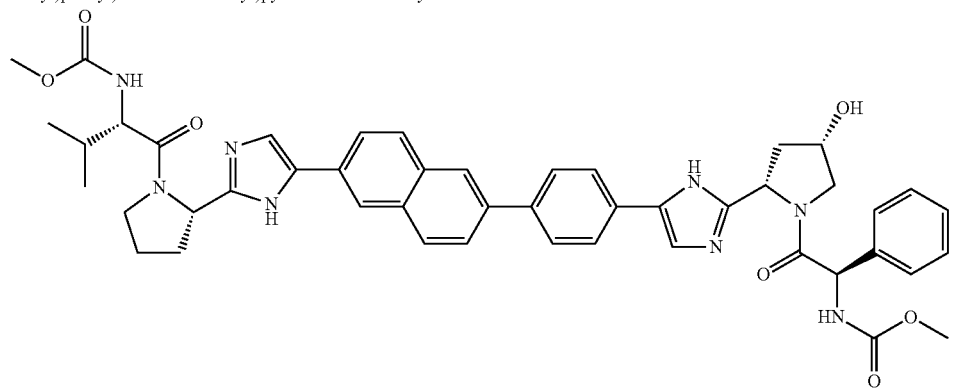

methyl (R)-2-((S)-2-(5-(4-(6-(2-((2S,4S)-4-hydroxy-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxo-1-phenylethylcarbamate (2S,4S)-2-(2-(4-bromophenyl)-2-oxoethyl) 1-tert-butyl 4-hydroxypyrrolidine-1,2-dicarboxylate To a solution of 2-bromo-1-(4-bromophenyl)ethanone (3.6 g, 12.98 mmol) and (2S,4S)-1-(tert-butoxycarbonyl)-4-hydroxypyrrolidine-2-carboxylic acid (2.0 g, 8.65 mmol) in MeCN (50 mL) was added Et$_3$N (1.8 mL, 12.98 mmol). After 3 h, the solution was diluted with EtOAc, sat. NaHCO$_3$, brine, dried over MgSO$_4$, and concentrated. The residue was taken on crude to yield product (3.1 g).

(2S,4S)-tert-butyl 2-(5-(4-bromophenyl)-1H-imidazol-2-yl)-4-hydroxypyrrolidine-1-carboxylate To a solution of (2S,4S)-2-(2-(4-bromophenyl)-2-oxoethyl) 1-tert-butyl 4-hydroxypyrrolidine-1,2-dicarboxylate (3.1 g, 7.24 mmol) in PhMe (75 mL) was added NH$_4$OAc (5.58 g, 72.38 mmol). The solution was heated to reflux for 4 h. The solution was cooled, and diluted with EtOAc, washed with H$_2$O, sat. NaHCO$_3$, brine, dried over MgSO$_4$, and concentrated. The residue was purified by silica gel chromatography to yield product (250 mg).

(2S,4S)-tert-butyl 4-hydroxy-2-(5-(4-(4,4,5,5-tetramethyl-1,3,2-dioxaborolan-2-yl)phenyl)-1H-imidazol-2-yl)pyrrolidine-1-carboxylate (2S,4S)-tert-butyl 2-(5-(4-bromophenyl)-1H-imidazol-2-yl)-4-hydroxypyrrolidine-1-carboxylate (250 mg, 0.61 mmol) in DMSO (8 mL) was added bis(pinacolato)diboron (187 mg, 0.74 mmol), KOAc (180 mg, 1.84 mmol), and Pd(dppf)$_2$Cl$_2$ (45 mg, 0.06 mmol). The solution was degassed with N$_2$ for 10 min, then heated to 80° C. for 18 h. The solution was cooled to rt, diluted with EtOAc, washed with sat. NaHCO$_3$, brine, dried over MgSO$_4$, and concentrated. Purified by silica gel chromatography to yield the product (112 mg).

(2S,4S)-tert-butyl 4-hydroxy-2-(5-(4-(6-(2-((S)-1-((S)-2-(methoxycarbonylamino)-3-methyl butanoyl)pyrrolidin-2-yl)-1H-imidazol-5-yl)naphthalen-2-yl)phenyl)-1H-imidazol-2-yl)pyrrolidine-1-carboxylate (2S,4S)-tert-butyl 4-hydroxy-2-(5-(4-(4,4,5,5-tetramethyl-1,3,2-dioxaborolan-2-yl)phenyl)-1H-imidazol-2-yl)

pyrrolidine-1-carboxylate (200 mg, 0.44 mmol) and methyl (S)-1-((S)-2-(5-(6-bromonaphthalen-2-yl)-1H-imidazol-2-yl)pyrrolidin-1-yl)-3-methyl-1-oxobutan-2-ylcarbamate (219 mg, 0.44 mmol) were combined in DME (5 mL). Pd(PPh₃)₄ (51 mg, 0.0446 mmol) and K₂CO₃ (2M H₂O, 0.73 mL, 1.45 mmol) were added, and the solution was degassed with N₂ for 10 min. The solution was heated to 85° C. and stirred o/n. The following morning, the solution was cooled to rt. The solution was diluted with EtOAc, washed with sat. NaHCO₃, brine, dried over MgSO₄, and concentrated. The residue was purified by silica gel chromatography to yield product (36 mg).

Methyl (R)-2-((S)-2-(5-(4-(6-(2-((2S,4S)-4-hydroxy-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxo-1-phenylethylcarbamate To (2S,4S)-tert-butyl 4-hydroxy-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate (36 mg, 0.048 mmol) in DCM (2.5 mL) and MeOH (1 mL) was added HCl (4M in dioxane, 0.25 mL). The solution stirred for 3 h, and the solvent was removed. The residue was dissolved in DMF (1 mL). (R)-2-(methoxycarbonylamino)-2-phenylacetic acid (11 mg, 0.05 mmol), COMU (23 mg, 0.048 mmol), and DIPEA (0.04 mL, 0.24 mmol) were added sequentially. The solution stirred o/n and the mixture was purified by HPLC to yield product (6.9 mg). LCMS-ESI⁺: calc'd for $C_{47}H_{50}N_8O_7$: 838.95 (M⁺). Found: 840.38 (M+H⁺)

Example AC

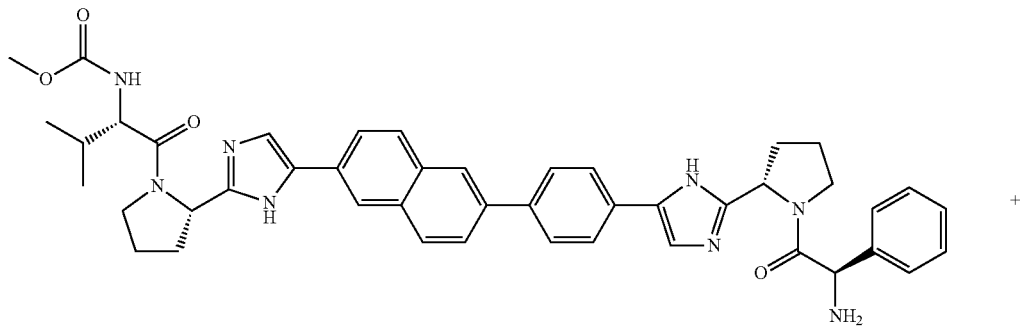

methyl (S)-1-((S)-2-(5-(6-(4-(2-((S)-1-((R)-2-amino-2-phenylacetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate

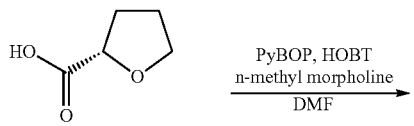

(S)-tetrahydrofuran-2-carboxylic acid

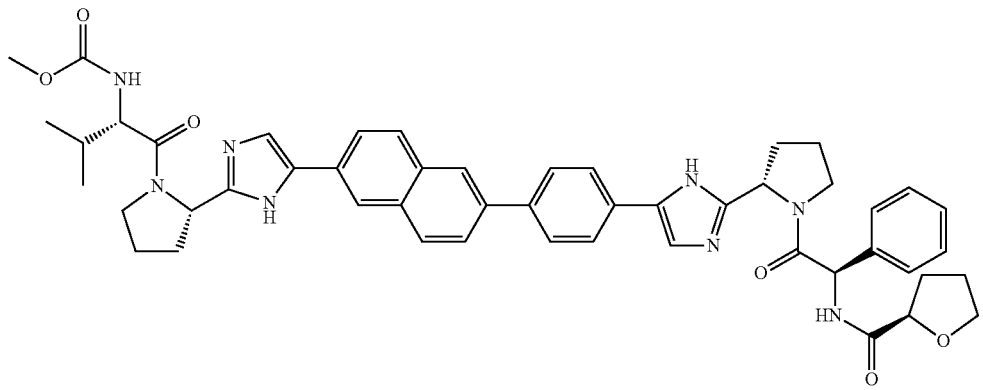

methyl (S)-3-methyl-1-oxo-1-((S)-2-(5-(6-(4-(2-((S)-1-((R)-2-phenyl-2-((S)-tetrahydrofuran-2-carboxamido)acetyl)pyrrolidin-2-yl)-1H-imidazol-5-yl)phenyl)naphthalen-2-yl)-1H-imidazol-2-yl)pyrrolidin-1-yl)butan-2-ylcarbamate Methyl (S)-3-methyl-1-oxo-1-((S)-2-(5-(6-(4-(2-((S)-1-((R)-2-phenyl-2-((R)-tetrahydrofuran-2-carboxamido)acetyl)pyrrolidin-2-yl)-1H-imidazol-5-yl)phenyl)naphthalen-2-yl)-1H-imidazol-2-yl)pyrrolidin-1-yl)butan-2-ylcarbamate To a 0° C. solution of methyl (S)-1-((S)-2-(5-(6-(4-(2-((S)-1-((R)-2-amino-2-phenylacetyl) pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate (70 mg, 0.08 mmol) in DMF (1 mL) was added (S)-tetrahydrofuran-2-carboxylic acid (10 mg, 0.09 mmol), PyBOP (52 mg, 0.10 mmol), HOBT (14 mg, 0.10 mmol), and N-methylmorpholine (40 mg, 0.4 mmol) successively. The solution was warmed to rt and allowed to stir for 2 h. The mixture was diluted with EtOAc, washed with 1N HCl, sat. NaHCO₃, and brine, dried over MgSO₄, and concentrated. The residue was purified by silica gel chromatography to yield product (9.5 mg). LCMS-ESI⁺: calc'd for $C_{50}H_{54}N_8O_6$: 863.01 (M⁺); Found: 863.31 (M+H⁺).

Example AD

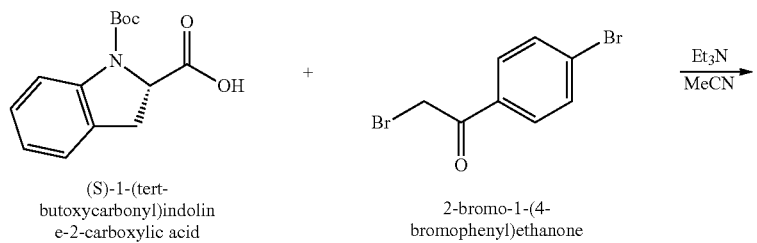

(S)-1-(tert-butoxycarbonyl)indoline-2-carboxylic acid 2-bromo-1-(4-bromophenyl)ethanone

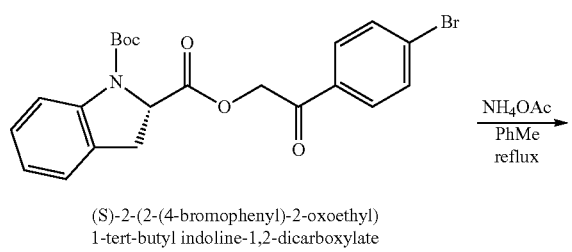

(S)-2-(2-(4-bromophenyl)-2-oxoethyl) 1-tert-butyl indoline-1,2-dicarboxylate

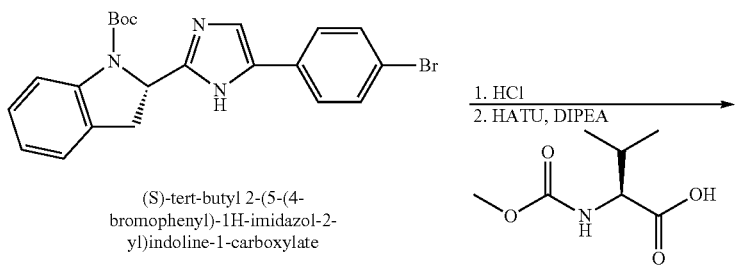

(S)-tert-butyl 2-(5-(4-bromophenyl)-1H-imidazol-2-yl)indoline-1-carboxylate

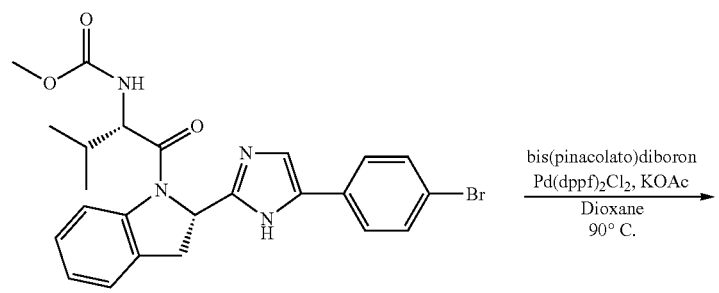

methyl (S)-1-((S)-2-(5-(4-bromophenyl)-1H-imidazol-2-yl)indolin-1-yl)-3-methyl-1-oxobutan-2-ylcarbamate

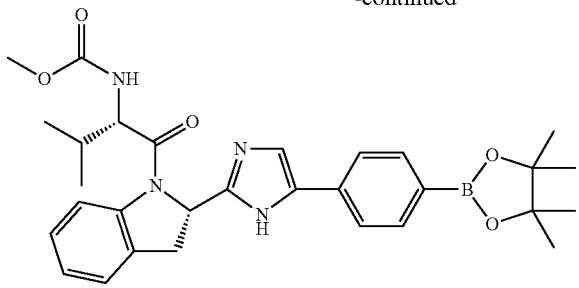

methyl (S)-3-methyl-1-oxo-1-((S)-2-(5-(4-
(4,4,5,5-tetramethyl-1,3,2-dioxaborolan-2-
yl)phenyl)-1H-imidazol-2-yl)indolin-1-yl)butan-2-
ylcarbamate

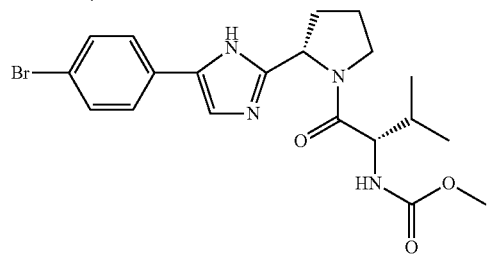

methyl (S)-1-((S)-2-(5-(4-bromophenyl)-
1H-imidazol-2-yl)pyrrolidin-1-yl)-3-
methyl-1-oxobutan-2-ylcarbamate

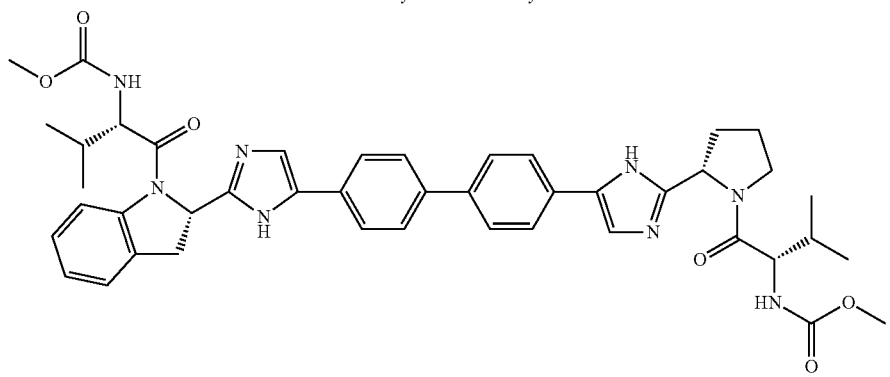

dimethyl (2S, 2'S)-1,1'-((2S, 2'S)-2,2'-(5,5'-(biphenyl-4,4'-(2-((S)-
indolin-2-yl)-1H-imidazol-5-yl)biphenyl-4-yl)-1H-imidazol-2-
yl)pyrrolidin-1-yl)-3-methyl-1-oxobutan-2-yl)dicarbamate (S)-2-(2-(4-bromophenyl)-2-oxoethyl) 1-tert-butyl indo-line-1,2-dicarboxylate To a solution of (S)-1-(tert-butoxycarbonyl)indoline-2-carboxylic acid (1.61 g, 6.11 mmol) and 2-bromo-1-(4-bromophenyl)ethanone (2.55 g, 9.17 mmol) in MeCN (25 mL) was added Et₃N (1.27 mL, 9.17 mmol). The solution was heated to 55° C. and stirred o/n. The solution was cooled to rt, diluted with EtOAc, sat. NaHCO₃, brine, dried with MgSO₄, and concentrated. The residue was taken onto the next step crude.

(S)-tert-butyl 2-(5-(4-bromophenyl)-1H-imidazol-2-yl)indoline-1-carboxylate

To a solution of (S)-2-(2-(4-bromophenyl)-2-oxoethyl) 1-tert-butyl indoline-1,2-dicarboxylate (2.81 g, 6.1 mmol) in PhMe (7 mL) was added NH₄OAc (4.7 g, 61.0 mmol). The solution was heated to reflux for 3 h. The solution was cooled, and diluted with EtOAc, washed with H₂O, sat. NaHCO₃, brine, dried over MgSO₄, and concentrated. The residue was purified by silica gel chromatography to yield product (1.41 g).

Methyl (S)-1-((S)-2-(5-(4-bromophenyl)-1H-imidazol-2-yl)indolin-1-yl)-3-methyl-1-oxobutan-2-ylcarbamate To (S)-tert-butyl 2-(5-(4-bromophenyl)-1H-imidazol-2-yl)indoline-1-carboxylate (1.41 g, 3.2 mmol) in DCM (20 mL) was added HCl (4M in dioxane, 4 mL). The solution stirred for 2 h, and the solvent was removed. The intermediate was dissolved in DMF (30 mL). (S)-2-(methoxycarbonylamino)-3-methylbutanoic acid (560 mg, 3.2 mmol), HATU (1.22 g, 3.2 mmol), and DIPEA (2.79 mL, 16 mmol)

were added sequentially. The solution stirred for 3 h, diluted with EtOAc, washed with sat. NaHCO$_3$, brine, dried over MgSO$_4$, and concentrated. The mixture was purified by silica gel chromatography to yield product (600 mg).

Methyl (S)-3-methyl-1-oxo-1-((S)-2-(5-(4-(4,4,5,5-tetramethyl-1,3,2-dioxaborolan-2-yl)phenyl)-1H-imidazol-2-yl)indolin-1-yl)butan-2-ylcarbamate Methyl (S)-1-((S)-2-(5-(4-bromophenyl)-1H-imidazol-2-yl)indolin-1-yl)-3-methyl-1-oxobutan-2-ylcarbamate (150 mg, 0.3 mmol) in dioxane (5 mL) was added bis(pinacolato)diboron (92 mg, 0.36 mmol), KOAc (89 mg, 0.09 mmol), and Pd(dppf)$_2$Cl$_2$ (23 mg, 0.03 mmol). The solution was degassed with N$_2$ for 10 min, then heated to 90° C. for 22 h. The solution was cooled to rt, diluted with EtOAc, washed with sat. NaHCO$_3$, brine, dried over MgSO$_4$, and concentrated. The crude oil was purified by silica gel chromatography to yield the product (107 mg).

Dimethyl (2S,2'S)-1,1'-((2S,2'S)-2,2'-(5,5'-(biphenyl-4,4'-(2-((S)-indolin-2-yl)-1H-imidazol-5-yl)biphenyl-4-yl)-1H-imidazol-2-yl)pyrrolidin-1-yl)-3-methyl-1-oxobutan-2-yl)dicarbamate To a solution of methyl (S)-1-((S)-2-(5-(4-bromophenyl)-1H-imidazol-2-yl)pyrrolidin-1-yl)-3-methyl-1-oxobutan-2-ylcarbamate (99 mg, 0.22 mmol) and methyl (S)-3-methyl-1-oxo-1-((S)-2-(5-(4-(4,4,5,5-tetramethyl-1,3,2-dioxaborolan-2-yl)phenyl)-1H-imidazol-2-yl)indolin-1-yl)butan-2-ylcarbamate (107 mg, 0.20 mmol) was added Pd(dppf)$_2$Cl$_2$ (15 mg, 0.02 mmol), Pd(PPh$_3$)$_4$ (23 mg, 0.02 mmol), and K$_2$CO$_3$ (2M H$_2$O, 0.33 mL, 0.66 mmol). The solution was degassed for 10 min, and then heated to 80° C. The solution was stirred for 18 h, then cooled to rt. The mixture was diluted with MeOH, filtered, and purified by HPLC to yield product (9.0 mg). LCMS-ESI$^+$: calc'd for C$_{44}$H$_{50}$N$_8$O$_6$: 786.92 (M$^+$); Found: 787.31 (M+H$^+$).

Example AE

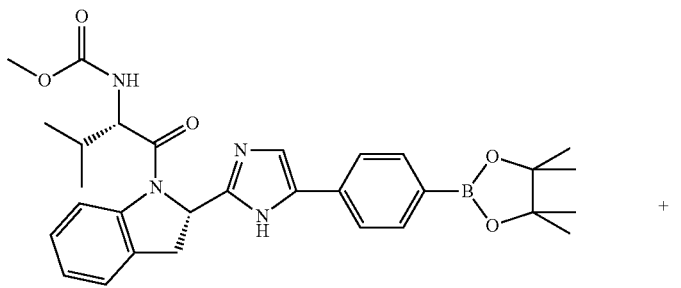

methyl (S)-3-methyl-1-oxo-1-((S)-2-(5-(4-(4,4,5,5-tetramethyl-1,3,2-dioxaborolan-2-yl)phenyl)-1H-imidazol-2-yl)indolin-1-yl)butan-2-ylcarbamate

+

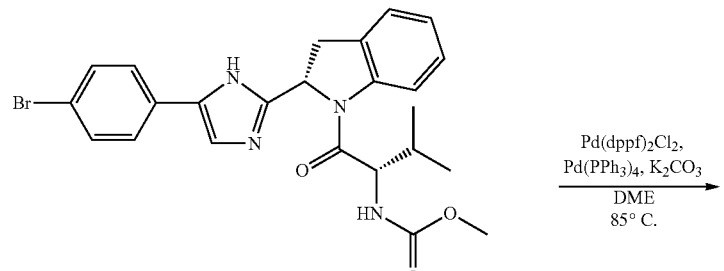

methyl (S)-1-((S)-2-(5-(4-bromophenyl)-1H-imidazol-2-yl)indolin-1-yl)-3-methyl-1-oxobutan-2-ylcarbamate Pd(dppf)$_2$Cl$_2$, Pd(PPh$_3$)$_4$, K$_2$CO$_3$
———————→
DME
85° C.

-continued

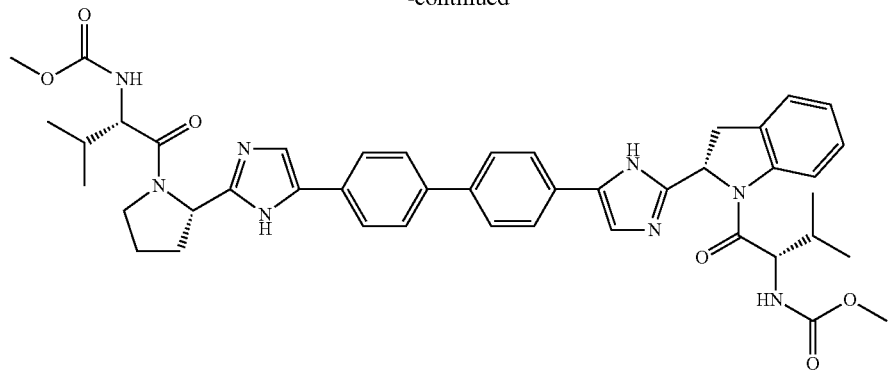

dimethyl (2S,2'S)-1,1'-((2S,2'S)-2,2'-(5,5'-biphenyl-4,4'-diyl)bis(1H-imidazole-5,2-diyl))bis(indoline-2,1-diyl))bis(3-methyl-1-oxobutane-2,1-diyl)dicarbamate

Dimethyl (2S,2'S)-1,1'-((2S,2'S)-2,2'-(5,5'-(biphenyl-4,4'-diyl)bis(1H-imidazole-5,2-diyl))bis(indoline-2,1-diyl))bis(3-methyl-1-oxobutane-2,1-diyl)dicarbamate To a solution of methyl (S)-3-methyl-1-oxo-1-((S)-2-(5-(4-(4,4,5,5-tetramethyl-1,3,2-dioxaborolan-2-yl)phenyl)-1H-imidazol-2-yl)indolin-1-yl)butan-2-ylcarbamate (130 mg, 0.24 mmol) and methyl (S)-1-((S)-2-(5-(4-bromophenyl)-1H-imidazol-2-yl)indolin-1-yl)-3-methyl-1-oxobutan-2-ylcarbamate (150 mg, 0.30 mmol) was added Pd(PPh$_3$)$_4$ (28 mg, 0.024 mmol), Pd(dppf)$_2$Cl$_2$ (18 mg, 0.024 mmol) and K$_2$CO$_3$ (2M H$_2$O, 0.4 mL, 0.79 mmol). The solution was degassed for 10 min, and then heated to 85° C. The solution was stirred for 18 h, then cooled to rt. The mixture was diluted with MeOH, filtered, and purified by HPLC to yield product (114 mg). LCMS-ESI$^+$: calc'd for C$_{48}$H$_{50}$N$_8$O$_6$: 834.96 (M$^+$); Found: 836.41 (M+H$^+$).

Example AF

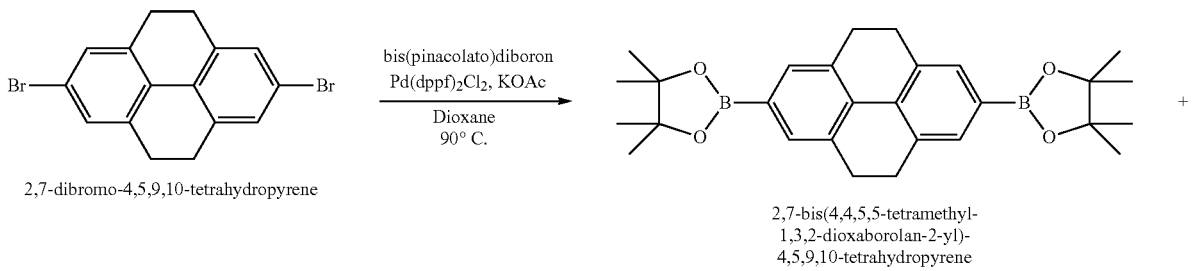

2,7-dibromo-4,5,9,10-tetrahydropyrene 2,7-bis(4,4,5,5-tetramethyl-1,3,2-dioxaborolan-2-yl)-4,5,9,10-tetrahydropyrene

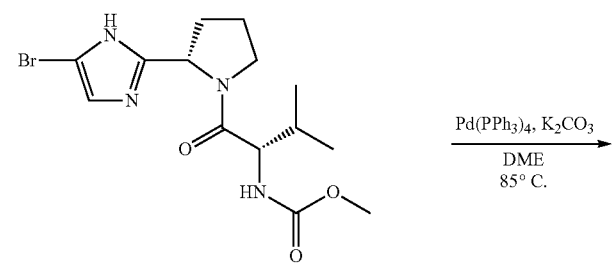

methyl (S)-1-((S)-2-(5-bromo-1H-imidazol-2-yl)pyrrolidin-1-yl)-3-methyl-1-oxobutan-2-ylcarbamate

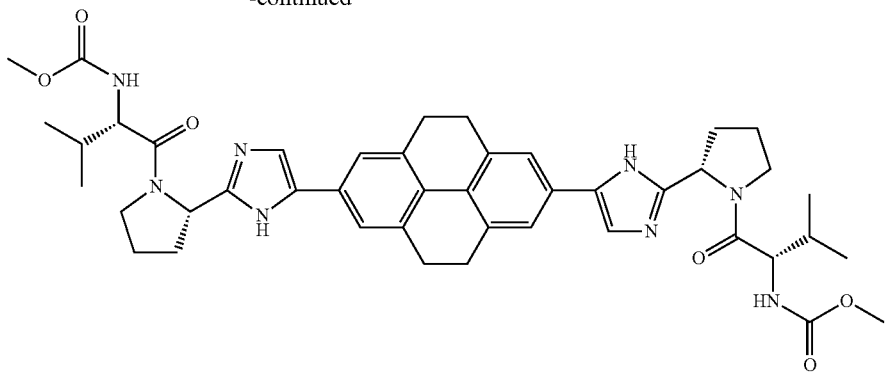

dimethyl (2S,2'S)-1,1'-((2S,2'S)-2,2'-(5,5'-(4,5,9,10-tetrahydropyrene-2,7-diyl)bis(1H-imidazole-5,2-diyl))bis(indoline-2,1-diyl))bis(3-methyl-1-oxobutane-2,1-diyl)dicarbamate

2,7-bis(4,4,5,5-tetramethyl-1,3,2-dioxaborolan-2-yl)-4,5,9,10-tetrahydropyrene To a solution of 2,7-dibromo-4,5,9,10-tetrahydropyrene (400 mg, 1.1 mmol) in dioxane (10 mL) was added bis(pinacolato)diboron (614 mg, 2.42 mmol), KOAc (648 mg, 6.6 mmol), and Pd(dppf)$_2$Cl$_2$ (161 mg, 0.22 mmol). The solution was degassed with N$_2$ for 10 min, then heated to 90° C. for 4 h. The solution was cooled to rt, diluted with EtOAc, washed with sat. NaHCO$_3$, brine, dried over MgSO$_4$, and concentrated. Purified by silica gel chromatography (5% EtOAc/hexanes) to yield the product (188 mg).

Dimethyl (2S,2'S)-1,1'-((2S,2'S)-2,2'-(5,5'-(4,5,9,10-tetrahydropyrene-2,7-diyl)bis(1H-imidazole-5,2-diyl))bis(pyrrolidine-2,1-diyl))bis(3-methyl-1-oxobutane-2,1-diyl) dicarbamate To a solution of 2,7-bis(4,4,5,5-tetramethyl-1,3,2-dioxaborolan-2-yl)-4,5,9,10-tetrahydropyrene (188 mg, 0.41 mmol) in DME (5 mL) was added methyl (S)-1-((S)-2-(5-bromo-1H-imidazol-2-yl)pyrrolidin-1-yl)-3-methyl-1-oxobutan-2-ylcarbamate (306 mg, 0.82 mmol), Pd(PPh$_3$)$_4$ (95 mg, 0.08 mmol), and K$_2$CO$_3$ (2M H$_2$O, 0.82 mL, 1.64 mmol). The solution was degassed for 10 min, then heated to 85° C. The solution was stirred for 24 h, then cooled to rt. The mixture was diluted with MeOH, filtered, and purified by HPLC to yield product (8.9 mg). LCMS-ESI$^+$: calc'd for C$_{44}$H$_{54}$N$_8$O$_6$: 790.95 (M$^+$); Found: 791.40 (M+H$^+$).

Example AG

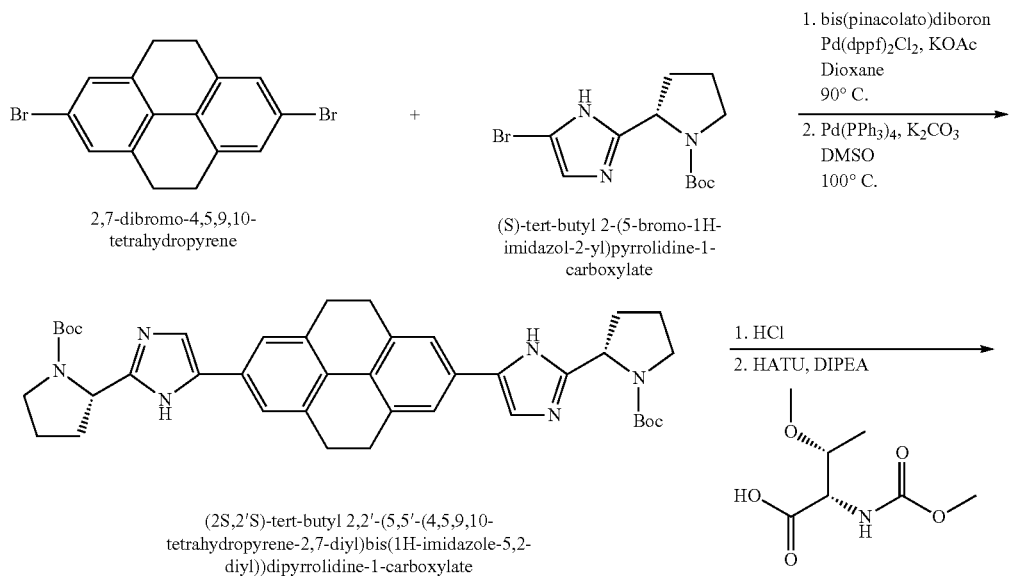

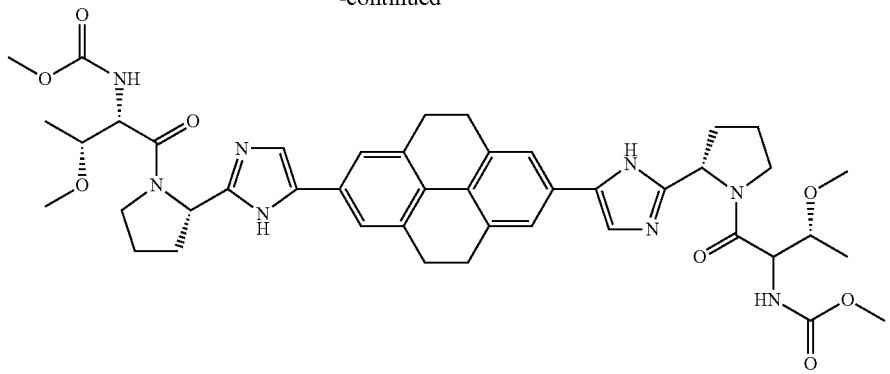

dimethyl (2S,2'S,3R,3'R)-1,1'-((2S,2'S)-2,2'-(5,5'-(4,5,9,10-tetrahydropyrene-2,7-diyl)bis(1H-imidazole-5,2-diyl))bis(pyrrolidine-2,1-diyl))bis(3-methoxy-1-oxobutane-2,1-diyl)dicarbamate

20

(2S,2'S)-tert-butyl 2,2'-(5,5'-(4,5,9,10-tetrahydropyrene-2,7-diyl)bis(1H-imidazole-5,2-diyl))dipyrrolidine-1-carboxylate To a solution of 2,7-dibromo-4,5,9,10-tetrahydropyrene (873 mg, 2.4 mmol) in dioxane (30 mL) was added bis(pinacolato)diboron (1.46 mg, 5.75 mmol), Pd(dppf)$_2$Cl$_2$ 351 mg, 0.48 mmol), and KOAc (1.41 mg, 14.4 mmol). The solution was degassed with N$_2$ for 10 min, and then the sealed tube was heated to 90° C. for 8 h. The reaction mixture was cooled to rt, then (S)-tert-butyl 2-(5-bromo-1H-imidazol-2-yl)pyrrolidine-1-carboxylate (1.67 g, 5.28 mmol), Pd(PPh$_3$)$_4$ (555 mg, 0.48 mmol), and K$_2$CO$_3$ (2M in H$_2$O, 7.2 mL, 14.4 mmol) was added with DMSO (30 mL). The solution was degassed with N$_2$ for 10 min, then the tube was sealed and heated to 100° C. for 14 h. The mixture was cooled to rt, diluted with EtOAc, and washed with sat. NaHCO$_3$, brine, dried over MgSO$_4$, and concentrated. The residue was purified by silica gel chromatography to yield product (115 mg).

Dimethyl (2S,2'S,3R,3'R)-1,1'-((2S,2'S)-2,2'-(5,5'-(4,5,9,10-tetrahydropyrene-2,7-diyl)bis(1H-imidazole-5,2-diyl))bis(pyrrolidine-2,1-diyl))bis(3-methoxy-1-oxobutane-2,1-diyl)dicarbamate To (2S,2'S)-tert-butyl 2,2'-(5,5'-(4,5,9,10-tetrahydropyrene-2,7-diyl)bis(1H-imidazole-5,2-diyl))dipyrrolidine-1-carboxylate (115 mg, 0.17 mmol) in DCM (2.5 mL) and MeOH (2.5 mL) was added HCl (4M in dioxane, 1 mL). The solution stirred for 1 h, and the solvent was removed. The residue (81 mg, 0.17 mmol) was dissolved in DMF (4 mL). (2S,3R)-3-methoxy-2-(methoxycarbonylamino)butanoic acid (71 mg, 0.37 mmol), HATU (139 mg, 0.36 mmol), and DIPEA (0.3 mL, 1.7 mmol) were added sequentially. The solution was stirred for 3 h and the mixture was purified by HPLC to yield product (15.6 mg). LCMS-ESI$^+$: calc'd for C$_{44}$H$_{54}$N$_8$O$_8$: 822.95 (M$^+$); Found: 824.27 (M+H$^+$).

Example AH

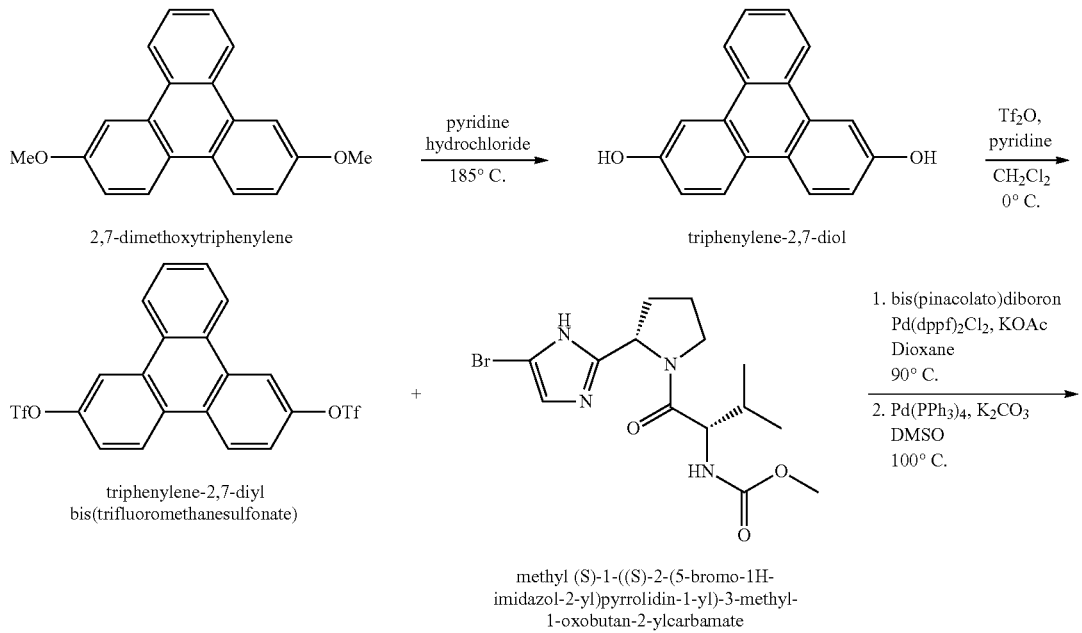

-continued

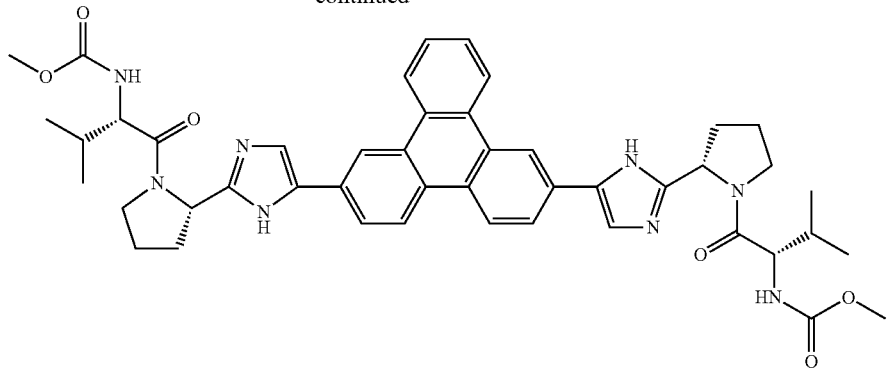

dimethyl (2S,2'S)-1,1'-((2S,2'S)-2,2'-(5,5'-(triphenylene-2,7-diyl)bis(1H-imidazole-5,2-diyl))bis(pyrrolidine-2,1-diyl))bis(3-methyl-1-oxobutane-2,1-diyl)dicarbamate

Triphenylene-2,7-diol 2,7-dimethoxytriphenylene (358 mg, 1.24 mmol) and pyridine hydrochloride (1.72 g, 14.9 mmol) were heated in a flask to 185° C. for 5 h. After cooling to rt, the remaining solid was diluted with $H_2O$ and EtOAc, separated, dried, and concentrated. Taken on crude.

Triphenylene-2,7-diyl bis(trifluoromethanesulfonate)

Triphenylene-2,7-diol (314 mg, 1.2 mmol) was dissolved in DCM (13 mL) and pyridine (1 mL). The solution was cooled to 0° C. and $Tf_2O$ (0.48 mL, 2.65 mmol) was added dropwise. After stirring for 2 h, the reaction mixture was poured into HCl (1N) and extracted with DCM. The organic layer was washed with brine, dried over $MgSO_4$, and concentrated. Taken on crude.

Dimethyl (2S,2'S)-1,1'-((2S,2'S)-2,2'-(5,5'-(triphenylene-2,7-diyl)bis(1H-imidazole-5,2-diyl))bis(pyrrolidine-2,1-diyl))bis(3-methyl-1-oxobutane-2,1-diyl)dicarbamate To a solution of triphenylene-2,7-diyl bis(trifluoromethanesulfonate) (200 mg, 0.38 mmol) in dioxane (5 mL) was added bis(pinacolato)diboron (231 mg, 0.91 mmol), Pd(dppf)$_2$Cl$_2$ (56 mg, 0.076 mmol), and KOAc (223 mg, 2.28 mmol). The solution was degassed with $N_2$ for 10 min, and then the sealed tube was heated to 90° C. for 18 h. The reaction mixture was cooled to rt, then methyl (S)-1-((S)-2-(5-bromo-1H-imidazol-2-yl)pyrrolidin-1-yl)-3-methyl-1-oxobutan-2-ylcarbamate (313 mg, 0.84 mmol), Pd(PPh$_3$)$_4$ (88 mg, 0.076 mmol), and K$_2$CO$_3$ (2M in H$_2$O, 1.14 mL, 2.28 mmol) was added with DMSO (5 mL). The solution was degassed with $N_2$ for 10 min, then the tube was sealed and heated to 100° C. for 23 h. The mixture was cooled to rt, diluted with EtOAc, and washed with sat. NaHCO$_3$, brine, dried over MgSO$_4$, and concentrated. The residue was purified by silica gel chromatography (0-30% MeOH/EtOAc) and then purified by HPLC to yield product (32.1 mg). LCMS-ESI$^+$: calc'd for C$_{46}$H$_{52}$N$_8$O$_6$: 812.96 (M$^+$); Found: 814.74 (M+H$^+$).

Example AI

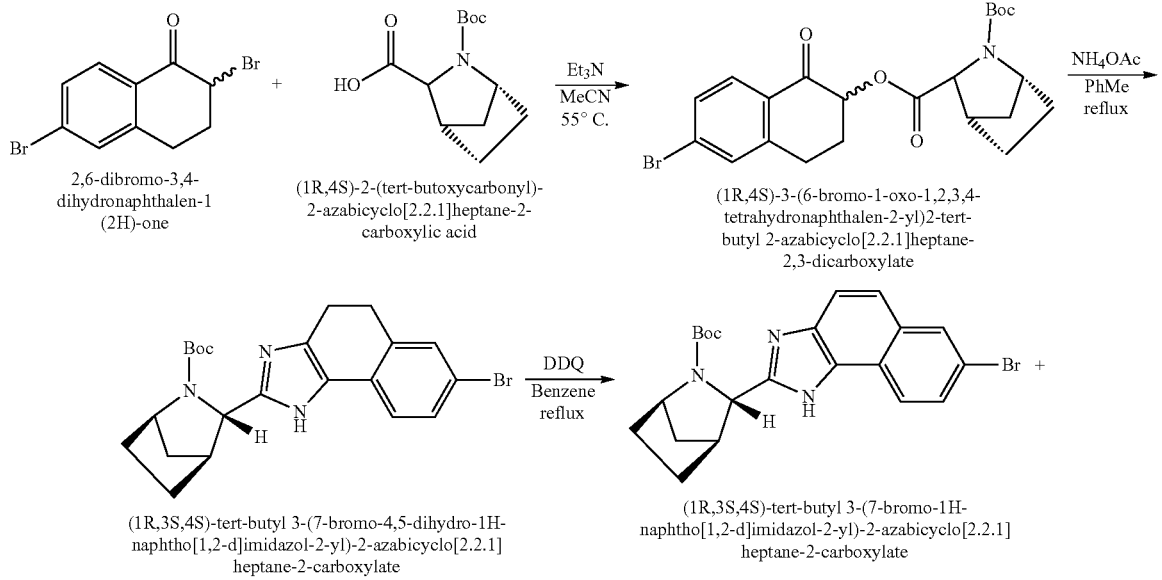

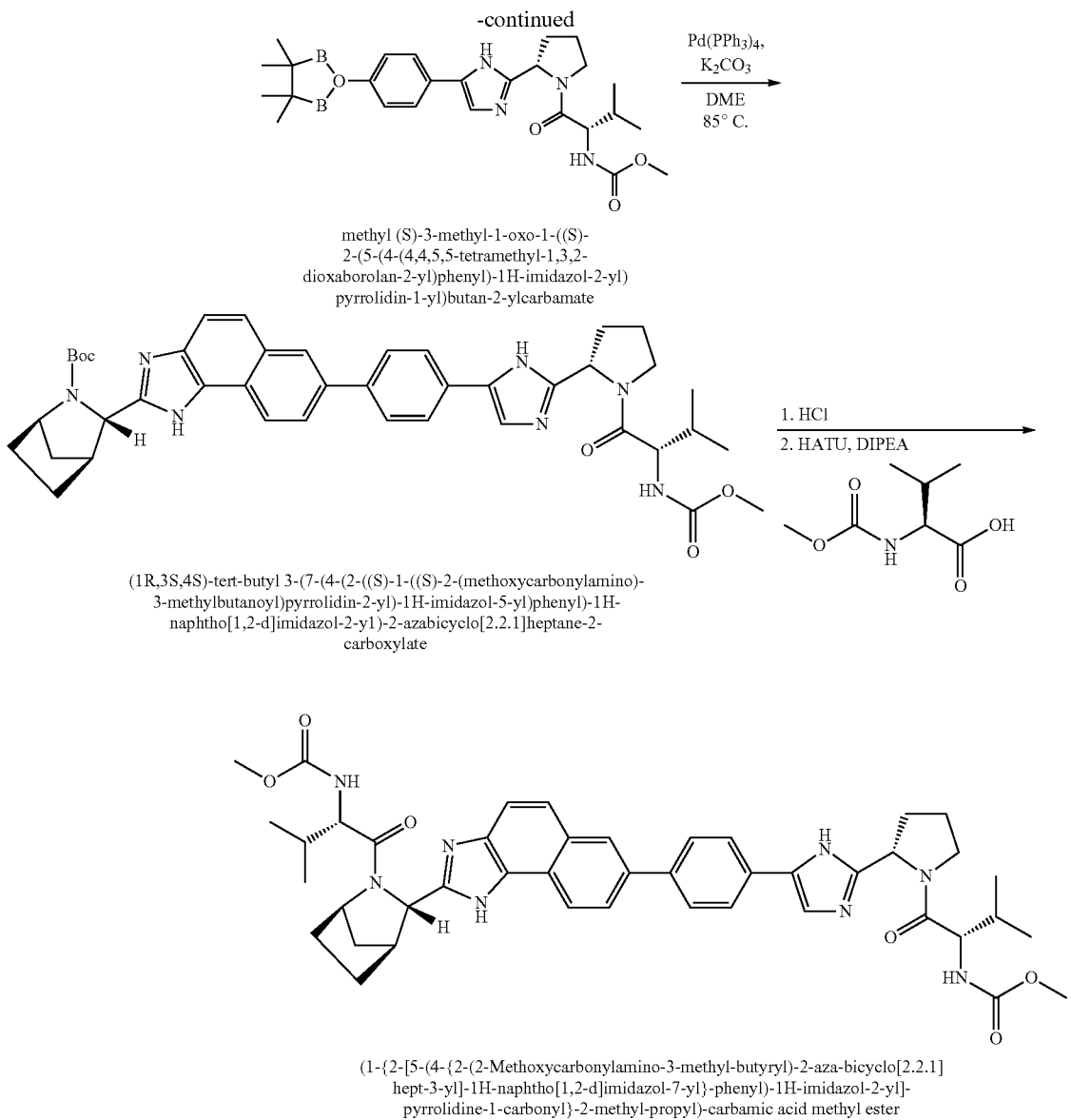

methyl (S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-ylcarbamate (1R,3S,4S)-tert-butyl 3-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-2-azabicyclo[2.2.1]heptane-2-carboxylate (1-{2-[5-(4-{2-(2-Methoxycarbonylamino-3-methyl-butyryl)-2-aza-bicyclo[2.2.1]hept-3-yl]-1H-naphtho[1,2-d]imidazol-7-yl}-phenyl)-1H-imidazol-2-yl]-pyrrolidine-1-carbonyl}-2-methyl-propyl)-carbamic acid methyl ester

(1R,4S)-3-(6-bromo-1-oxo-1,2,3,4-tetrahydronaphthalen-2-yl)-2-tert-butyl-2-azabicyclo[2.2.1]heptane-2,3-dicarboxylate To a solution of 2,6-dibromo-3,4-dihydronaphthalen-1(2H)-one (6.75 g, 22.21 mmol) and (1R,4S)-2-(tert-butoxycarbonyl)-2-azabicyclo[2.2.1]heptane-3-carboxylic acid (8.04 g, 33.32 mmol) in MeCN (100 mL) was added Et₃N (4.64 mL, 33.32 mmol). The solution was heated to 55° C. and stirred o/n. The solution was cooled to rt, diluted with EtOAc, sat. NaHCO₃, brine, dried over MgSO₄, and concentrated. The residue was purified by silica gel chromatography to yield product (6.6 g).

(1R,3S,4S)-tert-butyl-3-(7-bromo-4,5-dihydro-1H-naphtho[1,2-d]imidazol-2-yl)-2-azabicyclo[2.2.1]heptane-2-carboxylate To a solution of (1R,4S)-3-(6-bromo-1-oxo-1,2,3,4-tetrahydronaphthalen-2-yl)-2-tert-butyl-2-azabicyclo[2.2.1]heptane-2,3-dicarboxylate (6.6 g, 14.21 mmol) in PhMe (200 mL) was added NH₄OAc (21.9 g, 284.2 mmol). The solution was heated to reflux for 4 h. The solution was cooled, and diluted with EtOAc, washed with H₂O, sat. NaHCO₃, brine, dried over MgSO₄, and concentrated. The residue was purified by silica gel chromatography to yield product (2.4 g).

(1R,3S,4S)-tert-butyl-3-(7-bromo-1H-naphtho[1,2-d]imidazol-2-yl)-2-azabicyclo[2.2.1]heptane-2-carboxylate (1R,3 S,4S)-tert-butyl-3-(7-bromo-4,5-dihydro-1H-naphtho[1,2-d]imidazol-2-yl)-2-azabicyclo[2.2.1]heptane-2-carboxylate (1.25 g, 2.81 mmol) was diluted in benzene (50 mL). DDQ (0.7 g, 3.1 mmol) was added and the solution was heated to reflux for 1.5 h. After cooling, the reaction mixture was concentrated and the residue was purified by silica gel chromatography to yield product (1.1 g).

(1R,3S,4S)-tert-butyl-3-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-2-azabicyclo[2.2.1]heptane-2-carboxylate Methyl (S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-ylcarbamate (526 mg, 1.06 mmol) and (1R,3S,4S)-tert-butyl-3-(7-bromo-1H-naphtho[1,2-d]imidazol-2-yl)-2-azabicyclo[2.2.1]heptane-2-carboxylate (427 mg, 0.96 mmol) were combined in DME (10 mL). Pd(PPh$_3$)$_4$ (111 mg, 0.096 mmol) and K$_2$CO$_3$ (2M H$_2$O, 1.6 mL, 3.17 mmol) were added, and the solution was degassed with N$_2$ for 10 min. The solution was heated to 85° C. and stirred o/n. The following morning, the solution was cooled to rt. The solution was diluted with EtOAc, washed with sat. NaHCO$_3$, brine, dried with MgSO$_4$, and concentrated. The residue was purified by silica gel chromatography to yield product (280 mg).

Methyl (S)-3-methyl-1-((1R,3S,4S)-3-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-2-azabicyclo[2.2.1]heptan-2-yl)-1-oxobutan-2-ylcarbamate To (1R,3S,4S)-tert-butyl 3-(7-(4-(2-((S)-1-((S)-2-(methoxycarbonylamino)-3-methylbutanoyl) pyrrolidin-2-yl)-1H-imidazol-5-yl)phenyl)-1H-naphtho[1,2-d]imidazol-2-yl)-2-azabicyclo[2.2.1]heptane-2-carboxylate (280 mg, 0.38 mmol) in DCM (5 mL) was added HCl (4M in dioxane, 1 mL). The solution stirred for 2 h, and the solvent was removed. The intermediate (80 mg, 0.13 mmol) was dissolved in DMF(2 mL). (S)-2-(methoxycarbonylamino)-3-methylbutanoic acid (22 mg, 0.13 mmol), HATU (48 mg, 0.13 mmol), and DIPEA (0.11 mL, 0.64 mmol) were added sequentially. The solution stirred o/n and the mixture was purified by HPLC to yield product (51.8 mg). LCMS-ESI$^+$: calc'd for C$_{44}$H$_{54}$N$_8$O$_5$: 786.96 (M$^+$); Found: 789.23 (M+H$^+$).

Example AJ

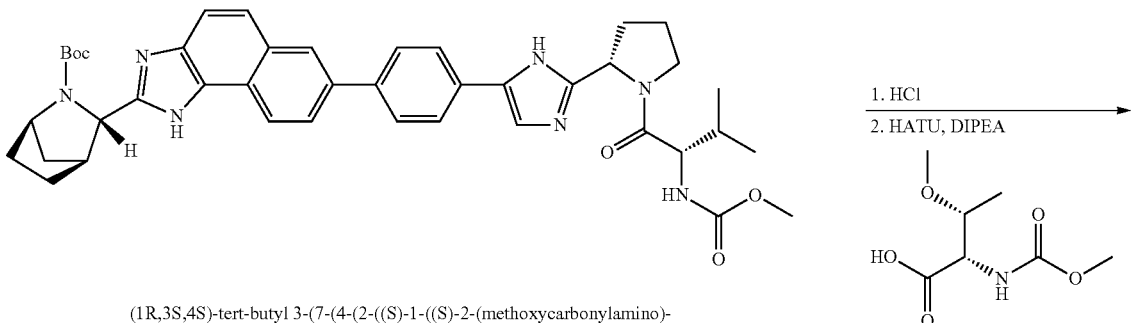

(1R,3S,4S)-tert-butyl 3-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-2-azabicyclo[2.2.1]heptane-2-carboxylate

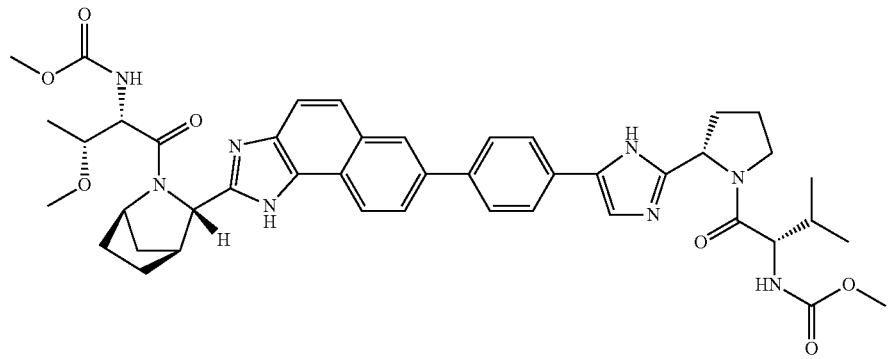

methyl (2S,3R)-3-methoxy-1-((1R,3S,4S)-3-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-2-azabicyclo[2.2.1]heptan-2-yl)-1-oxobutan-2-ylcarbamate

653

Methyl (2S,3R)-3-methoxy-1-((1R,3S,4S)-3-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-2-azabicyclo[2.2.1]heptan-2-yl)-1-oxobutan-2-ylcarbamate

To (1R,3 S,4S)-tert-butyl 3-(7-(4-(2-((S)-1-((S)-2-(methoxycarbonylamino)-3-methylbutanoyl) pyrrolidin-2-yl)-1H-imidazol-5-yl)phenyl)-1H-naphtho[1,2-d]imidazol-2-yl)-2-azabicyclo[2.2.1]heptane-2-carboxylate (280 mg, 0.38 mmol) in DCM (5 mL) was added HCl (4M in dioxane, 1 mL). The solution stirred for 2 h, and the solvent was removed. The intermediate (80 mg, 0.13 mmol) was dissolved in DMF(2 mL). (2S,3R)-3-methoxy-2-(methoxycarbonylamino)butanoic acid (24 mg, 0.13 mmol), HATU (48 mg, 0.13 mmol), and DIPEA (0.11 mL, 0.64 mmol) were added sequentially. The solution stirred o/n and the mixture was purified by HPLC to yield product (54.6 mg). LCMS-ESI$^+$: calc'd for $C_{44}H_{52}N_8O_7$: 804.93 (M$^+$); Found: 806.23 (M+H$^+$).

Example AK

654

Methyl (S)-2-((1R,3S,4S)-3-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-2-azabicyclo[2.2.1]heptan-2-yl)-2-oxo-1-(tetrahydro-2H-pyran-4-yl)ethylcarbamate

To (1R,3 S,4S)-tert-butyl 3-(7-(4-(2-((S)-1-((S)-2-(methoxycarbonylamino)-3-methylbutanoyl) pyrrolidin-2-yl)-1H-imidazol-5-yl)phenyl)-1H-naphtho[1,2-d]imidazol-2-yl)-2-azabicyclo[2.2.1]heptane-2-carboxylate (280 mg, 0.38 mmol) in DCM (5 mL) was added HCl (4M in dioxane, 1 mL). The solution stirred for 2 h, and the solvent was removed. The intermediate (80 mg, 0.13 mmol) was dissolved in DMF (2 mL). (S)-2-(methoxycarbonylamino)-2-(tetrahydro-2H-pyran-4-yl)acetic acid (28 mg, 0.13 mmol), HATU (48 mg, 0.13 mmol), and DIPEA (0.11 mL, 0.64 mmol) were added sequentially. The solution stirred o/n and the mixture was purified by HPLC to yield product (24.6 mg). LCMS-ESI$^+$: calc'd for $C_{46}H_{54}N_8O_7$: 830.97 (M$^+$); Found: 831.33 (M+H$^+$).

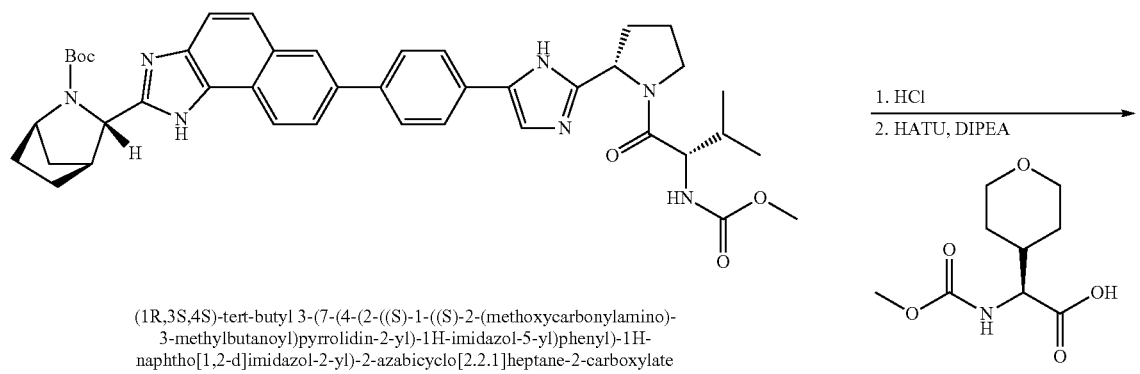

(1R,3S,4S)-tert-butyl 3-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-2-azabicyclo[2.2.1]heptane-2-carboxylate

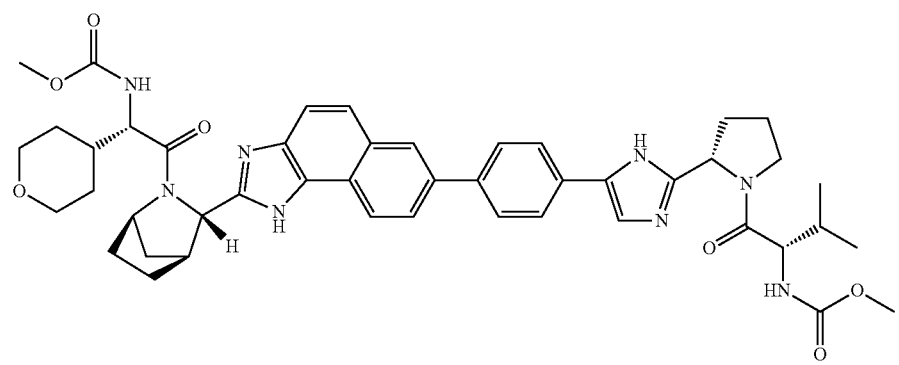

methyl (S)-2-((1R,3S,4S)-3-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-2-azabicyclo[2.2.1]heptan-2-yl)-2-oxo-1-(tetrahydro-2H-pyran-4-yl)ethylcarbamate Example AL
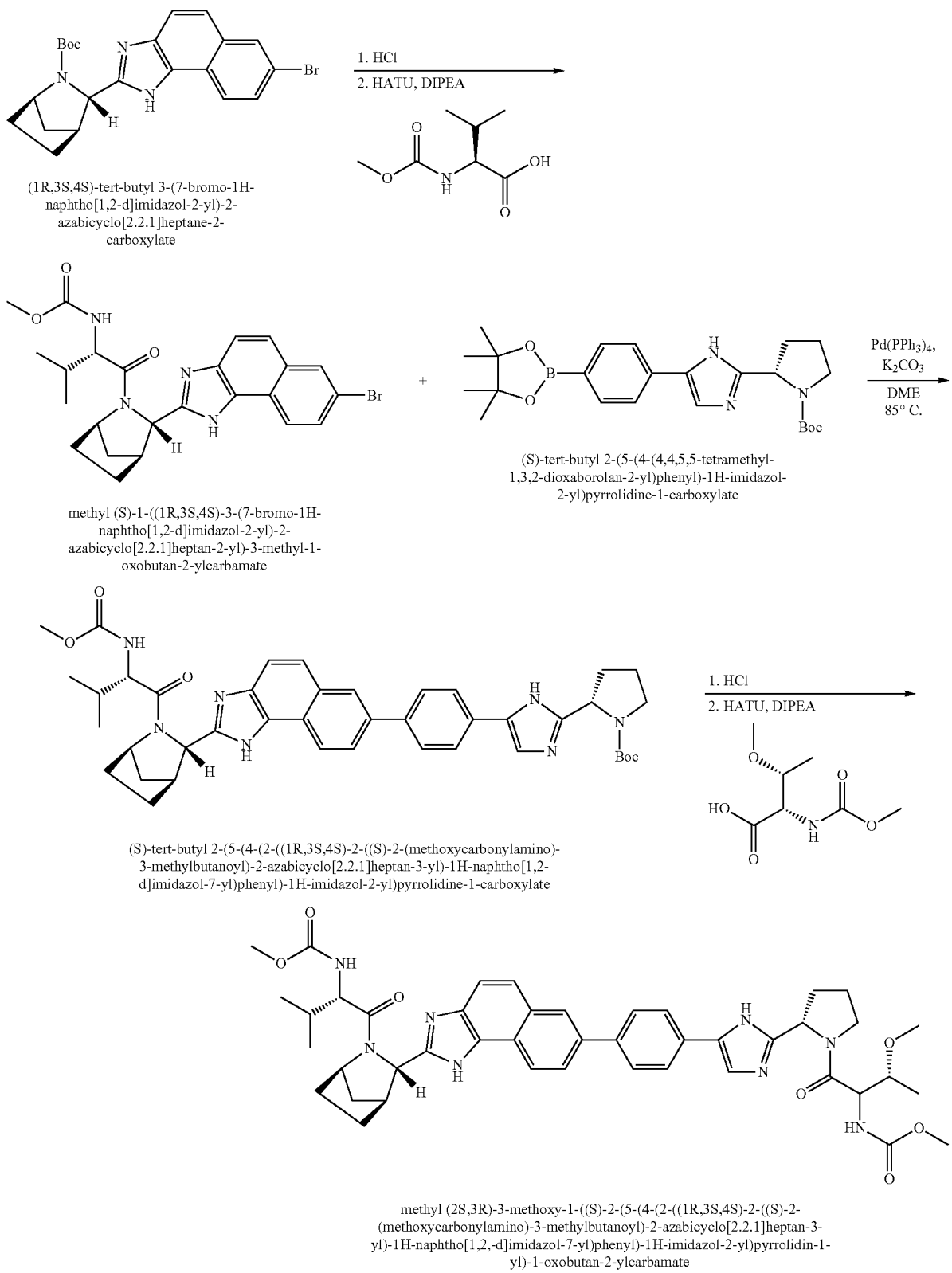

Methyl (S)-1-((1R,3S,4S)-3-(7-bromo-1H-naphtho[1,2-d]imidazol-2-yl)-2-azabicyclo[2.2.1]heptan-2-yl)-3-methyl-1-oxobutan-2-ylcarbamate (1R,3 S,4S)-tert-butyl 3-(7-bromo-1H-naphtho[1,2-d]imidazol-2-yl)-2-azabicyclo[2.2.1]heptane-2-carboxylate (200 mg, 0.45 mmol) in DCM (5 mL) was added HCl (4M in dioxane, 1 mL). The solution stirred for 1 h, after which the solvent was removed. The intermediate (154 mg, 0.45 mmol) was dissolved in DMF (5 mL). (S)-2-(methoxycarbonylamino)-3-methylbutanoic acid (79 mg, 0.45 mmol), HATU (171 mg, 0.45 mmol), and DIPEA (0.39 mL, 2.25 mmol) were added sequentially. After stirring o/n, the solution was diluted with EtOAc, washed with sat. NaHCO₃, brine, dried with MgSO₄, and concentrated. The mixture was purified by silica gel chromatography to yield product (122 mg).

(S)-tert-butyl 2-(5-(4-(2-((1R,3S,4S)-2-((S)-2-(methoxycarbonylamino)-3-methylbutanoyl)-2-azabicyclo[2.2.1]heptan-3-yl)-1H-naphtho[1,2-d]imidazol-7-yl)phenyl)-1H-imidazol-2-yl)pyrrolidine-1-carboxylate Methyl (S)-1-((1R,3 S,4S)-3-(7-bromo-1H-naphtho[1,2-d]imidazol-2-yl)-2-azabicyclo[2.2.1]heptan-2-yl)-3-methyl-1-oxobutan-2-ylcarbamate (122 mg, 0.24 mmol) and (S)-tert-butyl 2-(5-(4-(4,4,5,5-tetramethyl-1,3,2-dioxaborolan-2-yl)phenyl)-1H-imidazol-2-yl)pyrrolidine-1-carboxylate (114 mg, 0.26 mmol) were combined in DME (3 mL). Pd(PPh₃)₄ (28 mg, 0.024 mmol) and K₂CO₃ (2M H₂O, 0.4 mL, 0.79 mmol) were added, and the solution was degassed with N₂ for 10 min. The solution was heated to 85° C. and stirred o/n. The following morning, the solution was cooled to rt. The solution was diluted with EtOAc, washed with sat. NaHCO₃, brine, dried with MgSO₄, and concentrated. The residue was purified by silica gel chromatography to yield product (73 mg).

Methyl (2S,3R)-3-methoxy-1-((S)-2-(5-(4-(2-((1R,3S,4S)-2-((S)-2-(methoxycarbonylamino)-3-methylbutanoyl)-2-azabicyclo[2.2.1]heptan-3-yl)-1H-naphtho[1,2-d]imidazol-7-yl)phenyl)-1H-imidazol-2-yl)pyrrolidin-1-yl)-1-oxobutan-2-ylcarbamate (S)-tert-butyl 2-(5-(4-(2-((1R,3 S,4S)-2-((S)-2-(methoxycarbonylamino)-3-methylbutanoyl)-2-azabicyclo[2.2.1]heptan-3-yl)-1H-naphtho[1,2-d]imidazol-7-yl)phenyl)-1H-imidazol-2-yl)pyrrolidine-1-carboxylate (73 mg, 0.10 mmol) in DCM (3 mL) and MeOH (3 mL) was added HCl (4M in dioxane, 0.5 mL). The solution stirred for 3 h at 35° C., after which the solvent was removed. The intermediate (31 mg, 0.13 mmol) was dissolved in DMF (1 mL). (2S,3R)-3-methoxy-2-(methoxycarbonylamino)butanoic acid (9 mg, 0.05 mmol), HATU (19 mg, 0.05 mmol), and DIPEA (0.04 mL, 0.25 mmol) were added sequentially. The solution stirred o/n and the mixture was purified by HPLC to yield product (23.1 mg). LCMS-ESI⁺: calc'd for $C_{44}H_{52}N_8O_7$: 804.93 (M⁺); Found: 806.34 (M+H⁺).

Example AM

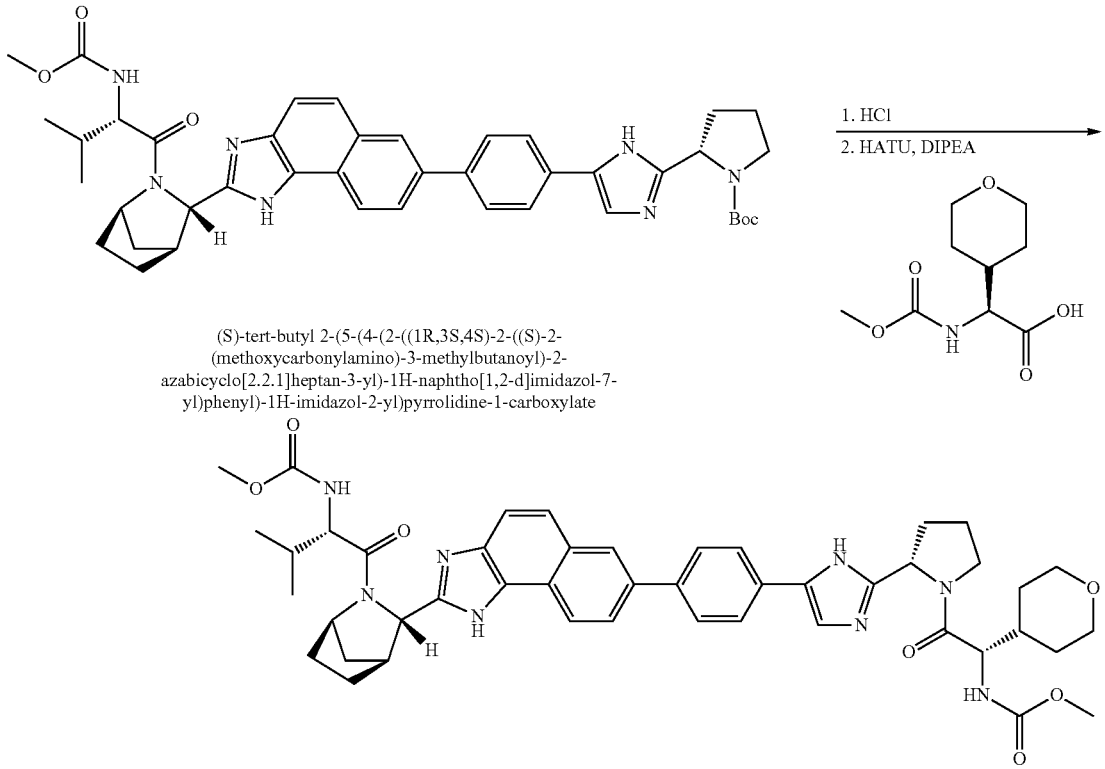

(S)-tert-butyl 2-(5-(4-(2-((1R,3S,4S)-2-((S)-2-(methoxycarbonylamino)-3-methylbutanoyl)-2-azabicyclo[2.2.1]heptan-3-yl)-1H-naphtho[1,2-d]imidazol-7-yl)phenyl)-1H-imidazol-2-yl)pyrrolidine-1-carboxylate methyl (S)-2-((S)-2-(5-(4-(2-((1R,3S,4S)-2-((S)-2-(methoxycarbonylamino)-3-methylbutanoyl)-2-azabicyclo[2.2.1]heptan-3-yl)-1H-naphtho[1,2-d]imidazol-7-yl)phenyl-1H-imidazol-2-yl)pyrrolidin-1-yl)-2-oxo-1-(tetrahydro-2H-pyran-4-yl)ethylcarbamate Methyl (S)-2-((S)-2-(5-(4-(2-((1R,3S,4S)-2-((S)-2-(methoxycarbonylamino)-3-methylbutanoyl)-2-azabicyclo[2.2.1]heptan-3-y)-1H-naphtho[1,2-d]imidazol-7-yl)phenyl)-1H-imidazol-2-yl)pyrrolidin-1-yl)-2-oxo-1-(tetrahydro-2H-pyran-4-yl) ethylcarbamate (S)-tert-butyl 2-(5-(4-(2-((1R,3 S,4S)-2-((S)-2-(methoxycarbonylamino)-3-methylbutanoyl)-2-azabicyclo[2.2.1]heptan-3-yl)-1H-naphtho[1,2-d]imidazol-7-yl)phenyl)-1H-imidazol-2-yl)pyrrolidine-1-carboxylate (73 mg, 0.10 mmol) in DCM (3 mL) and MeOH (3 mL) was added HCl (4M in dioxane, 0.5 mL). The solution stirred for 3 h at 35° C., after which the solvent was removed. The intermediate (31 mg, 0.13 mmol) was dissolved in DMF (1 mL). (S)-2-(methoxycarbonylamino)-2-(tetrahydro-2H-pyran-4-yl)acetic acid (16 mg, 0.05 mmol), HATU (19 mg, 0.05 mmol), and DIPEA (0.04 mL, 0.25 mmol) were added sequentially. The solution stirred o/n and the mixture was purified by HPLC to yield product (27.6 mg). LCMS-ESI$^+$: calc'd for $C_{46}H_{54}N_8O_7$: 830.97 (M$^+$); Found: 832.56 (M+H$^+$).

Example AN

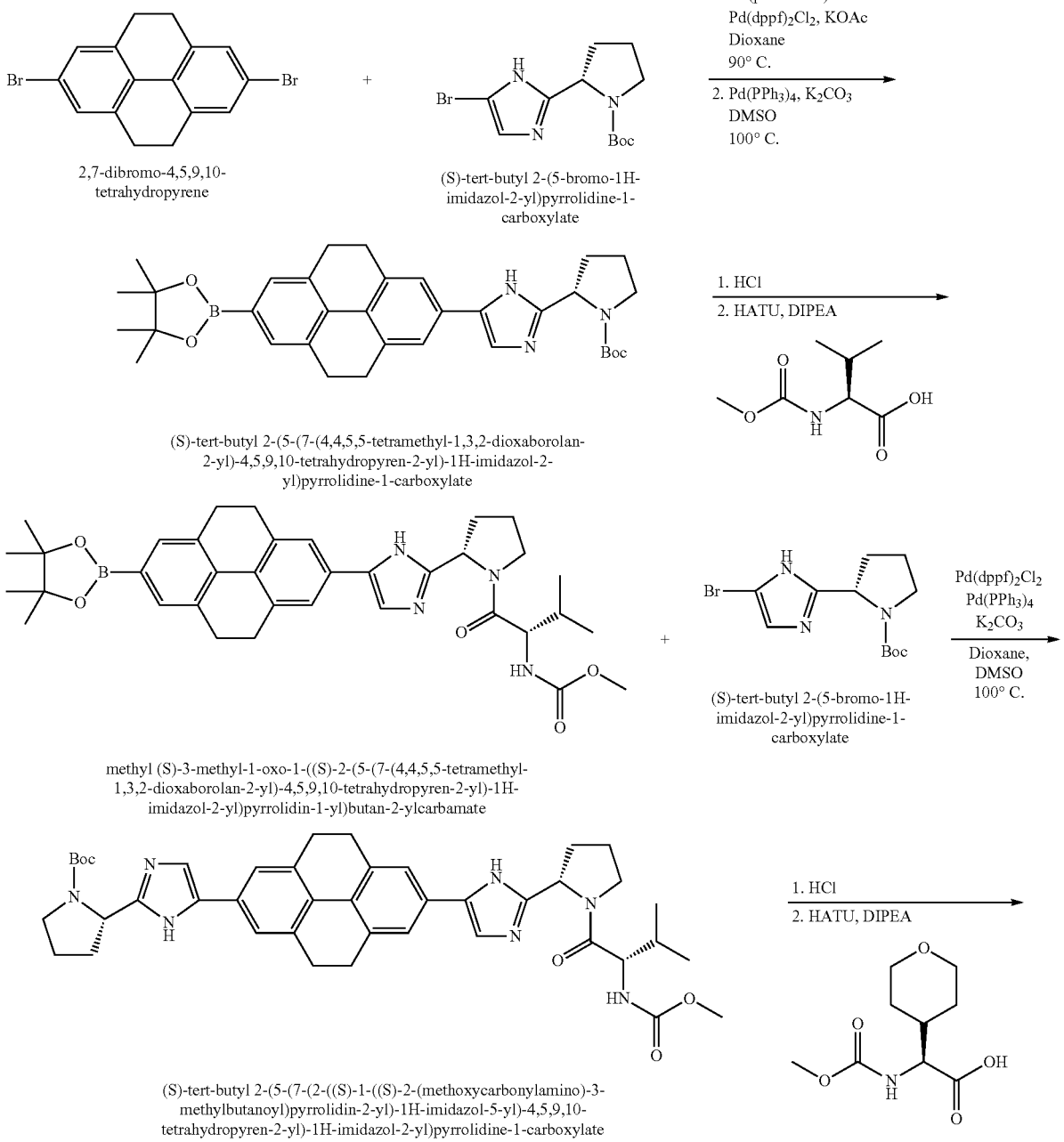

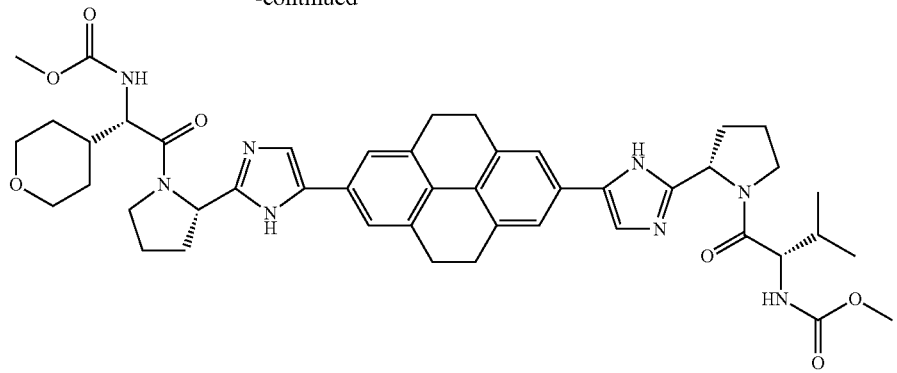

methyl (S)-2-((S)-2-(5-(7-(2-((S)-1-((S)-2-(methoxycarbonylamino)-3-methylbutanoyl)pyrrolidin-2-yl)-1H-imidazol-5-yl)-4,5,9,10-tetrahydropyren-2-yl)-1H-imidazol-2-yl)pyrrolidin-1-yl)-2-oxo-1-(tetrahydro-2H-pyran-4-yl)ethylcarbamate

(S)-tert-butyl 2-(5-(7-(4,4,5,5-tetramethyl-1,3,2-dioxaborolan-2-yl)-4,5,9,10-tetrahydropyren-2-yl)-1H-imidazol-2-yl)pyrrolidine-1-carboxylate To a solution of 2,7-dibromo-4,5,9,10-tetrahydropyrene (873 mg, 2.4 mmol) in dioxane (30 mL) was added bis(pinacolato)diboron (1.46 mg, 5.75 mmol), Pd(dppf)$_2$Cl$_2$ (351 mg, 0.48 mmol), and KOAc (1.41 mg, 14.4 mmol). The solution was degassed with N$_2$ for 10 min, and then the sealed tube was heated to 90° C. for 8 h. The reaction mixture was cooled to rt, then (S)-tert-butyl 2-(5-bromo-1H-imidazol-2-yl)pyrrolidine-1-carboxylate (1.67 g, 5.28 mmol), Pd(PPh$_3$)$_4$ (555 mg, 0.48 mmol), and K$_2$CO$_3$ (2M in H$_2$O, 7.2 mL, 14.4 mmol) was added with DMSO (30 mL). The solution was degassed with N$_2$ for 10 min, then the tube was sealed and heated to 100° C. for 14 h. The mixture was cooled to rt, diluted with EtOAc, and washed with sat. NaHCO$_3$, brine, dried with MgSO$_4$, and concentrated. The residue was purified by silica gel chromatography to yield product (699 mg).

Methyl (S)-3-methyl-1-oxo-1-((S)-2-(5-(7-(4,4,5,5-tetramethyl-1,3,2-dioxaborolan-2-yl)-4,5,9,10-tetrahydropyren-2-yl)-1H-imidazol-2-yl)pyrrolidin-1-yl)butan-2-ylcarbamate To (S)-tert-butyl 2-(5-(7-(4,4,5,5-tetramethyl-1,3,2-dioxaborolan-2-yl)-4,5,9,10-tetrahydropyren-2-yl)-1H-imidazol-2-yl)pyrrolidine-1-carboxylate (300 mg, 0.53 mmol) in DCM (5 mL) was added HCl (4M in dioxane, 1 mL). The solution stirred for 1 h, and the solvent was removed. The intermediate (247 mg, 0.53 mmol) was dissolved in DMF (5 mL). (S)-2-(methoxycarbonylamino)-3-methylbutanoic acid (93 mg, 0.53 mmol), HATU (200 mg, 0.53 mmol), and DIPEA (0.46 mL, 2.65 mmol) were added sequentially. The solution was stirred o/n. The mixture was diluted with EtOAc, and washed with sat. NaHCO$_3$, brine, dried with MgSO$_4$, and concentrated. and the mixture was purified by silica gel chromatography to yield product (139 mg).

(S)-tert-butyl 2-(5-(7-(2-((S)-1-((S)-2-(methoxycarbonylamino)-3-methylbutanoyl)pyrrolidin-2-yl)-1H-imidazol-5-yl)-4,5,9,10-tetrahydropyren-2-yl)-1H-imidazol-2-yl)pyrrolidine-1-carboxylate Methyl (S)-3-methyl-1-oxo-1-((S)-2-(5-(7-(4,4,5,5-tetramethyl-1,3,2-dioxaborolan-2-yl)-4,5,9,10-tetrahydropyren-2-yl)-1H-imidazol-2-yl)pyrrolidin-1-yl)butan-2-ylcarbamate (139 mg, 0.22 mmol) and (S)-tert-butyl 2-(5-bromo-1H-imidazol-2-yl)pyrrolidine-1-carboxylate (77 mg, 0.24 mmol) were dissolved in dioxane (2 mL) and DMSO (2 mL). Pd(dppf)$_2$Cl$_2$ (16 mg, 0.022 mmol), Pd(PPh$_3$)$_4$ (25 mg, 0.022 mmol), and K$_2$CO$_3$ (2M in H$_2$O, 0.33 mL, 0.66 mmol). The tube was sealed and heated to 100° C. for 20 h. The mixture was cooled to rt, diluted with EtOAc, and washed with sat. NaHCO$_3$, brine, dried with MgSO$_4$, and concentrated. The residue was purified by silica gel chromatography to yield product (54.5 mg).

Methyl (S)-2-((S)-2-(5-(7-(2-((S)-1-((S)-2-(methoxycarbonylamino)-3-methylbutanoyl)pyrrolidin-2-yl)-1H-imidazol-5-yl)-4,5,9,10-tetrahydropyren-2-yl)-1H-imidazol-2-yl)pyrrolidin-1-yl)-2-oxo-1-(tetrahydro-2H-pyran-4-yl)ethylcarbamate To (S)-tert-butyl 2-(5-(7-(2-((S)-1-((S)-2-(methoxycarbonylamino)-3-methylbutanoyl)pyrrolidin-2-yl)-1H-imidazol-5-yl)-4,5,9,10-tetrahydropyren-2-yl)-1H-imidazol-2-yl)pyrrolidine-1-carboxylate (55 mg, 0.08 mmol) in DCM (3 mL) was added HCl (4M in dioxane, 0.25 mL). The solution stirred for 1 h, and the solvent was removed. The intermediate was dissolved in DMF (2 mL). (S)-2-(methoxycarbonylamino)-2-(tetrahydro-2H-pyran-4-yl)acetic acid (16 mg, 0.08 mmol), HATU (29 mg, 0.08 mmol), and DIPEA (0.06 mL, 0.37 mmol) were added sequentially. The solution was stirred o/n and the mixture was purified by HPLC to yield product (17.9 mg). LCMS-ESI$^+$: calc'd for C$_{46}$H$_{56}$N$_8$O$_7$: 832.99 (M$^+$) Found: 833.25 (M+H$^+$).

Example AO
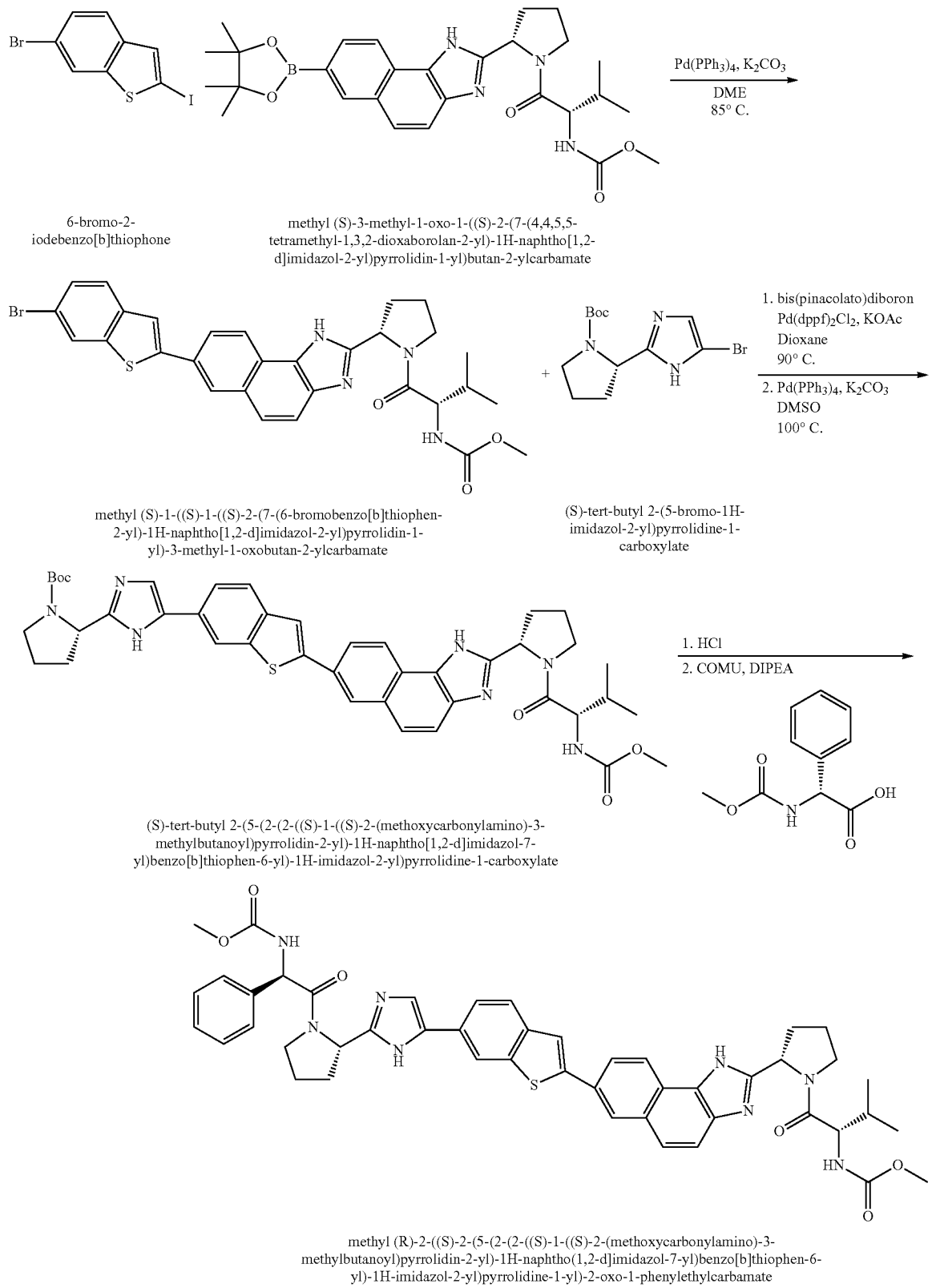

Methyl (S)-1-((S)-2-(7-(6-bromobenzo[b]thiophen-2-yl)-1H-naphtho[1,2-d]imidazol-2-yl) pyrrolidin-1-yl)-3-methyl-1-oxobutan-2-ylcarbamate To a solution of methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate (251 mg, 0.48 mmol) in DME (5 mL) was added 6-bromo-2-iodobenzo[b]thiophene (82 mg, 0.24 mmol), Pd(PPh$_3$)$_4$ (28 mg, 0.024 mmol), and K$_2$CO$_3$ (2M in H$_2$O, 0.8 mL, 1.58 mmol). The solution was degassed with N$_2$ for 10 min, then heated to 85° C. for 24 h. The mixture was cooled to rt, diluted with EtOAc, and washed with sat. NaHCO$_3$, brine, dried with MgSO$_4$, and concentrated. The residue was purified by silica gel chromatography to yield product (221 mg).

(S)-tert-butyl 2-(5-(2-(2-((S)-1-((S)-2-(methoxycarbonylamino)-3-methylbutanoyl) pyrrolidin-2-yl)-1H-naphtho[1,2-d]imidazol-7-yl)benzo[b]thiophen-6-yl)-1H-imidazol-2-yl)pyrrolidine-1-carboxylate To a solution of methyl (S)-1-((S)-2-(7-(6-bromobenzo[b]thiophen-2-yl)-1H-naphtho[1,2-d]imidazol-2-yl)pyrrolidin-1-yl)-3-methyl-1-oxobutan-2-ylcarbamate (221 mg, 0.37 mmol) in dioxane (5 mL) was added bis(pinacolato)diboron (111 mg, 0.44 mmol), Pd(dppf)$_2$Cl$_2$ (27 mg, 0.037 mmol), and KOAc (107 mg, 1.1 mmol). The solution was degassed with N$_2$ for 10 min, and then the sealed tube was heated to 90° C. for 18 h. The reaction mixture was cooled to rt, then methyl (S)-tert-butyl 2-(5-bromo-1H-imidazol-2-yl)pyrrolidine-1-carboxylate (127 mg, 0.4 mmol), Pd(PPh$_3$)$_4$ (43 mg, 0.037 mmol), and K$_2$CO$_3$ (2M in H$_2$O, 0.54 mL, 1.1 mmol) was added with DMSO (5 mL). The solution was degassed with N$_2$ for 10 min, then the tube was sealed and heated to 100° C. for 23 h. The mixture was cooled to rt, diluted with EtOAc, and washed with sat. NaHCO$_3$, brine, dried with MgSO$_4$, and concentrated. The residue was purified by silica gel chromatography to yield product (52.8 mg).

Methyl (R)-2-((S)-2-(5-(2-(2-((S)-1-((S)-2-(methoxycarbonylamino)-3-methylbutanoyl) pyrrolidin-2-yl)-1H-naphtho[1,2-d]imidazol-7-yl)benzo[b]thiophen-6-yl)-1H-imidazol-2-yl)pyrrolidin-1-yl)-2-oxo-1-phenylethylcarbamate To (S)-tert-butyl 2-(5-(2-(2-((S)-1-((S)-2-(methoxycarbonylamino)-3-methylbutanoyl)pyrrolidin-2-yl)-1H-naphtho[1,2-d]imidazol-7-yl)benzo[b]thiophen-6-yl)-1H-imidazol-2-yl)pyrrolidine-1-carboxylate (53 mg, 0.07 mmol) in DCM (3 mL) was added HCl (4M in dioxane, 0.25 mL). The solution stirred for 1 h, and the solvent was removed. The intermediate was dissolved in DMF (2 mL). (R)-2-(methoxycarbonylamino)-2-phenylacetic acid (15 mg, 0.07 mmol), COMU (36 mg, 0.08 mmol), and DIPEA (0.06 mL, 0.35 mmol) were added sequentially. The solution was stirred o/n and the mixture was purified by HPLC to yield product (14.8 mg). LCMS-ESI$^+$: calc'd for C$_{47}$H$_{48}$N$_8$O$_6$S: 853.00 (Me); Found: 853.22 (M+H$^+$).

Example AP

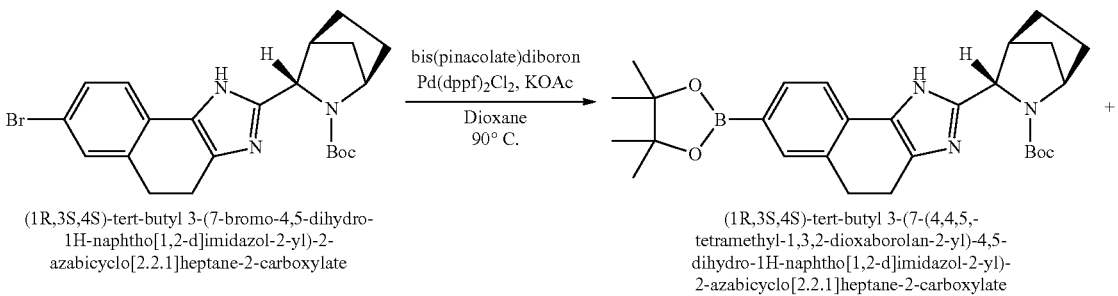

(1R,3S,4S)-tert-butyl 3-(7-bromo-4,5-dihydro-1H-naphtho[1,2-d]imidazol-2-yl)-2-azabicyclo[2.2.1]heptane-2-carboxylate (1R,3S,4S)-tert-butyl 3-(7-(4,4,5,-tetramethyl-1,3,2-dioxaborolan-2-yl)-4,5-dihydro-1H-naphtho[1,2-d]imidazol-2-yl)-2-azabicyclo[2.2.1]heptane-2-carboxylate

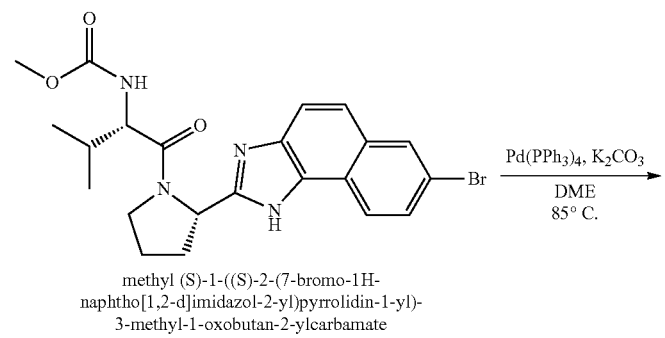

methyl (S)-1-((S)-2-(7-bromo-1H-naphtho[1,2-d]imidazol-2-yl)pyrrolidin-1-yl)-3-methyl-1-oxobutan-2-ylcarbamate -continued

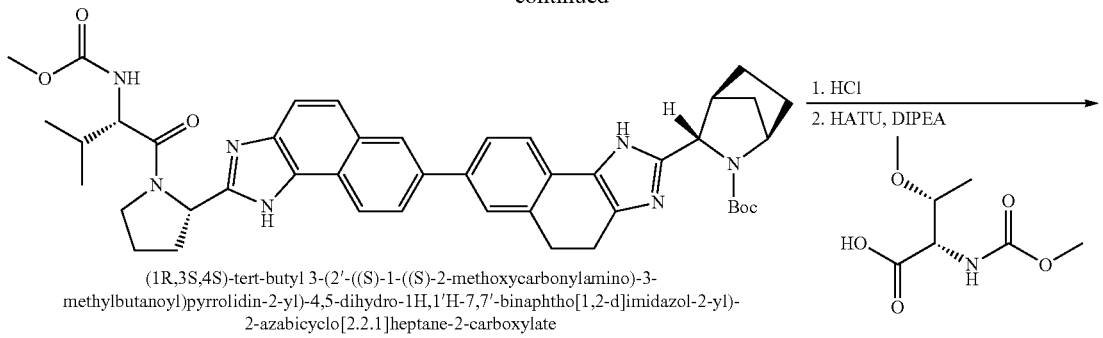

(1R,3S,4S)-tert-butyl 3-(2'-((S)-1-((S)-2-methoxycarbonylamino)-3-methylbutanoyl)pyrrolidin-2-yl)-4,5-dihydro-1H,1'H-7,7'-binaphtho[1,2-d]imidazol-2-yl)-2-azabicyclo[2.2.1]heptane-2-carboxylate

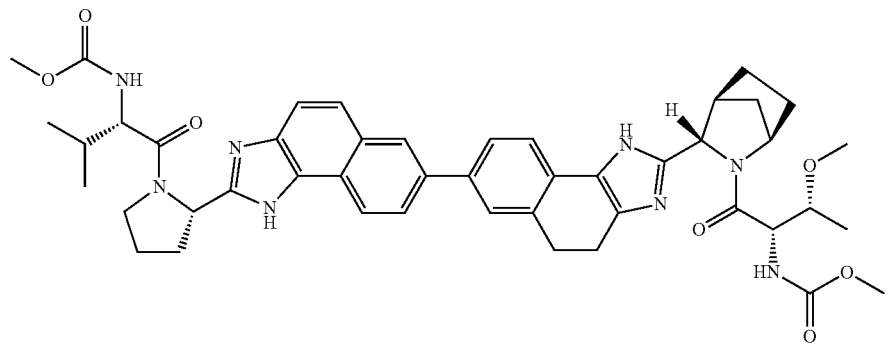

methyl (2S,3R)-3-methoxy-1-((1R,3S,4S)-3-(2'-((S)-1-((S)-2-(methoxycarbonylamino)-3-methylbutanoyl)pyrrolidin-2-yl)-4,5-dihydro-1H,1'H-7,7'-binaphtho[1,2-d]imidazol-2-yl)-2-azabicyclo[2.2.1]heptan-2-yl)-1-oxobutan-2-ylcarbamate (1R,3S,4S)-tert-butyl 3-(7-(4,4,5,5-tetramethyl-1,3,2-dioxaborolan-2-yl)-4,5-dihydro-1H-naphtho[1,2-d]imidazol-2-yl)-2-azabicyclo[2.2.1]heptane-2-carboxylate (1R,3S,4S)-tert-butyl-3-(7-bromo-4,5-dihydro-1H-naphtho[1,2-d]imidazol-2-yl)-2-azabicyclo[2.2.1]heptane-2-carboxylate (660 mg, 1.35 mmol) in dioxane (13 mL) was added bis(pinacolato)diboron (411 mg, 1.2 mmol), KOAc (398 mg, 4.08 mmol), and Pd(dppf)$_2$Cl$_2$ (99 mg, 0.135 mmol). The solution was degassed with N$_2$ for 10 min, then heated to 90° C. for 2 h. The solution was cooled to rt, diluted with EtOAc, washed with sat. NaHCO$_3$, brine, dried with MgSO$_4$, and concentrated. Purified by silica gel chromatography to yield the product (552 mg).

(1R,3S,4S)-tert-butyl-3-(2'-((S)-1-((S)-2-(methoxycarbonylamino)-3-methylbutanoyl) pyrrolidin-2-yl)-4,5-dihydro-1H,1'H-7,7'-binaphtho[1,2-d]imidazol-2-yl)-2-azabicyclo[2.2.1]heptane-2-carboxylate Methyl (S)-1-((S)-2-(7-bromo-1H-naphtho[1,2-d]imidazol-2-yl)pyrrolidin-1-yl)-3-methyl-1-oxobutan-2-ylcarbamate (482 mg, 1.02 mmol) and (1R,3S,4S)-tert-butyl 3-(7-(4,4,5,5-tetramethyl-1,3,2-dioxaborolan-2-yl)-4,5-dihydro-1H-naphtho[1,2-d]imidazol-2-yl)-2-azabicyclo[2.2.1]heptane-2-carboxylate (552 mg, 1.12 mmol) were combined in DME (12 mL). Pd(PPh$_3$)$_4$ (118 mg, 0.102 mmol) and K$_2$CO$_3$ (2M H$_2$O, 1.68 mL, 3.36 mmol) were added, and the solution was degassed with N$_2$ for 10 min. The solution was heated to 85° C. and stirred o/n. The following morning, the solution was cooled to it. The solution was diluted with EtOAc, washed with sat. NaHCO$_3$, brine, dried with MgSO$_4$, and concentrated. The residue was purified by silica gel chromatography to yield product (307 mg).

Methyl (2S,3R)-3-methoxy-1-((1R,3S,4S)-3-(2'-((S)-1-((S)-2-(methoxycarbonylamino)-3-methylbutanoyl)pyrrolidin-2-yl))-4,5-dihydro-1H,1'H-7,7'-binaphtho[1,2-d]imidazol-2-yl)-2-azabicyclo[2.2.1]heptan-2-yl)-1-oxobutan-2-ylcarbamate To (1R,3S,4S)-tert-butyl-3-(2'-((S)-1-((S)-2-(methoxycarbonylamino)-3-methylbutanoyl) pyrrolidin-2-yl)-4,5-dihydro-1H,1'H-7,7'-binaphtho[1,2-d]imidazol-2-yl)-2-azabicyclo[2.2.1]heptane-2-carboxylate (307 mg, 0.41 mmol) in DCM (5 mL) and MeOH (1 mL) was added HCl (4M in dioxane, 1 mL). The solution stirred for 2 h, and the solvent was removed. The intermediate (133 mg, 0.2 mmol) was dissolved in DMF (2.5 mL). (2S,3R)-3-methoxy-2-(methoxycarbonylamino)butanoic acid (38 mg, 0.2 mmol), HATU (76 mg, 0.2 mmol), and DIPEA (0.18 mL, 1.0 mmol) were added sequentially. The solution stirred o/n and the mixture was purified by HPLC to yield product (104.1 mg). LCMS-ESI$^+$: calc'd for $C_{46}H_{54}N_8O_7$: 830.97 (M$^+$); Found: 832.39 (M+H$^+$).

Example AQ

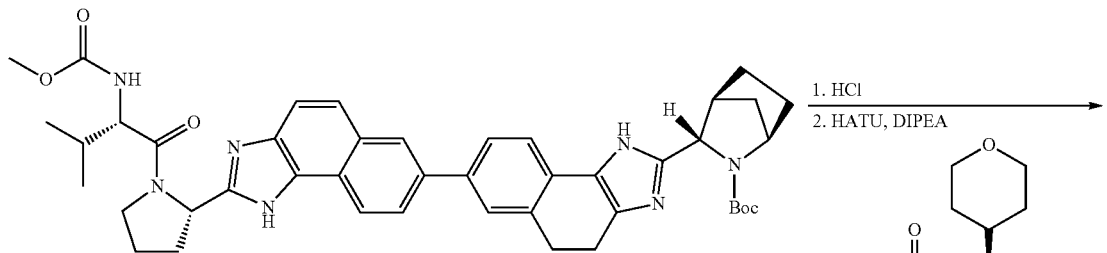

(1R,3S,4S)-tert-butyl 3-(2'-((S)-1-((S)-2-(methoxycarbonylamino)-3-methylbutanoyl)pyrrolidin-2-yl)-4,5-dihydro-1H,1'H-7,7'-binaphtho[1,2-d]imidazol-2-yl)-2-azabicyclo[2.2.1]heptane-2-carboxylate 1. HCl
2. HATU, DIPEA

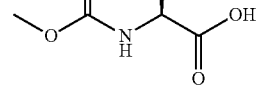

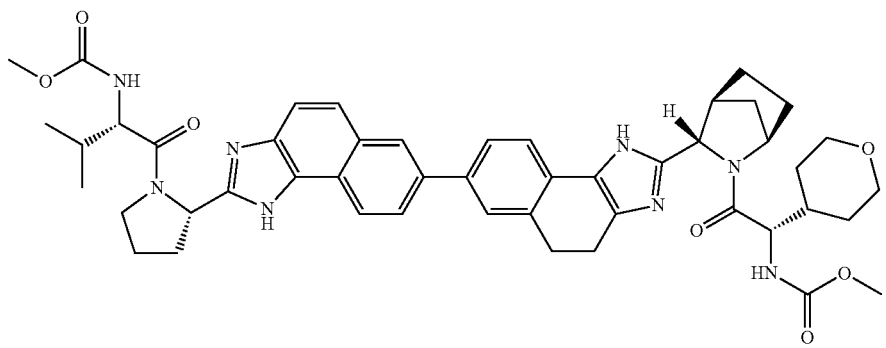

methyl (S)-2-((1R,3S,4S)-3-(2'-((S)-1-((S)-2-(methoxycarbonylamino)-3-methylbutanoyl)pyrrolidin-2-yl)-4,5-dihydro-1H,1'H-7,7'-binaphtho[1,2-d]imidazol-2-yl)-2-azabicyclo[2.2.1]heptan-2-yl)-2-oxo-1-(tetrahydro-2H-pyran-4-yl)ethylcarbamate

Methyl (S)-2-((1R,3S,4S)-3-(2'-((S)-1-((S)-2-(methoxycarbonylamino)-3-methylbutanoyl) pyrrolidin-2-yl)-4,5-dihydro-1H,1'H-7,7'-binaphtho[1,2-d]imidazol-2-yl)-2-azabicyclo[2.2.1]heptan-2-yl)-2-oxo-1-(tetrahydro-2H-pyran-4-yl)ethylcarbamate To (1R,3S,4S)-tert-butyl-3-(2'-((S)-1-((S)-2-(methoxycarbonylamino)-3-methylbutanoyl)pyrrolidin-2-yl)-4,5-dihydro-1H, 1'H-7,7'-binaphtho[1,2-d]imidazol-2-yl)-2-azabicyclo[2.2.1]heptane-2-carboxylate (307 mg, 0.41 mmol) in DCM (5 mL) and MeOH (1 mL) was added HCl (4M in dioxane, 1 mL). The solution stirred for 2 h, and the solvent was removed. The intermediate (133 mg, 0.2 mmol) was dissolved in DMF (2.5 mL). ((S)-2-(methoxycarbonylamino)-2-(tetrahydro-2H-pyran-4-yl)acetic acid (43 mg, 0.2 mmol), HATU (76 mg, 0.2 mmol), and DIPEA (0.18 mL, 1.0 mmol) were added sequentially. The solution stirred o/n and the mixture was purified by HPLC to yield product (100.8 mg). LCMS-ESI+: calc'd for $C_{48}H_{56}N_8O_7$: 857.01 (M+); Found: 857.42 (M+H+).

Example AR

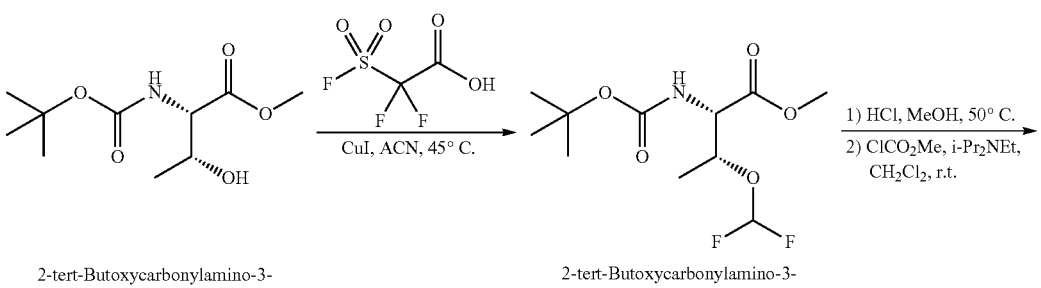

2-tert-Butoxycarbonylamino-3-hydroxy-butyric acid methyl ester

CuI, ACN, 45° C.

2-tert-Butoxycarbonylamino-3-difluoromethoxy-butyric acid methyl ester

1) HCl, MeOH, 50° C.
2) ClCO₂Me, i-Pr₂NEt, CH₂Cl₂, r.t.

-continued
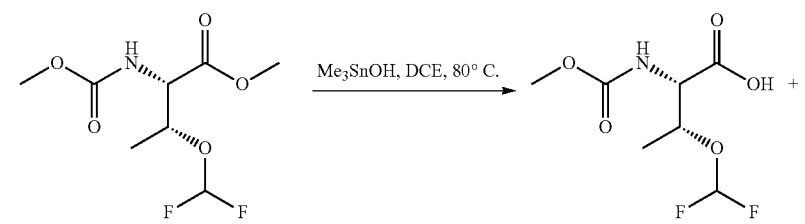
(2S,3R)-methyl 3-(difluoromethoxy)-2-(methoxycarbonylamino)butanoate
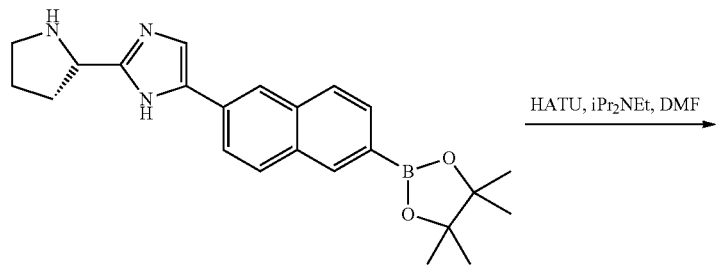
(S)-2-(pyrrolidin-2-yl)-5-(6-(4,4,5,5-tetramethyl-1,3,2-dioxaborolan-2-yl)naphthalen-2-yl)-1H-imidazole
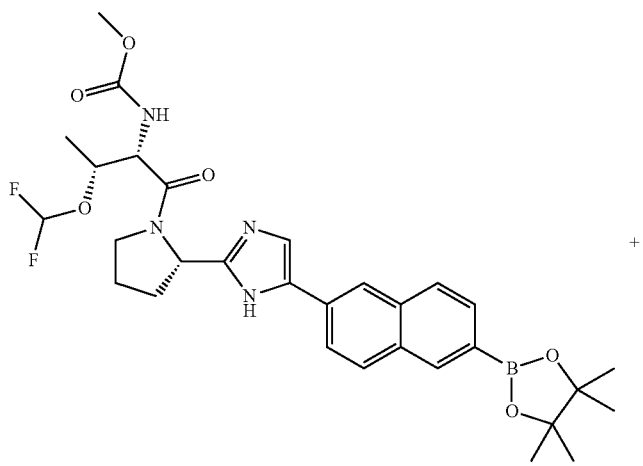
methyl (2S,3R)-3-(difluoromethoxy)-1-oxo-1-((S)-2-(5-(6-(4,4,5,5-tetramethyl-1,3,2-dioxaborolan-2-yl)naphthalen-2-yl)-1H-imidazol-2-yl)pyrrolidin-1-yl)butan-2-ylcarbamate
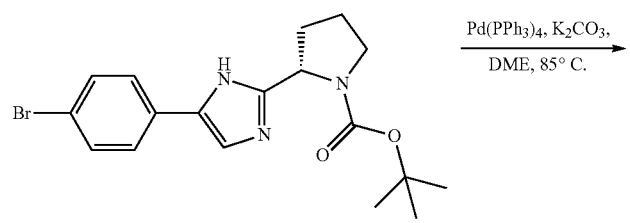
(S)-tert-butyl 2-(5-(4-bromophenyl)-1H-imidazol-2-yl)pyrrolidine-1-carboxylate -continued

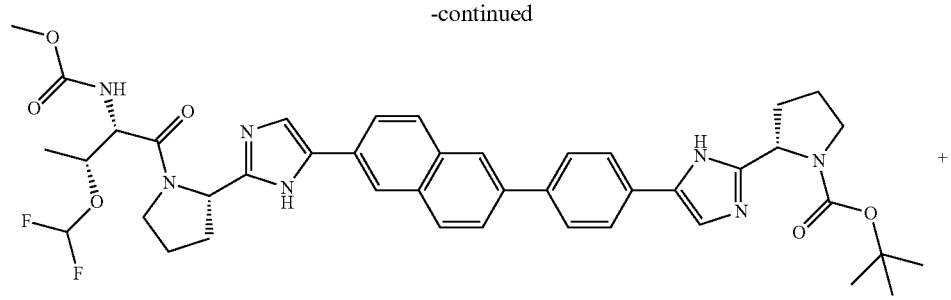

(S)-tert-butyl 2-(5-(4-(6-(2-((S)-1-((2S,3R)-3-(difluoromethoxy)-2-(methoxycarbonylamino)butanoyl)pyrrolidin-2-yl)-1H-imidazol-5-yl)naphthalen-2-yl)phenyl)-1H-imidazol-2-yl)pyrrolidine-1-carboxylate

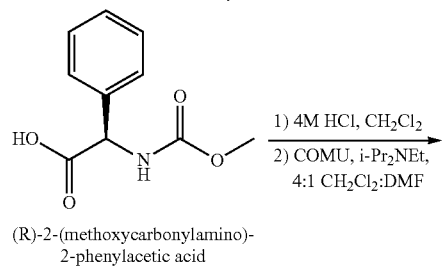

(R)-2-(methoxycarbonylamino)-2-phenylacetic acid 1) 4M HCl, CH$_2$Cl$_2$
2) COMU, i-Pr$_2$NEt, 4:1 CH$_2$Cl$_2$:DMF

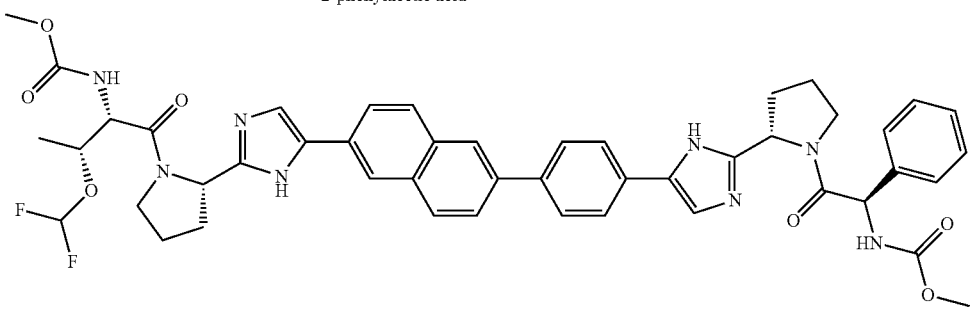

methyl (2S,3R)-1-((S)-2-(5-(6-(4-(2-((S)-1-((R)-2-methoxycarbonylamino-2-phenylacetyl)pyrrolidin-2-yl)-1H-imidazol-5-yl)phenyl)naphthalen-2-yl)-1H-imidazol-2-yl)pyrrolidin-1-yl)-3-(difluoromethoxy)-1-oxobutan-2-ylcarbamate 2-tert-Butoxycarbonylamino-3-difluoromethoxy-butyric acid methyl ester: To a mixture of 2-tert-butoxycarbonylamino-3-hydroxy-butyric acid methyl ester (630 mg, 2.70 mmol) and copper(I) iodide (105 mg, 0.55 mmol) in acetonitrile at 45° C. was added a solution of 2-(fluorosulfonyl)difluoroacetic acid (0.560 mL, 5.42 mmol) in acetonitrile (2 mL) by syringe pump over 45 minutes. The reaction was then stirred at 45° C. for 30 minutes. Another solution of 2-(fluorosulfonyl)difluoroacetic acid (0.560 mL, 5.42 mmol) in acetonitrile (2 mL) was added by syringe pump over 45 minutes at 45° C. The reaction was stirred for 30 minutes at 45° C. after the second syringe pump addition was complete. Water was carefully added to quench the reaction, and the mixture was diluted with ethyl acetate. The organic layer was separated, washed with water and brine, dried (MgSO$_4$) and concentrated. The crude material was purified by flash chromatography (10% ethyl acetate/hexanes) to yield 2-tert-butoxycarbonylamino-3-difluoromethoxy-butyric acid methyl ester (276 mg, 36%).
$^1$H-NMR: 400 MHz, (CDCl$_3$: 6.16 (t, J$_{HF}$=74.0 Hz, 1H), 5.23-5.16 (br, 1H), 4.86-4.80 (m, 1H), 4.40 (br d, J=9.8 Hz, 1H), 3.76 (s, 3H), 1.46 (br s, 9H), 1.36 (d, J=6.4 Hz, 3H) ppm.

(2S,3R)-methyl-3-(difluoromethoxy)-2-(methoxycarbonylamino)butanoate: To a solution of 2-tert-Butoxycarbonylamino-3-difluoromethoxy-butyric acid methyl ester (3 g, 10.6 mmol) in methanol (40 mL) was added concentrated HCl solution (10 mL) and the reaction was stirred at 50° C. for 1 hour. The reaction was concentrated on a rotary evaporator and the resulting residue was basified with saturated NaHCO$_3$ solution. The aqueous layer was extracted twice with ethyl acetate. The organic layer was separated, washed with brine, dried (MgSO4) and concentrated. To a solution of the crude material in dichloromethane (50 mL) was added diisopropylethylamine (4.2 mL, 24.2 mmol), followed by methyl chloroformate (0.95 mL, 12.3 mmol). The reaction was stirred at room temperature for 2 hours, quenched by the careful addition of saturated NH$_4$Cl solution and diluted with ethyl acetate. The organic layer was separated, washed with water and brine, dried (MgSO$_4$) and concentrated. The crude material was purified by flash chromatography to yield (2S,3R)-methyl-3-(difluoromethoxy)-2-(methoxycarbonylamino)butanoate (1.2 g, 47%).

(2S,3R)-3-(difluoromethoxy)-2-(methoxycarbonylamino)butanoic acid: To a solution of (2S,3R)-methyl-3-(difluoromethoxy)-2-(methoxycarbonylamino)butanoate (265 mg, 1.1 mmol) in dichloroethane (10 mL) was added trimethyltin hydroxide (1 g, 5.5 mmol) and the resulting mixture was heated to 80° C. for 1 hour. The reaction was cooled to room temperature, diluted with ethyl acetate, washed twice with 5% aqueous HCl solution and brine, dried (MgSO$_4$) and concentrated. The resulting crude material (209 mg, 84%) was used without further purification.

Methyl (2S,3R)-3-(difluoromethoxy)-1-oxo-1-((S)-2-(5-(6-(4,4,5,5-tetramethyl-1,3,2-dioxaborolan-2-yl)naphthalen-2-yl)-1H-imidazol-2-yl)pyrrolidin-1-yl)butan-2-ylcarbamate: To a solution of (2S,3R)-3-(difluoromethoxy)-2-(methoxycarbonylamino)butanoic acid (205 mg, 0.9 mmol) and (S)-2-(pyrrolidin-2-yl)-5-(6-(4,4,5,5-tetramethyl-1,3,2-dioxaborolan-2-yl)naphthalen-2-yl)-1H-imidazole (315 mg, 0.8 mmol) in dimethylformamide (8 mL) was added HATU (325 mg, 0.85 mmol) and diisopropylethylamine (0.565 mL, 3.2 mmol). The reaction was stirred for 1 hour and then diluted with ethyl acetate. The organic layer was washed twice with saturated NaHCO$_3$ solution and brine, dried (MgSO$_4$) and concentrated. The resulting residue was purified by falsh chromatography to yield methyl (2S,3R)-3-(difluoromethoxy)-1-oxo-1-((S)-2-(5-(6-(4,4,5,5-tetramethyl-1,3,2-dioxaborolan-2-yl)naphthalen-2-yl)-1H-imidazol-2-yl)pyrrolidin-1-yl)butan-2-ylcarbamate (230 mg, 47%). LCMS-ESI$^+$: calculated for C$_{30}$H$_{37}$BF$_2$N$_4$O$_6$: 598.45; observed [M+1]$^+$: 599.31.

(S)-tert-butyl 2-(5-(4-(6-(2-((S)-1-((2S,3R)-3-(difluoromethoxy)-2-(methoxycarbonylamino)butanoyl)pyrrolidin-2-yl)-1H-imidazol-5-yl)naphthalen-2-yl)phenyl)-1H-imidazol-2-yl)pyrrolidine-1-carboxylate: To a solution of methyl (2S,3R)-3-(difluoromethoxy)-1-oxo-1-((S)-2-(5-(6-(4,4,5,5-tetramethyl-1,3,2-dioxaborolan-2-yl)naphthalen-2-yl)-1H-imidazol-2-yl)pyrrolidin-1-yl)butan-2-ylcarbamate (120 mg, 0.20 mmol), (S)-tert-butyl 2-(5-(4-bromophenyl)-1H-imidazol-2-yl)pyrrolidine-1-carboxylate (87 mg, 0.22 mmol), and tetrakistriphenylphosphine palladium(0) (23 mg, 0.020 mmol) in dimethoxyethane (2 mL) was added a 2M aqueous potassium carbonate solution (0.40 mL, 0.80 mmol). The mixture was degassed with a stream of argon for 15 minutes, and then heated to 85° C. for three hours. The reaction was diluted with ethyl acetate, cooled to room temperature and filtered through Celite. The filtrate was washed with water and brine, dried (MgSO$_4$) and concentrated. The resulting residue was purified by flash chromatography to yield (S)-tert-butyl 2-(5-(4-(6-(2-((S)-1-((2S,3R)-3-(difluoromethoxy)-2-(methoxycarbonylamino)butanoyl)-1H-imidazol-2-yl)-1H-imidazol-5-yl)naphthalen-2-yl)phenyl)-1H-imidazol-2-yl)pyrrolidine-1-carboxylate (70 mg, 45%). LCMS-ESI$^+$: calculated for C$_{42}$H$_{47}$F$_2$N$_7$O$_6$: 783.86; observed [M+1]$^+$: 784.72.

Methyl (2S,3R)-1-((S)-2-(5-(6-(4-(2-((S)-1-((R)-2-methoxycarbonylamino-2-phenylacetyl)pyrrolidin-2-yl)-1H-imidazol-5-yl)phenyl)naphthalen-2-yl)-1H-imidazol-2-yl)pyrrolidin-1-yl)-3-(difluoromethoxy)-1-oxobutan-2-ylcarbamate: A solution of (S)-tert-butyl 2-(5-(4-(6-(2-((S)-1-((2S,3R)-3-(difluoromethoxy)-2-(methoxycarbonylamino)butanoyl)pyrrolidin-2-yl)-1H-imidazol-5-yl)naphthalen-2-yl)phenyl)-1H-imidazol-2-yl)pyrrolidine-1-carboxylate (68 mg, 0.09 mmol), dichloromethane (1 mL), 4M HCl in dioxane (0.07 mL, 0.28 mmol) and dimethylformamide (0.1 mL) was stirred at room temperature for one hour. Dichloromethane (5 mL) was added to the reaction and then concentrated to a solid. Dilution with dichloromethane and concentration was repeated a total of three times. The resulting solid was dissolved in methanol and filtered through a freebasing column (Stratospheres™ PL-HCO$_3$MP SPE, Part #: PL3540-C603). The filtrate was concentrated and used without further purification. The crude material was dissolved in a 4:1 dichloromethane:dimethylformamide solution (0.8 mL). To this solution was added (R)-2-(methoxycarbonylamino)-2-phenylacetic acid (25 mg, 0.12 mmol) and COMU (41 mg, 0.1 mmol) and the reaction was cooled to 0° C. Diisopropylethylamine (0.045 mL, 0.24 mmol) was added and the reaction was stirred at 0° C. for one hour. The reaction was diluted with ethyl acetate and the organic layer was washed with water and brine, dried (MgSO$_4$) and concentrated. The resulting residue was purified by preparative reverse phase HPLC (Gemini, 15 to 50% ACN/H$_2$O+ 0.1% HCO$_2$H) to yield methyl (2S,3R)-1-((S)-2-(5-(6-(4-(2-((S)-1-((R)-2-methoxycarbonylamino-2-phenylacetyl)pyrrolidin-2-yl)-1H-imidazol-5-yl)phenyl)naphthalen-2-yl)-1H-imidazol-2-yl)pyrrolidin-1-yl)-3-(difluoromethoxy)-1-oxobutan-2-ylcarbamate (34 mg, 45% over 2 steps). LCMS-ESI$^+$: calculated for C$_{47}$H$_{48}$F$_2$N$_8$O$_7$: 874.93; observed [M+1]$^+$: 875.78.

Example AS

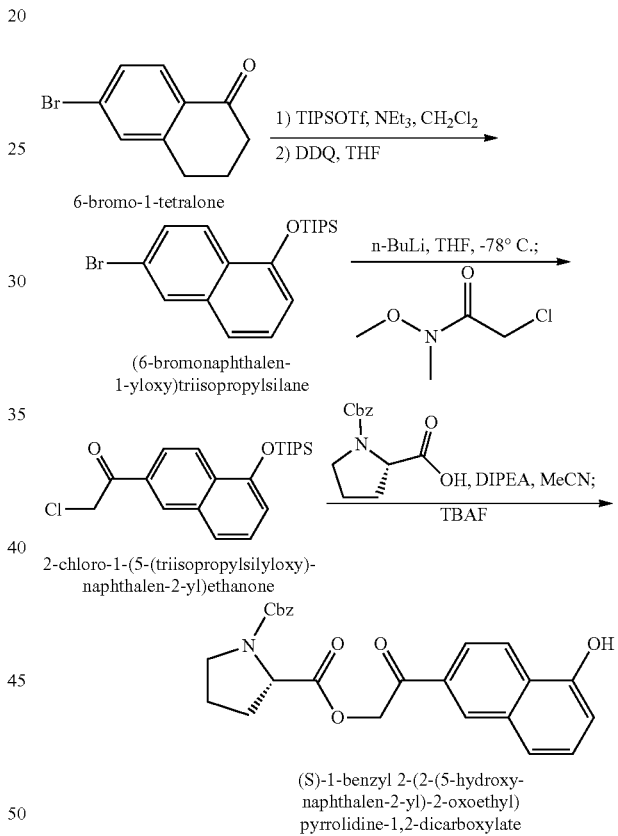

(6-bromonaphthalen-1-yloxy)triisopropylsilane: To a solution of 6-bromo-1-tetralone (10.6 g, 47.1 mmol) in dichloromethane (145 mL) cooled to 0° C. were sequentially added triethylamine (12 mL, 86.1 mmol) and triisopropylsilyl trifluoromethanesulfonate (15.3 mL, 56.7 mmol). After stirring for ten minutes, the ice bath was removed and the reaction was allowed to warm to room temperature for 30 minutes. The reaction was diluted with 1:1 ethyl acetate:hexanes and the organic layer was washed with water and brine. The organics were dried (MgSO$_4$), concentrated, and the resulting material was used without further purification. The crude enolsilane was dissolved in tetrahydrofuran (470 mL) and cooled to 0° C. To the solution was added solid 2,3-dichloro-5,6-dicyanobenzoquinone (16 g, 70.5 mmol) and the reaction was warmed to room temperature. After 30 minutes the reaction was concentrated and the crude material was purified by flash column chromatography (hexanes) to afford (6-bromonaphthalen-1-yloxy)triisopropylsilane (17.1 g, 96% over 2 steps).

2-chloro-1-(5-(triisopropylsilyloxy)-naphthalen-2-yl) ethanone: To a solution of (6-bromonaphthalen-1-yloxy) triisopropylsilane (10.4 g, 27.5 mmol) in tetrahydrofuran (180 mL) under argon at −78° C. was added n-butyllithium (2.5M in hexanes, 11.5 mL, 28.7 mmol). After stirring at this temperature for one hour, a solution of 2-chloro-N-methoxy-N-methyl acetamide (7.6 g, 55.2 mmol) in tetrahydrofuran (10 mL) was added to the reaction via cannula. The dry ice bath was removed and the reaction was allowed to warm to room temperature. After one hour at room temperature the reaction was diluted with ethyl acetate and the organics were washed with saturated aqueous $NH_4Cl$ solution, water and brine. The organic layer was dried ($MgSO_4$) and concentrated, and the resulting residue was purified by flash chromatography to yield 2-chloro-1-(5-(triisopropylsilyloxy)-naphthalen-2-yl)ethanone (7.8 g, 75%) as a pale yellow oil.

(S)-1-benzyl 2-(2-(5-hydroxy-naphthalen-2-yl)-2-oxoethyl) pyrrolidine-1,2-dicarboxylate: To a solution of 2-chloro-1-(5-(triisopropylsilyloxy)-naphthalen-2-yl)ethanone (7.8 g, 20.7 mmol) and N-benzyloxycarbonyl-L-proline (5.4 g, 21.7 mmol) in acetonitrile (105 mL) was added diisopropylethylamine (7.2 mL, 41.4 mmol). The reaction was heated to 60° C. for one hour until TLC confirmed that all of the of 2-chloro-1-(5-(triisopropylsilyloxy)-naphthalen-2-yl)ethanone was consumed. Then tetrabutylammonium fluoride solution (1M in THF, 41.4 mL, 41.4 mmol) was added and the reaction was allowed to stir at 60° C. After one hour at this temperature, the reaction was cooled to room temperature and diluted with ethyl acetate and water. The organic layer was separated, washed with water and brine, dried ($MgSO_4$) and concentrated. The crude material was purified by flash column chromatography to yield (S)-1-benzyl 2-(2-(5-hydroxy-naphthalen-2-yl)-2-oxoethyl) pyrrolidine-1,2-dicarboxylate (7.1 g, 79%). LCMS-ESI[+]: calculated for $C_{25}H_{23}NO_6$: 433.15; observed [M+1][+]: 433.97.

Example AT

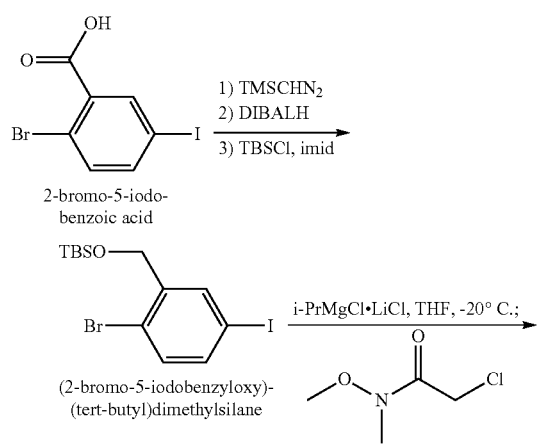

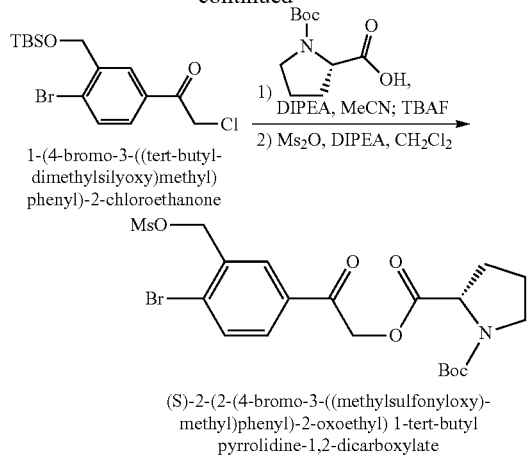

(2-bromo-5-iodobenzyloxy)-(tert-butyl)dimethylsilane: To a solution of 2-bromo-5-iodobenzoic acid (11.4 g, 34.8 mmol) in dichloromethane (140 mL) was added methanol (17 mL) followed by trimethylsilyldiazomethane solution (2M in hexanes, 19.2 mL, 38.4 mmol). The reaction was stirred at room temperature for twelve hours, quenched by the dropwise addition of acetic acid (5 mL) and thoroughly concentrated. The resulting residue was dissolved in tetrahydrofuran. To this solution was added diisobutylaluminum hydride solution (1M in DCM, 50 mL, 50 mmol) and the reaction was stirred at room temperature. After sixteen hours, more diisobutylaluminum hydride solution (1M in DCM, 50 mL, 50 mmol) was added. After 96 more hours at room temperature the reaction was diluted with ether (100 mL) and quenched by the sequential addition of water (4 mL), 15% aqueous NaOH solution (4 mL) and water (10 mL). After thirty minutes the mixture was filtered through Celite and the filtrate was concentrated. The resulting residue was dissolved in dimethylformamide (75 mL). To this solution was added imidazole (6.1 g, 89.6 mmol) and t-butyldimethylchlorosilane (6.8 g, 45.1 mmol). The reaction was stirred at room temperature for two hours and then diluted with ethyl acetate. The organics were washed with saturated aqueous $NH_4Cl$ solution, water and brine. The organic layer was dried ($MgSO_4$) and concentrated, and the resulting residue was purified by flash column chromatography to yield (2-bromo-5-iodobenzyloxy)-(tert-butyl)dimethylsilane (9.2 g, 62%).

1-(4-bromo-3-((tert-butyldimethylsilyloxy)methyl)phenyl)-2-chloroethanone: To a solution of (2-bromo-5-iodobenzyloxy)-(tert-butyl)dimethylsilane (8.7 g, 20.3 mmol) in tetrahydrofuran (135 mL) under argon at −20° C. was added i-propylmagnesium chloride-lithium chloride solution (1.3M in THF, 16.4 mL, 21.3 mmol). After stirring at this temperature for thirty minutes, a solution of 2-chloro-N-methoxy-N-methyl acetamide (3.4 g, 24.3 mmol) in tetrahydrofuran (5 mL) was added to the reaction via cannula. The reaction was stirred at −20° C. for one hour and then warmed to room temperature. After one hour at room temperature the reaction was diluted with ethyl acetate and the organics were washed with saturated aqueous $NH_4Cl$ solution, water and brine. The organic layer was dried ($MgSO_4$) and concentrated, and the resulting residue was purified by flash chromatography to yield 1-(4-bromo-3-((tert-butyldimethylsilyloxy)methyl)phenyl)-2-chloroethanone (5.1 g, 67%).

(S)-2-(2-(4-bromo-3-((methylsulfonyloxy)methyl)phenyl)-2-oxoethyl) 1-tert-butyl pyrrolidine-1,2-dicarboxylate: To a solution of 1-(4-bromo-3-((tert-butyldimethylsilyloxy)methyl)phenyl)-2-chloroethanone (5.1 g, 13.5 mmol) and N-t-butoxycarbonyl-L-proline (3.8 g, 17.6 mmol) in acetonitrile (68 mL) was added diisopropylethylamine (7.0 mL, 40.5 mmol). The reaction was heated to 60° C. for one hour until TLC confirmed that all of the of 1-(4-bromo-3-((tert-butyldimethylsilyloxy)methyl)phenyl)-2-chloroethanone was consumed. Then tetrabutylammonium fluoride solution (1M in THF, 27.0 mL, 27.0 mmol) was added and the reaction was allowed to stir at 60° C. After one hour at this temperature, the reaction was cooled to room temperature and diluted with ethyl acetate and water. The organic layer was separated, washed with water and brine, dried (MgSO$_4$) and concentrated. The crude material was purified by flash column chromatography to yield the free benzyl alcohol (4.7 g, 78%). The benzyl alcohol and diisopropylethylamine (6 mL, 34.5 mmol) were dissolved in dichloromethane (100 mL). To this solution was added methanesulfonic anhydride (2.3 g, 12.1 mmol) and the reaction was stirred for 45 minutes. The reaction was diluted with dichloromethane, and the organics were washed with water. The organic layer was dried (MgSO$_4$) and concentrated, and the resulting residue was purified by flash column chromatography to yield (S)-2-(2-(4-bromo-3-((methylsulfonyloxy)methyl)phenyl)-2-oxoethyl) 1-tert-butyl pyrrolidine-1,2-dicarboxylate (5.2 g, 94%).

Example AU

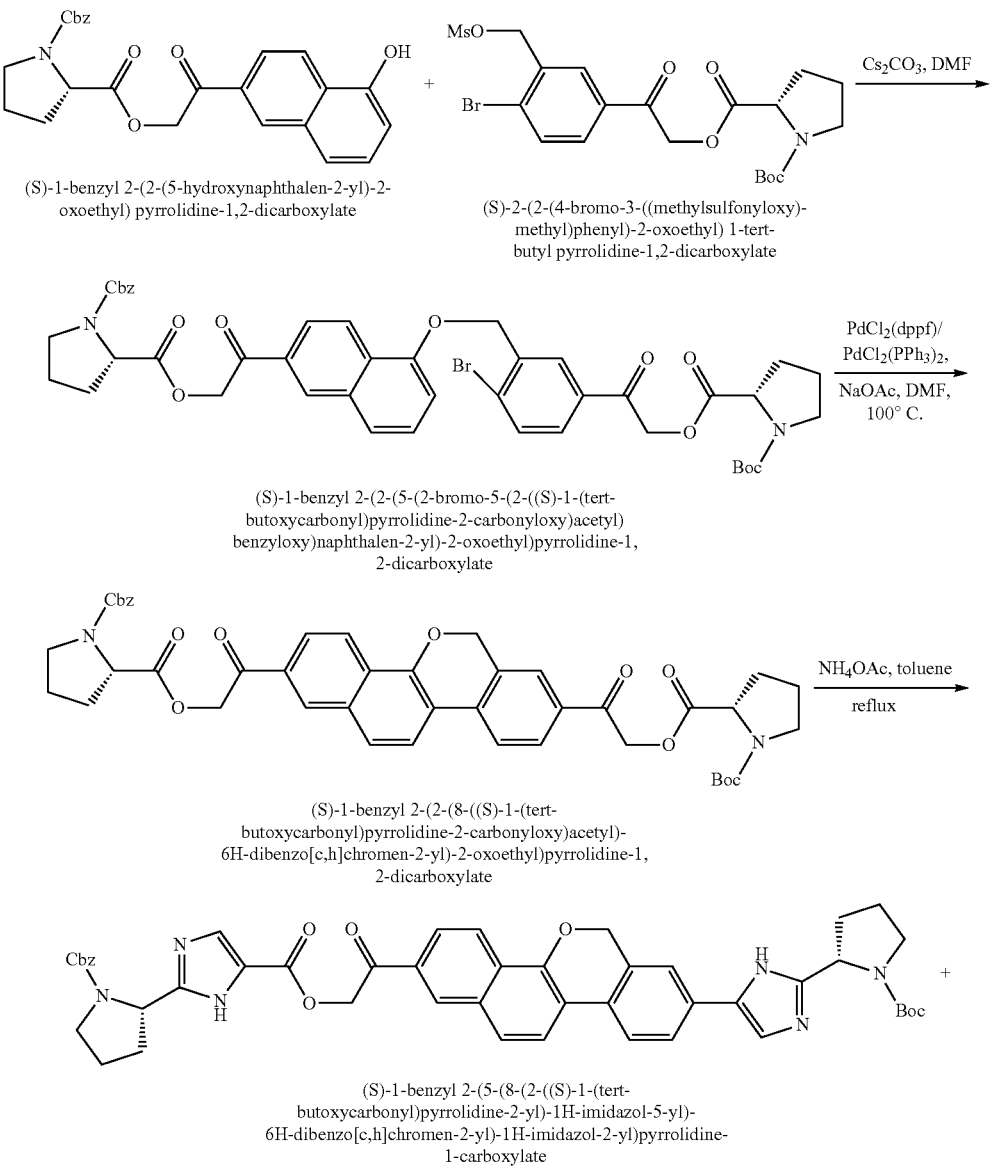

-continued

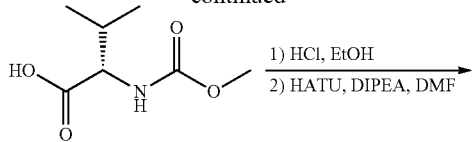

(S)-2-(methoxycarbonylamino)-
3-methylbutanoic acid

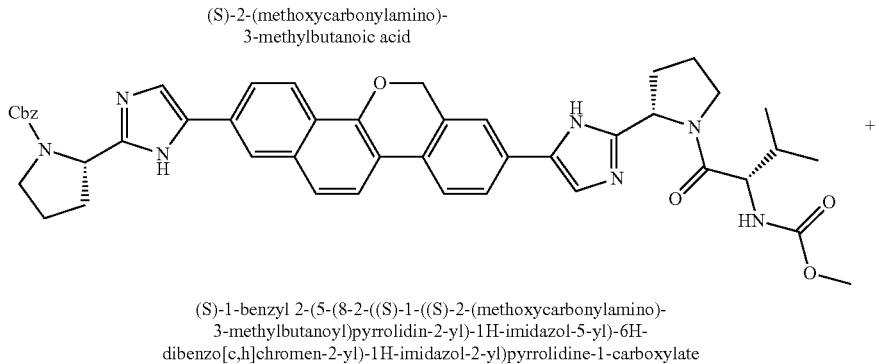

(S)-1-benzyl 2-(5-(8-2-((S)-1-((S)-2-(methoxycarbonylamino)-
3-methylbutanoyl)pyrrolidin-2-yl)-1H-imidazol-5-yl)-6H-
dibenzo[c,h]chromen-2-yl)-1H-imidazol-2-yl)pyrrolidine-1-carboxylate

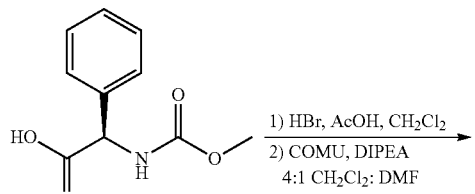

(R)-2-(methoxycarbonylamino)-
2-phenylacetic acid

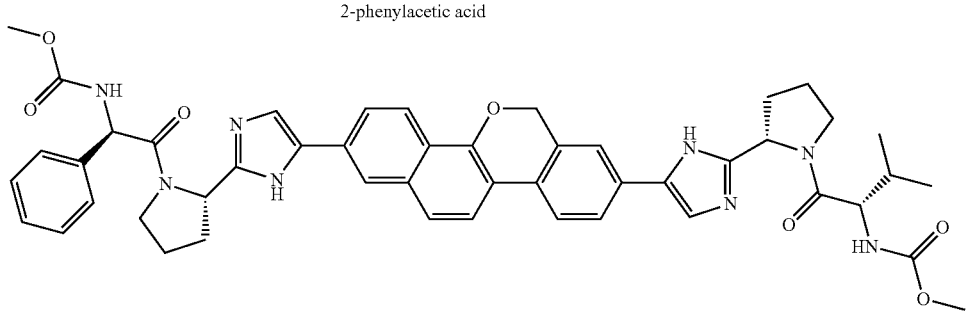

methyl (R)-2-((S)-2-(5-(8-(2-((S)-1-((SD)-2-methoxycarbonylamino-3-methylbutanoyl)pyrrolidin-2-yl)-
1H-imidazol-5-yl)-6H-dibenzo[c,h]chromen-2-yl)-1H-imidazol-2-yl)pyrrolidin-1-yl)-2-oxo-1-
phenylethylcarbamate (S)-1-benzyl 2-(2-(5-(2-bromo-5-(2-((S)-1-(tert-butoxycarbonyl)-pyrrolidine-2-carbonyloxy)acetyl)benzyloxy)naphthalen-2-yl)-2-oxoethyl) pyrrolidine-1,2-dicarboxylate:

To a solution of (S)-2-(2-(4-bromo-3-((methylsulfonyloxy)methyl)phenyl)-2-oxoethyl) 1-tert-butyl pyrrolidine-1,2-dicarboxylate (5.2 g, 10.0 mmol) and (S)-1-benzyl 2-(2-(5-hydroxy-naphthalen-2-yl)-2-oxoethyl) pyrrolidine-1,2-dicarboxylate (4.5g, 10.4 mmol) in dimethylformamide (100 mL) was added cesium carbonate (7.2 g, 22.1 mmol). The mixture was stirred at room temperature for two hours and diluted with ethyl acetate. The organics were washed with water and brine, dried (MgSO$_4$) and concentrated. The resulting residue was purified by flash column chromatography to yield (S)-1-benzyl 2-(2-(5-(2-bromo-5-(2-((S)-1-(tert-butoxycarbonyl)-pyrrolidine-2-carbonyloxy)acetyl)benzyloxy)naphthalen-2-yl)-2-oxoethyl) pyrrolidine-1,2-dicarboxylate (6.3 g, 74%). LCMS-ESI$^+$: calculated for $C_{44}H_{45}BrN_2O_{11}$: 856.22; observed [M+Na]$^+$: 879.21.

(S)-1-benzyl 2-(2-(8-(2-((S)-1-(tert-butoxycarbonyl)-pyrrolidine-2-carbonyloxy)acetyl)-6H-dibenzo-[c,h]chromen-2-yl)-2-oxoethyl) pyrrolidine-1,2-dicarboxylate: A mixture of (S)-1-benzyl 2-(2-(5-(2-bromo-5-(2-((S)-1-(tert-butoxycarbonyl)-pyrrolidine-2-carbonyloxy)acetyl)benzyloxy) naphthalen-2-yl)-2-oxoethyl) pyrrolidine-1,2-dicarboxylate (3.7 g, 4.3 mmol), PdCl$_2$(dppf) (0.63 g, 0.86 mmol), sodium acetate (1.1 g, 13.3 mmol) and dimethylformamide (43 mL) was degassed with a stream of argon for 15 minutes. The mixture was then heated to 110° C. for 6 hours. The reaction was cooled to room temperature, diluted with ethyl acetate and water, and the biphasic mixture was filtered through Celite. The organic portion of the filtrate was separated, washed with more water and brine, dried (MgSO$_4$) and concentrated. The resulting residue was purified by flash column chromatography to yield (S)-1-benzyl 2-(2-(8-(2-((S)-1-(tert-butoxycarbonyl)-pyrrolidine-2-carbonyloxy)acetyl)-6H-dibenzo-[c,h]chromen-2-yl)-2-oxoethyl) pyrrolidine-1,2-dicarboxylate (1.5 g, 46%). LCMS-ESI$^+$: calculated for $C_{44}H_{44}N_2O_{11}$: 776.29; observed [M-BOC+1]$^+$: 677.53.

(S)-benzyl 2-(5-(8-(2-((S)-1-(tert-butoxycarbonyl)pyrrolidin-2-yl)-1H-imidazol-5-yl)-6H-dibenzo[c,h]chromen-2-yl)-1H-imidazol-2-yl)pyrrolidine-1-carboxylate: To a solution of (S)-1-benzyl 2-(2-(8-(2-((S)-1-(tert-butoxycarbonyl)-pyrrolidine-2-carbonyloxy)acetyl)-6H-dibenzo-[c,h]chromen-2-yl)-2-oxoethyl) pyrrolidine-1,2-dicarboxylate (2.0 g, 2.6 mmol) in toluene (30 mL) was added ammonium acetate (3.5 g, 41.7 mmol). The resulting mixture was vigorously refluxed for three hours. The reaction was cooled to room temperature and diluted with ethyl acetate. The organic were washed with water and brine, dried (MgSO$_4$) and concentrated. The resulting crude material was purified by flash column chromatography to yield (S)-benzyl 2-(5-(8-(2-((S)-1-(tert-butoxycarbonyl)pyrrolidin-2-yl)-1H-imidazol-5-yl)-6H-dibenzo[c,h]chromen-2-yl)-1H-imidazol-2-yl)pyrrolidine-1-carboxylate (1.2 g, 62%). LCMS-ESI$^+$: calculated for C$_{44}$H$_{44}$N$_6$O$_5$: 736.34; observed [M+1]$^+$: 737.27.

(S)-benzyl 2-(5-(8-(2-((S)-1-((S)-2-(methoxycarbonylamino)-3-methylbutanoyl)pyrrolidin-2-yl)-1H-imidazol-5-yl)-6H-dibenzo[c,h]chromen-2-yl)-1H-imidazol-2-yl)pyrrolidine-1-carboxylate: A solution of (S)-benzyl 2-(5-(8-(2-((S)-1-(tert-butoxycarbonyl)pyrrolidin-2-yl)-1H-imidazol-5-yl)-6H-dibenzo[c,h]chromen-2-yl)-1H-imidazol-2-yl) pyrrolidine-1-carboxylate (1.2 g, 1.6 mmol), concentrated HCl (1.5 mL) and ethanol (10 mL) was heated to 60° C. for one hour. The reaction was concentrated and redissolved in a minimal amount of methanol. An equal volume of dichloromethane was added and the solution was again concentrated. Dichloromethane was added to the resulting residue and concentrated off three more times, until the crude material was a yellow powder. A portion of the crude amine (0.3 g, ~0.40 mmol) was dissolved in dimethylformamide (4.7 mL). To this solution was added (S)-2-(methoxycarbonylamino)-3-methylbutanoic acid (125 mg, 0.7 mmol), HATU (270 mg, 0.7 mmol) and diisopropylethylamine (0.82 mL, 4.7 mmol). The reaction was stirred at room temperature for one hour, and then diluted with acetonitrile (2 mL) and methanol (2 mL). To this solution was added ten drops of 5M aqueous NaOH solution and stirring was continued for 30 minutes. The reaction was diluted with ethyl acetate and the organic layer was washed with water and brine. The combined aqueous washings were extracted three times with ethyl acetate, and the combined organic layers were dried (MgSO$_4$) and concentrated. The crude material was purified by flash column chromatography to yield (S)-benzyl 2-(5-(8-(2-((S)-1-((S)-2-(methoxycarbonylamino)-3-methylbutanoyl)pyrrolidin-2-yl)-1H-imidazol-5-yl)-6H-dibenzo[c,h]chromen-2-yl)-1H-imidazol-2-yl)pyrrolidine-1-carboxylate (260 mg, ~80%). LCMS-ESI$^+$: calculated for C$_{46}$H$_{47}$N$_7$O$_6$: 793.91; observed [M+1]$^+$: 794.70.

Methyl (R)-2-((S)-2-(5-(8-(2-((S)-1-((S)-2-methoxycarbonylamino-3-methylbutanoyl)pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate: A mixture of (S)-benzyl 2-(5-(8-(2-((S)-1-((S)-2-(methoxycarbonylamino)-3-methylbutanoyl)pyrrolidin-2-yl)-1H-imidazol-5-yl)-6H-dibenzo[c,h]chromen-2-yl)-1H-imidazol-2-yl)pyrrolidine-1-carboxylate (260 mg, 0.33 mmol), 33% HBr in acetic acid (1 mL) and dichloromethane (4 mL) was vigorously stirred at room temperature for 30 minutes and then thoroughly concentrated. The crude material was diluted with dichloromethane and concentrated, letting the resulting residue sit under vacuum overnight. To this residue were sequentially added dichloromethane (2.4 mL), dimethylformamide (0.6 mL), (R)-2-(methoxycarbonylamino)-2-phenylacetic acid (88 mg, 0.42 mmol), and COMU (154 mg, 0.36 mmol) and diisopropylethylamine (0.16 mL, 0.9 mmol). After stirring for 30 minutes at room temperature the reaction was diluted with ethyl acetate and washed sequentially with saturated aqueous NaHCO$_3$ solution, water and brine. The organic layer was dried (MgSO$_4$), then filtered through a freebasing column (Stratospheres™ PL-HCO$_3$MP SPE, Part #: PL3540-C603). The filtrate was concentrated and purified by preparative reverse phase HPLC (Gemini, 15 to 50% ACN/H$_2$O+0.1% HCO$_2$H) to yield methyl (R)-2-((S)-2-(5-(8-(2-((S)-1-((S)-2-methoxycarbonylamino-3-methylbutanoyl)pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate (72 mg, 26%). LCMS-ESI$^+$: calculated for C$_{48}$H$_{50}$N$_8$O$_7$: 850.96; observed [M+1]$^+$: 851.93.

Example AV

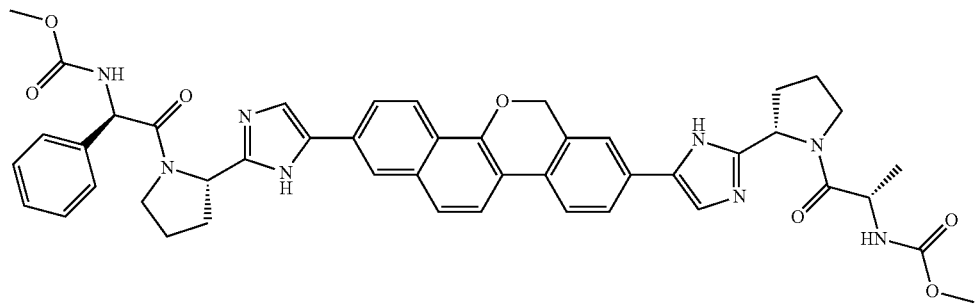

methyl (R)-2-((S)-2-(5-(8-(2-((S)-1-((S)-2-methoxycarbonylaminopropanoyl)-pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate Methyl (R)-2-((S)-2-(5-(8-(2-((S)-1-((S)-2-methoxycarbonylaminopropanoyl)-pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate: This compound was made in an analogous manner to methyl (R)-2-((S)-2-(5-(8-(2-((S)-1-((S)-2-methoxycarbonylamino-3-methylbutanoyl)pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate, substituting (S)-2-(methoxycarbonylamino)propanoic acid for (S)-2-(methoxycarbonylamino)-3-methylbutanoic acid in the first amide coupling. LCMS-ESI$^+$: calculated for C$_{46}$H$_{46}$N$_8$O$_7$: 822.91; observed [M+1]$^+$: 823.58.

Example AW

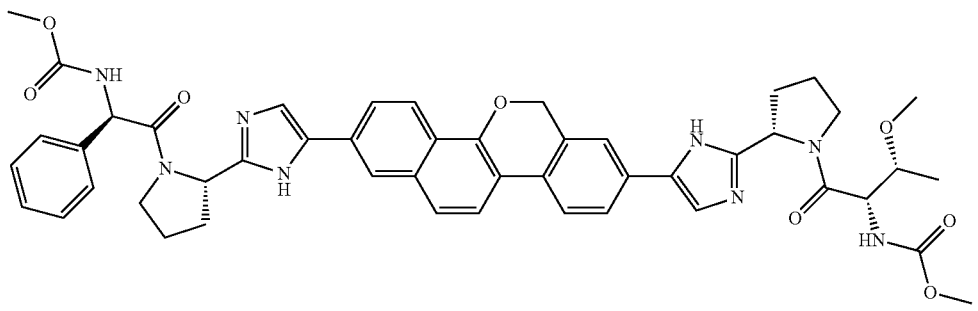

methyl (R)-2-((S)-2-(5-(8-(2-((S)-1-((2S,3R)-2-methoxycarbonylamino-3-methoxybutanoyl)pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate Methyl (R)-2-((S)-2-(5-(8-(2-((S)-1-((2S,3R)-2-methoxycarbonylamino-3-methoxybutanoyl)pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate: This compound was made in an analogous manner to methyl (R)-2-((S)-2-(5-(8-(2-((S)-1-((S)-2-methoxycarbonylamino-3-methylbutanoyl)pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate, substituting (2S,3R)-3-methoxy-2-(methoxycarbonylamino)butanoic acid for (S)-2-(methoxycarbonylamino)-3-methylbutanoic acid in the first amide coupling. LCMS-ESI$^+$: calculated for $C_{48}H_{50}N_8O_8$: 866.96; observed [M+1]$^+$: 867.58.

Example AX

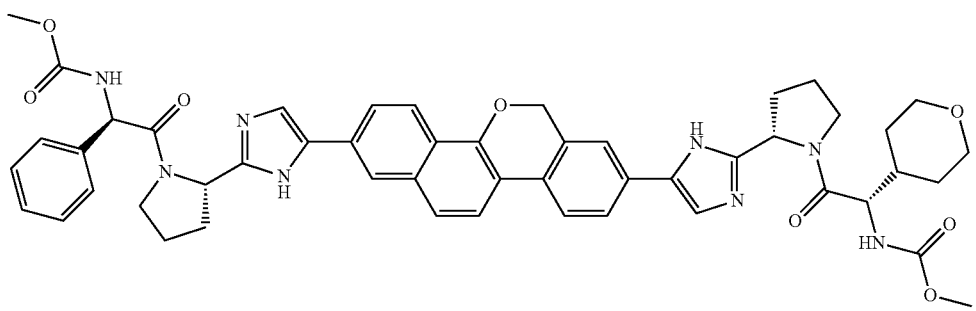

methyl (R)-2-((S)-2-(5-(8-(2-((S)-1-((S)-2-methoxycarbonylamino-2-(tetrahydro-2H-pyran-4-yl)acetyl)pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate Methyl (R)-2-((S)-2-(5-(8-(2-((S)-1-((S)-2-methoxycarbonylamino-2-(tetrahydro-2H-pyran-4-yl)acetyl)pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate: This compound was made in an analogous manner to methyl (R)-2-((S)-2-(5-(8-(2-((S)-1-((S)-2-methoxycarbonylamino-3-methylbutanoyl)pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate, substituting (S)-2-(methoxycarbonylamino)-2-(tetrahydro-2H-pyran-4-yl)acetic acid for (S)-2-(methoxycarbonylamino)-3-methylbutanoic acid in the first amide coupling. LCMS-ESI$^+$: calculated for $C_{50}H_{52}N_8O_8$: 893.00; observed [M+1]$^+$: 894.00.

Example AY

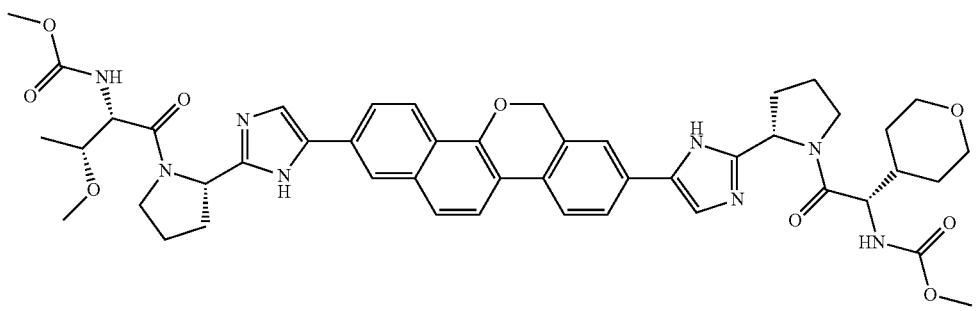

methyl (2S,3R)-1-((S)-2-(5-(8-(2-((S)-1-((S)-2-methoxycarbonylamino-2-(tetrahydro-2H-pyran-4-yl)acetyl)pyrrolidin-2-yl)-1H-imidazol-5-yl)-6H-dibenzo[c,h]chromen-2-yl)-1H-imidazol-2-yl)pyrrolidin-1-yl)-3-methoxy-1-oxobutan-2-ylcarbamate Methyl (2S,3R)-1-((S)-2-(5-(8-(2-((S)-1-((S)-2-methoxycarbonylamino-2-(tetrahydro-2H-pyran-4-yl)acetyl)pyrrolidin-2-yl)-1H-imidazol-5-yl)-6H-dibenzo[c,h]chromen-2-yl)-1H-imidazol-2-yl)pyrrolidin-1-yl)-3-methoxy-1-oxobutan-2-ylcarbamate: This compound was made in an analogous manner to methyl (R)-2-((S)-2-(5-(8-(2-((S)-1-((S)-2-methoxycarbonylamino-3-methylbutanoyl)pyrrolidin-2-yl)-1H-imidazol-5-yl)-6H-dibenzo[c,h]chromen-2-yl)-1H-imidazol-2-yl)pyrrolidin-1-yl)-2-oxo-1-phenylethylcarbamate, substituting (S)-2-(methoxycarbonylamino)-2-(tetrahydro-2H-pyran-4-yl) acetic acid for (S)-2-(methoxycarbonylamino)-3-methylbutanoic acid in the first amide coupling, and substituting (2S,3R)-3-methoxy-2-(methoxycarbonylamino) butanoic acid for (R)-2-(methoxycarbonylamino)-2-phenylacetic acid in the second amide coupling. LCMS-ESI$^+$: calculated for $C_{47}H_{54}N_8O_9$: 874.98; observed [M+1]$^+$: 876.01.

Example AZ

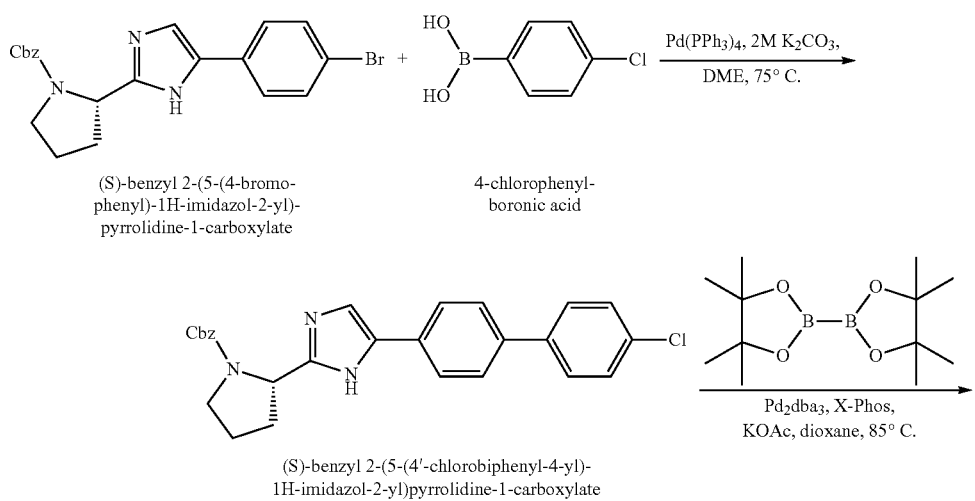

(S)-benzyl 2-(5-(4-bromophenyl)-1H-imidazol-2-yl)-pyrrolidine-1-carboxylate 4-chlorophenylboronic acid (S)-benzyl 2-(5-(4'-chlorobiphenyl-4-yl)-1H-imidazol-2-yl)pyrrolidine-1-carboxylate

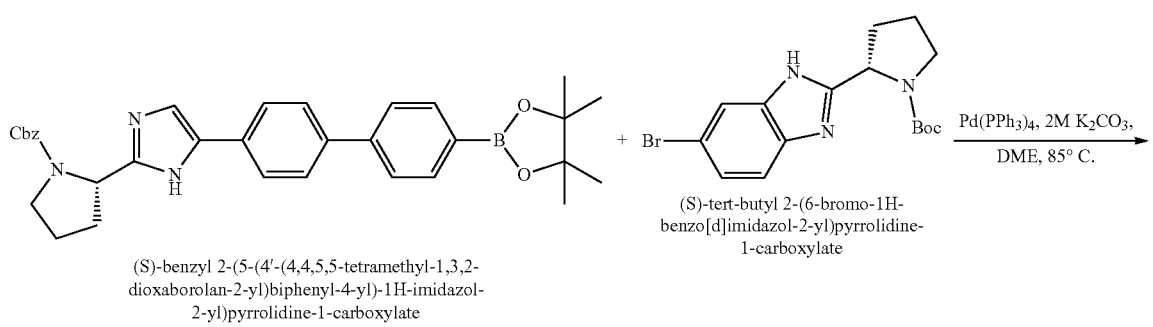

(S)-benzyl 2-(5-(4'-(4,4,5,5-tetramethyl-1,3,2-dioxaborolan-2-yl)biphenyl-4-yl)-1H-imidazol-2-yl)pyrrolidine-1-carboxylate (S)-tert-butyl 2-(6-bromo-1H-benzo[d]imidazol-2-yl)pyrrolidine-1-carboxylate

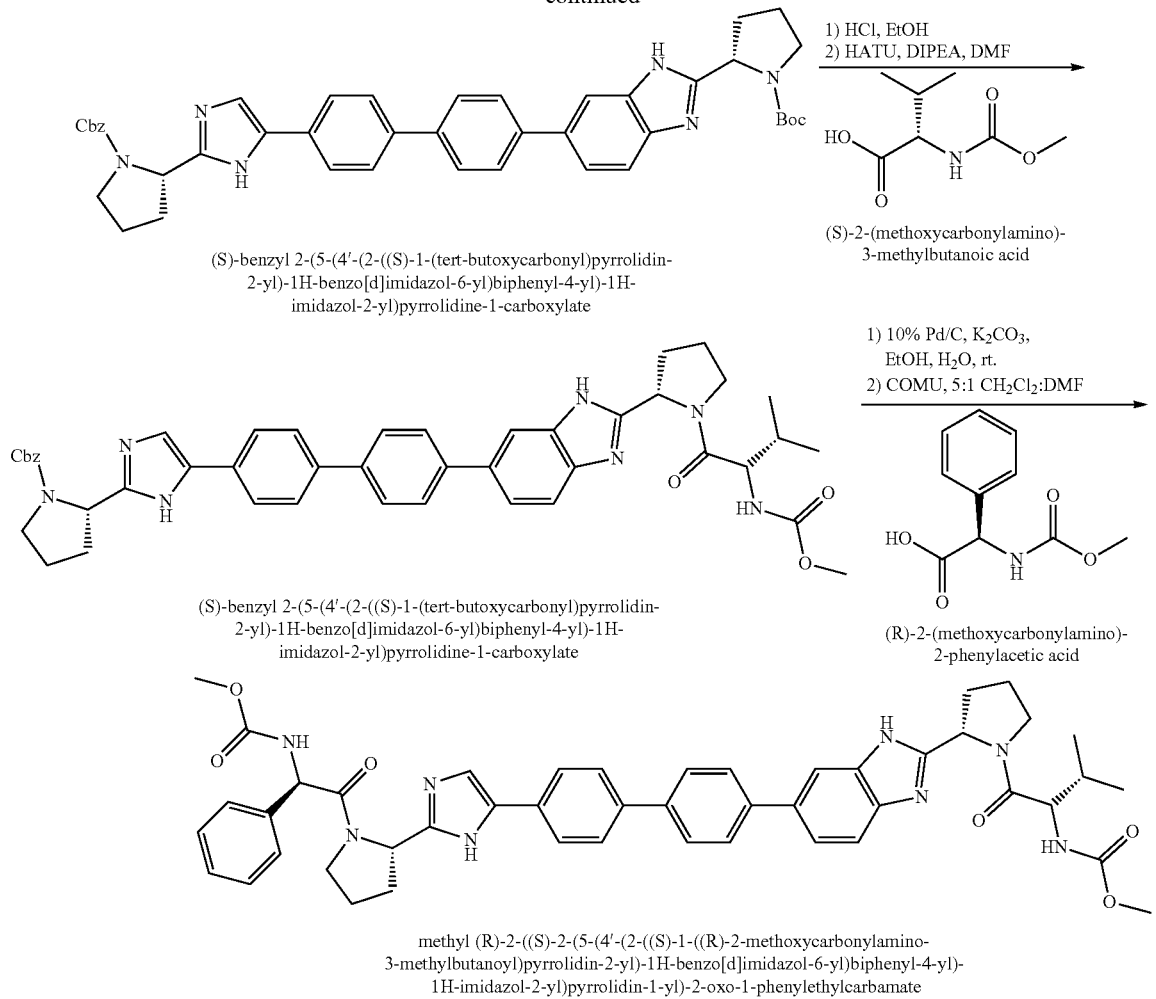

(S)-benzyl 2-(5-(4'-chlorobiphenyl-4-yl)-1H-imidazol-2-yl)pyrrolidine-1-carboxylate: A mixture of (S')-benzyl 2-(5-(4-bromophenyl)-1H-imidazol-2-yl)pyrrolidine-1-carboxylate (4.7 g, 11.0 mmol), 4-chlorophenylboronic acid (2.0 g, 12.1 mmol), tetrakis(triphenylphosphine)palladium(0) (1.3 g, 1.1 mmol), 2M aqueous potassium carbonate solution (22 mL, 44 mmol), and dimethylformamide (100 mL) was degassed under a stream of argon for 15 minutes. The reaction was heated to 75° C. for 3 hours. Upon completion, the reaction was cooled to room temperature, diluted with ethyl acetate and filtered through Celite. The filtrate was washed with water and brine, dried ($MgSO_4$) and concentrated. The resulting crude material was purified by flash column chromatography to yield (S)-benzyl 2-(5-(4'-chlorobiphenyl-4-yl)-1H-imidazol-2-yl)pyrrolidine-1-carboxylate (4.3 g, 85%).

(S)-benzyl 2-(5-(4'-(4,4,5,5-tetramethyl-1,3,2-dioxaborolan-2-yl)biphenyl-4-yl)-1H-imidazol-2-yl)pyrrolidine-1-carboxylate: A mixture of (S)-benzyl 2-(5-(4'-chlorobiphenyl-4-yl)-1H-imidazol-2-yl)pyrrolidine-1-carboxylate (4.3 g, 9.4 mmol), bis(pinacolato)diboron (4.8 g, 18.9 mmol), tris(dibenzylideneacetone)dipalladium(0) (0.44 g, 0.48 mmol), 2-dicyclohexylphosphino-2',4',6'-triisopropylbiphenyl (X-Phos, 0.92 g, 1.9 mmol), potassium acetate (2.8 g, 28.5 mmol), and dioxane (19 mL) was degassed under a stream of argon for 15 minutes. The reaction was heated to 85° C. for 30 minutes. Upon completion, the reaction was cooled to room temperature, diluted with ethyl acetate and filtered through Celite. The filtrate was washed with water and brine, dried ($MgSO_4$) and concentrated. The resulting crude material was purified by flash column chromatography to yield (S)-benzyl 2-(5-(4'-(4,4,5,5-tetramethyl-1,3,2-dioxaborolan-2-yl)biphenyl-4-yl)-1H-imidazol-2-yl)pyrrolidine-1-carboxylate (4.6 g, 89%).

(S)-benzyl 2-(5-(4'-(2-((S)-1-(tert-butoxycarbonyl)pyrrolidin-2-yl)-1H-benzo[d]imidazol-6-yl)biphenyl-4-yl)-1H-imidazol-2-yl)pyrrolidine-1-carboxylate: A mixture of (S)-benzyl 2-(5-(4'-(4,4,5,5-tetramethyl-1,3,2-dioxaborolan-2-yl)biphenyl-4-yl)-1H-imidazol-2-yl)pyrrolidine-1-carboxylate (2.1 g, 3.8 mmol), (S)-tert-butyl 2-(6-bromo-1H-benzo[d]imidazol-2-yl)pyrrolidine-1-carboxylate (1.6 g, 4.3 mmol), tetrakis(triphenylphosphine)palladium(0) (0.44 mg, 0.38 mmol), 2M aqueous potassium carbonate solution (7.7 mL, 15.4 mmol) and dimethoxyethane (26 mL) was degassed under a stream of argon for 15 minutes. The reaction was heated to 85 OC for 14 hours. Upon completion, the reaction was cooled to room temperature, diluted with ethyl acetate and filtered through Celite. The filtrate was washed with water and brine, dried ($MgSO_4$) and concentrated. The resulting crude material was purified by flash column chromatography to yield (S)-benzyl 2-(5-(4'-(2-((S)-1-(tert-butoxycarbonyl)pyrrolidin-2-yl)-1H-benzo

[d]imidazol-6-yl)biphenyl-4-yl)-1H-imidazol-2-yl)pyrrolidine-1-carboxylate (1.2 g, 44%). LCMS-ESI$^+$: calculated for $C_{43}H_{44}N_6O_4$: 708.85; observed [M+1]$^+$: 709.41.

(S)-benzyl 2-(5-(4'-(2-((S)-1-((R)-2-(methoxycarbonylamino)-3-methylbutanoyl)pyrrolidin-2-yl)-1H-benzo[d]imidazol-6-yl)biphenyl-4-yl)-1H-imidazol-2-yl)pyrrolidine-1-carboxylate: A solution of (S)-benzyl 2-(5-(4'-(2-((S)-1-(tert-butoxycarbonyl)pyrrolidin-2-yl)-1H-benzo[d]imidazol-6-yl)biphenyl-4-yl)-1H-imidazol-2-yl)pyrrolidine-1-carboxylate (0.6 g, 0.85 mmol), concentrated HCl (1.5 mL) and ethanol (10 mL) was heated to 60° C. for one hour. The reaction was concentrated and redissolved in a minimal amount of methanol. An equal volume of dichloromethane was added and the solution was again concentrated. Dichloromethane was added to the resulting residue and concentrated off three more times, until the crude material was a yellow powder. A portion of the crude amine (0.3 g, ~0.42 mmol) was dissolved in dimethylformamide (4.7 mL). To this solution was added (S)-2-(methoxycarbonylamino)-3-methylbutanoic acid (165 mg, 0.9 mmol), HATU (355 mg, 0.9 mmol) and diisopropylethylamine (0.82 mL, 4.7 mmol). The reaction was stirred at room temperature for one hour, and then diluted with acetonitrile (2 mL) and methanol (2 mL). To this solution was added ten drops of 5M aqueous NaOH solution and stirring was continued for 30 minutes. The reaction was diluted with ethyl acetate and the organic layer was washed with water and brine. The combined aqueous washings were extracted three times with ethyl acetate, and the combined organic layers were dried (MgSO$_4$) and concentrated. The crude material was purified by flash column chromatography to yield (S)-benzyl 2-(5-(4'-(2-((S)-1-((R)-2-(methoxycarbonylamino)-3-methylbutanoyl)pyrrolidin-2-yl)-1H-benzo[d]imidazol-6-yl)biphenyl-4-yl)-1H-imidazol-2-yl)pyrrolidine-1-carboxylate (0.28 g, ~74%). LCMS-ESI$^+$: calculated for $C_{45}H_{47}N_7O_5$: 765.90; observed [M+1]$^+$: 766.47.

Methyl (R)-2-((S)-2-(5-(4'-(2-((S)-1-((R)-2-methoxycarbonylamino-3-methylbutanoyl)pyrrolidin-2-yl)-1H-benzo[d]imidazol-6-yl)biphenyl-4-yl)-1H-imidazol-2-yl)pyrrolidin-1-yl)-2-oxo-1-phenylethylcarbamate: To a solution of (S)-benzyl 2-(5-(4'-(2-((S)-1-((R)-2-(methoxycarbonylamino)-3-methylbutanoyl)pyrrolidin-2-yl)-1H-benzo[d]imidazol-6-yl)biphenyl-4-yl)-1H-imidazol-2-yl)pyrrolidine-1-carboxylate (0.28 g, 0.37 mmol), potassium carbonate (105 mg, 0.75 mmol) and water (1 drop) in ethanol (5 mL) was added 10% palladium on carbon (200 mg). The reaction flask was flushed with argon for 2 minutes. Hydrogen gas was bubbled through the reaction mixture for 10 minutes. The reaction was stirred under hydrogen gas for 18 hours, and then flushed with argon. The mixture was diluted with methanol and filtered through Celite. The filtrate was concentrated and used without purification in the next step. This residue was dissolved in a 5:1 mixture of dichloromethane:dimethylformamide (4.3 mL) and cooled to 0° C. To the solution were sequentially added (R)-2-(methoxycarbonylamino)-2-phenylacetic acid (98 mg, 0.47 mmol) and COMU (202 mg, 0.47 mmol). After one hour, the reaction was diluted with acetonitrile (2 mL) and methanol (2 mL). To this solution was added ten drops of 5M aqueous NaOH solution and stirring was continued for 30 minutes. The reaction was diluted with ethyl acetate and the organic layer was washed with water and brine. The combined aqueous washings were extracted three times with ethyl acetate, and the combined organic layers were dried (MgSO$_4$) and concentrated. The crude material was purified by preparative reverse phase HPLC (Gemini, 15 to 50% ACN/H$_2$O+0.1% HCO$_2$H), followed by flash column chromatography to yield methyl (R)-2-((S)-2-(5-(4'-(2-((S)-1-((R)-2-methoxycarbonylamino-3-methylbutanoyl)pyrrolidin-2-yl)-1H-benzo[d]imidazol-6-yl)biphenyl-4-yl)-1H-imidazol-2-yl)pyrrolidin-1-yl)-2-oxo-1-phenylethylcarbamate (165 mg, 55%). LCMS-ESI$^+$: calculated for $C_{47}H_{50}N_8O_6$: 822.95; observed [M+1]$^+$: 823.87.

Example BA

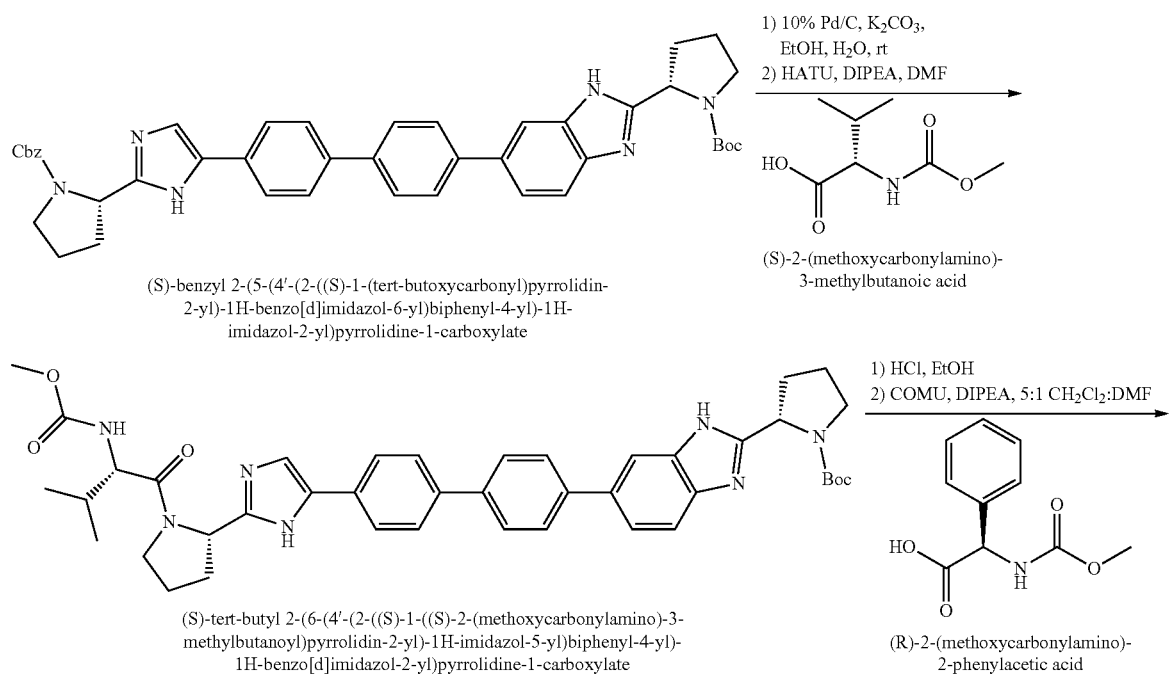

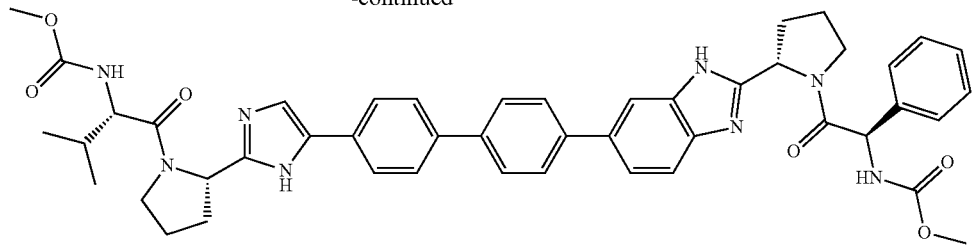

methyl (S)-1-((S)-2-(5-(4'-(2-((S)-1-((R)-2-methoxycarbonylamino-
2-phenylacetyl)pyrrolidin-2-yl)-1H-benzo[d]imidazol-6-yl)biphenyl-
4-yl)-1H-imidazol-2-yl)pyrrolidin-1-yl)-3-methyl-1-oxobutan-2-ylcarbamate (S)-tert-butyl 2-(6-(4'-(2-((S)-1-((S)-2-(methoxycarbonylamino)-3-methylbutanoyl)pyrrolidin-2-yl)-1H-imidazol-5-yl)biphenyl-4-yl)-1H-benzo[d]imidazol-2-yl)pyrrolidine-1-carboxylate: To a solution—of (S)-benzyl 2-(5-(4'-(2-((S)-1-(tert-butoxycarbonyl)pyrrolidin-2-yl)-1H-benzo[d]imidazol-6-yl)biphenyl-4-yl)-1H-imidazol-2-yl)pyrrolidine-1-carboxylate (0.65 g, 0.92 mmol), potassium carbonate (200 mg, 1.4 mmol) and water (2 drops) in ethanol (11.6 mL) was added 10% palladium on carbon (260 mg). The reaction flask was flushed with argon for 2 minutes. Hydrogen gas was bubbled through the reaction mixture for 10 minutes. The reaction was stirred under hydrogen gas for 18 hours, and then flushed with argon. The mixture was diluted with methanol and filtered through Celite. The filtrate was concentrated and used without purification in the next step. The crude material was dissolved in dimethylformamide (7.4 mL). To this solution was added (S)-2-(methoxycarbonylamino)-3-methylbutanoic acid (156 mg, 0.9 mmol), HATU (340 mg, 0.9 mmol) and diisopropylethylamine (0.39 mL, 2.2 mmol). The reaction was stirred at room temperature for one hour, and then diluted with acetonitrile (2 mL) and methanol (2 mL). To this solution was added ten drops of 5M aqueous NaOH solution and stirring was continued for 30 minutes. The reaction was diluted with ethyl acetate and the organic layer was washed with water and brine. The combined aqueous washings were extracted three times with ethyl acetate, and the combined organic layers were dried (MgSO$_4$) and concentrated. The crude material was purified by flash column chromatography to yield (S)-tert-butyl 2-(6-(4'-(2-((S)-1-((S)-2-(methoxycarbonylamino)-3-methylbutanoyl)pyrrolidin-2-yl)-1H-imidazol-5-yl)biphenyl-4-yl)-1H-benzo[d]imidazol-2-yl)pyrrolidine-1-carboxylate (368 mg, 68%). LCMS-ESI$^+$: calculated for C$_{42}$H$_{49}$N$_7$O$_5$: 731.88; observed [M+1]$^+$: 732.75.

Methyl (S)-1-((S)-2-(5-(4'-(2-((S)-1-((R)-2-methoxycarbonylamino-2-phenylacetyl)pyrrolidin-2-yl)-1H-benzo[d]imidazol-6-yl)biphenyl-4-yl)-1H-imidazol-2-yl)pyrrolidin-1-yl)-3-methyl-1-oxobutan-2-ylcarbamate: A solution of (S)-tert-butyl 2-(6-(4'-(2-((S)-1-((S)-2-(methoxycarbonylamino)-3-methylbutanoyl)pyrrolidin-2-yl)-1H-imidazol-5-yl)biphenyl-4-yl)-1H-benzo[d]imidazol-2-yl)pyrrolidine-1-carboxylate (368 mg, 0.50 mmol), concentrated HCl (1 mL) and ethanol (6 mL) was heated to 60° C. for one hour. The reaction was concentrated and redissolved in a minimal amount of methanol. An equal volume of dichloromethane was added and the solution was again concentrated. Dichloromethane was added to the resulting residue and concentrated off three more times, until the crude material was a yellow powder. The crude material was dissolved in a 5:1 mixture of dichloromethane:dimethylformamide (4.9 mL) and cooled to 0° C. To the solution are sequentially added (R)-2-(methoxycarbonylamino)-2-phenylacetic acid (119 mg, 0.57 mmol), COMU (232 mg, 0.54 mmol) and diisopropylethylamine (0.26 mL, 1.5 mmol). After one hour, the reaction is diluted with acetonitrile (2 mL) and methanol (2 mL). To this solution was added ten drops of 5M aqueous NaOH solution and stirring was continued for 30 minutes. The reaction was diluted with ethyl acetate and the organic layer was washed with water and brine. The combined aqueous washings were extracted three times with ethyl acetate, and the combined organic layers were dried (MgSO$_4$) and concentrated. The crude material was purified by preparative reverse phase HPLC (Gemini, 15 to 50% ACN/H$_2$O+0.1% HCO$_2$H), followed by flash column chromatography to yield methyl (S)-1-((S)-2-(5-(4'-2-((S)-1-((R)-2-methoxycarbonylamiino-2-phenylacetyl)pyrrolidin-2-yl)-1H-benzo[d]imidazol-6-yl)biphenyl-4-yl)-1H-imidazol-2-yl)pyrrolidin-1-yl)-3-methyl-1-oxobutan-2-ylcarbamate (270 mg, 66%). LCMS-ESI$^+$: calculated for C$_{47}$H$_{50}$N$_8$O$_6$: 822.95; observed [M+1]$^+$: 823.90.

Example BB

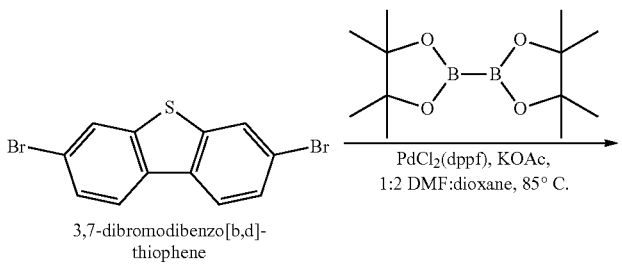

3,7-dibromodibenzo[b,d]-thiophene

PdCl$_2$(dppf), KOAc,
1:2 DMF:dioxane, 85° C.

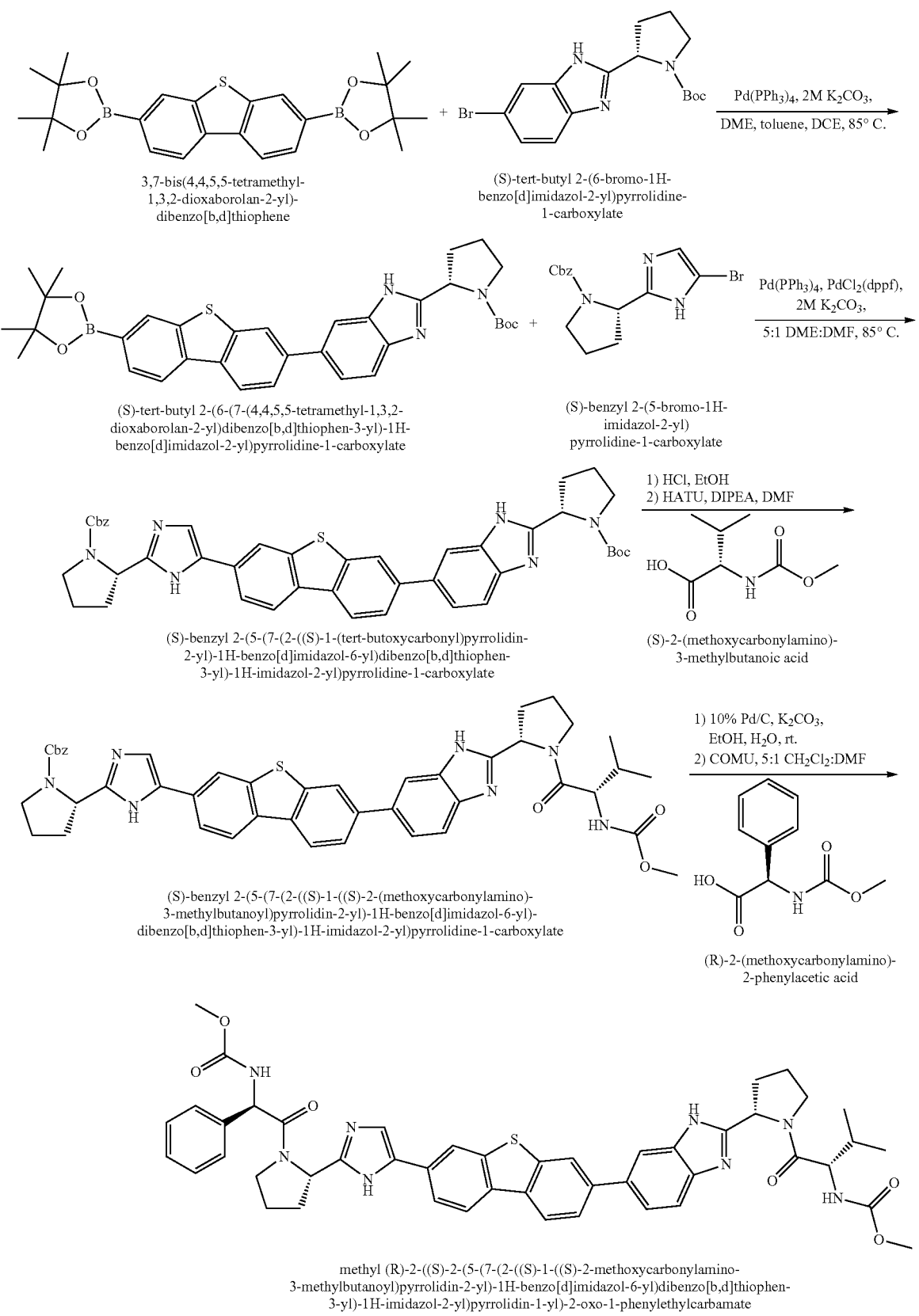

3,7-bis(4,4,5,5-tetramethyl-1,3,2-dioxaborolan-2-yl)-dibenzo[b,d]thiophene: A solution of 3,7-dibromodibenzo[b,d]thiophene (5.6 g, 16.4 mmol), bis(pinacolato)diboron (12.5 g, 49.2 mmol) and potassium acetate (9.7 g, 98.9 mmol) in 2:1 dioxane:dimethylformamide (165 mL) was degassed for fifteen minutes. To this solution was added $PdCl_2$(dppf) (1.2 g, 1.6 mmol) and the reaction was heated to 85° C. for 2 hours. The mixture was cooled to room temperature, diluted with ethyl acetate and filtered through Celite. The filtrate was washed with water and brine, dried ($MgSO_4$) and concentrated. The resulting residue was quickly passed through a silica gel plug. The fractions containing product were concentrated and recrystallized from a minimal amount of dichloromethane and a large amount of methanol to yield 3,7-bis(4,4,5,5-tetramethyl-1,3,2-dioxaborolan-2-yl)-dibenzo[b,d]thiophene (5.1 g, 71%).

(S)-tert-butyl 2-(6-(7-(4,4,5,5-tetramethyl-1,3,2-dioxaborolan-2-yl)dibenzo[b,d]thiophen-3-yl)-1H-benzo[d]imidazol-2-yl)pyrrolidine-1-carboxylate: A mixture of 3,7-bis(4,4,5,5-tetramethyl-1,3,2-dioxaborolan-2-yl)-dibenzo[b,d]thiophene (3.6 g, 8.2 mmol), (S)-tert-butyl 2-(6-bromo-1H-benzo[d]imidazol-2-yl)pyrrolidine-1-carboxylate (1.0 g, 2.7 mmol), tetrakis(triphenylphosphine)palladium(0) (0.31 mg, 0.27 mmol), 2M aqueous potassium carbonate solution (5 mL, 10 mmol), dimethoxyethane (25 mL), toluene (5 mL) and dichloroethane (2.5 mL) was degassed under a stream of argon for 15 minutes. The reaction was heated to 85° C. for 2 hours. Upon completion, the reaction was cooled to room temperature, diluted with ethyl acetate and filtered through Celite. The filtrate was washed with water and brine, dried ($MgSO_4$) and concentrated. The resulting crude material was purified by flash column chromatography to yield (S)-tert-butyl 2-(6-(7-(4,4,5,5-tetramethyl-1,3,2-dioxaborolan-2-yl)dibenzo[b,d]thiophen-3-yl)-1H-benzo[d]imidazol-2-yl)pyrrolidine-1-carboxylate (1.0 g, 62%).

(S)-benzyl 2-(5-(7-(2-((S)-1-(tert-butoxycarbonyl)pyrrolidin-2-yl)-1H-benzo[d]imidazol-6-yl)dibenzo[b,d]thiophen-3-yl)-1H-imidazol-2-yl)pyrrolidine-1-carboxylate: A mixture of (S)-tert-butyl 2-(6-(7-(4,4,5,5-tetramethyl-1,3,2-dioxaborolan-2-yl)dibenzo[b,d]thiophen-3-yl)-1H-benzo[d]imidazol-2-yl)pyrrolidine-1-carboxylate (870 mg, 1.5 mmol), (S)-benzyl 2-(5-bromo-1H-imidazol-2-yl)pyrrolidine-1-carboxylate (620 mg, 1.8 mmol), tetrakis(triphenylphosphine)palladium(0) (170 mg, 0.15 mmol), $PdCl_2$(dppf) (110 mg, 0.15 mmol), 2M aqueous potassium carbonate (2.2 mL, 4.4 mmol), dimethoxyethane (12.2 mL) and dimethylformamide (2.4 mL) was degassed with argon for 15 minutes. The reaction was then heated to 85° C. for 2 hours. Upon completion, the reaction was cooled to room temperature, diluted with ethyl acetate and filtered through Celite. The filtrate was washed with water and brine, dried ($MgSO_4$) and concentrated. The resulting crude material was purified by flash column chromatography to yield (S)-benzyl 2-(5-(7-(2-((S)-1-(tert-butoxycarbonyl)pyrrolidin-2-yl)-1H-benzo[d]imidazol-6-yl)dibenzo[b,d]thiophen-3-yl)-1H-imidazol-2-yl)pyrrolidine-1-carboxylate (750 mg, 70%). LCMS-ESI$^+$: calculated for $C_{43}H_{42}N_6O_4S$: 738.30; observed [M+1]$^+$: 739.19.

(S)-benzyl 2-(5-(7-(2-((S)-1-((S)-2-(methoxycarbonylamino)-3-methylbutanoyl)pyrrolidin-2-yl)-1H-benzo[d]imidazol-6-yl)-dibenzo[b,d]thiophen-3-yl)-1H-imidazol-2-yl)pyrrolidine-1-carboxylate: A solution of (S)-benzyl 2-(5-(7-(2-((S)-1-(tert-butoxycarbonyl)pyrrolidin-2-yl)-1H-benzo[d]imidazol-6-yl)dibenzo[b,d]thiophen-3-yl)-1H-imidazol-2-yl)pyrrolidine-1-carboxylate (0.75 g, 1.0 mmol), concentrated HCl (2.0 mL) and ethanol (12 mL) was heated to 60° C. for one hour. The reaction was concentrated and redissolved in a minimal amount of methanol. An equal volume of dichloromethane was added and the solution was again concentrated. Dichloromethane was added to the resulting residue and concentrated off three more times, until the crude material was a powder. A portion of the crude amine (0.29 g, ~0.40 mmol) was dissolved in dimethylformamide (3.9 mL). To this solution was added (S)-2-(methoxycarbonylamino)-3-methylbutanoic acid (82 mg, 0.47 mmol), HATU (163 mg, 0.43 mmol) and diisopropylethylamine (0.70 mL, 4.0 mmol). The reaction was stirred at room temperature for one hour, and then diluted with acetonitrile (2 mL) and methanol (2 mL). To this solution was added ten drops of 5M aqueous NaOH solution and stirring was continued for 30 minutes. The reaction was diluted with ethyl acetate and the organic layer was washed with water and brine. The combined aqueous washings were extracted three times with ethyl acetate, and the combined organic layers were dried ($MgSO_4$) and concentrated. The crude material was purified by flash column chromatography to yield (S)-benzyl 2-(5-(7-(2-((S)-1-((S)-2-(methoxycarbonylamino)-3-methylbutanoyl)pyrrolidin-2-yl)-1H-benzo[d]imidazol-6-yl)-dibenzo[b,d]thiophen-3-yl)-1H-imidazol-2-yl)pyrrolidine-1-carboxylate (0.19 g, ~60%). LCMS-ESI$^+$: calculated for $C_{45}H_{45}N_7O_5S$: 795.95; observed [M+1]$^+$: 796.73.

Methyl (R)-2-((S)-2-(5-(7-(2-((S)-1-((S)-2-methoxycarbonylamino-3-methylbutanoyl)pyrrolidin-2-yl)-1H-benzo[d]imidazol-6-yl)dibenzo[b,d]thiophen-3-yl)-1H-imidazol-2-yl)pyrrolidin-1-yl)-2-oxo-1-phenylethylcarbamate: To a solution of (S)-benzyl 2-(5-(7-(2-((S)-1-((S)-2-(methoxycarbonylamino)-3-methylbutanoyl)pyrrolidin-2-yl)-1H-benzo[d]imidazol-6-yl)-dibenzo[b,d]thiophen-3-yl)-1H-imidazol-2-yl)pyrrolidine-1-carboxylate (0.19 g, 0.24 mmol), potassium carbonate (70 mg, 0.50 mmol) and water (1 drop) in ethanol (3.5 mL) was added 10% palladium on carbon (175 mg). The reaction flask was flushed with argon for 2 minutes. Hydrogen gas was bubbled through the reaction mixture for 10 minutes. The reaction was stirred under hydrogen gas for 18 hours, and then flushed with argon. The mixture was diluted with methanol and filtered through Celite. The filtrate was concentrated and used without purification in the next step. This residue was dissolved in a 5:1 mixture of dichloromethane:dimethylformamide (3.0 mL) and cooled to 0° C. To the solution were sequentially added (R)-2-(methoxycarbonylamino)-2-phenylacetic acid (76 mg, 0.36 mmol) and COMU (150 mg, 0.35 mmol). After one hour, the reaction was diluted with ethyl acetate and the organic layer was washed with water and brine. The combined aqueous washings were extracted three times with ethyl acetate, and the combined organic layers were dried ($MgSO_4$) and concentrated. The crude material was purified by preparative reverse phase HPLC (Gemini, 15 to 50% ACN/$H_2O$+0.1% TFA) to yield methyl (R)-2-((S)-2-(5-(7-(2-((S)-1-((S)-2-methoxycarbonylamino-3-methylbutanoyl)pyrrolidin-2-yl)-1H-benzo[d]imidazol-6-yl)dibenzo[b,d]thiophen-3-yl)-1H-imidazol-2-yl)pyrrolidin-1-yl)-2-oxo-1-phenylethylcarbamate (95 mg, 47%). LCMS-ESI$^+$: calculated for $C_{47}H_{48}N_8O_6S$: 853.00; observed [M+1]$^+$: 853.85.

Example BC

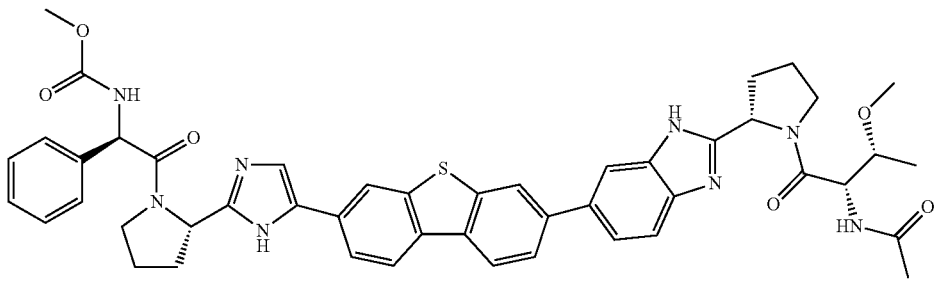 [SMILES: COC(=O)N[C@@H](C(=O)N1CCC[C@H]1c1ncc(-c2ccc3c(c2)sc2cc(-c4ccc5nc([C@@H]6CCCN6C(=O)[C@@H](NC(C)=O)[C@@H](C)OC)[nH]c5c4)ccc23)[nH]1)c1ccccc1]

methyl (R)-2-((S)-2-(5-(7-(2-((S)-1-((2S,3R)-2-methoxycarbonylamino-3-methoxybutanoyl)pyrrolidin-2-yl)-1H-benzo[d]imidazol-6-yl)dibenzo[b,d]thiophen-3-yl)-1H-imidazol-2-yl)pyrrolidin-1-yl)-2-oxo-1-phenylethylcarbamate Methyl (R)-2-((S)-2-(5-(7-(2-((S)-1-((2S,3R)-2-methoxycarbonylamino-3-methoxybutanoyl)pyrrolidin-2-yl)-1H-benzo[d]imidazol-6-yl)dibenzo[b,d]thiophen-3-yl)-1H-imidazol-2-yl)pyrrolidin-1-yl)-2-oxo-1-phenylethylcarbamate:

This compound was made in an analogous manner to Example BB, substituting (2S,3R)-3-methoxy-2-(methoxycarbonylamino)butanoic acid for (S)-2-(methoxycarbonylamino)-3-methylbutanoic acid in the first amide coupling. LCMS-ESI$^+$: calculated for $C_{47}H_{48}N_8O_7S$: 869.00; observed [M+1]$^+$: 869.92.

Example BD

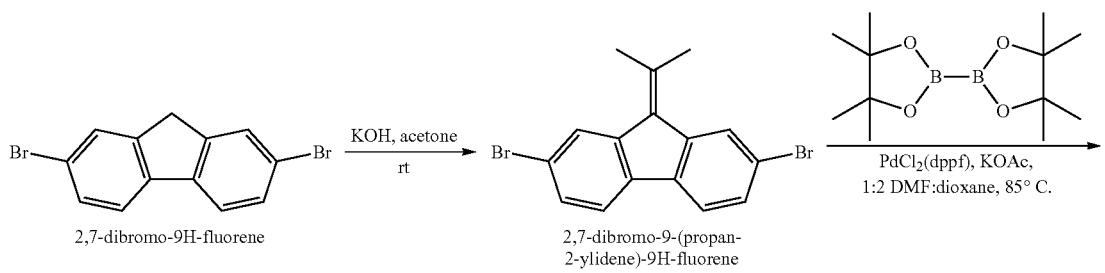

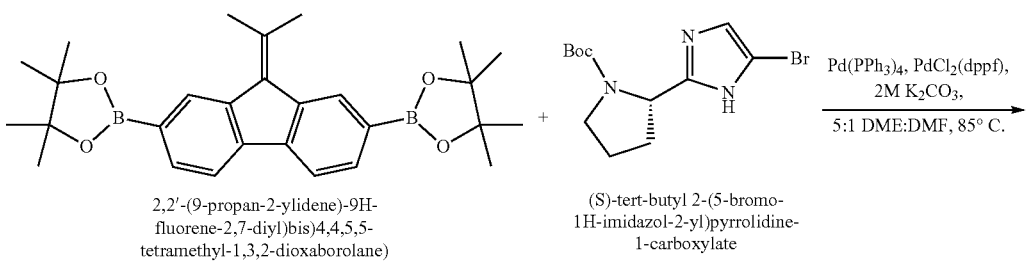

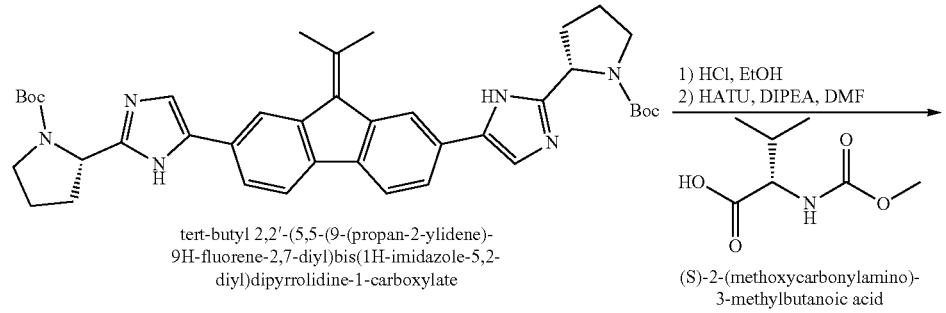

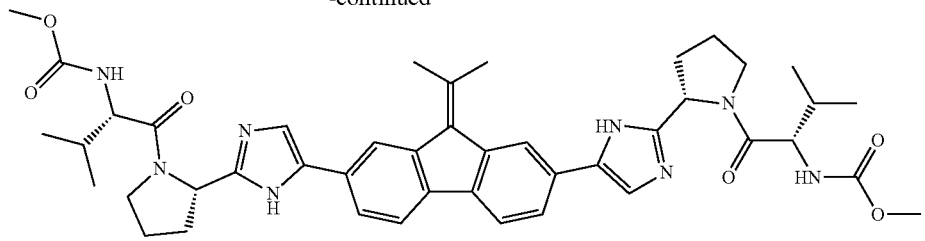

dimethyl (2S,2'S)-1,1'-((2S,2'S)-2,2'-(5,5'-(9-(propan-2-ylidene)-9H-fluorene-2,7-diyl)bis(1H-imidazole-5,2-diyl))bis(pyrrolidine-2,1-diyl))bis(3-methyl-1-oxobutane-2,1-diyl)dicarbamate 2,7-dibromo-9-(propan-2-ylidene)-9H-fluorene: To a mixture of solid 2,7-dibromo-9H-fluorene (1 g, 3.1 mmol) and solid potassium hydroxide (freshly ground, 530 mg, 9.4 mmol) was added acetone (15 mL). The reaction immediately turns dark. After 3 hours the reaction was diluted with ethyl acetate. The organics were washed with water and brine, dried (MgSO$_4$) and concentrated to a dark blue-green oil. This oil was dissolved in dichloromethane (10 mL) and formic acid (~10 drops) was added until the solution was bright orange. After concentration, the resulting residue was purified by flash column chromatography to yield 2,7-dibromo-9-(propan-2-ylidene)-9H-fluorene (145 mg, 13%) as an orange solid.

2,2'-(9-(propan-2-ylidene)-9H-fluorene-2,7-diyl)bis(4,4,5,5-tetramethyl-1,3,2-dioxaborolane): A solution of 2,7-dibromo-9-(propan-2-ylidene)-9H-fluorene (145 mg, 0.40 mmol), bis(pinacolato)diboron (305 mg, 1.2 mmol) and potassium acetate (235 mg, 2.4 mmol) in 2:1 dioxane: dimethylformamide (4 mL) was degassed for fifteen minutes. To this solution was added PdCl$_2$(dppf) (30 mg, 0.04 mmol) and the reaction was heated to 85° C. for 2 hours. The mixture was cooled to room temperature, diluted with ethyl acetate and filtered through Celite. The filtrate was washed with water and brine, dried (MgSO$_4$) and concentrated. The resulting residue was diluted with dichloromethane (10 mL) and concentrated. Solids precipitated immediately upon addition of methanol (10 mL) to the crude residue. This mixture was stirred for 30 minutes and then filtered to yield 2,2'-(9-(propan-2-ylidene)-9H-fluorene-2,7-diyl)bis(4,4,5,5-tetramethyl-1,3,2-dioxaborolane) (90 mg, 49%) as a grey solid. LCMS-ESI$^+$: calculated for C$_{28}$H$_{36}$B$_2$O$_4$: 458.21; observed [M+1]$^+$: 459.14.

tert-Butyl 2,2'-(5,5'-(9-(propan-2-ylidene)-9H-fluorene-2,7-diyl)bis(1H-imidazole-5,2-diyl))dipyrrolidine-1-carboxylate: A mixture of 2,2'-(9-(propan-2-ylidene)-9H-fluorene-2,7-diyl)bis(4,4,5,5-tetramethyl-1,3,2-dioxaborolane) (90 mg, 0.20 mmol), (S)-tert-butyl 2-(5-bromo-1H-imidazol-2-yl)pyrrolidine-1-carboxylate (155 mg, 0.50 mmol), tetrakis(triphenylphosphine)palladium(0) (23 mg, 0.02 mmol), PdCl$_2$(dppf) (15 mg, 0.02 mmol), 2M aqueous potassium carbonate (0.60 mL, 1.2 mmol), dimethoxyethane (1.7 mL) and dimethylformamide (0.3 mL) was degassed with argon for 15 minutes. The reaction was then heated to 85° C. for 2 hours. Upon completion, the reaction was cooled to room temperature, diluted with ethyl acetate and filtered through Celite. The filtrate was washed with water and brine, dried (MgSO$_4$) and concentrated. The resulting crude material was purified by flash column chromatography to yield tert-butyl 2,2'-(5,5'-(9-(propan-2-ylidene)-9H-fluorene-2,7-diyl)bis(H-imidazole-5,2-diyl))dipyrrolidine-1-carboxylate (70 mg, 53%). LCMS-ESI$^+$: calculated for C$_{40}$H$_{48}$N$_6$O$_4$: 676.37; observed [M+1]$^+$: 677.19.

Dimethyl (2S,2'S)-1,1'-((2S,2'S)-2,2'-(5,5'-(9-(propan-2-ylidene)-9H-fluorene-2,7-diyl)bis(1H-imidazole-5,2-diyl))bis(pyrrolidine-2,1-diyl))bis(3-methyl-1-oxobutane-2,1-diyl)dicarbamate: A solution of tert-butyl 2,2'-(5,5'-(9-(propan-2-ylidene)-9H-fluorene-2,7-diyl)bis(1H-imidazole-5,2-diyl))dipyrrolidine-1-carboxylate (70 mg, 0.10 mmol), concentrated HCl (0.5 mL) and ethanol (3 mL) was heated to 60° C. for one hour. The reaction was concentrated and redissolved in a minimal amount of methanol. An equal volume of dichloromethane was added and the solution was again concentrated. Dichloromethane was added to the resulting residue and concentrated off three more times, until the crude material was a powder. The crude amine was dissolved in dimethylformamide (1.2 mL). To this solution was added (S)-2-(methoxycarbonylamino)-3-methylbutanoic acid (49 mg, 0.28 mmol), HATU (93 mg, 0.24 mmol) and diisopropylethylamine (0.12 mL, 0.67 mmol). The reaction was stirred at room temperature for one hour. Upon completion, the reaction was diluted with ethyl acetate and the organic layer was washed with water and brine. The combined aqueous washings were extracted three times with ethyl acetate, and the combined organic layers were dried (MgSO$_4$) and concentrated. The crude material was purified by preparative reverse phase HPLC (Gemini, 15 to 50% ACN/H$_2$O+0.1% TFA) to yield dimethyl (2S,2'S)-1,1'-((2S,2'S)-2,2'-(5,5'-(9-(propan-2-ylidene)-9H-fluorene-2,7-diyl)bis(1H-imidazole-5,2-diyl))bis(pyrrolidine-2,1-diyl))bis(3-methyl-1-oxobutane-2,1-diyl)dicarbamate (51 mg, 62%). LCMS-ESI$^+$: calculated for C$_{44}$H$_{54}$N$_8$O$_6$: 790.95; observed [M+1]$^+$: 791.71.

Example BE

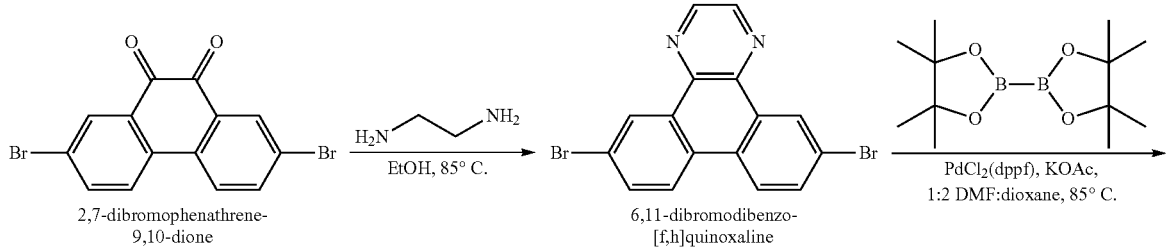

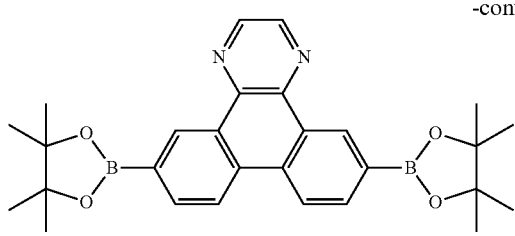

6,11-bis(4,4,5,5-tetramethyl-1,3,2-dioxaborolan-2-yl)dibenzo[f,h]quinoxaline

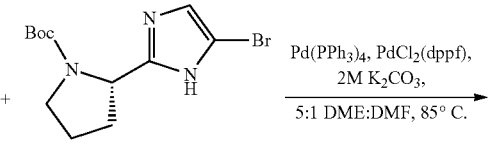

(S)-tert-butyl 2-(5-bromo-1H-imidazol-2-yl)pyrrolidine-1-carboxylate

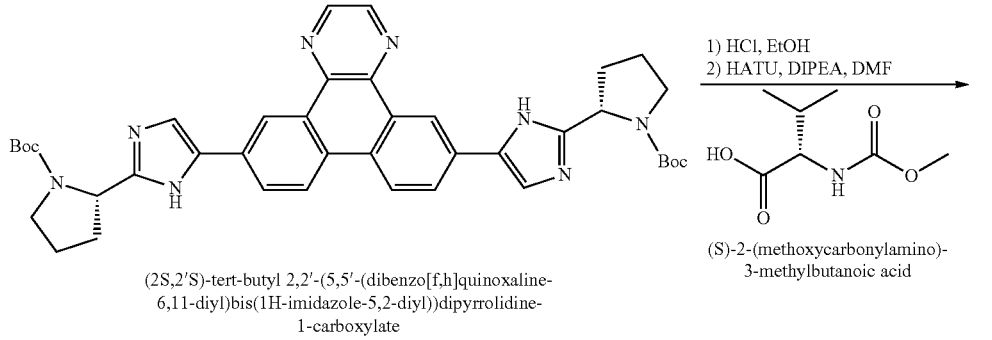

(2S,2'S)-tert-butyl 2,2'-(5,5'-(dibenzo[f,h]quinoxaline-6,11-diyl)bis(1H-imidazole-5,2-diyl))dipyrrolidine-1-carboxylate (S)-2-(methoxycarbonylamino)-3-methylbutanoic acid

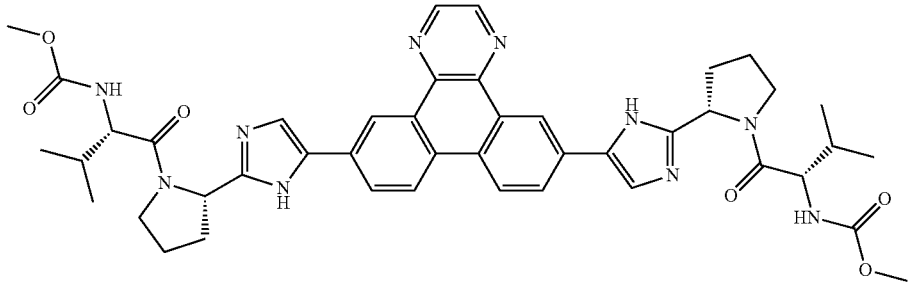

dimethyl (2S,2'S)-1,1'-((2S,2'S)-2,2'-(5,5'-(dibenzo[f,h]quinoxaline-6,11-diyl)bis(1H-imidazole-5,2-diyl))bis(pyrrolidine-2,1-diyl))bis(3-methyl-1-oxobutane-2,1-diyl)dicarbamate 6,11-Dibromodibenzo[f,h]quinoxaline: A mixture of 2,7-dibromophenanthrene-9,10-dione (1.0 g, 2.7 mmol), ethylenediamine (1.8 mL, 26.9 mmol) and ethanol (20 mL) was heated to 85° C. After 3 hours, the reaction was cooled to room temperature and the solids were filtered and thoroughly washed methanol to yield 6,11-dibromodibenzo[f,h]quinoxaline (360 mg, 34%).

6,11-bis(4,4,5,5-tetramethyl-1,3,2-dioxaborolan-2-yl)dibenzo[f,h]quinoxaline: A solution of 6,11-dibromodibenzo[f,h]quinoxaline (360 mg, 0.92 mmol), bis(pinacolato)diboron (700 mg, 2.8 mmol) and potassium acetate (545 mg, 5.5 mmol) in 2:1 dioxane:dimethylformamide (9.2 mL) was degassed for fifteen minutes. To this solution was added PdCl$_2$(dppf) (70 mg, 0.09 mmol) and the reaction was heated to 85° C. for 6 hours. The mixture was cooled to room temperature, diluted with ethyl acetate and filtered through Celite. The filtrate was washed with water and brine, dried (MgSO$_4$) and concentrated. The resulting residue was diluted with dichloromethane (10 mL) and concentrated. Solids precipitated immediately upon addition of methanol (10 mL) to the crude residue. This mixture was stirred for 30 minutes, filtered and thoroughly rinsed with methanol to yield 6,11-bis(4,4,5,5-tetramethyl-1,3,2-dioxaborolan-2-yl)dibenzo[f,h]quinoxaline (270 mg, 61%) as a grey solid.

(2S,2'S)-tert-butyl 2,2'-(5,5'-(dibenzo[f,h]quinoxaline-6,11-diyl)bis(1H-imidazole-5,2-diyl))dipyrrolidine-1-carboxylate: A mixture of 6,11-bis(4,4,5,5-tetramethyl-1,3,2-dioxaborolan-2-yl)dibenzo[f,h]quinoxaline (270 mg, 0.55 mmol), (S)-tert-butyl 2-(5-bromo-1H-imidazol-2-yl)pyrrolidine-1-carboxylate (435 mg, 1.40 mmol), tetrakis(triphenylphosphine)palladium(0) (65 mg, 0.06 mmol), PdCl$_2$(dppf) (40 mg, 0.06 mmol), 2M aqueous potassium carbonate (1.65 mL, 3.3 mmol), dimethoxyethane (4.6 mL) and dimethylformamide (0.9 mL) was degassed with argon for 15 minutes. The reaction was then heated to 85° C. for 16 hours. Upon completion, the reaction was cooled to room temperature, diluted with ethyl acetate and filtered through Celite. The filtrate was washed with water and brine, dried (MgSO$_4$) and concentrated. The resulting crude material was purified by flash column chromatography to (2S,2'S)-tert-butyl 2,2'-(5,5'-(dibenzo[f,h]quinoxaline-6,11-diyl)bis(1H-imidazole-5,2-diyl))dipyrrolidine-1-carboxylate (150 mg, 39%). LCMS-ESI$^+$: calculated for C$_{40}$H$_{44}$N$_8$O$_4$: 700.35; observed [M+1]$^+$: 701.21.

Dimethyl (2S,2'S)-1,1'-((2S,2'S)-2,2'-(5,5'-(dibenzo[f,h]quinoxaline-6,11-diyl)bis(1H-imidazole-5,2-diyl))bis(pyrrolidine-2,1-diyl))bis(3-methyl-1-oxobutane-2,1-diyl)dicarbamate: A solution (2S,2'S)-tert-butyl 2,2'-(5,5'-(dibenzo[f,h]quinoxaline-6,11-diyl)bis(1H-imidazole-5,2-diyl))dipyrrolidine-1-carboxylate (150 mg, 0.21 mmol), concentrated HCl (1.0 mL) and ethanol (6 mL) was heated to 60° C. for one hour. The reaction was concentrated and redissolved in a minimal amount of methanol. An equal volume of dichloromethane was added and the solution was again concentrated. Dichloromethane was added to the resulting residue and concentrated off three more times, until the crude material was a powder. The crude amine was dissolved in dimethylformamide (2.1 mL). To this solution was added (S)-2-(methoxycarbonylamino)-3-methylbutanoic acid (95 mg, 0.54 mmol), HATU (190 mg, 0.49 mmol) and diisopropylethylamine (0.225 mL, 1.3 mmol). The reaction was stirred at room temperature for one hour. Upon completion, the reaction was diluted with ethyl acetate and the organic layer was washed with water and brine. The combined aqueous washings were extracted three times with ethyl acetate, and the combined organic layers were dried (MgSO$_4$) and concentrated. The crude material was purified by preparative reverse phase HPLC (Gemini, 15 to 50% ACN/H$_2$O+0.1% TFA) to yield dimethyl (2S,2'S)-1,1'-((2S, 2'S)-2,2'-(5,5'-(dibenzo[f,h]quinoxaline-6,11-diyl)bis(1H-imidazole-5,2-diyl))bis(pyrrolidine-2,1-diyl))bis(3-methyl-1-oxobutane-2,1-diyl)dicarbamate (101 mg, 58%). LCMS-ESI$^+$: calculated for $C_{44}H_{50}N_{10}O_6$: 814.93; observed [M+1]$^+$: 815.83.

Example BF

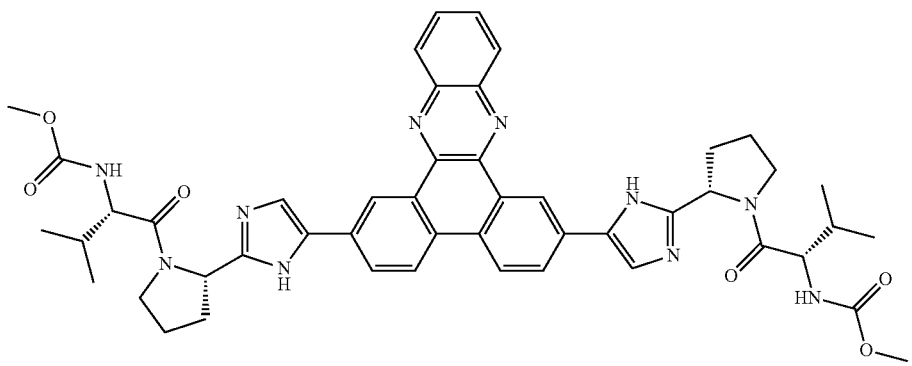

dimethyl (2S,2'S)-1,1'-((2S,2'S)-2,2'-(5,5'-(dibenzo[a,c]phenazine-2,7-diyl)bis(1H-imidazole-5,2-diyl))bis(pyrrolidine-2,1-diyl))bis(3-methyl-1-oxobutane-2,1-diyl)dicarbamate Dimethyl (2S,2'S)-1,1'-((2S,2'S)-2,2'-(5,5'-(dibenzo[a,c]phenazine-2,7-diyl)bis(1H-imidazole-5,2-diyl))bis(pyrrolidine-2,1-diyl))bis(3-methyl-1-oxobutane-2,1-diyl)dicarbamate: This compound was made in an analogous manner to (2S,2'S)-1,1'-((2S,2'S)-2,2'-(5,5'-(dibenzo[h]quinoxaline-6,11-diyl)bis(1H-imidazole-5,2-diyl))bis(pyrrolidine-2,1-diyl))bis(3-methyl-1-oxobutane-2,1-diyl)dicarbamate, substituting 1,2-phenylenediamine for ethylenediamine in the first step. LCMS-ESI$^+$: calculated for $C_{48}H_{52}N_{10}O_6$: 864.99; observed [M+1]$^+$: 865.92.

Example BG

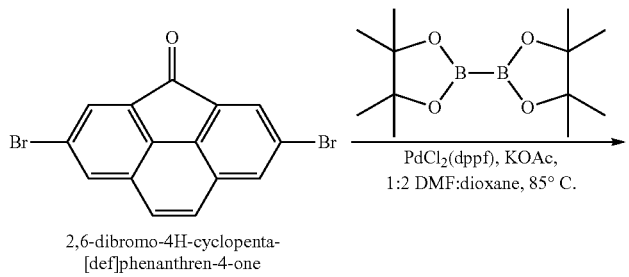

2,6-dibromo-4H-cyclopenta-[def]phenanthren-4-one

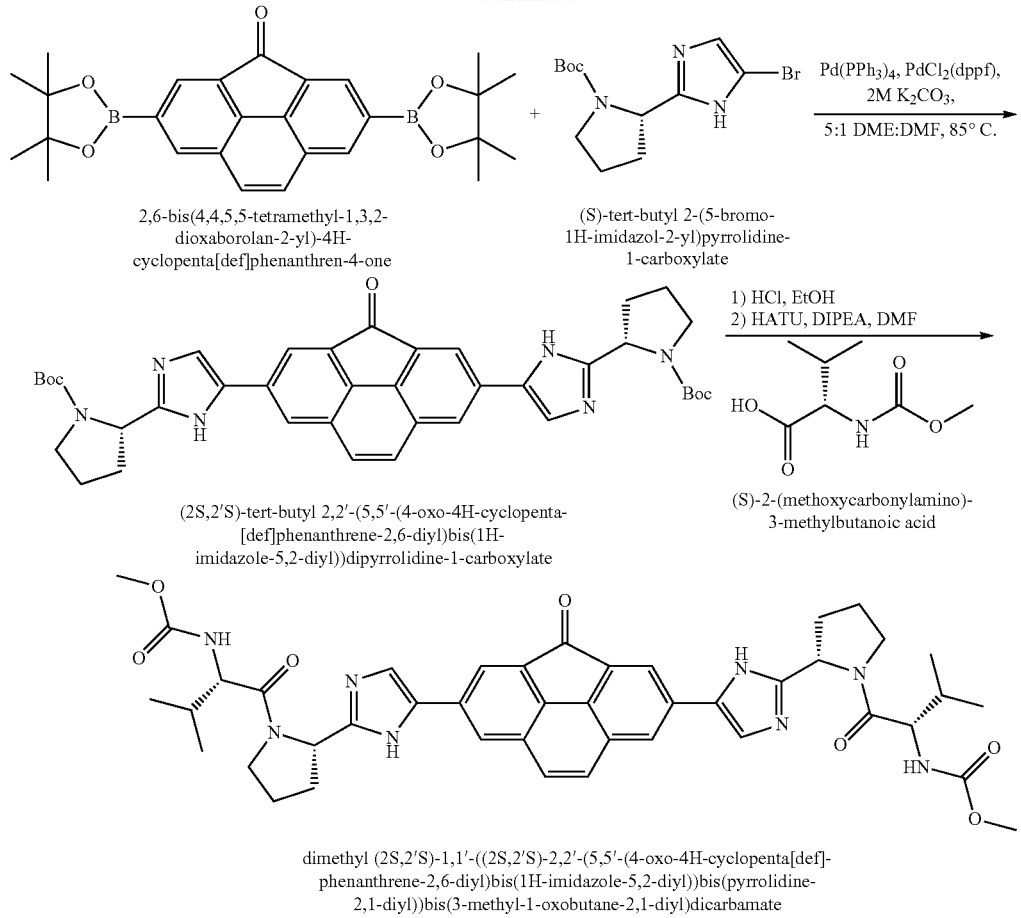

2,6-bis(4,4,5,5-tetramethyl-1,3,2-dioxaborolan-2-yl)-4H-cyclopenta[def]phenanthren-4-one (S)-tert-butyl 2-(5-bromo-1H-imidazol-2-yl)pyrrolidine-1-carboxylate (2S,2'S)-tert-butyl 2,2'-(5,5'-(4-oxo-4H-cyclopenta[def]phenanthrene-2,6-diyl)bis(1H-imidazole-5,2-diyl))dipyrrolidine-1-carboxylate (S)-2-(methoxycarbonylamino)-3-methylbutanoic acid dimethyl (2S,2'S)-1,1'-((2S,2'S)-2,2'-(5,5'-(4-oxo-4H-cyclopenta[def]-phenanthrene-2,6-diyl)bis(1H-imidazole-5,2-diyl))bis(pyrrolidine-2,1-diyl))bis(3-methyl-1-oxobutane-2,1-diyl)dicarbamate 2,6-bis(4,4,5,5-tetramethyl-1,3,2-dioxaborolan-2-yl)-4H-cyclopenta[def]phenanthren-4-one: A solution of 2,6-dibromo-4H-cyclopenta[def]phenanthren-4-one (425 mg, 1.2 mmol), bis(pinacolato)diboron (895 mg, 3.5 mmol) and potassium acetate (695 mg, 7.0 mmol) in 2:1 dioxane:dimethylformamide (12 mL) was degassed for fifteen minutes. To this solution was added PdCl$_2$(dppf) (86 mg, 0.12 mmol) and the reaction was heated to 85° C. for 2 hours. The mixture was cooled to room temperature, diluted with ethyl acetate and filtered through Celite. The filtrate was washed with water and brine, dried (MgSO$_4$) and concentrated. Solids precipitated immediately upon addition of methanol (30 mL) to the crude residue. This mixture was stirred for one hour, filtered and thoroughly rinsed with methanol to yield 2,6-bis(4,4,5,5-tetramethyl-1,3,2-dioxaborolan-2-yl)-4H-cyclopenta[def]phenanthren-4-one (260 mg, 49%) as a grey solid.

(2S,2'S)-tert-butyl 2,2'-(5,5'-(4-oxo-4H-cyclopenta[def]phenanthrene-2,6-diyl)bis(1H-imidazole-5,2-diyl))dipyrrolidine-1-carboxylate: A mixture of 2,6-bis(4,4,5,5-tetramethyl-1,3,2-dioxaborolan-2-yl)-4H-cyclopenta[def]phenanthren-4-one (260 mg, 0.57 mmol), (S)-tert-butyl 2-(5-bromo-1H-imidazol-2-yl)pyrrolidine-1-carboxylate (455 mg, 1.44 mmol), tetrakis(triphenylphosphine)palladium(0) (35 mg, 0.03 mmol), PdCl$_2$(dppf) (45 mg, 0.06 mmol), 2M aqueous potassium carbonate (1.75 mL, 3.5 mmol), dimethoxyethane (5.0 mL) and dimethylformamide (1.0 mL) was degassed with argon for 15 minutes. The reaction was then heated to 85° C. for 3 hours. Upon completion, the reaction was cooled to room temperature, diluted with ethyl acetate and filtered through Celite. The filtrate was washed with water and brine, dried (MgSO$_4$) and concentrated. The resulting crude material was purified by flash column chromatography to (2S,2'S)-tert-butyl 2,2'-(5,5'-(4-oxo-4H-cyclopenta[def]phenanthrene-2,6-diyl)bis(1H-imidazole-5,2-diyl))dipyrrolidine-1-carboxylate (148 mg, 38%). LCMS-ESI$^+$: calculated for C$_{39}$H$_{42}$N$_6$O$_5$: 674.32; observed [M+1]$^+$: 675.09.

Dimethyl (2S,2'S)-1,1'-((2S,2'S)-2,2'-(5,5'-(4-oxo-4H-cyclopenta[def]phenanthrene-2,6-diyl)bis(1H-imidazole-5,2-diyl))bis(pyrrolidine-2,1-diyl))bis(3-methyl-1-oxobutane-2,1-diyl)dicarbamate: A solution (2S,2'S)-tert-butyl 2,2'-(5,5'-(4-oxo-4H-cyclopenta[def]phenanthrene-2,6-diyl)bis(1H-imidazole-5,2-diyl))dipyrrolidine-1-carboxylate (148 mg, 0.22 mmol), concentrated HCl (1.0 mL) and ethanol (6 mL) was heated to 60° C. for one hour. The reaction was concentrated and redissolved in a minimal amount of methanol. An equal volume of dichloromethane was added and the solution was again concentrated. Dichloromethane was added to the resulting residue and concentrated off three more times, until the crude material was a powder. The crude amine was dissolved in dimethylformamide (2.2 mL). To this solution was added (S)-2-(methoxycarbonylamino)-3-methylbutanoic acid (95 mg, 0.54 mmol), HATU (190 mg, 0.49 mmol) and diisopropylethylamine (0.250 mL, 1.4 mmol). The reaction was stirred at room temperature for two hours. Upon completion, the reaction was diluted with ethyl acetate and the organic layer was washed with water and brine. The combined aqueous washings were extracted three times with ethyl acetate, and the combined organic layers were dried (MgSO$_4$), filtered through a freebasing column (Stratospheres™ PL-HCO$_3$MP SPE, Part #: PL3540-C603) and concentrated. The crude material was purified by preparative reverse phase HPLC (Gemini, 15 to 50% ACN/H$_2$O+0.1% TFA) to yield dimethyl (2S,2'S)-1,1'-((2S,2'S)-2,2'-(5,5'-(4-oxo-4H-cyclopenta[def]phenanthrene-2,6-diyl) bis(1H-imidazole-5,2-diyl))bis(pyrrolidine-2,1-diyl))bis(3-methyl-1-oxobutane-2,1-diyl)dicarbamate (92 mg, 53%). LCMS-ESI$^+$: calculated for C$_{43}$H$_{48}$N$_8$O$_7$: 788.89; observed [M+1]$^+$: 789.67.

Example BH

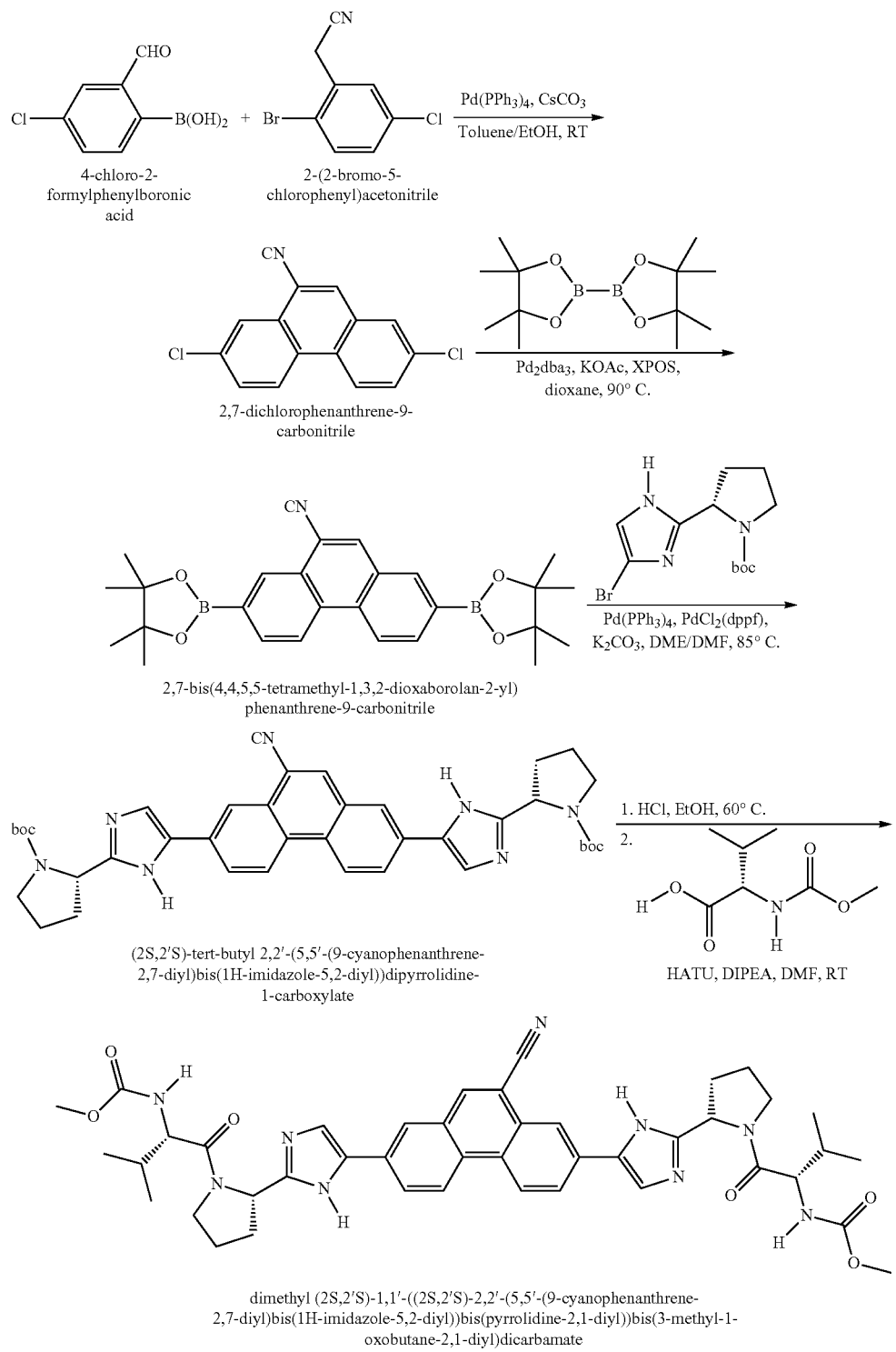

2,7-dichlorophenanthrene-9-carbonitrile. To a microwave vial was added 4-chloro-2-formylphenylboronic acid (480 mg, 2.6 mmol), 2-(2-bromo-5-chlorophenyl)acetonitrile (500 mg, 2 mmol), tetrakis(triphenyl phosphine)palladium (0) (100 mg, 0.085 mmol) and cesium carbonate (2.12g, 6.5 mmol) sequentially. The mixture was suspended in toluene (10 mL) and methanol (5 mL). Then the reaction vial was sealed and place in a microwave reactor and irradiated at 150° C. for 10 minutes. The reaction was cooled to room temperature, diluted with ethyl acetate, and filtered through a short celite pad. The solution was concentrated. The crude residue was purified by flash chromatography to yield 2,7-dichlorophenanthrene-9-carbonitrile (110 mg, 19%)

2,7-bis(4,4,5,5-tetramethyl-1,3,2-dioxaborolan-2-yl) phenanthrene-9-carbonitrile: A degassed mixture of 2,7-dichlorophenanthrene-9-carbonitrile (105 mg, 0.39 mmol), bis(pinacolato)diboron (294 mg, 1.15 mmol), potassium acetate (227 mg, 2.3 mmol), tris(dibenzylideneacetone)palladium (28 mg, 0.03 mmol) and 2-dicyclohexylphosphino-2',4',6'-tri-i-propyl-1,1'-biphenyl (29 mg, 0.06 mmol) in 1,4-dioxane (1.0 mL) was heated to 85° C. for 3 hours, cooled to room temperature and diluted with ethyl acetate. The organics were washed with water and brine, dried ($Na_2SO_4$), and concentrated. The crude residue was triturated with methanol, the precipitate was filtered off to yield 2,7-bis(4,4,5,5-tetramethyl-1,3,2-dioxaborolan-2-yl) phenanthrene-9-carbonitrile (82 mg, 47%)

(2S,2'S)-tert-butyl2,2'-(5,5'-(9-cyanophenanthrene-2,7-diyl)bis(1H-imidazole-5,2-diyl))dipyrrolidine-1-carboxylate. To a solution of 2,7-bis(4,4,5,5-tetramethyl-1,3,2-dioxaborolan-2-yl)phenanthrene-9-carbonitrile (147 mg, 0.32 mmol), (S)-tert-butyl 2-(4-bromo-1H-imidazol-2-yl)pyrrolidine-1-carboxylate (255 mg, 0.8 mmol), tetrakis(triphenylphosphine)palladium(0) (19 mg, 0.02 mmol) and dichloro[1,1'-bis(diphenylphosphino)ferrocene]palladium(II) (24 mg, 0.03 mmol) in a mixture of 1,2-dimethoxyethane (5.0 mL) and dimethylformamide (1 mL) was added a solution of potassium carbonate (2M in water, 0.5 mL, 0.96 mmol). The resulting mixture was degassed and then heated to 85° C. under argon for 18 hours. After cooling to room temperature, the reaction was diluted with ethyl acetate. The organics were washed with water and brine, dried ($Na_2SO_4$), and concentrated. The crude residue was purified by flash chromatography to yield (2S,2'S)-tert-butyl 2,2'-(5,5'-(9-cyanophenanthrene-2,7-diyl)bis(1H-imidazole-5,2-diyl))dipyrrolidine-1-carboxylate (119 mg, 55%)

Dimethyl (2S,2'S)-1,1'-((2S,2'S)-2,2'-(5,5'-(9-cyanophenanthrene-2,7-diyl)bis(1H-imidazole-5,2-diyl))bis(pyrrolidine-2,1-diyl))bis(3-methyl-1-oxobutane-2,1-diyl)dicarbamate: A solution of (2S,2'S)-tert-butyl 2,2'-(5,5'-(9-cyanophenanthrene-2,7-diyl)bis(1H-imidazole-5,2-diyl)) dipyrrolidine-1-carboxylate (119 mg, 0.18 mmol), ethanol (6 mL) and concentrated HCl (1 mL) was heated to 60° C. for 1 hour. The reaction was concentrated and the crude material dissolved in DCM (6 mL). This solution was concentrated and to this material was added a solution of 2-methoxycarbonylamino-3-methylbutyric acid (77 mg, 0.44 mmol) and HATU (154 mg, 0.41 mmol) in DMF (3 mL). To the resulting solution was added diisopropylethylamine (190 μL, 1.1 mmol). After stirring for 18 hours at room temperature, the reaction was diluted with ethyl acetate, washed with water and brine, dried ($Na_2SO_4$), concentrated and purified by preparative reverse phase HPLC (Gemini, 15 to 50% $ACN/H_2O+0.1\%$ TFA). The product fractions were lyophilized to give Dimethyl (2S,2'S)-1,1'-((2S,2'S)-2,2'-(5,5'-(9-cyanophenanthrene-2,7-diyl)bis(1H-imidazole-5,2-diyl))bis(pyrrolidine-2,1-diyl)) bis(3-methyl-1-oxobutane-2,1-diyl)dicarbamate (55 mg, 39%). LCMS-ESI$^+$: calculated for $C_{43}H_{49}N_9O_6$: 787.93; observed [M+1]$^+$: 788.75.

Example BI

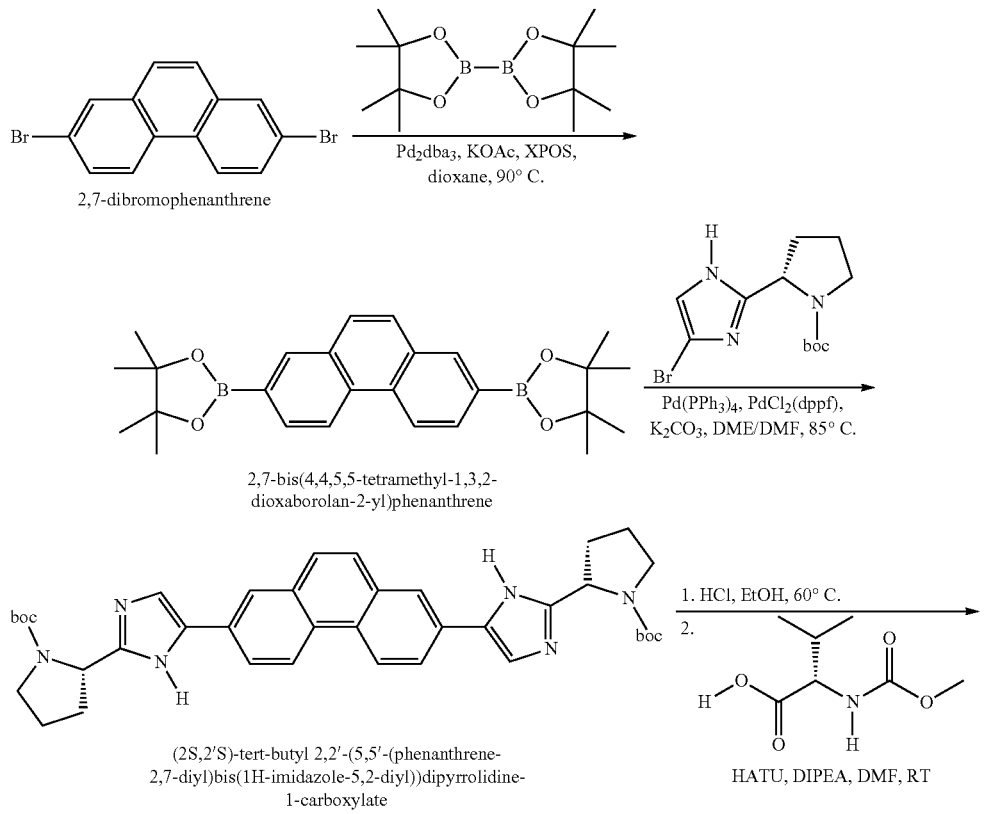

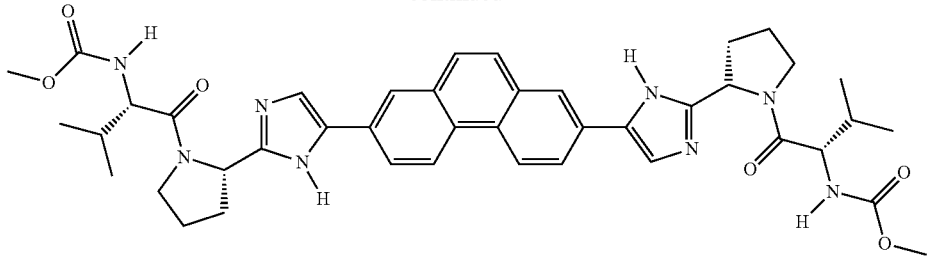

dimethyl (2S,2'S)-1,1'-((2S,2'S)-2,2'-(5,5'-(phenanthrene-2,7-diyl)bis(1H-imidazole-5,2-diyl))bis(pyrrolidine-2,1-diyl))bis(3-methyl-1-oxobutane-2,1-diyl)dicarbamate

15

2,7-bis(4,4,5,5-tetramethyl-1,3,2-dioxaborolan-2-yl) phenanthrene A degassed mixture of 2,7-dibromophenanthrene (1.21 g, 3.57 mmol), bis(pinacolato)diboron (2.72 g, 10.7 mmol), potassium acetate (2.10 g, 21.4 mmol), tris(dibenzylideneacetone)palladium (262 mg, 0.28 mmol) and 2-dicyclohexylphosphino-2',4',6'-tri-i-propyl-1,1'-biphenyl (272 mg, 0.57 mmol) in 1,4-dioxane (1.0 mL) was heated to 85° C. for 3 hours, cooled to room temperature and diluted with ethyl acetate. The organics were washed with water and brine, dried ($Na_2SO_4$), and concentrated. The crude residue was triturated with methanol, the precipitate was filtered off to yield 2,7-bis(4,4,5,5-tetramethyl-1,3,2-dioxaborolan-2-yl) phenanthrene (1.21 g, 77%)

(2S,2'S)-tert-butyl 2,2'-(5,5'-(phenanthrene-2,7-diyl)bis(1H-imidazole-5,2-diyl))dipyrrolidine-1-carboxylate. To a solution of 2,7-bis(4,4,5,5-tetramethyl-1,3,2-dioxaborolan-2-yl) phenanthrene (250 mg, 0.58 mmol), (S)-tert-butyl 2-(4-bromo-1H-imidazol-2-yl)pyrrolidine-1-carboxylate (459 mg, 1.45 mmol), tetrakis(triphenylphosphine)palladium(0) (36 mg, 0.03 mmol) and dichloro[1,1'-bis(diphenylphosphino)ferrocene]palladium(II) (43 mg, 0.06 mmol) in a mixture of 1,2-dimethoxyethane (5.0 mL) and dimethylformamide (1 mL) was added a solution of potassium carbonate (2M in water, 1.8 mL, 3.4 mmol). The resulting mixture was degassed and then heated to 85° C. under argon for 18 hours. After cooling to room temperature, the reaction was diluted with ethyl acetate. The organics were washed with water and brine, dried ($Na_2SO_4$), and concentrated. The crude residue was purified by flash chromatography to yield (2S,2'S)-tert-butyl 2,2'-(5,5'-(phenanthrene-2,7-diyl)bis(1H-imidazole-5,2-diyl))dipyrrolidine-1-carboxylate (237 mg, 38%)

dimethyl (2S,2'S)-1,1'-((2S,2'S)-2,2'-(5,5'-(phenanthrene-2,7-diyl)bis(1H-imidazole-5,2-diyl))bis(pyrrolidine-2,1-diyl))bis(3-methyl-1-oxobutane-2,1-diyl)dicarbamate: A solution of (2S,2'S)-tert-butyl 2,2'-(5,5'-(phenanthrene-2,7-diyl)bis(1H-imidazole-5,2-diyl))dipyrrolidine-1-carboxylate (235 mg, 0.36 mmol), ethanol (6 mL) and concentrated HCl (1 mL) was heated to 60° C. for 1 hour. The reaction was concentrated and the crude material dissolved in DCM (6 mL). This solution was concentrated and to this material was added a solution of 2-methoxycarbonylamino-3-methylbutyric acid (144 mg, 0.82 mmol) and HATU (287 mg, 0.75 mmol) in DMF (3 mL). To the resulting solution was added diisopropylethylamine (340 μL, 1.97 mmol). After stirring for 18 hours at room temperature, the reaction was diluted with ethyl acetate, washed with water and brine, dried ($Na_2SO_4$), concentrated and purified by preparative reverse phase HPLC (Gemini, 15 to 50% ACN/$H_2O$+0.1% TFA). The product fractions were lyophilized to give dimethyl (2S,2'S)-1,1'-((2S,2'S)-2,2'-(5,5'-(phenanthrene-2,7-diyl)bis(1H-imidazole-5,2-diyl))bis(pyrrolidine-2,1-diyl)) bis(3-methyl-1-oxobutane-2,1-diyl)dicarbamate (122 mg, 44%). LCMS-ESI$^+$: calculated for $C_{42}H_{50}N_8O_6$: 762.92; observed [M+1]$^+$: 763.47.

Example BJ

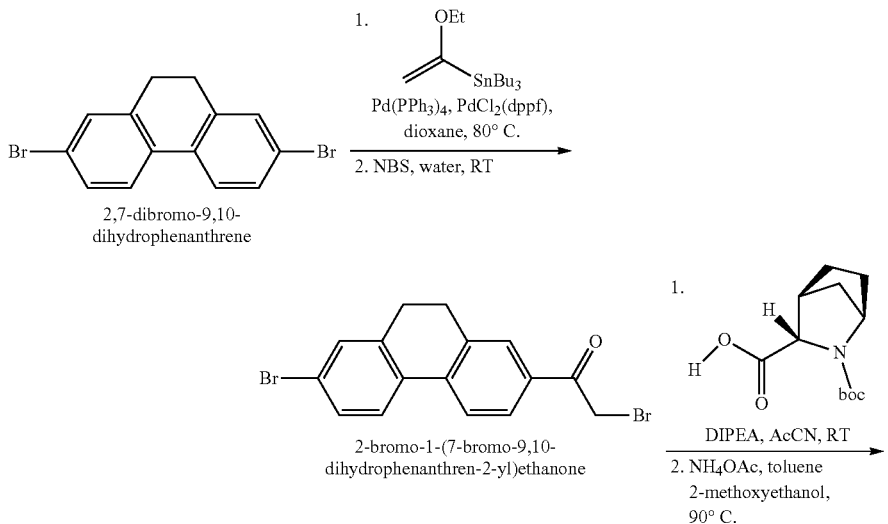

-continued

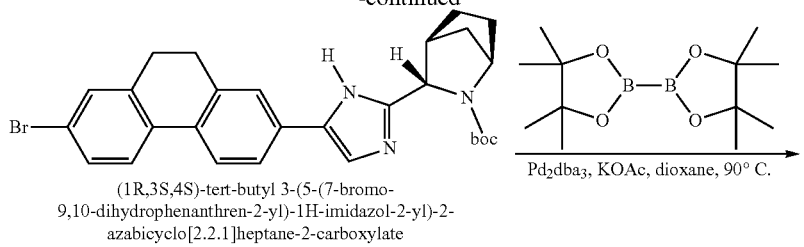

(1R,3S,4S)-tert-butyl 3-(5-(7-bromo-
9,10-dihydrophenanthren-2-yl)-1H-imidazol-2-yl)-2-
azabicyclo[2.2.1]heptane-2-carboxylate

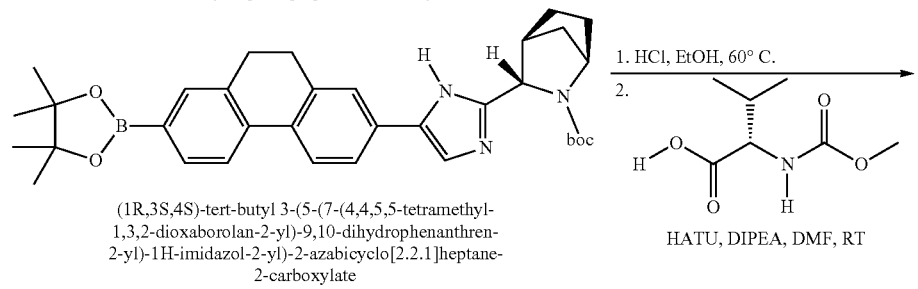

(1R,3S,4S)-tert-butyl 3-(5-(7-(4,4,5,5-tetramethyl-
1,3,2-dioxaborolan-2-yl)-9,10-dihydrophenanthren-
2-yl)-1H-imidazol-2-yl)-2-azabicyclo[2.2.1]heptane-
2-carboxylate

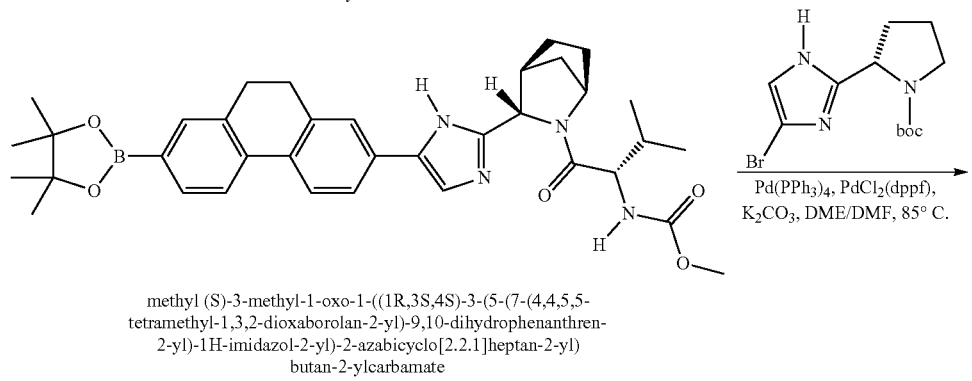

methyl (S)-3-methyl-1-oxo-1-((1R,3S,4S)-3-(5-(7-(4,4,5,5-
tetramethyl-1,3,2-dioxaborolan-2-yl)-9,10-dihydrophenanthren-
2-yl)-1H-imidazol-2-yl)-2-azabicyclo[2.2.1]heptan-2-yl)
butan-2-ylcarbamate

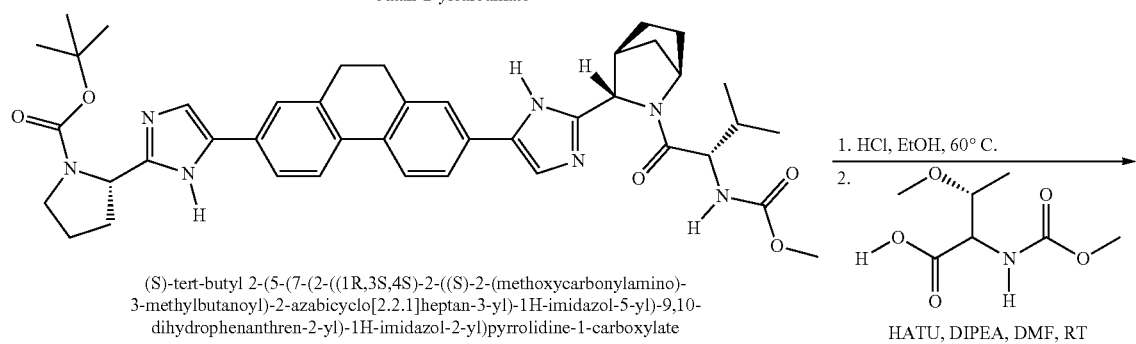

(S)-tert-butyl 2-(5-(7-(2-((1R,3S,4S)-2-((S)-2-(methoxycarbonylamino)-
3-methylbutanoyl)-2-azabicyclo[2.2.1]heptan-3-yl)-1H-imidazol-5-yl)-9,10-
dihydrophenanthren-2-yl)-1H-imidazol-2-yl)pyrrolidine-1-carboxylate

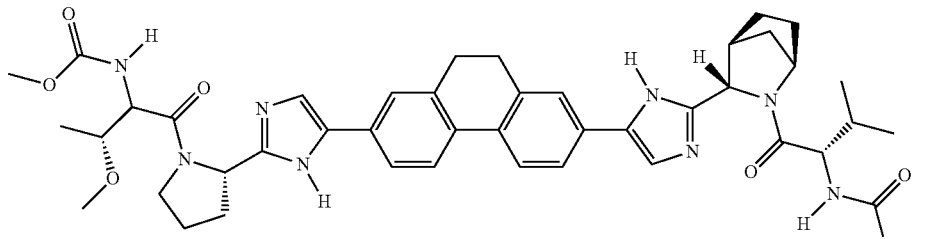

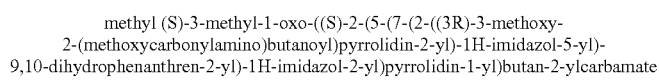

methyl (S)-3-methyl-1-oxo-((S)-2-(5-(7-(2-((3R)-3-methoxy-
2-(methoxycarbonylamino)butanoyl)pyrrolidin-2-yl)-1H-imidazol-5-yl)-
9,10-dihydrophenanthren-2-yl)-1H-imidazol-2-yl)pyrrolidin-1-yl)butan-2-ylcarbamate 2-bromo-1-(7-bromo-9,1-dihydrophenanthren-2-yl)ethanone. A degassed mixture of 2,7-dibromo-9,10-dihydrophenanthrene (3.5 g, 10.35 mmol), tributyl-(1-ethoxyvinyl)tin (3.8 mL, 11.4 mmol), tetrakis(triphenylphosphine) palladium(0) (598 mg, 0.52 mmol) and dichloro[1,1'-bis(diphenyl-phosphino) ferrocene]palladium(II) (378 mg, 0.52 mmol) in 1,4-dioxane (1.0 mL) was heated to 85° C. for 18 hours, cooled to room temperature and N-bromosuccinimide (2.21 g, 12.42 mmol) and water (25 mL) were added. The reaction mixture was stirred at room temperature for 2 hours, diluted with ethyl acetate. The organics were washed with water and brine, dried ($Na_2SO_4$), and concentrated. The crude residue was purified by flash chromatography to yield 2-bromo-1-(7-bromo-9,10-dihydrophenanthren-2-yl)ethanone (635 mg, 16%).

(1R,3S,4S)-tert-butyl 3-(5-(7-bromo-9,10-dihydrophenanthren-2-yl)-1H-imidazol-2-yl)-2-azabicyclo[2.2.1]heptane-2-carboxylate: To a solution of (4S)-2-(tert-butoxycarbonyl)-2-azabicyclo[2.2.1]heptane-3-carboxylic acid (443 mg, 1.83 mmol) and 2-bromo-1-(7-bromo-9,10-dihydrophenanthren-2-yl)ethanone (635 mg, 1.67 mmol) in acetonitrile (7 mL) was added diisopropylethylamine (0.6 mL, 3.34 mmol). The reaction was stirred at room temperature for 16 hours and was then diluted with ethyl acetate. The organics were washed with water and brine, dried ($MgSO_4$) and concentrated. The resulting crude residue was purified by flash chromatography to yield (1R,3S,4S)-tert-butyl 3-(5-(7-bromo-9,10-dihydrophenanthren-2-yl)-1H-imidazol-2-yl)-2-azabicyclo[2.2.1]heptane-2-carboxylate (670 mg, 74%).

To a solution of (1R,3S,4S)-tert-butyl 3-(5-(7-bromo-9,10-dihydrophenanthren-2-yl)-1H-imidazol-2-yl)-2-azabicyclo[2.2.1]heptane-2-carboxylate (665 mg, 1.23 mmol) in a mixture of toluene (1.8 mL) and 2-methoxyethanol (0.1 mL) was added ammonium acetate (474 mg, 6.15 mmol). The reaction mixture was heated to 90° C. for 18 hours, cooled to room temperature and diluted with ethyl acetate. The organics were washed with water and brine, dried ($Na_2SO_4$), and concentrated. The crude residue was purified by flash chromatography to yield (1R,3S,4S)-tert-butyl 3-(5-(7-bromo-9,10-dihydrophenanthren-2-yl)-1H-imidazol-2-yl)-2-azabicyclo[2.2.1]heptane-2-carboxylate (373 mg, 58%). LCMS-ESI$^+$: calculated for $C_{28}H_{30}BrN_3O_2$: 520.47; observed [M+1]$^+$: 520.97.

(1R,3S,4S)-tert-butyl 3-(5-(7-(4,4,5,5-tetramethyl-1,3,2-dioxaborolan-2-yl)-9,10-dihydrophenanthren-2-yl)-1H-imidazol-2-yl)-2-azabicyclo[2.2.1]heptane-2-carboxylate. A degassed mixture of 3-(5-(7-bromo-9,10-dihydrophenanthren-2-yl)-1H-imidazol-2-yl)-2-azabicyclo[2.2.1]heptane-2-carboxylate (369 mg, 0.71 mmol), bis(pinacolato)diboron (270 mg, 1.06 mmol), potassium acetate (209 mg, 2.13 mmol) and dichloro[1,1'-bis(diphenylphosphino)ferrocene]palladium(II) (26 mg, 0.035 mmol) in 1,4-dioxane (5 mL) was heated to 90° C. for 3 hours, cooled to room temperature and diluted with ethyl acetate. The organics were washed with water and brine, dried ($Na_2SO_4$), and concentrated. The crude (1R,3 S,4S)-tert-butyl-3-(5-(7-(4,4,5,5-tetramethyl-1,3,2-dioxaborolan-2-yl)-9,10-dihydrophenan-thren-2-yl)-1H-imidazol-2-yl)-2-azabicyclo[2.2.1]heptane-2-carboxylate was used without further purification. LCMS-ESI$^+$: calculated for $C_{34}H_{42}BN_3O_4$: 567.54; observed [M+1]$^+$: 568.09.

methyl (S)-3-methyl-1-oxo-1-((1R,3S,4S)-3-(5-(7-(4,4,5,5-tetramethyl-1,3,2-dioxaborolan-2-yl)-9,10-dihydrophenanthren-2-yl)-1H-imidazol-2-yl)-2-azabicyclo[2.2.1]heptan-2-yl)butan-2-ylcarbamate. A solution of (1R,3S,4S)-tert-butyl-3-(5-(7-(4,4,5,5-tetramethyl-1,3,2-dioxaborolan-2-yl)-9,10-dihydro-phenanthren-2-yl)-1H-imidazol-2-yl)-2-azabicyclo[2.2.1]heptane-2-carboxylate (~0.69 mmol), ethanol (6 mL) and concentrated HCl (2 mL) was heated to 60° C. for 1.5 hours. The reaction was concentrated and the crude material dissolved in DCM (10 mL). This solution was concentrated and to this material was added a solution of 2-methoxycarbonylamino-3-methylbutyric acid (162 mg, 0.9 mmol) and HATU (397 mg, 1.04 mmol) in DMF (5 mL). To the resulting solution was added diisopropylethylamine (360 µL, 2.08 mmol). After stirring for 18 hours at room temperature, the reaction was diluted with ethyl acetate, washed with water and brine, dried ($Na_2SO_4$), concentrated and the crude methyl (S)-3-methyl-1-oxo-1-((1R,3 S,4S)-3-(5-(7-(4,4,5,5-tetramethyl-1,3,2-dioxaborolan-2-yl)-9,10-dihydrophenanthren-2-yl)-1H-imidazol-2-yl)-2-azabicyclo[2.2.1]heptan-2-yl)butan-2-ylcarbamate was used without further purification. LCMS-ESI$^+$: calculated for $C_{36}H_{45}BN_4O_5$: 624.59; observed [M+1]$^+$: 625.35.

S)-tert-butyl-2-(5-(7-(2-((1R,3S,4S)-2-((S)-2-(methoxycarbonylamino)-3-methylbutanoyl)-2-azabicy-clo[2.2.1]heptan-3-yl)-1H-imidazol-5-yl)-9,10-dihydrophenanthren-2-yl)-1H-imidazol-2-yl)pyrro-lidine-1-carboxylate. To a solution of methyl (S)-3-methyl-1-oxo-1-((1R,3 S,4S)-3-(5-(7-(4,4,5,5-tetramethyl-1,3,2-dioxaborolan-2-yl)-9,10-dihydrophenanthren-2-yl)-1H-imidazol-2-yl)-2-azabicyclo[2.2.1]heptan-2-yl)butan-2-ylcarbamate (~0.67 mmol), (S)-tert-butyl 2-(4-bromo-1H-imidazol-2-yl)pyrrolidine-1-carboxylate (266 mg, 0.84 mmol), tetrakis(triphenylphosphine) palladium(0) (23 mg, 0.02 mmol) and dichloro[1,1'-bis(diphenylphosphino)ferrocene]palladium (II) (30 mg, 0.04 mmol) in a mixture of 1,2-dimethoxyethane (10.0 mL) and dimethylformamide (2 mL) was added a solution of potassium carbonate (2M in water, 1.0 mL, 2.0 mmol). The resulting mixture was degassed and then heated to 85° C. under argon for 18 hours. After cooling to room temperature, the reaction was diluted with ethyl acetate. The organics were washed with water and brine, dried ($Na_2SO_4$), and concentrated. The crude residue was purified by flash chromatography to yield S)-tert-butyl 2-(5-(7-(2-((1R,3 S,4S)-2-((S)-2-(methoxycarbonylamino)-3-methylbutanoyl)-2-azabicyclo [2.2.1]heptan-3-yl)-1H-imidazol-5-yl)-9,10-dihydrophenanthren-2-yl)-1H-imidazol-2-yl)pyrrolidine-1-carboxylate (182 mg, 56%)

Methyl (S)-3-methyl-1-oxo-1-((S)-2-(5-(7-(2-((3R)-3-methoxy-2-(methoxycarbonylamino) buta-noyl)pyrrolidin-2-yl)-1H-imidazol-5-yl)-9,10-dihydrophenanthren-2-yl)-1H-imidazol-2-yl) pyrrolidin-1-yl)butan-2-ylcarbamate. A solution of S)-tert-butyl 2-(5-(7-(2-((1R,3S,4S)-2-((S)-2-(methoxycarbonylamino)-3-methylbutanoyl)-2-azabicyclo[2.2.1]heptan-3-yl)-1H-imidazol-5-yl)-9,10-dihydrophenanthren-2-yl)-1H-imidazol-2-yl)pyrrolidine-1-carboxylate (86 mg, 0.12 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (3R)-3-methoxy-2-(methoxycarbonylamino)butanoic acid (29 mg, 0.15 mmol) and HATU (67 mg, 0.18 mmol) in DMF (1.5 mL). To the resulting solution was added diisopropylethylamine (600 µL, 3.5 mmol). After stirring for 18 hours at room temperature, the reaction was diluted with ethyl acetate, washed with water and brine, dried ($Na_2SO_4$), concentrated and purified by preparative reverse phase HPLC (Gemini, 15 to 50% ACN/$H_2O$+0.1% TFA). The product fractions were lyophilized to give Methyl (S)-3-methyl-1-oxo-1-((S)-2-(5-(7-(2-((3R)-3-methoxy-2-(methoxycarbonylamino) buta-noyl)pyrrolidin-2-yl)-1H-imidazol-5-yl)-9,10-dihydrophenanthren-2-yl)-1H-imidazol-2-yl) pyrrolidin-1-yl)butan-2-ylcarbamate (39 mg, 41%). LCMS-ESI$^+$: calculated for $C_{44}H_{54}N_8O_7$: 806.97; observed [M+1]$^+$: 807.74.

Example BK

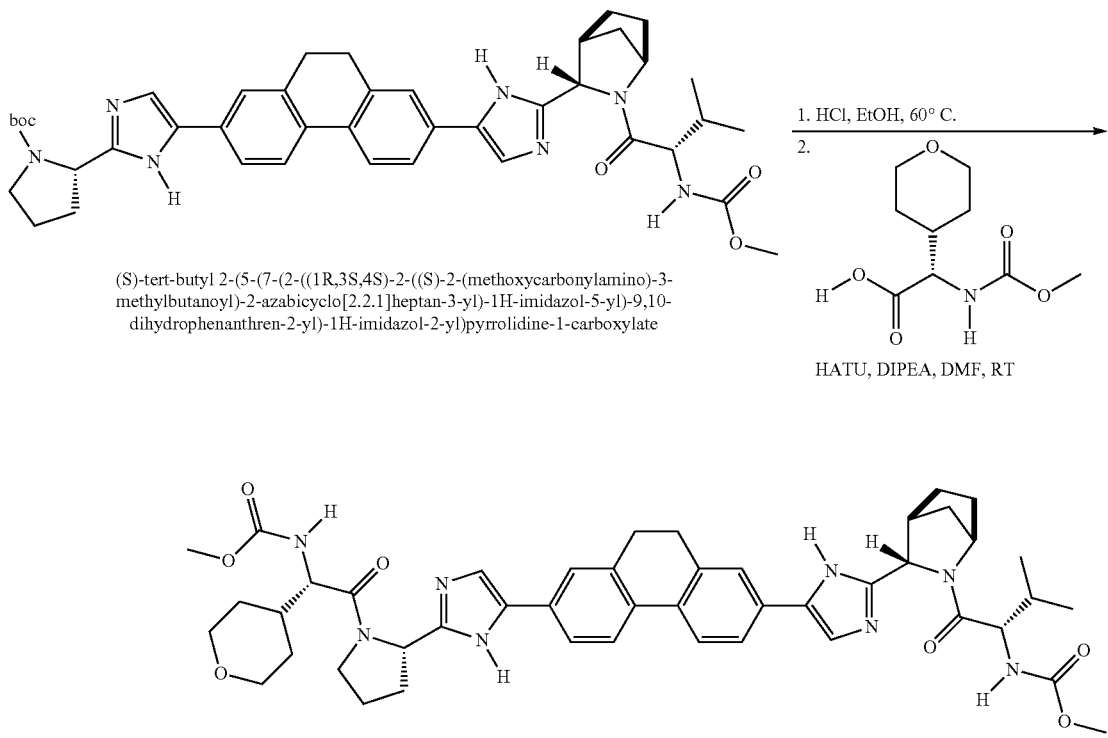

(S)-tert-butyl 2-(5-(7-(2-(((1R,3S,4S)-2-((S)-2-(methoxycarbonylamino)-3-methylbutanoyl)-2-azabicyclo[2.2.1]heptan-3-yl)-1H-imidazol-5-yl)-9,10-dihydrophenanthren-2-yl)-1H-imidazol-2-yl)pyrrolidine-1-carboxylate

HATU, DIPEA, DMF, RT methyl (S)-3-methyl-1-oxo-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-imidazol-2-yl)pyrrolidin-1-yl)butan-2-ylcarbamate methyl (S)-3-methyl-1-oxo-1-((S)-2-(methoxycarbonylamino)-2-(tetrahydro-2H-pyran-4-yl) acetyl) pyrrolidin-2-yl)-1H-imidazol-5-yl)-9,10-dihydrophenanthren-2-yl)-1H-imidazol-2-yl) pyrrolidin-1-yl) butan-2-ylcarbamate. A solution S)-tert-butyl 2-(5-(7-(2-(((1R,3S,4S)-2-((S)-2-(methoxycarbonylamino)-3-methylbutanoyl)-2-azabicyclo[2.2.1]heptan-3-yl)-1H-imidazol-5-yl)-9,10-dihydrophenanthren-2-yl)-1H-imidazol-2-yl)pyrrolidine-1-carboxylate (92 mg, 0.13 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (S)-2-(methoxycarbonylamino)-2-(tetrahydro-2H-pyran-4-yl)acetic acid (35 mg, 0.16 mmol) and HATU (71 mg, 0.19 mmol) in DMF (1.5 mL). To the resulting solution was added diisopropylethylamine (700 μL, 3.8 mmol). After stirring for 18 hours at room temperature, the reaction was diluted with ethyl acetate, washed with water and brine, dried (Na$_2$SO$_4$), concentrated and purified by preparative reverse phase HPLC (Gemini, 10 to 1% TFA/H$_2$O+1% TFA/CH$_3$CN). The product fractions were lyophilized to give methyl (S)-3-methyl-1-oxo-1-((S)-2-(methoxycarbonylamino)-2-(tetrahydro-2H-pyran-4-yl)acetyl) pyrro-lidin-2-yl)-1H-imidazol-5-yl)-9,10-dihydrophenanthren-2-yl)-1H-imidazol-2-yl) pyrrolidin-1-yl)butan-2-ylcarbamate (36 mg, 34%). LCMS-ESI$^+$: calculated for C$_{46}$H$_{56}$N$_8$O$_7$: 833.01; observed [M+1]$^+$: 833.58.

Example BL

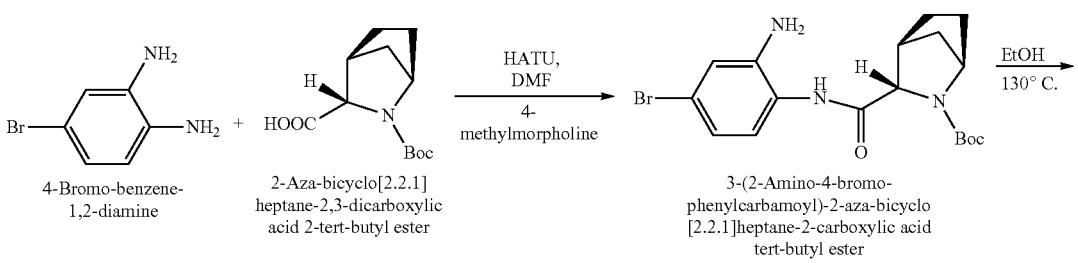

4-Bromo-benzene-1,2-diamine

2-Aza-bicyclo[2.2.1]heptane-2,3-dicarboxylic acid 2-tert-butyl ester

HATU, DMF
4-methylmorpholine 3-(2-Amino-4-bromo-phenylcarbamoyl)-2-aza-bicyclo[2.2.1]heptane-2-carboxylic acid tert-butyl ester EtOH
130° C.

-continued
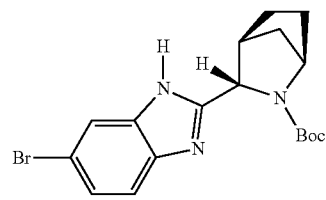
3-(6-bromo-1H-benzoimidazol-2-yl)-2-aza-bicyclo[2.2.1]heptane-2-carboxylic acid tert-butyl ester
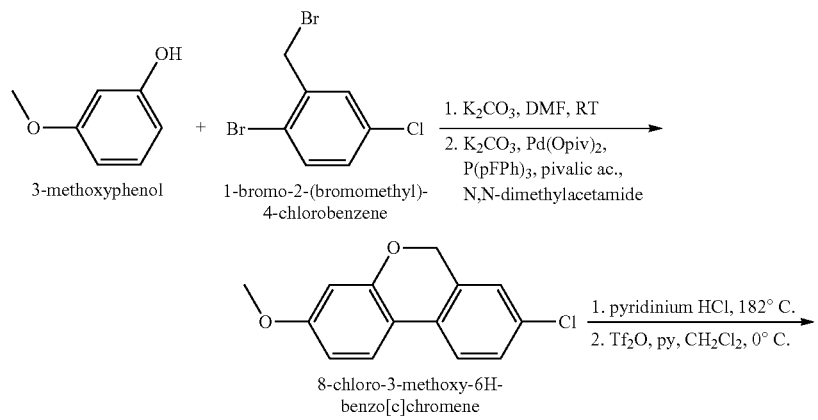
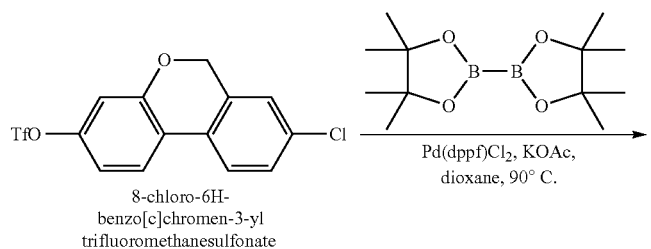
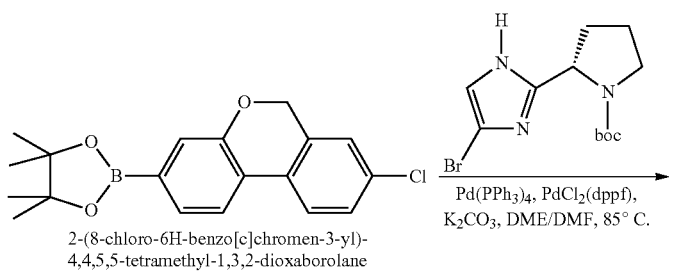
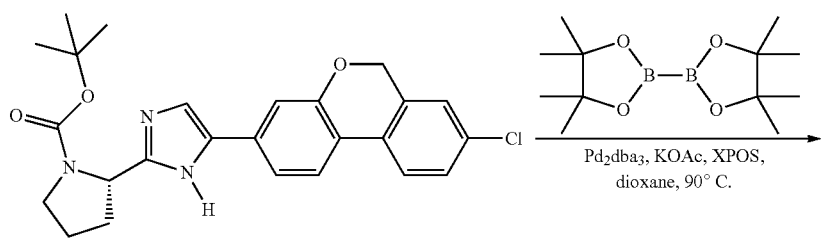

-continued

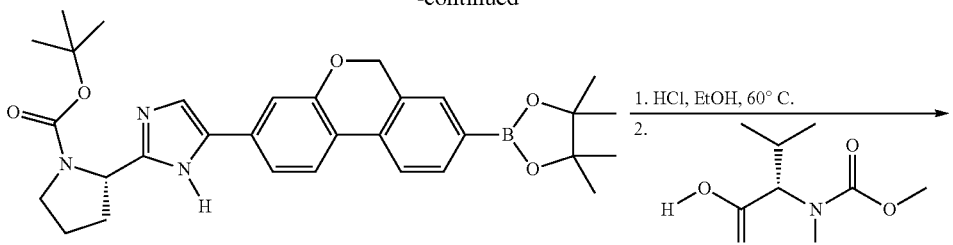

(S)-tert-butyl 2-(5-(8-(4,4,5,5-tetramethyl-1,3,2-dioxaborolan-2-yl)-6H-benzo[c]chromen-3-yl)-1H-imidazol-2-yl)pyrrolidine-1-carboxylate 1. HCl, EtOH, 60° C.
2. HATU, DIPEA, DMF, RT

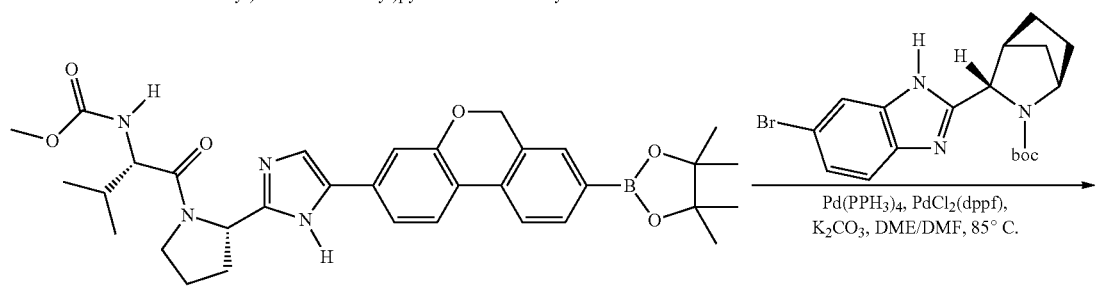

methyl-3-methyl-1-oxo-1-((S)-2-(5-(8-(4,4,5,5-tetramethyl-1,3,2-dioxaborolan-2-yl)-6H-benzo[c]chromen-3-yl)-1H-imidazol-2-yl)pyrrolidin-1-yl)butan-2-ylcarbamate Pd(PPH$_3$)$_4$, PdCl$_2$(dppf), K$_2$CO$_3$, DME/DMF, 85° C.

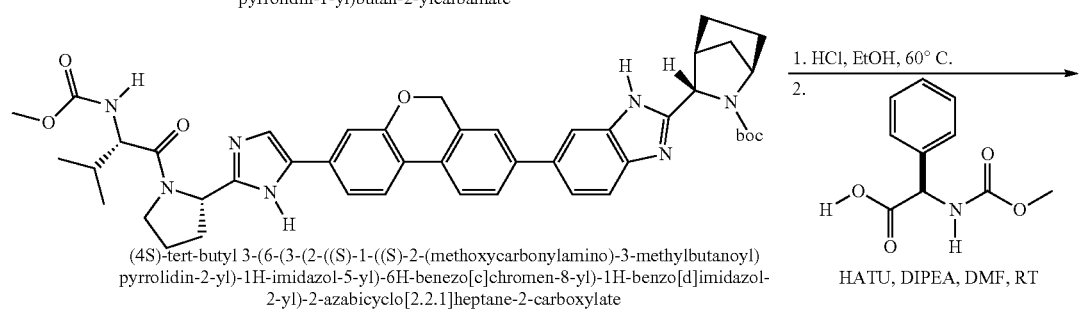

(4S)-tert-butyl 3-(6-(3-(2-((S)-1-((S)-2-(methoxycarbonylamino)-3-methylbutanoyl)pyrrolidin-2-yl)-1H-imidazol-5-yl)-6H-benzo[c]chromen-8-yl)-1H-benzo[d]imidazol-2-yl)-2-azabicyclo[2.2.1]heptane-2-carboxylate 1. HCl, EtOH, 60° C.
2. HATU, DIPEA, DMF, RT

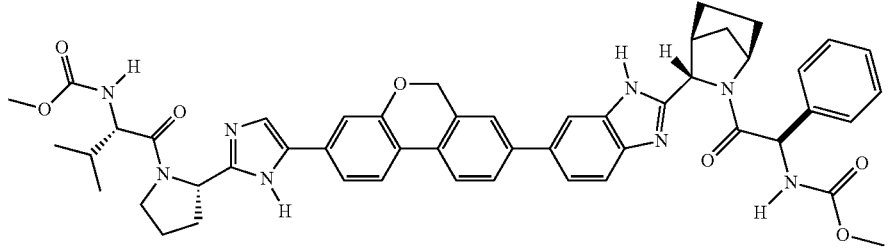

methyl (1R)-2-((4S)-3-methyl-3-(6-(3-(2-((methoxycarbonylamino-3-methylbutanoyl))-pyrrolidin-2-yl)-1H-imidazol-5-yl)-6H-benzo[c]chromen-8-yl)-1H-benzo[d]imidazol-2-yl)-2-azabicyclo[2.2.1]heptan-2-yl)-2-oxo-1-phenylethylcarbamate 3-(2-Amino-4-bromo-phenylcarbamoyl)-2-aza-bicyclo[2.2.1]heptane-2-carboxylic acid tert-butyl ester: To a solution of 2-Aza-bicyclo[2.2.1]heptane-2,3-dicarboxylic acid 2-tert-butyl ester (0.327 g, 1.36 mmol, 1 eq.), 4-Bromobenzene-1,2-diamine (0.507 g, 2.71 mmol, 2 eq.) and 4-methylmorpholine (0.299 mL, 2 eq.) in 10 mL DMF was added HATU (0.543g, 1.05 eq.). The reaction mixture was stirred at room temperature for 1 hour then concentrated down. The reaction mixture was diluted with ethyl acetate and washed with diluted NaHCO3 aqueous solution and brine. The organic layer was concentrated down and purified by flash column chromatography (silica gel, 20 to 80% ethyl acetate/hexane) to give a mixture of regioisomer 3-(2-Amino-4-bromo-phenylcarbamoyl)-2-aza-bicyclo[2.2.1]heptane-2-carboxylic acid tert-butyl ester.

3-(6-Bromo-1H-benzoimidazol-2-yl)-2-aza-bicyclo[2.2.1]heptane-2-carboxylic acid tert-butyl ester: The above mixture of regioisomer 3-(2-Amino-4-bromo-phenylcarbamoyl)-2-aza-bicyclo[2.2.1]heptane-2-carboxylic acid tert-butyl ester was dissolved in ethanol and heated to 130° C. in sealed tube overnight and continue heating at 170° C. for 3 days. LC-MS showed desired product and Boc cleaved product (about 1:1 ratio). The mixture was concentrated down and dissolved DCM. Di-tert-butyl dicarbonate (0.6 eq.) was added and reaction was stirred overnight at room temperature. The reaction mixture was concentrated down and purified by flash column chromatography (silica gel, 20 to 80% ethyl acetate/hexane) to give 3-(6-Bromo-1H-benzoimidazol-2-yl)-2-aza-bicyclo[2.2.1]heptane-2-carboxylic acid tert-butyl ester (0.383 g, 72%) as an orange foam.

8-chloro-3-methoxy-6H-benzo[c]chromene: To a solution of 3-methoxyphenol (0.84 mL, 7.3 mmol) and 1-bromo-2-(bromomethyl)-4-chlorobenzene (2 g, 7 mmol) in DMF (70 mL) was added potassium carbonate (1.94 g, 14 mmol). The reaction mixture was stirred at room temperature for 16 hours, then poured into water (500 mL) extracted into ethyl acetate. The organics were washed with water and brine, dried ($Na_2SO_4$), and concentrated. The crude residue was purified by flash chromatography to yield 1-bromo-4-chloro-2-((3-methoxyphenoxy)methyl) benzene (2 g, 87%)

To a degassed mixture of potassium carbonate (1.27 g, 9 mmol), palladium(II)trimethyl acetate (47 mg, 0.15 mmol), tris (p-fluorophenyl)phosphine (48 mg, 0.15 mmol) and trimethylacetic acid (93 mg, 0.9 mmol) was added 1-bromo-4-chloro-2-((3-methoxyphenoxy)methyl)benzene (1 g, 3 mmol) in N,N-dimethylacetamide (14 mL). The reaction was heated to 60° C. under argon for 18 hours. Upon completion, the reaction mixture was cooled to room temperature. The products were loaded directly onto a silica gel packed column and eluted using Hexanes/ethyl acetate to yield 8-chloro-3-methoxy-6H-benzo[c]chromene (739 mg, 98%)

8-chloro-6H-benzo[c]chromen-3-yl trifluoromethanesulfonate: 8-chloro-3-methoxy-6H-benzo[c]chromene (670 mg, 2.7 mmol) and pyridinium hydrochloride (3.16 g, 27.3 mmol) were heated to 185° C. for 2.5 hours. After cooling to room temperature, the reaction was diluted with water extracted into ethyl acetate. The organics were washed with water and brine, dried ($Na_2SO_4$), and concentrated. The crude residue was purified by flash chromatography to yield 8-chloro-6H-benzo[c]chromen-3-ol (523 mg, 82%)

To 8-chloro-6H-benzo[c]chromen-3-ol (798 mg, 3.4 mmol) in dichloromethane (25 mL) at 0° C. was added trifluoromethanesulfonic anhydride (0.36 mL, 4.5 mmol) dropwise, the mixture was stirred for 2 hours, then poured into 1.0M HCl solution (50 mL) extracted into ethyl acetate. The organics were washed with water and brine, dried ($Na_2SO_4$), and concentrated. The crude residue was purified by flash chromatography to yield 8-chloro-6H-benzo[c]chromen-3-yl trifluorome-thanesulfonate (1.16 g, 94%)

2-(8-chloro-6H-benzo[c]chromen-3-yl)-4,4,5,5-tetramethyl-1,3,2-dioxaborolane: A degassed mixture of -chloro-6H-benzo[c]chromen-3-yl trifluorome-thanesulfonate (744 mg, 2 mmol), bis(pinacolato)diboron (785 mg, 3 mmol), potassium acetate (607 mg, 6.2 mmol) and dichloro[1,1'-bis (diphenylphosphino)ferrocene]palladium(II) (75 mg, 0.103 mmol) in 1,4-dioxane (12 mL) was heated to 90° C. for 3 hours, cooled to room temperature and diluted with ethyl acetate. The organics were washed with water and brine, dried ($Na_2SO_4$), and concentrated. The crude residue was purified by flash chromatography to yield 2-(8-chloro-6H-benzo[c]chromen-3-yl)-4,4,5,5-tetramethyl-1,3,2-dioxaborolane (699 mg, 71%)

(S)-tert-butyl 2-(5-(8-chloro-6H-benzo[c]chromen-3-yl)-1H-imidazol-2-yl)pyrrolidine-1-carboxylate To a solution of 2-(8-chloro-6H-benzo[c]chromen-3-yl)-4,4,5,5-tetramethyl-1,3,2-dioxaborolane (773 mg, 2.24 mmol), (S)-tert-butyl 2-(4-bromo-1H-imidazol-2-yl)pyrrolidine-1-carboxylate (886 mg, 2.8 mmol), tetrakis(triphenylphosphine) palladium(0) (65 mg, 0.05 mmol) and dichloro[1,1'-bis (diphenylphosphino)ferrocene]palladium(II) (82 mg, 0.11 mmol) in a mixture of 1,2-dimethoxyethane (10.0 mL) and dimethylformamide (2 mL) was added a solution of potassium carbonate (2M in water, 3.5 mL, 7.0 mmol). The resulting mixture was degassed and then heated to 85° C. under argon for 18 hours. After cooling to room temperature, the reaction was diluted with ethyl acetate. The organics were washed with water and brine, dried ($Na_2SO_4$), and concentrated. The crude residue was purified by flash chromatography to yield (S)-tert-butyl 2-(5-(8-chloro-6H-benzo [c]chromen-3-yl)-1H-imidazol-2-yl) pyrrolidine-1-carboxylate (617 mg, 50%). LCMS-ESI$^+$: calculated for $C_{25}H_{26}ClN_3O_3$: 451.96; observed [M+1]$^+$: 452.53.

(S)-tert-butyl 2-(5-(8-(4,4,5,5-tetramethyl-1,3,2-dioxaborolan-2-yl)-6H-benzo[c]chromen-3-yl)-1H-imidazol-2-yl)pyrrolidine-1-carboxylate: A degassed mixture of (S)-tert-butyl 2-(5-(8-chloro-6H-benzo[c]chromen-3-yl)-1H-imidazol-2-yl) pyrrolidine-1-carboxylate (615 mg, 1.8 mmol), bis(pinacolato)diboron (429 mg, 1.69 mmol), potassium acetate (332 mg, 3.38 mmol), tris(dibenzylideneacetone)palladium (52 mg, 0.06 mmol) and 2-dicyclohexylphosphino-2',4',6'-tri-i-propyl-1,1'-biphenyl (54 mg, 0.11 mmol) in 1,4-dioxane (6 mL) was heated to 90° C. for 5 hours, cooled to room temperature and diluted with ethyl acetate. The organics were washed with water and brine, dried ($Na_2SO_4$), and concentrated. The crude residue was purified by flash chromatography to yield S)-tert-butyl 2-(5-(8-(4,4,5,5-tetramethyl-1,3,2-dioxaborolan-2-yl)-6H-benzo [c]chromen-3-yl)-1H-imidazol-2-yl) pyrrolidine-1-carboxylate (675 mg, 69%). LCMS-ESI$^+$: calculated for $C_{31}H_{38}BN_3O_5$: 543.48; observed [M+1]$^+$: 544.04.

methyl 3-methyl-1-oxo-1-((S)-2-(5-(8-(4,4,5,5-tetramethyl-1,3,2-dioxaborolan-2-yl)-6H-benzo[c]chromen-3-yl)-1H-imidazol-2-yl)pyrrolidin-1-yl)butan-2-ylcarbamate: A solution of (S)-tert-butyl 2-(5-(8-(4,4,5,5-tetramethyl-1,3,2-dioxaborolan-2-yl)-6H-benzo[c]chromen-3-yl)-1H-imidazol-2-yl) pyrrolidine-1-carboxylate (670 mg, 1.23 mmol), ethanol (6 mL) and concentrated HCl (2 mL) was heated to 60° C. for 1.5 hours. The reaction was concentrated and the crude material dissolved in DCM (10 mL). This solution was concentrated and to this material was added a solution of 2-methoxycarbonylamino-3-methylbutyric acid (268 mg, 1.6 mmol) and HATU (537 mg, 1.41 mmol) in DMF (6 mL). To the resulting solution was added diisopropylethylamine (640 μL, 3.68 mmol). After stirring for 18 hours at room temperature, the reaction was diluted with ethyl acetate, washed with water and brine, dried ($Na_2SO_4$), concentrated. The crude residue was purified by flash chromatography to yield methyl 3-methyl-1-oxo-1-((S)-2-(5-(8-(4,4,5,5-tetramethyl-1,3,2-dioxaborolan-2-yl)-6H-benzo[c]chromen-3-yl)-1H-imidazol-2-yl)pyrrolidin-1-yl)butan-2-ylcarbamate (205 mg, 28%). LCMS-ESI$^+$: calculated for $C_{33}H_{41}BN_4O_6$: 600.53; observed [M+1]$^+$: 601.39.

(4S)-tert-butyl3-(6-(3-(2-((S)-1-((S)-2-(methoxycarbonylamino)-3-methylbutanoyl)pyrrolidin-2-yl)-1H-imidazol-5-yl)-6H-benzo[c]chromen-8-yl)-1H-benzo[d]imidazol-2-yl)-2-azabicyclo[2.2.1]heptane-2-carboxylate: To a solution of methyl 3-methyl-1-oxo-1-((S)-2-(5-(8-(4,4,5,5-tetramethyl-1,3,2-dioxaborolan-2-yl)-6H-benzo[c]chromen-3-yl)-1H-imidazol-2-yl)pyrrolidin-1-yl)butan-2-ylcarbamate (196 mg, 0.32 mmol), (1R,3 S,4S)-tert-butyl 3-(6-bromo-1H-benzo[d]imidazol-2-yl)-2-azabicyclo[2.2.1]heptane-2-carboxylate (166 mg, 0.42 mmol), tetrakis(triphenylphosphine) palladium(0) (10 mg, 0.01 mmol) and dichloro[1,1'-bis (diphenylphosphino)ferrocene]palladium(II) (12 mg, 0.02 mmol) in a mixture of 1,2-dimethoxyethane (5 mL) and dimethylformamide (1 mL) was added a solution of potassium carbonate (2M in water, 0.51 mL, 0.31 mmol). The resulting mixture was degassed and then heated to 85° C. under argon for 18 hours. After cooling to room temperature, the reaction was diluted with ethyl acetate. The organics were washed with water and brine, dried ($Na_2SO_4$), and concentrated. The crude residue was purified by flash chromatography to yield S)-tert-butyl 4S)-tert-butyl 3-(6-(3-(2-

((S)-1-((S)-2-(methoxycarbonylamino)-3-methylbutanoyl)pyrrolidin-2-yl)-1H-imidazol-5-yl)-6H-benzo[c]chromen-8-yl)-1H-benzo[d]imidazol-2-yl)-2-azabicyclo[2.2.1]heptane-2-carboxylate (215 mg, 85%) LCMS-ESI+: calculated for $C_{45}H_{51}N_7O_6$: 785.95; observed [M+1]+: 786.43.

methyl (1R)-2-((4S)-3-methyl-3-(6-(3-(2-((methoxycarbonylamino)-3-methylbutanoyl))-pyrrolidin-2-yl)-1H-imidazol-5-yl)-6H-benzo[c]chromen-8-yl)-1H-benzo[d]imidazol-2-yl)-2-azabicyclo[2.2.1]heptan-2-yl)-2-oxo-1-phenylethylcarbamate: A solution yield S)-tert-butyl 4 S)-tert-butyl 3-(6-(3-(2-((S)-1-((S)-2-(methoxycarbonylamino)-3-methylbutanoyl)pyrrolidin-2-yl)-1H-imidazol-5-yl)-6H-benzo[c]chromen-8-yl)-1H-benzo[d]imidazol-2-yl)-2-azabicyclo[2.2.1]heptane-2-carboxylate (213 mg, 0.27 mmol), ethanol (3 mL) and concentrated HCl (1 mL) was heated to 60° C. for 1.5 hours. The reaction was concentrated and the crude material dissolved in DCM (6 mL). This solution was concentrated and to this material was added a solution of (R)-2-(methoxycarbonylamino)-2-phenylacetic acid (73 mg, 0.35 mmol) and COMU (132 mg, 0.31 mmol) in DMF (3 mL). To the resulting solution was added diisopropylethylamine (140 µL, 0.81 mmol). After stirring for 18 hours at room temperature, the reaction was diluted with ethyl acetate, washed with water and brine, dried ($Na_2SO_4$), concentrated and purified by preparative reverse phase HPLC (Gemini, 15 to 50% $ACN/H_2O$+0.1% TFA). The product fractions were lyophilized to give methyl (1R)-2-((4S)-3-methyl-3-(6-(3-(2-((methoxycarbonylamino)-3-methylbutanoyl))-pyrrolidin-2-yl)-1H-imidazol-5-yl)-6H-benzo[c]chromen-8-yl)-1H-benzo[d]imidazol-2-yl)-2-azabicyclo[2.2.1]heptan-2-yl)-2-oxo-1-phenylethylcarbamate (34 mg, 14%). LCMS-ESI+: calculated for $C_{50}H_{52}N_8O_7$: 877.02; observed [M+1]+: 877.80.

Example BM

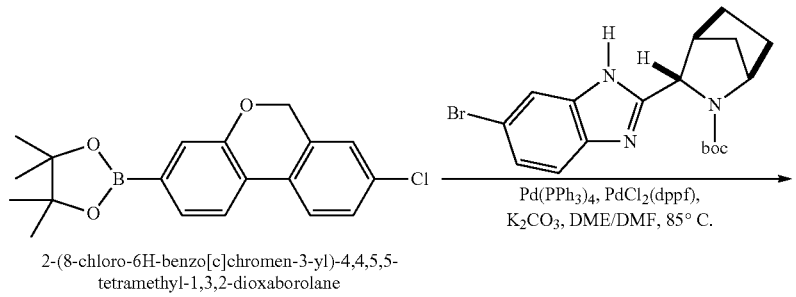

2-(8-chloro-6H-benzo[c]chromen-3-yl)-4,4,5,5-tetramethyl-1,3,2-dioxaborolane

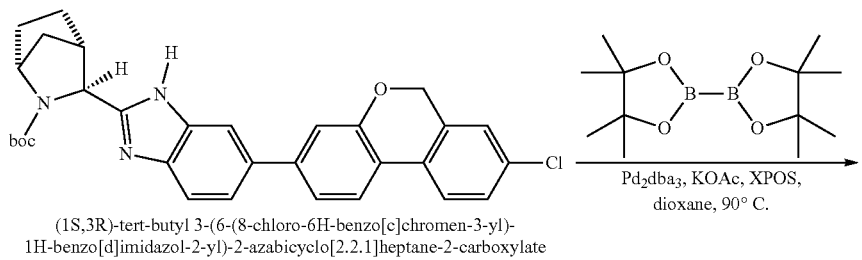

(1S,3R)-tert-butyl 3-(6-(8-chloro-6H-benzo[c]chromen-3-yl)-1H-benzo[d]imidazol-2-yl)-2-azabicyclo[2.2.1]heptane-2-carboxylate

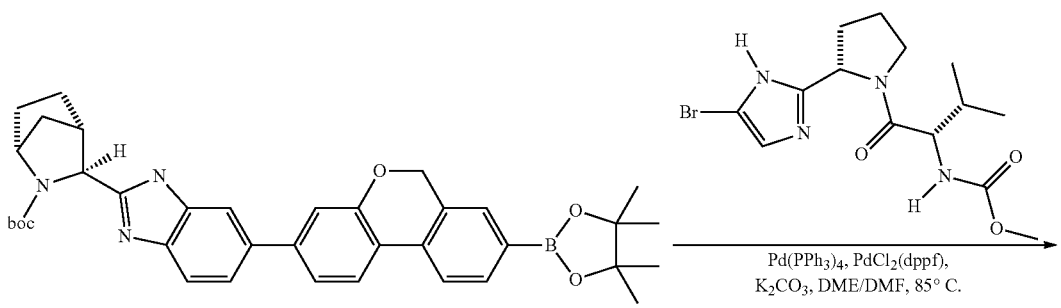

(1S,3R)-tert-butyl 3-(6-(8-(4,4,5,5-tetramethyl-1,3,2-dioxaborolan-2-yl)-6H-benzo[c]chromen-3-yl)-1H-benzo[d]imidazol-2-yl)-2-azabicyclo[2.2.1]heptane-2-carboxylate

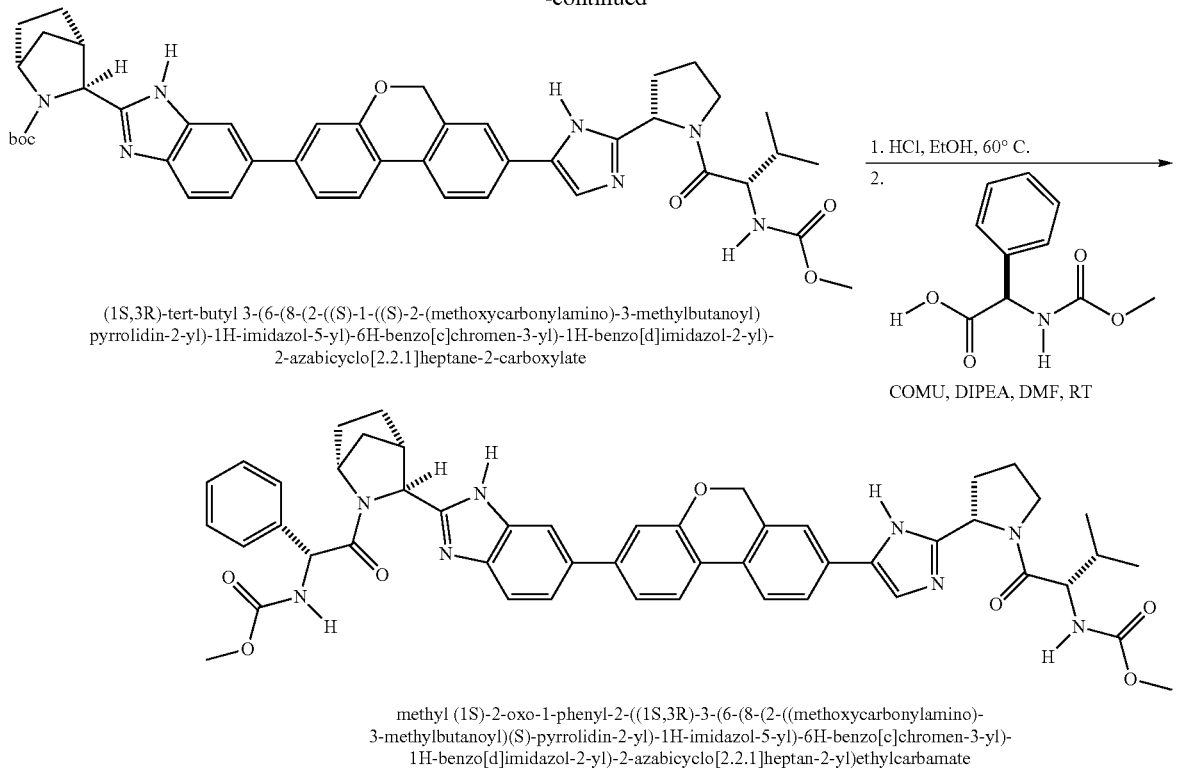

(1S,3R)-tert-butyl 3-(6-(8-(2-((S)-1-((S)-2-(methoxycarbonylamino)-3-methylbutanoyl)pyrrolidin-2-yl)-1H-imidazol-5-yl)-6H-benzo[c]chromen-3-yl)-1H-benzo[d]imidazol-2-yl)-2-azabicyclo[2.2.1]heptane-2-carboxylate 1. HCl, EtOH, 60° C.
2.

COMU, DIPEA, DMF, RT methyl (1S)-2-oxo-1-phenyl-2-((1S,3R)-3-(6-(8-(2-((methoxycarbonylamino)-3-methylbutanoyl)(S)-pyrrolidin-2-yl)-1H-imidazol-5-yl)-6H-benzo[c]chromen-3-yl)-1H-benzo[d]imidazol-2-yl)-2-azabicyclo[2.2.1]heptan-2-yl)ethylcarbamate (1 S,3 1R)-tert-butyl 3-(6-(8-chloro-6H-benzo[c]chromen-3-yl)-1H-benzo[d]imidazol-2-yl)-2-azabicyclo[2.2.1]heptane-2-carboxylate: To a solution of 2-(8-chloro-6H-benzo[c]chromen-3-yl)-4,4,5,5-tetramethyl-1,3,2-dioxaborolane (750 mg, 2.18 mmol), (1R,3 S,4S)-tert-butyl 3-(6-bromo-1H-benzo[d]imidazol-2-yl)-2-azabicyclo[2.2.1]heptane-2-carboxylate (1.07 mg, 2.72 mmol), tetrakis(triphenylphosphine) palladium(0) (75 mg, 0.07 mmol) and dichloro[1,1'-bis(diphenylphosphino)ferrocene]palladium (II) (96 mg, 0.13 mmol) in a mixture of 1,2-dimethoxyethane (10 mL) and dimethylformamide (2 mL) was added a solution of potassium carbonate (2M in water, 3.5 mL, 6.53 mmol). The resulting mixture was degassed and then heated to 85° C. under argon for 18 hours. After cooling to room temperature, the reaction was diluted with ethyl acetate. The organics were washed with water and brine, dried ($Na_2SO_4$), and concentrated. The crude residue was purified by flash chromatography to yield (1S,3R)-tert-butyl 3-(6-(8-chloro-6H-benzo[c]chromen-3-yl)-1H-benzo[d]imidazol-2-yl)-2-azabicyclo[2.2.1]heptane-2-carboxylate (285 mg, 25%) LCMS-ESI$^+$: calculated for $C_{31}H_{30}ClN_3O_3$: 528.06; observed [M+1]$^+$: 528.36.

(1S,3R)-tert-butyl 3-(6-(8-(4,4,5,5-tetramethyl-1,3,2-dioxaborolan-2-yl)-6H-benzo[c]chromen-3-yl)-1H-benzo[d]imidazol-2-yl)-2-azabicyclo[2.2.1]heptane-2-carboxylate: A degassed mixture of (1S,3R)-tert-butyl 3-(6-(8-chloro-6H-benzo[c]chromen-3-yl)-1H-benzo[d]imidazol-2-yl)-2-azabicyclo[2.2.1]heptane-2-carboxylate (282 mg, 0.53 mmol), bis(pinacolato)diboron (202 mg, 0.8 mmol), potassium acetate (156 mg, 1.6 mmol), tris(dibenzylideneacetone)palladium (24 mg, 0.03 mmol) and 2-dicyclohexylphosphino-2',4',6'-tri-i-propyl-1,1'-biphenyl (25 mg, 0.05 mmol) in 1,4-dioxane (5 mL) was heated to 90° C. for 2.5 hours, cooled to room temperature and diluted with ethyl acetate. The organics were washed with water and brine, dried ($Na_2SO_4$), and concentrated. The crude residue was purified by flash chromatography to yield (1S,3R)-tert-butyl 3-(6-(8-(4,4,5,5-tetramethyl-1,3,2-dioxaborolan-2-yl)-6H-benzo[c]chromen-3-yl)-1H-benzo[d]imidazol-2-yl)-2-azabi-cyclo[2.2.1]heptane-2-carboxylate (278 mg, 84%) LCMS-ESI$^+$: calculated for $C_{37}H_{42}BN_3O_5$: 619.58; observed [M+1]$^+$: 620.14.

(1S,3R)-tert-butyl 3-(6-(8-(2-((S)-1-((S)-2-(methoxycarbonylamino)-3-methylbutanoyl) pyrrolidin-2-yl)-1H-imidazol-5-yl)-6H-benzo[c]chromen-3-yl)-1H-benzo[d]imidazol-2-yl)-2-azabicyclo[2.2.1]heptane-2-carboxylate: To a solution of (1S,3R)-tert-butyl 3-(6-(8-(4,4,5,5-tetramethyl-1,3,2-dioxaborolan-2-yl)-6H-benzo[c]chromen-3-yl)-1H-benzo[d]imidazol-2-yl)-2-azabi-cyclo[2.2.1]heptane-2-carboxylate (275 mg, 0.44 mmol), methyl (S)-1-((S)-2-(5-bromo-1H-imidazol-2-yl)pyrrolidin-1-yl)-3-methyl-1-oxobutan-2-ylcarbamate (221 mg, 0.55 mmol), tetrakis(triphenylphosphine) palladium(0) (20 mg, 0.02 mmol) and dichloro[1,1'-bis(diphenylphosphino) ferrocene]palladium (II) (26 mg, 0.04 mmol) in a mixture of 1,2-dimethoxyethane (5.0 mL) and dimethylformamide (1 mL) was added a solution of potassium carbonate (2M in water, 0.7 mL, 1.3 mmol). The resulting mixture was degassed and then heated to 85° C. under argon for 18 hours. After cooling to room temperature, the reaction was diluted with ethyl acetate. The organics were washed with water and brine, dried ($Na_2SO_4$), and concentrated. The crude residue was purified by flash chromatography to yield (1S,3R)-tert-butyl 3-(6-(8-(2-((S)-1-((S)-2-(methoxycarbonylamino)-3-methyl-butanoyl) pyrrolidin-2-yl)-1H-imidazol-5-yl)-6H-benzo[c]chromen-3-yl)-1H-benzo[d]imidazol-2-yl)-2-azabicyclo[2.2.1]heptane-2-carboxylate (70 mg, 20%). LCMS-ESI$^+$: calculated for $C_{45}H_{51}N_7O_6$: 785.95; observed [M+1]$^+$: 786.85.

methyl (1S)-2-oxo-1-phenyl-2-((1S,3R)-3-(6-(8-(2-((methoxycarbonylamino)-3-methylbutanoyl)(S)-pyrrolidin-2-yl)-1H-imidazol-5-yl)-6H-benzo[c]chromen-3-yl)-1H-benzo[d]imidazol-2-yl)-2-azabicyclo[2.2.1]heptan-2-yl)ethylcarbamate: A solution yield (1S,3R)-tert-butyl 3-(6-(8-(2-((S)-1-((S)-2-(methoxycarbonylamino)-3-methylbutanoyl) pyrrolidin-2-yl)-1H-imidazol-5-yl)-6H-benzo[c]chromen-3-yl)-1H-benzo[d]imidazol-2-yl)-2-azabicyclo[2.2.1]heptane-2-carboxylate (70 mg, 0.08 mmol), ethanol (3 mL) and concentrated HCl (1 mL) was heated to 60° C. for 1.5 hours. The reaction was concentrated and the crude material dissolved in DCM (6 mL). This solution was concentrated and to this material was added a solution of (R)-2-(methoxycarbonylamino)-2-phenylacetic acid (48 mg, 0.23 mmol) and COMU (88 mg, 0.20 mmol) in DMF (3 mL). To the resulting solution was added diisopropylethylamine (0.54 mmol). After stirring for 18 hours at room temperature, the reaction was diluted with ethyl acetate, washed with water and brine, dried ($Na_2SO_4$), concentrated and purified by preparative reverse phase HPLC (Gemini, 15 to 50% ACN/$H_2O$+0.1% TFA). The product fractions were lyophilized to give methyl (1S)-2-oxo-1-phenyl-2-((1S,3R)-3-(6-(8-(2-((methoxycarbonylamino)-3-methylbutanoyl)(S)-pyrro-lidin-2-yl)-1H-imidazol-5-yl)-6H-benzo[c]chromen-3-yl)-1H-benzo[d]imidazol-2-yl)-2-azabicyclo[2.2.1]heptan-2-yl)ethylcarbamate (4.8 mg, 6%). LCMS-ESI$^+$: calculated for $C_{50}H_{52}N_8O_7$: 877.02; observed [M+1]$^+$: 877.72.

Example BN

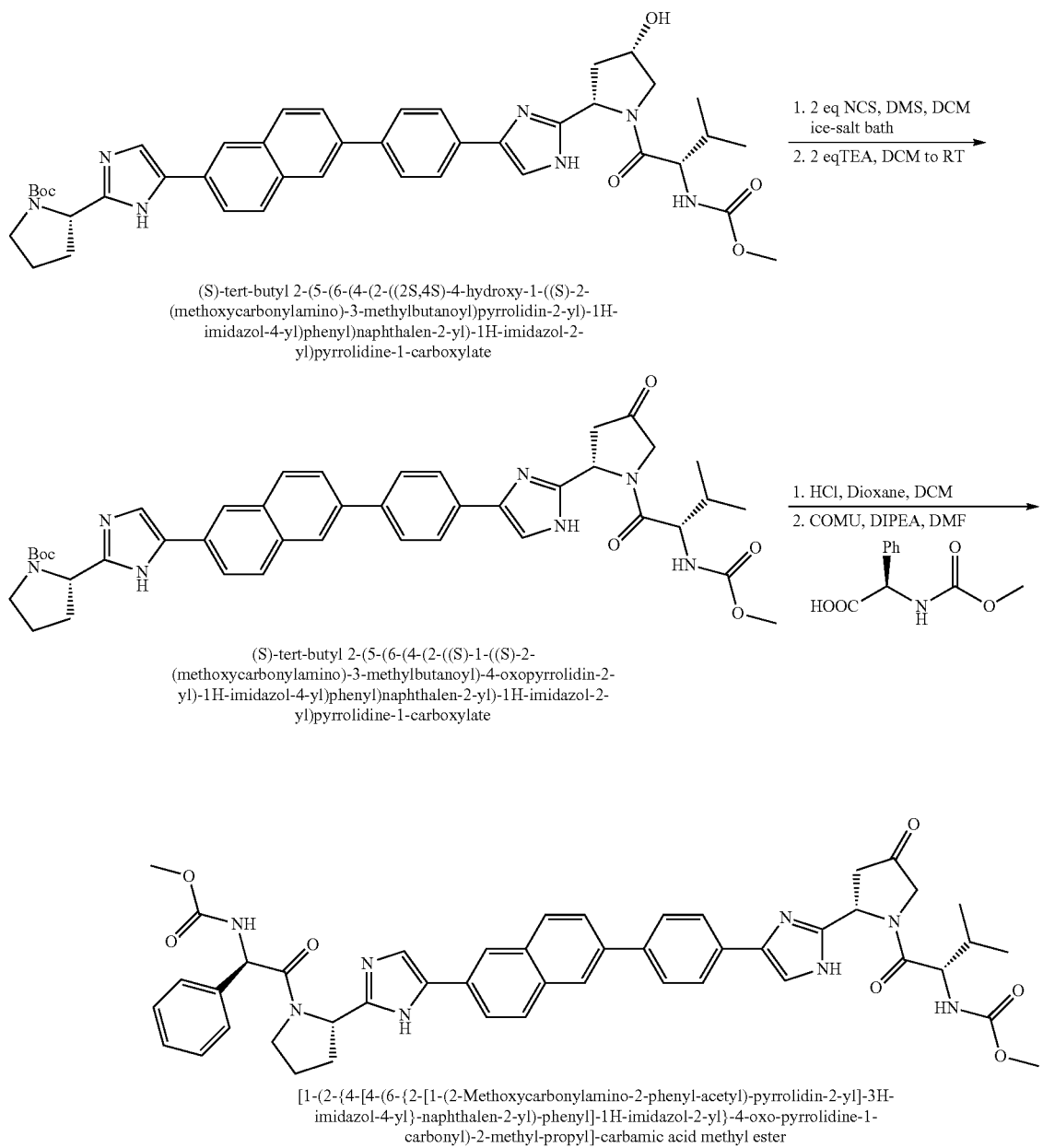

(S)-tert-butyl 2-(5-(6-(4-(2-((2S,4S)-4-hydroxy-1-((S)-2-(methoxycarbonylamino)-3-methylbutanoyl)pyrrolidin-2-yl)-1H-imidazol-4-yl)phenyl)naphthalen-2-yl)-1H-imidazol-2-yl)pyrrolidine-1-carboxylate (S)-tert-butyl 2-(5-(6-(4-(2-((S)-1-((S)-2-(methoxycarbonylamino)-3-methylbutanoyl)-4-oxopyrrolidin-2-yl)-1H-imidazol-4-yl)phenyl)naphthalen-2-yl)-1H-imidazol-2-yl)pyrrolidine-1-carboxylate

[1-(2-{4-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-4-oxo-pyrrolidine-1-carbonyl)-2-methyl-propyl]-carbamic acid methyl ester (S)-tert-butyl 2-(5-(6-(4-(2-((2S,4S)-4-hydroxy-1-((S)-2-(methoxycarbonylamino)-3-methylbutanoyl)pyrrolidin-2-yl)-1H-imidazol-4-yl)phenyl)naphthalen-2-yl)-1H-imidazol-2-yl)pyrrolidine-1-carboxylate. (S)-tert-butyl 2-(5-(6-(4-(2-((2S,4S)-4-hydroxy-1-((S)-2-(methoxycarbonylamino)-3-methylbutanoyl)pyrrolidin-2-yl)-1H-imidazol-4-yl)phenyl)naphthalen-2-yl)-1H-imidazol-2-yl)pyrrolidine-1-carboxylate was prepared following the procedure for 2-{5-[6-(4-{2-[1-(2-Methoxy-carbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester (Example EQ), substituting 4-Hydroxy-pyrrolidine-1,2-dicarboxylic acid 1-tert-butyl ester for Pyrrolidine-1,2-dicarboxylic acid 1-tert-butyl ester.

(S)-tert-Butyl 2-(5-(6-(4-(2-((S)-1-((S)-2-(methoxycarbonylamino)-3-methylbutanoyl)-4-oxopyrrolidin-2-yl)-1H-imidazol-4-yl)phenyl)naphthalen-2-yl)-1H-imidazol-2-yl)pyrrolidine-1-carboxylate: Dimethyl sulfide (164 μL, 2.23 mmol) was added dropwise to a solution of N-chlorosuccinimide (238 mg, 2.12 mmol) in dichloromethane (10 mL) at 0° C. After 15 minutes the mixture was cooled to −15° C. (ice-salt bath). A solution of (S)-tert-butyl 2-(5-(6-(4-(2-((2S,4S)-4-hydroxy-1-((S)-2-(methoxycarbonylamino)-3-methylbutanoyl)pyrrolidin-2-yl)-1H-imidazol-4-yl)phenyl)naphthalen-2-yl)-1H-imidazol-2-yl)pyrrolidine-1-carboxylate (809 mg, 1.06 mmol) in dichloromethane (5 mL) was added dropwise. The temperature was not allowed to go above −10° C. After 2 hours a solution of triethylamine (316 μL, 2.23 mmol) in dichloromethane (2 mL) was added dropwise and the mixture was allowed to warm to room temperature at which point the reaction was complete. The mixture was washed with saturated ammonium chloride (3×10 mL), dried over sodium sulfate and filtered. The solvent was removed under reduced pressure and the residue was subjected to flash chromatography with eluent of (10% methanol in ethyl acetate) and hexane. The product containing fractions were combined and the solvent was removed under reduced pressure to yield (S)-tert-butyl 2-(5-(6-(4-(2-((S)-1-((S)-2-(methoxycarbonylamino)-3-methylbutanoyl)-4-oxopyrrolidin-2-yl)-1H-imidazol-4-yl)phenyl)naphthalen-2-yl)-1H-imidazol-2-yl)pyrrolidine-1-carboxylate (734 mg, 0.96 mmol, 90%).

[1-(2-{4-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-4-oxo-pyrrolidine-1-carbonyl)-2-methyl-propyl]-carbamic acid methyl ester: A solution of (S)-tert-butyl 2-(5-(6-(4-(2-((S)-1-((S)-2-(methoxycarbonylamino)-3-methylbutanoyl)-4-oxopyrrolidin-2-yl)-1H-imidazol-4-yl)phenyl)naphthalen-2-yl)-1H-imidazol-2-yl)pyrrolidine-1-carboxylate (367 mg, 0.49 mmol) in dichloromethane (10 mL) was treated with a solution of hydrogen chloride in dioxane (4 N, 10 mL). After 1 hour the solvent was removed under reduced pressure and placed on high vacuum for 30 min. The solid was taken up in N,N-dimethylformamide (2 mL) and N-methylmorpholine (136 μL, 1.23 mmol) was added to the solution. In a separate vessel, COMU (232 mg, 0.541 mmol), and N-methylmorpholine (136 μL, 1.23 mmol) were added to a solution of (R)-2-(methoxycarbonylamino)-2-phenylacetic acid (113 mg, 0.541 mmol) in dichloromethane (2 mL). This was stirred for 5 minutes and both solutions were combined. After 15 minutes the mixture was neutralized with trifluoroacetic acid and the solvent was removed under reduced pressure. The resulting DMF solution was subject to reverse phase HPLC with eluant of acetonitrile eluent of 0.1% TFA in water and 0.1% TFA in acetonitrile. The product containing fractions were combined and the solvent was removed by lyopholization to provide [1-(2-{4-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-4-oxo-pyrrolidine-1-carbonyl)-2-methyl-propyl]-carbamic acid methyl ester (121 mg, 0.14 mmol, 28%). $C_{47}H_{48}N_8O_7$ calculated 836.3 observed $[M+1]^+$ 837.4; rt=1.71 min.

Example BO

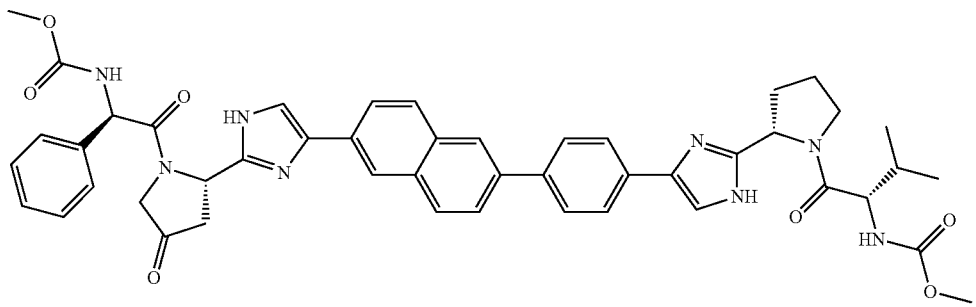

[1-(2-{4-[4-(6-{2-[1-(2-Methoxycarbonylamino-2-phenyl-acetyl)-4-oxo-pyrrolidin-2-yl]-1H-imidazol-4-yl}-naphthalen-2-yl)-phenyl]-1H-imidazol-2-yl}-pyrrolidine-1-carbonyl)-2-methyl-propyl]-carbamic acid methyl ester: [1-(2-{4-[4-(6-{2-[1-(2-Methoxycarbonylamino-2-phenyl-acetyl)-4-oxo-pyrrolidin-2-yl]-1H-imidazol-4-yl}-naphthalen-2-yl)-phenyl]-1H-imidazol-2-yl}-pyrrolidine-1-carbonyl)-2-methyl-propyl]-carbamic acid methyl ester was prepared following Example BN substituting (2S,4S)-tert-butyl 4-hydroxy-2-(4-(6-(4-(2-((S)-1-((S)-2-(methoxycarbonylamino)-3-methylbutanoyl)pyrrolidin-2-yl)-1H-imidazol-4-yl)phenyl)naphthalen-2-yl)-1H-imidazol-2-yl)pyrrolidine-1-carboxylate for (S)-tert-butyl 2-(5-(6-(4-(2-((2S,4S)-4-hydroxy-1-((S)-2-(methoxycarbonylamino)-3-methylbutanoyl)pyrrolidin-2-yl)-1H-imidazol-4-yl)phenyl)naphthalen-2-yl)-1H-imidazol-2-yl)pyrrolidine-1-carboxylate. $C_{47}H_{48}N_8O_7$ calculated 836.3 observed $[M+1]^+$ 837.4; rt=1.68 min.

Example BP

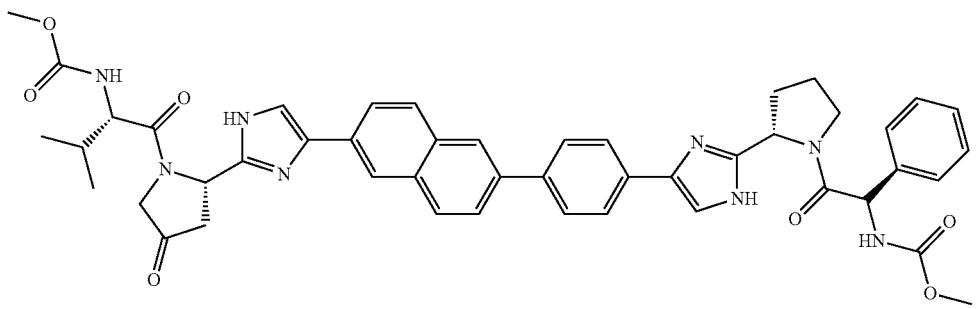

[1-(2-{4-[6-(4-{2-[1-(2-Methoxycarbonylamino-2-phenyl-acetyl)-pyrrolidin-2-yl]-1H-imidazol-4-yl}-phenyl)-naphthalen-2-yl]-1H-imidazol-2-yl}-4-oxo-pyrrolidine-1-carbonyl)-2-methyl-propyl]-carbamic acid methyl ester: [1-(2-{4-[6-(4-{2-[1-(2-Methoxycarbonylamino-2-phenyl-acetyl)-pyrrolidin-2-yl]-1H-imidazol-4-yl}-phenyl)-naphthalen-2-yl]-1H-imidazol-2-yl}-4-oxo-pyrrolidine-1-carbonyl)-2-methyl-propyl]-carbamic acid methyl ester was prepared following Example BN substituting (S)-tert-butyl 2-(4-(4-(6-(2-((2S,4S)-4-hydroxy-1-((S)-2-(methoxycarbonylamino)-3-methylbutanoyl)pyrrolidin-2-yl)-1H-imidazol-4-yl)naphthalen-2-yl)phenyl)-1H-imidazol-2-yl)pyrrolidine-1-carboxylate for (S)-tert-butyl 2-(5-(6-(4-(2-((2S,4S)-4-hydroxy-1-((S)-2-(methoxycarbonylamino)-3-methylbutanoyl)pyrrolidin-2-yl)-1H-imidazol-4-yl)phenyl)naphthalen-2-yl)-1H-imidazol-2-yl)pyrrolidine-1-carboxylate. $C_{47}H_{48}N_8O_7$ calculated 836.3 observed $[M+1]^+$ 837.5; rt=1.70 min.

Example BQ

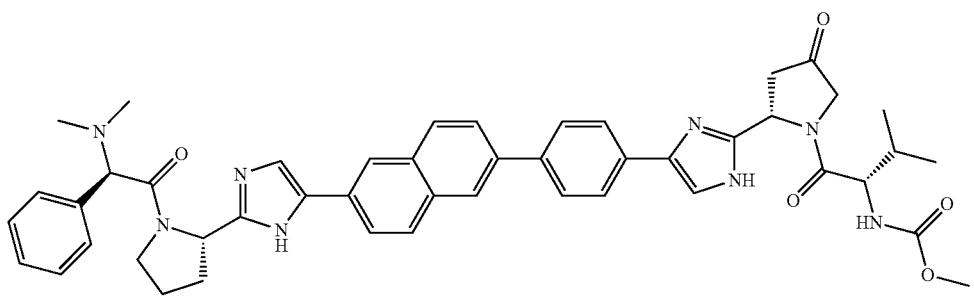 [SMILES: COC(=O)N[C@H](C(=O)N1CC(=O)C[C@H]1c1nc(-c2ccc(-c3ccc4cc(-c5cnc([C@@H]6CCCN6C(=O)[C@@H](c6ccccc6)N(C)C)[nH]5)ccc4c3)cc2)c[nH]1)C(C)C]

[1-(2-{4-[4-(6-{2-[1-(2-Dimethylamino-2-phenyl-acetyl)-pyrrolidin-2-yl]-3H-imidazol-4-yl}-naphthalen-2-yl)-phenyl]-1H-imidazol-2-yl}-4-oxo-pyrrolidine-1-carbonyl)-2-methyl-propyl]-carbamic acid methyl ester: [1-(2-{4-[4-(6-{2-[1-(2-Dimethylamino-2-phenyl-acetyl)-pyrrolidin-2-yl]-3H-imidazol-4-yl}-naphthalen-2-yl)-phenyl]-1H-imidazol-2-yl}-4-oxo-pyrrolidine-1-carbonyl)-2-methyl-propyl]-carbamic acid methyl ester was prepared following Example BN substituting (R)-2-(dimethylamino)-2-phenylacetic acid for (R)-2-(methoxycarbonylamino)-2-phenylacetic acid. $C_{47}H_{50}N_8O_5$ calculated 806.4 observed $[M+1]^+$ 807.4; rt=1.51 min.

Example BR

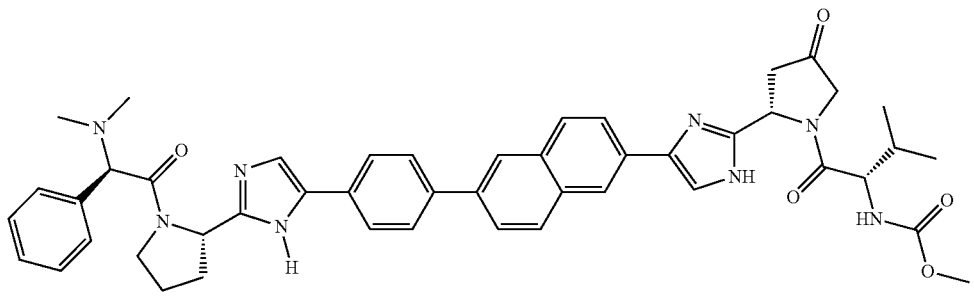 [SMILES: COC(=O)N[C@H](C(=O)N1CC(=O)C[C@H]1c1nc(-c2ccc3cc(-c4ccc(-c5cnc([C@@H]6CCCN6C(=O)[C@@H](c6ccccc6)N(C)C)[nH]5)cc4)ccc3c2)c[nH]1)C(C)C]

[1-(2-{4-[6-(4-{2-[1-(2-Dimethylamino-2-phenyl-acetyl)-pyrrolidin-2-yl]-3H-imidazol-4-yl}-phenyl)-naphthalen-2-yl]-1H-imidazol-2-yl}-4-oxo-pyrrolidine-1-carbonyl)-2-methyl-propyl]-carbamic acid methyl ester: [1-(2-{4-[6-(4-{2-[1-(2-Dimethylamino-2-phenyl-acetyl)-pyrrolidin-2-yl]-3H-imidazol-4-yl}-phenyl)-naphthalen-2-yl]-1H-imidazol-2-yl}-4-oxo-pyrrolidine-1-carbonyl)-2-methyl-propyl]-carbamic acid methyl ester was prepared following Example BN substituting (R)-2-(dimethylamino)-2-phenyl-lacetic acid for (R)-2-(methoxycarbonylamino)-2-phenyl-lacetic acid and (S)-tert-butyl 2-(5-(4-(6-(2-((2S,4S)-4-hydroxy-1-((S)-2-(methoxycarbonylamino)-3-methylbutanoyl)pyrrolidin-2-yl)-1H-imidazol-4-yl)naphthalen-2-yl)phenyl)-1H-imidazol-2-yl)pyrrolidine-1-carboxylate for (S)-tert-butyl 2-(5-(6-(4-(2-((2S,4S)-4-hydroxy-1-((S)-2-(methoxycarbonylamino)-3-methylbutanoyl)pyrrolidin-2-yl)-1H-imidazol-4-yl)phenyl)naphthalen-2-yl)-1H-imidazol-2-yl)pyrrolidine-1-carboxylate. $C_{47}H_{50}N_8O_5$ calculated 806.4 observed [M+1]$^+$ 807.3; rt=1.55 min.

Example BS

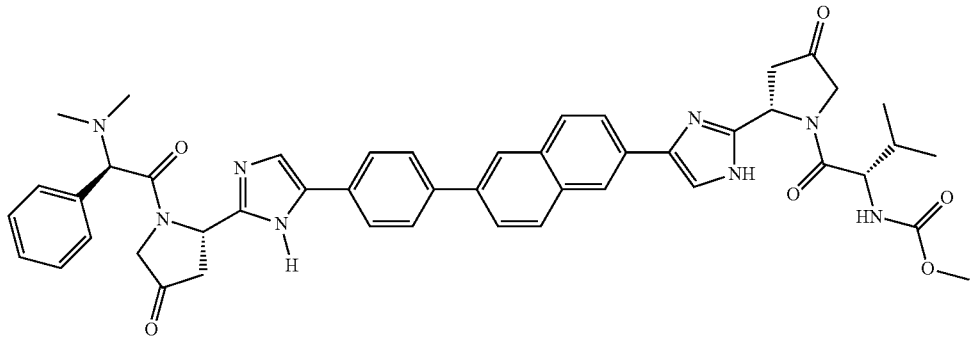 [SMILES: COC(=O)N[C@H](C(=O)N1CC(=O)C[C@H]1c1nc(-c2ccc3cc(-c4ccc(-c5cnc([C@@H]6CC(=O)CN6C(=O)[C@@H](c6ccccc6)N(C)C)[nH]5)cc4)ccc3c2)c[nH]1)C(C)C]

[1-(2-{4-[6-(4-{2-[1-(2-Dimethylamino-2-phenyl-acetyl)-4-oxo-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: [1-(2-{4-[6-(4-{2-[1-(2-Dimethylamino-2-phenyl-acetyl)-4-oxo-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester was prepared following Example BN substituting (R)-2-(dimethylamino)-2-phenyl-lacetic acid for (R)-2-(methoxycarbonylamino)-2-phenyl-lacetic acid and (2S,4S)-tert-butyl 4-hydroxy-2-(5-(4-(6-(2-((S)-1-((S)-2-(methoxycarbonylamino)-3-methylbutanoyl)pyrrolidin-2-yl)-1H-imidazol-4-yl)naphthalen-2-yl)phenyl)-1H-imidazol-2-yl)pyrrolidine-1-carboxylate for (S)-tert-butyl 2-(5-(6-(4-(2-((2S,4S)-4-hydroxy-1-((S)-2-(methoxycarbonylamino)-3-methylbutanoyl)pyrrolidin-2-yl)-1H-imidazol-4-yl)phenyl)naphthalen-2-yl)-1H-imidazol-2-yl)pyrrolidine-1-carboxylate. $C_{47}H_{50}N_8O_5$ calculated 806.4 observed [M+1]$^+$ 807.3; rt=1.53 min.

Example BT

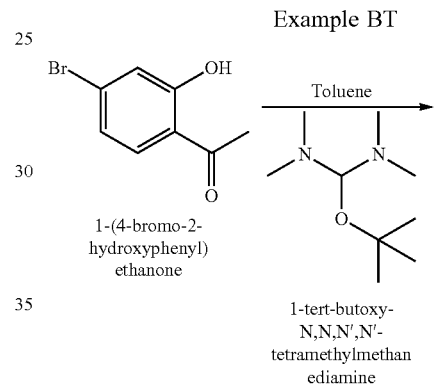

1-(4-bromo-2-hydroxyphenyl)ethanone 1-tert-butoxy-N,N,N',N'-tetramethylmethanediamine -continued

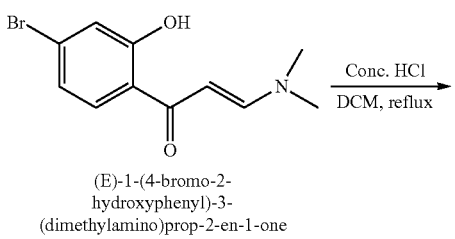

(E)-1-(4-bromo-2-hydroxyphenyl)-3-(dimethylamino)prop-2-en-1-one

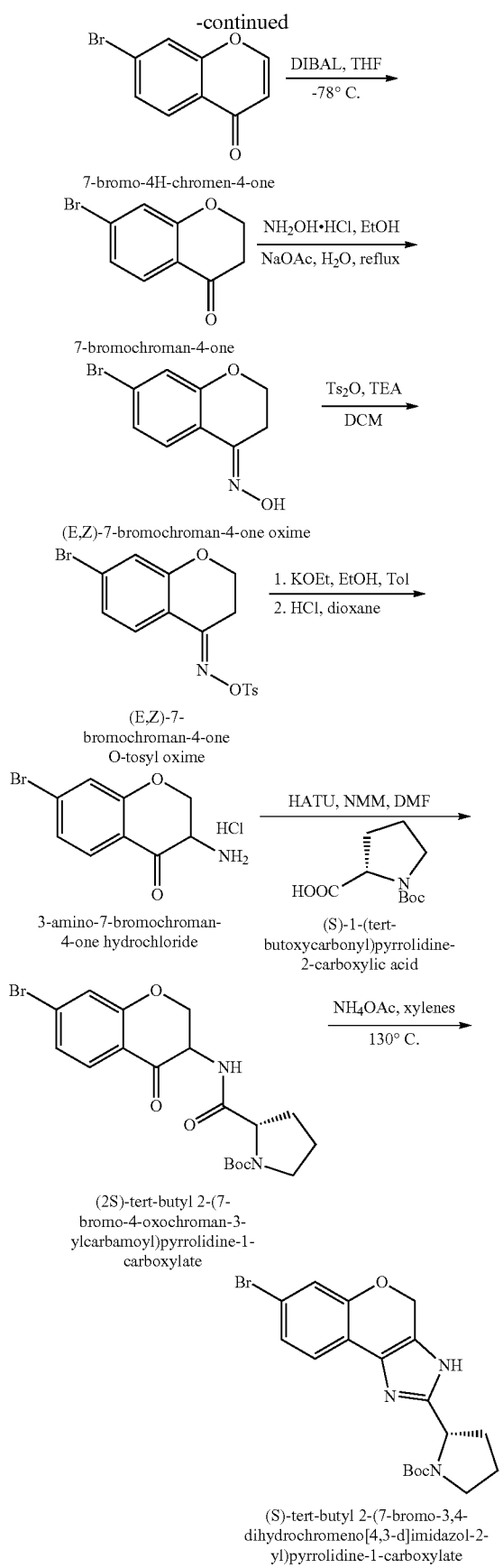

(E)-1-(4-Bromo-2-hydroxyphenyl)-3-(dimethylamino)prop-2-en-1-one: A solution of 1-tert-Butoxy-N,N,N',N'-tetramethylmethanediamine (19.2 mL, 93.0 mmol) and solution of 1-(4-bromo-2-hydroxyphenyl)ethanone (10 g, 46.5 mmol) in toluene (100 mL) was heated at 35° C. for 16 hours and at 80° C. for 1 hour. The solvent was removed under reduced pressure. The resulting solid was subjected to flash chromatography with eluant of dichloromethane. The product containing fractions were combined and the solvent was removed under reduced pressure to provide (E)-1-(4-bromo-2-hydroxyphenyl)-3-(dimethylamino)prop-2-en-1-one (10.4 g, 38.5 mmol, 82%).

7-Bromo-4H-chromen-4-one: A solution of concentrated hydrochloric acid (30 mL) was added to a solution of (E)-1-(4-bromo-2-hydroxyphenyl)-3-(dimethylamino)prop-2-en-1-one (10.4 g, 38.5 mmol) in dichloromethane (250 mL). The mixture was heated at reflux for 30 minutes and cooled to room temperature. The aqueous phase was extracted with dichloromethane (20 mL). The combined organic phases were washed with saturated sodium bicarbonate (50 mL), dried over sodium sulfate and filtered. The solvent was removed under reduced pressure to yield 7-bromo-4H-chromen-4-one (8.7 g, 38.5 mol, 100%).

7-Bromochroman-4-one: A solution of diisobutylaluminum hydride in heptane (1.0 M, 60 mL, 60.0 mmol) was added dropwise to a solution of 7-bromo-4H-chromen-4-one (4.5 g, 20.0 mmol) in tetrahydrofuran at −78° C. under an atmosphere of argon over a period of 30 minutes. After 30 minutes the reaction was quenched with a mixture of silica gel (10 g), and water (10 mL). The mixture was allowed to warm to room temperature and was filter through celite and the tetrahydrofuran was removed under reduced pressure. The residue was taken up in chloroform (100 mL) and washed with sodium hydroxide (1N, 25 mL) and dried over sodium sulfate. The mixture was filtered and the solvent was removed under reduced pressure. The residue was subjected to flash chromatography with eluant of dichloromethane. The product containing fractions were combined and the solvent was removed under reduced pressure to provide 7-bromochroman-4-one (3.57 g, 15.7 mmol, 78%).

(E,Z)-7-Bromochroman-4-one oxime: A solution of sodium acetate (3.86 g, 47.2 mmol) in water (30 mL) was added to a solution of 7-bromochroman-4-one (3.57 g, 15.7 mmol), and hydroxylamine hydrochloride (1.64 g, 23.5 mmol) in ethanol (70 mL). The mixture was heated at reflux for 15 minutes. The mixture was cooled to room temperature and diluted with water (50 mL). The resulting solid was isolated by filtration, washed with water (50 mL) and azeotroped with toluene to provide (E,Z)-7-bromochroman-4-one oxime (3.5 g, 14.5 mmol, 92%).

(E,Z)-7-Bromochroman-4-one O-tosyl oxime: p-Toluenesulfonic anhydride (5.19 g, 15.9 mmol) was added to a solution of E,Z)-7-bromochroman-4-one oxime (3.5 g, 14.5 mmol), and triethylamine (2.42 mL, 17.4 mmol) in dichloromethane (125 mL). After 1 hour the mixture was washed with water (3×20 mL), brine (20 mL), dried over sodium sulfate and filtered. The solvent was removed under reduced pressure to provide (E,Z)-7-bromochroman-4-one O-tosyl oxime (5.5 g, 14.3 mmol, 98%).

3-Amino-7-bromochroman-4-one hydrochloride: A solution of potassium ethoxide in ethanol (24% wt, 5.3 mL, 15.1 mmol) and then water (1 mL) were added to a solution of (E,Z)-7-bromochroman-4-one O-tosyl oxime (5.5 g, 14.3 mmol) in toluene (60 mL) and ethanol (30 mL). After 16 hours a solution of hydrogen chloride in dioxane (4 N, 20 mL) was added and the solvent was removed under reduced pressure. The residue was stirred with diethyl ether (50 mL).

The resulting solid was isolated by filtration to provide 3-amino-7-bromochroman-4-one hydrochloride (2.5 g, 8.9 mmol, 62%).

(2S)-tert-butyl 2-(7-bromo-4-oxochroman-3-ylcarbamoyl)pyrrolidine-1-carboxylate: N-Methylmorpholine (2.14 mL, 19.4 mmol) was added to a mixture of (S)-1-(tert-butoxycarbonyl)pyrrolidine-2-carboxylic acid (1.93 g, 8.98 mmol) and 2-(1H-7-Azabenzotriazol-1-yl)-1,1,3,3-tetramethyluronium hexafluorophosphate (3.41 g, 8.98 mmol), in N,N-dimethylformamide (6 mL). After 5 min solution of 3-amino-7-bromochroman-4-one hydrochloride (2.5 g, 8.9 mmol) and N-methylmorpholine (2.14 mL, 19.4 mmol) in N,N-dimethylformamide (6 mL) was added. After 1 hour the mixture was diluted with ethyl acetate (100 mL) and was with water (2×25 mL), saturated sodium bicarbonate (25 mL), saturated ammonium chloride (25 mL) and dried over sodium sulfate. The mixture was filtered and the solvent was removed under reduced pressure. The residue was subjected to flash chromatography with eluant of (10% methanol in ethylacetate) and hexane. The product containing fractions were combined and the solvent was removed under reduced pressure to provide (2S)-tert-butyl 2-(7-bromo-4-oxochroman-3-ylcarbamoyl)pyrrolidine-1-carboxylate (3.23 g, 7.35 mmol, 84%).

(S)-tert-butyl 2-(7-bromo-3,4-dihydrochromeno[4,3-d]imidazol-2-yl)pyrrolidine-1-carboxylate: A mixture of (2S)-tert-butyl 2-(7-bromo-4-oxochroman-3-ylcarbamoyl)pyrrolidine-1-carboxylate (3.23 g, 7.35 mmol) and ammonium acetate (5.6 g, 73.5 mmol) in xylenes (40 mL) was heated at 130° C. for 2 hours. The reaction was cooled to room temperature. The xylenes were removed under reduced pressure and the residue was diluted with dichloromethane (100 mL). Saturated sodium bicarbonate (200 mL) was added slowly with stirring until gas evolution had subsided. The phases were separated and the aqueous phase was extracted with dichloromethane (50 mL). The combined organic phases were washed with brine (50 mL) and dried over sodium sulfate. The mixture was filtered and the solvent was removed under reduced pressure. The residue was subjected to flash chromatography with eluant of (10% methanol in ethylacetate) and hexane. The product containing fractions were combined and the solvent was removed under reduced pressure to provide (S)-tert-butyl 2-(7-bromo-3,4-dihydrochromeno[4,3-d]imidazol-2-yl)pyrrolidine-1-carboxylate (1.77 g, 4.21 mmol, 57%).

Example BU

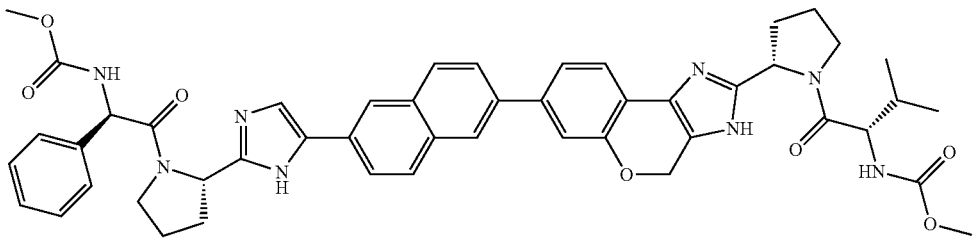

(1-{2-[7-(6-{2-[1-(2-Methoxycarbonylamino-2-phenyl-acetyl)-pyrrolidin-2-yl]-3H-imidazol-4-yl}-naphthalen-2-yl)-3,4-dihydro-chromeno[3,4-d]imidazol-2-yl]-pyrrolidine-1-carbonyl}-2-methyl-propyl)-carbamic acid methyl ester: (1-{2-[7-(6-{2-[1-(2-Methoxycarbonylamino-2-phenyl-acetyl)-pyrrolidin-2-yl]-3H-imidazol-4-yl}-naphthalen-2-yl)-3,4-dihydro-chromeno[3,4-d]imidazol-2-yl]-pyrrolidine-1-carbonyl}-2-methyl-propyl)-carbamic acid methyl ester was prepared following Example DG substituting (S)-tert-butyl 2-(7-bromo-3,4-dihydrochromeno[4,3-d]imidazol-2-yl)pyrrolidine-1-carboxylate for (S)-tert-butyl 2-(7-bromo-4,5-dihydro-1H-naphtho[1,2-d]imidazol-2-yl)pyrrolidine-1-carboxylate. $C_{48}H_{50}N_8O_7$ calculated 850.4 observed $[M+1]^+$ 851.2; rt=1.80 min.

Example BV

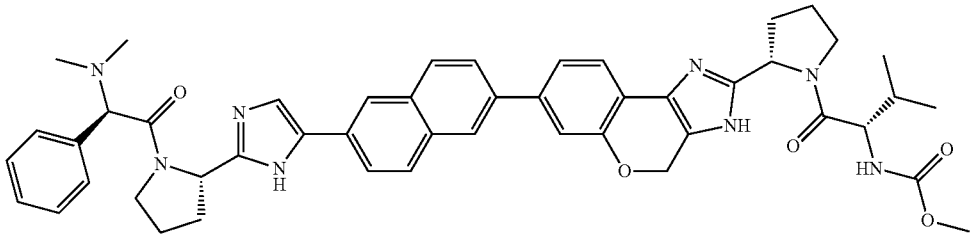 [SMILES: COC(=O)N[C@H](C(=O)N1CCC[C@H]1c1nc2c([nH]1)COc1cc(-c3ccc4cc(-c5cnc([C@@H]6CCCN6C(=O)[C@@H](c6ccccc6)N(C)C)[nH]5)ccc4c3)ccc1-2)C(C)C]

(1-{2-[7-(6-{2-[1-(2-Dimethylamino-2-phenyl-acetyl)-pyrrolidin-2-yl]-3H-imidazol-4-yl}-naphthalen-2-yl)-3,4-dihydro-chromeno[3,4-d]imidazol-2-yl]-pyrrolidine-1-carbonyl}-2-methyl-propyl)-carbamic acid methyl ester: (1-{2-[7-(6-{2-[1-(2-Dimethylamino-2-phenyl-acetyl)-pyrrolidin-2-yl]-3H-imidazol-4-yl}-naphthalen-2-yl)-3,4-dihydro-chromeno[3,4-d]imidazol-2-yl]-pyrrolidine-1-carbonyl}-2-methyl-propyl)-carbamic acid methyl ester was prepared was prepared following Example DG substituting (S)-tert-butyl 2-(7-bromo-3,4-dihydrochromeno[4,3-d]imidazol-2-yl)pyrrolidine-1-carboxylate for (S)-tert-butyl 2-(7-bromo-4,5-dihydro-1H-naphtho[1,2-d]imidazol-2-yl)pyrrolidine-1-carboxylate and Dimethylamino-phenyl-acetic acid for Methoxycarbonylamino-phenyl-acetic acid. $C_{48}H_{52}N_8O_5$ calculated 820.4 observed $[M+1]^+$ 821.3; rt=1.57 min.

Example BW

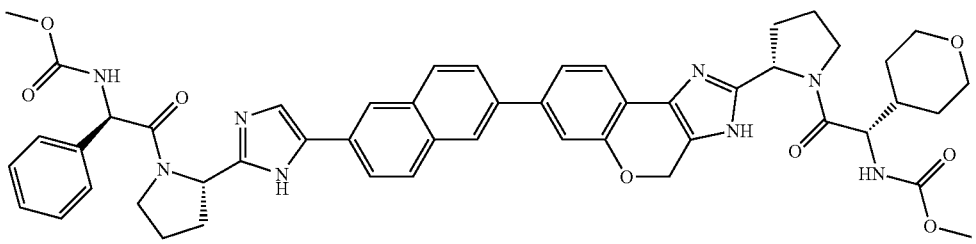

[2-{2-[7-(6-{2-[1-(2-Methoxycarbonylamino-2-phenyl-acetyl)-pyrrolidin-2-yl]-3H-imidazol-4-yl}-naphthalen-2-yl)-3,4-dihydro-chromeno[3,4-d]imidazol-2-yl]-pyrrolidin-1-yl}-2-oxo-1-(tetrahydro-pyran-4-yl)-ethyl]-carbamic acid methyl ester: [2-{2-[7-(6-{2-[1-(2-Methoxycarbonylamino-2-phenyl-acetyl)-pyrrolidin-2-yl]-3H-imidazol-4-yl}-naphthalen-2-yl)-3,4-dihydro-chromeno[3,4-d]imidazol-2-yl]-pyrrolidin-1-yl}-2-oxo-1-(tetrahydro-pyran-4-yl)-ethyl]-carbamic acid methyl ester was prepared following Example DG substituting (S)-tert-butyl 2-(7-bromo-3,4-dihydro-chromeno[4,3-d]imidazol-2-yl)pyrrolidine-1-carboxylate for (S)-tert-butyl 2-(7-bromo-4,5-dihydro-1H-naphtho[1,2-d]imidazol-2-yl)pyrrolidine-1-carboxylate and Methoxycarbonylamino-(tetrahydro-pyran-4-yl)-acetic acid for 2-Methoxycarbonylamino-3-methyl-butyric acid. $C_{50}H_{52}N_8O_8$ calculated 892.4 observed $[M+1]^+$ 893.3; rt=1.79 min.

Example BX

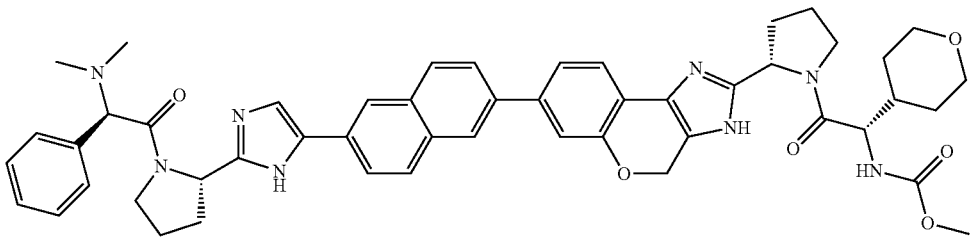 [SMILES: COC(=O)N[C@H](C(=O)N1CCC[C@H]1c1nc2c([nH]1)COc1cc(-c3ccc4cc(-c5cnc([C@@H]6CCCN6C(=O)[C@@H](c6ccccc6)N(C)C)[nH]5)ccc4c3)ccc1-2)C1CCOCC1]

[2-{2-[7-(6-{2-[1-(2-Dimethylamino-2-phenyl-acetyl)-pyrrolidin-2-yl]-3H-imidazol-4-yl}-naphthalen-2-yl)-3,4-dihydro-chromeno[3,4-d]imidazol-2-yl]-pyrrolidin-1-yl}-2-oxo-1-(tetrahydro-pyran-4-yl)-ethyl]-carbamic acid methyl ester: [2-{2-[7-(6-{2-[1-(2-Dimethylamino-2-phenyl-acetyl)-pyrrolidin-2-yl]-3H-imidazol-4-yl}-naphthalen-2-yl)-3,4-dihydro-chromeno[3,4-d]imidazol-2-yl]-pyrrolidin-1-yl}-2-oxo-1-(tetrahydro-pyran-4-yl)-ethyl]-carbamic acid methyl ester was prepared following Example DG substituting (S)-tert-butyl 2-(7-bromo-3,4-dihydrochromeno[4,3-d]imidazol-2-yl)pyrrolidine-1-carboxylate for (S)-tert-butyl 2-(7-bromo-4,5-dihydro-1H-naphtho[1,2-d]imidazol-2-yl)pyrrolidine-1-carboxylate and Dimethylamino-phenyl-acetic acid for Methoxycarbonylamino-phenyl-acetic acid and Methoxycarbonylamino-(tetrahydro-pyran-4-yl)-acetic acid for 2-Methoxycarbonylamino-3-methyl-butyric acid. $C_{50}H_{54}N_8O_6$ calculated 862.4 observed $[M+1]^+$ 863.2; rt=1.58 min.

Example BY

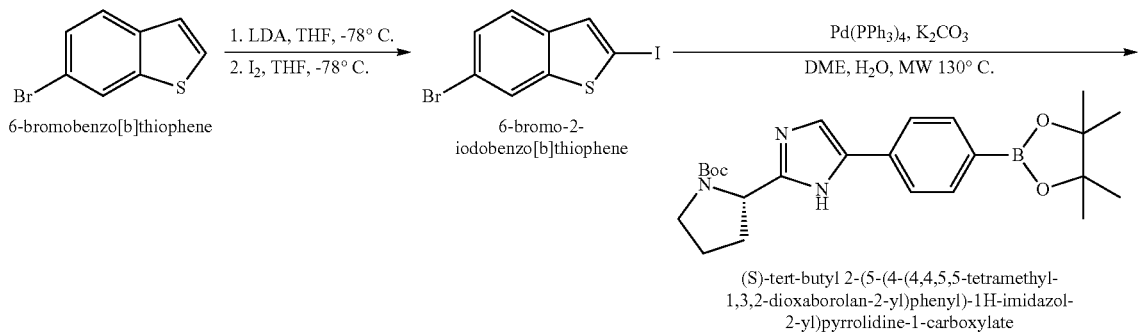

(S)-tert-butyl 2-(5-(4-(4,4,5,5-tetramethyl-1,3,2-dioxaborolan-2-yl)phenyl)-1H-imidazol-2-yl)pyrrolidine-1-carboxylate -continued

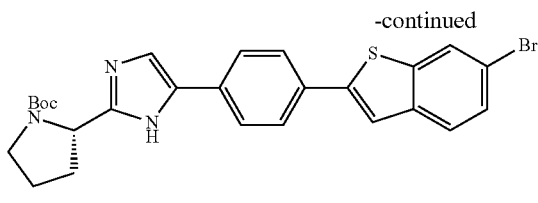 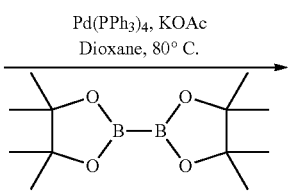

(S)-tert-butyl 2-(5-(4-(6-bromobenzo[b]thiophen-2-yl)phenyl)-1H-imidazol-2-yl)pyrrolidine-1-carboxylate

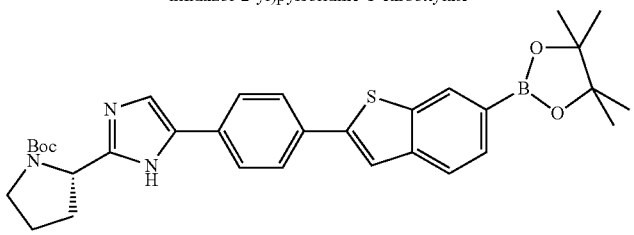 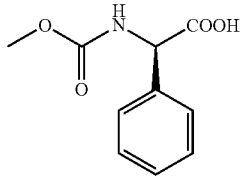

(S)-tert-butyl 2-(5-(4-(6-(4,4,5,5-tetramethyl-1,3,2-dioxaborolan-2-yl)benzo[b]thiophen-2-yl)phenyl)-1H-imidazol-2-yl)pyrrolidine-1-carboxylate (R)-2-(methoxycarbonylamino)-2-phenylacetic acid

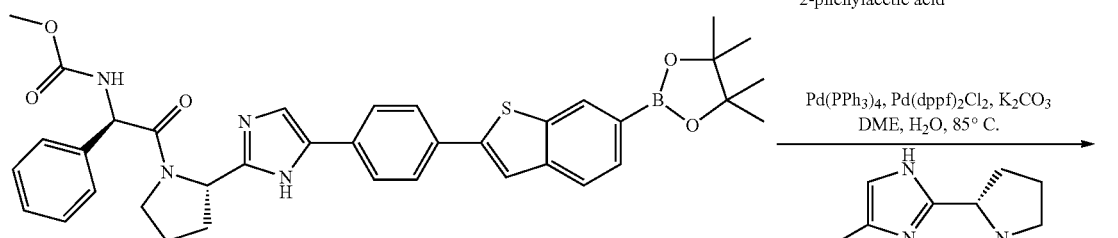

methyl (R)-2-oxo-1-phenyl-2-((S)-2-(5-(4-(6-(4,4,5,5-tetramethyl-1,3,2-dioxaborolan-2-yl)benzo[b]thiophen-2-yl)phenyl)-1H-imidazol-2-yl)pyrrolidin-1-yl)ethylcarbamate (S)-tert-butyl 2-(4-bromo-1H-imidazol-2-yl)pyrrolidine-1-carboxylate

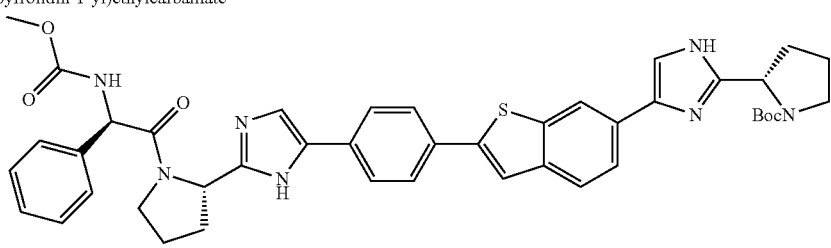

(S)-tert-butyl 2-(4-(2-(4-(2-((S)-1-((R)-2-(methoxycarbonylamino)-2-phenylacetyl)pyrrolidin-2-yl)-1H-imidazol-5-yl)phenyl)benzo[b]thiophen-6-yl)-1H-imidazol-2-yl)pyrrolidine-1-carboxylate 6-Bromo-2-iodobenzo[b]thiophene: A solution of lithium diisopropylamide (2.0 M, 1.41 mL, 2.8 mmol) was added dropwise to a solution of 6-bromobenzo[b]thiophene (500 mg, 2.4 mmol) in tetrahydrofuran (10 mL) at −78° C. under argon. After 30 minutes a solution of iodine (716 mg, 2.8 mmol) in tetrahydrofuran (3 mL) was added dropwise. The iodine quickly decolorized. After 30 minutes the reaction was quenched with an aqueous solution of sodium sulfite (1.0 M, 10 mL). Brine (50 mL) was added and the mixture was extracted with dichloromethane (3×25 mL), dried over sodium sulfate and filtered. The solvent was removed under reduced pressure to provide 6-bromobenzo[b]thiophene (702 mg, 2.07 mmol, 88%).

(S)-tert-butyl 2-(5-(4-(6-bromobenzo[b]thiophen-2-yl)phenyl)-1H-imidazol-2-yl)pyrrolidine-1-carboxylate: A mixture of 6-bromobenzo[b]thiophene (702 mg, 2.07 mmol), (S)-tert-butyl 2-(5-(4-(4,4,5,5-tetramethyl-1,3,2-dioxaborolan-2-yl)phenyl)-1H-imidazol-2-yl)pyrrolidine-1-carboxylate (700 mg, 1.59 mmol), tetrakis(triphenylphosphine) palladium (0) (184 mg, 0.15 mmol), potassium carbonate (440 mg, 3.19 mmol) in water (2 mL) and dimethoxyethane (10 mL) was heated in a microwave reactor at 130° C. for 30 minutes. The dimethoxyethane was removed under reduced pressure. The resulting residue was partitioned between water (15 mL) and dichloromethane (15 mL). The phases were separated and the aqueous phase was extracted with dichloromethane (20 mL). The combined organic extracts were dried over sodium sulfate and filtered. The solvent was removed under reduced pressure and the resulting residue was subjected to flash chromatography with eluant of (10% methanol in ethyl acetate) and hexane. The product containing fractions were combined and the solvent was removed under reduced pressure to provide (S)-tert-butyl 2-(5-(4-(6-bromobenzo[b]thiophen-2-yl)phenyl)-1H-imidazol-2-yl)pyrrolidine-1-carboxylate (302 mg, 0.58 mmol, 36%).

(S)-tert-butyl 2-(5-(4-(6-(4,4,5,5-tetramethyl-1,3,2-dioxaborolan-2-yl)benzo[b]thiophen-2-yl)phenyl)-1H-imidazol-2-yl)pyrrolidine-1-carboxylate: A mixture of (S)-tert-butyl 2-(5-(4-(6-bromobenzo[b]thiophen-2-yl)phenyl)-1H-imidazol-2-yl)pyrrolidine-1-carboxylate (302 mg, 0.57 mmol), bis(pinacolato)diboron (292 mg, 1.15 mmol), potassium acetate (113 mg, 1.15 mmol) and tetrakis(triphenylphosphine) palladium (0) (66 mg, 0.0575 mmol) in dimethoxyethane (5 mL) was heated at 80° C. for 16 h hours. The solvent was removed under reduced pressure. The resulting residue was taken up in dichloromethane (10 mL) and washed with half saturated sodium bicarbonate (5 mL), brine (5 mL) and dried over sodium sulfate. The mixture was filtered and the solvent was removed under reduced pressure. The resulting residue was subjected to flash chromatography with eluant of (10% methanol in ethyl acetate) and hexane. The product containing fractions were combined and the solvent was removed under reduced pressure to provide (S)-tert-butyl 2-(5-(4-(6-(4,4,5,5-tetramethyl-1,3,2-dioxaborolan-2-yl)benzo[b]thiophen-2-yl)phenyl)-1H-imidazol-2-yl)pyrrolidine-1-carboxylate (328 mg, 0.56 mmol, 98%).

Methyl (R)-2-oxo-1-phenyl-2-((S)-2-(5-(4-(6-(4,4,5,5-tetramethyl-1,3,2-dioxaborolan-2-yl)benzo[b]thiophen-2-yl)phenyl)-1H-imidazol-2-yl)pyrrolidin-1-yl)ethylcarbamate: A solution of hydrogen chloride in dioxane (4 N, 5 mL) was added to a solution of (S)-tert-butyl 2-(5-(4-(6-(4,4,5,5-tetramethyl-1,3,2-dioxaborolan-2-yl)benzo[b]thiophen-2-yl)phenyl)-1H-imidazol-2-yl)pyrrolidine-1-carboxylate (328 mg, 0.56 mmol) in dichloromethane (5 mL). Gas evolution was observed. After 20 min the solvent was removed under reduced pressure and the residue was placed under high vacuum for 30 min. The solid was taken up in N,N-dimethylformamide (3 mL) and N-methylmorpholine (158 µL, 1.43 mmol) was added to the solution. In a separate vessel, COMU (258 mg, 0.605 mmol), and N-methylmorpholine (158 µL, 1.43 mmol) were added to a solution of (R)-2-(methoxycarbonylamino)-2-phenylacetic acid (126 mg, 0.604 mmol) in dichloromethane (3 mL). This was stirred for 5 minutes and both solutions were combined. After 15 minutes the mixture was diluted with ethyl acetate (20 mL) and washed with water (5 mL) and brine (5 mL). The organic phase was dried over sodium sulfate and filtered. The solvent was removed under reduced pressure and the residue was subjected to flash chromatography with eluant of (10% methanol in ethyl acetate) and hexane. The product containing fractions were combined and the solvent was removed under reduced pressure to provide methyl (R)-2-oxo-1-phenyl-2-((S)-2-(5-(4-(6-(4,4,5,5-tetramethyl-1,3,2-dioxaborolan-2-yl)benzo[b]thiophen-2-yl)phenyl)-1H-imidazol-2-yl)pyrrolidin-1-yl)ethylcarbamate (261 mg, 0.39 mmol, 69%).

(S)-tert-Butyl 2-(4-(2-(4-(2-((S)-1-((R)-2-(methoxycarbonylamino)-2-phenylacetyl)pyrrolidin-2-yl)-1H-imidazol-5-yl)phenyl)benzo[b]thiophen-6-yl)-1H-imidazol-2-yl)pyrrolidine-1-carboxylate: A mixture of methyl (R)-2-oxo-1-phenyl-2-((S)-2-(5-(4-(6-(4,4,5,5-tetramethyl-1,3,2-dioxaborolan-2-yl)benzo[b]thiophen-2-yl)phenyl)-1H-imidazol-2-yl)pyrrolidin-1-yl)ethylcarbamate (261 mg, 0.39 mmol), (S)-tert-butyl 2-(4-bromo-1H-imidazol-2-yl)pyrrolidine-1-carboxylate (125 mg, 0.39 mmol), and tetrakis(triphenylphosphine) palladium (0) (45 mg, 0.039 mmol), 1,1'-Bis(diphenylphosphino)ferrocene-palladium(II)dichloride dichloromethane complex (29 mg, 0.039 mmol), potassium carbonate (109 mg, 0.78 mmol), dimethoxyethane (5 mL), and water (1 mL) was heated at 85° C. for 16 hours. The solvent was removed under reduced pressure and the residue was take up in dichloromethane (15 mL) and washed with water (5 mL) and brine (5 mL). The organic phase was dried over sodium sulfate and filtered. The solvent was removed under reduced pressure and the residue was subjected to flash chromatography with eluant of (10% methanol in ethyl acetate) and hexane. The product containing fractions were combined and the solvent was removed under reduced pressure to provide (S)-tert-Butyl 2-(4-(2-(4-(2-((S)-1-((R)-2-(methoxycarbonylamino)-2-phenylacetyl)pyrrolidin-2-yl)-1H-imidazol-5-yl)phenyl)benzo[b]thiophen-6-yl)-1H-imidazol-2-yl)pyrrolidine-1-carboxylate (88 mg, 0.011 mmol, 28%).

Example BZ

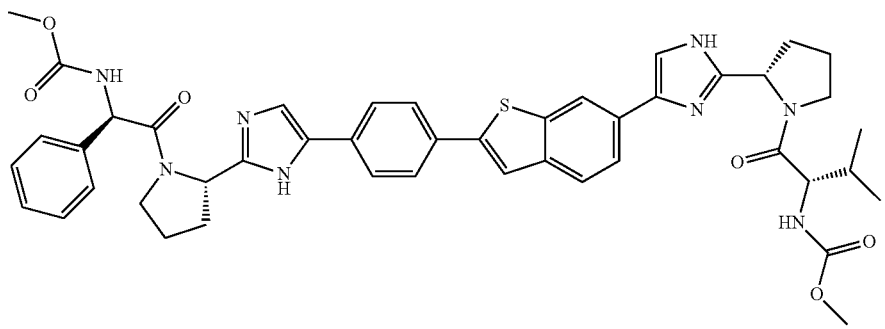 [SMILES: COC(=O)N[C@H](C(=O)N1CCC[C@H]1c1nc(-c2ccc3cc(-c4ccc(-c5cnc([C@@H]6CCCN6C(=O)[C@H](NC(=O)OC)c6ccccc6)[nH]5)cc4)sc3c2)c[nH]1)C(C)C]

[1-(2-{4-[2-(4-{2-[1-(2-Methoxycarbonylamino-2-phenyl-acetyl)-pyrrolidin-2-yl]-3H-imidazol-4-yl}-phenyl)-benzo[b]thiophen-6-yl]-1H-imidazol-2-yl}-pyrrolidine-1-carbonyl)-2-methyl-propyl]-carbamic acid methyl ester: [1-(2-{4-[2-(4-{2-[1-(2-Methoxycarbonylamino-2-phenyl-acetyl)-pyrrolidin-2-yl]-3H-imidazol-4-yl}-phenyl)-benzo[b]thiophen-6-yl]-1H-imidazol-2-yl}-pyrrolidine-1-carbonyl)-2-methyl-propyl]-carbamic acid methyl ester was prepared following Example AA substituting (S)-tert-Butyl 2-(4-(2-(4-(2-((S)-1-((R)-2-(methoxycarbonylamino)-2-phenylacetyl)pyrrolidin-2-yl)-1H-imidazol-5-yl)phenyl)benzo[b]thiophen-6-yl)-1H-imidazol-2-yl)pyrrolidine-1- carboxylate for (S)-tert-butyl 2-(5-(4-(6-(2-((2S,4S)-4-hydroxy-1-((S)-2-(methoxycarbonylamino)-3-methylbutanoyl)pyrrolidin-2-yl)-11H-imidazol-5-yl)naphthalen-2-yl)phenyl)-1H-imidazol-2-yl)pyrrolidine-1-carboxylate and 2-Methoxycarbonylamino-3-methyl-butyric acid for Methoxycarbonylamino-phenyl-acetic acid. $C_{45}H_{48}N_8O_6S$ calculated 828.3 observed $[M+1]^+$ 829.5; rt=1.90 min.

Example CA

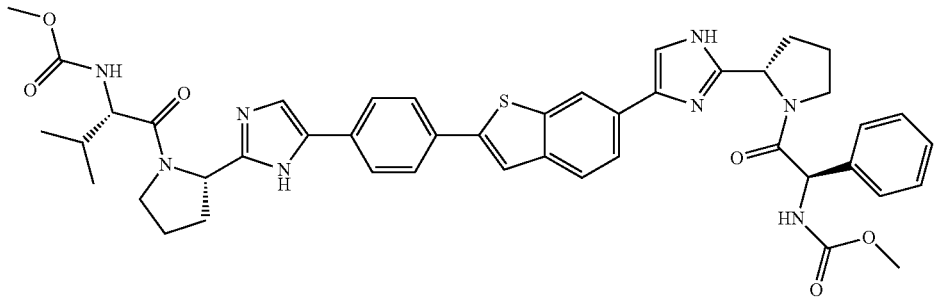 [SMILES: COC(=O)N[C@H](C(=O)N1CCC[C@H]1c1ncc(-c2ccc(-c3cc4ccc(-c5c[nH]c([C@@H]6CCCN6C(=O)[C@H](NC(=O)OC)c6ccccc6)n5)cc4s3)cc2)[nH]1)C(C)C]

[1-(2-{5-[4-(6-{2-[1-(2-Methoxycarbonylamino-2-phenyl-acetyl)-pyrrolidin-2-yl]-1H-imidazol-4-yl}-benzo[b]thiophen-2-yl)-phenyl]-1H-imidazol-2-yl}-pyrrolidine-1-carbonyl)-2-methyl-propyl]-carbamic acid methyl ester: [1-(2-{5-[4-(6-{2-[1-(2-Methoxycarbonylamino-2-phenyl-acetyl)-pyrrolidin-2-yl]-1H-imidazol-4-yl}-benzo[b]thiophen-2-yl)-phenyl]-1H-imidazol-2-yl}-pyrrolidine-1-carbonyl)-2-methyl-propyl]-carbamic acid methyl ester was prepared following Example AA substituting 2-{4-[2-(4-{2-[1-(2-Methoxycarbonylamino-3-methyl-butyryl)-pyrrolidin-2-yl]-3H-imidazol-4-yl}-phenyl)-benzo[b]thiophen-6-yl]-1H-imidazol-2-yl}-pyrrolidine-1-carboxylic acid tert-butyl ester for (S)-tert-butyl 2-(5-(4-(6-(2-((2S,4S)-4-hydroxy-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate. $C_{45}H_{48}N_8O_6S$ calculated 828.3 observed $[M+1]^+$ 829.5; rt=1.89 min.

Example CB

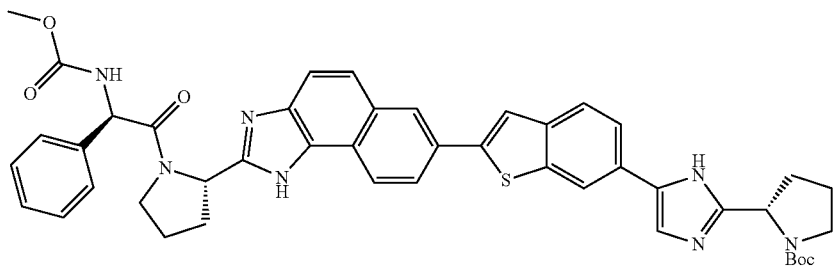 [SMILES: COC(=O)N[C@@H](C(=O)N1CCC[C@H]1c1nc2ccc3cc(-c4cc5ccc(-c6cnc([C@@H]7CCCN7C(=O)OC(C)(C)C)[nH]6)cc5s4)ccc3c2[nH]1)c1ccccc1]

(S)-tert-butyl 2-(5-(2-(2-((S)-1-((R)-2-(methoxycarbonylamino)-2-phenylacetyl)pyrrolidin-2-yl)-1H-naphtho[1,2-d]imidazol-7-yl)benzo[b]thiophen-6-yl)-1H-imidazol-2-yl)pyrrolidine-1-carboxylate: (S)-tert-butyl 2-(5-(2-(2-((S)-1-((R)-2-(methoxycarbonylamino)-2-phenylacetyl)pyrrolidin-2-yl)-1H-naphtho[1,2-d]imidazol-7-yl)benzo[b]thiophen-6-yl)-1H-imidazol-2-yl)pyrrolidine-1-carboxylate was prepared following Example BY substituting (S)-tert-butyl 2-(7-(4,4,5,5-tetramethyl-1,3,2-dioxaborolan-2-yl)-1H-naphtho[1,2-d]imidazol-2-yl)pyrrolidine-1-carboxylate for (S)-tert-butyl 2-(5-(4-(4,4,5,5-tetramethyl-1,3,2-dioxaborolan-2-yl)phenyl)-1H-imidazol-2-yl)pyrrolidine-1-carboxylate.

Example CC

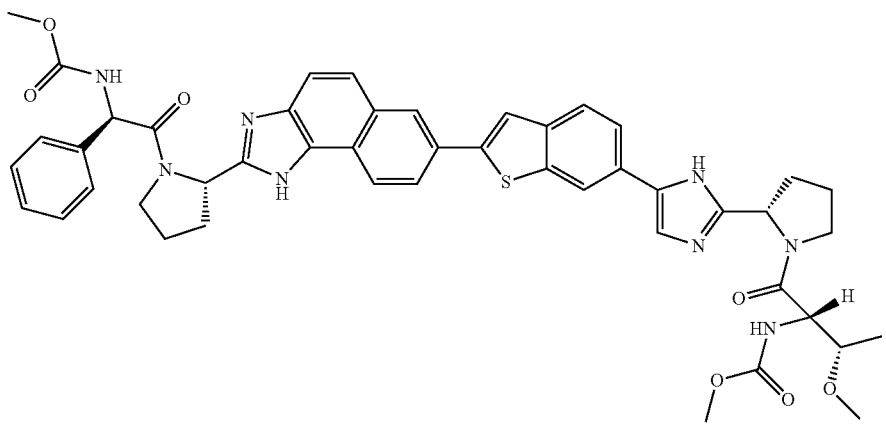 [SMILES: COC(=O)N[C@H](C(=O)N1CCC[C@H]1c1ncc(-c2ccc3cc(-c4ccc5c(ccc6nc([C@@H]7CCCN7C(=O)[C@H](NC(=O)OC)c7ccccc7)[nH]c65)c4)sc3c2)[nH]1)[C@H](C)OC]

(2-Methoxy-1-{2-[5-(2-{2-[1-(2-methoxycarbonylamino-2-phenyl-acetyl)-pyrrolidin-2-yl]-1H-naphtho[1,2-d]imidazol-7-yl}-benzo[b]thiophen-6-yl)-1H-imidazol-2-yl]-pyrrolidine-1-carbonyl}-propyl)-carbamic acid methyl ester: (2-Methoxy-1-{2-[5-(2-{2-[1-(2-methoxycarbonylamino-2-phenyl-acetyl)-pyrrolidin-2-yl]-1H-naphtho[1,2-d]imidazol-7-yl}-benzo[b]thiophen-6-yl)-1H-imidazol-2-yl]-pyrrolidine-1-carbonyl}-propyl)-carbamic acid methyl ester was prepared following Example BZ substituting (S)-tert-butyl 2-(7-(4,4,5,5-tetramethyl-1,3,2-dioxaborolan-2-yl)-1H-naphtho[1,2-d]imidazol-2-yl)pyrrolidine-1-carboxylate for (S)-tert-butyl 2-(5-(4-(4,4,5,5-tetramethyl-1,3,2-dioxaborolan-2-yl)phenyl)-1H-imidazol-2-yl)pyrrolidine-1-carboxylate and 3-Methoxy-2-methoxycarbonylamino-butyric acid for 2-Methoxycarbonylamino-3-methyl-butyric acid. $C_{47}H_{48}N_8O_7S$ calculated 868.3 observed $[M+1]^+$ 868.8; rt=2.06 min.

Example CD

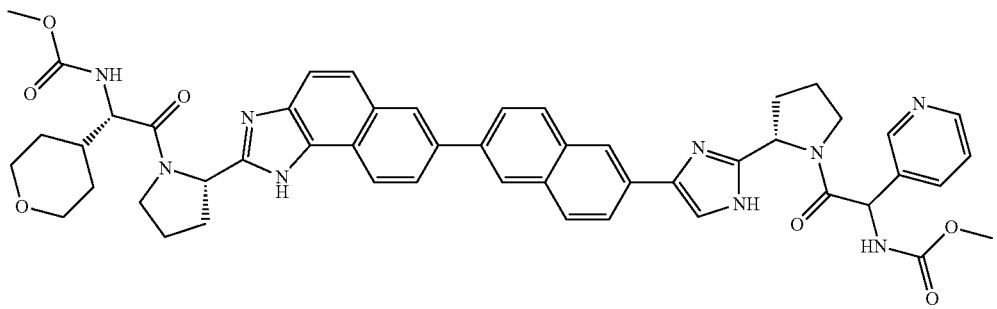

[2-{2-[7-(6-{2-[1-(2-Methoxycarbonylamino-2-pyridin-3-yl-acetyl)-pyrrolidin-2-yl]-1H-imidazol-4-yl}-naphthalen-2-yl)-1H-naphtho[1,2-d]imidazol-2-yl]-pyrrolidin-1-yl}-2-oxo-1-(tetrahydro-pyran-4-yl)-ethyl]-carbamic acid methyl ester: [2-{2-[7-(6-{2-[1-(2-Methoxycarbonylamino-2-pyridin-3-yl-acetyl)-pyrrolidin-2-yl]-1H-imidazol-4-yl}-naphthalen-2-yl)-1H-naphtho[1,2-d]imidazol-2-yl]-pyrrolidin-1-yl}-2-oxo-1-(tetrahydro-pyran-4-yl)-ethyl]-carbamic acid methyl ester was prepared following Example DR substituting Methoxycarbonylamino-(tetrahydro-pyran-4-yl)-acetic acid for 2-Methoxycarbonylamino-3-methyl-butyric acid and 2-(methoxycarbonylamino)-2-(pyridin-3-yl) acetic acid for (R)-2-(methoxycarbonylamino)-2-phenylacetic acid. $C_{50}H_{51}N_9O_7$ calculated 889.4 observed $[M+1]^+$ 890.1; rt=1.76 min.

Example CE

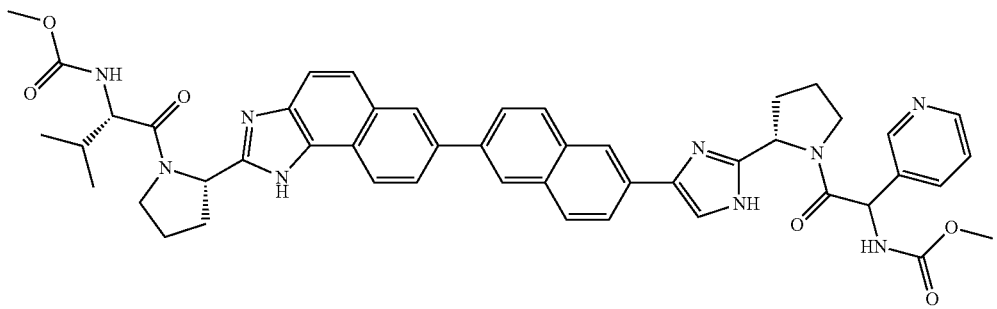

(1-{2-[7-(6-{2-[1-(2-Methoxycarbonylamino-2-pyridin-3-yl-acetyl)-pyrrolidin-2-yl]-1H-imidazol-4-yl}-naphthalen-2-yl)-1H-naphtho[1,2-d]imidazol-2-yl]-pyrrolidine-1-carbonyl}-2-methyl-propyl)-carbamic acid methyl ester: (1-{2-[7-(6-{2-[1-(2-Methoxycarbonylamino-2-pyridin-3-yl-acetyl)-pyrrolidin-2-yl]-1H-imidazol-4-yl}-naphthalen-2-yl)-1H-naphtho[1,2-d]imidazol-2-yl]-pyrrolidine-1-carbonyl}-2-methyl-propyl)-carbamic acid methyl ester was prepared following Example DR substituting 2-(methoxycarbonylamino)-2-(pyridin-3-yl)acetic acid for (R)-2-(methoxycarbonylamino)-2-phenylacetic acid. $C_{48}H_{49}N_9O_6$ calculated 847.4 observed $[M+1]^+$ 847.9; rt=1.81 min.

Example CF

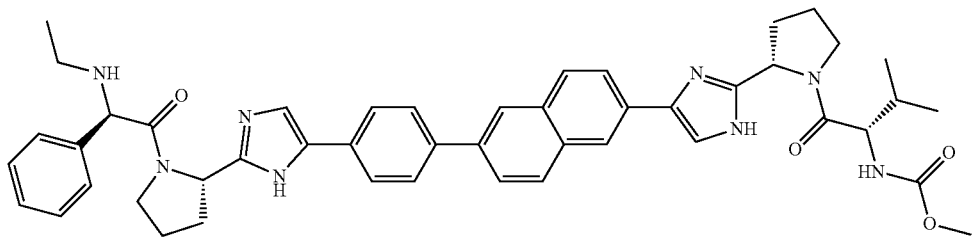 [SMILES: CCN[C@@H](C(=O)N1CCC[C@H]1c1ncc(-c2ccc(-c3ccc4cc(-c5c[nH]c([C@@H]6CCCN6C(=O)[C@@H](NC(=O)OC)C(C)C)n5)ccc4c3)cc2)[nH]1)c1ccccc1]

[1-(2-{4-[6-(4-{2-[1-(2-Ethylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: [1-(2-{4-[6-(4-{2-[1-(2-Ethylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester was prepared following Example ET substituting (R)-2-(ethylamino)-2-phenylacetic acid for 2-Methoxycarbonylamino-2-phenyl-propionic acid. $C_{47}H_{52}N_8O_4$ calculated 792.4 observed $[M+1]^+$ 793.4; rt=1.68 min.

Example CG

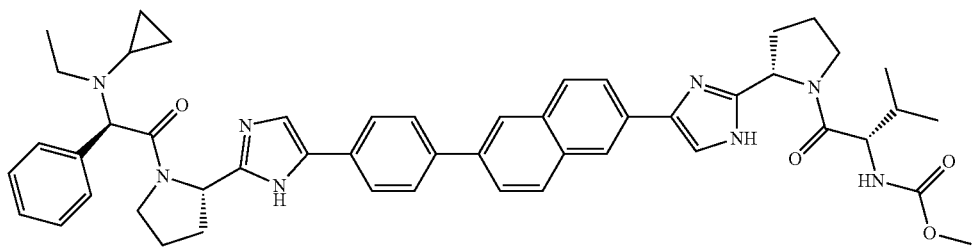 [SMILES: CCN(C1CC1)[C@@H](C(=O)N1CCC[C@H]1c1ncc(-c2ccc(-c3ccc4cc(-c5c[nH]c([C@@H]6CCCN6C(=O)[C@@H](NC(=O)OC)C(C)C)n5)ccc4c3)cc2)[nH]1)c1ccccc1]

Methyl (S)-1-((S)-2-(4-(6-(4-(2-((S)-1-((R)-2-(cyclopropyl(ethyl)amino)-2-phenylacetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate: methyl (S)-1-((S)-2-(4-(6-(4-(2-((S)-1-((R)-2-(cyclopropyl(ethyl)amino)-2-phenylacetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate was prepared following Example ET substituting (R)-2-(cyclopropyl(ethyl)amino)-2-phenylacetic acid for 2-Methoxycarbonylamino-2-phenyl-propionic acid. $C_{50}H_{56}N_8O_4$ calculated 832.4 observed $[M+1]^+$ 833.3; rt=2.23 min.

Example CH

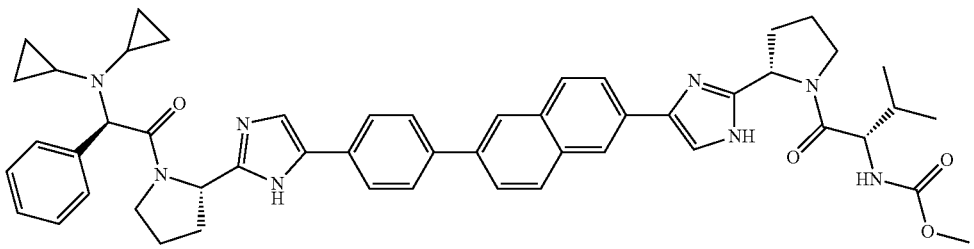 [SMILES: COC(=O)N[C@H](C(=O)N1CCC[C@H]1c1nc(-c2ccc3cc(-c4ccc(-c5cnc([C@@H]6CCCN6C(=O)[C@@H](c6ccccc6)N(C6CC6)C6CC6)[nH]5)cc4)ccc3c2)c[nH]1)C(C)C]

[1-(2-{4-[6-(4-{2-[1-(2-Dicyclopropylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: [1-(2-{4-[6-(4-{2-[1-(2-Dicyclopropylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester was prepared following Example ET substituting (R)-2-(dicyclopropylamino)-2-phenylacetic acid for 2-Methoxycarbonylamino-2-phenyl-propionic acid. $C_{51}H_{56}N_8O_4$ calculated 844.4 observed $[M+1]^+$ 845.2; rt=1.73 min.

Example CI

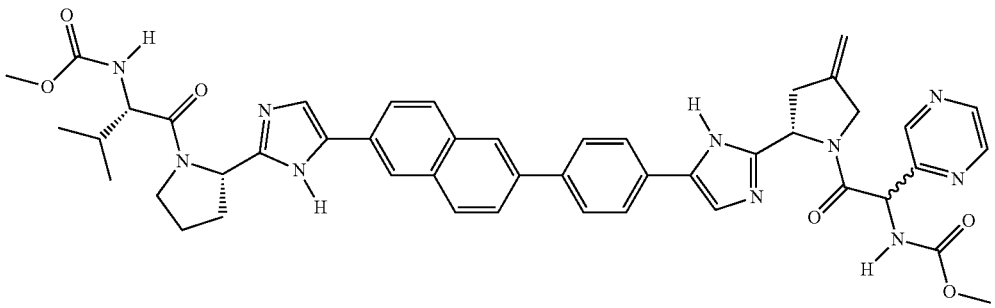

[1-(2-{5-[6-(4-{2-[1-(2-Methoxycarbonylamino-2-pyrazin-2-yl-acetyl)-4-methylene-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Prepared as {2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-4-methylene-pyrrolidin-1-yl]-2-oxo-1-pyridin-3-yl-ethyl}-carbamic acid methyl ester (Example CL) from 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester.

LCMS-ESI$^+$: calc'd for $C_{46}H_{48}N_{10}O_6$: 836.9 ($M^+$) found: 837.8 ($M+H^+$).

Example CJ

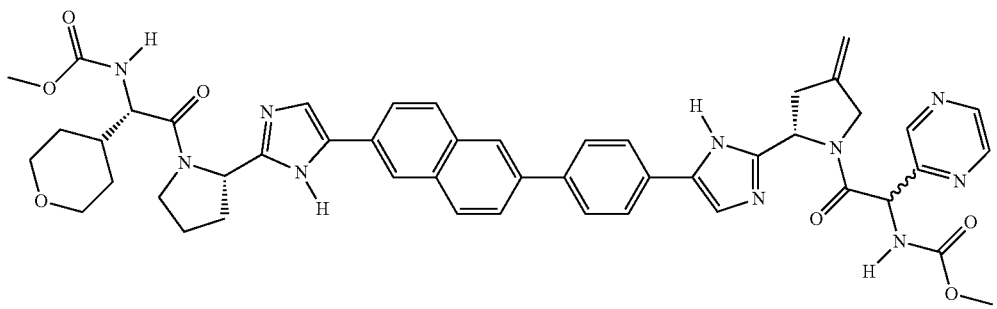

{2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-4-methylene-pyrrolidin-1-yl]-2-oxo-1-pyrazin-2-yl-ethyl}-carbamic acid methyl ester Prepared as {2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-4-methylene-pyrrolidin-1-yl]-2-oxo-1-pyridin-3-yl-ethyl}-carbamic acid methyl ester (Example CL) replacing the amino acid derivative in the final coupling step.
LCMS-ESI+: calc'd for $C_{48}H_{50}N_{10}O_7$: 878.9 (M+) found: 879.3 (M+H+).

Example CK

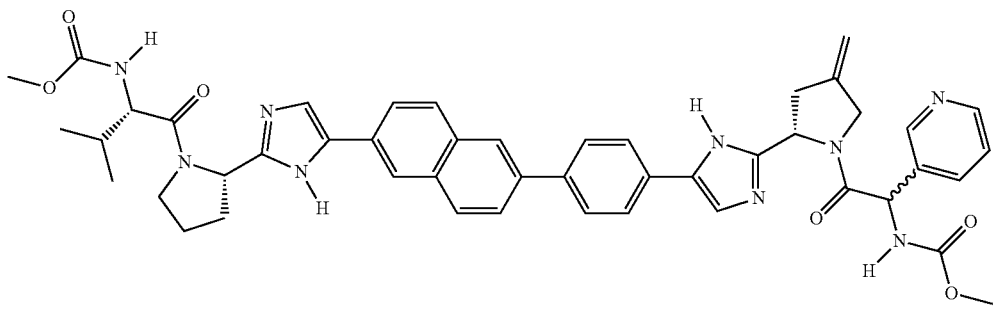

[1-(2-{5-[6-(4-{2-[1-(2-Methoxycarbonylamino-2-pyridin-3-yl-acetyl)-4-methylene-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Prepared as {2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-4-methylene-pyrrolidin-1-yl]-2-oxo-1-pyridin-3-yl-ethyl}-carbamic acid methyl ester (Example CL) from 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester. LCMS-ESI+: calc'd for $C_{47}H_{49}N_9O_6$: 835.9 (M+) found: 836.4 (M+H+).

Example CL
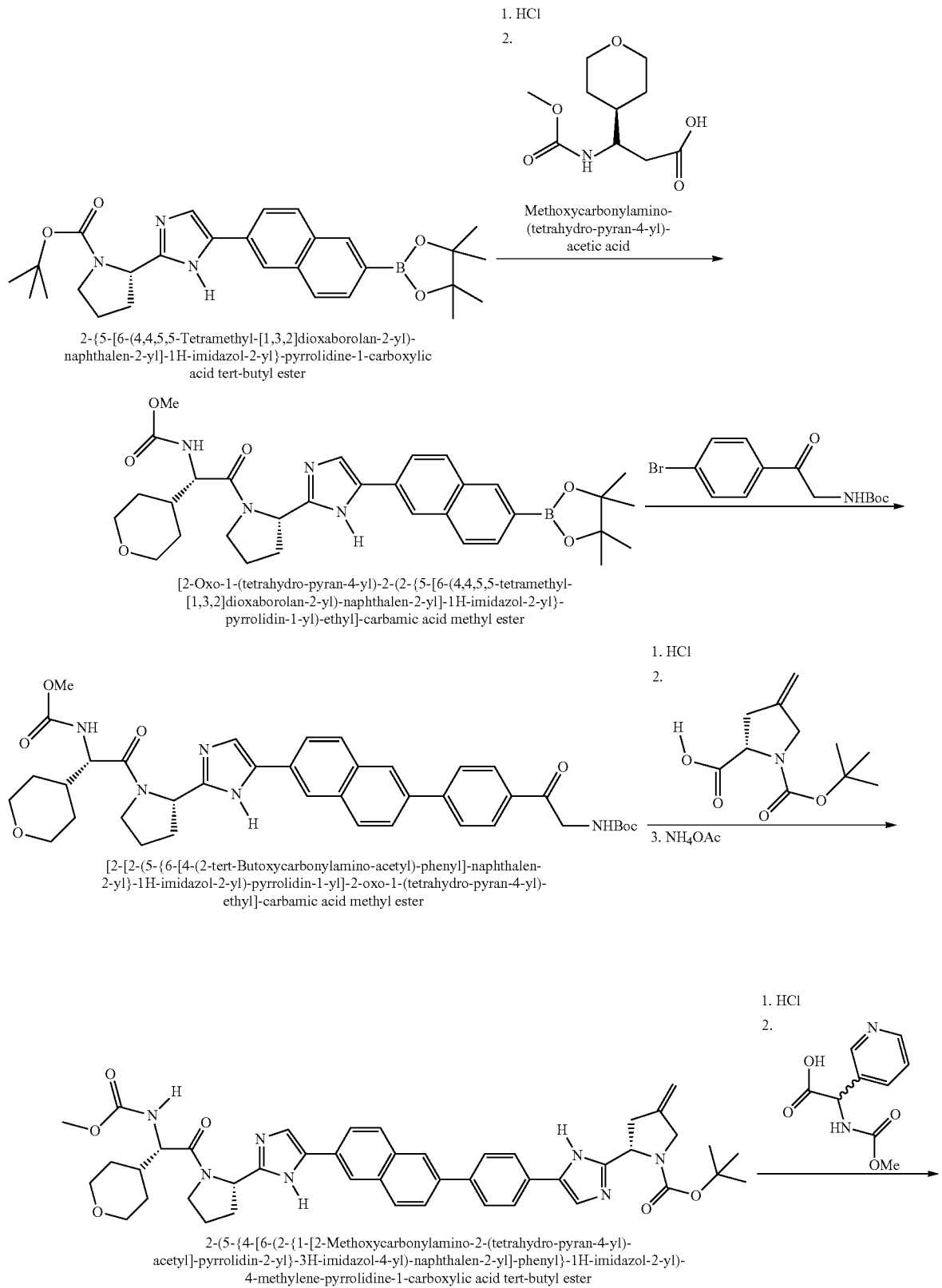

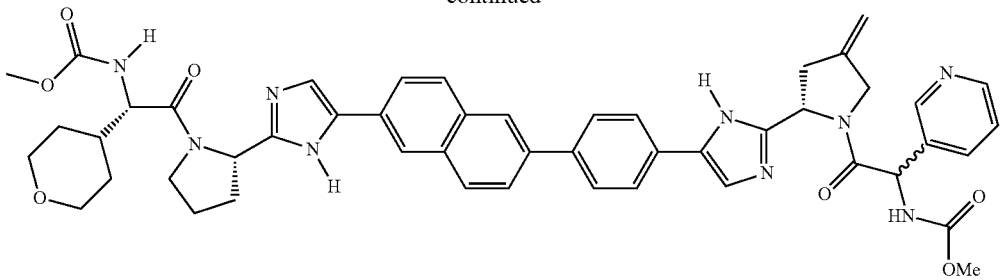

{2-[2-(5-{4-[6-(2-{1-[2-Methoxycarbonylamino-2-(tetrahydro-pyran-4-yl)-acetyl]-
pyrrolidin-2-yl}-3H-imidazik-4-yl)-naphthalen-2-yl]-phenyl}-1H-imidazol-2-yl)-4-methylene-
pyrrolidin-1-yl]-2-oxo-1-pyridin-3-yl-ethyl}-carbamic acid methyl ester

[2-Oxo-1-(tetrahydro-pyran-4-yl)-2-(2-{5-[6-(4,4,5,5-tetramethyl-[1,3,2]dioxaborolan-2-yl)-naphthalen-2-yl]-1H-imidazol-2-yl}-pyrrolidin-1-yl)-ethyl]-carbamic acid methyl ester:

2-{5-[6-(4,4,5,5-Tetramethyl-[1,3,2]dioxaborolan-2-yl)-naphthalen-2-yl]-1H-imidazol-2-yl}-pyrrolidine-1-carboxylic acid tert-butyl ester (350 mg, 0.717 mmol) was dissolved in DCM (8 mL) at room temperature. HCl (4N in dioxane, 8 mL) was added and stirring at room temperature was continued. After all starting material was consumed, the volatiles were removed in vacuo and the crude material was dissolved in DMF. Methoxy carbonylamino-(tetrahydro-pyran-4-yl)-acetic acid (155 mg, 0.715 mmol), DIEA (276.6 mg, 2.1 mmol), and HATU (272 mg, 0.715 mmol) were added. After all starting material was consumed, the reaction was diluted with EtOAc and was washed with brine/aqueous bicarbonate. The organic layer was dried over sodium sulfate. Filtration and evaporation of solvents in vacuo gave the crude product, which was purified via flash chromatography on silica gel (eluent: EtOAc/hexanes) to yield 355 mg.

[2-[2-(5-{6-[4-(2-tert-Butoxycarbonylamino-acetyl)-phenyl]-naphthalen-2-yl}-1H-imidazol-2-yl)-pyrrolidin-1-yl]-2-oxo-1-(tetrahydro-pyran-4-yl)-ethyl]-carbamic acid methyl ester [2-Oxo-1-(tetrahydro-pyran-4-yl)-2-(2-{5-[6-(4,4,5,5-tetramethyl-[1,3,2]dioxaborolan-2-yl)-naphthalen-2-yl]-1H-imidazol-2-yl}-pyrrolidin-1-yl)-ethyl]-carbamic acid methyl ester (200 mg, 0.34 mmol), [2-(4-Bromo-phenyl)-2-oxo-ethyl]-carbamic acid tert-butyl ester (106 mg, 0.34 mmol), Pd[PPh3]4 (39.2 mg, 0.034 mmol), potassium carbonate (117 mg, 0.85 mmol) was heated at 120 C in the microwave for 22 minutes in DME (2.5 mL) and water (0.3 mL). Brine (1 mL) was added and the organic layer was isolated and the volatiles were removed. The product was purified via flash chromatography on silica gel (eluent: EtOAc/hexanes) to yield 183 mg.

2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-4-methylene-pyrrolidine-1-carboxylic acid tert-butyl ester

[2-[2-(5-{6-[4-(2-tert-Butoxycarbonylamino-acetyl)-phenyl]-naphthalen-2-yl}-1H-imidazol-2-yl)-pyrrolidin-1-yl]-2-oxo-1-(tetrahydro-pyran-4-yl)-ethyl]-carbamic acid methyl ester (183 mg, 0.265 mmol) was dissolved in DCM (2 mL) and HCl (4N in dioxane) was added. Stirring at room temperature was continued. After all starting material was consumed, all volatiles were removed in vacuo. The crude material was dissolved in DMF (1.5 mL) and 4-Methylene-pyrrolidine-1,2-dicarboxylic acid 1-tert-butyl ester (60.1 mg, 0.265 mmol), DIEA (102 mg, 0.895 mmol), and HATU (100.7 mg, 0.265 mmol) were added and stirring at room temperature was continued. The crude reaction was diluted with EtOAc and washed with brine/aqueous bicarbonate solution. The organic layer was dried over sodium sulfate. Filtration and evaporation of solvents gave the crude product (240 mg). The material was dissolved in m-xylenes (4 mL) at 130° C. Ammonium acetate (200 mg) was added and the reaction was heated at 130° C. After 2 hours the reaction was cooled to room temperature. All volatiles were removed in vacuo and the crude material was partitioned between EtOAc and brine/aqueous sodium bicarbonate solution. The organic layer was dried over sodium sulfate. Filtration and evaporation of solvents gave the crude product. Purification via flash chromatography yielded the product (170.4 mg).

{2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-4-methylene-pyrrolidin-1-yl]-2-oxo-1-pyridin-3-yl-ethyl}-carbamic acid methyl ester 2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-4-methylene-pyrrolidine-1-carboxylic acid tert-butyl ester (64 mg, 0.0816 mmol) was dissolved in DCM (1 mL) and HCl (4N dioxane, 1 mL) was added. After 20 minutes all volatiles were removed in vacuo. The crude material was dissolved in DMF (1 mL) and Methoxycarbonylamino-pyridin-3-yl-acetic acid/NaCl (1:1, 22 mg, 0.0816 mmol), HATU (31 mg, 0.0816 mmol), and DIEA (31.5 mg, 0.245 mmol) were added and stirring at room temperature was continued. After 30 minutes, aqueous HCl (1N, 0.1 mL) was added and the reaction mixture was purified via RP-HPLC (eluent: water/MeCN w/0.1% TFA). The product containing fractions were lyophilized to yield the product (8.9 mg).

LCMS-ESI$^+$: calc'd for $C_{49}H_{51}N_9O_7$: 877.9 (M$^+$) found: 878.1 (M+H$^+$)

Example CM

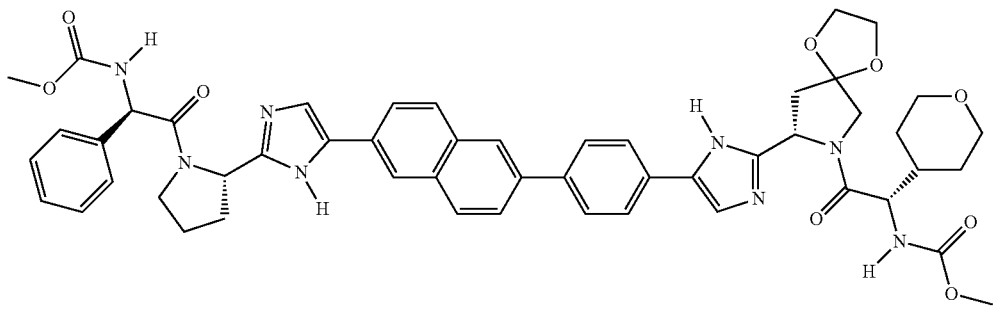

[2-(8-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-1,4-dioxa-7-aza-spiro[4.4]non-7-yl)-2-oxo-1-(tetrahydro-pyran-4-yl)-ethyl]-carbamic acid methyl ester Synthesized similar to (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester with the corresponding amino acid carbamate replacements.

LCMS-ESI+: calc'd for $C_{51}H_{54}N_8O_9$: 923.0 (M+) found: 923.8 (M+H+)

Example CN

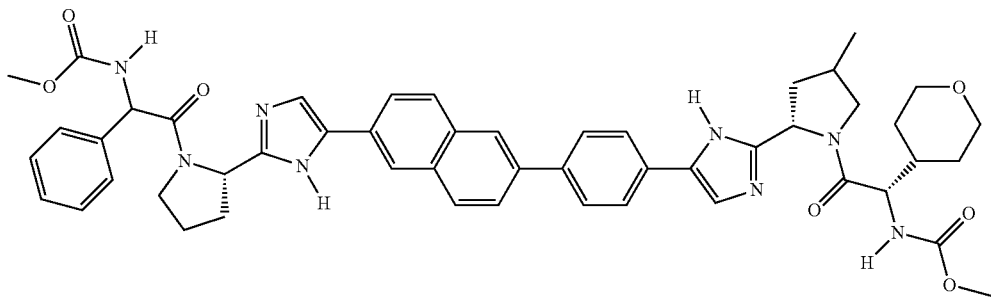

[2-(2-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-4-methylene-pyrrolidin-1-yl)-2-oxo-1-(tetrahydro-pyran-4-yl)-ethyl]-carbamic acid methyl ester Prepared as {2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-4-methylene-pyrrolidin-1-yl]-2-oxo-1-pyridin-3-yl-ethyl}-carbamic acid methyl ester from 2-{5-[4-(6-{2-[1-benzyloxycarbonyl-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester; using an HCl mediated deprotection and amide bond formation prior to an HBr mediated deprotection and second amide bond formation.

LCMS-ESI+: calc'd for $C_{50}H_{52}N_8O_7$: 876.9 (M+) found: 877.5 (M+H+).

Example CO

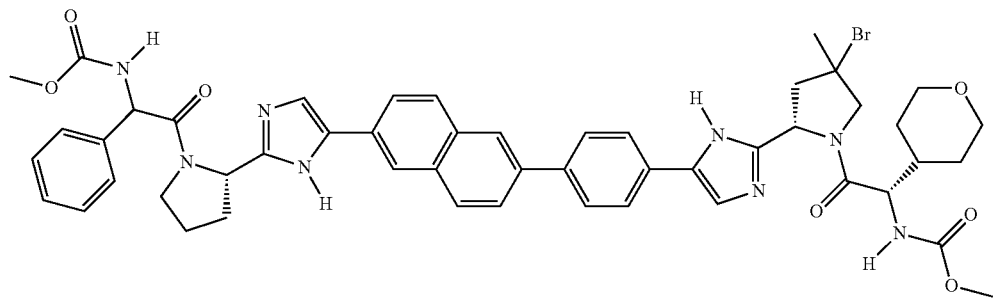

[2-(4-Bromo-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-4-methyl-pyrrolidin-1-yl)-2-oxo-1-(tetrahydro-pyran-4-yl)-ethyl]-carbamic acid methyl ester Isolated from the reaction mixture leading to [2-(2-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-4-methylene-pyrrolidin-1-yl)-2-oxo-1-(tetrahydro-pyran-4-yl)-ethyl]-carbamic acid methyl ester LCMS-ESI+: calc'd for $C_{50}H_{53}BrN_8O_7$: 957.9 ($M^+$) found: 956.9/959.7 ($M+H^+$)

Example CP

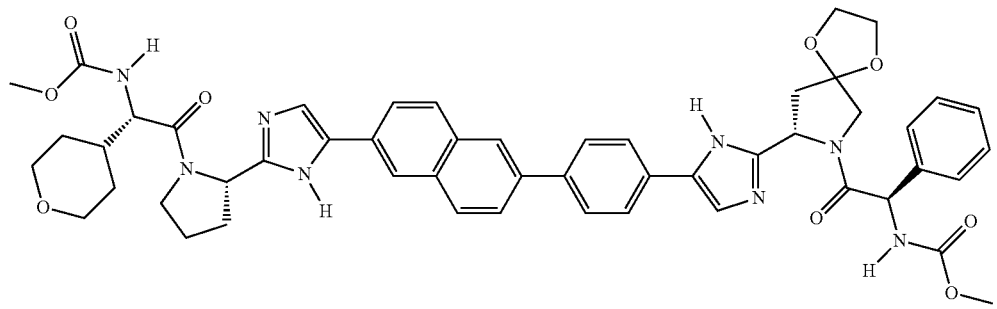

{2-[8-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-1,4-dioxa-7-aza-spiro[4.4]non-7-yl]-2-oxo-1-phenyl-ethyl}-carbamic acid methyl ester Synthesized similar to (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester with the corresponding amino acid carbamate replacements.

LCMS-ESI+: calc'd for $C_{51}H_{54}N_8O_9$: 923.0 ($M^+$) found: 923.3 ($M+H^+$)

Example CQ

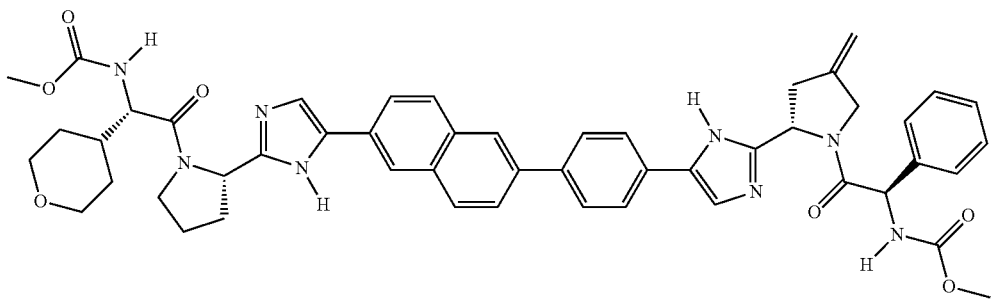

{2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-4-methylene-pyrrolidin-1-yl]-2-oxo-1-phenyl-ethyl}-carbamic acid methyl ester Prepared as {2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-4-methylene-pyrrolidin-1-yl]-2-oxo-1-pyridin-3-yl-ethyl}-carbamic acid methyl ester replacing the amino acid derivative in the final coupling step.

LCMS-ESI$^+$: calc'd for $C_{50}H_{52}N_8O_7$: 876.9 (M$^+$) found: 877.2 (M+H$^+$)

Example CR

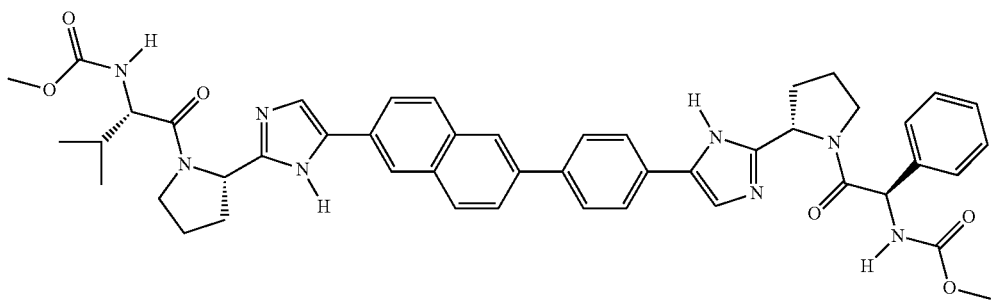

(1-{2-[5-(6-{2-[1-(2-Methoxycarbonylamino-2-phenyl-acetyl)-pyrrolidin-2-yl]-1,4-dihydro-chromeno[3,4-d]imidazol-7-yl}-naphthalen-2-yl)-1H-imidazol-2-yl]-pyrrolidine-1-carbonyl}-2-methyl-propyl)-carbamic acid methyl ester Synthesized similar to (1-{2-[7-(6-{2-[1-(2-Methoxycarbonylamino-2-phenyl-acetyl)-pyrrolidin-2-yl]-3H-imidazol-4-yl}-naphthalen-2-yl)-3,4-dihydro-chromeno[3,4-d]imidazol-2-yl]-pyrrolidine-1-carbonyl}-2-methyl-propyl)-carbamic acid methyl ester with the corresponding methoxycarbonylamino-phenyl-acetic acid replacement.

LCMS-ESI$^+$: calc'd for $C_{48}H_{50}N_8O_7$: 850.9 (M$^+$) found: 851.3 (M+H$^+$)

Example CS

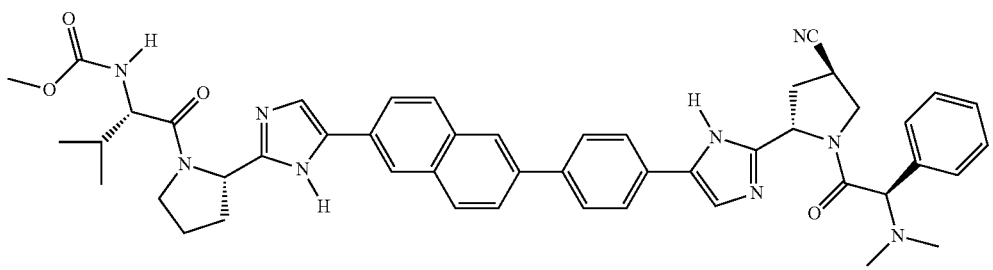 [SMILES: COC(=O)N[C@H](C(=O)N1CCC[C@H]1c1ncc(-c2ccc3cc(-c4ccc(-c5cnc([C@@H]6C[C@@H](C#N)CN6C(=O)[C@@H](c6ccccc6)N(C)C)[nH]5)cc4)ccc3c2)[nH]1)C(C)C]

[1-(2-{5-[6-(4-{2-[4-Cyano-1-(2-dimethylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Synthesized similar to [1-(2-{5-[6-(4-{2-[4-Cyano-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester replacing the methoxycarbonylamino-phenyl-acetic acid with dimethylamino-phenyl-acetic acid.

LCMS-ESI$^+$: calc'd for $C_{48}H_{51}N_9O_4$: 817.9 (M$^+$) found: 818.4 (M+H$^+$)

Example CT

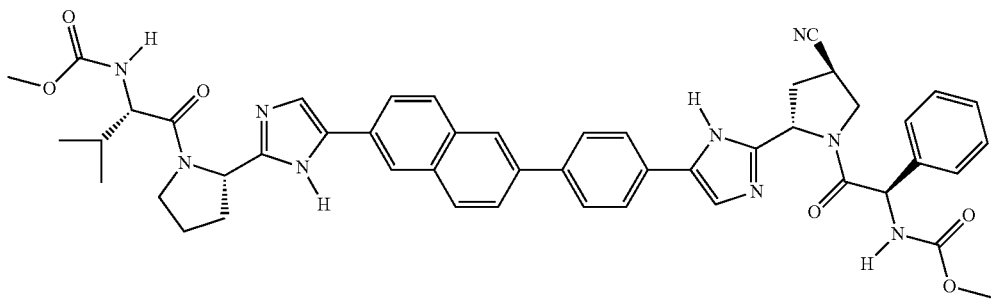

[1-(2-{5-[6-(4-{2-[4-Cyano-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Synthesized similar to [1-(2-{5-[6-(4-{2-[4-Cyano-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using [1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-2-methyl-propyl]-carbamic acid methyl ester and 2-[5-(4-Bromo-phenyl)-1H-imidazol-2-yl]-4-cyano-pyrrolidine-1-carboxylic acid tert-butyl ester and methoxycarbonylamino-phenyl-acetic acid.
LCMS-ESI$^+$: calc'd for $C_{48}H_{49}N_9O_6$: 847.9 (M$^+$) found: 848.6 (M+H$^+$)

Example CU

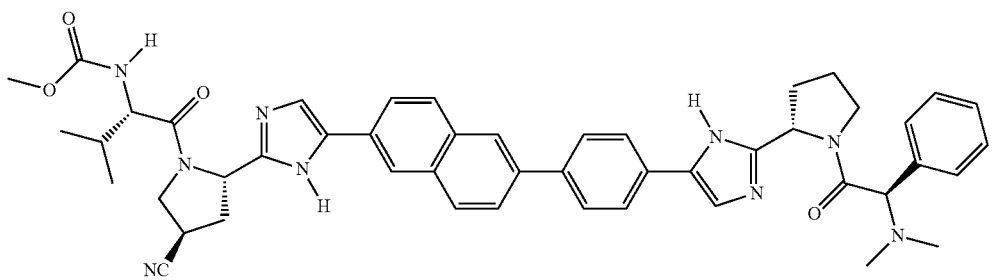 [SMILES: COC(=O)N[C@H](C(=O)N1C[C@H](C#N)C[C@H]1c1ncc(-c2ccc3cc(-c4ccc(-c5cnc([C@@H]6CCCN6C(=O)[C@@H](c6ccccc6)N(C)C)[nH]5)cc4)ccc3c2)[nH]1)C(C)C]

[1-(4-Cyano-2-{5-[6-(4-{2-[1-(2-dimethylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Synthesized similar to [1-(2-{5-[6-(4-{2-[4-Cyano-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using [1-(4-Cyano-2-{5-[6-(4,4,5,5-tetramethyl-[1,3,2]dioxaborolan-2-yl)-naphthalen-2-yl]-1H-imidazol-2-yl}-pyrrolidine-1-carbonyl)-2-methyl-propyl]-carbamic acid methyl ester and 2-[5-(4-Bromo-phenyl)-1H-imidazol-2-yl]-pyrrolidine-1-carboxylic acid tert-butyl ester and dimethylamino-phenyl-acetic acid.
LCMS-ESI$^+$: calc'd for $C_{48}H_{51}N_9O_4$: 817.9 (M$^+$) found: 818.5 (M+H$^+$)

Example CV

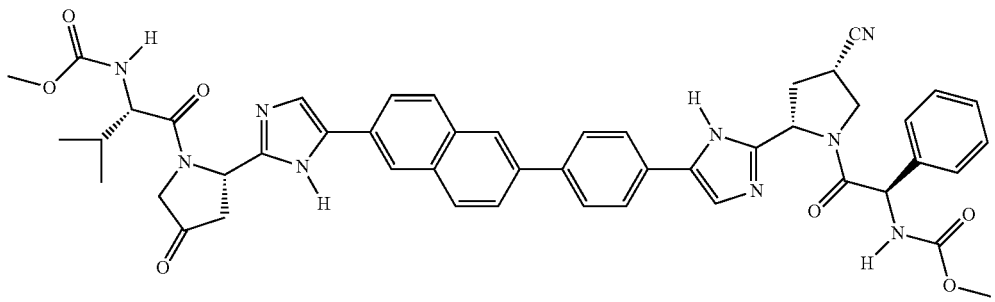

[1-(2-{5-[6-(4-{2-[4-Cyano-1-(2-methoxycarbo-
nylamino-2-phenyl-acetyl)-pyrrolidin-2-yl]-3H-imi-
dazol-4-yl}-phenyl)-naphthalen-2-yl]-1H-imidazol-
2-yl}-4-oxo-pyrrolidine-1-carbonyl)-2-methyl-
propyl]-carbamic acid methyl ester Synthesized similar to [1-(2-{4-[4-(6-{2-[1-(2-Methoxy-carbonylamino-2-phenyl-acetyl)-4-oxo-pyrrolidin-2-yl]-1H-imidazol-4-yl}-naphthalen-2-yl)-phenyl]-1H-imidazol-2-yl}-pyrrolidine-1-carbonyl)-2-methyl-propyl]-carbamic acid methyl ester with the corresponding amino acid carbamate replacements.

LCMS-ESI$^+$: calc'd for $C_{48}H_{47}N_9O_7$: 861.9 (M$^+$) found: 862.3 (M+H$^+$)

Example CW

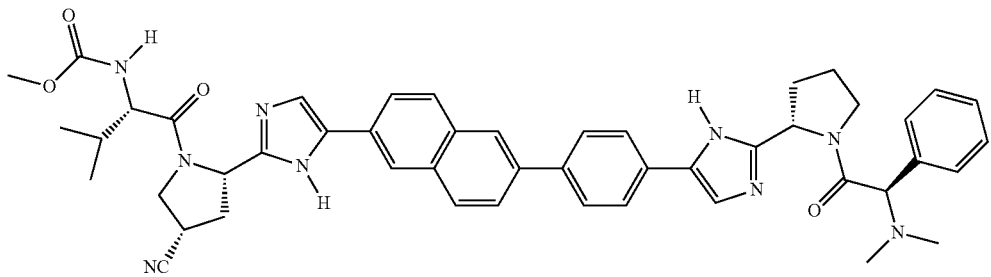 [SMILES: COC(=O)N[C@H](C(=O)N1C[C@@H](C#N)C[C@H]1c1ncc(-c2ccc3cc(-c4ccc(-c5cnc([C@@H]6CCCN6C(=O)[C@@H](c6ccccc6)N(C)C)[nH]5)cc4)ccc3c2)[nH]1)C(C)C]

[1-(4-Cyano-2-{5-[6-(4-{2-[1-(2-dimethylamino-2-
phenyl-acetyl)-pyrrolidin-2-yl]-3H-imidazol-4-yl}-
phenyl)-naphthalen-2-yl]-1H-imidazol-2-yl}-pyrroli-
dine-1-carbonyl)-2-methyl-propyl]-carbamic acid
methyl ester Synthesized similar to [1-(2-{5-[6-(4-{2-[4-Cyano-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using [1-(4-Cyano-2-{5-[6-(4,4,5,5-tetramethyl-[1,3,2]dioxaborolan-2-yl)-naphthalen-2-yl]-1H-imidazol-2-yl}-pyrrolidine-1-carbonyl)-2-methyl-propyl]-carbamic acid methyl ester and 2-[5-(4-Bromo-phenyl)-1H-imidazol-2-yl]-pyrrolidine-1-carboxylic acid tert-butyl ester and dimethylamino-phenyl-acetic acid.

LCMS-ESI$^+$: calc'd for $C_{48}H_{51}N_9O_4$: 817.9 (M$^+$) found: 818.5 (M+H$^+$).

Example CX

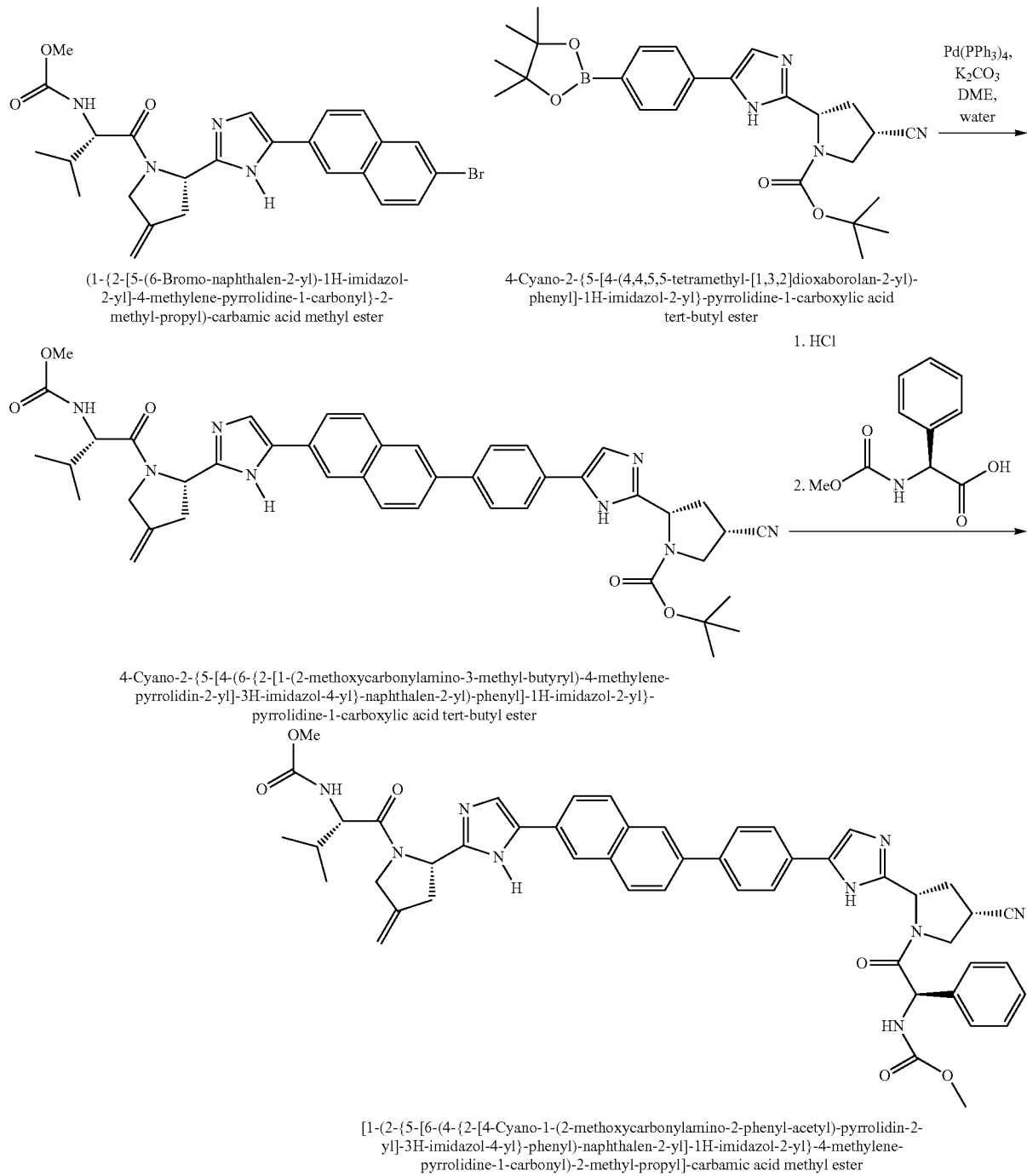

(1-{2-[5-(6-Bromo-naphthalen-2-yl)-1H-imidazol-2-yl]-4-methylene-pyrrolidine-1-carbonyl}-2-methyl-propyl)-carbamic acid methyl ester 4-Cyano-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester 4-Cyano-2-{5-[4-(6-{2-[1-(2-methoxycarbonylamino-3-methyl-butyryl)-4-methylene-pyrrolidin-2-yl]-3H-imidazol-4-yl}-naphthalen-2-yl)-phenyl]-1H-imidazol-2-yl}-pyrrolidine-1-carboxylic acid tert-butyl ester

[1-(2-{5-[6-(4-{2-[4-Cyano-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-4-methylene-pyrrolidine-1-carbonyl)-2-methyl-propyl]-carbamic acid methyl ester 4-Cyano-2-{5-[4-(6-{2-[1-(2-methoxycarbonylamino-3-methyl-butyryl)-4-methylene-pyrrolidin-2-yl]-3H-imidazol-4-yl}-naphthalen-2-yl)-phenyl]-1H-imidazol-2-yl}-pyrrolidine-1-carboxylic acid tert-butyl ester (1-{2-[5-(6-Bromo-naphthalen-2-yl)-1H-imidazol-2-yl]-4-methylene-pyrrolidine-1-carbonyl}-2-methyl-propyl)-carbamic acid methyl ester (202 mg, 0.392 mmol), 4-Cyano-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester (181 mg, 0.392 mmol), Pd[PPh$_3$](45.6 mg, 0.0392 mmol), potassium carbonate (108 mg, 0.784 mmol) were heated in DME (3 mL)/water (0.4 mL) at 120° C. for 20 minutes under microwave conditions. The volatiles were removed in vacuo and the crude was partitioned between EtOAc and brine/aqueous sodium bicarbonate solution. The organic layer was dried over sodium sulfate. Filtration and evaporation of solvents yielded the crude material, which was purified via flash chromatography on silica gel to yield the product. (161 mg).

[1-(2-{5-[6-(4-{2-[4-Cyano-1-(2-methoxycarbo-nylamino-2-phenyl-acetyl)-pyrrolidin-2-yl]-3H-imidazol-4-yl}-phenyl)-naphthalen-2-yl]-1H-imidazol-2-yl}-4-methylene-pyrrolidine-1-carbonyl)-2-methyl-propyl]-carbamic acid methyl ester 4-Cyano-2-{5-[4-(6-{2-[1-(2-methoxycarbonylamino-3-methyl-butyryl)-4-methylene-pyrrolidin-2-yl]-3H-imidazol-4-yl}-naphthalen-2-yl)-phenyl]-1H-imidazol-2-yl}-pyrrolidine-1-carboxylic acid tert-butyl ester (102.0 mg, 0.134 mmol) was stirred in DCM (2.0 mL)/HCl in dioxane (4M, 2.0 mL). After 40 minutes all volatiles were removed in vacuo. The crude material was dissolved in DMF (1.5 mL) and methoxycarbonylamino-phenyl-acetic acid (28.2 mg, 0.134 mmol), DIEA (52.2 mg, 0.4 mmol), and COMU (57.7 mg, 0.134 mmol) was added and stirring at room temperature was continued. After 15 minutes, the reaction was quenched with aqueous HCl (1N, 0.1 mL). The crude reaction mixture was purified via RP-HPLC (eluent: water/MeCN w/0.1% TFA). The product containing fractions were lyophilized to give the final compound (59.3.0 mg).

LCMS-ESI$^+$: calc'd for $C_{49}H_{49}N_9O_6$: 859.9 (M$^+$) found: 860.4 (M+H$^+$)

Example CY

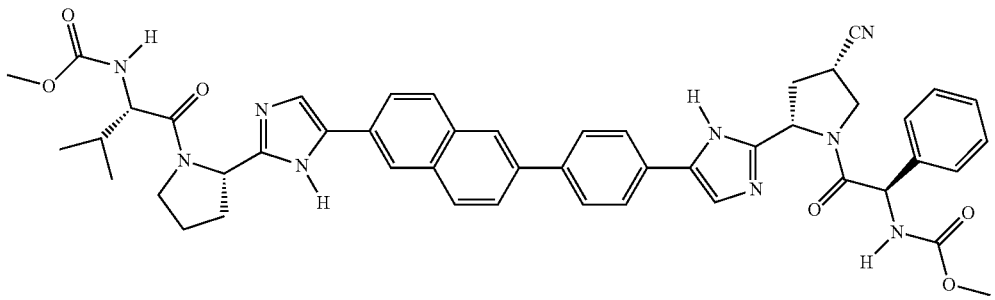

[1-(2-{5-[6-(4-{2-[4-Cyano-1-(2-methoxycarbo-nylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Synthesized similar to [1-(2-{5-[6-(4-{2-[4-Cyano-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, reverting the order of Suzuki coupling and reaction introduction of the amino acid moiety on the cyano proline using methoxycarbonylamino-phenyl-acetic acid.

LCMS-ESI$^+$: calc'd for $C_{48}H_{49}N_9O_6$: 847.9 (M$^+$) found: 848.5 (M+H$^+$).

Example CZ

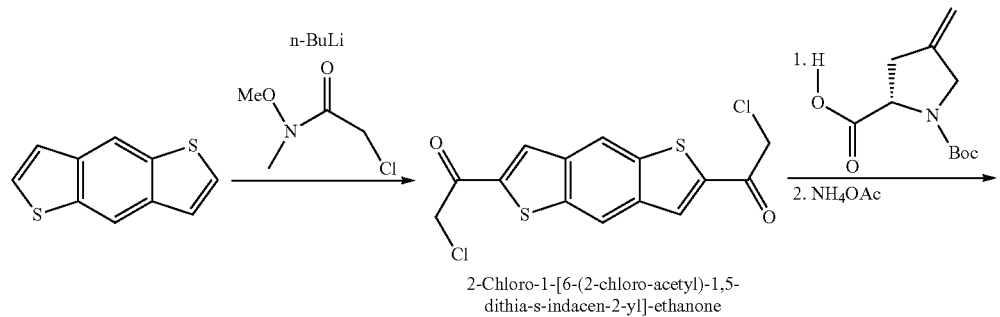

2-Chloro-1-[6-(2-chloro-acetyl)-1,5-dithia-s-indacen-2-yl]-ethanone

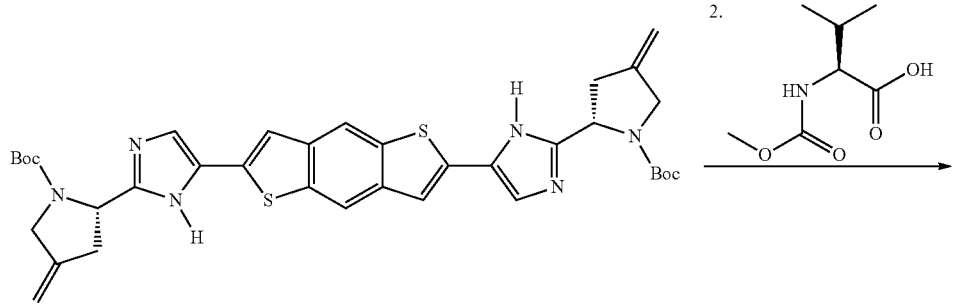

(1-{2-[5-(6-{2-[1-Boc-4-methylene-pyrrolidin-2-yl]-3H-imidazol-4-yl}-1,5-dithia-s-indacen-2-yl)-1H-imidazol-2-yl]-4-methylene-pyrrolidine-1-Boc

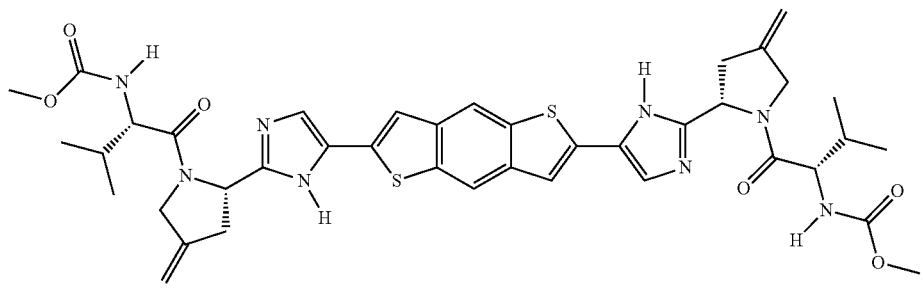

(1-{2-[5-(6-{2-[1-(2-Methoxycarbonylamino-3-methyl-butyryl)-4-methylene-pyrrolidin-2-yl]-3H-imidazol-4-yl}-1,5-dithia-s-indacen-2-yl)-1H-imidazol-2-yl]-4-methylene-pyrrolidine-1-carbonyl}-2-methyl-propyl)-carbamic acid methyl ester

2-Chloro-1-[6-(2-chloro-acetyl)-1,5-dithia-s-indacen-2-yl]-ethanone 1,5-Dithia-s-indacene (100 mg, 0.526 mmol) was dissolved in THF (8 mL) and cooled to −78° C. n-BuLi solution (1.6M, 0.723 mL) was added and stirring at −78° C. was continued. After 120 the amide was added as a solution in THF (0.5 mL). After 30 min the reaction was quenched with ammonium chloride aqueous solution and was warmed to room temperature. The aqueous layer was removed and MeOH (8 mL) was added. The resultant solid was collected; crude yield 132.6 mg.

(1-(2-[5-(6-{2-[1-Boc-4-methylene-pyrrolidin-2-yl]-3H-imidazol-4-yl}-1,5-dithia-s-indacen-2-yl)-1H-imidazol-2-yl]-4-methylene-pyrrolidine-1-Boc The crude material from the previous step (132.6 mg, 0.388 mmol), 4-methylene-pyrrolidine-1,2-dicarboxylic acid 1-tert-butyl ester (0.194 mg, 0.855 mmol), potassium carbonate (160 mg) and sodium iodide (20 mg) were heated in acetone at 60° C. for 2 hours and cooled to room temperature. The crude reaction mixture was partitioned between EtOAc and brine/aqueous sodium bicarbonate solution. The organic layer was dried over sodium sulfate. Filtration and evaporation of solvents gives the crude his ester product (259.2 mg).

The bis-ester (259.2 mg) was dissolved in m-xylenes and heated at 135° C. Solid ammonium acetate (270 mg) was added and the reaction was heated at 135° C. for 3 hours. The reaction was cooled to room temperature and the volatiles were removed in vacuo. The crude product was partitioned between EtOAc and brine/aqueous sodium bicarbonate solution. The organic layer was dried over sodium sulfate. Filtration and evaporation of solvents gives the crude product. Purification via chromatography on silica gel yielded the product (84.5 mg).

(1-{2-[5-(6-{2-[1-(2-Methoxycarbonylamino-3-methyl-butyryl)-4-methylene-pyrrolidin-2-yl]-3H-imidazol-4-yl}-1,5-dithia-s-indacen-2-yl)-1H-imidazol-2-yl]-4-methylene-pyrrolidine-1-carbonyl}-2-methyl-propyl)-carbamic acid methyl ester The product of the previous step (28.0 mg, 0.041 mmol) was stirred in DCM (0.7 mL)/HCl in dioxane (4M, 0.6 mL). After 45 minutes all volatiles were removed in vacuo. The crude material was dissolved in DMF (1 mL) and valine carbamate (15.7 mg, 0.0899 mmol), DIEA (23.2 mg, 0.180 mmol), and COMU (38.4 mg, 0.0899 mmol) was added and stirring at room temperature was continued. After 15 minutes, the reaction was quenched with water (0.1 mL). The crude reaction mixture was purified via RP-HPLC (eluent: water/McCN w/0.1% TFA). The product containing fractions were lyophilized to give the final compound (18.0 mg).

LCMS-ESI$^+$: calc'd for $C_{40}H_{46}N_8O_6S_2$: 798.9 (M$^+$) found: 799.4 (M+H$^+$)

Example DA

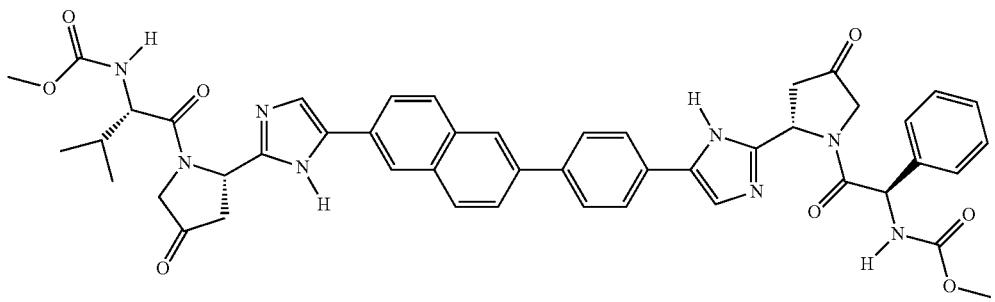

[1-(2-{5-[6-(4-{2-[1-(2-Methoxycarbonylamino-2-phenyl-acetyl)-4-oxo-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Synthesized similar to [1-(2-{4-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-4-oxo-pyrrolidine-1-carbonyl)-2-methyl-propyl]-carbamic acid methyl ester using 4-Hydroxy-2-{5-[4-(6-{2-[1-(2-methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester in the oxidation reaction.

LCMS-ESI$^+$: calc'd for $C_{47}H_{48}N_8O_7$: 836.9 ($M^+$) found: 837.4 ($M+H^+$)

Example DB

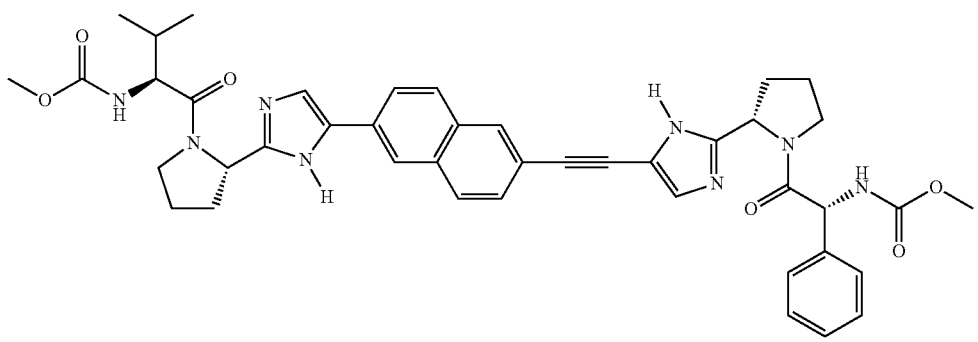

methyl (S)-1-((S)-2-(5-(6-(((2-((S)-1-((R)-2-methoxycarbonylamino-2-phenylacetyl)pyrrolidin-2-yl)-1H-imidazol-5-yl)ethynyl)naphthalen-2yl)-1H-imidazol-2-yl)pyrrolidin-1-yl)-3-methyl-1-oxobutan-2-ylcarbamate Methyl (S)-1-((S)-2-(5-(6-(((2-((S)-1-((R)-2-methoxycarbonylamino-2-phenylacetyl)pyrrolidin-2-yl)-1H-imidazol-5-yl)ethynyl)naphthalen-2-yl)-1H-imidazol-2-yl)pyrrolidin-1-yl)-3-methyl-1-oxobutan-2-ylcarbamate: MS (ESI) m/z 771 [M+H]$^+$.

Example DC

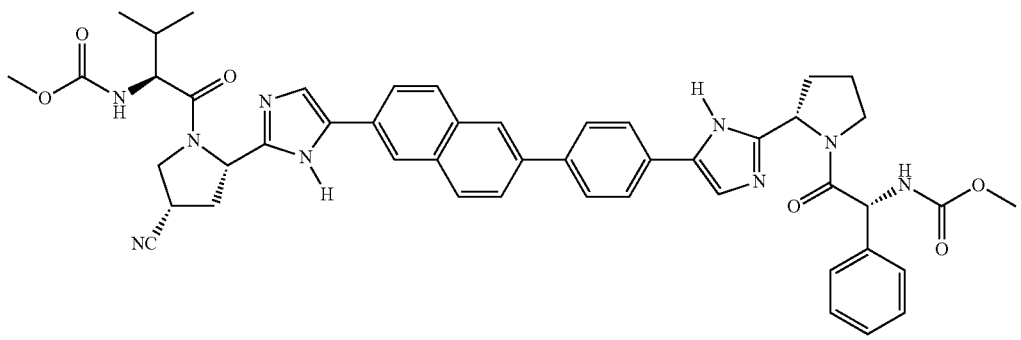

methyl (S)-1-((2S,4S)-2-(5-(6-(4-(2-((S)-1-((R)-2-methoxycarbonylamino-2-phenylacetyl)pyrrolidin-2-yl)-1H-imidazol-5-yl)phenyl)naphthalen-2-yl)-1H-imidazol-2-yl)-4-cyanopyrrolidin-1-yl)-3-methyl-1-oxobutan-2-ylcarbamate Methyl (S)-1-((2S,4S)-2-(5-(6-(4-(2-((S)-1-((R)-2-methoxycarbonylamino-2-phenylacetyl)pyrrolidin-2-yl)-1H-imidazol-5-yl)phenyl)naphthalen-2-yl)-1H-imidazol-2-yl)-4-cyanopyrrolidin-1-yl)-3-methyl-1-oxobutan-2-ylcarbamate: MS (ESI) m/z 848 [M+H]$^+$.

Example DD

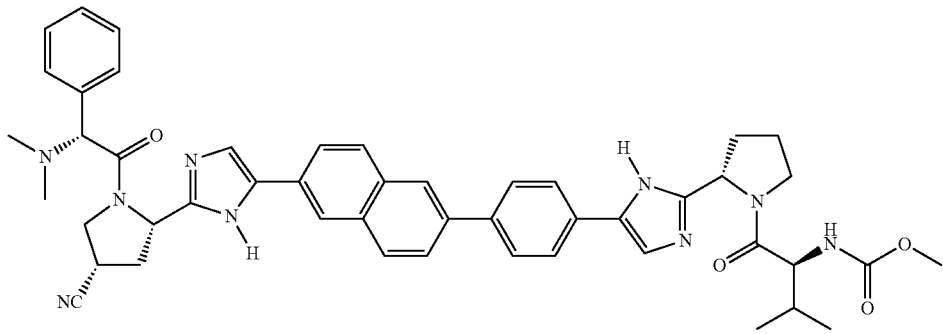

methyl (S)-1-((S)-2-(5-(4-(6-(2-((2S,4S)-4-cyano-1-((R)-2-(dimethylamino)-2-phenylacetyl)pyrrolidin-2-yl)-1H-imidazo-5-yl)naphthalen-2-yl)phenyl)-1H-imidazol-2-yl)pyrrolidin-1-yl)-3-methyl-1-oxobutan-2-ylcarbamate Methyl (S)-1-((S)-2-(5-(4-(6-(2-((2S,4S)-4-cyano-1-((R)-2-(dimethylamino)-2-phenylacetyl)pyrrolidin-2-yl)-1H-imidazo-5-yl)naphthalen-2-yl)phenyl)-1H-imidazol-2-yl)pyrrolidin-1-yl)-3-methyl-1-oxobutan-2-ylcarbamate: MS (ESI) m/z 818 [M+H]$^+$.

Example DE

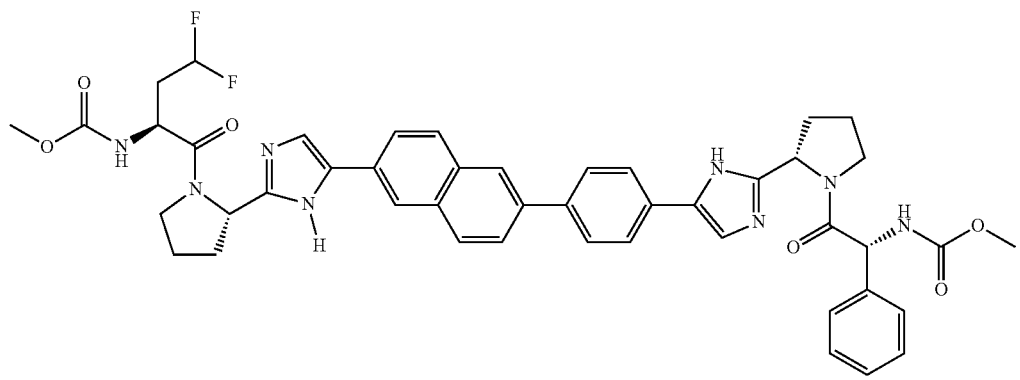

methyl (S)-1-((S)-2-(5-(6-(4-(2-((S)-1-((R)-2-methoxycarbonylamino-2-phenylacetyl)pyrrolidin-2-yl)-1H-imidazol-5-yl)phenyl)naphthalen-2-yl)-1H-imidazol-2-yl)pyrrolidin-1-yl)-4,4-difluoro-1-oxobutan-2-ylcarbamate Methyl (S)-1-((S)-2-(5-(6-(4-(2-((S)-1-((R)-2-methoxycarbonylamino-2-phenylacetyl)pyrrolidin-2-yl)-1H-imidazol-5-yl)phenyl)naphthalen-2-yl)-1H-imidazol-2-yl)pyrrolidin-1-yl)-4,4-difluoro-1-oxobutan-2-ylcarbamate: MS (ESI) m/z 845 [M+H]$^+$.

Example DF

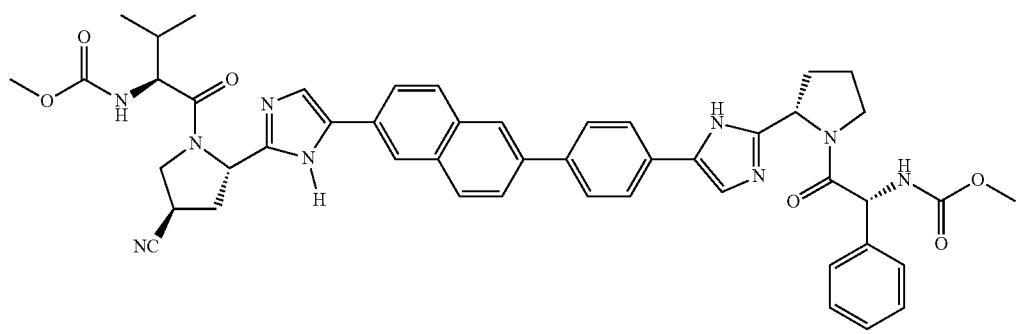

methyl (S)-1-((2S,4R)-2-(5-(6-(4-(2-((S)-1-((R)-2-methoxycarbonylamino-2-phenylacetyl)pyrrolidin-2-yl)-1H-imidazol-5-yl)phenyl)naphthalen-2-yl)-1H-imidazol-2-yl)-4-cyanopyrrolidin-1-yl)-3-methyl-1-oxobutan-2-ylcarbamate Methyl (S)-1-((2S,4R)-2-(5-(6-(4-(2-((S)-1-((R)-2-methoxycarbonylamino-2-phenylacetyl)pyrrolidin-2-yl)- 1H-imidazol-5-yl)phenyl)naphthalen-2-yl)-1H-imidazol-2-yl)-4-cyanopyrrolidin-1-yl)-3-methyl-1-oxobutan-2-ylcarbamate: MS (ESI) m/z 848 [M+H]$^+$.

Example DG

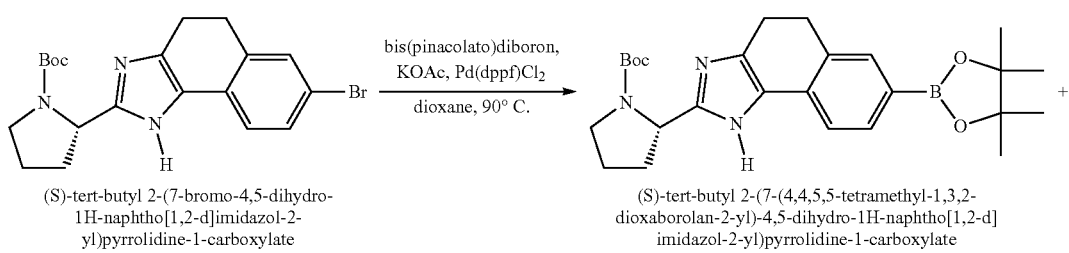

(S)-tert-butyl 2-(7-bromo-4,5-dihydro-1H-naphtho[1,2-d]imidazol-2-yl)pyrrolidine-1-carboxylate (S)-tert-butyl 2-(7-(4,4,5,5-tetramethyl-1,3,2-dioxaborolan-2-yl)-4,5-dihydro-1H-naphtho[1,2-d]imidazol-2-yl)pyrrolidine-1-carboxylate

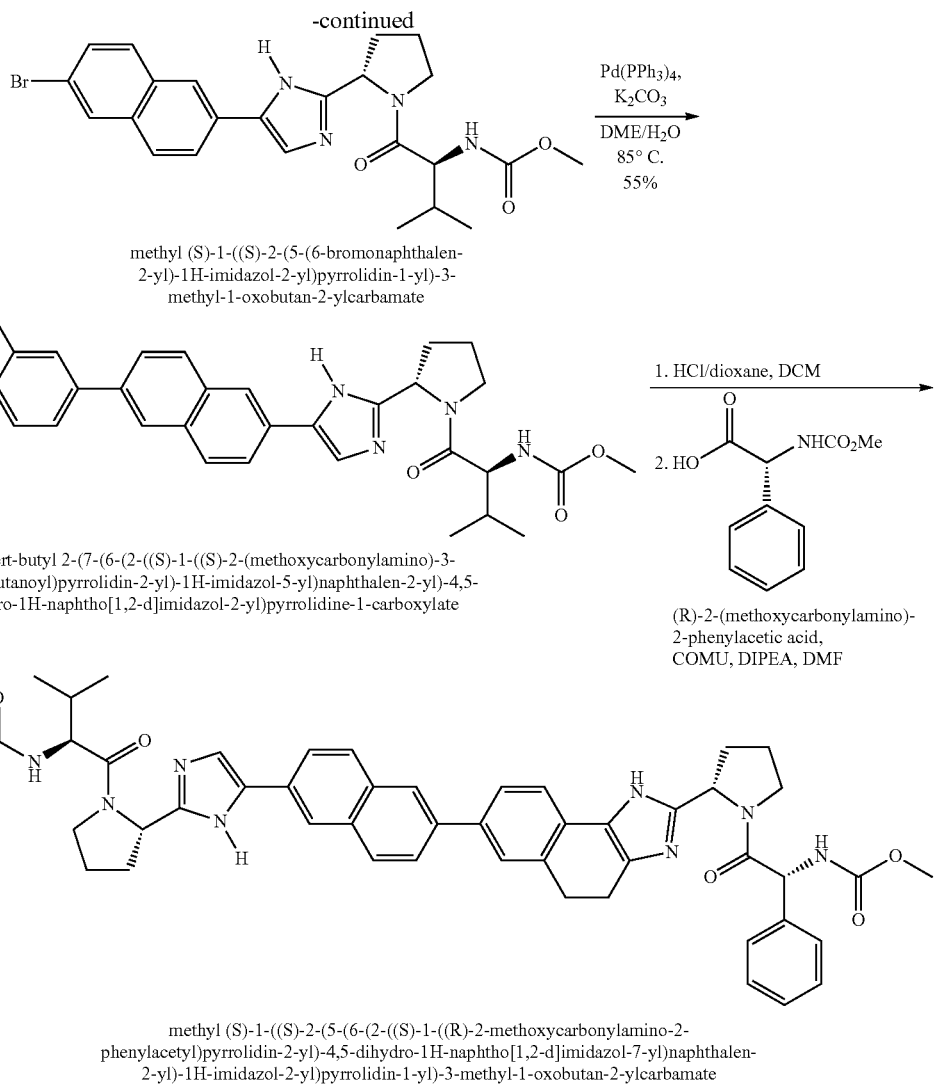

methyl (S)-1-((S)-2-(5-(6-bromonaphthalen-2-yl)-1H-imidazol-2-yl)pyrrolidin-1-yl)-3-methyl-1-oxobutan-2-ylcarbamate (S)-tert-butyl 2-(7-(6-(2-((S)-1-((S)-2-(methoxycarbonylamino)-3-methylbutanoyl)pyrrolidin-2-yl)-1H-imidazol-5-yl)naphthalen-2-yl)-4,5-dihydro-1H-naphtho[1,2-d]imidazol-2-yl)pyrrolidine-1-carboxylate (R)-2-(methoxycarbonylamino)-2-phenylacetic acid, COMU, DIPEA, DMF methyl (S)-1-((S)-2-(5-(6-(2-((S)-1-((R)-2-methoxycarbonylamino-2-phenylacetyl)pyrrolidin-2-yl)-4,5-dihydro-1H-naphtho[1,2-d]imidazol-7-yl)naphthalen-2-yl)-1H-imidazol-2-yl)pyrrolidin-1-yl)-3-methyl-1-oxobutan-2-ylcarbamate (S)-tert-butyl 2-(7-(4,4,5,5-tetramethyl-1,3,2-dioxaborolan-2-yl)-4,5-dihydro-1H-naphtho[1,2-d]imidazol-2-yl)pyrrolidine-1-carboxylate: (S)-tert-butyl 2-(7-bromo-4,5-dihydro-1H-naphtho[1,2-d]imidazol-2-yl)pyrrolidine-1-carboxylate (1.52 g, 3.63 mmol), bis(pinacolato)diboron (1.11 g, 4.36 mmol), KOAc (1.07 g, 10.89 mmol) and Pd(dppf)Cl$_2$ (266 mg, 0.363 mmol) were combined in dioxane (18 mL). The reaction mixture was degassed for 10 min with bubbling N$_2$, then heated to 90° C. for 2 h 15 min before being cooled to RT. The mixture was then diluted with EtOAc and washed with saturated aqueous NaHCO$_3$ and brine. The organic phase was dried over MgSO$_4$, filtered and concentrated. The crude residue was purified by silica column chromatography (50% to 100% EtOAc/hexane) to afford the title compound (1.23 g, 73%).

(S)-tert-butyl 2-(7-(6-(2-((S)-1-((S)-2-(methoxycarbonylamino)-3-methylbutanoyl)pyrrolidin-2-yl)-1H-imidazol-5-yl)naphthalen-2-yl)-4,5-dihydro-1H-naphtho[1,2-d]imidazol-2-yl)pyrrolidine-1-carboxylate: (S)-tert-butyl 2-(7-(4,4,5,5-tetramethyl-1,3,2-dioxaborolan-2-yl)-4,5-dihydro-1H-naphtho[1,2-d]imidazol-2-yl)pyrrolidine-1-carboxylate (574 mg, 1.23 mmol), methyl (S)-1-((S)-2-(5-(6-bromonaphthalen-2-yl)-1H-imidazol-2-yl)pyrrolidin-1-yl)-3-methyl-1-oxobutan-2-ylcarbamate (616 mg, 1.23 mmol), Pd(PPh$_3$)$_4$ (142 mg, 0.123 mmol), and K$_2$CO$_3$ (2M in H$_2$O, 1.2 mL, 2.4 mmol) were combined in DME. The reaction mixture was degassed with bubbling N$_2$ for 10 min, then heated to 85° C. After 16 h, the reaction mixture was cooled to RT and concentrated. The crude residue was purified by silica column chromatography (0% to 30% MeOH/EtOAc) to afford the title compound (516 mg, 55%).

Methyl (S)-1-((S)-2-(5-(6-(2-((S)-1-((R)-2-methoxycarbonylamino-2-phenylacetyl)pyrrolidin-2-yl)-4,5-dihydro-1H-naphtho[1,2-d]imidazol-7-yl)naphthalen-2-yl)-1H-imidazol-2-yl)pyrrolidin-1-yl)-3-methyl-1-oxobutan-2-ylcarbamate: (S)-tert-butyl 2-(7-(6-(2-((S)-1-((S)-2-(methoxycarbonylamino)-3-methylbutanoyl)pyrrolidin-2-yl)-1H-imidazol-5-yl)naphthalen-2-yl)-4,5-dihydro-1H-naphtho[1,2-d]imidazol-2-yl)pyrrolidine-1-carboxylate (246 mg, 0.325 mmol) was dissolved in dichloromethane (10 mL) and HCl (4 M in dioxane, 2 mL) was added. After stirring at RT for 1 h 40 min, the reaction mixture was concentrated. The crude residue was treated with (R)-2-(methoxycarbonylamino)-2-phenylacetic acid (75 mg, 0.358 mmol), COMU (139 mg, 0.325 mmol) and DMF (6 mL). DIPEA was added to the stirred reaction mixture dropwise. After 35 min, 1 mL H$_2$O was added and the crude solution was purified by HPLC to afford the title compound (177 mg, 64%). MS (ESI) m/z 849 [M+H]$^+$.

Example DH

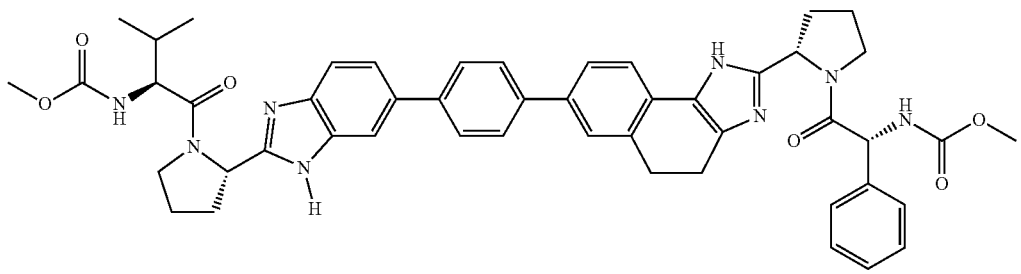

methyl (S)-1-((S)-2-(6-(4-(2-((S)-1-((R)-2-methoxy-carbonylamino-2-phenylacetyl)pyrrolidin-2-yl)-4,5-dihydro-1H-naphtho[1,2-d]imidazol-7-yl)phenyl)-1H-benzo[d]imidazol-2-yl)pyrrolidin-1-yl)-3-methyl-1-oxobutan-2-ylcarbamate Methyl (S)-1-((S)-2-(6-(4-(2-((S)-1-((R)-2-methoxycarbonylamino-2-phenylacetyl)pyrrolidin-2-yl)-4,5-dihydro-1H-naphtho[1,2-d]imidazol-7-yl)phenyl)-1H-benzo[d]imidazol-2-yl)pyrrolidin-1-yl)-3-methyl-1-oxobutan-2-ylcarbamate: MS (ESI) m/z 849 [M+H]$^+$.

Example DI

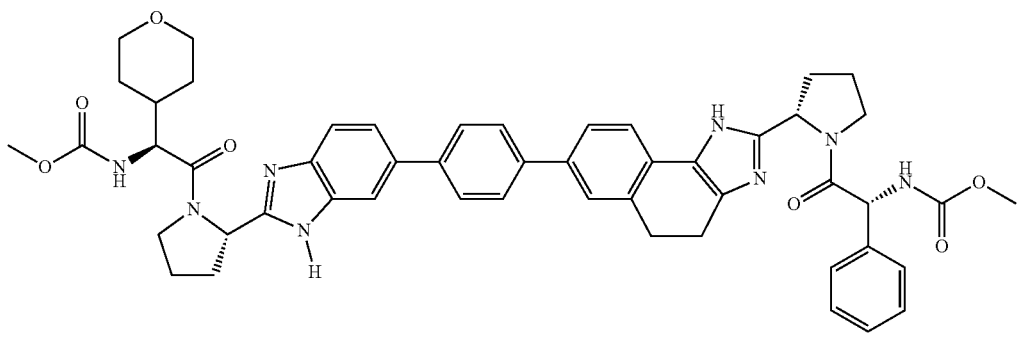

methyl (S)-2-((S)-2-(6-(4-(2-((S)-1-((R)-2-methoxy-carbonylamino-2-phenylacetyl)pyrrolidin-2-yl)-4,5-dihydro-1H-naphtho[1,2-d]imidazol-7-yl)phenyl)-1H-benzo[d]imidazol-2-yl)pyrrolidin-1-yl)-2-oxo-1-(tetrahydro-2H-pyran-4-yl)ethylcarbamate Methyl (S)-2-((S)-2-(6-(4-(2-((S)-1-((R)-2-methoxycarbonylamino-2-phenylacetyl)pyrrolidin-2-yl)-4,5-dihydro-1H-naphtho[1,2-d]imidazol-7-yl)phenyl)-1H-benzo[d]imidazol-2-yl)pyrrolidin-1-yl)-2-oxo-1-(tetrahydro-2H-pyran-4-yl)ethylcarbamate: MS (ESI) m/z 891 [M+H]$^+$.

Example DJ

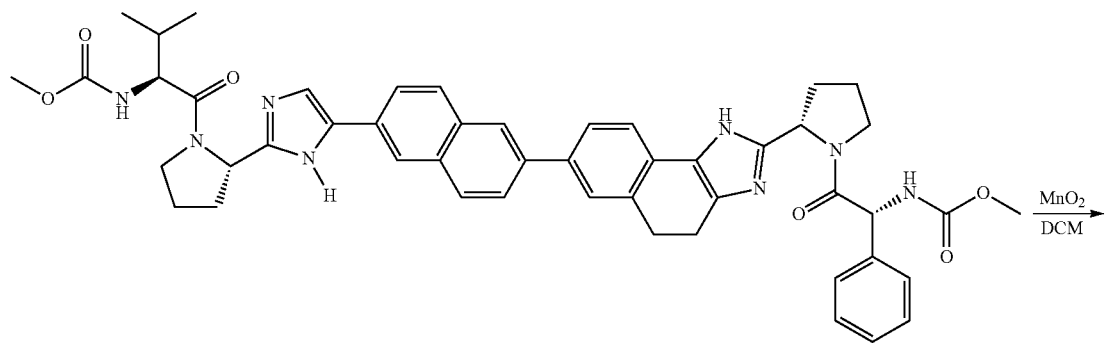

methyl (S)-1-((S)-2-(5-(6-(2-((S)-1-((R)-2-methoxycarbonylamino-2-phenylacetyl)pyrrolidin-2-yl)-4,5-dihydro-1H-naphtho[1,2-d]imidazol-7-yl)naphthalen-2-yl)-1H-imidazol-2-yl)pyrrolidin-1-yl)-3-methyl-1-oxobutan-2-ylcarbamate

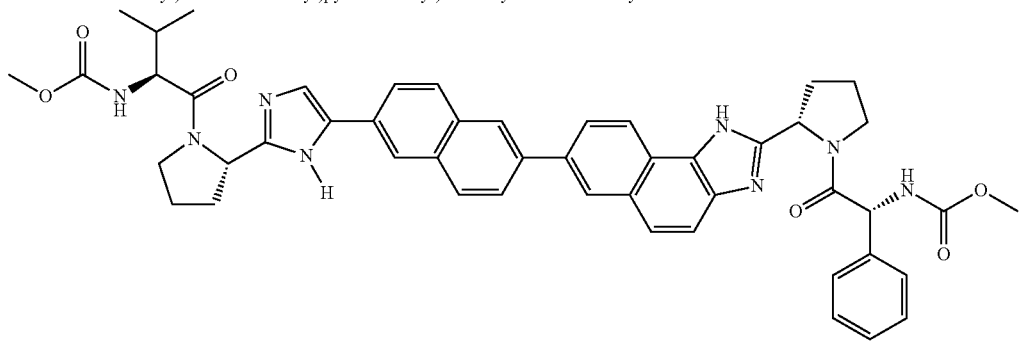

methyl (S)-1-((S)-2-(5-(6-(2-((S)-1-((R)-2-methoxycarbonylamino-2-phenylacetyl)pyrrolidin-2-yl)-1H-naphtho[1,2-d]imidazol-7-yl)naphthalen-2-yl)-1H-imidazol-2-yl)pyrrolidin-1-yl)-3-methyl-1-oxobutan-2-ylcarbamate Methyl (S)-1-((S)-2-(5-(6-(2-((S)-1-((R)-2-methoxycarbonylamino-2-phenylacetyl)pyrrolidin-2-yl)-1H-naphtho[1,2-d]imidazol-7-yl)naphthalen-2-yl)-1H-imidazol-2-yl)pyrrolidin-1-yl)-3-methyl-1-oxobutan-2-ylcarbamate: Methyl (S)-1-((S)-2-(5-(6-(2-((S)-1-((R)-2-methoxycarbonylamino-2-phenylacetyl)pyrrolidin-2-yl)-4,5-dihydro-1H-naphtho[1,2-d]imidazol-7-yl)naphthalen-2-yl)-1H-imidazol-2-yl)pyrrolidin-1-yl)-3-methyl-1-oxobutan-2-ylcarbamate (150 mg, 0.178 mmol) was dissolved in DCM (9 mL) and $MnO_2$ (155 mg, 1.78 mmol) was added. After stirring for 16.5 h, more $MnO_2$ (619 mg, 7.12 mmol) was added and the reaction mixture was heated to reflux. 1.5 h later, 9 mL DCM were added and $MnO_2$ (619 mg, 7.12 mmol) was added. After another 4 h, $MnO_2$ (619 mg, 7.12 mmol) was added. After and additional 16 h, the reaction mixture was filtered over celite and concentrated. The crude residue was purified by HPLC to afford the title compound (42 mg, 29%). MS (ESI) m/z 847 [M+H]+.

Example DK

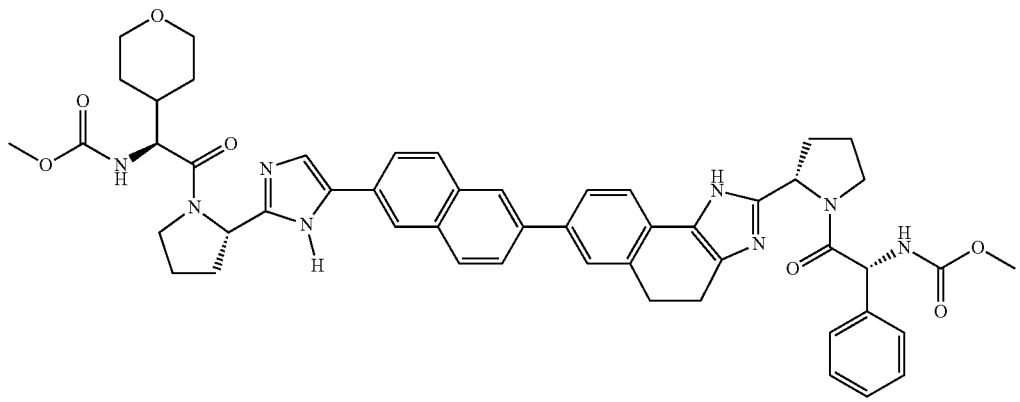

methyl (S)-2-((S)-2-(5-(6-(2-((S)-1-((R)-2-methoxy-carbonylamino-2-phenylacetyl)pyrrolidin-2-yl)-4,5-dihydro-1H-naphtho[1,2-d]imidazol-7-yl)naphthalen-2-yl)-1H-imidazol-2-yl)pyrrolidin-1-yl)-2-oxo-1-(tetrahydro-2H-pyran-4-yl)ethylcarbamate Methyl (S)-2-((S)-2-(5-(6-(2-((S)-1-((R)-2-methoxycarbonylamino-2-phenylacetyl)pyrrolidin-2-yl)-4,5-dihydro-1H-naphtho[1,2-d]imidazol-7-yl)naphthalen-2-yl)-1H-imidazol-2-yl)pyrrolidin-1-yl)-2-oxo-1-(tetrahydro-2H-pyran-4-yl)ethylcarbamate: Title compound was synthesized using methods analogous to the preparation of methyl (S)-1-((S)-2-(5-(6-(2-((S)-1-((R)-2-methoxycarbonylamino-2-phenyl-lacetyl)pyrrolidin-2-yl)-4,5-dihydro-1H-naphtho[1,2-d]imidazol-7-yl)naphthalen-2-yl)-1H-imidazol-2-yl)pyrrolidin-1-yl)-3-methyl-1-oxobutan-2-ylcarbamate, substituting methyl (S)-2-((S)-2-(5-(6-bromonaphthalen-2-yl)-1H-imidazol-2-yl)pyrrolidin-1-yl)-2-oxo-1-(tetrahydro-2H-pyran-4-yl)ethylcarbamate for methyl (S)-1-((S)-2-(5-(6-bromonaphthalen-2-yl)-1H-imidazol-2-yl)pyrrolidin-1-yl)-3-methyl-1-oxobutan-2-ylcarbamate. MS (ESI) m/z 891 [M+H]+.

Example DL

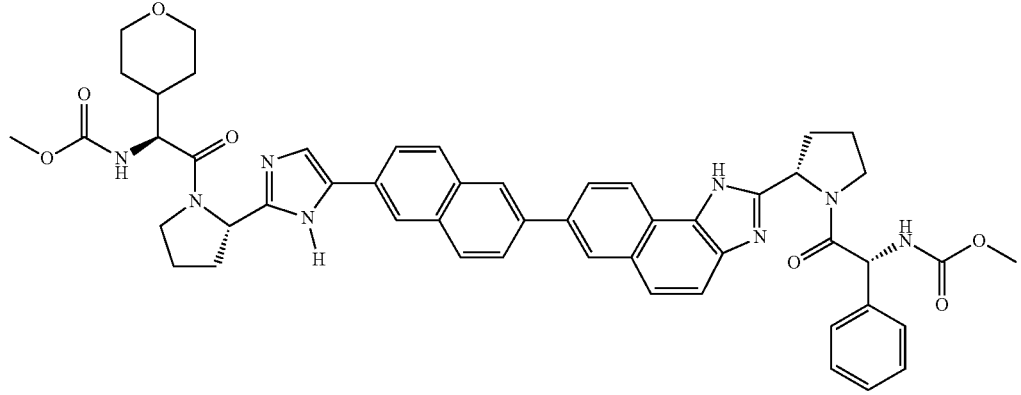

methyl (S)-2-((S)-2-(5-(6-(2-((S)-1-((R)-2-methoxy-carbonylamino-2-phenylacetyl)pyrrolidin-2-yl)-1H-naphtho[1,2-d]imidazol-7-yl)naphthalen-2-yl)-1H-imidazol-2-yl)pyrrolidin-1-yl)-2-oxo-1-(tetrahydro-2H-pyran-4-yl)ethylcarbamate Title compound was synthesized using methods analogous to the preparation of methyl (S)-1-((S)-2-(5-(6-(2-((S)-1-((R)-2-methoxycarbonylamino-2-phenylacetyl)pyrrolidin-2-yl)-1H-naphtho[1,2-d]imidazol-7-yl)naphthalen-2-yl)-1H-imidazol-2-yl)pyrrolidin-1-yl)-3-methyl-1-oxobutan-2-ylcarbamate, substituting methyl (S)-2-((S)-2-(5-(6-(2-((S)-1-((R)-2-methoxycarbonylamino-2-phenylacetyl)pyrrolidin-2-yl)-4,5-dihydro 1H-naphtho[1,2-d]imidazol-7-yl)naphthalen-2-yl)-1H-imidazol-2-yl)pyrrolidin-1-yl)-2-oxo-1-(tetrahydro-2H-pyran-4-yl)ethylcarbamate for methyl (S)-1-((S)-2-(5-(6-(2-((S)-1-((R)-2-methoxycarbonylamino-2-phenylacetyl)pyrrolidin-2-yl)-4,5-dihydro-1H-naphtho[1,2-d]imidazol-7-yl)naphthalen-2-yl)-1H-imidazol-2-yl)pyrrolidin-1-yl)-3-methyl-1-oxobutan-2-ylcarbamate. MS (ESI) m/z 889 [M+H]+.

Example DM

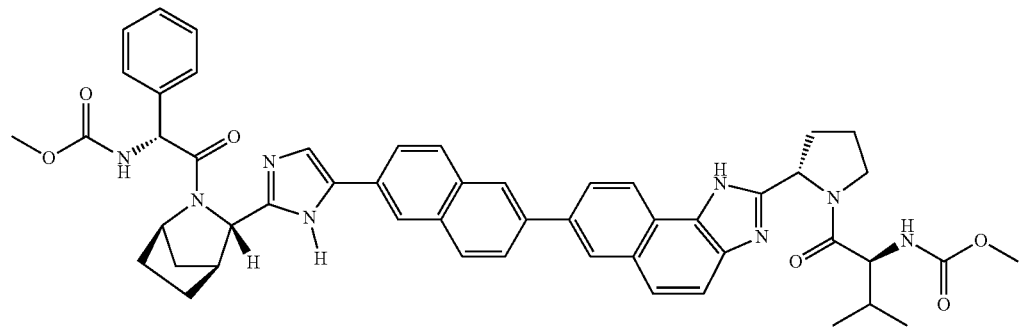

methyl (R)-2-((1R,3S,4S)-3-(5-(6-(2-((S)-1-((S)-2-methoxycarbonylamino-3-methylbutanoyl)pyrrolidin-2-yl)-1H-naphtho[1,2-d]imidazol-7-yl)naphthalen-2-yl)-1H-imidazol-2-yl)-2-azabicyclo[2.2.1]heptan-2-yl)-2-oxo-1-phenylethylcarbamate Methyl (R)-2-((1R,3S,4S)-3-(5-(6-(2-((S)-1-((S)-2-methoxycarbonylamino-3-methylbutanoyl)pyrrolidin-2-yl)-1H-naphtho[1,2-d]imidazol-7-yl)naphthalen-2-yl)-1H-imidazol-2-yl)-2-azabicyclo[2.2.1]heptan-2-yl)-2-oxo-1-phenylethylcarbamate: MS (ESI) m/z 874 [M+H]$^+$.

Example DN

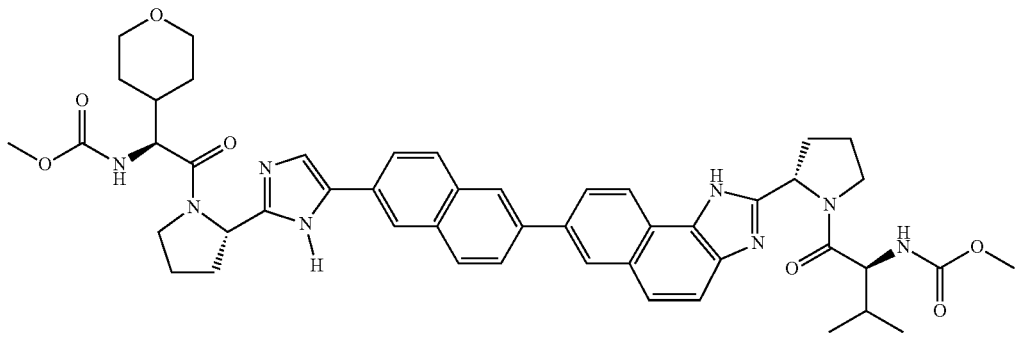

methyl (S)-2-((S)-2-(5-(6-(2-((S)-1-((S)-2-methoxycarbonylamino-3-methylbutanoyl)pyrrolidin-2-yl)-1H-naphtho[1,2-d]imidazol-7-yl)naphthalen-2-yl)-1H-imidazol-2-yl)pyrrolidin-1-yl)-2-oxo-1-(tetrahydro-2H-pyran-4-yl)ethylcarbamate Methyl (S)-2-((S)-2-(5-(6-(2-((S)-1-((S)-2-methoxycarbonylamino-3-methylbutanoyl)pyrrolidin-2-yl)-1H-naphtho[1,2-d]imidazol-7-yl)naphthalen-2-yl)-1H-imidazol-2-yl)pyrrolidin-1-yl)-2-oxo-1-(tetrahydro-2H-pyran-4-yl)ethylcarbamate: MS (ESI) m/z 856 [M+H]$^+$.

Example DO

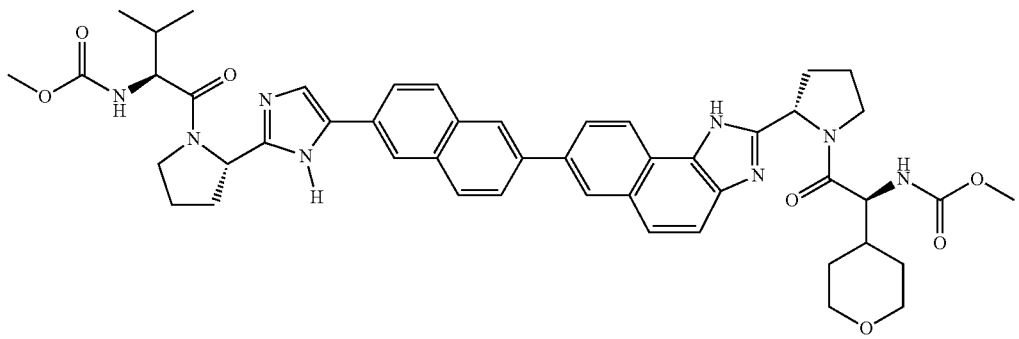

methyl (S)-1-((S)-2-(5-(6-(2-((S)-1-((S)-2-methoxycarbonylamino-2-(tetrahydro-2H-pyran-4-yl)acetyl)pyrrolidin-2-yl)-1H-naphtho[1,2-d]imidazol-7-yl)naphthalen-2-yl)-1H-imidazol-2-yl)pyrrolidin-1-yl)-3-methyl-1-oxobutan-2-ylcarbamate Methyl (S)-1-((S)-2-(5-(6-(2-((S)-1-((S)-2-methoxycarbonylamino-2-(tetrahydro-2H-pyran-4-yl)acetyl)pyrrolidin-2-yl)-1H-naphtho[1,2-d]imidazol-7-yl)naphthalen-2-yl)-1H-imidazol-2-yl)pyrrolidin-1-yl)-3-methyl-1-oxobutan-2-ylcarbamate. MS: (ESI) m/z 856 [M+H]$^+$.

Example DP
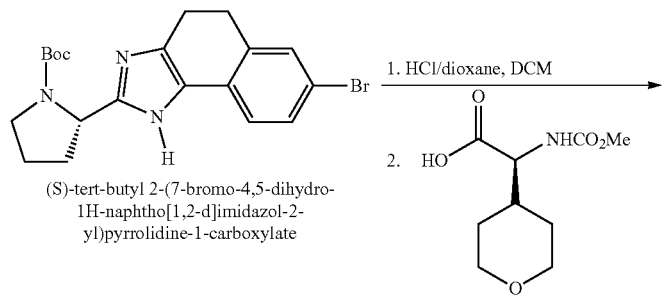
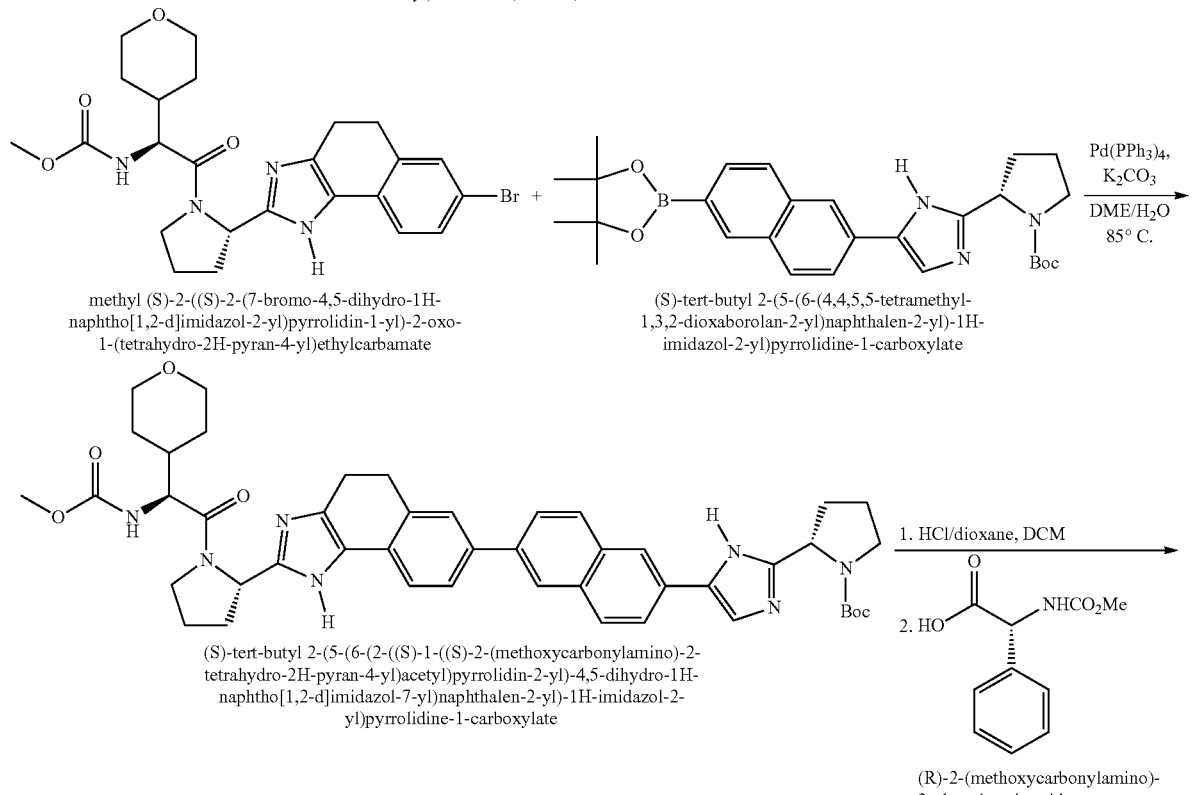
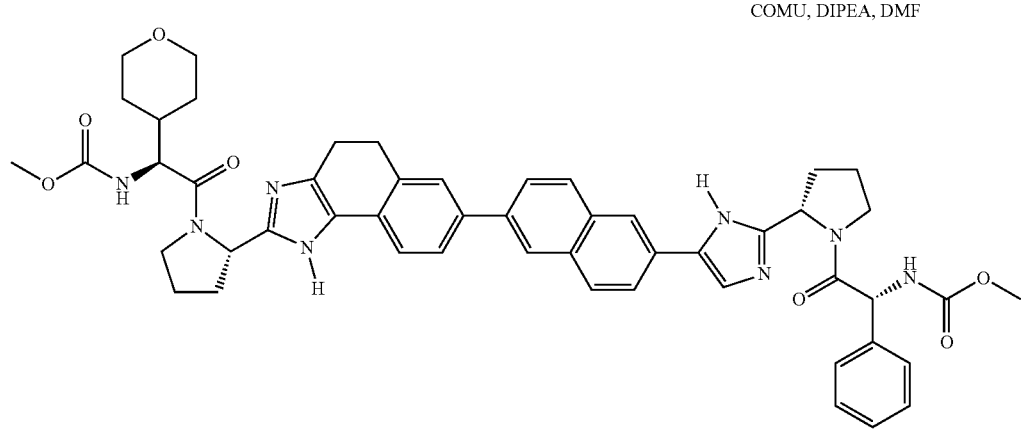
methyl (S)-2-((S)-2-(7-(6-(2-((S)-1-((R)-2-methoxycarbonylamino-2-phenylacetyl)pyrrolidin-2-yl)-1H-imidazol-5-yl)naphthalen-2-yl)-4,5-dihydro-1H-naphtho[1,2-d]imidazol-2-yl)pyrrolidin-1-yl)-2-oxo-1-(tetrahydro-2H-pyran-4-yl)ethylcarbamate Methyl (S)-2-((S)-2-(7-bromo-4,5-dihydro-1H-naphtho[1,2-d]imidazol-2-yl)pyrrolidin-1-yl)-2-oxo-1-(tetrahydro-2H-pyran-4-yl)ethylcarbamate: (S)-tert-butyl 2-(7-bromo-4,5-dihydro-1H-naphtho[1,2-d]imidazol-2-yl)pyrrolidine-1-carboxylate (314 mg, 0.750 mmol) was dissolved in DCM (5 mL) and HCl (4M in dioxane, 1 mL) was added. After stirring for 1 h, the reaction mixture was concentrated and the residue was treated with (S)-2-(methoxycarbonylamino)-2-(tetrahydro-2H-pyran-4-yl)acetic acid (163 mg, 0.750 mmol), HATU (285 mg, 0.750 mmol) and DMF (4 mL). After cooling to 0° C., DIPEA (0.65 mL, 3.75 mmol) was added dropwise and the reaction mixture was allowed to warm to RT. After 4 h, the mixture was diluted with EtOAc and washed with saturated aqueous NaHCO$_3$ and brine, dried over MgSO$_4$, filtered and concentrated. The crude residue was purified by silica column chromatography (0% to 30% MeOH/EtOAc) to afford the title compound (211 mg, 54%).

(S)-tert-butyl 2-(5-(6-(2-((S)-1-((S)-2-(methoxycarbonylamino)-2-(tetrahydro-2H-pyran-4-yl)acetyl)pyrrolidin-2-yl)-4,5-dihydro-1H-naphtho[1,2-d]imidazol-7-yl)naphthalen-2-yl)-1H-imidazol-2-yl)pyrrolidine-1-carboxylate: Methyl (S)-2-((S)-2-(7-bromo-4,5-dihydro-1H-naphtho[1,2-d]imidazol-2-yl)pyrrolidin-1-yl)-2-oxo-1-(tetrahydro-2H-pyran-4-yl)ethylcarbamate (211 mg, 0.408 mmol), (S)-tert-butyl 2-(5-(6-(4,4,5,5-tetramethyl-1,3,2-dioxaborolan-2-yl)naphthalen-2-yl)-1H-imidazol-2-yl)pyrrolidine-1-carboxylate (220 mg, 0.449 mmol), Pd(PPh$_3$)$_4$ (47 mg, 0.0408 mmol) and K$_2$CO$_3$ (2M in H$_2$O, 0.45 mL, 0.9 mmol) were suspended in DME (4 mL). The reaction mixture was degassed for 10 min with N$_2$ then heated to 85° C. After 17 h, it was cooled to RT, diluted with MeOH, filtered over a thiol SPE column and concentrated. The crude residue was purified by silica column chromatography (0% to 40% MeOH/EtOAc) to afford the title compound (130 mg, 40%).

Methyl (S)-2-((S)-2-(7-(6-(2-((S)-1-((R)-2-methoxycarbonylamino-2-phenylacetyl)pyrrolidin-2-yl)-1H-imidazol-5-yl)naphthalen-2-yl)-4,5-dihydro-1H-naphtho[1,2-d]imidazol-2-yl)pyrrolidin-1-yl)-2-oxo-1-(tetrahydro-2H-pyran-4-yl)ethylcarbamate: (S)-tert-butyl 2-(5-(6-(2-((S)-1-((S)-2-(methoxycarbonylamino)-2-(tetrahydro-2H-pyran-4-yl)acetyl)pyrrolidin-2-yl)-4,5-dihydro-1H-naphtho[1,2-d]imidazol-7-yl)naphthalen-2-yl)-1H-imidazol-2-yl)pyrrolidine-1-carboxylate (136 mg, 0.17 mmol) was dissolved in DCM (5 mL) and HCl (4M in dioxane, 1 mL) was added. After stirring for 1 h, the reaction mixture was concentrated and the residue was treated with (R)-2-(methoxycarbonylamino)-2-phenylacetic acid (36 mg, 0.170 mmol), COMU (73 mg, 0.170 mmol) and DMF (3 mL). DIPEA (0.12 mL, 0.68 mmol) was added dropwise. After 20 min, the reaction was quenched by addition of H$_2$O and the crude mixture was purified by HPLC to afford the title compound (57 mg, 38%). MS: (ESI) m/z 891 [M+H]$^+$.

Example DQ

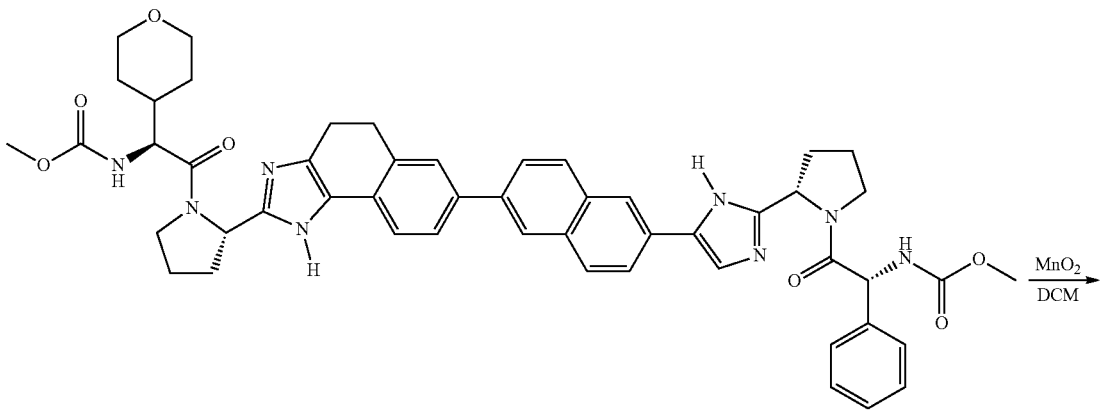

methyl (S)-2-((S)-2-(7-(6-(2-((S)-1-((R)-2-methoxycarbonylamino-2-phenylacetyl)pyrrolidin-2-yl)-1H-imidazol-5-yl)naphthalen-2-yl)-4,5-dihydro-1H-naphtho[1,2-d]imidazol-2-yl)pyrrolidin-1-yl)-2-oxo-1-(tetrahydro-2H-pyran-4-yl)ethylcarbamate

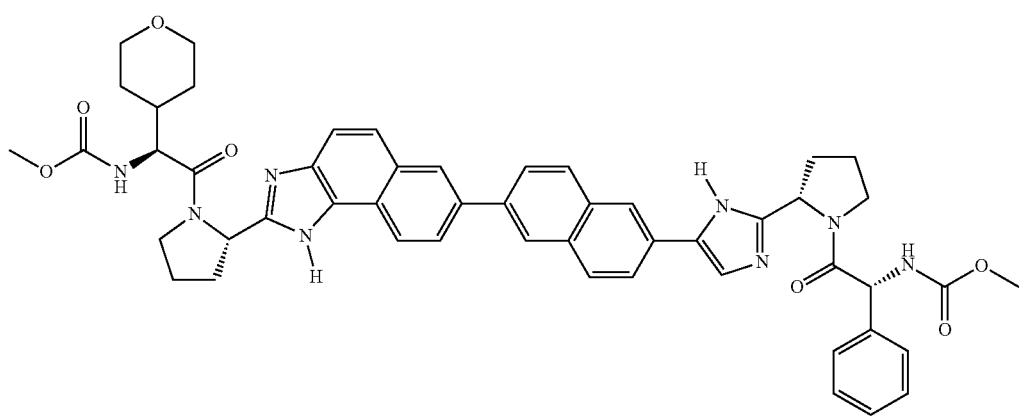

methyl (S)-2-((S)-2-(7-(6-(2-((S)-1-((R)-2-methoxycarbonylamino-2-phenylacetyl)pyrrolidin-2-yl)-1H-imidazol-5-yl)naphthalen-2-yl)-1H-naphtho[1,2-d]imidazol-2-yl)pyrrolidin-1-yl)-2-oxo-1-(tetrahydro-2H-pyran-4-yl)ethylcarbamate Methyl (S)-2-((S)-2-(7-(6-(2-((S)-1-((R)-2-methoxycarbonylamino-2-phenylacetyl)pyrrolidin-2-yl)-1H-imidazol-5-yl)naphthalen-2-yl)-1H-naphtho[1,2-d]imidazol-2-yl)pyrrolidin-1-yl)-2-oxo-1-(tetrahydro-2H-pyran-4-yl)ethylcarbamate:

Methyl (S)-2-((S)-2-(7-(6-(2-((S)-1-((R)-2-methoxycarbonylamino-2-phenylacetyl)pyrrolidin-2-yl)-1H-imidazol-5-yl)naphthalen-2-yl)-4,5-dihydro-1H-naphtho[1,2-d]imidazol-2-yl)pyrrolidin-1-yl)-2-oxo-1-(tetrahydro-2H-pyran-4-yl)ethylcarbamate (51 mg, 0.0572 mmol) was dissolved in DCM (10 mL) and MnO$_2$ (995 mg, 11.45 mmol) was added. After stirring at reflux for 4d, the reaction mixture was diluted with MeOH, filtered over celite and concentrated. The crude residue was dissolved in MeOH, filtered over a bicarbonate SPE and concentrated to afford the title compound (35 mg, 69%). MS: (ESI) m/z 889 [M+H]$^+$.

Example DR

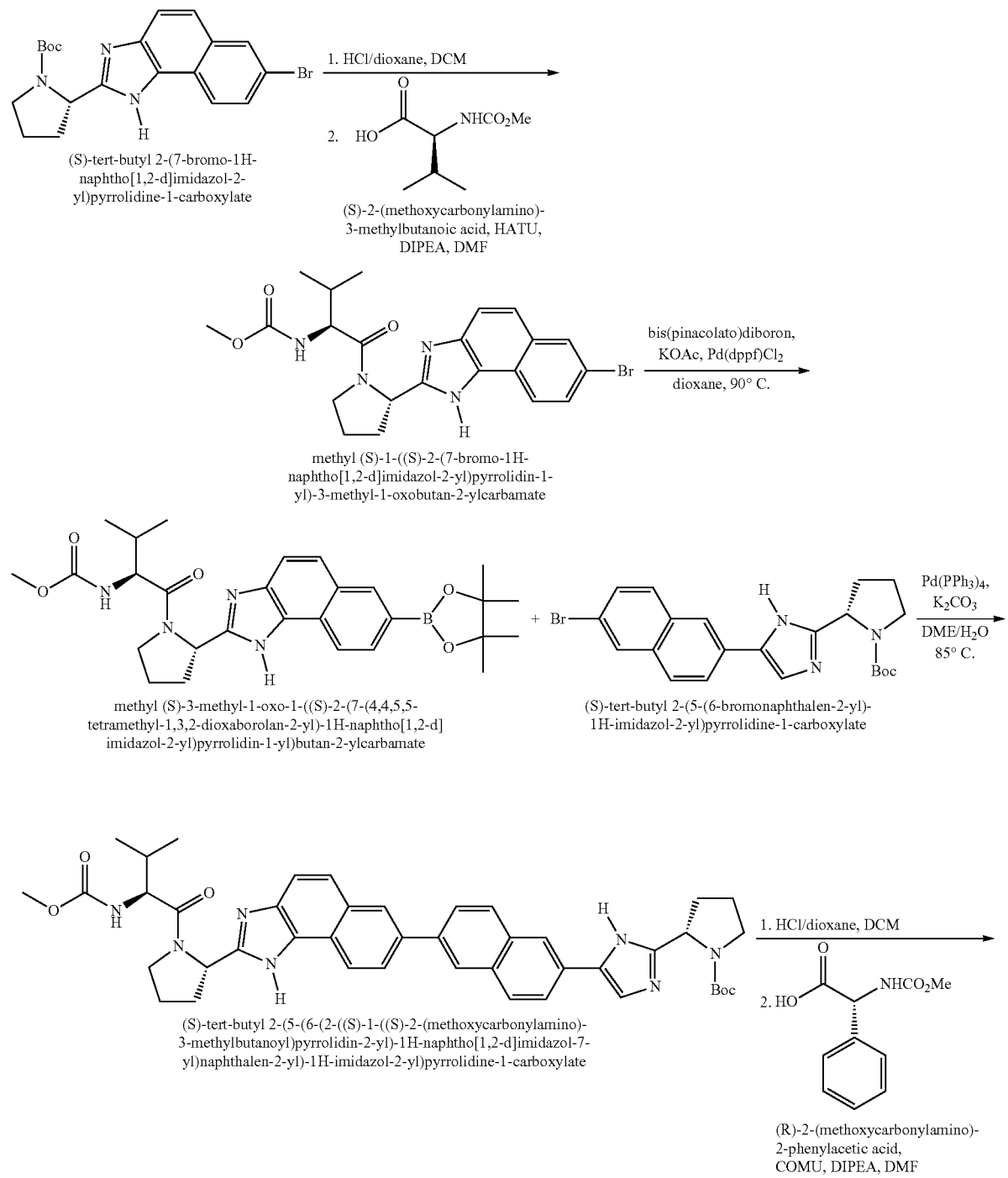

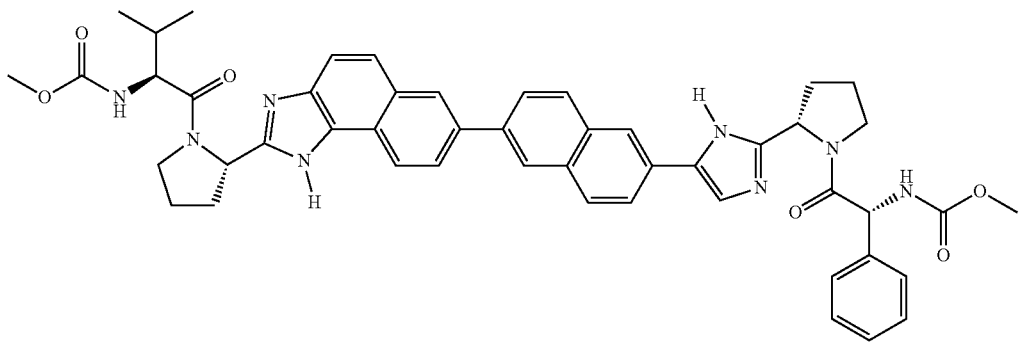

methyl (S)-1-((S)-2-(7-(6-(2-((S)-1-((R)-2-methoxycarbonylamino-2-phenylacetyl)pyrrolidin-2-yl)-1H-imidazol-5-yl)naphthalen-2-yl)-1H-naphtho[1,2-d]imidazol-2-yl)pyrrolidin-1-yl)-3-methyl-1-oxobutan-2-ylcarbamate Methyl (S)-1-((S)-2-(7-bromo-1H-naphtho[1,2-d]imidazol-2-yl)pyrrolidin-1-yl)-3-methyl-1-oxobutan-2-ylcarbamate: (S)-tert-butyl 2-(7-bromo-1H-naphtho[1,2-d]imidazol-2-yl)pyrrolidine-1-carboxylate (1.10 g, 2.64 mmol) was dissolved in DCM (15 mL) and HCl (4M in dioxane, 3 mL) was added. After stirring for 2.5 h, the reaction mixture was concentrated and the residue was treated with (S)-2-(methoxycarbonylamino)-3-methylbutanoic acid (462 mg, 2.64 mmol), HATU (1.003g, 2.64 mmol) and DMF (13 mL). The stirred mixture was cooled to 0° C. and DIPEA (2.3 mL, 13.2 mmol) was added. After 7 min, the reaction was allowed to warm to RT. 20 min later, the mixture was diluted with EtOAc and washed with saturated aqueous $NaHCO_3$ and brine. The organic phase was dried over $MgSO_4$, filtered and concentrated. The crude residue was purified by silica column chromatography (79% to 100% EtOAc/hexane) to afford the title compound (590 mg, 47%).

Methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate: Methyl (S)-1-((S)-2-(7-bromo-1H-naphtho[1,2-d]imidazol-2-yl)pyrrolidin-1-yl)-3-methyl-1-oxobutan-2-ylcarbamate (590 mg, 1.25 mmol), bis(pinacolato)diboron (353 mg, 1.50 mmol), KOAc (245 mg, 2.50 mmol) and Pd(dppf)Cl$_2$ (91 mg, 0.125 mmol) were suspended in dioxane (12 mL). The stirred mixture was degassed with $N_2$ for 11 min then heated to 90° C. After 2.5 h, the mixture was cooled to RT, diluted with EtOAc and washed with saturated aqueous $NaHCO_3$ and brine. The organic phase was dried over $MgSO_4$, filtered and concentrated. The crude residue was purified by silica column chromatography (80% to 100% EtOAc/hexane) to afford the title compound (425 mg, 65%).

(S)-tert-butyl 2-(5-(6-(2-((S)-1-((S)-2-(methoxycarbonylamino)-3-methylbutanoyl)pyrrolidin-2-yl)-1H-naphtho[1,2-d]imidazol-7-yl)naphthalen-2-yl)-1H-imidazol-2-yl)pyrrolidine-1-carboxylate: Methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate (267 mg, 0.513 mmol), (S)-tert-butyl 2-(5-(6-bromonaphthalen-2-yl)-1H-imidazol-2-yl)pyrrolidine-1-carboxylate (272 mg, 0.616 mmol), Pd(PPh$_3$)$_4$ (59 mg, 0.0513 mmol) and $K_2CO_3$ (2M in $H_2O$, 0.62 mL, 1.2 mmol) were suspended in DME (5 mL). The mixture was degassed with $N_2$ for 10 min then heated to reflux. After 5 h, the reaction mixture was cooled to RT, diluted with EtOAc and washed with brine. The organic phase was dried over $MgSO_4$, filtered and concentrated. The crude residue was purified by silica column chromatography (0% to 30% MeOH/EtOAc) to afford the title compound (201 mg, 52%).

Methyl (S)-1-((S)-2-(7-(6-(2-((S)-1-((R)-2-methoxycarbonylamino-2-phenylacetyl)pyrrolidin-2-yl)-1H-imidazol-5-yl)naphthalen-2-yl)-1H-naphtho[1,2-d]imidazol-2-yl)pyrrolidin-1-yl)-3-methyl-1-oxobutan-2-ylcarbamate: (S)-tert-butyl 2-(5-(6-(2-((S)-1-((S)-2-(methoxycarbonylamino)-3-methylbutanoyl)pyrrolidin-2-yl)-1H-naphtho[1,2-d]imidazol-7-yl)naphthalen-2-yl)-1H-imidazol-2-yl)pyrrolidine-1-carboxylate (88 mg, 0.116 mmol) was dissolved in DCM (5 mL) and HCl (4M in dioxane, 1 mL) was added. After stirring for 1 h, the reaction mixture was concentrated and the residue was treated with (R)-2-(methoxycarbonylamino)-2-phenylacetic acid (24 mg, 0.116 mmol), COMU (50 mg, 0.116 mmol) and DMF (3 mL). DIPEA (0.101 mL, 0.58 mmol) was added and the mixture was stirred for 13 min before being quenched with $H_2O$ and purified by HPLC to afford the title compound (61 mg, 62%). MS: (ESI) m/z 847 [M+H]$^+$.

Example DS

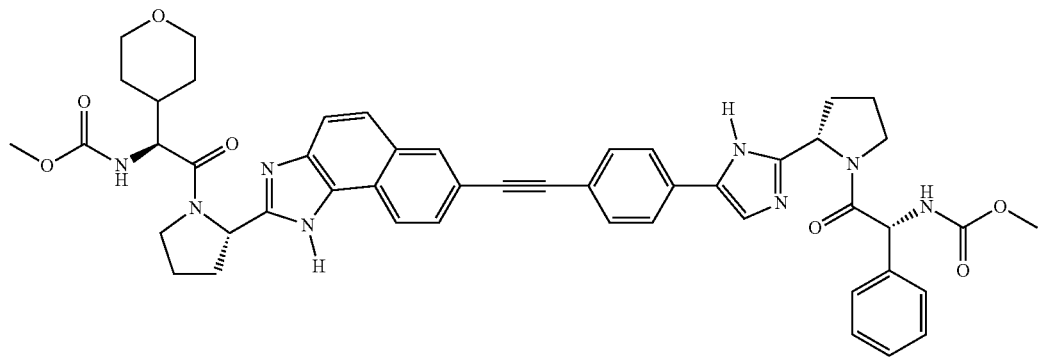

methyl (S)-2-((S)-2-(7-((4-(2-((S)-1-((R)-2-methoxycarbonylamino-2-phenylacetyl)pyrrolidin-2-yl)-1H-imidazol-5-yl)phenyl)ethynyl)-1H-naphtho[1,2-d]imidazol-2-yl)pyrrolidin-1-yl)-2-oxo-1-(tetrahydro-2H-pyran-4-yl)ethylcarbamate Methyl (S)-2-((S)-2-(7-((4-(2-((S)-1-((R)-2-methoxycarbonylamino-2-phenylacetyl)pyrrolidin-2-yl)-1H-imidazol-5-yl)phenyl)ethynyl)-1H-naphtho[1,2-d]imidazol-2-yl)pyrrolidin-1-yl)-2-oxo-1-(tetrahydro-2H-pyran-4-yl)ethylcarbamate: MS: (ESI) m/z 863 [M+H]+.

Example DT

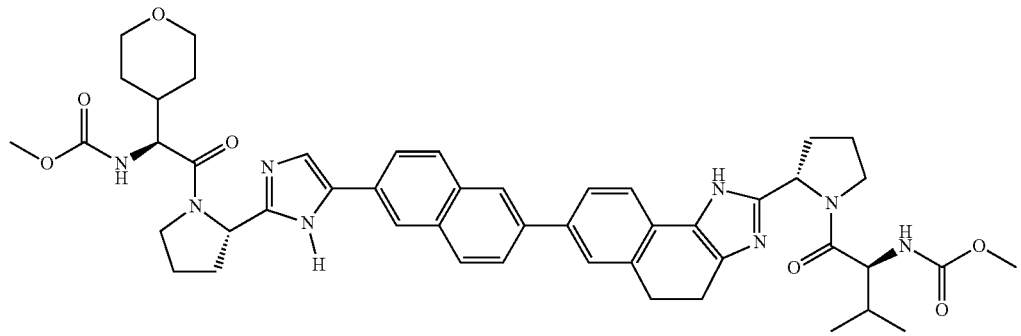

methyl (S)-2-((S)-2-(5-(6-(2-((S)-1-((S)-2-methoxycarbonylamino-3-methylbutanoyl)pyrrolidin-2-yl)-4,5-dihydro-1H-naphtho[1,2-d]imidazol-7-yl)naphthalen-2-yl)-1H-imidazol-2-yl)pyrrolidin-1-yl)-2-oxo-1-(tetrahydro-2H-pyran-4-yl)ethylcarbamate Methyl (S)-2-((S)-2-(5-(6-(2-((S)-1-((S)-2-methoxycarbonylamino-3-methylbutanoyl)pyrrolidin-2-yl)-4,5-dihydro-1H-naphtho[1,2-d]imidazol-7-yl)naphthalen-2-yl)-1H-imidazol-2-yl)pyrrolidin-1-yl)-2-oxo-1-(tetrahydro-2H-pyran-4-yl)ethylcarbamate: MS: (ESI) m/z 857 [M+H]+.

Example DU

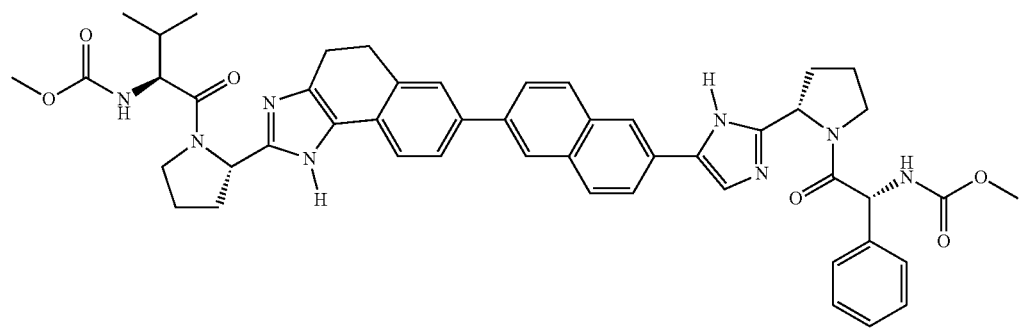

methyl (S)-1-((S)-2-(7-(6-(2-((S)-1-((R)-2-methoxy-carbonylamino-2-phenylacetyl)pyrrolidin-2-yl)-1H-imidazol-5-yl)naphthalen-2-yl)-4,5-dihydro-1H-naphtho[1,2-d]imidazol-2-yl)pyrrolidin-1-yl)-3-methyl-1-oxobutan-2-ylcarbamate Methyl (S)-1-((S)-2-(7-(6-(2-((S)-1-((R)-2-methoxycarbonylamino-2-phenylacetyl)pyrrolidin-2-yl)-1H-imidazol-5-yl)naphthalen-2-yl)-4,5-dihydro-1H-naphtho[1,2-d]imidazol-2-yl)pyrrolidin-1-yl)-3-methyl-1-oxobutan-2-ylcarbamate: MS: (ESI) m/z 850 [M+H]$^+$.

Example DV

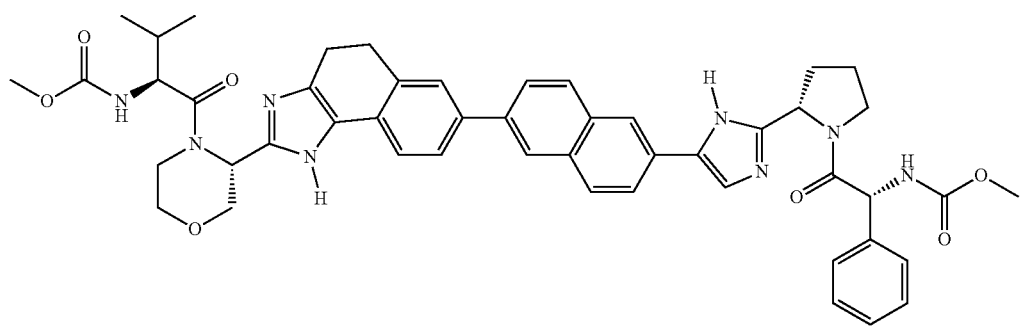

methyl (S)-1-((R)-3-(7-(6-(2-((S)-1-((R)-2-methoxy-carbonylamino-2-phenylacetyl)pyrrolidin-2-yl)-1H-imidazol-5-yl) naphthalen-2-yl)-4,5-dihydro-1H-naphtho[1,2-d]imidazol-2-yl) morpholino)-3-methyl-1-oxobutan-2-ylcarbamate Methyl (S)-1-((R)-3-(7-(6-(2-((S)-1-((R)-2-methoxycarbonylamino-2-phenylacetyl)pyrrolidin-2-yl)-1H-imidazol-5-yl)naphthalen-2-yl)-4,5-dihydro-1H-naphtho[1,2-d]imidazol-2-yl)morpholino)-3-methyl-1-oxobutan-2-ylcarbamate: MS: (ESI) m/z 866 [M+H]$^+$.

Example DW

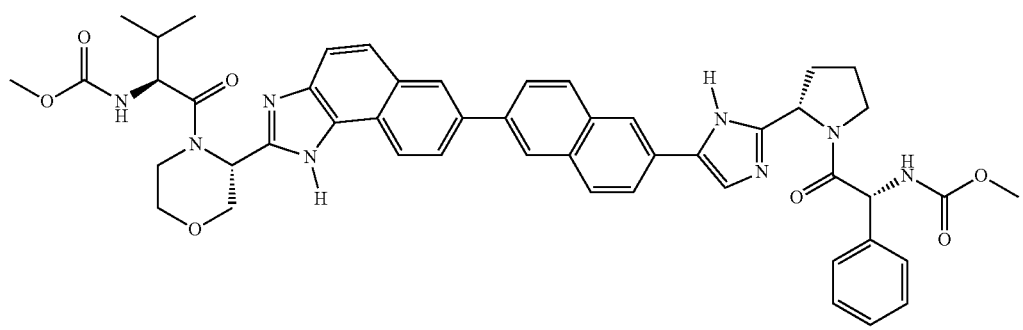

methyl (S)-1-((R)-3-(7-(6-(2-((S)-1-((R)-2-methoxy-carbonylamino-2-phenylacetyl)pyrrolidin-2-yl)-1H-imidazol-5-yl)naphthalen-2-yl)-1H-naphtho[1,2-d]imidazol-2-yl)morpholino)-3-methyl-1-oxobutan-2-ylcarbamate Methyl (S)-1-((R)-3-(7-(6-(2-((S)-1-((R)-2-methoxycarbonylamino-2-phenylacetyl)pyrrolidin-2-yl)-1H-imidazol-5-yl)naphthalen-2-yl)-1H-naphtho[1,2-d]imidazol-2-yl)morpholino)-3-methyl-1-oxobutan-2-ylcarbamate: (ESI) m/z 864 [M+H]$^+$.

Example DX

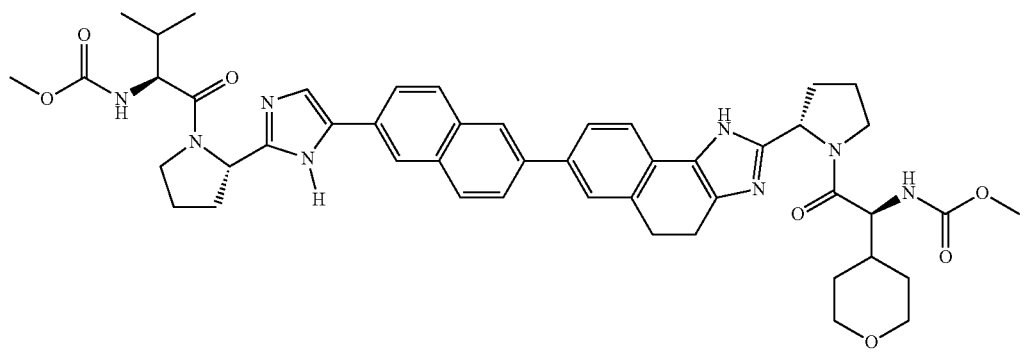

methyl (S)-1-((S)-2-(5-(6-(2-((S)-1-((S)-2-methoxy-carbonylamino-2-(tetrahydro-2H-pyran-4-yl)acetyl)pyrrolidin-2-yl)-4,5-dihydro-1H-naphtho[1,2-d]imidazol-7-yl)naphthalen-2-yl)-1H-imidazol-2-yl)pyrrolidin-1-yl)-3-methyl-1-oxobutan-2-ylcarbamate Methyl (S)-1-((S)-2-(5-(6-(2-((S)-1-((S)-2-methoxycarbonylamino-2-(tetrahydro-2H-pyran-4-yl)acetyl)pyrrolidin-2-yl)-4,5-dihydro-1H-naphtho[1,2-d]imidazol-7-yl)naphthalen-2-yl)-1H-imidazol-2-yl)pyrrolidin-1-yl)-3-methyl-1-oxobutan-2-ylcarbamate: (ESI) m/z 858 [M+H]$^+$.

Example DY

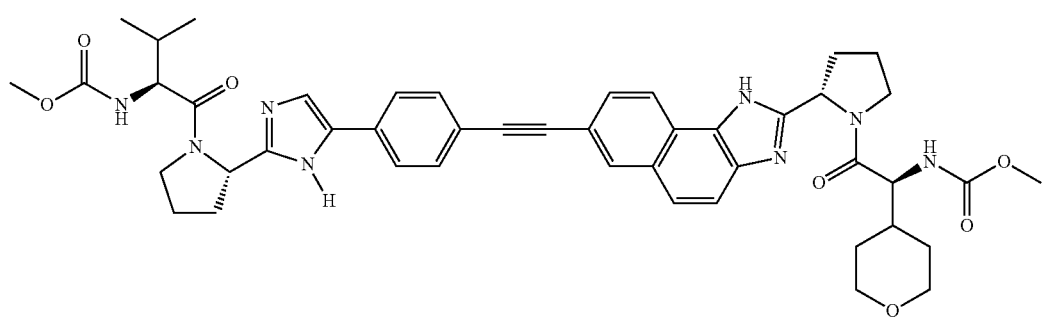

methyl (S)-1-((S)-2-(5-(4-((2-((S)-1-((S)-2-methoxy-carbonylamino-2-(tetrahydro-2H-pyran-4-yl)acetyl)pyrrolidin-2-yl)-1H-naphtho[1,2-d]imidazol-7-yl)ethynyl)phenyl)-1H-imidazol-2-yl)pyrrolidin-1-yl)-3-methyl-1-oxobutan-2-ylcarbamate Methyl (S)-1-((S)-2-(5-(4-((2-((S)-1-((S)-2-methoxycarbonylamino-2-(tetrahydro-2H-pyran-4-yl)acetyl)pyrrolidin-2-yl)-1H-naphtho[1,2-d]imidazol-7-yl)ethynyl)phenyl)-1H-imidazol-2-yl)pyrrolidin-1-yl)-3-methyl-1-oxobutan-2-ylcarbamate: (ESI) m/z 829 [M+H]+$^+$.

Example DZ

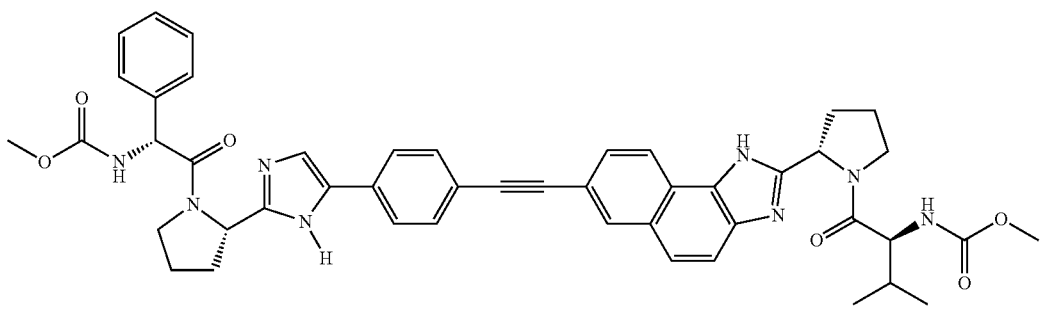

methyl (R)-2-((S)-2-(5-(4-((2-((S)-1-((S)-2-methoxycarbonylamino-3-methylbutanoyl)pyrrolidin-2-yl)-1H-naphtho[1,2-d]imidazol-7-yl)ethynyl)phenyl)-1H-imidazol-2-yl)pyrrolidin-1-yl)-2-oxo-1-phenylethylcarbamate Methyl (R)-2-((S)-2-(5-(4-((2-((S)-1-((S)-2-methoxycarbonylamino-3-methylbutanoyl)pyrrolidin-2-yl)-1H-naphtho[1,2-d]imidazol-7-yl)ethynyl)phenyl)-1H-imidazol-2-yl)pyrrolidin-1-yl)-2-oxo-1-phenylethylcarbamate: (ESI) m/z 821 [M+H]$^+$.

Example EA

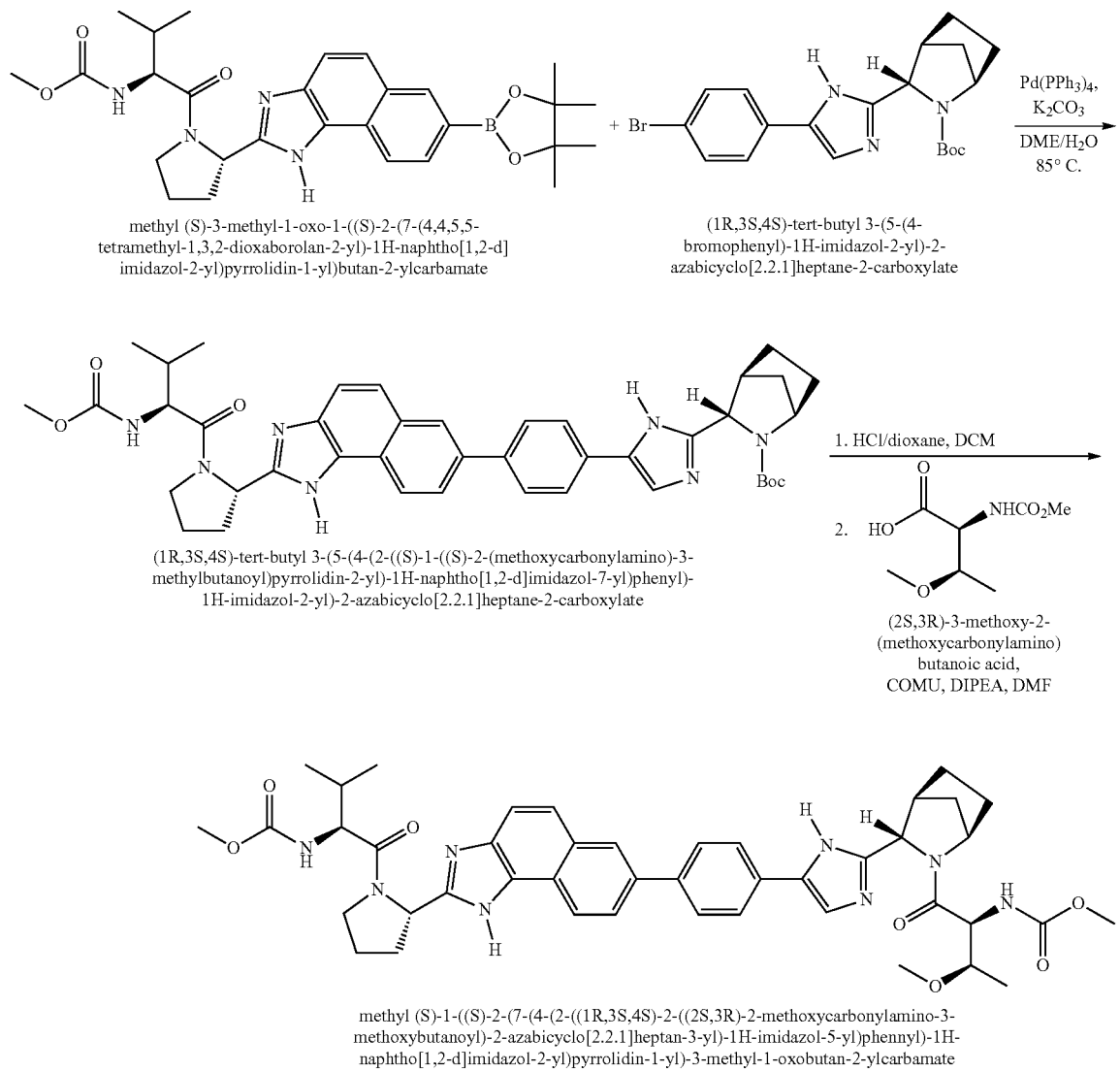

(1R,3S,4S)-tert-butyl 3-(5-(4-(2-((S)-1-((S)-2-(methoxycarbonylamino)-3-methylbutanoyl)pyrrolidin-2-yl)-1H-naphtho[1,2-d]imidazol-7-yl)phenyl)-1H-imidazol-2-yl)-2-azabicyclo[2.2.1]heptane-2-carboxylate: Methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate (396 mg, 0.761 mmol), (1R,3S,4S)-tert-butyl 3-(5-(4-bromophenyl)-1H-imidazol-2-yl)-2-azabicyclo[2.2.1]heptane-2-carboxylate (382 mg, 0.913 mmol), Pd(PPh$_3$)$_4$ (88 mg, 0.0761 mmol) and K$_2$CO$_3$ (2M in H$_2$O, 0.95 mL, 1.9 mmol) were suspended in DME (4 mL). The reaction mixture was degassed with N$_2$ for 6 min then heated to reflux. After 6.5 h, the reaction mixture was cooled to RT, diluted with MeOH, filtered over a thiol SPE column and concentrated. The crude residue was purified by column chromatography (0% to 30% MeOH/EtOAc) to afford the title compound (461 mg, 83%).

Methyl (S)-1-((S)-2-(7-(4-(2-((1R,3S,4S)-2-((2S,3R)-2-methoxycarbonylamino-3-methoxybutanoyl)-2-azabicyclo[2.2.1]heptan-3-yl)-1H-imidazol-5-yl)phenyl)-1H-naphtho[1,2-d]imidazol-2-yl)pyrrolidin-1-yl)-3-methyl-1-oxobutan-2-ylcarbamate:

(1R,3S,4S)-tert-butyl 3-(5-(4-(2-((S)-1-((S)-2-(methoxycarbonylamino)-3-methylbutanoyl)pyrrolidin-2-yl)-1H-naphtho[1,2-d]imidazol-7-yl)phenyl)-1H-imidazol-2-yl)-2-azabicyclo[2.2.1]heptane-2-carboxylate (73 mg, 0.0997 mmol) was dissolved in DCM (5 mL) and treated with HCl (4M in dioxane, 1 mL). After 3 h, the reaction mixture was concentrated. The residue was treated with (2S,3R)-3-methoxy-2-(methoxycarbonylamino)butanoic acid (23 mg, 0.120 mmol), COMU (51 mg, 0.120 mmol) and DMF (2 mL). DIPEA (0.090 mL, 0.499 mmol) was added and the reaction mixture was stirred for 25 min before being quenched with H$_2$O and purified by HPLC to afford the title compound (22 mg, 28%). (ESI) m/z 805 [M+H]$^+$.

Example EB

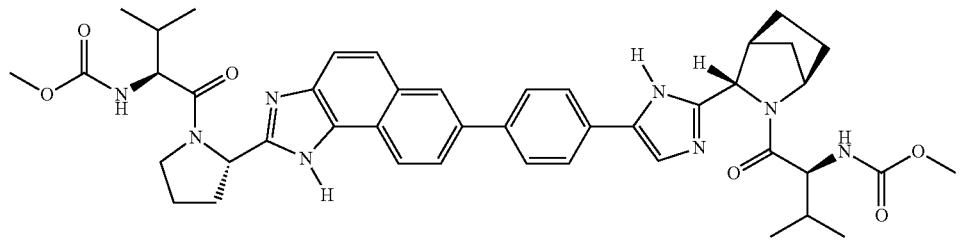

methyl (S)-1-((S)-2-(7-(4-(2-((1R,3S,4S)-2-((S)-2-methoxycarbonylamino-3-methylbutanoyl)-2-azabicyclo[2.2.1]heptan-3-yl)-1H-imidazol-5-yl)phenyl)-1H-naphtho[1,2-d]imidazol-2-yl)pyrrolidin-1-yl)-3-methyl-1-oxobutan-2-ylcarbamate Methyl (S)-1-((S)-2-(7-(4-(2-((1R,3S,4S)-2-((S)-2-methoxycarbonylamino-3-methylbutanoyl)-2-azabicyclo[2.2.1]heptan-3-yl)-1H-imidazol-5-yl)phenyl)-1H-naphtho[1,2-d]imidazol-2-yl)pyrrolidin-1-yl)-3-methyl-1-oxobutan-2-ylcarbamate: Title compound was prepared by methods analogous to those described for methyl (S)-1-((S)-2-(7-(4-(2-((1R,3 S,4S)-2-((2S,3R)-2-methoxycarbonylamino-3-methoxybutanoyl)-2-azabicyclo[2.2.1]heptan-3-yl)-1H-imidazol-5-yl)phenyl)-1H-naphtho[1,2-d]imidazol-2-yl)pyrrolidin-1-yl)-3-methyl-1-oxobutan-2-ylcarbamate, substituting (S)-2-(methoxycarbonylamino)-3-methylbutanoic acid for (2S,3R)-3-methoxy-2-(methoxycarbonylamino)butanoic acid. (ESI) m/z 789 [M+H]$^+$.

Example EC

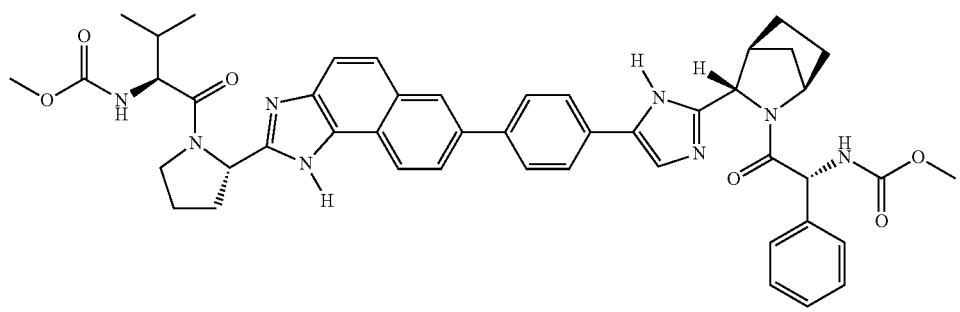

methyl (S)-1-((S)-2-(7-(4-(2-((1R,3 S,4S)-2-((R)-2-methoxycarbonylamino-2-phenylacetyl)-2-azabicyclo[2.2.1]heptan-3-yl)-1H-imidazol-5-yl)phenyl)-1H-naphtho[1,2-d]imidazol-2-yl)pyrrolidin-1-yl)-3-methyl-1-oxobutan-2-ylcarbamate Methyl (S)-1-((S)-2-(7-(4-(2-((1R,3S,4S)-2-((R)-2-methoxycarbonylamino-2-phenylacetyl)-2-azabicyclo[2.2.1]heptan-3-yl)-1H-imidazol-5-yl)phenyl)-1H-naphtho[1,2-d]imidazol-2-yl)pyrrolidin-1-yl)-3-methyl-1-oxobutan-2-ylcarbamate: Title compound was prepared by methods analogous to those described for methyl (S)-1-((S)-2-(7-(4-(2-((1R,3 S,4S)-2-((2S,3R)-2-methoxycarbonylamino-3-methoxybutanoyl)-2-azabicyclo[2.2.1]heptan-3-yl)-1H-imidazol-5-yl)phenyl)-1H-naphtho[1,2-d]imidazol-2-yl)pyrrolidin-1-yl)-3-methyl-1-oxobutan-2-ylcarbamate, substituting (R)-2-(methoxycarbonyl amino)-2-phenylacetic acid for (2S,3R)-3-methoxy-2-(methoxycarbonylamino)butanoic acid. (ESI) m/z 823 [M+H]⁺.

Example ED

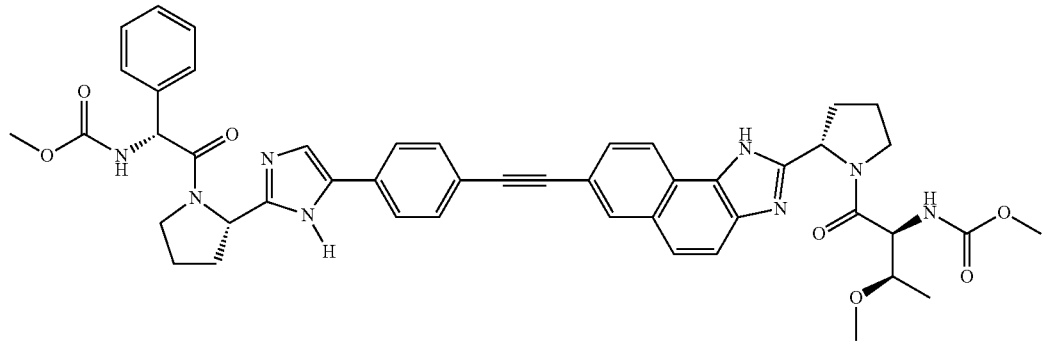

methyl (R)-2-((S)-2-(5-(4-((2-((S)-1-((2S,3R)-2-methoxycarbonylamino-3-methoxybutanoyl)pyrrolidin-2-yl)-1H-naphtho[1,2-d]imidazol-7-yl)ethynyl)phenyl)-1H-imidazol-2-yl)pyrrolidin-1-yl)-2-oxo-1-phenylethylcarbamate Methyl (R)-2-((S)-2-(5-(4-((2-((S)-1-((2S,3R)-2-methoxycarbonylamino-3-methoxybutanoyl)pyrrolidin-2-yl)-1H-naphtho[1,2-d]imidazol-7-yl)ethynyl)phenyl)-1H-imidazol-2-yl)pyrrolidin-1-yl)-2-oxo-1-phenylethylcarbamate: (ESI) m/z 837 [M+H]⁺.

Example EE

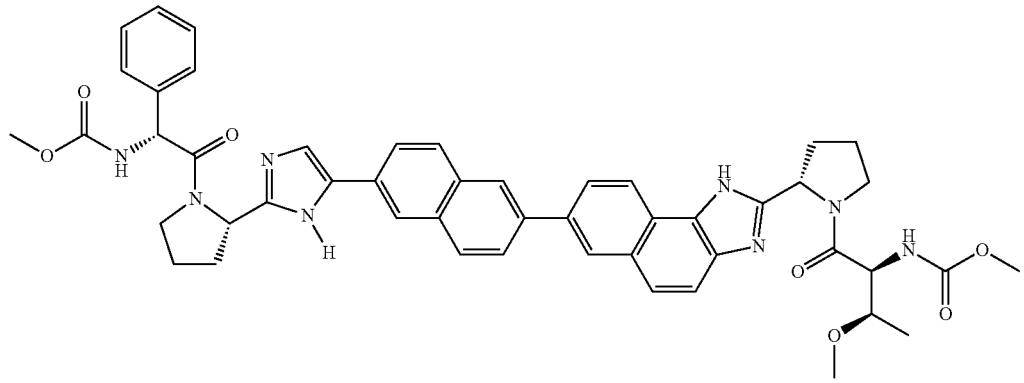

methyl (R)-2-((S)-2-(5-(6-(2-((S)-1-((2S,3R)-2-methoxycarbonylamino-3-methoxybutanoyl)pyrrolidin-2-yl)-1H-naphtho[1,2-d]imidazol-7-yl)naphthalen-2-yl)-1H-imidazol-2-yl)pyrrolidin-1-yl)-2-oxo-1-phenylethylcarbamate Methyl (R)-2-((S)-2-(5-(6-(2-((S)-1-((2S,3R)-2-methoxycarbonylamino-3-methoxybutanoyl)pyrrolidin-2-yl)-1H-naphtho[1,2-d]imidazol-7-yl)naphthalen-2-yl)-1H-imidazol-2-yl)pyrrolidin-1-yl)-2-oxo-1-phenylethylcarbamate: Title compound was prepared according to the methods described for methyl (S)-1-((S)-2-(7-(6-(2-((S)-1-((R)-2-methoxycarbonylamino-2-phenylacetyl)pyrrolidin-2-yl)-1H-imidazol-5-yl)naphthalen-2-yl)-1H-naphtho[1,2-d]imidazol-2-yl)pyrrolidin-1-yl)-3-methyl-1-oxobutan-2-ylcarbamate, substituting (2S,3R)-3-methoxy-2-(methoxycarbonylamino)butanoic acid for (S)-2-(methoxycarbonylamino)-3-methylbutanoic acid. (ESI) m/z 863 [M+H]$^+$.

Example EF

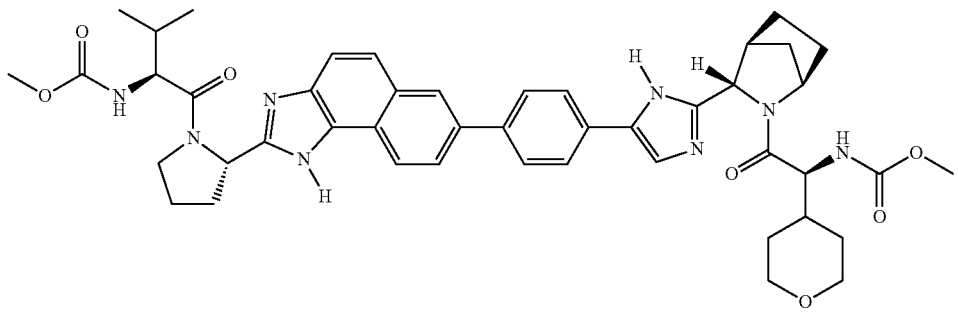

methyl (S)-1-((S)-2-(7-(4-(2-((1R,3S,4S)-2-((S)-2-methoxycarbonylamino-2-(tetrahydro-2H-pyran-4-yl)acetyl)-2-azabicyclo[2.2.1]heptan-3-yl)-1H-imidazol-5-yl)phenyl)-1H-naphtho[1,2-d]imidazol-2-yl)pyrrolidin-1-yl)-3-methyl-1-oxobutan-2-ylcarbamate Methyl (S)-1-((S)-2-(7-(4-(2-((1R,3S,4S)-2-((S)-2-methoxycarbonylamino-2-(tetrahydro-2H-pyran-4-yl)acetyl)-2-azabicyclo[2.2.1]heptan-3-yl)-1H-imidazol-5-yl)phenyl)-1H-naphtho[1,2-d]imidazol-2-yl)pyrrolidin-1-yl)-3-methyl-1-oxobutan-2-ylcarbamate: Title compound was prepared by methods analogous to those described for methyl (S)-1-((S)-2-(7-(4-(2-((1R,3S,4S)-2-((2S,3R)-2-methoxycarbonylamino-3-methoxybutanoyl)-2-azabicyclo[2.2.1]heptan-3-yl)-1H-imidazol-5-yl)phenyl)-1H-naphtho[1,2-d]imidazol-2-yl)pyrrolidin-1-yl)-3-methyl-1-oxobutan-2-ylcarbamate, substituting (S)-2-(methoxycarbonylamino)-2-(tetrahydro-2H-pyran-4-yl)acetic acid for (2S,3R)-3-methoxy-2-(methoxycarbonylamino)butanoic acid. (ESI) m/z 831 [M+H]$^+$.

Example EG

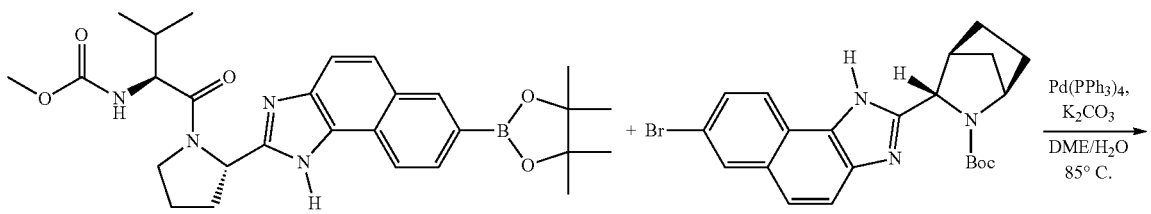

methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate (1R,3S,4S)-tert-butyl 3-(7-bromo-1H-naphtho[1,2-d]imidazol-2-yl)-2-azabicyclo[2.2.1]heptane-2-carboxylate

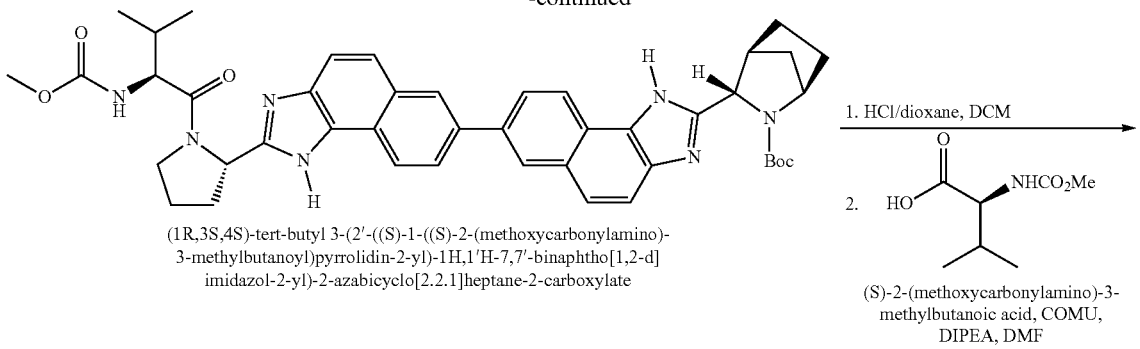

(1R,3S,4S)-tert-butyl 3-(2'-((S)-1-((S)-2-(methoxycarbonylamino)-3-methylbutanoyl)pyrrolidin-2-yl)-1H,1'H-7,7'-binaphtho[1,2-d]imidazol-2-yl)-2-azabicyclo[2.2.1]heptane-2-carboxylate 1. HCl/dioxane, DCM 2. (S)-2-(methoxycarbonylamino)-3-methylbutanoic acid, COMU, DIPEA, DMF

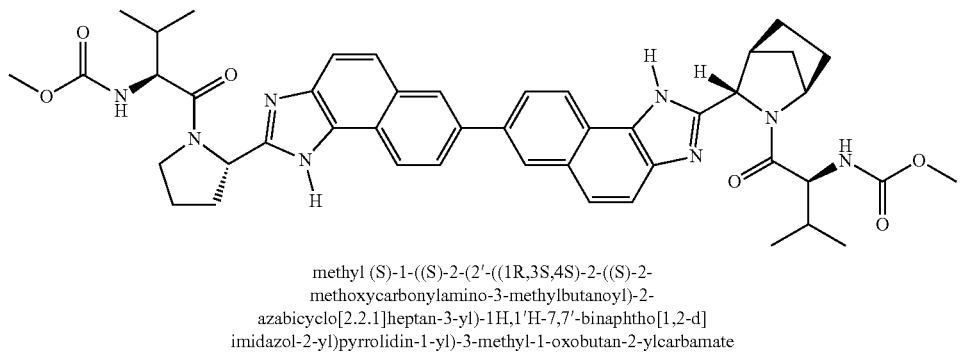

methyl (S)-1-((S)-2-(2'-((1R,3S,4S)-2-((S)-2-methoxycarbonylamino-3-methylbutanoyl)-2-azabicyclo[2.2.1]heptan-3-yl)-1H,1'H-7,7'-binaphtho[1,2-d]imidazol-2-yl)pyrrolidin-1-yl)-3-methyl-1-oxobutan-2-ylcarbamate (1R,3S,4S)-tert-butyl 3-(2'-((S)-1-((S)-2-(methoxycarbonylamino)-3-methylbutanoyl)pyrrolidin-2-yl)-1H,1'H-7,7'-binaphtho[1,2-d]imidazol-2-yl)-2-azabicyclo[2.2.1]heptane-2-carboxylate: Methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate (372 mg, 0.715 mmol), (1R,3S,4S)-tert-butyl 3-(7-bromo-1H-naphtho[1,2-d]imidazol-2-yl)-2-azabicyclo[2.2.1]heptane-2-carboxylate (317 mg, 0.715 mmol), Pd(PPh$_3$)$_4$ (83 mg, 0.0715 mmol) and K$_2$CO$_3$ (2M in H$_2$O, 0.7 mL, 1.4 mmol) were suspended in DME (3.6 mL). The mixture was degassed for 13 min with bubbling N$_2$, then heated to reflux. After 18 h, the reaction mixture was cooled to RT and 5 mL MeOH was added. EtOAc was added and the organics were washed with saturated aqueous NaHCO$_3$ and brine, dried over MgSO$_4$, filtered and concentrated. The crude residue was purified by silica column chromatography (0% to 33% MeOH/EtOAc) to afford the title compound (196 mg, 36%).

Methyl (S)-1-((S)-2-(2'-((1R,3S,4S)-2-((S)-2-methoxycarbonylamino-3-methylbutanoyl)-2-azabicyclo[2.2.1]heptan-3-yl)-1H,1'H-7,7'-binaphtho[1,2-d]imidazol-2-yl)pyrrolidin-1-yl)-3-methyl-1-oxobutan-2-ylcarbamate: (1R,3S,4S)-tert-butyl 3-(2'-((S)-1-((S)-2-(methoxycarbonylamino)-3-methylbutanoyl)pyrrolidin-2-yl)-1H,1'H-7,7'-binaphtho[1,2-d]imidazol-2-yl)-2-azabicyclo[2.2.1]heptane-2-carboxylate (102 mg, 0.135 mmol) was dissolved in DCM (5 mL) and treated with HCl (4M in dioxane, 1 mL). After 2 h, the reaction mixture was concentrated. The residue was treated with (S)-2-(methoxycarbonylamino)-3-methylbutanoic acid (28 mg, 0.149 mmol), COMU (58 mg, 0.135 mmol) and DMF (3 mL). DIPEA (0.12 mL, 0.675 mmol) was added and the reaction mixture was stirred for 1.5 h before being quenched with H$_2$O and purified by HPLC to afford the title compound (86 mg, 77%). (ESI) m/z 814 [M+H]$^+$.

Example EH

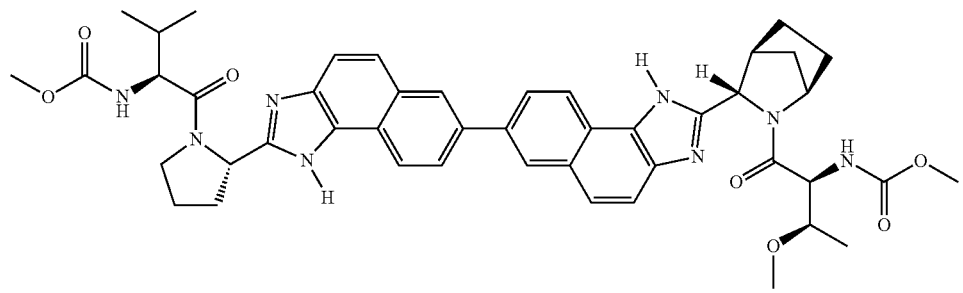

methyl (S)-1-((S)-2-(2'-((1R,3S,4S)-2-((2S,3R)-2-methoxycarbonylamino-3-methoxybutanoyl)-2-azabicyclo[2.2.1]heptan-3-yl)-1H, 1'H-7,7'-binaphtho[1,2-d]imidazol-2-yl)pyrrolidin-1-yl)-3-methyl-1-oxobutan-2-ylcarbamate Methyl (S)-1-((S)-2-(2'-((1R,3S,4S)-2-((2S,3R)-2-methoxycarbonylamino-3-methoxybutanoyl)-2-azabicyclo[2.2.1]heptan-3-yl)-1H,1'H-7,7'-binaphtho[1,2-d]imidazol-2-yl)pyrrolidin-1-yl)-3-methyl-1-oxobutan-2-ylcarbamate: Title compound was prepared by methods analogous to those described for methyl (S)-1-((S)-2-(2'-((1R,3S,4S)-2-((S)-2-methoxycarbonylamino-3-methylbutanoyl)-2-azabicyclo[2.2.1]heptan-3-yl)-1H,1'H-7,7'-binaphtho[1,2-d]imidazol-2-yl)pyrrolidin-1-yl)-3-methyl-1-oxobutan-2-ylcarbamate, substituting (2S,3R)-3-methoxy-2-(methoxycarbonylamino)butanoic acid for (S)-2-(methoxycarbonylamino)-3-methylbutanoic acid. (ESI) m/z 830 [M+H]$^+$.

Example EI

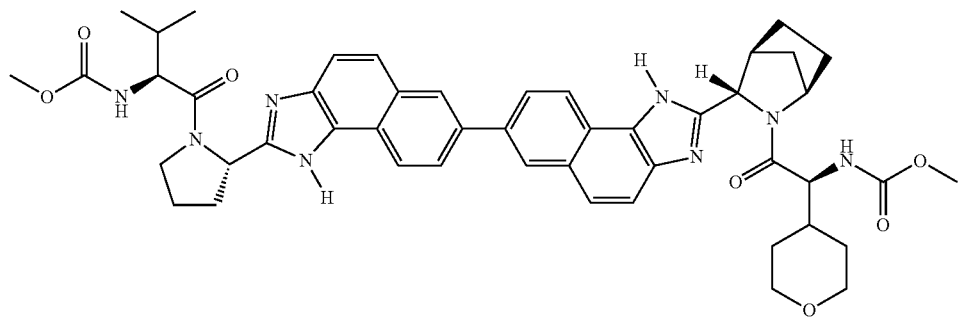

methyl (S)-1-((S)-2-(2'-((1R,3S,4S)-2-((S)-2-methoxycarbonylamino-2-(tetrahydro-2H-pyran-4-yl)acetyl)-2-azabicyclo[2.2.1]heptan-3-yl)-1H,1'H-7,7'-binaphtho[1,2-d]imidazol-2-yl)pyrrolidin-1-yl)-3-methyl-1-oxobutan-2-ylcarbamate Methyl (S)-1-((S)-2-(2'-((1R,3S,4S)-2-((S)-2-methoxycarbonylamino-2-(tetrahydro-2H-pyran-4-yl)acetyl)-2-azabicyclo[2.2.1]heptan-3-yl)-1H,1'H-7,7'-binaphtho[1,2-d]imidazol-2-yl)pyrrolidin-1-yl)-3-methyl-1-oxobutan-2-ylcarbamate: Title compound was prepared by methods analogous to those described for methyl (S)-1-((S)-2-(2'-((1R,3S,4S)-2-((S)-2-methoxycarbonylamino-3-methylbutanoyl)-2-azabicyclo[2.2.1]heptan-3-yl)-1H,1'H-7,7'-binaphtho[1,2-d]imidazol-2-yl)pyrrolidin-1-yl)-3-methyl-1-oxobutan-2-ylcarbamate, substituting (S)-2-(methoxycarbonylamino)-2-(tetrahydro-2H-pyran-4-yl)acetic acid for (S)-2-(methoxycarbonylamino)-3-methylbutanoic acid. (ESI) m/z 855 [M+H]$^+$.

Example EJ

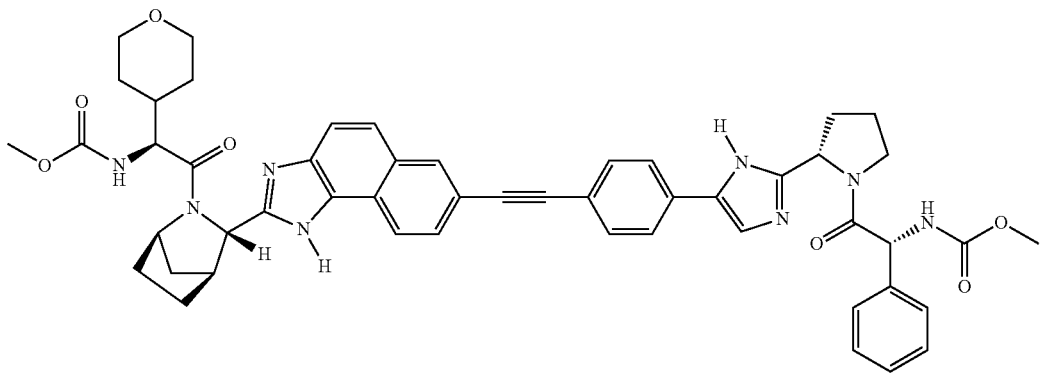

methyl (S)-2-((1R,3S,4S)-3-(7-((4-(2-((S)-1-((R)-2-methoxycarbonylamino-2-phenylacetyl)pyrrolidin-2-yl)-1H-imidazol-5-yl)phenyl)ethynyl)-1H-naphtho[1,2-d]imidazol-2-yl)-2-azabicyclo[2.2.1]heptan-2-yl)-2-oxo-1-(tetrahydro-2H-pyran-4-yl) ethylcarbamate Methyl (S)-2-((1R,3S,4S)-3-(7-((4-(2-((S)-1-((R)-2-methoxycarbonylamino-2-phenylacetyl)pyrrolidin-2-yl)-1H-imidazol-5-yl)phenyl)ethynyl)-1H-naphtho[1,2-d]imidazol-2-yl)-2-azabicyclo[2.2.1]heptan-2-yl)-2-oxo-1-(tetrahydro-2H-pyran-4-yl)ethylcarbamate: (ESI) m/z 890 [M+H]$^+$.

Example EK

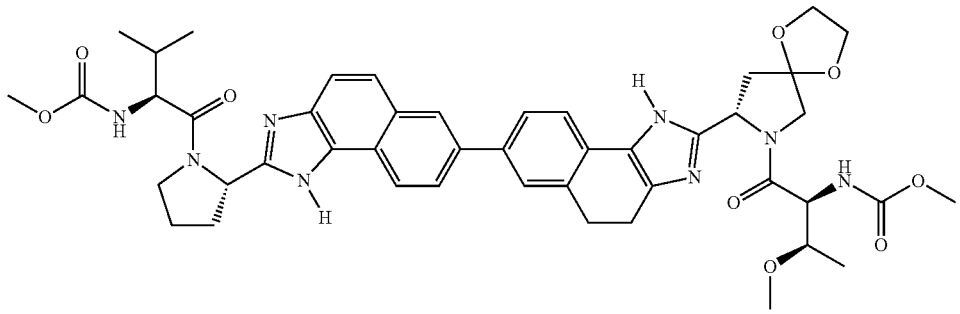

methyl (S)-1-((S)-2-(2'-((S)-7-((2S,3R)-2-methoxycarbonylamino-3-methoxybutanoyl)-1,4-dioxa-7-azaspiro[4.4]nonan-8-yl)-4',5'-dihydro-1H, 1'H-7,7'-binaphtho[1,2-d]imidazol-2-yl)pyrrolidin-1-yl)-3-methyl-1-oxobutan-2-ylcarbamate Methyl (S)-1-((S)-2-(2'-((S)-7-((2S,3R)-2-methoxycarbonylamino-3-methoxybutanoyl)-1,4-dioxa-7-azaspiro[4.4]nonan-8-yl)-4',5'-dihydro-1H,1'H-7,7'-binaphtho[1,2-d]imidazol-2-yl)pyrrolidin-1-yl)-3-methyl-1-oxobutan-2-ylcarbamate: (ESI) m/z 863 [M+H]$^+$.

Example EL

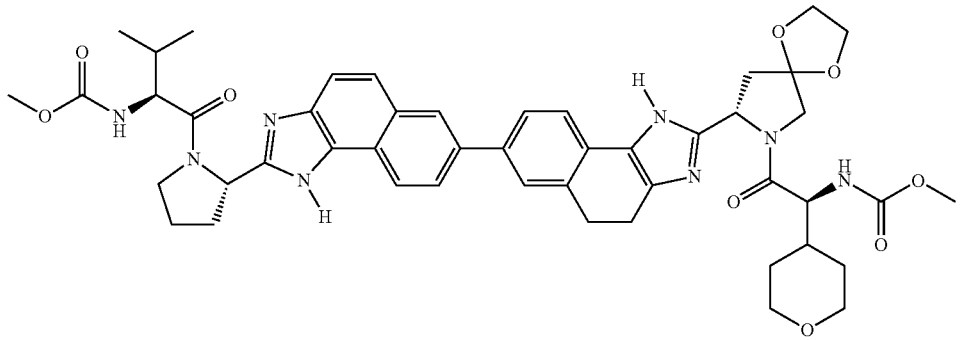

methyl (S)-1-((S)-2-(2'-((S)-7-((S)-2-methoxycarbonylamino-2-(tetrahydro-2H-pyran-4-yl)acetyl)-1,4-dioxa-7-azaspiro[4.4]nonan-8-yl)-4',5'-dihydro-1H, 1'H-7,7'-binaphtho[1,2-d]imidazol-2-yl)pyrrolidin-1-yl)-3-methyl-1-oxobutan-2-ylcarbamate Methyl (S)-1-((S)-2-(2'-((S)-7-((S)-2-methoxycarbonylamino-2-(tetrahydro-2H-pyran-4-yl)acetyl)-1,4-dioxa-7-azaspiro[4.4]nonan-8-yl)-4',5'-dihydro-1H, 1'H-7,7'-binaphtho[1,2-d]imidazol-2-yl)pyrrolidin-1-yl)-3-methyl-1-oxobutan-2-ylcarbamate: (ESI) m/z 889 [M+H]$^+$.

Example EM

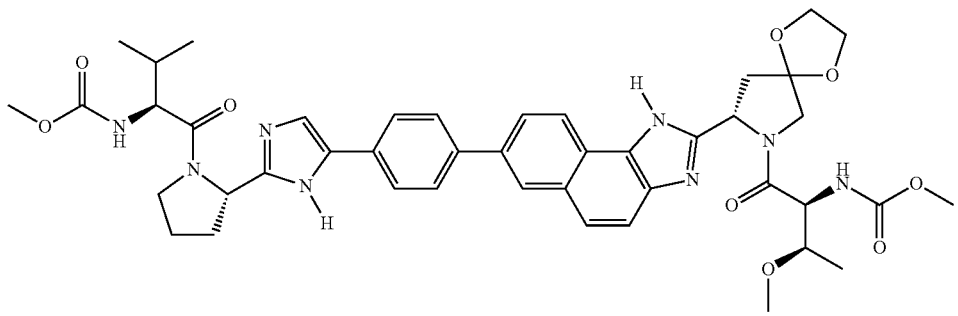

methyl (S)-1-((S)-2-(5-(4-(2-((S)-7-((2S,3R)-2-methoxycarbonylamino-3-methoxybutanoyl)-1,4-dioxa-7-azaspiro[4.4]nonan-8-yl)-1H-naphtho[1,2-d]imidazol-7-yl)phenyl)-1H-imidazol-2-yl)pyrrolidin-1-yl)-3-methyl-1-oxobutan-2-ylcarbamate Methyl (S)-1-((S)-2-(5-(4-(2-((S)-7-((2S,3R)-2-methoxycarbonylamino-3-methoxybutanoyl)-1,4-dioxa-7-azaspiro[4.4]nonan-8-yl)-1H-naphtho[1,2-d]imidazol-7-yl)phenyl)-1H-imidazol-2-yl)pyrrolidin-1-yl)-3-methyl-1-oxobutan-2-ylcarbamate: (ESI) m/z 838 [M+H]$^+$.

Example EN

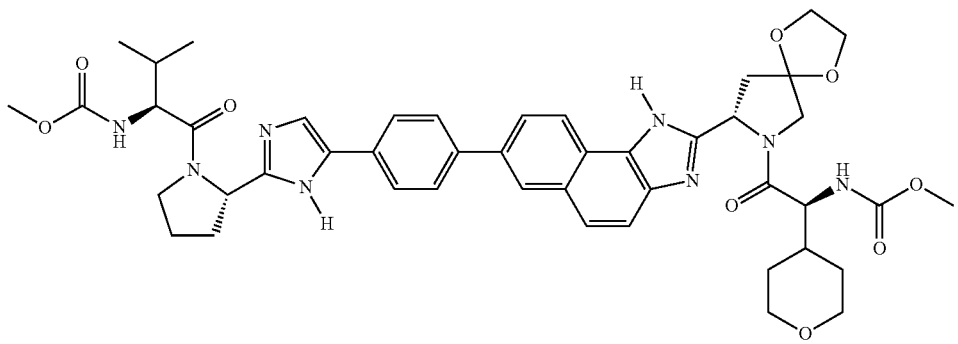

methyl (8)-1-((S)-2-(5-(4-(2-((S)-7-((S)-2-methoxycarbonylamino-2-(tetrahydro-2H-pyran-4-yl)acetyl)-1,4-dioxa-7-azaspiro[4.4]nonan-8-yl)-1H-naphtho[1,2-d]imidazol-7-yl)phenyl)-1H-imidazol-2-yl)pyrrolidin-1-yl)-3-methyl-1-oxobutan-2-ylcarbamate Methyl (S)-1-((S)-2-(5-(4-(2-((S)-7-((S)-2-methoxycarbonylamino-2-(tetrahydro-2H-pyran-4-yl)acetyl)-1,4-dioxa-7-azaspiro[4.4]nonan-8-yl)-1H-naphtho[1,2-d]imidazol-7-yl)phenyl)-1H-imidazol-2-yl)pyrrolidin-1-yl)-3-methyl-1-oxobutan-2-ylcarbamate: (ESI) m/z 864 [M+H]$^+$.

Example EO

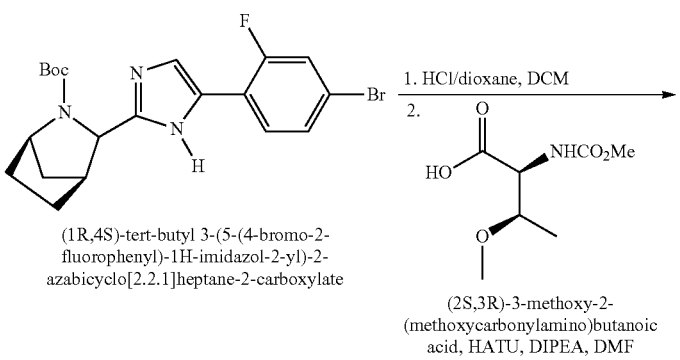

(1R,4S)-tert-butyl 3-(5-(4-bromo-2-fluorophenyl)-1H-imidazol-2-yl)-2-azabicyclo[2.2.1]heptane-2-carboxylate (2S,3R)-3-methoxy-2-(methoxycarbonylamino)butanoic acid, HATU, DIPEA, DMF -continued

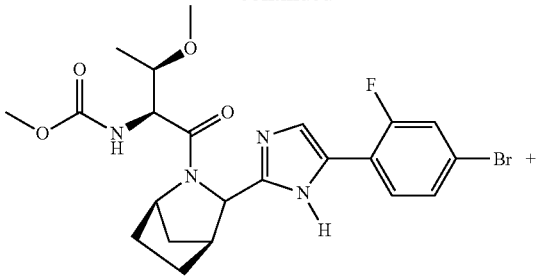

methyl (2S,3R)-1-((1R,4S)-3-(5-(4-bromo-2-fluorophenyl)-
1H-imidazol-2-yl)-2-azabicyclo[2.2.1]heptan-2-yl)-3-
methoxy-1-oxobutan-2-ylcarbamate

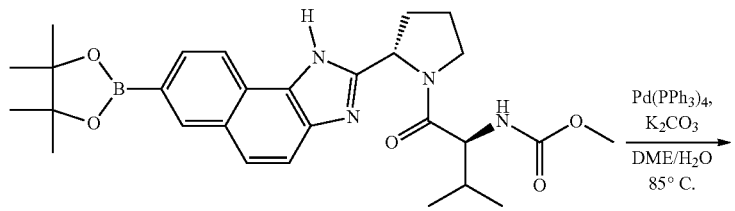

methyl (S)-3-methyl-1-oxo-1-((S)-2-(7-(4,4,5,5-
tetramethyl-1,3,2-dioxaborolan-2-yl)-1H-naphtho[1,2-d]
imidazol-2-yl)pyrrolidin-1-yl)butan-2-ylcarbamate

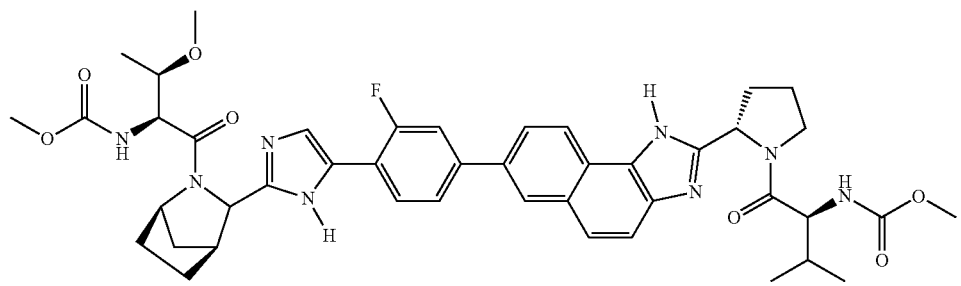

methyl (2S,3R)-1-((1R,4S)-3-(5-(4-(2-((S)-1-((S)-2-methoxycarbonylamino-3-
methylbutanoyl)pyrrolidin-2-yl)-1H-naphtho[1,2-d]imidazol-7-yl)-2-fluorophenyl)-1H-
imidazol-2-yl)-2-azabicyclo[2.2.1]heptan-2-yl)-3-methoxy-1-oxobutan-2-ylcarbamate (1R,4S)-tert-butyl 3-(5-(4-bromo-2-fluorophenyl)-1H-imidazol-2-yl)-2-azabicyclo[2.2.1]heptane-2-carboxylate: Title compound was prepared by methods analogous to those described for (1R,4S)-tert-butyl 3-(5-(4-bromophenyl)-1H-imidazol-2-yl)-2-azabicyclo[2.2.1]heptane-2-carboxylate, substituting 2-bromo-1-(4-bromo-3-fluorophenyl)ethanone for 2-bromo-1-(4-bromophenyl)ethanone.

Methyl (2S,3R)-1-((1R,4S)-3-(5-(4-bromo-2-fluorophenyl)-1H-imidazol-2-yl)-2-azabicyclo[2.2.1]heptan-2-yl)-3-methoxy-1-oxobutan-2-ylcarbamate: (1R,4S)-tert-butyl 3-(5-(4-bromo-2-fluorophenyl)-1H-imidazol-2-yl)-2-azabicyclo[2.2.1]heptane-2-carboxylate was dissolved in DCM (5 mL) and treated with HCl (4M in dioxane, 1 mL). After 1 h, the reaction mixture was concentrated. The residue was treated (2S,3R)-3-methoxy-2-(methoxycarbonylamino)butanoic acid (76 mg, 0.406 mmol), HATU (154 mg, 0.406 mmol) and DMF (4 mL). The stirred reaction mixture was cooled to 0° C., DIPEA (0.35 mL, 2.03 mmol) was added dropwise and the reaction mixture was warmed to RT. After 20 min, it was diluted with EtOAc and washed with saturated aqueous NaHCO$_3$ and brine, dried over MgSO$_4$, filtered and concentrated. The crude residue was purified by silica column chromatography (0% to 33% MeOH/EtOAc) to afford the title compound (162 mg, 78%).

Methyl (2S,3R)-1-((1R,4S)-3-(5-(4-(2-((S)-1-((S)-2-methoxycarbonylamino-3-methylbutanoyl)pyrrolidin-2-yl)-1H-naphtho[1,2-d]imidazol-7-yl)-2-fluorophenyl)-1H-imidazol-2-yl)-2-azabicyclo[2.2.1]heptan-2-yl)-3-methoxy-1-oxobutan-2-ylcarbamate: Methyl (2S,3R)-1-((1R,4S)-3-(5-(4-bromo-2-fluorophenyl)-1H-imidazol-2-yl)-2-azabicyclo[2.2.1]heptan-2-yl)-3-methoxy-1-oxobutan-2-ylcarbamate (162 mg, 0.318 mmol), methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate (199 mg, 0.382 mmol), Pd(PPh$_3$)$_4$ (37 mg, 0.0318 mmol) and K$_2$CO$_3$ (2M in H$_2$O, 0.4 mL, 0.8 mmol) were suspended in DME (3 mL). The reaction mixture was degassed with N$_2$ for 11 min then heated to reflux for 2.5 h. Upon completion, the reaction mixture was diluted with MeOH, filtered over a thiol SPE column and concentrated. The crude residue was purified by silica column chromatography (0% to 50% MeOH/EtOAc) to afford the title compound (125 mg, 48%). (ESI) m/z 823 [M+H]$^+$.

Example EP

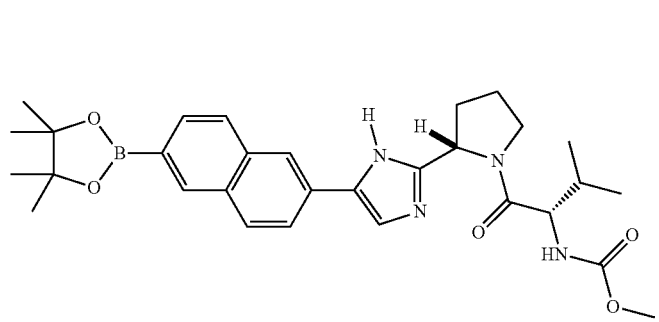

[2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]carbamic acid methyl ester

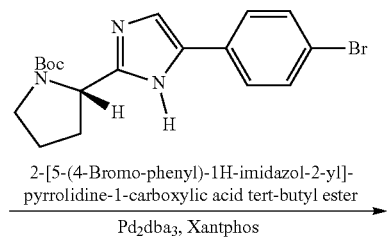

2-[5-(4-Bromo-phenyl)-1H-imidazol-2-yl]-pyrrolidine-1-carboxylic acid tert-butyl ester Pd₂dba₃, Xantphos

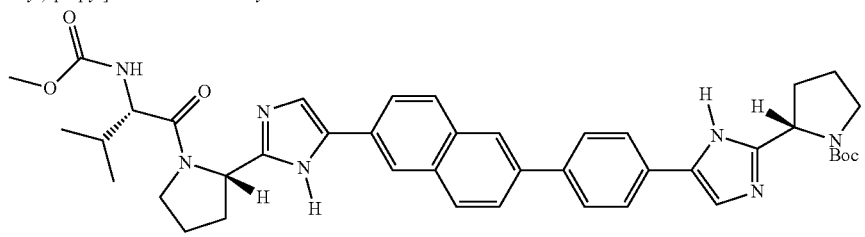

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester. To a solution of 2-[5-(4-Bromo-phenyl)-1H-imidazol-2-yl]-pyrrolidine-1-carboxylic acid tert-butyl ester (1.00 g, 2.5 mmol) and [2-Methyl-1-(2-{5-[6-(4,4,5,5-tetramethyl-[1,332]dioxaborolan-2-yl)-naphthalen-2-yl]-1H-imidazol-2-yl}-pyrrolidine-1-carbonyl)-propyl]-carbamic acid methyl ester (1.97 g, 3.6 mmol, 1.5 equiv.) in DME (12.5 mL) was added K₃PO₄ (aqueous, 2 M, 3.9 mL, 7.8 mmol, 3 equiv.), Pd₂dba₃ (0.12 g, 0.13 mmol, 0.05 equiv.), and Xantphos (0.15 g, 0.26 mmol, 0.1 equiv.). The slurry was degassed with argon for 5 minutes and heated to 80° C. for 18 hours. The resulting reaction mixture was diluted with EtOAc/MeOH (10:1) and filtered through celite. The solution was washed with water and brine. The aqueous layer was back-extracted with EtOAc and the combined organic layers were dried over Na₂SO₄ and concentrated. The crude oil was purified by column chromatography (SiO₂, 50→100% EtOAc in Hexanes) to provide 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester (0.93 g, 49%) as a yellow powder. LCMS-ESI⁺: calc'd for $C_{42}H_{49}N_7O_5$: 731.4 (M⁺); Found: 732.9 (M+H⁺).

Example EQ

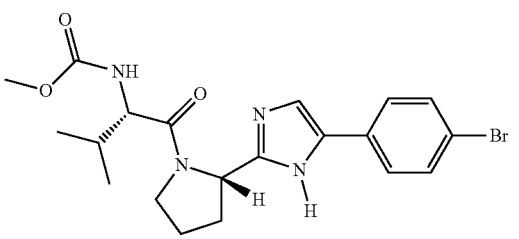

(1-{2-[5-(4-Bromo-phenyl)-1H-imidazol-2-yl]-pyrrolidine-1-carbonyl}-2-methyl-propyl)-carbamic acid methyl ester Pd₂dba₃, Xantphos

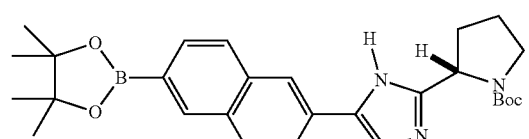

2-{5-[6-(4,4,5,5-Tetramethyl-[1,3,2]dioxaborolan-2-yl)-naphthalen-2-yl]-1H-imidazol-2-yl}-pyrrolidine-1-carboxylic acid tert-butyl ester -continued

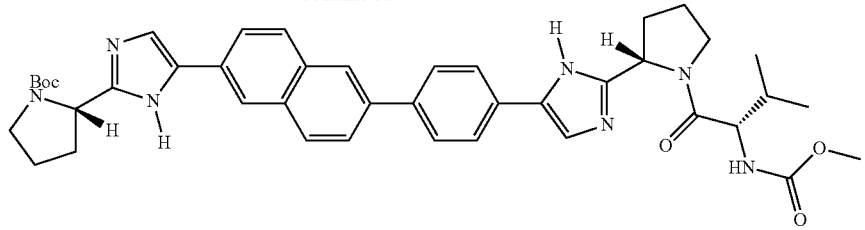

2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester 2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester. 2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester was prepared following the procedure for 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester, substituting (1-{2-[5-(4-Bromo-phenyl)-1H-imidazol-2-yl]-pyrrolidine-1-carbonyl}-2-methyl-propyl)-carbamic acid methyl ester for 2-[5-(4-Bromo-phenyl)-1H-imidazol-2-yl]-pyrrolidine-1-carboxylic acid tert-butyl ester and 2-{5-[6-(4,4,5,5-Tetramethyl-[1,3,2]dioxaborolan-2-yl)-naphthalen-2-yl]-1H-imidazol-2-yl}-pyrrolidine-1-carboxylic acid tert-butyl ester for [2-Methyl-1-(2-{5-[6-(4,4,5,5-tetramethyl-[1,3,2]dioxaborolan-2-yl)-naphthalen-2-yl]-1H-imidazol-2-yl}-pyrrolidine-1-carbonyl)-propyl]-carbamic acid methyl ester. LCMS-ESI⁺: calc'd for $C_{42}H_{49}N_7O_5$: 731.4 (M⁺); Found: 732.9 (M+H⁺).

Example ER

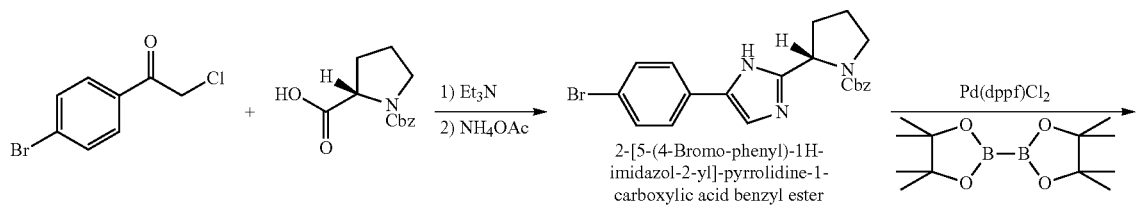

2-[5-(4-Bromo-phenyl)-1H-imidazol-2-yl]-pyrrolidine-1-carboxylic acid benzyl ester 2-{5-[4-(4,4,5,5-Tetramethyl-[1,3,2]dioxaborolan-2-yl)-phenyl]-1H-imidazol-2-yl}-pyrrolidine-1-carboxylic acid benzyl ester

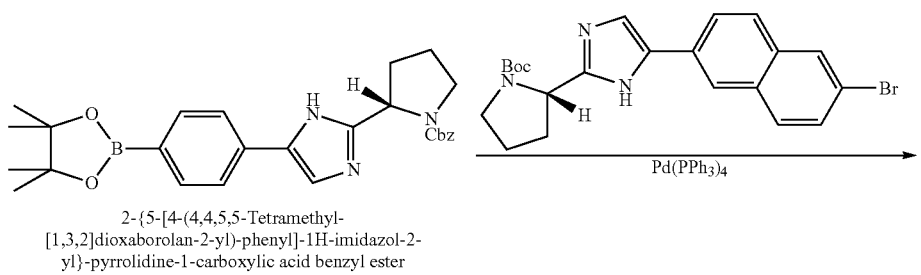

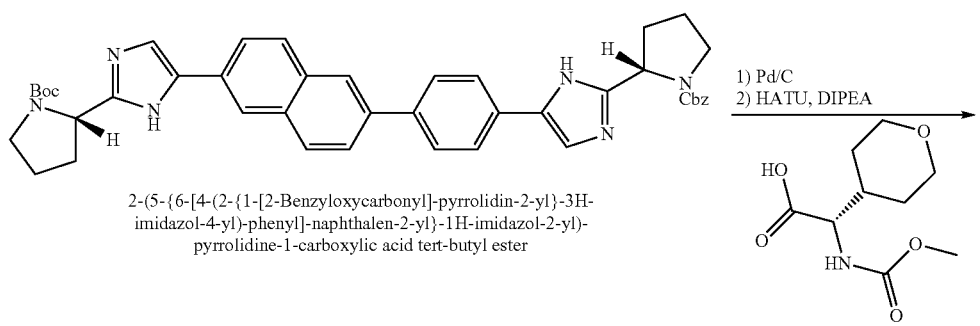

2-(5-{6-[4-(2-{1-[2-Benzyloxycarbonyl]-pyrrolidin-2-yl}-3H-imidazol-4-yl)-phenyl]-naphthalen-2-yl}-1H-imidazol-2-yl)-pyrrolidine-1-carboxylic acid tert-butyl ester -continued

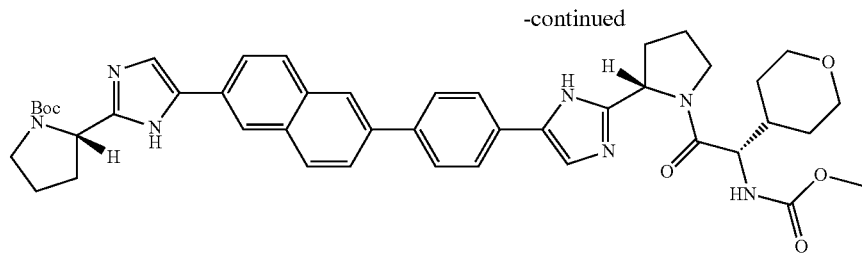

2-(5-{6-[4-(2-{1-[2-Methoxycarbonylamino-2-(tetrahydro-pyran-4-yl)-acetyl]-pyrrolidin-2-yl}-3H-imidazol-4-yl)-phenyl]-naphthalen-2-yl}-1H-imidazol-2-yl)-pyrrolidine-1-carboxylic acid tert-butyl ester

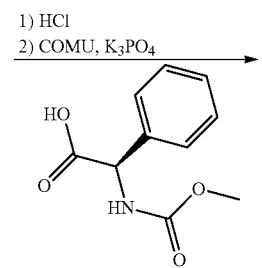

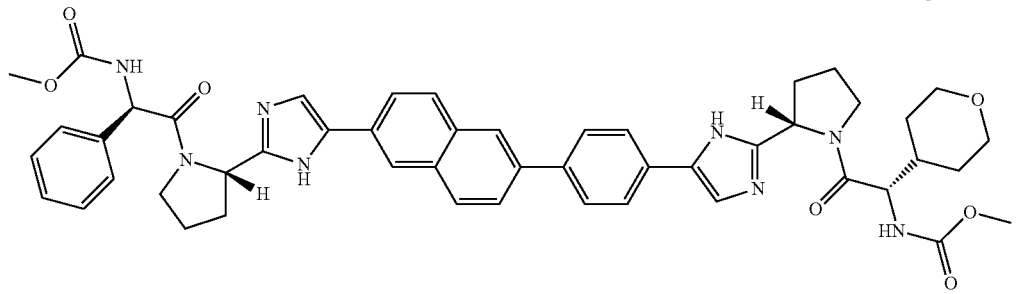

[2-(2-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester 2-{5-[4-(4,4,5,5-Tetramethyl-[1,3,2]dioxaborolan-2-yl)-phenyl]-1H-imidazol-2-yl}-pyrrolidine-1-carboxylic acid benzyl ester. 2-{5-[4-(4,4,5,5-Tetramethyl-[1,3,2]dioxaborolan-2-yl)-phenyl]-1H-imidazol-2-yl}-pyrrolidin-1-carboxylic acid benzyl ester was prepared following the procedure for Example A using pyrrolidine-1,2-dicarboxylic acid 1-benzyl ester in place of pyrrolidin-1,2-dicarboxylic acid 1-tert-Butyl ester. LCMS-ESI$^+$: calc'd for $C_{27}H_{32}BN_3O_4$: 473.37 ($M^+$); Found: 474.47 ($M+H^+$).

2-(5-{6-[4-(2-{1-[2-Benzyloxycarbonyl]-pyrrolidin-2-yl}-3H-imidazol-4-yl)-phenyl]-naphthalen-2-yl}-1H-imidazol-2-yl)-pyrrolidine-1-carboxylic acid tert-butyl ester. To a solution of 2-[5-(6-Bromo-naphthalen-2-yl)-1H-imidazol-2-yl]-pyrrolidine-1-carboxylic acid tert-butyl ester (2.26g, 5.11 mmol) and 2-{5-[4-(4,4,5,5-Tetramethyl-[1,3,2]dioxaborolan-2-yl)-phenyl]-1H-imidazol-2-yl}-pyrrolidine-1-carboxylic acid benzyl ester (3.00 g, 6.34 mmol) in DME (25 mL) was added Tetrakis(triphenylphosphine)Palladium (0.30 g, 0.26 mmol) and aqueous potassium phosphate (2M, 7.6 mL, 15.2 mmol). The solution was degassed with argon for 15 min and heated to 80° C. for 18 h with stirring. The solution was cooled, filtered and diluted with EtOAc. The organic layer was washed with brine, dried over $Na_2SO_4$ and concentrated. The crude oil was purified by column chromatography (SiO$_2$, 30→100% EtOAc (10% MeOH) in Hexanes) to provide 2-(5-{6-[4-(2-{1-[2-Methoxycarbonylamino-2-(tetrahydro-pyran-4-yl)-acetyl]-pyrrolidin-2-yl}-3H-imidazol-4-yl)-phenyl]-naphthalen-2-yl}-1H-imidazol-2-yl)-pyrrolidine-1-carboxylic acid tert-butyl ester (4.31 g, 84%). LCMS-ESI$^+$: calc'd for $C_{43}H_{44}N_6O_4$: 708.34 ($M^+$); Found: 709.58 ($M+H^+$).

2-(5-{6-[4-(2-{1-[2-Methoxycarbonylamino-2-(tetrahydro-pyran-4-yl)-acetyl]-pyrrolidin-2-yl}-3H-imidazol-4-yl)-phenyl]-naphthalen-2-yl}-1H-imidazol-2-yl)-pyrrolidine-1-carboxylic acid tert-butyl ester. To a solution of 2-(5-{6-[4-(2-{1-[2-Methoxycarbonylamino-2-(tetrahydro-pyran-4-yl)-acetyl]-pyrrolidin-2-yl}-3H-imidazol-4-yl)-phenyl]-naphthalen-2-yl}-1H-imidazol-2-yl)-pyrrolidine-1-carboxylic acid tert-butyl ester (0.25 g, 0.36 mmol) in EtOH (3.5 mL) was added Palladium on carbon (10%, 0.42 g, 0.39 mmol) and Potassium Carbonate (0.10 g, 0.70 mmol). The slurry was stirred at room temperature under an atmosphere of $H_2$ for 72 h. The slurry was filtered through celite and washed with EtOH. The filtrate was concentrated to an oil and diluted with $CH_2Cl_2$ (3 mL). Methoxycarbonylamino-(tetrahydro-pyran-4-yl)-acetic acid (0.12 g, 0.46 mmol), HATU (0.17 g, 0.46 mmol), and DIPEA (0.13 mL, 1.03 mmol) were added, and the solution was stirred at room temperature for 2 h. The solution was diluted with THF and LiOH (2.5 M, 0.25 mL) was added. The solution was concentrated to dryness and the crude oil was purified by column chromatography (SiO$_2$, 30→100% EtOAc (10% MeOH) in Hexanes to 60% MeOH in EtOAc) to provide 2-(5-{6-[4-(2-{1-[2-Methoxycarbonylamino-2-(tetrahydro-pyran-4-yl)-acetyl]-pyrrolidin-2-yl}-3H-imidazol-4-yl)-phenyl]-naphthalen-2-yl}-1H-imidazol-2-yl)-pyrrolidine-1-carboxylic acid tert-butyl ester (0.22 g, 79%). LCMS-ESI$^+$: calc'd for $C_{44}H_{51}N_7O_6$: 773.39 ($M^+$); Found: 774.77 ($M+H^+$).

[2-(2-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester. To a solution of 2-(5-{6-[4-(2-{1-[2-Methoxycarbonylamino-2-(tetrahydro-pyran-4-yl)-acetyl]-pyrrolidin-2-yl}-3H-imidazol-4-yl)-phenyl]-naphthalen-2-yl}-1H-imidazol-2-yl)-pyrrolidine-1-carboxylic acid tert-butyl ester (0.22 g, 0.28 mmol) in $CH_2Cl_2$ (2.5 mL) and MeOH (0.1 mL) was added HCl (in dioxane, 4 M, 0.7 mL, 2.80 mmol). The solution was stirred at room temperature for 2 h and concentrated to dryness. The resulting solid was slurried in $CH_2Cl_2$ (5 mL). Methoxycarbonylamino-phenyl-acetic acid (0.09 g, 0.42 mmol) and Potassium Phosphate (0.18 g, 0.84 mmol) were added and the resulting solution was cooled to 0° C. (external, ice). COMU (0.15 g, 0.35 mmol) was added and the reaction was stirred at 0° C. for 2 h. Additional COMU (0.10 g) and DIPEA (0.15 mL, 0.86 mmol) was added and the reaction was stirred for 2 h. The resulting red solution was concentrated and diluted with DMF and filtered. Purification by preparative HPLC (Gemini, 15→40% MeCN in H$_2$O (0.1% formic acid)) and lyophilization provided [2-(2-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester (0.05 g, 22%). LCMS-ESI$^+$: calc'd for C$_{49}$H$_{52}$N$_8$O$_7$: 864.40 (M$^+$); Found: 865.87 (M+H$^+$).

Example ES

CH$_2$Cl$_2$ (3 mL). Methoxycarbonylamino-phenyl-acetic acid (0.11 g, 0.54 mmol) and Potassium Phosphate (0.08 g, 0.35 mmol) were added and the resulting slurry was cooled to 0° C. (external, ice). COMU (0.19 g, 0.44 mmol) was added and the reaction was stirred at 0° C. for 2 h. The slurry was diluted with CH$_2$Cl$_2$ and filtered through celite. The filtrate was concentrated and purified by column chromatography (SiO$_2$, 30→100% EtOAc (10% MeOH) in Hexanes to 60% MeOH in EtOAc) to provide 2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carboxylic acid tert-butyl ester (0.20 g, 74%). LCMS-ESI$^+$: calc'd for C$_{45}$H$_{47}$N$_7$O$_5$: 765.36 (M$^+$); Found: 766.64 (M+H$^+$).

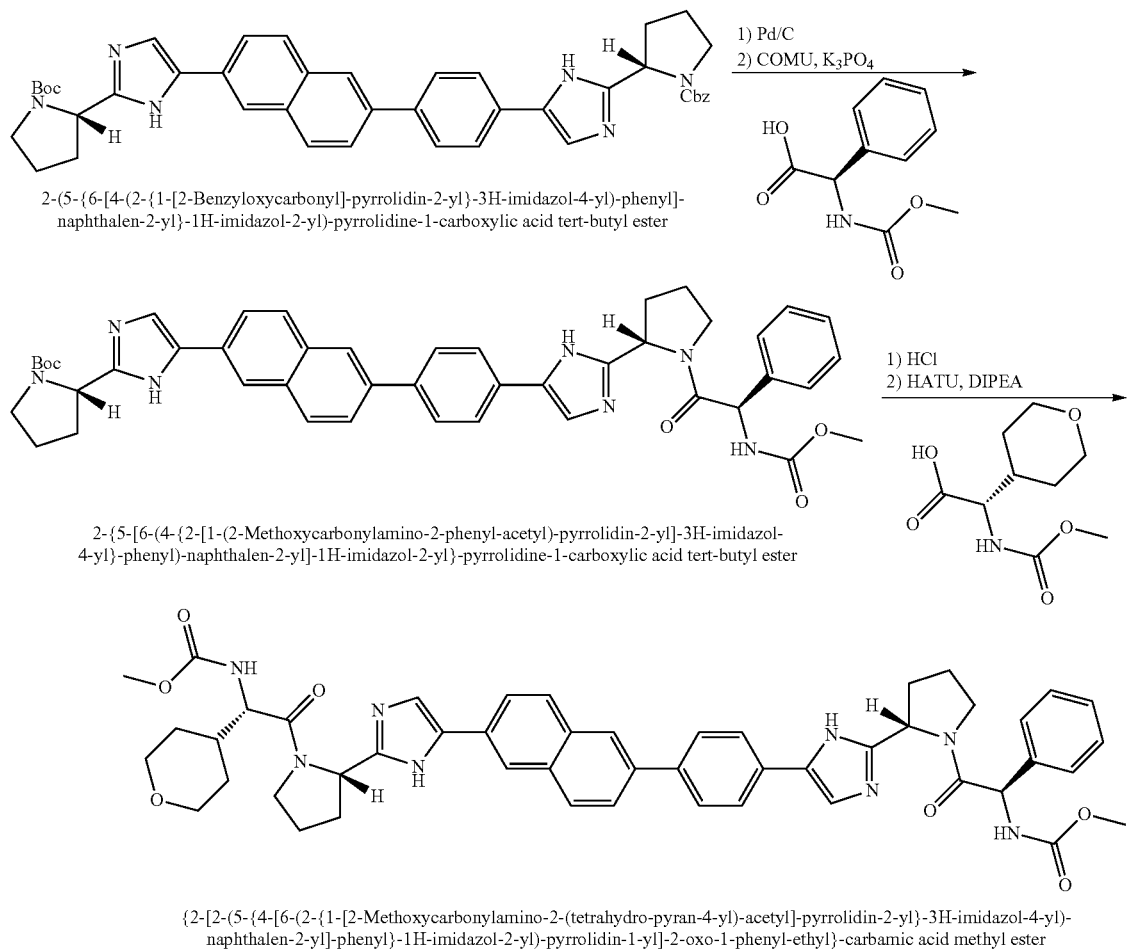

2-(5-{6-[4-(2-{1-[2-Benzyloxycarbonyl]-pyrrolidin-2-yl}-3H-imidazol-4-yl)-phenyl]-naphthalen-2-yl}-1H-imidazol-2-yl)-pyrrolidine-1-carboxylic acid tert-butyl ester 2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carboxylic acid tert-butyl ester {2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester 2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carboxylic acid tert-butyl ester. To a solution of 2-(5-{6-[4-(2-{1-[2-Methoxycarbonylamino-2-(tetrahydro-pyran-4-yl)-acetyl]-pyrrolidin-2-yl}-3H-imidazol-4-yl)-phenyl]-naphthalen-2-yl}-1H-imidazol-2-yl)-pyrrolidine-1-carboxylic acid tert-butyl ester (0.25 g, 0.36 mmol) in EtOH (3.5 mL) was added Palladium on carbon (10%, 0.42 g, 0.39 mmol) and Potassium Carbonate (0.10 g, 0.70 mmol). The slurry was stirred at room temperature under an atmosphere of H$_2$ for 72 h. The slurry was filtered through celite and washed with EtOH. The filtrate was concentrated to an oil and diluted with {2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester. To a solution of 2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carboxylic acid tert-butyl ester (0.20 g, 0.26 mmol) in CH$_2$Cl$_2$ (2.5 mL) and MeOH (0.1 mL) was added HCl (in dioxanes, 4 M, 0.7 mL, 2.80 mmol). The solution was stirred at room temperature for 3 h and concentrated to dryness. The resulting solid was slurried in CH$_2$Cl$_2$ (4 mL). Methoxycarbonylamino-(tetrahydro-pyran-4-yl)-acetic acid (0.12 g, 0.54 mmol), HATU (0.12 g, 0.33 mmol), and DIPEA (0.2 mL, 1.15 mmol) were added. The resulting solution was stirred at room temperature for 1 h. The solution was diluted with THF and LiOH (2.5 M, 0.1 mL) was added. The solution was concentrated to dryness and the crude oil was diluted with DMF and purified by preparative HPLC (Gemini, 15→40% MeCN in H$_2$O (0.1% formic acid)) and lyophilized to provide {2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester (0.083 g, 37%). LCMS-ESI$^+$: calc'd for C$_{49}$H$_{52}$N$_8$O$_7$: 864.40 (M$^+$); Found: 866.01 (M+H$^+$).

Example ET to provide 2-Methoxycarbonylamino-2-phenyl-propionic acid (0.66 g, 49%). LCMS-ESI$^+$: calc'd for C$_{11}$H$_{13}$NO$_4$: 223.08 (M$^+$); Found: 223.97 (M+H$^+$).

[1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. To a solution of 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester (0.15 g, 0.205 mmol) in CH$_2$Cl$_2$ (2 mL) and MeOH (0.2 mL) was added HCl (in dioxanes, 4 M, 1.0 mL, 4.1 mmol). The solution was stirred at room temperature for 1 h and concentrated to dryness. The result-

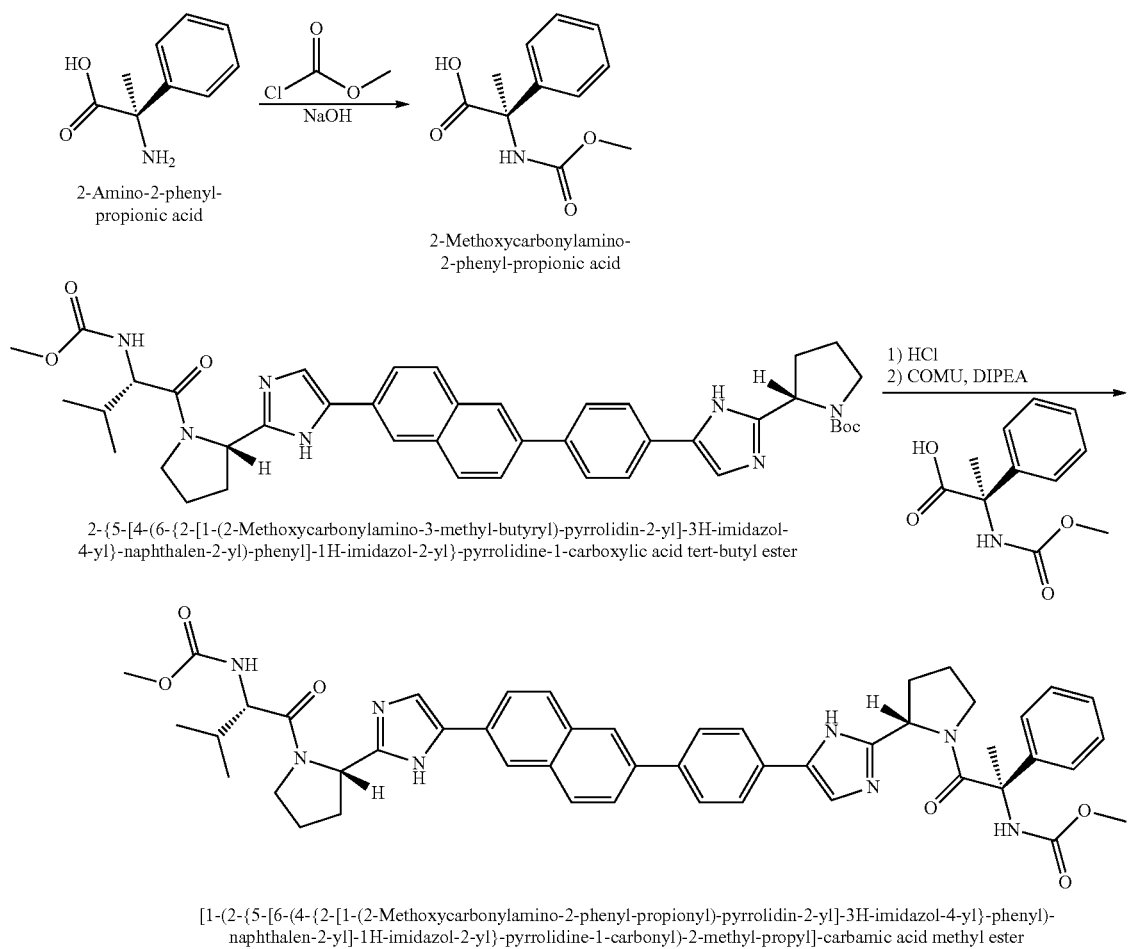

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester

[1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester 2-Methoxycarbonylamino-2-phenyl-propionic acid. To a solution of 2-Amino-2-phenyl-propionic acid (1.00 g, 6.06 mmol) in THF (17 mL), was added aqueous NaOH (6 M, 2.5 mL, 15.0 mmol) and Methyl Chloroformate (0.55 mL, 7.10 mmol). The solution was stirred for 18 h. Aqueous HCl (12 M, 1.5 mL, 18 mmol) was slowly added. The solution was diluted with HCl (1M) and extracted with Et$_2$O (3 times). The combined organic layers were extracted with NaOH (2N, 3 times). The aqueous layers were acidified with HCl (12 N) and extracted with Et$_2$O (3 times). The combined organic layers were dried over MgSO$_4$ and concentrated. The crude oil was diluted in CH$_2$Cl$_2$ and concentrated again ing solid was dissolved in DMF (2.3 mL). 2-Methoxycarbonylamino-2-phenyl-propionic acid (0.06 g, 0.29 mmol), COMU (0.12 g, 0.27 mmol) and DIPEA (0.2 mL, 1.15 mmol) were added. The reaction was stirred at room temperature for 18 h before HCl (6M, 0.1 mL) was added. The solution was purified by preparative HPLC (Gemini, 15→40% MeCN in H$_2$O (0.1% formic acid)) and lyophilized to provide [1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.072 g, 42%). LCMS-ESI$^+$: calc'd for C$_{48}$H$_{52}$N$_8$O$_6$: 836.40 (M$^+$); Found: 837.87 (M+H$^+$).

Example EU

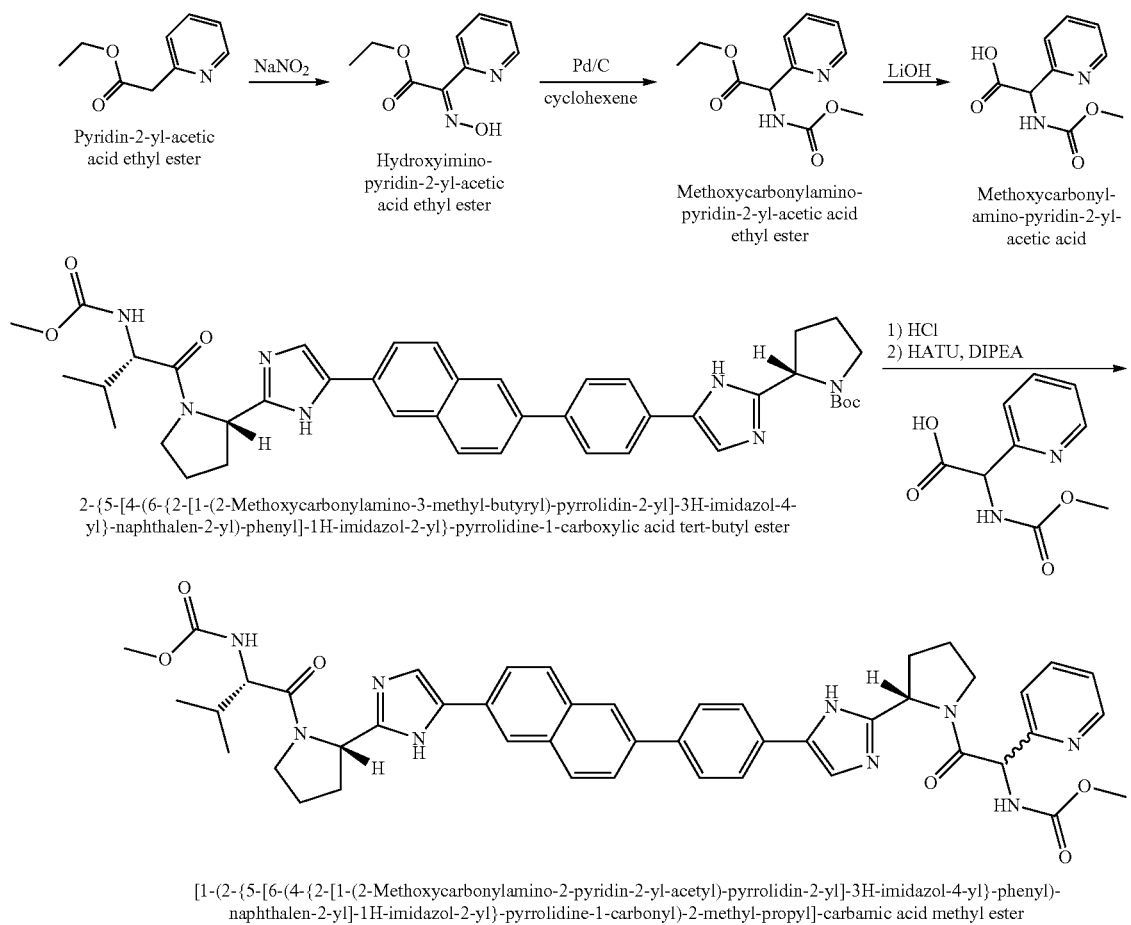

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester

[1-(2-{5-[6-(4-{2-[1-(2-Methoxycarbonylamino-2-pyridin-2-yl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester Hydroxyimino-pyridin-2-yl-acetic acid ethyl ester. Hydroxyimino-pyridin-2-yl-acetic acid ethyl ester was prepared from Pyridin-2-yl-acetic acid ethyl ester following the procedure described in *J. Org. Chem.* 1961, 26, 3373.

Methoxycarbonylamino-pyridin-2-yl-acetic acid ethyl ester. To a solution of Hydroxyimino-pyridin-2-yl-acetic acid ethyl ester (2.35 g, 12.1 mmol) in EtOH (24 mL) was added Palladium on Carbon (10%, 0.64 g, 0.61 mmol), Dimethyl dicarbonate (3.2 mL, 30.3 mmol) and cyclohexene (3.68 mL, 36.3 mmol). The reaction was heated to reflux for 4 h and then cooled to room temperature. The slurry was filtered and washed with EtOH. The filtrate was concentrated to dryness and purified by column chromatography ($SiO_2$, 2→10% MeOH in $CH_2Cl_2$) to provide Methoxycarbonylamino-pyridin-2-yl-acetic acid ethyl ester (0.90 g, 31%). LCMS-ESI$^+$: calc'd for $C_{11}H_{14}N_2O_4$: 238.10 (M$^+$); Found: 239.06 (M+H$^+$).

Methoxycarbonylamino-pyridin-2-yl-acetic acid. To a solution of Methoxycarbonylamino-pyridin-2-yl-acetic acid ethyl ester (0.26 g, 1.1 mmol) in THF (6.0 mL) and MeOH (2.0 mL) was added aqueous LiOH (2.5 M, 2.2 mL, 5.5 mmol). The solution was stirred at room temperature for 1.5 h. The reaction was diluted with $CH_2Cl_2$ and washed with aqueous ammonium chloride and brine. The aqueous layers were combined and concentrated. The resulting solid was triterated with MeOH and filtered. The filtrated was concentrated and triterated a second time with MeOH. Concentration of the filtrate provided Methoxycarbonylamino-pyridin-2-yl-acetic acid which was used crude in the next step. LCMS-ESI$^+$: calc'd for $C_9H_{10}N_2O_4$: 210.06 (M$^+$); Found: 210.98 (M+H$^+$).

[1-(2-{5-[6-(4-{2-[1-(2-Methoxycarbonylamino-2-pyridin-2-yl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. To a solution of 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester (0.10 g, 0.0.14 mmol) in $CH_2Cl_2$ (1.3 mL) and MeOH (0.1 mL) was added HCl (in dioxanes, 4 M, 0.35 mL, 1.4 mmol). The solution was stirred at room temperature for 2 h and concentrated to dryness. The resulting solid was dissolved in DMF (1.5 mL). Methoxycarbonylamino-pyridin-2-yl-acetic acid (assumed 0.23 g, 1.1 mmol), HATU (0.06 g, 0.15 mmol) and DIPEA (0.12 mL, 0.69 mmol) were added. The solution was stirred at room temperature for 2 h. Additional HATU (0.13 g, 0.30 mmol) was added and the solution was stirred for 2 h. LiOH (2.5 M, 0.1 mL) was added and the reaction was concentrated. The crude oil was purified by preparative HPLC (Gemini, 15→40% MeCN in $H_2O$ (0.1% formic acid)) and lyophilized to provide [1-(2-{5-[6-(4-{2-[1-(2-Methoxycarbonylamino-2-pyridin-2-yl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.02 g, 22%). LCMS-ESI$^+$: calc'd for $C_{46}H_{49}N_9O_6$: 823.38 (M$^+$); Found: 824.88 (M+H$^+$).

Example EV

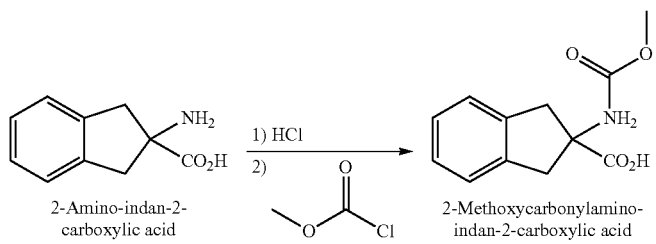

2-Amino-indan-2-carboxylic acid → 2-Methoxycarbonylamino-indan-2-carboxylic acid

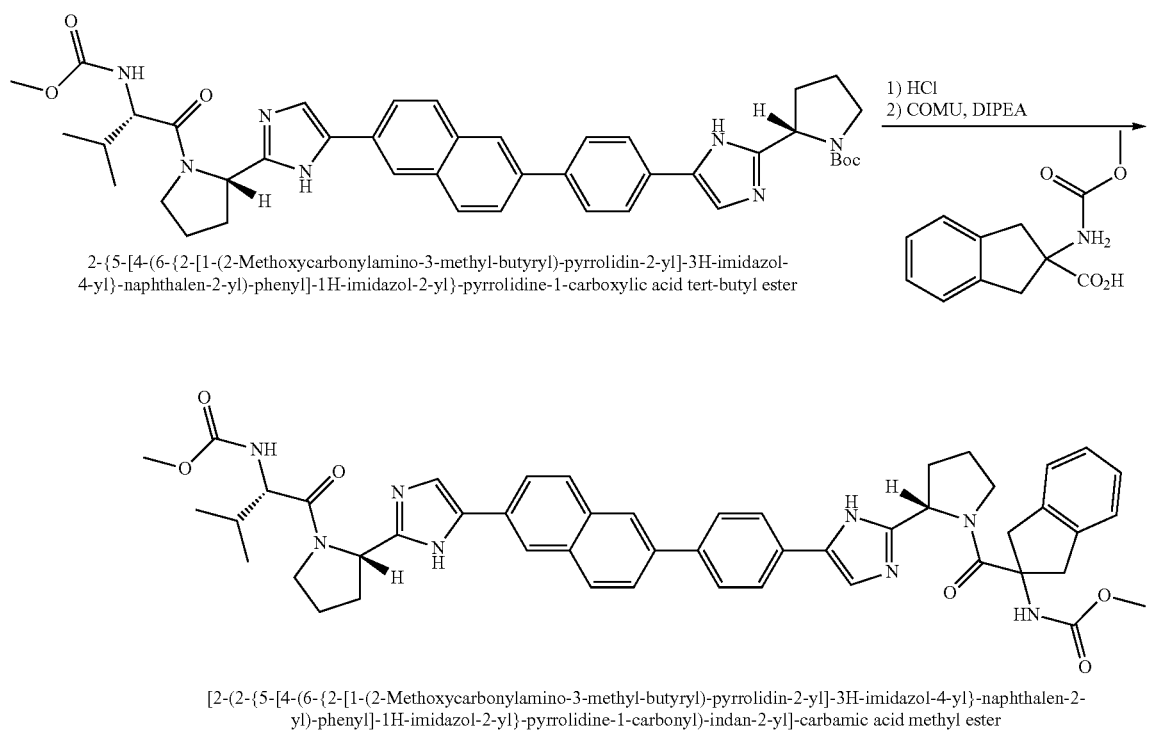

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester

[2-(2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-indan-2-yl]-carbamic acid methyl ester 2-Methoxycarbonylamino-indan-2-carboxylic acid. To a solution of 2-Amino-indan-2-carboxylic acid (0.45 g, 1.63 mmol) in $CH_2Cl_2$ (16 mL) was added HCl (in dioxanes, 4 M, 0.41 mL, 1.63 mmol). The solution was stirred at room temperature for 2 h and concentrated to dryness. The crude oil was dissolved in THF (6.5 mL). Aqueous NaOH (6 M, 0.92 mL, 5.5 mmol) and Methyl Chloroformate (0.15 mL, 1.95 mmol) were added and the resulting slurry was stirred at room temperature for 18 h. The reaction was diluted with HCl (1N) and extracted with $Et_2O$ (3 times). The combined organic layers were extracted with NaOH (2N, 3 times). The aqueous layers were acidified with HCl (6 N) and extracted with $Et_2O$ (3 times). The combined organic layers were dried over $MgSO_4$ and concentrated. The crude oil was diluted in hexanes and concentrated again to provide 2-Methoxycarbonylamino-indan-2-carboxylic acid (0.35 g, 92%). LCMS-ESI$^+$: calc'd for $C_{12}H_{13}NO_4$: 235.08 (M$^+$); Found: 235.94 (M+H$^+$).

[2-(2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-indan-2-yl]-carbamic acid methyl ester. To a solution of 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester (0.15 g, 0.205 mmol) in $CH_2Cl_2$ (2 mL) and MeOH (0.2 mL) was added HCl (in dioxanes, 4 M, 1.0 mL, 4.1 mmol). The solution was stirred at room temperature for 1 h and concentrated to dryness. The resulting solid was dissolved in DMF (2.5 mL). 2-2-Methoxycarbonylamino-indan-2-carboxylic acid (0.07 g, 0.31 mmol), COMU (0.12 g, 0.27 mmol) and DIPEA (0.25 mL, 1.4 mmol) were added. The reaction was stirred at room temperature for 18 h. The solution was purified by preparative HPLC (Gemini, 15→40% MeCN in $H_2O$ (0.1% formic acid)) and lyophilized to provide [2-(2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-indan-2-yl]-carbamic acid methyl ester (0.075 g, 31%). LCMS-ESI$^+$: calc'd for $C_{49}H_{52}N_8O_6$: 848.40 (M$^+$); Found: 849.97 (M+H$^+$).

Example EW

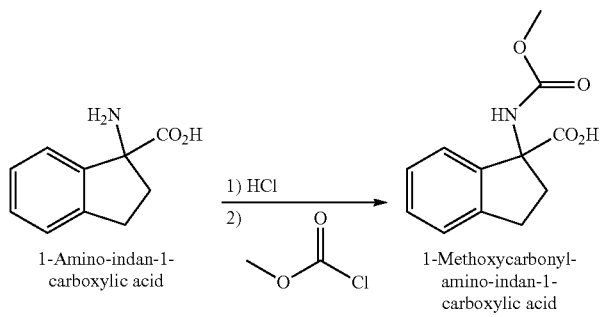

1-Amino-indan-1-carboxylic acid → 1-Methoxycarbonyl-amino-indan-1-carboxylic acid

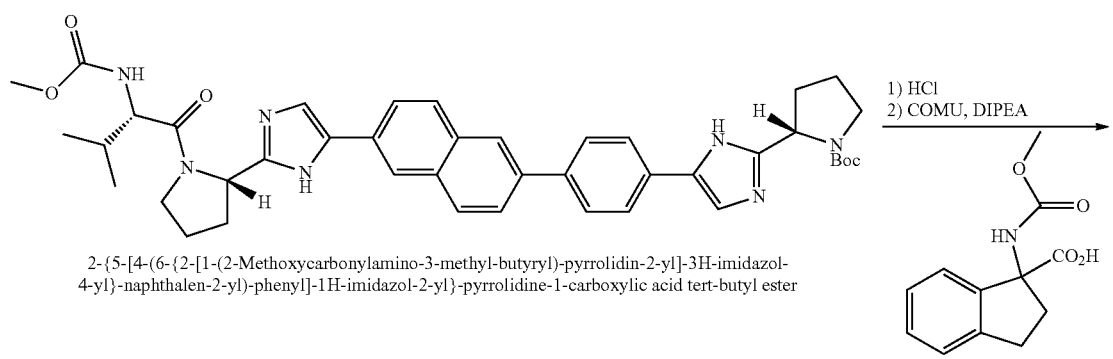

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester

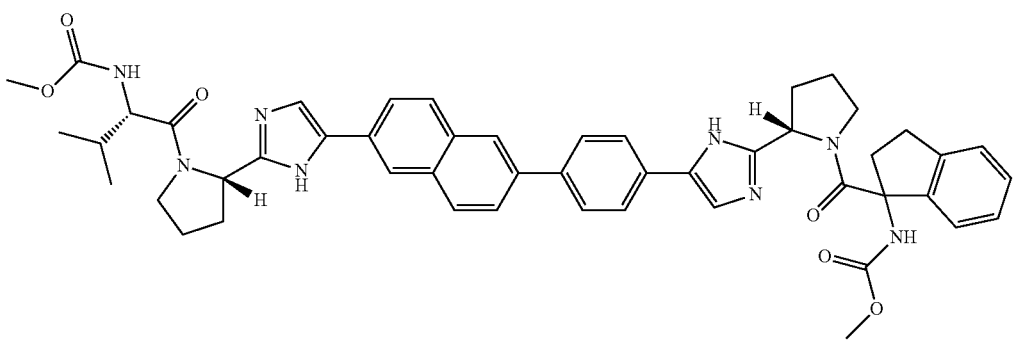

[1-(2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-indan-1-yl]-carbamic acid methyl ester

[1-(2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-indan-1-yl]-carbamic acid methyl ester. [1-(2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-indan-1-yl]-carbamic acid methyl ester (0.13 g, 38%) was prepared following the procedure for [2-(2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carbonyl)-indan-2-yl]-carbamic acid methyl ester, substituting 1-Amino-indan-1-carboxylic acid for 2-Amino-indan-2-carboxylic acid. LCMS-ESI$^+$: calc'd for $C_{49}H_{52}N_8O_6$: 848.40 (M$^+$); Found: 849.91 (M+H$^+$).

Example EX

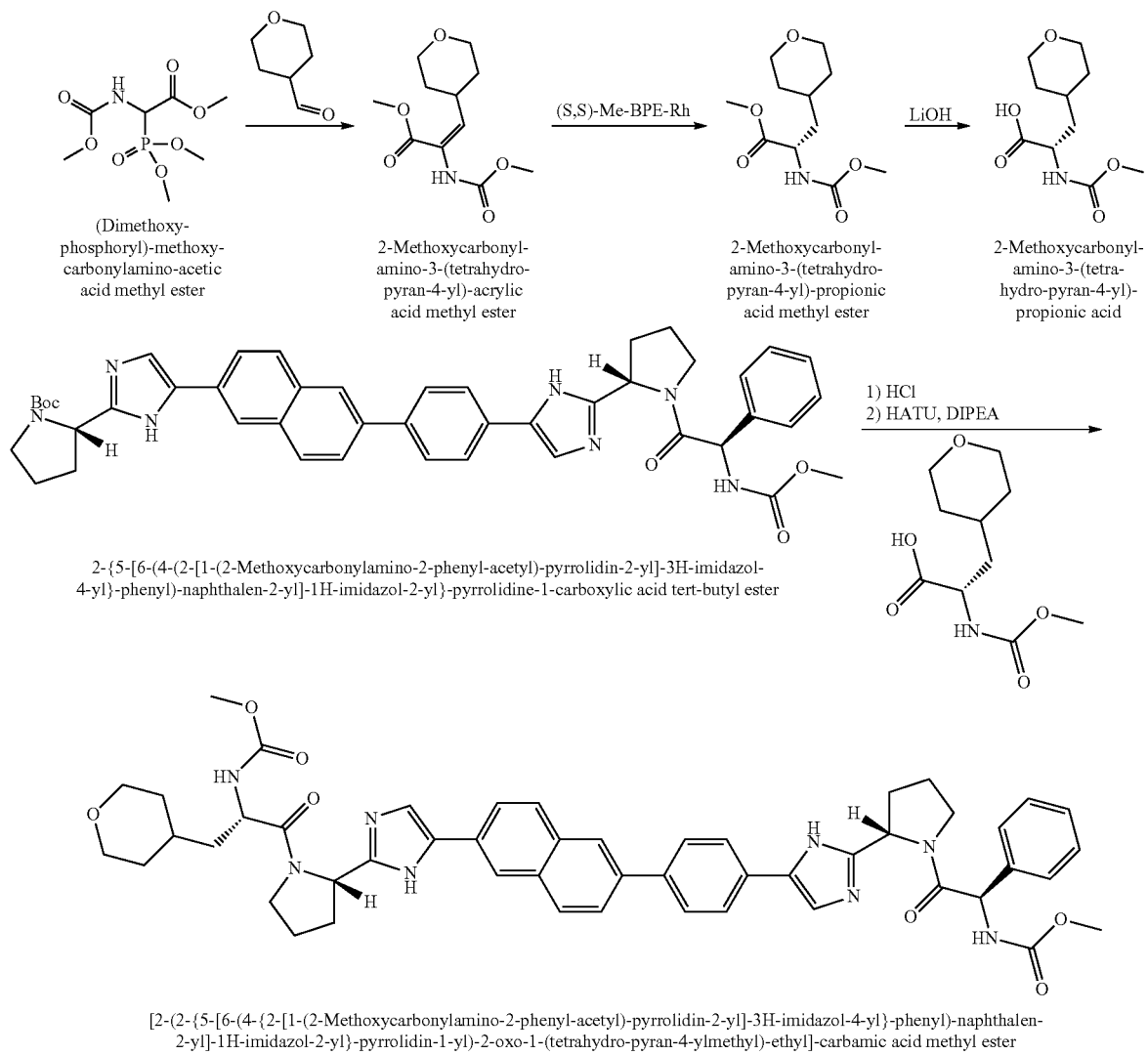

2-Methoxycarbonylamino-3-(tetrahydro-pyran-4-yl)-acrylic acid methyl ester. To a solution of (Dimethoxyphosphoryl)-methoxycarbonylamino-acetic acid methyl ester (0.34 g, 1.35 mmol) in THF (5.4 mL) at −78° C. (external, Acetone/CO$_2$ bath) was added 1,1,3,3-tetramethguanidine (0.17 mL, 1.35 mmol). The solution was stirred for 15 min before Tetrahydro-pyran-4-carbaldehyde (0.15 g, 1.35 mmol) was added. The reaction was stirred at −78° C. for 2 h and then allowed to warm to room temperature. The reaction was diluted with EtOAc and washed with HCl (1N) and brine. The aqueous layers were backextracted with EtOAc. The combined organic layers were dried over Na$_2$SO$_4$ and concentrated. The crude oil was purified by column chromatography (SiO$_2$, 20→100% EtOAc in Hexanes) to provide 2-Methoxycarbonylamino-3-(tetrahydro-pyran-4-yl)-acrylic acid methyl ester (0.15 g, 45%). LCMS-ESI$^+$: calc'd for C$_{11}$H$_{17}$NO$_5$: 243.11 (M$^+$); Found: 243.96 (M+H$^+$).

2-Methoxycarbonylamino-3-(tetrahydro-pyran-4-yl)-propionic acid methyl ester. A solution of 2-Methoxycarbonylamino-3-(tetrahydro-pyran-4-yl)-acrylic acid methyl ester (0.14 g, 0.57 mmol) in MeOH (2.1 mL) and CH$_2$Cl$_2$ (0.21 mL) was degassed with argon for 2 min. (S,S)-Me-BPE-Rh (0.02 g, 0.03 mmol) was added and the solution was degassed with argon for an additional 2 min. The solution was shaken on a Parr apparatus under an H$_2$ atmosphere (65 psi) for 3 days. The reaction was concentrated and the crude oil was purified by column chromatography (SiO$_2$, 20→100% EtOAc in Hexanes) to provide 2-Methoxycarbonylamino-3-(tetrahydro-pyran-4-yl)-propionic acid methyl ester (0.11 g, 77%). LCMS-ESI$^+$: calc'd for C$_{11}$H$_{19}$NO$_5$: 245.13 (M$^+$); Found: 246.1 (M+H$^+$).

2-Methoxycarbonylamino-3-(tetrahydro-pyran-4-yl)-propionic acid. To a solution of 2-Methoxycarbonylamino-3-(tetrahydro-pyran-4-yl)-propionic acid methyl ester (0.11 g, 1.1 mmol) in THF (3.3 mL) and MeOH (1.1 mL) at 0° C. (external, ice bath) was added aqueous LiOH (1 M, 0.88 mL, 0.88 mmol). The solution was stirred at room temperature for 18 h and concentrated to provide 2-Methoxycarbonylamino-3-(tetrahydro-pyran-4-yl)-propionic acid which was used crude in the next step. LCMS-ESI+: calc'd for $C_{10}H_{17}NO_5$: 231.11 (M+); Found: 231.99 (M+H+).

[2-(2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidin-1-yl)-2-oxo-1-(tetrahydro-pyran-4-ylmethyl)-ethyl]-carbamic acid methyl ester. To a solution of 2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carboxylic acid tert-butyl ester (0.12 g, 0.15 mmol) in $CH_2Cl_2$ (1.5 mL) and MeOH (0.2 mL) was added HCl (in dioxanes, 4 M, 0.75 mL, 3.0 mmol). The solution was stirred at room temperature for 2 h and concentrated to dryness. The resulting solid was dissolved in DMF (1.5 mL).

2-Methoxycarbonylamino-3-(tetrahydro-pyran-4-yl)-propionic acid (0.05 g, 0.22 mmol), HATU (0.07 g, 0.19 mmol) and DIPEA (0.13 mL, 0.74 mmol) were added. The resulting solution was stirred at room temperature for 18 h. The solution was purified twice by preparative HPLC (Gemini, 15-40% MeCN in $H_2O$ (0.1% TFA)) and lyophilized to provide [2-(2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidin-1-yl)-2-oxo-1-(tetrahydro-pyran-4-ylmethyl)-ethyl]-carbamic acid methyl ester (0.024 g, 18%). LCMS-ESI+: calc'd for $C_{50}H_{54}N_8O_7$: 878.41 (M+); Found: 879.97 (M+H+).

Example EY

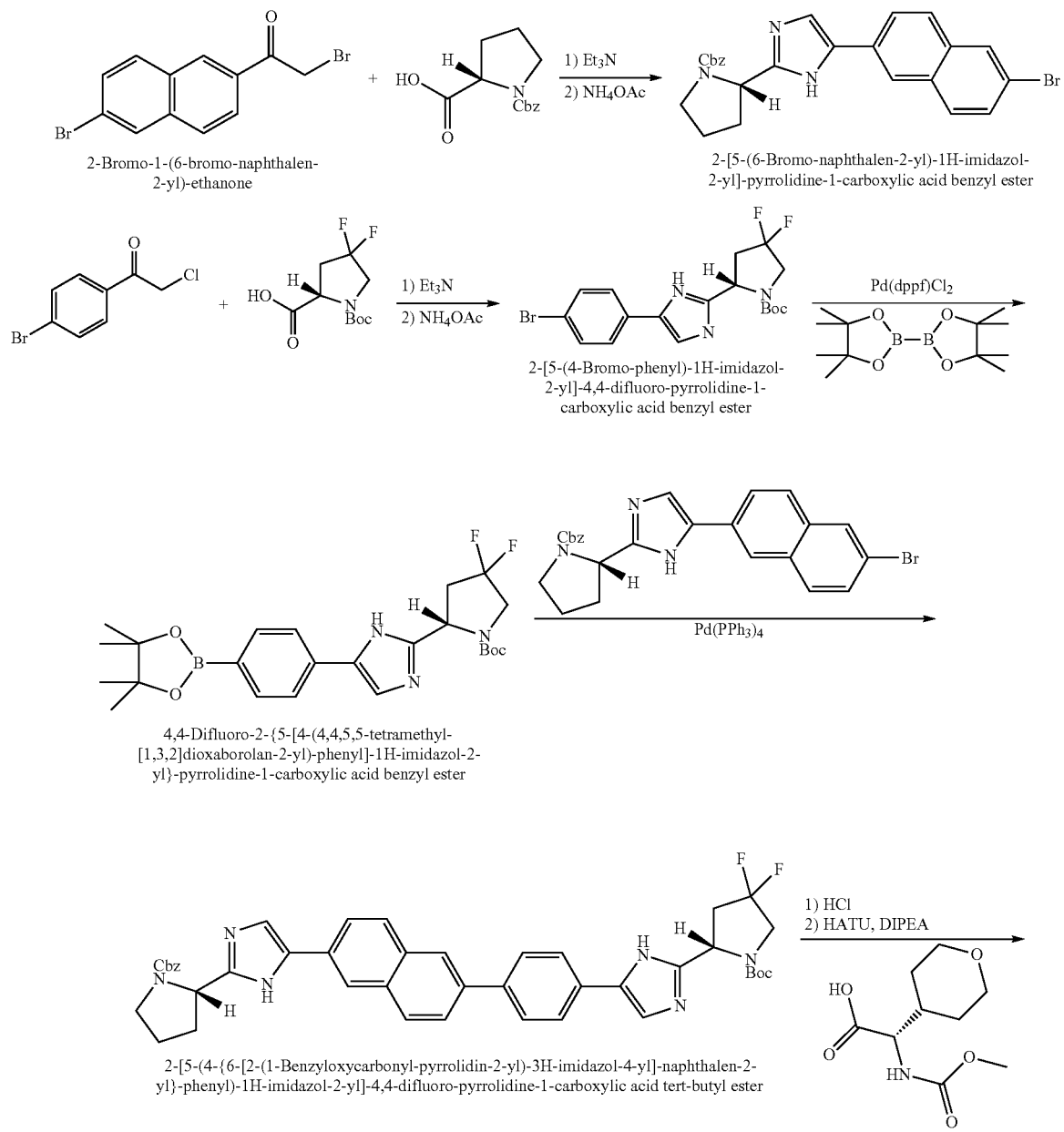

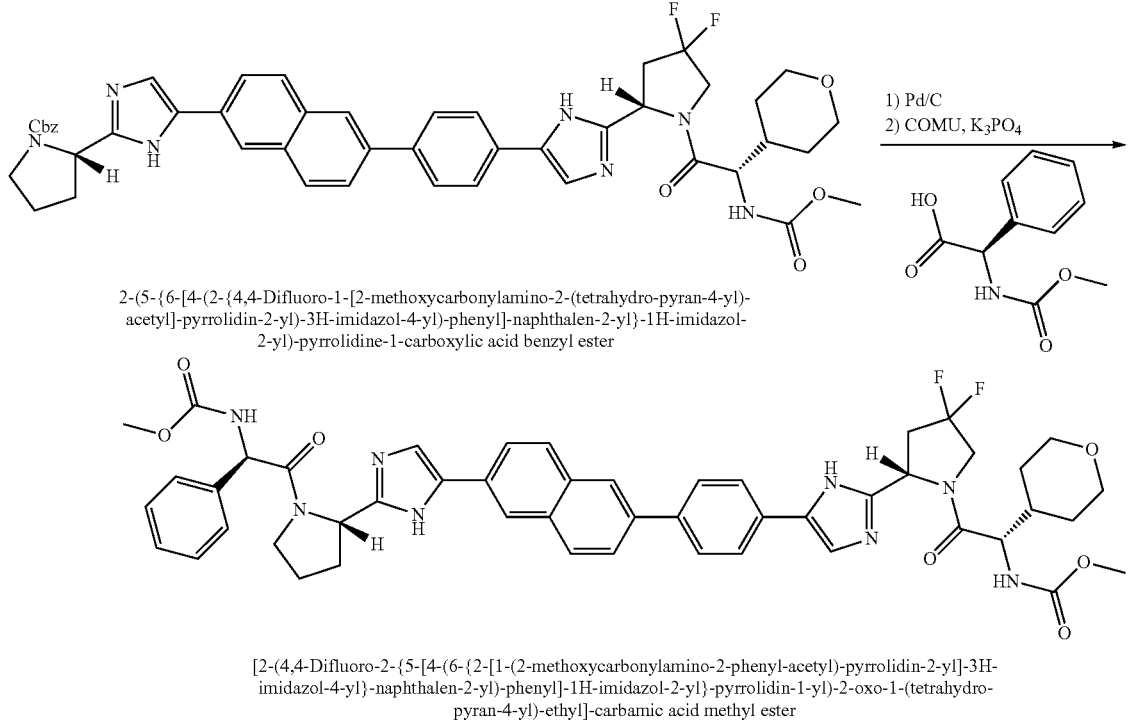

2-(5-{6-[4-(2-{4,4-Difluoro-1-[2-methoxycarbonylamino-2-(tetrahydro-pyran-4-yl)-
acetyl]-pyrrolidin-2-yl}-3H-imidazol-4-yl)-phenyl]-naphthalen-2-yl}-1H-imidazol-
2-yl)-pyrrolidine-1-carboxylic acid benzyl ester

[2-(4,4-Difluoro-2-{5-[4-(6-{2-[1-(2-methoxycarbonylamino-2-phenyl-acetyl)-pyrrolidin-2-yl]-3H-
imidazol-4-yl}-naphthalen-2-yl)-phenyl]-1H-imidazol-2-yl}-pyrrolidin-1-yl)-2-oxo-1-(tetrahydro-
pyran-4-yl)-ethyl]-carbamic acid methyl ester 2-[5-(6-Bromo-naphthalen-2-yl)-1H-imidazol-2-yl]-pyrrolidine-1-carboxylic acid benzyl ester. 2-[5-(6-Bromo-naphthalen-2-yl)-1H-imidazol-2-yl]-pyrrolidine-1-carboxylic acid benzyl ester (5.4 g, 74%) was prepared following the procedure for 2-[5-(6-Bromo-naphthalen-2-yl)-1H-imidazol-2-yl]-pyrrolidine-1-carboxylic acid tert-butyl ester, substituting Pyrrolidine-1,2-dicarboxylic acid 1-benzyl ester for Pyrrolidine-1,2-dicarboxylic acid 1-tert-butyl ester. LCMS-ESI$^+$: calc'd for $C_{25}H_{22}BrN_3O_2$: 475.09 (M$^+$); Found: 476.63 (M+H$^+$).

4,4-Difluoro-2-{5-[4-(4,4,5,5-tetramethyl-[1,3,2]dioxaborolan-2-yl)-phenyl]-1H-imidazol-2-yl}-pyrrolidine-1-carboxylic acid benzyl ester. 4,4-Difluoro-2-{5-[4-(4,4,5,5-tetramethyl-[1,3,2]dioxaborolan-2-yl)-phenyl]-1H-imidazol-2-yl}-pyrrolidine-1-carboxylic acid benzyl ester (2.28 g) was prepared following the procedure for 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester, substituting 4,4-Difluoro-pyrrolidine-1,2-dicarboxylic acid 1-tert-butyl ester for Pyrrolidine-1,2-dicarboxylic acid 1-tert-butyl ester. LCMS-ESI$^+$: calc'd for $C_{24}H_{32}BF_2N_3O_4$: 475.25 (M$^+$); Found: 476.42 (M+H$^+$).

2-[5-(4-{6-[2-(1-Benzyloxycarbonyl-pyrrolidin-2-yl)-3H-imidazol-4-yl]-naphthalen-2-yl}-phenyl)-1H-imidazol-2-yl]-4,4-difluoro-pyrrolidine-1-carboxylic acid tert-butyl ester. To a solution of 2-[5-(6-Bromo-naphthalen-2-yl)-1H-imidazol-2-yl]-pyrrolidine-1-carboxylic acid benzyl ester (1.5 g, 3.15 mmol) and 4,4-Difluoro-2-{5-[4-(4,4,5,5-tetramethyl-[1,3,2]dioxaborolan-2-yl)-phenyl]-1H-imidazol-2-yl}-pyrrolidine-1-carboxylic acid benzyl ester (1.8 g, 3.78 mmol) in DME (16 mL) was added Tetrakis(triphenylphosphine)Palladium (0.19 g, 0.16 mmol) and aqueous potassium phosphate (2M, 4.8 mL, 9.6 mmol). The solution was degassed with argon for 15 min and heated to 80° C. for 18 h with stirring. The solution was cooled, filtered and diluted with EtOAc (~5% MeOH). The organic layer was washed with brine, dried over $Na_2SO_4$ and concentrated. The crude oil was purified by column chromatography (SiO$_2$, 30→100% EtOAc (10% MeOH) in Hexanes to 70% MeOH in EtOAc) to provide 2-[5-(4-{6-[2-(1-Benzyloxycarbonyl-pyrrolidin-2-yl)-3H-imidazol-4-yl]-naphthalen-2-yl}-phenyl)-1H-imidazol-2-yl]-4,4-difluoro-pyrrolidine-1-carboxylic acid tert-butyl ester (2.1 g, 89%). LCMS-ESI$^+$: calc'd for $C_{43}H_{42}F_2N_6O_4$: 744.32 (M$^+$); Found: 745.20 (M+H$^+$).

2-(5-{6-[4-(2-{4,4-Difluoro-1-[2-methoxycarbonylamino-2-(tetrahydro-pyran-4-yl)-acetyl]-pyrrolidin-2-yl}-3H-imidazol-4-yl)-phenyl]-naphthalen-2-yl}-1H-imidazol-2-yl)-pyrrolidine-1-carboxylic acid benzyl ester. To a solution of 2-[5-(4-{6-[2-(1-Benzyloxycarbonyl-pyrrolidin-2-yl)-3H-imidazol-4-yl]-naphthalen-2-yl}-phenyl)-1H-imidazol-2-yl]-4,4-difluoro-pyrrolidine-1-carboxylic acid tert-butyl ester (0.25 g, 0.34 mmol) in $CH_2Cl_2$ (3.5 mL) and MeOH (0.25 mL) was added HCl (in dioxanes, 4 M, 1.7 mL, 7.8 mmol). The solution was stirred at room temperature for 2.5 h and concentrated to dryness. The resulting solid was slurried in $CH_2Cl_2$ (3 mL) and DMF (1 mL). Methoxycarbonylamino-(tetrahydro-pyran-4-yl)-acetic acid (0.11 g, 0.50 mmol), HATU (0.15 g, 0.40 mmol), and DIPEA (0.3 mL, 1.7 mmol) were added. The resulting solution was stirred at room temperature for 18 h. The solution was diluted with $CH_2Cl_2$ and washed with saturated sodium bicarbonate. The organic layer was dried over $Na_2SO_4$ and concentrated. The crude oil was purified by column chromatography (SiO$_2$, 2→20% MeOH in $CH_2Cl_2$), followed by preparative HPLC (Gemini, 15→50% MeCN in $H_2O$ (0.1% TFA)) to provide 2-(5-{6-[4-(2-{4,4-Difluoro-1-[2-methoxycarbonylamino-2-(tetrahydro-pyran-4-yl)-acetyl]-pyrrolidin-2-yl}-3H-imidazol-4-yl)-phenyl]-naphthalen-2-yl}-1H-imidazol-2-yl)-pyrrolidine-1-carboxylic acid benzyl ester (0.13 g, 46%). LCMS-ESI$^+$: calc'd for $C_{47}H_{47}F_2N_7O_6$: 843.36 (M$^+$); Found: 844.78 (M+H$^+$).

[2-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester. To a solution of 2-(5-{6-[4-(2-{4,4-Difluoro-1-[2-methoxycarbonylamino-2-(tetrahydro-pyran-4-yl)-acetyl]-pyrrolidin-2-yl}-3H-imidazol-4-yl)-phenyl]-naphthalen-2-yl}-1H-imidazol-2-yl)-pyrrolidine-1-carboxylic acid benzyl ester (0.13 g, 0.15 mmol) in EtOH (3.5 mL) was added Palladium on carbon (10%, 0.08 g, 0.08 mmol) and Potassium Carbonate (0.07 g, 0.48 mmol). The slurry was stirred at room temperature under an atmosphere of H₂ for 3 h. The slurry was filtered through celite and washed with EtOH. The filtrate was concentrated to an oil and diluted with CH₂Cl₂ (3 mL) and filtered an additional time. Methoxycarbonylamino-phenyl-acetic acid (0.05 g, 0.03 mmol) and Potassium Phosphate (0.04 g, 0.16 mmol) were added and the resulting slurry was cooled to 0° C. (external, ice). COMU (0.09 g, 0.02 mmol) was added and the reaction was stirred at 0° C. for 2 h. The slurry was diluted with CH₂Cl₂ and filtered through celite. The filtrate was concentrated and purified by preparative HPLC (Gemini, 15→50% MeCN in H₂O (0.1% TFA)) to provide to provide [2-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester (0.03 g, 17%). LCMS-ESI⁺: calc'd for $C_{49}H_{50}F_2N_8O_7$: 900.38 (M⁺); Found: 901.4 (M+H⁺).

Example EZ

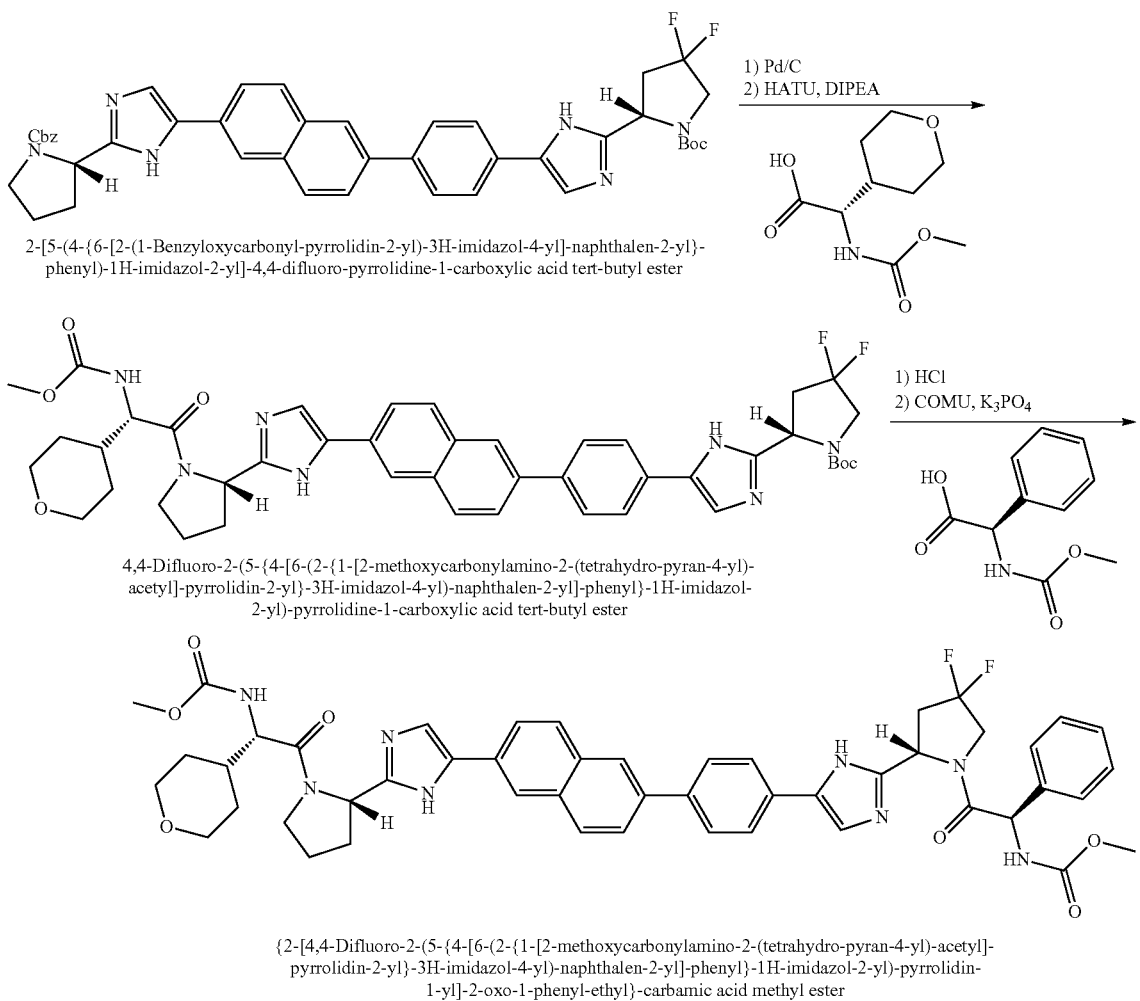

4,4-Difluoro-2-(5-{4-[6-(2-{1-[2-methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidine-1-carboxylic acid tert-butyl ester. To a solution of 2-[5-(4-{6-[2-(1-Benzyloxycarbonyl-pyrrolidin-2-yl)-3H-imidazol-4-yl]-naphthalen-2-yl}-phenyl)-1H-imidazol-2-yl]-4,4-difluoro-pyrrolidine-1-carboxylic acid tert-butyl ester (0.25 g, 0.34 mmol) in EtOH (3.5 mL) was added Palladium on carbon (10%, 0.18 g, 0.02 mmol) and Potassium Carbonate (0.14 g, 1.0 mmol). The slurry was stirred at room temperature under an atmosphere of H2 for 5 h. The slurry was filtered through celite and washed with EtOH. The filtrate was concentrated to an oil and diluted with CH₂Cl₂ (3 mL) and DMF (2 mL). Methoxycarbonylamino-(tetrahydro-pyran-4-yl)-acetic acid (0.11 g, 0.50 mmol), HATU (0.15 g, 0.40 mmol), and DIPEA (0.3 mL, 1.7 mmol) were added. The resulting solution was stirred at room temperature for 5 h. The solution was diluted with CH₂Cl₂ and washed with saturated sodium bicarbonate. The organic layer was dried over Na₂SO₄ and concentrated. The crude oil was concentrated and purified by preparative HPLC (Gemini, 15→50% MeCN in H₂O (0.1% TFA)) to provide to provide 4,4-Difluoro-2-(5-{4-[6-(2-{1-[2-methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidine-1-carboxylic acid tert-butyl ester (0.04 g, 14%). LCMS-ESI⁺: calc'd for $C_{44}H_{49}F_2N_7O_6$: 809.37 (M⁺); Found: 810.79 (M+H⁺).

{2-[4,4-Difluoro-2-(5-{4-[6-(2-{1-[2-methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester. To a solution of 4,4-Difluoro-2-(5-{4-[6-(2-{1-[2-methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidine-1-carboxylic acid tert-butyl ester (0.04 g, 0.05 mmol) in CH₂Cl₂ (0.5 mL) and MeOH (0.05 mL) was added HCl (in dioxanes, 4 M, 0.3 mL, 1.2 mmol). The solution was stirred at room temperature for 2 h and concentrated to dryness. The solid was slurried with CH₂Cl₂ (0.5 mL). Methoxycarbonylamino-phenyl-acetic acid (0.02 g, 0.07 mmol) and Potassium Phosphate (0.03 g, 0.14 mmol) were added and the resulting slurry was cooled to 0° C. (external, ice). COMU (0.03 g, 0.06 mmol) was added and the reaction was stirred at room temperature for 2 h. The slurry was diluted with CH₂Cl₂ and filtered through celite. The filtrate was concentrated and purified by preparative HPLC (Gemini, 15→50% MeCN in H₂O (0.1% TFA)) to provide to provide {2-[4,4-Difluoro-2-(5-{4-[6-(2-{1-[2-methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester (0.02 g, 49%). LCMS-ESI⁺: calc'd for $C_{49}H_{50}F_2N_8O_7$: 900.38 (M⁺); Found: 901.4 (M+H⁺).

Example FA

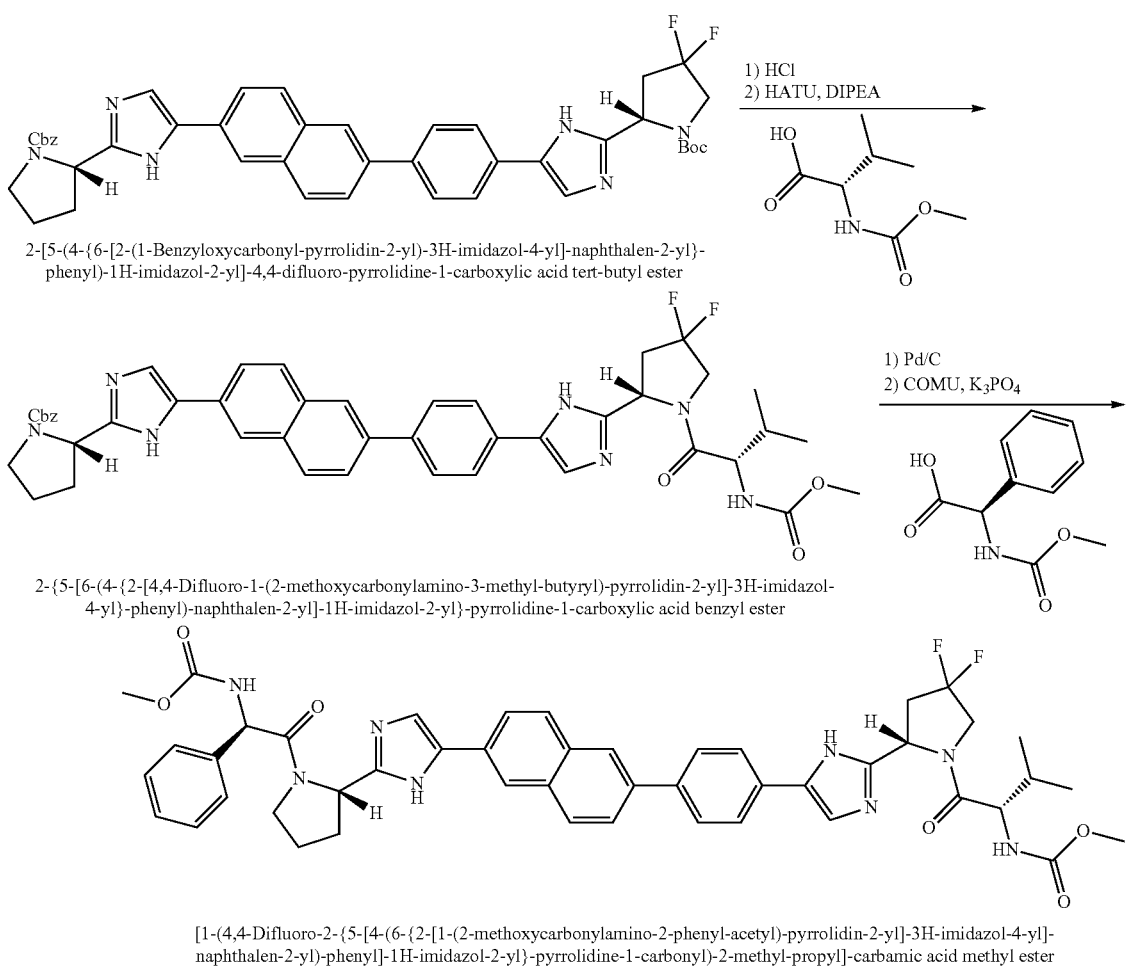

2-[5-(4-{6-[2-(1-Benzyloxycarbonyl-pyrrolidin-2-yl)-3H-imidazol-4-yl]-naphthalen-2-yl}-phenyl)-1H-imidazol-2-yl]-4,4-difluoro-pyrrolidine-1-carboxylic acid tert-butyl ester 2-{5-[6-(4-{2-[4,4-Difluoro-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid benzyl ester

[1-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester

[1-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]1H-imidazol-2-yl}pyrrolidine-1-carbonyl)-2-methyl-propyl]-carbamic acid methyl ester. [1-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester was prepared following the procedure for [2-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester, substituting 2-Methoxycarbonylamino-3-methyl-butyric acid for Methoxycarbonylamino-(tetrahydro-pyran-4-yl)-acetic acid. LCMS-ESI⁺: calc'd for $C_{47}H_{48}F_2N_8O_6$: 858.37 (M⁺); Found: 859.88 (M+H⁺).

Example FB
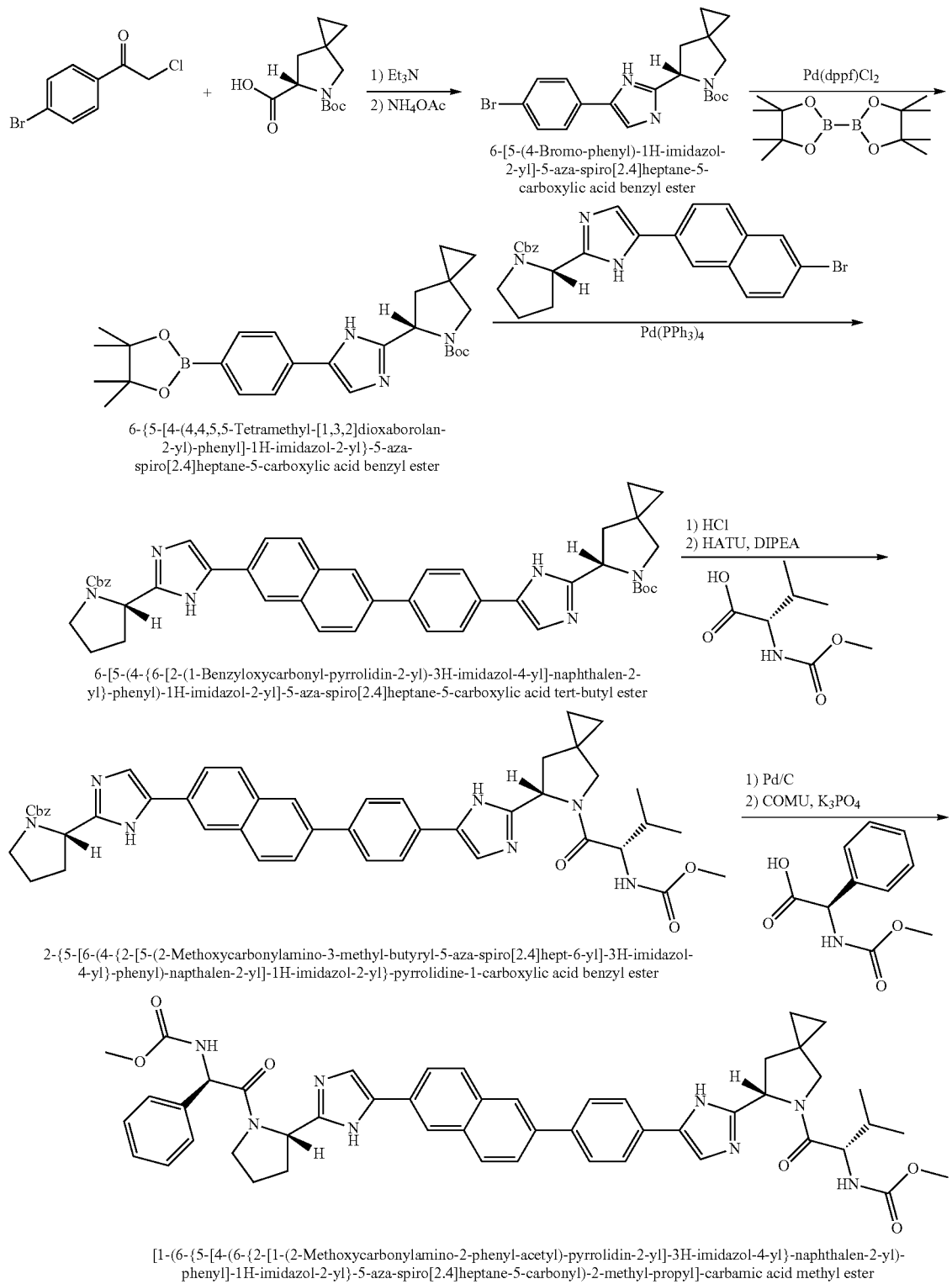
6-{5-[4-(4,4,5,5-Tetramethyl-[1,3,2]dioxaborolan-2-yl)-phenyl]-1H-imidazol-2-yl}-5-aza-spiro[2.4]heptane-5-carboxylic acid benzyl ester. 6-{5-[4-(4,4,5,5-Tetramethyl-[1,3,2]dioxaborolan-2-yl)-phenyl]-1H-imidazol-2-yl}-5-aza-spiro[2.4]heptane-5-carboxylic acid benzyl ester (3.05 g, 84%) was prepared following the procedure for 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester, substituting 5-Aza-spiro[2.4]heptane-5,6-dicarboxylic acid 5-tert-butyl ester for Pyrrolidine-1,2-dicarboxylic acid 1-tert-butyl ester. LCMS-ESC: calc'd for $C_{26}H_{36}BN_3O_4$: 465.28 (M⁺); Found: 466.64 (M+H⁺).

[1-(6-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester. [1-(6-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-5-aza-spiro[2.4]heptane-5-carbonyl)-2-methyl-propyl]-carbamic acid methyl ester (0.10 g, 34%) was prepared following the procedure for [2-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester, substituting 2-Methoxycarbonylamino-3-methyl-butyric acid for Methoxycarbonylamino-(tetrahydro-pyran-4-yl)-acetic acid and 6-{5-[4-(4,4,5,5-Tetramethyl-[1,3,2]dioxaborolan-2-yl)-phenyl]-1H-imidazol-2-yl}-5-aza-spiro[2.4]heptane-5-carboxylic acid benzyl ester for 4,4-Difluoro-2-{5-[4-(4,4,5,5-tetramethyl-[1,3,2]dioxaborolan-2-yl)-phenyl]-1H-imidazol-2-yl}-pyrrolidine-1-carboxylic acid benzyl ester. LCMS-ESI⁺: calc'd for $C_{49}H_{52}N_8O_6$: 848.40 (M⁺); Found: 849.96 (M+H⁺).

Example FC

[2-(6-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-5-aza-spiro[2.4]hept-5-yl)-2-oxo-1-(tetrahydro-pyran-4-yl)-ethyl]-carbamic acid methyl ester. [2-(6-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-5-aza-spiro[2.4]hept-5-yl)-2-oxo-1-(tetrahydro-pyran-4-yl)-ethyl]-carbamic acid methyl ester (0.10 g, 44%) was prepared following the procedure for [2-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester, substituting 6-{5-[4-(4,4,5,5-Tetramethyl-[1,3,2]dioxaborolan-2-yl)-phenyl]-1H-imidazol-2-yl}-5-aza-spiro[2.4]heptane-5-carboxylic acid benzyl ester for 4,4-Difluoro-2-{5-[4-(4,4,5,5-tetramethyl-[1,3,2]dioxaborolan-2-yl)-phenyl]-1H-imidazol-2-yl}-pyrrolidine-1-carboxylic acid benzyl ester. LCMS-ESI⁺: calc'd for $C_{51}H_{54}N_8O_7$: 890.41 (M⁺); Found: 891.99 (M+H⁺).

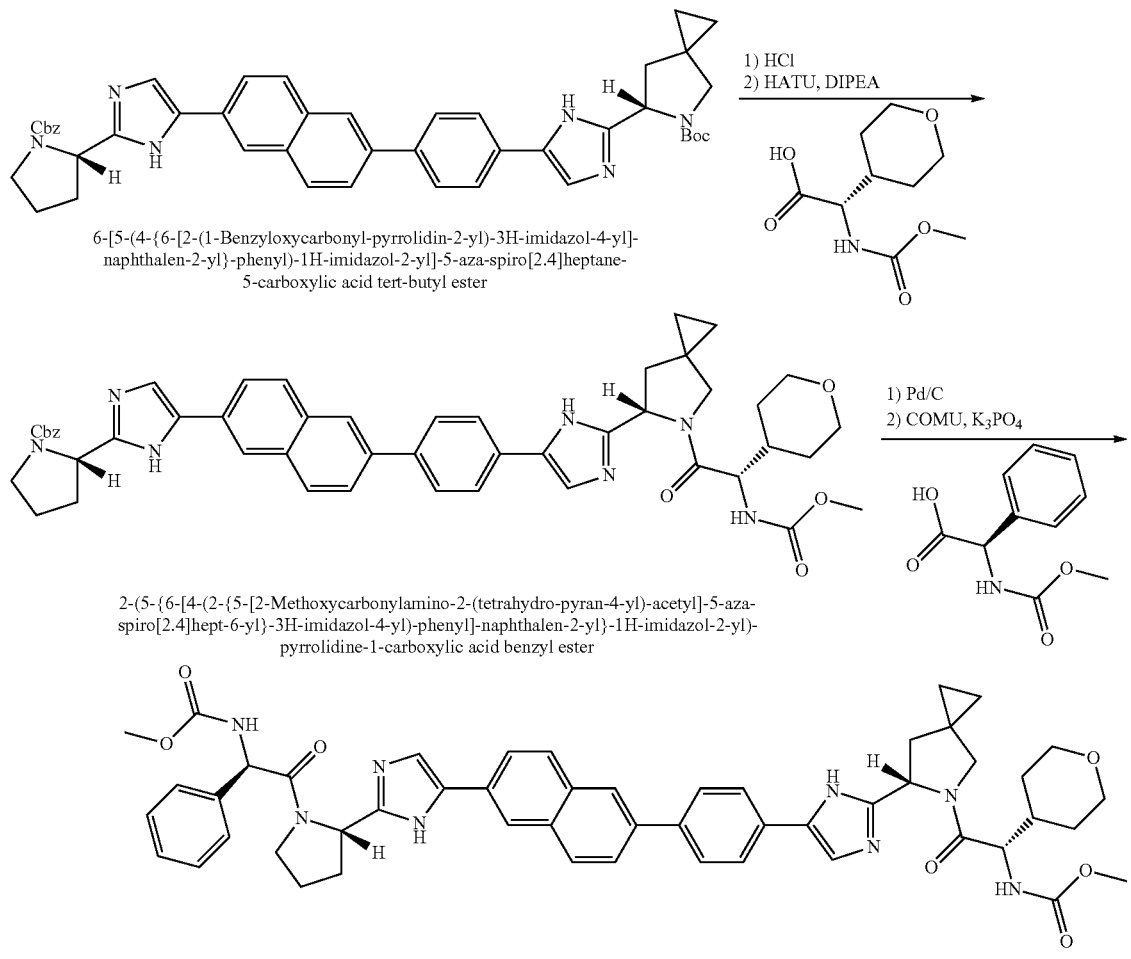

6-[5-(4-{6-[2-(1-Benzyloxycarbonyl-pyrrolidin-2-yl)-3H-imidazol-4-yl]-naphthalen-2-yl}-phenyl)-1H-imidazol-2-yl]-5-aza-spiro[2.4]heptane-5-carboxylic acid tert-butyl ester 2-(5-{6-[4-(2-{5-[2-Methoxycarbonylamino-2-(tetrahydro-pyran-4-yl)-acetyl]-5-aza-spiro[2.4]hept-6-yl}-3H-imidazol-4-yl)-phenyl]-naphthalen-2-yl}-1H-imidazol-2-yl)-pyrrolidine-1-carboxylic acid benzyl ester

[2-(6-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-5-aza-spiro[2.4]hept-5-yl)-2-oxo-1-(tetrahydro-pyran-4-yl)-ethyl]-carbamic acid methyl ester

Example FD

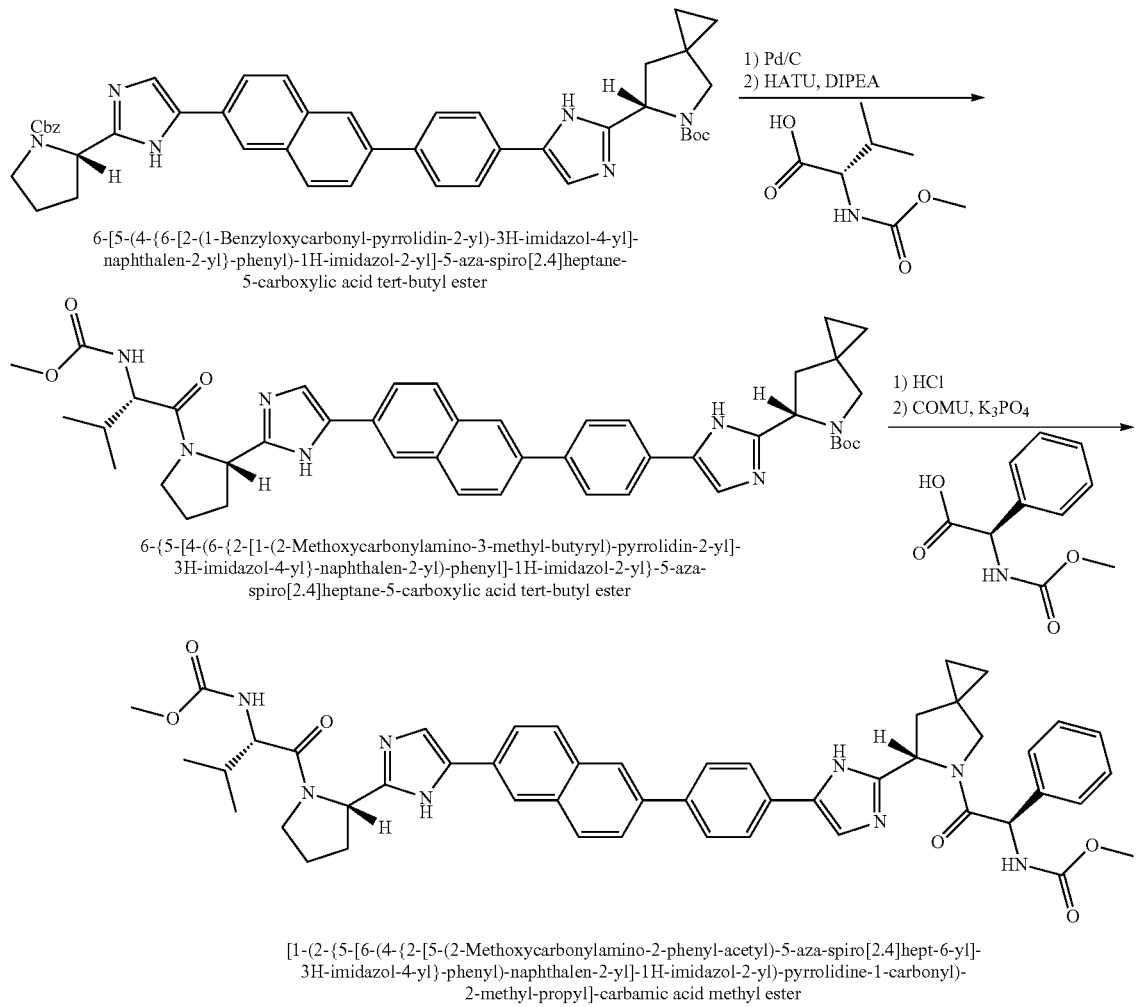

6-[5-(4-{6-[2-(1-Benzyloxycarbonyl-pyrrolidin-2-yl)-3H-imidazol-4-yl]-naphthalen-2-yl}-phenyl)-1H-imidazol-2-yl]-5-aza-spiro[2.4]heptane-5-carboxylic acid tert-butyl ester 6-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-5-aza-spiro[2.4]heptane-5-carboxylic acid tert-butyl ester

[1-(2-{5-[6-(4-{2-[5-(2-Methoxycarbonylamino-2-phenyl-acetyl)-5-aza-spiro[2.4]hept-6-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[5-(2-Methoxycarbonylamino-2-phenyl-acetyl)-5-aza-spiro[2.4]hept-6-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[5-(2-Methoxycarbonylamino-2-phenyl-acetyl)-5-aza-spiro[2.4]hept-6-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.08 g, 28%) was prepared following the procedure for {2-[4,4-Difluoro-2-(5-{4-[6-(2-{1-[2-methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester, substituting 2-Methoxycarbonylamino-3-methyl-butyric acid for Methoxycarbonylamino-(tetrahydro-pyran-4-yl)-acetic acid and 6-[5-(4-{6-[2-(1-Benzyloxycarbonyl-pyrrolidin-2-yl)-3H-imidazol-4-yl]-naphthalen-2-yl}-phenyl)-1H-imidazol-2-yl]-5-aza-spiro[2.4]heptane-5-carboxylic acid tert-butyl ester for 2-[5-(4-{6-[2-(1-Benzyloxycarbonyl-pyrrolidin-2-yl)-3H-imidazol-4-yl]-naphthalen-2-yl}-phenyl)-1H-imidazol-2-yl]-4,4-difluoro-pyrrolidine-1-carboxylic acid tert-butyl ester. LCMS-ESI$^+$: calc'd for $C_{49}H_{52}N_8O_6$: 848.40 (M$^+$); Found: 849.95 (M+H$^+$).

Example FE

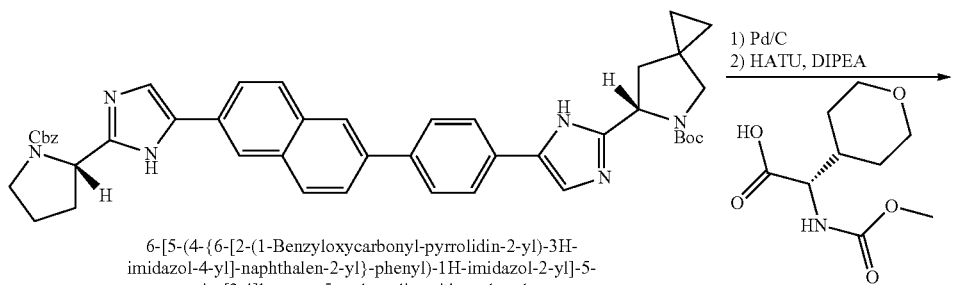

6-[5-(4-{6-[2-(1-Benzyloxycarbonyl-pyrrolidin-2-yl)-3H-imidazol-4-yl]-naphthalen-2-yl}-phenyl)-1H-imidazol-2-yl]-5-aza-spiro[2.4]heptane-5-carboxylic acid tert-butyl ester

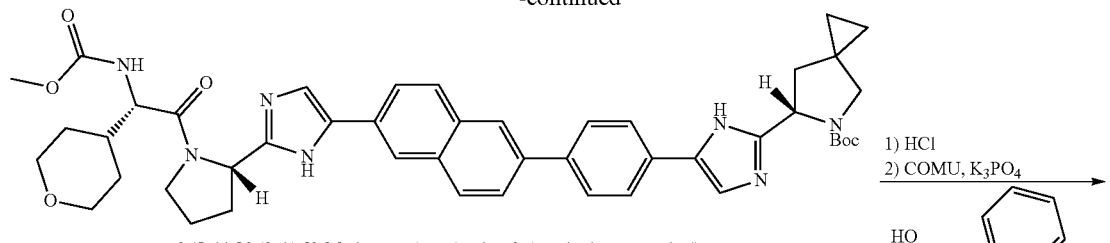

6-(5-{4-[6-(2-{1-[2-Methoxycarbonylamino-2-(tetrahydro-pyran-4-yl)-acetyl]-pyrrolidin-2-yl]-3H-imidazol-4-yl)-naphthalen-2-yl]-phenyl}-1H-imidazol-2-yl)-5-aza-spiro[2.4]heptane-5-carboxylic acid tert-butyl ester

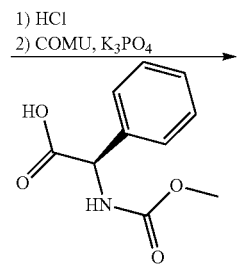

1) HCl
2) COMU, K₃PO₄

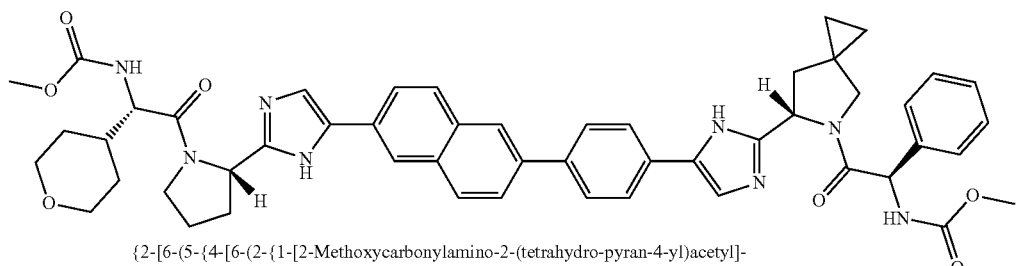

{2-[6-(5-{4-[6-(2-{1-[2-Methoxycarbonylamino-2-(tetrahydro-pyran-4-yl)acetyl]-pyrrolidin-2-yl}-3H-imidazol-4-yl)-naphthalen-2-yl]-phenyl}-1H-imidazol-2-yl)-5-aza-spiro[2.4]hept-5-yl]-2-oxo-1-phenyl-ethyl}-carbamic acid methyl ester {2-[6-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-5-aza-spiro[2.4]hept-5-yl]-2-oxo-1-phenyl-ethyl}-carbamic acid methyl ester. {2-[6-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-5-aza-spiro[2.4]hept-5-yl]-2-oxo-1-phenyl-ethyl}-carbamic acid methyl ester (0.09 g, 33%) was prepared following the procedure for {2-[4,4-Difluoro-2-(5-{4-[6-(2-{1-[2-methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester, substituting 6-[5-(4-{6-[2-(1-Benzyloxycarbonyl-pyrrolidin-2-yl)-3H-imidazol-4-yl]-naphthalen-2-yl}-phenyl)-1H-imidazol-2-yl]-5-aza-spiro[2.4]heptane-5-carboxylic acid tert-butyl ester for 2-[5-(4-{6-[2-(1-Benzyloxycarbonyl-pyrrolidin-2-yl)-3H-imidazol-4-yl]-naphthalen-2-yl}-phenyl)-1H-imidazol-2-yl]-4,4-difluoro-pyrrolidine-1-carboxylic acid tert-butyl ester. LCMS-ESI⁺: calc'd for $C_{51}H_{54}N_8O_7$: 890.41 (M⁺); Found: 891.96 (M+H⁺).

Example FF

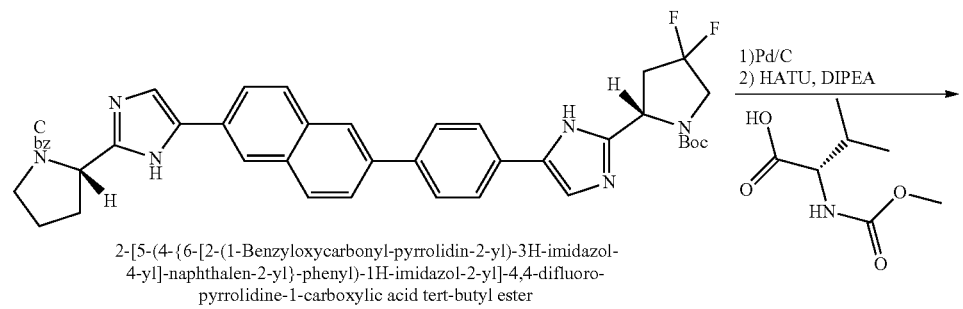

2-[5-(4-{6-[2-(1-Benzyloxycarbonyl-pyrrolidin-2-yl)-3H-imidazol-4-yl]-naphthalen-2-yl}-phenyl)-1H-imidazol-2-yl]-4,4-difluoro-pyrrolidine-1-carboxylic acid tert-butyl ester 1)Pd/C
2) HATU, DIPEA

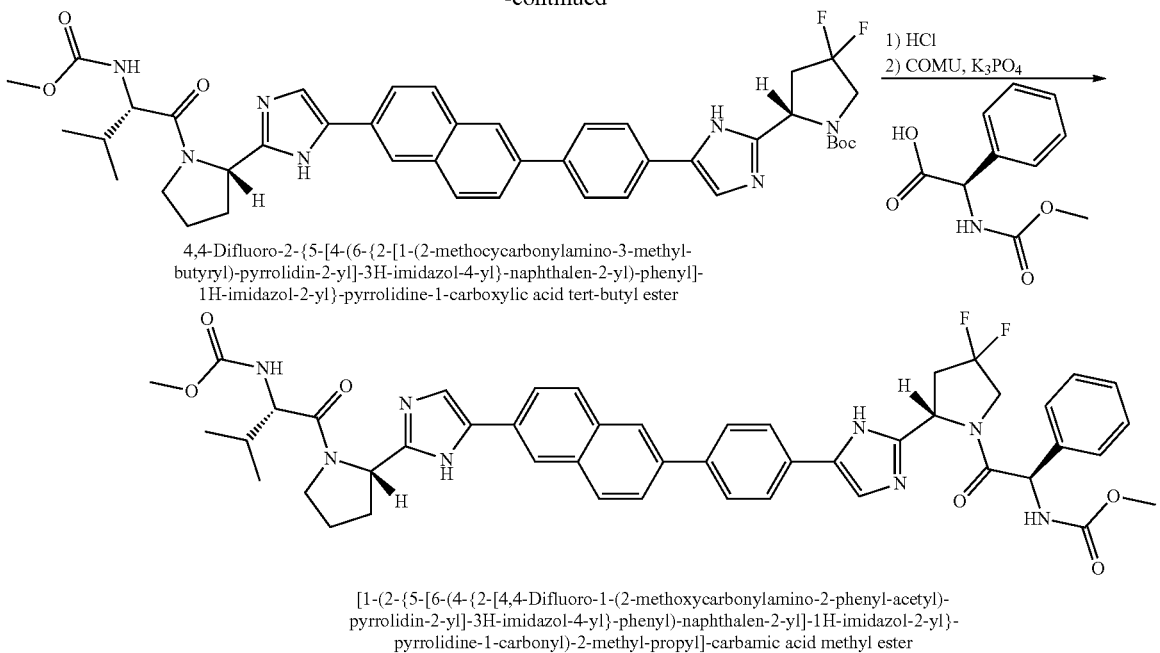

4,4-Difluoro-2-{5-[4-(6-{2-[1-(2-methocycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester

[1-(2-{5-[6-(4-{2-[4,4-Difluoro-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[4,4-Difluoro-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[4,4-Difluoro-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.05 g, 17%) was prepared following the procedure for {2-[4,4-Difluoro-2-(5-{4-[6-(2-{1-[2-methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester, substituting 2-Methoxycarbonylamino-3-methyl-butyric acid for Methoxycarbonylamino-(tetrahydro-pyran-4-yl)-acetic acid. LCMS-ESI+: calc'd for $C_{47}H_{48}F_2N_8O_6$: 858.37 (M+); Found: 859.92 (M+H+).

Example FG

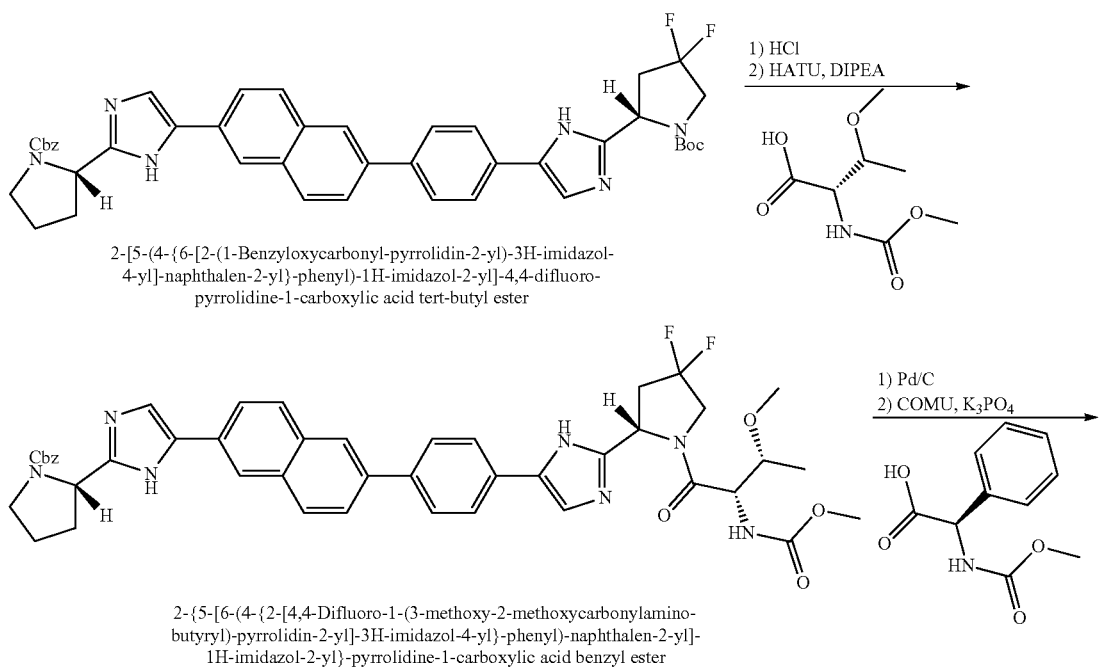

2-[5-(4-{6-[2-(1-Benzyloxycarbonyl-pyrrolidin-2-yl)-3H-imidazol-4-yl]-naphthalen-2-yl}-phenyl)-1H-imidazol-2-yl]-4,4-difluoro-pyrrolidine-1-carboxylic acid tert-butyl ester 2-{5-[6-(4-{2-[4,4-Difluoro-1-(3-methoxy-2-methoxycarbonylamino-butyryl)-pyrrolidin-2-yl]-3H-imidazol-4-yl}-phenyl)-naphthalen-2-yl]-1H-imidazol-2-yl}-pyrrolidine-1-carboxylic acid benzyl ester

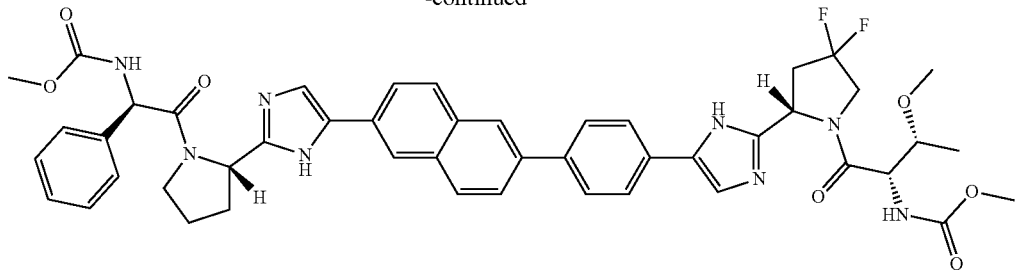

[1-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyal-propyl]-carbamic acid methyl ester

[1-(4,4-Difluoro-2-{5-[4-(6-{2-[1-(2-methoxycarbonylamino-2-phenyl-acetyl)pyrrolidin-2-yl]-3H-imidazol-4-yl}-napthalen-2-yl)-phenyl]-1H-imidazol-2-yl}-pyrrolidine-1-carbonyl)-2-methoxy-propyl]-carbamic acid methyl ester. [1-(4,4-Difluoro-2-{5-[4-(6-{2-[1-(2-methoxycarbonylamino-2-phenyl-acetyl)-pyrrolidin-2-yl]3H-imidazol-4-yl}-naphthalen-2-yl)-phenyl]-1H-imidazol-2-yl}-pyrrolidine-1-carbonyl)-2-methoxy-propyl]-carbamic acid methyl ester (0.07 g, 23%) was prepared following the procedure for [2-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester, substituting 3-Methoxy-2-methoxycarbonylamino-butyric acid for Methoxycarbonylamino-(tetrahydro-pyran-4-yl)-acetic acid. LCMS-ESI$^+$: calc'd for $C_{47}H_{48}F_2N_8O_7$: 874.36 (M$^+$); Found: 875.90 (M+H$^+$).

Example FH

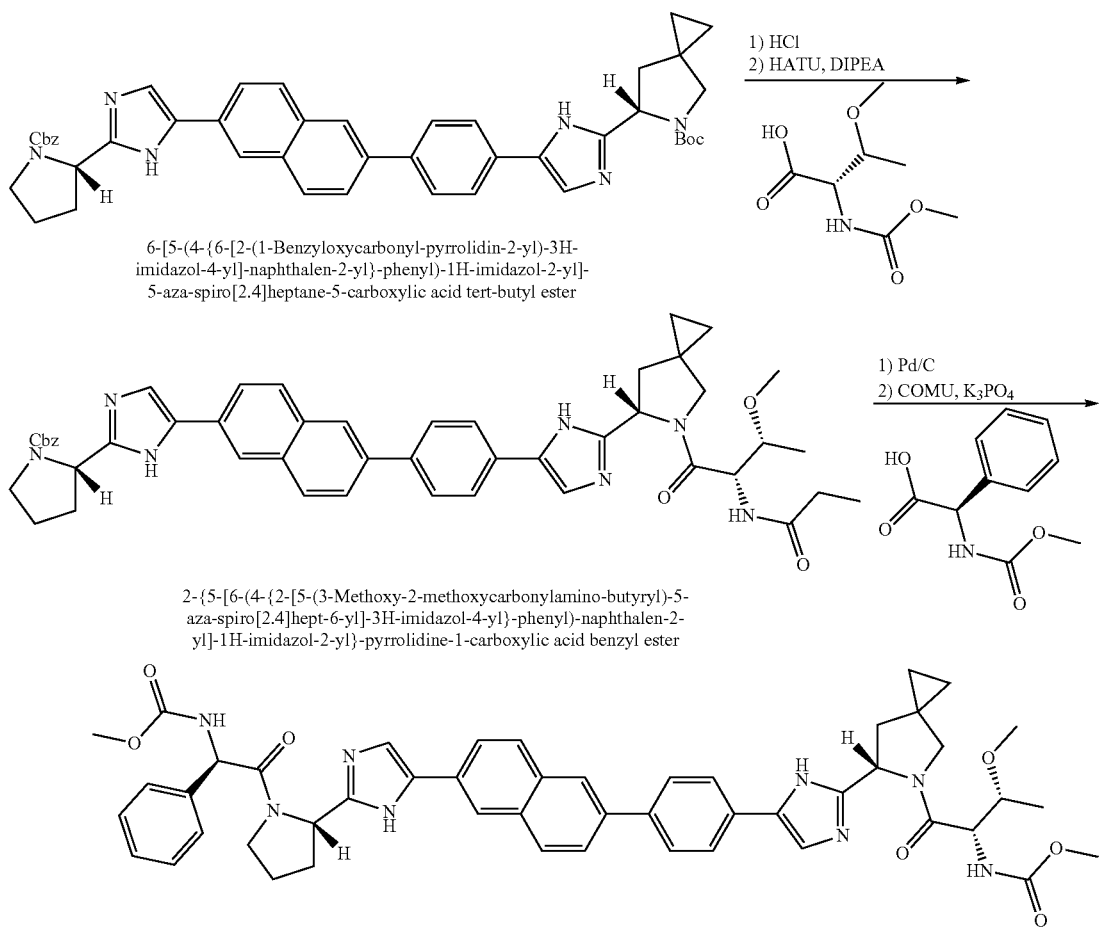

6-[5-(4-{6-[2-(1-Benzyloxycarbonyl-pyrrolidin-2-yl)-3H-imidazol-4-yl]-naphthalen-2-yl}-phenyl)-1H-imidazol-2-yl]-5-aza-spiro[2.4]heptane-5-carboxylic acid tert-butyl ester 2-{5-[6-(4-{2-[5-(3-Methoxy-2-methoxycarbonylamino-butyryl)-5-aza-spiro[2.4]hept-6-yl]-3H-imidazol-4-yl}-phenyl)-naphthalen-2-yl]-1H-imidazol-2-yl}-pyrrolidine-1-carboxylic acid benzyl ester

[2-Methoxy-1-(6-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-5-aza-spiro[2.4]heptane-5-carbonyl)-propyl]-carbamic acid methyl ester

[2-Methoxy-1-(6-{6-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-5-aza-spiro[2.4]heptane-5-carbonyl)-propyl]-carbamic acid methyl ester. [2-Methoxy-1-(6-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-5-aza-spiro[2.4]heptane-5-carbonyl)-propyl]-carbamic acid methyl ester (0.09 g, 29%) was prepared following the procedure for [2-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester, substituting 3-Methoxy-2-methoxycarbonylamino-butyric acid for Methoxycarbonylamino-(tetrahydro-pyran-4-yl)-acetic acid and 6-[5-(4-{6-[2-(1-Benzyloxycarbonyl-pyrrolidin-2-yl)-3H-imidazol-4-yl]-naphthalen-2-yl}-phenyl)-1H-imidazol-2-yl]-5-aza-spiro[2.4]heptane-5-carboxylic acid tert-butyl ester for 2-[5-(4-{6-[2-(1-Benzyloxycarbonyl-pyrrolidin-2-yl)-3H-imidazol-4-yl]-naphthalen-2-yl}-phenyl)-1H-imidazol-2-yl]-4,4-difluoro-pyrrolidine-1-carboxylic acid tert-butyl ester. LCMS-ESI+: calc'd for $C_{49}H_{52}N_8O_7$: 864.40 (M+); Found: 865.97 (M+H+).

Example FI

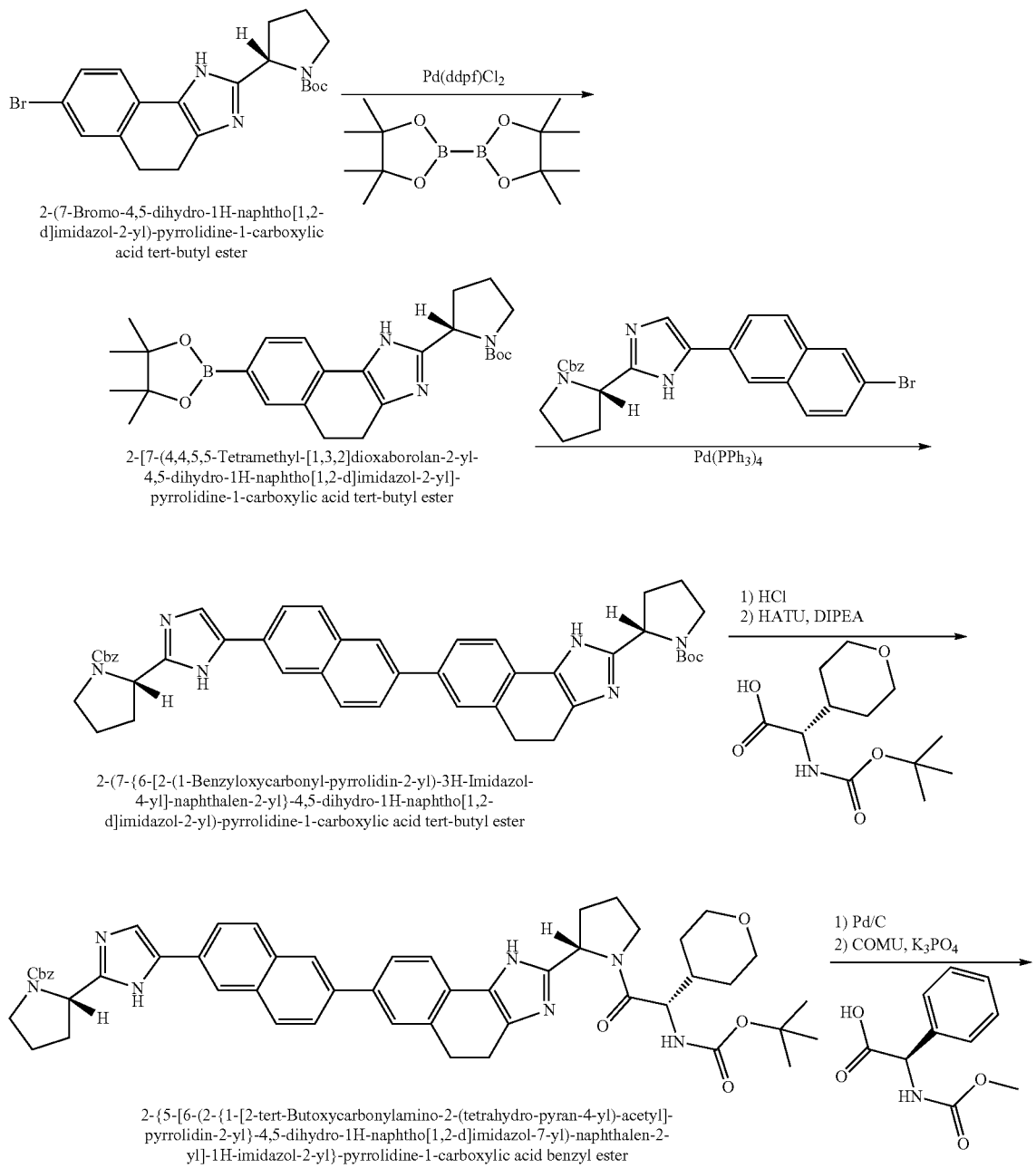

-continued

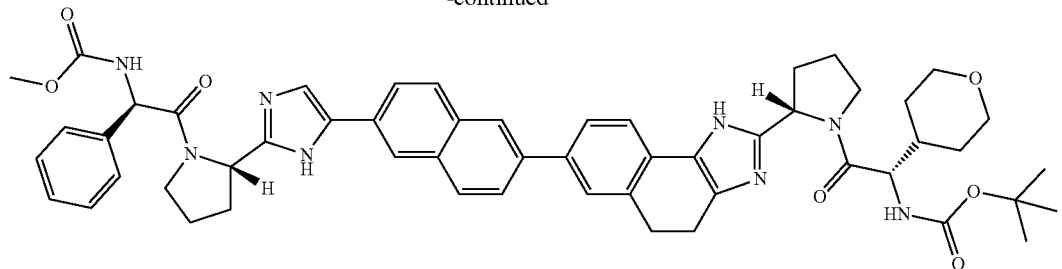

[2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyyrolidin-1-yl}-2-oxo-1-(tetrahydro-pyran-4-yl)-ethyl]-carbamic acid tert-butyl ester 2-[7-(4,4,5,5-Tetramethyl-[1,3,2]dioxaborolan-2-yl)-4,5-dihydro-1H-naphtho[1,2-d]imidazol-2-yl]-pyrrolidine-1-carboxylic acid tert-butyl ester. To a solution of 2-(7-Bromo-4,5-dihydro-1H-naphtho[1,2-d]imidazol-2-yl)-pyrrolidine-carboxylic acid tert-butyl ester (2.00 g, 7.17 mmol) in Dioxane (19 mL) was added 4,4,5,5,4',4',5',5'-Octamethyl-2,2'-bi(1,3,2)dioxaborolane (1.82 g, 7.17 mmol) and 1,1'-Bis(diphenylphosphino)ferrocenedichloride Palladium (0.18 g, 0.24 mmol). The solution was degassed with argon for 5 min and heated, with stirring to 85° C. (external, oil bath) for 3 h. The reaction was cooled to room temperature and diluted with EtOAc. The precipitate was filtered through celite and the filtrate was concentrated. The crude oil was purified by column chromatography (SiO$_2$, 20→100% EtOAc (10% MeOH) in Hexanes) to provide 2-[7-(4,4,5,5-Tetramethyl-[1,3,2]dioxaborolan-2-yl)-4,5-dihydro-1H-naphtho[1,2-d]imidazol-2-yl]-pyrrolidine-1-carboxylic acid tert-butyl ester (1.82 g, 82%). LCMS-ESI$^+$: calc'd for $C_{26}H_{36}BN_3O_4$: 465.28 (M$^+$); Found: 466.54 (M+H$^+$).

[2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-1-(tetrahydro-pyran-4-yl)-ethyl]-carbamic acid tert-butyl ester. [2-{2-[7-(6-{2-[1-(2-Methoxycarbonylamino-2-phenyl-acetyl)-pyrrolidin-2 1]-3H-imidazol-4-yl}-naphthalen-2-yl)-4,5-dihydro-1H-naphtho[1,2-d]imidazol-2-yl]-pyrrolidin-1-yl}-2-oxo-1-(tetrahydro-pyran-4-yl)-ethyl]-carbamic acid tert-butyl ester (0.04 g, 18%) was prepared following the procedure for [2-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester, substituting tert-Butoxycarbonylamino-(tetrahydro-pyran-4-yl)-acetic acid for Methoxycarbonylamino-(tetrahydro-pyran-4-yl)-acetic acid and 2-[7-(4,4,5,5-Tetramethyl-[1,3,2]dioxaborolan-2-yl)-4,5-dihydro-1H-naphtho[1,2-d]imidazol-2-yl]-pyrrolidine-1-carboxylic acid tert-butyl ester for 4,4-Difluoro-2-{5-[4-(4,4,5,5-tetramethyl-[1,3,2]dioxaborolan-2-yl)-phenyl]-1H-imidazol-2-yl}-pyrrolidine-1-carboxylic acid benzyl ester. LCMS-ESI$^+$: calc'd for $C_{54}H_{60}N_8O_7$: 932.46 (M$^+$); Found: 933.95 (M+H$^+$).

Example FJ

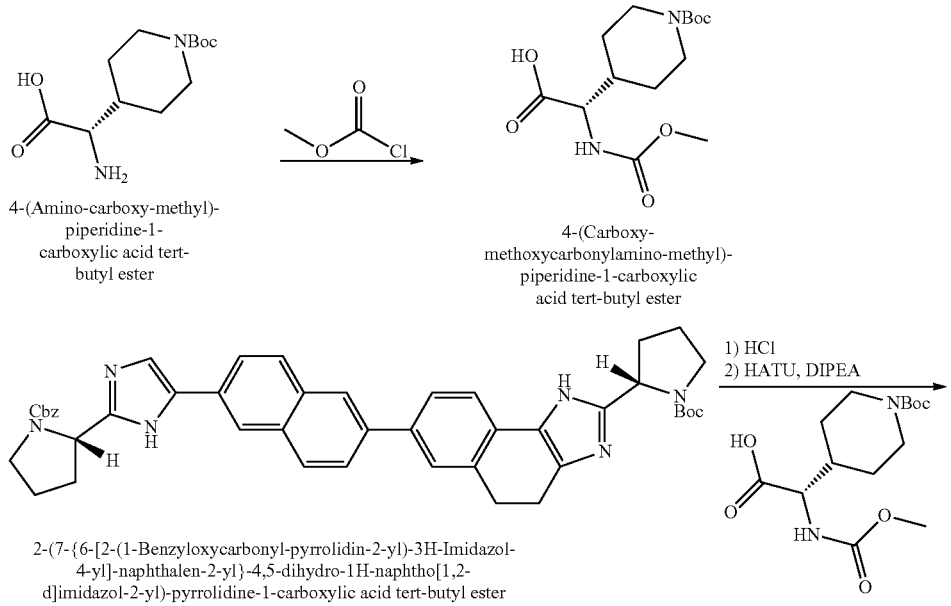

4-(Amino-carboxy-methyl)-piperidine-1-carboxylic acid tert-butyl ester 4-(Carboxy-methoxycarbonylamino-methyl)-piperidine-1-carboxylic acid tert-butyl ester 2-(7-{6-[2-(1-Benzyloxycarbonyl-pyrrolidin-2-yl)-3H-Imidazol-4-yl]-naphthalen-2-yl}-4,5-dihydro-1H-naphtho[1,2-d]imidazol-2-yl)-pyrrolidine-1-carboxylic acid tert-butyl ester 1) HCl
2) HATU, DIPEA -continued

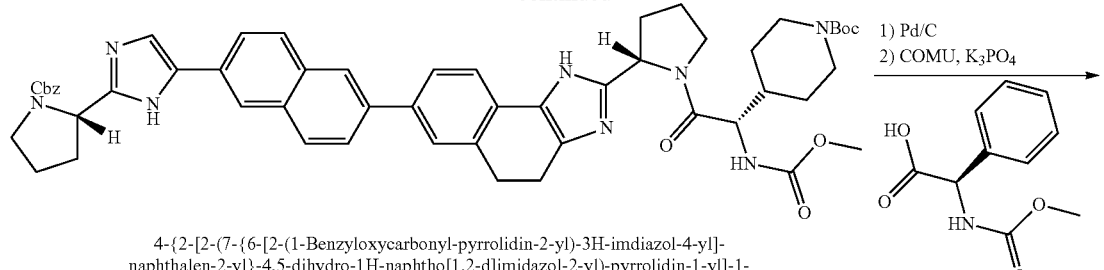

4-{2-[2-(7-{6-[2-(1-Benzyloxycarbonyl-pyrrolidin-2-yl)-3H-imdiazol-4-yl]-
naphthalen-2-yl}-4,5-dihydro-1H-naphtho[1,2-d]imidazol-2-yl)-pyrrolidin-1-yl]-1-
methoxycarbonylamino-2-oxo-ethyl}-piperidine-1-carboxylic acid tert-butyl ester

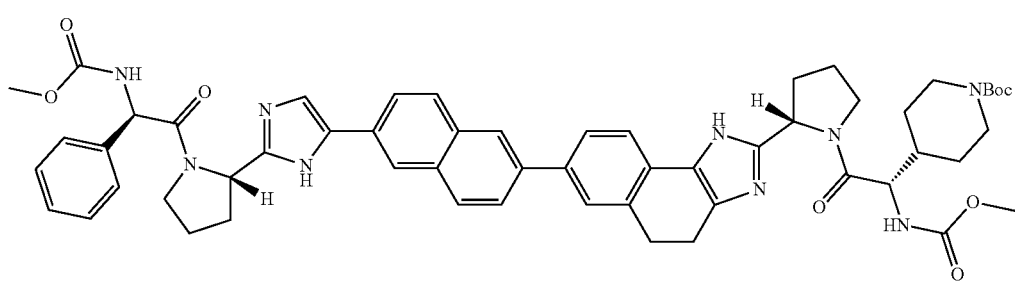

(2-{2-[7-(6-{2-[1-(2-Methoxycarbonylamino-2-phenyl-acetyl)-pyrrolidin-2-yl]-3H-
imidazol-4-yl}-naphthalen-2-yl)-4,5-dihydro-1H-naphto[1,2-d]imidazol-2-yl]-pyyrolidin-
1-yl}-2-oxo-1-tert-butoxycarbonylpiperidin-4-yl-ethyl)-carbamic acid metyl ester 4-(Carboxy-methoxycarbonylamino-methyl)-piperidine-1-carboxylic acid tert-butyl ester. 4-(Carboxy-methoxycarbonylamino-methyl)-piperidine-1-carboxylic acid tert-butyl ester (1.2 g, 97%) was prepared following the procedure for 2-Methoxycarbonylamino-2-phenyl-propionic acid, substituting 4-(Amino-carboxy-methyl)-piperidine-1-carboxylic acid tert-butyl ester for 2-Amino-2-phenyl-propionic acid. LCMS-ESI$^+$: calc'd for $C_{14}H_{24}N_2O_6$: 316.16 (M$^+$); Found: 339.02 (M+Na$^+$).

(2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-1-tert-butoxycarbonylpiperidin-4-yl-ethyl)-carbamic acid methyl ester. (2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-1-tert-butoxycarbonylpiperidin-4-yl-ethyl)-carbamic acid methyl ester (0.05 g, 20%) was prepared following the procedure for [2-(4,4-Difluoro-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidin-1-yl)-2-oxo-1-(tetrahydro-pyran-4-yl)-ethyl]-carbamic acid methyl ester, substituting 4-(Carboxy-methoxycarbonylamino-methyl)-piperidine-1-carboxylic acid tert-butyl ester for Methoxycarbonylamino-(tetrahydro-pyran-4-yl)-acetic acid and 2-[7-(4,4,5,5-Tetramethyl-[1,3,2]dioxaborolan-2-yl)-4,5-dihydro-1H-naphtho[1,2-d]imidazol-2-yl]-pyrrolidine-1-carboxylic acid tert-butyl ester for 4,4-Difluoro-2-{5-[4-(4,4,5,5-tetramethyl-[1,3,2]dioxaborolan-2-yl)-phenyl]-1H-imidazol-2-yl}-pyrrolidine-1-carboxylic acid benzyl ester. LCMS-ESI$^+$: calc'd for $C_{56}H_{63}N_9O_8$: 989.48 (M$^+$); Found: 991.11 (M+H$^+$).

Example FK

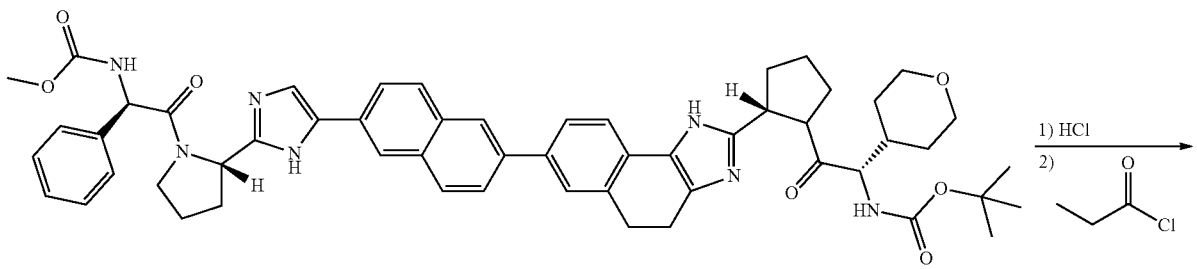

[2-{2-[7-(6-{2-[1-(2-Methoxycarbonylamino-2-phenyl-acetyl)-pyrrolidin-2-yl]-3H-
imidazol-4-yl}-naphthalen-2-yl)-4,5-dihydro-1H-naphtho[1,2-d]imidazol-2-yl]-
pyyrolidin-1-yl}-2-oxo-1-(tetrahydro-pyran-4-yl)-ethyl]-carbamic acid tert-butyl ester -continued

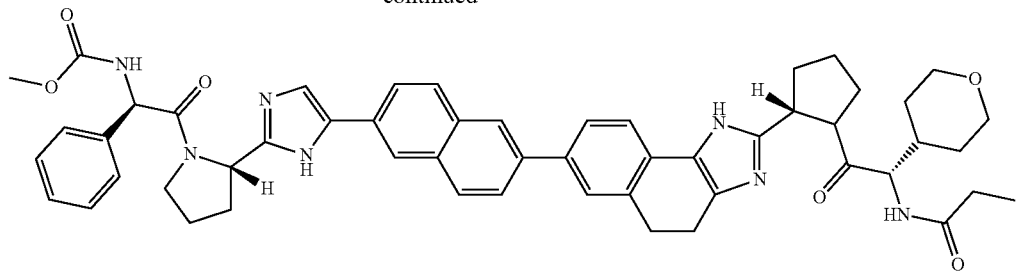

[2-Oxo-1-phenyl-2-(2-{5-[6-(2-{1-[2-propionylamino-2-(tetrahydro-pyran-4-yl)-
acetyl]-pyrrolidin-2-yl}-4,5-dihydro-1H-naphtho[1,2-d]imidazol-7-yl)-naphthalen-
2-yl]-1H-imidazol-2-yl}-pyrrolidin-1-yl)-ethyl]-carbamic acid methyl ester

[2-Oxo-1-phenyl-2-(2-{5-[6-(2-{1-[2-propionylamino-2-(tetrahydro-pyran-4-yl)-acetyl]-pyrrolidin-2-yl}-4,5-dihydro-1H-naphtho[1,2-d]imidazol-7-yl)-naphthalen-2-yl]-1H-imidazol-2-yl}-pyrrolidin-1-yl)-ethyl]-carbamic acid methyl ester. To a solution of [2-{2-[7-(6-{2-[1-(2-Methoxy-carbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-1-(tetrahydro-pyran-4-yl)-ethyl]-carbamic acid tert-butyl ester (0.018 g, 0.020 mmol) in $CH_2Cl_2$ (0.25 mL) and MeOH (0.03 mL) was added HCl (in dioxanes, 4 M, 0.05 mL, 0.2 mmol). The solution was stirred at room temperature for 3 days and concentrated to dryness. The resulting solid was dissolved in DMF (0.5 mL). DIPEA (0.02 mL, 0.12 mmol) and Propionyl chloride (0.003 mL, 0.03 mmol) were added, and the reaction was stirred at room temperature for 1 h. The solution was then purified by preparative HPLC (Gemini, 15→60% MeCN in $H_2O$ (0.1% TFA)) and lyophilized to provide to provide [2-Oxo-1-phenyl-2-(2-{5-[6-(2-{1-[2-propionylamino-2-(tetrahydro-pyran-4-yl)-acetyl]-pyrrolidin-2-yl}-4,5-dihydro-1H-naphtho[1,2-d]imidazol-7-yl)-naphthalen-2-yl]-1H-imidazol-2-yl}-pyrrolidin-1-yl)-ethyl]-carbamic acid methyl ester (0.01 g, 44%). LCMS-ESI$^+$: calc'd for $C_{52}H_{56}N_8O_6$: 888.43 (M$^+$); Found: 890.07 (M+H$^+$).

Example FL

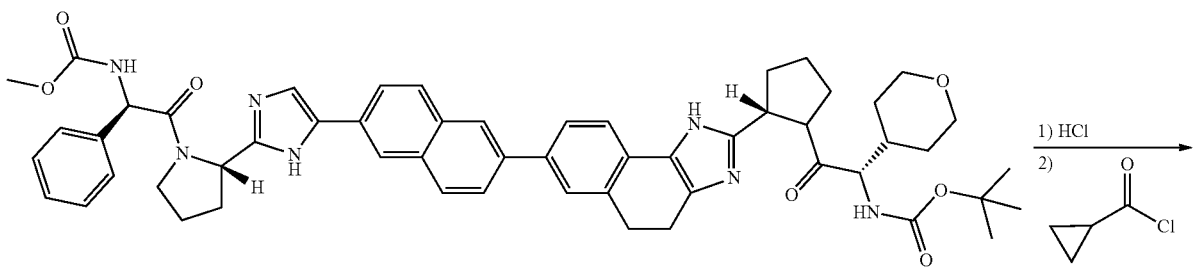

[2-{2-[7-(6-{2-[1-(2-Methoxycarbonylamino-2-phenyl-acetyl)-pyrrolidin-2-yl]-3H-
imidazol-4-yl}-naphthalen-2-yl)-4,5-dihydro-1H-naphtho[1,2-d]imidazol-2-yl]-
pyyrolidin-1-yl}-2-oxo-1-(tetrahydro-pyran-4-yl)-ethyl]-carbamic acid tert-butyl ester

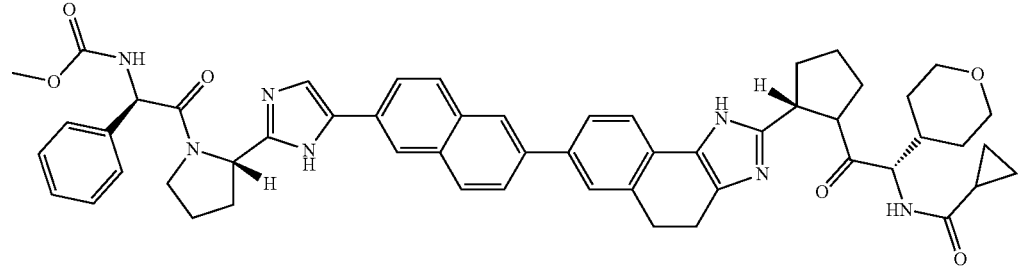

{2-(2-{5-[6-(2-{1-[2-Cyclopropanecarbonyl-amino)-2-(tetrahydro-pyran-4-yl)-acetyl]-
pyrrolidin-2-yl}-4,5-dihydro-1H-naphtho[1,2-d]imidazol-7-yl)-naphthalen-2-yl]-1H-
imidazol-2-yl}-pyrrolidin-1-yl)-2-oxo-1-phenyl-ethyl}-carbamic acid methyl ester

[2-(2-{5 [6-(2-{1-[2-(Cyclopropanecarbonyl-amino)-2-(tetrahydro-pyran-4-yl)-acetyl]-pyrrolidin-2-yl}-4,5-dihydro-1H-naphtho[1,2-d]imidazol-7-yl)-naphthalen-2-yl]-1H-imidazol-2-yl}-pyrrolidin-1-yl)-2-oxo-1-phenyl-ethyl]-carbamic acid methyl ester. [2-(2-{5-[6-(2-{1-[2-(Cyclopropanecarbonyl-amino)-2-(tetrahydro-pyran-4-yl)-acetyl]-pyrrolidin-2-yl}-4,5-dihydro-1H-naphtho[1,2-d]imidazol-7-yl)-naphthalen-2-yl]-1H-imidazol-2-yl}-pyrrolidin-1-yl)-2-oxo-1-phenyl-ethyl]-carbamic acid methyl ester (0.01 g, 38%) was prepared following the procedure for [2-Oxo-1-phenyl-2-(2-{5-[6-(2-{1-[2-propionylamino-2-(tetrahydro-pyran-4-yl)-acetyl]-pyrrolidin-2-yl}-4,5-dihydro-1H-naphtho[1,2-d]imidazol-7-yl)-naphthalen-2-yl]-1H-imidazol-2-yl}-pyrrolidin-1-yl)-ethyl]-carbamic acid methyl ester, substituting Cyclopropanecarbonyl chloride for Propionyl chloride. LCMS-ESI$^+$: calc'd for $C_{53}H_{56}N_8O_6$: 900.43 (M$^+$); Found: 902.07 (M+H$^+$).

Example FM

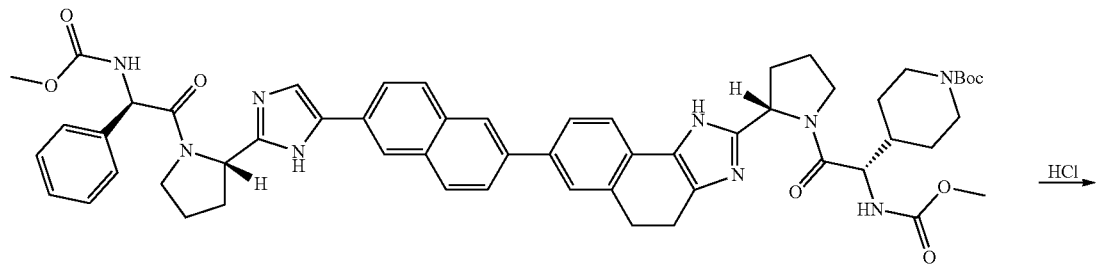

[2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphto[1,2-d]imidazol-2-yl]-pyyrolidin-1-yl}-2-oxo-1-tert-butoxycarbonylpiperidin-4-yl-ethyl)-carbamic acid metyl ester

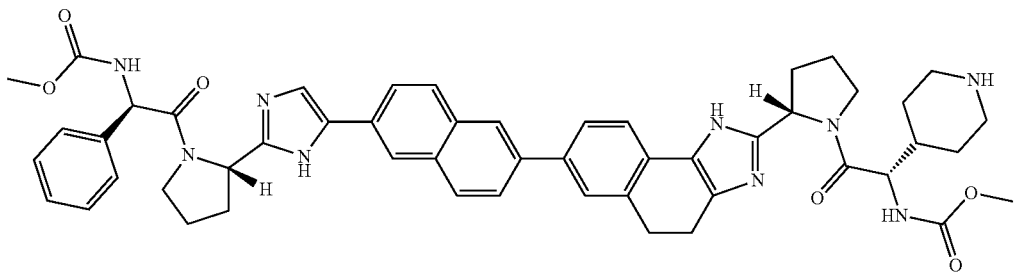

(2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-1-piperidin-4-yl-ethyl)-carbamic acid methyl ester (2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-1-piperidin-4-yl-ethyl)-carbamic acid methyl ester. To a solution of (2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-1-tert-butoxycarbonylpiperidin-4-yl-ethyl)-carbamic acid methyl ester (0.025 g, 0.025 mmol) in CH$_2$Cl$_2$ (0.25 mL) and MeOH (0.025 mL) was added HCl (in dioxane, 0.12 mL, 0.48 mmol). The solution was stirred at room temperature for 3 days and concentrated to dryness. The crude oil was purified by preparative HPLC (Gemini, 15→50% MeCN in H$_2$O (0.1% TFA)) and lyophilized to provide (2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-1-piperidin-4-yl-ethyl)-carbamic acid methyl ester (0.015 g, 66%). LCMS-ESI$^+$: calc'd for C$_{51}$H$_{55}$N$_9$O$_6$: 889.43 (M$^+$); Found: 890.29 (M+H$^+$).

Example FN

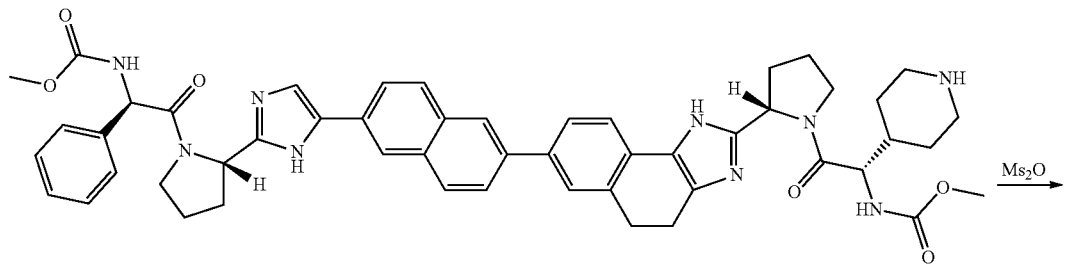

[2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphto[1,2-d]imidazol-2-yl]-pyyrolidin-1-yl}-2-oxo-1-piperidi-4-yl-ethyl)-carbamic acid methyl ester

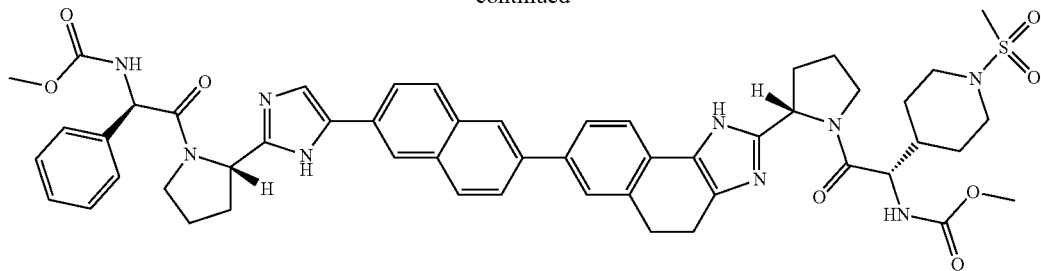

(1-(1-Methanesulfonyl-piperidin-4-yl)-2-{2-[7-(6-{2-[1-(2-methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-ethyl)-carbamic acid methyl ester (1-(1-Methanesulfonyl-piperidin-4-yl)-2-{2-[7-(6-{2-[1-(2-methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-ethyl)-carbamic acid methyl ester. To a solution of (2-{2-[7-(6-{2-[1-(2-Methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-1-piperidin-4-yl-ethyl)-carbamic acid methyl ester (0.022 g, 0.025 mmol) in CH$_2$Cl$_2$ (0.5 mL) and DMF (0.5 mL) was added DIPEA (0.025 mL, 0.14 mol) and Methanesulfonic anhydride (0.007 g, 0.04 mmol). The solution was stirred at room temperature for 1 h and concentrated. The crude oil was purified by preparative HPLC (Gemini, 15-60% MeCN in H$_2$O (0.1% TFA)) and lyophilized to provide (1-(1-Methanesulfonyl-piperidin-4-yl)-2-{2-[7-(6-{2-[1-(2-methoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidin-1-yl}-2-oxo-ethyl)-carbamic acid methyl ester (0.01 g, 46%). LCMS-ESI$^+$: calc'd for C$_{52}$H$_{57}$N$_9$O$_8$S: 967.41 (M$^+$); Found: 969.19 (M+H$^+$).

Example FO

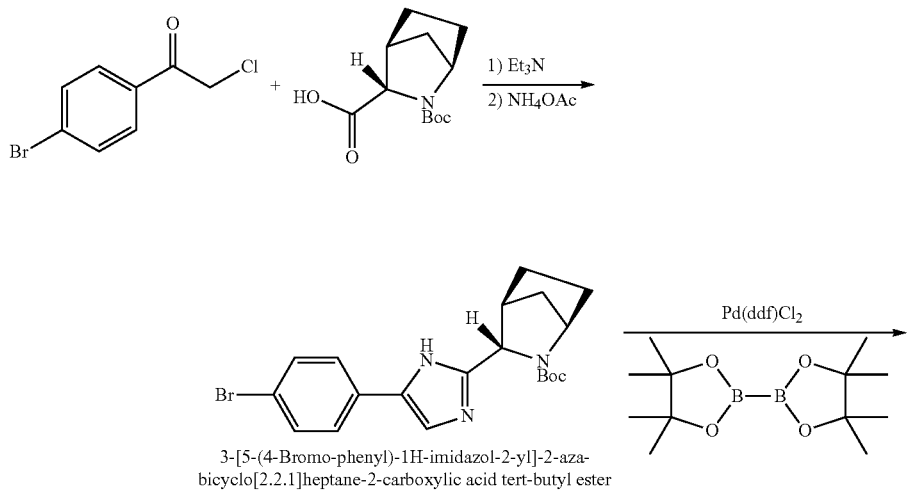

3-[5-(4-Bromo-phenyl)-1H-imidazol-2-yl]-2-aza-bicyclo[2.2.1]heptane-2-carboxylic acid tert-butyl ester

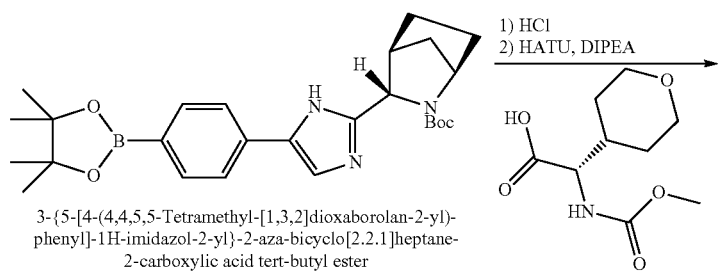

3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester

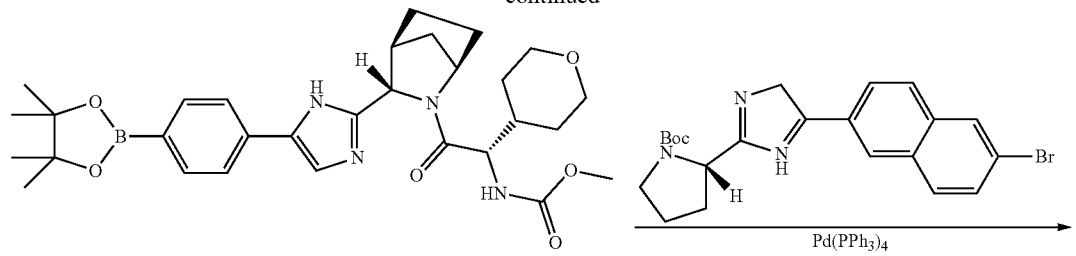

[2-Oxo-1-(tetrahydro-pyran-4-yl)-2-(3-{5-[4-(4,4,5,5-tetramethyl-
[1,3,2]dioxaborolan-2-yl)-phenyl]-1H-imidazol-2-yl}-2-aza-
bicyclo[2.2.1]hept-2-yl)-ethyl]-carbamic acid methyl ester

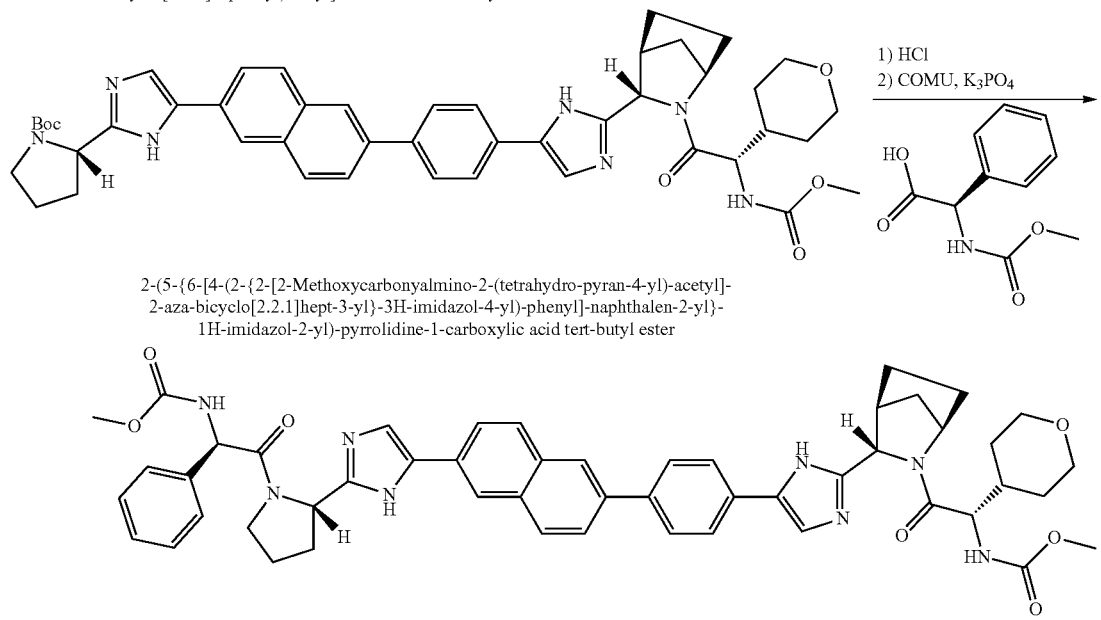

2-(5-{6-[4-(2-{2-[2-Methoxycarbonylamino-2-(tetrahydro-pyran-4-yl)-acetyl]-
2-aza-bicyclo[2.2.1]hept-3-yl}-3H-imidazol-4-yl)-phenyl]-naphthalen-2-yl}-
1H-imidazol-2-yl)-pyrrolidine-1-carboxylic acid tert-butyl ester

[2-(3-{5-[4-(6-{2-[1-(2-Methoxycarbonylamino-2-phenyl-acetyl)-pyrrolidin-2-yl]-3H-
imidazol-4-yl}-naphthalen-2-yl)-phenyl]-1H-imidazol-2-yl}-2-aza-bicycle[2.2.1]hept-
2-yl)-2-oxo-1-(tetrahydro-pyran-4-yl)-ethyl]-carbamic acid methyl ester 3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester. 3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester was prepared following the procedure for 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester, substituting 2-Aza-bicyclo[2.2.1]heptane-2,3-dicarboxylic acid 2-tert-butyl ester for Pyrrolidine-1,2-dicarboxylic acid 1-tert-butyl ester. LCMS-ESI$^+$: calc'd for $C_{26}H_{36}BN_3O_4$: 465.28 (M$^+$); Found: 466.21 (M+H$^+$).

[2-Oxo-1-(tetrahydro-pyran-4-yl)-2-(3-{5-[4-(4,4,5,5-tetramethyl-[1,3,2]dioxaborolan-2-yl)-phenyl]-1H-imidazol-2-yl}-2-aza-bicyclo[2.2.1]hept-2-yl)-ethyl]-carbamic acid methyl ester. To a solution of 3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester (0.25 g, 0.54 mmol) in CH$_2$Cl$_2$ (5 mL) and MeOH (0.5 mL) was added HCl (in dioxane, 4 M, 1.35 mL, 5.40 mmol). The solution was stirred at room temperature for 2 h and concentrated to dryness. The resulting solid was slurried in CH$_2$Cl$_2$ (5 mL) and DMF (1 mL). Methoxycarbonylamino-(tetrahydro-pyran-4-yl)-acetic acid (0.15 g, 0.71 mmol), COMU (0.25 g, 0.59 mmol), and DIPEA (0.50 mL, 0.59 mmol) were added, and the resulting solution was stirred at room temperature for 1 h. The reaction was diluted with EtOAc and washed with saturated sodium bicarbonate and brine. The aqueous layers were backextracted with EtOAc. The combined organic layers were dried over Na$_2$SO$_4$ and concentrated. The crude oil was purified by column chromatography (SiO$_2$, 10→100% EtOAc (10% MeOH) in Hexanes) to provide [2-Oxo-1-(tetrahydro-pyran-4-yl)-2-(3-{5-[4-(4,4,5,5-tetramethyl-[1,3,2]dioxaborolan-2-yl)-phenyl]-1H-imidazol-2-yl}-2-aza-bicyclo[2.2.1]hept-2-yl)-ethyl]-carbamic acid methyl ester (0.24 g, 79%). LCMS-ESI$^+$: calc'd for $C_{30}H_{41}BN_4O_6$: 564.31 (M$^+$); Found: 565.40 (M+H$^+$).

2-(5-{6-[4-(2-{2-[2-Methoxycarbonylamino-2-(tetrahydro-pyran-4-yl)-acetyl]-2-aza-bicyclo[2.2.1]hept-3-yl}-3H-imidazol-4-yl)-phenyl]-naphthalen-2-yl}-1H-imidazol-2-yl)-pyrrolidine-1-carboxylic acid tert-butyl ester. To a solution of [2-Oxo-1-(tetrahydro-pyran-4-yl)-2-(3-{5-[4-(4,4,5,5-tetramethyl-[1,3,2]dioxaborolan-2-yl)-phenyl]-1H-imidazol-2-yl}-2-aza-bicyclo[2.2.1]hept-2-yl)-ethyl]-carbamic acid methyl ester (0.24 g, 0.42 mmol) in DME (2.5 mL) was added 2-[5-(6-Bromo-naphthalen-2-yl)-1H-imidazol-2-yl]-pyrrolidine-1-carboxylic acid tert-butyl ester (0.19 g, 0.43 mmol), Tetrakis(triphenylphosphine)Palladium (0.03 g, 0.02 mmol) and aqueous potassium phosphate (2 M, 0.65 mL, 1.3 mmol). The solution was degassed with argon for 15 min and heated to 80° C. for 18 h with stirring. The solution was cooled and concentrated. The crude oil was purified by column chromatography (SiO$_2$, 30→100% EtOAc (10% MeOH) in Hexanes to 50% MeOH in EtOAc) to provide 2-(5-{6-[4-(2-{2-[2-Methoxycarbonylamino-2-(tetrahydro-pyran-4-yl)-acetyl]-2-azabicyclo[2.2.1]hept-3-yl}-3H-imidazol-4-yl)-phenyl]-naphthalen-2-yl}-1H-imidazol-2-yl)-pyrrolidine-1-carboxylic acid tert-butyl ester (0.26 g, 76%). LCMS-ESI$^+$: calc'd for C$_{46}$H$_{53}$N$_7$O$_6$: 799.41 (M$^+$); Found: 800.4 (M+H$^+$).

[2-(3-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-2-aza-bicyclo[2.2.1]hept-2-yl)-2-oxo-1-(tetrahydro-pyran-4-yl)-ethyl]-carbamic acid methyl ester. To a solution of 2-(5-{6-[4-(2-{2-[2-Methoxycarbonylamino-2-(tetrahydro-pyran-4-yl)-acetyl]-2-aza-bicyclo[2.2.1]hept-3-yl}-3H-imidazol-4-yl)-phenyl]-naphthalen-2-yl}-1H-imidazol-2-yl)-pyrrolidine-1-carboxylic acid tert-butyl ester (0.26 g, 0.32 mmol) in CH$_2$Cl$_2$ (3.5 mL) and MeOH (0.2 mL) was added HCl (in dioxanes, 4 M, 1.6 mL, 6.4 mmol). The resulting solution was stirred at room temperature for 2 h and concentrated. The resulting solid was slurried in CH$_2$Cl$_2$ (3.5 mL) and DMF (0.5 mL). Methoxycarbonylamino-phenyl-acetic acid (0.08 g, 0.39 mmol) and DIPEA (0.250 mL, 1.43 mmol) were added and the solution was cooled to 0° C. (external, ice bath). COMU (0.16 g, 0.36 mmol) was added and the reaction was stirred at 0° C. for 3 h. The solution was diluted with CH$_2$Cl$_2$ and washed with saturated sodium bicarbonate and brine. The aqueous layers were backextracted with CH$_2$Cl$_2$. The combined organic layers were dried over Na$_2$SO$_4$ and concentrated. The crude oil was purified by preparative HPLC (Gemini, 15→60% MeCN in H$_2$O (0.1% TFA)). The combined fractions were concentrated until the aqueous layer remained. A small amount of MeOH was added to make the solution homogenous before it was basified with saturated sodium bicarbonate. The resulting precipitate was filtered, washed with H$_2$O, and dried in vacuo to provide [2-(3-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-2-aza-bicyclo[2.2.1]hept-2-yl)-2-oxo-1-(tetrahydro-pyran-4-yl)-ethyl]-carbamic acid methyl ester (0.21 g, 72%). LCMS-ESI$^+$: calc'd for C$_{51}$H$_{54}$N$_8$O$_7$: 890.41 (M$^+$); Found: 891.95 (M+H$^+$).

Example FP

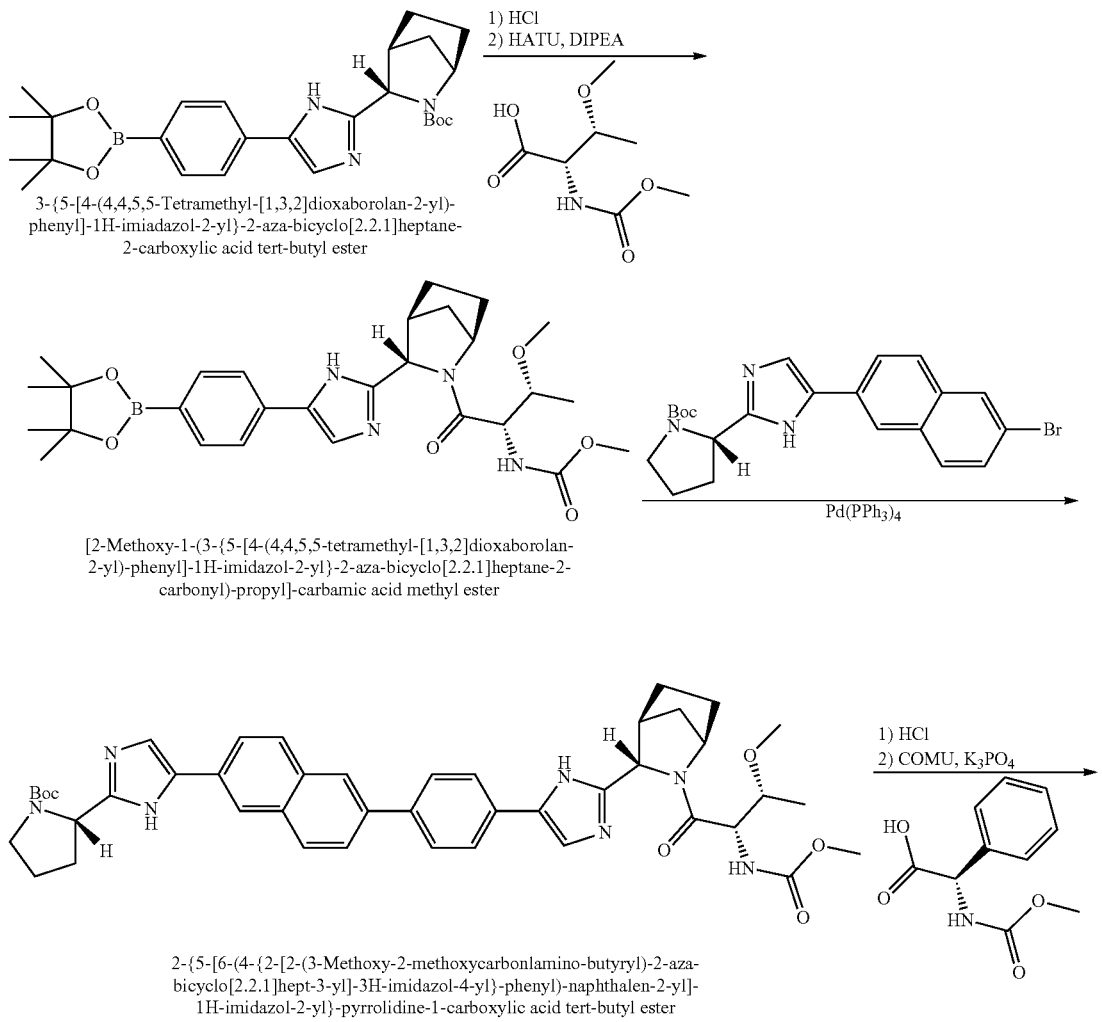

-continued

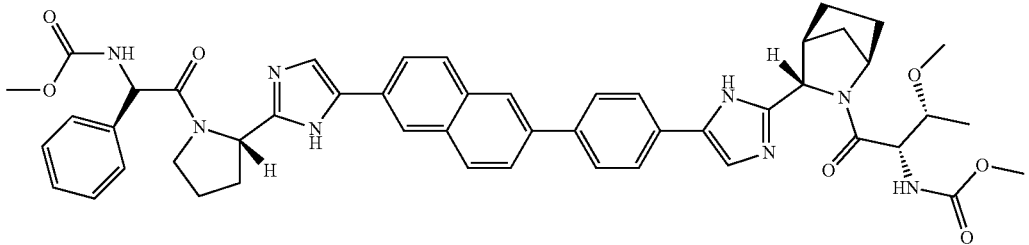

[2-Methoxy-1-(3-{5-[4-(6-{2-[1-(2-methoxycarbonylamino-2-phenyl-acetyl)-
pyrrolidin-2-yl]-3H-imidazol-4-yl}-naphthalen-2-yl)-phenyl]-1H-imidazol-2-yl}-2-
aza-bicyclo[2.2.1]heptane-2-carbonyl)-propyl]-carbamic acid methyl ester

[2-Methoxy-1-(3-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-2-aza-bicyclo[2.2.1]heptane-2-carbonyl)-propyl]-carbamic acid methyl ester. [2-Methoxy-1-(3-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-2-aza-bicyclo[2.2.1]heptane-2-carbonyl)-propyl]-carbamic acid methyl ester (0.18 g, 39%) was prepared following the procedure for [2-(3-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-2-aza-bicyclo[2.2.1]hept-2-yl)-2-oxo-1-(tetrahydro-pyran-4-yl)-ethyl]-carbamic acid methyl ester, substituting 3-Methoxy-2-methoxycarbonylamino-butyric acid for Methoxycarbonylamino-(tetrahydro-pyran-4-yl)-acetic acid. LCMS-ESI$^+$: calc'd for $C_{49}H_{52}N_8O_7$: 864.40 (M$^+$); Found: 865.87 (M+H$^+$).

Example FQ

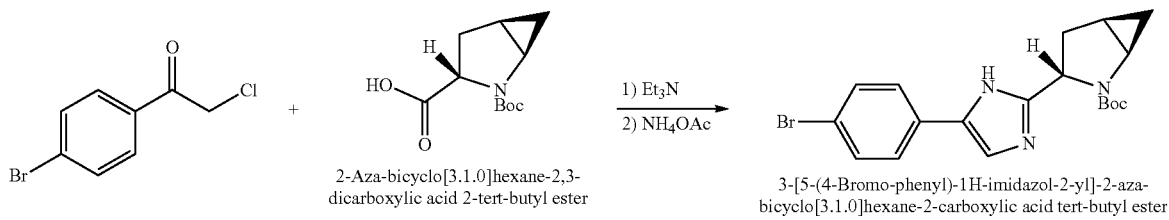

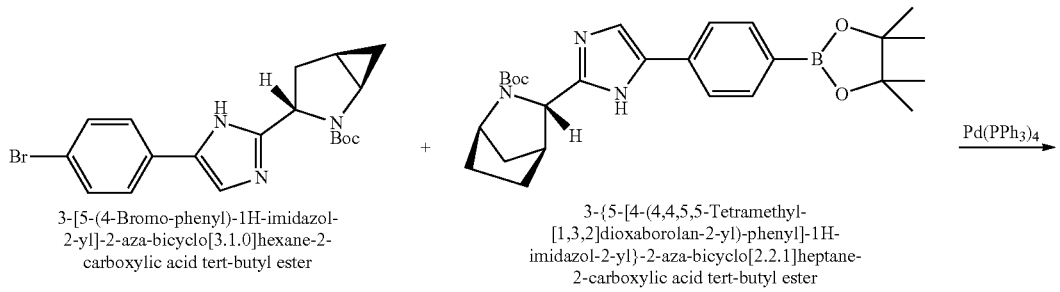

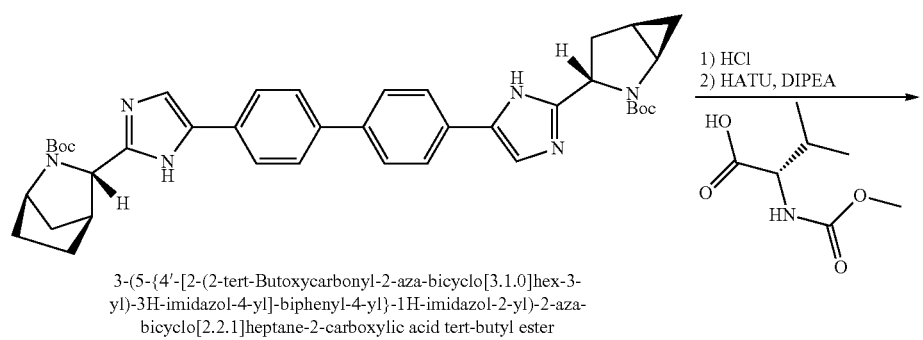

-continued

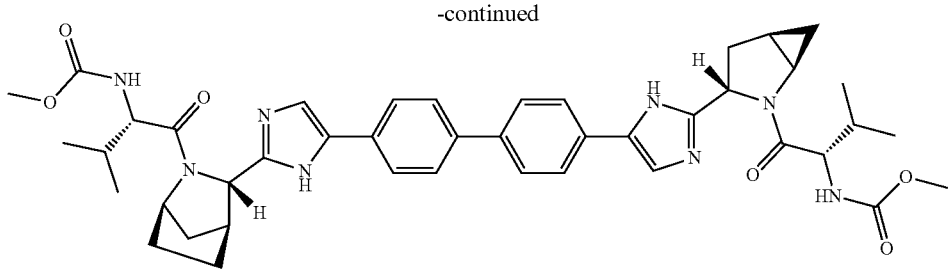

(1-{3-[5-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-imidazol-2-yl]-2-aza-bicyclo[3.1.0]hexane-2-carbonyl}-2-methyl-propyl-carbamic acid methyl ester 3-[5-(4-Bromo-phenyl)-1H-imidazol-2-yl]-2-aza-bicyclo[3.1.0]hexane-2-carboxylic acid tert-butyl ester. 3-[5-(4-Bromo-phenyl)-1H-imidazol-2-yl]-2-aza-bicyclo[3.1.0]hexane-2-carboxylic acid tert-butyl ester (0.16 g, 60%) was prepared following the procedure for 2-[5-(4-Bromo-phenyl)-1H-imidazol-2-yl]-pyrrolidine-1-carboxylic acid tert-butyl ester, substituting 2-Aza-bicyclo[3.1.0]hexane-2,3-dicarboxylic acid 2-tert-butyl ester for Pyrrolidine-1,2-dicarboxylic acid 1-tert-butyl ester. LCMS-ESI$^+$: calc'd for $C_{19}H_{22}BrN_3O_2$: 403.09 (M$^+$); Found: 404.76 (M+H$^+$).

3-(5-{4'-[2-(2-tert-Butoxycarbonyl-2-aza-bicyclo[3.1.0]hex-3-yl)-3H-imidazol-4-yl]-biphenyl-4-yl}-1H-imidazol-2-yl)-2-aza-bicyclo[2.2.1]heptane-2-carboxylic acid tert-butyl ester. To a solution of 3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester (0.19 g, 0.41 mmol) in DME (2.0 mL) was added 3-[5-(4-Bromo-phenyl)-1H-imidazol-2-yl]-2-aza-bicyclo[3.1.0]hexane-2-carboxylic acid tert-butyl ester (0.16 g, 0.41 mmol), Tetrakis(triphenylphosphine)Palladium (0.05 g, 0.04 mmol) and aqueous potassium phosphate (2 M, 0.60 mL, 1.2 mmol). The solution was degassed with argon for 15 min and heated to 80° C. for 18 h with stirring. The solution was cooled diluted with EtOAc and filtered. The filtrate was washed with H$_2$O and brine. The organic layers were dried over Na$_2$SO$_4$ and concentrated. The crude oil was purified by column chromatography (SiO$_2$, 30→100% EtOAc (10% MeOH) in Hexanes to 80% MeOH in EtOAc). The desired fractions were concentrated and combined with the filtered solid to provide 3-(5-{4'-[2-(2-tert-Butoxycarbonyl-2-aza-bicyclo[3.1.0]hex-3-yl)-3H-imidazol-4-yl]-biphenyl-4-yl}-1H-imidazol-2-yl)-2-aza-bicyclo[2.2.1]heptane-2-carboxylic acid tert-butyl ester (0.17 g, 62%). LCMS-ESI$^+$: calc'd for $C_{39}H_{46}N_6O_4$: 662.36 (M$^+$); Found: 663.39 (M+H$^+$).

(1-{3-[5-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-imidazol-2-yl]-2-aza-bicyclo[3.1.0]hexane-2-carbonyl}-2-methyl-propyl)-carbamic acid methyl ester. To a solution of 3-(5-{4'-[2-(2-tert-Butoxycarbonyl-2-aza-bicyclo[3.1.0]hex-3-yl)-3H-imidazol-4-yl]-biphenyl-4-yl}-1H-imidazol-2-yl)-2-aza-bicyclo[2.2.1]heptane-2-carboxylic acid tert-butyl ester (0.17 g, 0.25 mmol) in CH$_2$Cl$_2$ (3.0 mL) and MeOH (0.5 mL) was added HCl (in dioxane, 4 M, 2.0 mL, 8.0 mmol). The solution was stirred at room temperature for 2.5 h, then at 50° (external, oil bath) for 1 h. The solution was cooled and concentrated. The resulting solid was slurried in CH$_2$Cl$_2$ (3.0 mL) and DMF (0.5 mL). 2-Methoxycarbonylamino-3-methyl-butyric acid (0.12 g, 0.56 mmol), HATU (0.21 g, 0.54 mmol), and DIPEA (0.4 mL, 2.29 mmol) were added. The solution was stirred at room temperature for 1 h and concentrated. The crude oil was purified by preparative HPLC (Gemini, 15→50% MeCN in H$_2$O (0.1% TFA)). The combined fractions were concentrated until the aqueous layer remained. A small amount of MeOH was added to make the solution homogenous before it was basified with saturated sodium bicarbonate. The resulting precipitate was filtered, washed with H$_2$O, and dried in vacuo to provide (1-{3-[5-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-imidazol-2-yl]-2-aza-bicyclo[3.1.0]hexane-2-carbonyl}-2-methyl-propyl)-carbamic acid methyl ester (0.13 g, 64%). LCMS-ESI$^+$: calc'd for $C_{43}H_{52}N_8O_6$: 776.40 (M$^+$); Found: 777.64 (M+H$^+$).

Example FR

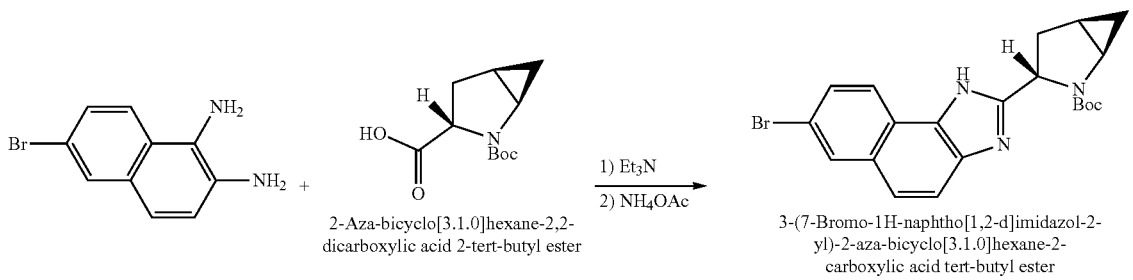

-continued

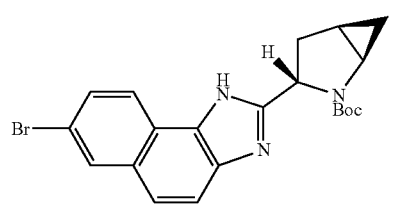

3-(7-Bromo-1H-naphtho[1,2-d]imidazol-2-yl)-2-aza-bicyclo[3.1.0]hexane-2-carboxylic acid tert-butyl ester

+

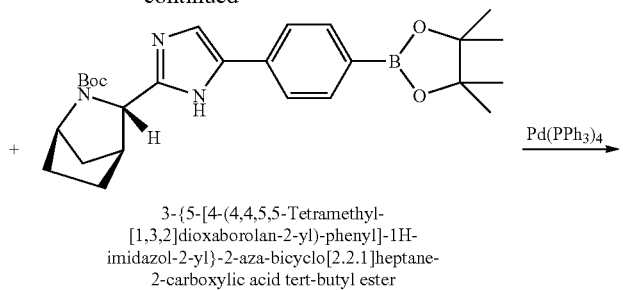

3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester Pd(PPh$_3$)$_4$ →

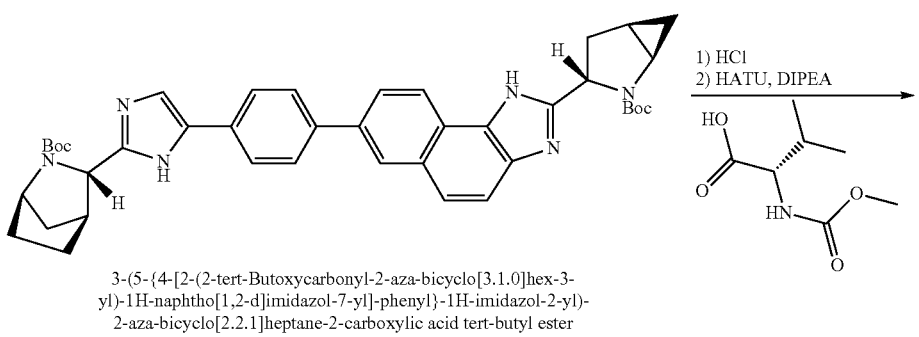

3-(5-{4-[2-(2-tert-Butoxycarbonyl-2-aza-bicyclo[3.1.0]hex-3-yl)-1H-naphtho[1,2-d]imidazol-7-yl]-phenyl}-1H-imidazol-2-yl)-2-aza-bicyclo[2.2.1]heptane-2-carboxylic acid tert-butyl ester 1) HCl
2) HATU, DIPEA →

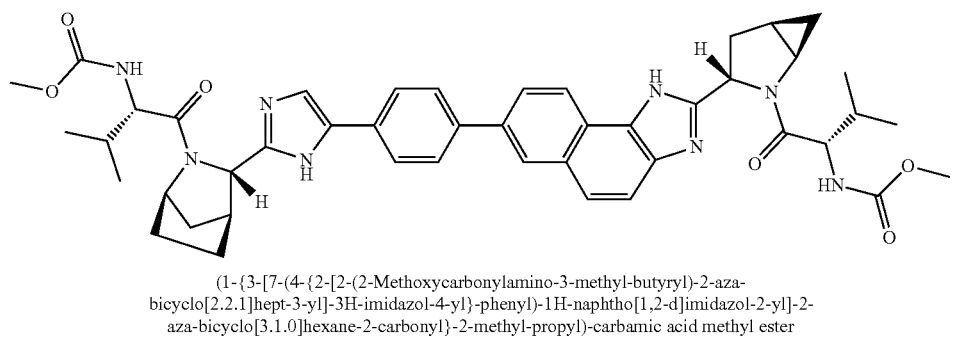

(1-{3-[7-(4-{2-[2-(2-Methoxycarbonylamino-3-methyl-butyryl)-2-aza-bicyclo[2.2.1]hept-3-yl]-3H-imidazol-4-yl}-phenyl)-1H-naphtho[1,2-d]imidazol-2-yl]-2-aza-bicyclo[3.1.0]hexane-2-carbonyl}-2-methyl-propyl)-carbamic acid methyl ester 3-(7-Bromo-1H-naphtho[1,2-d]imidazol-2-yl)-2-aza-bicyclo[3.1.0]hexane-2-carboxylic acid tert-butyl ester. To a solution of 2-Aza-bicyclo[3.1.0]hexane-2,3-dicarboxylic acid 2-tert-butyl ester (0.08 g, 0.34 mmol) in CH$_2$Cl$_2$ (3.5 mL) was added 6-Bromo-naphthalene-1,2-diamine (0.09 g, 0.041 mmol), HATU (0.16 g, 0.43 mmol), and DIPEA (0.3 mL, 1.72 mmol). The resulting solution was stirred at room temperature for 1.5 h and diluted with EtOAc. The organic layer was washed with H$_2$O and brine. The aqueous layers were backextracted with EtOAc. The combined organic layers were dried over Na$_2$SO4 and separated. The crude oil was purified by column chromatography (SiO$_2$, 10→100% EtOAc (2% MeOH) in hexanes) to provide an oil that was dissolved in AcOH (7.0 mL). The solution was stirred at 40° C. (external, oil bath) for 2 h. The solution was diluted with EtOAc and slowly basified with saturated sodium bicarbonate and NaOH (2N). The organic layer was separated, dried over Na$_2$SO$_4$, and concentrated. The crude oil was purified by column chromatography (SiO$_2$, 10→100% EtOAc (2% MeOH) in hexanes) to provide 3-(7-Bromo-1H-naphtho[1,2-d]imidazol-2-yl)-2-aza-bicyclo[3.1.0]hexane-2-carboxylic acid tert-butyl ester (0.15 g, 97%). LCMS-ESI$^+$: calc'd for C$_{21}$H$_{22}$BrN$_3$O$_2$: 427.09 (M$^+$); Found: 428.35 (M+H$^+$).

(1-{3-[7-(4-{2-[2-(2-Methoxycarbonylamino-3-methyl-butyryl)-2-aza-bicyclo[2.2.1]hept-3-yl]-3H-imidazol-4-yl}-phenyl)-1H-naphtho[1,2-d]imidazol-2-yl]-2-aza-bicyclo[3.1.0]hexane-2-carbonyl}-2-methyl-propyl)-carbamic acid methyl ester. (1-{3-[7-(4-{2-[2-(2-Methoxycarbonylamino-3-methyl-butyryl)-2-aza-bicyclo[2.2.1]hept-3-yl]-3H-imidazol-4-yl}-phenyl)-1H-naphtho[1,2-d]imidazol-2-yl]-2-aza-bicyclo[3.1.0]hexane-2-carbonyl}-2-methyl-propyl)-carbamic acid methyl ester (0.13 g, 45%) was prepared following the procedure for (1-{3-[5-(4'-{2-[2-(2-Methoxycarbonylamino-3-methyl-butyryl)-2-aza-bicyclo[2.2.1]hept-3-yl]-3H-imidazol-4-yl}-biphenyl-4-yl)-1H-imidazol-2-yl]-2-aza-bicyclo[3.1.0]hexane-2-carbonyl}-2-methyl-propyl)-carbamic acid methyl ester, substituting 3-(7-Bromo-1H-naphtho[1,2-d]imidazol-2-yl)-2-aza-bicyclo[3.1.0]hexane-2-carboxylic acid tert-butyl ester for 3-[5-(4-Bromo-phenyl)-1H-imidazol-2-yl]-2-aza-bicyclo[3.1.0]hexane-2-carboxylic acid tert-butyl ester. LCMS-ESI$^+$: calc'd for C$_{45}$H$_{52}$N$_8$O$_6$: 800.40 (M$^+$); Found: 801.73 (M+H$^+$).

Example FS

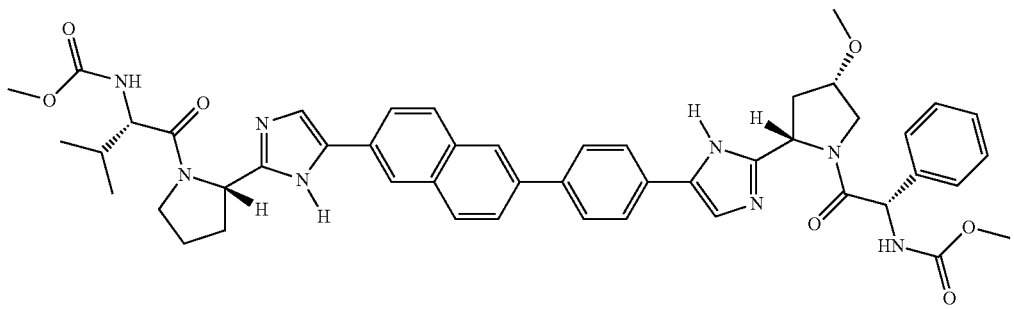

[1-(2-{5-[6-(4-{2-[4-Methoxy-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[4-Methoxy-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[4-Methoxy-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester was prepared following the procedure for [1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, substituting 4-Methoxy-pyrrolidine-1,2-dicarboxylic acid 1-tert-butyl ester for Pyrrolidine-1,2-dicarboxylic acid 1-tert-butyl ester and Methoxycarbonylamino-phenyl-acetic acid for 2-Methoxycarbonylamino-2-phenyl-propionic acid. LCMS-ESI$^+$: calc'd for $C_{48}H_{52}N_8O_7$: 852.40 (M$^+$); Found: 853.43 (M+H$^+$).

Example FT

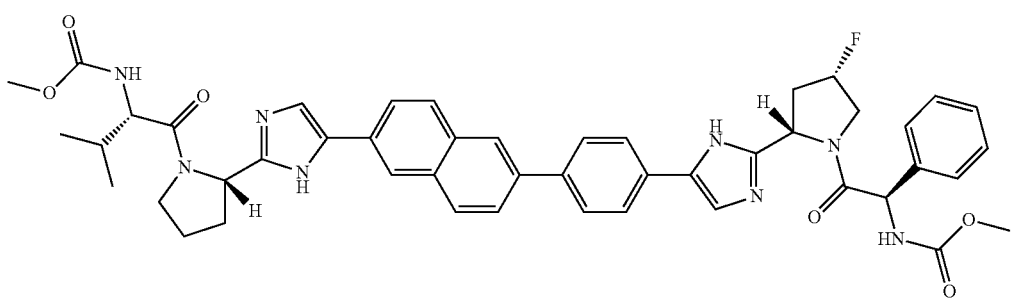

[1-(2-{5-[6-(4-{2-[4-Fluoro-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[4-Fluoro-1-(2-methoxycarbonylamino-2-phenyl-acetyl)- pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[4-Fluoro-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester was prepared following the procedure for [1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, substituting 4-Fluoro-pyrrolidine-1,2-dicarboxylic acid 1-tert-butyl ester for Pyrrolidine-1,2-dicarboxylic acid 1-tert-butyl ester and Methoxycarbonylamino-phenyl-acetic acid for 2-Methoxycarbonylamino-2-phenyl-propionic acid. LCMS-ESI$^+$: calc'd for $C_{47}H_{49}FN_8O_6$: 840.38 (M$^+$); Found: 841.45 (M+H$^+$).

Example FU

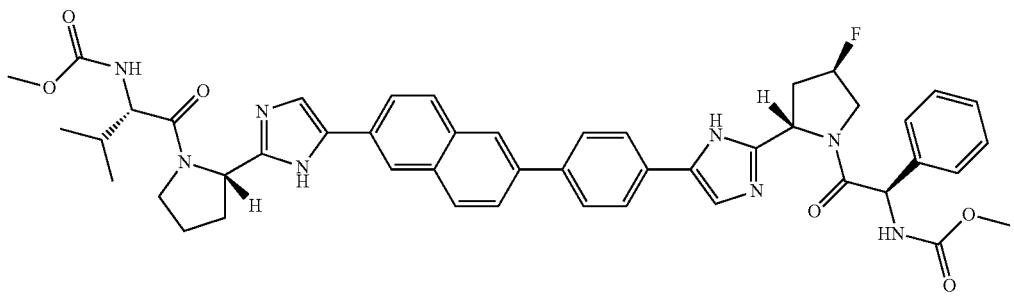

[1-(2-{5-[6-(4-{2-[4-Fluoro-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[4-Fluoro-1-(2-methoxycarbonylamino-2-phenyl-acetyl)- pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[4-Fluoro-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester was prepared following the procedure for [1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, substituting 4-Fluoro-pyrrolidine-1,2-dicarboxylic acid 1-tert-butyl ester for Pyrrolidine-1,2-dicarboxylic acid 1-tert-butyl ester and Methoxycarbonylamino-phenyl-acetic acid for 2-Methoxycarbonylamino-2-phenyl-propionic acid. LCMS-ESI$^+$: calc'd for $C_{47}H_{49}FN_8O_6$: 840.38 (M$^+$); Found: 842.1 (M+H$^+$).

Example FV

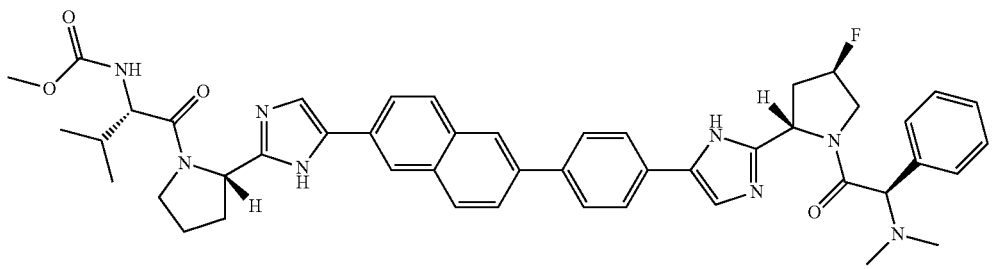 [SMILES: COC(=O)N[C@H](C(=O)N1CCC[C@H]1c1ncc(-c2ccc3cc(-c4ccc(-c5cnc([C@@H]6C[C@@H](F)CN6C(=O)[C@@H](c6ccccc6)N(C)C)[nH]5)cc4)ccc3c2)[nH]1)C(C)C]

[1-(2-{5-[6-(4-{2-[1-(2-Dimethylamino-2-phenyl-acetyl)-4-fluoro-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[1-(2-Dimethylamino-2-phenyl-acetyl)-4-fluoro- pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[1-(2-Dimethylamino-2-phenyl-acetyl)-4-fluoro-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester was prepared following the procedure for [1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, substituting 4-Fluoro-pyrrolidine-1,2-dicarboxylic acid 1-tert-butyl ester for Pyrrolidine-1,2-dicarboxylic acid 1-tert-butyl ester and Dimethylamino-phenyl-acetic acid for 2-Methoxycarbonylamino-2-phenyl-propionic acid. LCMS-ESI$^+$: calc'd for $C_{47}H_{51}FN_8O_4$: 810.40 (M$^+$); Found: 811.4 (M+H$^+$).

Example FW

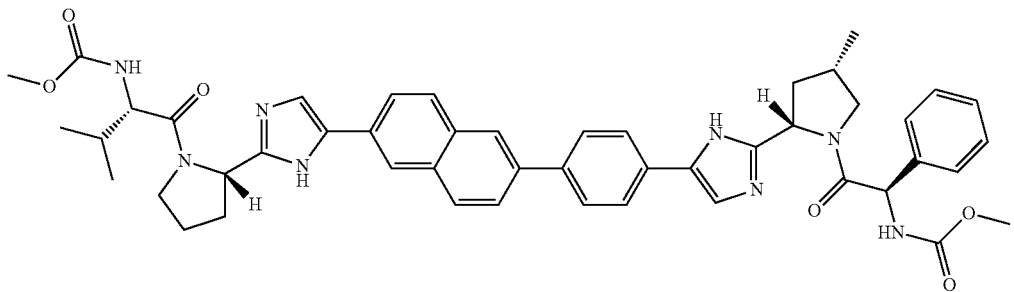

[1-(2-{5-[6-(4-{2-[1-(2-Methoxycarbonylamino-2-phenyl-acetyl)-4-methyl-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[1-(2-Methoxycarbonylamino-2-phenyl-acetyl)-4-methyl-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[1-(2-Methoxycarbonylamino-2-phenyl-acetyl)-4-methyl-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester was prepared following the procedure for [1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, substituting 4-Methyl-pyrrolidine-1,2-dicarboxylic acid 1-tert-butyl ester for Pyrrolidine-1,2-dicarboxylic acid 1-tert-butyl ester and Methoxycarbonylamino-phenyl-acetic acid for 2-Methoxycarbonylamino-2-phenyl-propionic acid. LCMS-ESI$^+$: calc'd for $C_{48}H_{52}N_8O_6$: 836.40 (M$^+$); Found: 837.70 (M+H$^+$).

Example FX

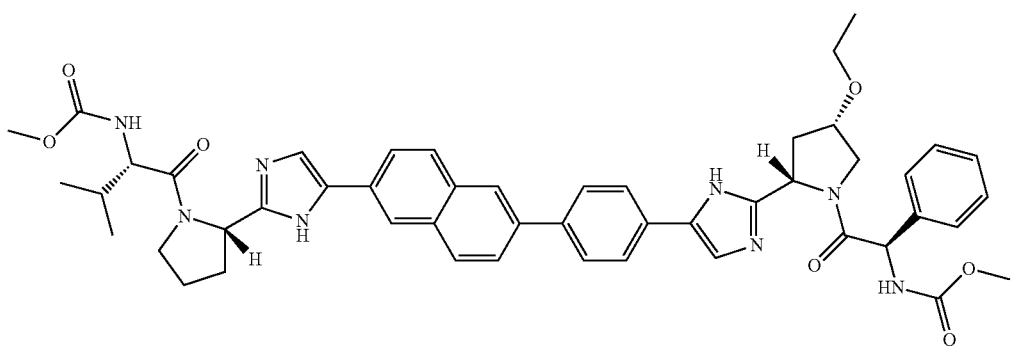

[1-(2-{5-[6-(4-{2-[4-Ethoxy-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[4-Ethoxy-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester. [1-(2-{5-[6-(4-{2-[4-Ethoxy-1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester was prepared following the procedure for [1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, substituting 4-Ethoxy-pyrrolidine-1,2-dicarboxylic acid 1-tert-butyl ester for Pyrrolidine-1,2-dicarboxylic acid 1-tert-butyl ester and Methoxycarbonylamino-phenyl-acetic acid for 2-Methoxycarbonylamino-2-phenyl-propionic acid. LCMS-ESI$^+$: calc'd for $C_{49}H_{54}N_8O_7$: 866.41 (M$^+$); Found: 867.35 (M+H$^+$).

Example FY

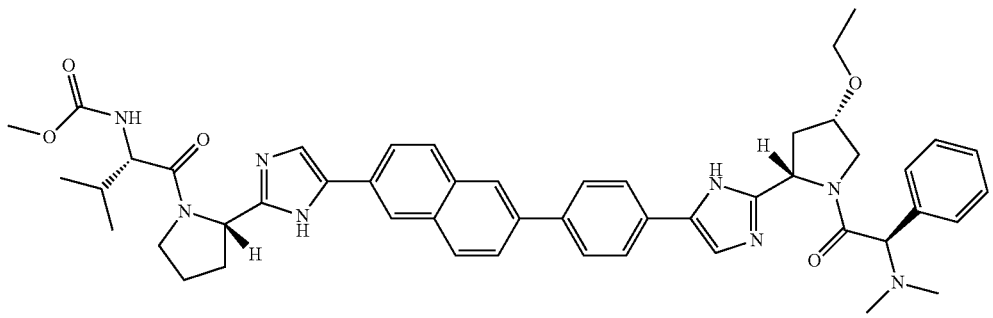 [SMILES: CCO[C@H]1C[C@@H](c2ncc(-c3ccc(-c4ccc5cc(-c6cnc([C@@H]7CCCN7C(=O)[C@@H](NC(=O)OC)C(C)C)[nH]6)ccc5c4)cc3)[nH]2)N(C(=O)[C@@H](c2ccccc2)N(C)C)C1]

[1-(2-{5-[6-(4-{2-[1-(2-Dimethylamino-2-phenyl-acetyl)-4-ethoxy-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[1-(2-Dimethylamino-2-phenyl-acetyl)-4-ethoxy-pyrrolidin-2-yl]-3H-imidazol-4-yl}-phenyl)-naphthalen-2-yl]-1H-imidazol-2-yl}-1-pyrrolidine-1-carbonyl)-2-methyl-propyl]-carbamic acid methyl ester. [1-(2-{5-[6-(4-{2-[1-(2-Dimethylamino-2-phenyl-acetyl)-4-ethoxy-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester was prepared following the procedure for [1-(2-{5-[6-(4-{(2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, substituting 4-Ethoxy-pyrrolidine-1,2-dicarboxylic acid 1-tert-butyl ester for Pyrrolidine-1,2-dicarboxylic acid 1-tert-butyl ester and Dimethylamino-phenyl-acetic acid for 2-Methoxycarbonylamino-2-phenyl-propionic acid. LCMS-ESI$^+$: calc'd for $C_{49}H_{56}N_8O_5$: 836.44 (M$^+$); Found: 837.80 (M+H$^+$).

Example FZ

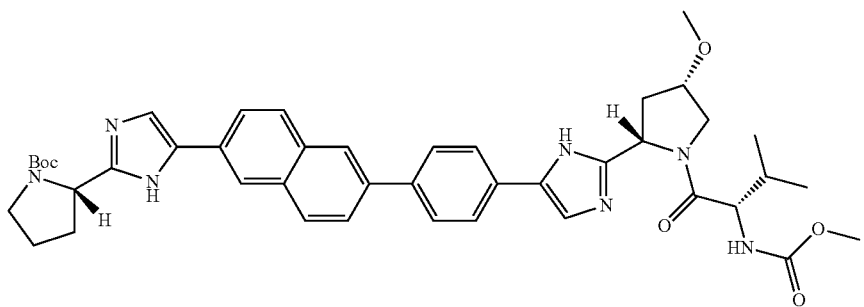 [SMILES: COC(=O)N[C@H](C(=O)N1C[C@@H](OC)C[C@H]1c1ncc(-c2ccc(-c3ccc4cc(-c5cnc([C@@H]6CCCN6C(=O)OC(C)(C)C)[nH]5)ccc4c3)cc2)[nH]1)C(C)C]

2-{5-[6-(4-{2-[4-Methoxy-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester 2-{5-[6-(4-{2-[4-Methoxy-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester. 2-{5-[6-(4-{2-[4-Methoxy-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester was prepared following the procedure for 2-{5-[6-(4-{2-[1-(2-Methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester, substituting 4-Methoxy-pyrrolidine-1,2-dicarboxylic acid 1-tert-butyl ester for Pyrrolidine-1,2-dicarboxylic acid 1-tert-butyl ester.

Example GA

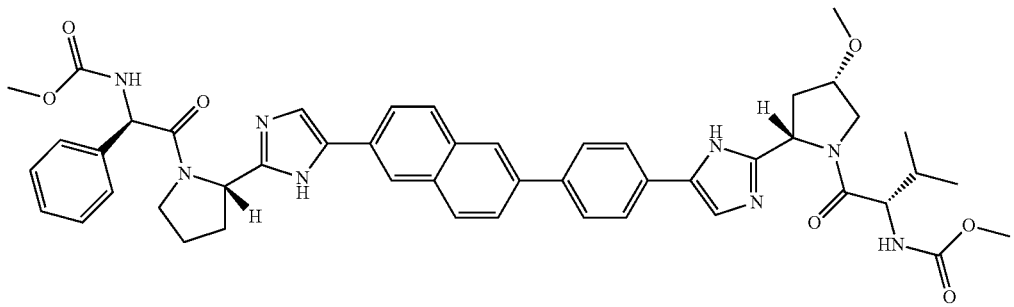

[1-(4-Methoxy-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester

[1-(4-Methoxy-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester. [1-(4-Methoxy-2-{5-[4-(6-{2-[1-(2-methoxycarbonylamino-2-phenyl-acetyl)-pyrrolidin-2-yl]-3H-imidazol-4-yl}-naphthalen-2-yl)-phenyl]-1H-imidazol-2-yl}-pyrrolidine-1-carbonyl)-2-methyl-propyl]-carbamic acid methyl ester was prepared following the procedure for [1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, substituting 2-{5-[6-(4-{2-[4-Methoxy-1-(2-methoxycarbonylamino-3-methyl-butyryl)-pyrrolidin-2-yl]-3H-imidazol-4-yl}-phenyl)-naphthalen-2-yl]-1H-imidazol-2-yl}-pyrrolidine-1-carboxylic acid tert-butyl ester for 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester and Methoxycarbonylamino-phenyl-acetic acid for 2-Methoxycarbonylamino-2-phenyl-propionic acid. LCMS-ESI+: calc'd for $C_{48}H_{52}N_8O_7$: 852.40 (M+); Found: 853.46 (M+H+).

Example GB

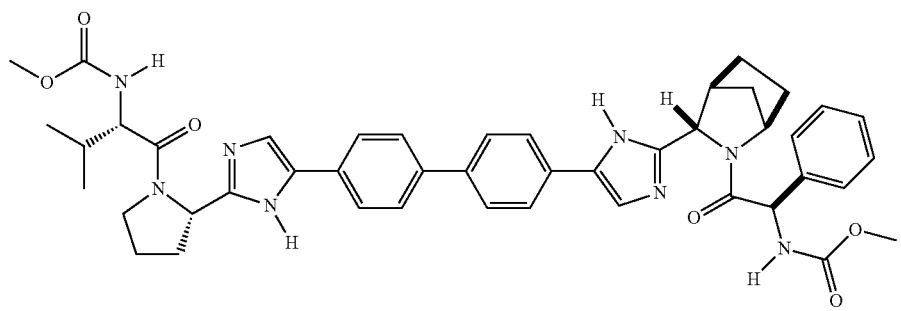

methyl (S)-1-((S)-2-(5-(4'-(2-((1R,3S,4S)-2-((R)-2-(methoxycarbonylamino)-2-phenylacetyl)-2-azabicyclo[2.2.1]heptan-3-yl)-1H-imidazol-5-yl)biphenyl-4-yl)-1H-imidazol-2-yl)pyrrolidin-1-yl)-3-methyl-1-oxobutan-2-ylcarbamate

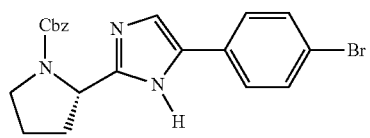

(S)-benzyl 2-(5-(4-bromophenyl)-1H-imidazol-2-yl)pyrrolidine-1-carboxylate

Methyl (S)-1-((S)-2-(5-(4'-(2-((1R,3S,4S)-2-((R)-2-(methoxycarbonylamino)-2-phenylacetyl)-2-azabicyclo[2.2.1]heptan-3-yl)-1H-imidazol-5-yl)biphenyl-4-yl)-1H-imidazol-2-yl)pyrrolidin-1-yl)-3-methyl-1-oxobutan-2-ylcarbamate: The title compound was prepared as described for {2-[4,4-Difluoro-2-(5-{4-[6-(2-{1-[2-methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester, substituting (S)-benzyl 2-(5-(4-bromophenyl)-1H-imidazol-2-yl)pyrrolidine-1-carboxylate for (S)-benzyl 2-(5-(6-bromonaphthalen-2-yl)-1H-imidazol-2-yl)pyrrolidine-1-carboxylate and 2-Aza-bicyclo[2.2.1]heptane-2,3-dicarboxylic acid 2-tert-butyl ester for 4,4-Difluoro-pyrrolidine-1,2-dicarboxylic acid 1-tert-butyl ester. LCMS-ESI$^+$: calculated for $C_{45}H_{51}N_8O_6$: 799.4; observed [M+1]$^+$: 799.4.

Example GC

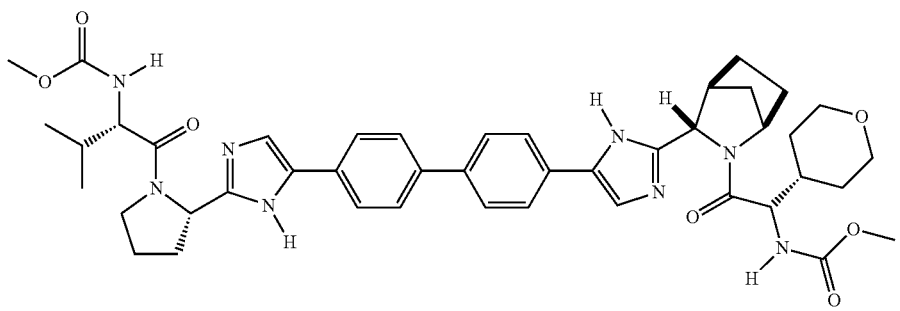

methyl (S)-1-((S)-2-(5-(4'-(2-((1R,3S,4S)-2-((S)-2-(methoxycarbonylamino)-2-(tetrahydro-2H-pyran-4-yl)acetyl)-2-azabicyclo[2.2.1]heptan-3-yl)-1H-imidazol-5-yl)biphenyl-4-yl)-1H-imidazol-2-yl)pyrrolidin-1-yl)-3-methyl-1-oxobutan-2-ylcarbamate

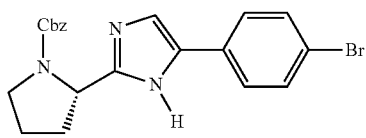

(S)-benzyl 2-(5-(4-bromophenyl)-1H-imidazol-2-yl)pyrrolidine-1-carboxylate

Methyl (S)-1-((S)-2-(5-(4'-(2-((1R,3S,4S)-2-((S)-2-(methoxycarbonylamino)-2-(tetrahydro-2H-pyran-4-yl)acetyl)-2-azabicyclo[2.2.1]heptan-3-yl)-1H-imidazol-5-yl)biphenyl-4-yl)-1H-imidazol-2-yl)pyrrolidin-1-yl)-3-methyl-1-oxobutan-2-ylcarbamate: The title compound was prepared as described for {2-[4,4-Difluoro-2-(5-{4-[6-(2-{1-[2-methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester, substituting (S)-benzyl 2-(5-(4-bromophenyl)-1H-imidazol-2-yl)pyrrolidine-1-carboxylate for (S)-benzyl 2-(5-(6-bromonaphthalen-2-yl)-1H-imidazol-2-yl)pyrrolidine-1-carboxylate, 2-Aza-bicyclo[2.2.1]heptane-2,3-dicarboxylic acid 2-tert-butyl ester for 4,4-Difluoro-pyrrolidine-1,2-dicarboxylic acid 1-tert-butyl ester, and Methoxycarbonylamino-(tetrahydro-pyran-4-yl)-acetic acid for Methoxycarbonylamino-phenyl-acetic acid. LCMS-ESI$^+$: calculated for $C_{44}H_{55}N_8O_7$: 807.4; observed [M+1]$^+$: 807.4.

Example GD

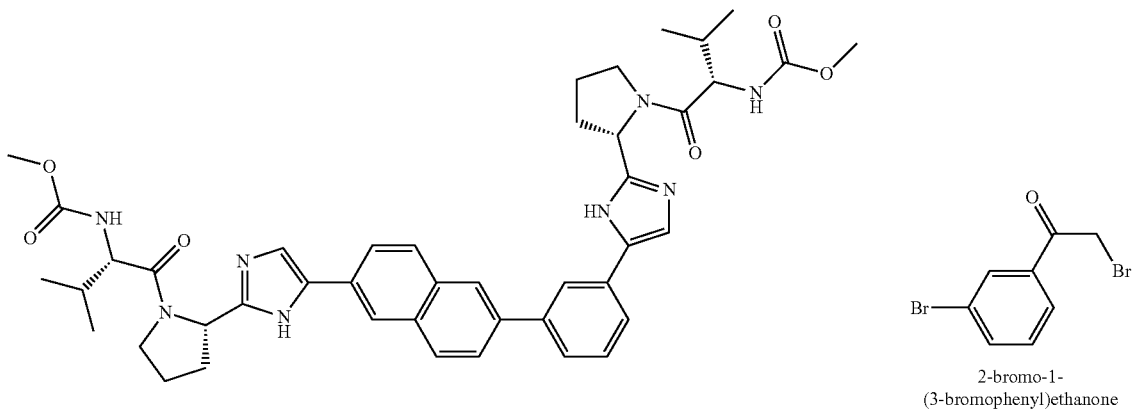

methyl (S)-1-((S)-2-(5-(6-(3-(2-((S)-1-((S)-2-(methoxycarbonylamino)-3-methylbutanoyl)pyrrolidin-2-yl)-1H-imidazol-5-yl)-phenyl)naphthalen-2-yl)-1H-imidazol-2-yl)pyrrolidin-1-yl)-3-methyl-1-oxobutan-2-ylcarbamate 2-bromo-1-(3-bromophenyl)ethanone Methyl (S)-1-((S)-2-(5-(6-(3-(2-((S)-1-((S)-2-(methoxycarbonylamino)-3-methylbutanoyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate: The title compound was prepared as described for [2-(3-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-2-aza-bicyclo[2.2.1]hept-2-yl)-2-oxo-1-(tetrahydro-pyran-4-yl)-ethyl]-carbamic acid methyl ester, substituting 2-bromo-1-(3-bromophenyl)ethanone for 1-(4-Bromo-phenyl)-2-chloro-ethanone, Pyrrolidine-1,2-dicarboxylic acid 1-tert-butyl ester for 2-Aza-bicyclo[2.2.1]heptane-2,3-dicarboxylic acid 2-tert-butyl ester, and (S)-2-(methoxycarbonylamino)-3-methylbutanoic acid for Methoxycarbonylamino-(tetrahydro-pyran-4-yl)-acetic acid.

LCMS-ESI$^+$: calculated for $C_{44}H_{53}N_8O_6$: 789.4; observed [M+1]$^+$: 789.6.

Example GE

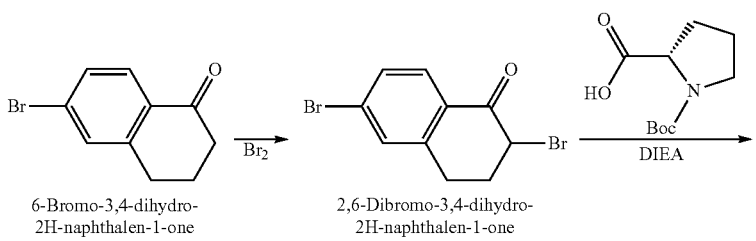

6-Bromo-3,4-dihydro-2H-naphthalen-1-one 2,6-Dibromo-3,4-dihydro-2H-naphthalen-1-one

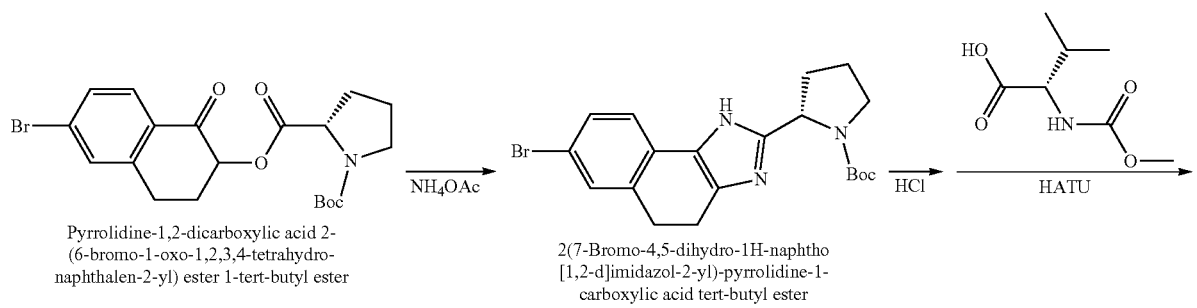

Pyrrolidine-1,2-dicarboxylic acid 2-(6-bromo-1-oxo-1,2,3,4-tetrahydro-naphthalen-2-yl) ester 1-tert-butyl ester 2(7-Bromo-4,5-dihydro-1H-naphtho[1,2-d]imidazol-2-yl)-pyrrolidine-1-carboxylic acid tert-butyl ester 901                                                                                                 902

-continued

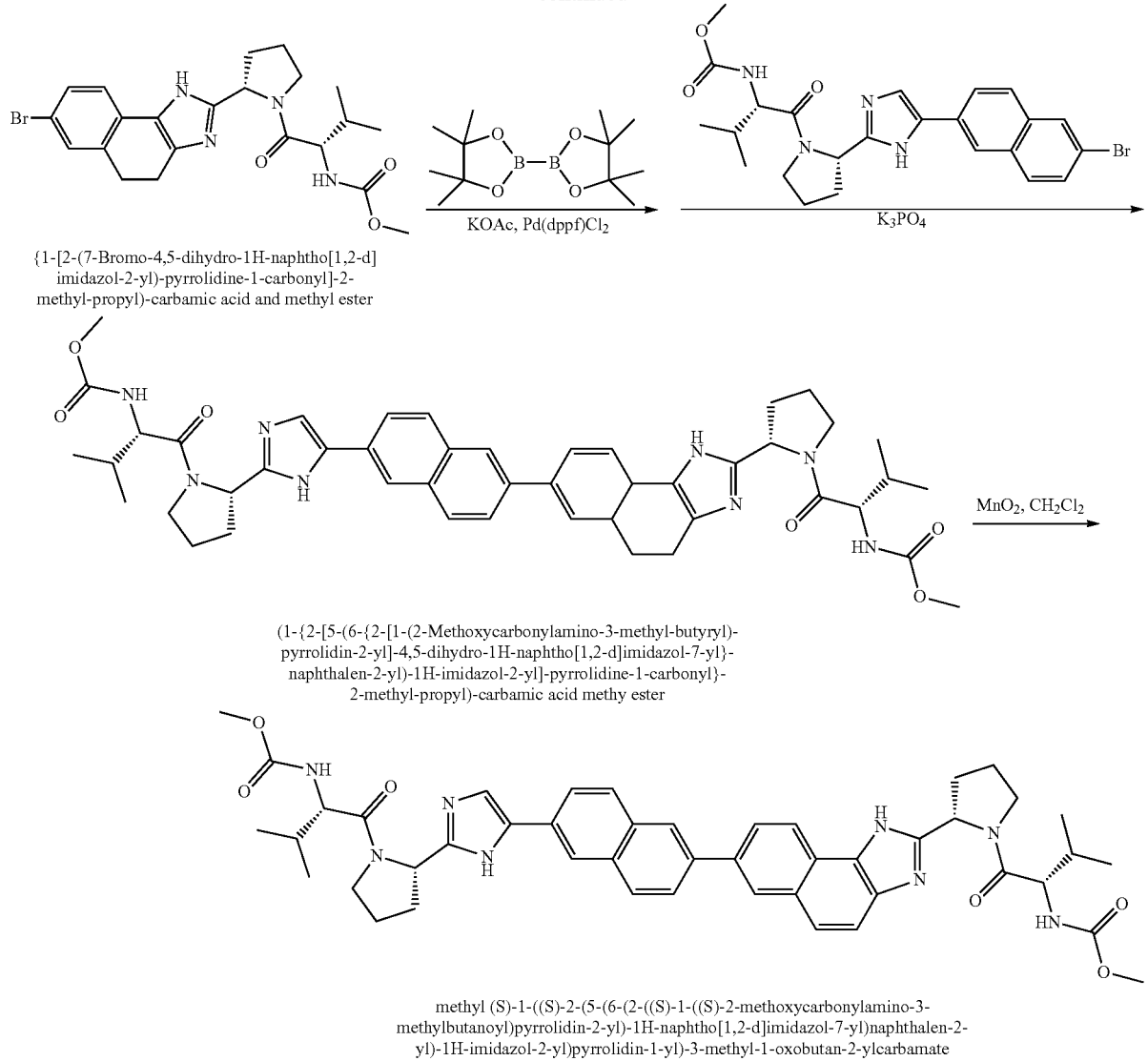

{1-[2-(7-Bromo-4,5-dihydro-1H-naphtho[1,2-d]
imidazol-2-yl)-pyrrolidine-1-carbonyl]-2-
methyl-propyl)-carbamic acid and methyl ester (1-{2-[5-(6-{2-[1-(2-Methoxycarbonylamino-3-methyl-butyryl)-
pyrrolidin-2-yl]-4,5-dihydro-1H-naphtho[1,2-d]imidazol-7-yl}-
naphthalen-2-yl)-1H-imidazol-2-yl]-pyrrolidine-1-carbonyl}-
2-methyl-propyl)-carbamic acid methy ester methyl (S)-1-((S)-2-(5-(6-(2-((S)-1-((S)-2-methoxycarbonylamino-3-
methylbutanoyl)pyrrolidin-2-yl)-1H-naphtho[1,2-d]imidazol-7-yl)naphthalen-2-
yl)-1H-imidazol-2-yl)pyrrolidin-1-yl)-3-methyl-1-oxobutan-2-ylcarbamate 2-6-Dibromo-3,4-dihydro-2H-naphthalen-1-one: 6-Bromo-3,4-dihydro-2H-naphthalen-1-one (2.0 g) was dissolved in ether (80 mL), and Br$_2$ (455 µl) was added at 0° C. over 30 min. After diluting with ether (80 mL), the reaction mixture was washed with 10% Na$_2$SO$_3$, sat. NaHCO$_3$ and brine. After the solvent was removed, the crude material was used for the next step without further purification.

Pyrrolidine-1,2-dicarboxylic acid 2-(6-bromo-1-oxo-1,2,3,4-tetrahydro-naphthalen-2-yl) ester 1-tert-butyl ester: The crude 2-6-dibromo-3,4-dihydro-2H-naphthalen-1-one and pyrrolidine-1,2-dicarboxylic acid 1-tert-butyl ester (3.15 g) were dissolved in MeCN (80 mL), and DIEA (2.55 mL) was added. The mixture was stirred at 65° C. for overnight and diluted with ethyl acetate. The mixture was washed with 1 N HCl, NaHCO$_3$ and brine. After the solvent was removed, the resulting material was subjected to silica gel chromatography using effluent of 10-40% ethyl acetate and hexanes. The fractions containing product were combined and the solvent was removed under reduced pressure to provide pyrrolidine-1,2-dicarboxylic acid 2-(6-bromo-1-oxo-1,2,3,4-tetrahydro-naphthalen-2-yl) ester 1-tert-butyl ester (1.54 g, 40% over 2 steps).

2-(7-Bromo-4,5-dihydro-1H-naphtho[1,2-d]imidazol-2-yl)-pyrrolidine-1-carboxylic acid tert-butyl ester: Pyrrolidine-1,2-dicarboxylic acid 2-(6-bromo-1-oxo-1,2,3,4-tetrahydro-naphthalen-2-yl) ester 1-tert-butyl ester (1.54 g) and ammonium acetate (2.71 g) were suspended in toluene (35 mL). The reaction mixture was stirred at 110° C. for overnight and evaporated under reduced pressure and resulting residue was taken up in ethyl acetate (100 mL). The organic phase was washed with saturated sodium bicarbonate (1×150 mL) and dried over sodium sulfate. After the solvent was removed, the resulting oil was subjected to silica gel chromatography using effluent of 60-90% ethyl acetate and hexanes. The fractions containing product were combined and the solvent was removed under reduced pressure to provide 2-(7-bromo-4,5-dihydro-1H-naphtho[1,2-d]imidazol-2-yl)-pyrrolidine-1-carboxylic acid tert-butyl ester (1.05 g, 71%) as a pale brown solid. MS (ESI) m/z 418.1 [M+H]$^+$.

(1-{2-[5-(6-{2-[1-(2-Methoxycarbonylamino-3-methyl-butyryl)-pyrrolidin-2-yl]-4,5-dihydro-1H-naphtho[1,2-d]imidazol-7-yl}-naphthalen-2-yl)-1H-imidazol-2-yl]-pyrrolidine-1-carbonyl}-2-methyl-propyl)-carbamic acid methyl ester: Title compound was prepared according to the method employed to [1-(6-{5-[6-(4-{2-[1-(2-Methoxycarbonylamino-3-methyl-butyryl)-4-(2-methoxy-ethoxy)-pyrrolidin-2-yl]-3H-imidazol-4-yl}-phenyl)-naphthalen-2-yl]-1H-imidazol-2-yl}-5-aza-spiro[2.4]heptane-5-carbonyl)-2-methyl-propyl]-carbamic acid methyl ester: MS (ESI) m/z 815.5 [M+H]⁺.

Methyl (S)-1-((S)-2-(5-(6-(2-((S)-1-((S)-2-methoxycarbonylamino-3-methylbutanoyl)pyrrolidin-2-yl)-1H-naphtho[1,2-d]imidazol-7-yl)naphthalen-2-yl)-1H-imidazol-2-yl)pyrrolidin-1-yl)-3-methyl-1-oxobutan-2-ylcarbamate: To (1-{2-[5-(6-{2-[1-(2-Methoxycarbonylamino-3-methyl-butyryl)-pyrrolidin-2-yl]-4,5-dihydro-1H-naphtho[1,2-d]imidazol-7-yl}-naphthalen-2-yl)-1H-imidazol-2-yl]-pyrrolidine-1-carbonyl}-2-methyl-propyl)-carbamic acid methyl ester (13.0 mg, 0.016 mmol) in CH$_2$Cl$_2$ (1 mL) was added MnO$_2$ (2.8 mg, 0.032 mmol). The reaction was stirred overnight then additional MnO$_2$ (1.4 mg, 0.016 mmol) was added. After stirring for 3 hours, the reaction was filtered through a Whatman 0.45 mM PTFE filter. The filtrate was concentrated then purified by preparative reverse phase HPLC (Gemini, 10 to 45% ACN/H$_2$O+0.1% TFA) to yield methyl (S)-1-((S)-2-(5-(6-(2-((S)-1-((S)-2-methoxycarbonylamino-3-methylbutanoyl)pyrrolidin-2-yl)-1H-naphtho[1,2-d]imidazol-7-yl)naphthalen-2-yl)-1H-imidazol-2-yl)pyrrolidin-1-yl)-3-methyl-1-oxobutan-2-ylcarbamate (6.3 mg, 48%). LCMS-ESI⁺: calculated for C$_{46}$H$_{53}$N$_8$O$_6$: 813.4; observed [M+1]⁺: 813.4.

Example GF

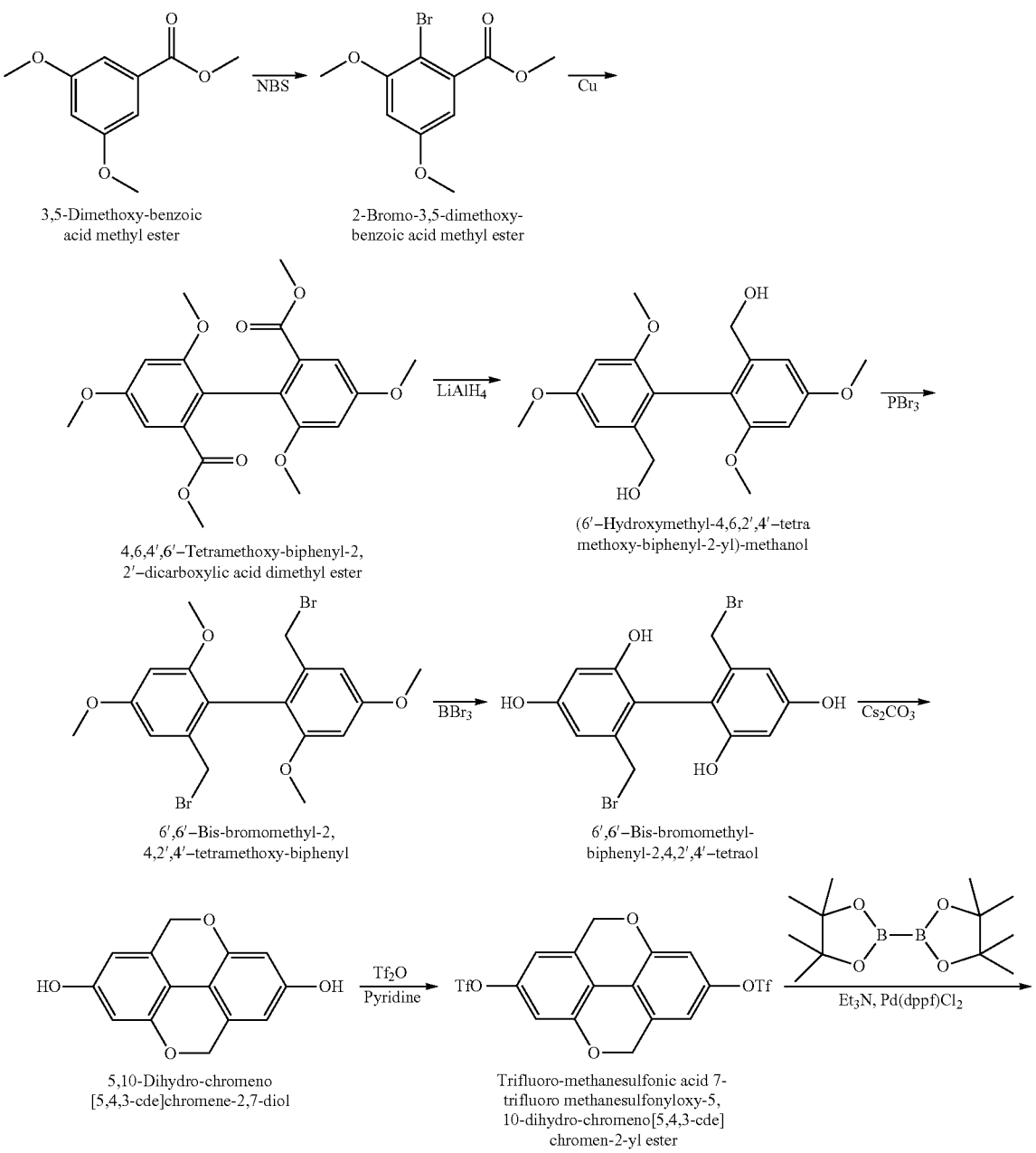

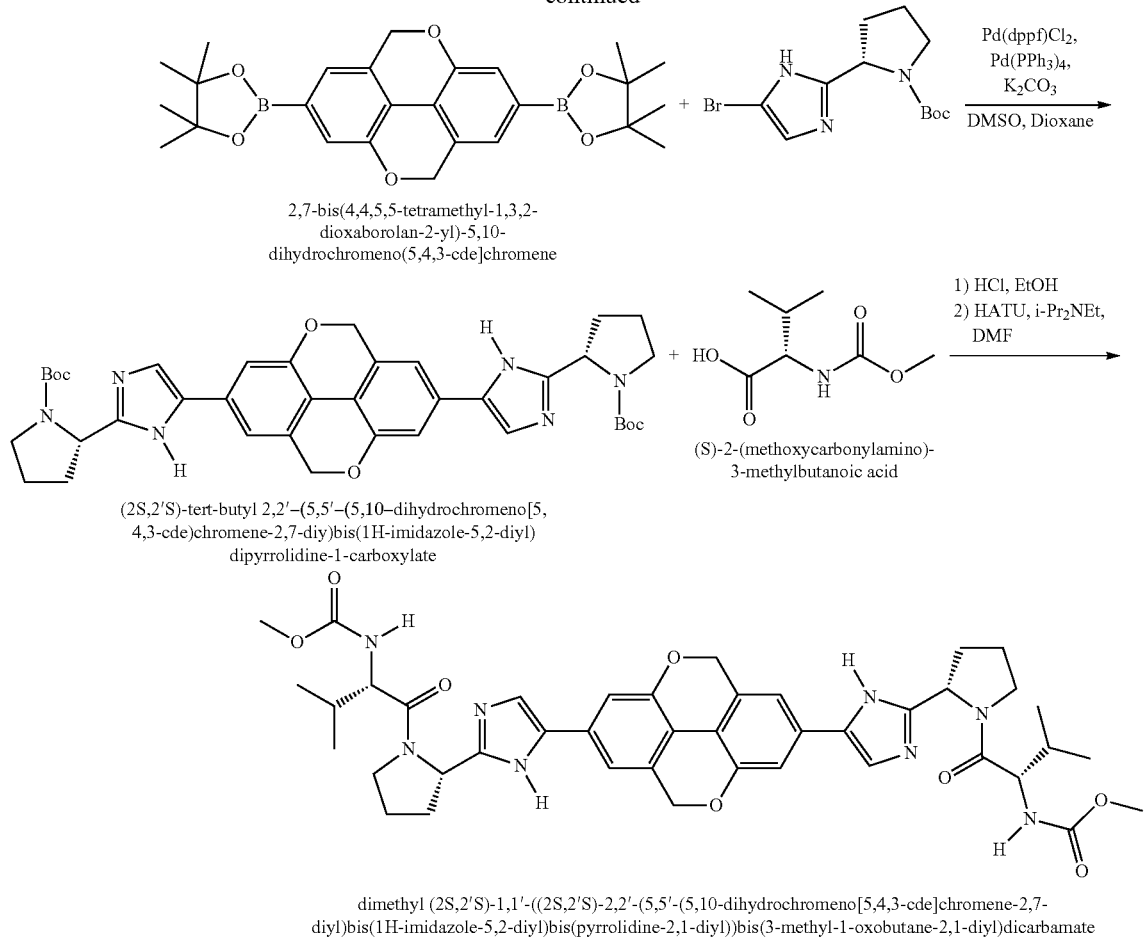

2-Bromo-3,5-dimethoxy-benzoic acid methyl ester: 3,5-Dimethoxy-benzoic acid methyl ester (4.0 g) was dissolved in MeCN (28 mL), and NBS (4.4 g) was added at 0° C. After stirring at room temperature for 3 hours, saturated $Na_2SO_3$ (15 mL) was added. The mixture was evaporated under vacuum and extracted with ether (1×, 500 mL). After the solvent was removed, the crude material was subjected to silica gel chromatography using effluent of 10-40% ethyl acetate and hexanes. The fractions containing product were combined and the solvent was removed under reduced pressure to provide 2-bromo-3,5-dimethoxy-benzoic acid methyl ester (5.2 g, 93%) as a clear oil.

4,6,4',6'-Tetramethoxy-biphenyl-2,2'-dicarboxylic acid dimethyl ester: 2-Bromo-3,5-dimethoxy-benzoic acid methyl ester (5.2 g) was dissolved in DMF (16 mL), and Cu powder (2.4 g) was added. After stirring at 150° C. for 3 days, the mixture was filtered and evaporated under vacuum. The crude material was subjected to silica gel chromatography using effluent of 30-60% ethyl acetate and hexanes. The fractions containing product were combined and the solvent was removed under reduced pressure to provide 4,6,4',6'-tetramethoxy-biphenyl-2,2'-dicarboxylic acid dimethyl ester (2.5 g, 68%) as a clear oil.

(6'-Hydroxymethyl-4,6,2',4'-tetramethoxy-biphenyl-2-yl)-methanol: 4,6,4',6'-tetramethoxy-biphenyl-2,2'-dicarboxylic acid dimethyl ester (2.5 g) was dissolved in THF (96 mL), and 1M $LiAlH_4$ in THF (9.6 mL) was added. After stirring at room temperature for overnight, the mixture was quenched with water and 2N HCl (24 mL) was added. The mixture was evaporated under vacuum and partitioned with DCM (300 mL) and water (200 mL). The organic layer was dried over $Na_2SO_4$ and crystallized with DCM to provide (6'-hydroxymethyl-4,6,2',4'-tetramethoxy-biphenyl-2-yl)-methanol (1.7 g, 77%) as a pale blue white triclinic crystals.

6,6'-Bis-bromomethyl-2,4,2',4'-tetramethoxy-biphenyl: (6'-hydroxymethyl-4,6,2',4'-tetramethoxy-biphenyl-2-yl)-methanol (779 mg) was dissolved in DCM (5.8 mL), and $PBr_3$ (527 uL) was slowly added at 0° C. After stirring at 0° C. for 30 min. and at room temperature for 1 hour, $H_2O$ (40 mL) was added. The mixture was extracted with ether (1×, 50 mL). After the solvent was removed, the crude material was subjected to silica gel chromatography using effluent of 10-40% ethyl acetate and hexanes. The fractions containing product were combined and the solvent was removed under reduced pressure to provide 6,6'-bis-bromomethyl-2,4,2',4'-tetramethoxy-biphenyl (700 mg, 65%) as a thick oil.

6,6'-Bis-bromomethyl-biphenyl-2,4,2',4'-tetraol: 6,6'-bis-bromomethyl-2,4,2',4'-tetramethoxy-biphenyl (685 mg) was dissolved in DCM (3.0 mL), and 1M $BBr_3$ in DCM (16.4 mL) was slowly added. After stirring for 2 days, the mixture was poured on to ice and concentrated. The crude material was used for the next step without a further purification.

5-10-Dihydro-chromeno[5,4,3-cde]chromene-2,7-diol: The crude 6,6'-bis-bromomethyl-biphenyl-2,4,2',4'-tetraol was dissolved in DMF (30 mL) and $Cs_2CO_3$ (1.9 g) was added. After stirring at room temperature for 1 hour, the mixture was partitioned with 1 N HCl (100 mL) and ethyl acetate (100 mL), and extracted with ethyl acetate (3×, 100 mL). After the solvent was removed, the crude material was subjected to silica gel chromatography using effluent of 10-15% methanol and DCM. The fractions containing product were combined and the solvent was removed under reduced pressure to provide 5-10-dihydro-chromeno[5,4,3-cde]chromene-2,7-diol (301 mg, 84%) as a white solid.

Trifluoro-methanesulfonic acid 7-trifluoromethanesulfonyloxy-5,10-dihydro-chromeno[5,4,3-cde]chromen-2-yl ester: 5-10-Dihydro-chromeno[5,4,3-cde]chromene-2,7-diol (290 mg) was dissolved in DCM (12 mL), and Tf$_2$O (1.2 mL) and pyridine (969 uL) were added. After stirring at room temperature for overnight, the mixture was partitioned with 2 N HCl (50 mL) and DCM (50 mL), and washed with 2 N HCl (2×50 mL) and saturated sodium bicarbonate (1×50 mL). After the solvent was removed, the resulting oil was subjected to silica gel chromatography using effluent of 0-30% ethyl acetate and hexanes. The fractions containing product were combined and the solvent was removed under reduced pressure to provide trifluoro-methanesulfonic acid 7-trifluoromethanesulfonyloxy-5,10-dihydro-chromeno[5,4,3-cde]chromen-2-yl ester (472 mg, 78%) as an off-white solid.

2,7-bis(4,4,5,5-tetramethyl-1,3,2-dioxaborolan-2-yl)-5,10-dihydrochromeno[5,4,3-cde]chromene:

A solution of trifluoro-methanesulfonic acid 7-trifluoromethanesulfonyloxy-5,10-dihydro-chromeno[5,4,3-cde]chromen-2-yl ester (5.18 g, 10.2 mmol), bis(pinacolato)diboron (10.39 g, 41 mmol) and triethylamine (7.11 mL, 51 mmol) 1,4-dioxanes (100 mL) was degassed with argon for fifteen minutes. To this solution was added PdCl$_2$(dppf) (1.49 g, 2.04 mmol) and the reaction was heated to 90° C. overnight. The mixture was cooled to room temperature and concentrated. The crude solid was suspended in MeOH and stirred for 30 minutes, filtered and thoroughly rinsed with methanol to yield 2,7-bis(4,4,5,5-tetramethyl-1,3,2-dioxaborolan-2-yl)-5,10-dihydrochromeno[5,4,3-cde]chromene (3.21 g, 68%) as a yellow solid.

(2S,2'S)-tert-butyl 2,2'-(5,5'-(5,10-dihydrochromeno[5,4,3-cde]chromene-2,7-diyl)bis(1H-imidazole-5,2-diyl))dipyrrolidine-1-carboxylate A mixture of 2,7-bis(4,4,5,5-tetramethyl-1,3,2-dioxaborolan-2-yl)-5,10-dihydrochromeno[5,4,3-cde]chromene (1.50 g, 3.25 mmol), (S)-tert-butyl 2-(5-bromo-1H-imidazol-2-yl)pyrrolidine-1-carboxylate (3.60 g, 11.4 mmol), tetrakis(triphenylphosphine)palladium(0) (751 mg, 0.65 mmol), PdCl$_2$(dppf) (476 mg, 0.65 mmol), 2M aqueous potassium carbonate (9.8 mL, 19.2 mmol), DMSO (33 mL) and 1,4-dioxanes (33 ml mL) was degassed with argon for 15 minutes. The reaction was then heated to 110° C. for 2 hours. Upon completion, the reaction was cooled to room temperature then poured into a saturated NaHCO$_3$ solution. The solution was extracted with EtOAc 2× then the organic phase was washed with brine. The resulting crude material was purified by flash column chromatography (0 to 10% MeOH/EtOAc) to afford (2S,2'S)-tert-butyl 2,2'-(5,5'-(5,10-dihydrochromeno[5,4,3-cde]chromene-2,7-diyl)bis(1H-imidazole-5,2-diyl))dipyrrolidine-1-carboxylate (1.58 mg, 68%).

Dimethyl (2S,2'S)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(3-methyl-1-oxobutane-2,1-diyl)dicarbamate: A solution of (2S,2'S)-tert-butyl 2,2'-(5,5'-(5,10-dihydrochromeno[5,4,3-cde]chromene-2,7-diyl)bis(1H-imidazole-5,2-diyl))dipyrrolidine-1-carboxylate (90 mg, 0.13 mmol), concentrated HCl (1.0 mL) and ethanol (2 mL) was heated to 60° C. for one hour. The reaction was concentrated and placed on the high-vac overnight. The crude amine was dissolved in dimethylformamide (2.2 mL). To this solution was added (S)-2-(methoxycarbonylamino)-3-methylbutanoic acid (58 mg, 0.33 mmol), HATU (104 mg, 0.27 mmol) and 4-methylmorpholine (0.075 mL, 0.65 mmol). The reaction was stirred at room temperature for two hours. Upon completion, the reaction was quenched with formic acid then purified by preparative reverse phase HPLC (Gemini, 10 to 45% ACN/H$_2$O+0.1% TFA) to yield dimethyl (2S,2'S)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(3-methyl-1-oxobutane-2,1-diyl)dicarbamate (64 mg, 62%). LCMS-ESI$^+$: calculated for $C_{42}H_{51}N_8O_8$: 795.4; observed [M+1]$^+$: 795.8.

Example GF-2

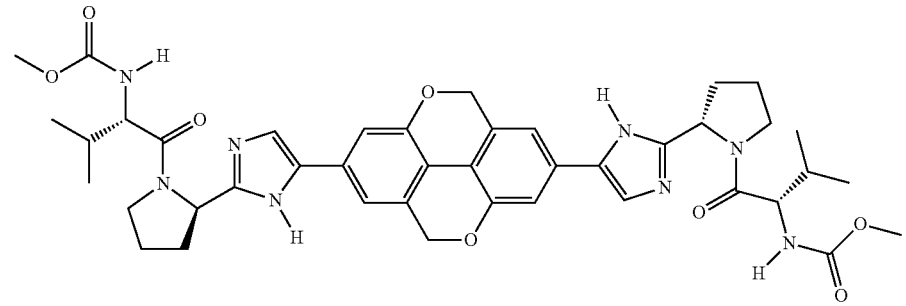

dimethyl (2S,2'S)-1,1'-((2R,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(3-methyl-1-oxobutane-2,1-diyl)dicarbamate Dimethyl (2S,2'S)-1,1'-((2R,2'S)-2,2'-(5,5'-(5,10-dihydrochromeno[5,4,3-cde]chromene-2,7-diyl)bis(1H-imidazole-5,2- diyl))bis(pyrrolidine-2,1diyl))bis(3-methyl-1-oxobutane-2,1-diyl)dicarbamate: The title compound was prepared as in dimethyl (2S,2'S)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(3-methyl-1-oxobutane-2,1-diyl)dicarbamate, using racemic tert-butyl 2-(5-bromo-1H-imidazol-2-yl)pyrrolidine-1-carboxylate instead of (S)-tert-butyl 2-(5-bromo-1H-imidazol-2-yl)pyrrolidine-1-carboxylate. The diastereomeric products were separated by preparative reverse phase HPLC (Gemini, 10 to 45% ACN/H$_2$O+0.1% TFA). LCMS-ESI$^+$: calculated for C$_{42}$H$_{51}$N$_8$O$_8$: 795.4; observed [M+1]$^+$: 795.8.

Dimethyl (2 S,2'S)-1,1'-((2R,2'R)-2,2'-(5,5'-(5,10-dihydrochromeno[5,4,3-cde]chromene-2,7-diyl)bis(1H-imidazole-5,2-diyl))bis(pyrrolidine-2,1-diyl))bis(3-methyl-1-oxobutane-2,1-diyl)dicarbamate: The title compound was prepared as in dimethyl (2S,2'S)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(3-methyl-1-oxobutane-2,1-diyl)dicarbamate, using racemic tert-butyl 2-(5-bromo-1H-imidazol-2-yl)pyrrolidine-1-carboxylate instead of (S)-tert-butyl 2-(5-bromo-1H-imidazol-2-yl)pyrrolidine-1-carboxylate. The diastereomeric products were separated by preparative reverse phase HPLC (Gemini, 10 to 45% ACN/H$_2$O+0.1% TFA). LCMS-ESI$^+$: calculated for C$_{42}$H$_{51}$N$_8$O$_8$: 795.4; observed [M+1]$^+$: 795.8.

Example GG

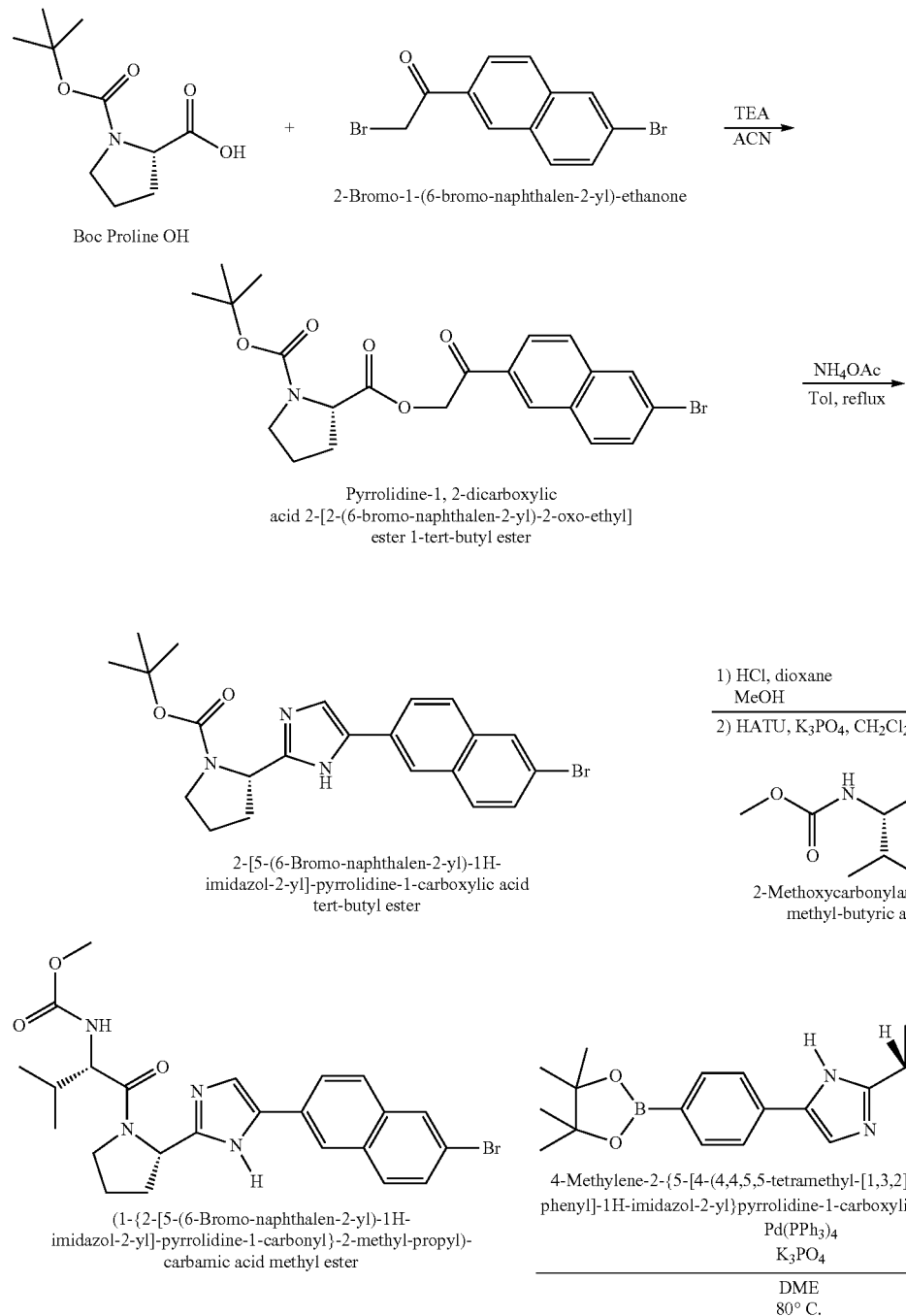

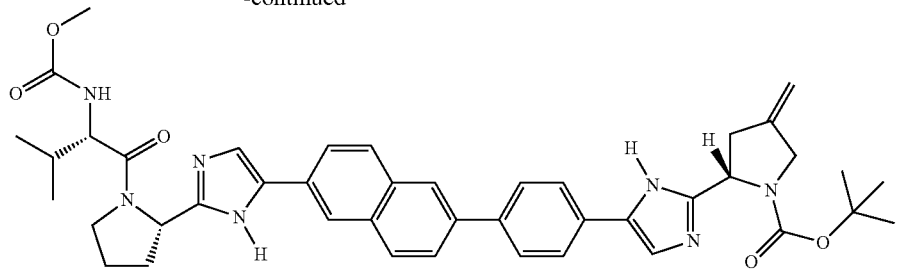

2-{5-[4-(6-{2-[1-(2-Methoxycarbonylamino-3-methyl-butyryl)-pyrrolidin-2-yl]-3H-
imidazol-4-yl}-naphthalen-2-yl}-phenyl]-1H-imidazol-2-yl}-4-methylene-pyrrolidine-1-
carboxylic acid tert-butyl ester Pyrrolidine-1,2-dicarboxylic acid 2-[2-(6-bromo-naphthalen-2-yl)-2-oxo-ethyl]ester 1-tert-butyl ester: 2-Bromo-1-(6-bromo-naphthalen-2-yl)-ethanone (20.01g, 61 mmol) and Boc Proline OH (12.51g, 58.1 mmol) were suspended in acetonitrile (290 mL). Triethylamine (8.9 mL, 63.9 mmol) was added, and the solution was allowed to stir at room temperature overnight. Upon completion, the reaction was concentrated in vacuo and purified by normal phase chromatography (0-40% Ethyl acetate in Hexanes) to give Pyrrolidine-1,2-dicarboxylic acid 2-[2-(6-bromo-naphthalen-2-yl)-2-oxo-ethyl](assumed 61 mmol).

2-[5-(6-Bromo-naphthalen-2-yl)-1H-imidazol-2-yl]-pyrrolidine-1-carboxylic acid tert-butyl ester: Pyrrolidine-1,2-dicarboxylic acid 2-[2-(6-bromo-naphthalen-2-yl)-2-oxo-ethyl] (61 mmol) and ammonium acetate (610 mmol) were suspended in toluene (300 mL) and heated to reflux for 18 hours. Solid precipitated during the course of the reaction and it was filtered off and washed with ethyl acetate to give 2-[5-(6-Bromo-naphthalen-2-yl)-1H-imidazol-2-yl]-pyrrolidine-1-carboxylic acid tert-butyl ester (13.3g, 50% over two steps) as a tan solid. LCMS-ESI$^+$: calc'd for $C_{22}H_{24}BrN_3O_2$: 441.11 and 443.10 (M$^+$); Found: 443.93 (M+H$^+$).

(1-{2-[5-(6-Bromo-naphthalen-2-yl)-1H-imidazol-2-yl]-pyrrolidine-1-carbonyl}-2-methyl-propyl)-carbamic acid methyl ester: To 2-[5-(6-Bromo-naphthalen-2-yl)-1H-imidazol-2-yl]-pyrrolidine-1-carboxylic acid tert-butyl ester (6.4g, 14.4 mmol) was added HCl in dioxane (36 mL, 144 mmol). The suspension was allowed to stir at room temperature for three hours. Upon completion by LCMS, the reaction was concentrated to dryness and the crude product (assumed 14.4 mmol) was suspended in dichloromethane. 2-Methoxycarbonylamino-3-methyl-butyric acid (3.8g, 21.7 mmol) and solid potassium phosphate (28.94 mmol) were added to the slurry. HATU (6.88g, 18.08 mL) was added and the reaction was stirred at room temperature for 18 hours. Upon completion, the crude reaction was filtered through a sintered glass funnel. The supernate was concentrated in vacuo and purified by normal phase silica gel chromatography (20-70% Ethyl acetate (with 10% MeOH) in Hexanes) to give (1-{2-[5-(6-Bromo-naphthalen-2-yl)-1H-imidazol-2-yl]-pyrrolidine-1-carbonyl}-2-methyl-propyl)-carbamic acid methyl ester (7.14g, >90% yield) as a thick oil. LCMS-ESI$^+$: calc'd for $C_{24}H_{27}BrN_4O_3$: 498.13 (M$^+$); Found: 499.96 (M+H$^+$).

4-Methylene-2-{5-[4-(4,4,5,5-tetramethyl-[1,3,2]dioxaborolan-2-yl)-phenyl]-1H-imidazol-2-yl}-pyrrolidine-1-carboxylic acid tert-butyl ester: This compound was made using the same procedure used to make [2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester using 4-Methylene-pyrrolidine-1,2-dicarboxylic acid 1-tert-butyl ester. LCMS-ESI$^+$: calc'd for $C_{25}H_{34}BN_3O_4$: 451.26 (M$^+$); Found: 452.33 (M+H$^+$).

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-m ethylene-pyrrolidine-1-carboxylic acid tert-butyl ester: 4-Methylene-2-{5-[4-(4,4,5,5-tetramethyl-[1,3,2]dioxaborolan-2-yl)-phenyl]-1H-imidazol-2-yl}-pyrrolidine-1-3carboxylic acid tert-butyl ester (0.20g, 0.443 mmol), (1-{2-[5-(6-Bromo-naphthalen-2-yl)-1H-imidazol-2-yl]-pyrrolidine-1-carbonyl}-2-methyl-propyl)-carbamic acid methyl ester (0.170g, 0.341 mmol) and potassium phosphate (2M, 0.51 mL, 1.023 mmol) were suspended in 1,2-dimethoxyethane (3.4 mL) and sparged with argon gas for 30 minutes. Palladium tetrakis triphenylphosphine (0.039g, 0.034 mmol) was added and the reaction mixture was capped and heated to 80° C. with a preheated external oil bath and a JChem temperature controller. Upon completion, the reaction was filtered through diatomaceous earth, washed with ethyl acetate, diluted in ethyl acetate, washed with bicarb. The organic phases were dried with sodium sulfate, filtered and concentrated. The crude product was purified by reverse phase HPLC (10-40% acetonitrile: water; 0.1% formic acid modifier), and lyophilized giving 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester (0.032g, 12% yield) as a white solid. LCMS-ESI$^+$: calc'd for $C_{43}H_{49}N_7O_5$: 743.38 (M$^+$); Found: 744.31 (M+H$^+$).

Example GH

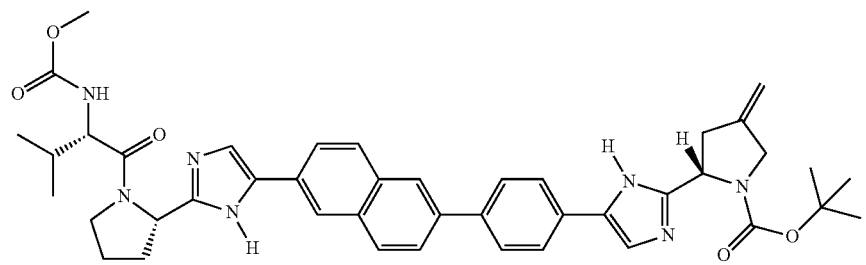

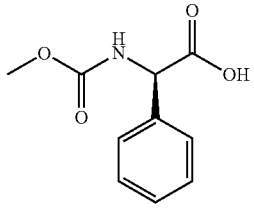

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester Methyoxycarbonylamino-phenyl-acetic acid

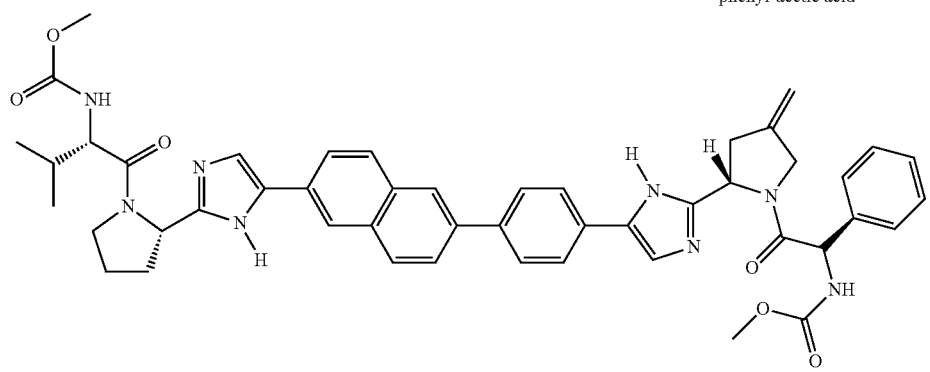

[1-(2-{5-[6-(4-{2-[1-(2-Methoxycarbonylamino-2-phenyl-acetyl)-4-methylene-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[1-(2-Methoxycarbonylamino-2-phenyl-acetyl)-4-methylene-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: This compound was made using the same procedure used to make [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester (0.032g, 0.043 mmol) to give [1-(2-{5-[6-(4-{2-[1-(2-Methoxycarbonylamino-2-phenyl-acetyl)-4-methylene-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.002g, 5.6% yield) was a white solid. LCMS-ESI$^+$: calc'd for $C_{48}H_{50}N_8O_6$: 834.39 (M$^+$); Found: 835.80 (M+H$^+$).

Example GI

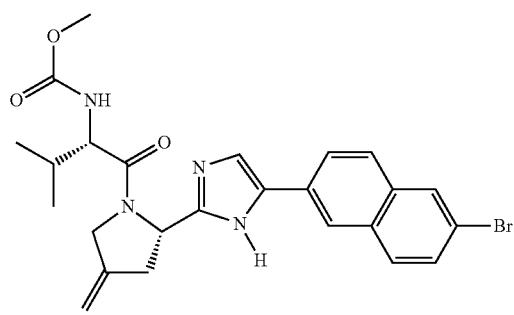

(1-{2-[5-(6-Bromo-naphthalen-2-yl)-1H-imidazol-2-yl]-4-methylene-pyrrolidine-1-carbonyl}-2-methyl-propyl)-carbamic acid methyl ester

+

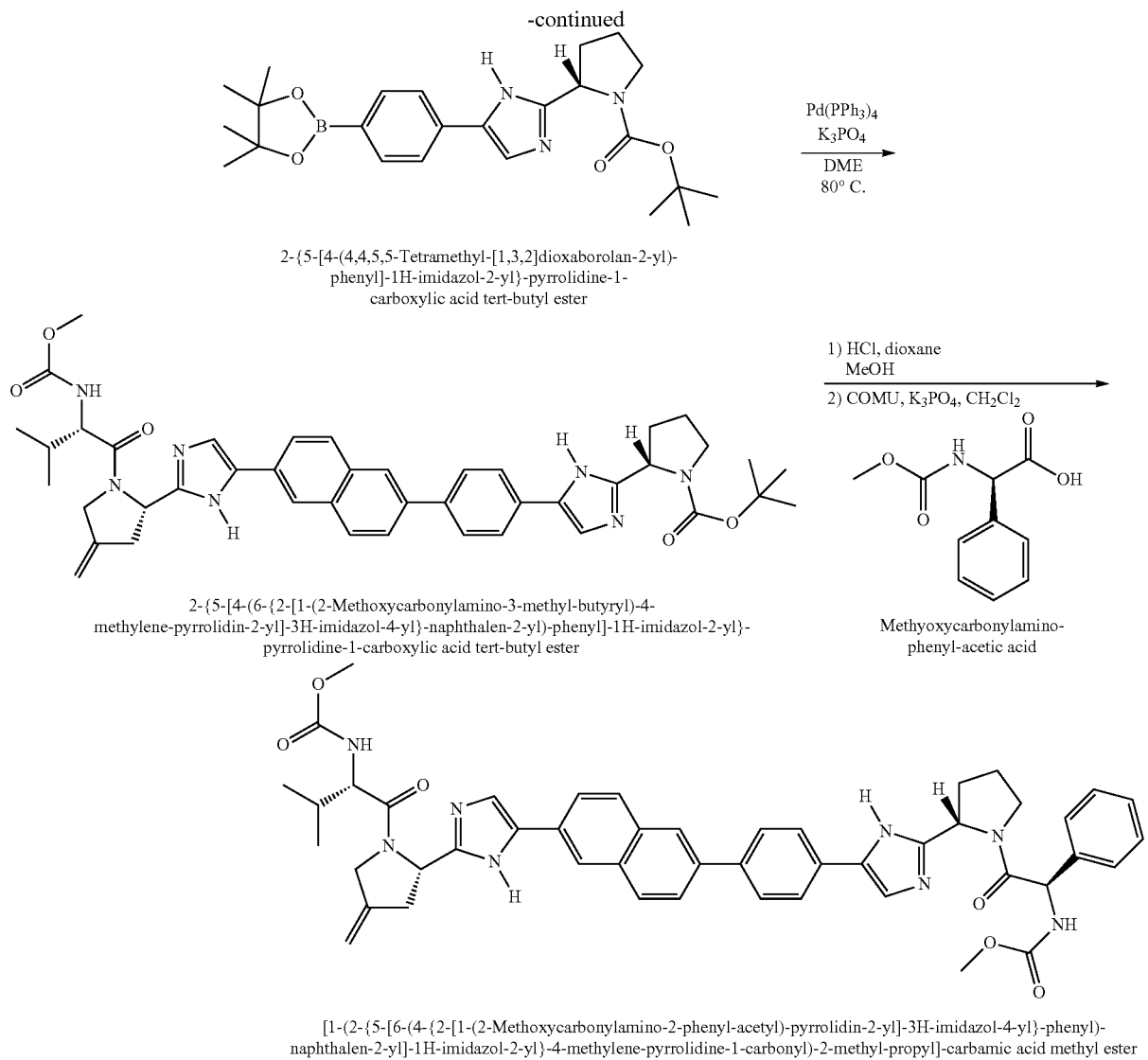

(1-{2-[5-(6-Bromo-naphthalen-2-yl)-1H-imidazol-2-yl]-4-methylene-pyrrolidine-1-carbonyl}-2-methyl-propyl)-carbamic acid methyl ester: This compound was made using the same procedure used to make 2-[5-(6-Bromo-naphthalen-2-yl)-1H-imidazol-2-yl]-pyrrolidine-1-carboxylic acid tert-butyl ester using 4-Methylene-pyrrolidine-1,2-dicarboxylic acid 1-tert-butyl ester (3.81g, 16.76 mmol) to give (1-{2-[5-(6-Bromo-naphthalen-2-yl)-1H-imidazol-2-yl]-4-methylene-pyrrolidine-1-carbonyl}-2-methyl-propyl)-carbamic acid methyl ester (5.76g, 83% yield). LCMS-ESI⁺: calc'd for $C_{25}H_{27}BrN_4O_3$: 510.13 (M⁺); Found: 511.63 (M+H⁺).

2-{5-[4-(6-{2-[1-(2-Methoxycarbonylamino-3-methyl-butyryl)-4-methylene-pyrrolidin-2-yl]-3H-imidazol-4-yl}-naphthalen-2-yl)-phenyl]-1H-imidazol-2-yl}-pyrrolidine-1-carboxylic acid tert-butyl ester: This compound was synthesized using the same method used to make 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester using (1-{2-[5-(6-Bromo-naphthalen-2-yl)-1H-imidazol-2-yl]-4-methylene-pyrrolidine-1-carbo- nyl}-2-methyl-propyl)-carbamic acid methyl ester (0.200g, 0.391 mmol) and 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester (0.223g, 0.508 mmol) to give 2-{5-[4-(6-{2-[1-(2-Methoxycarbonylamino-3-methyl-butyryl)-4-methylene-pyrrolidin-2-yl]-3H-imidazol-4-yl}-naphthalen-2-yl)-phenyl]-1H-imidazol-2-yl}-pyrrolidine-1-carboxylic acid tert-butyl ester (0.040g, 0.054 mmol). LCMS-ESI⁺: calc'd for $C_{43}H_{49}N_7O_5$: 743.38 (M⁺); Found: 744.73 (M+H⁺).

[1-(2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-4-methylene-pyrrolidine-1-carbonyl)-2-methyl-propyl]-carbamic acid methyl ester: This compound was made using the same procedure used to make [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, giving [1-(2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-4-methylene-pyrrolidine-1-carbonyl)-2-methyl-propyl]-carbamic acid methyl ester (0.005g, 2% yield) as a white solid.

LCMS-ESI⁺: calc'd for $C_{48}H_{50}N_8O_6$: 834.39 (M⁺); Found: 835.32 (M+H⁺).

Example GJ

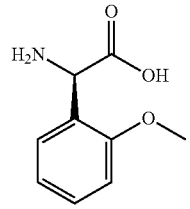

Amino-(2-methoxy-phenyl)-acetic acid

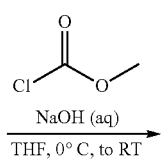

NaOH (aq)
THF, 0° C, to RT

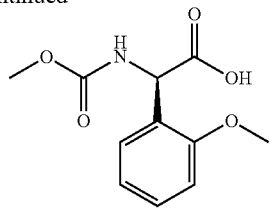

Methoxycarbonylamino-(2-methoxy-phenyl)-acetic acid

Methoxycarbonylamino-(2-methoxy-phenyl)-acetic acid: Methoxycarbonylamino-(2-methoxy-phenyl)-acetic acid was prepared using the procedure used to prepare (2-Fluoro-phenyl)-methoxycarbonylamino-acetic acid using Amino-(2-methoxy-phenyl)-acetic acid. LCMS-ESI⁺: calc'd for $C_{11}H_{13}NO_5$: 239.08 (M⁺); Found: 239.94 (M+H⁺).

Example GK

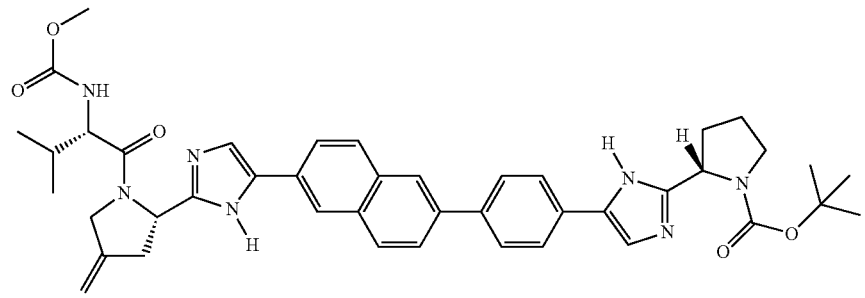

2-{5-[4-(6-{2-[1-(2-Methoxycarbonylamino-3-methyl-butyryl)-4-methylene-pyrrolidin-2-yl]-3H-imidazol-4-yl}-naphthalen-2-yl)-phenyl]-1H-imidazol-2-yl}-pyrrolidine-1-carboxylic acid tert-butyl ester 1) HCl, dioxane
   MeOH
2) COMU, K₃PO₄, CH₂Cl₂

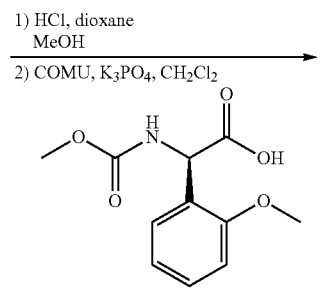

Methyoxycarbonylamino-(2-methoxy-phenyl)-acetic acid

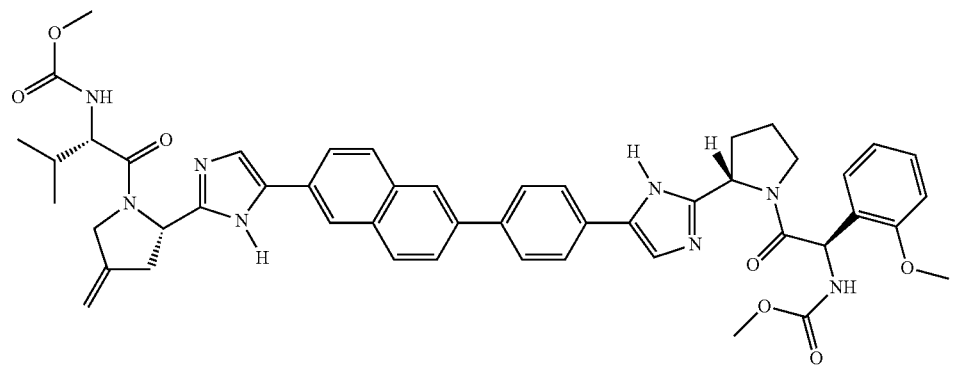

{1-[2-(5-{6-[4-(2-{1-[2-Methoxycarbonylamino-2-(2-methoxy-phenyl)-acetyl]-pyrrolidin-2-yl}-3H-imidazol-4-yl)-phenyl]-naphthalen-2-yl}-1H-imidazol-2-yl)-4-methylene-pyrrolidine-1-carbonyl]-2-methyl-propyl}-carbamic acid methyl ester {1-[2-(5-{6-[4-(2-{1-[2-Methoxycarbonylamino-2-(2-methoxy-phenyl)-acetyl]-pyrrolidin-2-yl}-3H-imidazol-4-yl)-phenyl]-naphthalen-2-yl}-1H-imidazol-2-yl)-4-methylene-pyrrolidine-1-carbonyl]-2-methyl-propyl}-carbamic acid methyl ester: This compound was synthesized using the same method used to synthesize [1-(2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-4-methylene-pyrrolidine-1-carbonyl)-2-methyl-propyl]-carbamic acid methyl ester using Methoxycarbonylamino-(2-methoxy-phenyl)-acetic acid (0.020g, 0.082 mmol) giving {1-[2-(5-{6-[4-(2-{1-[2-Methoxycarbonylamino-2-(2-methoxy-phenyl)-acetyl]-pyrrolidin-2-yl}-3H-imidazol-4-yl)-phenyl]-naphthalen-2-yl}-1H-imidazol-2-yl)-4-methylene-pyrrolidine-1-carbonyl]-2-methyl-propyl}-carbamic acid methyl ester (0.011g, 23% yield) as a white solid. LCMS-ESI$^+$: calc'd for $C_{49}H_{52}N_8O_7$: 864.40 (M$^+$); Found: 865.35 (M+H$^+$).

Example GL

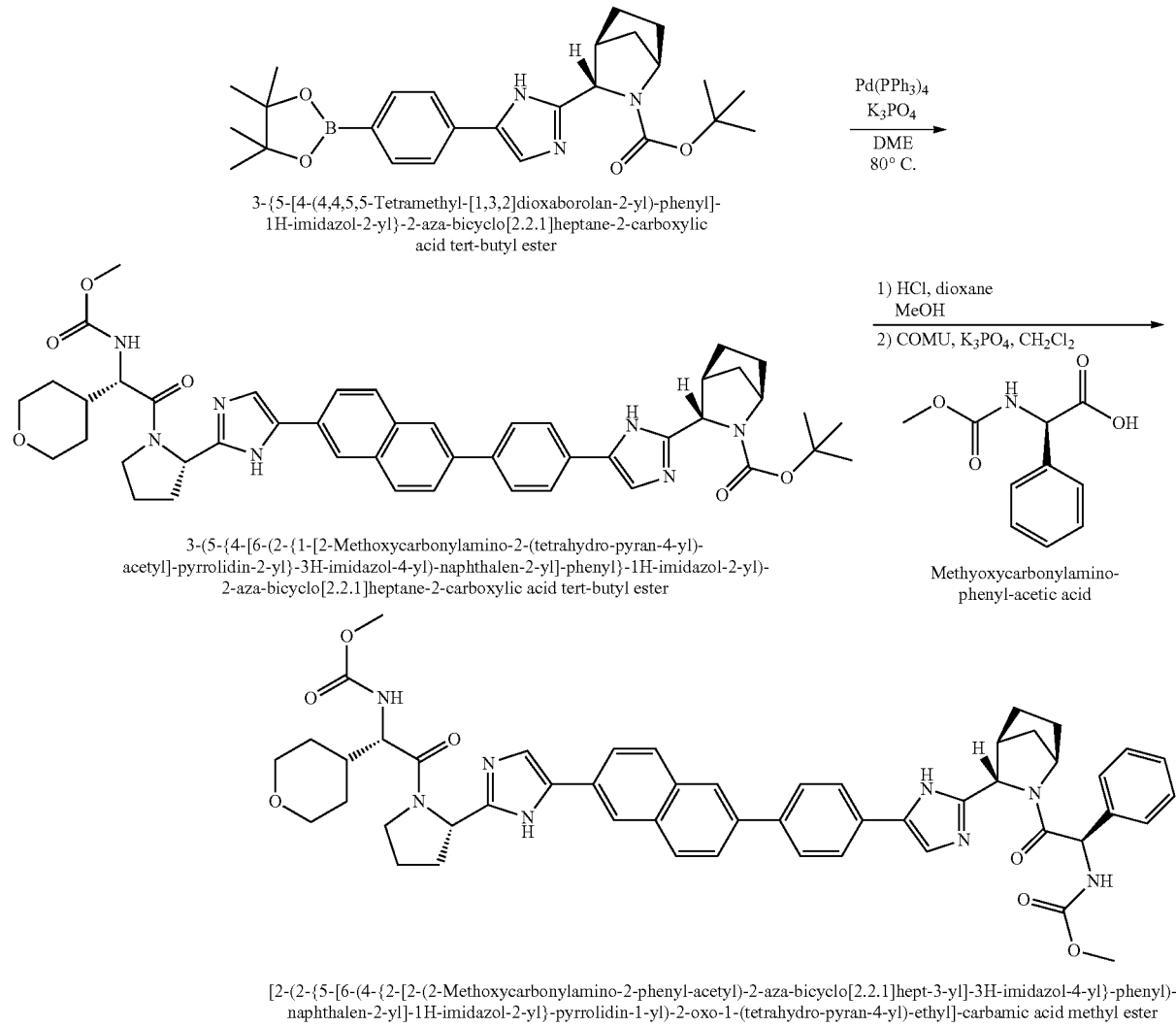

[2-{2-[5-(6-Bromo-naphthalen-2-yl)-1H-imidazol-2-yl]-pyrrolidin-1-yl}-2-oxo-1-(tetrahydro-pyran-4-yl)-ethyl]-carbamic acid methyl ester: This compound was synthesized using the same procedure used to synthesize (1-{2-[5-(6-Bromo-naphthalen-2-yl)-1H-imidazol-2-yl]-pyrrolidine-1-carbonyl)}-2-methyl-propyl)-carbamic acid methyl ester from 2-[5-(6-Bromo-naphthalen-2-yl)-1H-imidazol-2-yl]-pyrrolidine-1-carboxylic acid tert-butyl ester (0.469g, 1.13 mmol) using Methoxycarbonylamino-(tetrahydro-pyran-4-yl)-acetic acid (0.295 g, 1.356 mmol). [2-{2-[5-(6-Bromo-naphthalen-2-yl)-1H-imidazol-2-yl]-pyrrolidin-1-yl}-2-oxo-1-(tetrahydro-pyran-4-yl)-ethyl]-carbamic acid methyl ester (0.264g, 43% yield). LCMS-ESI$^+$: calc'd for $C_{26}H_{29}BrN_4O_4$: 540.14 (M$^+$); Found: 542.08 (M+H$^+$).

3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester: This compound was synthesized using the same procedure as [2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester using 2-Aza-bicyclo[2.2.1]heptane-2,3-dicarboxylic acid 2-tert-butyl ester. LCMS-ESI$^+$: calc'd for $C_{26}H_{36}BN_3O_4$: 465.28 (M$^+$); Found: 466.41 (M+H$^+$).

3-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-2-aza-bicyclo[2.2.1]heptane-2-carboxylic acid tert-butyl ester: This compound was synthesized using the same procedure used to make 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester using [2-{2-[5-(6-Bromo-naphthalen-2-yl)-1H-imidazol-2-yl]-pyrrolidin-1-yl}-2-oxo-1-(tetrahydro-pyran-4-yl)-ethyl]-carbamic acid methyl ester (0.150g, 0.277 mmol) and 3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester (0.155g, 0.332 mmol) to give 3-(5-{4-[6-(2-{I-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-2-aza-bicyclo[2.2.1]heptane-2-carboxylic acid tert-butyl ester (0.106g, 48% yield). LCMS-ESI$^+$: calc'd for $C_{46}H_{53}FN_7O_6$: 799.41 (M$^+$); Found: 800.85 (M+H$^+$).

[2-(2-{5-[6-(4-{2-[2-(2-Methoxycarbonylamino-2-phenyl-acetyl)-2-aza-bicyclo[2.2.1]hept-3-yl]-3H-imidazol-4-yl}-phenyl)-naphthalen-2-yl]-1H-imidazol-2-yl}-pyrrolidin-1-yl)-2-oxo-1-(tetrahydro-pyran-4-yl)-ethyl]-carbamic acid methyl ester: This compound was synthesized using the same procedure used to make [1-(2-{5-[6-(4-{2-[1-(2-Methoxycarbonylamino-2-phenyl-acetyl)-4-methylene-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester, giving the title compound (0.070g, 59% yield) as a white solid. LCMS-ESI$^+$: calc'd for $C_{51}H_{54}N_8O_7$: 890.41 (M$^+$); Found: 891.47 (M+H$^+$).

Example GM

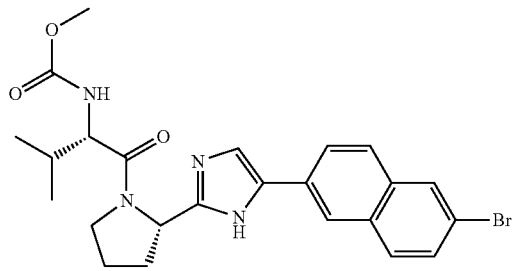

(1-{2-[5-(6-Bromo-naphthalen-2-yl)-1H-imidazol-2-yl]-pyrrolidine-1-carbonyl}-2-methyl-propyl)-carbamic acid methyl ester

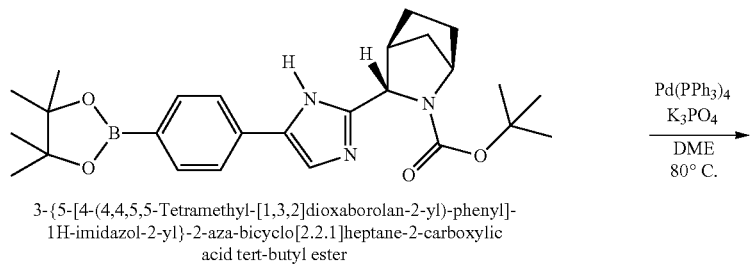

3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester -continued

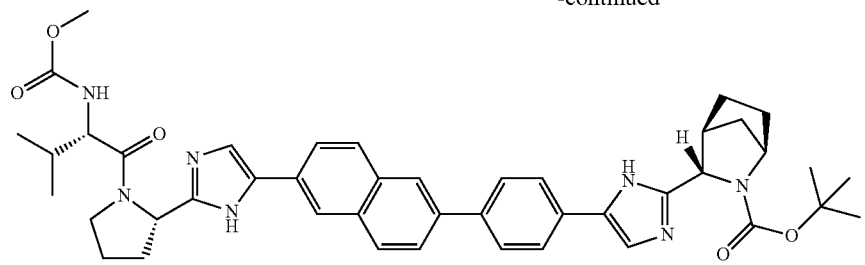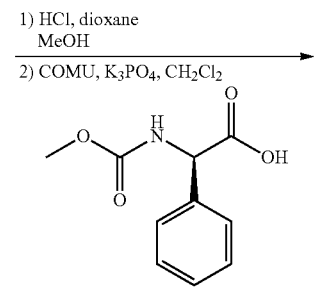

3-{5-[4-(6-{2-[1-(2-Methoxycarbonylamino-3-methyl-butyryl)-pyrrolidin-2-yl]-
3H-imidazol-4-yl}-naphthalen-2-yl)-phenyl]-1H-imidazol-2-yl}-
2-aza-bicyclo[2.2.1]heptane-2-carboxylic acid tert-butyl ester Methyoxycarbonylamino-
phenyl-acetic acid

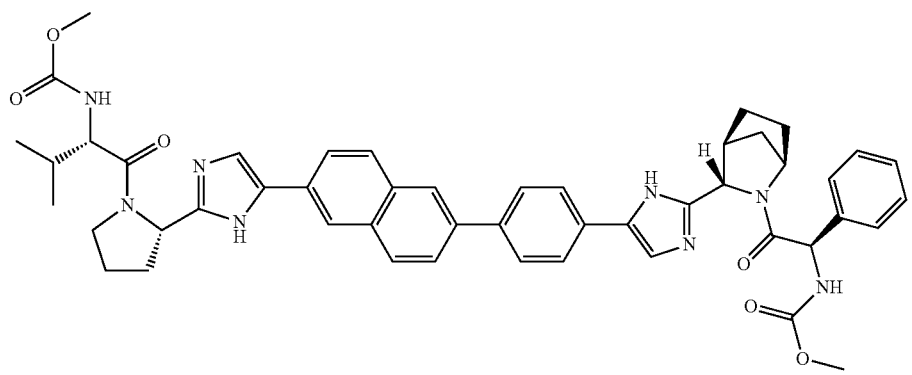

[1-(2-{5-[6-(4-{2-[2-(2-Methoxycarbonylamino-2-phenyl-acetyl)-2-aza-bicyclo[2.2.1]hept-3-yl]-3H-imidazol-4-yl}-phenyl)-
naphthalen-2-yl]-1H-imidazol-2-yl}-pyrrolidine-1-carbonyl)-2-methyl-propyl]-carbamic acid methyl ester 3-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-2-aza-bicyclo[2.2.1]heptane-2-carboxylic acid tert-butyl ester: This compound was synthesized using the procedure used to synthesize 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester using (1-{2-[5-(6-Bromo-naphthalen-2-yl)-1H-imidazol-2-yl]-pyrrolidin-1-carbonyl}-2-methyl-propyl)-carbamic acid methyl ester (0.200g, 0.400 mmol) and 3-{5-[4-(4,4,5,5-Tetramethyl-[1,3,2]dioxaborolan-2-yl)-phenyl]-11H-imidazol-2-yl}-2-aza-bicyclo[2.2.1]heptane-2-carboxylic acid tert-butyl ester (0.224g, 0.48 mmol) giving 3-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-2-aza-bicyclo[2.2.1]heptane-2-carboxylic acid tert-butyl ester (0.192g, 63% yield). LCMS-ESI$^+$: calc'd for $C_{44}H_{51}N_7O_5$: 757.40 (M$^+$); Found: 758.78 (M+H$^+$).

[1-(2-{5-[6-(4-{2-[2-(2-Methoxycarbonylamino-2-phenyl-acetyl)-2-aza-bicyclo[2.2.1]hept-3-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: This compound was synthesized using the procedure used to synthesize [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using Methoxycarbonylamino-phenyl-acetic acid (0.079g, 0.380 mmol) giving the title compound (0.100g, 46.6% yield) as a white solid. LCMS-ESI$^+$: calc'd for $C_{49}H_{52}N_8O_6$: 848.40 (M$^+$); Found: 849.50 (M+H$^+$).

Example GN

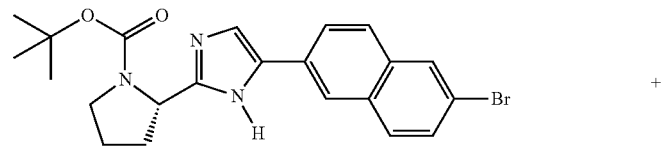

2-[5-(6-Bromo-naphthalen-2-yl)-1H-imidazol-2-yl]-
pyrrolidine-1-carboxylic acid tert-butyl ester

+

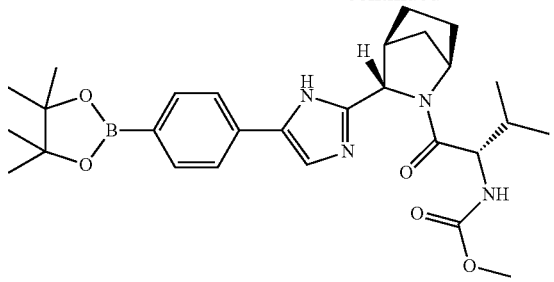

[2-Methyl-1-(3-{5-[4-(4,4,5,5-tetramethyl-[1,3,2]
dioxaborolan-2-yl)-phenyl]-1H-imidazol-2-yl}-2-aza-
bicyclo[2.2.1]heptane-2-carbonyl)-propyl]-carbamic acid methyl ester

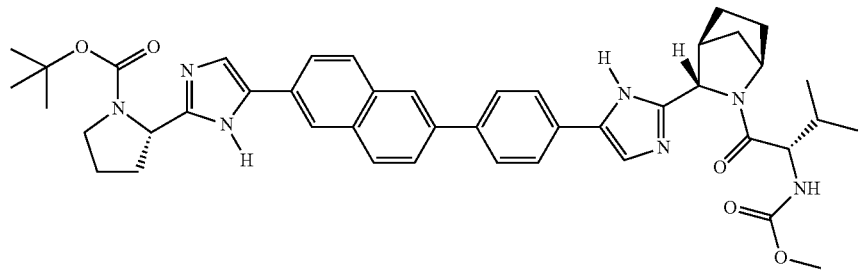

2-{5-[6-(4-{2-[2-(2-Methoxycarbonylamino-3-methyl-butyryl)-2-
aza-bicyclo[2.2.1]hept-3-yl]-3H-imidazol-4-yl}-phenyl)-naphthalen-2-yl]-1H-
imidazol-2-yl]-pyrrolidine-1-carboxylic acid tert-butyl ester Methyoxycarbonylamino-
phenyl-acetic acid

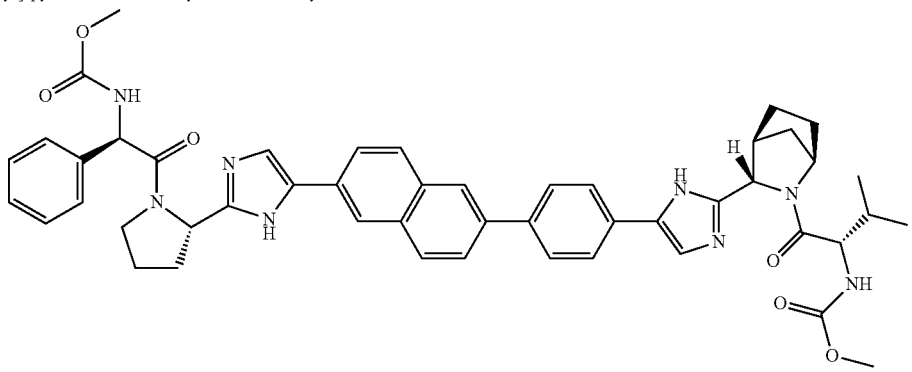

[1-(3-{5-[4-(6-{2-[1-(2-Methoxycarbonylamino-2-phenyl-acetyl)-pyrrolidin-2-yl]-3H-
imidazol-4-yl}-naphthalen-2-yl)-phenyl]-1H-imidazol-2-yl}-2-aza-bicyclo
[2.2.1]heptane-2-carbonyl)2-methyl-propyl]-carbamic acid methyl ester

[2-Methyl-1-(3-{5-[4-(4,4,5,5-tetramethyl-[1,3,2]dioxaborolan-2-yl)-phenyl]-1H-imidazol-2-yl}-2-aza-bicyclo[2.2.1]heptane-2-carbonyl)-propyl]-carbamic acid methyl ester: This compound was synthesized using the procedure used to make [2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester using 2-Aza-bicyclo[2.2.1]heptane-2,3-dicarboxylic acid 2-tert-butyl ester. LCMS-ESI$^+$: calc'd for $C_{28}H_{39}BN_4O_5$: 522.30 (M$^+$); Found: 523.31 (M+H$^+$).

2-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-pyrrolidine-1-carboxylic acid tert-butyl ester: This compound was synthesized using the procedure used to make 2-(5-[4-(6-{2-[1-(2-Methoxycarbonylamino-3-methyl-butyryl)-pyrrolidin-2-yl]-3H-imidazol-4-naphthalen-2-yl)-phenyl]-1H-imidazol-2-yl}-4-methylene-pyrrolidine-1-carboxylic acid tert-butyl ester using 2-[5-(6-Bromo-naphthalen-2-yl)-1H-imidazol-2-yl]-pyrrolidine-1-carboxylic acid tert-butyl ester (0.200g, 0.452 mmol) and [2-Methyl-1-(3-{5-[4-(4,4,5,5-tetramethyl-[1,3,2]dioxaborolan-2-yl)-phenyl]-1H-imidazol-2-yl}-2-aza-bicyclo[2.2.1]heptane-2-carbonyl)-propyl]-carbamic acid methyl ester (0.283g, 0.543 mmol) to give 2-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-pyrrolidine-1-carboxylic acid tert-butyl ester (0.242g, 71% yield). LCMS-ESI$^+$: calc'd for $C_{44}H_{51}N_7O_5$: 757.40 (M$^+$); Found: 758.50 (M+H$^+$).

[1-(3-{5-[4-(6-{2-[1-(2-Methoxycarbonylamino-2-phenyl-acetyl)-pyrrolidin-2-yl]-3H-imidazol-4-yl}-naphthalen-2-yl)-phenyl]-1H-imidazol-2-yl}-2-aza-bicyclo[2.2.1]heptane-2-carbonyl)-2-methyl-propyl]-carbamic acid methyl ester: This compound was synthesized using the procedure used to make [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using Methoxycarbonylamino-phenyl-acetic acid (0.100g, 0.479 mmol) to give the title compound (0.124g, 46% yield). LCMS-ESI$^+$: calc'd for $C_{49}H_{52}N_8O_6$: 848.40 (M$^+$); Found: 849.97 (M+H$^+$).

Example GO

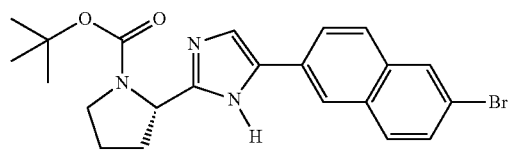

2-[5-(6-Bromo-naphthalen-2-yl)-1H-imidazol-2-yl]-
pyrrolidine-1-carboxylic acid tert-butyl ester

+

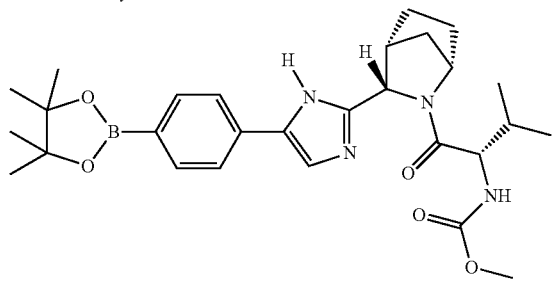 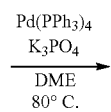

Pd(PPh₃)₄
K₃PO₄
―――――
DME
80° C.

[2-Methyl-1-(3-{5-[4-(4,4,5,5-tetramethyl-[1,3,2]
dioxaborolan-2-yl)-phenyl]-1H-imidazol-2-yl}-2-aza-
bicyclo[2.2.1]heptane-2-carbonyl)-propyl]-carbamic acid methyl ester

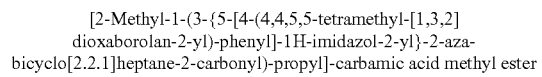

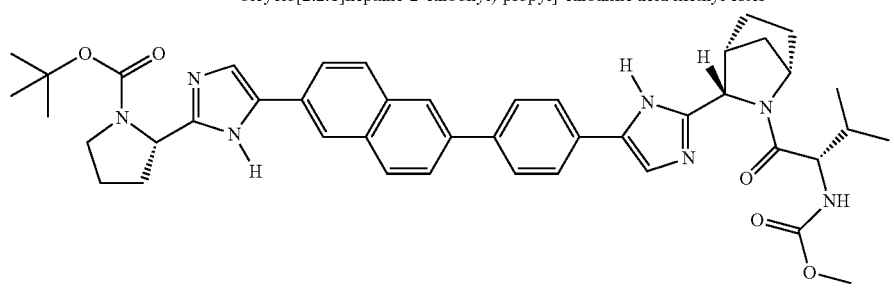

1) HCl, dioxane
MeOH
――――――――――→
2) HATU, NMM, CH₂Cl₂

2-{5-[6-(4-{2-[2-(2-Methoxycarbonylamino-3-methyl-butyryl)-2-aza-bicyclo[2.2.1]hept-3-yl]-3H-imidazol-4-yl}-
phenyl)-naphthalen-2-yl]-1H-imidazol-2-yl}-pyrrolidine-1-carboxylic acid tert-butyl ester

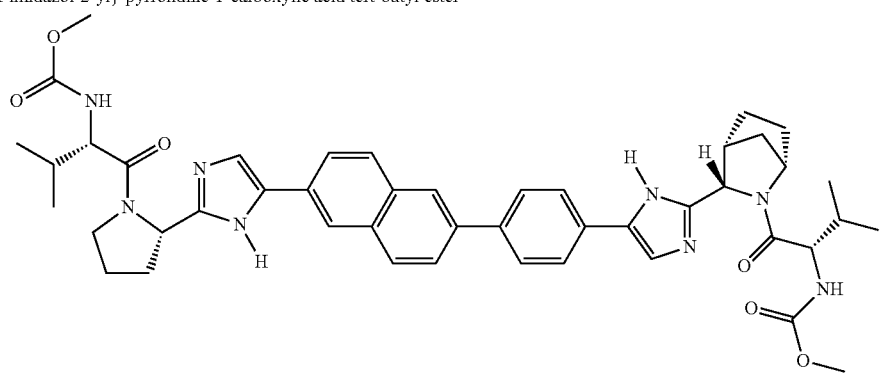

[1-(2-{5-[6-(4-{2-[2-(2-Methoxycarbonylamino-3-methyl-butyryl)-2-aza-bicyclo
[2.2.1]hept-3-yl]-3H-imidazol-4-yl)-phenyl)-naphthalen-2-yl]-1H-imidazol-2-yl}-pyrrolidine-1-
carbonyl)-2-methyl-propyl]-carbamic acid methyl ester

[2-Methyl-1-(3-{5-[4-(4,4,5,5-tetramethyl-[1,3,2]dioxaborolan-2-yl)-phenyl]-1H-imidazol-2-yl}-2-aza-bicyclo[2.2.1]heptane-2-carbonyl)-propyl]-carbamic acid methyl ester: This compound was synthesized using the procedure used to make [2-Methyl-1-(2-{5-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester using 2-Aza-bicyclo[2.2.1]heptane-2,3-dicarboxylic acid 2-tert-butyl ester. LCMS-ESI⁺: calc'd for $C_{28}H_{39}BN_4O_5$: 522.30 (M⁺); Found: 523.31 (M+H⁺).

2-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-pyrrolidine-1-carboxylic acid tert-butyl ester: This compound was synthesized using the procedure used to make 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester using 2-[5-(6-Bromo-naphthalen-2-yl)-1H-imidazol-2-yl]-pyrrolidine-1-carboxylic acid tert-butyl ester (0.124g, 0.279 mmol) and [2-Methyl-1-(3-{5-[4-(4,5,5-tetramethyl-[1,3,2]dioxaborolan-2-yl)-phenyl]-1H-imidazol-2-yl}-2-aza-bicyclo[2.2.1]heptane-2-carbonyl)-propyl]-carbamic acid methyl ester (0.219g, 0.419 mmol) to give 2-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-pyrrolidine-1-carboxylic acid tert-butyl ester (0.154g, 73% yield). LCMS-ESI⁺: calc'd for $C_{44}H_{51}N_7O_5$: 757.40 (M⁺); Found: 758.42 (M+H⁺).

[1-(2-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: This compound was synthesized using the procedure used to make (1-{2-[5-(6-Bromo-naphthalen-2-yl)-1H-imidazol-2-yl]-pyrrolidine-1-carbonyl}-2-methyl-propyl)-carbamic acid methyl ester using 2-{5-[6-(4-{2-[2-(2-Methoxycarbonylamino-3-methyl-butyryl)-2-aza-bicyclo[2.2.1]hept-3-yl]-3H-imidazol-4-yl}-phenyl)-naphthalen-2-yl]-1H-imidazol-2-yl}-pyrrolidine-1-carboxylic acid tert-butyl ester (0.154g, 0.203 mmol) giving the tile compound (0.041g, 24% yield) as a white solid. LCMS-ESI⁺: calc'd for $C_{46}H_{54}N_8O_6$: 814.42 (M⁺); Found: 815.49 (M+H⁺).

Example GP

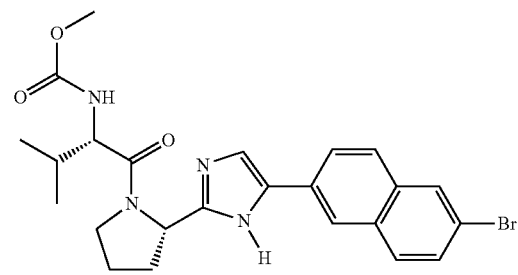

(1-{2-[5-(6-Bromo-naphthalen-2-yl)-1H-imidazol-2-yl]-pyrrolidine-1-carbonyl}-2-methyl-propyl)-carbamic acid methyl ester

+

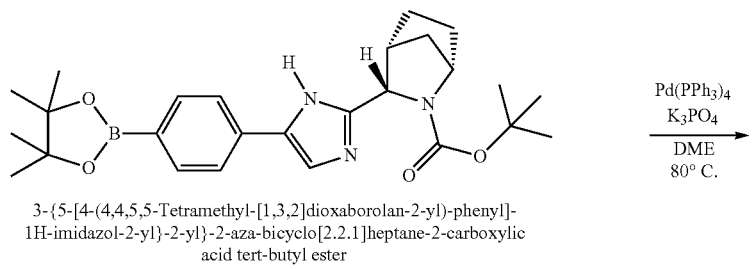

3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester Pd(PPh₃)₄
K₃PO₄
─────
DME
80° C.

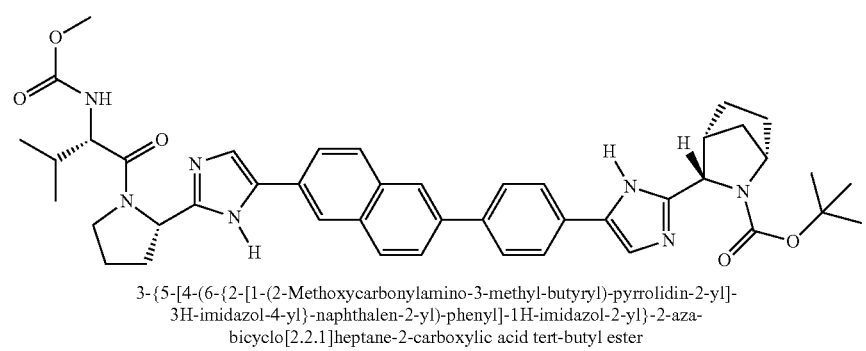

3-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-2-aza-bicyclo[2.2.1]heptane-2-carboxylic acid tert-butyl ester 1) HCl, dioxane
   MeOH
2) COMU, K₃PO₄, CH₂Cl₂

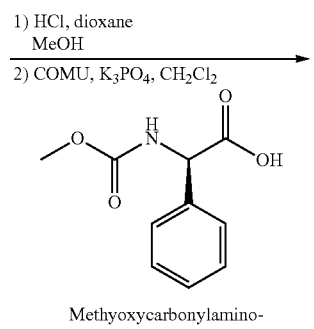

Methyoxycarbonylamino-phenyl-acetic acid

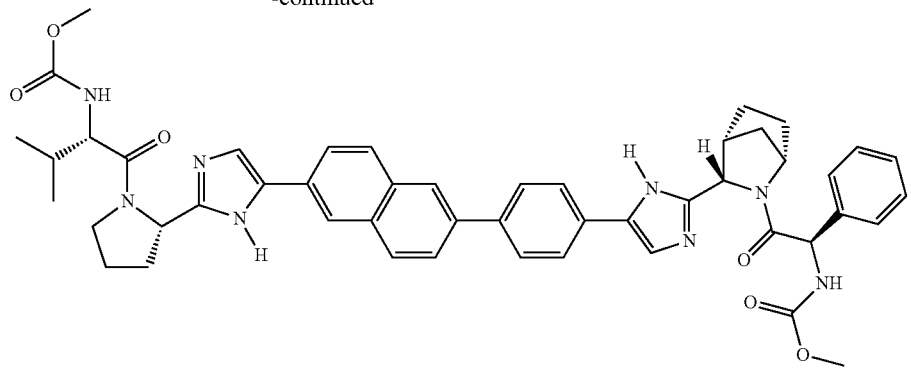

[1-(2-{5-[6-(4-{2-[2-(2-Methoxycarbonylamino-2-phenyl-acetyl)-2-aza-bicyclo[2.2.1]hept-3-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester 3-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-2-aza-bicyclo[2.2.1]heptane-2-carboxylic acid tert-butyl ester: This compound was synthesized using the procedure used to make 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester using (1-{2-[5-(6-Bromo-naphthalen-2-yl)-1H-imidazol-2-yl]-pyrrolidine-1-carbonyl}-2-methyl-propyl)-carbamic acid methyl ester (0.161 g, 0.322 mmol) and 3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester (0.195g, 0.419 mmol) to give 3-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-2-aza-bicyclo[2.2.1]heptane-2-carboxylic acid tert-butyl ester (0.133g, 46% yield). LCMS-ESI$^+$: calc'd for $C_{44}H_{51}N_7O_5$: 757.40 (M$^+$); Found: 758.26 (M+H$^+$).

[1-(2-{5-[6-(4-{2-[2-(2-Methoxycarbonylamino-2-phenyl-acetyl)-2-aza-bicyclo[2.2.1]hept-3-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester:

This compound was synthesized using the procedure used to make [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using Methoxycarbonylamino-phenyl-acetic acid (0.047g, 0.224 mmol) to give [1-(2-{5-[6-(4-{2-[2-(2-Methoxycarbonylamino-2-phenyl-acetyl)-2-aza-bicyclo[2.2.1]hept-3-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.044g, 34.8% yield). LCMS-ESI$^+$: calc'd for $C_{49}H_{52}N_8O_6$: 848.40 (M$^+$); Found: 849.96 (M+H$^+$).

Example GQ

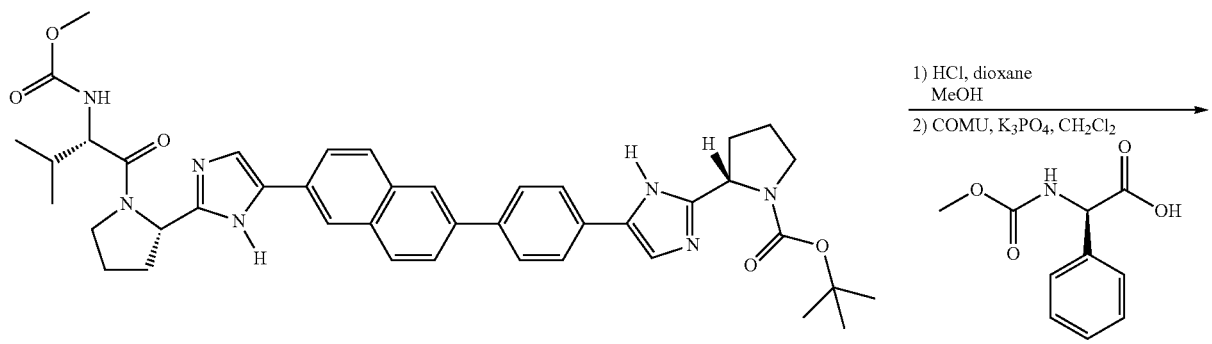

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester 1) HCl, dioxane MeOH
2) COMU, K$_3$PO$_4$, CH$_2$Cl$_2$ Methyoxycarbonylamino-phenyl-acetic acid

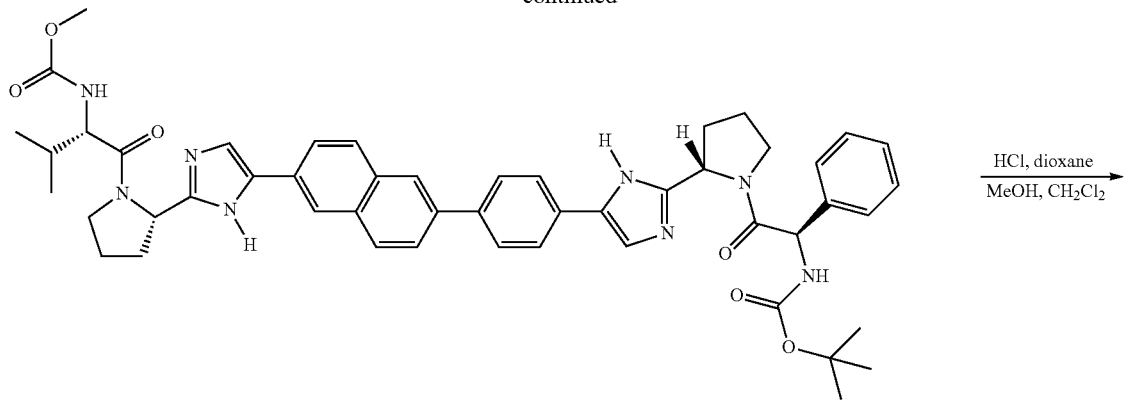

[1-(2-{5-[6-(4-{2-[1-(2-tert-Butoxycarbonylamino-2-phenyl-acetyl)-pyrrolidin-2-yl]-
3H-imidazol-4-yl}-phenyl)-naphthalen-2-yl]-1H-imidazol-2-yl}-pyrrolidine-1-carbonyl)-
2-methyl-propyl]-carbamic acid methyl ester

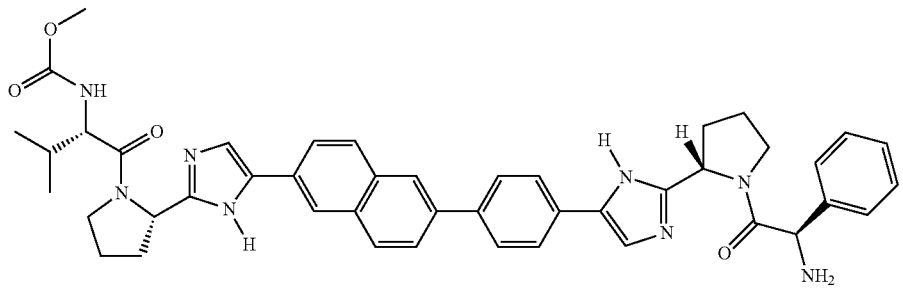

[1-(2-{5-[6-(4-[2-[1-(2-Amino-2-phenyl-acetyl)-pyrrolidin-2-yl]-3H-imidazol-4-yl}-phenyl)-naphthalen-2-yl]-
1H-imidazol-2-yl}-pyrrolidine-1-carbonyl)-2-methyl-propyl]-carbamic acid methyl ester 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester: This compound was made using the same procedure used to make 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester using 2-{5-[4-(4,4,5,5-Tetramethyl-[1,3,2]dioxaborolan-2-yl)-phenyl]-1H-imidazol-2-yl}-pyrrolidine-1-carboxylic acid tert-butyl ester. LCMS-ESI+: calc'd for $C_{42}H_{49}N_7O_5$: 731.38 (M+); Found: 732.81 (M+H+).

[1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: To a solution of 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester in DCM (4.76 mL) and MeOH (0.238 mL) was added HCl in dioxane(4N, 1.25 mL, 5 mmol). The solution was allowed to stir at room temperature for approximately 2 hours. Upon completion, the crude reaction mixture was concentrated in vacuo. The resulting solid was suspended in DCM (mL) and tert-Butoxycarbonylamino-phenyl-acetic acid was added. Solid potassium phosphate (0.318g, 1.5 mmol) was added and the suspension was cooled to 0° C. (external, ice/water bath). COMU was added at 0° C. and the slurry was allowed to stir at 0° C. for one hour. Upon completion, the crude reaction mixture was filtered through a syringe filter, and concentrated. The resulting slurry was diluted in DMF and purified by reverse phase HPLC (10-40% acetonitrile: water; 0.1% formic acid modifier), and lyophilized giving [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.305g, 61%) as a white solid. LCMS-ESI+: calc'd for $C_{50}H_{56}N_8O_6$: 864.43 (M+); Found: 865.77 (M+H+).

[1-(2-{5-[6-(4-{2-[1-(2-Amino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.211g, 0.244 mmol) was dissolved in DCM (2.439 mL). HCl in dioxane (4N, 0.610 mL, 2.44 mmol) was added at room temperature and the resulting solution was stirred for approximately one hour. Upon completion, the reaction was concentrated in vacuo to giving [1-(2-{5-[6-(4-{2-[1-(2-Amino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester as a white solid (assumed 0.244 mmol) that was used without further purification in subsequent reactions. LCMS-ESI+: calc'd for $C_{45}H_{48}N_8O_4$: 764.43 (M+); Found: 765.31 (M+H+).

Example GR

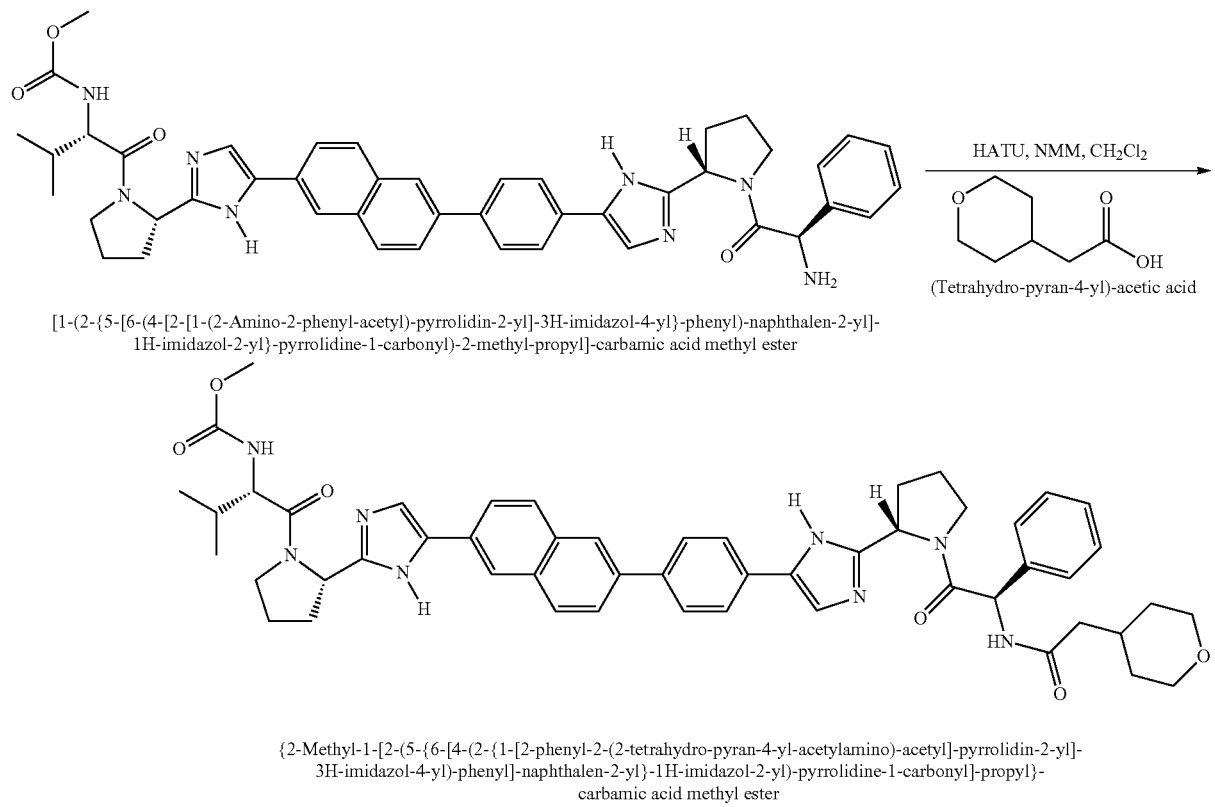

[1-(2-{5-[6-(4-[2-[1-(2-Amino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester {2-Methyl-1-[2-(5-{6-[4-(2-{1-[2-phenyl-2-(2-tetrahydro-pyran-4-yl-acetylamino)-acetyl]-pyrrolidin-2-yl]-3H-imidazol-4-yl)-phenyl]-naphthalen-2-yl}-1H-imidazol-2-yl)-pyrrolidine-1-carbonyl]-propyl}-carbamic acid methyl ester {2-Methyl-1-[2-(5-{6-[4-(2-{1-[2-phenyl-2-(2-tetrahydro-pyran-4-yl-acetylamino)-acetyl]-pyrrolidin-2-yl}-3H-imidazol-4-yl)-phenyl]-naphthalen-2-yl}-1H-imidazol-2-yl)-pyrrolidine-1-carbonyl]-propyl}-carbamic acid methyl ester: [1-(2-{5-[6-(4-{2-[1-(2-Amino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.085g, 0.097 mmol), (Tetrahydro-pyran-4-yl)-acetic acid (0.017g, 0.117 mmol), and N-methylmorpholine (0.032 mL, 0.292 mmol) were suspended in DMF (0.972 mL) at room temperature. Solid HATU (0.055g, 0.146 mmol) was added and the suspension was allowed to stir at room temperature overnight. Upon completion, the reaction was quenched with a small amount of formic acid and purified by reverse phase HPLC (10-45% acetonitrile:water; 0.1% formic acid modifier), and lyophilized giving {2-Methyl-1-[2-(5-{6-[4-(2-{1-[2-phenyl-2-(2-tetrahydro-pyran-4-yl-acetylamino)-acetyl]-pyrrolidin-2-yl}-3H-imidazol-4-yl)-phenyl]-naphthalen-2-yl}-1H-imidazol-2-yl)-pyrrolidine-1-carbonyl]-propyl}-carbamic acid methyl ester (0.062g, 62%) as a white solid. LCMS-ESI+: calc'd for $C_{52}H_{58}N_8O_6$: 890.45 ($M^+$); Found: 892.4 ($M+H^+$).

Example GS

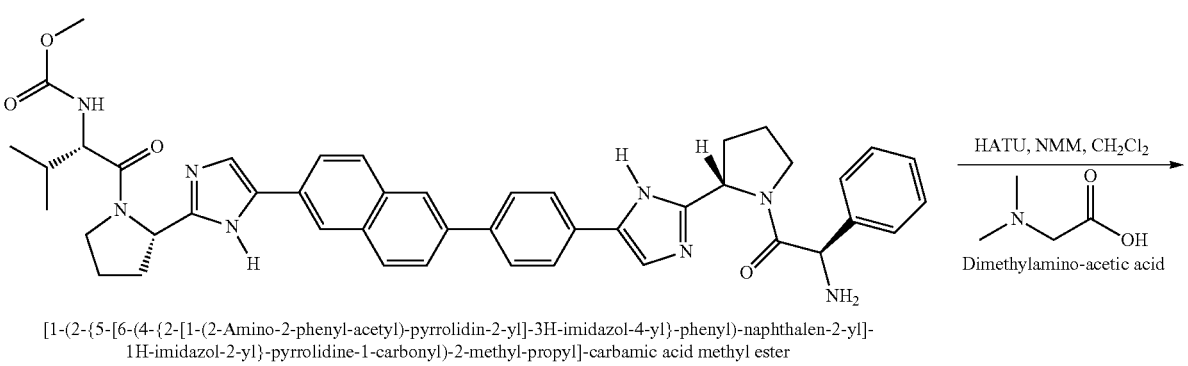

[1-(2-{5-[6-(4-{2-[1-(2-Amino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

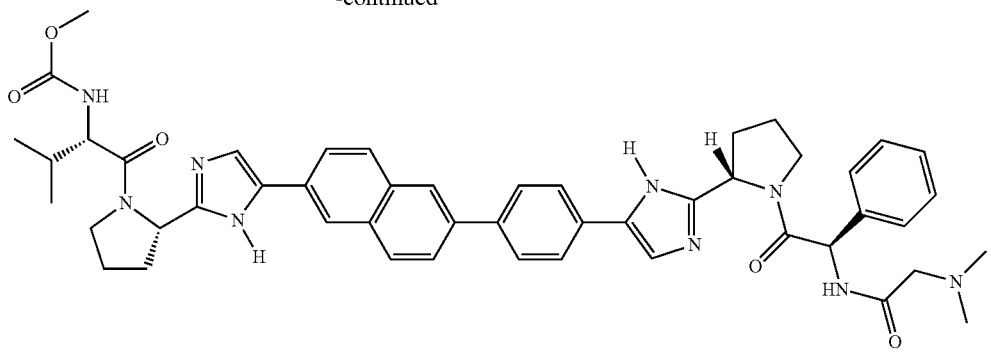

{1-[2-(5-{6-[4-(2-{1-[2-(2-Dimethylamino-acetylamino)-2-phenyl-acetyl]-pyrrolidin-2-yl}-
3H-imidazol-4-yl)-phenyl]-naphthalen-2-yl}-1H-imidazol-2-yl)-pyrrolidine-1-carbonyl]-2-methyl-propyl}-
carbamic acid methyl ester {1-[2-(5-{6-[4-(2-{1-[2-(2-Dimethylamino-acetylamino)-2-phenyl-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester: This compound was prepared using the procedure used to prepare {2-Methyl-1-[2-(5-{6-[4-(2-{1-[2-phenyl-2-(2-tetrahydro-pyran-4-yl-acetyl amino)-acetyl]-pyrrolidin-2-yl}-3H-imidazol-4-yl)-phenyl]-naphthalen-2-yl}-1H-imidazol-2-yl)-pyrrolidine-1-carbonyl]-propyl}-carbamic acid methyl ester using Dimethylamino-acetic acid (0.018g, 0.172 mmol) to provide {1-[2-(5-{6-[4-(2-{1-[2-(2-Dimethylamino-acetylamino)-2-phenyl-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester (0.106g, >99%) as a white solid. LCMS-ESI+: calc'd for C49H55N9O5: 849.43 (M+); Found: 850.60 (M+H+).

Example GT

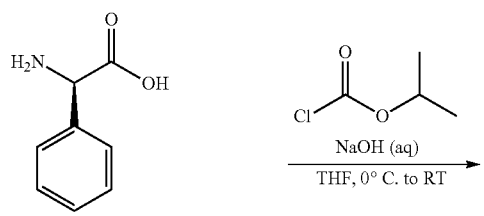

Amino-phenyl-acetic acid

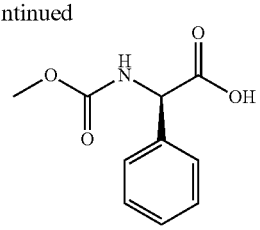

Isopropoxycarbonylamino-phenyl-acetic acid

Isopropoxycarbonylamino-phenyl-acetic acid: Amino-phenyl-acetic acid (0.505g, 2.44 mmol) was dissolved in THF (7 mL) and cooled to 0° C. in an external ice/brine bath. Aqueous sodium hydroxide (12.5M, 0.47 mL, 5.856 mmol) and isopropyl chloroformate (0.23 mL, 2.948 mmol) were added at 0° C. Upon completion of the addition, the solution was removed from the ice bath and allowed to warm to room temperature, and stirred. After 18 hours, the crude reaction mixture was adjusted to pH 1 with 1N HCl and extracted twice with diethyl ether. The combined organic layers were washed with brine, dried with magnesium sulfate and concentrated to give Isopropoxycarbonylamino-phenyl-acetic acid as an off-white solid. LCMS-ESI+: calc'd for C12H15NO4: 237.10 (M+); Found: 238.05 (M+H+).

Example GU

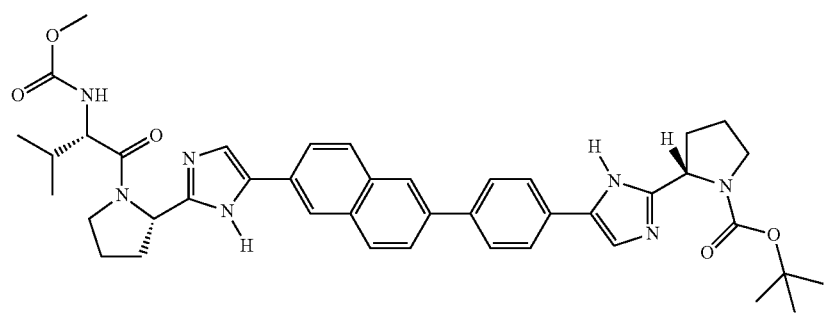

2-{5-[4-(6-{2-[1-(2-Methoxycarbonylamino-3-methyl-butyryl)-pyrrolidin-2-yl]-
3H-imidazol-4-yl}-naphthalen-2-yl)-phenyl]-1H-imidazol-2-yl}-
pyrrolidine-1-carboxylic acid tert-butyl ester 1) HCl, dioxane
   MeOH
2) COMU, K3PO4, CH2Cl2

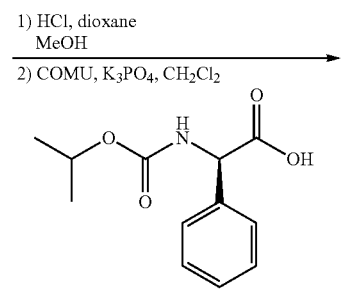

Isopropoxycarbonylamino-phenyl-acetic acid

-continued

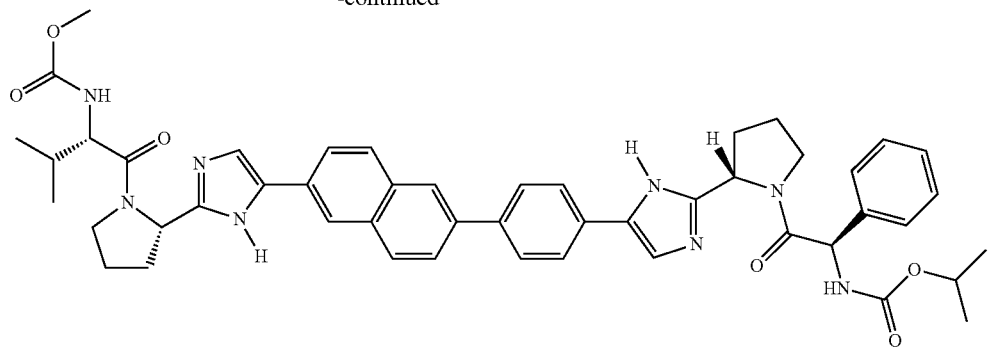

[1-(2-{5-[6-(4-{2-[1-(2-Isopropoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[1-(2-Isopropoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: This compound was prepared using the procedure used to prepare [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using Isopropoxycarbonylamino-phenyl-acetic acid (0.066g, 0.281 mmol) to provide {1-[2-(5-{6-[4-(2-{1-[2-(2-Fluoro-phenyl)-2-methoxycarbonylamino-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester (0.025g, 16%) as a white solid. LCMS-ESI$^+$: calc'd for $C_{49}H_{54}N_8O_6$: 850.42 (M$^+$); Found: 851.83 (M+H$^+$).

Example GV

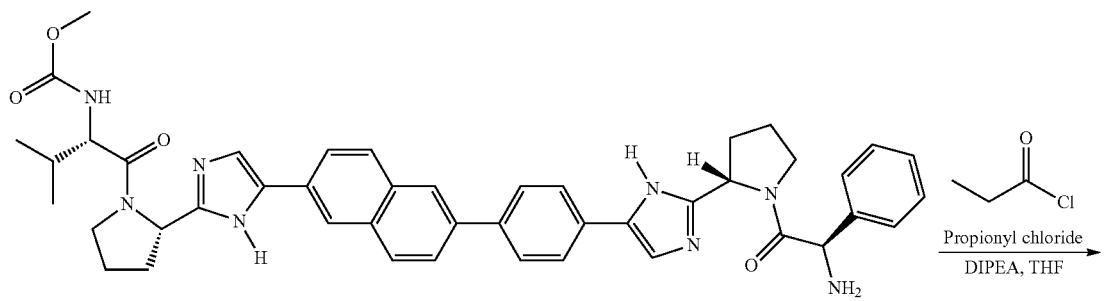

[1-(2-{5-[6-(4-{2-[1-(2-Amino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

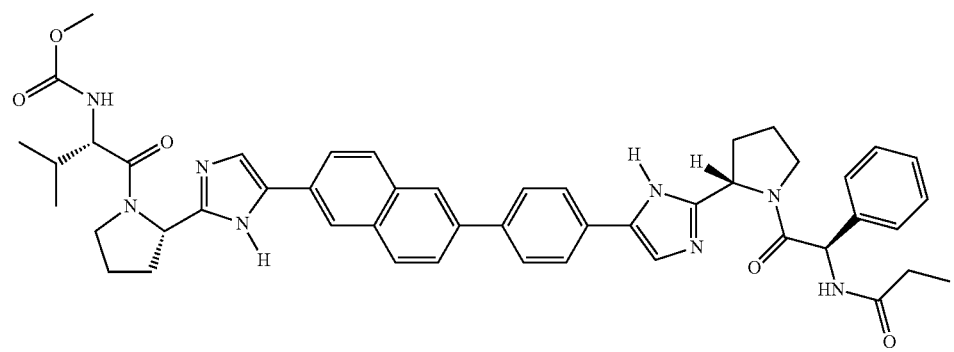

[2-Methyl-1-(2-{5-[6-(4-{2-[1-(2-phenyl-2-propionylamino-acetyl)-pyrrolidin-2-yl]-3H-imidazol-4-yl}-phenyl)-naphthalen-2-yl]-1H-imidazol-2-yl}-pyrrolidine-1-carbonyl)-propyl]-carbamic acid methyl ester

[2-Methyl-1-(2-{5-[6-(4-{2-[1-(2-phenyl-2-propionylamino-acetyl)-pyrrolidin-2-yl]-3H-imidazol-4-yl}-phenyl)-naphthalen-2-yl]-1H-imidazol-2-yl}-pyrrolidine-1-carbonyl)-propyl]-carbamic acid methyl ester: [1-(2-{5-[6-(4-{2-[1-(2-Amino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.05g, 0.057 mmol) was suspended in THF (0.572 mL). Upon addition of DIPEA (0.050 mL, 0.286 mmol), the slurry partially clarified. Propionyl chloride (0.005 mL, 0.057 mmol) was added at room temperature and the reaction was allowed to sit at room temperature overnight. Upon completion, the reaction was quenched with a small amount of formic acid and purified by reverse phase HPLC (10-45% acetonitrile:water; 0.1% formic acid modifier), and lyophilized giving [2-Methyl-1-(2-{5-[6-(4-{2-[1-(2-phenyl-2-propionylamino-acetyl)-pyrrolidin-2-yl]-3H-imidazol-4-yl}-phenyl)-naphthalen-2-yl]-1H-imidazol-2-yl}-pyrrolidine-1-carbonyl)-propyl]-carbamic acid methyl ester (0.008g, 17%) as a white solid. LCMS-ESI$^+$: calc'd for $C_{48}H_{52}N_8O_5$: 820.41 (M$^+$); Found: 821.51 (M+H$^+$).

Example GW

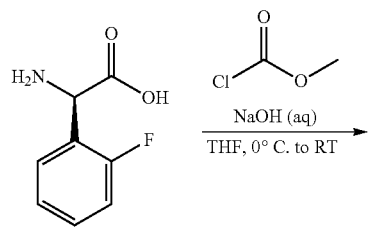

Amino-(2-fluoro-phenyl)-acetic acid

NaOH (aq)
THF, 0° C. to RT

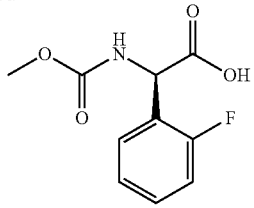

(2-Fluoro-phenyl)-methoxycarbonylamino-acetic acid (2-Fluoro-phenyl)-methoxycarbonylamino-acetic acid: Amino-(2-fluoro-phenyl)-acetic acid (0.5g, 2.44 mmol) was dissolved in THF (7 mL) and cooled to 0° C. in an external ice/brine bath. Aqueous sodium hydroxide (12.5M, 0.47 mL, 5.856 mmol) and methyl chloroformate (0.23 mL, 2.948 mmol) were added at 0° C. Upon completion of the addition, the solution was removed from the ice bath and allowed to warm to room temperature, and stirred. After 18 hours, the crude reaction mixture was adjusted to pH 1 with 1N HCl and extracted twice with diethyl ether. The combined organic layers were washed with brine, dried with magnesium sulfate and concentrated to give (2-Fluoro-phenyl)-methoxycarbonylamino-acetic acid as an off-white solid. LCMS-ESI$^+$: calc'd for $C_{10}H_{10}FNO_4$: 227.06 (M$^+$); Found: 228.17 (M+H$^+$).

Example GX

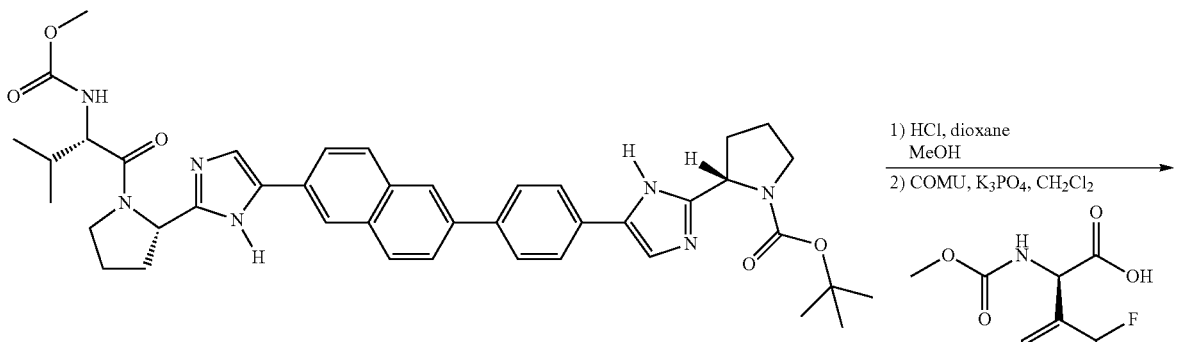

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester 1) HCl, dioxane MeOH
2) COMU, K$_3$PO$_4$, CH$_2$Cl$_2$ (2-Fluoro-phenyl)-methoxycarbonylamino-acetic acid

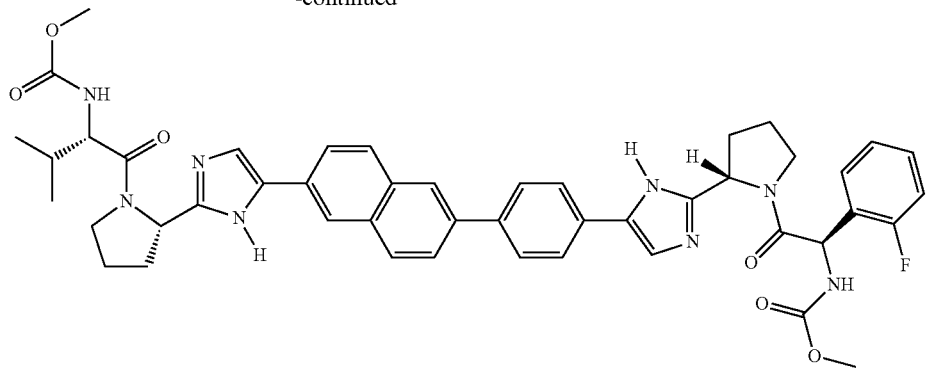

{1-[2-(5-{6-[4-(2-{1-[2-(2-Fluoro-phenyl)-2-methoxycarbonylamino-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester {1-[2-(5-{6-[4-(2-{1-[2-(2-Fluoro-phenyl)-2-methoxycarbonylamino-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester: This compound was prepared using the procedure used to prepare [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using (2-Fluoro-phenyl)-methoxycarbonylamino-acetic acid (0.061g, 0.269 mmol) to provide {1-[2-(5-{6-[4-(2-{1-[2-(2-Fluoro-phenyl)-2-methoxycarbonylamino-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester (0.012g, 8%) as a white solid. LCMS-ESI+: calc'd for $C_{47}H_{49}FN_8O_6$: 840.38 ($M^+$); Found: 841.86 ($M+H^+$).

Example GY

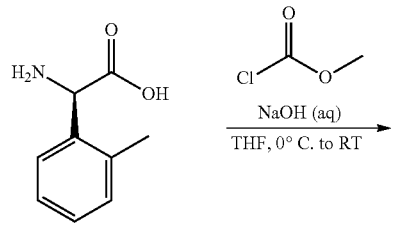

Amino-o-tolyl-acetic acid

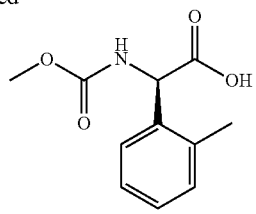

Methoxycarbonylamino-o-tolyl-acetic acid

Methoxycarbonylamino-o-tolyl-acetic acid: Methoxycarbonylamino-o-tolyl-acetic acid was prepared using the procedure used to prepare (2-Fluoro-phenyl)-methoxycarbonylamino-acetic acid using Amino-o-tolyl-acetic acid. LCMS-ESI+: calc'd for $C_{11}H_{13}NO_4$: 223.08 ($M^+$); Found: 223.94 ($M+H^+$).

Example GZ

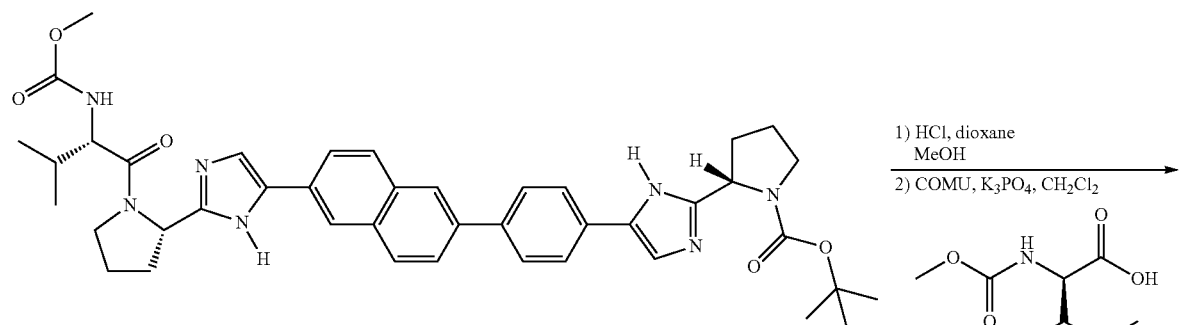

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester 1) HCl, dioxane MeOH
2) COMU, $K_3PO_4$, $CH_2Cl_2$

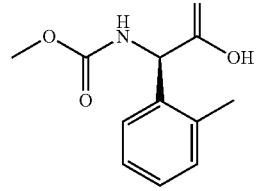

Methoxycarbonylamino-o-tolyl-acetic acid

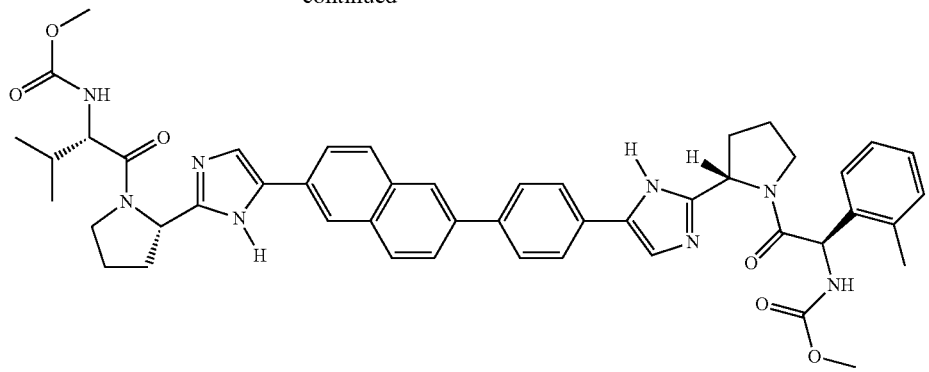

[1-(2-{5-[6-(4-{2-[1-(2-Methoxycarbonylamino-2-o-tolyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[1-(2-Methoxycarbonylamino-2-o-tolyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: This compound was prepared using the procedure used to prepare [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using Methoxycarbonylamino-o-tolyl-acetic acid (0.072g, 0.332 mmol) to provide [1-(2-{5-[6-(4-{2-[1-(2-Methoxycarbonylamino-2-o-tolyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.047g, 31.4%) as a white solid. LCMS-ESI$^+$: calc'd for $C_{48}H_{52}N_8O_6$: 836.40 (M$^+$); Found: 837.86 (M+H$^+$).

Example HA

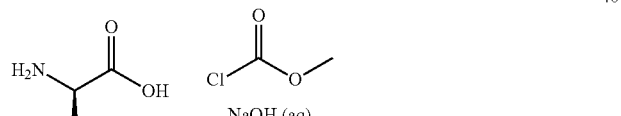

Amino-m-tolyl-acetic acid

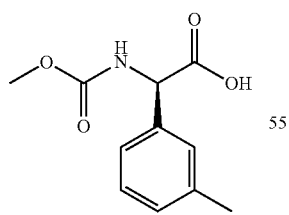

Methoxycarbonylamino-m-tolyl-acetic acid

Methoxycarbonylamino-m-tolyl-acetic acid: Methoxycarbonylamino-m-tolyl-acetic acid was prepared using the procedure used to prepare (2-Fluoro-phenyl)-methoxycarbonylamino-acetic acid using Amino-m-tolyl-acetic acid. LCMS-ESI$^+$: calc'd for $C_{11}H_{13}NO_4$: 223.08 (M$^+$); Found: 223.90 (M+H$^+$).

Example HB

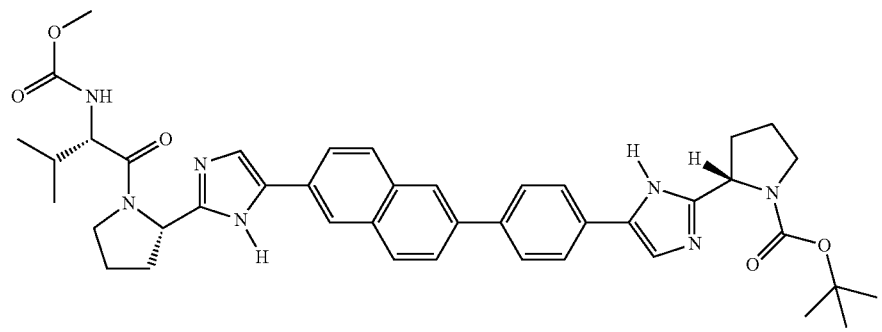

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester

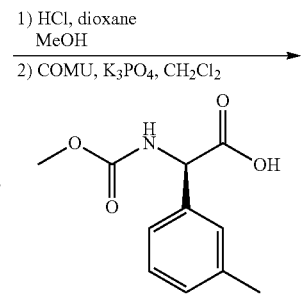

Methoxycarbonylamino-m-tolyl-acetic acid

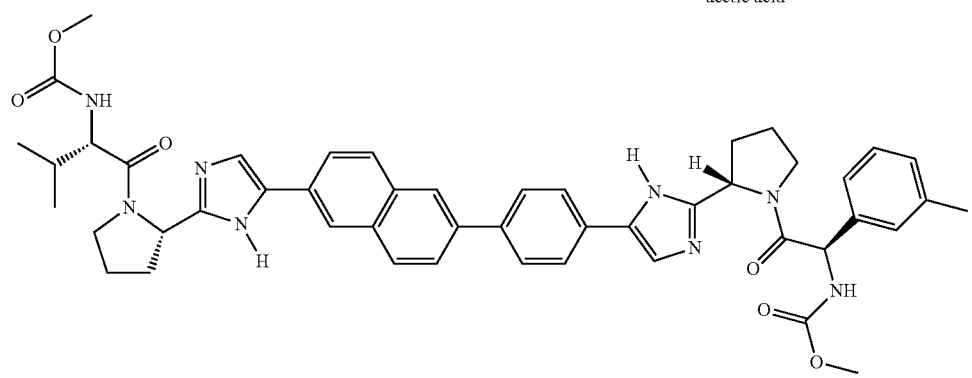

[1-(2-{5-[6-(4-{2-[1-(2-Methoxycarbonylamino-2-m-tolyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[1-(2-Methoxycarbonylamino-2-m-tolyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: This compound was prepared using the procedure used to prepare [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using Methoxycarbonylamino-m-tolyl-acetic acid (0.046g, 0.206 mmol) to provide [1-(2-{5-[6-(4-{2-[1-(2-Methoxycarbonylamino-2-m-tolyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.039g, 34%) as a white solid. LCMS-ESI$^+$: calc'd for $C_{48}H_{52}N_8O_6$: 836.40 (M$^+$); Found: 837.91 (M+H$^+$).

Example HC

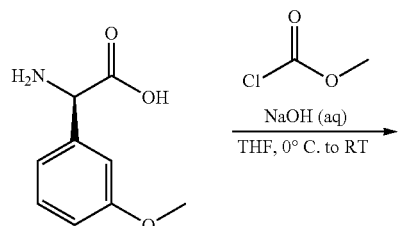

Amino-(3-methoxy-phenyl)-acetic acid

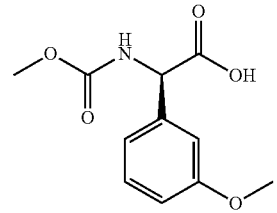

Methoxycarbonylamino-(3-methoxy-phenyl)-acetic acid

Methoxycarbonylamino-(3-methoxy-phenyl)-acetic acid: Methoxycarbonylamino-(3-methoxy-phenyl)-acetic acid was prepared using the procedure used to prepare (2-Fluoro-phenyl)-methoxycarbonylamino-acetic acid using Amino-(3-methoxy-phenyl)-acetic acid. LCMS-ESI$^+$: calc'd for $C_{11}H_{13}NO_5$: 239.08 (M$^+$); Found: 239.94 (M+H$^+$).

Example HD

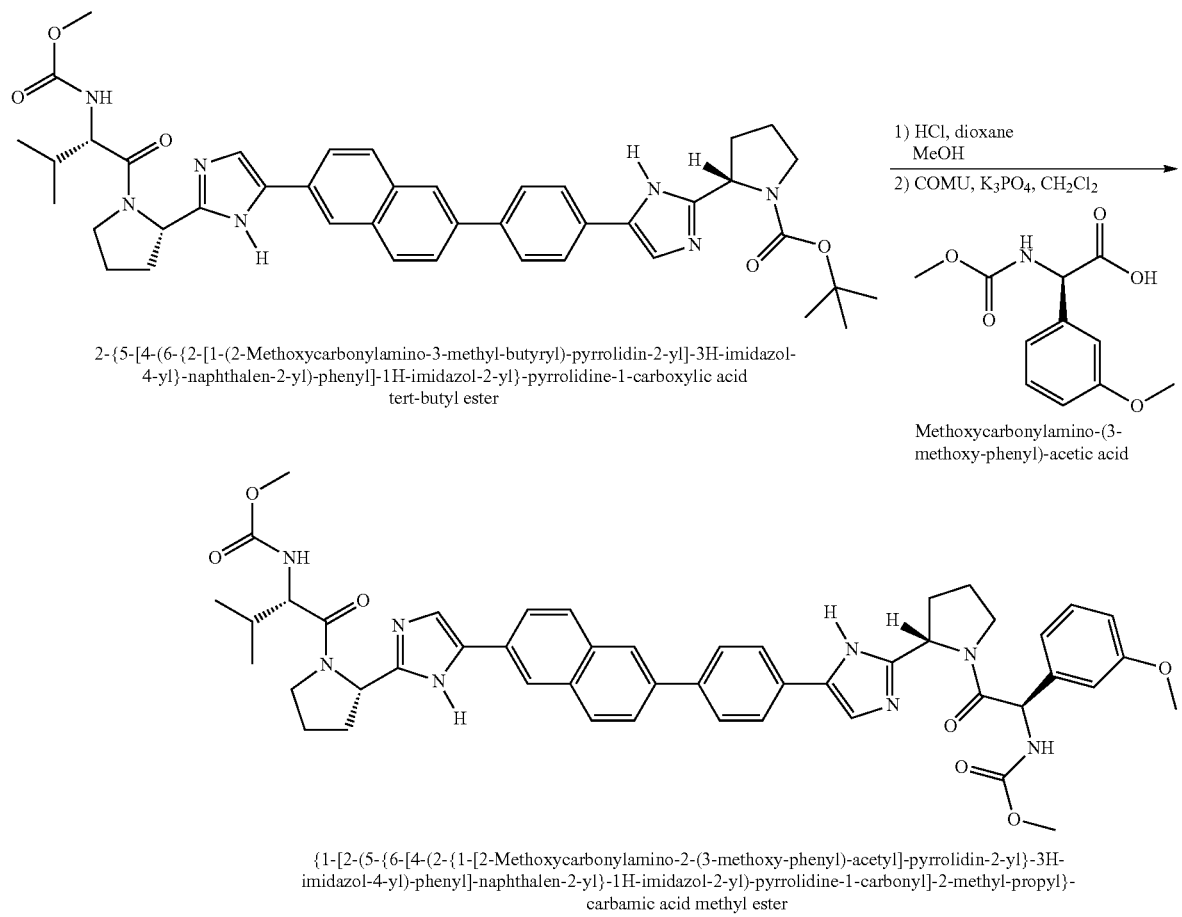

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester Methoxycarbonylamino-(3-methoxy-phenyl)-acetic acid {1-[2-(5-{6-[4-(2-{1-[2-Methoxycarbonylamino-2-(3-methoxy-phenyl)-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester {1-[2-(5-{6-[4-(2-{1-[2-Methoxycarbonylamino-2-(3-methoxy-phenyl)-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester: This compound was prepared using the procedure used to prepare [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using Methoxycarbonylamino-(3-methoxy-phenyl)-acetic acid (0.049g, 0.206 mmol) to provide {1-[2-(5-{6-[4-(2-{1-[2-Methoxycarbonylamino-2-(3-methoxy-phenyl)-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester (0.006g, 5%) as a white solid.

LCMS-ESI$^+$: calc'd for $C_{48}H_{52}N_8O_7$: 852.40 (M$^+$); Found: 853.33 (M+H$^+$).

Example HE

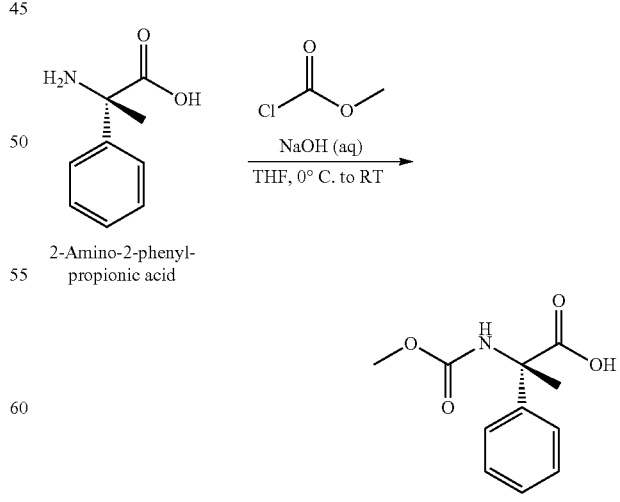

2-Amino-2-phenyl-propionic acid

2-Methoxycarbonylamino-2-phenyl-propionic acid

2-Methoxycarbonylamino-2-phenyl-propionic acid: 2-Methoxycarbonylamino-2-phenyl-propionic acid was prepared using the procedure used to prepare (2-Fluoro-phenyl)-methoxycarbonylamino-acetic acid using 2-Amino-2-phenyl-propionic acid. LCMS-ESI$^+$: calc'd for $C_{11}H_{13}NO_4$: 223.08 (M$^+$); Found: 223.96 (M+H$^+$).

Example HF

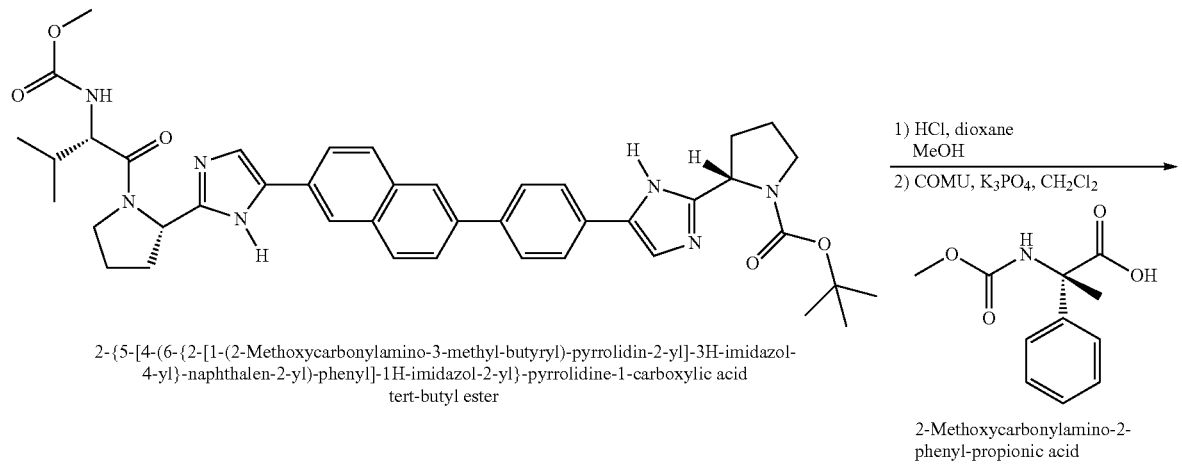

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester 2-Methoxycarbonylamino-2-phenyl-propionic acid

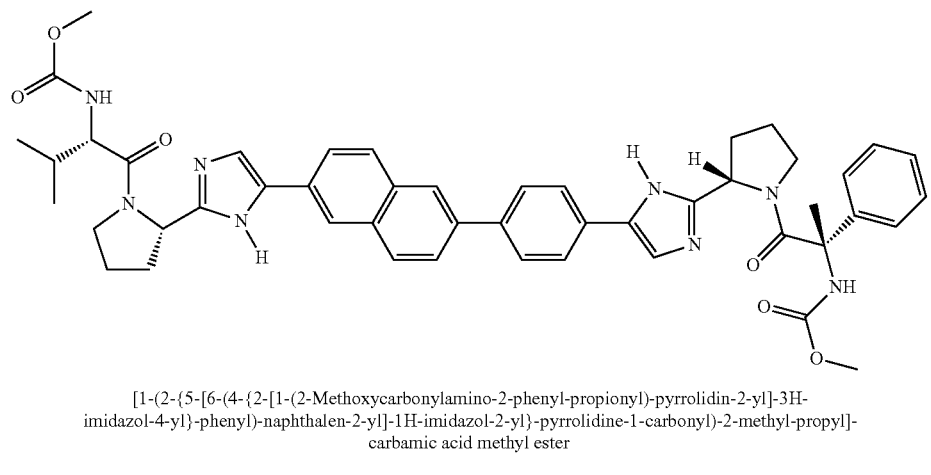

[1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester

[1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester: This compound was prepared using the procedure used to prepare [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using 2-Methoxycarbonylamino-2-phenyl-propionic acid (0.068g, 0.308 mmol) to provide [1-(2-{5-[6-(4-{2-[1-(2-Methoxycarbonylamino-2-phenyl-propionyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester (0.035g, 20%) as a white solid. LCMS-ESI$^+$: calc'd for $C_{48}H_{52}N_8O_6$: 836.40 (M$^+$); Found: 837.92 (M+H$^+$).

Example HG

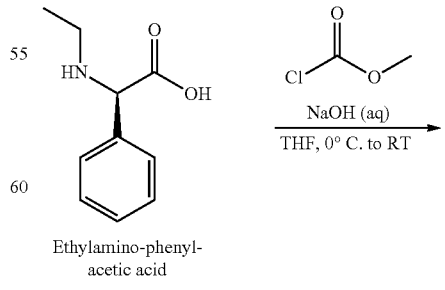

Ethylamino-phenyl-acetic acid

953
-continued

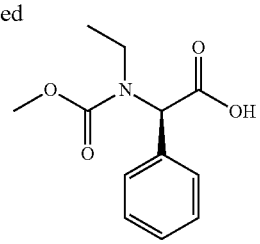

(Ethyl-methoxycarbonyl-
amino)-phenyl-acetic acid (Ethyl-methoxycarbonylamino)-phenyl-acetic acid: (Ethyl-methoxycarbonylamino)-phenyl-acetic acid was prepared using the procedure used to prepare (2-Fluoro-phenyl)-methoxycarbonylamino-acetic acid using Ethylamino-phenyl-acetic acid. LCMS-ESI+: calc'd for $C_{12}H_{15}NO_4$: 237.10 (M+); Found: 238.03 (M+H+).

Example HH

954

{1-[2-(5-{6-[4-(2-{1-[2-(Ethyl-methoxycarbonylamino)-2-phenyl-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester: This compound was prepared using the procedure used to prepare [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using (Ethyl-methoxycarbonylamino)-phenyl-acetic acid (0.097g, 0.410 mmol) to provide {1-[2-(5-{6-[4-(2-{1-[2-(Ethyl-methoxycarbonylamino)-2-phenyl-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester (0.120g, 52%) as a white solid. LCMS-ESI+: calc'd for $C_{49}H_{54}N_8O_6$: 840.38 (M+); Found: 851.91 (M+H+).

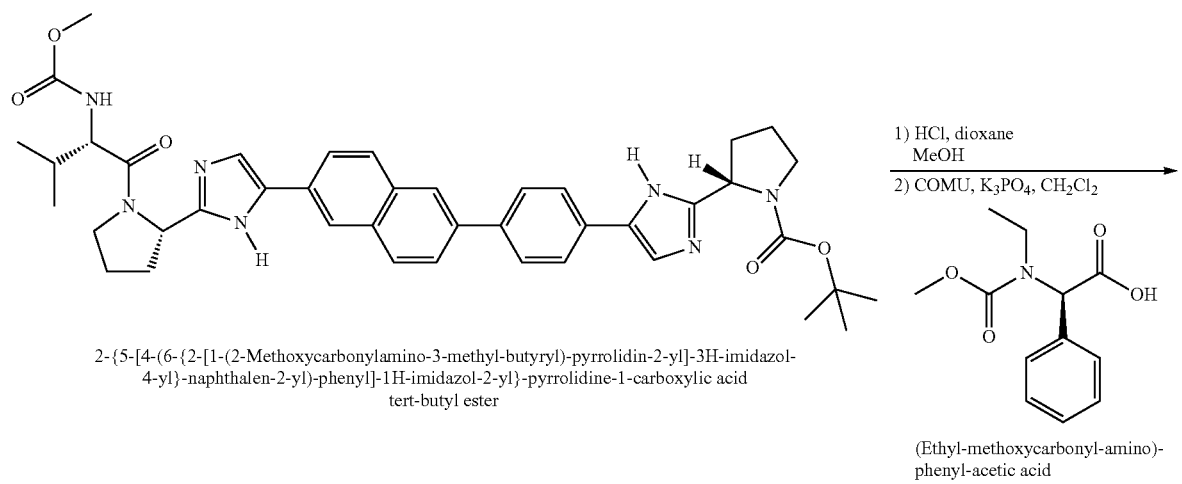

2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester 1) HCl, dioxane MeOH
2) COMU, $K_3PO_4$, $CH_2Cl_2$ (Ethyl-methoxycarbonyl-amino)-phenyl-acetic acid

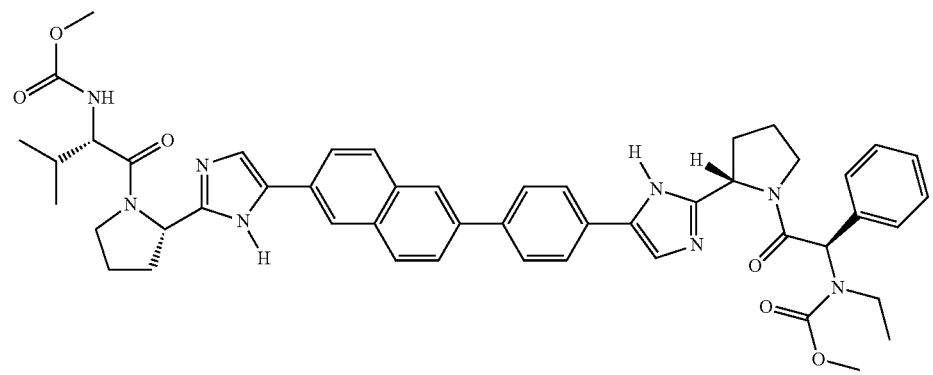

{1-[2-(5-{6-[4-(2-{1-[2-(Ethyl-methoxycarbonyl-amino)-2-phenyl-acetyl]-pyrrolidin-2-yl}-3H-imidazol-4-yl)-phenyl]-naphthalen-2-yl}-1H-imidazol-2-yl)-pyrrolidine-1-carbonyl]-2-methyl-propyl}-carbamic acid methyl ester Example HI

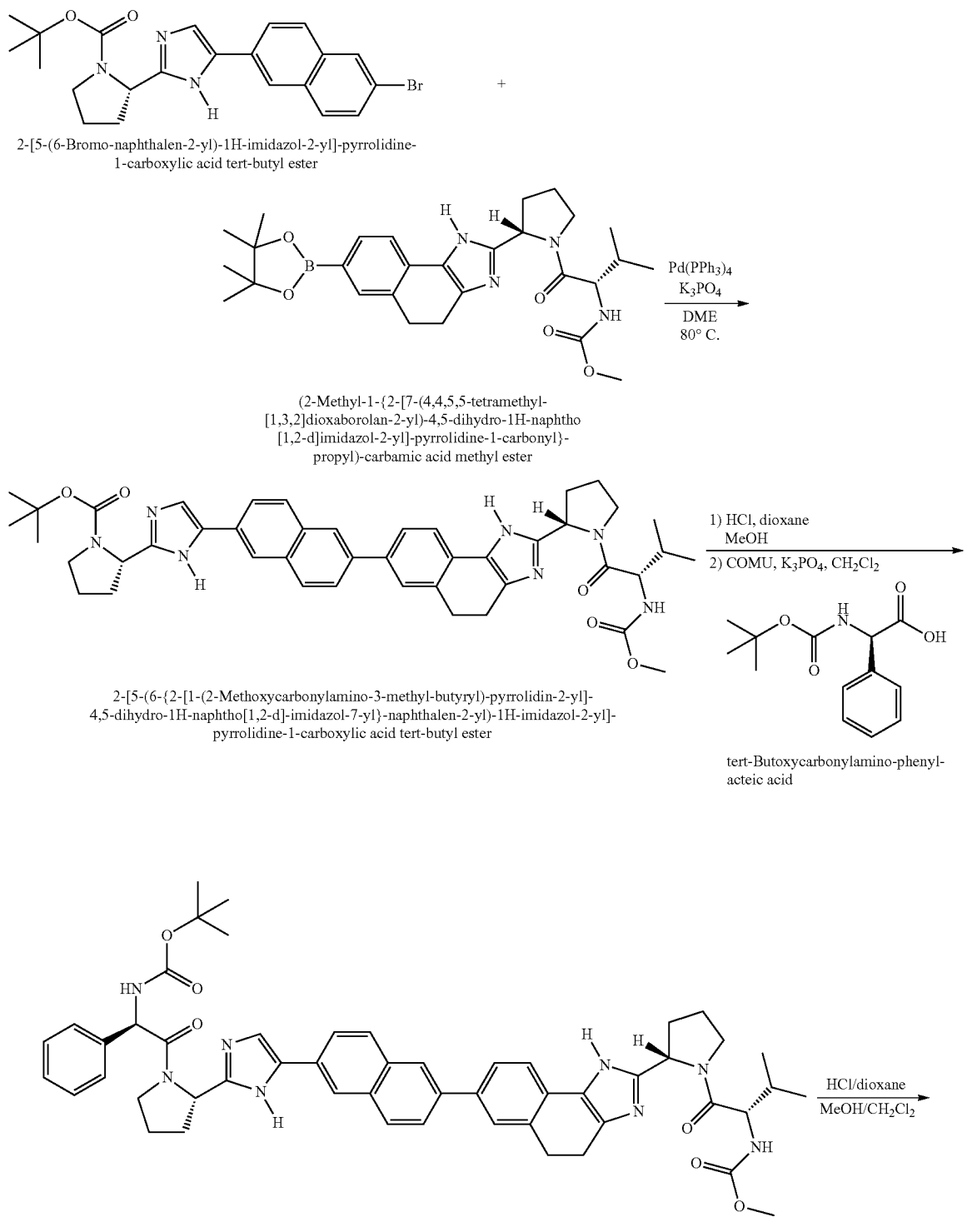

2-[5-(6-Bromo-naphthalen-2-yl)-1H-imidazol-2-yl]-pyrrolidine-1-carboxylic acid tert-butyl ester (2-Methyl-1-{2-[7-(4,4,5,5-tetramethyl-[1,3,2]dioxaborolan-2-yl)-4,5-dihydro-1H-naphtho[1,2-d]imidazol-2-yl]-pyrrolidine-1-carbonyl}-propyl)-carbamic acid methyl ester 2-[5-(6-{2-[1-(2-Methoxycarbonylamino-3-methyl-butyryl)-pyrrolidin-2-yl]-4,5-dihydro-1H-naphtho[1,2-d]imidazol-7-yl}-naphthalen-2-yl)-1H-imidazol-2-yl]-pyrrolidine-1-carboxylic acid tert-butyl ester tert-Butoxycarbonylamino-phenyl-acteic acid $C_{52}H_{58}N_8O_6$
Exact Mass: 890.45
(1-{2-[7-(6-{2-[1-(2-tert-Butoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester

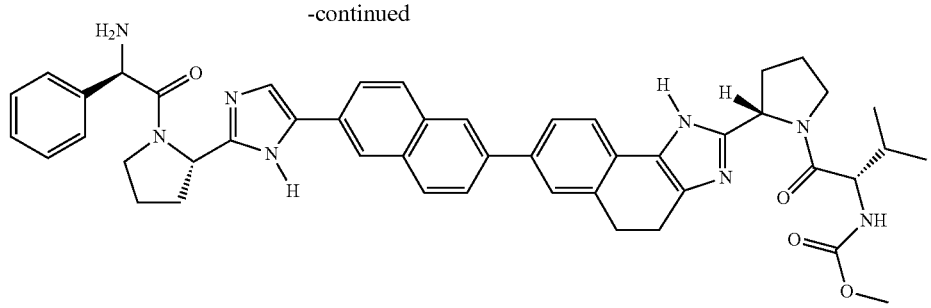

(1-{2-[7-(6-{2-[1-(2-Amino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester 2-[5-(6-{2-[1-(2-Methoxycarbonylamino-3-methyl-butyryl)-pyrrolidin-2-yl]-4,5-dihydro-1H-naphtho[1,2-d]imidazol-7-yl}-naphthalen-2-yl)-1H-imidazol-2-yl]-pyrrolidine-1-carboxylic acid tert-butyl ester: This compound was synthesized using the procedure used to make 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-4-methylene-pyrrolidine-1-carboxylic acid tert-butyl ester using 2-[5-(6-Bromo-naphthalen-2-yl)-1H-imidazol-2-yl]-pyrrolidine-1-carboxylic acid tert-butyl ester (0.641g, 1.449 mmol) and (2-Methyl-1-{2-[7-(4,4,5,5-tetramethyl-[1,3,2]dioxaborolan-2-yl)-4,5-dihydro-1H-naphtho[1,2-d]imidazol-2-yl]-pyrrolidine-1-carbonyl}-propyl)-carbamic acid methyl ester (1.06g, 2.029 mmol) to give 2-[5-(6-{2-[1-(2-Methoxycarbonylamino-3-methyl-butyryl)-pyrrolidin-2-yl]-4,5-dihydro-1H-naphtho[1,2-d]imidazol-7-yl}-naphthalen-2-yl)-1H-imidazol-2-yl]-pyrrolidine-1-carboxylic acid tert-butyl ester (0.812g, 74% yield) as a solid. LCMS-ESI+: calc'd for $C_{44}H_{51}N_7O_5$: 757.40 (M+); Found: 758.75 (M+H+).

(1-{2-[7-(6-{2-[1-(2-tert-Butoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester: This compound was synthesized using the procedure used to make [1-(2-{5-[6-(4-{2-[1-(2-tert-Butoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using 2-[5-(6-{2-[1-(2-Methoxycarbonylamino-3-methyl-butyryl)-pyrrolidin-2-yl]-4,5-dihydro-1H-naphtho[1,2-d]imidazol-7-yl}-naphthalen-2-yl)-1H-imidazol-2-yl]-pyrrolidine-1-carboxylic acid tert-butyl ester (0.400g, 0.528 mmol) to give (1-{2-[7-(6-{2-[1-(2-tert-Butoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester (0.180g, 38% yield). LCMS-ESI+: calc'd for $C_{52}H_{58}N_8O_6$: 890.45 (M+); Found: 891.88 (M+H+).

(1-{2-[7-(6-{2-[1-(2-Amino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester: This compound was synthesized using the procedure used to make [1-(2-{5-[6-(4-{2-[1-(2-Amino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester using (1-{2-[7-(6-{2-[1-(2-tert-Butoxycarbonylamino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester (0.180g, 0.202 mmol) to give the title compound (0.160, >99% yield). LCMS-ESI+: calc'd for $C_{47}H_{50}N_8O_4$: 790.40 (M+); Found: 791.39 (M+H+).

Example HJ

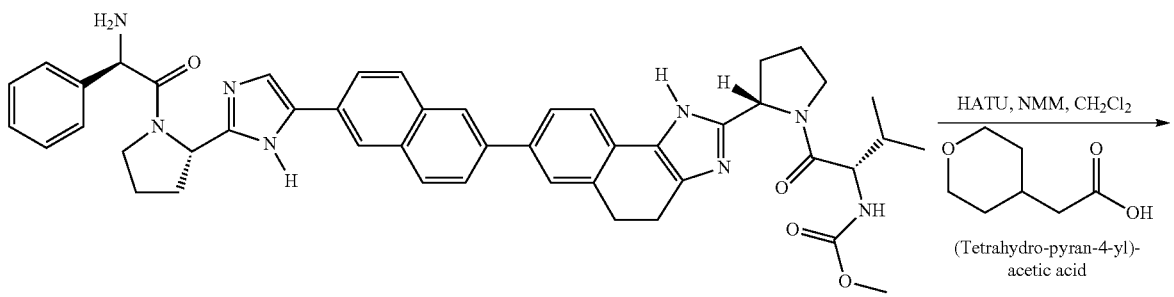

(1-{2-[7-(6-{2-[1-(2-Amino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester

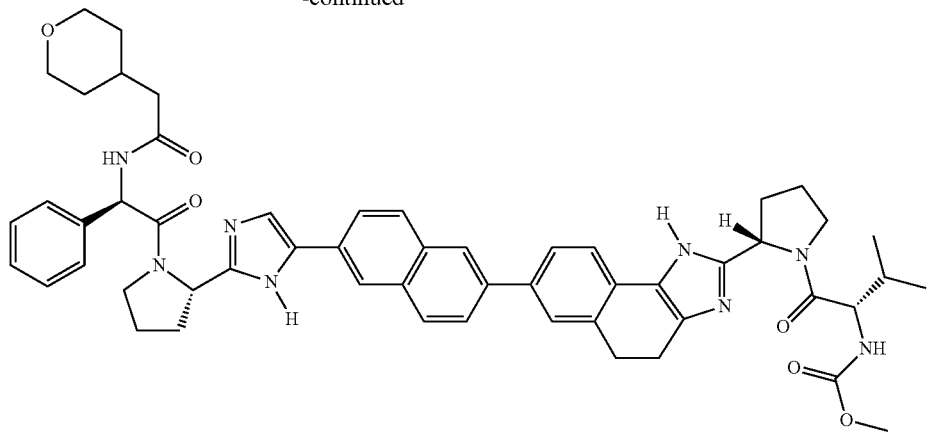

[2-Methyl-1-(2-{7-[6-(2-{1-[2-phenyl-2-(2-tetrahydro-pyran-4-yl-acetylamino)-acetyl]-
pyrrolidin-2-yl}-3H-imidazol-4-yl)-naphthalen-2-yl]-4,5-dihydro-1H-
naphtho[1,2-d]imidazol-2-yl}-pyrrolidine-1-carbonyl)-propyl]-carbamic acid methyl ester

[2-Methyl-1-(2-{7-[6-(2-{1-[2-phenyl-2-(2-tetrahydro-pyran-4-yl-acetylamino)-acetyl]-pyrrolidin-2-yl}-3H-imidazol-4-yl)-naphthalen-2-yl]-4,5-dihydro-1H-naphtho[1,2-d]imidazol-2-yl}-pyrrolidine-1-carbonyl)-propyl]-carbamic acid methyl ester: This compound was prepared using the same procedure used to make {2-Methyl-1-[2-(5-{6-[4-(2-{1-[2-phenyl-2-(2-tetrahydro-pyran-4-yl-acetylamino)-acetyl]-pyrrolidin-2-yl}-3H-imidazol-4-yl)-phenyl]-naphthalen-2-yl}-1H-imidazol-2-yl)-pyrrolidine-1-carbonyl]-propyl}-carbamic acid methyl ester using (1-{2-[7-(6-{2-[1-(2-Amino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester (0.020g, 0.022 mmol) to give [2-Methyl-1-(2-{7-[6-(2-{1-[2-phenyl-2-(2-tetrahydro-pyran-4-yl-acetylamino)-acetyl]-pyrrolidin-2-yl}-3H-imidazol-4-yl)-naphthalen-2-yl]-4,5-dihydro-1H-naphtho[1,2-d]imidazol-2-yl}-pyrrolidine-1-carbonyl)-propyl]-carbamic acid methyl ester (0.003g, 15% yield). LCMS-ESI$^+$: calc'd for $C_{54}H_{60}N_8O_6$: 916.46 (M$^+$); Found: 917.44 (M+H$^+$).

Example HK

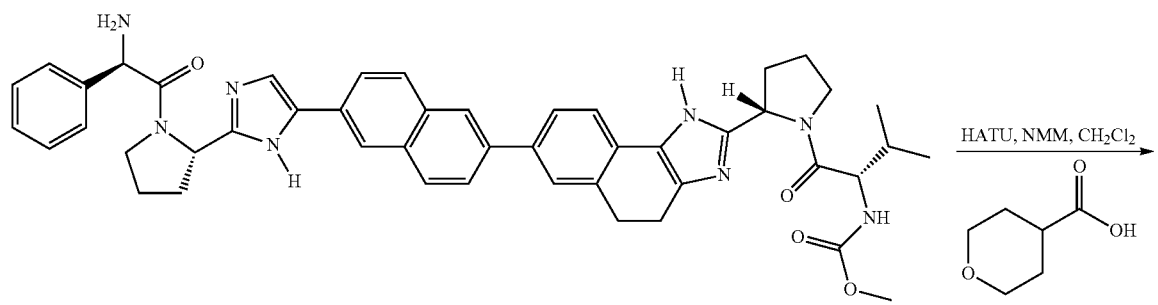

(1-{2-[7-(6-{2-[1-(2-Amino-2-phenyl-acetyl)-pyrrolidin-2-yl]-3H-imidazol-4-yl}-
naphthalen-2-yl)-4,5-dihydro-1H-naphtho[1,2-d]imidazol-2-yl]-pyrrolidine-
1-carbonyl}-2-methyl-propyl)-carbamic acid methyl ester Tetrahydro-pyran-4-
carboxylic acid

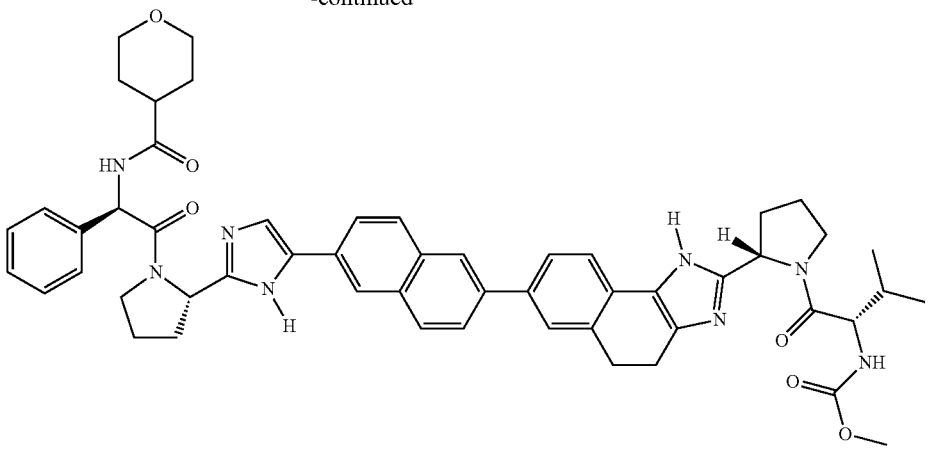

{2-Methyl-1-[2-(7-{6-[2-(1-{2-phenyl-2-[(tetrahydro-pyran-4-carbonyl)-amino]-acetyl}-pyrrolidin-2-yl)-3H-imidazol-4-yl]-naphthalen-2-yl}-4,5-dihydro-1H-naphtho[1,2-d]imidazol-2-yl)-pyrrolidine-1-carbonyl]-propyl}-carbamic acid methyl ester {2-Methyl-1-[2-(7-{6-[2-(1-{2-phenyl-2-[(tetrahydro-pyran-4-carbonyl)-amino]-acetyl}-pyrrolidin-2-yl)-3H-imidazol-4-yl]-naphthalen-2-yl}-4,5-dihydro-1H-naphtho[1,2-d]imidazol-2-yl)-pyrrolidine-1-carbonyl]-propyl}-carbamic acid methyl ester: This compound was prepared using the same procedure used to make {2-Methyl-1-[2-(5-{6-[4-(2-{1-[2-phenyl-2-(2-tetrahydro-pyran-4-yl-acetylamino)-acetyl]-pyrrolidin-2-yl}-3H-imidazol-4-yl)-phenyl]-naphthalen-2-yl}-1H-imidazol-2-yl)-pyrrolidine-1-carbonyl]-propyl}-carbamic acid methyl ester using (1-{2-[7-(6-{2-[1-(2-Amino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester (0.046g, 0.051 mmol) to give {2-Methyl-1-[2-(7-{6-[2-(1-{2-phenyl-2-[(tetrahydro-pyran-4-carbonyl)-amino]-acetyl}-pyrrolidin-2-yl)-3H-imidazol-4-yl]-naphthalen-2-yl}-4,5-dihydro-1H-naphtho[1,2-d]imidazol-2-yl)-pyrrolidine-1-carbonyl]-propyl}-carbamic acid methyl ester (0.061g, >99% yield). LCMS-ESI$^+$: calc'd for $C_{53}H_{58}N_8O_6$: 902.45 (M$^+$); Found: 904.02 (M+H$^+$).

Example HL

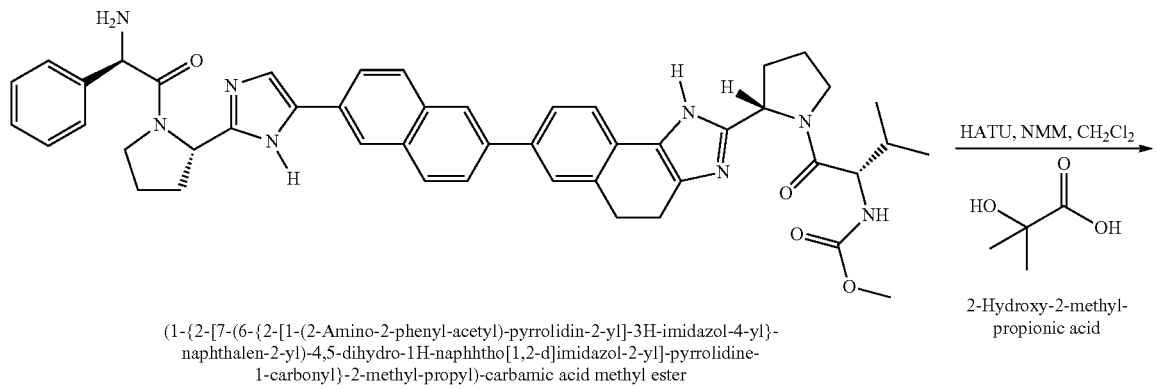

(1-{2-[7-(6-{2-[1-(2-Amino-2-phenyl-acetyl)-pyrrolidin-2-yl]-3H-imidazol-4-yl}-naphthalen-2-yl)-4,5-dihydro-1H-naphhtho[1,2-d]imidazol-2-yl]-pyrrolidine-1-carbonyl}-2-methyl-propyl)-carbamic acid methyl ester 2-Hydroxy-2-methyl-propionic acid

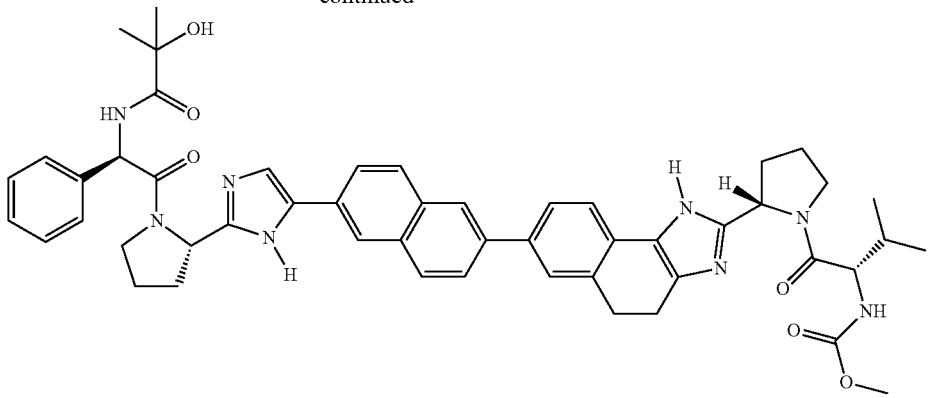

[1-(2-{7-[6-(2-{1-[2-(2-Hydroxy-2-methyl-propionylamino)-2-phenyl-acetyl]-
pyrrolidin-2-yl}-3H-imidazol-4-yl)-naphthalen-2-yl]-4,5-dihydro-1H-
naphtho[1,2-d]imidazol-2-yl}-pyrrolidine-1-carbonyl)-2-methyl-propyl]-
carbamic acid methyl ester

[1-(2-{7-[6-(2-{1-[2-(2-Hydroxy-2-methyl-propionylamino)-2-phenyl-acetyl]-pyrrolidin-2-yl}-3H-imidazol-4-yl)-naphthalen-2-yl]-4,5-dihydro-1H-naphtho[1,2-d]imidazol-2-yl}-pyrrolidine-1-carbonyl)-2-methyl-propyl]-carbamic acid methyl ester: This compound was prepared using the same procedure used to make {2-Methyl-1-[2-(5-{6-[4-(2-{1-[2-phenyl-2-(2-tetrahydro-pyran-4-yl-acetylamino)-acetyl]-pyrrolidin-2-yl}-3H-imidazol-4-yl)-phenyl]-naphthalen-2-yl}-1H-imidazol-2-yl)-pyrrolidine-1-carbonyl]-propyl}-carbamic acid methyl ester using (1-{2-[7-(6-{2-[1-(2-Amino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester (0.048g, 0.053 mmol) to give [1-(2-{7-[6-(2-{1-[2-(2-Hydroxy-2-methyl-propionylamino)-2-phenyl-acetyl]-pyrrolidin-2-yl}-3H-imidazol-4-yl)-naphthalen-2-yl]-4,5-dihydro-1H-naphtho[1,2-d]imidazol-2-yl}-pyrrolidine-1-carbonyl)-2-methyl-propyl]-carbamic acid methyl ester (0.0145g, 31% yield). LCMS-ESI+: calc'd for $C_{51}H_{56}N_8O_6$: 876.43 (M+); Found: 878.01 (M+H+).

Example HM

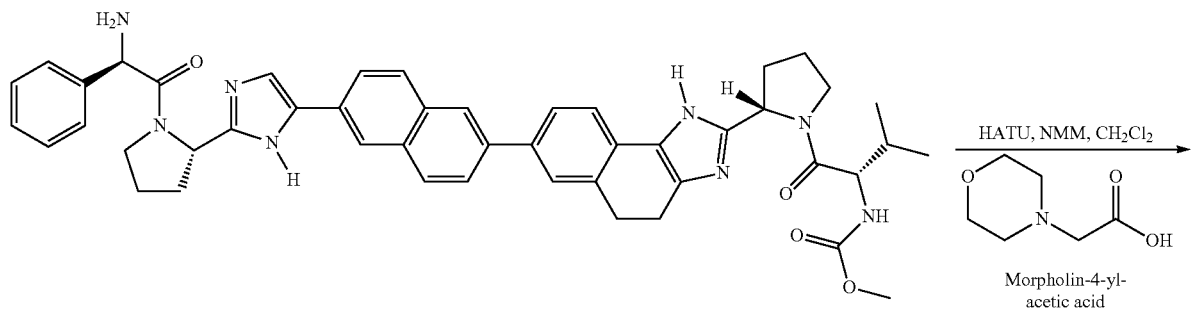

(1-{2-[7-(6-{2-[1-(2-Amino-2-phenyl-acetyl)-pyrrolidin-2-yl]-3H-imidazol-4-yl}-
naphthalen-2-yl)-4,5-dihydro-1H-naphtho[1,2-d]imidazol-2-yl]-pyrrolidine-
1-carbonyl}-2-methyl-propyl)-carbamic acid methyl ester Morpholin-4-yl-
acetic acid

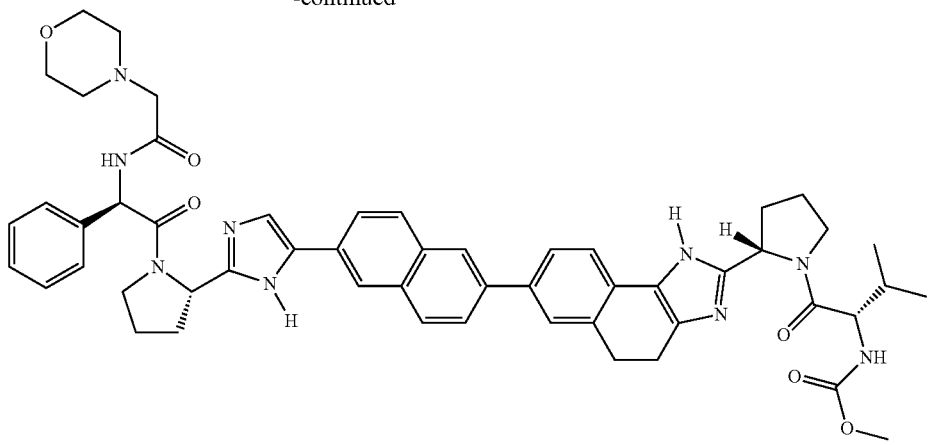

[2-Methyl-1-(2-{7-[6-(2-{1-[2-(2-morpholin-4-yl-acetylamino)-
2-phenyl-acetyl]-pyrrolidin-2-yl}-3H-imidazol-4-yl]-naphthalen-2-yl]-
4,5-dihydro-1H-naphtho[1,2-d]imidazol-2-yl}-pyrrolidine-1-carbonyl)-
propyl]-carbamic acid methyl ester

[2-Methyl-1-(2-{7-[6-(2-{1-[2-(2-morpholin-4-yl-acetylamino)-2-phenyl-acetyl]-pyrrolidin-2-yl}-3H-imidazol-4-yl)-naphthalen-2-yl]-4,5-dihydro-1H-naphtho[1,2-d]imidazol-2-yl}-pyrrolidine-1-carbonyl)-propyl]-carbamic acid methyl ester: This compound was prepared using the same procedure used to make {2-Methyl-1-[2-(5-{6-[4-(2-{1-[2-phenyl-2-(2-tetrahydro-pyran-4-yl-acetylamino)-acetyl]-pyrrolidin-2-yl}-3H-imidazol-4-yl)-phenyl]-naphthalen-2-yl}-1H-imidazol-2-yl)-pyrrolidine-1-carbonyl]-propyl}-carbamic acid methyl ester using (1-{2-[7-(6-{2-[1-(2-Amino-2-phenyl-acetyl)-pyrrolidin-2-yl]-3H-imidazol-4-yl}-naphthalen-2-yl)-4,5-dihydro-1H-naphtho[1,2-d]imidazol-2-yl]-pyrrolidine-1-carbonyl}-2-methyl-propyl)-carbamic acid methyl ester (0.043 g, 0.050 mmol) to give [2-Methyl-1-(2-{7-[6-(2-{1-[2-(2-morpholin-4-yl-acetylamino)-2-phenyl-acetyl]-pyrrolidin-2-yl}-3H-imidazol-4-yl)-naphthalen-2-yl]-4,5-dihydro-1H-naphtho[1,2-d]imidazol-2-yl}-pyrrolidine-1-carbonyl)-propyl]-carbamic acid methyl ester (0.021g, 45% yield). LCMS-ESI$^+$: calc'd for $C_{53}H_{59}N_9O_6$: 917.46 (M$^+$); Found: 918.54 (M+H$^+$).

Example HN

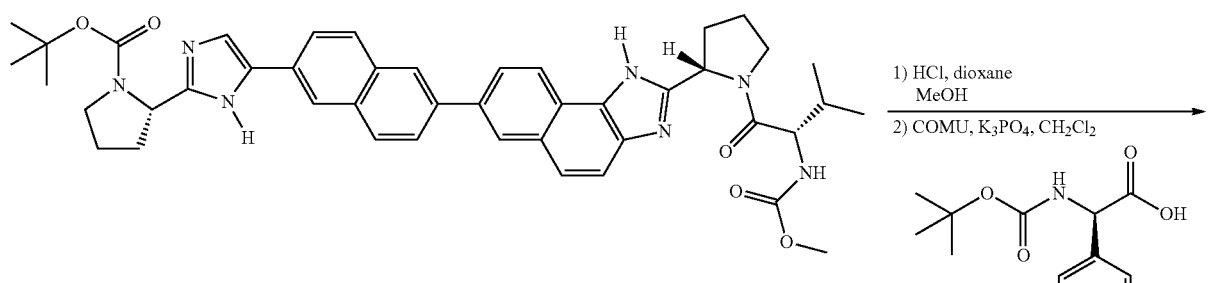

2-[5-(6-(2-[1-(2-Methoxycarbonylamino-3-methyl-butyryl)-pyrrolidin-2-yl]-
1H-naphtho[1,2-d]imidazol-7-yl}-naphthalen-2-yl)-1H-imidazol-2-yl]-
pyrrolidine-1-carboxylic acid tert-butyl ester tert-Butoxycarbonylamino-
phenyl-acetic acid

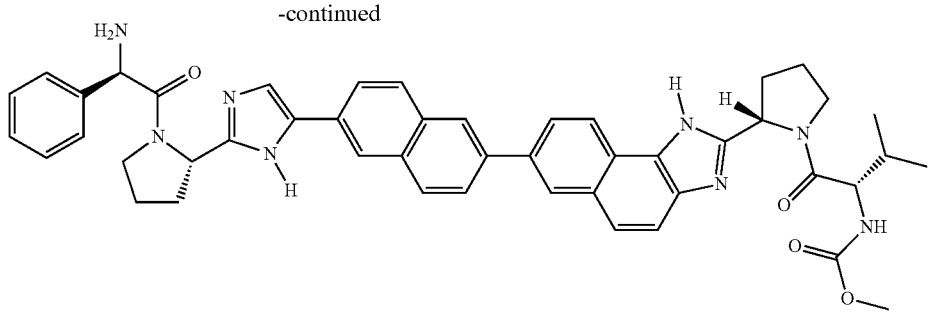

(1-{2-[7-(6-{2-[1-(2-Amino-2-phenyl-acetyl)-pyrrolidin-2-yl]-
3H-imidazol-4-yl}-naphthalen-2-yl)-1H-naphtho[1,2-d]imidazol-2-yl]-pyrrolidine-
1-carbonyl}-2-methyl-propyl)-carbamic acid methyl ester (1-{2-[7-(6-{2-[1-(2-Amino-2-phenyl-acetyl)-pyrrolidin-2-yl]-3H-imidazol-4-yl}-naphthalen-2-yl)-1H-naphtho[1,2-d]imidazol-2-yl]-pyrrolidine-1-carbonyl}-2-methyl-propyl)-carbamic acid methyl ester: This compound was synthesized from 2-[5-(6-{2-[1-(2-Methoxycarbonylamino-3-methyl-butyryl)-pyrrolidin-2-yl]-1H-naphtho[1,2-d]imidazol-7-yl}-naphthalen-2-yl)-1H-imidazol-2-yl]-pyrrolidine-1-carboxylic acid tert-butyl ester (0.590 g, 0.78 mmol) using the three step sequence used to make [1-(2-{5-[6-(4-{2-[1-(2-Amino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-2-methyl-propyl]-carbamic acid methyl ester from 2-{5-[4-(6-{2-[1-(2-Methoxycarbonylamino-3-methyl-butyryl)-pyrrolidin-2-yl]-3H-imidazol-4-yl}-naphthalen-2-yl)-phenyl]-1H-imidazol-2-yl}-pyrrolidine-1-carboxylic acid tert-butyl ester, giving the title compound (0.277 mmol, 35% yield over three steps). LCMS-ESI⁺: calc'd for $C_{47}H_{48}N_8O_4$: 788.38 (M⁺); Found: 790.1 (M+H⁺).

Example HO

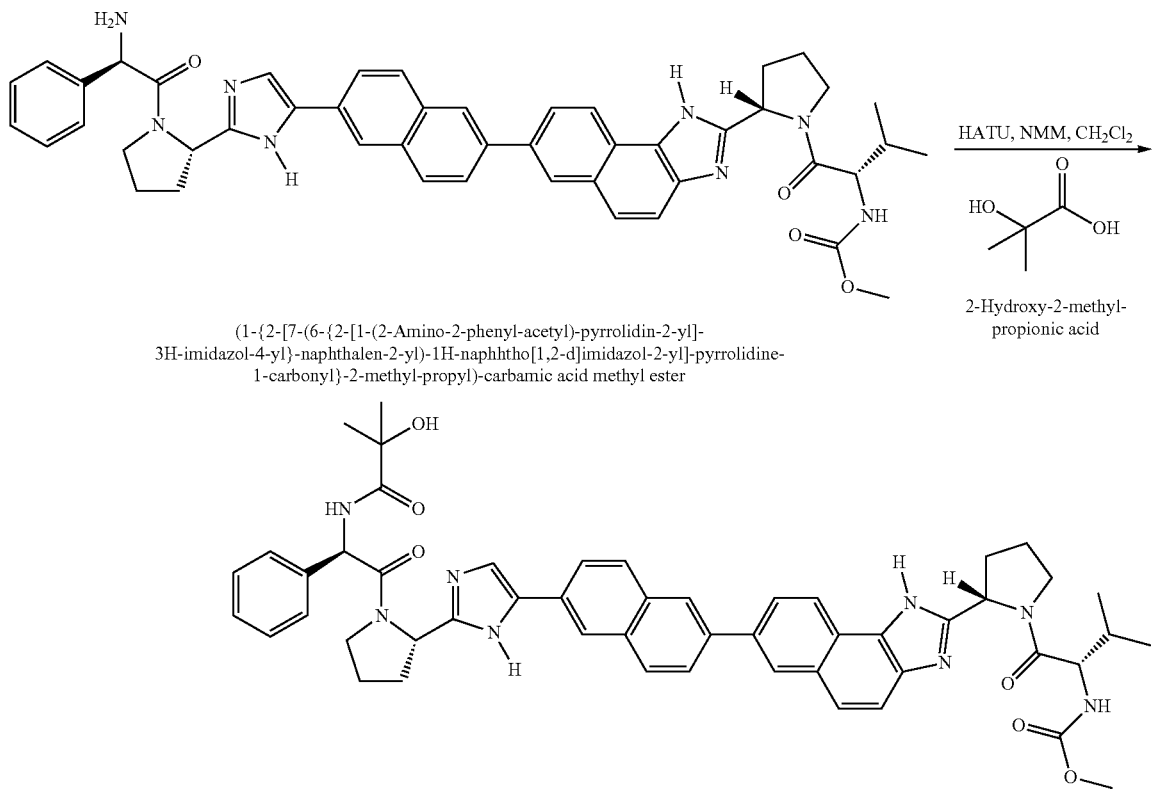

(1-{2-[7-(6-{2-[1-(2-Amino-2-phenyl-acetyl)-pyrrolidin-2-yl]-
3H-imidazol-4-yl}-naphthalen-2-yl)-1H-naphhtho[1,2-d]imidazol-2-yl]-pyrrolidine-
1-carbonyl}-2-methyl-propyl)-carbamic acid methyl ester 2-Hydroxy-2-methyl-
propionic acid

[1-(2-{7-[6-(2-{1-[2-(2-Hydroxy-2-methyl-propionylamino)-
2-phenyl-acetyl]-pyrrolidin-2-yl}-3H-imidazol-4-yl)-naphthalen-2-yl]-
1H-naphtho[1,2-d]imidazol-2-yl}-pyrrolidine-1-carbonyl)-2-methyl-propyl]-
carbamic acid methyl ester

[1-(2-{7-[6-(2-{1-[2-(2-Hydroxy-2-methyl-propionylamino)-2-phenyl-acetyl]-pyrrolidin-2-yl}-3H-imidazol-4-yl)-naphthalen-2-yl]-1H-naphtho[1,2-d]imidazol-2-yl}-pyrrolidine-1-carbonyl)-2-methyl-propyl]-carbamic acid methyl ester: This compound was prepared using the same procedure used to make {2-Methyl-1-[2-(5-{6-[4-(2-{1-[2-phenyl-2-(2-tetrahydro-pyran-4-yl-acetylamino)-acetyl]-pyrrolidin-2-yl}-3H-imidazol-4-yl)-phenyl]-naphthalen-2-yl}-1H-imidazol-2-yl)-pyrrolidine-1-carbonyl]-propyl}-carbamic acid methyl ester using (1-{2-[7-(6-{2-[1-(2-Amino-2-phenyl-acetyl)-pyrrolidin-2-yl]-3H-imidazol-4-yl}-naphthalen-2-yl)-1H-naphtho[1,2-d]imidazol-2-yl]-pyrrolidine-1-carbonyl}-2-methyl-propyl)-carbamic acid methyl ester (0.247g, 0.227 mmol) to give [1-(2-{7-[6-(2-{1-[2-(2-Hydroxy-2-methyl-propionylamino)-2-phenyl-acetyl]-pyrrolidin-2-yl}-3H-imidazol-4-yl)-naphthalen-2-yl]-1H-naphtho[1,2-d]imidazol-2-yl}-pyrrolidine-1-carbonyl)-2-methyl-propyl]-carbamic acid methyl ester (0.074g, 31% yield). LCMS-ESI⁺: calc'd for $C_{51}H_{54}N_8O_6$: 874.42 (M⁺); Found: 875.5 (M+H⁺).

Example HP

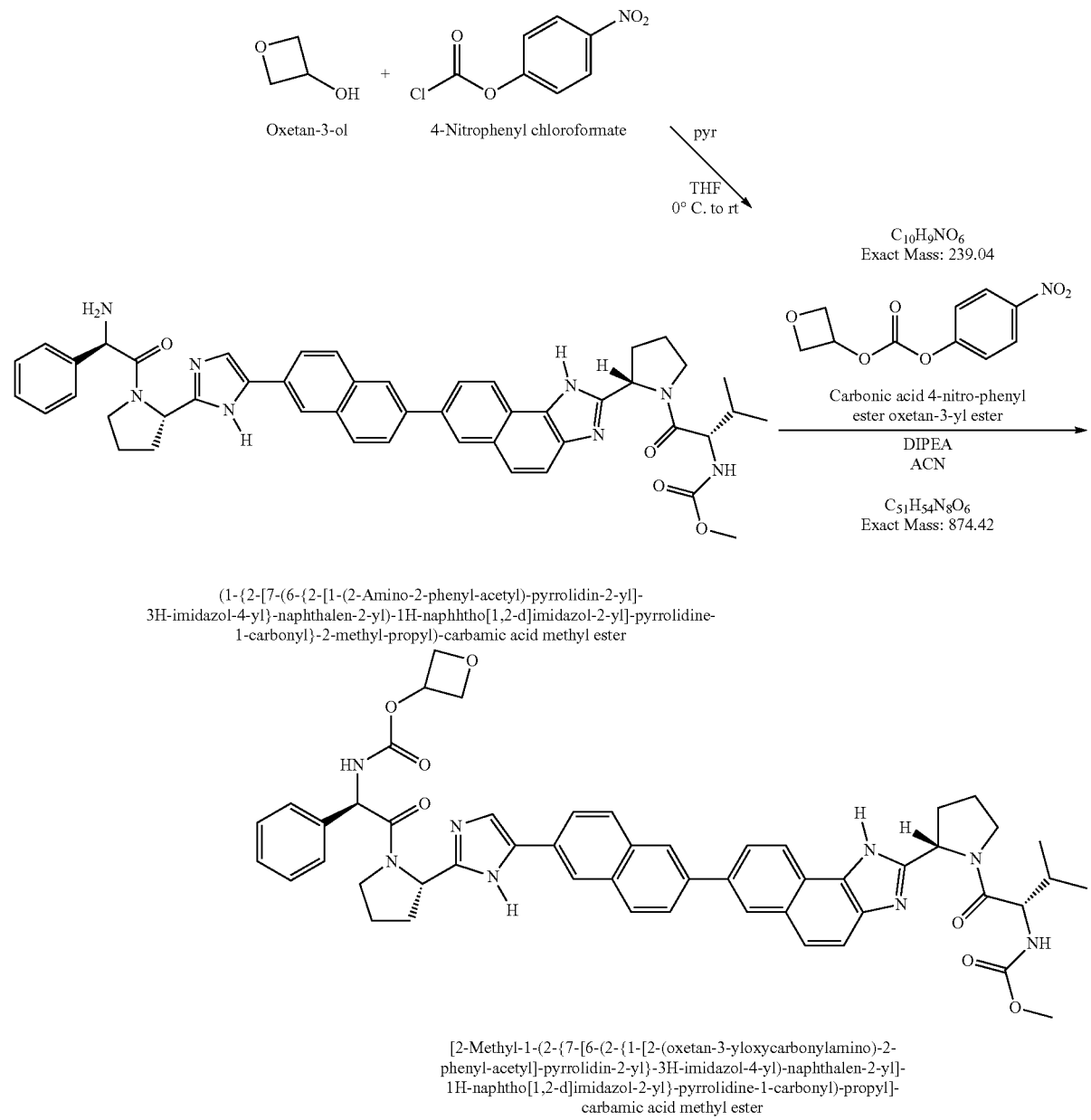

Carbonic acid 4-nitro-phenyl ester oxetan-3-yl ester: A solution of Oxetan-3-ol (0.100g, 1.35 mmol) and pyridine (0.13 mL, 1.62 mmol) in THF (2.5 mL) was cooled to 0° C. with an external ice bath, stirring. A solution of 4-Nitrophenyl chloroformate (0.299g, 1.485 mmol) in THF (2 mL) was added at 0° C. and the solution was allowed to warm to room temperature. The crude reaction was purified by normal phase silica gel (0-100% ethyl acetate:hexanes) chromatography to give Carbonic acid 4-nitro-phenyl ester oxetan-3-yl ester. LCMS-ESI+: calc'd for $C_{10}H_9NO_6$: 239.04 (M+); Found: 239.97 (M+H+).

[2-Methyl-1-(2-{7-[6-(2-{1-[2-(oxetan-3-yloxycarbonylamino)-2-phenyl-acetyl]-pyrrolidin-2-yl}-3H-imidazol-4-yl)-naphthalen-2-yl]-1H-naphtho[1,2-d]imidazol-2-yl}-pyrrolidine-1-carbonyl)-propyl]-carbamic acid methyl ester: (1-{2-[7-(6-{2-[1-(2-Amino-2-phenyl-acetyl)-pyrrolidin-2-yl]-3H-imidazol-4-yl}-naphthalen-2-yl)-1H-naphtho[1,2-d]imidazol-2-yl]-pyrrolidine-1-carbonyl}-2-methyl-propyl)-carbamic acid methyl ester (0.200g, 0.22 mmol) was dissolved in acetonitrile (2.2 mL). DIPEA (0.155 mL, 0.8905 mmol) and Carbonic acid 4-nitro-phenyl ester oxetan-3-yl ester (0.059g, 0.244 mmol) was added, and the solution was allowed to stir for about three hours. Upon completion, the crude product was purified by reverse phase HPLC (10-50% acetonitrile:water; 0.1% formic acid modifier), and lyophilized giving [2-Methyl-1-(2-{7-[6-(2-{1-[2-(oxetan-3-yloxycarbonylamino)-2-phenyl-acetyl]-pyrrolidin-2-yl}-3H-imidazol-4-yl)-naphthalen-2-yl]-1H-naphtho[1,2-d]imidazol-2-yl}-pyrrolidine-1-carbonyl)-propyl]-carbamic acid methyl ester (0.61g, 31% yield). LCMS-ESI+: calc'd for $C_{51}H_{52}N_8O_7$: 888.40 (M+); Found: 889.86 (M+H+).

Example HQ

{2-Methyl-1-[2-(7-{6-[2-(1-{2-[(morpholine-4-carbonyl)-amino]-2-phenyl-acetyl}-pyrrolidin-2-yl)-3H-imidazol-4-yl]-naphthalen-2-yl}-1H-naphtho[1,2-d]imidazol-2-yl)-pyrrolidine-1-carbonyl]-propyl}-carbamic acid methyl ester: This compound was synthesized using the same procedure used to make [2-Methyl-1-(2-{5-[6-(4-{2-[1-(2-phenyl-2-propionylamino-acetyl)-pyrrolidin-2-yl]-3H-imidazol-4-yl}-phenyl)-naphthalen-2-yl]-1H-imidazol-2-yl}-pyrrolidine-1-carbonyl)-propyl]-carbamic acid methyl ester using (1-{2-[7-(6-{2-[1-(2-Amino-2-phenyl-acetyl)-pyrrolidin-2-yl]-3H-imidazol-4-yl}-naphthalen-2-yl)-1H-naphtho[1,2-d]imidazol-2-yl]-pyrrolidine-1-carbonyl}-2-methyl-propyl)-carbamic acid methyl ester (0.200g, 0.222 mmol) to give {2-Methyl-1-[2-(7-{6-[2-(1-{2-[(morpholine-4-carbonyl)-amino]-2-phenyl-acetyl}-pyrrolidin-2-yl)-3H-imidazol-4-yl]-naphthalen-2-yl}-1H-naphtho[1,2-d]imidazol-2-yl)-pyrrolidine-1-carbonyl]-propyl}-carbamic acid methyl ester (0.036g, 18% yield). LCMS-ESI+: calc'd for $C_{52}H_{55}N_9O_6$: 901.43 (M+); Found: 902.60 (M+H+).

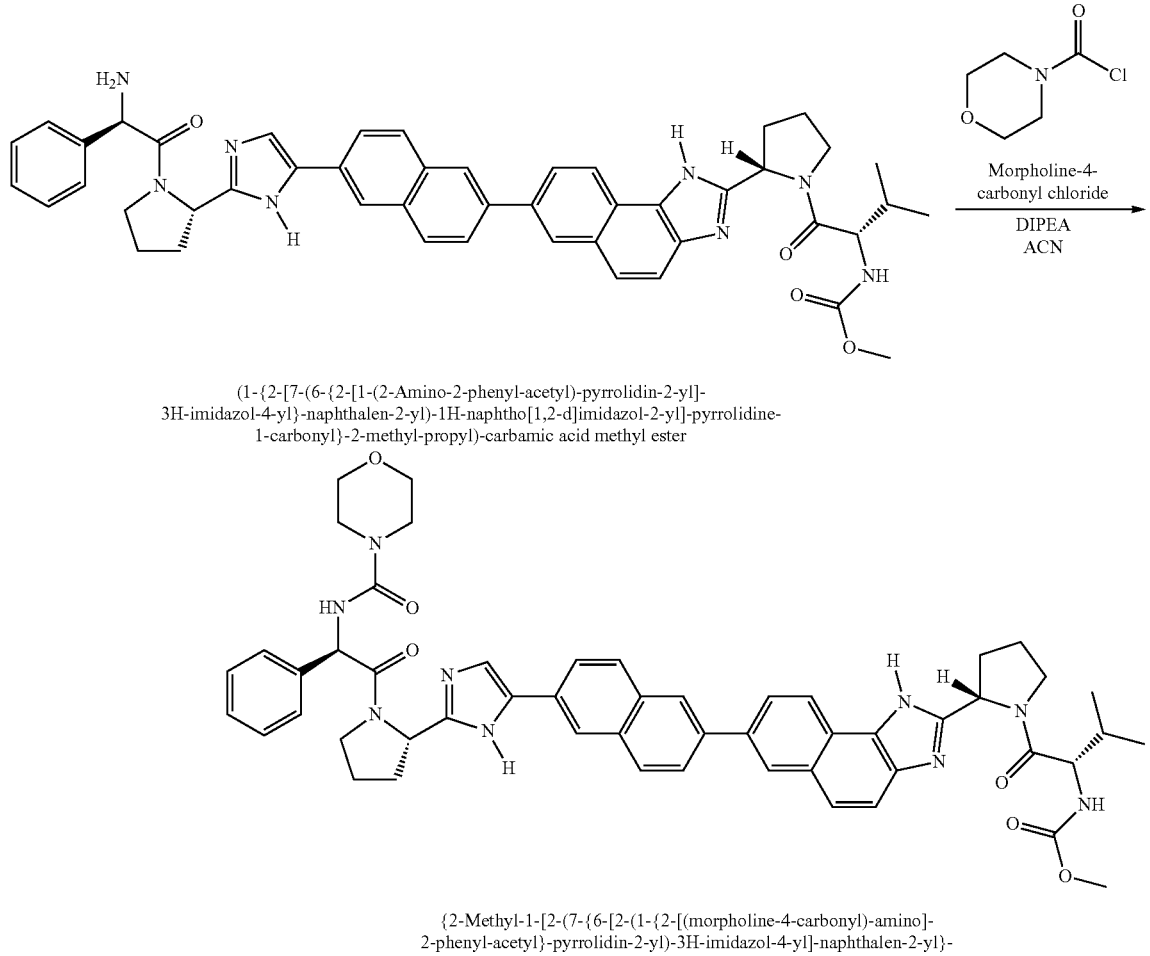

(1-{2-[7-(6-{2-[1-(2-Amino-2-phenyl-acetyl)-pyrrolidin-2-yl]-3H-imidazol-4-yl}-naphthalen-2-yl)-1H-naphtho[1,2-d]imidazol-2-yl]-pyrrolidine-1-carbonyl}-2-methyl-propyl)-carbamic acid methyl ester {2-Methyl-1-[2-(7-{6-[2-(1-{2-[(morpholine-4-carbonyl)-amino]-2-phenyl-acetyl}-pyrrolidin-2-yl)-3H-imidazol-4-yl]-naphthalen-2-yl}-1H-naphtho[1,2-d]imidazol-2-yl)-pyrrolidine-1-carbonyl]-propyl}-carbamic acid methyl ester Example HR
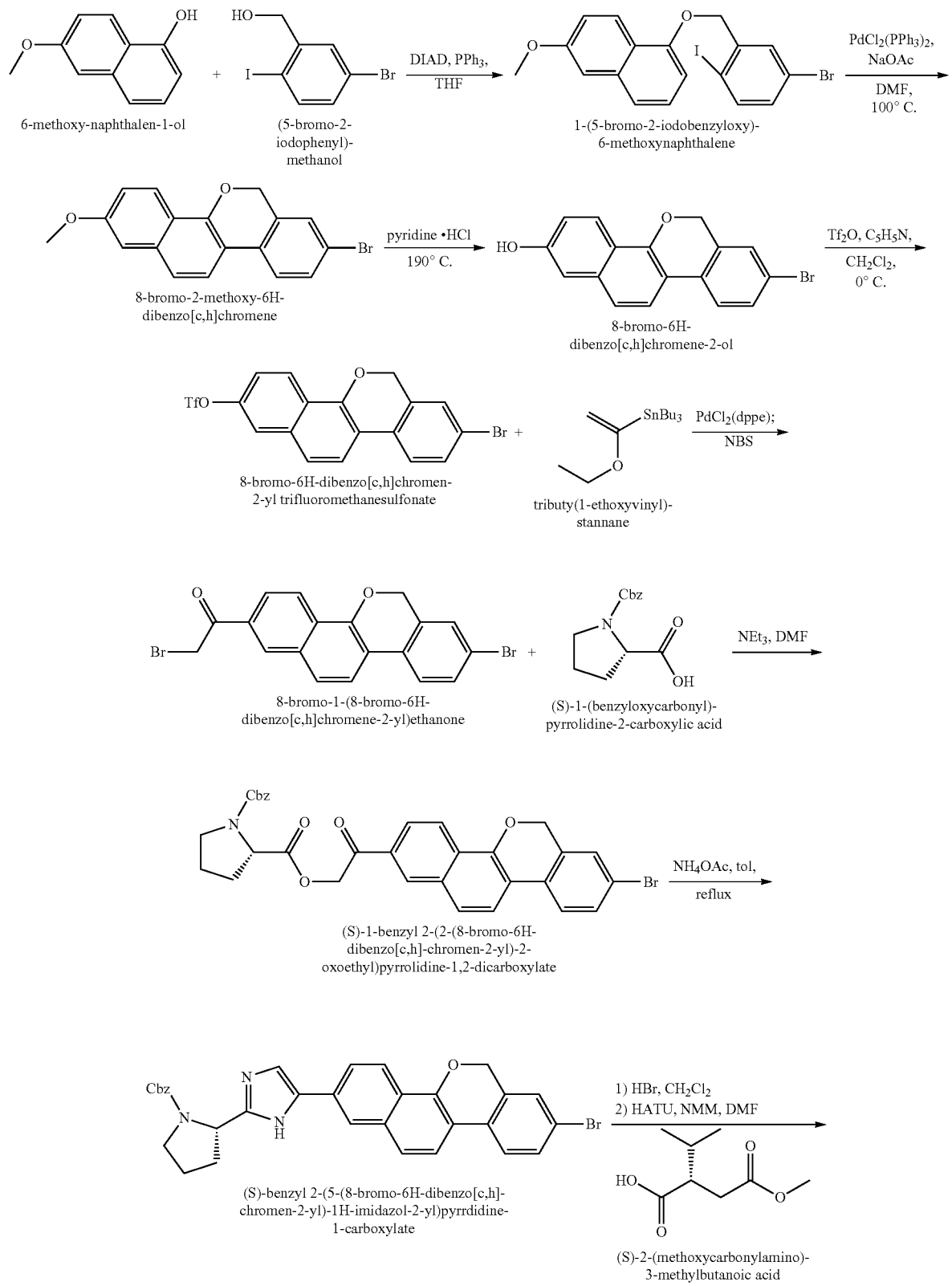

-continued

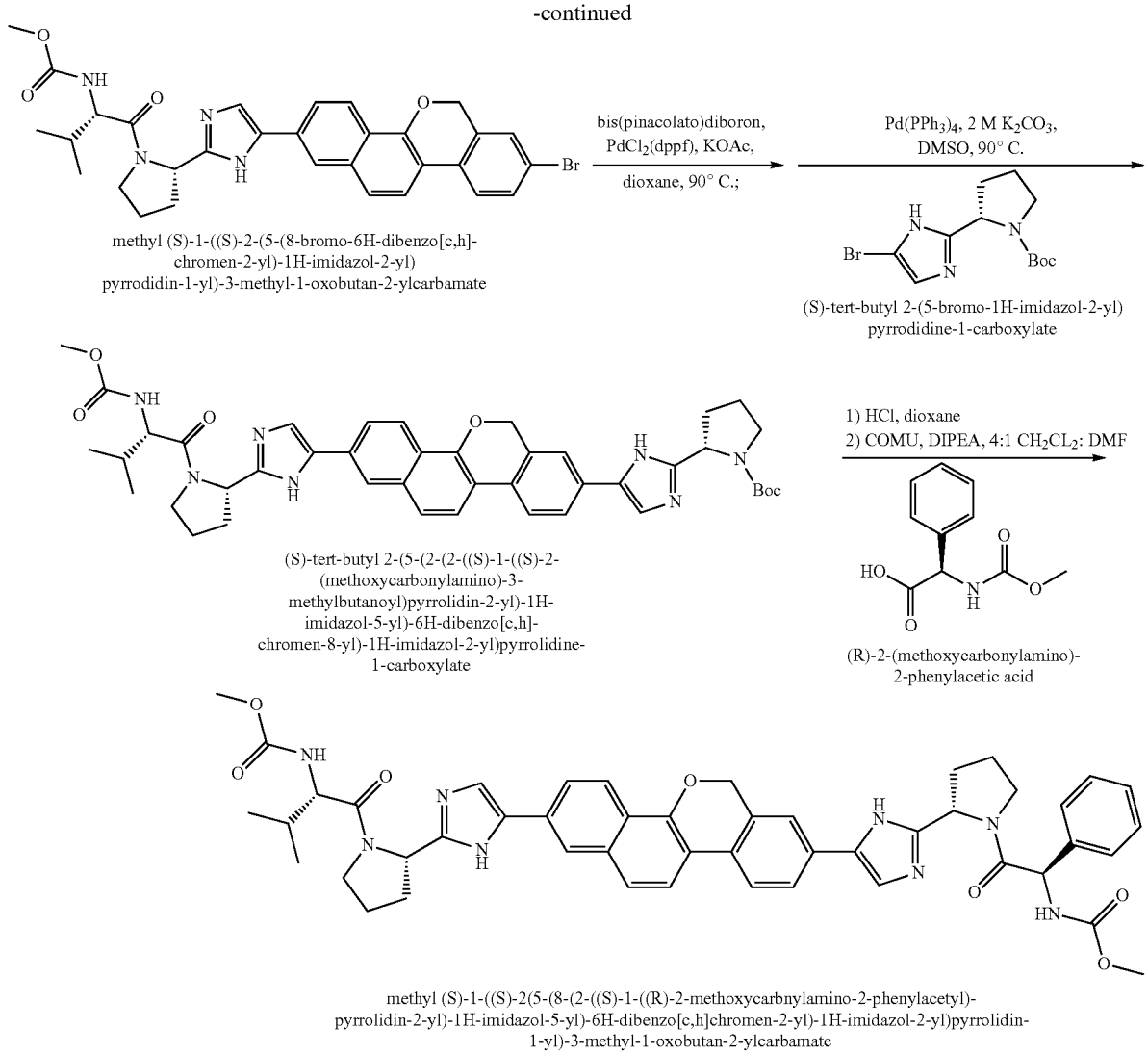

1-(5-bromo-2-iodobenzyloxy)-6-methoxynaphthalene:
To a solution of 6-methoxynaphthalen-1-ol (4.45 g, 25.6 mmol), (5-bromo-2-iodophenyl)methanol (8.0 g, 25.6 mmol) and triphenylphosphine (7.4 g, 28.2 mmol) in tetrahydrofuran (128 mL) at 0° C. was added diisopropyl azodicarboxylate (5.54 mL, 28.2 mmol). The reaction was allowed to warm to room temperature overnight. After 15 hours, more triphenylphosphine (1.3 g, 5 mmol) and diisopropyl azodicarboxylate (0.99 mL, 5 mmol) were added and the reaction was stirred at room temperature. After 24 hours, the reaction was concentrated and recrystallized from $CH_2Cl_2$ and hexanes to yield 1-(5-bromo-2-iodobenzyloxy)-6-methoxynaphthalene (7.82 g, 65%). The mother liquor was purified by flash column chromatography to yield more product (790 mg, 6.5%).

8-bromo-2-methoxy-6H-dibenzo[c,h]chromene: A mixture of 1-(5-bromo-2-iodobenzyloxy)-6-methoxynaphthalene (5.0 g, 10.7 mmol) and sodium acetate (2.64 g, 32.1 mmol) in dimethylformamide (100 mL) was degassed with a stream of argon for 15 minutes. $PdCl_2(PPh_3)_2$ was added and the reaction was heated to 110° C. After 16 hours the reaction was diluted with ethyl acetate, washed with water and brine, dried ($Na_2SO_4$) and concentrated. The resulting residue was purified by flash column chromatography to yield 8-bromo-2-methoxy-6H-dibenzo[c,h]chromene (1.29 g, 35%).

8-bromo-6H-dibenzo[c,h]-chromen-2-ol: Pyridine hydrochloride (4.4 g, 37.8 mmol) was heated to 190° C. 8-bromo-2-methoxy-6H-dibenzo[c,h]chromene (1.29 g, 3.8 mmol) was added and the reaction was stirred at 190° C. After four hours, the reaction was cooled to room temperature and diluted with water. A precipitate formed which was collected by filtration and purified by flash column chromatography to yield 8-bromo-6H-dibenzo[c,h]-chromen-2-ol (697 mg, 56%).

8-bromo-6H-dibenzo[c,h]chromen-2-yl trifluoromethanesulfonate: To a solution of 8-bromo-6H-dibenzo[c,h]-chromen-2-ol (697 mg, 2.1 mmol) and pyridine (0.23 mL, 2.8 mmol) in dichloromethane (25 mL) at 0° C. was added trifluoromethanesulfonic anhydride (0.39 mL, 2.3 mmol). After stirring for 2 hours, the reaction was poured into 1M aqueous HCl solution. The organic phase was separated and the aqueous phase was extracted with dichloromethane. The combined organic layers were washed with brine, dried ($Na_2SO_4$) and concentrated. The crude material was purified by flash column chromatography to yield 8-bromo-6H-dibenzo[c,h]chromen-2-yl trifluoromethanesulfonate (889 mg, 91%).

2-bromo-1-(8-bromo-6H-dibenzo[c,h]chromen-2-yl)ethanone: A solution of 8-bromo-6H-dibenzo[c,h]chromen-2-yl trifluoromethanesulfonate (780 mg, 1.7 mmol) and tributyl(1-ethoxyvinyl)stannane (0.86 mL, 2.6 mmol) in dimethylformamide was degassed with a stream of argon for 15 minutes. $PdCl_2$(dppe) (50 mg, 0.086 mmol) was added and the reaction was stirred at room temperature. After 30 hours, water (1 mL) and N-bromosuccinimide (756 mg, 4.2 mmol) were sequentially added to the reaction. After stirring for 2.5 hours at room temperature the reaction was diluted with dichloromethane. The organics were washed with 5% aqueous LiCl solution, saturated aqueous $NaHCO_3$ solution, and brine. After the organic layer was dried ($Na_2SO_4$) and concentrated, the crude material was recrystallized from dichloromethane and hexanes to yield 2-bromo-1-(8-bromo-6H-dibenzo[c,h]chromen-2-yl)ethanone (518 mg, 57%).

(S)-1-benzyl 2-(2-(8-bromo-6H-dibenzo[c,h]chromen-2-yl)-2-oxoethyl) pyrrolidine-1,2-dicarboxylate: To a mixture of 2-bromo-1-(8-bromo-6H-dibenzo[c,h]chromen-2-yl)ethanone (518 mg, 1.2 mmol) and (S)-1-(benzyloxycarbonyl)-pyrrolidine-2-carboxylic acid (449 mg, 1.8 mmol) in dimethylformamide (12 mL) was added triethylamine (0.25 mL, 1.8 mmol). After stirring for 2 hours at room temperature, the reaction was diluted with 5% aqueous LiCl solution. The aqueous phase was extracted twice with ethyl acetate. The combined organics were washed with 1M aqueous HCl solution, saturated aqueous $NaHCO_3$ solution and brine. After the organic layer was dried ($Na_2SO_4$) and concentrated, the crude material was purified by flash column chromatography to yield (S)-1-benzyl 2-(2-(8-bromo-6H-dibenzo[c,h]chromen-2-yl)-2-oxoethyl) pyrrolidine-1,2-dicarboxylate (620 mg, 86%).

(S)-benzyl 2-(5-(8-bromo-6H-dibenzo[c,h]chromen-2-yl)-1H-imidazol-2-yl)pyrrolidine-1-carboxylate: A mixture of (S)-1-benzyl 2-(2-(8-bromo-6H-dibenzo[c,h]chromen-2-yl)-2-oxoethyl) pyrrolidine-1,2-dicarboxylate (641 mg, 1.1 mmol) and ammonium acetate (823 mg, 10.7 mmol) in toluene (11 mL) was vigorously refluxed. After 8 hours, the reaction was cooled to room temperature and poured into water. The aqueous phase was extracted twice with ethyl acetate. The combined organic layers were washed with saturated aqueous $NaHCO_3$ and brine, dried ($Na_2SO_4$) and concentrated. The crude material was purified by flash column chromatography to yield (S)-benzyl 2-(5-(8-bromo-6H-dibenzo[c,h]chromen-2-yl)-1H-imidazol-2-yl)pyrrolidine-1-carboxylate (541 mg, 87%).

Methyl (S)-1-((S)-2-(5-(8-bromo-6H-dibenzo[c,h]chromen-2-yl)-1H-imidazol-2-yl)pyrrolidin-1-yl)-3-methyl-1-oxobutan-2-ylcarbamate: A solution of (S)-benzyl 2-(5-(8-bromo-6H-dibenzo[c,h]chromen-2-yl)-1H-imidazol-2-yl)pyrrolidine-1-carboxylate (485 mg, 0.84 mmol), hydrogen bromide (33% in acetic acid, 1 mL) and dichloromethane (2 mL) was stirred at room temperature for one hour. The reaction was concentrated, suspended in toluene, sonicated for one minute and re-concentrated. The resulting residue was suspended in methanol, sonicated for one minute and concentrated. The resulting residue was suspended in diethyl ether and the solids collected by filtration. This crude amine was dissolved in dimethylformamide (7 mL). To this solution were added (S)-2-(methoxycarbonylamino)-3-methylbutanoic acid (192 mg, 1.1 mmol), HATU (418 mg, 1.1 mmol) and N-methylmorpholine (0.24 mL, 2.2 mmol). The reaction was stirred at room temperature for one hour, and then diluted ethyl acetate. The organic layer was washed with 5% aqueous LiCl solution, saturated aqueous $NaHCO_3$ solution and brine, then dried ($Na_2SO_4$) and concentrated. The crude material was purified by flash column chromatography to yield methyl (S)-1-((S)-2-(5-(8-bromo-6H-dibenzo[c,h]chromen-2-yl)-1H-imidazol-2-yl)pyrrolidin-1-yl)-3-methyl-1-oxobutan-2-ylcarbamate (466 mg, 92%).

(S)-tert-butyl 2-(5-(2-(2-((S)-1-((S)-2-(methoxycarbonylamino)-3-methylbutanoyl)pyrrolidin-2-yl)-1H-imidazol-5-yl)-6H-dibenzo[c,h]-chromen-8-yl)-1H-imidazol-2-yl)pyrrolidine-1-carboxylate: A mixture of methyl (S)-1-((S)-2-(5-(8-bromo-6H-dibenzo[c,h]chromen-2-yl)-1H-imidazol-2-yl)pyrrolidin-1-yl)-3-methyl-1-oxobutan-2-ylcarbamate (466 mg, 0.77 mmol), bis(pinacolato)diboron (235 mg, 0.93 mmol) and potassium acetate (227 mg, 2.3 mmol) in dioxane (4 mL) was degassed with a stream of argon for fifteen minutes. To this mixture was added $PdCl_2$(dppf) (56 mg, 0.08 mmol) and the reaction was heated to 90° C. After 14 hours, the mixture was cooled to room temperature. To the reaction was added (S)-tert-butyl 2-(5-bromo-1H-imidazol-2-yl)pyrrolidine-1-carboxylate (341 mg, 1.1 mmol), 2M aqueous potassium carbonate solution (1.54 mL, 3.1 mmol) and DMSO (3.9 mL). The reaction was degassed with a stream of argon for fifteen minutes. Tetrakis(triphenylphosphine)palladium(0) (89 mg, 0.08 mmol) was added and the reaction was heated to 90° C. After 4.5 hours, the reaction was poured into water. The aqueous phase was extracted twice with ethyl acetate. The combined organic layers were washed with brine, dried ($Na_2SO_4$) and concentrated. The crude material was purified by flash column chromatography to yield (S)-tert-butyl 2-(5-(2-(2-((S)-1-((S)-2-(methoxycarbonylamino)-3-methylbutanoyl)pyrrolidin-2-yl)-1H-imidazol-5-yl)-6H-dibenzo[c,h]-chromen-8-yl)-1H-imidazol-2-yl)pyrrolidine-1-carboxylate (145 mg, 25%).

Methyl (S)-1-((S)-2-(5-(8-(2-((S)-1-((R)-2-methoxycarbonylamino-2-phenylacetyl)-pyrrolidin-2-yl)-1H-imidazol-5-yl)-6H-dibenzo[c,h]chromen-2-yl)-1H-imidazol-2-yl)pyrrolidin-1-yl)-3-methyl-1-oxobutan-2-ylcarbamate: A solution of (S)-tert-butyl 2-(5-(2-(2-((S)-1-((S)-2-(methoxycarbonylamino)-3-methylbutanoyl)pyrrolidin-2-yl)-1H-imidazol-5-yl)-6H-dibenzo[c,h]-chromen-8-yl)-1H-imidazol-2-yl)pyrrolidine-1-carboxylate (80 mg, 0.10 mmol), dioxanes (1 mL), methanol (1 mL), and 4M HCl in dioxane (0.07 mL, 0.28 mmol) was stirred at room temperature. The reaction was thoroughly concentrated after 24 hours.

The resulting residue was dissolved in a 4:1 dichloromethane:dimethylformamide solution (2.5 mL). To this solution was added (R)-2-(methoxycarbonylamino)-2-phenylacetic acid (27 mg, 0.13 mmol) and COMU (64 mg, 0.15 mmol) and the reaction was cooled to 0° C. Diisopropylethylamine (0.035 mL, 0.20 mmol) was added and the reaction was stirred at 0° C. for one hour. The reaction was quenched by the addition of formic acid (0.05 mL) and thoroughly concentrated. The resulting residue was purified by preparative reverse phase HPLC (Gemini, 10 to 60% ACN/$H_2O$+0.1% $HCO_2H$), followed by a second preparative reverse phase HPLC (Gemini, 10 to 60% ACN/$H_2O$+ 0.1% TFA) to yield methyl (S)-1-((S)-2-(5-(8-(2-((S)-1-((R)-2-methoxycarbonylamino-2-phenylacetyl)-pyrrolidin-2-yl)-1H-imidazol-5-yl)-6H-dibenzo[c,h]chromen-2-yl)-1H-imidazol-2-yl)pyrrolidin-1-yl)-3-methyl-1-oxobutan-2-ylcarbamate (47 mg, 52%). LCMS-ESI$^+$: calculated for $C_{48}H_{50}N_8O_7$: 850.96; observed [M+1]$^+$: 851.91.

Example HS

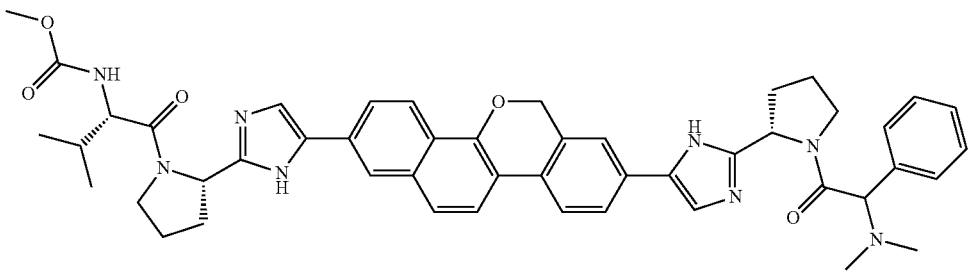 [SMILES: COC(=O)N[C@H](C(=O)N1CCC[C@H]1c1ncc(-c2ccc3c4c(ccc3c2)-c2ccc(-c3cnc([C@@H]5CCCN5C(=O)C(c5ccccc5)N(C)C)[nH]3)cc2CO4)[nH]1)C(C)C]

methyl (2S)-1-((2S)-2-(5-(8-(2-((2S)-1-(2-(dimethyl-amino)-2-phenylacetyl)pyrrolidin-2-yl)-1H-imidazol-5-yl)-6H-dibenzo[c,h]chromen-2-yl)-1H-imidazol-2-yl)pyrrolidin-1-yl)-3-methyl-1-oxobutan-2-ylcarbamate Methyl (2S)-1-((2S)-2-(5-(8-(2-((2S)-1-(2-(dimethyl-amino)-2-phenylacetyl)pyrrolidin-2-yl)-1H-imidazol-5-yl)-6H-dibenzo[c,h]chromen-2-yl)-1H-imidazol-2-yl)pyrrolidin-1-yl)-3-methyl-1-oxobutan-2-ylcarbamate: This compound was made in an analogous manner to methyl (S)-1-((S)-2-(5-(8-(2-((S)-1-((R)-2-methoxycarbonylamino-2-phenylacetyl)-pyrrolidin-2-yl)-1H-imidazol-5-yl)-6H-dibenzo[c,h]chromen-2-yl)-1H-imidazol-2-yl)pyrrolidin-1-yl)-3-methyl-1-oxobutan-2-ylcarbamate, substituting (R)-2-(dimethylamino)-2-phenylacetic acid for (R)-2-(methoxycarbonylamino)-2-phenylacetic acid in the second amide coupling. LCMS-ESI$^+$: calculated for $C_{48}H_{52}N_8O_5$: 820.41; observed [M+1]$^+$: 821.25.

Example HT

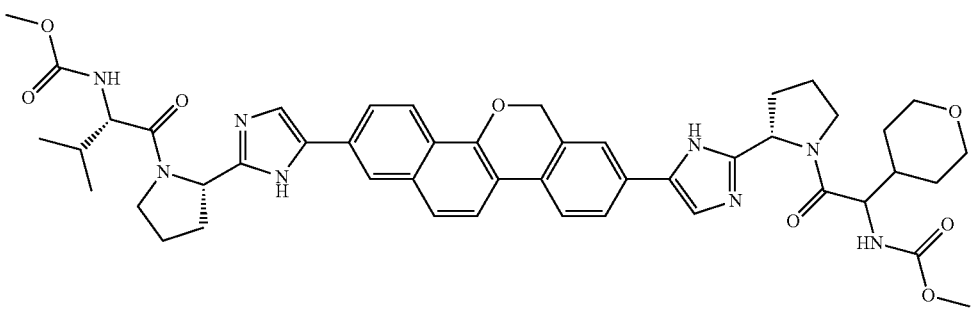

methyl (S)-1-((S)-2-(5-(8-(2-((S)-1-((S)-2-methoxy-carbonylamino-2-(tetrahydro-2H-pyran-4-yl)acetyl)pyrrolidin-2-yl)-1H-imidazol-5-yl)-6H-dibenzo[c,h]chromen-2-yl)-1H-imidazol-2-yl)pyrrolidin-1-yl)-3-methyl-1-oxobutan-2-ylcarbamate Methyl (S)-1-((S)-2-(5-(8-(2-((S)-1-((S)-2-methoxycarbonylamino-2-(tetrahydro-2H-pyran-4-yl)acetyl)pyrrolidin-2-yl)-1H-imidazol-5-yl)-6H-dibenzo[c,h]chromen-2-yl)-1H-imidazol-2-yl)pyrrolidin-1-yl)-3-methyl-1-oxobutan-2-ylcarbamate: This compound was made in an analogous manner to methyl (S)-1-((S)-2-(5-(8-(2-((S)-1-((R)-2-methoxycarbonylamino-2-phenylacetyl)-pyrrolidin-2-yl)-1H-imidazol-5-yl)-6H-dibenzo[c,h]chromen-2-yl)-1H-imidazol-2-yl)pyrrolidin-1-yl)-3-methyl-1-oxobutan-2-ylcarbamate, substituting (S)-2-(methoxycarbonylamino)-2-(tetrahydro-2H-pyran-4-yl)acetic acid for (R)-2-(methoxycarbonylamino)-2-phenylacetic acid in the second amide coupling. LCMS-ESI$^+$: calculated for $C_{47}H_{54}N_8O_8$: 858.98; observed [M+1]f: 860.02.

Example HU

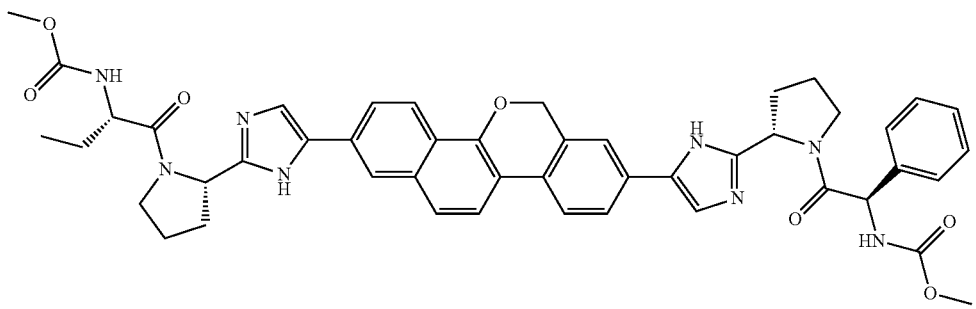

methyl (S)-1-((S)-2-(5-(8-(2-((S)-1-((R)-2-methoxy-
carbonylamino-2-phenylacetyl)pyrrolidin-2-yl)-1H-
imidazol-5-yl)-6H-dibenzo[c,h]chromen-2-yl)-1H-
imidazol-2-yl)pyrrolidin-1-yl)-1-oxobutan-2-
ylcarbamate Methyl (S)-1-((S)-2-(5-(8-(2-((S)-1-((R)-2-methoxycar-bonylamino-2-phenylacetyl)pyrrolidin-2-yl)-1H-imidazol-5-yl)-6H-dibenzo[c,h]chromen-2-yl)-1H-imidazol-2-yl)pyr-rolidin-1-yl)-1-oxobutan-2-ylcarbamate: This compound was made in an analogous manner to methyl (S)-1-((S)-2-(5-(2-((5)-1-((R)-2- methoxycarbonylamino-2-pheny-lacetyl)-pyrrolidin-2-yl)-1H-imidazol-5-yl)-6H-dibenzo[c,h]chromen-2-yl)-1H-imidazol-2-yl)pyrrolidin-1-yl)-3-methyl-1-oxobutan-2-ylcarbamate, substituting (S)-2-(methoxycarbonylamino)butanoic acid for (S)-2-(methoxycarbonylamino)-3-methylbutanoic acid in the first amide coupling. LCMS-ESI$^+$: calculated for $C_{47}H_{48}N_8O_7$: 836.93; observed [M+1]$^+$: 837.63.

Example HV

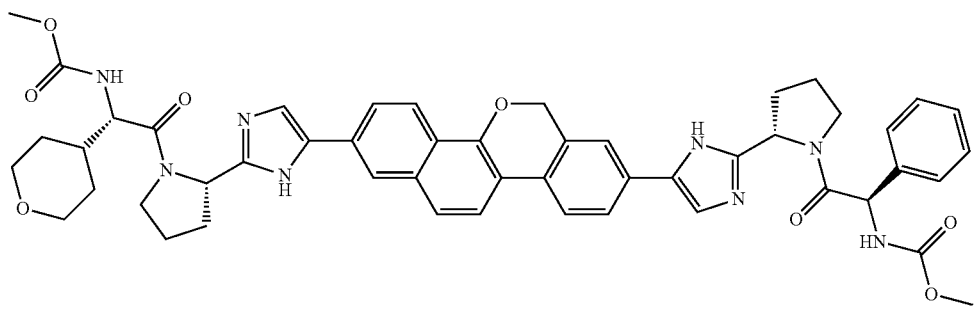

methyl (S)-2-((S)-2-(5-(8-(2-((S)-1-((R)-2-methoxy-
carbonylamino-2-phenylacetyl)pyrrolidin-2-yl)-1H-
imidazol-5-yl)-6H-dibenzo[c,h]chromen-2-yl)-1H-
imidazol-2-yl)pyrrolidin-1-yl)-2-oxo-1-(tetrahydro-
2H-pyran-4-yl)ethylcarbamate Methyl (S)-2-((S)-2-(5-(8-(2-((S)-1-((R)-2-methoxycar-bonylamino-2-phenylacetyl)pyrrolidin-2-yl)-1H-imidazol-5-yl)-6H-dibenzo[c,h]chromen-2-yl)-1H-imidazol-2-yl)pyr-rolidin-1-yl)-2-oxo-1-(tetrahydro-2H-pyran-4-yl) ethylcarbamate:

This compound was made in an analogous manner to methyl (S)-1-((S)-2-(5-(8-(2-((S)-1-((R)-2-methoxycarbo-nylamino-2-phenylacetyl)-pyrrolidin-2-yl)-6H-imidazol-5-yl)-6H-dibenzo[c,h]chromen-2-yl)-1H-imidazol-2-yl)pyrro-lidin-1-yl)-3-methyl-1-oxobutan-2-ylcarbamate, substituting (S)-2-(methoxycarbonylamino)-2-(tetrahydro-2H-pyran-4-yl)acetic acid for (S)-2-(methoxycarbo-nylamino)-3-methylbutanoic acid in the first amide cou-pling. LCMS-ESI$^+$: calculated for $C_{50}H_{52}N_8O_8$: 893.00; observed [M+1-1]$^+$: 894.07.

Example HW

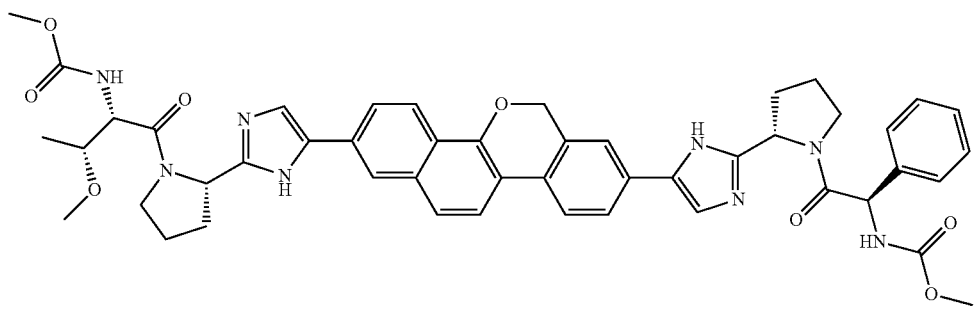

methyl (2S,3R)-1-((S)-2-(5-(8-(2-((S)-1-((R)-2-methoxycarbonylamino-2-phenylacetyl)pyrrolidin-2-yl)-1H-imidazol-5-yl)-6H-dibenzo[c,h]chromen-2-yl)-1H-imidazol-2-yl)pyrrolidin-1-yl)-3-methoxy-1-oxobutan-2-ylcarbamate Methyl (2S,3R)-1-((S)-2-(5-(8-(2-((S)-1-((R)-2-methoxycarbonylamino-2-phenylacetyl)pyrrolidin-2-yl)-1H-imidazol-5-yl)-6H-dibenzo[c,h]chromen-2-yl)-1H-imidazol-2-yl)pyrrolidin-1-yl)-3-methoxy-1-oxobutan-2-ylcarbamate:

This compound was made in an analogous manner to methyl (S)-1-((S)-2-(5-(8-(2-((S)-1-((R)-2-methoxycarbonylamino-2-phenylacetyl)-pyrrolidin-2-yl)-1H-imidazol-5-yl)-6H-dibenzo[c, h]chromen-2-yl)-1H-imidazol-2-yl)pyrrolidin-1-yl)-3-methyl-1-oxobutan-2-ylcarbamate, substituting (2S,3R)-3-methoxy-2-(methoxycarbonylamino) butanoic acid for (S)-2-(methoxycarbonylamino)-3-methylbutanoic acid in the first amide coupling. LCMS-ESI$^+$: calculated for $C_{48}H_{50}N_8O_8$: 866.96; observed $[M+1]^+$: 867.96.

Example HX

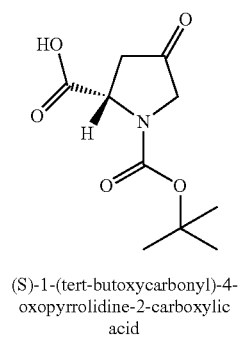

(S)-1-(tert-butoxycarbonyl)-4-oxopyrrolidine-2-carboxylic acid

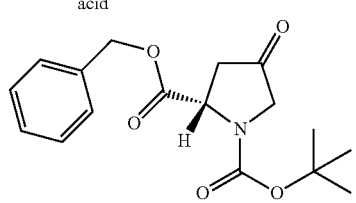

(S)-2-benzyl 1-tert-butyl 4-oxopyrrolidine-1,2-dicarboxylate

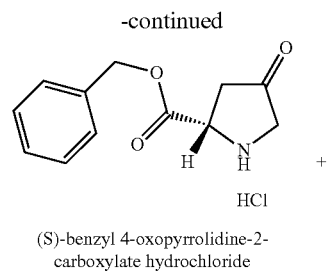

(S)-benzyl 4-oxopyrrolidine-2-carboxylate hydrochloride (S)-2-(methoxycarbonylamino)-3-methylbutanoic acid

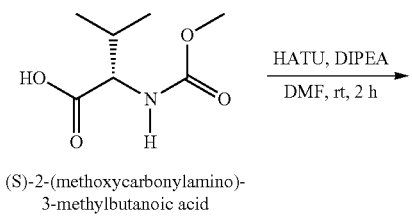

(S)-benzyl 1-((S)-2-(methoxycarbonylamino)-3-methylbutanoyl)-4-oxopyrrolidine-2-carboxylate

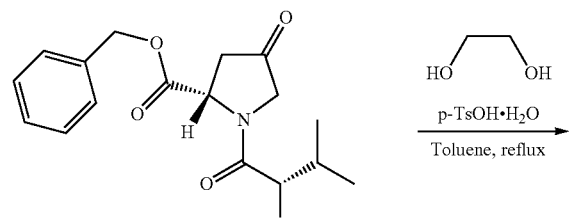

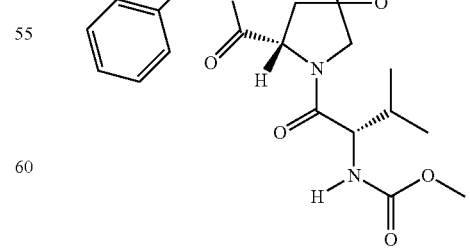

(S)-benzyl 7-((S)-2-(methoxycarbonylamino)-3-methylbutanoyl)-1-4-dioxa-7-azaspiro[4.4]nonane-8-carboxylate

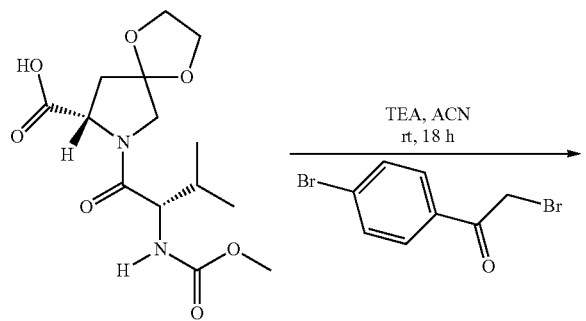

(S)-7-((S)-2-
(methoxycarbonylamino)-3-
methylbutanoyl)-1,4-dioxa-7-
azaspiro[4.4]nonane-
8-carboxylic acid

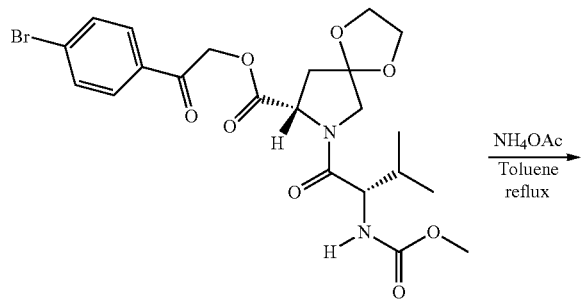

(S)-2-(4-bromophenyl)-2-oxoethyl 7-((S)-2-
(methoxycarbonylamino)-3-methylbutanoyl)-
1,4-dioxa-7-azaspiro[4.4]nonane-8-carboxylate

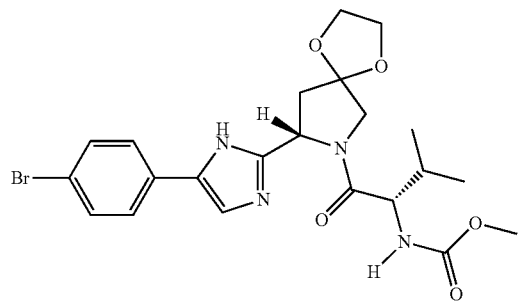

methyl (S)-1-((S)-8-(5-(4-bromophenyl)-1H-
imidazol-2-yl)-1,4-dioxa-7-azaspiro[4.4]nonan-
7-yl)-3-methyl-1-oxobutan-2-ylcarbamate (S)-2-benzyl 1-tert-butyl
4-oxopyrrolidine-1,2-dicarboxylate

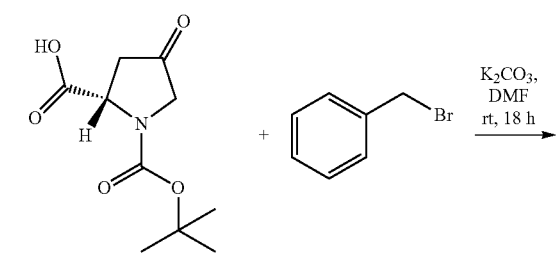

(S)-1-(tert-butoxycarbonyl)-4-
oxopyrrolidine-2-
carboxylic acid

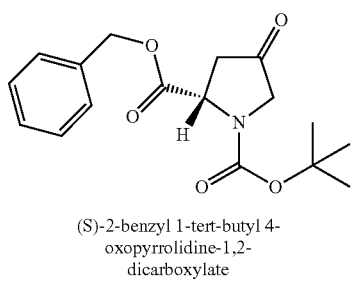

(S)-2-benzyl 1-tert-butyl 4-
oxopyrrolidine-1,2-
dicarboxylate

To a stirring solution of a mixture of (S)-1-(tert-butoxy-carbonyl)-4-oxopyrrolidine-2-carboxylic acid (2.85 g, 12.43 mmol) and potassium carbonate (4.33 g, 24.87 mmol) in anhydrous N,N-dimethylformamide (60 mL) was added benzyl bromide (4.25 g, 24.87 mmol). The mixture was stirred at room temperature overnight.

The resulting crude mixture was diluted with ethylacetate and the organic layer was washed with 10% sodium carbonate and brine. The organic layer was dried over sodium sulfate and volatiles were removed in-vacuo. The residue was purified on normal phase column. (2.82 g, 71%).

(S)-benzyl 4-oxopyrrolidine-2-carboxylate hydrochloride

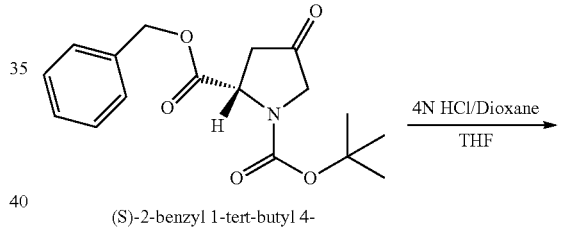

(S)-2-benzyl 1-tert-butyl 4-
oxopyrrolidine-1,2-
dicarboxylate

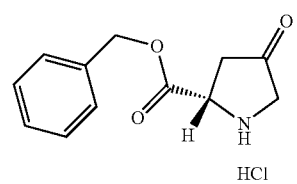

(S)-benzyl 4-oxopyrrolidine-2-
carboxylate hydrochloride

To a stirring solution of (S)-2-benzyl 1-tert-butyl 4-oxopyrrolidine-1,2-dicarboxylate (2.82 g, 8.8 mmol) in anhydrous tetrahydrofuran (44 mL) was added 4N HCl in 1,4-dioxane (9.3 mL) at room temperature. The mixture was stirred for 18 hours at room temperature. The product was then three times with tolune on rotovap to dryness to remove all the excess acid and further dried on a high vacuum overnight and used as is in the next step. Quantative yield.

987

(S)-Benzyl 1-((S)-2-(methoxycarbonylamino)-3-methylbutanoyl)-4-oxopyrrolidine-2-carboxylate

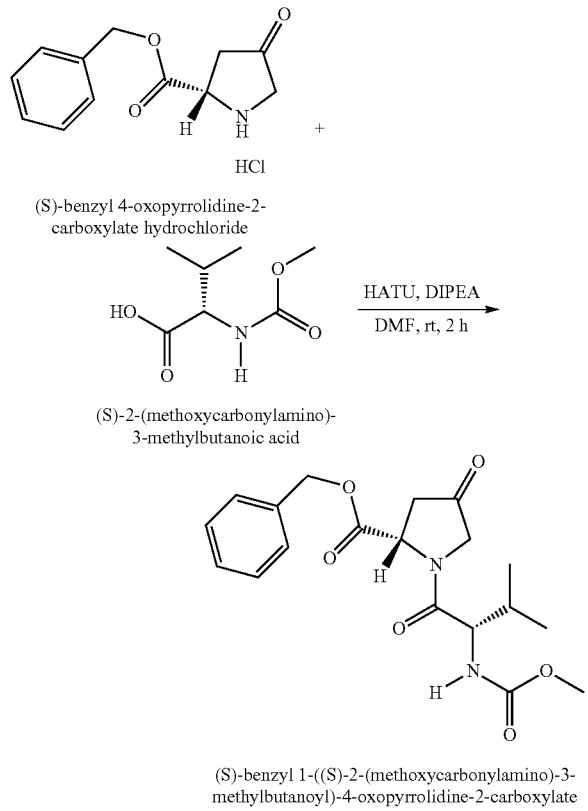

(S)-Benzyl 4-oxopyrrolidine-2-carboxylate hydrochloride (1.92 g, 8.8 mmol), the acid (in this case (S)-2-(methoxycarbonylamino)-3-methylbutanoic acid) (1.84 g, 10.56 mmol) and HATU (5.02 g, 13.2 mmol) were weighed out in a round bottom flask and dissolved in anhydrous DMF (44 mL). To this mixture was added DIPEA (6.82g, 52.8 mmol) at room temperature and the mixture was stirred for 2 h. The crude mixture was diluted with EtOAc and washed respectively with brine, 10% Na$_2$CO$_3$ and brine again, and the mixture was dried over MgSO$_4$, after filtration the mixture was concentrated down on rotovap. The residue was then purified on normal phase chromatography. (2.45 g, 74%).

(S)-benzyl 7-((S)-2-(methoxycarbonylamino)-3-methylbutanoyl)-1,4-dioxa-7-azaspiro[4.4]nonane-8-carboxylate

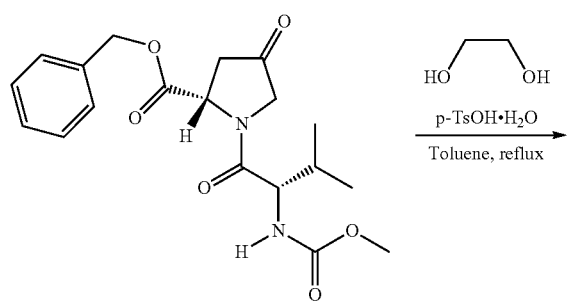

988

-continued

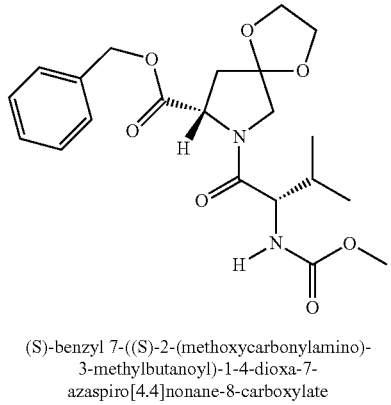

(S)-benzyl 7-((S)-2-(methoxycarbonylamino)-3-methylbutanoyl)-1-4-dioxa-7-azaspiro[4.4]nonane-8-carboxylate (S)-benzyl 1-((S)-2-(methoxycarbonylamino)-3-methylbutanoyl)-4-oxopyrrolidine-2-carboxylate (2.45 g, 6.51 mmol) in a round bottom flask was dissolved in anhydrous toluene (200 mL) and p-toluene sulfonic acid monohydride (124 mg, 0.1 mmol) and ethylene glycol (808 mg, 13.02 mmol) were added and the mixture was refluxed for 18 hours, removing the generated byproduct water with a Dean-Stark apparatus. The crude mixture was then diluted with ethyl acetate and washed, respectively, with 10% citric acid, saturated ammonium chloride, 10% sodium carbonate and finally with brine. The organic layers were combined and dried over sodium sulfate and concentrated down on rotovap. The crude residue was then purified on normal phase column chromatography with 5% MeOH/DCM. (2.3 g, 84%)

(S)-7-((S)-2-(methoxycarbonylamino)-3-methylbutanoyl)-1,4-dioxa-7-azaspiro[4.4]nonane-8-carboxylic acid

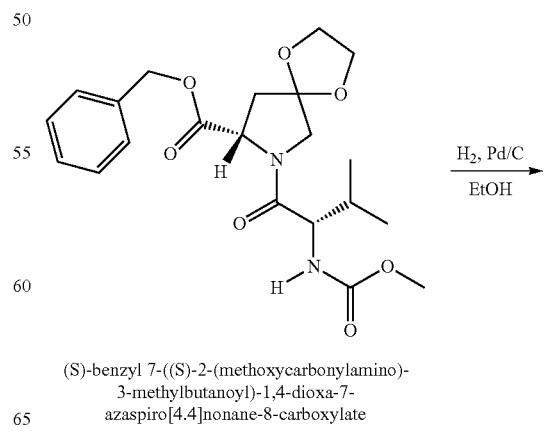

(S)-benzyl 7-((S)-2-(methoxycarbonylamino)-3-methylbutanoyl)-1,4-dioxa-7-azaspiro[4.4]nonane-8-carboxylate 989
-continued

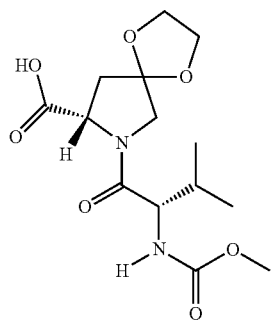

(S)-7-((S)-2-(methoxycarbonylamino)-3-methylbutanoyl)-1,4-dioxa-7-azaspiro[4.4]nonane-8-carboxylic acid (S)-benzyl 7-((S)-2-(methoxycarbonylamino)-3-methylbutanoyl)-1,4-dioxa-7-azaspiro[4.4]nonane-8-carboxylate (2.3 g, 5.47 mmol) was dissolved in ethyl alcohol (55 mL) and under Argon charged with 10% Pd/C (585 mg, 0.55 mmol) in a round bottom flask. The flask was then sealed with a rubber septa and the air was removed by vacuum and replaced with H₂ from a balloon. This process repeated three times and the mixture was stirred under H₂ atmosphere for 18 hours. The resulting mixture was then passed through a celite plug and concentrated down on rotovap. (1.76 g, 98%).

(S)-2-(4-bromophenyl)-2-oxoethyl 7-((S)-2-(methoxycarbonylamino)-3-methylbutanoyl)-1,4-dioxa-7-azaspiro[4.4]nonane-8-carboxylate

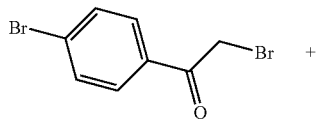

2-bromo-1-(4-bromophenyl)ethanone

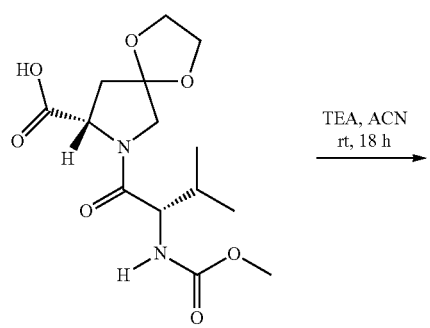

(S)-7-((S)-2-(methoxycarbonylamino)-3-methylbutanoyl)-1,4-dioxa-7-azaspiro[4.4]nonane-8-carboxylic acid TEA, ACN
rt, 18 h
→

990
-continued

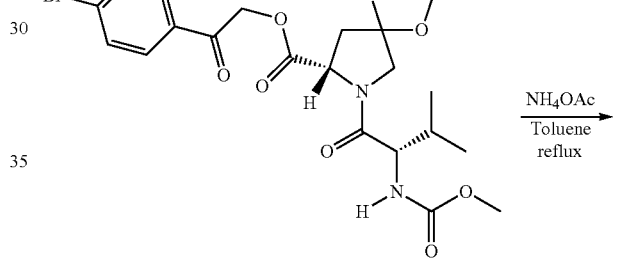

(S)-2-(4-bromophenyl)-2-oxoethyl 7-((S)-2-(methoxycarbonylamino)-3-methylbutanoyl)-1,4-dioxa-7-azaspiro[4.4]nonane-8-carboxylate Title compound was prepared according to the method employed to prepare (S)-2-(4-bromophenyl)-2-oxoethyl 5-((S)-2-(methoxycarbonylamino)-3-methylbutanoyl)-5-azaspiro[2.4]heptane-6-carboxylate (2.07g, 74%)

Methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate

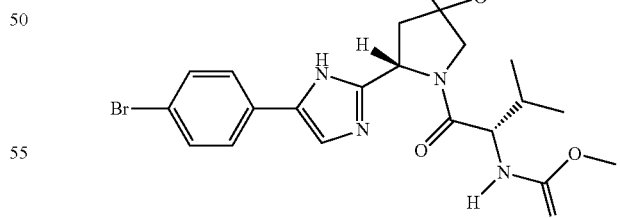

NH₄OAc
Toluene
reflux (S)-2-(4-bromophenyl)-2-oxoethyl 7-((S)-2-(methoxycarbonylamino)-3-methylbutanoyl)-1,4-dioxa-7-azaspiro[4.4]nonane-8-carboxylate methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate Title compound was prepared according to the method employed to prepare methyl (S)-1-((S)-6-(5-(4-bromophenyl)-1H-imidazol-2-yl)-5-azaspiro[2.4]heptan-5-yl)-3-methyl-1-oxobutan-2-ylcarbamate (1.64 g, 82.2%)

Example HY

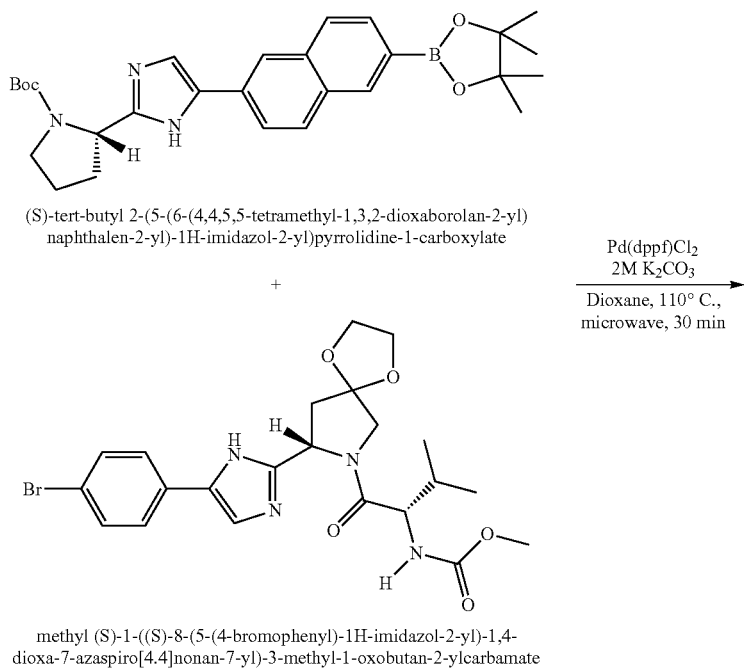

(S)-tert-butyl 2-(5-(6-(4,4,5,5-tetramethyl-1,3,2-dioxaborolan-2-yl)naphthalen-2-yl)-1H-imidazol-2-yl)pyrrolidine-1-carboxylate

+ methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate Pd(dppf)Cl$_2$
2M K$_2$CO$_3$
Dioxane, 110° C.,
microwave, 30 min

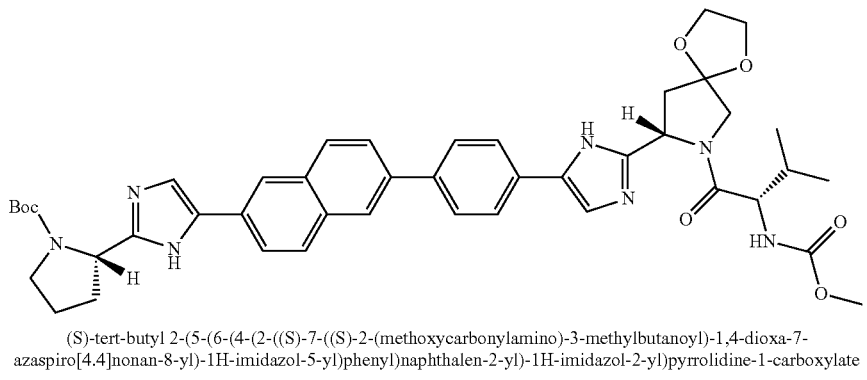

(S)-tert-butyl 2-(5-(6-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)naphthalen-2-yl)-1H-imidazol-2-yl)pyrrolidine-1-carboxylate (S)-tert-butyl 2-(5-(6-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)naphthalen-2-yl)-1H-imidazol-2-yl)pyrrolidine-1-carboxylate: (S)-tert-butyl 2-(5-(6-(4,4,5,5-tetramethyl-1,3,2-dioxaborolan-2-yl)naphthalen-2-yl)-1H-imidazol-2-yl)pyrrolidine-1-carboxylate (150 mg, 0.296 mmol) and methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate (174 mg, 0.355 mmol) were weighed out in a microwave vessel and dissolved in 1,4-dioxane (3 mL), followed by 2M potassium carbonate (444 uL, 0.888 mmol) and Pd(dppf)Cl$_2$ (21 mg, 0.03 mmol). The mixture was sonicated for 2 minutes and then bubbled with nitrogen gas for 3 min to degas. The vessel was sealed and the content was heated in microwave at 110° C. for 30 min. The crude reaction mixture was then diluted with EtOAc and washed twice with brine and saturated NaHCO$_3$ and once with brine again and dried over MgSO$_4$. The crude solution was then filtered and concentrated down. (233 mg, 99%).

Example HZ

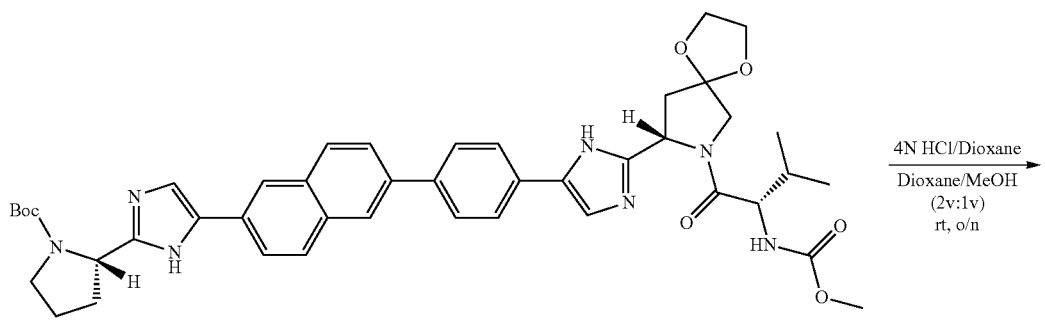

(S)-tert-butyl 2-(5-(6-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)naphthalen-2-yl)-1H-imidazol-2-yl)pyrrolidine-1-carboxylate

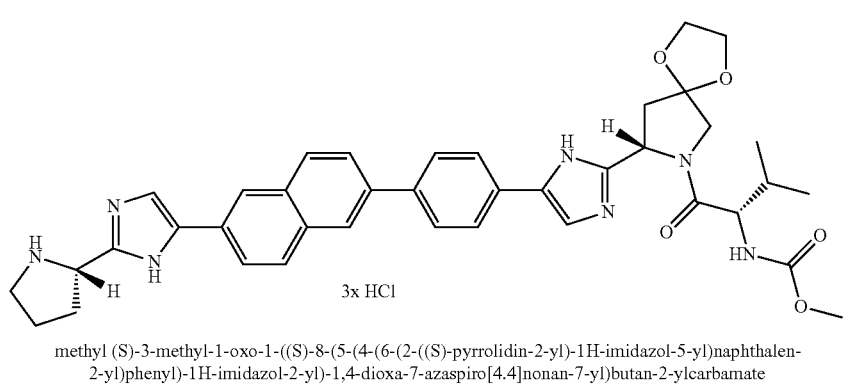

methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate Methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate: In a flask, (S)-tert-butyl 2-(5-(6-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)naphthalen-2-yl)-1H-imidazol-2-yl)pyrrolidine-1-carboxylate (233 mg, 0.296 mmol) was dissolved in a (2:1) mixture of 1,4-dioxane (6 ml) and methanol (3 mL) and to this solution was added 4N HCl/Dioxane (740 uL). The mixture was stirred at room temperature overnight. The reaction mixture was then concentrated down and dissolved in dioxane and concentrated down to dryness again and finally suspended in diethylether and concentrated down do dryness to obtain a beige color powder quantitatively as 3 HCl salt. The product used as-is in the next step.

Example IA

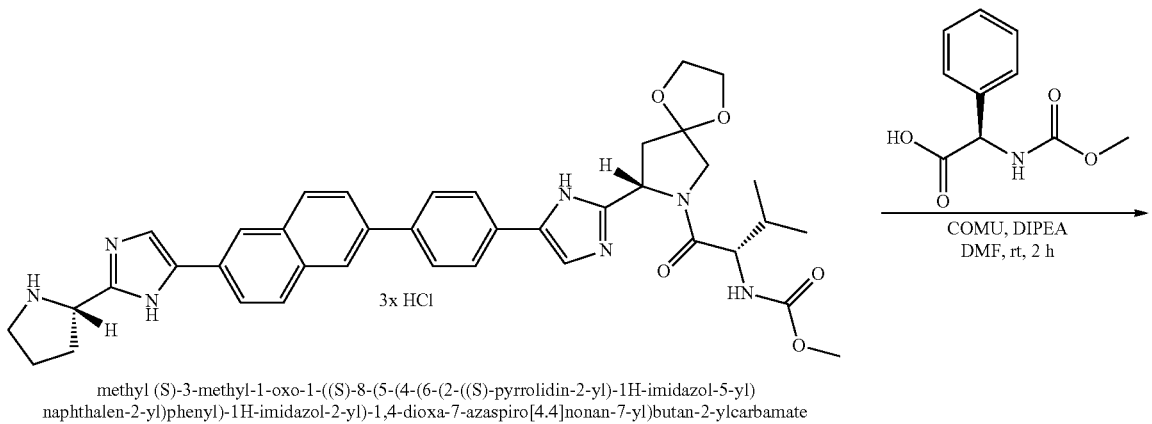

methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate

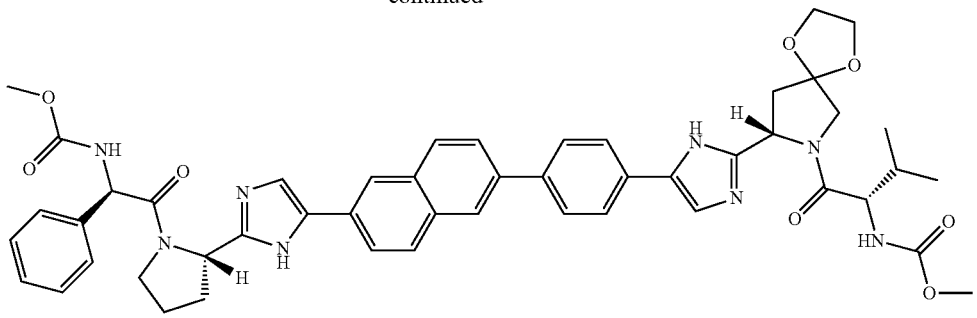

(S)-1-((S)-8-(5-(4-(6-(2-((S)-1-((R)-2-(methoxycarbonylamino)-2-phenylacetyl)pyrrolidin-2-yl)-1H-imidazol-5-yl) naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester: Methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate as 3HCl salt (200 mg, 0.24 mmol), (R)-2-(methoxycarbonylamino)-2-phenylacetic acid (60 mg, 0.288 mmol), and COMU (154 mg, 0.36 mmol) were all weighed out in a scintillation vial and anhydrous N,N-dimethylformamide (2.4 mL) was added and without stirring to this mixture was then added DIPEA (124 mg, 0.96 mmol) and the mixture was sonicated to dissolve all the reactants as quickly as possible. The mixture was then stirred for 2 h at room temperature. The crude mixture was diluted with EtOAc and washed with brine, 10% Na$_2$CO$_3$, brine and the organic layer was dried over MgSO$_4$. The filtrate was concentrated down and the residue was purified by normal phase column chromatography (5% MeOH/DCM). MS (ESI) m/z 881.84 [M+H]$^+$. (95 mg, 45%).

Example IB

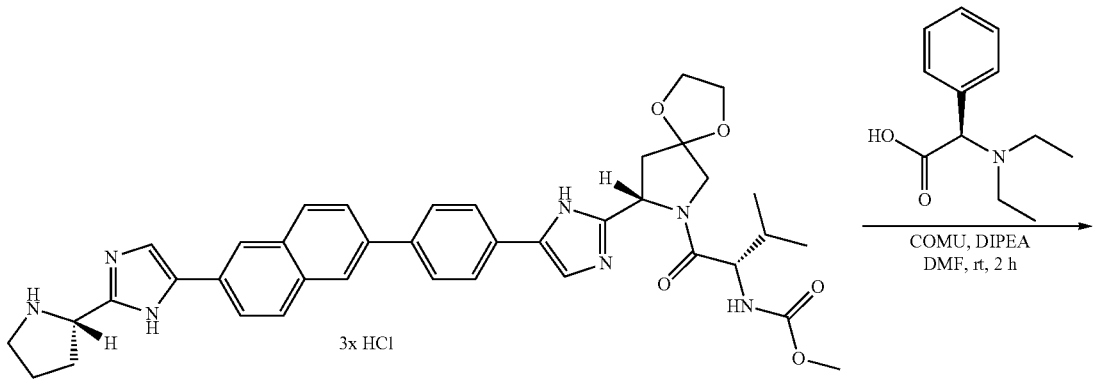

methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3HCl salt

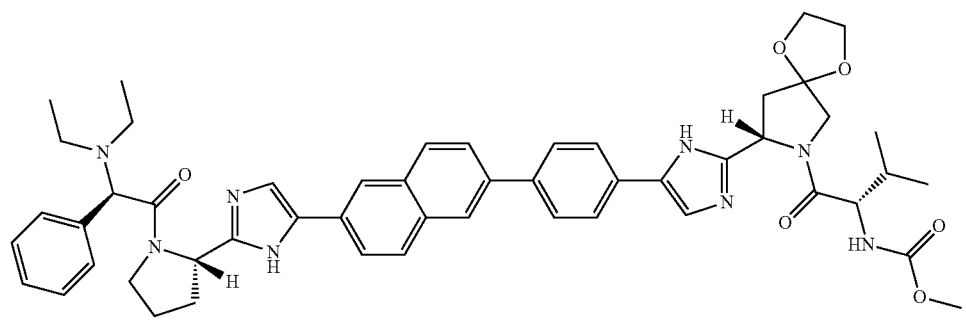

(S)-1-((S)-8-(5-(4-6-(2-((S)-1-((R)-2-(diethylamino)-2-phenylacetyl)pyrrolidin-2-yl)-1H-imidazol-5-yl)naphthalen-2-yl)phenyl)-1H-imidazol-2-yl)1,4-dioxa-7-azaspiro[4.4]nonan-7-yl)-3-methyl-1-oxobutan-2-ylcarbamic acid methyl ester (S)-1-((S)-8-(5-(4-(6-(2-((S)-1-((R)-2-(diethylamino)-2-phenylacetyl)pyrrolidin-2-yl)-1H-imidazol-5-yl) naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester: Title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3HCl salt. MS (ESI) m/z 879.82 [M+H]$^+$. (53 mg, 50%).

Example IC

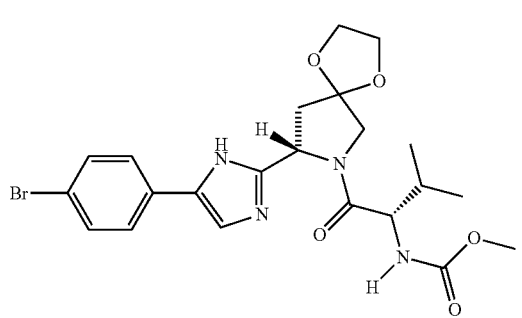

methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate

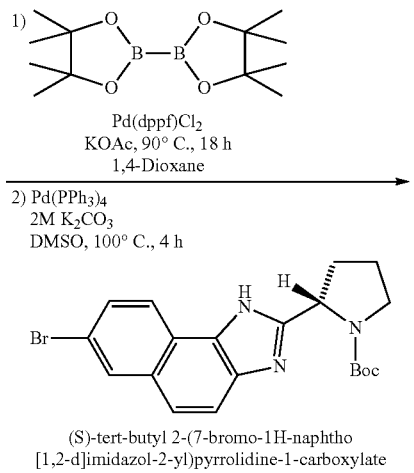

(S)-tert-butyl 2-(7-bromo-1H-naphtho[1,2-d]imidazol-2-yl)pyrrolidine-1-carboxylate

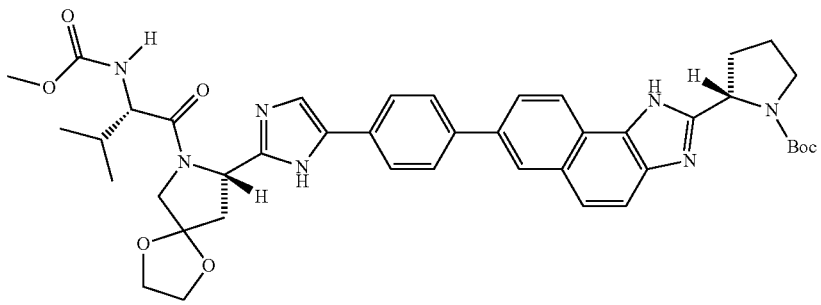

(S)-tert-butyl 2-(7-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)-1H-naphtho[1,2-d]imidazol-2-yl)pyrrolidine-1-carboxylate (S)-tert-butyl 2-(7-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)-1H-naphtho[1,2-d]imidazol-2-yl)pyrrolidine-1-carboxylate: Methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate (100 mg, 0.197 mmol), bis(pinacolato)diboron (51 mg, 0.2 mmol), potassium acetate (58 mg, 0.591 mmol), and Pd(dppf)Cl$_2$ (15 mg, 0.02 mmol) were all weighed out in a glass pressure vessel and anhydrous 1,4-Dioxane (1 mL) was added. The mixture was bubbled with nitrogen gas for about 5 min. The vessel was then capped and sealed and heated in an oil bath at 95° C. overnight with continuous stirring. The reaction vessel was cooled down to room temperature and (S)-tert-butyl 2-(7-bromo-1H-naphtho[1,2-d]imidazol-2-yl)pyrrolidine-1-carboxylate (83 mg, 0.29 mmol), 2M K$_2$CO$_3$ (296 uL), and Pd(PPh$_3$)$_4$ (23 mg, 0.02 mmol) were all added along with 1 mL of DMSO or 1,4-dioxane and the mixture was bubbled with nitrogen gas for 5 minutes. The vessel, again, was capped, sealed and placed in an oil bath at 100° C. for 4 hours. The resulting crude mixture was diluted with ethyl acetate and washed, respectively, with brine, 10% Na$_2$CO$_3$, 10% citric acid, saturated solution of NH$_4$Cl, and brine. The organic layer was then dried over Na$_2$SO$_4$ and the volatiles were removed on rotovap. The residue was purified on normal phase chromatography. (71 mg, 47%).

Example ID

999

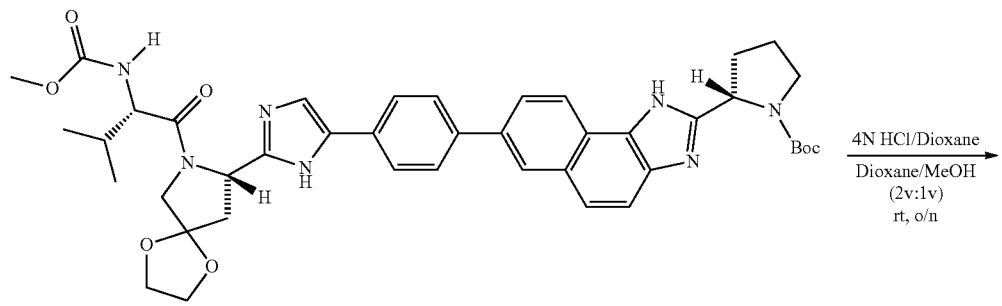

(S)-tert-butyl 2-(7-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)-1H-naphtho[1,2-d]imidazol-2-yl)pyrrolidine-1-carboxylate

1000

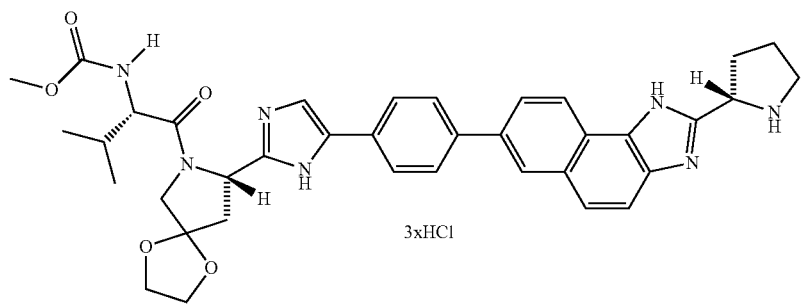

methyl (S)-3-methyl-1-oxo-1-((S)-8-(5-(4-(2-((S)-pyrrolidin-2-yl)-1H-naphtho[1,2-d]imidazol-7-yl)phenyl)-1H-imidazol-2-yl)-1,4-dioxa-7-azaspiro[4.4]nonan-7-yl)butan-2-ylcarbamate 3·HCl salt Methyl (S)-3-methyl-1-oxo-1-((S)-8-(5-(4-(2-((S)-pyrrolidin-2-yl)-1H-naphtho[1,2-d]imidazol-7-yl)phenyl)-1H-imidazol-2-yl)-1,4-dioxa-7-azaspiro[4.4]nonan-7-yl)butan-2-ylcarbamate 3.HCl salt: Same procedure was used as that of the synthesis of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate. (75 mg, 100%)

Example IE

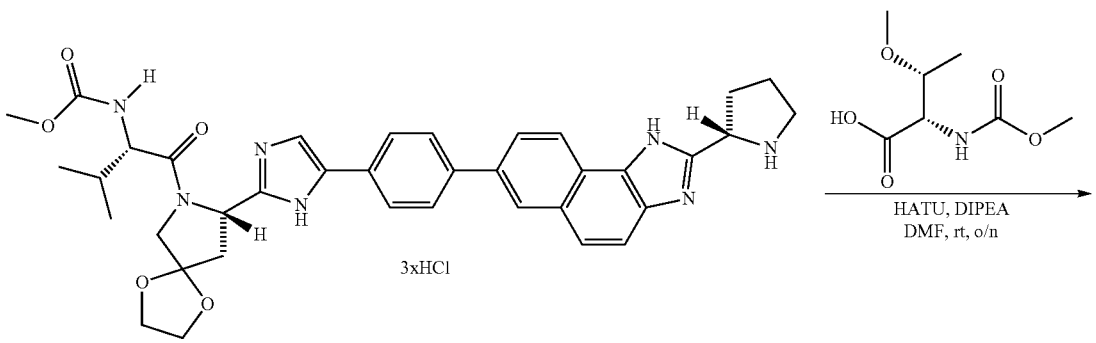

methyl (S)-3-methyl-1-oxo-1-((S)-8-(5-(4-(2-((S)-pyrrolidin-2-yl)-1H-naphtho[1,2-d]imidazol-7-yl)phenyl)-1H-imidazol-2-yl)-1,4-dioxa-7-azaspiro[4.4]nonan-7-yl)butan-2-ylcarbamate 3·HCl salt

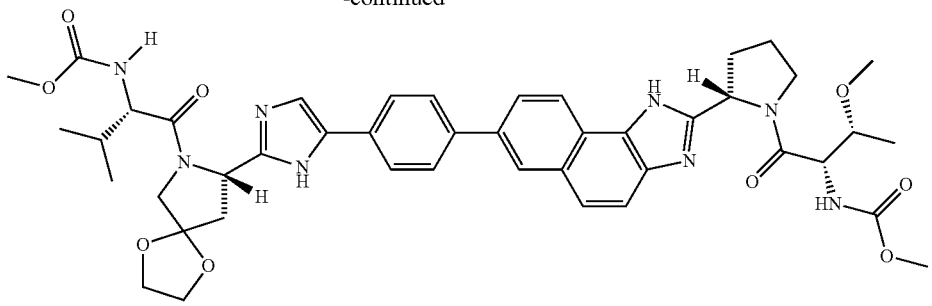

(2S,3R)-3-methoxy-1-((S)-2-(7-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)-1H-naphtho[1,2-d]imidazol-2-yl)pyrrolidin-1-yl)-1-oxobutan-2-ylcarbamic acid methyl ester (2S,3R)-3-methoxy-1-((S)-2-(7-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)-1H-naphtho[1,2-d]imidazol-2-yl)pyrrolidin-1-yl)-1-oxobutan-2-ylcarbamic acid methyl ester:

The title compound was prepared according to the method employed to prepare (S)-benzyl 1-((S)-2-(methoxycarbonylamino)-3-methylbutanoyl)-4-oxopyrrolidine-2-carboxylate, except that methyl (S)-3-methyl-1-oxo-1-((S)-8-(5-(4-(2-((S)-pyrrolidin-2-yl)-1H-naphtho[1,2-d]imidazol-7-yl)phenyl)-1H-imidazol-2-yl)-1,4-dioxa-7-azaspiro[4.4]nonan-7-yl)butan-2-ylcarbamate 3× HCl salt and (2S,3R)-3-methoxy-2-(methoxycarbonylamino)butanoic acid were used instead of (S)-benzyl 4-oxopyrrolidine-2-carboxylate hydrochloride and (S)-2-(methoxycarbonylamino)-3-methylbutanoic acid. MS (ESI) m/z 838.73 [M+H]$^+$. (45 mg, 54%).

Example IF

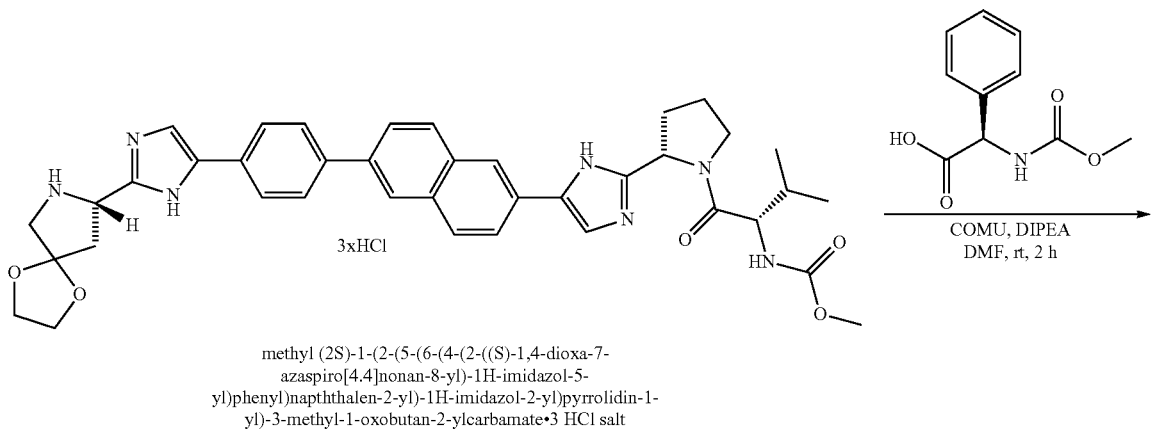

methyl (2S)-1-(2-(5-(6-(4-(2-((S)-1,4-dioxa-7-azaspiro[4.4]nonan-8-yl)-1H-imidazol-5-yl)phenyl)napthalen-2-yl)-1H-imidazol-2-yl)pyrrolidin-1-yl)-3-methyl-1-oxobutan-2-ylcarbamate•3 HCl salt

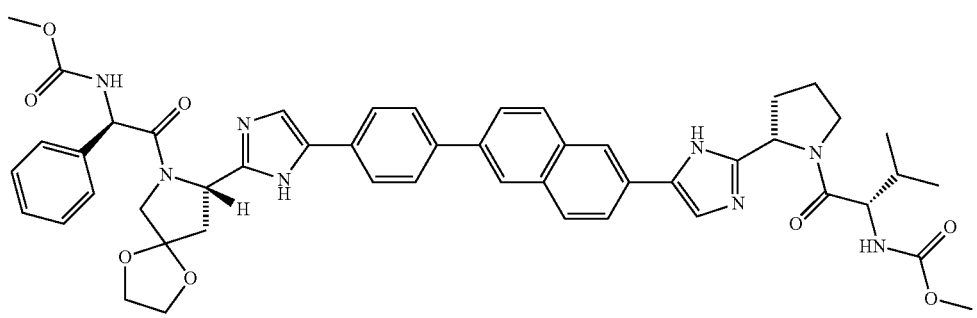

(S)-1-((S)-2-(5-(6-(4-(2-((S)-7-((R)-2-(methoxycarbonylamino)-2-phenylacetyl)-1,4-dioxa-7-azaspiro[4.4]nonan-8-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester

1003

(S)-1-((S)-2-(S-(6-(4-(2-((S)-7-((R)-2-(methoxycarbonylamino)-2-phenylacetyl)-1,4-dioxa-7-azaspiro[4.4]nonan-8-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester: Title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (2S)-1-(2-(5-(6-(4-(2-((S)-1,4-dioxa-7-azaspiro[4.4]nonan-8-yl)-1H-imidazol-5-yl)phenyl)naphthalen-2-yl)-1H-imidazol-2-yl)pyrrolidin-1-yl)-3-methyl-1-oxobutan-2-ylcarbamate 3× HCl salt was used instead of methyl (S)-3-methyl-1-oxo-1-((S)-8-(5-(4-(6-(2-((S)-1-pyrrolidin-2-yl)-1H-imidazol-5-yl)naphthalen-2-yl)phenyl)-11H-imidazol-2-yl)-1,4-dioxa-7-azaspiro[4.4]nonan-7-yl)butan-2-ylcarbamate 3 HCl salt. MS (ESI) m/z 881.91 [M+H]⁺. (137 mg, 38%).

Example IG

1004

(R)-2-((S)-2-(5-(4-(6-(2-((S)-7-((S)-2-(methoxycarbonylamino)-2-(tetrahydro-2H-pyran-4-yl)acetyl)-1,4-dioxa-7-azaspiro[4.4]nonan-8-yl)-1H-imidazo-5-yl)naphthalen-2-yl)phenyl)-1H-imidazol-2-yl)pyrrolidin-1-yl)-2-oxo-1-phenylethylcarbamic acid methyl ester: Title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-2-oxo-2-((S)-8-(5-(6-(4-(2-((S)-pyrrolidin-2-yl)-1H-imidazol-5-yl)phenyl)naphthalen-2-yl)-1H-imidazol-2-yl)-1,4-dioxa-7-azaspiro[4.4]nonan-7-yl)-1-(tetrahydro-2H-pyran-4-yl)ethylcarbamate 3× HCl salt was used instead of methyl (S)-3-methyl-1-oxo-1-((S)-8-(5-(4-(6-(2-((S)-pyrrolidin-2-yl)-1H-imidazol-5-yl)phenyl)naphthalen-2-yl)-1H-imidazol-2-yl)-1,4-dioxa-7-azaspiro[4.4]nonan-7-yl)butan-2-ylcarbamate 3× HCl salt. MS (ESI) m/z 923.83 [M+H]⁺. (73 mg, 77%).

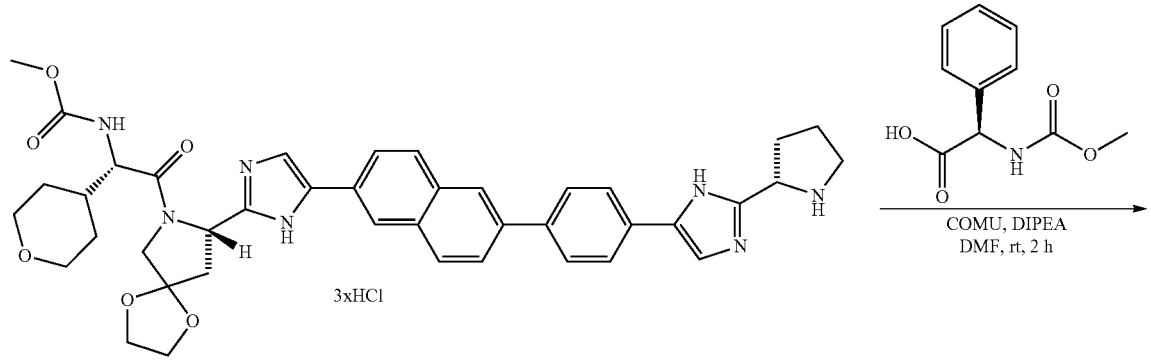

methyl (S)-2-oxo-2-((S)-8-(5-(6-(4-(2-((S)-pyrrolidin-2-yl)-1H-imidazol-5-yl)phenyl)naphthalen-2-yl)-1H-imidazol-2-yl)-1,4-dioxa-7-azaspiro[4.4]nonan-7-yl)-1-(tetrahydro-2H-pyran-4-yl)ethylcarbamate 3x HCl Salt

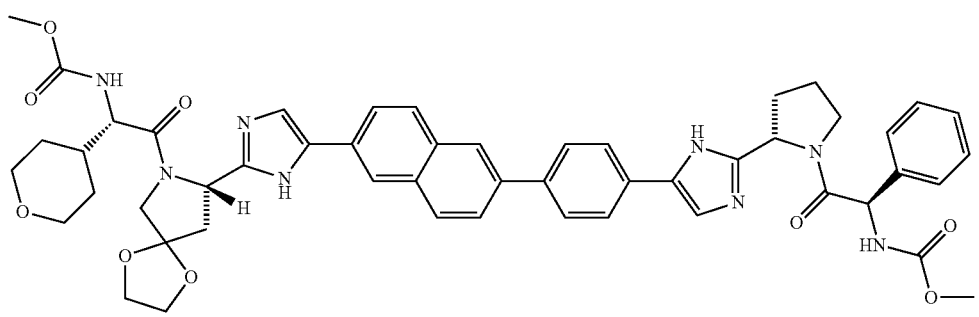

(R)-2-((S)-2-(5-(4-(6-(2-((S)-7-((S)-2-(methoxycarbonylamino)-2-(tetrahydro-2H-pyran-4-yl)acetyl)-1,4-dioxa-7-azaspiro[4.4]nonan-8-yl)-1H-imidazol-5-yl)naphthalen-2-yl)phenyl)-1H-imidazol-2-yl)pyrrolidin-1-yl)-2-oxo-1-phenylethylcarbamic acid methyl ester

Example 1H

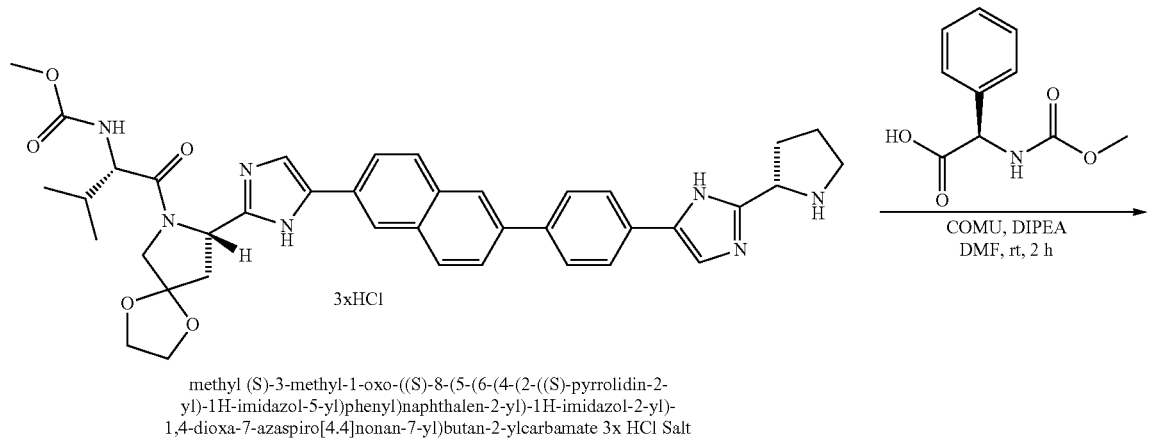

methyl (S)-3-methyl-1-oxo-((S)-8-(5-(6-(4-(2-((S)-pyrrolidin-2-yl)-1H-imidazol-5-yl)phenyl)naphthalen-2-yl)-1H-imidazol-2-yl)-1,4-dioxa-7-azaspiro[4.4]nonan-7-yl)butan-2-ylcarbamate 3x HCl Salt

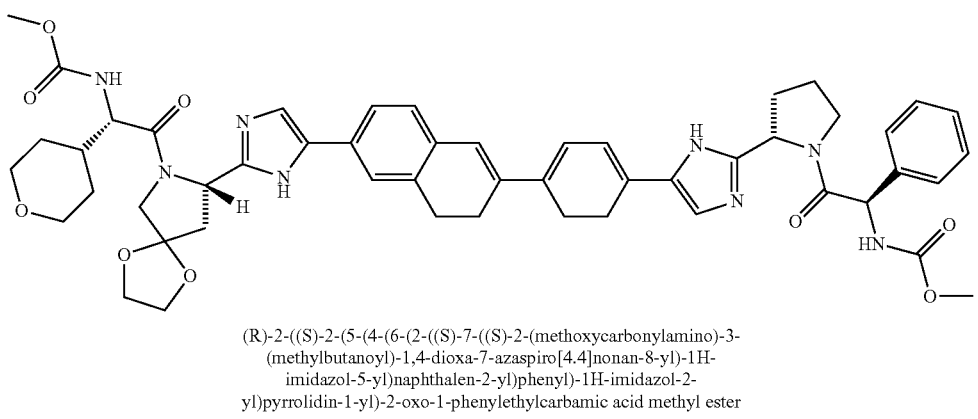

(R)-2-((S)-2-(5-(4-(6-(2-((S)-7-((S)-2-(methoxycarbonylamino)-3-(methylbutanoyl)-1,4-dioxa-7-azaspiro[4.4]nonan-8-yl)-1H-imidazol-5-yl)naphthalen-2-yl)phenyl)-1H-imidazol-2-yl)pyrrolidin-1-yl)-2-oxo-1-phenylethylcarbamic acid methyl ester R)-2-((S)-2-(5-(4-(6-(2-((S)-7-((S)-2-(methoxycarbonylamino)-3-methylbutanoyl)-1,4-dioxa-7-azaspiro[4.4]nonan-8-yl)-1H-imidazol-5-yl)naphthalen-2-yl)phenyl)-1H-imidazol-2-yl)pyrrolidin-1-yl)-2-oxo-1-phenylethylcarbamic acid methyl ester: Title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-3-methyl-1-oxo-1-((S)-8-(5-(6-(4-(2-((S)-pyrrolidin-2-yl)-1H-imidazol-5-yl)phenyl)naphthalen-2-yl)-1H-imidazol-2-yl)-1,4-dioxa-7-azaspiro[4.4]nonan-7-yl)butan-2-ylcarbamate 3x HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3x HCl salt. MS (ESI) m/z 881.90 [M+H]$^+$. (14 mg, 16%).

Example II

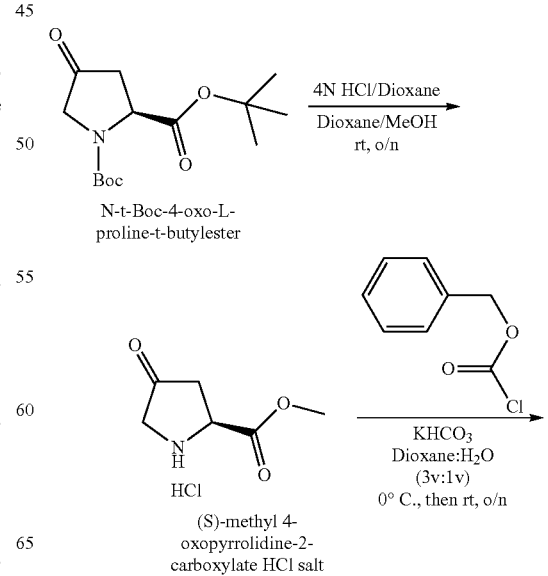

N-t-Boc-4-oxo-L-proline-t-butylester (S)-methyl 4-oxopyrrolidine-2-carboxylate HCl salt

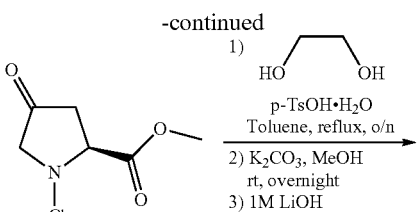

1) HO—OH
p-TsOH·H₂O
Toluene, reflux, o/n
2) K₂CO₃, MeOH
rt, overnight
3) 1M LiOH (S)-1-benzyl 2-methyl 4-oxopyrrolidine-1,2-dicarboxylate

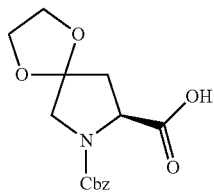

(S)-7-(benzyloxycarbonyl)-1,4-dioxa-7-azaspiro[4.4]nonane-8-carboxylic acid (S)-Methyl 4-oxopyrrolidine-2-carboxylate HCl salt:

The title compound was prepared in quantative yield according to the method employed to prepare methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate.

(S)-1-benzyl 2-methyl 4-oxopyrrolidine-1,2-dicarboxylate:

(S)-Methyl 4-oxopyrrolidine-2-carboxylate HCl salt (9.4 g, 52.6 mmol) was dissolved in 1,4-dioxane (210 mL) and a solution of potassiumbicarbonate (13.2 g, 131.5 mmol) in DI-water (70 mL) was added at 0° C., followed by slow addition of benzylchloroformate (15 mL, 105.2 mmol). The mixture was then let warm up to room temperature and it was stirred overnight. The resulting crude mixture was concentrated down as much as possible on the rotovap and it was diluted with EtOAc and washed twice with saturated NaHCO3 and 10% citric acid and once with saturated NaHCO3 again and then with brine. The organic layer was dried over Na2SO4 and after filtration it was concentrated down on rotovap. The crude product was then purified on normal phase column chromatography (15% EtOAc/Hexanes). (14.6 g, 100%)

(S)-7-(Benzyloxycarbonyl)-1,4-dioxa-7-azaspiro[4.4]nonane-8-carboxylic acid (S)-1-Benzyl 2-methyl 4-oxopyrrolidine-1,2-dicarboxylate (7.96 g, 28.71 mmol) was dissolved in toluene (300 mL) and to it was added ethylene glycol (17.82 g, 287.1 mmol) and p-toluene sulfonic acid monohydrate (546 mg). The flask that was equipped with a Dean-Stark apparatus with this mixture in it was stirred in a 120° C. oil bath overnight.

Upon the completion of the reaction the intermediate formed was the ethylene glycol ester instead of methyl ester due to trans-esterification. This intermediate was concentrated down on rotovap. The residue was taken up in MeOH (300 mL) and stirred in presence of solid K2CO3 (7.94 g, 57.42 mmol) overnight at room temperature to convert the ethylene glycol ester to methyl ester. After confirming the formation of methyl ester by LCMS and TLC, 1M LiOH (55 mL) was added to the mixture and it was then stirred at room temperature for 3 h. All the volatiles were removed on rotovap and the residue was taken up in toluene and concentrated down to dryness on rotovap and this was repeated three times. The resulting residue was further dried on high vacuum pump overnight.

The residue was taken up in DI-water and to it was added EtOAc and the organic layer was separated. The organic layer was checked for the absence of desired product. The water layer was then acidified using 2N HCl (about 70 mL) to adjust the pH to 5. Product was then extracted with EtOAc three times. Organic layers were combined washed with brine and dried over MgSO4 and further dried on high vacuum pump. (5.94 g, 67%).

Example IJ

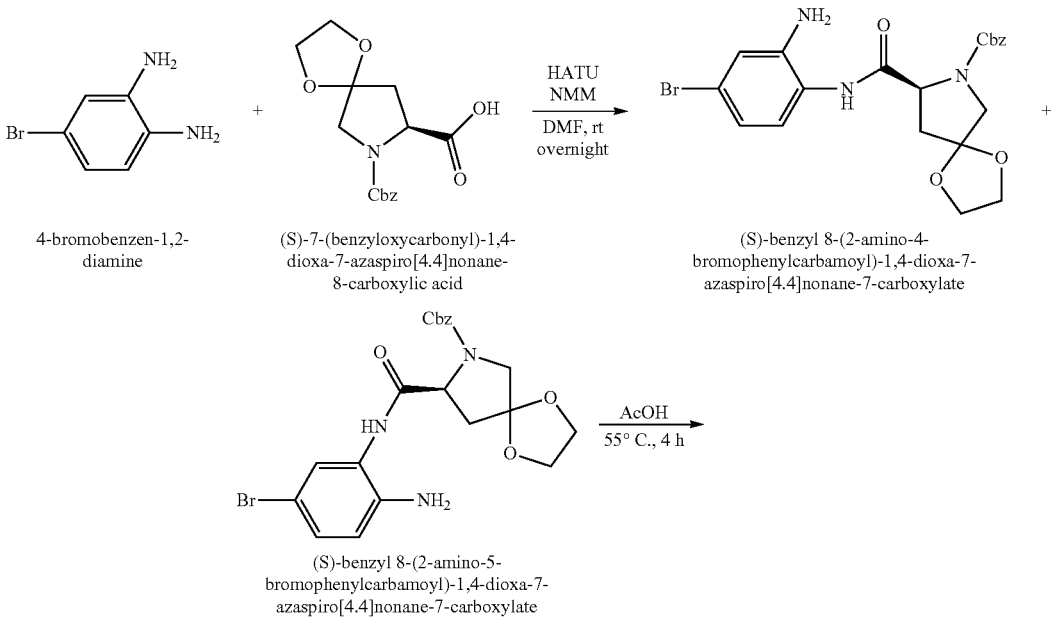

-continued

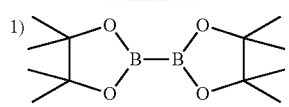

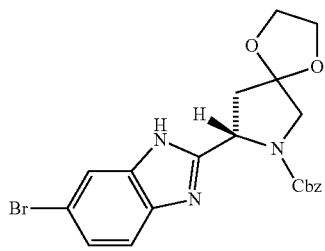

(S)-benzyl 8-(6-bromo-1H-benzo[d]imidazol-2-yl)-1,4-dioxa-7-azaspiro[4.4]nonane-7-carboxylate

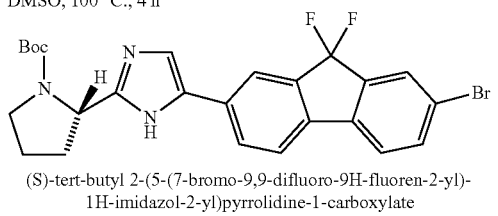

(S)-tert-butyl 2-(5-(7-bromo-9,9-difluoro-9H-fluoren-2-yl)-1H-imidazol-2-yl)pyrrolidine-1-carboxylate

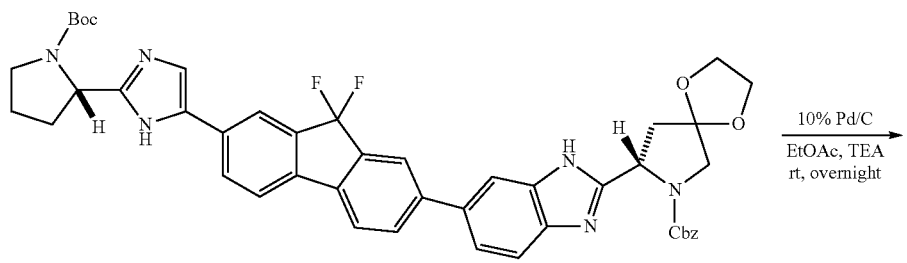

(S)-benzyl 8-(6-(7-(2-((S)-1-(tert-butoxycarbonyl)pyrrolidin-2-yl)-1H-imidazol-5-yl)-9,9-difluoro-9H-fluoren-2-yl)-1H-benzo[d]imidazol-2-yl)-1,4-dioxa-7-azaspiro[4.4]nonane-7-carboxylate

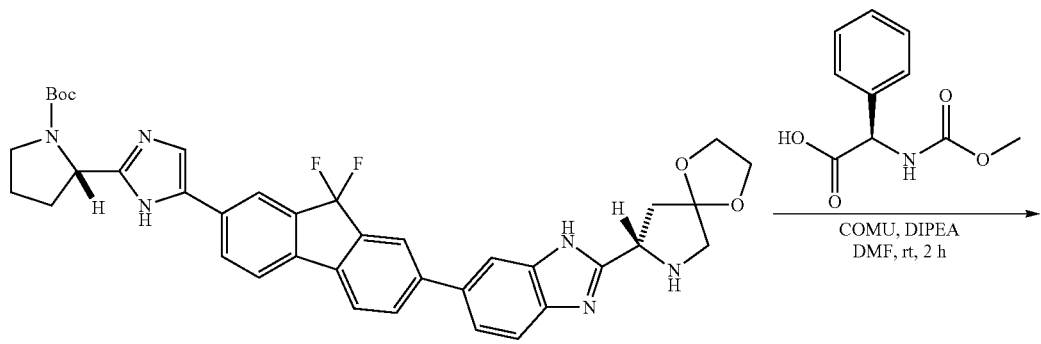

(S)-tert-butyl 2-(5-(7-(2-((S)-1,4-dioxa-7-azaspiro[4.4]nonan-8-yl)-1H-benzo[d]imidazol-6-yl)-9,9-difluoro-9H-fluoren-2-yl)-1H-imidazol-2-yl)pyrrolidine-1-carboxylate

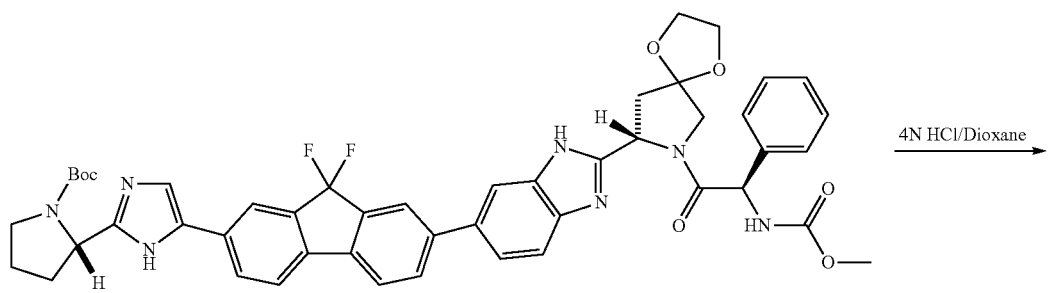

(S)-tert-butyl 2-(5-(9,9-difluoro-7-(2-((S)-7-((R)-2-(methoxycarbonylamino)-2-phenylacetyl)-1,4-dioxa-7-azaspiro[4.4]nonan-8-yl)-1H-benzo[d]imidazol-6-yl)-9H-fluoren-2-yl)-1H-imidazol-2-yl)pyrrolidine-1-carboxylate

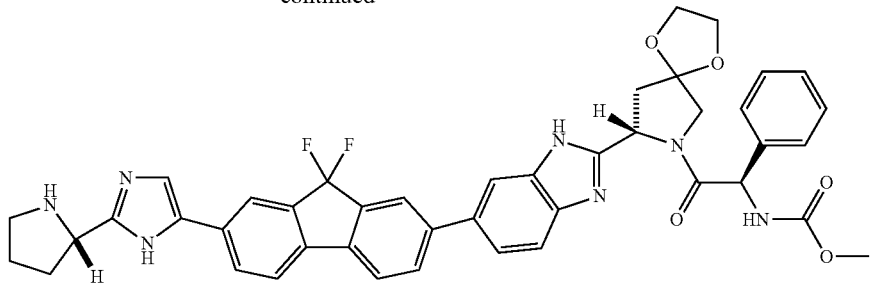

3xHCl
methyl (R)-2-((S)-8-6-(9,9-difluoro-7-(2-((S)-pyrrolidin-2-yl)-1H-imidazol-5-yl)-9H-fluoren-2-yl)-1H-benzo[d]imidazol-2-yl)-1,4-dioxa-7-azaspiro[4.4]nonan-7-yl)-2-oxo-1-phenylethylcarbamate 3x HCl Salt (S)-benzyl 8-(2-amino-4-bromophenylcarbamoyl)-1,4-dioxa-7-azaspiro[4.4]nonane-7-carboxylate:

Title compound was prepared in quantative yield according to the method employed to make 6-(2-Amino-5-bromophenylcarbamoyl)-5-aza-spiro[2.4]heptane-5-carboxylic acid benzyl ester and 6-(2-Amino-4-bromo-phenylcarbamoyl)-5-aza-spiro[2.4]heptane-5-carboxylic acid benzyl ester, substituting (S)-5-(benzyloxycarbonyl)-5-azaspiro[2.4]heptane-6-carboxylic acid with (S)-7-(benzyloxycarbonyl)-1,4-dioxa-7-azaspiro[4.4]nonane-8-carboxylic acid (357 mg, 99%).

(S)-benzyl 8-(6-bromo-1H-benzo[d]imidazol-2-yl)-1,4-dioxa-7-azaspiro[4.4]nonane-7-carboxylate:

Title compound was prepared according to the method employed to make 6-(6-Bromo-1H-benzoimidazol-2-yl)-5-aza-spiro[2.4]heptane-5-carboxylic acid benzyl ester (276 mg, 80%).

(S)-Benzyl 8-(6-(7-(2-((S)-1-(tert-butoxycarbonyl)pyrrolidin-2-yl)-1H-imidazol-5-yl)-9,9-difluoro-9H-fluoren-2-yl)-1H-benzo[d]imidazol-2-yl)-1,4-dioxa-7-azaspiro[4.4]nonane-7-carboxylate:

The title compound was prepared according to the method employed to prepare (S)-tert-butyl 2-(7-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)-1H-naphtho[1,2-d]imidazol-2-yl)pyrrolidine-1-carboxylate (377 mg, 77%).

(S)-tert-butyl 2-(5-(7-(2-((S)-1,4-dioxa-7-azaspiro[4.4]nonane-8-yl)-1H-benzo[d]imidazol-6-yl)-9,9-difluoro-9H-fluoren-2-yl)-1H-imidazol-2-yl)pyrrolidine-1-carboxylate:

(S)-Benzyl 8-(6-(7-(2-((S)-1-(tert-butoxycarbonyl)pyrrolidin-2-yl)-1H-imidazol-5-yl)-9,9-difluoro-9H-fluoren-2-yl)-1H-benzo[d]imidazol-2-yl)-1,4-dioxa-7-azaspiro[4.4]nonane-7-carboxylate (375 mg, 0.46 mmol) was dissolved in ethyl acetate (10 mL) and to it was added triethyl amine (140 mg, 1.38 mmol), followed by 10% Pd/C (Pearlman's catalyst)(196 mg, 0.09 mmol). The flask was purged with hydrogen gas three times by applying vacuum and purging hydrogen gas from a balloon and the mixture was stirred overnight at room temperature. The crude product was filtered through a 0.2 micron Nylon filter member and the filtrate was concentrated down on rotovap. (229 mg, 73%).

(S)-tert-butyl 2-(5-(9,9-difluoro-7-(2-((S)-7-((R)-2-(methoxycarbonylamino)-2-phenylacetyl)-1,4-dioxa-7-azaspiro[4.4]nonan-8-yl)-1H-benzo[d]imidazol-6-yl)-9H-fluoren-2-yl)-1H-imidazol-2-yl)pyrrolidine-1-carboxylate:

Title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester. (47 mg, 34%).

Methyl (R)-2-((S)-8-(6-(9,9-difluoro-7-(2-((S)-pyrrolidin-2-yl)-1H-imidazol-5-yl)-9H-fluoren-2-yl)-1H-benzo[d]imidazol-2-yl)-1,4-dioxa-7-azaspiro[4.4]nonan-7-yl)-2-oxo-1-phenylethylcarbamate 3x HCl Salt:

Title compound was prepared in quantative yield according to the method employed for making (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate.

Example IK

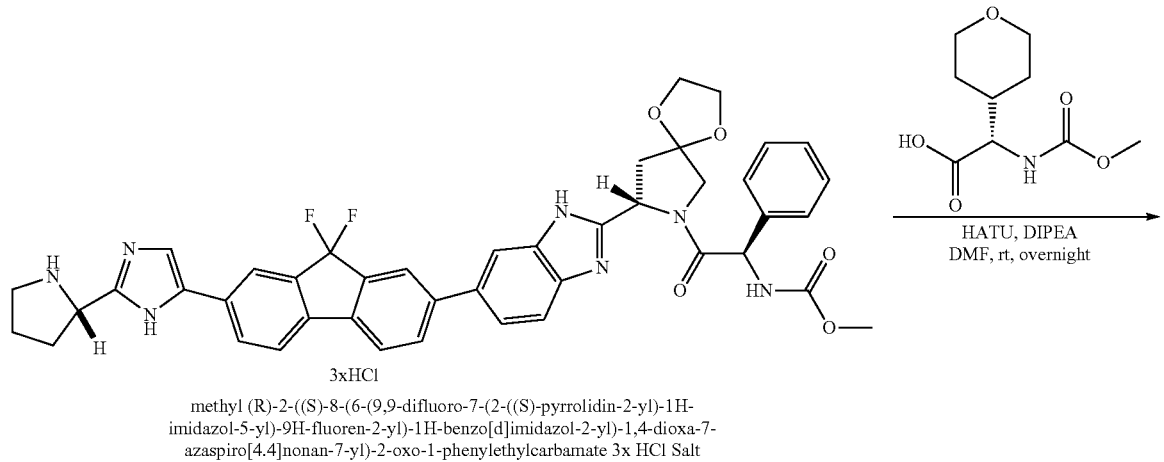

methyl (R)-2-((S)-8-(6-(9,9-difluoro-7-(2-((S)-pyrrolidin-2-yl)-1H-imidazol-5-yl)-9H-fluoren-2-yl)-1H-benzo[d]imidazol-2-yl)-1,4-dioxa-7-azaspiro[4.4]nonan-7-yl)-2-oxo-1-phenylethylcarbamate 3x HCl Salt

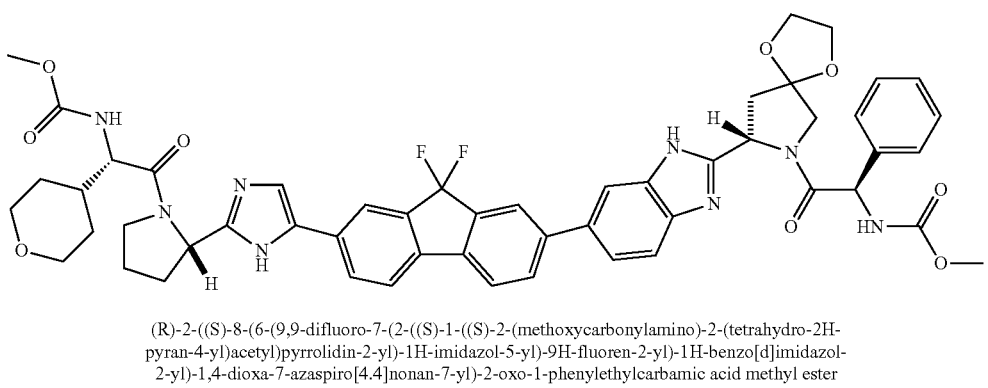

(R)-2-((S)-8-(6-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)-1H-benzo[d]imidazol-2-yl)-1,4-dioxa-7-azaspiro[4.4]nonan-7-yl)-2-oxo-1-phenylethylcarbamic acid methyl ester (R)-2-((S)-8-(6-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)-1H-benzo[d]imidazol-2-yl)-1,4-dioxa-7-azaspiro[4.4]nonan-7-yl)-2-oxo-1-phenylethylcarbamic acid methyl ester: The title compound was prepared according to the method employed to prepare (S)-benzyl 1-((S)-2-(methoxycarbonylamino)-3-methylbutanoyl)-4-oxopyrrolidine-2-carboxylate, except that (S)-2-(methoxycarbonylamino)-2-(tetrahydro-2H-pyran-4-yl)acetic acid and methyl (R)-2-((S)-8-(6-(9,9-difluoro-7-(2-((S)-pyrrolidin-2-yl)-1H-imidazol-5-yl)-9H-fluoren-2-yl)-1H-benzo[d]imidazol-2-yl)-1,4-dioxa-7-azaspiro[4.4]nonan-7-yl)-2-oxo-1-phenylethylcarbamate as 3HCl salt and (S)-2-(methoxycarbonylamino)-2-(tetrahydro-2H-pyran-4-yl)acetic acid were used instead of (S)-benzyl 4-oxopyrrolidine-2-carboxylate hydrochloride and (S)-2-(methoxycarbonylamino)-3-methylbutanoic acid. MS (ESI) m/z 972.29 [M+H]$^+$. (27.6 mg, 53%).

Example IL

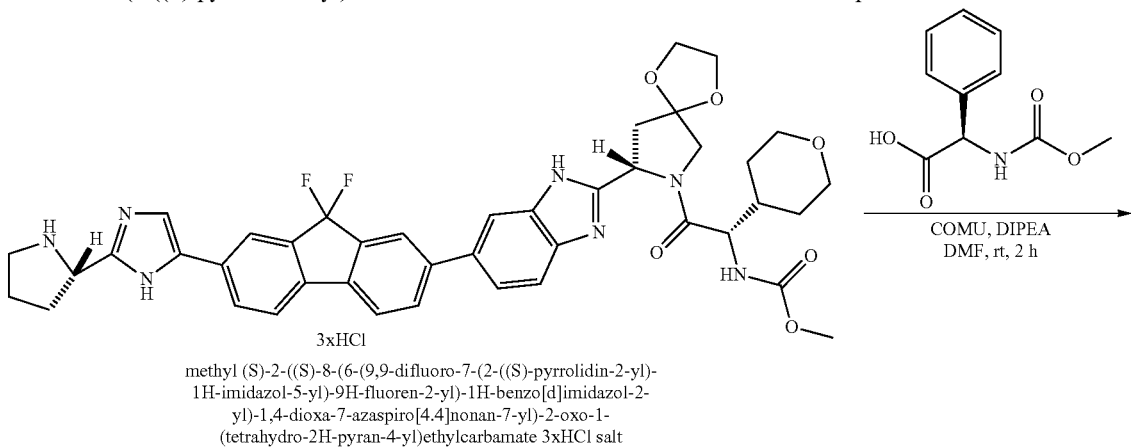

methyl (S)-2-((S)-8-(6-(9,9-difluoro-7-(2-((S)-pyrrolidin-2-yl)-1H-imidazol-5-yl)-9H-fluoren-2-yl)-1H-benzo[d]imidazol-2-yl)-1,4-dioxa-7-azaspiro[4.4]nonan-7-yl)-2-oxo-1-(tetrahydro-2H-pyran-4-yl)ethylcarbamate 3xHCl salt

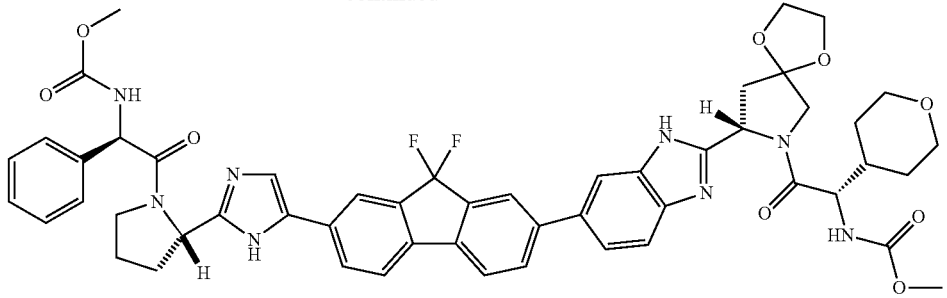

(S)-2-((S)-8-(6-(9,9-difluoro-7-(2-((S)-1-((R)-2-(methoxycarbonylamino)-
2-phennylacetyl)pyrrolidin-2-yl)-1H-imidazol-5-yl)-9H-fluoren-2-yl)-1H-
benzo[d]imidazol-2-yl)-1,4-dioxa-7-azaspiro[4.4]nonan-7-yl)-2-oxo-1-
(tetrahydro-2H-pyran-4-yl)ethylcarbamic acid methyl ester (S)-2-((S)-8-(6-(9,9-difluoro-7-(2-((S)-1-((R)-2-(methoxycarbonylamino)-2-phenylacetyl)pyrrolidin-2-yl)-1H-imidazol-5-yl)-9H-fluoren-2-yl)-1H-benzo[d]imidazol-2-yl)-1,4-dioxa-7-azaspiro[4.4]nonan-7-yl)-2-oxo-1-(tetrahydro-2H-pyran-4-yl)ethylcarbamic acid methyl ester: Title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-2-((S)-8-(6-(9,9-difluoro-7-(2-((S)-pyrrolidin-2-yl)-1H-imidazol-5-yl)-9H-fluoren-2-yl)-1H-benzo[d]imidazol-2-yl)-1,4-dioxa-7-azaspiro[4.4]nonan-7-yl)-2-oxo-1-(tetrahydro-2H-pyran-4-yl)ethylcarbamate 3× HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 972.54 [M+H]+. (30 mg, 43%).

Example 1M

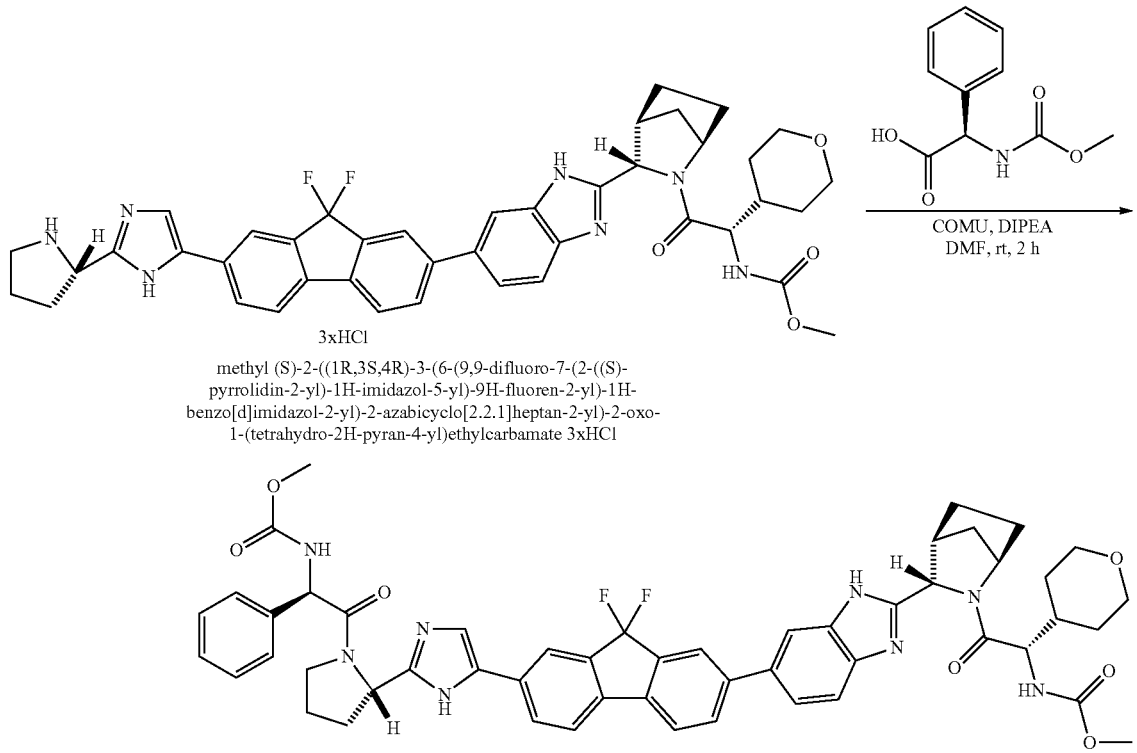

methyl (S)-2-((1R,3S,4R)-3-(6-(9,9-difluoro-7-(2-((S)-
pyrrolidin-2-yl)-1H-imidazol-5-yl)-9H-fluoren-2-yl)-1H-
benzo[d]imidazol-2-yl)-2-azabicyclo[2.2.1]heptan-2-yl)-2-oxo-
1-(tetrahydro-2H-pyran-4-yl)ethylcarbamate 3xHCl (S)-2-((1R,3S,4R)-3-(6-(9,9-difluoro-7-(2-((S)-1-((R)-2-
(methoxycarbonylamino)-2-phennylacetyl)pyrrolidin-2-yl)-1H-imidazol-5-
yl)-9H-fluoren-2-yl)-1H-benzo[d]imidazol-2-yl)-2-azabicyclo[2.2.1]heptan-
2-yl)-2-oxo-1-(tetrahydro-2H-pyran-4-yl)ethylcarbamic acid methyl ester

1017

(S)-2-((1R,3S,4R)-3-(6-(9,9-difluoro-7-(2-((S)-1-((R)-2-(methoxycarbonylamino)-2-phenylacetyl)pyrrolidin-2-yl)-1H-imidazol-5-yl)-9H-fluoren-2-yl)-1H-benzo[d]imidazol-2-yl)-2-azabicyclo[2.2.1]heptan-2-yl)-2-oxo-1-(tetrahydro-2H-pyran-4-yl)ethylcarbamic acid methyl ester: The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-2-((1R,3S,4R)-3-(6-(9,9-difluoro-7-(2-((S)-pyrrolidin-2-yl)-1H-imidazol-5-yl)-9H-fluoren-2-yl)-1H-benzo[d]imidazol-2-yl)-2-azabicyclo[2.2.1]heptan-2-yl)-2-oxo-1-(tetrahydro-2H-pyran-4-yl)ethylcarbamate 3× HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 939.91 [M+H]⁺. (102 mg, 57%).

Example IN

1018

(R)-2-((1R,3S,4R)-3-(6-(9,9-difluoro-7-(2-((S)-1-((S)-2-(methoxy carbonylamino)-2-(tetrahydro-2H-pyran-4-yl)acetyl)pyrrolidin-2-yl)-1H-imidazol-5-yl)-9H-fluoren-2-yl)-1H-benzo[d]imidazol-2-yl)-2-azabicyclo[2.2.1]heptan-2-yl)-2-oxo-1-phenylethylcarbamic acid methyl ester: The title compound was prepared according to the method employed to prepare (S)-benzyl 1-((S)-2-(methoxycarbonylamino)-3-methylbutanoyl)-4-oxopyrrolidine-2-carboxylate, except that methyl (R)-2-((1R,3S,4R)-3-(6-(9,9-difluoro-7-(2-((S)-pyrrolidin-2-yl)-1H-imidazol-5-yl)-9H-fluoren-2-yl)-1H-benzo[d]imidazol-2-yl)-2-azabicyclo[2.2.1]heptan-2-yl)-2-oxo-1-phenylethylcarbamate 3 HCl salt and (S)-2-(methoxycarbonylamino)-2-(tetrahydro-2H-pyran-4-yl)acetic acid were used instead of (S)-benzyl 4-oxopyrrolidine-2-carboxylate hydrochloride and (S)-2-(methoxycarbonylamino)-3-methylbutanoic acid. MS (ESI) m/z 939.92 [M+H]⁺. (34 mg, 23%).

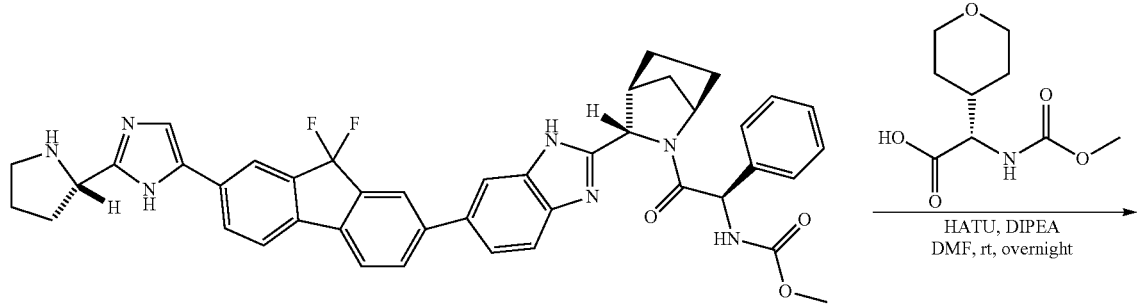

3 x HCl
methyl (R)-2-((1R,3S,4R)-3-(6-(9,9-difluoro-7-(2-((S)-pyrrolidin-2-yl)-1H-imidazol-5-yl)-9H-fluoren-2-yl)-1H-benzo[d]imidazol-2-yl)-2-azabicyclo[2.2.1]heptan-2-yl)-2-oxo-1-phenylethylcarbamate 3 HCl salt

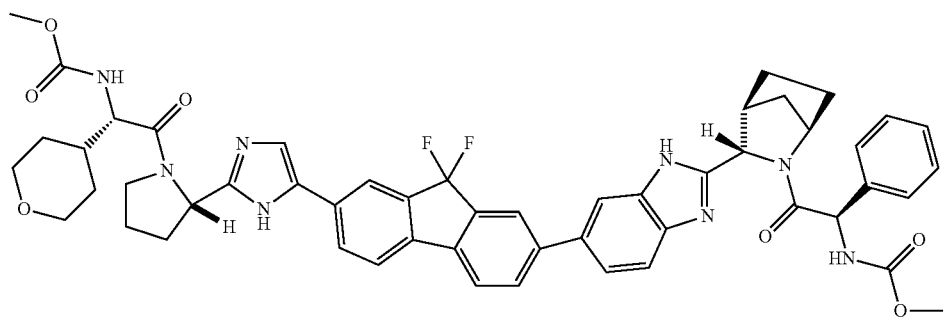

(R)-2-((1R,3S,4R)-3-(6-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)-1H-benzo[d]imidazol-2-yl)-2-azabicyclo[2.2.1]heptan-2-yl)-2-oxo-1-phenylethylcarbamic acid methyl ester

Example 10

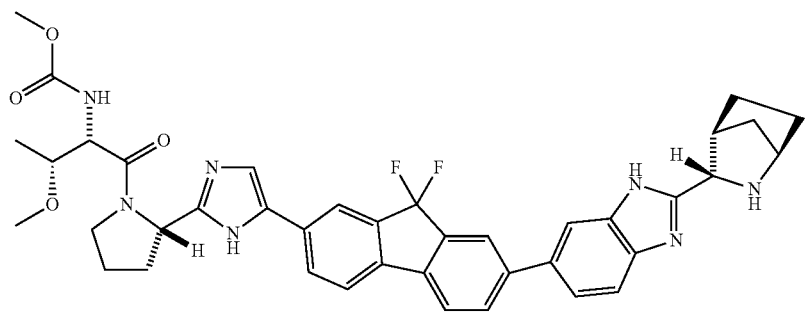 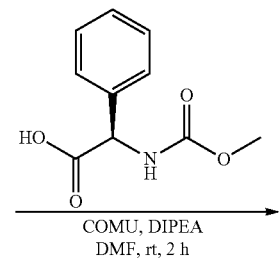

3 x HCl
methyl (2S,3R)-1-((S)-2-(5-(7-(2-((1R,3S,4R)-2-azabicyclo[2.2.1]heptan-3-yl)-1H-benzo[d]imidazol-6-yl)-9,9-difluoro-9H-fluoren-2-yl)-1H-imidazol-2-yl)pyrrolidin-1-yl)-3-methoxy-1-oxobutan-2-ylcarbamate 3HCl salt COMU, DIPEA
DMF, rt, 2 h

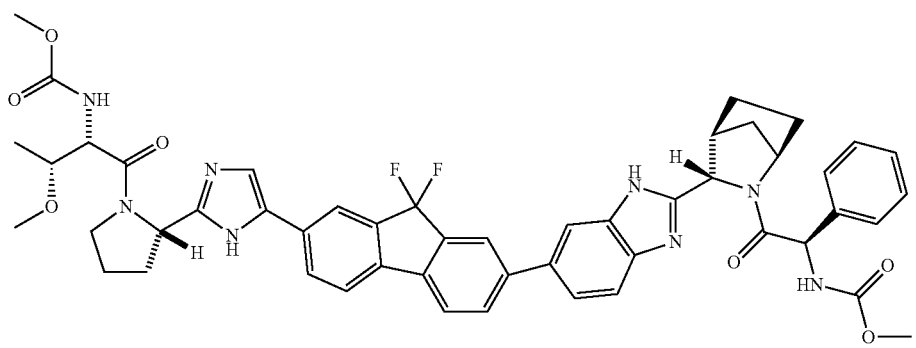

(R)-2-((1R,3S,4R)-3-(6-(9,9-difluoro-7-(2-((S)-1-((2S,3R)-3-methoxy-2-(methoxycarbonylamino)butanoyl)pyrrolidin-2-yl)-1H-imidazol-5-yl)-9H-fluoren-2-yl)-1H-benzo[d]imidazol-2-yl)-2-azabicyclo[2.2.1]heptan-2-yl)-2-oxo-1-phenylethylcarbamic acid methyl ester (R)-2-((1R,3S,4R)-3-(6-(9,9-difluoro-7-(2-((S)-1-((2S,3R)-3-methoxy-2-(methoxycarbonylamino)butanoyl)pyrrolidin-2-yl)-1H-imidazol-5-yl)-9H-fluoren-2-yl)-1H-benzo[d]imidazol-2-yl)-2-azabicyclo[2.2.1]heptan-2-yl)-2-oxo-1-phenylethylcarbamic acid methyl ester: nThe title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (2S,3R)-1-((S)-2-(5-(7-(2-((1R,3 S,4R)-2-azabicyclo[2.2.1]heptan-3-yl)-1H-benzo[d]imidazol-6-yl)-9,9-difluoro-9H-fluoren-2-yl)-1H-imidazol-2-yl)pyrrolidin-1-yl)-3-methoxy-1-oxobutan-2-ylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 913.69 [M+H]$^+$. (93 mg, 57%).

Example IP

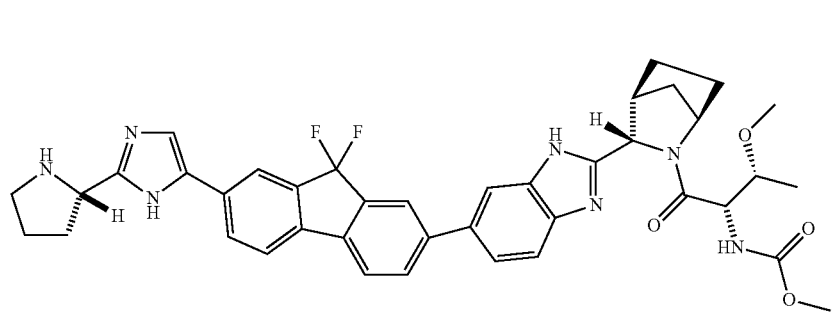
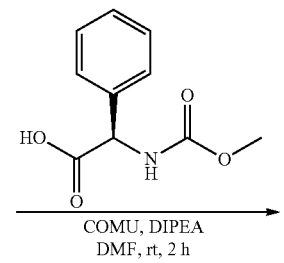

3 x HCl
methyl (2S,3R)-1-((1R,3S,4R)-3-(6-(9,9-difluoro-7-(2-((S)-pyrrolidin-2-yl)-1H-imidazol-5-yl)-9H-fluoren-2-yl)-1H-benzo[d]imidazol-2-yl)-2-azabicyclo[2.2.1]heptan-2-yl)-3-methoxy-1-oxobutan-2-ylcarbamate 3HCl salt

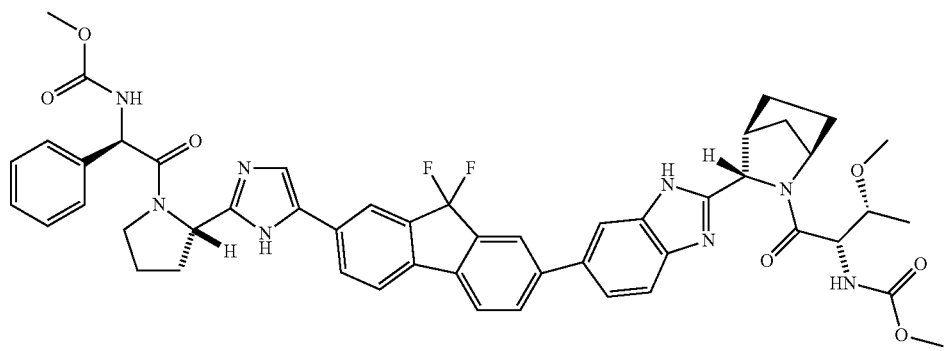

(2S,3R)-1-((1R,3S,4R)-3-(6-(9,9-difluoro-7-(2-((S)-1-((R)-2-(methoxycarbonylamino)-2-phenylacetyl)pyrrolidin-2-yl)-1H-imidazol-5-yl)-9H-fluoren-2-yl)-1H-benzo[d]imidazol-2-yl)-2-azabicyclo[2.2.1]heptan-2-yl)-3-methoxy-1-oxobutan-2-ylcarbamic acid methyl ester (2S,3R)-1-((1R,3S,4R)-3-(6-(9,9-difluoro-7-(2-((S)-1-((R)-2-(methoxycarbonylamino)-2-phenylacetyl)pyrrolidin-2-yl)-1H-imidazol-5-yl)-9H-fluoren-2-yl)-1H-benzo[d]imidazol-2-yl)-2-azabicyclo[2.2.1]heptan-2-yl)-3-methoxy-1-oxobutan-2-ylcarbamic acid methyl ester:

The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (2S,3R)-1-((1R,3S,4R)-3-(6-(9,9-difluoro-7-(2-((S)-pyrrolidin-2-yl)-1H-imidazol-5-yl)-9H-fluoren-2-yl)-1H-benzo[d]imidazol-2-yl)-2-azabicyclo[2.2.1]heptan-2-yl)-3-methoxy-1-oxobutan-2-ylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 913.74 [M+H]$^+$. (91.4 mg, 56%).

Example IQ

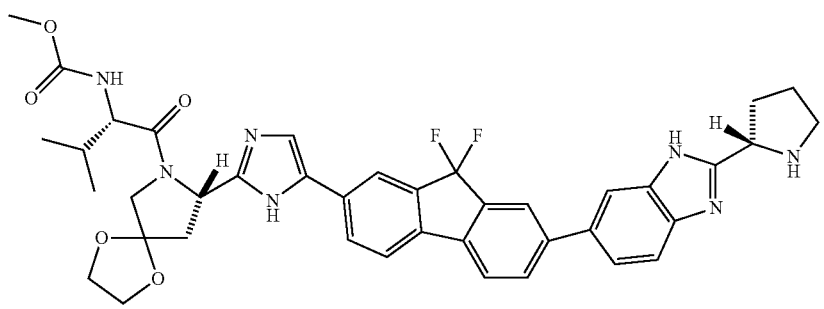 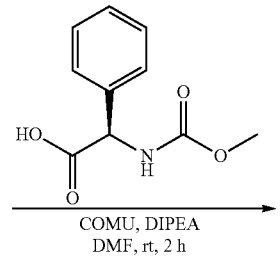

3 x HCl
methyl (S)-1-((S)-8-(5-(9,9-difluoro-7-(2-((S)-pyrrolidin-2-yl)-1H-benzo[d]imidazol-6-yl)-9H-fluoren-2-yl)-1H-imidazol-2-yl)-1,4-dioxa-7-azaspiro[4.4]nonan-7-yl)-3-methyl-1-oxobutan-2-ylcarbamate 3HCl salt

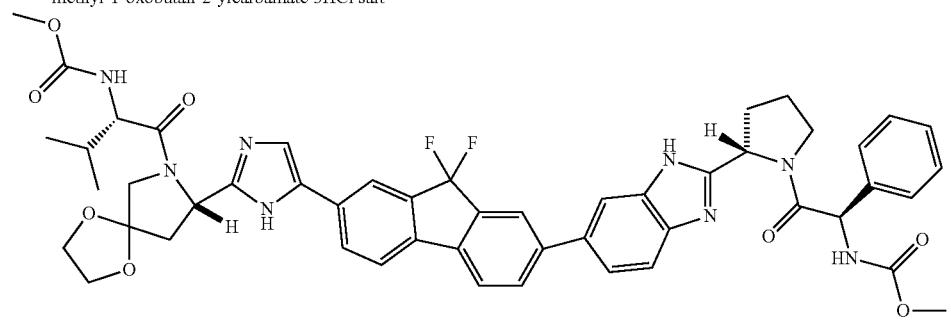

(R)-2-((S)-2-(6-(9,9-difluoro-7-(2-((S)-7-((S)-2-(methoxycarbonylamino)-3-methylbutanoyl-1,4-dioxa-7-azaspiro[4.4]nonan-8-yl)-1H-imidazol-5-yl)-9H-fluoren-2-yl)-1H-benzo[d]imidazol-2-yl)pyrrolidin-1-yl)-2-oxo-1-phenylethylcarbamic acid methyl ester (R)-2-((S)-2-(6-(9,9-difluoro-7-(2-((S)-7-((S)-2-(methoxycarbonylamino)-3-methylbutanoyl)-1,4-dioxa-7-azaspiro[4.4]nonan-8-yl)-1H-imidazol-5-yl)-9H-fluoren-2-yl)-1H-benzo[d]imidazol-2-yl)pyrrolidin-1-yl)-2-oxo-1-phenylethylcarbamic acid methyl ester:

The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-1-((S)-8-(5-(9,9-difluoro-7-(2-((S)-pyrrolidin-2-yl)-1H-benzo[d]imidazol-6-yl)-9H-fluoren-2-yl)-1H-imidazol-2-yl)-1,4-dioxa-7-azaspiro[4.4]nonan-7-yl)-3-methyl-1-oxobutan-2-ylcarbamate 3 HCl salt was used instead of methyl (S)-3-methyl-1-oxo-1-((S)-8-(5-(4-(6-2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 929.83 [M+H]$^+$. (90 mg, 63%).

Example IR

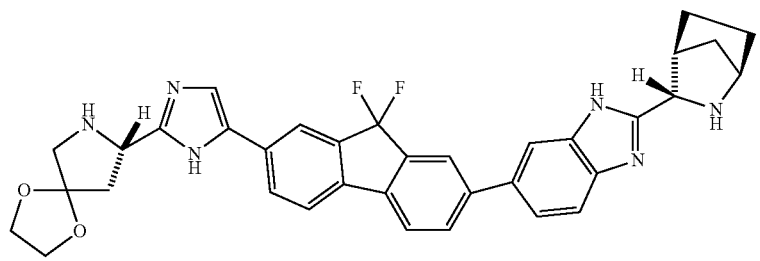 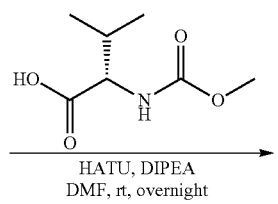

4 x HCl
(S)-8-(5-(7-(2-(((1R,3S,4R)-2-azabicyclo[2.2.1]heptan-3-yl)-1H-benzo[d]imidazol-6-yl)-9,9-difluoro-9H-fluoren-2-yl)-1H-imidazol-2-yl)-1,4-dioxa-7-azaspiro[4.4]nonane 4HCl salt

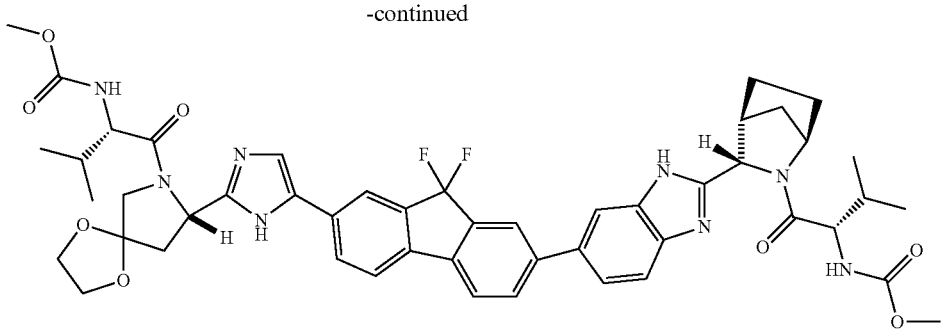

(S)-1-((1R,3S,4R)-3-(6-(9,9-difluoro-7-(2-((S)-7-((S)-2-(methoxycarbonylamino)-3-methylbutanoyl-1,4-dioxa-7-azaspiro[4.4]nonan-8-yl)-1H-imidazol-5-yl)-9H-fluoren-2-yl)-1H-benzo[d]imidazol-2-yl)-2-azabicyclo[2.2.1]heptan-2-yl)-3-methyl-1-oxobutan-2-ylcarbamic acid methyl ester (S)-1-((1R,3S,4R)-3-(6-(9,9-difluoro-7-(2-((S)-7-((S)-2-(methoxycarbonylamino)-3-methylbutanoyl)-1,4-dioxa-7-azaspiro[4.4]nonan-8-yl)-1H-imidazol-5-yl)-9H-fluoren-2-yl)-1H-benzo[d]imidazol-2-yl)-2-azabicyclo[2.2.1]heptan-2-yl)-3-methyl-1-oxobutan-2-ylcarbamic acid methyl ester: (S)-8-(5-(7-(2-((1R,3 S,4R)-2-Azabicyclo[2.2.1]heptan-3-yl)-1H-benzo[d]imidazol-6-yl)-9,9-difluoro-9H-fluoren-2-yl)-1H-imidazol-2-yl)-1,4-dioxa-7-azaspiro[4.4]nonane 4HCl salt (227 mg, 0.375 mmol), HATU (456 mg, 1.2 mmol), and (S)-2-(methoxycarbonylamino)-3-methylbutanoic acid (171 mg, 0.975 mmol) were all weighed out in a flask and dissolved in anhydrous DMF (3.75 mL), followed by addition of DIPEA (485 mg, 3.75 mmol). The mixture was stirred at room temperature overnight. The crude mixture was diluted with EtOAc and washed with brine, saturated sodium bicarbonate, brine, and dried over MgSO4. After filtration and concentration the residue was first purified on normal phase column (5% MeOH/DCM) and then on prep HPLC. MS (ESI) m/z 921.89 [M+H]$^+$. (72 mg, 21%).

Example IS

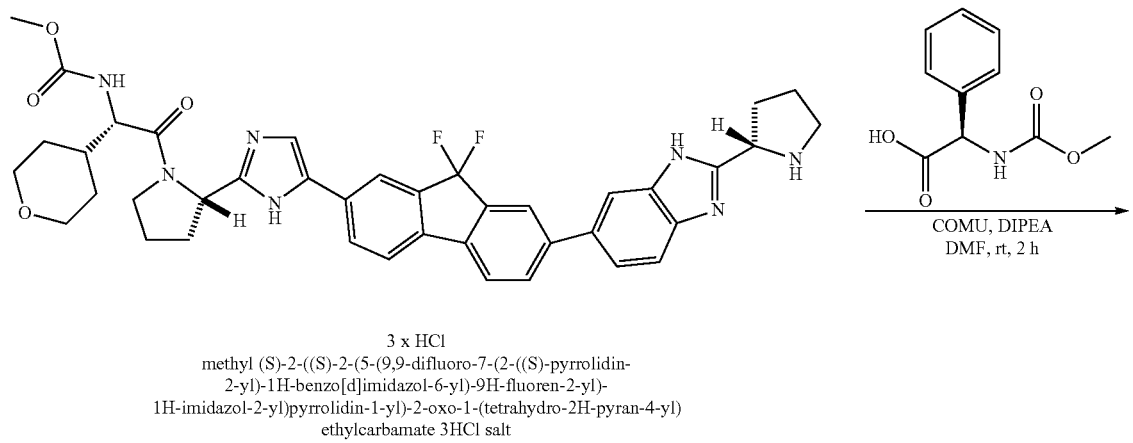

3 x HCl
methyl (S)-2-((S)-2-(5-(9,9-difluoro-7-(2-((S)-pyrrolidin-2-yl)-1H-benzo[d]imidazol-6-yl)-9H-fluoren-2-yl)-1H-imidazol-2-yl)pyrrolidin-1-yl)-2-oxo-1-(tetrahydro-2H-pyran-4-yl) ethylcarbamate 3HCl salt

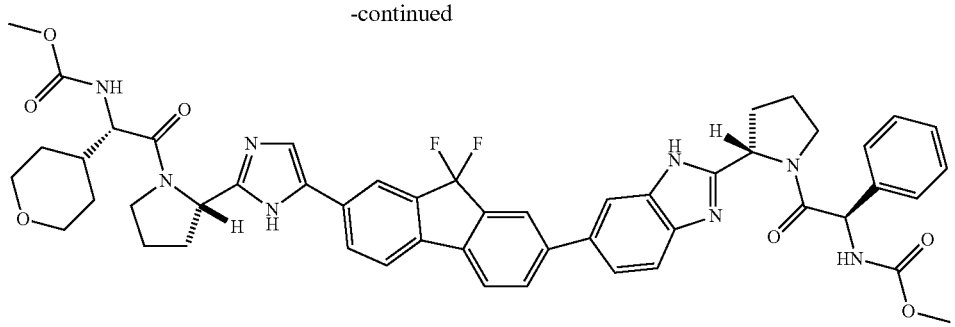

(R)-2-((S)-2-(6-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)-1H-benzo[d]imidazol-2-yl)pyrrolidin-1-yl)-2-oxo-1-phenylethylcarbamic acid methyl ester (R)-2-((S)-2-(6-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)-1H-benzo[d]imidazol-2-yl)pyrrolidin-1-yl)-2-oxo-1-phenylethylcarbamic acid methyl ester:

The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-2-((S)-2-(5-(9,9-difluoro-7-(2-((S)-pyrrolidin-2-yl)-1H-benzo[d]imidazol-6-yl)-9H-fluoren-2-yl)-1H-imidazol-2-yl)pyrrolidin-1-yl)-2-oxo-1-(tetrahydro-2H-pyran-4-yl)ethylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 914.51 [M+H]⁺. (86.2 mg, 53%).

Example IT

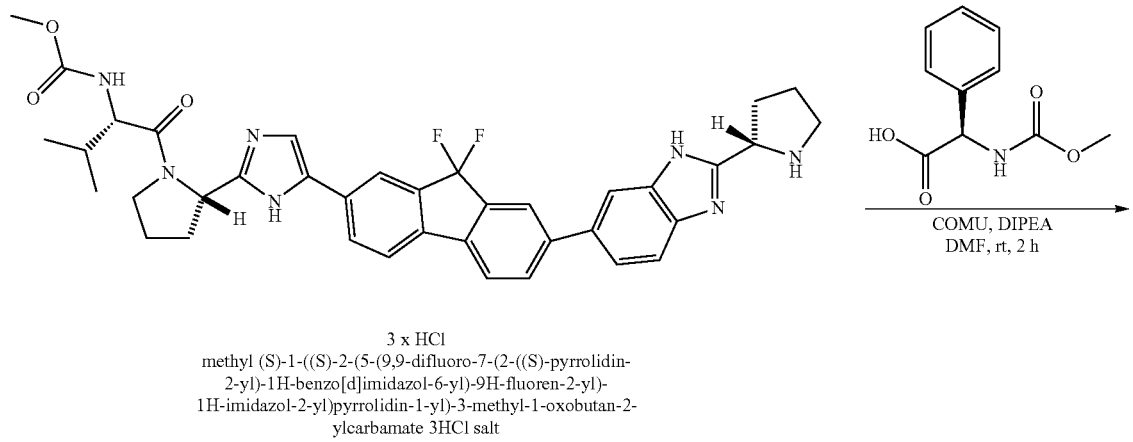

methyl (S)-1-((S)-2-(5-(9,9-difluoro-7-(2-((S)-pyrrolidin-2-yl)-1H-benzo[d]imidazol-6-yl)-9H-fluoren-2-yl)-1H-imidazol-2-yl)pyrrolidin-1-yl)-3-methyl-1-oxobutan-2-ylcarbamate 3HCl salt -continued

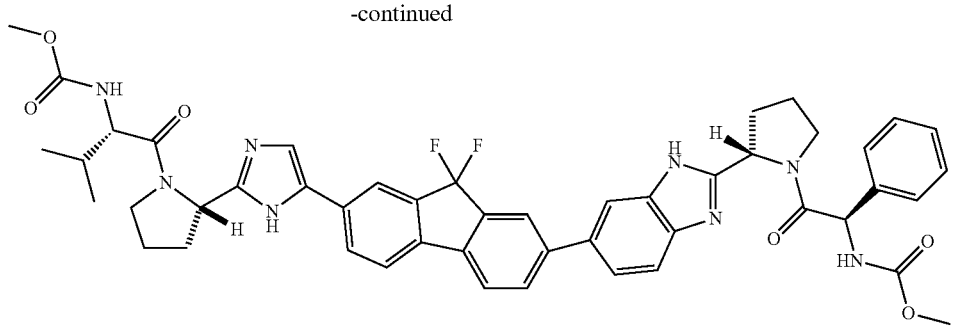

(R)-2-((S)-2-(6-(9,9-difluoro-7-(2-((S)-1-((S)-2-
(methoxycarbonylamino)-3-methylbutanoyl)pyrrolidin-2-yl)-1H-imidazol-5-yl)-
9H-fluoren-2-yl)-1H-benzo[d]imidazol-2-yl)pyrrolidin-1-yl)-2-oxo-1-phenylethylcarbamic
acid methyl ester (R)-2-((S)-2-(6-(9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)-1H-benzo[d]imidazol-2-yl)pyrrolidin-1-yl)-2-oxo-1-phenylethylcarbamic acid methyl ester: The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-1-((S)-2-(5-(9,9-difluoro-7-(2-((S)-pyrrolidin-2-yl)-1H-benzo[d]imidazol-6-yl)-9H-fluoren-2-yl)-1H-imidazol-2-yl)pyrrolidin-1-yl)-3-methyl-1-oxobutan-2-ylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 872.50 [M+H]⁺. (97.5 mg, 59%).

Example IU

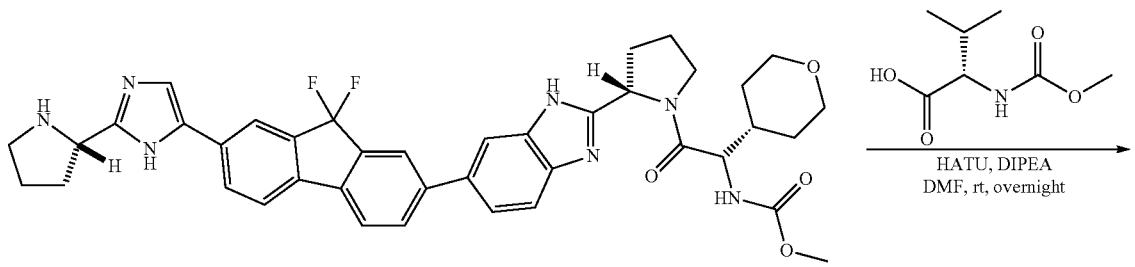

3 × HCl
methyl (S)-2-((S)-2-(6-(9,9-difluoro-7-(2-((S)-pyrrolidin-2-yl)-1H-
imidazol-5-yl)-9H-fluoren-2-yl)-1H-benzo[d]imidazol-2-yl)pyrrolidin-1-yl)-
2-oxo-1-(tetrahydro-2H-pyran-4-yl)ethylcarbamate 3 HCl salt

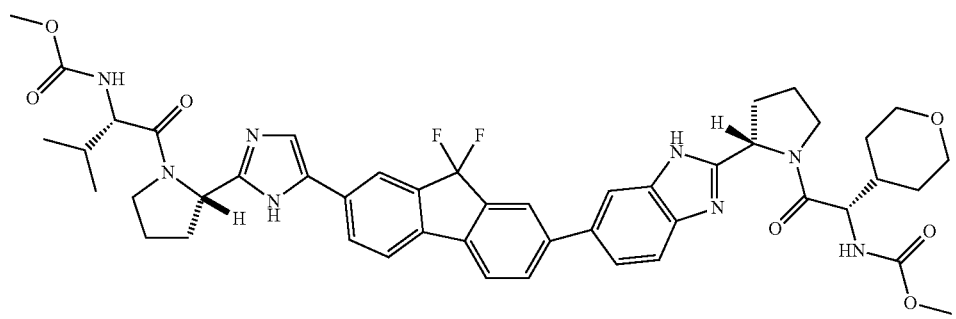

(S)-2-((S)-2-(6-(9,9-difluoro-7-(2-((S)-1-((S)-2-
(methoxycarbonylamino)-3-methylbutanoyl)pyrrolidin-2-yl)-1H-imidazol-5-yl)-
9H-fluoren-2-yl)-1H-benzo[d]imidazol-2-yl)pyrrolidin-1-yl)-2-oxo-1-(tetrahydro-2H-pyran-4-
yl)ethylcarbamic acid methyl ester (S)-2-((S)-2-(6-(9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)-1H-benzo[d]imidazol-2-yl)pyrrolidin-1-yl)-2-oxo-1-(tetrahydro-2H-pyran-4-yl)ethylcarbamic acid methyl ester:

The title compound was prepared according to the method employed to prepare (S)-benzyl 1-((S)-2-(methoxycarbonylamino)-3-methylbutanoyl)-4-oxopyrrolidine-2-carboxylate, except that methyl (S)-2-((S)-2-(6-(9,9-difluoro-7-(2-((S)-pyrrolidin-2-yl)-1H-imidazol-5-yl)-9H-fluoren-2-yl)-1H-benzo[d]imidazol-2-yl)pyrrolidin-1-yl)-2-oxo-1-(tetrahydro-2H-pyran-4-yl)ethylcarbamate 3HCl salt was used instead of (S)-benzyl 4-oxopyrrolidine-2-carboxylate hydrochloride. MS (ESI) m/z 879.88 [M+H]$^+$. (122 mg, 52%).

Example IV

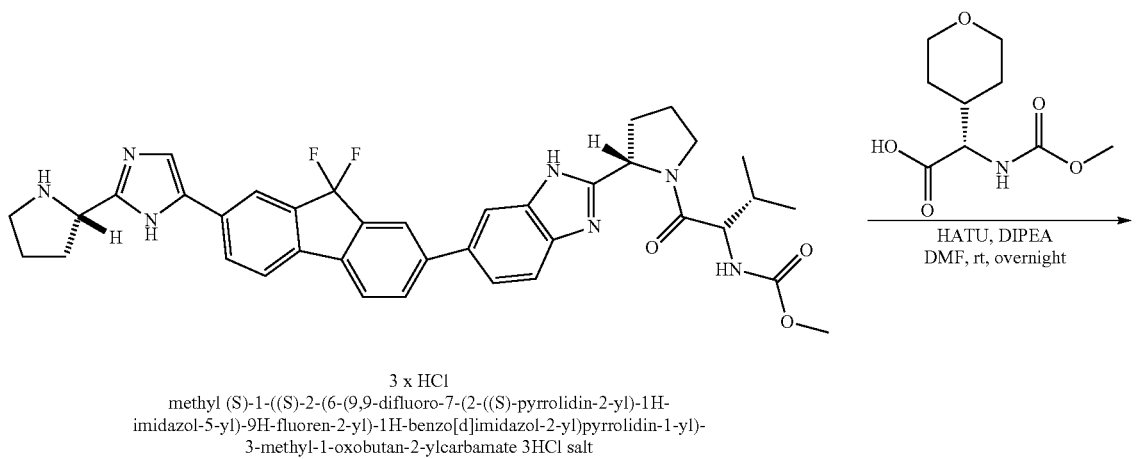

3 x HCl
methyl (S)-1-((S)-2-(6-(9,9-difluoro-7-(2-((S)-pyrrolidin-2-yl)-1H-imidazol-5-yl)-9H-fluoren-2-yl)-1H-benzo[d]imidazol-2-yl)pyrrolidin-1-yl)-3-methyl-1-oxobutan-2-ylcarbamate 3HCl salt

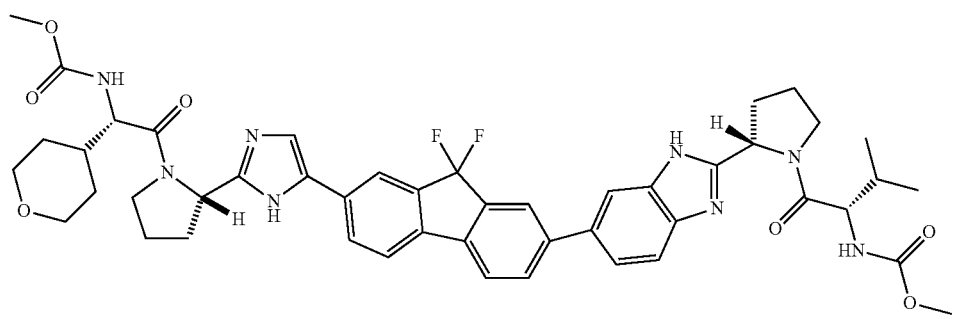

(S)-1-((S)-2-(6-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)-1H-benzo[d]imidazol-2-yl)pyrrolidin-1-yl)-3-methyl-1-oxobutan-2-ylcarbamic acid methyl ester (S)-1-((S)-2-(6-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)-1H-benzo[d]imidazol-2-yl)pyrrolidin-1-yl)-3-methyl-1-oxobutan-2-ylcarbamic acid methyl ester: The title compound was prepared according to the method employed to prepare (S)-benzyl 1-((S)-2-(methoxycarbonylamino)-3-methylbutanoyl)-4-oxopyrrolidine-2-carboxylate, except that methyl (S)-1-((S)-2-(6-(9,9-difluoro-7-(2-((S)-pyrrolidin-2-yl)-1H-imidazol-5-yl)-9H-fluoren-2-yl)-1H-benzo[d]imidazol-2-yl)pyrrolidin-1-yl)-3-methyl-1-oxobutan-2-ylcarbamate 3HCl salt and (S)-2-(methoxycarbonylamino)-2-(tetrahydro-2H-pyran-4-yl)acetic acid were used instead of (S)-benzyl 4-oxopyrrolidine-2-carboxylate hydrochloride and (S)-2-(methoxycarbonylamino)-3-methylbutanoic acid. MS (ESI) m/z 879.90 [M+H]$^+$. (105.8 mg, 50%).

Example IW

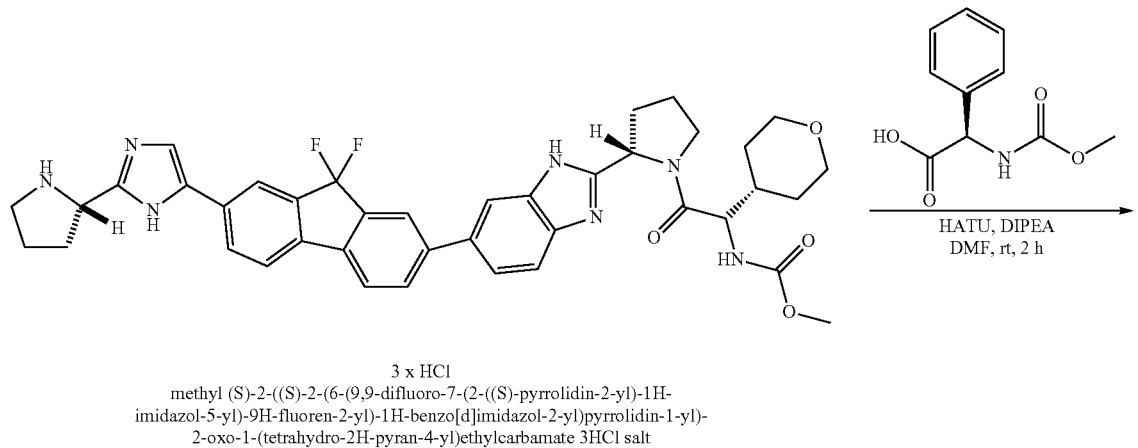

3 x HCl
methyl (S)-2-((S)-2-(6-(9,9-difluoro-7-(2-((S)-pyrrolidin-2-yl)-1H-imidazol-5-yl)-9H-fluoren-2-yl)-1H-benzo[d]imidazol-2-yl)pyrrolidin-1-yl)-2-oxo-1-(tetrahydro-2H-pyran-4-yl)ethylcarbamate 3HCl salt

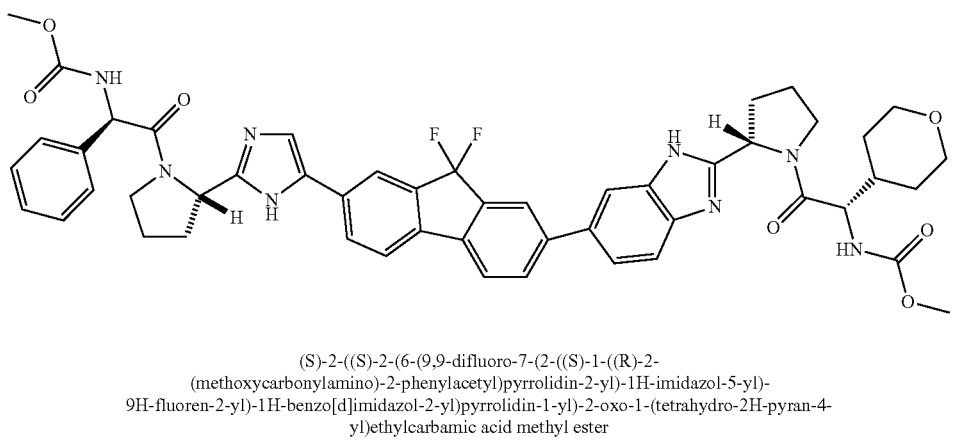

(S)-2-((S)-2-(6-(9,9-difluoro-7-(2-((S)-1-((R)-2-(methoxycarbonylamino)-2-phenylacetyl)pyrrolidin-2-yl)-1H-imidazol-5-yl)-9H-fluoren-2-yl)-1H-benzo[d]imidazol-2-yl)pyrrolidin-1-yl)-2-oxo-1-(tetrahydro-2H-pyran-4-yl)ethylcarbamic acid methyl ester (S)-2-((S)-2-(6-(9,9-difluoro-7-(2-((S)-1-((R)-2-(methoxycarbonylamino)-2-phenylacetyl)pyrrolidin-2-yl)-1H-imidazol-5-yl)-9H-fluoren-2-yl)-1H-benzo[d]imidazol-2-yl)pyrrolidin-1-yl)-2-oxo-1-(tetrahydro-2H-pyran-4-yl)ethylcarbamic acid methyl ester:

The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-2-((S)-2-(6-(9,9-difluoro-7-(2-((S)-pyrrolidin-2-yl)-1H-imidazol-5-yl)-9H-fluoren-2-yl)-1H-1-benzo[d]imidazol-2-yl)pyrrolidin-1-yl)-2-oxo-1-(tetrahydro-2H-pyran-4-yl)ethylcarbamate 3 HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 913.94 [M+H]$^+$. (77.4 mg, 24%).

Example IX

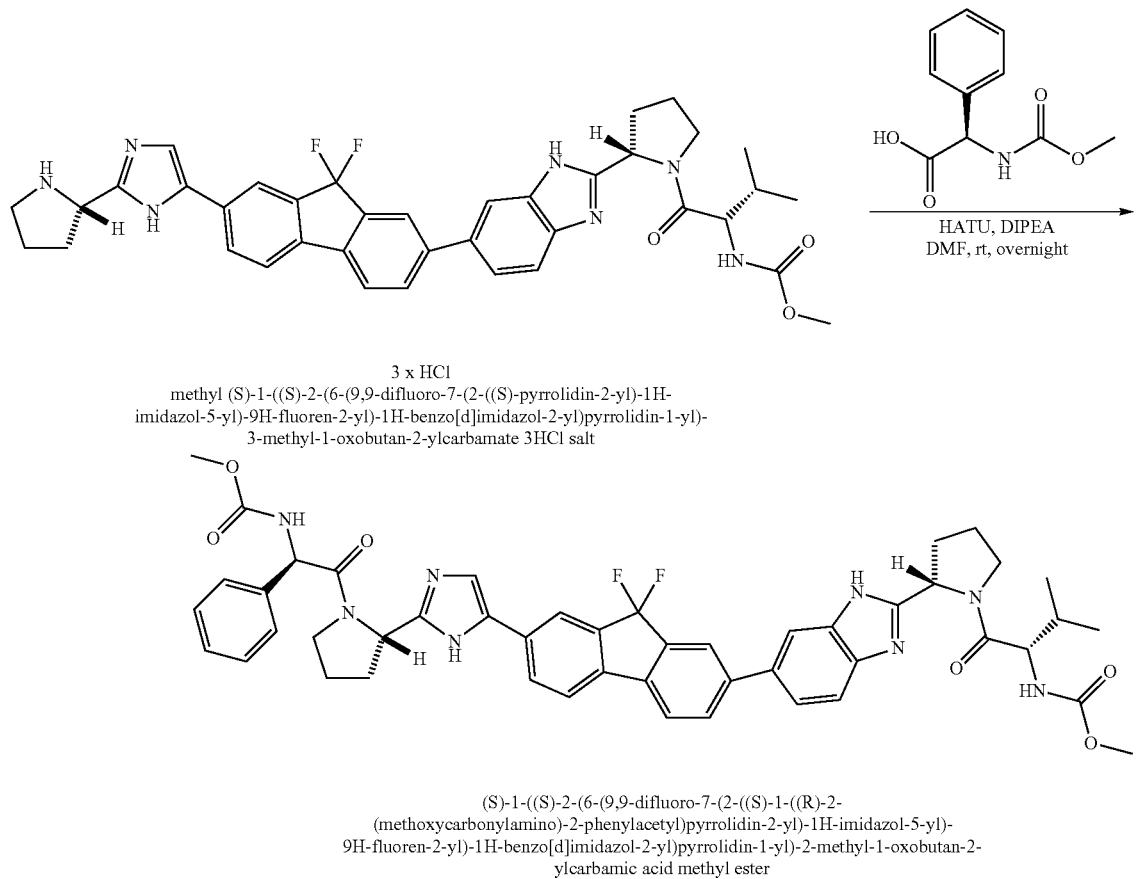

3 x HCl
methyl (S)-1-((S)-2-(6-(9,9-difluoro-7-(2-((S)-pyrrolidin-2-yl)-1H-imidazol-5-yl)-9H-fluoren-2-yl)-1H-benzo[d]imidazol-2-yl)pyrrolidin-1-yl)-3-methyl-1-oxobutan-2-ylcarbamate 3HCl salt (S)-1-((S)-2-(6-(9,9-difluoro-7-(2-((S)-1-((R)-2-(methoxycarbonylamino)-2-phenylacetyl)pyrrolidin-2-yl)-1H-imidazol-5-yl)-9H-fluoren-2-yl)-1H-benzo[d]imidazol-2-yl)pyrrolidin-1-yl)-2-methyl-1-oxobutan-2-ylcarbamic acid methyl ester (S)-1-((S)-2-(6-(9,9-difluoro-7-(2-((S)-1-((R)-2-(methoxycarbonylamino)-2-phenylacetyl)pyrrolidin-2-yl)-1H-imidazol-5-yl)-9H-fluoren-2-yl)-1H-benzo[d]imidazol-2-yl)pyrrolidin-1-yl)-3-methyl-1-oxobutan-2-ylcarbamic acid methyl ester: The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-1-((S)-2-(6-(9,9-difluoro-7-(2-((S)-pyrrolidin-2-yl)-1H-imidazol-5-yl)-9H-fluoren-2-yl)-1H-benzo[d]imidazol-2-yl)pyrrolidin-1-yl)-3-methyl-1-oxobutan-2-ylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 871.95 [M+H]+. (174 mg, 53%).

Example IY

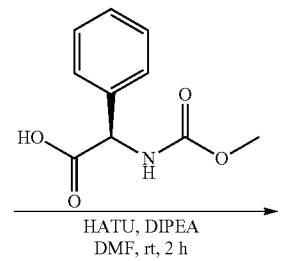

3 x HCl
methyl (S)-1-((S)-1-(4-(9,9-difluoro-7-(2-((S)-pyrrolidin-2-yl)-1H-benzo[d]imidazol-6-yl)-9H-fluoren-2-yl)-1H-imidazol-2-yl)-2-methylpropylamino)-3-methyl-1-oxobutan-2-ylcarbamate 3HCl salt

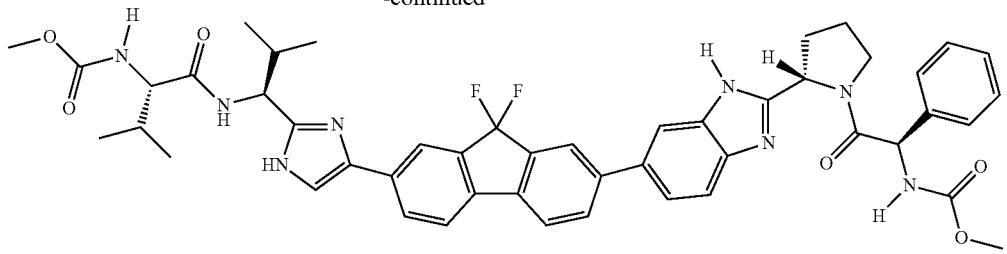

(R)-2-((S)-2-(6-(9,9-difluoro-7-(2-((S)-1-((S)-2-
(methoxycarbonylamino)-3-methylbutanamido)-2-methylpropyl)-1H-imidazol-4-yl)-
9H-fluoren-2-yl)-1H-benzo[d]imidazol-2-yl)pyrrolidin-1-yl)-2-oxo-1-phenylethylcarbamic acid methyl ester (R)-2-((S)-2-(6-(9,9-difluoro-7-(2-((S)-1-((S)-2-(methoxycarbonylamino)-3-methylbutanamido)-2-methylpropyl)-1H-imidazol-4-yl)-9H-fluoren-2-yl)-1H-benzo[d]imidazol-2-yl)pyrrolidin-1-yl)-2-oxo-1-phenylethylcarbamic acid methyl ester:

The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-1-((S)-1-(4-(9,9-difluoro-7-(2-((S)-pyrrolidin-2-yl)-1H-benzo[d]imidazol-6-yl)-9H-fluoren-2-yl)-1H-imidazol-2-yl)-2-methylpropylamino)-3-methyl-1-oxobutan-2-ylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 873.92 [M+H]+. (62 mg, 37%).

Example IZ

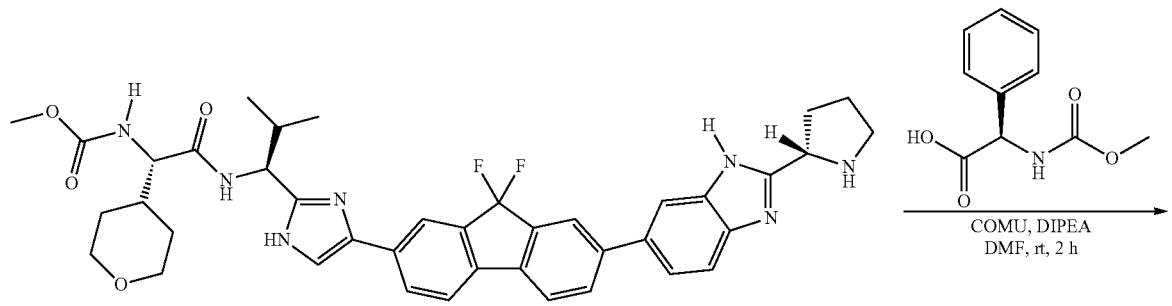

3 x HCl
methyl (S)-2-((S)-1-(4-(9,9-difluoro-7-(2-((S)-pyrrolidin-2-yl)-1H-
-benzo[d]imidazol-6-yl)-9H-fluoren-2-yl)-1H-imidazol-2-yl)-2-methylpropylamino)
-2-oxo-1-(tetrahydro-2H-pyran-4-yl)ethylcarbamate 3HCl salt

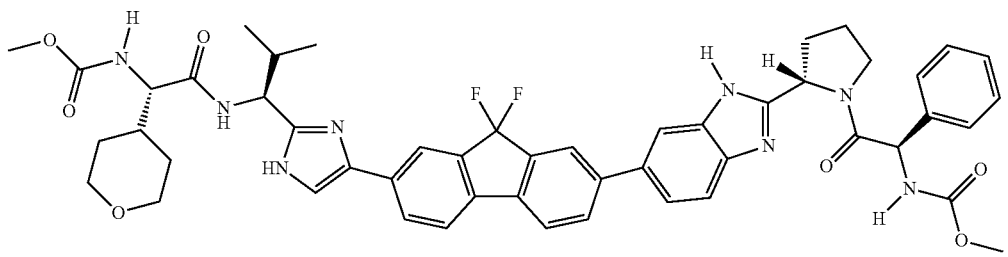

(R)-2-((S)-2-(6-(9,9-difluoro-7-(2-((S)-1-((S)-2-
(methoxycarbonylamino)-2-tetrahydro-2H-pyran-4-yl)acetamido-2-methylpropyl)-1H-imidazol-4-yl)-
9H-fluoren-2-yl)-1H-benzo[d]imidazol-2-yl)pyrrolidin-1-yl)-2-oxo-1-phenylethylcarbamic acid methyl ester (R)-2-((S)-2-(6-(9,9-difluoro-7-(2-((S)-1-((S)-2-(methoxycarbonylamino)-2-(tetrahydro-2H-pyran-4-yl)acetamido)-2-methylpropyl)-1H-imidazol-4-yl)-9H-fluoren-2-yl)-1H-benzo[d]imidazol-2-yl)pyrrolidin-1-yl)-2-oxo-1-phenylethylcarbamic acid methyl ester:

The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-2-((S)-1-(4-(9,9-difluoro-7-(2-((S)-pyrrolidin-2-yl)-1H-benzo[d]imidazol-6-yl)-9H-fluoren-2-yl)-1H-imidazol-2-yl)-2-methylpropylamino)-2-oxo-1-(tetrahydro-2H-pyran-4-yl)ethylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-yl-carbamate 3 HCl salt. MS (ESI) m/z 915.94 [M+H]$^+$. (52 mg, 32%).

Example JA

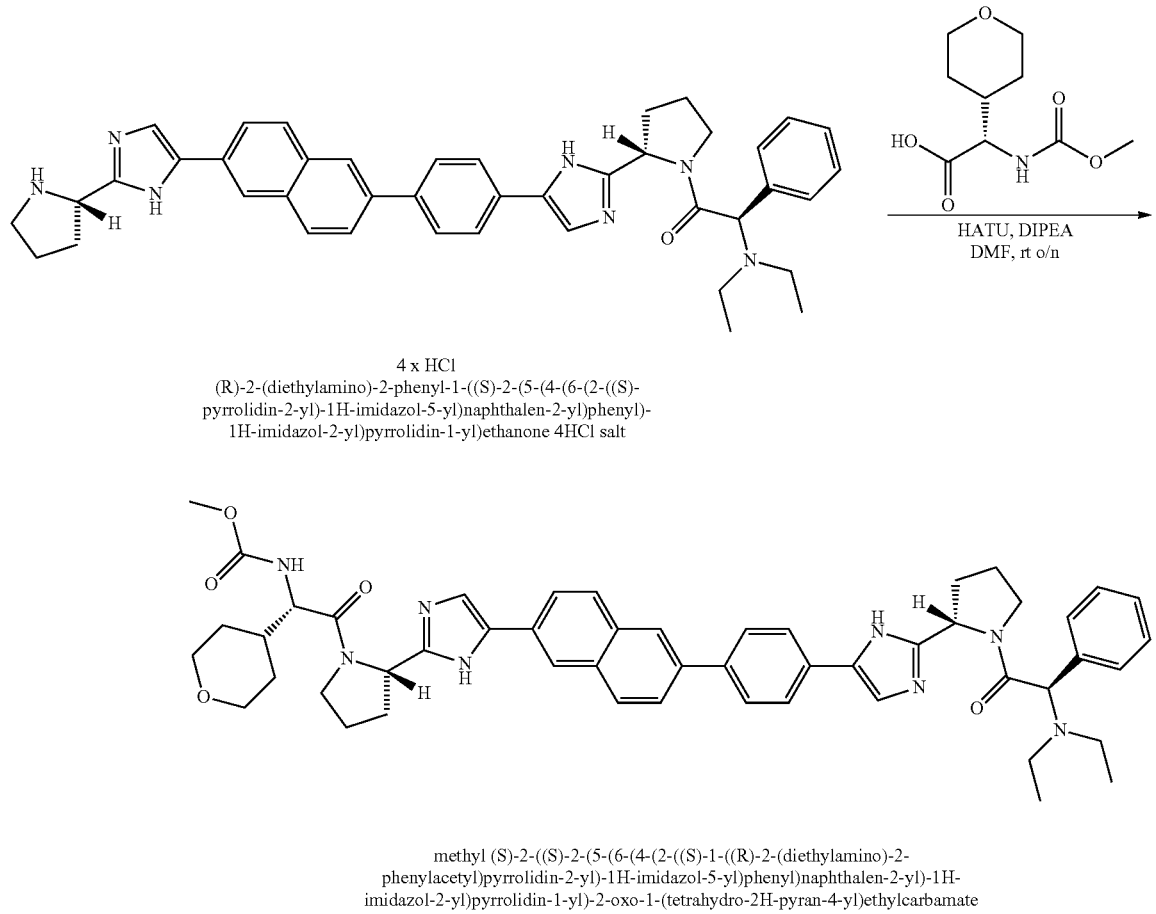

4 x HCl
(R)-2-(diethylamino)-2-phenyl-1-((S)-2-(5-(4-(6-(2-((S)-pyrrolidin-2-yl)-1H-imidazol-5-yl)naphthalen-2-yl)phenyl)-1H-imidazol-2-yl)pyrrolidin-1-yl)ethanone 4HCl salt methyl (S)-2-((S)-2-(5-(6-(4-(2-((S)-1-((R)-2-(diethylamino)-2-phenylacetyl)pyrrolidin-2-yl)-1H-imidazol-5-yl)phenyl)naphthalen-2-yl)-1H-imidazol-2-yl)pyrrolidin-1-yl)-2-oxo-1-(tetrahydro-2H-pyran-4-yl)ethylcarbamate Methyl (S)-2-((S)-2-(5-(6-(4-(2-((S)-1-((R)-2-(diethylamino)-2-phenylacetyl)pyrrolidin-2-yl)-1H-imidazol-5-yl)phenyl)naphthalen-2-yl)-1H-imidazol-2-yl)pyrrolidin-1-yl)-2-oxo-1-(tetrahydro-2H-pyran-4-yl)ethylcarbamate: The title compound was prepared according to the method employed to prepare (S)-benzyl 1-((S)-2-(methoxycarbonylamino)-3-methylbutanoyl)-4-oxopyrrolidine-2-carboxylate, except that (R)-2-(diethylamino)-2-phenyl-1-((S)-2-(5-(4-(6-(2-((S)-pyrrolidin-2-yl)-1H-imidazol-5-yl)naphthalen-2-yl)phenyl)-1H-imidazol-2-yl)pyrrolidin-1-yl)ethanone 4HCl salt and (S)-2-(methoxycarbonylamino)-2-(tetrahydro-2H-pyran-4-yl)acetic acid were used instead of (S)-benzyl 4-oxopyrrolidine-2-carboxylate hydrochloride and (S)-2-(methoxycarbonylamino)-3-methylbutanoic acid. MS (ESI) m/z 863.81 [M+H]$^+$. (34 mg, 39%).

Example JB

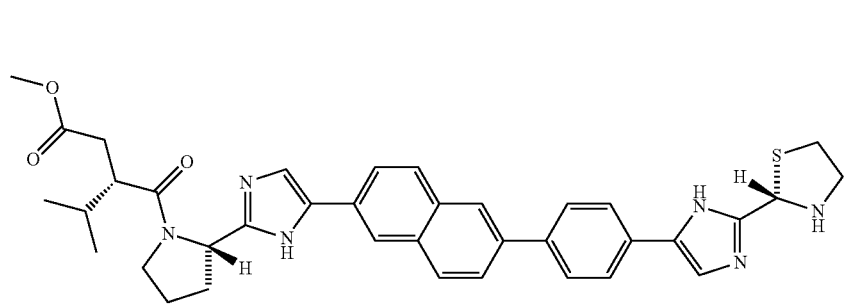 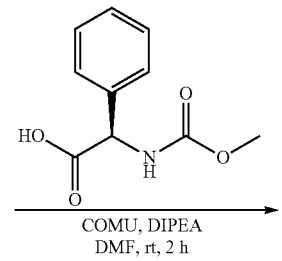

4 x HCl
methyl (S)-3-methyl-1-oxo-1-((S)-2-(5-(6-(4-(2-((S)-thiazolidin-2-yl)
-1H-imidazol-5-yl)phenyl)naphthalen-2-yl)-1H-imidazol-2-yl)
pyrrolidin-1-yl)butan-2-ylcarbamate 4HCl salt COMU, DIPEA
DMF, rt, 2 h

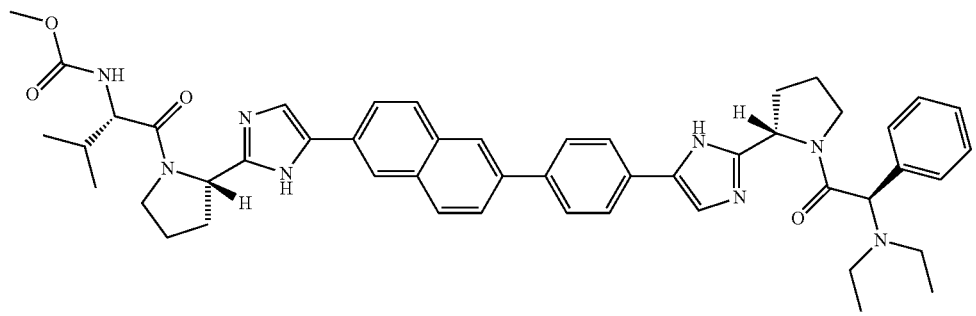

(R)-2-((S)-2-(5-(4-(6-(2-((S)-1-((S)-2-(methoxycarbonylamino)-3-
methylbutanoyl)pyrrolidin-2-yl)-1H-imidazol-5-yl)naphthalen-2-yl)phenyl)-1H-
imidazol-2-yl)thiazolidin-3-yl)-2-oxo-1-phenylethylcarbamic acid methyl ester (R)-2-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)thiazolidin-3-yl)-2-oxo-1-phenylethylcarbamic acid methyl ester: The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-3-methyl-1-oxo-1-((S)-2-(5-(6-(4-(2-((S)-thiazolidin-2-yl)-1H-imidazol-5-yl)phenyl)naphthalen-2-yl)-1H-imidazol-2-yl)pyrrolidin-1-yl)butan-2-ylcarbamate 4HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 841.83 [M+H]$^+$. (25 mg, 12%).

Example JC

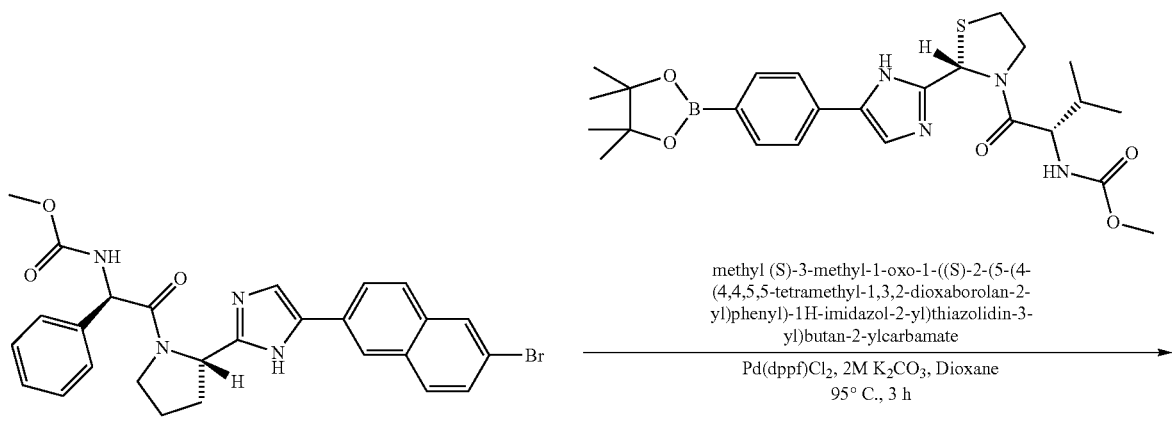

methyl (R)-2-((S)-2-(5-(6-bromonaphthalen-
2-yl)-1H-imidazol-2-yl)pyrrolidin-1-yl)-2-oxo-
1-phenylethylcarbamate methyl (S)-3-methyl-1-oxo-1-((S)-2-(5-(4-
(4,4,5,5-tetramethyl-1,3,2-dioxaborolan-2-
yl)phenyl)-1H-imidazol-2-yl)thiazolidin-3-
yl)butan-2-ylcarbamate Pd(dppf)Cl₂, 2M K₂CO₃, Dioxane
95° C., 3 h

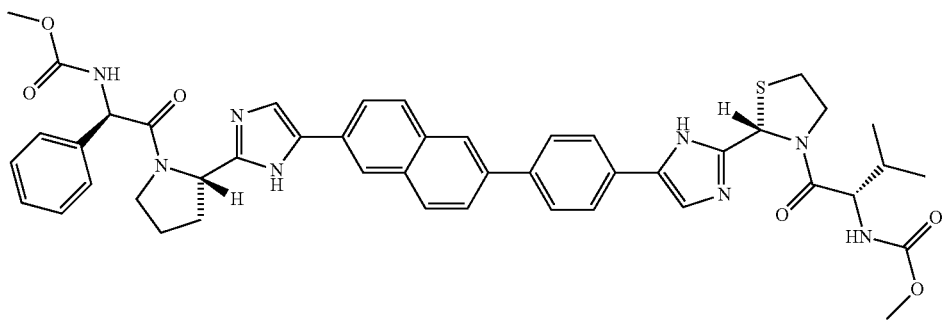

(S)-1-((S)-2-(5-(4-(6-(2-((S)-1-((R)-2-(methoxycarbonylamino)-
2-phenylacetyl)pyrrolidin-2-yl)-1H-imidazol-5-yl)naphthalen-2-
yl)phenyl)-1H-imidazol-2-yl)thiazolidin-3-yl)-3-methyl-1-
oxobutan-2-ylcarbamic acid methyl ester (S)-1-((S)-2-(5-(4-(6-(2-((S)-1-((R)-2-(methoxycarbo-nylamino)-2-phenylacetyl)pyrrolidin-2-yl)-1H-imidazol-5-yl)naphthalen-2-yl)phenyl)-1H-imidazol-2-yl)thiazolidin-3-yl)-3-methyl-1-oxobutan-2-ylcarbamic acid methyl ester: Methyl (R)-2-((S)-2-(5-(6-bromonaphthalen-2-yl)-1H-imidazol-2-yl)pyrrolidin-1-yl)-2-oxo-1-phenylethylcarbamate (155 mg, 0.29 mmol), methyl (S)-3-methyl-1-oxo-1-((S)-2-(5-(4-(4,4,5,5-tetramethyl-1,3,2-dioxaborolan-2-yl)phenyl)-1H-imidazol-2-yl)thiazolidin-3-yl)butan-2-ylcarbamate (195 mg, 0.37 mmol), Pd(dppf)Cl2 (43 mg, 0.058 mmol) and 2M K2CO3 (320 uL, 0.64 mmol) were all dissolved in 1,4-dioxane (1.5 mL) and the mixture was bubbled with nitrogen gas for 5 minutes. The vessel was capped, sealed and placed in an oil bath at 95° C. for 3 hours.

The resulting crude mixture was diluted with ethyl acetate and washed, respectively, with brine, 10% Na₂CO₃, 10% citric acid, saturated solution of NH₄Cl, and brine. The organic layer was then dried over Na₂SO₄ and the volatiles were removed on rotovap. The residue was purified on normal phase chromatography. (19 mg, 8%).

Example JD

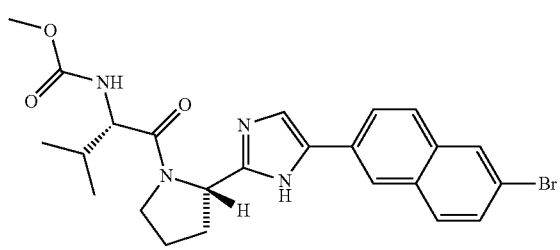

methyl (R)-2-((S)-2-(5-6-bromonaphthalen-2-yl)-1H-imidazol-2-yl)pyrrolidin-1-yl)-3-methyl-1-oxobutan-2-ylcarbamate

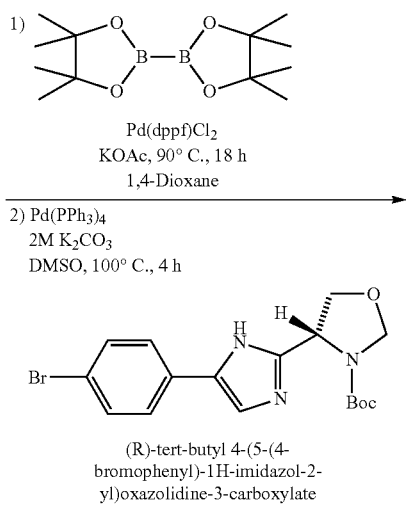

(R)-tert-butyl 4-(5-(4-bromophenyl)-1H-imidazol-2-yl)oxazolidine-3-carboxylate

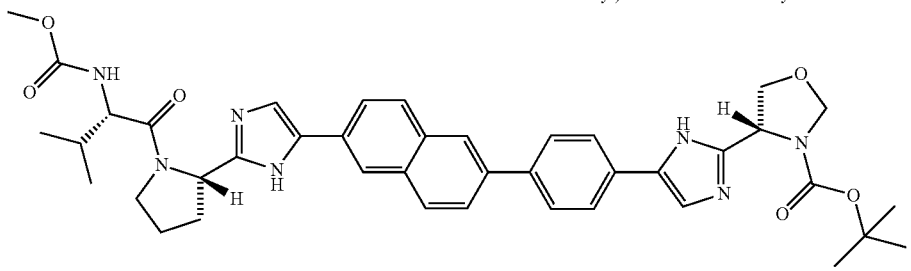

(R)-tert-butyl 4-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)oxazolidine-3-carboxylate (R)-tert-butyl 4-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)oxazolidine-3-carboxylate: The title compound was prepared according to the method employed to prepare (S)-Tert-butyl 2-(7-(4-(2-((S)-7-((S)-2-(methoxycarbonylamino)-3-methylbutanoyl)-1,4-dioxa-7-azaspiro[4.4]nonan-8-yl)-1H-imidazol-5-yl)phenyl)-1H-naphtho[1,2-d]imidazol-2-yl)pyrrolidine-1-carboxylate, except that, respectively, methyl (S)-1-((S)-2-(5-(6-bromonaphthalen-2-yl)-1H-imidazol-2-yl)pyrrolidin-1-yl)-3-methyl-1-oxobutan-2-ylcarbamate and (R)-tert-butyl 4-(5-(4-bromophenyl)-1H-imidazol-2-yl)oxazolidine-3-carboxylate were used instead of methyl (S)-1-((S)-8-(5-(4-bromophenyl)-1H-imidazol-2-yl)-1,4-dioxa-7-azaspiro[4.4]nonan-7-yl)-3-methyl-1-oxobutan-2-ylcarbamate (100 mg, 0.197 mmol), bis(pinacolato)diboron and (S)-tert-butyl 2-(7-bromo-1H-naphtho[1,2-d]imidazol-2-yl)pyrrolidine-1-carboxylate. MS (ESI) m/z 734.91 [M+H]$^+$. (110 mg, 45%).

Example JE

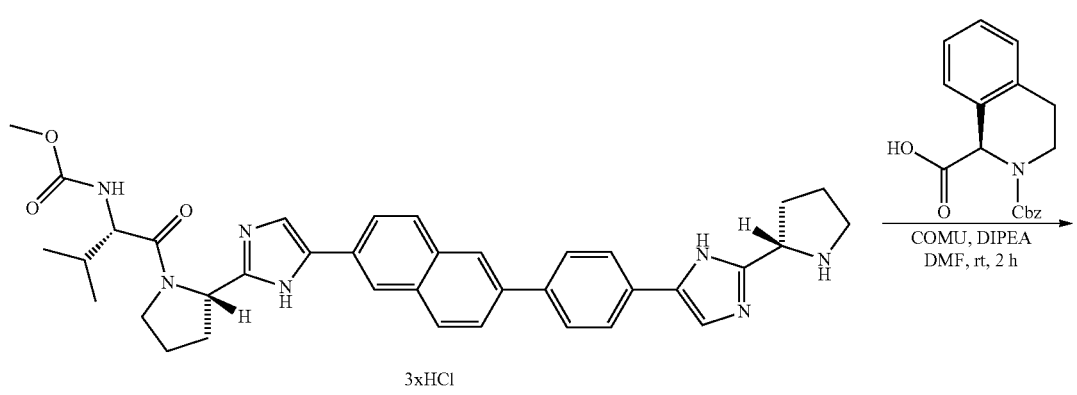

methyl (S)-3-methyl-1-oxo-1-((S)-2-(5-(6-(4-(2-((S)-pyrrolidin-2-yl)-1H-imidazol-5-yl)phenyl)naphthalen-2-yl)-1H-imidazol-2-yl)pyrrolidin-1-yl)butan-2-ylcarbamate 3HCl salt

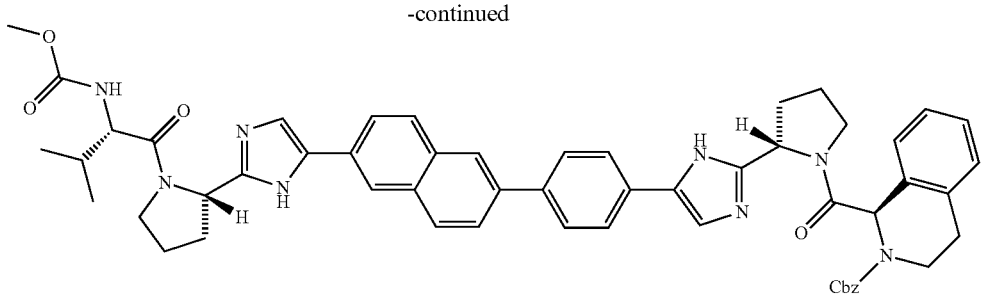

(R)-benzyl 1-((S)-2-(5-(4-(6-(2-((S)-1-((S)-2-
(methoxycarbonylamino)-3-methylbutanoyl)pyrrolidin-2-yl)-1H-
imidazol-5-yl)naphthalen-2-yl)phenyl)-1H-imidazol-2-yl)pyrrolidine-
1-carbonyl)-3,4-dihydroisoquinoline-2(1H)-carboxylate (R)-Benzyl 1-((S)-2-(5-(4-(6-(2-((S)-1-((S)-2-(methoxy-carbonylamino)-3-methylbutanoyl)pyrrolidin-2-yl)-1H-imidazol-5-yl)naphthalen-2-yl)phenyl)-1H-imidazol-2-yl)pyrrolidine-1-carbonyl)-3,4-dihydroisoquinoline-2(1H)-carboxylate: The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-3-methyl-1-oxo-1-((S)-2-(5-(6-(4-(2-((S)-pyrrolidin-2-yl)-1H-imidazol-5-yl)phenyl)naphthalen-2-yl)-1H-imidazol-2-yl)pyrrolidin-1-yl)butan-2-ylcarbamate 3HCl salt and (R)-2-(benzyloxycarbonyl)-1,2,3,4-tetrahydroisoquinoline-1-carboxylic acid were used instead of, respectively, methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt (R)-2-(methoxycarbonylamino)-2-phenylacetic acid. MS (ESI) m/z 841.83 [M+H]$^+$. (135 mg, 99%).

Example JF

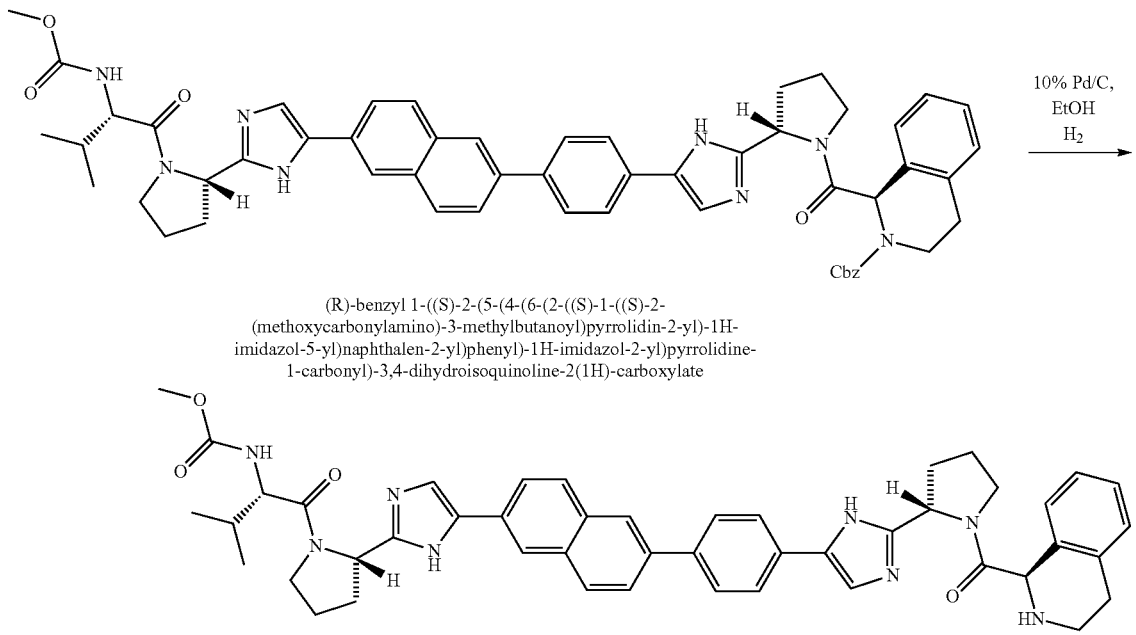

methyl (S)-3-methyl-1-oxo-1-((S)-2-(5-(6-(4-(2-((S)-1-((R)-1,2,3,4-
tetrahydroisoquinoline-1-carbonyl)pyrrolidin-2-yl)-1H-imidazol-5-
yl)phenyl)naphthalen-2-yl)-1H-imidazol-2-yl)pyrrolidin-1-yl)butan-2-ylcarbamate Methyl (S)-3-methyl-1-oxo-1-((S)-2-(5-(6-(4-(2-((S)-1-((R)-1,2,3,4-tetrahydroisoquinoline-1-carbonyl)pyrrolidin-2-yl)-1H-imidazol-5-yl)phenyl)naphthalen-2-yl)-1H-imidazol-2-yl)pyrrolidin-1-yl)butan-2-ylcarbamate: (R)-Benzyl 1-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carbonyl)-3,4-dihydroisoquinoline-2(1H)-carboxylate (137 mg, 0.148 mmol) was dissolved in ethyl alcohol (5 mL) and under Argon charged with 10% Pd/C (79 mg, 0.074 mmol) in a round bottom flask. The flask was then sealed with a rubber septa and the air was removed by vacuum and replaced with H2 from a balloon. This process repeated three times and the mixture was stirred under H2 atmosphere for 18 hours. The resulting mixture was then passed through a celite plug and concentrated down on rotovap. (117 mg, 99%).

Example JG

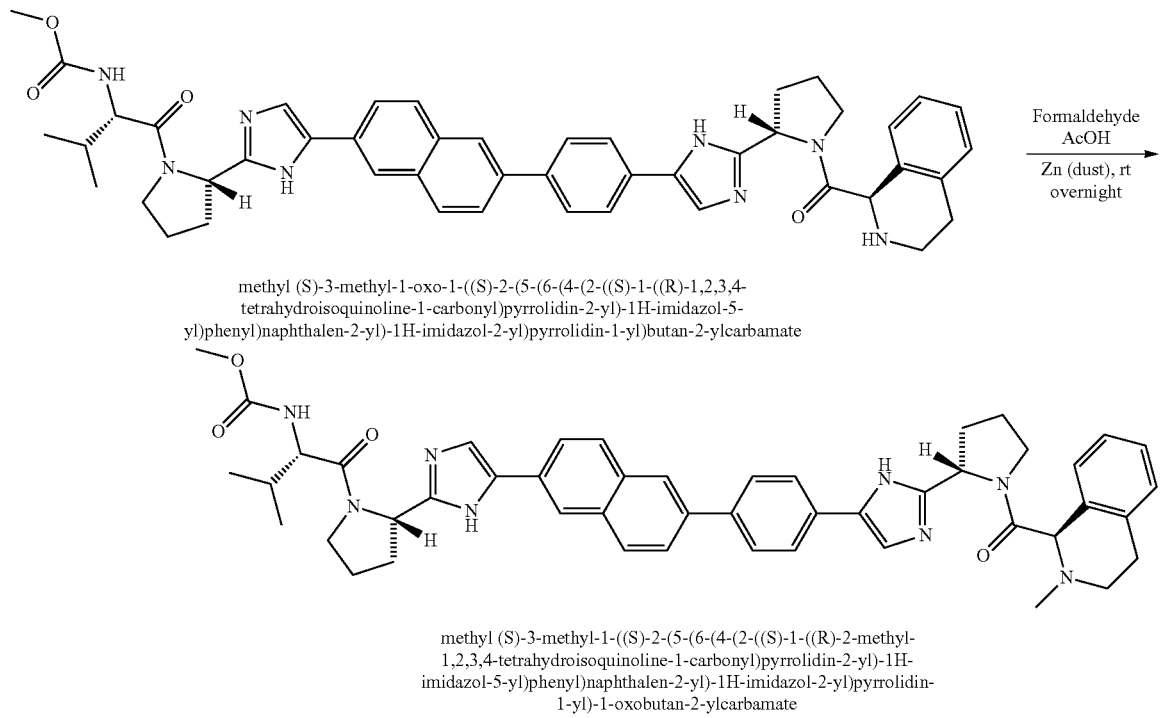

methyl (S)-3-methyl-1-oxo-1-((S)-2-(5-(6-(4-(2-((S)-1-((R)-1,2,3,4-tetrahydroisoquinoline-1-carbonyl)pyrrolidin-2-yl)-1H-imidazol-5-yl)phenyl)naphthalen-2-yl)-1H-imidazol-2-yl)pyrrolidin-1-yl)butan-2-ylcarbamate methyl (S)-3-methyl-1-((S)-2-(5-(6-(4-(2-((S)-1-((R)-2-methyl-1,2,3,4-tetrahydroisoquinoline-1-carbonyl)pyrrolidin-2-yl)-1H-imidazol-5-yl)phenyl)naphthalen-2-yl)-1H-imidazol-2-yl)pyrrolidin-1-yl)-1-oxobutan-2-ylcarbamate Methyl (S)-3-methyl-1-((S)-2-(5-(6-(4-(2-((S)-1-((R)-2-methyl-1,2,3,4-tetrahydroisoquinoline-1-carbonyl)pyrrolidin-2-yl)-1H-imidazol-5-yl)phenyl)naphthalen-2-yl)-1H-imidazol-2-yl)pyrrolidin-1-yl)-1-oxobutan-2-ylcarbamate: Methyl (S)-3-methyl-1-oxo-1-((S)-2-(5-(6-(4-(2-((S)-1-((R)-1,2,3,4-tetrahydroisoquinoline-1-carbonyl)pyrrolidin-2-yl)-1H-imidazol-5-yl)phenyl)naphthalen-2-yl)-1H-imidazol-2-yl)pyrrolidin-1-yl)butan-2-ylcarbamate (135 mg, 0.17 mmol), acetic acid (1.7 mL), zinc dust (111 mg, 1.7 mmol), and formaldehyde were all mixed in round bottom flask and stirred at room temperature overnight. The crude mixture was filtered through a celite plug and the filtrate was concentrated down to dryness on rotovap. The residue was then taken up in EtOAc and washed with 10% Na2CO3 and brine and dried over MgSO4. The filtrate was then concentrated down and the residue was purified on reverse phase HPLC. (13 mg, 10%). MS (ESI) m/z 805.77 [M+H]$^+$.

Example JH

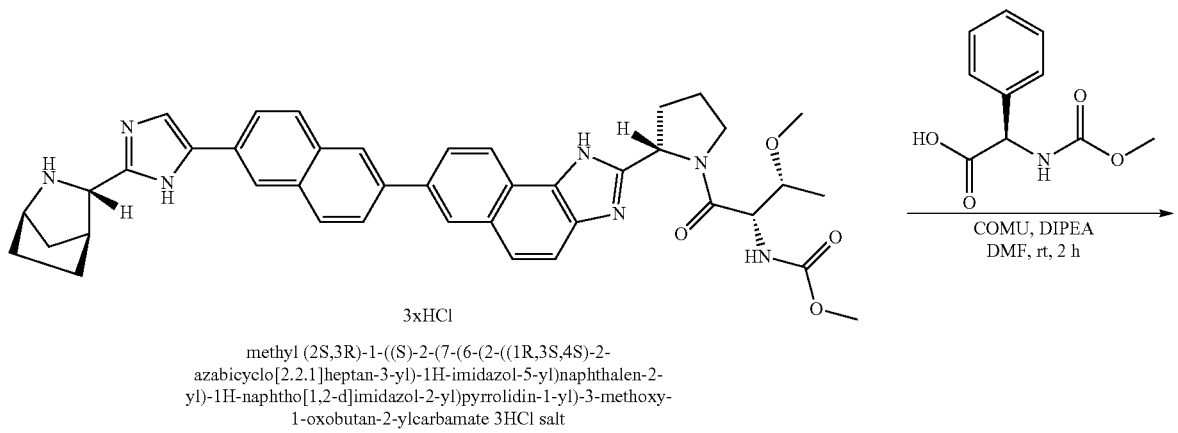

methyl (2S,3R)-1-((S)-2-(7-(6-(2-((1R,3S,4S)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-3-methoxy-1-oxobutan-2-ylcarbamate 3HCl salt

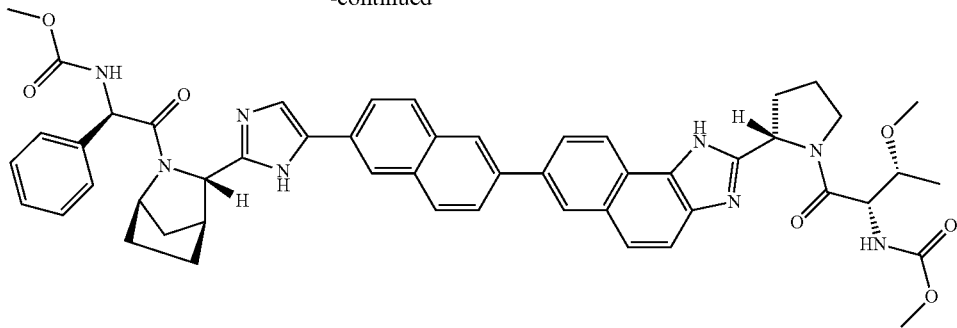

(2S,3R)-3-methoxy-1-((S)-2-(7-(6-(2-((1R,3S,4S)-2-((R)-2-(methoxycarbonlyamino)-2-phenylacetyl)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-1-oxobutan-2-ylcarbamic acid methyl ester (2S,3R)-3-Methoxy-1-((S)-2-(7-(6-(2-((1R,3S,4S)-2-((R)-2-(methoxycarbonylamino)-2-phenylacetyl)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-1-oxobutan-2-ylcarbamic acid methyl ester:

The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (2S,3R)-1-((S)-2-(7-(6-(2-((1R,3 S,4S)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-3-methoxy-1-oxobutan-2-ylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-11H-imidazol-2-yl)-1,4-dioxa-7-azaspiro[4.4]nonan-7-yl)butan-2-ylcarbamate 3 HCl salt. MS (ESI) m/z 889.43 [M+H]+. (100 mg, 43%).

Example JI

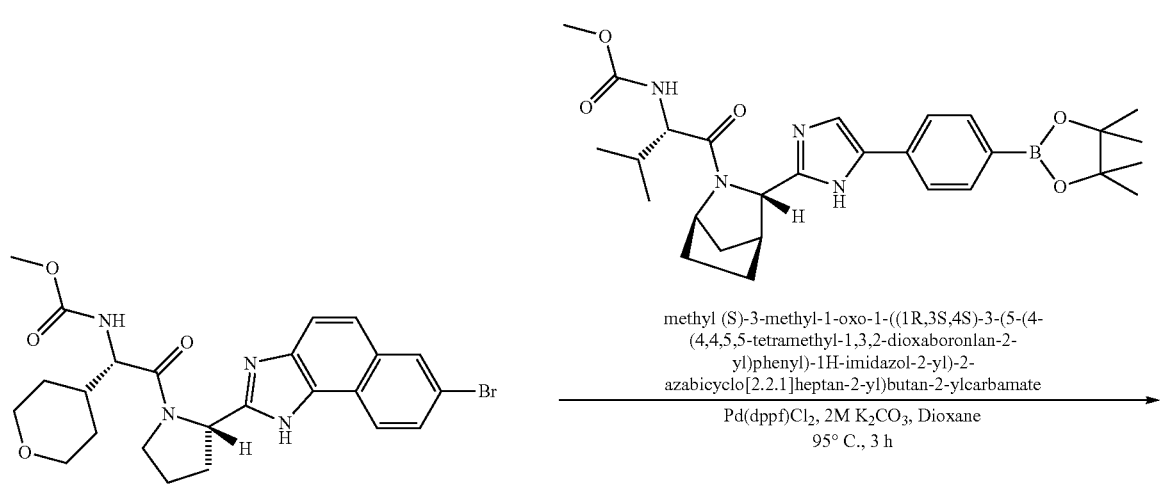

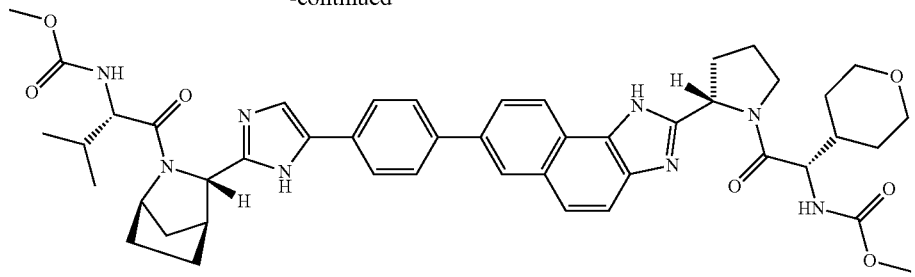

(S)-2-((S)-2-(7-(4-(2-((1R,3S,4S)-2-((S)-2-(methoxycarbonylamino)-3-methylbutanoyl)-2-azabicyclo[2.2.1]heptan-3-yl)-1H-imidazol-5-yl)phenyl)-1H-naphtho[1,2-d]imidazol-2-yl)pyrrolidin-1-yl)-2-oxo-1-(tetrahydro-2H-pyran-4-yl)ethylcarbamic acid methyl ester (S)-2-((S)-2-(7-(4-(2-((1R,3S,4S)-2-((S)-2-(methoxycarbonylamino)-3-methylbutanoyl)-2-azabicyclo[2.2.1]heptan-3-yl)-1H-imidazol-5-yl)phenyl)-1H-naphtho[1,2-d]imidazol-2-yl)pyrrolidin-1-yl)-2-oxo-1-(tetrahydro-2H-pyran-4-yl)ethylcarbamic acid methyl ester:

The title compound was prepared according to the method employed to prepare (S)-1-((S)-2-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)thiazolidin-3-yl)-3-methyl-1-oxobutan-2-ylcarbamic acid methyl ester, except that, respectively, methyl (S)-2-((S)-2-(7-bromo-1H-naphtho[1,2-d]imidazol-2-yl)pyrrolidin-1-yl)-2-oxo-1-(tetrahydro-2H-pyran-4-yl)ethylcarbamate and methyl (S)-3-methyl-1-oxo-1-((1R,3 S,4S)-3-(5-(4-(4,4,5,5-tetramethyl-1,3,2-dioxaborolan-2-yl)phenyl)-1H-imidazol-2-yl)-2-azabicyclo[2.2.1]heptan-2-yl)butan-2-ylcarbamate were used instead of methyl (R)-2-((S)-2-(5-(6-bromonaphthalen-2-yl)-1H-imidazol-2-yl)pyrrolidin-1-yl)-2-oxo-1-phenylethylcarbamate and methyl (S)-3-methyl-1-oxo-1-((S)-2-(5-(4-(4,4,5,5-tetramethyl-1,3,2-dioxaborolan-2-yl)phenyl)-1H-imidazol-2-yl)thiazolidin-3-yl)butan-2-ylcarbamate. MS (ESI) m/z 831.68 [M+H]+. (75 mg, 66%).

Example JJ

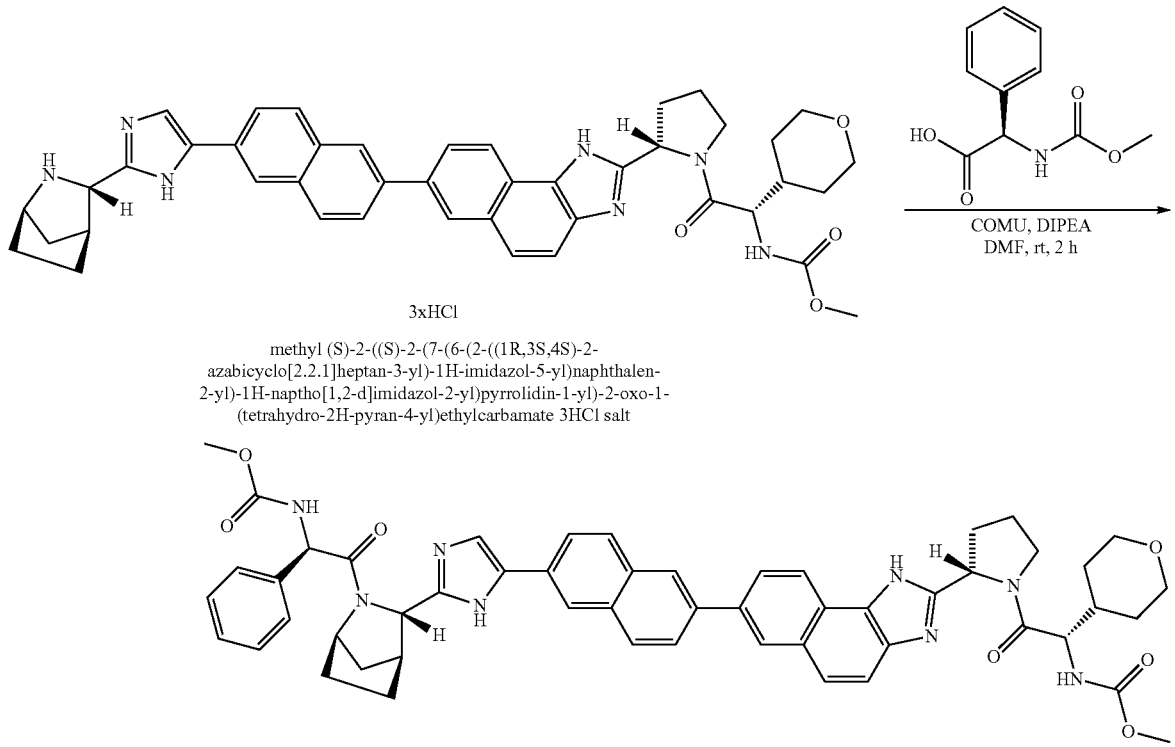

methyl (S)-2-((S)-2-(7-(6-(2-((1R,3S,4S)-2-azabicyclo[2.2.1]heptan-3-yl)-1H-imidazol-5-yl)naphthalen-2-yl)-1H-naptho[1,2-d]imidazol-2-yl)pyrrolidin-1-yl)-2-oxo-1-(tetrahydro-2H-pyran-4-yl)ethylcarbamate 3HCl salt (S)-2-((S)-2-(7-(6-(2-((1R,3S,4S)-2-((R)-2-(methoxycarbonylamino)-2-phenylacetyl)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-2-oxo-1-(tetrahydro-2H-pyran-4-yl)ethylcarbamic acid methyl ester (S)-2-((S)-2-(7-(6-(2-((1R,3S,4S)-2-((R)-2-(methoxycarbonylamino)-2-phenylacetyl)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-2-oxo-1-(tetrahydro-2H-pyran-4-yl)ethylcarbamic acid methyl ester: The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-2-((S)-2-(7-(6-(2-((1R,3 S,4 S)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-2-oxo-1-(tetrahydro-2H-pyran-4-yl)ethylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 915.83 [M+H]+. (44 mg, 60%).

Example JK (R)-2-((S)-2-(7-(6-(2-((1R,3 S,4S)-2-((S)-2-(methoxycarbonylamino)-2-(tetrahydro-2H-pyran-4-yl)acetyl)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-2-oxo-1-phenylethylcarbamic acid methyl ester: The title compound was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (S)-2-oxo-2-((1R,3 S,4S)-3-(5-(6-(2-((S)-pyrrolidin-2-yl)-1H-naphtho[1,2-d]imidazol-7-yl)naphthalen-2-yl)-1H-imidazol-2-yl)-2-azabicyclo[2.2.1]heptan-2-yl)-1-(tetrahydro-2H-pyran-4-yl)ethylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 915.83 [M+H]+. (59 mg, 88%).

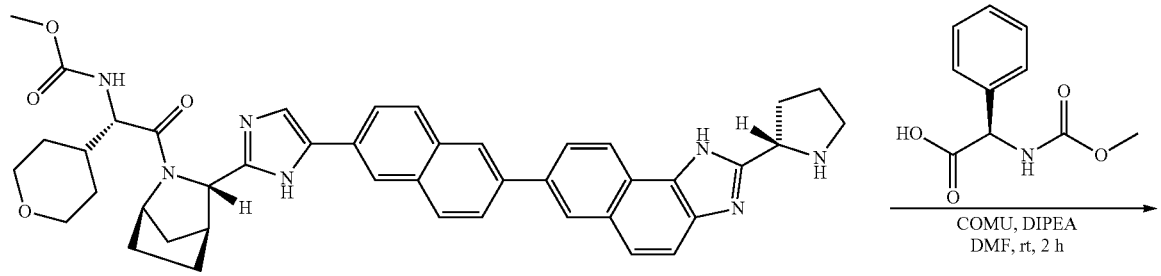

3xHCl methyl (S)-2-oxo-2-((1R,3S,4S)-3-(5-(6-(2-((S)-pyrrolidin-2-yl)-1H-naphtho[1,2-d]imidazol-7-yl)naphthalen-2-yl)-1H-imidazol-2-yl)-2-azabicyclo[2.2.1]heptan-2-yl)-1-(tetrahydro-2H-pyran-4-yl)ethylcarbamate 3HCl salt

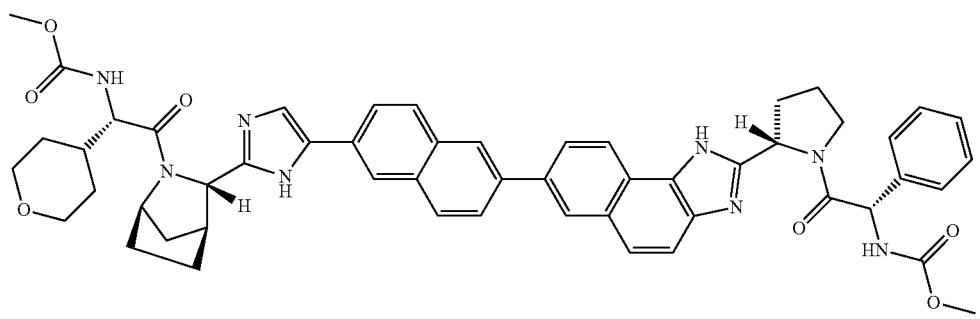

(R)-2-((S)-2-(7-(6-(2-((1R,3S,4S)-2-((S)-2-(methoxycarbonylamino)-2-(tetrahydro-2H-pyran-4-yl)acetyl)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-2-oxo-1-phenylethylcarbamic acid methyl ester

Example JL

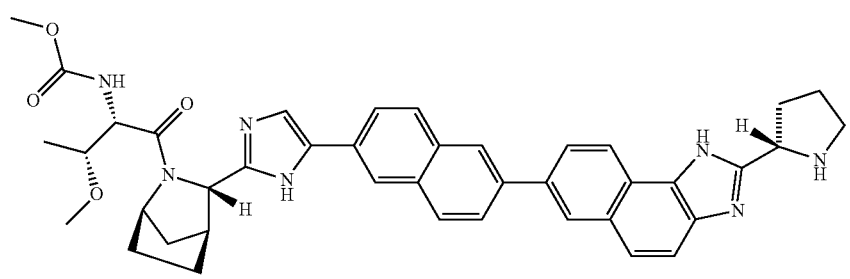

3xHCl methyl (2S,3R)-3-methoxy-1-oxo-1-((1R,3S,4S)-3-(5-(6-(2-((S)-pyrrolidin-2-yl)-1H-naphtho[1,2-d]imidazol-7-yl)naphthalen-2-yl)-1H-imidazol-2-yl)-2-azabicyclo[2.2.1]heptan-2-yl)butan-2-ylcarbamate 3HCl salt

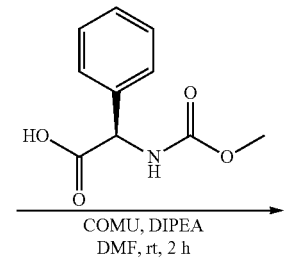

COMU, DIPEA
DMF, rt, 2 h

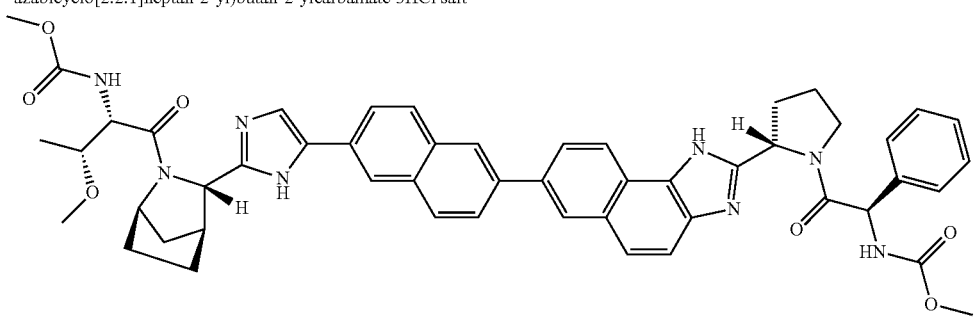

(R)-2-((S)-2-(7-(6-(2-((1R,3S,4S)-2-((2S,3R)-3-methoxy-2-(methoxycarbonylamino)butanoyl)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-2-oxo-1-phenylethylcarbamic acid methyl ester (R)-2-((S)-2-(7-(6-(2-((1R,3S,4S)-2-((2S,3R)-3-methoxy-2-(methoxycarbonylamino)butanoyl)-2-azabicyclo[2.2.1]heptan-3-yl)-1H-imidazol-5-yl)naphthalen-2-yl)-1H-naphtho[1,2-d]imidazol-2-yl)pyrrolidin-1-yl)-2-oxo-1-phenylethylcarbamic acid methyl ester was prepared according to the method employed to prepare (S)-1-((S)-8-(5-(4-(6-(2-((S)-1-((R)-2-(methoxycarbonylamino)-2-phenylacetyl)pyrrolidin-2-yl)-1H-imidazol-5-yl)naphthalen-2-yl)phenyl)-1H-imidazol-2-yl)-1,4-dioxa-7-azaspiro[4.4]nonan-7-yl)-3-methyl-1-oxobutan-2-ylcarbamic acid methyl ester, except that methyl (2S,3R)-3-methoxy-1-oxo-1-((1R,3S,4S)-3-(5-(6-(2-((S)-pyrrolidin-2-yl)-1H-naphtho[1,2-d]imidazol-7-yl)naphthalen-2-yl)-1H-imidazol-2-yl)-2-azabicyclo[2.2.1]heptan-2-yl)butan-2-ylcarbamate 3HCl salt was used instead of methyl (S)-3-methyl-1-oxo-1-((S)-8-(5-(4-(6-(2-((S)-pyrrolidin-2-yl)-1H-imidazol-5-yl)naphthalen-2-yl)phenyl)-1H-imidazol-2-yl)-1,4-dioxa-7-azaspiro[4.4]nonan-7-yl)butan-2-ylcarbamate 3 HCl salt. MS (ESI) m/z 889.79 [M+H]+. (56 mg, 79%).

Example JM

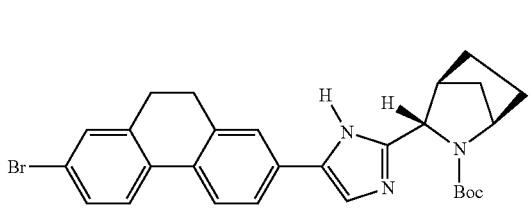

(1R,3S,4S)-tert-butyl 3-(5-(7-bromo-9,10-dihydrophenanthren-2-yl)-1H-imidazol-2-yl)-2-azabicyclo[2.2.1]heptane-2-carboxylate

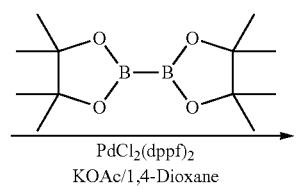

PdCl$_2$(dppf)$_2$
KOAc/1,4-Dioxane 1059                                                                                   1060

-continued

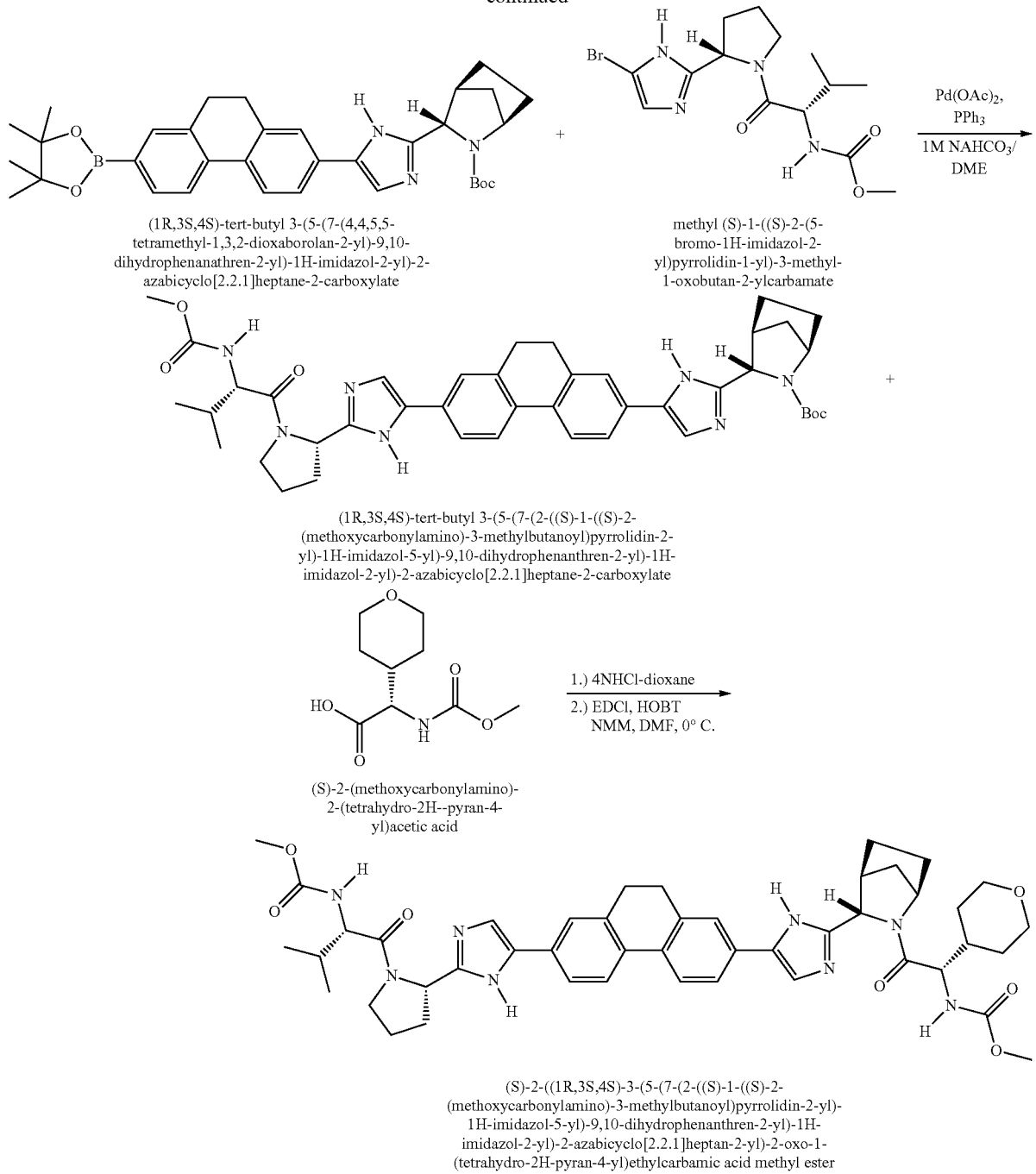

(S)-2-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-2-oxo-1-(tetrahydro-2H-pyran-4-yl)ethylcarbamic acid methyl ester: (1R,3S,4S)-tert-Butyl 3-(5-(7-bromo-9,10-dihydrophenanthren-2-yl)-1H-imidazol-2-yl)-2-azabicyclo[2.2.1]heptane-2-carboxylate (235 mg, 0.45 mmol), bis(pinacolato)diboron (234 mg, 0.92 mmol), potassium acetate (115 mg, 1.17 mmol), and Pd(dppf)Cl$_2$ (18 mg, 0.02 mmol) were all weighed out in a glass pressure vessel and DME (4.5 mL) was added. The mixture was bubbled with nitrogen gas for about 5 min. The vessel was then capped and sealed and heated in an oil bath at 90° C. overnight with continuous stirring. The reaction vessel was cooled down to room temperature and all volatiles were removed under reduced pressure and the resulting oil was subjected to silica gel chromatography with an eluent of ethyl acetate and hexane at a gradient of 0-50% with an ISCO column (12 g silica gel). The fractions containing product were combined and the solvent was removed under reduced pressure to provide 1R,3S,4S)-tert-butyl 3-(5-(7-(4,4,5,5-tetramethyl-1,3,2-dioxaborolan-2-yl)-9,10-dihydrophenanthren-2-yl)-1H-imidazol-2-yl)-2-azabicyclo[2.2.1]heptane-2-carboxylate (230 mg, 90%).

To 1R,3S,4S)-tert-butyl 3-(5-(7-(4,4,5,5-tetramethyl-1,3,2-dioxaborolan-2-yl)-9,10-dihydrophenanthren-2-yl)-1H-imidazol-2-yl)-2-azabicyclo[2.2.1]heptane-2-carboxylate (97 mg, 0.17 mmol), methyl (S)-1-((S)-2-(5-bromo-1H-imidazol-2-yl)pyrrolidin-1-yl)-3-methyl-1-oxobutan-2-ylcarbamate (67 mg, 0.18 mmol), Pd(PPh₃)₄ (10 mg, 0.009 mmol). DME (1.7 mL) was added and followed by 0.7 mL 1M NaHCO3 aqueous solution. The reaction was purged with Ar and heated to 120° C. at microwave synthesizer for 0.5 hour. The reaction was cooled to room temperature and concentrated down. EtOAc was added and washed with sat. NaHCO₃ aqueous (2×) and sat. NaCl aqueous (1×). The organic layer was concentrated down after drying over sodium sulfate and subject to silica gel chromatography with an eluent of ethyl acetate and hexane at a gradient of 40-100% with an ISCO column (12 g silica gel). The fractions containing product were combined and the solvent was removed under reduced pressure to provide (1R,3S,4S)-tert-butyl 3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptane-2-carboxylate (110 mg, 88%). MS (ESI) m/z 734 [M+H]⁺.

To (1R,3S,4S)-tert-butyl 3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptane-2-carboxylate (48 mg, 0.066 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

This HCl salts (35 mg 0.048 mmol) in DMF (0.5 mL) was added (S)-2-(methoxycarbonylamino)-2-(tetrahydro-2H-pyran-4-yl)acetic acid (12.5 mg, 0.058 mmol), N-(3-dimethylaminopropyl)-N'-ethylcarbodiimide hydrochloride (12 mg, 0.062 mmol) and hydroxybenzotriazole hydrate (HOBt), (8.4 mg, 0.062 mmol). The mixture was cooled down in an ice bath to 0° C. and N-methylmorpholine (NMM)(0.212 mmol) was added from a syringe to the mixture. The reaction content was stirred for 4 hours at room temperature. The resulting mixture was then directly purified on reverse phase prep. HPLC to afford title compound as white solid (28 mg, 70%). MS (ESI) m/z 833 [M+H]⁺.

Example JN

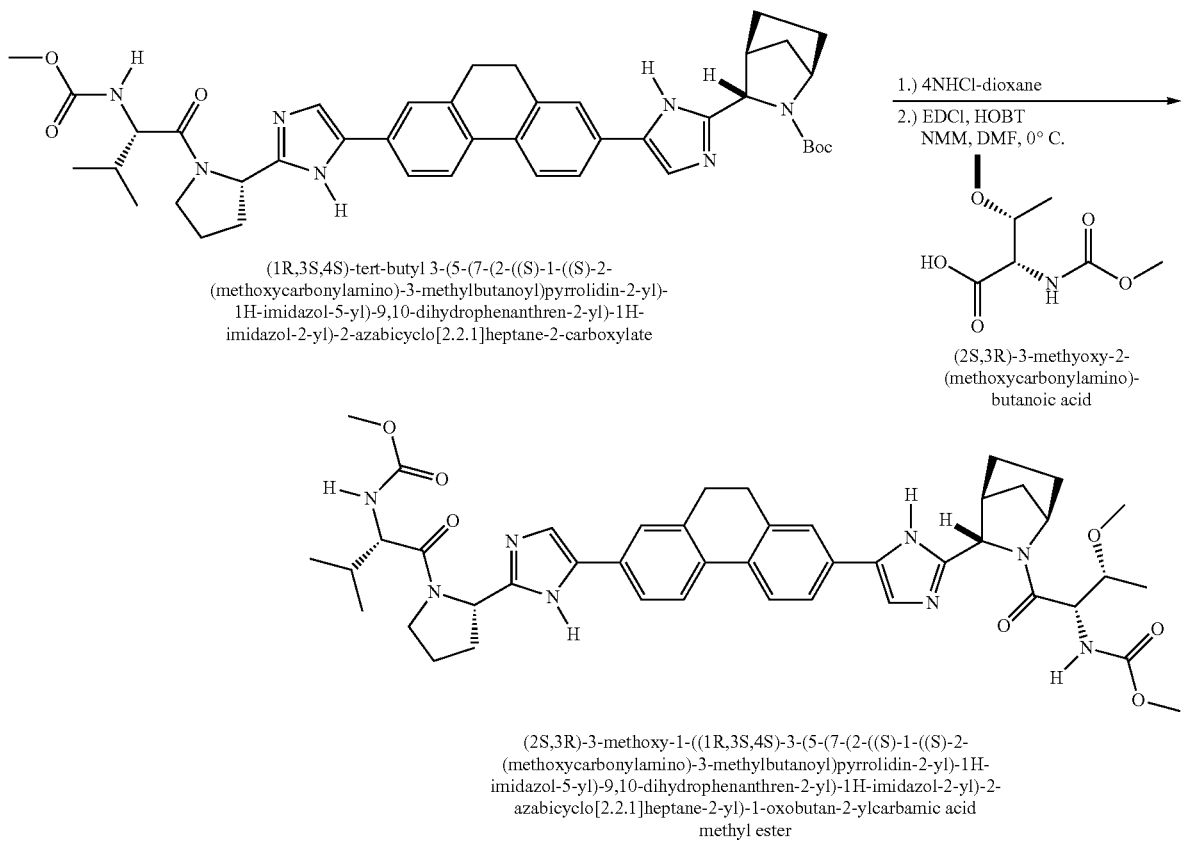

(2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptane-2-yl)-1-oxobutan-2-ylcarbamic acid methyl ester (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester:

To (1R,3S,4S)-tert-butyl 3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptane-2-carboxylate (48 mg, 0.066 mmol) in dichloromethane (0.8 mL) was added 4M HCl in dioxane (0.8 mL) and the reaction mixture was cooled to 0° C. and then stirred for 2 hours. After concentrated in vacuo to afford HCl salts.

This HCl salts (35 mg 0.048 mmol) in DMF (0.5 mL) was added (2S,3R)-3-methoxy-2-(methoxycarbonylamino)butanoic acid (11 mg, 0.058 mmol), N-(3-dimethylaminopropyl)-N'-ethylcarbodiimide hydrochloride (12 mg, 0.062 mmol) and hydroxybenzotriazole hydrate (HOBt), (8.4 mg, 0.062 mmol). The mixture was cooled down in an ice bath to 0° C. and N-methylmorpholine (NMM)(0.212 mmol) was added from a syringe to the mixture. The reaction content was stirred for 4 hours at room temperature. The resulting mixture was then directly purified on reverse phase prep. HPLC to afford title compound as white solid (29 mg, 75%). MS (ESI) m/z 807 [M+H]$^+$.

Example JO

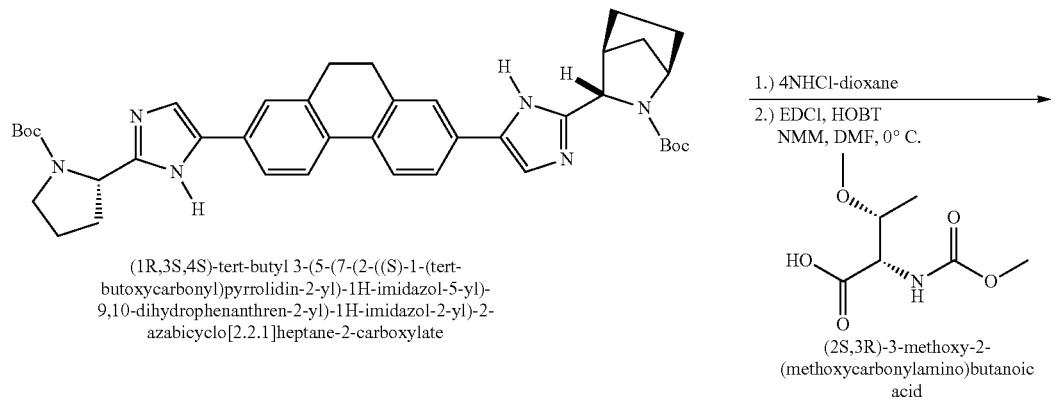

(1R,3S,4S)-tert-butyl 3-(5-(7-(2-((S)-1-(tert-butoxycarbonyl)pyrrolidin-2-yl)-1H-imidazol-5-yl)-9,10-dihydrophenanthren-2-yl)-1H-imidazol-2-yl)-2-azabicyclo[2.2.1]heptane-2-carboxylate 1.) 4NHCl-dioxane
2.) EDCl, HOBT
NMM, DMF, 0° C.

(2S,3R)-3-methoxy-2-(methoxycarbonylamino)butanoic acid

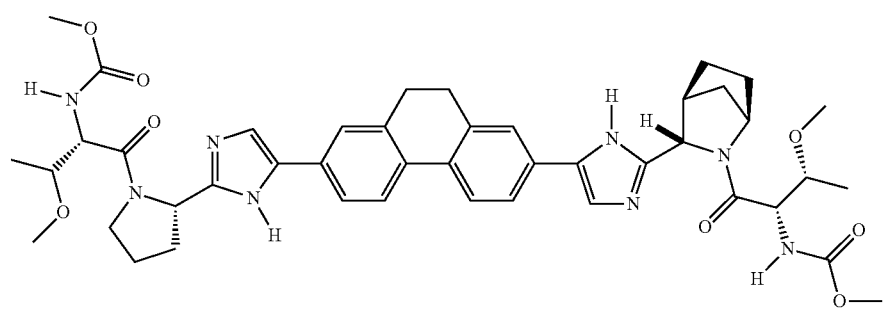

(2S,3R)-3-methoxy-1-((1R,3S,4S)-3-(5-(7-(2-((S)-1-((2S,3R)-3-methoxy-2-(methoxycarbonylamino)butanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester (2S,3R)-3-methoxy-1-((1R,3S,4S)-3-(5-(7-(2-((S)-1-((2S,3R)-3-methoxy-2-(methoxycarbonylamino)butanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester: To (1R,3S,4S)-tert-butyl 3-(5-(7-(2-((S)-1-(tert-butoxycarbonyl)pyrrolidin-2-yl)-1H-imidazol-5-yl)-9,10-dihydrophenanthren-2-yl)-1H-imidazol-2-yl)-2-azabicyclo[2.2.1]heptane-2-carboxylate (115 mg, 0.17 mmol) in dichloromethane (1 mL) was added 4M HCl in dioxane (0.8 mL) and the reaction mixture was cooled to 0° C. and then stirred for 4 hours. After concentrated in vacuo to afford HCl salts.

This HCl salts (80 mg, 0.13 mmol) in DMF (1.3 mL) was added (2S,3R)-3-methoxy-2-(methoxycarbonylamino)butanoic acid (58 mg, 0.3 mmol), N-(3-dimethylaminopropyl)-N'-ethylcarbodiimide hydrochloride (64 mg, 0.325 mmol) and hydroxybenzotriazole hydrate (HOBt), (44 mg, 0.325 mmol). The mixture was cooled down in an ice bath to 0° C. and N-methylmorpholine (NMM)(0.868 mmol) was added from a syringe to the mixture. The reaction content was stirred for 16 hours at room temperature. The resulting mixture was then directly purified on reverse phase prep. HPLC to afford title compound as white solid (90 mg, 85%). MS (ESI) m/z 823 [M+H]$^+$.

Example JP

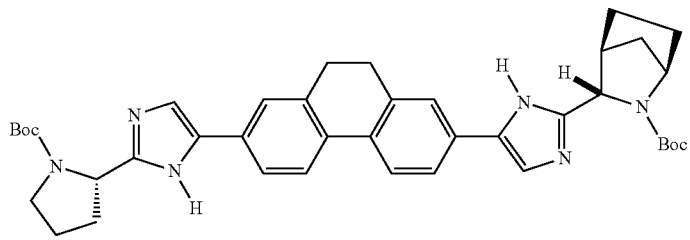

(1R,3S,4S)-tert-butyl 3-(5-(7-(2-((S)-1-(tert-butoxycarbonyl)pyrrolidin-2-yl)-1H-imidazol-5-yl)-9,10-dihydrophenanthren-2-yl)-1H-imidazol-2-yl)-2-azabicyclo[2.2.1]heptane-2-carboxylate 1.) 4NHCl-dioxane
2.) EDCl, HOBT NMM, DMF, 0° C.

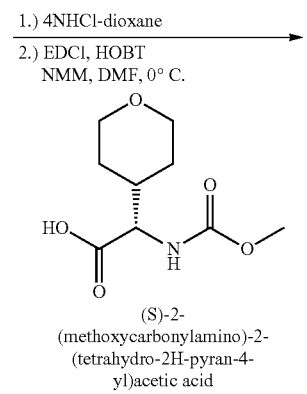

(S)-2-(methoxycarbonylamino)-2-(tetrahydro-2H-pyran-4-yl)acetic acid

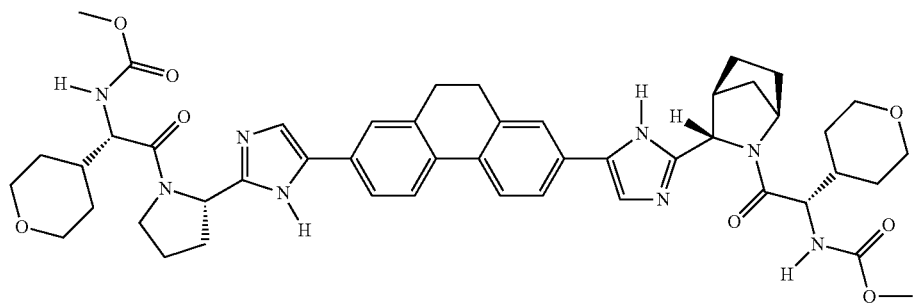

(S)-2-((1R,3S,4S)-3-(5-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-2-oxo-1-(tetrahydro-2H-pyran-4-yl)ethylcarbamic acid methyl ester (S)-2-((1R,3S,4S)-3-(5-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-2-oxo-1-(tetrahydro-2H-pyran-4-yl)ethylcarbamic acid methyl ester: To (1R,3S,4S)-tert-butyl 3-(5-(7-(2-((S)-1-(tert-butoxycarbonyl)pyrrolidin-2-yl)-1H-imidazol-5-yl)-9,10-dihydrophenanthren-2-yl)-1H-imidazol-2-yl)-2-azabicyclo[2.2.1]heptane-2-carboxylate (115 mg, 0.17 mmol) in dichloromethane (1 mL) was added 4M HCl in dioxane (0.8 mL) and the reaction mixture was cooled to 0° C. and then stirred for 4 hours. After concentrated in vacuo to afford HCl salts.

This HCl salts (25 mg, 0.04 mmol) in DMF (0.4 mL) was added (S)-2-(methoxycarbonylamino)-2-(tetrahydro-2H-pyran-4-yl)acetic acid (22 mg, 0.1 mmol), N-(3-dimethylaminopropyl)-N'-ethylcarbodiimide hydrochloride (19 mg, 0.1 mmol) and hydroxybenzotriazole hydrate (HOBt), (14 mg, 0.1 mmol). The mixture was cooled down in an ice bath to 0° C. and N-methylmorpholine (NMM)(0.262 mmol) was added from a syringe to the mixture. The reaction content was stirred for 16 hours at room temperature. The resulting mixture was then directly purified on reverse phase prep. HPLC to afford title compound as white solid (28 mg, 80%). MS (ESI) m/z 876 [M+H]$^+$.

Example JQ

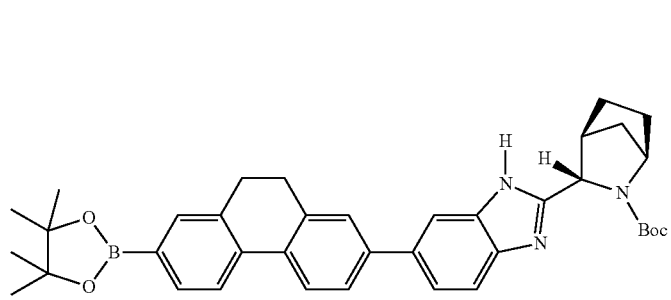

(1R,3S,4S)-tert-butyl 3-(6-(7-(4,4,5,5-tetramethyl-1,3,2-dioxaborolan-2-yl)-9,10-dihydrophenanthren-2-yl)-1H-benzo[d]imidazol-2-yl)-2-azabicyclo[2.2.1]heptane-2-carboxylate

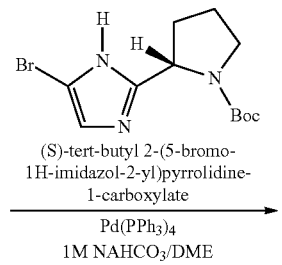

(S)-tert-butyl 2-(5-bromo-1H-imidazol-2-yl)pyrrolidine-1-carboxylate

Pd(PPh₃)₄
1M NAHCO₃/DME

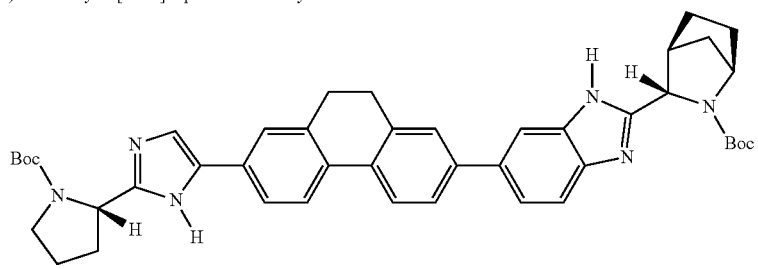

(1R,3S,4S)-tert-butyl 3-(6-(7-(2-((S)-1-(tert-butoxycarbonyl)pyrrolidin-2-yl)-1H-imidazol-5-yl)-9,10-dihydrophenanthren-2-yl)-1H-benzo[d]imidazol-2-yl)-2-azabicyclo[2.2.1]heptane-2-carboxylate (1R,3S,4S)-tert-butyl 3-(6-(7-(2-((S)-1-(tert-butoxycarbonyl)pyrrolidin-2-yl)-1H-imidazol-5-yl)-9,10-dihydrophenanthren-2-yl)-1H-benzo[d]imidazol-2-yl)-2-azabicyclo[2.2.1]heptane-2-carboxylate: To (1R,3 S,4S)-tert-butyl 3-(6-(7-(4,4,5,5-tetramethyl-1,3,2-dioxaborolan-2-yl)-9,10-dihydrophenanthren-2-yl)-1H-benzo[d]imidazol-2-yl)-2-azabicyclo[2.2.1]heptane-2-carboxylate (88 mg, 0.14 mmol), (S)-tert-butyl 2-(5-bromo-1H-imidazol-2-yl)pyrrolidine-1-carboxylate (53 mg, 0.168 mmol), Pd(PPh₃)₄ (8 mg, 0.007 mmol). DME (1.4 mL) was added and followed by 0.56 mL 1M NaHCO₃ aqueous solution. The reaction was purged with Ar and heated to 120° C. at microwave synthesizer for 0.5 hour. The reaction was cooled to room temperature and concentrated down. EtOAc was added and washed with sat. NaHCO₃ aqueous (2×) and sat. NaCl aqueous (1×). The organic layer was concentrated down after drying over sodium sulfate and subject to silica gel chromatography with an eluent of ethyl acetate and hexane at a gradient of 40-100% with an ISCO column (12 g silica gel). The fractions containing product were combined and the solvent was removed under reduced pressure to provide title compound (90 mg, 86%). MS (ESI) m/z 727 [M+H]⁺.

Example JR

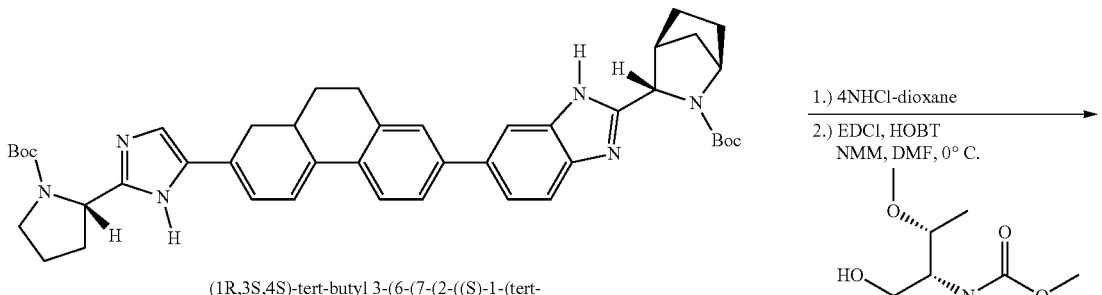

(1R,3S,4S)-tert-butyl 3-(6-(7-(2-((S)-1-(tert-butoxycarbonyl)pyrrolidin-2-yl)-1H-imidazol-5-yl)-9,10-dihydrophenanthren-2-yl)-1H-benzo[d]imidazol-2-yl)-2-azabicyclo[2.2.1]heptane-2-carboxylate 1.) 4NHCl-dioxane
2.) EDCl, HOBT
NMM, DMF, 0° C.

(2S,3R)-3-methoxy-2-(methoxycarbonylamino) butanoic acid

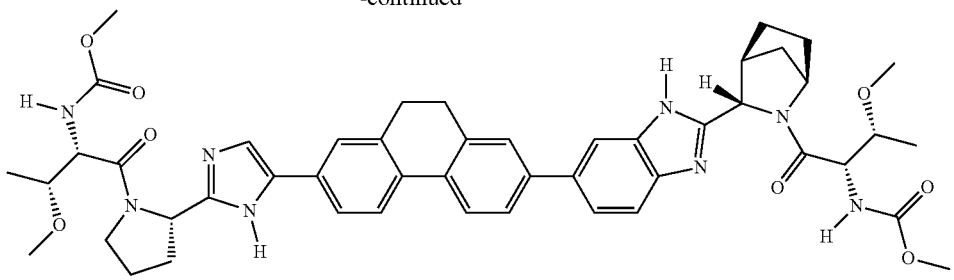

(2S,3R)-3-methoxy-1-((1R,3S,4S)-3-(6-(7-(2-((S)-1-((2S,3R)-3-methoxy-2-(methoxycarbonylamino)butanoyl)pyrrolidin-2-yl)-1H-imidazol-5-yl)-9,10-dihydrophenanthren-2-yl)-1H-benzo[d]imidazol-2-yl)-2-azabicyclo[2.2.1]heptan-2-yl)-1-oxobutan-2-ylcarbamic acid methyl ester (2S,3R)-3-methoxy-1-((1R,3S,4S)-3-(6-(7-(2-((S)-1-((2S,3R)-3-methoxy-2-(methoxycarbonylamino)butanoyl)pyrrolidin-2-yl)-1H-imidazol-5-yl)-9,10-dihydrophenanthren-2-yl)-1H-benzo[d]imidazol-2-yl)-2-azabicyclo[2.2.1]heptan-2-yl)-1-oxobutan-2-ylcarbamic acid methyl ester: To 1R,3S,4S)-tert-butyl 3-(6-(7-(2-((S)-1-(tert-butoxycarbonyl)pyrrolidin-2-yl)-1H-imidazol-5-yl)-9,10-dihydrophenanthren-2-yl)-1H-benzo[d]imidazol-2-yl)-2-azabicyclo[2.2.1]heptane-2-carboxylate (90 mg, 0.12 mmol) in dichloromethane (1.2 mL) was added 4M HCl in dioxane (1 mL) and the reaction mixture was cooled to 0° C. and then stirred for 2 hours. After concentrated in vacuo to afford HCl salts.

This HCl salts (30 mg 0.046 mmol) in DMF (0.5 mL) was added (2S,3R)-3-methoxy-2-(methoxycarbonylamino)butanoic acid (20 mg, 0.105 mmol), N-(3-dimethylaminopropyl)-N'-ethylcarbodiimide hydrochloride (22 mg, 0.12 mmol) and hydroxybenzotriazole hydrate (HOBt), (16 mg, 0.12 mmol). The mixture was cooled down in an ice bath to 0° C. and N-methylmorpholine (NMM)(0.223 mmol) was added from a syringe to the mixture. The reaction content was stirred for 4 hours at room temperature. The resulting mixture was then directly purified on reverse phase prep. HPLC to afford title compound as white solid (28 mg, 70%). MS (ESI) m/z 874 [M+H]$^+$.

Example JS

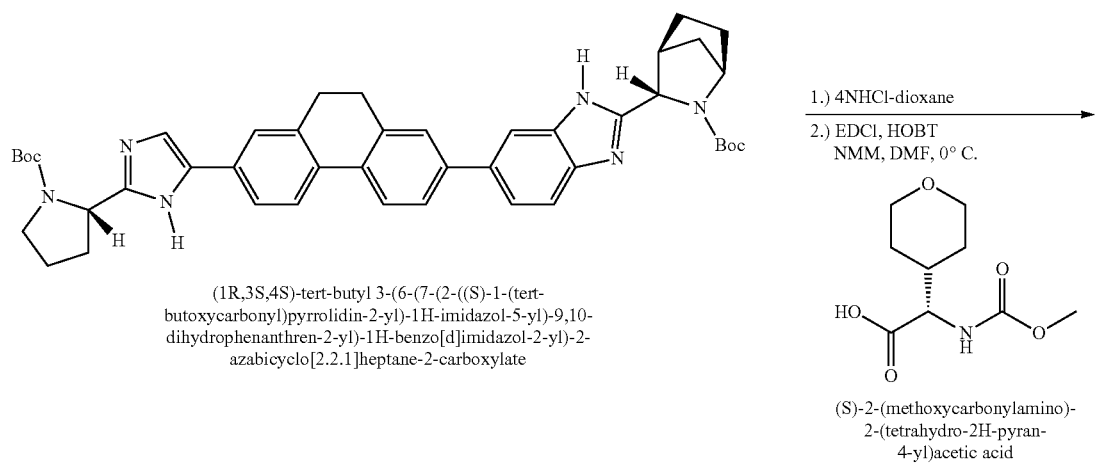

(1R,3S,4S)-tert-butyl 3-(6-(7-(2-((S)-1-(tert-butoxycarbonyl)pyrrolidin-2-yl)-1H-imidazol-5-yl)-9,10-dihydrophenanthren-2-yl)-1H-benzo[d]imidazol-2-yl)-2-azabicyclo[2.2.1]heptane-2-carboxylate (S)-2-(methoxycarbonylamino)-2-(tetrahydro-2H-pyran-4-yl)acetic acid -continued

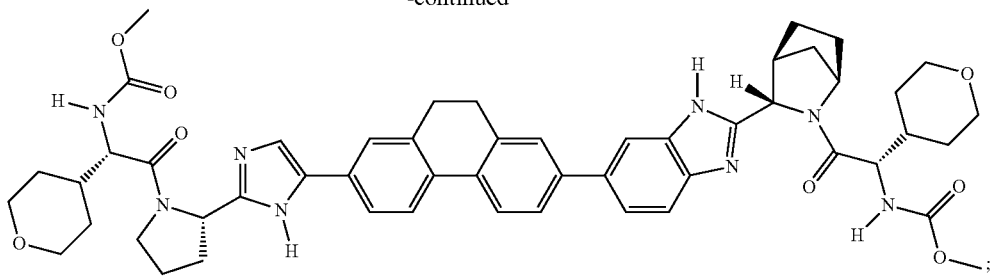

(S)-2-((1R,3S,4S)-3-(6-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-benzo[d]imidazol-2-yl)-2-azabicyclo[2.2.1]heptan-2-yl)-2-oxo-1-(tetrahydro-2H-pyran-4-yl)ethylcarbamic acid methyl ester (S)-2-((1R,3S,4S)-3-(6-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-benzo[d]imidazol-2-yl)-2-azabicyclo[2.2.1]heptan-2-yl)-2-oxo-1-(tetrahydro-2H-pyran-4-yl)ethylcarbamic acid methyl ester: To (1R,3S,4S)-tert-butyl 3-(6-(7-(2-((S)-1-(tert-butoxycarbonyl)pyrrolidin-2-yl)-1H-imidazol-5-yl)-9,10-dihydrophenanthren-2-yl)-1H-benzo[d]imidazol-2-yl)-2-azabicyclo[2.2.1]heptane-2-carboxylate (90 mg, 0.12 mmol) in dichloromethane (1.2 mL) was added 4M HCl in dioxane (1 mL) and the reaction mixture was cooled to 0° C. and then stirred for 2 hours. After concentrated in vacuo to afford HCl salts.

This HCl salts (25 mg 0.038 mmol) in DMF (0.4 mL) was added (S)-2-(methoxycarbonylamino)-2-(tetrahydro-2H-pyran-4-yl)acetic acid (19 mg, 0.09 mmol), N-(3-dimethylaminopropyl)-N'-ethylcarbodiimide hydrochloride (18 mg, 0.095 mmol) and hydroxybenzotriazole hydrate (HOBt), (13 mg, 0.095 mmol). The mixture was cooled down in an ice bath to 0° C. and N-methylmorpholine (NMM)(0.252 mmol) was added from a syringe to the mixture. The reaction content was stirred for 4 hours at room temperature. The resulting mixture was then directly purified on reverse phase prep. HPLC to afford title compound as white solid (24 mg, 68%). MS (ESI) m/z 926 [M+H]⁺.

Example JT

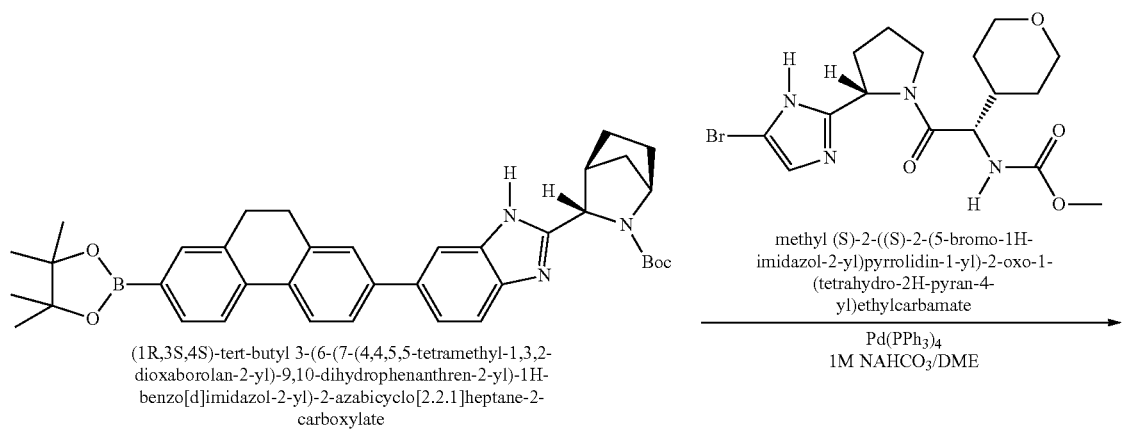

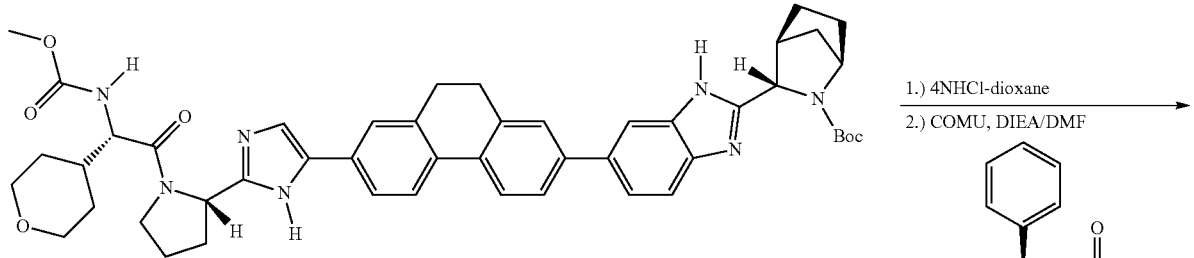

(1R,3S,4S,)-tert-butyl 3-(6-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-benzo[d]imidazol-2-yl)-2-azabicyclo[2.2.1]heptane-2-carboxylate (R)-2-(methoxycarbonylamino)-2-phenylacetic acid

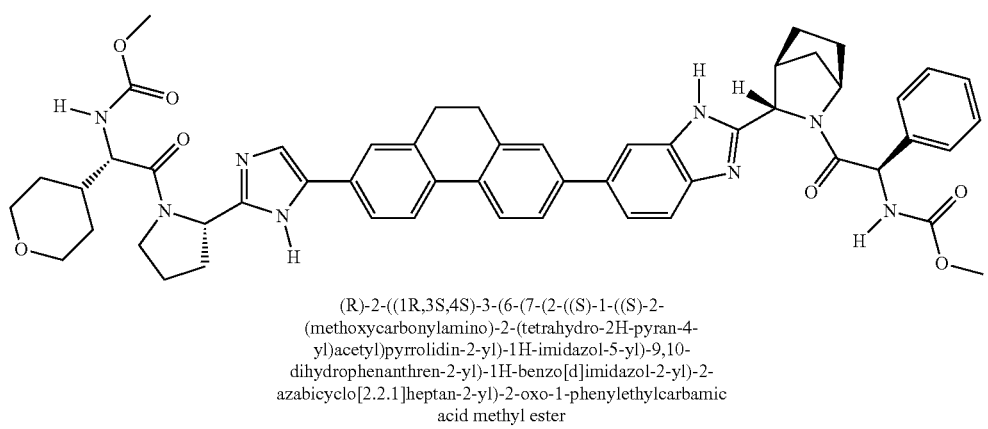

(R)-2-((1R,3S,4S)-3-(6-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-benzo[d]imidazol-2-yl)-2-azabicyclo[2.2.1]heptan-2-yl)-2-oxo-1-phenylethylcarbamic acid methyl ester (R)-2-((1R,3S,4S)-3-(6-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-benzo[d]imidazol-2-yl)-2-azabicyclo[2.2.1]heptan-2-yl)-2-oxo-1-phenylethylcarbamic acid methyl ester: To (1R,3S,4S)-tert-butyl 3-(6-(7-(4,4,5,5-tetramethyl-1,3,2-dioxaborolan-2-yl)-9,10-dihydrophenanthren-2-yl)-1H-benzo[d]imidazol-2-yl)-2-azabicyclo[2.2.1]heptane-2-carboxylate (190 mg, 0.3 mmol), methyl (S)-2-((S)-2-(5-bromo-1H-imidazol-2-yl)pyrrolidin-1-yl)-2-oxo-1-(tetrahydro-2H-pyran-4-yl)ethylcarbamate (149 mg, 0.36 mmol), Pd(PPh$_3$)$_4$ (17 mg, 0.015 mmol). DME (3 mL) was added and followed by 1.2 mL 1M NaHCO$_3$ aqueous solution. The reaction was purged with Ar and heated to 120° C. at microwave synthesizer for 0.5 hour. The reaction was cooled to room temperature and concentrated down. EtOAc was added and washed with sat. NaHCO$_3$ aqueous (2×) and sat. NaCl aqueous (1×). The organic layer was concentrated down after drying over sodium sulfate and subject to silica gel chromatography with an eluent of ethyl acetate and hexane at a gradient of 40-100% with an ISCO column (12 g silica gel). The fractions containing product were combined and the solvent was removed under reduced pressure to provide product (223 mg, 88%). MS (ESI) m/z 826 [M+H]$^+$.

(1R,3S,4S)-tert-butyl 3-(6-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-benzo[d]imidazol-2-yl)-2-azabicyclo[2.2.1]heptane-2-carboxylate (100 mg, 0.12 mmol) in dichloromethane (1.2 mL) was added 4M HCl in dioxane (1 mL) and the reaction mixture was cooled to 0° C. and then stirred for 2 hours. After concentrated in vacuo to afford HCl salts.

This HCl salts (20 mg 0.024 mmol) in DMF (0.25 mL) was added methoxycarbonylamino)-2-phenylacetic acid (5.4 mg, 0.026 mmol), COMU (13 mg, 0.03 mmol). The mixture was cooled down in an ice bath to 0° C. and DIEA (0.072 mmol) was added from a syringe to the mixture. The reaction content was stirred for 1 hour at room temperature. The resulting mixture was then directly purified on reverse phase prep. HPLC to afford title compound as white solid (14 mg, 65%). MS (ESI) m/z 918 [M+H]$^+$.

Example JU

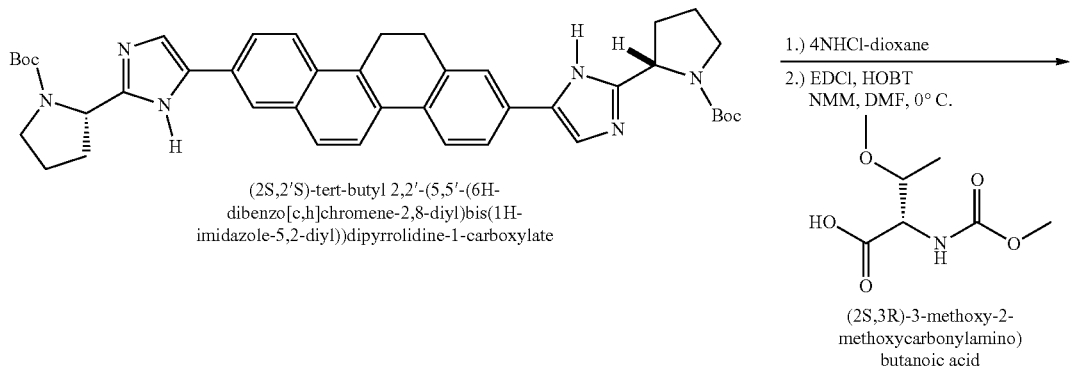

(2S,2'S)-tert-butyl 2,2'-(5,5'-(6H-dibenzo[c,h]chromene-2,8-diyl)bis(1H-imidazole-5,2-diyl))dipyrrolidine-1-carboxylate (2S,3R)-3-methoxy-2-methoxycarbonylamino) butanoic acid

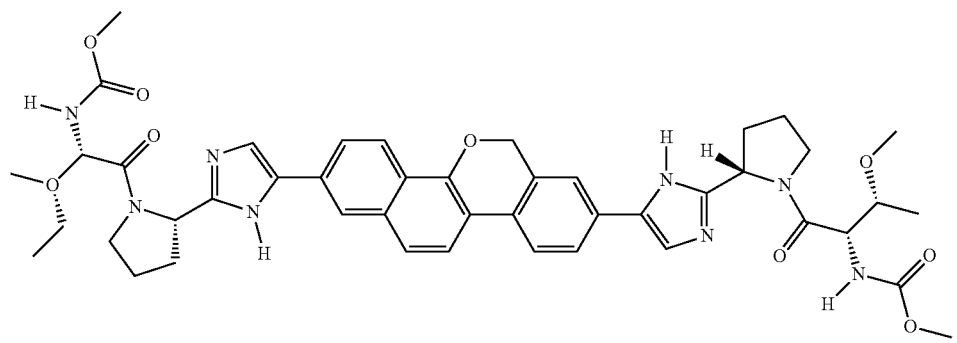

(2S,3R)-3-methoxy-1-((S)-2-(5-(2-(2-((S)-1-((2S,3R)-3-methoxy-2-(methoxycarbonylamino)butanoyl)pyrrolidin-2-yl)-1H-imidazol-5-yl)-6H-dibenzo[c,h]chromen-8-yl)-1H-imidazol-2-yl)pyrrolidin-1-yl)-1-oxobutan-2-ylcarbamic acid methyl mester (2S,3R)-3-methoxy-1-((S)-2-(5-(2-(2-((S)-1-((2S,3R)-3-methoxy-2-(methoxycarbonylamino)butanoyl)pyrrolidin-2-yl)-1H-imidazol-5-yl)-6H-dibenzo[c,h]chromen-8-yl)-1H-imidazol-2-yl)pyrrolidin-1-yl)-1-oxobutan-2-ylcarbamic acid methyl mester: To (2S,2'S)-tert-butyl 2,2'-(5,5'-(6H-dibenzo[c,h]chromene-2,8-diyl)bis(1H-imidazole-5,2-diyl))dipyrrolidine-1-carboxylate (90 mg, 0.128 mmol) in dichloromethane (1.2 mL) was added 4M HCl in dioxane (1 mL) and the reaction mixture was cooled to 0° C. and then stirred for 2 hours. After concentrated in vacuo to afford HCl salts.

This HCl salts (80 mg 0.125 mmol) in DMF (1.2 mL) was added (2S,3R)-3-methoxy-2-(methoxycarbonylamino)butanoic acid (62 mg, 0.33 mmol), N-(3-dimethylaminopropyl)-N'-ethylcarbodiimide hydrochloride (62 mg, 0.33 mmol) and hydroxybenzotriazole hydrate (HOBt), (44 mg, 0.33 mmol). The mixture was cooled down in an ice bath to 0° C. and N-methylmorpholine (NMM)(0.828 mmol) was added from a syringe to the mixture. The reaction content was stirred for 4 hours at room temperature. The resulting mixture was then directly purified on reverse phase prep. HPLC to afford title compound as white solid (74 mg, 70%). MS (ESI) m/z 849 [M+H]+.

Example JV

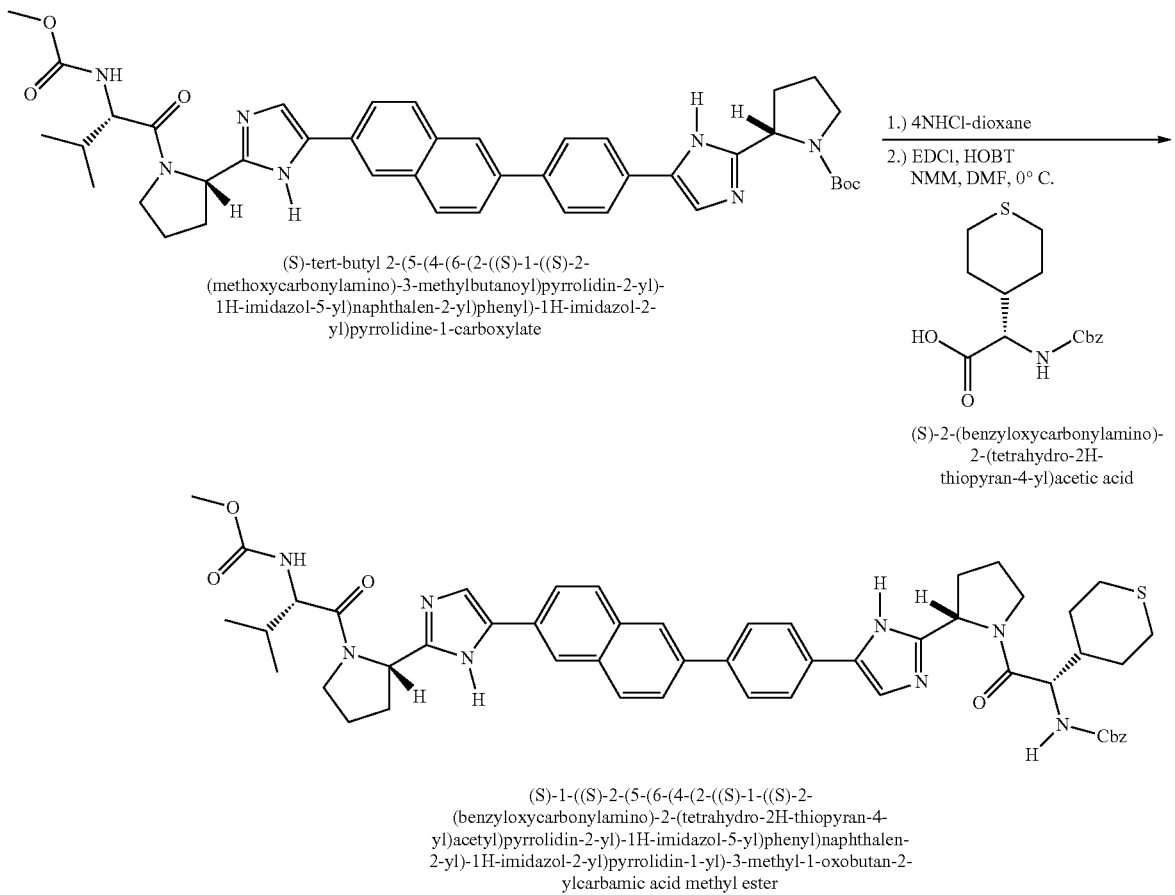

(S)-tert-butyl 2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate (S)-2-(benzyloxycarbonylamino)-2-(tetrahydro-2H-thiopyran-4-yl)acetic acid (S)-1-((S)-2-(5-(6-(4-(2-((S)-1-((S)-2-(benzyloxycarbonylamino)-2-(tetrahydro-2H-thiopyran-4-yl)acetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester (S) 1-((S)-2-(5-(6-(4-(2-((S)-1-((S)-2-(benzyloxycarbonylamino)-2-(tetrahydro-2H-thiopyran-4-yl)acetyl)pyrrolidin-2-yl)-1H-imidazole-5-yl)phenyl)naphthalen-2-yl)-1H-imidazol-2-yl)pyrrolidin-1-yl)-3-methyl-1-oxobutan-2-ylcarbamic acid methyl ester To (S)-tert-butyl 2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate (73 mg, 0.1 mmol) in dichloromethane (1.2 mL) was added 4M HCl in dioxane (1 mL) and the reaction mixture was cooled to 0° C. and then stirred for 2 hours. After concentrated in vacuo to afford HCl salts.

This HCl salts (68 mg 0.1 mmol) in DMF (1 mL) was added (S)-2-(benzyloxycarbonylamino)-2-(tetrahydro-2H-thiopyran-4-yl)acetic acid (40 mg, 0.13 mmol), N-(3-dimethylaminopropyl)-N'-ethylcarbodiimide hydrochloride (25 mg, 0.13 mmol) and hydroxybenzotriazole hydrate (HOBt), (18 mg, 0.13 mmol). The mixture was cooled down in an ice bath L, to 0° C. and N-methylmorpholine (NMM)(0.444 mmol) was added from a syringe to the mixture. The reaction content was stirred for 4 hours at room temperature. The resulting mixture was then directly purified on reverse phase prep. HPLC to afford title compound as white solid (77 mg, 90%). MS (ESI) m/z 924 [M+H]$^+$.

Example JW

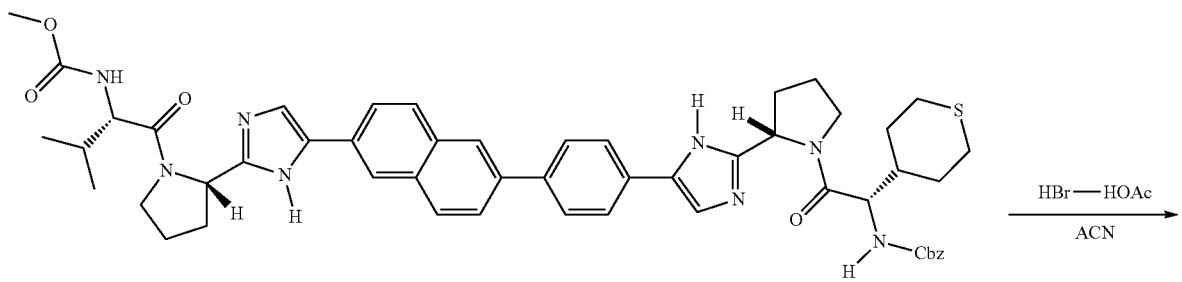

(S)-1-((S)-2-(5-(6-(4-(2-((S)-1-((S)-2-
(benzyloxycarbonylamino)-2-(tetrahydro-2H-thiopyran-4-
yl)acetyl)pyrrolidin-2-yl)-1H-imidazol-5-yl)phenyl)naphthalen-
2-yl)-1H-imidazol-2-yl)pyrrolidin-1-yl)-3-methyl-1-oxobutan-2-
ylcarbamic acid methyl ester

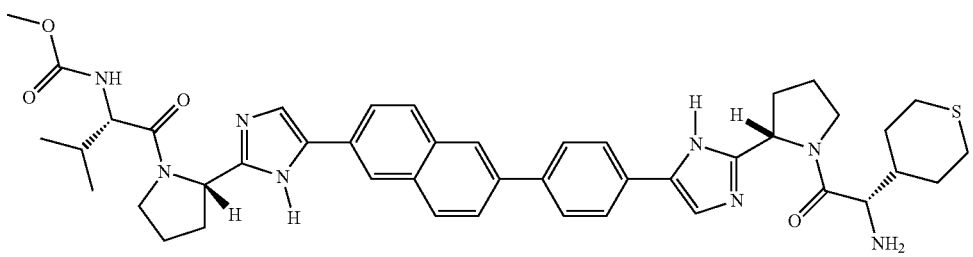

methyl (S)-1-((S)-2-(5-(6-(4-(2-((S)-1-((S)-2-amino-2-
(tetrahydro-2H-thiopyran-4-yl)acetyl)pyrrolidin-2-yl)-1H-
imidazol-5-yl)phenyl)naphthalen-2-yl)-1H-imidazol-2-
yl)pyrrolidin-1-yl)-3-methyl-1-oxobutan-2-ylcarbamate Methyl (S)-1-((S)-2-(5-(6-(4-(2-((S)-1-((S)-2-amino-2-(tetrahydro-2H-thiopyran-4-yl)acetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate: To (S)-1-((S)-2-(5-(6-(4-(2-((S)-1-((S)-2-(benzyloxycarbonylamino)-2-(tetrahydro-2H-thiopyran-4-yl)acetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester (46 mg, 0.05 mmol) in ACN (0.4 mL) was add 33% HBr in HOAc (0.1 mL) and reaction mixture was cooled to 0° C. and then stirred for 2 hours. After concentrated to afford title compound as white solid (33 mg, 85%). MS (ESI) m/z 790 [M+H]$^+$.

Example JX

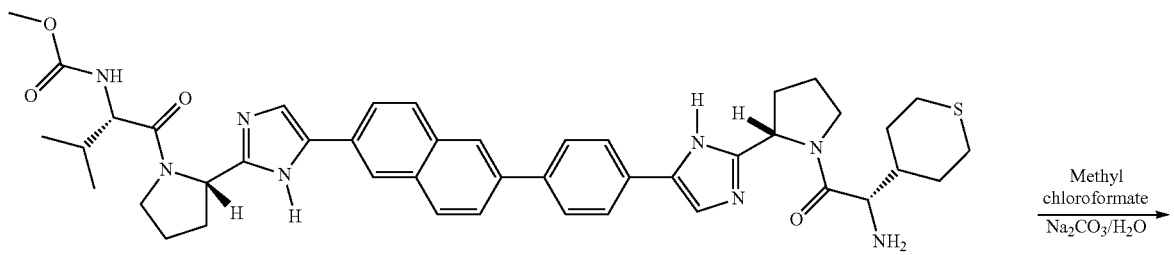

methyl (S)-1-((S)-2-(5-(6-(4-(2-((S)-1-((S)-2-amino-2-
(tetrahydro-2H-thiopyran-4-yl)acetyl)pyrrolidin-2-yl)-1H-
imidazol-5-yl)phenyl-naphthalen-2-yl)-1H-imidazol-2-
yl)pyrrolidin-1-yl)-3-methyl-1-oxobutan-2-ylcarbamate -continued

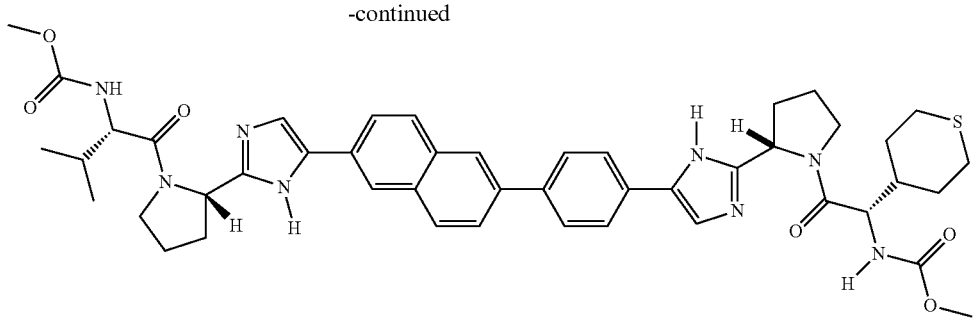

(S)-2-((S)-2-(5-(4-(6-(2-((S)-1-((S)-2-(methoxycarbonylamino)-
3-methylbutanoyl)pyrrolidin-2-yl)-1H-imidazol-5-yl)naphthalen-
2-yl)phenyl)-1H-imidazol-2-yl)pyrrolidin-1-yl)-2-oxo-1-
(tetrahydro-2H-thiopyran-4-yl)ethylcarbamic acid methyl ester (S)-2-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxo-1-(tetrahydro-2H-thiopyran-4-yl)ethylcarbamic acid methyl ester: To methyl (S)-1-((S)-2-(5-(6-(4-(2-((S)-1-((S)-2-amino-2-(tetrahydro-2H-thiopyran-4-yl)acetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate (30 mg, 0.06 mmol) in water (0.3 mL) was add Na$_2$CO$_3$ (13 L, 0.09 mmol). The reaction mixture was cooled to 0° C. and methyl chloroformate(0.12 mmol) was added and then stirred for 2 hours. The resulting mixture was then directly purified on reverse phase prep. HPLC to afford title compound as white solid (20 mg, 65%). MS (ESI) m/z 848 [M+H]$^+$.

Example JY

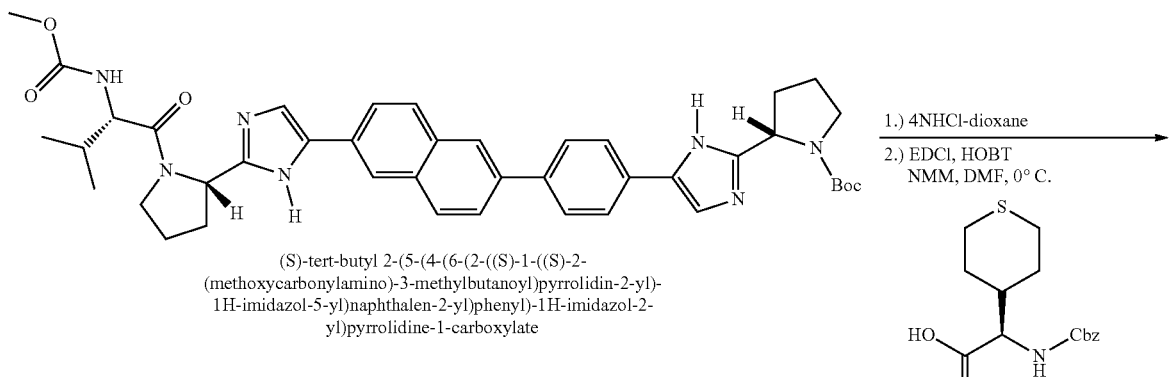

(S)-tert-butyl 2-(5-(4-(6-(2-((S)-1-((S)-2-
(methoxycarbonylamino)-3-methylbutanoyl)pyrrolidin-2-yl)-
1H-imidazol-5-yl)naphthalen-2-yl)phenyl)-1H-imidazol-2-
yl)pyrrolidine-1-carboxylate (R)-2-(benzyloxycarbonylamino)-
2-(tetrahydro-2H-
thiopyran-4-yl)acetic acid

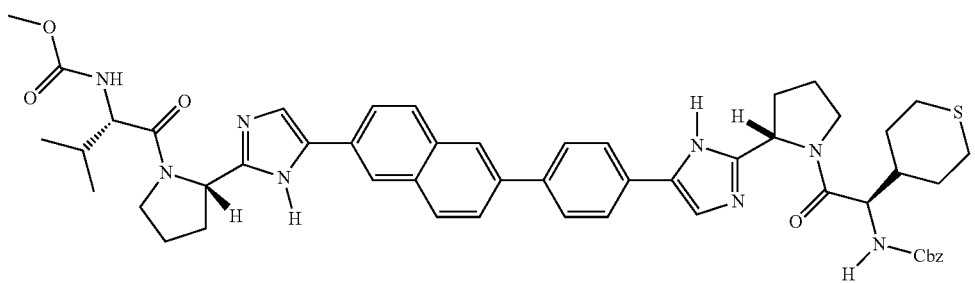

(S)-1-((S)-2-(5-(6-(4-(2-((S)-1-((R)-2-
(benzyloxycarbonylamino)-2-(tetrahydro-2H-thiopyran-4-
yl)acetyl)pyrrolidin-2-yl)-1H-imidazol-5-yl)phenyl)naphthalen-
2-yl)-1H-imidazol-2-yl)pyrrolidin-1-yl)-3-methyl-1-oxobutan-2-
ylcarbamic acid methyl ester (S)-1-((S)-2-(5-(6-(4-(2-((S)-1-((R)-2-(benzyloxycarbonylamino)-2-(tetrahydro-2H-thiopyran-4-yl)acetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester: Title compound was synthesized using methods analogous to the preparation of (S)-1-((S)-2-(5-(6-(4-(2-((S)-1-((S)-2-(benzyloxycarbonylamino)-2-(tetrahydro-2H-thiopyran-4-yl)acetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamic acid methyl ester, MS (ESI) m/z 924 [M+H]$^+$.

Example JZ

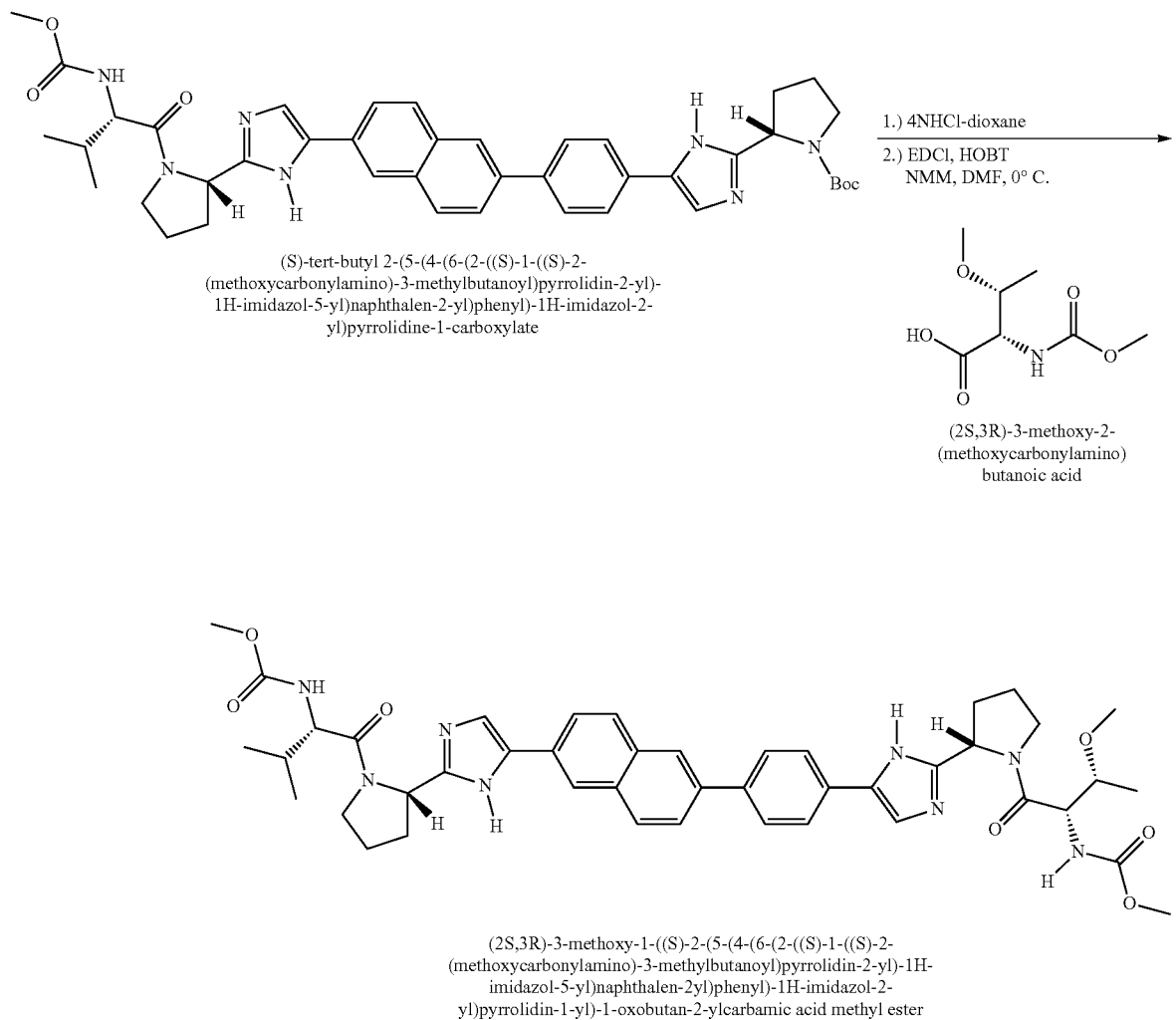

(S)-tert-butyl 2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate 1.) 4NHCl-dioxane
2.) EDCl, HOBT NMM, DMF, 0° C.

(2S,3R)-3-methoxy-2-(methoxycarbonylamino) butanoic acid (2S,3R)-3-methoxy-1-((S)-2-(5-(4-(6-(2-((S)-1-((S)-2-(methoxycarbonylamino)-3-methylbutanoyl)pyrrolidin-2-yl)-1H-imidazol-5-yl)naphthalen-2yl)phenyl)-1H-imidazol-2-yl)pyrrolidin-1-yl)-1-oxobutan-2-ylcarbamic acid methyl ester (2S,3R)-3-methoxy-1-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-1-oxobutan-2-ylcarbamic acid methyl ester: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 806 [M+H]$^+$.

Example KA

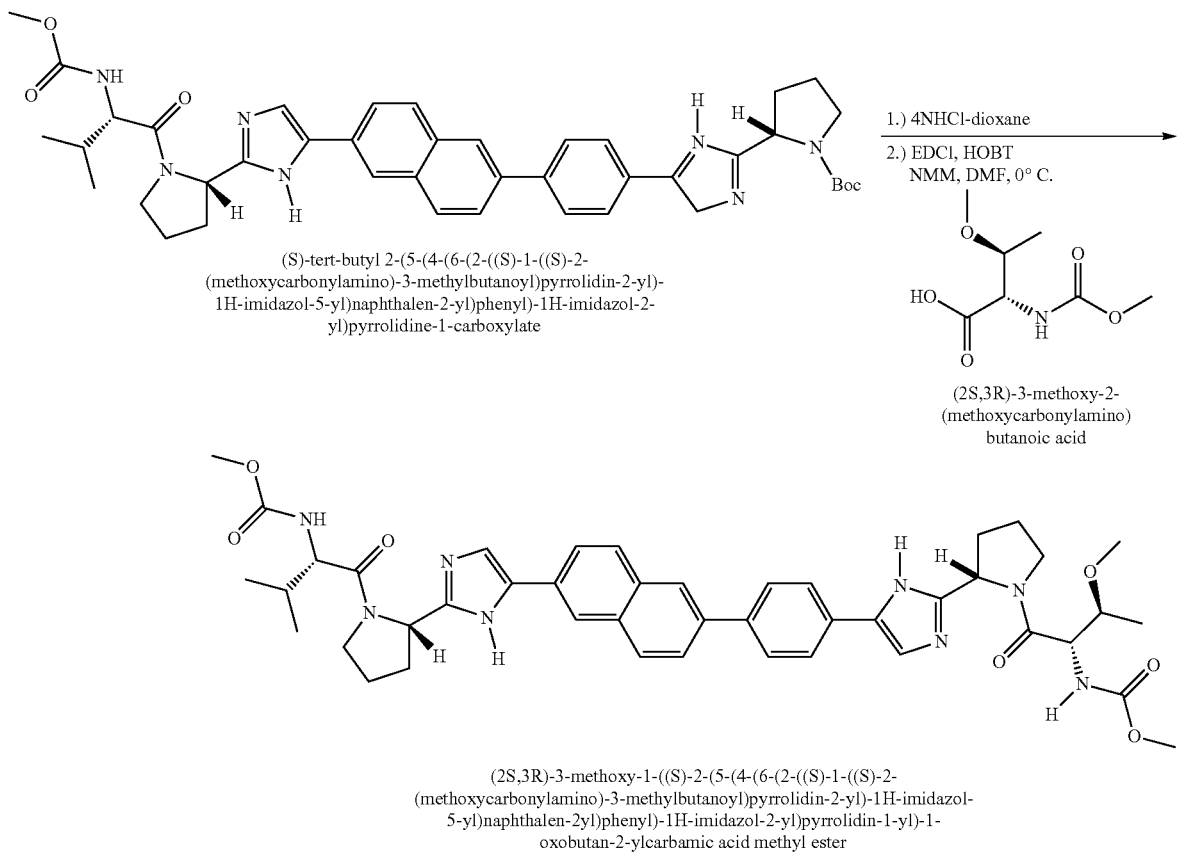

(2S,3S)-3-methoxy-1-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-1-oxobutan-2-ylcarbamic acid methyl ester: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 806 [M+H]+.

Example KB

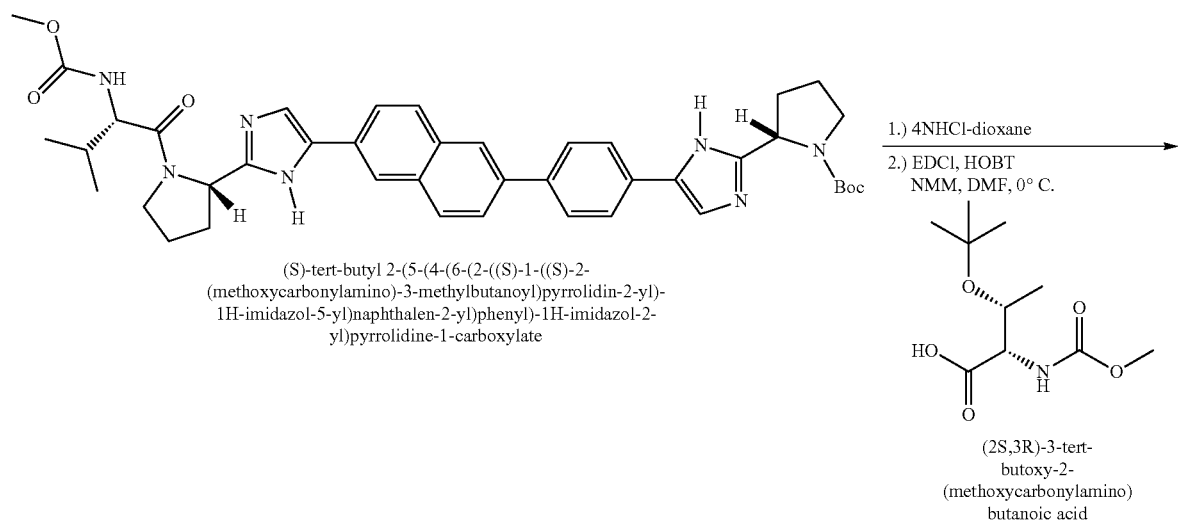

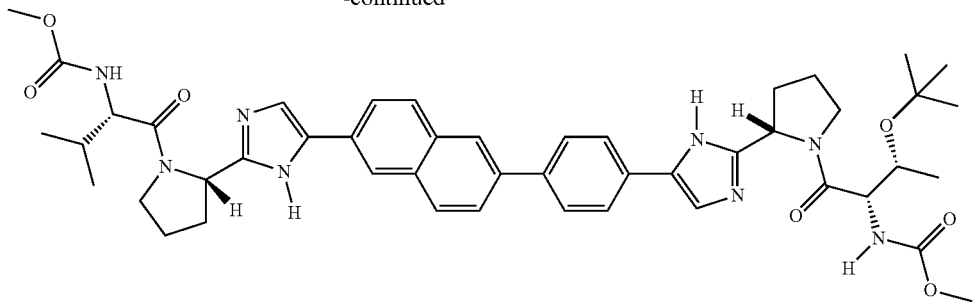

(2S,3R)-3-tert-butoxy-1-((S)-2-(5-(4-(6-(2-((S)-1-((S)-2-(methoxycarbonylamino)-3-methylbutanoyl)pyrrolidin-2-yl)-1H-imidazol-5-yl)naphthalen-2yl)phenyl)-1H-imidazol-2-yl)pyrrolidin-1-yl)-1-oxobutan-2-ylcarbamic acid methyl ester (2S,3R)-3-tert-butoxy-1-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-1-oxobutan-2-ylcarbamic acid methyl ester: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 848 [M+H]+

Example KC

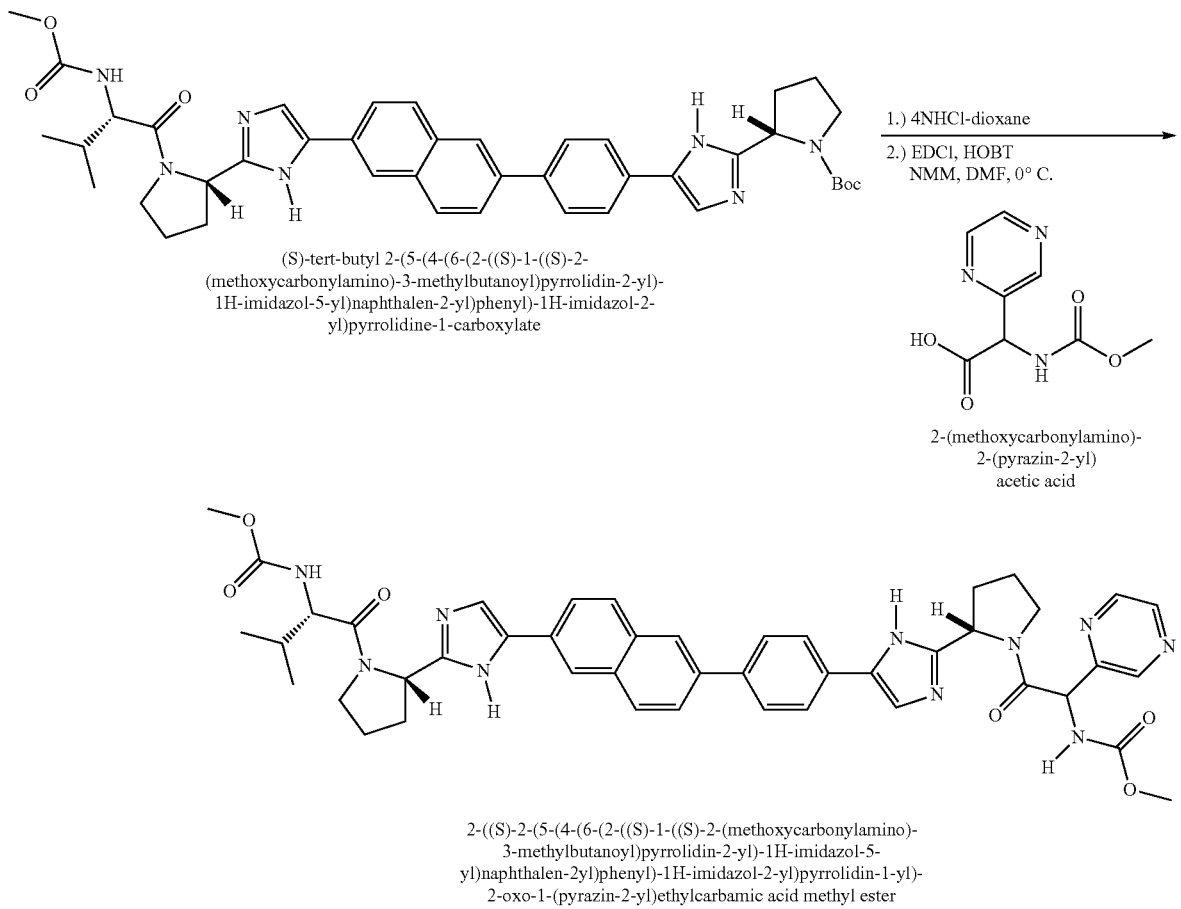

(S)-tert-butyl 2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate 1.) 4NHCl-dioxane
2.) EDCl, HOBT NMM, DMF, 0° C.

2-(methoxycarbonylamino)-2-(pyrazin-2-yl)acetic acid 2-((S)-2-(5-(4-(6-(2-((S)-1-((S)-2-(methoxycarbonylamino)-3-methylbutanoyl)pyrrolidin-2-yl)-1H-imidazol-5-yl)naphthalen-2yl)phenyl)-1H-imidazol-2-yl)pyrrolidin-1-yl)-2-oxo-1-(pyrazin-2-yl)ethylcarbamic acid methyl ester 2-((S)-2-(5-(4-(6-(2-((S)-1-((S)-2-(methoxycarbo-nylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxo-1-(pyrazin-2-yl)ethylcarbamic acid methyl ester: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 826[M+H]⁺.

Example KD

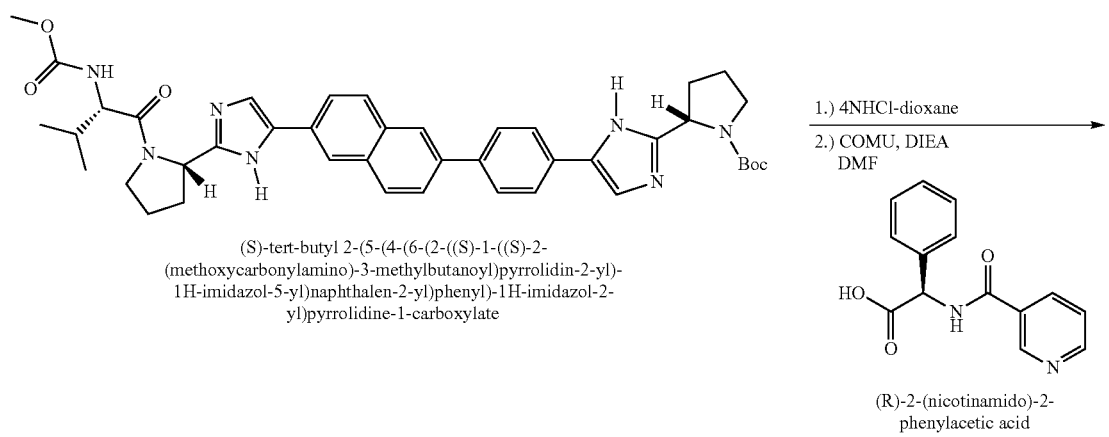

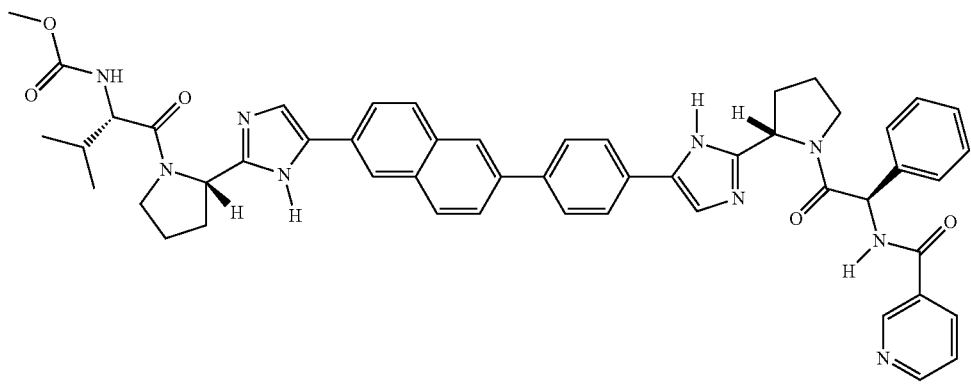

methyl (S)-3-methyl-1-((S)-2-(5-(6-(4-(2-((S)-1-((R)-2-(nicotinamido)-2-phenylacetyl)pyrrolidin-2-yl)-1H-imidazol-5-yl)phenyl)naphthalen-2-yl)-1H-imidazol 2-yl)pyrrolidin-1-yl)-1-oxobutan-2-ylcarbamate Methyl (S)-3-methyl-1-((S)-2-(5-(6-(4-(2-((S)-1-((R)-2-(nicotinamido)-2-phenylacetyl)pyrrolidin-2-yl)-1H-imidazol-5-yl)phenyl)naphthalen-2-yl)-1H-imidazol-2-yl)pyrrolidin-1-yl)-1-oxobutan-2-yl carbamate: Title compound was synthesized using methods analogous to the preparation of (R)-2-((1R,3S,4S)-3-(6-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-benzo[d]imidazol-2-yl)-2-azabicyclo[2.2.1]heptan-2-yl)-2-oxo-1-phenylethylcarbamic acid methyl ester, MS (ESI) m/z 871 [M+H]⁺.

Example KE

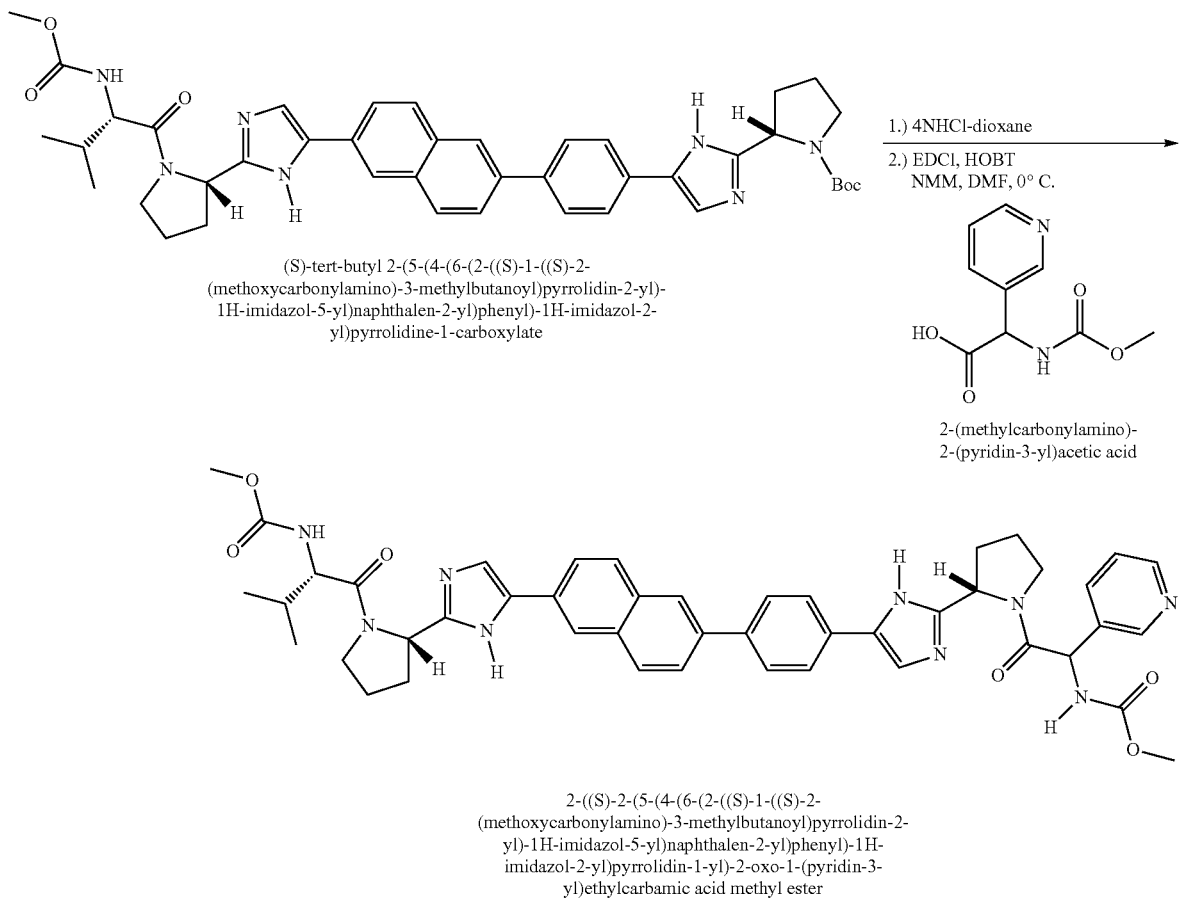

2-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxo-1-(pyridin-3-yl)ethylcarbamic acid methyl ester: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 825[M+H]+.

Example KF

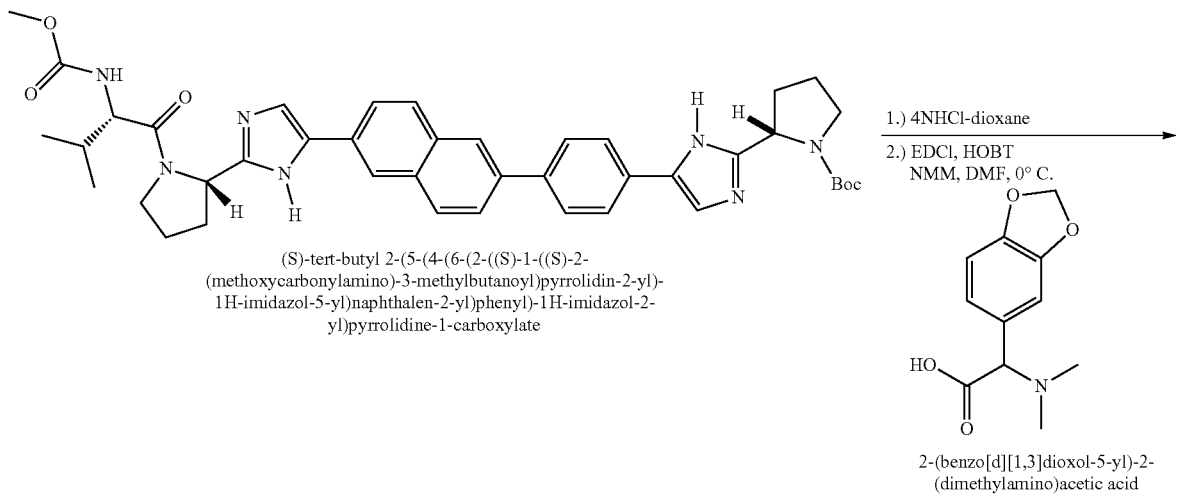

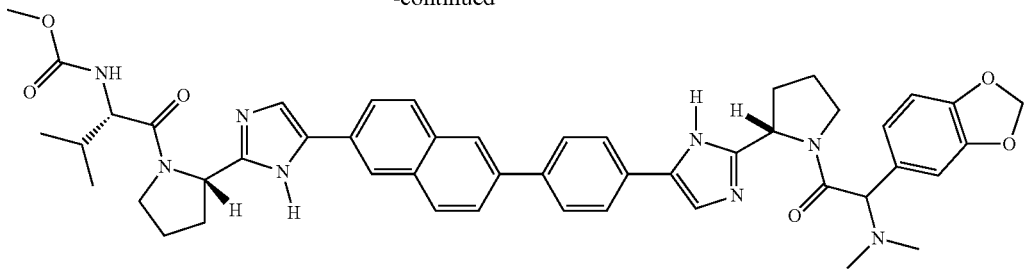

methyl (2S)-1-((2S)-2-(5-(6-(4-(2-((2S)-1-(2-(benzo[d][1,3]dioxol-5-yl)-2-(dimethylamino)acetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate Methyl (2S)-1-((2S)-2-(5-(6-(4-(2-((2S)-1-(2-(benzo[d][1,3]dioxol-5-yl)-2-(dimethylamino)acetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 838[M+H]⁺.

Example KG

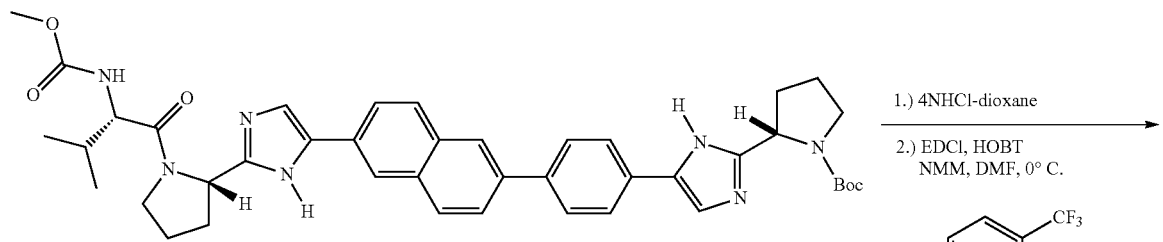

(S)-tert-butyl 2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate

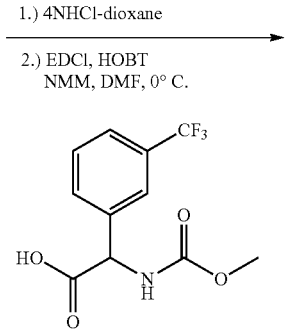

2-(methoxycarbonylamino)-2-(3-(trifluoromethyl)phenyl)acetic acid

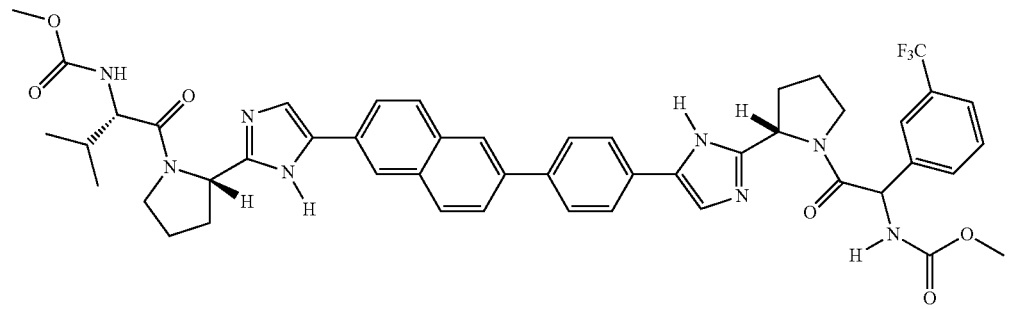

2-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxo-1-(3-(trifluoromethyl)phenyl)ethylcarbamic acid methyl ester 2-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxo-1-(3-(trifluoromethyl)phenyl)ethylcarbamic acid methyl ester: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 892[M+H]$^+$.

Example KH

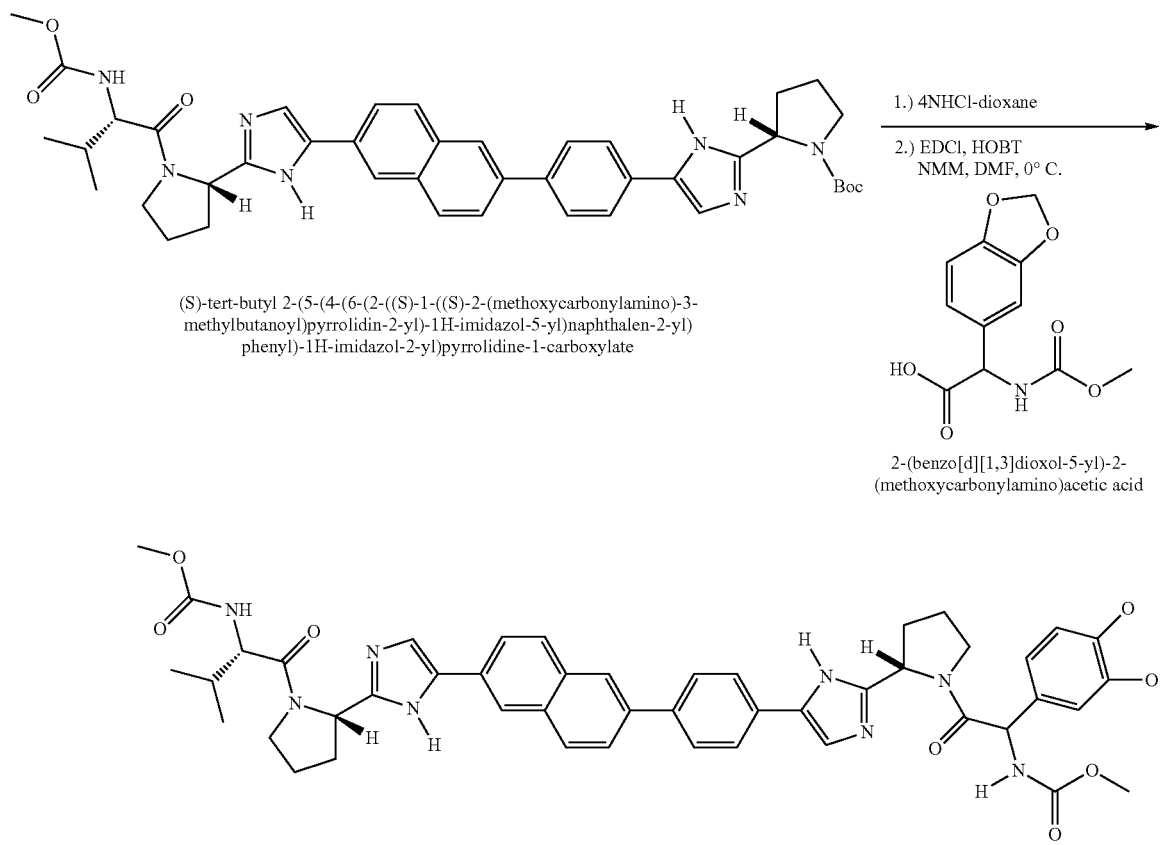

(S)-tert-butyl 2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate 2-(benzo[d][1,3]dioxol-5-yl)-2-(methoxycarbonylamino)acetic acid 1-(benzo[d][1,3]dioxol-5-yl)-2-((S)-2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidin-1-yl)-2-oxcethylcarbamic acid methyl ester 1-(Benzo[d][1,3]dioxol-5-yl)-2-((S)-2-(5-(4-(6-(2-((S)-1-((S)-2-(methoxycarbonylamino)-3-m ethylbutanoyl)pyrrolidin-2-yl)-1H-imidazol-5-yl)naphthalen-2-yl)phenyl)-1H-imidazol-2-yl)pyrrolidin-1-yl)-2-oxoethylcarbamic acid methyl ester: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 868[M+H]$^+$.

Example KI

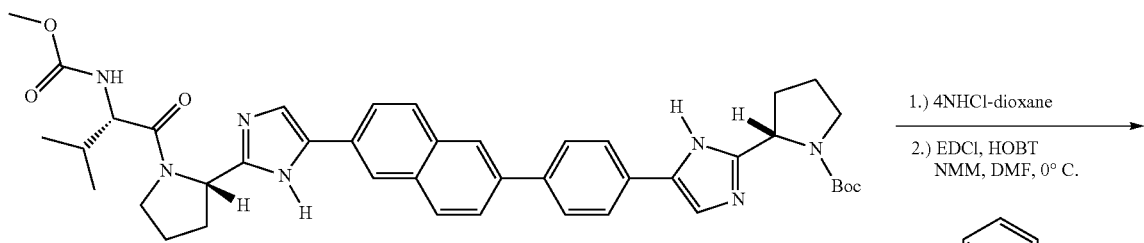

(S)-tert-butyl 2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate 1.) 4NHCl-dioxane
2.) EDCl, HOBT NMM, DMF, 0° C.

2-(diethylamino)-2-phenylacetic acid

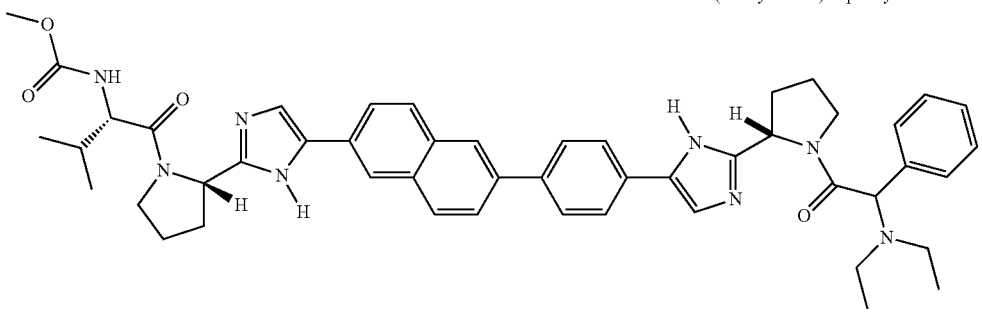

methyl (2S)-1-((2S)-2-(5-(6-(4-(2-((2S)-1-(2-(diethylamino-2-phenlacetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate Methyl (2S)-1-((2S)-2-(5-(6-(4-(2-((2S)-1-(2-(diethylamino)-2-phenylacetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 822[M+H]$^+$.

Example KJ

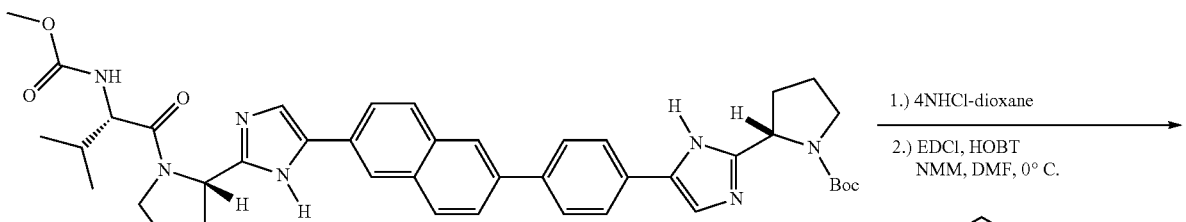

(S)-tert-butyl 2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate 1.) 4NHCl-dioxane
2.) EDCl, HOBT NMM, DMF, 0° C.

2-(dimethylamino)-2-phenylacetic acid

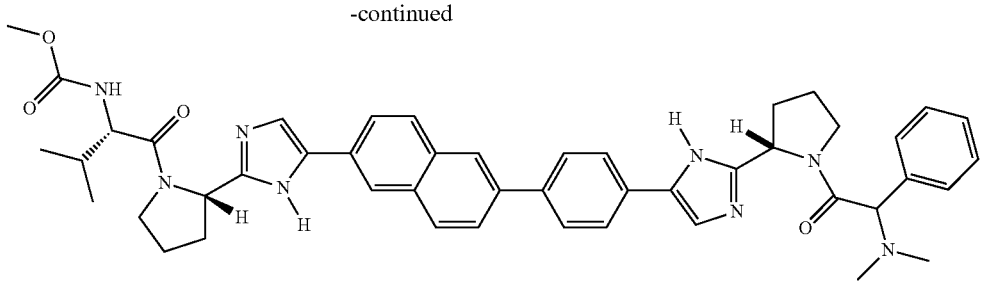

methyl (2S)-1-((2S)-2-(5-(6-(4-(2-((2S)-1-(2-dimethylamino-2-phenylacetyl)pyrrolidin-2-yl)-1H-imidazol-5-yl)phenyl)naphthalen-2-yl)-1H-imidazol-2-yl)pyrrolidin-1-yl)-3-methyl-1-oxobutan-2-ylcarbamate Methyl (2S)-1-((2S)-2-(5-(6-(4-(2-((2S)-1-(2-(dimethylamino)-2-phenylacetyl)pyrrolidin-2-yl)-t H-imidazol-5-yl)phenyl)naphthalen-2-yl)-1H-imidazol-2-yl)pyrrolidin-1-yl)-3-methyl-1-oxobutan-2-yl carbamate: Title compound was synthesized using methods analogous to the preparation of (2S,3R)-3-methoxy-1-((1R,3 S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 794[M+H]$^+$.

Example KK

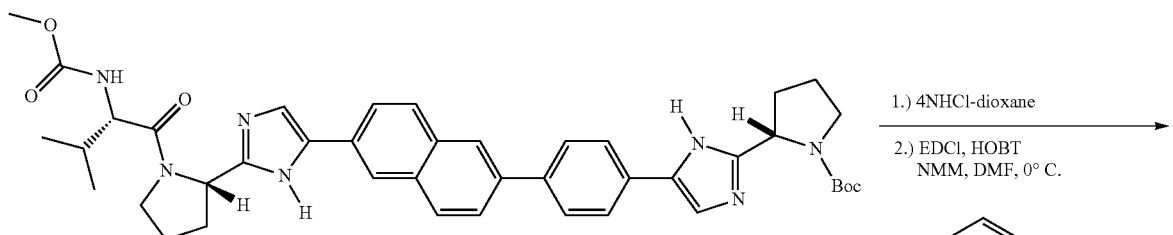

(S)-tert-butyl 2-(5-(4-(6-(2-((S)-1-((S)-2-(methoxycarbonylamino)-3-methylbutanoyl)pyrrolidin-2-yl)-1H-imidazol-5-yl)naphthalen-2-yl)phenyl)-1H-imidazol-2-yl)pyrrolidine-1-carboxylate 1.) 4NHCl-dioxane
2.) EDCl, HOBT NMM, DMF, 0° C.

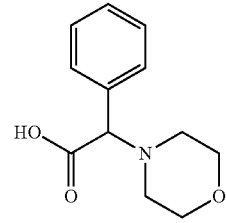

2-morpholino-2-phenylacetic acid

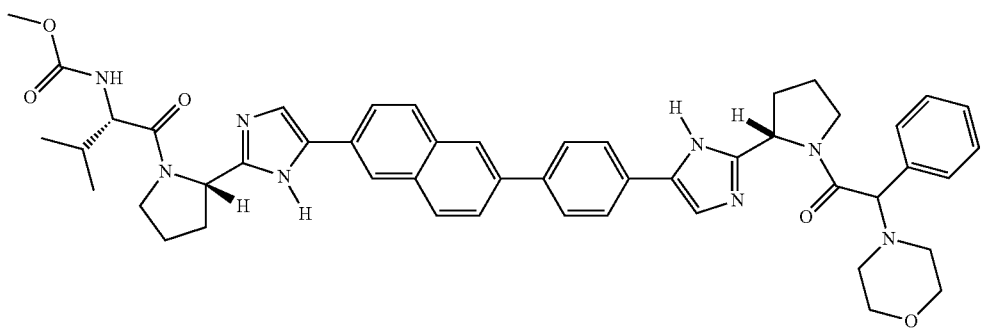

methyl (2S)-3-methyl-1-((2S)-2-(5-(6-(4-(2-((2S)-1-(2-morpholino-2-phenylacetyl)pyrrolidin-2-yl)-1H-imidazol-5-yl)phenyl)naphthalen-2-yl)-1H-imidazol-2-yl)pyrrolidin-1-yl)-1-oxobutan-2-ylcarbamate Methyl (2S)-3-methyl-1-((2S)-2-(5-(6-(4-(2-((2S)-1-(2-morpholino-2-phenylacetyl)pyrrolidin-2-yl)-1H-imidazol-5-yl)phenyl)naphthalen-2-yl)-1H-imidazol-2-yl)pyrrolidin-1-yl)-1-oxobutan-2-ylcarbamate: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 836[M+H]+.

Example KL

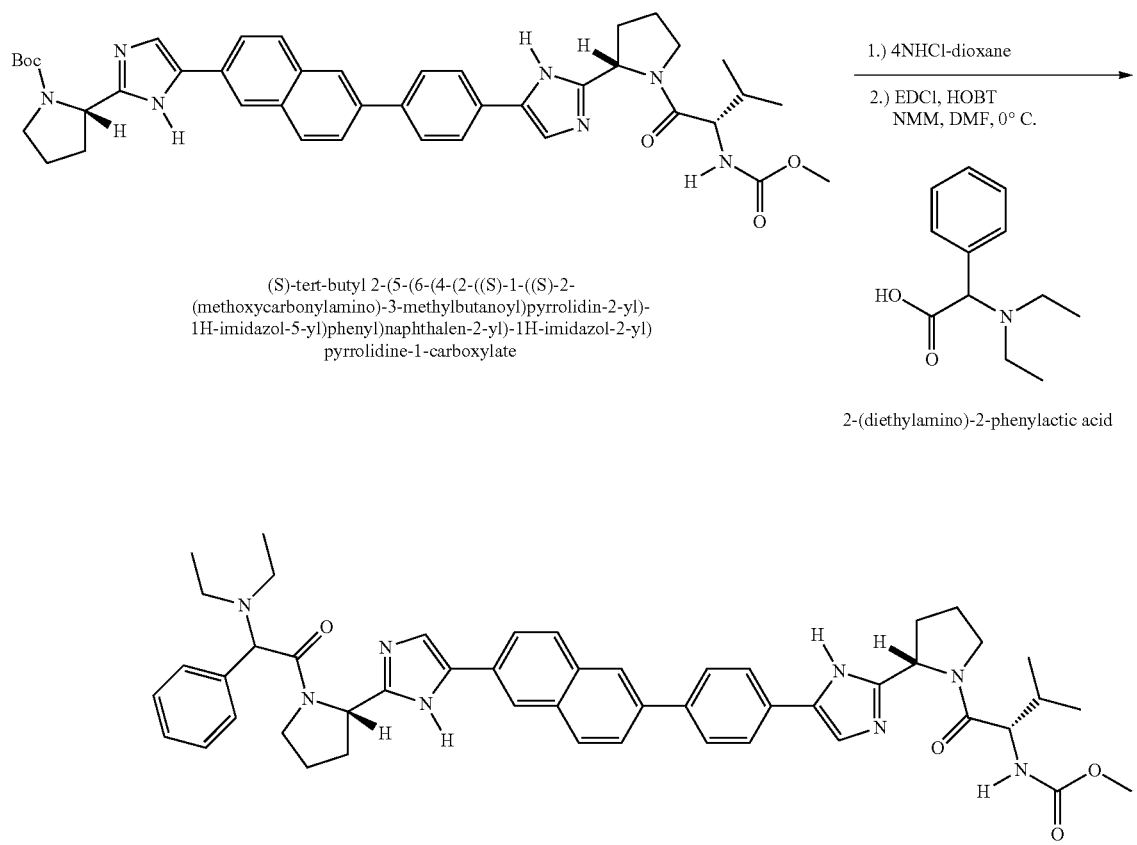

(S)-tert-butyl 2-(5-(6-(4-(2-((S)-1-((S)-2-(methoxycarbonylamino)-3-methylbutanoyl)pyrrolidin-2-yl)-1H-imidazol-5-yl)phenyl)naphthalen-2-yl)-1H-imidazol-2-yl)pyrrolidine-1-carboxylate 2-(diethylamino)-2-phenylactic acid methyl (2S)-1-((2S)-2-(5-(4-(6-(2-((2S)-1-(2-(diethylamino)-2-phenylacetyl)pyrrolidin-2-yl)-1H-imidazol-5-yl)naphthalen-2-yl)phenyl)-1H-imidazol-2-yl)pyrrolidin-1-yl)-3-methyl-1-oxobutan-2-ylcarbamate Methyl (2S)-1-((2S)-2-(5-(4-(6-(2-((2S)-1-(2-(diethylamino)-2-phenylacetyl)pyrrolidin-2-yl)-1H-imidazol-5-yl)naphthalen-2-yl)phenyl)-1H-imidazol-2-yl)pyrrolidin-1-yl)-3-methyl-1-oxobutan-2-ylcarbamate: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 822[M+H]+.

Example KM

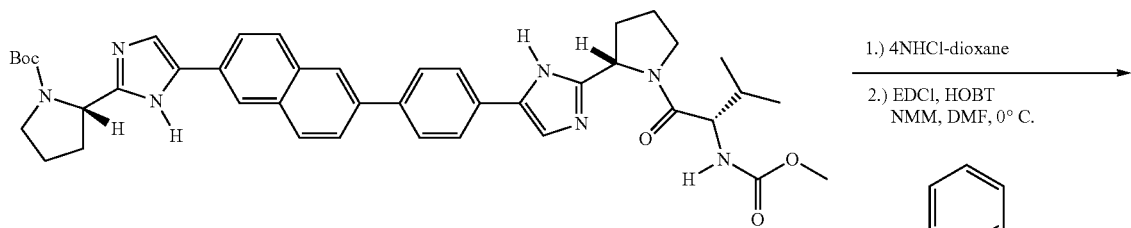

(S)-tert-butyl 2-(5-(6-(4-(2-((S)-1-((S)-2-(methoxycarbonylamino)-3-methylbutanoyl)pyrrolidin-2-yl)-1H-imidazol-5-yl)phenyl)naphthalen-2-yl)-1H-imidazol-2-yl)pyrrolidine-1-carboxylate 1.) 4NHCl-dioxane
2.) EDCl, HOBT NMM, DMF, 0° C.

2-phenyl-2-(pyrrolidin-1-yl)acetic acid

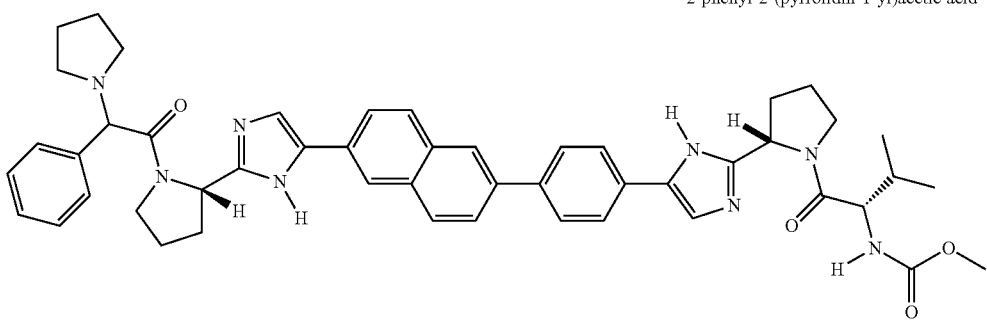

methyl (2S)-3-methyl-1-oxo-1-((2S)-2-(5-(4-(6-(2-((2S)-1-(2-phenyl-2-(pyrrolidin-1-yl)acetyl)pyrrolidin-2-yl)-1H-imidazol-5-yl)naphthalen-2-yl)phenyl)-1H-imidazol-2-yl)pyrrolidin-1-yl)butan-2-ylcarbamate Methyl (2S)-3-methyl-1-oxo-1-((2S)-2-(5-(4-(6-(2-((2S)-1-(2-phenyl-2-(pyrrolidin-1-yl)acetyl)pyrrolidin-2-yl)-1H-imidazol-5-yl)naphthalen-2-yl)phenyl)-1H-imidazol-2-yl)pyrrolidin-1-yl)butan-2-ylcarbamate: Title compound was synthesized using methods analogous to the preparation of (2S,3R)-3-methoxy-1-((1R,3 S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 820[M+H]$^+$.

Example KN

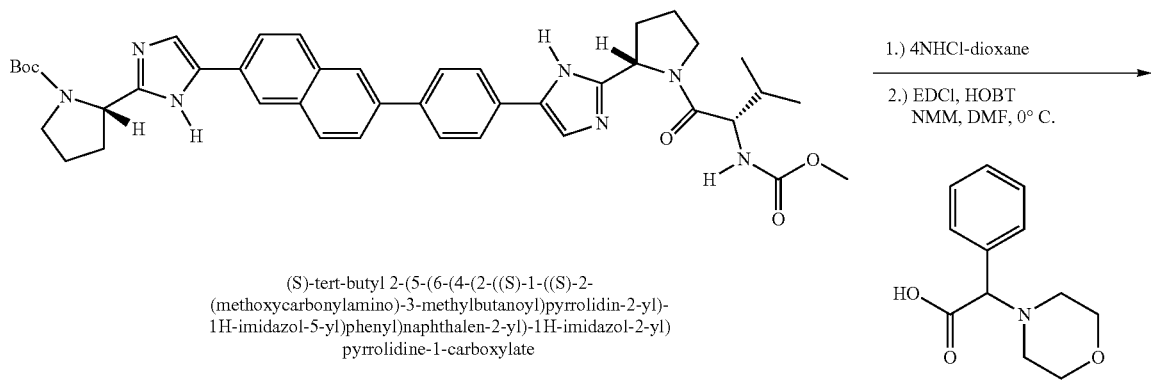

(S)-tert-butyl 2-(5-(6-(4-(2-((S)-1-((S)-2-(methoxycarbonylamino)-3-methylbutanoyl)pyrrolidin-2-yl)-1H-imidazol-5-yl)phenyl)naphthalen-2-yl)-1H-imidazol-2-yl)pyrrolidine-1-carboxylate 1.) 4NHCl-dioxane
2.) EDCl, HOBT NMM, DMF, 0° C.

2-morpholino-2-phenylacetic acid

-continued

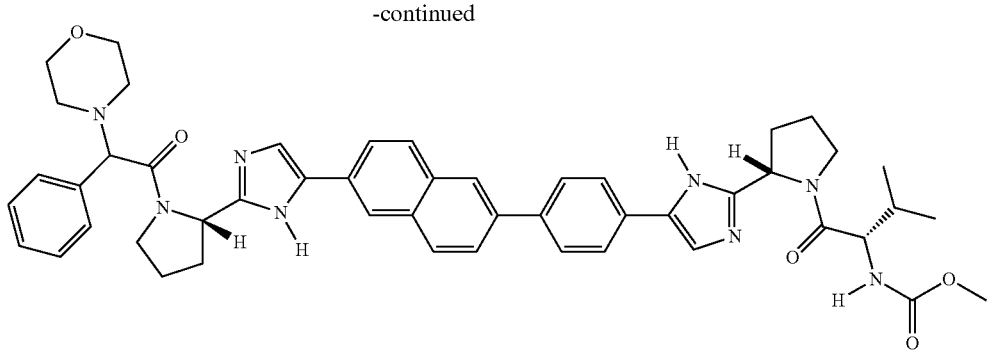

methyl (2S)-3-methyl-1-((2S)-2-(5-(4-(6-(2-((2S)-1-(2-morpholino-2-phenylacetyl)pyrrolidin-2-yl)-1H-imidazol-5-yl)naphthalen-2-yl)phenyl)-1H-imidazol-2-yl)pyrrolidin-1-yl)-1-oxobutan-2-ylcarbamate Methyl (2S)-3-methyl-1-((2S)-2-(5-(4-(6-(2-((2S)-1-(2-morpholino-2-phenylacetyl)pyrrolidin-2-yl)-1H-imidazol-5-yl)naphthalen-2-yl)phenyl)-1H-imidazol-2-yl)pyrrolidin-1-yl)-1-oxobutan-2-ylcarbamate: Title compound was synthesized using methods analogous to the preparation of (2S,3R)-3-methoxy-1-((1R,3 S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 836[M+H]$^+$.

Example KO

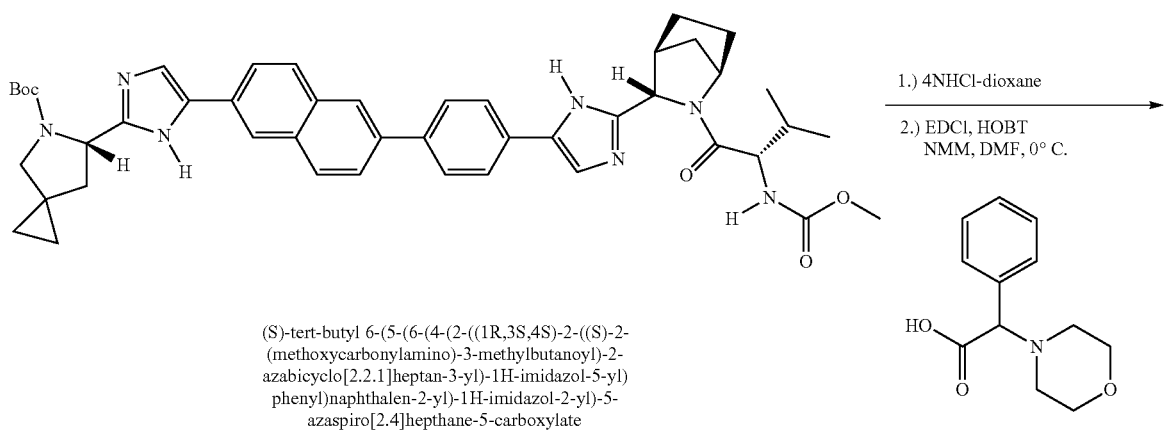

(S)-tert-butyl 6-(5-(6-(4-(2-((1R,3S,4S)-2-((S)-2-(methoxycarbonylamino)-3-methylbutanoyl)-2-azabicyclo[2.2.1]heptan-3-yl)-1H-imidazol-5-yl)phenyl)naphthalen-2-yl)-1H-imidazol-2-yl)-5-azaspiro[2.4]hepthane-5-carboxylate 2-morpholino-2-phenylacetic acid

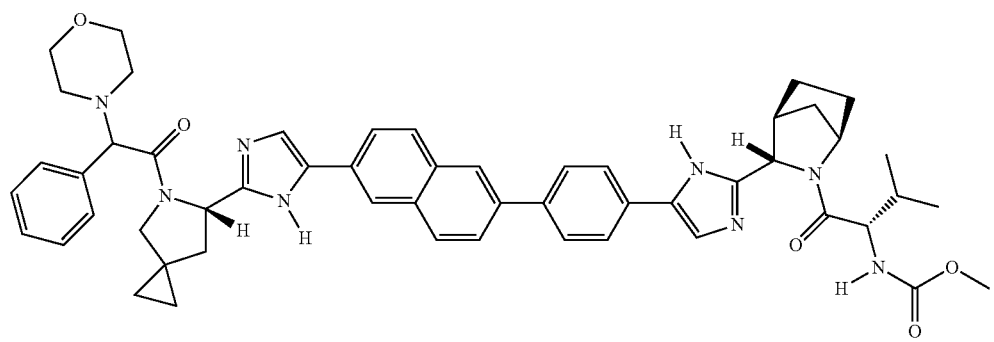

methyl (2S)-3-methyl-1-((1R, 3S, 4S)-3-(5-(4-(6-(2-((6S)-5-(2-morpholino-2-phenylacetyl)-5-azaspiro[2.4]heptan-6-yl)-1H-imidazol-5-yl)naphthalen-2-yl)phenyl)-1H-imidazol-2-yl)-2-azabicyclo[2.2.1]hepthan-2-yl)-1-oxobutan-2-ylcarbamate Methyl (2S)-3-methyl-1-((1R,3S,4S)-3-(5-(4-(6-(2-(((6S)-5-(2-morpholino-2-phenylacetyl)-5-azaspiro[2.4]heptan-6-yl)-1H-imidazol-5-yl)naphthalen-2-yl)phenyl)-1H-imidazol-2-yl)-2-azabicyclo[2.2.1]heptan-2-yl)-1-oxobutan-2-ylcarbamate: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 888[M+H]$^+$.

Example KP

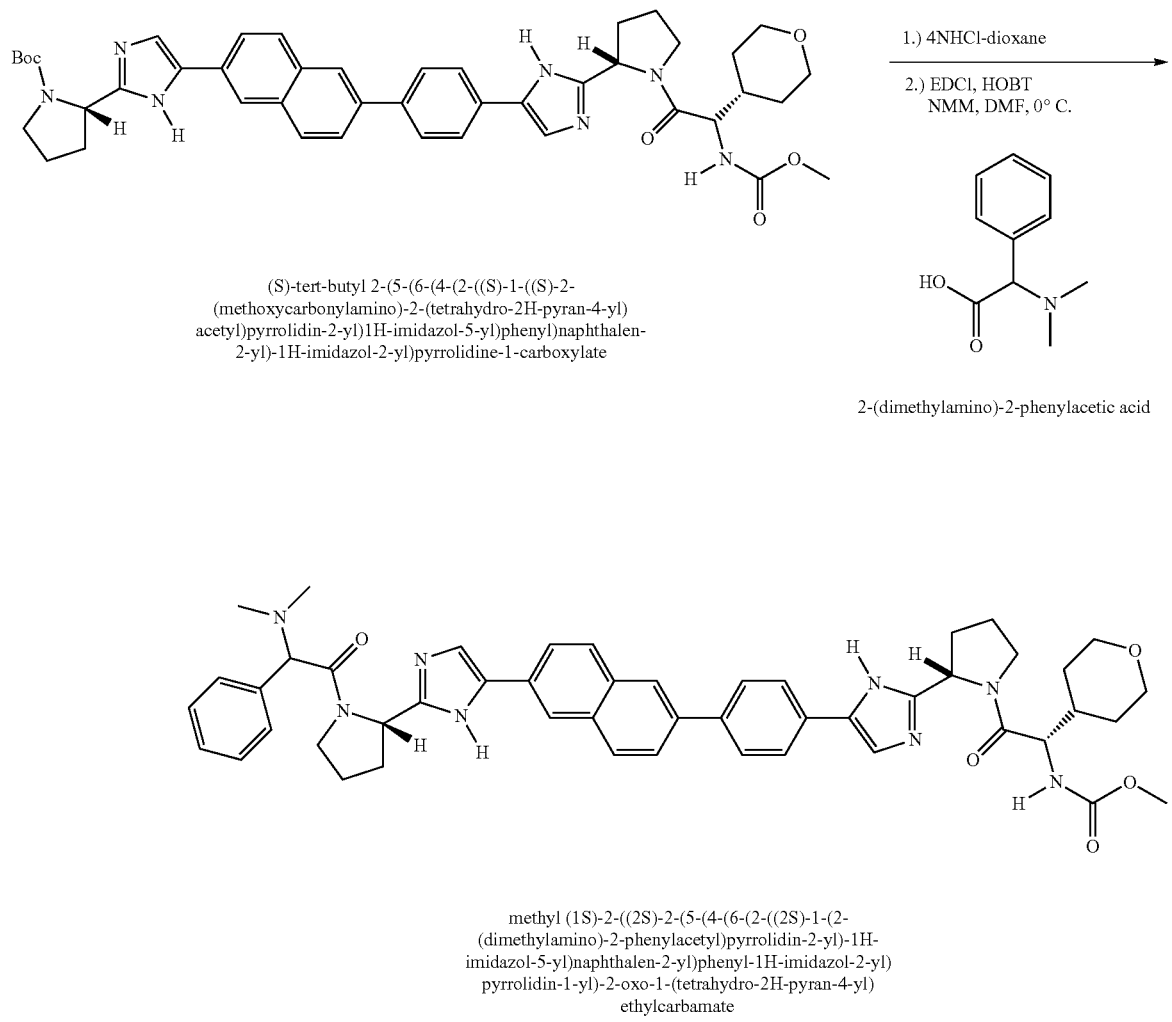

(S)-tert-butyl 2-(5-(6-(4-(2-((S)-1-((S)-2-(methoxycarbonylamino)-2-(tetrahydro-2H-pyran-4-yl)acetyl)pyrrolidin-2-yl)1H-imidazol-5-yl)phenyl)naphthalen-2-yl)-1H-imidazol-2-yl)pyrrolidine-1-carboxylate 2-(dimethylamino)-2-phenylacetic acid methyl (1S)-2-((2S)-2-(5-(4-(6-(2-((2S)-1-(2-(dimethylamino)-2-phenylacetyl)pyrrolidin-2-yl)-1H-imidazol-5-yl)naphthalen-2-yl)phenyl-1H-imidazol-2-yl)pyrrolidin-1-yl)-2-oxo-1-(tetrahydro-2H-pyran-4-yl)ethylcarbamate Methyl (1 S)-2-((2S)-2-(5-(4-(6-(2-((2S)-1-(2-(dimethylamino)-2-phenylacetyl)pyrrolidin-2-yl)-1H-imidazol-5-yl)naphthalen-2-yl)phenyl)-1H-imidazol-2-yl)pyrrolidin-1-yl)-2-oxo-1-(tetrahydro-2H-pyran-4-yl)ethylcarbamate: Title compound was synthesized using methods analogous to the preparation of (2S,3R)-3-methoxy-1-((1R,3 S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1 T-imidazol-2-yl)-2-azabicyclo[2.2.1]heptan-2-yl)-1-oxobutan-2-ylcarbamic acid methyl ester, MS (ESI) m/z 836[M+H]$^+$.

Example KQ

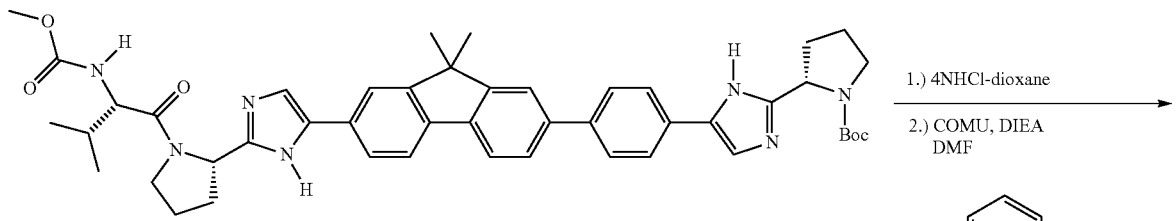

(S)-tert-butyl 2-(5-(4-(9,9-difluoro-7-(2-((S)-1-((S)-2-methoxycarbonylamino)-3-methylbuttanoyl)pyrrolidin-2-yl)-1H-imidazol-5-yl)9H-fluoren-2-yl)phenyl)-1H-imidazol-2-yl)pyrrolidine-1-carboxylate 1.) 4NHCl-dioxane
2.) COMU, DIEA DMF (R)-2-(methoxycarbonylamino)-2-phenylacetic acid

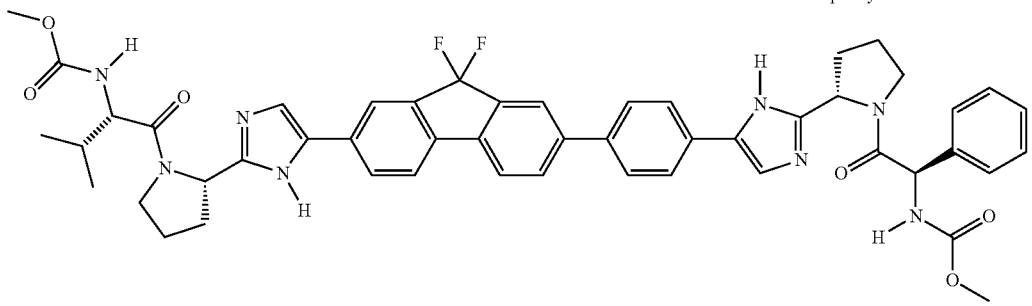

(R)-2-((S)-2-(5-(4-(9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)phenyl)-1H-imidazol-2-yl)pyrrolidin-1-yl)-2-oxo-1-phenylethylcarbamic acid methyl ester (R)-2-((S)-2-(5-(4-(9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)phenyl)-1H-imidazol-2-yl)pyrrolidin-1-yl)-2-oxo-1-phenylethylcarbamic acid methyl ester: Title compound was synthesized using methods analogous to the preparation of (R)-2-((1R,3S,4S)-3-(6-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-benzo[d]imidazol-2-yl)-2-azabicyclo[2.2.1]heptan-2-yl)-2-oxo-1-phenylethylcarbamic acid methyl ester, MS (ESI) m/z 898 [M+H]$^+$.

Example KR

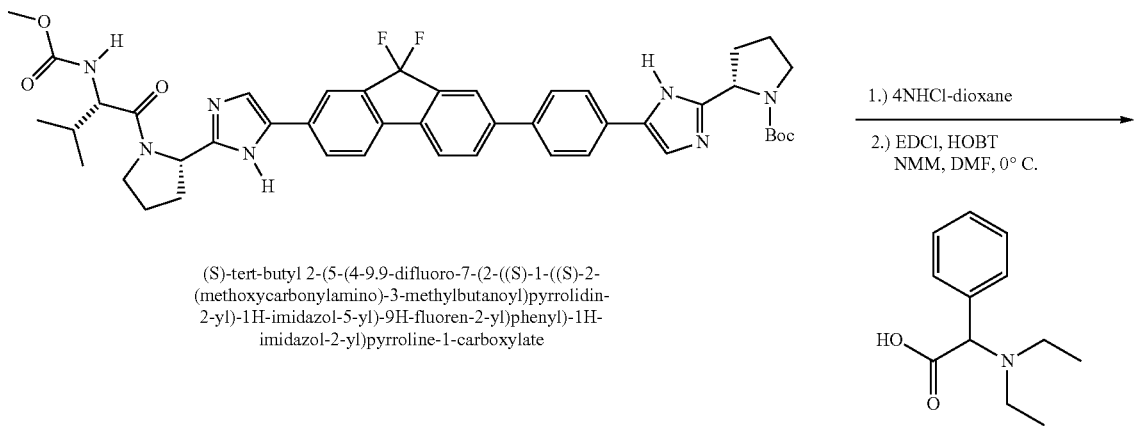

(S)-tert-butyl 2-(5-(4-9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)phenyl)-1H-imidazol-2-yl)pyrroline-1-carboxylate 1.) 4NHCl-dioxane
2.) EDCl, HOBT NMM, DMF, 0° C.

2-(diethylamino)-2-phenylactic acid

-continued

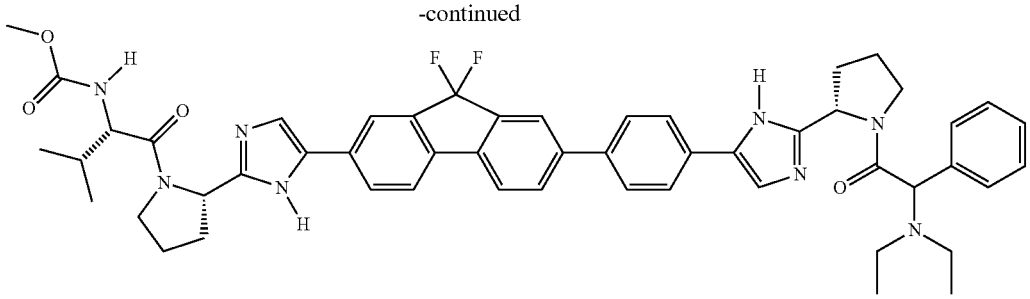

methyl (2S)-1-((2S)-2-(5-(7-(4-(2-((2s)-1-(2-(diethylamino)-2-phenylacetyl)pyrrolidin-2-yl)-1H-imidazol-5-yl)phenyl)-9,9-difluoro-9H-fluoren-2-yl)-1H-imidazol-2-yl)pyrrolidin-1-yl)3-methyl-1-oxobutan-2-ylcarbamate Methyl (2S)-1-((2S)-2-(5-(7-(4-(2-((2S)-1-(2-(diethylamino)-2-phenylacetyl)pyrrolidin-2-yl)-1H-imidazol-5-yl)phenyl)-9,9-difluoro-9H-fluoren-2-yl)-1H-imidazol-2-yl)pyrrolidin-1-yl)-3-methyl-1-oxobutan-2-ylcarbamate: Title compound was synthesized using methods analogous to the preparation of (2S,3R)-3-methoxy-1-((1R,3 S,4 S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 896[M+H]+.

Example KS

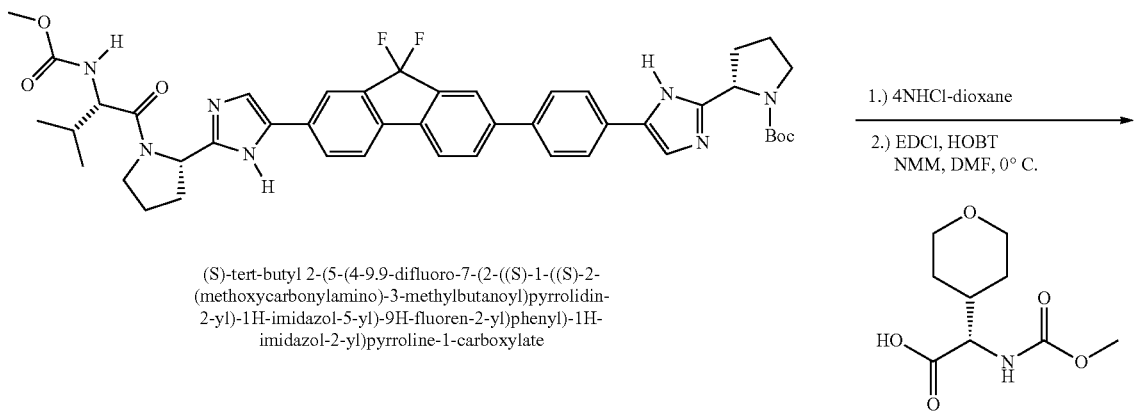

(S)-tert-butyl 2-(5-(4-9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)phenyl)-1H-imidazol-2-yl)pyrroline-1-carboxylate (S)-2-(methoxycarbonylamino)-2-(tetrahydro-2H-pyran-4-yl)acetic acid

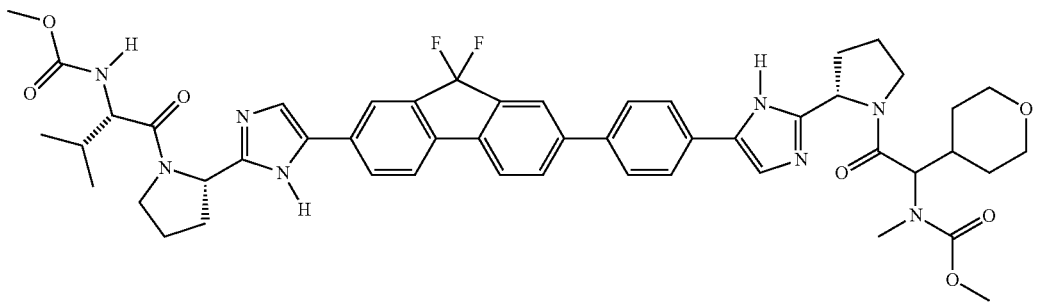

(S)-2-((S)-2-(5-(4-(9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)phenyl)-1H-imidazol-2-yl)pyrrolidin-1-yl)-2-oxo-1-(tetrahydro-2H-pyran-4-yl)ethylcarbamic acid methyl ester (S)-2-((S)-2-(5-(4-(9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)phenyl)-1H-imidazol-2-yl)pyrrolidin-1-yl)-2-oxo-1-(tetrahydro-2H-pyran-4-yl)ethylcarbamic acid methyl ester: Title compound was synthesized using methods analogous to the preparation of (2S,3R)-3-methoxy-1-((1R,3 S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 906[M+H]$^+$.

Example KT

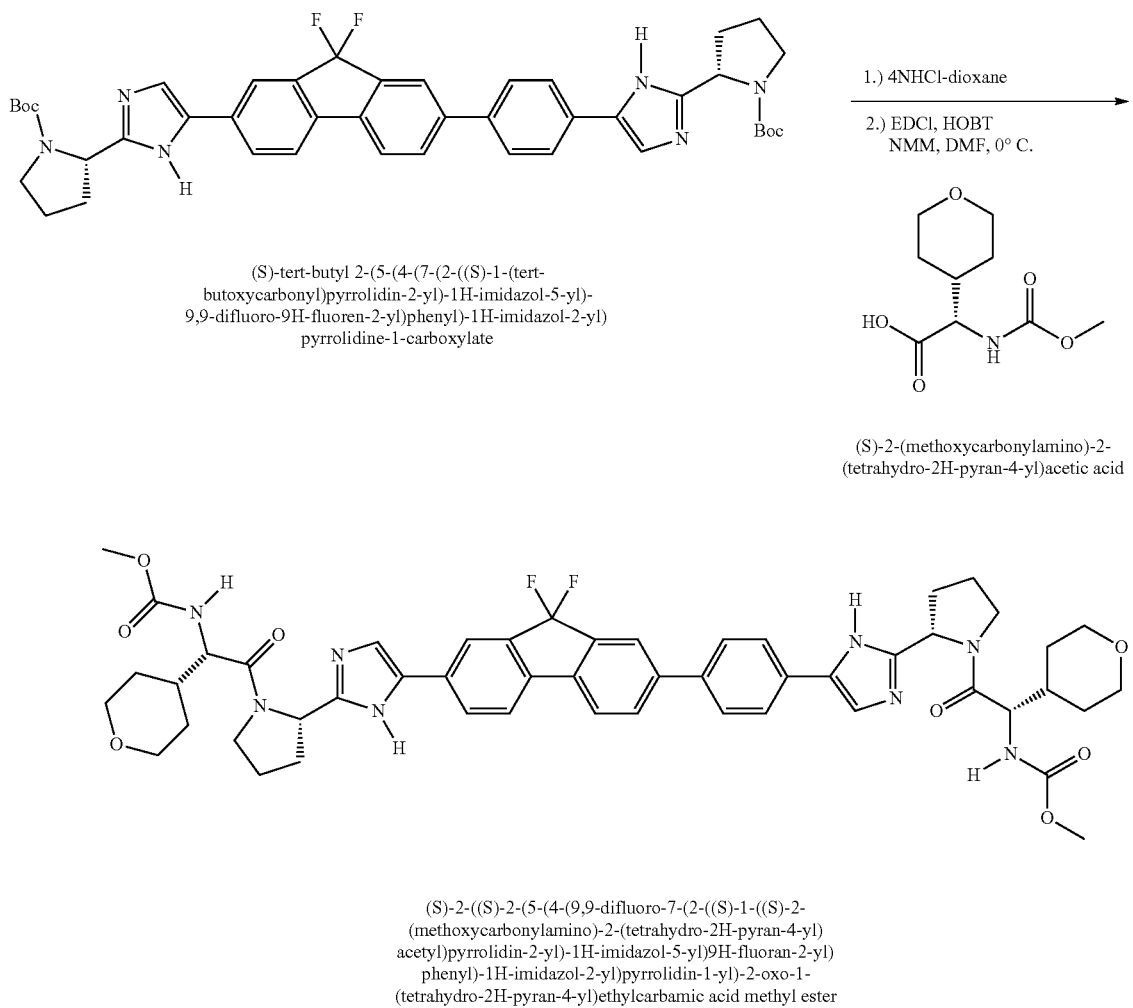 [SMILES: CC(C)(C)OC(=O)N1CCC[C@H]1c1ncc(-c2ccc(-c3ccc4c(c3)C(F)(F)c3cc(-c5cnc([C@@H]6CCCN6C(=O)OC(C)(C)C)[nH]5)ccc3-4)cc2)[nH]1 ; COC(=O)N[C@H](C(=O)O)C1CCOCC1 ; COC(=O)N[C@H](C(=O)N1CCC[C@H]1c1ncc(-c2ccc(-c3ccc4c(c3)C(F)(F)c3cc(-c5cnc([C@@H]6CCCN6C(=O)[C@@H](NC(=O)OC)C6CCOCC6)[nH]5)ccc3-4)cc2)[nH]1)C1CCOCC1]

(S)-tert-butyl 2-(5-(4-(7-(2-((S)-1-(tert-butoxycarbonyl)pyrrolidin-2-yl)-1H-imidazol-5-yl)-9,9-difluoro-9H-fluoren-2-yl)phenyl)-1H-imidazol-2-yl)pyrrolidine-1-carboxylate 1.) 4NHCl-dioxane 2.) EDCl, HOBT
NMM, DMF, 0° C.

(S)-2-(methoxycarbonylamino)-2-(tetrahydro-2H-pyran-4-yl)acetic acid (S)-2-((S)-2-(5-(4-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)9H-fluoran-2-yl)phenyl)-1H-imidazol-2-yl)pyrrolidin-1-yl)-2-oxo-1-(tetrahydro-2H-pyran-4-yl)ethylcarbamic acid methyl ester (S)-2-((S)-2-(5-(4-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)phenyl)-1H-imidazol-2-yl)pyrrolidin-1-yl)-2-oxo-1-(tetrahydro-2H-pyran-4-yl)ethylcarbamic acid methyl ester: Title compound was synthesized using methods analogous to the preparation of (2S,3R)-3-methoxy-1-((1R,3 S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 948[M+H]$^+$.

Example KU

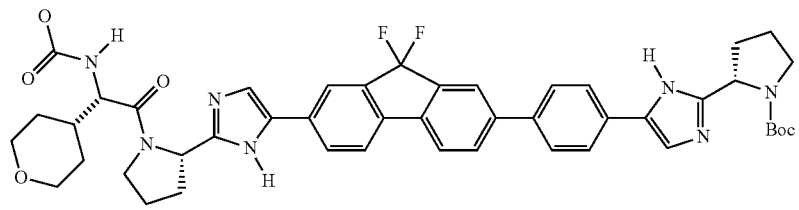

(S)-tert-butyl 2-(5-(4-9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)phenyl)-1H-imidazol-2-yl)pyrrolidine-1-carboxylate 1.) 4NHCl-dioxane
2.) COMU, DIEA, DMF

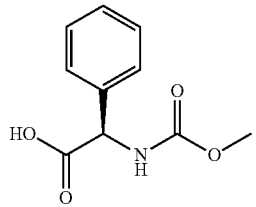

(R)-2-(methoxycarbonylamino)-2-phenylacetic acid

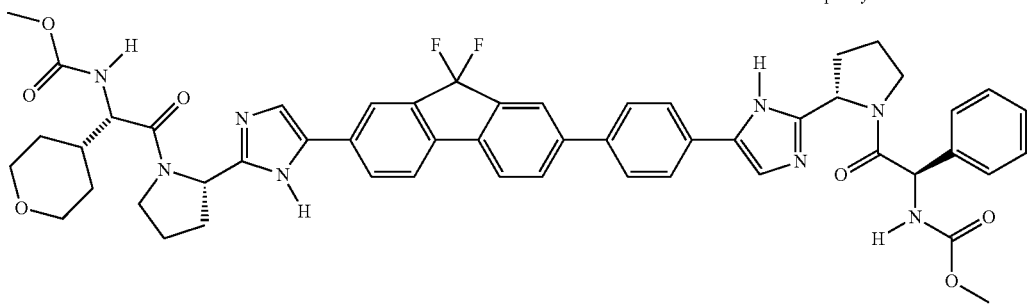

(R)-2-((S)-2-(5-(4-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)phenyl)-1H-imidazol-2-yl)pyrrolidin-1-yl)-2-oxo-1-phenylethylcarbamic acid methyl ester (R)-2-((S)-2-(5-(4-(9,9-difluoro-7-(2-((S)-1-((S)-2-(methoxycarbonylamino)-2-(tetrahydro-2H-pyran-4-yl)acetyl)pyrrolidin-2-yl)-1H-imidazol-5-yl)-9H-fluoren-2-yl)phenyl)-1H-imidazol-2-yl)pyrrolidin-1-yl)-2-oxo-1-phenylethylcarbamic acid methyl ester: Title compound was synthesized using methods analogous to the preparation of (R)-2-((1R,3S,4S)-3-(6-(7-(2-((S)-1-((S)-2-(methoxycarbonylamino)-2-(tetrahydro-2H-pyran-4-yl)acetyl)pyrrolidin-2-yl)-1H-imidazol-5-yl)-9,10-dihydrophenanthren-2-yl)-1H-benzo[d]imidazol-2-yl)-2-azabicyclo[2.2.1]heptan-2-yl)-2-oxo-1-phenylethylcarbamic acid methyl ester, MS (ESI) m/z 940[M+H]⁺.

Example KV

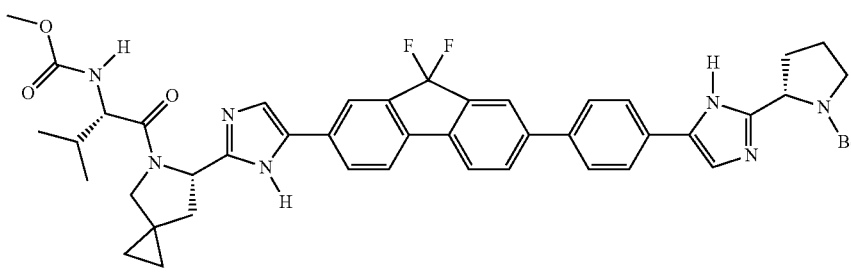

(S)-tert-butyl 2-(5-(4-(9,9-difluoro-7-(2-((S)-5-((S)-2-(methoxycarbonylamino)-3-methylbutanoly)-5-azaspiro[2.4]heptan-6-yl)-1H-imidazol-5-yl)-9H-fluoren-2-yl)phenyl)-1H-iimidazol-2-yl)-pyrrolidine-1-carboxylate 1.) 4NHCl-dioxane
2.) EDCl, HOBT NMM, DMF, 0° C.

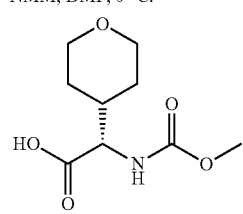

(S)-2-(methoxycarbonylamino)-2-(tetrahydro-2H-pyran-4-yl)acetic acid

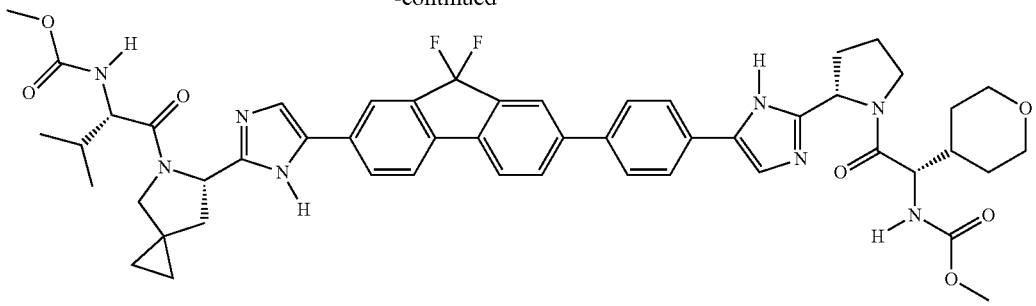

(S)-2-((S)-2-(5-(4-(9,9-difluoro-7-(2-((S)-5-((S)-2-(methoxycarbonylamino)-3-methylbutanoyl)-5-azaspiro[2.4]heptan-6-yl)-1H-imidazol-5-yl)-9H-fluoren-2-yl)phenyl)-1H-imidazol-2-yl)pyrrolidin-1-yl)-2-oxo-1-(tetrahydro-2H-pyran-4-yl)ethylcarbamic acid methyl ester (S)-2-((S)-2-(5-(4-(9,9-difluoro-7-(2-((S)-5-((S)-2-(methoxycarbonylamino)-3-methylbutanoyl)-5-azaspiro[2.4]heptan-6-yl)-1H-imidazol-5-yl)-9H-fluoren-2-yl)phenyl)-1H-imidazol-2-yl)pyrrolidin-1-yl)-2-oxo-1-(tetrahydro-2H-pyran-4-yl)ethylcarbamic acid methyl ester: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 932[M+H]$^+$.

Example KW

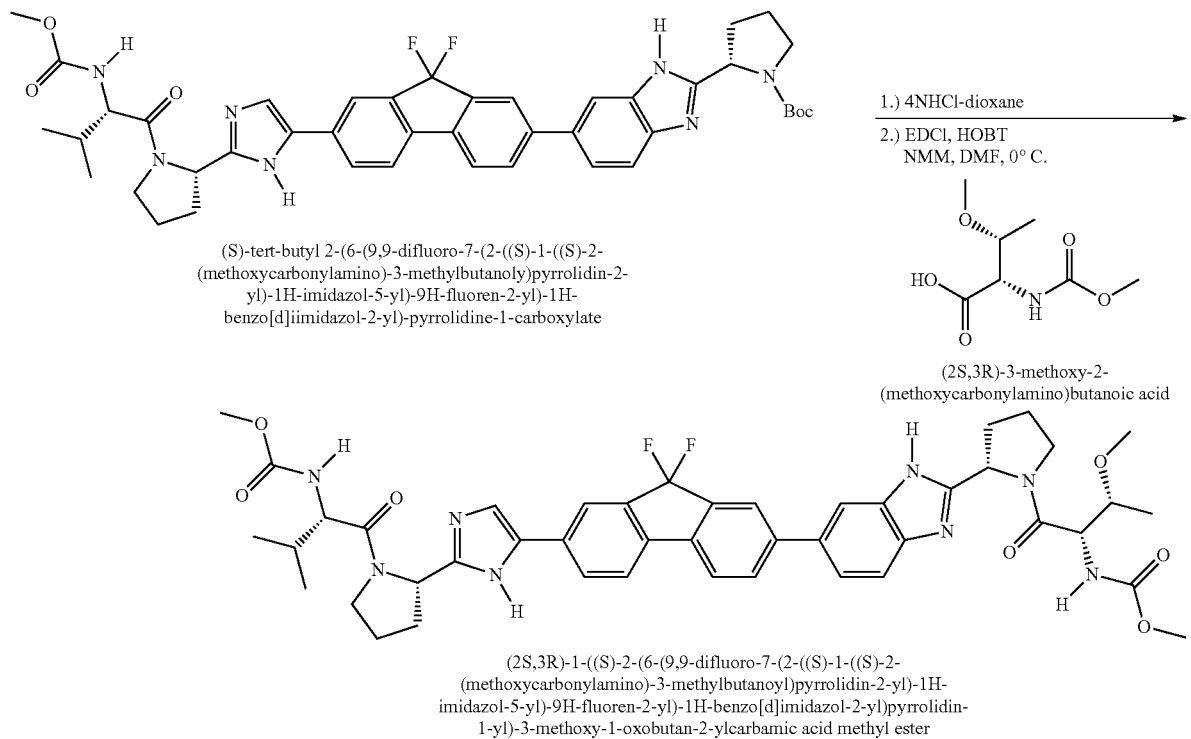

(S)-tert-butyl 2-(6-(9,9-difluoro-7-(2-((S)-1-((S)-2-(methoxycarbonylamino)-3-methylbutanoly)pyrrolidin-2-yl)-1H-imidazol-5-yl)-9H-fluoren-2-yl)-1H-benzo[d]iimidazol-2-yl)-pyrrolidine-1-carboxylate (2S,3R)-3-methoxy-2-(methoxycarbonylamino)butanoic acid (2S,3R)-1-((S)-2-(6-(9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)-1H-benzo[d]imidazol-2-yl)pyrrolidin-1-yl)-3-methoxy-1-oxobutan-2-ylcarbamic acid methyl ester (2S,3R)-1-((S)-2-(6-(9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)-1H-benzo[d]imidazol-2-yl)pyrrolidin-1-yl)-3-methoxy-1-oxobutan-2-ylcarbamic acid methyl ester: Title compound was synthesized using methods analogous to the preparation of (2S,3R)-3-methoxy-1-((1R,3S,4S)-3-(5-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-imidazol-2-yl)-2-azabicyclo[2.2.1]heptan-2-yl)-1-oxobutan-2-ylcarbamic acid methyl ester, MS (ESI) m/z 854[M+H]$^+$.

Example KX

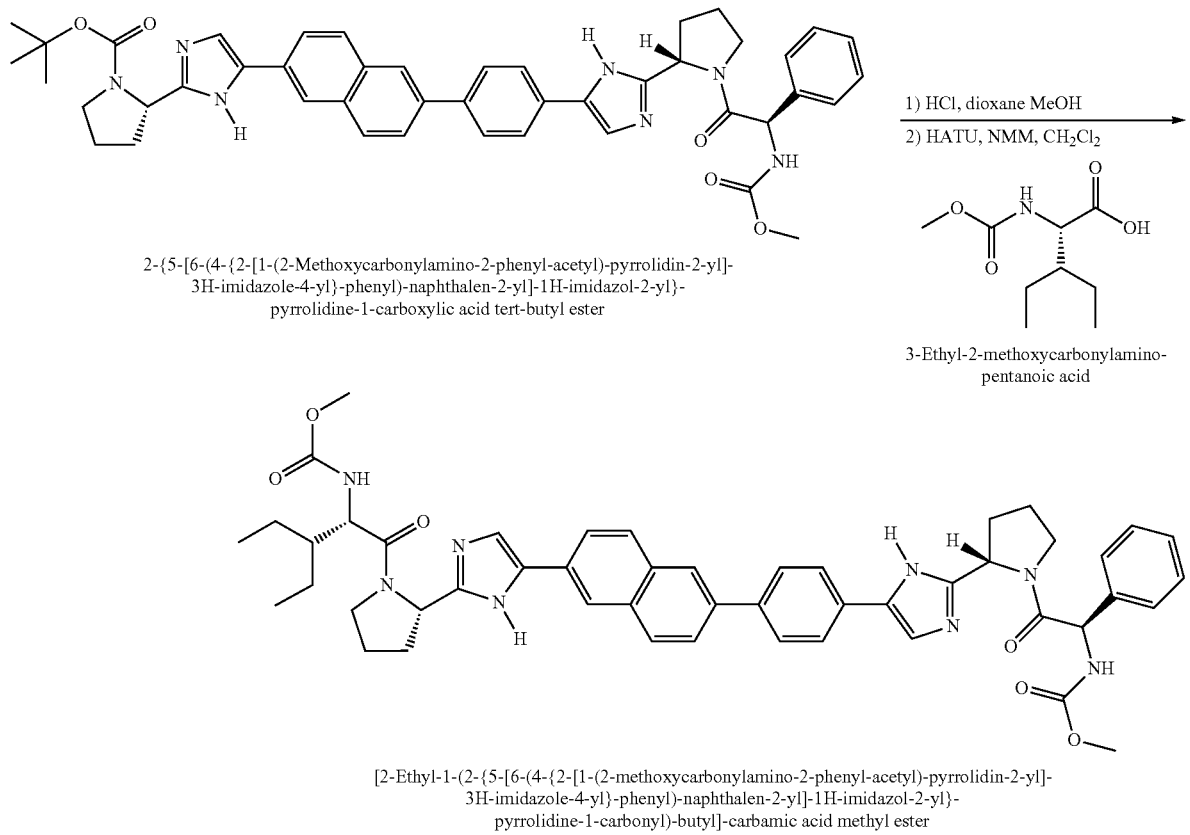

2-{5-[6-(4-{2-[1-(2-Methoxycarbonylamino-2-phenyl-acetyl)-pyrrolidin-2-yl]-3H-imidazole-4-yl}-phenyl)-naphthalen-2-yl]-1H-imidazol-2-yl}-pyrrolidine-1-carboxylic acid tert-butyl ester

[2-Ethyl-1-(2-{5-[6-(4-{2-[1-(2-methoxycarbonylamino-2-phenyl-acetyl)-pyrrolidin-2-yl]-3H-imidazole-4-yl}-phenyl)-naphthalen-2-yl]-1H-imidazol-2-yl}-pyrrolidine-1-carbonyl)-butyl]-carbamic acid methyl ester 2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carboxylic acid tert-butyl ester: This compound was prepared as described in Example ES.

[2-Ethyl-1-(2-{5-[6-(4-{2-[1-(2-methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidine-1-carbonyl)-butyl]-carbamic acid methyl ester: This compound was prepared according to the procedure used to prepare {2-[2-(5-{4-[6-(2-{1-[2-Methoxycarbonylamino-2-(tetrahydro-pyran-4-yl)-acetyl]-pyrrolidin-2-yl}-3H-imidazol-4-yl)-naphthalen-2-yl]-phenyl}-1H-imidazol-2-yl)-pyrrolidin-1-yl]-2-oxo-1-phenyl-ethyl}-carbamic acid methyl ester (Example ES) using 3-Ethyl-2-methoxycarbonylamino-pentanoic acid (0.032g, 0.156 mmol) to give the title compound (0.023, 21% yield) as a white solid. LCMS-ESI$^+$: calc'd for $C_{49}H_{54}N_8O_6$: 850.42 (M$^+$); Found: 851.5 (M+H$^+$).

Example KY

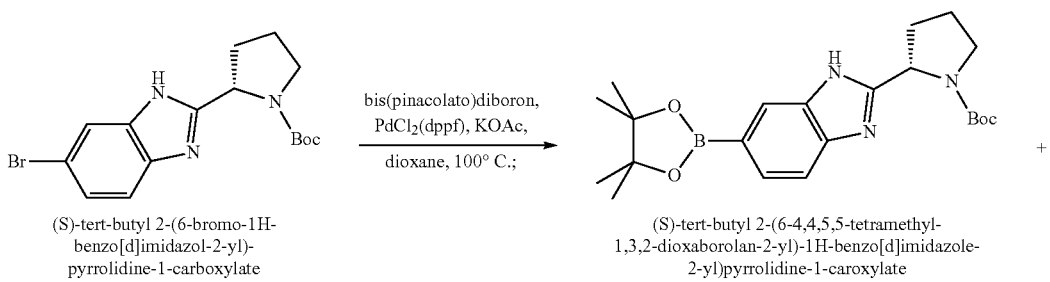

(S)-tert-butyl 2-(6-bromo-1H-benzo[d]imidazol-2-yl)-pyrrolidine-1-carboxylate (S)-tert-butyl 2-(6-4,4,5,5-tetramethyl-1,3,2-dioxaborolan-2-yl)-1H-benzo[d]imidazole-2-yl)pyrrolidine-1-caroxylate

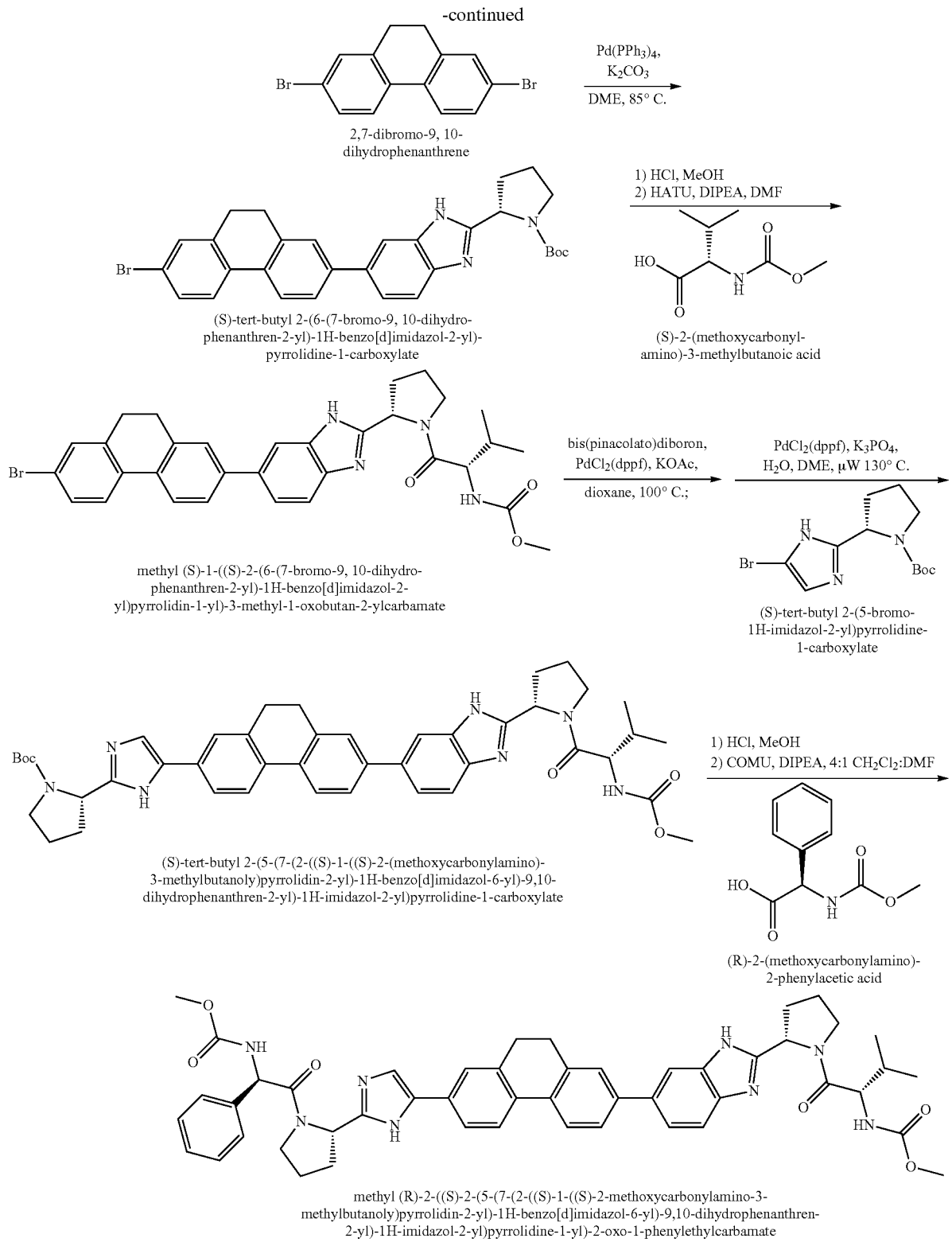

(S)-tert-butyl 2-(6-(4,4,5,5-tetramethyl-1,3,2-dioxaborolan-2-yl)-1H-benzo[d]imidazol-2-yl)pyrrolidine-1-carboxylate: A mixture of (S)-tert-butyl 2-(6-bromo-1H-benzo[d]imidazol-2-yl)-pyrrolidine-1-carboxylate (4.06 g, 11.1 mmol), bis(pinacolato)diboron (4.22 g, 16.6 mmol), PdCl$_2$(dppf) (406 mg, 0.55 mmol) and potassium acetate (3.3 g, 33.2 mmol) in dioxane (33 mL) was degassed with a stream of argon. After twenty minutes, this mixture was heated to 90° C. After 3 hours, the mixture was cooled to room temperature. The reaction was diluted with ethyl acetate, washed with saturated aqueous NaHCO$_3$ solution, dried (Na$_2$SO$_4$) and concentrated. The crude material was purified by flash column chromatography to yield (S)-tert-butyl 2-(6-(4,4,5,5-tetramethyl-1,3,2-dioxaborolan-2-yl)-1H-benzo[d]imidazol-2-yl)pyrrolidine-1-carboxylate (1.49 g, 33%).

(S)-tert-butyl 2-(6-(7-bromo-9,10-dihydro-phenanthren-2-yl)-1H-benzo[d]imidazol-2-yl)-pyrrolidine-1-carboxylate: A mixture of ((S)-tert-butyl 2-(6-(4,4,5,5-tetramethyl-1,3,2-dioxaborolan-2-yl)-1H-benzo[d]imidazol-2-yl)pyrrolidine-1-carboxylate (1.49 g, 3.6 mmol), 2,7-dibromo-9,10-dihydrophenanthrene (6.09 g, 18.0 mmol), 2M aqueous potassium carbonate solution (9 mL, 18.0 mmol), tetrakis(triphenylphosphine)palladium(0) (209 mg, 0.18 mmol) and dimethoxyethane (36 mL) was degassed with a stream of argon for twenty minutes. The reaction was heated to 85° C. After 16 hours, the reaction was cooled to room temperature and diluted with ethyl acetate. The organic phase was washed with saturated aqueous NaHCO$_3$ solution and brine, dried (Na$_2$SO$_4$) and concentrated. The crude material was purified by flash column chromatography to yield (S)-tert-butyl 2-(6-(7-bromo-9,10-dihydro-phenanthren-2-yl)-1H-benzo[d]imidazol-2-yl)-pyrrolidine-1-carboxylate (1.16 g, 59%).

Methyl (S)-1-((S)-2-(6-(7-bromo-9,10-dihydrophenanthren-2-yl)-1H-benzo[d]imidazol-2-yl)pyrrolidin-1-yl)-3-methyl-1-oxobutan-2-ylcarbamate: A solution of (S)-tert-butyl 2-(6-(7-bromo-9,10-dihydro-phenanthren-2-yl)-1H-benzo[d]imidazol-2-yl)-pyrrolidine-1-carboxylate (582 mg, 1.1 mmol), 4M HCl solution in dioxanes (5 mL, 20 mmol) and methanol (3 mL) was stirred at room temperature for twenty minutes. The reaction was concentrated, suspended in dichloromethane, and thoroughly concentrated. This crude amine was dissolved in dimethylformamide (5 mL). To this solution were added (S)-2-(methoxycarbonylamino)-3-methylbutanoic acid (281 mg, 1.6 mmol), HATU (691 mg, 1.8 mmol) and diisopropylethylamine (0.65 mL, 3.7 mmol). The reaction was stirred at room temperature for fifteen minutes, and then diluted ethyl acetate. The organic layer was washed with saturated aqueous NaHCO$_3$ solution and brine, dried (Na$_2$SO$_4$) and concentrated. The crude material was purified by flash column chromatography to yield Methyl (S)-1-((S)-2-(6-(7-bromo-9,10-dihydrophenanthren-2-yl)-1H-benzo[d]imidazol-2-yl)pyrrolidin-1-yl)-3-methyl-1-oxobutan-2-ylcarbamate (376 mg, 58%).

(S)-tert-butyl 2-(5-(7-(2-((S)-1-((S)-2-(methoxycarbonylamino)-3-methylbutanoyl)pyrrolidin-2-yl)-1H-benzo[d]imidazol-6-yl)-9,10-dihydrophenanthren-2-yl)-1H-imidazol-2-yl)pyrrolidine-1-carboxylate: A mixture of methyl S)-1-((S)-2-(6-(7-bromo-9,10-dihydrophenanthren-2-yl)-1H-benzo[d]imidazol-2-yl)pyrrolidin-1-yl)-3-methyl-1-oxobutan-2-ylcarbamate (376 mg, 0.62 mmol), bis(pinacolato)diboron (167 mg, 0.66 mmol), PdCl$_2$(dppf) (23 mg, 0.03 mmol) and potassium acetate (184 mg, 1.9 mmol) in dioxane (3 mL) was degassed with a stream of argon for twenty minutes. The reaction was heated to 100° C. After 1 hour, the mixture was cooled to room temperature. To the reaction was added (S)-tert-butyl 2-(5-bromo-1H-imidazol-2-yl)pyrrolidine-1-carboxylate (296 mg, 0.94 mmol), 2M aqueous potassium phosphate solution (0.94 mL, 1.9 mmol) and dimethoxyethane (4 mL). The reaction was degassed with a stream of argon for twenty minutes. The reaction was heated in a microwave to 130° C. for twenty minutes. After cooling, more PdCl$_2$(dppf) (23 mg, 0.03 mmol), 2M aqueous potassium phosphate solution (0.47 mL, 0.94 mmol), and (S)-tert-butyl 2-(5-bromo-1H-imidazol-2-yl)pyrrolidine-1-carboxylate (98 mg, 0.31 mmol) were added and the reaction was heated in a microwave to 120° C. for 140 minutes. The reaction was removed from the microwave and heated at 110° C. overnight. After 14 hours, the reaction was diluted with ethyl acetate, and the organic phase was washed with saturated aqueous NaHCO$_3$ solution and brine, dried (Na$_2$SO$_4$) and concentrated. The crude material was purified by flash column chromatography to yield (S)-tert-butyl 2-(5-(7-(2-((S)-1-((S)-2-(methoxycarbonylamino)-3-methylbutanoyl)pyrrolidin-2-yl)-1H-benzo[d]imidazol-6-yl)-9,10-dihydrophenanthren-2-yl)-1H-imidazol-2-yl)pyrrolidine-1-carboxylate (174 mg, 37%).

Methyl (R)-2-((S)-2-(5-(7-(2-((S)-1-((S)-2-methoxycarbonylamino-3-methylbutanoyl)pyrrolidin-2-yl)-1H-benzo[d]imidazol-6-yl)-9,10-dihydrophenanthren-2-yl)-1H-imidazol-2-yl)pyrrolidin-1-yl)-2-oxo-1-phenylethylcarbamate: A solution of (S)-tert-butyl 2-(5-(7-(2-((S)-1-((S)-2-(methoxycarbonylamino)-3-methylbutanoyl)pyrrolidin-2-yl)-1H-benzo[d]imidazol-6-yl)-9,10-dihydrophenanthren-2-yl)-1H-imidazol-2-yl)pyrrolidine-1-carboxylate (174 mg, 0.23 mol), methanol (0.5 mL), and 4M HCl in dioxane (2 mL, 8 mmol) was stirred at room temperature. The reaction was thoroughly concentrated after ten minutes. The resulting residue was dissolved in a 4:1 dichloromethane:dimethylformamide solution (2.3 mL). One half of this solution was removed and used in the subsequent reaction. To this solution (~1.15 mL) was added (R)-2-(methoxycarbonylamino)-2-phenylacetic acid (24 mg, 0.13 mmol) and COMU (49 mg, 0.11 mmol) and the reaction was cooled to 0° C. Diisopropylethylamine (0.080 mL, 0.46 mmol) was added and the reaction was stirred at 0° C. for twenty minutes. The reaction was quenched by the addition of formic acid (0.05 mL) and thoroughly concentrated. The resulting residue was purified by preparative reverse phase HPLC (Gemini, 10 to 60% ACN/H$_2$O+0.1% HCO$_2$H), followed by a second preparative reverse phase HPLC (Gemini, 10 to 60% ACN/H$_2$O+ 0.1% TFA) to yield methyl (R)-2-((S)-2-(5-(7-(2-((S)-1-((S)-2-methoxycarbonylamino-3-methylbutanoyl)pyrrolidin-2-yl)-1H-benzo[d]imidazol-6-yl)-9,10-dihydrophenanthren-2-yl)-1H-imidazol-2-yl)pyrrolidin-1-yl)-2-oxo-1-phenylethylcarbamate (51 mg, ~52%). LCMS-ESI$^+$: calculated for C$_{49}$H$_{52}$N$_8$O$_6$: 848.50; observed [M+1]$^+$: 849.59.

Example KZ

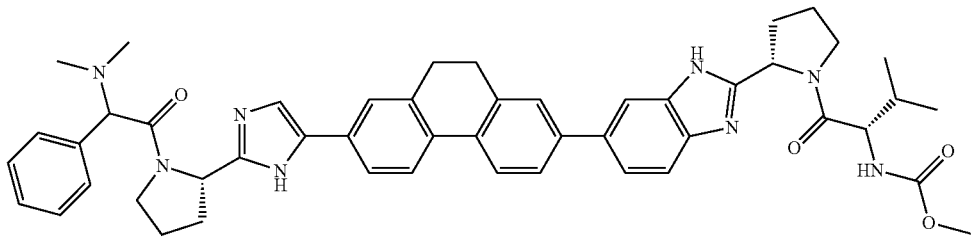 [SMILES: COC(=O)N[C@H](C(=O)N1CCC[C@H]1c1nc2ccc(-c3ccc4c(c3)CCc3cc(-c5cnc([C@@H]6CCCN6C(=O)C(c6ccccc6)N(C)C)[nH]5)ccc3-4)cc2[nH]1)C(C)C]

1125 methyl (2S)-1-((2S)-2-(6-(7-(2-((2S)-1-(2-(dimethyl-amino)-2-phenylacetyl)pyrrolidin-2-yl)-1H-imidazol-5-yl)-9,10-dihydrophenanthren-2-yl)-1H-benzo[d]imidazol-2-yl)pyrrolidin-1-yl)-3-methyl-1-oxobutan-2-ylcarbamate Methyl (2S)-1-((2S)-2-(6-(7-(2-((2S)-1-(2-(dimethylamino)-2-phenylacetyl)pyrrolidin-2-yl)-1H-imidazol-5-yl)-9,10-dihydrophenanthren-2-yl)-1H-benzo[d]imidazol-2-yl)pyrrolidin-1-yl)-3-methyl-1-oxobutan-2-ylcarbamate: This compound was made in an analogous manner to methyl (R)-2-((S)-2-(5-(7-(2-((S)-1-((S)-2-methoxycarbonylamino-3-methylbutanoyl)pyrrolidin-2-yl)-1H-benzo[d]imidazol-6-yl)-9,10-dihydrophenanthren-2-yl)-1H-imidazol-2-yl)pyrrolidin-1-yl)-2-oxo-1-phenylethylcarbamate, substituting (R)-2-(dimethylamino)-2-phenylacetic acid for (R)-2-(methoxycarbonylamino)-2-phenylacetic acid in the second amide coupling. LCMS-ESI$^+$: calculated for $C_{49}H_{54}N_8O_4$: 819.00; observed [M+1]$^+$: 819.80.

Example LA

1126

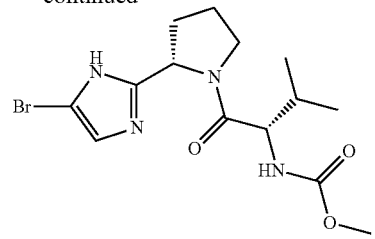

methyl (S)-1-((S)-2-(5-bromo-1H-imidazol-2-yl)pyrrolidin-1-yl)-3-methyl-1-oxobutan-2-ylcarbamate Methyl (S)-1-((S)-2-(5-bromo-1H-imidazol-2-yl)pyrrolidin-1-yl)-3-methyl-1-oxobutan-2-ylcarbamate: A solution of (S)-tert-butyl 2-(5-bromo-1H-imidazol-2-yl)pyrrolidine-1-carboxylate (1.0 g, 3.2 mmol), 4M HCl solution in dioxanes (3.95 mL, 15.8 mmol) and methanol (4 mL) was stirred at room temperature for thirty minutes. The reaction was concentrated, suspended in dichloromethane, and thoroughly concentrated. This crude amine was dissolved in dimethylformamide (6.4 mL). To this solution were added (S)-2-(methoxycarbonylamino)-3-methylbutanoic acid (582 mg, 3.3 mmol), HATU (1.3 g, 3.3 mmol) and diisopropylethylamine (1.9 mL, 11.1 mmol). The reaction was stirred at room temperature for twenty minutes, and then diluted with ethyl acetate. The organic layer was washed with water and brine, dried (Na$_2$SO$_4$) and concentrated. The crude material was purified by flash column chromatography to yield methyl (S)-1-((S)-2-(5-bromo-1H-imidazol-2-yl)pyrrolidin-1-yl)-3-methyl-1-oxobutan-2-ylcarbamate (985 mg, 83%).

Example LB

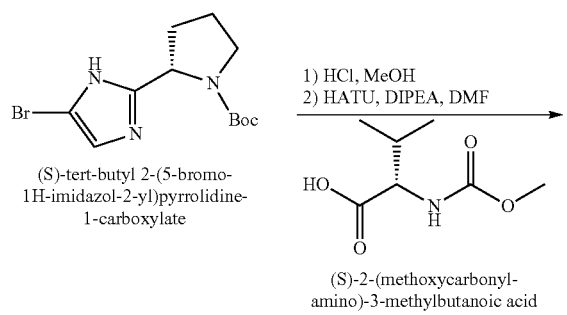

(S)-tert-butyl 2-(5-bromo-1H-imidazol-2-yl)pyrrolidine-1-carboxylate

1) HCl, MeOH
2) HATU, DIPEA, DMF (S)-2-(methoxycarbonyl-amino)-3-methylbutanoic acid

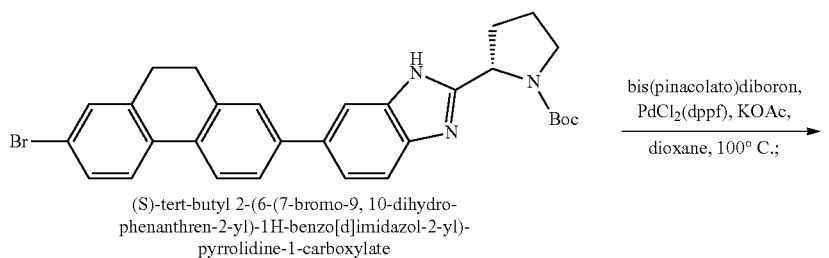

(S)-tert-butyl 2-(6-(7-bromo-9,10-dihydrophenanthren-2-yl)-1H-benzo[d]imidazol-2-yl)-pyrrolidine-1-carboxylate bis(pinacolato)diboron, PdCl$_2$(dppf), KOAc,
dioxane, 100° C.;

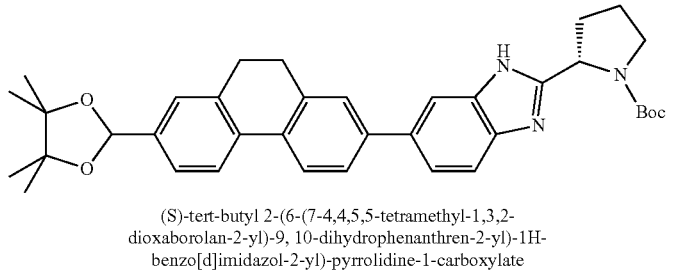

(S)-tert-butyl 2-(6-(7-4,4,5,5-tetramethyl-1,3,2-dioxaborolan-2-yl)-9,10-dihydrophenanthren-2-yl)-1H-benzo[d]imidazol-2-yl)-pyrrolidine-1-carboxylate

+

-continued

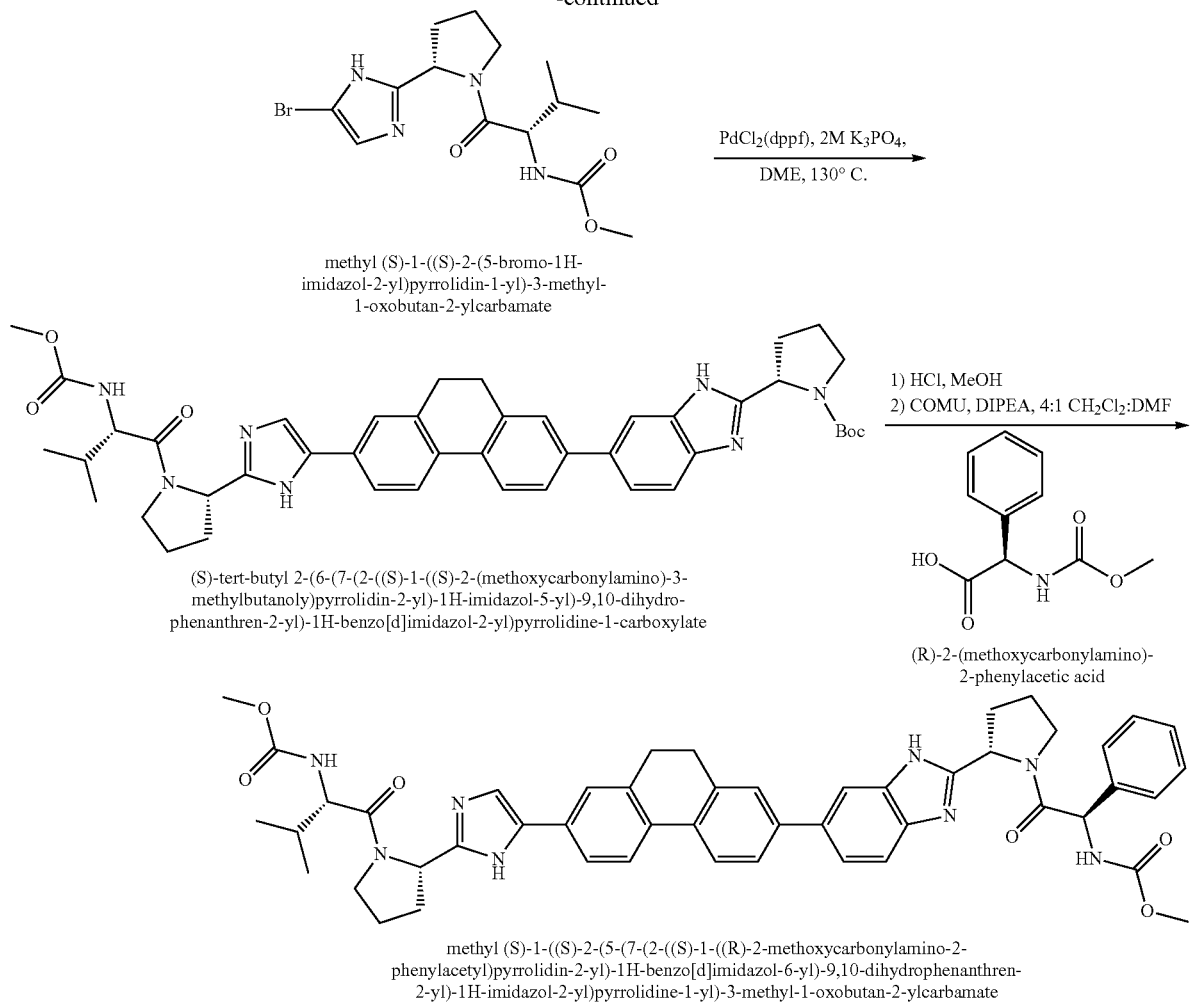

(S)-tert-butyl 2-(6-(7-(4,4,5,5-tetramethyl-1,3,2-dioxaborolan-2-yl)-9,10-dihydrophenanthren-2-yl)-1H-benzo[d]imidazol-2-yl)pyrrolidine-1-carboxylate: A mixture of (S)-tert-butyl 2-(6-(7-bromo-9,10-dihydrophenanthren-2-yl)-1H-benzo[d]imidazol-2-yl)-pyrrolidine-1-carboxylate (582 mg, 1.1 mmol), bis(pinacolato)diboron (407 mg, 1.6 mmol), PdCl$_2$(dppf) (39 mg, 0.05 mmol) and potassium acetate (315 mg, 3.2 mmol) in dioxane (5 mL) was degassed with a stream of argon for twenty minutes. The reaction was heated to 100° C. After forty minutes, the mixture was cooled to room temperature and diluted with ethyl acetate. The organic phase was washed with water and brine, dried (Na$_2$SO$_4$) and concentrated. The resulting residue was purified by flash column chromatography to yield (S)-tert-butyl 2-(6-(7-(4,4,5,5-tetramethyl-1,3,2-dioxaborolan-2-yl)-9,10-dihydrophenanthren-2-yl)-1H-benzo[d]imidazol-2-yl)pyrrolidine-1-carboxylate (590 mg, 93%).

(S)-tert-butyl 2-(6-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-benzo[d]imidazol-2-yl)pyrrolidine-1-carboxylate: A mixture of (S)-tert-butyl 2-(6-(7-(4,4,5,5-tetramethyl-1,3,2-dioxaborolan-2-yl)-9,10-dihydrophenanthren-2-yl)-1H-benzo[d]imidazol-2-yl)pyrrolidine-1-carboxylate (590 mg, 1.0 mmol), methyl (S)-1-((S)-2-(5-bromo-1H-imidazol-2-yl)pyrrolidin-1-yl)-3-methyl-1-oxobutan-2-ylcarbamate (492 mg, 1.3 mmol), PdCl$_2$(dppf) (37 mg, 0.05 mmol), 2M aqueous potassium phosphate solution (1.5 mL, 3.0 mmol), and dimethoxyethane (5 mL) was degassed with a stream of argon for twenty minutes. The reaction was heated to 90° C. After one hour, the reaction was cooled to room temperature and tetrakis(triphenylphosphine)palladium(0) (58 mg, 0.05 mmol) was added. The reaction was heated to 90° C. After three hours, the reaction was cooled to room temperature and more PdCl$_2$(dppf) (37 mg, 0.05 mmol) was added. The reaction was heated to 80° C. After 16 hours, the reaction was cooled to room temperature and diluted with ethyl acetate. The organic phase was washed with water and brine, dried (Na$_2$SO$_4$) and concentrated. The resulting residue was purified by flash column chromatography to yield (S)-tert-butyl 2-(6-(7-(2-((S)-1-((S)-2-(methoxycarbonylamino)-3-methylbutanoyl)pyrrolidin-2-yl)-1H-imidazol-5-yl)-9,10-dihydrophenanthren-2-yl)-1H-benzo[d]imidazol-2-yl) pyrrolidine-1-carboxylate (30 mg, 4%).

Methyl (S)-1-((S)-2-(5-(7-(2-((S)-1-((R)-2-methoxycarbonylamino-2-phenylacetyl)pyrrolidin-2-yl)-1H-benzo[d]imidazol-6-yl)-9,10-dihydrophenanthren-2-yl)-1H-imidazol-2-yl)pyrrolidin-1-yl)-3-methyl-1-oxobutan-2-ylcarbamate: A solution of (S)-tert-butyl 2-(6-(7-(2-((S)-1-((S)-2-(methoxycarbonylamino)-3-methylbutanoyl)

pyrrolidin-2-yl)-1H-imidazol-5-yl)-9,10-dihydrophenanthren-2-yl)-1H-benzo[d]imidazol-2-yl) pyrrolidine-1-carboxylate (30 mg, 0.04 mol), methanol (0.5 mL), and 4M HCl in dioxane (1 mL, 4 mmol) was stirred at room temperature. The reaction was thoroughly concentrated after twenty minutes. The resulting residue was dissolved in a 4:1 dichloromethane:dimethylformamide solution (1.0 mL). One half of this solution was removed and used in the subsequent reaction. To this solution (~0.5 mL) was added (R)-2-(methoxycarbonylamino)-2-phenylacetic acid (4.2 mg, 0.02 mmol) and COMU (8.5 mg, 0.02 mmol) and the reaction was cooled to 0° C. Diisopropylethylamine (0.011 mL, 0.06 mmol) was added and the reaction was stirred at 0° C. for twenty minutes. The reaction was quenched by the addition of formic acid (0.05 mL) and thoroughly concentrated. The resulting residue was purified by preparative reverse phase HPLC (Gemini, 10 to 60% ACN/H$_2$O+0.1% HCO$_2$H), followed by a second preparative reverse phase HPLC (Gemini, 10 to 60% ACN/H$_2$O+ 0.1% TFA) to yield methyl (S)-1-((S)-2-(5-(7-(2-((S)-1-((R)-2-methoxycarbonylamino-2-phenylacetyl)pyrrolidin-2-yl)-1H-benzo[d]imidazol-6-yl)-9,10-dihydrophenanthren-2-yl)-1H-imidazol-2-yl)pyrrolidin-1-yl)-3-methyl-1-oxobutan-2-ylcarbamate (6 mg, 36%). LCMS-ESI$^+$: calculated for C$_{49}$H$_{52}$N$_8$O$_6$: 848.99; observed [M+1]$^+$: 850.2.

Example LC

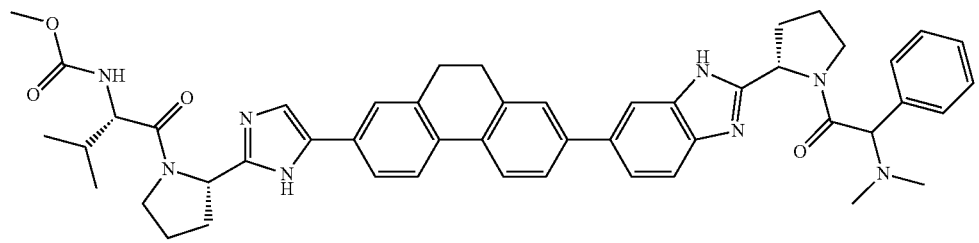 [SMILES: COC(=O)N[C@H](C(=O)N1CCC[C@H]1c1ncc(-c2ccc3c(c2)CCc2cc(-c4ccc5nc([C@@H]6CCCN6C(=O)C(c6ccccc6)N(C)C)[nH]c5c4)ccc2-3)[nH]1)C(C)C]

Methyl (2S)-1-((2S)-2-(5-(7-(2-((2S)-1-(2-(dimethylamino)-2-phenylacetyl)-pyrrolidin-2-yl)-1H-benzo[d]imidazol-6-yl)-9,10-dihydrophenanthren-2-yl)-1H-imidazol-2-yl)pyrrolidin-1-yl)-3-methyl-1-oxobutan-2-ylcarbamate: This compound was made in an analogous manner to methyl (S)-1-((S)-2-(5-(7-(2-((S)-1-((R)-2-methoxycarbonylamino-2-phenylacetyl)pyrrolidin-2-yl)-1H-benzo[d]imidazol-6-yl)-9,10-dihydrophenanthren-2-yl)-1H-imidazol-2-yl)pyrrolidin-1-yl)-3-methyl-1-oxobutan-2-ylcarbamate, substituting (R)-2-(dimethylamino)-2-phenylacetic acid for (R)-2-(methoxycarbonylamino)-2-phenylacetic acid in the final amide coupling step. LCMS-ESI$^+$: calculated for C$_{49}$H$_{54}$N$_8$O$_4$: 819.00; observed [M+1]$^+$: 820.3.

Example LD

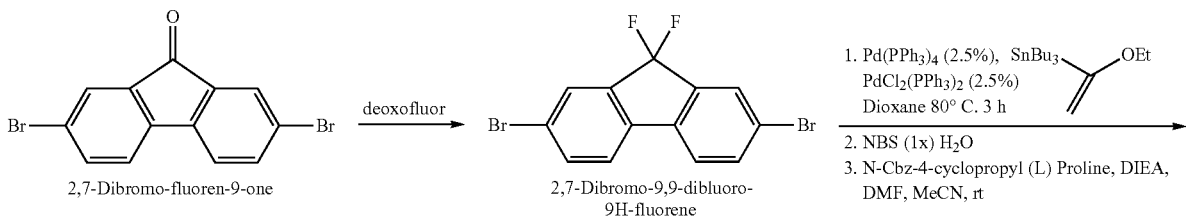

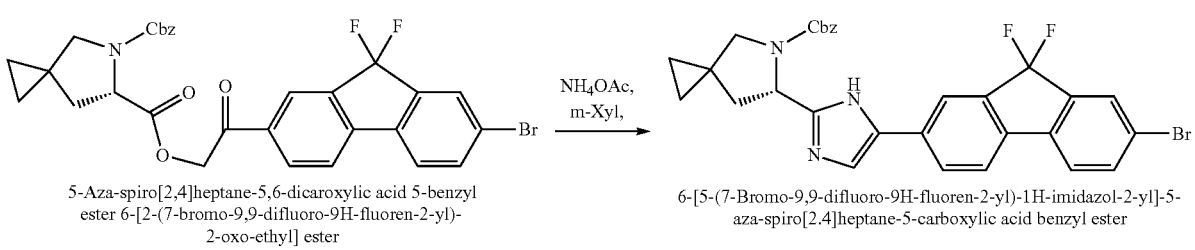

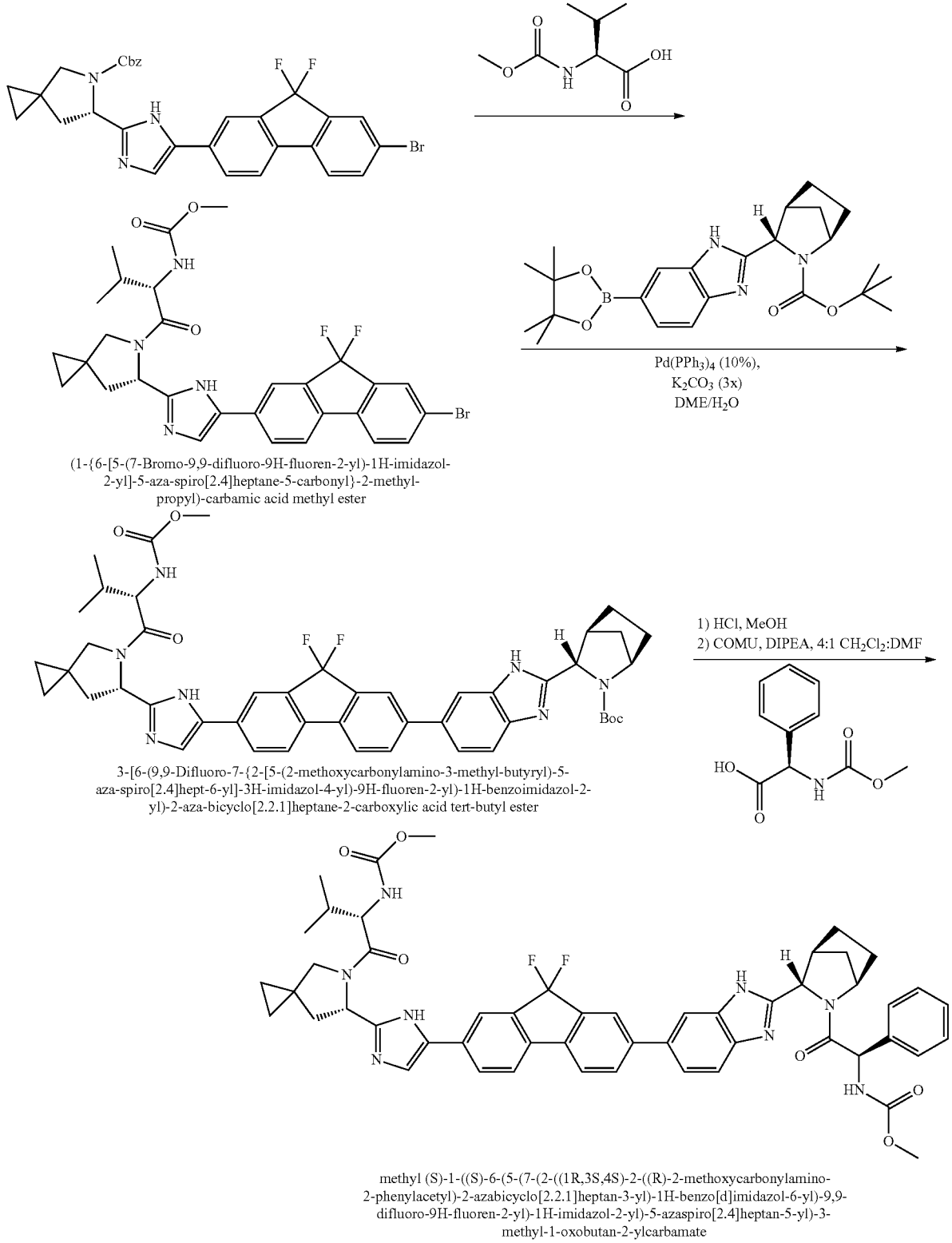
2,7-Dibromo-9,9-difluoro-9H-fluorene:
2,7-Dibromo-fluoren-9-one (4.0 g, 11.8 mmol) was suspended in deoxofluor (12 mL) at room temperature and EtOH (4 drops) was added. The stirred suspension was heated at T=90° C. for 24 hours (CAUTION: Use of deoxofluor at elevated temperatures, as described above, is strongly discouraged as rapid and violent exotherms may occur). The reaction was cooled to room temperature and poured onto ice containing sodium bicarbonate. A solid formed and was collected via filtration. The crude material was taken into EtOAc and was washed with aqueous HCl (1M) and brine. The solution was dried over sodium sulfate. Filtration and evaporation of solvents gave crude product, which was purified by silica gel chromatography (eluent: EtOAc/hexanes) to yield the product 2,7-Dibromo-9,9-difluoro-9H-fluorene (3.2 g). $^{19}$F-NMR: 282 MHz, (dmso-d$_6$) δ: −111.6 ppm.

Before using the material in the next step, it was exposed as a solution in EtOAc to charcoal.

5-Aza-spiro[2.4]heptane-5,6-dicarboxylic acid 5-benzyl ester 6-[2-(7-bromo-9,9-difluoro-9H-fluoren-2-yl)-2-oxo-ethyl]ester:

2,7-Dibromo-9,9-difluoro-9H-fluorene (372 mg, 1.04 mmol), Pd(PPh$_3$)$_4$ (30.0 mg, 0.026 mmol), PdCl$_2$(PPh$_3$)$_2$ (18.2 mg, 0.026 mmol), As(PPh$_3$)$_3$ (5.0 mg) were dissolved in dioxane (10 mL) under an argon atmosphere. Ethoxyvinyl-tributyl tin (376.4 mg, 1.04 mmol) was added. The mixture was heated for 140 minutes at 85° C. (oil bath). The reaction was cooled to room temperature. N-bromo succinimide (177 mg, 1.0 mmol) was added followed by water (2 mL). The reaction was stirred at room temperature for 3 hours, after which the majority of the dioxane was removed in vacuo. The crude reaction mixture was diluted with EtOAc and was washed with water. All volatiles were removed in vacuo. Toluene was added and all volatiles were removed in vacuo for a second time. The crude material was dissolved in DMF/MeCN (2 mL, 1:1) at room temperature. A solution of N-Cbz-4-cyclopropyl (L) Proline (0.84 mmol) and DIEA (268 mg, 2.08 mmol) in MeCN (2 mL) was added and stirring at room temperature was continued. After 14 hours, most of the MeCN was removed in vacuo and the crude reaction mixture was diluted with EtOAc. The mixture was washed with aqueous HCl (1M), aqueous LiCl solution (5%), brine, and was dried over sodium sulfate. Filtration and evaporation of solvents gave the crude reaction product, which was purified via silica gel chromatography (eluent: EtOAc/hexanes) to yield the product 5-Aza-spiro[2.4]heptane-5,6-dicarboxylic acid 5-benzyl ester 6-[2-(7-bromo-9,9-difluoro-9H-fluoren-2-yl)-2-oxo-ethyl]ester (176 mg). LCMS-ESI$^+$: calc'd for C$_{30}$H$_{24}$BrF$_2$NO$_5$: 596.4 (M$^+$); Found: 595.2/597.2 (M+H$^+$).

6-[5-(7-Bromo-9,9-difluoro-9H-fluoren-2-yl)-1H-imidazol-2-yl]-5-aza-spiro[2.4]heptane-5-carboxylic acid benzyl ester:

5-Aza-spiro[2.4]heptane-5,6-dicarboxylic acid 5-benzyl ester 6-[2-(7-bromo-9,9-difluoro-9H-fluoren-2-yl)-2-oxo-ethyl]ester (172 mg, 0.293 mmol) was dissolved in m-xylenes (6.0 mL). Ammonium acetate (226 mg, 2.93 mmol) was added and the reaction was stirred at 140° C. for 60 minutes under microwave conditions. The reaction was cooled to room temperature and all volatiles were removed in vacuo. The crude material was purified via silica gel chromatography (eluent: EtOAc/hexanes) to yield the product 6-[5-(7-Bromo-9,9-difluoro-9H-fluoren-2-yl)-1H-imidazol-2-yl]-5-aza-spiro[2.4]heptane-5-carboxylic acid benzyl ester (80.3 mg). LCMS-ESI$^+$: calc'd for C$_{30}$H$_{24}$BrF$_2$N$_3$O$_2$: 576.4 (M$^+$); Found: 575.2/577.2 (M+H$^+$).

(1-{6-[5-(7-Bromo-9,9-difluoro-9H-fluoren-2-yl)-1H-imidazol-2-yl]-5-aza-spiro[2.4]heptane-5-carbonyl}-2-methyl-propyl)-carbamic acid methyl ester:

6-[5-(7-Bromo-9,9-difluoro-9H-fluoren-2-yl)-1H-imidazol-2-yl]-5-aza-spiro[2.4]heptane-5-carboxylic acid benzyl ester (800 mg, 1.38 mmol) was dissolved in DCM (15 mL) and HBr in AcOH (37%, 2 mL) was added and stirring at room temperature was continued. After 180 minutes, the suspension was diluted with hexanes and the solid was collected via filtration and was washed with hexanes and subjected to vacuum. The crude material was used in the next step without further purification. The crude material was dissolved in DMF (4.0 mL) and DIEA (356 mg, 2.76 mmol) was added. A solution of 2-(L)-Methoxycarbonylamino-3-methyl-butyric acid (242 mg, 1.38 mmol), HATU (524 mg, 1.38 mmol) and DIEA (178 mg, 1.38 mmol) in DMF (1 mL) was added. The reaction was stirred at room temperature. After 50 minutes, the reaction was diluted with EtOAc and was washed with aqueous bicarbonate solution, aqueous LiCl solution (5%), brine, and was dried over sodium sulfate. Filtration and removal of solvents in vacuo gave the crude material, which was purified by silica gel chromatography (eluent: EtOAc/hexanes) to yield the slightly impure product (1-{6-[5-(7-Bromo-9,9-difluoro-9H-fluoren-2-yl)-1H-imidazol-2-yl]-5-aza-spiro[2.4]heptane-5-carbonyl}-2-methyl-propyl)-carbamic acid methyl ester (878 mg). LCMS-ESI$^+$: calc'd for C$_{29}$H$_{29}$BrF$_2$N$_4$O$_3$: 599.5 (M$^+$); Found: 598.5/600.5 (M+H$^+$).

3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester:

(1-{6-[5-(7-Bromo-9,9-difluoro-9H-fluoren-2-yl)-1H-imidazol-2-yl]-5-aza-spiro[2.4]heptane-5-carbonyl}-2-methyl-propyl)-carbamic acid methyl ester (840 mg, 1.4 mmol), 3-[6-(4,4,5,5-Tetramethyl-[1,3,2]dioxaborolan-2-yl)-1H-benzoimidazol-2-yl]-2-aza-bicyclo[2.2.1]heptane-2-carboxylic acid tert-butyl ester (615 mg, 1.4 mmol), Pd(PPh$_3$)$_4$ (161 mg, 0.14 mmol), K$_2$CO$_3$ (579 mg, 4.2 mmol), were dissolved in DME (15 mL)/water (3 mL) under an argon atmosphere. The mixture was heated for 120 minutes at 85-90° C. (oil bath). After 120 minutes additional boronate ester (61 mg, 0.14 mmol) was added and heating was continued. After 3 hours, the reaction was cooled to room temperature. Most of the DME was removed in vacuo and the crude reaction mixture was diluted with EtOAc. The mixture was washed with brine and was dried over sodium sulfate. Filtration and evaporation of solvents gave the crude reaction product, which was purified via silica gel chromatography (eluent: EtOAc/hexanes) to yield the product 3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1] heptane-2-carboxylic acid tert-butyl ester (878 mg). LCMS-ESI$^+$: calc'd for C$_{47}$H$_{51}$F$_2$N$_7$O$_5$: 831.9 (M$^+$); Found: 832.7 (M+H$^+$).

Methyl (S)-1-((S)-6-(5-(7-(2-((1R,3S,4S)-2-((R)-2-methoxycarbonylamino-2-phenylacetyl)-2-azabicyclo [2.2.1]heptan-3-yl)-1H-benzo[d]imidazol-6-yl)-9,9-difluoro-9H-fluoren-2-yl)-1H-imidazol-2-yl)-5-azaspiro[2.4]heptan-5-yl)-3-methyl-1-oxobutan-2-ylcarbamate: A solution of 3-[6-(9,9-Difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carboxylic acid tert-butyl ester (28 mg, 0.03 mmol), methanol (0.5 mL), and 4M HCl in dioxane (0.5 mL, 2 mmol) was stirred at room temperature. The reaction was thoroughly concentrated after twenty minutes. The resulting residue was dissolved in a 4:1 dichloromethane:dimethylformamide solution (0.5 mL). To this solution was added (R)-2-(methoxycarbonylamino)-2-phenylacetic acid (7.9 mg, 0.04 mmol) and COMU (16 mg, 0.04 mmol) and the reaction was cooled to 0° C. Diisopropylethylamine (0.024 mL, 0.14 mmol) was added and the reaction was stirred at 0° C. The reaction was quenched by the addition of formic acid (0.05 mL) and thoroughly concentrated. The resulting residue was purified by preparative reverse phase HPLC (Gemini, 10 to 60% ACN/H₂O+0.1% TFA) to yield methyl (S)-1-((S)-6-(5-(7-(2-((1R,3S,4S)-2-((R)-2-methoxycarbonylamino-2-phenylacetyl)-2-azabicyclo[2.2.1]heptan-3-yl)-1H-benzo[d]imidazol-6-yl)-9,9-difluoro-9H-fluoren-2-yl)-1H-imidazol-2-yl)-5-azaspiro[2.4]heptan-5-yl)-3-methyl-1-oxobutan-2-ylcarbamate (10 mg, 36%). LCMS-ESI⁺: calc'd for C₅₂H₅₂F₂N₈O₆: 923.02 (M⁺); Found: 924.5 (M+H⁺).

Example LE

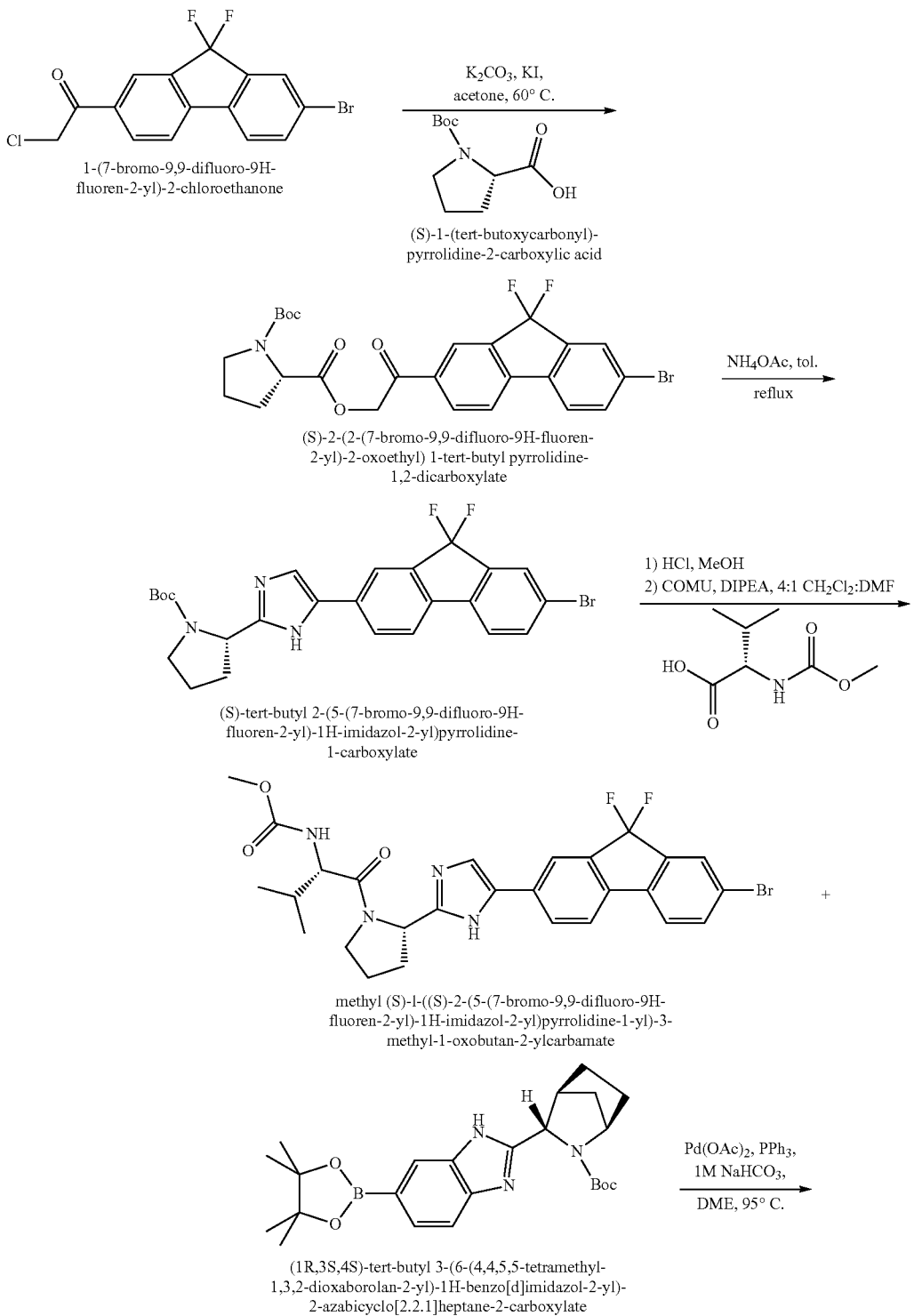

-continued

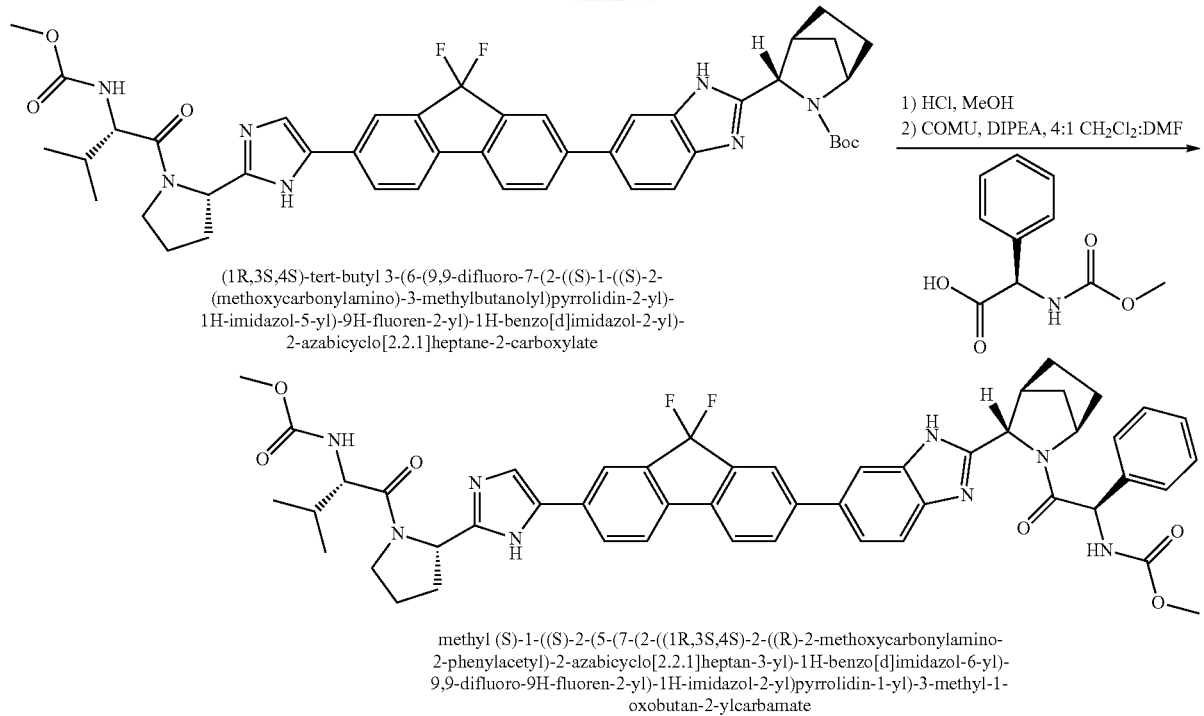

(1R,3S,4S)-tert-butyl 3-(6-(9,9-difluoro-7-(2-((S)-1-((S)-2-(methoxycarbonylamino)-3-methylbutanolyl)pyrrolidin-2-yl)-1H-imidazol-5-yl)-9H-fluoren-2-yl)-1H-benzo[d]imidazol-2-yl)-2-azabicyclo[2.2.1]heptane-2-carboxylate methyl (S)-1-((S)-2-(5-(7-(2-((1R,3S,4S)-2-((R)-2-methoxycarbonylamino-2-phenylacetyl)-2-azabicyclo[2.2.1]heptan-3-yl)-1H-benzo[d]imidazol-6-yl)-9,9-difluoro-9H-fluoren-2-yl)-1H-imidazol-2-yl)pyrrolidin-1-yl)-3-methyl-1-oxobutan-2-ylcarbamate (S)-2-(2-(7-bromo-9,9-difluoro-9H-fluoren-2-yl)-2-oxoethyl) 1-tert-butyl pyrrolidine-1,2-dicarboxylate: A mixture of 1-(7-bromo-9,9-difluoro-9H-fluoren-2-yl)-2-chloroethanone (2 g, 5.6 mmol), (S)-1-(tert-butoxycarbonyl)pyrrolidine-2-carboxylic acid (1.32 g, 6.1 mmol), potassium carbonate (1.55 g, 11.1 mmol) and potassium iodide (930 mg, 5.6 mmol) in acetone was heated to 60° C. After forty minutes, the reaction was cooled to room temperature and concentrated. The residue was dissolved in a mixture of ethyl acetate and water. The aqueous phase was extracted twice with ethyl acetate. The combined organic layers were washed with saturated aqueous NH₄Cl solution and brine, dried (Na₂SO₄) and concentrated. The crude material was purified by flash column chromatography to yield (S)-2-(2-(7-bromo-9,9-difluoro-9H-fluoren-2-yl)-2-oxoethyl) 1-tert-butyl pyrrolidine-1,2-dicarboxylate (2.65 g, 88%).

(S)-tert-butyl 2-(5-(7-bromo-9,9-difluoro-9H-fluoren-2-yl)-1H-imidazol-2-yl)pyrrolidine-1-carboxylate: A mixture of (S)-2-(2-(7-bromo-9,9-difluoro-9H-fluoren-2-yl)-2-oxoethyl) 1-tert-butyl pyrrolidine-1,2-dicarboxylate (2.65 g, 4.9 mmol), ammonium acetate (3.8g, 49 mmol) and toluene was vigorously refluxed. After 4.5 hours, the reaction was cooled to room temperature and diluted with ethyl acetate. The organic layer was washed with saturated aqueous NaHCO₃ solution and brine, dried (Na₂SO₄) and concentrated. The resulting crude residue was purified by flash column chromatography to yield (S)-tert-butyl 2-(5-(7-bromo-9,9-difluoro-9H-fluoren-2-yl)-1H-imidazol-2-yl)pyrrolidine-1-carboxylate (2.27g, 89%).

Methyl (S)-1-((S)-2-(5-(7-bromo-9,9-difluoro-9H-fluoren-2-yl)-1H-imidazol-2-yl)pyrrolidin-1-yl)-3-methyl-1-oxobutan-2-ylcarbamate: A solution of (S)-tert-butyl 2-(5-(7-bromo-9,9-difluoro-9H-fluoren-2-yl)-1H-imidazol-2-yl)pyrrolidine-1-carboxylate (1.09 g, 2.1 mmol), methanol (10 mL), and 4M HCl in dioxane (10 mL, 40 mmol) was stirred at room temperature. The reaction was thoroughly concentrated after one hour. The resulting residue was dissolved in dimethylformamide (10.6 mL). To this solution was added (S)-2-(methoxycarbonylamino)-3-methylbutanoic acid (390 mg, 2.2 mmol) and HATU (847 mg, 2.2 mmol). Diisopropylethylamine (1.3 mL, 7.5 mmol) was added and the reaction was stirred at room temperature. After thirty minutes, the reaction was diluted with ethyl acetate. The organic phase was washed with water and brine, dried (Na₂SO₄) and concentrated. The crude material was purified by flash column chromatography to yield methyl (S)-1-((S)-2-(5-(7-bromo-9,9-difluoro-9H-fluoren-2-yl)-1H-imidazol-2-yl)pyrrolidin-1-yl)-3-methyl-1-oxobutan-2-ylcarbamate (712 mg, 59%).

(1R,3S,4S)-tert-butyl 3-(6-(9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)-1H-benzo[d]imidazol-2-yl)-2-azabicyclo[2.2.1]heptane-2-carboxylate: A mixture of methyl (S)-1-((S)-2-(5-(7-bromo-9,9-difluoro-9H-fluoren-2-yl)-1H-imidazol-2-yl)pyrrolidin-1-yl)-3-methyl-1-oxobutan-2-ylcarbamate (192 mg, 0.33 mmol), (1R,3S,4S)-tert-butyl 3-(6-(4,4,5,5-tetramethyl-1,3,2-dioxaborolan-2-yl)-1H-benzo[d]imidazol-2-yl)-2-azabicyclo[2.2.1]heptane-2-carboxylate (177 mg, 0.40 mmol), 1M aqueous sodium bicarbonate solution (1.27 mL, 1.27 mmol), triphenylphosphine (9 mg, 0.03 mmol), palladium(II) acetate (4 mg, 0.02 mmol) and dimethoxyethane (3.5 mL) was degassed with a stream of argon for twenty minutes. The reaction was heated to 95° C. After four hours, the reaction was cooled to room temperature and diluted with ethyl acetate. The organic phase was washed with saturated aqueous NaHCO₃ solution and brine, dried (Na₂SO₄) and concentrated. The crude material was purified by flash column chromatography to yield (1R,3S,4S)-tert-butyl 3-(6-(9,9-difluoro-7-(2-((S)-1-((S)-2-(methoxycarbonylamino)-3-methylbutanoyl)pyrrolidin-2-yl)-1H-imidazol-5-yl)-9H- fluoren-2-yl)-1H-benzo[d]imidazol-2-yl)-2-azabicyclo[2.2.1]heptane-2-carboxylate (204 mg, 76%).

Methyl (S)-1-((S)-2-(5-(7-(2-((1R,3S,4S)-2-((R)-2-methoxycarbonylamino-2-phenylacetyl)-2-azabicyclo[2.2.1]heptan-3-yl)-1H-benzo[d]imidazol-6-yl)-9,9-difluoro-9H-fluoren-2-yl)-1H-imidazol-2-yl)pyrrolidin-1-yl)-3-methyl-1-oxobutan-2-ylcarbamate: A solution of (1R,3S,4S)-tert-butyl 3-(6-(9,9-difluoro-7-(2-((S)-1-((S)-2-(methoxycarbonylamino)-3-methylbutanoyl)pyrrolidin-2-yl)-1H-imidazol-5-yl)-9H-fluoren-2-yl)-1H-benzo[d]imidazol-2-yl)-2-azabicyclo[2.2.1]heptane-2-carboxylate (204 mg, 0.25 mmol), methanol (2 mL), and 4M HCl in dioxane (2 mL, 4 mmol) was stirred at room temperature. The reaction was thoroughly concentrated after thirty minutes. The resulting residue was dissolved in a 4:1 dichloromethane:dimethylformamide solution (2.4 mL). Half of this solution was removed and used in the next reaction. To this solution (~1.2 mL) was added (R)-2-(methoxycarbonylamino)-2-phenylacetic acid (24 mg, 0.12 mmol) and COMU (50 mg, 0.12 mmol) and the reaction was cooled to 0° C. Diisopropylethylamine (0.060 mL, 0.35 mmol) was added and the reaction was stirred at 0° C. for twenty minutes. The reaction was quenched by the addition of formic acid (0.05 mL) and thoroughly concentrated. The resulting residue was purified by preparative reverse phase HPLC (Gemini, 10 to 60% ACN/H$_2$O+0.1% TFA) to yield methyl (S)-1-((S)-2-(5-(7-(2-((1R,3S,4S)-2-((R)-2-methoxycarbonylamino-2-phenylacetyl)-2-azabicyclo[2.2.1]heptan-3-yl)-1H-benzo[d]imidazol-6-yl)-9,9-difluoro-9H-fluoren-2-yl)-1H-imidazol-2-yl)pyrrolidin-1-yl)-3-methyl-1-oxobutan-2-ylcarbamate (61 mg, 54%). LCMS-ESI$^+$: calculated for $C_{50}H_{50}F_2N_8O_6$: 897.0; observed [M+1]$^+$: 898.1.

Example LF

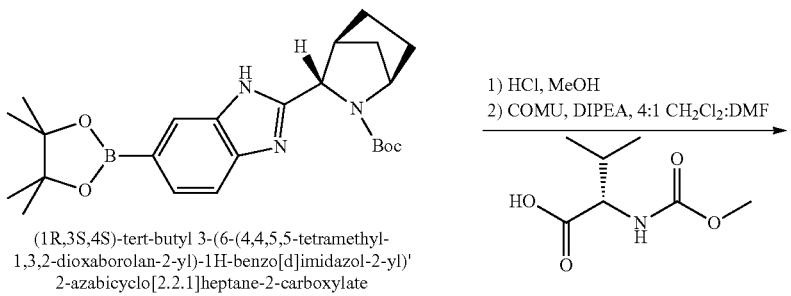

(1R,3S,4S)-tert-butyl 3-(6-(4,4,5,5-tetramethyl-1,3,2-dioxaborolan-2-yl)-1H-benzo[d]imidazol-2-yl)'2-azabicyclo[2.2.1]heptane-2-carboxylate

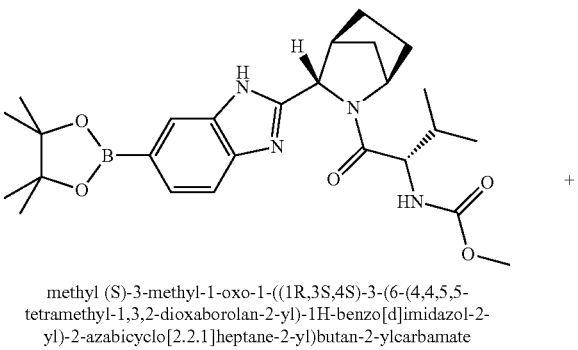

methyl (S)-3-methyl-1-oxo-1-((1R,3S,4S)-3-(6-(4,4,5,5-tetramethyl-1,3,2-dioxaborolan-2-yl)-1H-benzo[d]imidazol-2-yl)-2-azabicyclo[2.2.1]heptane-2-yl)butan-2-ylcarbamate

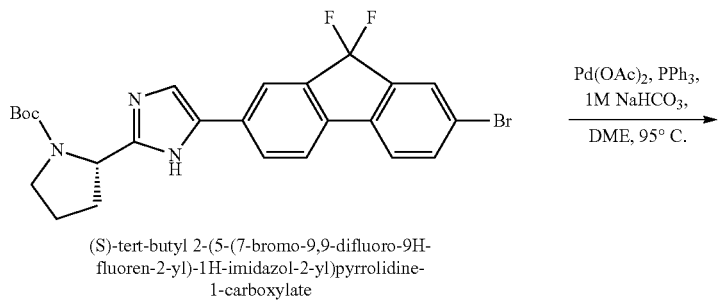

(S)-tert-butyl 2-(5-(7-bromo-9,9-difluoro-9H-fluoren-2-yl)-1H-imidazol-2-yl)pyrrolidine-1-carboxylate -continued

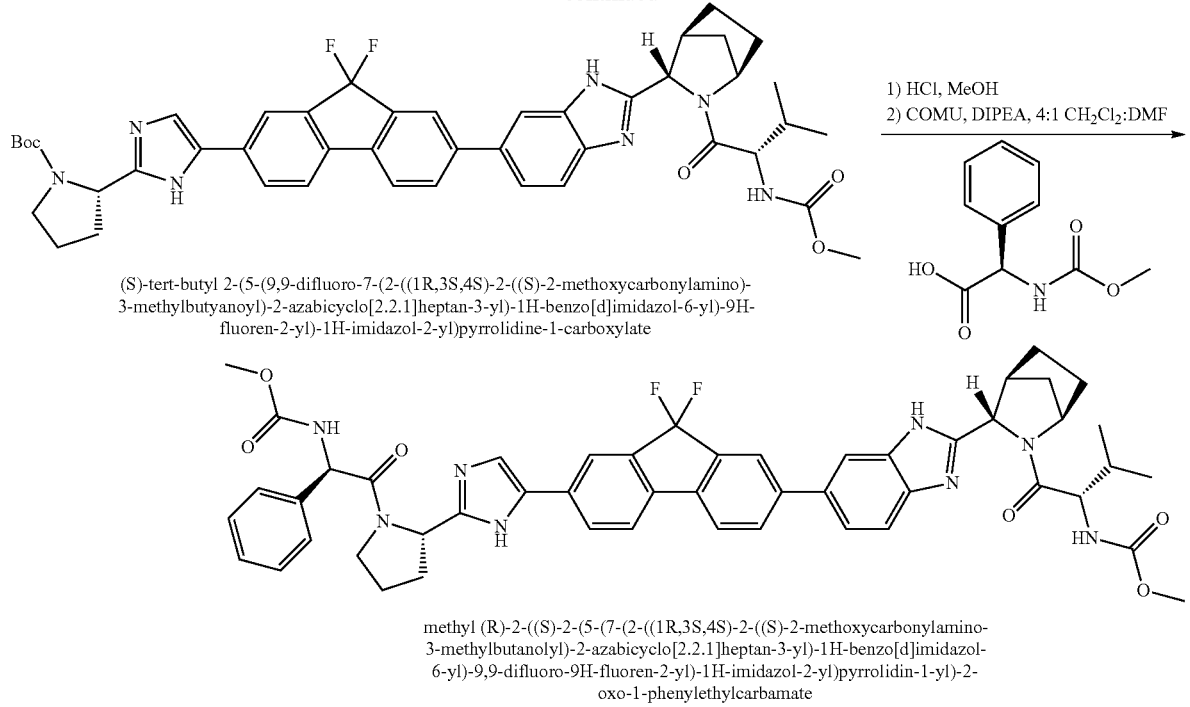

(S)-tert-butyl 2-(5-(9,9-difluoro-7-(2-((1R,3S,4S)-2-((S)-2-methoxycarbonylamino)-3-methylbutyanoyl)-2-azabicyclo[2.2.1]heptan-3-yl)-1H-benzo[d]imidazol-6-yl)-9H-fluoren-2-yl)-1H-imidazol-2-yl)pyrrolidine-1-carboxylate methyl (R)-2-((S)-2-(5-(7-(2-((1R,3S,4S)-2-((S)-2-methoxycarbonylamino-3-methylbutanolyl)-2-azabicyclo[2.2.1]heptan-3-yl)-1H-benzo[d]imidazol-6-yl)-9,9-difluoro-9H-fluoren-2-yl)-1H-imidazol-2-yl)pyrrolidin-1-yl)-2-oxo-1-phenylethylcarbamate Methyl (S)-3-methyl-1-oxo-1-((1R,3S,4S)-3-(6-(4,4,5,5-tetramethyl-1,3,2-dioxaborolan-2-yl)-1H-benzo[d]imidazol-2-yl)-2-azabicyclo[2.2.1]heptan-2-yl)butan-2-ylcarbamate: A solution of (1R,3S,4S)-tert-butyl 3-(6-(4,4,5,5-tetramethyl-1,3,2-dioxaborolan-2-yl)-1H-benzo[d]imidazol-2-yl)-2-azabicyclo[2.2.1]heptane-2-carboxylate (1.0 g, 2.3 mmol), methanol (10 mL), and 4M HCl in dioxane (11 mL, 44 mmol) was stirred at room temperature. The reaction was thoroughly concentrated after one hour. The resulting residue was dissolved in dimethylformamide (11.4 mL). To this solution was added (S)-2-(methoxycarbonylamino)-3-methylbutanoic acid (419 mg, 2.4 mmol) and HATU (909 mg, 2.4 mmol). Diisopropylethylamine (1.4 mL, 8.1 mmol) was added and the reaction was stirred at room temperature. After thirty minutes, the reaction was diluted with ethyl acetate. The organic phase was washed with water and brine, dried (Na$_2$SO$_4$) and concentrated. The crude material was purified by flash column chromatography to yield methyl (S)-3-methyl-1-oxo-1-((1R,3S,4S)-3-(6-(4,4,5,5-tetramethyl-1,3,2-dioxaborolan-2-yl)-1H-benzo[d]imidazol-2-yl)-2-azabicyclo[2.2.1]heptan-2-yl)butan-2-ylcarbamate (1.08 g, 95%).

(S)-tert-butyl 2-(5-(9,9-difluoro-7-(2-((1R,3S,4S)-2-((S)-2-(methoxycarbonylamino)-3-methylbutanoyl)-2-azabicyclo[2.2.1]heptan-3-yl)-1H-benzo[d]imidazol-6-yl)-9H-fluoren-2-yl)-1H-imidazol-2-yl)pyrrolidine-1-carboxylate: A mixture of methyl (S)-3-methyl-1-oxo-1-((1R,3S,4S)-3-(6-(4,4,5,5-tetramethyl-1,3,2-dioxaborolan-2-yl)-1H-benzo[d]imidazol-2-yl)-2-azabicyclo[2.2.1]heptan-2-yl)butan-2-ylcarbamate (122 mg, 0.25 mmol), (S)-tert-butyl 2-(5-(7-bromo-9,9-difluoro-9H-fluoren-2-yl)-1H-imidazol-2-yl)pyrrolidine-1-carboxylate (127 mg, 0.25 mmol), 1M aqueous sodium bicarbonate solution (0.93 mL, 0.93 mmol), triphenylphosphine (13 mg, 0.05 mmol), palladium(II) acetate (5.5 mg, 0.02 mmol) and dimethoxyethane (2.5 mL) was degassed with a stream of argon for twenty minutes. The reaction was heated to 95° C. After four hours, the reaction was cooled to room temperature and diluted with ethyl acetate. The organic phase was washed with saturated aqueous NaHCO$_3$ solution and brine, dried (Na$_2$SO$_4$) and concentrated. The crude material was purified by flash column chromatography to yield (S)-tert-butyl 2-(5-(9,9-difluoro-7-(2-((1R,3S,4S)-2-((S)-2-(methoxycarbonylamino)-3-methylbutanoyl)-2-azabicyclo[2.2.1]heptan-3-yl)-1H-benzo[d]imidazol-6-yl)-9H-fluoren-2-yl)-1H-imidazol-2-yl)pyrrolidine-1-carboxylate (106 mg, 54%).

Methyl (R)-2-((S)-2-(5-(7-(2-((1R,3S,4S)-2-((S)-2-methoxycarbonylamino-3-methylbutanoyl)-2-azabicyclo[2.2.1]heptan-3-yl)-1H-benzo[d]imidazol-6-yl)-9,9-difluoro-9H-fluoren-2-yl)-1H-imidazol-2-yl)pyrrolidin-1-yl)-2-oxo-1-phenylethylcarbamate: A solution of (S)-tert-butyl 2-(5-(9,9-difluoro-7-(2-((1R,3S,4S)-2-((S)-2-(methoxycarbonylamino)-3-methylbutanoyl)-2-azabicyclo[2.2.1]heptan-3-yl)-1H-benzo[d]imidazol-6-yl)-9H-fluoren-2-yl)-1H-imidazol-2-yl)pyrrolidine-1-carboxylate (106 mg, 0.13 mmol), methanol (1.5 mL), and 4M HCl in dioxane (1.5 mL, 6 mmol) was stirred at room temperature. The reaction was thoroughly concentrated after thirty minutes. The resulting residue was dissolved in a 4:1 dichloromethane:dimethylformamide solution (1.3 mL). To this solution was added (R)-2-(methoxycarbonylamino)-2-phenylacetic acid (28 mg, 0.13 mmol) and COMU (56 mg, 0.13 mmol) and the reaction was cooled to 0° C. Diisopropylethylamine (0.092 mL, 0.53 mmol) was added and the reaction was stirred at 0° C. for twenty minutes. The reaction was quenched by the addition of formic acid (0.05 mL) and thoroughly concentrated. The resulting residue was purified by preparative reverse phase HPLC (Gemini, 10 to 60% ACN/H$_2$O+0.1% TFA) to yield methyl (R)-2-((S)-2-(5-(7-(2-((1R,3S,4S)-2-((S)-2-methoxycarbonylamino-3-methylbutanoyl)-2-azabicyclo[2.2.1]heptan-3-yl)-1H-benzo[d]imidazol-6-yl)-9,9-difluoro-9H-fluoren-2-yl)-1H-imidazol-2-yl)pyrrolidin-1-yl)-2-oxo-1-phenylethylcarbamate (28 mg, 24%). LCMS-ESI$^+$: calculated for C$_{50}$H$_{50}$F$_2$N$_8$O$_6$: 897.0; observed [M+1]$^+$: 898.1.

Example LG

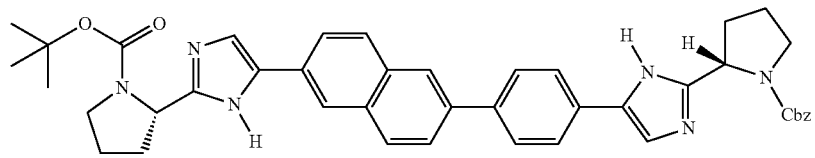

2-(5-{6-[4-(2-{1-[2-Benzylocycarbonyl]-pyrrolidin-2-yl}-3H-imidazol-4-yl)phenyl]-naphthalen-2-yl}-1H-imidazol-2-yl)-pyrrolidine-1-carboxylic acid tert-butyl ester

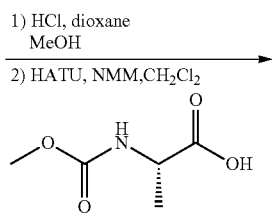

2-Methoxycarbonylamino-propionic acid

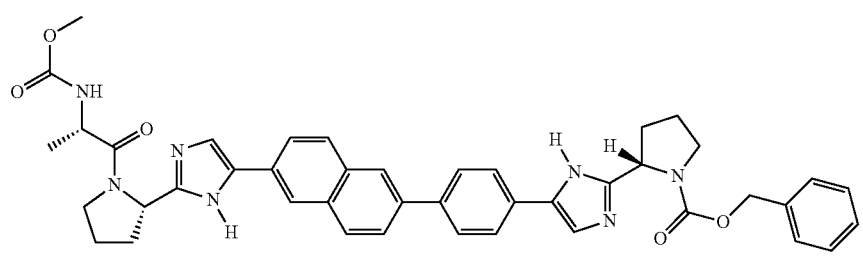

2-{5-[4-(6-{2-[1-(2-Methoxycarbonylamino-propionyl)-pyrrolidin-2-yl]-3H-imidazol-4-yl}-naphthalen-2-yl)-phenyl]-1H-imidazol-2-yl}-pyrrolidine-1-carboxylic acid benzyl ester

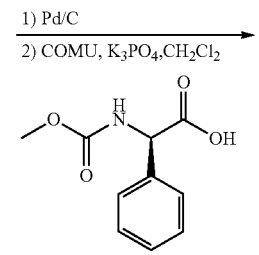

Methoxycarbonylamino-phenyl-acetic acid

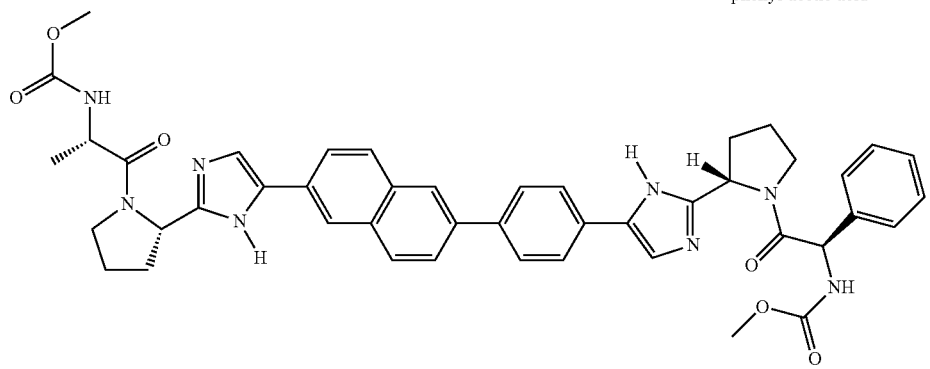

[2-(2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidin-1-yl)-1-methyl-2-oxo-ethyl]-carbamic acid methyl ester 2-(5-{6-[4-(2-{1-[2-Benzyloxycarbonyl]-pyrrolidin-2-yl}-3H-imidazol-4-yl)-phenyl]-naphthalen-2-yl}-1H-imidazol-2-yl)-pyrrolidine-1-carboxylic acid tert-butyl ester. This compound was prepared according to the procedure described in Example ER.

2-{5-[4-(6-{2-[1-(2-Methoxycarbonylamino-propionyl)-pyrrolidin-2-yl]-3H-imidazol-4-yl}-naphthalen-2-yl)-phenyl]-1H-imidazol-2-yl}-pyrrolidine-1-carboxylic acid benzyl ester:

This compound was prepared according to the procedure used to make (1-{2-[5-(6-Bromo-naphthalen-2-yl)-1H-imidazol-2-yl]-pyrrolidine-1-carbonyl}-2-methyl-propyl)-carbamic acid methyl ester (Example GG) using 2-(5-{6-[4-(2-{1-[2-Benzyloxycarbonyl]-pyrrolidin-2-yl}-3H-imidazol-4-yl)-phenyl]-naphthalen-2-yl}-1H-imidazol-2-yl)-pyrrolidine-1-carboxylic acid tert-butyl ester (0.502g, 0.708 mmol) and 2-Methoxycarbonylamino-propionic acid (0.190g, 1.29 mmol) to give 2-{5-[4-(6-{2-[1-(2-Methoxycarbonylamino-propionyl)-pyrrolidin-2-yl]-3H-imidazol-4-yl}-naphthalen-2-yl)-phenyl]-1H-imidazol-2-yl}-pyrrolidine-1-carboxylic acid benzyl ester (0.74g, >99% yield) as a white solid. LCMS-ESI$^+$: calc'd for $C_{43}H_{43}N_7O_5$: 737.33 (M$^+$); Found: 738.79 (M+H$^+$).

[2-(2-{5-[6-(4-{2-[1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidin-1-yl)-1-methyl-2-oxo-ethyl]-carbamic acid methyl ester: To a solution of 2-{5-[4-(6-{2-[1-(2-Methoxycarbonylamino-propionyl)-pyrrolidin-2-yl]-3H-imidazol-4-yl}-naphthalen-2-yl)-phenyl]-1H-imidazol-2-yl}-pyrrolidine-1-carboxylic acid benzyl ester (0.522 g, 0.708 mmol) in EtOH (7.1 mL) was added Palladium on carbon (10%, 0.015 g, 0.150 mmol) and Potassium Carbonate (0.196 g, 0.1.416 mmol). The slurry was stirred at room temperature under an atmosphere of H2 for 72 h. The slurry was filtered through celite and washed with EtOH. The filtrate was concentrated to an oil and slurried in CH2Cl2 (3.23 mL). Methoxycarbonylamino-phenyl-acetic acid (0.101 g, 0.0.484 mmol) and Potassium Phosphate (0.205 g, 0.968 mmol) were added and the resulting solution was cooled to 0° C. (external, ice). COMU (0.172 g, 0.403 mmol) was added and the reaction was stirred at 0° C. for 2 h. The resulting solution was concentrated, diluted with DMF and filtered. Purification by preparative HPLC (Gemini, 15→40% MeCN in H₂O (0.1% formic acid)) and lyophilization provided [2-(2-{5-[6-(4-{2- [1-(2-Methoxycarbonylamino-2-phenyl-acetyl)-pyrrolidin-2-yl]-3H-imidazol-4-yl}-phenyl)-naphthalen-2-yl]-1H-imidazol-2-yl}-pyrrolidin-1-yl)-1-methyl-2-oxo-ethyl]-carbamic acid methyl ester (0.174 g, 68%). LCMS-ESI⁺: calc'd for $C_{45}H_{46}N_8O_6$: 794.35 (M⁺); Found: 795.89 (M+H⁺).

Example LH

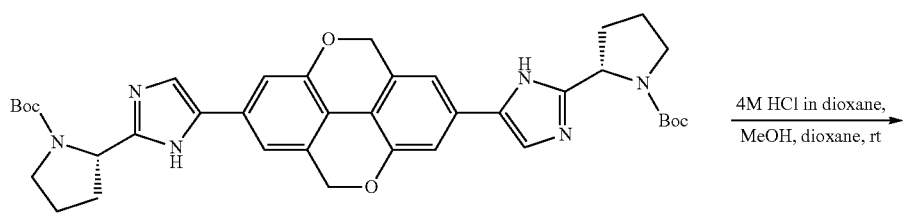

(2S,2'S)-tert-butyl 2,2'-(5,5'-(5,10-dihydrochromeno-[5,4,3-cde]chromene-2,7-diyl)bis(1H-imidazole-5,2-diyl))-dipyrrolidine-1-carboxylate

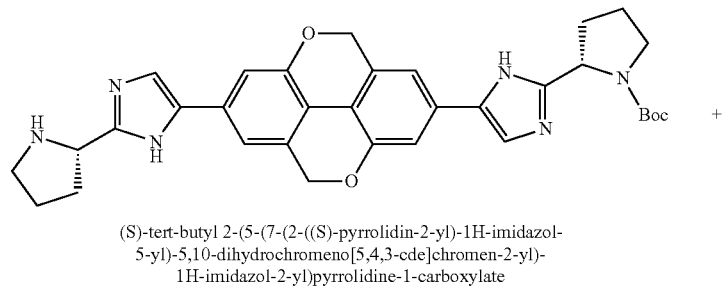

(S)-tert-butyl 2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidine-1-carboxylate

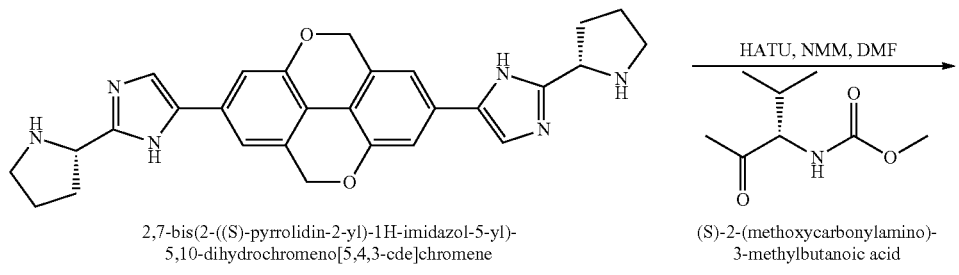

2,7-bis(2-((S)-pyrrolidin-2-yl)-1H-imidazol-5-yl)-5,10-dihydrochromeno[5,4,3-cde]chromene (S)-2-(methoxycarbonylamino)-3-methylbutanoic acid

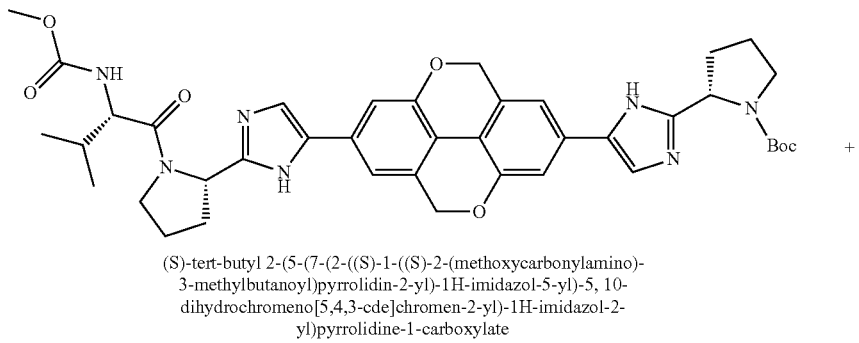

(S)-tert-butyl 2-(5-(7-(2-((S)-1-((S)-2-(methoxycarbonylamino)-3-methylbutanoyl)pyrrolidin-2-yl)-1H-imidazol-5-yl)-5, 10-dihydrochromeno[5,4,3-cde]chromen-2-yl)-1H-imidazol-2-yl)pyrrolidine-1-carboxylate

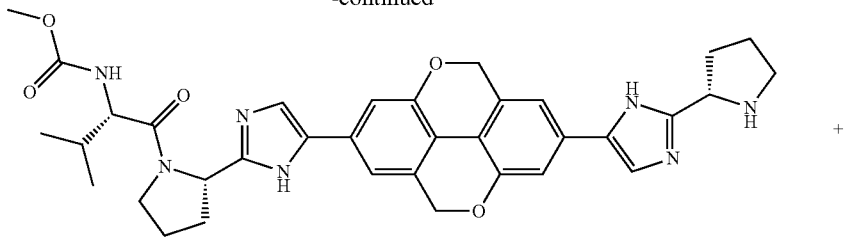

methyl (S)-3-methyl-1-oxo-1-((S)-2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidin-1-yl)butan-2-ylcarbamate

+

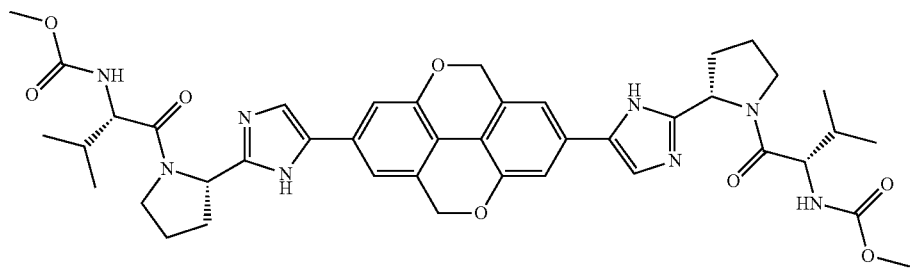

dimethyl (2S,2'S)-1,1'-((2S,2'S)-2,2'-(5,5'-(5,10-dihydrochromeno-[5,4,3-cde]chromene-2,7-diyl)bis(1H-imidazole-5,2-diyl))bis-(pyrrolidine-2, 1-diyl))bis(3-methyl-1-oxobutane-2,1-diyl)dicarbamate A Mixture of (S)-tert-butyl 2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidine-1-carboxylate and 2,7-bis(2-((S)-pyrrolidin-2-yl)-1H-imidazol-5-yl)-5,10-dihydrochromeno[5,4,3-cde]chromene: A solution of (2S,2'S)-tert-butyl 2,2'-(5,5'-(5,10-dihydrochromeno-[5,4,3-cde]chromene-2,7-diyl)bis(1H-imidazole-5,2-diyl))-dipyrrolidine-1-carboxylate (505 mg, 0.74 mmol), 4M hydrogen chloride in dioxane (1.85 mL, 7.4 mmol), dioxane (10 mL) and methanol (2 mL) was stirred at room temperature. After 2.5 hours, the reaction was concentrated. The resulting residue was suspended in toluene and thoroughly concentrated to yield a crude mixture containing (S)-tert-butyl 2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidine-1-carboxylate and 2,7-bis(2-((S)-pyrrolidin-2-yl)-1H-imidazol-5-yl)-5,10-dihydrochromeno[5,4,3-cde]chromene in a molar ratio of approximately 1:1. This mixture was used in the next step without further purification.

Methyl (S)-3-methyl-1-oxo-1-((S)-2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidin-1-yl)butan-2-ylcarbamate: The mixture of (S)-tert-butyl 2-(5-(7-(2-((S)-pyrrolidin-2-yl)-1H-imidazol-5-yl)-5,10-dihydrochromeno[5,4,3-cde]chromen-2-yl)-H-imidazol-2-yl)pyrrolidine-1-carboxylate and 2,7-bis(2-((S)-pyrrolidin-2-yl)-1H-imidazol-5-yl)-5,10-dihydrochromeno[5,4,3-cde]chromene obtained in the previous step was dissolved in dimethylformamide (6 mL). To this solution was added (S)-2-(methoxycarbonylamino)-3-methylbutanoic acid (194 mg, 1.11 mmol), HATU (309 mg, 0.81 mmol), and N-methylmorpholine (0.24 mL, 2.2 mmol). The reaction was stirred at room temperature for thirty minutes, and then quenched by the addition of formic acid (0.05 mL). The reaction was concentrated and the resulting residue was purified by preparative reverse phase HPLC (Gemini, 10 to 45% ACN/$H_2O$+ 0.1% TFA) to yield methyl (S)-3-methyl-1-oxo-1-((S)-2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidin-1-yl)butan-2-ylcarbamate (59 mg, 12%) as the tris-TFA salt. Also isolated from the reaction were (S)-tert-butyl 2-(5-(7-(2-((S)-1-((S)-2-(methoxycarbonylamino)-3-methylbutanoyl)pyrrolidin-2-yl)-1H-imidazol-5-yl)-5,10-dihydrochromeno[5,4,3-cde]chromen-2-yl)-1H-imidazol-2-yl)pyrrolidine-1-carboxylate (124 mg, 23%) and dimethyl (2S,2'S)-1,1'-((2S,2'S)-2,2'-(5,5'-(5,10-dihydrochromeno-[5,4,3-cde]chromene-2,7-diyl)bis(1H-imidazole-5,2-diyl))bis (pyrrolidine-2,1-diyl))bis(3-methyl-1-oxobutane-2,1-diyl) dicarbamate (50 mg, 8%).

Example LI

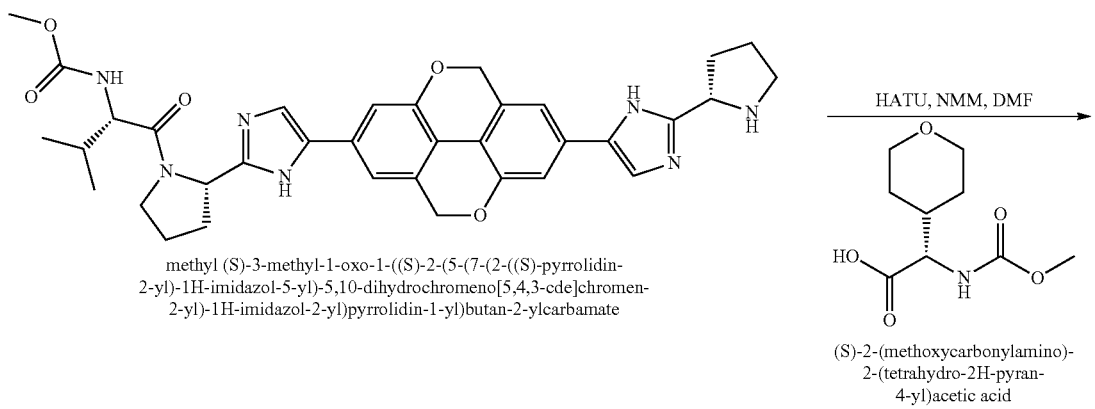

methyl (S)-3-methyl-1-oxo-1-((S)-2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidin-1-yl)butan-2-ylcarbamate (S)-2-(methoxycarbonylamino)-2-(tetrahydro-2H-pyran-4-yl)acetic acid

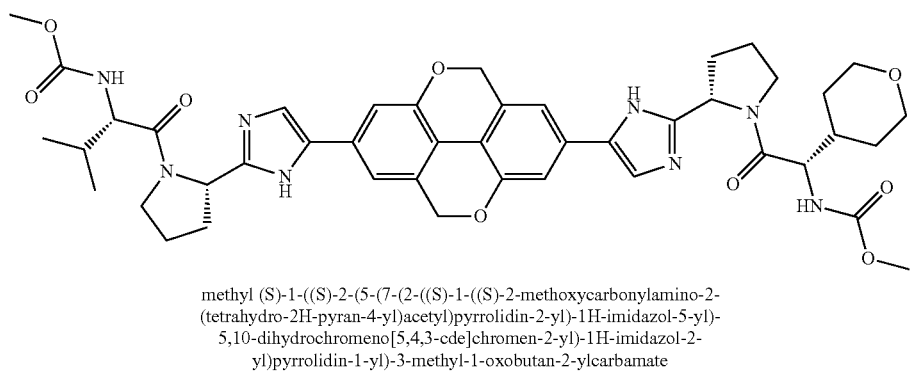

methyl (S)-1-((S)-2-(5-(7-(2-((S)-1-((S)-2-methoxycarbonylamino-2-(tetrahydro-2H-pyran-4-yl)acetyl)pyrrolidin-2-yl)-1H-imidazol-5-yl)-5,10-dihydrochromeno[5,4,3-cde]chromen-2-yl)-1H-imidazol-2-yl)pyrrolidin-1-yl)-3-methyl-1-oxobutan-2-ylcarbamate Methyl (S)-1-((S)-2-(5-(7-(2-((S)-1-((S)-2-methoxycarbonylamino-2-(tetrahydro-2H-pyran-4-yl)acetyl)pyrrolidin-2-yl)-1H-imidazol-5-yl)-5,10-dihydrochromeno[5,4,3-cde]chromen-2-yl)-1H-imidazol-2-yl)pyrrolidin-1-yl)-3-methyl-1-oxobutan-2-ylcarbamate: A solution of the tris-TFA salt of methyl (S)-3-methyl-1-oxo-1-((S)-2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidin-1-yl)butan-2-ylcarbamate (59 mg) in methanol was filtered through an ion exchange column (Stratospheres™ PL-HCO$_3$MP SPE, Part #: PL3540-C603). The column was rinsed with methanol and the filtrate was concentrated to yield methyl (S)-3-methyl-1-oxo-1-((S)-2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidin-1-yl)butan-2-ylcarbamate (36 mg, 0.056 mmol) as the freebase. This material was dissolved in dimethylformamide (2 mL). One half of this solution was used in the next reaction. To this solution (1 mL, 0.028 mmol) was added (S)-2-(methoxycarbonylamino)-2-(tetrahydro-2H-pyran-4-yl)acetic acid (12.3 mg, 0.057 mmol), HATU (12.8 mg, 0.034 mmol) and N-methylmorpholine (0.009 mL, 0.08 mmol). The reaction was stirred at room temperature for twenty minutes, and then quenched by the addition of formic acid (0.03 mL) The reaction was concentrated and the resulting residue was purified by preparative reverse phase HPLC (Gemini, 10 to 45% ACN/H$_2$O+0.1% TFA) to yield methyl (S)-1-((S)-2-(5-(7-(2-((S)-1-((S)-2-methoxycarbonylamino-2-(tetrahydro-2H-pyran-4-yl)acetyl)pyrrolidin-2-yl)-1H-imidazol-5-yl)-5,10-dihydrochromeno[5,4,3-cde]chromen-2-yl)-1H-imidazol-2-yl)pyrrolidin-1-yl)-3-methyl-1-oxobutan-2-ylcarbamate (20 mg, 85%). LCMS-ESI$^+$: calculated for $C_{44}H_{52}N_8O_9$: 836.39; observed [M+1]$^+$: 837.49.

Example LJ

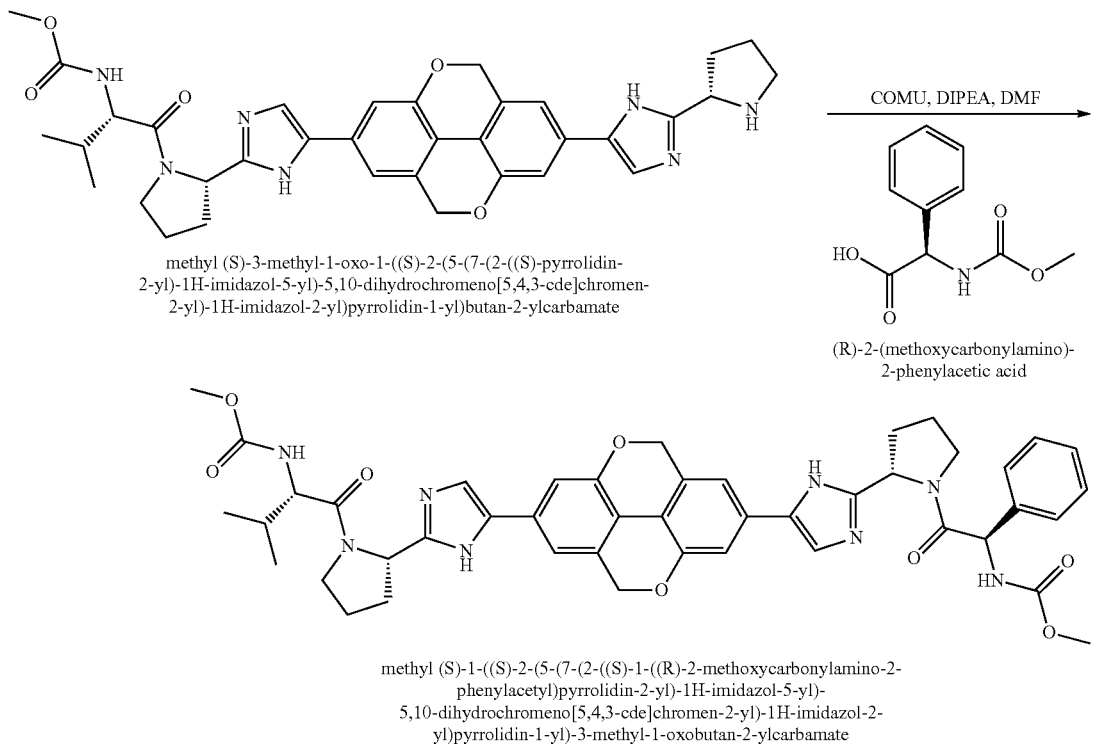

methyl (S)-3-methyl-1-oxo-1-((S)-2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidin-1-yl)butan-2-ylcarbamate (R)-2-(methoxycarbonylamino)-2-phenylacetic acid methyl (S)-1-((S)-2-(5-(7-(2-((S)-1-((R)-2-methoxycarbonylamino-2-phenylacetyl)pyrrolidin-2-yl)-1H-imidazol-5-yl)-5,10-dihydrochromeno[5,4,3-cde]chromen-2-yl)-1H-imidazol-2-yl)pyrrolidin-1-yl)-3-methyl-1-oxobutan-2-ylcarbamate Methyl (S)-1-((S)-2-(5-(7-(2-((S)-1-((R)-2-methoxycarbonylamino-2-phenylacetyl)pyrrolidin-2-yl)-1H-imidazol-5-yl)-5,10-dihydrochromeno[5,4,3-cde]chromen-2-yl)-1H-imidazol-2-yl)pyrrolidin-1-yl)-3-methyl-1-oxobutan-2-ylcarbamate:

A solution of the tris-TFA salt of methyl (S)-3-methyl-1-oxo-1-((S)-2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidin-1-yl)butan-2-ylcarbamate (59 mg) in methanol was filtered through an ion exchange column (Stratospheres™ PL-HCO$_3$MP SPE, Part #: PL3540-C603). The column was rinsed with methanol and the filtrate was concentrated to yield methyl (S)-3-methyl-1-oxo-1-((S)-2-(5-(7-(2-((S)-pyrrolidin-2-yl)-1H-imidazol-5-yl)-5,10-dihydrochromeno[5,4,3-cde]chromen-2-yl)-1H-imidazol-2-yl)pyrrolidin-1-yl)butan-2-ylcarbamate (36 mg, 0.056 mmol) as the freebase. This material was dissolved in dimethylformamide (2 mL). One half of this solution was used in the next reaction. To this solution (1 mL, 0.028 mmol) at 0° C. was added (R)-2-(methoxycarbonylamino)-2-phenylacetic acid (11.7 mg, 0.056 mmol), COMU (13.2 mg, 0.031 mmol) and diisopropylethylamine (0.015 mL, 0.084 mmol). The reaction was stirred at 0 OC for twenty minutes, and then quenched by the addition of formic acid (0.03 mL) The reaction was concentrated and the resulting residue was purified by preparative reverse phase HPLC (Gemini, 10 to 45% ACN/H$_2$O+0.1% TFA) to yield methyl (S)-1-((S)-2-(5-(7-(2-((S)-1-((R)-2-methoxycarbonylamino-2-phenylacetyl)pyrrolidin-2-yl)-1H-imidazol-5-yl)-5,10-dihydrochromeno[5,4,3-cde]chromen-2-yl)-1H-imidazol-2-yl)pyrrolidin-1-yl)-3-methyl-1-oxobutan-2-ylcarbamate (19 mg, 82%). LCMS-ESI$^+$: calculated for C$_{45}$H$_{48}$N$_8$O$_8$: 828.91; observed [M+1]$^+$: 829.75.

Example LK

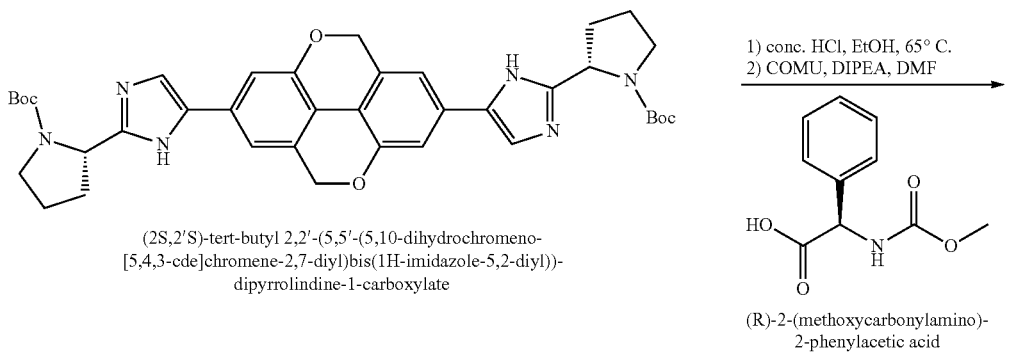

(2S,2'S)-tert-butyl 2,2'-(5,5'-(5,10-dihydrochromeno[5,4,3-cde]chromene-2,7-diyl)bis(1H-imidazole-5,2-diyl))-dipyrrolindine-1-carboxylate 1) conc. HCl, EtOH, 65° C.
2) COMU, DIPEA, DMF (R)-2-(methoxycarbonylamino)-2-phenylacetic acid

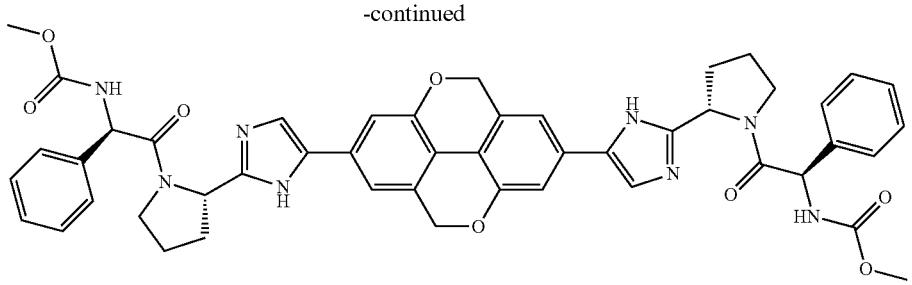

dimethyl (1R,1'R)-2,2'-((2S,2'S)-2,2'-(5,5'-(5,10-dihydrochromeno-
[5,4,3-cde]chromene-2,7-diyl)bis(1H-imidazole-5,2-diyl))bis(pyrrolidine-
2,1-diyl))bis(2-oxo-1-phenylethane-2,1-diyl)dicarbamate Dimethyl (1R,1'R)-2,2'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-oxo-1-phenylethane-2,1-diyl)dicarbamate: A solution of (2S,2'S)-tert-butyl 2,2'-(5,5'-(5,10-dihydrochromeno[5,4,3-cde]chromene-2,7-diyl)bis(1H-imidazole-5,2-diyl))-dipyrrolidine-1-carboxylate (190 mg, 0.28 mmol) and concentrated hydrogen chloride (1 mL) in ethanol (10 mL) was heated to 65° C. After thirty five minutes the reaction was concentrated. The residue was suspended in toluene and thoroughly concentrated. A portion of this deprotected amine (49 mg, 0.078 mmol) was dissolved in dimethylformamide (2 mL). To this solution at 0° C. was added (R)-2-(methoxycarbonylamino)-2-phenylacetic acid (49 mg, 0.23 mmol), COMU (73 mg, 0.17 mmol) and diisopropylethylamine (0.068 mL, 0.39 mmol). After thirty minutes, the reaction was quenched by the addition of formic acid (0.03 mL). The reaction was concentrated and the resulting residue was purified by preparative reverse phase HPLC (Gemini, 10 to 50% ACN/H$_2$O+0.1% TFA). The HPLC fractions containing product were combined and concentrated to remove most of the acetonitrile. Saturated aqueous NaHCO$_3$ solution was added until the product-containing solution became basic. The aqueous phase was extracted three times with ethyl acetate. The combined organic layers were washed once with brine, dried (Na$_2$SO$_4$) and concentrated to yield dimethyl (1R,1'R)-2,2'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-oxo-1-phenylethane-2,1-diyl)dicarbamate (45.4 mg, 67%). LCMS-ESI$^+$: calculated for C$_{48}$H$_{46}$N$_8$O$_8$: 862.93; observed [M+1]$^+$: 863.73.

Example LL

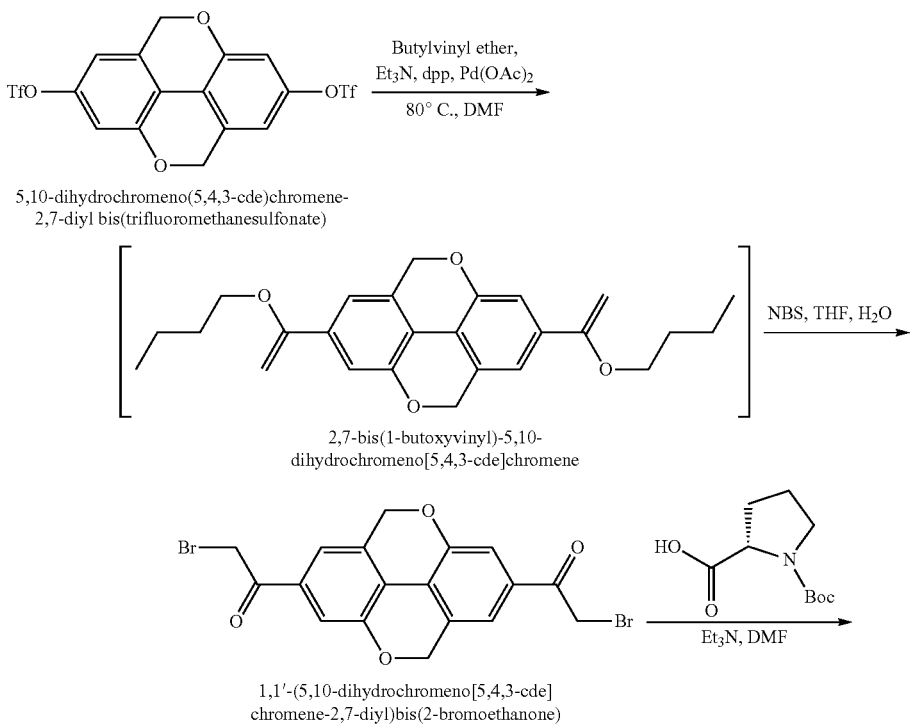

-continued

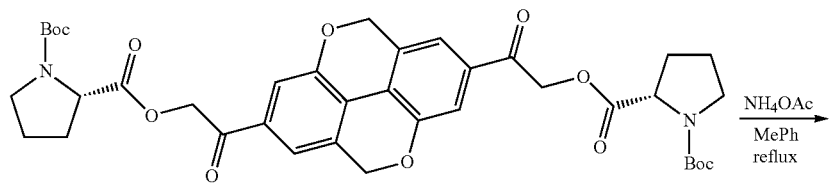

(2S,2'S)-1-tert-butyl¹,²,2-2,2'-(5,10-dihydrochromeno[5,4,3-cde]chromene-2,7-diyl)bis(2-oxoethane-2,1-diyl))dipyrrolidine-1,2-dicarboxylate

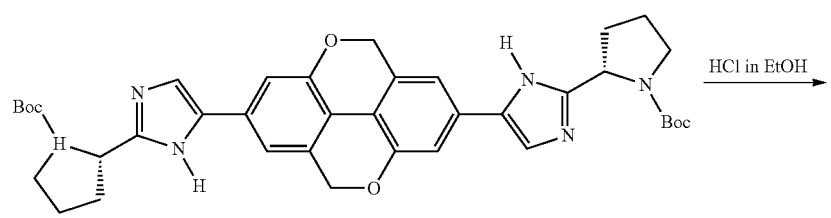

(2S,2'S)-tert-butyl 2,2'-(5,5'-(5,10-dihydrochromeno[5,4,3-cde]chromene-2,7-diyl)bis(1H-imidazole-5,2-diyl))dipyrrolidine-1-carboxylate

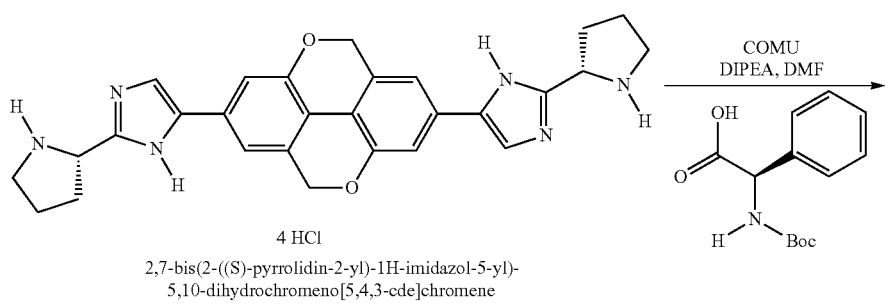

4 HCl
2,7-bis(2-((S)-pyrrolidin-2-yl)-1H-imidazol-5-yl)-5,10-dihydrochromeno[5,4,3-cde]chromene

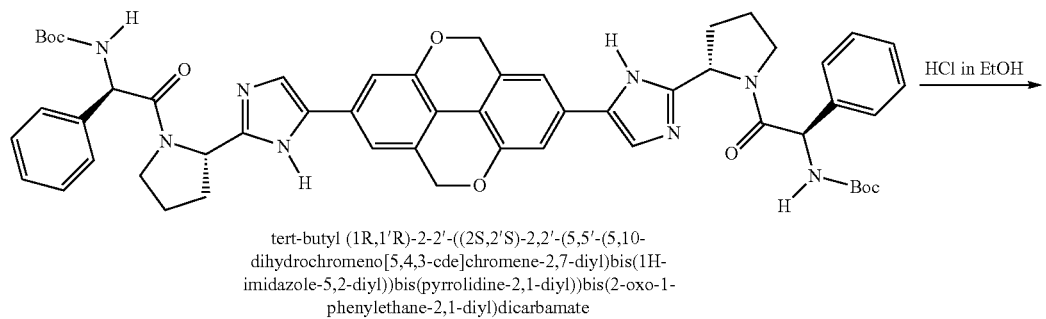

tert-butyl (1R,1'R)-2-2'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-oxo-1-phenylethane-2,1-diyl)dicarbamate

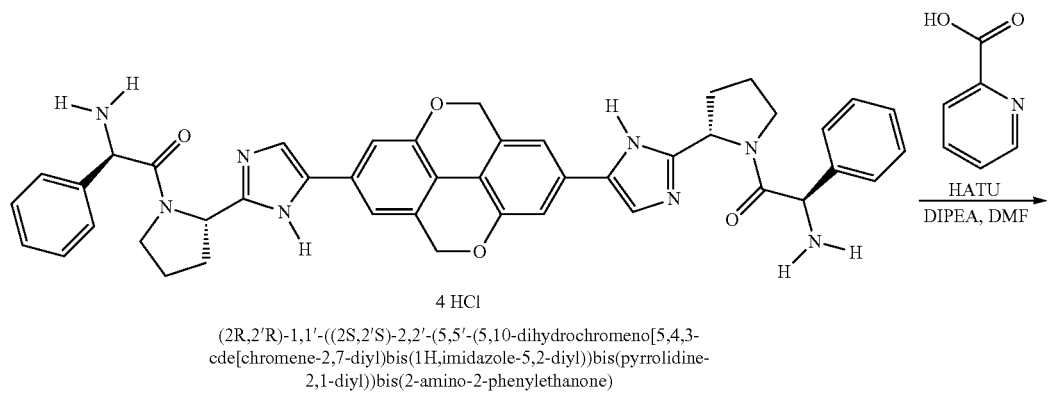

4 HCl
(2R,2'R)-1,1'-((2S,2'S)-2,2'-(5,5'-(5,10-dihydrochromeno[5,4,3-cde]chromene-2,7-diyl)bis(1H,imidazole-5,2-diyl))bis(pyrrolidine-2,1-diyl))bis(2-amino-2-phenylethanone)

-continued

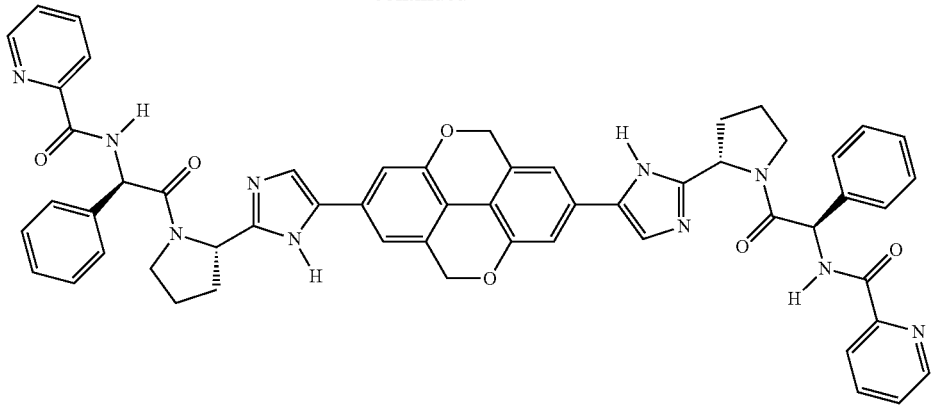

N,N'-(1R,1'R)-2,2'-((2S,2'S)-2,2'-(5,5'-(5,10-dihydrochromeno[5,4,3-cde[chromene-2,7-diyl)bis(1H,imidazole-5,2-diyl))bis(pyrrolidine-2,1-diyl))bis(2-oxo-1-phenylethane-2,1-diyl)dipicolinamide A solution of 5,10-dihydrochromeno[5,4,3-cde]chromene-2,7-diyl bis(trifluoromethanesulfonate) (5.06g, 10.09 mmol) and triethylamine (5.9 mL, 40 mmol) in DMF (100 mL) was degassed with argon for 15 minutes, then 1,3-diphenylphosphinopropane (412 mg, 1 mmol) and palladium acetate (224 mg, 1 mmol) were added under argon. The mixture was heated at 80° C. overnight. The reaction mixture was concentrated by rotary evaporation and then dried further under high vacuum overnight to obtain intermediate 2,7-bis(1-butoxyvinyl)-5,10-dihydrochromeno[5,4,3-cde]chromene as a crude brown solid. $^1$H-NMR of this solid in DMSO-$d_6$ is consistent with desired product and triethylammonium triflate.

Intermediate 2,7-bis(1-butoxyvinyl)-5,10-dihydrochromeno[5,4,3-cde]chromene was treated with THF (51 mL), water (17 mL), and then N-bromosuccinimide (3.74g, 21 mmol) and stirred at room temperature. The dark solution becomes an orange suspension within 15 minutes. After 1.5 hours, 200 mL of ethyl acetate was added and the mixture was filtered. The collected solid was washed with two 60 mL portions of water, three 60 ml portions of ethyl acetate, and three 60 mL portions of diethyl ether. The solid was air dried to give 3.15g (69.6% yield) as a yellow powder. $^1$H NMR in DMSO-$d_6$ is consistent with product C, containing a small amount of an unknown impurity. Note: product C requires some heating to dissolve in DMSO.

To a mixture of 1,1'-(5,10-dihydrochromeno[5,4,3-cde]chromene-2,7-diyl)bis(2-bromoethanone) (2.7g, 5.5 mmol) and (S)-1-(tert-butoxycarbonyl)pyrrolidine-2-carboxylic acid (2.61 g, 13.75 mmol) in 50 mL DMF was added triethylamine (2.4 mL, 13.75 mmol). The reaction was stirred at room temperature overnight. The crude reaction mixture was diluted with 150 mL water and the resulting precipitate was collected by vacuum filtration as a dark yellow solid, 3.18 g, 4.41 mmol) (2S,2'S)-1-tert-butyl '2,2-2,2'-(5,10-dihydrochromeno[5,4,3-cde]chromene-2,7-diyl)bis(2-oxoethane-2,1-diyl)dipyrrolidine-1,2-dicarboxylate A mixture of (2S,2'S)-1-tert-butyl '2,2-2,2'-(5,10-dihydrochromeno[5,4,3-cde]chromene-2,7-diyl)bis(2-oxoethane-2,1-diyl)dipyrrolidine-1,2-dicarboxylate (3.18g, 4.41 mmol), ammonium acetate (3.4g, 44.1 mmol) and toluene (40 mL) was heated at reflux for 2 hours then cooled to room temperature and diluted with ethyl acetate. This gave a precipitate which was collected by vacuum filtration (1.89g).

The filtrate was concentrated and chromatographed using 0-10% methanol in DCM for another 0.96g. Total yield 2.85g of (2S,2'S)-tert-butyl 2,2'-(5,5'-(5,10-dihydrochromeno[5,4,3-cde]chromene-2,7-diyl)bis(1H-imidazole-5,2-diyl))dipyrrolidine-1-carboxylate (2S,2'S)-tert-butyl 2,2'-(5,5'-(5,10-dihydrochromeno[5,4,3-cde]chromene-2,7-diyl)bis(1H-imidazole-5,2-diyl))dipyrrolidine-1-carboxylate (0.96g, 1.41 mmol) was treated with 20 mL 1.25N HCl in ethanol at 40° C. for 3 hours. Concentration followed by trituration with 100 mL diethyl ether gave 2,7-bis(2-((S)-pyrrolidin-2-yl)-1H-imidazol-5-yl)-5,10-dihydrochromeno[5,4,3-cde]chromene tetrahydrochloride (700.7 mg, 1.19 mmol) as a dark orange solid.

To a solution of (R)-2-(tert-butoxycarbonylamino)-2-phenylacetic acid (90 mg), 2,7-bis(2-((S)-pyrrolidin-2-yl)-1H-imidazol-5-yl)-5,10-dihydrochromeno[5,4,3-cde]chromene tetrahydrochloride (118 mg), and N,N-diisopropylethylamine (216 µL) in 2 mL DMF was added (1-Cyano-2-ethoxy-2-oxoethylidenaminooxy)dimethylamino-morpholino-carbenium hexafluorophosphate (172 mg) in an ice bath. Additional (R)-2-(tert-butoxycarbonylamino)-2-phenylacetic acid (60 mg, 0.238 mmol) and (1-Cyano-2-ethoxy-2-oxoethylidenaminooxy)dimethylamino-morpholino-carbenium hexafluorophosphate were added in small portions until the reaction was complete by LCMS. The crude reaction mixture was basified with saturated sodium bicarbonate and extracted into ethyl acetate. The ethyl acetate solution was dried over sodium sulfate, filtered, and concentrated. The crude product was purified by elution through a silica gel column with a gradient of 0-20% methanol in ethyl acetate to give 36.9 mg of tert-butyl (1R,1'R)-2,2'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-oxo-1-phenylethane-2,1-diyl)dicarbamate.

tert-butyl (1R,1'R)-2,2'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-oxo-1-phenylethane-2,1-diyl)dicarbamate (514 mg, 0.75 mmol) was treated with 10 mL of 1.25N hydrogen chloride in ethanol and warmed to 40° C. for 3 hours, then stirred at room temperature overnight. The crude reaction mixture was concentrated then dried under high vacuum for 5 hours to give 483 mg of (2R,2'R)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-amino-2-phenylethanone)tetrahydrochloride as an amber solid.

(2R,2'R)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-amino-2-phenylethanone) tetrahydrochloride (25 mg, 0.028 mmol), picolinic acid (8 mg, 0.063 mmol) and 2-(7-Aza-1H-benzotriazole-1-yl)-1,1,3,3-tetramethyluronium hexafluorophosphate (27 mg, 0.070 mmol) were combined with 1 mL of 10% N,N-diisopropylethyl amine in DMF and stirred at room temperature until complete by LCMS. The crude reaction mixture was diluted with 0.5 mL each of formic acid, water, and acetonitrile, filtered through a 0.2 µm syringe filter and purified by reverse phase HPLC using a gradient of 10-41% organic phase. Lyophilization gave N,N'-(1R,1'R)-2,2'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-oxo-1-phenylethane-2,1-diyl)dipicolinamide as the trifluoroacetate salt, 13.8 mg.

LCMS-ESI$^+$: calc'd for $C_{56}H_{48}N_{10}O_6$: 956.38 (M$^+$); Found: 957.8 (M+H$^+$).

(2R,2'R)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-amino-2-phenylethanone) tetrahydrochloride (20 mg, 0.022 mmol), pyrimidine-4-carboxylic acid (7 mg, 0.06 mmol) and 2-(7-Aza-1H-benzotriazole-1-yl)-1,1,3,3-tetramethyluronium hexafluorophosphate (30 mg, 0.073 mmol) were combined with 1 mL of 10% N,N-diisopropylethyl amine in DMF and stirred at room temperature until complete by LCMS. The crude reaction mixture was diluted with 0.5 mL each of formic acid, water, and acetonitrile, filtered through a 0.2 µm syringe filter and purified by reverse phase HPLC using a gradient of 10-52% organic phase. Lyophilization gave N,N'-(1R,1'R)-2,2'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-oxo-1-phenylethane-2,1-diyl)dipyrimidine-4-carboxamide as the trifluoroacetate salt, 2.5 mg.

LCMS-ESI$^+$: calc'd for $C_{54}H_{46}N_{12}O_6$: 958.37 (M$^+$); Found: 959.7 (M+H$^+$).

Example LL-1

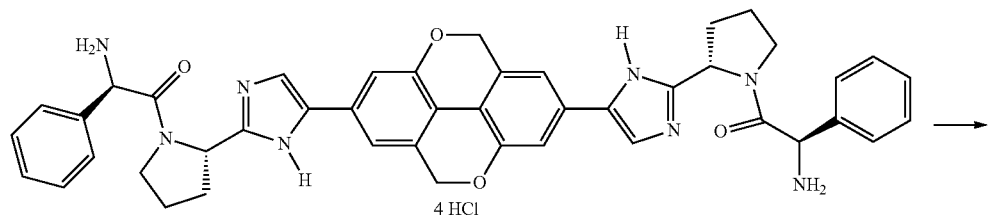

(2R,2'R)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-amino-2-phenylethanone)

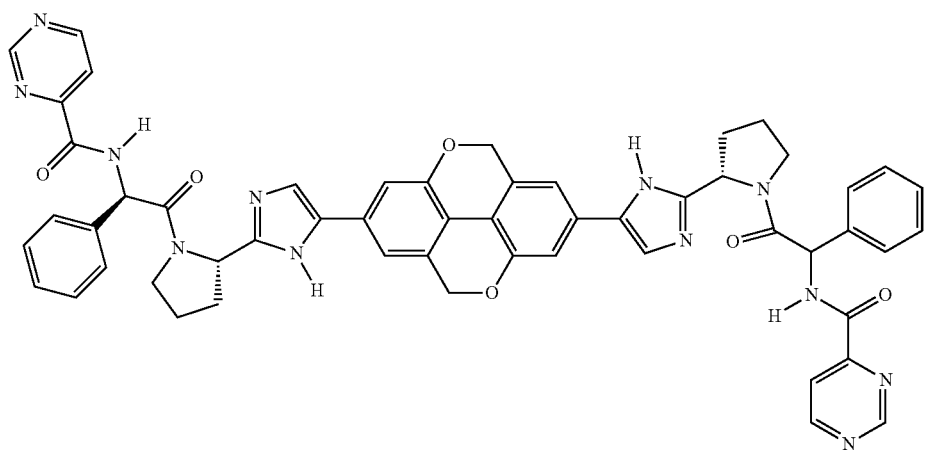

N,N'-(1R,1'R)-2,2'-((2S,2'S)-2,2'-(5,5'-(5,10-dihydrochromeno[5,4,3-cde]chromene-2,7-diyl)bis(2-oxo-1-phenylethane-2,1-diyl)dipyrimidine-4-carboxamide Example LM

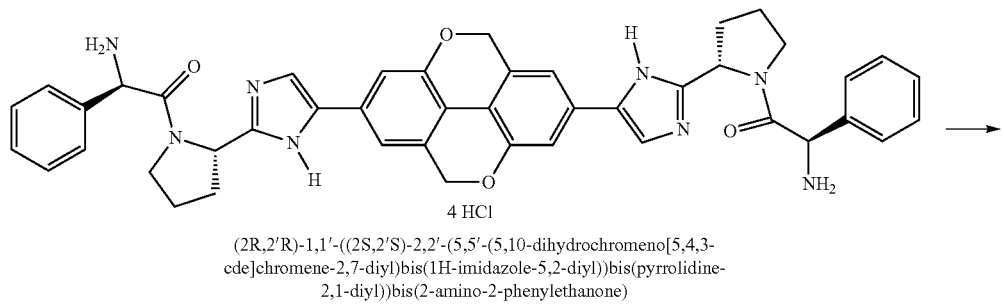

(2R,2'R)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-amino-2-phenylethanone)

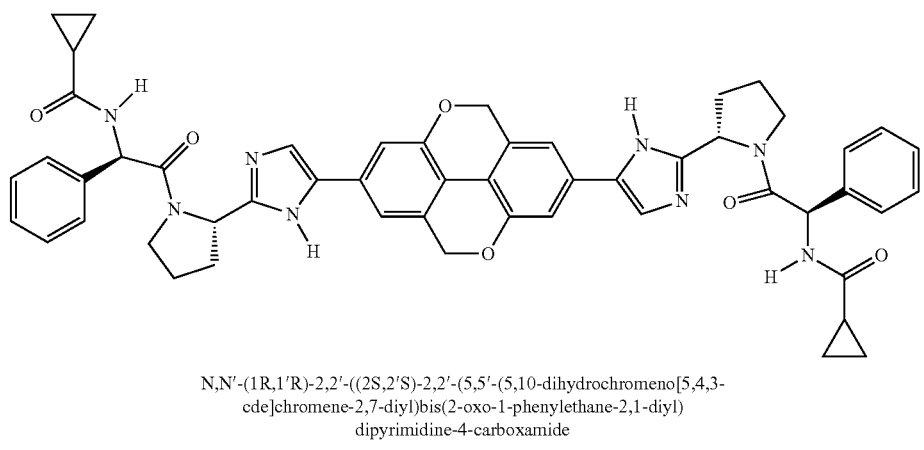

N,N'-(1R,1'R)-2,2'-((2S,2'S)-2,2'-(5,5'-(5,10-dihydrochromeno[5,4,3-cde]chromene-2,7-diyl)bis(2-oxo-1-phenylethane-2,1-diyl)dipyrimidine-4-carboxamide To a solution of (2R,2'R)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-amino-2-phenylethanone) tetrahydrochloride (24 mg, 0.027 mmol) and N,N-diisopropylethyl amine (28μL, 0.162 mmol) in dimethylformamide (300 μL) was added cyclopropane carbonyl chloride (5.5 mg, 0.053 mmol). The reaction was stirred at room temperature for 3 hours. The crude reaction mixture was diluted with 10 drops of formic acid, 5 drops of water, and methanol to a total volume of 1.2 mL, filtered through a 0.2 μm syringe filter and purified by reverse phase HPLC using a gradient of 10-60% organic phase. Lyophilization gave N,N'-(1R,1'R)-2,2'-((2S,2'S)-2,2'-(5,5' 10-dihydrochromeno[5,4,3-cde]chromene-2,7-diyl)bis(1H-imidazole-5,2-diyl))bis(pyrrolidine-2,1-diyl))bis(2-oxo-1-phenylethane-2,1-diyl)dicyclopropanecarboxamide as the trifluoroacetate salt, 6.3 mg.

LCMS-ESI+: calc'd for $C_{52}H_{50}N_8O_6$: 882.39 (M+); Found: 883.8 (M+H+).

Example LN

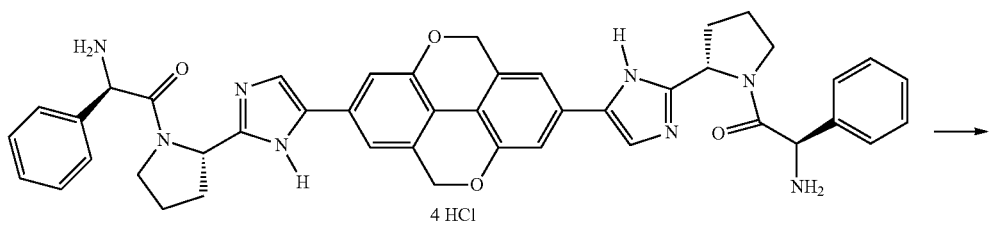

(2R,2'R)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-amino-2-phenylethanone)

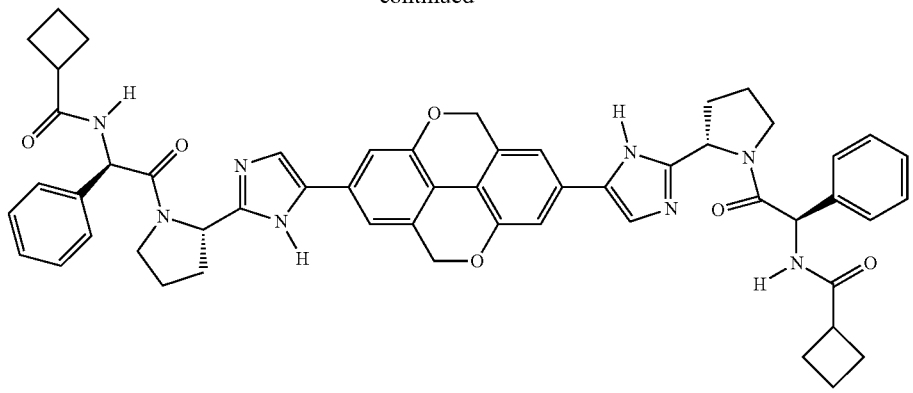

N,N'-(1R,1'R)-2,2'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-oxo-1-phenylethane-2,1-diyl)dicyclobutanecarboxamide To a solution of (2R,2'R)-1,1'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-amino-2-phenylethanone)tetrahydrochloride (24 mg, 0.027 mmol) and N,N-diisopropylethyl amine (28 μL, 0.162 mmol) in dimethylformamide (300 μL) was added cyclobutane carbonyl chloride (6.0 mg, 0.053 mmol). The reaction was stirred at room temperature for 3 hours. The crude reaction mixture was diluted with 10 drops of formic acid, 5 drops of water, and methanol to a total volume of 1.1 mL, filtered through a 0.2 μm syringe filter and purified by reverse phase HPLC using a gradient of 10-46% organic phase. Lyophilization gave N,N'-(1R,1'R)-2,2'-((2S,2'S)-2,2'-(5,5'-(5,10-dihydrochromeno[5,4,3-cde]chromene-2,7-diyl)bis(1H-imidazole-5,2-diyl))bis(pyrrolidine-2,1-diyl))bis(2-oxo-1-phenylethane-2,1-diyl)dicyclobutanecarboxamide as the trifluoroacetate salt, 4.5 mg.

LCMS-ESI+: calc'd for $C_{54}H_{54}N_8O_6$: 910.42 (M+); Found: 911.9 (M+H+).

Example LO

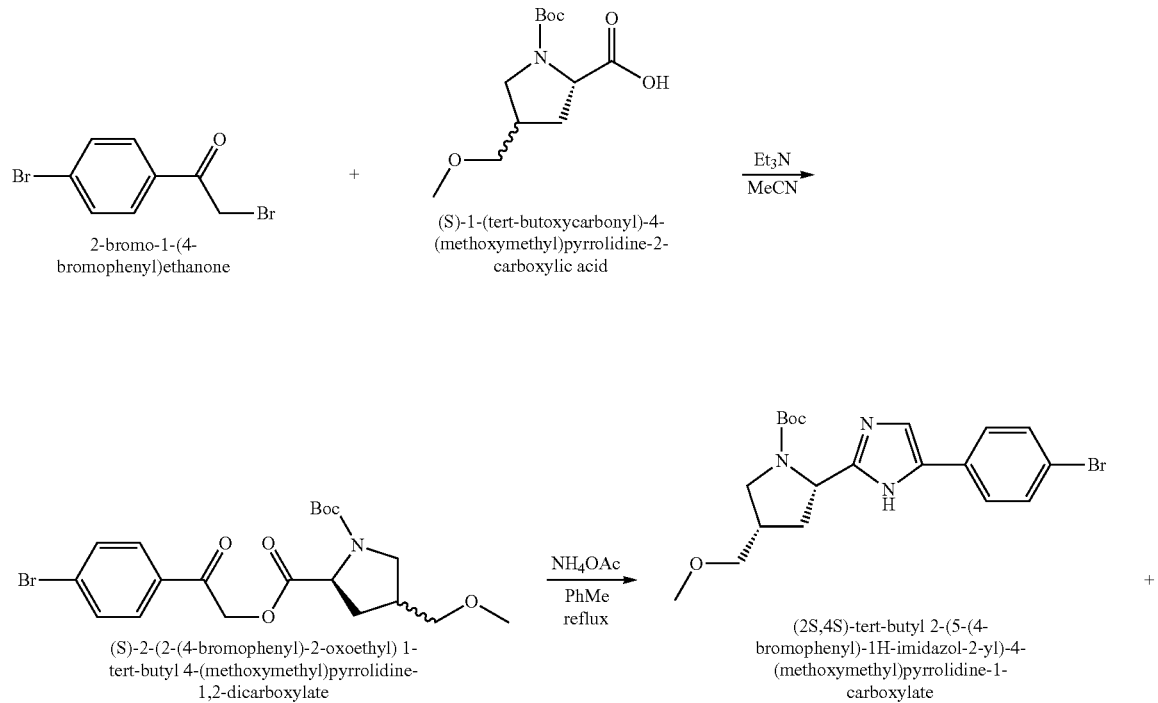

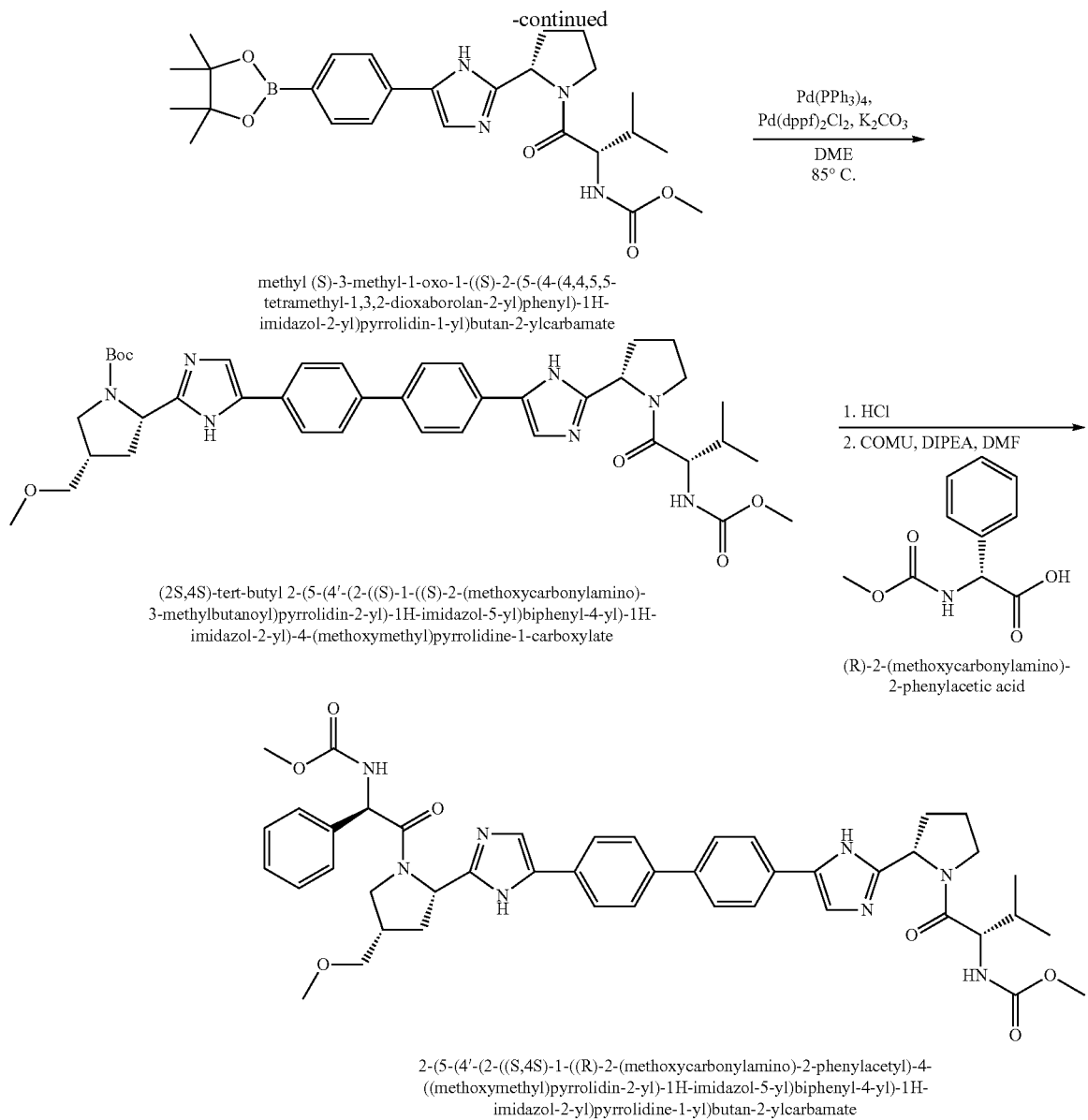

(S)-2-(2-(4-bromophenyl)-2-oxoethyl) 1-tert-butyl 4-(methoxymethyl)pyrrolidine-1,2-dicarboxylate To a solution of 2-bromo-1-(4-bromophenyl)ethanone (2.3 g, 8.39 mmol) and (S)-1-(tert-butoxycarbonyl)-4-(methoxymethyl)pyrrolidine-2-carboxylic acid (2.61 g, 10.06 mmol) in MeCN (100 mL) was added Et$_3$N (1.26 mL, 9.24 mmol). After stirring over night, the solution was diluted with EtOAc, washed with sat. NaHCO$_3$, brine, dried with MgSO$_4$, and concentrated. The residue was purified by silica gel chromatography to yield product (3.32 g).

(2S,4S)-tert-butyl 2-(5-(4-bromophenyl)-1H-imidazol-2-yl)-4-(methoxymethyl)pyrrolidine-1-carboxylate To a solution of (S)-2-(2-(4-bromophenyl)-2-oxoethyl) 1-tert-butyl 4-(methoxymethyl) pyrrolidine-1,2-dicarboxylate (3.32 g, 7.27 mmol) in PhMe (100 mL) was added NH$_4$OAc (11.2 g, 145.5 mmol). The solution was heated to reflux over night. The solution was cooled, and diluted with EtOAc, washed with H$_2$O, sat. NaHCO$_3$, brine, dried with MgSO$_4$, and concentrated. The residue was purified by silica gel chromatography to yield product (1.46 g).

(2S,4S)-tert-butyl-2-(5-(4'-(2-((S)-1-((S)-2-(methoxycarbonylamino)-3-methylbutanoyl) pyrrolidin-2-yl)-1H-imidazol-5-yl)biphenyl-4-yl)-1H-imidazol-2-yl)-4-(methoxymethyl) pyrrolidine-1-carboxylate (2S,4S)-tert-butyl 2-(5-(4-bromophenyl)-1H-imidazol-2-yl)-4-(methoxymethyl)pyrrolidine-1-carboxylate (520 mg, 1.19 mmol) and methyl (S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-ylcarbamate (651 mg, 1.31 mmol) were combined in DME (12 mL). Pd(PPh$_3$)$_4$ (138 mg, 0.12 mmol), Pd(dppf)$_2$Cl$_2$ (88 mg, 0.12 mmol) and K$_2$CO$_3$ (2M H$_2$O, 1.96 mL, 3.9 mmol) were added, and the solution was degassed with N$_2$ for 10 min. The solution was heated to 85° C. and stirred for 5 hours. After cooling to rt, the solution was diluted with EtOAc, washed with sat. NaHCO$_3$, brine, dried with MgSO$_4$, and concentrated. The residue was purified by silica gel chromatography to yield product (387 mg).

2-(5-(4'-(2-((2S,4S)-1-((R)-2-(methoxycarbonylamino)-2-phenylacetyl)-4-((methoxymethyl) pyrrolidin-2-yl)-1H-imidazol-5-yl)biphenyl-4-yl)-1H-imidazol-2-yl)pyrrolidine-1-yl)butan-2-ylcarbamate To (2S,4S)-tert-butyl-2-(5-(4'-(2-((S)-1-((S)-2-(methoxycarbonylamino)-3-methylbutanoyl)pyrrolidin-2-yl)-1H-imidazol-5-yl)biphenyl-4-yl)-1H-imidazol-2-yl)-4-(methoxymethyl)pyrrolidine-1-carboxylate (187 mg, 0.26 mmol) in DCM (5 mL) and MeOH (1 mL) was added HCl (4M in dioxane, 1.5 mL). The solution stirred for 4 h, and the solvent was removed. The intermediate was dissolved in DMF (3 mL). (R)-2-(methoxycarbonylamino)-2-phenylacetic acid (54 mg, 0.26 mmol), COMU (124 mg, 0.26 mmol), and DIPEA (0.23 mL, 1.3 mmol) were added sequentially. The solution stirred o/n and the mixture was purified by HPLC to yield product (58.8 mg). LCMS-ESI⁺: calc'd for $C_{47}H_{50}N_8O_7$: 816.94 ($M^+$); Found: 817.34 ($M+H^+$).

Example LP

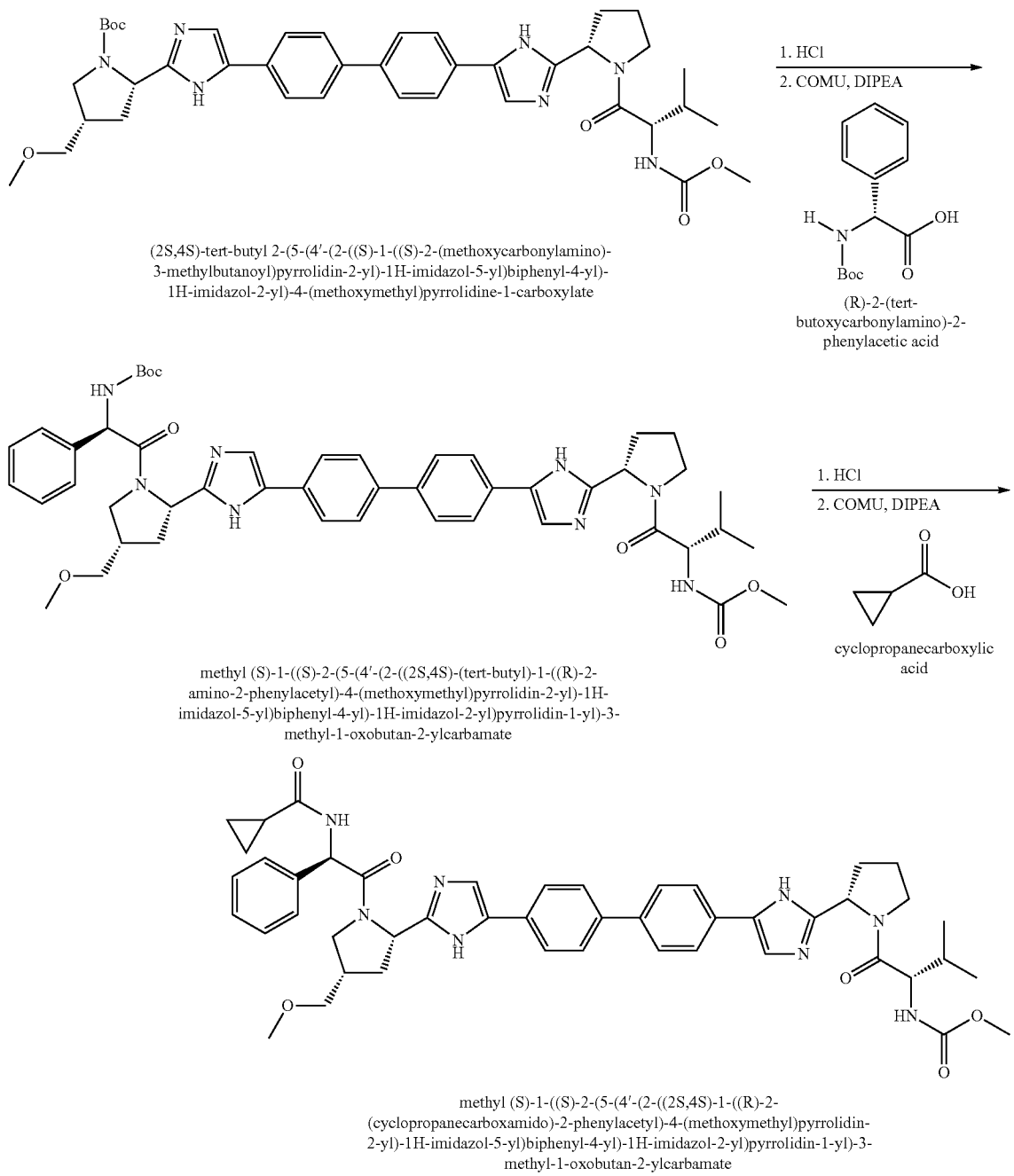

(2S,4S)-tert-butyl 2-(5-(4'-(2-((S)-1-((S)-2-(methoxycarbonylamino)-3-methylbutanoyl)pyrrolidin-2-yl)-1H-imidazol-5-yl)biphenyl-4-yl)-1H-imidazol-2-yl)-4-(methoxymethyl)pyrrolidine-1-carboxylate (R)-2-(tert-butoxycarbonylamino)-2-phenylacetic acid methyl (S)-1-((S)-2-(5-(4'-(2-((2S,4S)-(tert-butyl)-1-((R)-2-amino-2-phenylacetyl)-4-(methoxymethyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate cyclopropanecarboxylic acid methyl (S)-1-((S)-2-(5-(4'-(2-((2S,4S)-1-((R)-2-(cyclopropanecarboxamido)-2-phenylacetyl)-4-(methoxymethyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate

1169

Methyl-(S)-1-((S)-2-(5-(4'-(2-((2S,4S)-(tert-butyl)-1-((R)-2-amino-2-phenylacetyl)-4-(methoxymethyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate

To (2S,4S)-tert-butyl-2-(5-(4'-(2-((S)-1-((S)-2-(methoxycarbonylamino)-3-methylbutanoyl)pyrrolidin-2-yl)-1H-imidazol-5-yl)biphenyl-4-yl)-1H-imidazol-2-yl)-4-(methoxymethyl)pyrrolidine-1-carboxylate (191 mg, 0.26 mmol) in DCM (5 mL) and MeOH (1 mL) was added HCl (4M in dioxane, 1.0 mL). The solution stirred for 16 h, and the solvent was removed. The intermediate was dissolved in DMF (5 mL). (R)-2-(tert-butoxycarbonylamino)-2-phenylacetic acid (65 mg, 0.26 mmol), COMU (124 mg, 0.26 mmol), and DIPEA (0.23 mL, 1.3 mmol) were added sequentially. The solution stirred for 2 h., diluted with MeOH/EtOAc (1:10), washed with sat. NaHCO₃ twice, brine, dried over MgSO₄ and concentrated. It was purified by silica gel chromatography to yield product (187 mg).

Methyl (S)-1-((S)-2-(5-(4'-(2-((2S,4S)-1-((R)-2-(cyclopropanecarboxamido)-2-phenylacetyl)-4-(methoxymethyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate

To methyl (S)-1-((S)-2-(5-(4'-(2-((2S,4S)-(tert-butyl)-1-((R)-2-amino-2-phenylacetyl)-4-(methoxymethyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (187 mg, 0.22 mmol) in DCM (5 mL) and MeOH (1 mL) was added HCl (4M in dioxane, 1.0 mL). The solution was stirred for 16 h, and the solvent was removed. The intermediate was dissolved in DMF (5 mL). Cyclopropanecarboxylic acid (34 μL, 0.44 mmol), COMU (104 mg, 0.22 mmol), and DIPEA (0.19 mL, 1.09 mmol) were added sequentially. The solution stirred for 30 min. It was purified by HPLC to yield product (66.5 mg). LCMS-ESI⁺: calc'd for $C_{47}H_{50}N_8O_7$: 826.98 (M⁺); Found: 827.37 (M+H⁺).

Example LQ

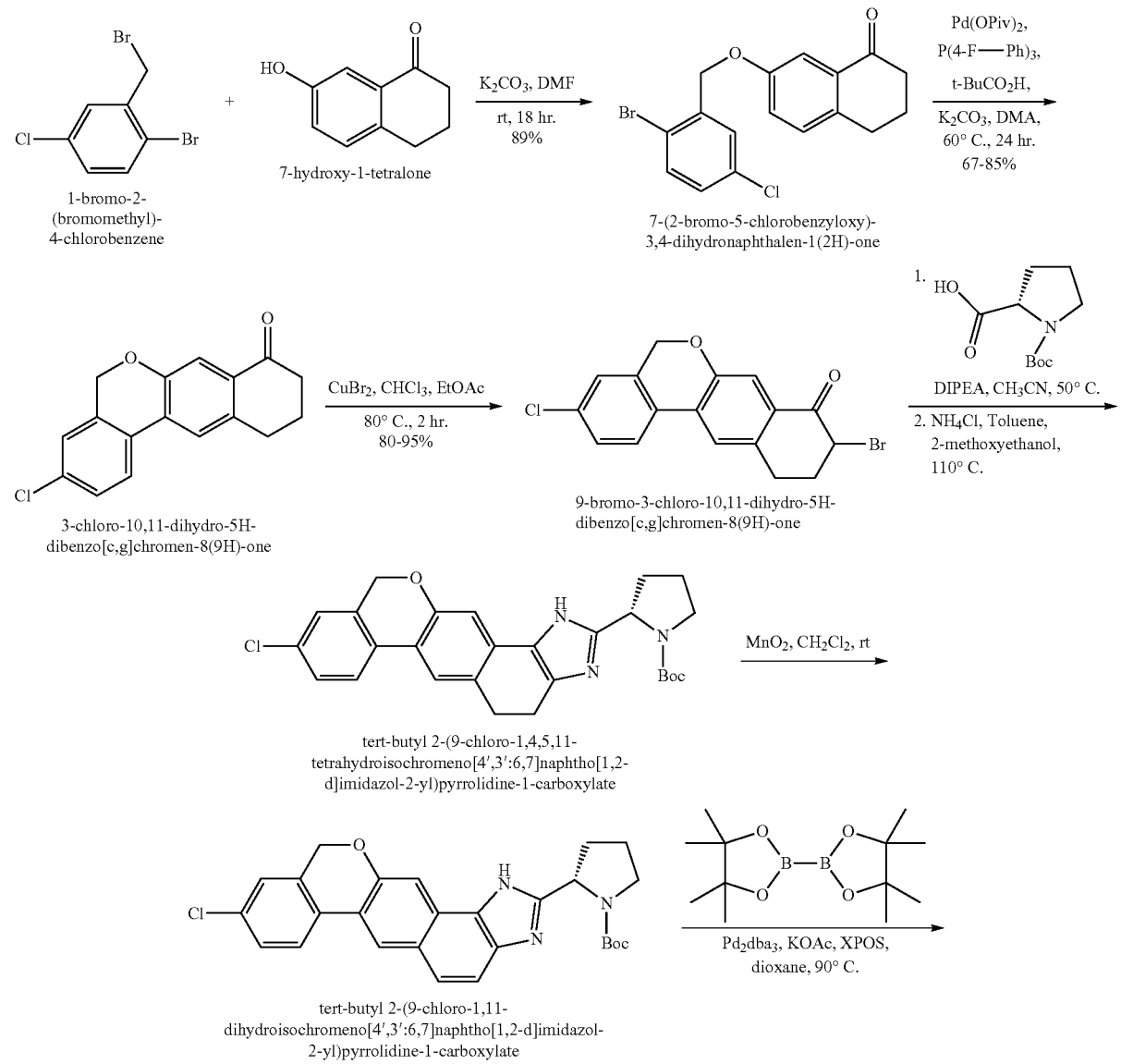

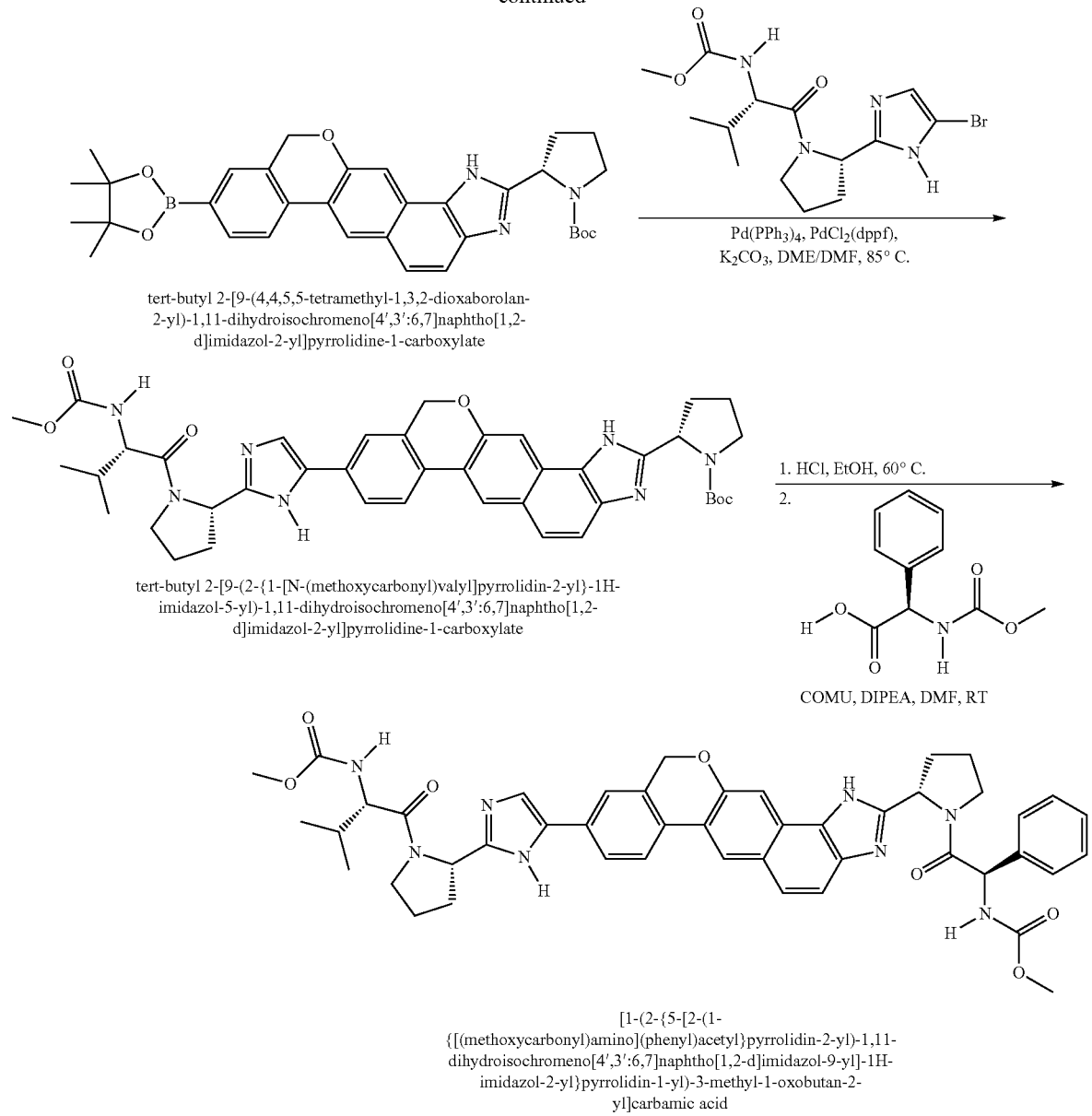

7-(2-bromo-5-chlorobenzyloxy)-3,4-dihydronaphthalen-1(2H)-one

To a stirred solution of 7-hydroxy-1-tetralone (13.9 g, 85.7 mmol) and 1-bromo-2-(bromomethyl)-4-chlorobenzene (25.6 g, 90.0 mmol) in dimethylformamide (850 mL) was added potassium carbonate (24 g, 172 mmol). The reaction was stirred under argon for 18 hours then diluted with ethyl acetate (1 L). The organics were washed three times with water and once with brine. The organic layer was then dried with magnesium sulfate, filtered and concentrated. To the resulting oil was added methanol (500 mL) and the suspension was agitated for thirty minutes. 7-(2-bromo-5-chlorobenzyloxy)-3,4-dihydronaphthalen-1(2H)-one (27.8 g, 89% yield) was isolated by filtration.

3-chloro-10,11-dihydro-5H-dibenzo[c,g]chromen-8(9H)-one

To a 1 L flask containing palladium(II) pivalate (1.18 g, 3.8 mmol), tri(4-fluorophenyl)phosphine (1.20 g, 3.8 mmol), pivalic acid (2.33 g, 22.8 mmol) and potassium carbonate (31.8 g, 228 mmol) was added a solution of 7-(2-bromo-5-chlorobenzyloxy)-3,4-dihydronaphthalen-1(2H)-one (27.8 g, 76.2 mmol) in dimethyacetamide (380 mL). The flask was evacuated and backfilled with argon 5 times and then stirred under argon at 60° C. for 24 hours. The reaction was cooled to room temperature and diluted with MTBE and water. The resulting biphasic mixture was stirred for 3 hours and filtered through Celite, rinsing with MTBE. The organic layer of the filtrate was separated and then washed twice with water and once with brine. The organics were then dried with magnesium sulfate, filtered, concentrated and purified by flash column chromatography (Hexanes/DCM) to yield 3-chloro-10,11-dihydro-5H-dibenzo[c,g]chromen-8(9H)-one (14.4 g, 67% yield) as an off-white solid.

9-bromo-3-chloro-10,11-dihydro-5H-dibenzo[c,g]chromen-8(9H)-one

To a mixture of 3-chloro-10,11-dihydro-5H-dibenzo[c,g]chromen-8(9H)-one (14.8 g, 52 mmol) in chloroform (50 mL) and ethyl acetate (50 mL) was added copper(II) bromide (24.3 g, 104 mmol). The reaction was heated to 80° C. for 2 hours and then cooled to room temperature. The mixture was diluted with dichloromethane and washed twice with a 5:1 solution of saturated aqueous ammonium chloride and aqueous ammonium hydroxide (~38%), and washed once with water. The organic layer was dried with magnesium sulfate, filtered and concentrated to yield 9-bromo-3-chloro-10,11-dihydro-5H-dibenzo[c,g]chromen-8(9H)-one (18.5 g, >95% yield) with >95% purity.

Note: This reaction is not always this clean. Sometimes there is over-bromination and sometimes there is significant starting material. These impurities can be removed by flash column chromatography.

tert-butyl 2-(9-chloro-1,4,5,11-tetrahydroisochromeno[4',3':6,7]naphtho[1,2-d]imidazol-2-yl)pyrrolidine-1-carboxylate: To a solution of (1R)-2-(tert-butoxycarbonyl)cyclopentanecarboxylic acid (10.17 g, 47.25 mmol) and 9-bromo-3-chloro 10,11-dihydro-6H-naphtho[2,3-c]chromen-8(9H)-one (5.7 mg, 15.7 mmol) in acetonitrile (50 mL) was added diisopropylethylamine (11.11 mL, 64 mmol). The reaction was stirred at 50° C. for 4 hours and was then diluted with ethyl acetate. The organics were washed with water and brine, dried (MgSO$_4$) and concentrated. The resulting crude residue was purified by flash chromatography to yield (2S)-1-tert-butyl 2-(3-chloro-8-oxo-8,9,10,11-tetrahydro-5H-naphtho[c,g]chromen-9-yl) pyrrolidine-1,2-dicarboxylate (4.52 g, 58%). To a solution of (2S)-1-tert-butyl 2-(3-chloro-8-oxo-8,9,10,11-tetrahydro-6H-naphtho[2,3-c]chromen-9-yl) pyrrolidine-1,2-dicarboxylate (3.27 mg, 6.56 mmol) in a mixture of toluene (11 mL) and 2-methoxyethanol (0.7 mL) was added ammonium acetate (5.06 g, 65.6 mmol). The reaction mixture was heated to 110° C. for 3 hours, cooled to room temperature and diluted with ethyl acetate. The organics were washed with water and brine, dried (Na$_2$SO$_4$), and concentrated. The crude residue was purified by flash chromatography to yield tert-butyl 2-(9-chloro-1,4,5,11-tetrahydroisochromeno[4',3':6,7]naphtho[1,2-d]imidazol-2-yl)pyrrolidine-1-carboxylate (1.95 g, 61%). LCMS-ESI$^+$: calculated for C27H28ClN$_3$O3$_{42}$: 477.98; observed [M+1]$^+$: 478.47.

tert-butyl 2-(9-chloro-1,11-dihydroisochromeno[4',3':6,7]naphtho[1,2-d]imidazol-2-yl)pyrrolidine-1-carboxylate. To a solution of tert-butyl 2-(9-chloro-1,4,5,11-tetrahydroisochromeno[4',3':6,7]naphtho[1,2-d]imidazol-2-yl)pyrrolidine-1-carboxylate (1.9 g, 3.96 mmol) in dichloromethane (35 mL) was added manganese(IV) oxide (17 g, 198 mmol). The reaction mixture was stirred at room temperature for 18 hours, diluted with ethyl acetate. The organics were washed with water and brine, dried (Na$_2$SO$_4$), and concentrated. The crude residue was purified by flash chromatography to yield tert-butyl 2-(9-chloro-1,11-dihydroisochromeno[4',3':6,7]naphtho[1,2-d]imidazol-2-yl)pyrrolidine-1-carboxylate (1.52 g, 81%). LCMS-ESI$^+$: calculated for C27H26ClN3O3$_{42}$: 475.9; observed [M+1]$^+$: 476.45.

tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate: A degassed mixture of tert-butyl 2-(9-chloro-1,11-dihydroisochromeno[4',3':6,7]naphtho[1,2-d]imidazol-2-yl)pyrrolidine-1-carboxylate (1.52 g, 3.17 mmol), bis(pinacolato)diboron (1.21 g, 4.75 mmol), potassium acetate (934 mg, 9.52 mmol), tris(dibenzylideneacetone)palladium (116 mg, 0.13 mmol) and 2-dicyclohexylphosphino-2',4',6'-tri-i-propyl-1,1'-biphenyl (121 mg, 0.08 mmol) in 1,4-dioxane (16 mL) was heated to 90° C. for 1.5 hours, cooled to room temperature and diluted with ethyl acetate. The organics were washed with water and brine, dried (Na$_2$SO$_4$), and concentrated. The crude residue was purified by flash chromatography to yield tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate (1.7 g, 94%).

tert-butyl 2-[9-(2-{1-[N-(methoxycarbonyl)valyl]pyrrolidin-2-yl}-1H-imidazol-5-yl)-1,11-dihydroisochromeno[4',3':6,7]naphtho[1,2-d]imidazol-2-yl]pyrrolidine-1-carboxylate: To a solution of methyl (S)-1-((S)-2-(5-bromo-1H-imidazol-2-yl)pyrrolidin-1-yl)-3-methyl-1-oxobutan-2-ylcarbamate (1.48 g, 3.97 mmol), tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate (1.88 g, 1.48 mmol), tetrakis(triphenyl phosphine)palladium(0) (191 mg, 0.16 mmol) and dichloro[1,1'-bis(diphenylphosphino) ferrocene]palladium (II) (242 mg, 0.33 mmol) in a mixture of 1,2-dimethoxyethane (37.0 mL) and dimethylformamide (6 mL) was added a solution of potassium carbonate (2M in water, 5 mL, 9.93 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield tert-butyl 2-[9-(2-{1-[N-(methoxycarbonyl)valyl]pyrrolidin-2-yl}-1H-imidazol-5-yl)-1,11-dihydroisochromeno[4',3':6,7]naphtho[1,2-d]imidazol-2-yl]pyrrolidine-1-carboxylate (1.45 mg, 59%). LCMS-ESI$^+$: calculated for C41H47N7O6$_{73}$ 733.86; observed [M+1]$^+$: 734.87.

[1-(2-{5-[2-(1-{[(methoxycarbonyl)amino](phenyl)acetyl}pyrrolidin-2-yl)-1,11-dihydroisochromeno[4',3':6,7]naphtho[1,2-d]imidazol-9-yl]-1H-imidazol-2-yl}pyrrolidin-1-yl)-3-methyl-1-oxobutan-2-yl]carbamic acid: A solution of tert-butyl 2-[9-(2-{1-[N-(methoxycarbonyl)valyl]pyrrolidin-2-yl}-1H-imidazol-5-yl)-1,11-dihydroisochromeno[4',3':6,7]naphtho[1,2-d]imidazol-2-yl]pyrrolidine-1-carboxylate (462 mg, 0.63 mmol), ethanol (6 mL) and concentrated HCl (2 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (172 mg, 0.82 mmol) and COMU (311 mg, 073 mmol) in DMF (6 mL). To the resulting solution was added diisopropylethylamine (330 µL, 1.89 mmol). After stirring for 18 hours at room temperature, the reaction was diluted with ethyl acetate, washed with water and brine, dried (Na$_2$SO$_4$), concentrated and purified by preparative reverse phase HPLC (Gemini, 15 to 45% ACN/H$_2$O+0.1% TFA). The product fractions were lyophilized to give [1-(2-{5-[2-(1-{[(methoxycarbonyl)amino](phenyl)acetyl}pyrrolidin-2-yl)-1,11-dihydroisochromeno[4',3':6,7]naphtho[1,2-d]imidazol-9-yl]-1H-imidazol-2-yl}pyrrolidin-1-yl)-3-methyl-1-oxobutan-2-yl]carbamnic acid (231 mg, 45%). LCMS-ESI$^+$: calculated for C46H48N8O7$_8$: 824.92; observed [M+1]$^+$: 826.00.

Example LR

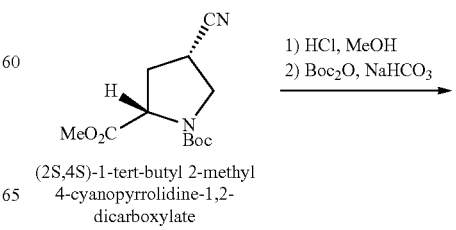

(2S,4S)-1-tert-butyl 2-methyl 4-cyanopyrrolidine-1,2-dicarboxylate

1) HCl, MeOH
2) Boc$_2$O, NaHCO$_3$
→

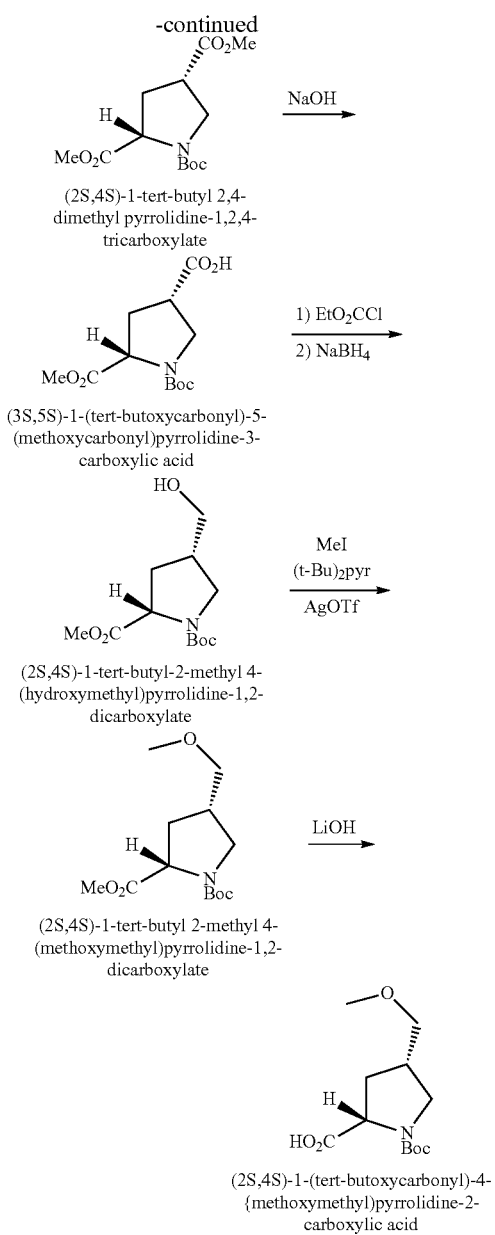

(2S,4S)-1-tert-butyl 2,4-dimethyl pyrrolidine-1,2,4-tricarboxylate (3S,5S)-1-(tert-butoxycarbonyl)-5-(methoxycarbonyl)pyrrolidine-3-carboxylic acid (2S,4S)-1-tert-butyl-2-methyl 4-(hydroxymethyl)pyrrolidine-1,2-dicarboxylate (2S,4S)-1-tert-butyl 2-methyl 4-(methoxymethyl)pyrrolidine-1,2-dicarboxylate (2S,4S)-1-(tert-butoxycarbonyl)-4-(methoxymethyl)pyrrolidine-2-carboxylic acid (2S,4S)-1-tert-butyl 2,4-dimethyl pyrrolidine-1,2,4-tricarboxylate. To a solution of (2S,4S)-1-tert-butyl 2-methyl 4-cyanopyrrolidine-1,2-dicarboxylate (9.0 g, 35.4 mmol) in MeOH (196 mL) was added HCl (4M in 1,4-dioxane, 100 mL, 403 mmol). The solution was stirred at room temperature for 16 h and concentrated in vacuo. The crude intermediate was dissolved in EtOAc (180 mL) and basified with aqueous bicarbonate (sat.). Di-tert-butyl dicarbonate (8.5 g, 38.9 mmol) was added and the biphsic solution was stirred at room temperature for 12 h. The layers were then separated and the aqueous layer was backextracted with EtOAc. The combined organic layers were washed with brine, dried over $Na_2SO_4$, and concentrated. The crude oil was purified by silica gel chromatography (15% to 40% to 100% EtOAc/Hexanes) to provide (2S,4S)-1-tert-butyl 2,4-dimethyl pyrrolidine-1,2,4-tricarboxylate (9.56 g, 94%).

(3S,5S)-1-(tert-butoxycarbonyl)-5-(methoxycarbonyl) pyrrolidine-3-carboxylic acid. To a solution of (2S,4S)-1-tert-butyl 2,4-dimethyl pyrrolidine-1,2,4-tricarboxylate (9.56 g, 33.3 mmol) in THF (70 mL) at 0° C. (external temperature, ice bath) was added NaOH (1N aqueous, 33 mL, 33.3 mmol) dropwise over 15 min. The solution was stirred at 0° C. for 5 h before acidification with HCl (1N). The solution was extracted with EtOAc (3×). The combined organic layers were dried over $Na_2SO_4$ and concentrated. The crude oil was purified by silica gel chromatography (2% to 5% to 10% MeOH/$CH_2Cl_2$) to provide (3S,5S)-1-(tert-butoxycarbonyl)-5-(methoxycarbonyl)pyrrolidine-3-carboxylic acid (6.38g, 70%).

(2S,4S)-1-tert-butyl 2-methyl 4-(hydroxymethyl)pyrrolidine-1,2-dicarboxylate. To a solution of (3S,5S)-1-(tert-butoxycarbonyl)-5-(methoxycarbonyl)pyrrolidine-3-carboxylic acid (6.38 g, 23.3 mmol) in THF (116 mL) at 0° C. (external temperature, ice bath) was added $Et_3N$ (4.9 mL, 35.0 mmol) and ethyl chloroformate (2.7 mL, 28.0 mmol). The resulting solution was stirred at 0° C. for 45 min, during which time a white precipitate forms. The reaction mixture was filtered through celite and concentrated.

The crude intermediate was dissolved in THF (59 mL) and cooled to 0° C. (external temperature, ice bath). $NaBH_4$ (4.41 g, 116.7 mmol) in $H_2O$ (59 mL) was slowly added and the resulting solution was stirred at 0° C. for 2 h. The reaction mixture was diluted with EtOAc and washed with $H_2O$. The aqueous layer was backextracted with EtOAc. The combined organic layers were dried over $Na_2SO_4$ and concentrated. The crude oil was purified by silica gel chromatography (42% to 69% to 100% EtOAc/Hexanes) to provide (2S,4S)-1-tert-butyl 2-methyl 4-(hydroxymethyl)pyrrolidine-1,2-dicarboxylate (3.63 g, 60%).

(2S,4S)-1-tert-butyl 2-methyl 4-(methoxymethyl)pyrrolidine-1,2-dicarboxylate. To a solution of (2S,4S)-1-tert-butyl 2-methyl 4-(hydroxymethyl)pyrrolidine-1,2-dicarboxylate (2.57 g, 9.9 mmol) in $CH_2Cl_2$ (50 mL) was added AgOTf (4.07 g, 15.8 mmol) and 2,6-di-tert-butylpyridine (4.4 mL, 19.8 mmol). The reaction mixture was cooled to 0° C. (external temperature, ice bath) and MeI (0.98 mL, 15.8 mmol) was slowly added. The resulting slurry was stirred at 0° C. for 1.5 h and at room temperature for 1.5 h. The slurry was diluted with $CH_2Cl_2$ and filtered through celite. The filtrate was concentrated to dryness, dissolved in $Et_2O$, and washed with HCl (1N) and brine. The aqueous layers were backextracted with $Et_2O$ and the combined organic layers were dried over $Na_2SO_4$ and concentrated. The crude oil was purified by silica gel chromatography (10% to 75% to 100% EtOAc/Hexanes) to provide (2S,4S)-1-tert-butyl 2-methyl 4-(methoxymethyl)pyrrolidine-1,2-dicarboxylate (2.11 g, 78%). $^1$H-NMR: 400 MHz, ($CDCl_3$) δ: (mixture of rotomers, major reported) 4.20 (t, 1H), 3.71 (s, 3H), 3.67 (m, 1H), 3.34 (m, 2H), 3.30 (s, 3H), 3.16 (t, 1H), 2.43 (m, 2H), 1.74 (m, 1H), 1.38 (s, 9H).

(2S,4S)-1-(tert-butoxycarbonyl)-4-(methoxymethyl)pyrrolidine-2-carboxylic acid. To a solution of (2S,4S)-1-tert-butyl 2-methyl 4-(methoxymethyl)pyrrolidine-1,2-dicarboxylate (2.11 g, 7.7 mmol) in a mixture of THF (38 mL) and McOH (15 mL) was added LiOH (2.5 M aqueous, 15 mL, 38.6 mmol). The resulting solution was stirred at room temperature for 2 h, and acidified with aqueous HCl (1N). The desired product was extracted with $CH_2C_2$ (4×). The combined organic layers were dried over $Na_2SO_4$ and concentrated to provide (2S,4S)-1-(tert-butoxycarbonyl)-4-(methoxymethyl)pyrrolidine-2-carboxylic acid (2.0 g, 99%). $^1$H-NMR: 400 MHz, ($CDCl_3$) δ: (mixture of rotomers, major reported) 4.33 (t, 1H), 3.65 (m, 1H), 3.35 (m, 2H), 3.32 (s, 3H), 3.16 (t, 1H), 2.45 (m, 2H), 2.12 (m, 1H), 1.46 (s, 9H).

Example LR-1
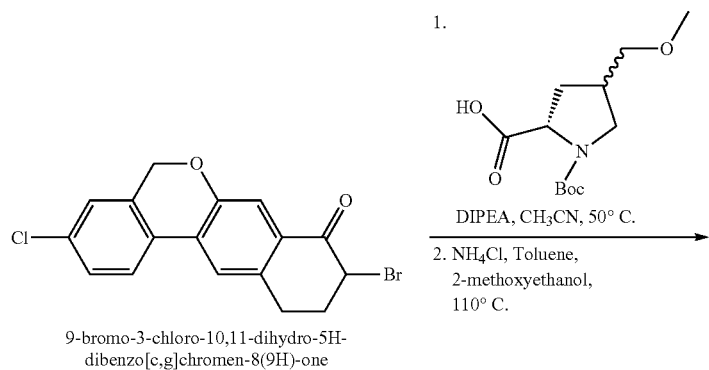
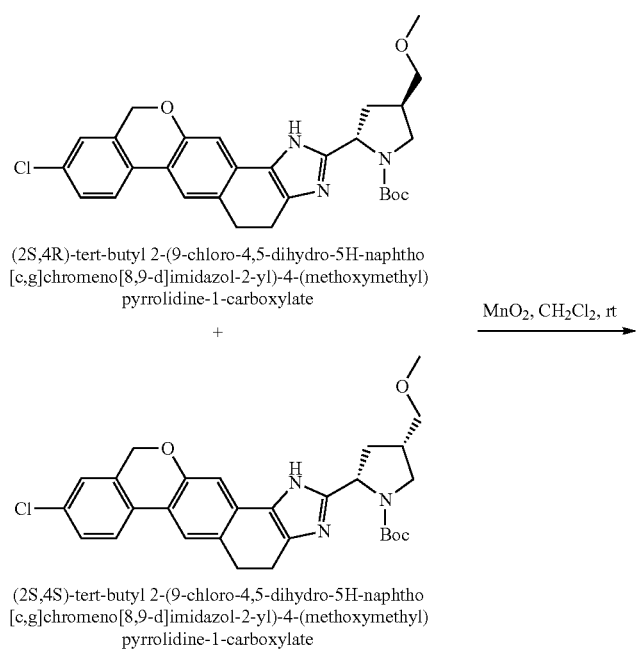
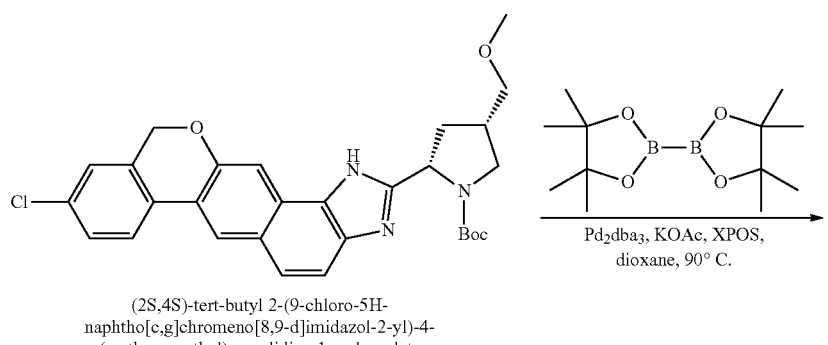

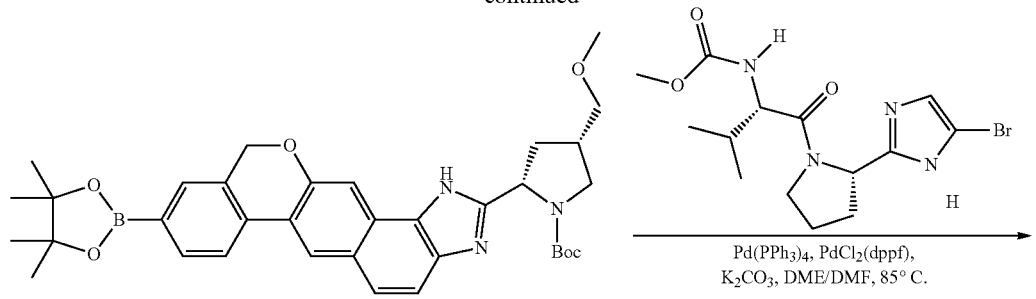

(2S,4S)-tert-butyl 4-(methoxymethyl)-2-(9-(4,4,5,5-tetramethyl-1,3,2-dioxaborolan-2-yl)-5H-naphtho[c,g]chromeno[8,9-d]imidazol-2-yl)pyrrolidine-1-carboxylate

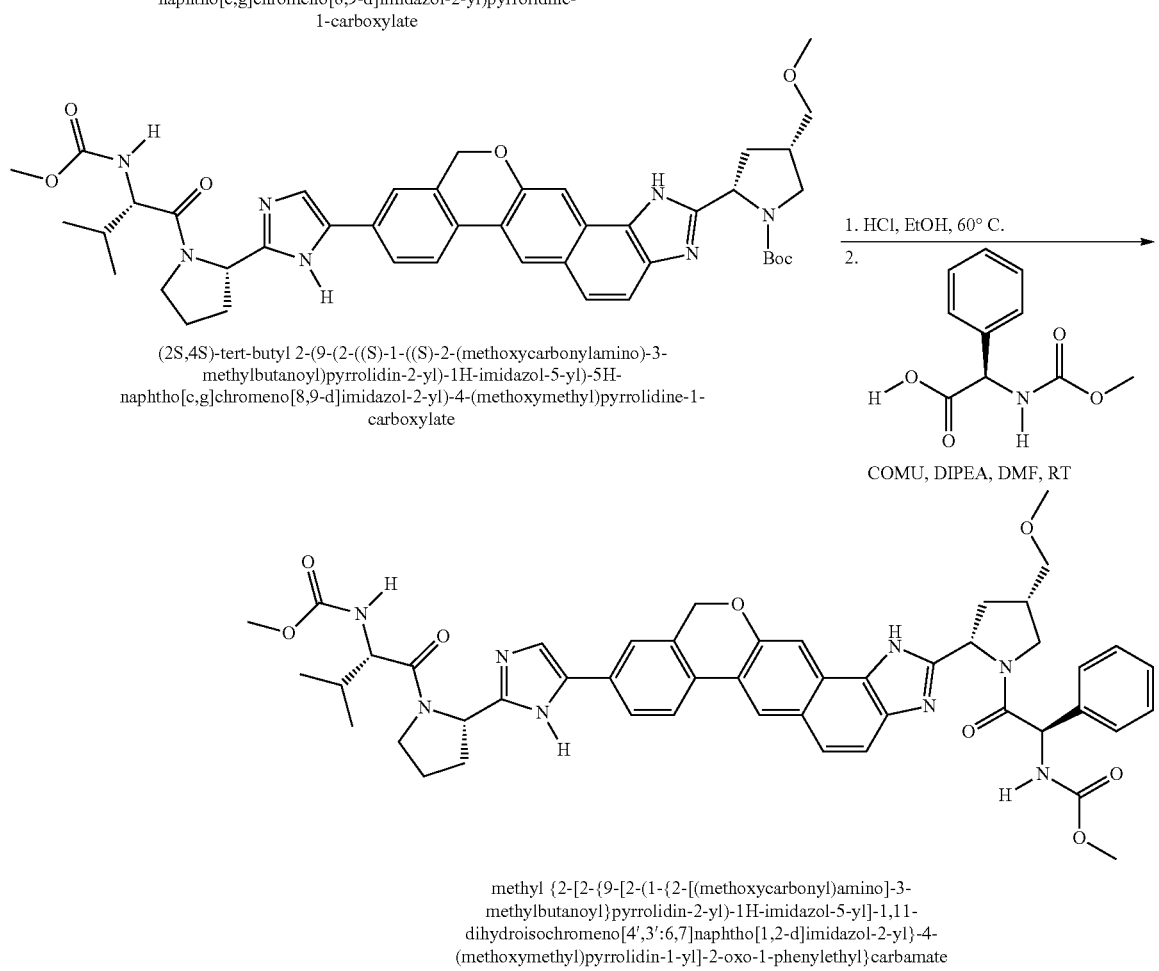

(2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-(methoxymethyl)pyrrolidine-1-carboxylate methyl {2-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate (2S,4S)-tert-butyl-2-(9-chloro-4,5-dihydro-5H-naphtho[2,3-c]chromeno[8,9-d]imidazol-2-yl)-4-(methoxymethyl)pyrrolidine-1-carboxylate: To a solution of ((S)-1-(tert-butoxycarbonyl)-4-(methoxymethyl)pyrrolidine-2-carboxylic acid (5.9 g, 23.1 mmol) and 9-bromo-3-chloro-10,11-dihydro-5H-naphtho[c,g]chromen-8(9H)-one (5.6 mg, 15.4 mmol) in acetonitrile (60 mL) was added diisopropylethylamine (5.35 mL, 30.8 mmol). The reaction was stirred at 50° C. for 18 hours and was then diluted with ethyl acetate. The organics were washed with water and brine, dried (MgSO$_4$) and concentrated. The resulting crude residue was purified by flash chromatography to yield (2S)-1-tert-butyl-2-(3-chloro-8-oxo-8,9,10,11-tetrahydro-6H-naphtho[2,3-c]chromen-9-yl)-4(methoxymethyl) pyrrolidine-1,2-dicarboxylate (5.12 g, 61%). To a solution of (2S)-1-tert-butyl-2-(3-chloro-8-oxo-8,9,10,11-tetrahydro-6H-naphtho[2,3-c]chromen-9-yl)-4(methoxymethyl)pyrrolidine-1,2-dicarboxylate (5.11 mg, 9.42 mmol) in a mixture of toluene (94 mL) and 2-methoxyethanol (0.1 mL) was added ammonium acetate (23.5 g, 304 mmol). The reaction mixture was heated to 110° C. for 18 hours, cooled to room temperature and diluted with ethyl acetate. The organics were washed with water and brine, dried (Na$_2$SO$_4$), and concentrated. The crude residue was purified by flash chromatography to yield (2S,4R)-tert-butyl 2-(9-chloro-4,5-dihydro-5H-naphtho[c,g]chromeno[8,9-d]imidazol-2-yl)-4-(methoxymethyl)pyrrolidine-1-carboxylate (1.05g, 21%) and (2S,4S)-tert-butyl-2-(9-chloro-4,5-dihydro-6H-naphtho[2,3-c]chromeno[8,9-d]imidazol-2-yl)-4-(methoxymethyl)pyrrolidine-1-carboxylate (2.0 g, 41%). LCMS-ESI+: calculated for $C_{29}H_{32}ClN_3O_{42}$: 522.0; observed [M+1]+: 522.2.

(2S,4S)-tert-butyl-2-(9-chloro-5H-naphtho[c,g]chromeno[8,9-d]imidazol-2-yl)-4-(methoxymethyl)pyrrolidine-1-carboxylate. To a solution of (2S,4S)-tert-butyl-2-(9-chloro-4,5-dihydro-5H-naphtho[c,g]chromeno[8,9-d]imidazol-2-yl)-4-(methoxymethyl)pyrrolidine-1-carboxylate (1.99 g, 3.82 mmol) in dichloromethane (30 mL) was added manganese (IV) oxide (10 g, 115 mmol). The reaction mixture was stirred at room temperature for 18 hours, diluted with ethyl acetate. The organics were washed with water and brine, dried (Na2SO4), and concentrated. The crude residue was purified by flash chromatography to yield (2S,4S)-tert-butyl-2-(9-chloro-6H-naphtho[2,3-c]chromeno[8,9-d]imidazol-2-yl)-4-methoxymethyl)pyrrolidine-1-carboxylate (1.05g, 21%) and (2S,4S)-tert-butyl-2-(9-chloro-4,5-dihydro-6H-naphtho[2,3-c]chromeno[8,9-d]imidazol-2-yl)-4-(methoxymethyl)pyrrolidine-1-carboxylate (1.64 g, 82%). LCMS-ESI+: calculated for $C_{29}H_{30}ClN_3O_{42}$: 520.02; observed [M+1]+: 520.97.

(2S,4S)-tert-butyl-4-(methoxymethyl)-2-(9-(4,4,5,5-tetramethyl-1,3,2-dioxaborolan-2-yl)-5H-naphtho[c,g]chromeno[8,9-d]imidazol-2-yl)pyrrolidine-1-carboxylate: A degassed mixture of -(2S,4S)-tert-butyl-2-(9-chloro-5H-naphtho[c,g]chromeno[8,9-d]imidazol-2-yl)-4-(methoxymethyl) pyrrolidine-1-carboxylate (649 mg 1.25 mmol), bis(pinacolato)diboron (635 mg, 2.5 mmol), potassium acetate (368 mg, 3.7 mmol), tris(dibenzylideneacetone)palladium (46 mg, 0.05 mmol) and 2-dicyclohexylphosphino-2',4',6'-tri-i-propyl-1,1'-biphenyl (60 mg, 0.12 mmol) in 1,4-dioxane (7 mL) was heated to 90° C. for 3 hours, cooled to room temperature and diluted with ethyl acetate. The organics were washed with water and brine, dried (Na2SO4), and concentrated. The crude residue was purified by flash chromatography to yield (2S,4S)-tert-butyl 4-(methoxymethyl)-2-(9-(4,4,5,5-tetramethyl-1,3,2-dioxaborolan-2-yl)-5H-naphtho[c,g]chromeno[8,9-d]imidazol-2-yl) pyrrolidine-1-carboxylate (467 mg, 61%) LCMS-ESI+: calculated for $C_{35}H_{42}BN_3O_6$: 611.54; observed [M+1]+: 612.96.

(2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4(methoxymethyl)pyrrolidine-1-carboxylate To a solution of (2S,4S)-tert-butyl 4-(methoxymethyl)-2-(9-(4,4,5,5-tetramethyl-1,3,2-dioxaborolan-2-yl)-5H-naphtho[c,g]chromeno[8,9-d]imidazol-2-yl)pyrrolidine-1-carboxylate (467 mg, 0.76 mmol), methyl (S)-1-((S)-2-(5-bromo-1H-imidazol-2-yl)pyrrolidin-1-yl)-3-methyl-1-oxobutan-2-ylcarbamate (342 mg, 0.92 mmol), tetrakis(triphenylphosphine) palladium(0) (44 mg, 0.04 mmol) and dichloro[1,1'-bis(diphenylphosphino)ferrocene]palladium(II) (56 mg, 0.07 mmol) in a mixture of 1,2-dimethoxyethane (11.0 mL) and dimethylformamide (1.9 mL) was added a solution of potassium carbonate (2M in water, 1.15 mL, 2.29 mmol). The resulting mixture was degassed and then heated to 85° C. under argon for 18 hours. After cooling to room temperature, the reaction was diluted with ethyl acetate. The organics were washed with water and brine, dried (Na2SO4), and concentrated. The crude residue was purified by flash chromatography to yield (2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-(methoxymethyl)pyrrolidine-1-carboxylate (180 mg, 67%). LCMS-ESI+: calculated for $C_{43}H_{51}N_7O_{73}$ 777.91; observed [M+1]+: 778.84.

methyl {2-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate: A solution of (2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-(methoxymethyl) pyrrolidine-1-carboxylate (196 mg, 0.25 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (69 mg, 0.33 mmol) and COMU (124 mg, 029 mmol) in DMF (4 mL). To the resulting solution was added diisopropylethylamine (130 μL, 0.76 mmol). After stirring for 2 hours at room temperature, the reaction was diluted with ethyl acetate, washed with water and brine, dried (Na2SO4), concentrated and purified by preparative reverse phase HPLC (Gemini, 15 to 45% ACN/H2O+0.1% TFA). The product fractions were lyophilized to give methyl {2-[2-{9-[2-(1-{2-[(methoxycarbonyl)amino]-3-methylbutanoyl}pyrrolidin-2-yl)-1H-imidazol-5-yl]-1,11-dihydroisochromeno[4',3': 6,7]naphtho[1,2-d]imidazol-2-yl}-4-(methoxymethyl)pyrrolidin-1-yl]-2-oxo-1-phenylethyl}carbamate (84 mg, 39%). LCMS-ESI+: calculated for $C_{48}H_{52}N_8O_8$: 868.98; observed [M+1]+: 870.11.

Example LS

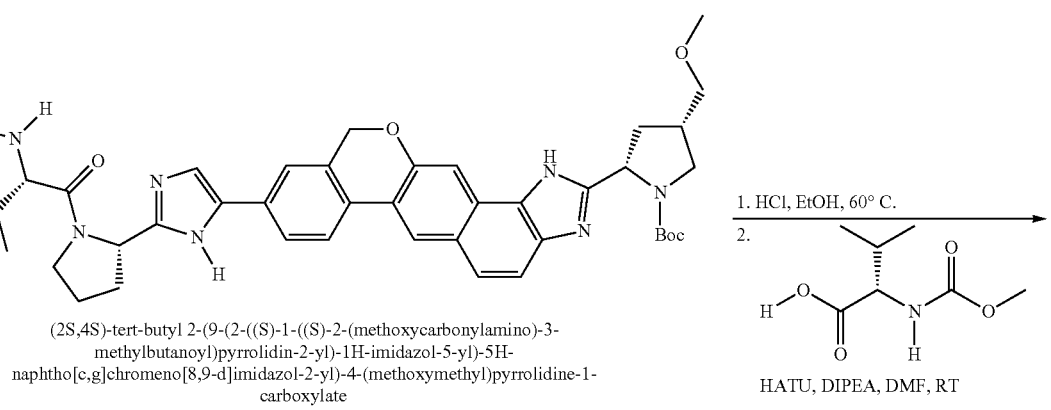

(2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-(methoxymethyl)pyrrolidine-1-carboxylate 1. HCl, EtOH, 60° C.
2.

HATU, DIPEA, DMF, RT

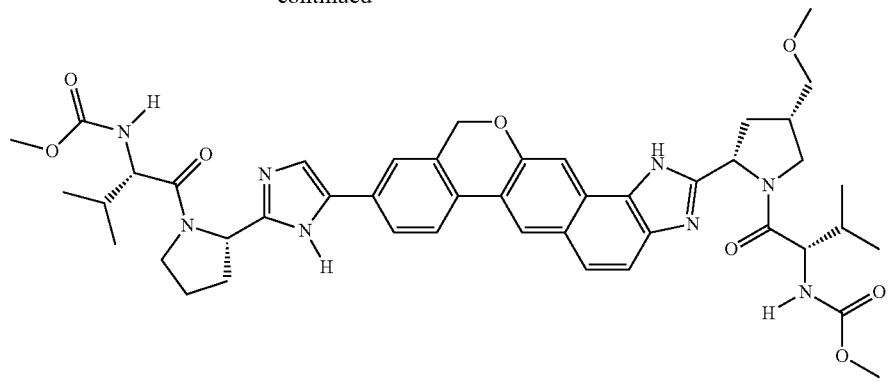

methyl {1-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate methyl {1-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate: A solution of (2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-(methoxymethyl)pyrrolidine-1-carboxylate (116 mg, 0.15 mmol), ethanol (5 mL) and concentrated HCl (1 mL) was heated to 60° C. for 1 hour. The reaction was concentrated and the crude material dissolved in DCM (10 mL). This solution was concentrated and to this material was added a solution of 2-methoxycarbonylamino-3-methylbutyric acid (38 mg, 0.22 mmol) and HATU (79 mg, 0.21 mmol) in DMF (1.4 mL). To the resulting solution was added diisopropylethylamine (270 µL, 1.5 mmol). After stirring for 18 hours at room temperature, the reaction was diluted with ethyl acetate, washed with water and brine, dried (Na$_2$SO$_4$), concentrated and purified by preparative reverse phase HPLC (Gemini, 15 to 45% ACN/H$_2$O+0.1% TFA). The product fractions were lyophilized to give methyl {1-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate (58 mg, 13%). LCMS-ESI$^+$: calculated for C$_{45}$H$_{54}$N$_8$O$_8$: 834.96; observed [M+1]$^+$: 835.70.

Example LT

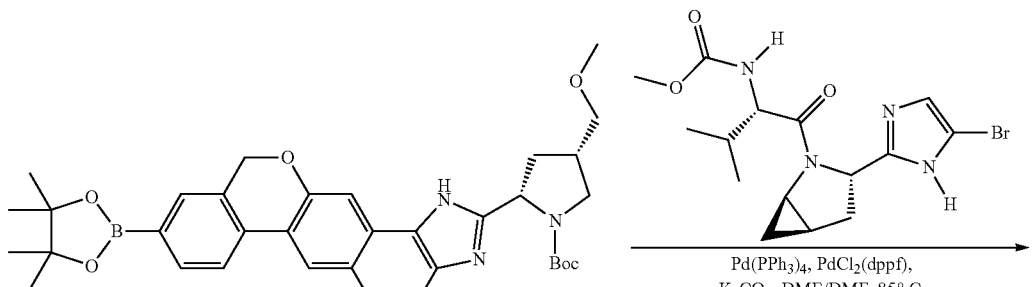

(2S,4S)-tert-butyl 4-(methoxymethyl)-2-(9-(4,4,5,5-tetramethyl-1,3,2-dioxaborolan-2-yl)-5H-naphtho[c,g]chromeno(8,9-d]imidazol-2-yl)pyrrolidine-1-carboxylate Pd(PPh$_3$)$_4$, PdCl$_2$(dppf), K$_2$CO$_3$, DME/DMF, 85° C.

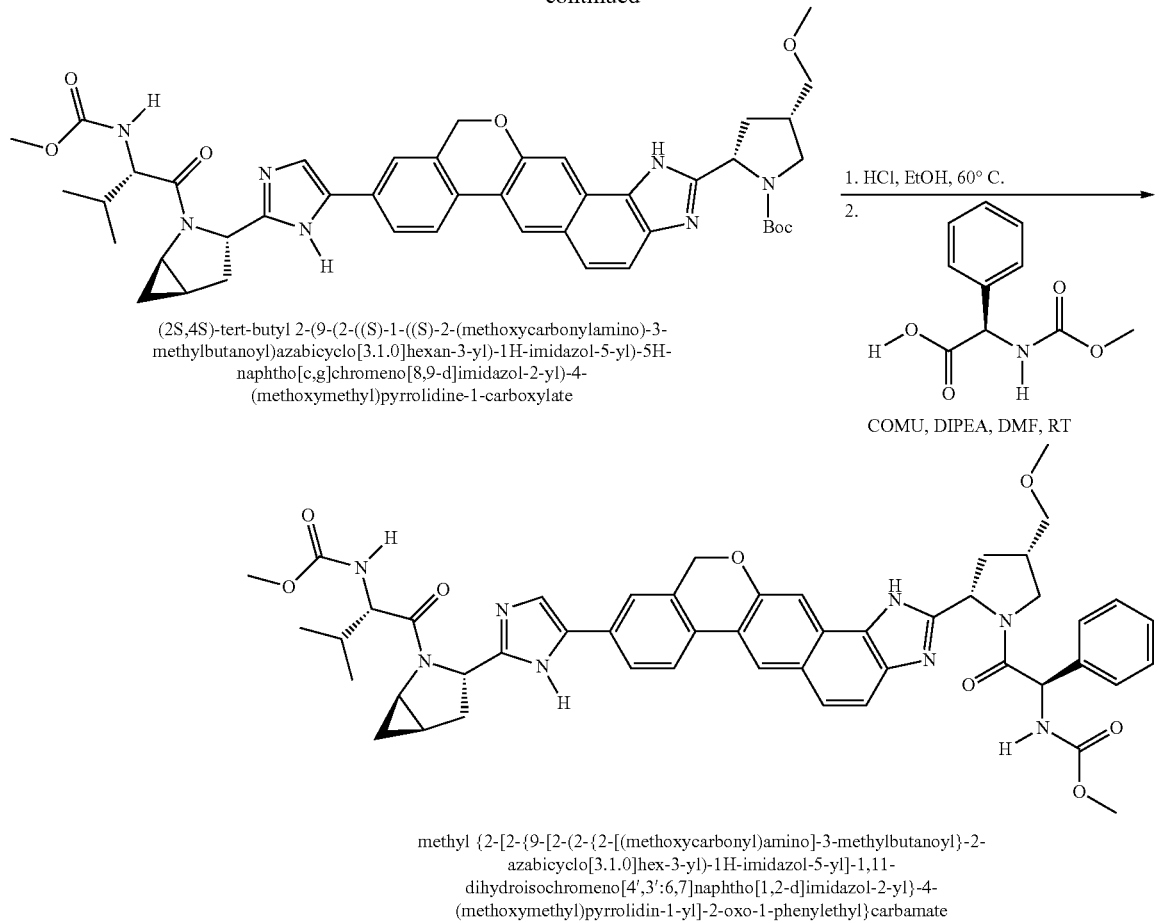

(2S,4S)-tert-butyl 2-(9-(2-((S)-1-((S)-2-(methoxycarbonylamino)-3-methylbutanoyl)azabicyclo[3.1.0]hexan-3-yl)-1H-imidazol-5-yl)-5H-naphtho[c,g]chromeno[8,9-d]imidazol-2-yl)-4-(methoxymethyl)pyrrolidine-1-carboxylate methyl {2-[2-{9-[2-(2-{2-[(methoxycarbonyl)amino]-3-methylbutanoyl}-2-azabicyclo[3.1.0]hex-3-yl)-1H-imidazol-5-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate (2S,4S)-tert-butyl-2-(9-(2-((S)-1-((S)-2-(methoxycarbonylamino)methylbutanoyl)azabicyclo[3.1.0]hexan-3-yl)-1H-imidazol-5-yl)-5H-naphtho[c,g]chromeno[8,9-d]imidazol-2-yl)-4-(methoxymethyl)pyrrolidine-1-carboxylate To a solution of (2S,4S)-tert-butyl 4-(methoxymethyl)-2-(9-(4,4,5,5-tetramethyl-1,3,2-dioxaborolan-2-yl)-5H-naphtho[c,g]chromeno[8,9-d]imidazol-2-yl)pyrrolidine-1-carboxylate (557 mg, 0.91 mmol), methyl (S)-1-((1 S,3S,5S)-3-(5-bromo-1H-imidazol-2-yl)-2-azabicyclo[3.1.0]hexan-2-yl)-3-methyl-1-oxobutan-2-ylcarbamate (350 mg, 0.91 mmol) tetrakis(triphenylphosphine) palladium(0) (53 mg, 0.04 mmol) and dichloro[1,1'-bis(diphenylphosphino)ferrocene] palladium(II) (67 mg, 0.07 mmol) in a mixture of 1,2-dimethoxyethane (11.0 mL) and dimethylformamide (1.9 mL) was added a solution of potassium carbonate (2M in water, 1.37 mL, 2.7 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield (2S,4S)-tert-butyl 2-(9-(2-((S)-1-((S)-2-(methoxycarbonylamino)-3-methylbutanoyl)azabicyclo[3.1.0]hexan-3-yl)-1H-imidazol-5-yl)-5H-naphtho[c,g]chromeno[8,9-d]imidazol-2-yl)-4-(methoxymethyl)pyrrolidine-1-carboxylate (271 mg, 38%). LCMS-ESI$^+$: calculated for C44H51N7O7. 789.92; observed [M+1]$^+$: 790.76.

methyl {2-[2-{9-[2-(2-{2-[(methoxycarbonyl)amino]-3-methylbutanoyl}-2-azabicyclo[3.1.0]hex-3-yl)-1H-imidazol-5-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate: A solution of (2S,4S)-tert-butyl 2-(9-(2-((S)-1-((S)-2-(methoxycarbonylamino)-3-methylbutanoyl)azabicyclo[3.1.0]hexan-3-yl)-1H-imidazol-5-yl)-5H-naphtho[c,g]chromeno[8,9-d]imidazol-2-yl)-4-(methoxymethyl)pyrrolidine-1-carboxylate (196 mg, 0.25 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (69 mg, 0.33 mmol) and COMU (124 mg, 029 mmol) in DMF (4 mL). To the resulting solution was added diisopropylethylamine (130 µL, 0.76 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 45% ACN/H$_2$O+0.1% TFA). The product fractions were lyophilized to give methyl {2-[2-{9-[2-(2-{2-[(methoxycarbonyl)amino]-3-methylbutanoyl}-2-azabicyclo[3.1.0]hex-3-yl)-1H-imidazol-5-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate (84 mg, 39%). LCMS-ESI$^+$: calculated for C49H52N8O8: 880.99; observed [M+1]$^+$: 882.09.

Example LU
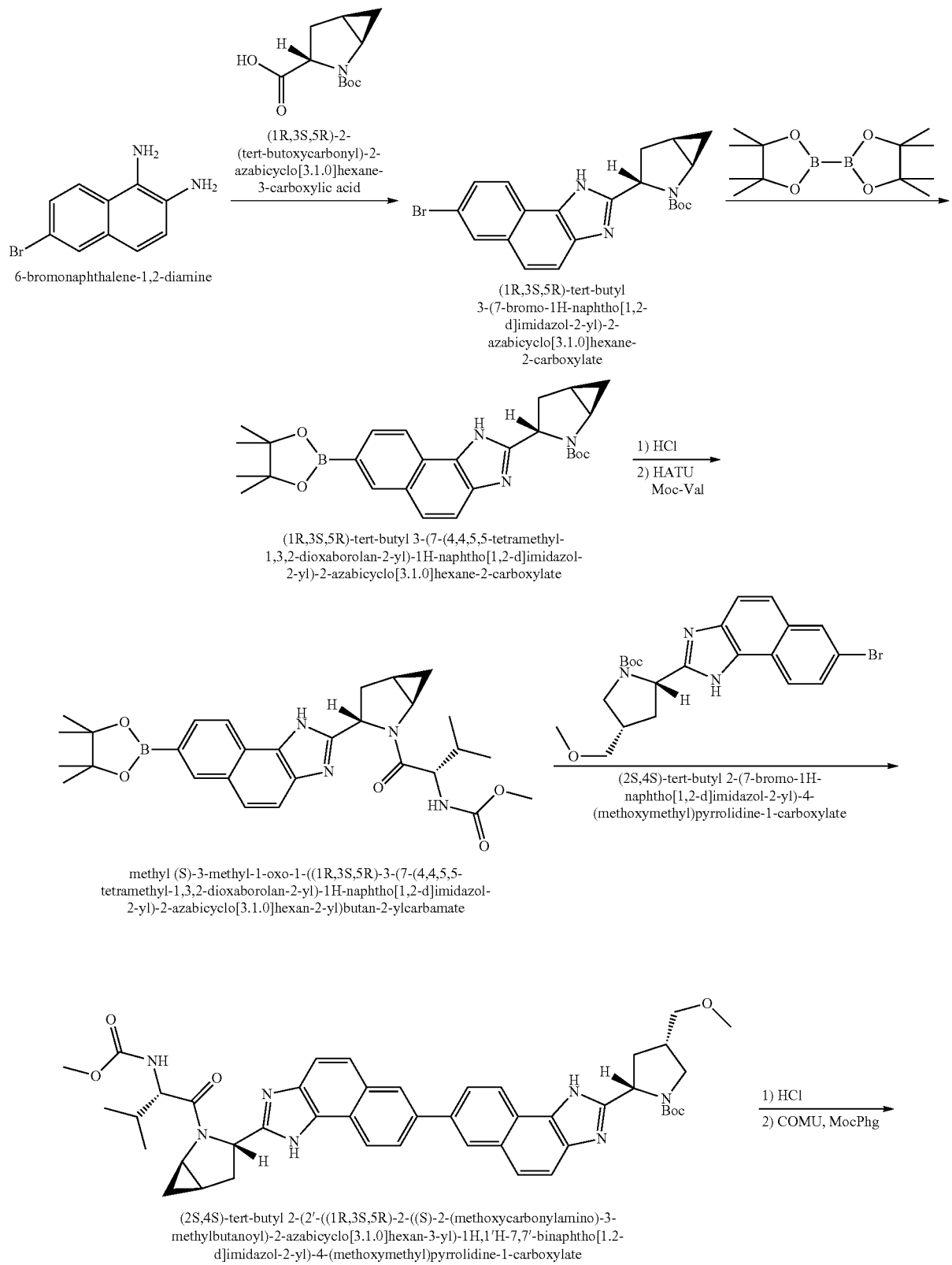

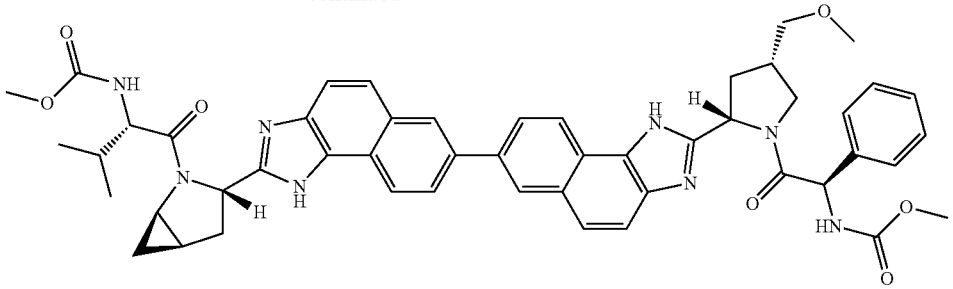

methyl (R)-((2S,4S)-4-(methoxymethyl)-2-(2'-((1R,3S,5R)-2-((S)-3-methyl-2-methoxycarbonylaminobutanoyl)-2-azabicyclo[3.1.0]hexan-3-yl)-1H,1'H-7,7'-binaphtho[1,2-d]imidazol-2-yl)pyrrolidin-1-yl)-2-oxo-1-phenylethylcarbamate (1R,3S,5R)-tert-butyl 3-(7-bromo-1H-naphtho[1,2-d]imidazol-2-yl)-2-azabicyclo[3.1.0]hexane-2-carboxylate. To a solution of (1R,3S,5R)-2-(tert-butoxycarbonyl)-2-azabicyclo[3.1.0]hexane-3-carboxylic acid (3.0 g, 13.5 mmol), 6-bromonaphthalene-1,2-diamine (3.1 g, 13.1 mmol), and HATU (5.6 g, 14.7 mmol) in CH$_2$Cl$_2$ (125 mL) was added DIPEA (10.8 mL, 61.8 mmol). The solution was stirred at room temperature for 4 hour and concentrated to dryness. The crude oil was dissolved in EtOAc and washed with water and brine.

The aqueous layers were backextracted with EtOAc, and the combined organic layers were dried over Na$_2$SO$_4$ and concentrated to dryness. The crude oil was purified by silica gel chromatography (20 to 100% EtOAc(5% MeOH)/Hexanes).

The resulting intermediate was dissolved in AcOH (125 mL), and stirred at room temperature for 18 h. The solution was concentrated and the crude oil was dissolved in EtOAc. The solution was washed with aqueous bicarbonate (sat.) and brine. The aqueous layers were backextracted with EtOAc and the combined organic layers were dried over Na$_2$SO$_4$ and concentrated. The crude oil was purified by silica gel chromatography (2 to 5% MeOH/CH$_2$Cl$_2$) to provide (1R,3S,5R)-tert-butyl 3-(7-bromo-1H-naphtho[1,2-d]imidazol-2-yl)-2-azabicyclo[3.1.0]hexane-2-carboxylate (5.08 g, 91%). LCMS-ESI$^+$: calc'd for C$_{21}$H$_{22}$BrN$_3$O$_2$: 427.09 (M$^+$); Found: 428.71 (M+H$^+$).

(1R,3S,5R)-tert-butyl 3-(7-(4,4,5,5-tetramethyl-1,3,2-dioxaborolan-2-yl)-1H-naphtho[1,2-d]imidazol-2-yl)-2-azabicyclo[3.1.0]hexane-2-carboxylate. To a solution of (1R,3S,5R)-tert-butyl 3-(7-bromo-1H-naphtho[1,2-d]imidazol-2-yl)-2-azabicyclo[3.1.0]hexane-2-carboxylate (2.06 g, 4.8 mmol), 4,4,4',4',5,5,5',5'-octamethyl-2,2'-bi(1,3,2-dioxaborolane) (1.84, 7.2 mmol), KOAc (1.41 g, 14.4 mmol) in 1,4-dioxane (50 mL) was added Pd(dppf)Cl$_2$ (0.18 g, 0.3 mmol). The slurry was degassed with argon for 5 min and heated to 80° C. (external temperature, oil bath). The reaction was stirred at 80° C. for 5 h, and then cooled to room temperature for 15 h. The solution was diluted with EtOAc and filtered through celite. After concentration of the solution, the crude oil was purified twice by silica gel chromatography (first column: 25 to 100% EtOAc(5% MeOH)/Hexanes); second column: 2 to 5% MeOH/CH$_2$Cl$_2$) to provide (1R,3 S,5R)-tert-butyl 3-(7-(4,4,5,5-tetramethyl-1,3,2-dioxaborolan-2-yl)-1H-naphtho[1,2-d]imidazol-2-yl)-2-azabicyclo[3.1.0]hexane-2-carboxylate (2.17 g, 95%). LCMS-ESI$^+$: calc'd for C$_{27}$H$_{34}$BN$_3$O$_4$: 475.26 (M$^+$); Found: 476.11 (M+H$^+$).

methyl (S)-3-methyl-1-oxo-1-((1R,3S,5R)-3-(7-(4,4,5,5-tetramethyl-1,3,2-dioxaborolan-2-yl)-1H-naphtho[1,2-d]imidazol-2-yl)-2-azabicyclo[3.1.0]hexan-2-yl)butan-2-ylcarbamate.

To a solution of (1R,3S,5R)-tert-butyl 3-(7-(4,4,5,5-tetramethyl-1,3,2-dioxaborolan-2-yl)-1H-naphtho[1,2-d]imidazol-2-yl)-2-azabicyclo[3.1.0]hexane-2-carboxylate (0.60 g, 1.3 mmol) in a mixture of CH$_2$Cl$_2$ (12.0 mL) and MeOH (2.5 mL) was added HCl (4M in 1,4-dioxane, 9.4 mL, 37.6 mmol). The solution was stirred at room temperature for 2.5 h and concentrated to dryness. The crude intermediate was suspended in CH$_2$Cl$_2$ (12 mL). (S)-2-(methoxycarbonylamino)-3-methylbutanoic acid (0.25 g, 1.4 mmol), HATU (0.58 g, 1.5 mmol), and DIPEA (0.7 mL, 4.0 mmol) were sequentially added to the reaction. The homogenous solution was then stirred at room temperature for 1.5 h. The solution was diluted with CH$_2$Cl$_2$ and washed with HCl (aqueous, 1N) and aqueous bicarbonate (sat.). The aqueous layers were backextracted with CH$_2$Cl$_2$ and the combined organic layers were dried over Na$_2$SO$_4$ and concentrated. The crude oil was then purified by silica gel chromatography (30 to 100% EtOAc(5% MeOH)/Hexanes) to provide methyl (S)-3-methyl-1-oxo-1-((1R,3S,5R)-3-(7-(4,4,5,5-tetramethyl-1,3,2-dioxaborolan-2-yl)-1H-naphtho[1,2-d]imidazol-2-yl)-2-azabicyclo[3.1.0]hexan-2-yl)butan-2-ylcarbamate (0.60 g, 89%). LCMS-ESI$^+$: calc'd for C$_{29}$H$_{37}$BN$_4$O$_5$: 532.29 (M$^+$); Found: 533.11 (M+H$^+$).

(2S,4S)-tert-butyl 2-(2'-((1R,3S,5R)-2-((S)-2-(methoxycarbonylamino)-3-methylbutanoyl)-2-azabicyclo[3.1.0]hexan-3-yl)-1H,1'H-7,7'-binaphtho[1,2-d]imidazol-2-yl)-4-(methoxymethyl)pyrrolidine-1-carboxylate. To a solution of methyl (S)-3-methyl-1-oxo-1-((1R,3 S,5R)-3-(7-(4,4,5,5-tetramethyl-1,3,2-dioxaborolan-2-yl)-1H-naphtho[1,2-d]imidazol-2-yl)-2-azabicyclo[3.1.0]hexan-2-yl)butan-2-ylcarbamate (0.60 g, 1.1 mmol) and (2S,4S)-tert-butyl 2-(7-bromo-1H-naphtho[1,2-d]imidazol-2-yl)-4-(methoxymethyl)pyrrolidine-1-carboxylate (0.46 g, 1.0 mmol) in DME (5 mL) was added Pd(PPh$_3$)$_4$ (0.08 g, 0.07 mmol) and K$_3$PO$_4$ (2M aqueous, 1.5 mL, 3.0 mmol). The resulting solution was degassed with argon for 5 min and heated to 80° C. (external temperature, oil bath) for 18 h. The reaction mixture was then cooled to room temperature and diluted with MeOH and CH$_2$Cl$_2$. The solution was washed with H$_2$O and brine, and the aqueous layers were backextracted with CH$_2$Cl$_2$ and MeOH (~10:1). The organic layers were combined and dried over Na$_2$SO$_4$ and concentrated. The crude oil was purified by silica gel chromatography (30 to 100% EtOAc(10% MeOH)/Hexanes to 80% MeOH/EtOAc) to provide (2S,4S)-tert-butyl 2-(2'-((1R,3S, 5R)-2-((S)-2-(methoxycarbonylamino)-3-methylbutanoyl)-2-azabicyclo[3.1.0]hexan-3-yl)-1H, 1'H-7,7'-binaphtho[1,2-d]imidazol-2-yl)-4-(methoxymethyl)pyrrolidine-1-carboxylate (0.79 g, 71%). LCMS-ESI$^+$: calc'd for $C_{45}H_{51}N_7O_6$: 785.39 (M$^+$); Found: 786.61 (M+H$^+$).

methyl (R)-2-((2S,4S)-4-(methoxymethyl)-2-(2'-((1R,3S,5R)-2-((S)-3-methyl-2-methoxycarbonylaminobutanoyl)-2-azabicyclo[3.1.0]hexan-3-yl)-1H,1'H-7,7'-binaphtho[1,2-d]imidazol-2-yl)pyrrolidin-1-yl)-2-oxo-1-phenylethylcarbamate. To a solution of (2S,4S)-tert-butyl 2-(2'-((1R,3 S,5R)-2-((S)-2-(methoxycarbonylamino)-3-methylbutanoyl)-2-azabicyclo[3.1.0]hexan-3-yl)-1H,1'H-7,7'-binaphtho[1,2-d]imidazol-2-yl)-4-(methoxymethyl)pyrrolidine-1-carboxylate (0.40 g, 0.5 mmol) in a mixture of $CH_2Cl_2$ (6.0 mL) and MeOH (1.0 mL) was added HCl (4M in 1,4-dioxane, 2.5 mL, 10.0 mmol). The solution was stirred at room temperature for 2.5 h and concentrated to dryness. The crude intermediate was purified by preparative HPLC (Gemini column, 10-50% MeCN/H$_2$O with 0.1% TFA). The combined fractions were basified with aqueous bicarbonate (sat.) and diluted with brine. The desired product was extracted with $CH_2Cl_2$ (3×). The combined organic layers were dried over $Na_2SO_4$ and concentrated.

The intermediate was dissolved in $CH_2Cl_2$ (2.5 mL). (R)-2-(methoxycarbonylamino)-2-phenylacetic acid (0.045 g, 0.21 mmol) and DIPEA (0.05 mL, 0.28 mmol) were then added to the solution. The reaction mixture was cooled to −40° C. (external temperature, MeCN/CO$_2$(s) bath). COMU (0.098 g, 0.23 mmol) was then added and solution was allowed to warm to 0° C. over 1 h. The solution was diluted with DMF and concentrated. The crude product was purified by preparative HPLC (Gemini column, 10-60% MeCN/H$_2$O with 0.1% TFA) and the desired fractions were combined. The solution was concentrated until the aqueous layer remained and aqueous bicarbonate (sat.) was slowly added until the solution was basic. The resulting slurry was stirred at room temperature for 2 h and filtered. The resulting solid was dried in vacuo to provide methyl (R)-2-((2S,4S)-4-(methoxymethyl)-2-(2'-((1R,3S,5R)-2-((S)-3-methyl-2-methoxycarbonylaminobutanoyl)-2-azabicyclo[3.1.0]hexan-3-yl)-1H,1'H-7,7'-binaphtho[1,2-d]imidazol-2-yl)pyrrolidin-1-yl)-2-oxo-1-phenylethylcarbamate (0.14 g, 75%). LCMS-ESI$^+$: calc'd for $C_{50}H_{52}N_8O_7$: 876.40 (M$^+$); Found: 877.82 (M+H$^+$).

Example LV

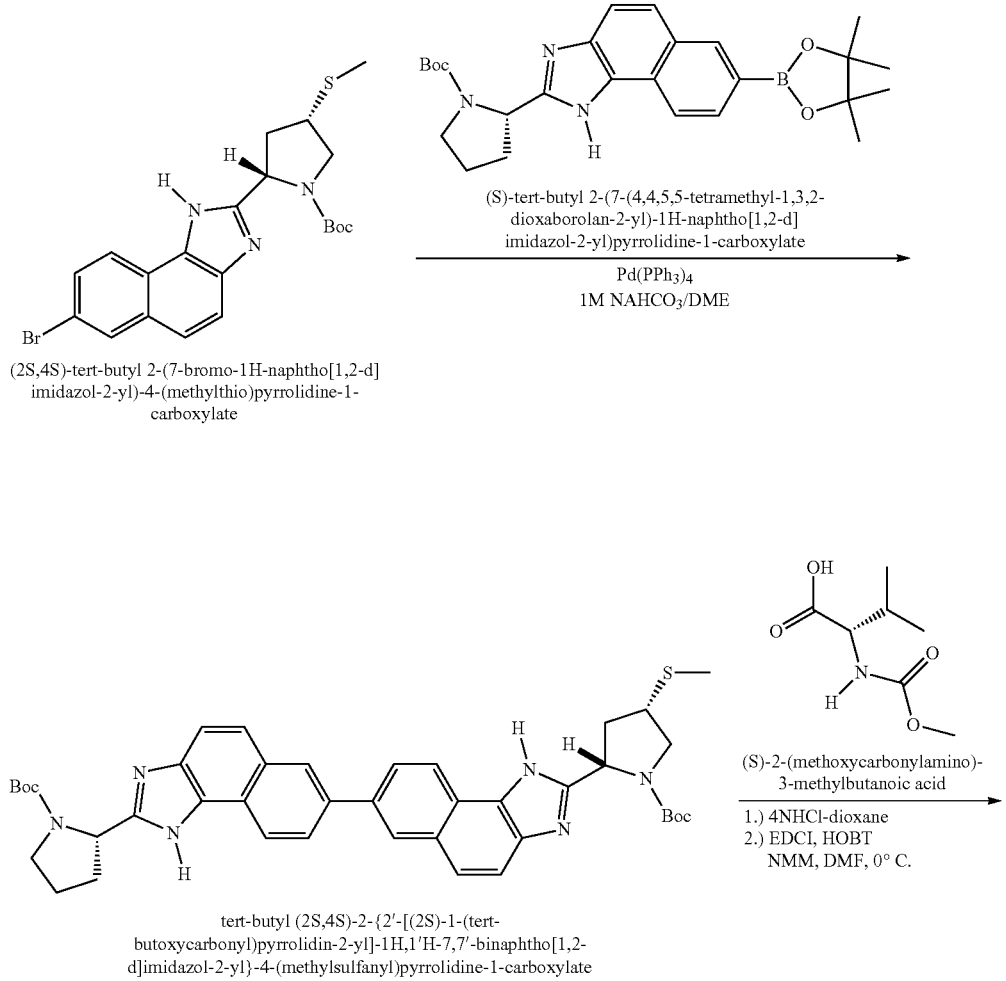

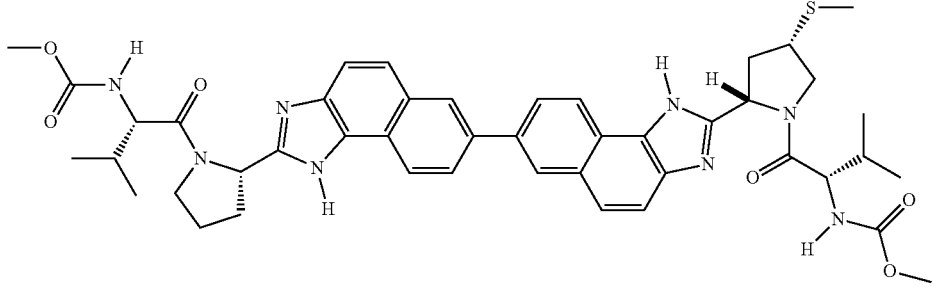

methyl {(2S)-1-[(2S,4S)-2-{2'-[(2S)-1-{(2S)-2-
[(methoxycarbonyl)amino]-3-methylbutanoyl}pyrrolidin-2-yl]-1H,1'H-
7,7'-binaphtho[1,2-d]imidazol-2-yl}-4-(methylsulfanyl)pyrrolidin-1-yl]-3-
methyl-1-oxobutan-2-yl]carbamate (2S,4S)-tert-butyl 2-(7-bromo-1H-naphtho[1,2-d]imidazol-2-yl)-4-(methylthio)pyrrolidine-1-carboxylate was synthesized using methods analogous to the preparation of (S)-tert-butyl 2-(7-bromo-1H-naphtho[1,2-d]imidazol-2-yl)pyrrolidine-1-carboxylate, substituting (2S,4S)-1-(tert-butoxycarbonyl)-4-(methylthio)pyrrolidine-2-carboxylic acid for (S)-1-(tert-butoxycarbonyl)pyrrolidine-2-carboxylic acid. (2S,4S)-1-(tert-butoxycarbonyl)-4-(methylthio)pyrrolidine-2-carboxylic acid is a known compound and may be prepared by one of the methods described in the following literature: J. Med. Chem. 38(1996), 137-149; Bioorganic & Medicinal Chemistry 14(2006), 2253-2265.

To (2S,4S)-tert-butyl 2-(7-bromo-1H-naphtho[1,2-d]imidazol-2-yl)-4-(methylthio)pyrrolidine-1-carboxylate (23 mg, 0.05 mmol), (S)-tert-butyl 2-(7-(4,4,5,5-tetramethyl-1,3,2-dioxaborolan-2-yl)-1H-naphtho[1,2-d]imidazol-2-yl)pyrrolidine-1-carboxylate (30 mg, 0.06 mmol), Pd(PPh$_3$)$_4$ (9 mg, 0.008 mmol). DME (0.5 mL) was added and followed by 0.25 mL 1M NaHCO$_3$ aqueous solution. The reaction was purged with Ar and heated to 120° C. at microwave synthesizer for 0.5 hour. The reaction was cooled to room temperature and concentrated down. EtOAc was added and washed with sat. NaHCO$_3$ aqueous (2x) and sat. NaCl aqueous (1x). The organic layer was concentrated down after drying over sodium sulfate and subject to reverse phase prep.HPLC to provide Intermediate LV1 (5.5 mg, 15%). MS (ESI) m/z 719 [M+H]$^+$.

To tert-butyl (2S,4S)-2-{2'-[(2S)-1-(tert-butoxycarbonyl)pyrrolidin-2-yl]-1H, 1'H-7,7'-binaphtho[1,2-d]imidazol-2-yl}-4-(methylsulfanyl)pyrrolidine-1-carboxylate (5 mg, 0.007 mmol) in dichloromethane (0.1 mL) was added 4M HCl in dioxane (0.1 mL) and the reaction mixture was cooled to 0° C. and then stirred for 2 hours. The reaction was then concentrated in vacuo to afford the HCl salt.

To the HCl salt in DMF (0.15 mL) was added (S)-2-(methoxycarbonylamino)-3-methylbutanoic acid (2.8 mg, 0.016 mmol), N-(3-dimethylaminopropyl)-N'-ethylcarbodiimide hydrochloride (2.8 mg, 0.015 mmol) and hydroxybenzotriazole hydrate (HOBt), (2 mg, 0.015 mmol). The mixture was cooled down in an ice bath to 0° C. and N-methylmorpholine (NMM)(4 µL, 0.035 mmol) was added from a syringe to the mixture. The reaction content was stirred for 4 hours at room temperature. The resulting mixture was then directly purified on reverse phase prep.HPLC to afford methyl {(2S)-1-[(2S,4S)-2-{2'-[(2S)-1-{(2S)-2-[(methoxycarbonyl)amino]-3-methylbutanoyl}pyrrolidin-2-yl]-1H,1'H-7,7'-binaphtho[1,2-d]imidazol-2-yl}-4-(methylsulfanyl)pyrrolidin-1-yl]-3-methyl-1-oxobutan-2-yl}carbamate as white solid (3.5 mg, 60%). MS (ESI) m/z 833.35 [M+H]$^+$.

Example LW

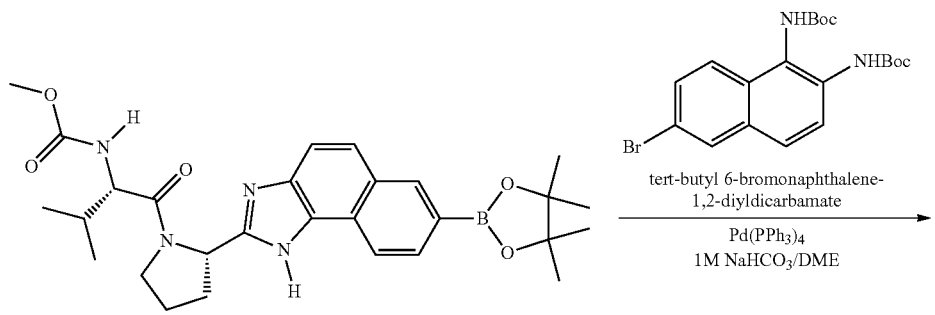

methyl (S)-3-methyl-1-oxo-1-((S)-2-(7-(4,4,5,5-tetramethyl-1,3,2-
dioxaborolan-2-yl)-1H-naphtho[1,2-d]imidazol-2-yl)pyrrolidin-1-yl)butan-2-
ylcarbamate tert-butyl 6-bromonaphthalene-
1,2-diyldicarbamate Pd(PPh$_3$)$_4$
1M NaHCO$_3$/DME -continued
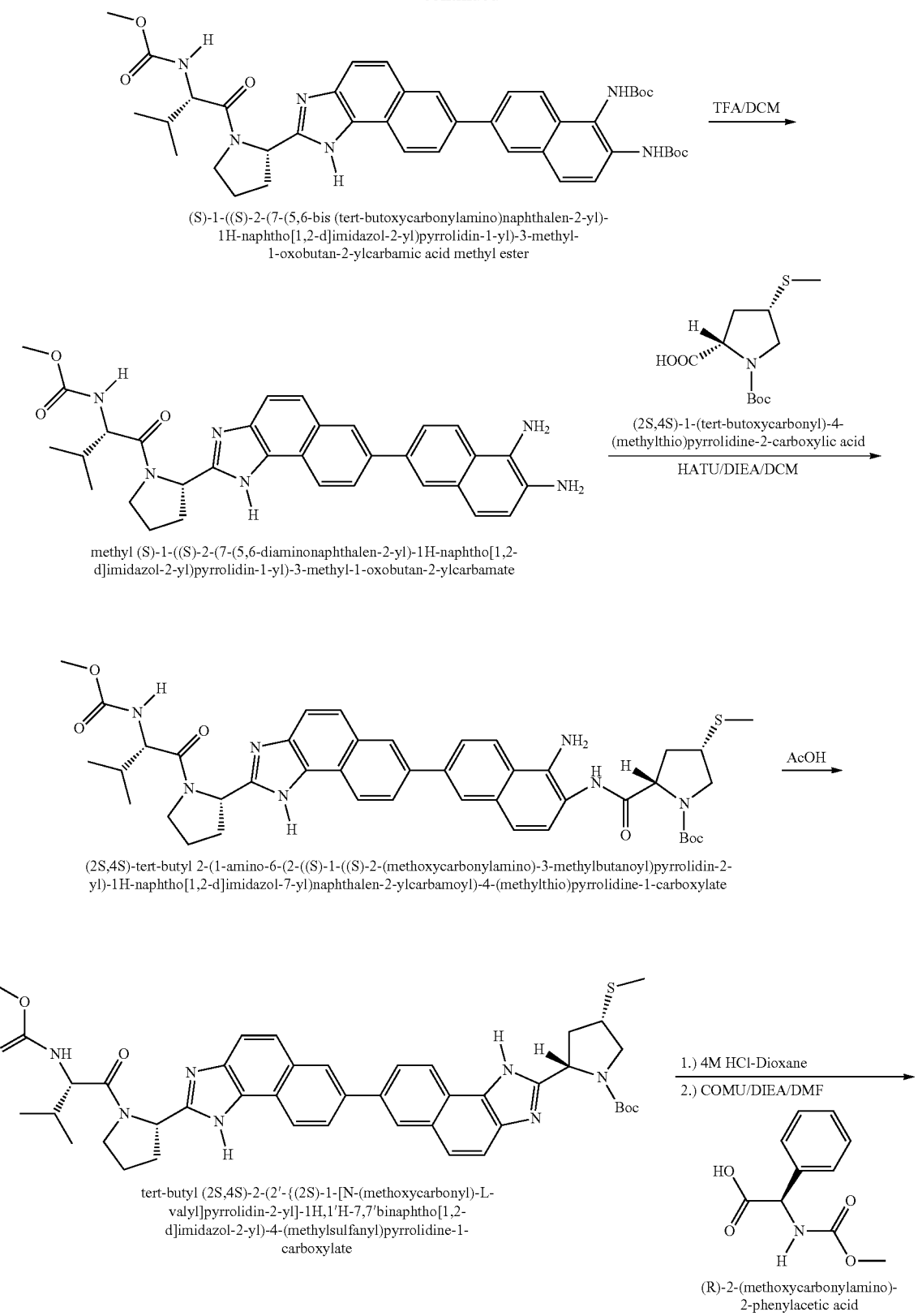

-continued

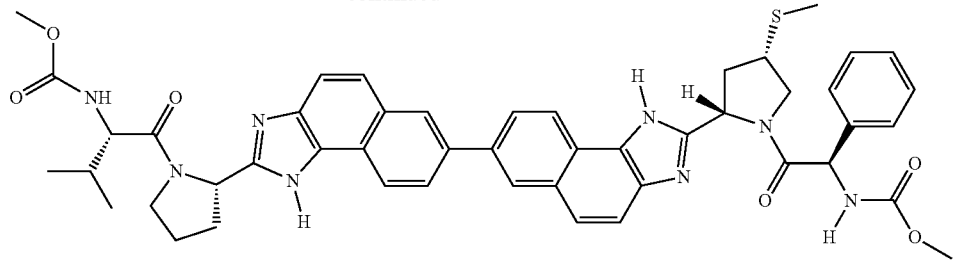

methyl {(1R)-2-[(2S,4S)-2-{2'-[(2S)-1-{(2S)-2-
[(methoxycarbonyl)amino]-3-methylbutanoyl}pyrrolidin-2-
yl]-1H,1'H-7,7'binaphtho[1,2-d]imidazol-2-yl}-4-
(methylsulfanyl)pyrrolidin-1-yl]-2-oxo-1-
phenylethyl}carbamate (S)-1-((S)-2-(7-(5,6-bis(tert-butoxycarbonylamino)naphthalen-2-yl)-1H-naphtho[1,2-d]imidazol-2-yl)pyrrolidin-1-yl)-3-methyl-1-oxobutan-2-ylcarbamic acid methyl ester: To methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate (190 mg, 0.36 mmol), tert-butyl 6-bromonaphthalene-1,2-diyldicarbamate (205 mg, 0.47 mmol), Pd(PPh$_3$)$_4$ (42 mg, 0.036 mmol). DME (1.5 mL) was added and followed by 1.08 mL 1M NaHCO$_3$ aqueous solution. The reaction was purged with Ar and heated to 120° C. at microwave synthesizer for 0.5 hour. The reaction was cooled to room temperature and concentrated down. EtOAc was added and washed with sat. NaHCO$_3$ aqueous (2×) and sat. NaCl aqueous (1×). The organic layer was concentrated down after drying over sodium sulfate and subject to silica gel chromatography with an eluent of ethyl acetate and hexane at a gradient of 40-100% with an ISCO column (12 g silica gel). The fractions containing product were combined and the solvent was removed under reduced pressure to provide the desired product (205 mg, 75%). MS (ESI) m/z 752 [M+H]$^+$.

Methyl (S)-1-((S)-2-(7-(5,6-diaminonaphthalene-2-yl)-1H-naphtho[1,2-d]imidazol-2-yl)pyrrolidin-1-yl)-3-methyl-1-oxobutan-2-ylcarbamate To (S)-1-((S)-2-(7-(5,6-bis(tert-butoxycarbonylamino) naphthalen-2-yl)-1H-naphtho[1,2-d]imidazol-2-yl)pyrrolidin-1-yl)-3-methyl-1-oxobutan-2-ylcarbamic acid methyl ester (165 mg, 0.22 mmol) in dichloromethane (2.2 mL) was added TFA (0.5 mL) and the reaction mixture stirred for 2 hours. The solvent was removed under reduced pressure to provide title compound as TFA salts.

(2S,4S)-tert-butyl 2-(1-amino-6-(2-((S)-1-((S)-2-(methoxycarbonylamino)-3-methylbutanoyl)pyrrolidin-2-yl)-1H-naphtho[1,2-d]imidazol-7-yl) naphthalen-2-ylcarbamoyl)-4-(methylthio)pyrrolidine-1-carboxylate To above TFA salts in DCM (2 mL) was added (2S,4S)-tert-butoxycarbonyl)-4-(methylthio)pyrrolidine-2-carboxylic acid (68 mg, 0.26 mmol), HATU (99 mg, 0.26 mmol). The mixture was cooled down in an ice bath to 0° C. and diisopropylethylamine (192 µL, 1.1 mmol) was added from a syringe to the mixture. The reaction mixture was stirred for 0.5 hours at room temperature. EtOAc was added and washed with sat. NaHCO$_3$ aqueous (2×) and sat. NaCl aqueous (1×). The organic layer was concentrated down after drying over sodium sulfate and subject to silica gel chromatography with an eluent of ethyl acetate and hexane at a gradient of 40-100% with an ISCO column (12 g silica gel). The fractions containing product were combined and the solvent was removed under reduced pressure to provide title compound (122 mg, 70%). MS (ESI) m/z 795 [M+H]$^+$.

tert-butyl (2S,4S)-2-(2'-{(2S)-1-[N-(methoxycarbonyl)-L-valyl]pyrrolidin-2-yl}-1H,1'H-7,7'-binaphtho[1,2-d]imidazol-2-yl)-4-(methylsulfanyl)pyrrolidine-1-carboxylate:

To (2S,4S)-tert-butyl 2-(1-amino-6-(2-((S)-1-((S)-2-(methoxycarbonylamino)-3-methylbutanoyl)pyrrolidin-2-yl)-1H-naphtho[1,2-d]imidazol-7-yl) naphthalen-2-ylcarbamoyl)-4-(methylthio)pyrrolidine-1-carboxylate (95 mg, 0.12 mmol) in acetic acid (4 mL) and the reaction mixture stirred for 16 hours. Concentrated in vacuo and diluted with EtOAc, washed with sat. NaHCO$_3$ aqueous (2×) and sat. NaCl aqueous (1×). The organic layer was concentrated down after drying over sodium sulfate and subject to silica gel chromatography with an eluent of ethyl acetate and hexane at a gradient of 40-100% with an ISCO column (12 g silica gel). The fractions containing product were combined and the solvent was removed under reduced pressure to provide tert-butyl (2S,4S)-2-(2'-{(2 S)-1-[N-(methoxycarbonyl)-L-valyl]pyrrolidin-2-yl}-1H,1'H-7,7'-binaphtho [1,2-d]imidazol-2-yl)-4-(methylsulfanyl)pyrrolidine-1-carboxylate (50 mg, 54%). MS (ESI) m/z 777 [M+H]$^+$.

methyl {(1R)-2-[(2S,4S)-2-{2'-[(2S)-1-{(2S)-2-[(methoxycarbonyl)amino]-3-methylbutanoyl}pyrrolidin-2-yl]-1H,1'H-7,7'-binaphtho[1,2-d]imidazol-2-yl}-4-(methylsulfanyl)pyrrolidin-1-yl]-2-oxo-1-phenylethyl}carbamate:

To tert-butyl (2S,4S)-2-(2'-{(2S)-1-[N-(methoxycarbonyl)-L-valyl]pyrrolidin-2-yl}-1H,1'H-7,7'-binaphtho[1,2-d] imidazol-2-yl)-4-(methylsulfanyl)pyrrolidine-1-carboxylate (15 mg, 0.02 mmol) in methanol (0.1 mL) was added 4M HCl in dioxane (0.1 mL) and the reaction mixture was stirred for 2 hours. After concentrated in vacuum to afford HCl salts.

This HCl salts in DMF (0.2 mL) was added (R)-2-(methoxycarbonylamino)-2-phenylacetic acid (5 mg, 0.024 mmol), COMU (10 mg, 0.024 mmol) and the mixture was cooled down in an ice bath to 0° C. and diisopropylethylamine (11 µL, 0.06 mmol) was added from a syringe to the mixture. The reaction mixture was stirred for 1 hour at room temperature. The resulting mixture was then directly purified on reverse phase prep.HPLC to afford methyl {(1R)-2-[(2S,4S)-2-{2'-[(2S)-1-{(2S)-2-[(methoxycarbonyl)amino]-3-methylbutanoyl}pyrrolidin-2-yl]-1H, 1'H-7,7'-binaphtho [1,2-d]imidazol-2-yl}-4-(methylsulfanyl)pyrrolidin-1-yl]-2-oxo-1-phenylethyl}carbamate as white solid (8 mg, 50%). MS (ESI) m/z 867.58[M+H]$^+$.

Example LX
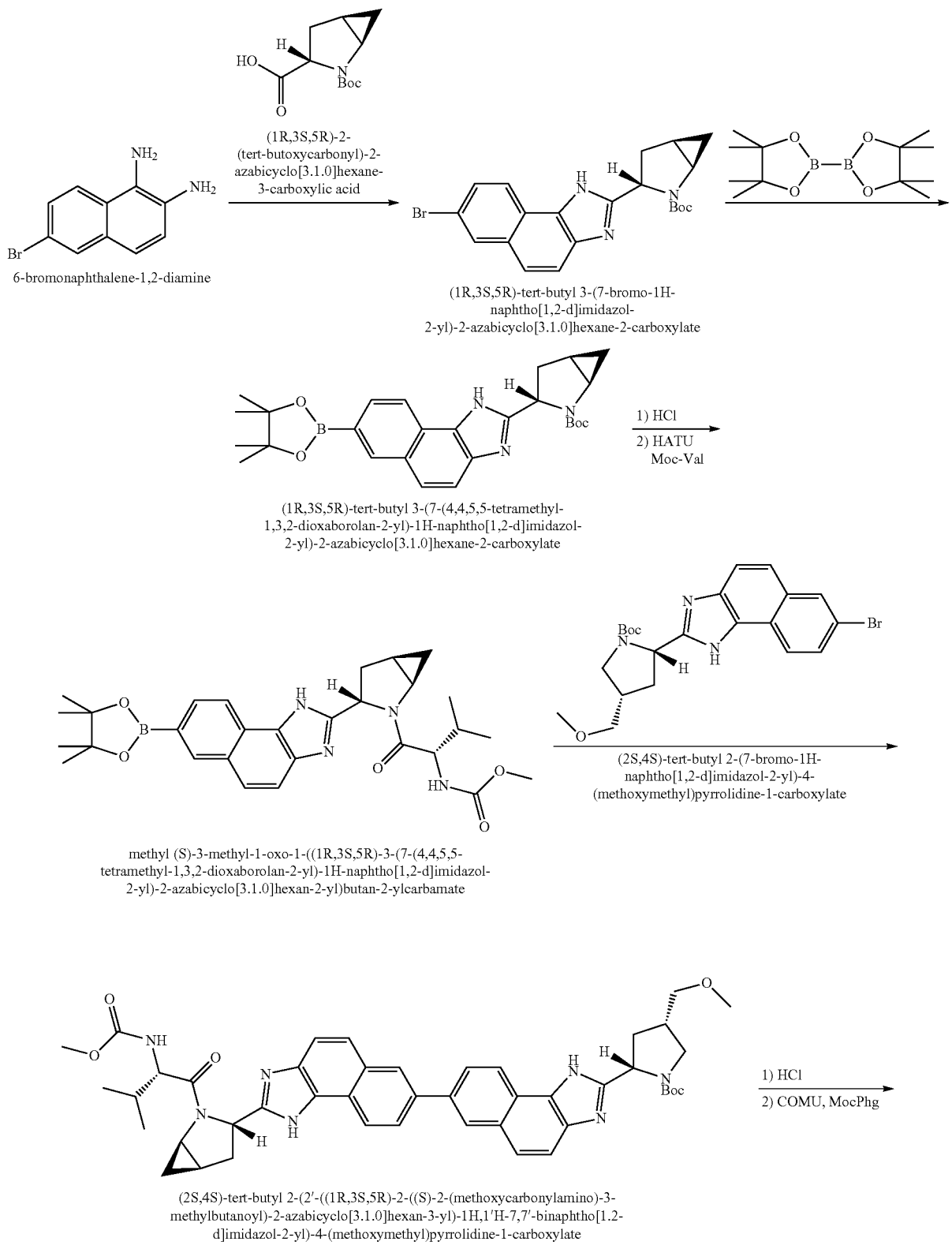

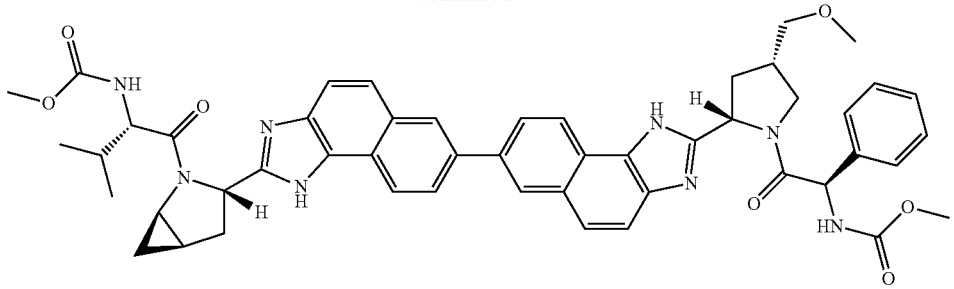

methyl (R)-((2S,4S)-4-(methoxymethyl)-2-(2'-((1R,3S,5R)-2-((S)-3-methyl-2-methoxycarbonylaminobutanoyl)-2-azabicyclo[3.1.0]hexan-3-yl)-1H,1'H-7,7'-binaphtho[1,2-d]imidazol-2-yl)pyrrolidin-1-yl)-2-oxo-1-phenylethylcarbamate (1R,3S,5R)-tert-butyl 3-(7-bromo-1H-naphtho[1,2-d]imidazol-2-yl)-2-azabicyclo[3.1.0]hexane-2-carboxylate. To a solution of (1R,3 S,5R)-2-(tert-butoxycarbonyl)-2-azabicyclo[3.1.0]hexane-3-carboxylic acid (3.0 g, 13.5 mmol), 6-bromonaphthalene-1,2-diamine (3.1 g, 13.1 mmol), and HATU (5.6 g, 14.7 mmol) in CH$_2$Cl$_2$ (125 mL) was added DIPEA (10.8 mL, 61.8 mmol). The solution was stirred at room temperature for 4 hour and concentrated to dryness. The crude oil was dissolved in EtOAc and washed with water and brine. The aqueous layers were backextracted with EtOAc, and the combined organic layers were dried over Na$_2$SO$_4$ and concentrated to dryness. The crude oil was purified by silica gel chromatography (20 to 100% EtOAc (5% MeOH)/Hexanes).

The resulting intermediate was dissolved in AcOH (125 mL), and stirred at room temperature for 18 h. The solution was concentrated and the crude oil was dissolved in EtOAc. The solution was washed with aqueous bicarbonate (sat.) and brine. The aqueous layers were backextracted with EtOAc and the combined organic layers were dried over Na$_2$SO$_4$ and concentrated. The crude oil was purified by silica gel chromatography (2 to 5% MeOH/CH$_2$Cl$_2$) to provide (1R,3 S,5R)-tert-butyl 3-(7-bromo-1H-naphtho[1,2-d]imidazol-2-yl)-2-azabicyclo[3.1.0]hexane-2-carboxylate (5.08 g, 91%). LCMS-ESI$^+$: calc'd for C$_{21}$H$_{22}$BrN$_3$O$_2$: 427.09 (M$^+$); Found: 428.71 (M+H$^+$).

(1R,3S,5R)-tert-butyl 3-(7-(4,4,5,5-tetramethyl-1,3,2-dioxaborolan-2-yl)-1H-naphtho[1,2-d]imidazol-2-yl)-2-azabicyclo[3.1.0]hexane-2-carboxylate. To a solution of (1R,3S,5R)-tert-butyl 3-(7-bromo-1H-naphtho[1,2-d]imidazol-2-yl)-2-azabicyclo[3.1.0]hexane-2-carboxylate (2.06 g, 4.8 mmol), 4,4,4',4',5,5,5',5'-octamethyl-2,2'-bi(1,3,2-dioxaborolane) (1.84, 7.2 mmol), KOAc (1.41 g, 14.4 mmol) in 1,4-dioxane (50 mL) was added Pd(dppf)Cl$_2$ (0.18 g, 0.3 mmol). The slurry was degassed with argon for 5 min and heated to 80° C. (external temperature, oil bath). The reaction was stirred at 80° C. for 5 h, and then cooled to room temperature for 15 h. The solution was diluted with EtOAc and filtered through celite. After concentration of the solution, the crude oil was purified twice by silica gel chromatography (first column: 25 to 100% EtOAc(5% MeOH)/Hexanes); second column: 2 to 5% MeOH/CH$_2$Cl$_2$) to provide (1R,3 S,5R)-tert-butyl 3-(7-(4,4,5,5-tetramethyl-1,3,2-dioxaborolan-2-yl)-1H-naphtho[1,2-d]imidazol-2-yl)-2-azabicyclo[3.1.0]hexane-2-carboxylate (2.17 g, 95%). LCMS-ESI$^+$: calc'd for C$_{27}$H$_{34}$BN$_3$O$_4$: 475.26 (M$^+$); Found: 476.11 (M+H$^+$).

methyl (S)-3-methyl-1-oxo-1-((1R,3S,5R)-3-(7-(4,4,5,5-tetramethyl-1,3,2-dioxaborolan-2-yl)-1H-naphtho[1,2-d]imidazol-2-yl)-2-azabicyclo[3.1.0]hexan-2-yl)butan-2-ylcarbamate.

To a solution of (1R,3S,5R)-tert-butyl 3-(7-(4,4,5,5-tetramethyl-1,3,2-dioxaborolan-2-yl)-1H-naphtho[1,2-d]imidazol-2-yl)-2-azabicyclo[3.1.0]hexane-2-carboxylate (0.60 g, 1.3 mmol) in a mixture of CH$_2$Cl$_2$ (12.0 mL) and MeOH (2.5 mL) was added HCl (4M in 1,4-dioxane, 9.4 mL, 37.6 mmol). The solution was stirred at room temperature for 2.5 h and concentrated to dryness.

The crude intermediate was suspended in CH$_2$Cl$_2$ (12 mL). (S)-2-(methoxycarbonylamino)-3-methylbutanoic acid (0.25 g, 1.4 mmol), HATU (0.58 g, 1.5 mmol), and DIPEA (0.7 mL, 4.0 mmol) were sequentially added to the reaction. The homogenous solution was then stirred at room temperature for 1.5 h. The solution was diluted with CH$_2$Cl$_2$ and washed with HCl (aqueous, 1N) and aqueous bicarbonate (sat.). The aqueous layers were backextracted with CH$_2$Cl$_2$ and the combined organic layers were dried over Na$_2$SO$_4$ and concentrated. The crude oil was then purified by silica gel chromatography (30 to 100% EtOAc(5% MeOH)/Hexanes) to provide methyl (S)-3-methyl-1-oxo-1-((1R,3 S,5R)-3-(7-(4,4,5,5-tetramethyl-1,3,2-dioxaborolan-2-yl)-1H-naphtho[1,2-d]imidazol-2-yl)-2-azabicyclo[3.1.0] hexan-2-yl)butan-2-ylcarbamate (0.60 g, 89%). LCMS-ESI$^+$: calc'd for C$_{29}$H$_{37}$BN$_4$O$_5$: 532.29 (M$^+$); Found: 533.11 (M+H$^+$).

(2S,4S)-tert-butyl 2-(2'-((1R,3S,5R)-2-((S)-2-(methoxycarbonylamino)-3-methylbutanoyl)-2-azabicyclo[3.1.0] hexan-3-yl)-1H,1'H-7,7'-binaphtho[1,2-d]imidazol-2-yl)-4-(methoxymethyl)pyrrolidine-1-carboxylate. To a solution of methyl (S)-3-methyl-1-oxo-1-((1R,3S,5R)-3-(7-(4,4,5,5-tetramethyl-1,3,2-dioxaborolan-2-yl)-1H-naphtho[1,2-d]imidazol-2-yl)-2-azabicyclo[3.1.0]hexan-2-yl)butan-2-ylcarbamate (0.60 g, 1.1 mmol) and (2S,4S)-tert-butyl 2-(7-bromo-1H-naphtho[1,2-d]imidazol-2-yl)-4-(methoxymethyl)pyrrolidine-1-carboxylate (0.46 g, 1.0 mmol) in DME (5 mL) was added Pd(PPh$_3$)$_4$ (0.08 g, 0.07 mmol) and K$_3$PO$_4$ (2M aqueous, 1.5 mL, 3.0 mmol). The resulting solution was degassed with argon for 5 min and heated to 80° C. (external temperature, oil bath) for 18 h. The reaction mixture was then cooled to room temperature and diluted with MeOH and CH$_2$Cl$_2$. The solution was washed with H$_2$O and brine, and the aqueous layers were backextracted with CH$_2$Cl$_2$ and MeOH (~10:1). The organic layers were combined and dried over Na$_2$SO$_4$ and concentrated. The crude oil was purified by silica gel chromatography (30 to 100% EtOAc(10% MeOH)/Hexanes to 80% MeOH/EtOAc) to provide (2S,4S)-tert-butyl 2-(2'-((1R,3S,5R)-2-((S)-2-(methoxycarbonylamino)-3-methylbutanoyl)-2-azabicyclo[3.1.0]hexan-3-yl)-1H, 1'H-7,7'-binaphtho[1,2-d]imidazol-2-yl)-4-(methoxymethyl)pyrrolidine-1- carboxylate (0.79 g, 71%). LCMS-ESI⁺: calc'd for $C_{45}H_{51}N_7O_6$: 785.39 (M⁺); Found: 786.61 (M+H⁺).

methyl (R)-2-((2S,4S)-4-(methoxymethyl)-2-(2'-((1R,3S,5R)-2-((S)-3-methyl-2-methoxycarbonylaminobutanoyl)-2-azabicyclo[3.1.0]hexan-3-yl)-1H,1'H-7,7'-binaphtho[1,2-d]imidazol-2-yl)pyrrolidin-1-yl)-2-oxo-1-phenylethylcarbamate. To a solution of (2S,4S)-tert-butyl 2-(2'-((1R,3 S,5R)-2-((S)-2-(methoxycarbonylamino)-3-methylbutanoyl)-2-azabicyclo[3.1.0]hexan-3-yl)-1H,1'H-7,7'-binaphtho[1,2-d]imidazol-2-yl)-4-(methoxymethyl)pyrrolidine-1-carboxylate (0.40 g, 0.5 mmol) in a mixture of $CH_2Cl_2$ (6.0 mL) and MeOH (1.0 mL) was added HCl (4M in 1,4-dioxane, 2.5 mL, 10.0 mmol). The solution was stirred at room temperature for 2.5 h and concentrated to dryness. The crude intermediate was purified by preparative HPLC (Gemini column, 10-50% MeCN/$H_2O$ with 0.1% TFA). The combined fractions were basified with aqueous bicarbonate (sat.) and diluted with brine. The desired product was extracted with $CH_2Cl_2$ (3×). The combined organic layers were dried over $Na_2SO_4$ and concentrated.

The intermediate was dissolved in $CH_2Cl_2$ (2.5 mL). (R)-2-(methoxycarbonylamino)-2-phenylacetic acid (0.045 g, 0.21 mmol) and DIPEA (0.05 mL, 0.28 mmol) were then added to the solution. The reaction mixture was cooled to −40° C. (external temperature, MeCN/$CO_2$(s) bath). COMU (0.098 g, 0.23 mmol) was then added and solution was allowed to warm to 0° C. over 1 h. The solution was diluted with DMF and concentrated. The crude product was purified by preparative HPLC (Gemini column, 10-60% MeCN/$H_2O$ with 0.1% TFA) and the desired fractions were combined. The solution was concentrated until the aqueous layer remained and aqueous bicarbonate (sat.) was slowly added until the solution was basic. The resulting slurry was stirred at room temperature for 2 h and filtered. The resulting solid was dried in vacuo to provide methyl (R)-2-((2S,4S)-4-(methoxymethyl)-2-(2'-((1R,3S,5R)-2-((S)-3-methyl-2-methoxycarbonylaminobutanoyl)-2-azabicyclo[3.1.0] hexan-3-yl)-1H, 1'H-7,7'-binaphtho[1,2-d]imidazol-2-yl) pyrrolidin-1-yl)-2-oxo-1-phenylethylcarbamate (0.14 g, 75%). LCMS-ESI⁺: calc'd for $C_{50}H_{52}N_8O_7$: 876.40 (M⁺); Found: 877.82 (M+H⁺). ¹H-NMR: 400 MHz, (MeOD) δ: (Mixture of rotomers) 8.57 (m, 1H), 8.28 (m, 2H), 7.97 (s, 2H), 7.75 (m, 4H), 7.38 (m, 4H), 5.54 (s, 1H), 5.31 (m, 2H), 4.61 (d, 1H), 3.77 (m, 3H), 3.65 (s, 6H), 3.46 (m, 1H), 3.32 (s, 3H), 3.20 (m, 2H), 2.57 (m, 3H), 2.17 (m, 1H), 2.06 (m, 2H), 1.13 (m, 1H), 1.00 (d, 3H), 0.89 (d, 3H), 0.84 (m, 1H).

Example LY

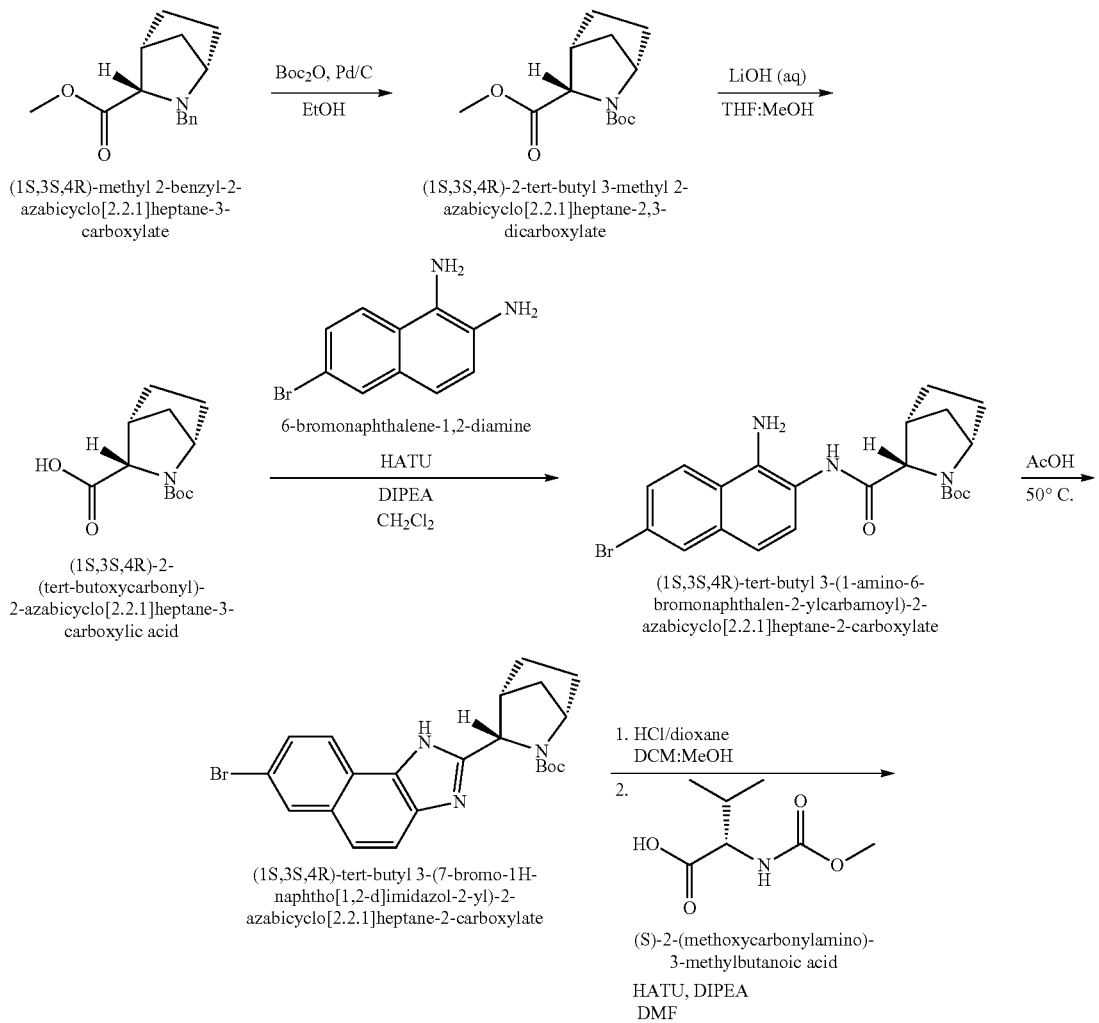

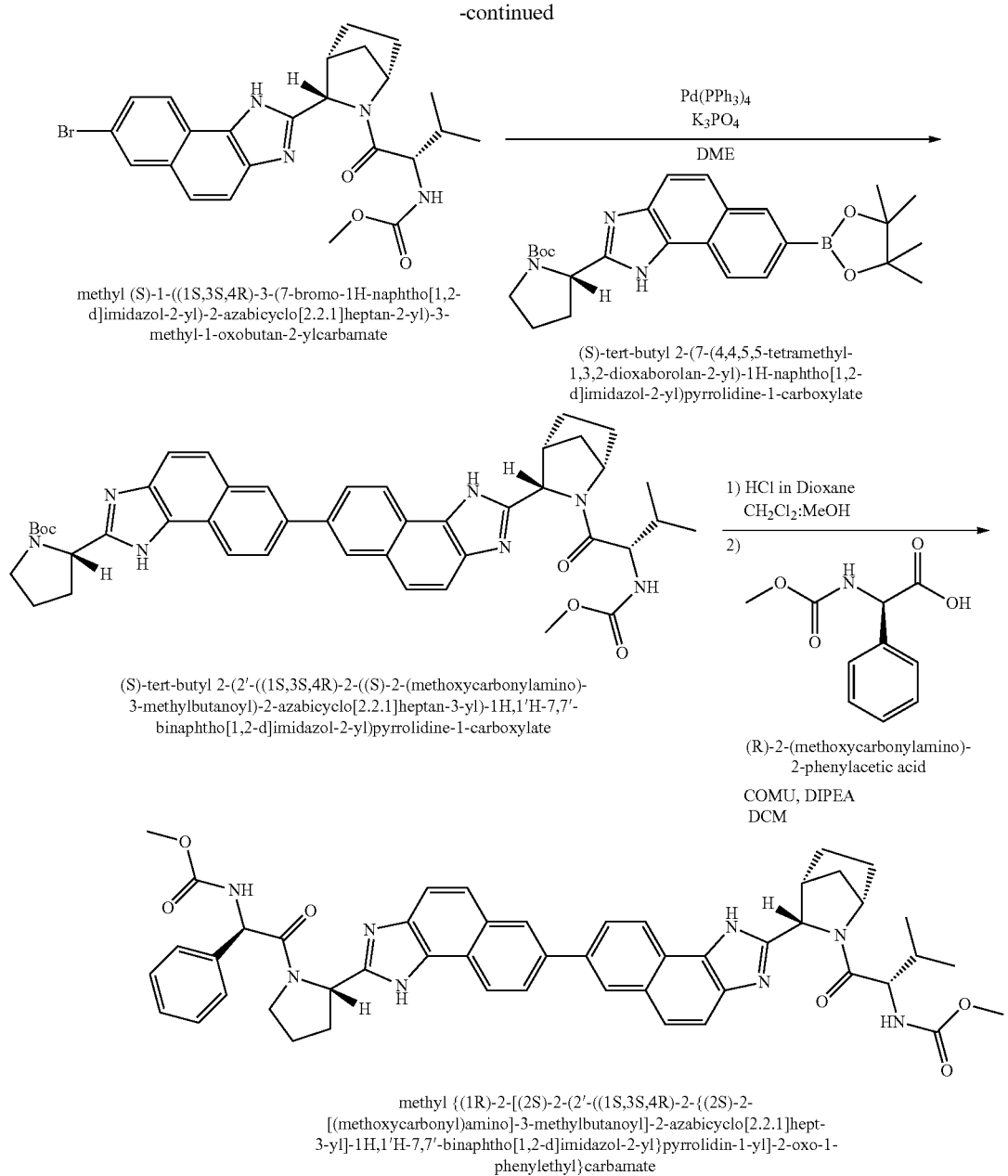

(1S,3S,4R)-methyl 2-benzyl-2-azabicyclo[2.2.1]heptane-3-carboxylate: (1S,3S,4R)-methyl 2-benzyl-2-azabicyclo[2.2.1]heptane-3-carboxylate was prepared as described in Org Lett 1999, 1, 1595-1597.

(1S,3S,4R)-2-tert-butyl 3-methyl 2-azabicyclo[2.2.1]heptane-2,3-dicarboxylate: (1S,3S,4R)-methyl 2-benzyl-2-azabicyclo[2.2.1]heptane-3-carboxylate (2.9g, 11.82 mmol) and boc anhydride (3.8g, 17.75 mmol) were added to 10% palladium on carbon (0.118g) in Ethanol (50 mL). The solution was stirred under an atmosphere of hydrogen for 16 hours. Upon completion, the reaction was flushed with nitrogen, filtered through a pad of diatomaceous earth and purified by normal phase chromatography (12-33% ethyl acetate in hexanes) to give (1S,3S,4R)-2-tert-butyl 3-methyl 2-azabicyclo[2.2.1]heptane-2,3-dicarboxylate (2.67g, 87%) as a clear oil. $^1$H NMR (400 MHz, CDCl$_3$, mixture of rotomers, major reported) δ 4.36 (s, 1H), 4.16 (d, 1H), 3.71 (s, 3H), 2.74 (s, 1H), 1.85-1.73 (m, 1H), 1.70-1.54 (m, 2H), 1.48-1.40 (m, 3H), 1.37 (s, 9H).

(1S,3S,4R)-2-(tert-butoxycarbonyl)-2-azabicyclo[2.2.1]heptane-3-carboxylic acid: To a solution of (1S,3S,4R)-2-tert-butyl 3-methyl 2-azabicyclo[2.2.1]heptane-2,3-dicarboxylate (1.67g, 6.54 mmol) in THF:MeOH (41 mL:13 mL) was added aqueous Lithium hydroxide (1M, 8.2 mL, 8.2 mmol) and the reaction was allowed to stir at room temperature overnight. Upon completion, the reaction was concentrated in vacuo, diluted with ethyl acetate and washed with 1N HCl. The aqueous layer was backextracted with ethyl acetate. The combined organic layers were dried over sodium sulfate, filtered and concentrated to give (1S,3S,4R)-2-(tert-butoxycarbonyl)-2-azabicyclo[2.2.1]heptane-3-carboxylic acid (1.36g, 86%). $^1$H NMR (400 MHz, Methanold4) δ 6.43 (s, 1H), 5.84 (s, 1H), 5.74 (d, 1H), 4.34 (s, 1H), 3.36-3.18 (m, 3H), 3.17-3.06 (m, 3H), 3.02 (s, 3H), 2.97 (s, 6H).

(1S,3S,4R)-tert-butyl 3-(1-amino-6-bromonaphthalen-2-ylcarbamoyl)-2-azabicyclo[2.2.1]heptane-2-carboxylate: To a solution of 6-bromonaphthalene-1,2-diamine (1.08g, 4.56 mmol), and (1 S,3S,4R)-2-(tert-butoxycarbonyl)-2-azabicyclo[2.2.1]heptane-3-carboxylic acid (1.10g, 4.56 mmol) and HATU (2.08g, 5.47 mmol) in methylene chloride (45 mL) was added DIPEA (3.98 mL, 22.79 mmol). The mixture was stirred at room temperature for two hours. Upon completion, the reaction was concentrated in vacuo, diluted with ethyl acetate and washed with water. The aqueous layer was backextracted with ethyl acetate twice. The combined organic layers were washed with brine, concentrated, and purified by normal phase chromatography (30-80% ethyl acetate(5% MeOH) in hexanes) to give (1 S,3 S,4R)-tert-butyl 3-(1-amino-6-bromonaphthalen-2-ylcarbamoyl)-2-azabicyclo[2.2.1]heptane-2-carboxylate (2.01g, 95%). LCMS-ESI$^+$: calc'd for $C_{22}H_{26}BrN_3O_3$: 459.12 (M$^+$); Found: 460.9 (M+H$^+$).

(1S,3S,4R)-tert-butyl 3-(7-bromo-1H-naphtho[1,2-d]imidazol-2-yl)-2-azabicyclo[2.2.11]heptane-2-carboxylate: (1S,3 S,4R)-tert-butyl 3-(1-amino-6-bromonaphthalen-2-ylcarbamoyl)-2-azabicyclo[2.2.1]heptane-2-carboxylate (2.01g, 4.36 mmol) was suspended in AcOH (8.73 mL, 152.7 mmol) and placed in a preheated 50° C. oil bath. The suspension was let stir at 50° C. for 4 hours and at room temperature for 14 hours. Upon completion, the reaction mixture was diluted with ethyl acetate and aqueous NaOH (6M, 25.4 mL, 152.7 mmol) was added slowly with stirring. The layers were separated and the aqueous layer was backextracted with ethyl acetate twice. The combined organic layers were dried over sodium sulfate and concentrated in vacuo. The resulting oil was purified by normal phase chromatography (30-55-100% ethyl acetate(5% MeOH) in hexanes) to give (1 S,3S,4R)-tert-butyl 3-(7-bromo-1H-naphtho[1,2-d]imidazol-2-yl)-2-azabicyclo[2.2.1]heptane-2-carboxylate (1.8g, 93%). LCMS-ESI$^+$: calc'd for $C_{22}H_{24}BrN_3O_2$: 441.11 (M$^+$); Found: 442.7 (M+H$^+$).

Methyl (S)-1-((1S,3S,4R)-3-(7-bromo-1H-naphtho[1,2-d]imidazol-2-yl)-2-azabicyclo[2.2.1]heptan-2-yl)-3-methyl-1-oxobutan-2-ylcarbamate: Hydrogen chloride in dioxane solution (4N, 6.78 mL, 27.18 mmol) was added to (1S,3S, 4R)-tert-butyl 3-(7-bromo-1H-naphtho[1,2-d]imidazol-2-yl)-2-azabicyclo[2.2.1]heptane-2-carboxylate (0.80g, 1.81 mmol) in methylene chloride: methanol (18.1 mL: 3.6 mL). The suspension was allowed to stir at room temperature for one hour. Upon completion by LCMS, the reaction was concentrated to dryness and the crude product (assumed 1.81 mmol) was suspended in methylene chloride (18 mL). (S)-2-(methoxycarbonylamino)-3-methylbutanoic acid (0.38g, 2.17 mmol) and DIPEA (1.58 mL, 9.04 mmol) were added to the slurry. HATU (1.03g, 2.71 mmol) was added and the reaction was stirred at room temperature for 3 hours. Upon completion, the crude reaction was diluted in methylene chloride and washed with 1N HCl, and aqueous sodium bicarbonate. The organic layer was concentrated and purified by normal phase chromatography (40-80% ethyl acetate (5% methanol) in hexanes) to give methyl (S)-1-((1S,3S,4R)-3-(7-bromo-1H-naphtho[1,2-d]imidazol-2-yl)-2-azabicyclo[2.2.1]heptan-2-yl)-3-methyl-1-oxobutan-2-ylcarbamate (0.949, >99%). LCMS-ESI$^+$: calc'd for $C_{24}H_{27}BrN_4O_3$: 498.13 (M$^+$); Found: 498.9 (M+H$^+$).

(S)-tert-butyl 2-(2'-((1S,3S,4R)-2-((S)-2-(methoxycarbonylamino)-3-methylbutanoyl)-2-azabicyclo[2.2.1]heptan-3-yl)-1H,1'H-7,7'-binaphtho[1,2-d]imidazol-2-yl)pyrrolidine-1-carboxylate: Methyl (S)-1-((1 S,3 S,4R)-3-(7-bromo-1H-naphtho[1,2-d]imidazol-2-yl)-2-azabicyclo[2.2.1]heptan-2-yl)-3-methyl-1-oxobutan-2-ylcarbamate (0.300g, 0.601 mmol), (S)-tert-butyl 2-(7-(4,4,5,5-tetramethyl-1,3,2-dioxaborolan-2-yl)-1H-naphtho[1,2-d]imidazol-2-yl)pyrrolidine-1-carboxylate (0.334g, 0.721 mmol), and aqueous potassium phosphate (2M, 0.901 mL, 1.802 mmol) were suspended in 1,2-dimethoxyethane (3.00 mL) and sparged with argon gas for 30 minutes. Palladium tetrakis triphenylphosphine (0.069g, 0.060 mmol) was added and the reaction mixture was capped and placed in a preheated 80° C. oil bath. The solution was heated for 18 hours and subsequently stirred at room temperature for two days. Upon completion, the reaction was diluted with ethyl acetate and washed with brine. The concentrated organic layer was purified by normal phase chromatography (40-100% ethyl acetate (10% MeOH) in hexanes) to give (S)-tert-butyl 2-(2'-((1S,3S,4R)-2-((S)-2-(methoxycarbonylamino)-3-methylbutanoyl)-2-azabicyclo[2.2.1]heptan-3-yl)-1H,1'H-7,7'-binaphtho[1,2-d]imidazol-2-yl)pyrrolidine-1-carboxylate (0.305g, 67%). LCMS-ESI$^+$: calc'd for $C_{44}H_{49}N_7O_5$: 755.38 (M$^+$); Found: 756.8 (M+H$^+$).

Methyl {(1R)-2-[(2S)-2-{2'-[(1S,3S,4R)-2-{(2S)-2-[(methoxycarbonyl)amino]-3-methylbutanoyl}-2-azabicyclo[2.2.1]hept-3-yl]-1H,1'H-7,7'-binaphtho[1,2-d]imidazol-2-yl}pyrrolidin-1-yl]-2-oxo-1-phenylethyl}carbamate: Hydrogen chloride in dioxane solution (4N, 1.51 mL, 6.05 mmol) was added to a solution of (S)-tert-butyl 2-(2'-((1 S,3S,4R)-2-((S)-2-(methoxycarbonylamino)-3-methylbutanoyl)-2-azabicyclo[2.2.1]heptan-3-yl)-1H,1'H-7,7'-binaphtho[1,2-d]imidazol-2-yl)pyrrolidine-1-carboxylate (0.305g, 0.403 mmol) in methylene chloride:methanol (4.0 mL: 0.80 mL). The suspension was allowed to stir at room temperature for two hours. Upon completion by LCMS, the reaction was concentrated to dryness and the crude product (assumed 0.403 mmol) was suspended in methylene chloride (4 mL). (R)-2-(methoxycarbonylamino)-2-phenylacetic acid (0.093g, 0.484 mmol) and DIPEA (0.282 mL, 1.61 mmol) were added and the slurry was cooled to −40° C. with an external dry ice/acetonitrile bath. COMU (0.259g, 0.605 mmol) was added at −40° C. and the solution was stirred at reduced temperature for one hour. Upon completion, the crude reaction was diluted with DMF and concentrated in vacuo. The crude product was purified by reverse phase HPLC (Gilson, Gemini, 10-45% acetonitrile/water with 0.1% TFA modifier). Fractions containing product were combined and concentrated until aqueous layer remained. Aqueous sodium bicarbonate was added to aqueous product mixture to obtain a pH of 7-8 (as measured by pH paper) and precipitation was observed. The precipitate was filtered and dried under vacuum for 18 hours to give methyl {(1R)-2-[(2S)-2-{2'-[(1 S,3S,4R)-2-{(2S)-2-[(methoxycarbonyl)amino]-3-methylbutanoyl}-2-azabicyclo[2.2.1]hept-3-yl]-1H, 1'H-7,7'-binaphtho[1,2-d]imidazol-2-yl}pyrrolidin-1-yl]-2-oxo-1-phenylethyl}carbamate (0.180g, 53%) as a while solid. LCMS-ESI$^+$: calc'd for $C_{49}H_{50}N_8O_6$: 846.39 (M$^+$); Found: 847.8 (M+H$^+$).

Example LZ
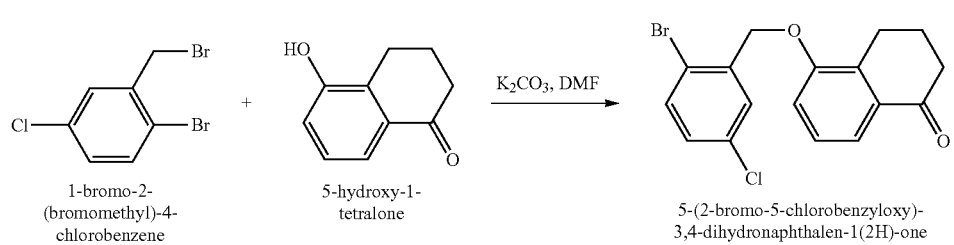
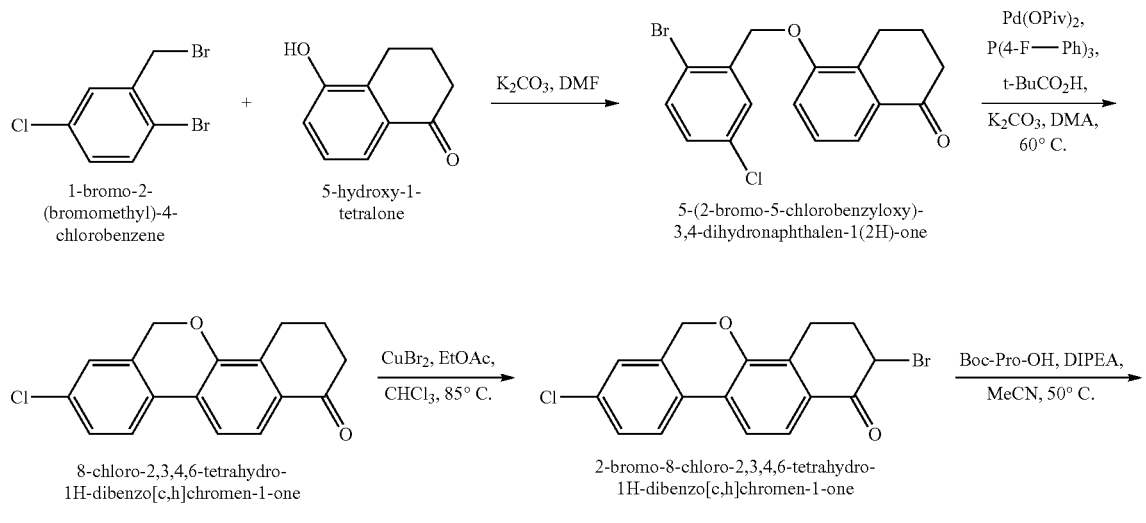
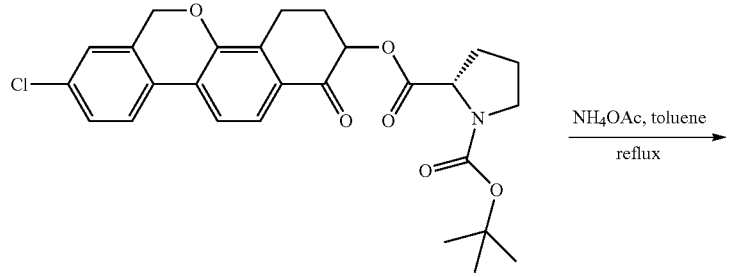
(2S)-1-tert-butyl 2-(8-chloro-1-
oxo-2,3,4,6-tetrahydro-1H-
dibenzo[c,h]chromen-2-yl)
pyrrolidine-1,2-dicarboxylate
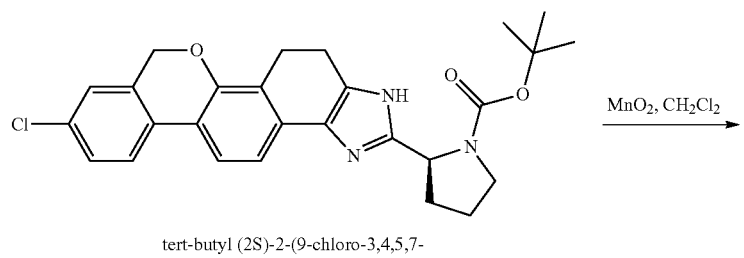
tert-butyl (2S)-2-(9-chloro-3,4,5,7-
tetrahydroisochromeno[3′,4′:5,6]naphtho[1,2-
d]imidazol-2-yl)pyrrolidine-1-carboxylate
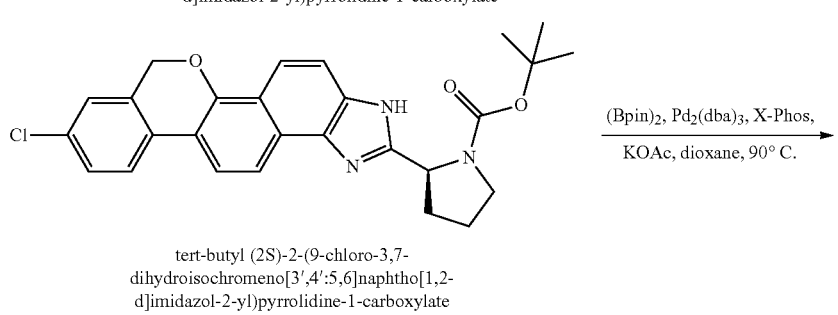
tert-butyl (2S)-2-(9-chloro-3,7-
dihydroisochromeno[3′,4′:5,6]naphtho[1,2-
d]imidazol-2-yl)pyrrolidine-1-carboxylate -continued

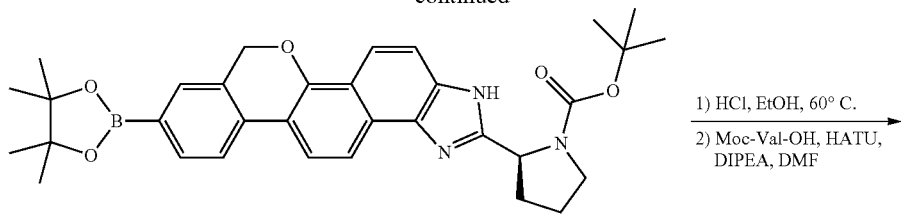

tert-butyl (2S)-2-[9-(4,4,5,5-tetramethyl-
1,3,2-dioxaborolan-2-yl)-3,7-
dihydroisochromeno[3',4':5,6]naphtho[1,2-
d]imidazol-2-yl]pyrrolidine-1-carboxylate

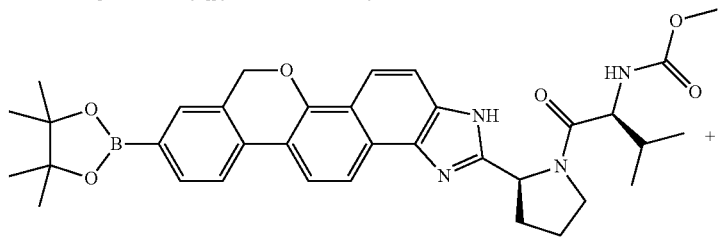

methyl [(2S)-3-methyl-1-oxo-1-{(2S)-2-[9-(4,4,5,5-
tetramethyl-1,3,2-dioxaborolan-2-yl)-3,7-
dihydroisochromeno[3',4':5,6]naphtho[1,2-
d]imidazol-2-yl]pyrrolidin-1-yl}butan-2-yl]carbamate

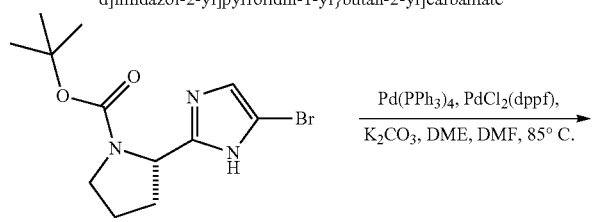

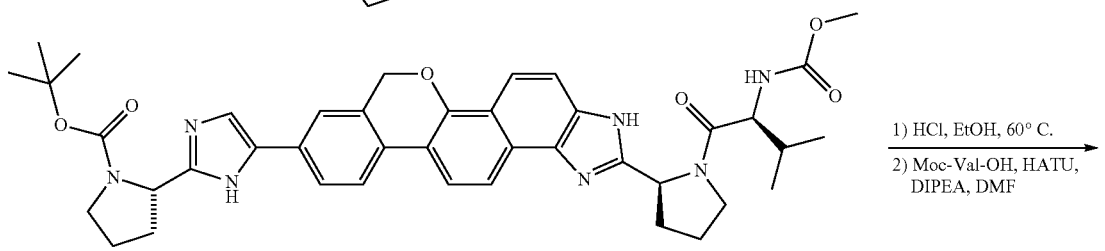

tert-butyl (2R)-2-[5-(2-{(2S)-1-[N-(methoxycarbonyl)-L-
valyl]pyrrolidin-2-yl}-3,7-
dihydroisochromeno[3',4':5,6]naphtho[1,2-d]imidazol-9-
yl)-1H-imidazol-2-yl]pyrrolidine-1-carboxylate

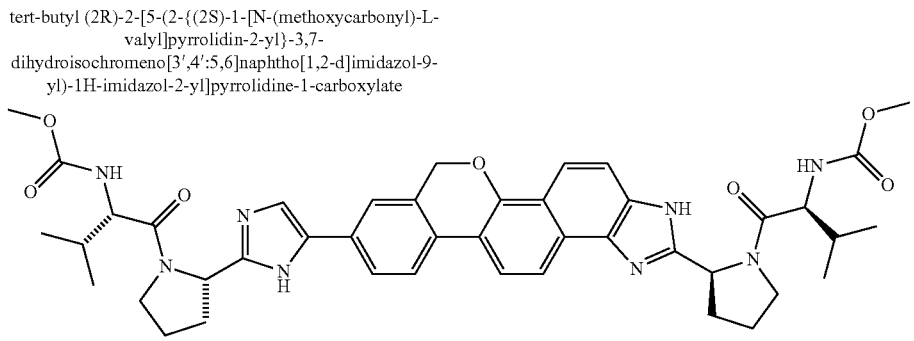

methyl {(2S)-1-[(2R)-2-(5-{2-[(2S)-1-{(2S)-2-
[(methoxycarbonyl)amino]-3-
methylbutanoyl}pyrrolidin-2-yl]-3,7-
dihydroisochromeno[3',4':5,6]naphtho[1,2-
d]imidazol-9-yl}-1H-imidazol-2-yl)pyrrolidin-1-yl]-
3-methyl-1-oxobutan-2-yl}carbamate 5-(2-bromo-5-chlorobenzyloxy)-3,4-dihydronaphthalen-1 (2H1)-one: To a stirred solution of 5-hydroxy-1-tetralone (2.0 g, 12.3 mmol) and 1-bromo-2-(bromomethyl)-4-chlorobenzene (3.6 g, 12.7 mmol) in dimethylformamide (125 mL) was added potassium carbonate (3.5 g, 25.1 mmol). The reaction was stirred under argon for 1 hour then diluted with ethyl acetate (1 L). The organics were washed three times with water and once with brine. The organic layer was then dried with magnesium sulfate, filtered and concentrated. To the resulting oil was added methanol (100 mL) and the suspension was agitated for thirty minutes. 5-(2-bromo-5-chlorobenzyloxy)-3,4-dihydronaphthalen-1 (2H)-one (4.25 g, 94% yield) was isolated by filtration.

8-chloro-2,3,4,6-tetrahydro-1H-dibenzo[c,h]chromen-1-one: To a flask containing palladium(II) pivalate (68 mg, 0.22 mmol), tri(4-fluorophenyl)phosphine (70 mg, 0.22 mmol), pivalic acid (135 mg, 1.3 mmol) and potassium carbonate (1.83 g, 13.1 mmol) was added a solution of 5-(2-bromo-5-chlorobenzyloxy)-3,4-dihydronaphthalen-1 (2H)-one (1.61 g, 4.4 mmol) in dimethyacetamide (23 mL). The flask was evacuated and backfilled with argon 5 times and then stirred under argon at 60° C. for 24 hours. The reaction was poured directly onto a silica gel column and purified by flash column chromatography (hexanes/DCM) to yield 8-chloro-2,3,4,6-tetrahydro-1H-dibenzo[c,h]chromen-1-one (1.22 g, 97% yield) as an off-white solid.

2-bromo-8-chloro-2,3,4,6-tetrahydro-1H-dibenzo[c,h] chromen-1-one: To a mixture of 8-chloro-2,3,4,6-tetrahydro-1H-dibenzo[c,h]chromen-1-one (2.58 g, 9.1 mmol) in chloroform (9.1 mL) and ethyl acetate (9.1 mL) was added copper(II) bromide (4.65 g, 19.9 mmol). The reaction was heated to 80° C. for 5 hours and then cooled to room temperature. The mixture was diluted with dichloromethane and washed twice with a 5:1 solution of saturated aqueous ammonium chloride and aqueous ammonium hydroxide (~28%), and washed once with water. The organic layer was dried with magnesium sulfate, filtered and concentrated. The crude material was purified by flash column chromatography (hexanes/DCM) to yield 2-bromo-8-chloro-2,3,4,6-tetrahydro-1H-dibenzo[c,h]chromen-1-one (2.45 g, 75% yield).

(2S)-1-tert-butyl 2-(8-chloro-1-oxo-2,3,4,6-tetrahydro-1H-dibenzo[c,h]chromen-2-yl) pyrrolidine-1,2-dicarboxylate: To a solution of 2-bromo-8-chloro-2,3,4,6-tetrahydro-1H-dibenzo[c,h]chromen-1-one (1.05 g, 2.9 mmol) and Boc-Pro-OH (1.75 g, 8.1 mmol) in acetonitrile (9.0 mL) was added diisopropylethylamine (1.5 mL, 8.7 mmol). The solution was stirred under argon at 50° C. for two hours. Extra Boc-Pro-OH (620 mg, 2.9 mmol) and diisopropylethylamine (0.5 mL, 2.9 mmol) were added and the reaction was stirred at 50° C. for 16 hours. The reaction was cooled to room temperature and diluted with ethyl acetate. The organics were washed with water and brine, dried with magnesium sulfate and concentrated. The crude material was purified by flash column chromatography and the product (2S)-1-tert-butyl 2-(8-chloro-1-oxo-2,3,4,6-tetrahydro-1H-dibenzo[c,h]chromen-2-yl) pyrrolidine-1,2-dicarboxylate was isolated as a mixture of diastereomers (0.99 g, 69% yield).

tert-butyl (2S)-2-(9-chloro-3,4,5,7-tetrahydroisochromeno[3',4':5,6]naphtho[1,2-d]imidazol-2-yl)pyrrolidine-1-carboxylate: To a solution of (2S)-1-tert-butyl 2-(8-chloro-1-oxo-2,3,4,6-tetrahydro-1H-dibenzo[c,h]chromen-2-yl) pyrrolidine-1,2-dicarboxylate (2.2 g, 4.4 mmol) in toluene (40 mL) was added ammonium acetate (7 g, 91 mmol). The reaction mixture was vigorously refluxed for 3 hours, then cooled to room temperature and diluted with ethyl acetate. The organics were washed with water and brine, dried with magnesium sulfate and concentrated. The crude material was purified by flash column chromatography to yield tert-butyl (2 S)-2-(9-chloro-3,4,5,7-tetrahydroisochromeno[3',4':5,6]naphtho[1,2-d]imidazol-2-yl)pyrrolidine-1-carboxylate (1.13 g, 54% yield) as well as recovered (2S)-1-tert-butyl 2-(8-chloro-1-oxo-2,3,4,6-tetrahydro-1H-dibenzo [c,h]chromen-2-yl) pyrrolidine-1,2-dicarboxylate (0.8 g, 36%). LCMS-ESI$^+$: calculated for $C_{27}H_{28}N_3O_3$: 477.98; observed [M+1]$^+$: 478.54.

tert-butyl (2S)-2-(9-chloro-3,7-dihydroisochromeno[3',4': 5,6]naphtho[1,2-d]imidazol-2-yl)pyrrolidine-1-carboxylate: To a solution of Intermediate tert-butyl (2S)-2-(9-chloro-3, 4,5,7-tetrahydroisochromeno[3',4':5,6]naphtho[1,2-d]imidazol-2-yl)pyrrolidine-1-carboxylate (1.43 g, 3.0 mmol) in dichloromethane (30 mL) was added manganese(IV) oxide (15 g, 198 mmol). The mixture was stirred for four hours at room temperature then filtered through Celite. The MnO$_2$ was thoroughly rinsed with dichloromethane and the total filtrate was concentrated to yield tert-butyl (2S)-2-(9-chloro-3,7-dihydroisochromeno[3',4':5,6]naphtho[1,2-d]imidazol-2-yl)pyrrolidine-1-carboxylate (1.37 g, 96% yield). This material was used without further purification.

tert-butyl (2S)-2-[9-(4,4,5,5-tetramethyl-1,3,2-dioxaborolan-2-yl)-3,7-dihydroisochromeno[3',4':5,6]naphtho[1,2-d] imidazol-2-yl]pyrrolidine-1-carboxylate: To a solution of tert-butyl (2S)-2-(9-chloro-3,7-dihydroisochromeno[3',4':5, 6]naphtho[1,2-d]imidazol-2-yl)pyrrolidine-1-carboxylate (1.4 g, 2.9 mmol) in dioxane (20 mL) was added bis (pinacolato)diboron (1.5 g, 5.9 mmol), tris(dibenzylideneacetone)dipalladium(0) (110 mg, 0.12 mmol), X-Phos (145 mg, 0.30 mmol) and potassium acetate (870 mg, 8.9 mmol). The mixture was degassed with a stream of argon for ten minutes. The degassed reaction was heated under argon to 90° C. for 2.5 hours then cooled to room temperature and diluted with ethyl acetate. The organics were washed with water and brine, dried with magnesium sulfate and concentrated. The crude material was purified by flash column chromatography (DCM/EtOAc) to yield tert-butyl (2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidine-1-carboxylate (1.5 g, 90% yield).

methyl [(2S)-3-methyl-1-oxo-1-{(2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidin-1-yl}butan-2-yl]carbamate: A solution of tert-butyl (2S)-2-[9-(4,4,5,5-tetramethyl-1,3,2-dioxaborolan-2-yl)-3,7-dihydroisochromeno[3',4':5,6]naphtho[1,2-d]imidazol-2-yl] pyrrolidine-1-carboxylate (0.98 g, 1.7 mmol), concentrated HCl (2 mL) and ethanol (20 mL) was heated to 60° C. for 2 hours. The reaction was concentrated and redissolved in a minimal amount of methanol. An equal volume of dichloromethane was added and the solution was again concentrated. Dichloromethane was added to the resulting residue and concentrated off two more times. The resulting crude material was dissolved in dimethylformamide (17 mL). To this solution was added (S)-2-(methoxycarbonylamino)-3-methylbutanoic acid (455 mg, 2.6 mmol), HATU (955 mg, 2.5 mmol) and diisopropylethylamine (3 mL, 17 mmol). The reaction was stirred at room temperature for one hour then diluted with ethyl acetate. The organics were washed with water (×2) and brine, dried with magnesium sulfate and concentrated. The resulting residue was purified by flash column chromatography to yield Intermediate methyl [(2S)-3-methyl-1-oxo-1-{(2S)-2-[9-(4,4,5,5-tetramethyl-1,3,2-dioxaborolan-2-yl)-3,7-dihydroisochromeno[3',4':5,6]naphtho [1,2-d]imidazol-2-yl]pyrrolidin-1-yl}butan-2-yl]carbamate (780 mg, 72% yield over 2 steps).

tert-butyl (2R)-2-[5-(2-{(2S)-1-[N-(methoxycarbonyl)-L-valyl]pyrrolidin-2-yl}-3,7-dihydroisochromeno[3',4':5,6] naphtho[1,2-d]imidazol-9-yl)-1H-imidazol-2-yl]pyrrolidine-1-carboxylate: A mixture of Pentacyclic Intermediate methyl [(2S)-3-methyl-1-oxo-1-{(2S)-2-[9-(4,4,5,5-tetramethyl-1,3,2-dioxaborolan-2-yl)-3,7-dihydroisochromeno[3', 4':5,6]naphtho[1,2-d]imidazol-2-yl]pyrrolidin-1-yl}butan-2-yl]carbamate (780 mg, 1.3 mmol), (S)-tert-butyl 2-(5-bromo-1H-imidazol-2-yl)pyrrolidine-1-carboxylate (450 mg, 1.4 mmol), tetrakis(triphenylphosphine)palladium(0) (30 mg, 0.03 mmol), PdCl$_2$(dppf) (60 mg, 0.08 mmol), 2M aqueous potassium carbonate (1.9 mL, 3.9 mmol), dimethoxyethane (10 mL) and dimethylformamide (2 mL) was degassed with argon for 15 minutes. The reaction was then heated to 85° C. for 3 hours. Upon completion, the reaction was cooled to room temperature, diluted with ethyl acetate and filtered through Celite. The filtrate was washed with water and brine, dried (MgSO$_4$) and concentrated. The resulting crude material was purified by flash column chromatography (EtOAc/MeOH) to yield Intermediate tert-butyl (2R)-2-[5-(2-{(2S)-1-[N-(methoxycarbonyl)-L-valyl]pyrrolidin-2-yl}-3,7-dihydroisochromeno[3',4':5,6]naphtho[1,2-d]imidazol-9-yl)-1H-imidazol-2-yl]pyrrolidine-1-carboxylate (390 mg, 43% yield).

methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate: A mixture of Intermediate tert-butyl (2R)-2-[5-(2-{(2S)-1-[N-(methoxycarbonyl)-L-valyl] pyrrolidin-2-yl}-3,7-dihydroisochromeno[3',4':5,6]naphtho[1,2-d]imidazol-9-yl)-1H-imidazol-2-yl]pyrrolidine-1-carboxylate (390 mg, 0.53 mmol), concentrated HCl (2 mL) and ethanol (10 mL) was heated to 60° C. for 2 hours. The reaction was concentrated and redissolved in a minimal amount of methanol. An equal volume of dichloromethane was added and the solution was again concentrated. Dichloromethane was added to the resulting residue and concentrated off two more times. One half of the crude material (~0.27 mmol) was dissolved in dimethylformamide (2.5 mL). To this solution was added (S)-2-(methoxycarbonylamino)-3-methylbutanoic acid (66 mg, 0.38 mmol), HATU (140 mg, 0.37 mmol) and diisopropylethylamine (0.48 mL, 2.7 mmol). The reaction was stirred at room temperature for 2 hours, and then diluted with acetonitrile (2 mL) and methanol (2 mL). To this solution was added ten drops of 5M aqueous NaOH solution and stirring was continued for 30 minutes. The reaction was diluted with ethyl acetate and the organic layer was washed with water and brine. The combined aqueous washings were extracted three times with ethyl acetate, and the combined organic layers were dried (MgSO$_4$) and concentrated. The crude material was purified by reverse phase HPLC (Gemini, 15 to 45% ACN/H$_2$O+0.1% TFA) to yield methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate (140 mg, 67% yield over 2 steps). LCMS-ESI$^+$: calculated for C$_{43}$H$_{50}$N$_8$O$_7$: 790.91; observed [M+1]$^+$: 791.71.

Example MA

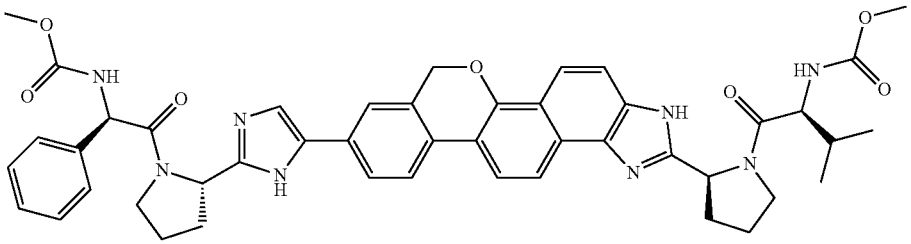

methyl {(1R)-2-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-2-oxo-1-phenylethyl}carbamate This compound was made in an analogous manner to Example methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate, substituting (R)-2-(methoxycarbonylamino)-2-phenylacetic acid for (S)-2-(methoxycarbonylamino)-3-methylbutanoic acid and substituting COMU for HATU in the final amide coupling step. LCMS-ESI$^+$: calculated for C$_{46}$H$_{48}$N$_8$O$_7$: 824.92; observed [M+1]$^+$: 825.72.

Example MB

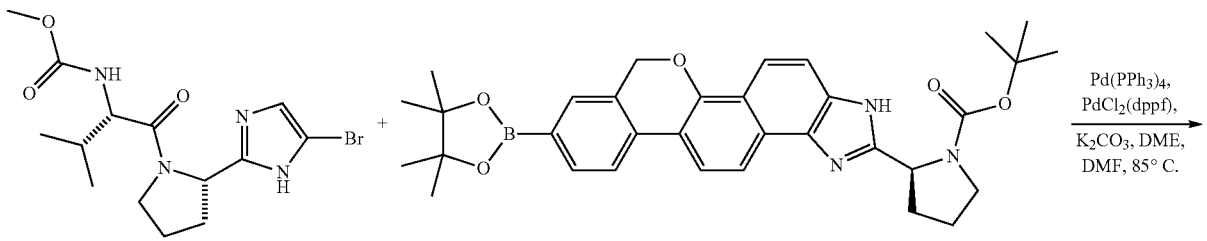

methyl (S)-1-((S)-2-(5-bromo-1H-imidazol-2-yl)pyrrolidin-1-yl)-3-methyl-1-oxobutan-2-ylcarbamate tert-butyl (2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidine-1-carboxylate -continued

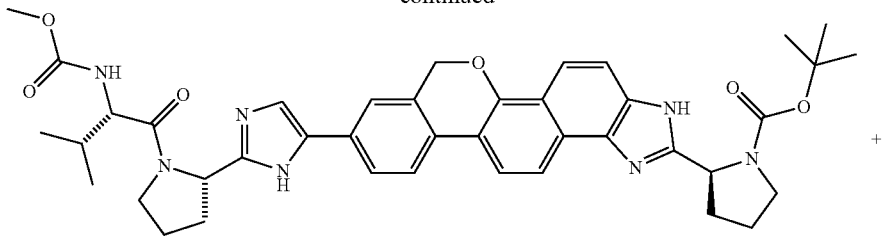

tert-butyl (2S)-2-[9-(2-{(2R)-1-[N-(methoxycarbonyl)-L-valyl]pyrrolidin-2-yl}-1H-imidazol-5-yl)-3,7-dihydroisochromeno[3',4':5,6]naphtho[1,2-d]imidazol-2-yl]pyrrolidine-1-carboxylate

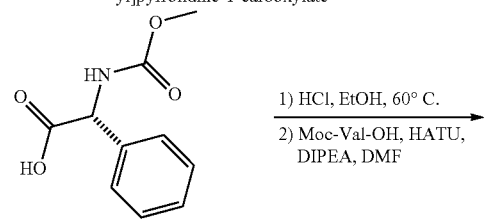

(R)-2-(methoxycarbonylamino)-2-phenylacetic acid

1) HCl, EtOH, 60° C.
2) Moc-Val-OH, HATU, DIPEA, DMF

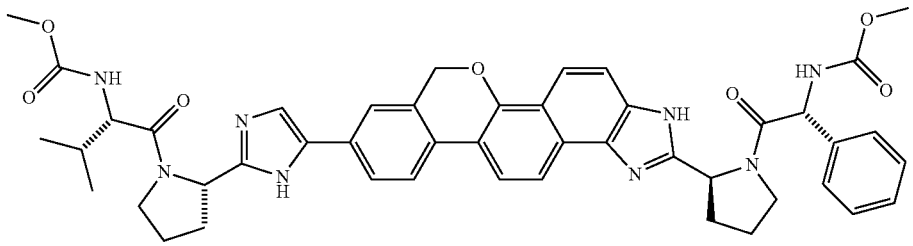

methyl {(2S)-1-[(2R)-2-(5-{2-[(2S)-1-{(2R)-2-[(methoxycarbonyl)amino]-2-phenylacetyl}pyrrolidin-2-yl]-3-7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate tert-butyl (2S)-2-[9-(2-{(2R)-1-[N-(methoxycarbonyl)-L-valyl]pyrrolidin-2-yl}-1H-imidazol-5-yl)-3,7-dihydroisochromeno[3',4':5,6]naphtho[1,2-d]imidazol-2-yl]pyrrolidine-1-carboxylate: A mixture of tert-butyl (2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidine-1-carboxylate (450 mg, 0.79 mmol), methyl (S)-1-((S)-2-(5-bromo-1H-imidazol-2-yl)pyrrolidin-1-yl)-3-methyl-1-oxobutan-2-ylcarbamate (325 mg, 0.87 mmol), tetrakis(triphenylphosphine)palladium(0) (30 mg, 0.02 mmol), PdCl$_2$(dppf) (35 mg, 0.05 mmol), 2M aqueous potassium carbonate (1.2 mL, 2.4 mmol), dimethoxyethane (6.8 mL) and dimethylformamide (1.2 mL) was degassed with argon for 15 minutes. The reaction was then heated to 85° C. for 2.5 hours. Upon completion, the reaction was cooled to room temperature, diluted with ethyl acetate and filtered through Celite. The filtrate was washed with water and brine, dried (MgSO$_4$) and concentrated. The resulting crude material was purified by flash column chromatography (EtOAc/MeOH) to yield tert-butyl (2S)-2-[9-(2-{(2R)-1-[N-(methoxycarbonyl)-L-valyl]pyrrolidin-2-yl}-1H-imidazol-5-yl)-3,7-dihydroisochromeno[3',4': 5,6]naphtho[1,2-d]imidazol-2-yl]pyrrolidine-1-carboxylate (270 mg, 46% yield).

methyl {(2S)-1-[(2R)-2-(5-{2-[(2S)-1-{(2R)-2-[(methoxycarbonyl)amino]-2-phenylacetyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate: A mixture of tert-butyl (2S)-2-[9-(2-{(2R)-1-[N-(methoxycarbonyl)-L-valyl]pyrrolidin-2-yl}-1H-imidazol-5-yl)-3,7-dihydroisochromeno[3',4':5,6]naphtho[1,2-d]imidazol-2-yl]pyrrolidine-1-carboxylate (270 mg, 0.37 mmol), concentrated HCl (1.5 mL) and ethanol (8 mL) was heated to 60° C. for 1 hour. The reaction was concentrated and redissolved in a minimal amount of methanol. An equal volume of dichloromethane was added and the solution was again concentrated. Dichloromethane was added to the resulting residue and concentrated off two more times. The crude material was dissolved in 5:1 dichloromethane/dimethylformamide (3.8 mL). To this solution was added (R)-2-(methoxycarbonylamino)-2-phenylacetic acid (96 mg, 0.46 mmol), COMU (190 mg, 0.44 mmol) and diisopropylethylamine (0.20 mL, 1.1 mmol). The reaction was stirred at 0° C. for 30 minutes then warmed to room temperature. Upon completion, the reaction was diluted with acetonitrile (2 mL) and methanol (2 mL). To this solution was added ten drops of 5M aqueous NaOH solution and stirring was continued for 30 minutes. The reaction was diluted with ethyl acetate and the organic layer was washed with water and brine. The combined aqueous washings were extracted three times with ethyl acetate, and the combined organic layers were dried (MgSO$_4$) and concentrated. The crude material was purified by reverse phase HPLC (Gemini, 15 to 45% ACN/H$_2$O+0.1% TFA) to yield methyl {(2S)-1-[(2R)-2-(5-{2-[(2S)-1-{(2R)-2-[(methoxycarbonyl)

amino]-2-phenylacetyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate (155 mg, 51% yield over 2 steps). LCMS-ESI+: calculated for $C_{46}H_{48}N_8O_7$: 824.92; observed [M+1]+: 825.67.

Example MC

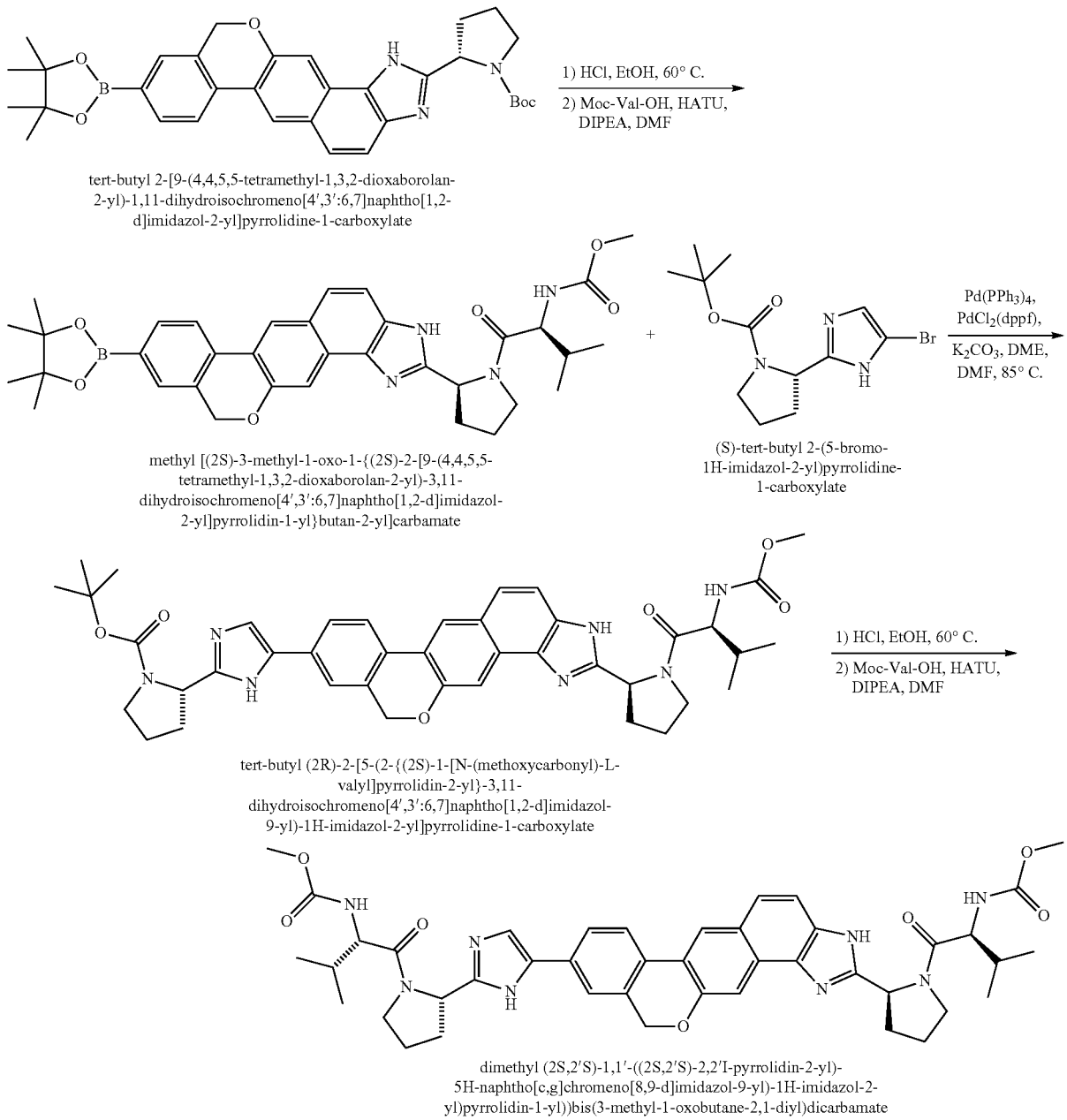

dimethyl (2S,2'S)-1,1'-((2S,2'S)-2,2'1-pyrrolidin-2-yl)-5H-naphtho[c,g]chromeno[8,9-d]imidazol-9-yl)-1H-imidazol-2-yl) pyrrolidin-1-yl))bis(3-methyl-1-oxobutane-2,1-diyl)dicarbamate: This compound was made in an analogous manner to methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate, substituting 7-hydroxy-1-tetralone for 5-hydroxy-1-tetralone in the first step of the sequence. All reactions in the synthesis of Example MC gave similar product yields as in the synthesis of methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate. LCMS-ESI+: calculated for $C_{43}H_{50}N_8O_7$: 790.91; observed [M+1]+: 791.6.

Example MD

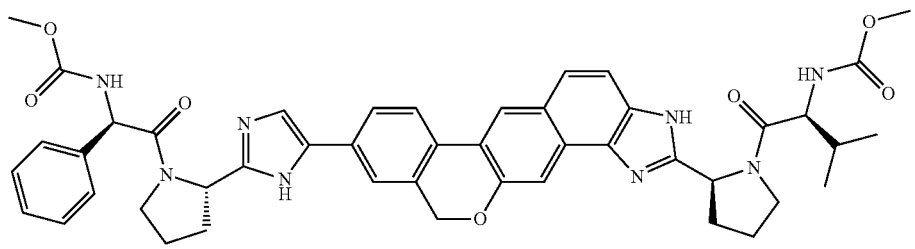

methyl [1-(2-{5-[2-(1-{[methoxycarbonyl]amino]-3-methyl-1-oxobutan-2-yl}pyrrolidin-2-yl)-1,11-dihydroisochromeno[4',3':6,7]naphtho[1,2-d]imidazol-9-yl]-1H-imidazol-2-yl}pyrrolidin-1-yl)-phenyl-1-oxoacet-2-yl]carbamate Example MD: This compound was made in an analogous manner to dimethyl (2S,2'S)-1,1'-((2S,2'S)-2,2'1-pyrrolidin-2-yl)-5H-naphtho[c,g]chromeno[8,9-d]imidazol-9-yl)-1H-imidazol-2-yl)pyrrolidin-1-yl))bis(3-methyl-1-oxobutane-2,1-diyl)dicarbamate, substituting (R)-2-(methoxycarbonylamino)-2-phenylacetic acid for (S)-2-(methoxycarbonylamino)-3-methylbutanoic acid and substituting COMU for HATU in the final amide coupling step. LCMS-ESI$^+$: calculated for $C_{46}H_{48}N_8O_7$: 824.92; observed [M+1]$^+$: 825.67.

Example ME

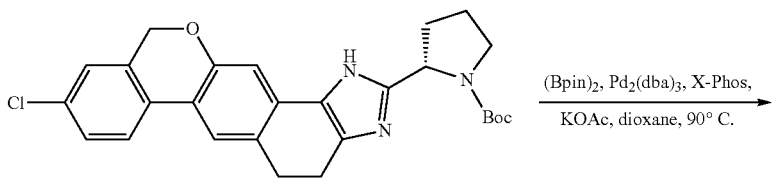

tert-butyl 2-(9-chloro-1,4,5,11-tetrahydroisochromeno[4',3':6,7]naphtho[1,2-d]imidazol-2-yl)pyrrolidine-1-carboxylate

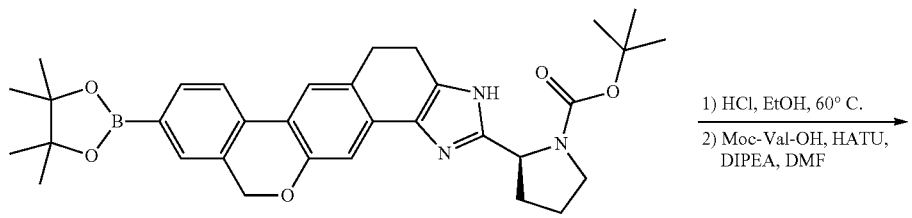

tert-butyl (2S)-2-[9-(4,4,5,5-tetramethyl-1,3,2-dioxaborolan-2-yl)-3,4,5,11-tetrahydroisochromeno[4',3':6,7]naphtho[1,2-d]imidazol-2-yl]pyrrolidine-1-carboxylate

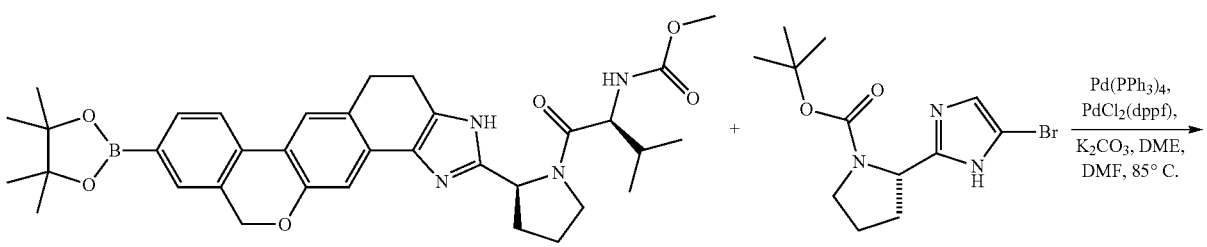

methyl [(2S)-3-methyl-1-oxo-1-{(2S)-2-[9-(4,4,5,5-tetramethyl-1,3,2-dioxaborolan-2-yl)-3,4,5,11-tetrahydroisochromeno[4',3':6,7]naphtho[1,2-d]imidazol-2-yl]pyrrolidin-1-yl}butan-2-yl]carbamate (S)-tert-butyl 2-(5-bromo-1H-imidazol-2-yl)pyrrolidine-1-carboxylate

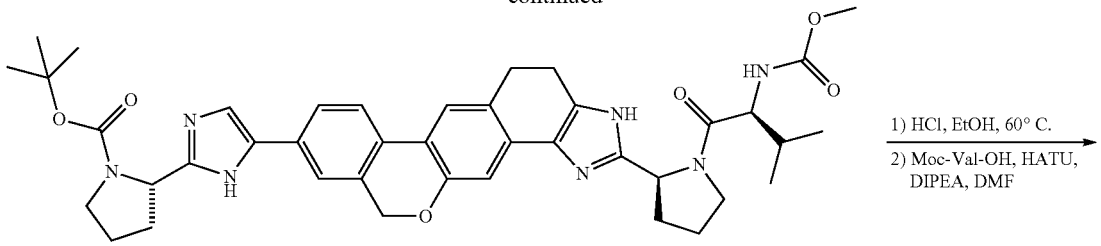

tert-butyl (2R)-2-[5-(2-{(2S)-1-[N-(methoxycarbonyl)-L-valyl]pyrrolidin-2-yl}-3,4,5,11-tetrahydroisochromeno[4',3':6,7]naphtho[1,2-d]imidazol-9-yl)-1H-imidazol-2-yl]pyrrolidine-1-carboxylate

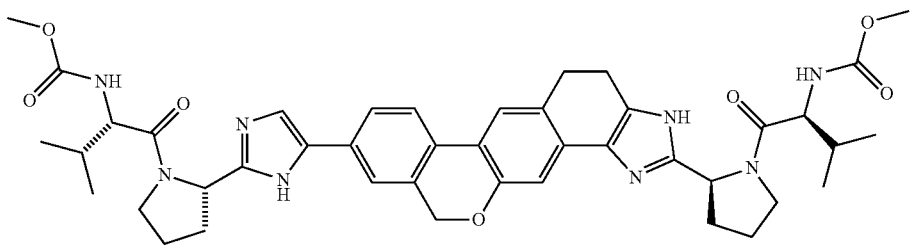

dimethyl (2S,2'S)-1,1'-((2S,2'S)-2,2'I-pyrrolidin-2-yl)-7H-dihydro-naphtho[c,g]chromeno[8,9-d]imidazol-9-yl)-1H-imidazol-2-yl)pyrrolidin-1-yl))bis(3-methyl-1-oxobutane-2,1-diyl)dicarbamate dimethyl (2S,2'S)-1,1'-((2S,2'S)-2,2'1-pyrrolidin-2-yl)-7H-dihydro-naphtho[c,g]chromeno[8,9-d]imidazol-9-yl)-1H-imidazol-2-yl) pyrrolidin-1-yl))bis(3-methyl-1-oxobutane-2,1-diyl)dicarbamate: This compound was made in an analogous manner to dimethyl (2 S,2'S)-1,1'-((2S,2'S)-2,2'1-pyrrolidin-2-yl)-5H-naphtho[c,g]chromeno[8,9-d]imidazol-9-yl)-1H-imidazol-2-yl)pyrrolidin-1-yl))bis(3-methyl-1-oxobutane-2,1-diyl)dicarbamate, omitting the $MnO_2$ oxidation of tert-butyl 2-(9-chloro-1,4,5,11-tetrahydroisochromeno[4',3':6,7]naphtho[1,2-d]imidazol-2-yl)pyrrolidine-1-carboxylate. LCMS-ESI$^+$: calculated for $C_{43}H_{52}N_8O_7$: 792.40; observed [M+1]$^+$: 793.69.

Example MF

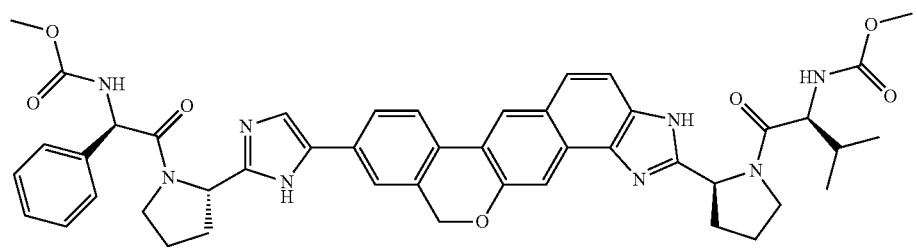

methyl [1-(2-{5-[2-(1-{[(methoxycarbonyl)amino]-3-methyl-1-oxobutan-2-yl}pyrrolidin-2-yl)-1,4,5,11-tetrahydroisochromeno[4',3':6,7]naphtho[1,2-d]imidazol-9-yl]-1H-imidazol-2-yl}pyrrolidin-1-yl)-phenyl-1-oxoacet-2-yl] carbamate: This compound was made in an analogous manner to dimethyl (2S,2'S)-1,1'-((2S,2'S)-2,2'1-pyrrolidin-2-yl)-7H-dihydro-naphtho[c,g]chromeno[8,9-d]imidazol-9-yl)-1H-imidazol-2-yl)pyrrolidin-1-yl))bis(3-methyl-1-oxobutane-2,1-diyl)dicarbamate, substituting (R)-2-(methoxycarbonylamino)-2-phenylacetic acid for (S)-2-(methoxycarbonylamino)-3-methylbutanoic acid and substituting COMU for HATU in the final amide coupling step. LCMS-ESI$^+$: calculated for $C_{46}H_{50}N_8O_7$: 826.94; observed [M+1]$^+$: 827.71.

Example MG

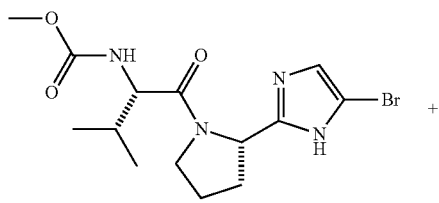

methyl (S)-1-((S)-2-(5-bromo-1H-imidazol-2-yl)pyrrolidin-1-yl)-3-methyl-1-oxobutan-2-ylcarbamate

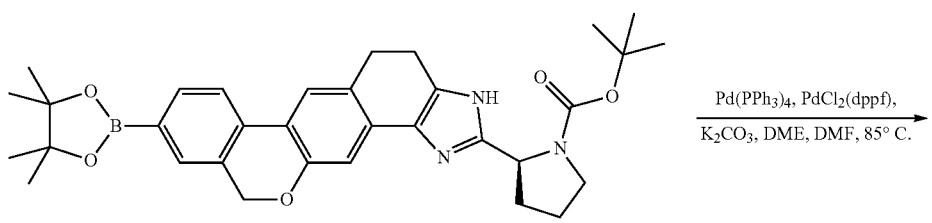

tert-butyl 2-(9-chloro-1,4,5,11-tetrahydroisochromeno[4′,3′:6,7]naphtho[1,2-d]imidazol-2-yl)pyrrolidine-1-carboxylate

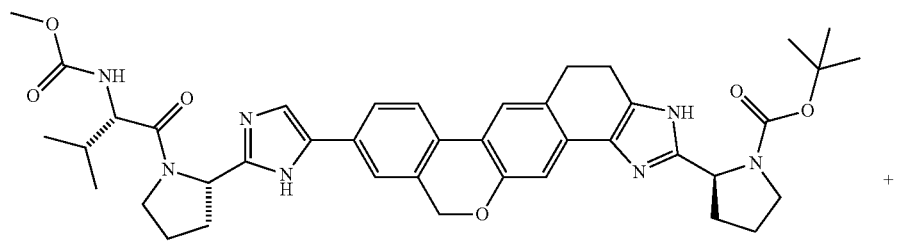

tert-butyl (2S)-2-[9-(2-{(2R)-1-[N-(methoxycarbonyl)-L-valyl]pyrrolidin-2-yl}-1H-imidazol-5-yl)-3,4,5,11-tetrahydroisochromeno[4′,3′:6,7]naphtho[1,2-d]imidazol-2-yl]pyrrolidine-1-carboxylate

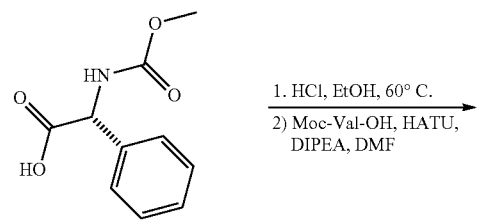

(R)-2-(methoxycarbonylamino)-2-phenylacetic acid

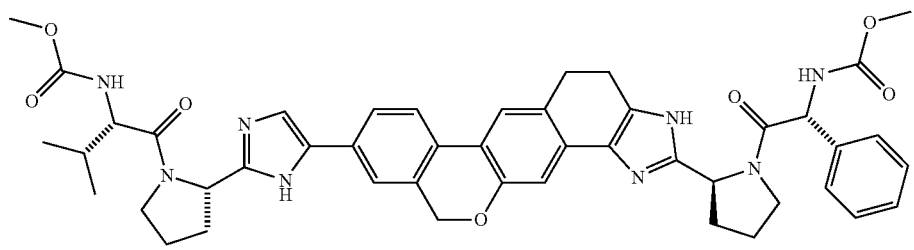

[1-(2-{5-[2-(1-{[(methoxycarbonyl)amino](phenyl)acetyl}pyrrolidin-2-yl)-1,4,5,11-tetrahydroisochromeno[4′,3′:6,7]naphtho[1,2-d]imidazol-9-yl]-1H-imidazol-2-yl}pyrrolidin-1-yl)-3-methyl-1-oxobutan-2-yl]carbamic acid Example MG: This compound was made in an analogous manner to methyl {(2S)-1-[(2R)-2-(5-{2-[(2S)-1-{(2R)-2-[(methoxycarbonyl)amino]-2-phenylacetyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate, substituting tert-butyl (2 S)-2-[9-(2-{(2R)-1-[N-(methoxycarbonyl)-L-valyl]pyrrolidin-2-yl}-1H-imidazol-5-yl)-3,4,5,11-tetrahydroisochromeno[4',3':6,7]naphtho[1,2-d]imidazol-2-yl]pyrrolidine-1-carboxylate for tert-butyl (2S)-2-[9-(2-{(2R)-1-[N-(methoxycarbonyl)-L-valyl]pyrrolidin-2-yl}-1H-imidazol-5-yl)-3,7-dihydroisochromeno[3',4':5,6]naphtho[1,2-d]imidazol-2-yl]pyrrolidine-1-carboxylate. LCMS-ESI+: calculated for $C_{46}H_{50}N_8O_7$: 826.94; observed [M+1]+: 827.64.

Example MH

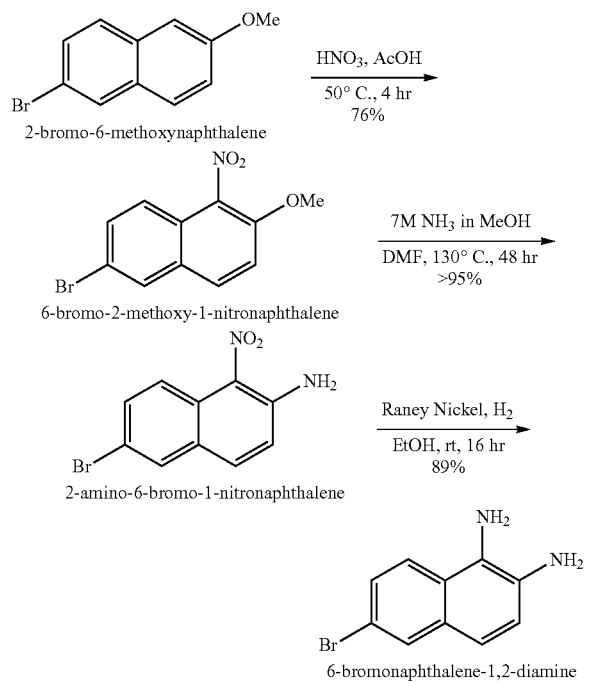

6-bromo-2-methoxy-1-nitronaphthalene: 2-Bromo-6-methoxynaphthalene (20 g, 84.4 mmol) was dissolved in acetic acid (140 mL) by stirring vigorously at 70° C. This solution was cooled to 50° C. and a solution of nitric acid (>90%, 4 mL) in acetic acid (28 mL) was added dropwise. The resulting reaction mixture was stirred at 50° C. for four hours and then cooled to room temperature. The yellow solid was isolated by filtration and recrystallized from acetic acid to yield 6-bromo-2-methoxy-1-nitronaphthalene (18.7 g, 76% yield).

2-amino-6-bromo-1-nitronaphthalene: 6-bromo-2-methoxy-1-nitronaphthalene (12.6 g, 44.7 mmol), dimethylformamide (25.6 mL) and 7N NH3 solution in MeOH (128 mL, purchased from Sigma Aldrich) were combined in a Parr bomb. The bomb was heated in a lab oven at 130° C. After 48 hours, the reactor was removed from the oven and cooled to room temperature. The contents of the bomb were transferred to a glass round bottom flask. The bomb was thoroughly rinsed with dichloromethane and methanol, and the rinsings added to the flask. The contents of the flask were thoroughly concentrated on a rotary evaporator, leaving a brown solid. Water (200 mL) was added to the flask and the resulting suspension was agitated with a stir bar for 30 minutes. The resulting light brown powder was isolated by filtration, rinsing a few times with water. The filter cake was air dried over night to yield 6-bromo-1-nitronaphthalen-2-amine (11.6 g, >95% yield).

6-bromonaphthalene-1,2-diamine: To a mixture of 6-bromo-1-nitronaphthalen-2-amine (11.6 g, 43.4 mmol) in ethanol (430 mL) under argon was added Raney Nickel (~5 g, NOTE: no effort was made to remove the water from the nickel). Hydrogen gas was bubbled through the reaction mixture for 2 minutes. The reaction was stirred under an atmosphere of hydrogen at room temperature. After 16 hours, the Raney Nickel was removed by filtration over Celite and rinsed with ethyl acetate. The filtrate was thoroughly concentrated to yield 6-bromonaphthalene-1,2-diamine (9.2 g, 88% yield).

Example MI

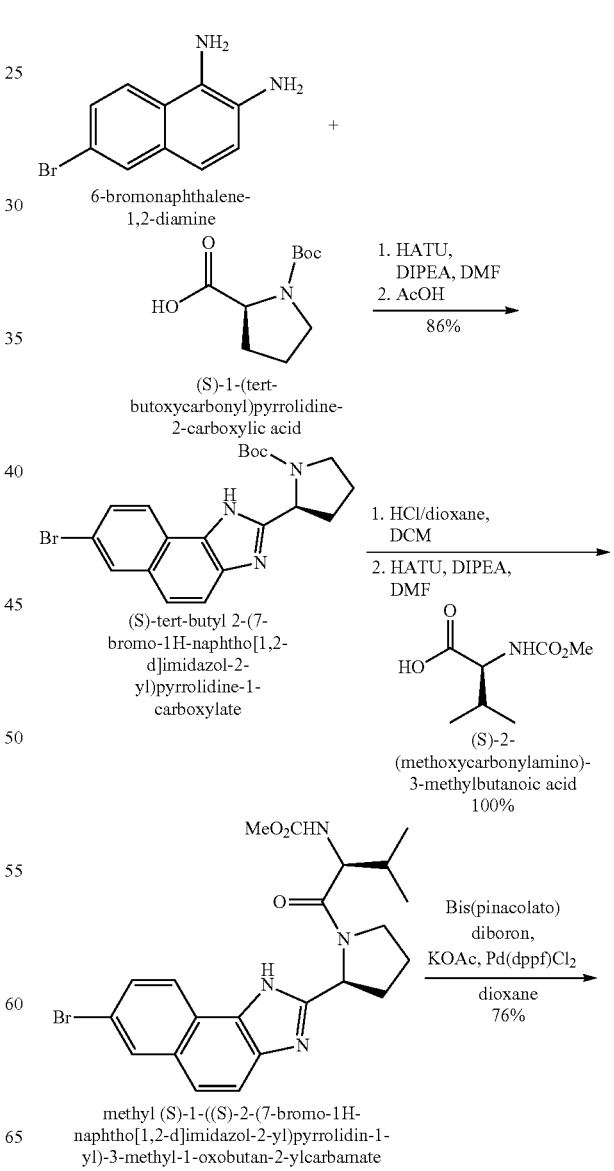

-continued

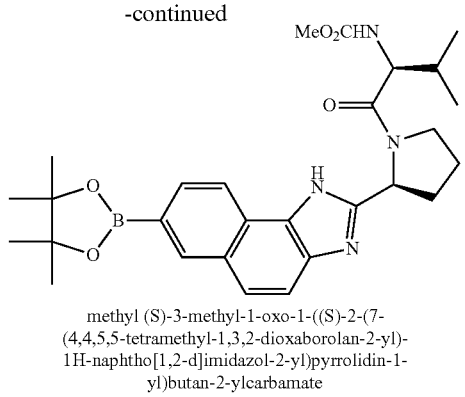

methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate (S)-tert-butyl 2-(7-bromo-1H-naphtho[1,2-d]imidazol-2-yl)pyrrolidine-1-carboxylate: 6-bromonaphthalene-1,2-diamine (1.92 g, 7.19 mmol), (S)-1-(tert-butoxycarbonyl)pyrrolidine-2-carboxylic acid (1.55 g, 7.19 mmol) and HATU (2.73 g, 7.19 mmol) were combined in DMF (18 mL). The stirred mixture was cooled to 0° C. before DIPEA (2.5 mL, 14.4 mmol) was added dropwise. After 3 h, the reaction mixture was diluted with EtOAc (200 mL) and washed successively with saturated aqueous NaHCO$_3$ and brine. The organics were dried over MgSO$_4$, filtered and concentrated under reduced pressure. The crude residue was purified by silica column chromatography (50% to 85% EtOAc/hexanes) to afford the amide adduct (regiochemistry undetermined, 2.71 g, 87%). The amide was dissolved in AcOH (50 mL) and heated to 40° C. for 18 h. After cooling to RT, the solution was concentrated under reduced pressure. The crude residue was dissolved in EtOAc (200 mL) and washed successively with saturated aqueous NaHCO$_3$ (2×) and brine. The organics were dried over MgSO4, filtered and concentrated under reduced pressure to afford (S)-tert-butyl 2-(7-bromo-1H-naphtho[1,2-d]imidazol-2-yl)pyrrolidine-1-carboxylate (2.57 g, 99%).

Methyl (S)-1-((S)-2-(7-bromo-1H-naphtho[1,2-d]imidazol-2-yl)pyrrolidin-1-yl)-3-methyl-1-oxobutan-2-ylcarbamate: (S)-tert-butyl 2-(7-bromo-1H-naphtho[1,2-d]imidazol-2-yl)pyrrolidine-1-carboxylate (1.50 g, 3.60 mmol) was dissolved in DCM (25 mL) and HCl (4 M solution in dioxane, 5 mL, 20 mmol) was added at once. After stirring for 3 h, the solution was concentrated under reduced pressure. The crude residue was treated with (S)-2-(methoxycarbonylamino)-3-methylbutanoic acid (631 mg, 3.60 mmol), HATU (1.37 g, 3.60 mmol) and DMF (18 mL). The stirred solution was cooled to 0° C. and DIPEA (1.9 mL, 10 mmol) was added dropwise. After stirring for 20 min, the reaction mixture was warmed to RT. After an additional 10 min, it was diluted with EtOAc (150 mL) and washed successively with saturated aqueous NaHCO$_3$ and brine. The organics were dried over MgSO$_4$, filtered and concentrated under reduced pressure. The crude residue was purified by silica column chromatography (0% to 33% MeOH/EtOAc) to afford the title compound (1.70 g, 100%).

Methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate: Methyl (S)-1-((S)-2-(7-bromo-1H-naphtho[1,2-d]imidazol-2-yl)pyrrolidin-1-yl)-3-methyl-1-oxobutan-2-ylcarbamate (827 mg, 1.75 mmol), bis(pinacolato)diboron (532 mg, 2.10 mmol), KOAc (515 mg, 5.25 mmol) and Pd(dppf)Cl$_2$ (128 mg, 0.175 mmol) were combined in dioxane (18 mL). The reaction mixture was degassed with bubbling N$_2$ for 10 min, then stirred at 90° C. for 1.5 h. It was then cooled to RT, diluted with EtOAc (150 mL) and washed successively with saturated aqueous NaHCO$_3$ and brine. The organics were dried over MgSO$_4$, filtered and concentrated under reduced pressure. The crude residue was purified by silica column chromatography to afford methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate (695 mg, 76%).

Example MJ

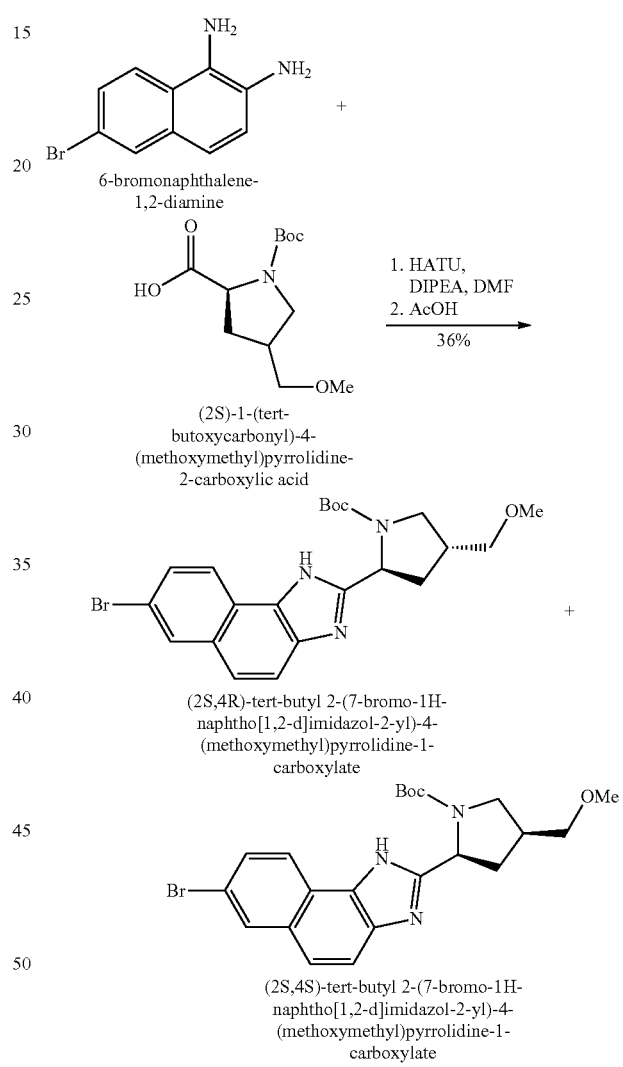

(2S,4R)-tert-butyl 2-(7-bromo-1H-naphtho[1,2-d]imidazol-2-yl)-4-(methoxymethyl)pyrrolidine-1-carboxylate and (2S,4S)-tert-butyl 2-(7-bromo-1H-naphtho[1,2-d]imidazol-2-yl)-4-(methoxymethyl)pyrrolidine-1-carboxylate: 6-bromonaphthalene-1,2-diamine (837 mg, 3.53 mmol), (2S)-1-(tert-butoxycarbonyl)-4-(methoxymethyl)pyrrolidine-2-carboxylic acid (929 mg, 3.58 mmol) and HATU (1.34 g, 3.53 mmol) were combined in DMF (18 mL). The stirred mixture was cooled to 0° C. before DIPEA (1.5 mL, 8.83 mmol) was added and the reaction was warmed to RT. After 18 h, the reaction mixture was diluted with EtOAc (200 mL) and washed successively with saturated aqueous NaHCO$_3$ and brine. The organics were dried over MgSO$_4$, filtered and concentrated under reduced pressure. The crude residue was purified by silica column chromatography (65% to 90% EtOAc/hexanes) to afford the amide adduct (regiochemistry undetermined, 1.48 g, 87%). The amide was dissolved in AcOH (50 mL) and heated to 40° C. for 10 h. After cooling to RT, the solution was concentrated under reduced pressure. The crude residue was dissolved in EtOAc (200 mL) and washed successively with saturated aqueous NaHCO$_3$ (2×) and brine. The organics were dried over MgSO$_4$, filtered and concentrated under reduced pressure. The crude residue was purified by silica column chromatography (50% to 75% EtOAc/hexanes) to afford (2S,4R)-tert-butyl 2-(7-bromo-1H-naphtho[1,2-d]imidazol-2-yl)-4-(methoxymethyl)pyrrolidine-1-carboxylate (less polar product, 641 mg, 45%) and (2S,4S)-tert-butyl 2-(7-bromo-1H-naphtho[1,2-d]imidazol-2-yl)-4-(methoxymethyl)pyrrolidine-1-carboxylate (more polar product, 582 mg, 41%).

Example MK

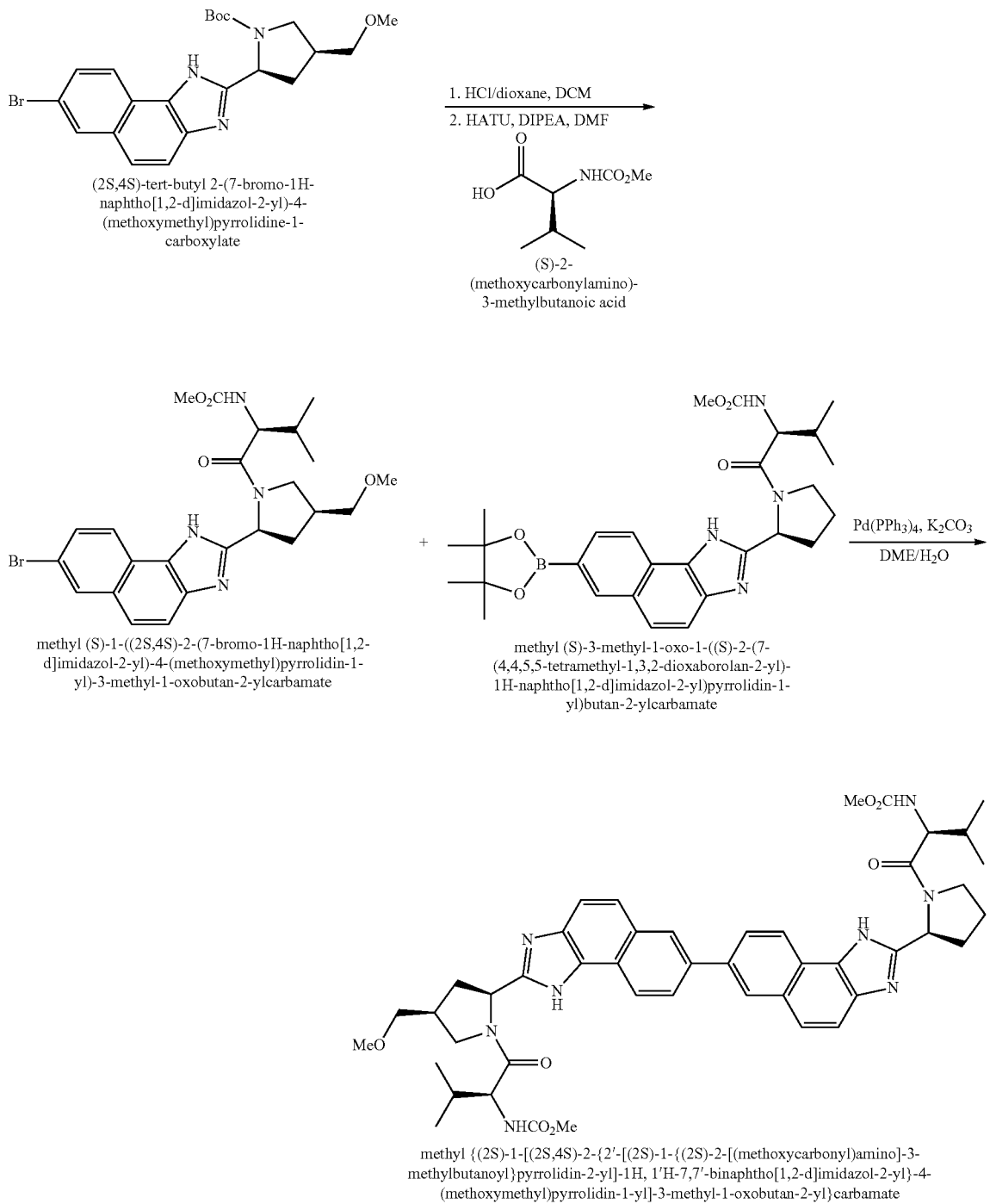

Methyl (S)-1-((2S,4S)-2-(7-bromo-1H-naphtho[1,2-d]imidazol-2-yl)-4-(methoxymethyl)pyrrolidin-1-yl)-3-methyl-1-oxobutan-2-ylcarbamate: (2S,4S)-tert-butyl 2-(7-bromo-1H-naphtho[1,2-d]imidazol-2-yl)-4-(methoxymethyl)pyrrolidine-1-carboxylate (526 mg, 1.14 mmol) was dissolved in DCM (15 mL) and HCl (4 M in dioxane, 3 mL, 12 mmol) was added. The reaction mixture was stirred for 2 h and then concentrated under reduced pressure. The crude residue was treated with (methoxycarbonylamino)-3-methylbutanoic acid (220 mg, 1.25 mmol), HATU (433 mg, 1.14 mmol) and DMF (11 mL), then cooled to 0° C. DIPEA (0.99 mL, 5.7 mmol) was added dropwise and the reaction mixture was immediately warmed to RT. After 45 min at RT, the mixture was diluted with EtOAc (100 mL) and washed successively with saturated aqueous NaHCO₃, water and brine. The organics were dried over MgSO₄, filtered and concentrated under reduced pressure. The crude residue was purified by silica column chromatography (0% to 33% MeOH/EtOAc) to afford methyl (S)-1-((2S,4S)-2-(7-bromo-1H-naphtho[1,2-d]imidazol-2-yl)-4-(methoxymethyl)pyrrolidin-1-yl)-3-methyl-1-oxobutan-2-ylcarbamate (584 mg, 99%).

Methyl {(2S)-1-[(2S,4S)-2-{2'-[(2S)-1-{(2S)-2-[(methoxycarbonyl)amino]-3-methylbutanoyl}pyrrolidin-2-yl]-1H,1'H-7,7'-binaphtho[1,2-d]imidazol-2-yl}-4-(methoxymethyl)pyrrolidin-1-yl]-3-methyl-1-oxobutan-2-yl}carbamate: Methyl (S)-1-((2S,4S)-2-(7-bromo-1H-naphtho[1,2-d]imidazol-2-yl)-4-(methoxymethyl)pyrrolidin-1-yl)-3-methyl-1-oxobutan-2-ylcarbamate (210 mg, 0.406 mmol), methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate (253 mg, 0.487 mmol), Pd(PPh₃)₄ (47 mg, 0.0406 mmol) and K₂CO₃ (2M in H₂O, 0.50 mL, 1.0 mmoL) were combined in DME (4 mL). The mixture was degassed with bubbling N₂ for 10 min the heated to 85° C. for 15 h. After cooling, the reaction mixture was diluted with 5 mL MeOH, filtered and concentrated. The crude residue was purified by reverse phase HPLC to afford methyl {(2S)-1-[(2S,4S)-2-{2'-[(2S)-1-{(2S)-2-[(methoxycarbonyl)amino]-3-methylbutanoyl}pyrrolidin-2-yl]-1H,1'H-7,7'-binaphtho[1,2-d]imidazol-2-yl]-4-(methoxymethyl)pyrrolidin-1-yl]-3-methyl-1-oxobutan-2-yl}carbamate (140 mg, 42%). MS (ESI) m/z 831 [M+H]⁺.

Example ML

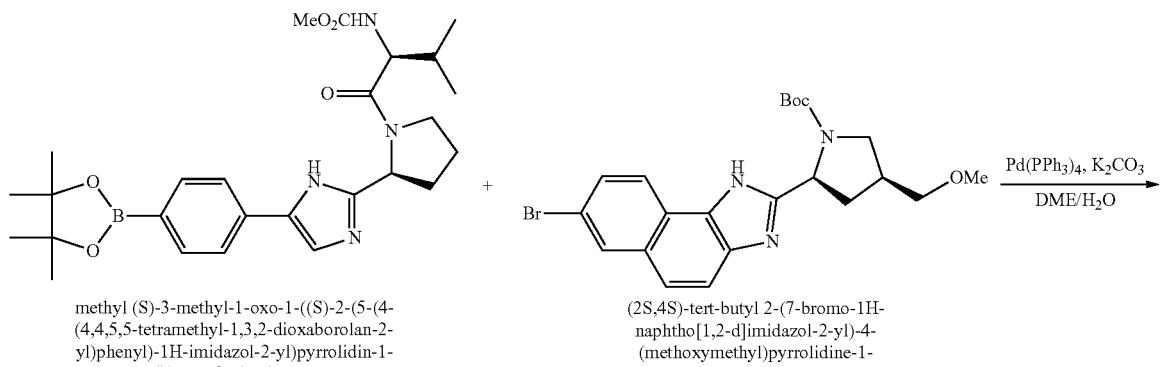

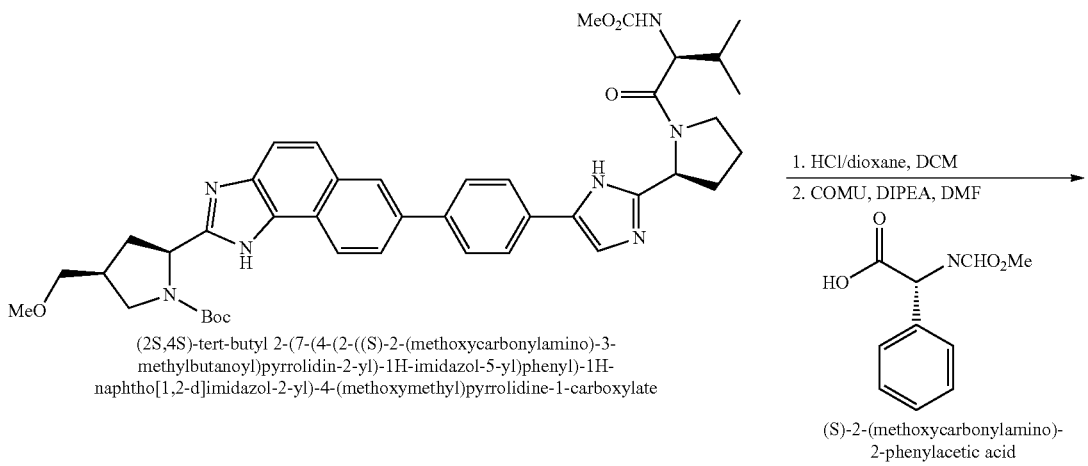

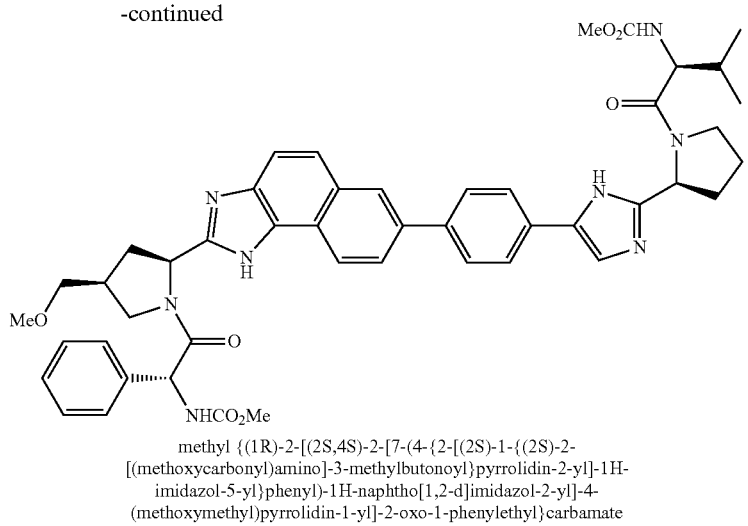

methyl {(1R)-2-[(2S,4S)-2-[7-(4-{2-[(2S)-1-{(2S)-2-[(methoxycarbonyl)amino]-3-methylbutonoyl}pyrrolidin-2-yl]-1H-imidazol-5-yl}phenyl)-1H-naphtho[1,2-d]imidazol-2-yl]-4-(methoxymethyl)pyrrolidin-1-yl]-2-oxo-1-phenylethyl}carbamate (2S,4S)-tert-butyl 2-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-4-(methoxymethyl)pyrrolidine-1-carboxylate: Methyl (S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-ylcarbamate (260 mg, 0.524 mmol), (2S,4S)-tert-butyl 2-(7-bromo-1H-naphtho[1,2-d]imidazol-2-yl)-4-(methoxymethyl)pyrrolidine-1-carboxylate (201 mg, 0.437 mmol), Pd(PPh$_3$)$_4$ (50 mg, 0.0437 mmol) and K$_2$CO$_3$ (2 M in H$_2$O, 0.55 mL, 1.1 mmol) were combined in DME (4 mL). The reaction mixture was degassed with bubbling N$_2$, then heated to 85° C. for 5 h. Upon completion, the reaction mixture was cooled to RT, diluted with 5 mL MeOH, filtered and concentrated. The crude residue was purified by silica column chromatography (0% to 45% MeOH/EtOAc) to afford (2S,4S)-tert-butyl 2-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-4-(methoxymethyl)pyrrolidine-1-carboxylate (163 mg, 50%).

Methyl {(1R)-2-[(2S,4S)-2-[7-(4-{2-[(2S)-1-{(2S)-2-[(methoxycarbonyl)amino]-3-methylbutanoyl}pyrrolidin-2-yl]-1H-imidazol-5-yl}phenyl)-1H-naphtho[1,2-d]imidazol-2-yl]-4-(methoxymethyl)pyrrolidin-1-yl]-2-oxo-1-phenylethyl}carbamate: (2S,4S)-tert-butyl 2-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-4-(methoxymethyl)pyrrolidine-1-carboxylate (140 mg, 0.187 mmol) was dissolved in DCM (5 mL) and HCl (4 M in dioxane, 1 mL, 4 mmol) was added. After stirring for 1.5 h, the reaction mixture was concentrated under reduced pressure. The crude residue was treated with (R)-2-(methoxycarbonylamino)-2-phenylacetic acid (43 mg, 0.206 mmol), COMU (80 mg, 0.187 mmol), DMF (3 mL) and DIPEA (0.33 mL, 1.9 mmol). After stirring at RT for 20 min, the solution was diluted with 30 mL 10% MeOH/EtOAc. The organic layer was washed successively with saturated aqueous NaHCO$_3$ and brine. The organics were dried over MgSO$_4$, filtered and concentrated under reduced pressure. The resulting residue was purified by silica column chromatography to afford methyl {(1R)-2-[(2S,4S)-2-[7-(4-{2-[(2S)-1-{(2 S)-2-[(methoxycarbonyl)amino]-3-methylbutanoyl}pyrrolidin-2-yl]-1H-imidazol-5-yl}phenyl)-1H-naphtho[1,2-d]imidazol-2-yl]-4-(methoxymethyl)pyrrolidin-1-yl]-2-oxo-1-phenylethyl}carbamate (106 mg, 68%). MS (ESI) m/z 841 [M+H]$^+$.

Example MM

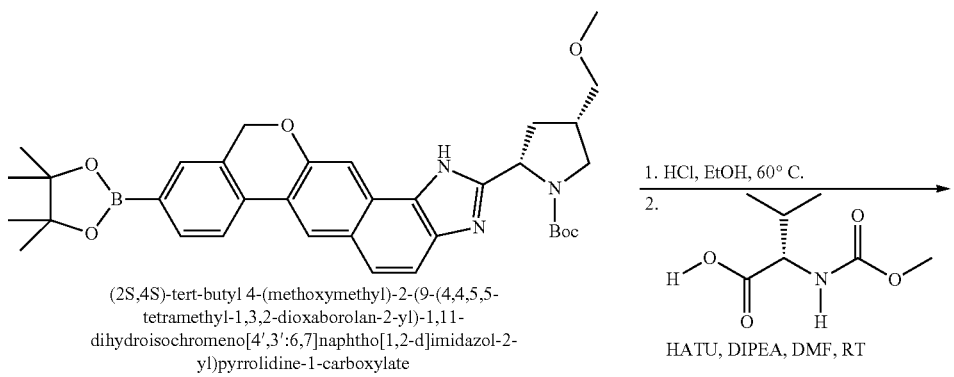

(2S,4S)-tert-butyl 4-(methoxymethyl)-2-(9-(4,4,5,5-tetramethyl-1,3,2-dioxaborolan-2-yl)-1,11-dihydroisochromeno[4′,3′:6,7]naphtho[1,2-d]imidazol-2-yl)pyrrolidine-1-carboxylate 1. HCl, EtOH, 60° C.
2.

HATU, DIPEA, DMF, RT

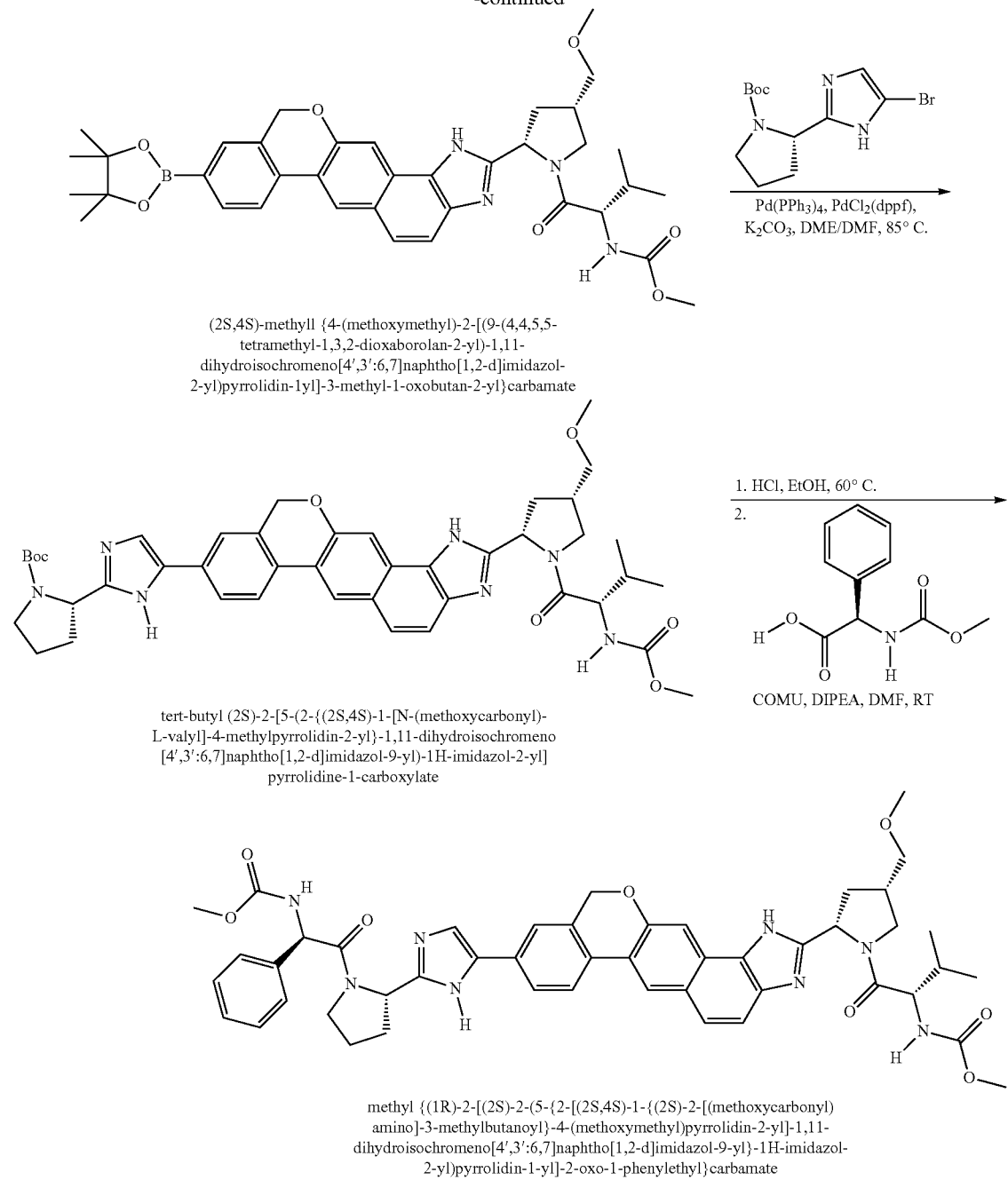

(2S,4S)-methyll {4-(methoxymethyl)-2-[(9-(4,4,5,5-tetramethyl-1,3,2-dioxaborolan-2-yl)-1,11-dihydroisochromeno[4',3':6,7]naphtho[1,2-d]imidazol-2-yl)pyrrolidin-1yl]-3-methyl-1-oxobutan-2-yl}carbamate tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl] pyrrolidine-1-carboxylate methyl {(1R)-2-[(2S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate (2S,4S)-methyll {4-(methoxymethyl)-2-[(9-(4,4,5,5-tetramethyl-1,3,2-dioxaborolan-2-yl)-1,11-dihydroisochromeno[4',3':6,7]naphtho[1,2-d]imidazol-2-yl) pyrrolidin-1-yl]-3-methyl-1-oxobutan-2-yl}carbamate: A solution of (2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl) pyrrolidine-1-carboxylate (424 mg, 0.69 mmol), ethanol (6 mL) and concentrated HCl (2 mL) was heated to 60° C. for 1 hour. The reaction was concentrated and the crude material dissolved in DCM (10 mL). This solution was concentrated and to this material was added a solution of 2-methoxycarbonylamino-3-methylbutyric acid (152 mg, 0.86 mmol) and HATU (303 mg, 0.79 mmol) in DMF (6 mL). To the resulting solution was added diisopropylethylamine (360 µL, 2.08 mmol). After stirring for 2 hours at room temperature, the reaction was diluted with ethyl acetate, washed with 5% NaHCO$_3$ solution, water and brine, dried (Na$_2$SO$_4$), concentrated and dried under vacuum to give (2S,4S)-methyll {4-(methoxymethyl)-2-[(9-(4,4,5,5-tetramethyl-1,3,2-dioxaborolan-2-yl)-1,11-dihydroisochromeno[4',3':6,7] naphtho[1,2-d]imidazol-2-yl)pyrrolidin-1-yl]-3-methyl-1-oxobutan-2-yl}carbamate.

tert-butyl(2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate. To a solution of (2S,4S)-methyll{4-(methoxymethyl)-2-[(9-(4,4,5,5-tetramethyl-1,3, 2-dioxaborolan-2-yl)-1,11-dihydroiso chromeno[4',3':6,7]naphtho[1,2-d]imidazol-2-yl)pyrrolidin-1yl]-3-methyl-1-oxobutan-2-yl}carbamate (0.69 mmol), (S)-tert-butyl 2-(5-bromo-1H-imidazol-2-yl)pyrrolidine-1-carboxylate (220 mg, 0.69 mmol), tetrakis(triphenylphosphine) palladium(0) (24 mg, 0.02 mmol) and dichloro[1,1'-bis(diphenylphosphino) ferrocene]palladium(II) (31 mg, 0.04 mmol) in a mixture of 1,2-dimethoxyethane (6.0 mL) and dimethylformamide (1.0 mL) was added a solution of potassium carbonate (2M in water, 1.04 mL, 2.0 mmol). The resulting mixture was degassed and then heated to 85° C. under argon for 18 hours. After cooling to room temperature, the reaction was diluted with ethyl acetate. The organics were washed with water and brine, dried ($Na_2SO_4$), and concentrated. The crude residue was purified by flash chromatography to yield (tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate (145 mg, 27%).

methyl{(1R)-2-[(2S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroiso chromeno[4',3':6,7]naphtho[1,2-d]imidazol-9-yl}-1H-imidazol-2-yl)pyrrolidin-1-yl]-2-oxo-1-phenylethyl}carbamate: A solution of tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate (145 mg, 0.18 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (51 mg, 0.24 mmol) and COMU (92 mg, 021 mmol) in DMF (3 mL). To the resulting solution was added diisopropylethylamine (100 µL, 0.56 mmol). After stirring for 2 hours at room temperature, the reaction was diluted with ethyl acetate, washed with water and brine, dried ($Na_2SO_4$), concentrated and purified by preparative reverse phase HPLC (Gemini, 15 to 43% $ACN/H_2O$+0.1% TFA). The product fractions were lyophilized to give methyl {(1R)-2-[(2S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate (68 mg, 39%). MS (ESI) m/z 870 [M+H]$^+$. 1H NMR (400 MHz, dmso) δ 8.71 (s, 1H), 8.22 (d, 1H, J=8 Hz), 8.09 (m, 1H), 7.88-7.63 (m, 6H), 7.36-7.29 (m, 6H), 5.41 (d, 1H, J=8.4 Hz), 5.30-5.24 (m, 2H), 5.14-5.10 (m, 1H), 4.13-3.09 (m, 15H), 2.47-1.80 (m, 8H), 0.80 (dd, 6H, J=6.4 Hz, J=23 Hz).

Example MN

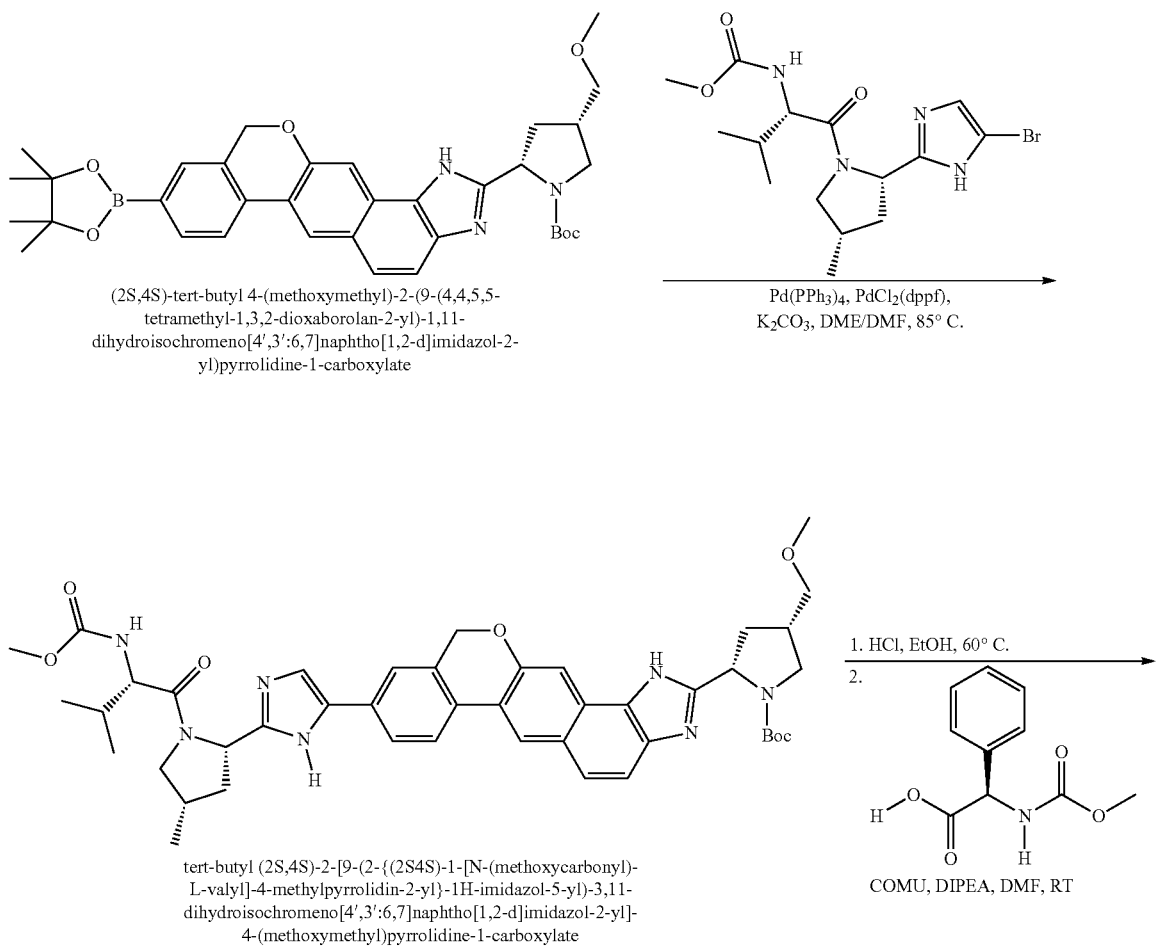

(2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate Pd(PPh$_3$)$_4$, PdCl$_2$(dppf), K$_2$CO$_3$, DME/DMF, 85° C.

tert-butyl (2S,4S)-2-[9-(2-{(2S4S)-1-[N-(methoxycarbonyl)-L-valyl]-4-methylpyrrolidin-2-yl}-1H-imidazol-5-yl)-3,11-dihydroisochromeno[4',3':6,7]naphtho[1,2-d]imidazol-2-yl]-4-(methoxymethyl)pyrrolidine-1-carboxylate 1. HCl, EtOH, 60° C.
2.

COMU, DIPEA, DMF, RT

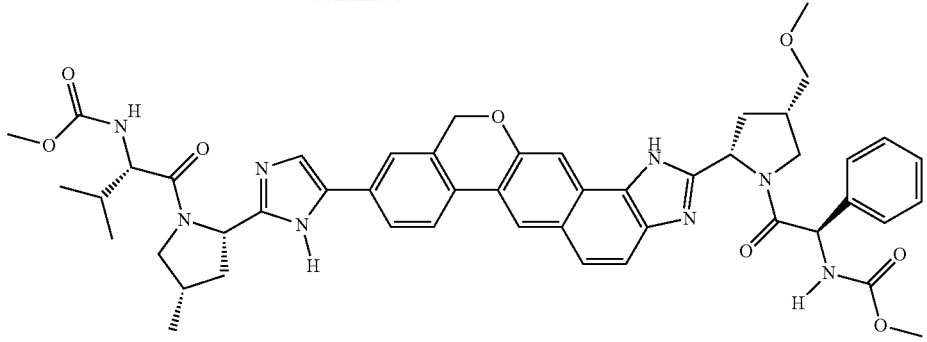

methyl {(2S)-1-[(2S,4S)-2-(5-{2-[(2S,4S)-1-{(2R)-2-[(methoxycarbonyl)amino]-2-phenylacetyl}-4-(methoxymethyl)pyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate tert-butyl(2S,4S)-2-[9-(2-{(2S4S)-1-[N-(methoxycarbonyl)-L-valyl]-4-methyl pyrrolidin-2-yl}-1H-imidazol-5-yl)-3,11-dihydroisochromeno[4',3':6,7]naphtho[1,2-d]imidazol-2-yl]-4-(methoxymethyl)pyrrolidine-1-carboxylate. To a solution of (2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate (438 mg, 0.72 mmol), methyl (S)-1-((2S,4S)-2-(5-bromo-1H-imidazol-2-yl)-4-methylpyrrolidin-1-yl)-3-methyl-1-oxobutan-2-ylcarbamate (276 mg, 0.72 mmol), tetrakis(triphenylphosphine) palladium(0) (41 mg, 0.04 mmol) and dichloro[1,1'-bis(diphenylphosphino) ferrocene]palladium(II) (52 mg, 0.07 mmol) in a mixture of 1,2-dimethoxyethane (8.6 mL) and dimethylformamide (1.5 mL) was added a solution of potassium carbonate (2M in water, 1.07 mL, 2.15 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield tert-butyl (2S,4S)-2-[9-(2-{(2S4S)-1-[N-(methoxycarbonyl)-L-valyl]-4-methylpyrrolidin-2-yl}-1H-imidazol-5-yl)-3,11-dihydroisochromeno[4',3':6,7]naphtho[1,2-d]imidazol-2-yl]-4-(methoxymethyl)pyrrolidine-1-carboxylate (182 mg, 32%).

methyl {(2S)-1-[(2S,4S)-2-(5-{2-[(2S,4S)-1-{(2R)-2-[(methoxycarbonyl)amino]-2-phenylacetyl}-4-(methoxymethyl)pyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate: A solution of tert-butyl (2S,4S)-2-[9-(2-{(2S4S)-1-[N-(methoxycarbonyl)-L-valyl]-4-methylpyrrolidin-2-yl}-1H-imidazol-5-yl)-3,11-dihydroisochromeno[4',3':6,7]naphtho[1,2-d]imidazol-2-yl]-4-(methoxy methyl) pyrrolidine-1-carboxylate (182 mg, 0.18 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (47 mg, 0.23 mmol) and COMU (85 mg, 0.2 mmol) in DMF (3 mL). To the resulting solution was added diisopropylethylamine (90 μL, 0.52 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 49% ACN/H$_2$O+0.1% TFA). The product fractions were lyophilized to give methyl{(2S)-1-[(2S,4S)-2-(5-{2-[(2S,4S)-1-{(2R)-2-[(methoxycarbonyl)amino]-2-phenylacetyl}-4-(methoxymethyl)pyrrolidin-2-yl]-1,11-dihydroisochromeno[4',3':6,7]naphtho[1,2-d]imidazol-9-yl}-1H-imidazol-2-yl)-methylpyrrolidin-1-yl]-3-methyl-1-oxobutan-2-yl}carbamate (32 mg, 39%). MS (ESI) m/z 884 [M+H]$^+$.

1H NMR (400 MHz, dmso) δ 8.70 (s, 1H), 8.21 (d, 1H, J=8 Hz), 8.08 (s, 1H), 7.90-7.64 (m, 6H), 7.34-7.31 (m, 3H), 7.64 (d, 1H, J=8.4 Hz), 5.47 (d, 1H, J=7.6 Hz), 5.28-5.25 (m, 3H), 5.05-5.01 (m, 1H), 4.19-4.04 (m, 3H), 3.67-3.15 (m, 15H), 2.51-2.46 (m, 4H), 1.95-1.92 (m, 2H), 1.82-1.76 (m, 1H), 1.10 (d, 3H, J=6 Hz), 0.75 (dd, 6H, J=6.8 Hz, J=14 Hz).

Example MO

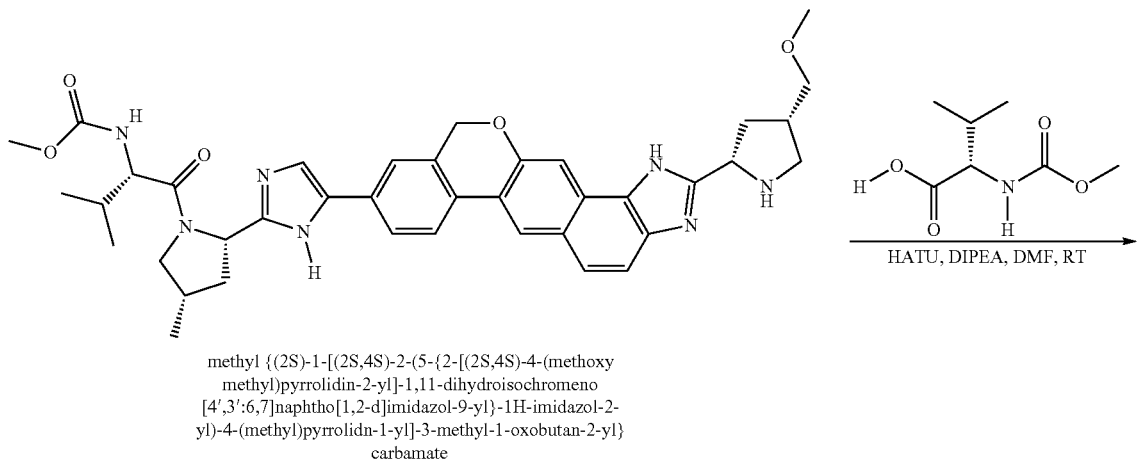

methyl {(2S)-1-[(2S,4S)-2-(5-{2-[(2S,4S)-4-(methoxymethyl)pyrrolidin-2-yl]-1,11-dihydroisochromeno[4',3':6,7]naphtho[1,2-d]imidazol-9-yl}-1H-imidazol-2-yl)-4-(methyl)pyrrolidn-1-yl]-3-methyl-1-oxobutan-2-yl}carbamate

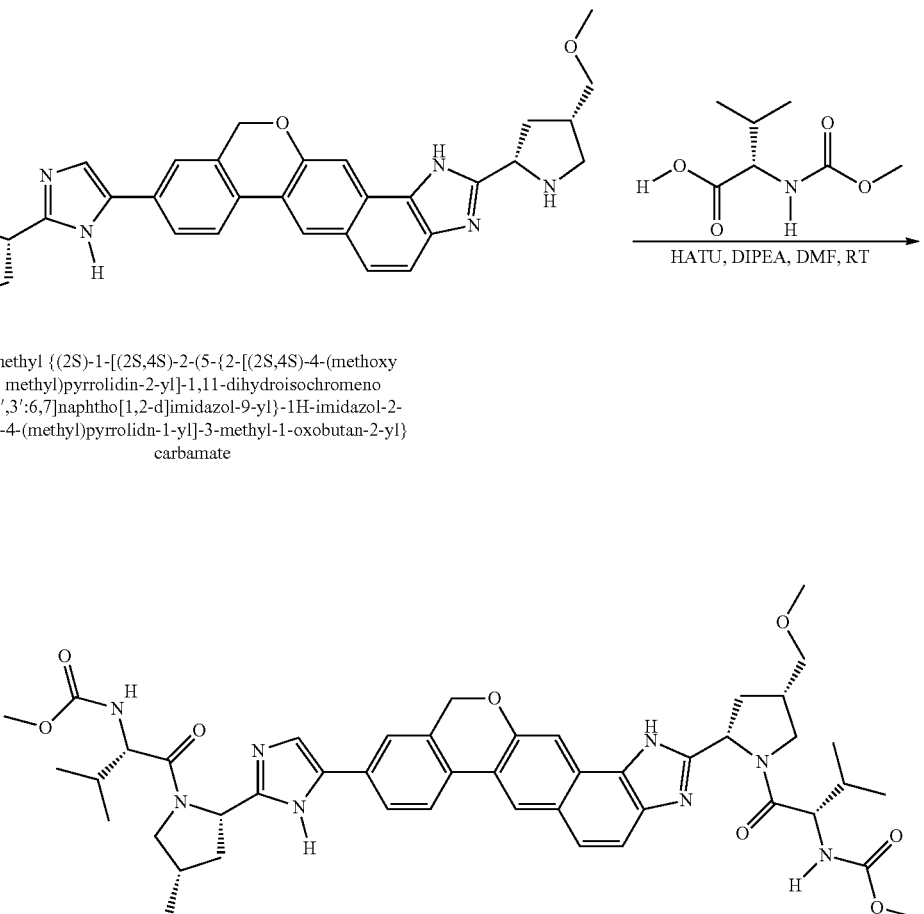

methyl {(2S)-1-[(2S,4S)-2-(5-{2-[(2S,4S)-1-{(2S)-2-[(methoxycarbonyl)amino]-3-methylbutanoyl}-4-methoxymethylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate methyl {(2S)-1-[(2S,4S)-2-(5-{2-[(2S,4S)-1-{(2S)-2-[(methoxycarbonyl)amino]-3-methylbutanoyl}-4-methoxymethylpyrrolidin-2-yl]-1,11-dihydroisochromeno[4',3':6,7]naphtho[1,2-d]imidazol-9-yl]-1H-imidazol-2-yl)-4-methylpyrrolidin-1-yl]-3-methyl-1-oxobutan-2-yl}carbamate: To a solution of methyl {(2S)-1-[(2S,4S)-2-(5-{2-[(2S,4S)-4-(methoxymethyl)pyrrolidi-2-yl]-1,11-dihydroisochromeno[4',3':6,7]naphtho[1,2-d]imidazol-9-yl}-1H-imidazol-2-yl)-4-(methyl)pyrrolidin-1-yl]-3-methyl-1-oxobutan-2-yl}carbamate (57 mg, 0.08 mmol), 2-methoxycarbonylamino-3-methylbutyric acid (19 mg, 0.1 mmol), HATU (303 mg, 0.79 mmol) in DMF (1 mL) was added diisopropylethylamine (43 μL, 0.24 mmol). After stirring for 2 hours at room temperature, the reaction was diluted with ethyl acetate, washed with 5% NaHCO$_3$ solution, water and brine, dried (Na$_2$SO$_4$), concentrated and purified by preparative reverse phase HPLC (Gemini, 15 to 43% ACN/H$_2$O+0.1% TFA). The product fractions were lyophilized to give methyl {(2S)-1-[(2S,4S)-2-(5-{2-[(2S,4S)-1-{(2S)-2-[(methoxycarbonyl)amino]-3-methylbutanoyl}-4-methoxymethylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate. (13 mg, 19%). MS (ESI) m/z 850 [M+H]$^+$.

1H NMR (400 MHz, dmso) δ 8.66 (s, 1H), 8.28-8.13 (m, 1H), 8.12-7.99 (m, 1H), 7.90-7.75 (m, 3H), 7.73-7.65 (m, 1H), 7.63-7.57 (m, 1H), 7.34-7.19 (m, 2H), 5.30-5.24 (m, 2H), 5.21-4.95 (m, 2H), 4.33-3.93 (m, 6H), 3.23-3.58 (m, 12H), 2.76-2.59 (m, 2H), 2.02-1.73 (m, 6H), 1.12-1.07 (m, 3H), 0.86-0.68 (m, 12H).

Example MP

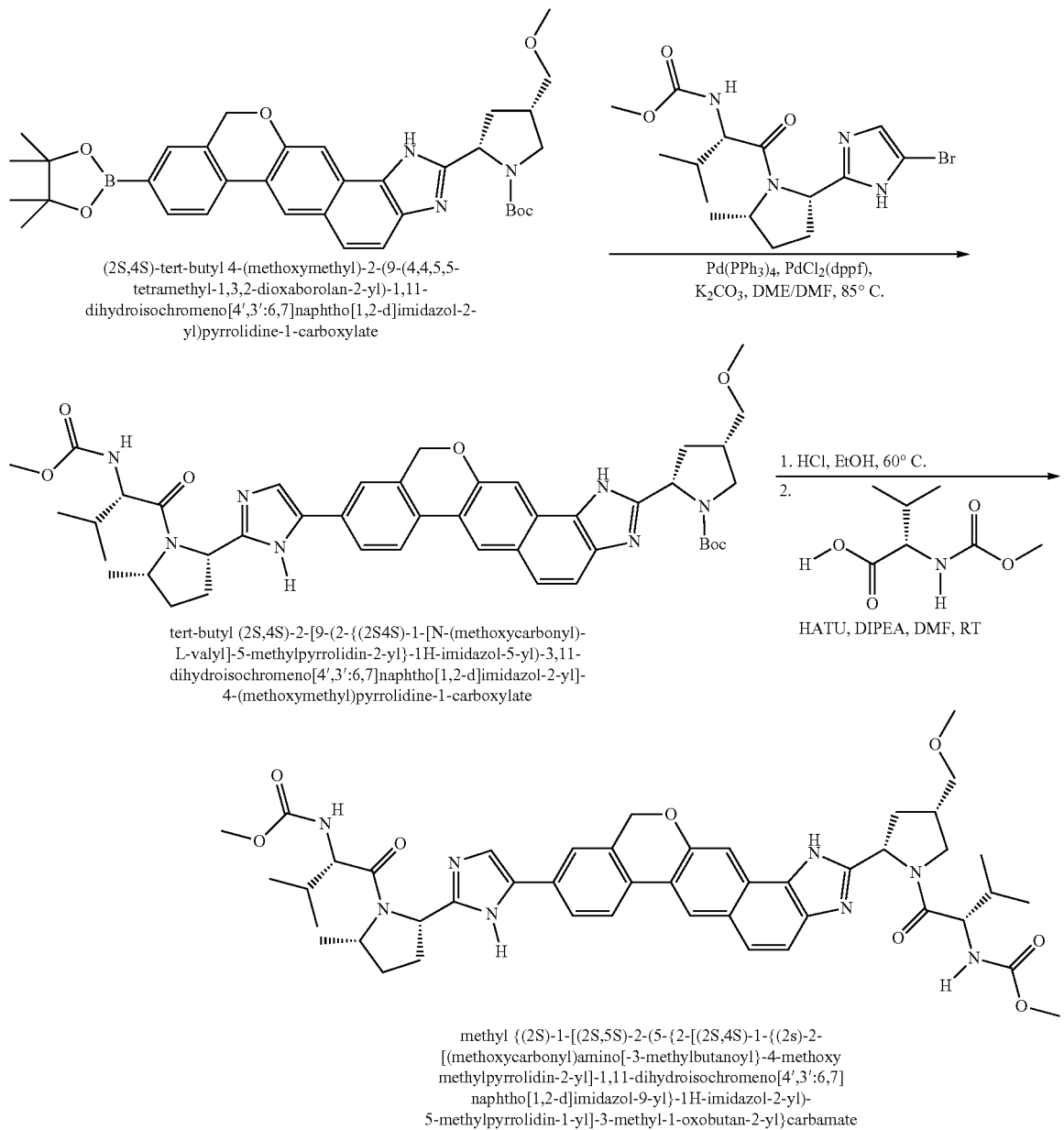

tert-butyl(2S,4S)-2-[9-(2-{(2S,5S)-1-[N-(methoxycarbonyl)-L-valyl]-5-methyl pyrrolidin-2-yl}-1H-imidazol-5-yl)-3,11-dihydroisochromeno[4',3':6,7]naphtho[1,2-d]imidazol-2-yl]-4-(methoxymethyl)pyrrolidine-1-carboxylate To a solution of (2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate (217 mg, 0.35 mmol), methyl (S)-1-((2S,5S)-2-(5-bromo-1H-imidazol-2-yl)-5-methylpyrrolidin-1-yl)-3-methyl-1-oxobutan-2-ylcarbamate (170 mg, 0.39 mmol), tetrakis(triphenylphosphine) palladium(0) (21 mg, 0.02 mmol) and dichloro[1,1'-bis(diphenylphosphino) ferrocene]palladium(II) (26 mg, 0.04 mmol) in a mixture of 1,2-dimethoxyethane (4.3 mL) and dimethylformamide (0.75 mL) was added a solution of potassium carbonate (2M in water, 0.53 mL, 1.06 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield tert-butyl (2S,4S)-2-[9-(2-{(2S,5S)-1-[N-(methoxycarbonyl)-L-valyl]-5-methylpyrrolidin-2-yl}-1H-imidazol-5-yl)-3,11-dihydroisochromeno[4',3':6,7]naphtho[1,2-d]imidazol-2-yl]-4-(methoxy methyl)pyrrolidine-1-carboxylate (110 mg, 39%).

methyl{(2S)-1-[(2S,5S)-2-(5-{2-[(2S,4S)-1-{(2S)-2-[(methoxycarbonyl)amino]-3-methylbutanoyl}-4-methoxymethylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2- yl}carbamate: A solution of tert-butyl (2S,4S)-2-[9-(2-{(2S,5S)-1-[N-(methoxycarbonyl)-L-valyl]-5-methylpyrrolidin-2-yl}-1H-imidazol-5-yl)-3,11-dihydroisochromeno[4',3':6,7]naphtho[1,2-d]imidazol-2-yl]-4-(methoxy methyl)pyrrolidine-1-carboxylate (108 mg, 0.14 mmol), ethanol (2 mL) and concentrated HCl (0.7 mL) was heated to 60° C. for 1 hour. The reaction was concentrated and the crude material dissolved in DCM (10 mL). This solution was concentrated and to this material was added a solution of 2-methoxycarbonylamino-3-methylbutyric acid (31 mg, 0.18 mmol) and HATU (60 mg, 0.16 mmol) in DMF (2 mL). To the resulting solution was added diisopropylethylamine (70 μL, 0.41 mmol). After stirring for 2 hours at room temperature, the reaction was diluted with ethyl acetate, washed with 5% NaHCO₃ solution, water and brine, dried (Na₂SO₄), After stirring for 2 hours at room temperature, the reaction was diluted with ethyl acetate, washed with 5% NaHCO₃ solution, water and brine, dried (Na₂SO₄), concentrated and purified by preparative reverse phase HPLC (Gemini, 15 to 43% ACN/H₂O+0.1% TFA). The product fractions were lyophilized to give methyl {(2S)-1-[(2S,5S)-2-(5-{2-[(2S,4S)-1-{(2S)-2-[(methoxycarbonyl)amino]-3-methylbutanoyl}-4-methoxy methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (52 mg, 45%). MS (ESI) m/z 850 [M+H]⁺.

1H NMR (400 MHz, dmso) δ 8.69 (s, 1H), 8.18 (d, 1H, J=7.6 Hz), 7.99-7.86 (m, 4H), 7.72 (s, 1H), 7.64 (d, 1H, J=8.8 Hz), 7.51 (d, 1H, J=8 Hz), 7.23 (d, 1H, J=8.4 Hz), 5.29 (s, 2H), 5.22-5.18 (m, 1H), 5.01-4.70 (m, 1H), 4.64-4.61 (m, 1H), 4.21-4.17 (m, 1H), 4.09-4.05 (m, 1H), 3.92-3.88 (m, 1H), 3.59-3.08 (m, 14H), 2.67-1.83 (m, 7H), 1.43 (d, 3H, J=6.4 Hz), 0.91-0.71 (m, 12H).

Example MQ

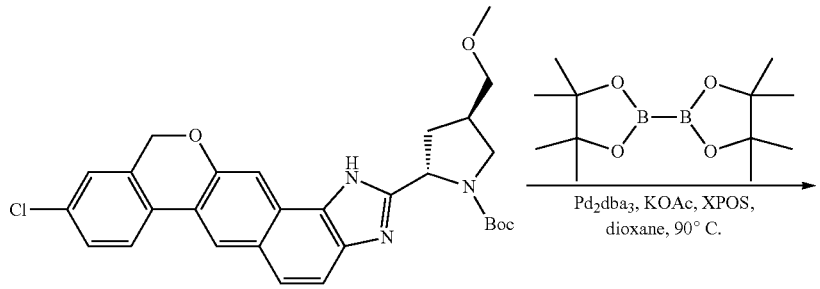

(2S,4R)-tert-butyl 2-(9-chloro-1,11-dihydroisochromeno[4',3':6,7]naphtho[1,2-d]imidazol-2-yl)-4-(methoxymethyl)pyrrolidine-1-carboxylate Pd₂dba₃, KOAc, XPOS, dioxane, 90° C.

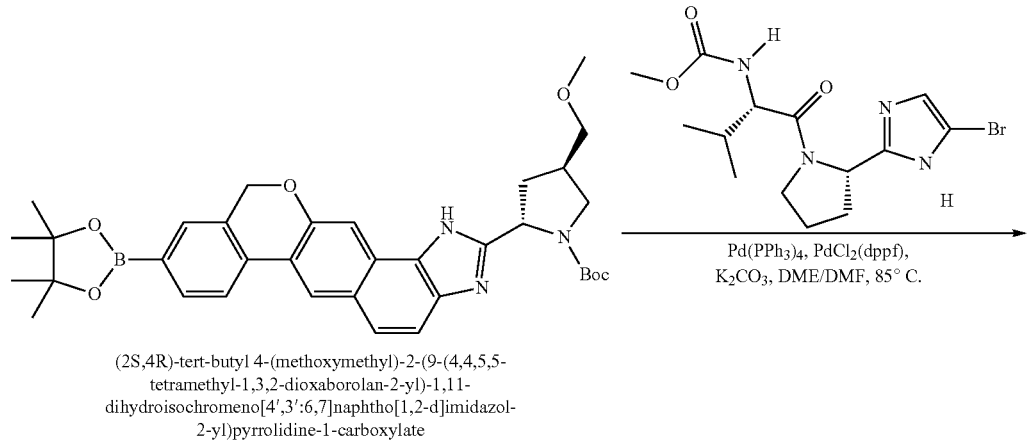

(2S,4R)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate Pd(PPh₃)₄, PdCl₂(dppf), K₂CO₃, DME/DMF, 85° C.

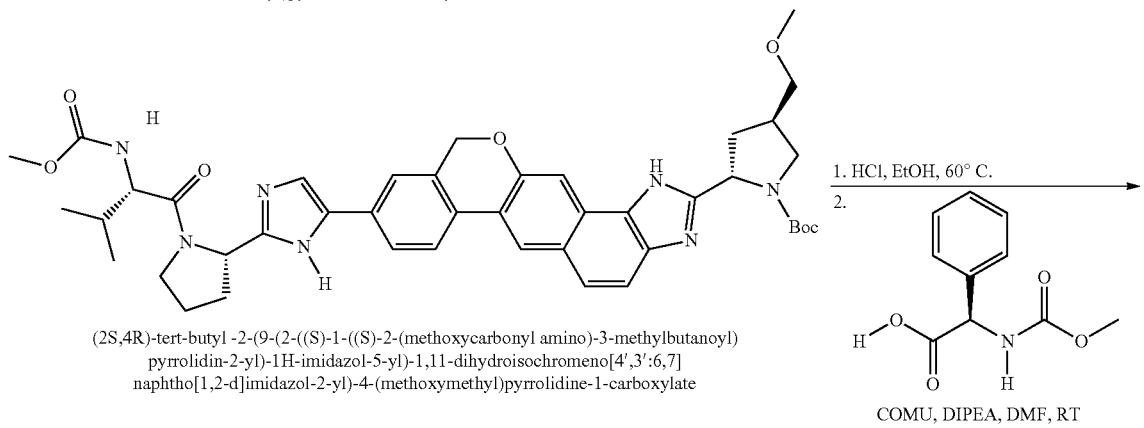

(2S,4R)-tert-butyl -2-(9-(2-((S)-1-((S)-2-(methoxycarbonyl amino)-3-methylbutanoyl)pyrrolidin-2-yl)-1H-imidazol-5-yl)-1,11-dihydroisochromeno[4',3':6,7]naphtho[1,2-d]imidazol-2-yl)-4-(methoxymethyl)pyrrolidine-1-carboxylate 1. HCl, EtOH, 60° C.
2.

COMU, DIPEA, DMF, RT

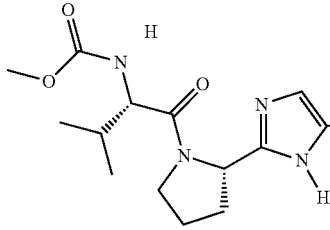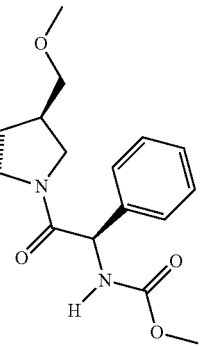

methyl {(1R)-2-]-(2S,4R)-2-(9-{2-[2S)-1-{(2S)-2-
[(methoxycarbonyl)amino]-3-methylbutanoyl}pyrrolidin-
2-yl)-1H-imidazol-5-yl]-1,11-dihydroisochromeno[4',3':6,7]-
naphtho[1,2-d]imidazol-2-yl}-4-(methoxymethyl)pyrrolidin-
1-yl]-2-oxo-phenylethyl}carbamate (2S,4R)-tert-butyl-4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl) pyrrolidine-1-carboxylate: A degassed mixture of -(2S,4R)-tert-butyl-2-(9-chloro-1,11-dihydroisochromeno[4',3':6,7]naphtho[1,2-d]imidazol-2-yl)-4-(methoxymethyl) pyrrolidine-1-carboxylate (335 mg, 0.64 mmol), bis(pinacolato)diboron (246 mg, 0.96 mmol), potassium acetate (190 mg, 1.9 mmol), tris(dibenzylideneacetone) palladium (24 mg, 0.02 mmol) and 2-dicyclohexylphosphino-2',4',6'-tri-i-propyl-1,1'-biphenyl (31 mg, 0.06 mmol) in 1,4-dioxane (3.3 mL) was heated to 90° C. for 3 hours, cooled to room temperature and diluted with ethyl acetate. The organics were washed with water and brine, dried (Na$_2$SO$_4$), and concentrated. The crude residue was purified by flash chromatography to yield (2S,4R)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate (379 mg, 96%).

(2S,4R)-tert-butyl2-(9-(2-((S)-1-((S)-2-(methoxycarbonylamino)-3-methyl butanoyl)pyrrolidin-2-yl)-1H-imidazol-5-yl)-1,11-dihydroisochromeno[4',3':6,7]naphtho[1,2-d]imidazol-2-yl)-4(methoxymethyl) pyrrolidine-1-carboxylate. To a solution of (2S,4R)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl) pyrrolidine-1-carboxylate (299 mg, 0.49 mmol), methyl (S)-1-((S)-2-(5-bromo-1H-imidazol-2-yl)pyrrolidin-1-yl)-3-methyl-1-oxobutan-2-ylcarbamate (217 mg, 0.58 mmol), tetrakis(triphenylphosphine) palladium(0) (28 mg, 0.02 mmol) and dichloro[1,1'-bis(diphenylphosphino)ferrocene]palladium(II) (35 mg, 0.04 mmol) in a mixture of 1,2-dimethoxyethane (4.3 mL) and dimethylformamide (0.75 mL) was added a solution of potassium carbonate (2M in water, 0.73 mL, 1.46 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield (2S,4R)-tert-butyl 2-(9-(2-((S)-1-((S)-2-(methoxycarbonylamino)-3-methylbutanoyl)pyrrolidin-2-yl)-1H-imidazol-5-yl)-1,11-dihydroisochromeno[4',3':6,7]naphtho[1,2-d]imidazol-2-yl)-4-(methoxymethyl)pyrrolidine-1-carboxylate (170 mg, 45%).

methyl{(1R)-2-[(2S,4R)-2-(9-{2-[(2S)-1-{(2S)-2-[(methoxycarbonyl)amino]-3-me thylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl) pyrrolidin-1-yl]-2-oxo-phenylethyl}carbamate: A solution of (2S,4S)-tert-butyl 2-(9-(2-((S)-1-((S)-2-(methoxycarbonylamino)-3-methylbutanoyl)pyrrolidin-2-yl)-1H-imidazol-5-yl)-1,11-dihydroisochromeno[4',3':6,7]naphtho[1,2-d]imidazol-2-yl)-4-(methoxymethyl)pyrrolidine-1-carboxylate (170 mg, 0.22 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (59 mg, 0.28 mmol) and COMU (108 mg, 025 mmol) in DMF (3 mL). To the resulting solution was added diisopropylethylamine (110 µL, 0.66 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 44% ACN/H$_2$O+0.1% TFA). The product fractions were lyophilized to give methyl {(1R)-2-[(2S,4R)-2-(9-{2-[(2S)-1-{(2S)-2-[(methoxycarbonyl)amino]-3-methylbutanoyl}pyrrolidin-2-yl)-1H-imidazol-5-yl]-1,11-dihydroisochromeno[4',3':6,7]-naphtho[1,2-d]imidazol-2-yl}-(methoxymethyl) pyrrolidin-1-yl]-2-oxo-phenylethyl}carbamate (67 mg, 35%). MS (ESI) m/z 870 [M+H]$^+$. 1H NMR (400 MHz, dmso) δ 8.71 (s, 11H), 8.20 (d, 1H, J=8.4 Hz), 8.01 (m, 1H), 7.91-7.64 (m, 6H), 7.38-7.28 (m, 6H), 6.85 (s, 1H), 5.51 (d, 1H, J=7.2 Hz), 5.39-5.29 (m, 3H), 5.13-5.09 (m, 1H), 4.11-3.04 (m, 15H), 2.77-1.98 (m, 8H), 0.79 (dd, 6H, J=6.8 Hz, J=12.8 Hz).

Example MR

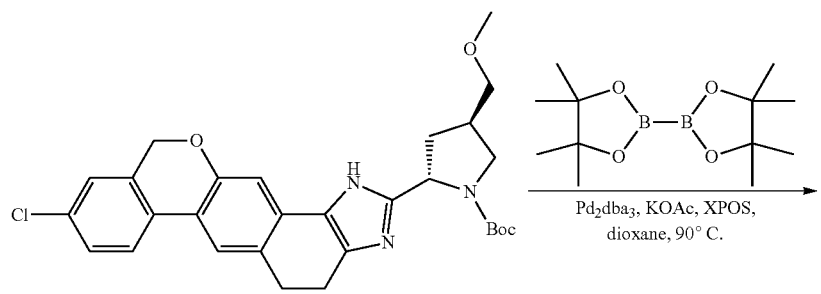

(2S,4R)-tert-butyl 2-(9-chloro-4,5-dihydro-1,11-dihydroisochromeno[4',3':6,7]naphtho[1,2-d]imidazol-2-yl)-4-(methoxymethyl)pyrrolidine-1-carboxylate

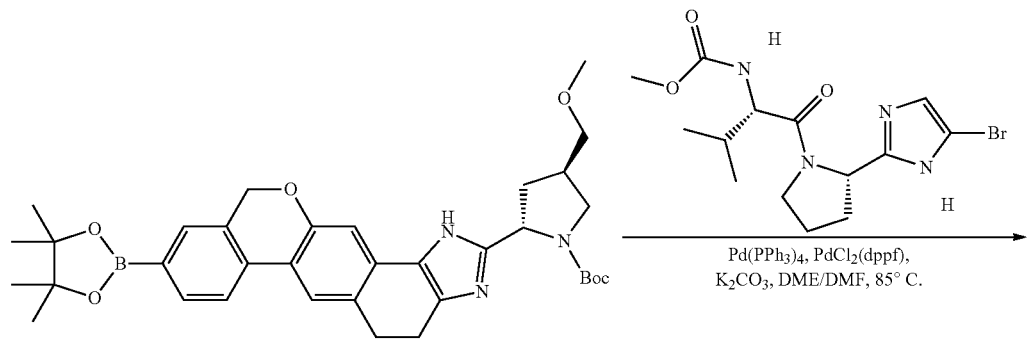

(2S,4R)-tert-butyl 4-(methoxymethyl)-2-(9-(4,4,5,5-tetramethyl-1,3,2-dioxaborolan-2-yl)-4,5-dihydro-1,11-dihydroisochromeno[4',3':6,7]naphtho[1,2-d]imidazol-2-yl)pyrrolidine-1-carboxylate

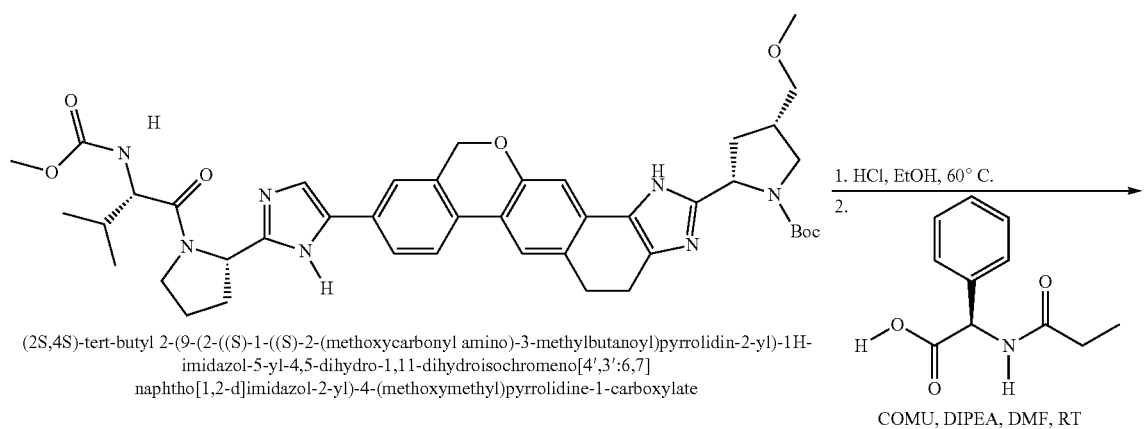

(2S,4S)-tert-butyl 2-(9-(2-((S)-1-((S)-2-(methoxycarbonyl amino)-3-methylbutanoyl)pyrrolidin-2-yl)-1H-imidazol-5-yl-4,5-dihydro-1,11-dihydroisochromeno[4',3':6,7]naphtho[1,2-d]imidazol-2-yl)-4-(methoxymethyl)pyrrolidine-1-carboxylate

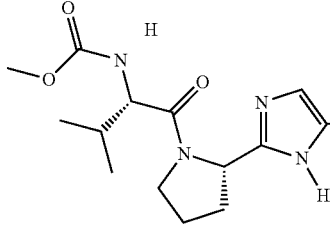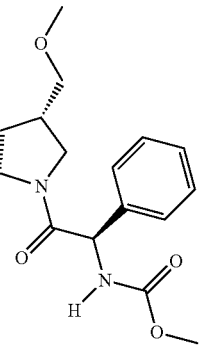

methyl {(1R)-2-]( 2S,4S)-2-(9-{2-[2S)-1-{(2S)-2-
[(methoxy carbonyl)amino]-3-methylbutanoyl}pyrrolidin-
2-yl)-1H-imidazol-5-yl]-1,11-dihydroisochromeno[4',3':6,7]-
4,5-dihydro-naphtho[1,2-d]imidazol-2-yl}-4-(methoxymethyl)pyrrolidin-
1-yl]-2-oxo-phenylethyl}carbamate (2S,4S)-tert-butyl 4-(methoxymethyl)-2-(9-(4,4,5,5-tetramethyl-1,3,2-dioxaborolan-2-yl)-4,5-dihydro-1,11-dihydroisochromeno[4',3':6,7]naphtho[1,2-d]imidazol-2-yl)pyrrolidine-1-carboxylate: A degassed mixture of (2S,4S)-tert-butyl 2-(9-chloro-4,5-dihydro-1,11-dihydroisochromeno[4',3':6,7]naphtho[1,2-d]imidazol-2-yl)-4-(methoxymethyl) pyrrolidine-1-carboxylate (322 mg, 0.61 mmol), bis(pinacolato)diboron (235 mg, 0.92 mmol), potassium acetate (182 mg, 1.9 mmol), tris(dibenzylideneacetone)palladium (23 mg, 0.02 mmol) and 2-dicyclohexylphosphino-2',4',6'-tri-i-propyl-1,1'-biphenyl (29 mg, 0.06 mmol) in 1,4-dioxane (3.3 mL) was heated to 90° C. for 3 hours, cooled to room temperature and diluted with ethyl acetate. The organics were washed with water and brine, dried ($Na_2SO_4$), and concentrated. The crude residue was purified by flash chromatography to yield (2S,4S)-tert-butyl 4-(methoxymethyl)-2-(9-(4,4,5,5-tetramethyl-1,3,2-dioxaborolan-2-yl)-4,5-dihydro-1,11-dihydroisochromeno[4',3':6,7]naphtho[1,2-d]imidazol-2-yl)pyrrolidine-1-carboxylate (267 mg, 70%).

(2S,4S)-tert-butyl 2-(9-(2-((S)-1-((S)-2-(methoxycarbonylamino)-3-methylbutanoyl) pyrrolidin-2-yl)-1H-imidazol-5-yl-4,5-dihydro-1,11-dihydroisochromeno [4',3':6,7] naphtho[1,2-d]imidazol-2-yl)-4-(methoxymethyl) pyrrolidine-1-carboxylate. To a solution of (2S,4S)-tert-butyl 4-(methoxymethyl)-2-(9-(4,4,5,5-tetramethyl-1,3,2-dioxaborolan-2-yl)-4,5-dihydro-1,11-dihydroisochromeno[4',3':6,7]naphtho[1,2-d]imidazol-2-yl)pyrrolidine-1-carboxylate (267 mg, 0.52 mmol), methyl (S)-1-((S)-2-(5-bromo-1H-imidazol-2-yl)pyrrolidin-1-yl)-3-methyl-1-oxobutan-2-ylcarbamate (195 mg, 0.52 mmol), tetrakis(triphenylphosphine) palladium(0) (25 mg, 0.02 mmol) and dichloro[1,1'-bis(diphenylphosphino)ferrocene]palladium (II) (32 mg, 0.04 mmol) in a mixture of 1,2-dimethoxyethane (4.3 mL) and dimethylformamide (0.75 mL) was added a solution of potassium carbonate (2M in water, 0.65 mL, 1.3 mmol). The resulting mixture was degassed and then heated to 85° C. under argon for 18 hours. After cooling to room temperature, the reaction was diluted with ethyl acetate. The organics were washed with water and brine, dried ($Na_2SO_4$), and concentrated. The crude residue was purified by flash chromatography to yield (2S,4S)-tert-butyl 2-(9-(2-((S)-1-((S)-2-(methoxycarbonylamino)-3-methylbutanoyl)pyrrolidin-2-yl)-1H-imidazol-5-yl-4,5-dihydro-1,11-dihydroisochromeno[4',3':6,7]naphtho[1,2-d]imidazol-2-yl)-4-(methoxymethyl)pyrrolidine-1-carboxy late (75 mg, 22%).

methyl{(1R)-2-[(2S,4S)-2-(9-{2-[(2S)-1-{(2S)-2-[(methoxycarbonyl)amino]-3-methylbutanoyl}pyrrolidin-2-yl)-1H-imidazol-5-yl]-1,11-dihydroisochromeno[4',3':6,7]-4,5-dihydro-naphtho[1,2-d]imidazol-2-yl}-(methoxymethyl)pyrrolidin-1-yl]-2-oxo-1-phenylethyl}carbamate: A solution of (2S,4S)-tert-butyl 2-(9-(2-((S)-1-((S)-2-(methoxy carbonylamino)-3-methylbutanoyl)pyrrolidin-2-yl)-1H-imidazol-5-yl-4,5-dihydro-1,11-dihydroisochromeno[4',3':6,7]naphtho[1,2-d]imidazol-2-yl)-4-(methoxymethyl) pyrrolidine-1-carboxylate (75 mg, 0.09 mmol), ethanol (2 mL) and concentrated HCl (0.6 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (26 mg, 0.13 mmol) and COMU (47 mg, 0.11 mmol) in DMF (2 mL). To the resulting solution was added diisopropylethylamine (50 µL, 0.29 mmol). After stirring for 2 hours at room temperature, the reaction was diluted with ethyl acetate, washed with water and brine, dried ($Na_2SO_4$), concentrated and purified by preparative reverse phase HPLC (Gemini, 15 to 44% $ACN/H_2O$+0.1% TFA). The product fractions were lyophilized to give methyl {(1R)-2-[(2S,4S)-2-(9-{2-[(2S)-1-{(2S)-2-[(methoxycarbonyl)amino]-3-methylbutanoyl}pyrrolidin-2-yl)-1H-imidazol-5-yl]-1,11-dihydroisochromeno[4',3':6,7]-4,5-dihydro-naphtho[1,2-d]imidazol-2-yl}-4-(methoxymethyl)pyrrolidin-1-yl]-2-oxo-1-phenylethyl}carbamate (15 mg, 18%).

MS (ESI) m/z 872 [M+H]$^+$.

1H NMR (400 MHz, dmso) δ 7.95-7.63 (m, 6H), 7.35-7.25 (m, 7H), 6.97 (s, 1H), 5.42 (d, 1H, J=6.8 Hz), 5.18 (s, 2H), 5.09 (s, 2H), 4.28-2.63 (m, 19H), 2.47-1.80 (m, 8H), 0.77 (dd, 6H, J=4.8 Hz, J=12.4 Hz).

Example MS

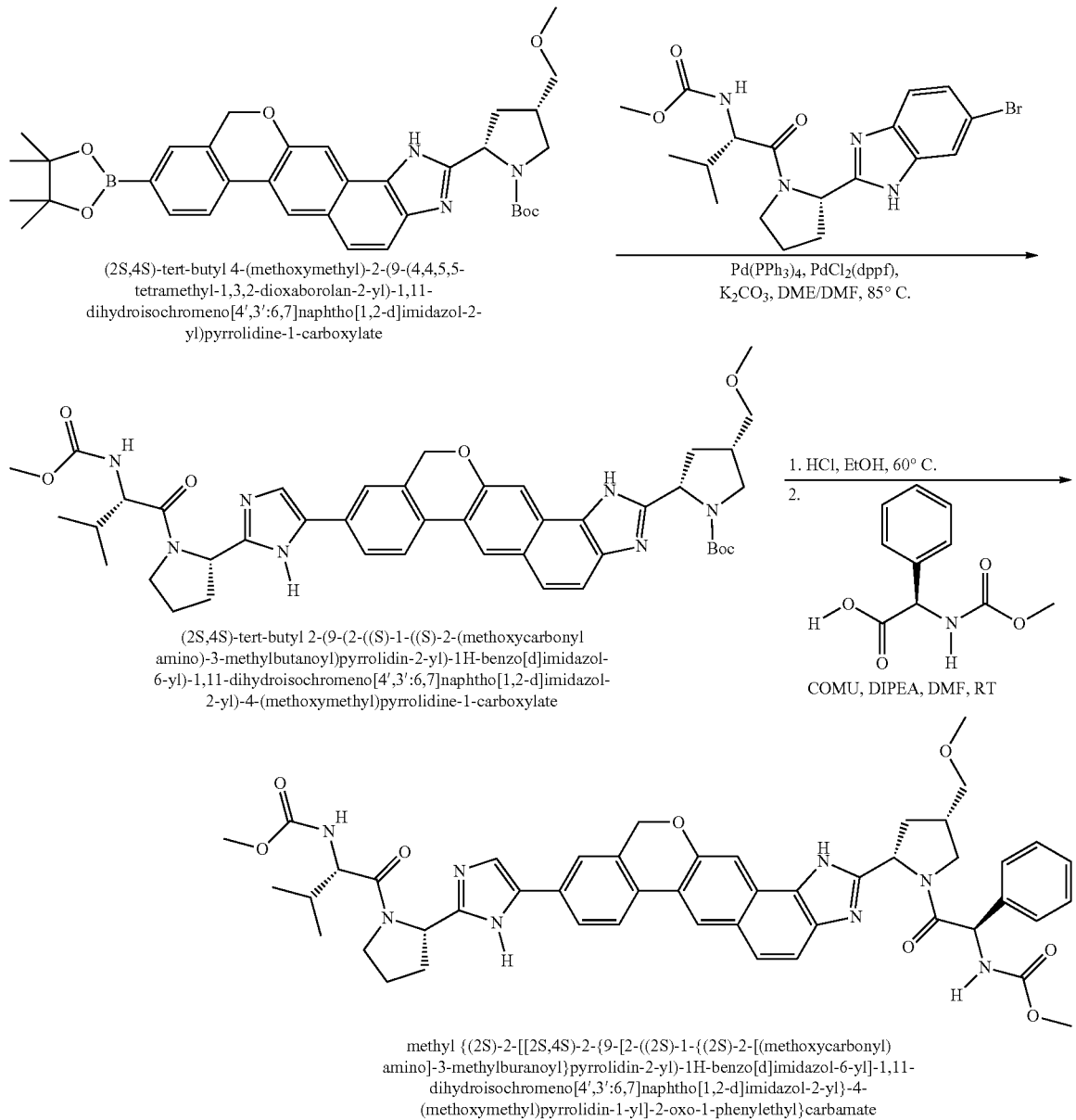

(2S,4S)-tert-butyl2-(9-(2-((S)-1-((S)-2-(methoxycarbonylamino)-3-methylbuta noyl)pyrrolidin-2-yl)-1H-benzo[d]imidazol-6-yl)-1,11-dihydroiso chromeno[4',3':6,7]naphtho[1,2-d]imidazol-2-yl)-4-(methoxymethyl) pyrrolidine-1-carboxylate. To a solution of (2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate (400 mg, 0.85 mmol), methyl (S)-1-((S)-2-(6-bromo-1H-benzo[d]imidazol-2-yl)pyrrolidin-1-yl)-3-methyl-1-oxobutan-2-yl-carbamate (360 mg, 0.85 mmol), tetrakis(triphenylphosphine) palladium(0) (38 mg, 0.03 mmol) and dichloro[1,1'-bis(diphenylphosphino) ferrocene]palladium(II) (48 mg, 0.07 mmol) in a mixture of 1,2-dimethoxyethane (8.0 mL) and dimethylformamide (1.4 mL) was added a solution of potassium carbonate (2M in water, 0.98 mL, 1.96 mmol). The resulting mixture was degassed and then heated to 85° C. under argon for 18 hours. After cooling to room temperature, the reaction was diluted with ethyl acetate. The organics were washed with water and brine, dried (Na₂SO₄), and concentrated. The crude residue was purified by flash chromatography to (2S,4S)-tert-butyl 2-(9-(2-((S)-1-((S)-2-(methoxycarbonylamino)-3-methylbutanoyl)pyrrolidin-2-yl)-1H-benzo[d]imidazol-6-yl)-1,11-dihydroisochromeno[4',3':6,7]naphtho[1,2-d]imidazol-2-yl)-4-(methoxymethyl) pyrrolidine-1-carboxylate (156 mg, 29%).

methyl{(2S)-2-[[(2S,4S)-2-{9-[2-((2S)-1-{(2S)-2-[(methoxycarbonyl)amino]-3-methylbutanoyl}pyrrolidin-2-yl)-1H-benzo[d]imidazol-6-yl]-1,1-dihydroiso chromeno[4', 3':6,7]naphtho[1,2-d]imidazol-2-yl}-4-(methoxymethyl) pyrrolidin-1-yl]-2-oxo-1-phenylethyl}carbamate: A solution of (2S,4S)-tert-butyl 2-(9-(2-((S)-1-((S)-2-(methoxycarbonylamino)-3-methylbutanoyl)pyrrolidin-2-yl)-1H-benzo[d]imidazol-6-yl)-1,11-dihydroisochromeno[4',3':6,7]naphtho[1,2-d]imidazol-2-yl)-4-(methoxymethyl)pyrrolidine-1-carboxylate (156 mg, 0.18 mmol), ethanol (3 mL) and concentrated HCl (1 mL) was heated to 60° C. for 1 hour. The reaction was concentrated and the crude material dissolved in DCM (6 mL). This solution was concentrated and to (90 mg, 0.12 mmol) of this material was added a solution of (R)-2-(methoxycarbonylamino)-2-phenylacetic acid (34 mg, 0.16 mmol) and COMU (61 mg, 014 mmol) in DMF (2 mL). To the resulting solution was added diisopropylethylamine (60 µL, 0.37 mmol). After stirring for 2 hours at room temperature, the reaction was diluted with ethyl acetate, washed with water and brine, dried ($Na_2SO_4$), concentrated and purified by preparative reverse phase HPLC (Gemini, 15 to 49% ACN/$H_2O$+0.1% TFA). The product fractions were lyophilized to give methyl {(2S)-2-[[(2S,4S)-2-{9-[2-((2S)-1-{(2S)-2-[(methoxycarbonyl)amino]-3-methylbutanoyl}pyrrolidin-2-yl)-1H-benzo[d]imidazol-6-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate (62 mg, 56%). MS (ESI) m/z 920 [M+H]$^+$.

1H NMR (400 MHz, dmso) δ 8.73 (s, 1H), 8.17 (d, 2H, J=8.4 Hz), 7.94 (d, 3H, J=8.8 Hz), 7.84-7.67 (m, 6H), 7.37-7.29 (m, 6H), 5.48 (d, 1H, J=7.6 Hz), 5.35-5.20 (m, 5H), 4.14-3.12 (m, 15H), 2.52-1.92 (m, 8H), 0.80 (dd, 6H, J=6.8 Hz, J=6.4 Hz).

Example MT methyl{(2S)-2-[(2S,4S)-2-{9-[2-((2S)-1-{(2S)-2-[(methoxycarbonyl)amino]-3-methylbutanoyl}pyrrolidin-2-yl)-1H-benzo[d]imidazol-6-yl]-1,11-dihydroiso chromeno[4',3':6,7]naphtho[1,2-d]imidazol-2-yl}-4-(methoxymethyl)pyrrolidin-1-yl]-3-methyl-1-oxobutan-2-yl}carbamate: A solution of (2S,4S)-tert-butyl-2-(9-(2-((S)-1-((S)-2-(methoxycarbonylamino)-3-methylbutanoyl)pyrrolidin-2-yl)-1H-benzo[d]imidazol-6-yl)-1,11-dihydroisochromeno[4',3':6,7]naphtho[1,2-d]imidazol-2-yl)-4-(methoxymethyl)pyrrolidine-1-carboxylate (156 mg, 0.18 mmol), ethanol (3 mL) and concentrated HCl (1 mL) was heated to 60° C. for 1 hour. The reaction was concentrated and the crude material dissolved in DCM (6 mL). This solution was concentrated and to (68 mg, 0.09 mmol) of this material was added a solution of (R)-2-(methoxycarbonylamino)-2-phenylacetic acid (21 mg, 0.12 mmol) and COMU (41 mg, 01 mmol) in DMF (1 mL). To the resulting solution was added diisopropylethylamine (50 µL, 0.28 mmol). After stirring for 2 hours at room temperature, the reaction was diluted with ethyl acetate, washed with water and brine, dried ($Na_2SO_4$), concentrated and purified by preparative reverse phase HPLC (Gemini, 15 to 44% ACN/$H_2O$+0.1% TFA). The product fractions were lyophilized to give methyl {(2S)-2-[(2S,4S)-2-{9-[2-((2S)-1-{(2S)-2-[(methoxycarbonyl)amino]-3-methylbutanoyl}pyrrolidin-2-yl)-1H-benzo[d]imidazol-6-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate (32 mg, 40%). MS (ESI) m/z 886 [M+H]$^+$.

1H NMR (400 MHz, dmso) δ 8.71 (s, 1H), 8.15 (d, 1H, J=8 Hz), 7.95-7.64 (m, 8H), 7.28 (dd, 2H, J=8.8 Hz, J=14.4 Hz), 5.31 (s, 2H), 5.23-5.19 (m, 2H), 4.09-3.85 (m, 5H), 3.58-3.28 (m, 14H), 2.47-1.89 (m, 9H), 0.83-0.72 (m, 12H).

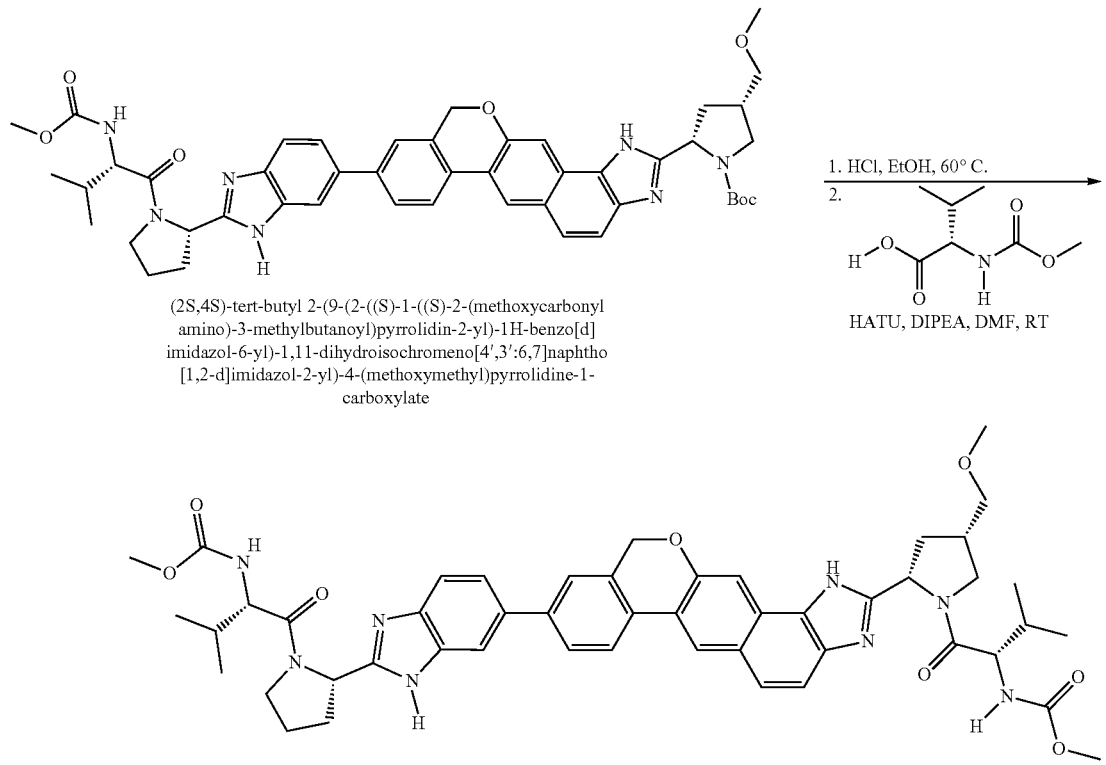

(2S,4S)-tert-butyl 2-(9-(2-((S)-1-((S)-2-(methoxycarbonylamino)-3-methylbutanoyl)pyrrolidin-2-yl)-1H-benzo[d]imidazol-6-yl)-1,11-dihydroisochromeno[4',3':6,7]naphtho[1,2-d]imidazol-2-yl)-4-(methoxymethyl)pyrrolidine-1-carboxylate 1. HCl, EtOH, 60° C.
2.

HATU, DIPEA, DMF, RT methyl {(2S)-2-[(2S,4S)-2-{9-[2-((2S)-1-{(2S)-2-[(methoxycarbonyl)amino]-3-methylbutanoyl}pyrrolidin-2-yl)-1H-benzo[d]imidazol-6-y]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate Example MU

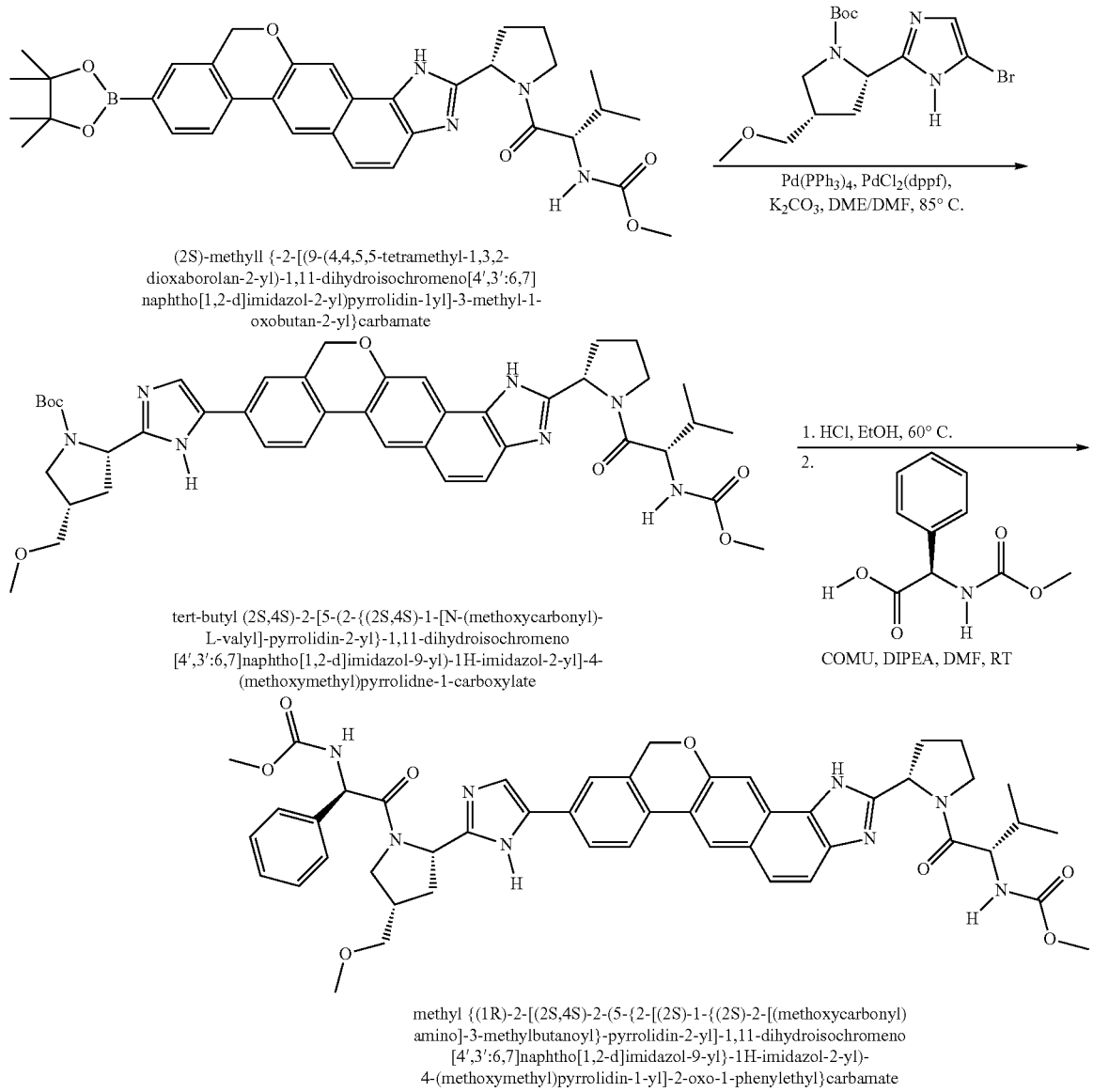

(2S)-methyl1 {-2-[(9-(4,4,5,5-tetramethyl-1,3,2-dioxaborolan-2-yl)-1,11-dihydroisochromeno[4',3':6,7]naphtho[1,2-d]imidazol-2-yl)pyrrolidin-1yl]-3-methyl-1-oxobutan-2-yl}carbamate tert-butyl (2S,4S)-2-[5-(2-{(2S,4S)-1-[N-(methoxycarbonyl)-L-valyl]-pyrrolidin-2-yl}-1,11-dihydroisochromeno[4',3':6,7]naphtho[1,2-d]imidazol-9-yl)-1H-imidazol-2-yl]-4-(methoxymethyl)pyrrolidne-1-carboxylate methyl {(1R)-2-[(2S,4S)-2-(5-{2-[(2S)-1-{(2S)-2-[(methoxycarbonyl)amino]-3-methylbutanoyl}-pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate tert-butyl (2S,4S)-2-[5-(2-{(2S,4S)-1-[N-(methoxycarbonyl)-L-valyl]-pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. To a solution of (2S)-methyl1 {-2-[(9-(4,4,5,5-tetramethyl-1,3,2-dioxaborolan-2-yl)-1,11-dihydroisochromeno[4',3':6,7]naphtho[1,2-d]imidazol-2-yl)pyrrolidin-1yl]-3-methyl-1-oxobutan-2-yl}carbamate (460 mg, 0.74 mmol), (2S,4S)-tert-butyl 2-(5-bromo-1H-imidazol-2-yl)-4-(methoxymethyl)pyrrolidin-1-carboxylate (250 mg, 0.61 mmol), tetrakis(triphenylphosphine) palladium(0) (35 mg, 0.03 mmol) and dichloro[1,1'-bis(diphenylphosphino) ferrocene]palladium (II) (45 mg, 0.06 mmol) in a mixture of 1,2-dimethoxyethane (9.0 mL) and dimethylformamide (1.5 mL) was added a solution of potassium carbonate (2M in water, 0.92 mL, 1.84 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to tert-butyl (2S,4S)-2-[5-(2-{(2S,4S)-1-[N-(methoxycarbonyl)-L-valyl]-pyrrolidin-2-yl}-1,11-dihydroisochromeno[4',3':6,7]naphtho[1,2-d]imidazol-9-yl)-1H-imidazol-2-yl]-4-(methoxymethyl) pyrrolidine-1-carboxylate (123 mg).

methyl {(1R)-2-[(2S,4S)-2-(5-{2-[(2S)-1-{(2S)-2-[(methoxycarbonyl)amino]-3-me thylbutanoyl}-pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate: A solution tert-butyl (2S,4S)-2-[5-(2-{(2S,4S)-1-[N-(methoxy carbonyl)-L-valyl]-pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-carboxylate (122 mg, 0.16 mmol), ethanol (3 mL) and concentrated HCl (1 mL) was heated to 60° C. for 1 hour. The reaction was concentrated and the crude material dissolved in DCM (3 mL). This solution was concentrated and to this material was added a solution of (R)-2-(methoxycarbonylamino)-2-phenylacetic acid (43 mg, 0.2 mmol) and COMU (77 mg, 018 mmol) in DMF (3 mL). To the resulting solution was added diisopropylethylamine (80 µL, 0.37 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 44% ACN/H$_2$O+0.1% TFA). The product fractions were lyophilized to give methyl {(1R)-2-[(2S,4S)-2-(5-{2-[(2S)-1-{(2S)-2-[(methoxycarbonyl)amino]-3-methylbutanoyl}-pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate (60 mg, 44%). MS (ESI) m/z 870 [M+H]$^+$.

1H NMR (400 MHz, dmso) δ 8.71 (s, 1H), 8.22 (d, 1H, J=8 Hz), 8.09 (m, 1H), 7.88-7.63 (m, 6H), 7.36-7.29 (m, 6H), 5.41 (d, 1H, J=8.4 Hz), 5.30-5.24 (m, 2H), 5.14-5.10 (m, 1H), 4.13-3.09 (m, 15H), 2.47-1.80 (m, 8H), 0.80 (dd, 6H, J=6.4 Hz, J=23 Hz).

Example MV

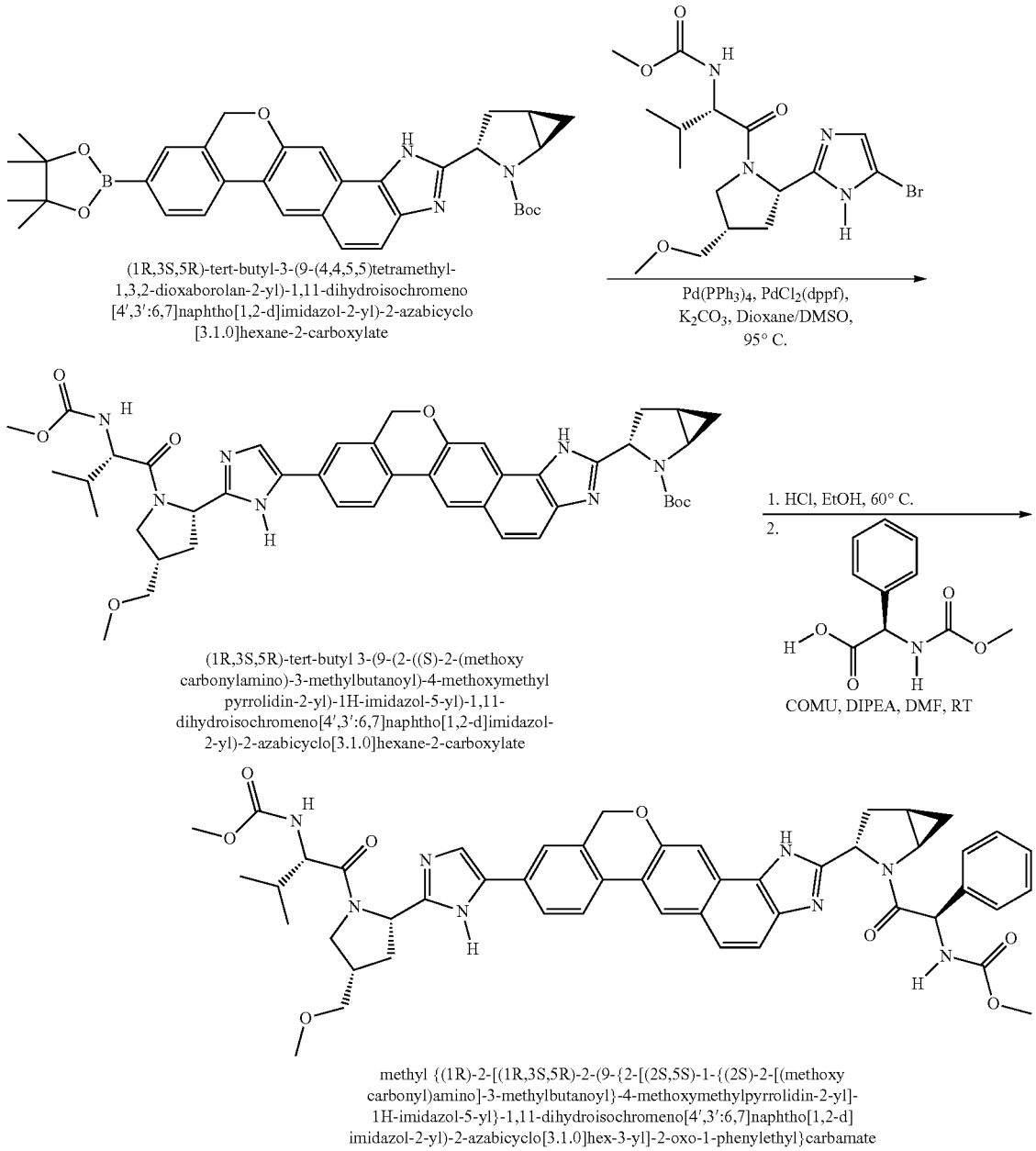

(1R,3S,5R)-tert-butyl-3-(9-(4,4,5,5)tetramethyl-1,3,2-dioxaborolan-2-yl)-1,11-dihydroisochromeno[4',3':6,7]naphtho[1,2-d]imidazol-2-yl)-2-azabicyclo[3.1.0]hexane-2-carboxylate Pd(PPh$_3$)$_4$, PdCl$_2$(dppf), K$_2$CO$_3$, Dioxane/DMSO, 95° C.

(1R,3S,5R)-tert-butyl 3-(9-(2-((S)-2-(methoxycarbonylamino)-3-methylbutanoyl)-4-methoxymethyl pyrrolidin-2-yl)-1H-imidazol-5-yl)-1,11-dihydroisochromeno[4',3':6,7]naphtho[1,2-d]imidazol-2-yl)-2-azabicyclo[3.1.0]hexane-2-carboxylate 1. HCl, EtOH, 60° C.
2. COMU, DIPEA, DMF, RT methyl {(1R)-2-[(1R,3S,5R)-2-(9-{2-[(2S,5S)-1-{(2S)-2-[(methoxycarbonyl)amino]-3-methylbutanoyl}-4-methoxymethylpyrrolidin-2-yl}-1H-imidazol-5-yl]-1,11-dihydroisochromeno[4',3':6,7]naphtho[1,2-d]imidazol-2-yl)-2-azabicyclo[3.1.0]hex-3-yl]-2-oxo-1-phenylethyl}carbamate (1R,3 S,5R)-tert-butyl3-(9-(2-((S)-1-((S)-2-(methoxycarbonylamino)-3-methylbutanoyl)-4-methoxymethylpyrrolidin-2-yl)-1H-imidazol-5-yl)-1,11-dihydroisochromeno[4',3':6,7]naphtho[1,2-d]imidazol-2-yl)-2-azabicyclo 13.1.01 hexane-2-carboxylate. To a solution of (1R,3 S,5R)-tert-butyl-3-(9-(4,4,5,5-tetramethyl-1,3,2-dioxaborolan-2-yl)-1,11-dihydroisochromeno[4',3':6,7]naphtho[1,2-d]imidazol-2-yl)-2-azabicyclo[3.1.0]hexane-2-carboxylate (213 mg, 0.37 mmol), methyl (S)-1-((2S,4S)-2-(5-bromo-1H-imidazol-2-yl)-4-(methoxymethyl)pyrrolidin-1-yl)-3-methyl-1-oxobutan-2-ylcarbamate (142 mg, 0.31 mmol), tetrakis (triphenylphosphine) palladium(0) (35 mg, 0.03 mmol) and dichloro[1,1'-bis(diphenylphosphino) ferrocene]palladium (II) (22 mg, 0.03 mmol) in a mixture of 1,4-dioxane (3.0 mL) and dimethylsulfoxide (3.0 mL) was added a solution of potassium carbonate (2M in water, 0.46 mL, 0.9 mmol). The resulting mixture was degassed and then heated to 95° C. under argon for 7 hours. After cooling to room temperature, the reaction was diluted with ethyl acetate. The organics were washed with water and brine, dried ($Na_2SO_4$), and concentrated. The crude residue was purified by flash chromatography to (1R,3S,5R)-tert-butyl 3-(9-(2-((S)-1-((S)-2-(methoxycarbonyl amino)-3-methylbutanoyl)-4-methoxymethylpyrrolidin-2-yl)-1H-imidazol-5-yl)-1,11-dihydroisochromeno[4',3':6,7]naphtho[1,2-d]imidazol-2-yl)-2-azabicyclo[3.1.0]hexane-2-carboxylate (101 mg, 42%).

nylacetic acid (35 mg, 0.17 mmol) and COMU (63 mg, 015 mmol) in DMF (3 mL). To the resulting solution was added diisopropylethylamine (70 µL, 0.38 mmol). After stirring for 2 hours at room temperature, the reaction was diluted with ethyl acetate, washed with water and brine, dried ($Na_2SO_4$), concentrated and purified by preparative reverse phase HPLC (Gemini, 15 to 44% $ACN/H_2O$+0.1% TFA). The product fractions were lyophilized to give methyl methyl {(1R)-2-[(1R,3S,5R)-2-(9-{2-[(2S,5S)-1-{(2S)-2-[(methoxy carbonyl)amino]-3-methylbutanoyl}-4-methoxymethylpyrrolidin-2-yl]-1H-imidazol-5 yl}-1,11-dihydroisochromeno[4',3':6,7]naphtho[1,2-d]imidazol-2-yl)-2-azabicyclo[3.1.0]hex-3-yl]-2-oxo-1-phenylethyl}carbamate (71 mg, 63).

MS (ESI) m/z 882 [M+H]$^+$.

1H NMR (400 MHz, dmso) δ 8.66 (s, 1H), 8.17 (d, 1H, J=8.8 Hz), 8.04 (s, 1H), 7.87-7.59 (m, 6H), 7.39-7.22 (m, 6H), 5.72 (d, 1H, J=7.6 Hz), 5.68 (s, 1H), 5.25 (s, 1H), 5.13-5.01 (m, 2H), 4.12-4.00 (m, 2H), 3.81-3.00 (m, 13H), 2.60 (m, 1H), 2.43-2.37 (m, 3H), 1.92-1.82 (m, 3H), 0.83-0.58 (m, 7H), 0.59 (s, 1H), 0.00 (s, 1H).

Example MW

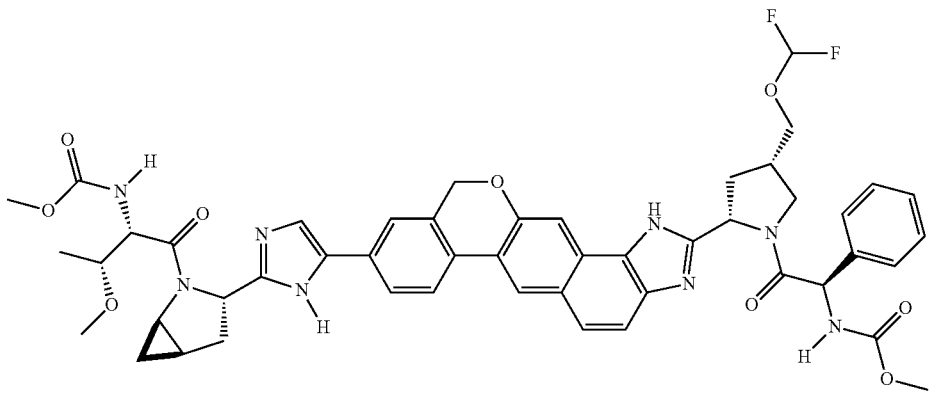

methyl{(1R)-2-[(1R,3S,5R)-2-(9-{2-[(2S,5S)-1-{(2S)-2-[(methoxycarbonyl)amino]-3-methylbutanoyl}-4-methoxymethylpyrrolidin-2-yl]-1H-imidazol-5-yl}-1,11-dihydroisochromeno[4',3':6,7]naphtho[1,2-d]imidazol-2-yl)-azabicyclo[3.1.0]hex-3-yl]-2-oxo-1-phenylethyl}carbamate: A solution (1R,3S,5R)-tert-butyl 3-(9-(2-((S)-1-((S)-2-(methoxycarbonylamino)-3-methylbutanoyl)-4-methoxymethylpyrrolidin-2-yl)-1H-imidazol-5-yl)-1,11-dihydroisochromeno[4',3':6,7]naphtho[1,2-d]imidazol-2-yl)-2-aza bicyclo[3.1.0]hexane-2-carboxylate (101 mg, 0.16 mmol), ethanol (3 mL) and concentrated HCl (1 mL) was heated to 60° C. for 1 hour. The reaction was concentrated and the crude material dissolved in DCM (3 mL). This solution was concentrated and to this material was added a solution of (R)-2-(methoxycarbonylamino)-2-phemethyl {(1R)-2-[(2S,4S)-2-(9-{2-[(1R,3S,5R)-1-{(2S)-2-[(methoxycarbonyl)amino]-3-methylbutanoyl}-5-azabicyclo [3.1.0]hex-3-yl]-1H-imidazol-5-yl}-1,11-dihydroisochromeno [4',3':6,7]naphtho[1,2-d]imidazol-2-yl)-4-(difluoromethoxy) methylpyrrolidin-1-yl]-2-oxo-1-phenylethyl}carbamate This compound was synthesized using the same conditions as example OO substituting with the respective (1R,3 S,5R)-2-((S)-2-(methoxycarbonylamino)-3-methylbutanoyl)-2-azabicyclo[3.1.0]hexane-3-carboxylic acid and (2S,4S)-1-(tert-butoxycarbonyl)-4-((difluoromethoxy) methyl)pyrrolidine-2-carboxylic acid as appropriate.

MS (ESI) m/z 918 [M+H]$^+$.

Example MX

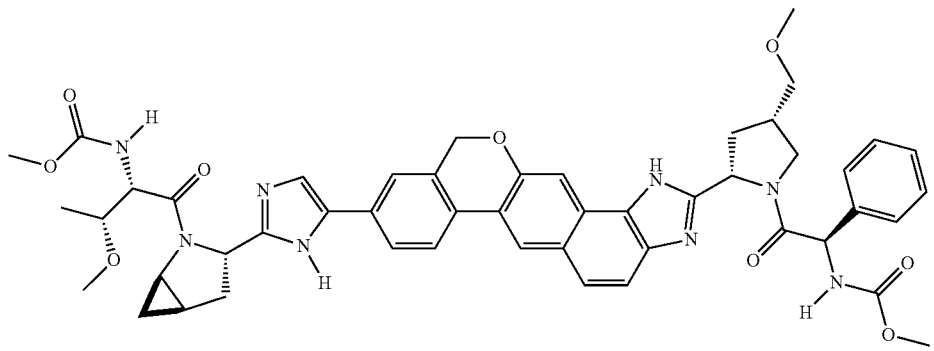

methyl {(1R)-2-[(2S,4S)-2-(9-{2-[(1R,3S,5R)-1-{(2S,3S)-3-methoxy-2-[(methoxycarbonyl)amino]butanoyl}-5-azabicyclo [3.1.0]hex-3-yl]-1H-imidazol-5-yl}-1,11-dihydroisochromeno [4',3':6,7]naphtho[1,2-d]imidazol-2-yl)-4-(difluoromethoxy)methylpyrrolidin-1-yl]-2-oxo-1-phenylethyl}carbamate This compound was synthesized using the same conditions as example OO substituting with the respective (1R, 3S,5R)-2-((2S,3S)-3-methoxy-2(methoxycarbonylamino)butanoyl)-2-azabicyclo[3.1.0]hexane-3-carboxylic acid and (2S,3R)-3-methoxy-2-(methoxycarbonylamino)butanoic acid as appropriate.

MS (ESI) m/z 898 [M+H]+.

Example MY

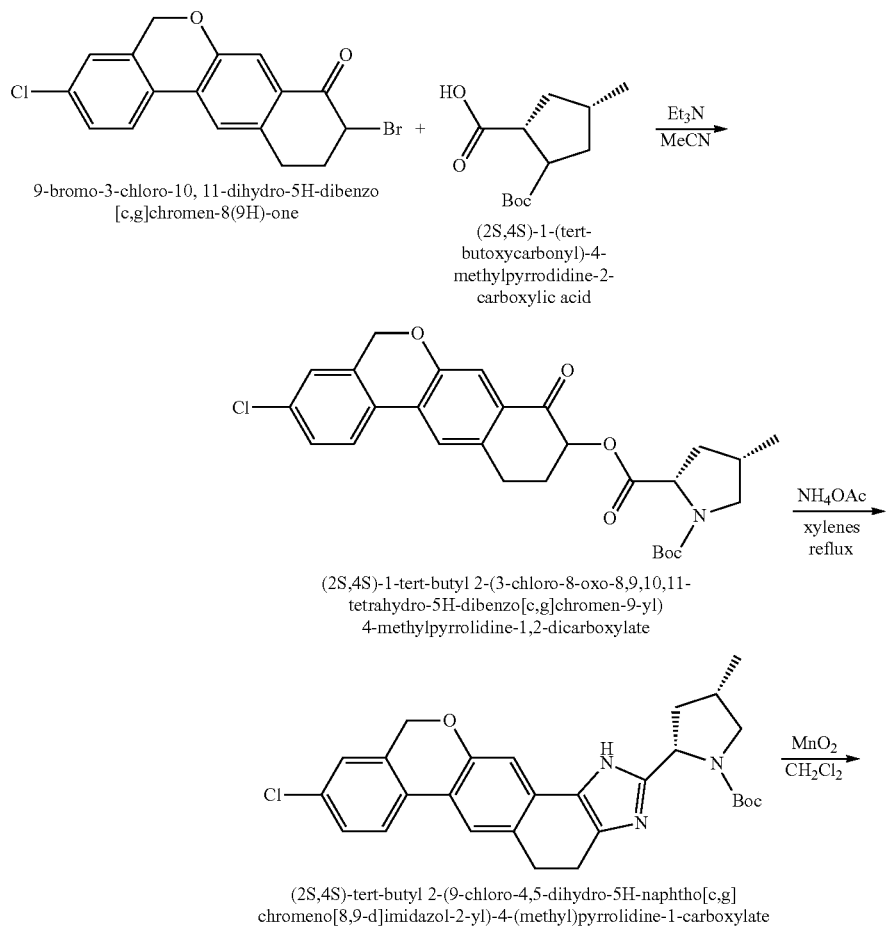

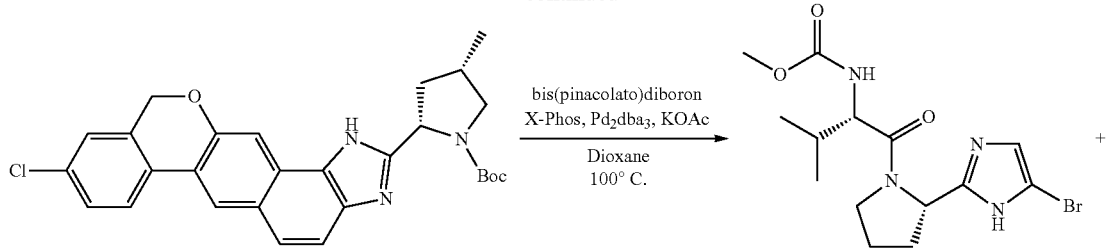

(2S,4S)-tert-butyl 2-(9-chloro-5H-naphtho[c,g]chromeno[8,9-d]imidazol-2-yl)-4-methylpyrrolidine-1-carboxylate methyl (S)-1-((S)-2-(5-bromo-1H-imidazol-2-yl)pyrrolidin-1-yl)-3-methyl-1-oxobutan-2-ylcarbamate

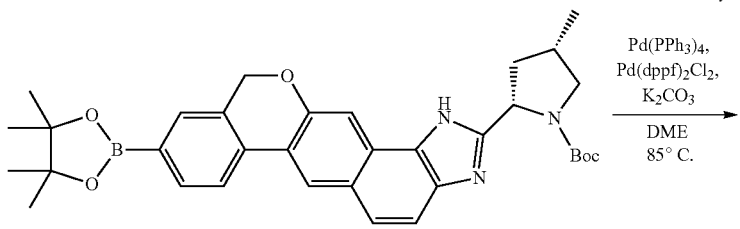

(2S,4S)-tert-butyl-2-(9-(2-((S)-1-((S)-2-(methoxycarbonylamino)methylbutanoyl)azabicyclo[3.1.0]hexan-3-yl)-1H-imidazol-5-yl)-5H-naphtho[c,g]chromeno[8,9-d]imidazol-2-yl)-4-methylpyrrolidine-1-carboxylate

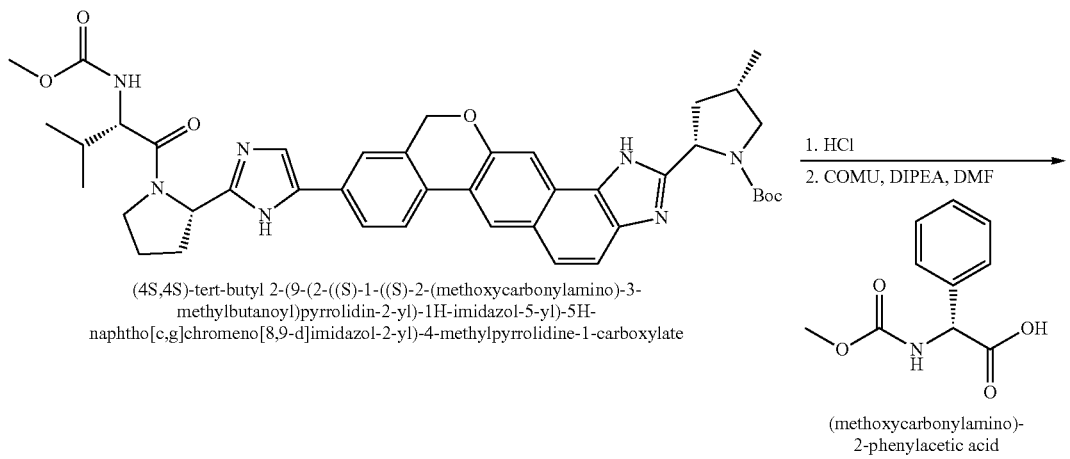

(4S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-methylpyrrolidine-1-carboxylate (methoxycarbonylamino)-2-phenylacetic acid

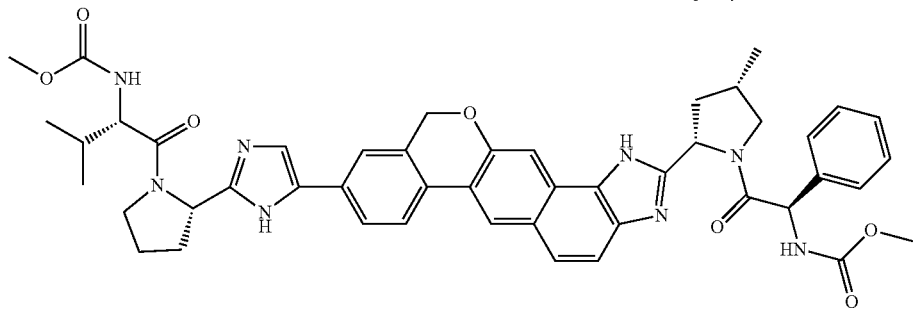

methyl {2-[2-{9-[2-(1-{2[[(methoxycarbonyl)amino]-3-methylbutanoyl}pyrrolidin-2-yl)-1H-imidazol-5-yl]-1,11-dihydroisochromeno[4′,3′:6,7]naphtho[1,2-d]imidazol-2-yl)-4-methylpyrrolidin-1-yl]-2-oxo-1-phenylethyl]carbamate (2S,4S)-1-tert-butyl 2-(3-chloro-8-oxo-8,9,10,11-tetrahydro-5H-dibenzo[c,g]chromen-9-yl)4-methylpyrrolidine-1,2-dicarboxylate: To a solution of 9-bromo-3-chloro-10,11-dihydro-5H-dibenzo[c,g]chromen-8(9H)-one (1.32 g, 3.63 mmol) in MeCN (40 mL) was added (2S,4S)-1-(tert-butoxycarbonyl)-4-methylpyrrolidine-2-carboxylic acid (1.0 g, 4.36 mmol) and DIPEA (0.7 mL, 3.99 mmol). After stirring for 18 h, the solution was diluted with EtOAc and washed successively with saturated aqueous NaHCO$_3$ and brine. The organics were dried over MgSO$_4$, filtered and concentrated under reduced pressure. The crude residue was purified by silica column chromatography (10% to 40% EtOAc/hexanes) to afford (2S,4S)-1-tert-butyl 2-(3-chloro-8-oxo-8,9,10,11-tetrahydro-5H-dibenzo[c,g]chromen-9-yl) 4-methylpyrrolidine-1,2-dicarboxylate (1.31 g, 70%).

(2S,4S)-tert-butyl 2-(9-chloro-4,5-dihydro-5H-naphtho[c,g]chromeno[8,9-d]imidazol-2-yl)-4-methylpyrrolidine-1-carboxylate: (2S,4S)-1-tert-butyl 2-(3-chloro-8-oxo-8,9,10,11-tetrahydro-5H-dibenzo[c,g]chromen-9-yl) 4-methylpyrrolidine-1,2-dicarboxylate (1.31 g, 2.56 mmol) was added xylenes (25 mL) and ammonium acetate (3.95 g, 51.2 mmol) and the solution was heated to 136° C. and stirred overnight. The following morning, the solution was cooled to rt and was diluted with EtOAc and washed successively with water, saturated aqueous $NaHCO_3$ and brine. The organics were dried over $MgSO_4$, filtered and concentrated under reduced pressure. The crude residue was purified by silica column chromatography (60% to 100% EtOAc/hexanes) to afford (2S,4S)-tert-butyl 2-(9-chloro-4,5-dihydro-5H-naphtho[c,g]chromeno[8,9-d]imidazol-2-yl)-4-methylpyrrolidine-1-carboxylate (711 mg, 56%).

(2S,4S)-tert-butyl 2-(9-chloro-5H-naphtho[c,g]chromeno[8,9-d]imidazol-2-yl)-4-methylpyrrolidine-1-carboxylate: To a solution of (2S,4S)-tert-butyl 2-(9-chloro-4,5-dihydro-5H-naphtho[c,g]chromeno[8,9-d]imidazol-2-yl)-4-(methyl)pyrrolidine-1-carboxylate (935 mg, 1.9 mmol) in $CH_2Cl_2$ (20 mL) was added $MnO_2$ (8.25 g, 95 mmol). The reaction mixture was stirred for 3 h, and then filtered over celite. The filter cake was washed with copious $CH_2Cl_2$ and MeOH, and the filtrate was concentrated under reduced pressure. The crude residue was purified by silica column chromatography (0% to 10% MeOH/EtOAc) to afford (2S,4S)-tert-butyl 2-(9-chloro-5H-naphtho[c,g]chromeno[8,9-d]imidazol-2-yl)-4-methylpyrrolidine-1-carboxylate (692 mg, 74%).

(2S,4S)-tert-butyl-2-(9-(2-((S)-1-((S)-2-(methoxycarbonylamino)methylbutanoyl)azabicyclo[3.1.0]hexan-3-yl)-1H-imidazol-5-yl)-5H-naphtho[c,g]chromeno[8,9-d]imidazol-2-yl)-4-methylpyrrolidine-1-carboxylate: (2S,4S)-tert-butyl 2-(9-chloro-5H-naphtho[c,g]chromeno[8,9-d]imidazol-2-yl)-4-methylpyrrolidine-1-carboxylate (692 mg, 1.41 mmol) in dioxane (15 mL) was added bis(pinacolato)diboron (1.07 g, 4.23 mmol), KOAc (415 mg, 4.23 mmol), X-Phos (52 mg, 0.11 mmol), and $Pd_2dba_3$ (26 mg, 0.03 mmol). The solution was degassed with $N_2$ for 10 min, then heated to 100° C. for 16 h. The solution was cooled to rt, diluted with EtOAc, washed with saturated aqueous $NaHCO_3$, brine, dried with $MgSO_4$, and concentrated. Purified by silica gel chromatography (0% to 30% MeOH/EtOAc) to afford (2S,4S)-tert-butyl-2-(9-(2-((S)-1-((S)-2-(methoxycarbonylamino)methylbutanoyl)azabicyclo[3.1.0]hexan-3-yl)-1H-imidazol-5-yl)-5H-naphtho[c,g]chromeno[8,9-d]imidazol-2-yl)-4-methylpyrrolidine-1-carboxylate (821 mg, quant).

(2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4(methyl)pyrrolidine-1-carboxylate: To a solution of (2S,4S)-tert-butyl-2-(9-(2-((S)-1-((S)-2-(methoxycarbonylamino)methylbutanoyl)azabicyclo[3.1.0]hexan-3-yl)-1H-imidazol-5-yl)-5H-naphtho[c,g]chromeno[8,9-d]imidazol-2-yl)-4-methylpyrrolidine-1-carboxylate (821 mg, 1.41 mmol), methyl (S)-1-((S)-2-(5-bromo-1H-imidazol-2-yl)pyrrolidin-1-yl)-3-methyl-1-oxobutan-2-ylcarbamate (1.05 g, 2.82 mmol), tetrakis(triphenylphosphine) palladium(0) 162 mg, 0.14 mmol) and dichloro[1,1'-bis(diphenylphosphino)ferrocene]palladium(II) (102 mg, 0.14 mmol) in DME (15 mL) was added a solution of potassium carbonate (2M in water, 2.32 mL, 4.65 mmol). The resulting mixture was degassed and then heated to 85° C. for 18 hours. After cooling to room temperature, the reaction was diluted with ethyl acetate. The organics were washed with saturated sodium bicarbonate and brine, dried over $MgSO_4$ and concentrated. The crude residue was purified by flash chromatography to yield (2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4methylpyrrolidine-1-carboxylate (386 mg, 37%).

Methyl {2-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methyl)pyrrolidin-1-yl]-2-oxo-1-phenylethyl}carbamate: A solution of (2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4methylpyrrolidine-1-carboxylate (386 mg, 0.52 mmol), $CH_2C2$ (8 mL), MeOH (2 mL) and HCl (4M in Dioxane, 2 mL) and was stirred overnight. The reaction was concentrated and the crude material dissolved in DMF (8 mL). This solution was concentrated and to this material was added a solution of (R)-2-(methoxycarbonylamino)-2-phenylacetic acid (108 mg, 0.52 mmol) and COMU (248 mg, 0.52 mmol). To the resulting solution was added diisopropylethylamine (0.45 mL, 2.6 mmol). After stirring for 2 hours at room temperature, the reaction was diluted with 10% MeOH/EtOAc, washed with saturated $NaHCO_3$ water and brine, dried ($Na_2SO_4$), concentrated and purified by HPLC to give methyl {2-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-methylpyrrolidin-1-yl]-2-oxo-1-phenylethyl}carbamate (27 mg, 6%)_LCMS-ESI$^+$: calculated for $C_{47}H_{50}N_8O_7$: 838.38; observed $[M+1]^+$: 840.12.

Example MZ

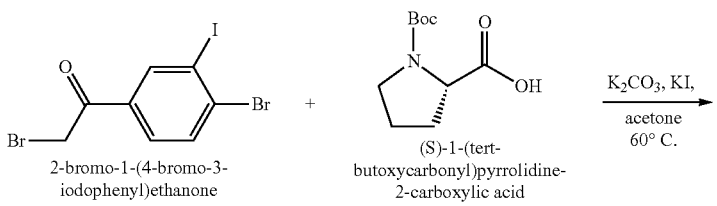

1271	1272
-continued
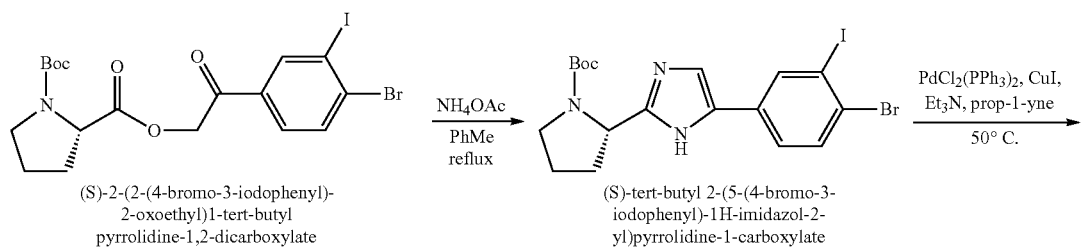
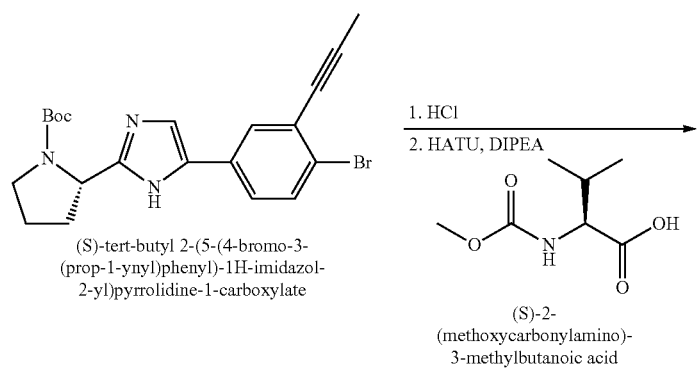
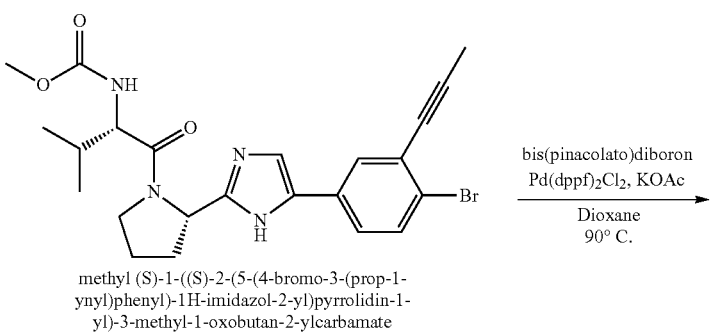
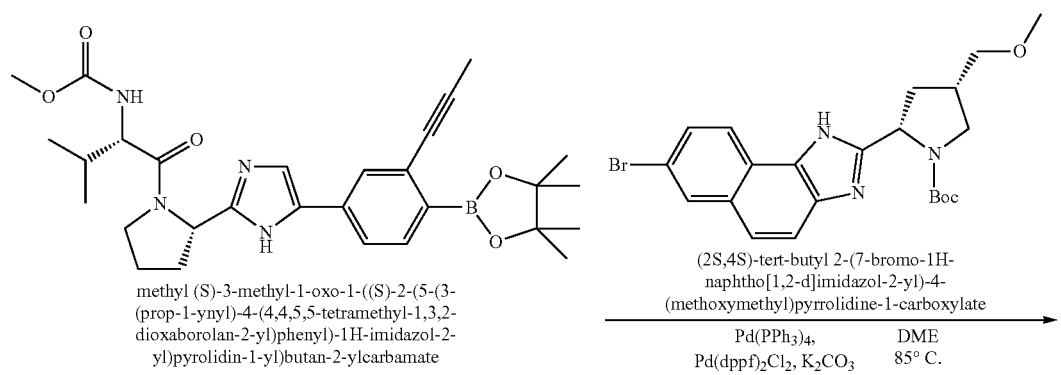

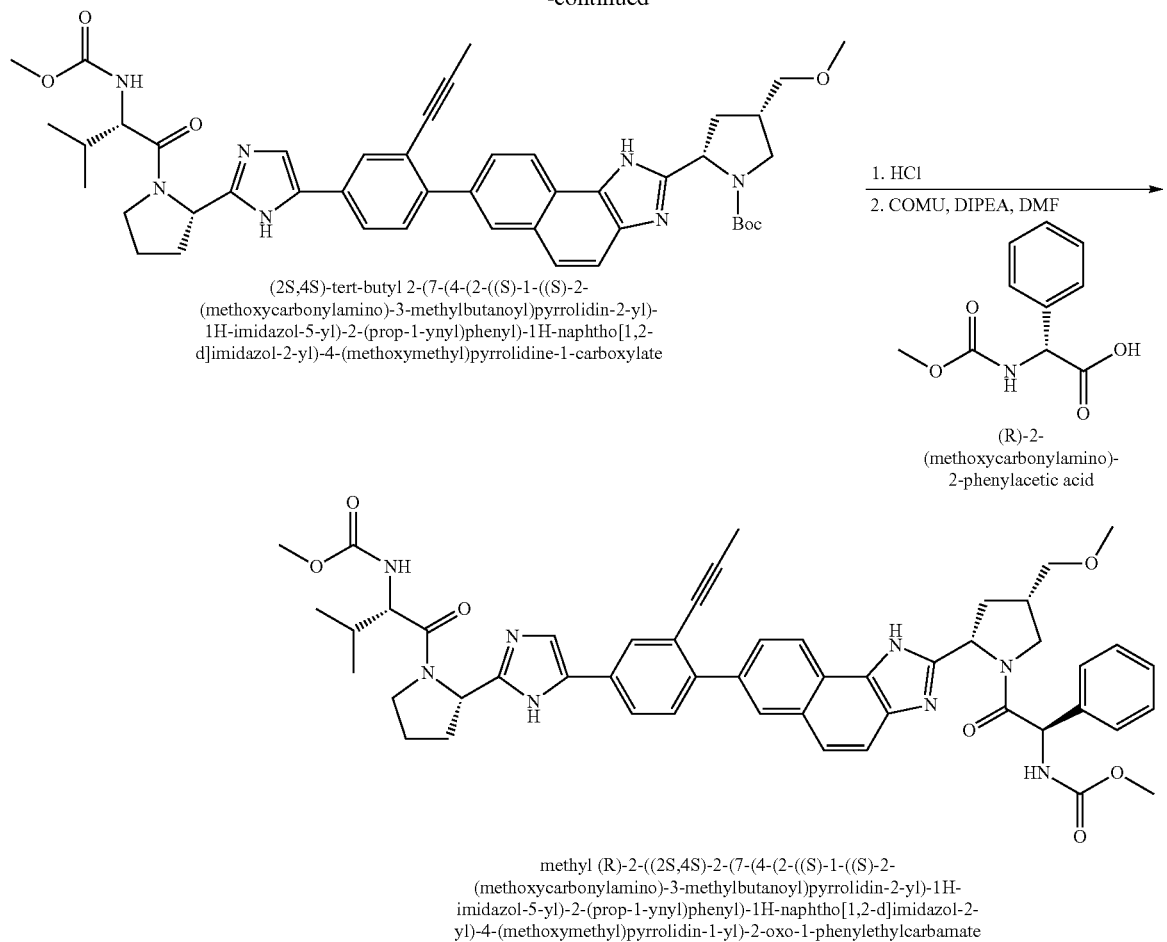

(2S,4S)-tert-butyl 2-(7-(4-(2-((S)-1-((S)-2-(methoxycarbonylamino)-3-methylbutanoyl)pyrrolidin-2-yl)-1H-imidazol-5-yl)-2-(prop-1-ynyl)phenyl)-1H-naphtho[1,2-d]imidazol-2-yl)-4-(methoxymethyl)pyrrolidine-1-carboxylate (R)-2-(methoxycarbonylamino)-2-phenylacetic acid methyl (R)-2-((2S,4S)-2-(7-(4-(2-((S)-1-((S)-2-(methoxycarbonylamino)-3-methylbutanoyl)pyrrolidin-2-yl)-1H-imidazol-5-yl)-2-(prop-1-ynyl)phenyl)-1H-naphtho[1,2-d]imidazol-2-yl)-4-(methoxymethyl)pyrrolidin-1-yl)-2-oxo-1-phenylethylcarbamate (S)-2-(2-(4-bromo-3-iodophenyl)-2-oxoethyl) 1-tert-butyl pyrrolidine-1,2-dicarboxylate:

To a solution of 2-bromo-1-(4-bromo-3-iodophenyl)ethanone (20 mmol) in acetone (65 mL) was added (S)-1-(tert-butoxycarbonyl)pyrrolidine-2-carboxylic acid (3, 14 mmol), $K_2CO_3$ (2.5 g, 18 mmol), and KI (235 mg, 1.4 mmol). After stirring for 15 h, the solution was diluted with EtOAc and washed successively with saturated aqueous $NaHCO_3$ and brine. The organics were dried over $MgSO_4$, filtered and concentrated under reduced pressure. The crude residue was purified by silica column chromatography to afford (S)-2-(2-(4-bromo-3-iodophenyl)-2-oxoethyl) 1-tert-butyl pyrrolidine-1,2-dicarboxylate (3.6 g, 34%).

(S)-tert-butyl 2-(5-(4-bromo-3-iodophenyl)-1H-imidazol-2-yl)pyrrolidine-1-carboxylate: To (S)-2-(2-(4-bromo-3-iodophenyl)-2-oxoethyl) 1-tert-butyl pyrrolidine-1,2-dicarboxylate (3.6 g, 6.7 mmol) was added PhMe (65 mL) and ammonium acetate (5.5 g, 67 mmol) and the solution was heated to 110° C. and stirred overnight. The following morning, the solution was cooled to rt and was diluted with EtOAc and washed successively with water, saturated aqueous $NaHCO_3$ and brine. The organics were dried over $MgSO_4$, filtered and concentrated under reduced pressure. The crude residue was purified by silica column chromatography (40% to 100% EtOAc/hexanes) to afford (S)-tert-butyl 2-(5-(4-bromo-3-iodophenyl)-1H-imidazol-2-yl)pyrrolidine-1-carboxylate (2.9 g, 84%).

(S)-tert-butyl 2-(5-(4-bromo-3-(prop-1-ynyl)phenyl)-1H-imidazol-2-yl)pyrrolidine-1-carboxylate: To (S)-tert-butyl 2-(5-(4-bromo-3-iodophenyl)-1H-imidazol-2-yl)pyrrolidine-1-carboxylate (1.5 g, 2.9 mmol) was added $PdCl_2(PPh_3)_4$ (145 mg, 0.2 mmol), CuI (77 mg, 0.4 mmol) and $Et_3N$ (29 mL). Prop-1-yne was bubbled through the solution and the reaction mixture was heated to 50° C. for 1.5 h. After cooling, the solution was diluted with EtOAc, washed with $NH_4Cl$, water, and brine. The organics were dried over $MgSO_4$, filtered and concentrated under reduced pressure. The crude residue was purified by silica gel chromatography to afford (S)-tert-butyl 2-(5-(4-bromo-3-(prop-1-ynyl)phenyl)-1H-imidazol-2-yl)pyrrolidine-1-carboxylate (1.25 g).

Methyl (S)-1-((S)-2-(5-(4-bromo-3-(prop-1-ynyl)phenyl)-1H-imidazol-2-yl)pyrrolidin-1-yl)-3-methyl-1-oxobutan-2-ylcarbamate: (S)-tert-butyl 2-(5-(4-bromo-3-(prop-1-ynyl)phenyl)-1H-imidazol-2-yl)pyrrolidine-1-carboxylate (400 mg, 0.98 mmol) was dissolved in DCM (8 mL), MeOH (2 mL) and HCl (4 M in dioxane, 2 mL) was added. The reaction mixture was stirred for 22 h and then concentrated under reduced pressure. The crude residue was treated with (S)-2-(methoxycarbonylamino)-3-methylbutanoic acid (163 mg, 0.93 mmol), HATU (354 mg, 0.98 mmol) and DMF (10 mL), then DIPEA (0.81 mL, 4.65 mmol) was added dropwise. After 2 h, the mixture was diluted with EtOAc and washed successively with saturated aqueous $NaHCO_3$ and brine. The organics were dried over $MgSO_4$, filtered and concentrated under reduced pressure. The crude residue was purified by silica gel chromatography (0% to 30% MeOH/EtOAc) to afford methyl (S)-1-((S)-2-(5-(4-bromo-3-(prop-1-ynyl)phenyl)-1H-imidazol-2-yl)pyrrolidin-1-yl)-3-methyl-1-oxobutan-2-ylcarbamate (369 mg, 81%).

Methyl (S)-3-methyl-1-oxo-1-((S)-2-(5-(3-(prop-1-ynyl)-4-(4,4,5,5-tetramethyl-1,3,2-dioxaborolan-2-yl)phenyl)-1H-imidazol-2-yl)pyrrolidin-1-yl)butan-2-ylcarbamate: Methyl (S)-1-((S)-2-(5-(4-bromo-3-(prop-1-ynyl)phenyl)-1H-imidazol-2-yl)pyrrolidin-1-yl)-3-methyl-1-oxobutan-2-ylcarbamate (369 mg, 0.76 mmol) in dioxane (10 mL) was added bis(pinacolato)diboron (232 mg, 0.91 mmol), KOAc (223 mg, 2.28 mmol), and Pd(dppf)$_2$Cl$_2$ (56 mg, 0.076 mmol). The solution was degassed with N$_2$ for 10 min, then heated to 90° C. for 5 h. The solution was cooled to rt, diluted with EtOAc, washed with saturated aqueous NaHCO$_3$, brine, dried with MgSO$_4$, and concentrated. Purified by silica gel chromatography (0% to 30% MeOH/EtOAc) to afford methyl (S)-3-methyl-1-oxo-1-((S)-2-(5-(3-(prop-1-ynyl)-4-(4,4,5,5-tetramethyl-1,3,2-dioxaborolan-2-yl)phenyl)-1H-imidazol-2-yl)pyrrolidin-1-yl)butan-2-ylcarbamate (153 mg, 38%).

(2S,4S)-tert-butyl 2-(7-(4-(2-((S)-1-((S)-2-(methoxycarbonylamino)-3-methylbutanoyl)pyrrolidin-2-yl)-1H-imidazol-5-yl)-2-(prop-1-ynyl)phenyl)-1H-naphtho[1,2-d]imidazol-2-yl)-4-(methoxymethyl)pyrrolidine-1-carboxylate: Methyl (S)-3-methyl-1-oxo-1-((S)-2-(5-(3-(prop-1-ynyl)-4-(4,4,5,5-tetramethyl-1,3,2-dioxaborolan-2-yl)phenyl)-1H-imidazol-2-yl)pyrrolidin-1-yl)butan-2-ylcarbamate (153 mg, 0.28 mmol), (2S,4S)-tert-butyl 2-(7-bromo-1H-naphtho[1,2-d]imidazol-2-yl)-4-(methoxymethyl)pyrrolidine-1-carboxylate (158 mg, 0.34 mmol), Pd(PPh$_3$)$_4$ (32 mg, 0.028 mmol), Pd(dppf)$_2$Cl$_2$ (20 mg, 0.028 mmol), and K$_2$CO$_3$ (2M in H$_2$O, 0.46 mL, 0.92 mmoL) were combined in DME (4 mL). The mixture was degassed with bubbling N$_2$ for 10 min the heated to 85° C. for 16 h. After cooling, the reaction mixture was diluted with EtOAc, and washed successively with saturated aqueous NaHCO$_3$ and brine. The organics were dried over MgSO$_4$, filtered and concentrated under reduced pressure. The crude residue was purified by silica column chromatography (0% to % MeOH/EtOAc) to afford (2S,4S)-tert-butyl 2-(7-(4-(2-((S)-1-((S)-2-(methoxycarbonylamino)-3-methylbutanoyl)pyrrolidin-2-yl)-1H-imidazol-5-yl)-2-(prop-1-ynyl)phenyl)-1H-naphtho[1,2-d]imidazol-2-yl)-4-(methoxymethyl)pyrrolidine-1-carboxylate (66 mg, 30%).

Methyl (R)-2-((2S,4S)-2-(7-(4-(2-((S)-1-((S)-2-(methoxycarbonylamino)-3-methylbutanoyl)pyrrolidin-2-yl)-1H-imidazol-5-yl)-2-(prop-1-ynyl)phenyl)-1H-naphtho[1,2-d]imidazol-2-yl)-4-(methoxymethyl)pyrrolidin-1-yl)-2-oxo-1-phenylethylcarbamate: (2S,4S)-tert-butyl 2-(7-(4-(2-((S)-1-((S)-2-(methoxycarbonylamino)-3-methylbutanoyl)pyrrolidin-2-yl)-1H-imidazol-5-yl)-2-(prop-1-ynyl)phenyl)-1H-naphtho[1,2-d]imidazol-2-yl)-4-(methoxymethyl)pyrrolidine-1-carboxylate (66 mg, 0.084 mmol) was dissolved in DCM (2 mL), MeOH (0.5 mL) and HCl (4 M in dioxane, 0.5 mL) was added. The reaction mixture was stirred for 2 h and then concentrated under reduced pressure. The crude residue was treated with (R)-2-(methoxycarbonylamino)-2-phenylacetic acid (18 mg, 0.084 mmol), COMU (40 mg, 0.084 mmol) and DMF (3 mL), then DIPEA (0.73 mL, 0.42 mmol) was added dropwise. After 15 h, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl (R)-2-((2S,4S)-2-(7-(4-(2-((S)-1-((S)-2-(methoxycarbonylamino)-3-methylbutanoyl)pyrrolidin-2-yl)-1H-imidazol-5-yl)-2-(prop-1-ynyl)phenyl)-1H-naphtho[1,2-d]imidazol-2-yl)-4-(methoxymethyl)pyrrolidin-1-yl)-2-oxo-1-phenylethylcarbamate (16 mg, 21%). LCMS-ESI$^+$: calculated for C50H54N8O7: 878.41; observed [M+1]$^+$: 879.60.

Example NA

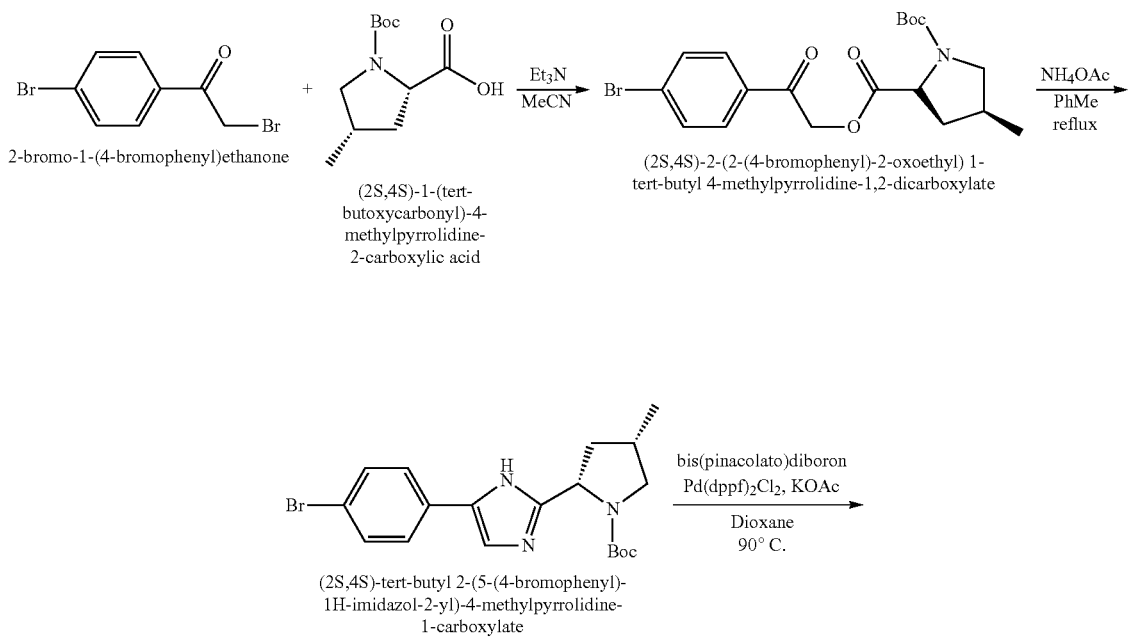

-continued

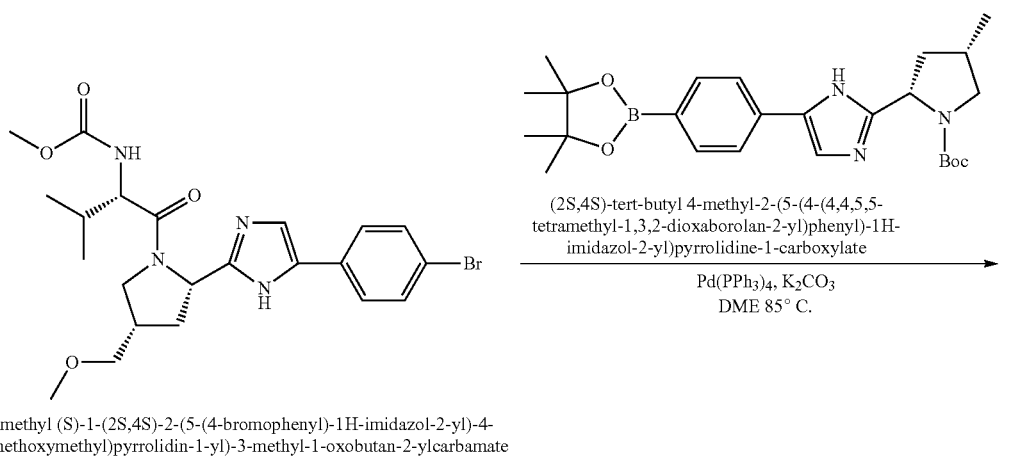

methyl (S)-1-(2S,4S)-2-(5-(4-bromophenyl)-1H-imidazol-2-yl)-4-(methoxymethyl)pyrrolidin-1-yl)-3-methyl-1-oxobutan-2-ylcarbamate (2S,4S)-tert-butyl 4-methyl-2-(5-(4-(4,4,5,5-tetramethyl-1,3,2-dioxaborolan-2-yl)phenyl)-1H-imidazol-2-yl)pyrrolidine-1-carboxylate Pd(PPh$_3$)$_4$, K$_2$CO$_3$
DME 85° C.

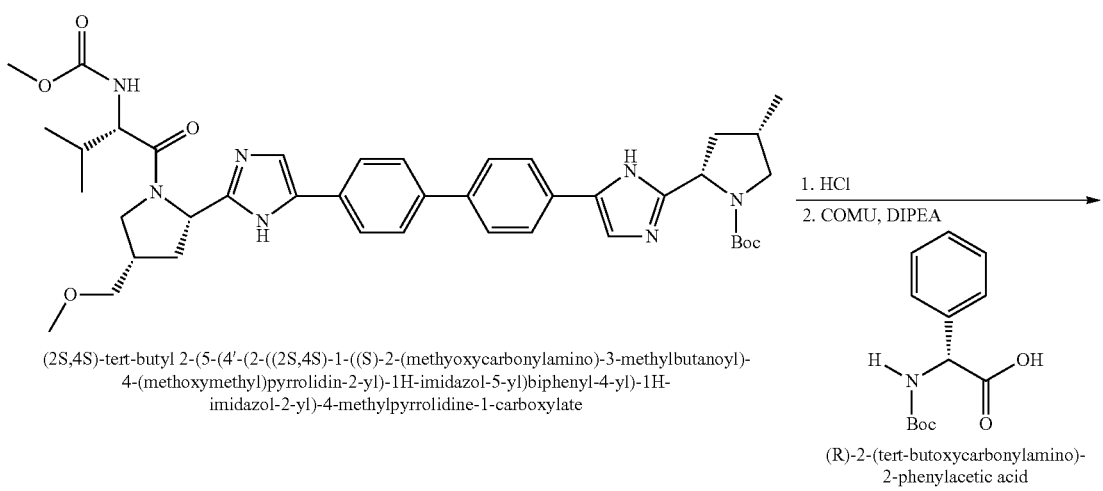

(2S,4S)-tert-butyl 2-(5-(4'-(2-((2S,4S)-1-((S)-2-(methyoxycarbonylamino)-3-methylbutanoyl)-4-(methoxymethyl)pyrrolidin-2-yl)-1H-imidazol-5-yl)biphenyl-4-yl)-1H-imidazol-2-yl)-4-methylpyrrolidine-1-carboxylate 1. HCl
2. COMU, DIPEA (R)-2-(tert-butoxycarbonylamino)-2-phenylacetic acid

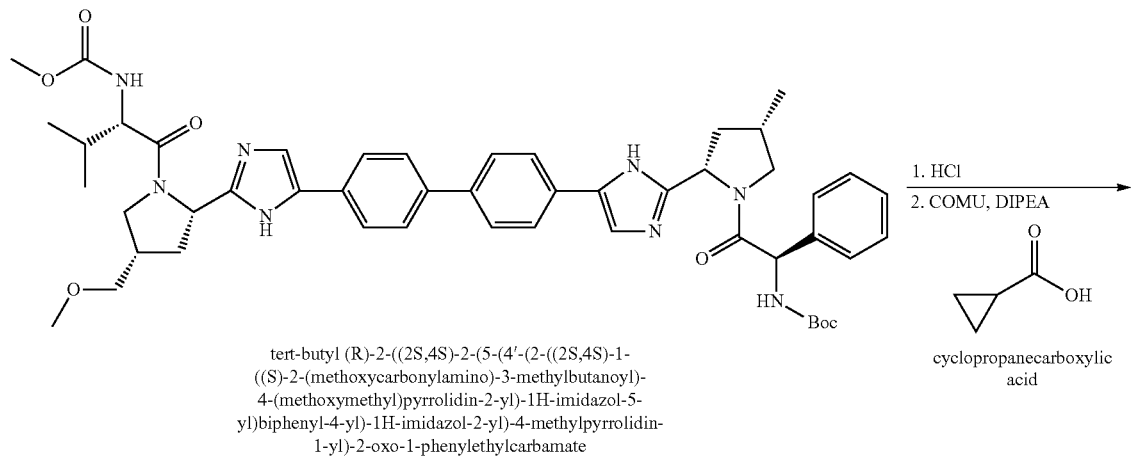

tert-butyl (R)-2-((2S,4S)-2-(5-(4'-(2-((2S,4S)-1-((S)-2-(methoxycarbonylamino)-3-methylbutanoyl)-4-(methoxymethyl)pyrrolidin-2-yl)-1H-imidazol-5-yl)biphenyl-4-yl)-1H-imidazol-2-yl)-4-methylpyrrolidin-1-yl)-2-oxo-1-phenylethylcarbamate 1. HCl
2. COMU, DIPEA cyclopropanecarboxylic acid

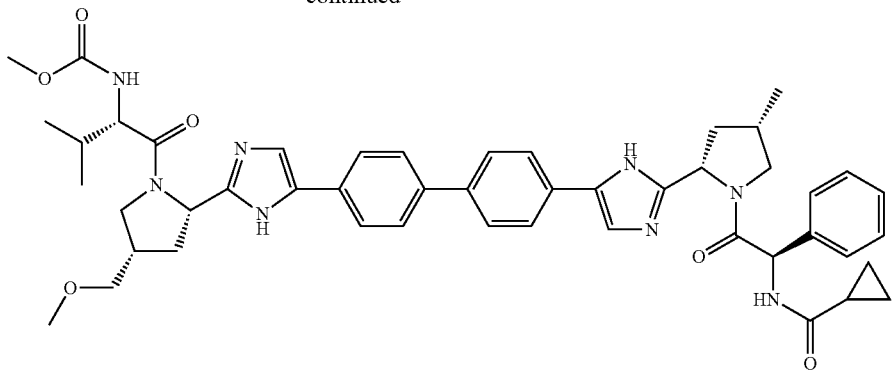

methyl (S)-1-((2S,4S)-2-(5-(4'-(2-((2S,4S)-1-((R)-2-(cyclopropanecarboxamido)-2-phenylacetyl)-4-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate (2S,4S)-2-(2-(4-bromophenyl)-2-oxoethyl) 1-tert-butyl 4-methylpyrrolidine-1,2-dicarboxylate: To a solution of 2-bromo-1-(4-bromophenyl)ethanone (505 mg, 1.82 mmol) in MeCN (18 mL) was added (2S,4S)-1-(tert-butoxycarbonyl)-4-methylpyrrolidine-2-carboxylic acid (500 mg, 2.18 mmol) and triethyl amine (0.27 mL, 2.0 mmol). After stirring for 15 h, the solution was diluted with EtOAc and washed successively with saturated aqueous NaHCO₃ and brine. The organics were dried over MgSO₄, filtered and concentrated under reduced pressure. The crude residue was purified by silica column chromatography (10% to 35% EtOAc/hexanes) to afford (2S,4S)-2-(2-(4-bromophenyl)-2-oxoethyl) 1-tert-butyl 4-methylpyrrolidine-1,2-dicarboxylate (748 mg, 97%).

(2S,4S)-tert-butyl 2-(5-(4-bromophenyl)-1H-imidazol-2-yl)-4-methylpyrrolidine-1-carboxylate: (2S,4S)-2-(2-(4-bromophenyl)-2-oxoethyl) 1-tert-butyl 4-methylpyrrolidine-1,2-dicarboxylate (748 mg, 1.75 mmol) was added PhMe (17 mL) and ammonium acetate (2.7 g, 35 mmol) and the solution was heated to 110° C. and stirred overnight. The following morning, the solution was cooled to rt and was diluted with EtOAc and washed successively with water, saturated aqueous NaHCO₃ and brine. The organics were dried over MgSO₄, filtered and concentrated under reduced pressure. The crude residue was purified by silica column chromatography (60% to 100% EtOAc/hexanes) to afford (2S,4S)-tert-butyl 2-(5-(4-bromophenyl)-1H-imidazol-2-yl)-4-methylpyrrolidine-1-carboxylate (606 mg, 85%).

(2S,4S)-tert-butyl 4-methyl-2-(5-(4-(4,4,5,5-tetramethyl-1,3,2-dioxaborolan-2-yl)phenyl)-1H-imidazol-2-yl)pyrrolidine-1-carboxylate: (2S,4S)-tert-butyl 2-(5-(4-bromophenyl)-1H-imidazol-2-yl)-4-methylpyrrolidine-1-carboxylate (606 mg, 1.49 mmol) in dioxane (15 mL) was added bis(pinacolato)diboron (455 mg, 1.79 mmol), KOAc (439 mg, 4.47 mmol), and Pd(dppf)₂Cl₂ (109 mg, 0.15 mmol). The solution was degassed with N₂ for 10 min, then heated to 90° C. for 2.5 h. The solution was cooled to rt, diluted with EtOAc, washed with saturated aqueous NaHCO₃, brine, dried with MgSO₄, and concentrated. Purified by silica gel chromatography (0% to 30% MeOH/EtOAc) to afford (2S,4S)-tert-butyl 4-methyl-2-(5-(4-(4,4,5,5-tetramethyl-1,3,2-dioxaborolan-2-yl)phenyl)-1H-imidazol-2-yl)pyrrolidine-1-carboxylate (628 mg, 93%).

(2S,4S)-tert-butyl 2-(5-(4'-(2-((2S,4S)-1-((S)-2-(methoxycarbonylamino)-3-methylbutanoyl)-4-(methoxymethyl)pyrrolidin-2-yl)-1H-imidazol-5-yl)biphenyl-4-yl)-1H-imidazol-2-yl)-4-methylpyrrolidine-1-carboxylate: Methyl (S)-1-((2S,4S)-2-(5-(4-bromophenyl)-1H-imidazol-2-yl)-4-(methoxymethyl)pyrrolidin-1-yl)-3-methyl-1-oxobutan-2-ylcarbamate (621 mg, 1.26 mmol), (2S,4S)-tert-butyl 4-methyl-2-(5-(4-(4,4,5,5-tetramethyl-1,3,2-dioxaborolan-2-yl)phenyl)-1H-imidazol-2-yl)pyrrolidine-1-carboxylate (628 mg, 1.39 mmol), Pd(PPh₃)₄ (145 mg, 0.13 mmol), and K₂CO₃ (2M in H₂O, 2.0 mL, 4.16 mmoL) were combined in DME (13 mL). The mixture was degassed with bubbling N₂ for 10 min the heated to 85° C. for 16 h. After cooling, the reaction mixture was diluted with EtOAc, and washed successively with saturated aqueous NaHCO₃ and brine. The organics were dried over MgSO₄, filtered and concentrated under reduced pressure. The crude residue was purified by silica column chromatography (0% to 30% MeOH/EtOAc) to afford (2S,4S)-tert-butyl 2-(5-(4'-(2-((2S,4S)-1-((S)-2-(methoxycarbonylamino)-3-methylbutanoyl)-4-(methoxymethyl)pyrrolidin-2-yl)-1H-imidazol-5-yl)biphenyl-4-yl)-1H-imidazol-2-yl)-4-methylpyrrolidine-1-carboxylate (342 mg, 37%).

Tert-butyl (R)-2-((2S,4S)-2-(5-(4'-(2-((2S,4S)-1-((S)-2-(methoxycarbonylamino)-3-m ethylbutanoyl)-4-(methoxymethyl)pyrrolidin-2-yl)-1H-imidazol-5-yl) biphenyl-4-yl)-1H-imidazol-2-yl)-4-methylpyrrolidin-1-yl)-2-oxo-1-phenylethylcarbamate: (2S,4S)-tert-butyl 2-(5-(4'-(2-((2S,4S)-1-((S)-2-(methoxycarbonylamino)-3-methylbutanoyl)-4-(methoxymethyl)pyrrolidin-2-yl)-1H-imidazol-5-yl)biphenyl-4-yl)-1H-imidazol-2-yl)-4-methylpyrrolidine-1-carboxylate (342 mg, 0.46 mmol) was dissolved in DCM (4 mL), MeOH (1 mL) and HCl (4 M in dioxane, 1 mL) was added. The reaction mixture was stirred over night and then concentrated under reduced pressure. The crude residue was treated with (R)-2-(tert-butoxycarbonylamino)-2-phenylacetic acid (116 mg, 0.46 mmol), COMU (220 mg, 0.64 mmol) and DMF (5 mL), then DIPEA (0.4 mL, 2.31 mmol) was added dropwise. After 2 h, the mixture was diluted with EtOAc and washed successively with saturated aqueous NaHCO₃ and brine. The organics were dried over MgSO₄, filtered and concentrated under reduced pressure. The crude residue was purified by silica column chromatography (0% to 30% MeOH/EtOAc) to afford tert-butyl (R)-2-((2S,4S)-2-(5-(4'-(2-((2S,4S)-1-((S)-2-(methoxycarbonylamino)-3-methylbutanoyl)-4-(methoxymethyl)pyrrolidin-2-yl)-1H-imidazol-5-yl)biphenyl-4-yl)-1H-imidazol-2-yl)-4-methylpyrrolidin-1-yl)-2-oxo-1-phenylethylcarbamate (296 mg, 74%).

Methyl (S)-1-((2S,4S)-2-(5-(4'-(2-((2S,4S)-1-((R)-2-(cyclopropanecarboxamido)-2-phenylacetyl)-4-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate: Tert-butyl (R)-2-((2S,4S)-2-(5-(4'-(2-((2S,4S)-1-((S)-2-(methoxycarbonylamino)-3-methylbutanoyl)-4-(methoxymethyl)pyrrolidin-2-yl)-1H-imidazol-5-yl)biphenyl-4-yl)-1H-imidazol-2-yl)-4-methylpyrrolidin-1-yl)-2-oxo-1-phenylethylcarbamate (296 mg, 0.33 mmol) was dissolved in DCM (4 mL), MeOH (1 mL) and HCl (4 M in dioxane, 1 mL) was added. The reaction mixture was stirred over night and then concentrated under reduced pressure. The crude residue was treated with cyclopropanecarboxylic acid (38 µL, 0.28 mmol), COMU (162 mg, 0.34 mmol) and DMF (4 mL), then DIPEA (0.29 mL, 1.65 mmol) was added dropwise. After 30 min, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl (S)-1-((2S,4S)-2-(5-(4'-(2-((2S,4S)-1-((R)-2-(cyclopropanecarboxamido)-2-phenylacetyl)-4-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate (68 mg, 24%). LCMS-ESI$^+$: calculated for C48H56N8O6: 840.43; observed [M+1]$^+$: 842.14.

Example NB

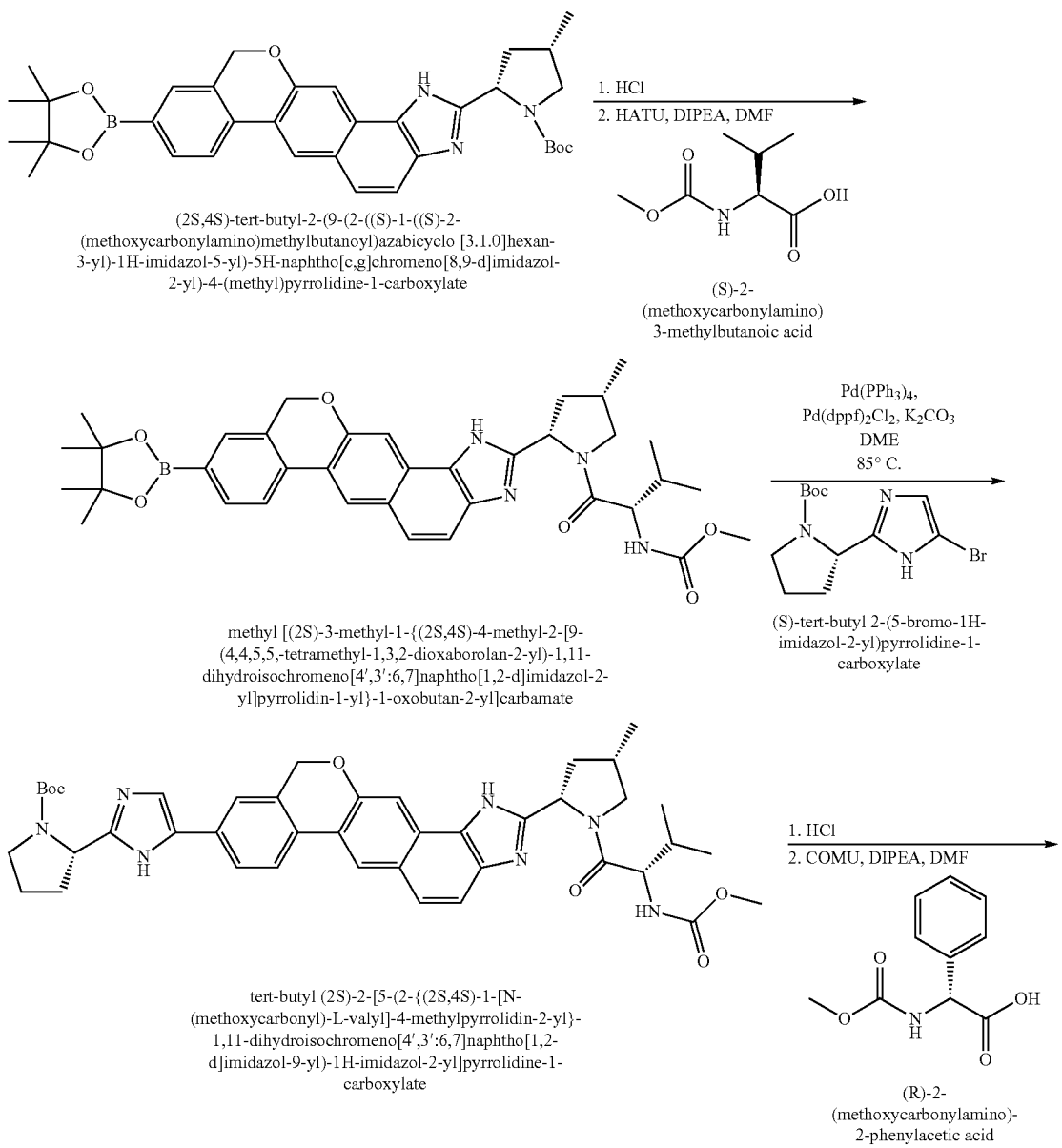

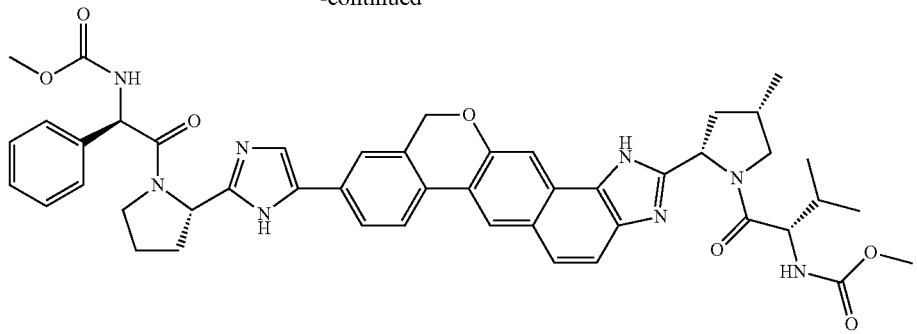

methyl {(1R)-2-[(2S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate Methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate: (2S,4S)-tert-butyl-2-(9-(2-((S)-1-((S)-2-(methoxycarbonylamino)methylbutanoyl)azabicyclo[3.1.0]hexan-3-yl)-1H-imidazol-5-yl)-5H-naphtho[c,g]chromeno[8,9-d]imidazol-2-yl)-4-(methyl)pyrrolidine-1-carboxylate (950 mg, 1.63 mmol) was dissolved in DCM (12 mL), MeOH (3 mL) and HCl (4 M in dioxane, 3 mL) was added. The reaction mixture was stirred for 4 h and then concentrated under reduced pressure. The crude residue was treated with (S)-2-(methoxycarbonylamino)-3-methylbutanoic acid (285 mg, 1.63 mmol), HATU (620 mg, 1.63 mmol) and DMF (15 mL), then DIPEA (1.42 mL, 8.15 mmol) was added dropwise. After 1 h, the mixture was diluted with EtOAc and washed successively with saturated aqueous $NaHCO_3$ and brine. The organics were dried over $MgSO_4$, filtered and concentrated under reduced pressure. The crude residue was purified by silica column chromatography (0% to 30% MeOH/EtOAc) to afford methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (596 mg, 57%).

Tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate: Methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (298 mg, 0.47 mmol), (S)-tert-butyl 2-(5-bromo-1H-imidazol-2-yl)pyrrolidine-1-carboxylate (443 mg, 1.4 mmol), $Pd(PPh_3)_4$ (54 mg, 0.05 mmol), $PdCl_2(dppf)_2$ (36 mg, 0.05 mmol), and $K_2CO_3$ (2M in $H_2O$, 0.78 mL, 1.55 mmol) were combined in DME (5 mL). The mixture was degassed with bubbling $N_2$ for 10 min the heated to 85° C. for 16 h. After cooling, the reaction mixture was diluted with EtOAc, and washed successively with saturated aqueous $NaHCO_3$ and brine. The organics were dried over $MgSO_4$, filtered and concentrated under reduced pressure. The crude residue was purified by silica column chromatography (0% to 30% MeOH/EtOAc) to afford tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate (84 mg, 24%).

Methyl {(1R)-2-[(2S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate: Tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate (84 mg, 0.11 mmol) was dissolved in DCM (2.5 mL), MeOH (0.5 mL) and HCl (4 M in dioxane, 0.5 mL) was added. The reaction mixture was stirred for 18 h and then concentrated under reduced pressure. The crude residue was treated with (R)-2-(methoxycarbonylamino)-2-phenylacetic acid (23 mg, 0.11 mmol), COMU (53 mg, 0.11 mmol) and DMF (3 mL), then DIPEA (0.10 mL, 0.56 mmol) was added dropwise. After 30 min, the mixture was diluted with 10% MeOH/EtOAc and washed successively with saturated aqueous $NaHCO_3$ and brine. The organics were dried over $MgSO_4$, filtered and concentrated under reduced pressure. The crude residue was purified by HPLC to afford methyl {(1R)-2-[(2S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3': 6,7]naphtho[1,2-d]imidazol-9-yl}-1H-imidazol-2-yl)pyrrolidin-1-yl]-2-oxo-1-phenylethyl}carbamate (41 mg, 45%). LCMS-ESI$^+$: calculated for $C_{47}H_{50}N_8O_7$: 838.38; observed [M+1]$^+$: 839.39.

Example NC

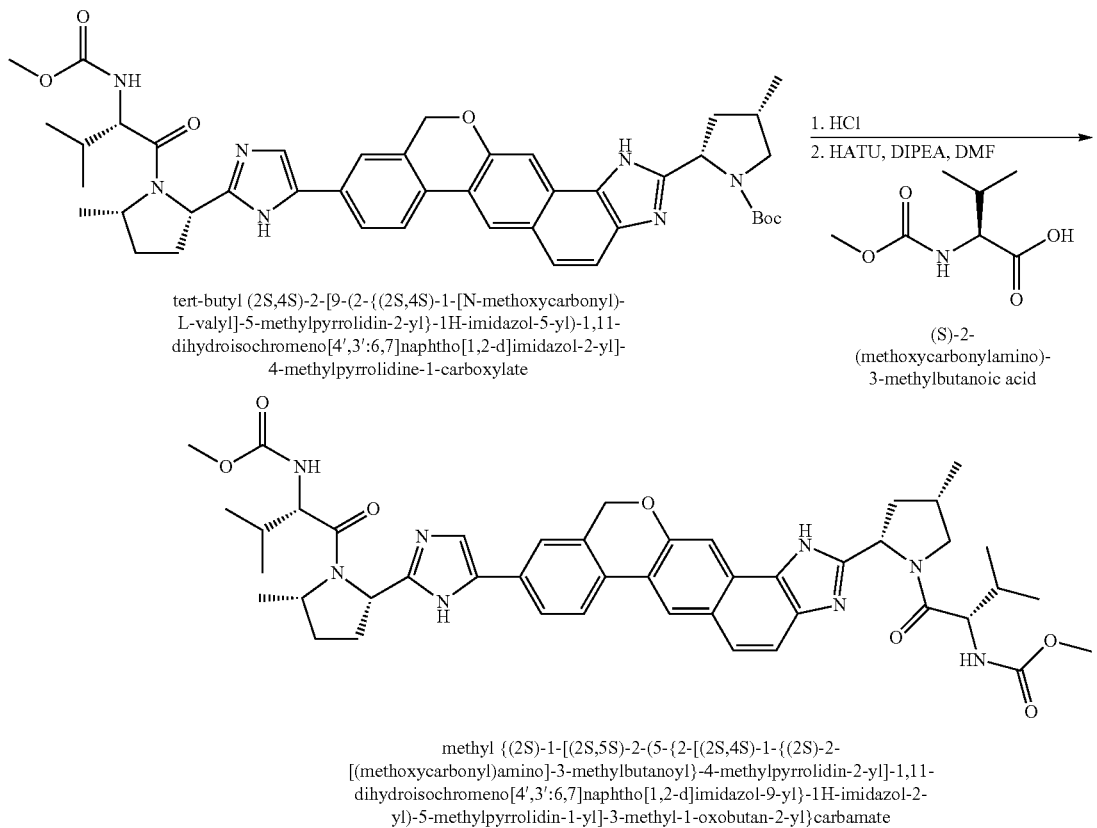

Methyl {(2S)-1-[(2S,5S)-2-(5-{2-[(2S,4S)-1-{(2S)-2-[(methoxycarbonyl)amino]-3-methylbutanoyl}-4-methyl-pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate: Tert-butyl (2S,4S)-2-[9-(2-{(2S,4S)-1-[N-(methoxycarbonyl)-L-valyl]-5-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (164 mg, 0.23 mmol) was dissolved in DCM (2.57 mL), MeOH (0.7 mL) and HCl (4 M in dioxane, 0.7 mL) was added. The reaction mixture was stirred for 16 h and then concentrated under reduced pressure. The crude residue was treated with (S)-2-(methoxycarbonylamino)-3-methylbutanoic acid (30 mg, 0.17 mmol), HATU (65 mg, 0.17 mmol) and DMF (3 mL), then DIPEA (0.15 mL, 0.85 mmol) was added dropwise. After 45 min, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl {(2S)-1-[(2S,5S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (23 mg, 16%).

LCMS-ESI$^+$: calculated for C$_{45}$H$_{54}$N$_8$O$_7$: 818.41; observed [M+1]$^+$: 820.70.

Example ND

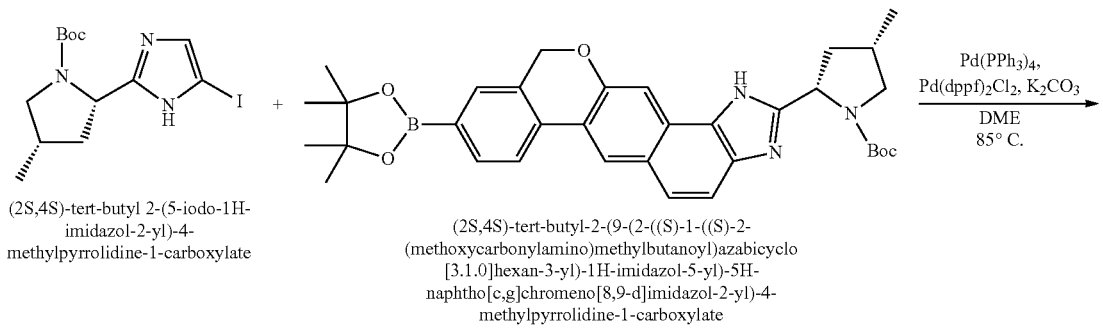

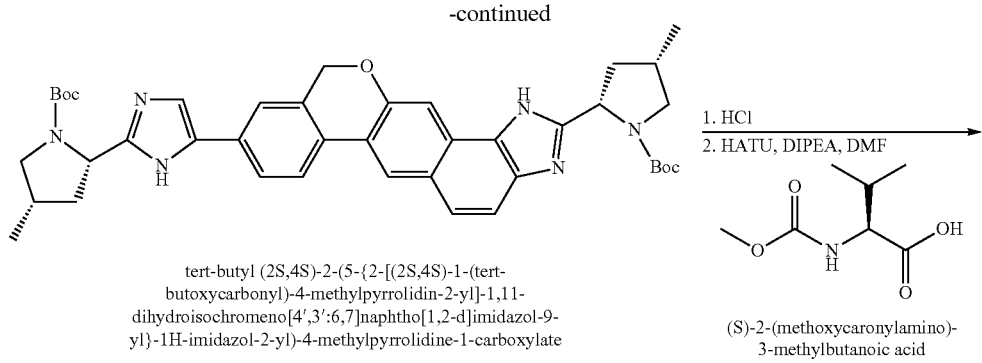

tert-butyl (2S,4S)-2-(5-{2-[(2S,4S)-1-(tert-butoxycarbonyl)-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-carboxylate (S)-2-(methoxycaronylamino)-3-methylbutanoic acid

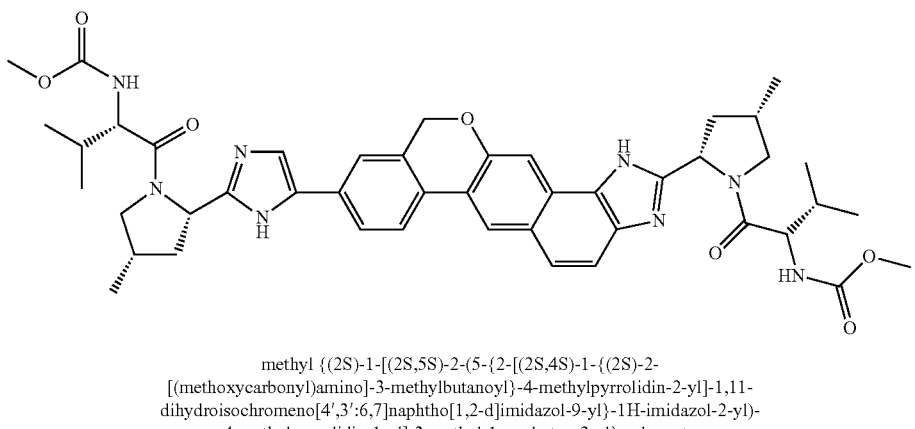

methyl {(2S)-1-[(2S,5S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate Tert-butyl (2S,4S)-2-(5-{2-[(2S,4S)-1-(tert-butoxycarbonyl)-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-carboxylate: (2S,4S)-tert-butyl-2-(9-(2-((S)-1-((S)-2-(methoxycarbonylamino)methylbutanoyl)azabicyclo[3.1.0]hexan-3-yl)-1H-imidazol-5-yl)-5H-naphtho[c,g]chromeno[8,9-d]imidazol-2-yl)-4-methylpyrrolidine-1-carboxylate (293 mg, 0.0.78 mmol), (2S,4S)-tert-butyl 2-(5-iodo-1H-imidazol-2-yl)-4-methylpyrrolidine-1-carboxylate (300 mg, 0.52 mmol), Pd(PPh$_3$)$_4$ (60 mg, 0.052 mmol), PdCl$_2$(dppf)$_2$ (38 mg, 0.052 mmol), and K$_2$CO$_3$ (2M in H$_2$O, 0.86 mL, 1.72 mmoL) were combined in DME (6 mL). The mixture was degassed with bubbling N$_2$ for 10 min the heated to 85° C. for 16 h. After cooling, the reaction mixture was diluted with EtOAc, and washed successively with saturated aqueous NaHCO$_3$ and brine. The organics were dried over MgSO$_4$, filtered and concentrated under reduced pressure. The crude residue was purified by silica column chromatography (100% EtOAc) to afford tert-butyl (2S,4S)-2-(5-{2-[(2S,4S)-1-(tert-butoxycarbonyl)-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-carboxylate (183 mg, 50%).

Methyl {(2S)-1-[(2S,5S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate: Tert-butyl (2S,4S)-2-(5-{2-[(2S,4S)-1-(tert-butoxycarbonyl)-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-carboxylate (183 mg, 0.26 mmol) was dissolved in DCM (4 mL), MeOH (1 mL) and HCl (4 M in dioxane, 1 mL) was added. The reaction mixture was stirred for 2 h and then concentrated under reduced pressure. The crude residue was treated with (S)-2-(methoxycarbonylamino)-3-methylbutanoic acid (91 mg, 0.52 mmol), HATU (198 mg, 0.52 mmol) and DMF (5 mL), then DIPEA (0.45 mL, 2.6 mmol) was added dropwise. After 1 h, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl {(2S)-1-[(2S,5S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate (6 mg, 3%). LCMS-ESI$^+$: calculated for C45H54N8O7: 818.41; observed [M+1]$^+$: 819.41.

Example NE
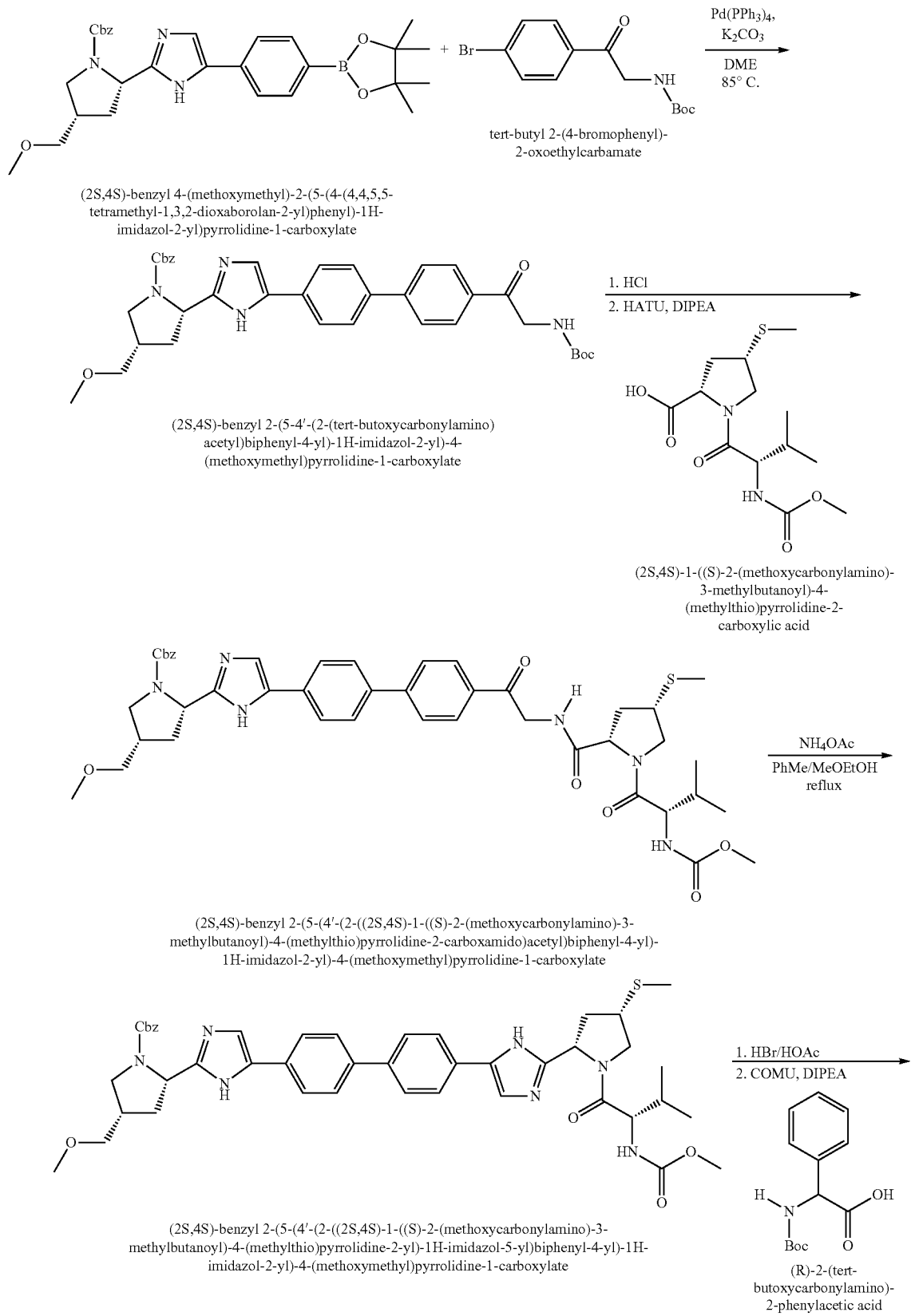

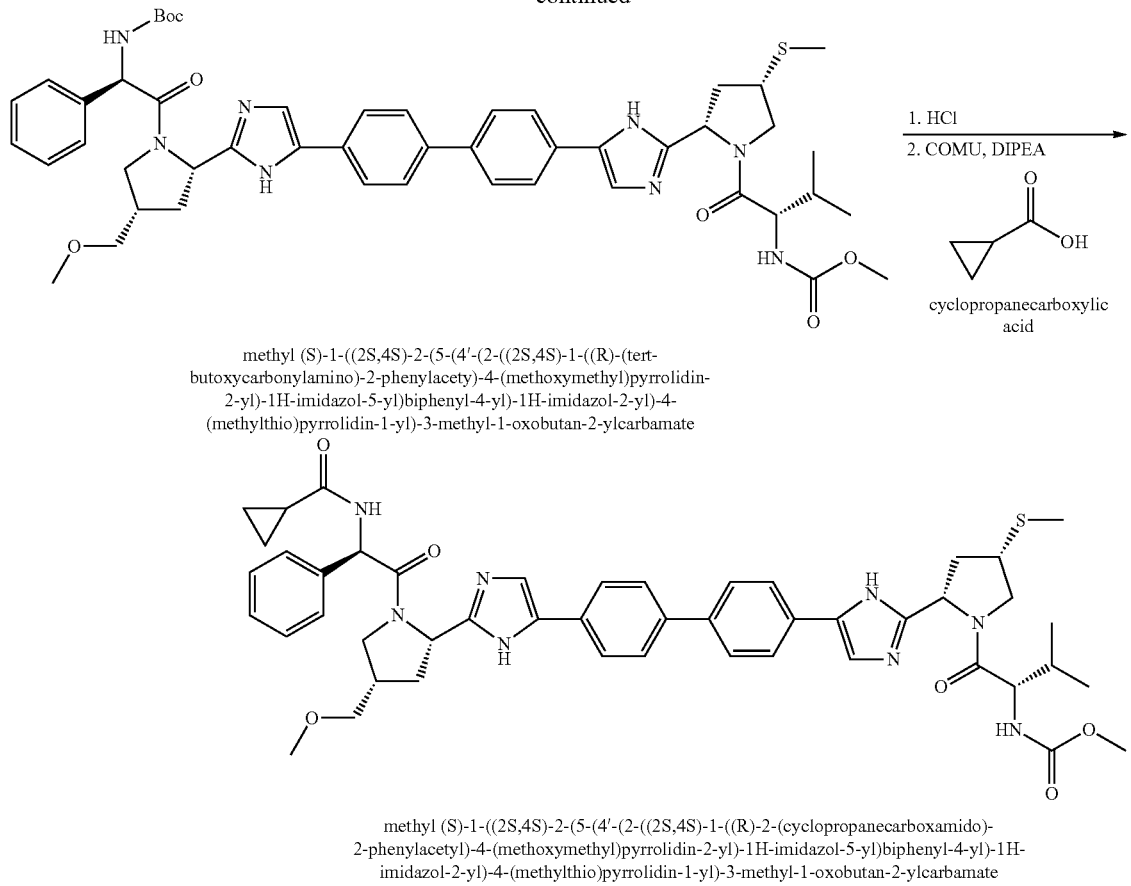

methyl (S)-1-((2S,4S)-2-(5-(4'-(2-((2S,4S)-1-((R)-(tert-butoxycarbonylamino)-2-phenylacety)-4-(methoxymethyl)pyrrolidin-2-yl)-1H-imidazol-5-yl)biphenyl-4-yl)-1H-imidazol-2-yl)-4-(methylthio)pyrrolidin-1-yl)-3-methyl-1-oxobutan-2-ylcarbamate methyl (S)-1-((2S,4S)-2-(5-(4'-(2-((2S,4S)-1-((R)-2-(cyclopropanecarboxamido)-2-phenylacetyl)-4-(methoxymethyl)pyrrolidin-2-yl)-1H-imidazol-5-yl)biphenyl-4-yl)-1H-imidazol-2-yl)-4-(methylthio)pyrrolidin-1-yl)-3-methyl-1-oxobutan-2-ylcarbamate (2S,4S)-benzyl 2-(5-(4'-(2-(tert-butoxycarbonylamino)acetyl)biphenyl-4-yl)-1H-imidazol-2-yl)-4-(methoxymethyl)pyrrolidine-1-carboxylate: (2S,4S)-benzyl 4-(methoxymethyl)-2-(5-(4-(4,4,5,5-tetramethyl-1,3,2-dioxaborolan-2-yl)phenyl)-1H-imidazol-2-yl)pyrrolidine-1-carboxylate (500 mg, 0.97 mmol), tert-butyl 2-(4-bromophenyl)-2-oxoethylcarbamate (364 mg, 1.16 mmol), Pd(PPh₃)₄ (112 mg, 0.097 mmol), and K₂CO₃ (2M in H₂O, 1.6 mL, 3.2 mmoL) were combined in DME (10 mL). The mixture was degassed with bubbling N₂ for 10 min the heated to 85° C. for 18 h. After cooling, the reaction mixture was diluted with EtOAc, and washed successively with saturated aqueous NaHCO₃ and brine. The organics were dried over MgSO₄, filtered and concentrated under reduced pressure. The crude residue was purified by silica column chromatography (0% to 30% MeOH/EtOAc) to afford product (357 mg, 56%).

(2S,4S)-benzyl 2-(5-(4'-(2-((2S,4S)-1-((S)-2-(methoxycarbonylamino)-3-methylbutanoyl)-4-(methylthio)pyrrolidine-2-carboxamido)acetyl)biphenyl-4-yl)-1H-imidazol-2-yl)-4-(methoxymethyl)pyrrolidine-1-carboxylate: (2S,4S)-benzyl 2-(5-(4'-(2-(tert-butoxycarbonylamino)acetyl)biphenyl-4-yl)-1H-imidazol-2-yl)-4-(methoxymethyl)pyrrolidine-1-carboxylate (640 mg, 1.02 mmol) was dissolved in DCM (8 mL), MeOH (2 mL) and HCl (4 M in dioxane, 2 mL) was added. The reaction mixture was stirred for 14 h and then concentrated under reduced pressure. The crude residue was treated with (2S,4S)-1-((S)-2-(methoxycarbonylamino)-3-methylbutanoyl)-4-(methylthio)pyrrolidine-2-carboxylic acid (324 mg, 1.02 mmol), HATU (388 mg, 1.02 mmol) and DMF (10 mL), then DIPEA (0.9 mL, 5.12 mmol) was added dropwise. After 1 h, the mixture was diluted with EtOAc and washed successively with saturated aqueous NaHCO₃ and brine. The organics were dried over MgSO₄, filtered and concentrated under reduced pressure. The crude residue was purified by silica column chromatography (0% to 30% MeOH/EtOAc) to afford (2S,4S)-benzyl 2-(5-(4'-(2-((2S,4S)-1-((S)-2-(methoxycarbonylamino)-3-methylbutanoyl)-4-(methylthio)pyrrolidine-2-carboxamido)acetyl)biphenyl-4-yl)-1H-imidazol-2-yl)-4-(methoxymethyl)pyrrolidine-1-carboxylate (487 mg, 58%).

(2S,4S)-benzyl 2-(5-(4'-(2-((2S,4S)-1-((S)-2-(methoxycarbonylamino)-3-methylbutanoyl)-4-(methylthio)pyrrolidin-2-yl)-1H-imidazol-5-yl)biphenyl-4-yl)-1H-imidazol-2-yl)-4-(methoxymethyl)pyrrolidine-1-carboxylate: To (2S,4S)-benzyl 2-(5-(4'-(2-((2S,4S)-1-((S)-2-(methoxycarbonylamino)-3-methylbutanoyl)-4-(methylthio)pyrrolidine-2-carboxamido)acetyl)biphenyl-4-yl)-H-imidazol-2-yl)-4-(methoxymethyl)pyrrolidine-1-carboxylate (487 mg, 0.59 mmol) was added PhMe (6 mL), MeOEtOH (1 mL), and ammonium acetate (0.91 g, 11.8 mmol) and the solution was heated to 110° C. The solution was stirred for 3 h and then cooled to rt and was diluted with EtOAc and washed successively with water, saturated aqueous NaHCO₃ and brine. The organics were dried over MgSO₄, filtered and concentrated under reduced pressure. The crude residue was purified by silica column chromatography (0% to 30% MeOH/EtOAc) to afford (2S,4S)-benzyl 2-(5-(4'-(2-((2S,4S)-1-((S)-2-(methoxycarbonylamino)-3-methylbutanoyl)-4-(methylthio)pyrrolidin-2-yl)-1H-imidazol-5-yl)biphenyl-4-yl)-1H-imidazol-2-yl)-4-(methoxymethyl)pyrrolidine-1-carboxylate (276 mg, 58%).

Methyl (S)-1-((2S,4S)-2-(5-(4'-(2-((2S,4S)-1-((R)-(tert-butoxycarbonylamino)-2-phenylacetyl)-4-(methoxymethyl)pyrrolidin-2-yl)-1H-imidazol-5-yl)biphenyl-4-yl)-1H-imidazol-2-yl)-4-(methylthio)pyrrolidin-1-yl)-3-methyl-1-oxobutan-2-ylcarbamate:

(2S,4S)-benzyl 2-(5-(4'-(2-((2S,4S)-1-((S)-2-(methoxycarbonylamino)-3-methylbutanoyl)-4-(methylthio)pyrrolidin-2-yl)-1H-imidazol-5-yl)biphenyl-4-yl)-1H-imidazol-2-yl)-4-(methoxymethyl)pyrrolidine-1-carboxylate (220 mg, 0.27 mmol) was dissolved in DCM (5 mL), MeOH (0.4 mL) and cooled to 0° C. HBr (33% in AcOH, 1 mL) was added dropwise. After stirring for 1 hr, the mixture was concentrated under reduced pressure, coevaporating with PhMe. The crude residue was treated with (R)-2-(tert-butoxycarbonylamino)-2-phenylacetic acid (68 mg, 0.27 mmol), COMU (129 mg, 0.27 mmol) and DMF (5 mL), then DIPEA (0.24 mL, 1.35 mmol) was added dropwise. After 1 h, the mixture was diluted with EtOAc and washed successively with saturated aqueous NaHCO$_3$ and brine. The organics were dried over MgSO$_4$, filtered and concentrated under reduced pressure. The crude residue was purified by silica column chromatography (0% to 40% MeOH/EtOAc) to afford methyl (S)-1-((2S,4S)-2-(5-(4'-(2-((2S,4S)-1-((R)-(tert-butoxycarbonylamino)-2-phenylacetyl)-4-(methoxymethyl)pyrrolidin-2-yl)-1H-imidazol-5-yl)biphenyl-4-yl)-1H-imidazol-2-yl)-4-(methylthio)pyrrolidin-1-yl)-3-methyl-1-oxobutan-2-ylcarbamate (179 mg, 73%).

Methyl (S)-1-((2S,4S)-2-(5-(4'-(2-((2S,4S)-1-((R)-2-(cyclopropanecarboxamido)-2-phenylacetyl)-4-(methoxymethyl)pyrrolidin-2-yl)-1H-imidazol-5-yl)biphenyl-4-yl)-1H-imidazol-2-yl)-4-(methylthio)pyrrolidin-1-yl)-3-methyl-1-oxobutan-2-ylcarbamate: Methyl (S)-1-((2S,4S)-2-(5-(4'-(2-((2S,4S)-1-((R)-(tert-butoxycarbonylamino)-2-phenylacety)-4-(methoxymethyl)pyrrolidin-2-yl)-1H-imidazol-5-yl)biphenyl-4-yl)-1H-imidazol-2-yl)-4-(methylthio)pyrrolidin-1-yl)-3-methyl-1-oxobutan-2-ylcarbamate (179 mg, 0.20 mmol) was dissolved in DCM (5 mL), MeOH (1 mL) and HCl (4 M in dioxane, 1 mL) was added. The reaction mixture was stirred for 20 h and then concentrated under reduced pressure. The crude residue was treated with cyclopropanecarboxylic acid (16 μL, 0.20 mmol), COMU (96 mg, 0.20 mmol) and DMF (5 mL), then DIPEA (0.17 mL, 1.0 mmol) was added dropwise. After 30 min, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl (S)-1-((2S,4S)-2-(5-(4'-(2-((2S,4S)-1-((R)-2-(cyclopropanecarboxamido)-2-phenylacetyl)-4-(methoxymethyl)pyrrolidin-2-yl)-1H-imidazol-5-yl)biphenyl-4-yl)-1H-imidazol-2-yl)-4-(methylthio)pyrrolidin-1-yl)-3-methyl-1-oxobutan-2-ylcarbamate (34 mg, 20%). LCMS-ESI$^+$: calculated for C48H56N8O6S: 872.40; observed [M+1]$^+$: 874.38.

Example NF

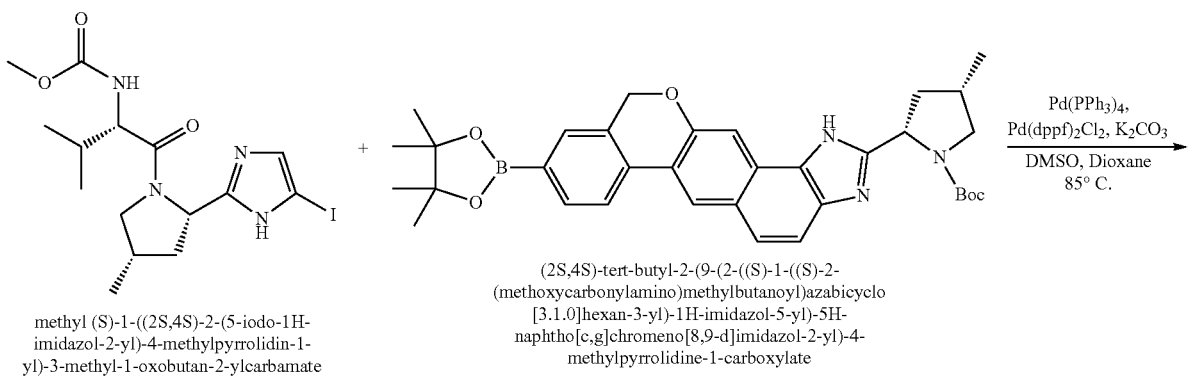

methyl (S)-1-((2S,4S)-2-(5-iodo-1H-imidazol-2-yl)-4-methylpyrrolidin-1-yl)-3-methyl-1-oxobutan-2-ylcarbamate (2S,4S)-tert-butyl-2-(9-(2-((S)-1-((S)-2-(methoxycarbonylamino)methylbutanoyl)azabicyclo[3.1.0]hexan-3-yl)-1H-imidazol-5-yl)-5H-naphtho[c,g]chromeno[8,9-d]imidazol-2-yl)-4-methylpyrrolidine-1-carboxylate

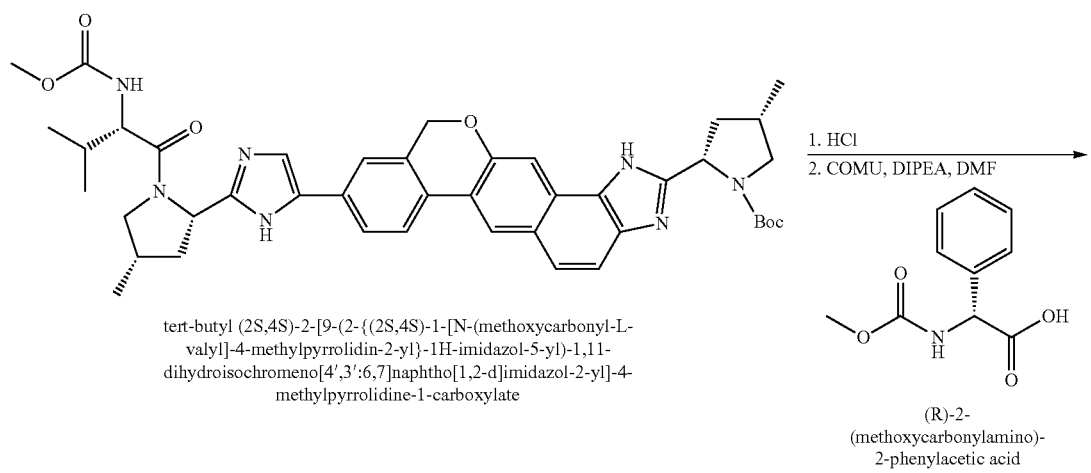

tert-butyl (2S,4S)-2-[9-(2-{(2S,4S)-1-[N-(methoxycarbonyl-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (R)-2-(methoxycarbonylamino)-2-phenylacetic acid

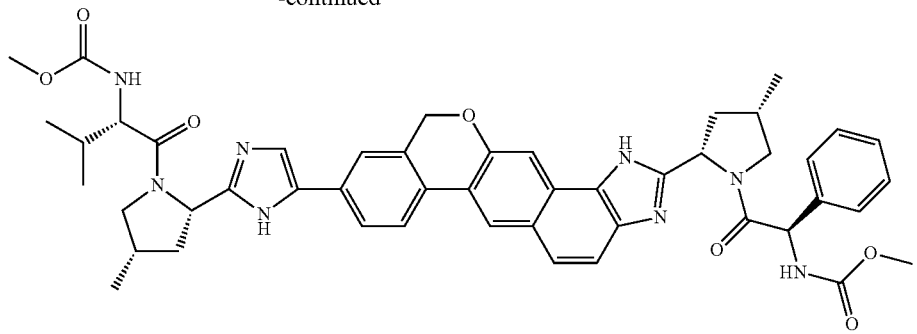

methyl {(2S)-1-[(2S,4S)-2-(5-{2-[(2S,4S)-1-{(2R)-2-[(methoxycarbonyl)amino]-2-phenylacetyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate Tert-butyl (2S,4S)-2-[9-(2-{(2S,4S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate: (2S,4S)-tert-butyl-2-(9-(2-((S)-1-((S)-2-(methoxycarbonylamino)methylbutanoyl)azabicyclo[3.1.0]hexan-3-yl)-1H-imidazol-5-yl)-5H-naphtho[c,g]chromeno[8,9-d]imidazol-2-yl)-4-methylpyrrolidine-1-carboxylate (558 mg, 0.96 mmol), methyl (S)-1-((2S,4S)-2-(5-iodo-1H-imidazol-2-yl)-4-methylpyrrolidin-1-yl)-3-methyl-1-oxobutan-2-ylcarbamate (501 mg, 1.15 mmol), Pd(PPh₃)₄ (111 mg, 0.096 mmol), PdCl₂(dppf)₂ (70 mg, 0.096 mmol), and K₂CO₃ (2M in H₂O, 1.6 mL, 3.17 mmoL) were combined in DMSO (6 mL) and dioxane (6 mL). The mixture was degassed with bubbling N₂ for 10 min the heated to 95° C. for 14 h. After cooling, the reaction mixture was diluted with EtOAc, and washed successively with saturated aqueous NaHCO₃ and brine. The organics were dried over MgSO₄, filtered and concentrated under reduced pressure. The crude residue was purified by silica column chromatography (0%-30% MeOH/EtOAc) to afford tert-butyl (2S,4S)-2-[9-(2-{(2S,4S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (257 mg, 35%).

Methyl {(2S)-1-[(2S,4S)-2-(5-{2-[(2S,4S)-1-{(2R)-2-[(methoxycarbonyl)amino]-2-phenylacetyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate: Tert-butyl (2S,4S)-2-[9-(2-{(2S,4S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (257 mg, 0.34 mmol) was dissolved in DCM (4 mL), MeOH (1 mL) and HCl (4 M in dioxane, 1 mL) was added. The reaction mixture was stirred for 3 h and then concentrated under reduced pressure. The crude residue was treated with (R)-2-(methoxycarbonylamino)-2-phenylacetic acid (71 mg, 0.34 mmol), COMU (161 mg, 0.34 mmol) and DMF (6 mL), then DIPEA (0.3 mL, 1.67 mmol) was added dropwise. After 15 h, the mixture was diluted with 10% MeOH/EtOAc and washed successively with saturated aqueous NaHCO₃ and brine. The organics were dried over MgSO₄, filtered and concentrated under reduced pressure. The crude residue was purified by HPLC to afford methyl {(2S)-1-[(2S,4S)-2-(5-{2-[(2S,4S)-1-{(2R)-2-[(methoxycarbonyl)amino]-2-phenylacetyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate (152 mg, 53%). LCMS-ESI⁺: calculated for C48H52N8O7: 852.40; observed [M+1]⁺: 854.26. ¹H NMR (CD₃OD): 8.677 (s, 1H), 8.232-7.837 (m, 5H), 7.695-7.673 (m, 2H), 7.496-7.426 (m, 5H), 5.499 (s, 1H), 5.445-5.401 (m, 1H), 5.337 (s, 1H), 5.253-5.208 (q, 1H, J=7.2 Hz), 4.870 (m, 1H), 4.230 (d, 1H, J=7.2 Hz), 3.781 (m, 1H), 3.671 (s, 3H), 3.607 (s, 3H), 3.425 (m, 3H), 2.750-2.689 (m, 2H), 2.683 (m, 2H), 2.384 (m, 1H), 1.894 (quint, 2H, J=12 Hz), 1.249-1.151 (m, 6H), 0.974-0.890 (m, 6H).

Example NG

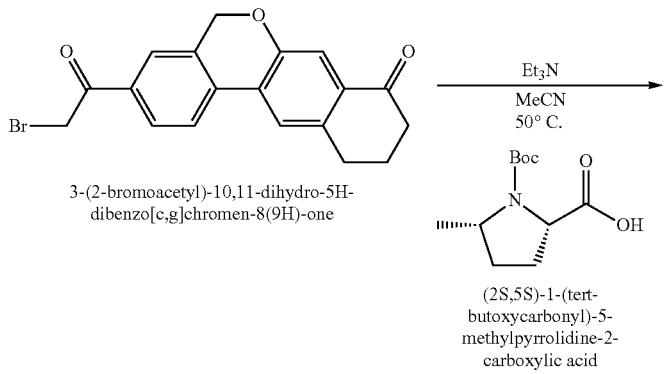

3-(2-bromoacetyl)-10,11-dihydro-5H-dibenzo[c,g]chromen-8(9H)-one (2S,5S)-1-(tert-butoxycarbonyl)-5-methylpyrrolidine-2-carboxylic acid

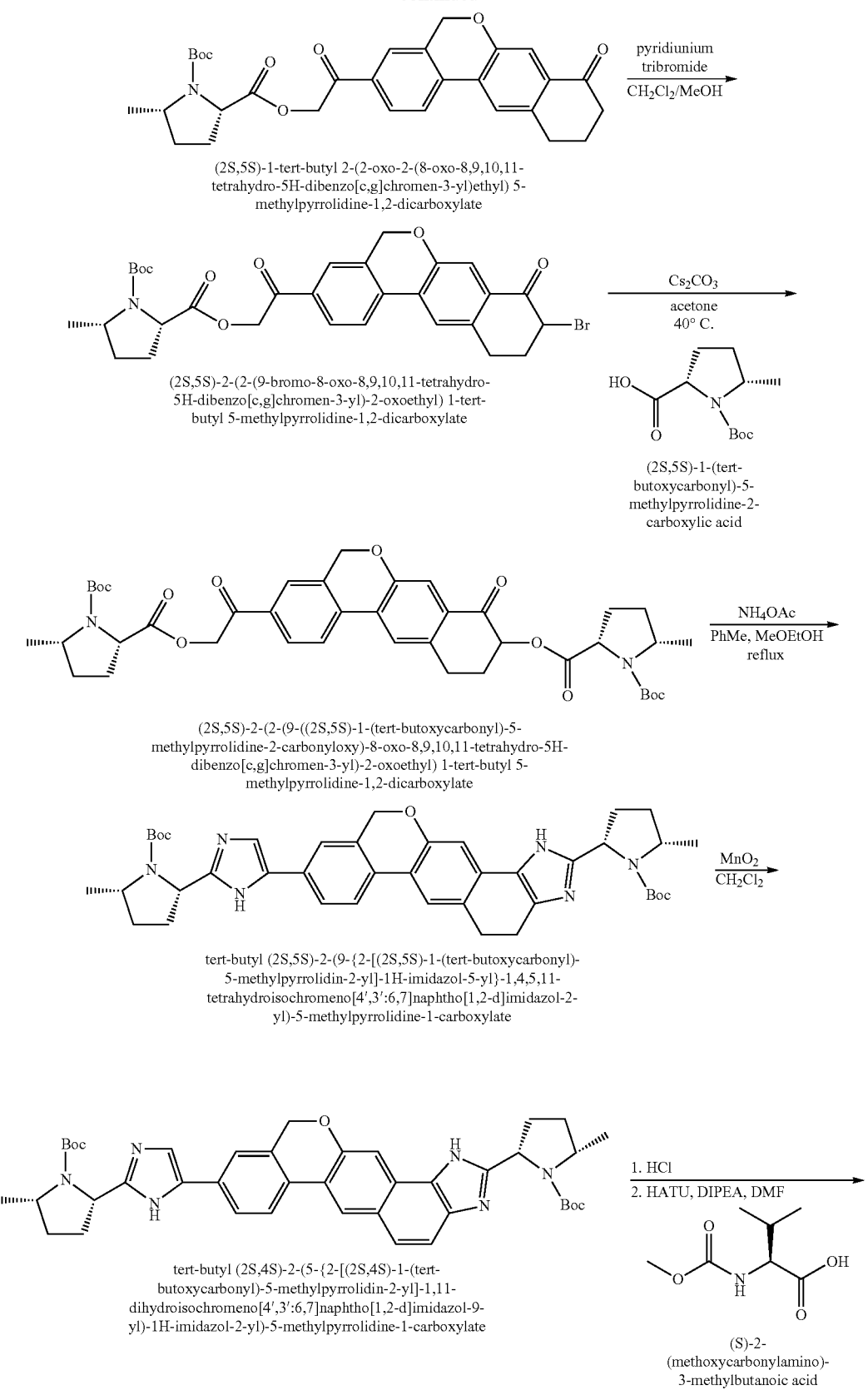

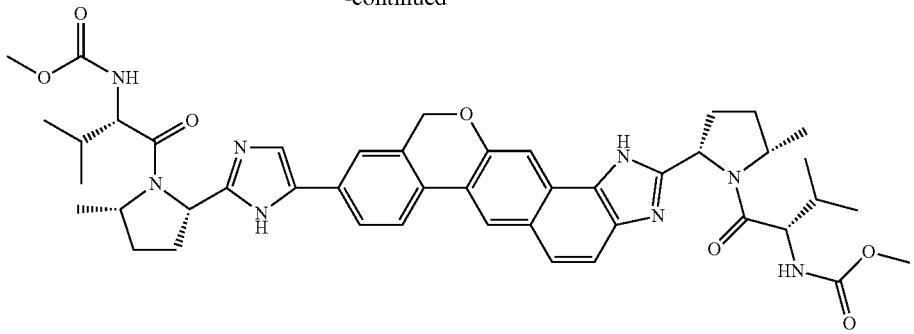

methyl {(2S)-1-[(2S,5S)-2-(5-{2-[(2S,4S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (2S,5S)-1-tert-butyl 2-(2-oxo-2-(8-oxo-8,9,10,11-tetrahydro-5H-dibenzo[c,g]chromen-3-yl)ethyl) 5-methylpyrrolidine-1,2-dicarboxylate: To a solution of 3-(2-bromoacetyl)-10,11-dihydro-5H-dibenzo[c,g]chromen-8(9H)-one in MeCN (30 mL) was added (2S,5S)-1-(tert-butoxycarbonyl)-5-methylpyrrolidine-2-carboxylic acid (1.2 g, 3.23 mmol) and triethyl amine (0.48 mL, 3.55 mmol) and the solution was heated to 50° C. After stirring for 15 h, the solution was cooled to rt, and diluted with EtOAc and washed successively with saturated aqueous NaHCO₃ and brine. The organics were dried over MgSO₄, filtered and concentrated under reduced pressure. The crude residue was purified by silica column chromatography (20% to 50% EtOAc/hexanes) to afford (2S,5S)-1-tert-butyl 2-(2-oxo-2-(8-oxo-8,9,10,11-tetrahydro-5H-dibenzo[c,g]chromen-3-yl)ethyl) 5-methylpyrrolidine-1,2-dicarboxylate (1.09 g, 65%).

(2S,5S)-2-(2-(9-bromo-8-oxo-8,9,10,11-tetrahydro-5H-dibenzo[c,g]chromen-3-yl)-2-oxoethyl) 1-tert-butyl 5-methylpyrrolidine-1,2-dicarboxylate: (2S,5S)-1-tert-butyl 2-(2-oxo-2-(8-oxo-8,9,10,11-tetrahydro-5H-dibenzo[c,g]chromen-3-yl)ethyl) 5-methylpyrrolidine-1,2-dicarboxylate (1.29 g, 2.48 mmol) was dissolved in a solution of DCM (17.5 mL) and MeOH (7 mL), then treated with pyridinium tribromide (873 mg, 2.73 mmol). After stirring at RT for 1 h, the reaction mixture was diluted with DCM and 10% HCl, and extracted with DCM. The organic phase was dried over MgSO₄, filtered and concentrated under reduced pressure and the crude material was carried on without further purification.

(2S,5S)-2-(2-(9-((2S,5S)-1-(tert-butoxycarbonyl)-5-methylpyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate: (2S,5S)-2-(2-(9-bromo-8-oxo-8,9,10,11-tetrahydro-5H-dibenzo[c,g]chromen-3-yl)-2-oxoethyl) 1-tert-butyl 5-methylpyrrolidine-1,2-dicarboxylate (700 mg, 1.17 mmol) was treated with a solution of (2S,5S)-1-(tert-butoxycarbonyl)-5-methylpyrrolidine-2-carboxylic acid (375 mg, 1.64 mmol) in acetone (6 mL) and Cs₂CO₃ (267 mg, 0.82 mmol). The stirred reaction mixture was heated to 40° C. for 16 h, then cooled to RT and diluted with CH₂Cl₂ and extracted 3×. The organic phase was washed with brine, then dried over MgSO₄, filtered and concentrated under reduced pressure. The crude residue was purified by silica column chromatography (40% to 100% EtOAc/hexanes) to afford (2S,5S)-2-(2-(9-((2S,5S)-1-(tert-butoxycarbonyl)-5-methylpyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate (464 mg, 53%).

Tert-butyl (2S,5S)-2-(9-{2-[(2S,5S)-1-(tert-butoxycarbonyl)-5-methylpyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate: (2S,5S)-2-(2-(9-((2S,5S)-1-(tert-butoxycarbonyl)-5-methylpyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate (464 mg, 0.62 mmol) and NH₄OAc (8.48 g, 110.0 mmol) were suspended in a solution of 10:1 PhMe/2-methoxyethanol (22 mL). The stirred reaction mixture was heated to 110° C. for 20 h, then cooled to RT and diluted with EtOAc. The organic phase was washed with water, saturated aqueous NaHCO₃, and brine, then dried over MgSO₄, filtered and concentrated under reduced pressure. The crude residue was purified by silica column chromatography (0% to 30% MeOH/EtOAc) to afford tert-butyl (2S,5S)-2-(9-{2-[(2S,5S)-1-(tert-butoxycarbonyl)-5-methylpyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate (393 mg, 90%).

Tert-butyl (2S,4S)-2-(5-{2-[(2S,4S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate: Tert-butyl (2S,5S)-2-(9-{2-[(2S,5S)-1-(tert-butoxycarbonyl)-5-methylpyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate (393 mg, 0.55 mmol) was suspended in DCM (7 mL) and activated MnO₂ (1.45 g, 16.7 mmol) was added in a single portion. The reaction mixture was heated to 40° C. After stirring for 2.5 h, the mixture was cooled to rt and the slurry was filtered over celite. The filter cake was washed with copious CH₂Cl₂ and MeOH and the filtrate was concentrated under reduced pressure. The crude material was taken on to the next step without further purification to afford tert-butyl (2S,4S)-2-(5-{2-[(2S,4S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate (328 g, 85%).

Methyl {(2S)-1-[(2S,5S)-2-(5-{2-[(2S,4S)-1-{(2S)-2-[(methoxycarbonyl)amino]-3-methylbutanoyl}-5-methylpyrrolidin-2-yl]-1,11-dihydroisochromeno[4',3':6,7]naphtho

[1,2-d]imidazol-9-yl}-1H-imidazol-2-yl)-5-methylpyrrolidin-1-yl]-3-methyl-1-oxobutan-2-yl}carbamate: Tert-butyl (2S,4S)-2-(5-{2-[(2S,4S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate (164 mg, 0.23 mmol) was dissolved in DCM (7 mL), MeOH (1.5 mL) and HCl (4 M in dioxane, 1.5 mL) was added. The reaction mixture was stirred for 16 h and then concentrated under reduced pressure. The crude residue was treated with (S)-2-(methoxycarbonylamino)-3-methylbutanoic acid (81 mg, 0.46 mmol), HATU (175 mg, 0.46 mmol) and DMF (5 mL), then DIPEA (0.4 mL, 2.34 mmol) was added dropwise. After 35 min, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl {(2S)-1-[(2S,5S)-2-(5-{2-[(2S,4S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (132 mg, 69%). LCMS-ESI$^+$: calculated for C$_{45}$H$_{54}$N$_8$O$_7$: 818.41; observed [M+1]$^+$: 820.19. $^1$H NMR (CD$_3$OD): 8.492 (m, 1H), 8.179-7.538 (m, 7H), 5.267-5.201 (m, 3H), 5.125-5.082 (m, 1H), 4.070 (m, 1H), 3.383-3.592 (m, 4H), 3.225 (s, 3H), 2.466-2.249 (m, 5H), 1.992-1.892 (m, 3H), 1.568 (d, 3H, J=6.4 Hz), 1.490 (d, 3H, J=6.8 Hz), 1.266 (m, 2H), 1.020-0.806 (m, 14H).

Example NH

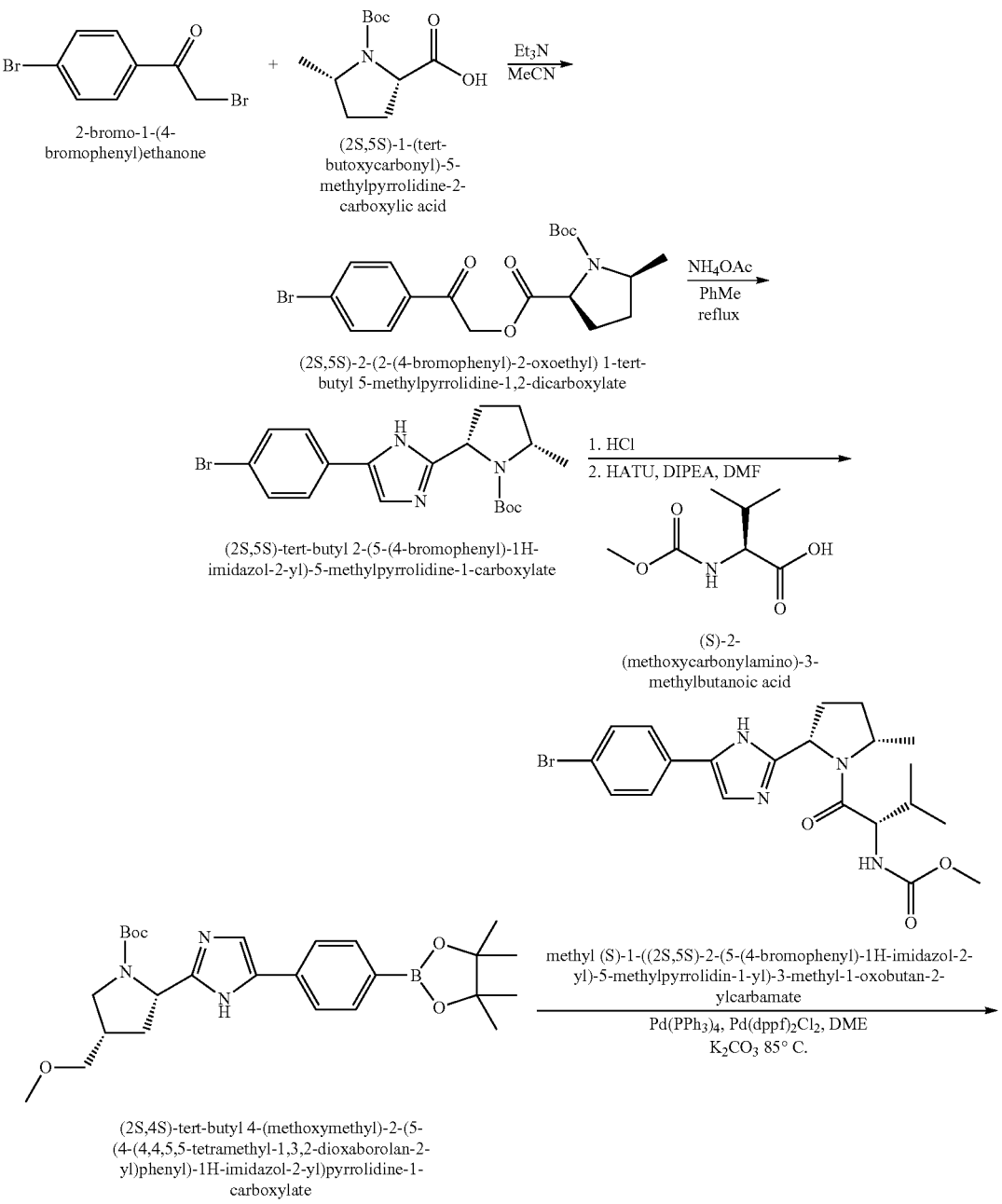

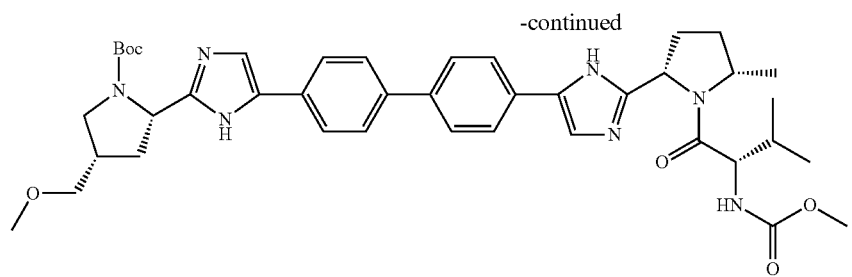
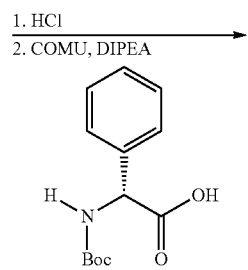

(2S,4S)-tert-butyl 2-(5-(4'-(2-((2S,5S)-1-((S)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidine-1-carboxylate (R)-2-tert-butoxycarbonylamino)-2-phenylacetic acid

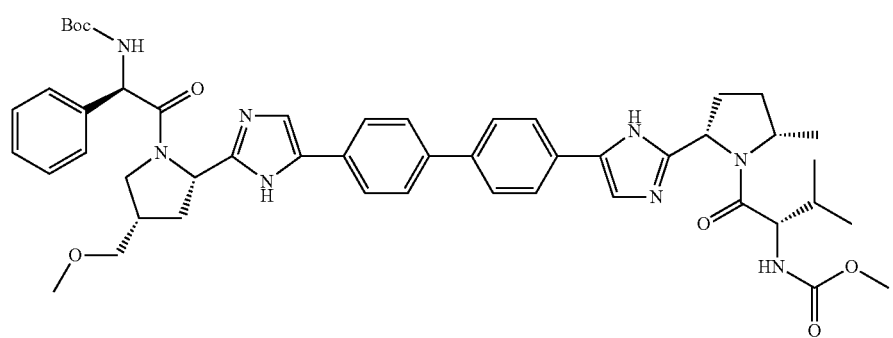
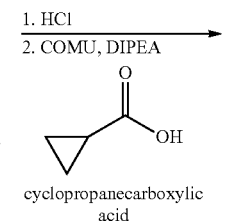

tert-butyl (R)-2-((2S-4S)-2-(5-(4'-(2-((2S,5S)-1-((S)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-2-oxo-1-phenylethylcarbamate cyclopropanecarboxylic acid

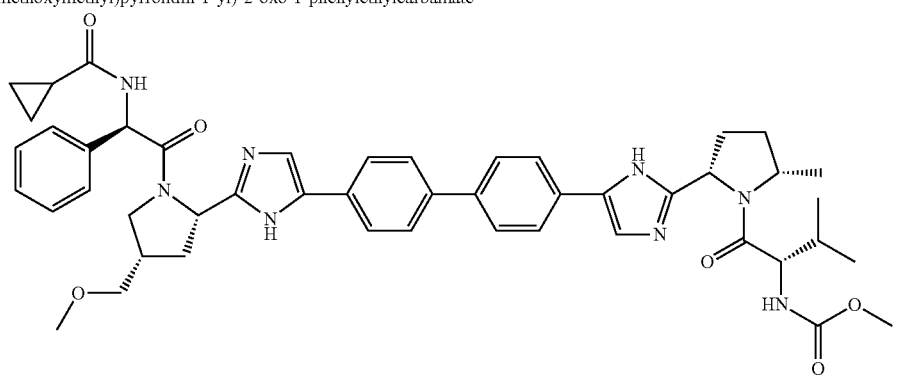

methyl (S)-1-((2S,5S)-2-(5-(4'-(2-((2S,4S)-1-((R)-2-(cyclopropanecarboxamido)-2-phenylacetyl)-4-(methoxymethyl)pyrrolidin-2-yl)-1H-imidazol-5-yl)biphenyl-4-yl)-1H-imidazol-2-yl)-5-methylpyrrolidin-1-yl)-3-methyl-1-oxobutan-2-ylcarbamate (2S,5S)-2-(2-(4-bromophenyl)-2-oxoethyl) 1-tert-butyl 5-methylpyrrolidine-1,2-dicarboxylate: To a solution of 2-bromo-1-(4-bromophenyl)ethanone (505 mg, 1.82 mmol) in MeCN (18 mL) was added (2S,5S)-1-(tert-butoxycarbonyl)-5-methylpyrrolidine-2-carboxylic acid (500 mg, 2.18 mmol) and triethyl amine (0.27 mL, 2.0 mmol). After stirring for 15 h, the solution was diluted with EtOAc and washed successively with saturated aqueous NaHCO$_3$ and brine. The organics were dried over MgSO$_4$, filtered and concentrated under reduced pressure. The crude residue was purified by silica column chromatography (10% to 40% EtOAc/hexanes) to afford (2S,5S)-2-(2-(4-bromophenyl)-2-oxoethyl) 1-tert-butyl 5-methylpyrrolidine-1,2-dicarboxylate (640 mg, 82%).

(2S,5S)-tert-butyl 2-(5-(4-bromophenyl)-1H-imidazol-2-yl)-5-methylpyrrolidine-1-carboxylate: (2S,5S)-2-(2-(4-bromophenyl)-2-oxoethyl) 1-tert-butyl 5-methylpyrrolidine-1,2-dicarboxylate (640 mg, 1.5 mmol) was added PhMe (12 mL), MeOEtOH (3 mL) and ammonium acetate (2.3 g, 30 mmol) and the solution was heated to 110° C. After stirring for 2 h, the solution was cooled to rt and was diluted with EtOAc and washed successively with water, saturated aqueous NaHCO$_3$ and brine. The organics were dried over MgSO$_4$, filtered and concentrated under reduced pressure.

The crude residue was purified by silica column chromatography (100% EtOAc) to afford (2S,5S)-tert-butyl 2-(5-(4-bromophenyl)-1H-imidazol-2-yl)-5-methylpyrrolidine-1-carboxylate (562 mg, 92%).

Methyl (S)-1-((2S,5S)-2-(5-(4-bromophenyl)-1H-imidazol-2-yl)-5-methylpyrrolidin-1-yl)-3-methyl-1-oxobutan-2-ylcarbamate: (2S,5S)-tert-butyl 2-(5-(4-bromophenyl)-1H-imidazol-2-yl)-5-methylpyrrolidine-1-carboxylate (562 mg, 1.38 mmol) was dissolved in DCM (8 mL), MeOH (2 mL) and HCl (4 M in dioxane, 2 mL) was added. The reaction mixture was stirred for 4 h and then concentrated under reduced pressure. The crude residue was treated with (S)-2-(methoxycarbonylamino)-3-methylbutanoic acid (241 mg, 1.38 mmol), HATU (525 mg, 1.38 mmol) and DMF (14 mL), then DIPEA (1.2 mL, 6.9 mmol) was added dropwise. After 30 min, the mixture was diluted with EtOAc and washed successively with saturated aqueous NaHCO₃ and brine. The organics were dried over MgSO₄, filtered and concentrated under reduced pressure. The crude residue was purified by silica column chromatography (0% to 10% MeOH/EtOAc) to afford methyl (S)-1-((2S,5S)-2-(5-(4-bromophenyl)-1H-imidazol-2-yl)-5-methylpyrrolidin-1-yl)-3-methyl-1-oxobutan-2-ylcarbamate (503 mg, 79%).

(2S,4S)-tert-butyl 2-(5-(4'-(2-((2S,5S)-1-((S)-2-(methoxycarbonylamino)-3-m ethylbutanoyl)-5-methylpyrrolidin-2-yl)-1H-imidazol-5-yl)biphenyl-4-yl)-1H-imidazol-2-yl)-4-(methoxymethyl)pyrrolidine-1-carboxylate: (2S,4S)-tert-butyl 4-(methoxymethyl)-2-(5-(4-(4,4,5,5-tetramethyl-1,3,2-dioxaborolan-2-yl)phenyl)-1H-imidazol-2-yl)pyrrolidine-1-carboxylate (461 mg, 095 mmol), methyl (S)-1-((2S,5S)-2-(5-(4-bromophenyl)-1H-imidazol-2-yl)-5-methylpyrrolidin-1-yl)-3-methyl-1-oxobutan-2-ylcarbamate (503 mg, 1.08 mmol) Pd(PPh₃)₄ (110 mg, 0.095 mmol), PdCl₂(dppf)₂ (70 mg, 0.095 mmol), and K₂CO₃ (2M in H₂O, 1.56 mL, 3.1 mmoL) were combined in DME (10 mL). The mixture was degassed with bubbling N₂ for 10 min the heated to 85° C. for 16 h. After cooling, the reaction mixture was diluted with EtOAc, and washed successively with saturated aqueous NaHCO₃ and brine. The organics were dried over MgSO₄, filtered and concentrated under reduced pressure. The crude residue was purified by silica column chromatography (0% to 30% MeOH/EtOAc) to afford (2S,4S)-tert-butyl 2-(5-(4'-(2-((2S,5S)-1-((S)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidine-1-carboxylatecarboxylate (289 mg, 41%).

Tert-butyl (R)-2-((2S,4S)-2-(5-(4'-(2-((2S,5S)-1-((S)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-2-oxo-1-phenylethylcarbamate: (2S,4S)-tert-butyl 2-(5-(4'-(2-((2S,5S)-1-((S)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidine-1-carboxylate (289 mg, 0.39 mmol) was dissolved in DCM (4 mL), MeOH (1 mL) and HCl (4 M in dioxane, 1 mL) was added. The reaction mixture was stirred for 2 h and then concentrated under reduced pressure. The crude residue was treated with (R)-2-(tert-butoxycarbonylamino)-2-phenylacetic acid (98 mg, 0.39 mmol), COMU (186 mg, 0.39 mmol) and DMF (5 mL), then DIPEA (0.34 mL, 1.96 mmol) was added dropwise. After 30 min, the mixture was diluted with EtOAc and washed successively with saturated aqueous NaHCO₃ and brine. The organics were dried over MgSO₄, filtered and concentrated under reduced pressure. The crude residue was purified by silica column chromatography (0% to 30% MeOH/EtOAc) to afford tert-butyl (R)-2-((2S,4S)-2-(5-(4'-(2-((2S,5S)-1-((S)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-2-oxo-1-phenylethylcarbamate (201 mg, 59%).

Methyl (S)-1-((2S,5S)-2-(5-(4'-(2-((2S,4S)-1-((R)-2-(cyclopropanecarboxamido)-2-phenylacetyl)-4-(methoxymethyl)pyrrolidin-2-yl)-1H-imidazol-5-yl)biphenyl-4-yl)-1H-imidazol-2-yl)-5-methylpyrrolidin-1-yl)-3-methyl-1-oxobutan-2-ylcarbamate: Tert-butyl (R)-2-((2S,4S)-2-(5-(4'-(2-((2S5S)-1-((S)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-2-oxo-1-phenylethylcarbamate (201 mg, 0.23 mmol) was dissolved in DCM (4 mL), MeOH (1 mL) and HCl (4 M in dioxane, 1 mL) was added. The reaction mixture was stirred for 4 h and then concentrated under reduced pressure. The crude residue was treated with cyclopropanecarboxylic acid (18 µL, 0.23 mmol), COMU (110 mg, 0.23 mmol) and DMF (5 mL), then DIPEA (0.20 mL, 1.15 mmol) was added dropwise. After 30 min, the mixture was diluted with 10% MeOH/EtOAc and washed successively with saturated aqueous NaHCO₃ and brine. The organics were dried over MgSO₄, filtered and concentrated under reduced pressure. The crude residue was purified by HPLC to afford methyl (S)-1-((2S,5S)-2-(5-(4'-(2-((2S,4S)-1-((R)-2-(cyclopropanecarboxamido)-2-phenylacetyl)-4-(methoxymethyl)pyrrolidin-2-yl)-1H-imidazol-5-yl)biphenyl-4-yl)-1H-imidazol-2-yl)-5-methylpyrrolidin-1-yl)-3-methyl-1-oxobutan-2-ylcarbamate (25 mg, 13%). LCMS-ESI⁺: calculated for C48H56N8O6: 840.43; observed [M+1]⁺: 842.39.

Example NI

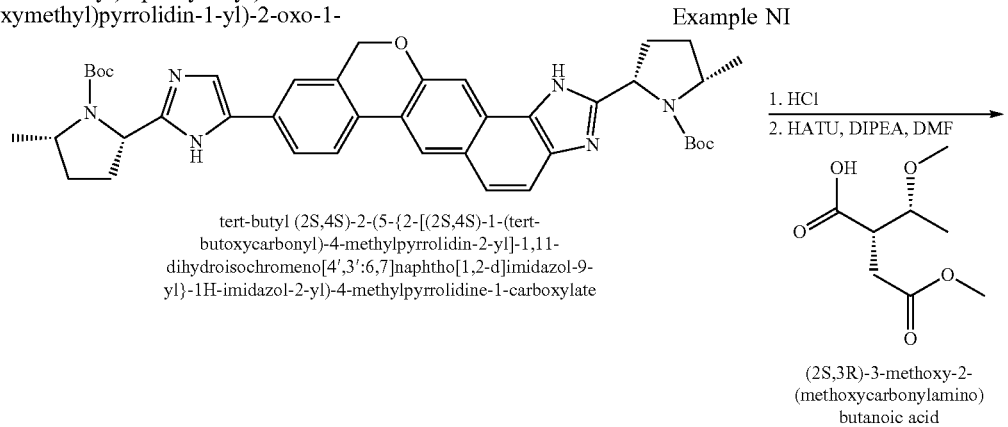

tert-butyl (2S,4S)-2-(5-{2-[(2S,4S)-1-(tert-butoxycarbonyl)-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-carboxylate (2S,3R)-3-methoxy-2-(methoxycarbonylamino) butanoic acid

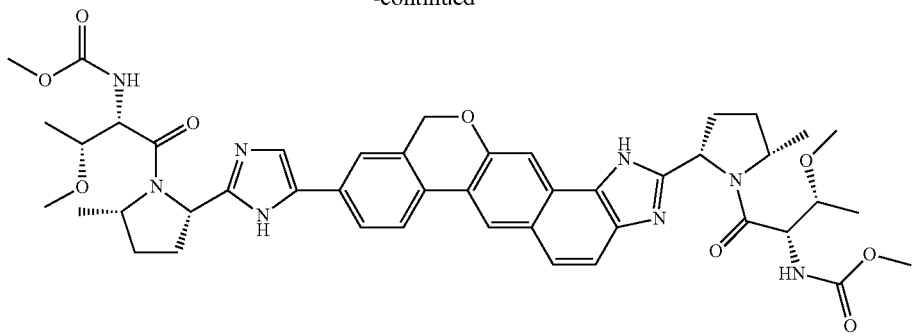

methyl [(2S,3R)-3-methoxy-1-{(2S,5S)-2-[9-(2-{(2S,5S)-1-[N-(methoxycarbonyl-O-methyl-L-threonyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-1-oxobutan-2-yl]carbamate Methyl [(2S,3R)-3-methoxy-1-{(2S,5S)-2-[9-(2-{(2S,5S)-1-[N-(methoxycarbonyl)-O-methyl-L-threonyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-1-oxobutan-2-yl]carbamate: Tert-butyl (2S,4S)-2-(5-{2-[(2S,4S)-1-(tert-butoxycarbonyl)-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-carboxylate (164 mg, 0.23 mmol) was dissolved in DCM (7 mL), MeOH (1.5 mL) and HCl (4 M in dioxane, 1.5 mL) was added. The reaction mixture was stirred for 16 h and then concentrated under reduced pressure. The crude residue was treated with (2S,3R)-3-methoxy-2-(methoxycarbonylamino)butanoic acid (90 mg, 0.46 mmol), HATU (175 mg, 0.46 mmol) and DMF (6 mL), then DIPEA (0.4 mL, 2.34 mmol) was added dropwise. After 30 min, the mixture was diluted with 10% MeOH/EtOAc and washed successively with saturated aqueous NaHCO₃ and brine. The organics were dried over MgSO₄, filtered and concentrated under reduced pressure. The crude residue was purified by HPLC to afford methyl [(2S,3R)-3-methoxy-1-{(2S,5S)-2-[9-(2-{(2S,5S)-1-[N-(methoxycarbonyl)-O-methyl-L-threonyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-1-oxobutan-2-yl]carbamate (97 mg, 50%). LCMS-ESI⁺: calculated for C45H54N8O9: 850.40; observed [M+1]⁺: 851.58. ¹H NMR (CD₃OD): 8.631 (s, 1H), 8.191-7.938 (m, 7 H), 6.100 (m, 1H), 5.925 (m, 1H), 5.303 (m, 3H), 5.179 (t, 1H, J=6.8 Hz), 4.406-4.358 (m, 2H), 3.754-3.598 (m, 8H), 3.376 (s, 3H), 3.263 (s, 3H), 2.625-2.256 (m, 6H), 2.038-1.955 (m, 2H), 1.598 (d, 3H, J=6.4 Hz), 1.530 (d, 3H, J=6.8 Hz), 1.302-1.099 (m, 6H).

Example NJ

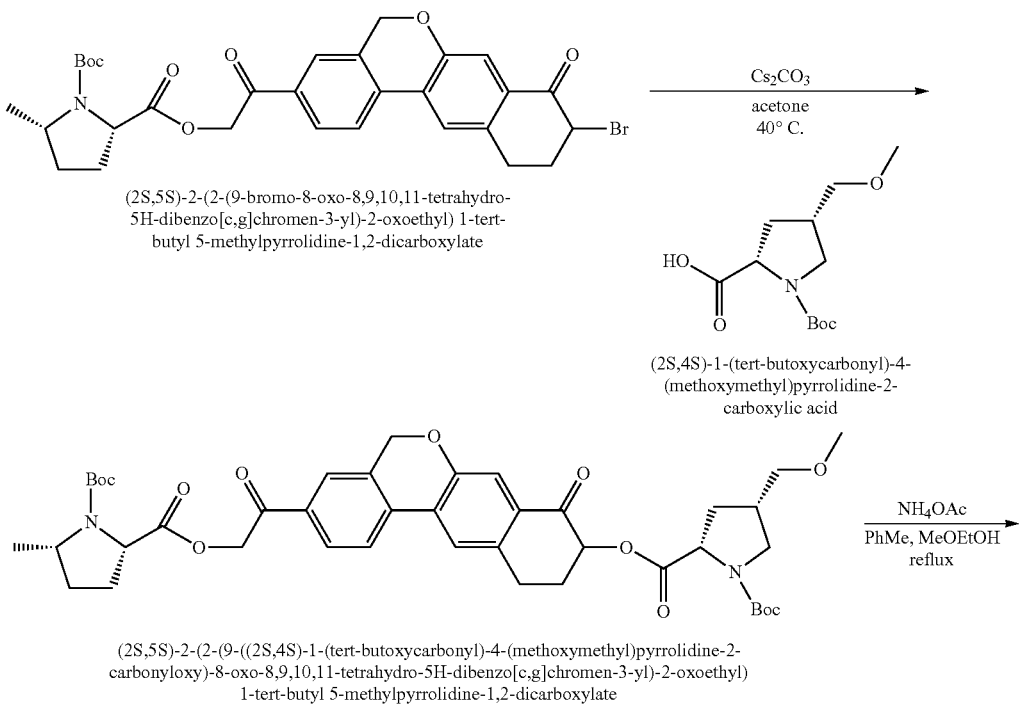

(2S,5S)-2-(2-(9-bromo-8-oxo-8,9,10,11-tetrahydro-5H-dibenzo[c,g]chromen-3-yl)-2-oxoethyl) 1-tert-butyl 5-methylpyrrolidine-1,2-dicarboxylate (2S,4S)-1-(tert-butoxycarbonyl)-4-(methoxymethyl)pyrrolidine-2-carboxylic acid (2S,5S)-2-(2-(9-((2S,4S)-1-(tert-butoxycarbonyl)-4-(methoxymethyl)pyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate -continued

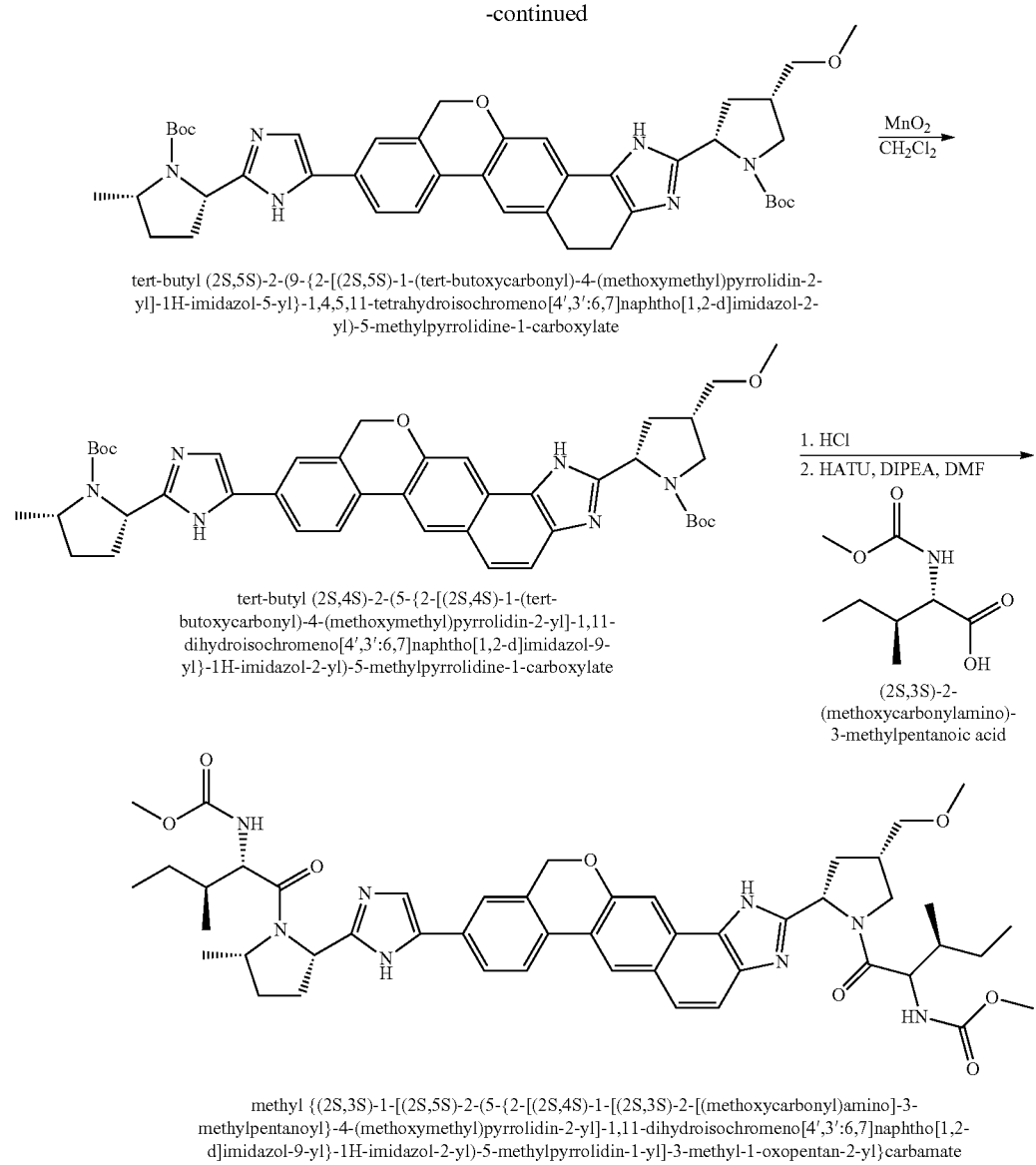

tert-butyl (2S,5S)-2-(9-{2-[(2S,5S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate tert-butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate (2S,3S)-2-(methoxycarbonylamino)-3-methylpentanoic acid methyl {(2S,3S)-1-[(2S,5S)-2-(5-{2-[(2S,4S)-1-[(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate (2S,5S)-2-(2-(9-((2S,4S)-1-(tert-butoxycarbonyl)-4-(methoxymethyl) pyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate: (2S,5S)-2-(2-(9-bromo-8-oxo-8,9,10,11-tetrahydro-5H-dibenzo[c,g]chromen-3-yl)-2-oxoethyl) 1-tert-butyl 5-methylpyrrolidine-1,2-dicarboxylate (800 mg, 1.34 mmol) was treated with a solution of (2S,4S)-1-(tert-butoxycarbonyl)-4-(methoxymethyl)pyrrolidine-2-carboxylic acid (485 mg, 1.87 mmol) in acetone (6 mL) and $Cs_2CO_3$ (306 mg, 0.94 mmol). The stirred reaction mixture was heated to 40° C. for 16 h, then cooled to RT and diluted with $CH_2Cl_2$ and extracted 3×. The organic phase was washed with brine, then dried over $MgSO_4$, filtered and concentrated under reduced pressure. The crude residue was purified by silica column chromatography (40% to 100% EtOAc/hexanes) to afford (2S,5S)-2-(2-(9-((2S,5S)-1-(tert-butoxycarbonyl)-5-methyl-pyrrolidine-2-carbonyloxy)-R-oxo-8,9,10,11-tetrahydro-5H-dibenzo[c,g]chromen-3-yl)-2-oxoethyl) 1-tert-butyl 5-methylpyrrolidine-1,2-dicarboxylate (680 mg, 65%).

Tert-butyl (2S,5S)-2-(9-{2-[(2S,5S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate: (2S,5S)-2-(2-(9-((2S,5S)-1-(tert-butoxycarbonyl)-5-methylpyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate (680 mg, 0.87 mmol) and $NH_4OAc$ (10.0 g, 130.0 mmol) were suspended in a solution of 10:1 PhMe/2-methoxyethanol (22 mL). The stirred reaction mixture was heated to 110° C. for 24 h, then cooled to RT and diluted with EtOAc. The organic phase was washed with water, saturated aqueous $NaHCO_3$, and brine, then dried over $MgSO_4$, filtered and concentrated under reduced pressure. The crude residue was purified by silica column chromatography (0% to 30% MeOH/EtOAc) to afford tert-butyl (2S,5S)-2-(9-{2-[(2S,5S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate (461 mg, 72%).

Tert-butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate: Tert-butyl (2S,5S)-2-(9-{2-[(2S,5S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate (461 mg, 0.62 mmol) was suspended in DCM (7 mL) and activated MnO$_2$ (1.6 g, 18.8 mmol) was added in a single portion. The reaction mixture was heated to 40° C. After stirring for 5.5 h, the mixture was cooled to rt and the slurry was filtered over celite. The filter cake was washed with copious CH$_2$Cl$_2$ and MeOH and the filtrate was concentrated under reduced pressure. The crude material was taken on to the next step without further purification to afford tert-butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate (414 g, 90%).

Methyl {(2S,3S)-1-[(2S,5S)-2-(5-{2-[(2S,4S)-1-{(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate: Tert-butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate (207 mg, 0.28 mmol) was dissolved in DCM (4 mL), MeOH (1 mL) and HCl (4 M in dioxane, 1 mL) was added. The reaction mixture was stirred for 1.5 h and then concentrated under reduced pressure. The crude residue was treated with (2S,3S)-2-(methoxycarbonylamino)-3-methylpentanoic acid (106 mg, 0.56 mmol), HATU (214 mg, 0.56 mmol) and DMF (5 mL), then DIPEA (0.49 mL, 2.8 mmol) was added dropwise. After 30 min, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl {(2S,3S)-1-[(2S,5S)-2-(5-{2-[(2S,4S)-1-{(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate (132 mg, 69%). LCMS-ESI$^+$: calculated for C$_{45}$H$_{54}$N$_8$O$_7$: 876.45; observed [M+1]$^+$: 879.02.

Example NK

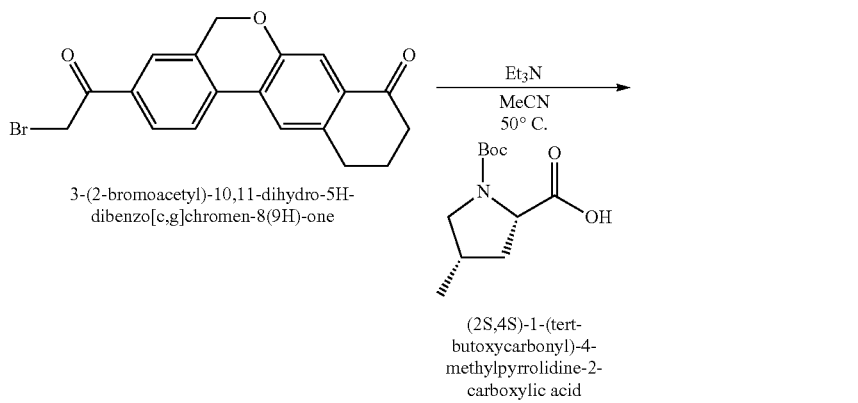

3-(2-bromoacetyl)-10,11-dihydro-5H-dibenzo[c,g]chromen-8(9H)-one (2S,4S)-1-(tert-butoxycarbonyl)-4-methylpyrrolidine-2-carboxylic acid

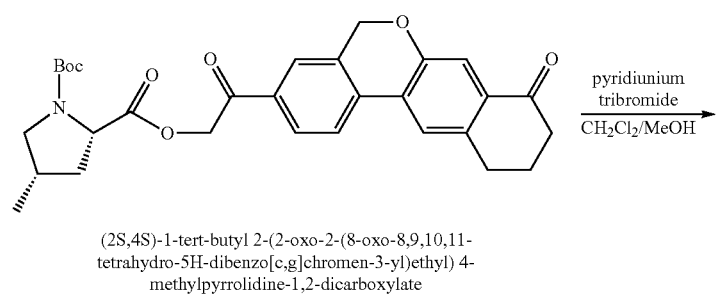

(2S,4S)-1-tert-butyl 2-(2-oxo-2-(8-oxo-8,9,10,11-tetrahydro-5H-dibenzo[c,g]chromen-3-yl)ethyl) 4-methylpyrrolidine-1,2-dicarboxylate -continued
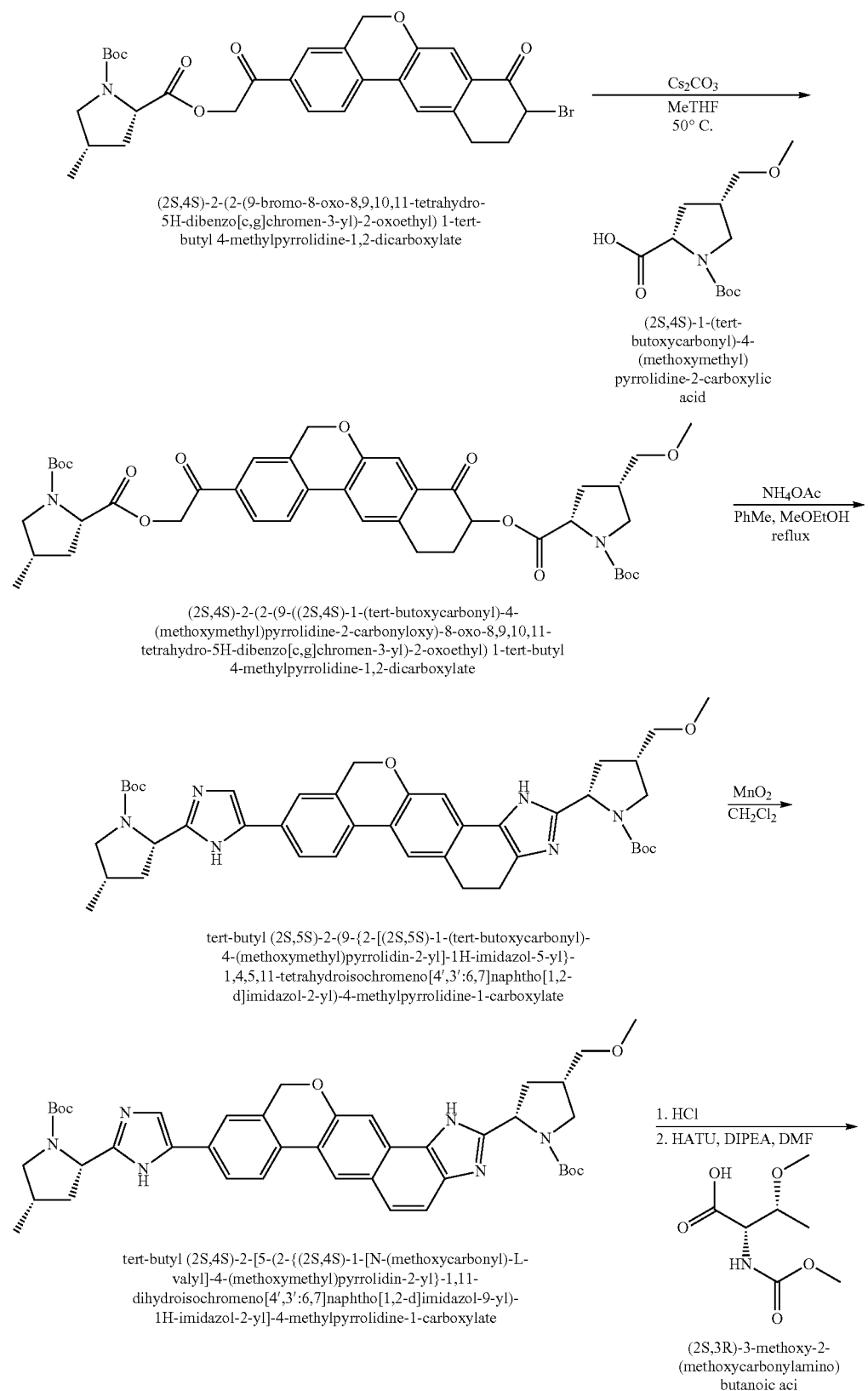

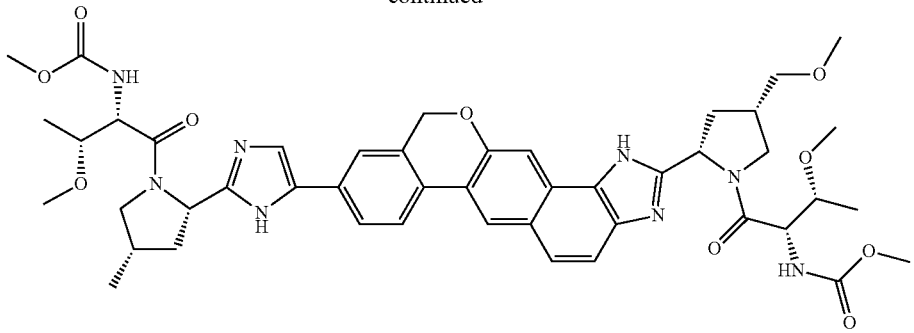

methyl {(2S,3R)-3-methoxy-1-[(2S,4S)-2-[9-(2-{(2S,4S)-1-[N-(methoxycarbonyl)-O-methyl-L-threonyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidin-1-yl]-1-oxobutan-2-yl}carbamate (2S,4S)-1-tert-butyl 2-(2-oxo-2-(8-oxo-8,9,10,11-tetrahydro-5H-dibenzo[c,g]chromen-3-yl)ethyl) 4-methylpyrrolidine-1,2-dicarboxylate: To a solution of 3-(2-bromoacetyl)-10,11-dihydro-5H-dibenzo[c,g]chromen-8(9H)-one (647 mg, 1.74 mmol) in MeCN (20 mL) was added ((2S, 4S)-1-(tert-butoxycarbonyl)-4-methylpyrrolidine-2-carboxylic acid (559 mg, 2.44 mmol) and DIPEA (0.36 mL, 2.09 mmol) and the solution was heated to 60° C. After stirring for 3 h, the solution was cooled to rt, and diluted with EtOAc and washed successively with saturated aqueous NaHCO3 and brine. The organics were dried over MgSO$_4$, filtered and concentrated under reduced pressure. The crude residue was purified by silica column chromatography (20% to 50% EtOAc/hexanes) to afford (2S,4S)-1-tert-butyl 2-(2-oxo-2-(8-oxo-8,9,10,11-tetrahydro-5H-dibenzo[c,g]chromen-3-yl)ethyl) 4-methylpyrrolidine-1,2-dicarboxylate (621 mg, 69%).

(2S,4S)-2-(2-(9-bromo-8-oxo-8,9,10,11-tetrahydro-5H-dibenzo[c,g]chromen-3-yl)-2-oxoethyl) 1-tert-butyl 4-methylpyrrolidine-1,2-dicarboxylate: (2S,4S)-1-tert-butyl 2-(2-oxo-2-(8-oxo-8,9,10,11-tetrahydro-5H-dibenzo[c,g]chromen-3-yl)ethyl) 4-methylpyrrolidine-1,2-dicarboxylate (621 mg, 1.19 mmol) was dissolved in a solution of DCM (10 mL) and MeOH (4 mL), then treated with pyridinium tribromide (421 mg, 1.3 mmol). After stirring at RT for 1.5 h, the reaction mixture was diluted with DCM and 10% HCl, and extracted with DCM. The organic phase was dried over MgSO$_4$, filtered and concentrated under reduced pressure and the crude material was carried on without further purification.

(2S,4S)-2-(2-(9-((2S,4S)-1-(tert-butoxycarbonyl)-4-(methoxymethyl)pyrrolidine-2-carbonyloxy)-8-oxo-8,9,10,11-tetrahydro-5H-dibenzo[c,g]chromen-3-yl)-2-oxoethyl) 1-tert-butyl 4-methylpyrrolidine-1,2-dicarboxylate: (2S,4S)-2-(2-(9-bromo-8-oxo-8,9,10,11-tetrahydro-5H-dibenzo[c,g]chromen-3-yl)-2-oxoethyl) 1-tert-butyl 4-methylpyrrolidine-1,2-dicarboxylate (709 mg, 1.18 mmol) was treated with a solution of (2S,4S)-1-(tert-butoxycarbonyl)-4-(methoxymethyl)pyrrolidine-2-carboxylic acid (614 mg, 2.36 mmol) in Me-THF (12 mL) and Cs$_2$CO$_3$ (384 mg, 1.18 mmol). The stirred reaction mixture was heated to 50° C. for 16 h, then cooled to RT and diluted with CH$_2$Cl$_2$ and extracted 3×. The organic phase was washed with brine, then dried over MgSO$_4$, filtered and concentrated under reduced pressure. The crude residue was purified by silica column chromatography (40% to 100% EtOAc/hexanes) to afford (2S,4S)-2-(2-(9-((2S,4S)-1-(tert-butoxycarbonyl)-4-(methoxymethyl)pyrrolidine-2-carbonyloxy)-8-oxo-8,9,10,11-tetrahydro-5H-dibenzo[c,g]chromen-3-yl)-2-oxoethyl) 1-tert-butyl 4-methylpyrrolidine-1,2-dicarboxylate (651 mg, 71%).

Tert-butyl (2S,5S)-2-(9-{2-[(2S,5S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-4-methylpyrrolidine-1-carboxylate: (2S,4S)-2-(2-(9-((2S,4S)-1-(tert-butoxycarbonyl)-4-(methoxymethyl)pyrrolidine-2-carbonyloxy)-8-oxo-8,9,10,11-tetrahydro-5H-dibenzo[c,g]chromen-3-yl)-2-oxoethyl) 1-tert-butyl 4-methylpyrrolidine-1,2-dicarboxylate (651 mg, 0.84 mmol) and NH$_4$OAc (10.0 g, 129.7 mmol) were suspended in a solution of 10:1 PhMe/2-methoxyethanol (22 mL). The stirred reaction mixture was heated to 110° C. for 20 h, then cooled to RT and diluted with EtOAc. The organic phase was washed with water, saturated aqueous NaHCO$_3$, and brine, then dried over MgSO$_4$, filtered and concentrated under reduced pressure. The crude residue was purified by silica column chromatography (0% to 30% MeOH/EtOAc) to afford tert-butyl (2S,5S)-2-(9-{2-[(2S,5S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-4-methylpyrrolidine-1-carboxylate (382 mg, 62%).

Tert-butyl (2S,4S)-2-[5-(2-{(2S,4S)-1-[N-(methoxycarbonyl)-L-valyl]-4-(methoxymethyl)pyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate: Tert-butyl (2S,5S)-2-(9-{2-[(2S,5S)-1-(tert-butoxycarbonyl)-4-(methoxymethyl)pyrrolidin-2-yl]-1H-imidazol-5-yl}-1,4,5,11-tetrahydroisochromeno[4',3': 6,7]naphtho[1,2-d]imidazol-2-yl)-4-methylpyrrolidine-1-carboxylate (382 mg, 0.52 mmol) was suspended in DCM (8 mL) and activated MnO$_2$ (1.35 g, 15.5 mmol) was added in a single portion. The reaction mixture was heated to 35° C. After stirring for 15 h, the mixture was cooled to rt and the slurry was filtered over celite. The filter cake was washed with copious CH$_2$Cl$_2$ and MeOH and the filtrate was concentrated under reduced pressure. The crude material was taken on to the next step without further purification to afford tert-butyl (2S,4S)-2-[5-(2-{(2S,4S)-1-[N-(methoxycarbonyl)-L-valyl]-4-(methoxymethyl)pyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (347 g, 91%).

Methyl {(2S,3R)-3-methoxy-1-[(2S,4S)-2-[9-(2-{(2S,4S)-1-[N-(methoxycarbonyl)-O-methyl-L-threonyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidin-1-yl]-1-oxobutan-2-yl}carbamate: Tert-butyl (2S,4S)-2-[5-(2-{(2S,4S)-1-[N-(methoxycarbonyl)-L-valyl]-4-(methoxymethyl)pyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (174 mg, 0.24 mmol) was dissolved in DCM (4 mL), MeOH (1 mL) and HCl (4 M in dioxane, 1 mL) was added. The reaction mixture was stirred for 5 h and then concentrated under reduced pressure. The crude residue was treated with ((2S,3R)-3-methoxy-2-(methoxycarbonylamino)butanoic acid (92 mg, 0.48 mmol), HATU (182 mg, 0.48 mmol) and DMF (5 mL), then DIPEA (0.31 mL, 2.4 mmol) was added dropwise. After 35 min, the mixture was diluted with 10% MeOH/EtOAc and washed successively with saturated aqueous NaHCO₃ and brine. The organics were dried over MgSO₄, filtered and concentrated under reduced pressure. The crude residue was purified by HPLC to afford methyl {(2S,3R)-3-methoxy-1-[(2S,4S)-2-[9-(2-{(2S,4S)-1-[N-(methoxycarbonyl)-O-methyl-L-threonyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidin-1-yl]-1-oxobutan-2-yl}carbamate (72 mg, 34%). LCMS-ESI$^+$: calculated for $C_{46}H_{56}N_8O_{10}$: 880.41; observed [M+1]$^+$: 882.39. $^1$H NMR (CD₃OD): 8.558 (s, 1H), 8.123-7.572 (m, 7H), 5.436-5.391 (dd, 1H, J=7.2, 3.6 Hz), 5.252 (s, 2H), 5.220 (m, 1H), 4.493-4.444 (m, 2H), 4.287-4.206 (m, 2H), 3.756-3.256 (m, 2H), 2.834 (m, 1H), 2.717-2.621 (m, 2H), 2.500 (m, 1H), 2.150 (m, 1H), 1.882 (m, 1H), 1.208 (d, 3H, J=6.4 Hz), 1.159-1.099 (m, 6H).

Example NL

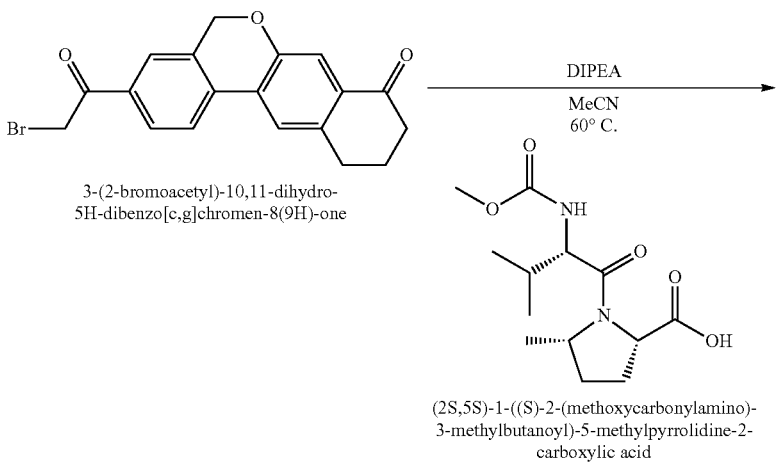

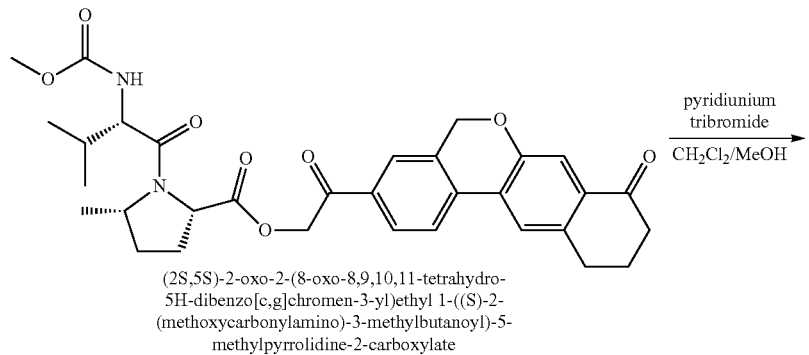

-continued

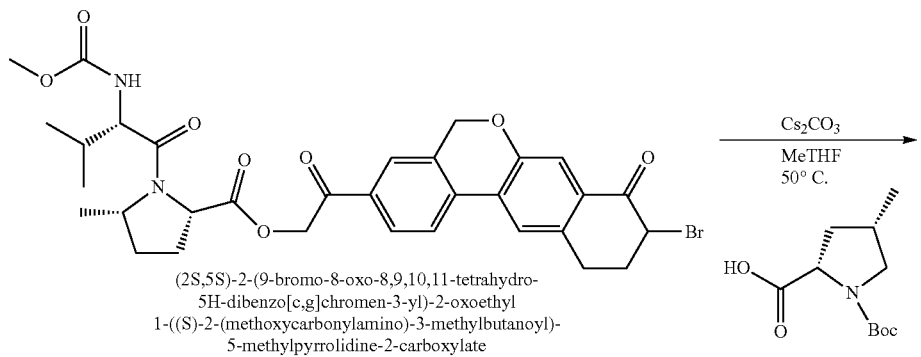

(2S,5S)-2-(9-bromo-8-oxo-8,9,10,11-tetrahydro-5H-dibenzo[c,g]chromen-3-yl)-2-oxoethyl 1-((S)-2-(methoxycarbonylamino)-3-methylbutanoyl)-5-methylpyrrolidine-2-carboxylate (2S,4S)-1-(tert-butoxycarbonyl)-4-methylpyrrolidine-2-carboxylic acid

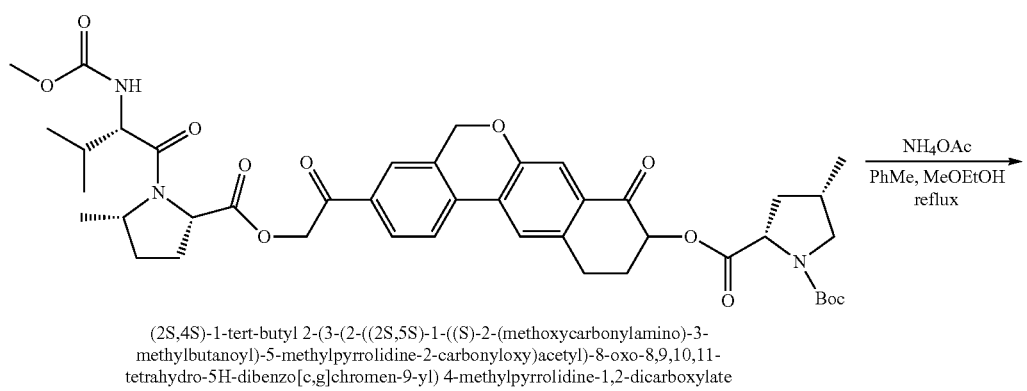

(2S,4S)-1-tert-butyl 2-(3-(2-(((2S,5S)-1-((S)-2-(methoxycarbonylamino)-3-methylbutanoyl)-5-methylpyrrolidine-2-carbonyloxy)acetyl)-8-oxo-8,9,10,11-tetrahydro-5H-dibenzo[c,g]chromen-9-yl) 4-methylpyrrolidine-1,2-dicarboxylate

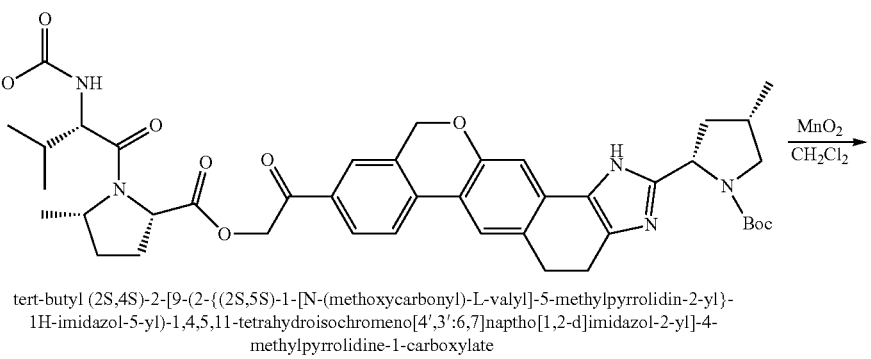

tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4′,3′:6,7]naptho[1,2-d]imidazol-2-yl]-4-methylpyrrolidine-1-carboxylate

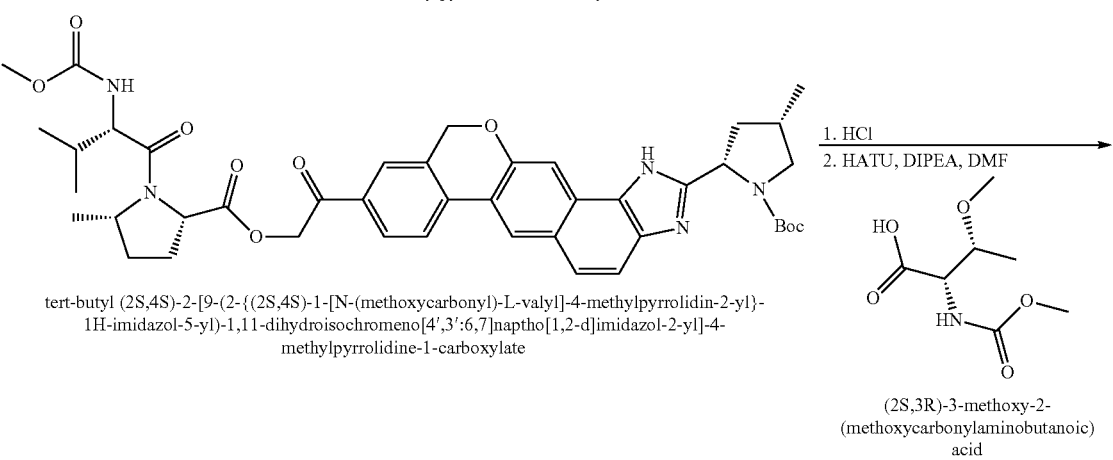

tert-butyl (2S,4S)-2-[9-(2-{(2S,4S)-1-[N-(methoxycarbonyl)-L-valyl]-4-methylpyrrolidin-2-yl}-1H-imidazol-5-yl)-1,11-dihydroisochromeno[4′,3′:6,7]naptho[1,2-d]imidazol-2-yl]-4-methylpyrrolidine-1-carboxylate (2S,3R)-3-methoxy-2-(methoxycarbonylaminobutanoic) acid

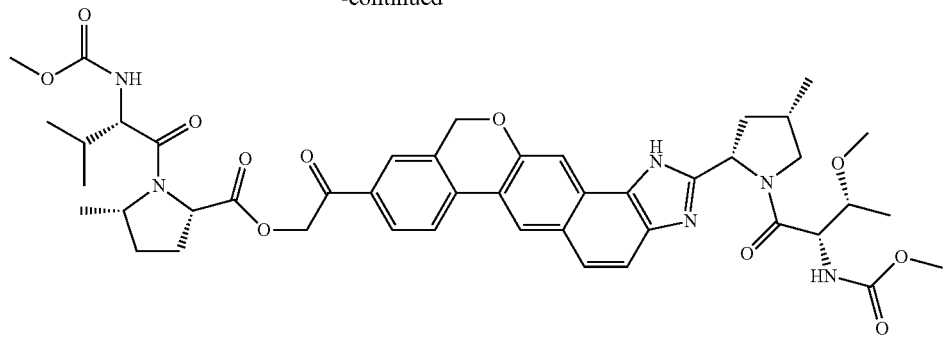

methyl {(2S)-1-[(2S,5S)-2-(5-{2-[(2S,4S)-1-{(2S,3R)-3-methoxy-2-[(methoxycarbonyl)amino]butanoyl}-4-methylpyrrolidin-2-yl]-1,11-dihydroisochromeno[4',3':6,7]naptho[1,2-d]imidazol-9-yl}-1H-imidazol-2-yl)-5-methylpyrrolidine-1-yl]-3-methyl-1-oxobutan-2-yl}carbamate (2S,5S)-2-oxo-2-(8-oxo-8,9,10,11-tetrahydro-5H-dibenzo[c,g]chromen-3-yl)ethyl 1-((S)-2-(methoxycarbonylamino)-3-methylbutanoyl)-5-methylpyrrolidine-2-carboxylate: To a solution of 3-(2-bromoacetyl)-10,11-dihydro-5H-dibenzo[c,g]chromen-8(9H)-one (750 mg, 2.02 mmol) in MeCN (20 mL) was added (2S,5S)-1-((S)-2-(methoxycarbonylamino)-3-methylbutanoyl)-5-methylpyrrolidine-2-carboxylic acid (600 mg, 2.09 mmol) and DIPEA (0.35 mL, 2.02 mmol) and the solution was heated to 60° C. After stirring for 4 h, the solution was cooled to rt, and diluted with EtOAc and washed successively with saturated aqueous NaHCO₃ and brine. The organics were dried over MgSO₄, filtered and concentrated under reduced pressure. The crude residue was purified by silica column chromatography (40% to 80% EtOAc/hexanes) to afford (2S,5S)-2-oxo-2-(8-oxo-8,9,10,11-tetrahydro-5H-dibenzo[c,g]chromen-3-yl)ethyl 1-((S)-2-(methoxycarbonylamino)-3-methylbutanoyl)-5-methylpyrrolidine-2-carboxylate (1.16 g, quant.).

(2S,5S)-2-(9-bromo-8-oxo-8,9,10,11-tetrahydro-5H-dibenzo[c,g]chromen-3-yl)-2-oxoethyl 1-((S)-2-(methoxycarbonylamino)-3-methylbutanoyl)-5-methylpyrrolidine-2-carboxylate:

(2S,5S)-2-oxo-2-(8-oxo-8,9,10,11-tetrahydro-5H-dibenzo[c,g]chromen-3-yl)ethyl 1-((S)-2-(methoxycarbonylamino)-3-methylbutanoyl)-5-methylpyrrolidine-2-carboxylate (400 mg, 0.61 mmol) was dissolved in a solution of DCM (15 mL) and MeOH (6 mL), then treated with pyridinium tribromide (409 mg, 1.28 mmol). At 2 h, an additional portion of pyridinium tribromide (40 mg) was added. After stirring at RT for another 20 min, the reaction mixture was diluted with DCM and 10% HCl, and extracted with DCM. The organic phase was dried over MgSO₄, filtered and concentrated under reduced pressure and the crude material was carried on without further purification.

(2S,4S)-1-tert-butyl 2-(3-(2-((2S,5S)-1-((S)-2-(methoxycarbonylamino)-3-methylbutanoyl)-5-methylpyrrolidine-2-carbonyloxy)acetyl)-8-oxo-8,9,10,11-tetrahydro-5H-dibenzo[c,g]chromen-9-yl) 4-methylpyrrolidine-1,2-dicarboxylate: (2S,5S)-2-(9-bromo-8-oxo-8,9,10,11-tetrahydro-5H-dibenzo[c,g]chromen-3-yl)-2-oxoethyl 1-((S)-2-(methoxycarbonylamino)-3-methylbutanoyl)-5-methylpyrrolidine-2-carboxylate) was treated with a solution of (2S,4S)-1-(tert-butoxycarbonyl)-4-methylpyrrolidine-2-carboxylic acid (280 mg, 1.22 mmol) in Me-THF (6 mL) and Cs₂CO₃ (199 mg, 0.61 mmol). The stirred reaction mixture was heated to 50° C. for 2.5 h, then cooled to RT and diluted with CH₂Cl₂ and extracted 3x. The organic phase was washed with brine, then dried over MgSO₄, filtered and concentrated under reduced pressure. The crude residue was purified by silica column chromatography (50% to 100% EtOAc/hexanes) to afford (2S,4S)-1-tert-butyl 2-(3-(2-((2S,5S)-1-((S)-2-(methoxycarbonylamino)-3-methylbutanoyl)-5-methylpyrrolidine-2-carbonyloxy)acetyl)-8-oxo-8,9,10,11-tetrahydro-5H-dibenzo[c,g]chromen-9-yl) 4-methylpyrrolidine-1,2-dicarboxylate (441 mg, 90%).

Tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4',3':6,7]naphtho[1,2-d]imidazol-2-yl]-4-methylpyrrolidine-1-carboxylate: (2S,4S)-1-tert-butyl 2-(3-(2-((2S,5S)-1-((S)-2-(methoxycarbonylamino)-3-methylbutanoyl)-5-methylpyrrolidine-2-carbonyloxy)acetyl)-8-oxo-8,9,10,11-tetrahydro-5H-dibenzo[c,g]chromen-9-yl) 4-methylpyrrolidine-1,2-dicarboxylate (441 mg, 0.55 mmol) and NH₄OAc (5 g, 65.0 mmol) were suspended in a solution of 10:1 PhMe/2-methoxyethanol (11 mL). The stirred reaction mixture was heated to 110° C. for 7 h, then cooled to RT and diluted with EtOAc. The organic phase was washed with water, saturated aqueous NaHCO₃, and brine, then dried over MgSO₄, filtered and concentrated under reduced pressure. The crude residue was purified by silica column chromatography (0% to 30% MeOH/EtOAc) to afford tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4',3':6,7]naphtho[1,2-d]imidazol-2-yl]-4-methylpyrrolidine-1-carboxylate (266 mg, 63%).

Tert-butyl (2S,4S)-2-[9-(2-{(2S,4S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate: Tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11 tetrahydroisochromeno[4',3':6,7]naphtho[1,2-d]imidazol-2-yl]-4-methylpyrrolidine-1-carboxylate (266 mg, 0.35 mmol) was suspended in DCM (7 mL) and activated MnO₂ (908 mg, 10.45 mmol) was added in a single portion. The reaction mixture was stirred overnight. After stirring for 15 h, additional activated MnO₂ (500 mg, 5.75 mmol) was added in a single portion. After stirring 2 h at 35° C., the mixture was cooled to rt and the slurry was filtered over celite. The filter cake was washed with copious CH₂Cl₂ and MeOH and the filtrate was concentrated under reduced pressure. The crude material was taken on to the next step without further purification to afford tert-butyl (2S,4S)-2-[9-(2-{(2S,4S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (266 mg, quant).

Methyl {(2S)-1-[(2S,5S)-2-(5-{2-[(2S,4S)-1-{(2S,3R)-3-methoxy-2-[(methoxycarbonyl)amino]butanoyl}-4-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate: Tert-butyl (2S,4S)-2-[9-(2-{(2S,4S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (266 mg, 0.23 mmol) was dissolved in DCM (4 mL), MeOH (1 mL) and HCl (4 M in dioxane, 1 mL) was added. The reaction mixture was stirred for 1.5 h and then concentrated under reduced pressure. The crude residue was treated with (2S,3R)-3-methoxy-2-(methoxycarbonylamino)butanoic acid (44 mg, 0.23 mmol), HATU (87 mg, 0.23 mmol) and DMF (5 mL), then DIPEA (0.3 mL, 1.75 mmol) was added dropwise. After 30 min, the mixture was diluted with 10% MeOH/EtOAc and washed successively with saturated aqueous NaHCO₃ and brine. The organics were dried over MgSO₄, filtered and concentrated under reduced pressure. The crude residue was purified by HPLC to afford methyl {(2S)-1-[(2S,5S)-2-(5-{2-[(2S,4S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (59 mg, 31%). LCMS-ESI$^+$: calculated for C, 45; H, 54; N, 8; O, 8: 834.41; observed [M+1]$^+$: 836.89. $^1$H NMR (CD$_3$OD): 8.186 (s, 1H), 7.800-7.291 (m, 7H), 5.258-5.213 (dd, 1H, J=7.2, 3.6 Hz), 5.027-4.918 (m, 4H), 4.620 (t, 1H, J=6.8 Hz), 4.246 (m, 1H), 4.116 (m, 1H), 3.972 (d, 1H, J=8.8 Hz), 3.701-3.675 (m, 1H), 3.503 (s, 3H), 3.479 (s, 3H), 3.177 (s, 3H), 2.554-2.191 (m, 3H), 1.906-1.821 (m, 6H), 1.392 (d, 2H, J=6.4 Hz), 1.113-0.728 (m, 12H).

Example NM

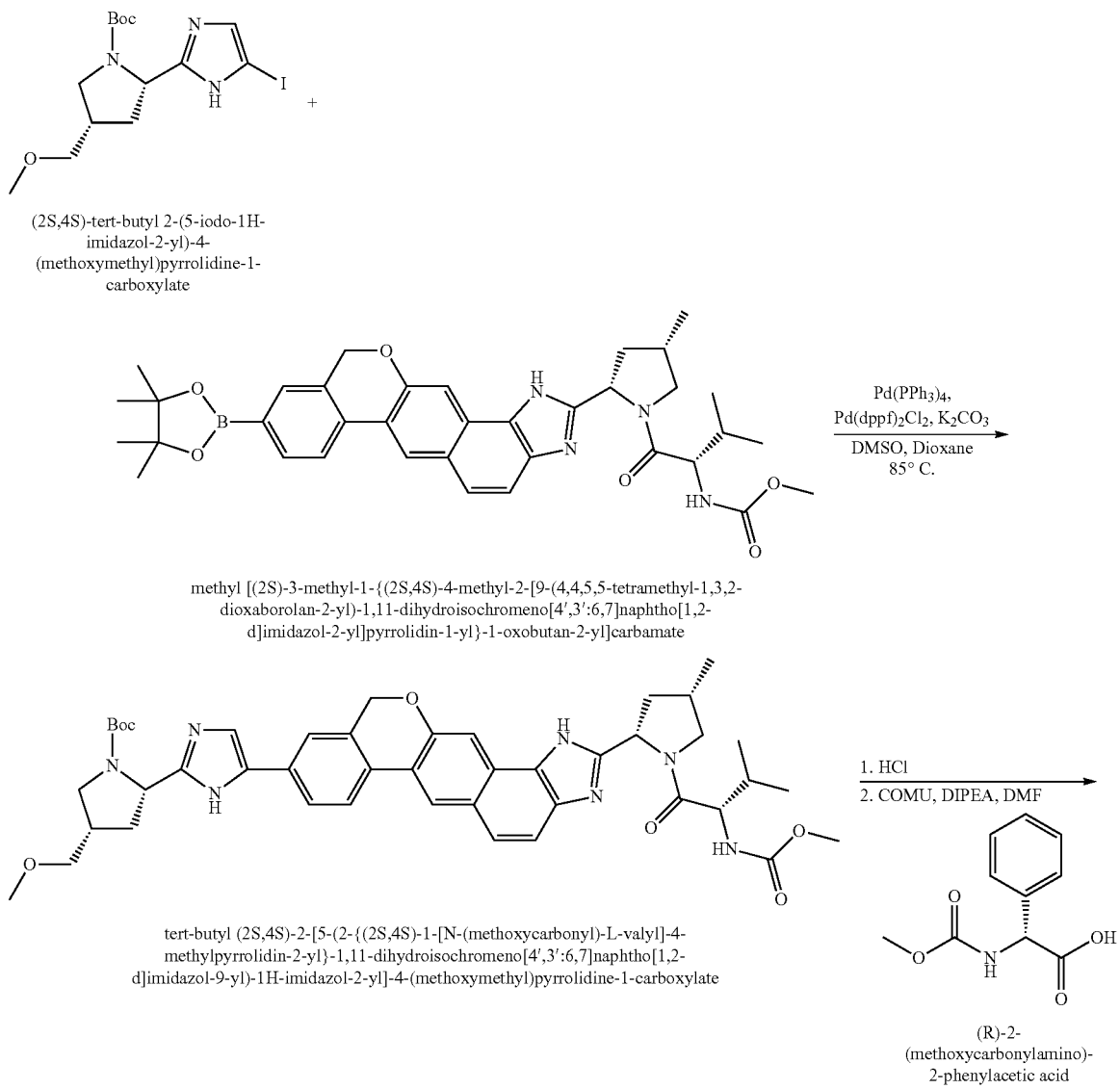

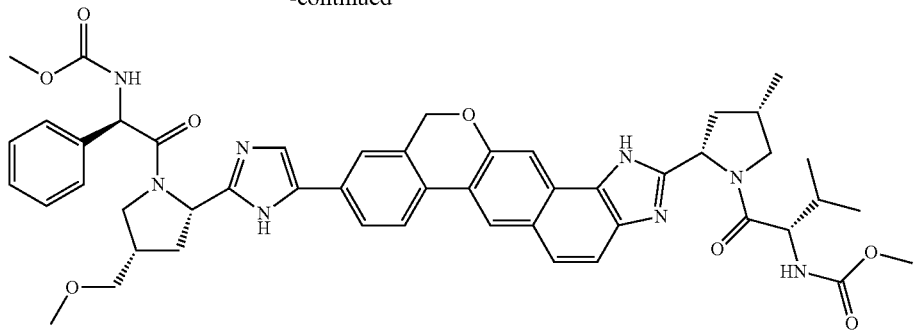

methyl {(1R)-2-[(2S,4S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-(methyloxymethyl)pyrrolidin-1-yl]-2-oxo-1-phenylethyl}carbamate Tert-butyl (2S,4S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate: Methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (312 mg, 0.49 mmol), methyl (S)-1-((2S,4S)-2-(5-iodo-1H-imidazol-2-yl)-4-methylpyrrolidin-1-yl)-3-methyl-1-oxobutan-2-ylcarbamate (219 mg, 0.54 mmol), Pd(PPh$_3$)$_4$ (58 mg, 0.05 mmol), PdCl$_2$(dppf)$_2$ (36 mg, 0.05 mmol), and K$_2$CO$_3$ (2M in H$_2$O, 0.8 mL, 1.6 mmoL) were combined in DMSO (5 mL) and dioxane (5 mL). The mixture was degassed with bubbling N$_2$ for 10 min the heated to 95° C. for 5 h. After cooling, the reaction mixture was diluted with EtOAc, and washed successively with saturated aqueous NaHCO$_3$ and brine. The organics were dried over MgSO$_4$, filtered and concentrated under reduced pressure. The crude residue was purified by silica column chromatography (0%-30% MeOH/EtOAc) to afford tert-butyl (2S,4S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (166 mg, 43%).

Methyl {(1R)-2-[(2S,4S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate: Tert-butyl (2S,4S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (166 mg, 0.21 mmol) was dissolved in DCM (4 mL), MeOH (1 mL) and HCl (4 M in dioxane, 1 mL) was added. The reaction mixture was stirred for 2 h and then concentrated under reduced pressure. The crude residue was treated with (R)-2-(methoxycarbonylamino)-2-phenylacetic acid (44 mg, 0.21 mmol), COMU (100 mg, 0.21 mmol) and DMF (5 mL), then DIPEA (0.18 mL, 1.05 mmol) was added dropwise. After 1 h, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl {(1R)-2-[(2S,4S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate (71 mg, 38%). LCMS-ESI$^+$: calculated for C49H54N8O8: 882.41; observed [M+1]$^+$: 884.34. $^1$H NMR (CD$_3$OD): 8.462 (s, 1H), 8.029-7.471 (m, 7H), 7.394-7.343 (m, 5H), 5.410 (d, 2H, J=6.8 Hz), 5.300 (m, 1H), 5.233 (m, 2H), 4.341 (m, 1H), 4.236 (d, 1H, J=7.2 Hz), 3.603 (s, 3H), 3.551 (s, 3H), 3.522-3.241 (m, 8H), 2.650 (m, 1H), 2.550 (m, 2H), 1.977-1.926 (m, 4H), 1.221 (d, 3H, J=3.2 Hz), 0.897-0.779 (dd, 6H, J=19.2, 6.8 Hz).

Example NN

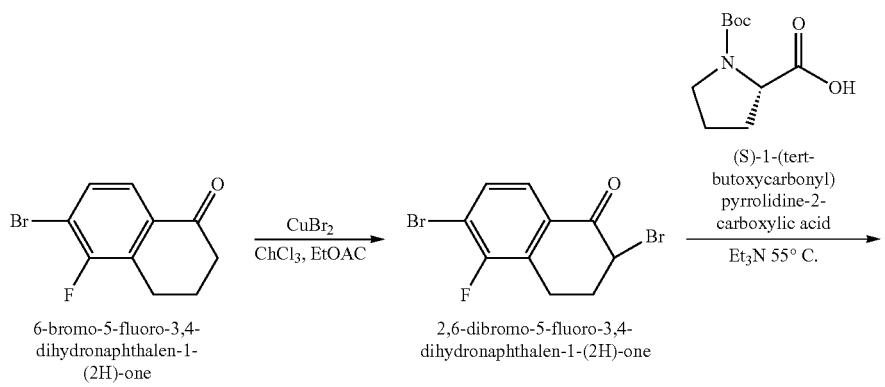

-continued

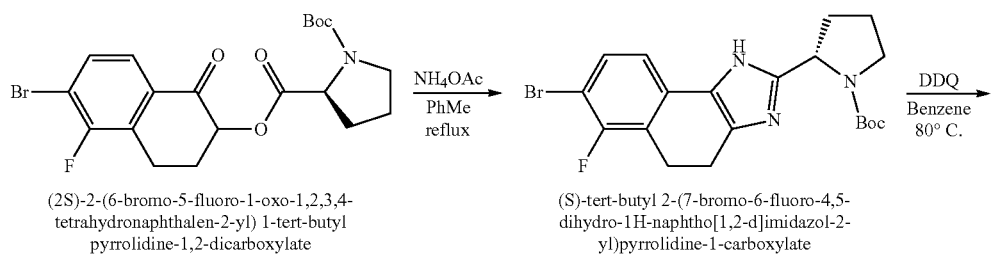

(2S)-2-(6-bromo-5-fluoro-1-oxo-1,2,3,4-tetrahydronaphthalen-2-yl) 1-tert-butyl pyrrolidine-1,2-dicarboxylate (S)-tert-butyl 2-(7-bromo-6-fluoro-4,5-dihydro-1H-naphtho[1,2-d]imidazol-2-yl)pyrrolidine-1-carboxylate

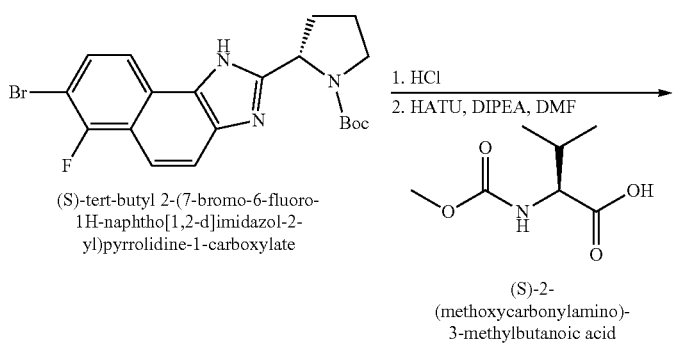

(S)-tert-butyl 2-(7-bromo-6-fluoro-1H-naphtho[1,2-d]imidazol-2-yl)pyrrolidine-1-carboxylate (S)-2-(methoxycarbonylamino)-3-methylbutanoic acid

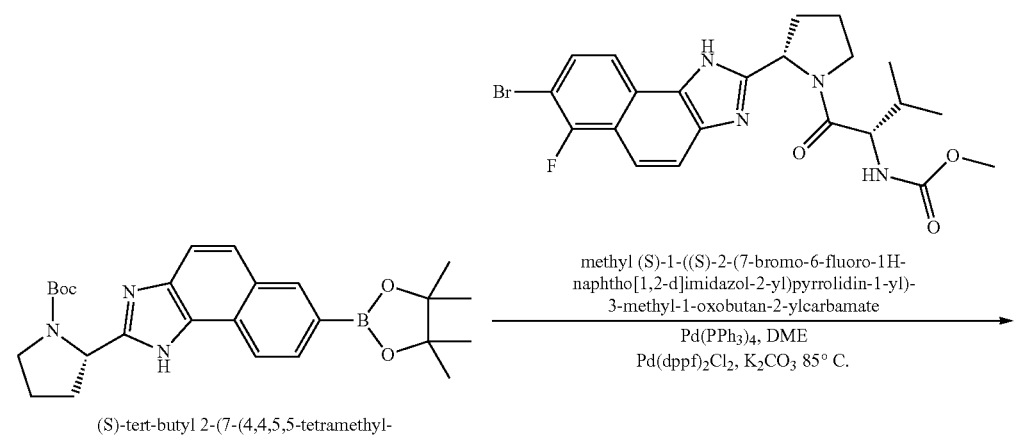

methyl (S)-1-((S)-2-(7-bromo-6-fluoro-1H-naphtho[1,2-d]imidazol-2-yl)pyrrolidin-1-yl)-3-methyl-1-oxobutan-2-ylcarbamate (S)-tert-butyl 2-(7-(4,4,5,5-tetramethyl-1,3,2-dioxaborolan-2-yl)-1H-naphtho[1,2-d]imidazol-2-yl)pyrrolidine-1-carboxylate

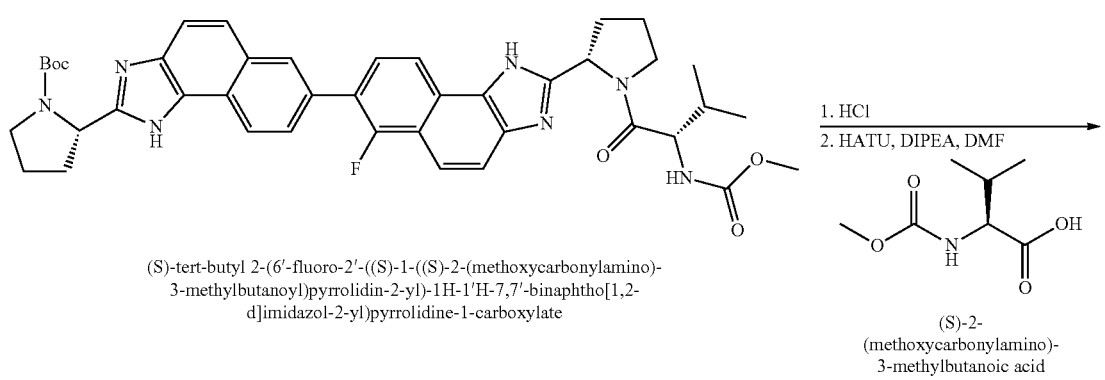

(S)-tert-butyl 2-(6'-fluoro-2'-((S)-1-((S)-2-(methoxycarbonylamino)-3-methylbutanoyl)pyrrolidin-2-yl)-1H-1'H-7,7'-binaphtho[1,2-d]imidazol-2-yl)pyrrolidine-1-carboxylate (S)-2-(methoxycarbonylamino)-3-methylbutanoic acid

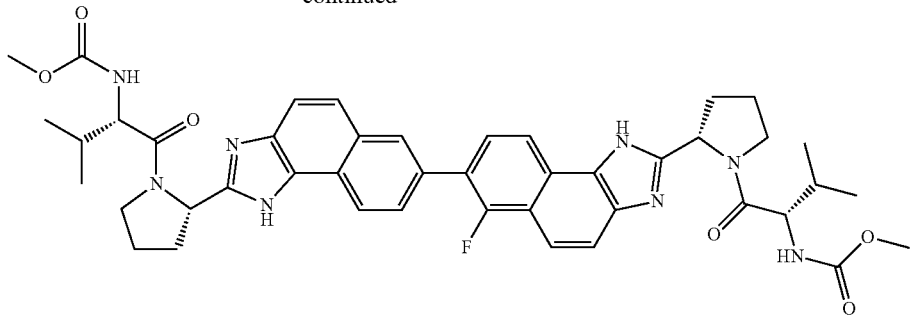

dimethyl (2S,2'S)-1,1'-((2S,2'S)-2,2'-(6-fluoro-1H,1'H-7,7'-binaphtho[1,2-d]imidazole-2,2'-diyl)bis(pyrrolidine-2,1-diyl))bis(3-methyl-1-oxobutane-2,1-diyl)carbamate 2,6-dibromo-5-fluoro-3,4-dihydronaphthalen-1(2H)-one: To a solution of 6-bromo-5-fluoro-3,4-dihydronaphthalen-1(2H)-one (900 mg, 3.7 mmol) in CHCl₃ (25 mL) and EtOAc (25 mL) was added copper II bromide (1.65 g, 7.4 mmol), and the mixture was heated to 80° C. for 7 h. After heating, the mixture was cooled to rt, diluted with CH₂Cl₂ and saturated aqueous NH₄Cl and separated. The organics were dried over MgSO₄, filtered and concentrated under reduced pressure. The crude residue was taken on to the next step with out purification.

(2S)-2-(6-bromo-5-fluoro-1-oxo-1,2,3,4-tetrahydronaphthalen-2-yl) 1-tert-butyl pyrrolidine-1,2-dicarboxylate: To a solution of 2,6-dibromo-5-fluoro-3,4-dihydronaphthalen-1(2H)-one in MeCN (30 mL) was added (S)-1-(tert-butoxycarbonyl)pyrrolidine-2-carboxylic acid (1.12g, 5.2 mmol) and triethyl amine (0.62 mL, 4.48 mmol) and the solution was heated to 55° C. After stirring for 15 h, the solution was cooled to rt, and diluted with EtOAc and washed successively with saturated aqueous NaHCO₃ and brine. The organics were dried over MgSO₄, filtered and concentrated under reduced pressure. The crude residue was purified by silica column chromatography (10% to 35% EtOAc/hexanes) to afford (2S)-2-(6-bromo-5-fluoro-1-oxo-1,2,3,4-tetrahydronaphthalen-2-yl) 1-tert-butyl pyrrolidine-1,2-dicarboxylate (648 mg, 38%).

(S)-tert-butyl 2-(7-bromo-6-fluoro-4,5-dihydro-1H-naphtho[1,2-d]imidazol-2-yl)pyrrolidine-1-carboxylate: To (2S)-2-(6-bromo-5-fluoro-1-oxo-1,2,3,4-tetrahydronaphthalen-2-yl) 1-tert-butyl pyrrolidine-1,2-dicarboxylate (773 mg, 1.69 mmol) was added PhMe (15 mL) and ammonium acetate (2.6 g, 33.88 mmol) and the solution was heated to 110° C. and stirred overnight. The following morning, the solution was cooled to rt and was diluted with EtOAc and washed successively with water, saturated aqueous NaHCO₃ and brine. The organics were dried over MgSO₄, filtered and concentrated under reduced pressure. The crude residue was purified by silica column chromatography (40% to 100% EtOAc/hexanes) to afford (S)-tert-butyl 2-(7-bromo-6-fluoro-4,5-dihydro-1H-naphtho[1,2-d]imidazol-2-yl)pyrrolidine-1-carboxylate (648 mg, 88%).

(S)-tert-butyl 2-(7-bromo-6-fluoro-1H-naphtho[1,2-d]imidazol-2-yl)pyrrolidine-1-carboxylate: To a solution of (S)-tert-butyl 2-(7-bromo-6-fluoro-4,5-dihydro-1H-naphtho[1,2-d]imidazol-2-yl)pyrrolidine-1-carboxylate (324 mg, 0.74 mmol) in benzene (7 mL) was added DDQ (185 mg, 0.82 mmol) and the mixture was heated to 80° C. After stirring for 16 h, the reaction mixture was cooled to rt and concentrated under reduced pressure. The crude residue was purified by silica column chromatography (45% to 100% EtOAc/hexanes) to afford (S)-tert-butyl 2-(7-bromo-6-fluoro-1H-naphtho[1,2-d]imidazol-2-yl)pyrrolidine-1-carboxylate (204 mg, 63%).

Methyl (S)-1-((S)-2-(7-bromo-6-fluoro-1H-naphtho[1,2-d]imidazol-2-yl)pyrrolidin-1-yl)-3-methyl-1-oxobutan-2-yl-carbamate: (S)-tert-butyl 2-(7-bromo-6-fluoro-1H-naphtho[1,2-d]imidazol-2-yl)pyrrolidine-1-carboxylate (204 mg, 0.47 mmol) was dissolved in DCM (5 mL), MeOH (1 mL) and HCl (4 M in dioxane, 1 mL) was added. The reaction mixture was stirred for 16 h and then concentrated under reduced pressure. The crude residue was treated with (S)-2-(methoxycarbonylamino)-3-methylbutanoic acid (82 mg, 0.47 mmol), HATU (179 mg, 0.47 mmol) and DMF (6 mL), then DIPEA (0.41 mL, 2.35 mmol) was added dropwise. After 3 h, the mixture was diluted with EtOAc and washed successively with saturated aqueous NaHCO₃ and brine. The organics were dried over MgSO₄, filtered and concentrated under reduced pressure. The crude residue was purified by silica column chromatography (0% to 30% MeOH/EtOAc) to afford methyl (S)-1-((S)-2-(7-bromo-6-fluoro-1H-naphtho[1,2-d]imidazol-2-yl)pyrrolidin-1-yl)-3-methyl-1-oxobutan-2-ylcarbamate (238 mg, 49%).

(S)-tert-butyl 2-(6'-fluoro-2'-((S)-1-((S)-2-(methoxycarbonylamino)-3-methylbutanoyl)pyrrolidin-2-yl)-1H,1'H-7,7'-binaphtho[1,2-d]imidazol-2-yl)pyrrolidine-1-carboxylate: (S)-tert-butyl 2-(7-(4,4,5,5-tetramethyl-1,3,2-dioxaborolan-2-yl)-1H-naphtho[1,2-d]imidazol-2-yl)pyrrolidine-1-carboxylate (250 mg, 0.48 mmol) and methyl (S)-1-((S)-2-(7-bromo-6-fluoro-1H-naphtho[1,2-d]imidazol-2-yl)pyrrolidin-1-yl)-3-methyl-1-oxobutan-2-ylcarbamate (200 mg, 0.4 mmol), Pd(PPh₃)₄ (46 mg, 0.04 mmol), Pd(dppf)₂Cl₂ (29 mg, 0.04 mmol), and K₂CO₃ (2M in H₂O, 0.67 mL, 1.34 mmoL) were combined in DME (6 mL). The mixture was degassed with bubbling N₂ for 10 min the heated to 85° C. for 16 h. After cooling, the reaction mixture was diluted with EtOAc, and washed successively with saturated aqueous NaHCO₃ and brine. The organics were dried over MgSO₄, filtered and concentrated under reduced pressure. The crude residue was purified by silica column chromatography (0% to 30% MeOH/EtOAc) to afford (S)-tert-butyl 2-(6'-fluoro-2'-((S)-1-((S)-2-(methoxycarbonylamino)-3-methylbutanoyl)pyrrolidin-2-yl)-1H,1'H-7,7'-binaphtho[1,2-d]imidazol-2-yl)pyrrolidine-1-carboxylate (213 mg, 71%).

Dimethyl (2S,2'S)-1,1'-((2S,2'S)-2,2'-(6-fluoro-1H,1'H-7,7'-binaphtho[1,2-d]imidazole-2,2'-diyl)bis(pyrrolidine-2,1-diyl))bis(3-methyl-1-oxobutane-2,1-diyl)Dicarbamate: (S)-tert-butyl 2-(6'-fluoro-2'-((S)-1-((S)-2-(methoxycarbonylamino)-3-methylbutanoyl)pyrrolidin-2- yl)-1H,1'H-7,7'-binaphtho[1,2-d]imidazol-2-yl)pyrrolidine-1-carboxylate (213 mg, 0.28 mmol) was dissolved in DCM (7 mL), MeOH (1.5 mL) and HCl (4 M in dioxane, 1.5 mL) was added. The reaction mixture was stirred for 2 h and then concentrated under reduced pressure. The crude residue was treated with (S)-2-(methoxycarbonylamino)-3-methylbutanoic acid (49 mg, 0.28 mmol), HATU (106 mg, 0.28 mmol) and DMF (5 mL), then DIPEA (0.25 mL, 1.42 mmol) was added dropwise. After 35 min, the mixture was diluted with EtOAc and washed successively with saturated aqueous NaHCO₃ and brine. The organics were dried over MgSO₄, filtered and concentrated under reduced pressure. The crude residue was purified by HPLC to afford dimethyl (2S,2'S)-1,1'-((2S,2'S)-2,2'-(6-fluoro-1H, 1'H-7,7'-binaphtho[1,2-d]imidazole-2,2'-diyl)bis(pyrrolidine-2,1-diyl))bis(3-methyl-1-oxobutane-2,1-diyl)dicarbamate (126 mg, 56%). LCMS-ESI⁺: calculated for C44H49FN8O6: 804.38; observed [M+1]⁺: 805.41.

Example NO

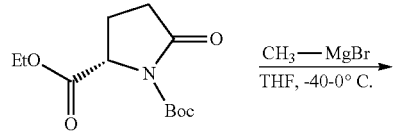

(S)-1-tert-butyl 2-ethyl 5-oxopyrrolidine-1,2-dicarboxylate

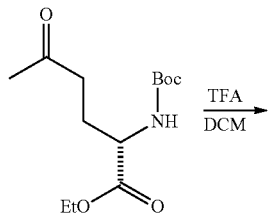

(S)-ethyl 2-(tert-butoxycarbonylamino)-5-oxohexanoate

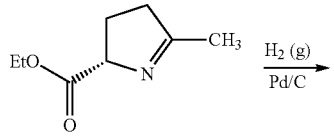

(S)-ethyl 5-methyl-3,4-dihydro-2H-pyrrole-2-carboxylate

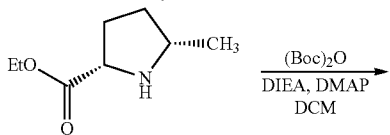

(2S,5S)-ethyl 5-methylpyrrolidine-2-carboxylate

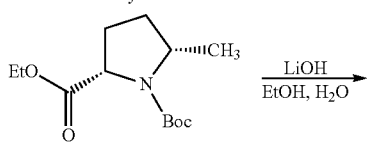

(2S,5S)-1-tert-butyl 2-ethyl 5-methylpyrrolidine-1,2-carboxylate

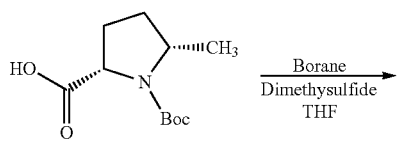

(2S,5S)-1-(tert-butoxycarbonyl)-5-methylpyrrolidine-2-carboxylic acid

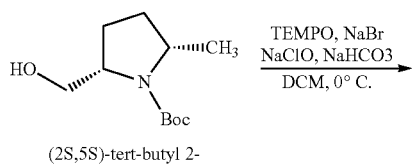

(2S,5S)-tert-butyl 2-(hydroxymethyl)-5-methylpyrrolidine-1-carboxylate

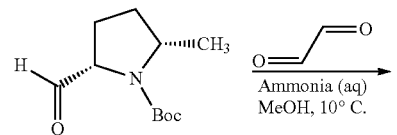

(2S,5S)-tert-butyl 2-formyl 5-methylpyrrolidine-1-carboxylate

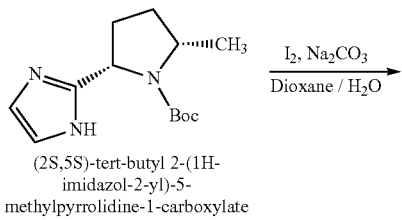

(2S,5S)-tert-butyl 2-(1H-imidazol-2-yl)-5-methylpyrrolidine-1-carboxylate

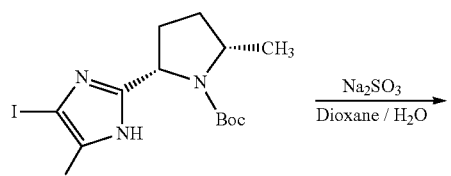

(2S,5S)-tert-butyl 2-(4,5-diiodo-1H-imidazol-2-yl)-5-methylpyrrolidine-1-carboxylate

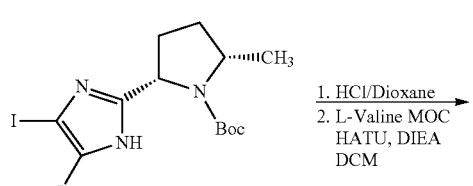

(2S,5S)-tert-butyl 2-(5-iodo-1H-imidazol-2-yl)-5-methylpyrrolidine-1-carboxylate -continued

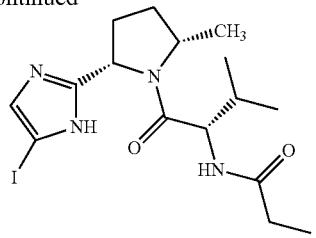

(2S)-1-[(2S,5S)-2-(5-iodo-1H-imidazol-2-yl)-5-methylpyrrolidin-1-yl]-2-[(1-methoxyethenyl)amino]-3-methylbutan-1-one (S)-ethyl 2-(tert-butoxycarbonylamino)-5-oxohexanoate. A solution of ethyl N-Boc (S)-pyroglutamate (20.0 g, 77.7 mmol) was in anhydrous THF (150 mL) in a two neck round bottom under argon was cooled to −40° C. Methyl-magnesium bromide solution (3.0 M in Ether, 28.5 mL, 85.5 mmol) was added to the reaction mixture dropwise over 30 minutes. The reaction was stirred for 4 hrs at −40° C. then for 1 hr at 0° C. The reaction was partitioned between ethyl acetate and saturated ammonium chloride solution and acidified with 1 N HCl. The aqueous layer was extracted two more times with ethylacetate. The organic layers were combined and dried with sodium sulfate. The crude material was purified by column chromatography (20%-40% EtOAc/hexanes) to yield (S)-ethyl 2-(tert-butoxycarbonylamino)-5-oxohexanoate as a viscous oil and was used directly in the following step.

(S)-ethyl 5-methyl-3,4-dihydro-2H-pyrrole-2-carboxylate. (S)-ethyl 2-(tert-butoxycarbonylamino)-5-oxohexanoate in a 1 L flask was treated with a trifluoro acetic acid/dichloromethane solution (1:1 mixture, 100 mL). Effervescence was observed and the mixture was allowed to stir for 4 hours at room temperature. After which time the volatiles were removed in vacuo to yield (S)-ethyl 5-methyl-3,4-dihydro-2H-pyrrole-2-carboxylate as an oil, and used directly in the following step.

(2S,5S)-ethyl 5-methylpyrrolidine-2-carboxylate. The crude imine in a 1 L flask was dissolved with ethanol (400 mL) was evacuated and charged with argon three times (3×). Palladium on carbon (apprx. 750 mg, 10% w/w, dry) was added and the reaction was evacuated of gas and charged with hydrogen gas (3×). The reaction was allowed to stir under atmospheric hydrogen for 16 hours. The mixture was filtered through a plug of celite and the filtrate was concentrated in vacuo. Diethyl ether was added to the oil and a precipitate formed. The mixture was filtered to yield (2S, 5S)-ethyl 5-methylpyrrolidine-2-carboxylate, as a white solid (10.6 g, 67.4 mmol, 86.7% over three steps). $^1$H NMR (400 MHz, cdcl$_3$) δ 4.48 (dd, 1H), 4.27 (q, 2H), 3.92-3.80 (m, 1H), 2.52-2.36 (m, 1H), 2.32-2.13 (m, 2H), 1.75-1.60 (m, 1H), 1.51 (d, 3H), 1.30 (t, 3H).

(2S,5S)-1-tert-butyl 2-ethyl 5-methylpyrrolidine-1,2-dicarboxylate. To a solution of (2S,5S)-ethyl 5-methylpyrrolidine-2-carboxylate (7.0 g, 44.5 mmol) in dichloromethane (250 mL), ditertbutylanhydride (10.7 g, 49.0 mmol), diisopropylethylamine (17.1 mL, 98.0 mmol) dropwise over 10 minutes, and dimethyl amino pyridine (0.27 g, 2.23 mmol) were added successively. Effervescence was observed and the mixture was allowed to stir for 16 hours at room temperature. The reaction was washed with HCl (250 mL, of 1N). The organic layer was then dried with sodium sulfate. The crude material was purified by column chromatography (5%-25% EtOAc/hexanes) to yield (2S,5S)-1-tert-butyl 2-ethyl 5-methylpyrrolidine-1,2-dicarboxylate as an oil (6.46 g, 25.1 mmol, 56%). LCMS-ESI$^+$: calc'd for $C_{13}H_{23}NO_4$: 257.16 (M$^+$); Found: 258.70 (M+H$^+$).

(2S,5S)-1-(tert-butoxycarbonyl)-5-methylpyrrolidine-2-carboxylic acid. To a solution of (2S,5S)-1-tert-butyl 2-ethyl 5-methylpyrrolidine-1,2-dicarboxylate (6.46 g, 25.1 mmol) in ethanol (20 mL) was added lithium hydroxide mono hydrate (2.11 g, 50.2 mmol) and deionized water (12 mL). The mixture was allowed to stir for 16 hours then partitioned between ethylacetate and a 1:1 mixture of saturated brine and 1N HCl. The aqueous layer was extracted an additional time with ethyl acetate. The organic layers were combined, dried with sodium sulfate and the solvent was removed in vacuo to yield (2S,5S)-1-(tert-butoxycarbonyl)-5-methylpyrrolidine-2-carboxylic acid as a white solid (quant.) and was used directly in the following step.

(2S,5S)-tert-butyl 2-(hydroxymethyl)-5-methylpyrrolidine-1-carboxylate. To a solution of (2S,5S)-1-(tert-butoxycarbonyl)-5-methylpyrrolidine-2-carboxylic acid (5.91 g, 25.8 mmol) in tetrahydrofuran at 0° C., was added borane in dimethylsulfide (1.0 M, 3.4 mL, 34 mmol) dropwise. The reaction was stirred for 4 hours at 0° C. then 18 hours at room temperature. The mixture was then cooled to 0° C. and methanol (70 mL) was added dropwise. The reaction was warmed to room temperature and the solvents were removed in vacuo. The residue was taken up in dichloromethane (200 mL) and extracted with saturated sodium bicarbonate. The organic layer was dried with sodium sulfate and the solvent was removed in vacuo to yield (2S,5S)-tert-butyl 2-(hydroxymethyl)-5-methylpyrrolidine-1-carboxylate as a clear oil (5.15 g, 23.9 mmol, 93%) and was used directly in the following step.

(2S,5S)-tert-butyl 2-formyl-5-methylpyrrolidine-1-carboxylate. To a solution of (2S,5S)-tert-butyl 2-(hydroxymethyl)-5-methylpyrrolidine-1-carboxylate (5.15 g, 23.9 mmol) in dichloromethane, was added TEMPO (0.075 g, 0.48 mmol), sodium bromide (0.246 g, 2.39 mmol) and sodium bicarbonate (0.442 g, 5.26 mmol). Sodium hypochlorite (2.67 g, 35.9 mmol) of a 6% solution was added and the biphasic mixture was vigorously stirred for 2 hours at room temperature. The reaction mixture was extracted two times with dichloromethane (2×100 mL). The organic layers were combined and washed with saturated sodium thiosulfate solution, dried with sodium sulfate and the solvent was removed in vacuo to yield (2S,5S)-tert-butyl 2-formyl-5-methylpyrrolidine-1-carboxylate (3.9 g, 18.29 mmol, 77%) as a slight colored oil and was used directly in the following step.

(2S,5S)-tert-butyl 2-(1H-imidazol-2-yl)-5-methylpyrrolidine-1-carboxylate. To a solution of (2S,5S)-tert-butyl 2-formyl-5-methylpyrrolidine-1-carboxylate (3.9g, 18.30 mmol) in MeOH (15 mL) and ammonium hydroxide (15 mL, 99.9%), glyoxal (11.7 mL, 40% w/v in water, 102.40 mmol) was added dropwise. The biphasic mixture turned orange and turbid. The reaction was stirred vigorously overnight at room temperature. The solvent was removed in vacuo. The crude mixture was redissolved in ethyl acetate and washed with water. The aqueous layer was washed an additional time with ethyl acetate. The organic layers were combined and washed with brine, dried with sodium sulfate and the solvent was removed in vacuo. The crude material was purified by column chromatography 85% to 100% ethyl acetate in hexanes to yield (2S,5S)-tert-butyl 2-(1H-imidazol-2-yl)-5-methylpyrrolidine-1-carboxylate as an off white solid (3.47 g, 13.8 mmol, 75%). LCMS-ESI$^+$: calc'd for $C_{13}H_{21}N_3O_2$: 251.16 (M$^+$); Found: 252.20 (M+H$^+$).

(2S,5S)-tert-butyl 2-(4,5-diiodo-1H-imidazol-2-yl)-5-methylpyrrolidine-1-carboxylate. A 500 ml round bottom flask was charged with (2S,5S)-tert-butyl 2-(1H-imidazol-2-yl)-5-methylpyrrolidine-1-carboxylate (3.47 g, 13.8 mmol), iodine (7.7 g, 30.4 mmol) and sodium carbonate (4.54 g, 42.8 mmol). Dioxane (70 mL) and water (45 mL) was added to mixture and the reaction was stirred vigorously overnight in the dark. The reaction was then partitioned between ethyl acetate and a 10% aqueous solution of sodium thiosulfate and extracted. The aqueous layer was extracted an additional time with ethyl acetate. The organic layers were combined, dried with sodium sulfate and the solvent was removed in vacuo. The crude material was filtered through a plug of silica with 25% ethyl acetate in hexanes to yield (2S,5S)-tert-butyl 2-(4,5-diiodo-1H-imidazol-2-yl)-5-methylpyrrolidine-1-carboxylate as a white solid (4.28 g, 8.50 mmol, 62%). LCMS-ESI$^+$: calc'd for $C_{13}H_{19}I_2N_3O_2$: 502.96 (M$^+$); Found: 503.94 (M+H$^+$).

(2S,5S)-tert-butyl 2-(5-iodo-1H-imidazol-2-yl)-5-methylpyrrolidine-1-carboxylate. To a solution of (2S,5S)-tert-butyl 2-(4,5-diiodo-1H-imidazol-2-yl)-5-methylpyrrolidine-1-carboxylate (4.28 g, 8.50 mmol) in ethanol (75 mL) and water (75 mL), sodium thiosulfate (10.72 g, 85.1 mmol) was added and the reaction mixture was stirred vigorously for 1 hour at 100° C., 16 hours at 90° C., and 5 hours at 100° C. The reaction mixture was partitioned between ethyl acetate and water. The aqueous layer was washed additionally with ethyl acetate and the organic layers were combined. The organic layer was dried with sodium sulfate, concentrated and the crude material was purified by column chromatography to yield (2S,5S)-tert-butyl 2-(5-iodo-1H-imidazol-2-yl)-5-methylpyrrolidine-1-carboxylate as a white solid (2.34 g, 6.20 mmol, 73%). $^1$H NMR (400 MHz, cdcl$_3$) δ 7.04 (s, 1H), 4.89 (dd, 1H), 3.92 (m, 1H), 2.91 (s, 1H), 2.18-2.06 (m, 2H), 1.78 (m, 1H), 1.52 (m, 1H), 1.48 (s, 9H), 1.13 (d, 3H).

(2S)-1-[(2S,5S)-2-(5-iodo-1H-imidazol-2-yl)-5-methylpyrrolidin-1-yl]-2-[(1-methoxyethenyl)amino]-3-methylbutan-1-one. A round bottom flask was charged with (2S,5S)-tert-butyl 2-(5-iodo-1H-imidazol-2-yl)-5-methylpyrrolidine-1-carboxylate (1.5 g, 3.98 mmol) and treated with an excess of hydrochloric acid (100 mL of 4.0M in dioxane). The mixture was stirred vigorously for 3 hours in which time a precipitate formed and the solvent was removed in vacuo. To a mixture of the crude intermediate, (S)-2-(methoxycarbonylamino)-3-methylbutanoic acid (0.836 g, 4.77 mmol), HATU (1.81 g, 4.77 mmol) in dichloromethane (25 mL), diisopropylethylamine (3.46 mL, 19.9 mmol) was then added dropwise and was stirred over night under nitrogen. The reaction mixture was partitioned ethyl acetate and saturated sodium bicarbonate. The organic layer was dried with sodium sulfate, the solvent removed in vacuo. The crude product was purified by column chromatography to yield (2S)-1-[(2S,5S)-2-(5-iodo-1H-imidazol-2-yl)-5-methylpyrrolidin-1-yl]-2-[(1-methoxyethenyl)amino]-3-methylbutan-1-one as a white solid (1.63 g, 3.75 mmol, 94%). LCMS-ESI$^+$: calc'd for $C_{15}H_{23}IN_4O_3$: 434.08 (M$^+$); Found: 435.51 (M+H$^+$).

Example NP

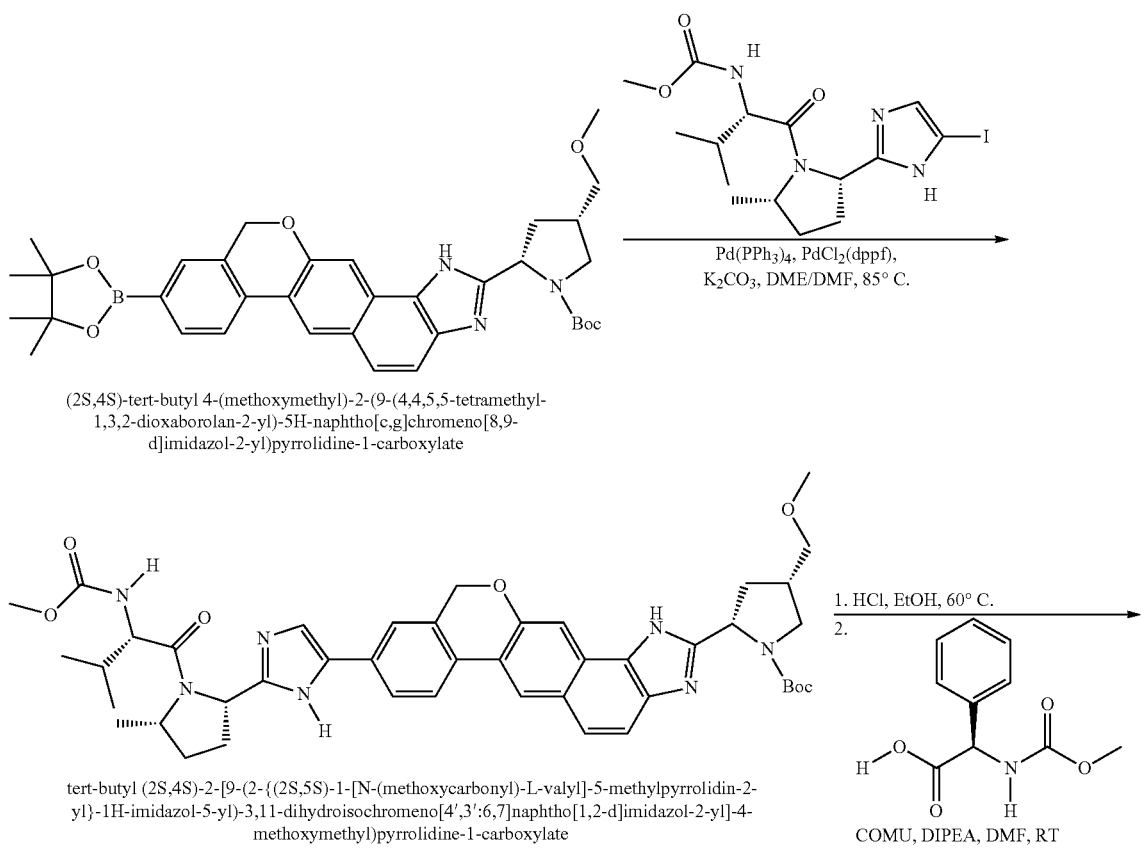

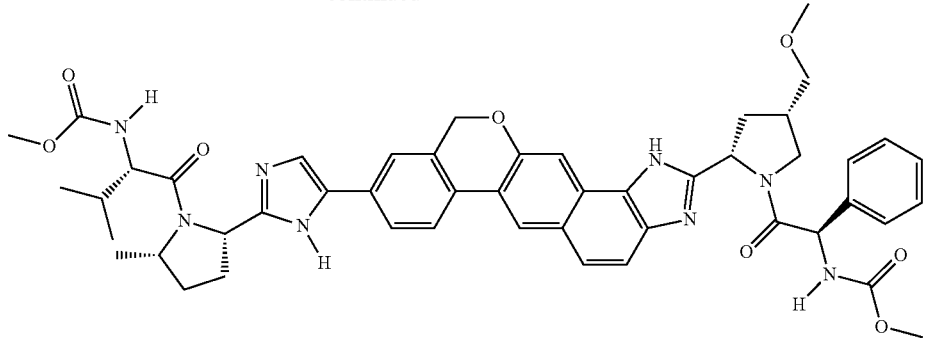

Methyl {(2S)-1-[(2S,5S)-2-(5-{2-[(2S,4S)-1-{(2R)-2-[(methoxycarbonyl)amino]-2-phenylacetyl}-4-(methoxymethyl)pyrrolidin-2-yl]-1,11 dihydroisochromeno[4′,3′:6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S,4S)-1-{(2R)-2-[(methoxycarbonyl)amino]-2-phenylacetyl}-4-(methoxymethyl)pyrrolidin-2-yl]-1,11 dihydroisochromeno[4′,3′:6,7]naphtho[1,2-d]imidazol-9-yl}-1H-imidazol-2-yl)-5-methylpyrrolidin-1-yl]-3-methyl-1-oxobutan-2-yl}carbamate. The synthesis of this compound was prepared according to the procedure of example LR-1 with the following modification. During the suzuki coupling, methyl (S)-1-((2S,5S)-2-(5-iodo-1H-imidazol-2-yl)-5-methylpyrrolidin-1-yl)-3-methyl-1-oxobutan-2-ylcarbamate was used in lieu of methyl (S)-1-((S)-2-(5-bromo-1H-imidazol-2-yl)pyrrolidin-1-yl)-3-methyl-1-oxobutan-2-ylcarbamate. The crude material was purified by preparative HPLC to provide methyl {(2S)-1-[(2S,5S)-2-(5-{2-[(2S,4S)-1-{(2R)-2-[(2S,4S)-1-{(2R)-2-[(methoxycarbonyl)amino]-2-phenylacetyl}-4-(methoxymethyl) pyrrolidin-2-yl]-1,11 dihydroisochromeno[4′,3′:6,7]naphtho[1,2-d]imidazol-9-yl}-1H-imidazol-2-yl)-5-methylpyrrolidin-1-yl]-3-methyl-1-oxobutan-2-yl}carbamate as a white solid (17 mg, 0.019 mmol, 17%). $^1$H NMR (400 MHz, cd$_3$od) δ 8.63 (s, 1H), 8.19 (d, 1H), 8.04 (m, 1H), 7.87 (m, 2H), 7.66 (m, 2H), 7.52-7.39 (m, 6H), 5.50 (m, 2H), 5.32 (s, 2H), 5.16 (m, 1H), 4.12 (m, 1H), 3.80 (m, 4H), 3.66 (s, 6H), 3.43 (m, 4H), 3.23 (s, 3H), 2.72-1.99 (m, 9H), 1.56 (d, 3H), 1.29 (m, 1H), 0.99 (d, 3H), 0.88 (d, 3H).

Example NQ

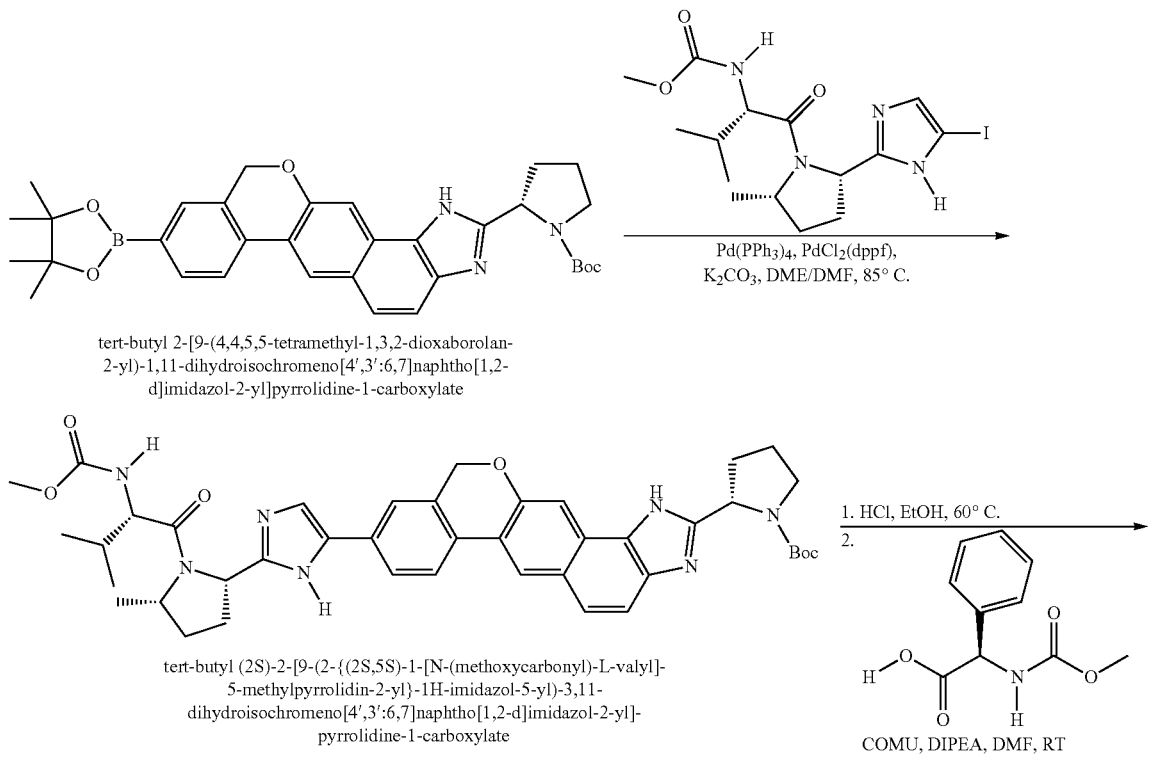

tert-butyl 2-[9-(4,4,5,5-tetramethyl-1,3,2-dioxaborolan-2-yl)-1,11-dihydroisochromeno[4′,3′:6,7]naphtho[1,2-d]imidazol-2-yl]pyrrolidine-1-carboxylate tert-butyl (2S)-2-[9-(2-{(2S,5S)-1-[N-(methoxycarbonyl)-L-valyl]-5-methylpyrrolidin-2-yl}-1H-imidazol-5-yl)-3,11-dihydroisochromeno[4′,3′:6,7]naphtho[1,2-d]imidazol-2-yl]-pyrrolidine-1-carboxylate

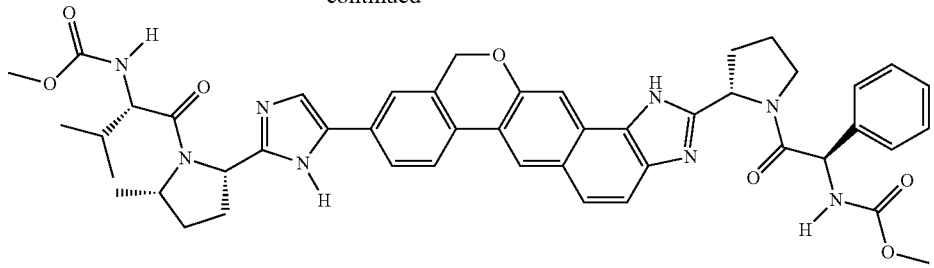

methyl {(2S)-1-[(2S,5S)-2-(5-{2-[(2S)-1-{(2R)-2-[(methoxycarbonyl)amino]-2-phenylacetyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S)-1-{(2R)-2-[(methoxycarbonyl)amino]-2-phenylacetyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate. The synthesis of this compound was prepared according to the procedure of example LQ with the following modification. During the Suzuki coupling, (2S)-1-[(2S,5S)-2-(5-iodo-1H-imidazol-2-yl)-5-methylpyrrolidin-1-yl]-2-[(1-methoxyethenyl)amino]-3-methylbutan-1-one was used in lieu of (2S)-1-[(2S)-2-(5-bromo-1H-imidazol-2-yl)pyrrolidin-1-yl]-2-[(1-methoxyethenyl)amino]-3-methylbutan-1-one. The crude material was purified by preparative HPLC to provide methyl {(2S)-1-[(2S,5S)-2-(5-{2-[(2S)-1-{(2R)-2-[(methoxycarbonyl)amino]-2-phenylacetyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate as a white solid (110 mg, 0.131 mmol, 57%). $^1$H NMR (400 MHz, cd$_3$od) δ 8.65 (s, 1H), 8.21 (d, 1H), 8.04 (m, 2H), 7.91 (s, 1H), 7.81 (m, 1H), 7.67 (m, 2H), 7.46 (m, 6H), 5.59 (s, 1H), 5.50 (dd, 1H), 5.33 (s, 2H), 5.22-5.09 (m, 1H), 4.14 (m, 2H), 3.74 (s, 1H), 3.65 (m, 6H), 3.52-3.37 (m, 2H), 2.60-1.89 (m, 11H), 1.56 (d, 3H), 1.29 (d, 1H), 0.99 (d, 3H), 0.88 (d, 3H).

Example NR

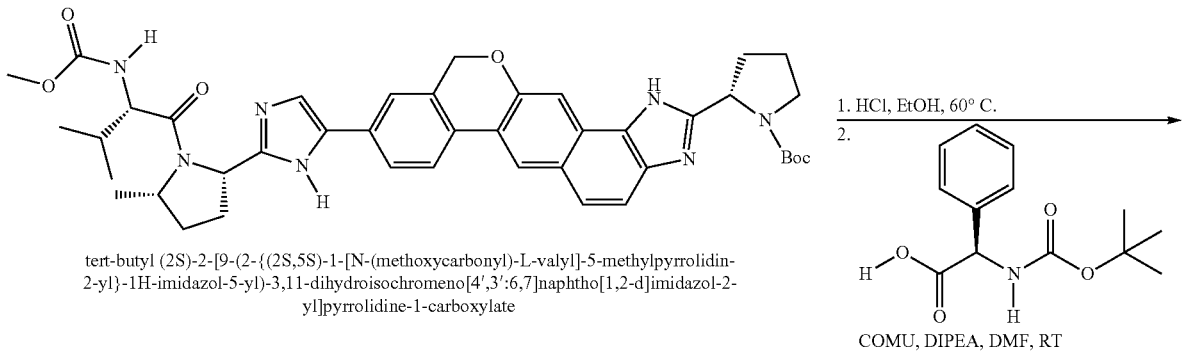

tert-butyl (2S)-2-[9-(2-{(2S,5S)-1-[N-(methoxycarbonyl)-L-valyl]-5-methylpyrrolidin-2-yl}-1H-imidazol-5-yl)-3,11-dihydroisochromeno[4',3':6,7]naphtho[1,2-d]imidazol-2-yl]pyrrolidine-1-carboxylate

COMU, DIPEA, DMF, RT

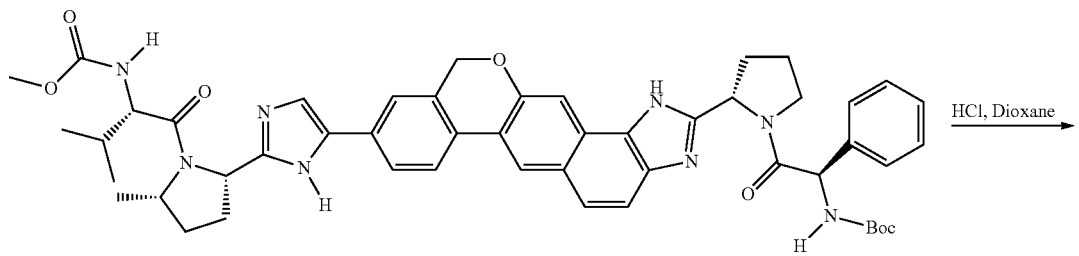

methyl {(2S)-1-[(2S,5S)-2-(5-{2-[(2S)-1-{(2R)-2-[(tert-butoxycarbonyl)amino]-2-phenylacetyl}pyrrolidin-2-yl]-3,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate -continued

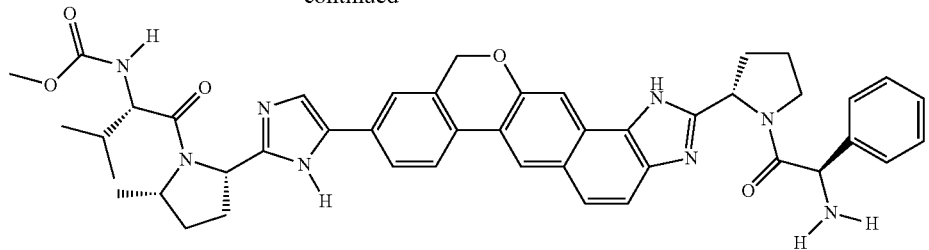

methyl [(2S)-1-{(2S,5S)-2-[5-(2-{(2S)-1-[(2R)-2-amino-2-phenylacetyl]pyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl]carbamate Methyl [(2S)-1-{(2S,5S)-2-[5-(2-{(2S)-1-[(2R)-2-amino-2-phenylacetyl]pyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl]carbamate. The synthesis of this compound was prepared according to the procedure of NQ with the following modifications. During the amide coupling, (R)-2-(tert-butoxycarbonylamino)-2-phenylacetic acid was used in lieu of (R)-2-(methoxycarbonylamino)-2-phenylacetic acid. This was then treated with an excess of hydrochloric acid (15 ml, 4.0 M in Dioxane) for 2 hours. The crude product was purified by HPLC to provide methyl [(2S)-1-{(2S,5S)-2-[5-(2-{(2S)-1-[(2R)-2-amino-2-phenylacetyl]pyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl]carbamate as a white solid (153 mg, 0.196 mmol, 74%). $^1$H NMR (400 MHz, cd$_3$od) δ 8.63 (s, 1H), 8.20 (d, 1H), 7.99 (m, 1H), 7.93 (m, 2H), 7.80 (m, 2H), 7.72-7.64 (m, 2H), 7.63-7.52 (m, 5H), 5.52 (dd, 1H), 5.44 (m, 1H), 5.33 (s, 2H), 5.21-5.10 (m, 1H), 4.80 (m, 2H), 4.14 (m, 1H), 4.02 (m, 1H), 3.75 (s, 1H), 3.67 (s, 3H), 3.12 (dd, 1H), 2.72-2.13 (m, 7H), 2.00 (m, 3H), 1.56 (d, 3H), 1.30 (d, 1H), 0.98 (d, 3H), 0.88 (d, 3H).

Example NS

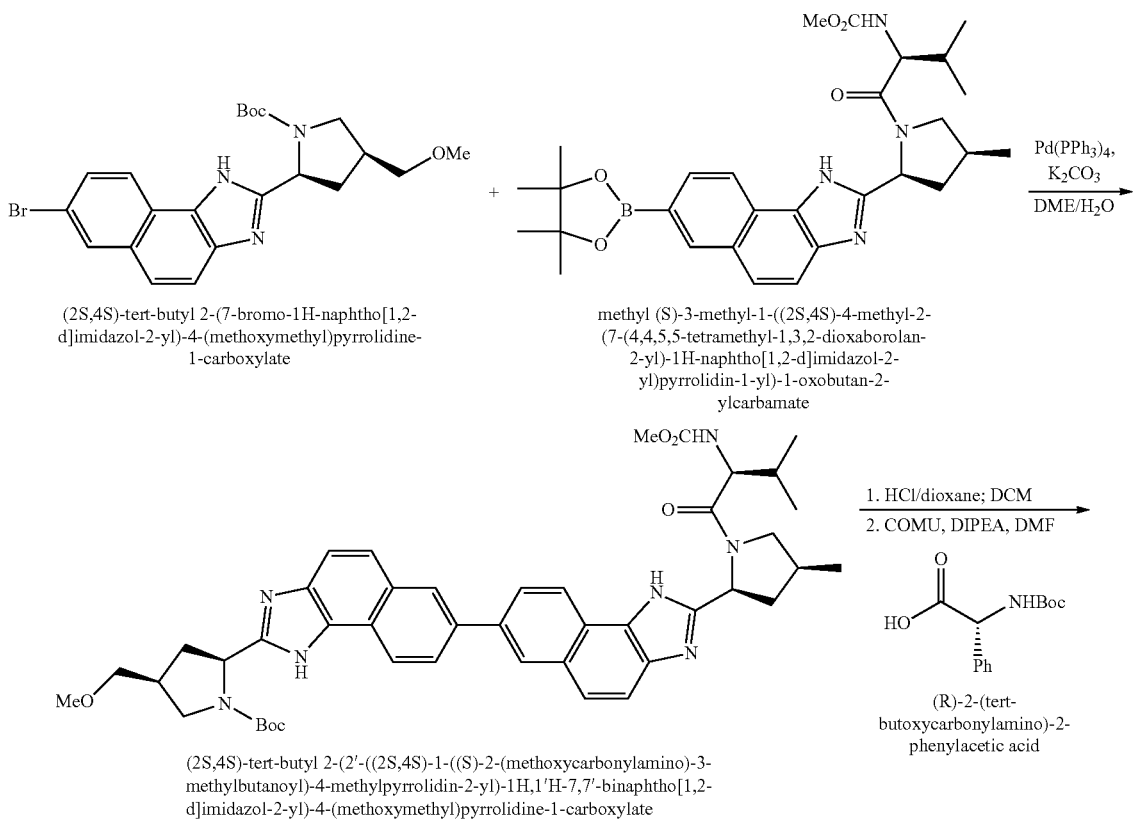

-continued

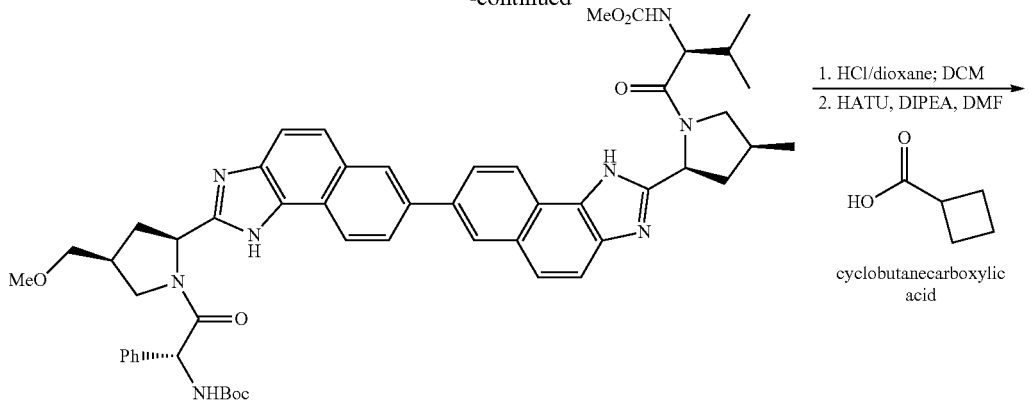

methyl (S)-1-((2S,4S)-2-(2'-((2S,4S)-1-((R)-2-tert-butoxycarbonylamino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate 1. HCl/dioxane; DCM
2. HATU, DIPEA, DMF cyclobutanecarboxylic acid

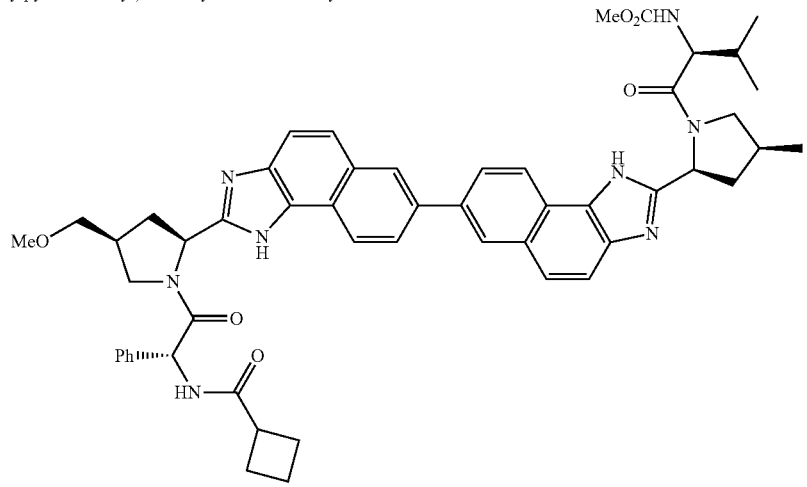

methyl (S)-1-((2S,4S)-2-(2'-((2S,4S)-1-((R)-2-(cyclobutanecarboxamido)-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate (2S,4S)-tert-Butyl 2-(2'-((2S,4S)-1-((S)-2-(methoxycarbonylamino)-3-methylbutanoyl)-4-methylpyrrolidin-2-yl)-1H, 1'H-7,7'-binaphtho[1,2-d]imidazol-2-yl)-4-(methoxymethyl)pyrrolidine-1-carboxylate was synthesized from (2S,4S)-tert-butyl 2-(7-bromo-1H-naphtho[1,2-d]imidazol-2-yl)-4-(methoxymethyl)pyrrolidine-1-carboxylate and methyl (S)-3-methyl-1-((2S,4S)-4-methyl-2-(7-(4,4,5,5-tetramethyl-1,3,2-dioxaborolan-2-yl)-1H-naphtho[1,2-d]imidazol-2-yl)pyrrolidin-1-yl)-1-oxobutan-2-ylcarbamate using the same conditions employed in the synthesis of methyl {(2S)-1-[(2S,4S)-2-{2'-[(2S)-1-{(2S)-2-[(methoxycarbonyl)amino]-3-methylbutanoyl}pyrrolidin-2-yl]-1H,1'H-7,7'-binaphtho[1,2-d]imidazol-2-yl]-4-(methoxymethyl)pyrrolidin-1-yl]-3-methyl-1-oxobutan-2-yl}carbamate.

Methyl (S)-1-((2S,4S)-2-(2'-((2S,4S)-1-((R)-2-tert-butoxycarbonylamino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate was synthesized from (2S,4S)-tert-butyl 2-(2'-((2S,4S)-1-((S)-2-(methoxycarbonylamino)-3-methylbutanoyl)-4-methylpyrrolidin-2-yl)-1H,1'H-7,7'-binaphtho[1,2-d]imidazol-2-yl)-4-(methoxymethyl)pyrrolidine-1-carboxylate using the same methods employed in the synthesis of methyl {(1R)-2-[(2S,4S)-2-[7-(4-{2-[(2S)-1-{(2S)-2-[(methoxycarbonyl)amino]-3-methylbutanoyl}pyrrolidin-2-yl]-1H-imidazol-5-yl}phenyl)-1H-naphtho[1,2-d]imidazol-2-yl]-4-(methoxymethyl)pyrrolidin-1-yl]-2-oxo-1-phenylethyl}carbamate from (2S,4S)-tert-butyl 2-(7-(4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-4-(methoxymethyl)pyrrolidine-1-carboxylate, substituting (R)-2-(tert-butoxycarbonylamino)-2-phenylacetic acid for (R)-2-(methoxycarbonylamino)-2-phenylacetic acid.

Methyl (S)-1-((2S,4S)-2-(2'-((2S,4S)-1-((R)-2-(cyclobutanecarboxamide)-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate: Methyl (S)-1-((2S,4S)-2-(2'-((2S,4S)-1-((R)-2-tert-butoxycarbonylamino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate (98 mg, 0.106 mmol) was dissolved in DCM (2.5 mL) and treated with HCl (4.0 M in dioxane, 0.5 mL). After stirring for 1 h, the reaction mixture was concentrated under vacuum. The crude residue was treated with cyclobutanecarboxylic acid (0.051 mL, 0.53 mmol), HATU (48 mg, 0.13 mmol), DMF (2 mL) and DIPEA (0.185 mL, 1.06 mmol). After stirring at RT for 20 min, the reaction was quenched with water and the mixture was purified by reverse-phase HPLC to afford methyl (S)-1-((2S,4S)-2-(2'-((2S,4S)-1-((R)-2-(cyclobutanecarboxamide)-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate (87 mg). MS (ESI) m/z 904 [M+H]+. 1H NMR (400 MHz, cd3od) δ 8.62 (d, J=8.5 Hz, 1H), 8.40 (d, J=12.4 Hz, 3H), 8.10 (d, J=6.5 Hz, 2H), 8.01 (d, J=9.0 Hz, 2H), 7.71 (d, J=8.9 Hz, 2H), 7.53 (dd, J=7.8, 1.4 Hz, 2H), 7.50-7.40 (m, 3H), 5.68 (s, 1H), 5.61 (t, J=8.2 Hz, 1H), 5.43 (dd, J=10.9, 7.0 Hz, 1H), 4.41 (t, J=8.5 Hz, 1H), 4.35 (d, J=7.0 Hz, 1H), 3.92 (t, J=9.5 Hz, 1H), 3.81 (dd, J=21.9, 12.1 Hz, 1H), 3.68 (s, 3H), 3.61 (t, J=10.5 Hz, 1H), 3.44 (qd, J=9.6, 5.4 Hz, 2H), 3.27-3.11 (m, 4H), 2.78 (dt, J=12.5, 7.8 Hz, 2H), 2.64 (td, J=12.6, 6.5 Hz, 2H), 2.45-2.27 (m, 1H), 2.26-1.85 (m, 8H), 1.86-1.71 (m, 1H), 1.29 (d, J=6.3 Hz, 4H), 1.07-0.80 (m, 7H).

Example NT

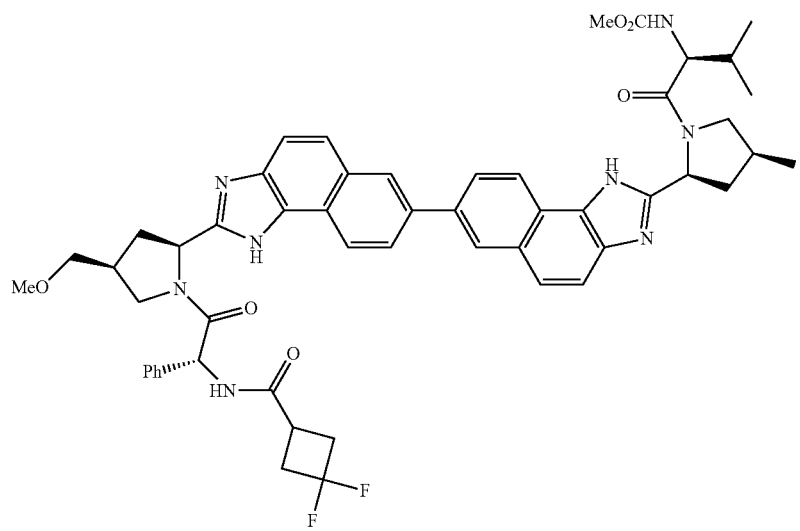

methyl (S)-1-((2S,4S)-2-(2'-((2S,4S)-1-((R)-2-(3,3-difluorocyclobutanecarboxamido)-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate Methyl (S)-1-((2S,4S)-2-(2'-((2S,4S)-1-((R)-2-(3,3-difluorocyclobutanecarboxamido)-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate was synthesized from methyl (S)-1-((2S,4S)-2-(2'-((2S,4S)-1-((R)-2-tert-butoxycarbonylamino-2-phenylacetyl)-4-(methoxymethyl)pyrrolidin-2-yl)-1H, 1'H-7,7'-binaphtho[1,2-d]imidazol-2-yl)-4-methylpyrrolidin-1-yl)-3-methyl-1-oxobutan-2-ylcarbamate using the same methods employed in the synthesis of methyl (S)-1-((2S,4S)-2-(2'-((2S,4S)-1-((R)-2-(cyclobutanecarboxamide)-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate, substituting 3,3-difluorocyclobutanecarboxylic acid for cyclobutanecarboxylic acid. MS (ESI) m/z 940 [M+H]+.

Example NU

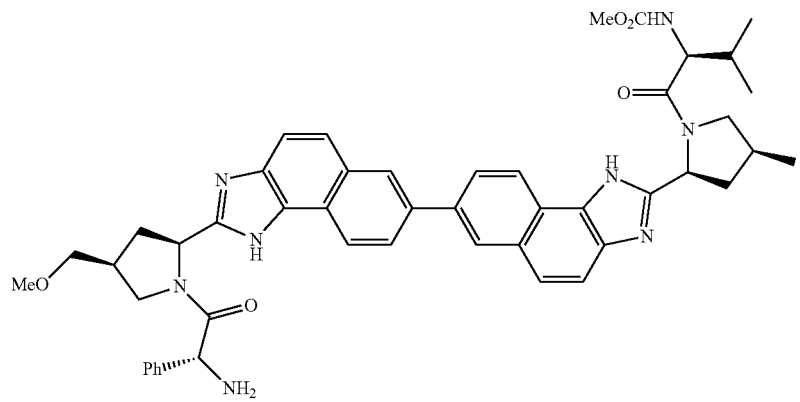

methyl (S)-1-((2S,4S)-2-(2'-((2S,4S)-1-((R)-2-amino-2-phenylacetyl)-4-(methoxymethyl)pyrrolidin-2-yl)-1H, 1'H-7,7'-binaphtho[1,2-d]imidazol-2-yl)-4-methylpyrrolidin-1-yl)-3-methyl-1-oxobutan-2-ylcarbamate Methyl (S)-1-((2S,4S)-2-(2'-((2S,4S)-1-((R)-2-amino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate was synthesized from methyl (S)-1-((2S,4S)-2-(2'-((2S,4S)-1-((R)-2-tert-butoxycarbonylamino-2-phenylacetyl)-4-(methoxymethyl)pyrrolidin-2-yl)-1H, 1'H-7,7'-binaphtho[1,2-d]imidazol-2-yl)-4-methylpyrrolidin-1-yl)-3-methyl-1-oxobutan-2-ylcarbamate using the same methods employed in the synthesis of methyl (S)-1-((2S,4S)-2-(2'-((2S,4S)-1-((R)-2-(cyclobutanecarboxamide)-2-phenylacetyl)-4-(methoxymethyl)pyrrolidin-2-yl)-1H, 1'H-7,7'-binaphtho[1,2-d]imidazol-2-yl)-4-methylpyrrolidin-1-yl)-3-methyl-1-oxobutan-2-ylcarbamate, omitting the final HATU coupling step. MS (ESI) m/z 821 [M+H]+.

Example NV

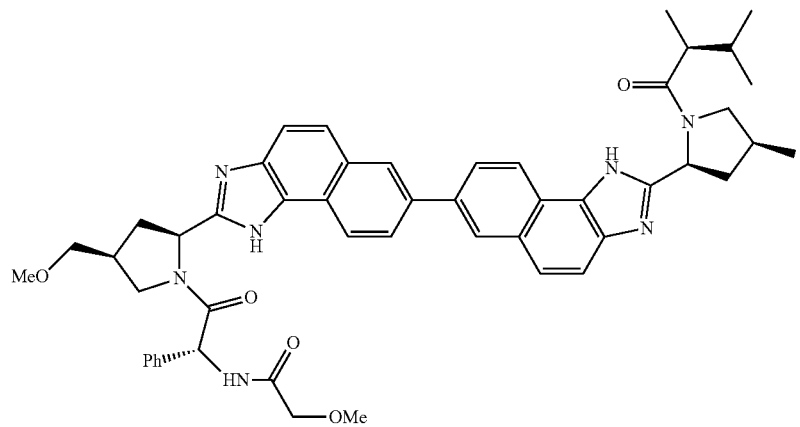 [SMILES: COCC(=O)N[C@@H](C(=O)N1C[C@@H](COC)C[C@H]1c1nc2ccc3cc(-c4ccc5c(ccc6nc([C@@H]7C[C@H](C)CN7C(=O)[C@@H](C)C(C)C)[nH]c65)c4)ccc3c2[nH]1)c1ccccc1]

methyl (S)-1-((2S,4S)-2-(2'-((2S,4S)-1-((R)-2-(2-methoxyacetamido)-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate Methyl (S)-1-((2S,4S)-2-(2'-((2S,4S)-1-((R)-2-(2-methoxyacetamido)-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate was synthesized from methyl (S)-1-((2S,4S)-2-(2'-((2S,4S)-1-((R)-2-tert-butoxycarbonylamino-2-phenylacetyl)-4-(methoxymethyl)pyrrolidin-2-yl)-1H, 1'H-7,7'-binaphtho[1,2-d]imidazol-2-yl)-4-methylpyrrolidin-1-yl)-3-methyl-1-oxobutan-2-ylcarbamate using the same methods employed in the synthesis of methyl (S)-1-((2S,4S)-2-(2'-((2S,4S)-1-((R)-2-(cyclobutanecarboxamide)-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate, substituting 2-methoxyacetic acid for cyclobutanecarboxylic acid. MS (ESI) m/z 894 [M+H]$^+$.

Example NW

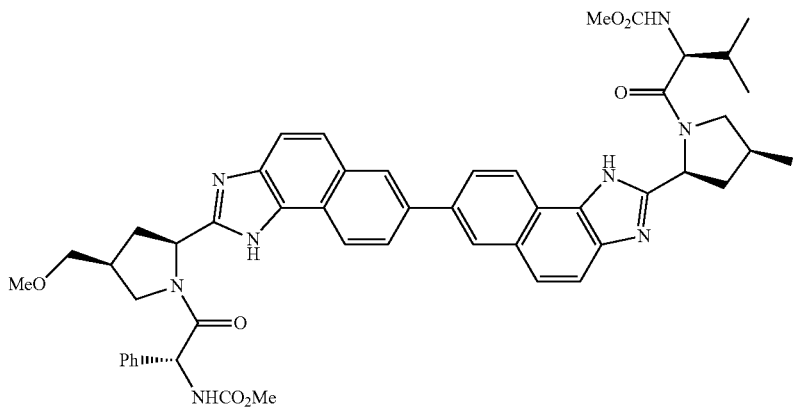

methyl (S)-1-((2S,4S)-2-(2'-((2S,4S)-1-((R)-2-methoxycarbonylamino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate Methyl (S)-1-((2S,4S)-2-(2'-((2S,4S)-1-((R)-2-methoxycarbonylamino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate was synthesized from (2S,4S)-tert-butyl 2-(2'-((2S,4S)-1-((S)-2-(methoxycarbonylamino)-3-methylbutanoyl)-4-methylpyrrolidin-2-yl)-1H,1'H-7,7'-binaphtho[1,2-d]imidazol-2-yl)-4-(methoxymethyl)pyrrolidine-1-carboxylate using the same method employed in the synthesis of methyl (S)-1-((2S,4S)-2-(2'-((2S,4S)-1-((R)-2-tert-butoxycarbonylamino-2-phenylacetyl)-4-(methoxymethyl)pyrrolidin-2-yl)-1H, 1'H-7,7'-binaphtho[1,2-d]imidazol-2-yl)-4-methylpyrrolidin-1-yl)-3-methyl-1-oxobutan-2-ylcarbamate, substituting (R)-2-(methoxycarbonylamino)-2-phenylacetic acid for (R)-2-(tert-butoxycarbonylamino)-2-phenylacetic acid. MS (ESI) m/z 880 [M+H]$^+$. $^1$H NMR (400 MHz, cd$_3$od) δ 8.31 (dd, J=21.3, 7.6 Hz, 4H), 7.96 (d, J=8.4 Hz, 2H), 7.88 (dd, J=8.7, 3.3 Hz, 2H), 7.66-7.54 (m, 2H), 7.46 (ddd, J=21.7, 14.4, 6.9 Hz, 4H), 5.62-5.49 (m, 2H), 5.43 (dd, J=10.8, 7.1 Hz, 1H), 4.54-4.18 (m, 2H), 3.88 (t, J=9.8 Hz, 1H), 3.77 (dd, J=22.6, 13.3 Hz, 1H), 3.73-3.54 (m, 6H), 3.46 (ddd, J=15.6, 9.6, 5.5 Hz, 2H), 3.36-3.29 (m, 1H), 2.73 (dd, J=12.5, 6.7 Hz, 2H), 2.67-2.49 (m, 2H), 2.30-2.11 (m, 2H), 2.09-1.94 (m, 1H), 1.36-1.17 (m, 4H), 1.10-0.83 (m, 6H).

Example NX

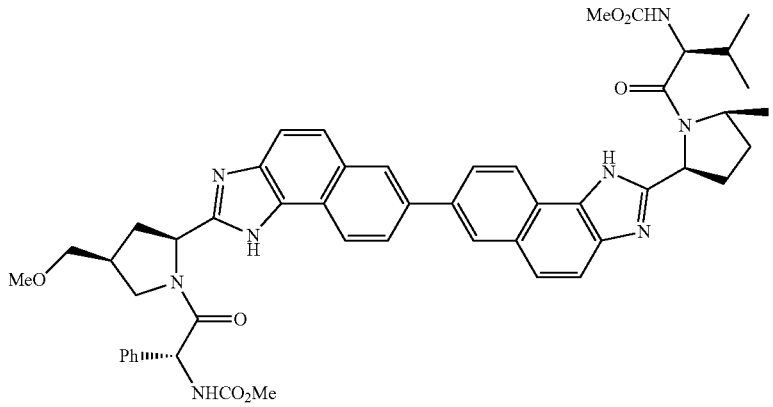

methyl (S)-1-((2S,5S)-2-(2'-((2S,4S)-1-((R)-2-methoxycarbonylamino-2-phenylacetyl)-4-(methoxymethyl)pyrrolidin-2-yl)-1H, 1'H-7,7'-binaphtho[1,2-d]imidazol-2-yl)-5-methylpyrrolidin-1-yl)-3-methyl-1-oxobutan-2-ylcarbamate Methyl (S)-1-((2S,5S)-2-(2'-((2S,4S)-1-((R)-2-methoxycarbonylamino-2-phenylacetyl)-4-(methoxymethyl)pyrrolidin-2-yl)-1H,1'H-7,7'-binaphtho[1,2-d]imidazol-2-yl)-5-methylpyrrolidin-1-yl)-3-methyl-1-oxobutan-2-ylcarbamate was synthesized according to the method described for the synthesis of methyl (S)-1-((2S,4S)-2-(2'-((2S,4S)-1-((R)-2-methoxycarbonylamino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate, substituting methyl (S)-3-methyl-1-((2S,5S)-2-methyl-5-(7-(4,4,5,5-tetramethyl-1,3,2-dioxaborolan-2-yl)-1H-naphtho[1,2-d]imidazol-2-yl)pyrrolidin-1-yl)-1-oxobutan-2-ylcarbamate for methyl (S)-3-methyl-1-((2S,4S)-4-methyl-2-(7-(4,4,5,5-tetramethyl-1,3,2-dioxaborolan-2-yl)-1H-naphtho[1,2-d]imidazol-2-yl)pyrrolidin-1-yl)-1-oxobutan-2-ylcarbamate. MS (ESI) m/z 880 [M+H]$^+$. $^1$H NMR (400 MHz, cd$_3$od) δ 8.58-8.52 (m, 1H), 8.47 (d, J=9.5 Hz, 2H), 8.27 (d, J=8.3 Hz, 1H), 8.17 (dd, J=19.0, 10.0 Hz, 2H), 8.09 (t, J=9.9 Hz, 1H), 7.82 (ddd, J=26.2, 18.1, 8.9 Hz, 2H), 7.45 (tt, J=13.5, 6.9 Hz, 5H), 5.56 (d, J=8.5 Hz, 2H), 5.37 (dd, J=10.7, 7.0 Hz, 1H), 4.23 (dd, J=23.8, 8.5 Hz, 1H), 3.88 (t, J=9.7 Hz, 1H), 3.82-3.65 (m, 4H), 3.62 (s, 3H), 3.54-3.38 (m, 2H), 3.35 (s, 1H), 3.26 (s, 3H), 2.80 (ddd, J=25.6, 20.1, 6.8 Hz, 1H), 2.68-2.27 (m, 4H), 2.24-1.89 (m, 3H), 1.67 (d, J=6.6 Hz, 2H), 1.32 (d, J=6.2 Hz, 1H), 1.20-1.02 (m, 1H), 0.94 (dd, J=26.4, 6.7 Hz, 5H).

Example NY

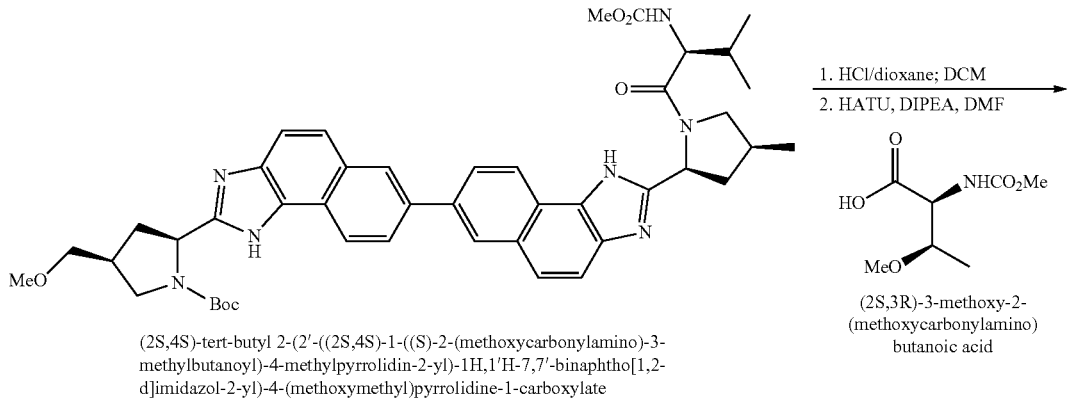

(2S,4S)-tert-butyl 2-(2'-((2S,4S)-1-((S)-2-(methoxycarbonylamino)-3-methylbutanoyl)-4-methylpyrrolidin-2-yl)-1H,1'H-7,7'-binaphtho[1,2-d]imidazol-2-yl)-4-(methoxymethyl)pyrrolidine-1-carboxylate (2S,3R)-3-methoxy-2-(methoxycarbonylamino) butanoic acid -continued

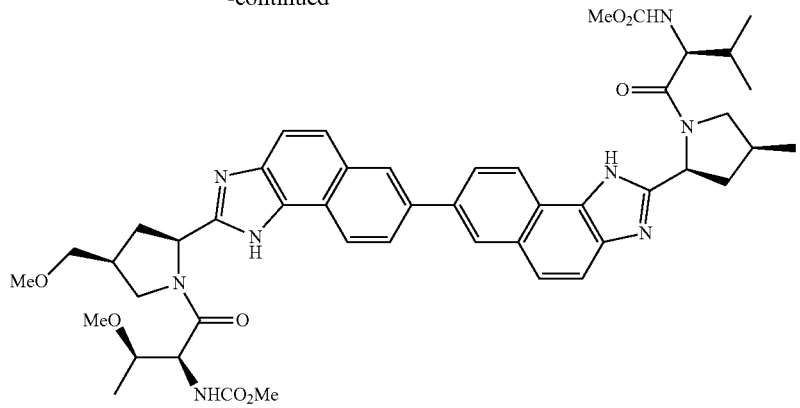

methyl (S)-1-((2S,4S)-2-(2'-((2S,4S)-1-((2S,3R)-2-methoxycarbonylamino-3-methoxybutanoyl)-4-(methoxymethyl)pyrrolidin-2-yl)-1H,1'H-7,7'–binaphtho[1,2-d]imidazol-2-yl)-4-methylpyrrolidin-1-yl)-3-methyl-1-oxobutan-2-ylcarbamate Methyl (S)-1-((2S,4S)-2-(2'-((2S,4S)-1-((2S,3R)-2-methoxycarbonylamino-3-methoxybutanoyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate: (2S,4S)-tert-Butyl 2-(2'-((2S,4S)-1-((S)-2-(methoxycarbonylamino)-3-methylbutanoyl)-4-methylpyrrolidin-2-yl)-1H,1'H-7,7'-binaphtho[1,2-d]imidazol-2-yl)-4-(methoxymethyl)pyrrolidine-1-carboxylate (120 mg, 0.152 mmol) was dissolved in DCM (5 mL) and treated with HCl (4.0 mL in dioxane, 1 mL). After stirring for 1 h, the reaction mixture was concentrated under reduced pressure. The crude residue was treated with (2S,3R)-3-methoxy-2-(methoxycarbonylamino)butanoic acid (35 mg, 0.18 mmol), HATU (69 mg, 0.18 mmol), DMF (1 mL) and DIPEA (0.26 mL, 1.5 mmol). After 20 min, the reaction was quenched with water. The product was purified by reverse-phase HPLC to afford methyl (S)-1-((2S,4S)-2-(2'-((2S,4S)-1-((2S,3R)-2-methoxycarbonylamino-3-methoxybutanoyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate (120 mg). MS (ESI) m/z 862 [M+H]$^+$.

Example NZ

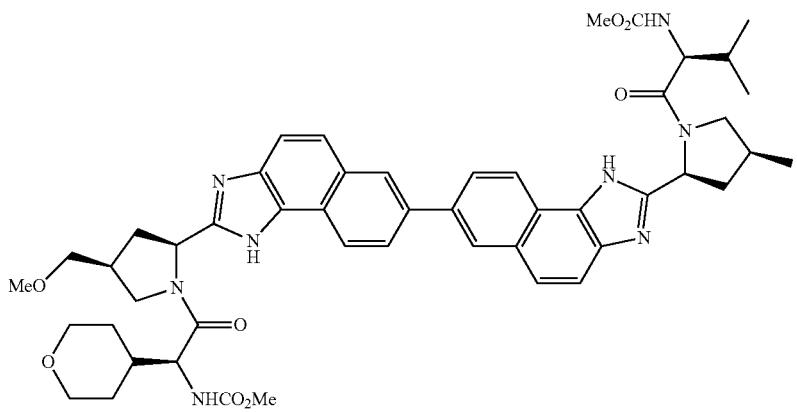

1355 methyl (S)-1-((2S,4S)-2-(2'-((2S,4S)-1-((S)-2-methoxycarbonylamino-2-(tetrahydro-2H-pyran-4-yl)acetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate Methyl (S)-1-((2S,4S)-2-(2'-((2S,4S)-1-((S)-2-methoxycarbonylamino-2-(tetrahydro-2H-pyran-4-yl)acetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate was prepared using a method analogous to that employed in the synthesis of methyl (S)-1-((2S,4S)-2-(2'-((2S,4S)-1-((2S,3R)-2-methoxycarbonylamino-3-methoxybutanoyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate, substituting (S)-2-(methoxycarbonylamino)-2-(tetrahydro-2H-pyran-4-yl)acetic acid for (2S,3R)-3-methoxy-2-(methoxycarbonylamino)butanoic acid. MS (ESI) m/z 888 [M+H]+.

Example OA

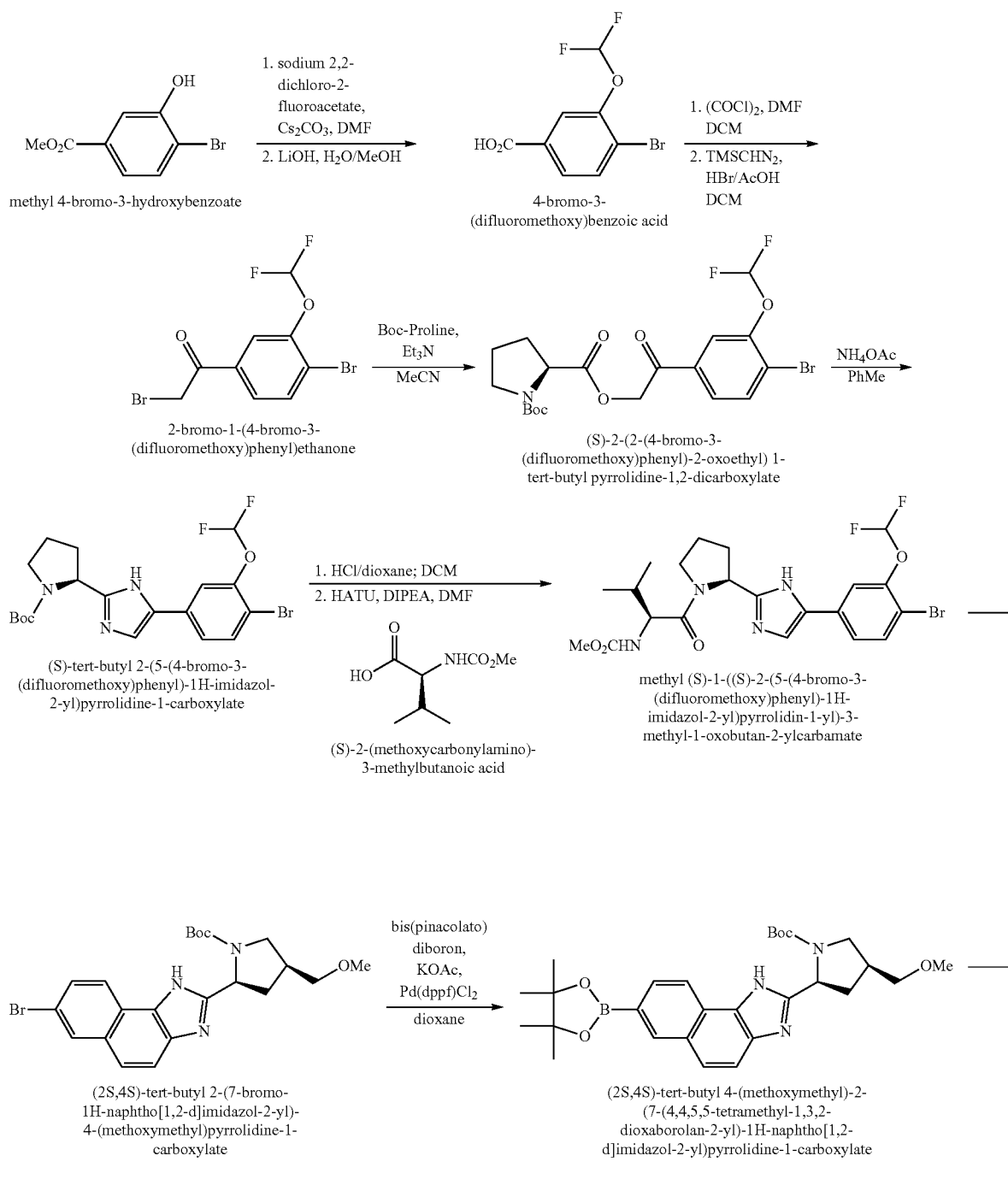

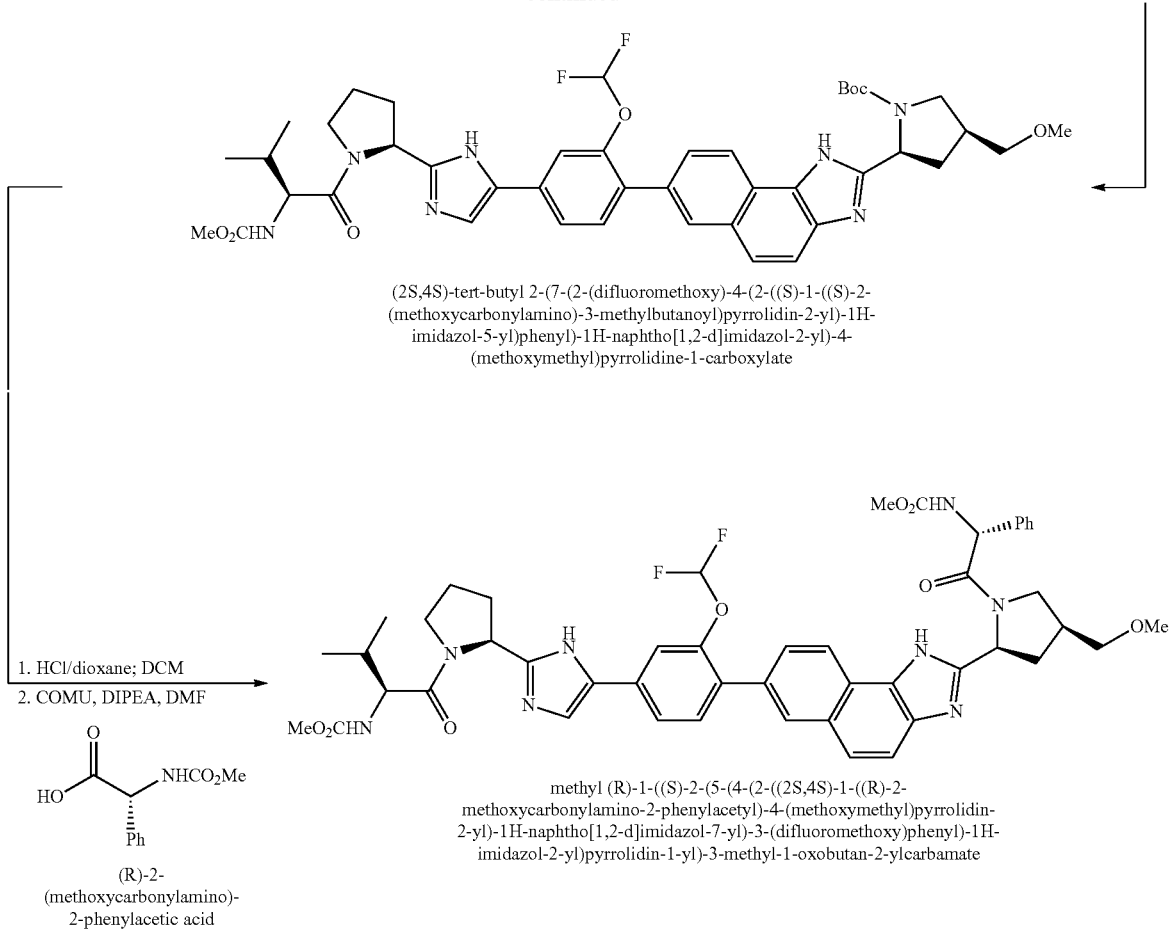

(2S,4S)-tert-butyl 2-(7-(2-(difluoromethoxy)-4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-4-(methoxymethyl)pyrrolidine-1-carboxylate 1. HCl/dioxane; DCM
2. COMU, DIPEA, DMF (R)-2-(methoxycarbonylamino)-2-phenylacetic acid methyl (R)-1-((S)-2-(5-(4-(2-((2S,4S)-1-((R)-2-methoxycarbonylamino-2-phenylacetyl)-4-(methoxymethyl)pyrrolidin-2-yl)-1H-naphtho[1,2-d]imidazol-7-yl)-3-(difluoromethoxy)phenyl)-1H-imidazol-2-yl)pyrrolidin-1-yl)-3-methyl-1-oxobutan-2-ylcarbamate 4-Bromo-3-(difluoromethoxy)benzoic acid: Methyl 4-bromo-3-hydroxybenzoate (2.31 g, 10 mmol), sodium 2,2-dichloro-2-fluoroacetate (4.57 g, 30 mmol) and Cs$_2$CO$_3$ (4.89 g, 15 mmol) were combined in DMF (50 mL). The stirred reaction mixture was heated to 80° C. for 22 h then cooled to RT. The reaction mixture was diluted with EtOAc and washed with water, saturated aqueous NaHCO$_3$ and brine, then dried over MgSO$_4$, filtered and concentrated. The crude residue was purified by silica column chromatography (0% to 20% EtOAc/Hex) to afford the difluoromethyl ether (1.87 g, 67%). The purified material was dissolved in MeOH (40 mL) and treated with LiOH (1.0 M in water, 10 mL). The reaction mixture was stirred at RT for 3d, then concentrated under reduced pressure to remove most of the MeOH. The aqueous solution was then poured into a separatory funnel containing water. The solution was acidified to pH 1-2 with 10% HCl, then extracted 3× with DCM. The combined organic fractions were dried over MgSO$_4$, filtered and concentrated to provide 4-bromo-3-(difluoromethoxy)benzoic acid (yield undetermined, material carried on crude assuming total conversion).

2-Bromo-1-(4-bromo-3-(difluoromethoxy)phenyl)ethanone: 4-Bromo-3-(difluoromethoxy)benzoic acid (6.65 mmol) was suspended in DCM (33 mL) and thionyl chloride (2.9 mL, 33 mmol) was added, followed by DMF (5 drops). After stirring at RT for 2 h, the reaction mixture was concentrated under reduced pressure. The crude residue was dissolved in DCM (17 mL) and treated with TMS-diazomethane (2.0 M in hexane, 8.3 mL, 16.6 mmol). After stirring at RT for 2 h, HBr (33% w/w in AcOH) (5.8 mL, 33 mmol) was added dropwise. After stirring for 1 h more at RT, the reaction mixture was concentrated under reduced pressure. The crude residue was diluted with EtOAc. The organic solution was washed with saturated aqueous NaHCO$_3$ and brine, then dried over MgSO$_4$, filtered and concentrated to afford 2-Bromo-1-(4-bromo-3-(difluoromethoxy)phenyl)ethanone (yield undetermined, material carried on crude assuming total conversion).

(S)-2-(2-(4-Bromo-3-(difluoromethoxy)phenyl)-2-oxoethyl) 1-tert-butyl pyrrolidine-1,2-dicarboxylate: 2-Bromo-1-(4-bromo-3-(difluoromethoxy)phenyl)ethanone (6.65 mmol) and Boc-proline (1.72 g, 7.98 mmol) were suspended in MeCN (13 mL) and triethylamine (1.00 mL, 7.32 mmol) was added. The reaction mixture was stirred at RT for 14 h, then diluted with EtOAc. The organic solution was washed with water saturated aqueous NaHCO$_3$ and brine, then dried over MgSO$_4$, filtered and concentrated under reduced pressure. The crude residue was purified by silica column chromatography (19% to 40% EtOAc/Hex) to afford (S)-2-(2-(4-bromo-3-(difluoromethoxy)phenyl)-2-oxoethyl) 1-tert-butyl pyrrolidine-1,2-dicarboxylate (2.48 g, 78% over 4 steps).

(S)-tert-Butyl 2-(5-(4-bromo-3-(difluoromethoxy)phenyl)-1H-imidazol-2-yl)pyrrolidine-1-carboxylate: (S)-2-(2-(4-Bromo-3-(difluoromethoxy)phenyl)-2-oxoethyl) 1-tert-butyl pyrrolidine-1,2-dicarboxylate (2.48 g, 5.19 mmol) and NH₄OAc (8.00 g, 104 mmol) were combined in PhMe. The stirred reaction mixture was heated to 100° C. for 3 h 20 min then cooled to RT and diluted with EtOAc. The organic solution was washed with water saturated aqueous NaHCO₃ 3× then dried over MgSO₄, filtered and concentrated under reduced pressure. The crude residue was purified by silica column chromatography (45% to 75% EtOAc/Hex) to afford (S)-tert-butyl 2-(5-(4-bromo-3-(difluoromethoxy)phenyl)-1H-imidazol-2-yl)pyrrolidine-1-carboxylate (1.51 g, 63%).

Methyl (S)-1-((S)-2-(5-(4-bromo-3-(difluoromethoxy)phenyl)-1H-imidazol-2-yl)pyrrolidin-1-yl)-3-methyl-1-oxobutan-2-ylcarbamate:

(S)-tert-Butyl 2-(5-(4-bromo-3-(difluoromethoxy)phenyl)-1H-imidazol-2-yl)pyrrolidine-1-carboxylate (400 mg, 0.873 mmol) was dissolved in DCM (10 mL) and treated with HCl (4.0 M in dioxane, 2 mL). The reaction mixture was stirred at RT for 50 min, then concentrated under reduced pressure. The crude residue was treated with (S)-2-(methoxycarbonylamino)-3-methylbutanoic acid (168 mg, 0.960 mmol), HATU (365 mg, 0.960 mmol) and DMF (4 mL) then cooled to 0° C. DIPEA (0.760 mL, 4.37 mmol) was added dropwise and the reaction mixture was stirred for 30 min. After warming to RT, the mixture was diluted with EtOAc and the organic solution was washed with saturated aqueous NaHCO₃, and brine then dried over MgSO₄, filtered and concentrated under reduced pressure. The crude residue was purified by silica column chromatography (0% to 33% MeOH/EtOAc) to afford methyl (S)-1-((S)-2-(5-(4-bromo-3-(difluoromethoxy)phenyl)-1H-imidazol-2-yl)pyrrolidin-1-yl)-3-methyl-1-oxobutan-2-ylcarbamate (333 mg, 74%).

(2S,4S)-tert-Butyl 4-(methoxymethyl)-2-(7-(4,4,5,5-tetramethyl-1,3,2-dioxaborolan-2-yl)-1H-naphtho[1,2-d]imidazol-2-yl)pyrrolidine-1-carboxylate was prepared according to the method utilized in the synthesis of methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate, substituting (2S,4S)-tert-butyl 2-(7-bromo-1H-naphtho[1,2-d]imidazol-2-yl)-4-(methoxymethyl)pyrrolidine-1-carboxylate for methyl (S)-1-((S)-2-(7-bromo-1H-naphtho[1,2-d]imidazol-2-yl)pyrrolidin-1-yl)-3-methyl-1-oxobutan-2-ylcarbamate.

(2S,4S)-tert-Butyl 2-(7-(2-(difluoromethoxy)-4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-4-(methoxymethyl)pyrrolidine-1-carboxylate was prepared from methyl (S)-1-((S)-2-(5-(4-bromo-3-(difluoromethoxy)phenyl)-1H-imidazol-2-yl)pyrrolidin-1-yl)-3-methyl-1-oxobutan-2-ylcarbamate and (2S,4S)-tert-butyl 4-(methoxymethyl)-2-(7-(4,4,5,5-tetramethyl-1,3,2-dioxaborolan-2-yl)-1H-naphtho[1,2-d]imidazol-2-yl)pyrrolidine-1-carboxylate using the same conditions employed in the synthesis of methyl {(2S)-1-[(2S,4S)-2-{2'-[(2S)-1-{(2S)-2-[(methoxycarbonyl)amino]-3-methylbutanoyl}pyrrolidin-2-yl]-1H,1'H-7,7'-binaphtho[1,2-d]imidazol-2-yl}-4-(methoxymethyl)pyrrolidin-1-yl]-3-methyl-1-oxobutan-2-yl}carbamate.

Methyl (R)-1-((S)-2-(5-(4-(2-((2S,4S)-1-((R)-2-methoxycarbonylamino-2-phenylacetyl)-4-(methoxymethyl)pyrrolidin-2-yl)-1H-naphtho[1,2-d]imidazol-7-yl)-3-(difluoromethoxy)phenyl)-1H-imidazol-2-yl)pyrrolidin-1-yl)-3-methyl-1-oxobutan-2-ylcarbamate was prepared according to the method employed in the synthesis of methyl (S)-1-((2S,4S)-2-(2'-((2S,4S)-1-((R)-2-tert-butoxycarbonylamino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate, substituting (2S,4S)-tert-butyl 2-(2'-((2S,4S)-1-((S)-2-(methoxycarbonylamino)-3-methylbutanoyl)-4-methylpyrrolidin-2-yl)-1H,1'H-7,7'-binaphtho[1,2-d]imidazol-2-yl)-4-(methoxymethyl)pyrrolidine-1-carboxylate with (2S,4S)-tert-butyl 2-(7-(2-(difluoromethoxy)-4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-4-(methoxymethyl)pyrrolidine-1-carboxylate and (R)-2-(tert-butoxycarbonylamino)-2-phenylacetic acid with (R)-2-(methoxycarbonylamino)-2-phenylacetic acid. MS (ESI) m/z 907 [M+H]⁺.

Example OB

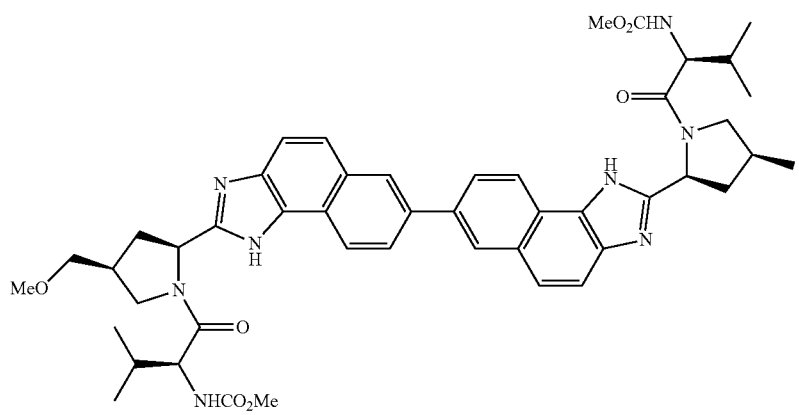

1361 methyl (S)-1-((2S,4S)-2-(2'-((2S,4S)-1-((S)-2-methoxycarbonylamino-3-methylbutanoyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate Methyl (S)-1-((2S,4S)-2-(2'-((2S,4S)-1-((S)-2-methoxycarbonylamino-3-methylbutanoyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate was prepared using a method analogous to that employed in the synthesis of methyl (S)-1-((2S,4S)-2-(2'-((2S,4S)-1-((2S,3R)-2-methoxycarbonylamino-3-methoxybutanoyl)-4-(methoxymethyl)pyrrolidin-2-yl)-1H,1'H-7,7'-binaphtho[12-d]imidazol-2-yl)-4-methylpyrrolidin-1-yl)-3-methyl-1-oxobutan-2-ylcarbamate, substituting (S)-2-(methoxycarbonylamino)-3-methylbutanoic acid for (2S,3R)-3-methoxy-2-(methoxycarbonylamino)butanoic acid. MS (ESI) m/z 846 [M+H]$^+$. $^1$H NMR (400 MHz, cd$_3$od) δ 8.51 (s, 2H), 8.45 (d, J=8.6 Hz, 2H), 8.17 (d, J=8.5 Hz, 2H), 8.10 (d, J=9.0 Hz, 2H), 7.76 (d, J=8.9 Hz, 2H), 5.43 (td, J=11.4, 7.2 Hz, 2H), 4.40 (s, 2H), 4.29 (d, J=7.1 Hz, 2H), 3.91-3.72 (m, 1H), 3.73-3.47 (m, 8H), 3.41 (d, J=9.4 Hz, 3H), 3.35 (s, 1H), 2.87 (d, J=5.8 Hz, 1H), 2.76 (tt, J=13.0, 6.6 Hz, 2H), 2.63 (d, J=5.6 Hz, 1H), 2.30-2.13 (m, 1H), 2.13-1.92 (m, 3H), 1.41-1.20 (m, 3H), 1.08-0.90 (m, 6H), 0.87 (d, J=6.6 Hz, 6H).

Example OC

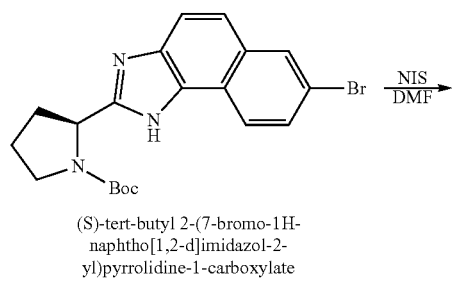

(S)-tert-butyl 2-(7-bromo-1H-naphtho[1,2-d]imidazol-2-yl)pyrrolidine-1-carboxylate

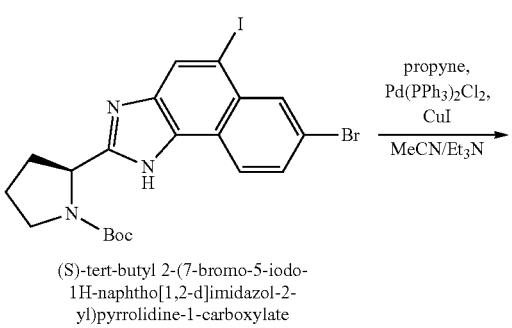

(S)-tert-butyl 2-(7-bromo-5-iodo-1H-naphtho[1,2-d]imidazol-2-yl)pyrrolidine-1-carboxylate

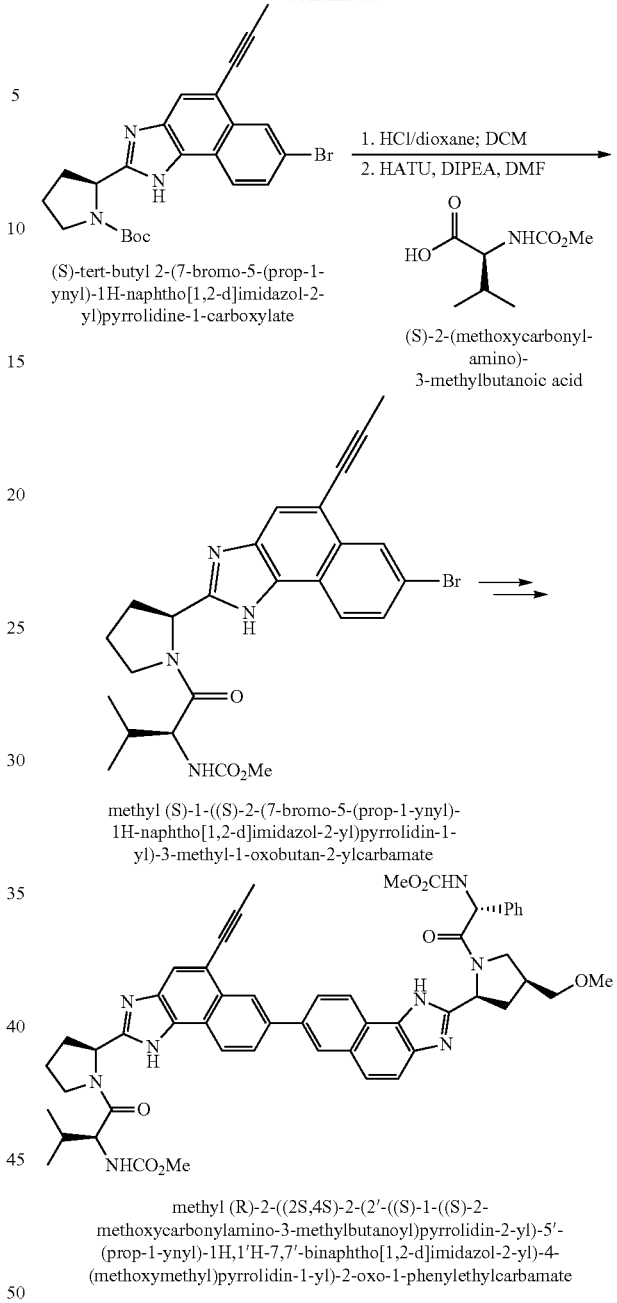

(S)-tert-butyl 2-(7-bromo-5-(prop-1-ynyl)-1H-naphtho[1,2-d]imidazol-2-yl)pyrrolidine-1-carboxylate (S)-2-(methoxycarbonylamino)-3-methylbutanoic acid methyl (S)-1-((S)-2-(7-bromo-5-(prop-1-ynyl)-1H-naphtho[1,2-d]imidazol-2-yl)pyrrolidin-1-yl)-3-methyl-1-oxobutan-2-ylcarbamate methyl (R)-2-((2S,4S)-2-(2'-((S)-1-((S)-2-methoxycarbonylamino-3-methylbutanoyl)pyrrolidin-2-yl)-5'-(prop-1-ynyl)-1H,1'H-7,7'-binaphtho[1,2-d]imidazol-2-yl)-4-(methoxymethyl)pyrrolidin-1-yl)-2-oxo-1-phenylethylcarbamate (S)-tert-Butyl 2-(7-bromo-5-iodo-1H-naphtho[1,2-d]imidazol-2-yl)pyrrolidine-1-carboxylate: (S)-tert-butyl 2-(7-bromo-1H-naphtho[1,2-d]imidazol-2-yl)pyrrolidine-1-carboxylate (0.990 g, 2.38 mmol) was suspended in DMF (8 mL) and treated with NIS (1.03 g, 4.59 mmol). The reaction mixture was stirred at 70° C. for 2d, then cooled to RT. The mixture was then diluted with EtOAc and the organic solution was washed with 3x with brine then dried over MgSO$_4$, filtered and concentrated under reduced pressure. The crude residue was purified by silica column chromatography (30% to 55% EtOAc/Hex) to afford (S)-tert-butyl 2-(7-bromo-5-iodo-1H-naphtho[1,2-d]imidazol-2-yl)pyrrolidine-1-carboxylate (753 mg, 58%).

(S)-tert-Butyl 2-(7-bromo-5-(prop-1-ynyl)-1H-naphtho[1,2-d]imidazol-2-yl)pyrrolidine-1-carboxylate: In a screwtop glass tube capped with a rubber septum, (S)-tert-Butyl 2-(7-bromo-5-iodo-1H-naphtho[1,2-d]imidazol-2-yl)pyrrolidine-1-carboxylate (524 mg, 1.00 mmol) was dissolved in a solution of MeCN (4 mL) and triethylamine (1 mL) and cooled to 0° C. Propyne gas was bubbled through the solution for 10 min and the vessel was charged with Pd(PPh₃)Cl₂ (70 mg, 0.10 mmol) and CuI (57 mg, 0.30 mmol). Propyne was bubbled through the suspension for another 7 min and the tube was sealed with a Teflon screw cap. The reaction mixture was warmed to RT and stirred for 2 h after which the tube was carefully opened to air, allowing the propyne to bubble out of solution. The contents of the tube were filtered over celite and rinsed with EtOAc then concentrated under reduced pressure. The crude residue was purified by silica column chromatography (40% to 65% EtOAc/Hex) to afford (S)-tert-butyl 2-(7-bromo-5-(prop-1-ynyl)-1H-naphtho[1,2-d]imidazol-2-yl)pyrrolidine-1-carboxylate (415 mg, 91%).

Methyl (S)-1-((S)-2-(7-bromo-5-(prop-1-ynyl)-1H-naphtho[1,2-d]imidazol-2-yl)pyrrolidin-1-yl)-3-methyl-1-oxobutan-2-ylcarbamate was prepared according to the procedure described for the synthesis of methyl (S)-1-((S)-2-(5-(4-bromo-3-(difluoromethoxy)phenyl)-1H-imidazol-2-yl)pyrrolidin-1-yl)-3-methyl-1-oxobutan-2-ylcarbamate, substituting (S)-tert-butyl 2-(7-bromo-5-(prop-1-ynyl)-1H-naphtho[1,2-d]imidazol-2-yl)pyrrolidine-1-carboxylate for (S)-tert-Butyl 2-(5-(4-bromo-3-(difluoromethoxy)phenyl)-1H-imidazol-2-yl)pyrrolidine-1-carboxylate.

Methyl (R)-2-((2S,4S)-2-(2'-((S)-1-((S)-2-methoxycarbonylamino-3-methylbutanoyl)pyrrolidin-2-yl)-5'-(prop-1-ynyl)-1H,1'H-7,7'-binaphtho[1,2-d]imidazol-2-yl)-4-(methoxymethyl)pyrrolidin-1-yl)-2-oxo-1-phenylethylcarbamate was prepared according to the method employed in the synthesis of methyl (R)-1-((S)-2-(5-(4-(2-((2S,4S)-1-((R)-2-methoxycarbonylamino-2-phenylacetyl)-4-(methoxymethyl)pyrrolidin-2-yl)-1H-naphtho[1,2-d]imidazol-7-yl)-3-(difluoromethoxy)phenyl)-1H-imidazol-2-yl)pyrrolidin-1-yl)-3-methyl-1-oxobutan-2-ylcarbamate, substituting methyl (S)-1-((S)-2-(7-bromo-5-(prop-1-ynyl)-1H-naphtho[1,2-d]imidazol-2-yl)pyrrolidin-1-yl)-3-methyl-1-oxobutan-2-ylcarbamate for methyl (S)-1-((S)-2-(5-(4-bromo-3-(difluoromethoxy)phenyl)-1H-imidazol-2-yl)pyrrolidin-1-yl)-3-methyl-1-oxobutan-2-ylcarbamate. MS (ESI) m/z 904 [M+H]⁺. ¹H NMR (400 MHz, cd₃od) δ 8.56 (s, 1H), 8.38-8.28 (m, 1H), 8.22 (dd, J=22.7, 16.8 Hz, 2H), 8.02-7.84 (m, 3H), 7.64 (d, J=12.9 Hz, 2H), 7.56-7.36 (m, 5H), 5.62-5.50 (m, 2H), 5.45 (t, J=7.6 Hz, 1H), 4.37 (t, J=11.2 Hz, 1H), 4.23 (s, 1H), 4.06 (dd, J=30.6, 23.2 Hz, 1H), 3.88 (t, J=9.8 Hz, 1H), 3.79 (t, J=8.8 Hz, 1H), 3.70 (s, 3H), 3.65-3.56 (m, 3H), 3.54-3.38 (m, 2H), 3.30-3.26 (m, 3H), 2.85-2.70 (m, 1H), 2.62 (dd, J=27.6, 22.5 Hz, 2H), 2.48-1.99 (m, 8H), 1.17-0.82 (m, 6H).

Example OD

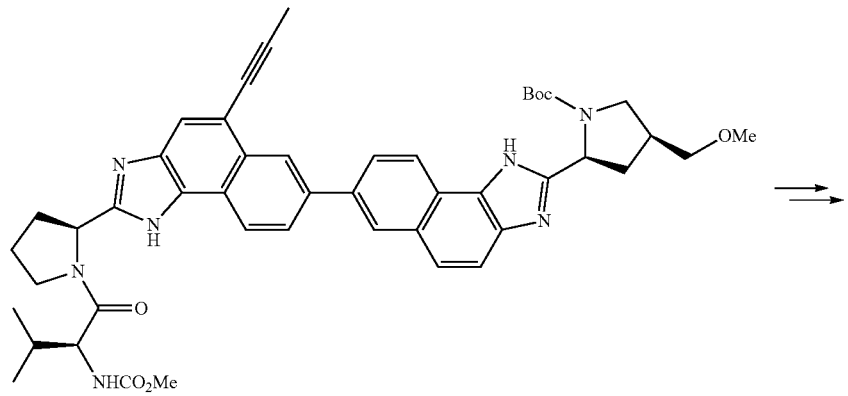

(2S,4S)-tert-butyl 2-(2'-((S)-1-((S)-2-(methoxycarbonylamino)-3-methylbutanoyl)pyrrolidin-2-yl)-5'-(prop-1-ynyl)-1H,1'H-7,7'binaphtho[1,2-d]imidazol-2-yl)-4-(methoxymethyl)pyrrolidine-1-carboxylate

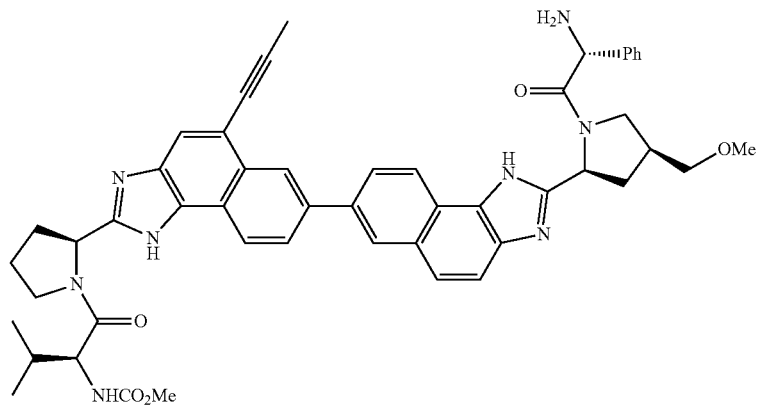

methyl (S)-1-((S)-2-(2'-((2S,4S)-1-((R)-2-amino-2-phenylacetyl)-4-(methoxymethyl)pyrrolidin-2-yl)-5-(prop-1-ynyl)-1H,1'H-7,7'-binaphtho[1,2-d]imidazol-2-yl)pyrrolidin-1-yl)-3-methyl-1-oxobutan-2-ylcarbamate (2S,4S)-tert-Butyl 2-(2'-((S)-1-((S)-2-(methoxycarbonylamino)-3-methylbutanoyl)pyrrolidin-2-yl)-5'-(prop-1-ynyl)-1H,1'H-7,7'-binaphtho[1,2-d]imidazol-2-yl)-4-(methoxymethyl)pyrrolidine-1-carboxylate was prepared according to the method described for the synthesis of (2S,4S)-tert-butyl 2-(7-(2-(difluoromethoxy)-4-(2-((S)-1-((S)-2-(methoxycarbonylamino)-3-methylbutanoyl)pyrrolidin-2-yl)-1H-imidazol-5-yl)phenyl)-1H-naphtho[1,2-d]imidazol-2-yl)-4-(methoxymethyl)pyrrolidine-1-carboxylate, replacing methyl (S)-1-((S)-2-(5-(4-bromo-3-(difluoromethoxy)phenyl)-1H-imidazol-2-yl)pyrrolidin-1-yl)-3-methyl-1-oxobutan-2-ylcarbamate with methyl (S)-1-((S)-2-(7-bromo-5-(prop-1-ynyl)-1H-naphtho[1,2-d]imidazol-2-yl)pyrrolidin-1-yl)-3-methyl-1-oxobutan-2-ylcarbamate.

Methyl (S)-1-((S)-2-(2'-((2S,4S)-1-((R)-2-amino-2-phenylacetyl)-4-(methoxymethyl)pyrrolidin-2-yl)-5'-(prop-1-ynyl)-1H,1'H-7,7'-binaphtho[1,2-d]imidazol-2-yl)pyrrolidin-1-yl)-3-methyl-1-oxobutan-2-ylcarbamate was prepared according to the method described for the synthesis of methyl (S)-1-((2S,4S)-2-(2'-((2S,4S)-1-((R)-2-amino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate, substituting (2S,4S)-tert-butyl 2-(2'-((S)-1-((S)-2-(methoxycarbonylamino)-3-methylbutanoyl)pyrrolidin-2-yl)-5'-(prop-1-ynyl)-1H,1'H-7,7'-binaphtho[1,2-d]imidazol-2-yl)-4-(methoxymethyl)pyrrolidine-1-carboxylate for (2S,4S)-tert-butyl 2-(2'-((2S,4S)-1-((S)-2-(methoxycarbonylamino)-3-methylbutanoyl)-4-methylpyrrolidin-2-yl)-1H,1'H-7,7'-binaphtho[1,2-d]imidazol-2-yl)-4-(methoxymethyl)pyrrolidine-1-carboxylate. MS (ESI) m/z 844 [M+H]+.

Example OE

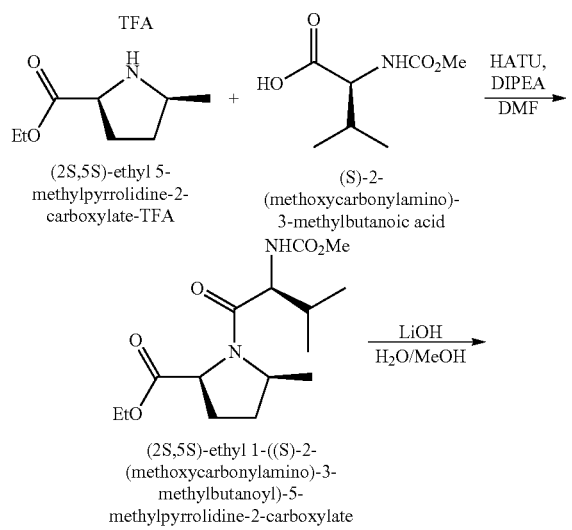

(2S,5S)-ethyl 5-methylpyrrolidine-2-carboxylate-TFA (S)-2-(methoxycarbonylamino)-3-methylbutanoic acid (2S,5S)-ethyl 1-((S)-2-(methoxycarbonylamino)-3-methylbutanoyl)-5-methylpyrrolidine-2-carboxylate -continued

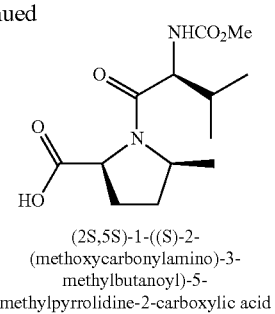

(2S,5S)-1-((S)-2-(methoxycarbonylamino)-3-methylbutanoyl)-5-methylpyrrolidine-2-carboxylic acid (2S,5S)-Ethyl 1-((S)-2-(methoxycarbonylamino)-3-methylbutanoyl)-5-methylpyrrolidine-2-carboxylate: (2S,5S)-Ethyl 5-methylpyrrolidine-2-carboxylate-TFA (10.0 g, 39.3 mmol), (S)-2-(methoxycarbonylamino)-3-methylbutanoic acid (6.88 g, 39.3 mmol) and HATU (14.9 g, 39.3 mmol) were combined in DMF (100 mL) and DIPEA (15.0 mL, 86.5 mmol) was added. After stirring for 1 h at RT, the reaction mixture was diluted with EtOAc. The organic phase was washed successively with 10% HCl, saturated aqueous NaHCO3 and brine, then dried over MgSO4, filtered and concentrated under reduced pressure to afford (2S,5S)-ethyl 1-((S)-2-(methoxycarbonylamino)-3-methylbutanoyl)-5-methylpyrrolidine-2-carboxylate. The crude material was carried on without further purification.

(2S,5S)-1-((S)-2-(Methoxycarbonylamino)-3-methylbutanoyl)-5-methylpyrrolidine-2-carboxylic acid: (2S,5S)-Ethyl 1-((S)-2-(methoxycarbonylamino)-3-methylbutanoyl)-5-methylpyrrolidine-2-carboxylate (39.3 mmol, assuming complete conversion from the previous transformation) was suspended in MeOH (200 mL) and aqueous LiOH (1.0 M, 100 mL, 100 mmol) was added. The reaction mixture was stirred o/n, then concentrated under reduced pressure to remove most of the MeOH. The aqueous solution was washed 2× with DCM before being acidified to pH-1-2 with 10% HCl. The acidic aqueous phase was then extracted 5× with EtOAc. The combined EtOAc extracts were dried over MgSO4 filtered and concentrated under reduced pressure to afford (2S,5S)-1-((S)-2-(Methoxycarbonylamino)-3-methylbutanoyl)-5-methylpyrrolidine-2-carboxylic acid (6.89 g, 56% over 2 steps).

Example OF

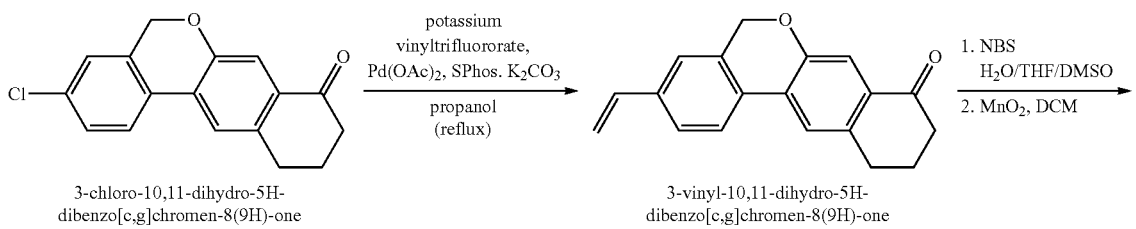

3-chloro-10,11-dihydro-5H-dibenzo[c,g]chromen-8(9H)-one 3-vinyl-10,11-dihydro-5H-dibenzo[c,g]chromen-8(9H)-one -continued

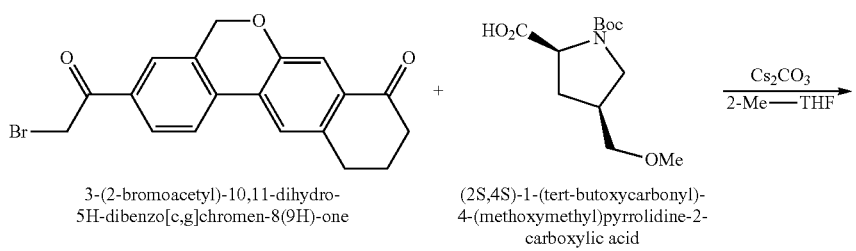

3-(2-bromoacetyl)-10,11-dihydro-
5H-dibenzo[c,g]chromen-8(9H)-one (2S,4S)-1-(tert-butoxycarbonyl)-
4-(methoxymethyl)pyrrolidine-2-
carboxylic acid

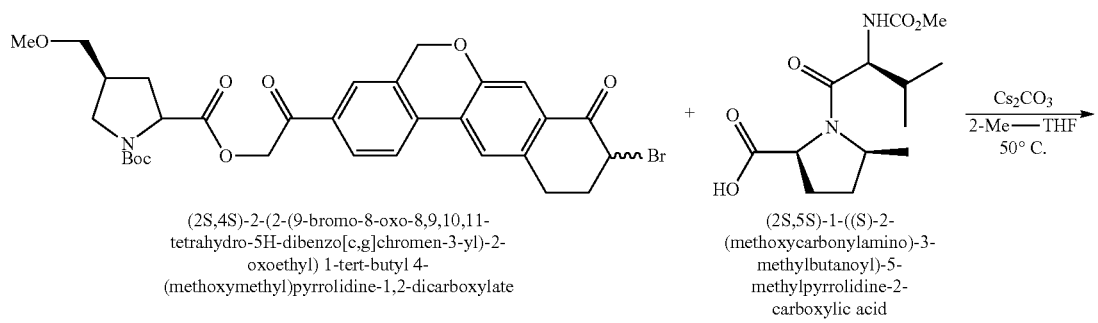

(4S)-1-tert-butyl 2-(2-oxo-2-(8-oxo-8,9,10,11-
tetrahydro-5H-dibenzo[c,g]chromen-3-yl)ethyl)
4-(methoxymethyl)pyrrolidine-1,2-dicarboxylate (2S,4S)-2-(2-(9-bromo-8-oxo-8,9,10,11-
tetrahydro-5H-dibenzo[c,g]chromen-3-yl)-2-
oxoethyl) 1-tert-butyl 4-
(methoxymethyl)pyrrolidine-1,2-dicarboxylate (2S,5S)-1-((S)-2-
(methoxycarbonylamino)-3-
methylbutanoyl)-5-
methylpyrrolidine-2-
carboxylic acid

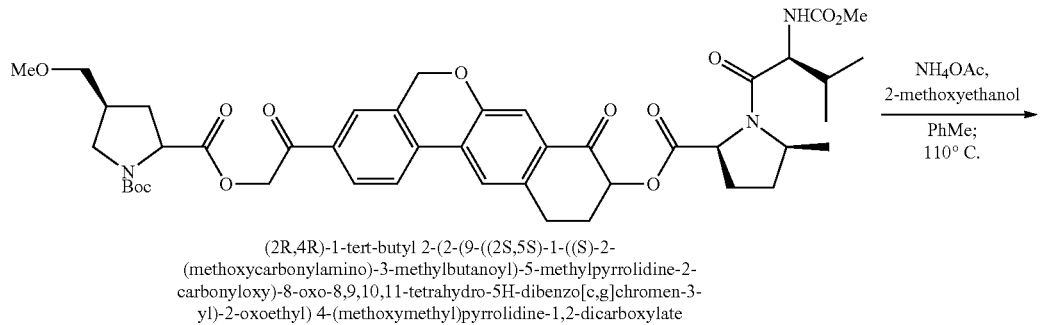

(2R,4R)-1-tert-butyl 2-(2-(9-((2S,5S)-1-((S)-2-
(methoxycarbonylamino)-3-methylbutanoyl)-5-methylpyrrolidine-2-
carbonyloxy)-8-oxo-8,9,10,11-tetrahydro-5H-dibenzo[c,g]chromen-3-
yl)-2-oxoethyl) 4-(methoxymethyl)pyrrolidine-1,2-dicarboxylate

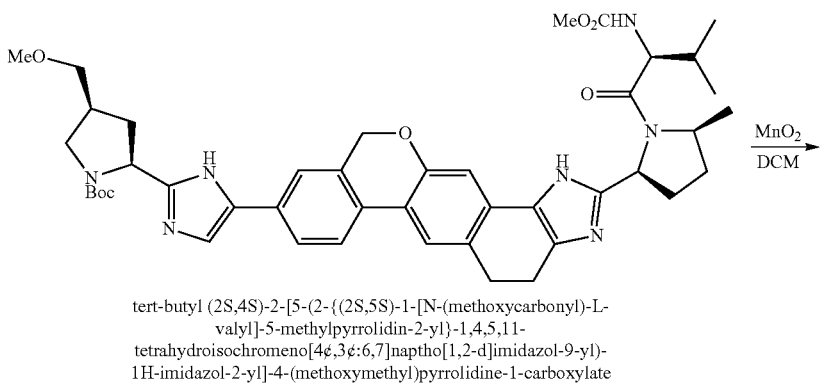

tert-butyl (2S,4S)-2-[5-(2-{(2S,5S)-1-[N-(methoxycarbonyl)-L-
valyl]-5-methylpyrrolidin-2-yl}-1,4,5,11-
tetrahydroisochromeno[4¢,3¢:6,7]naptho[1,2-d]imidazol-9-yl)-
1H-imidazol-2-yl]-4-(methoxymethyl)pyrrolidine-1-carboxylate

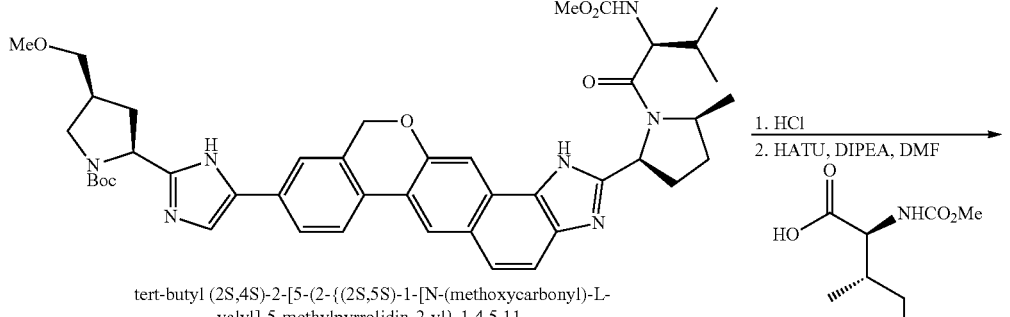

tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naptho[1,2-d]imidazol-9-yl)-1H-imidazol-2-yl]-4-(methoxymethyl)pyrrolidine-1-carboxylate (2S,3R)-2-(methoxycarbonylamino)-3-methylpentanoicacid

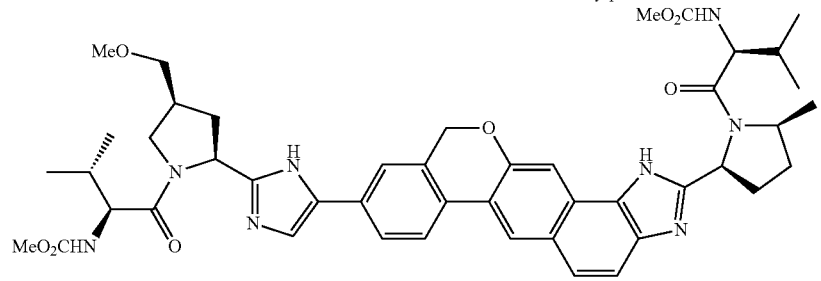

methyl {(2S,3S)-1-[(2S,4S)-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naptho[1,2-d]imidazol-9-yl}-1H-imidazol-2-yl]-4-(methoxymethyl)pyrrolidin-1-yl]-3-methyl-1-oxopentan-2-yl}carbamate 3-Vinyl-10,11-dihydro-5H-dibenzo[c,g]chromen-8(9H)-one: A 3-neck oven-dried 500 mL round-bottom flask was cooled under Ar, then charged with 3-Chloro-10,11-dihydro-5H-dibenzo[c,g]chromen-8(9H)-one (12.0 g, 42.1 mmol), potassium vinyltrifluoroborate (8.47 g, 6.32 mmol), Pd(OAc)$_2$ (473 mg, 2.11 mmol), SPhos (1.74 g, 4.25 mmol), K$_2$CO$_3$ (17.5 g, 126 mmol) and anhydrous propanol (120 mL). The reaction mixture was sparged with Ar for 16 min, then heated to reflux for 5.5 h. Upon completion, the reaction mixture was cooled to RT and concentrated under reduced pressure. The crude residue was suspended in DCM, then washed with H$_2$O and brine. The organic solution was dried over MgSO$_4$, filtered and concentrated under reduced pressure. The resulting residue was further purified via silica plug, eluting with DCM to afford 3-vinyl-10,11-dihydro-5H-dibenzo[c,g]chromen-8(9H)-one (10.2 g, 87%).

3-(2-Bromoacetyl)-10,11-dihydro-5H-dibenzo[c,g]chromen-8(9H)-one: 3-Vinyl-10,11-dihydro-5H-dibenzo[c,g]chromen-8(9H)-one (9.98 g, 36.1 mmol) was dissolved in a stirred solution of THF (70 mL), DMSO (70 mL) and H$_2$O (35 mL). NBS (6.75 g, 37.9 mmol) was added in a single portion and the reaction mixture was stirred at RT for 33 min. Upon completion, the reaction medium was diluted with EtOAc and washed twice with H$_2$O and once with brine. The organic phase was dried over MgSO$_4$, filtered and concentrated under reduced pressure. The resulting crude bromohydrin was suspended in DCM (200 mL) and treated with activated MnO$_2$ (62.7 g, 722 mmol). After stirring for 15 h at RT, the reaction mixture was filtered over celite and the filter cake was rinsed several times with DCM. The combined filtrate (~400 mL) was treated with MeOH (~100 mL) and the mixture was gradually concentrated under reduced pressure, causing solid material to precipitate from solution. When the liquid volume reached ~200 mL, the solid was filtered off and rinsed with MeOH. The concentration/precipitation/filtration/rinsing sequence was performed 2× more, resulting in the collection of 3 crops of powdered 3-(2-bromoacetyl)-10,11-dihydro-5H-dibenzo[c,g]chromen-8(9H)-one (7.49 g, 56% over 2 steps).

(4S)-1-tert-Butyl 2-(2-oxo-2-(8-oxo-8,9,10,11-tetrahydro-5H-dibenzo[c,g]chromen-3-yl)ethyl) 4-(methoxymethyl)pyrrolidine-1,2-dicarboxylate: 3-(2-Bromoacetyl)-10,11-dihydro-5H-dibenzo[c,g]chromen-8(9H)-one (7.47 g, 20.1 mmol) and (2S,4S)-1-(tert-butoxycarbonyl)-4-(methoxymethyl)pyrrolidine-2-carboxylic acid (5.22 g, 20.1 mmol) were suspended in 2-Me-THF (75 mL) and treated with Cs$_2$CO$_3$ (3.27 g, 10.1 mmol). After stirring 4 h at RT, the reaction mixture was diluted with diluted with DCM. The organic layer was washed with H$_2$O. The aqueous layer was then back extracted 2× with DCM. The combined organics were dried over MgSO$_4$, filtered and concentrated under reduced pressure. The crude residue was purified by silica column chromatography (10% to 50% EtOAc/DCM) to afford (4S)-1-tert-butyl 2-(2-oxo-2-(8-oxo-8,9,10,11-tetrahydro-5H-dibenzo[c,g]chromen-3-yl)ethyl) 4-(methoxymethyl)pyrrolidine-1,2-dicarboxylate (7.73 g, 70%).

(2S,4S)-2-(2-(9-Bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate: (4S)-1-tert-Butyl 2-(2-oxo-2-(8-oxo-8,9,10,11-tetrahydro-5H-dibenzo[c,g]chromen-3-yl)ethyl) 4-(methoxymethyl)pyrrolidine-1,2-dicarboxylate (7.66 g, 13.9 mmol) was dissolved in a solution of DCM (100 mL) and MeOH (40 mL), then treated with pyridinium tribromide (4.90 g, 15.3 mmol). After stirring at RT for 1.75 h, the reaction mixture was diluted with DCM and washed successively with 10% HCl, saturated aqueous NaHCO$_3$ and brine. The organic phase was dried over MgSO$_4$, filtered and concentrated under reduced pressure and the crude material was carried on without further purification.

(2R,4R)-1-tert-Butyl 2-(2-(9-((2S,5S)-1-((S)-2-(methoxycarbonylamino)-3-methylbutanoyl)-5-methylpyrrolidine-2-carbonyloxy)-8-oxo-8,9,10,11-tetrahydro-5H-dibenzo[c,g]chromen-3-yl)-2-oxoethyl) 4-(methoxymethyl)pyrrolidine-1,2-dicarboxylate: (2S,4S)-2-(2-(9-Bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate (8.76 g, 13.94 mmol) was treated with a solution of (2S,5S)-1-((S)-2-(methoxycarbonylamino)-3-methylbutanoyl)-5-methylpyrrolidine-2-carboxylic acid (6.85 g, 23.92 mmol) in 2-Me-THF (70 mL) and Cs$_2$CO$_3$ (3.63 g, 11.15 mmol). The stirred reaction mixture was heated to 50° C. for 20 h, then cooled to RT and diluted with EtOAc. The organic phase was washed with H$_2$O and brine, then dried over MgSO$_4$, filtered and concentrated under reduced pressure. The crude residue was purified by silica column chromatography (0% to 30% MeOH/EtOAc) to afford (2R,4R)-1-tert-butyl 2-(2-(9-((2S,5S)-1-((S)-2-(methoxycarbonylamino)-3-methylbutanoyl)-5-methylpyrrolidine-2-carbonyloxy)-8-oxo-8,9,10,11-tetrahydro-5H-dibenzo[c,g]chromen-3-yl)-2-oxoethyl) 4-(methoxymethyl)pyrrolidine-1,2-dicarboxylate (10.47 g, 90%).

tert-Butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate: (2R,4R)-1-tert-Butyl 2-(2-(9-((2S,5S)-1-((S)-2-(methoxycarbonylamino)-3-methylbutanoyl)-5-methylpyrrolidine-2-carbonyloxy)-8-oxo-8,9,10,11-tetrahydro-5H-dibenzo[c,g]chromen-3-yl)-2-oxoethyl) 4-(methoxymethyl)pyrrolidine-1,2-dicarboxylate (10.47 g, 12.56 mmol) and NH$_4$OAc (50.9 g, 660 mmol) were suspended in a solution of 10:1 PhMe/2-methoxyethanol (132 mL). The stirred reaction mixture was heated to 110° C. for 4.5 h, then cooled to RT and diluted with EtOAc. The organic phase was washed 3× with saturated aqueous NaHCO$_3$, then dried over MgSO$_4$, filtered and concentrated under reduced pressure. The crude residue was purified by silica column chromatography (0% to 30% MeOH/EtOAc) to afford tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate (8.33 g, 84%).

tert-Butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate:

tert-Butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate (8.33 g, 1.049 mmol) was suspended in DCM and activated MnO$_2$ (55.0 g, 630 mmol) was added in a single portion. After 13 h, MeOH (200 mL) was added and the slurry was filtered over celite. The filter cake was washed with MeOH (600 mL) and the filtrate was concentrated under reduced pressure. The crude material was purified by silica column chromatography (0% to 45% MeOH/EtOAc) to afford tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (4.85 g, 58%).

Methyl {(2S,3S)-1-[(2S,4S)-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate: tert-Butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (179 mg, 0.226 mmol) was dissolved in DCM (4 mL) and HCl (4.0 M in dioxane, 1 mL) was added. The reaction mixture was stirred for 1 h at RT then concentrated under reduced pressure. The resulting residue was treated with (2S,3S)-2-(methoxycarbonylamino)-3-methylpentanoic acid (51 mg, 0.27 mmol), HATU (95 mg, 0.25 mmol), DMF (2 mL) and DIPEA (0.39 mL, 2.3 mmol). After stirring for 6 min, the reaction was quenched with H$_2$O, filtered and purified by reverse phase HPLC to afford methyl {(2S,3S)-1-[(2S,4S)-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate (116 mg, 59%). MS (ESI) m/z 864 [M+H]$^+$. $^1$H NMR (400 MHz, cd$_3$od) δ 8.57 (d, J=14.7 Hz, 1H), 8.45 (s, 1H), 8.20 (d, J=14.4 Hz, 1H), 8.15-7.98 (m, 2H), 7.91 (dd, J=21.8, 14.1 Hz, 2H), 7.85-7.69 (m, 2H), 7.69-7.48 (m, 2H), 5.42-5.12 (m, 5H), 4.34 (dd, J=22.3, 13.7 Hz, 1H), 4.30-4.10 (m, 2H), 3.87-3.73 (m, 1H), 3.73-3.63 (m, 7H), 3.62-3.48 (m, 2H), 3.48-3.38 (m, 4H), 3.35 (s, 3H), 2.95-2.70 (m, 1H), 2.70-2.55 (m, 2H), 2.55-2.20 (m, 2H), 2.20-1.91 (m, 3H), 1.77 (d, J=42.0 Hz, 1H), 1.65 (d, J=6.6 Hz, 3H), 1.43 (t, J=24.6 Hz, 1H), 1.28 (d, J=6.2 Hz, 1H), 1.23-1.01 (m, 3H), 0.98 (d, J=6.6 Hz, 3H), 0.90 (dd, J=13.1, 5.9 Hz, 10H).

Example OG

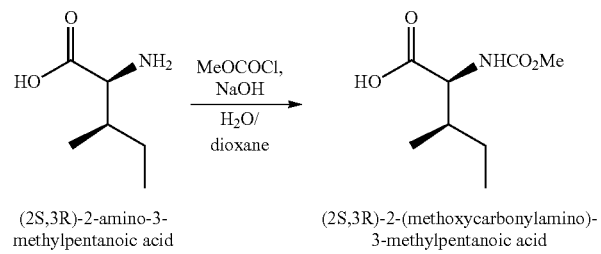

(2S,3R)-2-amino-3-methylpentanoic acid (2S,3R)-2-(methoxycarbonylamino)-3-methylpentanoic acid

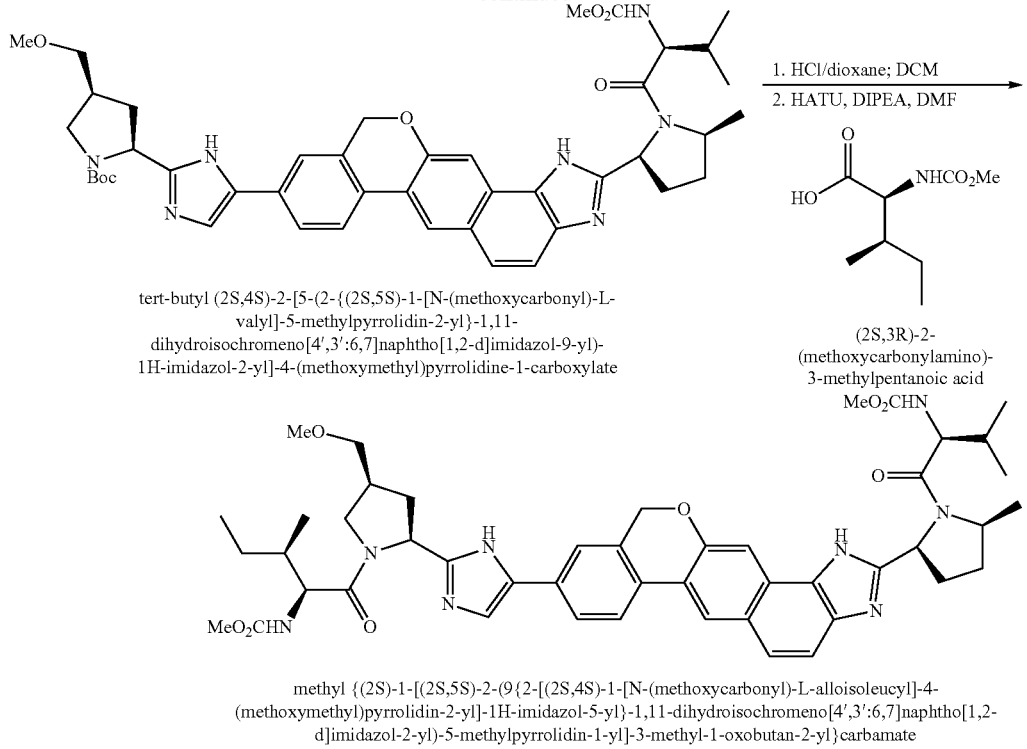

tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (2S,3R)-2-(methoxycarbonylamino)-3-methylpentanoic acid methyl {(2S)-1-[(2S,5S)-2-(9{2-[(2S,4S)-1-[N-(methoxycarbonyl)-L-alloisoleucyl]-4-(methoxymethyl)pyrrolidin-2-yl]-1H-imidazol-5-yl)-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,4S)-1-[N-(methoxycarbonyl)-1-alloisoleucyl]-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate was prepared from tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate by the same method employed in the synthesis of {(2S,3S)-1-[(2S,4S)-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate, replacing (2S,3S)-2-(methoxycarbonylamino)-3-methylpentanoic acid with (2S,3R)-2-(methoxycarbonylamino)-3-methylpentanoic acid. MS (ESI) m/z 864 [M+H]+. 1H NMR (400 MHz, cd3od) δ 8.62-8.41 (m, 1H), 8.22 (s, 1H), 8.07 (dt, J=20.1, 10.0 Hz, 1H), 7.89 (dt, J=35.6, 15.6 Hz, 2H), 7.77 (dd, J=20.3, 7.0 Hz, 2H), 7.68-7.48 (m, 2H), 5.95 (d, J=5.0 Hz, 1H), 5.42-5.13 (m, 4H), 4.47 (t, J=5.5 Hz, 1H), 4.40-4.09 (m, 2H), 3.80-3.73 (m, 1H), 3.73-3.62 (m, 6H), 3.57 (dt, J=16.1, 9.7 Hz, 2H), 3.40 (s, 3H), 3.34 (d, J=7.5 Hz, 1H), 2.81 (dd, J=18.4, 12.5 Hz, 1H), 2.63 (td, J=13.3, 6.8 Hz, 2H), 2.55-2.18 (m, 2H), 2.16-1.77 (m, 4H), 1.65 (d, J=6.6 Hz, 3H), 1.50-1.31 (m, 1H), 1.26 (dd, J=15.6, 6.7 Hz, 2H), 1.17-1.03 (m, 2H), 0.98 (dd, J=6.7, 4.5 Hz, 5H), 0.89 (dd, J=15.5, 7.8 Hz, 3H), 0.86-0.74 (m, 3H).

Example OH

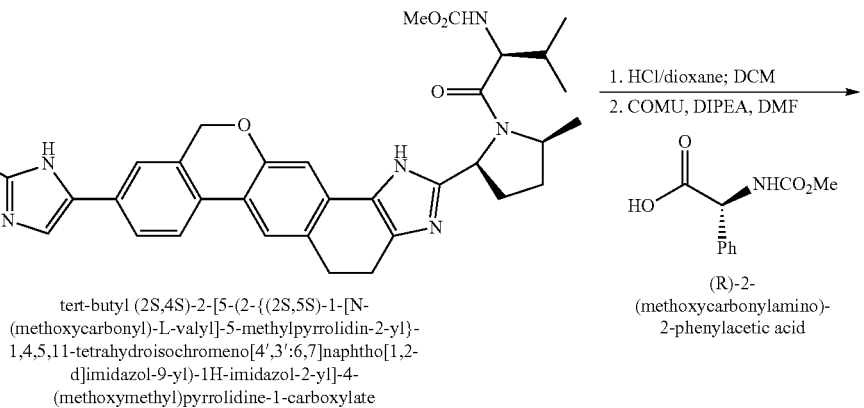

tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate (R)-2-(methoxycarbonylamino)-2-phenylacetic acid -continued

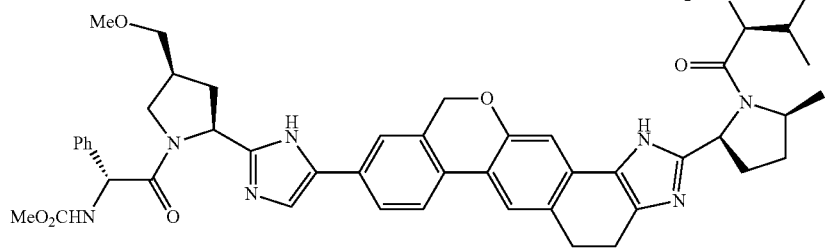

methyl {(1R)-2-[(2S,4S)-2-(5{2-[(2S,5S)-1-{(2S)-2-[(methoxycarbonyl)amino]-
3-methylbutanoyl}-5-methylpyrrolidin-2-yl]-1,4,5,11-
tetrahydroisochromeno[4',3':6,7]naphtho[1,2-d]imidazol-9-yl}-1H-imidazol-2-
yl)-4-(methoxymethyl)pyrrolidin-1-yl]-2-oxo-1-phenylethyl}carbamate Methyl {(1R)-2-[(2S,4S)-2-(5-{2-[(2S,5S)-1-{(2S)-2-[(methoxycarbonyl)amino]-3-methylbutanoyl}-5-methyl-pyrrolidin-2-yl]-1,4,5,11-tetrahydroisochromeno[4',3':6,7] naphtho[1,2-d]imidazol-9-yl}-1H-imidazol-2-yl)-4-(methoxymethyl)pyrrolidin-1-yl]-2-oxo-1-phenylethyl}carbamate: tert-Butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl) pyrrolidine-1-carboxylate (102 mg, 0.128 mmol) was dissolved in DCM (4 mL) and HCl (4.0 M in dioxane, 2.0 mL, 8.0 mmol) was added. After stirring at RT for 30 min, the solution was concentrated under reduced pressure. The residue was treated with (R)-2-(methoxycarbonylamino)-2-phenylacetic acid (29 mg, 0.141 mmol), COMU (60 mg, 0.141 mmol), DMF (3.0 mL) and DIPEA (0.223 mL, 1.28 mmol). After stirring at RT for 20 min, the reaction mixture was diluted with EtOAc. The organic solution was washed with saturated aqueous NaHCO₃ and brine, then dried over MgSO₄, filtered and concentrated under reduced pressure. The crude material was purified by reverse-phase HPLC to afford methyl {(1R)-2-[(2S,4S)-2-(5-{2-[(2S,5S)-1-{(2 S)-2-[(methoxycarbonyl)amino]-3-methylbutanoyl}-5-methyl-pyrrolidin-2-yl]-1,4,5,11-tetrahydroisochromeno[4',3':6,7] naphtho[1,2-d]imidazol-9-yl}-1H-imidazol-2-yl)-4-(methoxymethyl)pyrrolidin-1-yl]-2-oxo-1-phenylethyl}carbamate as the bis-TFA salt (82.4 mg, 60%). MS (ESI) m/z 866 [M+H]⁺. ¹H NMR (400 MHz, cd₃od) δ 7.94-7.67 (m, 4H), 7.59 (d, J=9.1 Hz, 1H), 7.52 (s, 1H), 7.48-7.33 (m, 4H), 7.11 (d, J=18.7 Hz, 1H), 5.68 (d, J=6.3 Hz, 1H), 5.48-5.33 (m, 1H), 5.23 (dd, J=24.1, 15.7 Hz, 1H), 5.17-5.03 (m, 3H), 4.22 (dd, J=17.0, 9.6 Hz, 1H), 4.16-4.01 (m, 1H), 3.91 (d, J=24.1 Hz, 1H), 3.83-3.68 (m, 1H), 3.68-3.59 (m, 3H), 3.59-3.49 (m, 3H), 3.38 (ddd, J=15.9, 9.6, 5.7 Hz, 2H), 3.28-3.14 (m, 5H), 3.10 (dd, J=14.0, 8.2 Hz, 1H), 3.00 (dd, J=17.8, 9.6 Hz, 1H), 2.92 (dd, J=14.5, 6.7 Hz, 1H), 2.73-2.41 (m, 2H), 2.40-2.11 (m, 2H), 2.11-1.83 (m, 2H), 1.54 (t, J=9.7 Hz, 2H), 1.24 (d, J=6.2 Hz, 1H), 1.06 (t, J=8.0 Hz, 1H), 0.99 (d, J=6.8 Hz, 1H), 0.94 (d, J=6.6 Hz, 2H), 0.85 (d, J=6.7 Hz, 2H).

Example OI

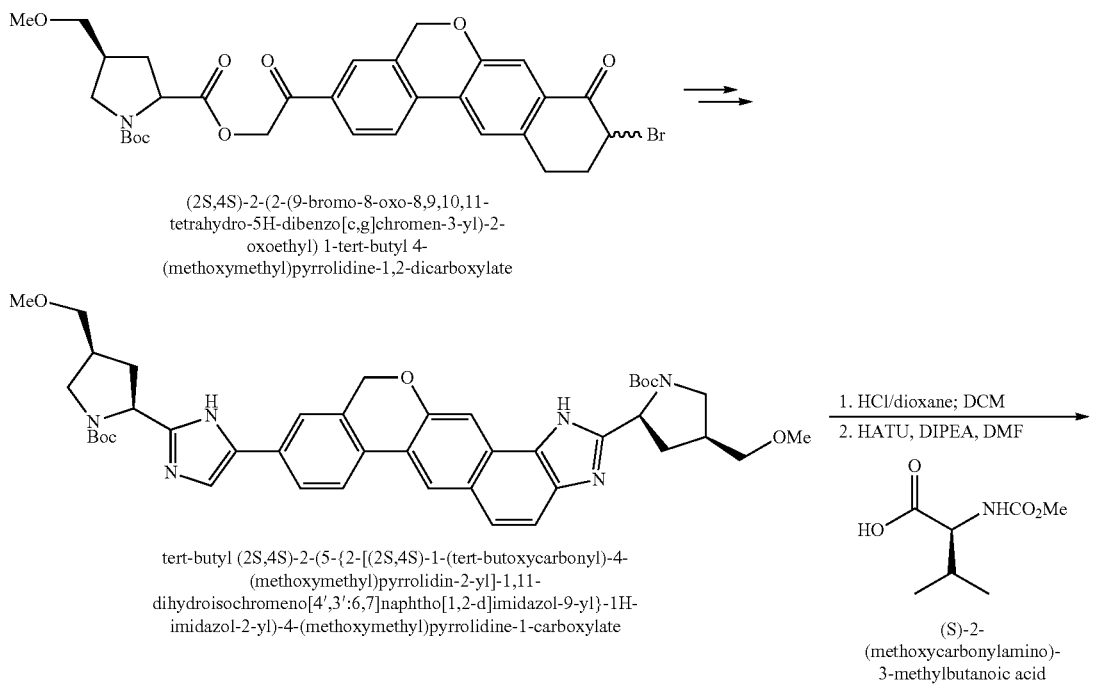

(2S,4S)-2-(2-(9-bromo-8-oxo-8,9,10,11-
tetrahydro-5H-dibenzo[c,g]chromen-3-yl)-2-
oxoethyl) 1-tert-butyl 4-
(methoxymethyl)pyrrolidine-1,2-dicarboxylate tert-butyl (2S,4S)-2-(5-{2-[(2S,4S)-1-(tert-butoxycarbonyl)-4-
(methoxymethyl)pyrrolidin-2-yl]-1,11-
dihydroisochromeno[4',3':6,7]naphtho[1,2-d]imidazol-9-yl}-1H-
imidazol-2-yl)-4-(methoxymethyl)pyrrolidine-1-carboxylate 1. HCl/dioxane; DCM
2. HATU, DIPEA, DMF (S)-2-
(methoxycarbonylamino)-
3-methylbutanoic acid -continued

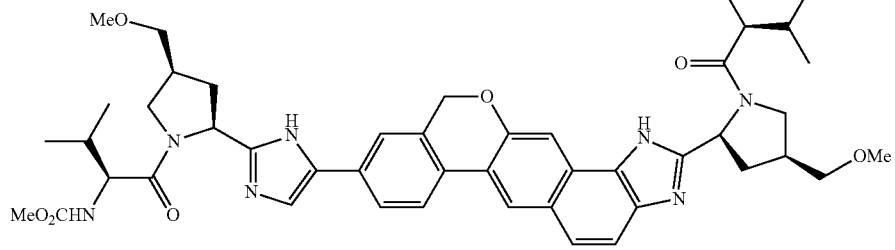

methyl {(2S)-1-[(2S,4S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate tert-Butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidine-1-carboxylate was prepared from (2S,4S)-2-(2-(9-bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate by the same method employed in the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate, replacing (2S,5S)-1-((S)-2-(methoxycarbonylamino)-3-methylbutanoyl)-5-methylpyrrolidine-2-carboxylic acid with (2S,4S)-1-(tert-butoxycarbonyl)-4-(methoxymethyl)pyrrolidine-2-carboxylic acid.

Methyl {(2S)-1-[(2S,4S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate: tert-Butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidine-1-carboxylate (137 mg, 0.179 mmol) was dissolved in DCM (5 mL) and HCl (4.0 M in dioxane, 1 mL) was added. After stirring at RT for 1.5 h, the reaction mixture was concentrated under reduced pressure. The crude residue was treated with (S)-2-(methoxycarbonylamino)-3-methylbutanoic acid (69 mg, 0.39 mmol), HATU (149 mg, 0.393 mmol), DMF (2.0 mL) and DIPEA (0.31 mL, 1.8 mmol). After stirring for 15 min at RT, the reaction mixture was quenched with water and purified by HPLC to provide methyl {(2S)-1-[(2S,4S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate (123 mg). MS (ESI) m/z 880 [M+H]$^+$. $^1$H NMR (400 MHz, cd$_3$od) δ 8.48 (s, 1H), 8.05 (t, J=11.2 Hz, 1H), 7.92 (dd, J=19.7, 10.1 Hz, 2H), 7.74 (s, 2H), 7.59-7.44 (m, 2H), 5.49 (s, 1H), 5.40 (dt, J=16.3, 8.1 Hz, 1H), 5.31-5.15 (m, 3H), 4.47-4.10 (m, 4H), 3.86-3.44 (m, 12H), 3.39 (dd, J=13.2, 7.1 Hz, 6H), 2.94-2.57 (m, 4H), 2.25-1.94 (m, 4H), 1.02-0.82 (m, 12H).

Example OJ

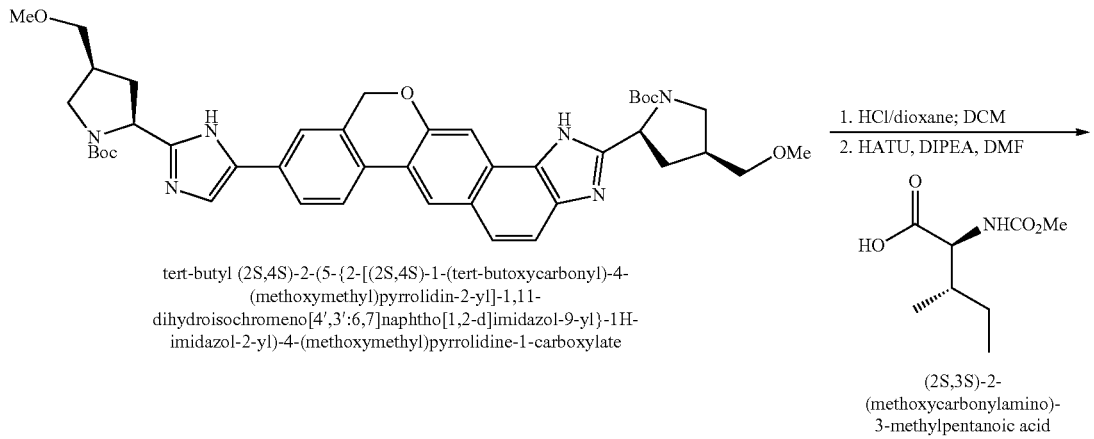

tert-butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidine-1-carboxylate 1. HCl/dioxane; DCM
2. HATU, DIPEA, DMF (2S,3S)-2-(methoxycarbonylamino)-3-methylpentanoic acid

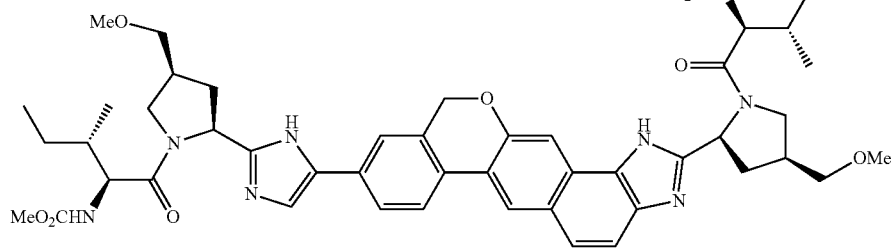

methyl {(2S,3S)-1-[(2S,4S)-2-(5-{2-[(2S,4S)-1-{(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate Methyl {(2S,3S)-1-[(2S,4S)-2-(5-{2-[(2S,4S)-1-{(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate was prepared from tert-Butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidine-1-carboxylate using the same method employed in the synthesis of methyl {(2S)-1-[(2S,4S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate, replacing with (S)-2-(methoxycarbonylamino)-3-methylbutanoic acid with (2S,3S)-2-(methoxycarbonylamino)-3-methylpentanoic acid. MS (ESI) m/z 908 [M+H]$^+$.

Example OK

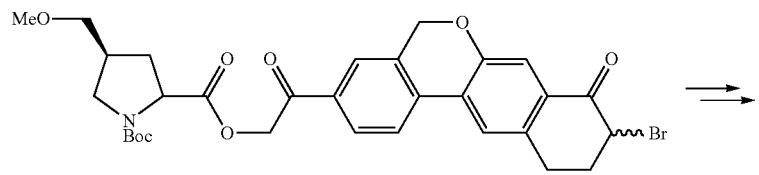

(2S,4S)-2-(2-(9-bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate

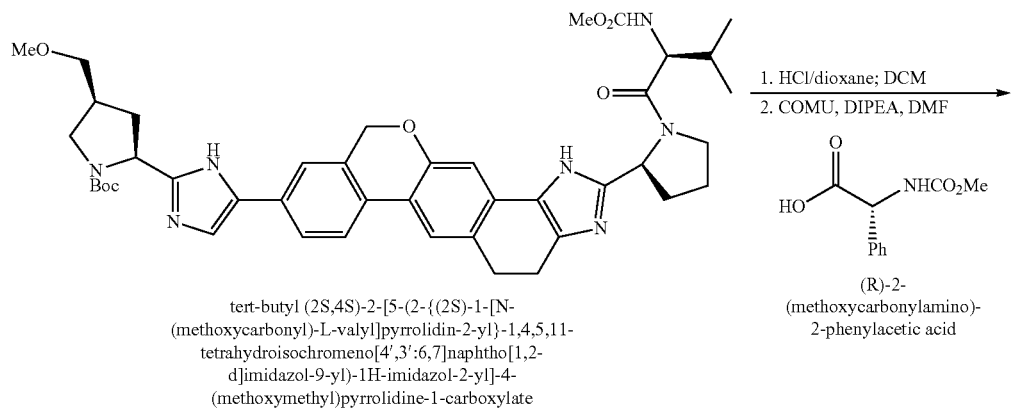

tert-butyl (2S,4S)-2-[5-(2-{(2S)-1-[N-(methoxycarbonyl)-L-valyl]pyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate (R)-2-(methoxycarbonylamino)-2-phenylacetic acid

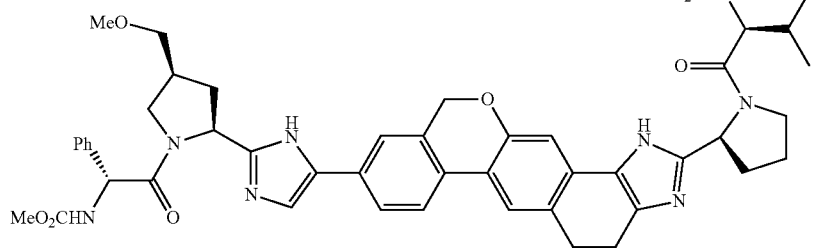

methyl {(1R)-2-[(2S,4S)-2-(5-{2-[(2S)-1-{(2S)-2-[(methoxycarbonyl)amino]-3-methylbutanoyl}pyrrolidin-2-yl]-1,4,5,11-tetrahydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate tert-Butyl (2S,4S)-2-[5-(2-{(2S)-1-[N-(methoxycarbonyl)-L-valyl]pyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate was synthesized from (2S,4S)-2-(2-(9-bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate using the same methods described for the synthesis of tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate, substituting (S)-1-((S)-2-(methoxycarbonylamino)-3-methylbutanoyl)pyrrolidine-2-carboxylic acid for (2S,5S)-1-((S)-2-(methoxycarbonylamino)-3-methylbutanoyl)-5-methylpyrrolidine-2-carboxylic acid.

Methyl {(1R)-2-[(2S,4S)-2-(5-{2-[(2S)-1-{(2S)-2-[(methoxycarbonyl)amino]-3-methylbutanoyl}pyrrolidin-2-yl]-1,4,5,11-tetrahydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate was synthesized from tert-butyl (2S,4S)-2-[5-(2-{(2S)-1-[N-(methoxycarbonyl)-L-valyl]pyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate using the same method employed for the synthesis of methyl {(1R)-2-[(2S,4S)-2-(5-{2-[(2S,5S)-1-{(2S)-2-[(methoxycarbonyl)amino]-3-methylbutanoyl}-5-methylpyrrolidin-2-yl]-1,4,5,11-tetrahydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate substituting tert-butyl (2S,4S)-2-[5-(2-{(2S)-1-[N-(methoxycarbonyl)-L-valyl]pyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate for tert-Butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 871 [M+H]$^+$.
$^1$H NMR (400 MHz, cd$_3$od) δ 7.87 (ddd, J=20.5, 15.3, 6.8 Hz, 4H), 7.65 (s, 1H), 7.50-7.38 (m, 5H), 7.17 (s, 1H), 5.41 (d, J=24.5 Hz, 1H), 5.28 (t, J=8.3 Hz, 1H), 5.20 (d, J=7.3 Hz, 3H), 4.24 (d, J=7.2 Hz, 1H), 4.12 (d, J=10.3 Hz, 1H), 4.03-3.94 (m, 1H), 3.89 (dd, J=15.4, 8.6 Hz, 1H), 3.77 (t, J=9.6 Hz, 1H), 3.72-3.64 (m, 4H), 3.63-3.52 (m, 4H), 3.43 (qd, J=9.5, 5.6 Hz, 3H), 3.30 (s, 3H), 3.24-3.08 (m, 2H), 2.97 (dd, J=11.6, 5.4 Hz, 2H), 2.59 (dt, J=21.1, 7.8 Hz, 3H), 2.29 (s, 1H), 2.24-2.14 (m, 2H), 2.11-1.85 (m, 2H), 0.92 (dd, J=15.8, 6.7 Hz, 6H).

Example OL

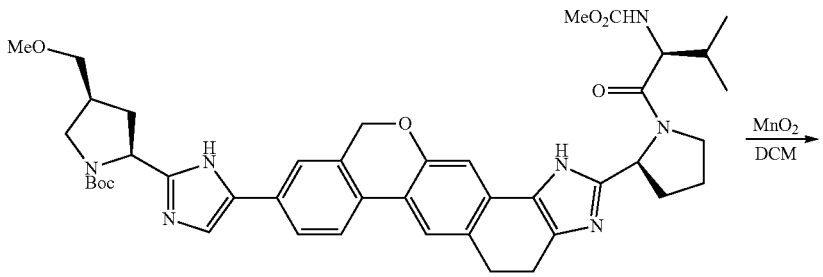

tert-butyl (2S,4S)-2-[5-(2-{(2S)-1-[N-(methoxycarbonyl)-L-valyl]pyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate

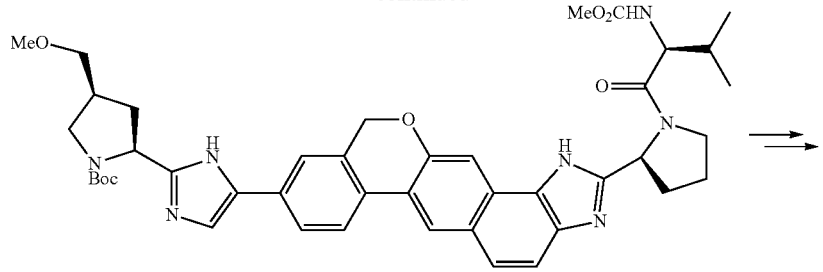

tert-butyl (2S,4S)-2-[5-(2-{(2S)-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate

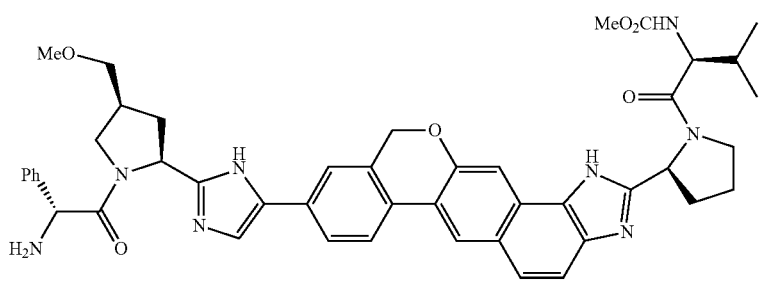

methyl {(2S)-1-[(2S)-2-(9-{2-[(2S,4S)-1-[(2R)-2-amino-2-phenylacetyl]-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-3-methyl-1-oxobutan-2-yl}carbamate tert-Butyl (2S,4S)-2-[5-(2-{(2S)-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate was prepared according to the method described for the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate, substituting tert-butyl (2S,4S)-2-[5-(2-{(2S)-1-[N-(methoxycarbonyl)-L-valyl]pyrrolidin-2-yl}-1,4,5,11-tetrahydroisochromeno-[4',3':6,7]naphtho[1,2-d]imidazol-9-yl)-1H-imidazol-2-yl]-4-(methoxymethyl)pyrrolidine-1-carboxylate for tert-Butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate.

Methyl {(2S)-1-[(2S)-2-(9-{2-[(2S,4S)-1-[(2R)-2-amino-2-phenylacetyl]-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-3-methyl-1-oxobutan-2-yl}carbamate was prepared according to the method described for the synthesis of methyl (S)-1-((2S,4S)-2-(2'-((2S,4S)-1-((R)-2-amino-2-phenylacetyl)-4-(methoxymethyl)pyrrolidin-2-yl)-1H, 1'H-7,7'-binaphtho[1,2-d]imidazol-2-yl)-4-methylpyrrolidin-1-yl)-3-methyl-1-oxobutan-2-ylcarbamate, substituting methyl (S)-1-((2S,4S)-2-(2'-((2S,4S)-1-((R)-2-tert-butoxycarbonylamino-2-phenylacetyl)-4-(methoxymethyl)pyrrolidin-2-yl)-1H, 1'H-7,7'-binaphtho[1,2-d]imidazol-2-yl)-4-methylpyrrolidin-1-yl)-3-methyl-1-oxobutan-2-ylcarbamate with tert-butyl (2S,4S)-2-[5-(2-{(2S)-1-[N-(methoxycarbonyl)-L-valyl]pyrrolidin-2-yl}-1,11-dihydroisochromeno[4',3': 6,7]naphtho[1,2-d]imidazol-9-yl)-1H-imidazol-2-yl]-4-(methoxymethyl)pyrrolidine-1-carboxylate. MS (ESI) m/z 811 [M+H]$^+$.

Example OM

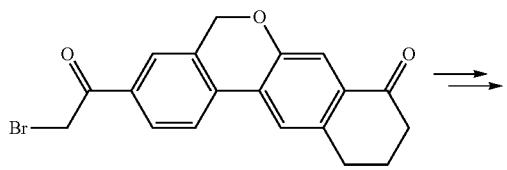

3-(2-bromoacetyl)-10,11-dihydro-5H-dibenzo[c,g]chromen-8(9H)-one

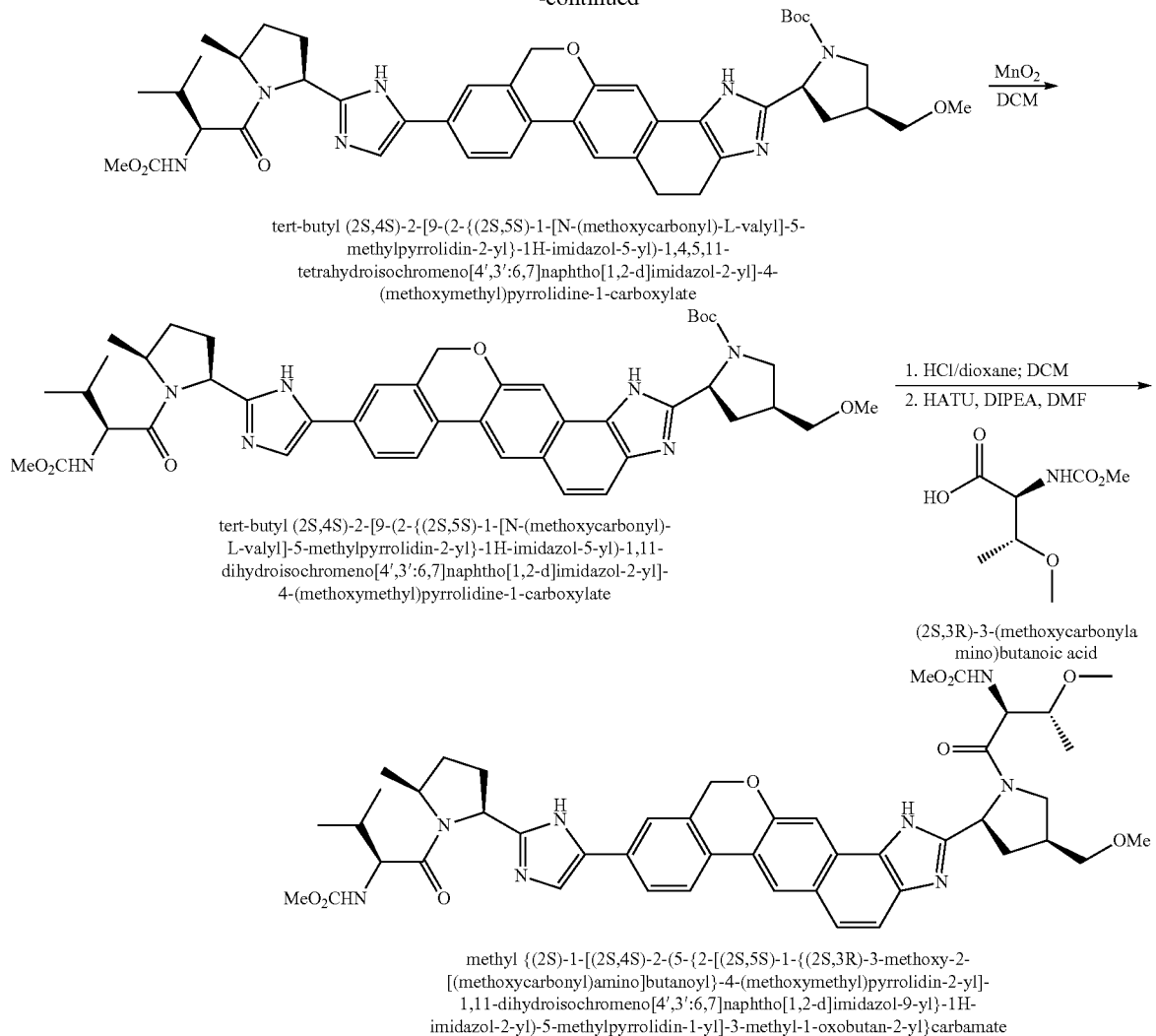

tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4′,3′:6,7]naphtho[1,2-d]imidazol-2-yl]-4-(methoxymethyl)pyrrolidine-1-carboxylate tert-butyl (2S,4S)-2-[9-(2-{(2S,5S)-1-[N-(methoxycarbonyl)-L-valyl]-5-methylpyrrolidin-2-yl}-1H-imidazol-5-yl)-1,11-dihydroisochromeno[4′,3′:6,7]naphtho[1,2-d]imidazol-2-yl]-4-(methoxymethyl)pyrrolidine-1-carboxylate (2S,3R)-3-(methoxycarbonylamino)butanoic acid methyl {(2S)-1-[(2S,4S)-2-(5-{2-[(2S,5S)-1-{(2S,3R)-3-methoxy-2-[(methoxycarbonyl)amino]butanoyl}-4-(methoxymethyl)pyrrolidin-2-yl]-1,11-dihydroisochromeno[4′,3′:6,7]naphtho[1,2-d]imidazol-9-yl}-1H-imidazol-2-yl)-5-methylpyrrolidin-1-yl]-3-methyl-1-oxobutan-2-yl}carbamate tert-Butyl (2S,4S)-2-[9-(2-{(2S,5S)-1-[N-(methoxycarbonyl)-1-valyl]-5-methylpyrrolidin-2-yl}-1H-imidazol-5-yl)-1,4,5,11-tetrahydroisochromeno[4′,3′:6,7]naphtho[1,2-d]imidazol-2-yl]-4-(methoxymethyl)pyrrolidine-1-carboxylate was synthesized from 3-(2-bromoacetyl)-10,11-dihydro-5H-dibenzo[c,g]chromen-8(9H)-one, by the same methods employed in the synthesis of tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4′,3′:6,7]naphtho[1,2-d]imidazol-9-yl)-1H-imidazol-2-yl]-4-(methoxymethyl)pyrrolidine-1-carboxylate, substituting (2S,5S)-1-((S)-2-(methoxycarbonylamino)-3-methylbutanoyl)-5-methylpyrrolidine-2-carboxylic acid for (2S,4S)-1-(tert-butoxycarbonyl)-4-(methoxymethyl)pyrrolidine-2-carboxylic acid and (2S,4S)-1-(tert-butoxycarbonyl)-4-(methoxymethyl)pyrrolidine-2-carboxylic acid for (2S,5S)-1-((S)-2-(methoxycarbonylamino)-3-methylbutanoyl)-5-methylpyrrolidin-2-carboxylic acid.

tert-Butyl (2S,4S)-2-[9-(2-{(2S,5S)-1-[N-(methoxycarbonyl)-L-valyl]-5-methylpyrrolidin-2-yl}-1H-imidazol-5-yl)-1,11-dihydroisochromeno[4′,3′:6,7]naphtho[1,2-d]imidazol-2-yl]-4-(methoxymethyl)pyrrolidine-1-carboxylate was prepared according to the method described for the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4′,3′:6,7]naphtho[1,2-d]imidazol-9-yl)-1H-imidazol-2-yl]-4-(methoxymethyl)pyrrolidine-1-carboxylate, substituting tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4′,3′:6,7]naphtho[1,2-d]imidazol-2-yl]-4-(methoxymethyl)pyrrolidine-1-carboxylate for tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4′,3′:6,7]naphtho[1,2-d]imidazol-9-yl)-1H-imidazol-2-yl]-4-(methoxymethyl)pyrrolidine-1-carboxylate.

Methyl {(2S)-1-[(2S,4S)-2-(5-{2-[(2S,5S)-1-{(2S,3R)-3-methoxy-2-[(methoxycarbonyl)amino]butanoyl}-4-(methoxymethyl)pyrrolidin-2-yl]-1,11-dihydroisochromeno[4′,3′:6,7]naphtho[1,2-d]imidazol-9-yl}-1H-imidazol-2-yl)-5-methylpyrrolidin-1-yl]-3-methyl-1-oxobutan-2-yl}carbamate was prepared from tert-butyl (2S,4S)-2-[9-(2-{(2S,5S)-1-[N-(methoxycarbonyl)-L-valyl]-5-methylpyrrolidin-2-yl}-1H-imidazol-5-yl)-1,11-dihydroisochromeno[4′,3′:6,7]naphtho[1,2-d]imidazol-2-yl]-4-(methoxymethyl)pyrrolidine-1-carboxylate according to the same method described for the synthesis of methyl (S)-1-((2S,4S)-2-(2′-((2S,4S)-1-((2S,3R)-2-methoxycarbonylamino-3-methoxybutanoyl)-4-(methoxymethyl)pyrrolidin-2-yl)-1H, 1'H-7,7'-binaphtho[1,2-d]imidazol-2-yl)-4-methylpyrrolidin-1-yl)-3-methyl-1-oxobutan-2-ylcarbamate, substituting (2S,4S)-tert-Butyl 2-(2'-((2S,4S)-1-((S)-2-(methoxycarbonylamino)-3-methylbutanoyl)-4-methylpyrrolidin-2-yl)-1H, 1'H-7,7'-binaphtho[1,2-d]imidazol-2-yl)-4-(methoxymethyl)pyrrolidine-1-carboxylate with tert-butyl (2S,4S)-2-[9-(2-{(2S,5S)-1-[N-(methoxycarbonyl)-L-valyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate. MS (ESI) m/z 866 [M+H]⁺. ¹H NMR (400 MHz, cd₃od) δ 8.44 (d, J=19.8 Hz, 1H), 8.02 (t, J=8.6 Hz, 2H), 7.98-7.81 (m, 3H), 7.74 (dd, J=22.2, 13.6 Hz, 2H), 7.63-7.41 (m, 2H), 5.79 (d, J=6.0 Hz, 1H), 5.42 (dt, J=43.3, 21.5 Hz, 2H), 5.31-5.10 (m, 5H), 4.85-4.70 (m, 1H), 4.52 (d, J=3.8 Hz, 1H), 4.31 (t, J=8.2 Hz, 1H), 4.17 (dd, J=20.8, 8.8 Hz, 1H), 3.80 (dt, J=19.0, 7.3 Hz, 2H), 3.73-3.63 (m, 7H), 3.63-3.49 (m, 3H), 3.39 (d, J=9.7 Hz, 4H), 3.35 (s, 5H), 3.28 (d, J=4.4 Hz, 3H), 2.84 (d, J=8.8 Hz, 1H), 2.72 (dd, J=12.5, 6.6 Hz, 1H), 2.59-2.45 (m, 1H), 2.45-2.11 (m, 4H), 2.11-1.82 (m, 2H), 1.56 (d, J=6.6 Hz, 3H), 1.35-1.21 (m, 1H), 1.22-1.12 (m, 4H), 1.10-1.01 (m, 2H), 0.99 (d, J=6.6 Hz, 3H), 0.91 (d, 0.1=6.7 Hz, 3H).

Example ON

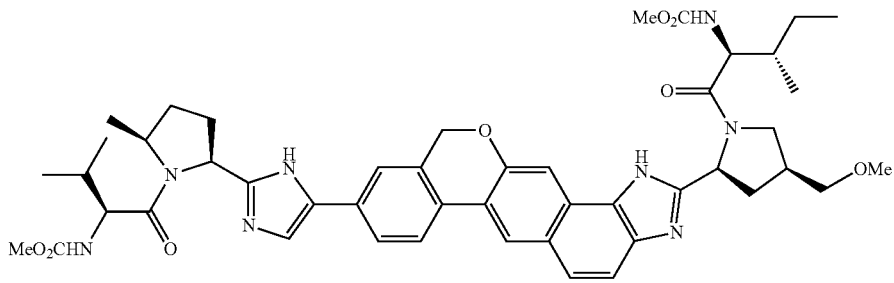

methyl {(2S)-1-[(2S,4S)-2-(5-{2-[(2S,5S)-1-{(2S,3S)-2-[(methoxycarbonyl)amino]-3-methylpentanoyl}-4-(methoxymethyl)-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,4S)-2-(5-{2-[(2S,5S)-1-{(2S,3S)-2-[(methoxycarbonyl)amino]-3-methylpentanoyl}-4-(methoxymethyl)-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate was prepared according to the method described for the synthesis of methyl {(2S,3S)-1-[(2S,4S)-2-(5-{2-[(2S,4S)-1-{(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate substituting tert-butyl (2S,4S)-2-[9-(2-{(2S)-1-[N-(methoxycarbonyl)-L-valyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate for tert-Butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 863 [M+H]⁺. ¹H NMR (400 MHz, cd₃od) δ 8.43 (d, J=24.6 Hz, 1H), 8.01 (dt, J=16.1, 8.0 Hz, 1H), 7.95-7.78 (m, 2H), 7.77-7.64 (m, 2H), 7.59-7.41 (m, 2H), 5.79 (d, J=5.8 Hz, 1H), 5.39 (dt, J=46.2, 23.1 Hz, 1H), 5.27-5.07 (m, 3H), 4.85-4.72 (m, 1H), 4.42 (t, J=8.6 Hz, 1H), 4.31 (d, J=7.9 Hz, 1H), 4.17 (dd, J=19.7, 8.7 Hz, 1H), 3.81 (dd, J=23.6, 13.3 Hz, 1H), 3.69 (d, J=10.0 Hz, 5H), 3.60 (dd, J=14.7, 7.8 Hz, 2H), 3.42 (s, 3H), 3.17 (d, J=6.1 Hz, 1H), 3.07 (s, 1H), 2.99-2.91 (m, 1H), 2.85 (s, 1H), 2.73 (dd, J=12.5, 6.4 Hz, 1H), 2.62-2.48 (m, 1H), 2.45-2.14 (m, 3H), 2.10-1.91 (m, 2H), 1.83 (s, 1H), 1.57 (d, J=6.6 Hz, 3H), 1.44 (d, J=7.4 Hz, 1H), 1.34-1.23 (m, 1H), 1.20-0.96 (m, 5H), 0.90 (dt, J=14.8, 6.7 Hz, 9H).

Example OO

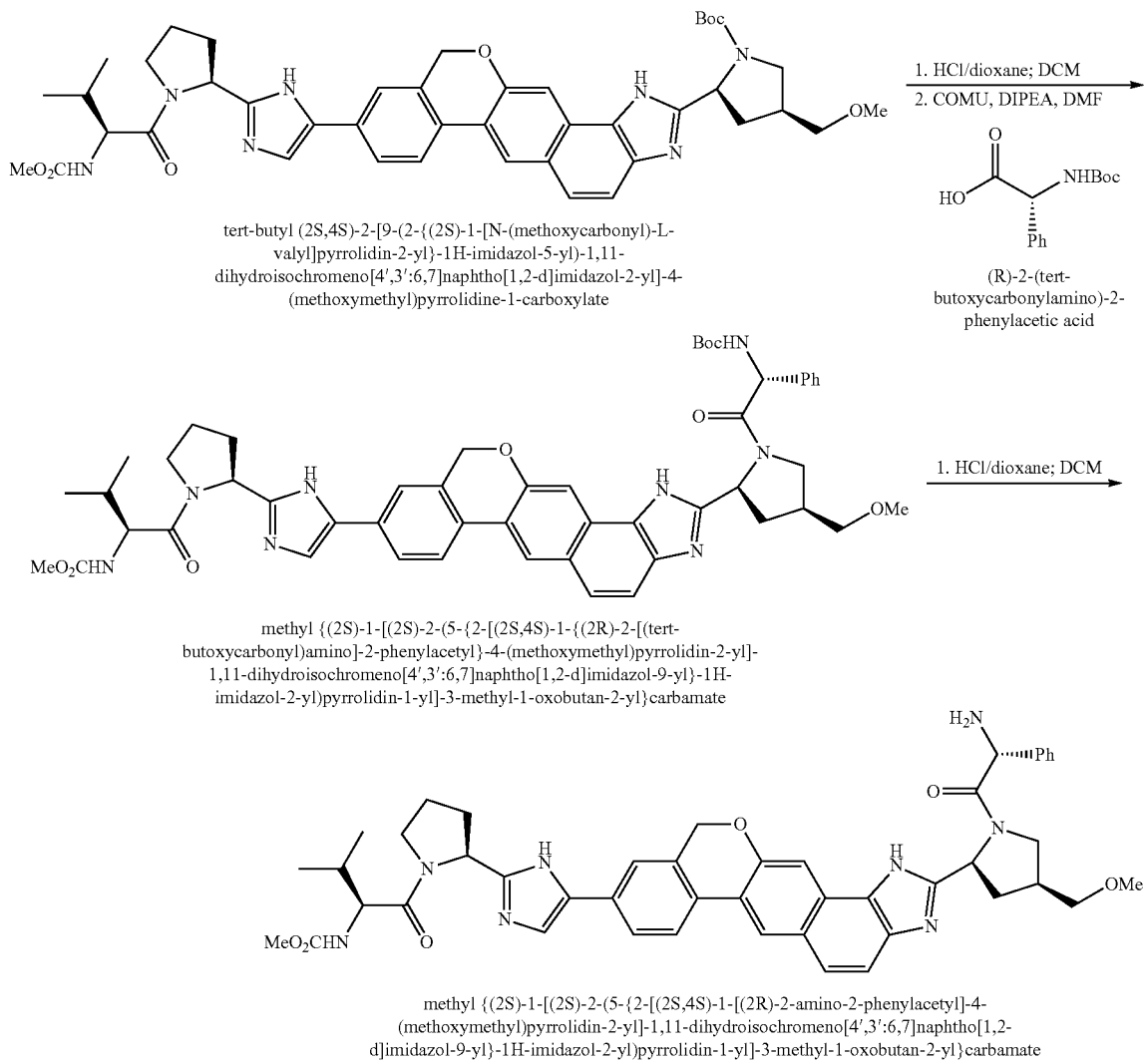

tert-butyl (2S,4S)-2-[9-(2-{(2S)-1-[N-(methoxycarbonyl)-L-valyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (R)-2-(tert-butoxycarbonylamino)-2-phenylacetic acid methyl {(2S)-1-[(2S)-2-(5-{2-[(2S,4S)-1-{(2R)-2-[(tert-butoxycarbonyl)amino]-2-phenylacetyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate methyl {(2S)-1-[(2S)-2-(5-{2-[(2S,4S)-1-[(2R)-2-amino-2-phenylacetyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate Methyl {(2S)-1-[(2S)-2-(5-{2-[(2S,4S)-1-[(2R)-2-amino-2-phenylacetyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate was prepared according to the method described for the synthesis of methyl (S)-1 ((2S,4S)-2-(2'-((2S,4S)-1-((R)-2-amino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate, substituting tert-butyl (2S,4S)-2-[9-(2-{(2S)-1-[N-(methoxycarbonyl)-L-valyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate for (2S,4S)-tert-butyl 2-(2'-((2S,4S)-1-((S)-2-(methoxycarbonylamino)-3-methylbutanoyl)-4-methylpyrrolidin-2-yl) 1H, 1'H-7,7'-binaphtho[1,2-d]imidazol-2-yl)-4-(methoxymethyl)pyrrolidin-1-carboxylate. MS (ESI) m/z 811 [M+H]$^+$.

Example OP

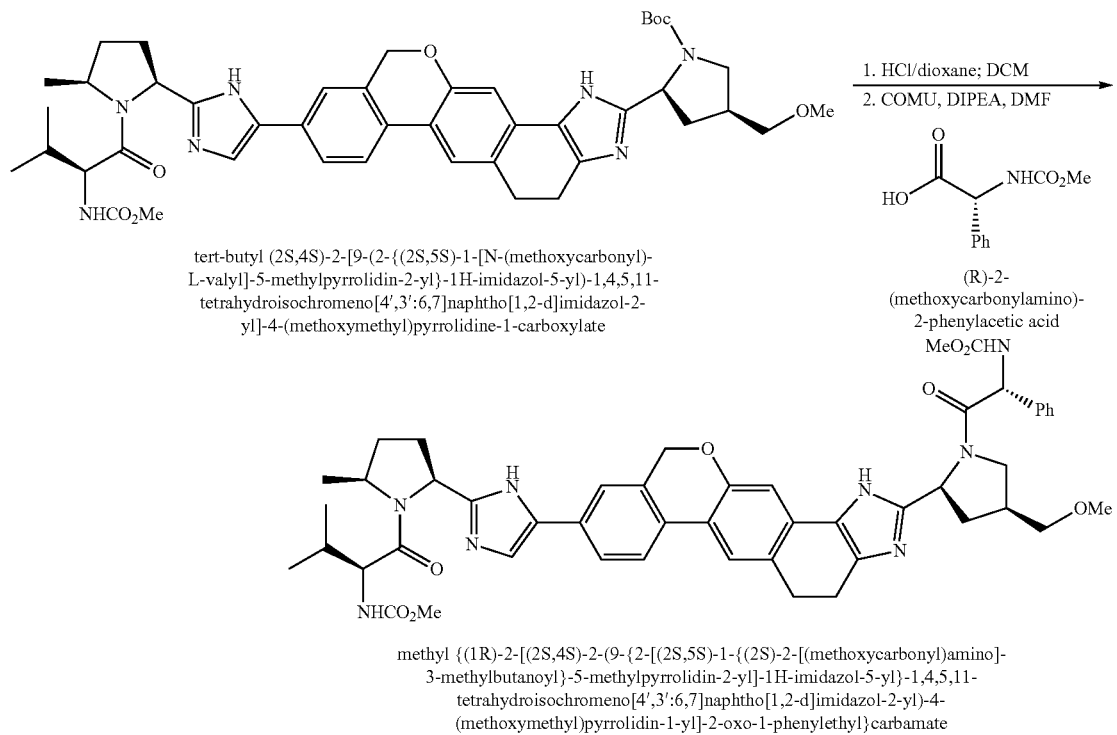

tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4',3':6,7]naphtho[1,2-d]imidazol-2-yl]-4-(methoxymethyl)pyrrolidine-1-carboxylate 1. HCl/dioxane; DCM
2. COMU, DIPEA, DMF (R)-2-(methoxycarbonylamino)-2-phenylacetic acid methyl {(1R)-2-[(2S,4S)-2-(9-{2-[(2S,5S)-1-{(2S)-2-[(methoxycarbonyl)amino]-3-methylbutanoyl}-5-methylpyrrolidin-2-yl]-1H-imidazol-5-yl}-1,4,5,11-tetrahydroisochromeno[4',3':6,7]naphtho[1,2-d]imidazol-2-yl)-4-(methoxymethyl)pyrrolidin-1-yl]-2-oxo-1-phenylethyl}carbamate Methyl {(1R)-2-[(2S,4S)-2-(9-{2-[(2S,5S)-1-{(2 S)-2-[(methoxycarbonyl)amino]-3-methylbutanoyl}-5-methyl-pyrrolidin-2-yl]-1H-imidazol-5-yl}-1,4,5,11-tetrahydroisochromeno[4',3':6,7]naphtho[1,2-d]imidazol-2-yl)-4-(methoxymethyl)pyrrolidin-1-yl]-2-oxo-1-phenylethyl}carbamate was synthesized according to the protocol described for the preparation of methyl {(1R)-2-[(2S,4S)-2-(5-{2-[(2S)-1-{(2S)-2-[(methoxycarbonyl)amino]-3-methylbutanoyl}pyrrolidin-2-yl]-1,4,5,11-tetrahydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}-carbamate, substituting tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4',3':6,7]naphtho-[1,2-d]imidazol-2-yl]-4-(methoxymethyl)pyrrolidine-1-carboxylate for tert-butyl (2S,4S)-2-[5-(2-{(2S)-1-[N-(methoxycarbonyl)-L-valyl]pyrrolidin-2-yl}-1,4,5,11 tetrahydroisochromeno-[4',3':6,7]naphtho[1,2-d]imidazol-9-yl)-1H-imidazol-2-yl]-4-(methoxymethyl)pyrrolidine-1-carboxylate. MS (ESI) m/z 886 [M+H]$^+$. 1H NMR (400 MHz, cd$_3$od) δ 8.02-7.85 (m, 2H), 7.85-7.68 (m, 2H), 7.58 (d, J=21.5 Hz, 1H), 7.55-7.35 (m, 4H), 7.31 (d, J=13.6 Hz, 1H), 5.43 (d, J=19.1 Hz, 1H), 5.28 (t, J=8.3 Hz, 1H), 5.25-5.10 (m, 3H), 4.13 (t, J=9.5 Hz, 1H), 3.93-3.54 (m, 7H), 3.42 (qd, J=9.5, 5.5 Hz, 2H), 3.34 (d, J=7.9 Hz, 1H), 3.28 (s, 3H), 3.19 (t, J=7.8 Hz, 2H), 3.00 (t, J=7.8 Hz, 2H), 2.74-2.46 (m, 3H), 2.44-2.15 (m, 2H), 2.12-1.86 (m, 2H), 1.56 (d, J-6.7 Hz, 2H), 1.29 (d, J=6.3 Hz, 1H), 1.15-1.01 (m, 1H), 0.98 (d, J=6.7 Hz, 2H), 0.88 (d, J=6.8 Hz, 2H).

Example OQ

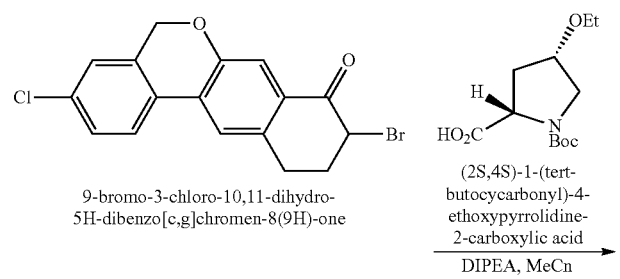

9-bromo-3-chloro-10,11-dihydro-5H-dibenzo[c,g]chromen-8(9H)-one (2S,4S)-1-(tert-butocycarbonyl)-4-ethoxypyrrolidine-2-carboxylic acid DIPEA, MeCn

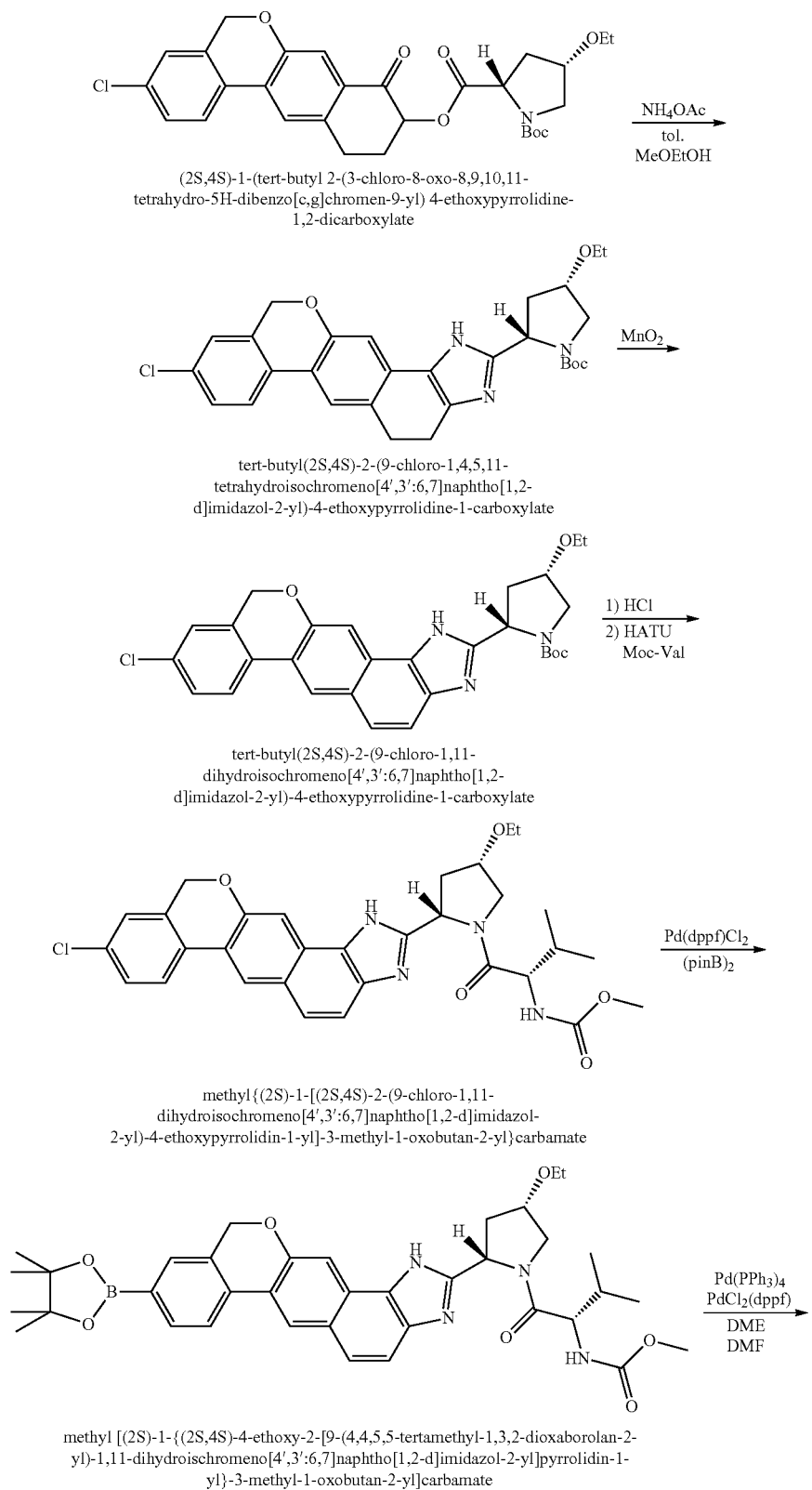

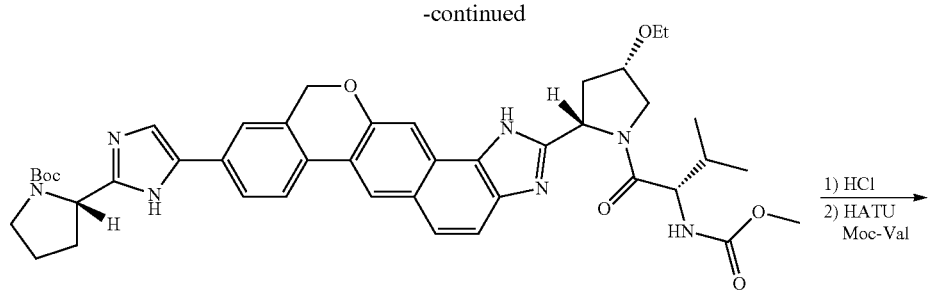

tert-butyl (2S)-2-[5-(2-{(2S,4S)-4-ethoxy-1-[N-(methoxycarbonyl)-L-valyl]pyrrolidin-2-yl)-1,11-dihydroisochromeno[4',3':6,7]naphtho[1,2-d]imidazol-2-yl]pyrrolidine-1-carboxylate

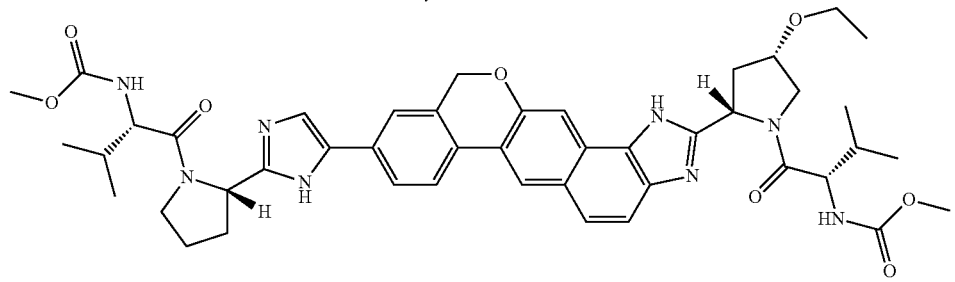

methyl {(2S)-1-[(2S)-2-(5-{2-[(2S,4S)-4-ethoxy-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate (2S,4S)-1-Tert-butyl 2-(3-chloro-8-oxo-8,9,10,11-tetrahydro-5H-dibenzo[c,g]chromen-9-yl)4-ethoxypyrrolidine-1,2-dicarboxylate. To a slurry of 9-bromo-3-chloro-10,11-dihydro-5H-dibenzo[c,g]chromen-8(9H)-one (2.50 g, 6.8 mmol) in MeCN (20 mL) was added (2S,4S)-1-(tert-butoxycarbonyl)-4-ethoxypyrrolidine-2-carboxylic acid (2.68 g, 10.3 mmol) and DIPEA (1.3 mL, 7.5 mmol). The reaction was heated with stirring to 50° C. for 18 h. The reaction was then cooled to room temperature and diluted with EtOAc. The solution was washed with HCl (1N) and brine. The aqueous layers were backextracted with EtOAc and the resulting organic layers were combined, dried (Na$_2$SO$_4$) and concentrated under reduced pressure. The crude residue was purified by silica column chromatography (15% to 50% EtOAc/Hexanes) to afford (2S,4S)-1-tert-butyl 2-(3-chloro-8-oxo-8,9,10,11-tetrahydro-5H-dibenzo[c,g]chromen-9-yl) 4-ethoxypyrrolidine-1,2-dicarboxylate (2.08 g, 56%).

Tert-butyl (2S,4S)-2-(9-chloro-1,4,5,11-tetrahydroisochromeno[4',3':6,7]naphtho[1,2-d]imidazol-2-yl)-4-ethoxypyrrolidine-1-carboxylate. To a solution of (2S,4S)-1-tert-butyl 2-(3-chloro-8-oxo-8,9,10,11-tetrahydro-5H-dibenzo[c,g]chromen-9-yl) 4-ethoxypyrrolidine-1,2-dicarboxylate (2.08 g, 3.8 mmol) in a mixture of toluene (30 mL) and methoxyethanol (4 mL) was added ammonium acetate (2.90 g, 37.7 mmol). The solution was heated with stirring to 80° C. for 18 h. The reaction was then cooled to room temperature and diluted with EtOAc. The solution was washed with brine, and the resulting aqueous layer was backextracted with EtOAc. The resulting organic layers were combined, dried (Na$_2$SO$_4$), and concentrated under reduced pressure. The crude residue was purified by silica column chromatography (10% to 75% EtOAc(w/5% MeOH)/Hexanes) to afford tert-butyl (2S,4S)-2-(9-chloro-1,4,5,11-tetrahydroisochromeno[4',3':6,7]naphtho[1,2-d]imidazol-2-yl)-4-ethoxypyrrolidine-1-carboxylate (0.99 g, 50%).

Tert-butyl (2S,4S)-2-(9-chloro-1,11-dihydroisochromeno[4',3':6,7]naphtho[1,2-d]imidazol-2-yl)-4-ethoxypyrrolidine-1-carboxylate. To a solution of (2S,4S)-2-(9-chloro-1,4,5,11-tetrahydroisochromeno[4',3':6,7]naphtho[1,2-d]imidazol-2-yl)-4-ethoxypyrrolidine-1-carboxylate (0.99 g, 1.9 mmol) in CH$_2$Cl$_2$ (18 mL) was added MnO$_2$ (4.52 g, 52.0 mmol). The resulting slurry was stirred at room temperature for 18 h. The reaction was filtered through celite, washed with CH$_2$Cl$_2$, and concentrated under reduced pressure. The crude residue was purified by silica column chromatography (10% to 75% EtOAc(w/5% MeOH)/Hexanes) to afford tert-butyl (2S,4S)-2-(9-chloro-1,11-dihydroisochromeno[4',3':6,7]naphtho[1,2-d]imidazol-2-yl)-4-ethoxypyrrolidine-1-carboxylate (0.71 g, 72%).

Methyl {(2S)-1-[(2S,4S)-2-(9-chloro-1,11-dihydroisochromeno[4',3':6,7]naphtho[1,2-d]imidazol-2-yl)-4-ethoxypyrrolidin-1-yl]-3-methyl-1-oxobutan-2-yl}carbamate. To a solution of (2S,4S)-2-(9-chloro-1,11-dihydroisochromeno[4',3':6,7]naphtho[1,2-d]imidazol-2-yl)-4-ethoxypyrrolidine-1-carboxylate (0.46 g, 0.9 mmol) in a mixture of CH$_2$Cl$_2$ (9.0 mL) and MeOH (1.5 mL) was added HCl (in dioxanes, 4M, 6.5 mL, 26.0 mmol). The resulting solution was stirred at room temperature for 2 h. The solution was concentrated to dryness under reduced pressure. To the crude intermediate in CH$_2$Cl$_2$ (10.0 mL) was added (S)-2-(methoxycarbonylamino)-3-methylbutanoic acid (0.17 g, 0.9 mmol), HATU (0.41 g, 1.1 mmol), and DIPEA (0.5 mL, 2.9 mmol). The resulting solution was stirred at room temperature for 48 h and diluted with CH$_2$Cl$_2$. The solution was washed with aqueous HCl (1N) and brine. The aqueous layers were backextracted with CH$_2$Cl$_2$ (2×). The resulting organic layers were combined, dried (Na$_2$SO$_4$), and concentrated under reduced pressure. The crude residue was purified by silica column chromatography (20% to 100% EtOAc (w/5% MeOH)/Hexanes to 80% MeOH/EtOAc) to afford methyl {(2S)-1-[(2S,4S)-2-(9-chloro-1,11-dihydroisochromeno[4',3':6,7]naphtho[1,2-d]imidazol-2-yl)-4-ethoxy-pyrrolidin-1-yl]-3-methyl-1-oxobutan-2-yl}carbamate (0.46 g, 90%).

Methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate. To a solution of methyl {(2S)-1-[(2S,4S)-2-(9-chloro-1,11-dihydroisochromeno[4',3':6,7]naphtho[1,2-d]imidazol-2-yl)-4-ethoxypyrrolidin-1-yl]-3-methyl-1-oxobutan-2-yl}carbamate (0.46 g, 0.84 mmol) in dioxane (8.5 mL) was added 4,4,4',4',5,5,5',5'-octamethyl-2,2'-bi(1,3,2-dioxaborolane) (0.32 g, 1.3 mmol), potassium acetate (0.25 g, 2.5 mmol), bis(dibenzylideneacetone)palladium (0.032 g, 0.035 mmol), and 2-dicyclohexylphosphino-2',4',6'-triisopropylbiphenyl (Xphos, 0.032 g, 0.067 mmol). The resulting solution was degassed with argon for 5 min and heated, with stirring, to 90° C. for 6 h. The reaction was cooled to room temperature, diluted with EtOAc, and filtered through celite. The crude residue was purified by silica column chromatography (20% to 100% EtOAc(w/5% MeOH)/Hexanes to 90% MeOH/EtOAc) to afford methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate (0.41 g, 73%).

Tert-butyl (2S)-2-[5-(2-{(2S,4S)-4-ethoxy-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate. To a solution of methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate (0.41 g, 0.61 mmol) in a mixture of DME (6.1 mL) and DMF (1.0 mL) was added (S)-tert-butyl 2-(5-bromo-1H-imidazol-2-yl)pyrrolidine-1-carboxylate (0.39 g, 1.2 mmol), tetrakis(triphenylphosphine)palladium (0.021 g, 0.018 mmol), [1,1'-bis(diphenylphosphino)ferrocene]dichloropalladium (0.030 g, 0.041 mmol), and aqueous potassium carbonate (2M, 1.0 mL, 2.0 mmol). The solution was degasses with argon for 5 min and heated, with stirring, to 85° C. for 6 h. The solution was cooled to room temperature and diluted with EtOAc. The organic layer was washed with water and brine. The aqueous layers were backextracted with EtOAc (3×). The combined organic layers were dried over $Na_2SO_4$ and concentrated under reduced pressure. The crude residue was purified by silica column chromatography (20% to 100% EtOAc(w/5% MeOH)/Hexanes to 80% MeOH/EtOAc) to afford tert-butyl (2S)-2-[5-(2-{(2S,4S)-4-ethoxy-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate (0.16 g, 33%).

Methyl {(2S)-1-[(2S)-2-(5-{2-[(2S,4S)-4-ethoxy-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate.

To a solution of tert-butyl (2S)-2-[5-(2-{(2S,4S)-4-ethoxy-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate (0.048 g, 0.062 mmol) in a mixture of $CH_2Cl_2$ (1.0 mL) and MeOH (0.25 mL) was added HCl (in dioxanes, 4M, 0.47 mL, 1.9 mmol). The solution was stirred at room temperature for 3 h, and then concentrated to dryness under reduced pressure. To the crude intermediate suspended in $CH_2Cl_2$ (1.5 mL) was added (S)-2-(methoxycarbonylamino)-3-methylbutanoic acid (0.012 g, 0.069 mmol), HATU (0.029 g, 0.076 mmol), and DIPEA (0.050 mL, 0.28 mmol). The resulting solution was stirred at room temperature for 1.5 h. The reaction was diluted with DMF and aqueous LiOH (2.5 M, 4 drops) was added. The solution was concentrated to remove the $CH_2Cl_2$ and the crude residue was purified by preparative reverse phase HPLC (10% to 52% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(2S)-1-[(2S)-2-(5-{2-[(2S,4S)-4-ethoxy-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate (0.008 g, 17%). 1H-NMR: 400 MHz, (MeOD) δ: (Mixture of rotomers) 8.37 (s, 1H), 7.97 (s, 2H), 7.37-7.76 (m, 5H), 5.38-5.54 (m, 1H), 5.18 (s, 2H), 5.14-5.16 (m, 1H), 4.21-4.31 (m, 4H), 3.87-4.09 (m, 1H), 3.79-3.85 (m, 2H), 3.66 (s, 3H), 3.64 (s, 3H), 3.46-3.55 (m, 2H), 2.30-2.35 (m, 3H), 2.04-2.06 (m, 3H), 1.11 (m, 2H), 0.95 (d, 3H), 0.88 (d, 3H). MS (ESI) m/z 836.02 [M+H]$^+$.

Example OR

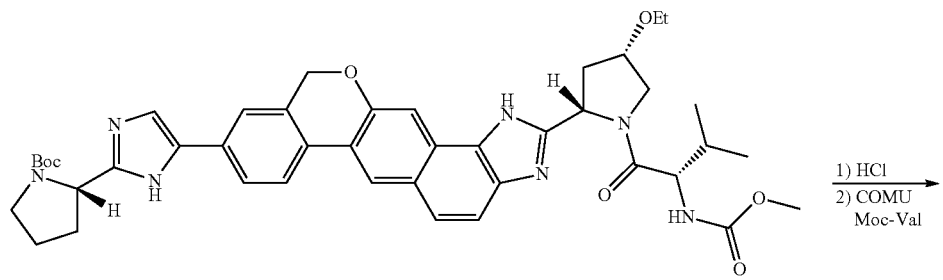

tert-butyl(2S)-2-[5-(2-{(2S,4S)-4-ethoxy-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-]pyrrolidine-1-carboxylate -continued

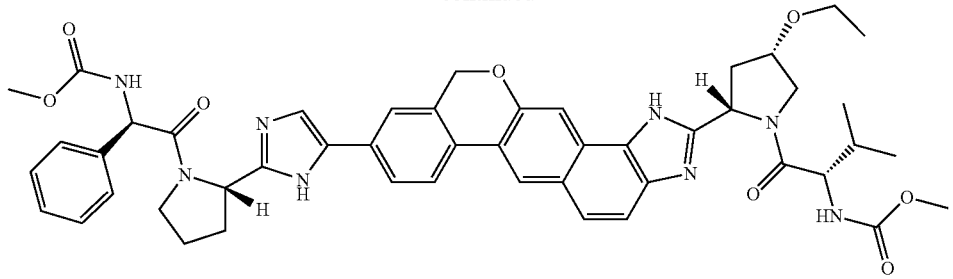

methyl {(1R)-2-[(2S)-2-(5-{2-[(2S,4S)-4-ethoxy-1-{(2S)-
[(methoxycarbonyl)amino]-3-methylbutanoyl}pyrrolidin-2-yl]-1,11-
dihydroisochromeno[4',3':6,7]naphtho[1,2-d]imidazol-9-yl}-1H-imidazol-2-yl)pyrrolidin-
1-yl]-2oxo-1-phenylemethyl}carbamate Methyl {(1R)-2-[(2S)-2-(5-{2-[(2S,4S)-4-ethoxy-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate. To a solution of tert-butyl (2S)-2-[5-(2-{(2S,4S)-4-ethoxy-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate (0.11 g, 0.14 mmol) in a mixture of CH$_2$Cl$_2$ (2.0 mL) and MeOH (0.5 mL) was added HCl (in dioxanes, 4M, 1.0 mL, 4.0 mmol). The solution was stirred at room temperature for 3 h, and then concentrated to dryness under reduced pressure. To the crude intermediate suspended in CH$_2$Cl$_2$ (1.5 mL) was added (R)-2-(methoxycarbonylamino)-2-phenylacetic acid (0.044 g, 0.21 mmol) and DIPEA (0.075 mL, 0.43 mmol). The resulting solution was cooled to −40° C. and COMU (0.096 g, 0.22 mmol) was added. The reaction was allowed to slowly warm to 0° C. over 1 h. The reaction was diluted with DMF. The solution was concentrated to remove the CH$_2$Cl$_2$ and the crude residue was purified by preparative reverse phase HPLC (10% to 55% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(1R)-2-[(2S)-2-(5-{2-[(2S,4S)-4-ethoxy-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate (0.022 g, 18%). 1H-NMR: 400 MHz, (MeOD) δ: (Mixture of rotomers) 8.28 (d, 1H), 7.88 (d, 1H), 7.52-7.70 (m, 3H), 7.28-7.38 (m, 5H), 6.90-6.96 (m, 2H), 5.44-5.47 (m, 1H), 5.31 (s, 1H), 5.12 (s, 2H), 4.16-4.48 (m, 3H), 3.81-3.19 (m, 1H), 3.62-3.76 (m, 2H), 3.58 (s, 3H), 2.56 (s, 3H), 2.42-2.57 (m, 1H), 2.31 (m, 1H), 1.81-2.41 (m, 5H), 1.04 (t, 3H), 0.87 (d, 3H), 0.81 (d, 3H). MS (ESI) m/z 869.55 [M+H]$^+$.

Example OS

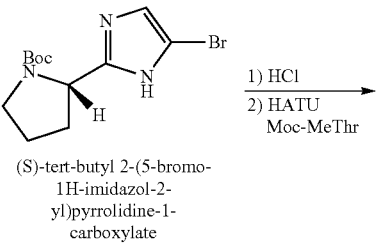

(S)-tert-butyl 2-(5-bromo-
1H-imidazol-2-
yl)pyrrolidine-1-
carboxylate

1) HCl
2) HATU
Moc-MeThr

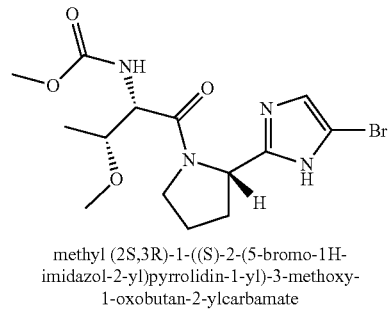

methyl (2S,3R)-1-((S)-2-(5-bromo-1H-
imidazol-2-yl)pyrrolidin-1-yl)-3-methoxy-
1-oxobutan-2-ylcarbamate Methyl (2S,3R)-1-((S)-2-(5-bromo-1H-imidazol-2-yl)pyrrolidin-1-yl)-3-methoxy-1-oxobutan-2-ylcarbamate. To a solution of (S)-tert-butyl 2-(5-bromo-1H-imidazol-2-yl)pyrrolidine-1-carboxylate (1.00 g, 3.2 mmol) in a mixture of CH$_2$Cl$_2$ (30 mL) and MeOH (5 mL) was added HCl (in dioxane, 4 M, 11.5 mL, 46.0 mmol). The solution was stirred at 40° C. for 1 h, cooled to room temperature, and concentrated to dryness under reduced pressure. To the crude intermediate suspended in CH$_2$Cl$_2$ (30 mL) was added (2S,3R)-3-methoxy-2-(methoxycarbonylamino)butanoic acid (0.67 g, 3.5 mmol), HATU (1.47 g, 3.8 mmol), and DIPEA (1.00 mL, 6.0 mmol), The resulting solution was stirred at room temperature for 24 h. DMF (2 mL) and aqueous LiOH (2.5 M, 1 mL) were added and the reaction was concentrated to dryness under reduced pressure. The crude material was diluted with EtOAc and washed with H$_2$O and brine. The aqueous layers were backextracted with EtOAc. The combined organic layers were dried over Na$_2$SO$_4$ and concentrated under reduced pressure. The crude residue was purified by silica column chromatography (20% to 100% EtOAc(w/5% MeOH)/CH$_2$Cl$_2$) to afford methyl (2S,3R)-1-((S)-2-(5-bromo-1H-imidazol-2-yl)pyrrolidin-1-yl)-3-methoxy-1-oxobutan-2-ylcarbamate (1.2g, 100%).

Example OT

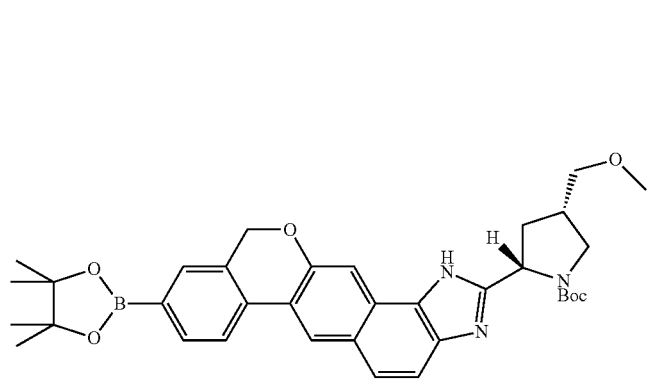

tert-butyl 4-(methoxymethyl)-2-[9-(4,4,5,5-tertamethyl-1,3,2-dioxaborolan-2-yl)-1,11-dihydroischromeno[4',3':6,7]naphtho[1,2-d]imidazol-2-yl]pyrrolidin-1-carboxylate

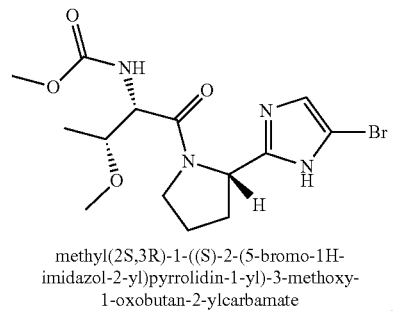

methyl(2S,3R)-1-((S)-2-(5-bromo-1H-imidazol-2-yl)pyrrolidin-1-yl)-3-methoxy-1-oxobutan-2-ylcarbamate

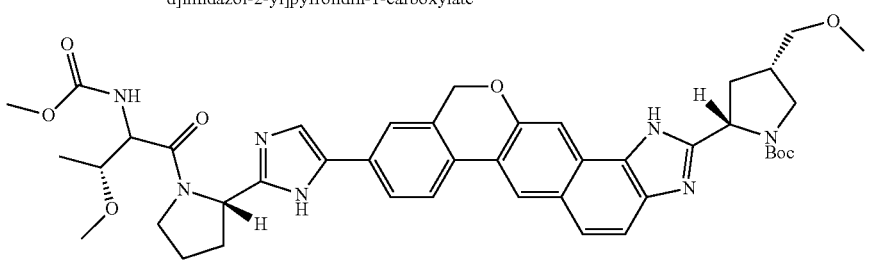

tert-butyl (2S,4S)-2-[9-{(2S)-1-[N-(methoxycarbonyl)-O-methyl-L-threonyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate 1) HCl
2) COMU
   Moc-Phg

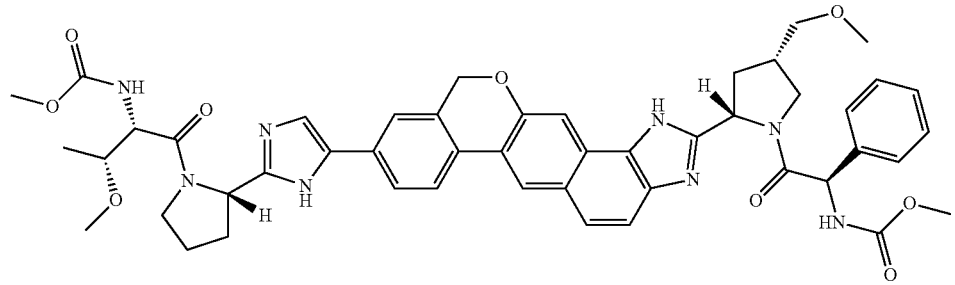

methyl{(1R)-2-[(2S,4S)-2-(9-{2-[(2S)-1-ethoxy-1-{(2S,3R)-3-methoxy-2-[(methoxycarbonyl)amino]butanoyl}pyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate Tert-butyl (2S,4S)-2-[9-(2-{(2S)-1-[N-(methoxycarbonyl)-O-methyl-L-threonyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate.

To a solution of tert-butyl 4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate (1.0 g, 3.2 mmol) in a mixture of DMSO (2.0 mL) and dioxanes (2.0 mL) was added methyl (2S,3R)-1-((S)-2-(5-bromo-1H-imidazol-2-yl)pyrrolidin-1-yl)-3-methoxy-1-oxobutan-2-ylcarbamate (0.24 g, 0.62 mmol), tetrakis(triphenylphosphine)palladium (0.050 g, 0.043 mmol), [1,1'-bis(diphenylphosphino)ferrocene]dichloropalladium (0.030 g, 0.041 mmol), and aqueous potassium carbonate (2M, 0.65 mL, 1.3 mmol). The solution was degassed with argon for 5 min and heated, with stirring, to 85° C. for 6 h. The solution was cooled to room temperature and diluted with EtOAc. The organic layer was washed with water and brine. The aqueous layers were backextracted with EtOAc (3×). The combined organic layers were dried over $Na_2SO_4$ and concentrated under reduced pressure. The crude residue was purified by silica column chromatography (20% to 100% EtOAc(w/5% MeOH)/Hexanes to 60% MeOH/EtOAc) to afford tert-butyl (2S,4S)-2-[9-(2-{(2 S)-1-[N-(methoxycarbonyl)-O-methyl-L-threonyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (0.20 g, 63%).

Methyl {(1R)-2-[(2S,4S)-2-(9-{2-[(2S)-1-{(2S,3R)-3-methoxy-2-[(methoxycarbonyl)amino]butanoyl}pyrrolidin-2-yl]-1H-imidazol-5-yl}-1,11-dihydroisochromeno[4',3':6,7]naphtho[1,2-d]imidazol-2-yl)-4-(methoxymethyl)

pyrrolidin-1-yl]-2-oxo-1-phenylethyl}carbamate. To a solution of tert-butyl (2S,4S)-2-[9-(2-{(2S)-1-[N-(methoxycarbonyl)-O-methyl-L-threonyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (0.20 g, 0.26 mmol) in a mixture of CH$_2$Cl$_2$ (3.0 mL) and MeOH (0.5 mL) was added HCl (in dioxanes, 4M, 2.0 mL, 8.0 mmol). The solution was stirred at 40° C. for 1 h, and then cooled to room temperature and concentrated to dryness under reduced pressure. To the crude intermediate suspended in CH$_2$Cl$_2$ (3.0 mL) was added (R)-2-(methoxycarbonylamino)-2-phenylacetic acid (0.081 g, 0.39 mmol) and DIPEA (0.150 mL, 0.86 mmol). The resulting solution was cooled to −40° C. and COMU (0.180 g, 0.42 mmol) was added. The reaction was allowed to slowly warm to room temperature over 30 min and maintained for 1.5 h. The solution was diluted with CH$_2$Cl$_2$ and washed with aqueous bicarb. The aqueous layer was backextracted with CH$_2$Cl$_2$. The combined organic layers were dried over Na$_2$SO$_4$ and concentrated under reduced pressure. The crude residue was purified by preparative reverse phase HPLC (10% to 50% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(1R)-2-[(2S,4S)-2-(9-{2-[(2S)-1-{(2S,3R)-3-methoxy-2-[(methoxycarbonyl)amino]butanoyl}pyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate (0.10 g, 46%). 1H-NMR: 400 MHz, (MeOD) δ: (Mixture of rotamers) 8.34 (s, 1H), 7.92-7.97 (m, 2H), 7.33-7.69 (m, 10H), 5.53 (s, 1H), 5.36-5.39 (m, 1H), 5.15-5.21 (m, 3H), 4.44 (d, 1H), 3.86-3.93 (m, 2H), 3.68-3.75 (m, 2H), 3.66 (s, 3H), 3.65 (s, 3H), 3.46-3.57 (m, 2H), 3.28 (s, 3H), 3.19 (s, 3H), 2.47-2.60 (m, 3H), 2.22-2.36 (m, 4H), 1.99-2.08 (m, 3H), 1.15 (d, 3H). MS (ESI) m/z 886.19 [M+H]$^+$.

Example OU

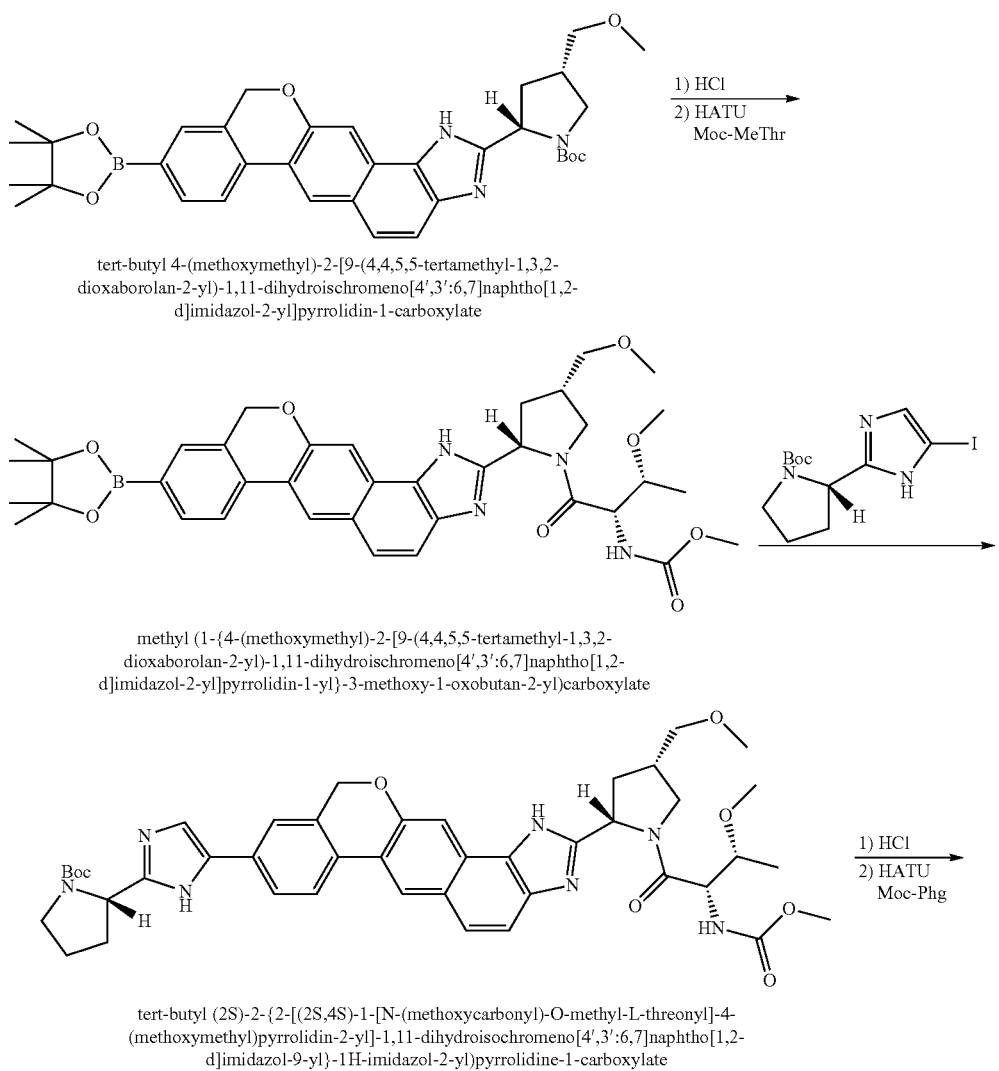

tert-butyl 4-(methoxymethyl)-2-[9-(4,4,5,5-tertamethyl-1,3,2-dioxaborolan-2-yl)-1,11-dihydroischromeno[4',3':6,7]naphtho[1,2-d]imidazol-2-yl]pyrrolidin-1-carboxylate methyl (1-{4-(methoxymethyl)-2-[9-(4,4,5,5-tertamethyl-1,3,2-dioxaborolan-2-yl)-1,11-dihydroischromeno[4',3':6,7]naphtho[1,2-d]imidazol-2-yl]pyrrolidin-1-yl}-3-methoxy-1-oxobutan-2-yl)carboxylate tert-butyl (2S)-2-{2-[(2S,4S)-1-[N-(methoxycarbonyl)-O-methyl-L-threonyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidine-1-carboxylate -continued

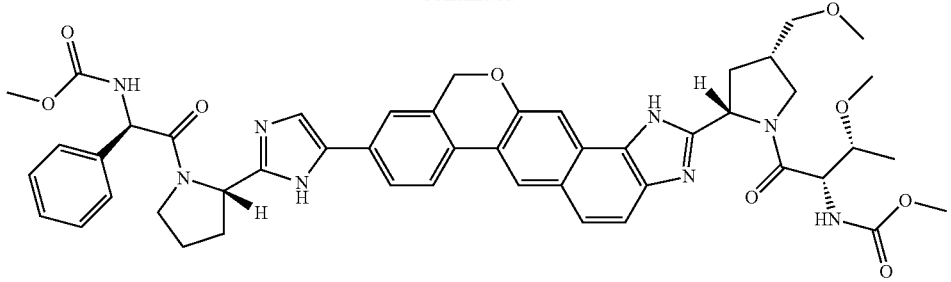

methyl {(1R)-2-[(2S)-2-(5-{2-[(2S,4S)-1-{(2S)-2-[(methoxycarbonyl)amino]-3-methoxybutanoyl}-4-
(methoxymethyl)pyrrolidin-2-yl]-1,11-dihydroisochromeno[4',3':6,7]naphtho[1,2-d]-1H-imidazol-9-yl}-1H-
imidazol-2-yl)pyrrolidin-1-yl]-2-oxo-1-phenylethyl}carbamate Methyl (1-{4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methoxy-1-oxobutan-2-yl)carbamate. To a solution of tert-butyl 4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate (0.25 g, 0.41 mmol) in a mixture of $CH_2Cl_2$ (4.0 mL) and MeOH (1.0 mL) was added HCl (in dioxanes, 4M, 3.0 mL, 12.0 mmol). The resulting solution was stirred at 40° C. for 45 min. The solution was cooled to room temperature and concentrated to dryness under reduced pressure. To the crude intermediate in $CH_2Cl_2$ (4.0 mL) was added (2S,3R)-3-methoxy-2-(methoxycarbonylamino)butanoic acid (0.08 g, 0.42 mmol), HATU (0.17 g, 0.45 mmol), and DIPEA (0.4 mL, 2.3 mmol). The resulting solution was stirred at room temperature for 48 h and diluted with $CH_2Cl_2$. The solution was washed with brine. The aqueous layer was backextracted with $CH_2Cl_2$ (2×). The resulting organic layers were combined, dried ($Na_2SO_4$), and concentrated under reduced pressure. The crude residue was purified by silica column chromatography (30% to 100% EtOAc(w/5% MeOH)/Hexanes to 80% MeOH/EtOAc) to afford methyl (1-{4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methoxy-1-oxobutan-2-yl)carbamate (0.24 g, 92%).

Tert-butyl (2S)-2-(5-{2-[(2S,4S)-1-[N-(methoxycarbonyl)-O-methyl-L-threonyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidine-1-carboxylate. To a solution of methyl (1-{4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methoxy-1-oxobutan-2-yl)carbamate (0.15 g, 0.22 mmol) in a mixture of DMSO (2.0 mL) and dioxane (2.0 mL) was added (S)-tert-butyl 2-(5-iodo-1H-imidazol-2-yl)pyrrolidine-1-carboxylate (0.15 g, 0.40 mmol), tetrakis(triphenylphosphine)palladium (0.028 g, 0.024 mmol), [1,1'-bis(diphenylphosphino)ferrocene]dichloropalladium (0.018 g, 0.025 mmol), and aqueous potassium carbonate (2M, 0.35 mL, 0.70 mmol). The solution was degassed with argon for 5 min and heated, with stirring, to 90° C. for 6 h. The solution was cooled to room temperature and diluted with EtOAc. The organic layer was washed with water and brine. The aqueous layers were backextracted with EtOAc (3×). The combined organic layers were dried over $Na_2SO_4$ and concentrated under reduced pressure. The crude residue was purified by preparative reverse phase HPLC (10% to 55% MeCN/water with 0.1% TFA). The desired fractions were combined and concentrated under reduced pressure to remove volatile organics. The remaining solution was basified with aqueous bicarbonate and extracted with $CH_2Cl_2$ (3×). The combined organic layers were dried over $Na_2SO_4$ and concentrated under reduced pressure to provide tert-butyl (2S)-2-(5-{2-[(2S,4S)-1-[N-(methoxycarbonyl)-O-methyl-L-threonyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidine-1-carboxylate (0.013 g, 7%).

Methyl {(1R)-2-[(2S)-2-(5-{2-[(2S,4S)-1-{(2S)-2-[(methoxycarbonyl)amino]-3-methoxybutanoyl}-4-(methoxymethyl)pyrrolidin-2-yl]-1,11-dihydroisochromeno[4',3':6,7]naphtho[1,2-d]imidazo-9-yl}-1H-imidazol-2-yl)pyrrolidin-1-yl]-2-oxo-1-phenylethyl}carbamate. To a solution of tert-butyl (2S)-2-(5-{2-[(2S,4S)-1-[N-(methoxycarbonyl)-L-valyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidine-1-carboxylate (0.013 g, 0.016 mmol) in a mixture of $CH_2Cl_2$ (0.5 mL) and MeOH (0.02 mL) was added HCl (in dioxanes, 4M, 0.20 mL, 0.80 mmol). The solution was stirred at room temperature for 1 h, and then concentrated to dryness under reduced pressure. To the crude intermediate suspended in $CH_2Cl_2$ (0.5 mL) was added (R)-2-(methoxycarbonylamino)-2-phenylacetic acid (0.006 g, 0.029 mmol) and DIPEA (0.05 mL, 0.28 mmol). The resulting solution was cooled to 0° C. and COMU (0.012 g, 0.028 mmol) was added. The reaction was stirred at 0° C. for 30 min. The solution was diluted with DMF and aqueous LiOH (2.5 M, 2 drops) and concentrated under reduced pressure to remove the $CH_2Cl_2$. The crude residue was purified by preparative reverse phase HPLC (10% to 55% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(1R)-2-[(2S)-2-(5-{2-[(2S,4S)-1-{(2S)-2-[(methoxycarbonyl)amino]-3-methoxybutanoyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate (0.008 g, 61%). $^1$H-NMR: 400 MHz, (MeOD) 6: (Mixture of rotomers) 8.37 (m, 1H), 7.96-7.98 (m, 2H), 7.60-7.79 (m, 3H), 7.35-7.52 (m, 6H), 6.98-7.03 (m, 1H), 5.52 (s, 1H), 5.26-5.39 (m, 2H), 5.20 (s, 2H), 4.44 (m, 1H), 4.27 (m, 1H), 3.64 (s, 6H), 3.50-3.57 (m, 3H), 3.37 (s, 3H), 3.29-3.44 (m, 3H), 3.20 (s, 3H), 2.68-2.72 (m, 2H), 2.57-2.62 (m, 2H), 1.89-2.15 (m, 6H), 1.18 (d, 3H). MS (ESI) m/z 885.73 [M+H]$^+$.

Example OV

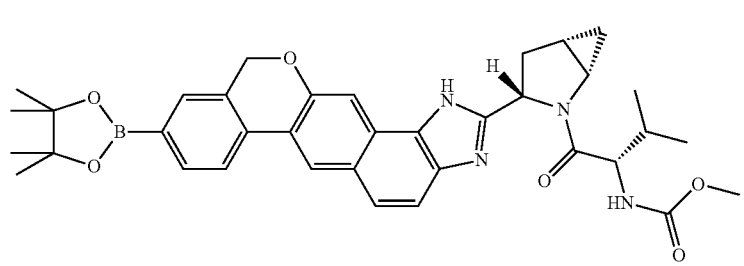

methyl [(2S)-1-{(2S,4S)-3-[9-(4,4,5,5-tertamethyl-1,3,2-dioxaborolan-2-yl)-1,11-dihydroisochromeno[4',3':6,7]naphtho[1,2-d]imidazol-2-yl]-2-azabicyclo[3.1.0]hex-2-yl}-3-methyl-1-oxobutan-2-yl]carbamate

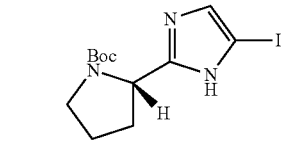

(2S,4S)-tert-butyl 2-(5-iodo-1H-imidazol-2-yl)-4-(methoxymethyl)pyrrolidine-1-carboxylate Pd(PPh₃)₄
PdCl₂(dppf)
DME, DMF

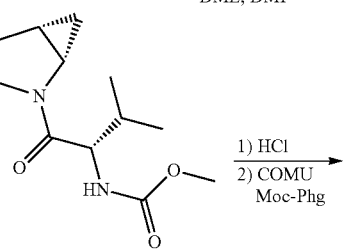

tert-butyl (2S,4S)-2-[5-(2-{(1S,3S,5S)-2-[N-(methoxycarbonyl)-L-valyl]-2-azabicylclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate 1) HCl
2) COMU
   Moc-Phg

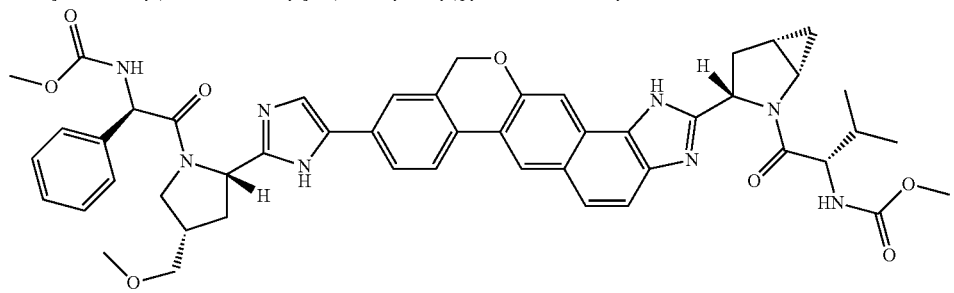

methyl {(1R)-2-[(2S,4S)-2-(5-{2-[(1S,3S,5S)-2-{(2S)-2-[(methoxycarbonyl)amino]-3-methylbutanoyl}-2-azabicyclo[3.1.0]hex-3-yl}-1,11-dihydroisochromeno[4',3':6,7]naphtho[1,2-d]imidazol-9-yl}1H-imidazol-2-yl]-4-(methoyxmethyl)pyrrolidin-1-yl]-2-oxo-1-phenylethyl}carbamate Methyl [(2S)-1-{(2S,4S)-3-[9-(4,4,5,5-tetramethyl-1,3,2-dioxaborolan-2-yl)-1,11-dihydroisochromeno[4',3':6,7]naphtho[1,2-d]imidazol-2-yl]-2-azabicyclo[3.1.0]hex-2-yl}-3-methyl-1-oxobutan-2-yl]carbamate. Methyl [(2S)-1-{(2S,4S)-3-[9-(4,4,5,5-tetramethyl-1,3,2-dioxaborolan-2-yl)-1,11-dihydroisochromeno[4',3':6,7]naphtho[1,2-d]imidazol-2-yl]-2-azabicyclo[3.1.0]hex-2-yl}-3-methyl-1-oxobutan-2-yl]carbamate was prepared following the procedure for methyl [(2S)-1-{(2S,4S)-4-ethoxy-2-[9-(4,4,5,5-tetramethyl-1,3,2-dioxaborolan-2-yl)-1,11-dihydroisochromeno[4',3:6,7]naphtho[1,2-d]imidazol-2-yl]pyrrolidin-1-yl}-3-methyl-1-oxobutan-2-yl]carbamate by substitution of (1 S,3 S,5 S)-2-(tert-butoxycarbonyl)-2-azabicyclo[3.1.0] hexane-3-carboxylic acid for (2S,4S)-1-(tert-butoxycarbonyl)-4-ethoxypyrrolidine-2-carboxylic acid.

Tert-butyl (2S,4S)-2-[5-(2-{(1 S,3S,5S)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. To a solution of methyl [(2S)-1-{(2S,4S)-3-[9-(4,4,5,5-tetramethyl-1,3,2-dioxaborolan-2-yl)-1,11-dihydroisochromeno[4',3':6,7]naphtho[1,2-d]imidazol-2-yl]-2-azabicyclo[3.1.0]hex-2-yl}-3-methyl-1-oxobutan-2-yl]carbamate (0.19 g, 0.30 mmol) in a mixture of DMSO (2.0 mL) and dioxane (2.0 mL) was added (2S,4S)-tert-butyl 2-(5-iodo-1H-imidazol-2-yl)-4-(methoxymethyl)pyrrolidine-1-carboxylate (0.20 g, 0.55 mmol), tetrakis(triphenylphosphine)palladium (0.035 g, 0.030 mmol), [1,1'-bis(diphenylphosphino)ferrocene]dichloropalladium (0.025 g, 0.034 mmol), and aqueous potassium carbonate (2M, 0.5 mL, 1.0 mmol). The solution was degassed with argon for 5 min and heated, with stirring, to 90° C. for 6 h. The solution was cooled to room temperature, diluted with EtOAc, and filtered through celite. The filtrate was concentrated under reduced pressure and purified by silica column chromatography (2% to 25% CH₂Cl₂/MeOH) and preparative reverse phase HPLC (10% to 55% MeCN/water with 0.1% TFA). The desired fractions were combined and concentrated under reduced pressure to remove volatile organics. The aqueous layer was basified with aqueous sodium bicarbonate and extracted with CH₂Cl₂ (3×). The organic layers were combine, dried over Na₂SO₄, and concentrated under reduced pressure to afford tert-butyl (2S,4S)-2-[5-(2-{(1S,3S,5S)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (0.025 g, 11%).

Methyl {(1R)-2-[(2S,4S)-2-(5-{2-[(1S,3S,5S)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate. To a solution of tert-butyl (2S,4S)-2-[5-(2-{(1S,3S,5S)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (0.025 g, 0.032 mmol) in a mixture of CH₂Cl₂ (1.0 mL) and MeOH (0.25 mL) was added HCl (in dioxanes, 4M, 0.50 mL, 2.0 mmol). The solution was stirred at room temperature for 12 h, and then concentrated to dryness under reduced pressure. To the crude intermediate suspended in CH₂Cl₂ (0.5 mL) was added (R)-2-(methoxycarbonylamino)-2-phenylacetic acid (0.012 g, 0.057 mmol) and DIPEA (0.05 mL, 0.28 mmol). The resulting solution was cooled to 0° C. and COMU (0.023 g, 0.054 mmol) was added. The reaction was stirred at 0° C. for 30 min. The solution was diluted with DMF and aqueous LiOH (2.5 M, 2 drops) and concentrated under reduced pressure to remove the CH₂Cl₂. The crude residue was purified by preparative reverse phase HPLC (10% to 55% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(1R)-2-[(2S,4S)-2-(5-{2-[(1S,3S,5S)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate (0.015 g, 55%). ¹H-NMR: 400 MHz, (MeOD) δ: (Mixture of rotomers) 8.35 (m, 1H), 7.94-7.96 (m, 2H), 7.54-7.78 (m, 6H), 6.93-7.00 (m, 1H), 5.72 (m, 1H), 5.46 (s, 1H), 5.19 (s, 2H), 5.14-5.16 (m, 1H), 3.95 (m, 1H), 3.67 (s, 3H), 3.63 (s, 3H), 3.42-3.49 (m, 2H), 3.24 (s, 3H), 2.67-2.78 (m, 2H), 2.41-2.62 (m, 3H), 2.01-2.13 (m, 2H), 1.86-1.99 (m, 3H), 0.99-1.03 (m, 2H), 0.90 (d, 3H). MS (ESI) m/z 882.23 [M+H]⁺.

Example OW

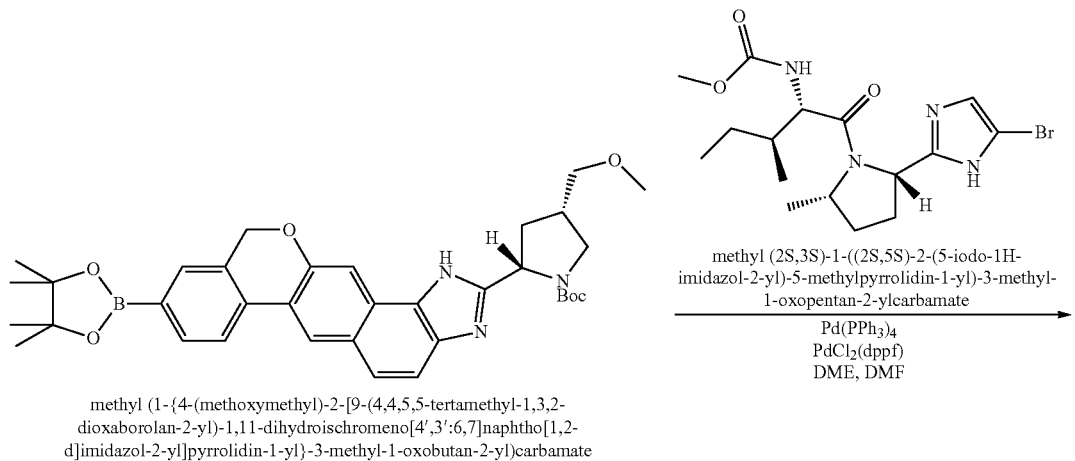

methyl (1-{4-(methoxymethyl)-2-[9-(4,4,5,5-tertamethyl-1,3,2-dioxaborolan-2-yl)-1,11-dihydroischromeno[4',3':6,7]naphtho[1,2-d]imidazol-2-yl]pyrrolidin-1-yl}-3-methyl-1-oxobutan-2-yl)carbamate methyl (2S,3S)-1-((2S,5S)-2-(5-iodo-1H-imidazol-2-yl)-5-methylpyrrolidin-1-yl)-3-methyl-1-oxopentan-2-ylcarbamate Pd(PPh₃)₄
PdCl₂(dppf)
DME, DMF

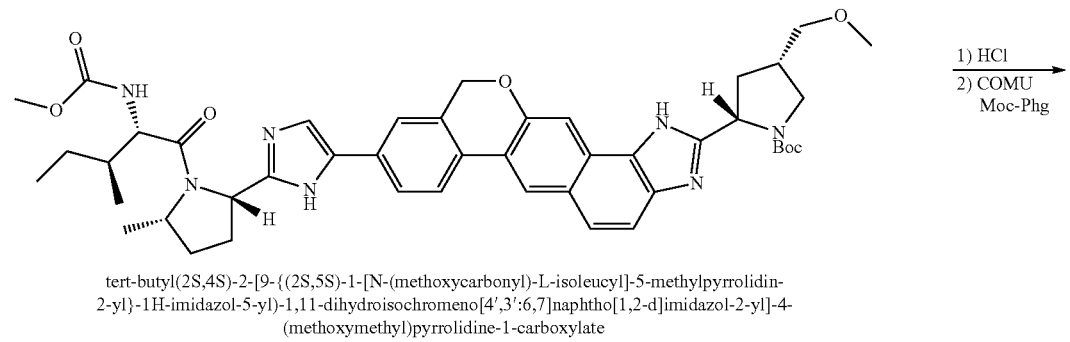

tert-butyl(2S,4S)-2-[9-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate 1) HCl
2) COMU
Moc-Phg

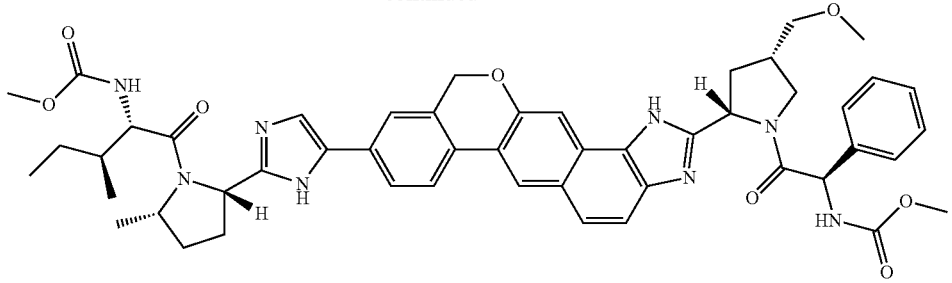

methyl {(1R)-2-[(2S, 4S)-2-(9-{2-[(2S,5S)-1-{(2S,3S)-2-[(methoxycarbonyl)amino]-3-methylpentanoyl}-5-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate Tert-butyl (2S,4S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate. To a solution of methyl (1-{4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl)carbamate (0.47 g, 0.78 mmol) in a mixture of DMSO (4.0 mL) and dioxane (4.0 mL) was added methyl (2S,3S)-1-((2S,5S)-2-(5-iodo-1H-imidazol-2-yl)-5-methylpyrrolidin-1-yl)-3-methyl-1-oxopentan-2-ylcarbamate (0.26 g, 0.72 mmol), tetrakis(triphenylphosphine)palladium (0.090 g, 0.078 mmol), [1,1'-bis(diphenylphosphino)ferrocene]dichloropalladium (0.061 g, 0.083 mmol), and aqueous potassium carbonate (2M, 1.2 mL, 2.4 mmol). The solution was degassed with argon for 5 min and heated, with stirring, to 90° C. for 6 h. The solution was cooled to room temperature, diluted with EtOAc, and filtered through celite. The filtrate was concentrated under reduced pressure and diluted with EtOAc. The organic solution was washed water and brine and the aqueous layers were backextracted with EtOAc. The combined organic layers were dried over $Na_2SO_4$ and concentrated under reduced pressure. The crude residue was purified by silica column chromatography (10% to 100% EtOAc (5% MeOH)/$CH_2Cl_2$) to afford tert-butyl (2S,4S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3': 6,7]naphtho[1,2-d]imidazol-2-yl]-4-(methoxymethyl)pyrrolidine-1-carboxylate (0.25 g, 40%).

Methyl {(1R)-2-[(2S,4S)-2-(9-{2-[(2S,5S)-1-{(2S,3S)-2-[(methoxycarbonyl)amino]-3-methylpentanoyl}-5-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate. To a solution of tert-butyl (2S,4S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (0.175 g, 0.21 mmol) in a mixture of $CH_2Cl_2$ (2.0 mL) and MeOH (0.5 mL) was added HCl (in dioxanes, 4M, 1.6 mL, 6.4 mmol). The solution was stirred at 40° C. for 1 h, cooled to room temperature, and then concentrated to dryness under reduced pressure. To the crude intermediate suspended in $CH_2Cl_2$ (3.0 mL) was added (R)-2-(methoxycarbonylamino)-2-phenylacetic acid (0.070 g, 0.34 mmol) and DIPEA (0.15 mL, 0.86 mmol). The resulting solution was cooled to −40° C. and COMU (0.15 g, 0.35 mmol) was added. The reaction was warmed to room temperature over 30 min and diluted with $CH_2Cl_2$. The solution was washed with saturated aqueous sodium bicarbonate. The aqueous layer was back-extracted with $CH_2Cl_2$, and the combined organic layers were dried over $Na_2SO_4$ and concentrated under reduced pressure. The crude residue was purified by preparative reverse phase HPLC (10% to 58% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(1R)-2-[(2S,4S)-2-(9-{2-[(2S,5S)-1-{(2S,3S)-2-[(methoxycarbonyl)amino]-3-methylpentanoyl}-5-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate (0.079 g, 41%). $^1$H-NMR: 400 MHz, (MeOD) δ: (Mixture of rotomers) 8.36 (m, 1H), 7.93-7.98 (m, 2H), 7.66-7.84 (m, 3H), 7.35-7.48 (m, 7H), 5.53 (s, 1H), 5.36-5.39 (m, 1H), 5.17 (d, 2H), 5.08 (m, 1H), 4.14-4.35 (m, 1H), 3.74 (m, 4H), 3.64 (s, 3H), 3.62 (s, 3H), 3.46 (m, 1H), 3.19 (s, 3H), 2.76 (m, 1H), 2.46-2.60 (m, 3H), 2.24-2.35 (m, 1H), 2.08-2.18 (m, 2H), 1.91 (m, 1H), 1.61-1.87 (m, 2H), 1.48 (d, 3H), 1.13-1.21 (m, 3H), 0.80-0.97 (m, 3H). MS (ESI) m/z 898.24 [M+H]$^+$.

Example OX

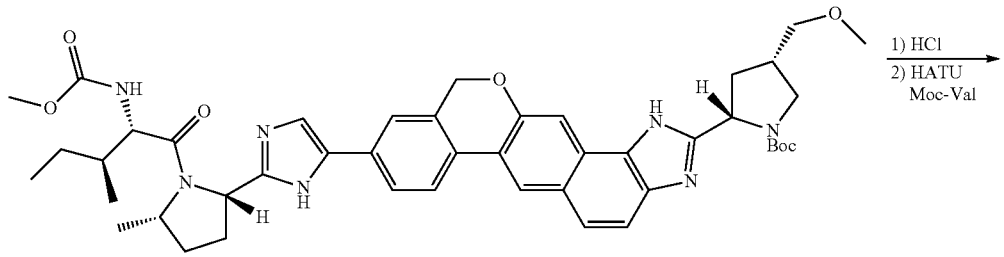

tert-butyl (2S,4S)-2-[9-(2S,5S)-1-[N-(methoxycarbonyl)-L-isoleucyl]-5-methylpyrrolidin-2-yl}-1H-imidazol-5-yl}-1,11-dihydroisochromeno[4',3':6,7]naphtho[1,2-d]imidazol-2-yl]-4-(methoxymethyl)pyrrolidine-1-carboxylate

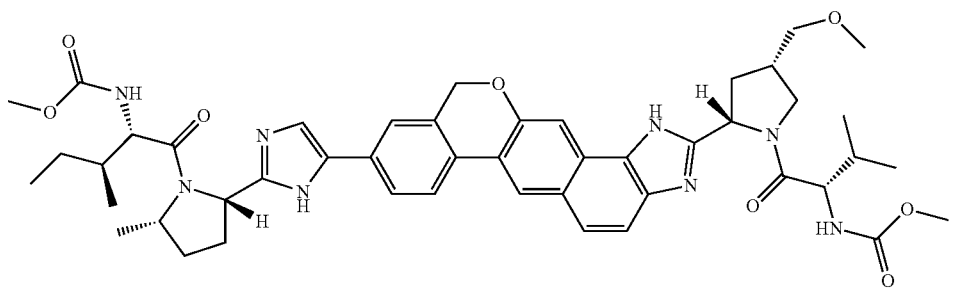

methyl {(2S)-1-[(2S,4S)-2-(9-{2-[(2S,5S)-1-{(2S,3S)-2-[(methoxycarbonyl)amino]-3-methylpentanoyl}-5-methylpyrrolidin-2-yl]-1H-imidazol-5-yl}-1,11-dihydroisochromeno[4',3':6,7]naphtho[1,2-d]imidazol-2-yl]-4-(methoxymethyl)pyrrolidin-1-yl]-3-methyl-1-oxobutan-2-yl}carbamate Methyl {(2S)-1-[(2S,4S)-2-(9-{2-[(2S,5S)-1-{(2S,3S)-2-[(methoxycarbonyl)amino]-3-methylpentanoyl}-5-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxobutan-2-yl}carbamate. To a solution of tert-butyl (2S,4S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (0.075 g, 0.09 mmol) in a mixture of $CH_2Cl_2$ (1.0 mL) and MeOH (0.25 mL) was added HCl (in dioxanes, 4M, 0.7 mL, 2.8 mmol). The solution was stirred at 40° C. for 1 h, cooled to room temperature, and then concentrated to dryness under reduced pressure. To the crude intermediate suspended in $CH_2Cl_2$ (3.0 mL) was added (S)-2-(methoxycarbonylamino)-3-methylbutanoic acid (0.020 g, 0.14 mmol), HATU (0.043 g, 0.11 mmol) and DIPEA (0.10 mL, 0.57 mmol). The reaction was stirred at room temperature for 2 h. The reaction was diluted with DMF and aqueous LiOH (2.5 M, 3 drops) and the $CH_2Cl_2$ was removed under reduced pressure. The crude residue was purified by preparative reverse phase HPLC (10% to 58% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(2S)-1-[(2S,4S)-2-(9-{2-[(2S,5S)-1-{(2S,3S)-2-[(methoxycarbonyl)amino]-3-methylpentanoyl}-5-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxobutan-2-yl}carbamate (0.031 g, 38%). $^1$H-NMR: 400 MHz, (MeOD) δ: (Mixture of rotomers) 8.34 (m, 1H), 7.91-9.97 (m, 2H), 7.50-7.81 (m, 3H), 7.35-7.38 (m, 2H), 5.17-5.26 (m, 3H), 5.08 (m, 1H), 4.14-4.33 (m, 4H), 3.64 (s, 3H), 3.63 (s, 3H), 3.51-3.59 (m, 3H), 3.37 (s, 3H), 2.71 (m, 1H), 2.55-2.59 (m, 1H), 2.23-2.33 (m, 1H), 1.92-2.10 (m, 2H), 1.77-1.89 (m, 1H), 1.60 (m, 1H), 1.48 (d, 1H), 1.11-1.22 (m, 2H), 0.81-0.98 (m, 12H). MS (ESI) m/z 864.27 [M+H]$^+$.

Example OY

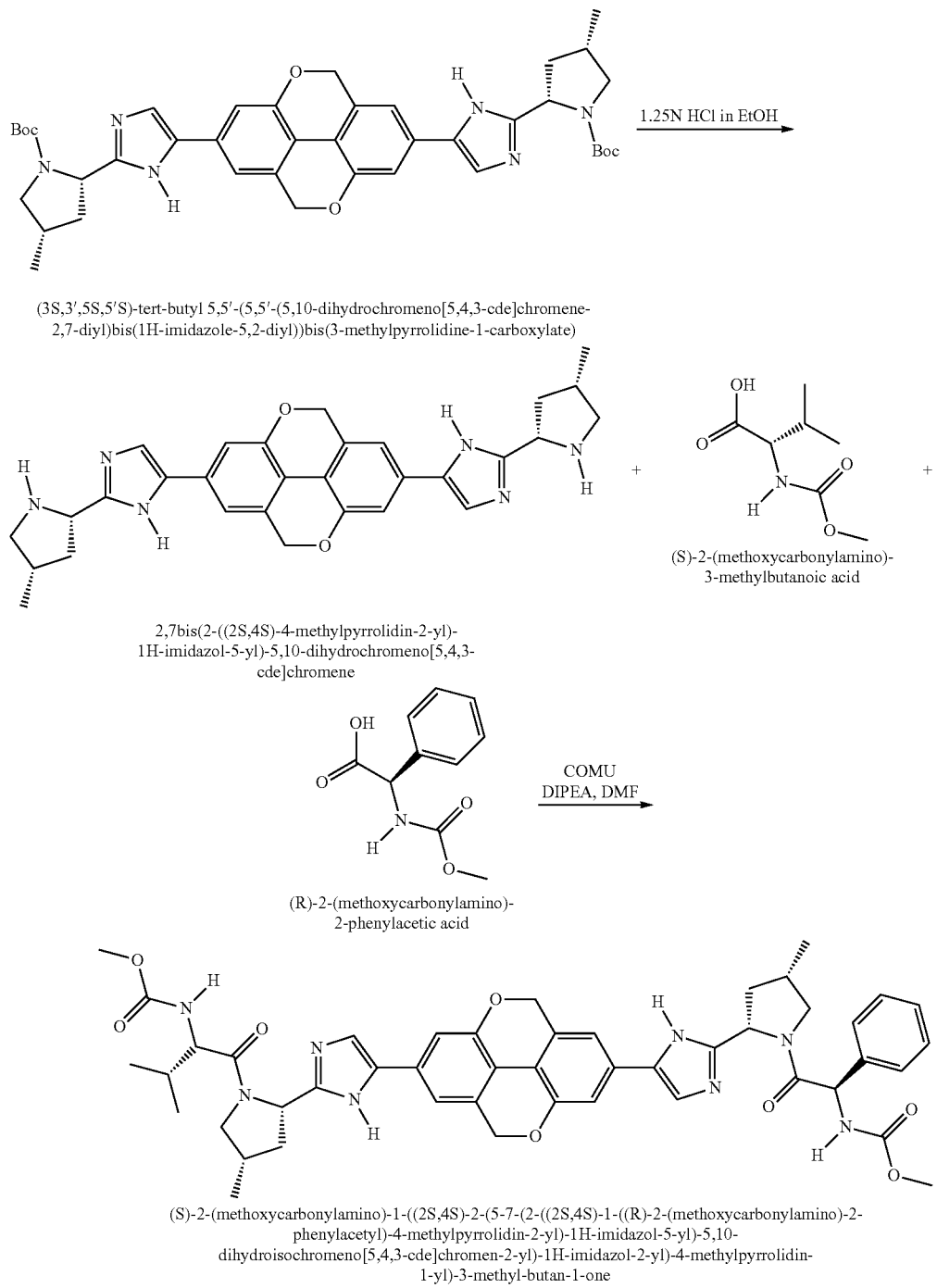

(3S,3′,5S,5′S)-tert-butyl 5,5′-(5,5′-(5,10-dihydrochromeno[5,4,3-cde]chromene-2,7-diyl)bis(1H-imidazole-5,2-diyl))bis(3-methylpyrrolidine-1-carboxylate)

2,7bis(2-((2S,4S)-4-methylpyrrolidin-2-yl)-1H-imidazol-5-yl)-5,10-dihydrochromeno[5,4,3-cde]chromene (S)-2-(methoxycarbonylamino)-3-methylbutanoic acid (R)-2-(methoxycarbonylamino)-2-phenylacetic acid (S)-2-(methoxycarbonylamino)-1-((2S,4S)-2-(5-7-(2-((2S,4S)-1-((R)-2-(methoxycarbonylamino)-2-phenylacetyl)-4-methylpyrrolidin-2-yl)-1H-imidazol-5-yl)-5,10-dihydroisochromeno[5,4,3-cde]chromen-2-yl)-1H-imidazol-2-yl)-4-methylpyrrolidin-1-yl)-3-methyl-butan-1-one (S)-2-(methoxycarbonylamino)-1-((2S,4S)-2-(5-(7-(2-((2S,4S)-1-((R)-2-(methoxycarbonylamino)-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-3-methylbutan-1-one: (3S,3′S,5S,5′S)-tert-butyl 5,5′-(5,5′-(5,10-dihydrochromeno[5,4,3-cde]chromene-2,7-diyl)bis(1H-imidazole-5,2-diyl))bis(3-methylpyrrolidine-1-carboxylate) was obtained as in example LL but using (2S,4S)-1-(tert-butoxycarbonyl)-4-methylpyrrolidine-2-carboxylic acid in place of (S)-1-(tert-butoxycarbonyl)pyrrolidine-2-carboxylic acid. (3 S,3′S,5 S,5′S)-tert-butyl 5,5′-(5,5′-(5,10-dihydrochromeno[5,4,3-cde]chromene-2,7-diyl)bis(1H-imidazole-5,2-diyl))bis(3-methylpyrrolidine-1-carboxylate) (500 mg, 0.706 mmol) was treated with 5.7 mL 1.25N HCl in ethanol and heated at 50° C. for 4 hours. The reaction mixture was concentrated under reduced pressure to give 2,7-bis(2-((2S,4S)-4-methylpyrrolidin-2-yl)-1H-imidazol-5-yl)-5,10-dihydrochromeno[5,4,3-cde]chromene. A mixture of (S)-2-(methoxycarbonylamino)-3-methylbutanoic acid (124 mg, 0.706 mmol), (R)-2-(methoxycarbonylamino)-2-phenylacetic acid (148 mg, 0.706 mmol), COMU (665 mg, 1.55 mmol) in DMF was allowed to preactivate for 15 minutes before it was added to the crude amine in 3.5 mL DMF and 0.74 mL DIPEA. Once starting material was consumed, by LCMS monitoring, the reaction mixture was neutralized with formic acid, diluted with methanol and purified by reverse phase HPLC in 6 injections to provide three products, two homodimers and the heterodimer (S)-2-(methoxycarbonylamino)-1-((2S,4S)-2-(5-(7-(2-((2S,4S)-1-((R)-2-(methoxycarbonylamino)-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-3-methylbutan-1-one (220.3 mg) as a salt of trifluoroacetic acid.

MS (ESI) m/z 857.1 [M+H]+;

$^1$H NMR (CD$_3$CN) 7.46-7.31 (m, 7H), 6.901-6.746 (m, 4H), 6.045 (m, 1H), 5.222 (d, 1H, J=7.6 Hz), 5.169 (m, 1H), 5.095 (d, 4H, J=7.2 Hz), 4.370 (m, 1H), 4.158 (m, 1H), 3.775 (m, 1H), 3.630 (s, 6H), 3.533 (m, 2H), 2.487 (m, 6H), 2.229 (m, 2H), 1.777 (m, 1H), 1.162 (d, 3H, J=6.0 Hz), 1.073 (d, 3H, J=6.4 Hz), 1.024 (d, 3H, J=6.8 Hz), 0.929 (d, 3H, J=6.4 Hz).

Example OZ

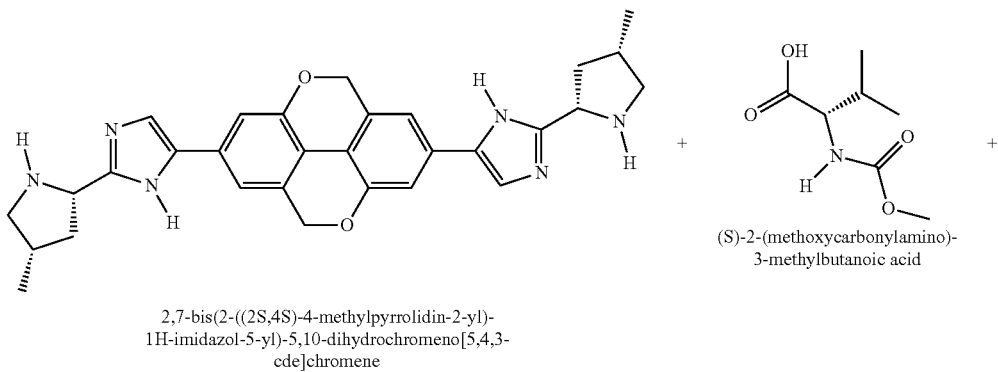

2,7-bis(2-((2S,4S)-4-methylpyrrolidin-2-yl)-1H-imidazol-5-yl)-5,10-dihydrochromeno[5,4,3-cde]chromene (S)-2-(methoxycarbonylamino)-3-methylbutanoic acid

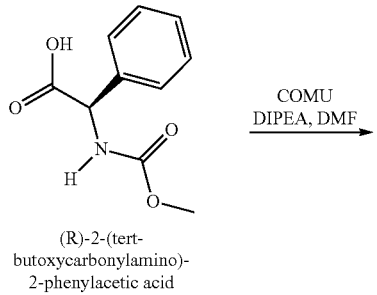

(R)-2-(tert-butoxycarbonylamino)-2-phenylacetic acid

COMU
DIPEA, DMF

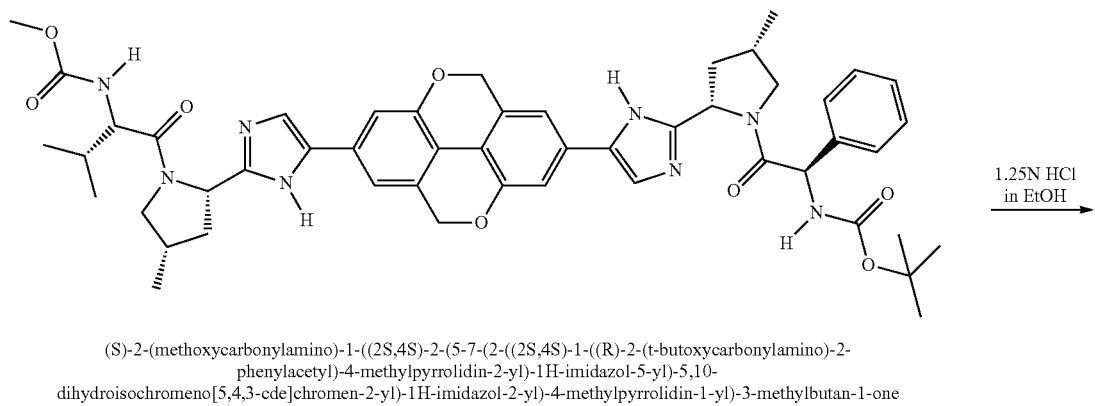

(S)-2-(methoxycarbonylamino)-1-((2S,4S)-2-(5-7-(2-((2S,4S)-1-((R)-2-(t-butoxycarbonylamino)-2-phenylacetyl)-4-methylpyrrolidin-2-yl)-1H-imidazol-5-yl)-5,10-dihydroisochromeno[5,4,3-cde]chromen-2-yl)-1H-imidazol-2-yl)-4-methylpyrrolidin-1-yl)-3-methylbutan-1-one 1.25N HCl in EtOH

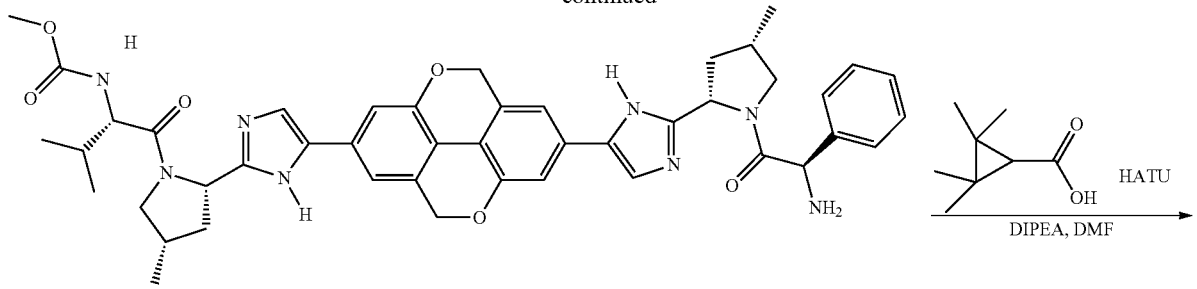

methyl (S)-1-((2S,4S)-2-(5-(7-(2-((2S,4S)-1-((R)-2-amino-2-phenylacetyl)-4-methylpyrrolidin-2-yl)-1H-imidazol-5-yl)-5,10-dihydroisochromeno[5,4,3-cde]chromen-2-yl)-1H-imidazol-2-yl)-4-methylpyrrolidin-1-yl)-3-methyl-1-oxobutan-2-ylcarbamate

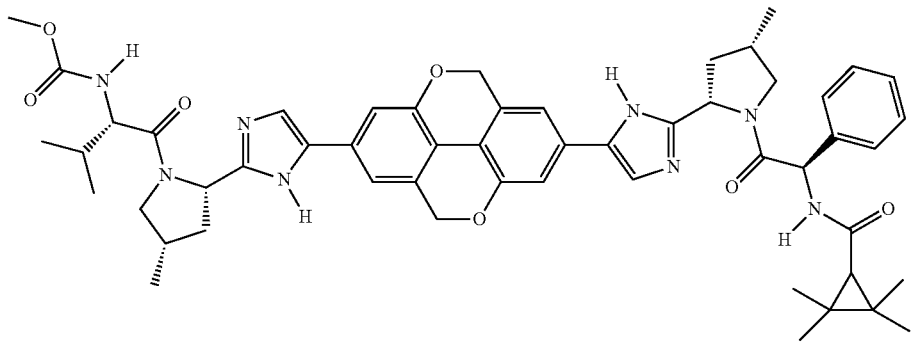

methyl (S)-3-methy-1-((2S,4S)-4-methyl-2-(5-(7-(2-((2S,4S)-4-methyl-1-((R)-2-phenyl-2-(2,2,3,3-tetramethylcyclopropanecarboxamido)acetyl)pyrrolidin-2-yl)-1H-imidazol-5-yl)-5,10-dihydrochromeno[5,4,3-cde]chromen-2-yl)-1H-imidazol-2-yl)-2-yl)pyrrolidin-1-yl)-1-oxobutan-2-ylcarbamate (S)-2-(methoxycarbonylamino)-1-((2S,4S)-2-(5-(7-(2-((2S,4S)-1-((R)-2-(t-butoxycarbonylamino)-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-3-methylbutan-1-one:

2,7-bis(2-((2S,4S)-4-methylpyrrolidin-2-yl)-1H-imidazol-5-yl)-5,10-dihydrochromeno[5,4,3-cde]chromene was obtained as in Example OY. A mixture of (S)-2-(methoxycarbonylamino)-3-methylbutanoic acid (124 mg, 0.706 mmol), (R)-2-(tert-butoxycarbonylamino)-2-phenylacetic acid (177 mg, 0.706 mmol), COMU (665 mg, 1.55 mmol) in 3.7 mL DMF was allowed to preactivate for 20 minutes before it was added to 449 mg of the crude amine in 3.7 mL DMF with 0.74 mL DIPEA. Once starting material was consumed, by LCMS monitoring, the reaction mixture was neutralized with formic acid, diluted with methanol and purified by reverse phase HPLC three products, two homodimers and the heterodimer (S)-2-(methoxycarbonylamino)-1-((2S,4S)-2-(5-(7-(2-((2S,4S)-1-((R)-2-(t-butoxycarbonylamino)-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-3-methylbutan-1-one as the trifluoroacetate salts. The eluted fractions were concentrated under reduced pressure, basified with saturated sodium bicarbonate solution and extracted into dichloromethane. Concentration under reduced pressure gave product (86 mg).

methyl (S)-1-((2S,4S)-2-(5-(7-(2-((2S,4S)-1-((R)-2-amino-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-3-methyl-1-oxobutan-2-ylcarbamate:

(S)-2-(methoxycarbonylamino)-1-((2S,4S)-2-(5-(7-(2-((2S,4S)-1-((R)-2-(t-butoxycarbonylamino)-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-3-methylbutan-1-one, 86 mg, was treated with 0.76 mL 1.25N HCl in Ethanol at room temperature overnight, then at 50° C. for 1 hour. The mixture was concentrated under reduced pressure and further dried under high vacuum to give product (90 mg).

Methyl (S)-3-methyl-1-((2S,4S)-4-methyl-2-(5-(7-(2-((2S,4S)-4-methyl-1-((R)-2-phenyl-2-(2,2,3,3-tetramethylcyclopropanecarboxamido)acetyl)pyrrolidin-2-yl)-1H-imidazol-5-yl)-5,10-dihydrochromeno[5,4,3-cde]chromen-2-yl)-1H-imidazol-2-yl)pyrrolidin-1-yl)-1-oxobutan-2-ylcarbamate:

Methyl (S)-1-((2S,4S)-2-(5-(7-(2-((2S,4S)-1-((R)-2-amino-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-3-methyl-1-oxobutan-2-ylcarbamate (45 mg, 0.049 mmol) in 0.5 mL 10% DIPEA in DMF was added to a mixture of 2,2,3,3-tetramethylcyclopropanecarboxylic acid (8.4 mg, 0.059 mmol) and HATU (22 mg, 0.059 mmol) in 0.2 mL 10% DIPEA in DMF. After 20 minutes stirring at room temperature, the reaction mixture was diluted with 0.2 mL water, 5 drops formic acid, and methanol to a total volume of 2.4 mL and purified by reverse phase HPLC to give 22.6 mg product as a trifluoroacetate salt.

MS (ESI) m/z 923.9 [M+H]$^+$.

1421

Example PA

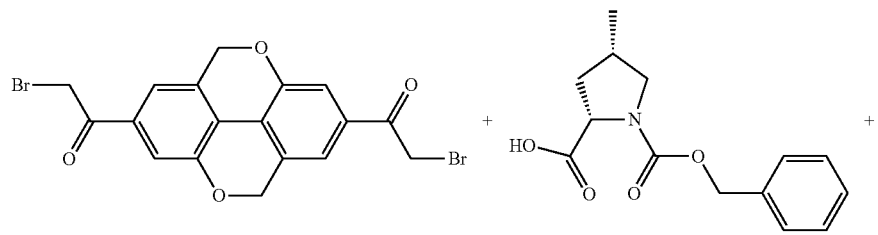

1,1'-(5,10-dihydrochromeno[5,4,3-cde]chromene-2,7-diyl)bis(2-bromoethane)

(2S,4S)-1-(benzyloxycarbonyl)-4-methylpyrrolidine-2-carboxylic acid (2S,4S)-1-(tert-butoxycarbonyl)-4-(methoxymethyl)pyrrolidine-2-carboxylic acid 1. Et$_3$N, DMF, 80° C.
2. NH$_4$OAc, MePh, reflux

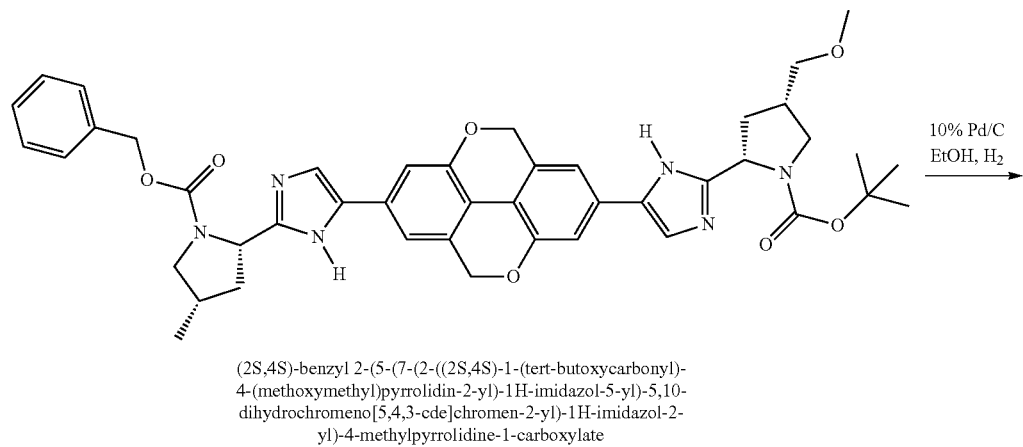

(2S,4S)-benzyl 2-(5-(7-(2-((2S,4S)-1-(tert-butoxycarbonyl)-4-(methoxymethyl)pyrrolidin-2-yl)-1H-imidazol-5-yl)-5,10-dihydrochromeno[5,4,3-cde]chromen-2-yl)-1H-imidazol-2-yl)-4-methylpyrrolidine-1-carboxylate 10% Pd/C
EtOH, H$_2$

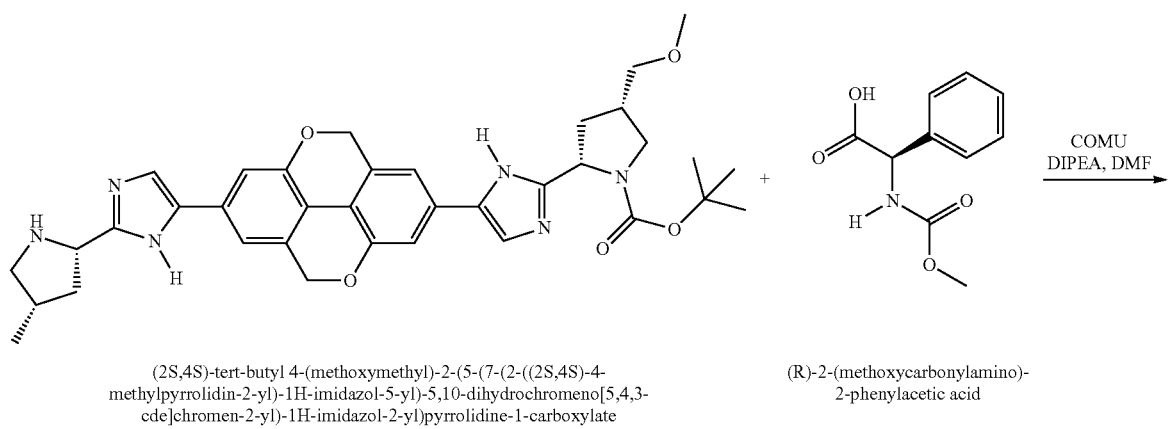

(2S,4S)-tert-butyl 4-(methoxymethyl)-2-(5-(7-(2-((2S,4S)-4-methylpyrrolidin-2-yl)-1H-imidazol-5-yl)-5,10-dihydrochromeno[5,4,3-cde]chromen-2-yl)-1H-imidazol-2-yl)pyrrolidine-1-carboxylate (R)-2-(methoxycarbonylamino)-2-phenylacetic acid

COMU
DIPEA, DMF

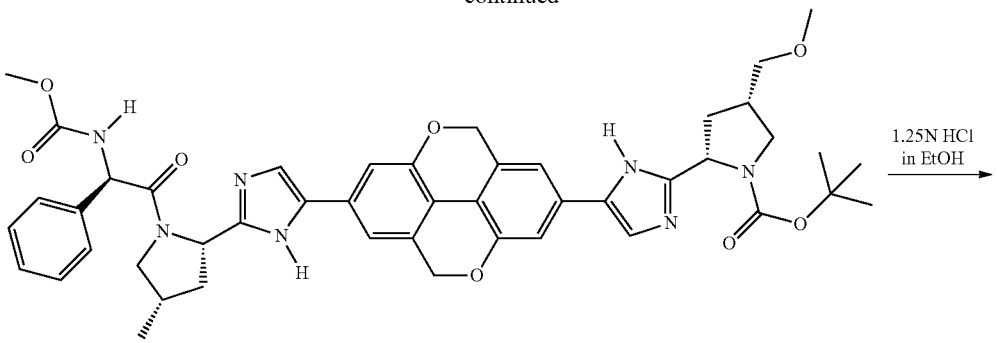

(2S,4S)-tert-butyl 2-(5-(7-(2-((2S,4S)-1-((R)-2-(methoxycarbonylamino)-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate

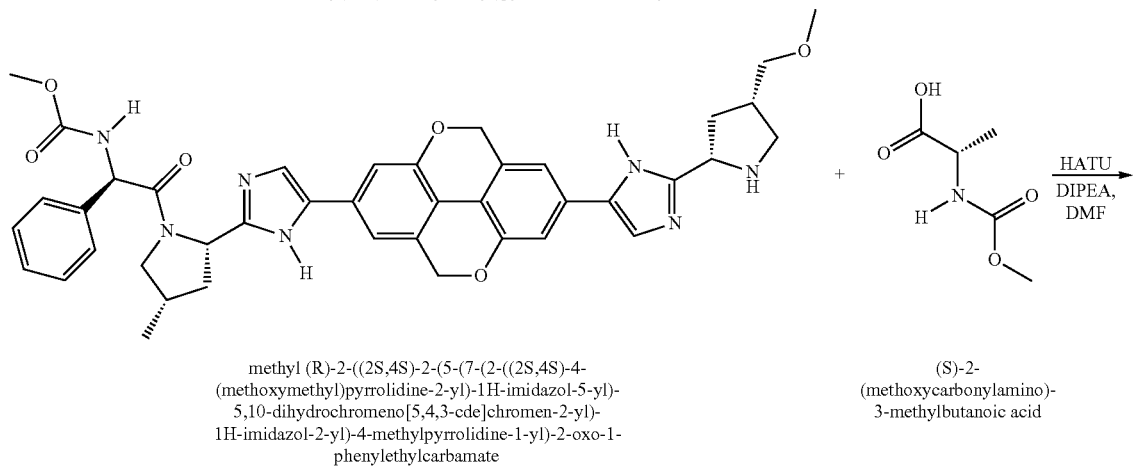

methyl (R)-2-((2S,4S)-2-(5-(7-(2-((2S,4S)-4-(methoxymethyl)pyrrolidin-2-yl)-1H-imidazol-5-yl)-5,10-dihydrochromeno[5,4,3-cde]chromen-2-yl)-1H-imidazol-2-yl)-4-methylpyrrolidine-1-yl)-2-oxo-1-phenylethylcarbamate (S)-2-(methoxycarbonylamino)-3-methylbutanoic acid

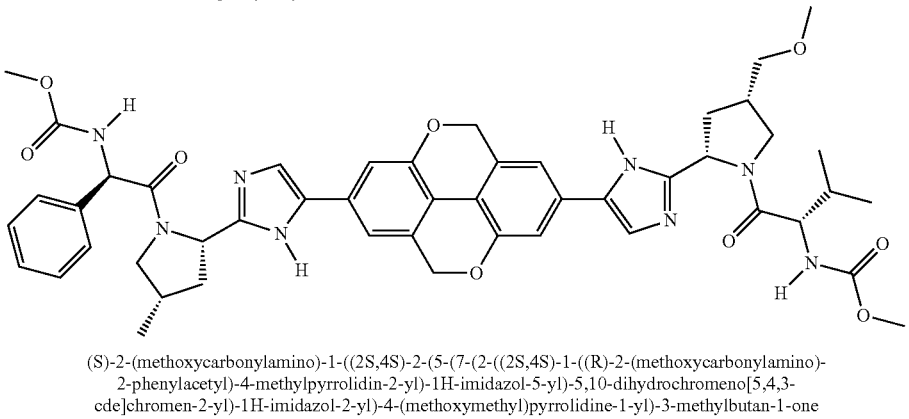

(S)-2-(methoxycarbonylamino)-1-((2S,4S)-2-(5-(7-(2-((2S,4S)-1-((R)-2-(methoxycarbonylamino)-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-yl)-3-methylbutan-1-one (2S,4S)-Benzyl 2-(5-(7-(2-((2S,4S)-1-tert-butoxycarbonyl)-4-(methoxymethyl)pyrrolidin-2-yl)-1H-imidazol-5-yl)-5,10-dihydrochromeno[5,4,3-cde]chromen-2-yl)-1H-imidazol-2-yl)-4-methylpyrrolidine-1-carboxylate:

A mixture of 1,1'-(5,10O-dihydrochromeno[5,4,3-cde]chromene-2,7-diyl)bis(2-bromoethanone) (1.27g, 2.8 mmol), (2S,4S)-1-(benzyloxycarbonyl)-4-methylpyrrolidin-2-carboxylic acid (810 mg, 3.08 mmol), and (2S,4S)-1-(tert-butoxycarbonyl)-4-(methoxymethyl)pyrrolidine-2-carboxylic acid (800 mg, 3.08 mmol) in 28 mL THF with 0.98 mL triethylamine was heated at 80° C. overnight. This gave a crude mixture of three diester products. The reaction mixture was partitioned between ethyl acetate and water, and further extracted the aqueous layer with ethyl acetate. The combined organic phase was dried over sodium sulphate, filtered, concentrated and then treated directly with ammonium acetate (2.17g, 28 mmol), toluene (28 mL) and 2-methoxypropanol (2.8 mL) and heated at reflux for 26 hours. The crude product mixture of three bis-imidazole products was concentrated and the three products were separated by reverse phase HPLC. Product (2S,4S)-benzyl 2-(5-(7-(2-((2S,4S)-1-(tert-butoxycarbonyl)-4-(methoxymethyl)pyrrolidin-2-yl)-1H-imidazol-5-yl)-5,10-dihydrochromeno[5,4,3-cde]chromen-2-yl)-1H-imidazol-2-yl)-4-methylpyrrolidine-1-carboxylate, 490 mg, was isolated by concentration of the appropriate fraction, basification with saturated sodium bicarbonate, extraction into dichloromethane, and concentration under reduced pressure.

(2S,4S)-tert-butyl 4-(methoxymethyl)-2-(5-(7-(2-((2S,4S)-4-methylpyrrolidin-2-yl)-1H-imidazol-5-yl)-5,10-dihydrochromeno[5,4,3-cde]chromen-2-yl)-1H-imidazol-2-yl)pyrrolidine-1-carboxylate:

A mixture of (2S,4S)-benzyl 2-(5-(7-(2-((2S,4S)-1-(tert-butoxycarbonyl)-4-(methoxymethyl)pyrrolidin-2-yl)-1H-imidazol-5-yl)-5,10-dihydrochromeno[5,4,3-cde]chromen-2-yl)-1H-imidazol-2-yl)-4-methylpyrrolidine-1-carboxylate (475 mg, 0.591 mmol) 60 mL ethanol, and 92 mg 10% Pd/C was stirred under an atmosphere of hydrogen (balloon) overnight. Filtration through celite, concentration and purification by reverse phase HPLC gave (2S,4S)-tert-butyl 4-(methoxymethyl)-2-(5-(7-(2-((2S,4S)-4-methylpyrrolidin-2-yl)-1H-imidazol-5-yl)-5,10-dihydrochromeno[5,4,3-cde]chromen-2-yl)-1H-imidazol-2-yl)pyrrolidine-1-carboxylate as a trifluoroacetate salt. Addition of saturated sodium bicarbonate solution, extraction into ethyl acetate and concentration of the extract gave 102 mg as the free base.

(2S,4S)-tert-butyl 2-(5-(7-(2-((2S,4S)-1-((R)-2-(methoxycarbonylamino)-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate:

A mixture of (2S,4S)-tert-butyl 4-(methoxymethyl)-2-(5-(7-(2-((2S,4S)-4-methylpyrrolidin-2-yl)-1H-imidazol-5-yl)-5,10-dihydrochromeno[5,4,3-cde]chromen-2-yl)-1H-imidazol-2-yl)pyrrolidine-1-carboxylate (102 mg, 0.159 mmol), (R)-2-(methoxycarbonylamino)-2-phenylacetic acid (33 mg, 0.159 mmol), COMU (75 mg, 0.175 mmol) in 1.59 mL 10% DIPEA in DMF was stirred at room temperature for 1 hr. Saturated sodium bicarbonate was added and the crude product was extracted into ethyl acetate. Concentration and purification by silica gel chromatography gave product (245 mg).

methyl (R)-2-((2S,4S)-2-(5-(7-(2-((2S,4S)-4-(methoxymethyl)pyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-2-oxo-1-phenylethylcarbamate:

A mixture of (2S,4S)-tert-butyl 2-(5-(7-(2-((2S,4S)-1-((R)-2-(methoxycarbonylamino)-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate (245 mg) and 5 mL 1.25N HCl in ethanol was stirred at room temperature overnight, then at 60° C. for 1 hour, then concentrated to an orange solid as an HCl salt (180 mg) that was used without further purification.

(S)-2-(methoxycarbonylamino)-1-((2S,4S)-2-(5-(7-(2-((2S,4S)-1-((R)-2-(methoxycarbonylamino)-2-phenylacetyl)-4-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidin-1-yl)-3-methylbutan-1-one:

A mixture of methyl (R)-2-((2S,4S)-2-(5-(7-(2-((2S,4S)-4-(methoxymethyl)pyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-2-oxo-1-phenylethylcarbamate (90 mg, >0.123 mmol), (S)-2-(methoxycarbonylamino)-3-methylbutanoic acid (24 mg, 0.135 mmol), HATU (51 mg, 0.135 mmol) in 1.5 mL 10% DIPEA in DMF was stirred for 1 hour. An additional 0.135 mmol of (S)-2-(methoxycarbonylamino)-3-methylbutanoic acid and HATU were added and stirring continued for 4 hours. The crude product was purified by reverse phase HPLC to product (28 mg) as a trifluoroacetate salt.

MS (ESI) m/z 887.1 [M+H]$^+$;

$^1$H NMR (CD$_3$CN) 7.460-7.314 (m, 6H), 6.907-6.807 (m, 3H), 6.746 (m, 1H), 6.042 (m, 1H), 5.518 (d, 1H, J=7.2 Hz), 5.166 (m, 1H), 5.095 (d, 4H, J=7.2 Hz), 4.348 (m, 1H), 4.181 (m, 1H), 3.718 (m, 1H), 3.634 (s, 6H), 3.495 (m, 2H), 3.334 (m, 3H), 2.641 (m, 2H), 2.488 (m, 4H), 2.205 (m, 2H), 2.070 (m, 4H), 1.073 (d, 3H, J=6.4 Hz), 1.020 (d, 3H, J=6.8 Hz), 0.934 (d, 3H, J=6.4 Hz).

Example PB

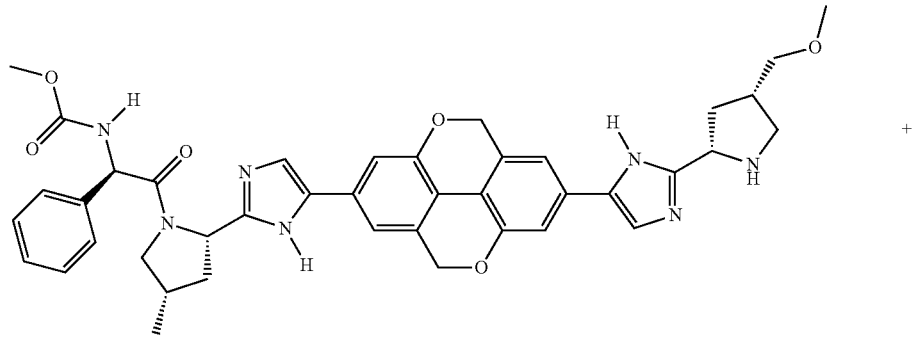

methyl (R)-2-((2S,4S)-2-(5-(7-(2-((2S,4S)-4-(methoxymethyl)pyrrolidin-2-yl)-1H-imidazol-5-yl)-5,10-dihydroisochromeno[5,4,3-cde]chromen-2-yl)-1H-imidazol-2-yl)-4-methylpyrrolidin-1-yl)-2-oxo-1-phenylethylcarbamate

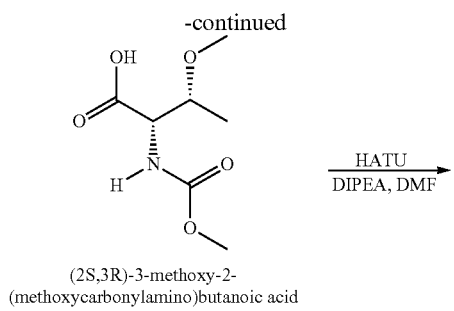

(2S,3R)-3-methoxy-2-
(methoxycarbonylamino)butanoic acid

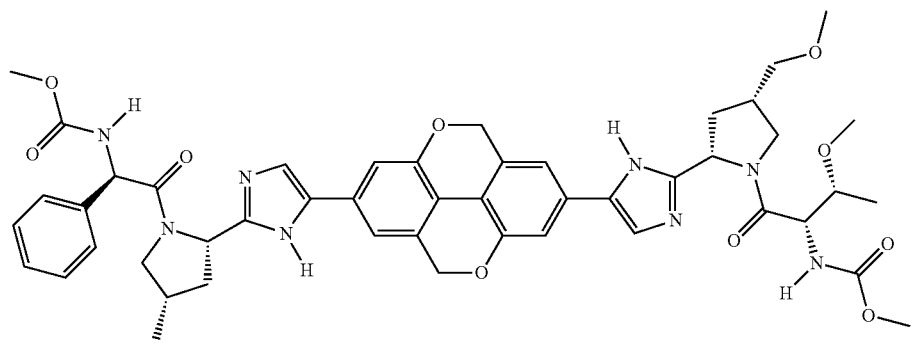

methyl (R)-2-((2S,4S)-2-(5-(7-(2-((2S,4S)-1-((2S,3R)-2-(methoxycarbonylamino)-3-methoxybutanoyl)-4-
(methoxymethyl)pyrrolidin-2-yl)-1H-
imidazol-5-yl)-5,10-dihydroisochromeno[5,4,3-cde]chromen-2-yl)-1H-
imidazol-2-yl)-1H-imidazol-2-yl)-4-methylpyrrolidin-1-yl)-2-oxo-1-phenylethylcarbamate Methyl (R)-2-((2S,4S)-2-(5-(7-(2-((2S,4S)-1-((2S,3R)-2-(methoxycarbonylamino)-3-methoxybutanoyl)-4-(methoxymethyl)pyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-2-oxo-1-phenylethylcarbamate:

A mixture of methyl (R)-2-((2S,4S)-2-(5-(7-(2-((2S,4S)-4-(methoxymethyl)pyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-2-oxo-1-phenylethylcarbamate (90 mg, >0.123 mmol), (2S,3R)-3-methoxy-2-(methoxycarbonylamino)butanoic acid (26 mg, 0.135 mmol), HATU (51 mg, 0.135 mmol) in 1.5 mL 10% DIPEA in DMF was stirred for 1 hour. An additional 0.135 mmol of (2S,3R)-3-methoxy-2-(methoxycarbonylamino)butanoic acid and HATU were added and stirring continued for 3 hours. The crude product was purified by reverse phase HPLC to product (22 mg) as a trifluoroacetate salt.

MS (ESI) m/z 903.2 [M+H]$^+$;

$^1$H NMR (CD$_3$OD) 7.850 (m, 2H), 7.449 (m, 5H), 7.359 (s, 1H), 7.263 (s, 2H), 7.220 (s, 1H), 5.420 (s, 1H), 5.360 (d, 4H, J=2.2 Hz), 5.261 (m, 1H), 5.197 (m, 1H), 4.478 (m, 1H), 4.266 (m, 1H), 4.118 (m, 1H), 3.684 (m, 1H), 3.684 (s, 6H), 3.623 (s, 3H), 3.550 (m, 2H), 3.408 (s, 3H), 2.771 (m, 1H), 2.628 (m, 2H), 2.278 (m, 1H), 2.055 (m, 1H), 1.780 (m, 1H), 1.345 (t, 2H, J=7.0 Hz), 1.128 (d, 6H, J=6.0 Hz).

Example PC

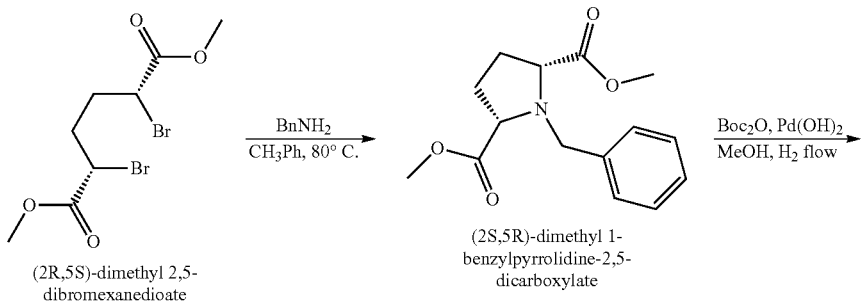

-continued

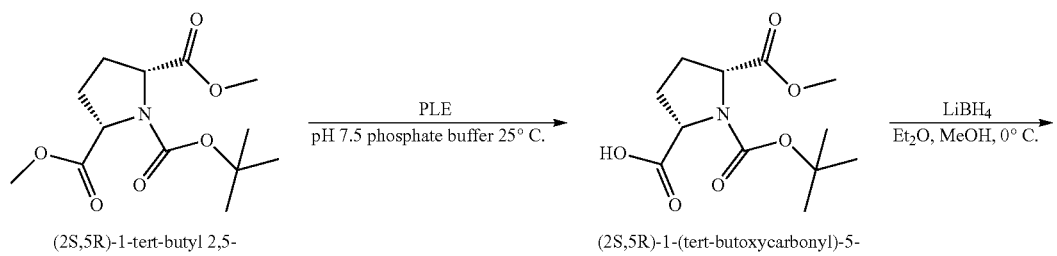

(2S,5R)-1-tert-butyl 2,5-dimethyl pyrrolidine-1,2,5-tricarboxylate (2S,5R)-1-(tert-butoxycarbonyl)-5-(methoxycarbonyl)pyrrolidine-2-carboxylic acid

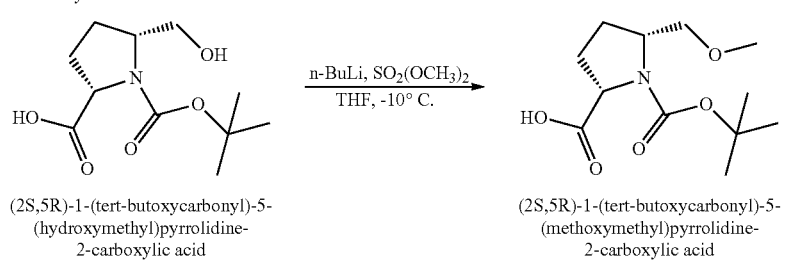

(2S,5R)-1-(tert-butoxycarbonyl)-5-(hydroxymethyl)pyrrolidine-2-carboxylic acid (2S,5R)-1-(tert-butoxycarbonyl)-5-(methoxymethyl)pyrrolidine-2-carboxylic acid

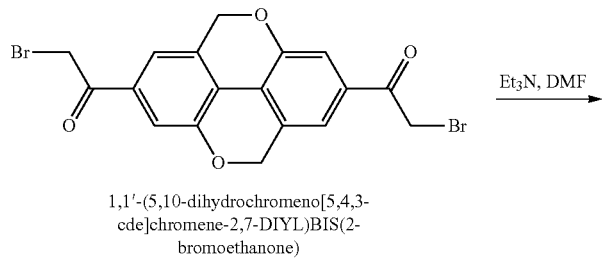

1,1'-(5,10-dihydrochromeno[5,4,3-cde]chromene-2,7-DIYL)BIS(2-bromoethanone)

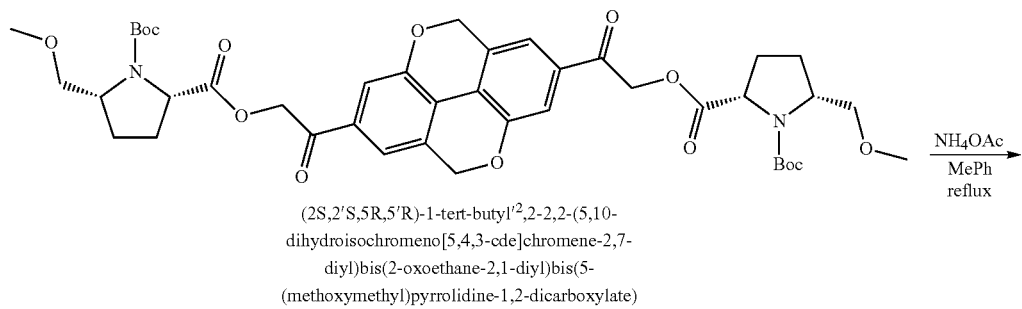

(2S,2'S,5R,5'R)-1-tert-butyl'²,2-2,2-(5,10-dihydroisochromeno[5,4,3-cde]chromene-2,7-diyl)bis(2-oxoethane-2,1-diyl)bis(5-(methoxymethyl)pyrrolidine-1,2-dicarboxylate)

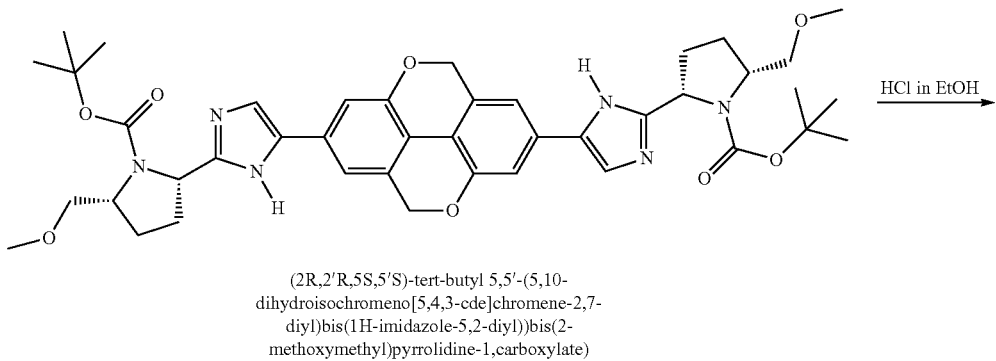

(2R,2'R,5S,5'S)-tert-butyl 5,5'-(5,10-dihydroisochromeno[5,4,3-cde]chromene-2,7-diyl)bis(1H-imidazole-5,2-diyl))bis(2-methoxymethyl)pyrrolidine-1,carboxylate)

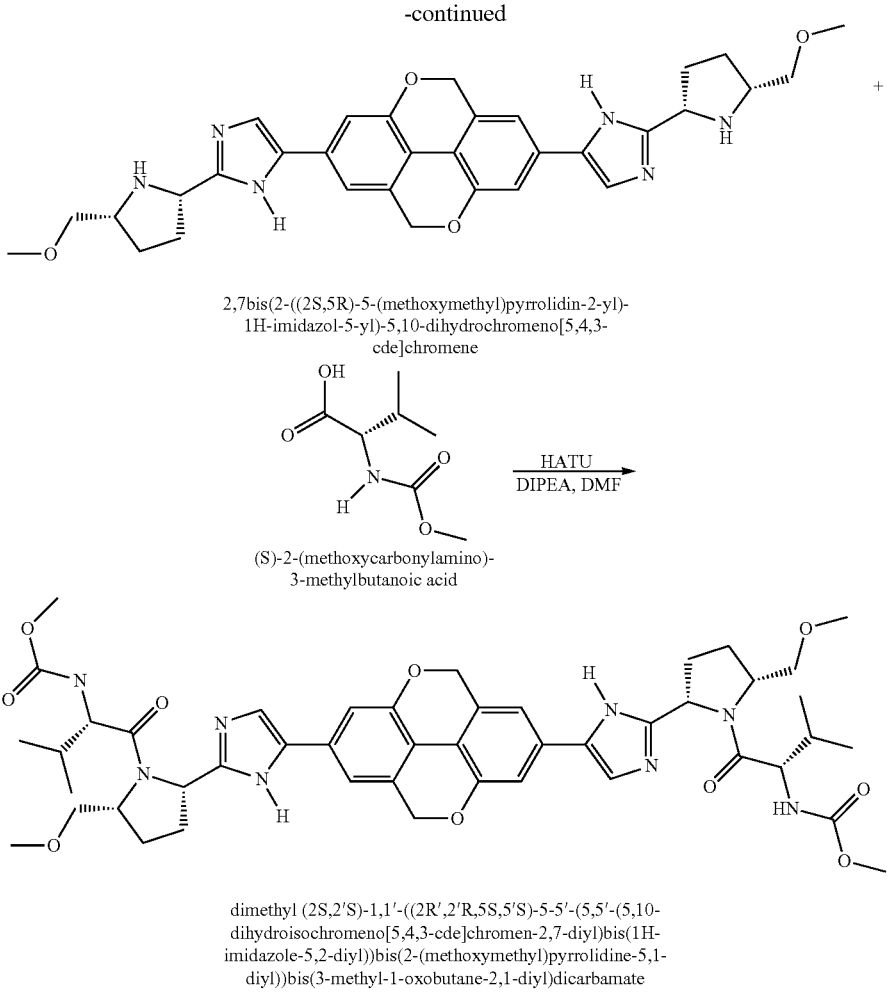

2,7bis(2-((2S,5R)-5-(methoxymethyl)pyrrolidin-2-yl)-1H-imidazol-5-yl)-5,10-dihydrochromeno[5,4,3-cde]chromene (S)-2-(methoxycarbonylamino)-3-methylbutanoic acid

HATU
DIPEA, DMF dimethyl (2S,2′S)-1,1′-((2R′,2′R,5S,5′S)-5-5′-(5,5′-(5,10-dihydroisochromeno[5,4,3-cde]chromen-2,7-diyl)bis(1H-imidazole-5,2-diyl))bis(2-(methoxymethyl)pyrrolidine-5,1-diyl))bis(3-methyl-1-oxobutane-2,1-diyl)dicarbamate (2S,5R)-dimethyl-1-benzylpyrrolidine-2,5-dicarboxylate:

To an 80° C. solution of (2R,5S)-dimethyl 2,5-dibromohexanedioate (25.0g, 69.0 mmol) in 100 mL toluene was added benzylamnnine (25.2 mL, 230 mmol) drop wise over 30 minutes. After 16 hours at 80° C., the reaction was cooled to room temperature and filtered. The filter cake was washed with three 60 mL portions of toluene and the combined filtrate was washed with water and saturated ammonium chloride, then concentrated under reduced pressure to give 21.63g product whose NMR is consistent with the title compound.

(2S,5R)-1-tert-butyl 2,5-dimethyl pyrrolidine-1,2,5-tricarboxylate:

A 0.05M solution of (2S,5R)-dimethyl 1-benzylpyrrolidine-2,5-dicarboxylate (1.53g, 5.0 mmol) in methanol containing di-tert-butyl dicarbonate (1.18g, 5.5 mmol) was hydrogenated by 1 mL/min flow through a 55 mm 20% Pd(OH)$_2$ catalyst cartridge at atmospheric pressure with full H$_2$ saturation. The effluent was concentrated under reduced pressure and further dried under high vacuum overnight to give 2.21g product as a colorless oil.

(2S,5R)-1-(tert-butoxycarbonyl)-5-(methoxycarbonyl)pyrrolidine-2-carboxylic acid:

(2S,5R)-1-tert-butyl 2,5-dimethyl pyrrolidine-1,2,5-tricarboxylate (2.21g, 7.01 mmol) was suspended in 100 mL pH 7.5 phosphate buffer and treated with Pig Liver Esterase (500 mg) at 25° C. for 10 days, with occasional pH adjustment to maintain pH 7.5. Acidified to pH 4 with 2N HCl and extracted into dichloromethane. The extract was dried over sodium sulphate, filtered, and concentrated under reduced pressure to give 1.17g crude product.

(2S,5R)-1-(tert-butoxycarbonyl)-5-(hydroxymethyl)pyrrolidine-2-carboxylic acid:

To an ice cold solution of (2S,5R)-1-(tert-butoxycarbonyl)-5-(methoxycarbonyl)pyrrolidine-2-carboxylic acid (1.17g, 4.07 mmol) in 70 mL diethyl ether and 0.330 mL methanol was added lithium borohydride (2M in THF, 4.0 mL, 8.14 mmol). After 10 minutes, the ice bath was removed and the reaction was heated at reflux overnight. As the reaction had not proceeded, a solvent swap to THF was performed, and the resulting mixture was heated at 70° C. overnight. The reaction mixture was cooled to 0° C. and quenched with 1N HCl and then extracted into ethyl acetate, dried over sodium sulphate, filtered and concentrated under reduced pressure to give the crude product as a white semi-solid (886 mg)

(2S,5R)-1-(tert-butoxycarbonyl)-5-(methoxymethyl)pyrrolidine-2-carboxylic acid:

A solution of (2S,5R)-1-(tert-butoxycarbonyl)-5-(hydroxymethyl)pyrrolidine-2-carboxylic acid (820 mg, 3.34 mmol) in 11 mL THF was cooled in a –10° C. bath and treated with n-butyl lithium (1.6M in hexanes, 6.5 mL, 10.36 mmol) and kept cold for 1 hour, then dimethyl sulphate (0.380 mL, 4.01 mmol) was added. The temperature was held at −5° C. to 5° C. and then the reaction mixture was held in the −20° C. freezer overnight. The reaction was quenched cold, with water. Next, the mixture was concentrated under reduced pressure to remove THF. The aqueous mixture was acidified with 2N HCl and extracted with ethyl acetate. The organic layer was dried over sodium sulphate, filtered, and concentrated under reduced pressure to give 788 mg crude product, which was then purified by silica gel chromatography to give 199 mg clean product, 140 mg recovered starting material, and 317 mg of a mixture of starting material and product.

(2S,2'S,5R,5'R)-1-tert-butyl '2,2-2,2'-(5,10-dihydrochromeno[5,4,3-cde]chromene-2,7-diyl)bis(2-oxoethane-2,1-diyl)bis(5-(methoxymethyl)pyrrolidine-1,2-dicarboxylate):

A mixture of 1,1'-(5,10-dihydrochromeno[5,4,3-cde]chromene-2,7-diyl)bis(2-bromoethanone) (139 mg, 0.31 mmol)), and (2S,5R)-1-(tert-butoxycarbonyl)-5-(methoxymethyl)pyrrolidine-2-carboxylic acid (199 mg, 0.77 mmol) in 3 mL DMF with 0.107 mL triethylamine was heated at 80° C. for 4 hours. Water (10 mL) was added and the precipitate that formed was collected by vacuum filtration, washed with water, and air dried for 1 hour before drying under high vacuum overnight to give crude product (229 mg) as a dark yellow solid.

(2R,2'R,5S,5'S)-tert-butyl 5,5'-(5,5'-(5,10-dihydrochromeno[5,4,3-cde]chromene-2,7-diyl)bis(1H-imidazole-5,2-diyl))bis(2-(methoxymethyl)pyrrolidine-1-carboxylate):

A mixture of (2S,2'S,5R,5'R)-1-tert-butyl '2,2-2,2'-(5,10-dihydrochromeno[5,4,3-cde]chromene-2,7-diyl)bis(2-oxoethane-2,1-diyl)bis(5-(methoxymethyl)pyrrolidine-1,2-dicarboxylate) (204 mg, 0.252 mmol), ammonium acetate (195 mg, 2.52 mmol), toluene (2.5 mL) and 2-methoxypropanol (0.25 mL) was heated at 110° C. overnight. The mixture was concentrated under reduced pressure and purified by silica gel chromatography. (254 mg)

2,7-bis(2-((2S,5R)-5-(methoxymethyl)pyrrolidin-2-yl)-1H-imidazol-5-yl)-5,10-dihydrochromeno[5,4,3-cde]chromene:

A solution of (2R,2'R,5S,5'S)-tert-butyl 5,5'-(5,5'-(5,10-dihydrochromeno[5,4,3-cde]chromene-2,7-diyl)bis(H-imidazole-5,2-diyl))bis(2-(methoxymethyl)pyrrolidine-1-carboxylate) (254 mg, 0.33 mmol) and 1.25N HCl in ethanol (6 mL) was heated at 50° C. for 3 hours, then concentrated under reduced pressure and further dried under high vacuum and used in the next step.

dimethyl (2S,2'S)-1,1'-((2R,2'R,5S,5'S)-5,5'-(5,10-dihydrochromeno[5,4,3-cde]chromene-2,7-diyl)bis(1H-imidazole-5,2-diyl))bis(2-(methoxymethyl)pyrrolidine-5,1-diyl))bis(3-methyl-1-oxobutane-2,1-diyl)dicarbamate:

A solution of 2,7-bis(2-((2S,5R)-5-(methoxymethyl)pyrrolidin-2-yl)-1H-imidazol-5-yl)-5,10-dihydrochromeno[5,4,3-cde]chromene from the previous step, (S)-2-(methoxycarbonylamino)-3-methylbutanoic acid (127 mg, 0.726 mmol), HATU (276 mg, 0.0726 mmol) and DIPEA (0.576 mL, 3.3 mmol) in DMF (1.8 mL) was stirred at room temperature for 1 hour. The crude product was purified by reverse phase HPLC to give the product as a trifluoroacetate salt (75.7 mg)

MS (ESI) m/z 883.8 [M+H]$^+$;

$^1$H NMR (CD$_3$CN) 7.62 (m, 1H), 7.526 (m, 1H), 7.281 (m, 1H), 7.208 (m, 1H), 7.128 (m, 1H), 7.052 (m, 1H), 6.073 (m, 1H), 5.724 (m, 1H), 5.389-5.201 (m, 4H), 4.240 (m, 1H), 4.070 (m, 1H), 4.070 (m, 1H), 3.962 (s, 1H), 3.615 (m, 2H), 3.507 (m, 8H), 3.332 (m, 6H), 2.375 (m, 2H), 2.303 (m, 4H), 2.128 (m, 2H), 2.108 (m, 4H), 0.966 (m, 12H).

Example PE

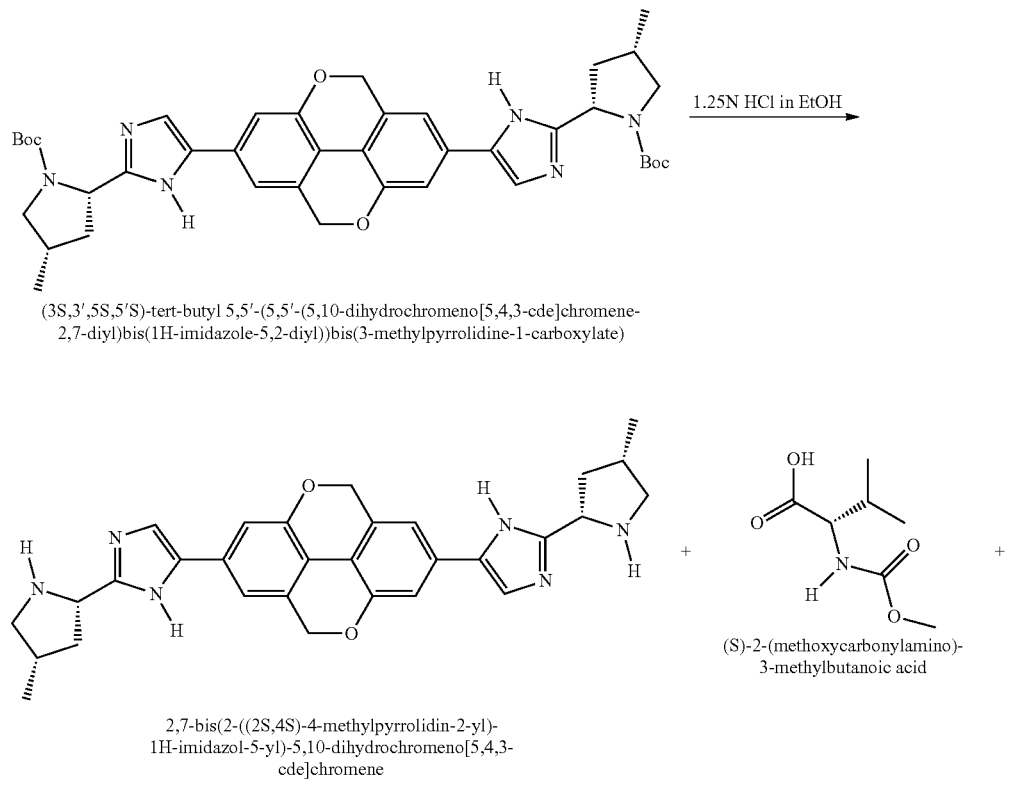

(3S,3',5S,5'S)-tert-butyl 5,5'-(5,5'-(5,10-dihydrochromeno[5,4,3-cde]chromene-2,7-diyl)bis(1H-imidazole-5,2-diyl))bis(3-methylpyrrolidine-1-carboxylate)

2,7-bis(2-((2S,4S)-4-methylpyrrolidin-2-yl)-1H-imidazol-5-yl)-5,10-dihydrochromeno[5,4,3-cde]chromene (S)-2-(methoxycarbonylamino)-3-methylbutanoic acid

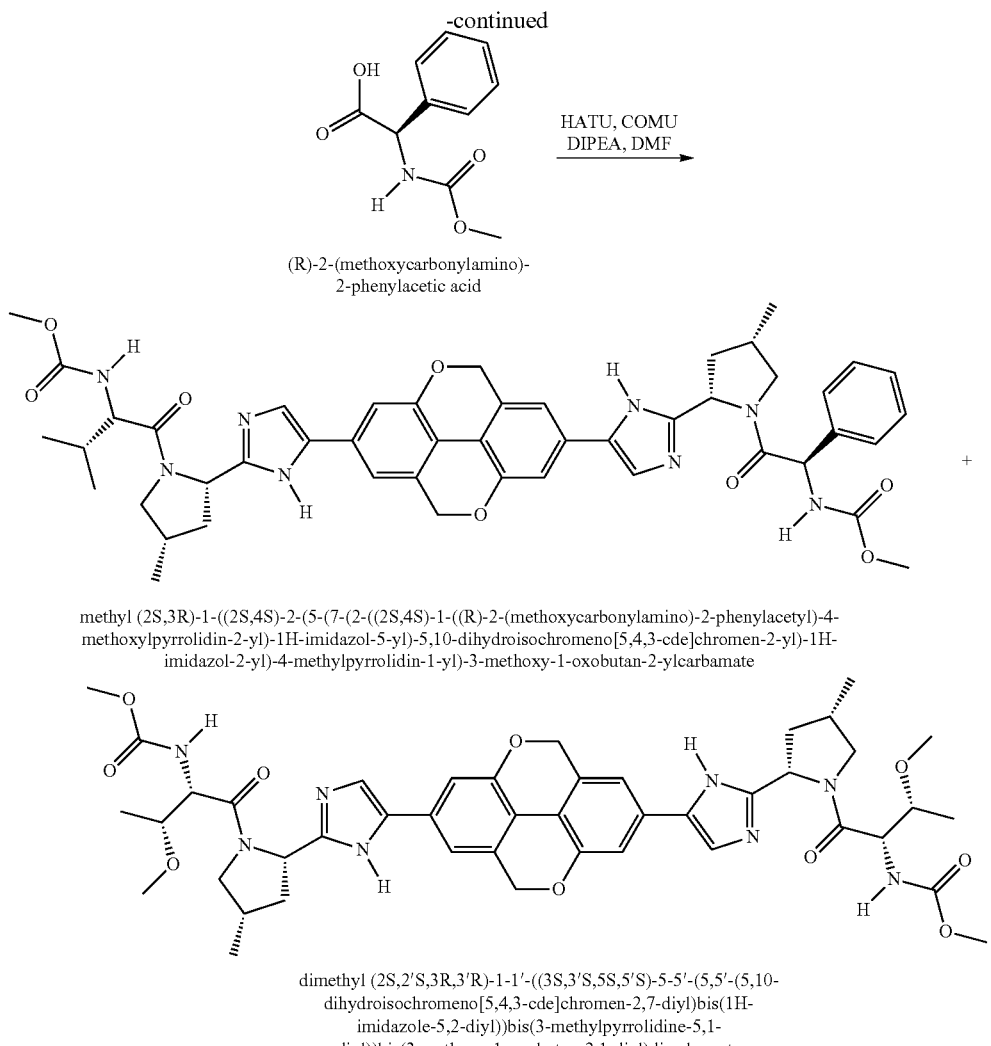

Methyl (2S,3R)-1-((2S,4S)-2-(5-(7-(2-((2S,4S)-1-((R)-2-(methoxycarbonylamino)-2-phenylacetyl)-4-m ethylpyrrolidin-2-yl)-1H-imidazol-5-yl)-5,10-dihydrochromeno[5,4,3-cde]chromen-2-yl)-1H-imidazol-2-yl)-4-methylpyrrolidin-1-yl)-3-methoxy-1-oxobutan-2-ylcarbamate and Dimethyl (2S,2'S,3R,3'R)-1,1'-((3S,3'S,5S,5'S)-5,5'-(5,5'-(5,10-dihydrochromeno[5,4,3-cde]chromene-2,7-diyl)bis(1H-imidazole-5,2-diyl))bis(3-methylpyrrolidine-5,1-diyl))bis(3-methoxy-1-oxobutane-2,1-diyl)dicarbamate:

(3S,3'S,5S,5'S)-tert-butyl 5,5'-(5,5'-(5,10-dihydrochromeno[5,4,3-cde]chromene-2,7-diyl)bis(1H-imidazole-5,2-diyl))bis(3-methylpyrrolidine-1-carboxylate) (321 mg, 0.63 mmol) was deprotected with 4 mL 1.25N HCl in ethanol at 50° C. for 2 hours, then concentrated. A mixture of (2S,3R)-3-methoxy-2-(methoxycarbonylamino)butanoic acid (131 mg, 0.67 mmol) and HATU (251 mg, 0.67 mmol), in 3 mL 10% DIPEA in DMF was mixed and then was added to the crude amine. An additional portion of (2S,3R)-3-methoxy-2-(methoxycarbonylamino)butanoic acid (48 mg) and HATU (80 mg) were added. After 2 hours at room temperature, (R)-2-(methoxycarbonylamino)-2-phenylacetic acid (100 mg) and COMU (400 mg) was added and the reaction was allowed to stir at room temperature for 3 hours. The intermediate and title compounds were purified from the product mixture by reverse phase HPLC as salts of trifluoroacetic acid.

Dimethyl (2S,2'S,3R,3'R)-1,1'-((3S,3'S,5S,5'S)-5,5'-(5,5'-(5,10-dihydrochromeno[5,4,3-cde]chromene-2,7-diyl)bis(1H-imidazole-5,2-diyl))bis(3-methylpyrrolidine-5,1-diyl))bis(3-methoxy-1-oxobutane-2,1-diyl)dicarbamate (59.5 mg)

MS (ESI) m/z 855.2 [M+H]$^+$;

$^1$H NMR (CD$_3$CN) 7.296 (m, 2H), 7.214 (m, 4H), 5.861 (m, 2H), 5.240 (s, 4H), 5.085 (m, 2H), 4.710 (m, 2H), 4.061 (m, 2H), 3.637 (s, 6H), 3.630 (m, 2H), 3.292 (m, 2H), 3.212 (s, 6H), 2.469 (m, 2H), 2.320 (m, 2H), 1.147 (d, 6H, J=6.4 Hz), 1.087 (m, 6H).

Methyl (2S,3R)-3-methoxy-1-((2S,4S)-4-methyl-2-(5-(7-(2-((2S,4S)-4-methylpyrrolidin-2-yl)-1H-imidazol-5-yl)-5,10-dihydrochromeno[5,4,3-cde]chromen-2-yl)-1H-imidazol-2-yl)pyrrolidin-1-yl)-1-oxobutan-2-ylcarbamate (intermediate, 46 mg, 0.0675 mmol) was then treated with more (R)-2-(methoxycarbonylamino)-2-phenylacetic acid (14 mg, 0.0675 mmol) and COMU (29 mg, 0.0675 mmol) in 1 mL 10% DIPEA in DMF at room temperature for 1 hour. The mixture was partitioned between saturated sodium bicarbonate and ethyl acetate. The organic layer was dried over sodium sulphate, filtered, and concentrated, then purified by reverse phase HPLC to give the product as a trifluoroacetate salt. (18.6 mg)

MS (ESI) m/z 873.7 [M+H]+;

1H NMR (CDCl3) 7.389 (m, 5H), 7.177 (m, 6H), 5.720 (m, 1H), 5.401 (m, 1H), 5.219 (m, 6H), 4.559 (m, 1H), 3.969 (m, 1H), 3.691 (s, 3H), 3.645 (s, 3H), 3.589 (m, 2H), 3.54 (m, 1H), 3.173 (s, 3H), 2.507 (m, 2H), 2.427 (m, 2H), 2.348 (m, 1H), 1.826 (m, 2H), 1.167 (m, 6H), 1.036 (m, 3H).

Example PF

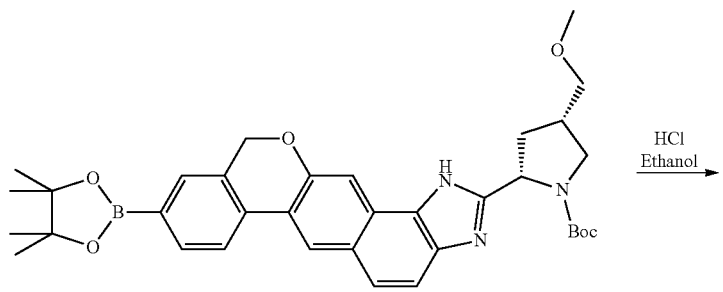

tert-butyl (2S,4S)-4-(methoxymethyl)-2-[9-4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate

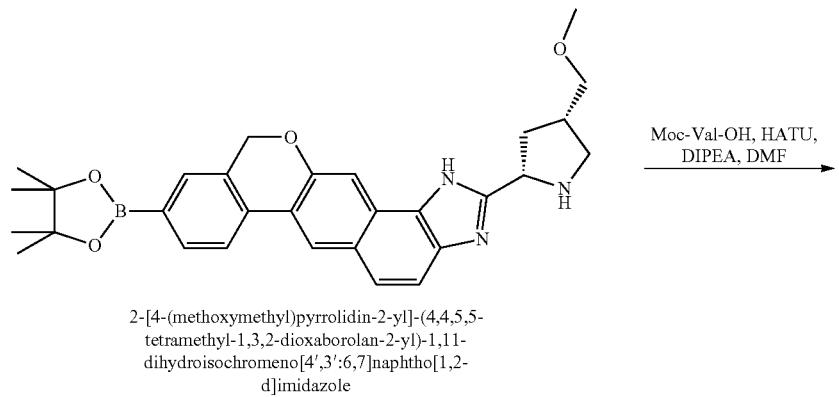

2-[4-(methoxymethyl)pyrrolidin-2-yl]-(4,4,5,5-tetramethyl-1,3,2-dioxaborolan-2-yl)-1,11-dihydroisochromeno[4',3':6,7]naphtho[1,2-d]imidazole

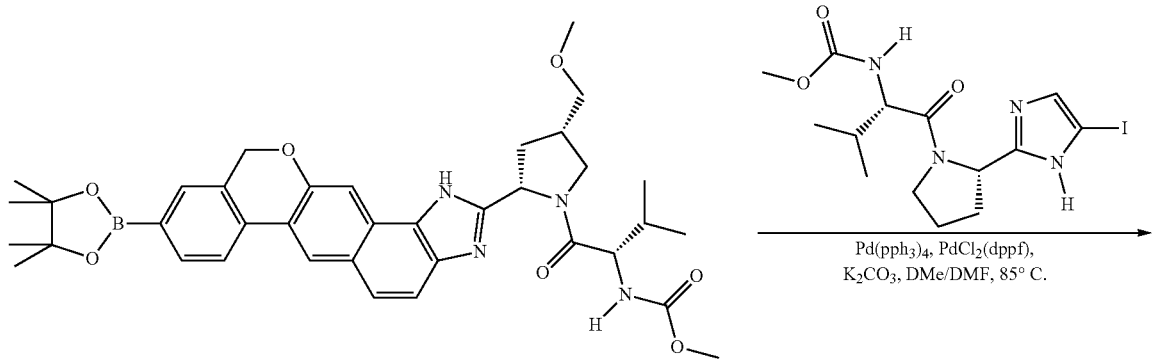

methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate

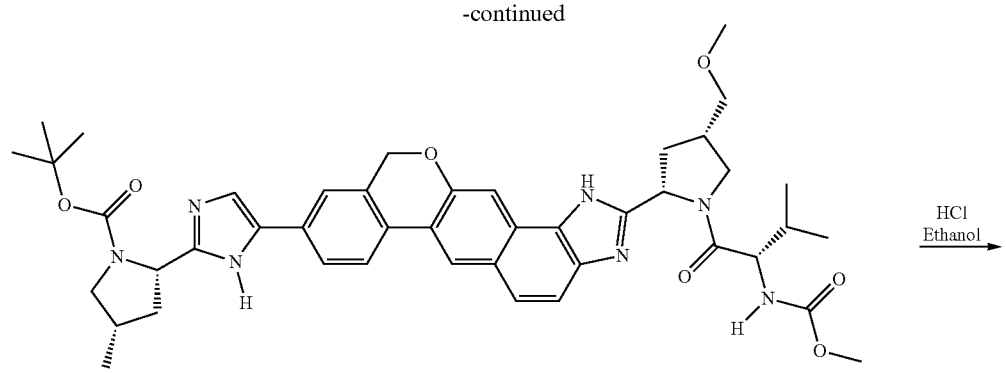

tert-butyl 2-[5-(2-{1-[N-methoxycarbonyl)valyl]-4-(methoxymethyl)pyrrolidin-
2-yl}-1,11-dihydroisochromeno[4',3':6,7]naphtho[1,2-d]imidazol-9-yl)-1H-
imidazol-2-yl]-4-methylpyrrolidine-1-carboxylate

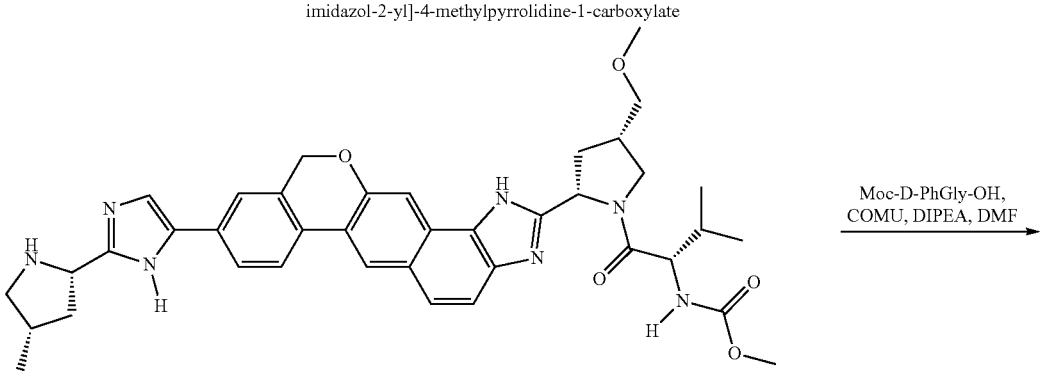

methyl {1-[4-(methoxymethyl)-2-{9-[2-(4-methylpyrrolidin-2-yl)-1H-
imidazol-5-yl]-1,11-dihydroisochromeno[4',3':6,7]naphtho[1,2-d]imidazol-2-yl}pyrrolidin-
1-yl]-3-methyl-1-oxobutan-1-yl}carbamate

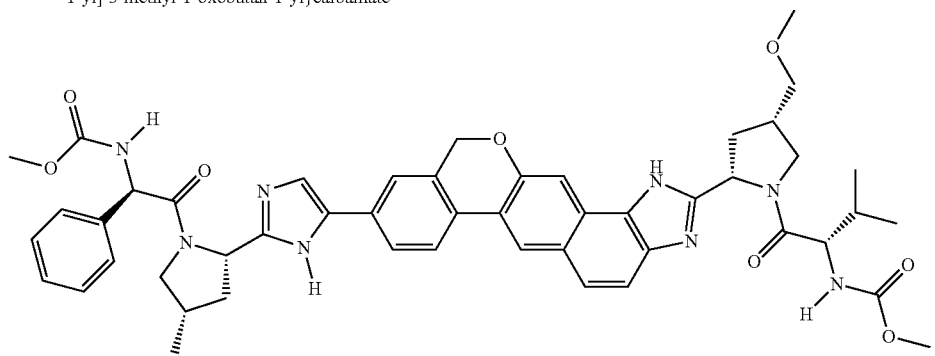

methyl {1-[2-{9-[2-(1-{[(methoxycarbonyl)amino}(phenyl)acetyl}-4-methylpyrrolidin-
2-yl)-1H-imidazol-5-yl]-1,11-dihydroisochromeno[4',3':6,7]naphtho[1,2-d]imidazol-
2-yl}-4-(methoxymethyl)pyrrolidin-1-yl]-
3-methyl-1-oxobutan-2-yl}carbamate tert-butyl (2S,4S)-4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate:

The title compound was obtained as in example LQ but using (2S,4S)-1-(tert-butoxycarbonyl)-4-(methoxymethyl)pyrrolidine-2-carboxylic acid in place of (S)-1-(tert-butoxycarbonyl)pyrrolidine-2-carboxylic acid.

2-[4-(methoxymethyl)pyrrolidin-2-yl]-9-(4,4,5,5-tetramethyl-1,3,2-dioxaborolan-2-yl)-1,11-dihydroisochromeno[4',3':6,7]naphtho[1,2-d]imidazole:

Tert-butyl (2S,4S)-4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate (310 mg, 0.507 mmol) was treated with 2 mL 1.25N HCl in ethanol and stirred at room temperature for 2 h then at 50° C. for 2 h. The reaction mixture was concentrated under reduced pressure to give a dark yellow solid that was used directly in the next step.

methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate:

A mixture of (S)-2-(methoxycarbonylamino)-3-methylbutanoic acid (107 mg, 0.608 mmol), HATU (231 mg, 0.608 mmol) and 6 mL 10% DIPEA in DMF was preactivated for 5 minutes, then it was added to the amine salt from the step above and allowed to stir overnight. The reaction mixture was partitioned between ethyl acetate and saturated sodium bicarbonate. The organic phase was concentrated and purified by silica gel chromatography. (103 mg)

tert-butyl 2-[5-(2-{1-[N-(methoxycarbonyl)valyl]-4-(methoxymethyl)pyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate:

the title compound was obtained as in example LQ but using methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate (103 mg, 0.154 mmol) in place of tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate and methyl (S)-1-((S)-2-(5-iodo-1H-imidazol-2-yl)pyrrolidin-1-yl)-3-methyl-1-oxobutan-2-ylcarbamate (58 mg, 0.154 mmol) in place of methyl (S)-1-((S)-2-(5-bromo-1H-imidazol-2-yl)pyrrolidin-1-yl)-3-methyl-1-oxobutan-2-ylcarbamate. (50.0 mg)

methyl {1-[4-(methoxymethyl)-2-{9-[2-(4-methylpyrrolidin-2-yl)-1H-imidazol-5-yl]-1,11-dihydroisochromeno[4',3':6,7]naphtho[1,2-d]imidazol-2-yl}pyrrolidin-1-yl]-3-methyl-1-oxobutan-2-yl}carbamate:

tert-butyl 2-[5-(2-{1-[N-(methoxycarbonyl)valyl]-4-(methoxymethyl)pyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (50 mg, 0.063 mmol) was treated with 2 mL 1.25N HCl in ethanol and heated at 60° C. for 2 h, then it was concentrated under reduced pressure and pumped dry under high vacuum and used directly in the next step.

methyl {1-[2-{9-[2-(1-{[(methoxycarbonyl)amino](phenyl)acetyl}-4-methylpyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate:

A mixture of (R)-2-(methoxycarbonylamino)-2-phenylacetic acid (13 mg, 0.063 mmol), COMU (30 mg, 0.069 mmol) in 0.500 mL DMF and DIPEA (0.033 mL, 0.189 mmol) was allowed to preactivate for 15 minutes before it was added to the solid crude amine salt from the previous step and stirred overnight. The product was purified by reverse phase HPLC. The product was converted to the free base by dissolution in 2 mL 1:1 acetonitrile:methanol and passage through a prepacked cartridge of polymer supported carbonate. Concentration and drying gave an off white powder. (23.3 mg).

MS (ESI) m/z 883.8 [M+H]+

$^1$H NMR (CD$_3$CN) 8.176 (s, 1H), 7.778 (m, 1H), 7.596-7.521 (m, 4H), 7.455-7.347 (m, 6H), 7.218 (s, 1H), 5.482 (s, 1H), 5.310 (m, 1H), 5.192 (m, 1H), 4.999 (q, 2H, J=14 Hz), 4.372 (d, 1H, J=6.4 Hz), 4.279 (m, 1H), 3.800-3.697 (m, 2H), 3.632 (s, 3H) 3.597-3.445 (m, 7H), 3.355 (m, 3H), 2.876 (m, 2H), 2.761 (m, 1H), 2.583 (m, 2H), 2.220 (m, 2H), 1.764 (m, 1H), 1.070 (d, 3H, J=6.4 Hz), 1.020 (d, 3H, J=6.4 Hz), 0.898 (d, 3H, J=6.4 Hz).

Example PG

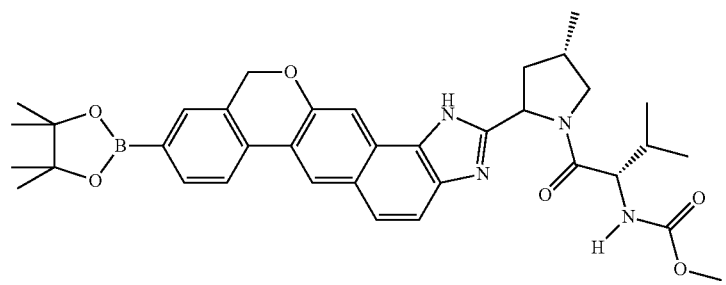

methyl [(2S-3-methyl-1-{(2S,4S)-4-methyl-2-[9-4,4,5,5-tetramethyl-1,3,2-dioxaborolan-2-yl)-1,11-dihydroisochromeno[4',3':6,7]naphtho[1,2-d]imidazol-2-yl]pyrrolidine-1-yl}-1-oxobutan-2-yl]carbamate

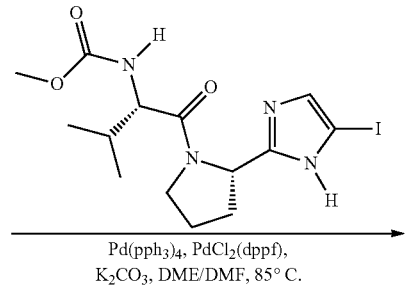

Pd(pph$_3$)$_4$, PdCl$_2$(dppf),
K$_2$CO$_3$, DME/DMF, 85° C.

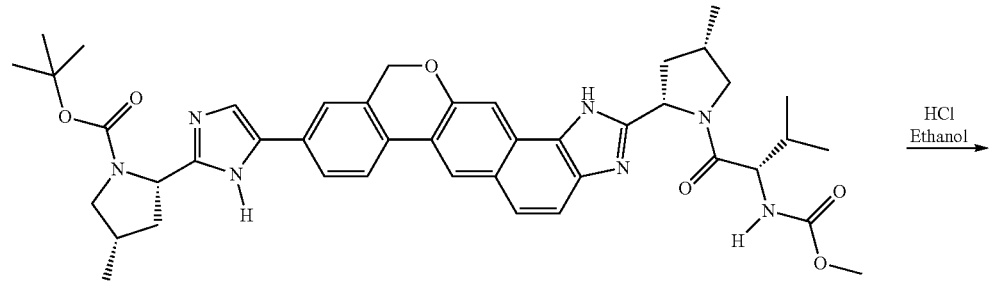

HCl
Ethanol tert-butyl (2S,4S)-[5-(2-{(2S,4S)-1-[N-methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate

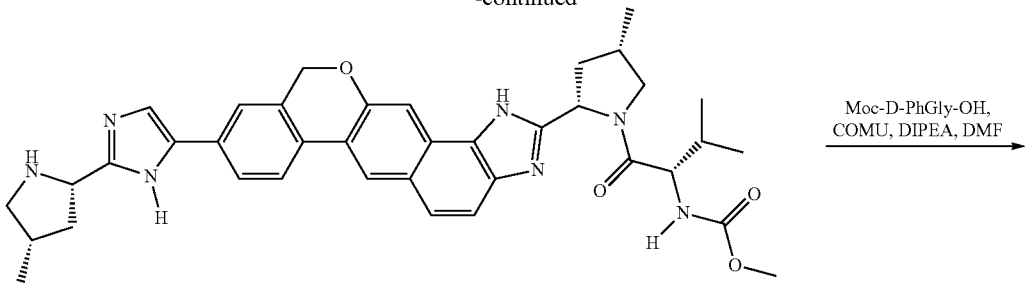

methyl {(2S)-3-methyl-1-[(2S,4S)-4-methyl-2-(9-{2-[(2S,4S)-4-methylpyrrolidin-2-yl]-1H-imidazol-5-yl}-1,11-dihydroisochromeno[4',3':6,7]naphtho[1,2-d]imidazol-2-yl)-pyrrolidin-1-yl]-1-oxobutan-2-yl}carbamate

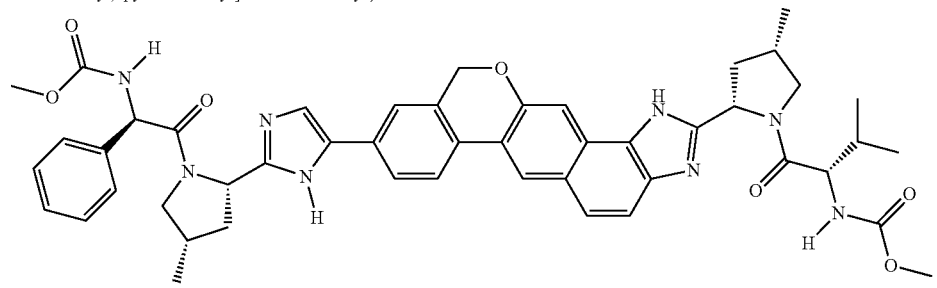

methyl {(1R)-2-[(2S,4S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-yl]-2-oxo-1-phenylethyl}carbamate tert-butyl (2S,4S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate:

The title compound was obtained as in example LQ but using methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (307 mg, 0.481 mmol) in place of tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate and methyl (S)-1-((S)-2-(5-iodo-1H-imidazol-2-yl)pyrrolidin-1-yl)-3-methyl-1-oxobutan-2-ylcarbamate (181 mg, 0.481 mmol) in place of methyl (S)-1-((S)-2-(5-bromo-1H-imidazol-2-yl)pyrrolidin-1-yl)-3-methyl-1-oxobutan-2-ylcarbamate. (200.8 mg)

methyl {(2S)-3-methyl-1-[(2S,4S)-4-methyl-2-(9-{2-[(2S,4S)-4-methylpyrrolidin-2-yl]-1H-imidazol-5-yl}-1,11-dihydroisochromeno[4',3':6,7]naphtho[1,2-d]imidazol-2-yl)pyrrolidin-1-yl]-1-oxobutan-2-yl}carbamate:

Tert-butyl (2S,4S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (200 mg, 0.262 mmol) was treated with 2 mL 1.25N HCl in ethanol and heated at 60° C. for 2 h, then it was concentrated under reduced pressure and pumped dry under high vacuum and used directly in the next step.

methyl {(1R)-2-[(2S,4S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-2-oxo-1-phenylethyl}carbamate:

A mixture of (R)-2-(methoxycarbonylamino)-2-phenylacetic acid (13 mg, 0.063 mmol), COMU (30 mg, 0.069 mmol) in 1.5 mL DMF was allowed to preactivate for 5 minutes before it was added to a solution of the amine from the previous salt in 1.5 mL DMF and DIPEA (0.137 mL, 0.786 mmol) and stirred overnight. The product was purified by reverse phase HPLC. The product was converted to the free base by dissolution in 2 mL 1:1 acetonitrile:methanol and passage through a prepacked cartridge of polymer supported carbonate. Concentration and drying gave an off white powder. (25.8 mg).

MS (ESI) m/z 853.8 [M+H]$^+$.

$^1$H NMR (CD$_3$CN) 8.164 (s, 1H), 7.781 (m, 1H), 7.609 (m, 2H), 7.535 (m, 2H), 7.433-7.305 (m, 6H), 7.229 (s, 1H), 5.482 (s, 1H), 5.290 (m, 1H), 5.191 (m, 1H), 4.997 (m, 2H), 4.372 (d, 1H, J=6.4 Hz), 4.267 (m, 1H), 3.735-3.445 (m, 10H), 2.573 (m, 4H), 2.197 (m, 2H), 2.017 (m, 1H), 1.760 (m, 1H), 1.204 (d, 3H, J=6.4 Hz), 1.068 (d, 3H, J=6.4 Hz), 1.010 (d, 3H, J=6.8 Hz), 0.887 (d, 3H, J=6.8 Hz).

Example PH

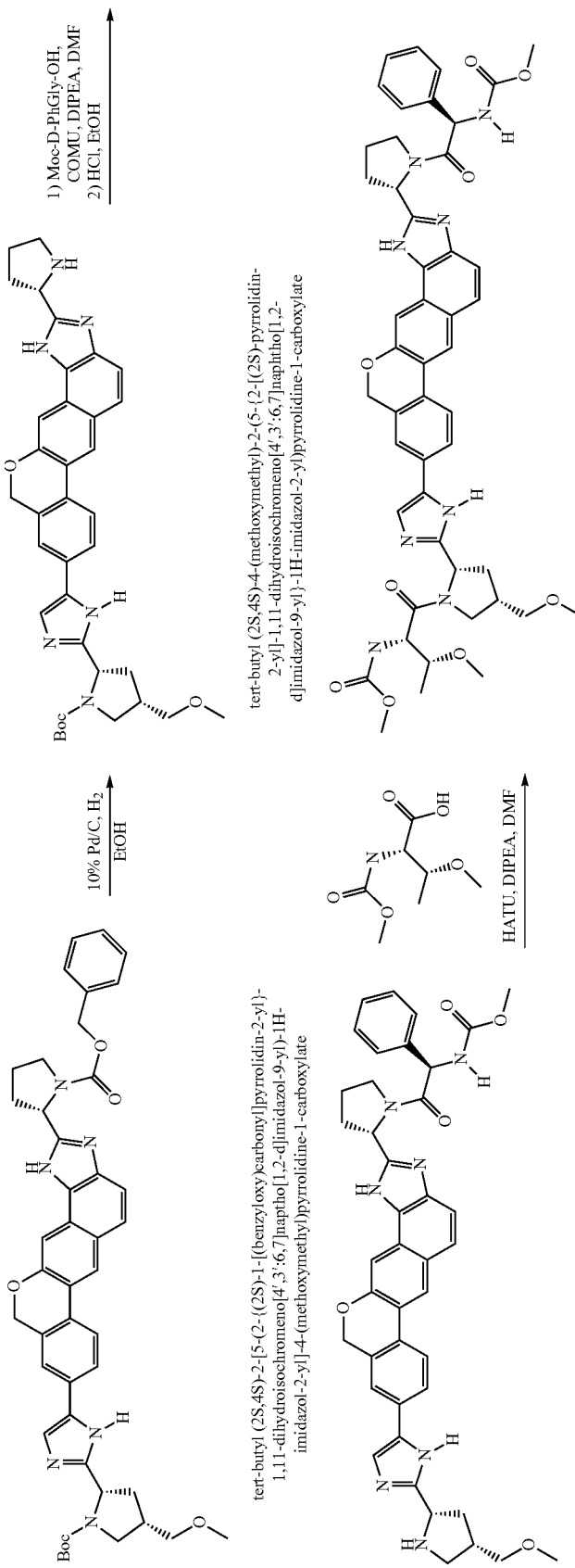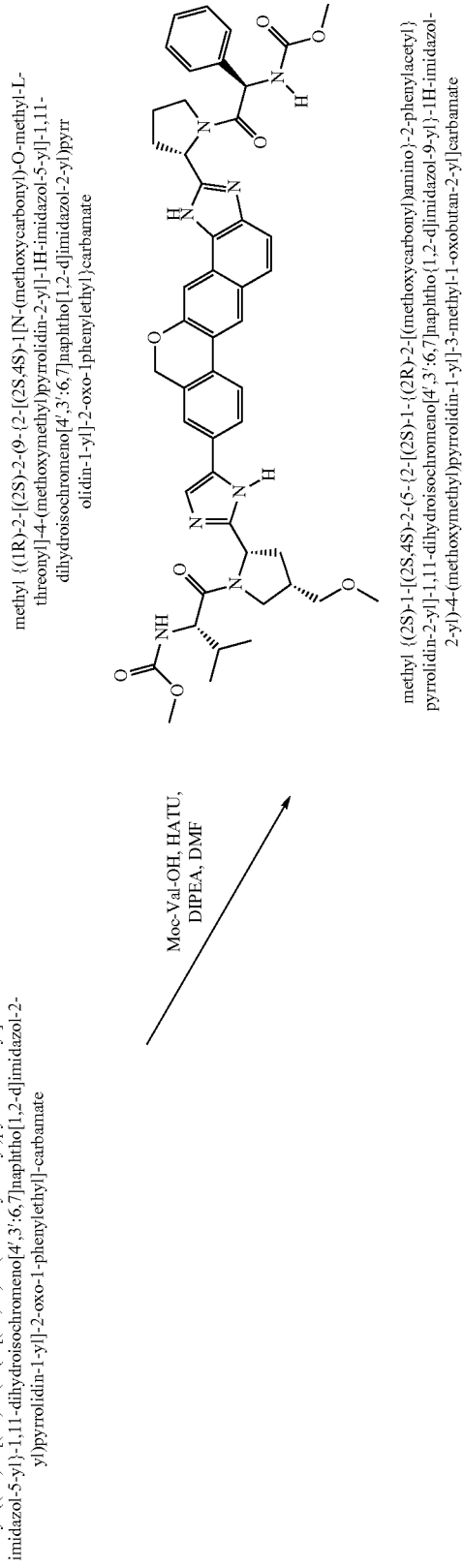

tert-butyl (2S,4S)-2-[5-(2-{(2S)-1-[(benzyloxy)carbonyl] pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate:

the title compound was obtained as in example OF (compound tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate) but using (S)-1-(benzyloxycarbonyl)pyrrolidine-2-carboxylic acid in place of (2S,5S)-1-((S)-2-(methoxycarbonylamino)-3-methylbutanoyl)-5-methylpyrrolidine-2-carboxylic acid in step 6.

tert-butyl (2S,4S)-4-(methoxymethyl)-2-(5-{2-[(2S)-pyrrolidin-2-yl]-1,11-dihydroisochromeno[4',3':6,7]naphtho[1,2-d]imidazol-9-yl}-1H-imidazol-2-yl)pyrrolidine-1-carboxylate:

A mixture of tert-butyl (2S,4S)-2-[5-(2-{(2S)-1-[(benzyloxy)carbonyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (724 mg, 0.96 mmol) and 70 mg 10% Pd/C in 20 mL ethanol was hydrogenated at 1 atm overnight. Additional 10% Pd/C (300 mg) and a portion of solid NaHCO3 was added and hydrogenation continued for 4 hours. Filtration through celite and concentration of the filtrate under reduced pressure gave the product as a dark brown solid, 454 mg. Purification by reverse phase HPLC gave 65 mg purified product.

methyl {(1R)-2-[(2S)-2-(9-{2-[(2S,4S)-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-phenylethyl}carbamate:

A mixture of (R)-2-(methoxycarbonylamino)-2-phenylacetic acid (22 mg, 0.105 mmol), COMU (45 mg, 0.069 mmol), and tert-butyl (2S,4S)-4-(methoxymethyl)-2-(5-{2-[(2S)-pyrrolidin-2-yl]-1,11-dihydroisochromeno[4',3':6,7]naphtho[1,2-d]imidazol-9-yl}-1H-imidazol-2-yl)pyrrolidine-1-carboxylate (65 mg, 0.105 mmol) in 1.5 mL 10% DIPEA in DMF was stirred for 1.5 h. The reaction mixture was partitioned between ethyl acetate and saturated sodium bicarbonate. The organic phase was dried over sodium sulphate, filtered and concentrated under reduced pressure. The crude intermediate was treated with 8 mL 1.25N HCl in ethanol at 50° C. for 4 h. Added saturated sodium bicarbonate and extracted the free base into dichloromethane. (106 mg)

methyl {(2S)-1-[(2S,4S)-2-(5-{2-[(2S)-1-{(2R)-2-[(methoxycarbonyl)amino]-2-phenylacetyl}pyrrolidin-2-yl]-1,11-dihydroisochromeno[4',3': 6,7]naphtho[1,2-d]imidazol-9-yl}-1H-imidazol-2-yl)-4-(methoxymethyl)pyrrolidin-1-yl]-3-methyl-1-oxobutan-2-yl}carbamate:

A mixture of methyl {(1R)-2-[(2S)-2-(9-{2-[(2S,4S)-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-phenylethyl}carbamate (55 mg, 0.077 mmol), (S)-2-(methoxycarbonylamino)-3-methylbutanoic acid (14 mg, 0.077 mmol), HATU (32 mg, 0.085 mmol) and 0.4 mL 10% DIPEA in DMF was stirred at room temperature for 1 hour. The product was purified by reverse phase HPLC. The product was converted to the free base by dissolution in 2 mL 1:1 acetonitrile:methanol and passage through a prepacked cartridge of polymer supported carbonate. The eluent was concentrated, the taken up in 1% TFA in 1:1 acetonitrile:water, frozen, and lyophilized to give the product as a trifluoroacetate salt. (30.7 mg): MS (ESI) m/z 869.9 [M+H]+.

methyl {(1R)-2-[(2S)-2-(9-{2-[(2S,4S)-1-[N-(methoxycarbonyl)-O-methyl-L-threonyl]-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-phenylethyl}carbamate:

A mixture of methyl {(1R)-2-[(2S)-2-(9-{2-[(2S,4S)-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-phenylethyl}carbamate (51 mg, 0.072 mmol), (2S,3R)-3-methoxy-2-(methoxycarbonylamino)butanoic acid (14 mg, 0.072 mmol), HATU (30 mg, 0.079 mmol) and 0.4 mL 10% DIPEA in DMF was stirred at room temperature for 1 hour. The product was purified by reverse phase HPLC. The product was converted to the free base by dissolution in 2 mL 1:1 acetonitrile:methanol and passage through a prepacked cartridge of polymer supported carbonate. The eluent was concentrated, taken up in 1% TFA in 1:1 acetonitrile:water, frozen, and lyophilized to give the product as a trifluoroacetate salt. (24 mg)

MS (ESI) m/z 885.8 [M+H]+;

1H NMR (CD3CN) 7.635 (s, 1H), 7.434 (m, 3H), 7.330 (m, 4H), 7.233 (m, 1H), 7.164 (m, 1H), 6.983 (m, 1H), 6.747 (m, 2H), 6.127 (m, 1H), 5.584 (d, 1H, J=6.4 Hz), 5.431 (m, 1H), 5.145 (m, 1H), 4.729 (s, 2H), 4.442 (m, 1H), 4.029 (m, 2H), 3.838 (m, 1H), 3.662-3.534 (m, 2H), 3.572 (s, 3H) 3.552 (s, 3H), 3.444-3.310 (m, 3H), 3.240 (s, 3H), 3.225 (s, 3H), 2.618 (m, 1H), 2.464 (m, 1H), 2.304 (m, 1H), 2.129 (m, 1H), 2.041 (m, 1H), 1.899 (m, 2H), 1.107 (d, 3H, J=6.4 Hz).

Example PI

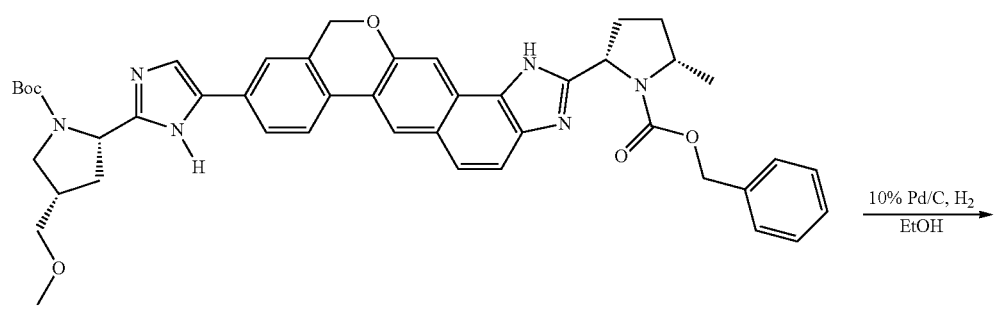

tert-butyl (2S,4S)-2-[5(2-{(2S,5S)-1-[(benzyloxy)carbonyl)-5-methylpyrrolidin-2-yl)-1,11-dihydroisochromeno(4',3':6,7)naphtho[1,2-d]imidazol-9-yl)-1H-imidazol-2-yl]-4-(methoxymethyl)pyrrolidine-1-carboxlate

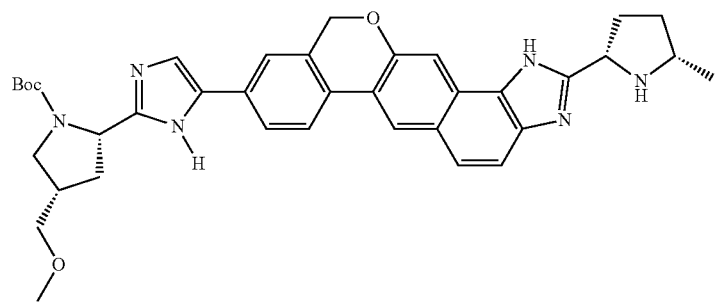

(2S,3R)-3-methoxyl-2-(methoxycarbonylamino)butanoic acid

1) HATU, DIPEA, DMF
2) HCl in Ethanol

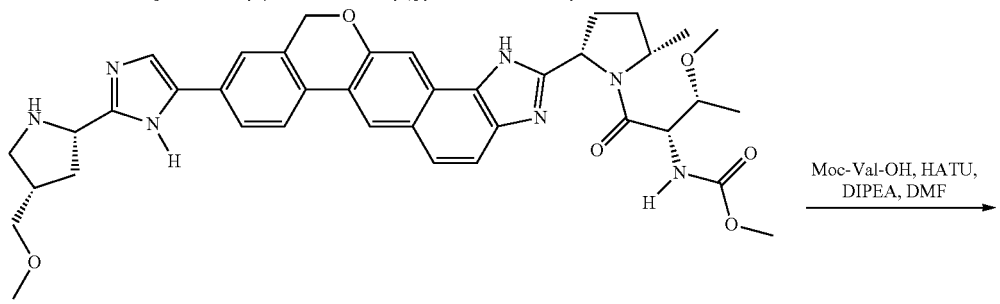

tert-butyl (2S, 4S)-4-(methoxymethyl)-2-(5-{2-[(2S,5S)-5-methylpyrrolidin-2-yl]-1,11-dihydroisochromeno[4',3':6,7]naphtho[1,2-d]imidazol-9-yl}-1H-imidazol-2-yl)pyrrolidine-1-carboxylate Moc-Val-OH, HATU, DIPEA, DMF

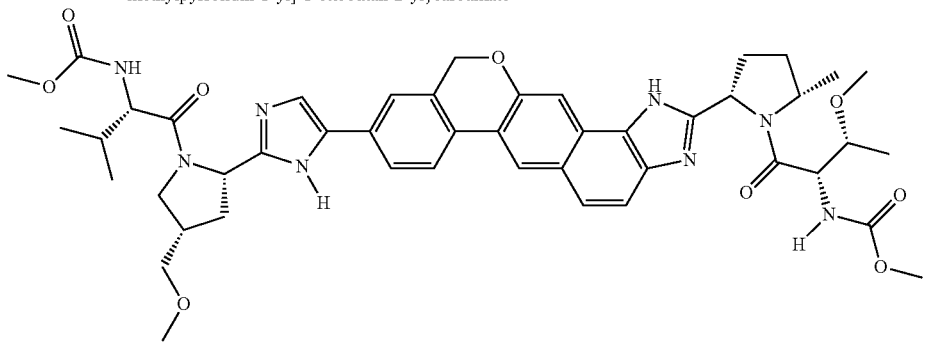

methyl {(2S,3R)-3-methoxy-1-[(2S,5S)-2-(9-{2-[(2S,4S)-4-(methoxymethyl)pyrrolidin-2-yl]-1H-imidazol-5-yl]-1,11-dihydroisochromeno[4',3':6,7]naphtho[1,2-d]imidazol-2-yl)-5-methylpyrrolidin-1-yl]-1-oxobutan-2-yl}carbamate methyl {(2S,4S)-2-(5-{2-[(2S,5S)-1-[(2S,3R)-3-methoxy-2-[(methoxycarbonyl)amino]butanoyl}-5-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate tert-butyl (2S,4S)-2-[5-(2-{(2S,5S)-1-[(benzyloxy)carbonyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate:

The title compound was obtained as in example OF (compound tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl) pyrrolidine-1-carboxylate) but using (2S,5S)-1-(benzyloxycarbonyl)-5-methylpyrrolidine-2-carboxylic acid in place of (2S,5S)-1-((S)-2-(methoxycarbonylamino)-3-methylbutanoyl)-5-methylpyrrolidin-2-carboxylic acid.

tert-butyl (2S,4S)-4-(methoxymethyl)-2-(5-{2-[(2S,5S)-5-methylpyrrolidin-2-yl]-1,11-dihydroisochromeno[4',3':6,7]naphtho[1,2-d]imidazol-9-yl}-1H-imidazol-2-yl)pyrrolidine-1-carboxylate:

A mixture of the proline (830 mg, 1.08 mmol) and 100 mg 10% Pd/C in 20 mL ethanol was hydrogenated at 1 atm overnight. Additional 10% Pd/C (300 mg) and a portion of solid NaHCO3 was added and hydrogenation continued for 4 hours. Filtration through celite and concentration of the filtrate under reduced pressure gave the product as a dark brown solid, 722 mg. Purification by reverse phase HPLC gave 100 mg purified product.

methyl {(2S,3R)-3-methoxy-1-[(2S,5S)-2-(9-{2-[(2S,4S)-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-1-oxobutan-2-yl}carbamate:

A mixture of tert-butyl (2S,4S)-4-(methoxymethyl)-2-(5-{2-[(2S,5S)-5-methylpyrrolidin-2-yl]-1,11-dihydroisochromeno[4',3': 6,7]naphtho[1,2-d]imidazol-9-yl}-1H-imidazol-2-yl)pyrrolidine-1-carboxylate (101 mg, 0.159 mmol), (2S,3R)-3-methoxy-2-(methoxycarbonylamino)butanoic acid (30 mg, 0.159 mmol), HATU (61 mg, 0.159 mmol) and 2 mL 10% DIPEA in DMF was stirred at room temperature for 1.5 hours. Saturated sodium bicarbonate was added and the product was extracted into dichloromethane, dried over sodium sulphate, filtered and concentrated under reduced pressure. This crude product was treated with 5 mL 1.25N HCl in ethanol at 50° C. for 4 h and then it was concentrated under reduced pressure. Saturated sodium bicarbonate was added and the product was extracted into dichloromethane, dried over sodium sulphate, filtered and concentrated under reduced pressure. (74.6 mg)

methyl {(2S)-1-[(2S,4S)-2-(5-{2-[(2S,5S)-1-{(2S,3R)-3-methoxy-2-[(methoxycarbonyl)amino]butanoyl}-5-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate:

A mixture of methyl {(2S,3R)-3-methoxy-1-[(2S,5S)-2-(9-{2-[(2S,4S)-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-1-oxobutan-2-yl}carbamate (74.6 mg, 0.105 mmol), (S)-2-(methoxycarbonylamino)-3-methylbutanoic acid (18.5 mg, 0.105 mmol), HATU (44 mg, 0.116 mmol) and 0.6 mL 10% DIPEA in DMF was stirred at room temperature for 1 hour. The product was purified by reverse phase HPLC. (48.1 mg)

MS (ESI) m/z 866.1 [M+H]+.

Example PJ

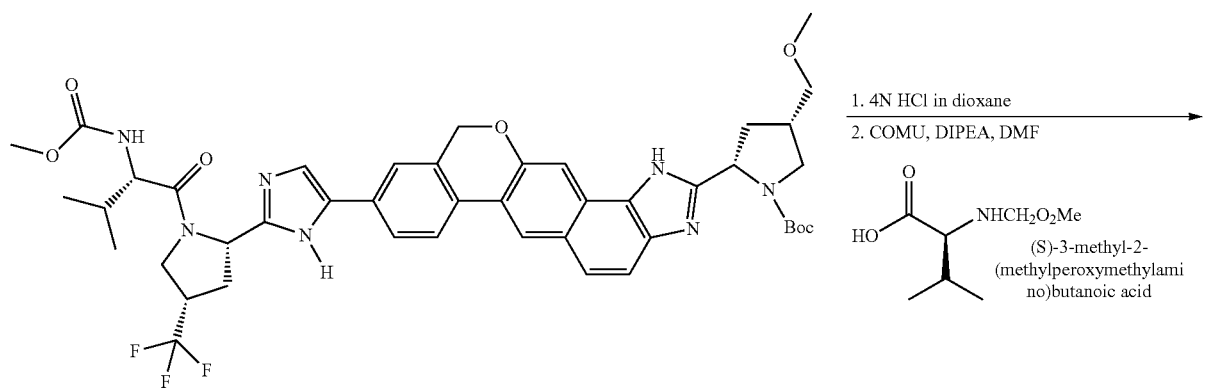

tert-butyl (2S,4S)-2-(9-{2-[(2S,4S)-1-[N-(methoxycarbonyl)-L-valyl]-4-(trifluoromethyl)pyrrolidin-2-yl]-1H-imidazol-5-yl}-1,11-dihydroisochromeno[4',3':6,7]naphtho[1,2-d]imidazol-2-yl)-4-(methoxymethyl)pyrrolidine-1-carboxylate

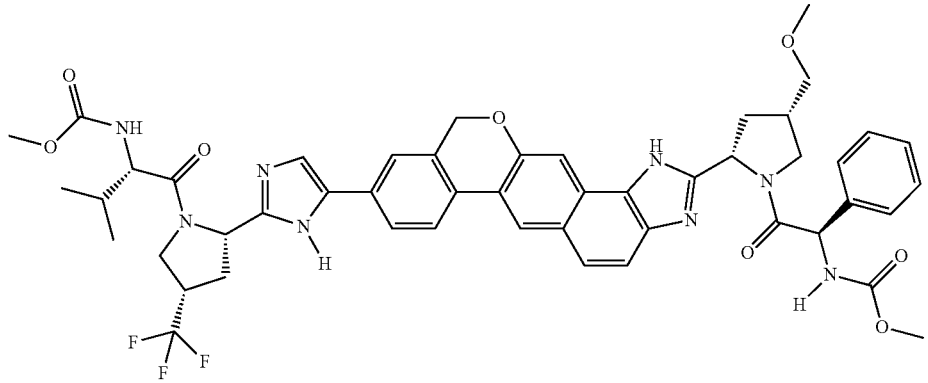

methyl {(1R)-2-[(2S,4S)-2-(9-{2-{(2S,4S)-1-{(2S)-2-[(methoxycarbonyl)amino]-3-methylbutanoyl}-4-(trifluoromethyl)pyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate tert-butyl (2S,4S)-2-(9-{2-[(2S,4S)-1-[N-(methoxycarbonyl)-L-valyl]-4-(trifluoromethyl)pyrrolidin-2-yl]-1H-imidazol-5-yl}-1,11-dihydroisochromeno[4',3':6,7]naphtho[1,2-d]imidazol-2-yl)-4-(methoxymethyl) pyrrolidine-1-carboxylate:

the title compound was prepared as in example OF for compound tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate, by using (2S,4S)-1-((S)-2-(methoxycarbonylamino)-3-methylbutanoyl)-4-(trifluoromethyl)pyrrolidine-2-carboxylic acid in place of (2S,4S)-1-(tert-butoxycarbonyl)-4-(methoxymethyl)pyrrolidine-2-carboxylic acid and (2S,4S)-1-(tert-butoxycarbonyl)-4-(methoxymethyl)pyrrolidine-2-carboxylic acid in place of (2S,5S)-1-((S)-2-(methoxycarbonylamino)-3-methylbutanoyl)-5-methylpyrrolidine-2-carboxylic acid.

methyl {(1R)-2-[(2S,4S)-2-(9-{2-[(2S,4S)-1-{(2S)-2-[(methoxycarbonyl)amino]-3-methylbutanoyl}-4-(trifluoromethyl)pyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate:

tert-butyl (2S,4S)-2-(9-{2-[(2S,4S)-1-[N-(methoxycarbonyl)-L-valyl]-4-(trifluoromethyl)pyrrolidin-2-yl]-1H-imidazol-5-yl}-1,11-dihydroisochromeno[4',3':6,7]naphtho[1,2-d]imidazol-2-yl)-4-(methoxymethyl) pyrrolidine-1-carboxylate (<0.412 mmol, crude from previous step) was treated with 6 mL 4N HCl in dioxane at room temperature overnight and then at 50° C. for 1 hour. Diethyl ether (20 mL) was added and the precipitate of hydrochloride salt was collected by vacuum filtration. (126 mg, 0.16 mmol). This material was combined with (R)-2-(methoxycarbonylamino)-2-phenylacetic acid (34 mg, 0.16 mmol), COMU (70 mg, 0.16 mmol), and 1.6 mL of 10% DIPEA in DMF. After 1 hour at room temperature, the mixture was added dropwise into 25 mL saturated sodium bicarbonate, with stirring and the resulting precipitate was collected by vacuum filtration and washed with 2 mL water. The product was purified, then re-purified by reverse phase HPLC. (3.5 mg).

MS (ESI) m/z 938.1 [M+H]$^+$.

Example PK

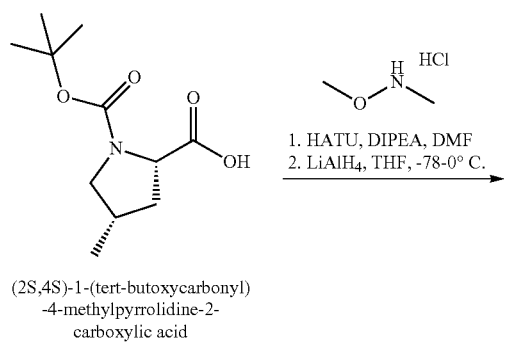

(2S,4S)-1-(tert-butoxycarbonyl)-4-methylpyrrolidine-2-carboxylic acid

1. HATU, DIPEA, DMF
2. LiAlH$_4$, THF, -78-0° C.

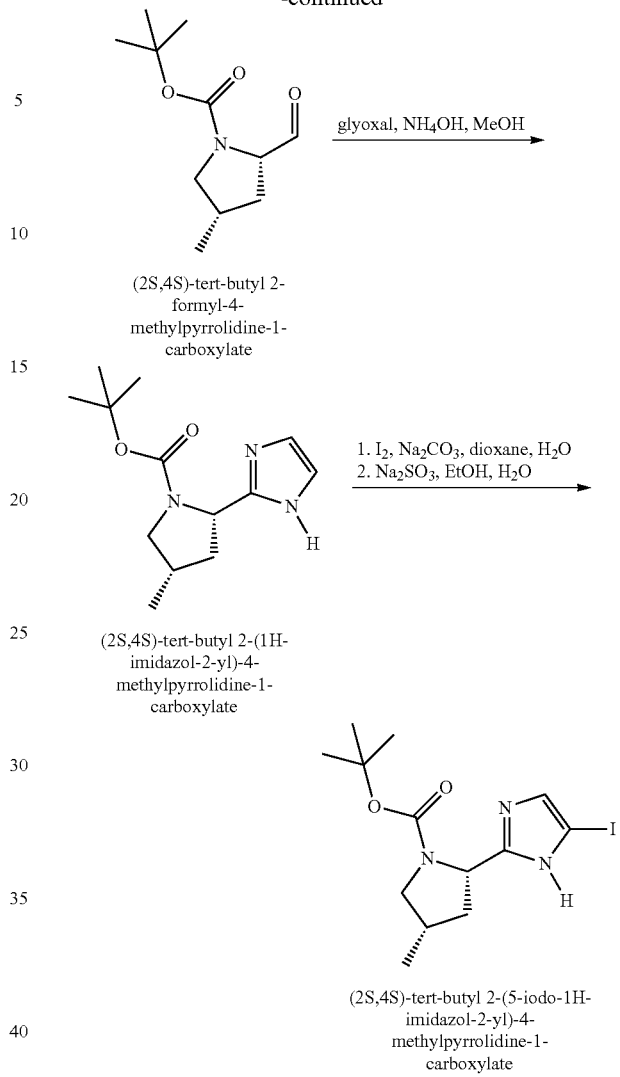

(2S,4S)-tert-butyl 2-formyl-4-methylpyrrolidine-1-carboxylate glyoxal, NH$_4$OH, MeOH (2S,4S)-tert-butyl 2-(1H-imidazol-2-yl)-4-methylpyrrolidine-1-carboxylate 1. I$_2$, Na$_2$CO$_3$, dioxane, H$_2$O
2. Na$_2$SO$_3$, EtOH, H$_2$O (2S,4S)-tert-butyl 2-(5-iodo-1H-imidazol-2-yl)-4-methylpyrrolidine-1-carboxylate (2S,4S)-tert-butyl 2-formyl-4-methylpyrrolidine-1-carboxylate:

A mixture of (2S,4S)-1-(tert-butoxycarbonyl)-4-methylpyrrolidine-2-carboxylic acid (5.2g, 22.7 mmol), O,N-dimethylhydroxylamine hydrochloride (2.4g, 24.9 mmol), HATU (10.4g, 27.2 mmol) and DIPEA (9.5 mL, 54.5 mmol) in 114 mL DMF was stirred at room temperature overnight. The mixture was extracted into ethyl acetate and washed with saturated bicarbonate and water, dried over sodium sulphate, filtered, and concentrated. It was then dissolved in diethyl ether (100 mL) and washed with water to remove residual DMF, dried, filtered, and concentrated to a pale yellow oil (5.30g, 19.5 mmol) of (2S,4S)-tert-butyl 2-(methoxy(methyl)carbamoyl)-4-methylpyrrolidine-1-carboxylate.

(2S,4S)-tert-butyl 2-(methoxy(methyl)carbamoyl)-4-methylpyrrolidine-1-carboxylate (5.30g, 19.5 mmol) was dissolved in 120 mL THF, cooled to -78° C. and treated with lithium aluminium hydride (1M in THF, 19.5 mL, 19.5 mmol) dropwise via addition funnel. After 1 hour, the mixture was brought to 0° C. and kept at that temperature for 2 hours. It was quenched by dropwise addition of a 50 mL solution of 3.0g KHSO4 in water, removed from the ice bath, and stirred 15 minutes at room temperature. The product was extracted with three 75 mL portions of ethyl acetate and washed with brine. The organic phase was dried over sodium sulphate, filtered, and concentrated to give crude (2S,4S)-tert-butyl 2-formyl-4-methylpyrrolidine-1-carboxylate. (4.89g)

(2S,4S)-tert-butyl 2-(1H-imidazol-2-yl)-4-methylpyrrolidine-1-carboxylate:

To a solution of (2S,4S)-tert-butyl 2-formyl-4-methylpyrrolidine-1-carboxylate (4.89 g, 22.9 mmol), ammonium hydroxide (17 mL) and water (17 mL) was added, dropwise, glyoxal (40% in water, 14.6 mL, 128 mmol) and the resulting mixture was stirred at room temperature overnight. Saturated sodium bicarbonate (100 mL) was added and the mixture was extracted with four 75 mL portions of dichloromethane. The organic phase was washed with water, dried over sodium sulphate, filtered and concentrated, and then purified by silica gel chromatography to give a total of 3.76g product.

(2S,4S)-tert-butyl 2-(5-iodo-1H-imidazol-2-yl)-4-methylpyrrolidine-1-carboxylate:

A mixture of (2S,4S)-tert-butyl 2-(1H-imidazol-2-yl)-4-methylpyrrolidine-1-carboxylate (1.0g, 3.97 mmol), iodine (2.22g, 8.75 mmol) and sodium carbonate (1.3g, 12.31 mmol) in 20 mL dioxane and 13.25 mL water was covered in foil and stirred at room temperature overnight. The mixture was diluted with ethyl acetate and treated with 10% sodium thiosulfate (5 mL) and stirred for 10 minutes. The organic phase was washed with brine, and then the aqueous phase was back extracted with ethyl acetate. The combined organic phases were dried over sodium sulphate, filtered and concentrated to provide crude (2S,4S)-tert-butyl 2-(4,5-diiodo-1H-imidazol-2-yl)-4-methylpyrrolidine-1-carboxylate (2.25g) as a pale yellow solid.

A solution of (2S,4S)-tert-butyl 2-(4,5-diiodo-1H-imidazol-2-yl)-4-methylpyrrolidine-1-carboxylate (2.25g, 4.4 mmol) in 18 mL ethanol and 18 mL water was treated with sodium sulfite (5.59g, 44.4 mmol) and heated at 90° C. overnight. The mixture was partitioned between ethyl acetate and water. The aqueous phase was extracted with more ethyl acetate and the combined organic phase was washed with brine, dried over sodium sulphate, filtered, concentrated, and purified by silica gel chromatography to give 766 mg (2S,4S)-tert-butyl 2-(5-iodo-1H-imidazol-2-yl)-4-methylpyrrolidine-1-carboxylate.

Example PL

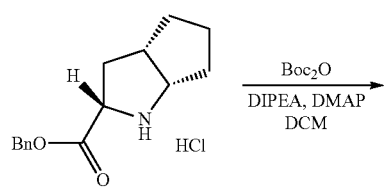

(2S,3aS,6aS)-benzyl octahydrocyclopenta[b]pyrrole-2-carboxylate hydrochloride

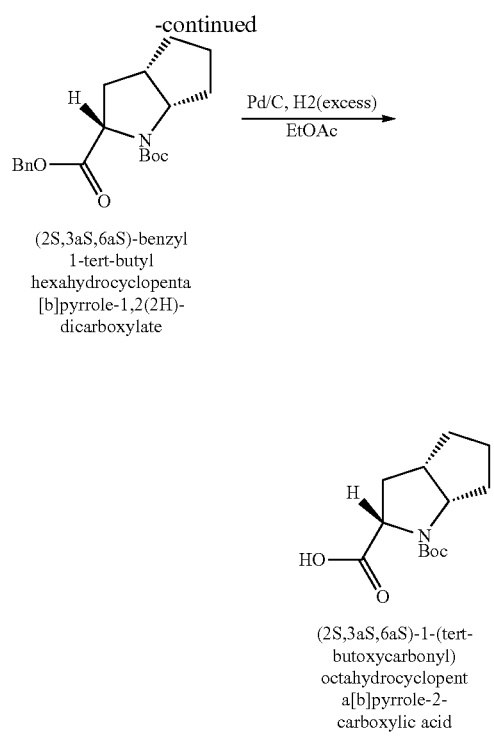

(2S,3aS,6aS)-benzyl 1-tert-butyl hexahydrocyclopenta[b]pyrrole-1,2(2H)-dicarboxylate (2S,3aS,6aS)-1-(tert-butoxycarbonyl) octahydrocyclopenta[b]pyrrole-2-carboxylic acid (2S,3aS,6aS)-2-benzyl 1-tert-butyl hexahydrocyclopenta[b]pyrrole-1,2(2H)-dicarboxylate:

To a solution of commercially available (2S,3aS,6aS)-2-benzyl 1-tert-butyl hexahydrocyclopenta[b]pyrrole-1,2(2H)-dicarboxylate (4.70 g, 16.68 mmol) in methylene chloride (42 mL) was added Di-tert-butyl dicarbonate (7.28 g, 33.36 mmol) N,N-diisopropylethylamine (5.82 mL, 33.36 mmol) and 4-(Dimethylamino)pyridine (0.20 g, 1.67 mmol). The solution was stirred under air for 16 hours. Upon completion, the reaction was concentrated in vacuo, diluted in ethyl acetate, and washed with 1N HCl. The aqueous layers were backextracted twice with ethyl acetate and the combined organic layers were dried over sodium sulfate, filtered and concentrated. The resulting residue was purified by silica gel chromatography (5-40% ethyl acetate in hexanes) to afford (2S,3aS,6aS)-2-benzyl 1-tert-butyl hexahydrocyclopenta[b]pyrrole-1,2(2H)-dicarboxylate which was used without further purification. MS (ESI) m/z 368.47 [M+Na]$^+$.

(2S,3aS,6aS)-1-(tert-butoxycarbonyl)octahydrocyclopenta[b]pyrrole-2-carboxylic acid: To a 250 mL round bottom flask charged with a stirbar and (2S,3aS,6aS)-2-benzyl 1-tert-butyl hexahydrocyclopenta[b]pyrrole-1,2(2H)-dicarboxylate (5.76 g, 16.68 mmol) was added 10% Palladium on carbon (1.77g). Ethanol was poured over the mixture and the reaction mixture was evacuated and flushed with hydrogen gas three times. The suspension was stirred at room temperature under and atmosphere of hydrogen for 24 hours. Upon completion, the reaction mixture was filtered through celite and concentrated to give (2S,3aS,6aS)-1-(tert-butoxycarbonyl)octahydrocyclopenta[b]pyrrole-2-carboxylic acid (4.45g, >99%). MS (ESI) m/z 256.21 [M+H]$^+$.

Example PM
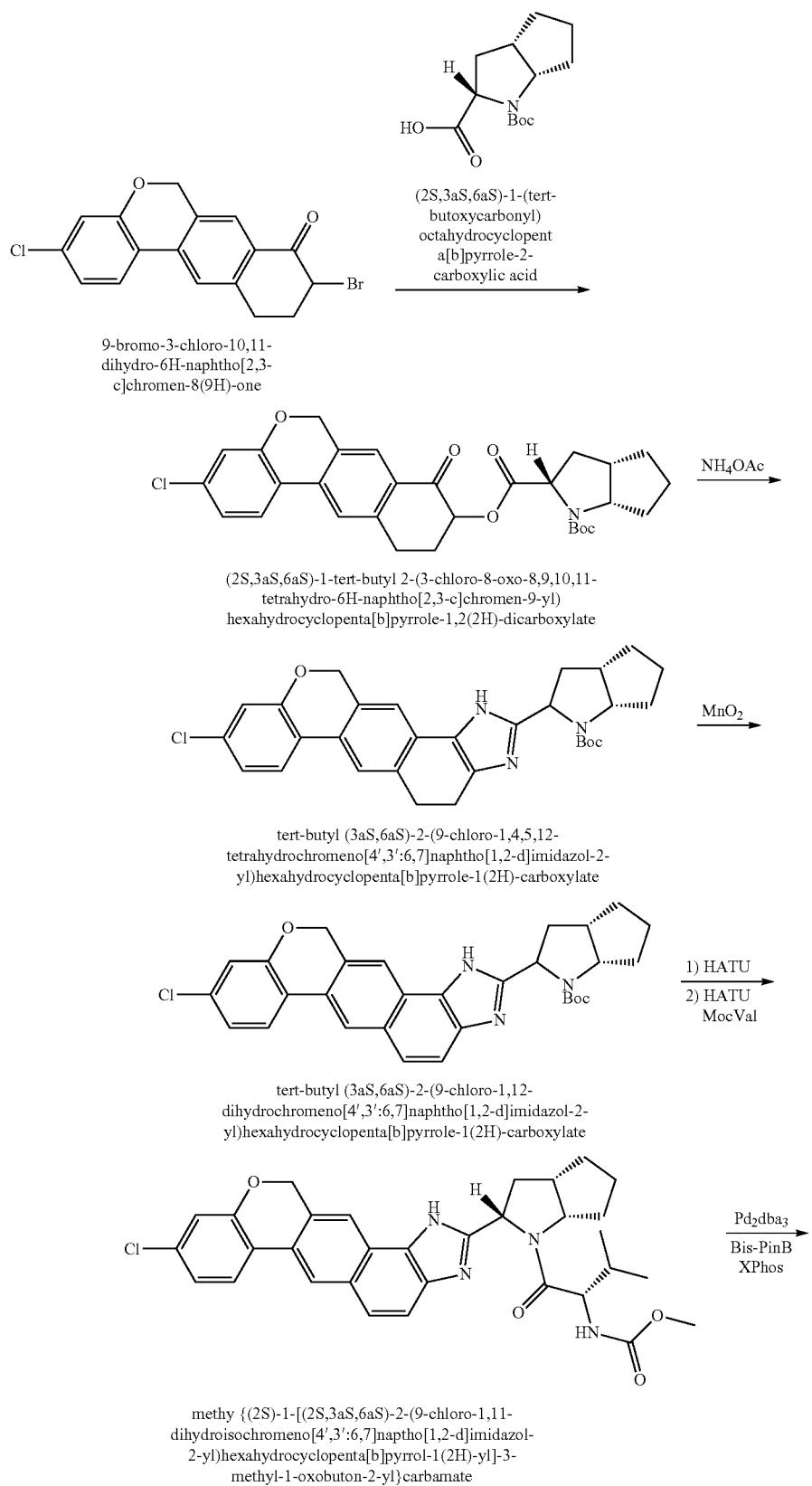

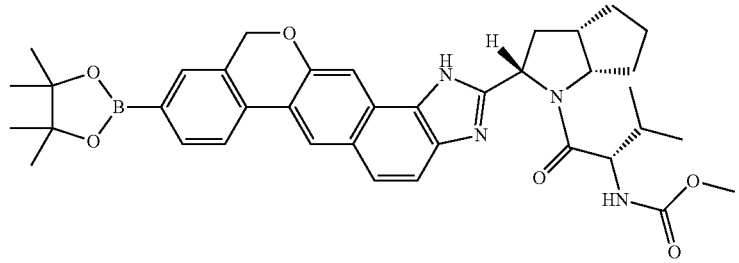
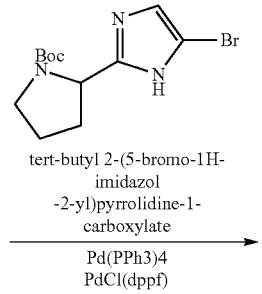

tert-butyl 2-(5-bromo-1H-imidazol-2-yl)pyrrolidine-1-carboxylate

Pd(PPh3)4
PdCl(dppf)

methyl {(2S)-3-methyl-1-oxo-1-[(2S,3aS,6aS)-2-[9-(4,4,5,5-tetramethyl-1,3,2-dioxaborolan-2-yl)-1,11-dihydroisochromeno[4',3':6,7]naphtho[1,2-d]imidazol-2-yl]hexahydrocyclopenta[b]pyrrol-1(2H)-yl]butan-2-yl}carbamate

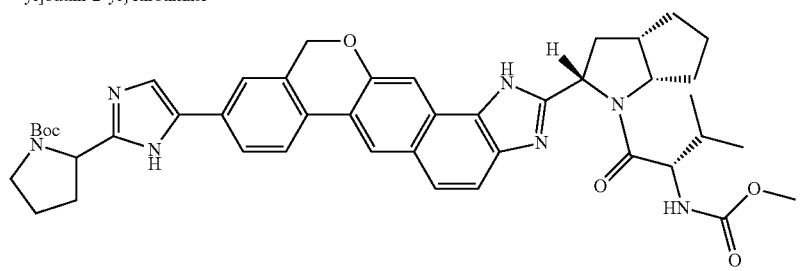

tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate tert-butyl 2-[5-(2-{(2S,3aS,6aS)-1-[N-(methoxycarbonyl)-1-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate: This compound was made in an analogous manner to tert-butyl (2R)-2-[5-(2-{(2S)-1-[N-(methoxycarbonyl)-L-valyl]pyrrolidin-2-yl}-3,11-dihydroisochromeno[4',3':6,7]naphtho[1,2-d]imidazol-9-yl)-1H-imidazol-2-yl]pyrrolidine-1-carboxylate substituting (2S,3aS,6aS)-1-(tert-butoxycarbonyl)octahydrocyclopenta[b]pyrrole-2-carboxylic acid for the initial alkylation of 9-bromo-3-chloro-10,11-dihydro-6H-naphtho[2,3-c]chromen-8(9H)-one. Reactions in the synthesis of tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate gave similar product yields as in the synthesis of tert-butyl (2R)-2-[5-(2-{(2S)-1-[N-(methoxycarbonyl)-L-valyl]pyrrolidin-2-yl}-3,11-dihydroisochromeno[4',3':6,7]naphtho[1,2-d]imidazol-9-yl)-1H-imidazol-2-yl]pyrrolidine-1-carboxylate. MS (ESI) m/z 774.1 [M+H]+.

Example PN

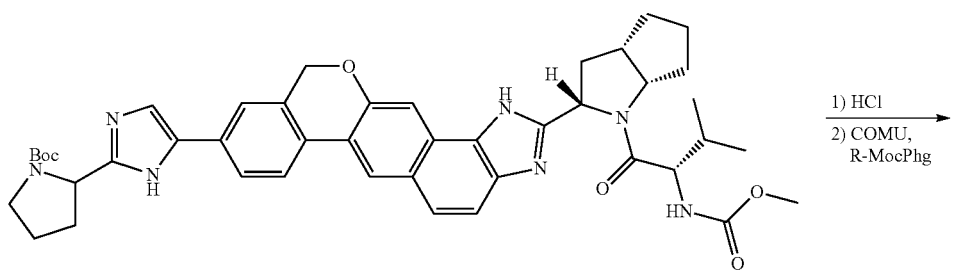

tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate 1) HCl
2) COMU, R-MocPhg

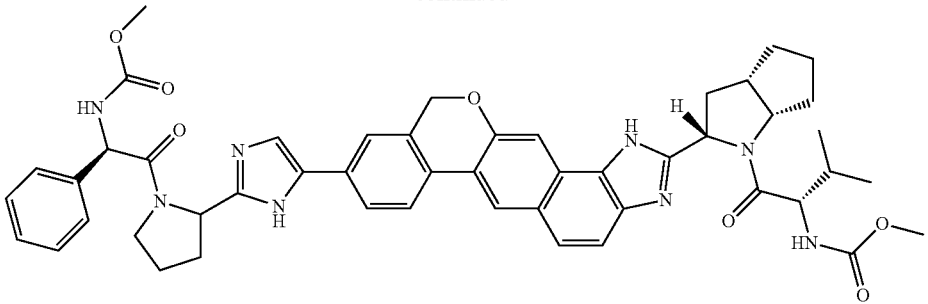

methyl {(1R)-2-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate methyl {(1R)-2-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate: To a solution of tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate (0.128 g, 0.165 mmol) in a mixture of $CH_2Cl_2$ (1.6 mL) and MeOH (0.33 mL) was added HCl (4M in 1,4-dioxane, 1.24 mL, 4.9 mmol). The solution was stirred at room temperature for 1.5 h and concentrated to dryness.

The intermediate was dissolved in $CH_2Cl_2$ (1.6 mL). (R)-2-(methoxycarbonylamino)-2-phenylacetic acid (0.052 g, 0.25 mmol) and DIPEA (0.087 mL, 0.496 mmol) were then added to the solution. The reaction mixture was cooled to −40° C. (external temperature, $MeCN/CO_2(s)$ bath). COMU (0.113 g, 0.265 mmol) was then added and solution was allowed to warm to 0° C. over 1.5 h. Upon completion by LCMS, the solution was diluted with DMF and concentrated. The crude product was purified by preparative HPLC (Gemini column, 10-47% MeCN/$H_2O$ with 0.1% TFA) and the desired fractions were combined. The solution was concentrated until the aqueous layer remained and aqueous bicarbonate (sat.) was slowly added until the solution was basic. The resulting slurry was stirred at room temperature for 2 h and filtered. The resulting solid was dried in vacuo to provide methyl {(1R)-2-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate (0.068 g, 48%).

MS (ESI) m/z 865.7 $[M+H]^+$. $^1$H NMR (400 MHz, cd$_3$od) δ 8.44-8.30 (m, 1H), 8.02-7.82 (m, 2H), 7.81-7.58 (m, 4H), 7.50-7.11 (m, 6H), 7.09-6.83 (m, 2H), 5.72-5.45 (m, 2H), 5.41 (s, 1H), 5.34-5.28 (m, 1H), 5.22 (s, 3H), 4.69-4.64 (m, 1H), 4.26-4.19 (m, 1H), 4.03-3.98 (m, 1H), 3.96-3.91 (m, 1H), 3.66 (d, 4H), 2.98-2.91 (m, 1H), 2.88-2.83 (m, 1H), 2.58-2.48 (m, 1H), 2.27-2.12 (m, 4H), 2.11-2.00 (m, 3H), 2.00-1.89 (m, 2H), 1.77-1.72 (m, 1H), 1.31-1.04 (m, 3H), 0.93 (d, 6H).

Example PO

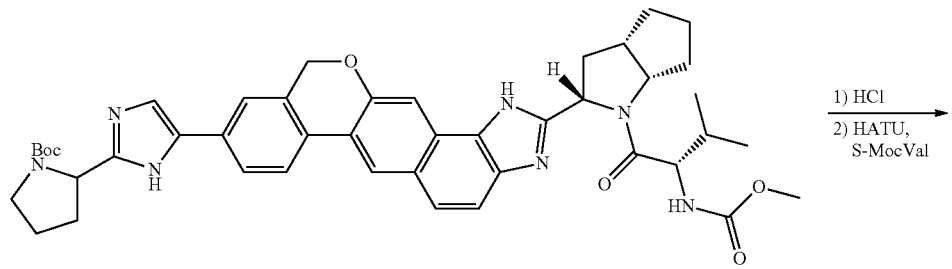

tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate 1) HCl
2) HATU, S-MocVal

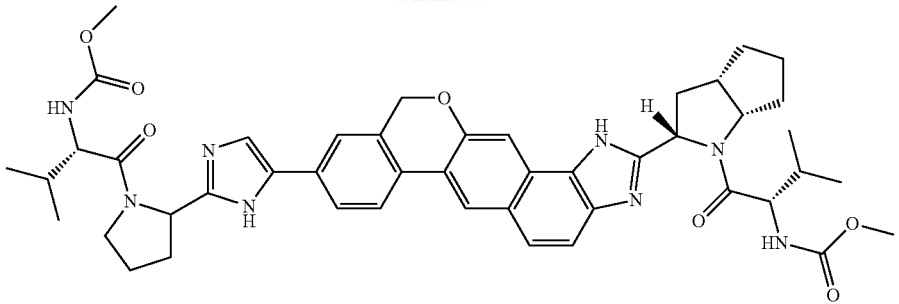

methyl {(2S)-1-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate methyl {(2S)-1-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate: To a solution of tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate (0.030 g, 0.039 mmol) in a mixture of CH$_2$Cl$_2$ (0.39 mL) and MeOH (0.078 mL) was added HCl (4M in 1,4-dioxane, 0.29 mL, 1.16 mmol). The solution was stirred at room temperature for 1.5 h and concentrated to dryness.

The intermediate was dissolved in CH$_2$Cl$_2$ (0.39 mL). (S)-2-(methoxycarbonylamino)-3-methylbutanoic acid (0.007 g, 0.043 mmol) and DIPEA (0.020 mL, 0.116 mmol) were then added to the solution. HATU (0.018 g, 0.047 mmol) was added and solution was allowed to stir at room temp. Upon completion, the solution was diluted with DMF and concentrated. The crude product was purified by preparative HPLC (Gemini column, 10-47% MeCN/H$_2$O with 0.1% TFA) and the desired fractions were combined and lyophilized to provide methyl {(2S)-1-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate (0.010g, 31%). MS (ESI) m/z 832.2 [M+H]$^+$.

Example PP methyl [(1S)-2-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-2-oxo-1-(tetrahydro-2H-pyran-4-yl)ethyl]carbamate methyl [(1S)-2-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-2-oxo-1-(tetrahydro-2H-pyran-4-yl)ethyl]carbamate: This compound was made in an analogous manner to methyl {(2S)-1-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate, substituting (S)-2-(methoxycarbonylamino)-2-(tetrahydro-2H-pyran-4-yl) acetic acid for (S)-2-(methoxycarbonylamino)-3-methylbutanoic acid to give methyl [(1S)-2-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-2-oxo-1-(tetrahydro-2H-pyran-4-yl)ethyl]carbamate (0.039, 56%). MS (ESI) m/z 874.34 [M+H]$^+$. $^1$H NMR (400 MHz, cd$_3$od) δ 8.58 (s, 2H), 8.26-8.08 (m, 2H), 7.96-7.75 (m, 4H), 7.65-7.54 (m, 5H), 5.36-5.11 (m, 4H), 4.34-4.04 (m, 4H), 3.97-3.79 (m, 4H), 3.65 (s, 4H), 3.53-3.44 (m, 2H), 2.68-2.47 (m, 4H), 2.32-2.02 (m, 7H), 1.95-1.82 (m, 3H), 1.77-1.54 (m, 4H), 1.49-1.24 (m, 5H), 1.10-0.99 (m, 3H), 0.92-0.85 (m, 4H).

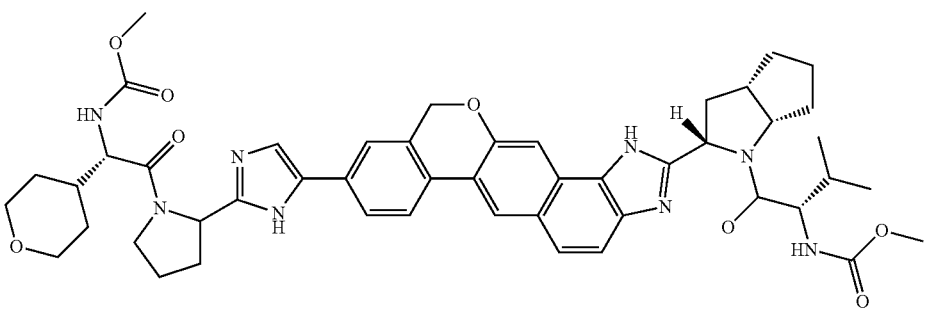 [SMILES: COC(=O)N[C@@H](C(C)C)C(O)N1[C@H](c2nc3ccc4cc5c(cc4c3[nH]2)OCc2cc(-c3cnc(C4CCCN4C(=O)[C@@H](NC(=O)OC)C4CCOCC4)[nH]3)ccc2-5)C[C@@H]2CCC[C@@H]21]

Example PQ

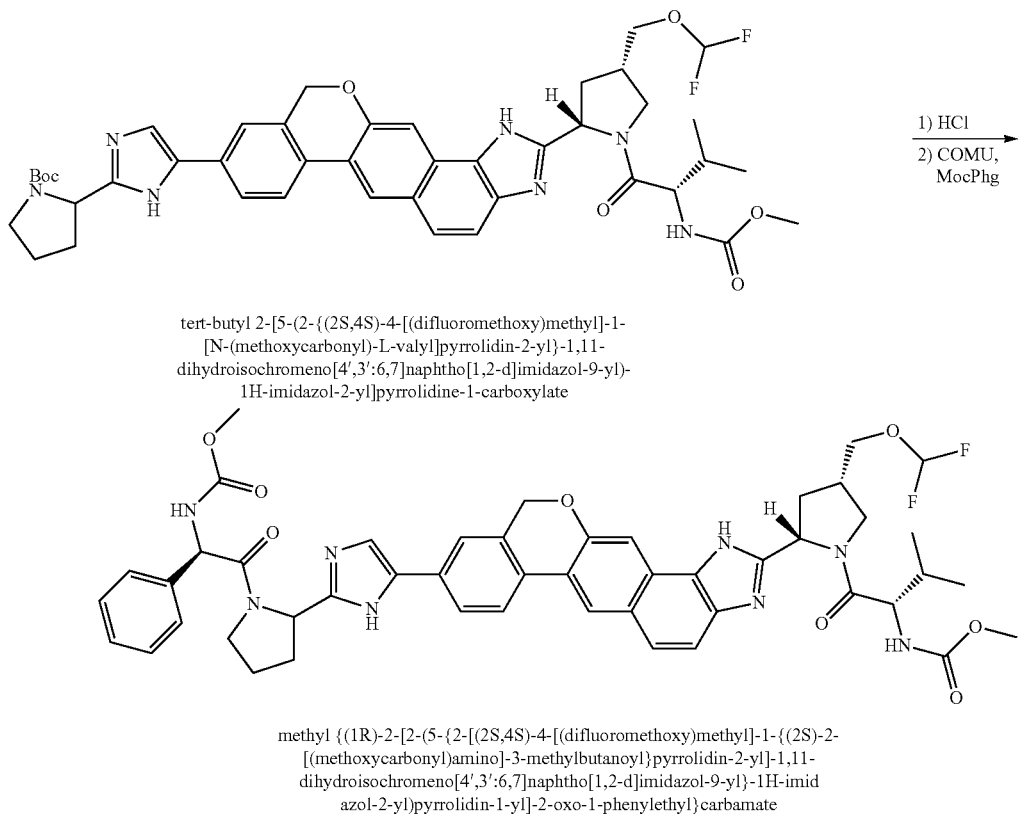

tert-butyl 2-[5-(2-{(2S,4S)-4-[(difluoromethoxy)methyl]-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate methyl {(1R)-2-[2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate tert-butyl 2-[5-(2-{(2S,4S)-4-[(difluoromethoxy)methyl]-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate: This compound was made in an analogous manner to tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate substituting (2S,4S)-1-(tert-butoxycarbonyl)-4-((difluoromethoxy)methyl)pyrrolidine-2-carboxylic acid for the initial alkylation of 9-bromo-3-chloro-10,11-dihydro-6H-naphtho[2,3-c]chromen-8(9H)-one. Reactions in the synthesis of tert-butyl 2-[5-(2-{(2S,4S)-4-[(difluoromethoxy)methyl]-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate gave similar product yields as in the synthesis of tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate. MS (ESI) m/z 815.04 [M+H]$^+$. $^1$H NMR (400 MHz, cd$_3$od) δ 8.58 (s, 1H), 8.18 (d, 1H), 7.96-7.85 (m, 3H), 7.70 (s, 1H), 7.60 (d, 1H), 7.50-7.38 (m, 4H), 7.10 (s, 1H), 6.46 (t, 1H), 5.51 (s, 1H), 5.39-5.36 (m, 1H), 5.31-5.28 (m, 21-), 4.43-4.36 (m, 1H), 4.24 (d, 1H), 4.13-4.02 (m, 3H), 3.75-3.62 (m, 7H), 3.51-3.47 (m, 1H), 3.18-3.11 (m, 2H), 2.93-2.83 (m, 2H), 2.75-2.69 (m, 1H), 2.47-2.36 (m, 2H), 2.23-2.09 (m, 3H), 2.01-1.94 (m, 2H), 0.87 (dd, 6H).

Example PR

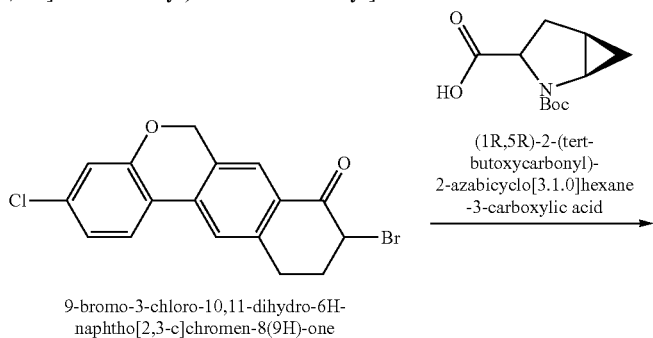

9-bromo-3-chloro-10,11-dihydro-6H-naphtho[2,3-c]chromen-8(9H)-one (1R,5R)-2-(tert-butoxycarbonyl)-2-azabicyclo[3.1.0]hexane-3-carboxylic acid -continued

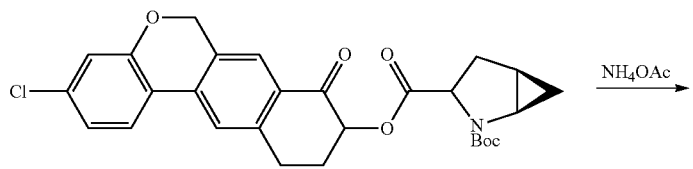

(1R,5R)-2-tert-butyl 3-(3-chloro-8-oxo-8,9,10,11-tetrahydro-6H-naphtho[2,3-c]chromen-9-yl) 2-azabicyclo[3.1.0]hexane-2,3-dicarboxylate

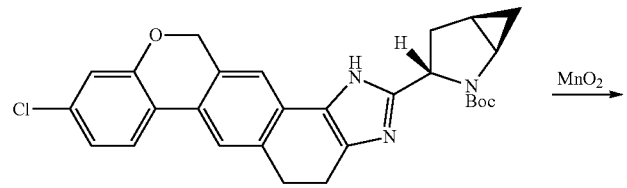

tert-butyl (1R,3S,5R)-3-(9-chloro-1,4,5,11-tetrahydroisochromeno[4',3':6,7]naphtho[1,2-d]imidazol-2-yl)-2-azabicyclo[3.1.0]hexane-2-carboxylate

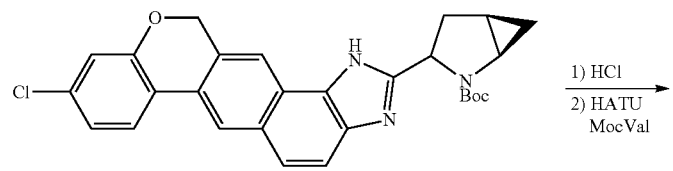

tert-butyl (1R,5R)-3-(9-chloro-1,12-dihydrochromeno[4',3':6,7]naphtho[1,2-d]imidazol-2-yl)-2-azabicyclo[3.1.0]hexane-2-carboxylate

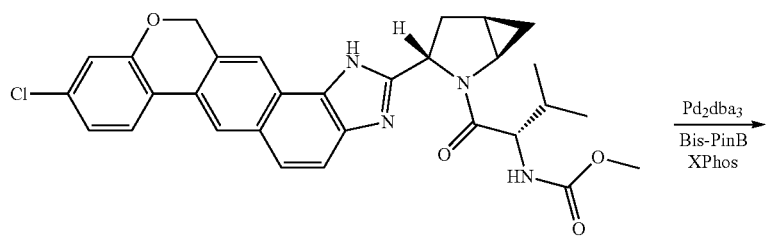

methyl {(2S)-1-(1R,3R,5R)-3-(9-chloro-1,11-dihydroisochromeno[4',3':6,7]naphtho[1,2-d]imidazol-2-yl)-2-azabicyclo[3.1.0]hex-2-yl]-3-methyl-1-oxobutan-2-yl}carbamate

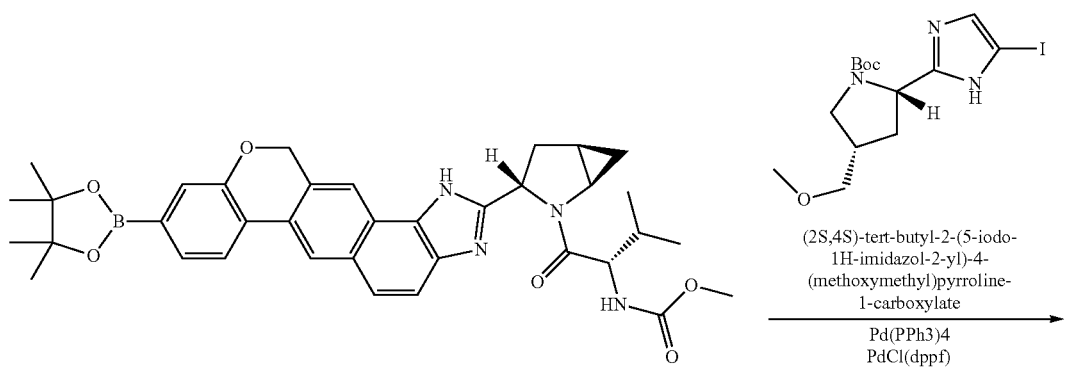

methyl [(2S)-3-methyl-1-oxo-1-{(1R,3S,5R)-3-[9-(4,4,5,5-tetramethyl-1,3,2-dioxaborolan-2-yl)-1,11-dihydroisochromeno[4',3':6,7]naphtho[1,2-d]imidazol-2-yl]-2-azabicyclo[3.1.0]hex-2-yl}butan-2-yl]carbamate (2S,4S)-tert-butyl-2-(5-iodo-1H-imidazol-2-yl)-4-(methoxymethyl)pyrroline-1-carboxylate

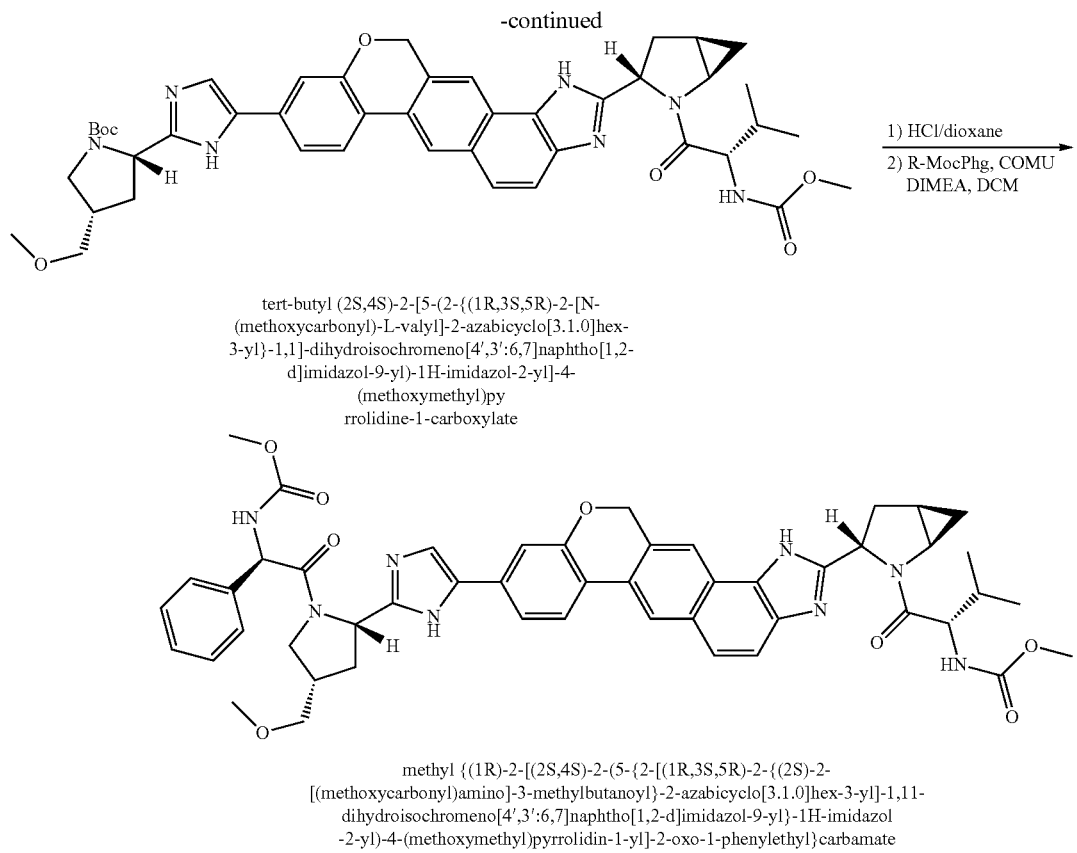

tert-butyl (2S,4S)-2-[5-(2-{(1R,3S,5R)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate methyl {(1R)-2-[(2S,4S)-2-(5-{2-[(1R,3S,5R)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate tert-butyl (2S,4S)-2-[5-(2-{(1R,3S,5R)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate: This compound was made in an analogous manner to tert-butyl (2R)-2-[5-(2-{(2S)-1-[N-(methoxycarbonyl)-L-valyl]pyrrolidin-2-yl}-3,11-dihydroisochromeno[4',3':6,7]naphtho[1,2-d]imidazol-9-yl)-1H-imidazol-2-yl]pyrrolidine-1-carboxylate substituting (1R,5R)-2-(tert-butoxycarbonyl)-2-azabicyclo[3.1.0]hexane-3-carboxylic acid for the initial alkylation of 9-bromo-3-chloro-10,11-dihydro-6H-naphtho[2,3-c]chromen-8(9H)-one, and substituting (2S,4S)-tert-butyl 2-(5-iodo-1H-imidazol-2-yl)-4-(methoxymethyl)pyrrolidine-1-carboxylate for the Suzuki-Miyara couping. Reactions in the synthesis of tert-butyl (2S,4S)-2-[5-(2-{(1R,3S,5R)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate gave similar product yields as in the synthesis of tert-butyl (2R)-2-[5-(2-{(2S)-1-[N-(methoxycarbonyl)-L-valyl]pyrrolidin-2-yl}-3,11-dihydroisochromeno[4',3':6,7]naphtho[1,2-d]imidazol-9-yl)-1H-imidazol-2-yl]pyrrolidine-1-carboxylate. MS (ESI) m/z 791.0 [M+H]$^+$.

methyl {(1R)-2-[(2S,4S)-2-(5-{2-[(1R,3S,5R)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate: To a solution of tert-butyl (2S,4S)-2-[5-(2-{(1R,3 S,5R)-2-[N-(methoxycarbonyl)-L-valyl]-2-azabicyclo[3.1.0]hex-3-yl}-1,11-dihydroisochromeno[4',3': 6,7]naphtho[1,2-d]imidazol-9-yl)-1H-imidazol-2-yl]-4-(methoxymethyl)pyrrolidine-1-carboxylate (0.060 g, 0.076 mmol) in a mixture of $CH_2Cl_2$ (0.76 mL) and MeOH (0.15 mL) was added HCl (4M in 1,4-dioxane, 0.570 mL, 2.28 mmol). The solution was stirred at room temperature for 2 h and concentrated to dryness.

The intermediate was dissolved in $CH_2Cl_2$ (0.76 mL). (R)-2-(methoxycarbonylamino)-2-phenylacetic acid (0.024 g, 0.114 mmol) and DIPEA (0.040 mL, 0.228 mmol) were then added to the solution. The reaction mixture was cooled to −40° C. (external temperature, MeCN/$CO_2$(s) bath). COMU (0.052 g, 0.122 mmol) was then added and solution was allowed to warm to 0° C. over 1.5 h. Upon completion by LCMS, the solution was diluted with DMF and concentrated. The crude product was purified by preparative HPLC (Gemini column, 10-45% MeCN/$H_2O$ with 0.1% TFA) and lyophilized to provide methyl {(1R)-2-[(2S,4S)-2-(5-{2-[(1R,3S,5R)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate (0.028 g, 42%). MS (ESI) m/z 881.8 [M+H]$^+$. $^1$H NMR (400 MHz, cd$_3$od) δ 8.45-8.33 (m, 1H), 8.02-7.94 (m, 1H), 7.91-7.75 (m, 2H), 7.72-7.67 (m, 1H), 7.61 (s, 1H), 7.59-7.34 (m, 6H), 7.09-6.91 (m, 2H), 5.62-5.38 (m, 2H), 5.29 (t, 1H), 5.24-5.09 (m, 3H), 4.61 (d, 1H), 4.37-4.26 (m, 1H), 3.83-3.73 (m, 1H), 3.69-3.56 (m, 6H), 3.50-3.40 (m, 1H), 3.20-3.11 (m, 1H), 2.99 (s, 1H), 2.83 (d, 1H), 2.63-2.50 (m, 2H), 2.47-2.34 (m, 2H), 2.29-2.13 (m, 2H), 2.10-1.95 (m, 2H), 1.37-1.23 (m, 3H), 1.19-1.10 (m, 1H), 1.03-0.78 (m, 7H).

Example PS

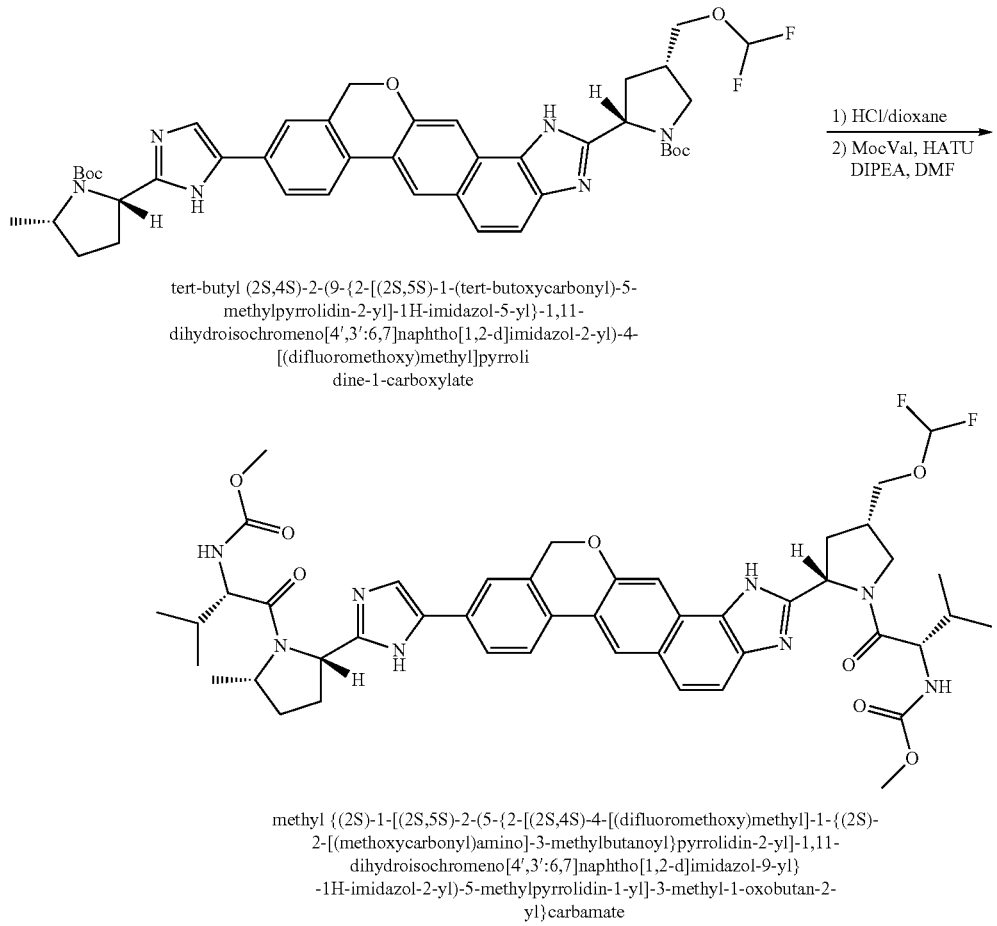

tert-butyl (2S,4S)-2-(9-{2-[(2S,5S)-1-(tert-butoxycarbonyl)-5-methylpyrrolidin-2-yl]-1H-imidazol-5-yl}-1,11-dihydroisochromeno[4',3':6,7]naphtho[1,2-d]imidazol-2-yl)-4-[(difluoromethoxy)methyl]pyrrolidine-1-carboxylate methyl {(2S)-1-[(2S,5S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate tert-butyl (2S,4S)-2-(9-{2-[(2S,5S)-1-(tert-butoxycarbonyl)-5-methylpyrrolidin-2-yl]-1H-imidazol-5-yl}-1,11-dihydroisochromeno[4',3':6,7]naphtho[1,2-d]imidazol-2-yl)-4-[(difluoromethoxy)methyl]pyrrolidine-1-carboxylate: This compound was made in an analogous manner to tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate substituting (2S,5S)-1-(tert-butoxycarbonyl)-5-methylpyrrolidine-2-carboxylic acid for the initial alkylation of 3-(2-bromoacetyl)-10,11-dihydro-5H-dibenzo[c,g]chromen-8(9H)-one, and substituting (2S,4S)-1-(tert-butoxycarbonyl)-4-((difluoromethoxy)methyl)pyrrolidine-2-carboxylic acid for the other alkylation in the sequence. Reactions in the synthesis of tert-butyl (2S,4S)-2-(9-{2-[(2S,5S)-1-(tert-butoxycarbonyl)-5-methylpyrrolidin-2-yl]-1H-imidazol-5-yl}-1,11-dihydroisochromeno[4',3':6,7]naphtho[1,2-d]imidazol-2-yl)-4-[(difluoromethoxy)methyl]pyrrolidine-1-carboxylate gave similar product yields as in the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 772.03 [M+H]$^+$.

methyl {(2S)-1-[(2S,5S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate To a solution of tert-butyl (2S,4S)-2-(9-{2-[(2S,5S)-1-(tert-butoxycarbonyl)-5-methylpyrrolidin-2-yl]-1H-imidazol-5-yl}-1,11-dihydroisochromeno[4',3':6,7]naphtho[1,2-d]imidazol-2-yl)-4-[(difluoromethoxy)methyl]pyrrolidine-1-carboxylate (0.081 g, 0.105 mmol) in a mixture of $CH_2Cl_2$ (1.05 mL) and MeOH (0.210 mL) was added HCl (4M in 1,4-dioxane, 0.788 mL, 3.15 mmol). The solution was stirred at room temperature for 2 h and concentrated to dryness. The intermediate was dissolved in $CH_2Cl_2$ (1.05 mL). (S)-2-(methoxycarbonylamino)-3-methylbutanoic acid (0.040 g, 0.231 mmol) and DIPEA (0.055 mL, 0.315 mmol) were then added to the solution. HATU (0.176 g, 0.462 mmol) was added and solution was allowed to stir at room temp. Upon completion, the solution was diluted with DMF and concentrated. The crude product was purified by preparative HPLC (Gemini column, 10-45% MeCN/$H_2O$ with 0.1% TFA) and the desired fractions were combined. The solution was concentrated until the aqueous layer remained and aqueous bicarbonate (sat.) was slowly added until the solution was basic. The resulting slurry was stirred at room temperature for 2 h and filtered. The resulting solid was dried in vacuo to provide methyl {(2S)-1-[(2S,5S)-2-(5-{2-[(2S,4S)-4-[(difluoromethoxy)methyl]-1-{(2

S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (0.025 g, 27%). MS (ESI) m/z 886.1 [M+H]$^+$. $^1$H NMR (400 MHz, cd$_3$od) δ 8.49-8.25 (m, 2H), 8.08-7.82 (m, 2H), 7.79-7.27 (m, 5H), 6.45 (t, 1H), 5.36-5.26 (m, 1H), 5.22-5.07 (m, 3H), 4.78-4.49 (m, 2H), 4.45-4.19 (m, 3H), 4.16-4.05 (m, 2H), 3.99-3.92 (m, 1H), 3.85-3.71 (m, 2H), 3.66 (s, 3H), 2.88-2.70 (m, 2H), 2.69-2.49 (m, 2H), 2.42-2.26 (m, 2H), 2.23-2.10 (m, 2H), 2.07-1.87 (m, 3H), 1.51 (d, 2H), 1.34-1.20 (m, 2H), 1.17-0.76 (m, 12H).

Example PT

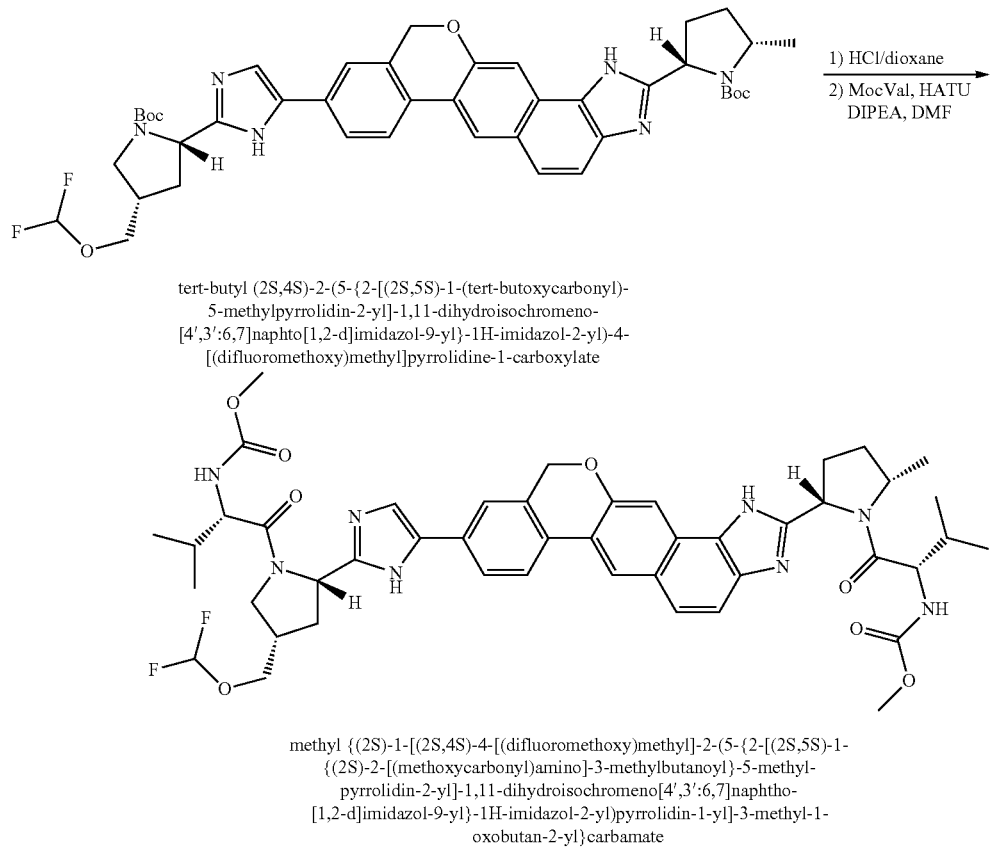

tert-butyl (2S,4S)-2-(5-{2-[(2S,5S)-1-(tert-butoxycarbonyl)-5-methylpyrrolidin-2-yl]-1,11-dihydroisochromeno-[4',3':6,7]naphto[1,2-d]imidazol-9-yl}-1H-imidazol-2-yl)-4-[(difluoromethoxy)methyl]pyrrolidine-1-carboxylate methyl {(2S)-1-[(2S,4S)-4-[(difluoromethoxy)methyl]-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho-[1,2-d]imidazol-9-yl}-1H-imidazol-2-yl)pyrrolidin-1-yl]-3-methyl-1-oxobutan-2-yl}carbamate tert-Butyl (2S,4S)-2-(5-{2-[(2S,5S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-4-[(difluoromethoxy)methyl]pyrrolidine-1-carboxylate: This compound was made in an analogous manner to tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate substituting (2S,4S)-1-(tert-butoxycarbonyl)-4-((difluoromethoxy)methyl)pyrrolidine-2-carboxylic acid for the initial alkylation of 3-(2-bromoacetyl)-10,11-dihydro-5H-dibenzo[c,g]chromen-8(9H)-one, and substituting (2S,5S)-1-(tert-butoxycarbonyl)-5-methylpyrrolidine-2-carboxylic acid for the other alkylation in the sequence. Reactions in the synthesis of tert-butyl (2S,4S)-2-(5-{2-[(2S,5S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-4-[(difluoromethoxy)methyl]pyrrolidine-1-carboxylate gave similar product yields as in the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 772.31 [M+H]$^+$.

methyl {(2S)-1-[(2S,4S)-4-[(difluoromethoxy)methyl]-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate: To tert-butyl (2S,4S)-2-(5-{2-[(2S,5S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-4-[(difluoromethoxy)methyl]pyrrolidine-1-carboxylate (0.057 g, 0.074 mmol) in a mixture of CH$_2$Cl$_2$ (0.739 mL) and MeOH (0.148 mL) was added HCl (4M in 1,4-dioxane, 0.555 mL, 2.218 mmol). The solution was stirred at room temperature for 2 h and concentrated to dryness.

The intermediate was dissolved in CH$_2$Cl$_2$ (0.739 mL). (S)-2-(methoxycarbonylamino)-3-methylbutanoic acid (0.028 g, 0.163 mmol) and DIPEA (0.039 mL, 0.222 mmol) were then added to the solution. HATU (0.124 g, 0.325 mmol) was added and solution was allowed to stir at room temp. Upon completion, the solution was diluted with DMF and concentrated. The crude product was purified by preparative HPLC (Gemini column, 10-46% MeCN/H$_2$O with 0.1% TFA) and the desired fractions were combined and lyophilized to provide methyl {(2S)-1-[(2S,4S)-4-[(difluoromethoxy)methyl]-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate (0.011 g, 17%). MS (ESI) m/z 886.1 [M+H]+. 1H NMR (400 MHz, cd3od) δ 8.67-8.51 (m, 1H), 8.26-8.11 (m, 1H), 8.04-7.75 (m, 3H), 7.69-7.58 (m, 2H), 6.43 (t, 1H), 5.41-5.15 (m, 4H), 4.48-3.90 (m, 6H), 3.82 (s, 1H), 3.71-3.57 (m, 5H), 3.53-3.43 (m, 1H), 3.20-3.01 (m, 2H), 2.92-2.63 (m, 3H), 2.60-2.25 (m, 4H), 2.15-1.86 (m, 4H), 1.57 (d, 3H), 1.24 (d, 2H), 1.07 (dd, 2H), 0.98-0.77 (m, 9H).

Example PU carboxylate substituting (2S,4S)-1-(tert-butoxycarbonyl)-4-(methoxymethyl)pyrrolidine-2-carboxylic acid for the initial alkylation of 3-(2-bromoacetyl)-10,11-dihydro-5H-dibenzo[c,g]chromen-8(9H)-one, and substituting (2S,4S)-1-(tert-butoxycarbonyl)-4-((difluoromethoxy)methyl)pyrrolidine-2-carboxylic acid for the other alkylation in the sequence. Reactions in the synthesis of tert-butyl (2S,4S)-2-[5-(2-{(2S,4S)-1-(tert-butoxycarbonyl)-4-[(difluoromethoxy)methyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate gave similar product yields as in the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 801.1 [M+H]+.

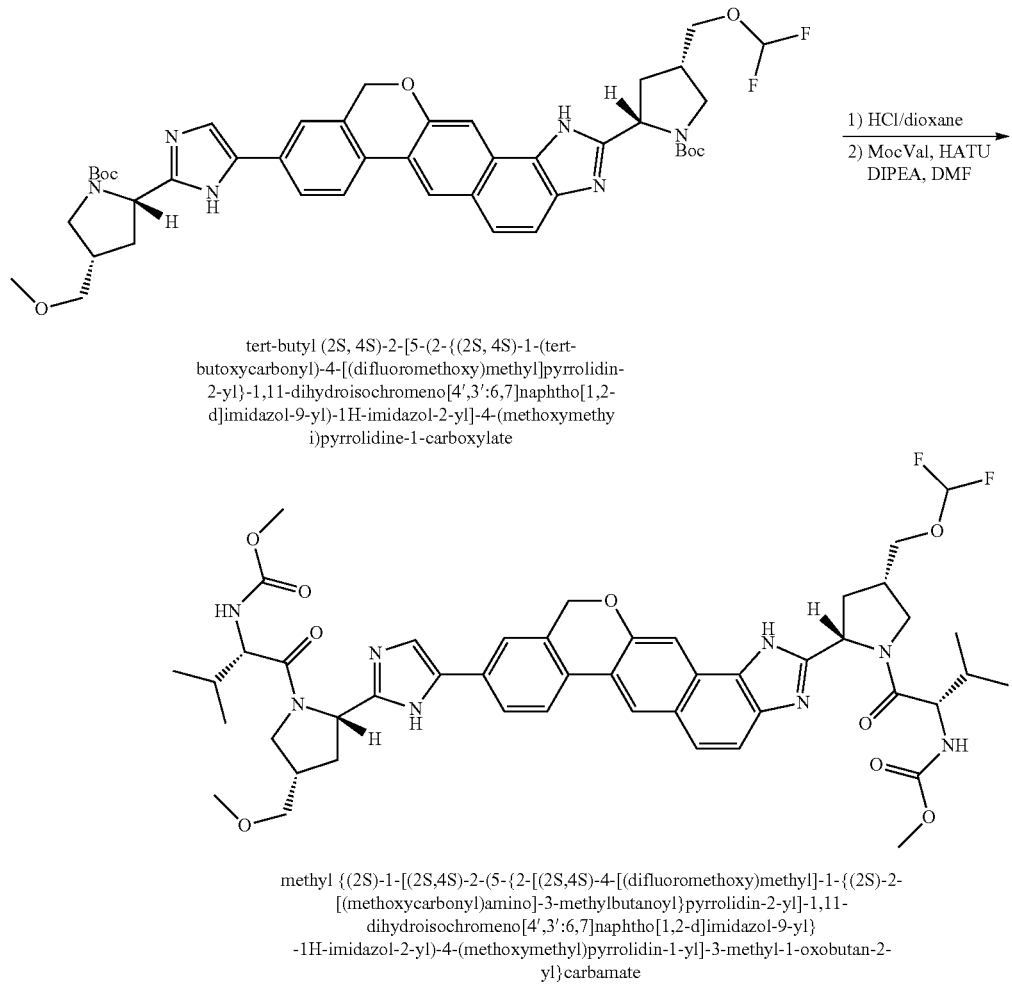

tert-butyl (2S, 4S)-2-[5-(2-{(2S, 4S)-1-(tert-butoxycarbonyl)-4-[(difluoromethoxy)methyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate methyl {(2S)-1-[(2S,4S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate tert-butyl (2S,4S)-2-[5-(2-{(2S,4S)-1-(tert-butoxycarbonyl)-4-[(difluoromethoxy)methyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate: This compound was made in an analogous manner to tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1- methyl {(2S)-1-[(2S,4S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl)-1H-imidazol-2-yl]-4-(methoxymethyl)pyrrolidin-1-yl]-3-methyl-1-oxobutan-2-yl}carbamate: To tert-butyl (2S,4S)-2-[5-(2-{(2S,4S)-1-(tert-butoxycarbonyl)-4-[(difluoromethoxy)methyl]pyrrolidin-2-yl}-1,11 dihydroisochromeno[4',3':6,7]naphtho[1,2-d]imidazol-9-yl)-1H-imidazol-2-yl]-4-

(methoxymethyl)pyrrolidine-1-carboxylate (0.092 g, 0.115 mmol) in a mixture of CH$_2$Cl$_2$ (1.15 mL) and MeOH (0.230 mL) was added HCl (4M in 1,4-dioxane, 0.862 mL, 3.446 mmol). The solution was stirred at room temperature for 2 h and concentrated to dryness.

The intermediate was dissolved in CH$_2$Cl$_2$ (1.149 mL). (S)-2-(methoxycarbonylamino)-3-methylbutanoic acid (0.044 g, 0.253 mmol) and DIPEA (0.060 mL, 0.345 mmol) were then added to the solution. HATU (0.192 g, 0.505 mmol) was added and solution was allowed to stir at room temp. Upon completion, the solution was diluted with DMF and concentrated. The crude product was purified by preparative HPLC (Gemini column, 10-45% MeCN/H$_2$O with 0.1% TFA) and the desired fractions were combined. The solution was concentrated until the aqueous layer remained and aqueous bicarbonate (sat.) was slowly added until the solution was basic. The resulting slurry was stirred at room temperature for 2 h and filtered. The resulting solid was dried in vacuo to provide methyl {(2S)-1-[(2S,4S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate (0.042 g, 40%). MS (ESI) m/z 916.30 [M+H]$^+$. $^1$H NMR (400 MHz, cd$_3$od) δ 8.55-8.25 (m, 1H), 8.15-7.85 (m, 2H), 7.83-7.26 (m, 5H), 6.44 (t, 1H), 5.37-5.02 (m, 4H), 4.47-4.35 (m, 1H), 4.33-4.18 (m, 3H), 4.15-3.90 (m, 3H), 3.81-3.45 (m, 11H), 3.39 (s, 3H), 2.90-2.27 (m, 5H), 2.22-1.92 (m, 4H), 1.12-0.73 (m, 13H).

Example PV

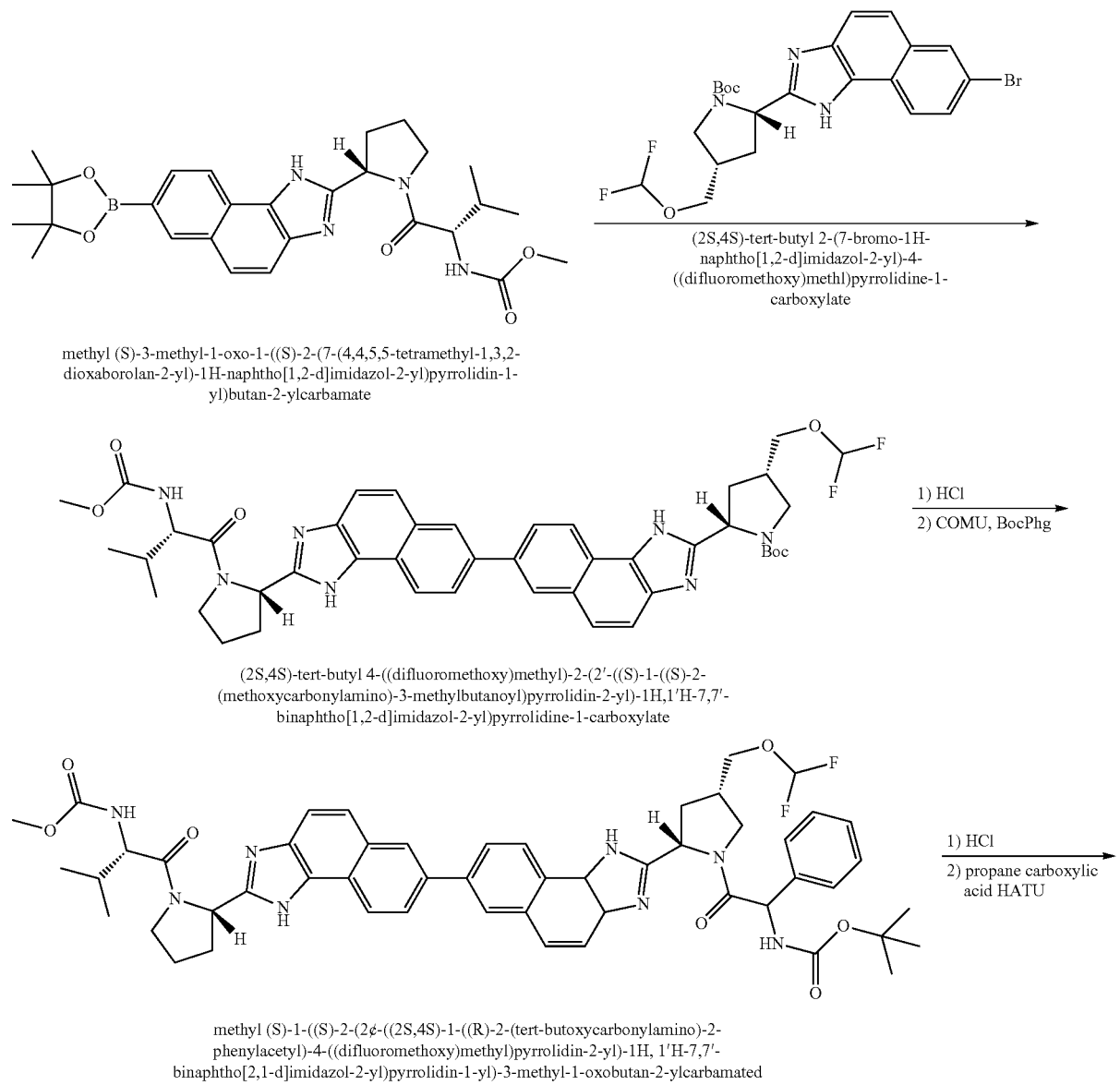

-continued

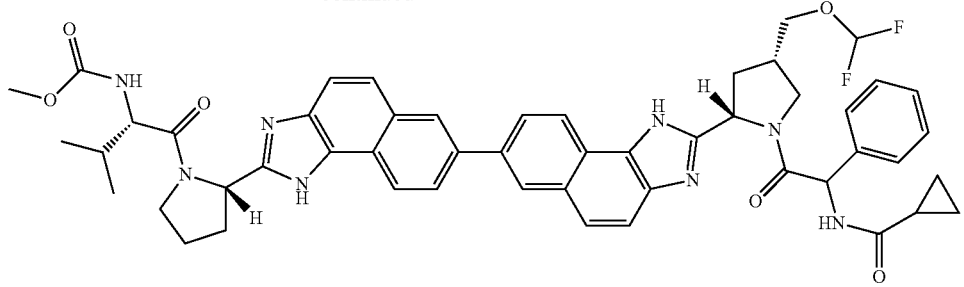

methyl (S)-1-((S)-2-(2'-((2S,4S)-1-((R)-2-(cyclopropanecarboxamido)-2-phenylacetyl)-4-((difluoromethoxy)methyl)pyrrolidin-2-yl)-1H,1'H-7,7'-binaphtho[2,1-d]imidazol-2-yl)pyrrolidin-1-yl)-3-methyl-1 oxobutan-2-ylcarbamate methyl (S)-1-((S)-2-(2'-((2S,4S)-1-((R)-2-(tert-butoxycarbonylamino)-2-phenylacetyl)-4-((difluoromethoxy)methyl)pyrrolidin-2-yl)-1H,1'H-7,7'-1-binaphtho[2,1-d]imidazol-2-yl)pyrrolidin-1-yl)-3-methyl-1-oxobutan-2-ylcarbamate: This compound was made using a similar procedure as was used to make methyl (R)-2-((2S,4S)-4-(methoxymethyl)-2-(2'-((1R,3 S,5R)-2-((S)-3-methyl-2-methoxycarbonylaminobutanoyl)-2-azabicyclo[3.1.0]hexan-3-yl)-1H, 1'H-7,7'-binaphtho[1,2-d]imidazol-2-yl)pyrrolidin-1-yl)-2-oxo-1-phenylethylcarbamate, using methyl (S)-3-methyl-1-oxo-1-((S)-2-(7-(4,4,5,5-tetramethyl-1,3,2-dioxaborolan-2-yl)-1H-naphtho[1,2-d]imidazol-2-yl)pyrrolidin-1-yl)butan-2-ylcarbamate and (2R,4S)-tert-butyl 2-(7-bromo-1H-naphtho[1,2-d]imidazol-2-yl)-4-((difluoromethoxy)methyl)pyrrolidine-1-carboxylate in the Suzuki-Miyaura cross coupling to give methyl (S)-1-((S)-2-(2'-((2S,4S)-1-((R)-2-(tert-butoxycarbonylamino)-2-phenylacetyl)-4-((difluoromethoxy)methyl)pyrrolidin-2-yl)-1H,1'H-7,7'-binaphtho[2,1-d]imidazol-2-yl)pyrrolidin-1-yl)-3-methyl-1-oxobutan-2-ylcarbamate (0.203g, 56%). MS (ESI) m/z 944.10 [M+H]+.

methyl (S)-1-((S)-2-(2'-((2S,4S)-1-((R)-2-(cyclopropanecarboxamido)-2-phenylacetyl)-4-((difluoromethoxy)methyl)pyrrolidin-2-yl)-1H,1'H-7,7'-binaphtho[2,1-d]imidazol-2-yl)pyrrolidin-1-yl)-3-methyl-1 oxobutan-2-ylcarbamate: To a solution of methyl (S)-1-((S)-2-(2'-((2S,4S)-1-((R)-2-(tert-butoxycarbonylamino)-2-phenylacetyl)-4-((difluoromethoxy)methyl)pyrrolidin-2-yl)-1H,1'H-7,7'-binaphtho[2,1-d]imidazol-2-yl)pyrrolidin-1-yl)-3-methyl-1-oxobutan-2-ylcarbamate (0.203g, 0.215 mmol) in a mixture of DCM (2.15 mL) and MeOH (0.43 mL) was added HCl (2.15 mL, 4N in 1,4-dioxane, 8.6 mmol). The reaction was stirred at room temp for 30 minutes. Upon completion, the crude reaction mixture was concentrated in vacuuo.

The residue was dissolved in DMF (2.15 mL). DIPEA (0.15 mL, 0.861 mmol), propane carboxylic acid (0.020 mL, 0.258 mmol), and HATU (0.123g, 0.323 mmol). Upon completion, the reaction mixture was filtered through a syringe filter, the crude product was purified by preparative HPLC (Gemini column, 10-52% MeCN/H$_2$O with 0.1% TFA) and the desired fractions were combined. The solution was concentrated until the aqueous layer remained and aqueous bicarbonate (sat.) was slowly added until the solution was basic. The resulting slurry was stirred at room temperature for 2 h and filtered. The resulting solid was dried in vacuo to provide methyl (S)-1-((S)-2-(2'-((2S,4S)-1-((R)-2-(cyclopropanecarboxamido)-2-phenylacetyl)-4-((difluoromethoxy)methyl)pyrrolidin-2-yl)-1H,1'H-7,7'-binaphtho[2,1-d]imidazol-2-yl)pyrrolidin-1-yl)-3-methyl-1 oxobutan-2-ylcarbamate (0.098 g, 50%). MS (ESI) m/z 911.7 [M+H]+. $^1$H NMR (400 MHz, cd$_3$od) δ 8.68-8.50 (m, 2H), 8.42-8.23 (m, 2H), 8.14-7.90 (m, 2H), 7.86-7.67 (m, 3H), 7.62-7.51 (m, J=6.2 Hz, 2H), 7.49-7.39 (m, J=15.3, 7.6 Hz, 2H), 6.86-6.01 (m, 5H), 5.83-5.67 (m, 1H), 5.59 (s, 1H), 5.49-5.33 (m, 2H), 4.64-4.18 (m, 3H), 4.13-3.92 (m, 2H), 3.87-3.76 (m, J=7.2 Hz, 2H), 3.68 (s, 2H), 2.89-2.22 (m, 7H), 2.19-2.00 (m, 3H), 1.77-1.48 (m, 2H), 1.11-0.85 (m, 7H), 0.80-0.68 (m, J=4.5 Hz, 2H).

Example PW

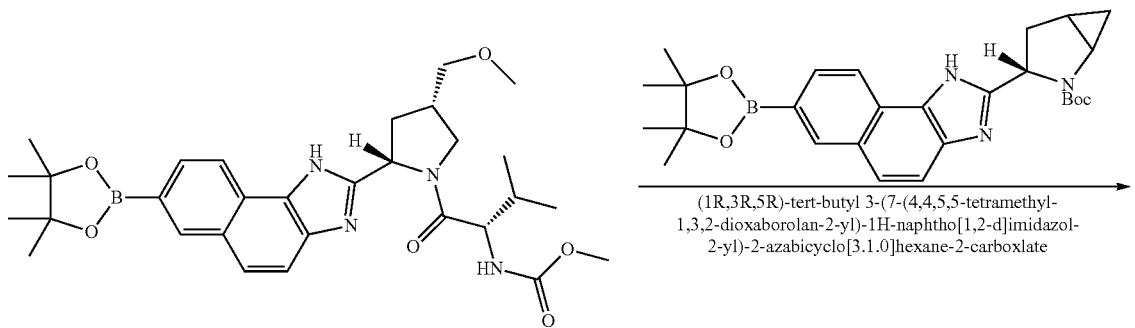

methyl (S)-1-((2S,4S)-4-(methoxymethyl)-2-(7-(4,4,5,5-tetramethyl-1,3,2-dioxaborolan-2-yl)-1H-naphtho[1,2-d]imidazol-2-yl)pyrrolidin-1-yl)-3-methyl-1-oxobutan-2-ylcarbamate (1R,3R,5R)-tert-butyl 3-(7-(4,4,5,5-tetramethyl-1,3,2-dioxaborolan-2-yl)-1H-naphtho[1,2-d]imidazol-2-yl)-2-azabicyclo[3.1.0]hexane-2-carboxylate

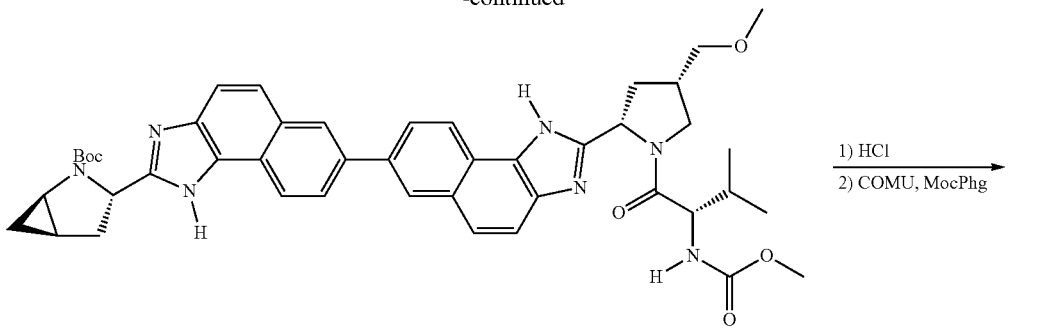

(1R,3S,5R)-tert-butyl 3-(2'-((2S,4S)-1-((S)-2-(methoxycarbonylamino)-3-methylbutanoyl)-4-(methoxymethyl)pyrrolidin-2-yl)-1H,1'H-7,7'-binaphtho[2,1-d]imidazol-2-yl)-2-azabicyclo[3.1.0]hexane-2-carboxylate

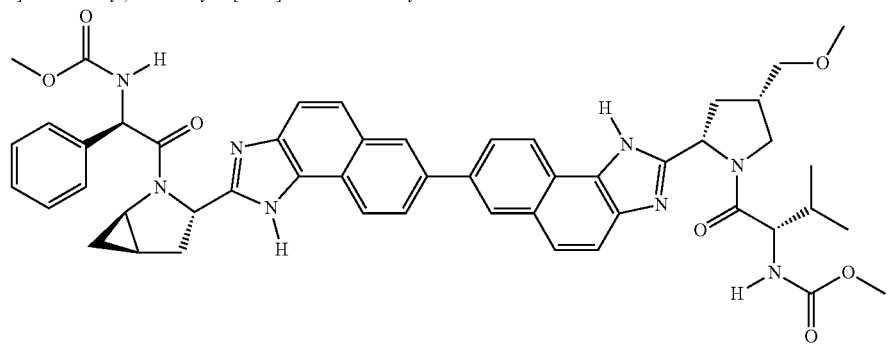

methyl (S)-1-((2S,4S)-2-(2'-((1R,3S,5R)-2-((R)-2-(methoxycarbonylamino)-2-phenylacetyl)-2-azabicyclo[3.1.0]hexan-3-yl)-1H, 1'H-7,7'-binaphtho[2,1-d]imidazol-2-yl)-4-(methoxymethyl)pyrroldin-1-yl)-3-methyl-1-oxobutan-2-ylcarbamate methyl (S)-1-((2S,4S)-2-(2'-((1R,3S,5R)-2-((R)-2-(methoxycarbonylamino)-2-phenylacetyl)-2-azabicyclo[3.1.0]hexan-3-yl)-1H,1'H-7,7'-binaphtho[2,1-d]imidazol-2-yl)-4-(methoxymethyl)pyrrolidin-1-yl)-3-methyl-1-oxobutan-2-ylcarbamate: This compound was made using the same procedure as was used to make methyl (R)-2-((2S,4S)-4-(methoxymethyl)-2-(2'-((1R,3 S, 5R)-2-((S)-3-methyl-2-methoxycarbonylaminobutanoyl)-2-azabicyclo[3.1.0]hexan-3-yl)-1H, 1'H-7,7'-binaphtho[1,2-d]imidazol-2-yl)pyrrolidin-1-yl)-2-oxo-1-phenylethylcarbamate, using methyl (S)-1-((2S,4S)-4-(methoxymethyl)-2-(7-(4,4,5,5-tetramethyl-1,3,2-dioxaborolan-2-yl)-1H-naphtho[1,2-d]imidazol-2-yl)pyrrolidin-1-yl)-3-methyl-1-oxobutan-2-ylcarbamate and (1R,3 S,5R)-tert-butyl 3-(7-(4,4,5,5-tetramethyl-1,3,2-dioxaborolan-2-yl)-1H-naphtho[1,2-d]imidazol-2-yl)-2-azabicyclo[3.1.0]hexane-2-carboxylate in the Suzuki-Miyaura cross coupling to give methyl (S)-1-((2S,4S)-2-(2'-((1R,3S,5R)-2-((R)-2-(methoxycarbonylamino)-2-phenylacetyl)-2-azabicyclo[3.1.0]hexan-3-yl)-1H, 1'H-7,7'-binaphtho[2,1-d]imidazol-2-yl)-4-(methoxymethyl)pyrrolidin-1-yl)-3-methyl-1-oxobutan-2-ylcarbamate (0.048g, 27%). MS (ESI) m/z 877.71 [M+H]$^+$. $^1$H NMR (400 MHz, cd$_3$od) δ 8.68-8.50 (m, 2H), 8.42-8.23 (m, 2H), 8.14-7.90 (m, 2H), 7.86-7.67 (m, 3H), 7.62-7.51 (m, J=6.2 Hz, 2H), 7.49-7.39 (m, J=15.3, 7.6 Hz, 2H), 6.86-6.01 (m, 5H), 5.83-5.67 (m, 1H), 5.59 (s, 1H), 5.49-5.33 (m, 2H), 4.64-4.18 (m, 3H), 4.13-3.92 (m, 2H), 3.87-3.76 (m, J=7.2 Hz, 2H), 3.68 (s, 2H), 2.89-2.22 (m, 7H), 2.19-2.00 (m, 3H), 1.77-1.48 (m, 2H), 1.11-0.85 (m, 7H), 0.80-0.68 (m, J=4.5 Hz, 2H).

Example PX

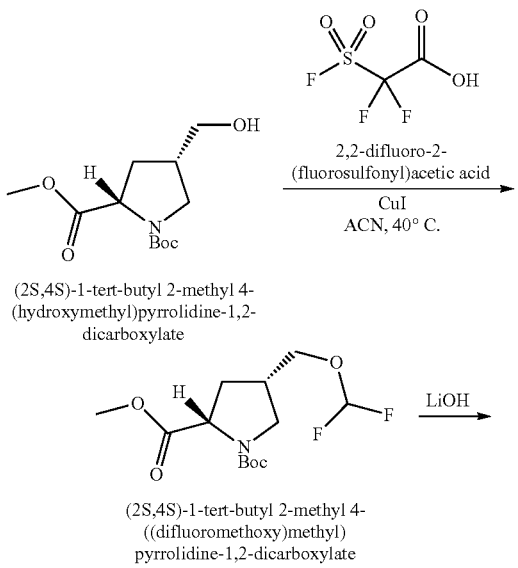

(2S,4S)-1-tert-butyl 2-methyl 4-(hydroxymethyl)pyrrolidine-1,2-dicarboxylate (2S,4S)-1-tert-butyl 2-methyl 4-((difluoromethoxy)methyl)pyrrolidine-1,2-dicarboxylate

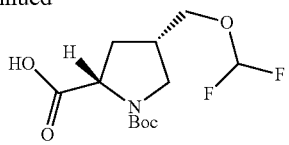

(2S,4S)-1-(tert-butoxycarbonyl)-4-
((difluoromethoxy)methyl)
pyrrolidine-2-carboxylic acid (2S,4S)-1-tert-butyl 2-methyl 4-((difluoromethoxy)methyl)pyrrolidine-1,2-dicarboxylate: A 100 mL round-bottom flask was charged with (2S,4S)-1-tert-butyl 2-methyl 4-(hydroxymethyl)pyrrolidine-1,2-dicarboxylate (3.33 g, 12.84 mmol), CuI (0.489 g, 2.56 mmol), and anhydrous acetonitrile (57.1 mL). The reaction was heated to 45° C. (ext. oil bath). 2,2-difluoro-2-(fluorosulfonyl)acetic acid (2.655 mL, 25.68 mmol) was added at 45° C. over 30 minutes via syringe pump. The reaction was heated for 30 minutes. Upon completion as monitored by TLC, the reaction mixture was cooled to room temperature and concentrated in vacuo. The crude residue was diluted in EtOAc and washed with sodium bicarbonate (aq). The bicarbonate layer was back extracted with ethyl acetate twice. Combined organic layers were washed with brine, dried over sodium sulphate, filtered and concentrated. The resulting residue was further purified via silica gel chromatography (10 to 40% EtOAc/Hexanes) to afford (2S,4S)-1-tert-butyl 2-methyl 4-((difluoromethoxy)methyl)pyrrolidine-1,2-dicarboxylate (2.41 g, 61%). MS (ESI) m/z 210.21 [M+H-Boc]⁺.

(2S,4S)-1-(tert-butoxycarbonyl)-4-((difluoromethoxy)methyl)pyrrolidine-2-carboxylic acid: To a solution of (2S,4S)-1-tert-butyl 2-methyl 4((difluoromethoxy)methyl) pyrrolidine-1,2-dicarboxylate (2.41 g, 7.79 mmol) in a mixture of THF (39 mL) and MeOH (15.6 mL) was added LiOH (2.5 M aqueous, 15.6 mL, 38.9 mmol). The resulting solution was stirred at room temperature for 1 h. Upon completion by TLC the reaction mixture was and acidified with aqueous HCl (1N). The desired product was extracted with $CH_2Cl_2$ (3x). The combined organic layers were dried over $Na_2SO_4$ and concentrated to provide (2S,4S)-1-(tert-butoxycarbonyl)-4-((difluoromethoxy)methyl)pyrrolidine-2-carboxylic acid (2.4 g, 99%). MS (ESI) m/z 294.96 [M−H]⁻. ¹H-NMR: 400 MHz, (acetone-$d_6$) δ (mixture of rotomers): 6.50 (t, 1H), 4.36-4.17 (m, 1H), 3.93 (d, 2H), 3.77-3.67 (m, 1H), 3.63-3.59 (m, 1H), 3.26-3.12 (m, 1H), 2.72-2.41 (m, 2H), 1.89-1.73 (m, 2H), 1.41 (s, 9H).

Example PY

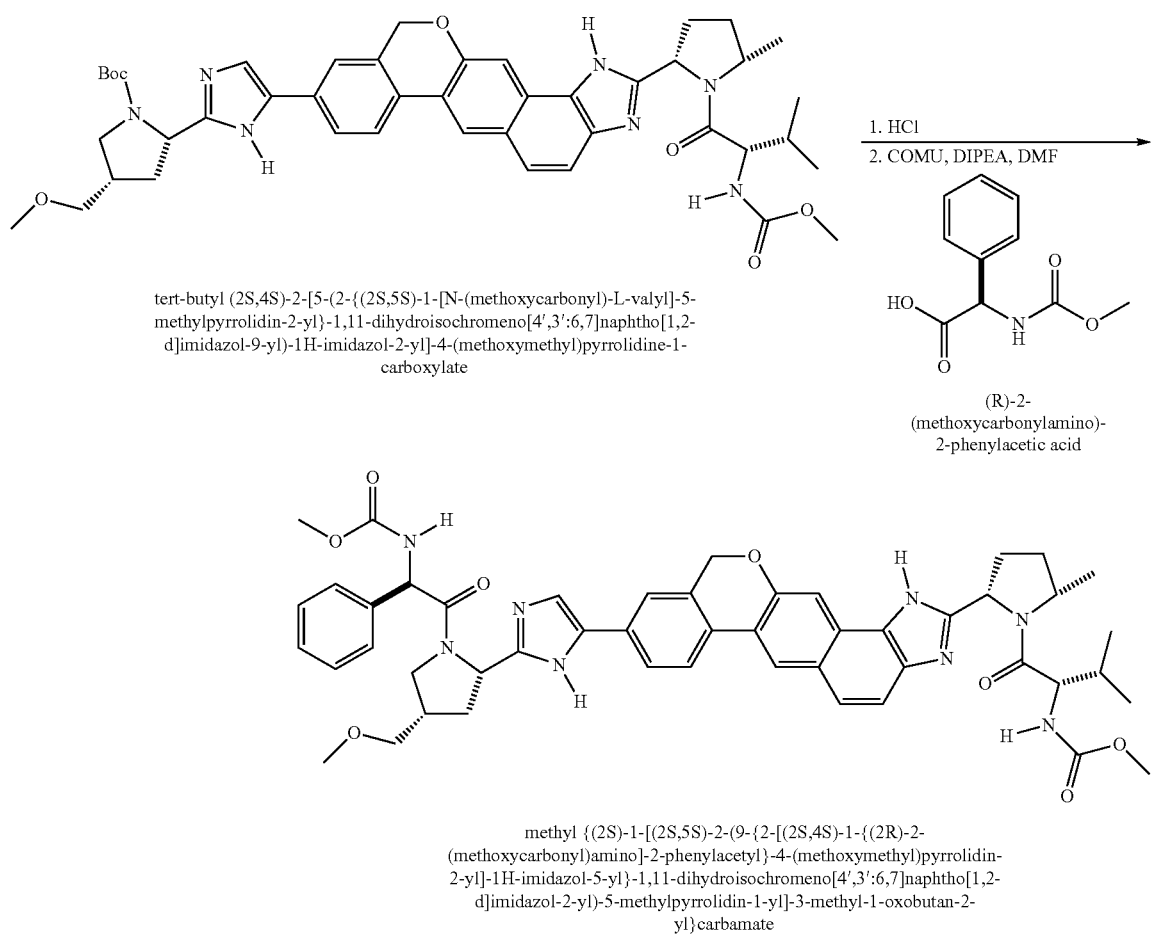

tert-butyl (2S,4S)-2-[5-(2-{(2S,5S)-1-[N-(methoxycarbonyl)-L-valyl]-5-methylpyrrolidin-2-yl}-1,11-dihydroisochromeno[4′,3′:6,7]naphtho[1,2-d]imidazol-9-yl)-1H-imidazol-2-yl]-4-(methoxymethyl)pyrrolidine-1-carboxylate (R)-2-(methoxycarbonylamino)-2-phenylacetic acid methyl {(2S)-1-[(2S,5S)-2-(9-{2-[(2S,4S)-1-{(2R)-2-(methoxycarbonyl)amino]-2-phenylacetyl}-4-(methoxymethyl)pyrrolidin-2-yl]-1H-imidazol-5-yl}-1,11-dihydroisochromeno[4′,3′:6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-

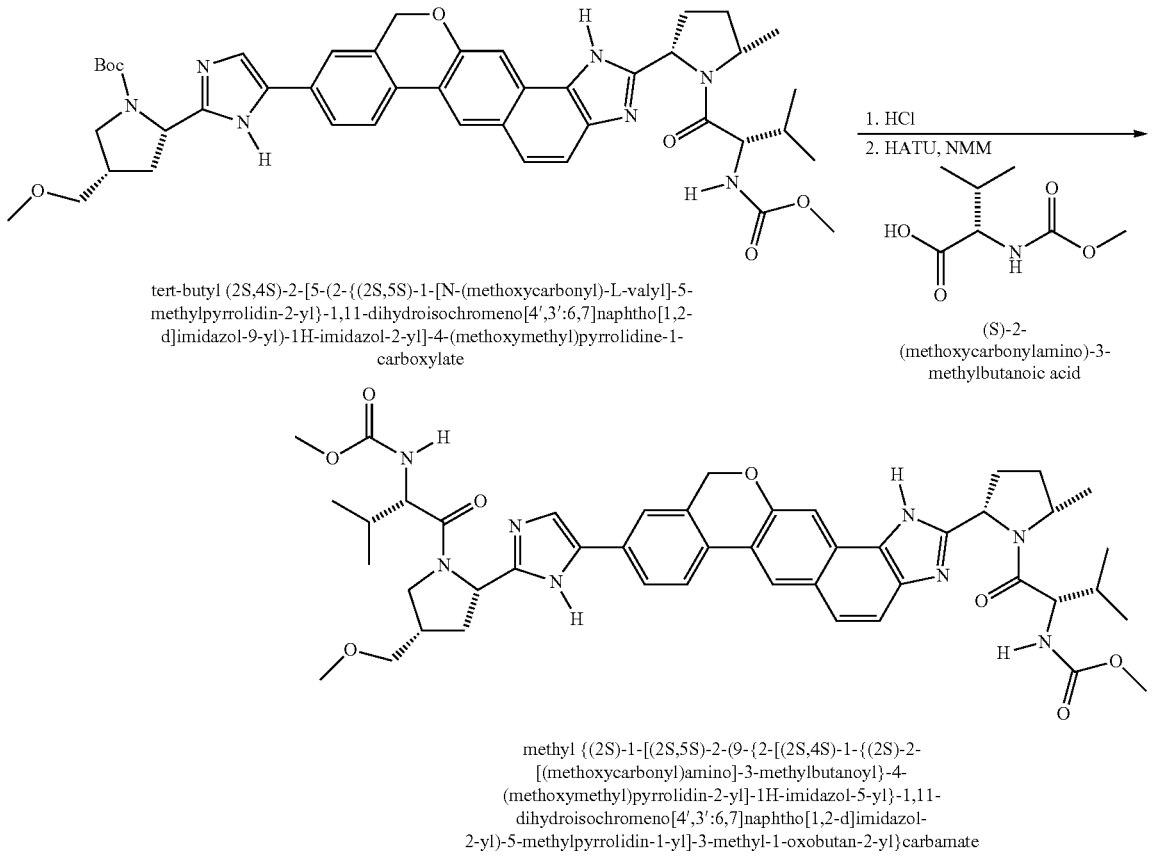

Example PZ yl}carbamate: A solution of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (150 mg, 0.19 mmol) in 1.25 N HCl in EtOH (3 mL) was stirred overnight then heated to 50° C. for 3 h. The reaction was concentrated and the crude material dissolved in DMF (2 mL). To this solution was added a solution of (R)-2-(methoxycarbonylamino)-2-phenylacetic acid (52 mg, 0.25 mmol) and COMU (90 mg, 0.21 mmol). To the resulting solution was added diisopropylethylamine (0.099 mL, 0.57 mmol). After stirring for 2 h at room temperature, the reaction was quenched with 1N HCl (0.200 mL) and purified by HPLC. After lyophilization, the TFA salt was dissolved in EtOAc and washed with saturated NaHCO$_3$. The organic phase was dried over Na$_2$SO$_4$ and concentrated. The free base was then dissolved in MeCN/H$_2$O and lyophilized to afford methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (65 mg, 39%). LCMS-ESI$^+$: calculated for C$_{49}$H$_{54}$N$_8$O$_8$: 882.4; observed [M+1]$^+$: 884.1. Diagnostic peaks in NMR$^1$H NMR (CD$_3$OD): 8.28 (s, 1H), 8.21 (s, 1H), 8.04 (s, 1H), 7.91-7.01 (m, 10H), 3.62 (s, 3H), 3.34 (s, 3H), 3.23 (s, 3H), 1.56 (d, 3H), 1.03 (d, 3H), 0.94 (d, 3H).

Methyl {(2S)-1-[(2S,5S)-2-(9-{2-[(2S,4S)-1-{(2S)-2-[(methoxycarbonyl)amino]-3-methylbutanoyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate: Tert-butyl (2S,4S)-2-[5-(2-({(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (100 mg, 0.13 mmol) in 1.25 N HCl in EtOH (3 mL) was heated to 50° C. for 3 h and then concentrated under reduced pressure. The crude residue was treated with (S)-2-(methoxycarbonylamino)-3-methylbutanoic acid (34 mg, 0.20 mmol), HATU (54 mg, 0.14 mmol) and DMF (1.3 mL), then N-methylmorpholine (0.043 mL, 0.39 mmol) was added dropwise. After 3 h, the mixture was quenched with 1N HCl (0.100 mL) and then purified by HPLC to afford methyl {(2S)-1-[(2S,5S)-2-(9-{2-[(2S,4S)-1-{(2S)-2-[(methoxycarbonyl)amino]-3-methylbutanoyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (91 mg, 82%).

LCMS-ESI$^+$: calculated for C$_{46}$H$_{56}$N$_8$O$_8$: 848.4; observed [M+1]$^+$: 850.2.

Example QA

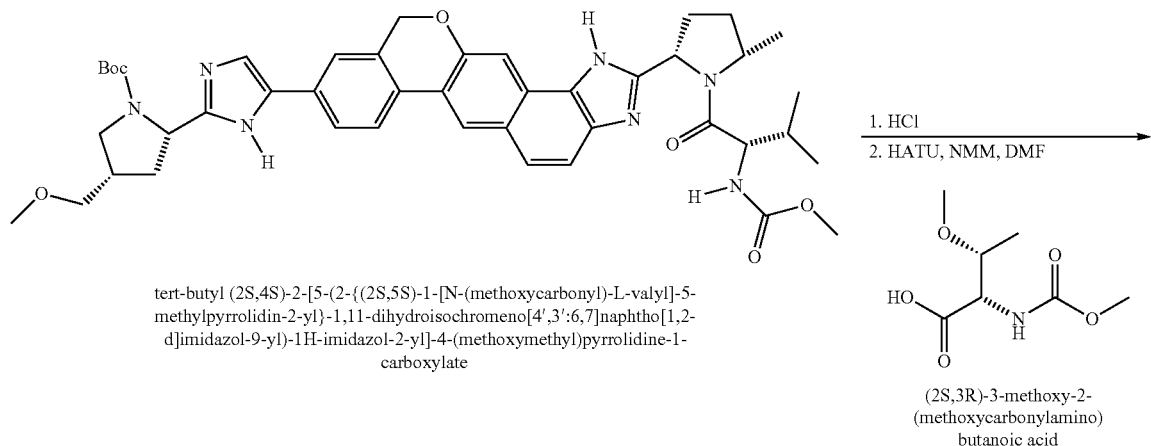

tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (2S,3R)-3-methoxy-2-(methoxycarbonylamino)butanoic acid

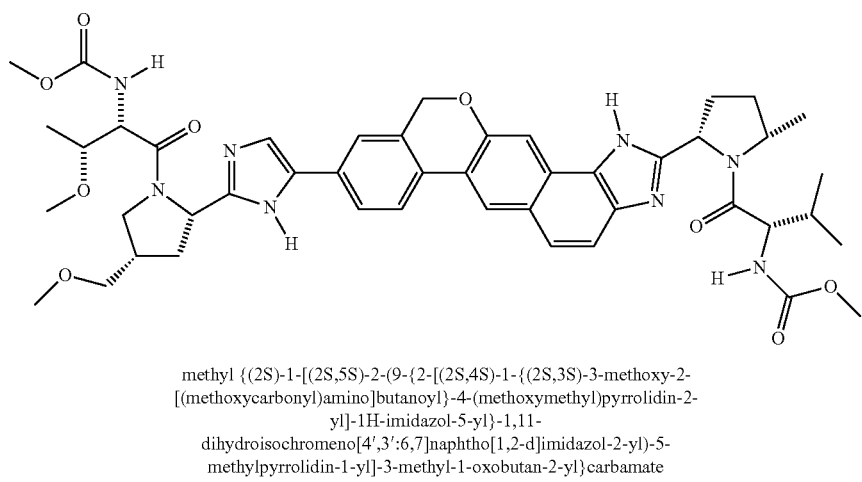

methyl {(2S)-1-[(2S,5S)-2-(9-{2-[(2S,4S)-1-{(2S,3S)-3-methoxy-2-[(methoxycarbonyl)amino]butanoyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,4S)-1-{(2S,3S)-3-methoxy-2-[(methoxycarbonyl)amino]butanoyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate: Tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (119 mg, 0.15 mmol) in 1.25 N HCl in EtOH (3 mL) was heated to 50° C. for 3 h and then concentrated under reduced pressure. The crude residue was treated with (2S,3R)-3-methoxy-2-(methoxycarbonylamino)butanoic acid (43 mg, 0.23 mmol), HATU (63 mg, 0.17 mmol) and DMF (2 mL), then N-methylmorpholine (0.050 mL, 0.45 mmol) was added dropwise. After 3 hr, the mixture was quenched with 1N HCl (0.100 mL) and then purified by HPLC to afford methyl {(2S)-1-[(2S,5S)-2-(9-{2-[(2S,4S)-1-{(2S,3S)-3-methoxy-2-[(methoxycarbonyl)amino]butanoyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (76 mg, 59%).

LCMS-ESI$^+$: calculated for $C_{46}H_{56}N_8O_9$: 864.4; observed [M+1]$^+$: 866.1.

Example QB
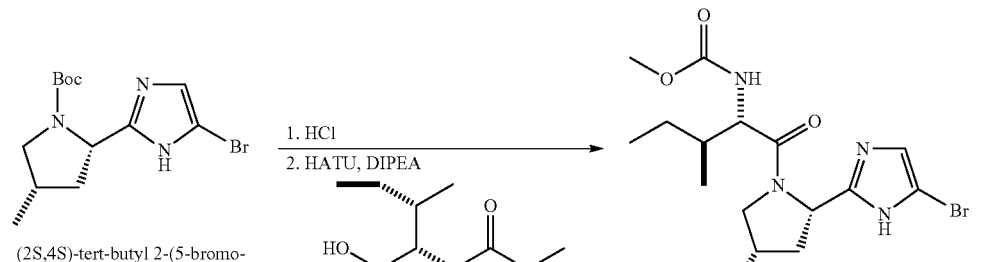
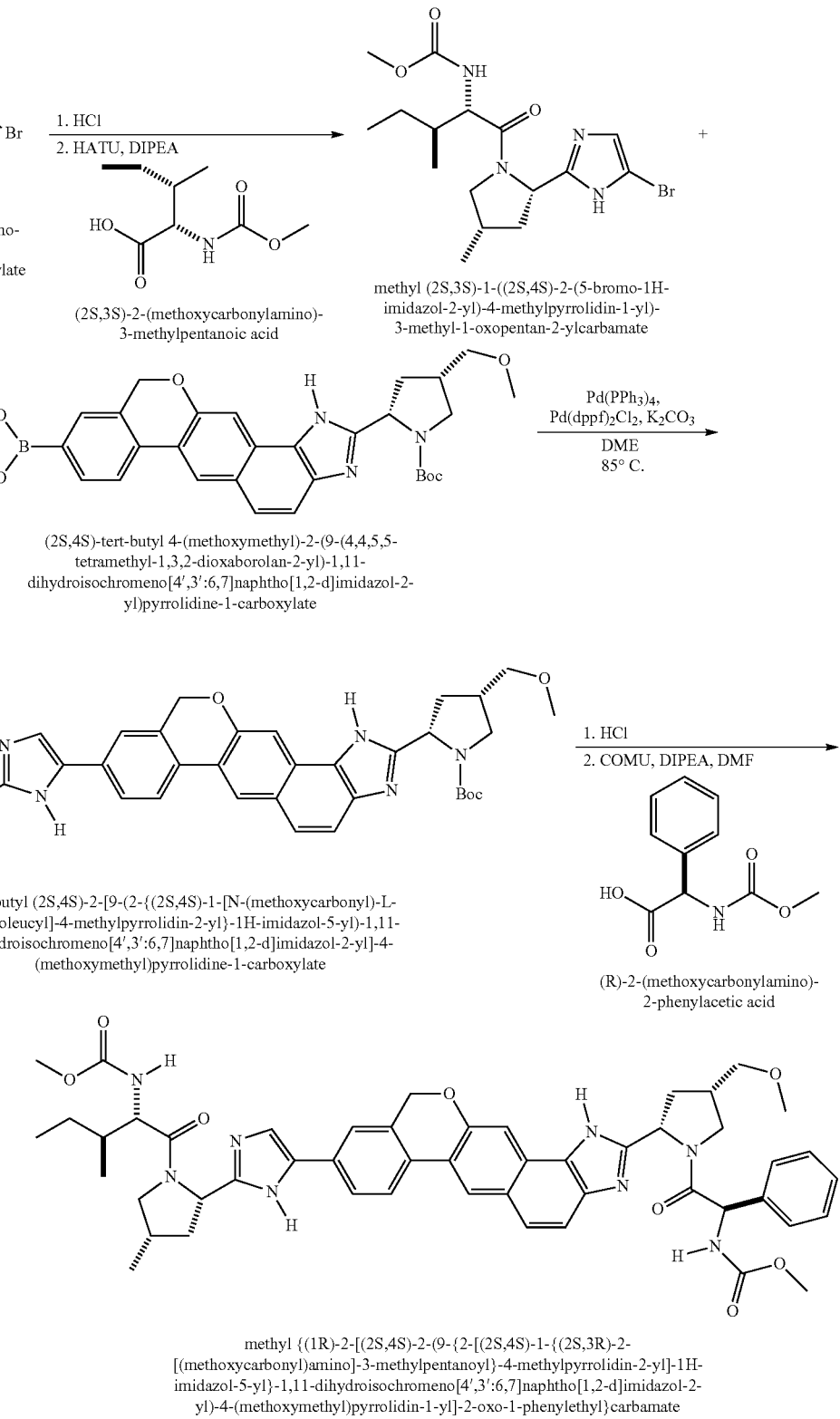
Methyl (2S,3S)-1-((2S,4S)-2-(5-bromo-1H-imidazol-2-yl)-4-methylpyrrolidin-1-yl)-3-methyl-1-oxopentan-2-ylcarbamate: (2S,4S)-tert-butyl 2-(5-bromo-1H-imidazol-2-yl)-4-methylpyrrolidine-1-carboxylate (100 mg, 0.13 mmol) in 1.25 N HCl in EtOH (15 mL) was heated to 50° C. for 3 h and then concentrated under reduced pressure. The crude residue was treated with (2S,3S)-2-(methoxycarbonylamino)-3-methylpentanoic acid (625 mg, 3.30 mmol), HATU (1.05 g, 2.77 mmol) and DMF (10 mL), then DIPEA (1.33 mL, 7.62 mmol) was added dropwise. After 2 h, the mixture was poured into saturated aqueous NaHCO$_3$ and then extracted with EtOAc. The organic phase was washed with successively with 5% aqueous LiCl and Brine. The organics were dried over Na$_2$SO$_4$, filtered and concentrated under reduced pressure. The crude residue was purified by silica column chromatography (30 to 90% of 10% MeOH/EtoAc to Hexanes) afforded methyl (2S,3S)-1-((2S,4S)-2-(5-bromo-1H-imidazol-2-yl)-4-methylpyrrolidin-1-yl)-3-methyl-1-oxopentan-2-ylcarbamate (932 mg, 81%).

Tert-butyl (2S,4S)-2-[9-(2-{(2S,4S)-1-[N-(methoxycarbonyl)-1-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate: (2S,4S)-Tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate (856 mg, 1.4 mmol), methyl (2S,3S)-1-((2S,4S)-2-(5-bromo-1H-imidazol-2-yl)-4-methylpyrrolidin-1-yl)-3-methyl-1-oxopentan-2-ylcarbamate (932 mg, 2.1 mmol), Pd(PPh$_3$)$_4$ (162 mg, 0.14 mmol), PdCl$_2$(dppf)$_2$ (102 mg, 0.14 mmol), and K$_2$CO$_3$ (2M in H$_2$O, 2.31 mL, 4.62 mmol) were combined in DMSO (8 mL) and dioxanes (8 mL). The mixture was degassed with bubbling Argon for 10 min the heated to 95° C. for 1 h. After cooling, the reaction mixture was diluted with EtOAc, and washed successively with saturated aqueous NaHCO$_3$ and brine. The organics were dried over Na$_2$SO$_4$, filtered and concentrated under reduced pressure. The crude residue was purified by silica column chromatography (1% to 20% MeOH/EtOAc) to afford tert-butyl (2S,4S)-2-[9-(2-{(2S,4S)-1-[N-(methoxycarbonyl)-1-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (701 mg, 62%).

Methyl {(1R)-2-[(2S,4S)-2-(9-{2-[(2S,4S)-1-{(2S,3R)-2-[(methoxycarbonyl)amino]-3-methylpentanoyl}-4-methyl-pyrrolidin-2-yl]-1H-imidazol-5-yl}-1,11-dihydroisochrom-eno[4',3':6,7]naphtho[1,2-d]imidazol-2-yl)-4-(methoxymethyl)pyrrolidin-1-yl]-2-oxo-1-phenylethyl}carbamate: A solution of tert-butyl (2S,4S)-2-[9-(2-{(2S,4S)-1-[N-(methoxycarbonyl)-1-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (218 mg, 0.27 mmol) in 1.25 N HCl in EtOH (3 mL) was heated to 50° C. for 3 h. The reaction was concentrated and the crude material dissolved in DMF (3 mL). To this solution was added a solution of (R)-2-(methoxycarbonylamino)-2-phenylacetic acid (73 mg, 0.35 mmol) and COMU (127 mg, 0.30 mmol). To the resulting solution was added diisopropylethylamine (0.141 mL, 0.81 mmol). After stirring for 2 h at room temperature, the reaction was quenched with 1N HCl (0.200 mL) and purified by HPLC. After lyophilization, the TFA salt was dissolved in EtOAc and washed with saturated NaHCO$_3$. The organic phase was dried over Na$_2$SO$_4$ and concentrated. The free base was then dissolved in MeCN/H$_2$O and lyophilized to afford methyl {(1R)-2-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate: (121 mg, 50%). LCMS-ESI$^+$: calculated for C$_{50}$H$_{56}$N$_8$O$_8$: 896.4; observed [M+1]$^+$: 897.5.

Example QC

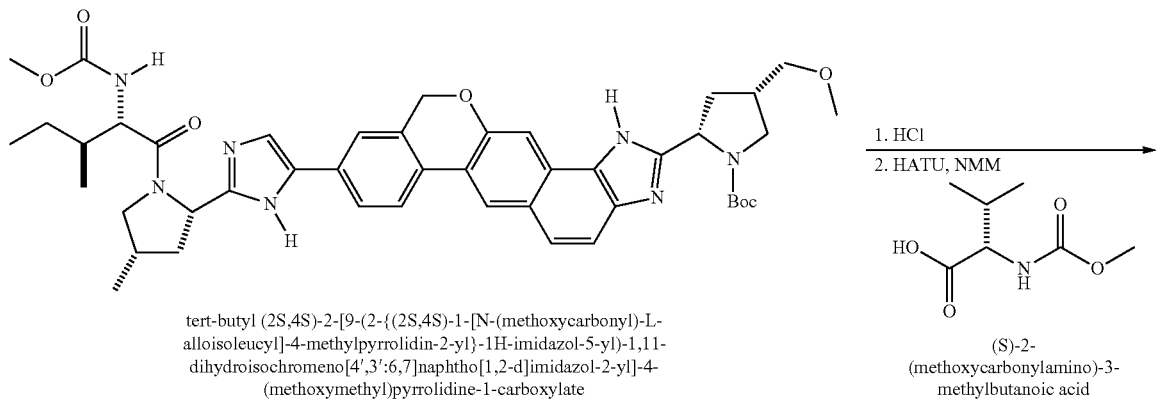

tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (S)-2-(methoxycarbonylamino)-3-methylbutanoic acid

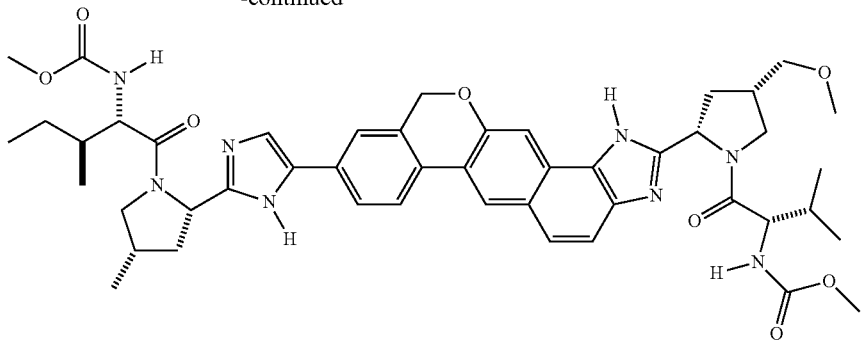

methyl {(2S)-1-[(2S,4S)-2-(9-{2-[(2S,4S)-1-{(2S,3R)-2-
[(methoxycarbonyl)amino]-3-methylpentanoyl}-4-methylpyrrolidin-2-yl]-
1H-imidazol-5-yl}-1,11-dihydroisochromeno[4',3':6,7]naphtho[1,2-
d]imidazol-2-yl)-4-(methoxymethyl)pyrrolidin-1-yl]-3-methyl-1-
oxobutan-2-yl}carbamate Methyl {(2S)-1-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxobutan-2-yl}carbamate: tert-butyl (2S,4S)-2-[9-(2-{(2S,4S)-1-[N-(methoxycarbonyl)-1-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (105 mg, 0.13 mmol) in 1.25 N HCl in EtOH (3 mL) was heated to 50° C. for 3 h and then concentrated under reduced pressure. The crude residue was treated with (S)-2-(methoxycarbonylamino)-3-methylbutanoic acid (32 mg, 0.18 mmol), HATU (59 mg, 0.16 mmol) and DMF (1.3 mL), then N-methylmorpholine (0.043 mL, 0.39 mmol) was added dropwise. After 3 h, the mixture was quenched with 1N HCl (0.100 mL) and then purified by HPLC to afford methyl {(2S)-1-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxobutan-2-yl}carbamate (80 mg, 71%).

LCMS-ESI$^+$: calculated for $C_{47}H_{58}N_8O_8$: 862.4; observed [M+1]$^+$: 864.2.

Example QD

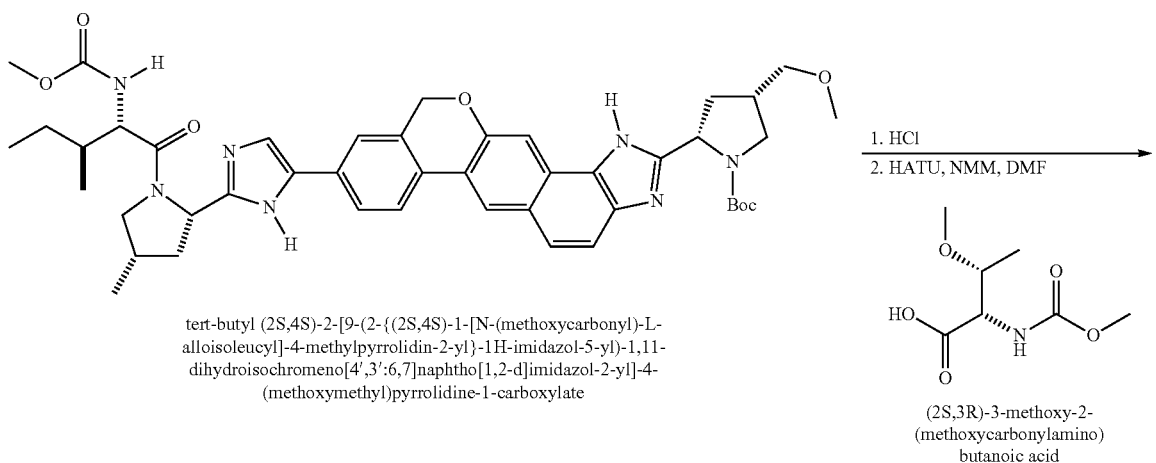

tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate 1. HCl
2. HATU, NMM, DMF (2S,3R)-3-methoxy-2-(methoxycarbonylamino) butanoic acid

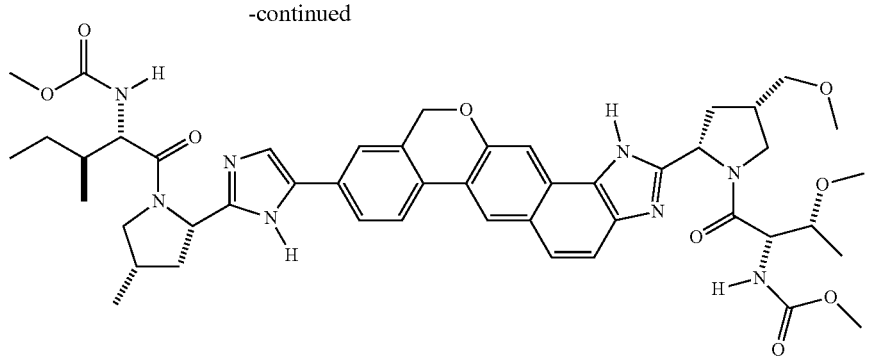

methyl {(2S,3R)-1-[(2S,4S)-2-(5-{2-[(2S,4S)-1-[N-(methoxycarbonyl)-O-methyl-L-allothreonyl]-4-(methoxymethyl)pyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxopentan-2-yl}carbamate Methyl {(2S,3R)-1-[(2S,4S)-2-(5-{2-[(2S,4S)-1-[N-(methoxycarbonyl)-O-methyl-1-allothreonyl]-4-(methoxymethyl)pyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxopentan-2-yl}carbamate: tert-butyl (2S,4S)-2-[9-(2-{(2S,4S)-1-[N-(methoxycarbonyl)-1-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (105 mg, 0.13 mmol) in 1.25 N HCl in EtOH (3 mL) was heated to 50° C. for 3 h and then concentrated under reduced pressure. The crude residue was treated with (2S,3R)-3-methoxy-2-(methoxycarbonylamino)butanoic acid (35 mg, 0.18 mmol), HATU (59 mg, 0.16 mmol) and DMF (1.3 mL), then N-methylmorpholine (0.043 mL, 0.39 mmol) was added dropwise. After 3 hr, the mixture was quenched with 1N HCl (0.100 mL) and then purified by HPLC to afford methyl {(2S,3R)-1-[(2S,4S)-2-(5-{2-[(2S,4S)-1-[N-(methoxycarbonyl)-O-methyl-1-allothreonyl]-4-(methoxymethyl)pyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxopentan-2-yl}carbamate (92 mg, 81%).

LCMS-ESI$^+$: calculated for $C_{47}H_{58}N_8O_9$: 878.4; observed [M+1]$^+$: 879.3.

Example QE

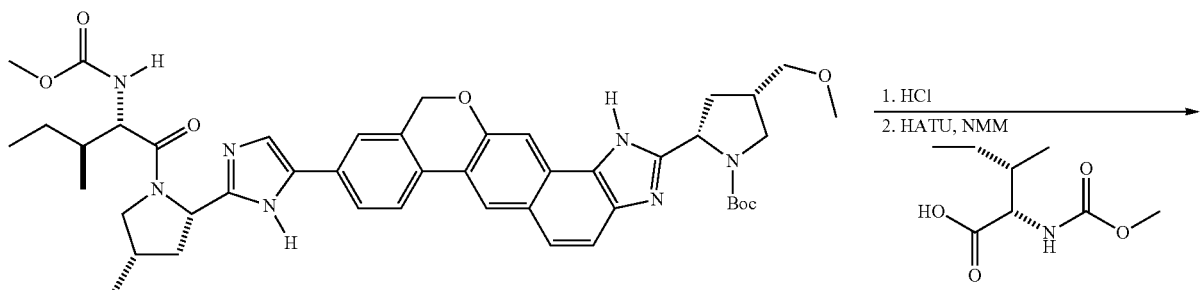

tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate 1. HCl
2. HATU, NMM (2S,3S)-2-(methoxycarbonylamino)-3-methylpentanoic acid -continued

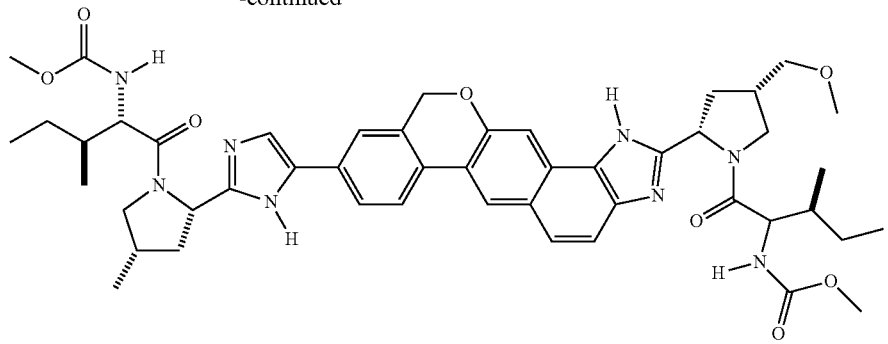

methyl {(3R)-1-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxopentan-2-yl}carbamate Methyl {(3R)-1-[(2S,4S)-2-(9-{2-[(2S,4S)-1-{(2S,3R)-2-[(methoxycarbonyl)amino]-3-methylpentanoyl}-4-methyl-pyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxopentan-2-yl}carbamate: tert-butyl (2S,4S)-2-[9-(2-{(2S,4S)-1-[N-(methoxycarbonyl)-1-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl) pyrrolidine-1-carboxylate (105 mg, 0.13 mmol) in 1.25 N HCl in EtOH (3 mL) was heated to 50° C. for 3 h and then concentrated under reduced pressure. The crude residue was treated with (2S,3S)-2-(methoxycarbonylamino)-3-methyl-pentanoic acid (34 mg, 0.18 mmol), HATU (59 mg, 0.16 mmol) and DMF (1.3 mL), then N-methylmorpholine (0.043 mL, 0.39 mmol) was added dropwise. After 3 h, the mixture was quenched with 1N HCl (0.100 mL) and then purified by HPLC to afford methyl {(3R)-1-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxopentan-2-yl}carbamate (98 mg, 86%).

LCMS-ESI$^+$: calculated for $C_{48}H_{60}N_8O_8$: 876.5; observed [M+1]$^+$: 878.2.

Example QF

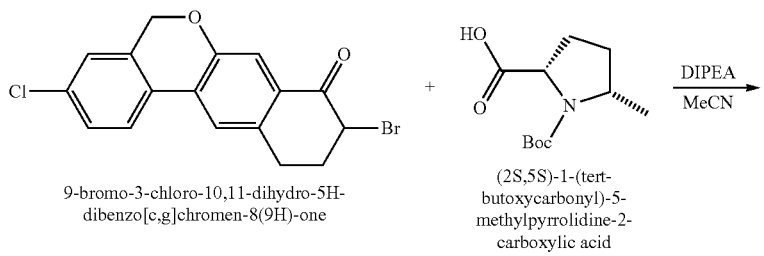

9-bromo-3-chloro-10,11-dihydro-5H-dibenzo[c,g]chromen-8(9H)-one (2S,5S)-1-(tert-butoxycarbonyl)-5-methylpyrrolidine-2-carboxylic acid

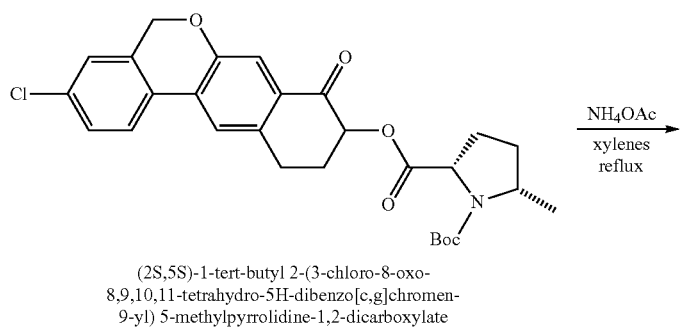

(2S,5S)-1-tert-butyl 2-(3-chloro-8-oxo-8,9,10,11-tetrahydro-5H-dibenzo[c,g]chromen-9-yl) 5-methylpyrrolidine-1,2-dicarboxylate -continued

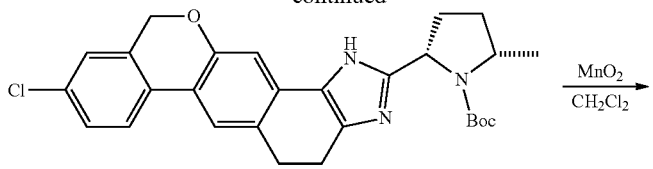

(2S,5S)-tert-butyl 2-(9-chloro-4,5-dihydro-5H-naphtho[c,g]chromeno[8,9-d]imidazol-2-yl)-5-(methyl)pyrrolidine-1-carboxylate

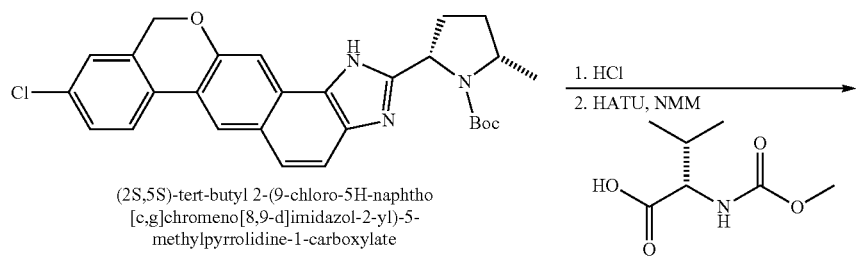

(2S,5S)-tert-butyl 2-(9-chloro-5H-naphtho[c,g]chromeno[8,9-d]imidazol-2-yl)-5-methylpyrrolidine-1-carboxylate

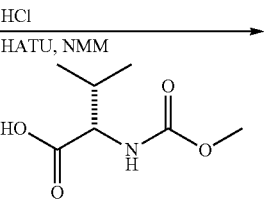

(S)-2-(methoxycarbonylamino)-3-methylbutanoic acid

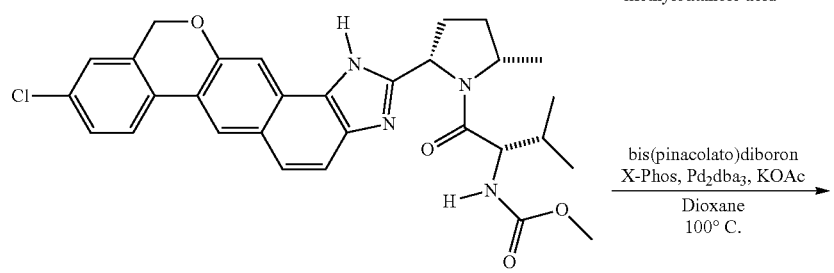

methyl {(2S)-1-[(2S,5S)-2-(9-chloro-1,11-dihydroisochromeno[4′,3′:6,7]naphtho[1,2-d]imidazol-2-yl)-5-methylpyrrolidin-1-yl]-3-methyl-1-oxobutan-2-yl}carbamate

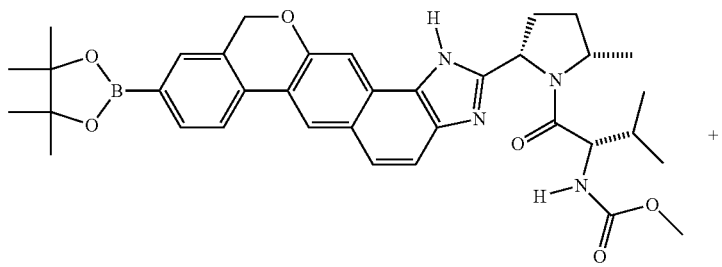

methyl [(2S)-3-methyl-1-{(2S,5S)-2-methyl-5-[9-(4,4,5,5-tetramethyl-1,3,2-dioxaborolan-2-yl)-1,11-dihydroisochromeno[4′,3′:6,7]naphtho[1,2-d]imidazol-2-yl)pyrrolidine-1-yl}-1-oxobutan-2-yl]carbamate

+

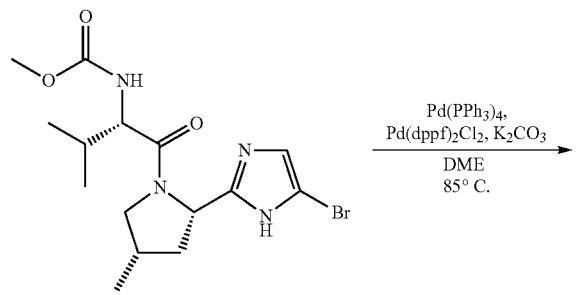

methyl (S)-1-((2S,4S)-2-(5-bromo-1H-imidazol-2-yl)-4-methylpyrrolidin-1-yl)-3-methyl-1-oxobutan-2-ylcarbamate

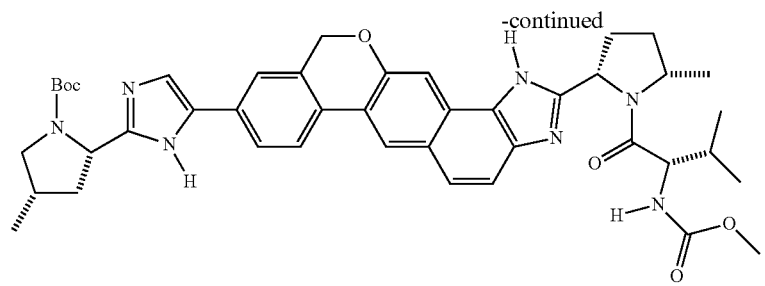

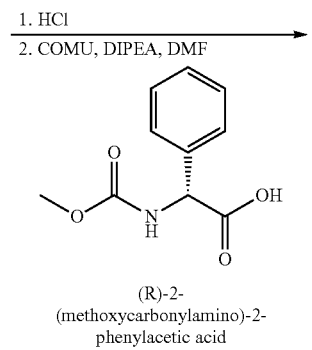

tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (R)-2-(methoxycarbonylamino)-2-phenylacetic acid

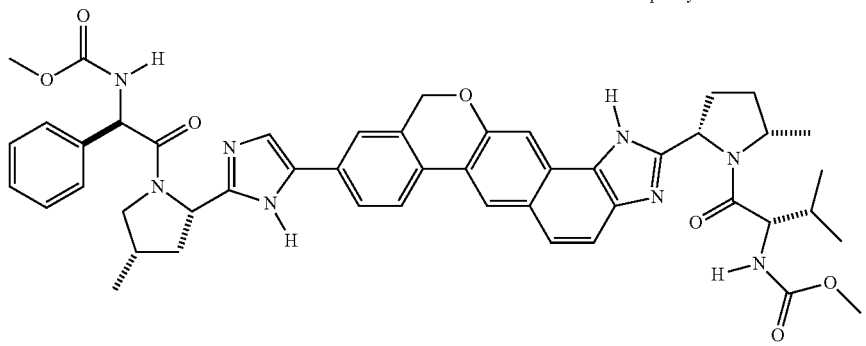

methyl {(2S)-1-[(2S,5S)-2-(9-{2-[(2S,4S)-1-{(2R)-2-[(methoxycarbonyl)amino]-2-phenylacetyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (2S,5S)-1-tert-butyl 2-(3-chloro-8-oxo-8,9,10,11-tetrahydro-5H-dibenzo[c,g]chromen-9-yl)5-methylpyrrolidine-1,2-dicarboxylate: To a solution of 9-bromo-3-chloro-10,11-dihydro-5H-dibenzo[c,g]chromen-8(9H)-one (1.41 g, 3.88 mmol) in MeCN (17 mL) was added (2S,5S)-1-(tert-butoxycarbonyl)-5-methylpyrrolidine-2-carboxylic acid (980 mg, 4.27 mmol) and DIPEA (1.49 mL, 8.54 mmol). After stirring for 18 h at 50° C., the solution was diluted with EtOAc and washed successively with 1N HCl, saturated aqueous NaHCO₃ and brine. The organics were dried over $Na_2SO_4$, filtered and concentrated under reduced pressure. The crude residue was purified by silica column chromatography (10% to 30% EtOAc/hexanes) to afford (2S,5S)-1-tert-butyl 2-(3-chloro-8-oxo-8,9,10,11-tetrahydro-5H-dibenzo[c,g]chromen-9-yl) 5-methylpyrrolidine-1,2-dicarboxylate (1.63 g, 81%).

(2S,5S)-tert-butyl 2-(9-chloro-4,5-dihydro-5H-naphtho[c,g]chromeno[8,9-d]imidazol-2-yl)-5-(methyl)pyrrolidine-1-carboxylate: (2S,5S)-1-tert-butyl 2-(3-chloro-8-oxo-8,9,10,11-tetrahydro-5H-dibenzo[c,g]chromen-9-yl) 5-methylpyrrolidine-1,2-dicarboxylate (1.63 g, 3.18 mmol) was added toluene (30 mL), 2-methoxyethanol (3 mL), and ammonium acetate (3.68 g, 77.1 mmol) and the solution was heated to reflux overnight. The following morning, the solution was cooled to rt and was diluted with EtOAc and washed successively with water, saturated aqueous NaHCO₃ and brine. The organics were dried over $Na_2SO_4$, filtered and concentrated under reduced pressure. The crude residue was purified by silica column chromatography (40% to 80% EtOAc/hexanes) to afford (2S,5S)-tert-butyl 2-(9-chloro-4,5-dihydro-5H-naphtho[c,g]chromeno[8,9-d]imidazol-2-yl)-5-methylpyrrolidine-1-carboxylate (1.13 g, 72%).

((2S,5S)-tert-butyl 2-(9-chloro-5H-naphtho[c,g]chromeno[8,9-d]imidazol-2-yl)-5-methylpyrrolidine-1-carboxylate: To a solution of (2S,5S)-tert-butyl 2-(9-chloro-4,5-dihydro-5H-naphtho[c,g]chromeno[8,9-d]imidazol-2-yl)-5-(methyl)pyrrolidine-1-carboxylate (1.13 g, 2.3 mmol) in $CH_2Cl_2$ (25 mL) was added $MnO_2$ (9.98 g, 115 mmol). The reaction mixture was stirred overnight then filtered over celite. The filter cake was washed with copious $CH_2Cl_2$ and MeOH, and the filtrate was concentrated under reduced pressure to afford the crude product (2S,5S)-tert-butyl 2-(9-chloro-5H-naphtho[c,g]chromeno[8,9-d]imidazol-2-yl)-5-methylpyrrolidine-1-carboxylate (931 mg, 83%).

Methyl {(2S)-1-[(2S,5S)-2-(9-chloro-1,11-dihydroisochromeno[4',3':6,7]naphtho[1,2-d]imidazol-2-yl)-5-methylpyrrolidin-1-yl]-3-methyl-1-oxobutan-2-yl}carbamate: (2S,5S)-tert-butyl 2-(9-chloro-5H-naphtho[c,g]chromeno[8,9-d]imidazol-2-yl)-5-methylpyrrolidine-1-carboxylate (931 mg, 1.9 mmol) in 1.25 N HCl in EtOH (8 mL) was heated to 50° C. for 3 h and then concentrated under reduced pressure. The crude residue was treated with (S)-2-(methoxycarbonylamino)-3-methylbutanoic acid (499 mg, 2.9 mmol), HATU (795 mg, 2.1 mmol) and DMF (10 mL), then N-methylmorpholine (0.627 mL, 5.7 mmol) was added dropwise. After stirring for 1 h, the reaction was diluted with EtOAc and washed successively with saturated aqueous NaHCO₃, 5% LiCl, and brine. The organics were dried over $Na_2SO_4$, filtered and concentrated under reduced pressure. The crude residue was purified by silica column chromatography (50% to 100% EtOAc/hexanes) to afford methyl {(2S)-1-[(2S,5S)-2-(9-chloro-1,11-dihydroisochromeno[4',3':6,7]naphtho[1,2-d]imidazol-2-yl)-5-methylpyrrolidin-1-yl]-3-methyl-1-oxobutan-2-yl}carbamate (950 mg, 91%).

Methyl [(2S)-3-methyl-1-{(2S,5S)-2-methyl-5-[9-(4,4,5,5-tetramethyl-1,3,2-dioxaborolan-2-yl)-1,11-dihydroisochromeno[4',3':6,7]naphtho[1,2-d]imidazol-2-yl]pyrolidin-1-yl]-1-oxobutan-2-yl]carbamate: To methyl {(2S)-1-[(2S,5S)-2-(9-chloro-1,11-dihydroisochromeno[4',3':6,7]naphtho[1,2-d]imidazol-2-yl)-5-methylpyrrolidin-1-yl]-3-methyl-1-oxobutan-2-yl}carbamate (950 mg, 1.74 mmol) in dioxane (17 mL) was added bis(pinacolato)diboron (662 mg, 2.61 mmol), KOAc (512 mg, 5.22 mmol), X-Phos (25 mg, 0.05 mmol), and Pd₂dba₃ (80 mg, 0.08 mmol). The solution was degassed with N₂ for 10 min, then heated to 90° C. for 16 h. The solution was cooled to rt, diluted with EtOAc, washed with saturated aqueous NaHCO₃, brine, dried with Na₂SO₄, and concentrated. Purification by silica gel chromatography (30% to 75% gradient using 5% MeOH/EtOAc to Hexanes) to afford methyl [(2S)-3-methyl-1-{(2S,5S)-2-methyl-5-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl]-1-oxobutan-2-yl]carbamate (800 mg, 72%).

tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate: To a solution of [(2S)-3-methyl-1-{(2S,5S)-2-methyl-5-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl]-1-oxobutan-2-yl]carbamate (269 mg, 0.42 mmol), methyl (S)-1-((2S,4S)-2-(5-bromo-1H-imidazol-2-yl)-4-methylpyrrolidin-1-yl)-3-methyl-1-oxobutan-2-ylcarbamate (206 mg, 0.54 mmol), tetrakis(triphenylphosphine) palladium(0) (49 mg, 0.042 mmol) and dichloro[1,1'-bis(diphenylphosphino)ferrocene]palladium(II) (31 mg, 0.042 mmol) in DMSO (3 mL) and dioxanes (3 mL) was added a solution of potassium carbonate (2M in water, 0.69 mL, 1.39 mmol). The resulting mixture was degassed and then heated to 95° C. for 2 h. After cooling to room temperature, the reaction was diluted with ethyl acetate. The organics were washed with saturated sodium bicarbonate and brine, dried over Na₂SO₄ and concentrated. The crude residue was purified by flash chromatography (1 to 20% MeOH/EtOAc) to yield tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (202 mg, 63%).

Methyl {(2S)-1-[(2S,5S)-2-(9-{2-[(2S,4S)-1-{(2R)-2-[(methoxycarbonyl)amino]-2-phenylacetyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate: A solution of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (80 mg, 0.11 mmol) in 1.25 N HCl in EtOH (2 mL) was heated to 50° C. for 3 h. The reaction was concentrated and the crude material dissolved in DMF (1.5 mL). To this solution was added a solution of (R)-2-(methoxycarbonylamino)-2-phenylacetic acid (29 mg, 0.14 mmol) and COMU (52 mg, 0.12 mmol). To the resulting solution was added diisopropylethylamine (0.057 mL, 0.33 mmol). After stirring for 2 h at room temperature, the reaction was quenched with 1N HCl (0.200 mL) and purified by HPLC. After lyophilization, the TFA salt was dissolved in EtOAc and washed with saturated NaHCO₃. The organic phase was dried over Na₂SO₄ and concentrated. The free base was then dissolved in MeCN/H₂O and lyophilized to afford methyl {(2S)-1-[(2S,5S)-2-(9-{2-[(2S,4S)-1-{(2R)-2-[(methoxycarbonyl)amino]-2-phenylacetyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate: (42 mg, 45%). LCMS-ESI⁺: calculated for $C_{48}H_{52}N_8O_7$: 852.4; observed [M+1]⁺: 854.2.

Example QG

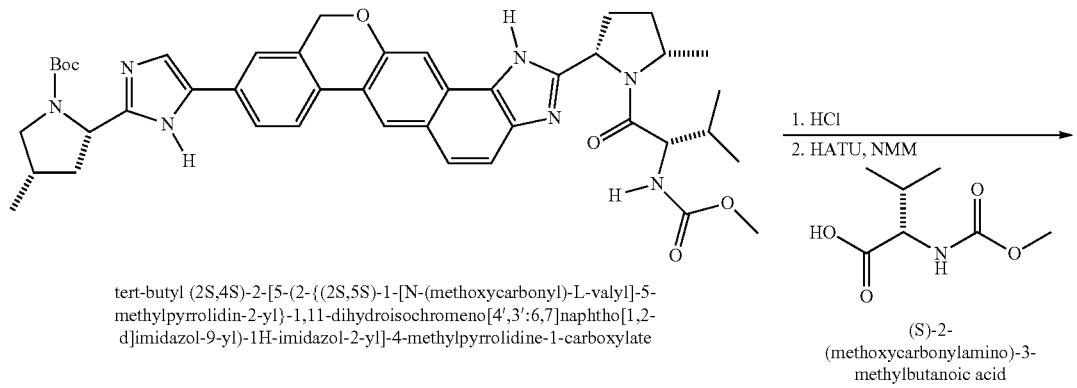

tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (S)-2-(methoxycarbonylamino)-3-methylbutanoic acid

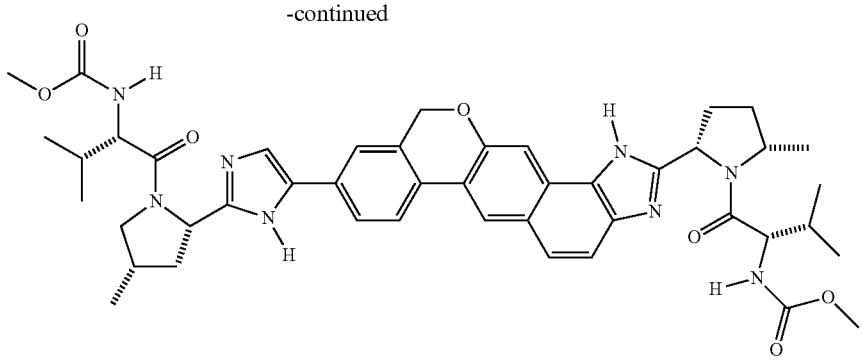

methyl {(2S)-1-[(2S,5S)-2-(9-{2-[(2S,4S)-1-{(2S)-2-[(methoxycarbonyl)amino]-3-methylbutanoyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,4S)-1-{(2S)-2-[(methoxycarbonyl)amino]-3-methylbutanoyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate: tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (60 mg, 0.079 mmol) in 1.25 N HCl in EtOH (2 mL) was heated to 50° C. for 3 h and then concentrated under reduced pressure. The crude residue was treated with (S)-2-(methoxycarbonylamino)-3-methylbutanoic acid (21 mg, 0.12 mmol), HATU (36 mg, 0.095 mmol) and DMF (1.5 mL), then N-methylmorpholine (0.027 mL, 0.24 mmol) was added dropwise. After 3 h, the mixture was quenched with 1N HCl (0.100 mL) and then purified by HPLC to afford methyl {(2S)-1-[(2S,5S)-2-(9-{2-[(2S,4S)-1-{(2S)-2-[(methoxycarbonyl)amino]-3-methylbutanoyl}-4-methylpyrrolidin-2-yl]-1H-imidazol-5-yl}-1,11-dihydroisochromeno[4',3:6,7]naphtho[1,2-d]imidazol-2-yl)-5-methylpyrrolidin-1-yl]-3-methyl-1-oxobutan-2-yl}carbamate (33 mg, 51%).

LCMS-ESI$^+$: calculated for $C_{45}H_{54}N_8O_7$: 818.4; observed [M+1]$^+$: 820.2.

Example QH

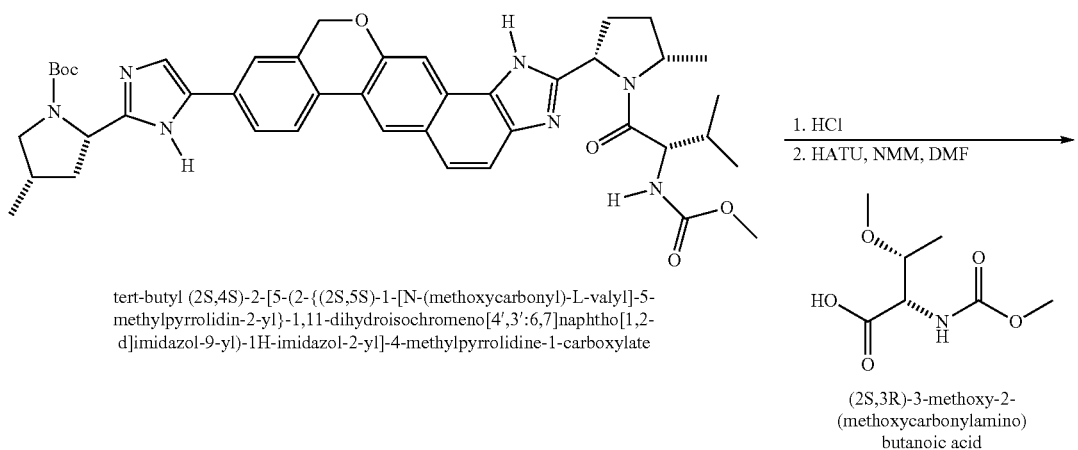

tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (2S,3R)-3-methoxy-2-(methoxycarbonylamino) butanoic acid

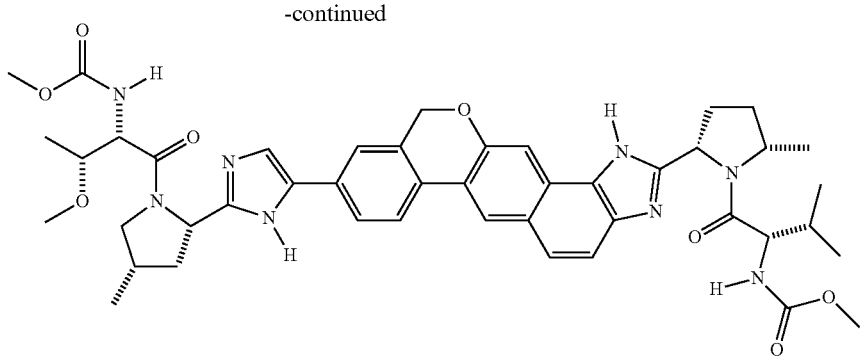

methyl {(2S)-1-[(2S,5S)-2-(9-{2-[(2S,4S)-1-{(2S,3S)-3-methoxy-2-[(methoxycarbonyl)amino]butanoyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,4S)-1-{(2S,3S)-3-methoxy-2-[(methoxycarbonyl)amino]butanoyl}-4-methyl-pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate: tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (20 mg, 0.079 mmol) in 1.25 N HCl in EtOH (2 mL) was heated to 50° C. for 3 h and then concentrated under reduced pressure. The crude residue was treated with (2S,3R)-3-methoxy-2-(methoxycarbonylamino)butanoic acid (8 mg, 0.04 mmol), HATU (12 mg, 0.03 mmol) and DMF (0.5 mL), then N-methylmorpholine (0.009 mL, 0.078 mmol) was added dropwise. After 3 h, the mixture was quenched with 1N HCl (0.100 mL) and then purified by HPLC to afford methyl {(2S)-1-[(2S,5S)-2-(9-{2-[(2S,4S)-1-{(2S,3S)-3-methoxy-2-[(methoxycarbonyl)amino]butanoyl}-4-methyl-pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (7.5 mg, 35%).

LCMS-ESI$^+$: calculated for $C_{45}H_{54}N_8O_8$: 834.4; observed [M+1]$^+$: 835.7.

Example QI

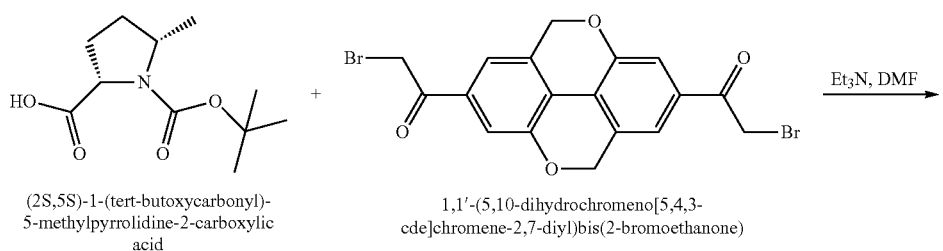

(2S,5S)-1-(tert-butoxycarbonyl)-5-methylpyrrolidine-2-carboxylic acid 1,1'-(5,10-dihydrochromeno[5,4,3-cde]chromene-2,7-diyl)bis(2-bromoethanone)

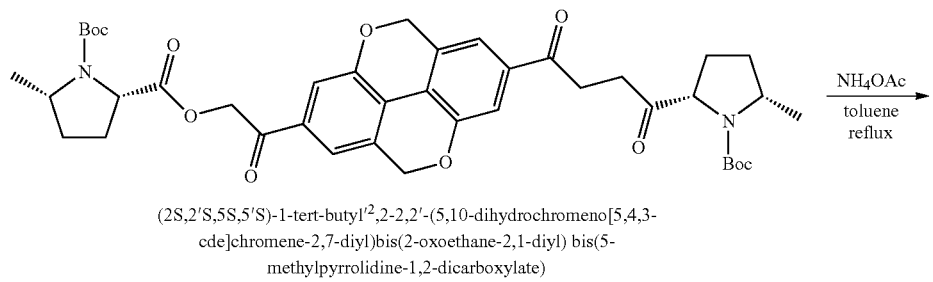

(2S,2'S,5S,5'S)-1-tert-butyl'$^2$,2-2,2'-(5,10-dihydrochromeno[5,4,3-cde]chromene-2,7-diyl)bis(2-oxoethane-2,1-diyl) bis(5-methylpyrrolidine-1,2-dicarboxylate)

-continued

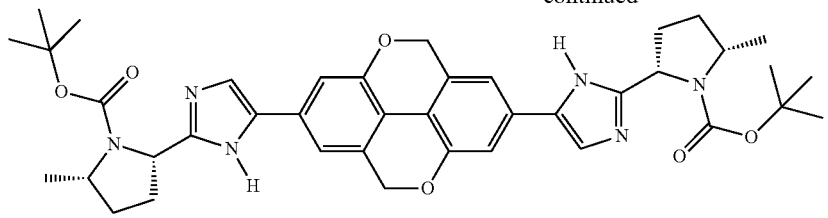

(2S,2'S,5S,5'S)-tert-butyl 5,5'-(5,5'-(5,10-dihydrochromeno[5,4,3-cde]chromene-2,7-diyl)bis(1H-imidazole-5,2-diyl))bis(2-methylpyrrolidine-1-carboxylate)

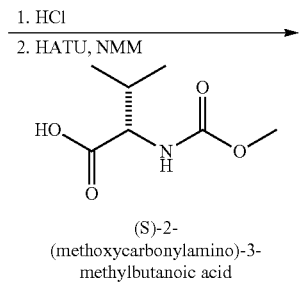

1. HCl
2. HATU, NMM (S)-2-(methoxycarbonylamino)-3-methylbutanoic acid

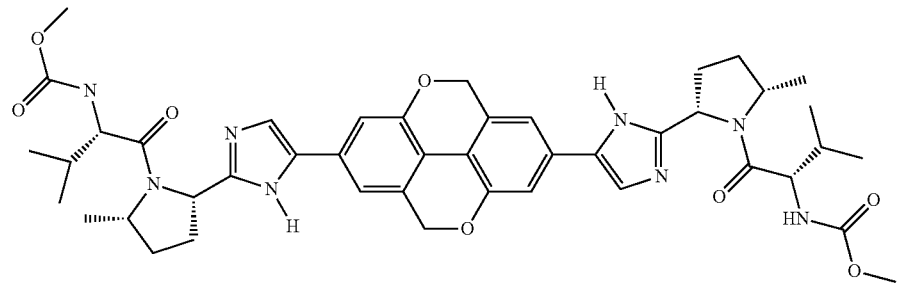

Dimethyl (2S,2'S)-1,1'-((2S,2'S,5S,5'S)-5,5'-(5,5'-(5,10-dihydrochromeno[5,4,3-cde]chromene-2,7-diyl)bis(1H-imidazole-5,2-diyl))bis(2-methylpyrrolidine-5,1-diyl))bis(3-methyl-1-oxobutane-2,1-diyl)dicarbamate (2S,2'S,5S,5'S)-1-tert-butyl '2,2-2,2'-(5,10-dihydrochromeno[5,4,3-cde]chromene-2,7-diyl)bis(2-oxoethane-2,1-diyl)bis(5-methylpyrrolidine-1,2-dicarboxylate):

A mixture of 1,1'-(5,10-dihydrochromeno[5,4,3-cde]chromene-2,7-diyl)bis(2-bromoethanone) (400 mg, 0.88 mmol)), and (2S,5S)-1-(tert-butoxycarbonyl)-5-methylpyrrolidine-2-carboxylic acid (507 mg, 2.21 mmol) in 10 mL DMF with triethylamine (0.385 mL, 2.21 mmol) was heated at 80° C. for 4 hours. The solution was cooled to rt then diluted with EtOAc and washed successively with 1N HCl, saturated aqueous NaHCO₃, and brine. The organic phase was dried over Na₂SO₄, concentrated, and purified by silica gel chromatography (20% to 50% EtOAc/Hexanes) to afford (2S,2'S,5S,5'S)-1-tert-butyl '2,2-2,2'-(5,10-dihydrochromeno[5,4,3-cde]chromene-2,7-diyl)bis(2-oxoethane-2,1-diyl)bis(5-methylpyrrolidine-1,2-dicarboxylate): (208 mg, 32%).

(2S,2'S,5S,5'S)-tert-butyl 5,5'-(5,5'-(5,10-dihydrochromeno[5,4,3-cde]chromene-2,7-diyl)bis(1H-imidazole-5,2-diyl))bis(2-methylpyrrolidine-1-carboxylate): A mixture of (2S,2'S,5R,5'R)-1-tert-butyl (2S,2'S,5S,5'S)-1-tert-butyl '2,2-2,2'-(5,10-dihydrochromeno[5,4,3-cde]chromene-2,7-diyl)bis(2-oxoethane-2,1-diyl)bis(5-methylpyrrolidine-1,2-dicarboxylate) (208 mg, 0.28 mmol), ammonium acetate (323 mg, 4.2 mmol), toluene (2.5 mL) and 2-methoxypropanol (0.25 mL) was heated at reflux for 4 h. The solution was cooled to rt then diluted with EtOAc and washed successively with saturated aqueous NaHCO₃ and brine. The organic phase was dried over Na₂SO₄, concentrated, and purified by silica gel chromatography (20% to 50% EtOAc/Hexanes) to afford (2S,2'S,5S,5'S)-tert-butyl 5,5'-(5,5'-(5,10-dihydrochromeno[5,4,3-cde]chromene-2,7-diyl)bis(1H-imidazole-5,2-diyl))bis(2-methylpyrrolidine-1-carboxylate) (163 mg, 82%).

Dimethyl (2S,2'S)-1,1'-((2S,2'S,5S,5'S)-5,5'-(5,5'-(5,10-dihydrochromeno[5,4,3-cde]chromene-2,7-diyl)bis(1H-imidazole-5,2-diyl))bis(2-methylpyrrolidine-5,1-diyl))bis(3-methyl-1-oxobutane-2,1-diyl)dicarbamate: (2S,2'S,5 S,5'S)-tert-butyl 5,5'-(5,5'-(5,10-dihydrochromeno[5,4,3-cde]chromene-2,7-diyl)bis(1H-imidazole-5,2-diyl))bis(2-methylpyrrolidine-1-carboxylate) (81 mg, 0.11 mmol) in 1.25 N HCl in EtOH (2 mL) was heated to 50° C. for 3 h and then concentrated under reduced pressure. The crude residue was treated with (S)-2-(methoxycarbonylamino)-3-methylbutanoic acid (50 mg, 0.12 mmol), HATU (88 mg, 0.23 mmol) and DMF (1 mL), then N-methylmorpholine (0.060 mL, 0.55 mmol) was added dropwise. After 3 h, the mixture was quenched with 1N HCl (0.100 mL) and then purified by HPLC to afford dimethyl (2S,2'S)-1,1'-((2S,2'S,5S,5'S)-5,5'-(5,5'-(5,10-dihydrochromeno[5,4,3-cde]chromene-2,7-diyl)bis(1H-imidazole-5,2-diyl))bis(2-methylpyrrolidine-5,1-diyl))bis(3-methyl-1-oxobutane-2,1-diyl)dicarbamate (62 mg, 68%).

LCMS-ESI⁺: calculated for $C_{45}H_{54}N_8O_8$: 822.4; observed [M+1]⁺: 823.2.

Example QJ

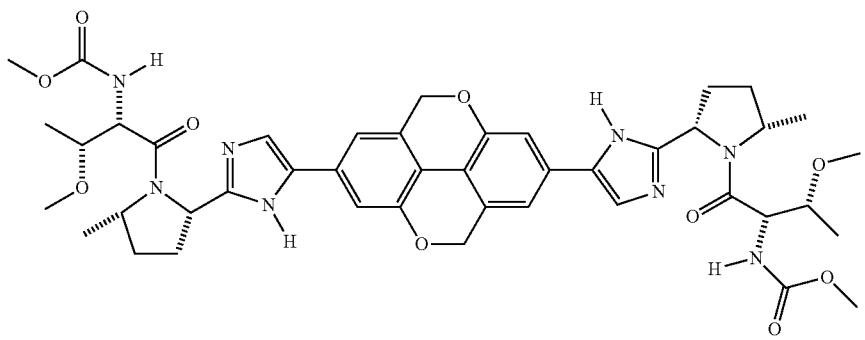

Dimethyl (2S,2'S,3R,3'R)-1,1'-((2S,2'S,5S,5'S)-5,5'-(5,5'-(5,10-dihydrochromeno[5,4,3-cde]chromene-2,7-diyl)bis(1H-imidazole-5,2-diyl))bis(2-methylpyrrolidine-5,1-diyl))bis(3-methoxy-1-oxobutane-2,1-diyl)dicarbamate Dimethyl (2S,2'S,3R,3'R)-1,1'-((2S,2'S,5S,5'S)-5,5'-(5,5'-(5,10-dihydrochromeno[5,4,3-cde]chromene-2,7-diyl)bis(1H-imidazole-5,2-diyl))bis(2-methylpyrrolidine-5,1-diyl))bis(3-methoxy-1-oxobutane-2,1-diyl)dicarbamate: The title compound was prepared as described for Example QI, substituting (2S,3R)-3-methoxy-2-(methoxycarbonylamino)butanoic acid for (S)-2-(methoxycarbonylamino)-3-methylbutanoic acid. LCMS-ESI$^+$: calculated for $C_{44}H_{54}N_8O_{10}$: 854.4; observed [M+1]$^+$: 856.0. $^1$H NMR (CD$_3$CN with D$_2$O) 7.600 (s, 2H), 7.303 (s, 1H), 7.189 (s, 1H), 7.093 (m, 4H), 5.237 (s, 4H), 4.581 (m, 2H), 4.344 (m, 2H), 3.608 (s, 6H), 3.580 (m, 2H), 3.294 (s, 2H), 3.243 (s, 6H), 2.460 (m, 2H), 2.3-2.1 (m, 4H), 1.9-1.82 (m, 2H), 1.425 (d, 6H, J=6.4 Hz), 1.067 (d, 6H, J=6.0 Hz).

Example QK

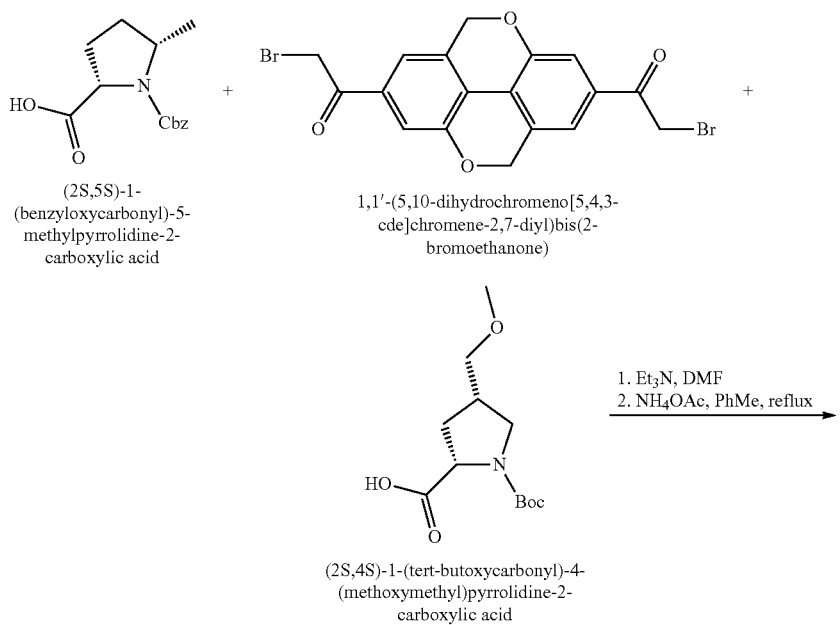

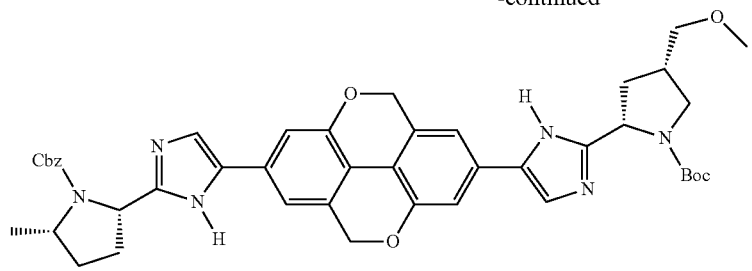

(2S,4S)-tert-butyl 2-(5-(7-(2-((2S,5S)-1-(benzyloxycarbonyl)-5-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate

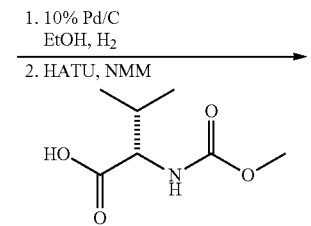

(S)-2-(methoxycarbonylamino)-3-methylbutanoic acid 1. 10% Pd/C EtOH, H₂
2. HATU, NMM

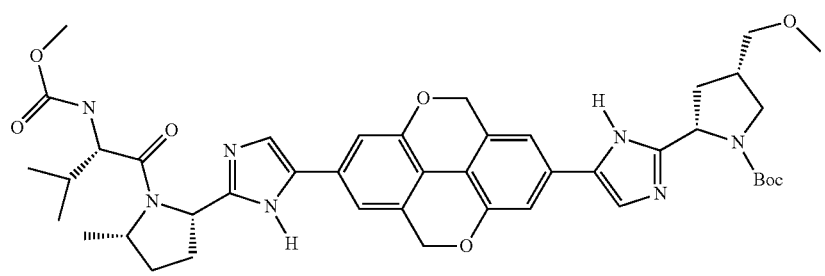

(2S,4S)-tert-butyl 2-(5-(7-(2-((2S,5S)-1-((S)-2-(methoxycarbonylamino)-3-methylbutanoyl)-5-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate

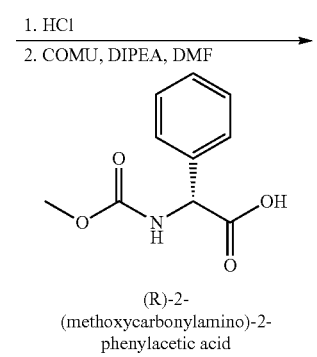

(R)-2-(methoxycarbonylamino)-2-phenylacetic acid

1. HCl
2. COMU, DIPEA, DMF

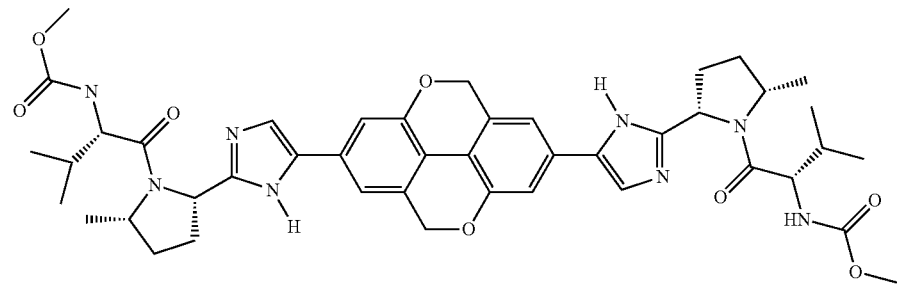

Dimethyl (2S,2'S)-1,1'-((2S,2'S,5S,5'S)-5,5'-(5,5'-(5,10-dihydrochromeno[5,4,3-cde]chromene-2,7-diyl)bis(1H-imidazole-5,2-diyl))bis(2-methylpyrrolidine-5,1-diyl))bis(3-methyl-1-oxobutane-2,1-diyl)dicarbamate (2S,4S)-tert-butyl 2-(5-(7-(2-((2S,5S)-1-(benzyloxycarbonyl)-5-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate: A mixture of 1,1'-(5,10-dihydrochromeno[5,4,3-cde]chromene-2,7-diyl)bis(2-bromoethanone) (1.08 g, 2.39 mmol)), (2S,5S)-1-(tert-butoxycarbonyl)-5-methylpyrrolidine-2-carboxylic acid (819 mg, 3.11 mmol), and (2S,4S)-1-(tert-butoxycarbonyl)-4-(methoxymethyl)pyrrolidine-2-carboxylic acid (806 mg, 3.11 mmol) in 24 mL DMF with triethylamine (1.25 mL, 7.18 mmol) was heated at 80° C. overnight. The solution was cooled to rt then diluted with EtOAc and washed successively with 1N HCl, saturated aqueous NaHCO₃, and brine. The organic phase was dried over Na₂SO₄ then concentrated to afford the crude mixture (1.86 grams). To the crude mixture (1.86 grams) ammonium acetate (2.65 g, 34.3 mmol), toluene (20 mL) and 2-methoxypropanol (2.5 mL) was heated at reflux overnight. The solution was cooled to rt then diluted with EtOAc and washed successively with saturated aqueous NaHCO₃ and brine. The organic phase was dried over Na₂SO₄, concentrated, and purified by silica gel chromatography (50% to 100% EtOAc/Hexanes) to afford (2S,4S)-tert-butyl 2-(5-(7-(2-((2S,5S)-1-(benzyloxycarbonyl)-5-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate (610 mg, 33%).

(2S,4S)-tert-butyl 2-(5-(7-(2-((2S,5S)-1-((S)-2-(methoxycarbonylamino)-3-methylbutanoyl)-5-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate: (2S,4S)-tert-butyl 2-(5-(7-(2-((2S,5S)-1-(benzyloxycarbonyl)-5-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate (300 mg, 0.38 mmol) 10 mL ethanol, and 19 mg 10% Pd/C was stirred under an atmosphere of hydrogen (balloon) overnight. Filtration through celite and concentration afforded the crude amine. The crude amine was dissolved in DMF (4 mL) and then (S)-2-(methoxycarbonylamino)-3-methylbutanoic acid (66 mg, 0.38 mmol), HATU (160 mg, 0.42 mmol) and N-methylmorpholine (0.084 mL, 0.76 mmol) were added. After 2 h, the reaction was diluted with EtOAc and washed successively with saturated aqueous NaHCO₃, 5% LiCl, and brine. The organic phase was dried over Na₂SO₄, concentrated, and purified by silica gel chromatography (1% to 20% MeOH/EtOAc) to afford (2S,4S)-tert-butyl 2-(5-(7-(2-((2S,5S)-1-((S)-2-(methoxycarbonylamino)-3-methylbutanoyl)-5-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate (177 mg, 58%).

Dimethyl (2S,2'S)-1,1'-((2S,2'S,5S,5'S)-5,5'-(5,5'-(5,10-dihydrochromeno[5,4,3-cde]chromene-2,7-diyl)bis(1H-imidazole-5,2-diyl))bis(2-methylpyrrolidine-5,1-diyl))bis(3-methyl-1-oxobutane-2,1-diyl)dicarbamate: A solution of (2S,4S)-tert-butyl 2-(5-(7-(2-((2S,5S)-1-((S)-2-(methoxycarbonylamino)-3-methylbutanoyl)-5-methylpyrrolidin-2-yl)-1H-imidazol-5-yl)-5,10-dihydrochromeno[5,4,3-cde]chromen-2-yl)-1H-imidazol-2-yl)-4-(methoxymethyl)pyrrolidine-1-carboxylate (177 mg, 0.11 mmol) in 1.25 N HCl in EtOH (3 mL) was heated to 50° C. for 3 h. The reaction was concentrated to afford the crude HCl salt of methyl (S)-1-((2S,5S)-2-(5-(7-(2-((2S,4S)-4-(methoxymethyl)pyrrolidin-2-yl)-1H-imidazol-5-yl)-5,10-dihydrochromeno[5,4,3-cde]chromen-2-yl)-1H-imidazol-2-yl)-5-methylpyrrolidin-1-yl)-3-methyl-1-oxobutan-2-ylcarbamate (164 mg). A portion of the HCl salt of methyl (S)-1-((2S,5S)-2-(5-(7-(2-((2S,4S)-4-(methoxymethyl)pyrrolidin-2-yl)-1H-imidazol-5-yl)-5,10-dihydrochromeno[5,4,3-cde]chromen-2-yl)-1H-imidazol-2-yl)-5-methylpyrrolidin-1-yl)-3-methyl-1-oxobutan-2-ylcarbamate (124 mg) was dissolved in DMF (2 mL) and then (R)-2-(methoxycarbonylamino)-2-phenylacetic acid (38 mg, 0.18 mmol), COMU (64 mg, 0.15 mmol), diisopropylethylamine (0.078 mL, 0.45 mmol) were added. After stirring for 2 h at room temperature, the reaction was quenched with 1N HCl (0.200 mL) and purified by HPLC. After lyophilization, the TFA salt was dissolved in EtOAc and washed with saturated NaHCO₃. The organic phase was dried over Na₂SO₄ and concentrated. The free base was then dissolved in MeCN/H₂O and lyophilized to afford dimethyl (2S,2'S)-1,1'-((2S,2'S,5S,5'S)-5,5'-(5,5'-(5,10-dihydrochromeno[5,4,3-cde]chromene-2,7-diyl)bis(1H-imidazole-5,2-diyl))bis(2-methylpyrrolidine-5,1-diyl))bis(3-methyl-1-oxobutane-2,1-diyl)dicarbamate (42 mg, 45%). LCMS-ESI⁺: calculated for $C_{44}H_{54}N_8O_8$: 886.4; observed [M+1]⁺: 888.1.

Example QL

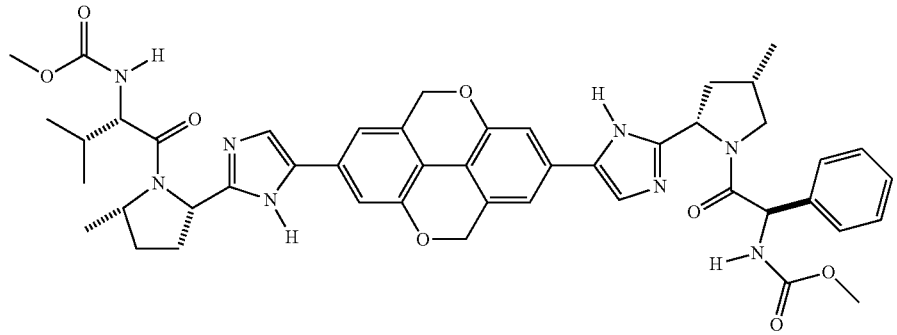

1517 methyl [(1R)-2-{(2S,4S)-2-[5-(7-{2-[(2S,5S)-1-{(2S)-2-[(methoxycarbonyl)amino]-3-methylbutanoyl}-5-methylpyrrolidin-2-yl]-1H-imidazol-5-yl}-5,10-dihydrochromeno[5,4,3-cde]chromen-2-yl)-1H-imidazol-2-yl]-4-methylpyrrolidin-1-yl}-2-oxo-1-phenylethyl]carbamate Methyl [(1R)-2-{(2S,4S)-2-[5-(7-{2-[(2S,5S)-1-{(2S)-2-[(methoxycarbonyl)amino]-3-methylbutanoyl}-5-methylpyrrolidin-2-yl]-1H-imidazol-5-yl}-5,10-dihydrochromeno[5,4,3-cde]chromen-2-yl)-1H-imidazol-2-yl]-4-methylpyrrolidin-1-yl}-2-oxo-1-phenylethyl]carbamate: The title compound was prepared as described for Example QK, substituting (2S,4S)-1-(tert-butoxycarbonyl)-4-methylpyrrolidine-2-carboxylic acid for (2S,4S)-1-(tert-butoxycarbonyl)-4-(methoxymethyl)pyrrolidine-2-carboxylic acid. LCMS-ESI$^+$: calculated for $C_{47}H_{52}N_8O_8$: 856.4; observed [M+1]$^+$: 858.3.

Example QM

1518

Methyl {(2S)-1-[(2S,4S)-2-[5-(7-{2-[(2S,5S)-1-{(2S)-2-[(methoxycarbonyl)amino]-3-methylbutanoyl}-5-methylpyrrolidin-2-yl]-1H-imidazol-5-yl}-5,10-dihydrochromeno[5,4,3-cde]chromen-2-yl)-1H-imidazol-2-yl]-4-(methoxymethyl)pyrrolidin-1-yl]-3-methyl-1-oxobutan-2-yl}carbamate: To the HCl salt of methyl (S)-1-((2S,5S)-2-(5-(7-(2-((2S,4S)-4-(methoxymethyl)pyrrolidin-2-yl)-1H-imidazol-5-yl)-5,10-dihydrochromeno[5,4,3-cde]chromen-2-yl)-1H-imidazol-2-yl)-5-methylpyrrolidin-1-yl)-3-methyl-1-oxobutan-2-ylcarbamate (40 mg) in DMF (1 mL) was added (S)-2-(methoxycarbonylamino)-3-methylbutanoic acid (13 mg, 0.075 mmol), HATU (21 mg, 0.055 mmol) and N-methylmorpholine (0.016 mL, 0.15 mmol). After 3 h, the mixture was quenched with 1N HCl (0.100 mL) and then purified by HPLC to afford methyl {(2S)-1-[(2S,4S)-2-[5-(7-{2-[(2S,5S)-1-{(2S)-2-[(methoxycarbonyl)amino]-3-methylbutanoyl}-5-methylpyrrolidin-2-yl]-1H-imidazol-5-yl}-5,10-dihydrochromeno[5,4,3-cde]chromen-2-yl)-1H-imidazol-2-yl]-4-(methoxymethyl)pyrrolidin-1-yl]-3-methyl-1-oxobutan-2-yl}carbamate (43 mg). LCMS-ESI$^+$: calculated for $C_{45}H_{56}N_8O_9$: 852.4; observed [M+1]$^+$: 853.1.

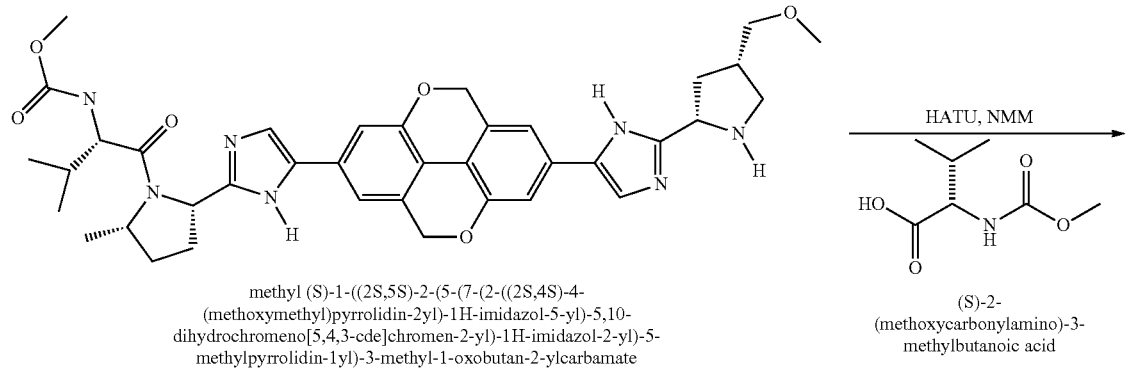

methyl (S)-1-((2S,5S)-2-(5-(7-(2-((2S,4S)-4-(methoxymethyl)pyrrolidin-2yl)-1H-imidazol-5-yl)-5,10-dihydrochromeno[5,4,3-cde]chromen-2-yl)-1H-imidazol-2-yl)-5-methylpyrrolidin-1yl)-3-methyl-1-oxobutan-2-ylcarbamate (S)-2-(methoxycarbonylamino)-3-methylbutanoic acid

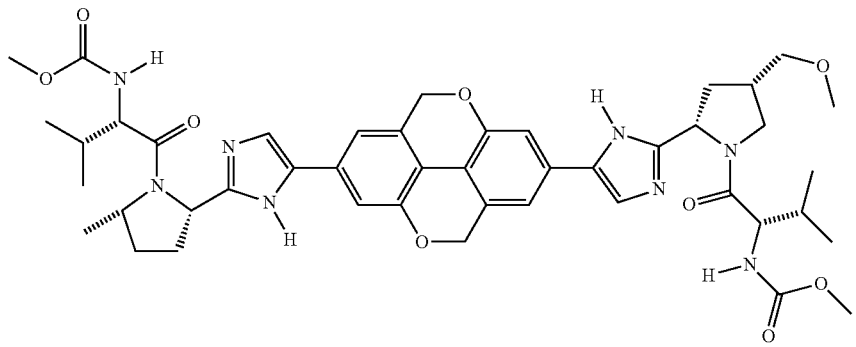

methyl {(2S)-1-[(2S,4S)-2-[5-(7-{2-[(2S,5S)-1-{(2S)-2-[(methoxycarbonyl)amino]-3-methylbutanoyl}-5-methylpyrrolidin-2-yl]-1H-imidazol-5-yl}-5,10-dihydrochromeno[5,4,3-cde]chromen-2-yl)-1H-imidazol-2-yl]-4-(methoxymethyl)pyrrolidin-1-yl]-3-methyl-1-oxobutan-2-yl}carbamate Compounds 290-539
Using procedures similar to those described herein, the following compounds of the invention were prepared.
| # | Compound | LCMS (observed (M + H)+) |
|---|---|---|
| 290 | 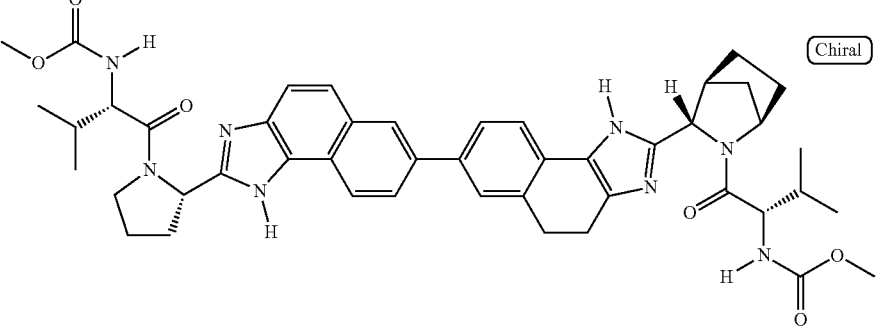 | 816.41 |
| 291 | 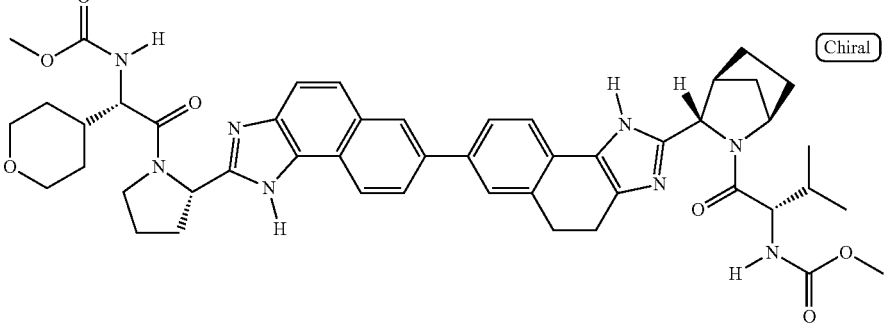 | 858.39 |
| 292 | 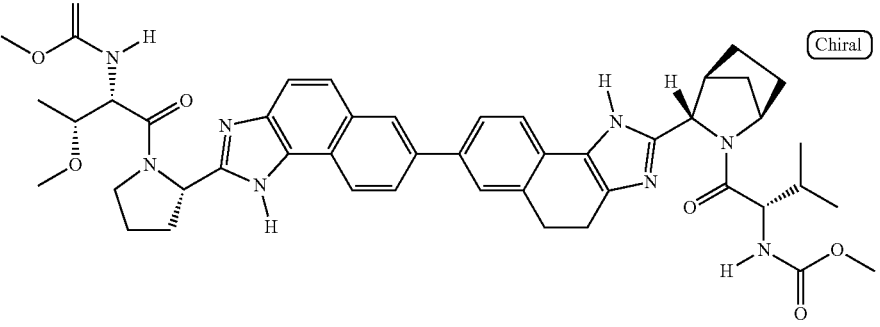 | 832.68 |
| 293 | 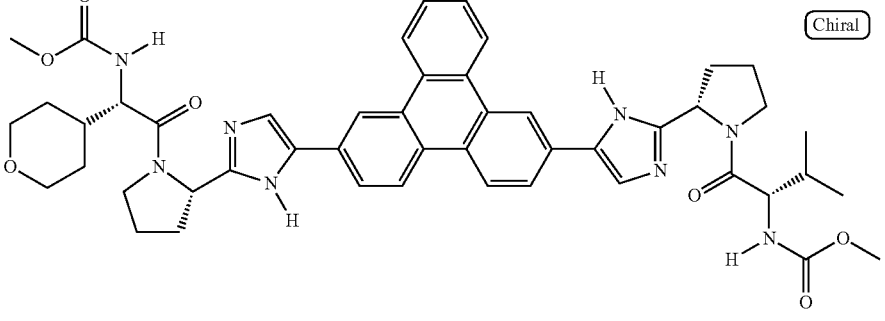 | 856.31 |

| # | Compound | LCMS (observed) (M + H)+ |
|---|---|---|
| 294 | | 893.82 |
| 295 | | 837.18 |
| 296 | | 855.81 |
| 297 | | 898.16 |

| # | Compound | LCMS (observed (M + H)+) |
|---|----------|--------------------------|
| 298 | 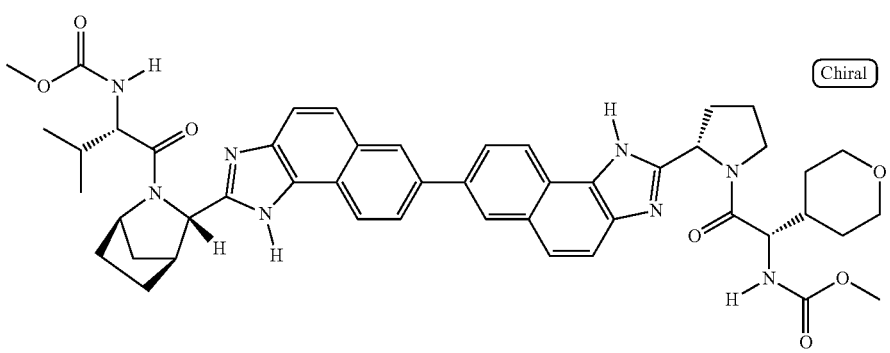 [SMILES: COC(=O)N[C@H](C(=O)N1[C@@H]2CC[C@@H](C2)[C@H]1c1nc2ccc3cc(-c4ccc5c(ccc6nc([C@@H]7CCCN7C(=O)[C@@H](NC(=O)OC)C7CCOCC7)[nH]c65)c4)ccc3c2[nH]1)C(C)C] | 855.39 |
| 299 | 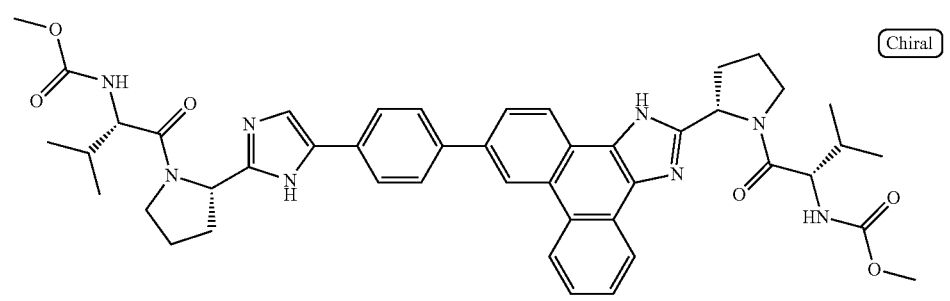 | 813.74 |
| 300 | 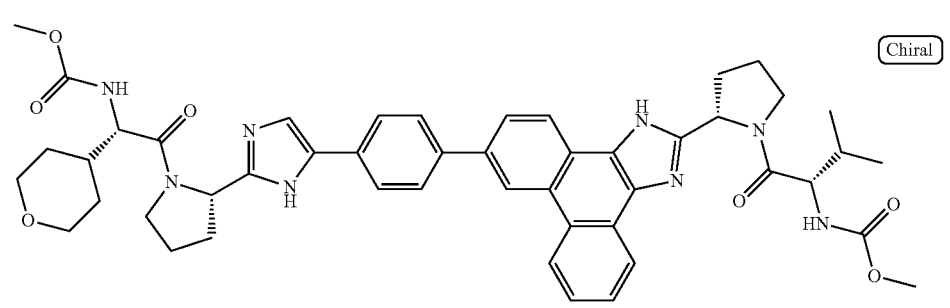 | 855.76 |
| 301 | 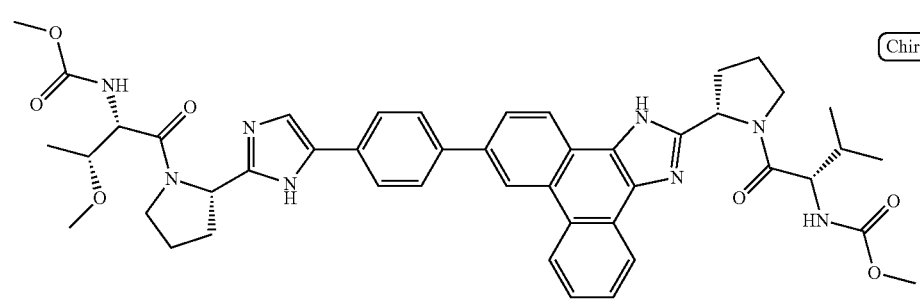 | 829.68 |

1525　　　　　　　　　　　　　　　　　　　　1526
-continued
| # | Compound | LCMS (observed (M + H)+) |
|---|---|---|
| 302 | 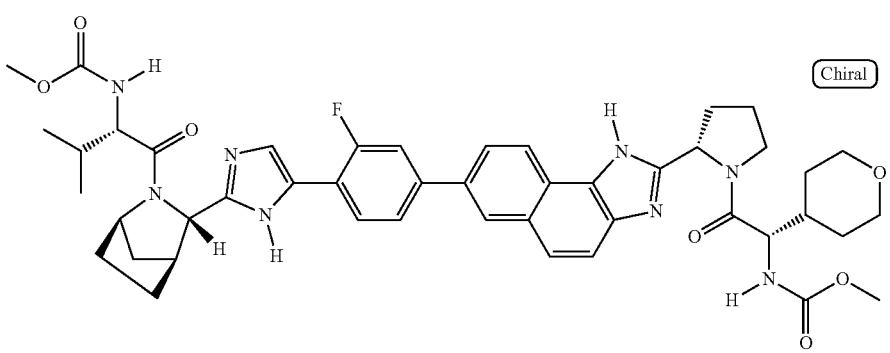 [SMILES: COC(=O)N[C@H](C(=O)N1[C@@H]2CC[C@@H](C2)[C@H]1c1ncc(-c2ccc(-c3ccc4c(ccc5nc([C@@H]6CCCN6C(=O)[C@@H](NC(=O)OC)C6CCOCC6)[nH]c54)c3)cc2F)[nH]1)C(C)C] | 849.29 |
| 303 | 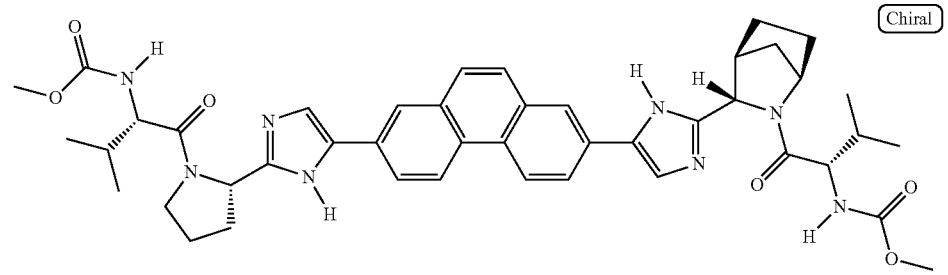 | 789.67 |
| 304 | 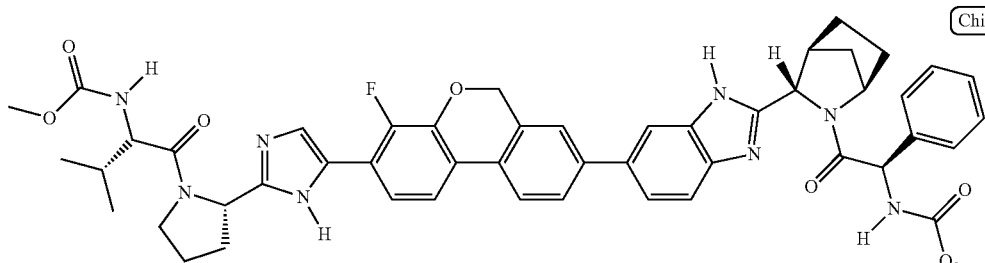 | 895.76 |
| 305 | 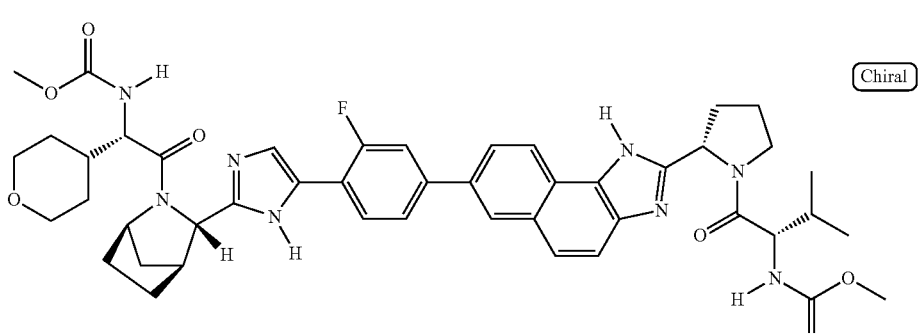 | 849.65 |

| # | Compound | LCMS (observed (M + H)+) |
|---|----------|--------------------------|
| 306 | 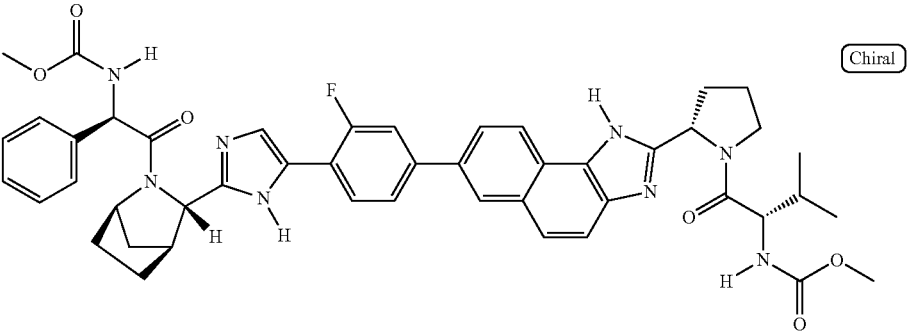 Chiral | 841.99 |
| 307 | 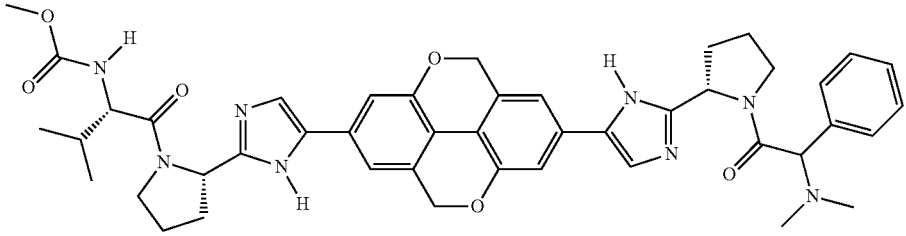 [SMILES: COC(=O)N[C@H](C(=O)N1CCC[C@H]1c1ncc(-c2cc3c4c(c2)OCc2cc(-c5cnc([C@@H]6CCCN6C(=O)C(c6ccccc6)N(C)C)[nH]5)cc(c2-4)OC3)[nH]1)C(C)C] | 799.2 |
| 308 | 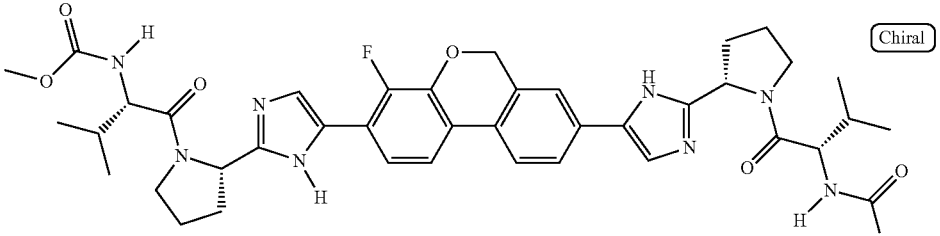 Chiral | 785.61 |
| 309 | 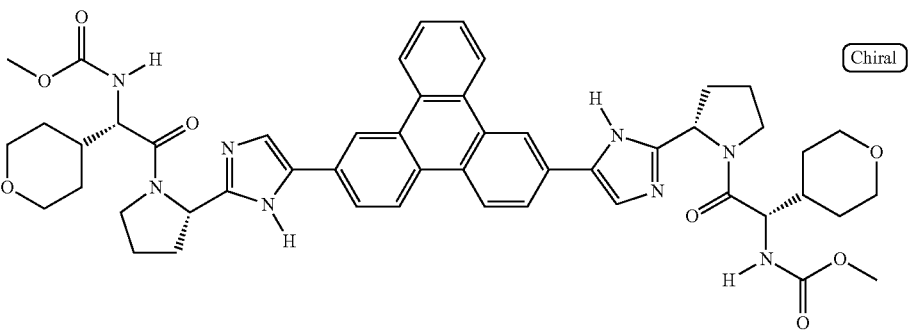 [SMILES: COC(=O)N[C@H](C(=O)N1CCC[C@H]1c1ncc(-c2ccc3c4ccc(-c5cnc([C@@H]6CCCN6C(=O)[C@@H](NC(=O)OC)C6CCOCC6)[nH]5)cc4c4ccccc4c3c2)[nH]1)C1CCOCC1] Chiral | 897.6 |
| 310 | 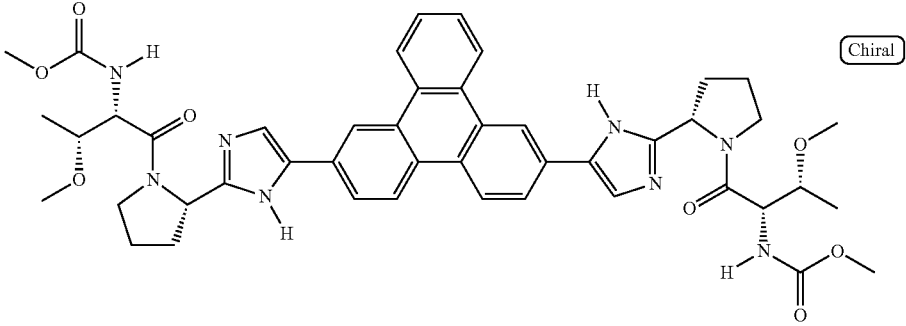 Chiral | 846.18 |

| # | Compound | LCMS (observed (M + H)+) |
|---|---|---|
| 311 | 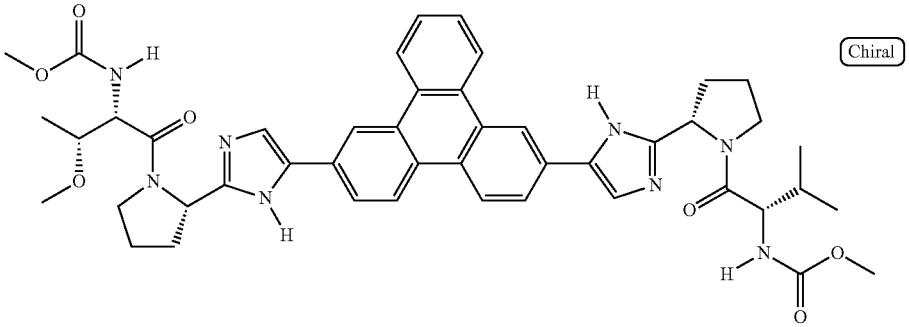 | 830.27 |
| 312 | 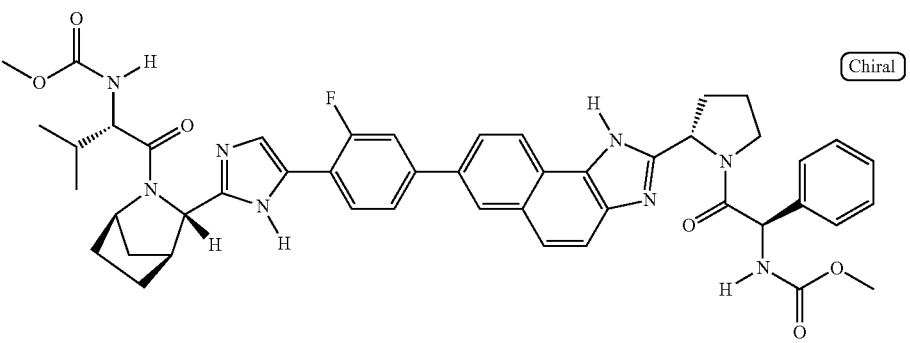 [SMILES: COC(=O)N[C@H](C(=O)N1[C@@H]2CC[C@@H](C2)[C@H]1c1ncc(-c2ccc(-c3ccc4c(ccc5nc([C@@H]6CCCN6C(=O)[C@H](NC(=O)OC)c6ccccc6)[nH]c54)c3)cc2F)[nH]1)C(C)C] | 842.39 |
| 313 | 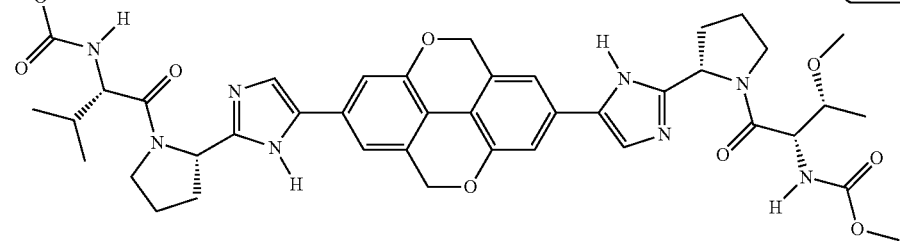 | 811.4 |
| 314 | 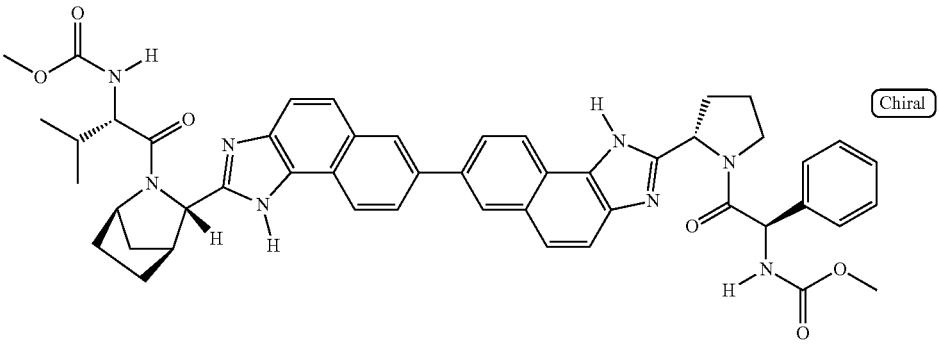 [SMILES: COC(=O)N[C@H](C(=O)N1[C@@H]2CC[C@@H](C2)[C@H]1c1nc2ccc3cc(-c4ccc5c(ccc6nc([C@@H]7CCCN7C(=O)[C@H](NC(=O)OC)c7ccccc7)[nH]c65)c4)ccc3c2[nH]1)C(C)C] | 847.27 |

-continued
| # | Compound | LCMS (observed) (M + H)+ |
|---|---|---|
| 315 | 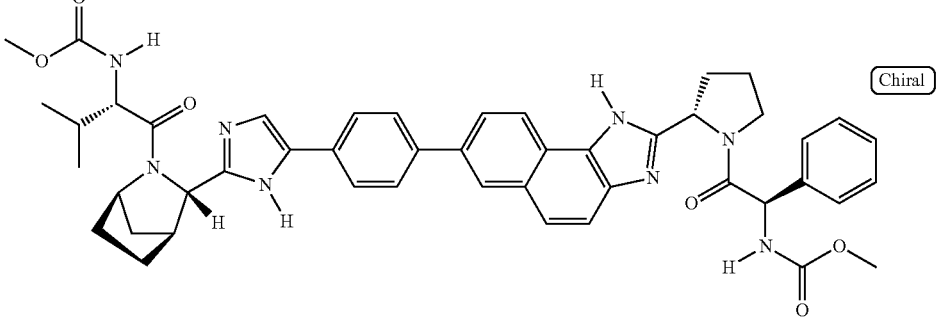 | 823.33 |
| 316 | 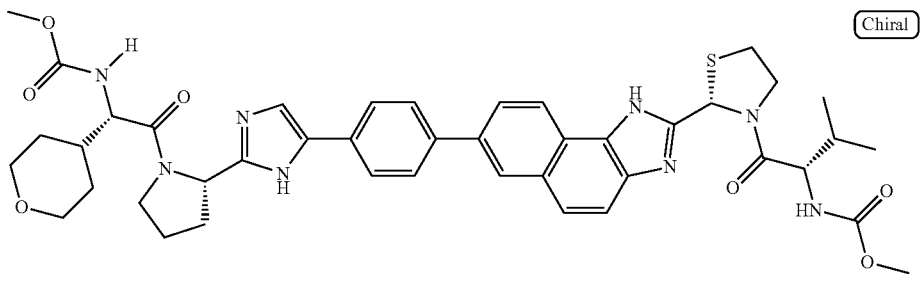 | 823.58 |
| 317 | 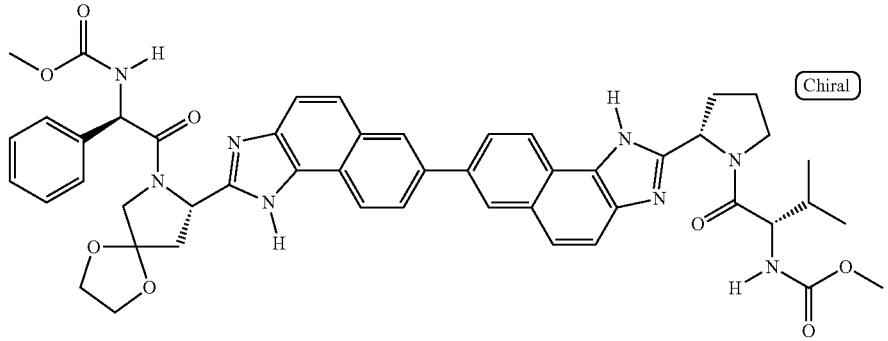 | 879.39 |
| 318 | 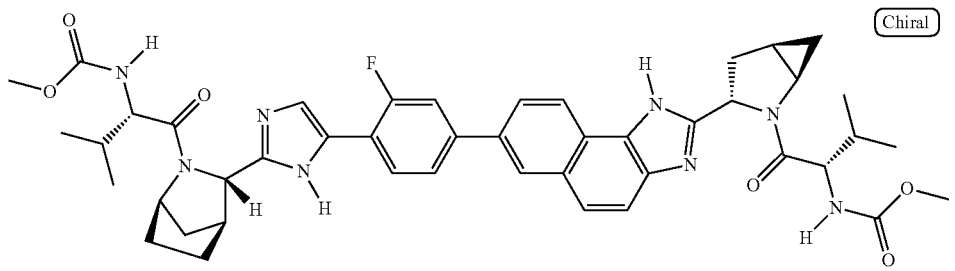 | 819.76 |
| 319 | 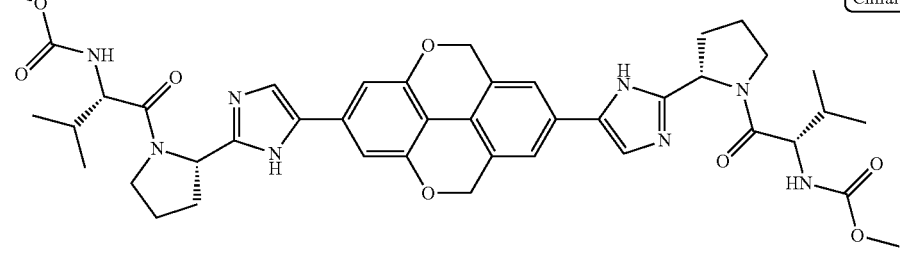 | 795.63 |

-continued

| # | Compound | LCMS (observed (M + H)+) |
|---|---|---|
| 320 | | 861.72 |
| 321 | | 835.74 |
| 322 | | 869.71 |
| 323 | | 880.29 |
| 324 | | 853.27 |

-continued

| # | Compound | LCMS (observed (M + H)+) |
|---|---|---|
| 325 | | 847.8 |
| 326 | | 873.2 |
| 327 | | 915.18 |
| 328 | | 889.76 |

-continued
| # | Compound | LCMS (observed (M + H)+) |
|---|---|---|
| 329 | 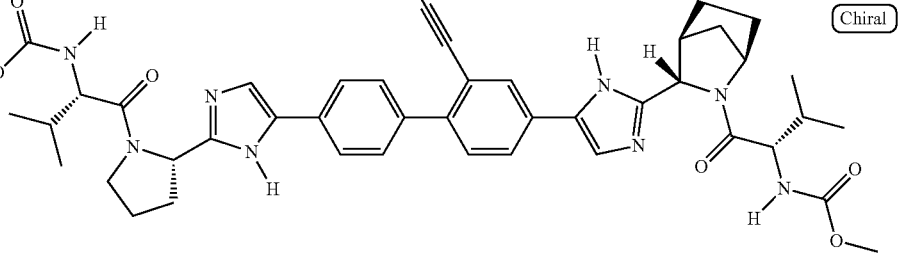 | 803.61 |
| 330 | 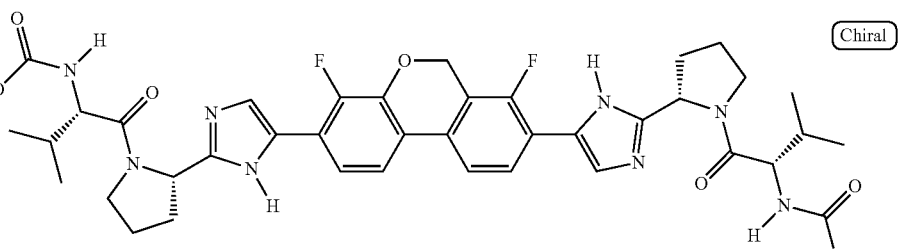 | 803.71 |
| 331 | 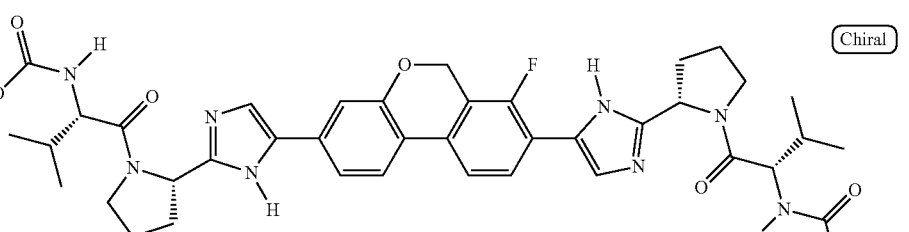 | 785.7 |
| 332 | 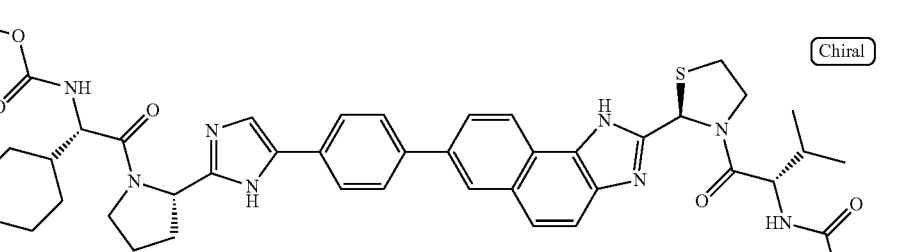 | 823.69 |
| 333 | 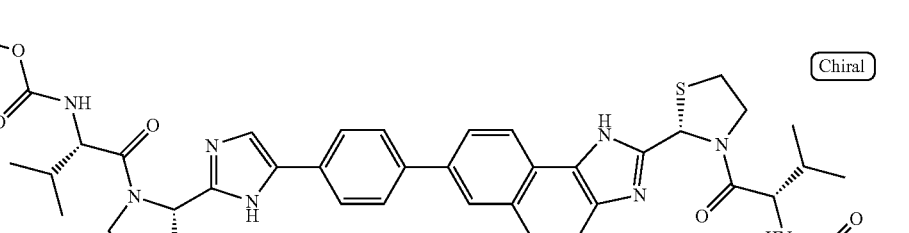 | 781.73 |

| # | Compound | LCMS (observed (M + H)+) |
|---|---|---|
| 334 | 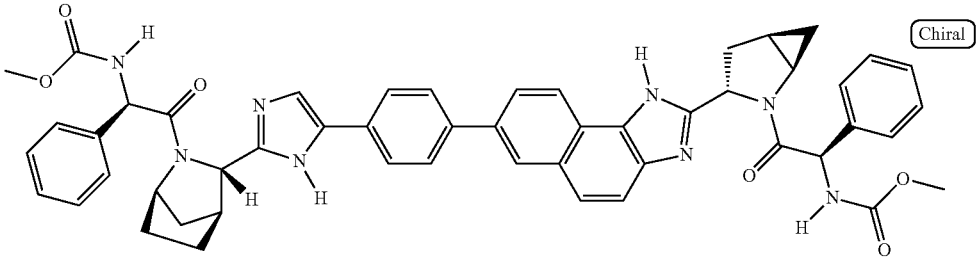 | 869.76 |
| 335 | 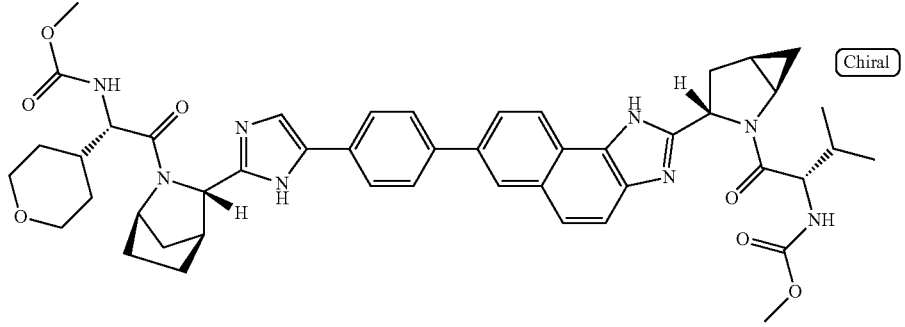 [SMILES: COC(=O)N[C@H](C(=O)N1[C@@H]2C[C@@H]2C[C@H]1c1nc2ccc3cc(-c4ccc(-c5cnc([C@@H]6[C@H]7CC[C@H](C7)N6C(=O)[C@@H](NC(=O)OC)C6CCOCC6)[nH]5)cc4)ccc3c2[nH]1)C(C)C] | 843.79 |
| 336 | 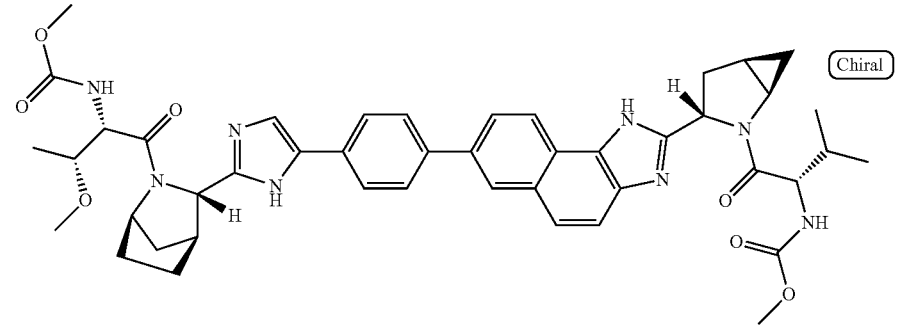 [SMILES: COC(=O)N[C@H](C(=O)N1[C@@H]2C[C@@H]2C[C@H]1c1nc2ccc3cc(-c4ccc(-c5cnc([C@@H]6[C@H]7CC[C@H](C7)N6C(=O)[C@@H](NC(=O)OC)[C@@H](C)OC)[nH]5)cc4)ccc3c2[nH]1)C(C)C] | 817.78 |
| 337 | 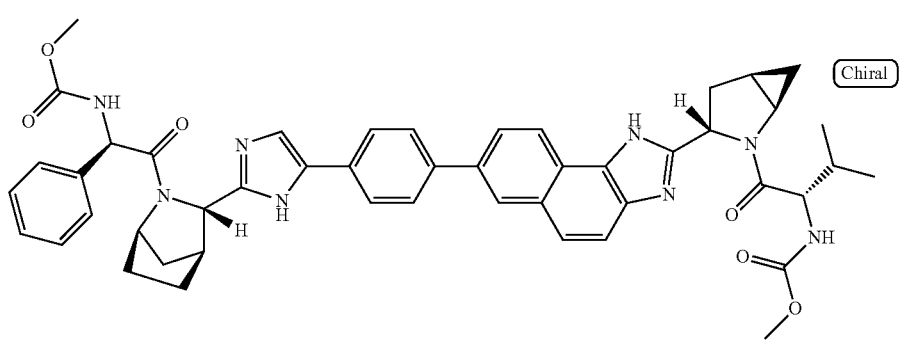 [SMILES: COC(=O)N[C@H](C(=O)N1[C@@H]2C[C@@H]2C[C@H]1c1nc2ccc3cc(-c4ccc(-c5cnc([C@@H]6[C@H]7CC[C@H](C7)N6C(=O)[C@H](NC(=O)OC)c6ccccc6)[nH]5)cc4)ccc3c2[nH]1)C(C)C] | 835.72 |

| # | Compound | LCMS (observed (M + H)+) |
|---|----------|--------------------------|
| 338 | 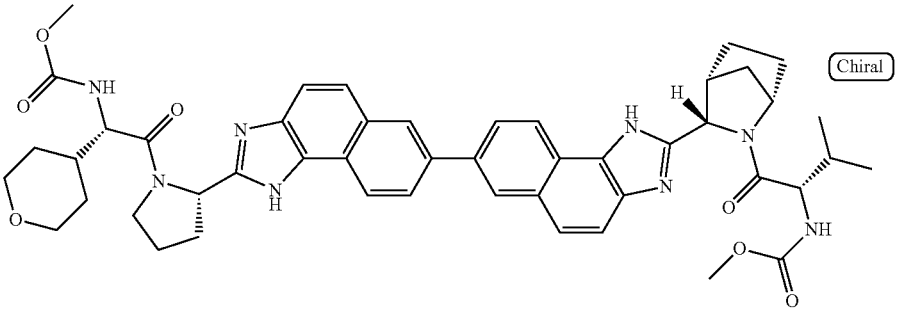 [SMILES: COC(=O)N[C@H](C(=O)N1[C@H]2CC[C@H](C2)[C@H]1c1nc2ccc3cc(-c4ccc5c(ccc6nc([C@@H]7CCCN7C(=O)[C@@H](NC(=O)OC)C7CCOCC7)[nH]c65)c4)ccc3c2[nH]1)C(C)C] | 855.75 |
| 339 | 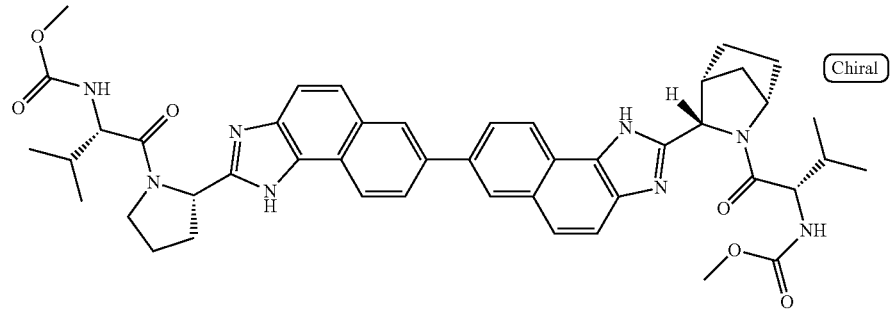 [SMILES: COC(=O)N[C@H](C(=O)N1CCC[C@H]1c1nc2ccc3cc(-c4ccc5c(ccc6nc([C@@H]7[C@@H]8CC[C@@H](C8)N7C(=O)[C@@H](NC(=O)OC)C(C)C)[nH]c65)c4)ccc3c2[nH]1)C(C)C] | 813.78 |
| 340 | 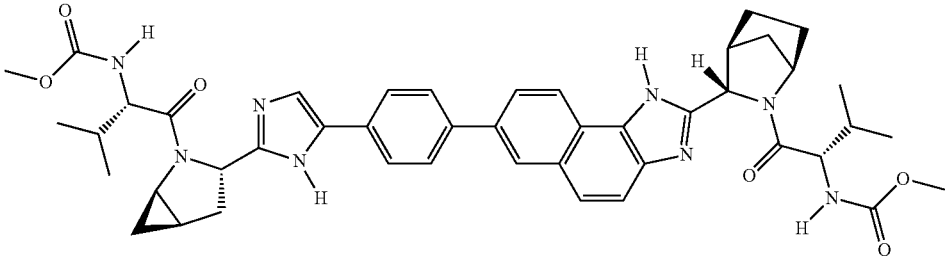 | 801.75 |
| 341 | 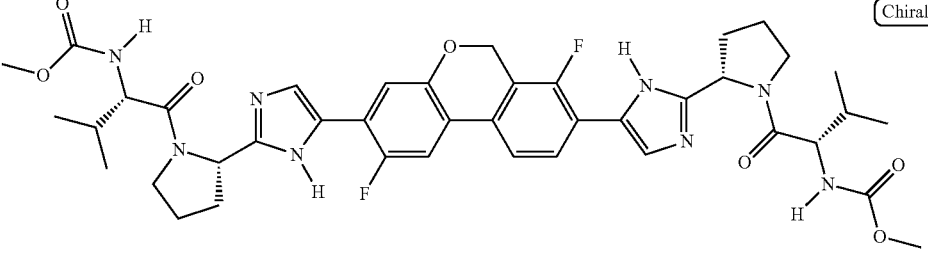 | 803.66 |
| 342 | 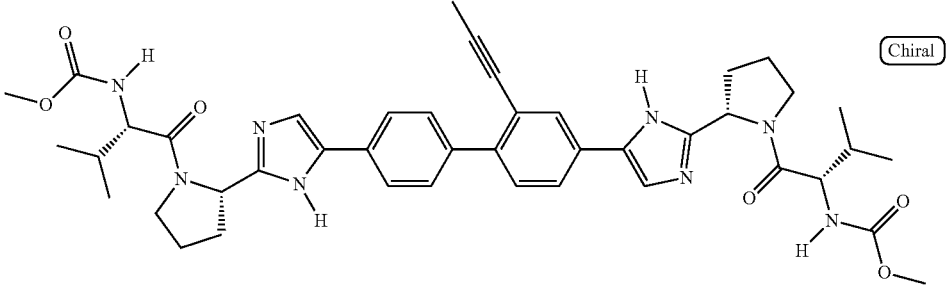 | 777.68 |

-continued
| # | Compound | LCMS (observed) (M + H)+ |
|---|---|---|
| 343 | 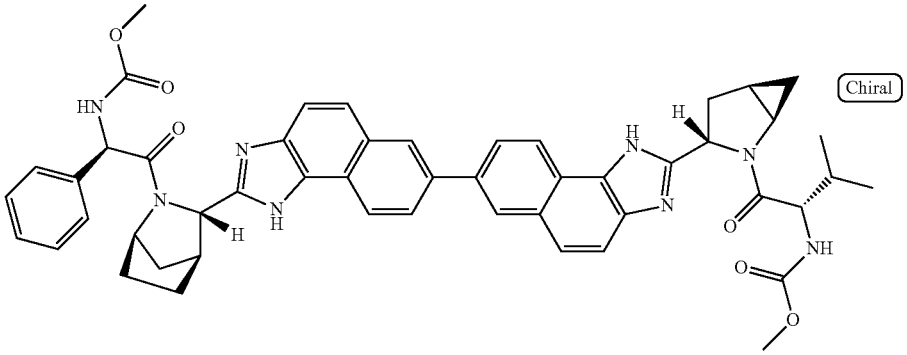 [SMILES: COC(=O)N[C@H](C(=O)N1[C@@H]2C[C@@H]2C[C@H]1c1nc2ccc3cc(-c4ccc5c(ccc6nc([C@@H]7[C@H]8CC[C@H](C8)N7C(=O)[C@H](NC(=O)OC)c7ccccc7)[nH]c65)c4)ccc3c2[nH]1)C(C)C] | 859.8 |
| 344 | 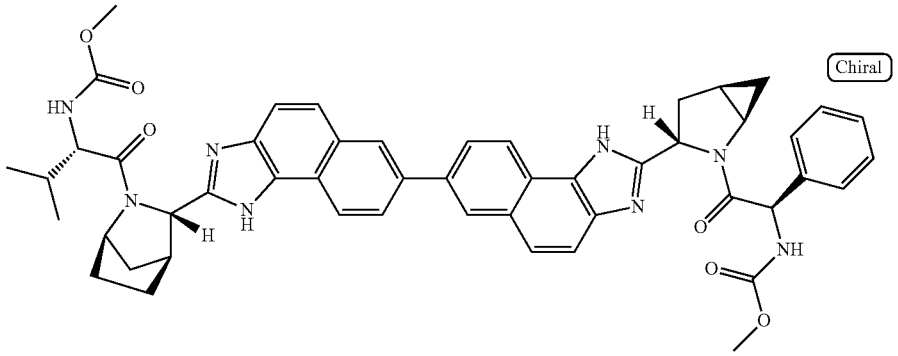 [SMILES: COC(=O)N[C@H](C(=O)N1[C@@H]2CC[C@@H](C2)[C@H]1c1nc2ccc3cc(-c4ccc5c(ccc6nc([C@@H]7C[C@H]8C[C@H]8N7C(=O)[C@H](NC(=O)OC)c7ccccc7)[nH]c65)c4)ccc3c2[nH]1)C(C)C] | 859.8 |
| 345 | 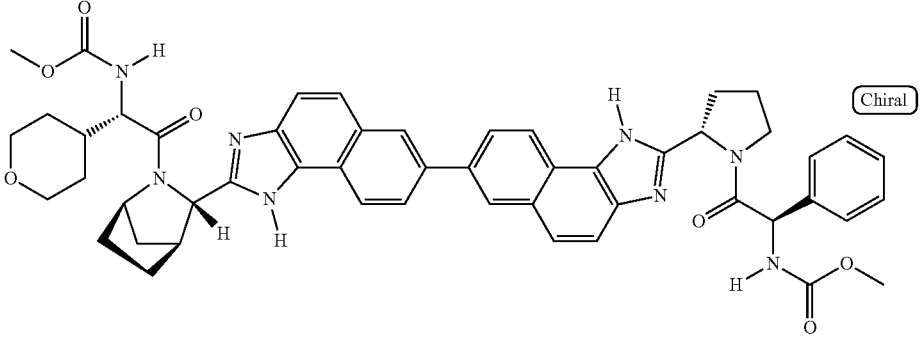 | 889.78 |
| 346 | 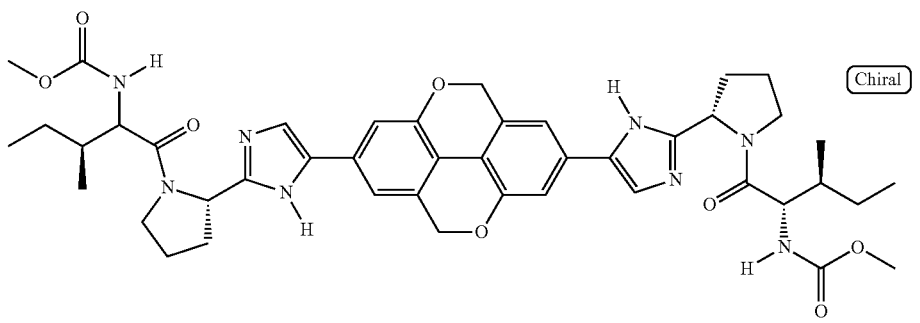 | 823.9 |

-continued

| # | Compound | LCMS (observed (M + H)+) |
|---|---|---|
| 347 | | 819.71 |
| 348 | | 811.67 Chiral |
| 349 | | 827.76 Chiral |
| 350 | | 869.82 Chiral |

| # | Compound | LCMS (observed (M + H)+) |
|---|----------|--------------------------|
| 351 | 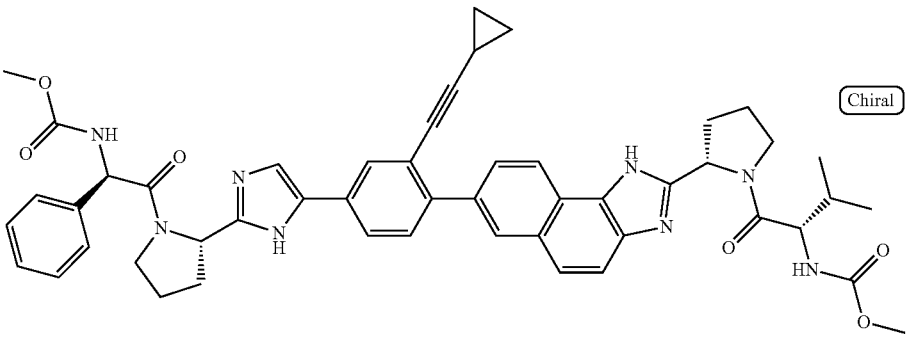 | 861.75 |
| 352 | 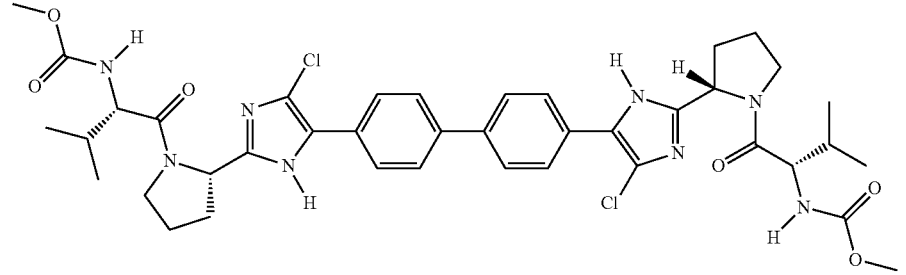 | 808.8 |
| 353 | 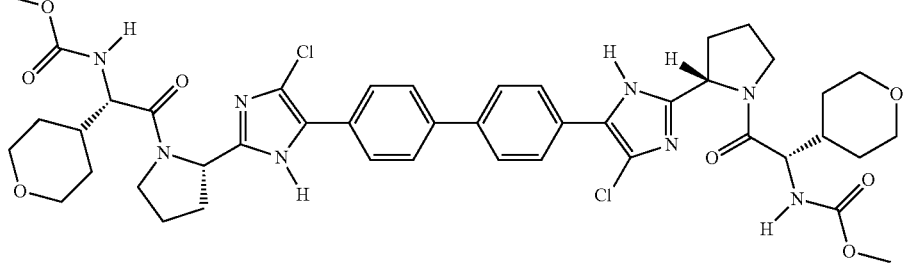 | 891.91 |
| 354 | 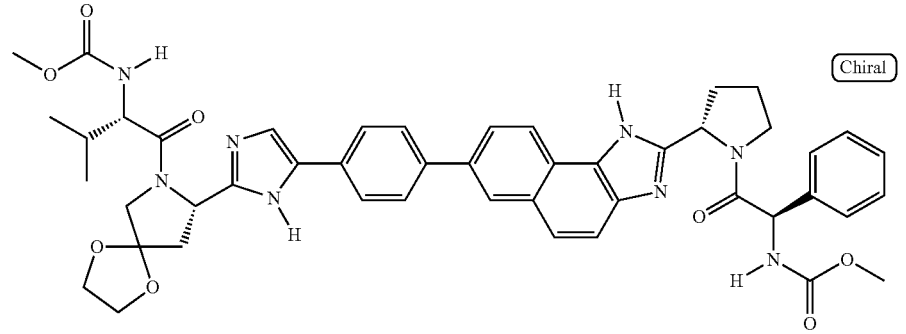 [SMILES: COC(=O)N[C@H](C(=O)N1CC2(C[C@H]1c1ncc(-c3ccc(-c4ccc5c(ccc6nc([C@@H]7CCCN7C(=O)[C@H](NC(=O)OC)c7ccccc7)[nH]c65)c4)cc3)[nH]1)OCCO2)C(C)C] | 856.3 |

| # | Compound | LCMS (observed (M + H)+) |
|---|---|---|
| 355 | 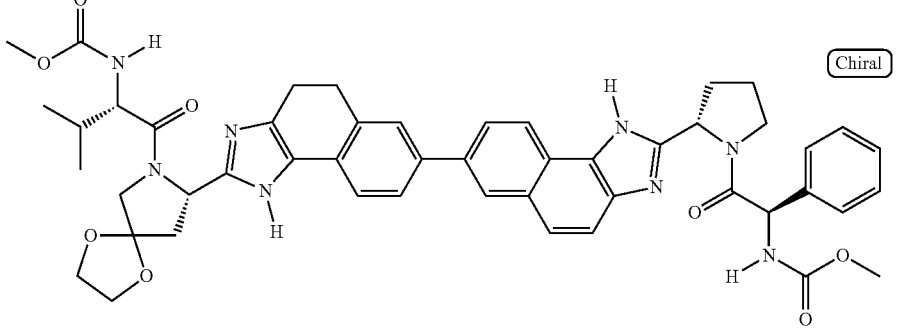 | 881.96 |
| 356 | 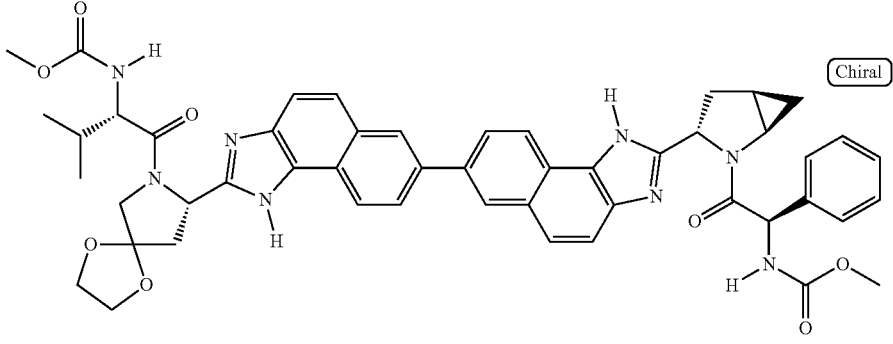 [SMILES: COC(=O)N[C@H](C(=O)N1CC2(C[C@H]1c1nc3ccc4cc(-c5ccc6c(ccc7nc([C@@H]8C[C@H]9C[C@H]9N8C(=O)[C@H](NC(=O)OC)c8ccccc8)[nH]c76)c5)ccc4c3[nH]1)OCCO2)C(C)C] | 891.68 |
| 357 | 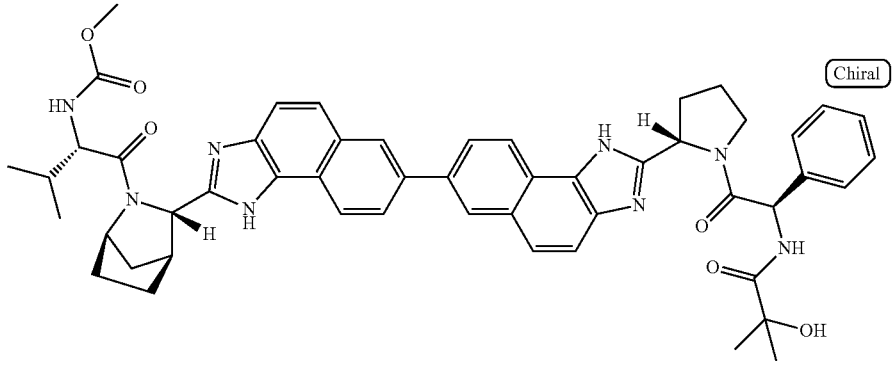 [SMILES: COC(=O)N[C@H](C(=O)N1[C@@H]2CC[C@@H](C2)[C@H]1c1nc2ccc3cc(-c4ccc5c(ccc6nc([C@@H]7CCCN7C(=O)[C@H](NC(=O)C(C)(C)O)c7ccccc7)[nH]c65)c4)ccc3c2[nH]1)C(C)C] | 875.8 |
| 358 | 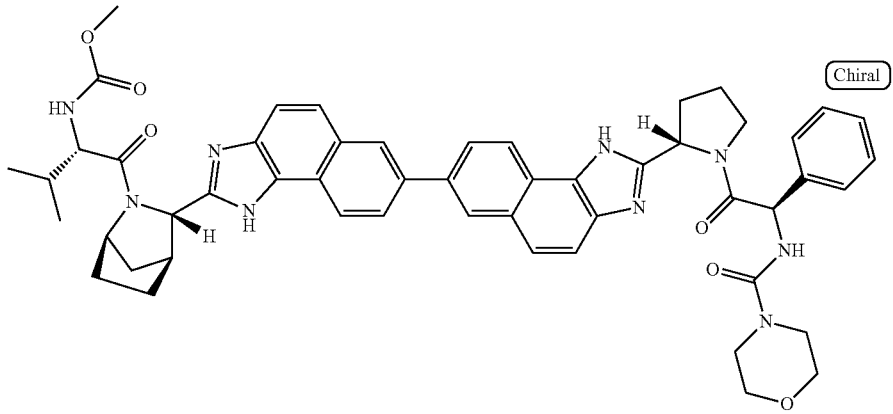 [SMILES: COC(=O)N[C@H](C(=O)N1[C@@H]2CC[C@@H](C2)[C@H]1c1nc2ccc3cc(-c4ccc5c(ccc6nc([C@@H]7CCCN7C(=O)[C@H](NC(=O)N7CCOCC7)c7ccccc7)[nH]c65)c4)ccc3c2[nH]1)C(C)C] | 902.8 |

-continued

| # | Compound | LCMS (observed (M + H)+) |
|---|---|---|
| 359 | | 775.29 |
| 360 | | 850.56 |
| 361 | | 785.64 |
| 362 | | 815.68 |
| 363 | | 845.74 |

-continued
| # | Compound | LCMS (observed (M + H)+) |
|---|---|---|
| 364 | 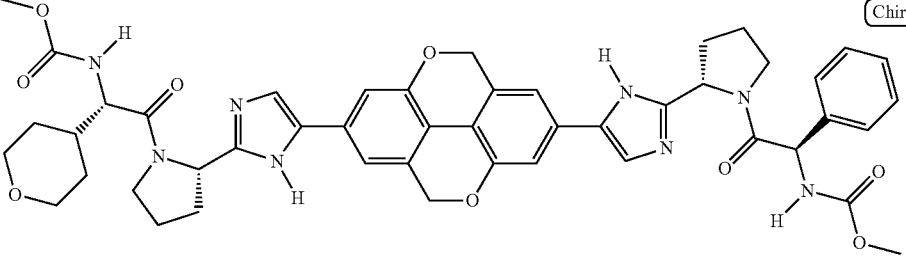 | 872.1 |
| 365 | 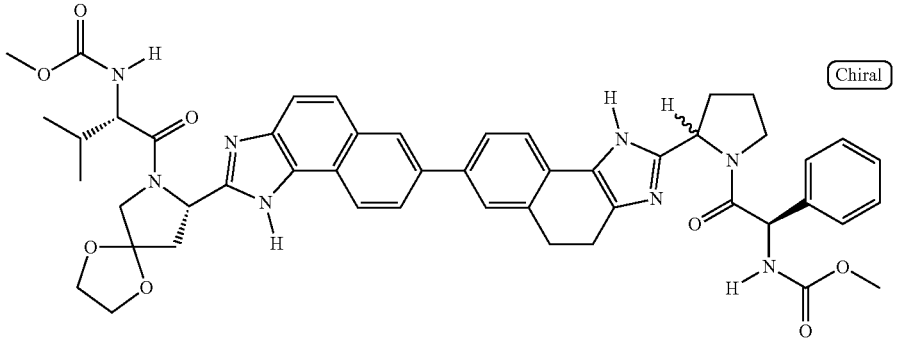 [SMILES: COC(=O)N[C@H](C(=O)N1CC2(C[C@H]1c1nc3ccc4cc(-c5ccc6c(c5)CCc5nc(C7CCCN7C(=O)[C@H](NC(=O)OC)c7ccccc7)[nH]c5-6)ccc4c3[nH]1)OCCO2)C(C)C] | 882.02 |
| 366 | 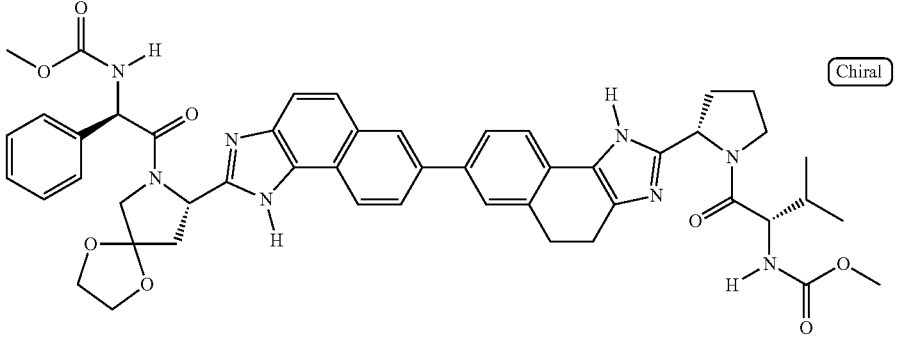 | 881.85 |
| 367 | 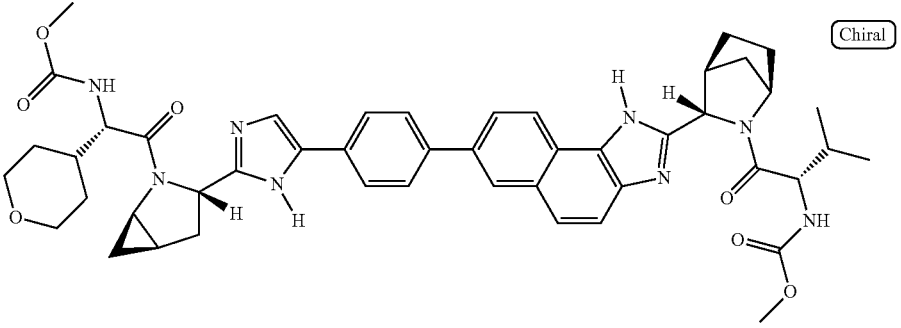 [SMILES: COC(=O)N[C@H](C(=O)N1[C@@H]2CC[C@@H](C2)[C@H]1c1nc2ccc3cc(-c4ccc(-c5cnc([C@@H]6C[C@H]7C[C@H]7N6C(=O)[C@@H](NC(=O)OC)C6CCOCC6)[nH]5)cc4)ccc3c2[nH]1)C(C)C] | 843.8 |

-continued
| # | Compound | LCMS (observed (M + H)+) |
|---|---|---|
| 368 | 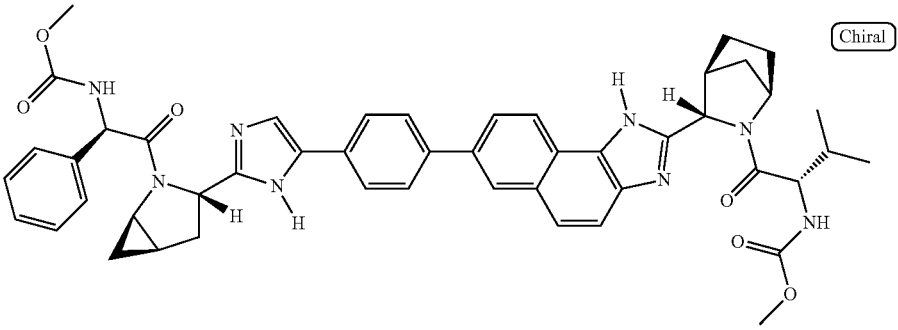 [SMILES: COC(=O)N[C@H](C(=O)N1[C@@H]2CC[C@@H](C2)[C@H]1c1nc2ccc3cc(-c4ccc(-c5cnc([C@@H]6C[C@H]7C[C@H]7N6C(=O)[C@H](NC(=O)OC)c6ccccc6)[nH]5)cc4)ccc3c2[nH]1)C(C)C] | 835.8 |
| 369 | 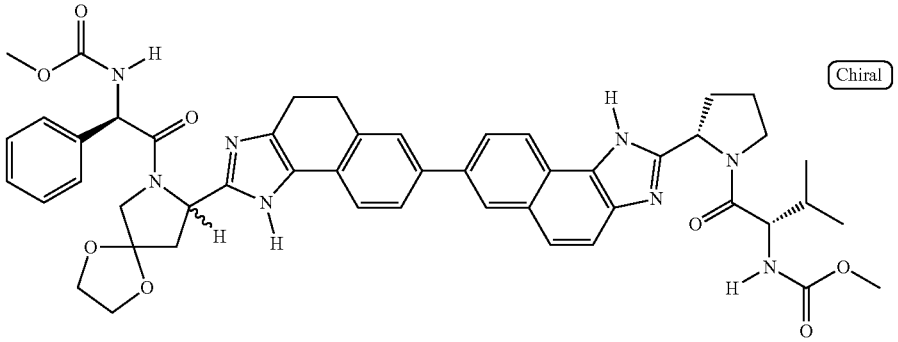 | 881.03 |
| 370 | 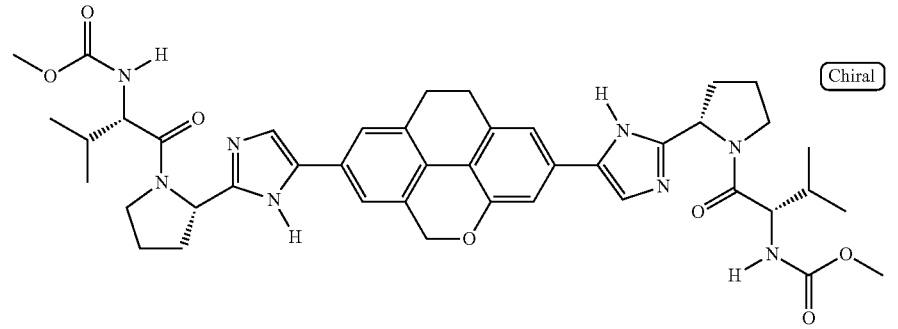 | 794.21 |
| 371 | 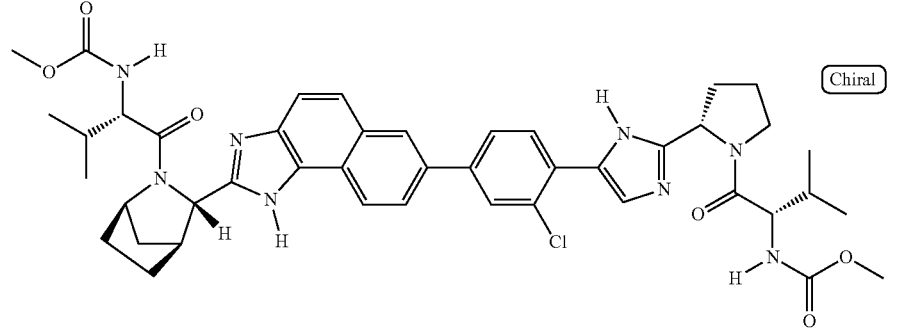 | 823.25 |

| # | Compound | LCMS (observed (M + H)+) |
|---|---|---|
| 372 | | 801.63 |
| 373 | | 873.22 |
| 374 | | 835.67 |
| 375 | | 839.73 |
| 376 | | 819.2 |

-continued
| # | Compound | LCMS (observed (M + H)+) |
|---|---|---|
| 377 | 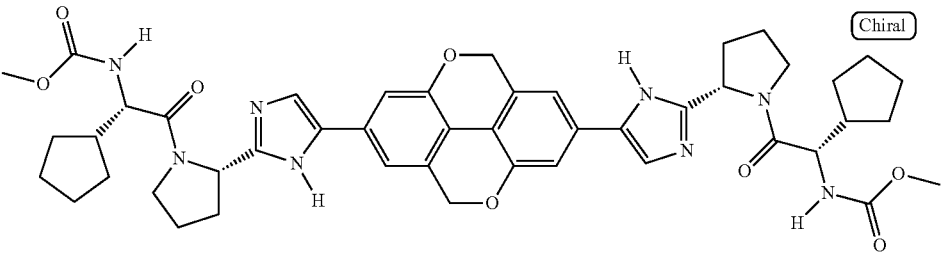 | 847.2 |
| 378 | 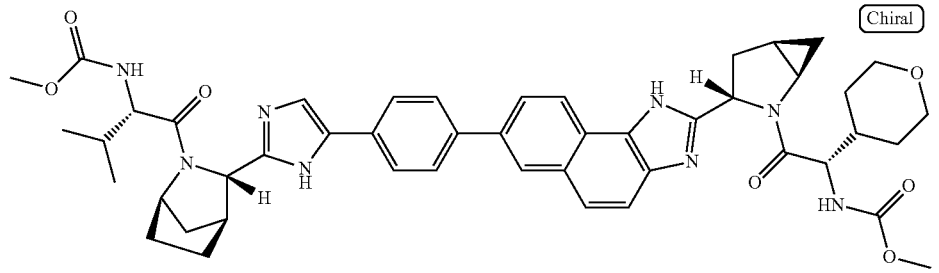 | 844.1 |
| 379 | 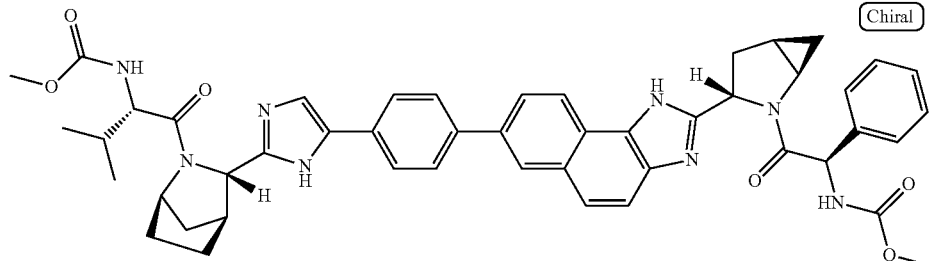 | 835.8 |
| 380 | 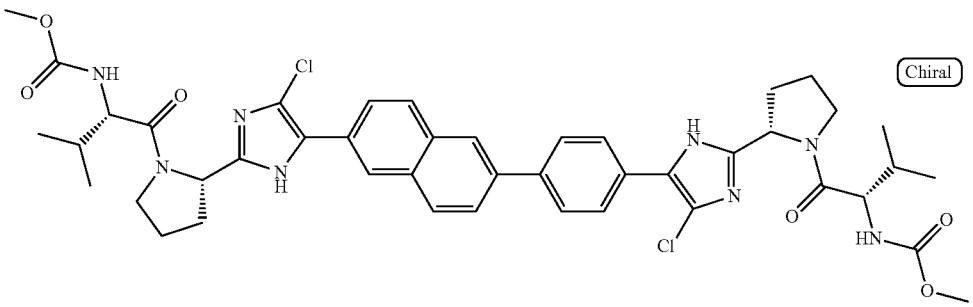 | 857.99 |
| 381 | 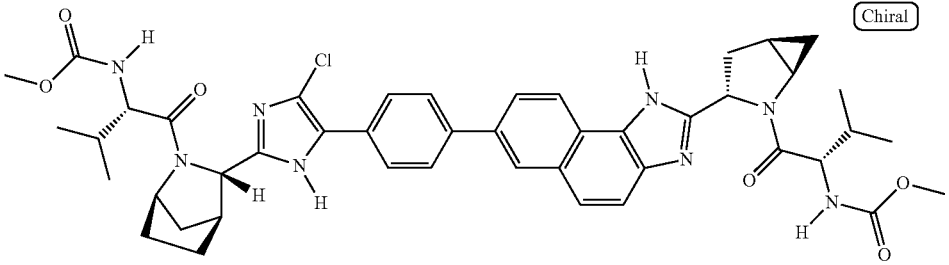 | 837.2 |

-continued
| # | Compound | LCMS (observed (M + H)+) |
|---|----------|--------------------------|
| 382 | 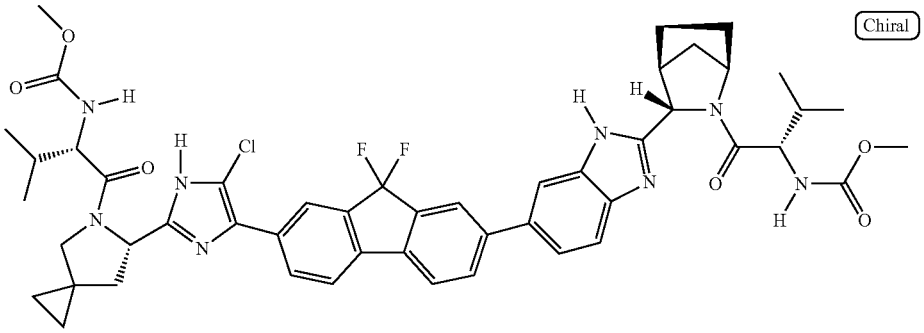 Chiral | 925.0 |
| 383 | 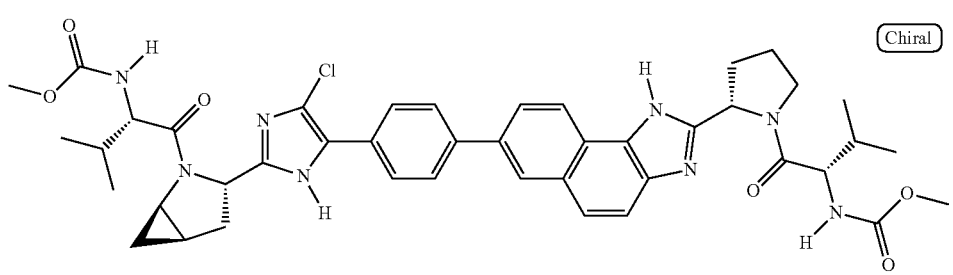 Chiral | 811.0 |
| 384 | 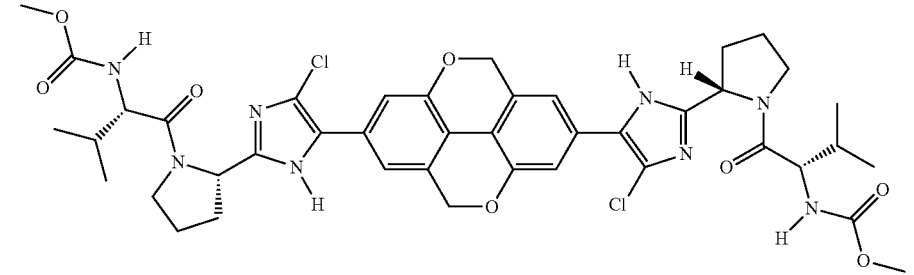 | 864.76 |
| 385 | 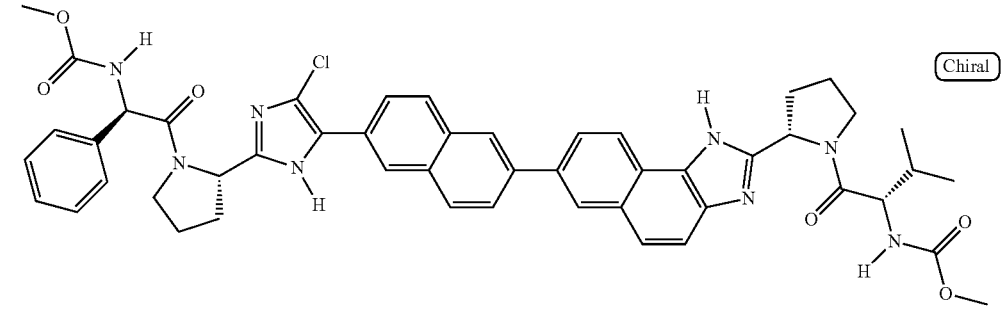 Chiral | 882.2 |
| 386 | 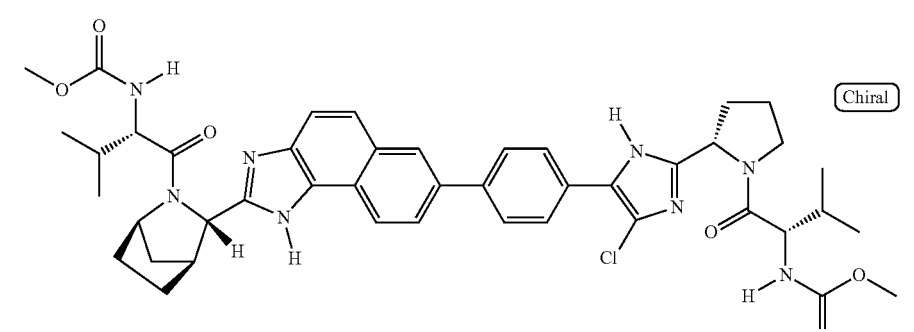 Chiral | 824.18 |

| # | Compound | LCMS (observed (M + H)+) |
|---|---|---|
| 387 | | 815.88 |
| 388 | | 824.18 |
| 389 | | 830.18 |
| 390 | | 805.76 |
| 391 | | 819.85 |

-continued

| # | Compound | LCMS (observed (M + H)+) |
|---|---|---|
| 392 | | 861.79 |
| 393 | | 785.68 Chiral |
| 394 | | 822.28 |
| 395 | | 840.26 |
| 396 | | 914.1 (+Na) Chiral |

| # | Compound | LCMS (observed (M + H)+) |
|---|---|---|
| 397 | 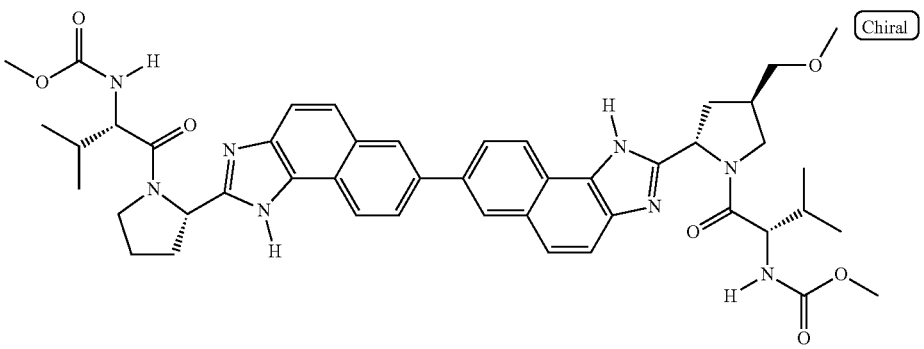 | 831.76 |
| 398 | 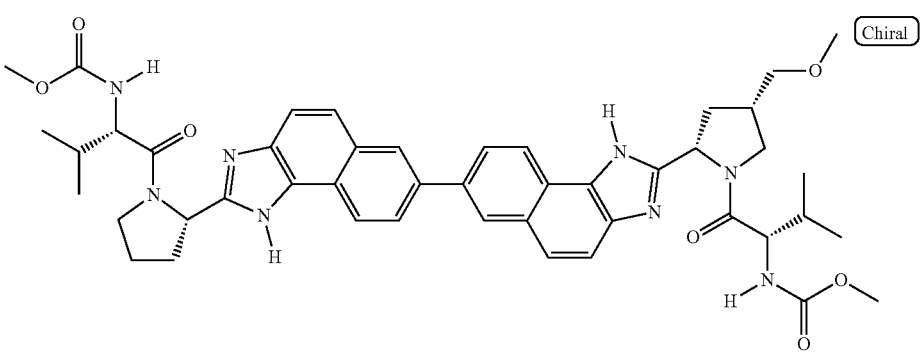 | 831.81 |
| 399 | 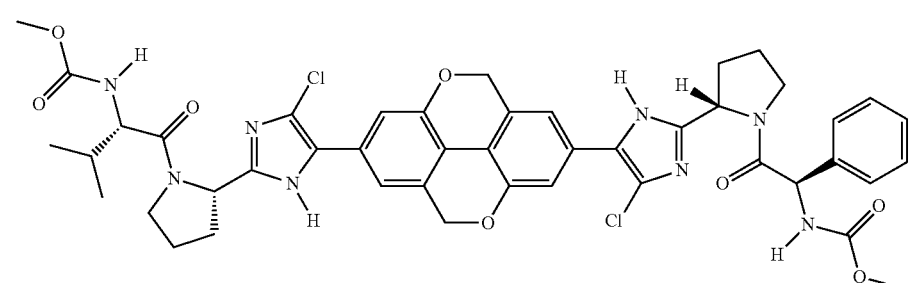 | 897.45 |
| 400 | 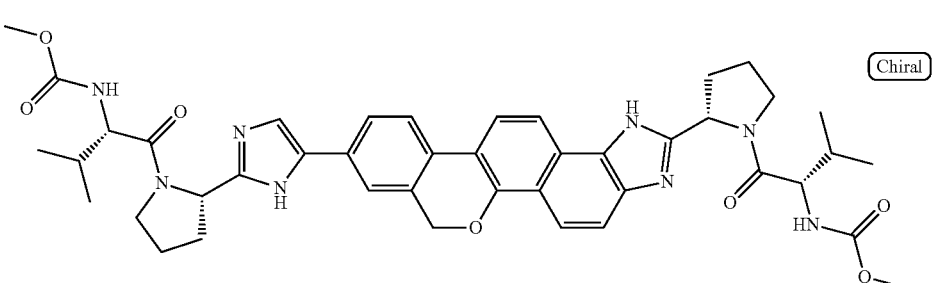 | 791.7 |
| 401 | 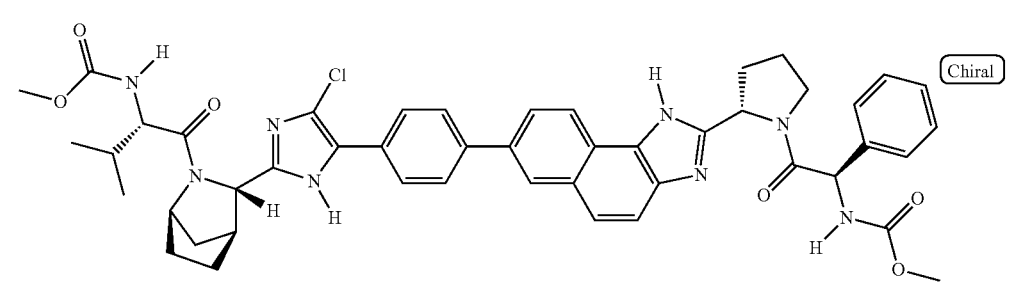 | 858.18 |

-continued
| # | Compound | LCMS (observed (M + H)+) |
|---|---|---|
| 402 | 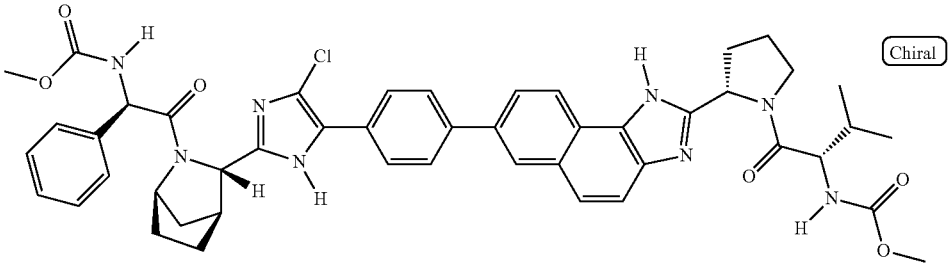 | 858.12 |
| 403 | 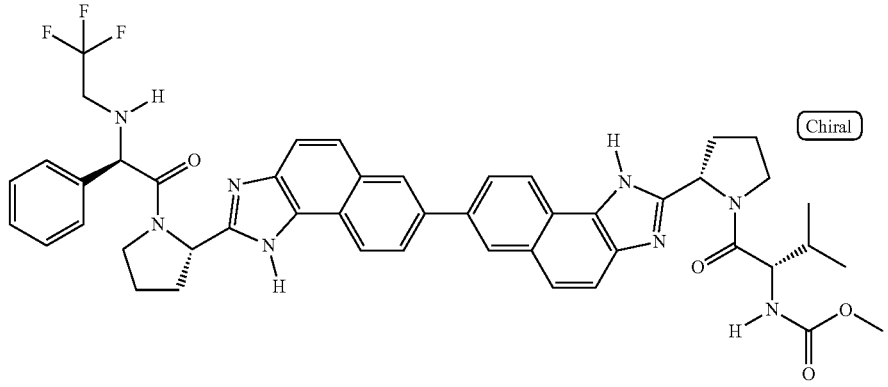 [SMILES: COC(=O)N[C@H](C(=O)N1CCC[C@H]1c1nc2ccc3cc(-c4ccc5c(ccc6nc([C@@H]7CCCN7C(=O)[C@H](NCC(F)(F)F)c7ccccc7)[nH]c65)c4)ccc3c2[nH]1)C(C)C] | 845.63 |
| 404 | 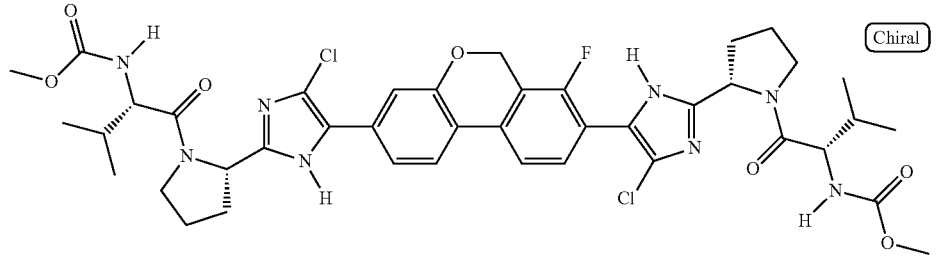 | 854.48 |
| 405 | 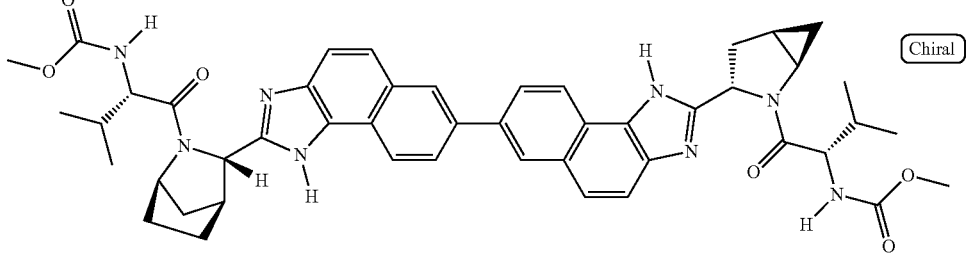 | 825.78 |
| 406 | 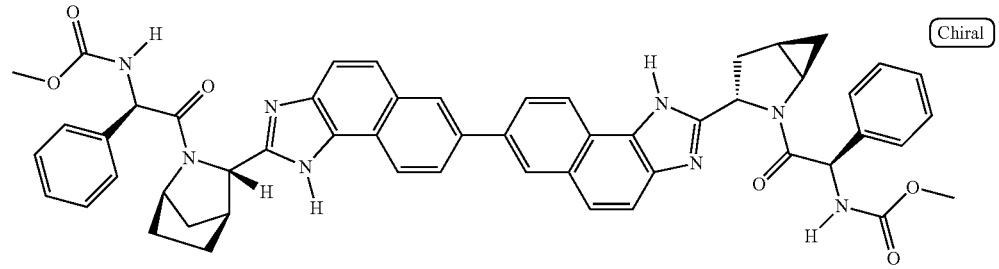 | 893.76 |

-continued
| # | Compound | LCMS (observed (M + H)+) |
|---|---|---|
| 407 | 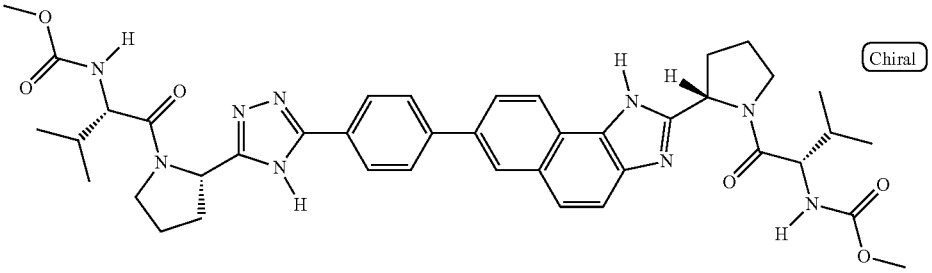 | 764.8 |
| 408 | 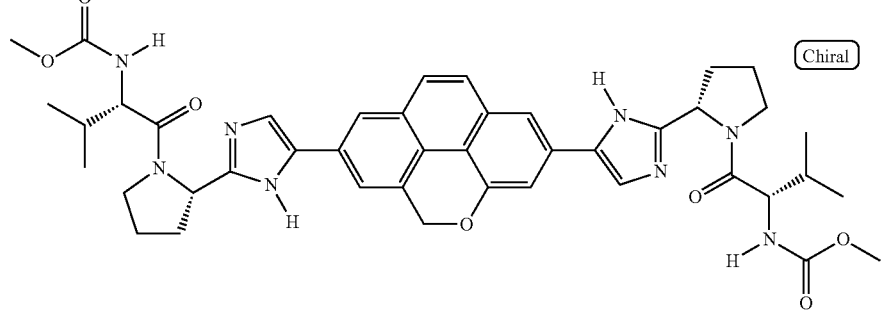 | 792.41 |
| 409 | 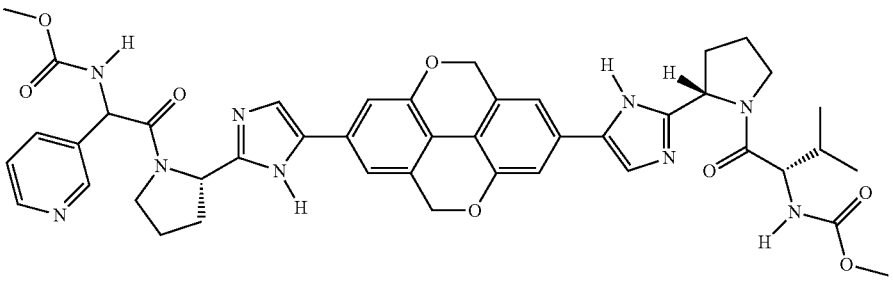 | 830.93 |
| 410 | 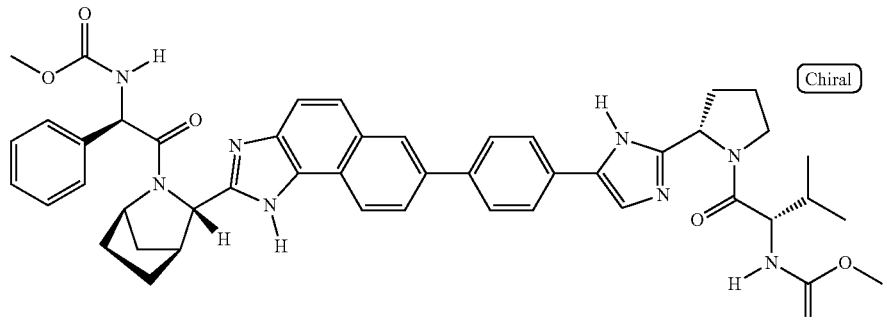 | 823.75 |

| # | Compound | LCMS (observed (M + H)+) |
|---|---|---|
| 411 | 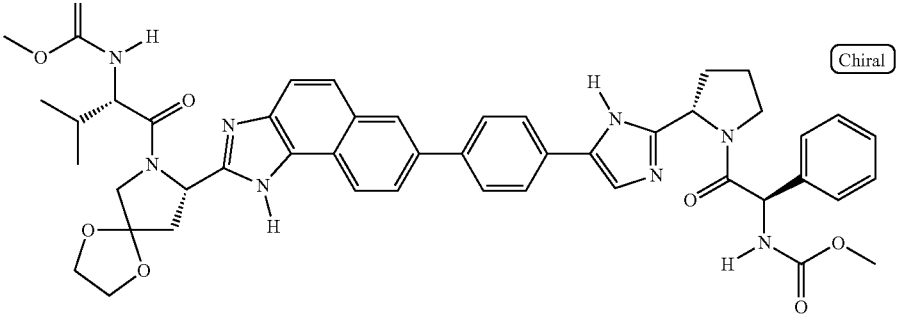 | 855.68 |
| 412 | 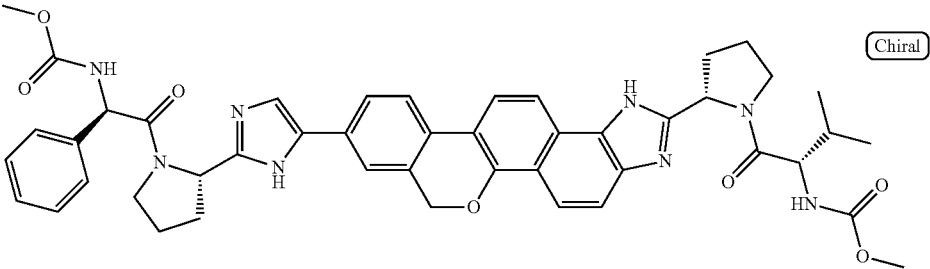 | 825.72 |
| 413 | 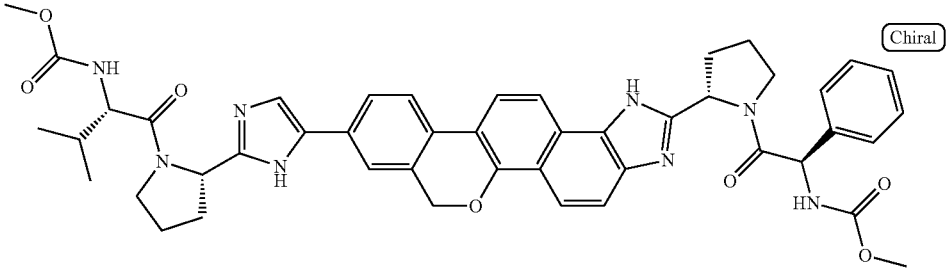 | 825.67 |
| 414 | 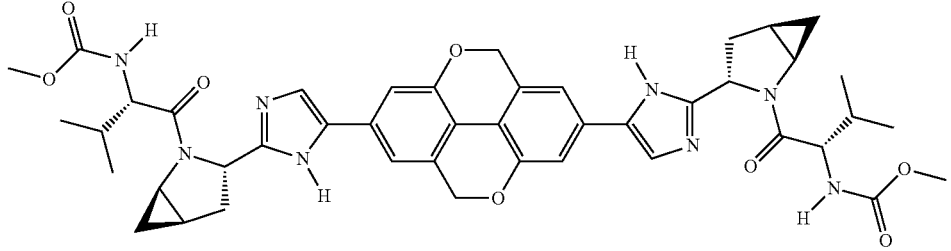 | 819.79 |
| 415 | 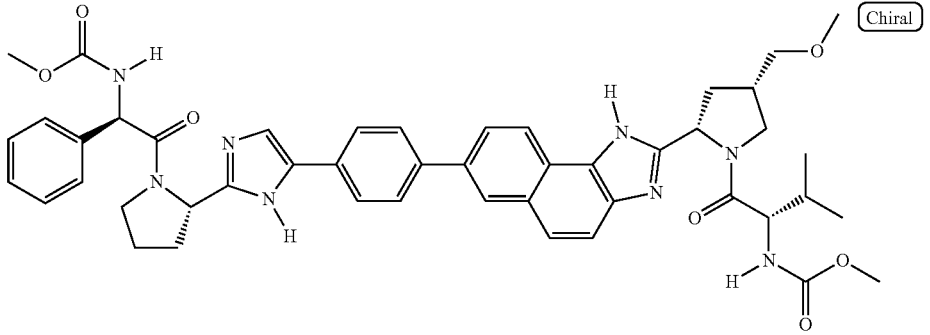 [SMILES: COC[C@H]1C[C@@H](c2nc3ccc4cc(-c5ccc(-c6cnc([C@@H]7CCCN7C(=O)[C@H](NC(=O)OC)c7ccccc7)[nH]6)cc5)ccc4c3[nH]2)N(C(=O)[C@@H](NC(=O)OC)C(C)C)C1] | 841.65 |

| # | Compound | LCMS (observed (M + H)+) |
|---|---|---|
| 416 | 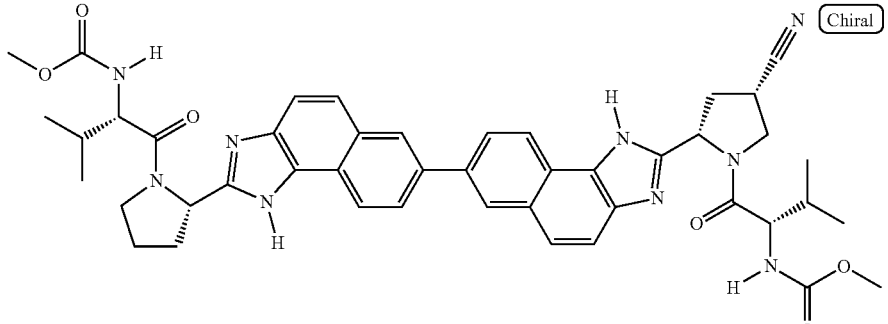 | 812.66 |
| 417 | 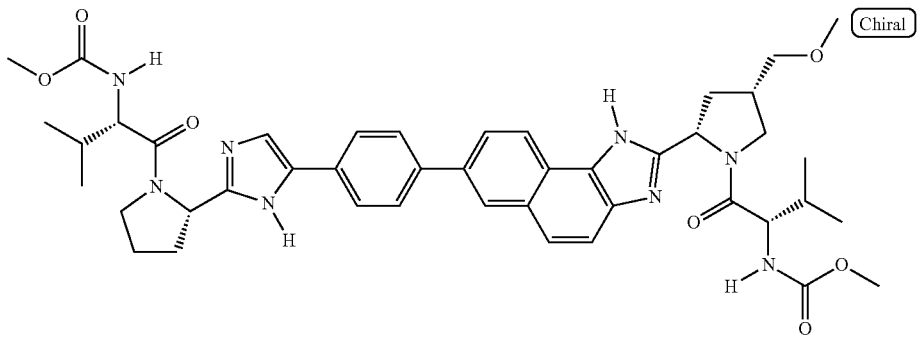 | 807.59 |
| 418 | 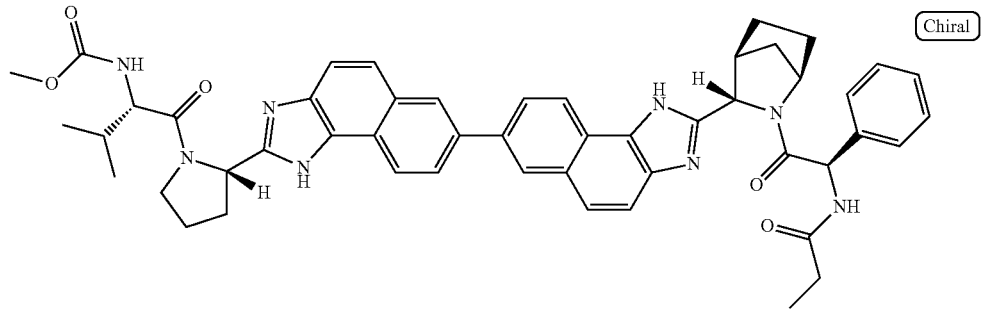 [SMILES: CCC(=O)N[C@@H](C(=O)N1[C@@H]2CC[C@@H](C2)[C@H]1c1nc2ccc3cc(-c4ccc5c(ccc6nc([C@@H]7CCCN7C(=O)[C@@H](NC(=O)OC)C(C)C)[nH]c65)c4)ccc3c2[nH]1)c1ccccc1] | 845.8 |
| 419 | 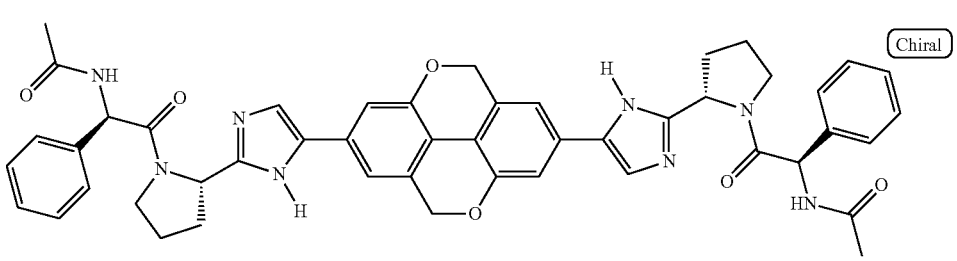 [SMILES: CC(=O)N[C@@H](C(=O)N1CCC[C@H]1c1ncc(-c2cc3c4c(c2)OCc2cc(-c5cnc([C@@H]6CCCN6C(=O)[C@H](NC(C)=O)c6ccccc6)[nH]5)cc(c2-4)OC3)[nH]1)c1ccccc1] | 831.8 |
| 420 | 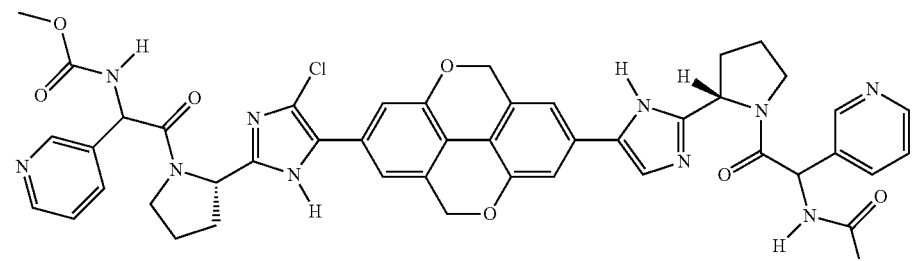 | 899.99 |

-continued

| # | Compound | LCMS (observed (M + H)+) |
|---|---|---|
| 421 | | 931.17 |
| 422 | | 791.6 |
| 423 | | 825.61 |
| 424 | | 823.68 |
| 425 | | 851.14 |

| # | Compound | LCMS (observed (M + H)+) |
|---|---|---|
| 426 | 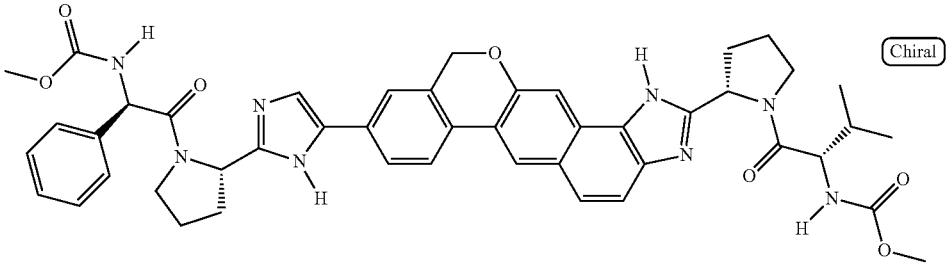 | 825.67 |
| 427 | 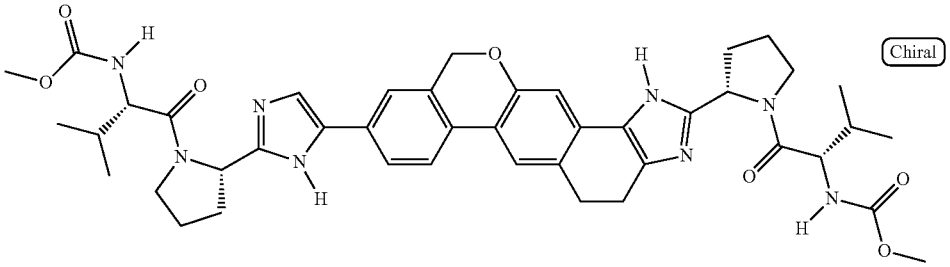 | 793.69 |
| 428 | 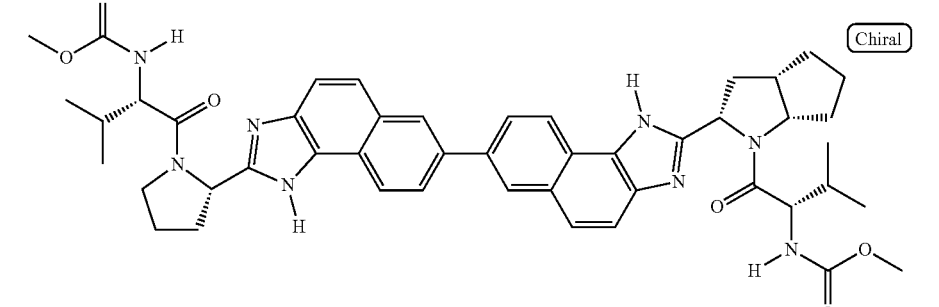 | 827.2 |
| 429 | 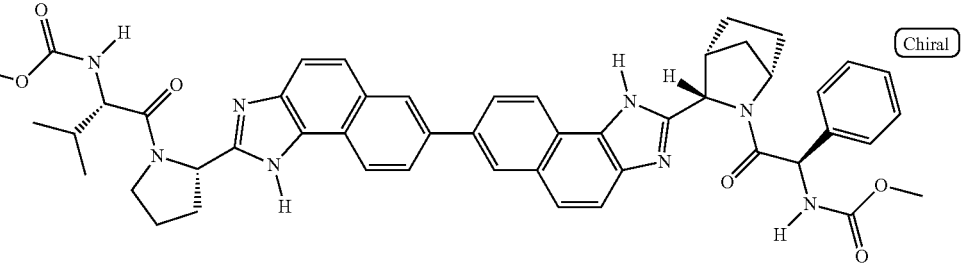 | 847.8 |
| 430 | 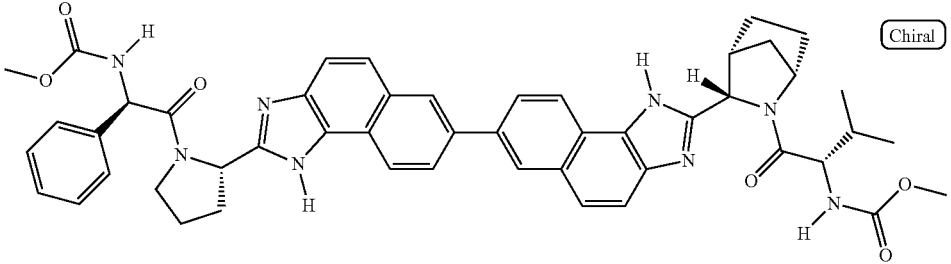 | 847.8 |

-continued
| # | Compound | LCMS (observed (M + H)+) |
|---|---|---|
| 431 | 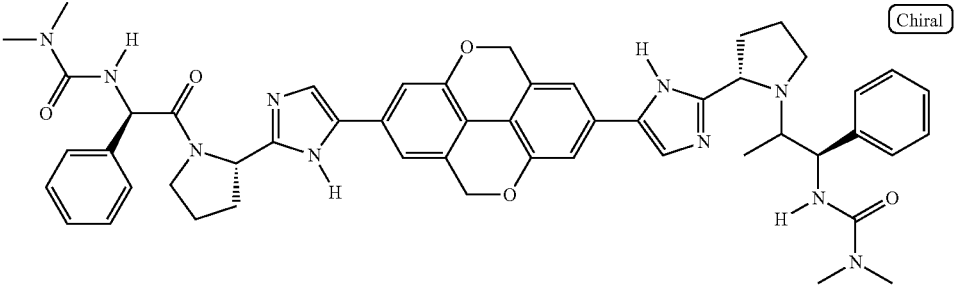 [SMILES: CC([C@H](NC(=O)N(C)C)c1ccccc1)N1CCC[C@H]1c1ncc(-c2cc3c4c(c2)OCc2cc(-c5cnc([C@@H]6CCCN6C(=O)[C@H](NC(=O)N(C)C)c6ccccc6)[nH]5)cc(c2-4)OC3)[nH]1] | 890.1 |
| 432 | 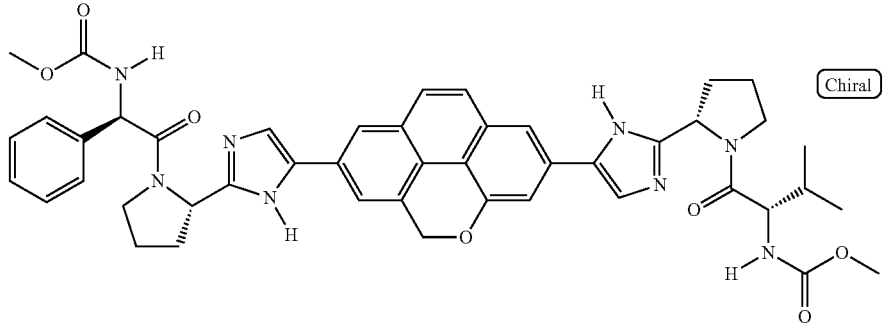 | 825.28 |
| 433 | 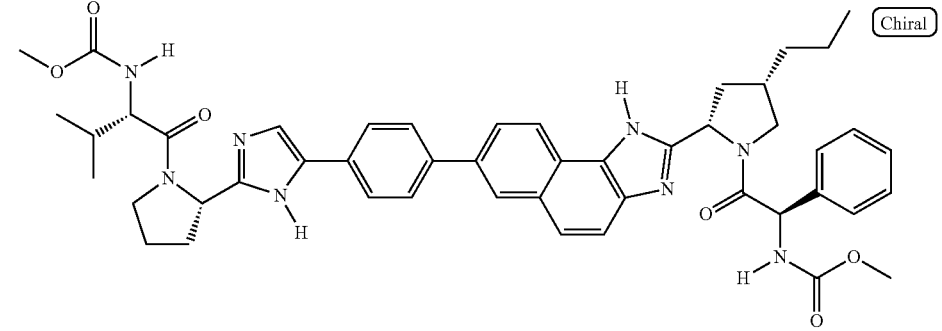 [SMILES: CCC[C@H]1C[C@@H](c2nc3ccc4cc(-c5ccc(-c6cnc([C@@H]7CCCN7C(=O)[C@@H](NC(=O)OC)C(C)C)[nH]6)cc5)ccc4c3[nH]2)N(C(=O)[C@H](NC(=O)OC)c2ccccc2)C1] | 841.66 |
| 434 | 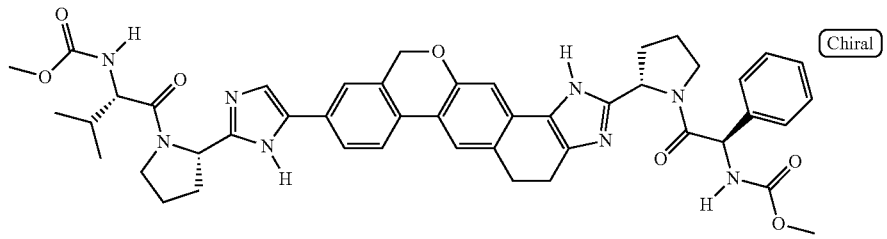 | 827.64 |
| 435 | 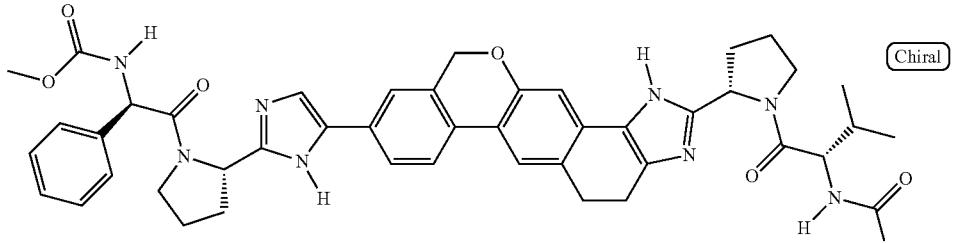 | 827.71 |

| # | Compound | LCMS (observed (M + H)+) |
|---|---|---|
| 436 | 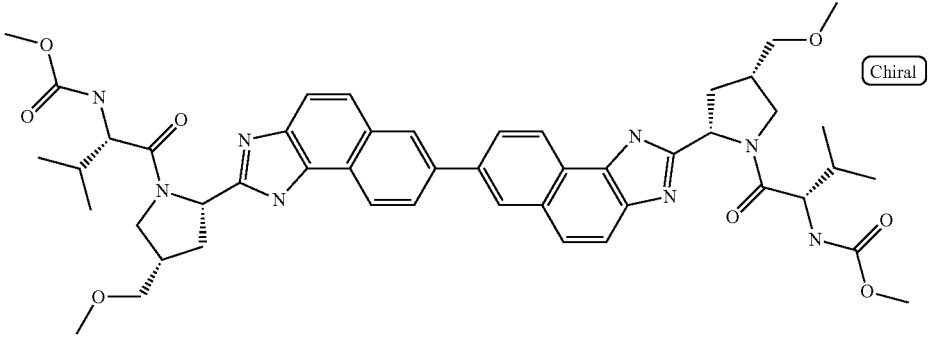 | 875.7 |
| 437 | 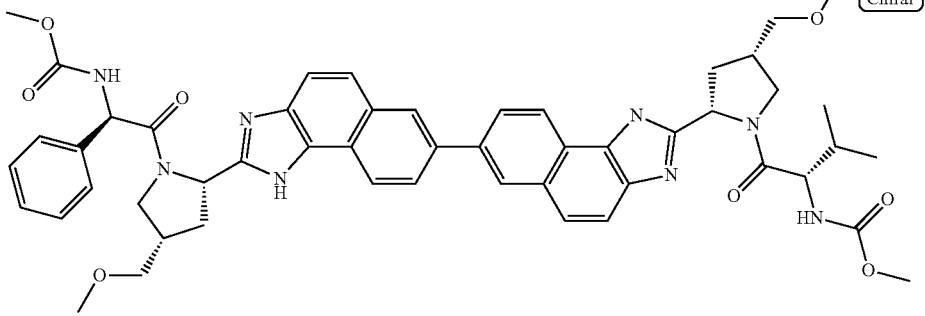 | 909.79 |
| 438 | 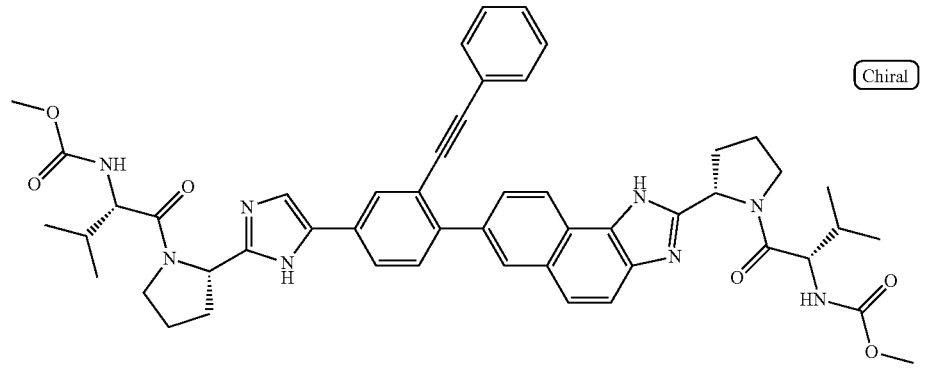 | 863.77 |
| 439 | 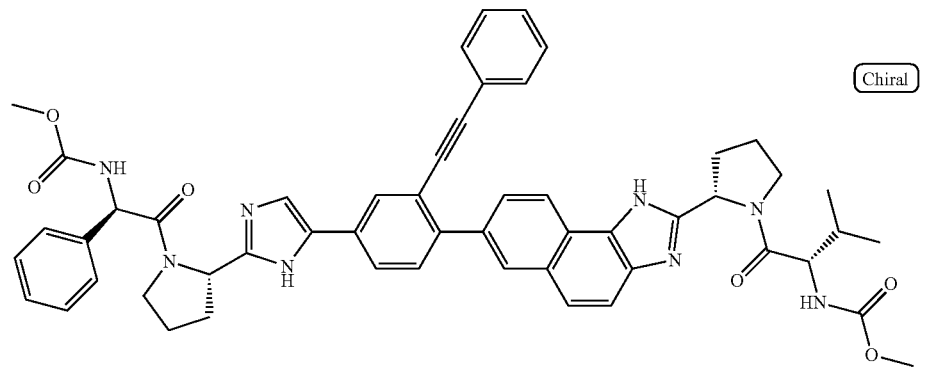 | 897.78 |

-continued

| # | Compound | LCMS (observed) (M + H)+ |
|---|---|---|
| 440 | | 851.23 |
| 441 | | 808.29 |
| 442 | | 841.76 |
| 443 | | 883.8 |

-continued
| # | Compound | LCMS (observed (M + H)+) |
|---|---|---|
| 444 | 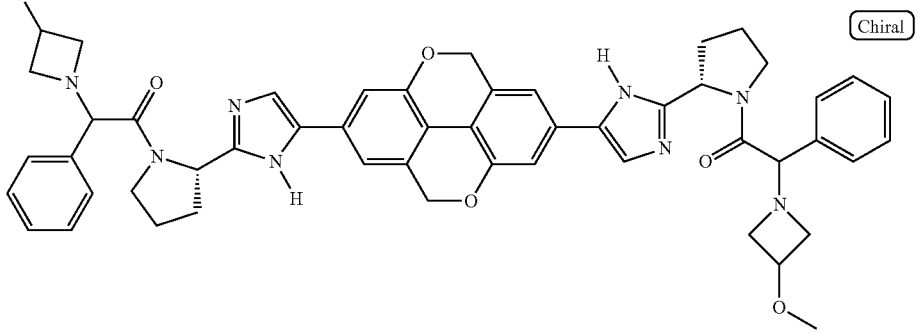 Chiral | 887.1 |
| 445 | 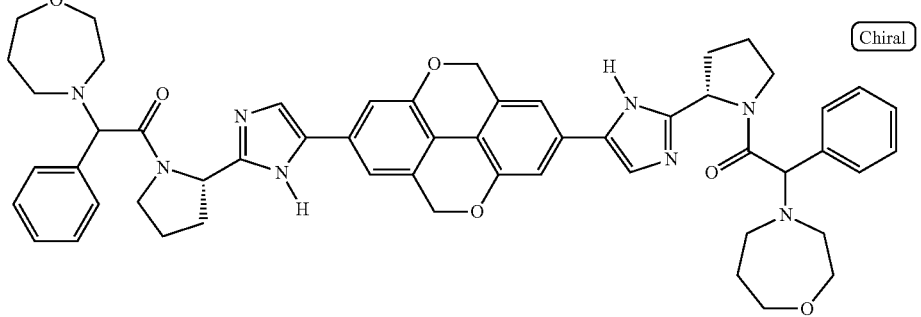 Chiral | 916.1 |
| 446 | 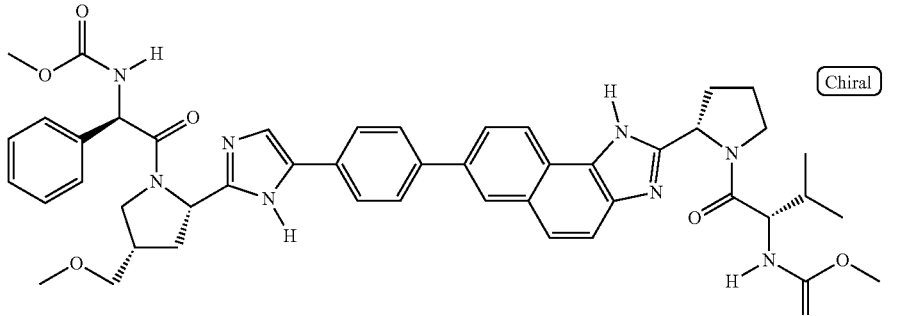 Chiral | 842.16 |
| 447 | 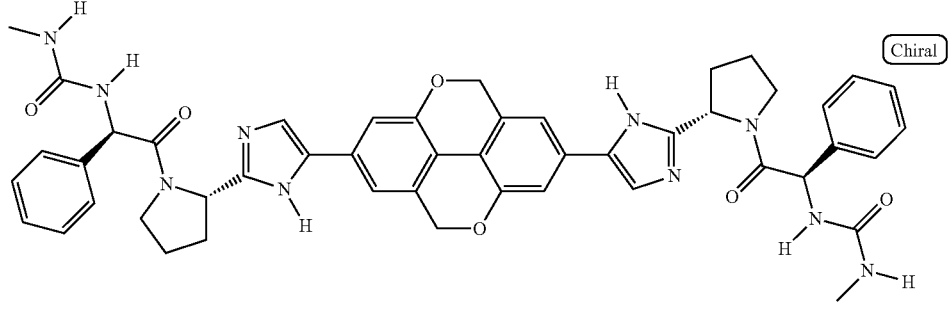 [SMILES: CNC(=O)N[C@@H](C(=O)N1CCC[C@H]1c1ncc(-c2cc3c4c(c2)OCc2cc(-c5cnc([C@@H]6CCCN6C(=O)[C@H](NC(=O)NC)c6ccccc6)[nH]5)cc(c2-4)OC3)[nH]1)c1ccccc1] Chiral | 861.1 |
| 448 | 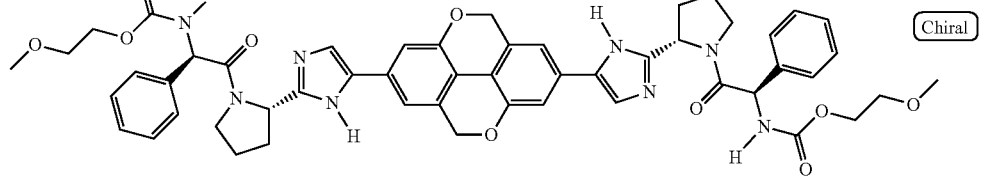 Chiral | 973.0 (+Na) |

-continued
| # | Compound | LCMS (observed (M + H)+) |
|---|---|---|
| 449 | 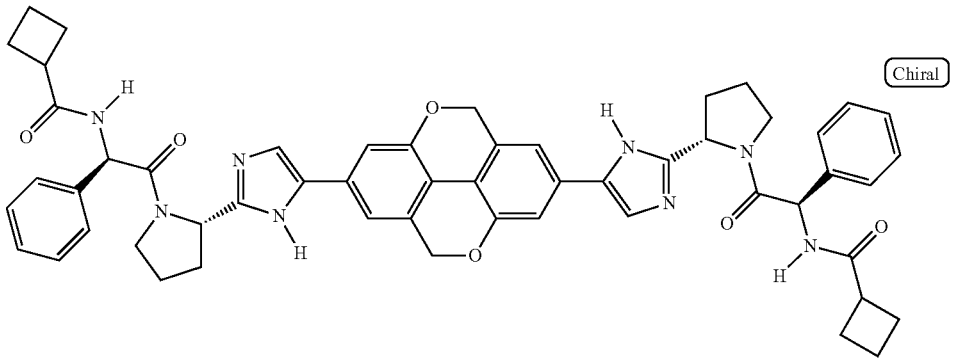 [SMILES: O=C(N[C@@H](C(=O)N1CCC[C@H]1c1ncc(-c2cc3c4c(c2)OCc2cc(-c5cnc([C@@H]6CCCN6C(=O)[C@H](NC(=O)C6CCC6)c6ccccc6)[nH]5)cc(c2-4)OC3)[nH]1)c1ccccc1)C1CCC1] | 911.9 |
| 450 | 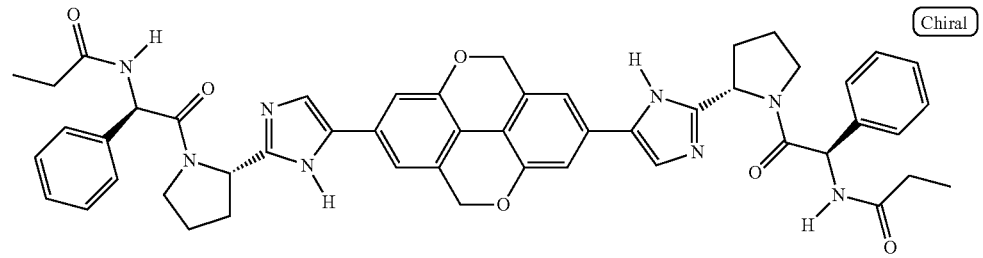 [SMILES: CCC(=O)N[C@@H](C(=O)N1CCC[C@H]1c1ncc(-c2cc3c4c(c2)OCc2cc(-c5cnc([C@@H]6CCCN6C(=O)[C@H](NC(=O)CC)c6ccccc6)[nH]5)cc(c2-4)OC3)[nH]1)c1ccccc1] | 859.1 |
| 451 | 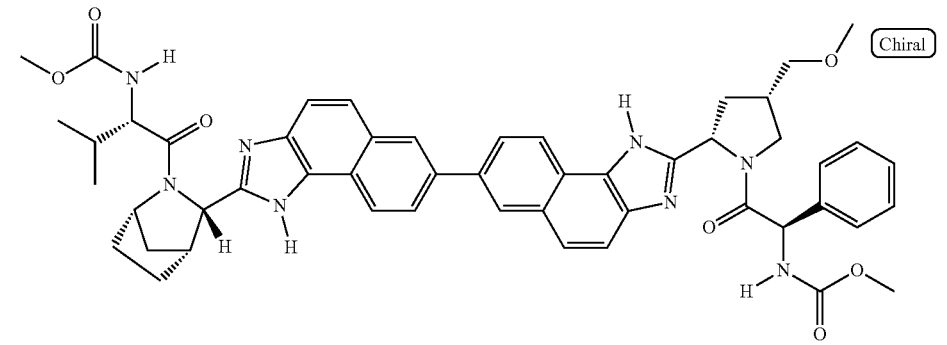 [SMILES: COC[C@H]1C[C@@H](c2nc3ccc4cc(-c5ccc6c(ccc7nc([C@@H]8[C@@H]9CC[C@@H](C9)N8C(=O)[C@@H](NC(=O)OC)C(C)C)[nH]c76)c5)ccc4c3[nH]2)N(C(=O)[C@H](NC(=O)OC)c2ccccc2)C1] | 891.8 |
| 452 | 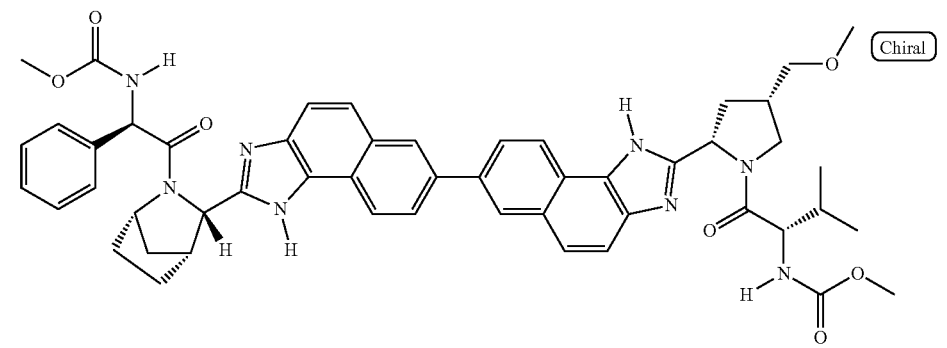 | 891.7 |

-continued

| # | Compound | LCMS (observed (M + H)+) |
|---|---|---|
| 453 | | 865.2 |
| 454 | | 865.8 |
| 455 | | 857.2 |
| 456 | | 852.44 |

| # | Compound | LCMS (observed (M + H)+) |
|---|---|---|
| 457 | 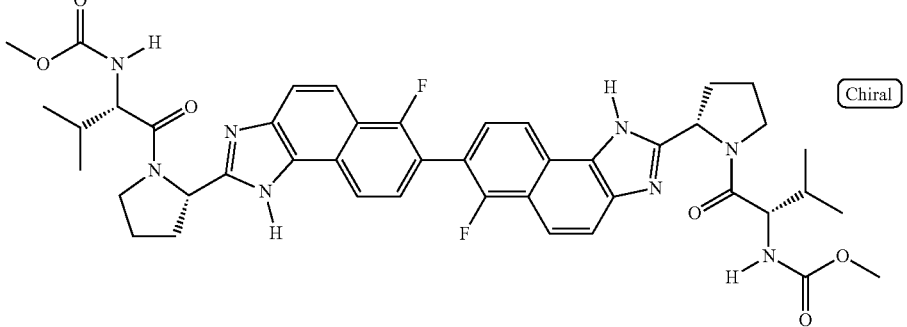 | 824.22 |
| 458 | 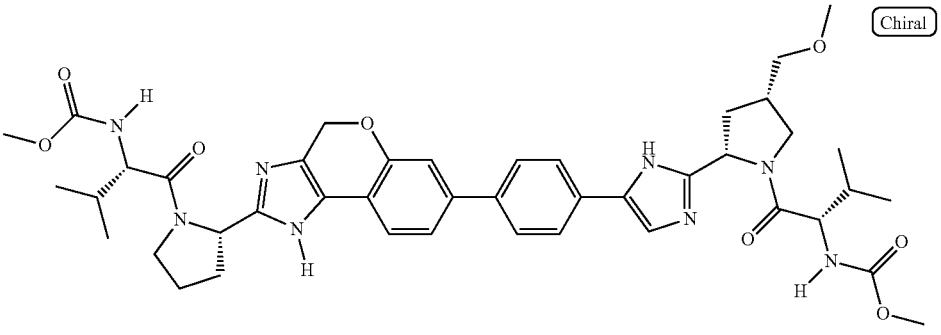 | 811.24 |
| 459 | 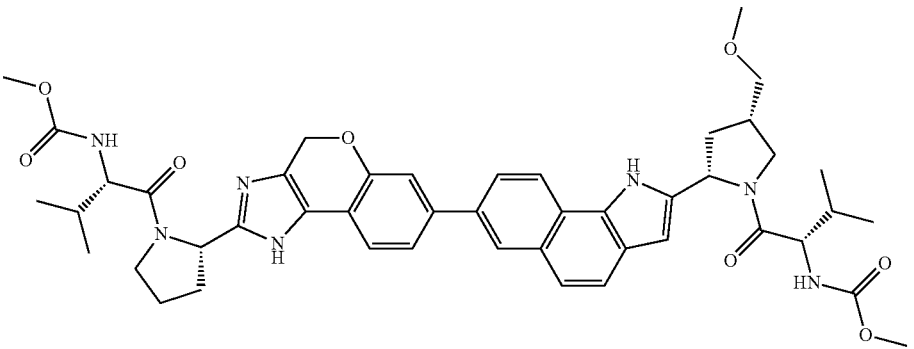 | 835.6 |
| 460 | 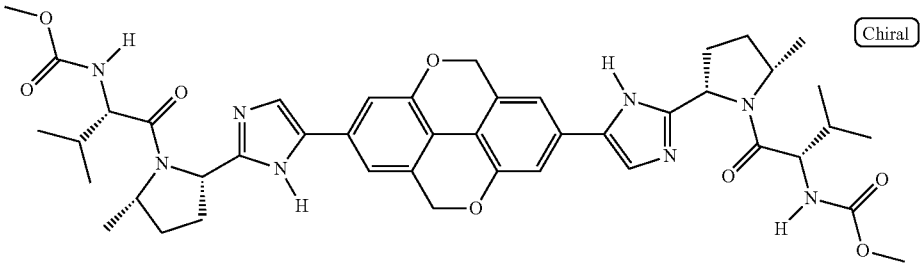 | 824.2 |

-continued

| # | Compound | LCMS (observed (M + H)+) |
|---|---|---|
| 461 | | 891.8 |
| 462 | | 917.2 |
| 463 | | 903.1 |
| 464 | | 1000.1 |

| # | Compound | LCMS (observed (M + H)+) |
|---|---|---|
| 465 | 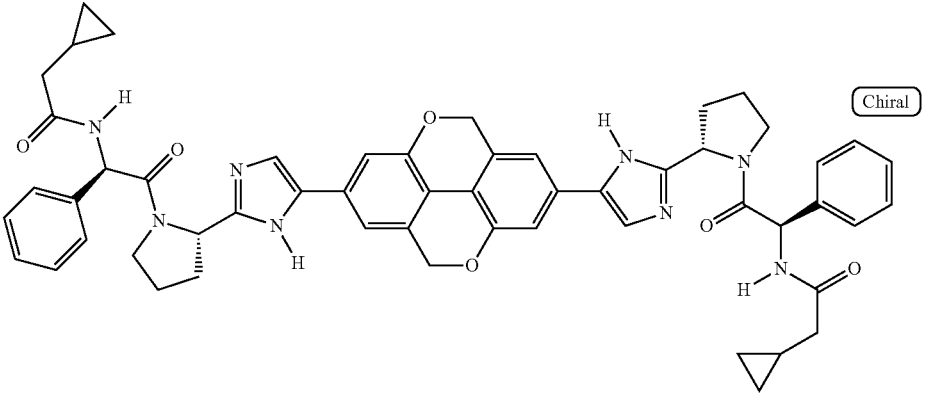 [SMILES: O=C(CC1CC1)N[C@@H](C(=O)N1CCC[C@H]1c1ncc(-c2cc3c4c(c2)OCc2cc(-c5cnc([C@@H]6CCCN6C(=O)[C@H](NC(=O)CC6CC6)c6ccccc6)[nH]5)cc(c2-4)OC3)[nH]1)c1ccccc1] Chiral | 911.8 |
| 466 | 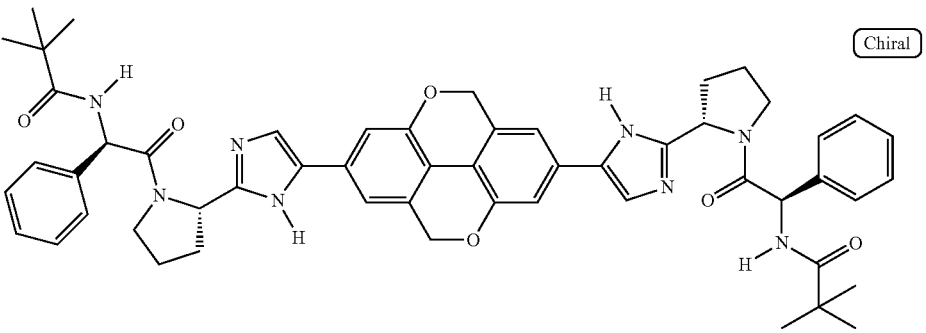 [SMILES: CC(C)(C)C(=O)N[C@@H](C(=O)N1CCC[C@H]1c1ncc(-c2cc3c4c(c2)OCc2cc(-c5cnc([C@@H]6CCCN6C(=O)[C@H](NC(=O)C(C)(C)C)c6ccccc6)[nH]5)cc(c2-4)OC3)[nH]1)c1ccccc1] Chiral | 915.2 |
| 467 | 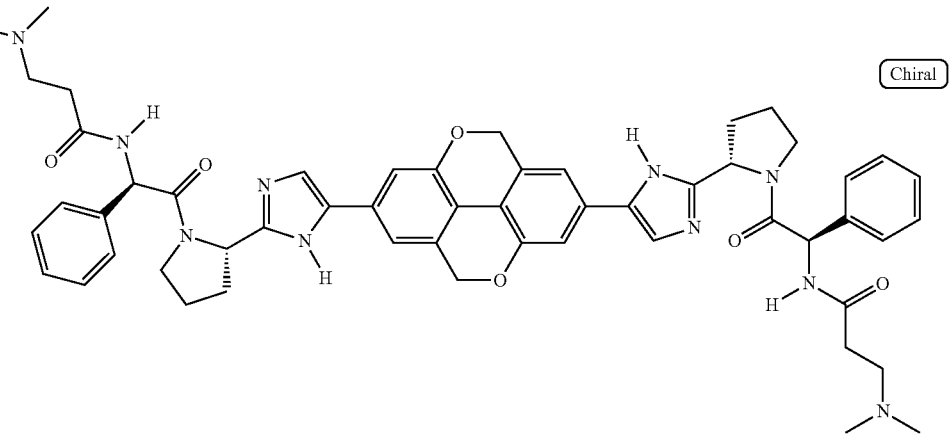 Chiral | 946.2 |
| 468 | 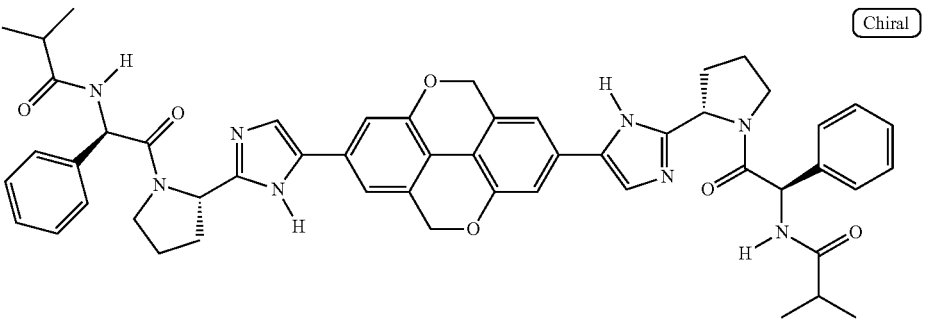 [SMILES: CC(C)C(=O)N[C@@H](C(=O)N1CCC[C@H]1c1ncc(-c2cc3c4c(c2)OCc2cc(-c5cnc([C@@H]6CCCN6C(=O)[C@H](NC(=O)C(C)C)c6ccccc6)[nH]5)cc(c2-4)OC3)[nH]1)c1ccccc1] Chiral | 887.8 |

| # | Compound | LCMS (observed (M + H)+) |
|---|----------|--------------------------|
| 469 | 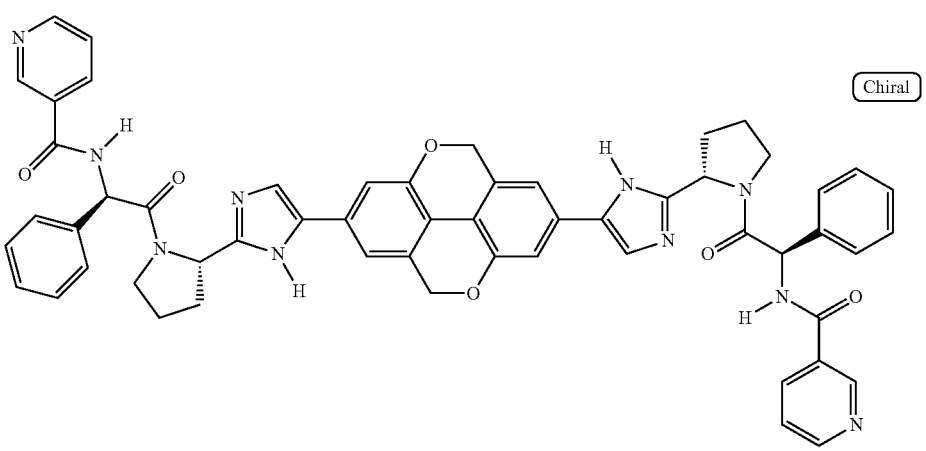 [SMILES: O=C(N[C@@H](C(=O)N1CCC[C@H]1c1ncc(-c2cc3c4c(c2)OCc2cc(-c5cnc([C@@H]6CCCN6C(=O)[C@H](NC(=O)c6cccnc6)c6ccccc6)[nH]5)cc(c2-4)OC3)[nH]1)c1ccccc1)c1cccnc1] | 958.1 |
| 470 | 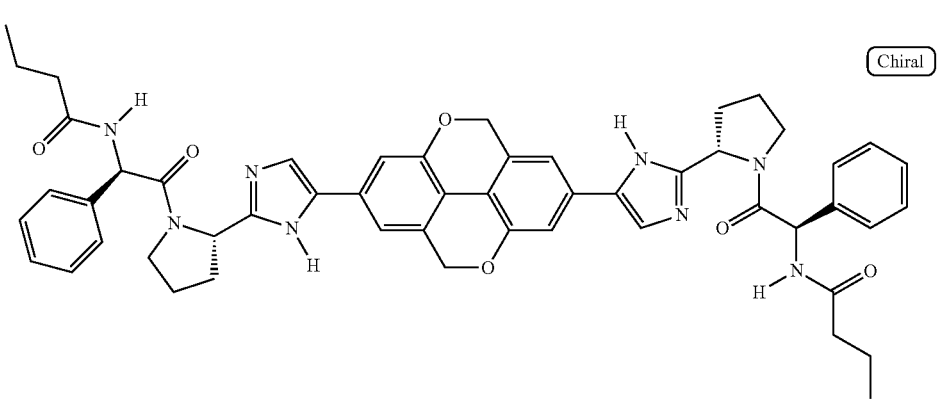 [SMILES: CCCC(=O)N[C@@H](C(=O)N1CCC[C@H]1c1ncc(-c2cc3c4c(c2)OCc2cc(-c5cnc([C@@H]6CCCN6C(=O)[C@H](NC(=O)CCC)c6ccccc6)[nH]5)cc(c2-4)OC3)[nH]1)c1ccccc1] | 887.2 |
| 471 | 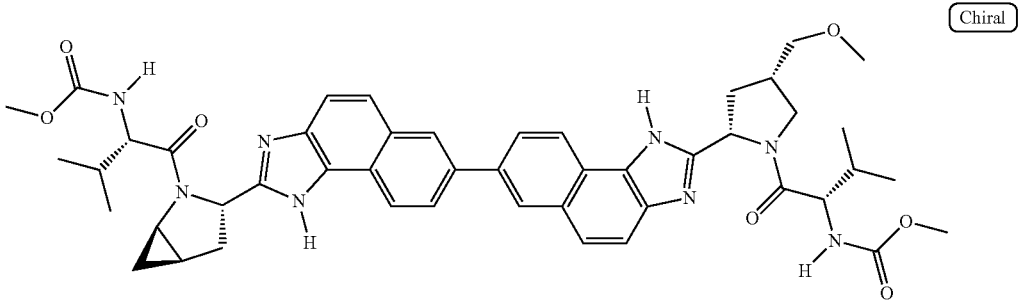 | 843.8 |
| 472 | 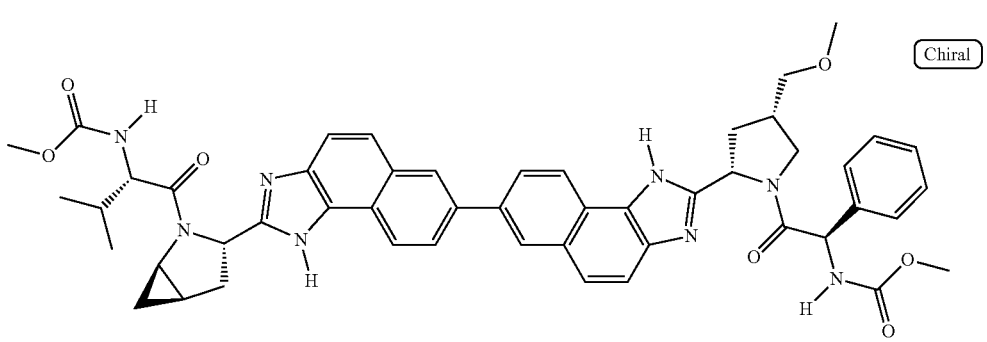 | 877.82 |

-continued
| # | Compound | LCMS (observed (M + H)+) |
|---|---|---|
| 473 | 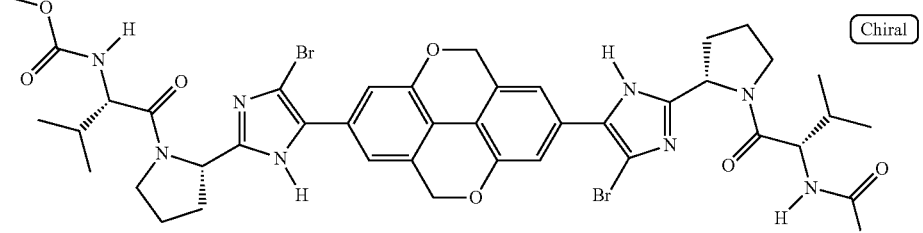 | 950.8 |
| 474 | 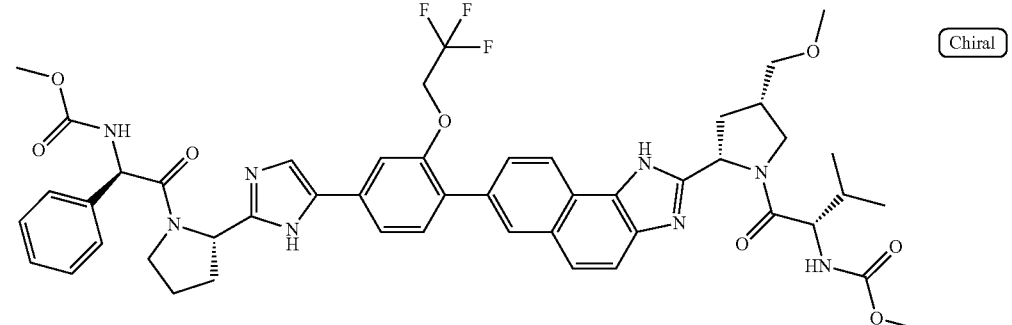 | 939.23 |
| 475 | 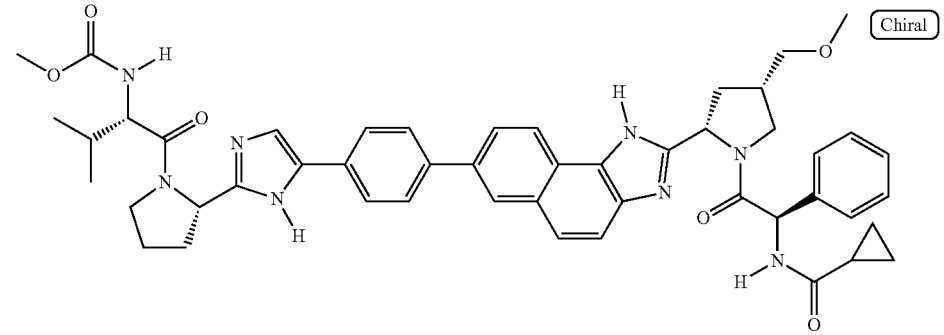 [SMILES: COC[C@H]1C[C@@H](c2nc3ccc4cc(-c5ccc(-c6cnc([C@@H]7CCCN7C(=O)[C@@H](NC(=O)OC)C(C)C)[nH]6)cc5)ccc4c3[nH]2)N(C(=O)[C@H](NC(=O)C2CC2)c2ccccc2)C1] | 851.33 |
| 476 | 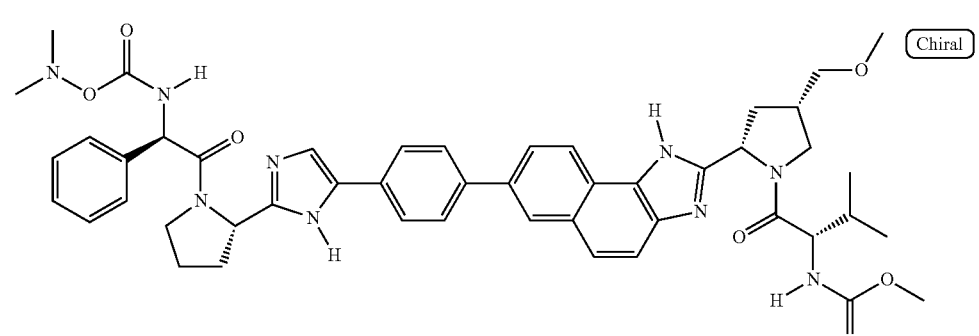 | 868.34 |

-continued

| # | Compound | LCMS (observed (M + H)+) |
|---|---|---|
| 477 | | 783.43 |
| 478 | | 879.4 |
| 479 | | 839.59 |
| 480 | | 919.4 |

-continued
| # | Compound | LCMS (observed (M + H)+) |
|---|---|---|
| 481 | 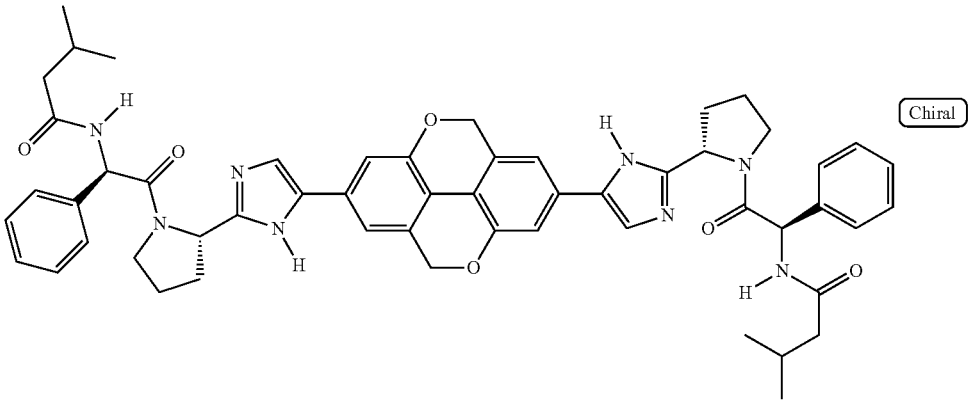 [SMILES: CC(C)CC(=O)N[C@@H](C(=O)N1CCC[C@H]1c1ncc(-c2cc3c4c(c2)OCc2cc(-c5cnc([C@@H]6CCCN6C(=O)[C@H](NC(=O)CC(C)C)c6ccccc6)[nH]5)cc(c2-4)OC3)[nH]1)c1ccccc1] | 937.3 |
| 482 | 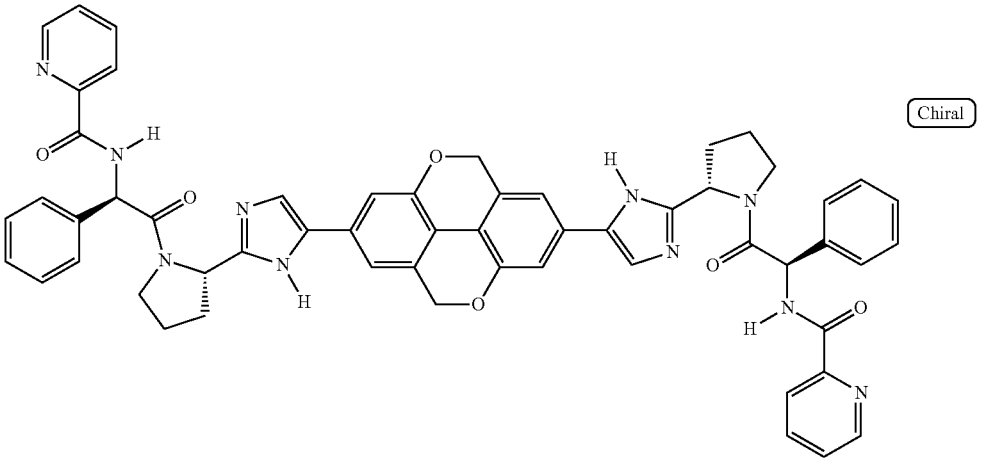 [SMILES: O=C(N[C@@H](C(=O)N1CCC[C@H]1c1ncc(-c2cc3c4c(c2)OCc2cc(-c5cnc([C@@H]6CCCN6C(=O)[C@H](NC(=O)c6ccccn6)c6ccccc6)[nH]5)cc(c2-4)OC3)[nH]1)c1ccccc1)c1ccccn1] | 957.8 |
| 483 | 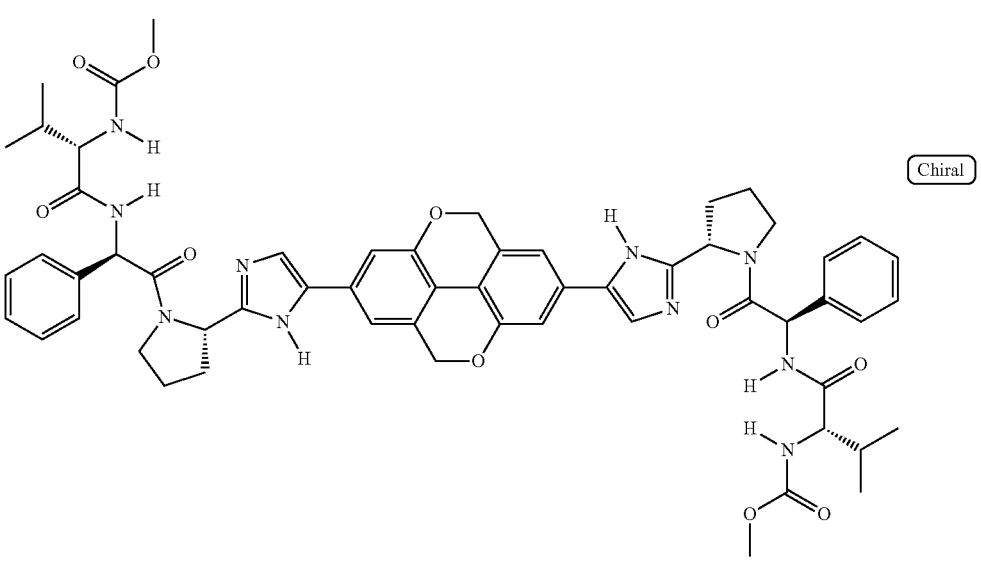 [SMILES: COC(=O)N[C@H](C(=O)N[C@@H](C(=O)N1CCC[C@H]1c1ncc(-c2cc3c4c(c2)OCc2cc(-c5cnc([C@@H]6CCCN6C(=O)[C@H](NC(=O)[C@@H](NC(=O)OC)C(C)C)c6ccccc6)[nH]5)cc(c2-4)OC3)[nH]1)c1ccccc1)C(C)C] | 1061.9 |

| # | Compound | LCMS (observed (M + H)+) |
|---|---|---|
| 484 |  | 1002.0 |
| 485 | 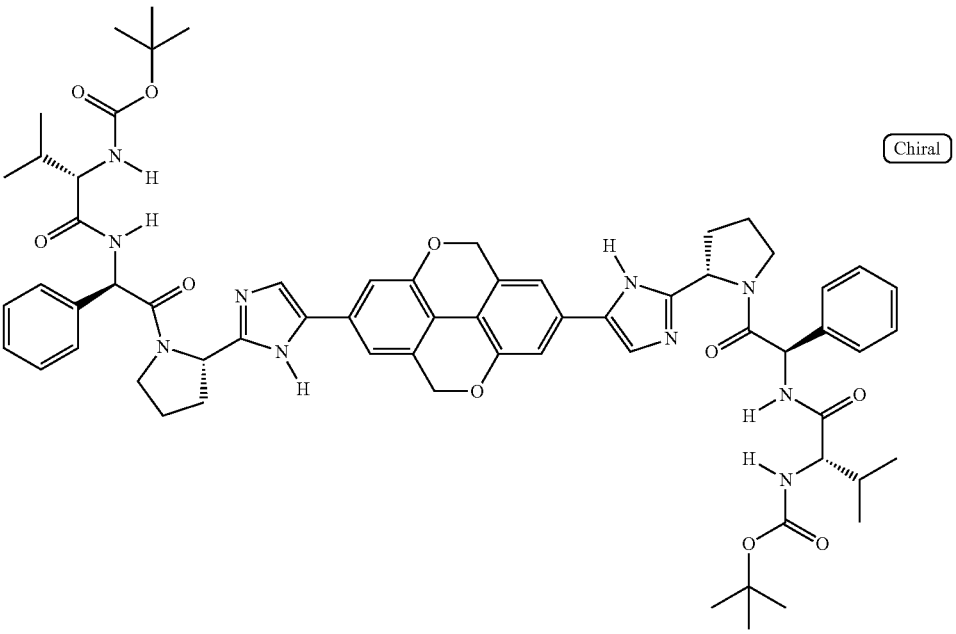 [SMILES: CC(C)[C@H](NC(=O)OC(C)(C)C)C(=O)N[C@@H](C(=O)N1CCC[C@H]1c1ncc(-c2cc3c4c(c2)OCc2cc(-c5cnc([C@@H]6CCCN6C(=O)[C@H](NC(=O)[C@@H](NC(=O)OC(C)(C)C)C(C)C)c6ccccc6)[nH]5)cc(c2-4)OC3)[nH]1)c1ccccc1] | 1145.8 |
| 486 | 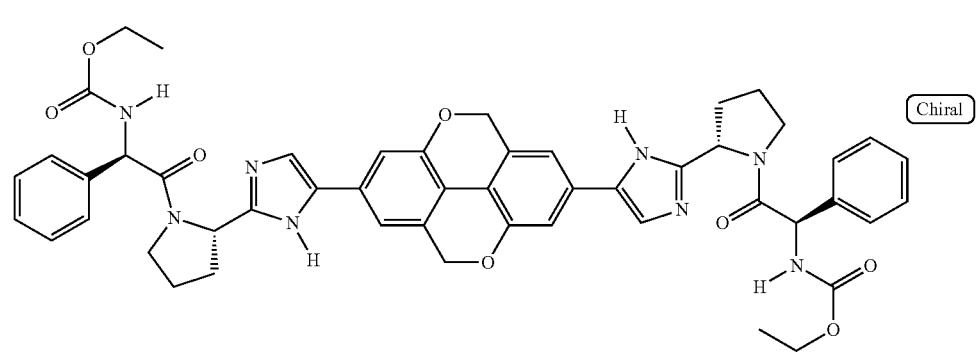 [SMILES: CCOC(=O)N[C@@H](C(=O)N1CCC[C@H]1c1ncc(-c2cc3c4c(c2)OCc2cc(-c5cnc([C@@H]6CCCN6C(=O)[C@H](NC(=O)OCC)c6ccccc6)[nH]5)cc(c2-4)OC3)[nH]1)c1ccccc1] | 891.8 |

| # | Compound | LCMS (observed (M + H)+) |
|---|----------|--------------------------|
| 487 | 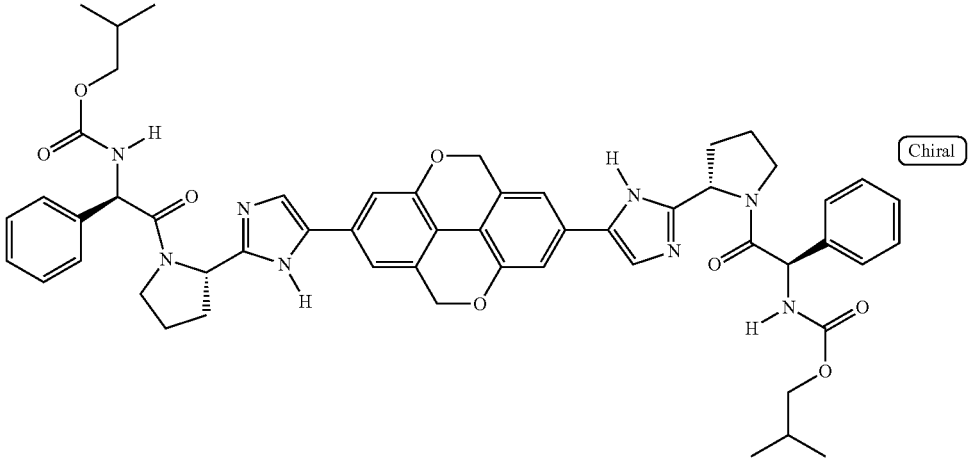 [SMILES: CC(C)COC(=O)N[C@@H](C(=O)N1CCC[C@H]1c1ncc(-c2cc3c4c(c2)OCc2cc(-c5cnc([C@@H]6CCCN6C(=O)[C@H](NC(=O)OCC(C)C)c6ccccc6)[nH]5)cc(c2-4)OC3)[nH]1)c1ccccc1] | 948.2 |
| 488 | 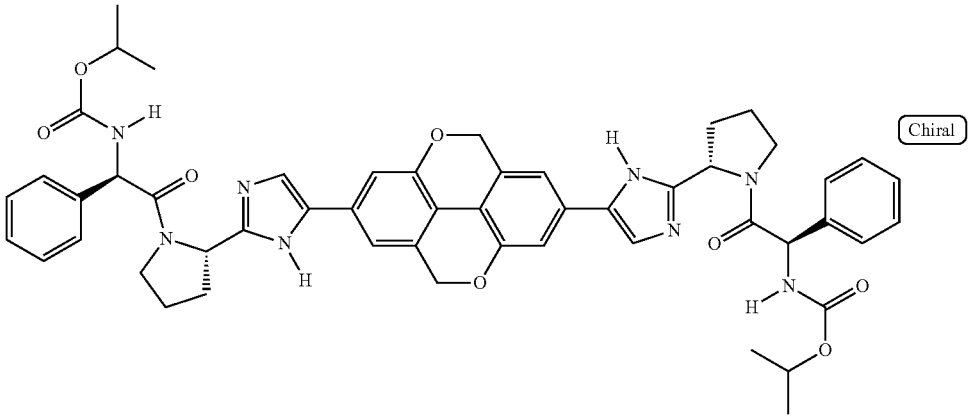 [SMILES: CC(C)OC(=O)N[C@@H](C(=O)N1CCC[C@H]1c1ncc(-c2cc3c4c(c2)OCc2cc(-c5cnc([C@@H]6CCCN6C(=O)[C@H](NC(=O)OC(C)C)c6ccccc6)[nH]5)cc(c2-4)OC3)[nH]1)c1ccccc1] | 919.8 |
| 489 | 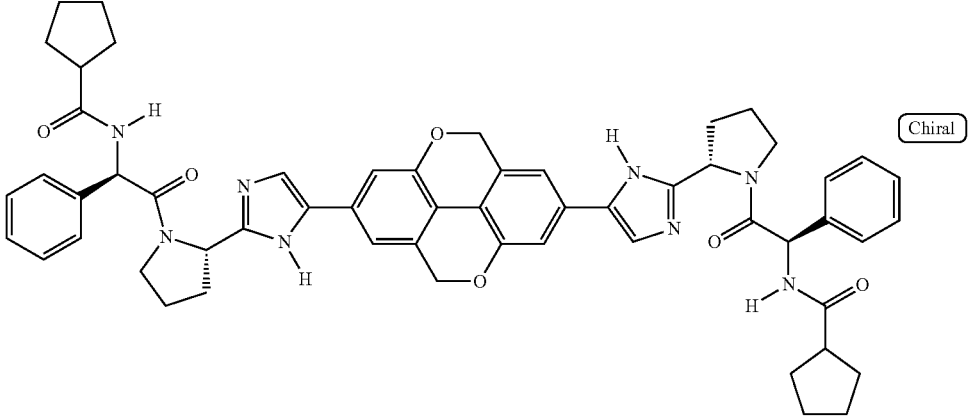 [SMILES: O=C(N[C@@H](C(=O)N1CCC[C@H]1c1ncc(-c2cc3c4c(c2)OCc2cc(-c5cnc([C@@H]6CCCN6C(=O)[C@H](NC(=O)C6CCCC6)c6ccccc6)[nH]5)cc(c2-4)OC3)[nH]1)c1ccccc1)C1CCCC1] | 939.9 |

| # | Compound | LCMS (observed (M + H)+) |
|---|---|---|
| 490 | 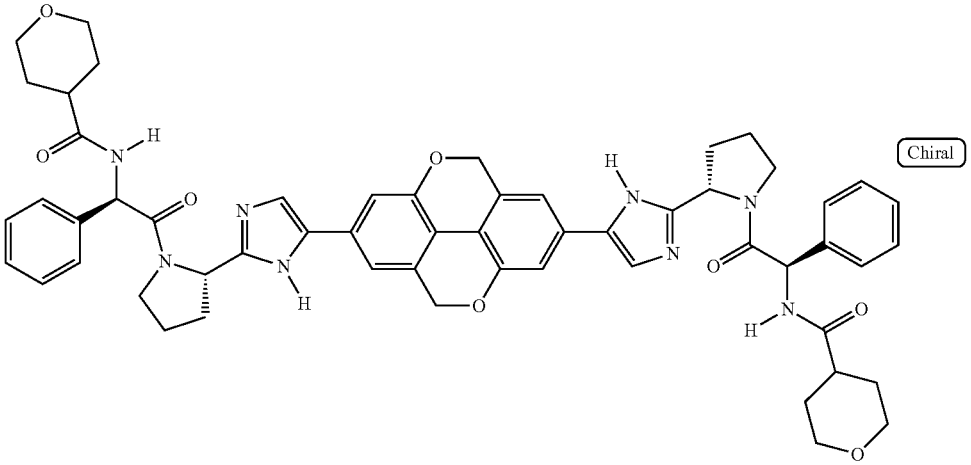 [SMILES: O=C(N[C@@H](C(=O)N1CCC[C@H]1c1ncc(-c2cc3c4c(c2)OCc2cc(-c5cnc([C@@H]6CCCN6C(=O)[C@H](NC(=O)C6CCOCC6)c6ccccc6)[nH]5)cc(c2-4)OC3)[nH]1)c1ccccc1)C1CCOCC1] | 972.1 |
| 491 | 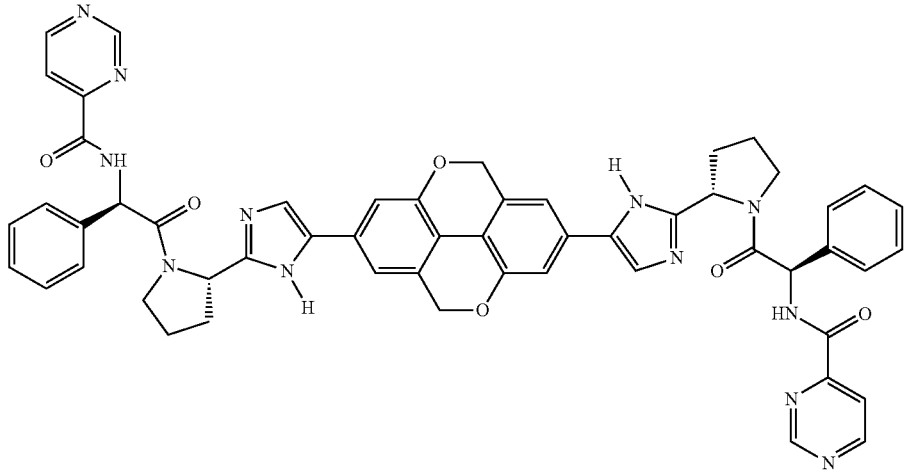 [SMILES: O=C(N[C@@H](C(=O)N1CCC[C@H]1c1ncc(-c2cc3c4c(c2)OCc2cc(-c5cnc([C@@H]6CCCN6C(=O)[C@H](NC(=O)c6ccncn6)c6ccccc6)[nH]5)cc(c2-4)OC3)[nH]1)c1ccccc1)c1ccncn1] | 959.7 |
| 492 | 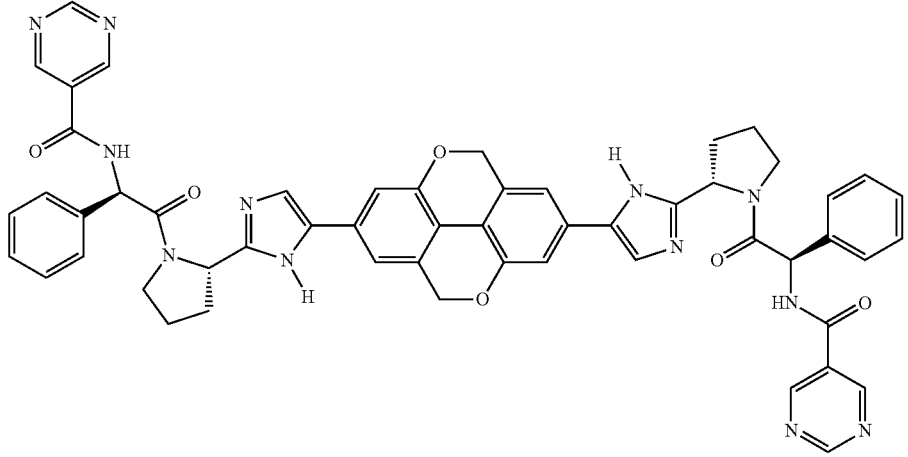 [SMILES: O=C(N[C@@H](C(=O)N1CCC[C@H]1c1ncc(-c2cc3c4c(c2)OCc2cc(-c5cnc([C@@H]6CCCN6C(=O)[C@H](NC(=O)c6cncnc6)c6ccccc6)[nH]5)cc(c2-4)OC3)[nH]1)c1ccccc1)c1cncnc1] | 959.1 |

-continued

| # | Compound | LCMS (observed (M + H)+) |
|---|---|---|
| 493 | | 838.2 |
| 494 | | 837.3 |
| 495 | | 835.7 |
| 496 | | 887.69 |

-continued
| # | Compound | LCMS (observed (M + H)+) |
|---|---|---|
| 497 | 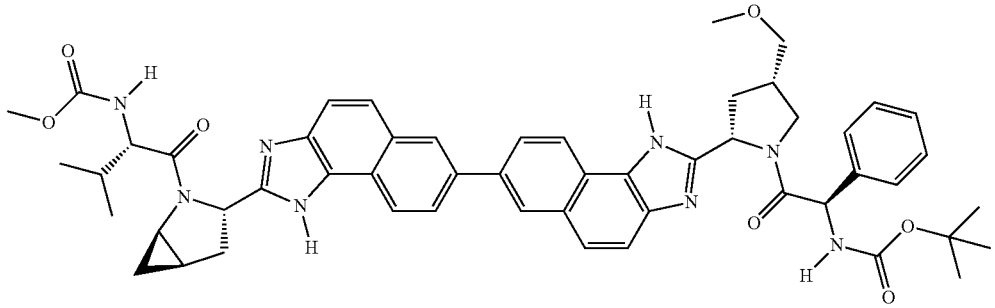 [SMILES: COC[C@H]1C[C@@H](c2nc3ccc4cc(-c5ccc6c(ccc7nc([C@@H]8C[C@H]9C[C@H]9N8C(=O)[C@@H](NC(=O)OC)C(C)C)[nH]c76)c5)ccc4c3[nH]2)N(C(=O)[C@H](NC(=O)OC(C)(C)C)c2ccccc2)C1] | 920 |
| 498 | 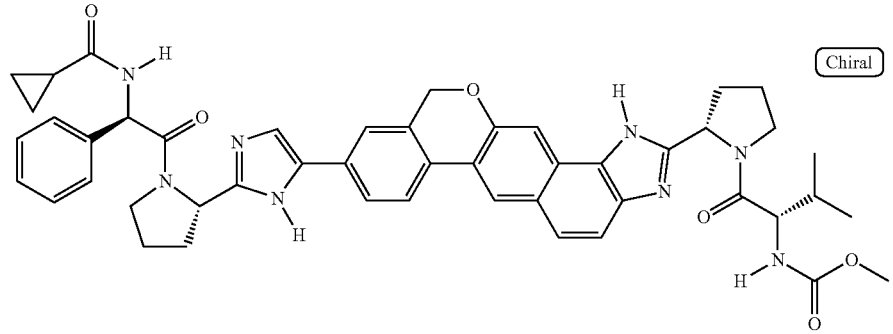 [SMILES: COC(=O)N[C@H](C(=O)N1CCC[C@H]1c1nc2ccc3cc4c(cc3c2[nH]1)OCc1cc(-c2cnc([C@@H]3CCCN3C(=O)[C@H](NC(=O)C3CC3)c3ccccc3)[nH]2)ccc1-4)C(C)C] Chiral | 835.34 |
| 499 | 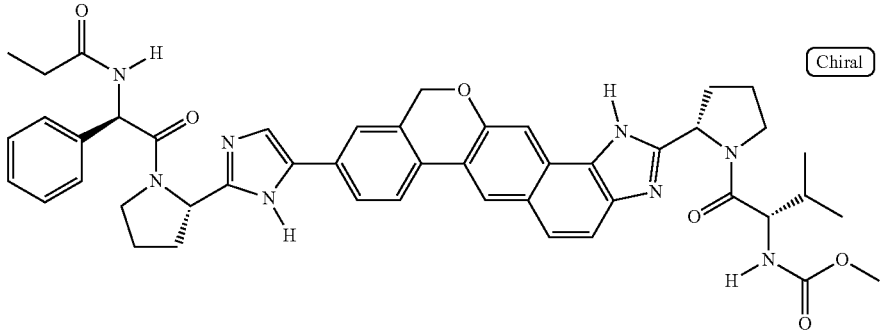 [SMILES: CCC(=O)N[C@@H](C(=O)N1CCC[C@H]1c1ncc(-c2ccc3c(c2)COc2cc4c(ccc5nc([C@@H]6CCCN6C(=O)[C@@H](NC(=O)OC)C(C)C)[nH]c54)cc2-3)[nH]1)c1ccccc1] Chiral | 823.35 |
| 500 | 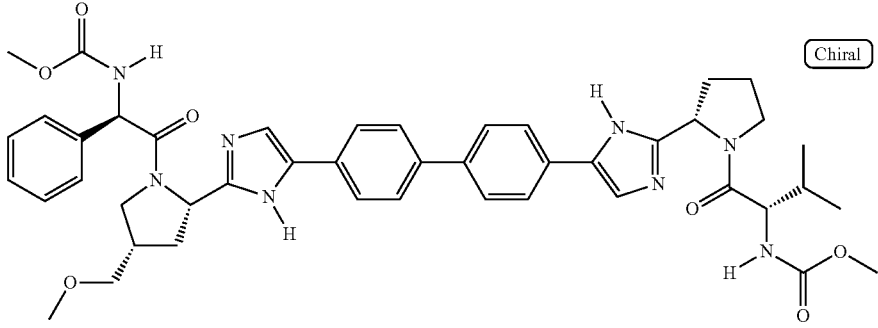 [SMILES: COC[C@H]1C[C@@H](c2ncc(-c3ccc(-c4ccc(-c5cnc([C@@H]6CCCN6C(=O)[C@@H](NC(=O)OC)C(C)C)[nH]5)cc4)cc3)[nH]2)N(C(=O)[C@H](NC(=O)OC)c2ccccc2)C1] Chiral | 817.34 |

| # | Compound | LCMS (observed (M + H)+) |
|---|---|---|
| 501 | 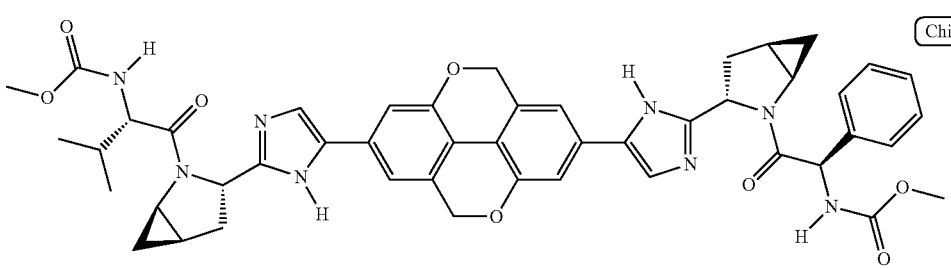 | 853.1 |
| 502 | 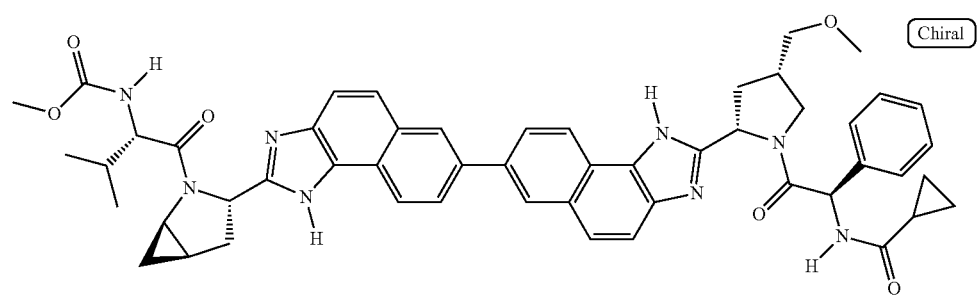 [SMILES: COC[C@H]1C[C@@H](c2nc3ccc4cc(-c5ccc6c(ccc7nc([C@@H]8C[C@H]9C[C@H]9N8C(=O)[C@@H](NC(=O)OC)C(C)C)[nH]c76)c5)ccc4c3[nH]2)N(C(=O)[C@H](NC(=O)C2CC2)c2ccccc2)C1] | 887.8 |
| 503 | 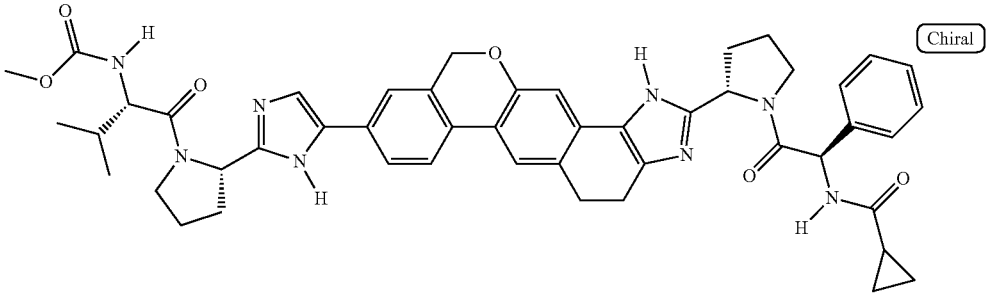 [SMILES: COC(=O)N[C@H](C(=O)N1CCC[C@H]1c1ncc(-c2ccc3c(c2)COc2cc4c(cc2-3)CCc2nc([C@@H]3CCCN3C(=O)[C@H](NC(=O)C3CC3)c3ccccc3)[nH]c2-4)[nH]1)C(C)C] | 837.35 |
| 504 | 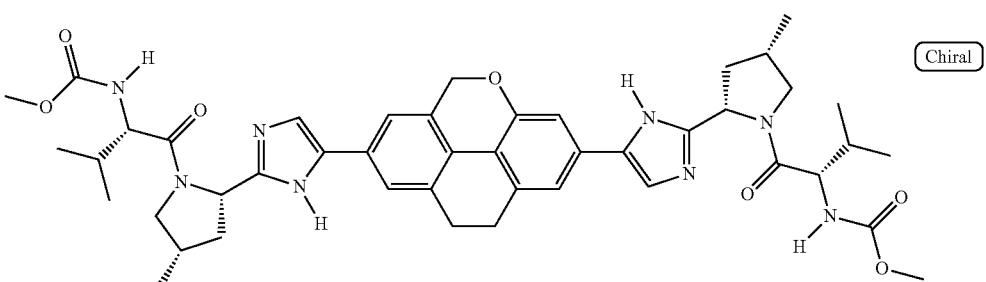 | 823.2 |
| 505 | 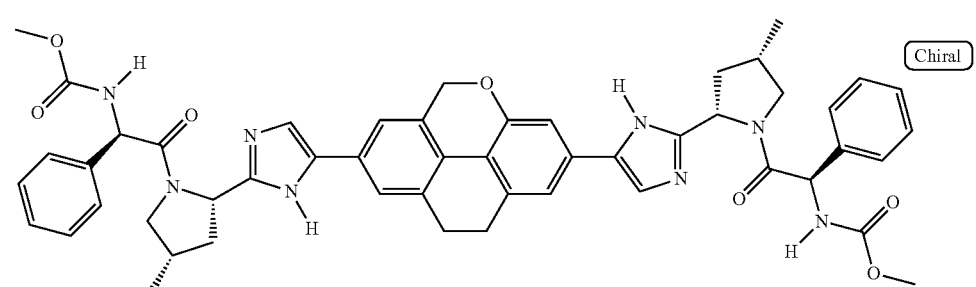 | 891.3 |

-continued
| # | Compound | LCMS (observed (M + H)+) |
|---|----------|--------------------------|
| 506 | 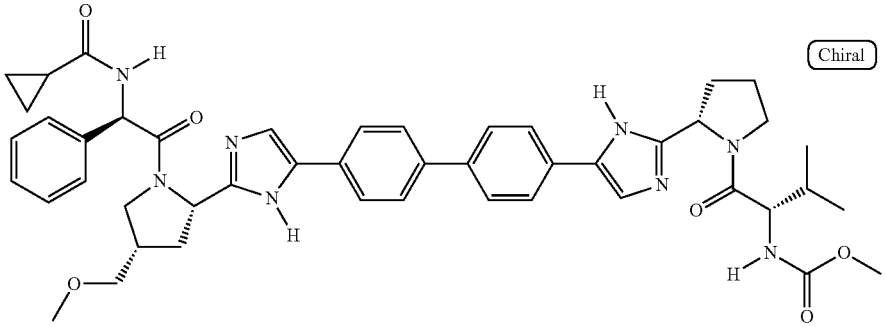 [SMILES: COC[C@H]1C[C@@H](c2ncc(-c3ccc(-c4ccc(-c5cnc([C@@H]6CCCN6C(=O)[C@@H](NC(=O)OC)C(C)C)[nH]5)cc4)cc3)[nH]2)N(C(=O)[C@H](NC(=O)C2CC2)c2ccccc2)C1] | 827.37 |
| 507 | 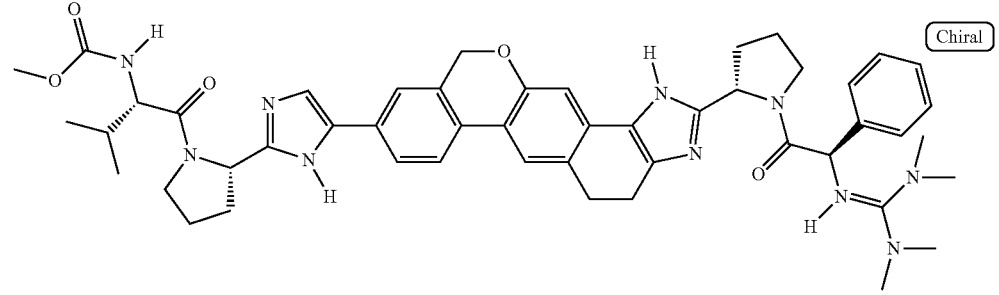 | 865.32 |
| 508 | 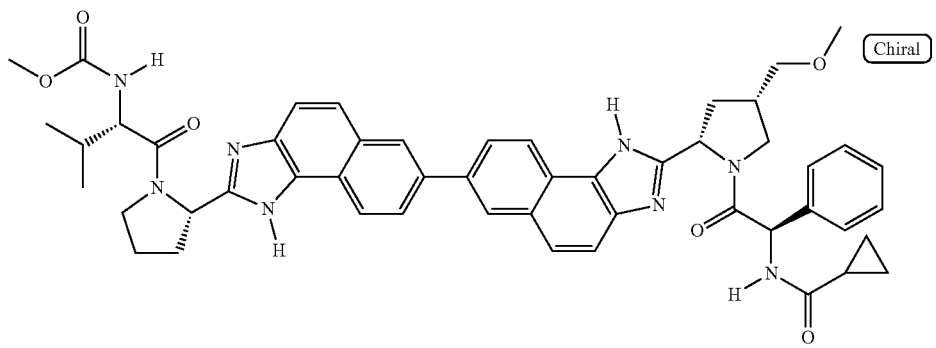 [SMILES: COC[C@H]1C[C@@H](c2nc3ccc4cc(-c5ccc6c(ccc7nc([C@@H]8CCCN8C(=O)[C@@H](NC(=O)OC)C(C)C)[nH]c76)c5)ccc4c3[nH]2)N(C(=O)[C@H](NC(=O)C2CC2)c2ccccc2)C1] | 875.71 |
| 509 | 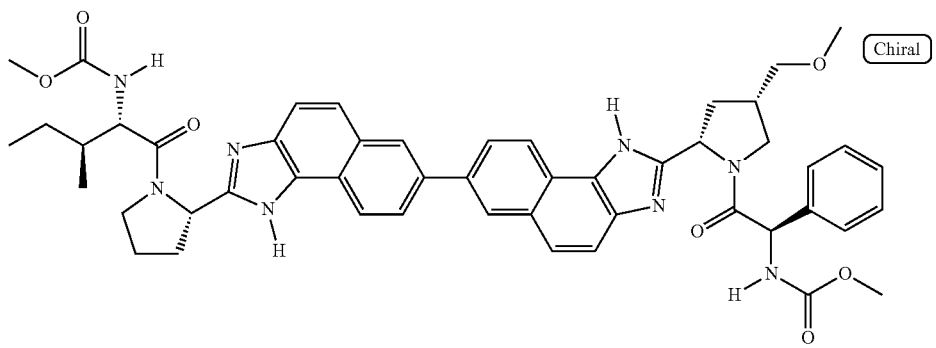 | 880.03 |

| # | Compound | LCMS (observed (M + H)+) |
|---|---|---|
| 510 | 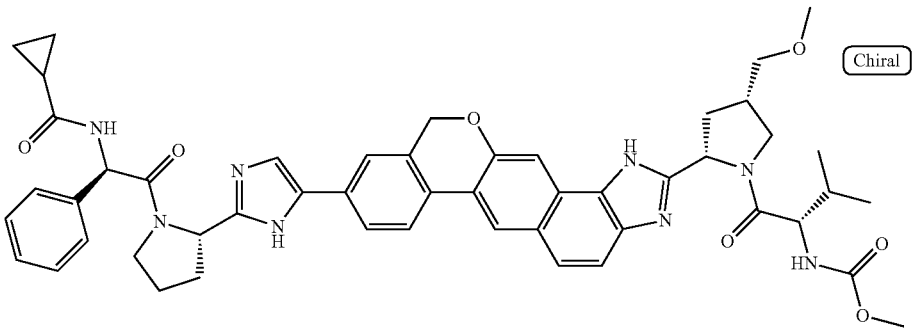 [SMILES: COC[C@H]1C[C@@H](c2nc3ccc4cc5c(cc4c3[nH]2)OCc2cc(-c3cnc([C@@H]4CCCN4C(=O)[C@H](NC(=O)C4CC4)c4ccccc4)[nH]3)ccc2-5)N(C(=O)[C@@H](NC(=O)OC)C(C)C)C1] |  |
| 511 | 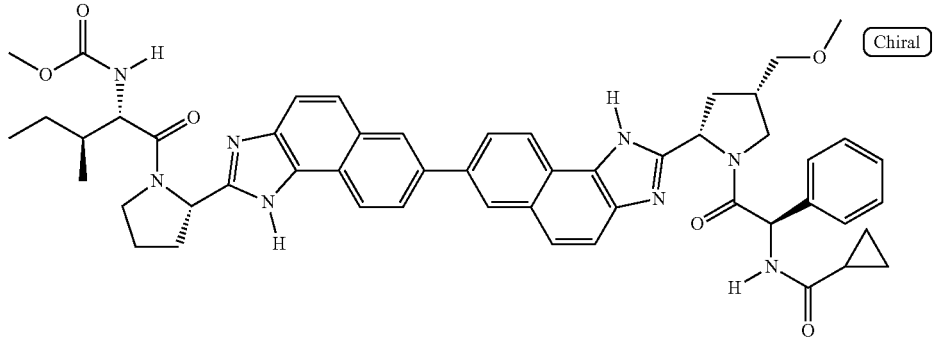 [SMILES: CC[C@H](C)[C@H](NC(=O)OC)C(=O)N1CCC[C@H]1c1nc2ccc3cc(-c4ccc5c(ccc6nc([C@@H]7C[C@H](COC)CN7C(=O)[C@H](NC(=O)C7CC7)c7ccccc7)[nH]c65)c4)ccc3c2[nH]1] | 889.68 |
| 512 | 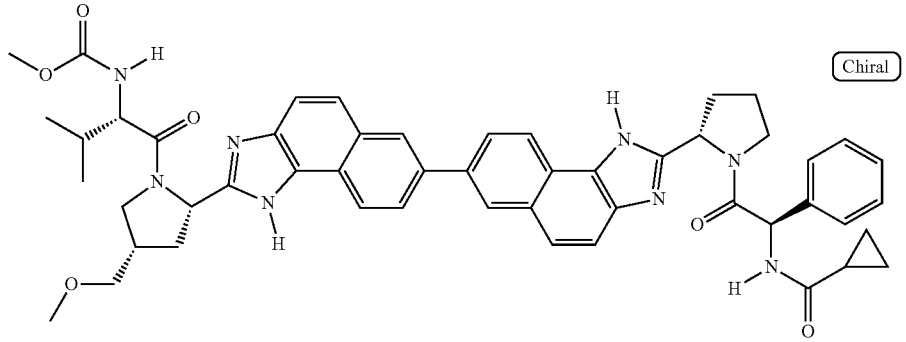 [SMILES: COC[C@H]1C[C@@H](c2nc3ccc4cc(-c5ccc6c(ccc7nc([C@@H]8CCCN8C(=O)[C@H](NC(=O)C8CC8)c8ccccc8)[nH]c76)c5)ccc4c3[nH]2)N(C(=O)[C@@H](NC(=O)OC)C(C)C)C1] | 876 |
| 513 | 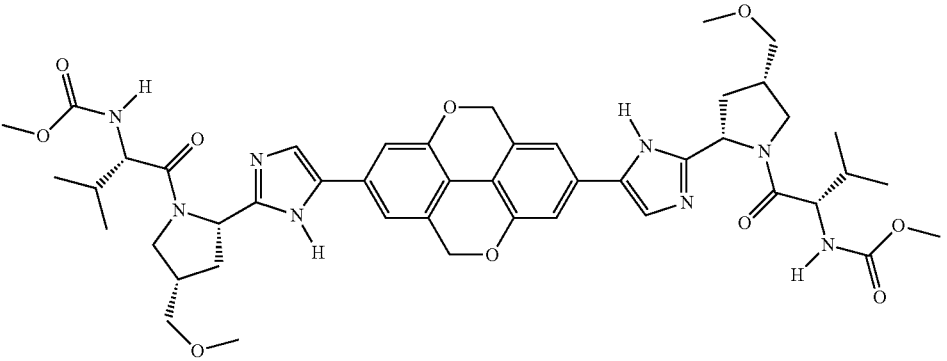 | 884.13 |

| # | Compound | LCMS (observed (M + H)+) |
|---|---|---|
| 514 | | 867.8 |
| 515 | | 833.35 |
| 516 | | 836.04 |
| 517 | | 841.47 |
| 518 | | 803.2 |

-continued

| # | Compound | LCMS (observed (M + H)+) |
|---|---|---|
| 519 | | 839.48 |
| 520 | | 839.9 |
| 521 | | 853.1 |
| 522 | | 876.1 |

-continued

| # | Compound | LCMS (observed (M + H)+) |
|---|---|---|
| 523 | | 878.0 |
| 524 | | 822.2 |
| 525 | | 866 |
| 526 | | 806.11 |

-continued

| # | Compound | LCMS (observed (M + H)+) |
|---|---|---|
| 527 | | 839.91 |
| 528 | | 902.05 |
| 529 | | 892.07 |
| 530 | | 892.15 |
| 531 | | 902.21 |

| # | Compound | LCMS (observed) (M + H)+ |
|---|---|---|
| 532 | 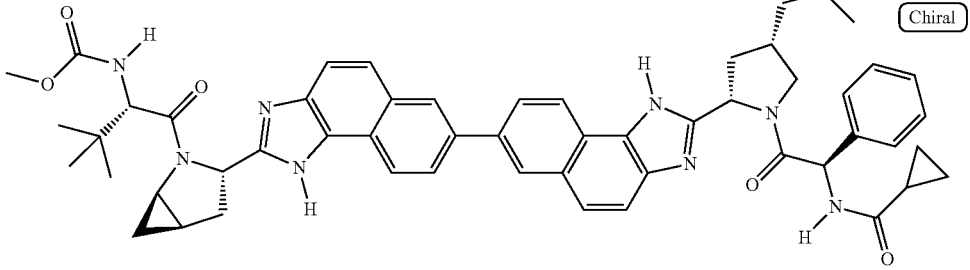 | 902.13 |
| 533 | 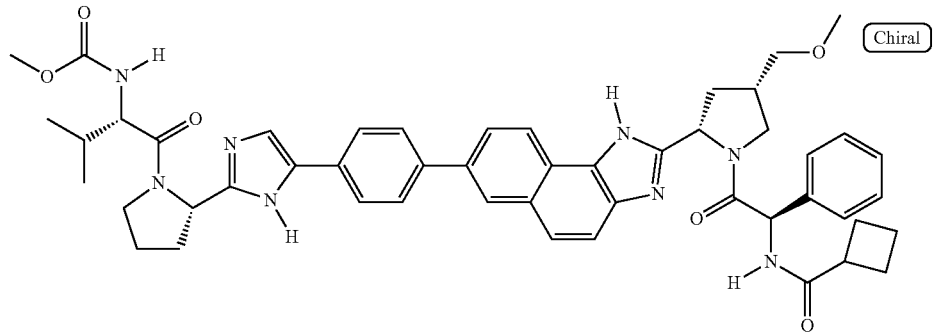 [SMILES: COC[C@H]1C[C@@H](c2nc3ccc4cc(-c5ccc(-c6cnc([C@@H]7CCCN7C(=O)[C@@H](NC(=O)OC)C(C)C)[nH]6)cc5)ccc4c3[nH]2)N(C(=O)[C@H](NC(=O)C2CCC2)c2ccccc2)C1] | 866.3 |
| 534 | 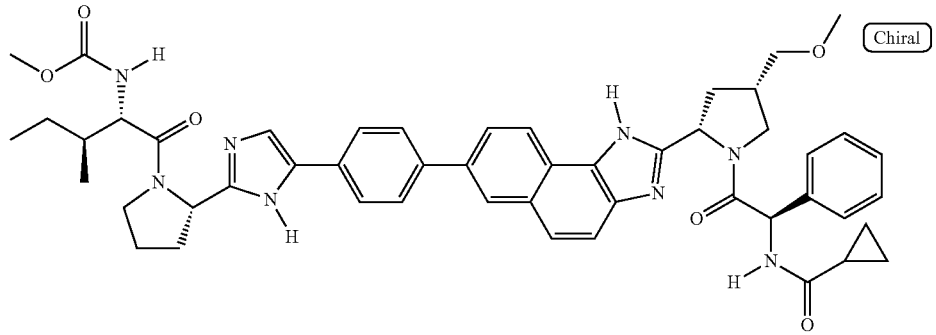 [SMILES: CC[C@H](C)[C@H](NC(=O)OC)C(=O)N1CCC[C@H]1c1ncc(-c2ccc(-c3ccc4c(ccc5nc([C@@H]6C[C@H](COC)CN6C(=O)[C@H](NC(=O)C6CC6)c6ccccc6)[nH]c54)c3)cc2)[nH]1] | 866.11 |
| 535 | 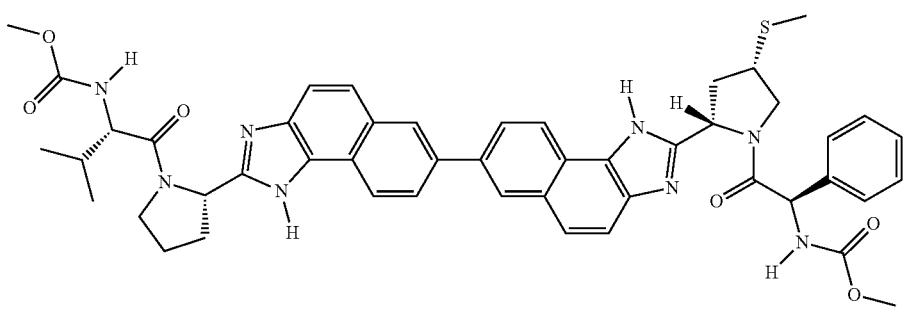 [SMILES: COC(=O)N[C@H](C(=O)N1CCC[C@H]1c1nc2ccc3cc(-c4ccc5c(ccc6nc([C@@H]7C[C@H](SC)CN7C(=O)[C@H](NC(=O)OC)c7ccccc7)[nH]c65)c4)ccc3c2[nH]1)C(C)C] | 867.58 |
| 536 | 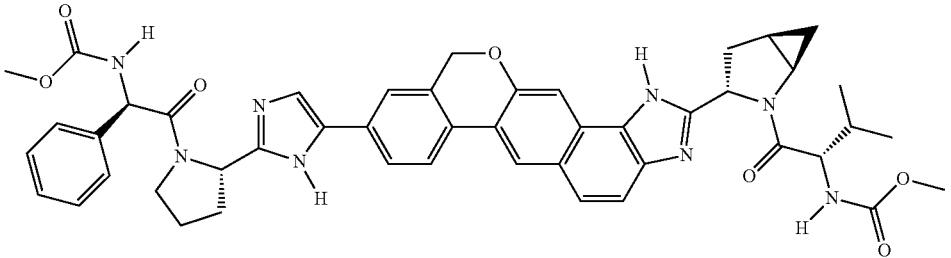 | 838.29 |

| # | Compound | LCMS (observed) (M + H)+ |
|---|---|---|
| 537 | | 890.14 |
| 538 | | 870.11 |
| 539 | | 882.09 |

Biological Assays

Effect of serum proteins on replicon potency: Replicon assays are conducted in normal cell culture medium (DMEM+10% FBS) supplemented with physiologic concentrations of human serum albumin (40 mg/mL) or α-acid glycoprotein (1 mg/mL). $EC_{50}$s in the presence of human serum proteins are compared to the $EC_{50}$ in normal medium to determine the fold shift in potency.

MT-4 Cell Cytotoxicity: MT4 cells are treated with serial dilutions of compounds for a five day period. Cell viability is measured at the end of the treatment period using the Promega CellTiter-Glo assay and non-linear regression is performed to calculate $CC_{50}$.

Compound Concentration Associated with Cells at $EC_{50}$: Huh-luc cultures are incubated with compound at concentrations equal to $EC_{50}$. At multiple time points (0-72 hours), cells are washed 2× with cold medium and extracted with 85% acetonitrile; a sample of the media at each time-point will also be extracted. Cell and media extracts are analyzed by LC/MS/MS to determine the Molar concentration of compounds in each fraction. Representative compounds of the invention have shown activity.

Solubility and Stability: Solubility is determined by taking an aliquot of 10 mM DMSO stock solution and preparing the compound at a final concentration of 100 μM in the test media solutions (PBS, pH 7.4 and 0.1 N HCl, pH 1.5) with a total DMSO concentration of 1%. The test media solutions are incubated at room temperature with shaking for 1 hr. The solutions will then be centrifuged and the recovered supernatants are assayed on the HPLC/UV. Solubility will be calculated by comparing the amount of compound detected in the defined test solution compared to the amount detected in DMSO at the same concentration. Stability of compounds after an 1 hour incubation with PBS at 37° C. will also be determined.

Stability in Cryopreserved Human, Dog, and Rat Hepatocytes: Each compound is incubated for up to 1 hour in hepatocyte suspensions (100 μl, 80,000° Cells per well) at 37° C. Cryopreserved hepatocytes are reconstituted in the serum-free incubation medium. The suspension is transferred into 96-well plates (50 μL/well). The compounds are diluted to 2 µM in incubation medium and then are added to hepatocyte suspensions to start the incubation. Samples are taken at 0, 10, 30 and 60 minutes after the start of incubation and reaction will be quenched with a mixture consisting of 0.3% formic acid in 90% acetonitrile/10% water. The concentration of the compound in each sample is analyzed using LC/MS/MS. The disappearance half-life of the compound in hepatocyte suspension is determined by fitting the concentration-time data with a monophasic exponential equation. The data will also be scaled up to represent intrinsic hepatic clearance and/or total hepatic clearance.

Stability in Hepatic S9 Fraction from Human, Dog, and Rat: Each compound is incubated for up to 1 hour in S9 suspension (500 µl, 3 mg protein/mL) at 37° C. (n=3). The compounds are added to the S9 suspension to start the incubation. Samples are taken at 0, 10, 30, and 60 minutes after the start of incubation. The concentration of the compound in each sample is analyzed using LC/MS/MS. The disappearance half-life of the compound in S9 suspension is determined by fitting the concentration-time data with a monophasic exponential equation.

Caco-2 Permeability: Compounds are assayed via a contract service (Absorption Systems, Exton, Pa.). Compounds are provided to the contractor in a blinded manner. Both forward (A-to-B) and reverse (B-to-A) permeability will be measured. Caco-2 monolayers are grown to confluence on collagen-coated, microporous, polycarbonate membranes in 12-well Costar TRANSWELL® plates. The compounds are dosed on the apical side for forward permeability (A-to-B), and are dosed on the basolateral side for reverse permeability (B-to-A). The cells are incubated at 37° C. with 5% $CO_2$ in a humidified incubator. At the beginning of incubation and at 1 hr and 2 hr after incubation, a 200-µL aliquot is taken from the receiver chamber and replaced with fresh assay buffer. The concentration of the compound in each sample is determined with LC/MS/MS. The apparent permeability, Papp, is calculated.

Plasma Protein Binding: Plasma protein binding is measured by equilibrium dialysis. Each compound is spiked into blank plasma at a final concentration of 2 µM. The spiked plasma and phosphate buffer is placed into opposite sides of the assembled dialysis cells, which will then be rotated slowly in a 37° C. water bath. At the end of the incubation, the concentration of the compound in plasma and phosphate buffer is determined. The percent unbound is calculated using the following equation:

$$\% \text{ Unbound} = 100 \cdot \left( \frac{C_f}{C_b + C_f} \right)$$

Where $C_f$ and $C_b$ are free and bound concentrations determined as the post-dialysis buffer and plasma concentrations, respectively.

CYP450 Profiling: Each compound is incubated with each of 5 recombinant human CYP450 enzymes, including CYP1A2, CYP2C9, CYP3A4, CYP2 D6 and CYP2C19 in the presence and absence of NADPH. Serial samples will be taken from the incubation mixture at the beginning of the incubation and at 5, 15, 30, 45 and 60 minutes after the start of the incubation. The concentration of the compound in the incubation mixture is determined by LC/MS/MS. The percentage of the compound remaining after incubation at each time point is calculated by comparing with the sampling at the start of incubation.

Stability in Rat, Dog, Monkey and Human Plasma: Compounds will be incubated for up to 2 hours in plasma (rat, dog, monkey, or human) at 37° C. Compounds are added to the plasma at final concentrations of 1 and 10 µg/mL. Aliquots are taken at 0, 5, 15, 30, 60, and 120 minutes after adding the compound. Concentration of compounds and major metabolites at each timepoint are measured by LC/MS/MS.

Evaluation of cell-based anti-HCV activity: Antiviral potency ($EC_{50}$) was determined using a Renilla luciferase (RLuc)-based HCV replicon reporter assay. To perform the assay for genotype 1 and 2a JFH-1, HCV 1b RLuc cells (harboring a dicistronic genotype 1b Con1 replicon that encodes a RLuc reporter), or HCV 1a RLuc cells (harboring a dicistronic genotype 1a H77 replicon that encodes a RLuc reporter), or HCV 2a JFH-1 Rluc cells (harboring a dicistronic genotype 2a JFH-1 replicon that encodes a RLuc reporter) were dispensed into 384-well plates. To perform the assay for genotype 2a (with M31 present) or 2b, HCV 2a Rluc or 2b Rluc cells (both with M31 present) harboring a dicistronic NS5A chimeric genotype 2a JFH-1 replicon that encodes a RLuc reporter and either genotype 2a J6 strain NS5A gene or genotype 2b MD2b-1 NS5A gene (based on Los Alamos HCV database isolates, both with M31 present) respectively, were dispensed into 384-well plates. To perform the assay for genotype 3 and 4, HCV 3a RLuc or 4a Rluc cells harboring a dicistronic NS5A chimeric genotype 1b Con1 replicon that encodes a RLuc reporter and either a consensus genotype 3a NS5A gene or genotype 4a NS5A gene (based on Los Alamos HCV database isolates) respectively, were dispensed into 384-well plates. Compounds were re-suspended in DMSO at a concentration of 10 mM and serially diluted in DMSO either manually or using an automated pipeting instrument. Serially diluted compounds were mixed with cell culture media and added to the seeded cells. DMSO was used as a negative (solvent) control, and the protease inhibitor ITMN-191 was included at a concentration >100×$EC_{50}$ as a positive control. 72 hours later, cells were lysed and Renilla luciferase activity quantified as recommended by the manufacturer (Promega-Madison, Wis.). Non-linear regression was performed to calculate $EC_{50}$ values.

To determine the antiviral potency ($EC_{50}$) against resistance mutants, resistance mutations, including M28T, Q30R, Q30H, L31M, and Y93C in genotype 1a NS5A and Y93H in genotype 1b NS5A, were introduced individually into either 1a Rluc or 1b Rluc replicons described above by site directed mutagenesis. Replicon RNA of each resistant mutant was transfected into Huh-7 cured-51 cells and antiviral potency was determined on these transfected cells as described above.

TABLE 1

| # | 1b (nM) | 1a | 1a Q30R | 2a JFH | 2a J6 | 2b | 3a | 4a |
|---|---|---|---|---|---|---|---|---|
| 1 | 0.008 | C | C | C | A | A | C | C |
| 2 | 0.005 | C | C | C | A | A | C | C |
| 3 | 0.011 | C | C | C | | | C | |

TABLE 1-continued

| # | 1b (nM) | 1a | 1a Q30R | 2a JFH | 2a J6 | 2b | 3a | 4a |
|---|---|---|---|---|---|---|---|---|
| 4 | 0.11 | C | C | C | | | C | C |
| 5 | 0.037 | A | B | B | | | C | C |
| 6 | 0.051 | B | B | B | | | A | C |

TABLE 1-continued

| # | | 1b (nM) | 1a | 1a Q30R | 2a JFH | 2a J6 | 2b | 3a | 4a |
|---|---|---|---|---|---|---|---|---|---|
| 7 | (structure) | 0.008 | C | C | C | C | C | C | C |
| 8 | (structure) | 0.006 | C | C | C | A | A | B | C |
| 9 | (structure) | 0.022 | C | C | C | A | B | C | C |

TABLE 1-continued
| # | | 1b (nM) | 1a | 1a Q30R | 2a JFH | 2a J6 | 2b | 3a | 4a |
|---|---|---------|----|---------|--------|-------|----|----|----|
| 10 | 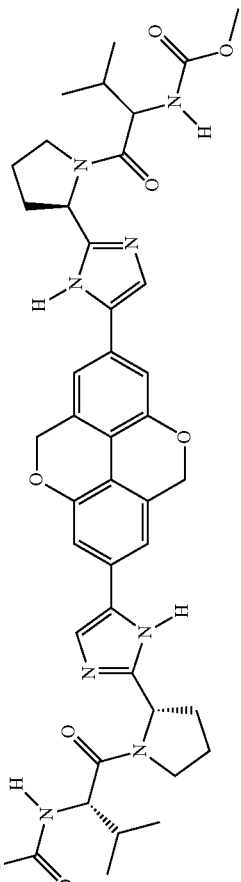 | 0.406 | B | | C | | | C | C |
| 11 | 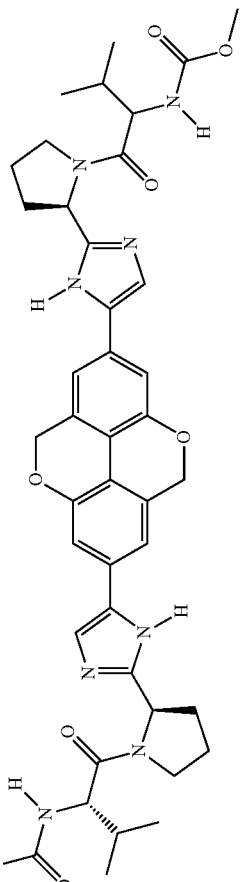 | 0.258 | B | | C | | | | |
| 12 | 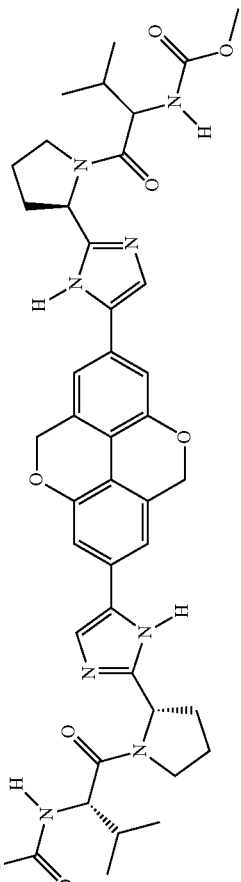 | 0.008 | C | | C | A | A | C | C |

TABLE 1-continued
| # | | 1b (nM) | 1a | 1a Q30R | 2a JFH | 2a J6 | 2b | 3a | 4a |
|---|---|---|---|---|---|---|---|---|---|
| 13 | 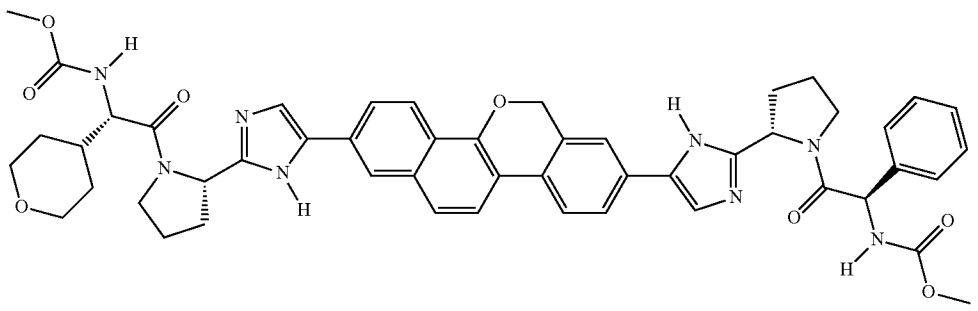 | 0.015 | C | C | C | B | C | C | C |
| 14 | 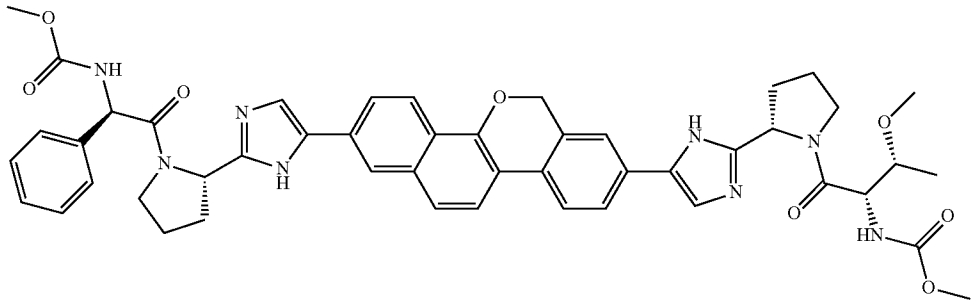 | 0.010 | C | C | C | | | C | C |
| 15 | 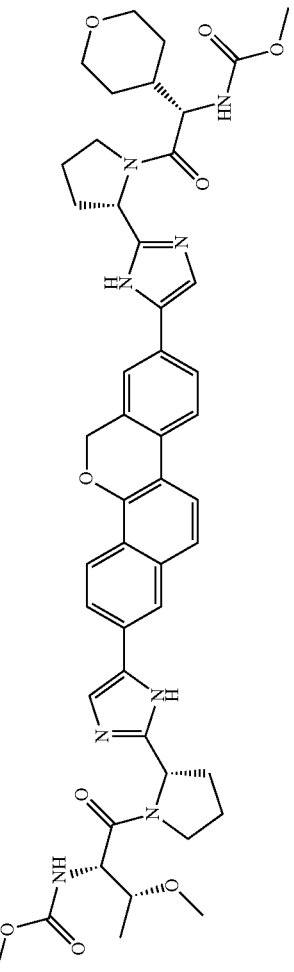 | 0.026 | C | C | C | | | C | C |

TABLE 1-continued

| # | 1b (nM) | 1a | 1a Q30R | 2a JFH | 2a J6 | 2b | 3a | 4a |
|---|---|---|---|---|---|---|---|---|
| 16 | 0.011 | C | C | C | B | B | C | C |
| 17 | 0.014 | C | C | C | | | A | C |
| 18 | 0.018 | C | C | C | | | B | C |

TABLE 1-continued

| # | | 1b (nM) | 1a | 1a Q30R | 2a JFH | 2a J6 | 2b | 3a | 4a |
|---|---|---|---|---|---|---|---|---|---|
| 19 | Chiral | 0.010 | B | B | B | | | A | C |
| 20 | Chiral | 0.021 | C | C | C | | | C | C |
| 21 | Chiral | 0.060 | C | C | C | | | C | C |

TABLE 1-continued

| # | | 1b (nM) | 1a | 1a Q30R | 2a JFH | 2a J6 | 2b | 3a | 4a |
|---|---|---|---|---|---|---|---|---|---|
| 22 | Chiral | 0.005 | C | C | C | A | A | C | C |
| 23 | Chiral | 0.067 | C | C | C | | | C | C |
| 24 | Chiral | 0.013 | C | C | C | A | A | C | C |

TABLE 1-continued
| # | | 1b (nM) | 1a | 1a Q30R | 2a JFH | 2a J6 | 2b | 3a | 4a |
|---|---|---|---|---|---|---|---|---|---|
| 25 | Chiral | 0.021 | C | C | C | | | | C | C |
| 25b | Chiral | 0.176 | C | C | C | B | | C | C |
| 25c | Chiral | 0.031 | C | C | C | B | C | C | C |
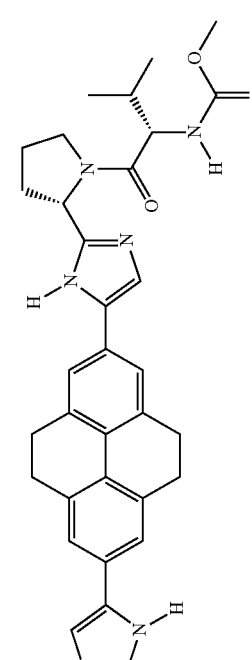
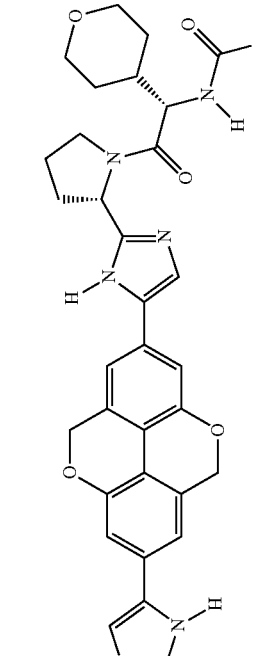
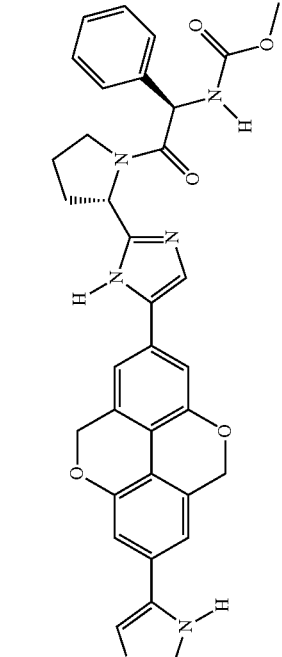

TABLE 1-continued
| # | 1b (nM) | 1a | 1a Q30R | 2a JFH | 2a J6 | 2b | 3a | 4a |
|---|---|---|---|---|---|---|---|---|
| 25d | 0.048 | C | C | C | C | C | C | C |
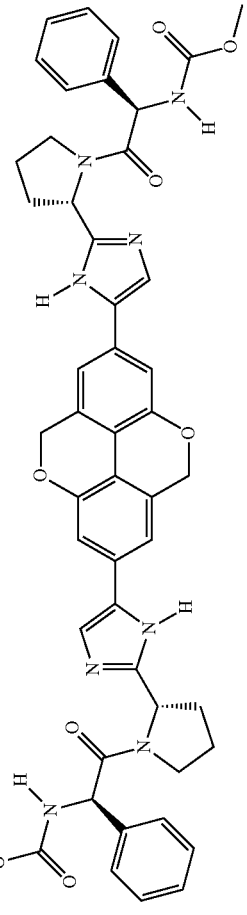
1b (nM); 1a, Q30R, 2a JFH, 2a J6, 2b-A ≥ 44 nM, B = 1-43.99 nM, C = 0.001-0.999 nM; 3a, 4a-A ≥ 5 nM, B = 1-4.99 nM, C = 0.001-0.99 nM

TABLE 2

| # | 1b (nM) | 1a | 1a Q30R | 2a JFH | 2a J6 | 2b | 3a | 4a |
|---|---|---|---|---|---|---|---|---|
| 26 | 0.012 | C | C | C | B | B | C | C |
| 27 | 0.011 | C | | C | | | C | |
| 28 | 0.023 | B | | B | | | C | |

TABLE 2-continued

| # | 1b (nM) | 1a | 1a Q30R | 2a JFH | 2a J6 | 2b | 3a | 4a |
|---|---|---|---|---|---|---|---|---|
| 29 | 0.014 | C | | C | | | C | |
| 30 | 0.008 | C | | C | | | C | |
| 31 | 0.014 | C | | C | | | C | |

TABLE 2-continued

| # | 1b (nM) | 1a | 1a Q30R | 2a JFH | 2a J6 | 2b | 3a | 4a |
|---|---|---|---|---|---|---|---|---|
| 32 | 0.020 | C | | C | | | A | |
| 33 | 0.009 | C | | C | | | C | |

TABLE 2-continued

| # | 1b (nM) | 1a | 1a Q30R | 2a JFH | 2a J6 | 2b | 3a | 4a |
|---|---------|----|---------|--------|-------|----|----|----|
| 34 | 0.018 | C | | C | | | C | |
| 35 | 0.008 | C | | C | | | C | |
| 36 | 0.010 | C | | C | | | C | |

TABLE 2-continued

| # | 1b (nM) | 1a | 1a Q30R | 2a JFH | 2a J6 | 2b | 3a | 4a |
|---|---|---|---|---|---|---|---|---|
| 37 | 0.004 | C | | B | | | | C |
| 38 | 0.003 | C | | B | | | | A |

TABLE 2-continued
| # | 1b (nM) | 1a | 1a Q30R | 2a JFH | 2a J6 | 2b | 3a | 4a |
|---|---------|----|---------|--------|-------|----|----|----|
| 39 | 0.009 | C | | B | | | B | C |
| 40 | 0.005 | C | | C | | | B | C |
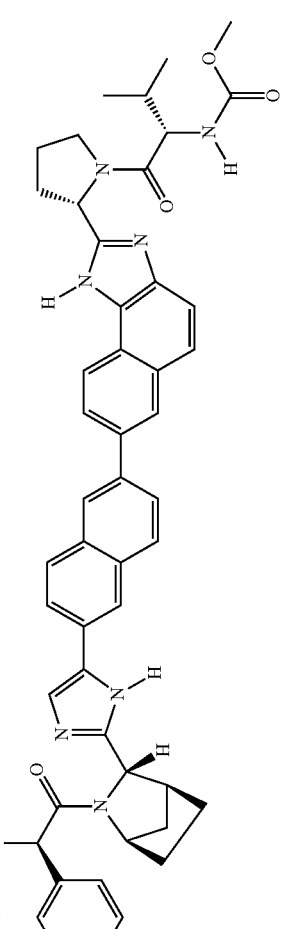
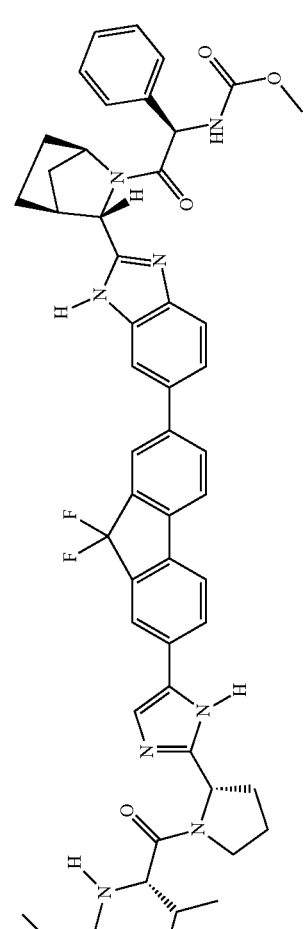

TABLE 2-continued

| # | 1b (nM) | 1a | 1a Q30R | 2a JFH | 2a J6 | 2b | 3a | 4a |
|---|---|---|---|---|---|---|---|---|
| 41 | 0.005 | C | C | C | | | C | C |
| 42 | 0.008 | C | C | C | | B | C | C |
| 43 | 0.009 | C | C | C | | B | C | C |

TABLE 2-continued

| # | 1b (nM) | 1a | 1a Q30R | 2a JFH | 2a J6 | 2b | 3a | 4a |
|---|---|---|---|---|---|---|---|---|
| 44 | 0.032 | C | | C | | | B | C |
| 45 | 0.014 | C | | C | | | B | C |
| 46 | 0.007 | C | | C | | | B | C |

TABLE 2-continued
| # | 1b (nM) | 1a | 1a Q30R | 2a JFH | 2a J6 | 2b | 3a | 4a |
|---|---|---|---|---|---|---|---|---|
| 47 | 0.037 | C | | C | | B | C | |
| 48 | 0.007 | C | | B | | B | C | |
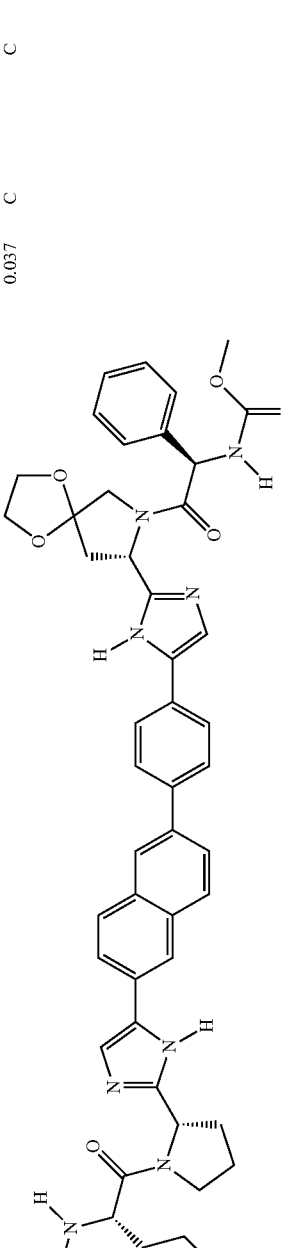
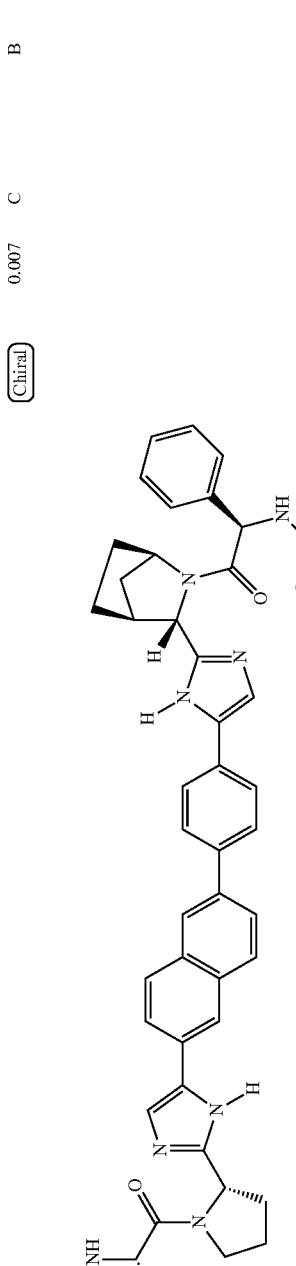

TABLE 2-continued

| # | 1b (nM) | 1a | 1a Q30R | 2a JFH | 2a J6 | 2b | 3a | 4a |
|---|---------|----|---------|--------|-------|----|----|----|
| 49 | 0.014 | C | | C | | | C | C |
| 50 | 0.031 | C | | C | | | | |

TABLE 2-continued
| # | 1b (nM) | 1a | 1a Q30R | 2a JFH | 2a J6 | 2b | 3a | 4a |
|---|---|---|---|---|---|---|---|---|
| 51 | 0.012 | B | | B | | | B | C |
| 52 | 0.009 | C | | B | | | B | C |
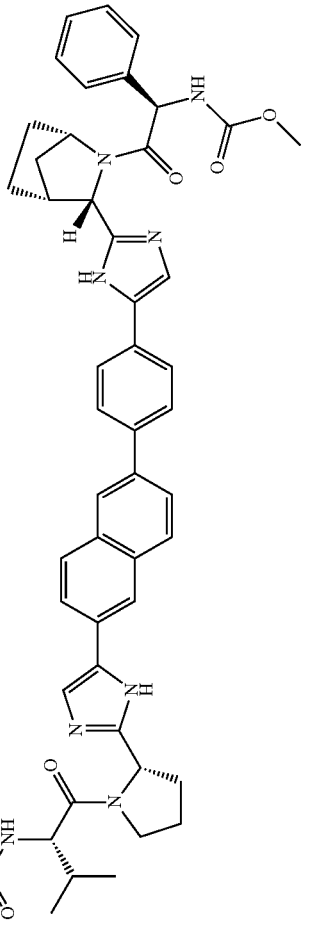
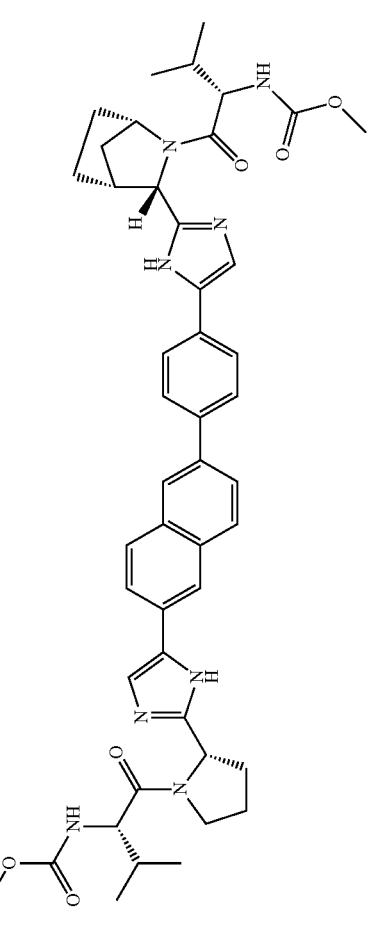

TABLE 2-continued

| # | 1b (nM) | 1a | 1a Q30R | 2a JFH | 2a J6 | 2b | 3a | 4a |
|---|---|---|---|---|---|---|---|---|
| 53 | 0.010 | C | | C | A | | C | C |
| 54 | 0.014 | C | | C | A | | C | C |
| 55 | 0.015 | C | | C | A | | C | C |

TABLE 2-continued
| # | | 1b (nM) | 1a | 1a Q30R | 2a JFH | 2a J6 | 2b | 3a | 4a |
|---|---|---|---|---|---|---|---|---|---|
| 56 | 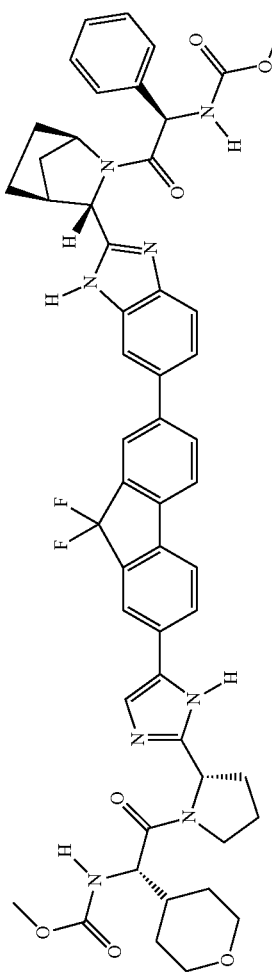 | 0.010 | C | | C | | | C | C |
| 57 | 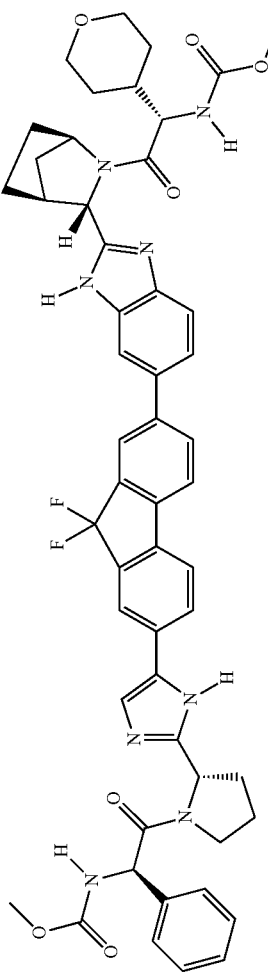 | 0.009 | C | | C | | | C | C |
| 58 | 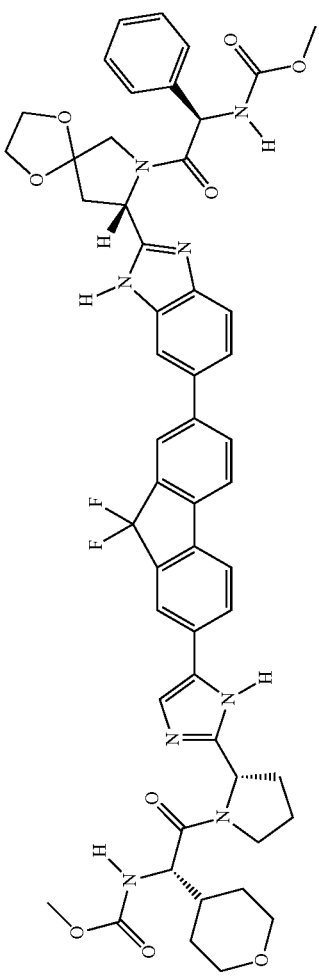 | 0.017 | C | | C | | | B | C |

TABLE 2-continued
| # | | 1b (nM) | 1a | 1a Q30R | 2a JFH | 2a J6 | 2b | 3a | 4a |
|---|---|---|---|---|---|---|---|---|---|
| 59 | 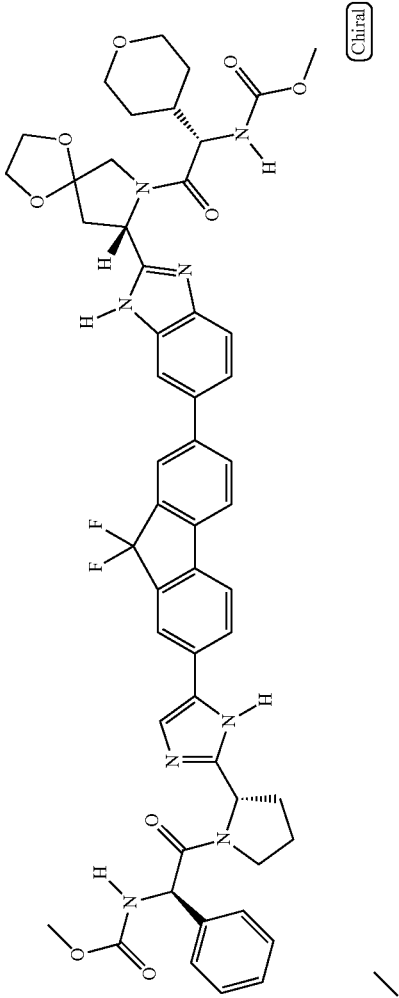 | 0.016 | C | | C | | | C | C |
| 60 | 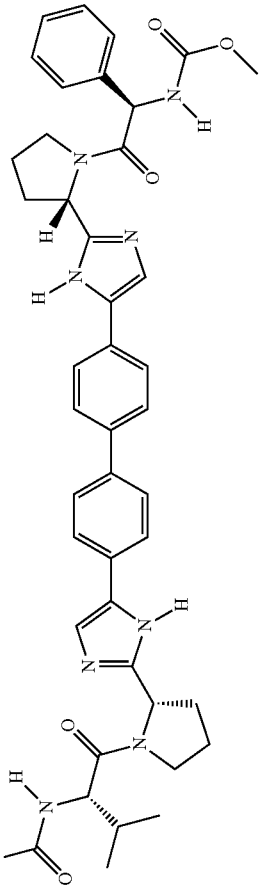 | 0.020 | B | | C | | | C | C |
| 61 | 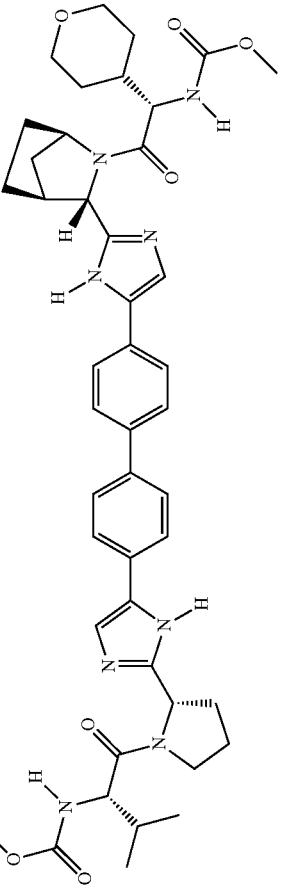 | 0.087 | C | | C | | | B | C |

TABLE 2-continued

| # | 1b (nM) | 1a | 1a Q30R | 2a JFH | 2a J6 | 2b | 3a | 4a |
|---|---|---|---|---|---|---|---|---|
| 62 | 0.034 | C | | C | | | C | C |
| 63 | 0.019 | C | B | C | B | A | C | C |
| 64 | 0.018 | C | | C | | | C | C |

TABLE 2-continued
| # | 1b (nM) | 1a | 1a Q30R | 2a JFH | 2a J6 | 2b | 3a | 4a |
|---|---------|----|---------|--------|-------|----|----|----|
| 65 | 0.015 | C | | C | A | | C | C |
| 66 | 0.022 | C | | C | A | | C | C |
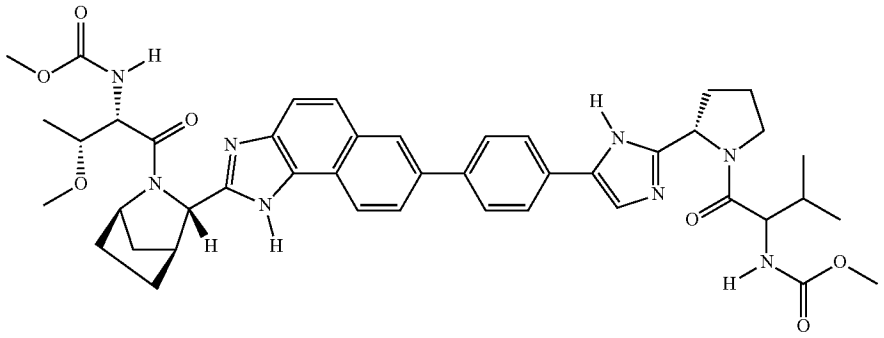

TABLE 2-continued

| # | 1b (nM) | 1a | 1a Q30R | 2a JFH | 2a J6 | 2b | 3a | 4a |
|---|---------|----|---------|--------|-------|----|----|----|
| 67 | 0.044 | C | | C | | | B | C |
| 68 | 0.025 | C | | C | B | | C | C |

TABLE 2-continued

| # | 1b (nM) | 1b | 1a Q30R | 2a JFH | 2a J6 | 2b | 3a | 4a |
|---|---|---|---|---|---|---|---|---|
| 69 | 0.035 | C | C | C | | | C | C |
| 70 | 0.008 | C | B | B | | | B | C |
| 71 | 0.013 | C | C | C | | | C | C |

TABLE 2-continued

| # | 1b (nM) | 1a | 1a Q30R | 2a JFH | 2a J6 | 2b | 3a | 4a |
|---|---|---|---|---|---|---|---|---|
| 72 | 0.006 | C | C | C | | | C | C |
| 73 | 0.038 | C | | C | | B | | C |
| 74 | 0.006 | C | | C | | | C | C |

TABLE 2-continued

| # | 1b (nM) | 1a | 1a Q30R | 2a JFH | 2a J6 | 2b | 3a | 4a |
|---|---|---|---|---|---|---|---|---|
| 75 | 0.005 | C | | C | | | C | C |
| 76 | 0.010 | C | | B | | | B | C |
| 77 | 0.029 | C | | C | | | C | C |

TABLE 2-continued

| # | 1b (nM) | 1a | 1a Q30R | 2a JFH | 2a J6 | 2b | 3a | 4a |
|---|---------|----|---------|--------|-------|----|----|----|
| 78 | 0.013 | C | C | C | | | C | C |
| 79 | 0.231 | C | | C | | | C | C |
| 80 | 0.072 | C | | C | A | | C | C |

TABLE 2-continued

| # | 1b (nM) | 1a | 1a Q30R | 2a JFH | 2a J6 | 2b | 3a | 4a |
|---|---|---|---|---|---|---|---|---|
| 81 | 0.006 | C | | C | | | C | C |
| 82 | 0.042 | C | | C | | | C | |
| 83 | 0.094 | C | | C | A | B | | C |

TABLE 2-continued

| # | 1b (nM) | 1a | 1a Q30R | 2a JFH | 2a J6 | 2b | 3a | 4a |
|---|---|---|---|---|---|---|---|---|
| 84 | 0.007 | C | C | C | | | C | C |
| 85 | 0.016 | C | C | C | | | B | C |
| 86 | 0.034 | C | C | C | | | B | C |

TABLE 2-continued
| # | 1b (nM) | 1a | 1a Q30R | 2a JFH | 2a J6 | 2b | 3a | 4a |
|---|---|---|---|---|---|---|---|---|
| 87 | 0.163 | C | | C | | | C | |
| 88 | 0.019 | C | | C | | | C | C |
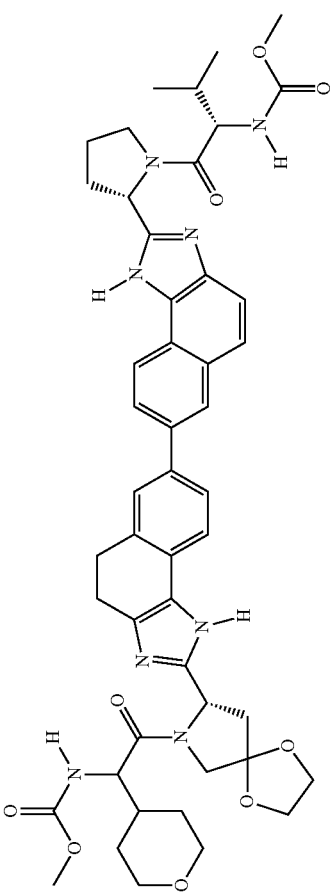
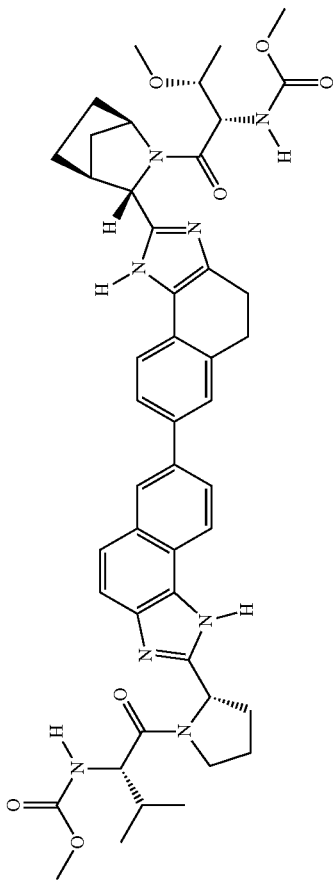

TABLE 2-continued
| # | 1b (nM) | 1a | 1a Q30R | 2a JFH | 2a J6 | 2b | 3a | 4a |
|---|---------|----|---------|--------|-------|----|----|----|
| 89 | 0.064 | C | | C | | | C | C |
| 90 | 0.044 | C | | C | | | B | C |

TABLE 2-continued

| # | 1b (nM) | 1a | 1a Q30R | 2a JFH | 2a J6 | 2b | 3a | 4a |
|---|---|---|---|---|---|---|---|---|
| 91 | 0.100 | C | | C | | | B | C |
| 92 | 0.047 | C | | C | | | C | C |
| 93 | 0.023 | C | | C | | | C | C |

TABLE 2-continued
| # | 1b (nM) | 1a | 1a Q30R | 2a JFH | 2a J6 | 2b | 3a | 4a |
|---|---|---|---|---|---|---|---|---|
| 94 | 0.007 | C | | C | C | | C | C |
| 95 | 0.028 | C | | C | C | B | C | C |

TABLE 2-continued

| # | 1b (nM) | 1a | 1a Q30R | 2a JFH | 2a J6 | 2b | 3a | 4a |
|---|---------|----|---------|--------|-------|-----|-----|-----|
| 96 | 0.006 | C | | B | | | B | C |
| 97 | 0.009 | B | | B | | | A | C |

TABLE 2-continued

| # | 1b (nM) | 1a | 1a Q30R | 2a JFH | 2a J6 | 2b | 3a | 4a |
|---|---------|----|---------|--------|-------|----|----|-----|
| 98 | 0.010 | C | | C | A | | B | C |
| 99 | 0.021 | C | | C | | | B | C |

TABLE 2-continued

| # | 1b (nM) | 1a | 1a Q30R | 2a JFH | 2a J6 | 2b | 3a | 4a |
|---|---|---|---|---|---|---|---|---|
| 100 | 0.004 | C | C | C | | | C | C |
| 101 | 0.011 | C | | C | | | C | C |
| 102 | 0.009 | C | | C | | | C | C |

1b (nM); 1a, 1a Q30R, 2a JFH, 2a J6, 2b-A ≥ 44 nM, B = 1-43.99 nM, C = 0.001-0.999 nM; 3a, 4a-A ≥ 5 nM, B = 1-4.99 nM, C = 0.001-0.99 nM

TABLE 3
| # | 1b (nM) | 1a | 1a Q30R | 2a JFH | 2a J6 | 2b | 3a | 4a |
|---|---|---|---|---|---|---|---|---|
| 103 | 0.007 | C | | C | | | | C |
| 104 | 0.007 | C | | C | | | | C |
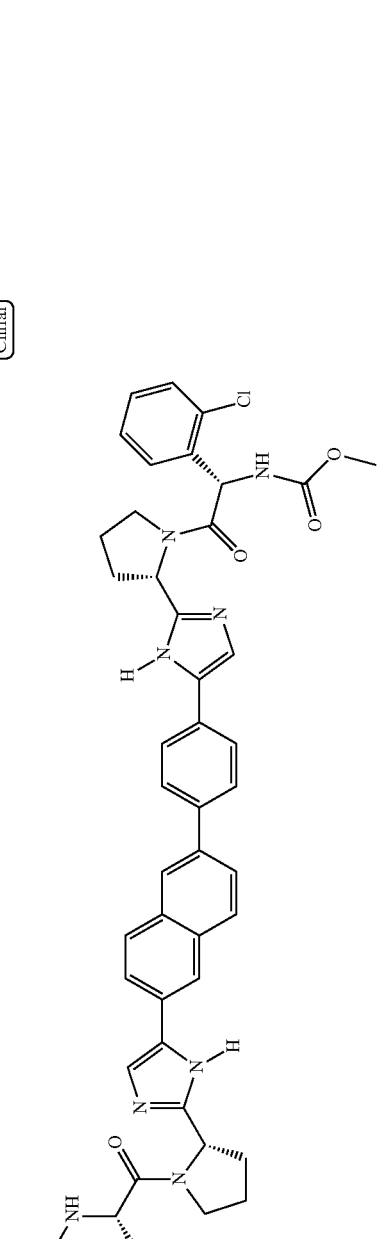
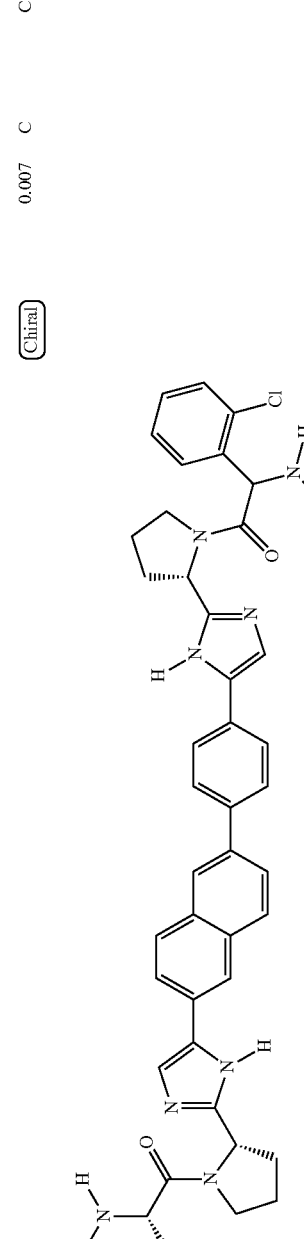

TABLE 3-continued
| # | | 1b (nM) | 1a | 1a Q30R | 2a JFH | 2a J6 | 2b | 3a | 4a |
|---|---|---|---|---|---|---|---|---|---|
| 105 | 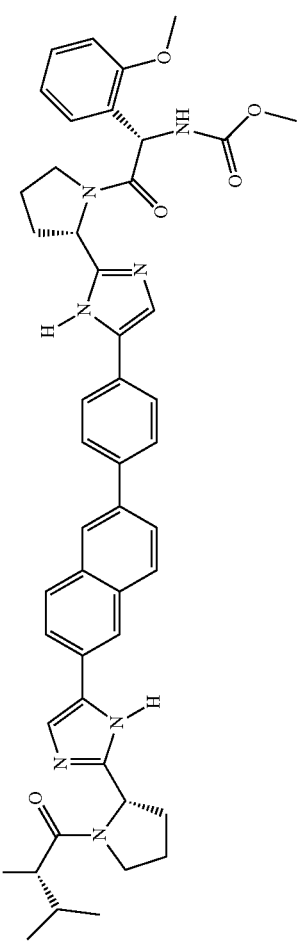 | 0.042 | B | | B | | | | B |
| 106 | 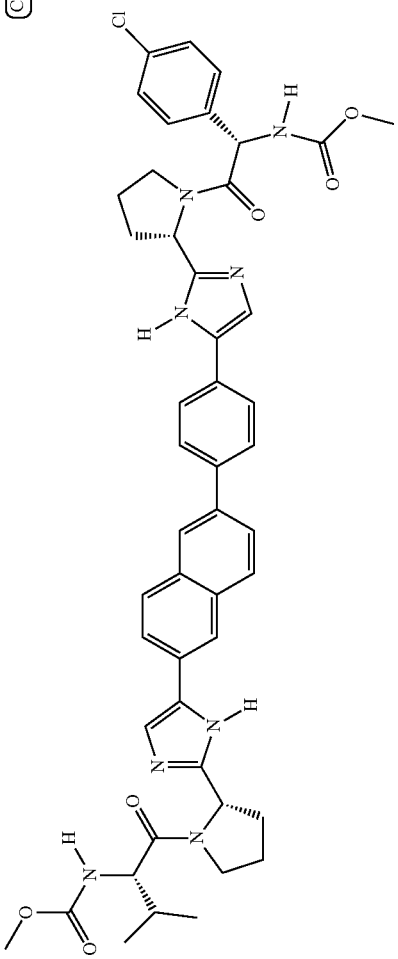 | 0.024 | B | | B | | | | B |

TABLE 3-continued
| # | | 1b (nM) | 1a | 1a Q30R | 2a JFH | 2a J6 | 2b | 3a | 4a |
|---|---|---|---|---|---|---|---|---|---|
| 107 | 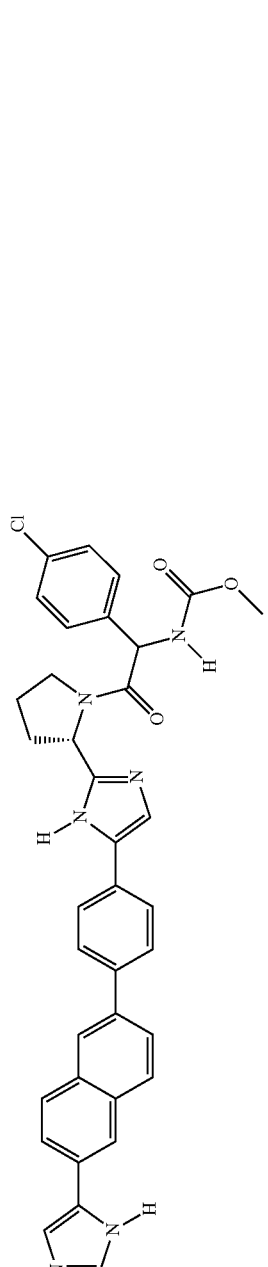 | 0.024 | B | | B | | B | | B |
| 108 | 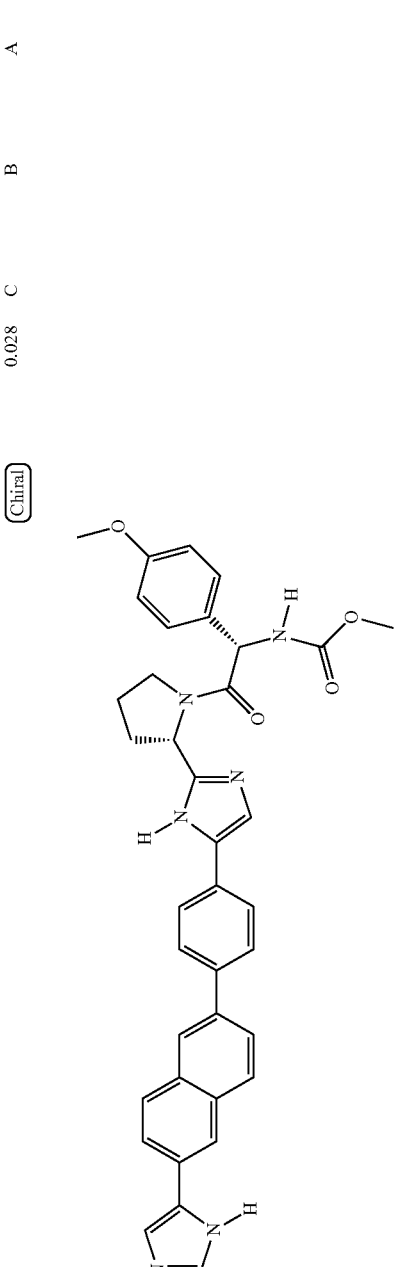 | 0.028 | C | | B | | | A | |

TABLE 3-continued
| # | 1b (nM) | 1a | 1a Q30R | 2a JFH | 2a J6 | 2b | 3a | 4a |
|---|---|---|---|---|---|---|---|---|
| 109 | 1.597 | B | | A | | | | A |
| 110 | 0.009 | C | | C | | | | C |
| 111 | 0.160 | B | | A | | | | A |
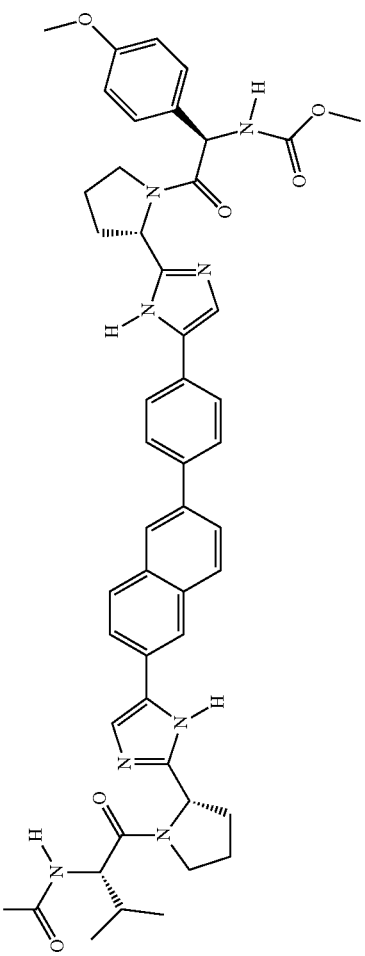

TABLE 3-continued
| # | 1b (nM) | 1a | 1a Q30R | 2a JFH | 2a J6 | 2b | 3a | 4a |
|---|---|---|---|---|---|---|---|---|
| 112 | 0.018 | C | | B | | | | A |
| 113 | 0.014 | C | | C | | | | C |
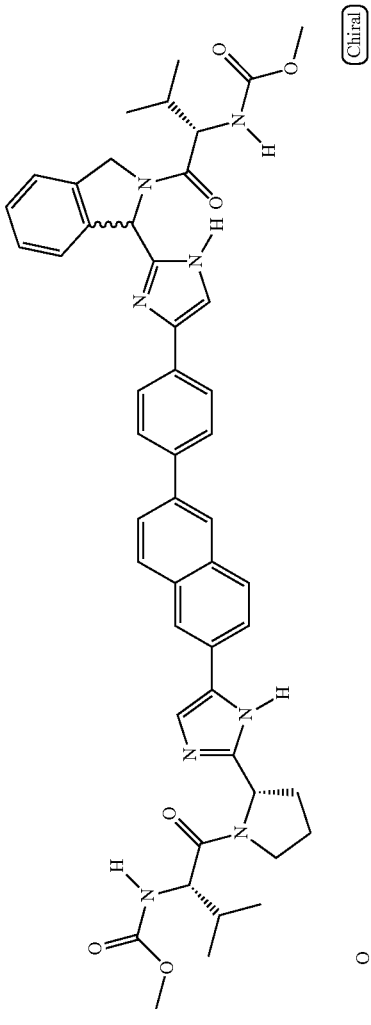
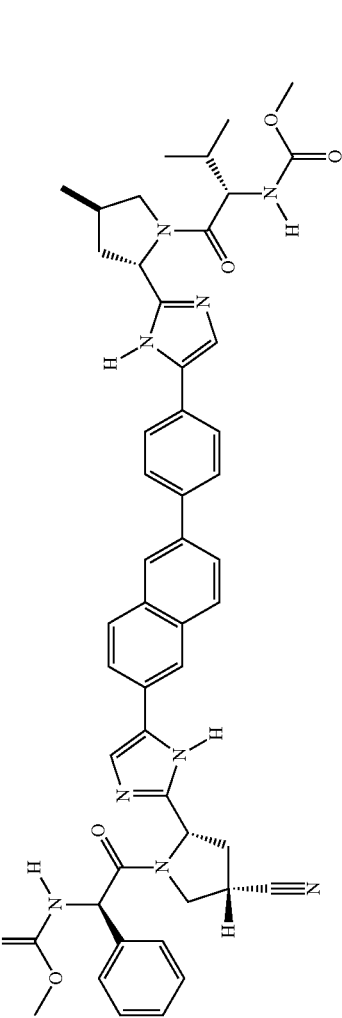

TABLE 3-continued

| # | 1b (nM) | 1a | 1a Q30R | 2a JFH | 2a J6 | 2b | 3a | 4a |
|---|---|---|---|---|---|---|---|---|
| 114 | 0.011 | C | | B | A | A | B | C |
| 115 | 0.019 | C | | C | | | | C |

TABLE 3-continued

| # | 1b (nM) | 1a | 1a Q30R | 2a JFH | 2a J6 | 2b | 3a | 4a |
|---|---|---|---|---|---|---|---|---|
| 116 | 0.008 | C | C | C | C | C | C | C |
| 117 | 0.007 | C | | C | | | C | |
| 118 | 0.027 | C | | C | | | C | |

TABLE 3-continued

| # | 1b (nM) | 1a | 1a Q30R | 2a JFH | 2a J6 | 2b | 3a | 4a |
|---|---|---|---|---|---|---|---|---|
| 119 | 0.020 | C | C | C | | | | C |
| 120 | 0.014 | C | C | C | | | | C |
| 121 | 0.011 | C | C | C | | | | B |

TABLE 3-continued

| # | 1b (nM) | 1a | 1a Q30R | 2a JFH | 2a J6 | 2b | 3a | 4a |
|---|---|---|---|---|---|---|---|---|
| 122 | 0.009 | C | | C | A | A | C | C |
| 123 | 0.014 | C | | C | A | A | C | C |
| 124 | 0.011 | C | | C | | | C | |

TABLE 3-continued
| # | | 1b (nM) | 1a | 1a Q30R | 2a JFH | 2a J6 | 2b | 3a | 4a |
|---|---|---|---|---|---|---|---|---|---|
| 125 | 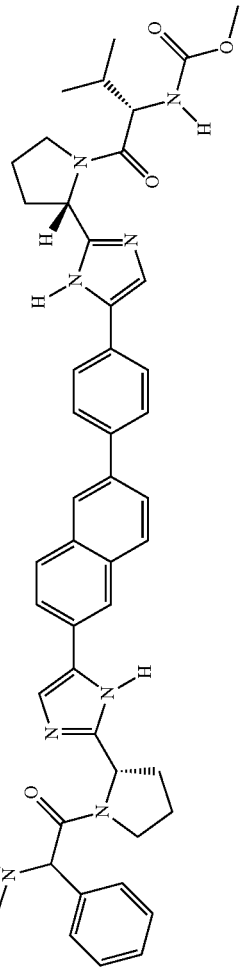 | 0.032 | C | | | | | | C |
| 126 | 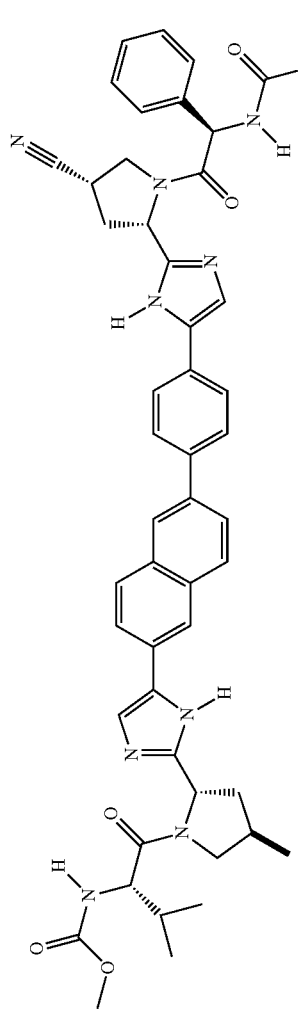 | | | | | | | | |
| 127 | 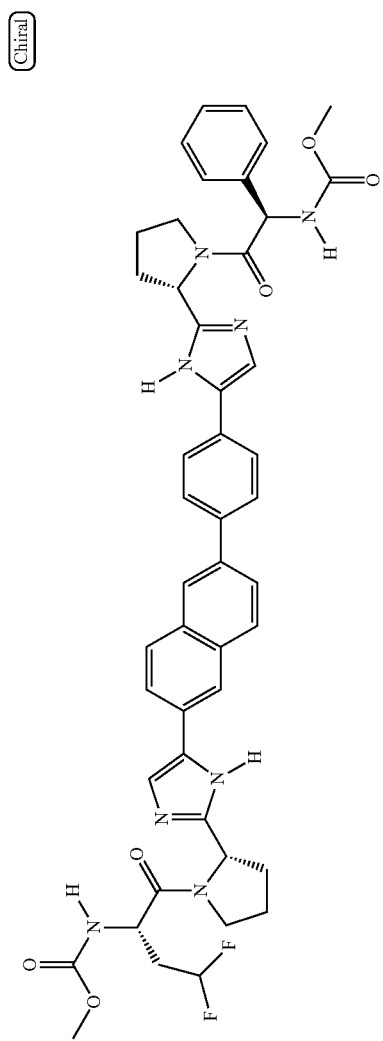 | 0.006 | C | | C | | | | C |

TABLE 3-continued

| # | 1b (nM) | 1a | 1a Q30R | 2a JFH | 2a J6 | 2b | 3a | 4a |
|---|---|---|---|---|---|---|---|---|
| 128 | 0.005 | C | | C | A | A | C | C |
| 129 | 0.007 | C | | C | A | A | C | C |
| 130 | 0.006 | C | | C | | | | C |

TABLE 3-continued

| # | 1b (nM) | 1a | 1a Q30R | 2a JFH | 2a J6 | 2b | 3a | 4a |
|---|---|---|---|---|---|---|---|---|
| 131 | 0.009 | C | C | C | C | | C | |
| 132 | 0.003 | C | | C | | | C | |
| 133 | | | | | | | | |

TABLE 3-continued

| # | 1b (nM) | 1a | 1a Q30R | 2a JFH | 2a J6 | 2b | 3a | 4a |
|---|---|---|---|---|---|---|---|---|
| 134 | 0.007 | C | | C | | | | C |
| 135 | 0.006 | C | | C | | A | | |
| 136 | 0.005 | C | | C | | C | | C |

TABLE 3-continued

| # | 1b (nM) | 1a | 1a Q30R | 2a JFH | 2a J6 | 2b | 3a | 4a |
|---|---|---|---|---|---|---|---|---|
| 137 | 0.012 | C | C | C | | C | | C |
| 138 | 0.006 | C | C | C | | C | | C |
| 139 | 0.004 | C | C | B | | C | | C |

TABLE 3-continued

| # | 1b (nM) | 1a | 1a Q30R | 2a JFH | 2a J6 | 2b | 3a | 4a |
|---|---|---|---|---|---|---|---|---|
| 140 | 0.004 | C | B | B | | | | C |
| 141 | 0.181 | B | | B | | | | A |

TABLE 3-continued

| # | 1b (nM) | 1a | 1a Q30R | 2a JFH | 2a J6 | 2b | 3a | 4a |
|---|---|---|---|---|---|---|---|---|
| 142 | 0.013 | C | C | C | | | | C |
| 143 | 0.025 | C | | B | | | | A |
| 144 | 0.013 | C | | C | | | | C |

TABLE 3-continued

| # | 1b (nM) | 1a | 1a Q30R | 2a JFH | 2a J6 | 2b | 3a | 4a |
|---|---|---|---|---|---|---|---|---|
| 145 | 0.010 | C | | C | | | | B |
| 146 | 0.048 | B | | B | | | | A |
| 147 | 0.012 | C | | C | | | | C |

TABLE 3-continued

| # | 1b (nM) | 1a | 1a Q30R | 2a JFH | 2a J6 | 2b | 3a | 4a |
|---|---|---|---|---|---|---|---|---|
| 148 | 0.020 | C | C | C | | | | B |
| 149 | 0.005 | C | | C | | | | C |

TABLE 3-continued

| # | (nM) 1b | 1a | 1a Q30R | 2a JFH | 2a J6 | 2b | 3a | 4a |
|---|---|---|---|---|---|---|---|---|
| 150 | 0.006 | C | C | C | | | | C |
| 151 | 0.038 | B | B | B | | | | B |
| 152 | 0.751 | A | A | A | | | | B |

TABLE 3-continued

| # | (nM) 1b | 1a | 1a Q30R | 2a JFH | 2a J6 | 2b | 3a | 4a |
|---|---|---|---|---|---|---|---|---|
| 153 | 0.012 | C | C | C | | C | | C |
| 154 | 0.014 | C | C | C | | C | | C |
| 155 | 0.013 | C | C | B | | C | | C |

TABLE 3-continued

| # | 1b (nM) | 1a | 1a Q30R | 2a JFH | 2a J6 | 2b | 3a | 4a |
|---|---|---|---|---|---|---|---|---|
| 156 | 0.028 | C | C | C | | | | C |
| 157 | 0.008 | C | | C | A | B | B | C |
| 158 | 0.010 | C | | C | | | | C |

TABLE 3-continued

| # | | 1b (nM) | 1a | 1a Q30R | 2a JFH | 2a J6 | 2b | 3a | 4a |
|---|---|---|---|---|---|---|---|---|---|
| 159 | | 0.006 | C | C | C | A | B | C | C |
| 160 | | 0.017 | C | | C | | | C | |
| 161 | | 0.019 | C | | C | | | C | |

TABLE 3-continued
| # | 1b (nM) | 1a | 1a Q30R | 2a JFH | 2a J6 | 2b | 3a | 4a | |
|---|---------|----|---------|--------|-------|----|----|-----|---|
| 162 | 0.010 | B | | B | | | | B | 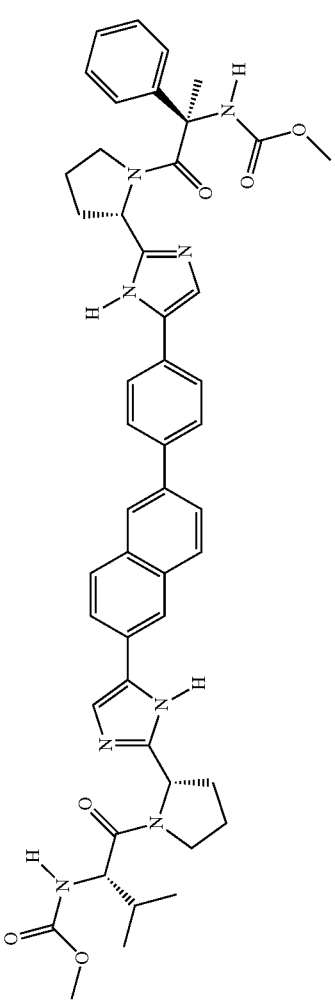 |
| 163 | 0.031 | B | | B | | | | A | 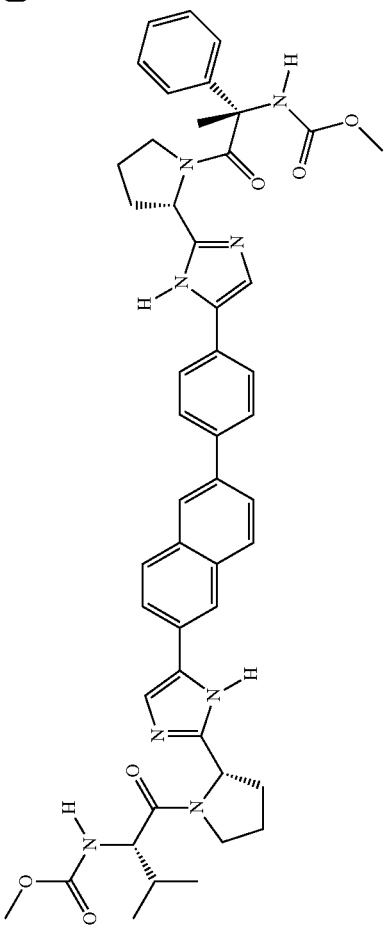 |

TABLE 3-continued

| # | 1b (nM) | 1a | 1a Q30R | 2a JFH | 2a J6 | 2b | 3a | 4a |
|---|---|---|---|---|---|---|---|---|
| 164 | 0.010 | C | C | C | | | C | |
| 165 | 0.009 | C | C | C | | | C | |

TABLE 3-continued

| # | (structure) | 1b (nM) | 1a | 1a Q30R | 2a JFH | 2a J6 | 2b | 3a | 4a |
|---|---|---|---|---|---|---|---|---|---|
| 166 | | 0.018 | B | | C | | | | C |
| 167 | | 0.048 | C | | C | | | | C |
| 168 | | 0.010 | B | | B | | | | C |

TABLE 3-continued

| # | | 1b (nM) | 1a | 1a Q30R | 2a JFH | 2a J6 | 2b | 3a | 4a |
|---|---|---------|----|---------|--------|-------|----|----|----|
| 169 | (Chiral) | 0.006 | C | C | C | A | A | C | C |
| 170 | (Chiral) | 0.032 | C | C | C | | | C | |

TABLE 3-continued

| # | 1b (nM) | 1a | 1a Q30R | 2a JFH | 2a J6 | 2b | 3a | 4a |
|---|---|---|---|---|---|---|---|---|
| 171 | 0.026 | C | C | C | | | | C |
| 172 | 0.011 | C | | C | | | | C |
| 173 | 0.024 | C | | C | | | | C |

TABLE 3-continued

| # | 1b (nM) | 1a | 1a Q30R | 2a JFH | 2a J6 | 2b | 3a | 4a |
|---|---|---|---|---|---|---|---|---|
| 174 | 0.015 | C | C | C | C | C | C | C |
| 175 | 0.011 | C | | C | | | C | |

TABLE 3-continued
| # | | 1b (nM) | 1b 1a | 1a Q30R | 2a JFH | 2a J6 | 2b | 3a | 4a |
|---|---|---|---|---|---|---|---|---|---|
| 176 | 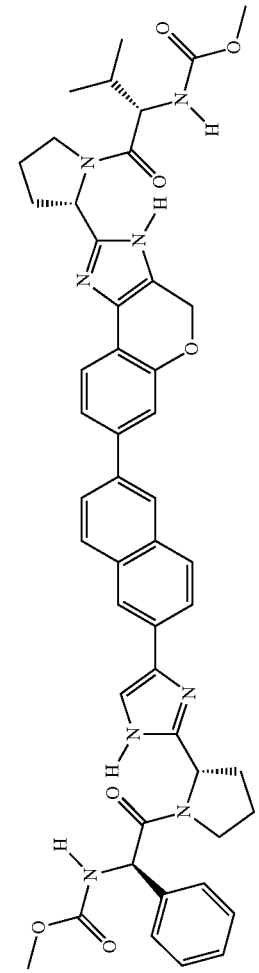 | 0.006 | C | C | C | | C | | C |
| 177 | 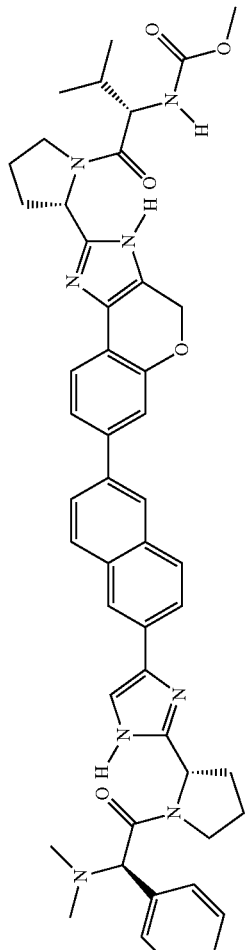 | 0.010 | C | C | C | | C | C | C |
| 178 | 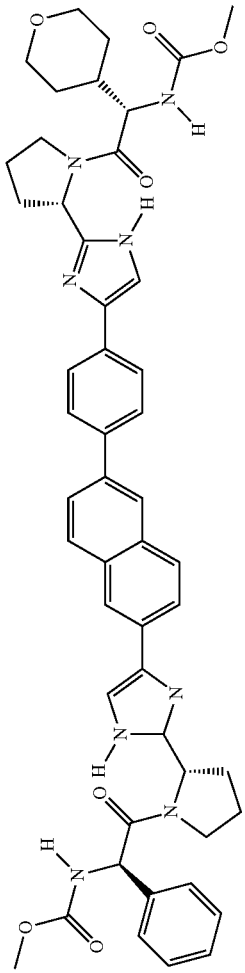 | 0.024 | C | C | C | | C | | |

TABLE 3-continued

| # | | 1b (nM) | 1a | 1a Q30R | 2a JFH | 2a J6 | 2b | 3a | 4a |
|---|---|---|---|---|---|---|---|---|---|
| 179 | | 0.041 | B | B | B | | | | A |
| 180 | | 0.007 | C | C | C | | | | C |
| 181 | | 0.010 | C | C | C | | | | C |

TABLE 3-continued
| # | 1b (nM) | 1a | 1a Q30R | 2a JFH | 2a J6 | 2b | 3a | 4a |
|---|---|---|---|---|---|---|---|---|
| 182 | 0.050 | | C | C | | | | C |
| 183 | 0.013 | C | | C | | | B | |
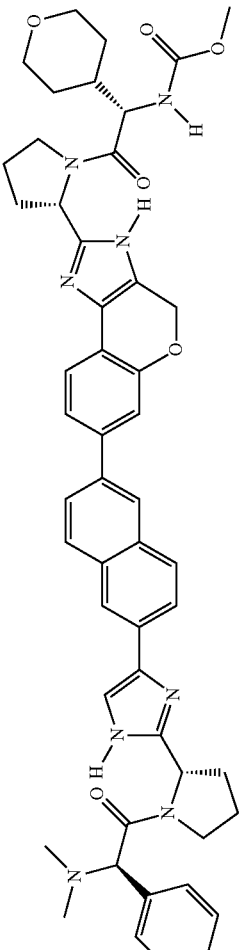
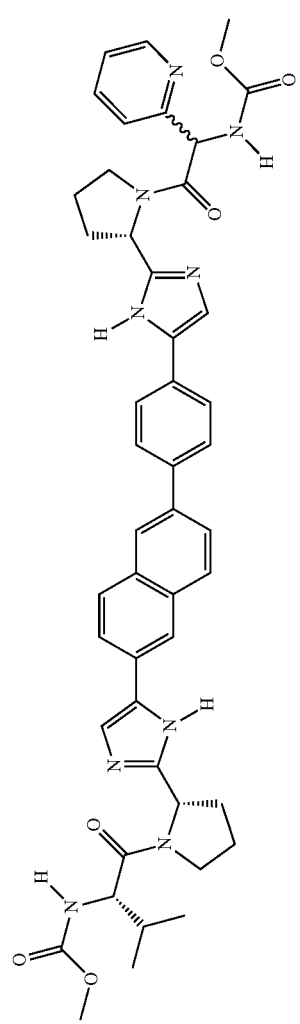

TABLE 3-continued
| # | 1b (nM) | 1a | 1a Q30R | 2a JFH | 2a J6 | 2b | 3a | 4a |
|---|---|---|---|---|---|---|---|---|
| 184 | 0.009 | C | C | C | C | | C | |
| 185 | 0.008 | B | | C | | | C | |
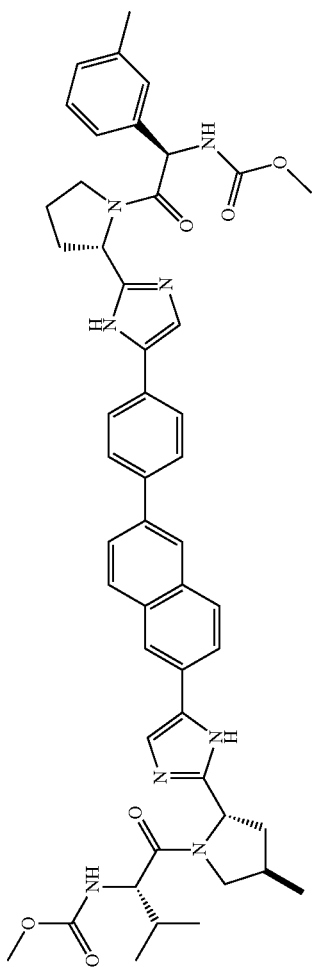
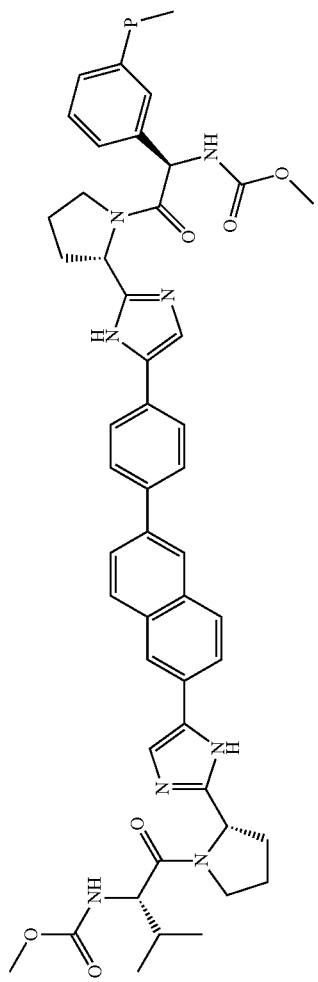

TABLE 3-continued

| # | 1b (nM) | 1a | 1a Q30R | 2a JFH | 2a J6 | 2b | 3a | 4a |
|---|---|---|---|---|---|---|---|---|
| 186 | 0.004 | C | | C | | | | |
| 187 | 0.007 | C | | C | | C | | |

TABLE 3-continued
| # | 1b (nM) | 1a | 1a Q30R | 2a JFH | 2a J6 | 2b | 3a | 4a |
|---|---|---|---|---|---|---|---|---|
| 188 | 0.012 | C | | C | | | | C |
| 189 | 0.006 | C | | C | | | | C |
| 190 | | | | | | | | C |
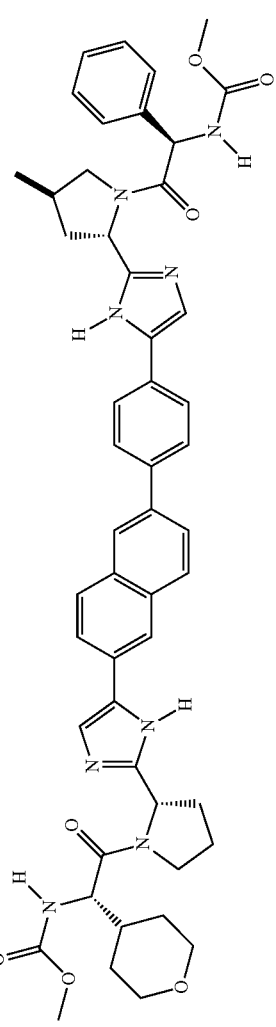
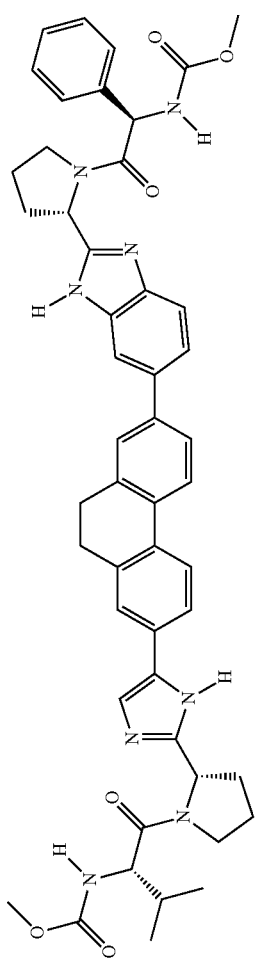
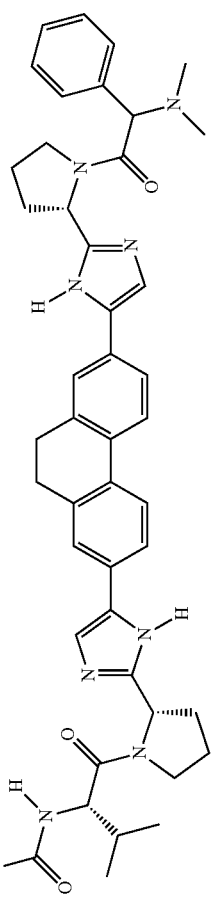

TABLE 3-continued

| # | 1b (nM) | 1a | 1a Q30R | 2a JFH | 2a J6 | 2b | 3a | 4a |
|---|---|---|---|---|---|---|---|---|
| 191 | 0.253 | B | | A | | A | | A |
| 192 | 0.004 | C | | C | | C | | C |
| 193 | 0.005 | C | | C | | C | | C |

TABLE 3-continued

| # | 1b (nM) | 1a | 1a Q30R | 2a JFH | 2a J6 | 2b | 3a | 4a |
|---|---|---|---|---|---|---|---|---|
| 194 | 0.010 | B | | B | | | B | |
| 195 | 0.023 | C | | C | | | B | C |
| 196 | 0.036 | B | | B | | | A | C |

TABLE 3-continued

| # | 1b (nM) | 1a | 1a Q30R | 2a JFH | 2a J6 | 2b | 3a | 4a |
|---|---|---|---|---|---|---|---|---|
| 197 | 0.010 | B | | B | | | C | C |
| 198 | 0.018 | C | | C | A | A | B | C |
| 199 | 0.010 | B | | B | | | B | C |

TABLE 3-continued

| # | 1b (nM) | 1a | 1a Q30R | 2a JFH | 2a J6 | 2b | 3a | 4a |
|---|---|---|---|---|---|---|---|---|
| 200 | 0.009 | B | | B | | | B | C |
| 201 | 0.018 | C | | B | | | A | C |
| 202 | 0.017 | C | | B | | | A | C |

TABLE 3-continued

| # | | 1b (nM) | 1a | 1a Q30R | 2a JFH | 2a J6 | 2b | 3a | 4a |
|---|---|---|---|---|---|---|---|---|---|
| 203 | | 0.124 | A | | B | | | A | C |
| 204 | | 0.030 | C | | C | | | C | C |
| 205 | | 0.016 | C | | C | | | B | C |

TABLE 3-continued

| # | 1b (nM) | 1a | 1a Q30R | 2a JFH | 2a J6 | 2b | 3a | 4a |
|---|---|---|---|---|---|---|---|---|
| 206 | 0.005 | C | C | C | B | A | C | C |
| 207 | 0.017 | C | | B | | A | | C |
| 208 | 0.009 | C | | C | | C | C | C |

TABLE 3-continued

| # | 1b (nM) | 1a | 1a Q30R | 2a JFH | 2a J6 | 2b | 3a | 4a |
|---|---|---|---|---|---|---|---|---|
| 209 | 0.014 | C | | C | | | | C |
| 210 | 0.008 | C | | | | C | | |

TABLE 3-continued
| # | 1b (nM) | 1a | 1a Q30R | 2a JFH | 2a J6 | 2b | 3a | 4a |
|---|---|---|---|---|---|---|---|---|
| 211 | 0.009 | C | | B | | | | B |
| 212 | 0.018 | C | | C | | | | C |
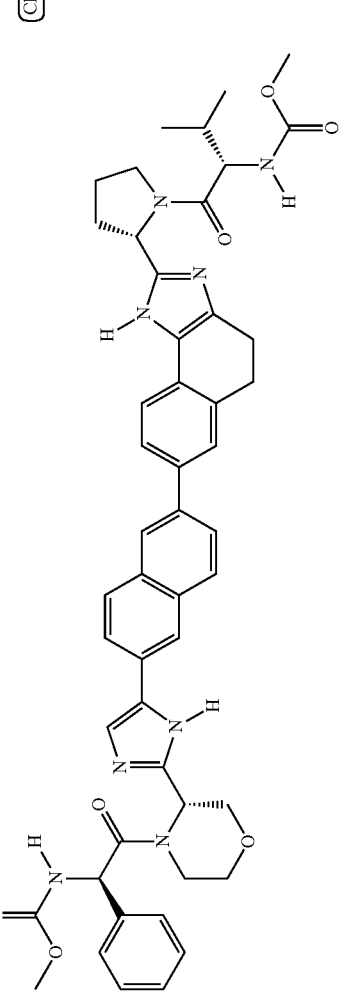
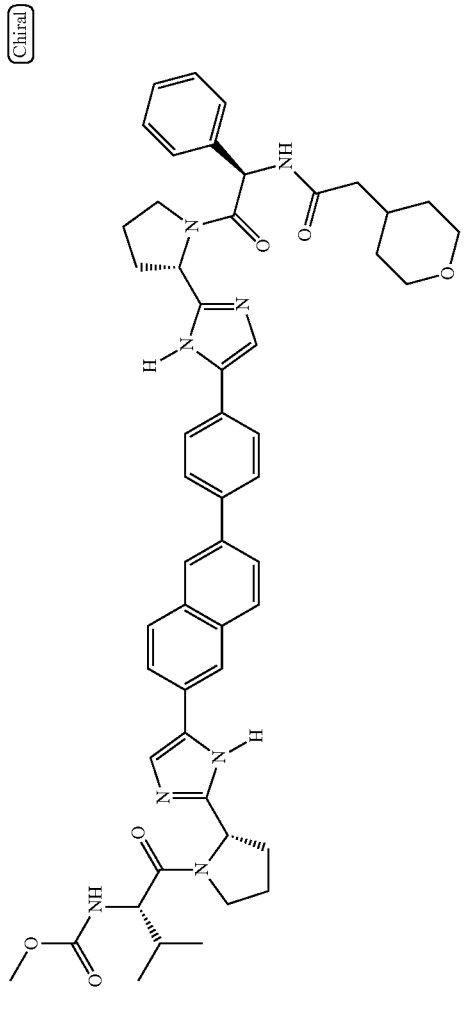

TABLE 3-continued

| # | 1b (nM) | 1a | 1a Q30R | 2a JFH | 2a J6 | 2b | 3a | 4a |
|---|---|---|---|---|---|---|---|---|
| 213 | 0.030 | C | C | C | | | | |
| 214 | 0.060 | C | | C | | | | |
| 215 | 0.023 | C | | C | | | C | C |

TABLE 3-continued

| # | 1b (nM) | 1a | 1a Q30R | 2a JFH | 2a J6 | 2b | 3a | 4a | Structure |
|---|---|---|---|---|---|---|---|---|---|
| 216 | 0.006 | C | | C | | | | C | |
| 217 | 0.009 | C | | C | | | | C | |
| 218 | 0.010 | C | | C | | | | C | |

TABLE 3-continued

| # | (nM) 1b | 1a | 1a Q30R | 2a JFH | 2a J6 | 2b | 3a | 4a |
|---|---|---|---|---|---|---|---|---|
| 219 | 0.008 | C | | C | | | B | C |
| 220 | 0.011 | C | | C | | | B | C |
| 221 | 0.017 | C | | C | | | C | C |

TABLE 3-continued

| # | 1b (nM) | 1a | 1a Q30R | 2a JFH | 2a J6 | 2b | 3a | 4a |
|---|---|---|---|---|---|---|---|---|
| 222 | 0.023 | C | C | C | | | | C |
| 223 | 0.022 | B | | C | | | B | C |
| 224 | 0.008 | C | | C | | | C | C |

| # | structure | 1b (nM) | 1b 1a | 1a Q30R | 2a JFH | 2a J6 | 2b | 3a | 4a |
|---|---|---|---|---|---|---|---|---|---|
| 225 | | 0.009 | C | | C | | C | | C |
| 226 | | 0.009 | B | | B | | B | | C |
| 227 | | 0.025 | B | | C | | C | | C |

TABLE 3-continued

| # | 1b (nM) | 1a | 1a Q30R | 2a JFH | 2a J6 | 2b | 3a | 4a |
|---|---|---|---|---|---|---|---|---|
| 228 | 0.015 | C | C | C | | C | C | C |
| 229 | 0.018 | C | | C | | B | C | |
| 230 | 0.012 | C | | B | | B | B | |

TABLE 3-continued
| # | 1b (nM) | 1a | 1a Q30R | 2a JFH | 2a J6 | 2b | 3a | 4a |
|---|---|---|---|---|---|---|---|---|
| 231 | 0.019 | C | | B | | | B | C |
| 232 | 0.004 | C | | C | | | C | C |
| 233 | 0.005 | C | | C | | | C | C |
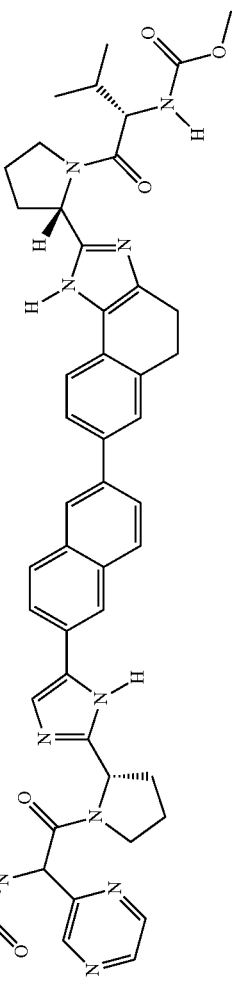

TABLE 3-continued

| # | 1b (nM) | 1a | 1a Q30R | 2a JFH | 2a J6 | 2b | 3a | 4a |
|---|---|---|---|---|---|---|---|---|
| 234 | 0.011 | C | | C | | | | C |
| 235 | 0.004 | C | | C | | B | | C |
| 236 | 0.011 | C | | C | | C | | C |

TABLE 3-continued

| # | 1b (nM) | 1a | 1a Q30R | 2a JFH | 2a J6 | 2b | 3a | 4a |
|---|---|---|---|---|---|---|---|---|
| 237 | 0.023 | C | C | C | C | C | C | C |
| 238 | 0.005 | C | C | C | C | C | C | C |

TABLE 3-continued

| # | 1b (nM) | 1a | 1a Q30R | 2a JFH | 2a J6 | 2b | 3a | 4a |
|---|---|---|---|---|---|---|---|---|
| 239 | 0.078 | C | | C | | | | C |
| 240 | 0.010 | C | | C | | | B | C |
| 241 | 0.011 | C | | B | | | B | C |

TABLE 3-continued

| # | 1b (nM) | 1a | 1a Q30R | 2a JFH | 2a J6 | 2b | 3a | 4a |
|---|---|---|---|---|---|---|---|---|
| 242 | 0.008 | C | | C | | | | C |
| 243 | 4.587 | A | | A | | | A | C |

TABLE 3-continued

| # | 1b (nM) | 1a | 1a Q30R | 2a JFH | 2a J6 | 2b | 3a | 4a |
|---|---|---|---|---|---|---|---|---|
| 244 | 0.014 | C | C | C | C | C | C | C |
| 245 | 0.017 | C | C | C | C | C | C | C |

TABLE 3-continued

| # | 1b (nM) | 1a | 1a Q30R | 2a JFH | 2a J6 | 2b | 3a | 4a |
|---|---|---|---|---|---|---|---|---|
| 246 | 0.045 | C | | C | | | C | C |
| 247 | 0.758 | B | | A | | | A | C |
| 248 | 0.024 | B | | B | | | A | C |

TABLE 3-continued
| # | 1b (nM) | 1a | 1a Q30R | 2a JFH | 2a J6 | 2b | 3a | 4a |
|---|---|---|---|---|---|---|---|---|
| 249 | 0.014 | B | | B | | | A | C |
| 250 | 0.004 | C | | C | | | C | C |
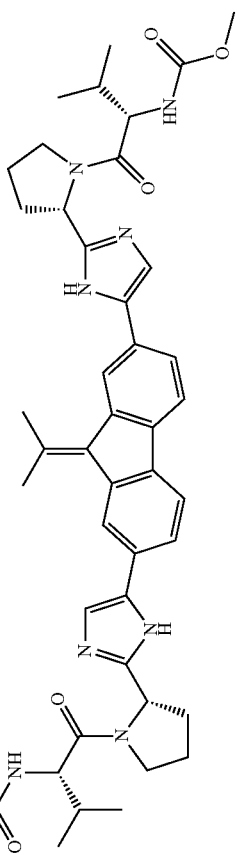
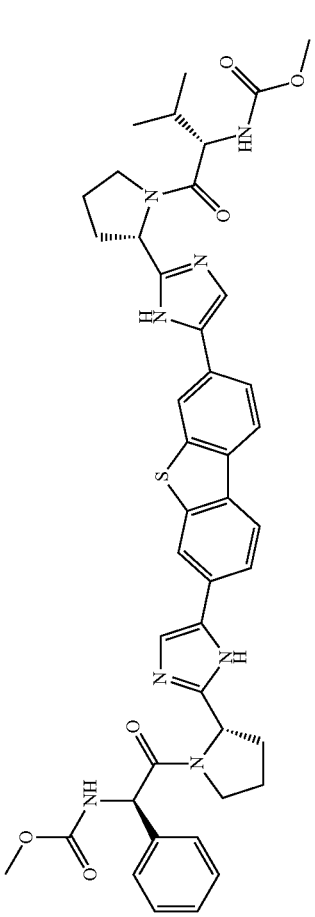

TABLE 3-continued

| # | 1b (nM) | 1a | 1a Q30R | 2a JFH | 2a J6 | 2b | 3a | 4a |
|---|---------|----|---------|--------|-------|----|----|----|
| 251 | 0.010 | C | | C | | | | C |
| 252 | 0.004 | C | | C | | | C | |

TABLE 3-continued

| # | | 1b (nM) | 1a | 1a Q30R | 2a JFH | 2a J6 | 2b | 3a | 4a |
|---|---|---|---|---|---|---|---|---|---|
| 253 | Chiral | 0.005 | C | C | C | | | C | C |
| 254 | | 0.077 | C | | C | | | | |
| 255 | | 0.015 | C | | B | | | | |

TABLE 3-continued

| # | 1b (nM) | 1a | 1a Q30R | 2a JFH | 2a J6 | 2b | 3a | 4a |
|---|---|---|---|---|---|---|---|---|
| 256 | 0.015 | C | | C | | | C | C |
| 257 | 0.013 | C | | C | | | C | C |
| 258 | 0.005 | C | | C | | | C | C |

TABLE 3-continued

| # | 1b (nM) | 1a | 1a Q30R | 2a JFH | 2a J6 | 2b | 3a | 4a |
|---|---|---|---|---|---|---|---|---|
| 259 | 0.014 | C | C | C | | | | C | C |
| 260 | 0.004 | C | | C | A | A | C | C |
| 261 | 0.011 | C | | C | | | | C | C |

TABLE 3-continued

| # | 1b (nM) | 1a | 1a Q30R | 2a JFH | 2a J6 | 2b | 3a | 4a |
|---|---|---|---|---|---|---|---|---|
| 262 | 0.008 | C | | C | | | | C |
| 263 | 0.006 | C | | C | | | | C |
| 264 | 0.006 | C | | B | | B | | C |

TABLE 3-continued

| # | 1b (nM) | 1a | 1a Q30R | 2a JFH | 2a J6 | 2b | 3a | 4a |
|---|---|---|---|---|---|---|---|---|
| 265 | 0.042 | B | | B | | | B | C |
| 266 | 0.009 | C | | B | | | B | C |
| 267 | 0.045 | B | | A | | | A | C |

TABLE 3-continued

| # | 1b (nM) | 1a | 1a Q30R | 2a JFH | 2a J6 | 2b | 3a | 4a |
|---|---|---|---|---|---|---|---|---|
| 268 | 0.007 | C | C | C | | | | C |
| 269 | 0.076 | A | | B | | A | | C |
| 270 | 0.032 | C | | C | | C | | C |

TABLE 3-continued

| # | 1b (nM) | 1a | 1a Q30R | 2a JFH | 2a J6 | 2b | 3a | 4a |
|---|---|---|---|---|---|---|---|---|
| 271 | 0.008 | C | | C | | | C | C |
| 272 | #### | A | | A | | | A | B |

TABLE 3-continued

| # | 1b (nM) | 1a | 1a Q30R | 2a JFH | 2a J6 | 2b | 3a | 4a |
|---|---|---|---|---|---|---|---|---|
| 273 | 0.042 | C | | C | | | C | C |
| 274 | 0.011 | B | | B | | | B | C |

TABLE 3-continued

| # | 1b (nM) | 1a | 1a Q30R | 2a JFH | 2a J6 | 2b | 3a | 4a |
|---|---|---|---|---|---|---|---|---|
| 275 | 2.145 | B | | A | | | A | A |
| 276 | #### | A | | A | | | | |
| 277 | 1.058 | B | | A | | | A | B |

TABLE 3-continued

| # | 1b (nM) | 1a | 1a Q30R | 2a JFH | 2a J6 | 2b | 3a | 4a |
|---|---------|----|---------|--------|-------|----|----|----|
| 278 | 0.013 | C | | C | | | B | C |
| 279 | 0.031 | B | | B | | | C | C |
| 280 | 0.047 | B | | B | | | C | C |

TABLE 3-continued

| # | 1b (nM) | 1a | 1a Q30R | 2a JFH | 2a J6 | 2b | 3a | 4a |
|---|---|---|---|---|---|---|---|---|
| 281 | 0.063 | C | | C | | | C | C |
| 282 | 0.007 | C | | C | A | A | C | C |
| 283 | 0.007 | C | | C | | | C | C |

TABLE 3-continued

| # | 1b (nM) | 1a | 1a Q30R | 2a JFH | 2a J6 | 2b | 3a | 4a |
|---|---|---|---|---|---|---|---|---|
| 284 | 4.620 | B | | B | | | A | C |
| 285 | 0.006 | C | | C | | | C | C |
| 286 | 0.003 | C | | C | | | C | C |

TABLE 3-continued
| # | 1b (nM) | 1a | 1a Q30R | 2a JFH | 2a J6 | 2b | 3a | 4a |
|---|---|---|---|---|---|---|---|---|
| 287 | 0.006 | C | | C | | | C | C |
| 288 | 0.009 | C | | C | | | C | C |
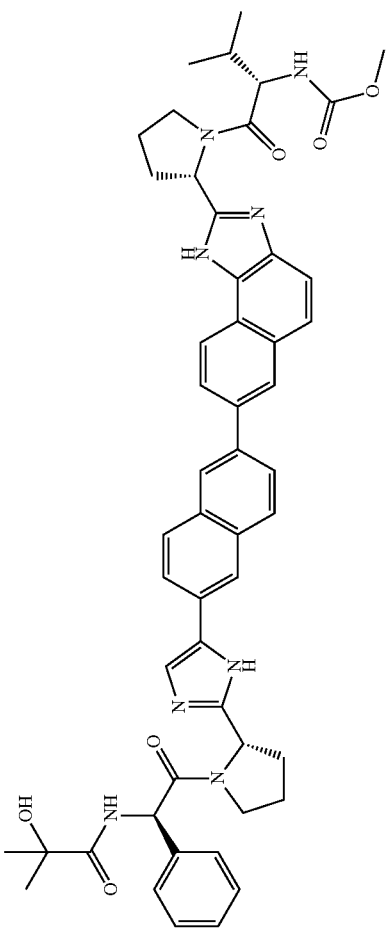
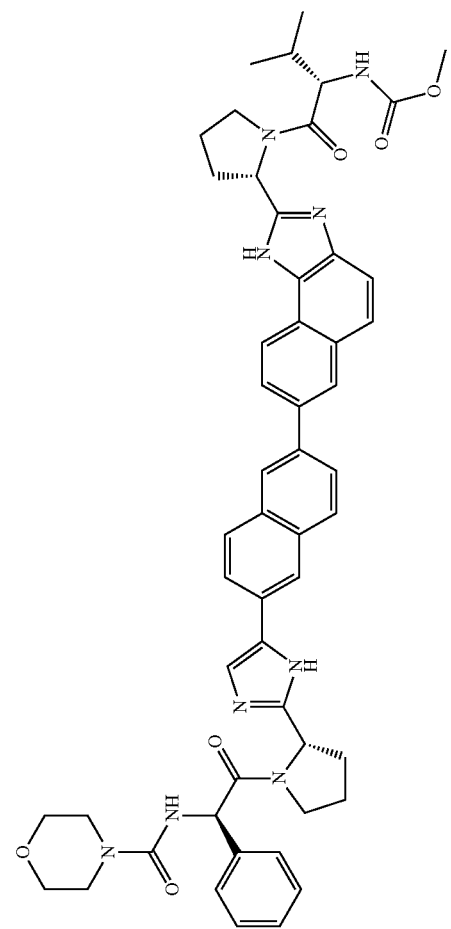

TABLE 3-continued
| # | 1b (nM) | 1a | 1a Q30R | 2a JFH | 2a J6 | 2b | 3a | 4a |
|---|---|---|---|---|---|---|---|---|
| 289 | 0.010 | C | C | C | C | C | C | C |
1b (nM); 1a, 1a Q30R, 2a JFH, 2a J6, 2b-A ≥ 44 nM, B = 1-43.99 nM, C = 0.001-0.999 nM; 3a, 4a-A ≥ 5 nM, B = 1-4.99 nM, C = 0.001-0.99 nM

TABLE 4

| # | 1b (nM) | 1a | 1a Q30R | 2a JFH | 2a J6 | 2b | 3a | 4a |
|---|---|---|---|---|---|---|---|---|
| 290 | 0.017 | C | | C | | | C | C |
| 291 | 0.103 | C | | C | | | C | C |
| 292 | 0.059 | C | | C | | | C | C |
| 293 | 0.042 | C | | C | | | C | C |
| 294 | 0.010 | C | | C | | | C | C |

TABLE 4-continued

| # | 1b (nM) | 1a | 1a Q30R | 2a JFH | 2a J6 | 2b | 3a | 4a |
|---|---|---|---|---|---|---|---|---|
| 295 | 0.050 | B | | C | | | C | C |
| 296 | 0.063 | C | | C | | | C | C |
| 297 | 0.357 | C | | C | | | C | C |
| 298 | 0.077 | C | | C | C | B | C | C |
| 299 | 0.017 | B | | B | | | A | C |

TABLE 4-continued
| # | | 1b (nM) | 1a | 1a Q30R | 2a JFH | 2a J6 | 2b | 3a | 4a |
|---|---|---|---|---|---|---|---|---|---|
| 300 | 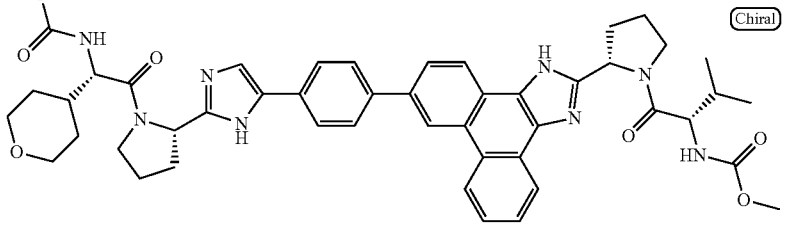 | 0.023 | B | | C | | | B | C |
| 301 | 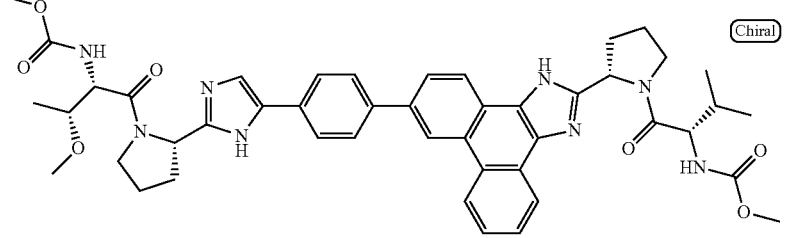 | 0.019 | B | | B | | | B | C |
| 302 | 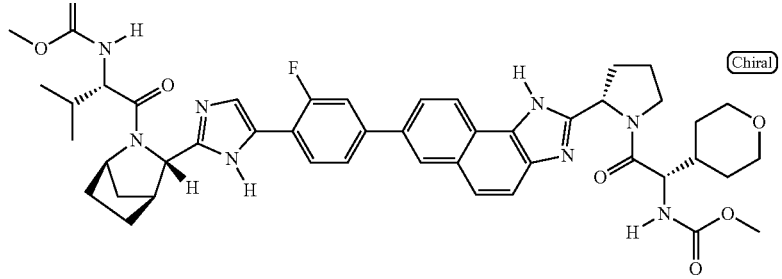 | 0.021 | C | | C | | | C | C |
| 303 | 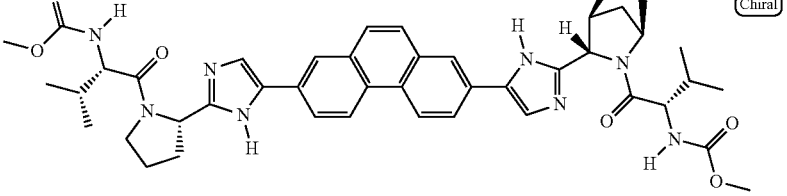 | 0.008 | C | | C | | | C | C |
| 304 | 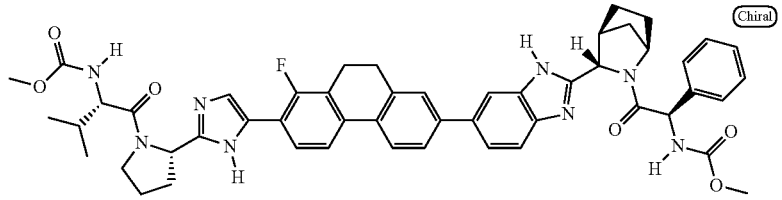 | 0.004 | B | | C | | | B | C |
| 305 | 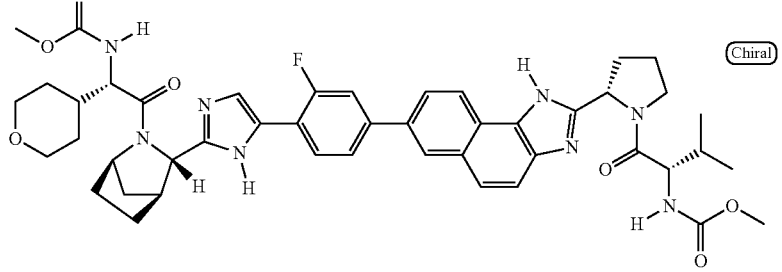 | 0.017 | C | | C | | | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 306 | 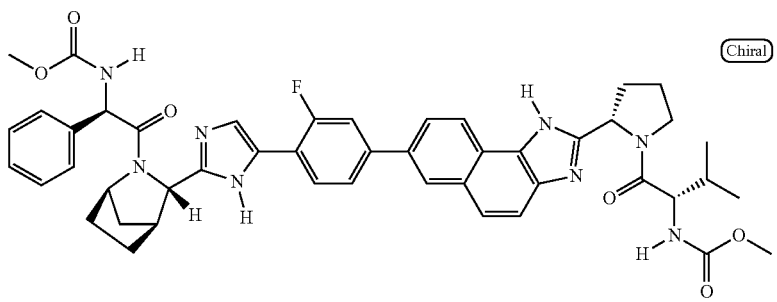 (Chiral) | 0.011 | C | | C | A | | C | C |
| 307 | 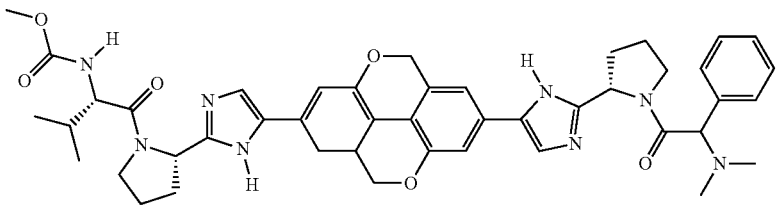 [SMILES: COC(=O)N[C@H](C(=O)N1CCC[C@H]1c1ncc(C2=CC3=C4c5c(cc(-c6cnc([C@@H]7CCCN7C(=O)C(c7ccccc7)N(C)C)[nH]6)cc5OCC4C2)CO3)[nH]1)C(C)C] | 0.091 | C | | C | | | C | C |
| 308 | 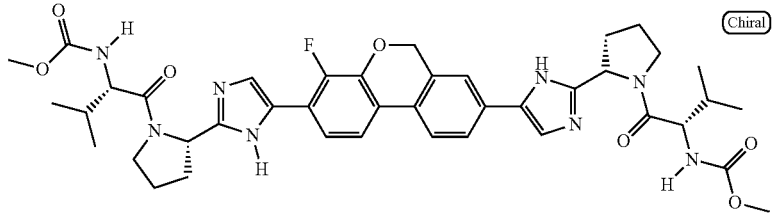 (Chiral) | 0.008 | C | | C | | | C | C |
| 309 | 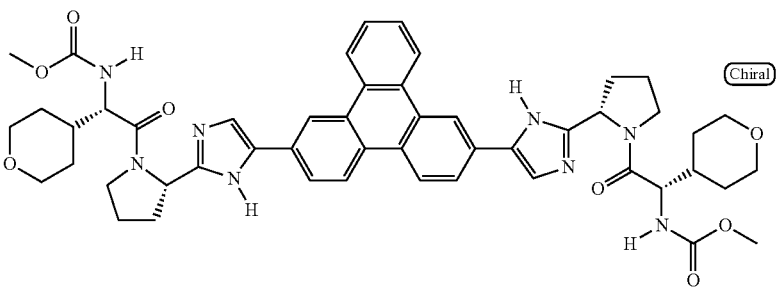 [SMILES: COC(=O)N[C@H](C(=O)N1CCC[C@H]1c1ncc(-c2ccc3c4ccc(-c5cnc([C@@H]6CCCN6C(=O)[C@@H](NC(=O)OC)C6CCOCC6)[nH]5)cc4c4ccccc4c3c2)[nH]1)C1CCOCC1] (Chiral) | 0.219 | C | | C | | | C | C |
| 310 | 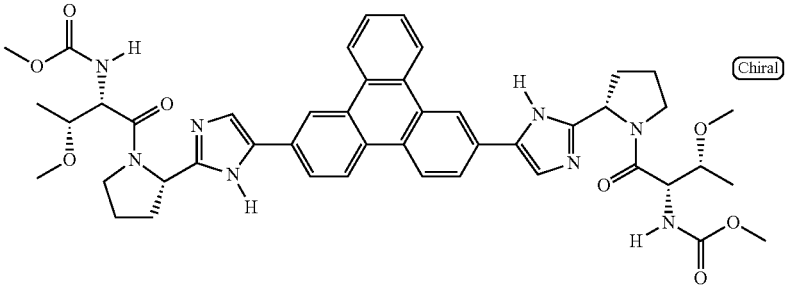 (Chiral) | 0.041 | C | | C | | | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 311 | | 0.025 | C | | C | | | C | C |
| 312 | | 0.011 | B | | C | | | C | C |
| 313 | | 0.079 | C | | C | | | C | C |
| 314 | | 0.026 | C | | C | C | C | C | C |
| 315 | | 0.023 | C | | C | B | | C | C |

TABLE 4-continued

| # | 1b (nM) | 1a | 1a Q30R | 2a JFH | 2a J6 | 2b | 3a | 4a |
|---|---|---|---|---|---|---|---|---|
| 316 | 0.242 | C | | C | | | C | C |
| 317 | 0.023 | C | C | C | C | C | C | C |
| 318 | 0.005 | C | | C | | | B | C |
| 319 | 0.021 | C | | C | C | | C | C |
| 320 | 0.010 | C | | C | | | C | C |
| 321 | 0.006 | C | | C | | | C | C |

TABLE 4-continued

| # | 1b (nM) | 1a | 1a Q30R | 2a JFH | 2a J6 | 2b | 3a | 4a |
|---|---|---|---|---|---|---|---|---|
| 322 | 0.021 | C | | C | | | C | C |
| 323 | 0.043 | C | | C | C | C | C | C |
| 324 | 0.006 | C | | C | | | C | C |
| 325 | 0.018 | C | B | C | C | B | C | C |
| 326 | 0.005 | C | | C | | | B | C |

TABLE 4-continued
| # | | 1b (nM) | 1a | 1a Q30R | 2a JFH | 2a J6 | 2b | 3a | 4a |
|---|---|---------|----|---------|--------|-------|----|----|-----|
| 327 | 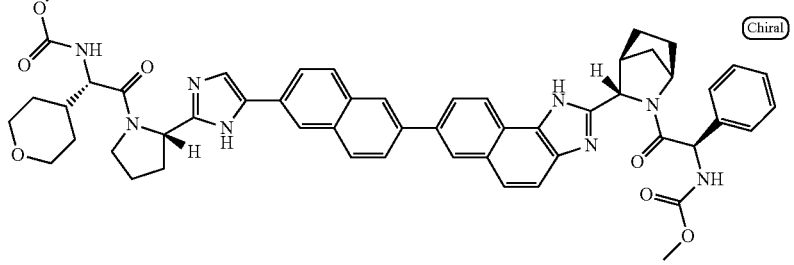 | 0.011 | C | | C | | | C | C |
| 328 | 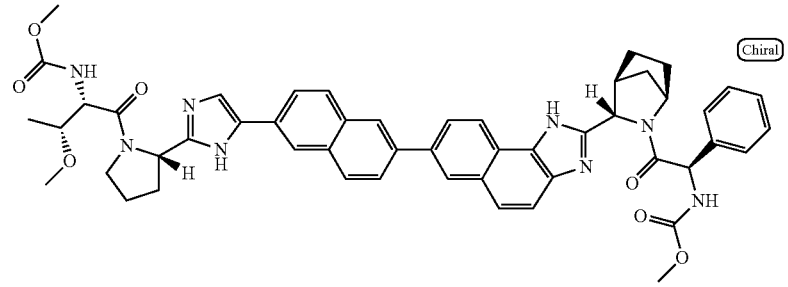 [SMILES: COC(=O)N[C@H](C(=O)N1CCC[C@H]1c1ncc(-c2ccc3cc(-c4ccc5c(ccc6nc([C@@H]7[C@H]8CC[C@H](C8)N7C(=O)[C@H](NC(=O)OC)c7ccccc7)[nH]c65)c4)ccc3c2)[nH]1)[C@@H](C)OC] | 0.008 | C | | C | | | B | C |
| 329 | 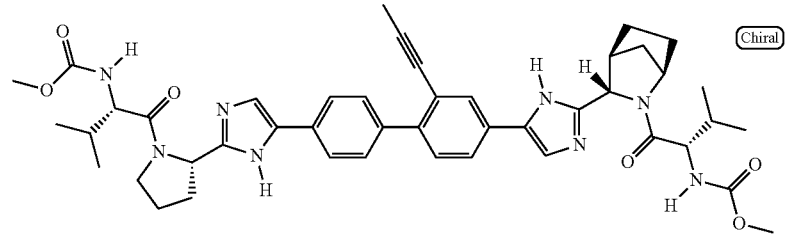 | 0.008 | C | | C | | | B | C |
| 330 | 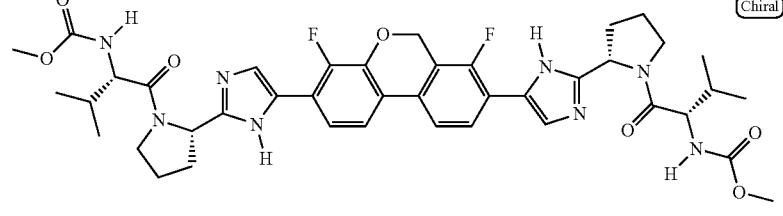 | 0.006 | C | | C | | | C | C |
| 331 | 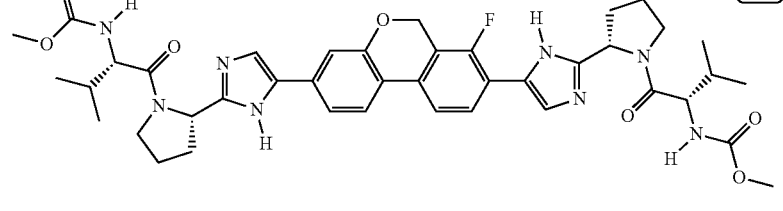 | 0.006 | C | | C | | | C | C |
| 332 | 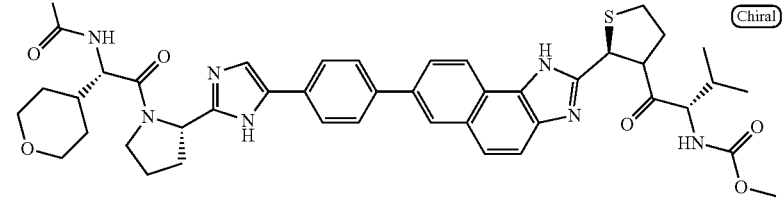 | 1.255 | B | | C | | | B | C |

TABLE 4-continued
| # | | 1b (nM) | 1a | 1a Q30R | 2a JFH | 2a J6 | 2b | 3a | 4a |
|---|---|---|---|---|---|---|---|---|---|
| 333 | 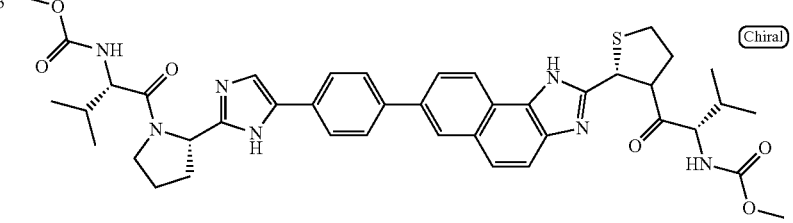 | 0.646 | B | | C | | | B | C |
| 334 | 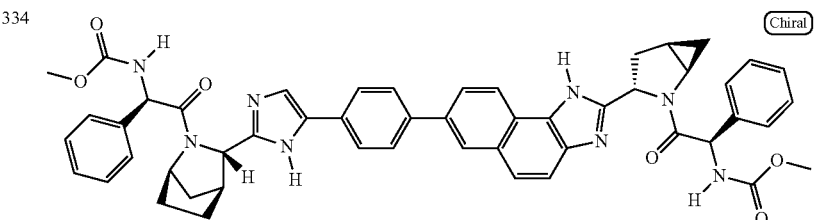 | 0.009 | C | | C | | | C | C |
| 335 | 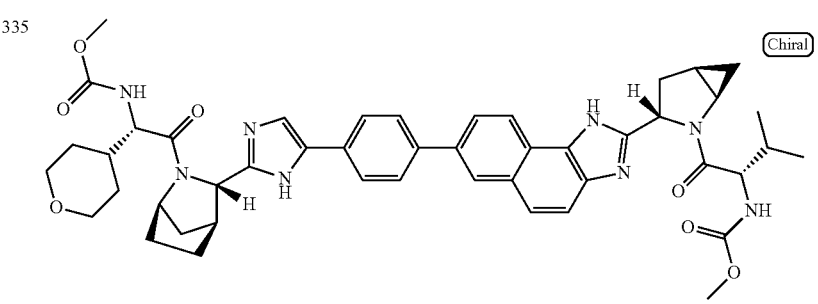 | 0.027 | C | | C | | | C | C |
| 336 | 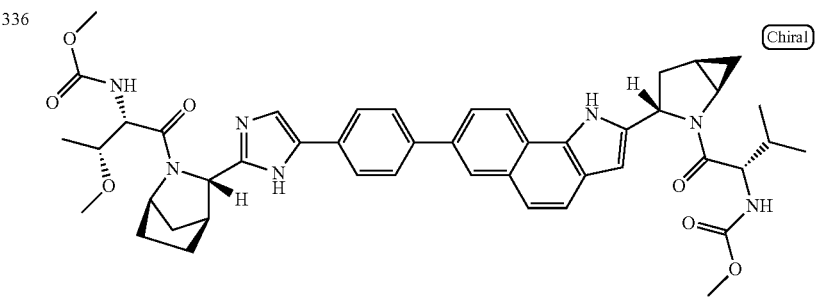 | 0.013 | C | | C | | | B | C |
| 337 | 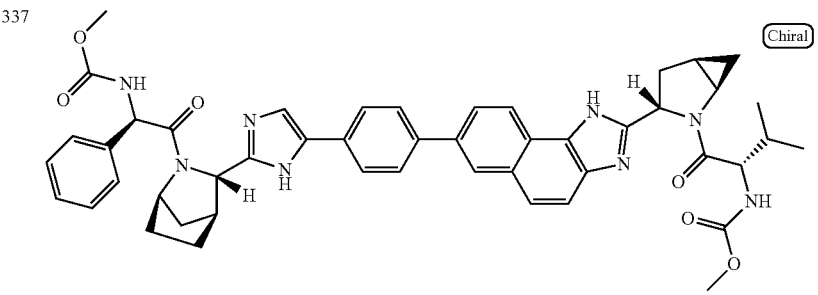 | 0.010 | C | | C | | | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 338 | 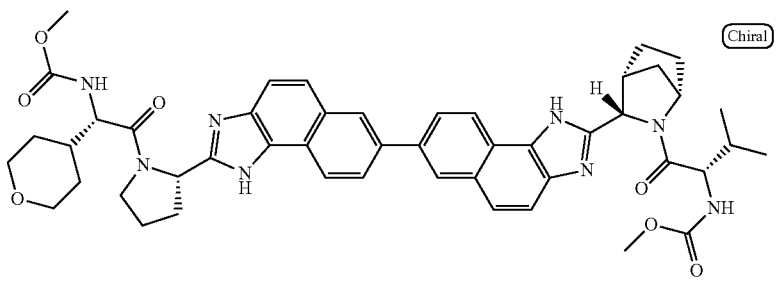 [SMILES: COC(=O)N[C@H](C(=O)N1[C@H]2CC[C@H](C2)[C@H]1c1nc2ccc3cc(-c4ccc5c(ccc6nc([C@@H]7CCCN7C(=O)[C@@H](NC(=O)OC)C7CCOCC7)[nH]c65)c4)ccc3c2[nH]1)C(C)C] | 0.127 | C | | C | | | C | C |
| 339 | 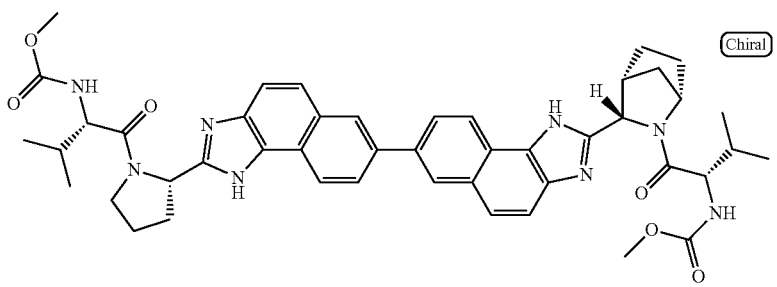 [SMILES: COC(=O)N[C@H](C(=O)N1CCC[C@H]1c1nc2ccc3cc(-c4ccc5c(ccc6nc([C@@H]7[C@@H]8CC[C@@H](C8)N7C(=O)[C@@H](NC(=O)OC)C(C)C)[nH]c65)c4)ccc3c2[nH]1)C(C)C] | 0.026 | C | B | C | C | B | C | C |
| 340 | 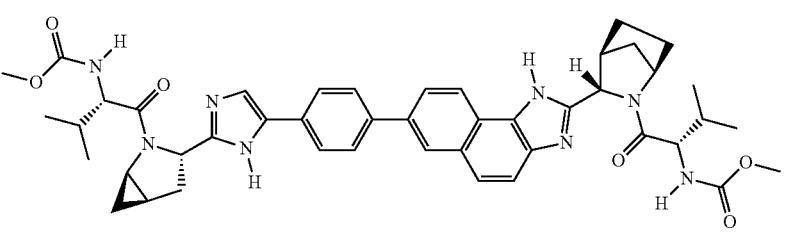 | 0.013 | C | | C | | | C | C |
| 341 | 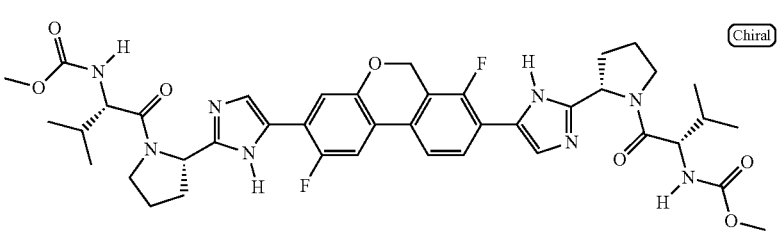 | 0.006 | C | | C | | | C | C |
| 342 | 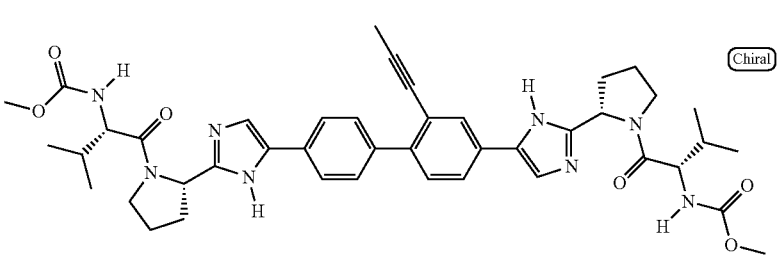 | 0.010 | C | | C | | | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 343 | 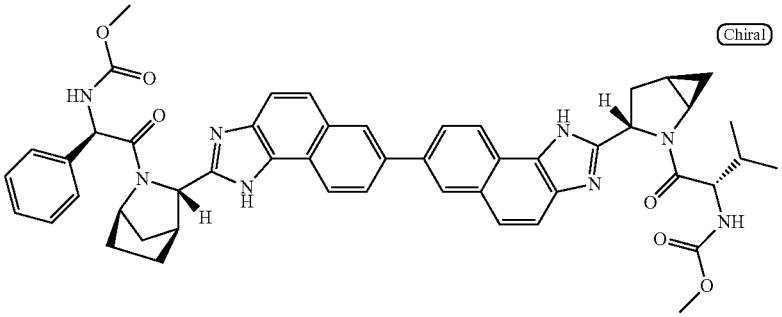 [SMILES: COC(=O)N[C@H](C(=O)N1[C@@H]2C[C@@H]2C[C@H]1c1nc2ccc3cc(-c4ccc5c(ccc6nc([C@@H]7[C@H]8CC[C@H](C8)N7C(=O)[C@H](NC(=O)OC)c7ccccc7)[nH]c65)c4)ccc3c2[nH]1)C(C)C] | 0.012 | C | | C | | | C | C |
| 344 | 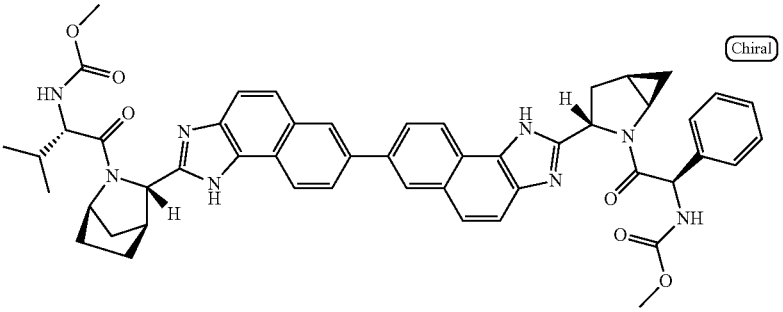 [SMILES: COC(=O)N[C@H](C(=O)N1[C@@H]2CC[C@@H](C2)[C@H]1c1nc2ccc3cc(-c4ccc5c(ccc6nc([C@@H]7C[C@H]8C[C@H]8N7C(=O)[C@H](NC(=O)OC)c7ccccc7)[nH]c65)c4)ccc3c2[nH]1)C(C)C] | 0.010 | C | | C | | | C | C |
| 345 | 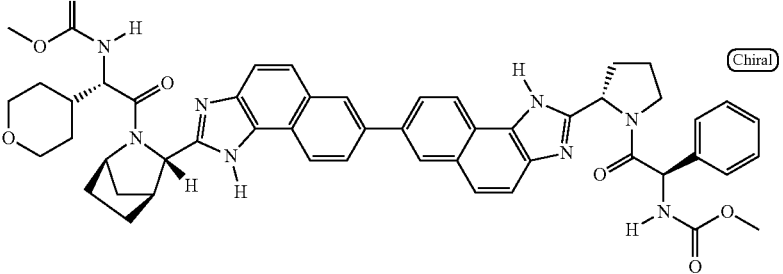 | 0.066 | C | | C | C | | C | C |
| 346 | 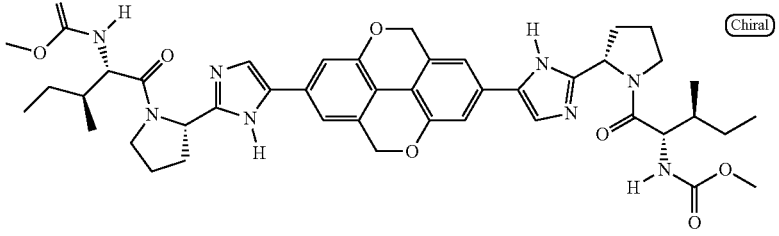 | 0.019 | C | | C | | B | C | C |
| 347 | 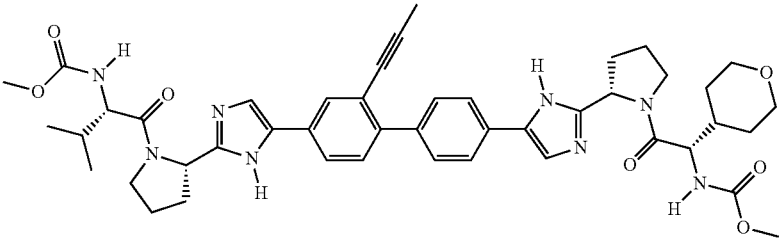 | 0.055 | C | | C | | | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 348 | [structure] | 0.011 | C | | C | | | C | C |
| 349 | [structure] | 0.005 | C | | C | | | C | C |
| 350 | [structure] | 0.020 | C | | C | | | C | C |
| 351 | [structure] | 0.008 | C | | C | | | C | C |
| 352 | [structure] | 0.011 | C | | C | B | B | C | C |

TABLE 4-continued

| # | 1b (nM) | 1a | 1a Q30R | 2a JFH | 2a J6 | 2b | 3a | 4a |
|---|---------|----|---------|--------|-------|----|----|----|
| 353 | 0.493 | C | | C | | | C | C |
| 354 | 0.031 | C | | C | | | C | C |
| 355 | 0.095 | C | | C | B | B | C | C |
| 356 | 0.022 | C | | C | C | C | C | C |
| 357 | 0.044 | C | | C | C | C | C | C |

TABLE 4-continued

| # | 1b (nM) | 1a | 1a Q30R | 2a JFH | 2a J6 | 2b | 3a | 4a |
|---|---|---|---|---|---|---|---|---|
| 358 | 0.057 | C |  | C | C | C | C | C |
| 359 | 0.011 | C |  | C |  | C | C |  |
| 360 | 0.053 | C |  | C |  | C | C |  |
| 361 | 0.013 | C |  | C |  | C | C |  |
| 362 | 0.011 | C |  | C |  | C | C |  |

TABLE 4-continued
| # | | 1b (nM) | 1a | 1a Q30R | 2a JFH | 2a J6 | 2b | 3a | 4a |
|---|---|---|---|---|---|---|---|---|---|
| 363 | 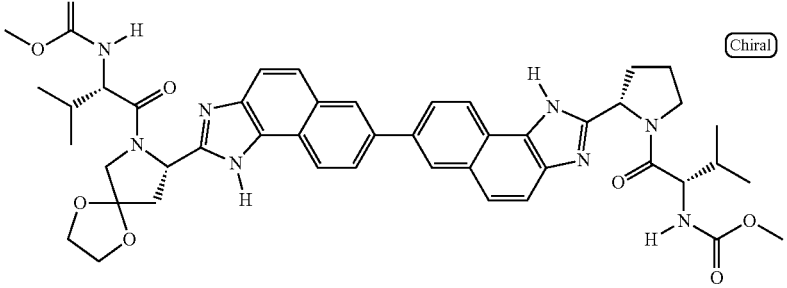 | 0.025 | C | | C | B | A | B | C |
| 364 | 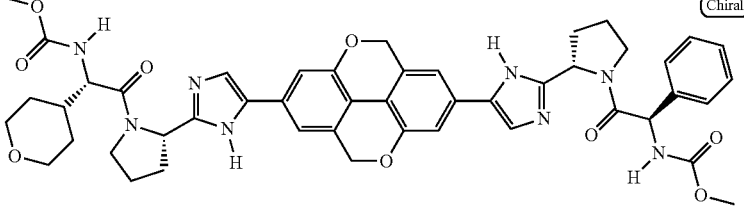 | 0.335 | C | | C | C | C | C | C |
| 365 | 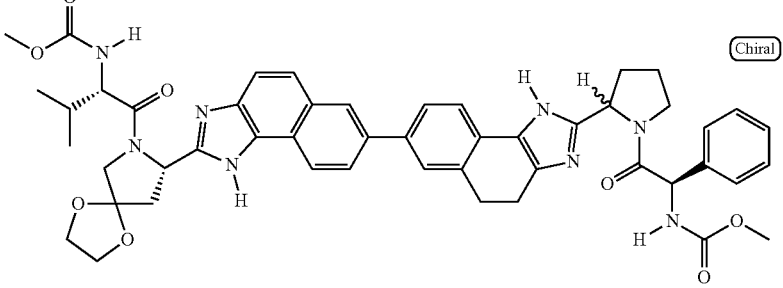 | 0.110 | C | | C | C | C | C | C |
| 366 | 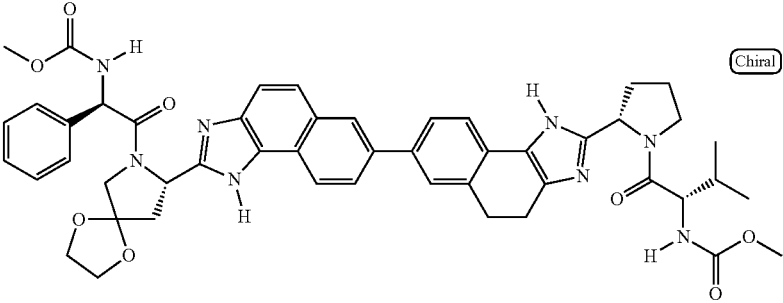 | 0.075 | C | | C | | | C | C |
| 367 | 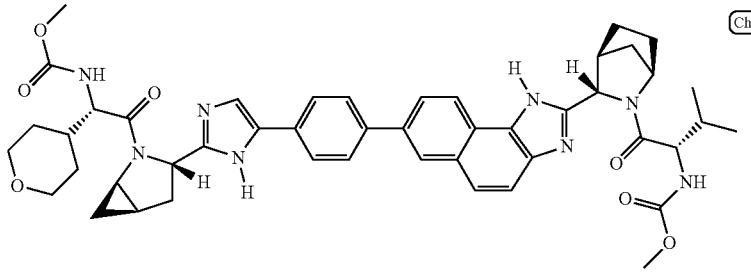 | 0.049 | C | | C | | | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 368 | 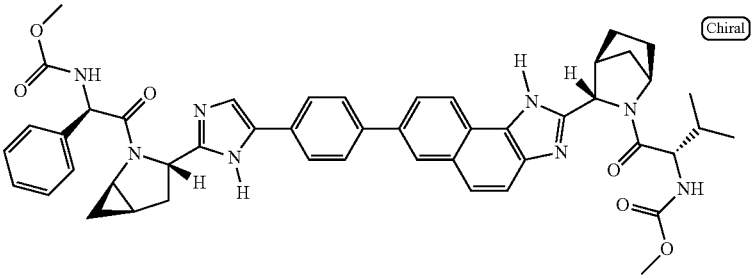 [SMILES: COC(=O)N[C@H](C(=O)N1[C@@H]2CC[C@@H](C2)[C@H]1c1nc2ccc3cc(-c4ccc(-c5cnc([C@@H]6C[C@H]7C[C@H]7N6C(=O)[C@H](NC(=O)OC)c6ccccc6)[nH]5)cc4)ccc3c2[nH]1)C(C)C] | 0.012 | C | | C | | | C | C |
| 369 | 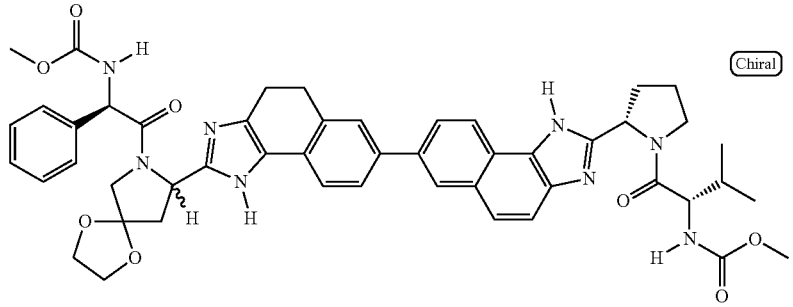 | 0.047 | C | | C | | | C | C |
| 370 | 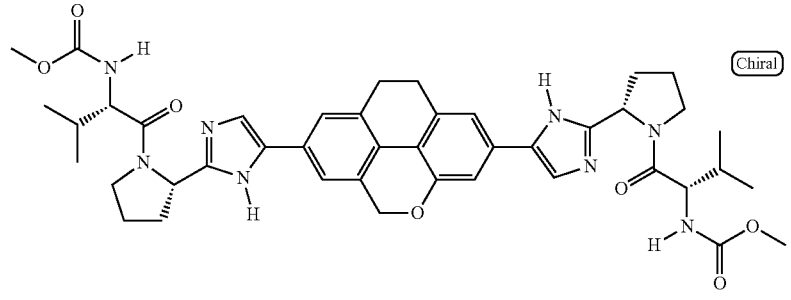 | 0.028 | C | | C | A | | C | C |
| 371 | 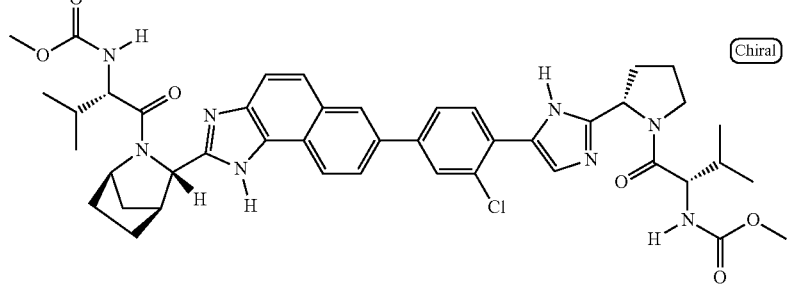 | 0.007 | C | | C | | | A | C |
| 372 | 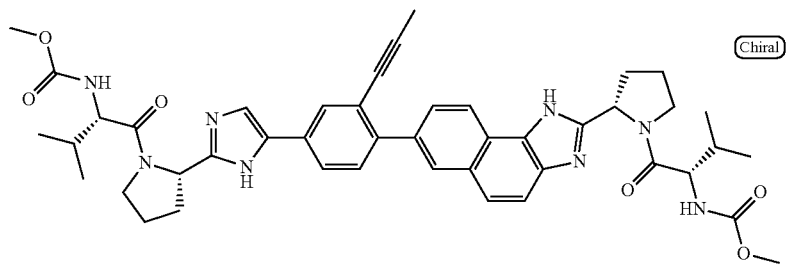 | 0.008 | C | | C | | | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 373 | 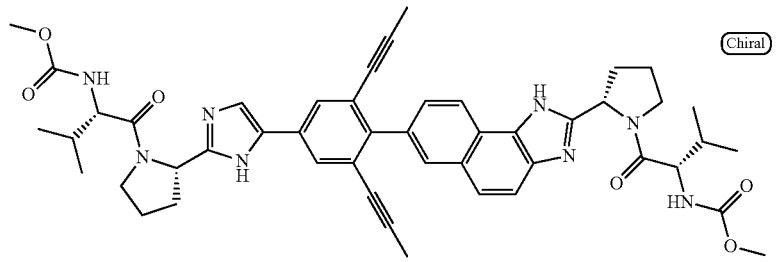 (Chiral) | 0.013 | C | | C | B | B | C | C |
| 374 | 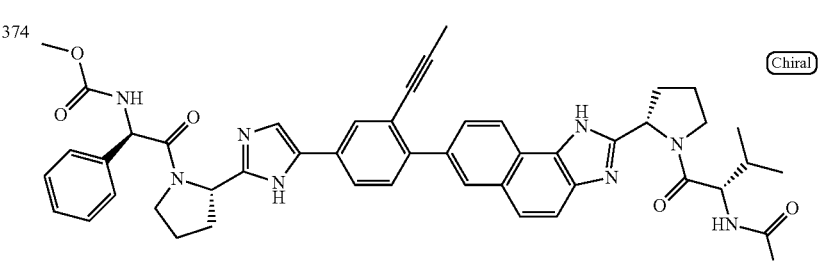 (Chiral) | 0.019 | C | | C | C | B | C | C |
| 375 | 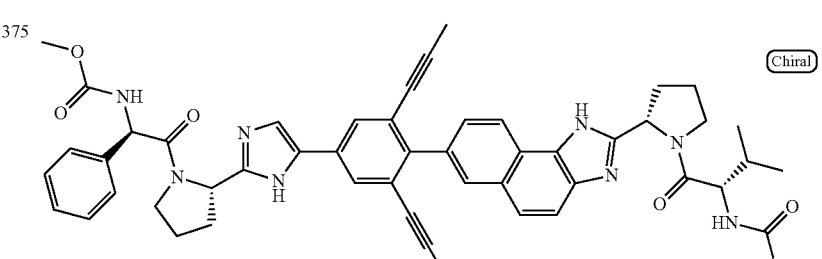 (Chiral) | 0.015 | B | | C | C | C | C | C |
| 376 | 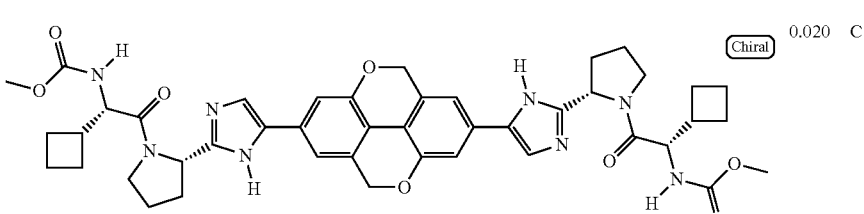 (Chiral) | 0.020 | C | | C | | | C | C |
| 377 | 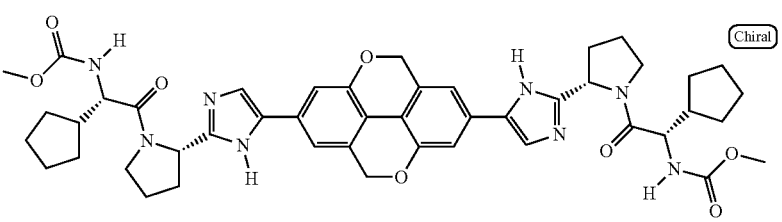 (Chiral) | 0.022 | C | | C | | | C | C |
| 378 | 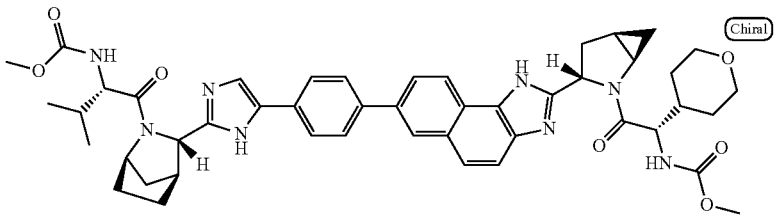 (Chiral) | 0.036 | C | | C | | | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 379 | 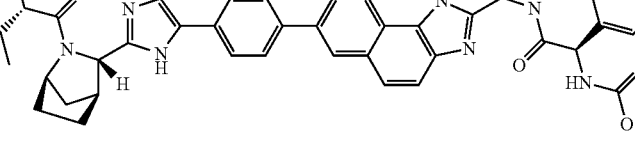 | 0.009 | C | | C | C | A | C | C |
| 380 | 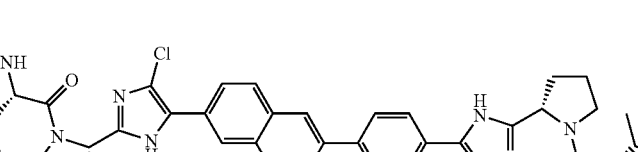 | 0.006 | C | | C | | | A | C |
| 381 |  | 0.008 | C | | C | A | | C | C |
| 382 | 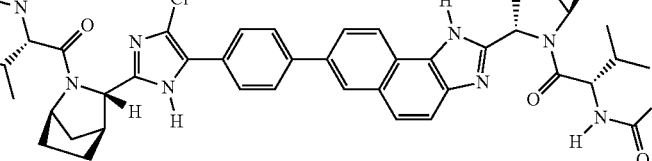 | 0.006 | C | | A | | | A | C |
| 383 |  | 0.008 | C | | C | | | C | C |
| 384 | 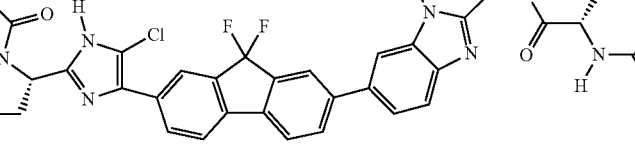 | 0.013 | C | B | C | B | | C | C |

TABLE 4-continued
| # | | 1b (nM) | 1a Q30R | 2a JFH | 2a J6 | 2b | 3a | 4a |
|---|---|---|---|---|---|---|---|---|
| 385 | 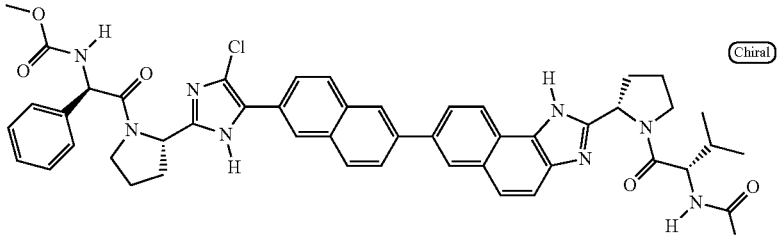 (Chiral) | 0.007 | C | | C | B | B | C | C |
| 386 | 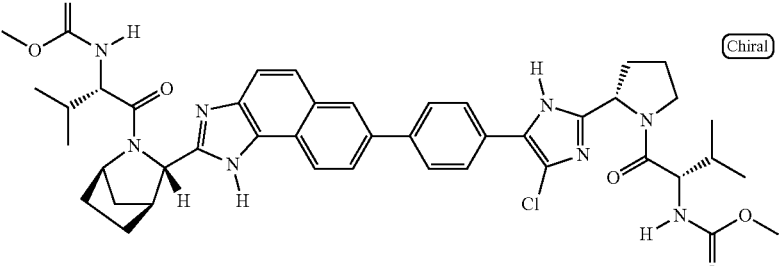 (Chiral) | 0.015 | C | | C | A | A | C | C |
| 387 | 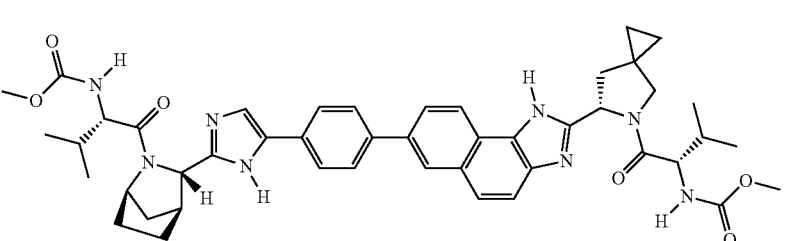 | 0.009 | C | | C | A | A | C | C |
| 388 | 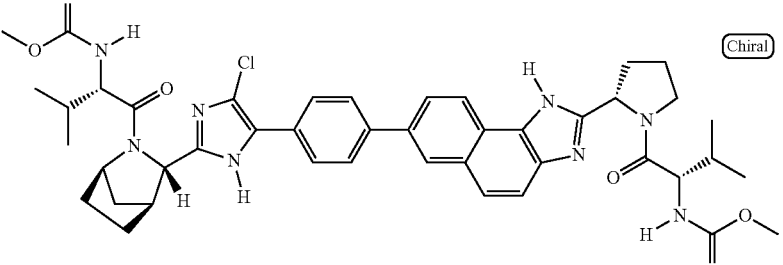 (Chiral) | 0.008 | C | | C | A | A | C | C |
| 389 | 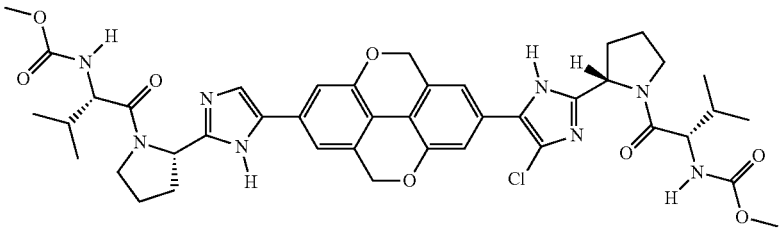 | 0.015 | C | | C | B | | C | C |
| 390 | 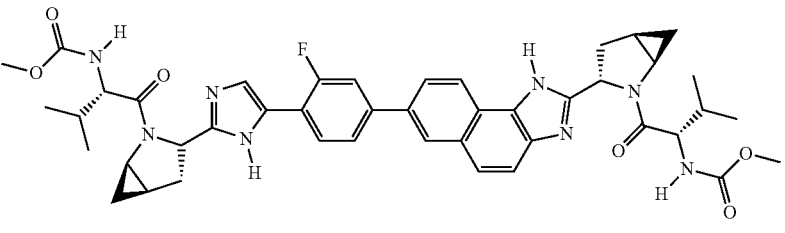 | 0.003 | C | | C | A | | B | C |

TABLE 4-continued

| # | 1b (nM) | 1a | 1a Q30R | 2a JFH | 2a J6 | 2b | 3a | 4a |
|---|---|---|---|---|---|---|---|---|
| 391 | 0.009 | C | | C | A | | A | C |
| 392 | 0.022 | C | | C | A | | B | C |
| 393 | 0.012 | C | | C | A | | C | C |
| 394 | 0.008 | C | | C | B | A | C | C |
| 395 | 0.004 | C | | C | A | A | C | C |
| 396 | 0.019 | C | | C | A | | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 397 | 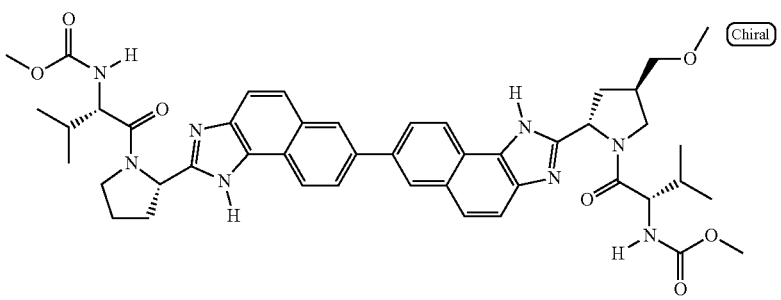 | 0.017 | C | C | C | C | C | C | C |
| 398 | 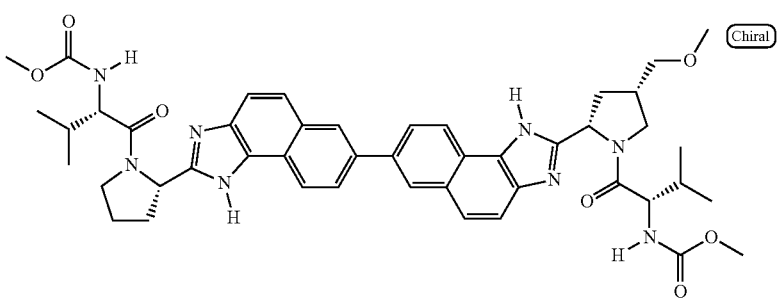 | 0.023 | C | C | C | C | C | C | C |
| 399 | 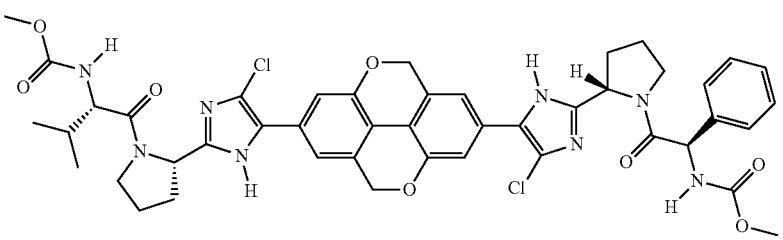 | 0.017 | C | | C | C | | C | C |
| 400 | 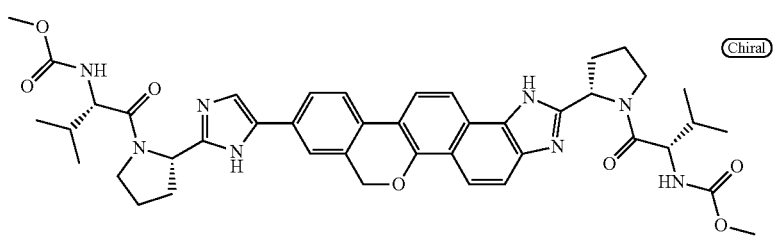 | 0.017 | C | | C | A | A | C | C |
| 401 | 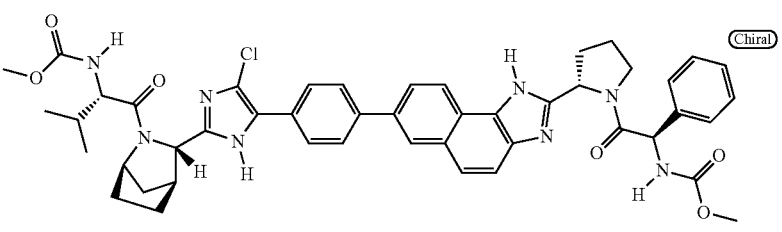 | 0.015 | C | | C | B | | C | C |
| 402 | 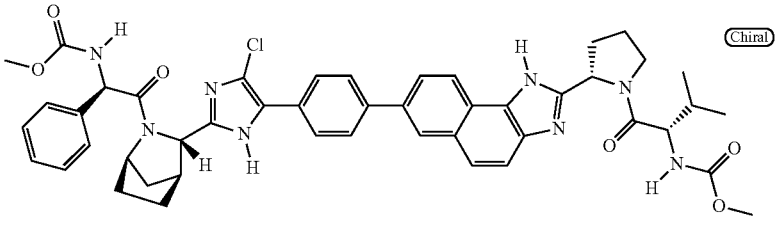 | 0.015 | C | | C | A | | C | C |

TABLE 4-continued
| # | 1b (nM) | 1a | 1a Q30R | 2a JFH | 2a J6 | 2b | 3a | 4a |
|---|---|---|---|---|---|---|---|---|
| 403 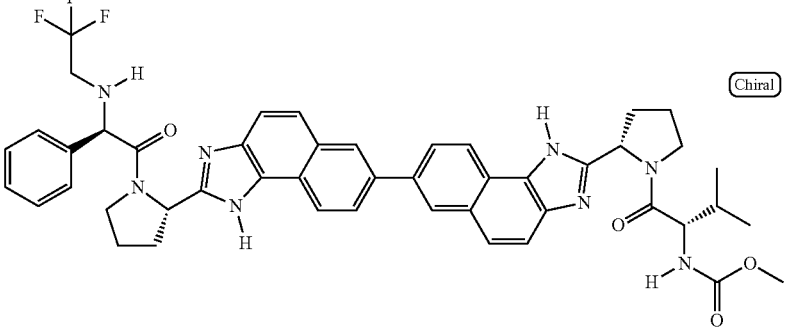 | 0.014 | C | | C | | C | C | C |
| 404 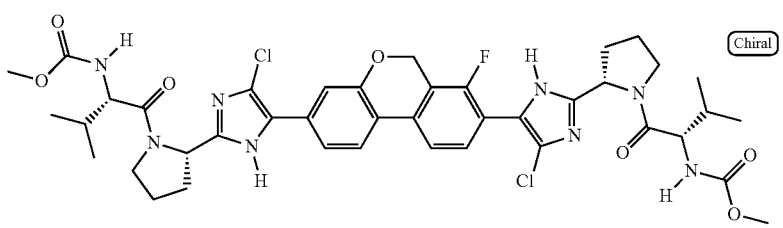 | 0.008 | C | | C | A | | C | C |
| 405 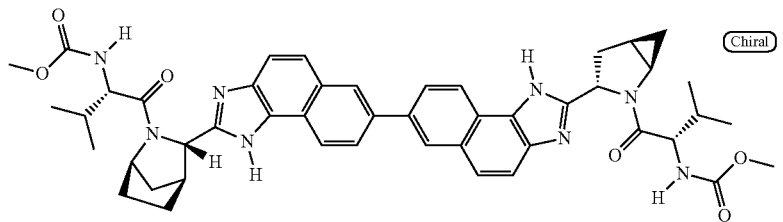 | 0.009 | C | | C | B | | C | C |
| 406 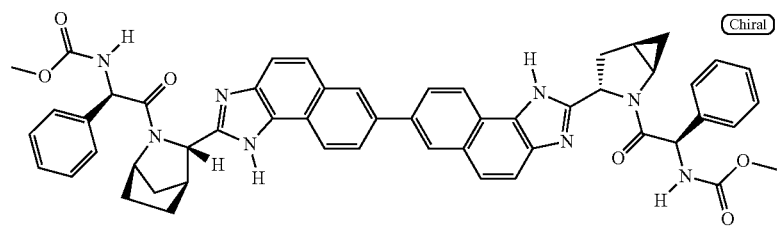 | 0.017 | C | | C | C | | C | C |
| 407 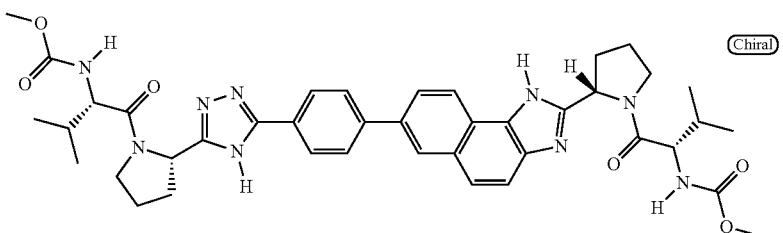 | 0.048 | C | | C | A | | B | C |
| 408 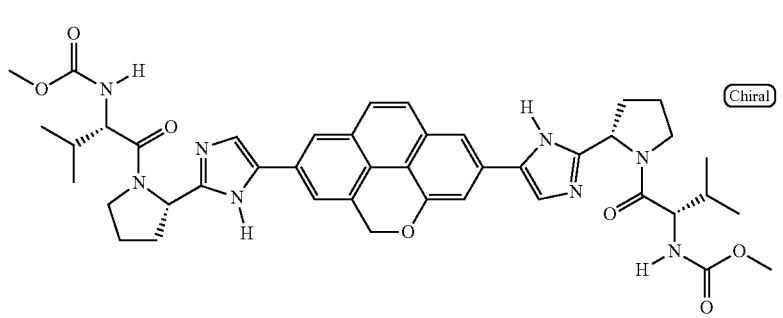 | 0.022 | C | | C | A | A | C | C |

TABLE 4-continued

| # | 1b (nM) | 1a | 1a Q30R | 2a JFH | 2a J6 | 2b | 3a | 4a |
|---|---------|----|---------|--------|-------|----|----|----|
| 409 | 0.584 | C | | C | B | B | C | C |
| 410 | 0.018 | C | | C | B | A | C | C |
| 411 | 0.034 | C | | C | B | B | C | C |
| 412 | 0.018 | C | | C | B | C | C | C |
| 413 | 0.017 | C | | C | B | B | C | C |
| 414 | 0.022 | C | B | C | B | B | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 415 | 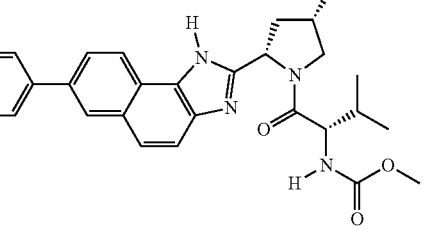 | 0.034 | C | | C | C | C | C | C |
| 416 | 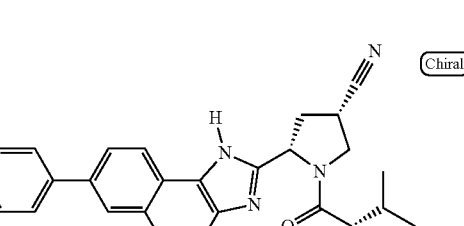 | 0.043 | C | | C | C | B | C | C |
| 417 | 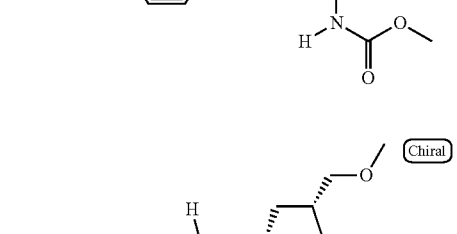 | 0.024 | C | | C | B | B | C | C |
| 418 | 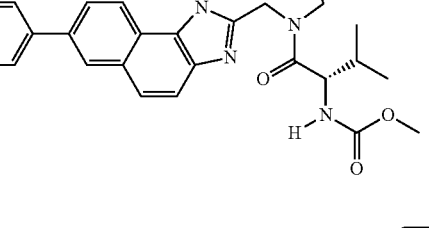 | 0.035 | C | B | C | C | C | C | C |
| 419 | 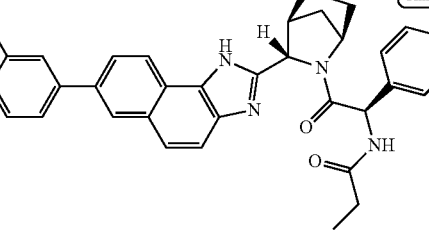 | 0.786 | B | | C | C | C | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 420 | | 4.662 | B | | C | B | B | C | B |
| 421 | | 0.041 | C | | C | C | C | C | C |
| 422 | (Chiral) | 0.017 | C | C | C | B | C | C | C |
| 423 | (Chiral) | 0.020 | C | C | C | C | C | C | C |
| 424 | (Chiral) | 0.028 | C | B | C | C | C | C | C |
| 425 | (Chiral) | 0.034 | C | C | C | C | C | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 426 | 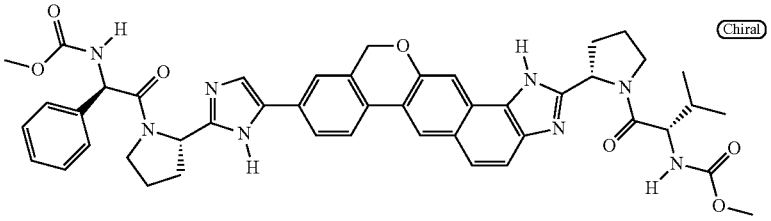 (Chiral) | 0.033 | C | C | C | C | C | C | C |
| 427 | 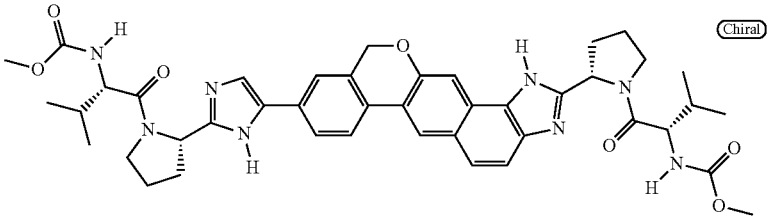 (Chiral) | 0.049 | C | B | C | B | C | C | C |
| 428 | 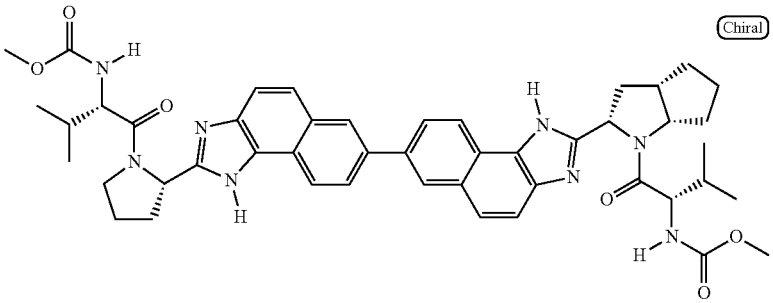 (Chiral) | 0.011 | C | | C | C | B | C | C |
| 429 | 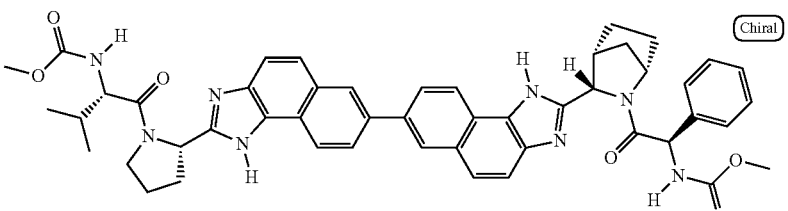 (Chiral) | 0.033 | C | | C | B | B | C | C |
| 430 | 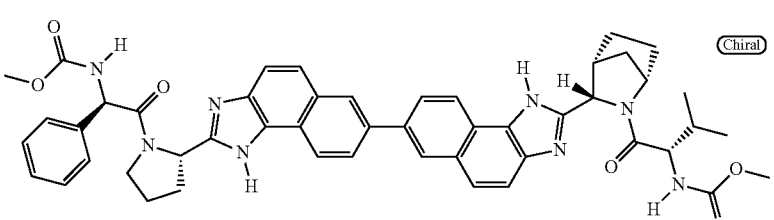 (Chiral) | 0.036 | C | B | C | C | C | C | C |
| 431 | 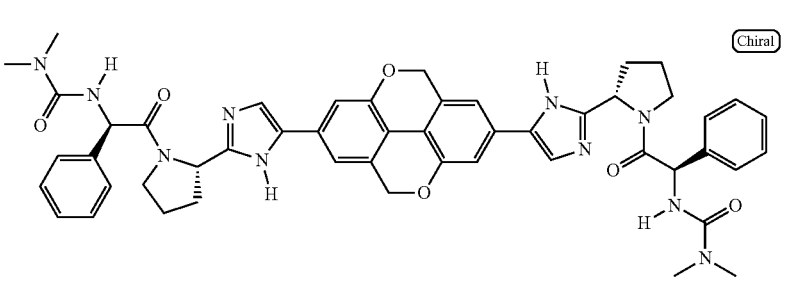 [SMILES: CN(C)C(=O)N[C@@H](C(=O)N1CCC[C@H]1c1ncc(-c2cc3c4c(c2)OCc2cc(-c5cnc([C@@H]6CCCN6C(=O)[C@H](NC(=O)N(C)C)c6ccccc6)[nH]5)cc(c2-4)OC3)[nH]1)c1ccccc1] (Chiral) | 0.436 | C | | C | C | C | C | C |

TABLE 4-continued

| # | 1b (nM) | 1a | 1a Q30R | 2a JFH | 2a J6 | 2b | 3a | 4a |
|---|---|---|---|---|---|---|---|---|
| 432 | 0.022 | C | | C | B | B | C | C |
| 433 | 0.020 | C | C | C | C | C | C | C |
| 434 | 0.055 | C | C | C | C | C | C | C |
| 435 | 0.058 | C | C | C | C | C | C | C |
| 436 | 0.051 | C | C | C | C | C | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 437 | 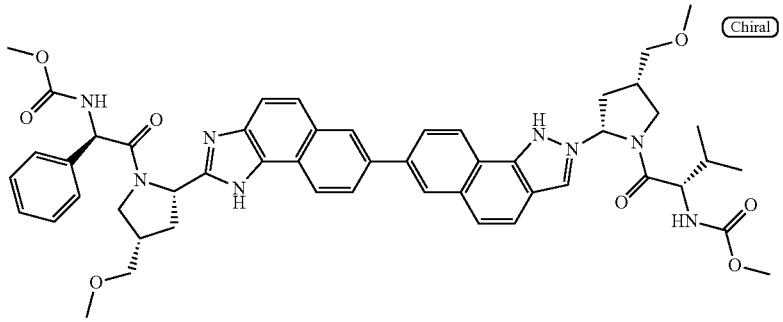 | 0.048 | C | C | C | C | C | C | C |
| 438 | 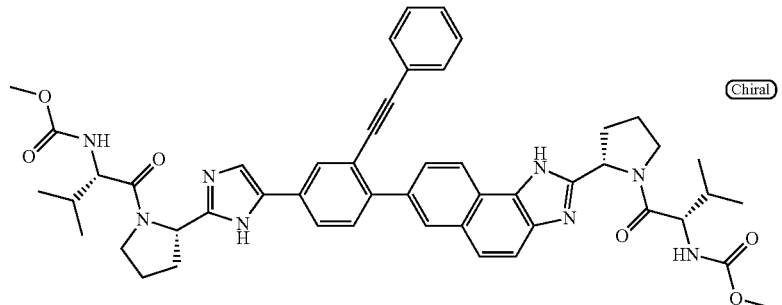 | 0.003 | C | B | C | A | A | C | C |
| 439 | 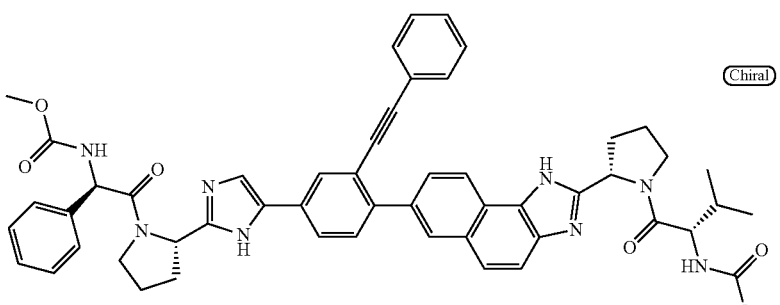 | 0.004 | C |   | C | B | A | C | C |
| 440 | 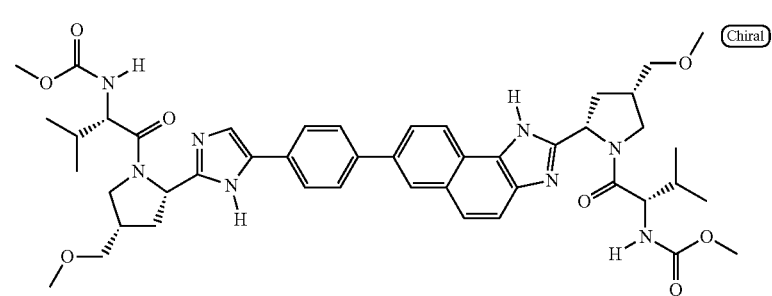 | 0.048 | C |   | C | C | B | B | C |
| 441 | 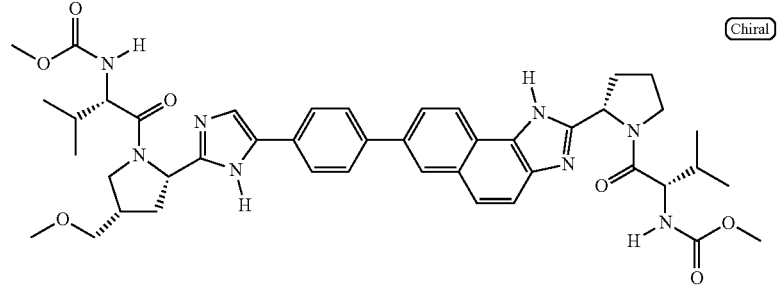 | 0.030 | C |   | C | B | A | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 442 | 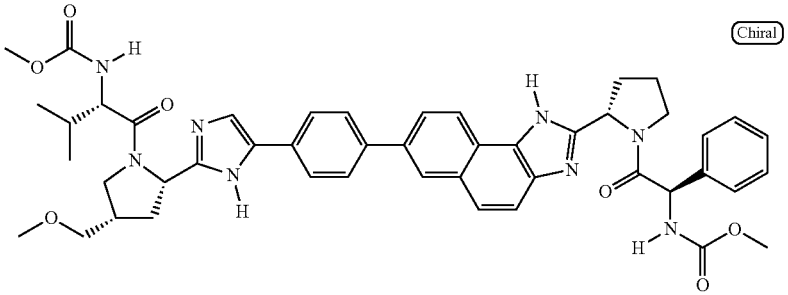 [SMILES: COC[C@H]1C[C@@H](c2ncc(-c3ccc(-c4ccc5c(ccc6nc([C@@H]7CCCN7C(=O)[C@H](NC(=O)OC)c7ccccc7)[nH]c65)c4)cc3)[nH]2)N(C(=O)[C@@H](NC(=O)OC)C(C)C)C1] | 0.029 | C | | C | C | C | C | C |
| 443 | 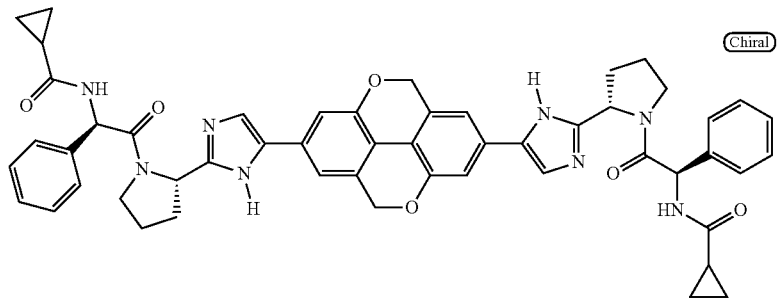 [SMILES: O=C(N[C@@H](C(=O)N1CCC[C@H]1c1ncc(-c2cc3c4c(c2)OCc2cc(-c5cnc([C@@H]6CCCN6C(=O)[C@H](NC(=O)C6CC6)c6ccccc6)[nH]5)cc(c2-4)OC3)[nH]1)c1ccccc1)C1CC1] | 0.167 | C | | C | C | C | C | C |
| 444 | 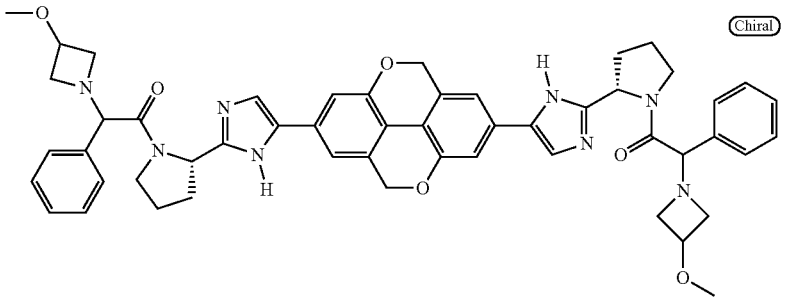 [SMILES: COC1CN(C(C(=O)N2CCC[C@H]2c2ncc(-c3cc4c5c(c3)OCc3cc(-c6cnc([C@@H]7CCCN7C(=O)C(c7ccccc7)N7CC(OC)C7)[nH]6)cc(c3-5)OC4)[nH]2)c2ccccc2)C1] | 1.763 | B | | C | B | B | C | B |
| 445 | 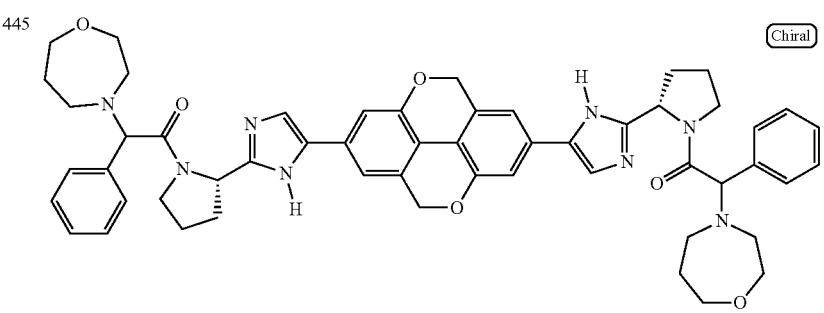 | 0.336 | B | | C | B | B | C | C |
| 446 | 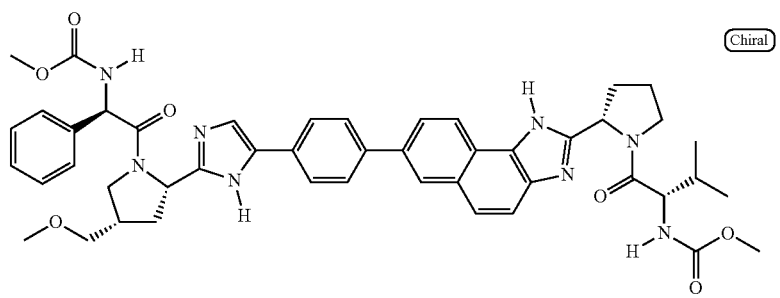 | 0.030 | C | C | C | C | C | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 447 | 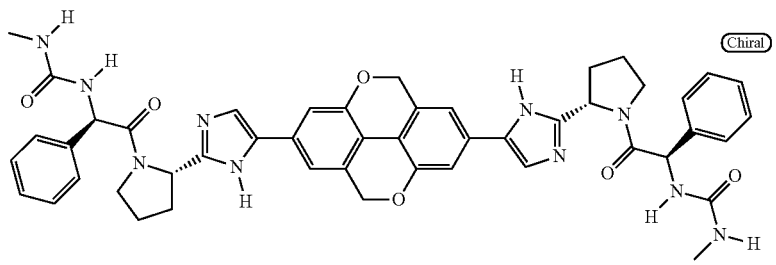 [SMILES: CNC(=O)N[C@@H](C(=O)N1CCC[C@H]1c1ncc(-c2cc3c4c(c2)OCc2cc(-c5cnc([C@@H]6CCCN6C(=O)[C@H](NC(=O)NC)c6ccccc6)[nH]5)cc(c2-4)OC3)[nH]1)c1ccccc1] | 2.046 | B | | C | C | C | C | C |
| 448 | 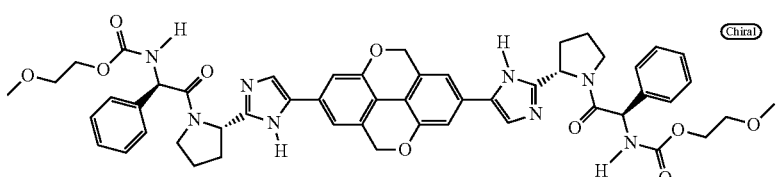 | 0.459 | C | | C | B | C | C | C |
| 449 | 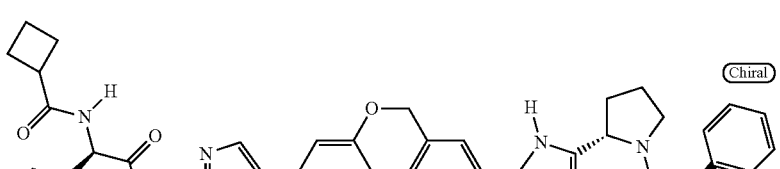 | 0.139 | C | | C | C | C | C | C |
| 450 | 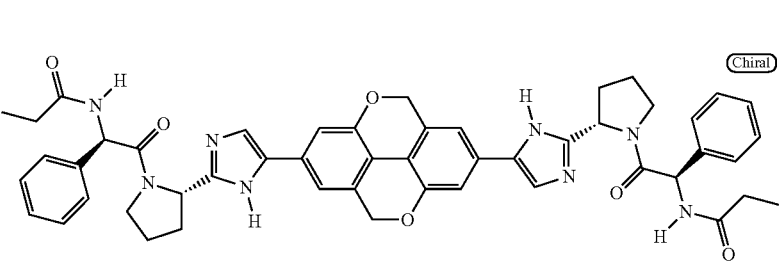 [SMILES: CCC(=O)N[C@@H](C(=O)N1CCC[C@H]1c1ncc(-c2cc3c4c(c2)OCc2cc(-c5cnc([C@@H]6CCCN6C(=O)[C@H](NC(=O)CC)c6ccccc6)[nH]5)cc(c2-4)OC3)[nH]1)c1ccccc1] | 0.427 | C | | C | C | C | C | C |
| 451 | 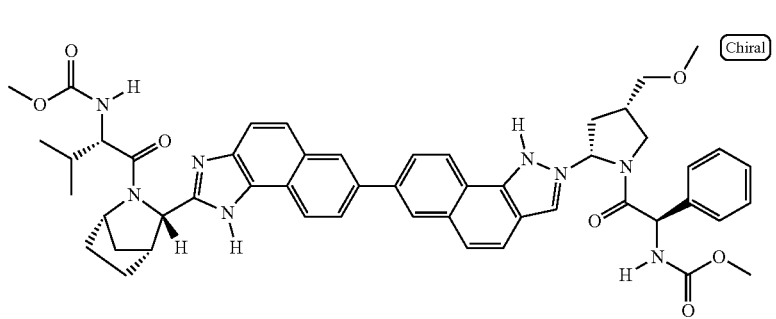 | 0.070 | C | | C | C | C | C | C |

TABLE 4-continued

| # | 1b (nM) | 1a | 1a Q30R | 2a JFH | 2a J6 | 2b | 3a | 4a |
|---|---|---|---|---|---|---|---|---|
| 452 | 0.047 | C | | C | C | B | C | C |
| 453 | 0.018 | C | C | C | C | C | C | C |
| 454 | 0.028 | C | C | C | C | C | C | C |
| 455 | 0.029 | C | | C | C | C | C | C |
| 456 | 0.040 | C | | C | C | C | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 457 | 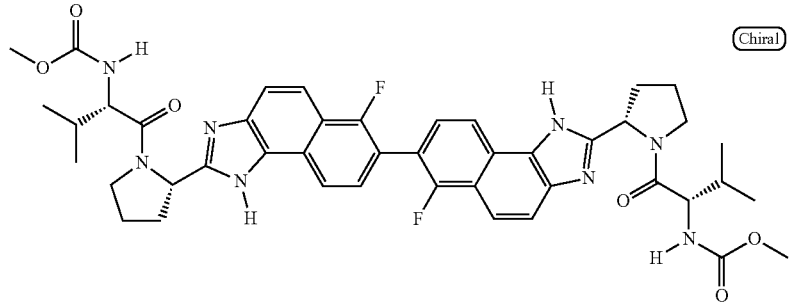 | 0.009 | C | | C | A | A | C | C |
| 458 | 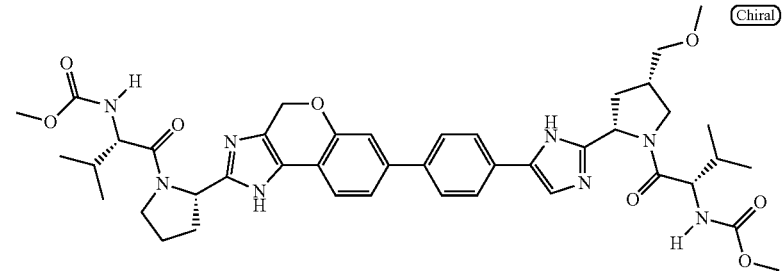 | 0.085 | C | | C | A | A | B | C |
| 459 | 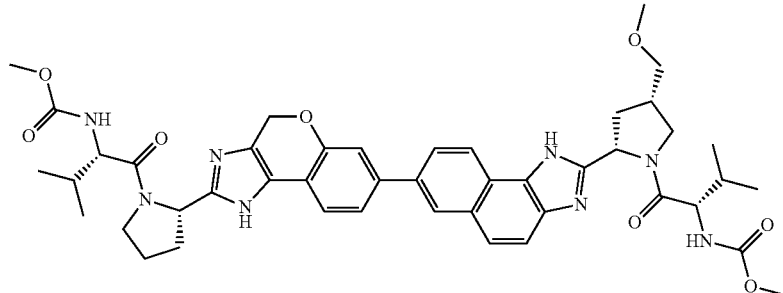 | 0.033 | C | | C | C | A | C | C |
| 460 | 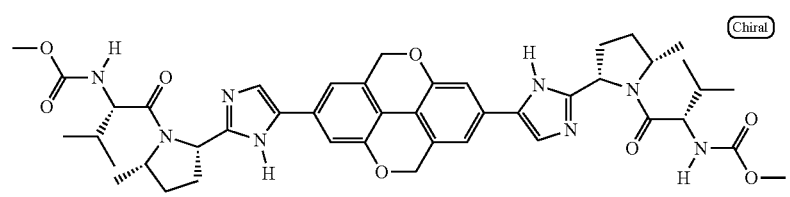 | 0.018 | C | | C | B | C | C | C |
| 461 | 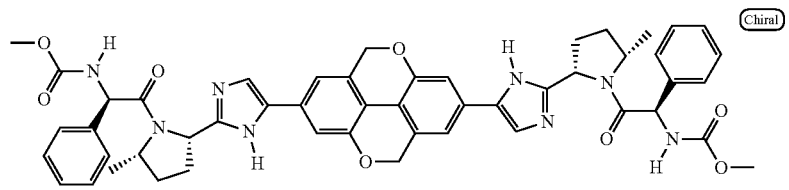 | 0.020 | C | | C | B | C | C | C |
| 462 | 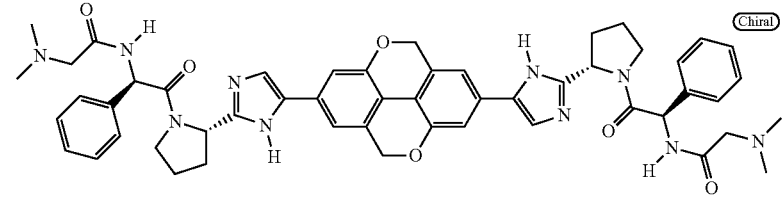 | 8.764 | B | | C | B | B | C | B |

TABLE 4-continued
| # | | 1b (nM) | 1a | 1a Q30R | 2a JFH | 2a J6 | 2b | 3a | 4a |
|---|---|---|---|---|---|---|---|---|---|
| 463 | 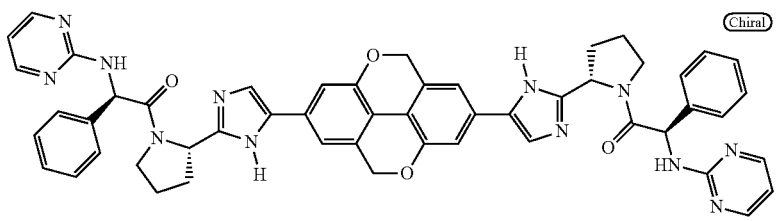 [SMILES: O=C([C@H](Nc1ncccn1)c1ccccc1)N1CCC[C@H]1c1ncc(-c2cc3c4c(c2)OCc2cc(-c5cnc([C@@H]6CCCN6C(=O)[C@H](Nc6ncccn6)c6ccccc6)[nH]5)cc(c2-4)OC3)[nH]1] | #### | B | | B | A | A | B | A |
| 464 | 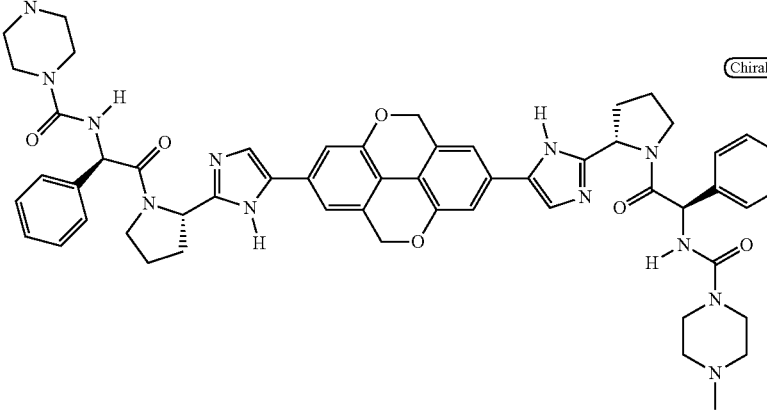 | #### | A | | B | B | A | B | A |
| 465 | 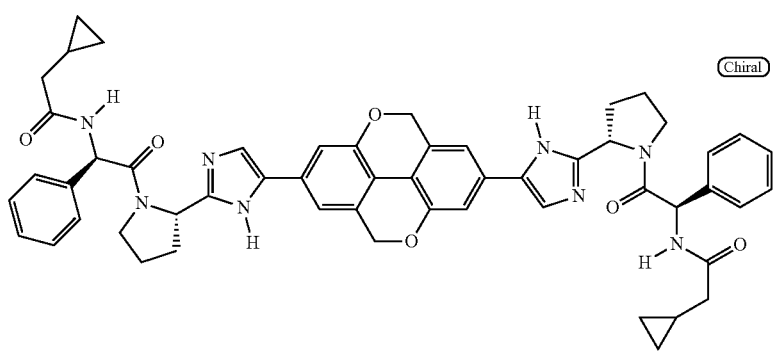 [SMILES: O=C(CC1CC1)N[C@@H](C(=O)N1CCC[C@H]1c1ncc(-c2cc3c4c(c2)OCc2cc(-c5cnc([C@@H]6CCCN6C(=O)[C@H](NC(=O)CC6CC6)c6ccccc6)[nH]5)cc(c2-4)OC3)[nH]1)c1ccccc1] | 0.176 | C | | C | C | C | C | C |
| 466 | 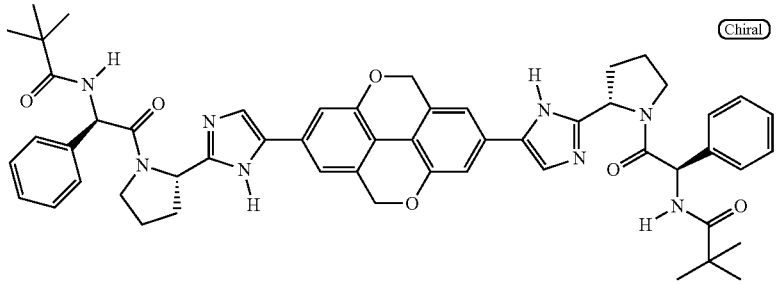 [SMILES: CC(C)(C)C(=O)N[C@@H](C(=O)N1CCC[C@H]1c1ncc(-c2cc3c4c(c2)OCc2cc(-c5cnc([C@@H]6CCCN6C(=O)[C@H](NC(=O)C(C)(C)C)c6ccccc6)[nH]5)cc(c2-4)OC3)[nH]1)c1ccccc1] | 0.042 | C | | C | B | B | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 467 | 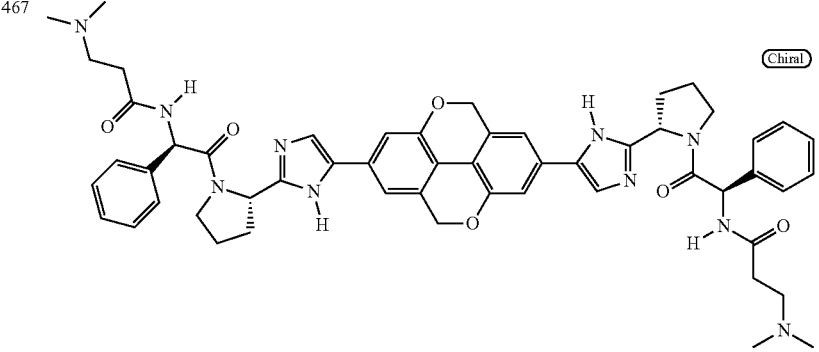 | #### | A | | A | A | A | A | A |
| 468 | 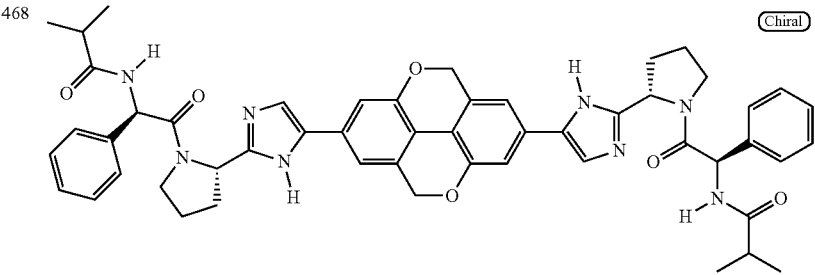 | 0.113 | C | | C | C | C | C | C |
| 469 | 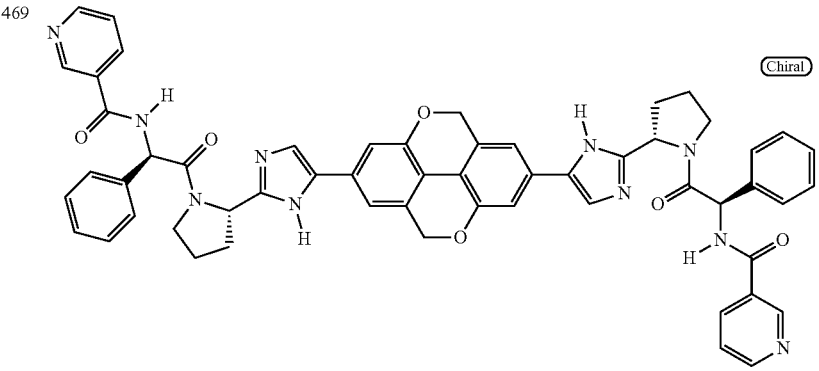 | 0.752 | C | | C | C | C | C | C |
| 470 | 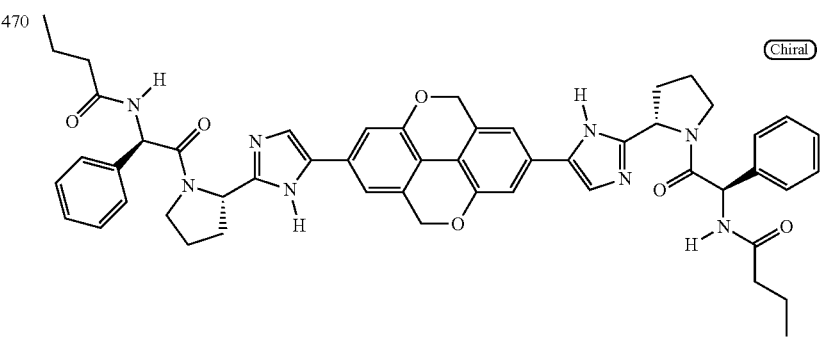 | 0.148 | C | | C | C | C | C | C |

TABLE 4-continued

| # | 1b (nM) | 1a | 1a Q30R | 2a JFH | 2a J6 | 2b | 3a | 4a |
|---|---|---|---|---|---|---|---|---|
| 471 | 0.015 | C | | C | C | B | C | C |
| 472 | 0.010 | C | C | C | C | C | C | C |
| 473 | 0.015 | C | | C | B | B | C | C |
| 474 | 0.025 | C | | C | B | B | C | C |
| 475 | 0.019 | C | C | C | C | C | C | C |

TABLE 4-continued

| # | 1b (nM) | 1a | 1a Q30R | 2a JFH | 2a J6 | 2b | 3a | 4a |
|---|---|---|---|---|---|---|---|---|
| 476 | 0.099 | C | | C | C | C | C | C |
| 477 | 0.089 | C | | C | C | C | C | C |
| 478 | 0.048 | C | | C | B | C | C | C |
| 479 | 0.034 | C | | C | C | C | C | C |
| 480 | 0.684 | C | | C | B | C | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 481 | | 0.058 | C | | C | C | C | C | C |
| 482 | | 0.034 | C | | C | C | C | C | C |
| 483 | | 0.814 | B | | C | A | C | C | C |
| 484 | | 0.953 | A | | C | A | A | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 485 | 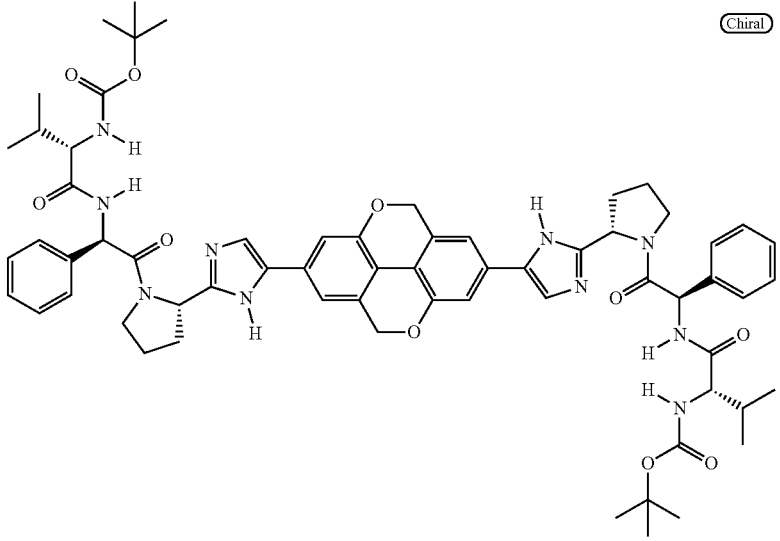 [SMILES: CC(C)[C@H](NC(=O)OC(C)(C)C)C(=O)N[C@@H](C(=O)N1CCC[C@H]1c1ncc(-c2cc3c4c(c2)OCc2cc(-c5cnc([C@@H]6CCCN6C(=O)[C@H](NC(=O)[C@@H](NC(=O)OC(C)(C)C)C(C)C)c6ccccc6)[nH]5)cc(c2-4)OC3)[nH]1)c1ccccc1] | 0.170 | B | | C | A | A | C | C |
| 486 | 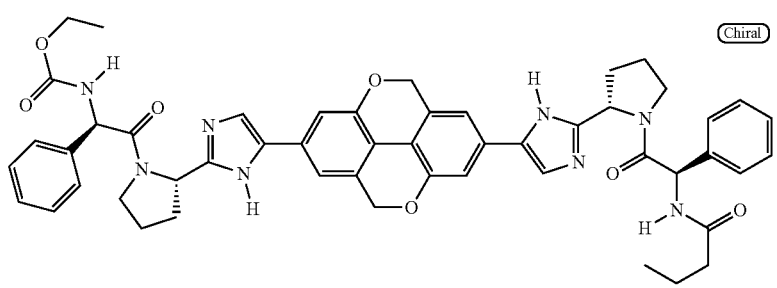 [SMILES: CCCC(=O)N[C@@H](C(=O)N1CCC[C@H]1c1ncc(-c2cc3c4c(c2)OCc2cc(-c5cnc([C@@H]6CCCN6C(=O)[C@H](NC(=O)OCC)c6ccccc6)[nH]5)cc(c2-4)OC3)[nH]1)c1ccccc1] | 0.030 | C | | C | B | C | C | C |
| 487 | 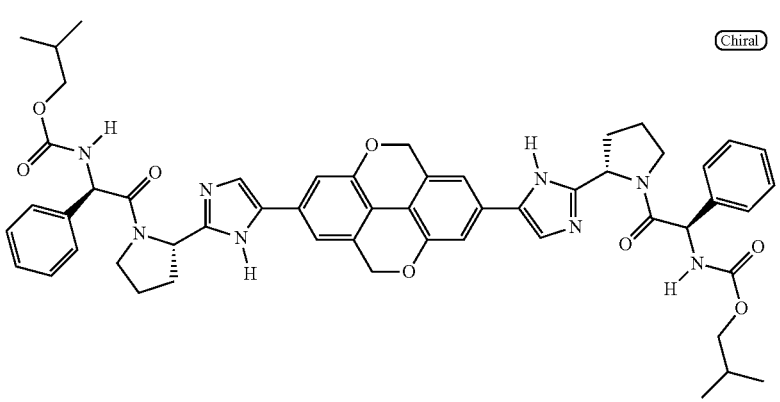 [SMILES: CC(C)COC(=O)N[C@@H](C(=O)N1CCC[C@H]1c1ncc(-c2cc3c4c(c2)OCc2cc(-c5cnc([C@@H]6CCCN6C(=O)[C@H](NC(=O)OCC(C)C)c6ccccc6)[nH]5)cc(c2-4)OC3)[nH]1)c1ccccc1] | 0.027 | C | | C | A | B | C | C |
| 488 | 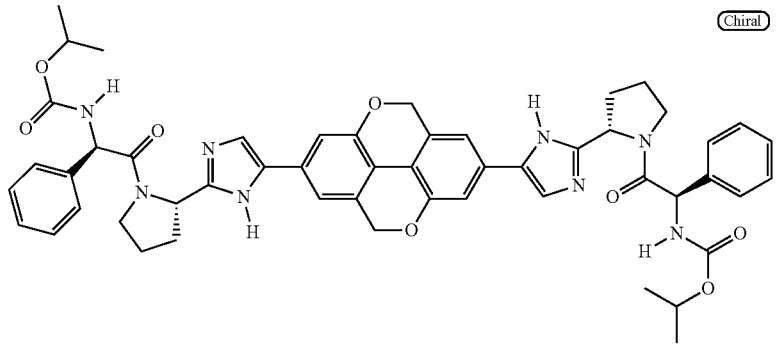 [SMILES: CC(C)OC(=O)N[C@@H](C(=O)N1CCC[C@H]1c1ncc(-c2cc3c4c(c2)OCc2cc(-c5cnc([C@@H]6CCCN6C(=O)[C@H](NC(=O)OC(C)C)c6ccccc6)[nH]5)cc(c2-4)OC3)[nH]1)c1ccccc1] | 0.030 | C | | C | B | C | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 489 | 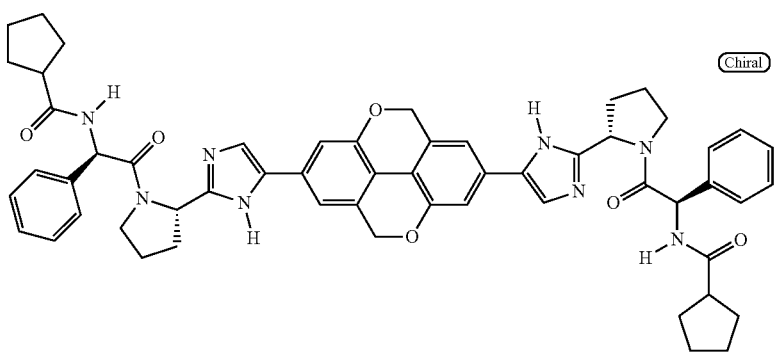 [SMILES: O=C(N[C@@H](C(=O)N1CCC[C@H]1c1ncc(-c2cc3c4c(c2)OCc2cc(-c5cnc([C@@H]6CCCN6C(=O)[C@H](NC(=O)C6CCCC6)c6ccccc6)[nH]5)cc(c2-4)OC3)[nH]1)c1ccccc1)C1CCCC1] (Chiral) | 0.048 | C | | C | C | C | C | C |
| 490 | 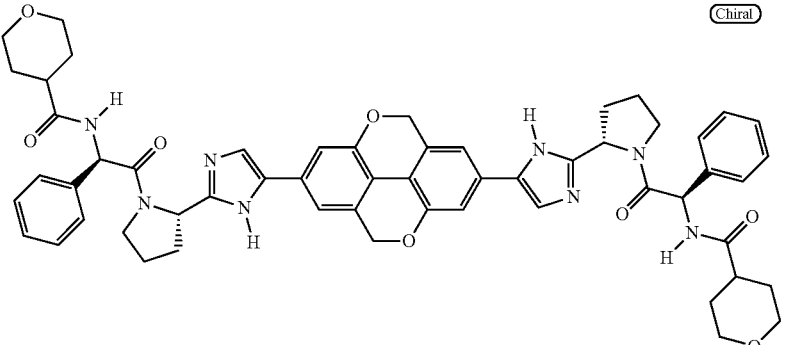 (Chiral) | 0.989 | B | | C | C | C | C | C |
| 491 | 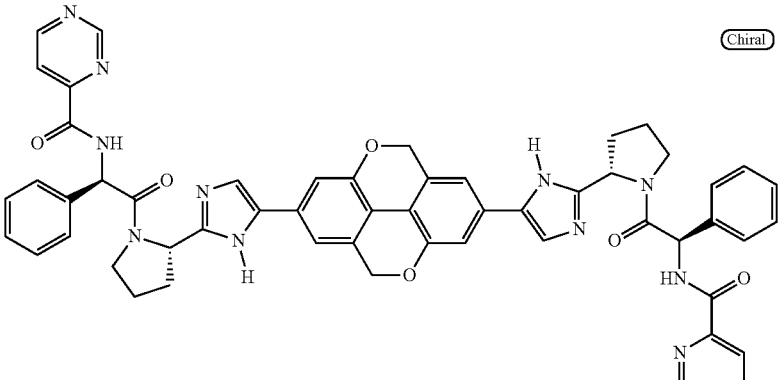 (Chiral) | 0.066 | C | | C | C | C | C | C |
| 492 | 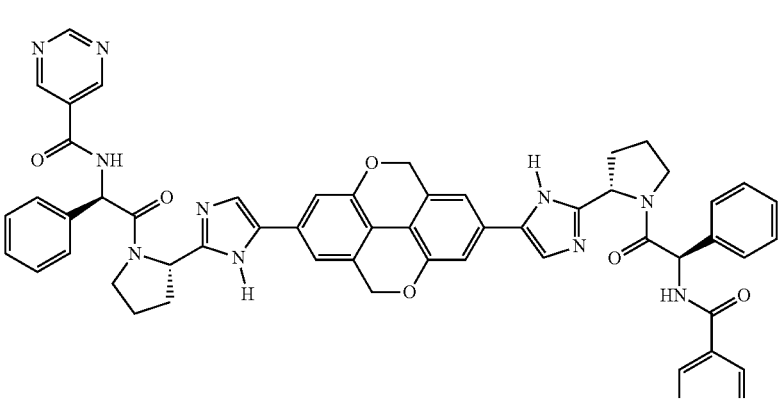 | 0.898 | B | | C | A | B | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 493 | | 0.030 | C | | C | A | C | C | C |
| 494 | | 0.021 | C | | C | C | C | C | C |
| 495 | | 0.026 | C | C | C | C | C | C | C |
| 496 | | 0.011 | C | | C | C | C | C | C |
| 497 | | 0.008 | C | | C | C | C | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 498 | (Chiral) | 0.016 | C | C | C | C | C | C | C |
| 499 | (Chiral) | 0.032 | C | | C | C | C | C | C |
| 500 | (Chiral) | 0.028 | C | C | C | B | C | C | C |
| 501 | (Chiral) | 0.021 | C | | C | A | B | C | C |
| 502 | (Chiral) | 0.016 | C | C | C | C | C | C | C |

TABLE 4-continued
| # | | 1b (nM) | 1a | 1a Q30R | 2a JFH | 2a J6 | 2b | 3a | 4a |
|---|---|---|---|---|---|---|---|---|---|
| 503 | 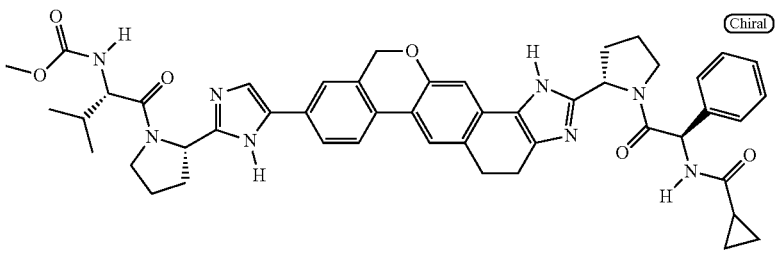 [SMILES: COC(=O)N[C@H](C(=O)N1CCC[C@H]1c1ncc(-c2ccc3c(c2)COc2cc4c(cc2-3)CCc2nc([C@@H]3CCCN3C(=O)[C@H](NC(=O)C3CC3)c3ccccc3)[nH]c2-4)[nH]1)C(C)C] (Chiral) | 0.041 | C | | C | C | C | C | C |
| 504 | 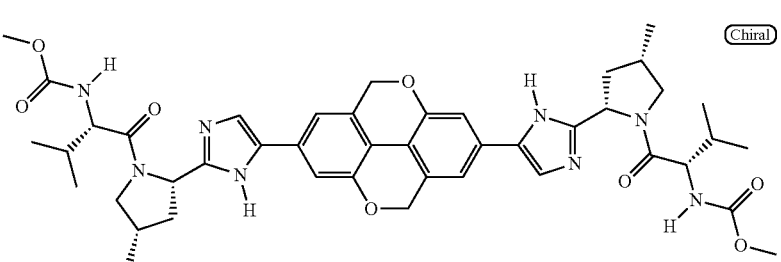 (Chiral) | 0.020 | C | | C | B | B | C | C |
| 505 | 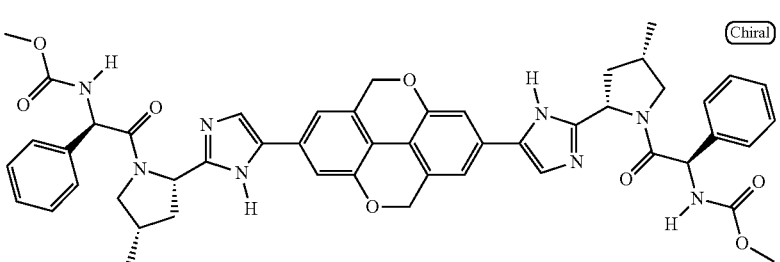 [SMILES: COC(=O)N[C@@H](C(=O)N1C[C@@H](C)C[C@H]1c1ncc(-c2cc3c4c(c2)OCc2cc(-c5cnc([C@@H]6C[C@H](C)CN6C(=O)[C@H](NC(=O)OC)c6ccccc6)[nH]5)cc(c2-4)OC3)[nH]1)c1ccccc1] (Chiral) | 0.019 | C | | C | C | C | C | C |
| 506 | 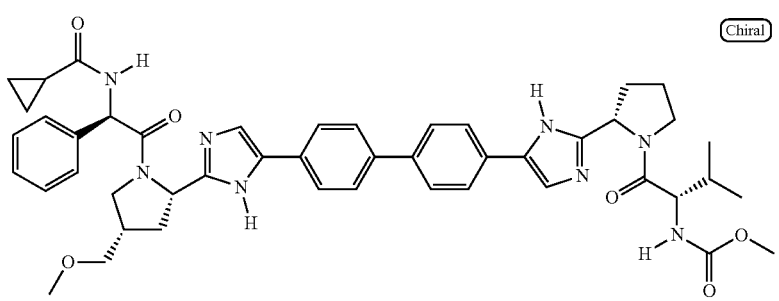 [SMILES: COC[C@H]1C[C@@H](c2ncc(-c3ccc(-c4ccc(-c5cnc([C@@H]6CCCN6C(=O)[C@@H](NC(=O)OC)C(C)C)[nH]5)cc4)cc3)[nH]2)N(C(=O)[C@H](NC(=O)C2CC2)c2ccccc2)C1] (Chiral) | 0.036 | C | C | C | C | C | C | C |
| 507 | 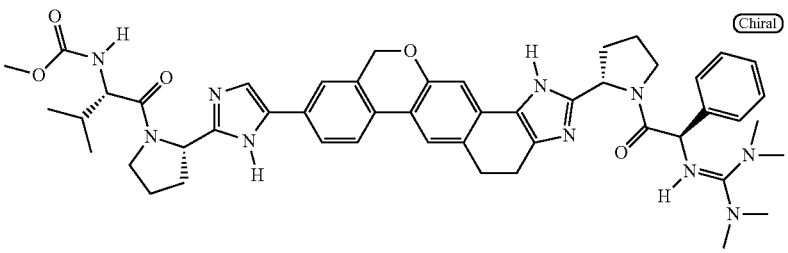 (Chiral) | 1.503 | B | | C | A | B | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 508 | (Chiral) | 0.026 | C | | C | C | C | C | C |
| 509 | (Chiral) | 0.028 | C | | C | C | C | C | C |
| 510 | (Chiral) | 0.050 | C | | C | C | C | C | C |
| 511 | (Chiral) | 0.019 | C | | C | C | C | C | C |
| 512 | (Chiral) | 0.035 | C | | C | C | C | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 513 | (Chiral) | 0.068 | C | | C | B | B | C | C |
| 514 | (Chiral) | 0.010 | C | | C | C | C | C | C |
| 515 | | 0.047 | C | | C | C | B | C | C |
| 516 | (Chiral) | 0.024 | C | | C | C | C | C | C |
| 517 | (Chiral) | 0.025 | C | | C | C | C | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 518 | Chiral | 0.010 | C | | C | B | C | C | C |
| 519 | Chiral | 0.010 | C | | C | | C | C | | C |
| 520 | Chiral | 0.033 | C | | C | | C | C | | C |
| 521 | Chiral | 0.028 | C | | C | | C | C | | C |
| 522 | Chiral | 0.023 | C | | C | A | C | | C |

TABLE 4-continued

| # | 1b (nM) | 1a | 1a Q30R | 2a JFH | 2a J6 | 2b | 3a | 4a |
|---|---|---|---|---|---|---|---|---|
| 523 | 0.037 | C | | C | B | C | | C |
| 524 | 0.020 | C | | C | A | B | | C |
| 525 | 0.038 | C | C | C | C | C | C | C |
| 526 | 0.018 | C | C | C | C | C | C | C |
| 527 | 0.022 | C | C | C | C | C | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 528 | (Chiral) | 0.010 | C | | C | C | C | | C |
| 529 | (Chiral) | 0.013 | C | | C | C | C | | C |
| 530 | (Chiral) | 0.011 | C | | C | C | C | | C |
| 531 | (Chiral) | 0.018 | C | | C | C | C | | C |
| 532 | (Chiral) | 0.009 | C | | C | C | C | | C |
| 533 | (Chiral) | 0.012 | C | | C | C | C | | C |

TABLE 4-continued

| # | | 1b (nM) | 1a | 1a Q30R | 2a JFH | 2a J6 | 2b | 3a | 4a |
|---|---|---|---|---|---|---|---|---|---|
| 534 | (structure) | 0.011 | C | | C | C | C | | C |
| 535 | (structure) | 0.022 | C | | C | C | C | | C |
| 536 | (structure) | 0.013 | C | C | C | C | C | C | C |
| 537 | (structure) | 0.014 | C | | C | C | C | | C |
| 538 | (structure) | 0.016 | C | C | C | C | C | C | C |

TABLE 4-continued

| # | | 1b (nM) | 1a | 1a Q30R | 2a JFH | 2a J6 | 2b | 3a | 4a |
|---|---|---|---|---|---|---|---|---|---|
| 539 | Chiral | 0.016 | C | C | C | C | C | C | C |

1b (nM); 1a, 1a Q30R, 2a JFH, 2a J6, 2b - A ≥ 44 nM, B = 1-43.99 nM, C = 0.001-0.999 nM; 3a, 4a - A ≥ 5 nM, B = 1-4.99 nM, C = 0.001-0.99 nM

TABLE 5

| # | | 1b (nM) | 1a | 1a Q30R | 2a JFH | 2a J6 | 2b | 3a | 4a |
|---|---|---|---|---|---|---|---|---|---|
| 540 | Chiral | 0.018 | C | C | C | C | C | C | C |
| 541 | Chiral | 0.034 | C | | C | C | C | | C |
| 542 | Chiral | 0.050 | C | | C | C | C | | C |

TABLE 5-continued

| # | | 1b (nM) | 1a | 1a Q30R | 2a JFH | 2a J6 | 2b | 3a | 4a |
|---|---|---|---|---|---|---|---|---|---|
| 543 | (Chiral) | 0.015 | C | C | C | C | C | C | C |
| 544 | (Chiral) | 0.026 | C | C | C | C | C | C | C |
| 545 | (Chiral) | 0.075 | C | C | C | C | C | C | C |
| 546 | | 0.048 | C | C | C | C | C | C | C |
| 547 | (Chiral) | 0.005 | C | | C | C | C | C | C |

TABLE 5-continued

| # | 1b (nM) | 1a | 1a Q30R | 2a JFH | 2a J6 | 2b | 3a | 4a |
|---|---|---|---|---|---|---|---|---|
| 548 | 0.006 | C | C | C | C | C | C | C |
| 549 | 0.007 | C |  | C | C | C | C | C |
| 550 | 0.013 | C | C | C | C | C | C | C |
| 551 | 0.018 | C | C | C | C | C | C | C |
| 552 | 0.033 | C | C | C | C | C | C | C |

TABLE 5-continued
| # | | 1b (nM) | 1a | 1a Q30R | 2a JFH | 2a J6 | 2b | 3a | 4a |
|---|---|---|---|---|---|---|---|---|---|
| 553 | (Chiral) 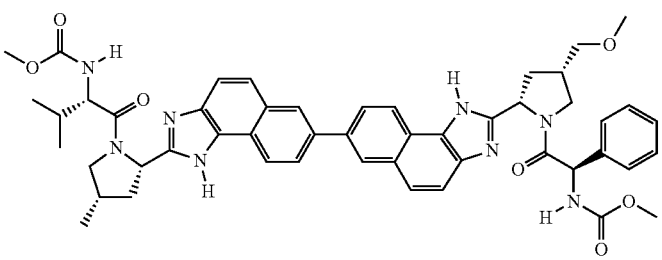 | 0.014 | C | | C | C | C | C | C |
| 554 | (Chiral) 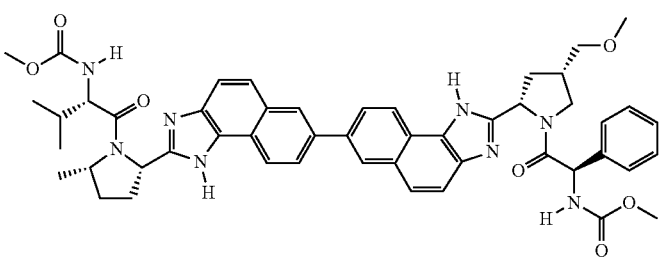 | 0.012 | C | C | C | C | C | C | C |
| 555 | (Chiral) 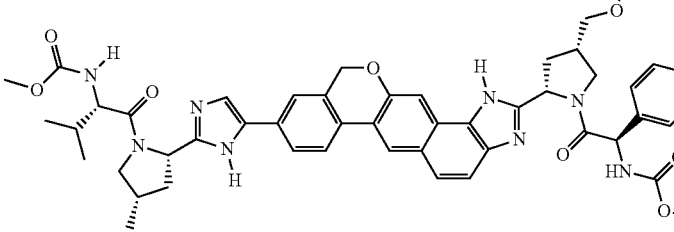 | 0.021 | C | C | C | C | C | C | C |
| 556 | (Chiral) 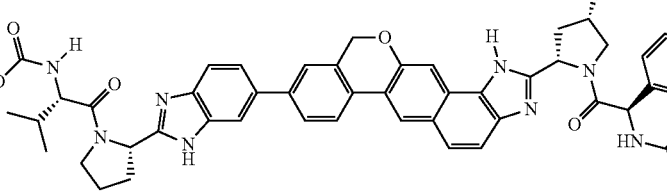 | 0.008 | C | | C | A | A | | C |
| 557 | (Chiral) 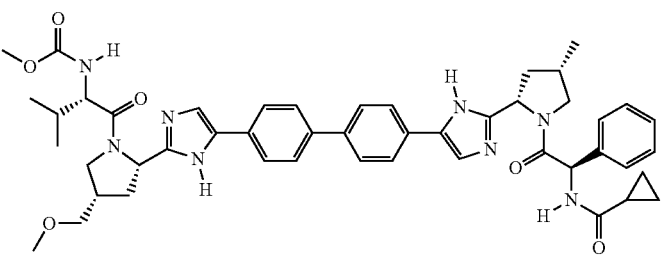 | 0.028 | C | | C | C | C | | C |

TABLE 5-continued
| # | | 1b (nM) | 1a | 1a Q30R | 2a JFH | 2a J6 | 2b | 3a | 4a |
|---|---|---|---|---|---|---|---|---|---|
| 558 | (Chiral) | 0.014 | C | C | C | C | C | | C |
| 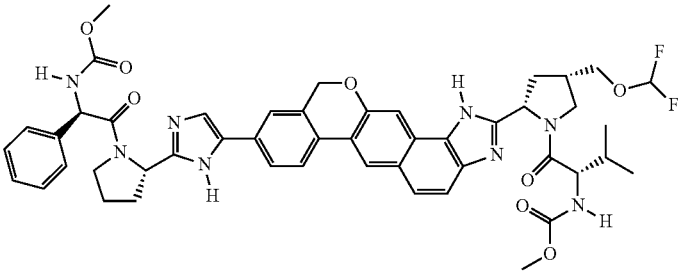 | | | | | | | | | |
| 559 | (Chiral) | 0.080 | C | C | C | C | C | C | C |
| 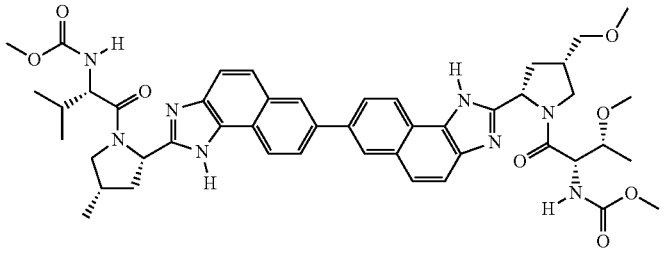 | | | | | | | | | |
| 560 | (Chiral) | 0.092 | C | C | C | C | C | C | C |
| 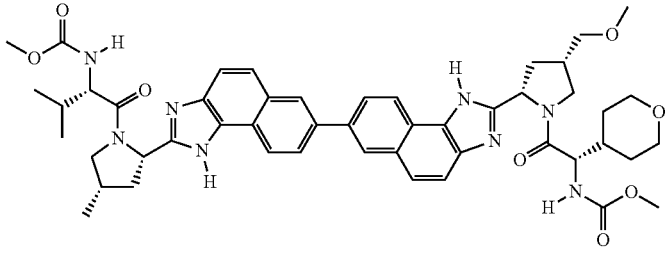 | | | | | | | | | |
| 561 | (Chiral) | 0.010 | C | C | C | C | C | C | C |
| 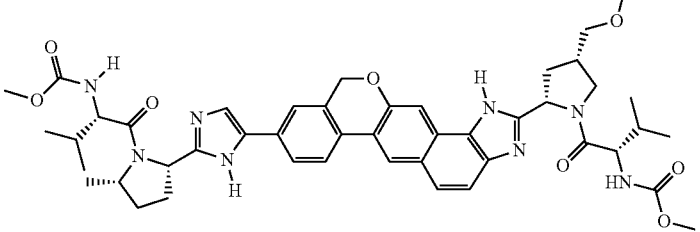 | | | | | | | | | |
| 562 | (Chiral) | 0.019 | C | C | C | C | C | C | C |
| 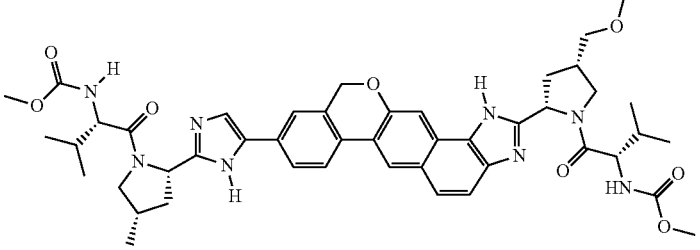 | | | | | | | | | |

TABLE 5-continued

| # | | 1b (nM) | 1a | 1a Q30R | 2a JFH | 2a J6 | 2b | 3a | 4a |
|---|---|---|---|---|---|---|---|---|---|
| 563 | Chiral | 0.007 | C | | C | A | A | B | C |
| 564 | Chiral | 0.012 | C | | C | B | C | C | C |
| 565 | Chiral | 0.017 | C | C | C | C | C | C | C |
| 566 | Chiral | 0.009 | C | C | C | C | C | C | C |
| 567 | Chiral | 0.007 | C | C | C | C | C | C | C |

TABLE 5-continued
| # | | 1b (nM) | 1a | 1a Q30R | 2a JFH | 2a J6 | 2b | 3a | 4a |
|---|---|---|---|---|---|---|---|---|---|
| 568 | Chiral 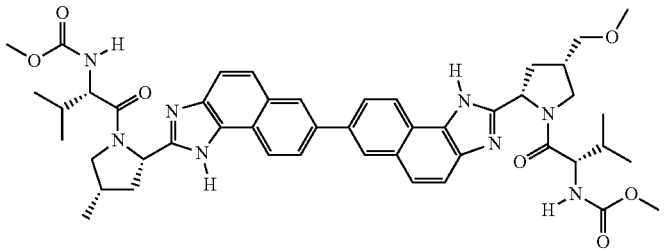 | 0.021 | C | C | C | C | C | C | C |
| 569 | Chiral 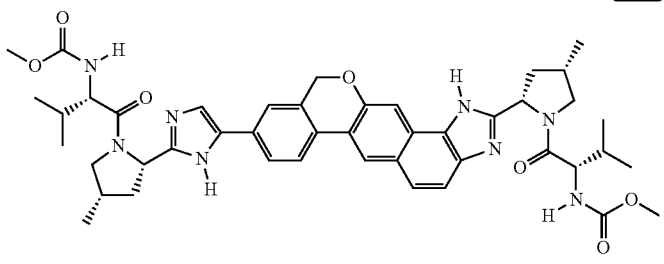 | 0.024 | C | C | C | C | C | C | C |
| 570 | 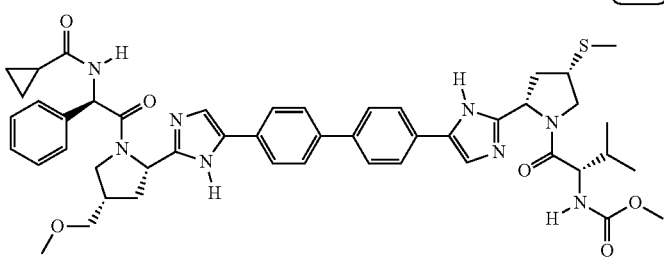 | 0.033 | C | | C | C | C | C | C |
| 571 | Chiral 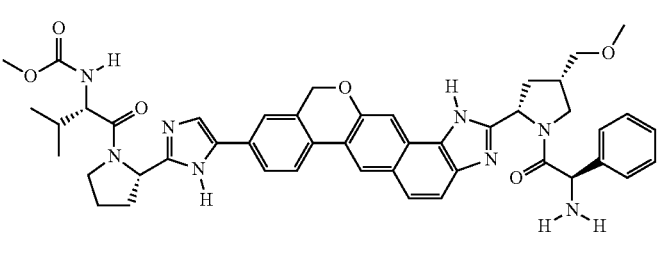 | 0.114 | C | C | C | C | C | C | C |
| 572 | Chiral 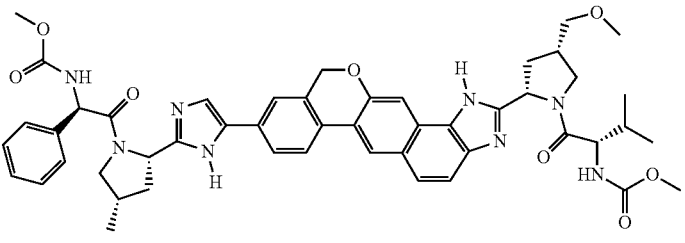 | 0.044 | C | C | C | C | C | C | C |

TABLE 5-continued

| # | | 1b (nM) | 1a | 1a Q30R | 2a JFH | 2a J6 | 2b | 3a | 4a |
|---|---|---|---|---|---|---|---|---|---|
| 573 | Chiral | 0.030 | C | C | C | C | C | C | C |
| 574 | Chiral | 0.016 | C | C | C | C | C | C | C |
| 575 | Chiral | 0.029 | C | C | C | C | C | C | C |
| 576 | Chiral | 0.014 | C | | C | B | C | C | C |
| 577 | Chiral | 0.017 | C | | C | A | B | C | C |

TABLE 5-continued
| # | | 1b (nM) | 1a | 1a Q30R | 2a JFH | 2a J6 | 2b | 3a | 4a |
|---|---|---|---|---|---|---|---|---|---|
| 578 | Chiral | 0.022 | C | | C | A | A | C | C |
| 579 | Chiral | 0.034 | C | C | C | C | C | C | C |
| 580 | Chiral | 0.017 | C | | C | C | C | C | C |
| 581 | Chiral | 0.007 | C | C | C | C | C | C | C |
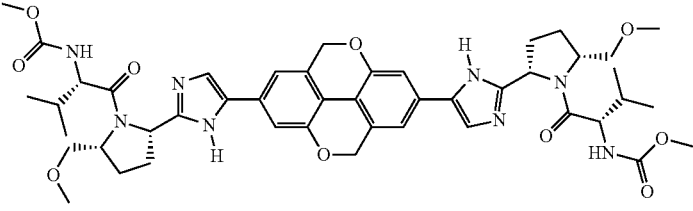
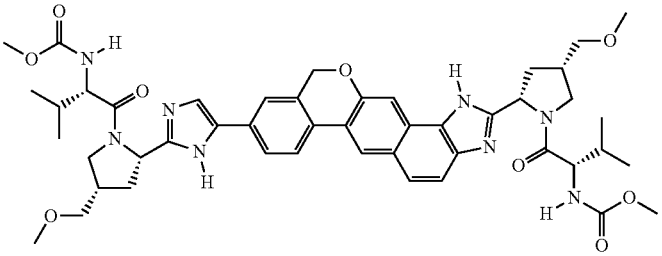
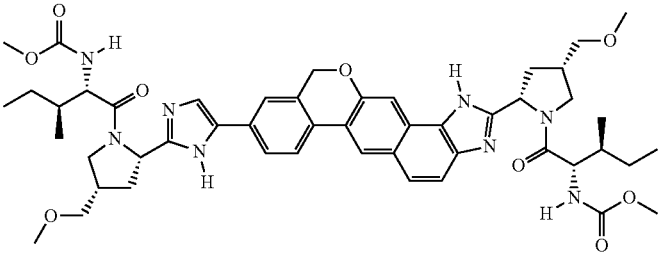
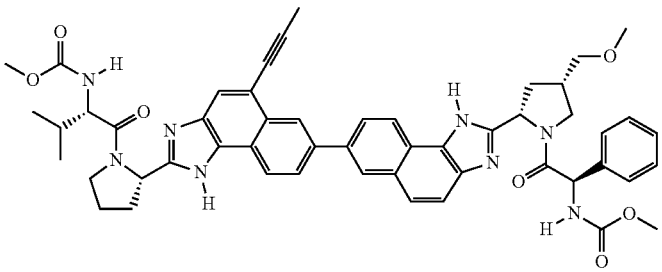

TABLE 5-continued

| # | | 1b (nM) | 1a | 1a Q30R | 2a JFH | 2a J6 | 2b | 3a | 4a |
|---|---|---|---|---|---|---|---|---|---|
| 582 | (Chiral) | 0.010 | C | C | C | C | C | C | C |
| 583 | | 0.018 | C | | C | C | C | C | C |
| 584 | | 0.015 | C | C | C | C | C | C | C |
| 585 | (Chiral) | 0.009 | C | C | C | C | C | C | C |

TABLE 5-continued
| # | | 1b (nM) | 1a | 1a Q30R | 2a JFH | 2a J6 | 2b | 3a | 4a |
|---|---|---|---|---|---|---|---|---|---|
| 586 | 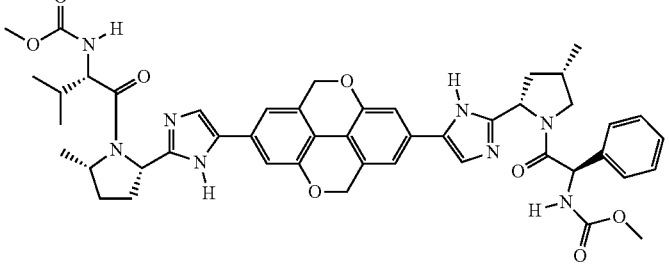 | 0.011 | C | C | C | C | C | C | |
| 587 | 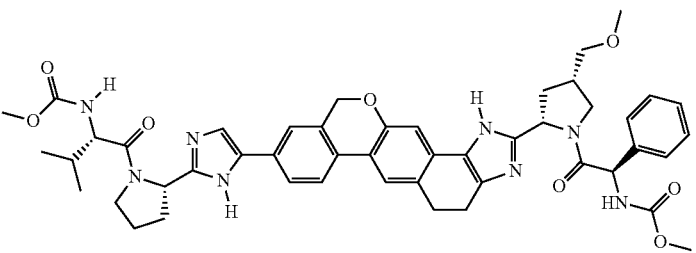 Chiral | 0.041 | C | C | C | C | C | C | C |
| 588 | 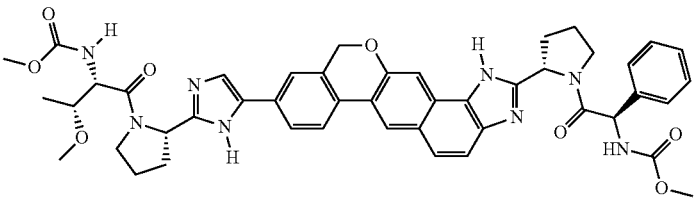 Chiral | 0.017 | C | C | C | C | C | C | C |
| 589 | 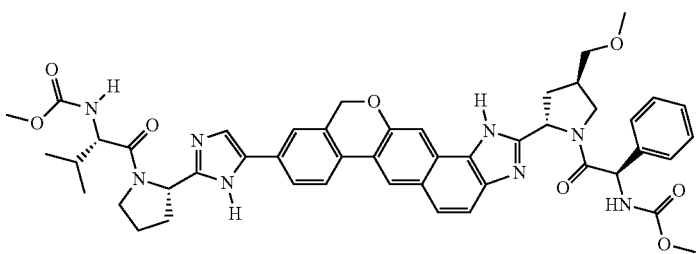 Chiral | 0.011 | C | C | C | C | C | C | C |
| 590 | 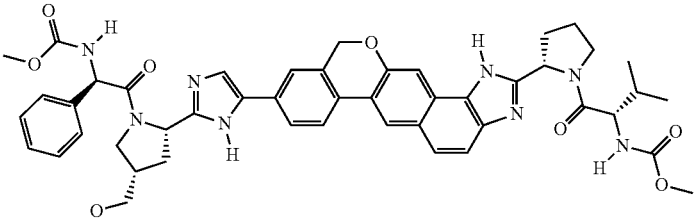 Chiral | 0.014 | C | C | C | C | C | C | C |

TABLE 5-continued
| # | | 1b (nM) | 1a | 1a Q30R | 2a JFH | 2a J6 | 2b | 3a | 4a |
|---|---|---|---|---|---|---|---|---|---|
| 591 | 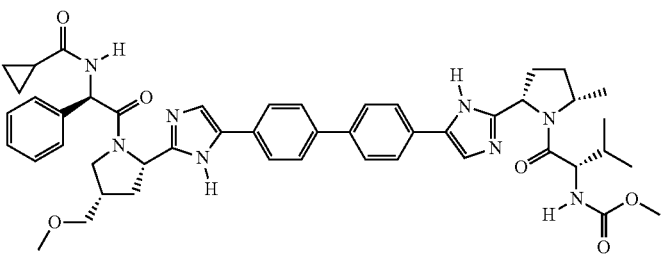 | 0.016 | C | | C | C | C | C | C |
| 592 | 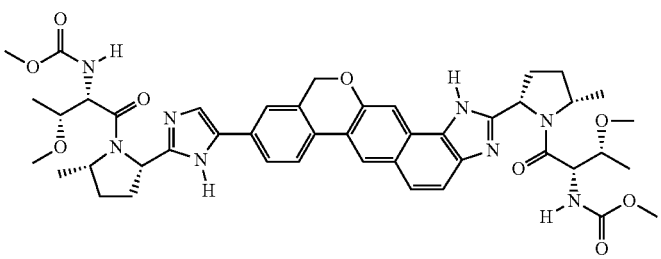 | 0.015 | C | C | C | C | C | C | C |
| 593 | 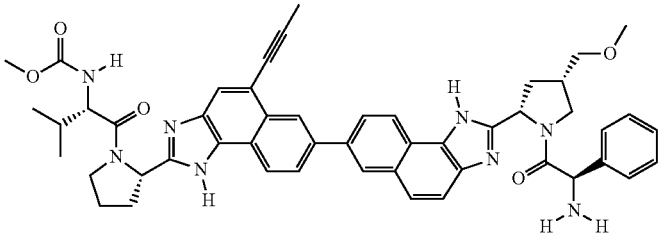 | 0.014 | C | B | C | C | B | | C |
| 594 | 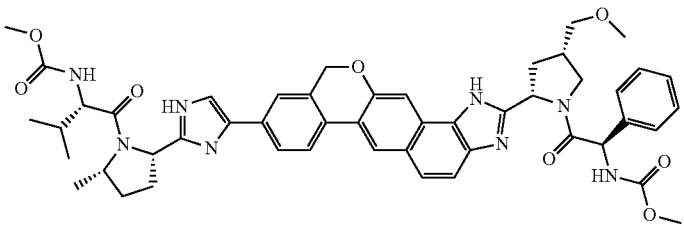 | 0.013 | C | C | C | C | C | | C |
| 595 | 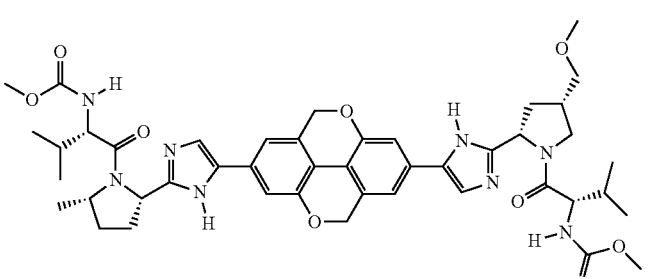 | 0.020 | C | | C | A | B | C | C |

TABLE 5-continued

| # | | 1b (nM) | 1a | 1a Q30R | 2a JFH | 2a J6 | 2b | 3a | 4a |
|---|---|---|---|---|---|---|---|---|---|
| 596 | (Chiral) | 0.013 | C | C | C | C | C | C | C |
| 597 | (Chiral) | 0.005 | C | C | C | C | C | C | |
| 598 | (Chiral) | 0.022 | C | C | C | C | C | | |
| 599 | (Chiral) | 0.009 | C | C | C | C | C | C | |
| 600 | (Chiral) | 0.007 | C | C | C | C | C | | |

TABLE 5-continued
| # | | 1b (nM) | 1a | 1a Q30R | 2a JFH | 2a J6 | 2b | 3a | 4a |
|---|---|---|---|---|---|---|---|---|---|
| 601 | 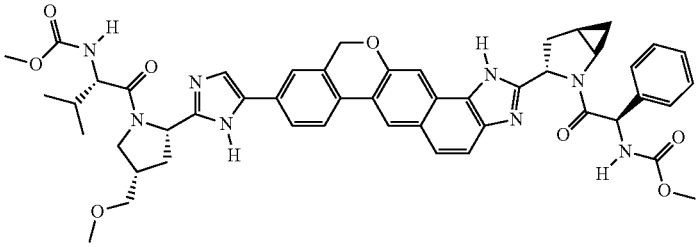 Chiral | 0.014 | C | C | C | C | C | C | |
| 602 | 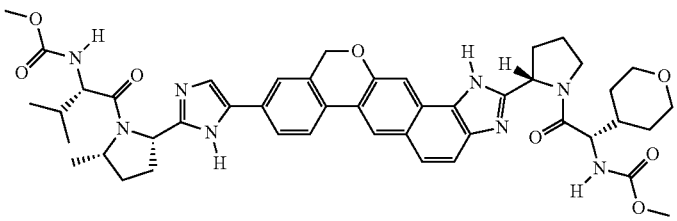 [SMILES: COC(=O)N[C@H](C(=O)N1[C@@H](C)CC[C@H]1c1ncc(-c2ccc3c(c2)COc2cc4c(ccc5nc([C@@H]6CCCN6C(=O)[C@@H](NC(=O)OC)C6CCOCC6)[nH]c54)cc2-3)[nH]1)C(C)C] | 0.025 | C | | C | C | C | | |
| 603 | 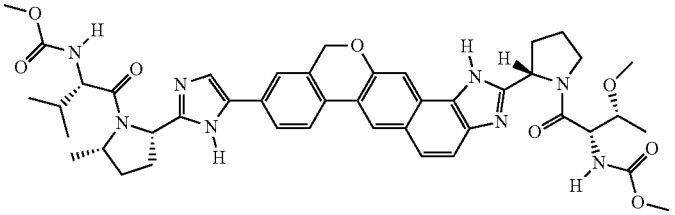 | 0.015 | C | C | C | C | C | C | |
| 604 | 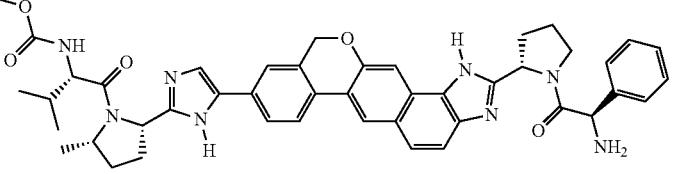 | 0.020 | C | | C | C | C | | |
| 605 | 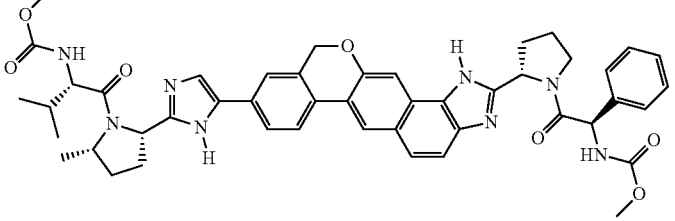 | 0.015 | C | C | C | C | C | C | |
| 606 | 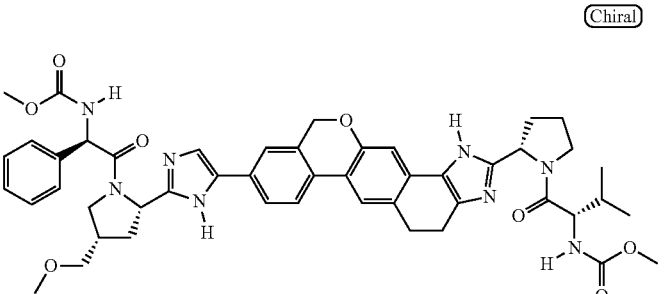 Chiral | 0.034 | C | C | C | C | C | C | |

TABLE 5-continued
| # | | 1b (nM) | 1a | 1a Q30R | 2a JFH | 2a J6 | 2b | 3a | 4a |
|---|---|---|---|---|---|---|---|---|---|
| 607 | (Chiral) 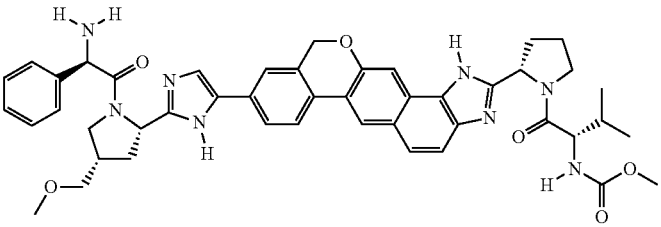 | 0.067 | C | | C | C | C | | |
| 608 | (Chiral) 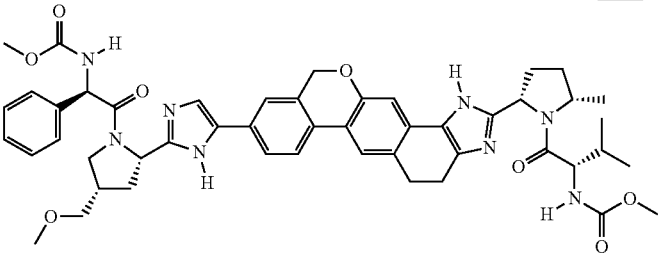 | 0.017 | C | C | C | C | C | | |
| 609 | (Chiral) 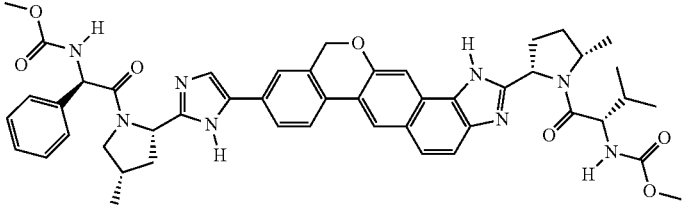 | 0.005 | C | C | C | C | C | C | |
| 610 | (Chiral) 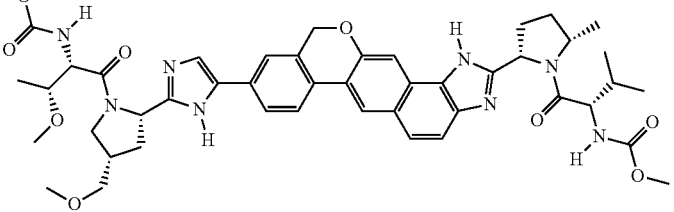 | 0.013 | C | C | C | C | C | C | |
| 611 | (Chiral) 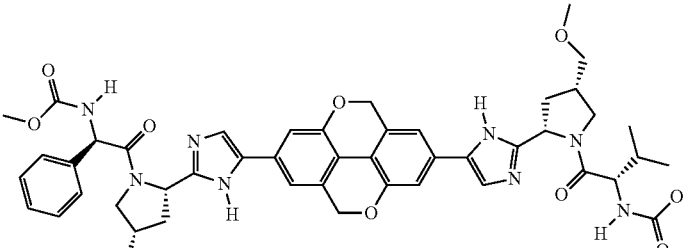 | 0.013 | C | C | C | C | C | C | |

TABLE 5-continued
| # | | 1b (nM) | 1a | 1a Q30R | 2a JFH | 2a J6 | 2b | 3a | 4a |
|---|---|---|---|---|---|---|---|---|---|
| 612 | (Chiral) 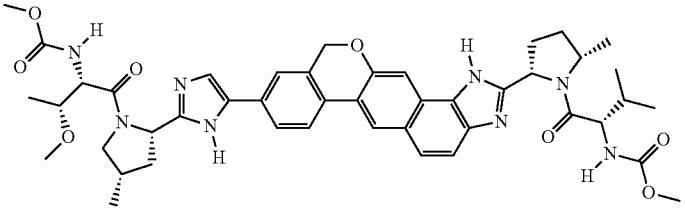 | 0.005 | C | C | C | C | C | C | |
| 613 | (Chiral) 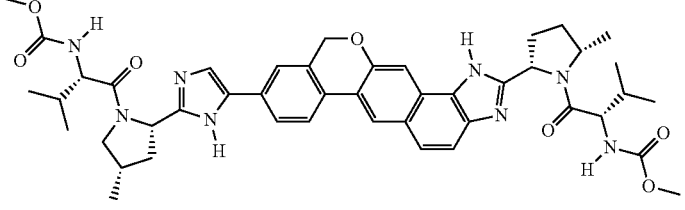 | 0.005 | C | C | C | C | C | C | |
| 614 | (Chiral) 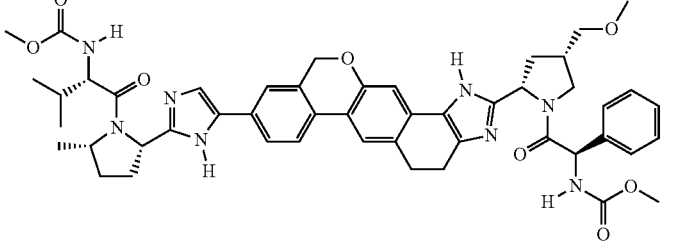 | 0.013 | C | C | C | C | C | C | |
| 615 | (Chiral) 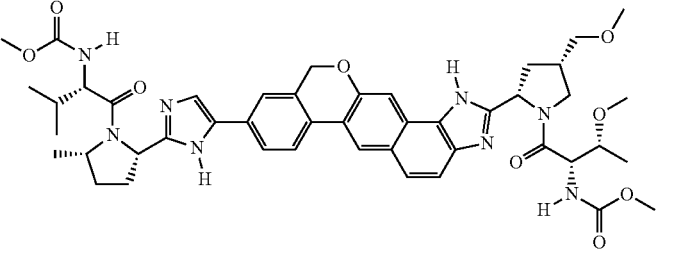 | 0.019 | C | C | C | C | C | C | |
| 616 | (Chiral) 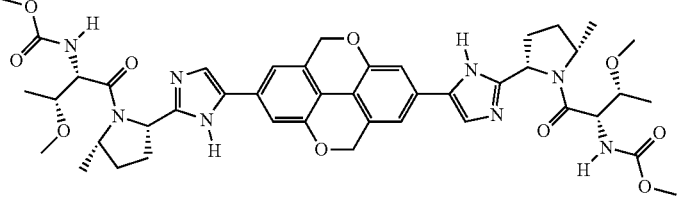 | 0.018 | C | C | C | C | C | C | |

TABLE 5-continued

| # | 1b (nM) | 1a | 1a Q30R | 2a JFH | 2a J6 | 2b | 3a | 4a |
|---|---|---|---|---|---|---|---|---|
| 617 | 0.005 | C | C | C | C | C | C | |
| 618 | 0.020 | C | C | C | C | C | C | |
| 619 | 0.007 | C | | C | C | C | | |
| 620 | 0.081 | C | | C | C | C | | |
| 621 | 0.013 | C | | C | C | C | | |

TABLE 5-continued

| # | | 1b (nM) | 1a | 1a Q30R | 2a JFH | 2a J6 | 2b | 3a | 4a |
|---|---|---|---|---|---|---|---|---|---|
| 622 | (Chiral) | 0.016 | C | C | C | C | C | C | |
| 623 | (Chiral) | 0.006 | C | | C | C | C | | |
| 624 | | | | | | | | | |
| 625 | (Chiral) | 0.031 | C | C | C | C | C | C | |
| 626 | (Chiral) | 0.030 | C | C | C | C | C | C | |

TABLE 5-continued
| # | | 1b (nM) | 1a | 1a Q30R | 2a JFH | 2a J6 | 2b | 3a | 4a |
|---|---|---|---|---|---|---|---|---|---|
| 627 | 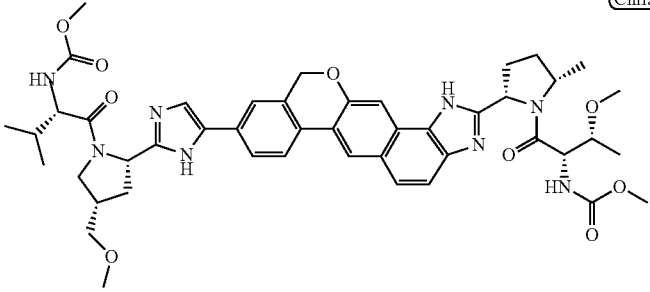 Chiral | 0.039 | C | C | C | C | C | C | |
| 628 | 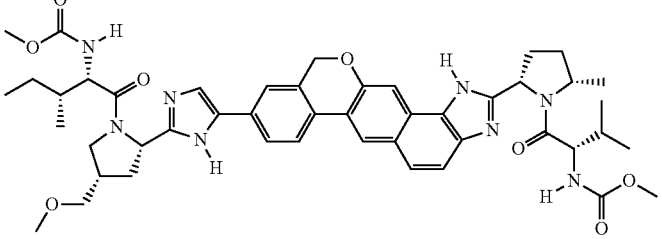 Chiral | 0.009 | C | | C | C | C | | |
| 629 | 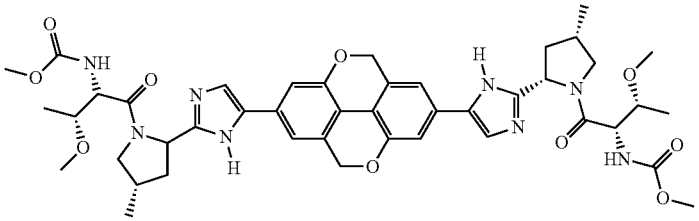 Chiral | | | | | | | | |
| 630 | 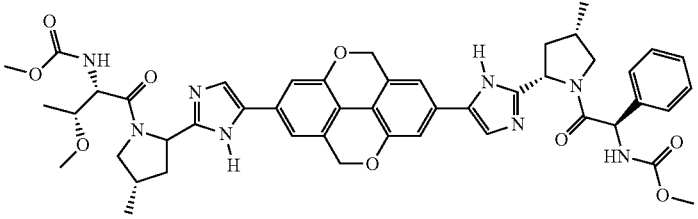 Chiral | | | | | | | | |
| 631 | 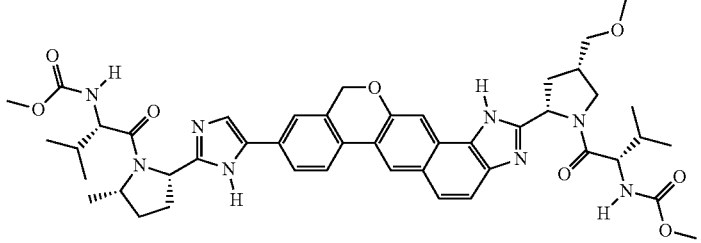 Chiral | 0.006 | C | | C | C | C | A | |

TABLE 5-continued
| # | | 1b (nM) | 1a | 1a Q30R | 2a JFH | 2a J6 | 2b | 3a | 4a |
|---|---|---|---|---|---|---|---|---|---|
| 632 | 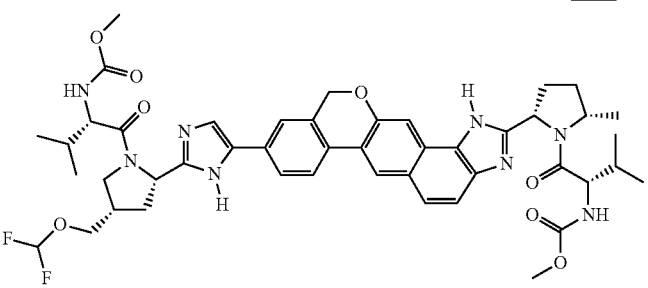 Chiral | 0.008 | C | | C | C | C | | |
| 633 | 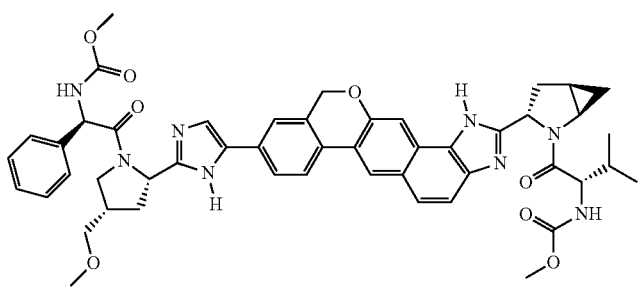 Chiral | 0.020 | C | C | C | C | C | C | |
| 634 | 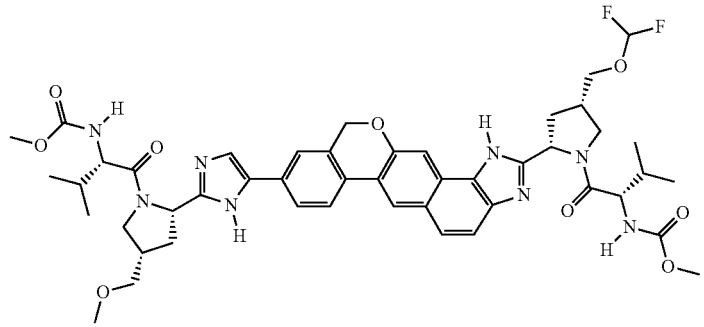 Chiral | 0.015 | C | | C | C | C | | |
| 635 | 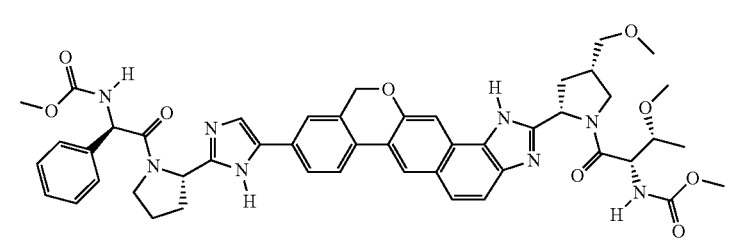 Chiral | 0.041 | C | | C | C | C | | |
| 636 | 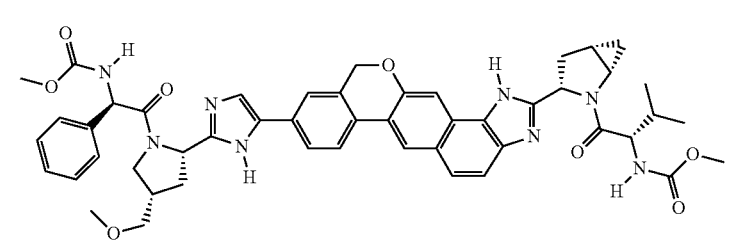 Chiral | 0.011 | C | C | C | C | C | C | |

TABLE 5-continued

| # | | 1b (nM) | 1a | 1a Q30R | 2a JFH | 2a J6 | 2b | 3a | 4a |
|---|---|---|---|---|---|---|---|---|---|
| 637 | Chiral | 0.009 | C | C | C | C | C | C | |
| 638 | Chiral | 0.009 | C | | C | C | C | | |
| 639 | Chiral | 0.011 | C | C | C | C | C | C | |
| 640 | Chiral | 0.015 | C | | C | C | C | | |
| 641 | Chiral | 0.030 | C | | C | C | C | | |

TABLE 5-continued

| # | 1b (nM) | 1a | 1a Q30R | 2a JFH | 2a J6 | 2b | 3a | 4a |
|---|---|---|---|---|---|---|---|---|
| 642 | 0.014 | C | | C | C | C | | |
| 643 | 0.015 | C | | C | C | C | | |
| 644 | | | | | | | | |
| 645 | | | | | | | | |
| 646 | | | | | | | | |

TABLE 5-continued

| # | 1b (nM) | 1a | 1a Q30R | 2a JFH | 2a J6 | 2b | 3a | 4a |
|---|---|---|---|---|---|---|---|---|

647 (Chiral)

648 (Chiral)

1b (nM); 1a, 1a Q30R, 2a JFH, 2a J6, 2b – A ≥ 44 nM, B = 1-43.99 nM, C = 0.001-0.999 nM; 3a, 4a – A ≥ 5 nM, B = 1-4.99 nM, C = 0.001-0.99 nM

What is claimed is:

1. A compound selected from the group consisting of:

(60)

(61)

(361)

(500)

(506)

(517)

(519)

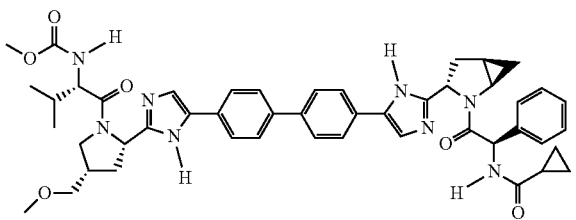

(527)

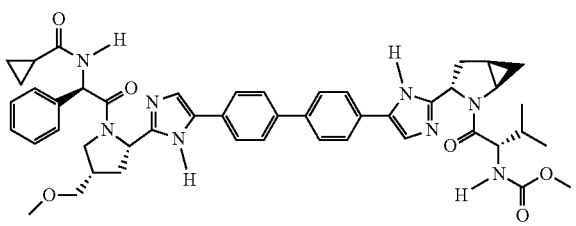

(557)

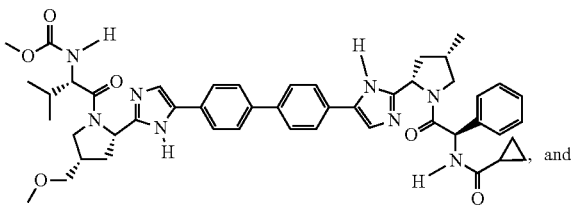

, and (570)

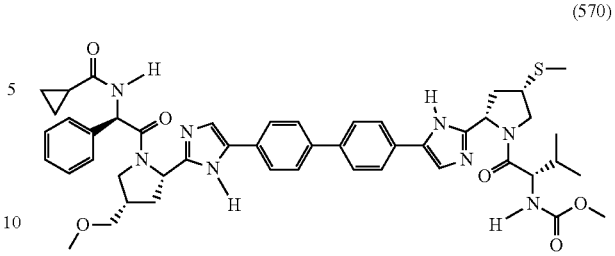

or a pharmaceutically acceptable salt thereof.

2. A pharmaceutical composition comprising a compound of claim 1 or a pharmaceutically acceptable salt thereof, and at least one pharmaceutically acceptable carrier.

3. The pharmaceutical composition of claim 2, further comprising at least one additional therapeutic agent.

4. The pharmaceutical composition of claim 3, wherein said additional therapeutic agent is a ribavirin analog, NS3 protease inhibitor, NS5b polymerase inhibitor, alpha-glucosidase 1 inhibitor, hepatoprotectant, non-nucleoside inhibitor of hepatitis C virus (HCV), or other drug for inhibiting HCV.

5. The pharmaceutical composition of claim 2, further comprising a nucleoside analogue.

6. The pharmaceutical composition of claim 5, wherein said nucleoside analogue is selected from the group consisting of ribavirin, viramidine, levovirin, a L-nucleoside, and isatoribine.

7. A method of inhibiting hepatitis C virus in a human patient in need thereof, said method comprising administering to the patient a pharmaceutical composition which comprises a therapeutically effective amount of a compound of claim 1 or a pharmaceutically acceptable salt thereof.

* * * * *